US012649750B2

(12) United States Patent
Liao et al.

(10) Patent No.: US 12,649,750 B2
(45) **Date of Patent: *Jun. 9, 2026**

(54) MACROCYCLIC COMPOUNDS, COMPOSITIONS, AND METHODS OF USING THEREOF

(71) Applicants: Sionna Therapeutics Inc., Waltham, MA (US); Genzyme Corporation, Cambridge, MA (US)

(72) Inventors: Junkai Liao, Andover, MA (US); John E. Macor, Washington Crossing, PA (US); George Topalov, Pittsburgh, PA (US); Mark Munson, Acton, MA (US); Sukanthini Thurairatnam, Dover, MA (US); Bradford Hirth, Littleton, MA (US); Zhongli Gao, Waltham, MA (US); Gregory Donald Hurlbut, Boxborough, MA (US); Andrew Good, Bideford (GB); Roy Vaz, Southborough, MA (US); Jinyu Liu, Union City, CA (US); Yi Li, Weston, MA (US); Anatoly Ruvinsky, Lexington, MA (US); Michael Kothe, Medway, MA (US); David Borcherding, Bangor, PA (US); Patrick Bernardelli, Paris (FR); Arielle Genevois Borella, Paris (FR); Franck Caussanel, Paris (FR); Ingrid Devillers, Paris (FR); Eric Nicolai, Paris (FR); Franck Slowinski, Paris (FR); Fabienne Thompson, Paris (FR); Lothar Schwink, Frankfurt am Main (DE); Heiner Glombik, Frankfurt am Main (DE); Stefan Guessregen, Frankfurt am Main (DE); Michael Podeschwa, Frankfurt am Main (DE); Nils Rackelmann, Frankfurt am Main (DE); Sven Ruf, Frankfurt am Main (DE)

(73) Assignees: Sionna Therapeutics Inc., Waltham, MA (US); Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/327,867

(22) Filed: Sep. 12, 2025

(65) Prior Publication Data

US 2026/0008785 A1 Jan. 8, 2026

Related U.S. Application Data

(63) Continuation of application No. 19/071,495, filed on Mar. 5, 2025, which is a continuation of application No. PCT/US2023/073543, filed on Sep. 6, 2023.

(Continued)

(51) Int. Cl.

| | |
|---|---|
| *C07D 515/18* | (2006.01) |
| *A61K 31/4162* | (2006.01) |
| *A61K 31/4188* | (2006.01) |
| *A61K 31/4192* | (2006.01) |
| *A61K 31/4196* | (2006.01) |
| *A61K 31/422* | (2006.01) |
| *A61K 31/424* | (2006.01) |
| *A61K 31/429* | (2006.01) |
| *A61K 31/433* | (2006.01) |
| *A61K 31/439* | (2006.01) |
| *A61K 31/4439* | (2006.01) |

(Continued)

(52) U.S. Cl.

CPC ........ *C07D 515/18* (2013.01); *A61K 31/4162* (2013.01); *A61K 31/4188* (2013.01); *A61K 31/4192* (2013.01); *A61K 31/4196* (2013.01); *A61K 31/422* (2013.01); *A61K 31/424* (2013.01); *A61K 31/429* (2013.01); *A61K 31/433* (2013.01); *A61K 31/439* (2013.01); *A61K 31/4439* (2013.01); *A61K 31/444* (2013.01); *A61K 31/496* (2013.01); *A61K 31/497* (2013.01); *A61K 31/504* (2013.01); *A61K 31/5377* (2013.01); *A61P 11/12* (2018.01); *C07D 513/22* (2013.01); *C07D 515/22* (2013.01)

(58) Field of Classification Search

CPC .................................................... C07D 515/18

See application file for complete search history.

(56) References Cited

U.S. PATENT DOCUMENTS

| | | | |
|---|---|---|---|
| 8,999,976 | B2 | 4/2015 | Binch et al. |
| 2015/0005275 | A1 | 1/2015 | Plas et al. |

(Continued)

FOREIGN PATENT DOCUMENTS

| | | | |
|---|---|---|---|
| WO | WO-2005120497 | A2 | 12/2005 |
| WO | WO-2006002421 | | 1/2006 |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

"Find ETDs Home > Thesis Resources > Find ETDs" Online: "https://ndltd.org/thesis-resources/find-etds/" Accessed Jan. 31, 2023.*

Irwin "ZINC—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

(Continued)

*Primary Examiner* — Nizal S Chandrakumar

(74) *Attorney, Agent, or Firm* — Goodwin Procter LLP

(57) ABSTRACT

The present disclosure includes, among other things, CFTR modulators, pharmaceutical compositions, and methods of making and using the same.

22 Claims, No Drawings

Related U.S. Application Data

(60) Provisional application No. 63/404,440, filed on Sep. 7, 2022.

(51) Int. Cl.

| | |
|---|---|
| ***A61K 31/444*** | (2006.01) |
| ***A61K 31/496*** | (2006.01) |
| ***A61K 31/497*** | (2006.01) |
| ***A61K 31/504*** | (2006.01) |
| ***A61K 31/5377*** | (2006.01) |
| ***A61P 11/12*** | (2006.01) |
| ***C07D 513/22*** | (2006.01) |
| ***C07D 515/22*** | (2006.01) |

(56) References Cited

U.S. PATENT DOCUMENTS

| | | | |
|---|---|---|---|
| 2015/0045327 | A1 | 2/2015 | Van Der Plas et al. |
| 2016/0095858 | A1 | 4/2016 | Miller et al. |
| 2016/0120841 | A1 | 5/2016 | Kym et al. |
| 2016/0122331 | A1 | 5/2016 | Kym et al. |
| 2016/0355480 | A1 | 12/2016 | Altenbach et al. |
| 2024/0279220 | A1 | 8/2024 | Liao et al. |
| 2025/0197420 | A1 | 6/2025 | Liao et al. |
| 2025/0197422 | A1 | 6/2025 | Liao et al. |
| 2025/0248975 | A1 | 8/2025 | Liao et al. |
| 2026/0008786 | A1 | 1/2026 | Liao et al. |

FOREIGN PATENT DOCUMENTS

| | | | | |
|---|---|---|---|---|
| WO | WO-2008147952 | A1 | 4/2008 | |
| WO | WO-2009074575 | A2 | 6/2009 | |
| WO | WO-2009076593 | A1 | 6/2009 | |
| WO | WO-2010048573 | A1 | 4/2010 | |
| WO | WO-2011072241 | A1 | 6/2011 | |
| WO | WO-2011113894 | A1 | 9/2011 | |
| WO | WO-2012170889 | A1 | 12/2012 | |
| WO | WO-2013003837 | A1 | 1/2013 | |
| WO | WO-2013038373 | A1 | 3/2013 | |
| WO | WO-2013038381 | A1 | 3/2013 | |
| WO | WO-2013038386 | A1 | 3/2013 | |
| WO | WO-2013038390 | A1 | 3/2013 | |
| WO | WO-2013043720 | A1 | 3/2013 | |
| WO | WO-2014180562 | A1 | 11/2014 | |
| WO | WO-2014186704 | A2 | 11/2014 | |
| WO | WO-2015018823 | A1 | 2/2015 | |
| WO | WO-2015138909 | A1 | 9/2015 | |
| WO | WO-2015138934 | A1 | 9/2015 | |
| WO | WO-2016130929 | A1 | 8/2016 | |
| WO | WO-2016130943 | A1 | 8/2016 | |
| WO | WO-2018167690 | A1 | 9/2018 | |
| WO | WO-2019161078 | | 8/2019 | |
| WO | WO-2022032068 | | 2/2022 | |
| WO | WO-2022076622 | | 4/2022 | |
| WO | WO-2022109573 | A1 | 5/2022 | |
| WO | WO 2023/034992 | * | 3/2023 | ........... C07D 403/12 |
| WO | WO-2023034946 | A1 | 3/2023 | |
| WO | WO-2024054845 | A1 | 3/2024 | |
| WO | WO-2024054851 | A1 | 3/2024 | |
| WO | WO-2024097227 | A1 | 5/2024 | |
| WO | WO-2025189008 | A1 | 9/2025 | |

OTHER PUBLICATIONS

STN Registry/Zregistry (CAS Registrysm) Sep. 2016 2 pages.*

Meanwell, Top Med Chem (2015) 9: 283-382.*

Fang, Future Medicinal Chemistry, 6(8), 885-901, May 2014.*

Chandrakumar, Journal of Medicinal Chemistry (1992), 35(16), 2928-38.*

Chandrakumar, Journal of Medicinal Chemistry (1992), 35(2), 223-33.*

Snyder, Journal of the American Chemical Society (2000), 122(3), 544-545.*

Lankin, Journal of the American Chemical Society (1993), 115(8), 3356-7.*

Patani et al., Bioisosterism: A Rational Approach in Drug Design, Chem. Rev., (96):3147-3176 (1996).

Co-pending U.S. Appl. No. 19/327,881, filed Sep. 12, 2025.

Derichs, Targeting a genetic defect: cystic fibrosis transmembrane conductance regulator modulators in cystic fibrosis, European Respiratory Review, 22:127, 58-65 (2013).

Gregory, R. J. et al., Expression and charaterization of the cystic fibrosis transmembrane conductance regulator, Nature, 347:382-386 (1990).

He, et al., Restoration of NBD1 thermal stability is necessary and sufficient to correct F508 CFTR folding and assembly, J Mol Biol., 427(1): 106-120 (2015).

PCT/US2023/073543 International Preliminary Report on Patentability mailed Mar. 20, 2025.

PCT/US2023/073543 International Search Report and Written Opinion mailed Nov. 21, 2023.

PCT/US2023/073551 International Preliminary Report on Patentability mailed Mar. 20, 2025.

PCT/US2023/073551 International Search Report and Written Opinion mailed Nov. 21, 2023.

PCT/US2023/073558 International Preliminary Report on Patentability mailed Mar. 20, 2025.

PCT/US2023/073558 International Search Report and Written Opinion mailed Oct. 26, 2023.

Rich, D. P. et al., Expression of cystic fibrosis transmembrane conductance regulator corrects defective chloride channel regulation in cystic fibrosis airway epithelial cells, Nature, 347:358-362 (1990).

Riordan, J. R. et al., Identification of the Cystic Fibrosis Gene: Cloning and Characterization of Complementary DNA, Science, 245:1066-1073 (1989).

* cited by examiner

MACROCYCLIC COMPOUNDS, COMPOSITIONS, AND METHODS OF USING THEREOF

CROSS-REFERENCE TO RELATED APPLICATIONS

This application is a continuation of U.S. patent application Ser. No. 19/071,495, filed Mar. 5, 2025, which is a continuation of International Application No. PCT/US2023/073543, filed Sep. 6, 2023, which claims the benefit of and priority to U.S. Provisional Patent Application No. 63/404,440, filed Sep. 7, 2022, each of which are hereby incorporated by reference in their entireties for all purposes.

BACKGROUND

Cystic fibrosis (CF), an autosomal recessive disorder, is caused by functional deficiency of the cAMP-activated plasma membrane chloride channel, cystic fibrosis transmembrane conductance regulator (CFTR), which results in pulmonary and other complications. The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). CFTR, a member of the ATP binding cassette (ABC) superfamily is composed of two six membrane-spanning domains (MSD1 and MSD2), two nucleotide bind domains (NBD1 and NBD2), a regulatory region (R) and four cytosolic loops (CL1-4). CFTR protein is located primarily in the apical membrane of epithelial cells where it functions to conduct anions, including chloride, bicarbonate, and thiocyanate into and out of the cell. CFTR may have a regulatory role over other electrolyte channels, including the epithelial sodium channel ENaC.

In cystic fibrosis patients, the absence or dysfunction of CFTR leads to exocrine gland dysfunction and a multisystem disease, characterized by pancreatic insufficiency and malabsorption, as well as abnormal mucociliary clearance in the lung, mucostasis, chronic lung infection and inflammation, decreased lung function and ultimately respiratory failure.

While more than 1,900 mutations have been identified in the CFTR gene, a detailed understanding of how each CFTR mutation may impact channel function is known for only a few. (Derichs, European Respiratory Review, 22:127, 58-65 (2013)). The most frequent CFTR mutation is the in-frame deletion of phenylalanine at residue 508 (ΔF508) in the first nucleotide binding domain (NBD1). Over 70% of cystic fibrosis patients have a deletion at residue 508 in at least one CFTR allele. The loss of this key phenylalanine renders NBD1 conformationally unstable at physiological temperature and compromises the integrity of the interdomain interface between NDB1 and CFTR's second transmembrane domain (ICL4). The ΔF508 mutation causes production of misfolded CFTR protein which, rather than traffic to the plasma membrane, is instead retained in the endoplasmic reticulum and targeted for degradation by the ubiquitin-proteasome system.

The loss of a functional CFTR channel at the plasma membrane disrupts ionic homeostasis and airway surface hydration leading to reduced lung function. Reduced periciliary liquid volume and increased mucus viscosity impede mucociliary clearance resulting in chronic infection and inflammation. In the lung, the loss of CFTR-function leads to numerous physiological effects downstream of altered anion conductance that result in the dysfunction of additional organs such as the pancreas, intestine and gall bladder.

By studying the mechanistic aspects of CFTR misfolding and corrections, small molecules have been identified as CF modulators, that can act as stabilizers.

Despite the identification of compounds that modulate CFTR, there is no cure for this fatal disease and identification of new compounds and new methods of therapy are needed as well as new methods for treating or lessening the severity of cystic fibrosis and other CFTR mediated conditions and diseases in a patient.

SUMMARY

The present disclosure includes a compound of formula A:

A

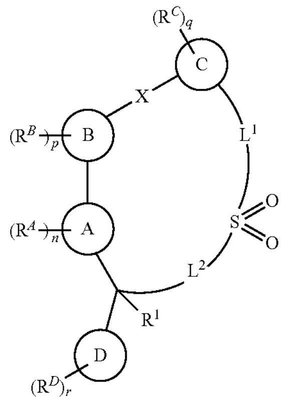

or a pharmaceutically acceptable salt thereof. Additionally, the present disclosure includes, among other things, pharmaceutical compositions, methods of using and methods of making a compound of formula A.

DETAILED DESCRIPTION

In some embodiments, the present disclosure includes a compound of Formula A:

A

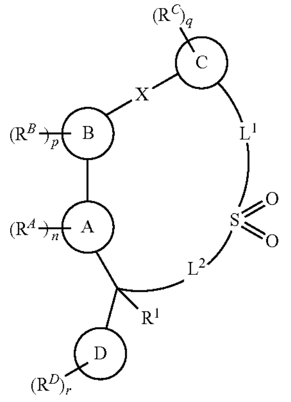

or a pharmaceutically acceptable salt thereof, wherein $L^1$ is an optionally substituted $C_{1-6}$ alkylene chain wherein 1-3 of the methylene units is optionally and independently replaced by —O—, —N($R^2$), —C(O)—, —S—, —S(O)—, —S(O)$_2$—, an optionally substituted 3-6 membered carbocyclyl,

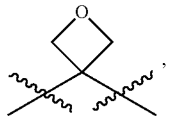 [SMILES: *C1(*)COC1]

optionally substituted $C_2$ alkenylene, or optionally substituted 5-6-membered heteroaryl;

$L^2$ is an optionally substituted $C_{1-6}$ alkylene chain wherein 1-3 of the methylene units is optionally and independently replaced by —C($CD_3$)$_2$-, —O—, —N($R^2$), —C(O)—, —S—, —S(O)—, an optionally substituted 3-6 membered carbocyclyl, —S(O)$_2$—, optionally substituted $C_2$ alkenylene, or optionally substituted 5-6-membered heteroaryl;

Ring A is optionally substituted 5-membered heteroaryl comprising 1-3 heteroatoms selected from the group consisting of N, O or S;

Ring B is optionally substituted phenyl or optionally substituted 6-membered heteroaryl;

Ring C is optionally substituted phenyl or optionally substituted 5-10-membered heteroaryl;

Ring D is optionally substituted phenyl or optionally substituted 5-6-membered heteroaryl;

X is selected from the group consisting of —O—, —S—, —$CH_2$—, —C(OH)H—, —SO—, —CO—, —$SO_2$—, —CFH—, —$CF_2$—, and —N($R^2$)—;

each $R^A$ is independently selected from the group consisting of halogen, cyano, optionally substituted $C_1$-$C_6$ aliphatic, optionally substituted $C_1$-$C_6$ alkoxy, and —$CD_3$;

each $R^B$ is independently selected from the group consisting of halogen, cyano, —C(O)N($R^2$)$_2$, C(O)O$R^2$, —O$R^2$, —N($R^2$)$_2$, optionally substituted $C_1$-$C_6$ aliphatic and optionally substituted $C_1$-$C_6$ alkoxy;

each $R^C$ is independently halogen, cyano, optionally substituted $C_1$-$C_6$ aliphatic or optionally substituted $C_1$-$C_6$ alkoxy;

each $R^D$ is independently selected from the group consisting of halogen, cyano, —C(O)N($R^2$)$_2$, —C(O)O$R^2$, —O$R^2$, —N($R^2$)$_2$, optionally substituted $C_1$-$C_6$ aliphatic, optionally substituted $C_1$-$C_3$ alkoxy, optionally substituted 5-6-membered heteroaryl, and optionally substituted 3-6-membered heterocyclyl comprising 1-3 heteroatoms selected from the group consisting of N, O or S, wherein each $R^D$ is optionally substituted with 1-6 instances of $R^d$.

each $R^d$ is independently selected from the group consisting of hydrogen, —OH, —$CD_3$, —C(O)N($R^2$)$_2$, C(O)O$R^2$, —O$R^2$, —N($R^2$)$_2$, optionally substituted $C_1$-$C_6$ aliphatic, optionally substituted 5-6-membered heteroaryl, and optionally substituted 3-6-membered heterocyclyl comprising 1-3 heteroatoms selected from the group consisting of N, O or S $R^1$ is selected from the group consisting of hydrogen, cyano, —O$R^2$, —($CH_2$)$_{0-3}$N($R^2$)$_2$, optionally substituted $C_1$-$C_3$ aliphatic, and —$CD_3$;

each $R^2$ is independently selected from hydrogen, optionally substituted $C_1$-$C_6$ aliphatic, —OH, $C_1$-$C_6$ alkoxy, —S(O)$_2$ (optionally substituted $C_1$-$C_6$ aliphatic);

n is 0, 1, 2 or 3;

p is 0, 1, 2, 3 or 4;

q is 0, 1 or 2; and r is 0, 1, 2, 3, 4 or 5.

In some embodiments, the present disclosure includes a compound of Formula I:

I

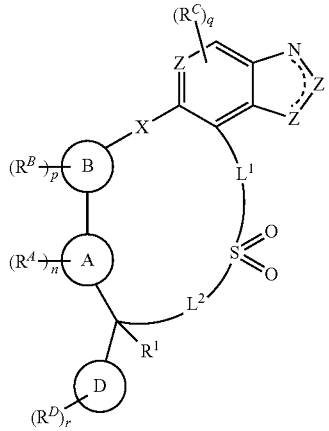

or a pharmaceutically acceptable salt thereof, wherein $L^1$ is an optionally substituted $C_{1-6}$ alkylene chain wherein 1-3 of the methylene units is optionally and independently replaced by —O—, —N($R^2$), —C(O)—, —S—, —S(O)—, —S(O)$_2$—, an optionally substituted 3-6 membered carbocyclyl,

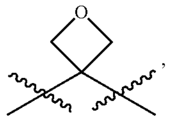 [SMILES: *C1(*)COC1]

optionally substituted $C_2$ alkenylene, or optionally substituted 5-6-membered heteroaryl;

$L^2$ is an optionally substituted $C_{1-6}$ alkylene chain wherein 1-3 of the methylene units is optionally and independently replaced by —C($CD_3$)$_2$-, —O—, —N($R^2$)—, —C(O)—, —S—, —S(O)—, an optionally substituted 3-6 membered carbocyclyl, —S(O)$_2$—, optionally substituted $C_2$ alkenylene, or optionally substituted 5-6-membered heteroaryl;

Ring A is an optionally substituted 5-membered heteroaryl comprising 1-4 heteroatoms selected from the group consisting of N, O or S;

Ring B is optionally substituted phenyl or optionally substituted 6-membered heteroaryl;

Ring D is optionally substituted phenyl or optionally substituted 5-6-membered heteroaryl;

X is selected from the group consisting of —O—, —S—, —$CH_2$—, —C(OH)H—, —$CHCH_3$, —SO—, —CO—, —$SO_2$—, —CFH—, —$CF_2$—, and —N($R^2$)—;

each $R^A$ is independently selected from the group consisting of halogen, cyano, optionally substituted $C_1$-$C_6$ aliphatic, optionally substituted $C_1$-$C_6$ alkoxy, and —$CD_3$;

each $R^B$ is independently selected from the group consisting of halogen, cyano, —C(O)N($R^2$)$_2$, C(O)O$R^2$, $-OR^2$, $-N(R^2)_2$, optionally substituted $C_1$-$C_6$ aliphatic and optionally substituted $C_1$-$C_6$ alkoxy;

each $R^C$ is independently selected from the group consisting of hydrogen, halogen, cyano, $-(CH_2)_{0-3}C(O)OH$, optionally substituted $C_1$-$C_6$ aliphatic or optionally substituted $C_1$-$C_6$ alkoxy;

each $R^D$ is independently selected from the group consisting of halogen, cyano, $-C(O)N(R^2)_2$, $-C(O)OR^2$, $-OR^2$, $-N(R^2)_2$, optionally substituted $C_1$-$C_6$ aliphatic, optionally substituted $C_1$-$C_3$ alkoxy, optionally substituted 5-6-membered heteroaryl, and optionally substituted 3-6-membered heterocyclyl comprising 1-3 heteroatoms selected from the group consisting of N, O or S, wherein each $R^D$ is optionally substituted with 1-6 instances of $R^d$.

wherein two instances of $R^D$ may be taken together to form an optionally substituted 5-7 membered carbocyclic ring, optionally substituted 5-6-membered heteroaryl, and optionally substituted 3-6-membered heterocyclyl comprising 1-3 heteroatoms selected from the group consisting of N, O or S;

each $R^d$ is independently selected from the group consisting of hydrogen, —OH, $-CD_3$, $-C(O)N(R^2)_2$, $C(O)OR^2$, $-OR^2$, $-N(R^2)_2$, $-S(O)_2R^2$ optionally substituted $C_1$-$C_6$ aliphatic, optionally substituted 5-6-membered heteroaryl, and optionally substituted 3-6-membered heterocyclyl comprising 1-3 heteroatoms selected from the group consisting of N, O or S;

$R^1$ is selected from the group consisting of hydrogen, cyano, $-OR^2$, $-(CH_2)_{0-3}N(R^2)_2$, optionally substituted $C_1$-$C_3$ aliphatic, 3-6-membered heterocyclyl comprising 1-3 heteroatoms selected from the group consisting of N, O or S, and $-CD_3$;

each $R^2$ is independently selected from hydrogen, optionally substituted $C_1$-$C_6$ aliphatic, —OH, $C_1$-$C_6$ alkoxy, $-S(O)_2$ (optionally substituted $C_1$-$C_6$ aliphatic);

each Z independently is —CH=, —N= or —NH—;

n is 0, 1, 2 or 3;

p is 0, 1, 2, 3 or 4;

q is 0, 1 2, or 3; and r is 0, 1, 2, 3, 4 or 5.

In some embodiments, the present disclosure includes a compound of formula I-a, I-b, I-c, or I-d:

(I-a)

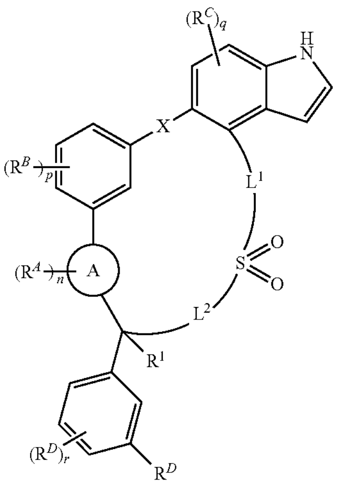

,

-continued (I-b)

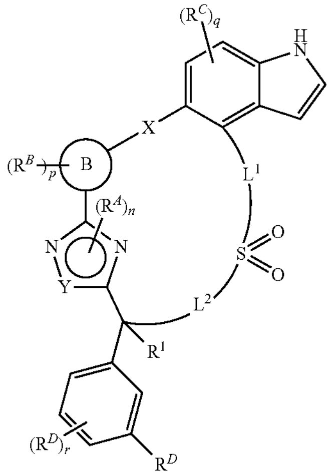

, (I-c)

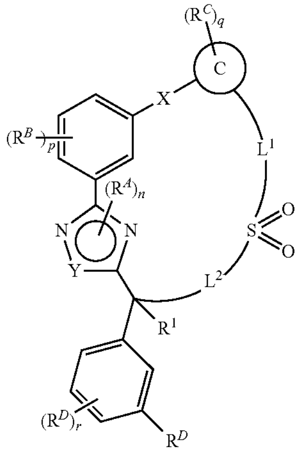

or (I-d)

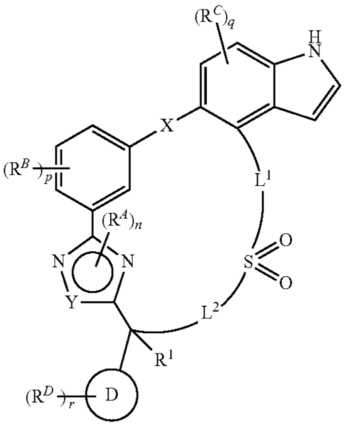

or a pharmaceutically acceptable salt thereof, wherein Ring A, Ring B, Ring C, Ring D, $L^1$, $L^2$, X, Y, $R^1$, $R^A$, $R^B$, $R^C$, $R^D$, n, p, q, and r are defined herein.

In some embodiments, a compound is of formula (I-a1), (I-a2), (I-a3), (I-a4), or (I-a5):
(I-a1)
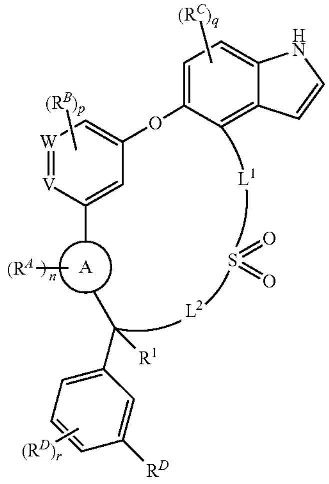
,
(I-a2)
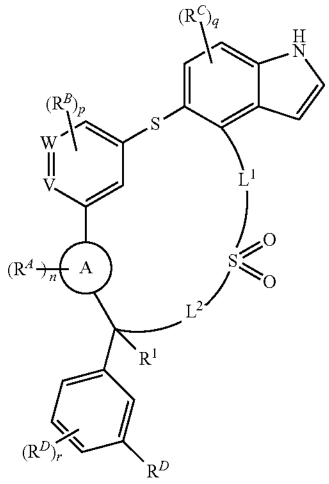
,
(I-a3)
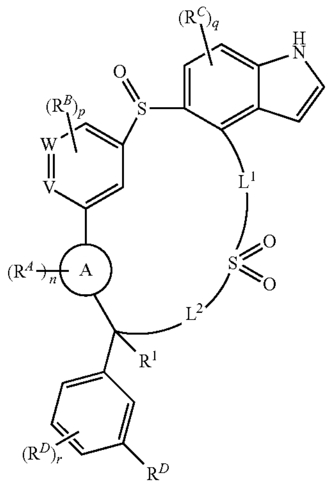
,
-continued
(I-a4)
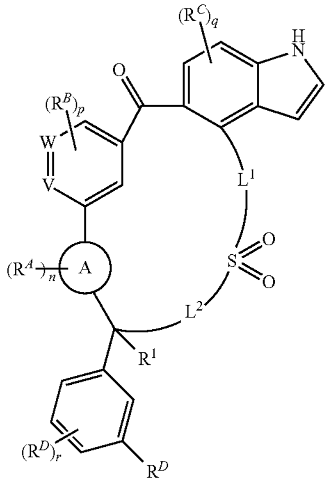
, or
(I-a5)
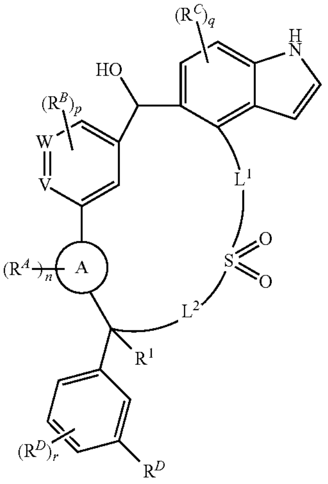
,
or a pharmaceutically acceptable salt thereof.
wherein Ring A, $L^1$, $L^2$, W, V, $R^1$, $R^A$, $R^B$, $R^C$, $R^D$, n, p, q, and rare defined herein.
In some embodiments, a compound is of formula (I-d1), (I-d2), (I-d3), (I-d4), or (I-d5)
(I-d1)
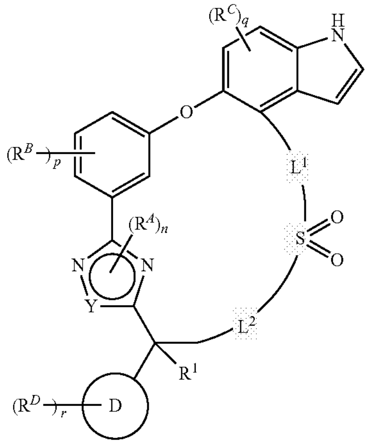

-continued (I-d2)

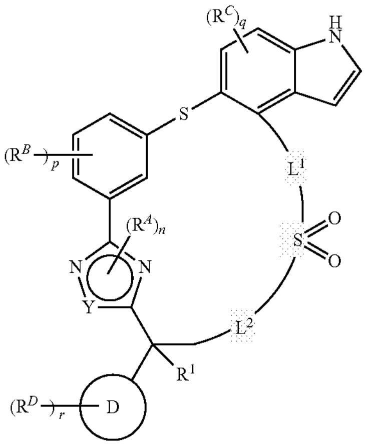

(I-d3)

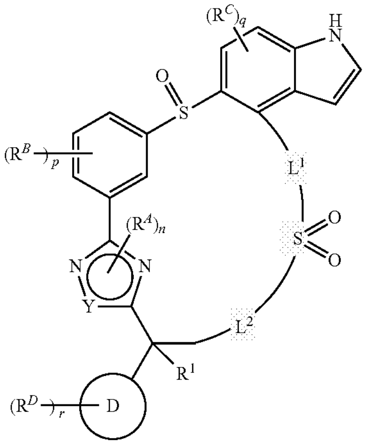

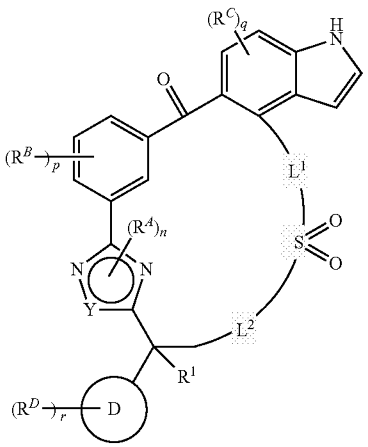

-continued

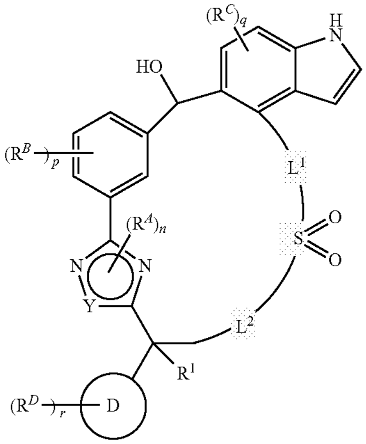

or a pharmaceutically acceptable salt thereof, wherein Ring D, $L^1$, $L^2$, Y, $R^1$, $R^A$, $R^B$, $R^C$, $R^D$, n, p, q, and rare defined herein.

In some embodiments, the present disclosure includes compound is of formula (I-e):

I-e

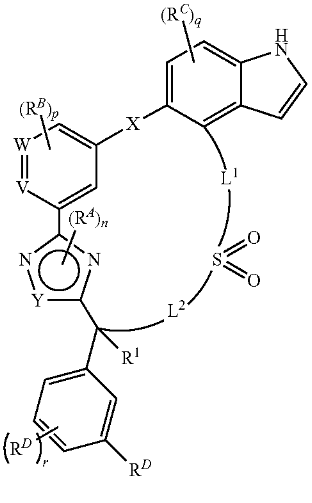

, or a pharmaceutically acceptable salt thereof, wherein $L^1$, $L^2$, V, W, X, Y, $R^1$, $R^A$, $R^B$, $R^C$, $R^D$, n, p, q, and rare defined herein.

In some embodiments, the present disclosure includes a compound of formula I-f:

I-f

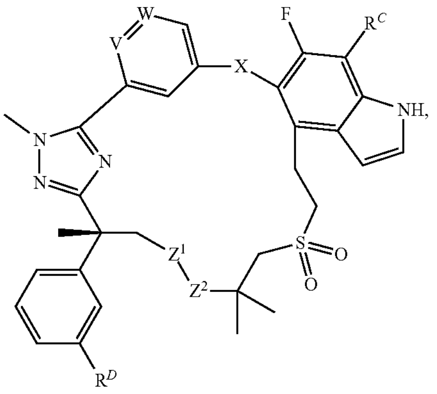

or a pharmaceutically acceptable salt thereof, wherein V, W, X, $Z^1$, $Z^2$, $R^C$, and $R^D$ are defined herein.

In some embodiments, the present disclosure includes a compound of formula I-g:

I-g

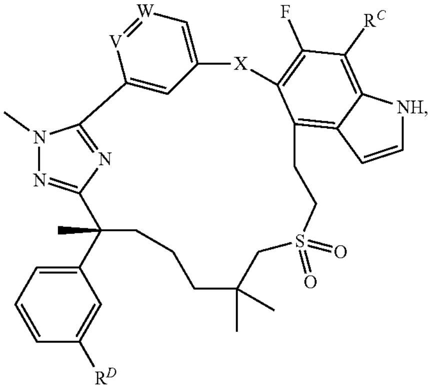

or a pharmaceutically acceptable salt thereof, wherein V, W, X, $R^C$, and $R^D$ are defined herein.

In some embodiments, the present disclosure includes a compound is of formula (I-g1) or (I-g2)

(I-g1)

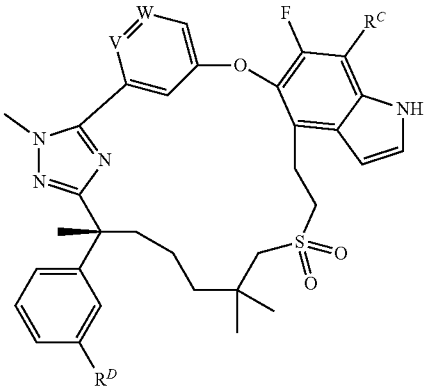

or

-continued (I-g2)

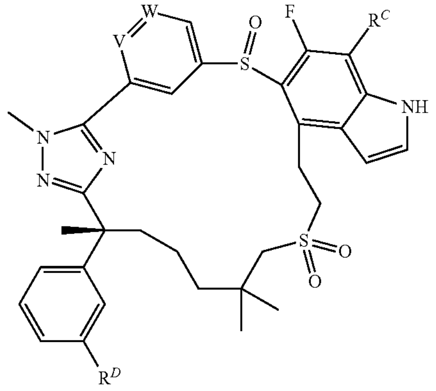

or a pharmaceutically acceptable salt thereof, wherein V, W, $R^C$, and $R^D$ are defined herein.

In some embodiments, the present disclosure includes a compound of formula I-h:

I-h

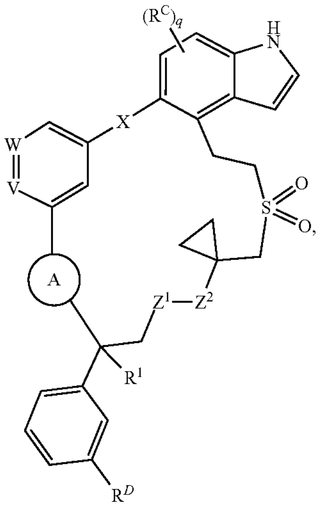

or a pharmaceutically acceptable salt thereof, wherein Ring A, W, V, X, $Z^1$, $Z^2$, $R^1$, $R^A$, $R^C$, $R^D$, n, and q are defined herein.

In some embodiments, the present disclosure includes a compound of formula I-i:

I-i

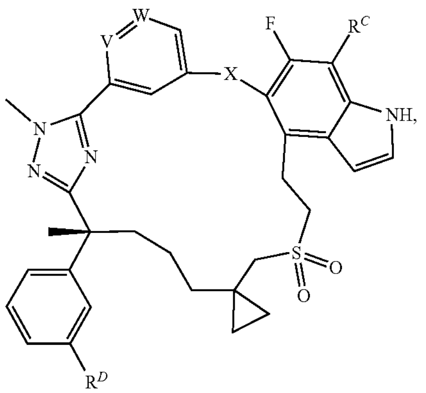

or a pharmaceutically acceptable salt thereof, wherein Ring A, V, W, X, $R^1$, $R^C$, and $R^D$ are defined herein.

Ring A

In some embodiments, Ring A is an optionally substituted 5-membered heteroaryl comprising 1-4 heteroatoms selected from the group consisting of N, O or S. In some embodiments, Ring A is an optionally substituted 5-membered heteroaryl comprising 1-3 heteroatoms selected from the group consisting of N and O. In some embodiments, Ring A is an optionally substituted 5-membered heteroaryl comprising 1 nitrogen atom. In some embodiments, Ring A is an optionally substituted 5-membered heteroaryl comprising 2 nitrogen atoms. In some embodiments, Ring A is an optionally substituted 5-membered heteroaryl comprising 3 nitrogen atoms.

In some embodiments, Ring A is selected from the group consisting of furan, pyrrole, thiophene, pyrazole, oxazole, thiazole, imidazole, triazole, tetrazole, oxadiazole, and thiadiazole. In some embodiments, Ring A is selected from the group consisting of furan, pyrrole, thiophene, pyrazole, oxazole, thiazole, imidazole, triazole, tetrazole, oxadiazole, and thiadiazole. In some embodiments, Ring A is selected from the ground consisting of imidazole, pyrazole, and triazole. In some embodiments, Ring A is selected from the group consisting of imidazole and triazole.

In some embodiments, Ring A is

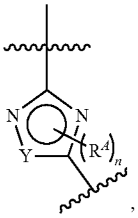
,
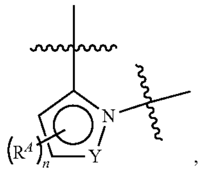
, or
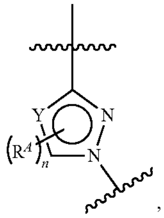
, wherein Y is C or N.

In some embodiments, Ring A is selected from the ground consisting of

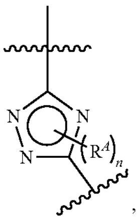
,
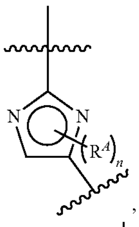
,
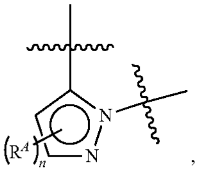
, and
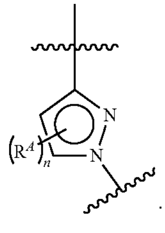
.

In some embodiments, Ring A is selected from the group consisting of

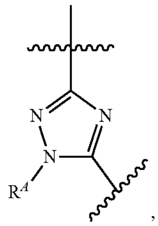
,
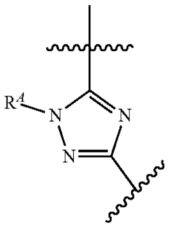
,
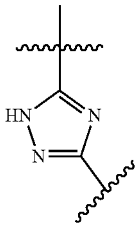
,
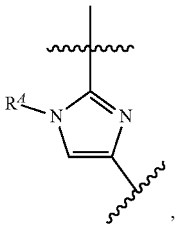
,
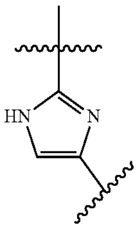
,
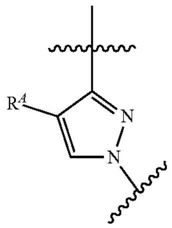
,
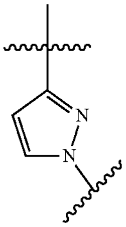
, and
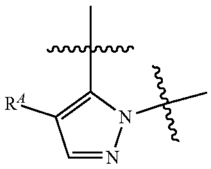

Ring B

In some embodiments, Ring B is optionally substituted phenyl or optionally substituted 6-membered heteroaryl. In some embodiments, Ring B is optionally substituted phenyl, optionally substituted pyridine, or optionally substituted pyridone. In some embodiments, Ring B is optionally substituted phenyl. In some embodiments, Ring B is optionally substituted pyridyl. In some embodiments, Ring B is optionally substituted pyridone.

In some embodiments, Ring B is

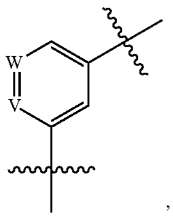
, wherein

W is —CH═, —C($R^B$)═ or —N═; and

V is —CH═, —C($R^B$)═ or —N═.

In some embodiments, Ring B is selected from the group consisting of

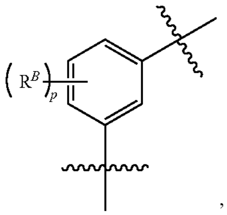
,
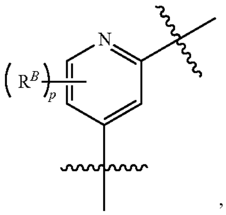
,
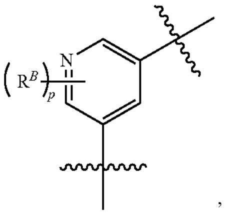
,
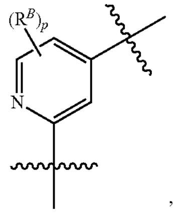
, and
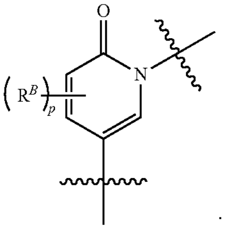
.

In some embodiments, Ring B is selected from the group consisting of

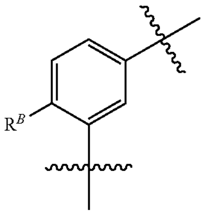
,
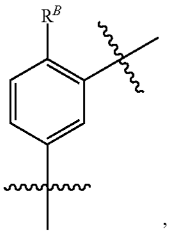
,
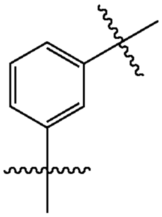
,
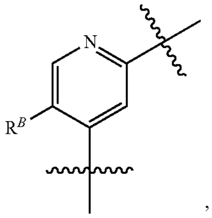
,
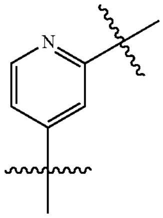
,
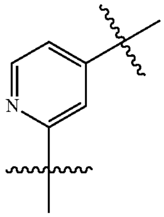
,
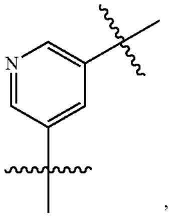
, -continued

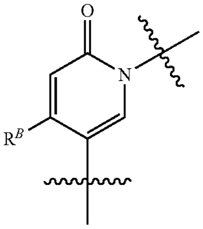
, and
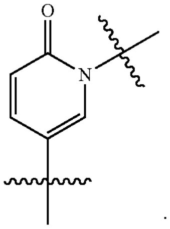
.

In some embodiments, Ring B is

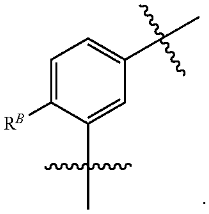
.

In some embodiments, Ring B is

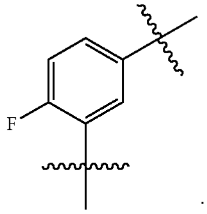 [SMILES: *c1ccc(F)c(*)c1]
.

Ring C

In some embodiments, Ring C is optionally substituted 5-10-membered heteroaryl comprising 1-3 heteroatoms selected from the group consisting of O, S, and N. In some embodiments, Ring C is optionally substituted 9-10-membered heteroaryl comprising 1-3 heteroatoms selected from the group consisting of O, S, and N. In some embodiments, Ring C is selected from the group consisting of optionally substituted indole, optionally substituted indazole, optionally substituted benzimidazole, optionally substituted 6-azaindole, and optionally substituted 7-azaindole. In some embodiments, Ring C is optionally substituted indole.

In some embodiments, Ring C is

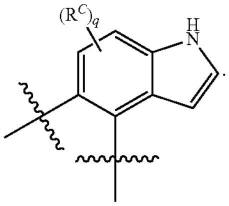
.

In some embodiments, Ring C is

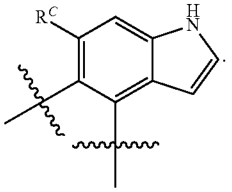

In some embodiments, Ring C is

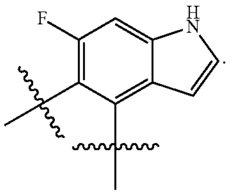 [SMILES: *c1c(F)cc2[nH]ccc2c1*]

In some embodiments, Ring C is

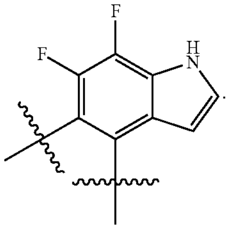 [SMILES: *c1c(F)c(F)c2[nH]ccc2c1*]

In some embodiments, Ring C is

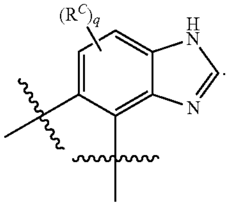

In some embodiments, Ring C is

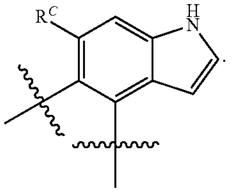

In some embodiments, Ring C is

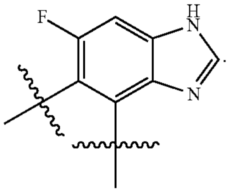 [SMILES: *c1c(F)cc2[nH]cnc2c1*]

Ring D

In some embodiments, Ring D is optionally substituted phenyl or optionally substituted 5-6-membered heteroaryl comprising 1-3 heteroatoms selected from the group consisting of O, S, and N. In some embodiments, Ring D is optionally substituted phenyl. In some embodiments, Ring D is optionally substituted 5-6-membered heteroaryl comprising 1-3 heteroatoms selected from the group consisting of O, S, and N. In some embodiments, Ring D is optionally substituted 5-membered heteroaryl comprising 1-3 heteroatoms selected from the group consisting of O, S, and N. In some embodiments, Ring D is 6-membered heteroaryl comprising 1-3 heteroatoms selected from the group consisting of O, S, and N. In some embodiments Ring D is optionally substituted pyridine.

In some embodiments, Ring D is

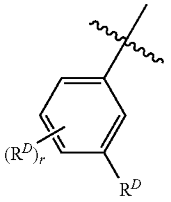 or 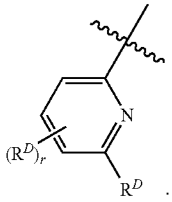 .

In some embodiments, Ring D is

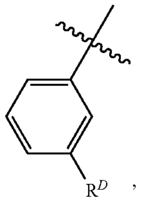 , 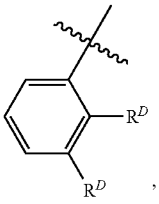 , 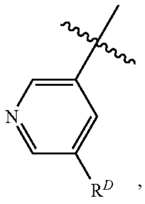 ,

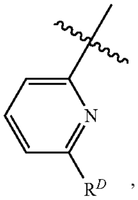 , 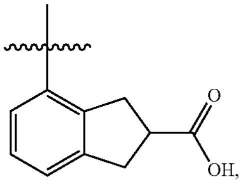 or

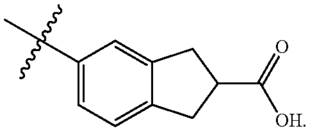

In some embodiments, Ring D is

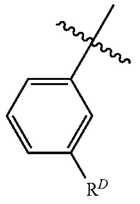

or

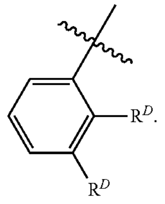

In some embodiments, Ring D is

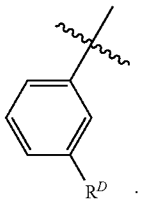

In some embodiments, Ring D is

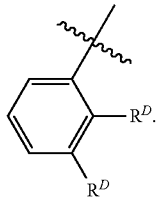

In some embodiments, Ring D is

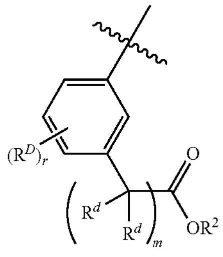

or

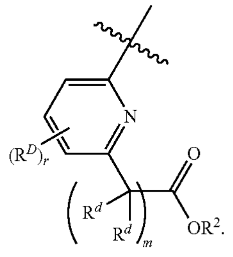

In some embodiments, Ring D is

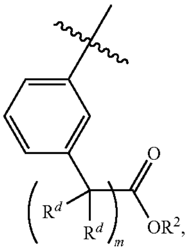

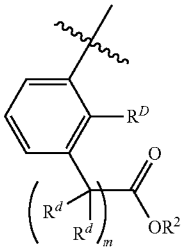

or

-continued

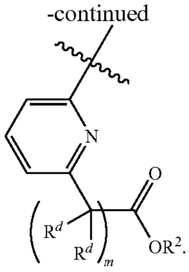

In some embodiments, Ring is

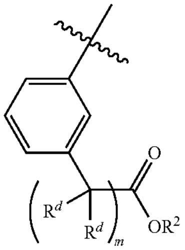

or

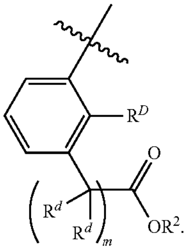

In some embodiments, Ring D is

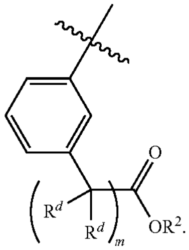

In some embodiments, Ring D is

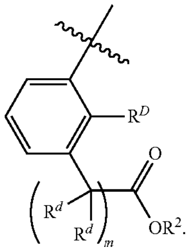

$L^1$ and $L^2$

In some embodiments, $L^1$ is an optionally substituted $C_{1-6}$ alkylene chain wherein 1-3 of the methylene units is optionally and independently replaced by —O—, —N($R^2$)—, —C(O)—, —S—, —S(O)—, —S(O)$_2$—, an optionally substituted 3-6 membered carbocyclyl,

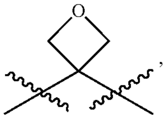 [SMILES: *C1(*)COC1]

optionally substituted $C_2$ alkenylene, or optionally substituted 5-6-membered heteroaryl. In some embodiments, $L^2$ is an optionally substituted $C_{1-6}$ alkylene chain wherein 1-3 of the methylene units is optionally and independently replaced by —$C(CD_3)_2$-, —O—, —$N(R^2)$, —C(O)—, —S—, —S(O)—, an optionally substituted 3-6 membered carbocyclyl, —$S(O)_2$—, optionally substituted $C_2$ alkenylene, or optionally substituted 5-6-membered heteroaryl. In some embodiments, $L^1$ is an optionally substituted $C_{1-6}$ alkylene chain wherein 1-3 of the methylene units is optionally and independently replaced by —O—, —$N(R^2)$—, —C(O)—, —$S(O)_2$—,

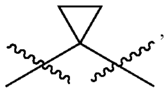 [SMILES: *C1(*)CC1]

, or optionally substituted 5-6-membered heteroaryl, and $L^2$ is an optionally substituted $C_{1-6}$ alkylene chain wherein 1-3 of the methylene units is optionally and independently replaced by —$C(CD_3)_2$-, —O—, —$N(R^2)$—, —C(O)—, —$S(O)_2$—,

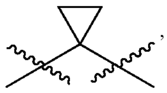 [SMILES: *C1(*)CC1]

, or optionally substituted 5-6-membered heteroaryl. In some embodiments, $L^1$ is an optionally substituted $C_{1-6}$ alkylene chain and $L^2$ is an optionally substituted $C_{1-6}$ alkylene chain, wherein one of the methylene units of $L^2$ is optionally replaced with —O—. In some embodiments, $L^1$ is a $C_{1-6}$ alkylene chain substituted with 1-3 instances of methyl, and $L^2$ is $C_{1-6}$ alkylene chain, wherein one of the methylene units of $L^2$ is optionally replaced with —O— and wherein $L^2$ is optionally substituted with 1-3 instances of methyl. In some embodiments, $L^1$ is an unsubstituted $C_2$ alkylene chain. In some embodiments, $L^2$ is a $C_5$ alkylene chain, wherein one of the methylene units of $L^2$ is optionally replaced with —O— and wherein $L^2$ is optionally substituted with 1-3 instances of methyl. In some embodiments, $L^2$ is a $C_5$ alkylene chain, wherein $L^2$ is optionally substituted with 1-3 instances of methyl. In some embodiments, $L^2$ is optionally substituted with 1-3 instances of methyl.

In some embodiments, $L^1$ is

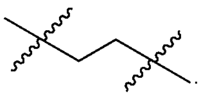 [SMILES: *CC*]

.

In some embodiments, $L^2$ is

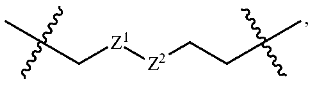

,

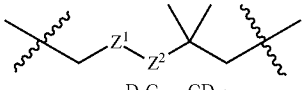

,

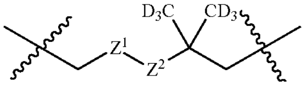

or

-continued

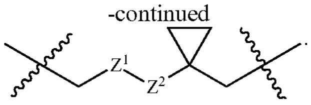

.

wherein $Z^1$ is —$CH_2$—, —$CF_2$—, —C(O)—, or —O—; and $Z^2$ is —$CH_2$—, —$CF_2$—, —C(O)—, or —O—.

In some embodiments, $L^2$ is

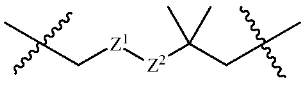

or

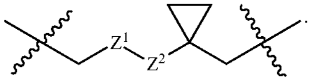

.

wherein $Z^1$ is —$CH_2$— or —O—; and $Z^2$ is —$CH_2$— or —O—.

In some embodiments, $L^2$ is

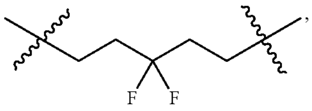

,

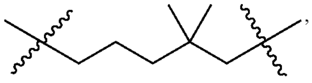

,

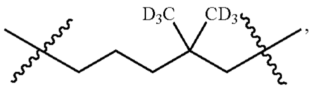

,

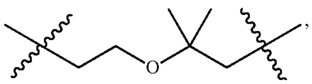

,

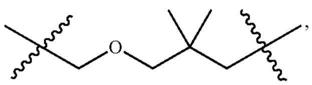

,

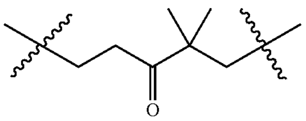

or

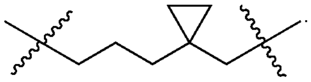

.

In some embodiments, $L^2$ is

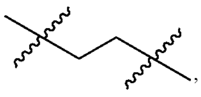

, or

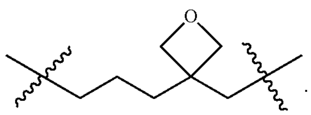

.

In some embodiments, $Z^1$ is —$CH_2$—, and $Z^2$ is —O—. In some embodiments, $Z^1$ is —O—, and $Z^1$ is —$CH_2$—.

$R^A$

In some embodiments, each $R^A$ is independently selected from the group consisting of halogen, cyano, optionally substituted $C_1$-$C_6$ aliphatic, optionally substituted $C_1$-$C_6$ alkoxy, and —$CD_3$. In some embodiments, each $R^A$ is independently selected from cyano and optionally substituted $C_1$-$C_6$ aliphatic. In some embodiments, each $R^A$ is independently selected from cyano and optionally substituted $C_1$-$C_3$ aliphatic. In some embodiments, each $R^A$ is independently optionally substituted $C_1$-$C_3$ aliphatic. In some embodiments, $R^A$ is methyl.

$R^B$

In some embodiments, each $R^B$ is independently selected from the group consisting of halogen, cyano, —C(O)N($R^2$)$_2$, C(O)OR$^2$, —OR$^2$, —N($R^2$)$_2$, optionally substituted $C_1$-$C_6$ aliphatic and optionally substituted $C_1$-$C_6$ alkoxy. In some embodiments, each $R^B$ is independently selected from halogen and cyano. In some embodiments, each $R^B$ is independently selected from the group consisting of halogen and optionally substituted $C_1$-$C_3$ alkyl. In some embodiments, each $R^B$ is independently selected from halogen. In some embodiments, $R^B$ is fluoro.

$R^C$

In some embodiments, each $R^C$ is independently selected from the group consisting of halogen, cyano, optionally substituted $C_1$-$C_6$ aliphatic or optionally substituted $C_1$-$C_6$ alkoxy. In some embodiments, each $R^C$ is independently selected from halogen, cyano, and optionally substituted $C_1$-$C_6$ alkyl. In some embodiments, each $R^C$ is independently selected from halogen. In some embodiments, $R^C$ is fluoro.

$R^D$

In some embodiments, each $R^D$ is independently selected from the group consisting of halogen, cyano, —C(O)N($R^2$)$_2$, —C(O)OR$^2$, —OR$^2$, —N($R^2$)$_2$, optionally substituted $C_1$-$C_6$ aliphatic, optionally substituted $C_1$-$C_3$ alkoxy, optionally substituted 5-6-membered heteroaryl, and optionally substituted 3-6-membered heterocyclyl comprising 1-3 heteroatoms selected from the group consisting of N, O or S, wherein each $R^D$ is optionally substituted with 1-6 instances of $R^d$;

wherein two instances of $R^D$ may be taken together to form an optionally substituted 5-7 membered carbocyclic ring, optionally substituted 5-6-membered heteroaryl, and optionally substituted 3-6-membered heterocyclyl comprising 1-3 heteroatoms selected from the group consisting of N, O or S;

In some embodiments, each $R^D$ is independently selected from the group consisting of halogen, cyano, —C(O)N($R^2$)$_2$, —C(O)OR$^2$, —OR$^2$, —N($R^2$)$_2$, optionally substituted $C_1$-$C_6$ aliphatic, optionally substituted $C_1$-$C_3$ alkoxy, optionally substituted 5-6-membered heteroaryl, and optionally substituted 3-6-membered heterocyclyl comprising 1-3 heteroatoms selected from the group consisting of N, O or S, wherein each $R^D$ is optionally substituted with 1-6 instances of $R^d$.

In some embodiments, each $R^D$ is independently selected from the group consisting of halogen, cyano, —C(O)N($R^2$)$_2$, —C(O)OR$^2$, —OR$^2$, —N($R^2$)$_2$, optionally substituted $C_1$-$C_6$ aliphatic, optionally substituted $C_1$-$C_3$ alkoxy, optionally substituted 5-6-membered heteroaryl, and optionally substituted 3-6-membered heterocyclyl comprising 1-3 heteroatoms selected from the group consisting of N, O or S.

In some embodiments, each $R^D$ is independently selected from the group consisting of halogen, OR$^2$, and optionally substituted $C_1$-$C_6$ aliphatic. In some embodiments, each $R^D$ is independently selected from the group consisting of halogen, OR$^2$, and optionally substituted $C_1$-$C_6$ aliphatic. In some embodiments, each $R^D$ is independently selected from the group consisting of halogen, OR$^2$, optionally substituted $C_1$-$C_3$ alkyl, and optionally substituted $C_2$-$C_3$ alkenyl. In some embodiments, each $R^D$ is independently selected from the group consisting of OR$^2$, optionally substituted $C_1$-$C_3$ alkyl, and optionally substituted $C_2$-$C_3$ alkenyl.

In some embodiments, each $R^D$ is independently selected from halogen, —C($R^d$)$_2$OR$^2$,

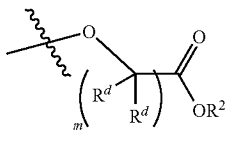

and

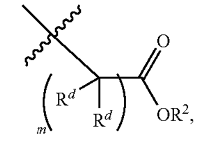

wherein each $R^d$ is independently selected from the group consisting of hydrogen, optionally substituted methyl, —OH, —OMe, or —CD$_3$, wherein, two instances $R^d$ may, with the atoms on which they are attached, form a cyclopropyl ring; and m is 0, 1, 2, or 3.

In some embodiments, r is 1 and $R^D$ is —C($R^d$)$_2$OR$^2$ or

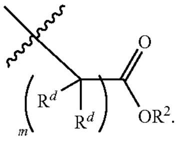

In some embodiments, r is 1 and $R^D$ is —C($R^d$)$_2$OH or

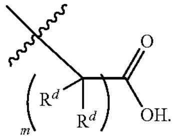

In some embodiments, $R^D$ is selected from the group consisting of

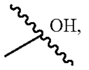

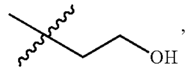

,

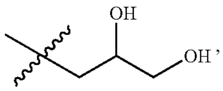

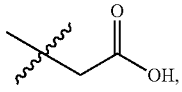

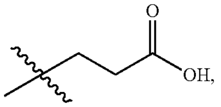

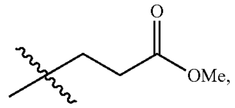

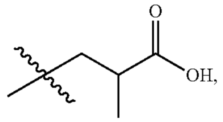

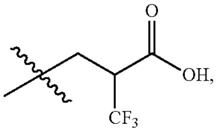

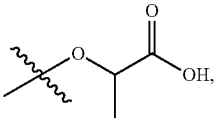

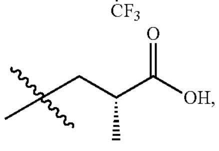

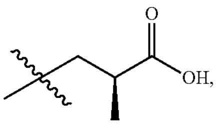

-continued
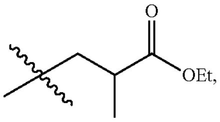
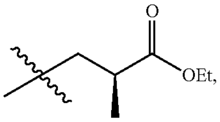
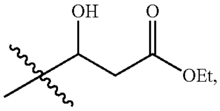
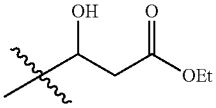
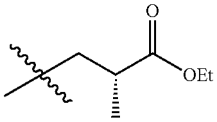
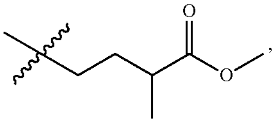
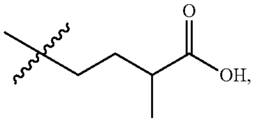
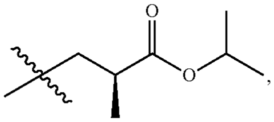
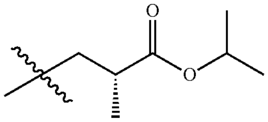
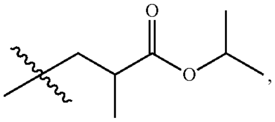
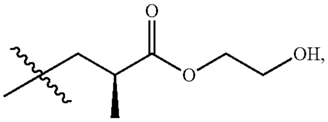
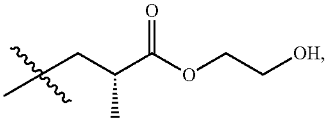
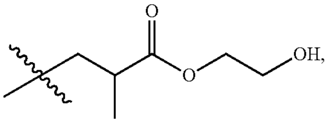
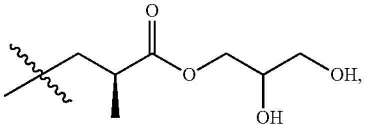
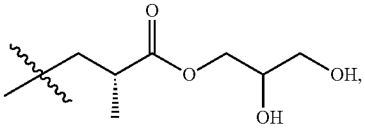
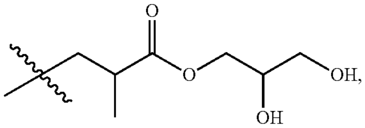
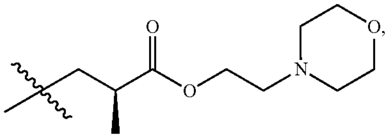
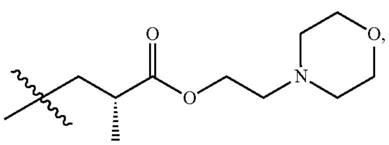
-continued
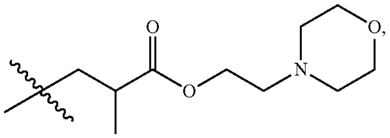
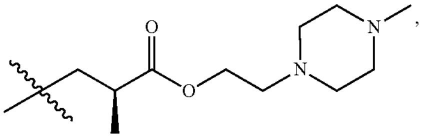
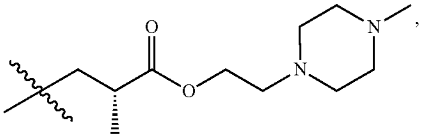
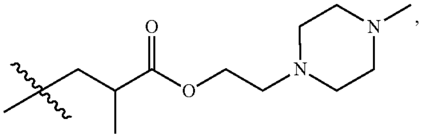
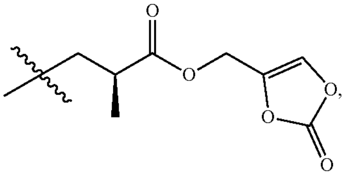
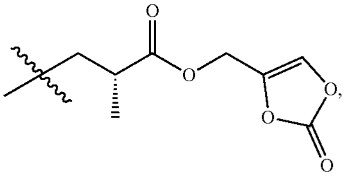
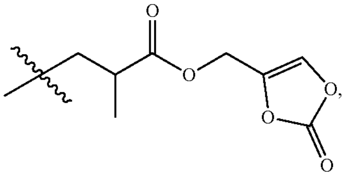
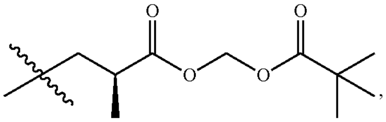
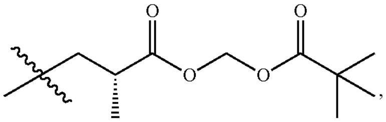
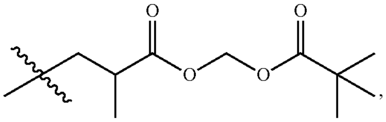
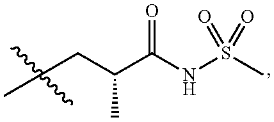
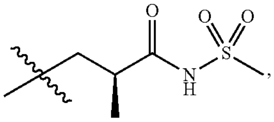
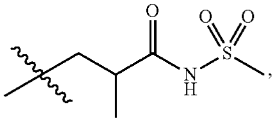
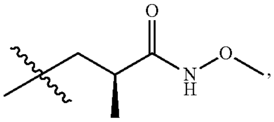

-continued
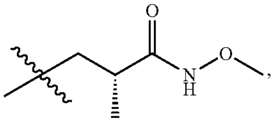
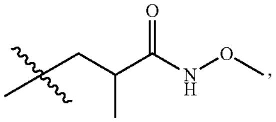
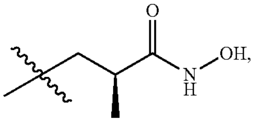
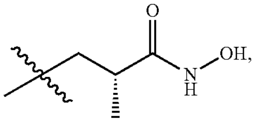
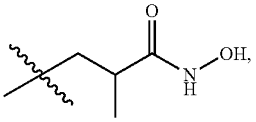
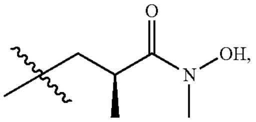
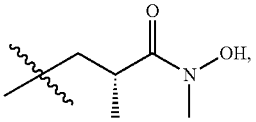
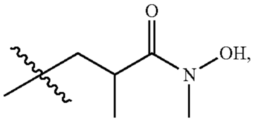
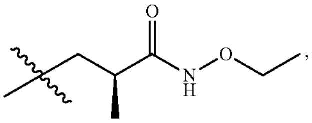
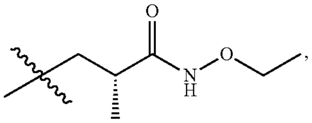
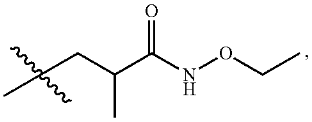
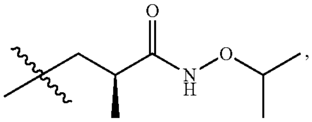
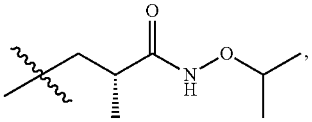
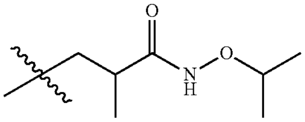
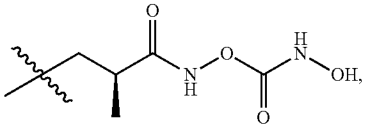
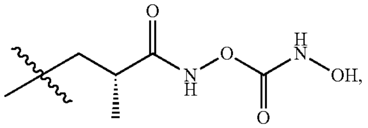
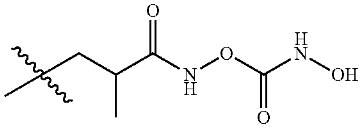
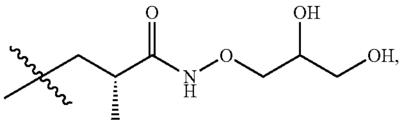
-continued
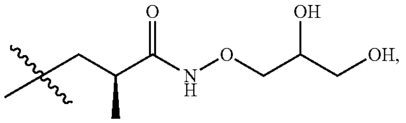
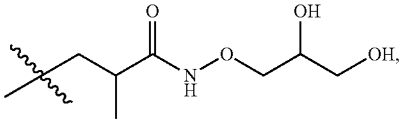
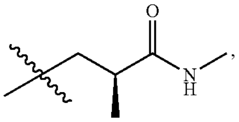
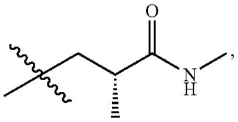
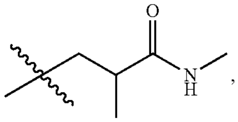
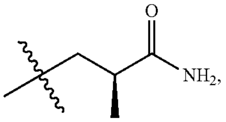
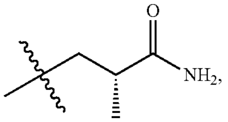
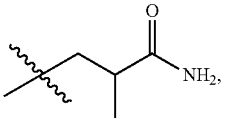
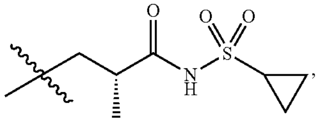
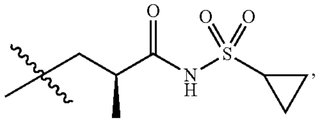
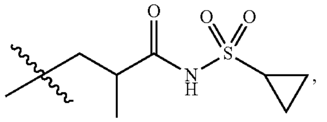
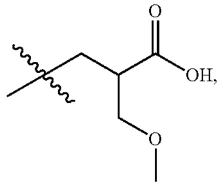
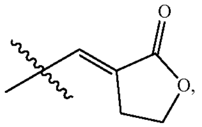
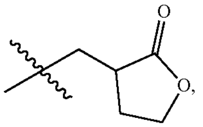
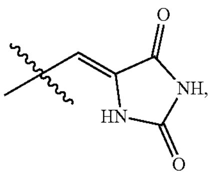
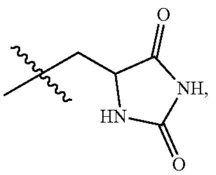
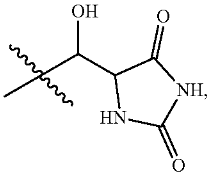
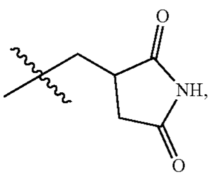
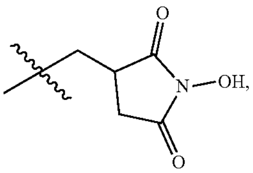
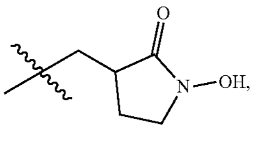

-continued
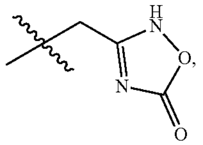
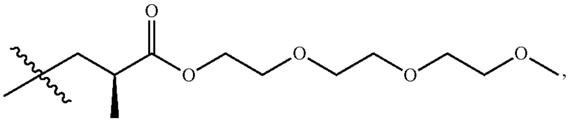
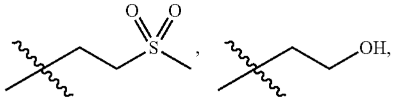
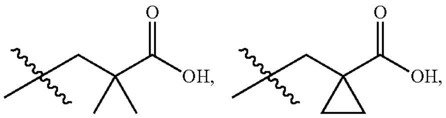
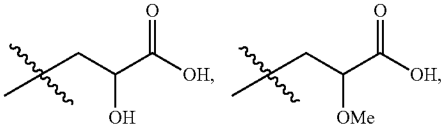
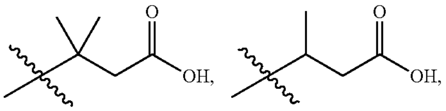
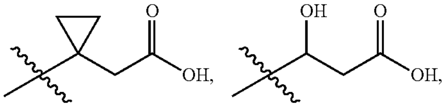
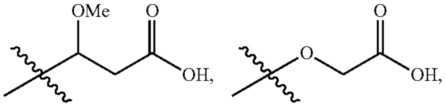
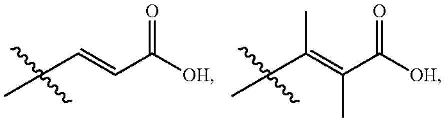
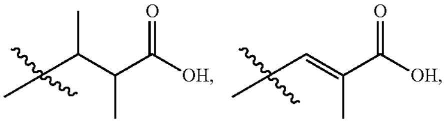
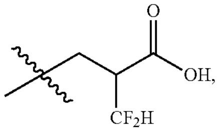
and
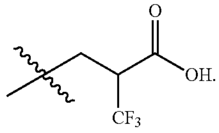
In some embodiments, $R^D$ is selected from the group consisting of
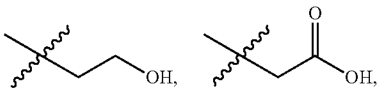
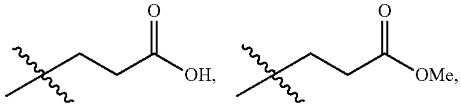
-continued
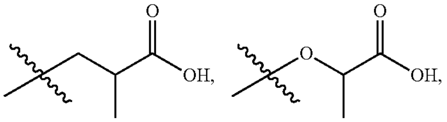
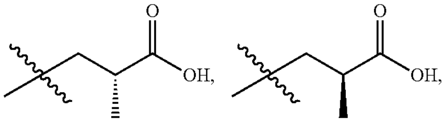
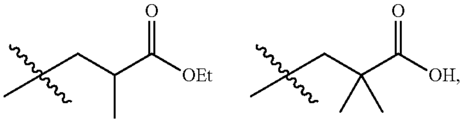
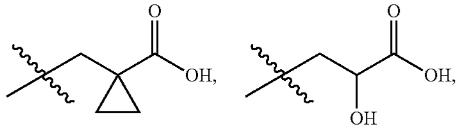
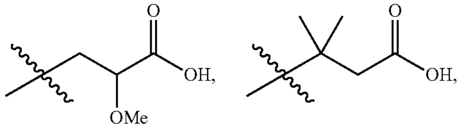
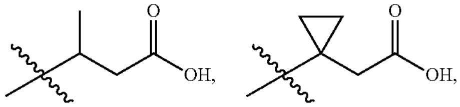
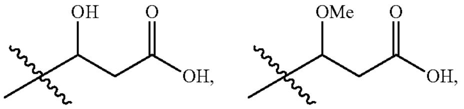
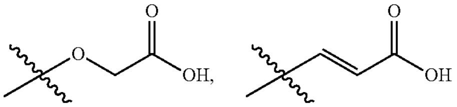
and
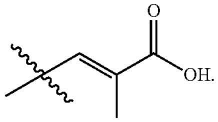
In some embodiments, $R^D$ is selected from the group consisting of
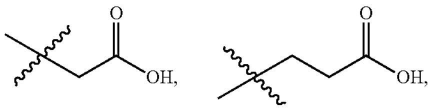
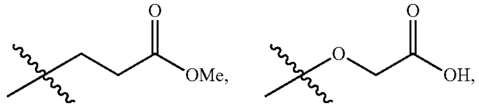
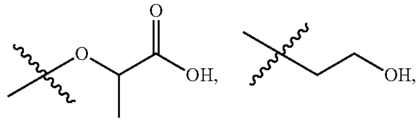
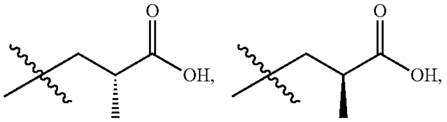

-continued

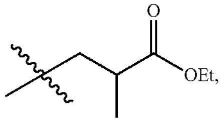,

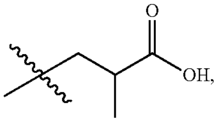,

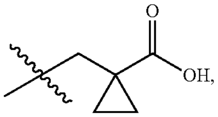,

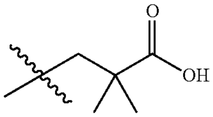

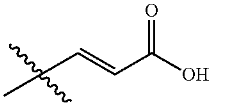

and

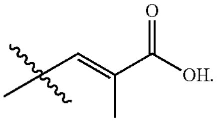.

In some embodiments, $R^D$ is selected from the group consisting of

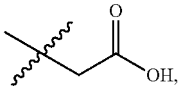,

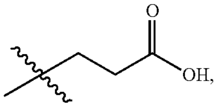,

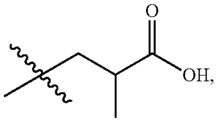,

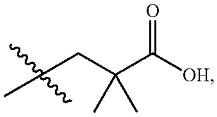, and

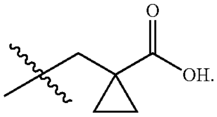.

In some embodiments, $R^D$ is

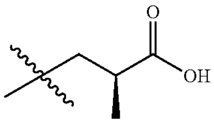

or

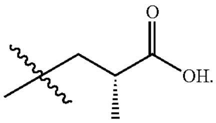.

$R^1$

In some embodiments, $R^1$ is selected from the group consisting of hydrogen, cyano, —$OR^2$, —$(CH_2)_{0-3}N(R^2)_2$, optionally substituted $C_1$-$C_3$ aliphatic, 3-6-membered heterocyclyl comprising 1-3 heteroatoms selected from the group consisting of N, O or S, and —$CD_3$, In some embodiments, $R^1$ is selected from the group consisting of hydrogen, cyano, —$OR^2$, —$(CH_2)_{0-3}N(R^2)_2$, optionally substituted $C_1$-$C_3$ aliphatic, and —$CD_3$. In some embodiments, $R^1$ is selected from the group consisting of hydrogen, cyano, and optionally substituted $C_1$-$C_3$ aliphatic. In some embodiments, $R^1$ is selected from the group consisting of hydrogen, cyano, optionally substituted methyl, and —$CD_3$. In some embodiments, $R^1$ is optionally substituted methyl. In some embodiments, $R^1$ is —$CH_3$. In some embodiments, $R^1$ is hydrogen. In some embodiments, $R^1$ is cyano. In some embodiments, $R^1$ is —$CD_3$. In some embodiments, $R^1$ is —$CH_2NHCH_2CF_3$. In some embodiments, $R^1$ is $CH_2NH_2$.

$R^2$

In some embodiments, each $R^2$ is independently selected from hydrogen, optionally substituted $C_1$-$C_6$ aliphatic, —OH, $C_1$-$C_6$ alkoxy, —$S(O)_2$ (optionally substituted $C_1$-$C_6$ aliphatic). In some embodiments, each $R^2$ is independently hydrogen or optionally substituted $C_1$-$C_6$ aliphatic. In some embodiments, each $R^2$ is independently hydrogen or optionally substituted $C_1$-$C_3$ aliphatic. In some embodiments, each $R^2$ is independently hydrogen or optionally substituted methyl. In some embodiments, $R^2$ is optionally substituted $C_1$-$C_6$ aliphatic. In some embodiments, $R^2$ is hydrogen. In some embodiments, each $R^2$ is independently optionally substituted methyl or optionally substituted ethyl. In some embodiments, each $R^2$ is independently optionally substituted methyl.

$R^d$

In some embodiments, each $R^d$ is independently selected from the group consisting of hydrogen, —OH, —$CD_3$, —$C(O)N(R^2)_2$, $C(O)OR^2$, —$OR^2$, —$N(R^2)_2$, optionally substituted $C_1$-$C_6$ aliphatic, optionally substituted 5-6-membered heteroaryl, and optionally substituted 3-6-membered heterocyclyl comprising 1-3 heteroatoms selected from the group consisting of N, O or S. In some embodiments, each $R^d$ is independently selected from the group consisting of hydrogen, optionally substituted $C_{1-3}$ alkyl, —OH, —OMe, or —$CD_3$, wherein, two instances $R^d$ may, with the atoms on which they are attached, form a cyclopropyl ring. In some embodiments, each $R^d$ is independently selected from the group consisting of hydrogen, methyl, —$CF_3$, —$CF_2H$, or —$CFH_2$. In some embodiments, each $R^d$ is independently selected from hydrogen and methyl. In some embodiments, $R^d$ is hydrogen.

X

In some embodiments, X is selected from the group consisting of —O—, —S—, —$CH_2$—, —C(OH)H—, —SO—, —CO—, —$SO_2$—, —CFH—, —$CF_2$—, and —$N(R^2)$—. In some embodiments, X is selected from the group consisting of —O—, —S—, —$CH_2$—, —SO—, —CO—, —C(OH)H—, and —$SO_2$—. In some embodiments, X is —O—. In some embodiments, X is —S—. In some embodiments, X is —$CH_2$—. In some embodiments, X is —SO—. In some embodiments, X is —CO—. In some embodiments, X is —C(OH)H—. In some embodiments, X is —$SO_2$—. In some embodiments, X is

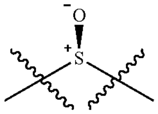

or

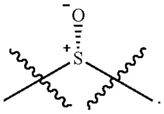.

In some embodiments, X is

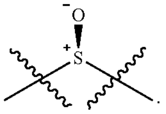.

In some embodiments, X is

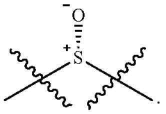.

m, n, p, q, and r

In some embodiments, m is 0, 1, 2, or 3. In some embodiments, m is 1, 2, or 3. In some embodiments, m is 0.

In some embodiments, m is 1. In some embodiments, m is 2. In some embodiments, m is 3.

In some embodiments, n is 0, 1, 2, or 3. In some embodiments, n is 1, 2, or 3. In some embodiments, n is 0. In some embodiments, n is 1. In some embodiments, n is 2. In some embodiments, n is 3.

In some embodiments, p is 0, 1, 2, 3, or 4. In some embodiments, p is 1, 2, 3, or 4. In some embodiments, p is 0. In some embodiments, p is 1. In some embodiments, p is 2. In some embodiments, p is 3. In some embodiments, p is 4.

In some embodiments, q is 0, 1, or 2. In some embodiments, q is 1 or 2. In some embodiments, q is 0. In some embodiments, q is 1. In some embodiments, q is 2.

In some embodiments, r is 0, 1, 2, 3, 4, or 5. In some embodiments, r is 1, 2, 3, or 4. In some embodiments, r is 0. In some embodiments, r is 1. In some embodiments, r is 2. In some embodiments, r is 3. In some embodiments, r is 4. In some embodiments, r is 5.

In some embodiments, the present disclosure includes compounds listed in Table 1.

| Compound No. | Structures |
| --- | --- |
| 1A | 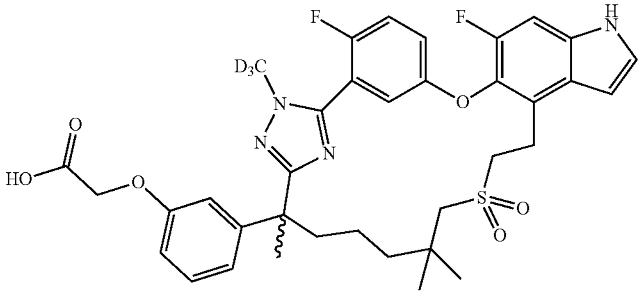 [SMILES: [2H]C([2H])([2H])n1nc2nc1-c1cc(ccc1F)Oc1c(F)cc3[nH]ccc3c1CCS(=O)(=O)CC(C)(C)CCCC2(C)c1cccc(OCC(=O)O)c1] |
| 1B | 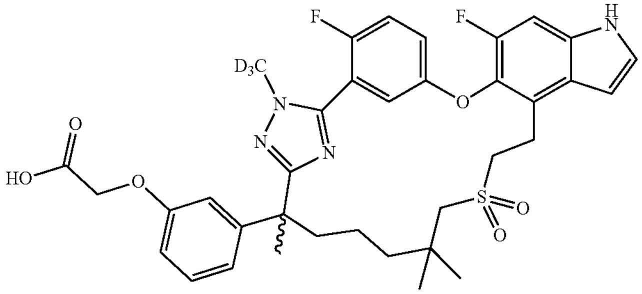 [SMILES: [2H]C([2H])([2H])n1nc2nc1-c1cc(ccc1F)Oc1c(F)cc3[nH]ccc3c1CCS(=O)(=O)CC(C)(C)CCCC2(C)c1cccc(OCC(=O)O)c1] |
| 2A | 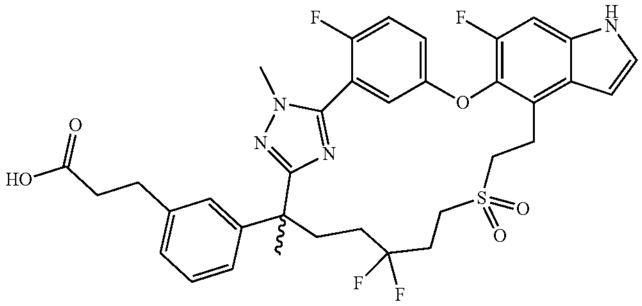 [SMILES: Cn1nc2nc1-c1cc(ccc1F)Oc1c(F)cc3[nH]ccc3c1CCS(=O)(=O)CCC(F)(F)CCC2(C)c1cccc(CCC(=O)O)c1] |
| 2B | 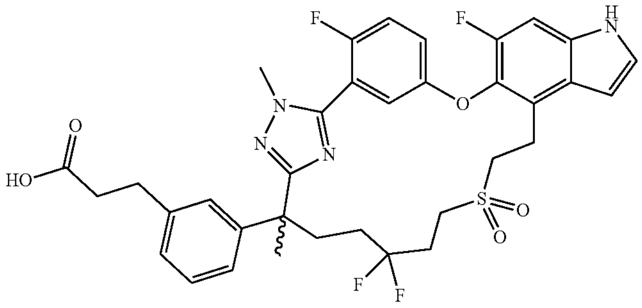 [SMILES: Cn1nc2nc1-c1cc(ccc1F)Oc1c(F)cc3[nH]ccc3c1CCS(=O)(=O)CCC(F)(F)CCC2(C)c1cccc(CCC(=O)O)c1] |

-continued
| Compound No. | Structures |
| --- | --- |
| 3 | 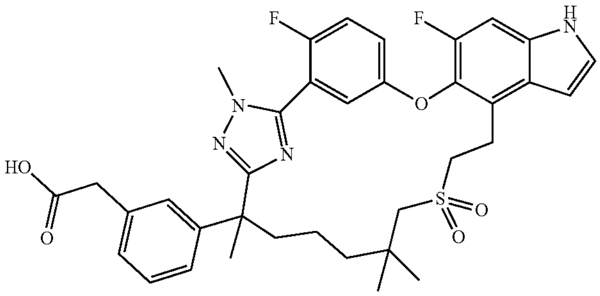 [SMILES: Cn1nc2nc1-c1cc(ccc1F)Oc1c(F)cc3[nH]ccc3c1CCS(=O)(=O)CC(C)(C)CCCC2(C)c1cccc(CC(=O)O)c1] |
| 4A | 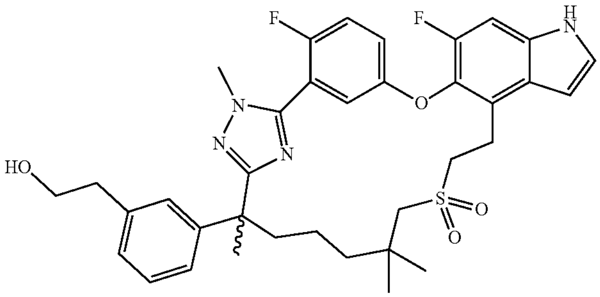 [SMILES: Cn1nc2nc1-c1cc(ccc1F)Oc1c(F)cc3[nH]ccc3c1CCS(=O)(=O)CC(C)(C)CCCC2(C)c1cccc(CCO)c1] |
| 4B | 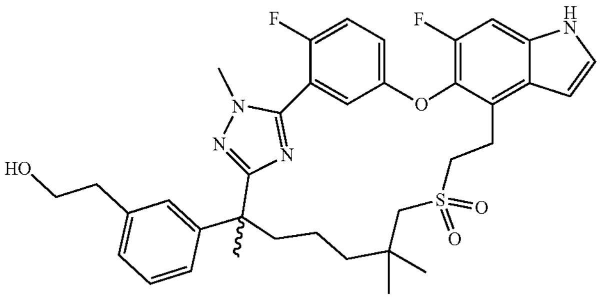 [SMILES: Cn1nc2nc1-c1cc(ccc1F)Oc1c(F)cc3[nH]ccc3c1CCS(=O)(=O)CC(C)(C)CCCC2(C)c1cccc(CCO)c1] |
| 5A | 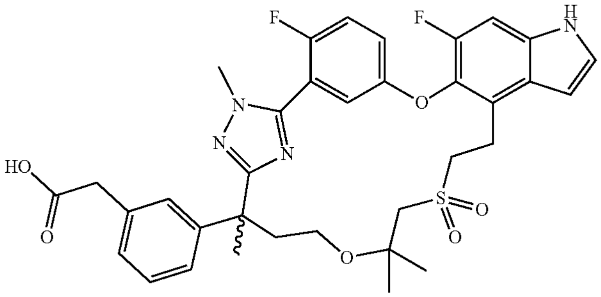 [SMILES: Cn1nc2nc1-c1cc(ccc1F)Oc1c(F)cc3[nH]ccc3c1CCS(=O)(=O)CC(C)(C)OCCC2(C)c1cccc(CC(=O)O)c1] |
| 5B | 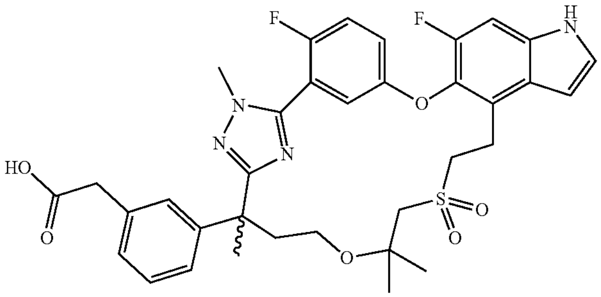 [SMILES: Cn1nc2nc1-c1cc(ccc1F)Oc1c(F)cc3[nH]ccc3c1CCS(=O)(=O)CC(C)(C)OCCC2(C)c1cccc(CC(=O)O)c1] |

-continued
| Compound No. | Structures |
| --- | --- |
| 6A | 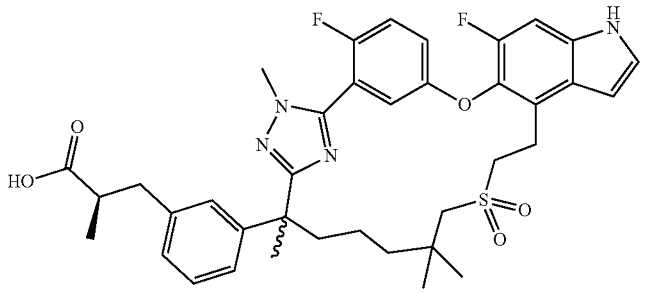 [SMILES: C[C@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O] |
| 6B | 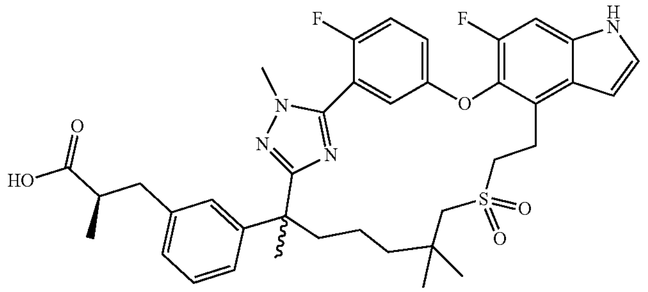 [SMILES: C[C@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O] |
| 7 | 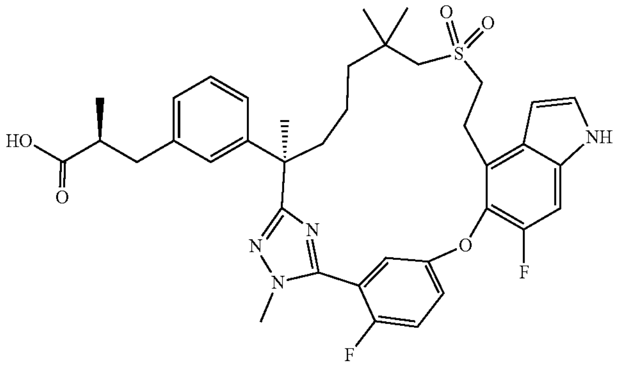 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3nc2nn3C)c1)C(=O)O] |
| 8A | 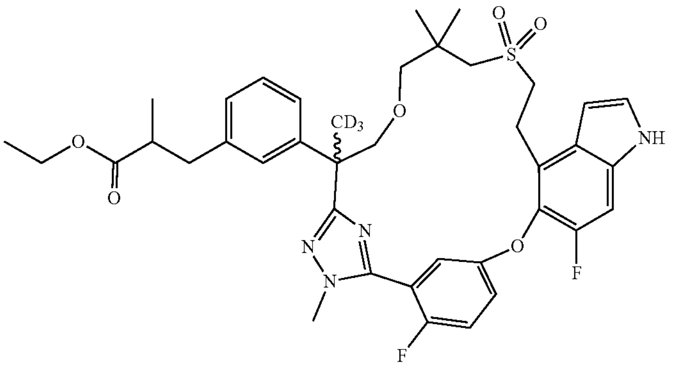 [SMILES: [2H]C([2H])([2H])C1(c2cccc(CC(C)C(=O)OCC)c2)COCC(C)(C)CS(=O)(=O)CCc2c(c(F)cc3[nH]ccc23)Oc2ccc(F)c(c2)-c2nc1nn2C] |

-continued
| Compound No. | Structures |
|---|---|
| 8B | 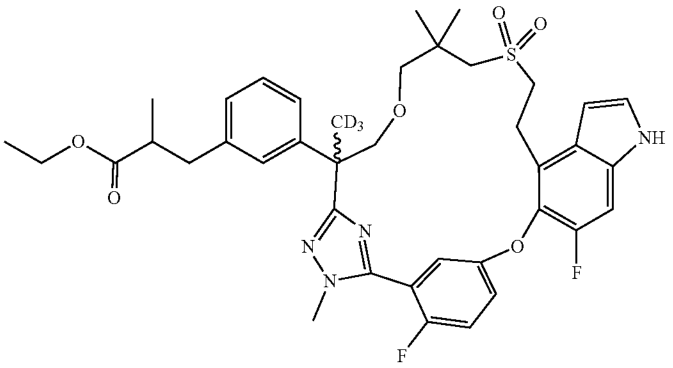 [SMILES: [2H]C([2H])([2H])C1(c2cccc(CC(C)C(=O)OCC)c2)COCC(C)(C)CS(=O)(=O)CCc2c(c(F)cc3[nH]ccc23)Oc2ccc(F)c(c2)-c2nc1nn2C] |
| 9A | 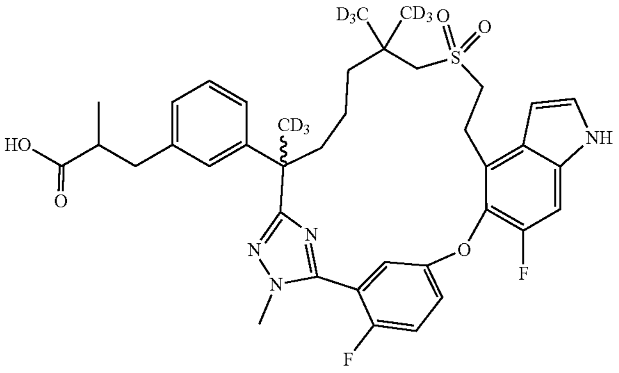 [SMILES: [2H]C([2H])([2H])C1(c2cccc(CC(C)C(=O)O)c2)CCCC(C([2H])([2H])[2H])(C([2H])([2H])[2H])CS(=O)(=O)CCc2c(c(F)cc3[nH]ccc23)Oc2ccc(F)c(c2)-c2nc1nn2C] |
| 9B | 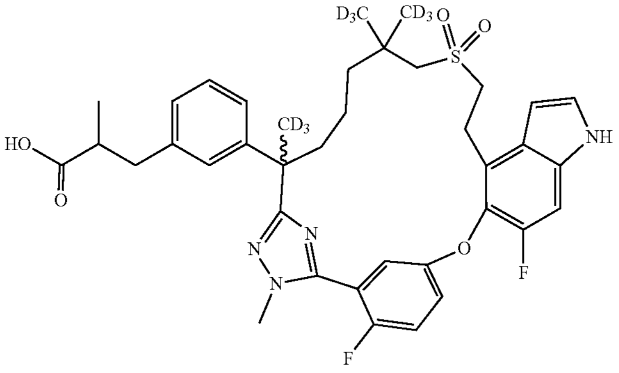 [SMILES: [2H]C([2H])([2H])C1(c2cccc(CC(C)C(=O)O)c2)CCCC(C([2H])([2H])[2H])(C([2H])([2H])[2H])CS(=O)(=O)CCc2c(c(F)cc3[nH]ccc23)Oc2ccc(F)c(c2)-c2nc1nn2C] |
| 10A | 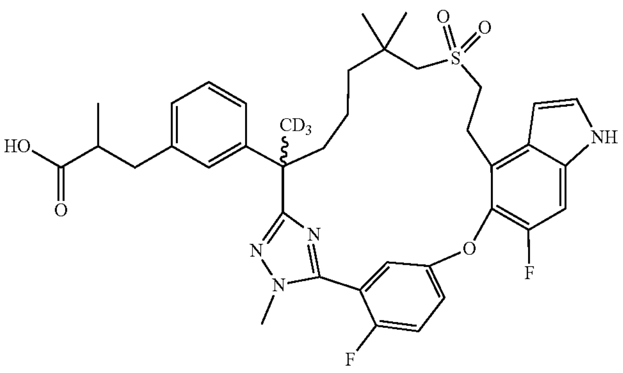 [SMILES: [2H]C([2H])([2H])C1(c2cccc(CC(C)C(=O)O)c2)CCCC(C)(C)CS(=O)(=O)CCc2c(c(F)cc3[nH]ccc23)Oc2ccc(F)c(c2)-c2nc1nn2C] |

-continued
| Compound No. | Structures |
| --- | --- |
| 10B | 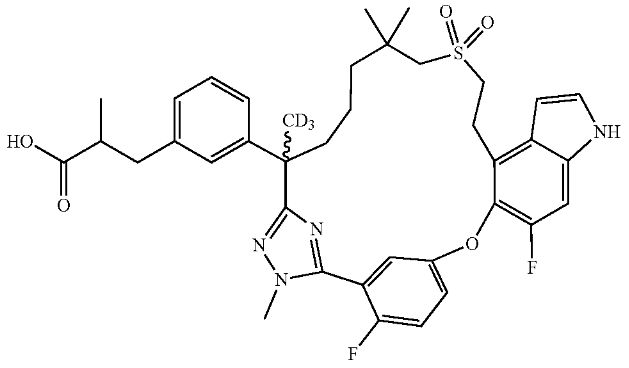 [SMILES: [2H]C([2H])([2H])C1(c2cccc(CC(C)C(=O)O)c2)CCCC(C)(C)CS(=O)(=O)CCc2c(c(F)cc3[nH]ccc23)Oc2ccc(F)c(c2)-c2nc1nn2C] |
| 11A | 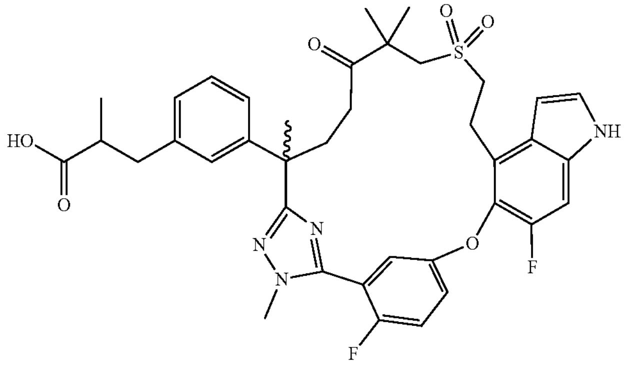 [SMILES: CC(Cc1cccc(C2(C)CCC(=O)C(C)(C)CS(=O)(=O)CCc3c(c(F)cc4[nH]ccc34)Oc3ccc(F)c(c3)-c3nc2nn3C)c1)C(=O)O] |
| 11B | 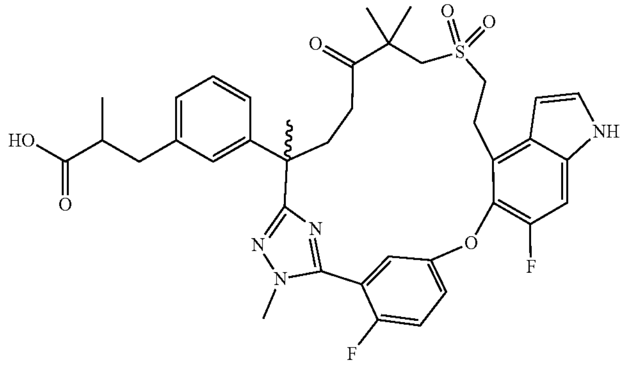 [SMILES: CC(Cc1cccc(C2(C)CCC(=O)C(C)(C)CS(=O)(=O)CCc3c(c(F)cc4[nH]ccc34)Oc3ccc(F)c(c3)-c3nc2nn3C)c1)C(=O)O] |
| 12A | 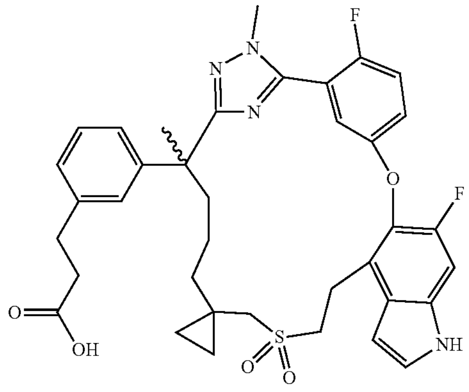 [SMILES: Cn1nc2nc1-c1cc(ccc1F)Oc1c(F)cc3[nH]ccc3c1CCS(=O)(=O)CC1(CCCC2(C)c2cccc(CCC(=O)O)c2)CC1] |

-continued
| Compound No. | Structures |
| --- | --- |
| 12B | 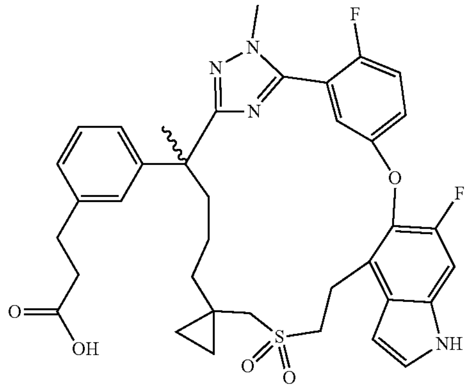 [SMILES: Cn1nc2nc1-c1cc(ccc1F)Oc1c(F)cc3[nH]ccc3c1CCS(=O)(=O)CC1(CCCC2(C)c2cccc(CCC(=O)O)c2)CC1] |
| 13A | 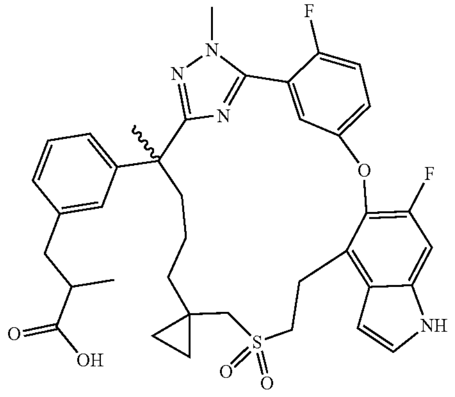 [SMILES: CC(Cc1cccc(C2(C)CCCC3(CC3)CS(=O)(=O)CCc3c(c(F)cc4[nH]ccc34)Oc3ccc(F)c(c3)-c3nc2nn3C)c1)C(=O)O] |
| 13B | 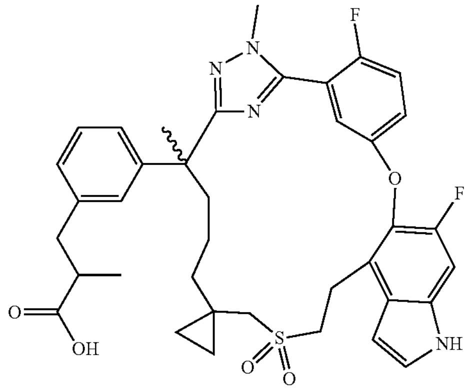 [SMILES: CC(Cc1cccc(C2(C)CCCC3(CC3)CS(=O)(=O)CCc3c(c(F)cc4[nH]ccc34)Oc3ccc(F)c(c3)-c3nc2nn3C)c1)C(=O)O] |
| 14 | 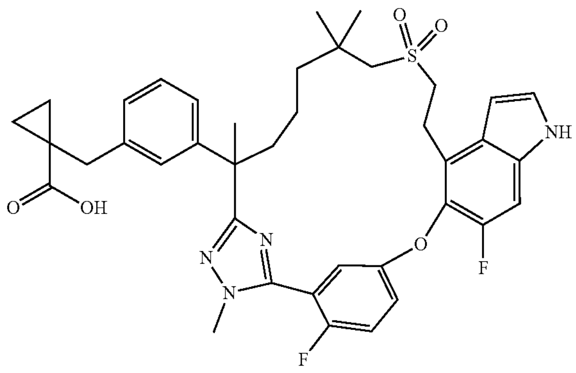 [SMILES: Cn1nc2nc1-c1cc(ccc1F)Oc1c(F)cc3[nH]ccc3c1CCS(=O)(=O)CC(C)(C)CCCC2(C)c1cccc(CC2(C(=O)O)CC2)c1] |

-continued
| Compound No. | Structures |
| --- | --- |
| 15A | 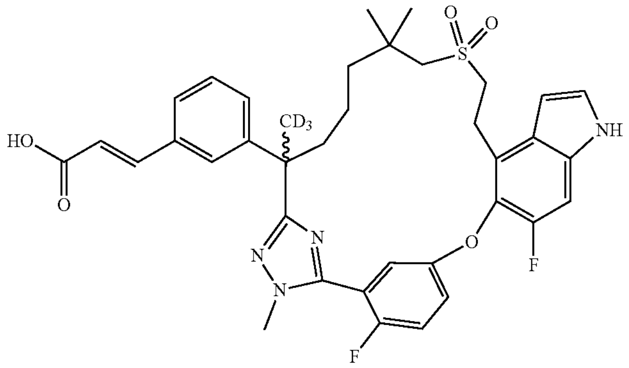 [SMILES: [2H]C([2H])([2H])C1(c2cccc(/C=C/C(=O)O)c2)CCCC(C)(C)CS(=O)(=O)CCc2c(c(F)cc3[nH]ccc23)Oc2ccc(F)c(c2)-c2nc1nn2C] |
| 15B | 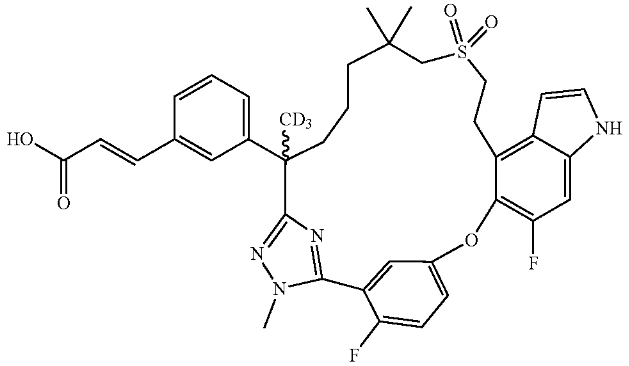 [SMILES: [2H]C([2H])([2H])C1(c2cccc(/C=C/C(=O)O)c2)CCCC(C)(C)CS(=O)(=O)CCc2c(c(F)cc3[nH]ccc23)Oc2ccc(F)c(c2)-c2nc1nn2C] |
| 16A | 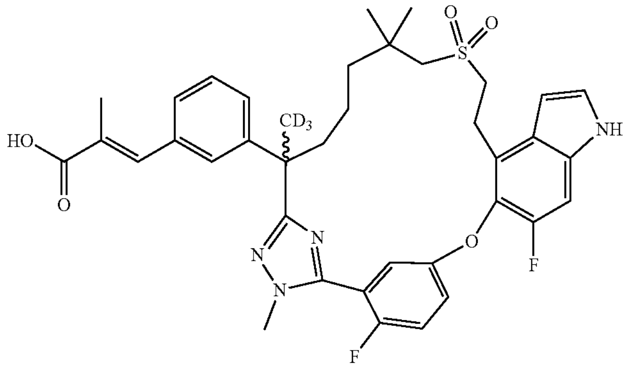 [SMILES: [2H]C([2H])([2H])C1(c2cccc(/C=C(\C)C(=O)O)c2)CCCC(C)(C)CS(=O)(=O)CCc2c(c(F)cc3[nH]ccc23)Oc2ccc(F)c(c2)-c2nc1nn2C] |
| 16B | 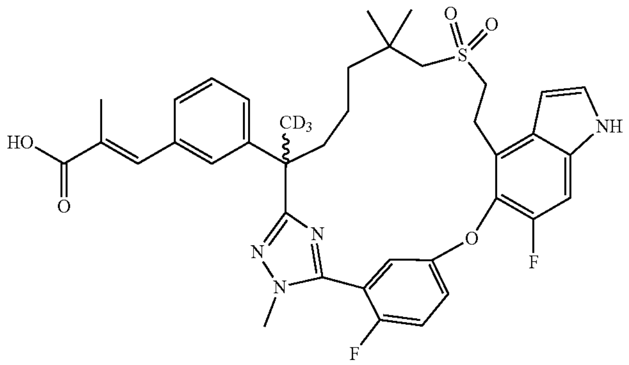 [SMILES: [2H]C([2H])([2H])C1(c2cccc(/C=C(\C)C(=O)O)c2)CCCC(C)(C)CS(=O)(=O)CCc2c(c(F)cc3[nH]ccc23)Oc2ccc(F)c(c2)-c2nc1nn2C] |

-continued
| Compound No. | Structures |
|---|---|
| 17A | 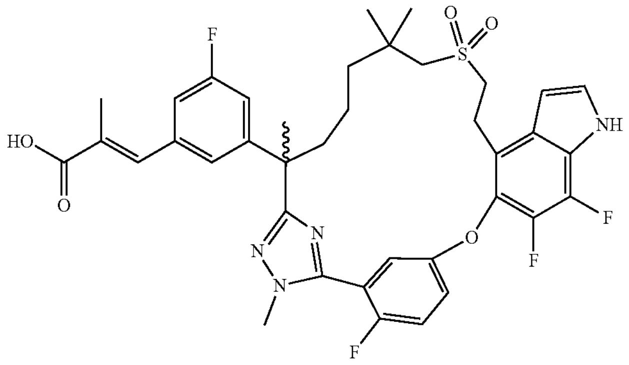 [SMILES: C/C(=C\c1cc(F)cc(C2(C)CCCC(C)(C)CS(=O)(=O)CCc3c(c(F)c(F)c4[nH]ccc34)Oc3ccc(F)c(c3)-c3nc2nn3C)c1)C(=O)O] |
| 17B | 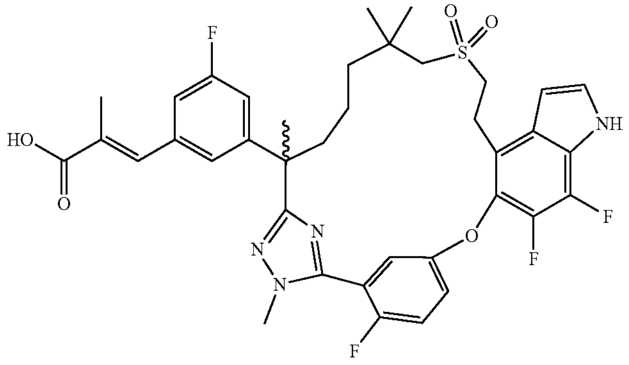 [SMILES: C/C(=C\c1cc(F)cc(C2(C)CCCC(C)(C)CS(=O)(=O)CCc3c(c(F)c(F)c4[nH]ccc34)Oc3ccc(F)c(c3)-c3nc2nn3C)c1)C(=O)O] |
| 18A | 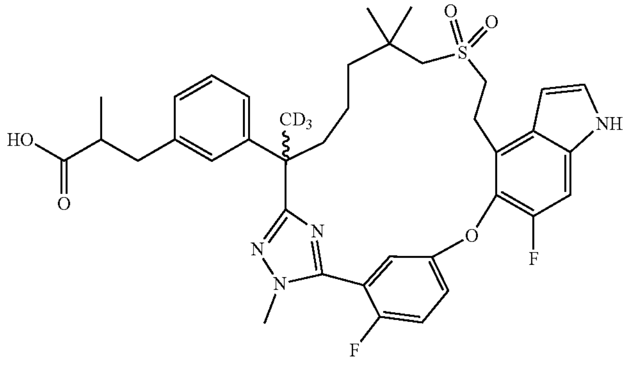 [SMILES: [2H]C([2H])([2H])C1(c2cccc(CC(C)C(=O)O)c2)CCCC(C)(C)CS(=O)(=O)CCc2c(c(F)cc3[nH]ccc23)Oc2ccc(F)c(c2)-c2nc1nn2C] |
| 18B | 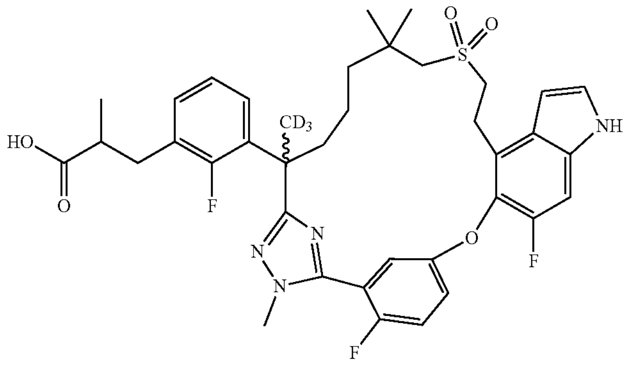 [SMILES: [2H]C([2H])([2H])C1(c2cccc(CC(C)C(=O)O)c2F)CCCC(C)(C)CS(=O)(=O)CCc2c(c(F)cc3[nH]ccc23)Oc2ccc(F)c(c2)-c2nc1nn2C] |

-continued
| Compound No. | Structures |
| --- | --- |
| 19A | 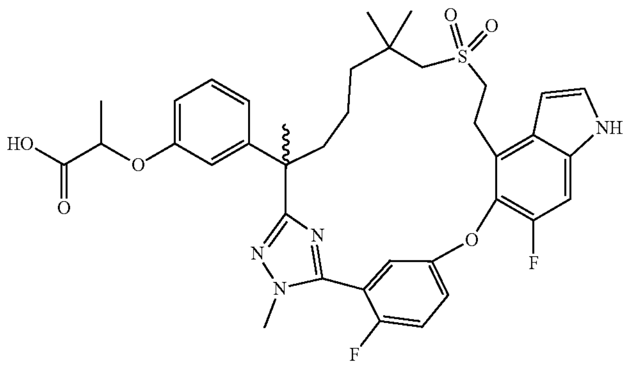 |
| 19B | 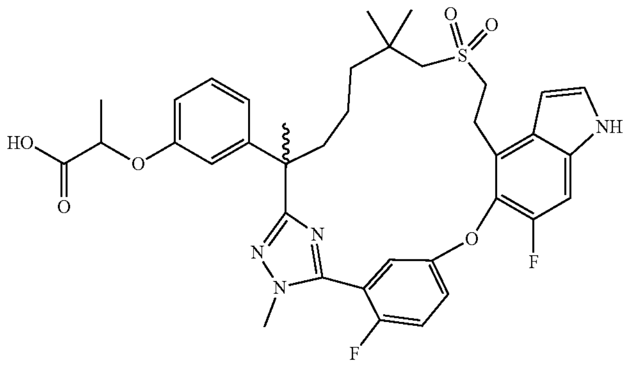 |
| 20A | 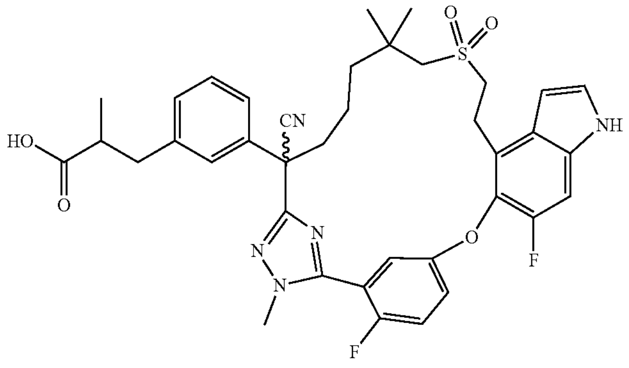 [SMILES: CC(Cc1cccc(C2(C#N)CCCC(C)(C)CS(=O)(=O)CCc3c(c(F)cc4[nH]ccc34)Oc3ccc(F)c(c3)-c3nc2nn3C)c1)C(=O)O] |
| 20B | 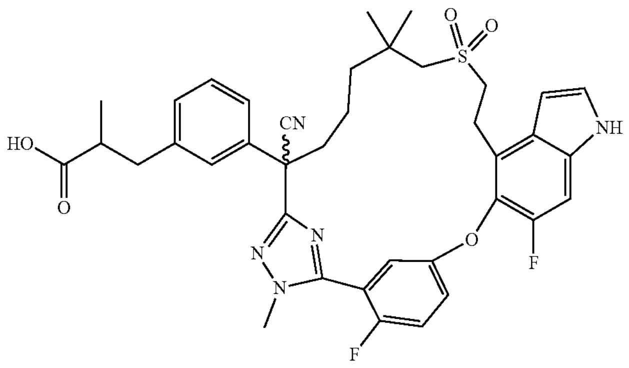 [SMILES: CC(Cc1cccc(C2(C#N)CCCC(C)(C)CS(=O)(=O)CCc3c(c(F)cc4[nH]ccc34)Oc3ccc(F)c(c3)-c3nc2nn3C)c1)C(=O)O] |

-continued
| Compound No. | Structures |
| --- | --- |
| 21 | 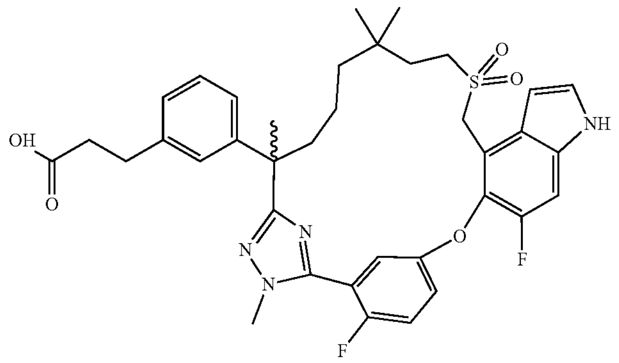 [SMILES: Cn1nc2nc1-c1cc(ccc1F)Oc1c(F)cc3[nH]ccc3c1CS(=O)(=O)CCC(C)(C)CCCC2(C)c1cccc(CCC(=O)O)c1] |
| 22A | 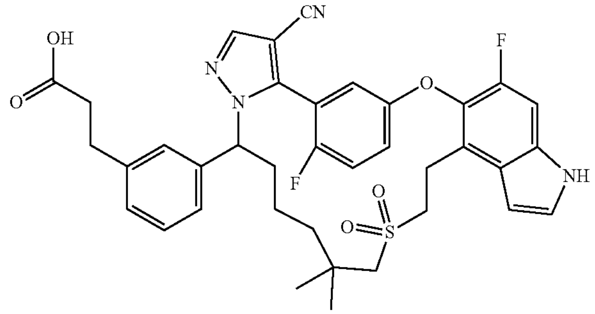 [SMILES: CC1(C)CCCC(c2cccc(CCC(=O)O)c2)n2ncc(C#N)c2-c2cc(ccc2F)Oc2c(F)cc3[nH]ccc3c2CCS(=O)(=O)C1] |
| 22B | 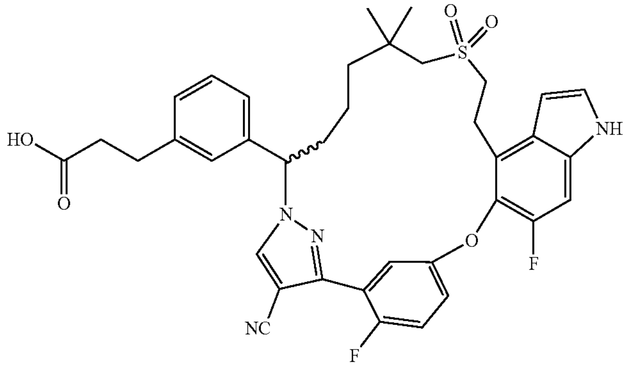 [SMILES: CC1(C)CCCC(c2cccc(CCC(=O)O)c2)n2cc(C#N)c(n2)-c2cc(ccc2F)Oc2c(F)cc3[nH]ccc3c2CCS(=O)(=O)C1] |
| 22C | 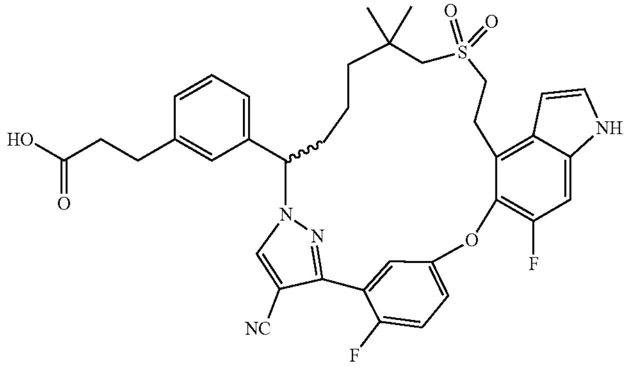 [SMILES: CC1(C)CCCC(c2cccc(CCC(=O)O)c2)n2cc(C#N)c(n2)-c2cc(ccc2F)Oc2c(F)cc3[nH]ccc3c2CCS(=O)(=O)C1] |

-continued
| Compound No. | Structures |
|---|---|
| 23 | 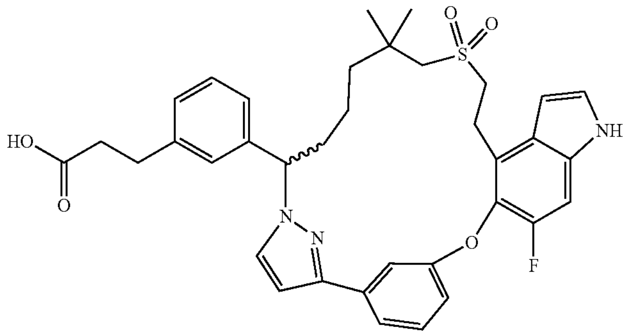 [SMILES: CC1(C)CCCC(c2cccc(CCC(=O)O)c2)n2ccc(n2)-c2cccc(c2)Oc2c(F)cc3[nH]ccc3c2CCS(=O)(=O)C1] |
| 24A | 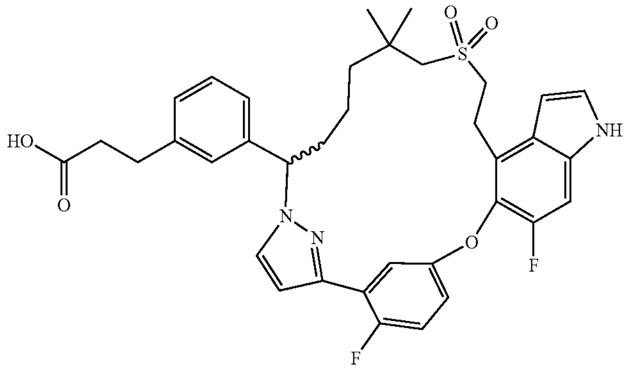 [SMILES: CC1(C)CCCC(c2cccc(CCC(=O)O)c2)n2ccc(n2)-c2cc(ccc2F)Oc2c(F)cc3[nH]ccc3c2CCS(=O)(=O)C1] |
| 24B | 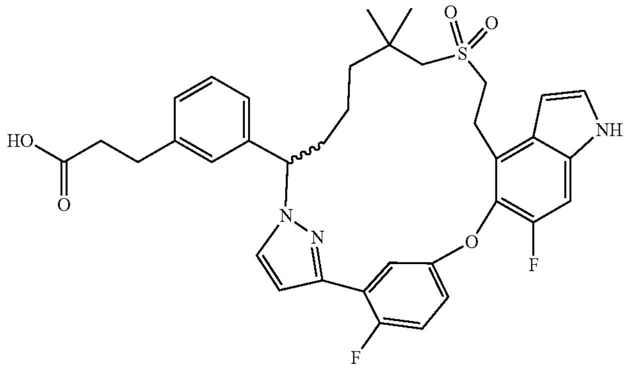 [SMILES: CC1(C)CCCC(c2cccc(CCC(=O)O)c2)n2ccc(n2)-c2cc(ccc2F)Oc2c(F)cc3[nH]ccc3c2CCS(=O)(=O)C1] |
| 25 | 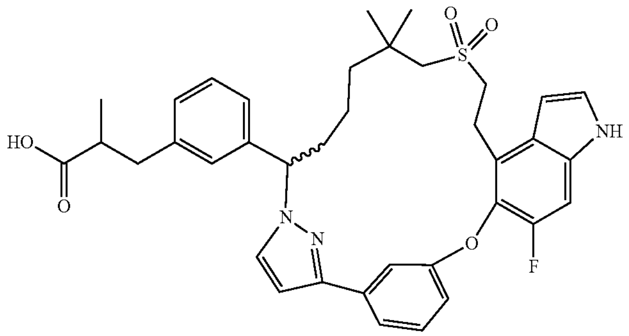 [SMILES: CC(Cc1cccc(C2CCCC(C)(C)CS(=O)(=O)CCc3c(c(F)cc4[nH]ccc34)Oc3cccc(c3)-c3ccn2n3)c1)C(=O)O] |

-continued
| Compound No. | Structures |
| --- | --- |
| 26 | 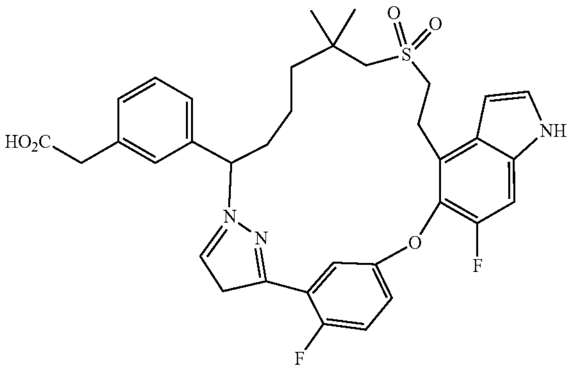 |
| 27A | 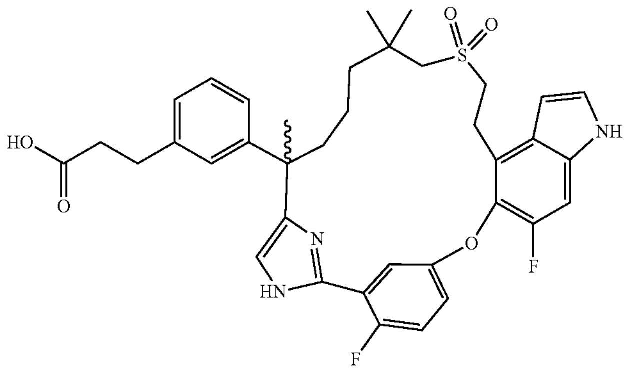 [SMILES: CC1(C)CCCC(C)(c2cccc(CCC(=O)O)c2)c2c[nH]c(n2)-c2cc(ccc2F)Oc2c(F)cc3[nH]ccc3c2CCS(=O)(=O)C1] |
| 27B | 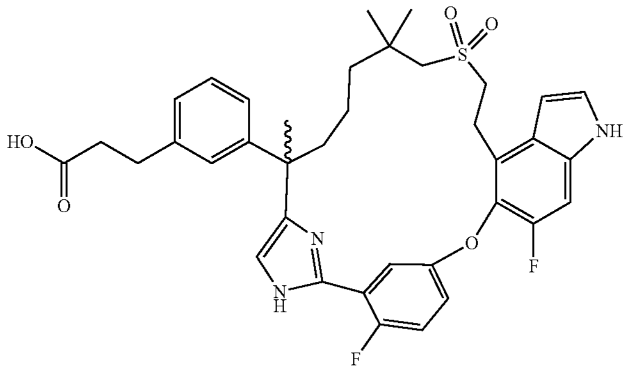 [SMILES: CC1(C)CCCC(C)(c2cccc(CCC(=O)O)c2)c2c[nH]c(n2)-c2cc(ccc2F)Oc2c(F)cc3[nH]ccc3c2CCS(=O)(=O)C1] |
| 28A | 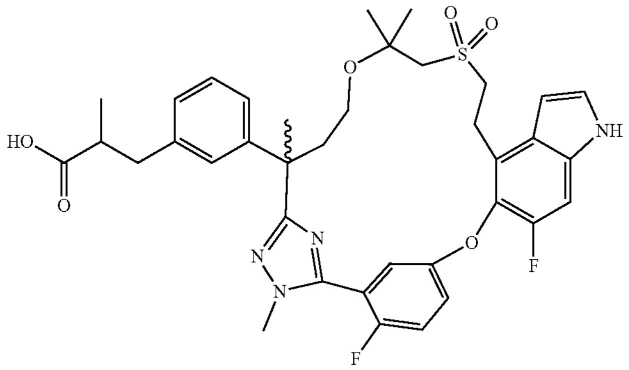 |

-continued
| Compound No. | Structures |
| --- | --- |
| 28B | 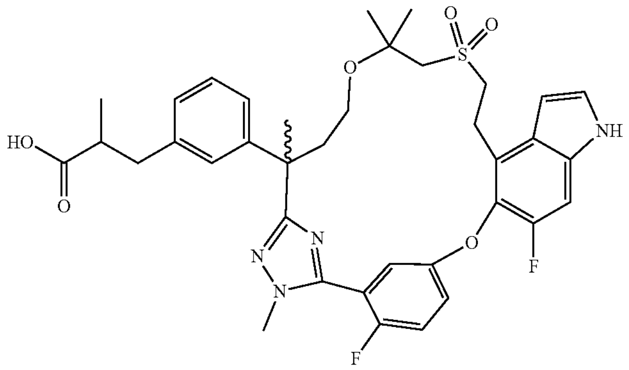 [SMILES: CC(Cc1cccc(C2(C)CCOC(C)(C)CS(=O)(=O)CCc3c(c(F)cc4[nH]ccc34)Oc3ccc(F)c(c3)-c3nc2nn3C)c1)C(=O)O] |
| 29A | 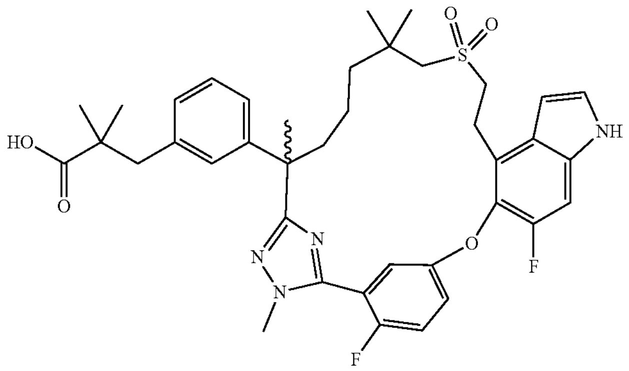 [SMILES: Cn1nc2nc1-c1cc(ccc1F)Oc1c(F)cc3[nH]ccc3c1CCS(=O)(=O)CC(C)(C)CCCC2(C)c1cccc(CC(C)(C)C(=O)O)c1] |
| 29B | 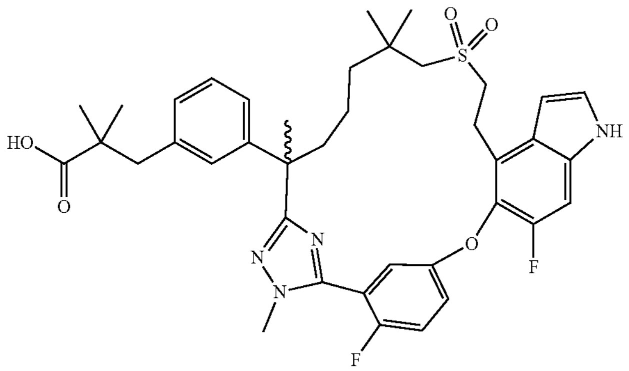 [SMILES: Cn1nc2nc1-c1cc(ccc1F)Oc1c(F)cc3[nH]ccc3c1CCS(=O)(=O)CC(C)(C)CCCC2(C)c1cccc(CC(C)(C)C(=O)O)c1] |
| 30A | 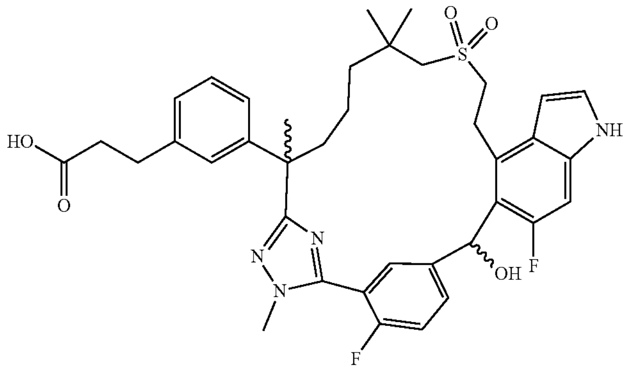 [SMILES: Cn1nc2nc1-c1cc(ccc1F)C(O)c1c(F)cc3[nH]ccc3c1CCS(=O)(=O)CC(C)(C)CCCC2(C)c1cccc(CCC(=O)O)c1] |

-continued
| Compound No. | Structures |
| --- | --- |
| 30B | 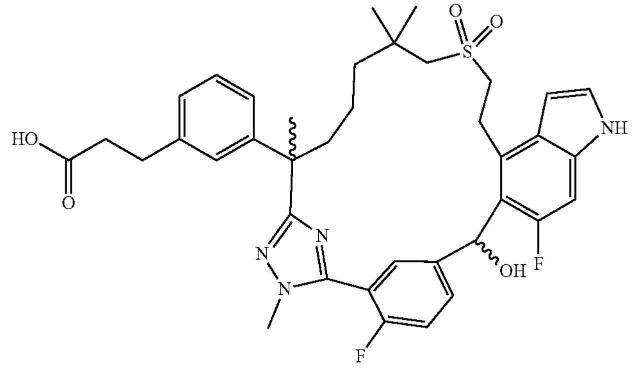 [SMILES: Cn1nc2nc1-c1cc(ccc1F)C(O)c1c(F)cc3[nH]ccc3c1CCS(=O)(=O)CC(C)(C)CCCC2(C)c1cccc(CCC(=O)O)c1] |
| 30C | 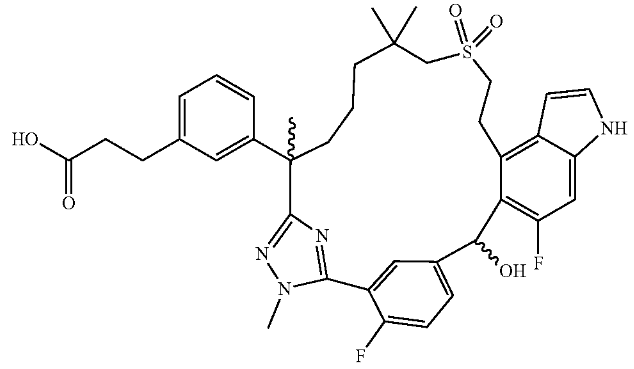 [SMILES: Cn1nc2nc1-c1cc(ccc1F)C(O)c1c(F)cc3[nH]ccc3c1CCS(=O)(=O)CC(C)(C)CCCC2(C)c1cccc(CCC(=O)O)c1] |
| 30D | 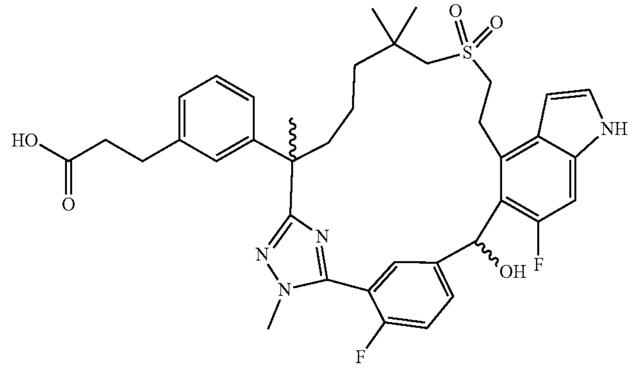 [SMILES: Cn1nc2nc1-c1cc(ccc1F)C(O)c1c(F)cc3[nH]ccc3c1CCS(=O)(=O)CC(C)(C)CCCC2(C)c1cccc(CCC(=O)O)c1] |
| 31A | 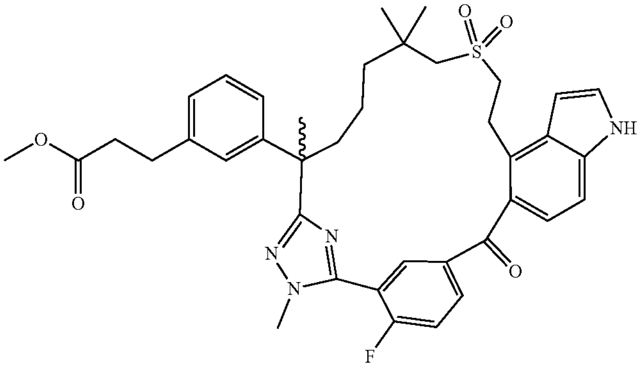 [SMILES: COC(=O)CCc1cccc(C2(C)CCCC(C)(C)CS(=O)(=O)CCc3c(ccc4[nH]ccc34)C(=O)c3ccc(F)c(c3)-c3nc2nn3C)c1] |

-continued
| Compound No. | Structures |
| --- | --- |
| 31B | 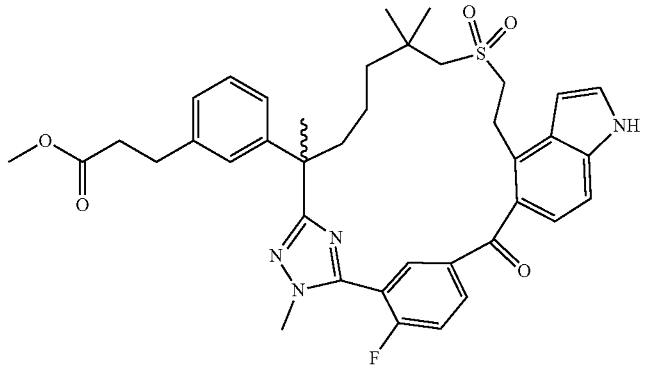 [SMILES: COC(=O)CCc1cccc(C2(C)CCCC(C)(C)CS(=O)(=O)CCc3c(ccc4[nH]ccc34)C(=O)c3ccc(F)c(c3)-c3nc2nn3C)c1] |
| 31C | 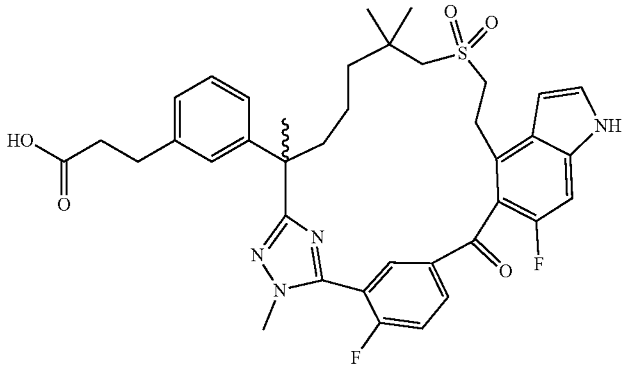 [SMILES: Cn1nc2nc1-c1cc(ccc1F)C(=O)c1c(F)cc3[nH]ccc3c1CCS(=O)(=O)CC(C)(C)CCCC2(C)c1cccc(CCC(=O)O)c1] |
| 31D | 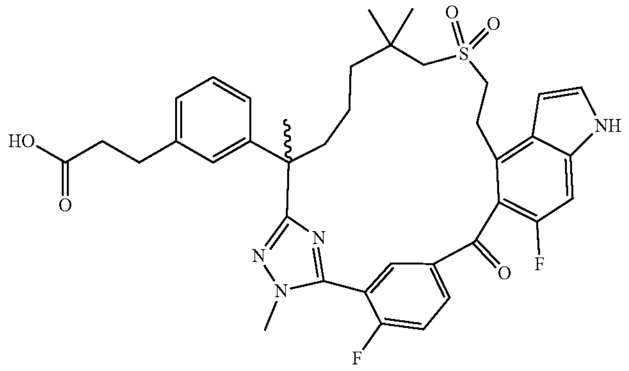 [SMILES: Cn1nc2nc1-c1cc(ccc1F)C(=O)c1c(F)cc3[nH]ccc3c1CCS(=O)(=O)CC(C)(C)CCCC2(C)c1cccc(CCC(=O)O)c1] |
| 32A | 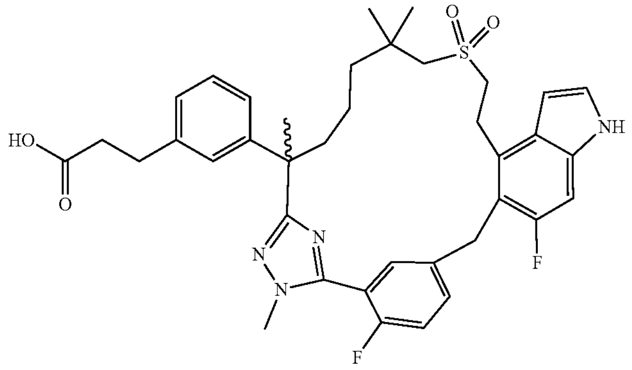 [SMILES: Cn1nc2nc1-c1cc(ccc1F)Cc1c(F)cc3[nH]ccc3c1CCS(=O)(=O)CC(C)(C)CCCC2(C)c1cccc(CCC(=O)O)c1] |

-continued
| Compound No. | Structures |
| --- | --- |
| 32B | 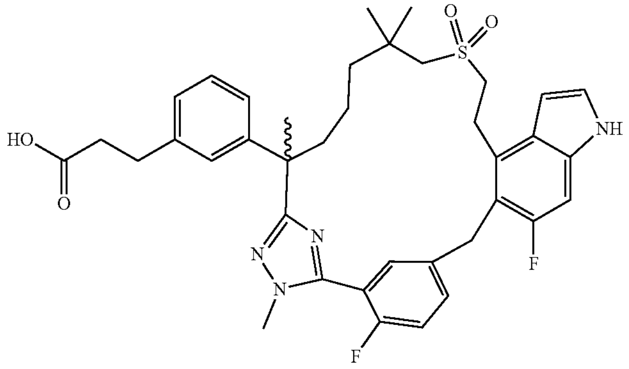 [SMILES: Cn1nc2nc1-c1cc(ccc1F)Cc1c(F)cc3[nH]ccc3c1CCS(=O)(=O)CC(C)(C)CCCC2(C)c1cccc(CCC(=O)O)c1] |
| 33A | 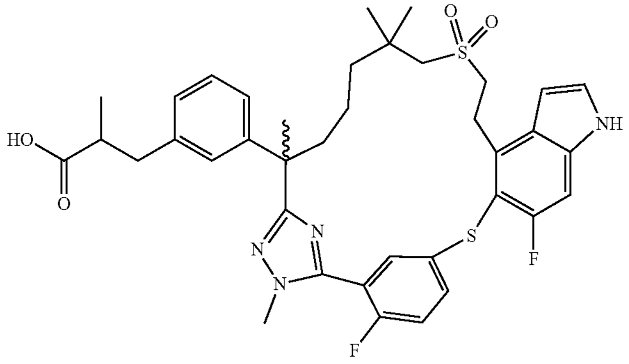 [SMILES: CC(Cc1cccc(C2(C)CCCC(C)(C)CS(=O)(=O)CCc3c(c(F)cc4[nH]ccc34)Sc3ccc(F)c(c3)-c3nc2nn3C)c1)C(=O)O] |
| 33B | 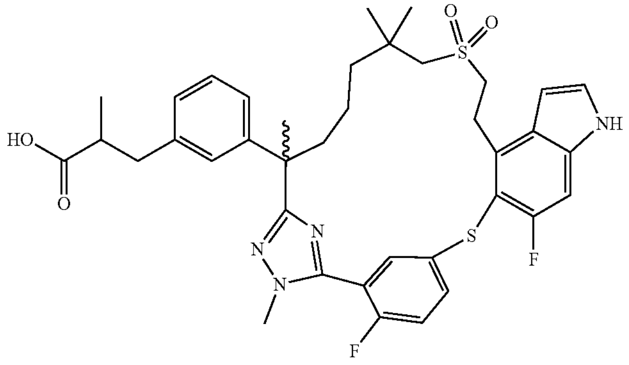 [SMILES: CC(Cc1cccc(C2(C)CCCC(C)(C)CS(=O)(=O)CCc3c(c(F)cc4[nH]ccc34)Sc3ccc(F)c(c3)-c3nc2nn3C)c1)C(=O)O] |
| 34A | 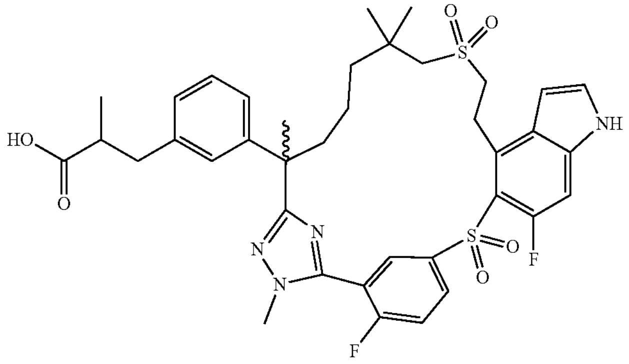 [SMILES: CC(Cc1cccc(C2(C)CCCC(C)(C)CS(=O)(=O)CCc3c(c(F)cc4[nH]ccc34)S(=O)(=O)c3ccc(F)c(c3)-c3nc2nn3C)c1)C(=O)O] |

-continued
| Compound No. | Structures |
| --- | --- |
| 34B | 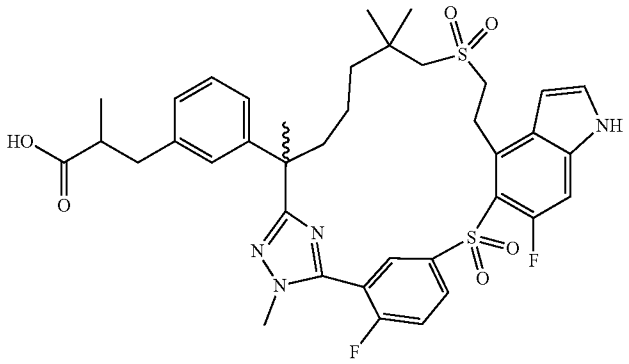 [SMILES: CC(Cc1cccc(C2(C)CCCC(C)(C)CS(=O)(=O)CCc3c(c(F)cc4[nH]ccc34)S(=O)(=O)c3ccc(F)c(c3)-c3nc2nn3C)c1)C(=O)O] |
| 35 | 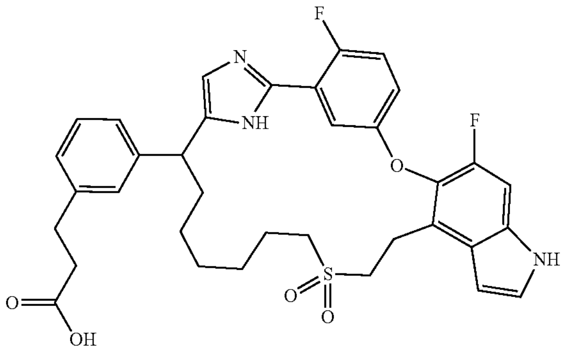 [SMILES: O=C(O)CCc1cccc(C2CCCCCCS(=O)(=O)CCc3c(c(F)cc4[nH]ccc34)Oc3ccc(F)c(c3)-c3ncc2[nH]3)c1] |
| 36 | 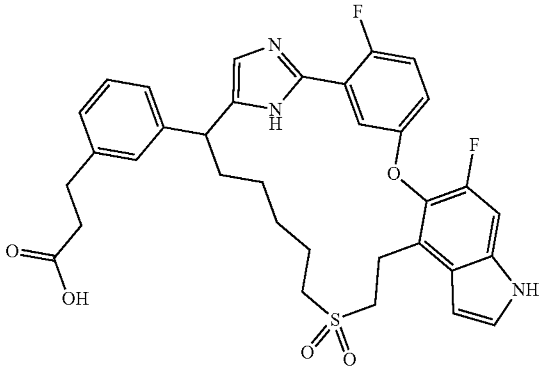 [SMILES: O=C(O)CCc1cccc(C2CCCCCS(=O)(=O)CCc3c(c(F)cc4[nH]ccc34)Oc3ccc(F)c(c3)-c3ncc2[nH]3)c1] |
| 37 | 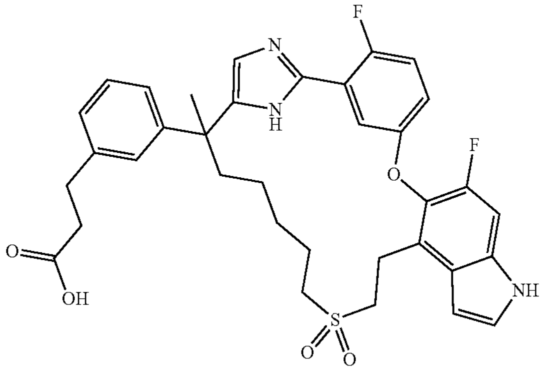 [SMILES: CC1(c2cccc(CCC(=O)O)c2)CCCCCS(=O)(=O)CCc2c(c(F)cc3[nH]ccc23)Oc2ccc(F)c(c2)-c2ncc1[nH]2] |

-continued
| Compound No. | Structures |
|---|---|
| 38 | 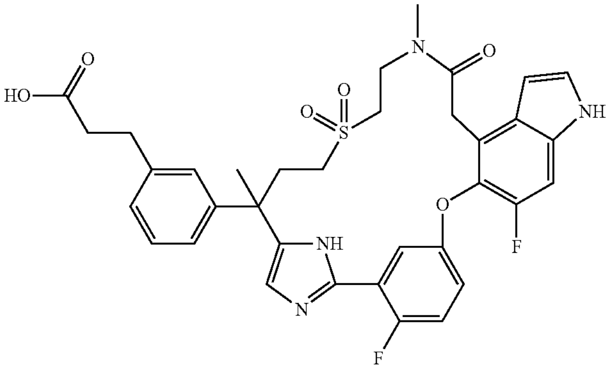 [SMILES: CN1CCS(=O)(=O)CCC(C)(c2cccc(CCC(=O)O)c2)c2cnc([nH]2)-c2cc(ccc2F)Oc2c(F)cc3[nH]ccc3c2CC1=O] |
| 39 | 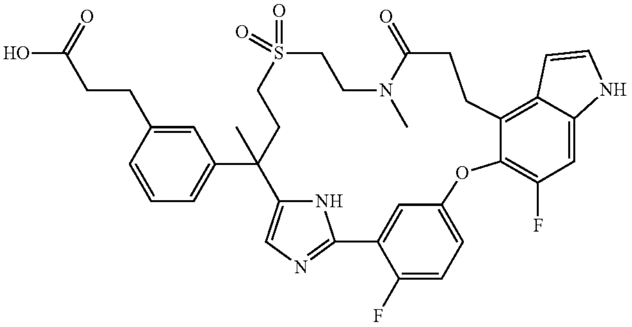 [SMILES: CN1CCS(=O)(=O)CCC(C)(c2cccc(CCC(=O)O)c2)c2cnc([nH]2)-c2cc(ccc2F)Oc2c(F)cc3[nH]ccc3c2CCC1=O] |
| 40 | 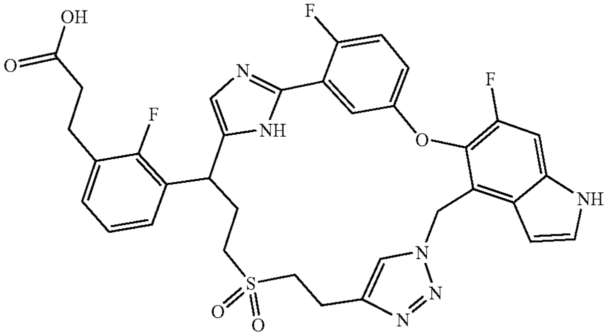 [SMILES: O=C(O)CCc1cccc(C2CCS(=O)(=O)CCc3cn(nn3)Cc3c(c(F)cc4[nH]ccc34)Oc3ccc(F)c(c3)-c3ncc2[nH]3)c1F] |
| 41 | 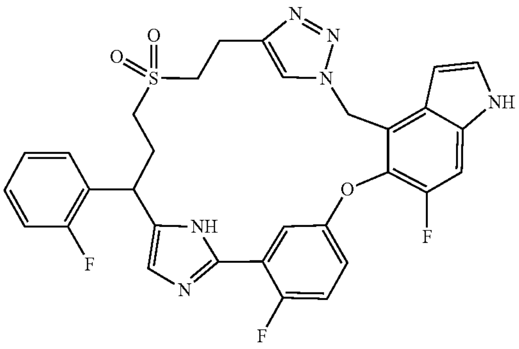 [SMILES: O=S1(=O)CCc2cn(nn2)Cc2c(c(F)cc3[nH]ccc23)Oc2ccc(F)c(c2)-c2ncc([nH]2)C(c2ccccc2F)CC1] |

-continued
| Compound No. | Structures |
| --- | --- |
| 42 | 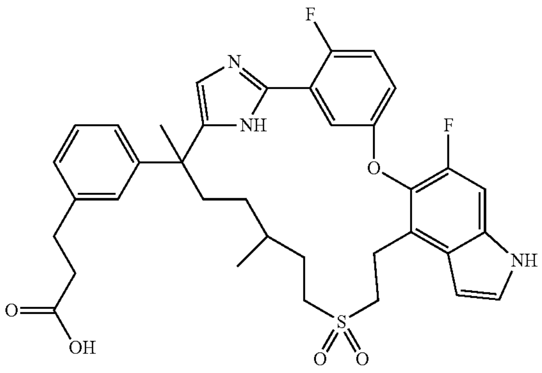 [SMILES: CC1CCC(C)(c2cccc(CCC(=O)O)c2)c2cnc([nH]2)-c2cc(ccc2F)Oc2c(F)cc3[nH]ccc3c2CCS(=O)(=O)CC1] |
| 43A | 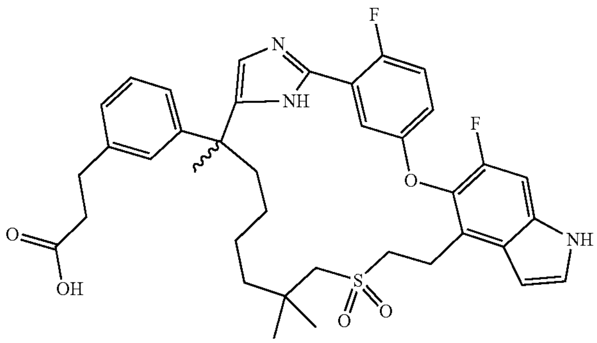 [SMILES: CC1(C)CCCCC(C)(c2cccc(CCC(=O)O)c2)c2cnc([nH]2)-c2cc(ccc2F)Oc2c(F)cc3[nH]ccc3c2CCS(=O)(=O)C1] |
| 43B | 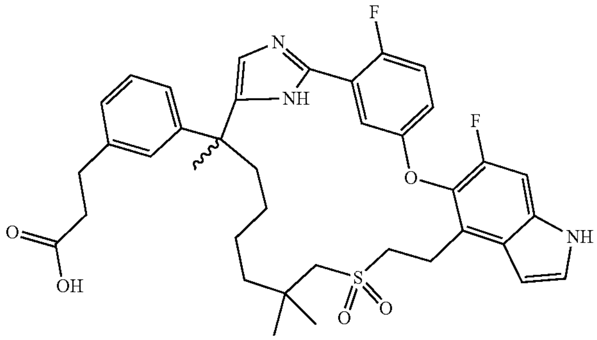 [SMILES: CC1(C)CCCCC(C)(c2cccc(CCC(=O)O)c2)c2cnc([nH]2)-c2cc(ccc2F)Oc2c(F)cc3[nH]ccc3c2CCS(=O)(=O)C1] |
| 44 | 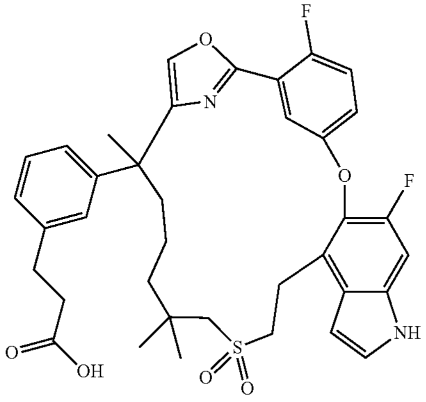 [SMILES: CC1(C)CCCC(C)(c2cccc(CCC(=O)O)c2)c2coc(n2)-c2cc(ccc2F)Oc2c(F)cc3[nH]ccc3c2CCS(=O)(=O)C1] |

-continued
| Compound No. | Structures |
| --- | --- |
| 45A | 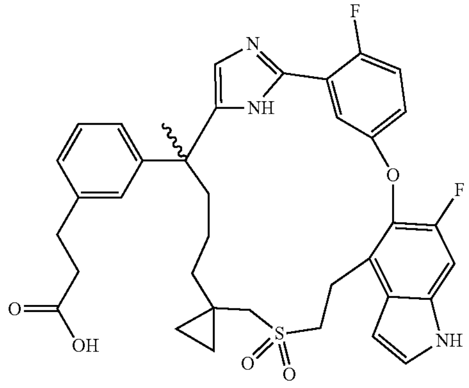 [SMILES: CC1(c2cccc(CCC(=O)O)c2)CCCC2(CC2)CS(=O)(=O)CCc2c(c(F)cc3[nH]ccc23)Oc2ccc(F)c(c2)-c2ncc1[nH]2] |
| 45B | 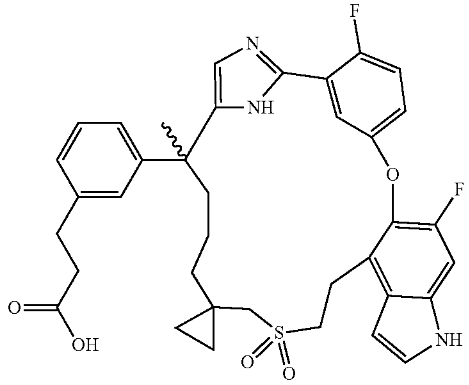 [SMILES: CC1(c2cccc(CCC(=O)O)c2)CCCC2(CC2)CS(=O)(=O)CCc2c(c(F)cc3[nH]ccc23)Oc2ccc(F)c(c2)-c2ncc1[nH]2] |
| 46 | 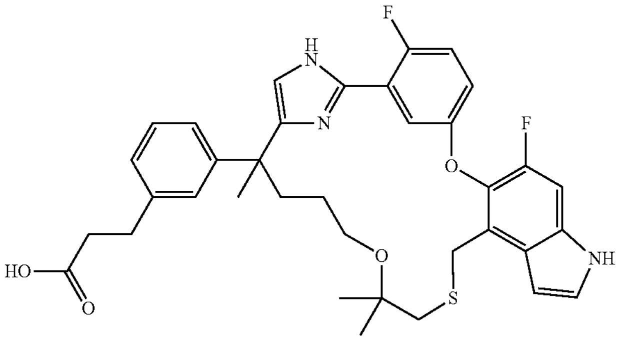 [SMILES: CC1(C)CSCc2c(c(F)cc3[nH]ccc23)Oc2ccc(F)c(c2)-c2nc(c[nH]2)C(C)(c2cccc(CCC(=O)O)c2)CCCO1] |
| 47 | 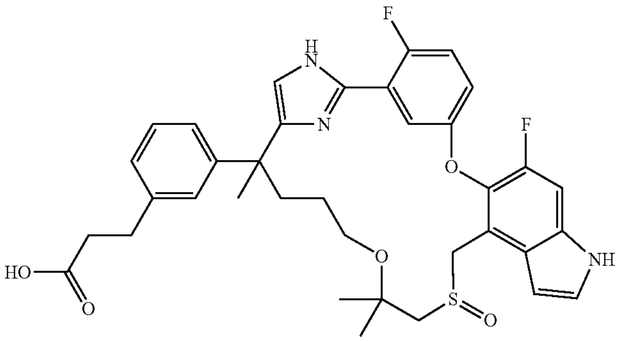 [SMILES: CC1(C)CS(=O)Cc2c(c(F)cc3[nH]ccc23)Oc2ccc(F)c(c2)-c2nc(c[nH]2)C(C)(c2cccc(CCC(=O)O)c2)CCCO1] |

-continued
| Compound No. | Structures |
| --- | --- |
| 48 | 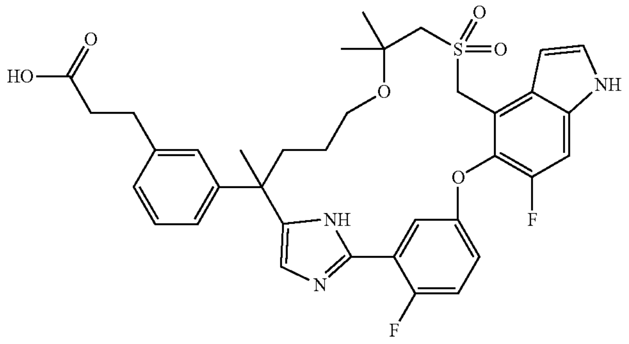 [SMILES: CC1(C)CS(=O)(=O)Cc2c(c(F)cc3[nH]ccc23)Oc2ccc(F)c(c2)-c2ncc([nH]2)C(C)(c2cccc(CCC(=O)O)c2)CCCO1] |
| 49 | 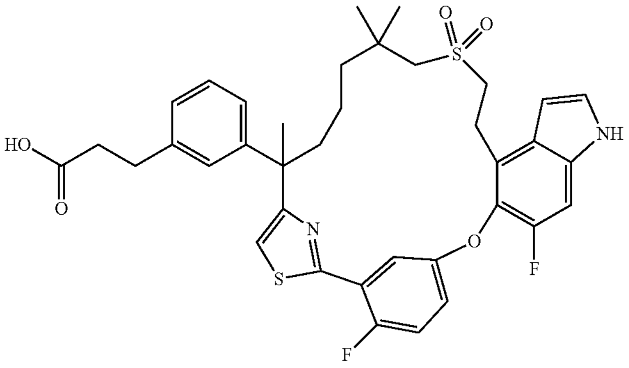 [SMILES: CC1(C)CCCC(C)(c2cccc(CCC(=O)O)c2)c2csc(n2)-c2cc(ccc2F)Oc2c(F)cc3[nH]ccc3c2CCS(=O)(=O)C1] |
| 50 | 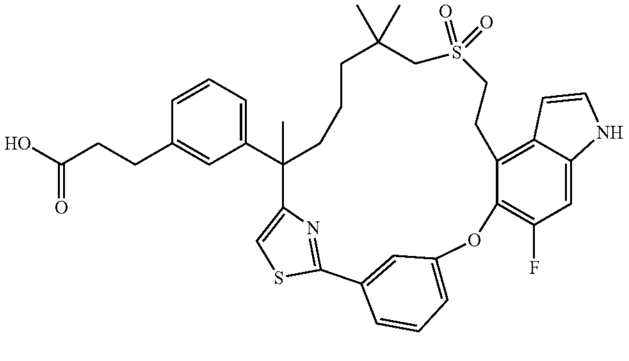 [SMILES: CC1(C)CCCC(C)(c2cccc(CCC(=O)O)c2)c2csc(n2)-c2cccc(c2)Oc2c(F)cc3[nH]ccc3c2CCS(=O)(=O)C1] |
| 51 | 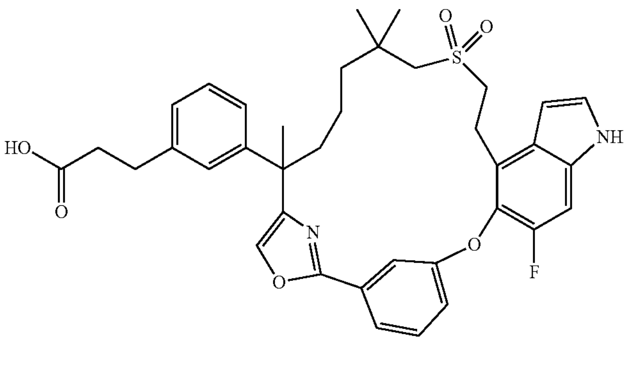 [SMILES: CC1(C)CCCC(C)(c2cccc(CCC(=O)O)c2)c2coc(n2)-c2cccc(c2)Oc2c(F)cc3[nH]ccc3c2CCS(=O)(=O)C1] |

-continued
| Compound No. | Structures |
| --- | --- |
| 52 | 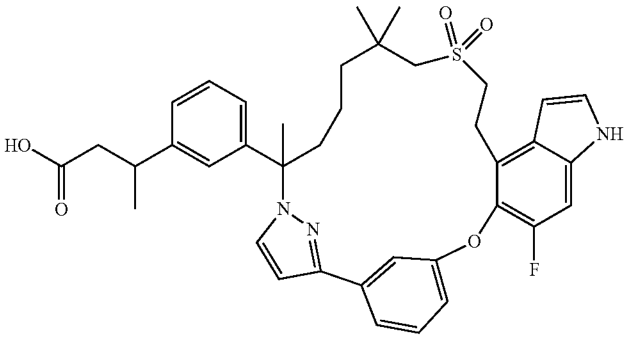 [SMILES: CC(CC(=O)O)c1cccc(C2(C)CCCC(C)(C)CS(=O)(=O)CCc3c(c(F)cc4[nH]ccc34)Oc3cccc(c3)-c3ccn2n3)c1] |
| 53 | 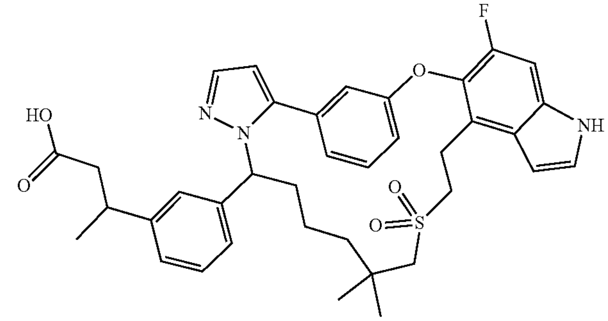 [SMILES: CC(CC(=O)O)c1cccc(C2CCCC(C)(C)CS(=O)(=O)CCc3c(c(F)cc4[nH]ccc34)Oc3cccc(c3)-c3ccnn32)c1] |
| 54A | 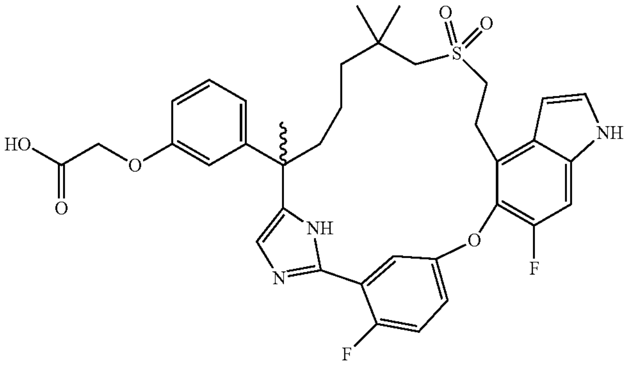 [SMILES: CC1(C)CCCC(C)(c2cccc(OCC(=O)O)c2)c2cnc([nH]2)-c2cc(ccc2F)Oc2c(F)cc3[nH]ccc3c2CCS(=O)(=O)C1] |
| 54B | 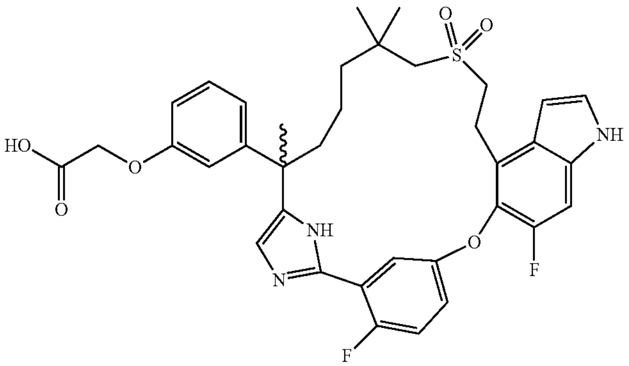 [SMILES: CC1(C)CCCC(C)(c2cccc(OCC(=O)O)c2)c2cnc([nH]2)-c2cc(ccc2F)Oc2c(F)cc3[nH]ccc3c2CCS(=O)(=O)C1] |

-continued
| Compound No. | Structures |
| --- | --- |
| 55A | 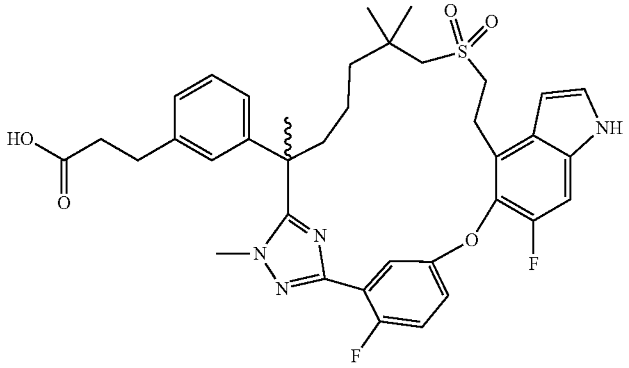 [SMILES: Cn1nc2nc1C(C)(c1cccc(CCC(=O)O)c1)CCCC(C)(C)CS(=O)(=O)CCc1c(c(F)cc3[nH]ccc13)Oc1ccc(F)c-2c1] |
| 55B | 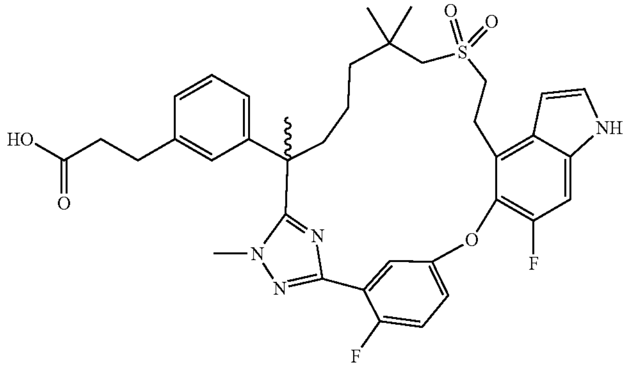 [SMILES: Cn1nc2nc1C(C)(c1cccc(CCC(=O)O)c1)CCCC(C)(C)CS(=O)(=O)CCc1c(c(F)cc3[nH]ccc13)Oc1ccc(F)c-2c1] |
| 56 | 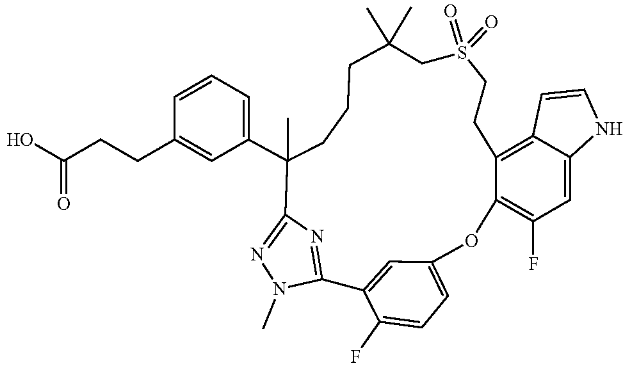 [SMILES: Cn1nc2nc1-c1cc(ccc1F)Oc1c(F)cc3[nH]ccc3c1CCS(=O)(=O)CC(C)(C)CCCC2(C)c1cccc(CCC(=O)O)c1] |
| 57 | 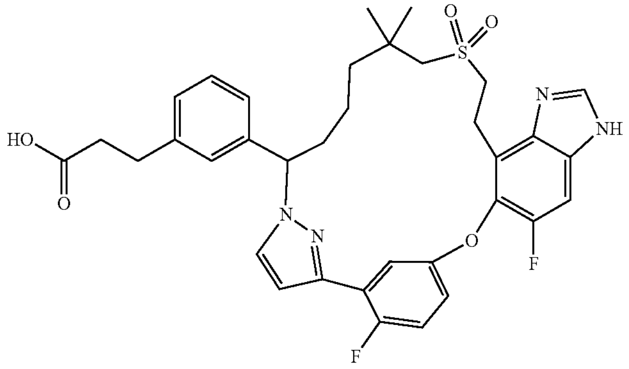 [SMILES: CC1(C)CCCC(c2cccc(CCC(=O)O)c2)n2ccc(n2)-c2cc(ccc2F)Oc2c(F)cc3[nH]cnc3c2CCS(=O)(=O)C1] |

-continued
| Compound No. | Structures |
| --- | --- |
| 58 | 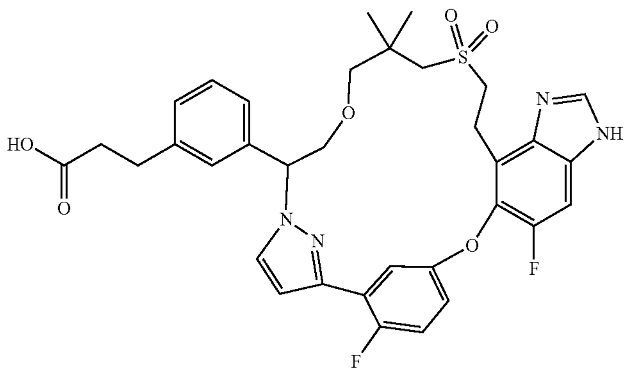 [SMILES: CC1(C)COCC(c2cccc(CCC(=O)O)c2)n2ccc(n2)-c2cc(ccc2F)Oc2c(F)cc3[nH]cnc3c2CCS(=O)(=O)C1] |
| 59 | 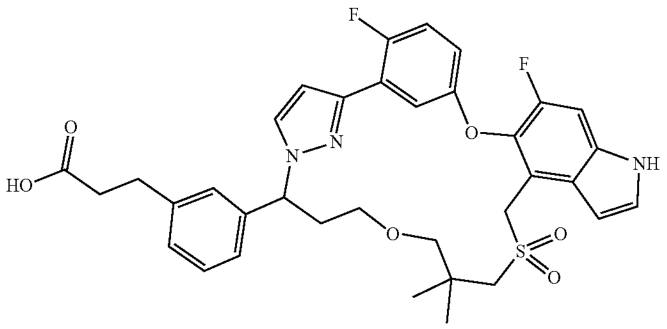 [SMILES: CC1(C)COCCC(c2cccc(CCC(=O)O)c2)n2ccc(n2)-c2cc(ccc2F)Oc2c(F)cc3[nH]ccc3c2CS(=O)(=O)C1] |
| 60 | 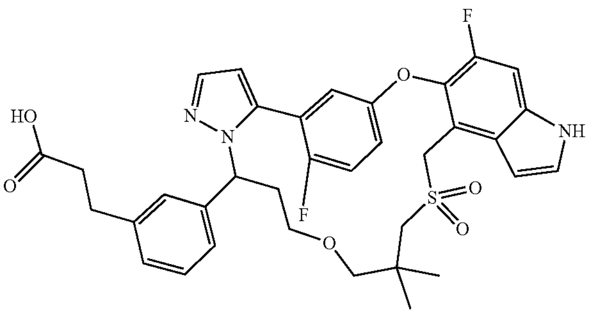 [SMILES: CC1(C)COCCC(c2cccc(CCC(=O)O)c2)n2nccc2-c2cc(ccc2F)Oc2c(F)cc3[nH]ccc3c2CS(=O)(=O)C1] |
| 61 | 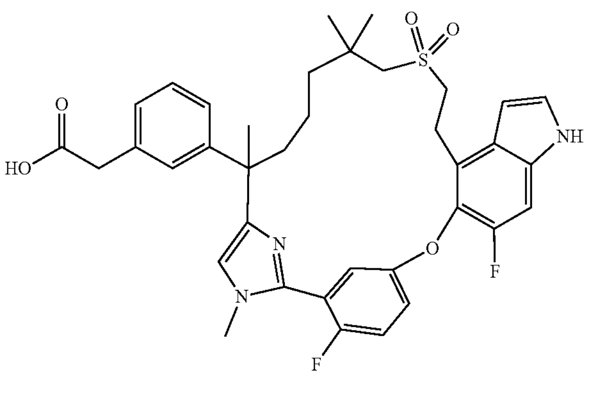 [SMILES: Cn1cc2nc1-c1cc(ccc1F)Oc1c(F)cc3[nH]ccc3c1CCS(=O)(=O)CC(C)(C)CCCC2(C)c1cccc(CC(=O)O)c1] |

-continued
| Compound No. | Structures |
|---|---|
| 62 | 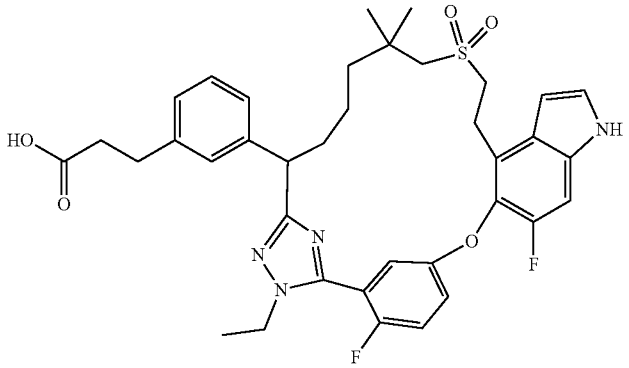 [SMILES: CCn1nc2nc1-c1cc(ccc1F)Oc1c(F)cc3[nH]ccc3c1CCS(=O)(=O)CC(C)(C)CCCC2c1cccc(CCC(=O)O)c1] |
| 63A | 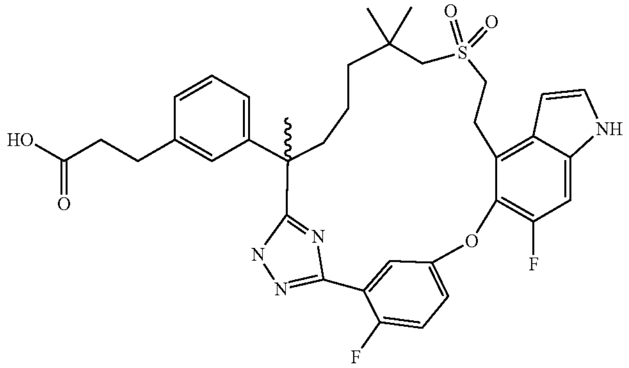 [SMILES: CC1(C)CCCC(C)(c2cccc(CCC(=O)O)c2)c2nc(n[nH]2)-c2cc(ccc2F)Oc2c(F)cc3[nH]ccc3c2CCS(=O)(=O)C1] |
| 63B | 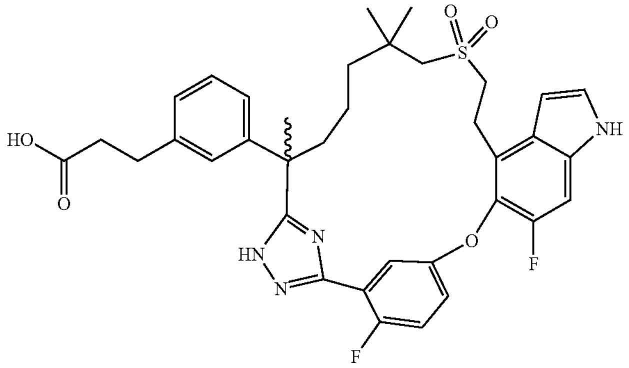 [SMILES: CC1(C)CCCC(C)(c2cccc(CCC(=O)O)c2)c2nc(n[nH]2)-c2cc(ccc2F)Oc2c(F)cc3[nH]ccc3c2CCS(=O)(=O)C1] |
| 64 | 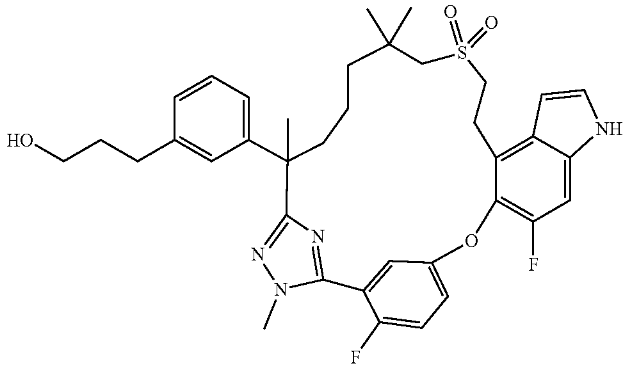 [SMILES: Cn1nc2nc1-c1cc(ccc1F)Oc1c(F)cc3[nH]ccc3c1CCS(=O)(=O)CC(C)(C)CCCC2(C)c1cccc(CCCO)c1] |

-continued
| Compound No. | Structures |
| --- | --- |
| 65A | 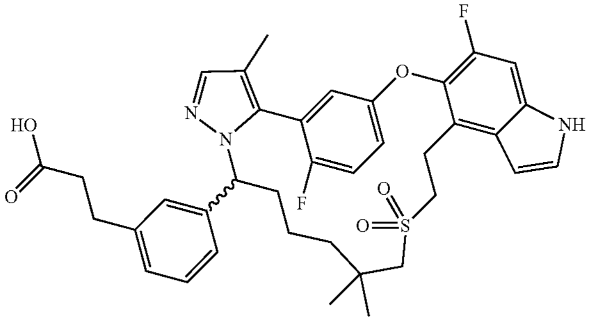 |
| 65B | 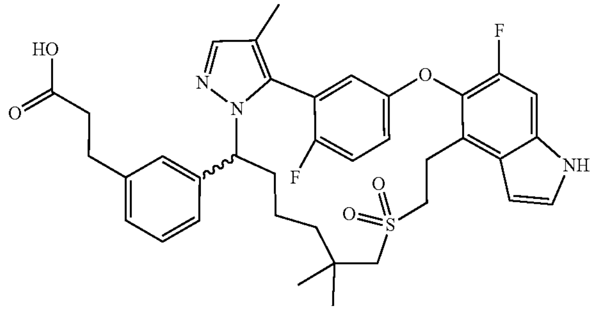 [SMILES: Cc1cnn2c1-c1cc(ccc1F)Oc1c(F)cc3[nH]ccc3c1CCS(=O)(=O)CC(C)(C)CCCC2c1cccc(CCC(=O)O)c1] |
| 66 | 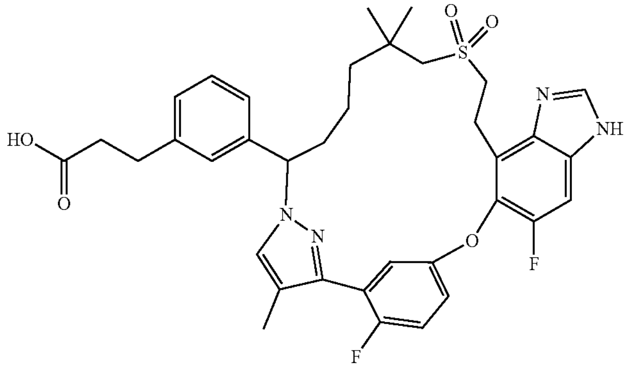 [SMILES: Cc1cn2nc1-c1cc(ccc1F)Oc1c(F)cc3[nH]cnc3c1CCS(=O)(=O)CC(C)(C)CCCC2c1cccc(CCC(=O)O)c1] |
| 67A | 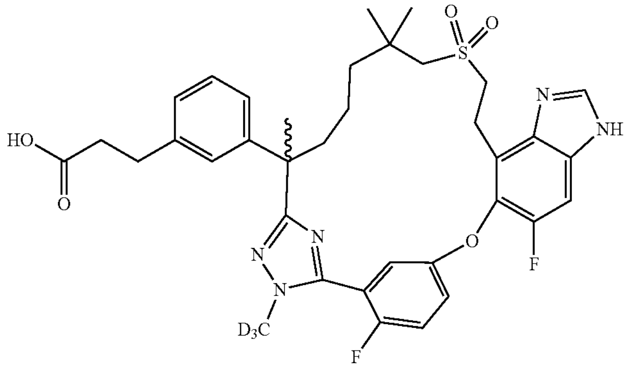 [SMILES: [2H]C([2H])([2H])n1nc2nc1-c1cc(ccc1F)Oc1c(F)cc3[nH]cnc3c1CCS(=O)(=O)CC(C)(C)CCCC2(C)c1cccc(CCC(=O)O)c1] |

-continued
| Compound No. | Structures |
| --- | --- |
| 67B | 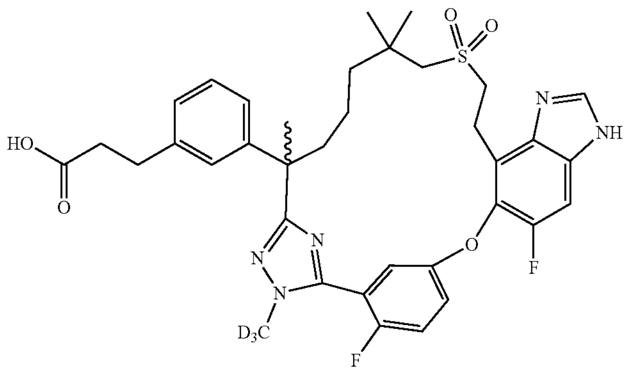 [SMILES: [2H]C([2H])([2H])n1nc2nc1-c1cc(ccc1F)Oc1c(F)cc3[nH]cnc3c1CCS(=O)(=O)CC(C)(C)CCCC2(C)c1cccc(CCC(=O)O)c1] |
| 68 | 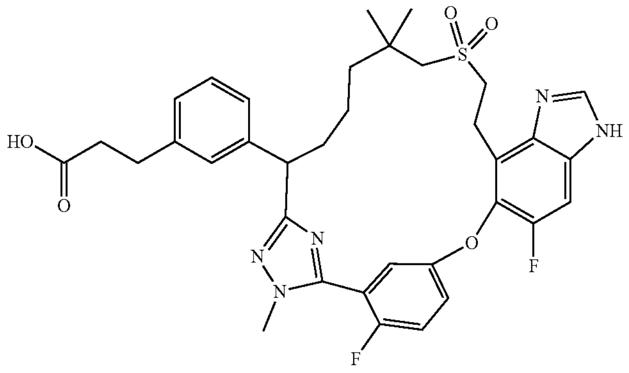 [SMILES: Cn1nc2nc1-c1cc(ccc1F)Oc1c(F)cc3[nH]cnc3c1CCS(=O)(=O)CC(C)(C)CCCC2c1cccc(CCC(=O)O)c1] |
| 69 | 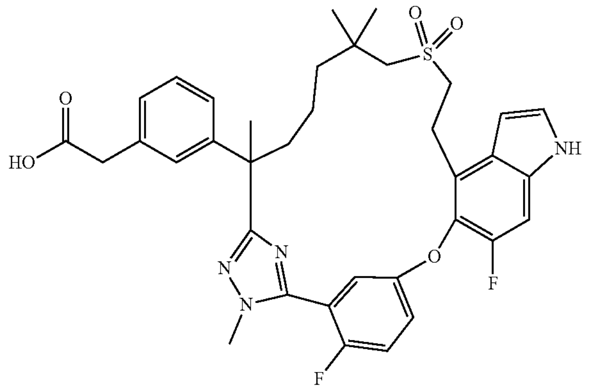 |
| 70 | 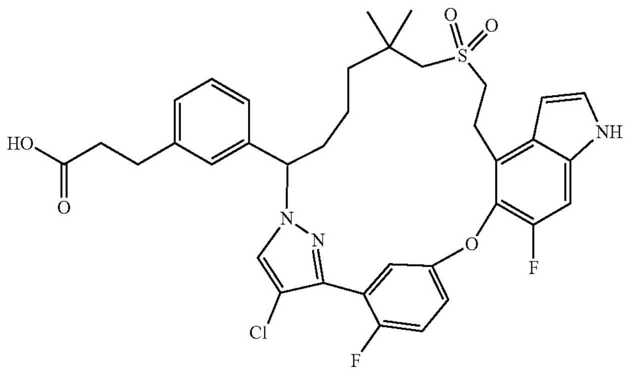 [SMILES: CC1(C)CCCC(c2cccc(CCC(=O)O)c2)n2cc(Cl)c(n2)-c2cc(ccc2F)Oc2c(F)cc3[nH]ccc3c2CCS(=O)(=O)C1] |

-continued
| Compound No. | Structures |
| --- | --- |
| 71 | 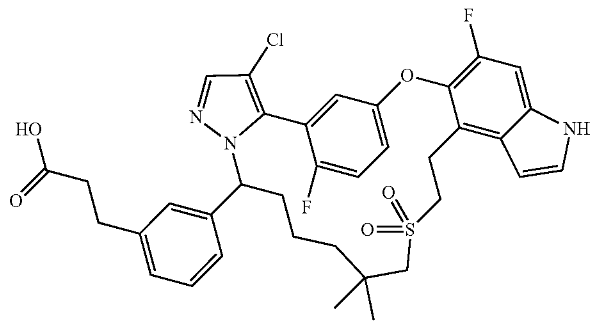 [SMILES: CC1(C)CCCC(c2cccc(CCC(=O)O)c2)n2ncc(Cl)c2-c2cc(ccc2F)Oc2c(F)cc3[nH]ccc3c2CCS(=O)(=O)C1] |
| 72A | 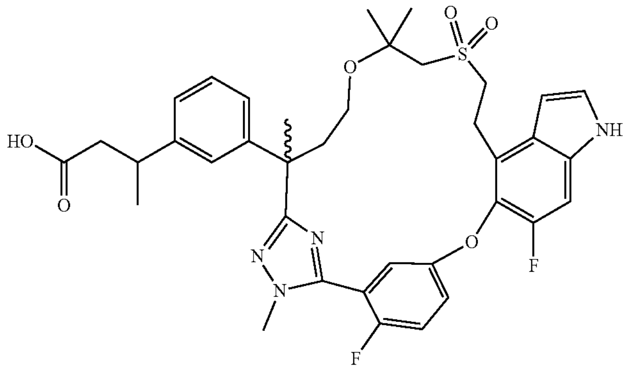 |
| 72B | 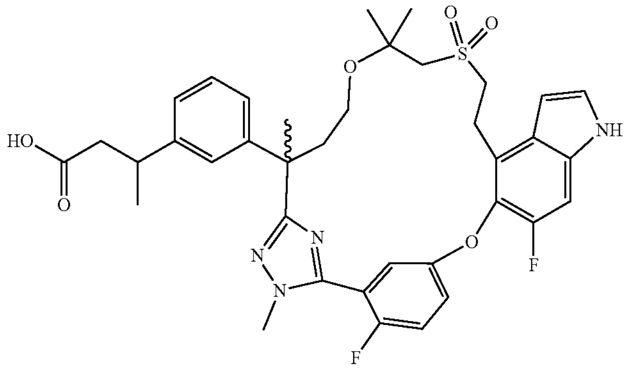 |
| 73A | 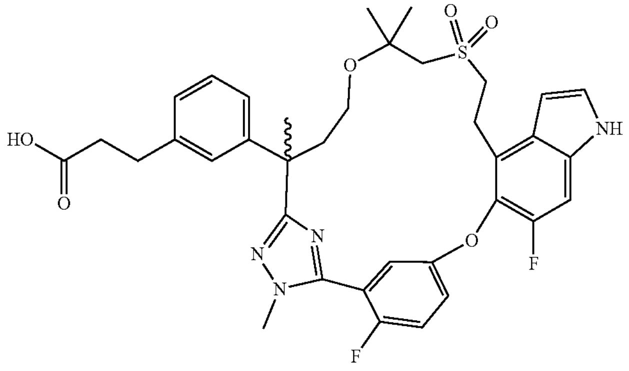 [SMILES: Cn1nc2nc1-c1cc(ccc1F)Oc1c(F)cc3[nH]ccc3c1CCS(=O)(=O)CC(C)(C)OCCC2(C)c1cccc(CCC(=O)O)c1] |

-continued
| Compound No. | Structures |
| --- | --- |
| 73B | 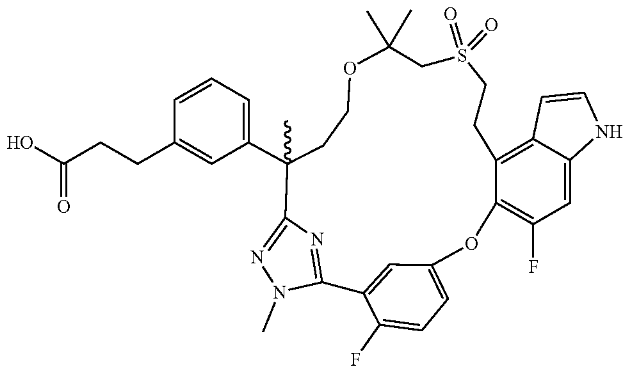 [SMILES: Cn1nc2nc1-c1cc(ccc1F)Oc1c(F)cc3[nH]ccc3c1CCS(=O)(=O)CC(C)(C)OCCC2(C)c1cccc(CCC(=O)O)c1] |
| 74 | 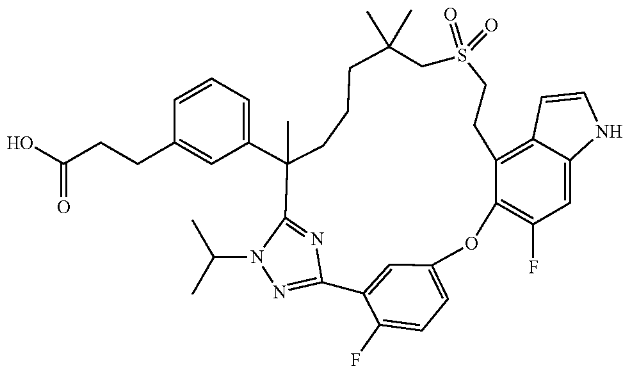 [SMILES: CC(C)n1nc2nc1C(C)(c1cccc(CCC(=O)O)c1)CCCC(C)(C)CS(=O)(=O)CCc1c(c(F)cc3[nH]ccc13)Oc1ccc(F)c-2c1] |
| 75 | 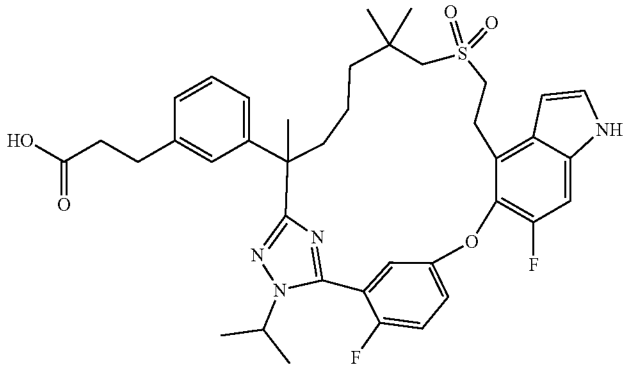 [SMILES: CC(C)n1nc2nc1-c1cc(ccc1F)Oc1c(F)cc3[nH]ccc3c1CCS(=O)(=O)CC(C)(C)CCCC2(C)c1cccc(CCC(=O)O)c1] |
| 76 | 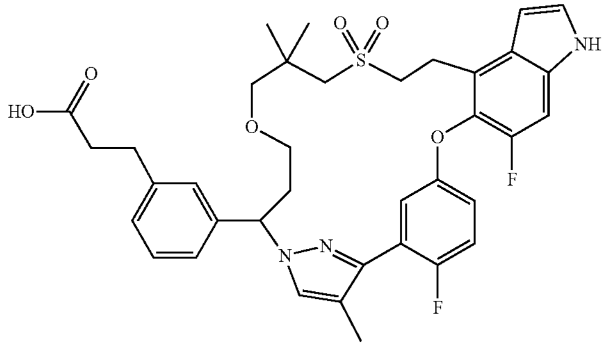 [SMILES: Cc1cn2nc1-c1cc(ccc1F)Oc1c(F)cc3[nH]ccc3c1CCS(=O)(=O)CC(C)(C)COCCC2c1cccc(CCC(=O)O)c1] |

-continued
| Compound No. | Structures |
| --- | --- |
| 77 | 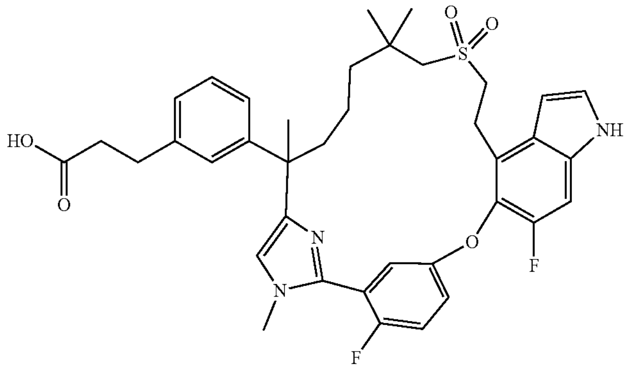 [SMILES: Cn1cc2nc1-c1cc(ccc1F)Oc1c(F)cc3[nH]ccc3c1CCS(=O)(=O)CC(C)(C)CCCC2(C)c1cccc(CCC(=O)O)c1] |
| 78 | 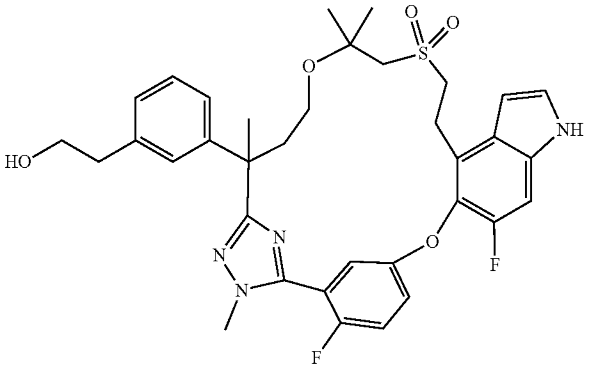 [SMILES: Cn1nc2nc1-c1cc(ccc1F)Oc1c(F)cc3[nH]ccc3c1CCS(=O)(=O)CC(C)(C)OCCC2(C)c1cccc(CCO)c1] |
| 79A | 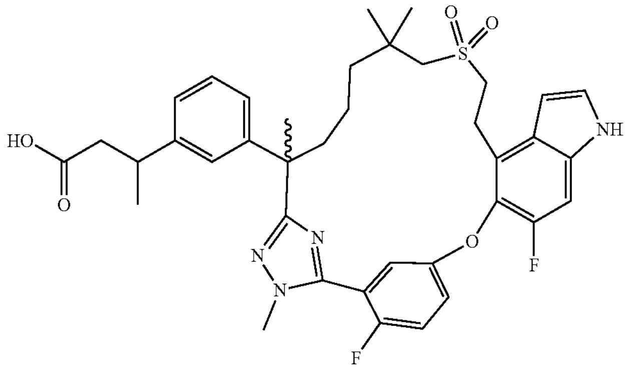 [SMILES: CC(CC(=O)O)c1cccc(C2(C)CCCC(C)(C)CS(=O)(=O)CCc3c(c(F)cc4[nH]ccc34)Oc3ccc(F)c(c3)-c3nc2nn3C)c1] |
| 79B | 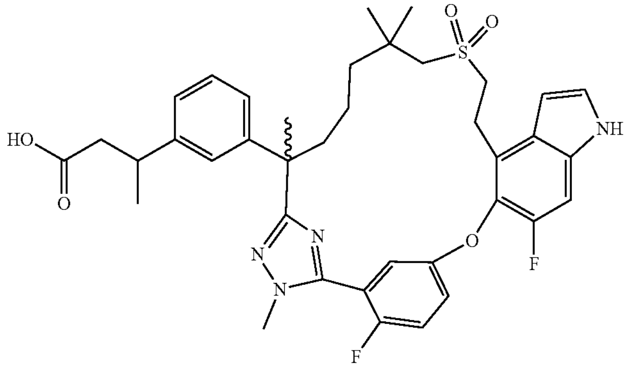 [SMILES: CC(CC(=O)O)c1cccc(C2(C)CCCC(C)(C)CS(=O)(=O)CCc3c(c(F)cc4[nH]ccc34)Oc3ccc(F)c(c3)-c3nc2nn3C)c1] |

-continued
| Compound No. | Structures |
| --- | --- |
| 80 | 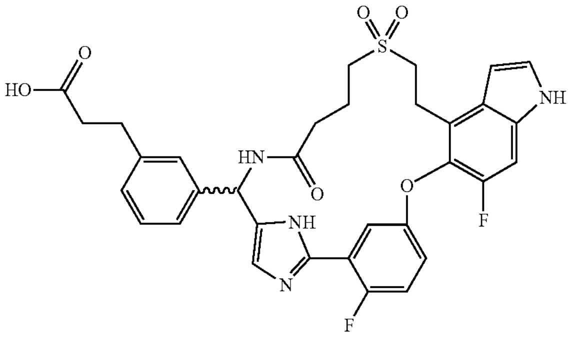 [SMILES: O=C(O)CCc1cccc(C2NC(=O)CCCS(=O)(=O)CCc3c(c(F)cc4[nH]ccc34)Oc3ccc(F)c(c3)-c3ncc2[nH]3)c1] |
| 81 | 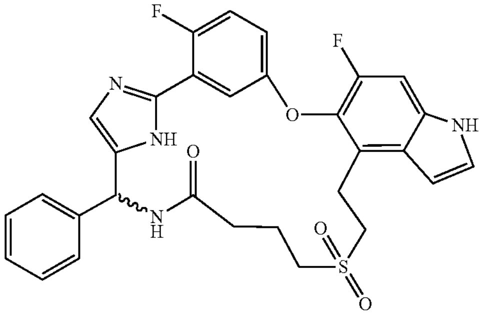 [SMILES: O=C1CCCS(=O)(=O)CCc2c(c(F)cc3[nH]ccc23)Oc2ccc(F)c(c2)-c2ncc([nH]2)C(c2ccccc2)N1] |
| 82 | 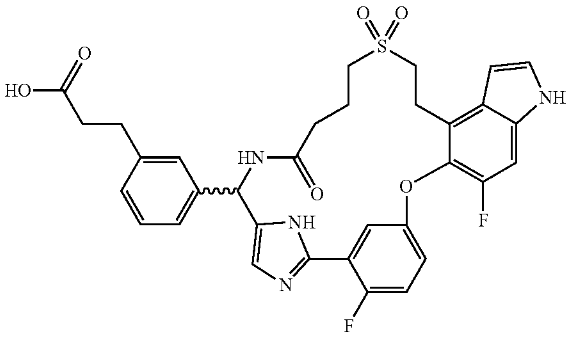 [SMILES: O=C(O)CCc1cccc(C2NC(=O)CCCS(=O)(=O)CCc3c(c(F)cc4[nH]ccc34)Oc3ccc(F)c(c3)-c3ncc2[nH]3)c1] |
| 83 | 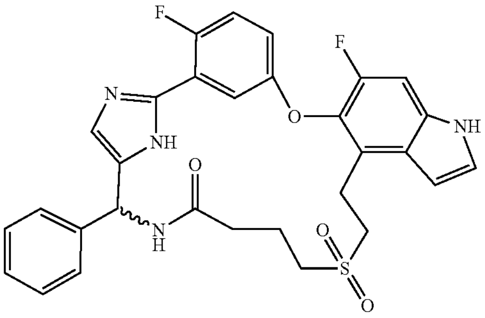 [SMILES: O=C1CCCS(=O)(=O)CCc2c(c(F)cc3[nH]ccc23)Oc2ccc(F)c(c2)-c2ncc([nH]2)C(c2ccccc2)N1] |

-continued
| Compound No. | Structures |
| --- | --- |
| 84A | 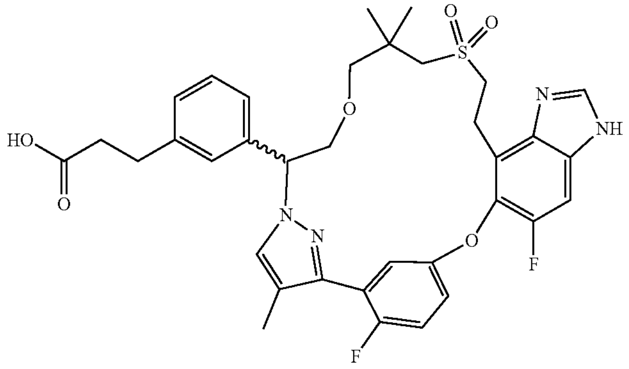 |
| 84B | 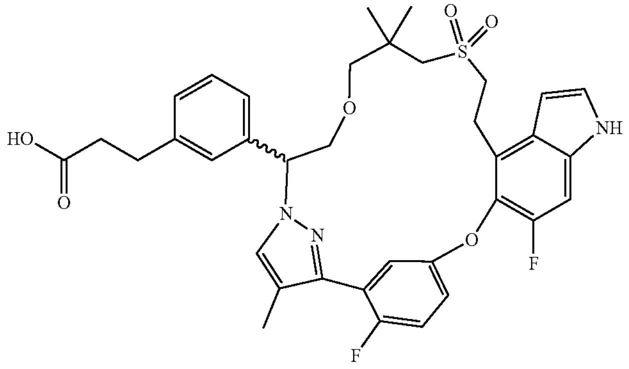 [SMILES: Cc1cn2nc1-c1cc(ccc1F)Oc1c(F)cc3[nH]ccc3c1CCS(=O)(=O)CC(C)(C)COCC2c1cccc(CCC(=O)O)c1] |
| 85 | 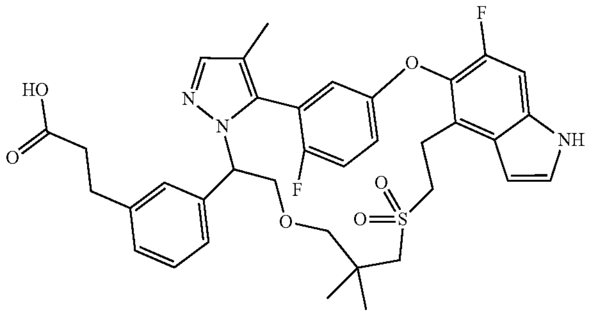 [SMILES: Cc1cnn2c1-c1cc(ccc1F)Oc1c(F)cc3[nH]ccc3c1CCS(=O)(=O)CC(C)(C)COCC2c1cccc(CCC(=O)O)c1] |
| 86A | 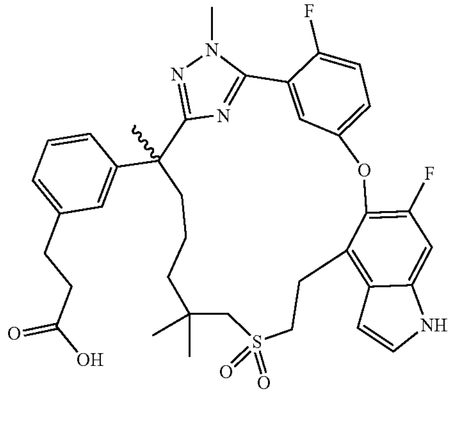 [SMILES: Cn1nc2nc1-c1cc(ccc1F)Oc1c(F)cc3[nH]ccc3c1CCS(=O)(=O)CC(C)(C)CCCC2(C)c1cccc(CCC(=O)O)c1] |

-continued
| Compound No. | Structures |
|---|---|
| 86B | 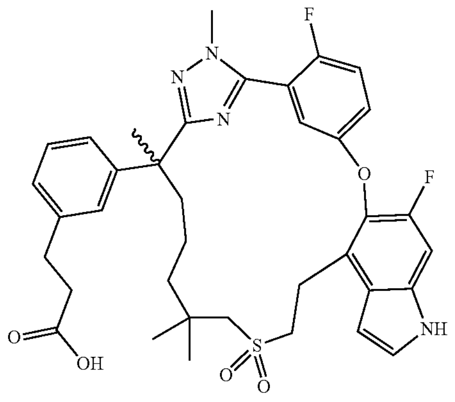 [SMILES: Cn1nc2nc1-c1cc(ccc1F)Oc1c(F)cc3[nH]ccc3c1CCS(=O)(=O)CC(C)(C)CCCC2(C)c1cccc(CCC(=O)O)c1] |
| 87A | 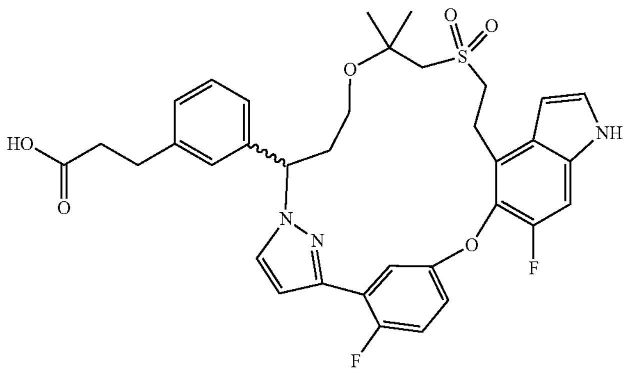 [SMILES: CC1(C)CS(=O)(=O)CCc2c(c(F)cc3[nH]ccc23)Oc2ccc(F)c(c2)-c2ccn(n2)C(c2cccc(CCC(=O)O)c2)CCO1] |
| 87B | 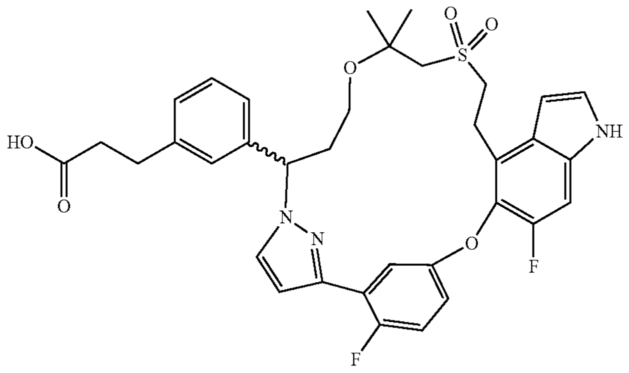 [SMILES: CC1(C)CS(=O)(=O)CCc2c(c(F)cc3[nH]ccc23)Oc2ccc(F)c(c2)-c2ccn(n2)C(c2cccc(CCC(=O)O)c2)CCO1] |
| 88 | 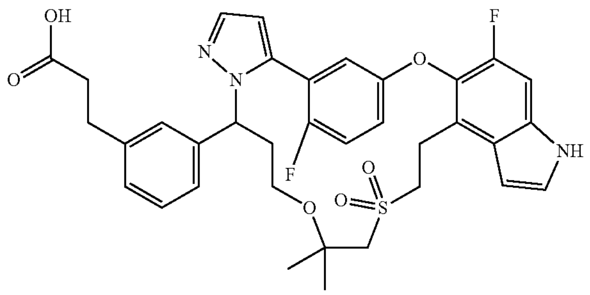 [SMILES: CC1(C)CS(=O)(=O)CCc2c(c(F)cc3[nH]ccc23)Oc2ccc(F)c(c2)-c2ccnn2C(c2cccc(CCC(=O)O)c2)CCO1] |

-continued
| Compound No. | Structures |
|---|---|
| 89A | 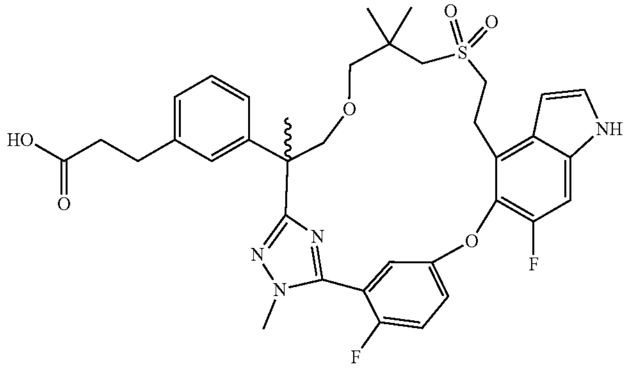 [SMILES: Cn1nc2nc1-c1cc(ccc1F)Oc1c(F)cc3[nH]ccc3c1CCS(=O)(=O)CC(C)(C)COCC2(C)c1cccc(CCC(=O)O)c1] |
| 89B | 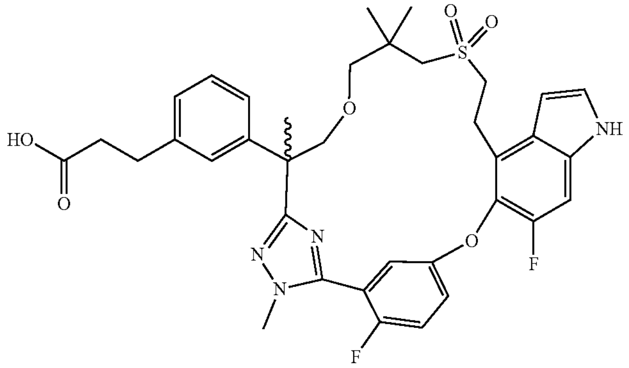 [SMILES: Cn1nc2nc1-c1cc(ccc1F)Oc1c(F)cc3[nH]ccc3c1CCS(=O)(=O)CC(C)(C)COCC2(C)c1cccc(CCC(=O)O)c1] |
| 90A | 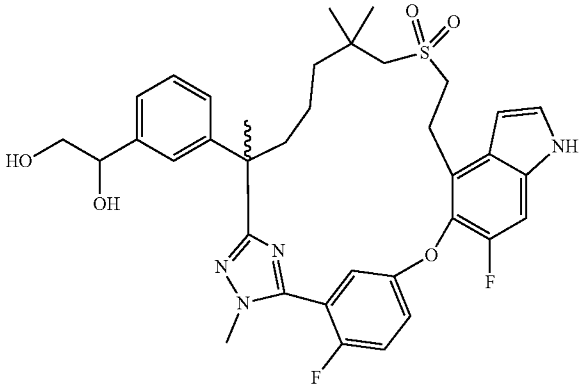 [SMILES: Cn1nc2nc1-c1cc(ccc1F)Oc1c(F)cc3[nH]ccc3c1CCS(=O)(=O)CC(C)(C)CCCC2(C)c1cccc(C(O)CO)c1] |
| 90B | 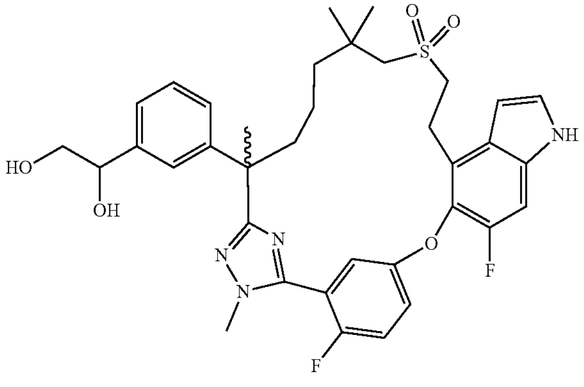 [SMILES: Cn1nc2nc1-c1cc(ccc1F)Oc1c(F)cc3[nH]ccc3c1CCS(=O)(=O)CC(C)(C)CCCC2(C)c1cccc(C(O)CO)c1] |

-continued
| Compound No. | Structures |
| --- | --- |
| 91A | 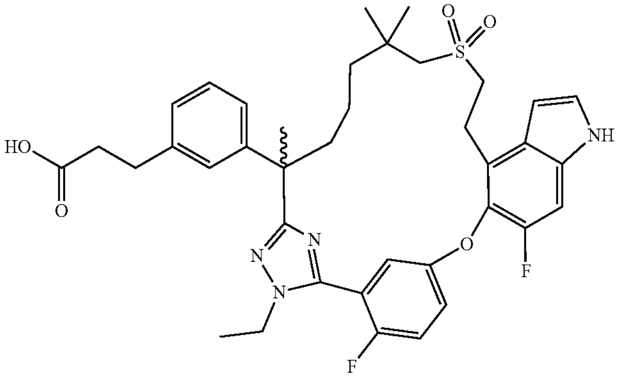 [SMILES: CCn1nc2nc1-c1cc(ccc1F)Oc1c(F)cc3[nH]ccc3c1CCS(=O)(=O)CC(C)(C)CCCC2(C)c1cccc(CCC(=O)O)c1] |
| 91B | 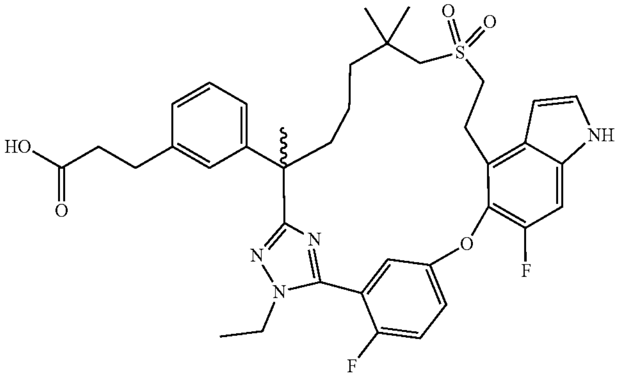 [SMILES: CCn1nc2nc1-c1cc(ccc1F)Oc1c(F)cc3[nH]ccc3c1CCS(=O)(=O)CC(C)(C)CCCC2(C)c1cccc(CCC(=O)O)c1] |
| 92 | 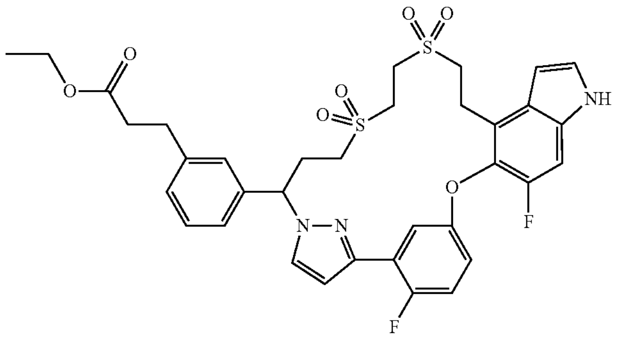 [SMILES: CCOC(=O)CCc1cccc(C2CCS(=O)(=O)CCS(=O)(=O)CCc3c(c(F)cc4[nH]ccc34)Oc3ccc(F)c(c3)-c3ccn2n3)c1] |
| 93 | 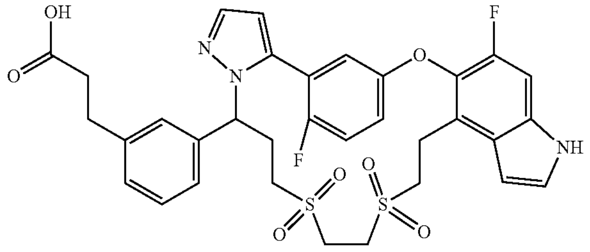 [SMILES: O=C(O)CCc1cccc(C2CCS(=O)(=O)CCS(=O)(=O)CCc3c(c(F)cc4[nH]ccc34)Oc3ccc(F)c(c3)-c3ccnn32)c1] |

-continued
| Compound No. | Structures |
| --- | --- |
| 94 | 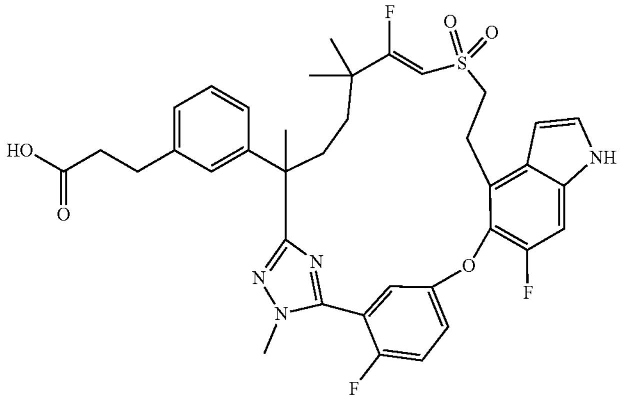 [SMILES: Cn1nc2nc1-c1cc(ccc1F)Oc1c(F)cc3[nH]ccc3c1CCS(=O)(=O)/C=C(\F)C(C)(C)CCC2(C)c1cccc(CCC(=O)O)c1] |
| 95A | 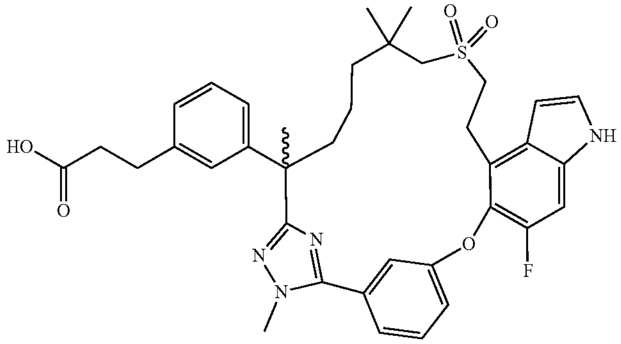 [SMILES: Cn1nc2nc1-c1cccc(c1)Oc1c(F)cc3[nH]ccc3c1CCS(=O)(=O)CC(C)(C)CCCC2(C)c1cccc(CCC(=O)O)c1] |
| 95B | 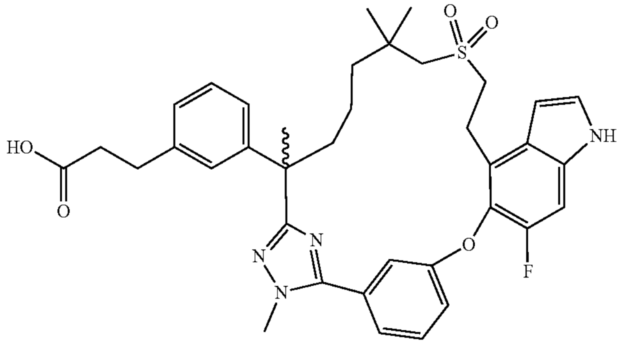 [SMILES: Cn1nc2nc1-c1cccc(c1)Oc1c(F)cc3[nH]ccc3c1CCS(=O)(=O)CC(C)(C)CCCC2(C)c1cccc(CCC(=O)O)c1] |
| 96A | 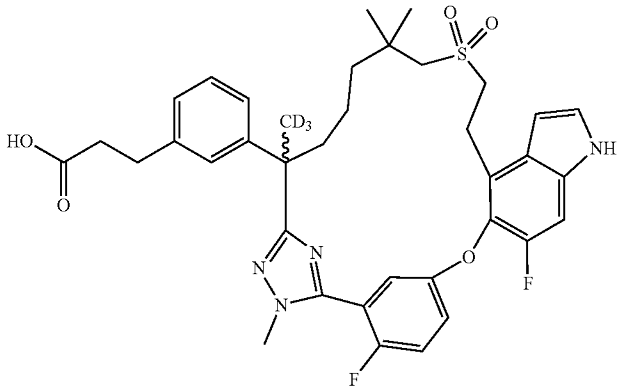 [SMILES: [2H]C([2H])([2H])C1(c2cccc(CCC(=O)O)c2)CCCC(C)(C)CS(=O)(=O)CCc2c(c(F)cc3[nH]ccc23)Oc2ccc(F)c(c2)-c2nc1nn2C] |

-continued
| Compound No. | Structures |
|---|---|
| 96B | 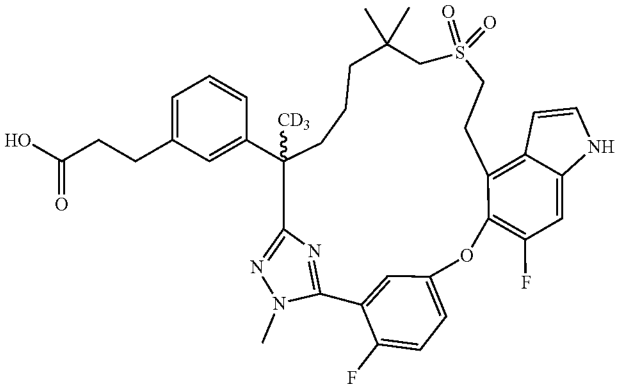 [SMILES: [2H]C([2H])([2H])C1(c2cccc(CCC(=O)O)c2)CCCC(C)(C)CS(=O)(=O)CCc2c(c(F)cc3[nH]ccc23)Oc2ccc(F)c(c2)-c2nc1nn2C] |
| 97A | 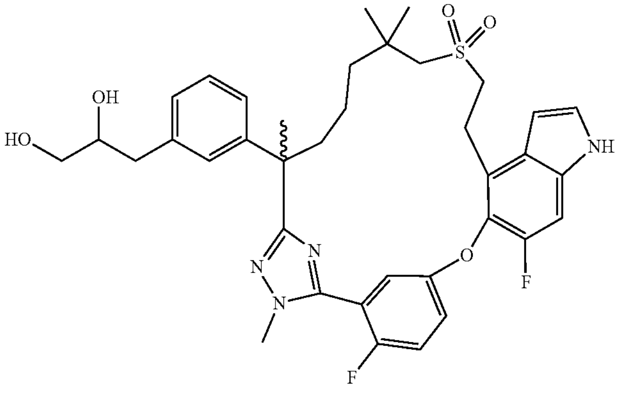 [SMILES: Cn1nc2nc1-c1cc(ccc1F)Oc1c(F)cc3[nH]ccc3c1CCS(=O)(=O)CC(C)(C)CCCC2(C)c1cccc(CC(O)CO)c1] |
| 97B | 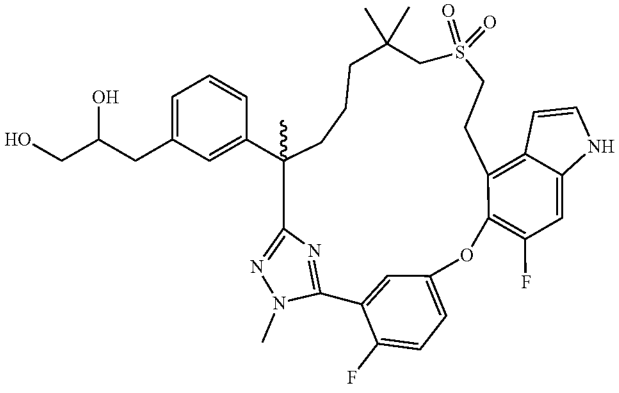 [SMILES: Cn1nc2nc1-c1cc(ccc1F)Oc1c(F)cc3[nH]ccc3c1CCS(=O)(=O)CC(C)(C)CCCC2(C)c1cccc(CC(O)CO)c1] |
| 98A | 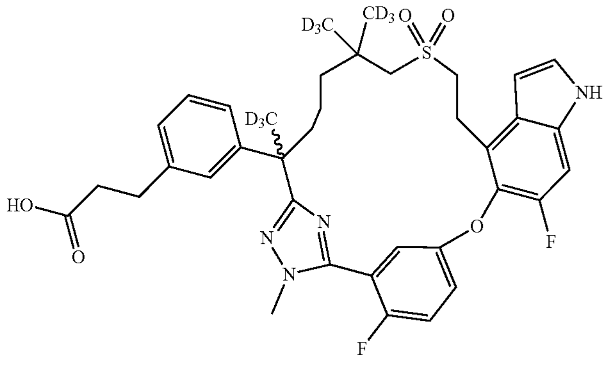 [SMILES: [2H]C([2H])([2H])C1(c2cccc(CCC(=O)O)c2)CCCC(C([2H])([2H])[2H])(C([2H])([2H])[2H])CS(=O)(=O)CCc2c(c(F)cc3[nH]ccc23)Oc2ccc(F)c(c2)-c2nc1nn2C] |

-continued
| Compound No. | Structures |
| --- | --- |
| 98B | 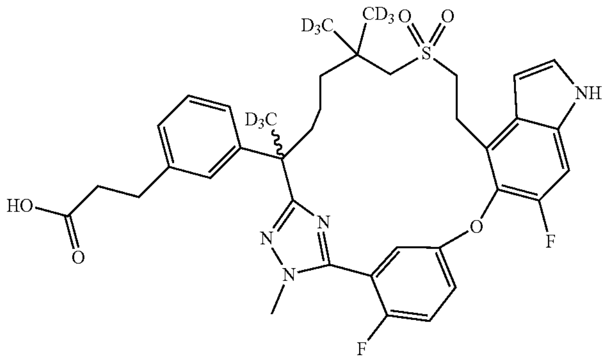 [SMILES: [2H]C([2H])([2H])C1(c2cccc(CCC(=O)O)c2)CCCC(C([2H])([2H])[2H])(C([2H])([2H])[2H])CS(=O)(=O)CCc2c(c(F)cc3[nH]ccc23)Oc2ccc(F)c(c2)-c2nc1nn2C] |
| 99 | 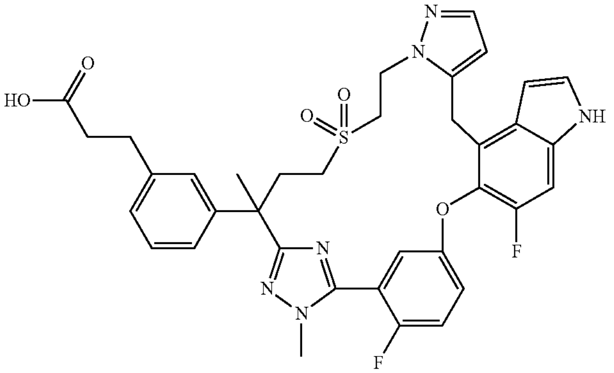 [SMILES: Cn1nc2nc1-c1cc(ccc1F)Oc1c(F)cc3[nH]ccc3c1Cc1ccnn1CCS(=O)(=O)CCC2(C)c1cccc(CCC(=O)O)c1] |
| 100A | 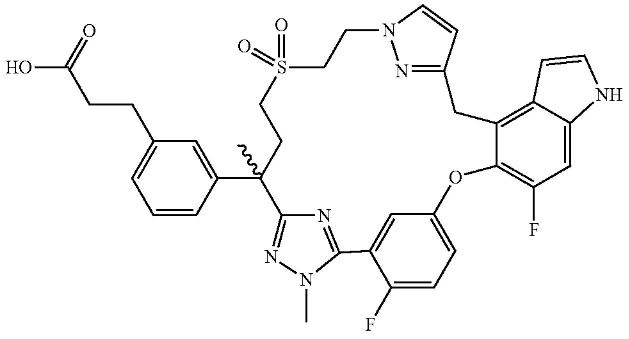 [SMILES: Cn1nc2nc1-c1cc(ccc1F)Oc1c(F)cc3[nH]ccc3c1Cc1ccn(n1)CCS(=O)(=O)CCC2(C)c1cccc(CCC(=O)O)c1] |
| 100B | 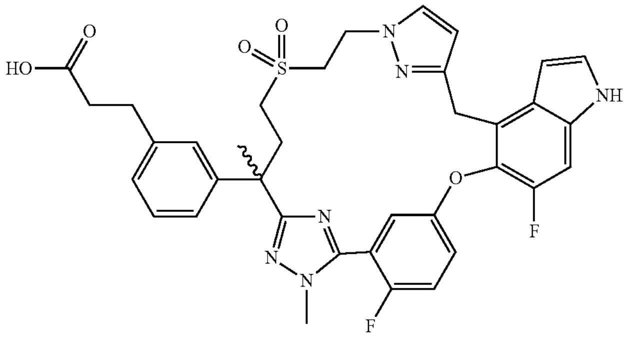 [SMILES: Cn1nc2nc1-c1cc(ccc1F)Oc1c(F)cc3[nH]ccc3c1Cc1ccn(n1)CCS(=O)(=O)CCC2(C)c1cccc(CCC(=O)O)c1] |

-continued
| Compound No. | Structures |
| --- | --- |
| 101A | 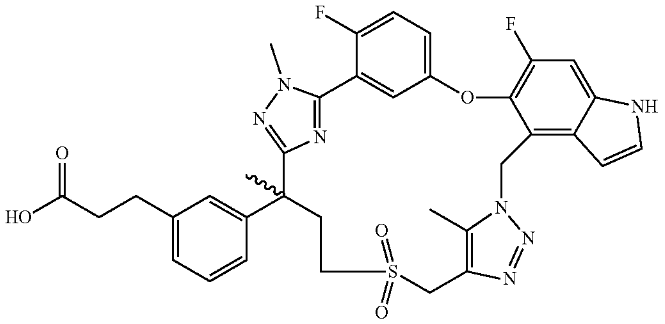 [SMILES: Cc1c2nnn1Cc1c(c(F)cc3[nH]ccc13)Oc1ccc(F)c(c1)-c1nc(nn1C)C(C)(c1cccc(CCC(=O)O)c1)CCS(=O)(=O)C2] |
| 101B | 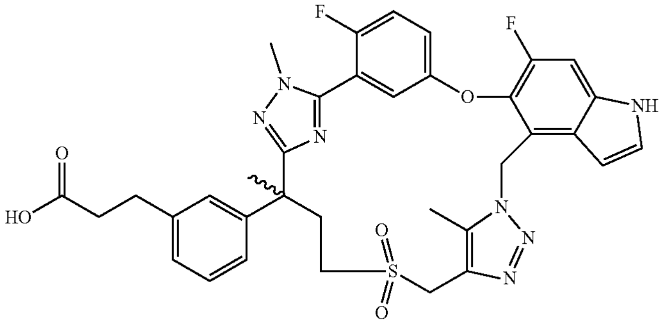 [SMILES: Cc1c2nnn1Cc1c(c(F)cc3[nH]ccc13)Oc1ccc(F)c(c1)-c1nc(nn1C)C(C)(c1cccc(CCC(=O)O)c1)CCS(=O)(=O)C2] |
| 102A | 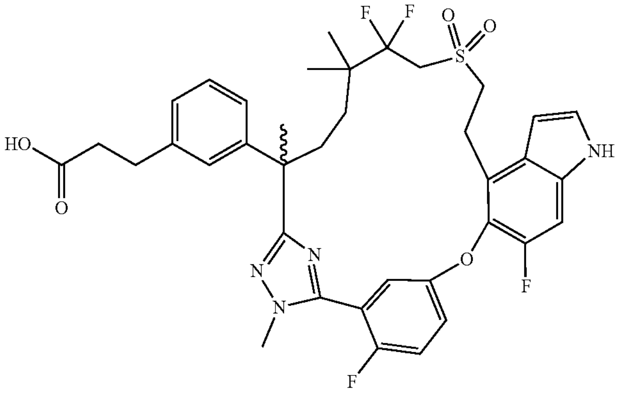 [SMILES: Cn1nc2nc1-c1cc(ccc1F)Oc1c(F)cc3[nH]ccc3c1CCS(=O)(=O)CC(F)(F)C(C)(C)CCC2(C)c1cccc(CCC(=O)O)c1] |
| 102B | 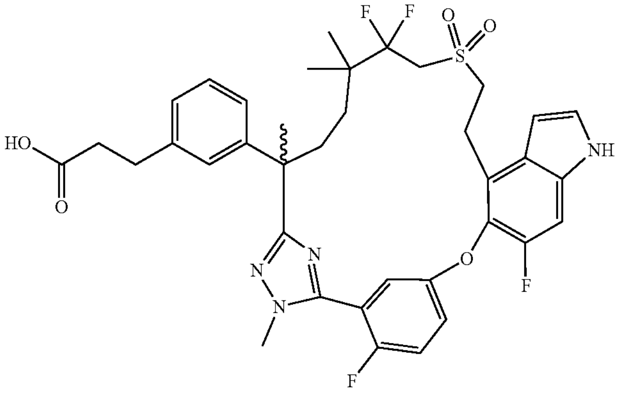 [SMILES: Cn1nc2nc1-c1cc(ccc1F)Oc1c(F)cc3[nH]ccc3c1CCS(=O)(=O)CC(F)(F)C(C)(C)CCC2(C)c1cccc(CCC(=O)O)c1] |

-continued
| Compound No. | Structures |
| --- | --- |
| 103 | 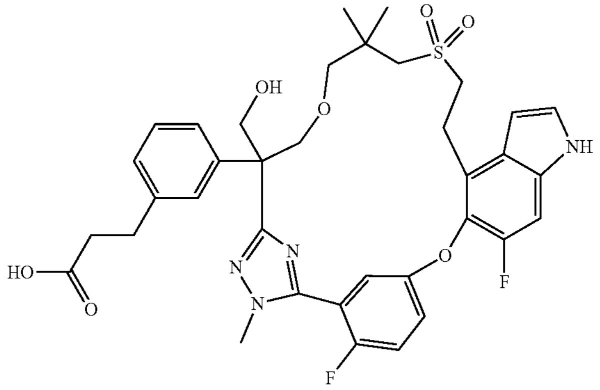 [SMILES: Cn1nc2nc1-c1cc(ccc1F)Oc1c(F)cc3[nH]ccc3c1CCS(=O)(=O)CC(C)(C)COCC2(CO)c1cccc(CCC(=O)O)c1] |
| 104 | 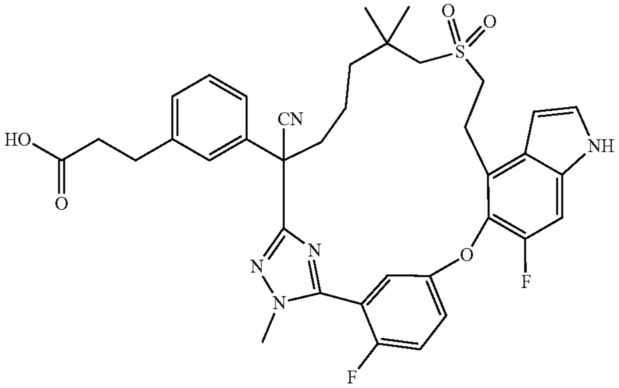 [SMILES: Cn1nc2nc1-c1cc(ccc1F)Oc1c(F)cc3[nH]ccc3c1CCS(=O)(=O)CC(C)(C)CCCC2(C#N)c1cccc(CCC(=O)O)c1] |
| 105 | 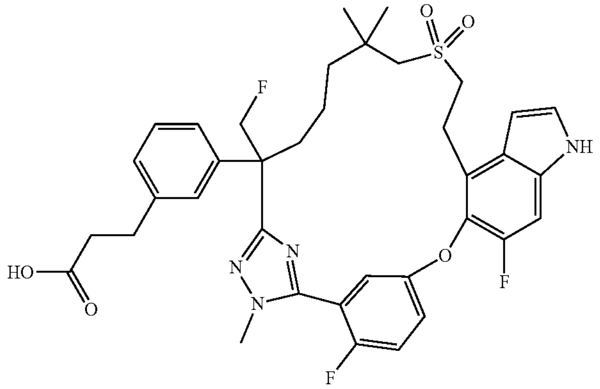 [SMILES: Cn1nc2nc1-c1cc(ccc1F)Oc1c(F)cc3[nH]ccc3c1CCS(=O)(=O)CC(C)(C)CCCC2(CF)c1cccc(CCC(=O)O)c1] |
| 106 | 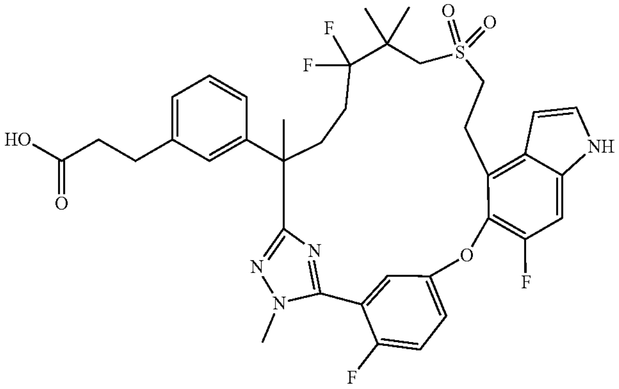 [SMILES: Cn1nc2nc1-c1cc(ccc1F)Oc1c(F)cc3[nH]ccc3c1CCS(=O)(=O)CC(C)(C)C(F)(F)CCC2(C)c1cccc(CCC(=O)O)c1] |

-continued
| Compound No. | Structures |
|---|---|
| 107 | 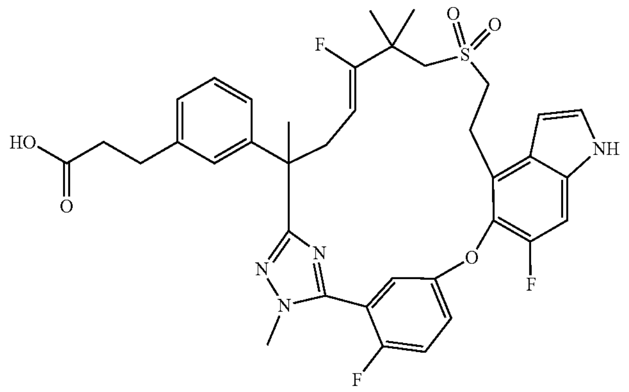 [SMILES: Cn1nc2nc1-c1cc(ccc1F)Oc1c(F)cc3[nH]ccc3c1CCS(=O)(=O)CC(C)(C)/C(F)=C/CC2(C)c1cccc(CCC(=O)O)c1] |
| 108A | 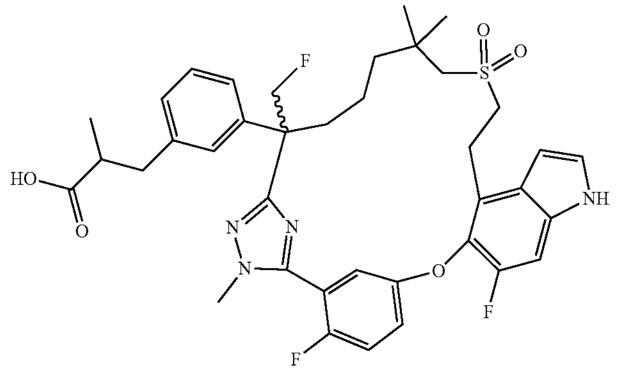 [SMILES: CC(Cc1cccc(C2(CF)CCCC(C)(C)CS(=O)(=O)CCc3c(c(F)cc4[nH]ccc34)Oc3ccc(F)c(c3)-c3nc2nn3C)c1)C(=O)O] |
| 108B | 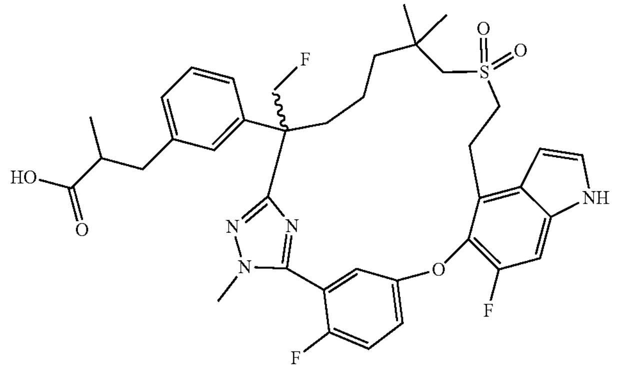 [SMILES: CC(Cc1cccc(C2(CF)CCCC(C)(C)CS(=O)(=O)CCc3c(c(F)cc4[nH]ccc34)Oc3ccc(F)c(c3)-c3nc2nn3C)c1)C(=O)O] |
| 109A | 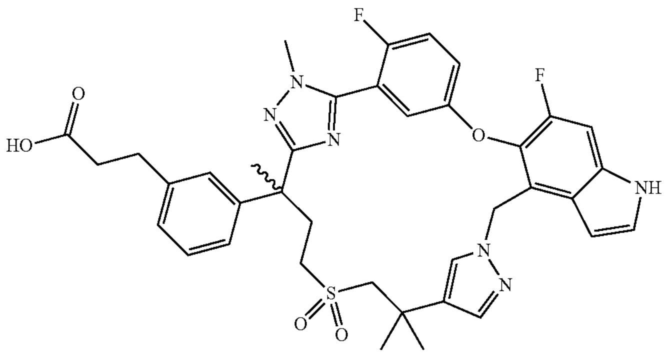 [SMILES: Cn1nc2nc1-c1cc(ccc1F)Oc1c(F)cc3[nH]ccc3c1Cn1cc(cn1)C(C)(C)CS(=O)(=O)CCC2(C)c1cccc(CCC(=O)O)c1] |

-continued
| Compound No. | Structures |
| --- | --- |
| 109B | 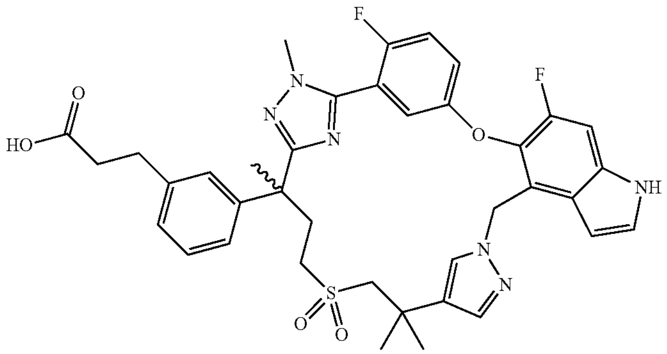 [SMILES: Cn1nc2nc1-c1cc(ccc1F)Oc1c(F)cc3[nH]ccc3c1Cn1cc(cn1)C(C)(C)CS(=O)(=O)CCC2(C)c1cccc(CCC(=O)O)c1] |
| 110 | 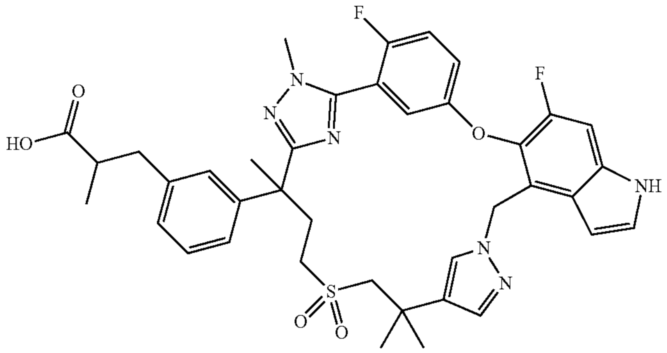 [SMILES: CC(Cc1cccc(C2(C)CCS(=O)(=O)CC(C)(C)c3cnn(c3)Cc3c(c(F)cc4[nH]ccc34)Oc3ccc(F)c(c3)-c3nc2nn3C)c1)C(=O)O] |
| 111 | 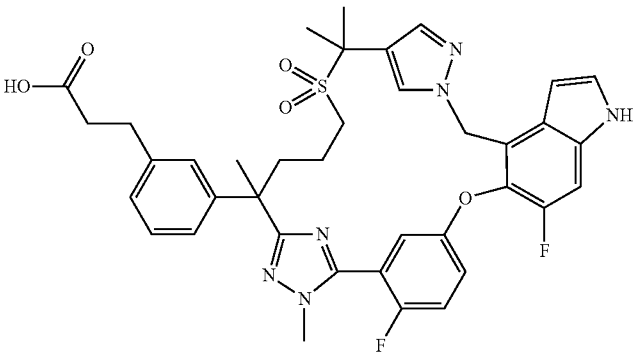 [SMILES: Cn1nc2nc1-c1cc(ccc1F)Oc1c(F)cc3[nH]ccc3c1Cn1cc(cn1)C(C)(C)S(=O)(=O)CCCC2(C)c1cccc(CCC(=O)O)c1] |
| 112 | 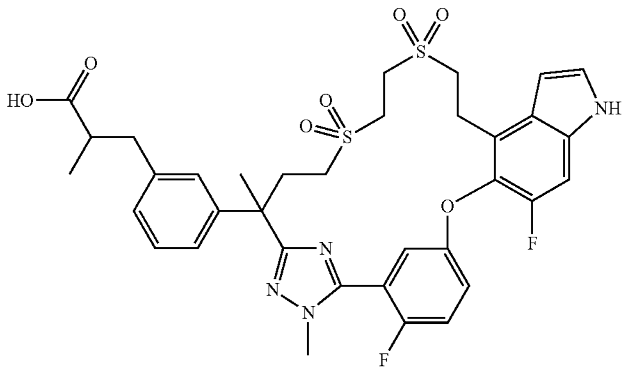 [SMILES: CC(Cc1cccc(C2(C)CCS(=O)(=O)CCS(=O)(=O)CCc3c(c(F)cc4[nH]ccc34)Oc3ccc(F)c(c3)-c3nc2nn3C)c1)C(=O)O] |

-continued
| Compound No. | Structures |
| --- | --- |
| 113A | 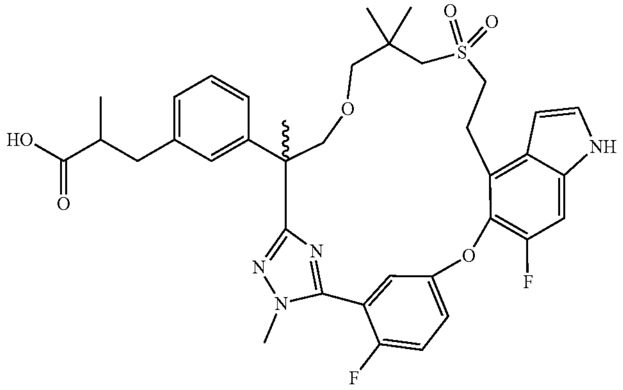 [SMILES: CC(Cc1cccc(C2(C)COCC(C)(C)CS(=O)(=O)CCc3c(c(F)cc4[nH]ccc34)Oc3ccc(F)c(c3)-c3nc2nn3C)c1)C(=O)O] |
| 113B | 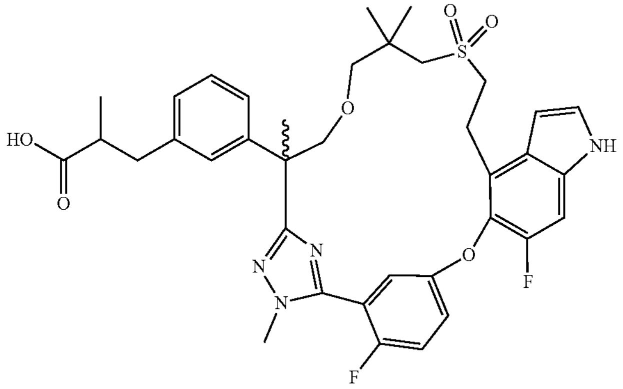 [SMILES: CC(Cc1cccc(C2(C)COCC(C)(C)CS(=O)(=O)CCc3c(c(F)cc4[nH]ccc34)Oc3ccc(F)c(c3)-c3nc2nn3C)c1)C(=O)O] |
| 114 | 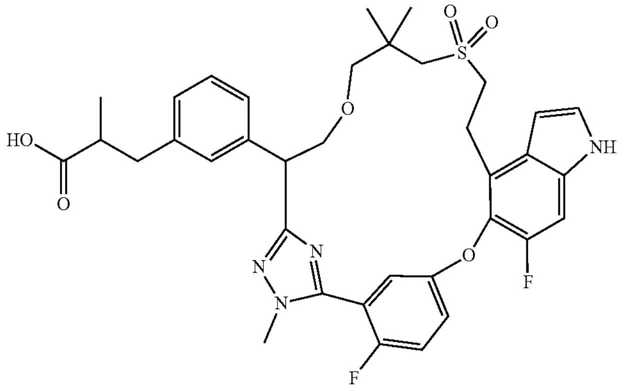 [SMILES: CC(Cc1cccc(C2COCC(C)(C)CS(=O)(=O)CCc3c(c(F)cc4[nH]ccc34)Oc3ccc(F)c(c3)-c3nc2nn3C)c1)C(=O)O] |
| 115 | 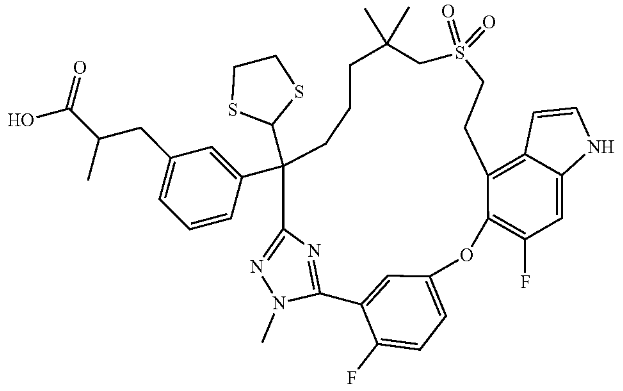 [SMILES: CC(Cc1cccc(C2(C3SCCS3)CCCC(C)(C)CS(=O)(=O)CCc3c(c(F)cc4[nH]ccc34)Oc3ccc(F)c(c3)-c3nc2nn3C)c1)C(=O)O] |

-continued
| Compound No. | Structures |
| --- | --- |
| 116 | 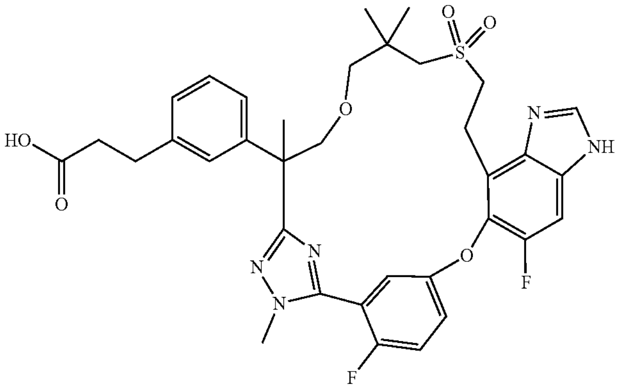 [SMILES: Cn1nc2nc1-c1cc(ccc1F)Oc1c(F)cc3[nH]cnc3c1CCS(=O)(=O)CC(C)(C)COCC2(C)c1cccc(CCC(=O)O)c1] |
| 117 | 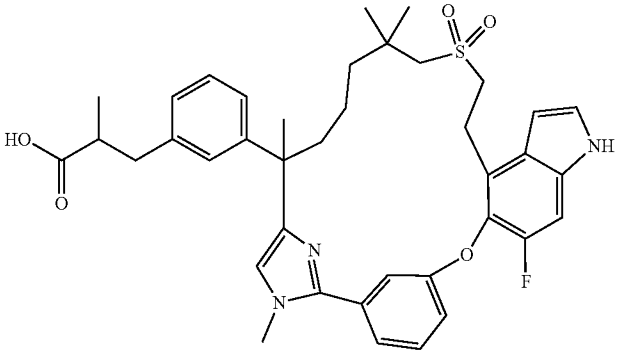 [SMILES: CC(Cc1cccc(C2(C)CCCC(C)(C)CS(=O)(=O)CCc3c(c(F)cc4[nH]ccc34)Oc3cccc(c3)-c3nc2cn3C)c1)C(=O)O] |
| 118A | 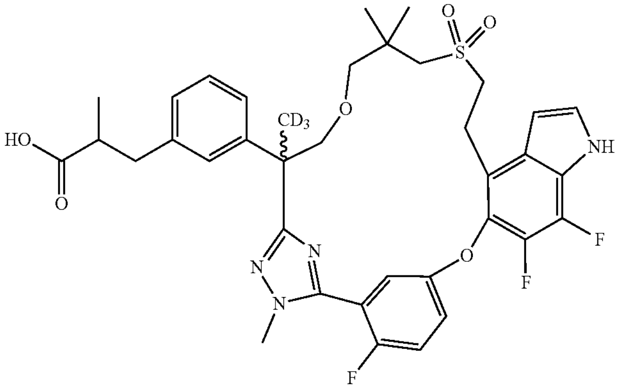 [SMILES: [2H]C([2H])([2H])C1(c2cccc(CC(C)C(=O)O)c2)COCC(C)(C)CS(=O)(=O)CCc2c(c(F)c(F)c3[nH]ccc23)Oc2ccc(F)c(c2)-c2nc1nn2C] |
| 118B | 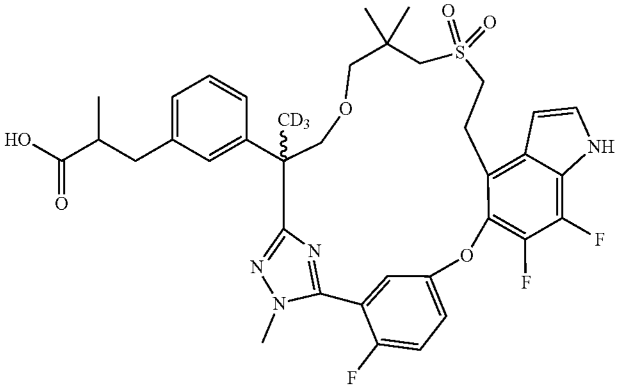 [SMILES: [2H]C([2H])([2H])C1(c2cccc(CC(C)C(=O)O)c2)COCC(C)(C)CS(=O)(=O)CCc2c(c(F)c(F)c3[nH]ccc23)Oc2ccc(F)c(c2)-c2nc1nn2C] |

-continued
| Compound No. | Structures |
|---|---|
| 119A | 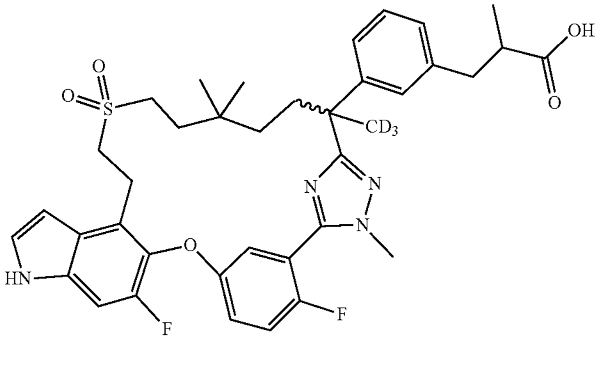 [SMILES: [2H]C([2H])([2H])C1(c2cccc(CC(C)C(=O)O)c2)CCC(C)(C)CCS(=O)(=O)CCc2c(c(F)cc3[nH]ccc23)Oc2ccc(F)c(c2)-c2nc1nn2C] |
| 119B | 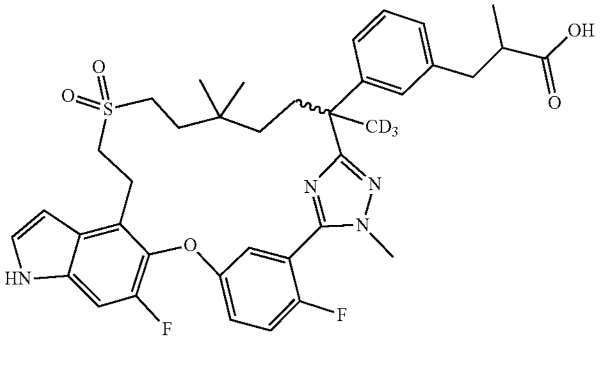 [SMILES: [2H]C([2H])([2H])C1(c2cccc(CC(C)C(=O)O)c2)CCC(C)(C)CCS(=O)(=O)CCc2c(c(F)cc3[nH]ccc23)Oc2ccc(F)c(c2)-c2nc1nn2C] |
| 120A | 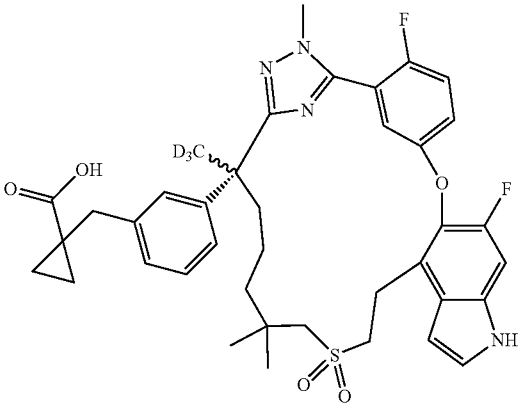 |
| 120B | 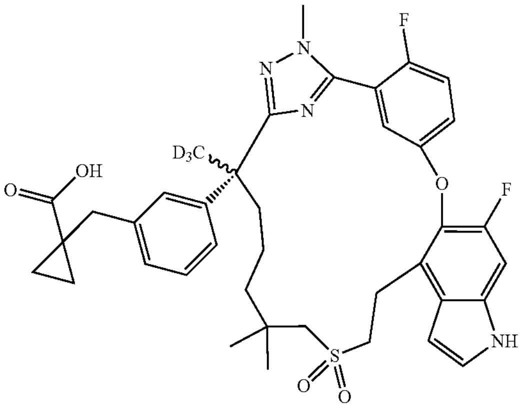 |

-continued
| Compound No. | Structures |
| --- | --- |
| 121A | 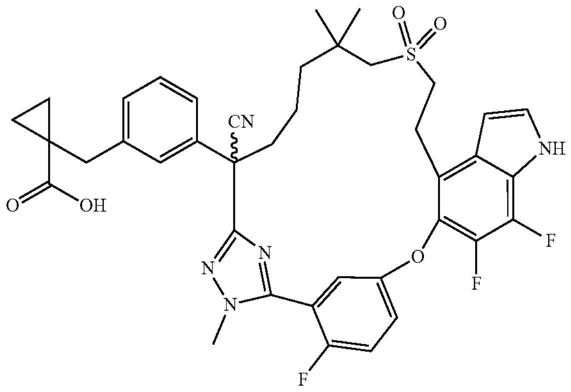 [SMILES: Cn1nc2nc1-c1cc(ccc1F)Oc1c(F)c(F)c3[nH]ccc3c1CCS(=O)(=O)CC(C)(C)CCCC2(C#N)c1cccc(CC2(C(=O)O)CC2)c1] |
| 121B | 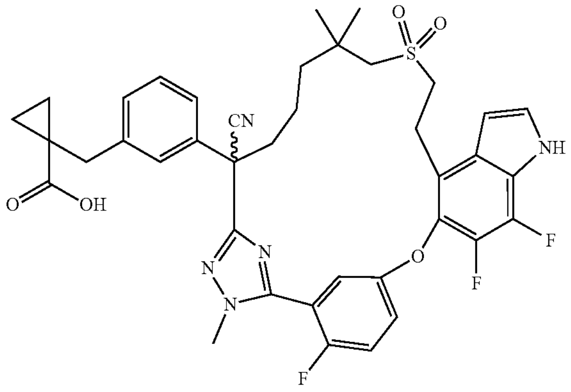 [SMILES: Cn1nc2nc1-c1cc(ccc1F)Oc1c(F)c(F)c3[nH]ccc3c1CCS(=O)(=O)CC(C)(C)CCCC2(C#N)c1cccc(CC2(C(=O)O)CC2)c1] |
| 122A | 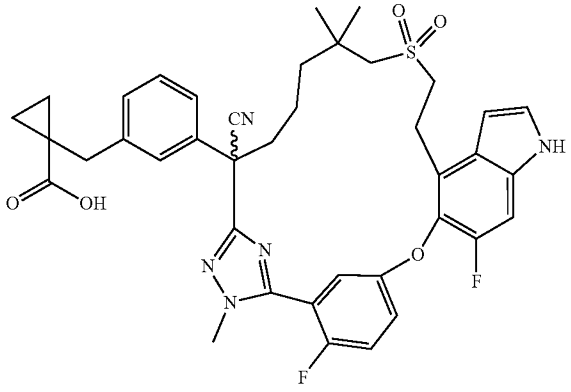 |
| 122B | 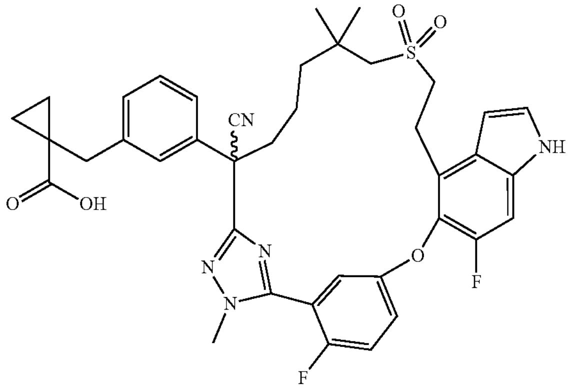 |

-continued
| Compound No. | Structures |
|---|---|
| 123A | 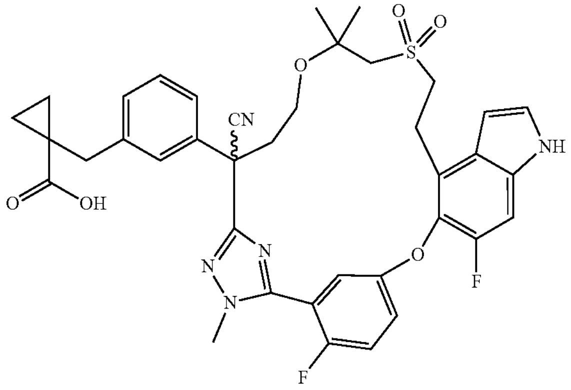 |
| 123B | 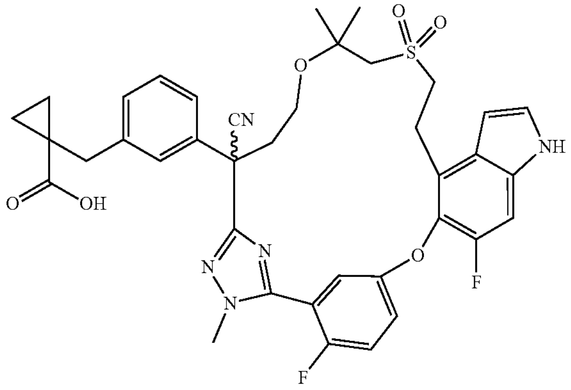 |
| 124A | 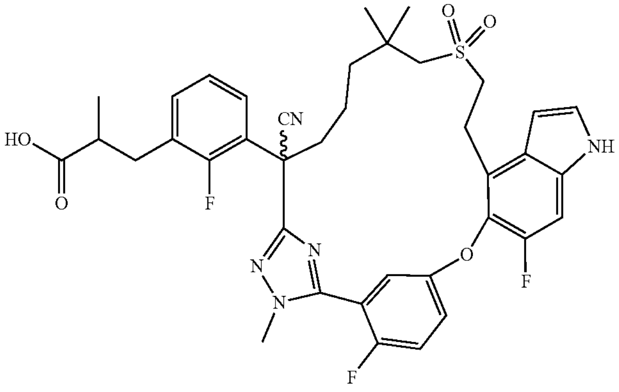 [SMILES: CC(Cc1cccc(C2(C#N)CCCC(C)(C)CS(=O)(=O)CCc3c(c(F)cc4[nH]ccc34)Oc3ccc(F)c(c3)-c3nc2nn3C)c1F)C(=O)O] |
| 124B | 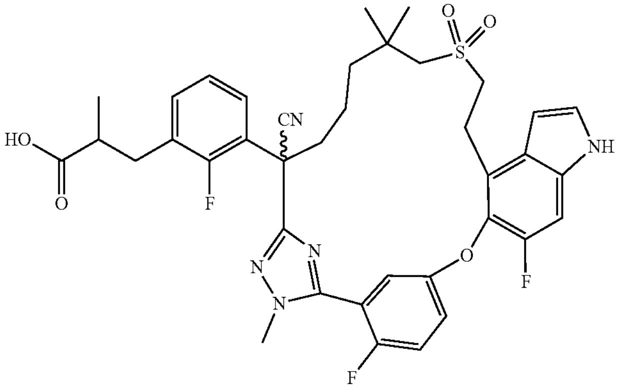 [SMILES: CC(Cc1cccc(C2(C#N)CCCC(C)(C)CS(=O)(=O)CCc3c(c(F)cc4[nH]ccc34)Oc3ccc(F)c(c3)-c3nc2nn3C)c1F)C(=O)O] |

-continued
| Compound No. | Structures |
|---|---|
| 125A | 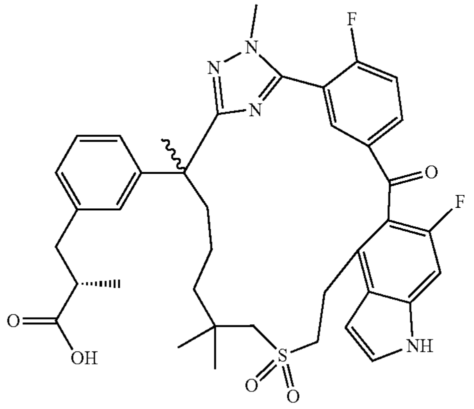 [SMILES: C[C@@H](Cc1cccc(C2(C)CCCC(C)(C)CS(=O)(=O)CCc3c(c(F)cc4[nH]ccc34)C(=O)c3ccc(F)c(c3)-c3nc2nn3C)c1)C(=O)O] |
| 125B | 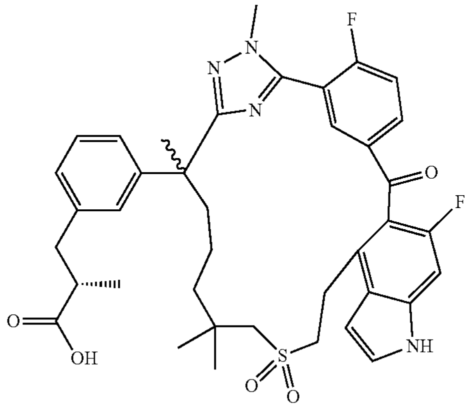 [SMILES: C[C@@H](Cc1cccc(C2(C)CCCC(C)(C)CS(=O)(=O)CCc3c(c(F)cc4[nH]ccc34)C(=O)c3ccc(F)c(c3)-c3nc2nn3C)c1)C(=O)O] |
| 126A | 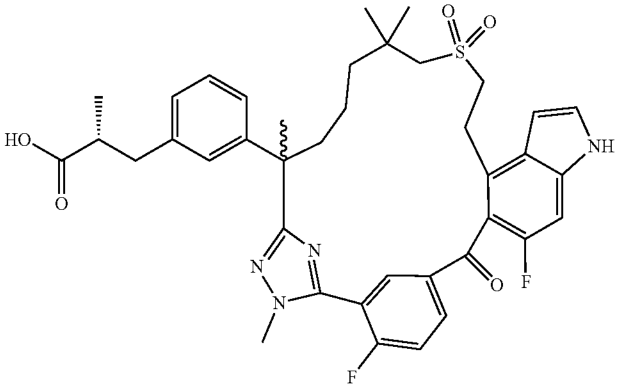 [SMILES: C[C@H](Cc1cccc(C2(C)CCCC(C)(C)CS(=O)(=O)CCc3c(c(F)cc4[nH]ccc34)C(=O)c3ccc(F)c(c3)-c3nc2nn3C)c1)C(=O)O] |
| 126B | 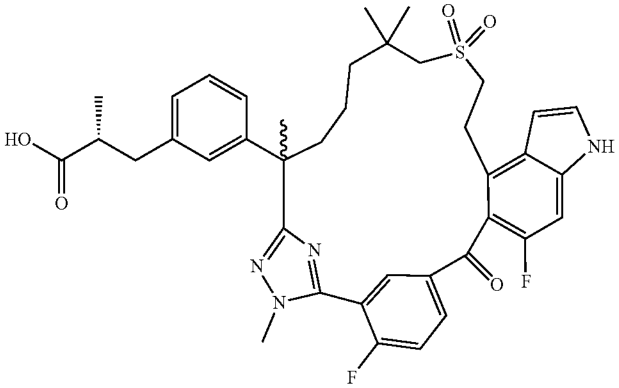 [SMILES: C[C@H](Cc1cccc(C2(C)CCCC(C)(C)CS(=O)(=O)CCc3c(c(F)cc4[nH]ccc34)C(=O)c3ccc(F)c(c3)-c3nc2nn3C)c1)C(=O)O] |

-continued
| Compound No. | Structures |
|---|---|
| 127A | 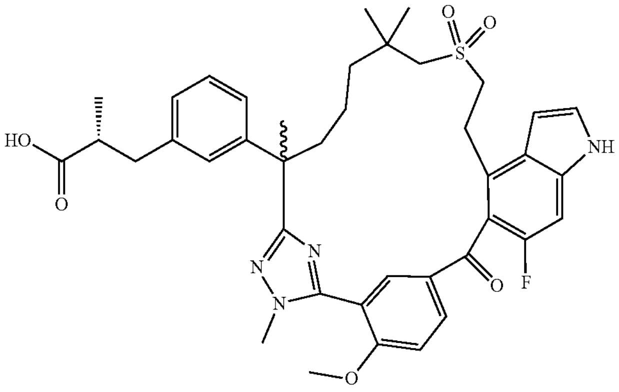 [SMILES: COc1ccc2cc1-c1nc(nn1C)C(C)(c1cccc(C[C@@H](C)C(=O)O)c1)CCCC(C)(C)CS(=O)(=O)CCc1c(c(F)cc3[nH]ccc13)C2=O] |
| 127B | 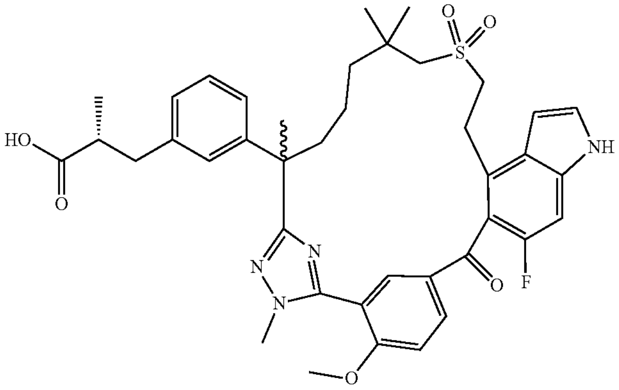 [SMILES: COc1ccc2cc1-c1nc(nn1C)C(C)(c1cccc(C[C@@H](C)C(=O)O)c1)CCCC(C)(C)CS(=O)(=O)CCc1c(c(F)cc3[nH]ccc13)C2=O] |
| 128 | 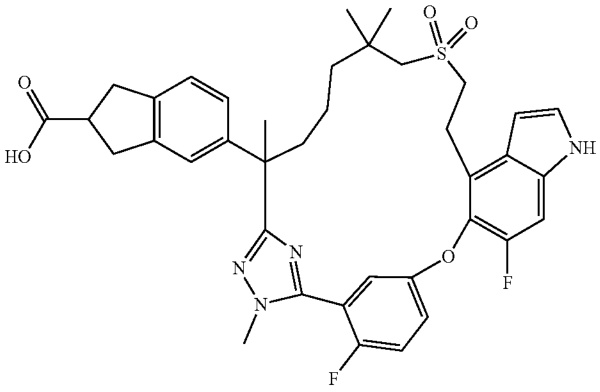 [SMILES: Cn1nc2nc1-c1cc(ccc1F)Oc1c(F)cc3[nH]ccc3c1CCS(=O)(=O)CC(C)(C)CCCC2(C)c1ccc2c(c1)CC(C(=O)O)C2] |
| 129A | 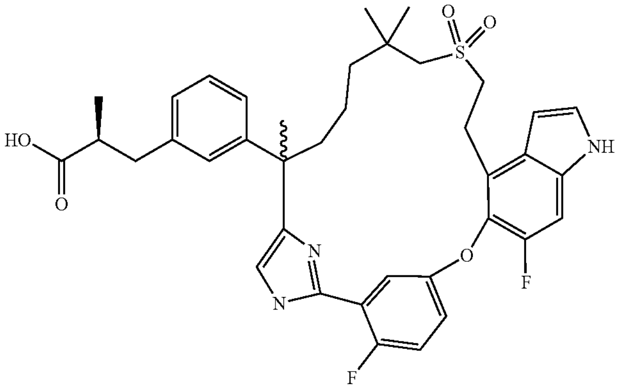 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2c[nH]3)c1)C(=O)O] |

-continued
| Compound No. | Structures |
| --- | --- |
| 129B | 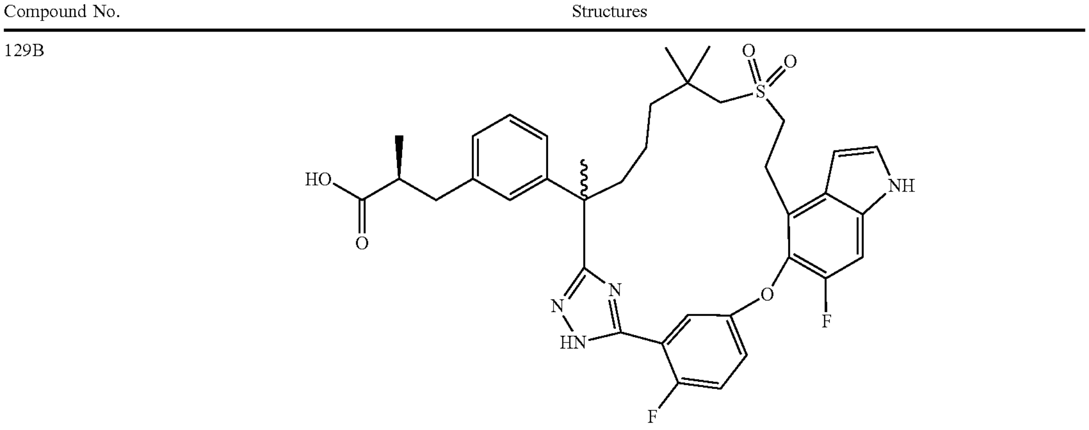 |
| 130A | 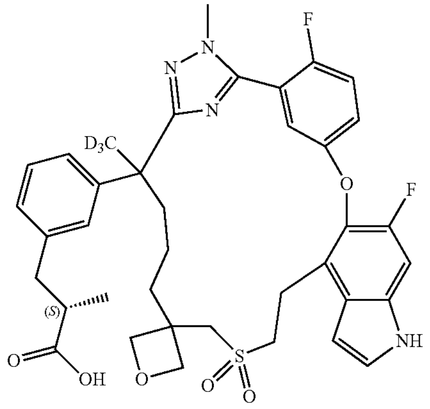 |
| 130B | 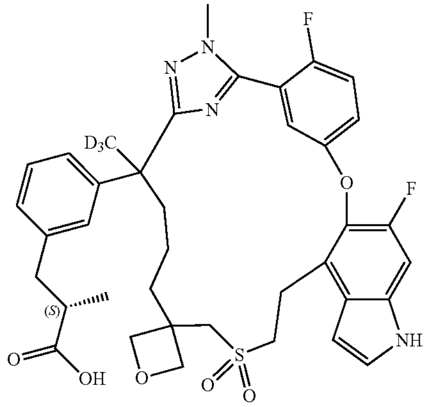 |
| 131 | 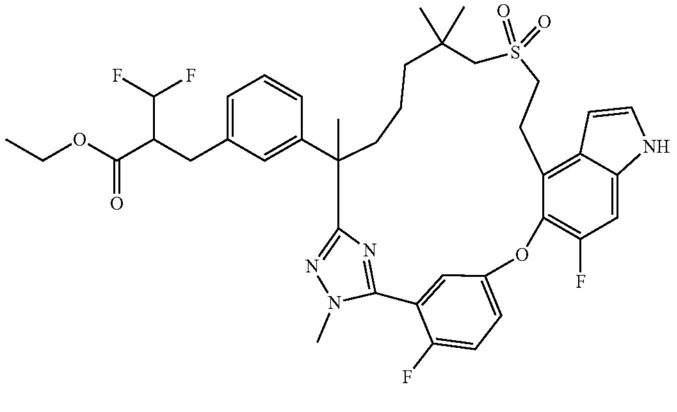 [SMILES: CCOC(=O)C(Cc1cccc(C2(C)CCCC(C)(C)CS(=O)(=O)CCc3c(c(F)cc4[nH]ccc34)Oc3ccc(F)c(c3)-c3nc2nn3C)c1)C(F)F] |

-continued
| Compound No. | Structures |
| --- | --- |
| 132A | 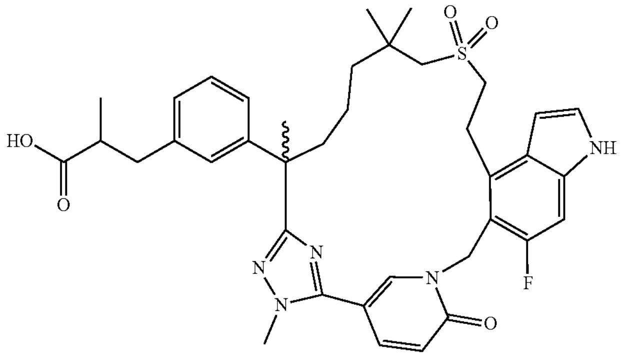 [SMILES: CC(Cc1cccc(C2(C)CCCC(C)(C)CS(=O)(=O)CCc3c(c(F)cc4[nH]ccc34)Cn3cc(ccc3=O)-c3nc2nn3C)c1)C(=O)O] |
| 132B | 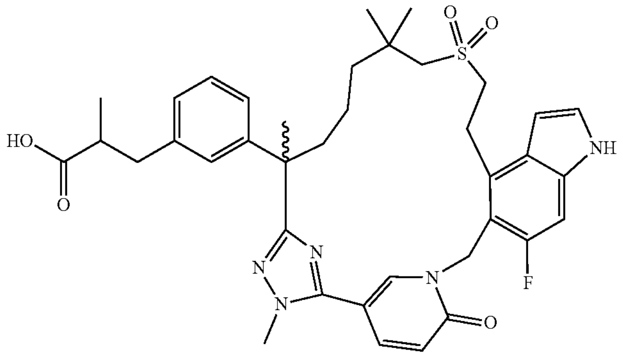 [SMILES: CC(Cc1cccc(C2(C)CCCC(C)(C)CS(=O)(=O)CCc3c(c(F)cc4[nH]ccc34)Cn3cc(ccc3=O)-c3nc2nn3C)c1)C(=O)O] |
| 133A | 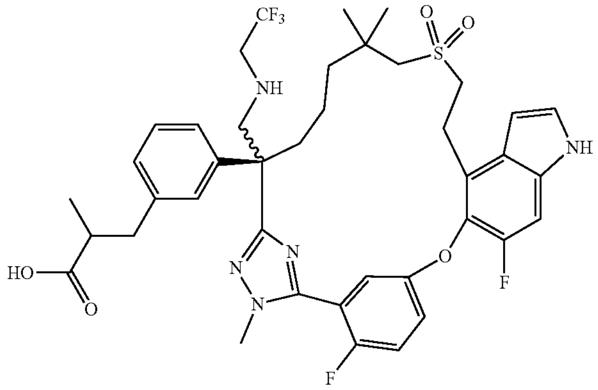 |
| 133B | 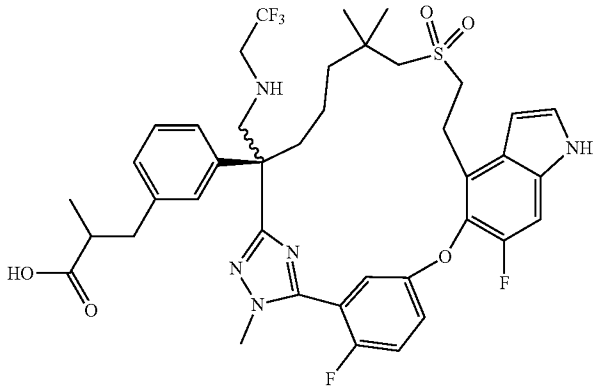 |

-continued
| Compound No. | Structures |
| --- | --- |
| 134A | 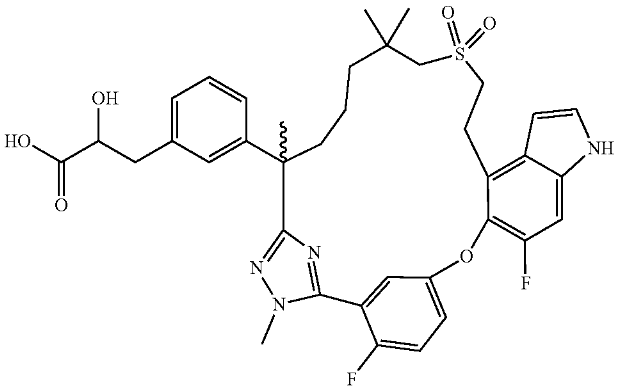 [SMILES: Cn1nc2nc1-c1cc(ccc1F)Oc1c(F)cc3[nH]ccc3c1CCS(=O)(=O)CC(C)(C)CCCC2(C)c1cccc(CC(O)C(=O)O)c1] |
| 134B | 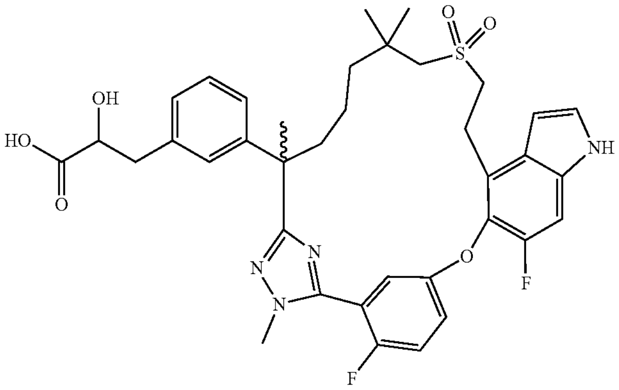 [SMILES: Cn1nc2nc1-c1cc(ccc1F)Oc1c(F)cc3[nH]ccc3c1CCS(=O)(=O)CC(C)(C)CCCC2(C)c1cccc(CC(O)C(=O)O)c1] |
| 135A | 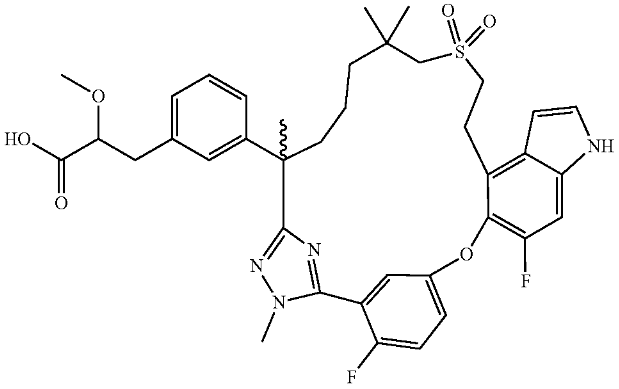 [SMILES: COC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O] |
| 135B | 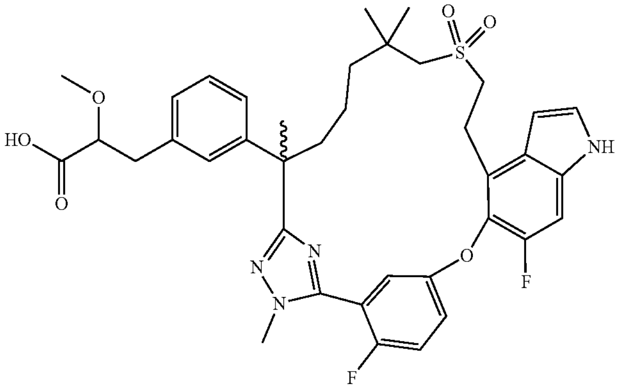 [SMILES: COC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O] |

-continued
| Compound No. | Structures |
| --- | --- |
| 136A | 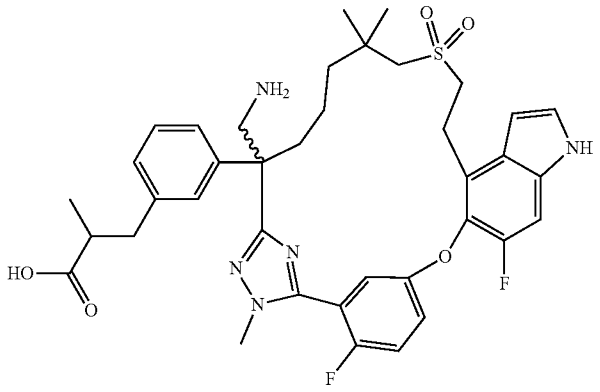 [SMILES: CC(Cc1cccc(C2(CN)CCCC(C)(C)CS(=O)(=O)CCc3c(c(F)cc4[nH]ccc34)Oc3ccc(F)c(c3)-c3nc2nn3C)c1)C(=O)O] |
| 136B | 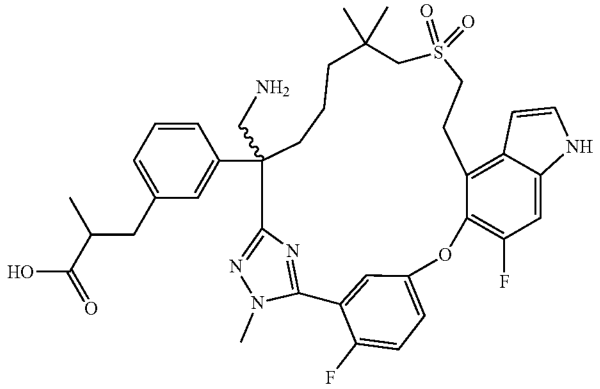 [SMILES: CC(Cc1cccc(C2(CN)CCCC(C)(C)CS(=O)(=O)CCc3c(c(F)cc4[nH]ccc34)Oc3ccc(F)c(c3)-c3nc2nn3C)c1)C(=O)O] |
| 137A | 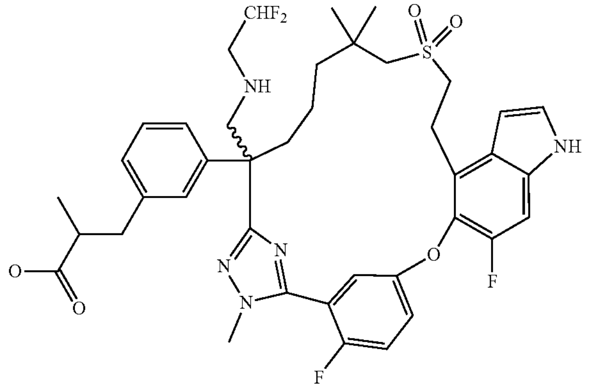 [SMILES: CC(Cc1cccc(C2(CNCC(F)F)CCCC(C)(C)CS(=O)(=O)CCc3c(c(F)cc4[nH]ccc34)Oc3ccc(F)c(c3)-c3nc2nn3C)c1)C(=O)O] |
| 137B | 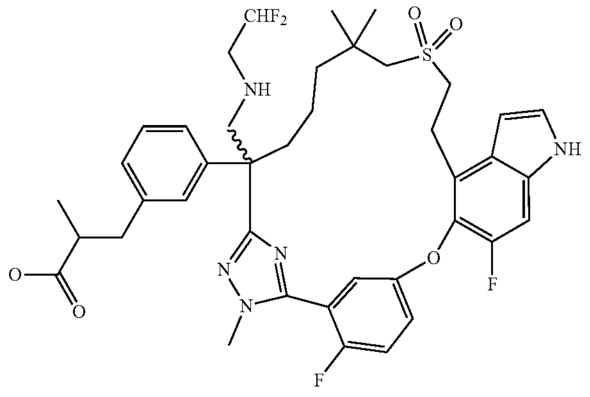 [SMILES: CC(Cc1cccc(C2(CNCC(F)F)CCCC(C)(C)CS(=O)(=O)CCc3c(c(F)cc4[nH]ccc34)Oc3ccc(F)c(c3)-c3nc2nn3C)c1)C(=O)O] |

-continued
| Compound No. | Structures |
|---|---|
| 138 | 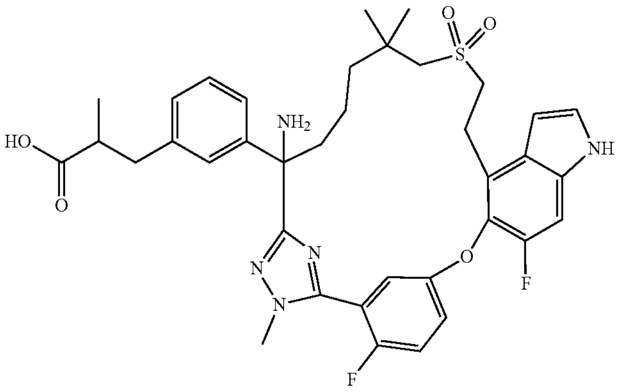 [SMILES: CC(Cc1cccc(C2(N)CCCC(C)(C)CS(=O)(=O)CCc3c(c(F)cc4[nH]ccc34)Oc3ccc(F)c(c3)-c3nc2nn3C)c1)C(=O)O] |
| 139 | 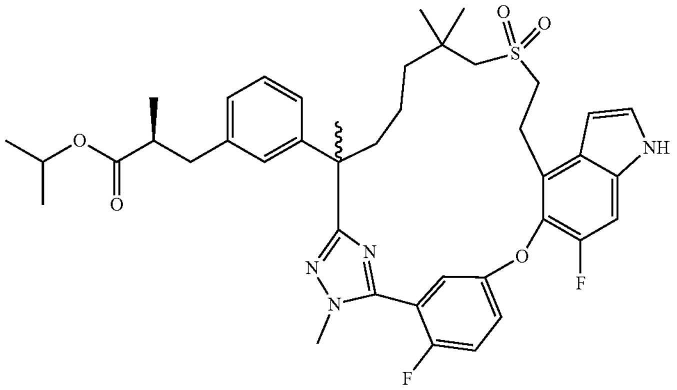 [SMILES: CC(C)OC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1] |
| 140 | 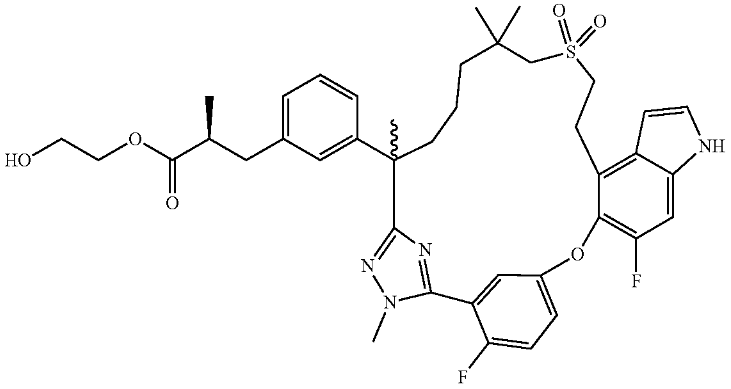 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCCO] |
| 141 | 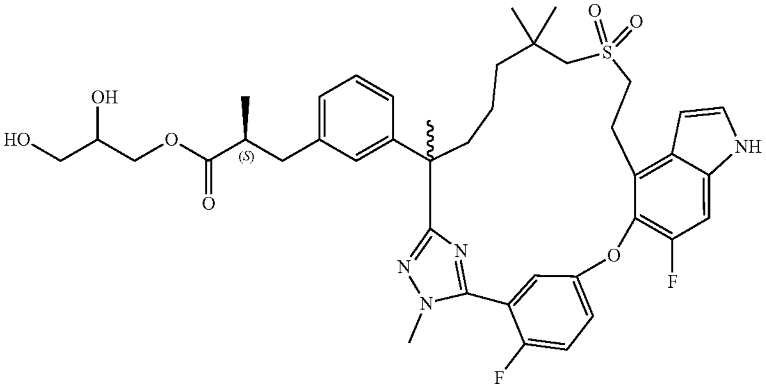 |

-continued
| Compound No. | Structures |
|---|---|
| 142 | 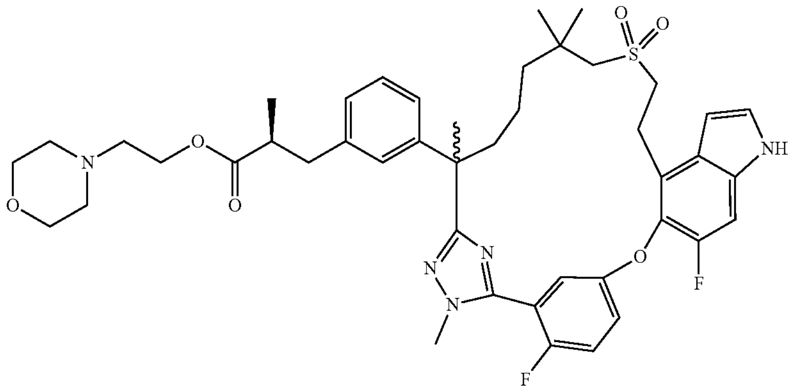 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCCN1CCOCC1] |
| 143 | 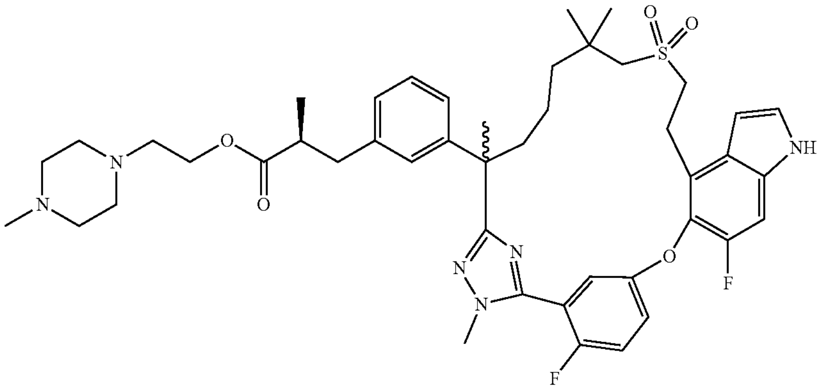 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCCN1CCN(C)CC1] |
| 144 | 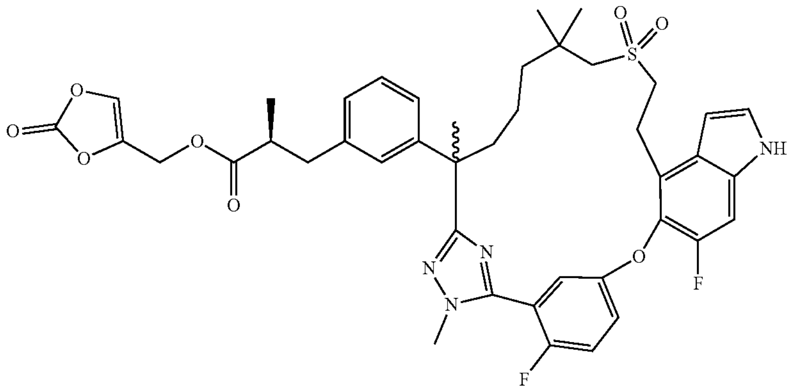 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCc1coc(=O)o1] |
| 145 | 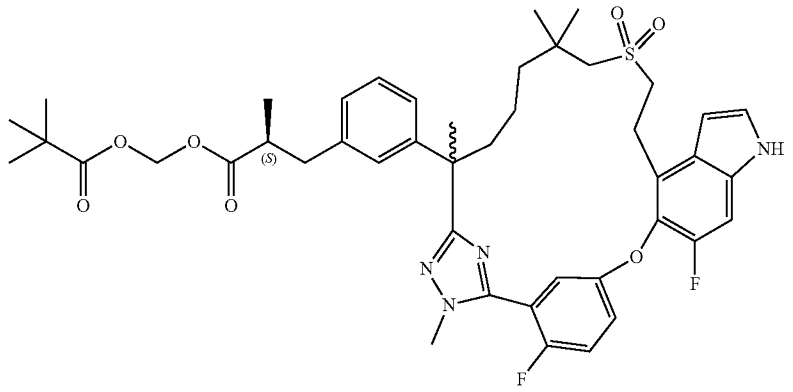 |

-continued
| Compound No. | Structures |
| --- | --- |
| 146 | 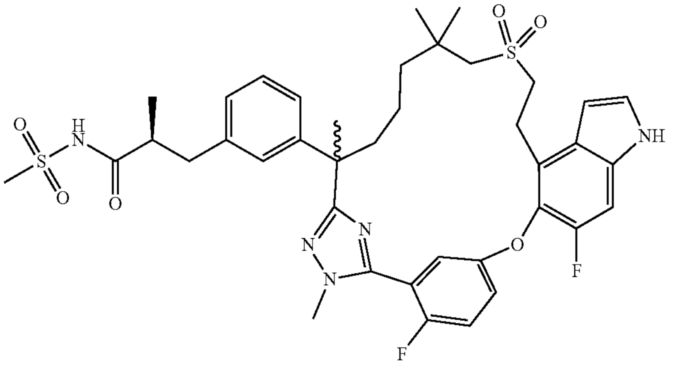 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NS(C)(=O)=O] |
| 147 | 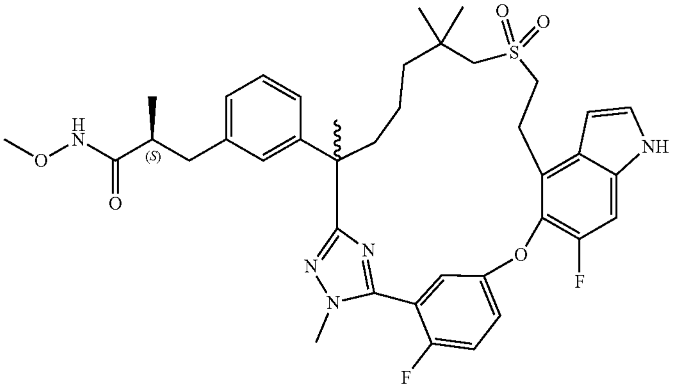 |
| 148 | 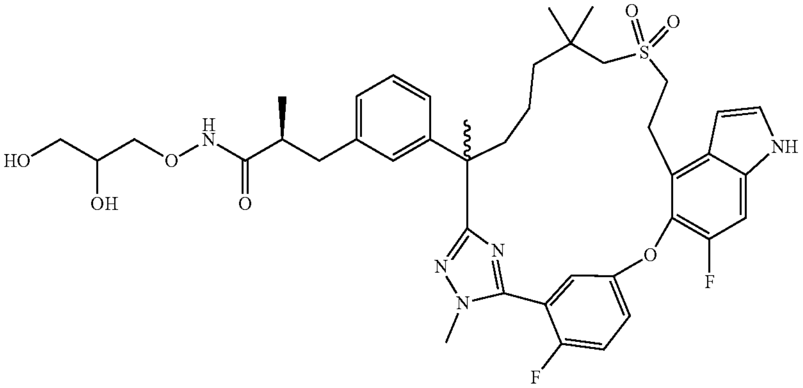 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NOCC(O)CO] |
| 149 | 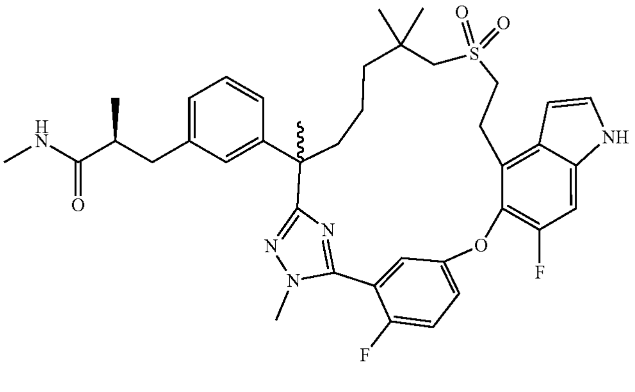 [SMILES: CNC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1] |

-continued
| Compound No. | Structures |
| --- | --- |
| 150 | 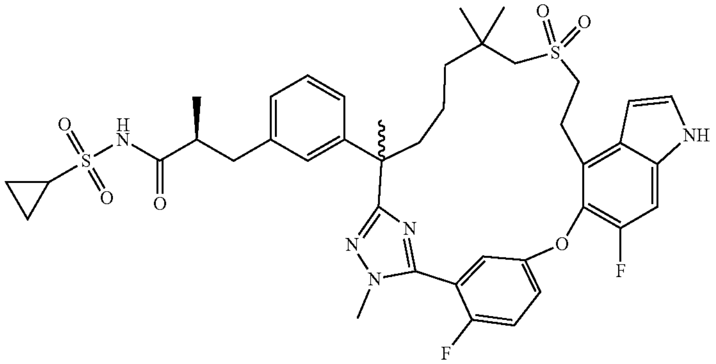 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NS(=O)(=O)C1CC1] |
| 151 | 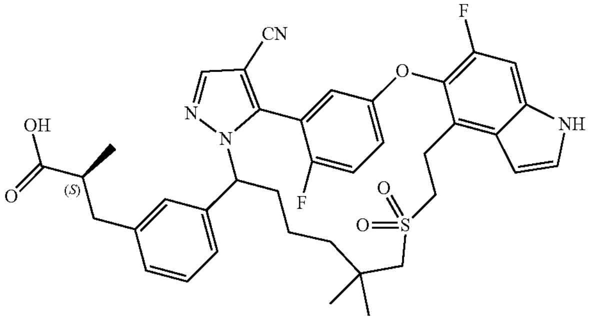 |
| 152 | 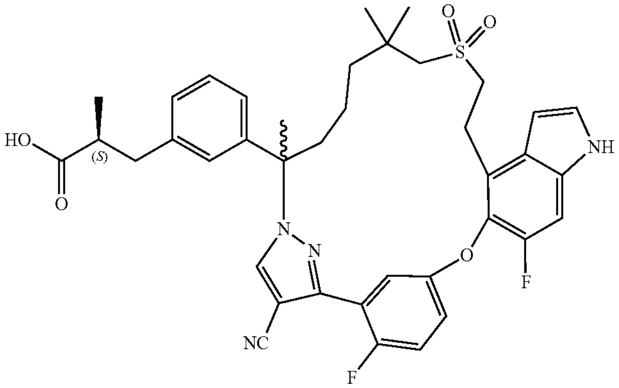 |
| 153A | 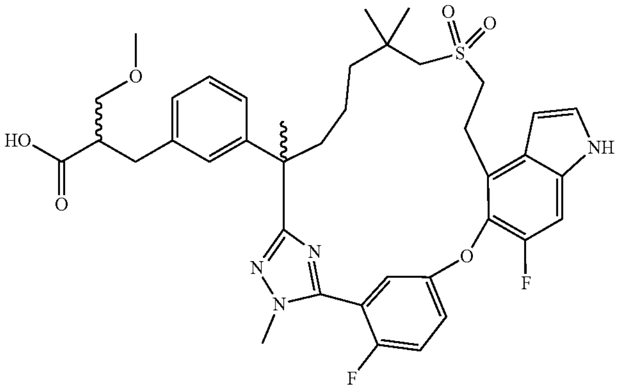 [SMILES: COCC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O] |

-continued
| Compound No. | Structures |
|---|---|
| 153B | 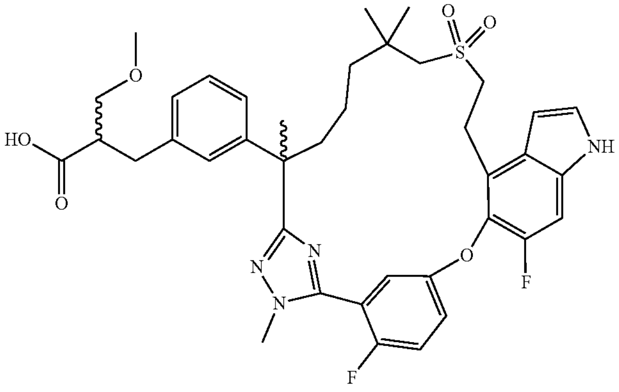 [SMILES: COCC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O] |
| 153C | 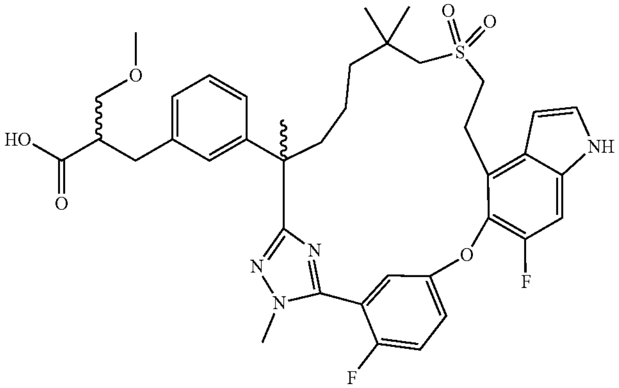 [SMILES: COCC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O] |
| 154 | 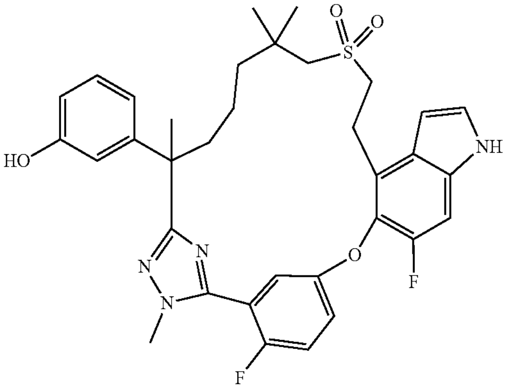 [SMILES: Cn1nc2nc1-c1cc(ccc1F)Oc1c(F)cc3[nH]ccc3c1CCS(=O)(=O)CC(C)(C)CCCC2(C)c1cccc(O)c1] |
| 155 | 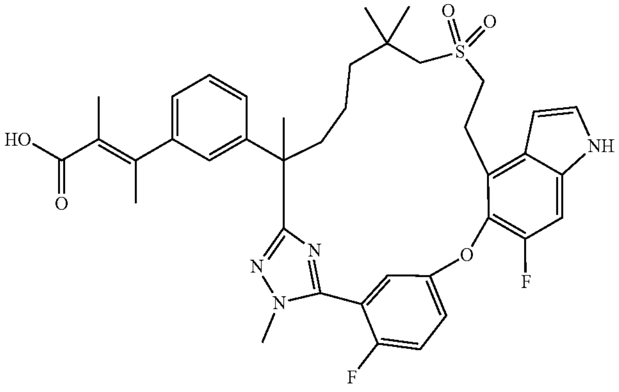 [SMILES: C/C(C(=O)O)=C(/C)c1cccc(C2(C)CCCC(C)(C)CS(=O)(=O)CCc3c(c(F)cc4[nH]ccc34)Oc3ccc(F)c(c3)-c3nc2nn3C)c1] |

-continued
| Compound No. | Structures |
| --- | --- |
| 156 | 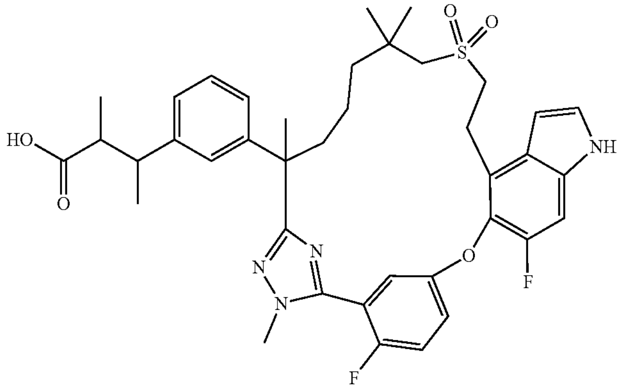 [SMILES: CC(C(=O)O)C(C)c1cccc(C2(C)CCCC(C)(C)CS(=O)(=O)CCc3c(c(F)cc4[nH]ccc34)Oc3ccc(F)c(c3)-c3nc2nn3C)c1] |
| 157A | 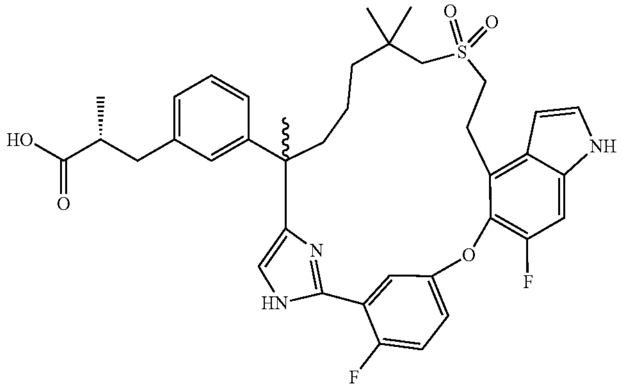 [SMILES: C[C@H](Cc1cccc(C2(C)CCCC(C)(C)CS(=O)(=O)CCc3c(c(F)cc4[nH]ccc34)Oc3ccc(F)c(c3)-c3nc2c[nH]3)c1)C(=O)O] |
| 157B | 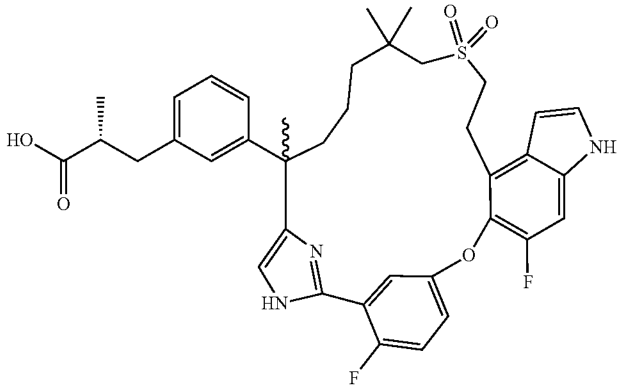 [SMILES: C[C@H](Cc1cccc(C2(C)CCCC(C)(C)CS(=O)(=O)CCc3c(c(F)cc4[nH]ccc34)Oc3ccc(F)c(c3)-c3nc2c[nH]3)c1)C(=O)O] |
| 158 | 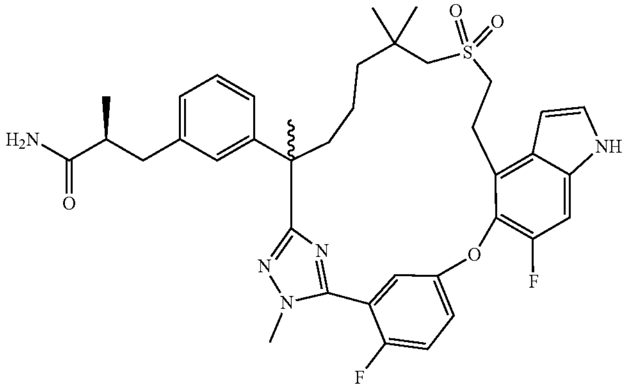 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(N)=O] |

-continued
| Compound No. | Structures |
|---|---|
| 159 | 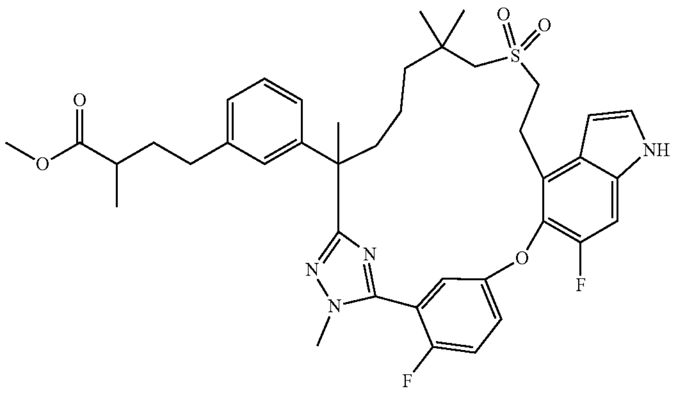 [SMILES: COC(=O)C(C)CCc1cccc(C2(C)CCCC(C)(C)CS(=O)(=O)CCc3c(c(F)cc4[nH]ccc34)Oc3ccc(F)c(c3)-c3nc2nn3C)c1] |
| 160 | 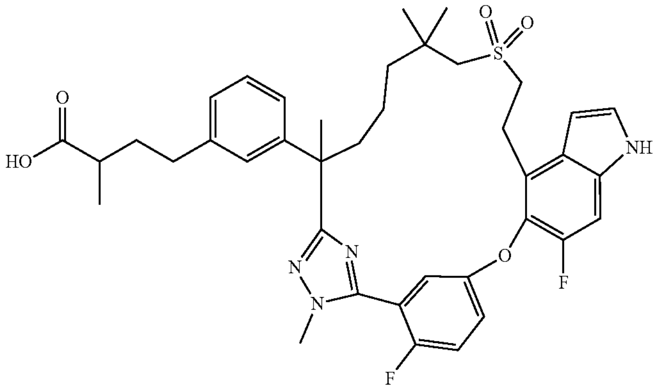 [SMILES: CC(CCc1cccc(C2(C)CCCC(C)(C)CS(=O)(=O)CCc3c(c(F)cc4[nH]ccc34)Oc3ccc(F)c(c3)-c3nc2nn3C)c1)C(=O)O] |
| 161 | 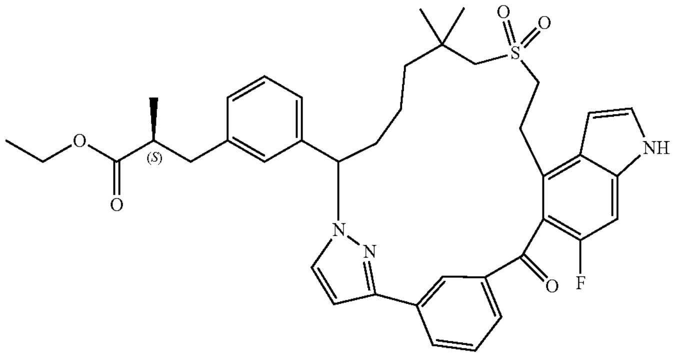 |
| 162 | 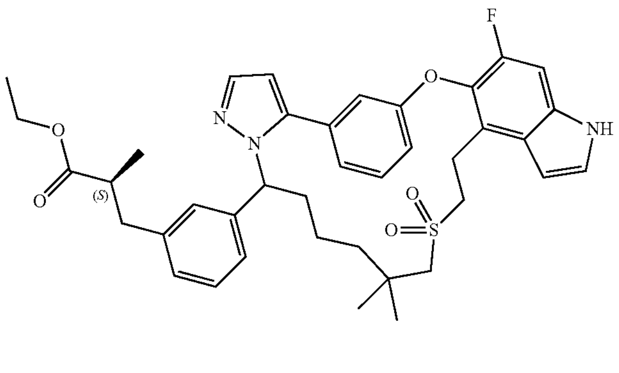 |

-continued
| Compound No. | Structures |
| --- | --- |
| 163 | 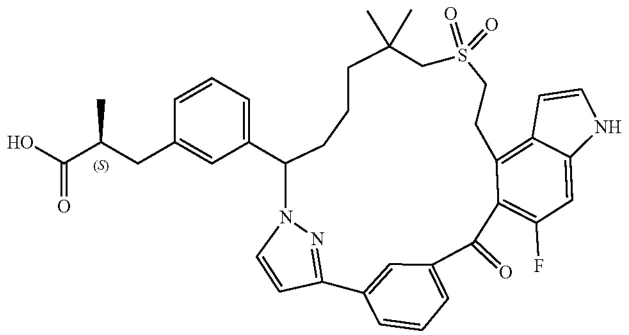 |
| 164 | 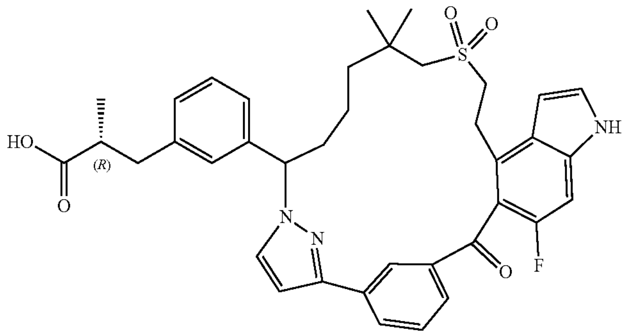 |
| 165 | 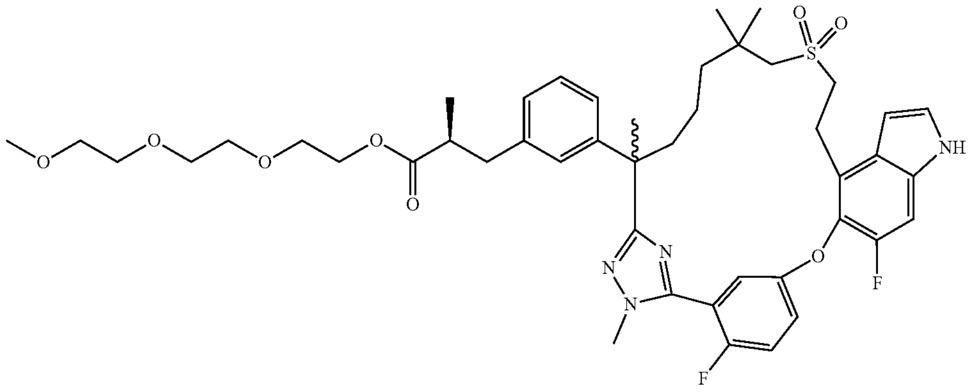 [SMILES: COCCOCCOCCOC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1] |
| 166A | 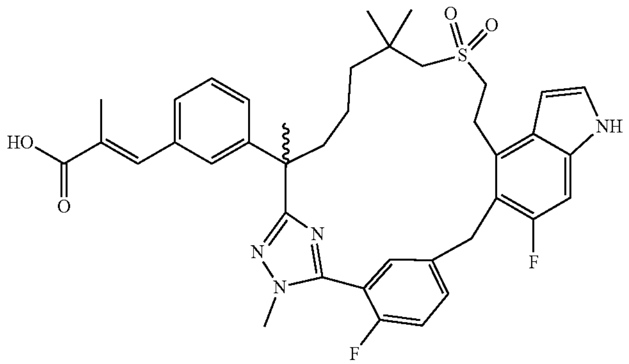 [SMILES: C/C(=C\c1cccc(C2(C)CCCC(C)(C)CS(=O)(=O)CCc3c(c(F)cc4[nH]ccc34)Cc3ccc(F)c(c3)-c3nc2nn3C)c1)C(=O)O] |

-continued
| Compound No. | Structures |
| --- | --- |
| 166B | 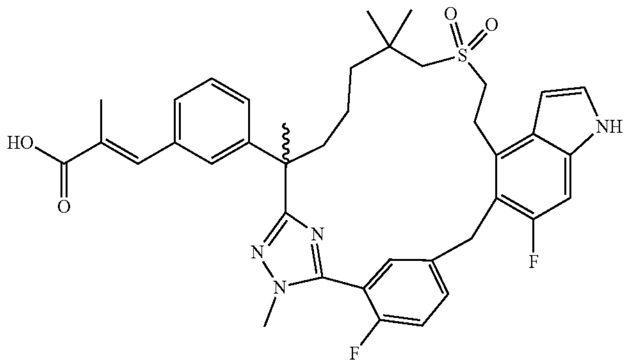 [SMILES: C/C(=C\c1cccc(C2(C)CCCC(C)(C)CS(=O)(=O)CCc3c(c(F)cc4[nH]ccc34)Cc3ccc(F)c(c3)-c3nc2nn3C)c1)C(=O)O] |
| 167 | 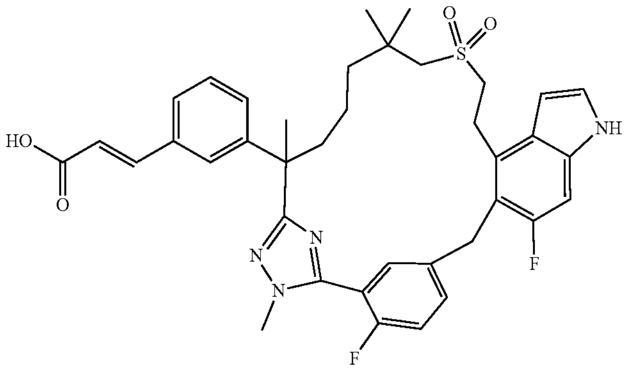 [SMILES: Cn1nc2nc1-c1cc(ccc1F)Cc1c(F)cc3[nH]ccc3c1CCS(=O)(=O)CC(C)(C)CCCC2(C)c1cccc(/C=C/C(=O)O)c1] |
| 168 | 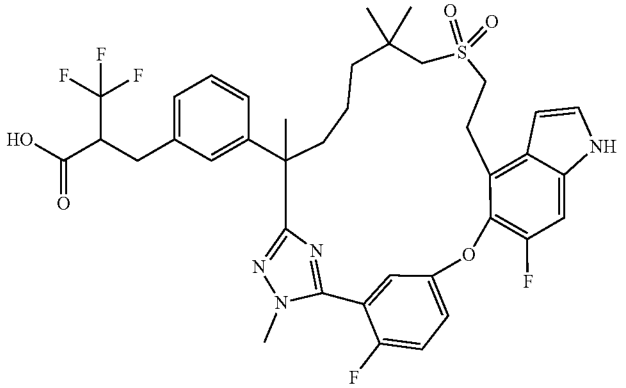 [SMILES: Cn1nc2nc1-c1cc(ccc1F)Oc1c(F)cc3[nH]ccc3c1CCS(=O)(=O)CC(C)(C)CCCC2(C)c1cccc(CC(C(=O)O)C(F)(F)F)c1] |
| 169A | 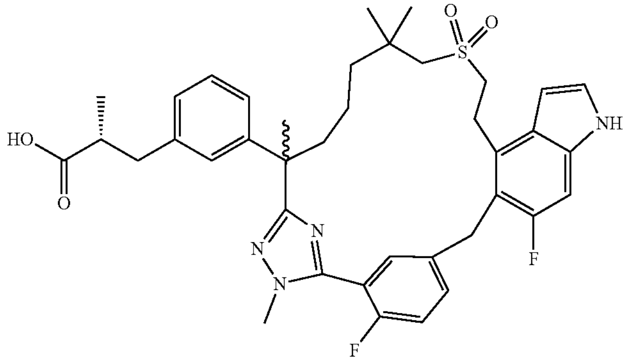 [SMILES: C[C@H](Cc1cccc(C2(C)CCCC(C)(C)CS(=O)(=O)CCc3c(c(F)cc4[nH]ccc34)Cc3ccc(F)c(c3)-c3nc2nn3C)c1)C(=O)O] |

-continued
| Compound No. | Structures |
|---|---|
| 169B | 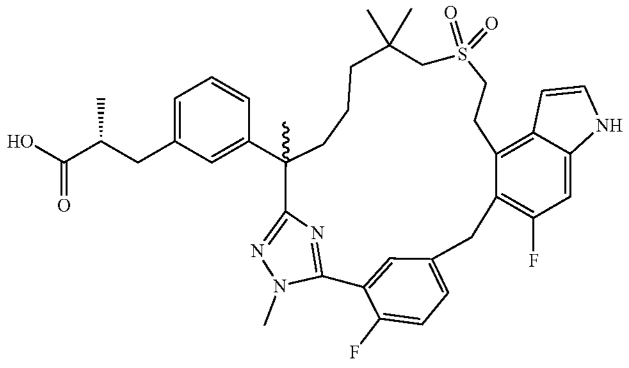 [SMILES: C[C@H](Cc1cccc(C2(C)CCCC(C)(C)CS(=O)(=O)CCc3c(c(F)cc4[nH]ccc34)Cc3ccc(F)c(c3)-c3nc2nn3C)c1)C(=O)O] |
| 170 | 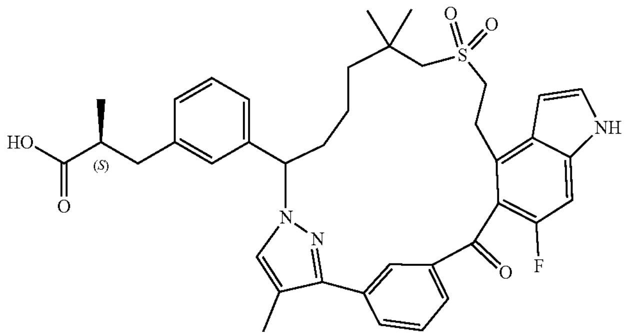 |
| 171A | 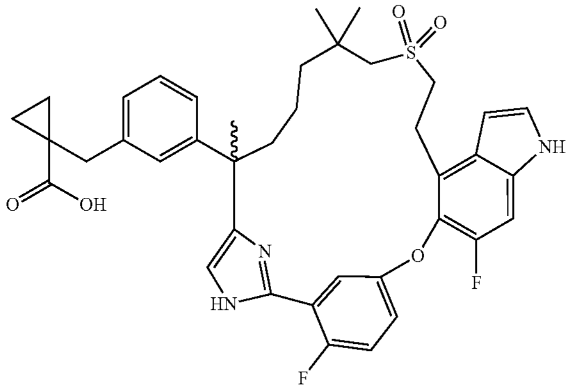 [SMILES: CC1(C)CCCC(C)(c2cccc(CC3(C(=O)O)CC3)c2)c2c[nH]c(n2)-c2cc(ccc2F)Oc2c(F)cc3[nH]ccc3c2CCS(=O)(=O)C1] |
| 171B | 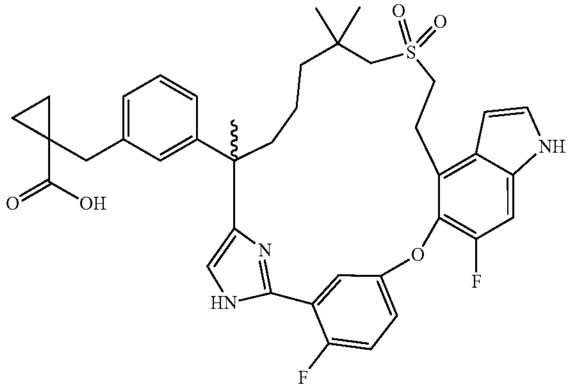 [SMILES: CC1(C)CCCC(C)(c2cccc(CC3(C(=O)O)CC3)c2)c2c[nH]c(n2)-c2cc(ccc2F)Oc2c(F)cc3[nH]ccc3c2CCS(=O)(=O)C1] |

-continued
| Compound No. | Structures |
| --- | --- |
| 172 | 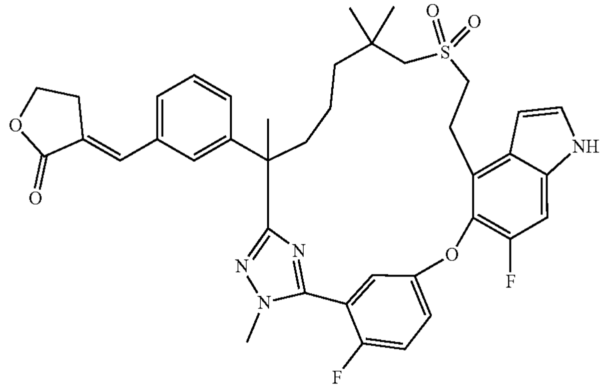 [SMILES: Cn1nc2nc1-c1cc(ccc1F)Oc1c(F)cc3[nH]ccc3c1CCS(=O)(=O)CC(C)(C)CCCC2(C)c1cccc(/C=C2\CCOC2=O)c1] |
| 173 | 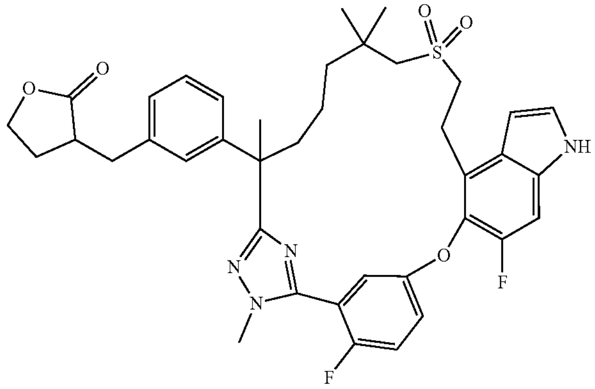 [SMILES: Cn1nc2nc1-c1cc(ccc1F)Oc1c(F)cc3[nH]ccc3c1CCS(=O)(=O)CC(C)(C)CCCC2(C)c1cccc(CC2CCOC2=O)c1] |
| 174 | 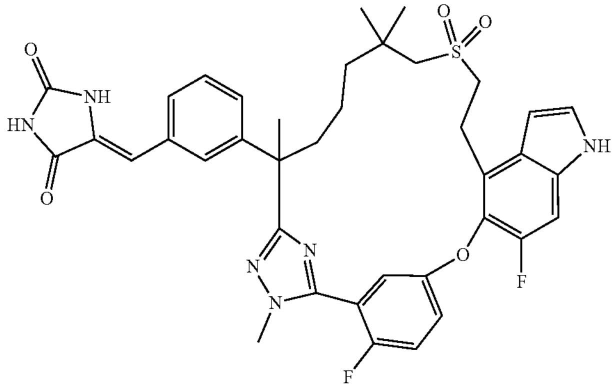 [SMILES: Cn1nc2nc1-c1cc(ccc1F)Oc1c(F)cc3[nH]ccc3c1CCS(=O)(=O)CC(C)(C)CCCC2(C)c1cccc(/C=C2\NC(=O)NC2=O)c1] |
| 175 | 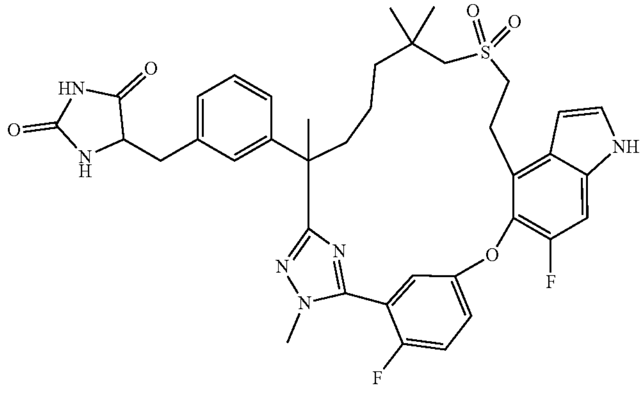 [SMILES: Cn1nc2nc1-c1cc(ccc1F)Oc1c(F)cc3[nH]ccc3c1CCS(=O)(=O)CC(C)(C)CCCC2(C)c1cccc(CC2NC(=O)NC2=O)c1] |

-continued
| Compound No. | Structures |
| --- | --- |
| 176 | 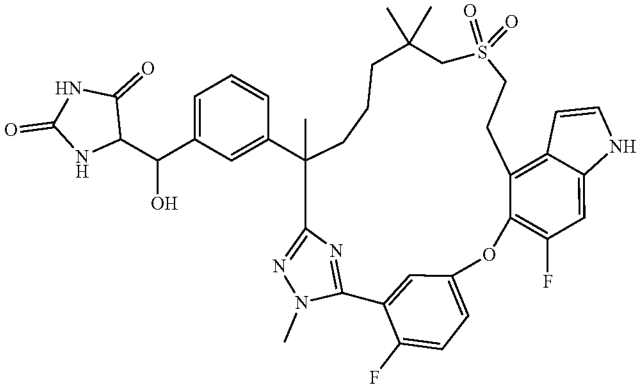 [SMILES: Cn1nc2nc1-c1cc(ccc1F)Oc1c(F)cc3[nH]ccc3c1CCS(=O)(=O)CC(C)(C)CCCC2(C)c1cccc(C(O)C2NC(=O)NC2=O)c1] |
| 177 | 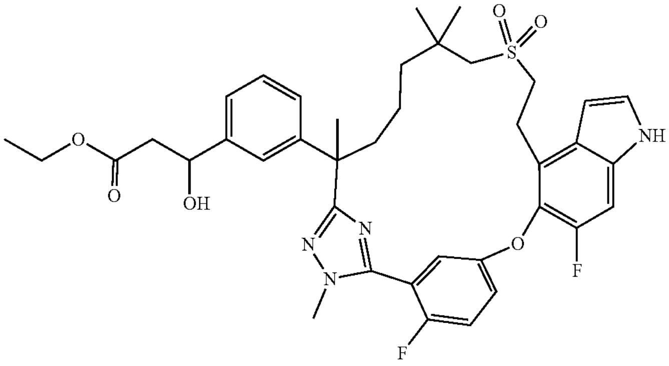 [SMILES: CCOC(=O)CC(O)c1cccc(C2(C)CCCC(C)(C)CS(=O)(=O)CCc3c(c(F)cc4[nH]ccc34)Oc3ccc(F)c(c3)-c3nc2nn3C)c1] |
| 178 | 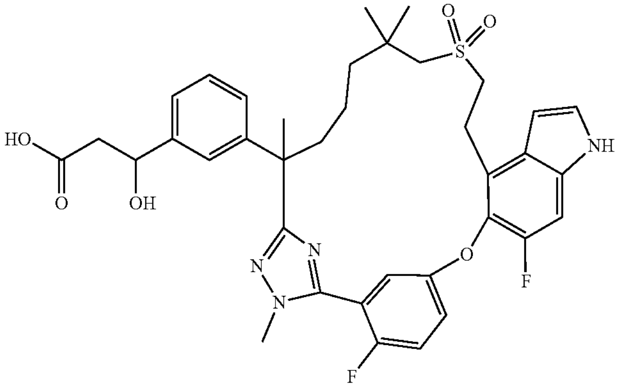 [SMILES: Cn1nc2nc1-c1cc(ccc1F)Oc1c(F)cc3[nH]ccc3c1CCS(=O)(=O)CC(C)(C)CCCC2(C)c1cccc(C(O)CC(=O)O)c1] |
| 179A | 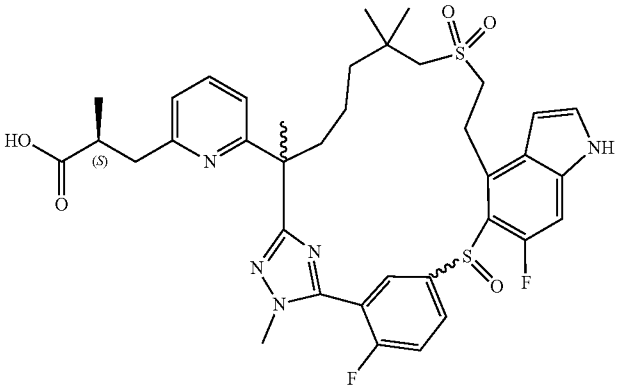 |

-continued
| Compound No. | Structures |
| --- | --- |
| 179B | 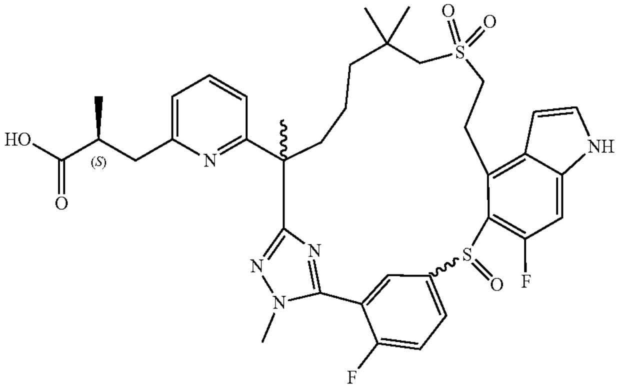 |
| 179C | 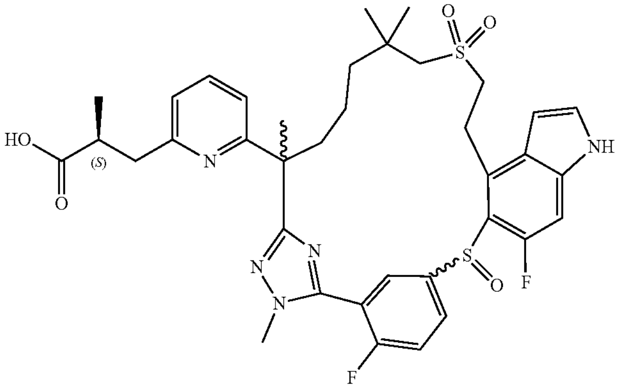 |
| 179D | 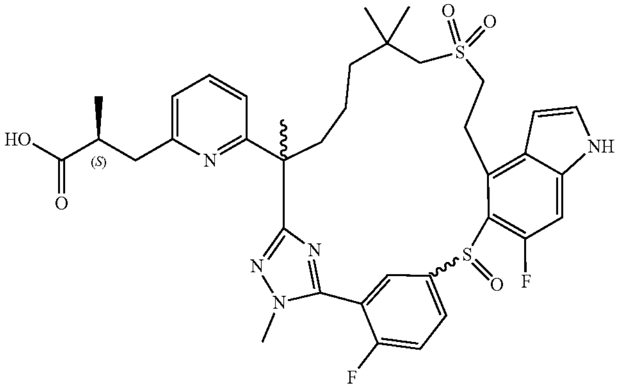 |
| 180A | 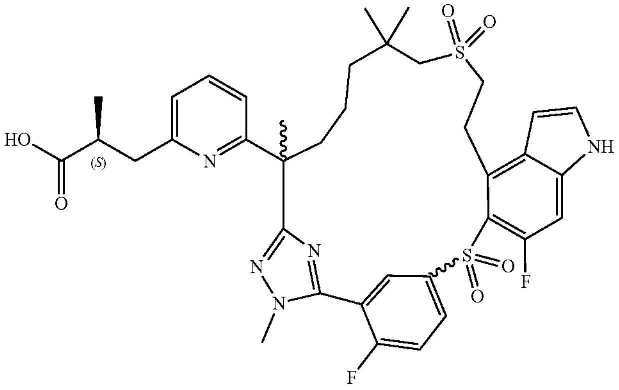 |

-continued
| Compound No. | Structures |
| --- | --- |
| 180B | 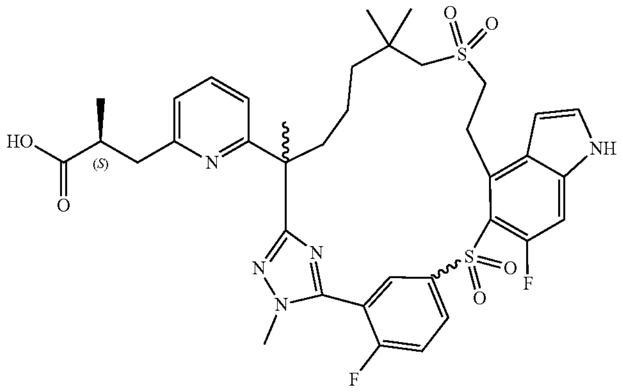 |
| 181A | 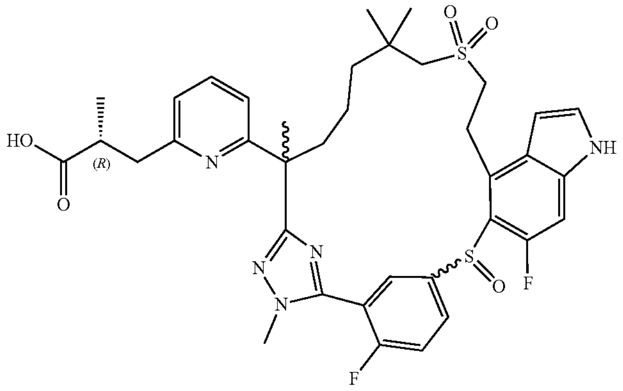 |
| 181B | 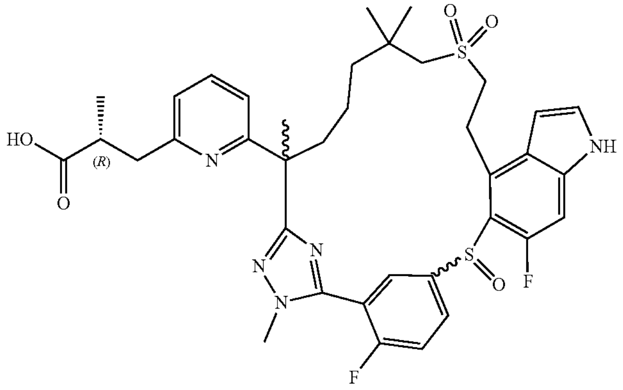 |
| 181C | 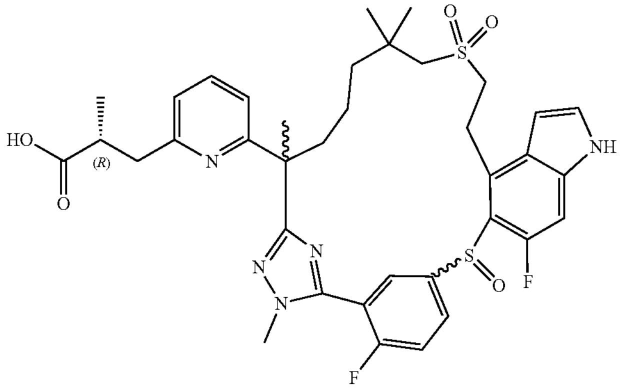 |

-continued
| Compound No. | Structures |
|---|---|
| 181D | 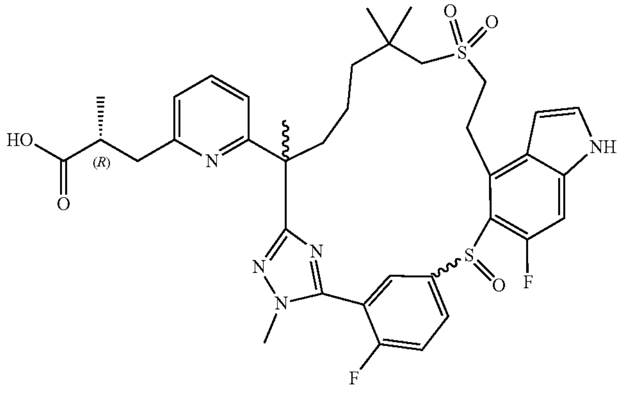 |
| 182 | 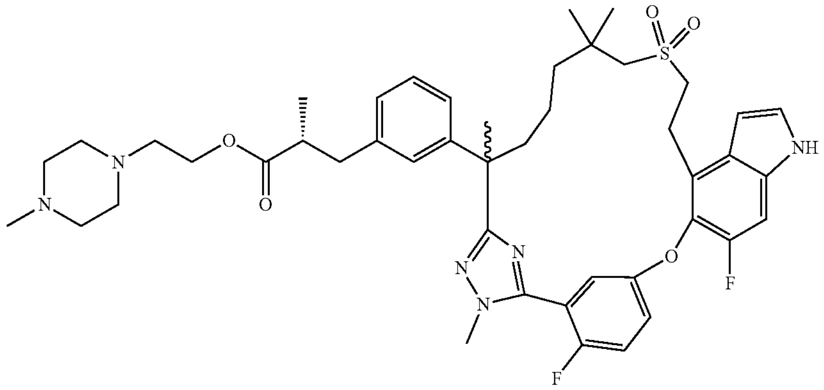 [SMILES: C[C@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCCN1CCN(C)CC1] |
| 183A | 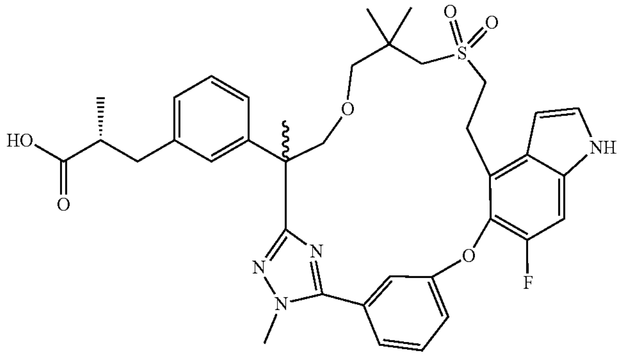 [SMILES: C[C@H](Cc1cccc(C2(C)COCC(C)(C)CS(=O)(=O)CCc3c(c(F)cc4[nH]ccc34)Oc3cccc(c3)-c3nc2nn3C)c1)C(=O)O] |
| 183B | 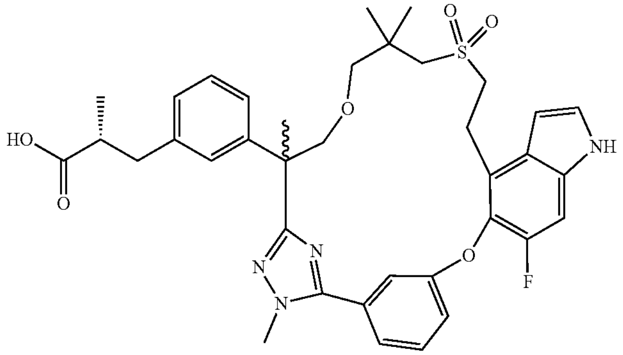 [SMILES: C[C@H](Cc1cccc(C2(C)COCC(C)(C)CS(=O)(=O)CCc3c(c(F)cc4[nH]ccc34)Oc3cccc(c3)-c3nc2nn3C)c1)C(=O)O] |

-continued
| Compound No. | Structures |
|---|---|
| 184 | 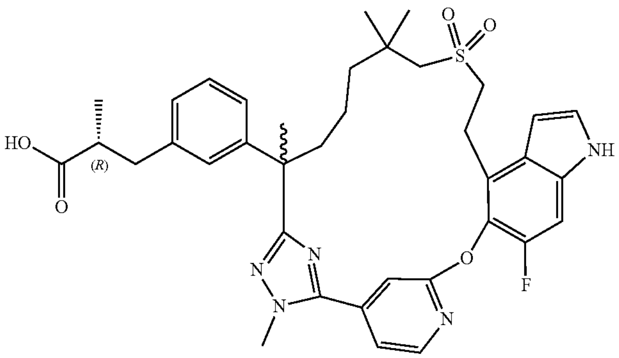 |
| 185 | 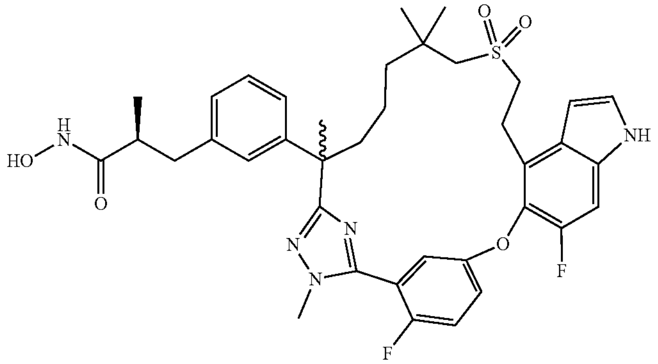 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NO] |
| 186 | 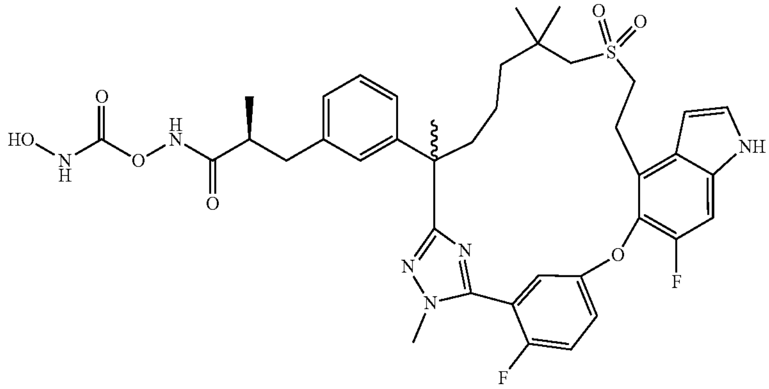 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NOC(=O)NO] |
| 187 | 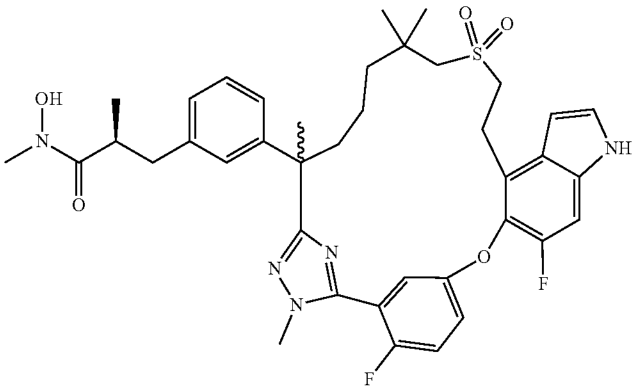 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)N(C)O] |

-continued
| Compound No. | Structures |
|---|---|
| 188 | 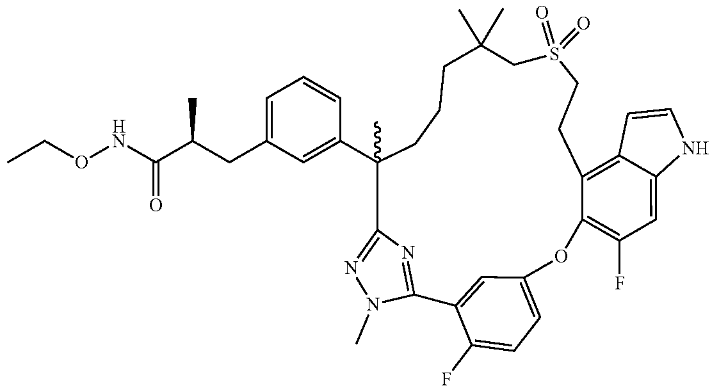 [SMILES: CCONC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1] |
| 189 | 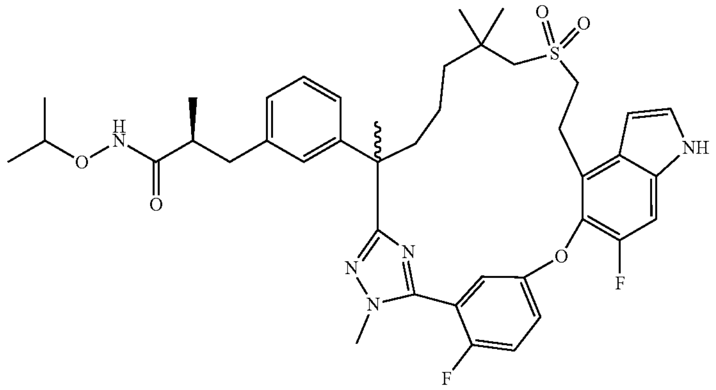 [SMILES: CC(C)ONC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1] |
| 190 | 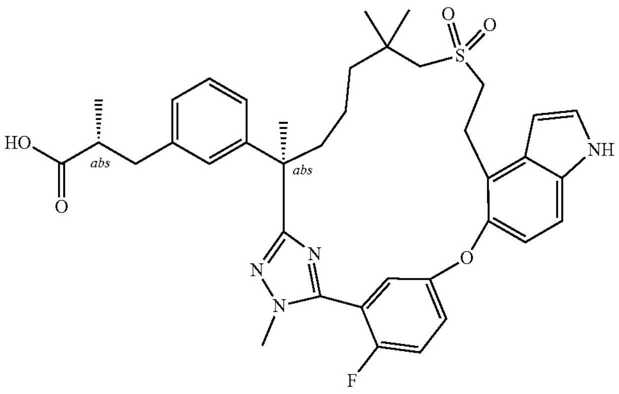 [SMILES: C[C@H](Cc1cccc([C@@]2(C)CCCC(C)(C)CS(=O)(=O)CCc3c(ccc4[nH]ccc34)Oc3ccc(F)c(c3)-c3nc2nn3C)c1)C(=O)O] |
| 191 | 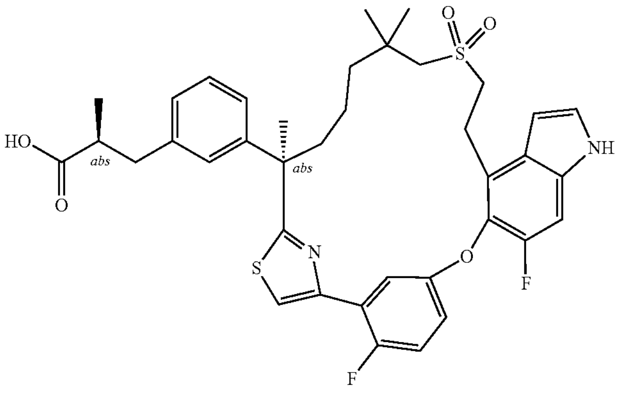 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3csc2n3)c1)C(=O)O] |

-continued
| Compound No. | Structures |
|---|---|
| 192 | 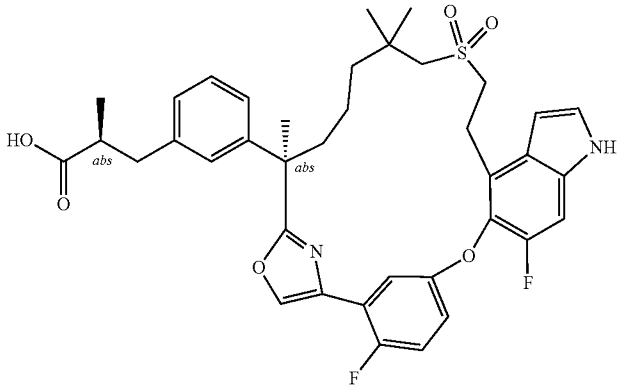 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3coc2n3)c1)C(=O)O] |
| 193 | 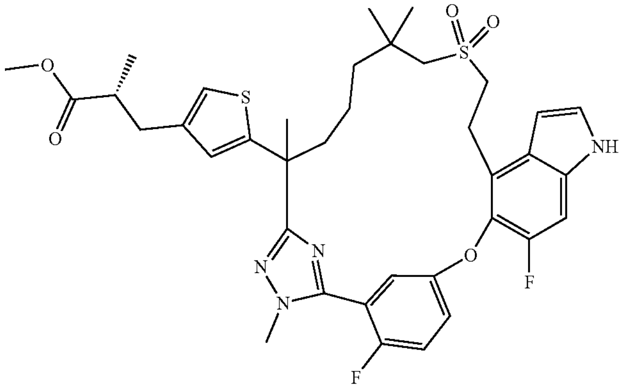 [SMILES: COC(=O)[C@H](C)Cc1csc(C2(C)CCCC(C)(C)CS(=O)(=O)CCc3c(c(F)cc4[nH]ccc34)Oc3ccc(F)c(c3)-c3nc2nn3C)c1] |
| 194 | 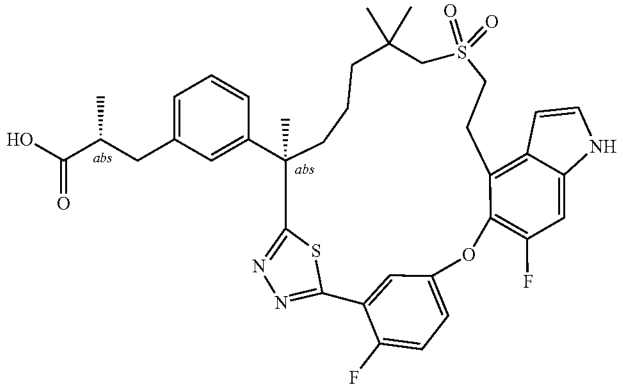 [SMILES: C[C@H](Cc1cccc([C@@]2(C)CCCC(C)(C)CS(=O)(=O)CCc3c(c(F)cc4[nH]ccc34)Oc3ccc(F)c(c3)C3=NN=C2S3)c1)C(=O)O] |
| 195A | 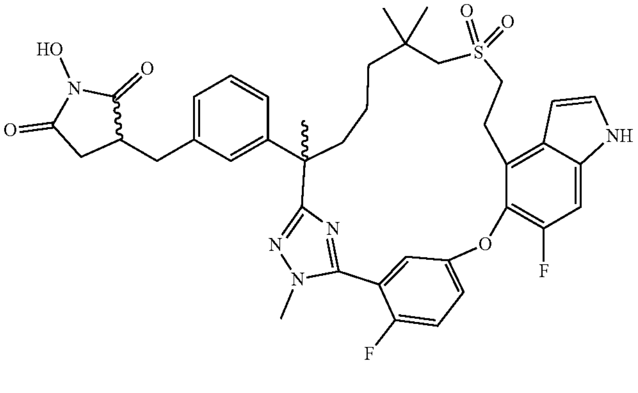 [SMILES: Cn1nc2nc1-c1cc(ccc1F)Oc1c(F)cc3[nH]ccc3c1CCS(=O)(=O)CC(C)(C)CCCC2(C)c1cccc(CC2CC(=O)N(O)C2=O)c1] |

-continued
| Compound No. | Structures |
| --- | --- |
| 195B | 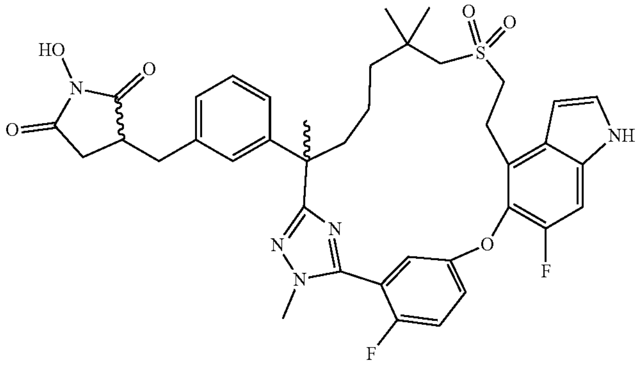 [SMILES: Cn1nc2nc1-c1cc(ccc1F)Oc1c(F)cc3[nH]ccc3c1CCS(=O)(=O)CC(C)(C)CCCC2(C)c1cccc(CC2CC(=O)N(O)C2=O)c1] |
| 196A | 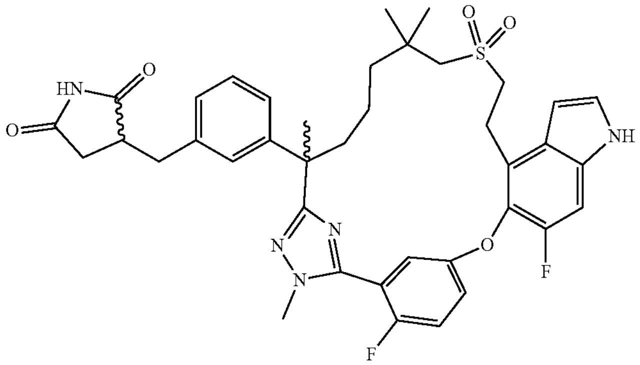 [SMILES: Cn1nc2nc1-c1cc(ccc1F)Oc1c(F)cc3[nH]ccc3c1CCS(=O)(=O)CC(C)(C)CCCC2(C)c1cccc(CC2CC(=O)NC2=O)c1] |
| 196B | 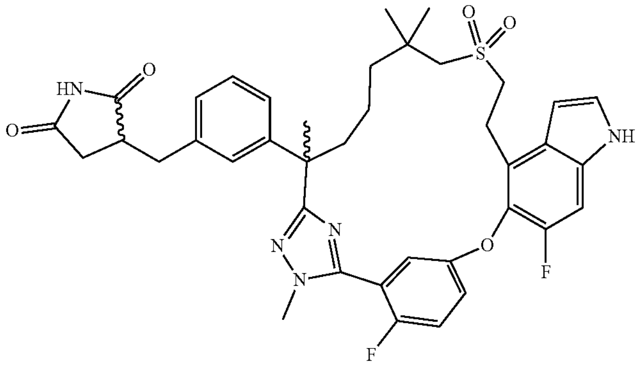 [SMILES: Cn1nc2nc1-c1cc(ccc1F)Oc1c(F)cc3[nH]ccc3c1CCS(=O)(=O)CC(C)(C)CCCC2(C)c1cccc(CC2CC(=O)NC2=O)c1] |
| 197 | 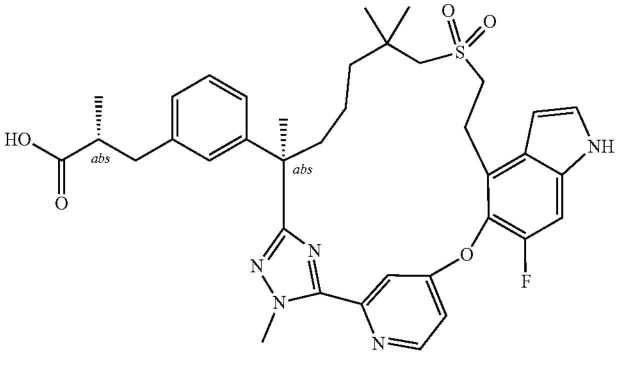 [SMILES: C[C@H](Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O] |

-continued
| Compound No. | Structures |
|---|---|
| 198 | 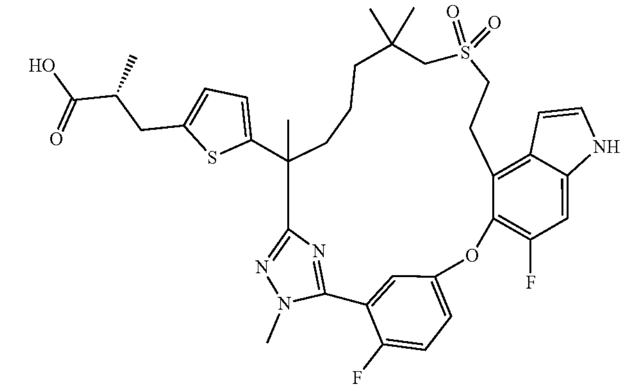 [SMILES: C[C@H](Cc1ccc(C2(C)CCCC(C)(C)CS(=O)(=O)CCc3c(c(F)cc4[nH]ccc34)Oc3ccc(F)c(c3)-c3nc2nn3C)s1)C(=O)O] |
| 199 | 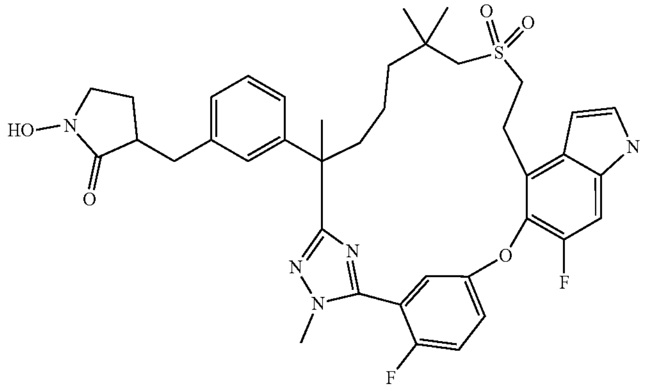 [SMILES: Cn1nc2nc1-c1cc(ccc1F)Oc1c(F)cc3[nH]ccc3c1CCS(=O)(=O)CC(C)(C)CCCC2(C)c1cccc(CC2CCN(O)C2=O)c1] |
| 200 | 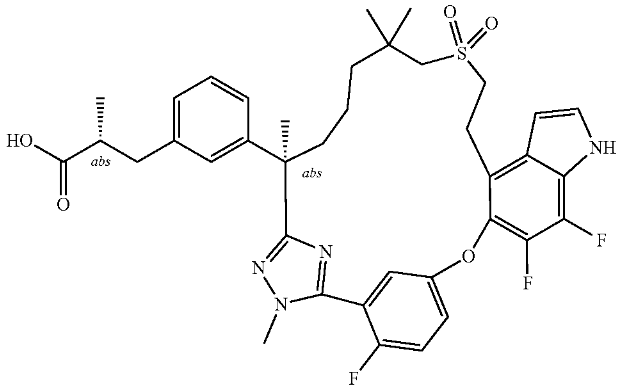 [SMILES: C[C@H](Cc1cccc([C@@]2(C)CCCC(C)(C)CS(=O)(=O)CCc3c(c(F)c(F)c4[nH]ccc34)Oc3ccc(F)c(c3)-c3nc2nn3C)c1)C(=O)O] |
| 201 | 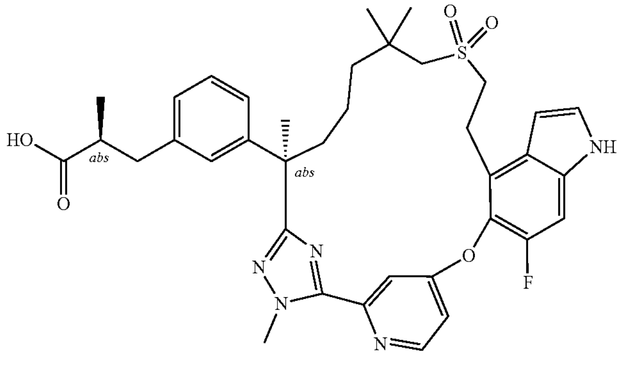 [SMILES: C[C@@H](Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O] |

-continued
| Compound No. | Structures |
| --- | --- |
| 202 | 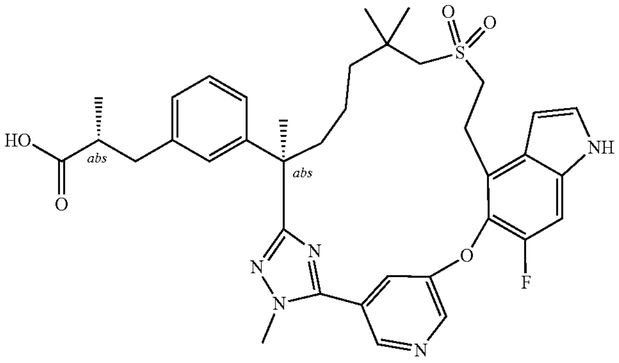 [SMILES: C[C@H](Cc1cccc([C@@]2(C)CCCC(C)(C)CS(=O)(=O)CCc3c(c(F)cc4[nH]ccc34)Oc3cncc(c3)-c3nc2nn3C)c1)C(=O)O] |
| 204 | 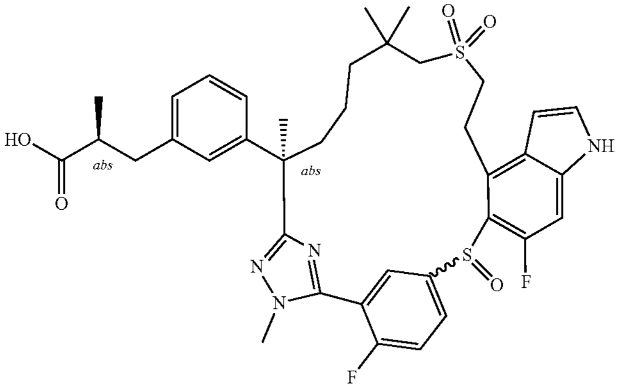 |
| 205 | 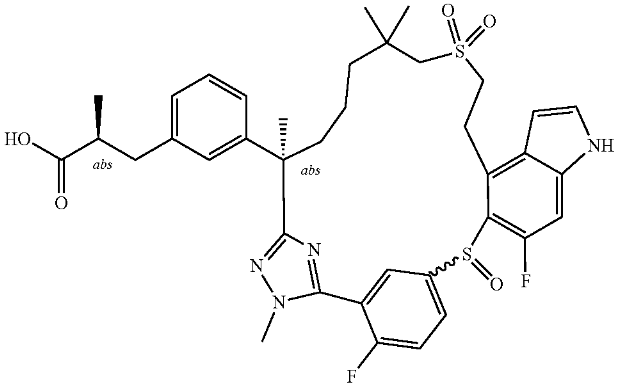 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O] |
| 206A | 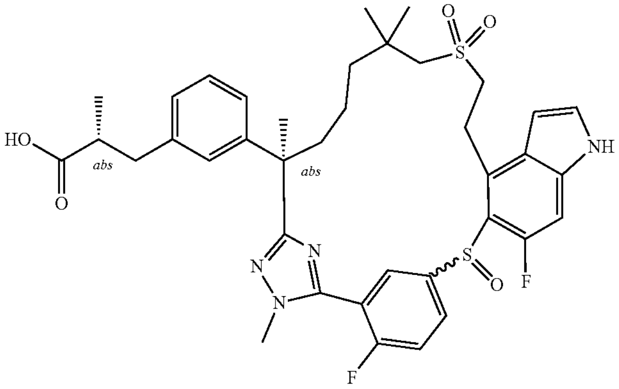 [SMILES: C[C@H](Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O] |

-continued
| Compound No. | Structures |
|---|---|
| 206B | 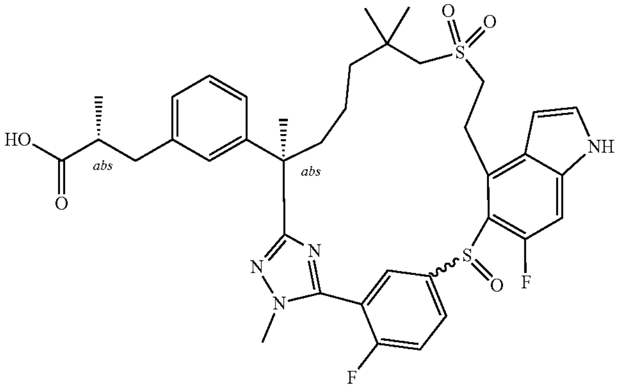 [SMILES: C[C@H](Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O] |
| 209A | 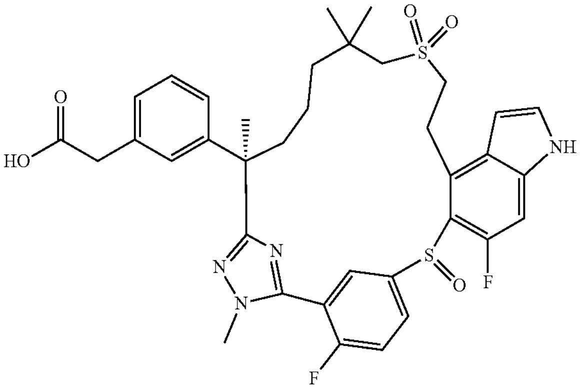 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CC(=O)O)c1] |
| 209B | 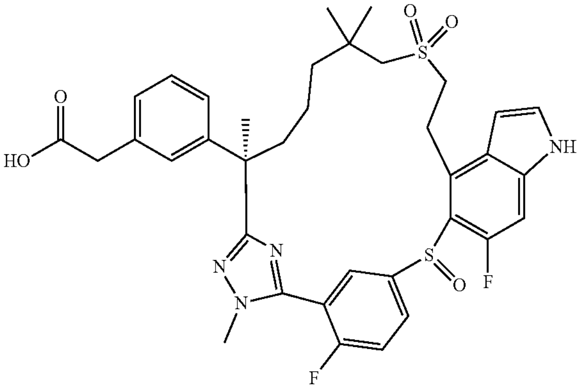 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CC(=O)O)c1] |
| 210A | 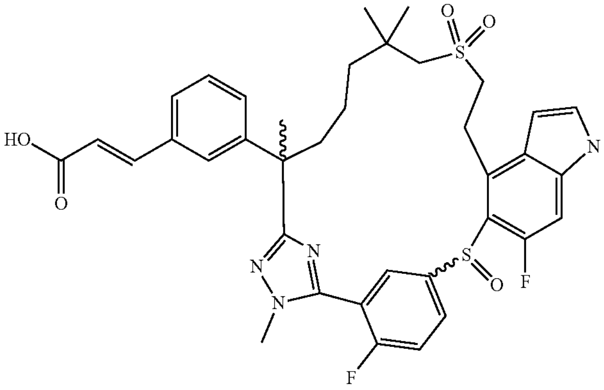 [SMILES: Cn1nc2nc1-c1cc(ccc1F)S(=O)c1c(F)cc3[nH]ccc3c1CCS(=O)(=O)CC(C)(C)CCCC2(C)c1cccc(/C=C/C(=O)O)c1] |

-continued
| Compound No. | Structures |
| --- | --- |
| 210B | 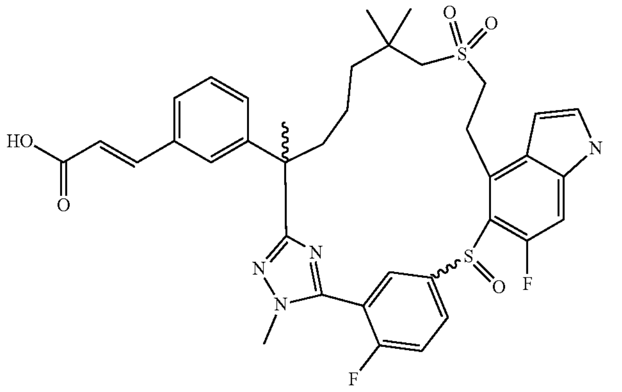 [SMILES: Cn1nc2nc1-c1cc(ccc1F)S(=O)c1c(F)cc3[nH]ccc3c1CCS(=O)(=O)CC(C)(C)CCCC2(C)c1cccc(/C=C/C(=O)O)c1] |
| 210C | 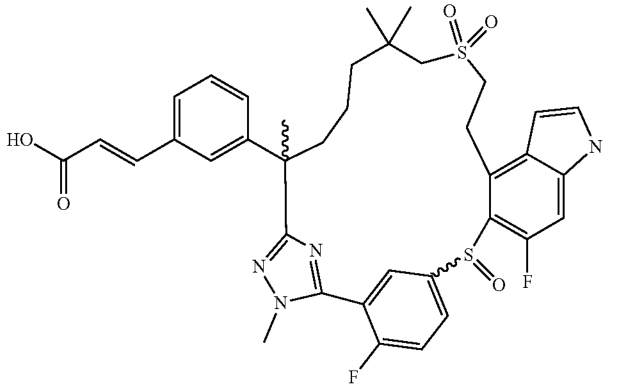 [SMILES: Cn1nc2nc1-c1cc(ccc1F)S(=O)c1c(F)cc3[nH]ccc3c1CCS(=O)(=O)CC(C)(C)CCCC2(C)c1cccc(/C=C/C(=O)O)c1] |
| 210D | 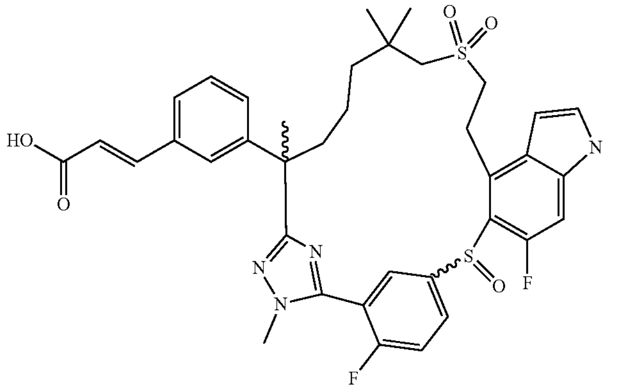 [SMILES: Cn1nc2nc1-c1cc(ccc1F)S(=O)c1c(F)cc3[nH]ccc3c1CCS(=O)(=O)CC(C)(C)CCCC2(C)c1cccc(/C=C/C(=O)O)c1] |
| 211A | 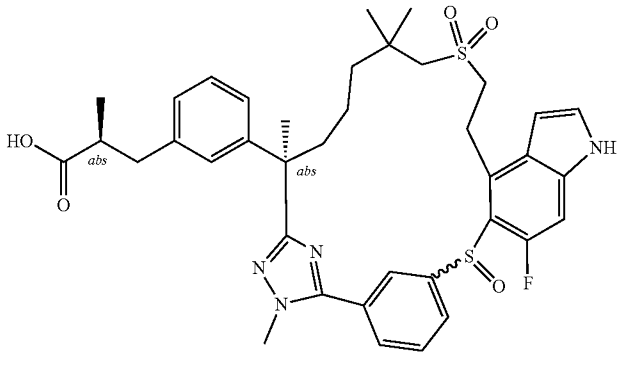 [SMILES: C[C@@H](Cc1cccc([C@@]2(C)CCCC(C)(C)CS(=O)(=O)CCc3c(c(F)cc4[nH]ccc34)S(=O)c3cccc(c3)-c3nc2nn3C)c1)C(=O)O] |

-continued
| Compound No. | Structures |
|---|---|
| 211B | 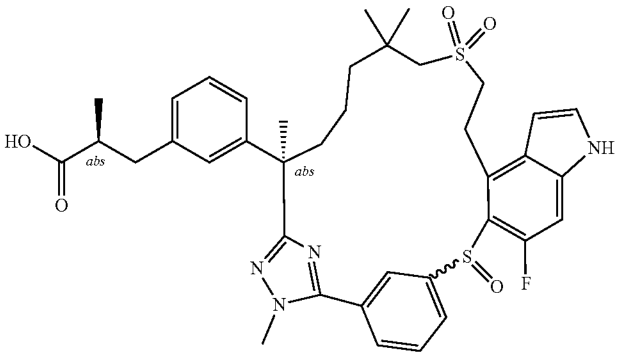 [SMILES: C[C@@H](Cc1cccc([C@@]2(C)CCCC(C)(C)CS(=O)(=O)CCc3c(c(F)cc4[nH]ccc34)S(=O)c3cccc(c3)-c3nc2nn3C)c1)C(=O)O] |
| 215A | 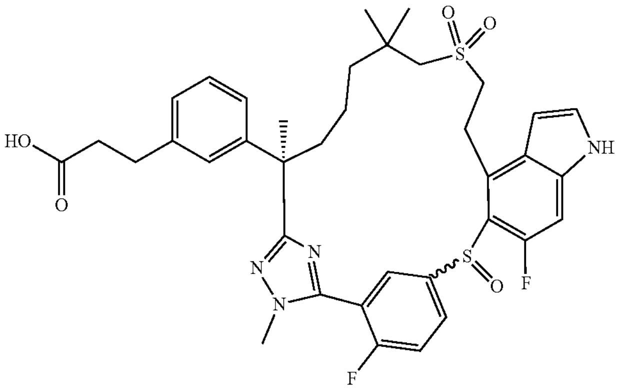 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCC(=O)O)c1] |
| 215B | 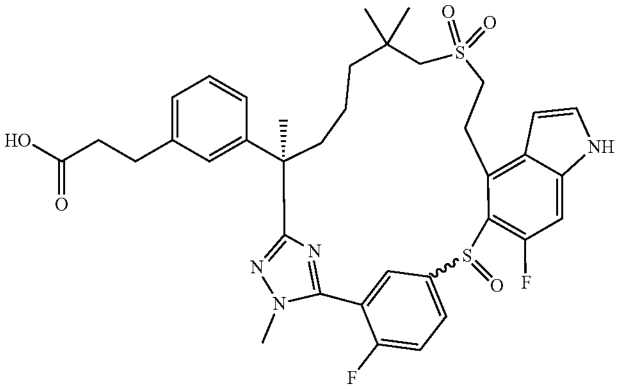 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCC(=O)O)c1] |
| 216A | 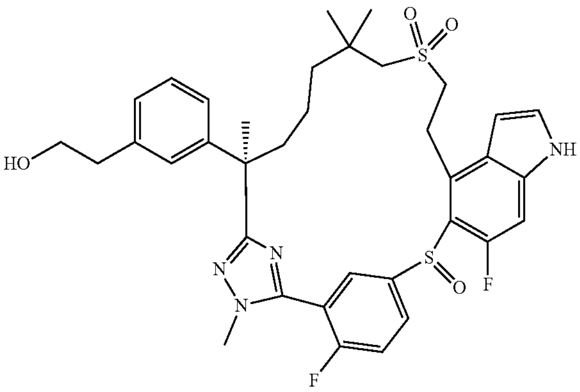 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCO)c1] |

-continued
| Compound No. | Structures |
|---|---|
| 216B | 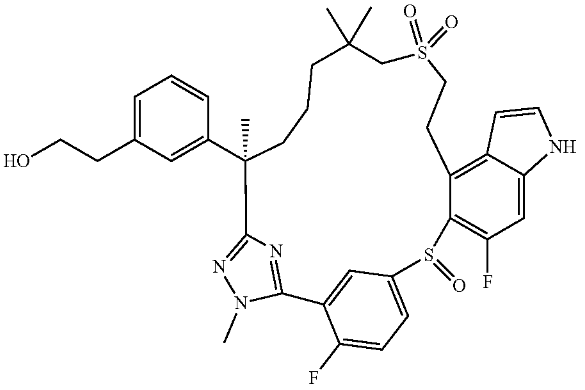 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCO)c1] |
| 217A | 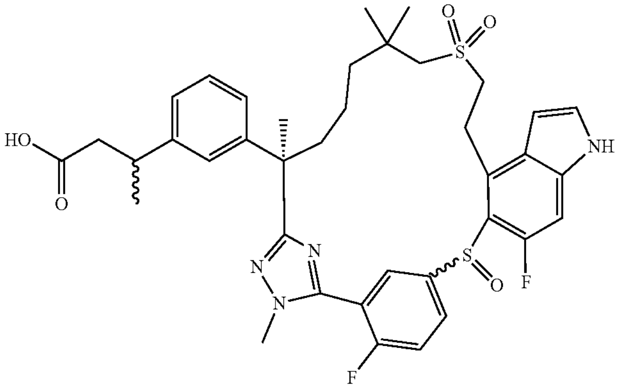 [SMILES: CC(CC(=O)O)c1cccc([C@@]2(C)CCCC(C)(C)CS(=O)(=O)CCc3c(c(F)cc4[nH]ccc34)S(=O)c3ccc(F)c(c3)-c3nc2nn3C)c1] |
| 217B | 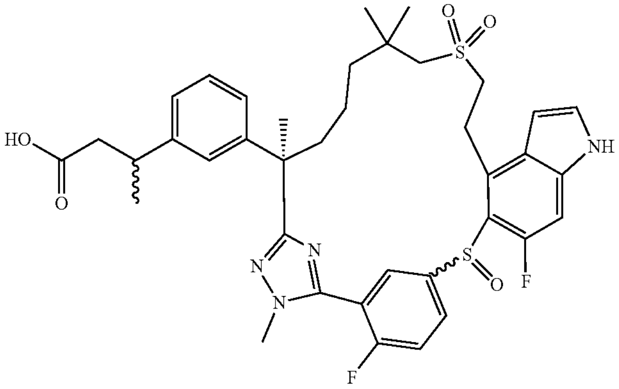 [SMILES: CC(CC(=O)O)c1cccc([C@@]2(C)CCCC(C)(C)CS(=O)(=O)CCc3c(c(F)cc4[nH]ccc34)S(=O)c3ccc(F)c(c3)-c3nc2nn3C)c1] |
| 218A | 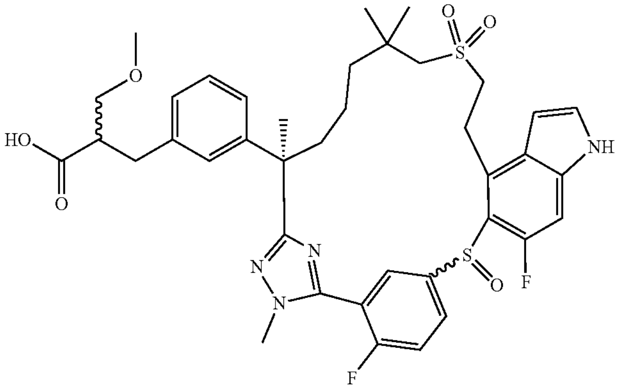 [SMILES: COCC(Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O] |

-continued
| Compound No. | Structures |
| --- | --- |
| 218B | 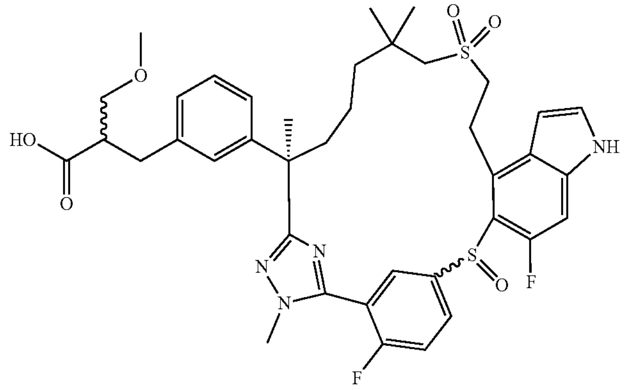 [SMILES: COCC(Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O] |
| 219 | 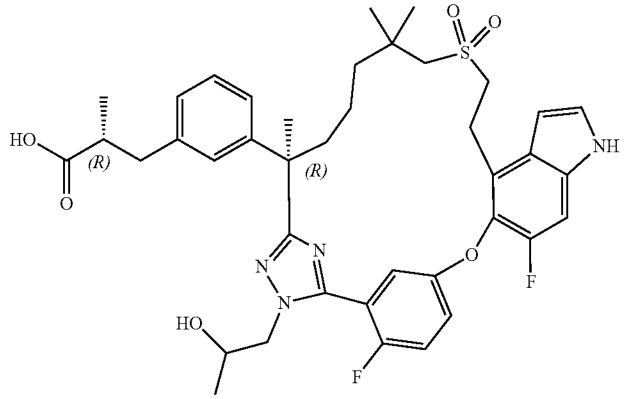 |
| 220A | 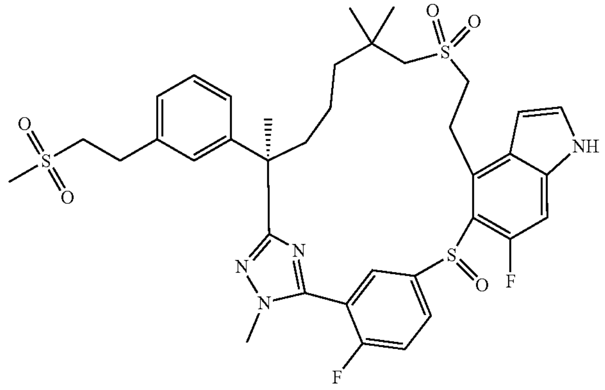 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCS(C)(=O)=O)c1] |
| 220B | 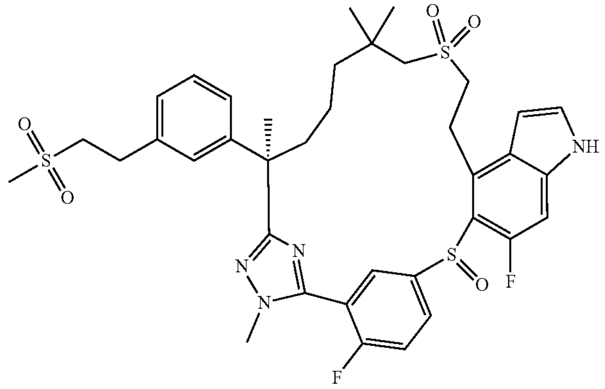 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCS(C)(=O)=O)c1] |

-continued
| Compound No. | Structures |
| --- | --- |
| 221 | 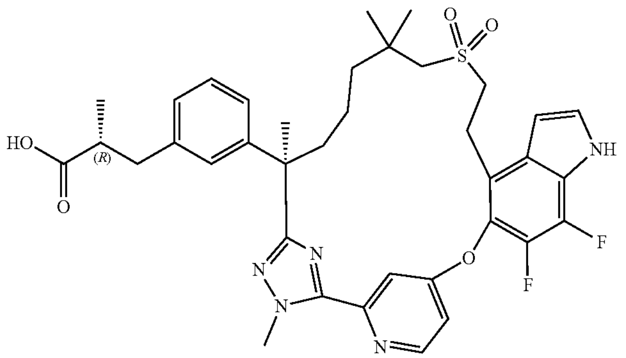 |
| 222A | 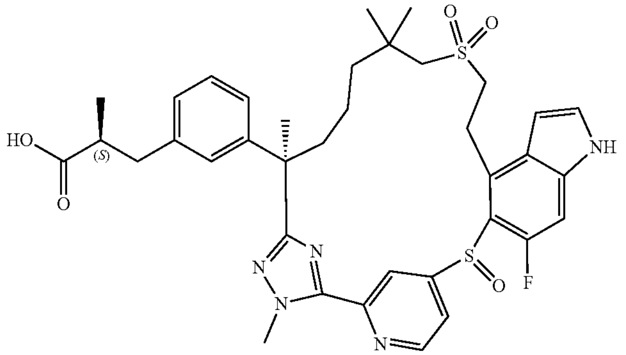 |
| 222B | 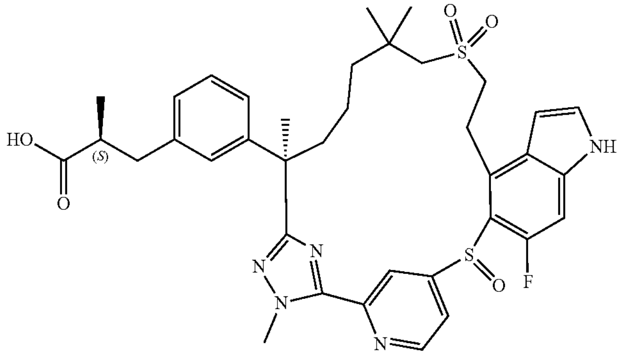 |
| 223A | 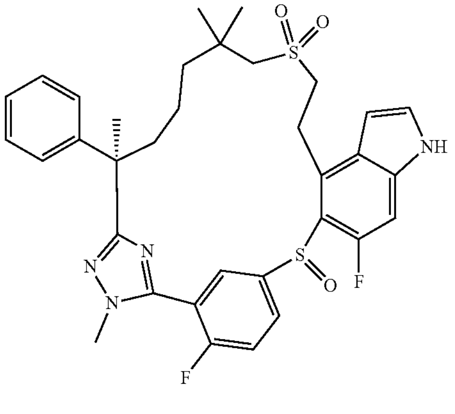 [SMILES: Cn1nc2nc1-c1cc(ccc1F)S(=O)c1c(F)cc3[nH]ccc3c1CCS(=O)(=O)CC(C)(C)CCC[C@]2(C)c1ccccc1] |

-continued
| Compound No. | Structures |
| --- | --- |
| 223B | 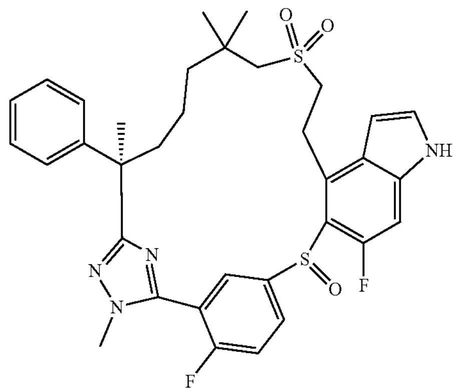 [SMILES: Cn1nc2nc1-c1cc(ccc1F)S(=O)c1c(F)cc3[nH]ccc3c1CCS(=O)(=O)CC(C)(C)CCC[C@]2(C)c1ccccc1] |
| 224 | 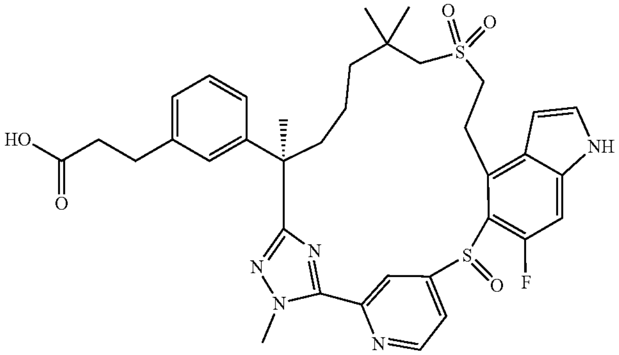 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCC(=O)O)c1] |
| 225A | 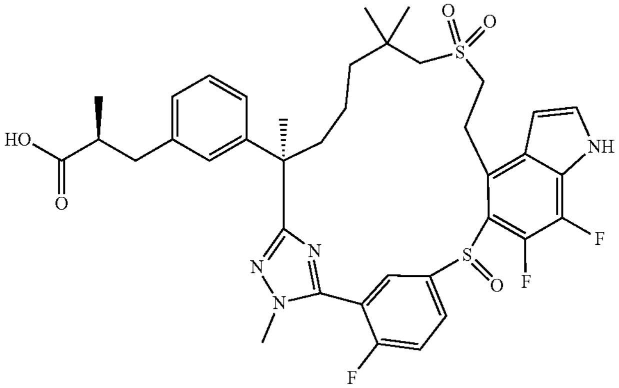 [SMILES: C[C@@H](Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O] |
| 225B | 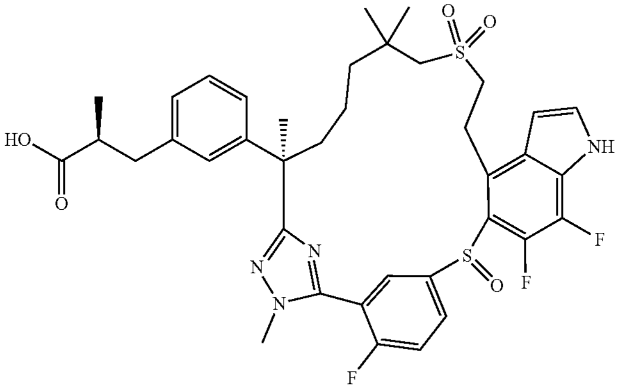 [SMILES: C[C@@H](Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O] |

-continued
| Compound No. | Structures |
|---|---|
| 226 | 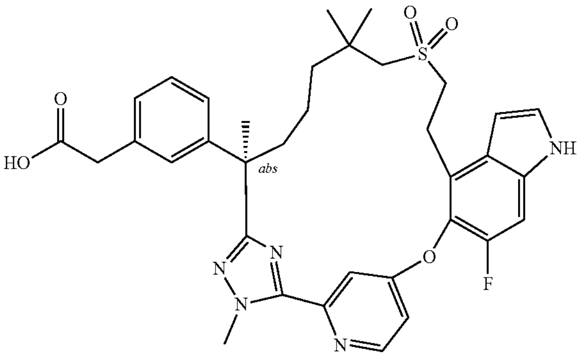 [SMILES: Cn1nc2nc1-c1cc(ccn1)Oc1c(F)cc3[nH]ccc3c1CCS(=O)(=O)CC(C)(C)CCC[C@]2(C)c1cccc(CC(=O)O)c1] |
| 227 | 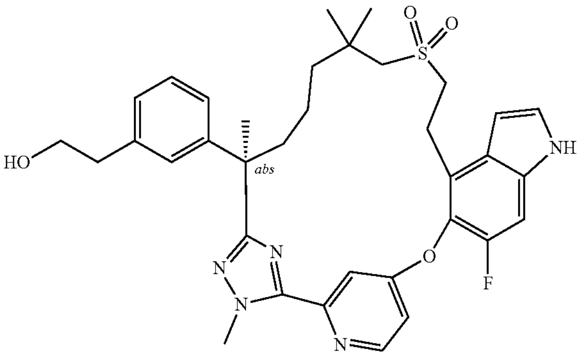 [SMILES: Cn1nc2nc1-c1cc(ccn1)Oc1c(F)cc3[nH]ccc3c1CCS(=O)(=O)CC(C)(C)CCC[C@]2(C)c1cccc(CCO)c1] |
| 228 | 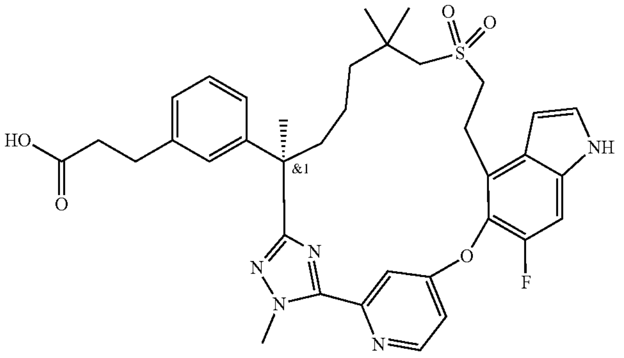 [SMILES: Cn1nc2nc1-c1cc(ccn1)Oc1c(F)cc3[nH]ccc3c1CCS(=O)(=O)CC(C)(C)CCC[C@]2(C)c1cccc(CCC(=O)O)c1] |
| 229 | 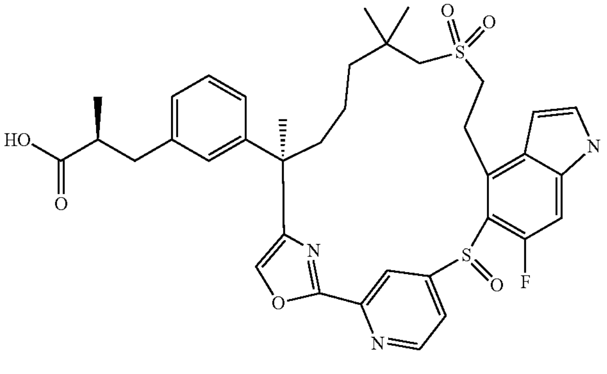 [SMILES: C[C@@H](Cc1cccc([C@@]2(C)CCCC(C)(C)CS(=O)(=O)CCc3c(c(F)cc4[nH]ccc34)S(=O)c3ccnc(c3)-c3nc2co3)c1)C(=O)O] |

-continued
| Compound No. | Structures |
|---|---|
| 230 | 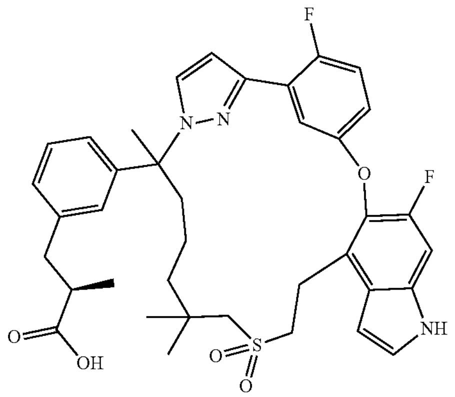 [SMILES: C[C@H](Cc1cccc(C2(C)CCCC(C)(C)CS(=O)(=O)CCc3c(c(F)cc4[nH]ccc34)Oc3ccc(F)c(c3)-c3ccn2n3)c1)C(=O)O] |
| 231 | 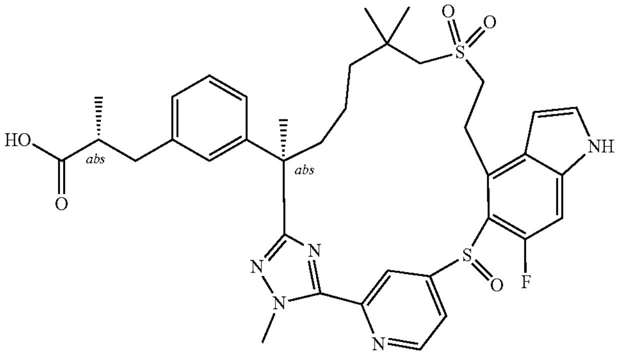 [SMILES: C[C@H](Cc1cccc([C@@]2(C)CCCC(C)(C)CS(=O)(=O)CCc3c(c(F)cc4[nH]ccc34)S(=O)c3ccnc(c3)-c3nc2nn3C)c1)C(=O)O] |
| 233 | 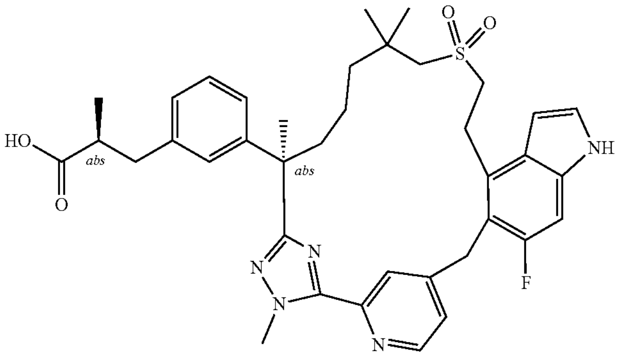 |
| 234 | 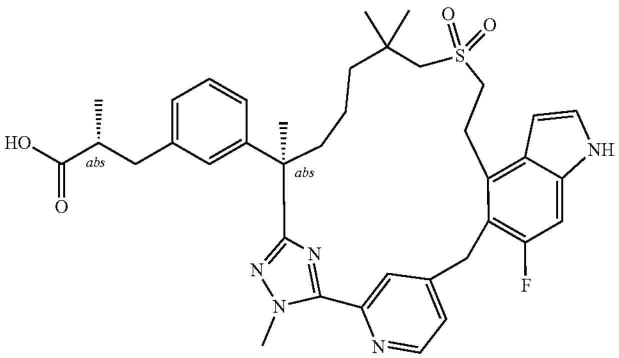 |

-continued
| Compound No. | Structures |
| --- | --- |
| 235A | 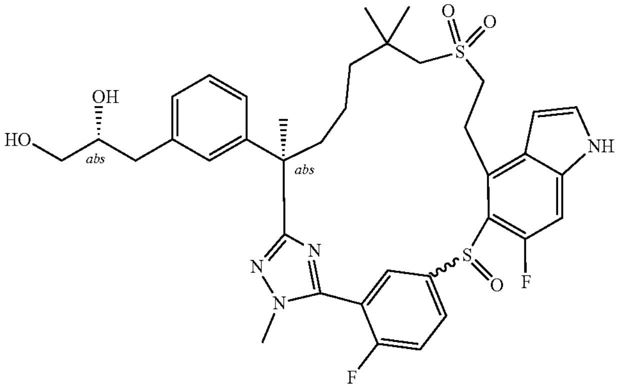 [SMILES: Cn1nc2nc1-c1cc(ccc1F)S(=O)c1c(F)cc3[nH]ccc3c1CCS(=O)(=O)CC(C)(C)CCC[C@]2(C)c1cccc(C[C@@H](O)CO)c1] |
| 235B | 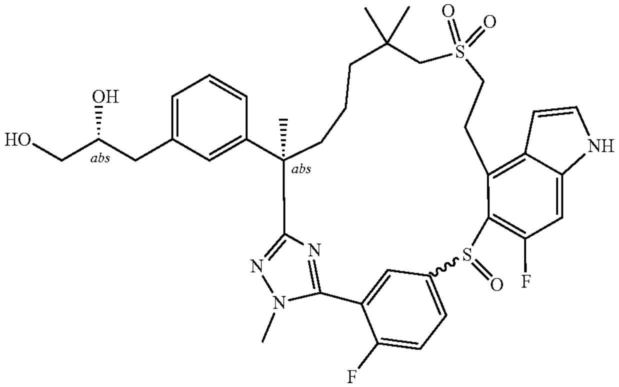 [SMILES: Cn1nc2nc1-c1cc(ccc1F)S(=O)c1c(F)cc3[nH]ccc3c1CCS(=O)(=O)CC(C)(C)CCC[C@]2(C)c1cccc(C[C@@H](O)CO)c1] |
| 236A | 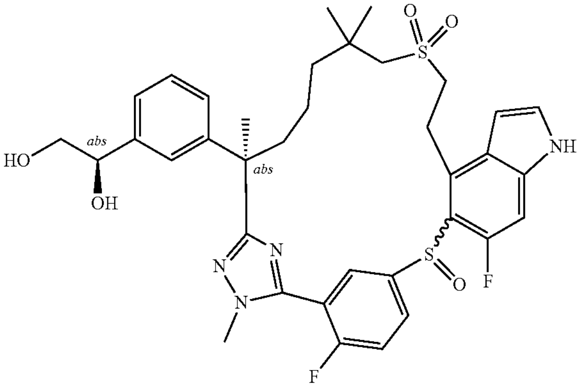 [SMILES: Cn1nc2nc1-c1cc(ccc1F)S(=O)c1c(F)cc3[nH]ccc3c1CCS(=O)(=O)CC(C)(C)CCC[C@]2(C)c1cccc([C@@H](O)CO)c1] |
| 236B | 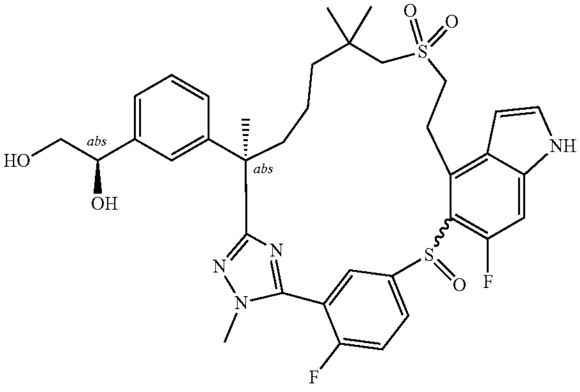 [SMILES: Cn1nc2nc1-c1cc(ccc1F)S(=O)c1c(F)cc3[nH]ccc3c1CCS(=O)(=O)CC(C)(C)CCC[C@]2(C)c1cccc([C@@H](O)CO)c1] |

-continued
| Compound No. | Structures |
| --- | --- |
| 237A | 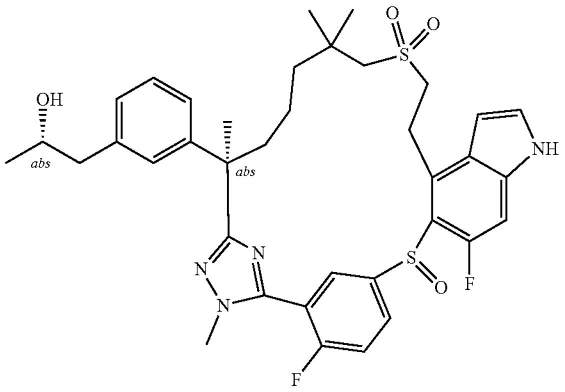 [SMILES: C[C@H](O)Cc1cccc([C@@]2(C)CCCC(C)(C)CS(=O)(=O)CCc3c(c(F)cc4[nH]ccc34)S(=O)c3ccc(F)c(c3)-c3nc2nn3C)c1] |
| 237B | 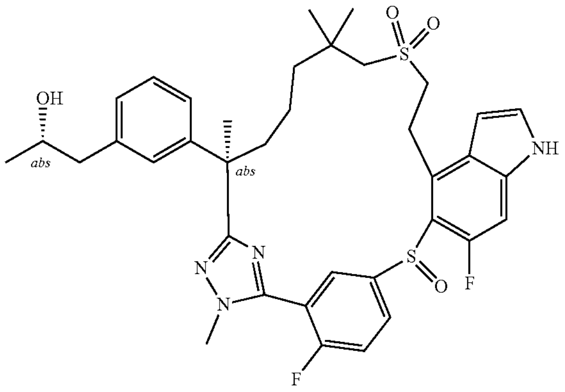 [SMILES: C[C@H](O)Cc1cccc([C@@]2(C)CCCC(C)(C)CS(=O)(=O)CCc3c(c(F)cc4[nH]ccc34)S(=O)c3ccc(F)c(c3)-c3nc2nn3C)c1] |
| 238 | 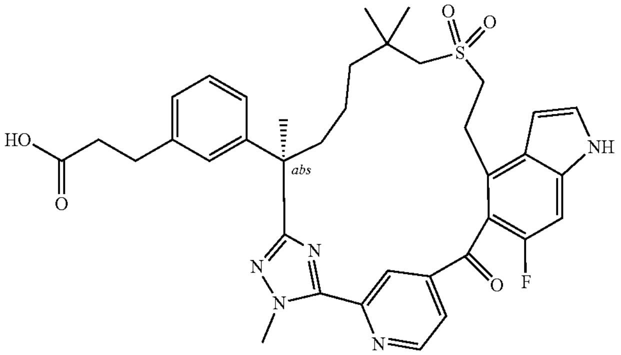 [SMILES: Cn1nc2nc1-c1cc(ccn1)C(=O)c1c(F)cc3[nH]ccc3c1CCS(=O)(=O)CC(C)(C)CCC[C@]2(C)c1cccc(CCC(=O)O)c1] |
| 239A | 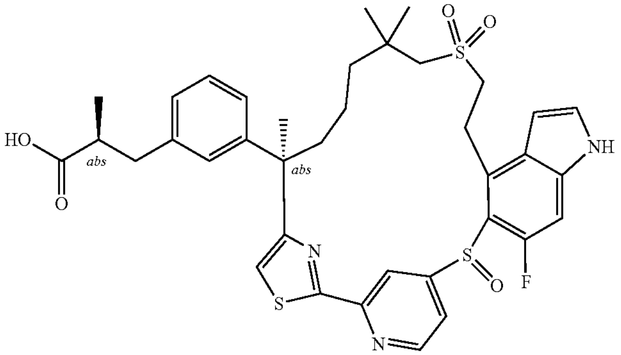 [SMILES: C[C@@H](Cc1cccc([C@@]2(C)CCCC(C)(C)CS(=O)(=O)CCc3c(c(F)cc4[nH]ccc34)S(=O)c3ccnc(c3)-c3nc2cs3)c1)C(=O)O] |

-continued
| Compound No. | Structures |
|---|---|
| 239B | 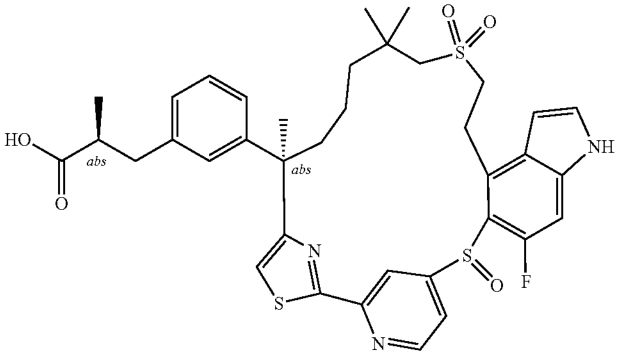 [SMILES: C[C@@H](Cc1cccc([C@@]2(C)CCCC(C)(C)CS(=O)(=O)CCc3c(c(F)cc4[nH]ccc34)S(=O)c3ccnc(c3)-c3nc2cs3)c1)C(=O)O] |
| 240 | 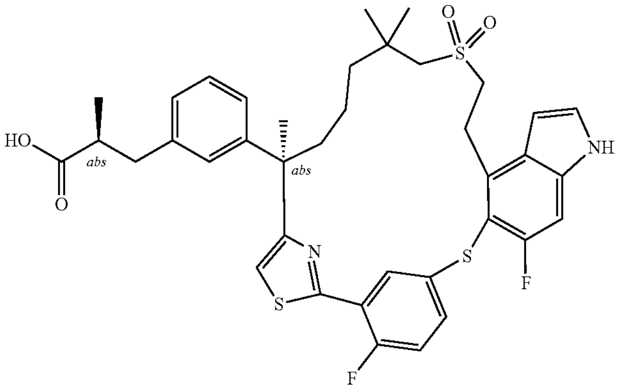 [SMILES: C[C@@H](Cc1cccc([C@@]2(C)CCCC(C)(C)CS(=O)(=O)CCc3c(c(F)cc4[nH]ccc34)Sc3ccc(F)c(c3)-c3nc2cs3)c1)C(=O)O] |
| 241A | 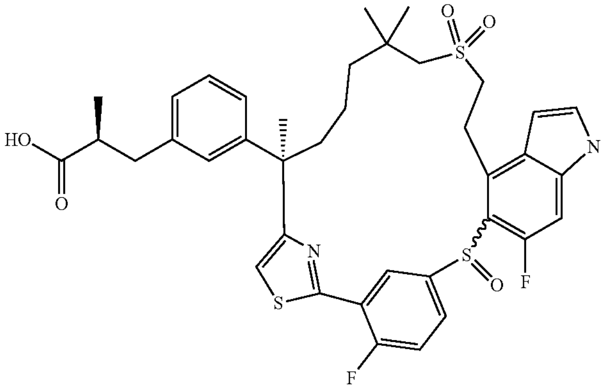 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2cs3)c1)C(=O)O] |
| 241B | 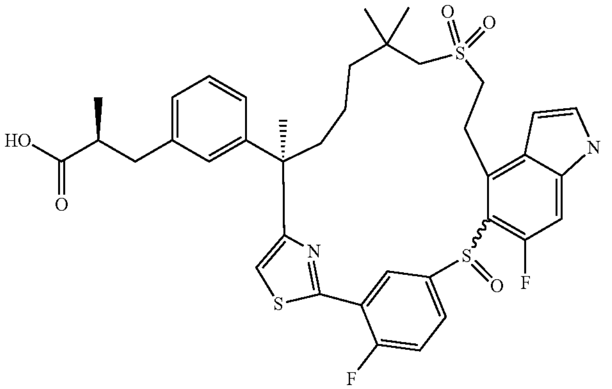 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2cs3)c1)C(=O)O] |

-continued
| Compound No. | Structures |
| --- | --- |
| 242 | 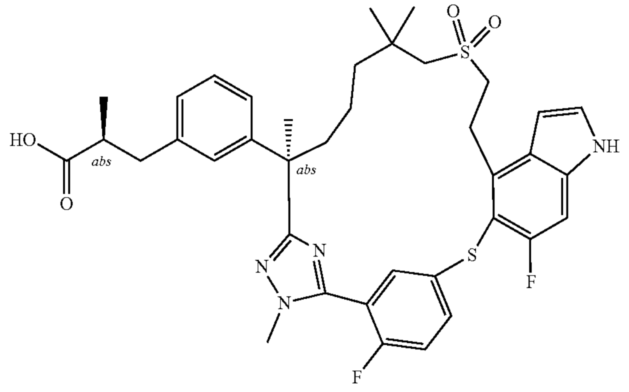 [SMILES: C[C@@H](Cc1cccc([C@@]2(C)CCCC(C)(C)CS(=O)(=O)CCc3c(c(F)cc4[nH]ccc34)Sc3ccc(F)c(c3)-c3nc2nn3C)c1)C(=O)O] |
| 243A | 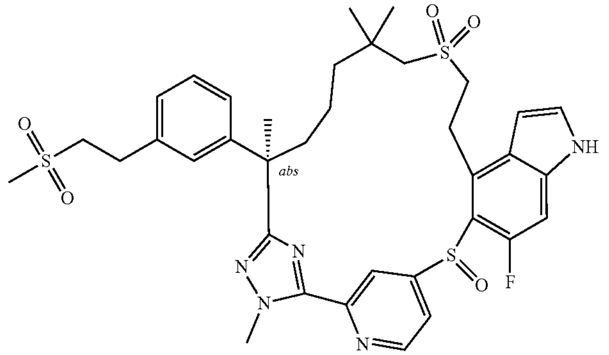 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCS(C)(=O)=O)c1] |
| 243B | 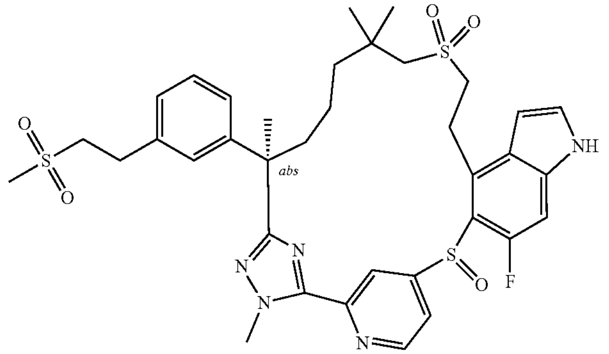 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCS(C)(=O)=O)c1] |
| 244 | 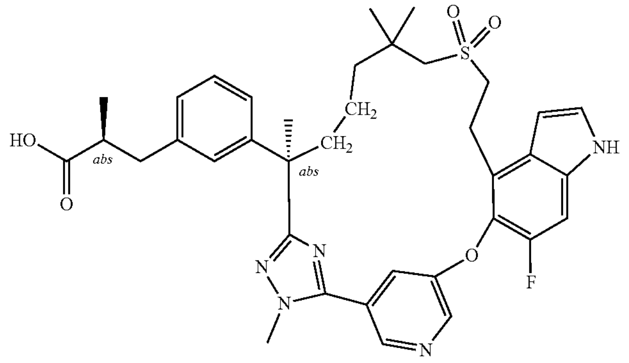 [SMILES: C[C@@H](Cc1cccc([C@@]2(C)CCCC(C)(C)CS(=O)(=O)CCc3c(c(F)cc4[nH]ccc34)Oc3cncc(c3)-c3nc2nn3C)c1)C(=O)O] |

-continued
| Compound No. | Structures |
| --- | --- |
| 245 | 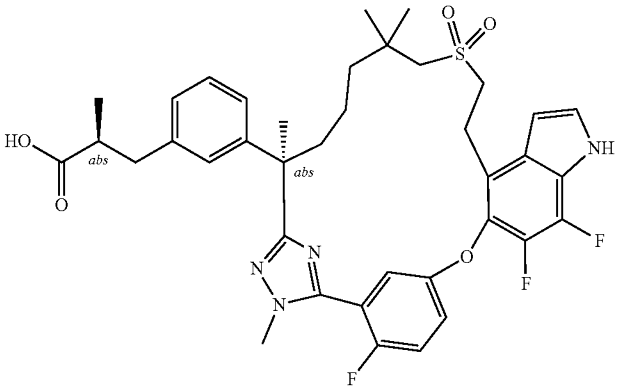 [SMILES: C[C@@H](Cc1cccc([C@@]2(C)CCCC(C)(C)CS(=O)(=O)CCc3c(c(F)c(F)c4[nH]ccc34)Oc3ccc(F)c(c3)-c3nc2nn3C)c1)C(=O)O] |
| 246A | 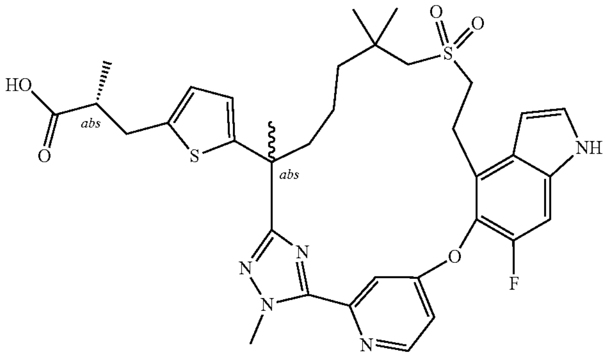 [SMILES: C[C@H](Cc1ccc(C2(C)CCCC(C)(C)CS(=O)(=O)CCc3c(c(F)cc4[nH]ccc34)Oc3ccnc(c3)-c3nc2nn3C)s1)C(=O)O] |
| 246B | 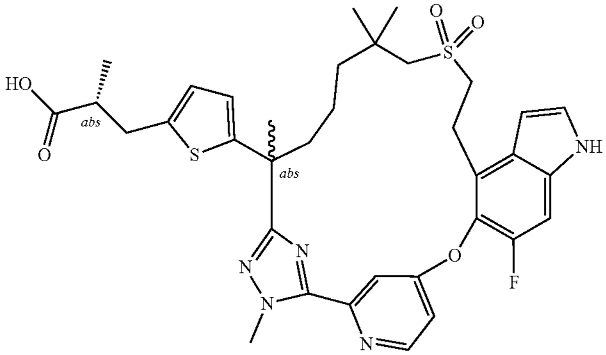 [SMILES: C[C@H](Cc1ccc(C2(C)CCCC(C)(C)CS(=O)(=O)CCc3c(c(F)cc4[nH]ccc34)Oc3ccnc(c3)-c3nc2nn3C)s1)C(=O)O] |
| 247 | 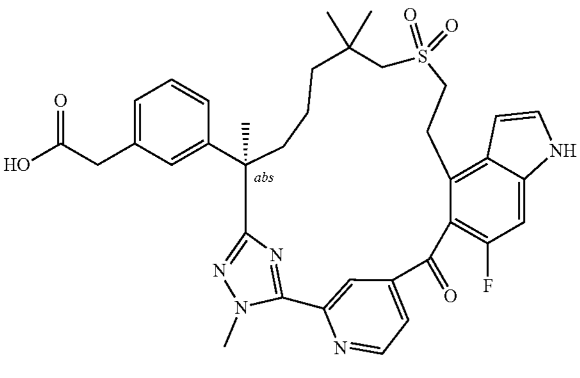 [SMILES: Cn1nc2nc1-c1cc(ccn1)C(=O)c1c(F)cc3[nH]ccc3c1CCS(=O)(=O)CC(C)(C)CCC[C@]2(C)c1cccc(CC(=O)O)c1] |

-continued
| Compound No. | Structures |
| --- | --- |
| 248A | 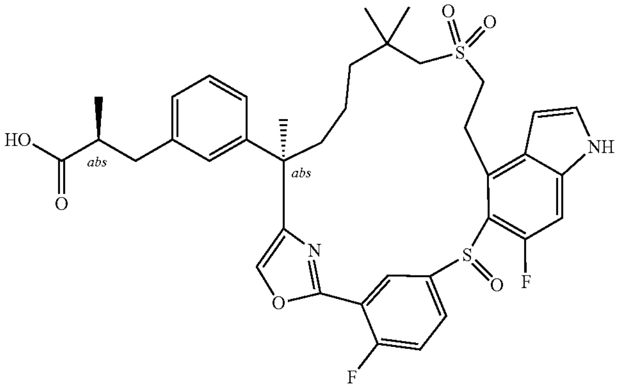 |
| 248B | 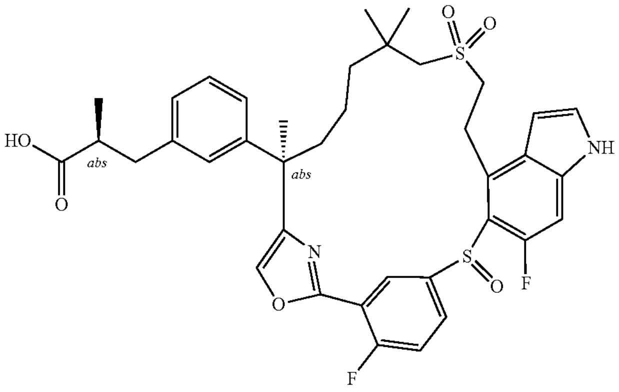 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2co3)c1)C(=O)O] |
| 249A | 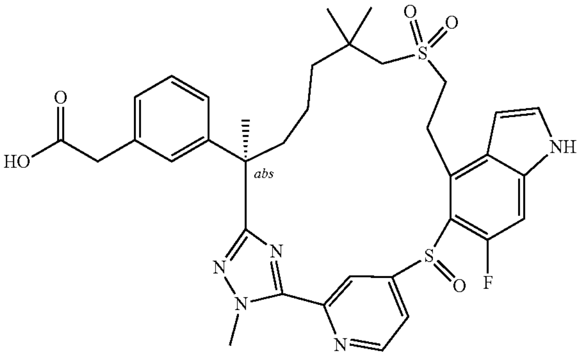 [SMILES: Cn1nc2nc1-c1cc(ccn1)S(=O)c1c(F)cc3[nH]ccc3c1CCS(=O)(=O)CC(C)(C)CCC[C@]2(C)c1cccc(CC(=O)O)c1] |
| 249B | 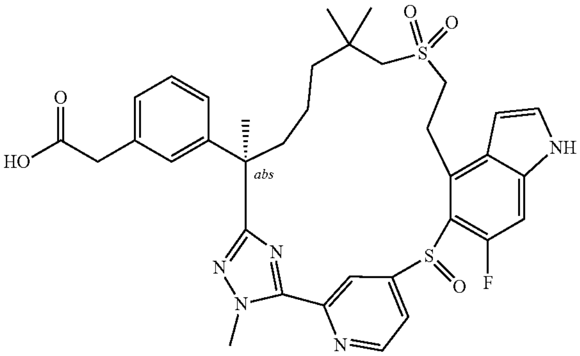 [SMILES: Cn1nc2nc1-c1cc(ccn1)S(=O)c1c(F)cc3[nH]ccc3c1CCS(=O)(=O)CC(C)(C)CCC[C@]2(C)c1cccc(CC(=O)O)c1] |

-continued
| Compound No. | Structures |
| --- | --- |
| 250 | 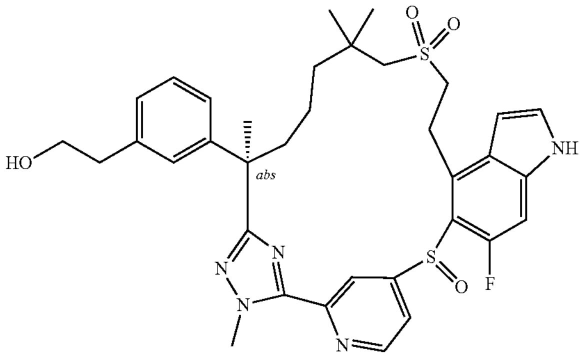 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCO)c1] |
| 251 | 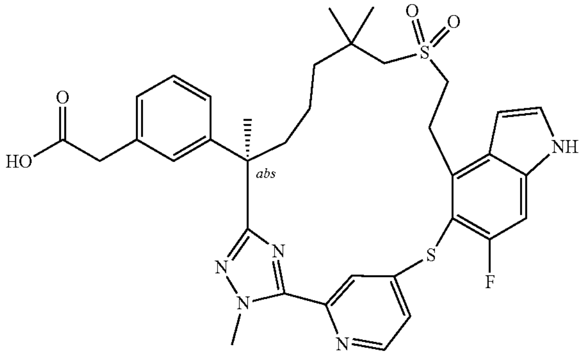 [SMILES: Cn1nc2nc1-c1cc(ccn1)Sc1c(F)cc3[nH]ccc3c1CCS(=O)(=O)CC(C)(C)CCC[C@]2(C)c1cccc(CC(=O)O)c1] |
| 252 | 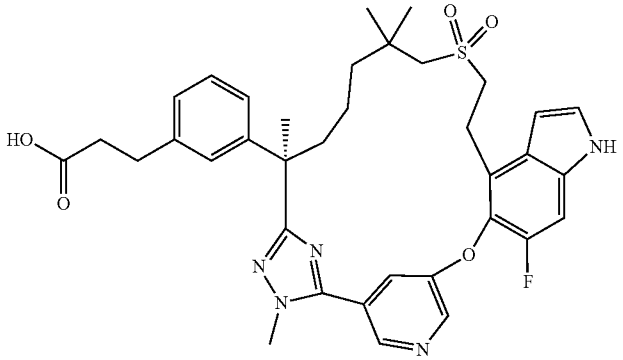 [SMILES: Cn1nc2nc1-c1cncc(c1)Oc1c(F)cc3[nH]ccc3c1CCS(=O)(=O)CC(C)(C)CCC[C@]2(C)c1cccc(CCC(=O)O)c1] |
| 253 | 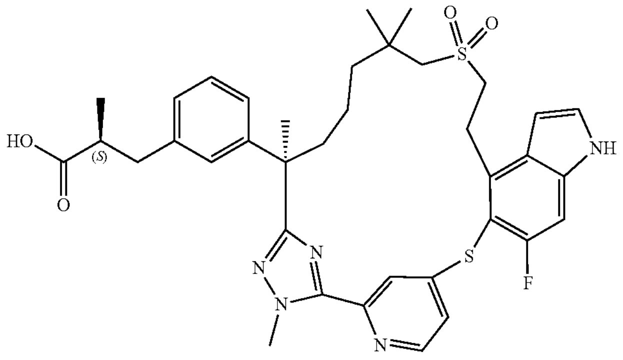 |

-continued
| Compound No. | Structures |
|---|---|
| 254 | 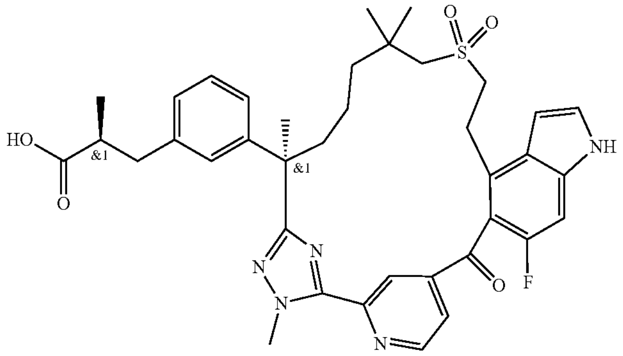 [SMILES: C[C@@H](Cc1cccc([C@@]2(C)CCCC(C)(C)CS(=O)(=O)CCc3c(c(F)cc4[nH]ccc34)C(=O)c3ccnc(c3)-c3nc2nn3C)c1)C(=O)O] |
| 255A | 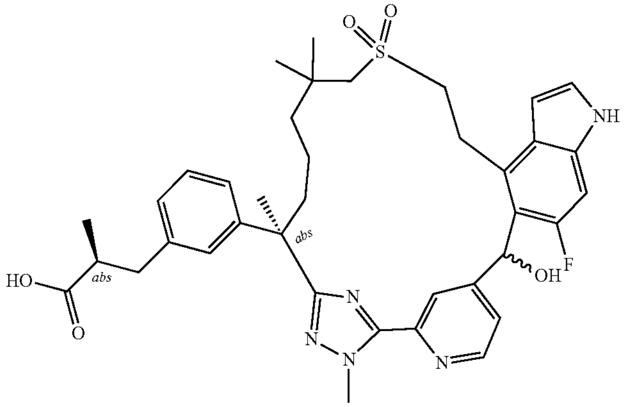 [SMILES: C[C@@H](Cc1cccc([C@@]2(C)CCCC(C)(C)CS(=O)(=O)CCc3c(c(F)cc4[nH]ccc34)C(O)c3ccnc(c3)-c3nc2nn3C)c1)C(=O)O] |
| 255B | 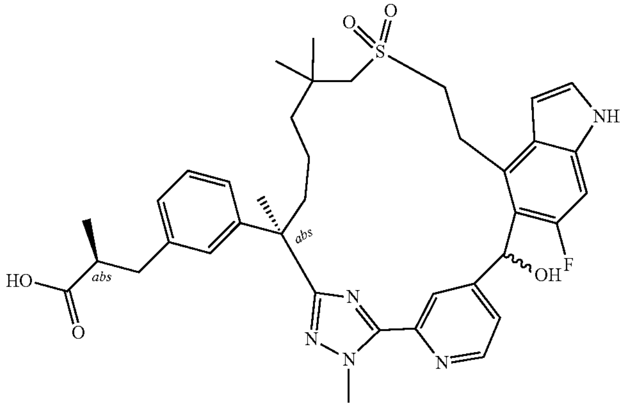 [SMILES: C[C@@H](Cc1cccc([C@@]2(C)CCCC(C)(C)CS(=O)(=O)CCc3c(c(F)cc4[nH]ccc34)C(O)c3ccnc(c3)-c3nc2nn3C)c1)C(=O)O] |
| 256 | 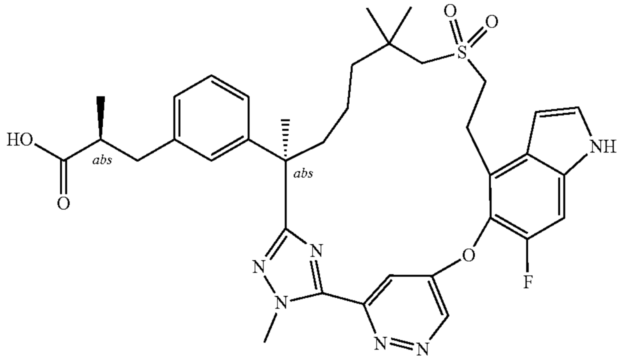 [SMILES: C[C@@H](Cc1cccc([C@@]2(C)CCCC(C)(C)CS(=O)(=O)CCc3c(c(F)cc4[nH]ccc34)Oc3cnnc(c3)-c3nc2nn3C)c1)C(=O)O] |

-continued
| Compound No. | Structures |
| --- | --- |
| 257 | 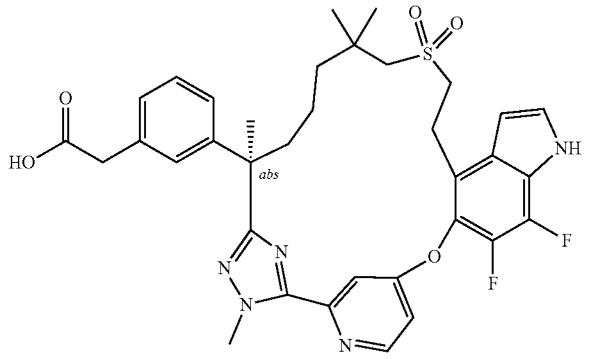 [SMILES: Cn1nc2nc1-c1cc(ccn1)Oc1c(F)c(F)c3[nH]ccc3c1CCS(=O)(=O)CC(C)(C)CCC[C@]2(C)c1cccc(CC(=O)O)c1] |
| 258 | 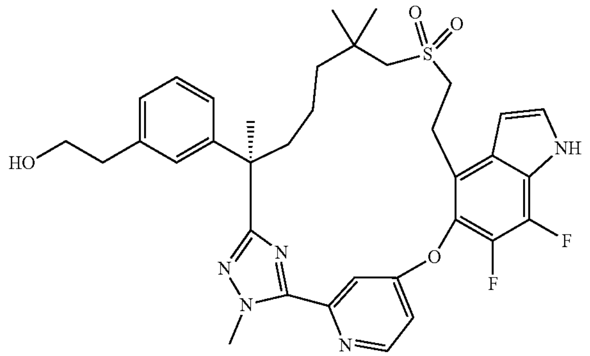 [SMILES: Cn1nc2nc1-c1cc(ccn1)Oc1c(F)c(F)c3[nH]ccc3c1CCS(=O)(=O)CC(C)(C)CCC[C@]2(C)c1cccc(CCO)c1] |
| 259 | 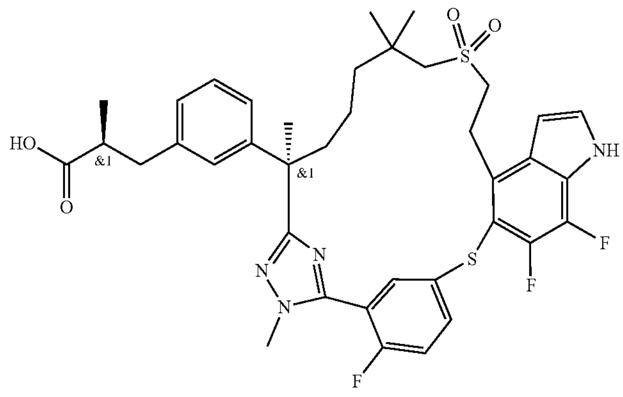 [SMILES: C[C@@H](Cc1cccc([C@@]2(C)CCCC(C)(C)CS(=O)(=O)CCc3c(c(F)c(F)c4[nH]ccc34)Sc3ccc(F)c(c3)-c3nc2nn3C)c1)C(=O)O] |
| 260A | 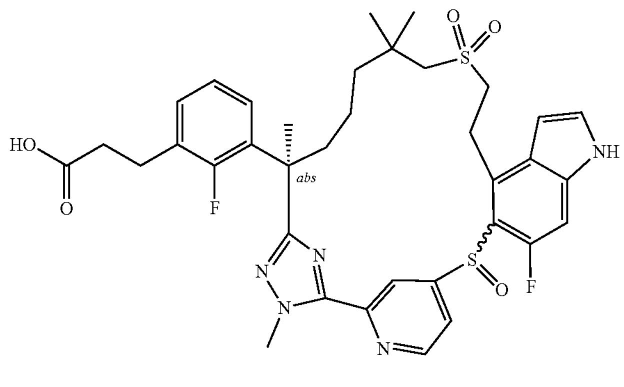 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCC(=O)O)c1F] |

-continued
| Compound No. | Structures |
| --- | --- |
| 260B | 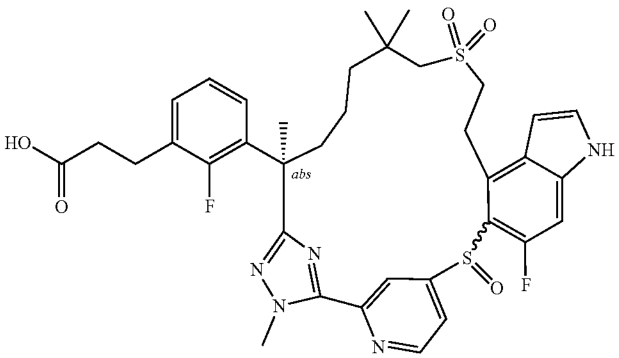 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCC(=O)O)c1F] |
| 261A | 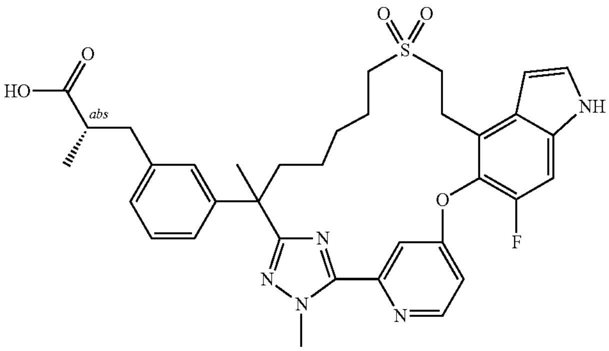 [SMILES: C[C@@H](Cc1cccc(C2(C)CCCCCS(=O)(=O)CCc3c(c(F)cc4[nH]ccc34)Oc3ccnc(c3)-c3nc2nn3C)c1)C(=O)O] |
| 261B | 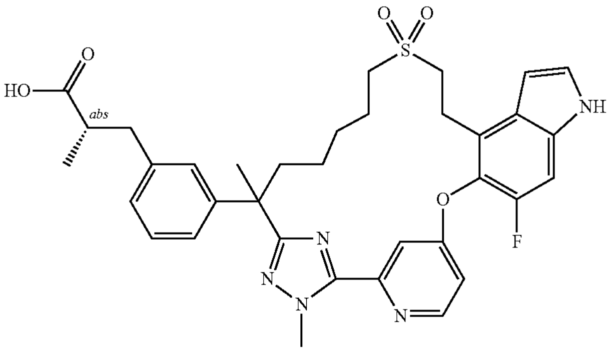 [SMILES: C[C@@H](Cc1cccc(C2(C)CCCCCS(=O)(=O)CCc3c(c(F)cc4[nH]ccc34)Oc3ccnc(c3)-c3nc2nn3C)c1)C(=O)O] |
| 262 | 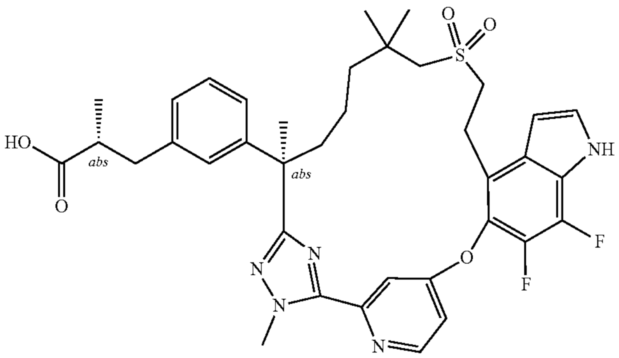 |

-continued
| Compound No. | Structures |
| --- | --- |
| 263 | 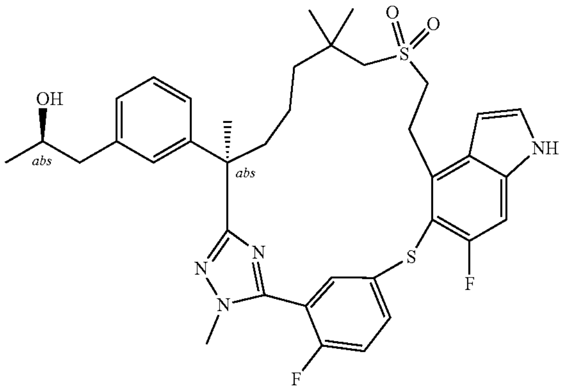 [SMILES: C[C@@H](O)Cc1cccc([C@@]2(C)CCCC(C)(C)CS(=O)(=O)CCc3c(c(F)cc4[nH]ccc34)Sc3ccc(F)c(c3)-c3nc2nn3C)c1] |
| 264 | 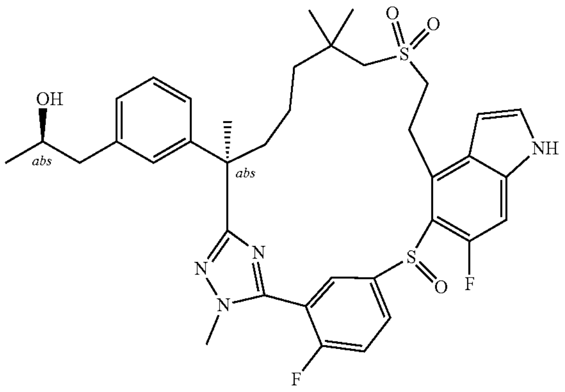 [SMILES: C[C@@H](O)Cc1cccc([C@@]2(C)CCCC(C)(C)CS(=O)(=O)CCc3c(c(F)cc4[nH]ccc34)S(=O)c3ccc(F)c(c3)-c3nc2nn3C)c1] |
| 265 | 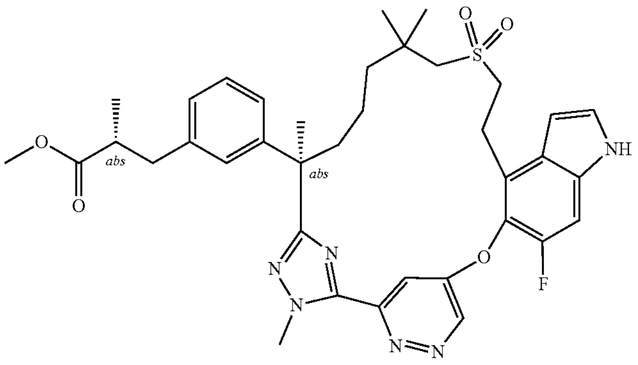 [SMILES: COC(=O)[C@H](C)Cc1cccc([C@@]2(C)CCCC(C)(C)CS(=O)(=O)CCc3c(c(F)cc4[nH]ccc34)Oc3cnnc(c3)-c3nc2nn3C)c1] |
| 266A | 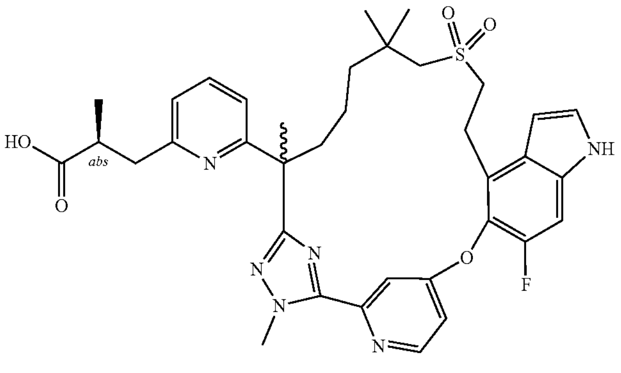 [SMILES: C[C@@H](Cc1cccc(C2(C)CCCC(C)(C)CS(=O)(=O)CCc3c(c(F)cc4[nH]ccc34)Oc3ccnc(c3)-c3nc2nn3C)n1)C(=O)O] |

-continued
| Compound No. | Structures |
| --- | --- |
| 266B | 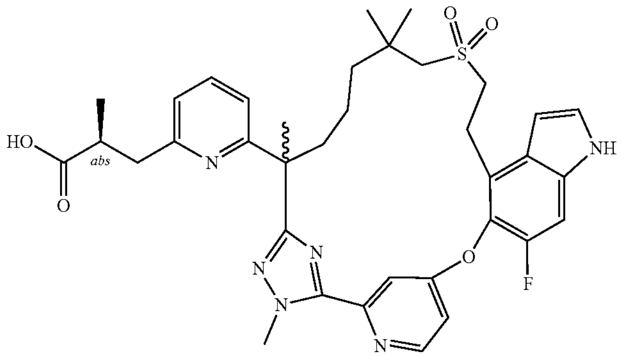 [SMILES: C[C@@H](Cc1cccc(C2(C)CCCC(C)(C)CS(=O)(=O)CCc3c(c(F)cc4[nH]ccc34)Oc3ccnc(c3)-c3nc2nn3C)n1)C(=O)O] |
| 267 | 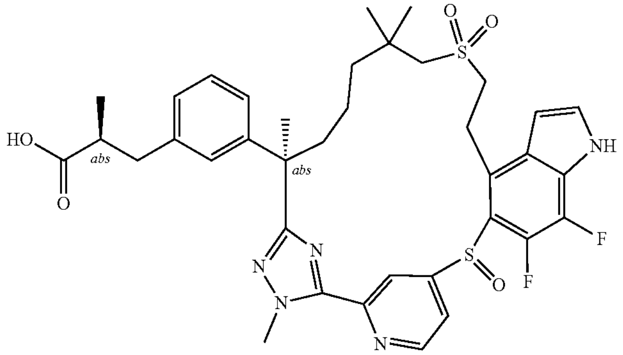 [SMILES: C[C@@H](Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O] |
| 268 | 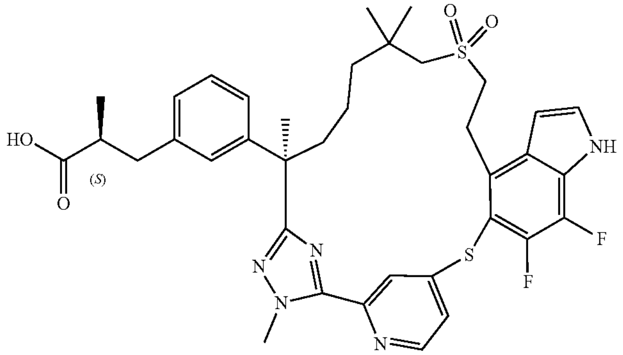 |
| 269 | 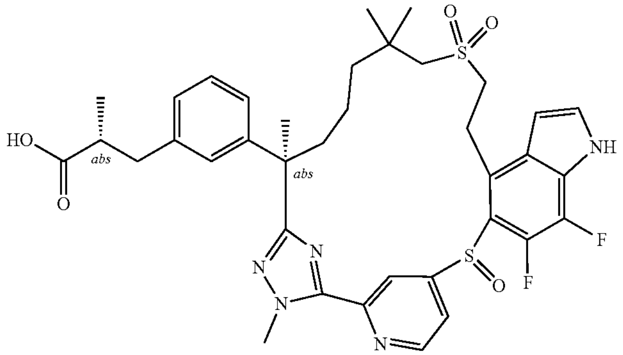 [SMILES: C[C@H](Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O] |

-continued
| Compound No. | Structures |
| --- | --- |
| 270 | 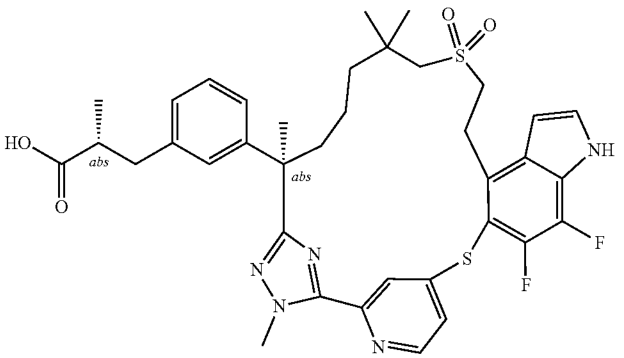 [SMILES: C[C@H](Cc1cccc([C@@]2(C)CCCC(C)(C)CS(=O)(=O)CCc3c(c(F)c(F)c4[nH]ccc34)Sc3ccnc(c3)-c3nc2nn3C)c1)C(=O)O] |
| 271 | 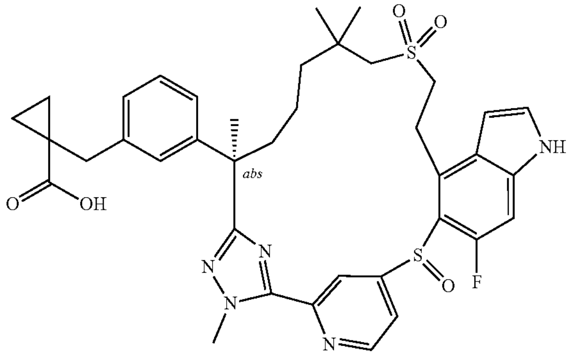 [SMILES: Cn1nc2nc1-c1cc(ccn1)S(=O)c1c(F)cc3[nH]ccc3c1CCS(=O)(=O)CC(C)(C)CCC[C@]2(C)c1cccc(CC2(C(=O)O)CC2)c1] |
| 272 | 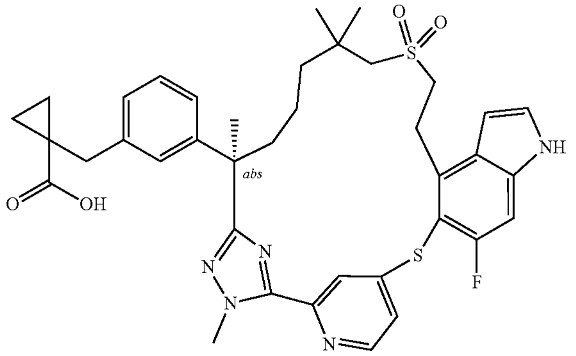 |
| 273 | 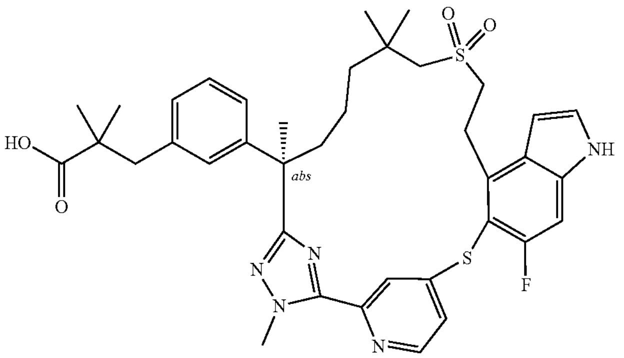 |

-continued
| Compound No. | Structures |
| --- | --- |
| 274 | 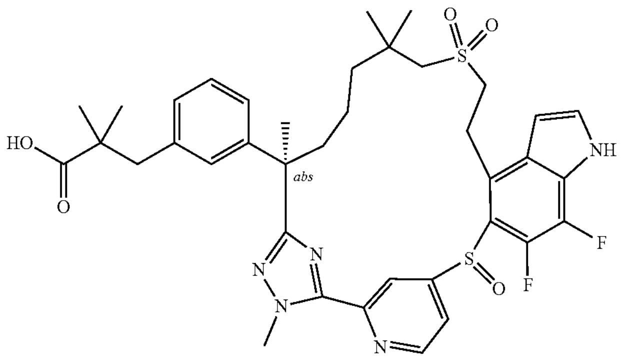 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(CC(C)(C)C(=O)O)c1] |
| 275 | 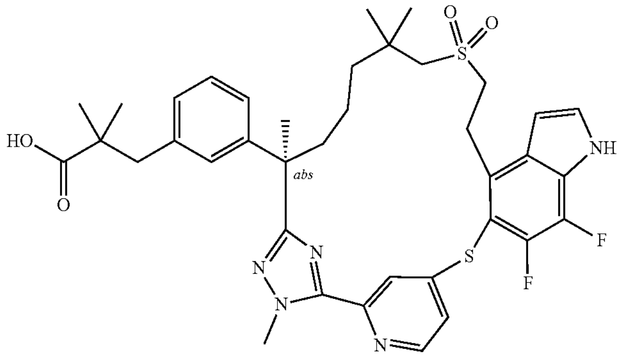 [SMILES: Cn1nc2nc1-c1cc(ccn1)Sc1c(F)c(F)c3[nH]ccc3c1CCS(=O)(=O)CC(C)(C)CCC[C@]2(C)c1cccc(CC(C)(C)C(=O)O)c1] |
| 276 | 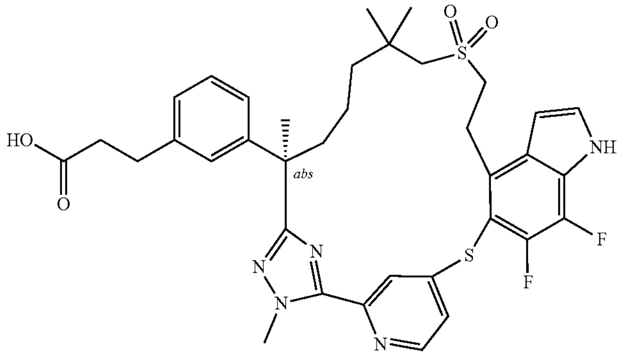 [SMILES: Cn1nc2nc1-c1cc(ccn1)Sc1c(F)c(F)c3[nH]ccc3c1CCS(=O)(=O)CC(C)(C)CCC[C@]2(C)c1cccc(CCC(=O)O)c1] |
| 277 | 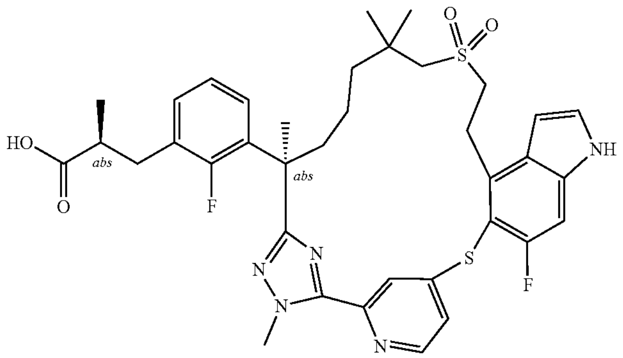 [SMILES: C[C@@H](Cc1cccc([C@@]2(C)CCCC(C)(C)CS(=O)(=O)CCc3c(c(F)cc4[nH]ccc34)Sc3ccnc(c3)-c3nc2nn3C)c1F)C(=O)O] |

-continued
| Compound No. | Structures |
|---|---|
| 278 | 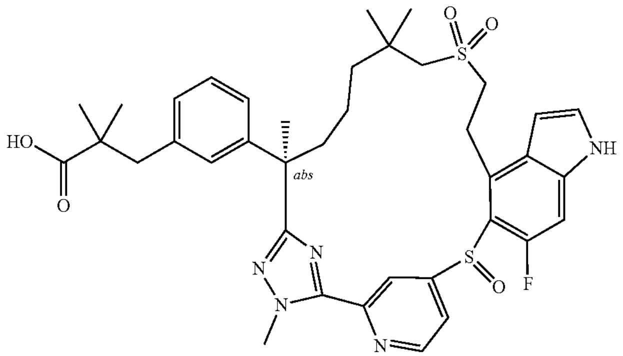 [SMILES: Cn1nc2nc1-c1cc(ccn1)S(=O)c1c(F)cc3[nH]ccc3c1CCS(=O)(=O)CC(C)(C)CCC[C@]2(C)c1cccc(CC(C)(C)C(=O)O)c1] |
| 279 | 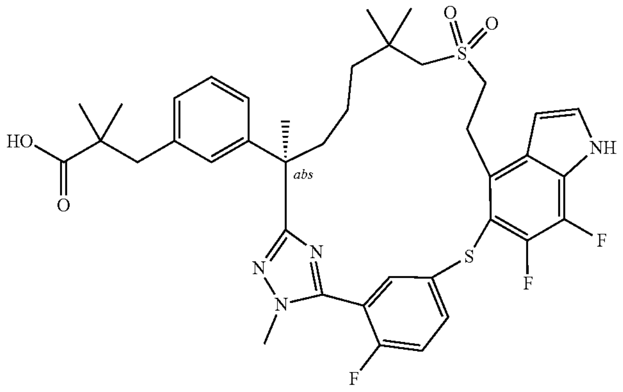 [SMILES: Cn1nc2nc1-c1cc(ccc1F)Sc1c(F)c(F)c3[nH]ccc3c1CCS(=O)(=O)CC(C)(C)CCC[C@]2(C)c1cccc(CC(C)(C)C(=O)O)c1] |
| 280 | 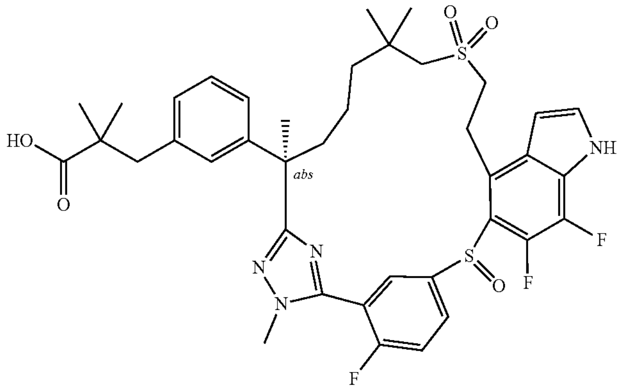 [SMILES: Cn1nc2nc1-c1cc(ccc1F)S(=O)c1c(F)c(F)c3[nH]ccc3c1CCS(=O)(=O)CC(C)(C)CCC[C@]2(C)c1cccc(CC(C)(C)C(=O)O)c1] |
| 281 | 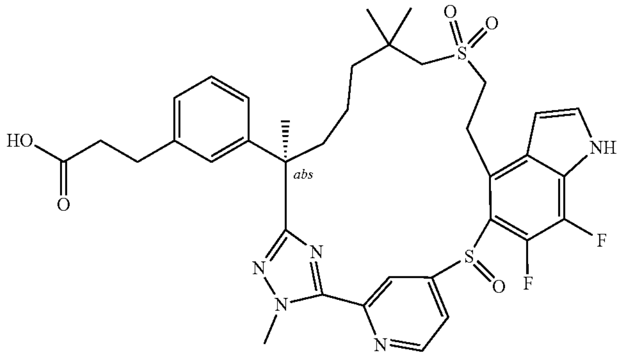 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(CCC(=O)O)c1] |

-continued
| Compound No. | Structures |
|---|---|
| 282 | 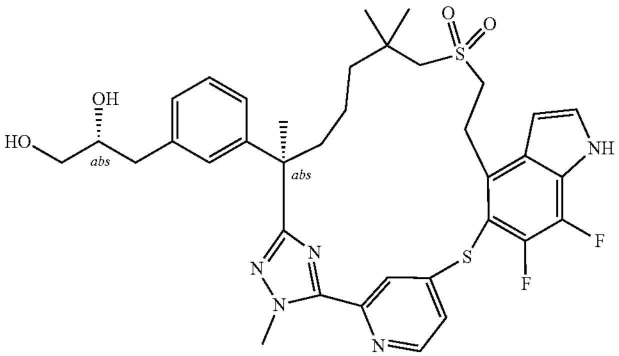 [SMILES: Cn1nc2nc1-c1cc(ccn1)Sc1c(F)c(F)c3[nH]ccc3c1CCS(=O)(=O)CC(C)(C)CCC[C@]2(C)c1cccc(C[C@@H](O)CO)c1] |
| 283 | 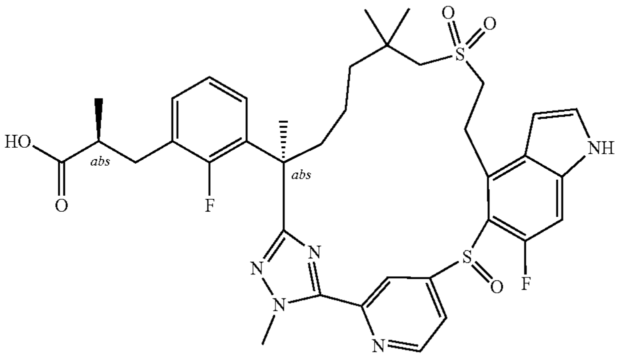 [SMILES: C[C@@H](Cc1cccc([C@@]2(C)CCCC(C)(C)CS(=O)(=O)CCc3c(c(F)cc4[nH]ccc34)S(=O)c3ccnc(c3)-c3nc2nn3C)c1F)C(=O)O] |
| 284 | 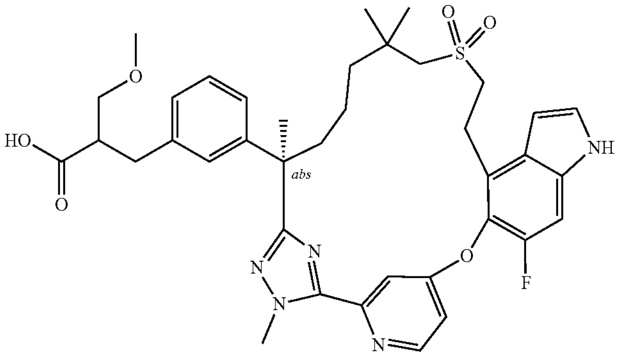 [SMILES: COCC(Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O] |
| 285 | 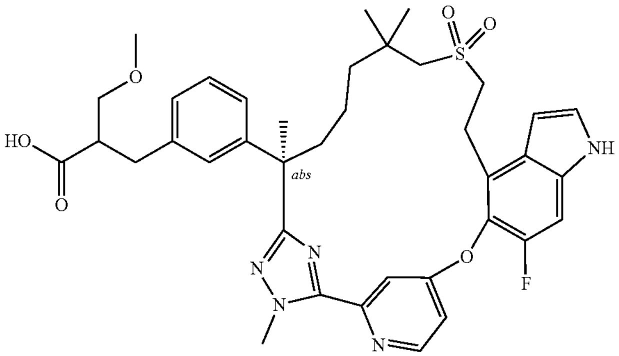 [SMILES: COCC(Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O] |

-continued
| Compound No. | Structures |
|---|---|
| 286 | 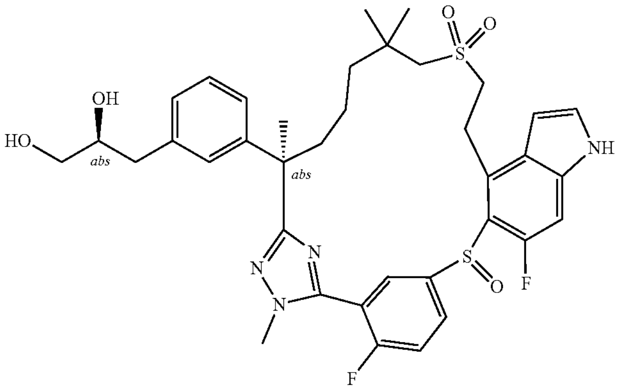 [SMILES: Cn1nc2nc1-c1cc(ccc1F)S(=O)c1c(F)cc3[nH]ccc3c1CCS(=O)(=O)CC(C)(C)CCC[C@]2(C)c1cccc(C[C@H](O)CO)c1] |
| 287 | 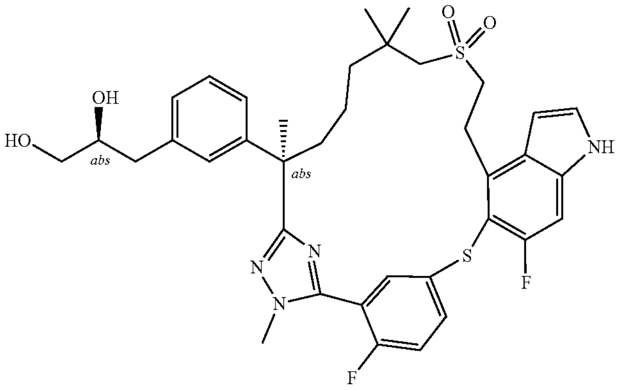 [SMILES: Cn1nc2nc1-c1cc(ccc1F)Sc1c(F)cc3[nH]ccc3c1CCS(=O)(=O)CC(C)(C)CCC[C@]2(C)c1cccc(C[C@H](O)CO)c1] |
| 288 | 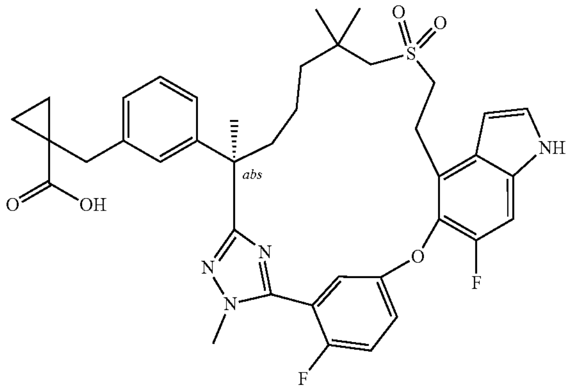 [SMILES: Cn1nc2nc1-c1cc(ccc1F)Oc1c(F)cc3[nH]ccc3c1CCS(=O)(=O)CC(C)(C)CCC[C@]2(C)c1cccc(CC2(C(=O)O)CC2)c1] |
| 289 | 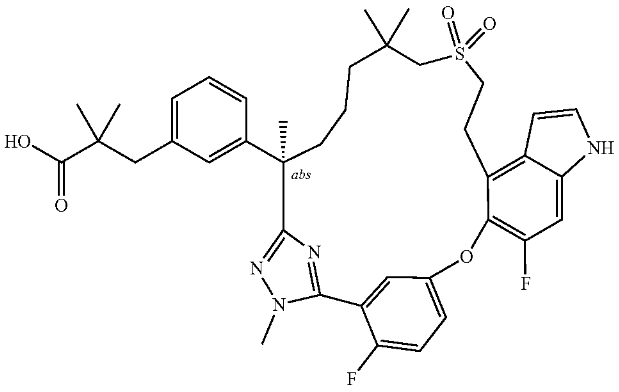 [SMILES: Cn1nc2nc1-c1cc(ccc1F)Oc1c(F)cc3[nH]ccc3c1CCS(=O)(=O)CC(C)(C)CCC[C@]2(C)c1cccc(CC(C)(C)C(=O)O)c1] |

-continued
| Compound No. | Structures |
| --- | --- |
| 290 | 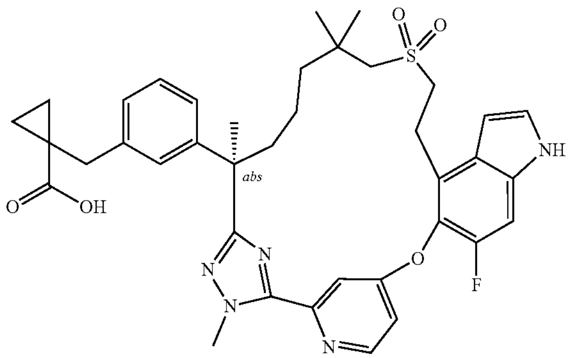 [SMILES: Cn1nc2nc1-c1cc(ccn1)Oc1c(F)cc3[nH]ccc3c1CCS(=O)(=O)CC(C)(C)CCC[C@]2(C)c1cccc(CC2(C(=O)O)CC2)c1] |
| 291 | 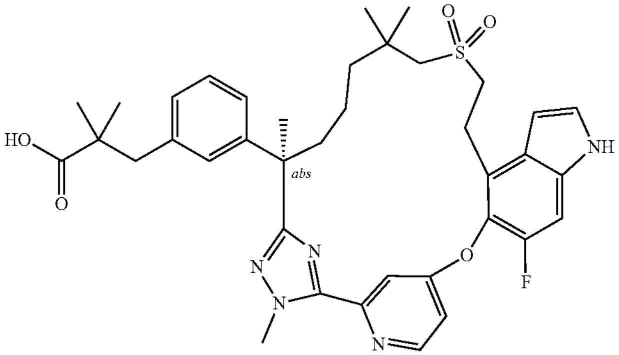 [SMILES: Cn1nc2nc1-c1cc(ccn1)Oc1c(F)cc3[nH]ccc3c1CCS(=O)(=O)CC(C)(C)CCC[C@]2(C)c1cccc(CC(C)(C)C(=O)O)c1] |
| 292 | 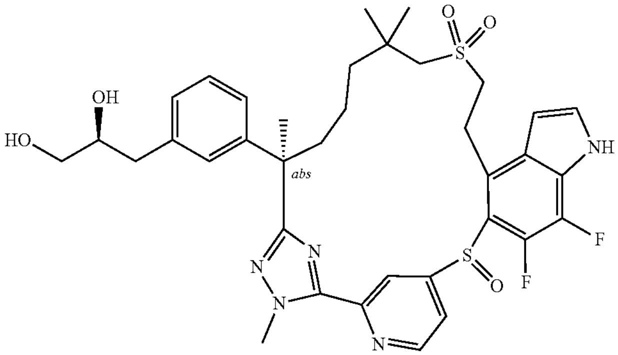 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(C[C@H](O)CO)c1] |
| 293 | 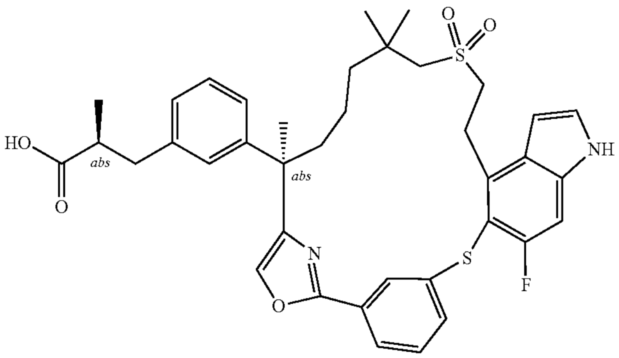 [SMILES: C[C@@H](Cc1cccc([C@@]2(C)CCCC(C)(C)CS(=O)(=O)CCc3c(c(F)cc4[nH]ccc34)Sc3cccc(c3)-c3nc2co3)c1)C(=O)O] |

-continued
| Compound No. | Structures |
| --- | --- |
| 294 | 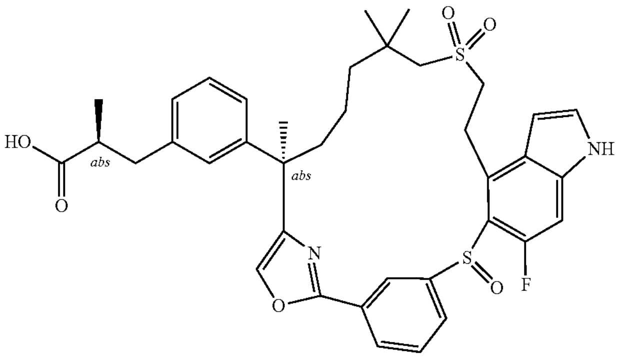 [SMILES: C[C@@H](Cc1cccc([C@@]2(C)CCCC(C)(C)CS(=O)(=O)CCc3c(c(F)cc4[nH]ccc34)S(=O)c3cccc(c3)-c3nc2co3)c1)C(=O)O] |
| 295 | 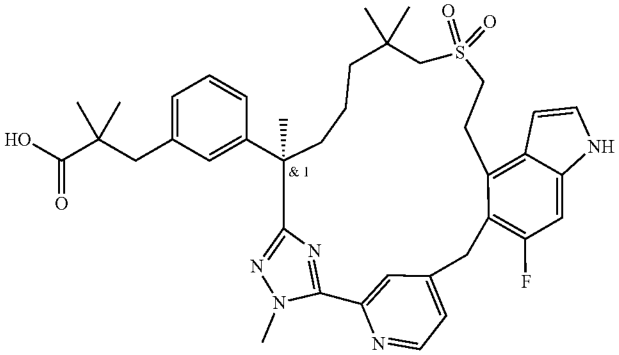 |
| 296 | 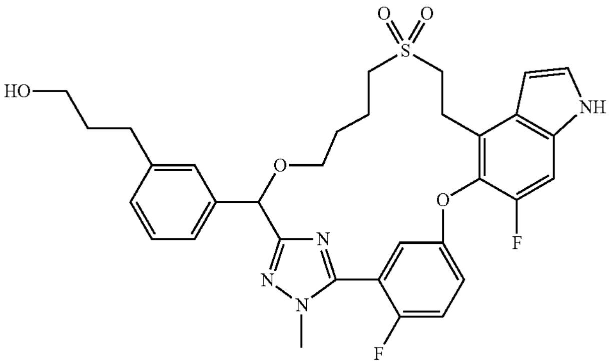 [SMILES: Cn1nc2nc1-c1cc(ccc1F)Oc1c(F)cc3[nH]ccc3c1CCS(=O)(=O)CCCCOC2c1cccc(CCCO)c1] |
| 297 | 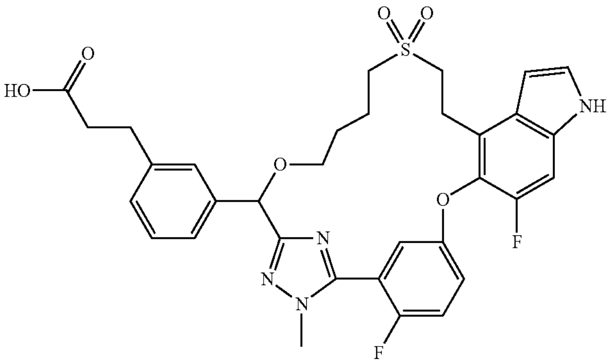 [SMILES: Cn1nc2nc1-c1cc(ccc1F)Oc1c(F)cc3[nH]ccc3c1CCS(=O)(=O)CCCCOC2c1cccc(CCC(=O)O)c1] |

-continued
| Compound No. | Structures |
| --- | --- |
| 299A | 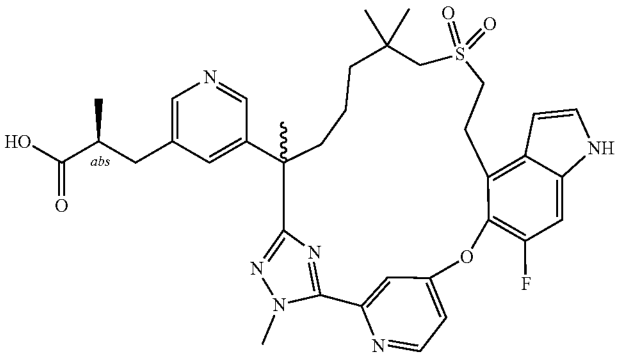 [SMILES: C[C@@H](Cc1cncc(C2(C)CCCC(C)(C)CS(=O)(=O)CCc3c(c(F)cc4[nH]ccc34)Oc3ccnc(c3)-c3nc2nn3C)c1)C(=O)O] |
| 299B | 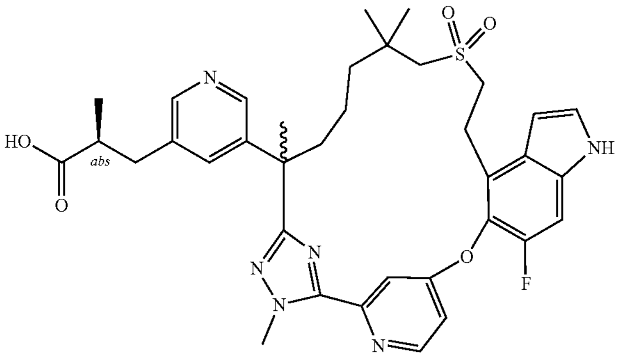 [SMILES: C[C@@H](Cc1cncc(C2(C)CCCC(C)(C)CS(=O)(=O)CCc3c(c(F)cc4[nH]ccc34)Oc3ccnc(c3)-c3nc2nn3C)c1)C(=O)O] |
| 300A | 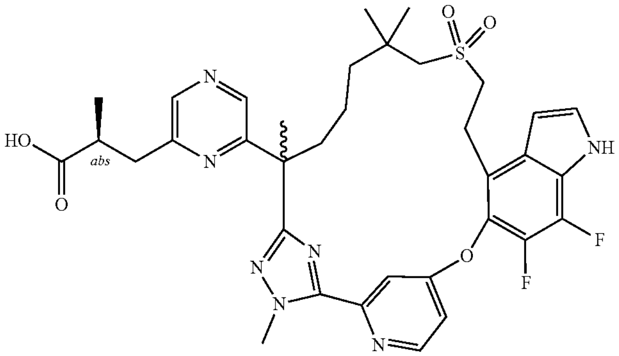 [SMILES: C[C@@H](Cc1cncc(C2(C)CCCC(C)(C)CS(=O)(=O)CCc3c(c(F)c(F)c4[nH]ccc34)Oc3ccnc(c3)-c3nc2nn3C)n1)C(=O)O] |
| 300B | 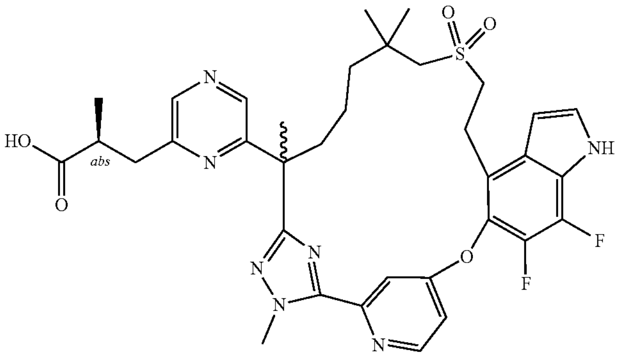 [SMILES: C[C@@H](Cc1cncc(C2(C)CCCC(C)(C)CS(=O)(=O)CCc3c(c(F)c(F)c4[nH]ccc34)Oc3ccnc(c3)-c3nc2nn3C)n1)C(=O)O] |

-continued
| Compound No. | Structures |
| --- | --- |
| 301 | 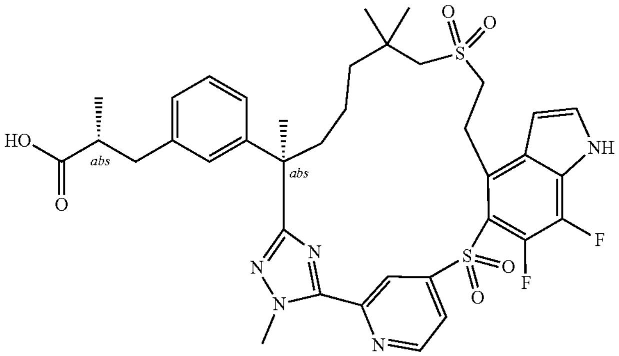 [SMILES: C[C@H](Cc1cccc([C@@]2(C)CCCC(C)(C)CS(=O)(=O)CCc3c(c(F)c(F)c4[nH]ccc34)S(=O)(=O)c3ccnc(c3)-c3nc2nn3C)c1)C(=O)O] |
| 302A | 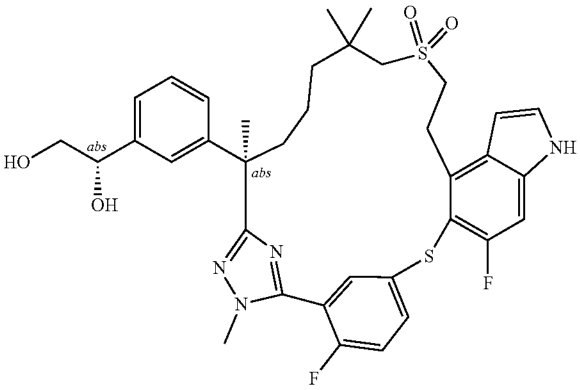 [SMILES: Cn1nc2nc1-c1cc(ccc1F)Sc1c(F)cc3[nH]ccc3c1CCS(=O)(=O)CC(C)(C)CCC[C@]2(C)c1cccc([C@H](O)CO)c1] |
| 302B | 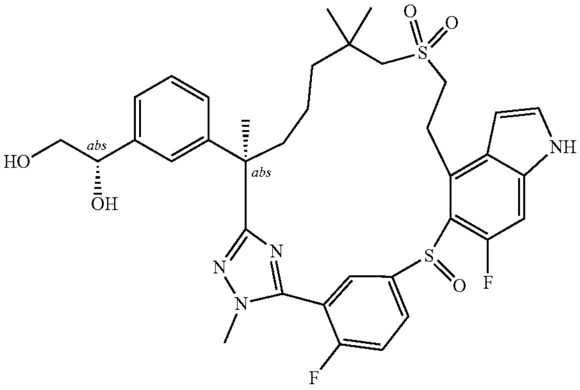 [SMILES: Cn1nc2nc1-c1cc(ccc1F)S(=O)c1c(F)cc3[nH]ccc3c1CCS(=O)(=O)CC(C)(C)CCC[C@]2(C)c1cccc([C@H](O)CO)c1] |
| 303A | 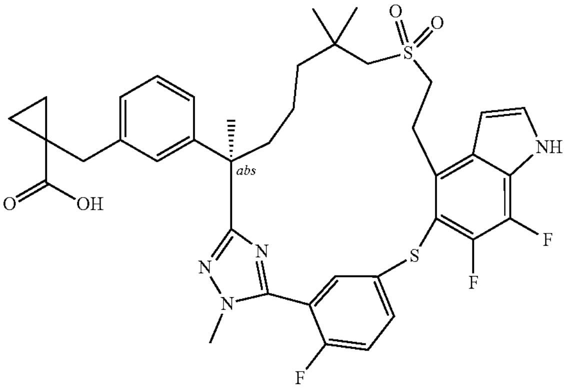 [SMILES: Cn1nc2nc1-c1cc(ccc1F)Sc1c(F)c(F)c3[nH]ccc3c1CCS(=O)(=O)CC(C)(C)CCC[C@]2(C)c1cccc(CC2(C(=O)O)CC2)c1] |

-continued
| Compound No. | Structures |
|---|---|
| 303B | 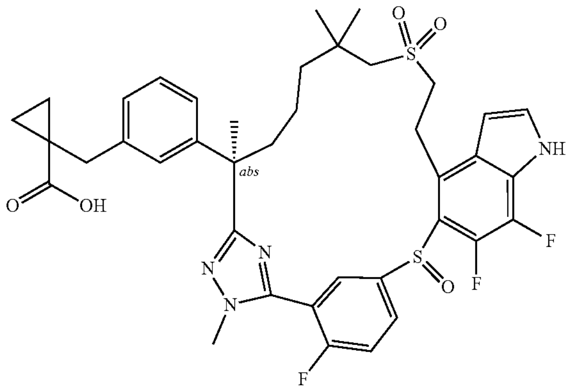 [SMILES: Cn1nc2nc1-c1cc(ccc1F)S(=O)c1c(F)c(F)c3[nH]ccc3c1CCS(=O)(=O)CC(C)(C)CCC[C@]2(C)c1cccc(CC2(C(=O)O)CC2)c1] |
| 304 | 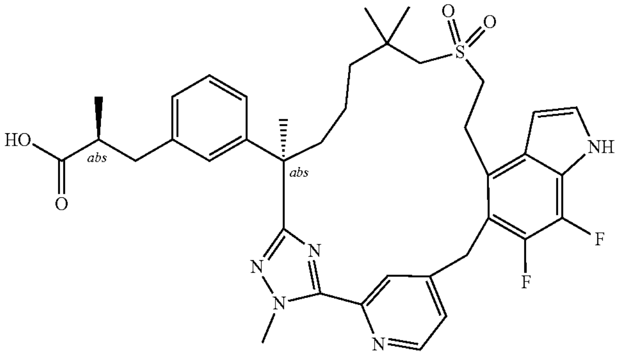 [SMILES: C[C@@H](Cc1cccc([C@@]2(C)CCCC(C)(C)CS(=O)(=O)CCc3c(c(F)c(F)c4[nH]ccc34)Cc3ccnc(c3)-c3nc2nn3C)c1)C(=O)O] |
| 305 | 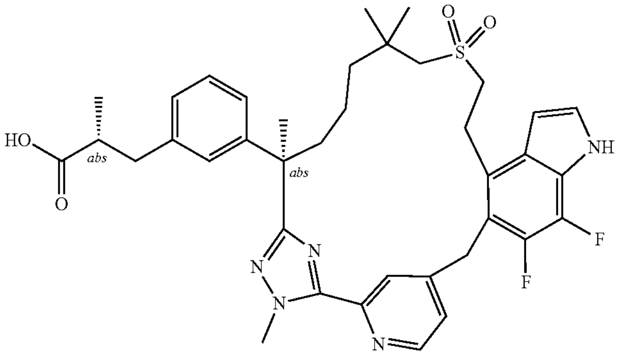 [SMILES: C[C@H](Cc1cccc([C@@]2(C)CCCC(C)(C)CS(=O)(=O)CCc3c(c(F)c(F)c4[nH]ccc34)Cc3ccnc(c3)-c3nc2nn3C)c1)C(=O)O] |
| 306 | 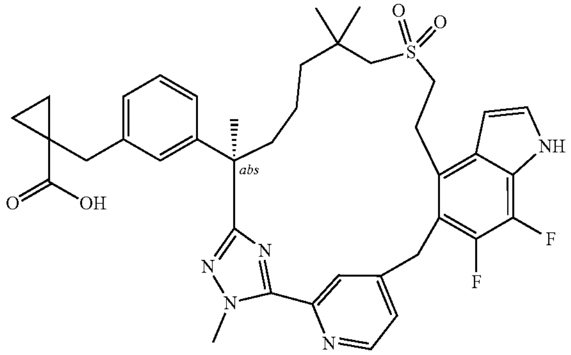 |

-continued
| Compound No. | Structures |
| --- | --- |
| 307 | 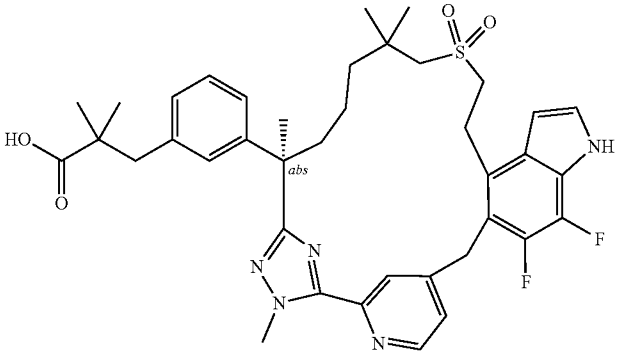 [SMILES: Cn1nc2nc1-c1cc(ccn1)Cc1c(F)c(F)c3[nH]ccc3c1CCS(=O)(=O)CC(C)(C)CCC[C@]2(C)c1cccc(CC(C)(C)C(=O)O)c1] |
| 308 | 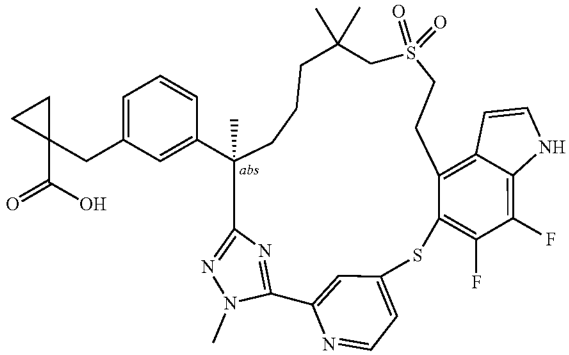 [SMILES: Cn1nc2nc1-c1cc(ccn1)Sc1c(F)c(F)c3[nH]ccc3c1CCS(=O)(=O)CC(C)(C)CCC[C@]2(C)c1cccc(CC2(C(=O)O)CC2)c1] |
| 309 | 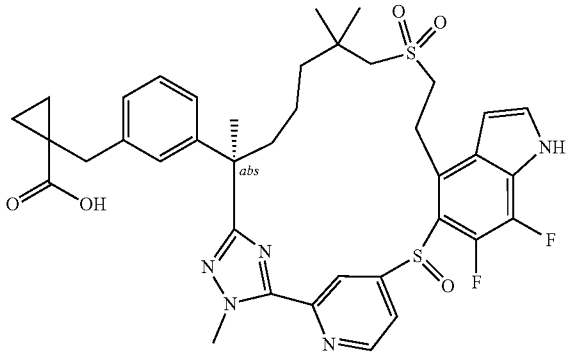 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(CC2(C(=O)O)CC2)c1] |
| 310 | 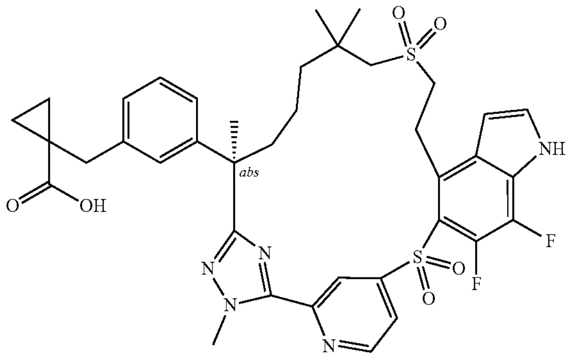 [SMILES: Cn1nc2nc1-c1cc(ccn1)S(=O)(=O)c1c(F)c(F)c3[nH]ccc3c1CCS(=O)(=O)CC(C)(C)CCC[C@]2(C)c1cccc(CC2(C(=O)O)CC2)c1] |

-continued
| Compound No. | Structures |
| --- | --- |
| 311 | 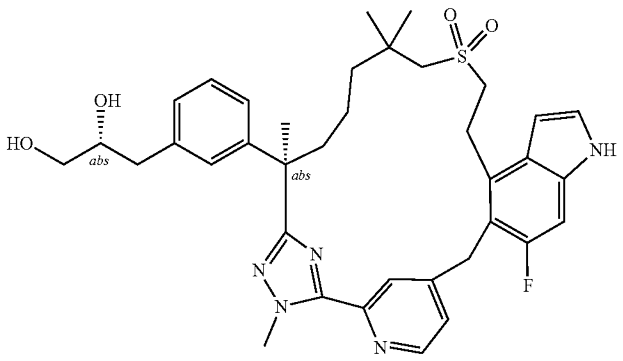 [SMILES: Cn1nc2nc1-c1cc(ccn1)Cc1c(F)cc3[nH]ccc3c1CCS(=O)(=O)CC(C)(C)CCC[C@]2(C)c1cccc(C[C@@H](O)CO)c1] |
| 312 | 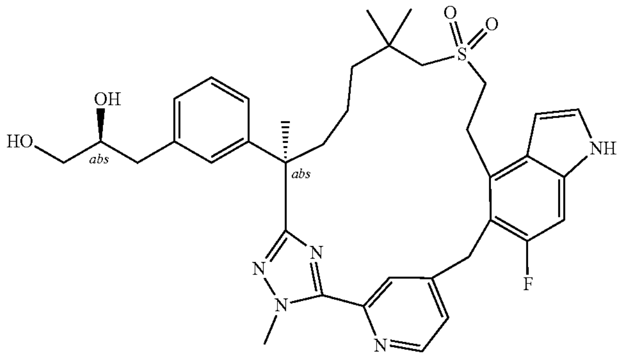 [SMILES: Cn1nc2nc1-c1cc(ccn1)Cc1c(F)cc3[nH]ccc3c1CCS(=O)(=O)CC(C)(C)CCC[C@]2(C)c1cccc(C[C@H](O)CO)c1] |
| 313 | 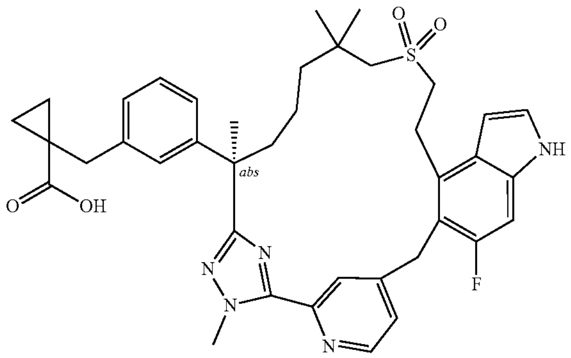 |
| 314A | 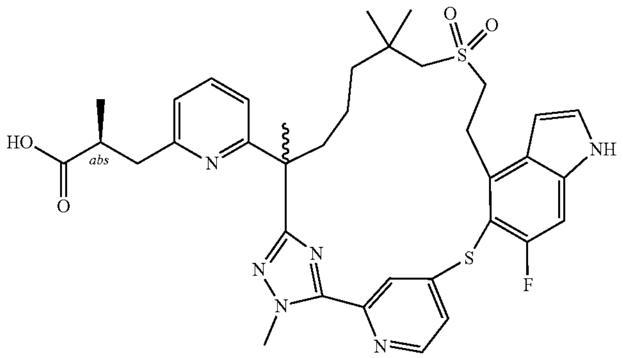 [SMILES: C[C@@H](Cc1cccc(C2(C)CCCC(C)(C)CS(=O)(=O)CCc3c(c(F)cc4[nH]ccc34)Sc3ccnc(c3)-c3nc2nn3C)n1)C(=O)O] |

-continued
| Compound No. | Structures |
| --- | --- |
| 314B | 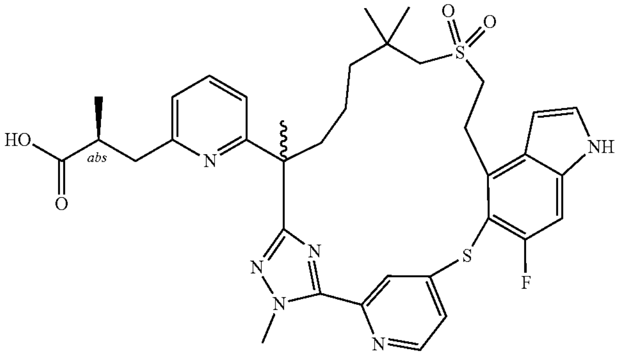 [SMILES: C[C@@H](Cc1cccc(C2(C)CCCC(C)(C)CS(=O)(=O)CCc3c(c(F)cc4[nH]ccc34)Sc3ccnc(c3)-c3nc2nn3C)n1)C(=O)O] |
| 315A | 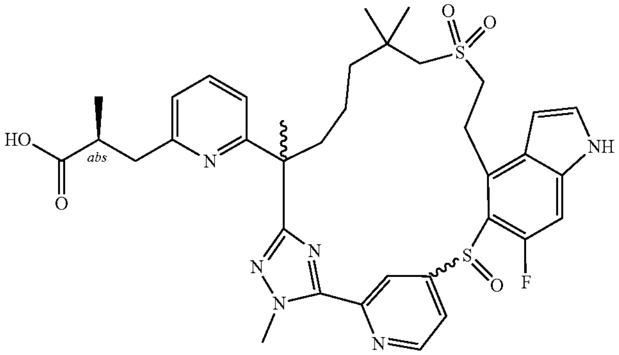 [SMILES: C[C@@H](Cc1cccc(C2(C)CCCC(C)(C)CS(=O)(=O)CCc3c(c(F)cc4[nH]ccc34)S(=O)c3ccnc(c3)-c3nc2nn3C)n1)C(=O)O] |
| 315B | 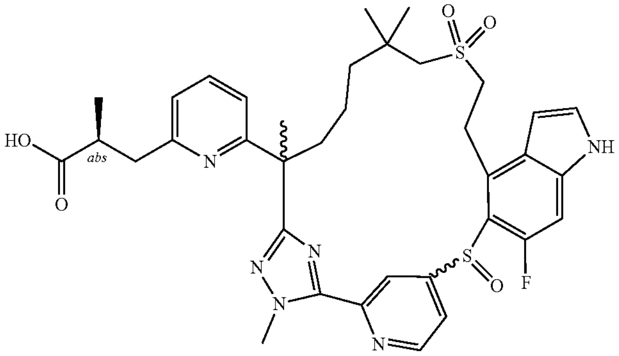 [SMILES: C[C@@H](Cc1cccc(C2(C)CCCC(C)(C)CS(=O)(=O)CCc3c(c(F)cc4[nH]ccc34)S(=O)c3ccnc(c3)-c3nc2nn3C)n1)C(=O)O] |
| 315C | 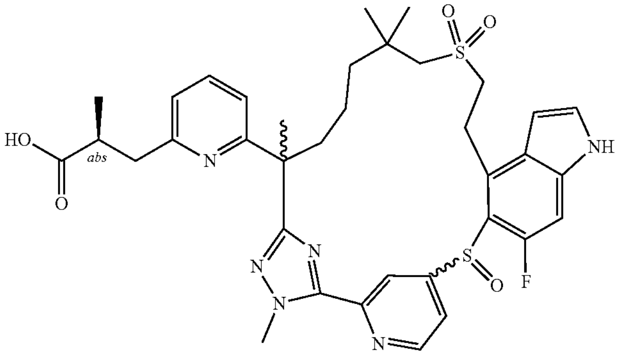 [SMILES: C[C@@H](Cc1cccc(C2(C)CCCC(C)(C)CS(=O)(=O)CCc3c(c(F)cc4[nH]ccc34)S(=O)c3ccnc(c3)-c3nc2nn3C)n1)C(=O)O] |

-continued
| Compound No. | Structures |
|---|---|
| 315D | 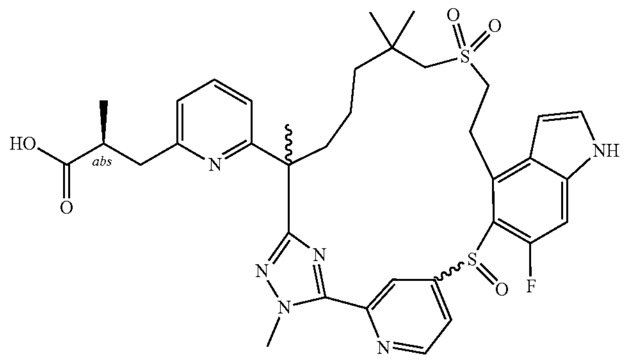 [SMILES: C[C@@H](Cc1cccc(C2(C)CCCC(C)(C)CS(=O)(=O)CCc3c(c(F)cc4[nH]ccc34)S(=O)c3ccnc(c3)-c3nc2nn3C)n1)C(=O)O] |
| 315E | 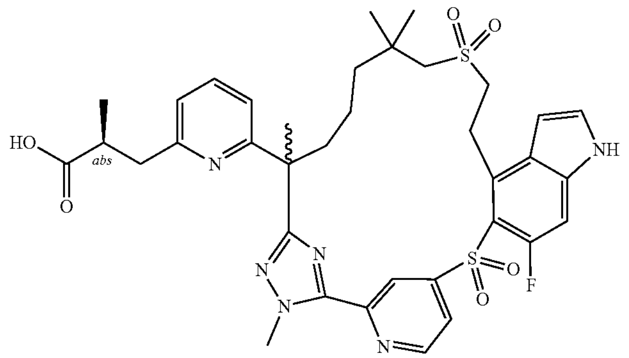 [SMILES: C[C@@H](Cc1cccc(C2(C)CCCC(C)(C)CS(=O)(=O)CCc3c(c(F)cc4[nH]ccc34)S(=O)(=O)c3ccnc(c3)-c3nc2nn3C)n1)C(=O)O] |
| 316A | 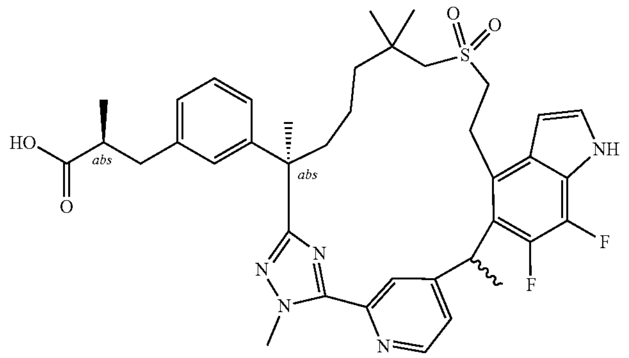 [SMILES: CC1c2ccnc(c2)-c2nc(nn2C)[C@@](C)(c2cccc(C[C@H](C)C(=O)O)c2)CCCC(C)(C)CS(=O)(=O)CCc2c1c(F)c(F)c1[nH]ccc21] |
| 316B | 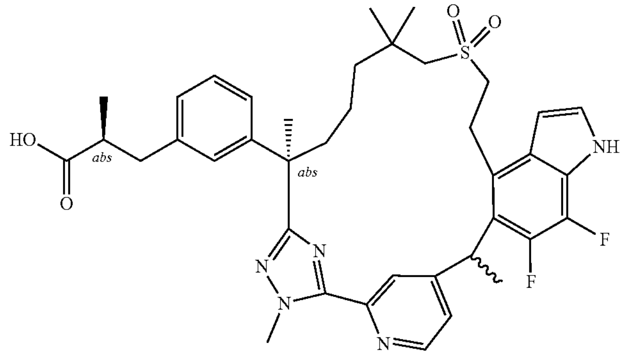 [SMILES: CC1c2ccnc(c2)-c2nc(nn2C)[C@@](C)(c2cccc(C[C@H](C)C(=O)O)c2)CCCC(C)(C)CS(=O)(=O)CCc2c1c(F)c(F)c1[nH]ccc21] |

-continued
| Compound No. | Structures |
|---|---|
| 317A | 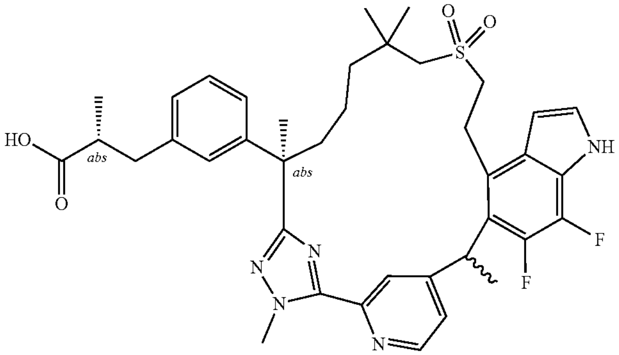 [SMILES: CC1c2ccnc(c2)-c2nc(nn2C)[C@@](C)(c2cccc(C[C@@H](C)C(=O)O)c2)CCCC(C)(C)CS(=O)(=O)CCc2c1c(F)c(F)c1[nH]ccc21] |
| 317B | 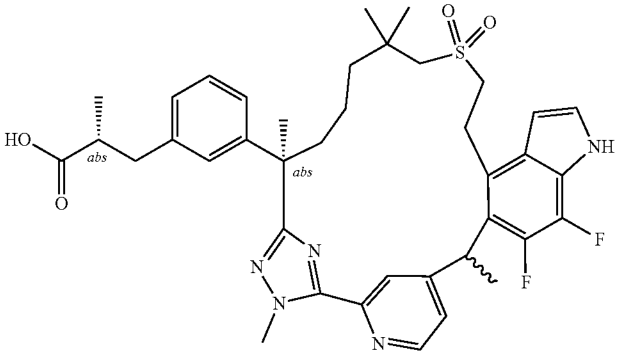 [SMILES: CC1c2ccnc(c2)-c2nc(nn2C)[C@@](C)(c2cccc(C[C@@H](C)C(=O)O)c2)CCCC(C)(C)CS(=O)(=O)CCc2c1c(F)c(F)c1[nH]ccc21] |
| 318A | 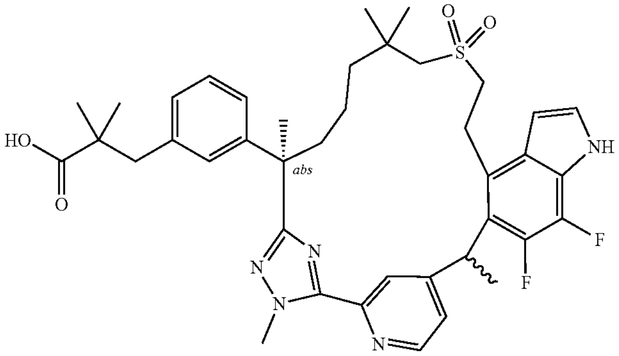 [SMILES: CC1c2ccnc(c2)-c2nc(nn2C)[C@@](C)(c2cccc(CC(C)(C)C(=O)O)c2)CCCC(C)(C)CS(=O)(=O)CCc2c1c(F)c(F)c1[nH]ccc21] |
| 318B | 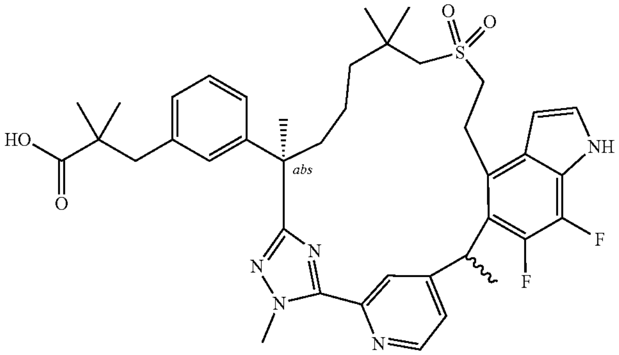 [SMILES: CC1c2ccnc(c2)-c2nc(nn2C)[C@@](C)(c2cccc(CC(C)(C)C(=O)O)c2)CCCC(C)(C)CS(=O)(=O)CCc2c1c(F)c(F)c1[nH]ccc21] |

-continued
| Compound No. | Structures |
| --- | --- |
| 319 | 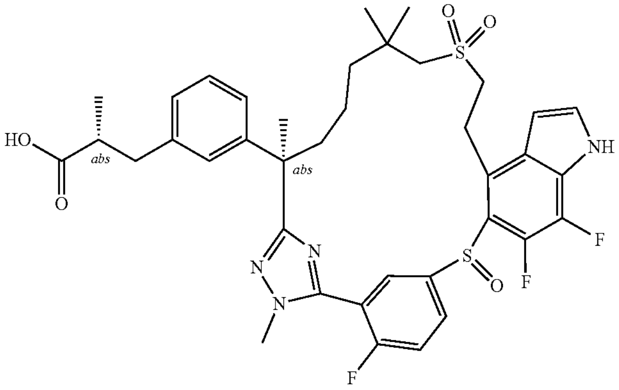 [SMILES: C[C@H](Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O] |
| 320 | 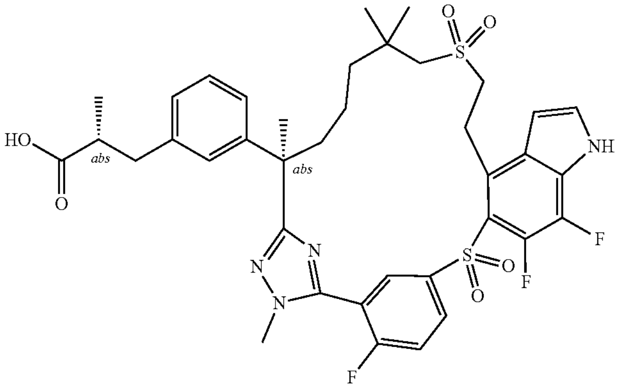 [SMILES: C[C@H](Cc1cccc([C@@]2(C)CCCC(C)(C)CS(=O)(=O)CCc3c(c(F)c(F)c4[nH]ccc34)S(=O)(=O)c3ccc(F)c(c3)-c3nc2nn3C)c1)C(=O)O] |
| 321 | 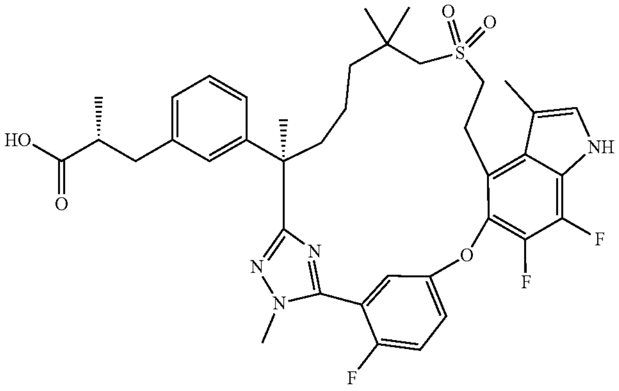 [SMILES: Cc1c[nH]c2c(F)c(F)c3c(c12)CCS(=O)(=O)CC(C)(C)CCC[C@](C)(c1cccc(C[C@@H](C)C(=O)O)c1)c1nc(n(C)n1)-c1cc(ccc1F)O3] |
| 322 | 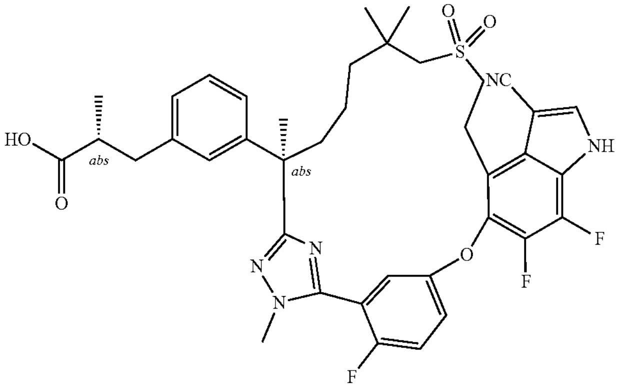 [SMILES: C[C@H](Cc1cccc([C@@]2(C)CCCC(C)(C)CS(=O)(=O)CCc3c(c(F)c(F)c4[nH]cc(C#N)c34)Oc3ccc(F)c(c3)-c3nc2nn3C)c1)C(=O)O] |

-continued
| Compound No. | Structures |
| --- | --- |
| 323 | 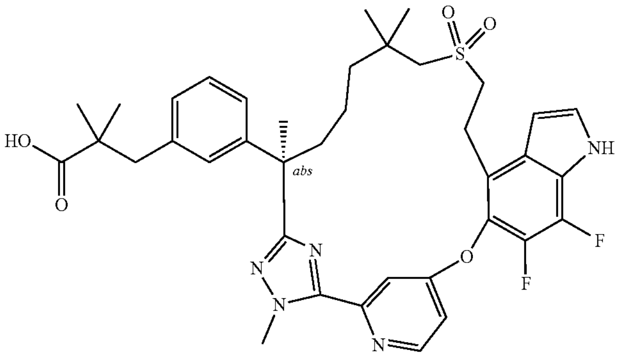 |
| 324 | 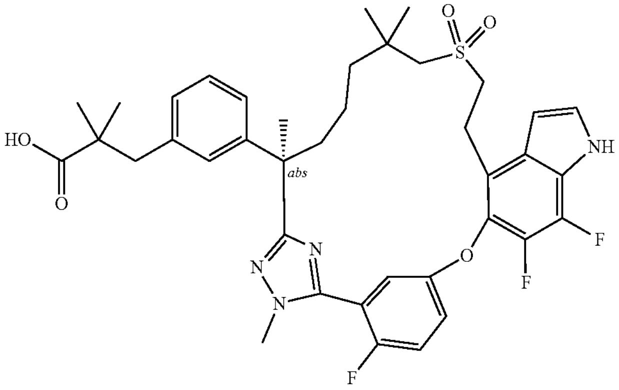 |
| 325 | 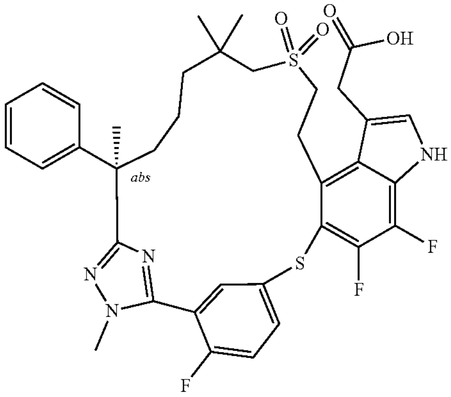 [SMILES: Cn1nc2nc1-c1cc(ccc1F)Sc1c(F)c(F)c3[nH]cc(CC(=O)O)c3c1CCS(=O)(=O)CC(C)(C)CCC[C@]2(C)c1ccccc1] |
| 326 | 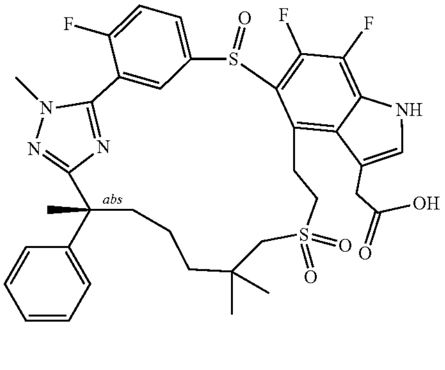 [SMILES: Cn1nc2nc1-c1cc(ccc1F)S(=O)c1c(F)c(F)c3[nH]cc(CC(=O)O)c3c1CCS(=O)(=O)CC(C)(C)CCC[C@]2(C)c1ccccc1] |

-continued
| Compound No. | Structures |
| --- | --- |
| 327 | 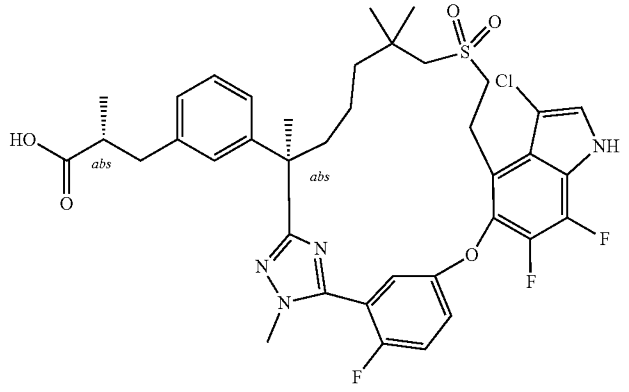 [SMILES: C[C@H](Cc1cccc([C@@]2(C)CCCC(C)(C)CS(=O)(=O)CCc3c(c(F)c(F)c4[nH]cc(Cl)c34)Oc3ccc(F)c(c3)-c3nc2nn3C)c1)C(=O)O] |
| 328 | 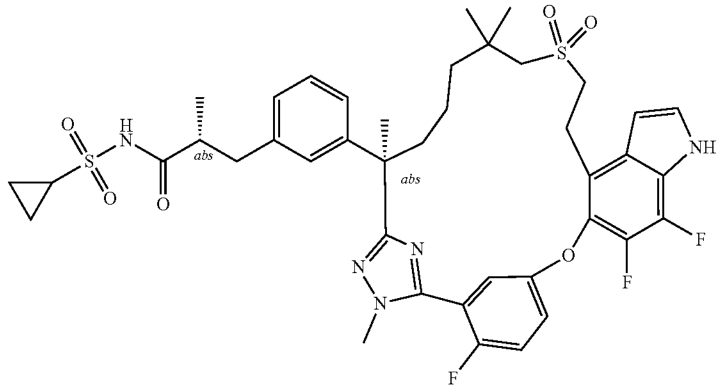 [SMILES: C[C@H](Cc1cccc([C@@]2(C)CCCC(C)(C)CS(=O)(=O)CCc3c(c(F)c(F)c4[nH]ccc34)Oc3ccc(F)c(c3)-c3nc2nn3C)c1)C(=O)NS(=O)(=O)C1CC1] |
| 329 | 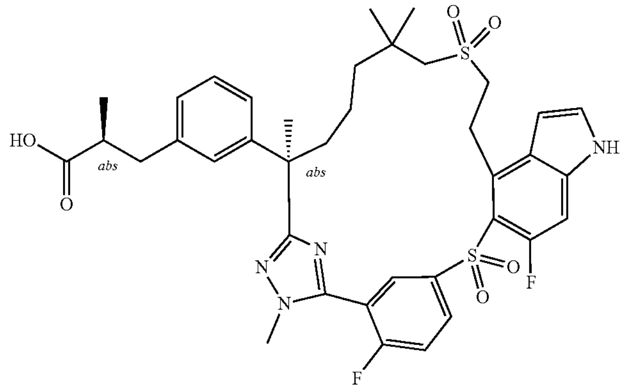 [SMILES: C[C@@H](Cc1cccc([C@@]2(C)CCCC(C)(C)CS(=O)(=O)CCc3c(c(F)cc4[nH]ccc34)S(=O)(=O)c3ccc(F)c(c3)-c3nc2nn3C)c1)C(=O)O] |
| 330 | 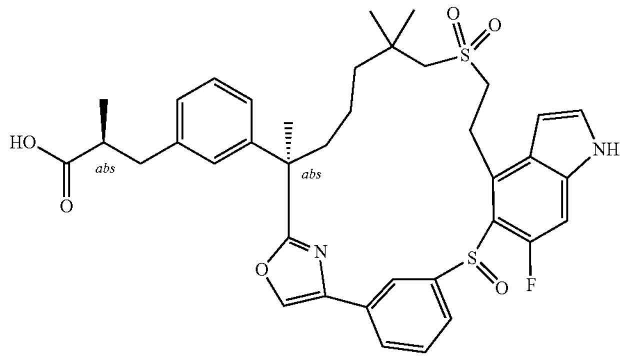 [SMILES: C[C@@H](Cc1cccc([C@@]2(C)CCCC(C)(C)CS(=O)(=O)CCc3c(c(F)cc4[nH]ccc34)S(=O)c3cccc(c3)-c3coc2n3)c1)C(=O)O] |

-continued
| Compound No. | Structures |
| --- | --- |
| 331 | 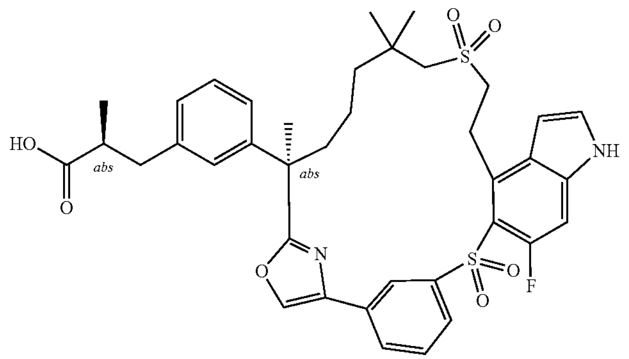 [SMILES: C[C@@H](Cc1cccc([C@@]2(C)CCCC(C)(C)CS(=O)(=O)CCc3c(c(F)cc4[nH]ccc34)S(=O)(=O)c3cccc(c3)-c3coc2n3)c1)C(=O)O] |
| 332 | 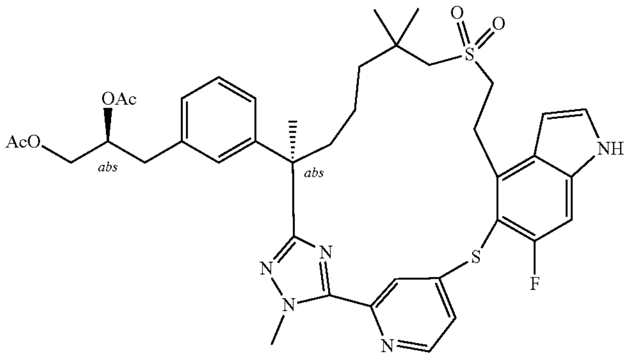 [SMILES: CC(=O)OC[C@H](Cc1cccc([C@@]2(C)CCCC(C)(C)CS(=O)(=O)CCc3c(c(F)cc4[nH]ccc34)Sc3ccnc(c3)-c3nc2nn3C)c1)OC(C)=O] |
| 333 | 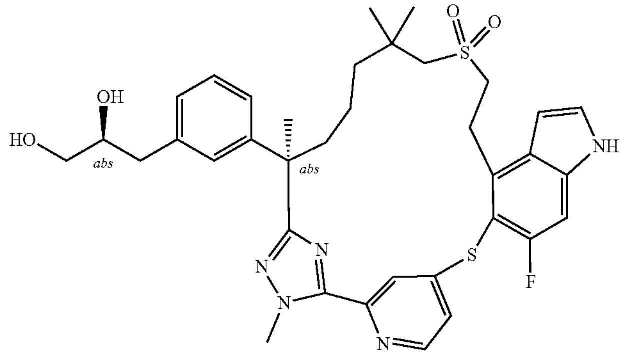 [SMILES: Cn1nc2nc1-c1cc(ccn1)Sc1c(F)cc3[nH]ccc3c1CCS(=O)(=O)CC(C)(C)CCC[C@]2(C)c1cccc(C[C@H](O)CO)c1] |
| 334 | 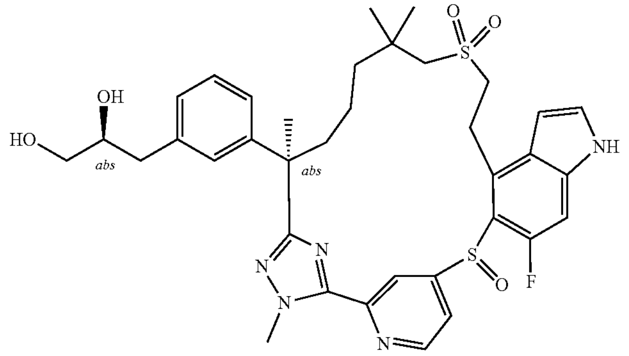 [SMILES: Cn1nc2nc1-c1cc(ccn1)S(=O)c1c(F)cc3[nH]ccc3c1CCS(=O)(=O)CC(C)(C)CCC[C@]2(C)c1cccc(C[C@H](O)CO)c1] |

-continued
| Compound No. | Structures |
| --- | --- |
| 335 | 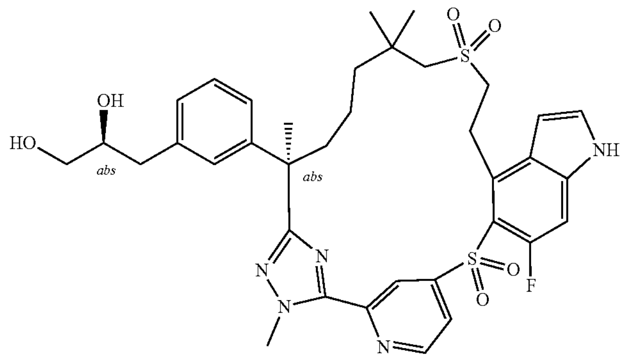 [SMILES: Cn1nc2nc1-c1cc(ccn1)S(=O)(=O)c1c(F)cc3[nH]ccc3c1CCS(=O)(=O)CC(C)(C)CCC[C@]2(C)c1cccc(C[C@H](O)CO)c1] |
| 336A | 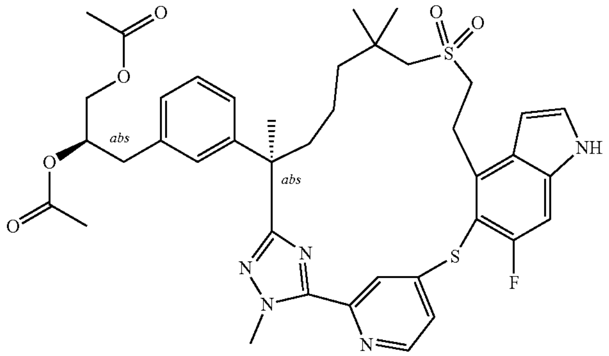 [SMILES: CC(=O)OC[C@@H](Cc1cccc([C@@]2(C)CCCC(C)(C)CS(=O)(=O)CCc3c(c(F)cc4[nH]ccc34)Sc3ccnc(c3)-c3nc2nn3C)c1)OC(C)=O] |
| 336B | 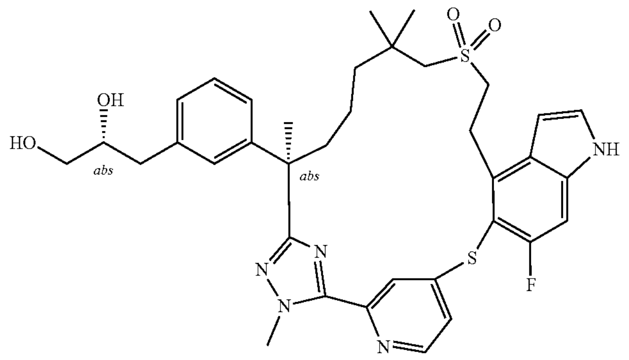 [SMILES: Cn1nc2nc1-c1cc(ccn1)Sc1c(F)cc3[nH]ccc3c1CCS(=O)(=O)CC(C)(C)CCC[C@]2(C)c1cccc(C[C@@H](O)CO)c1] |
| 337 | 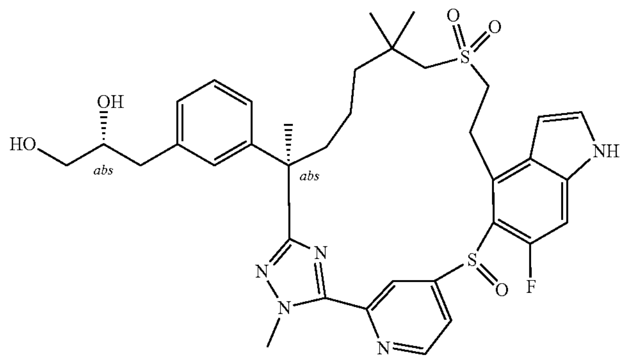 [SMILES: Cn1nc2nc1-c1cc(ccn1)S(=O)c1c(F)cc3[nH]ccc3c1CCS(=O)(=O)CC(C)(C)CCC[C@]2(C)c1cccc(C[C@@H](O)CO)c1] |

-continued
| Compound No. | Structures |
| --- | --- |
| 338 | 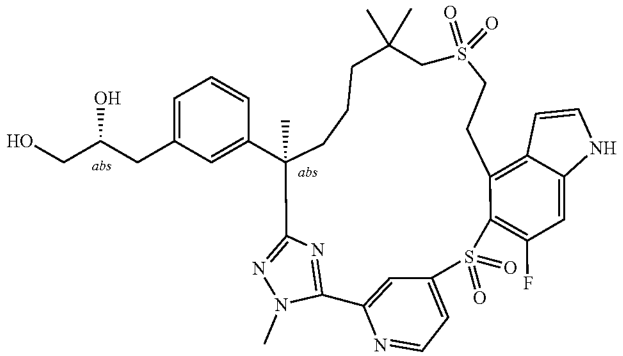 [SMILES: Cn1nc2nc1-c1cc(ccn1)S(=O)(=O)c1c(F)cc3[nH]ccc3c1CCS(=O)(=O)CC(C)(C)CCC[C@]2(C)c1cccc(C[C@@H](O)CO)c1] |
| 339 | 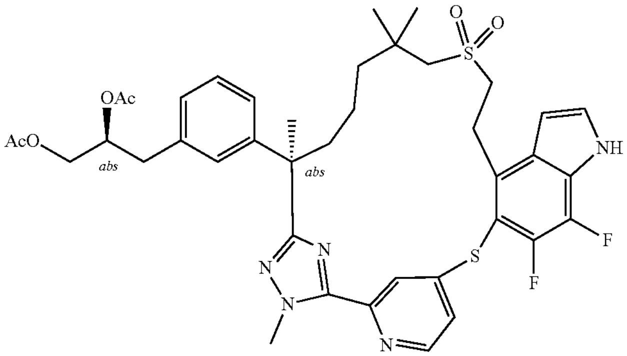 [SMILES: CC(=O)OC[C@H](Cc1cccc([C@@]2(C)CCCC(C)(C)CS(=O)(=O)CCc3c(c(F)c(F)c4[nH]ccc34)Sc3ccnc(c3)-c3nc2nn3C)c1)OC(C)=O] |
| 340 | 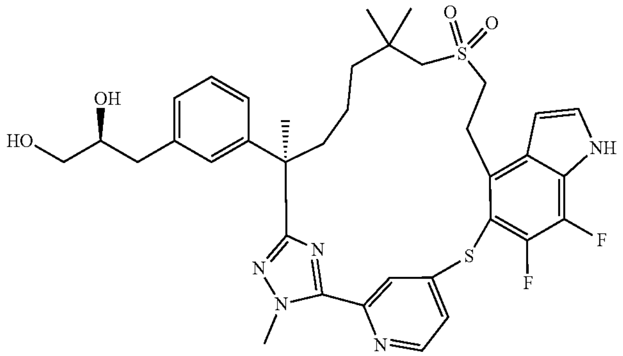 [SMILES: Cn1nc2nc1-c1cc(ccn1)Sc1c(F)c(F)c3[nH]ccc3c1CCS(=O)(=O)CC(C)(C)CCC[C@]2(C)c1cccc(C[C@H](O)CO)c1] |
| 341 | 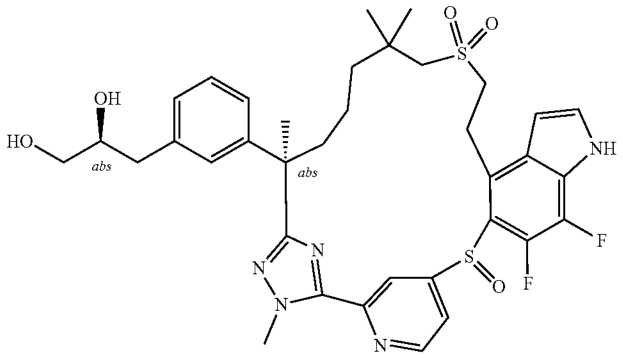 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(C[C@H](O)CO)c1] |

-continued
| Compound No. | Structures |
| --- | --- |
| 342 | 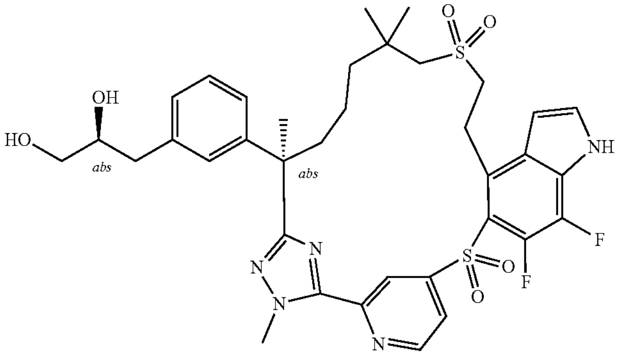 [SMILES: Cn1nc2nc1-c1cc(ccn1)S(=O)(=O)c1c(F)c(F)c3[nH]ccc3c1CCS(=O)(=O)CC(C)(C)CCC[C@]2(C)c1cccc(C[C@H](O)CO)c1] |
| 345 | 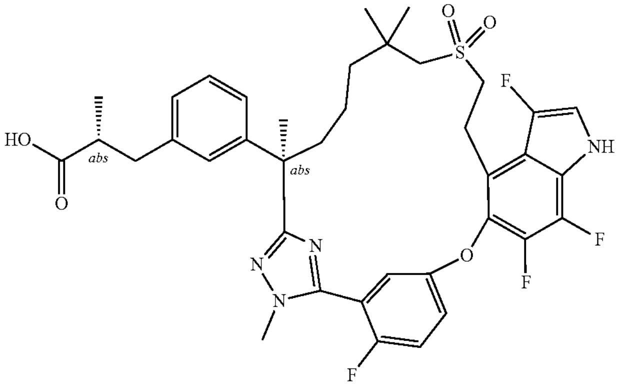 [SMILES: C[C@H](Cc1cccc([C@@]2(C)CCCC(C)(C)CS(=O)(=O)CCc3c(c(F)c(F)c4[nH]cc(F)c34)Oc3ccc(F)c(c3)-c3nc2nn3C)c1)C(=O)O] |
| 346 | 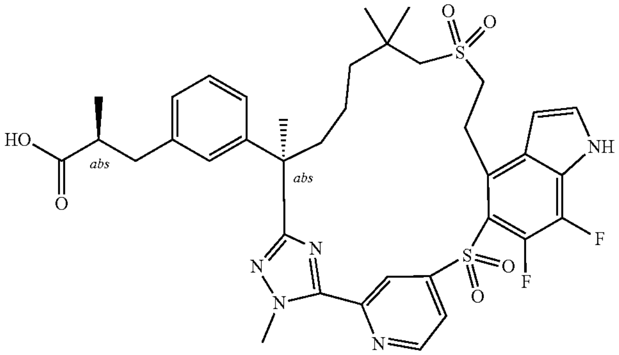 [SMILES: C[C@@H](Cc1cccc([C@@]2(C)CCCC(C)(C)CS(=O)(=O)CCc3c(c(F)c(F)c4[nH]ccc34)S(=O)(=O)c3ccnc(c3)-c3nc2nn3C)c1)C(=O)O] |
| 347 | 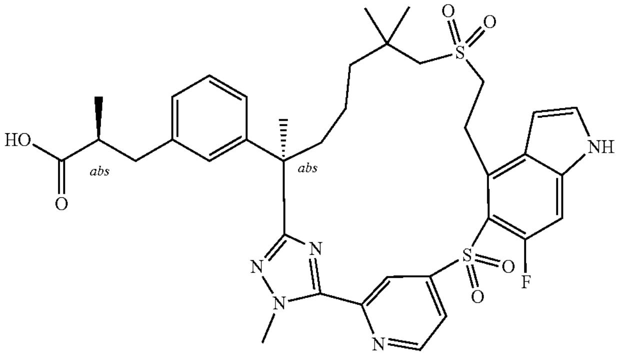 [SMILES: C[C@@H](Cc1cccc([C@@]2(C)CCCC(C)(C)CS(=O)(=O)CCc3c(c(F)cc4[nH]ccc34)S(=O)(=O)c3ccnc(c3)-c3nc2nn3C)c1)C(=O)O] |

-continued
| Compound No. | Structures |
| --- | --- |
| 348A | 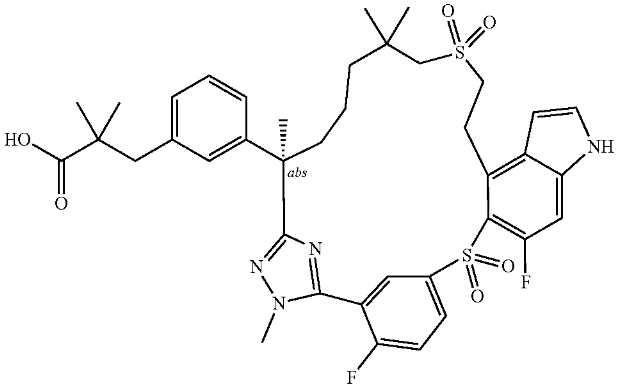 [SMILES: Cn1nc2nc1-c1cc(ccc1F)S(=O)(=O)c1c(F)cc3[nH]ccc3c1CCS(=O)(=O)CC(C)(C)CCC[C@]2(C)c1cccc(CC(C)(C)C(=O)O)c1] |
| 348B | 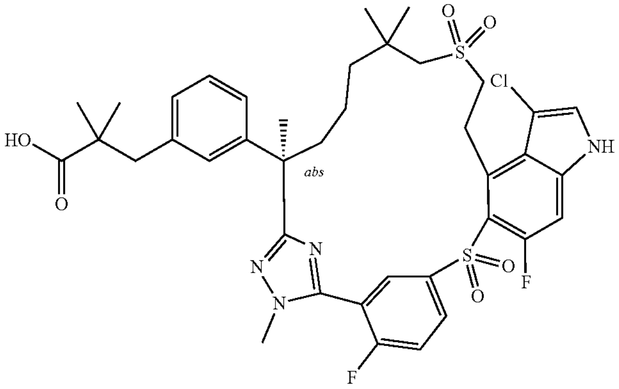 [SMILES: Cn1nc2nc1-c1cc(ccc1F)S(=O)(=O)c1c(F)cc3[nH]cc(Cl)c3c1CCS(=O)(=O)CC(C)(C)CCC[C@]2(C)c1cccc(CC(C)(C)C(=O)O)c1] |
| 349 | 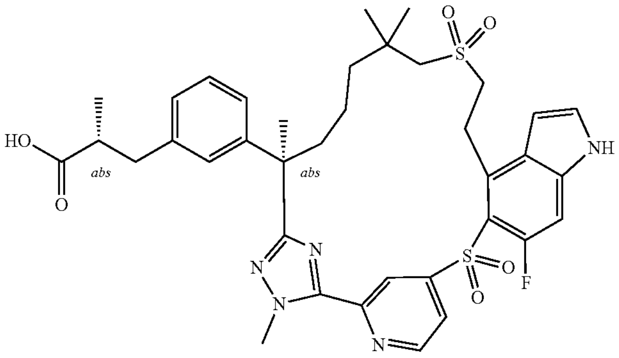 [SMILES: C[C@H](Cc1cccc([C@@]2(C)CCCC(C)(C)CS(=O)(=O)CCc3c(c(F)cc4[nH]ccc34)S(=O)(=O)c3ccnc(c3)-c3nc2nn3C)c1)C(=O)O] |
| 350 | 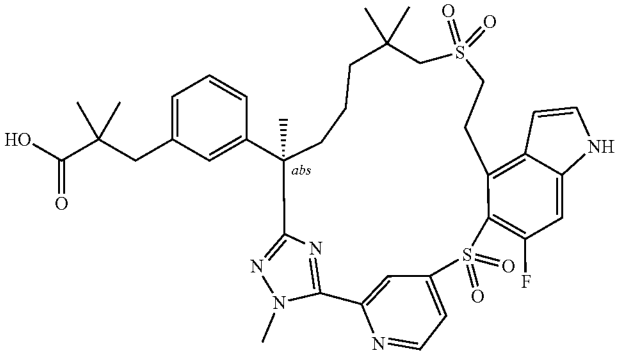 [SMILES: Cn1nc2nc1-c1cc(ccn1)S(=O)(=O)c1c(F)cc3[nH]ccc3c1CCS(=O)(=O)CC(C)(C)CCC[C@]2(C)c1cccc(CC(C)(C)C(=O)O)c1] |

-continued
| Compound No. | Structures |
| --- | --- |
| 351 | 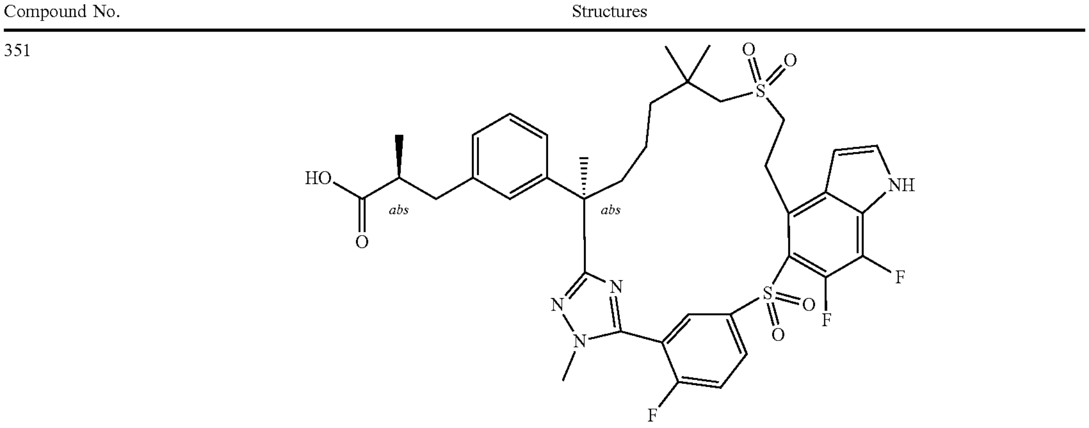 |
| 352 | 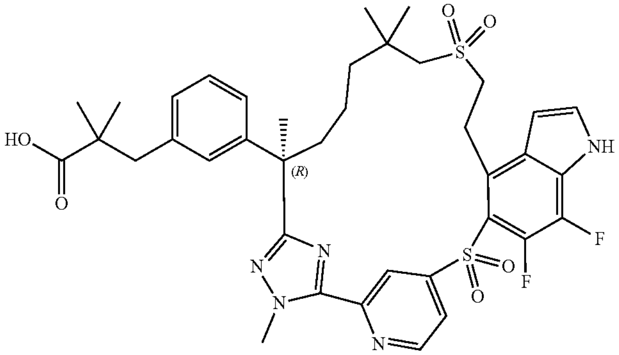 |
| 353 | 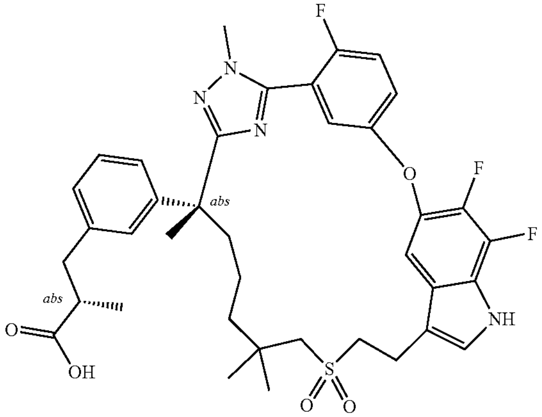 [SMILES: C[C@@H](Cc1cccc([C@@]2(C)CCCC(C)(C)CS(=O)(=O)CCc3c[nH]c4c(F)c(F)c(cc34)Oc3ccc(F)c(c3)-c3nc2nn3C)c1)C(=O)O] |
| 354 | 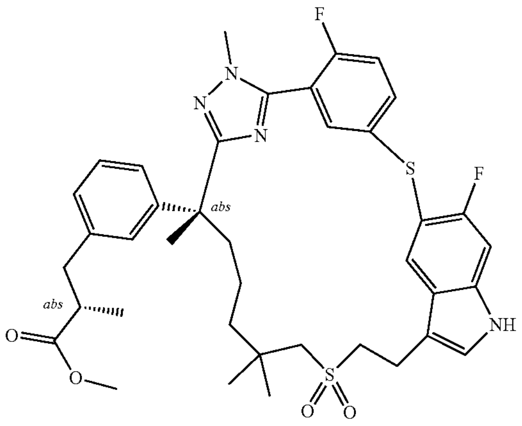 [SMILES: COC(=O)[C@@H](C)Cc1cccc([C@@]2(C)CCCC(C)(C)CS(=O)(=O)CCc3c[nH]c4cc(F)c(cc34)Sc3ccc(F)c(c3)-c3nc2nn3C)c1] |

-continued
| Compound No. | Structures |
| --- | --- |
| 355 | 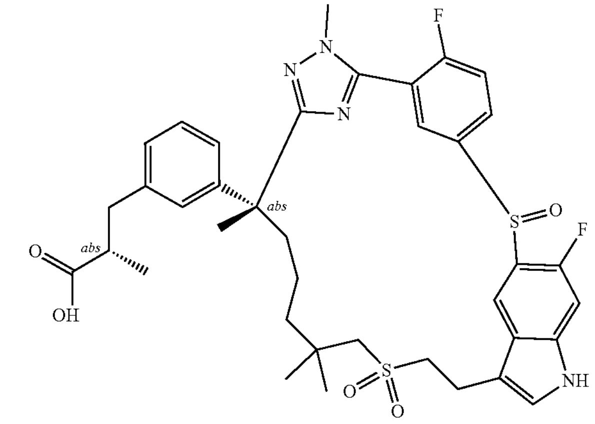 [SMILES: C[C@@H](Cc1cccc([C@@]2(C)CCCC(C)(C)CS(=O)(=O)CCc3c[nH]c4cc(F)c(cc34)S(=O)c3ccc(F)c(c3)-c3nc2nn3C)c1)C(=O)O] |
| 356 | 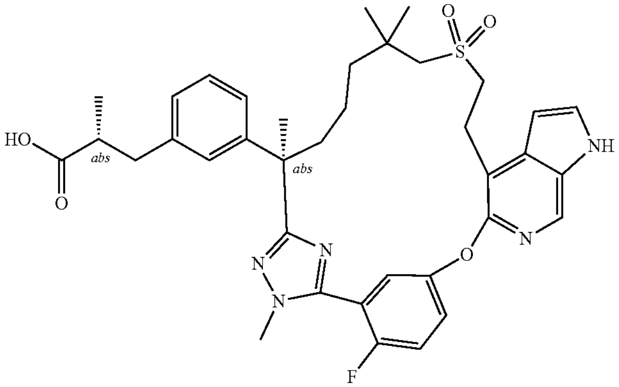 [SMILES: C[C@H](Cc1cccc([C@@]2(C)CCCC(C)(C)CS(=O)(=O)CCc3c(ncc4[nH]ccc34)Oc3ccc(F)c(c3)-c3nc2nn3C)c1)C(=O)O] |
| 357 | 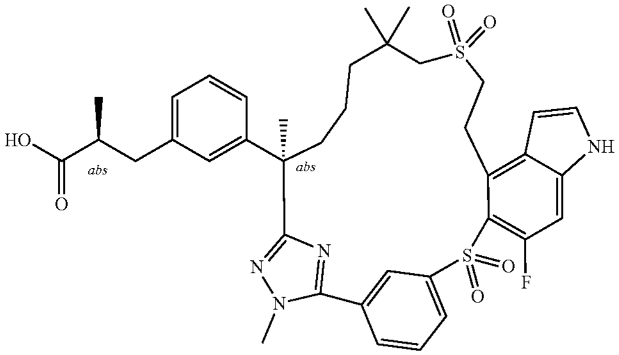 [SMILES: C[C@@H](Cc1cccc([C@@]2(C)CCCC(C)(C)CS(=O)(=O)CCc3c(c(F)cc4[nH]ccc34)S(=O)(=O)c3cccc(c3)-c3nc2nn3C)c1)C(=O)O] |
| 358 | 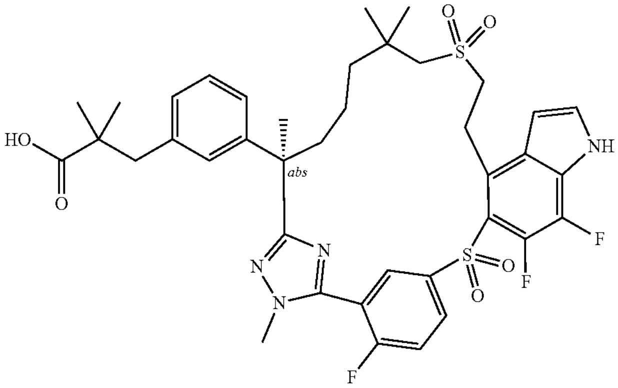 [SMILES: Cn1nc2nc1-c1cc(ccc1F)S(=O)(=O)c1c(F)c(F)c3[nH]ccc3c1CCS(=O)(=O)CC(C)(C)CCC[C@]2(C)c1cccc(CC(C)(C)C(=O)O)c1] |

-continued
| Compound No. | Structures |
| --- | --- |
| 359 | 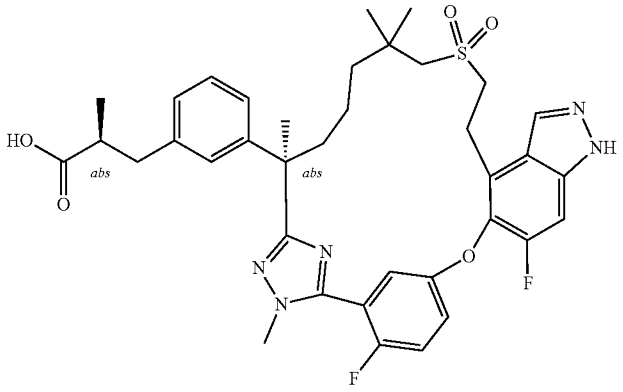 [SMILES: C[C@@H](Cc1cccc([C@@]2(C)CCCC(C)(C)CS(=O)(=O)CCc3c(c(F)cc4[nH]ncc34)Oc3ccc(F)c(c3)-c3nc2nn3C)c1)C(=O)O] |
| 360A | 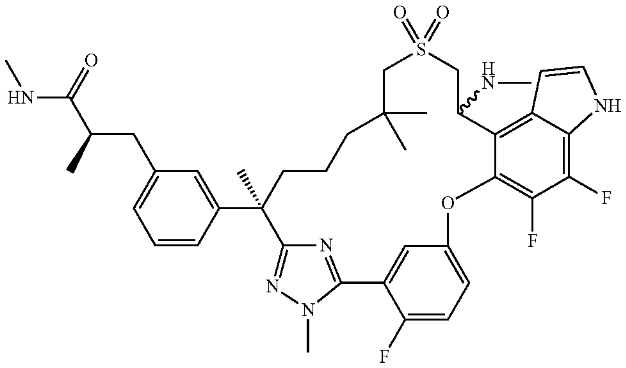 [SMILES: CNC(=O)[C@H](C)Cc1cccc([C@@]2(C)CCCC(C)(C)CS(=O)(=O)CC(NC)c3c(c(F)c(F)c4[nH]ccc34)Oc3ccc(F)c(c3)-c3nc2nn3C)c1] |
| 360B | 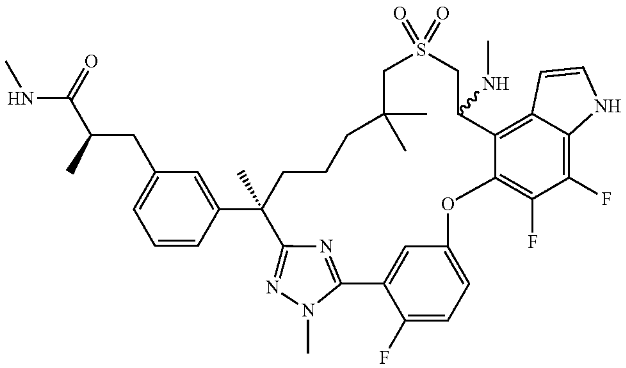 [SMILES: CNC(=O)[C@H](C)Cc1cccc([C@@]2(C)CCCC(C)(C)CS(=O)(=O)CC(NC)c3c(c(F)c(F)c4[nH]ccc34)Oc3ccc(F)c(c3)-c3nc2nn3C)c1] |
| 360C | 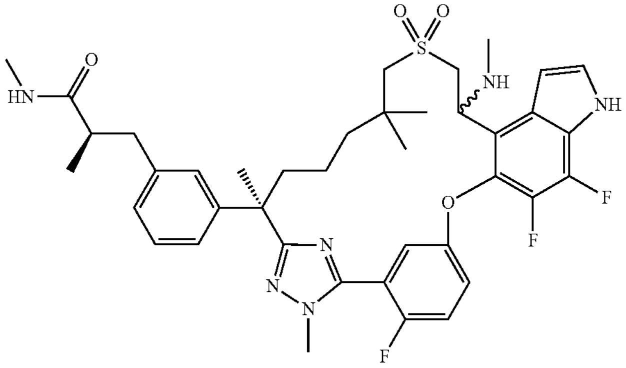 [SMILES: CNC(=O)[C@H](C)Cc1cccc([C@@]2(C)CCCC(C)(C)CS(=O)(=O)CC(NC)c3c(c(F)c(F)c4[nH]ccc34)Oc3ccc(F)c(c3)-c3nc2nn3C)c1] |

-continued
| Compound No. | Structures |
| --- | --- |
| 360D | 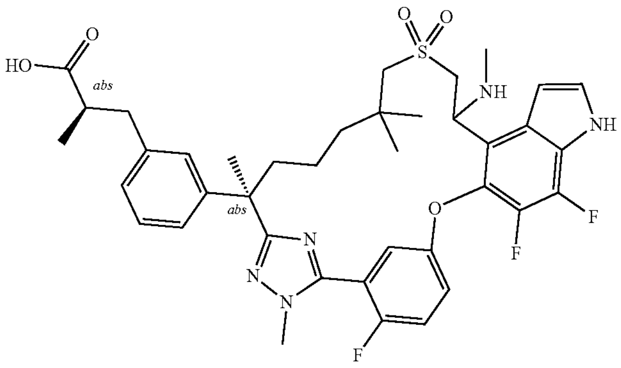 [SMILES: CNC1CS(=O)(=O)CC(C)(C)CCC[C@](C)(c2cccc(C[C@@H](C)C(=O)O)c2)c2nc(n(C)n2)-c2cc(ccc2F)Oc2c(F)c(F)c3[nH]ccc3c21] |
| 361 | 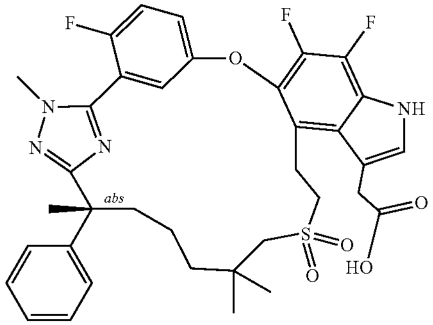 [SMILES: Cn1nc2nc1-c1cc(ccc1F)Oc1c(F)c(F)c3[nH]cc(CC(=O)O)c3c1CCS(=O)(=O)CC(C)(C)CCC[C@]2(C)c1ccccc1] |
| 362 | 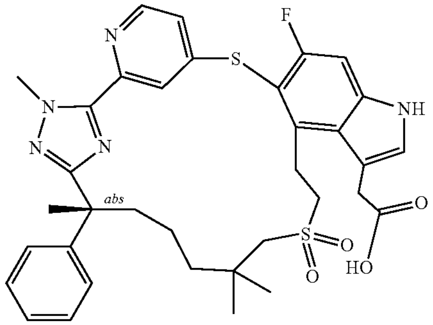 [SMILES: Cn1nc2nc1-c1cc(ccn1)Sc1c(F)cc3[nH]cc(CC(=O)O)c3c1CCS(=O)(=O)CC(C)(C)CCC[C@]2(C)c1ccccc1] |
| 363 | 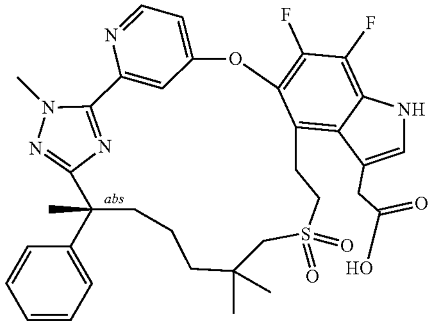 [SMILES: Cn1nc2nc1-c1cc(ccn1)Oc1c(F)c(F)c3[nH]cc(CC(=O)O)c3c1CCS(=O)(=O)CC(C)(C)CCC[C@]2(C)c1ccccc1] |

-continued
| Compound No. | Structures |
| --- | --- |
| 364 | 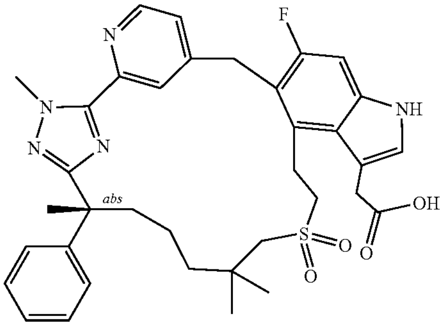 [SMILES: Cn1nc2nc1-c1cc(ccn1)Cc1c(F)cc3[nH]cc(CC(=O)O)c3c1CCS(=O)(=O)CC(C)(C)CCC[C@]2(C)c1ccccc1] |
| 365 | 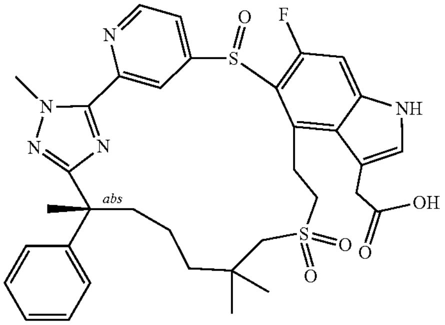 [SMILES: Cn1nc2nc1-c1cc(ccn1)S(=O)c1c(F)cc3[nH]cc(CC(=O)O)c3c1CCS(=O)(=O)CC(C)(C)CCC[C@]2(C)c1ccccc1] |
| 366 | 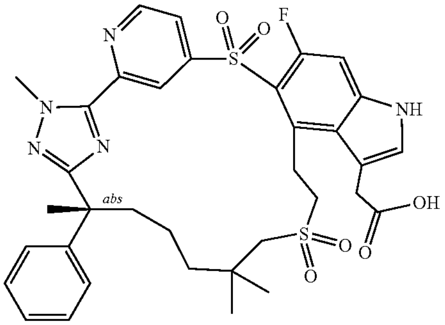 [SMILES: Cn1nc2nc1-c1cc(ccn1)S(=O)(=O)c1c(F)cc3[nH]cc(CC(=O)O)c3c1CCS(=O)(=O)CC(C)(C)CCC[C@]2(C)c1ccccc1] |
| 367A | 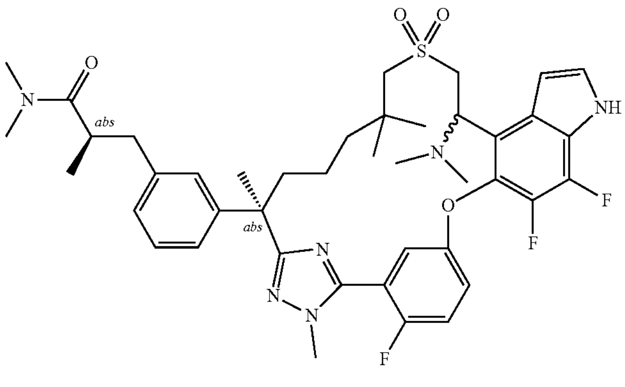 [SMILES: C[C@H](Cc1cccc([C@@]2(C)CCCC(C)(C)CS(=O)(=O)CC(N(C)C)c3c(c(F)c(F)c4[nH]ccc34)Oc3ccc(F)c(c3)-c3nc2nn3C)c1)C(=O)N(C)C] |

-continued
| Compound No. | Structures |
| --- | --- |
| 367B | 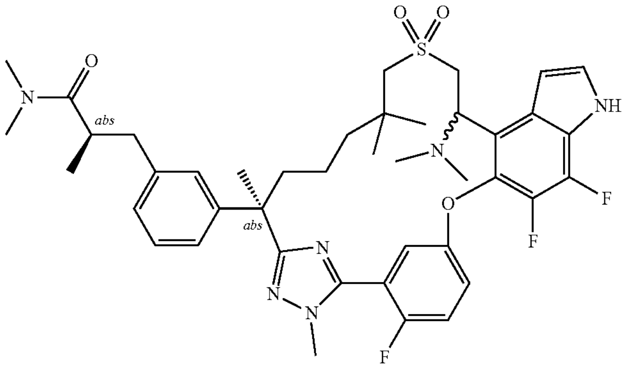 [SMILES: C[C@H](Cc1cccc([C@@]2(C)CCCC(C)(C)CS(=O)(=O)CC(N(C)C)c3c(c(F)c(F)c4[nH]ccc34)Oc3ccc(F)c(c3)-c3nc2nn3C)c1)C(=O)N(C)C] |
| 368A | 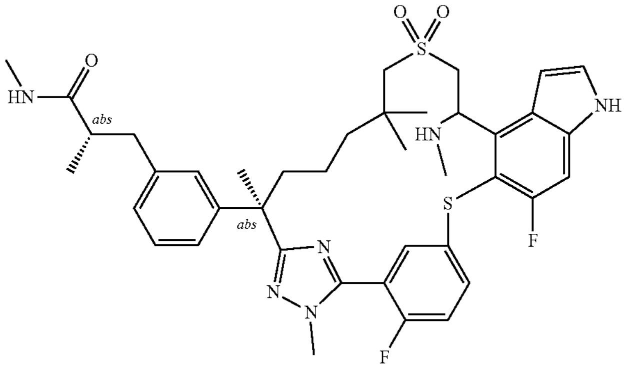 [SMILES: CNC(=O)[C@@H](C)Cc1cccc([C@@]2(C)CCCC(C)(C)CS(=O)(=O)CC(NC)c3c(c(F)cc4[nH]ccc34)Sc3ccc(F)c(c3)-c3nc2nn3C)c1] |
| 368B | 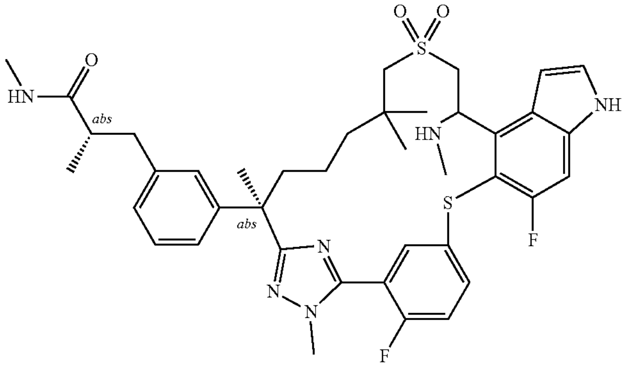 [SMILES: CNC(=O)[C@@H](C)Cc1cccc([C@@]2(C)CCCC(C)(C)CS(=O)(=O)CC(NC)c3c(c(F)cc4[nH]ccc34)Sc3ccc(F)c(c3)-c3nc2nn3C)c1] |
| 369A | 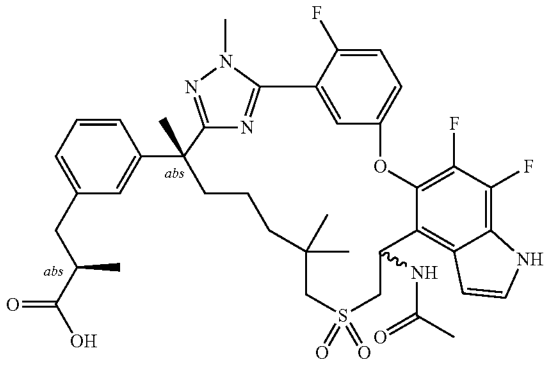 [SMILES: CC(=O)NC1CS(=O)(=O)CC(C)(C)CCC[C@](C)(c2cccc(C[C@@H](C)C(=O)O)c2)c2nc(n(C)n2)-c2cc(ccc2F)Oc2c(F)c(F)c3[nH]ccc3c21] |

-continued
| Compound No. | Structures |
| --- | --- |
| 369B | 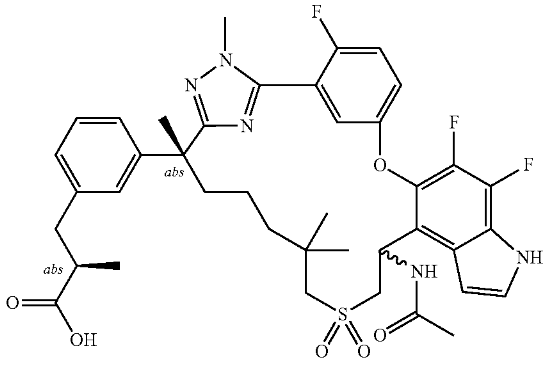 [SMILES: CC(=O)NC1CS(=O)(=O)CC(C)(C)CCC[C@](C)(c2cccc(C[C@@H](C)C(=O)O)c2)c2nc(n(C)n2)-c2cc(ccc2F)Oc2c(F)c(F)c3[nH]ccc3c21] |
| 370A | 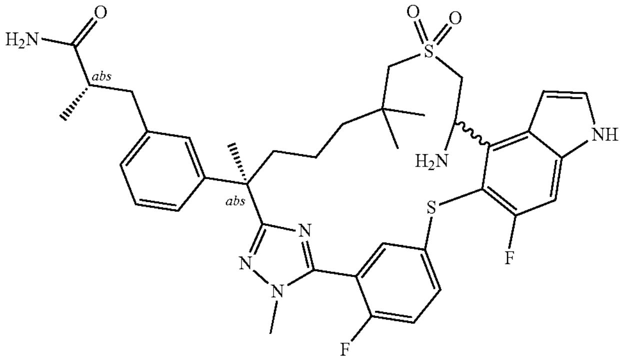 [SMILES: C[C@@H](Cc1cccc([C@@]2(C)CCCC(C)(C)CS(=O)(=O)CC(N)c3c(c(F)cc4[nH]ccc34)Sc3ccc(F)c(c3)-c3nc2nn3C)c1)C(N)=O] |
| 370B | 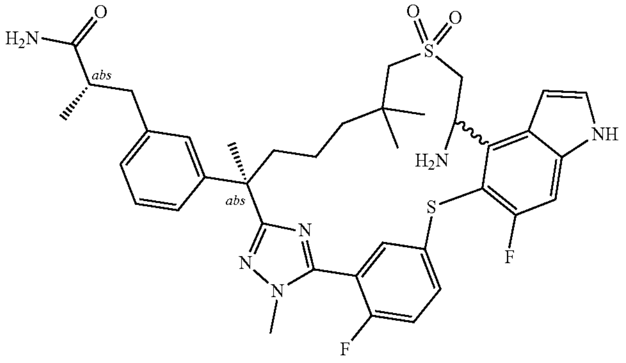 [SMILES: C[C@@H](Cc1cccc([C@@]2(C)CCCC(C)(C)CS(=O)(=O)CC(N)c3c(c(F)cc4[nH]ccc34)Sc3ccc(F)c(c3)-c3nc2nn3C)c1)C(N)=O] |
| 371 | 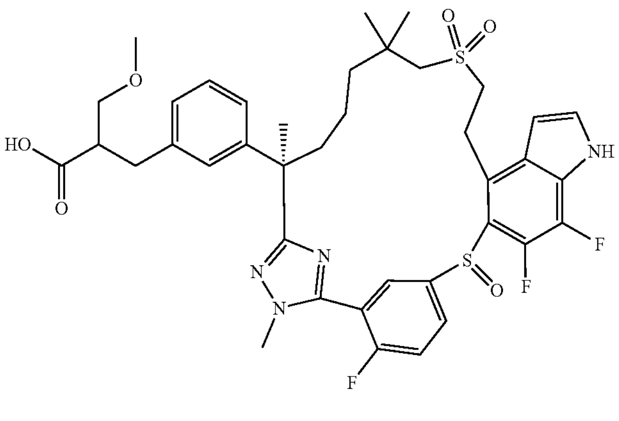 [SMILES: COCC(Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O] |

-continued
| Compound No. | Structures |
|---|---|
| 372 | 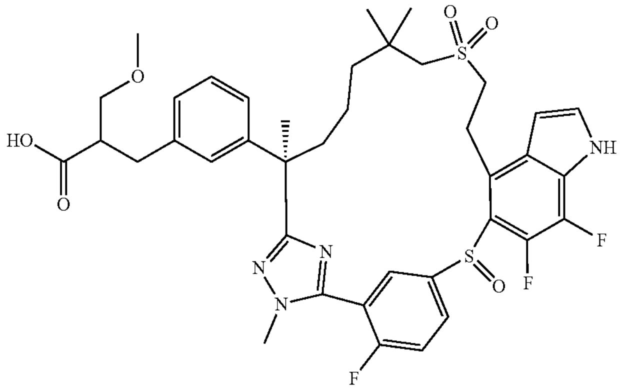 [SMILES: COCC(Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O] |
| 373 | 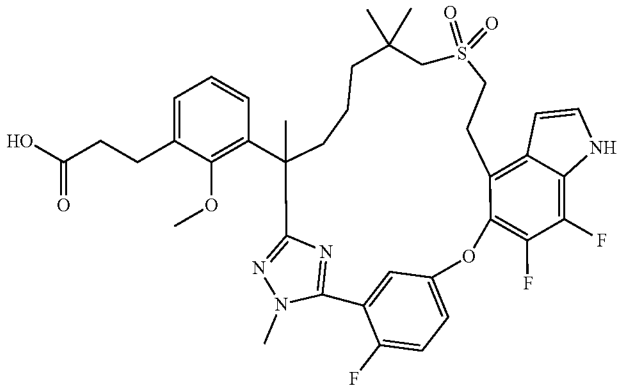 [SMILES: COc1c(CCC(=O)O)cccc1C1(C)CCCC(C)(C)CS(=O)(=O)CCc2c(c(F)c(F)c3[nH]ccc23)Oc2ccc(F)c(c2)-c2nc1nn2C] |
| 374 | 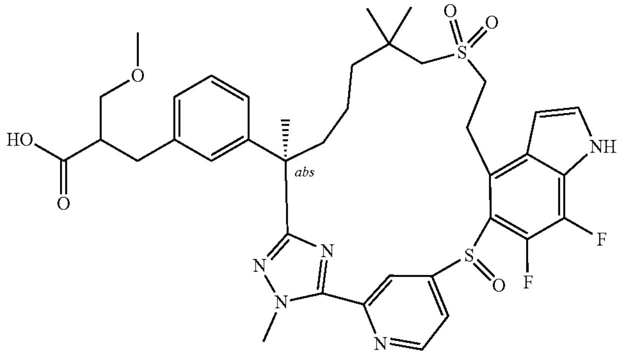 [SMILES: COCC(Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O] |
| 375 | 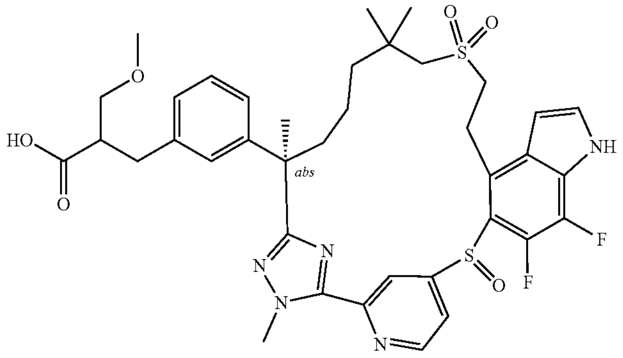 [SMILES: COCC(Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O] |

-continued
| Compound No. | Structures |
| --- | --- |
| 376 | 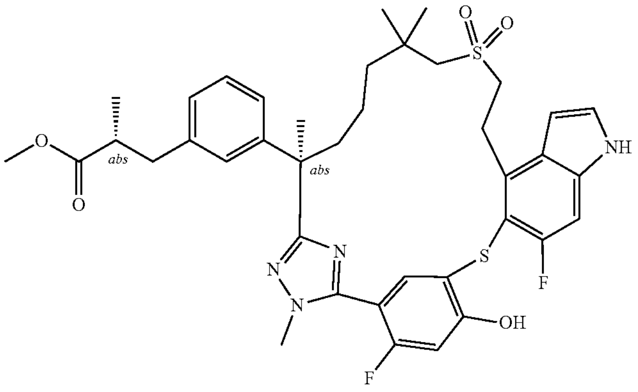 [SMILES: COC(=O)[C@H](C)Cc1cccc([C@@]2(C)CCCC(C)(C)CS(=O)(=O)CCc3c(c(F)cc4[nH]ccc34)Sc3cc(c(F)cc3O)-c3nc2nn3C)c1] |
| 377 | 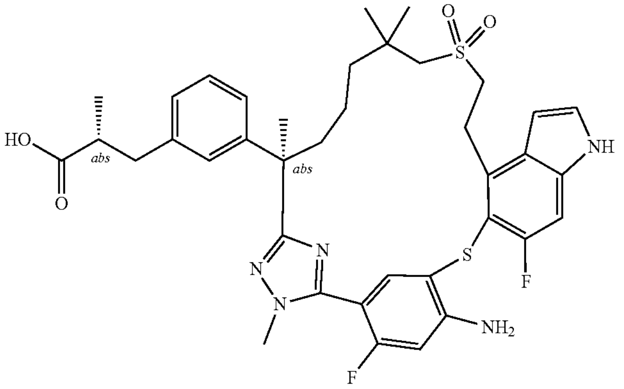 [SMILES: C[C@H](Cc1cccc([C@@]2(C)CCCC(C)(C)CS(=O)(=O)CCc3c(c(F)cc4[nH]ccc34)Sc3cc(c(F)cc3N)-c3nc2nn3C)c1)C(=O)O] |
| 378 | 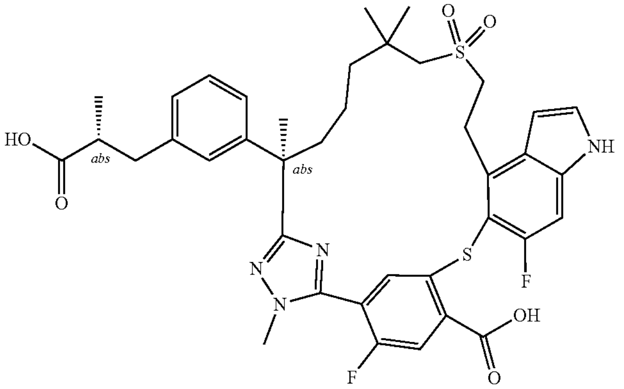 [SMILES: C[C@H](Cc1cccc([C@@]2(C)CCCC(C)(C)CS(=O)(=O)CCc3c(c(F)cc4[nH]ccc34)Sc3cc(c(F)cc3C(=O)O)-c3nc2nn3C)c1)C(=O)O] |
| 379A | 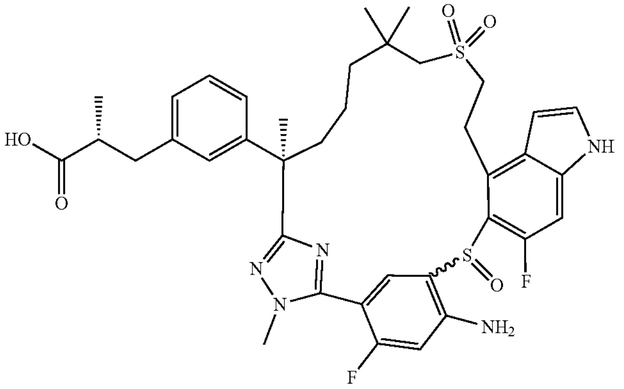 [SMILES: C[C@H](Cc1cccc([C@@]2(C)CCCC(C)(C)CS(=O)(=O)CCc3c(c(F)cc4[nH]ccc34)S(=O)c3cc(c(F)cc3N)-c3nc2nn3C)c1)C(=O)O] |

-continued
| Compound No. | Structures |
| --- | --- |
| 379B | 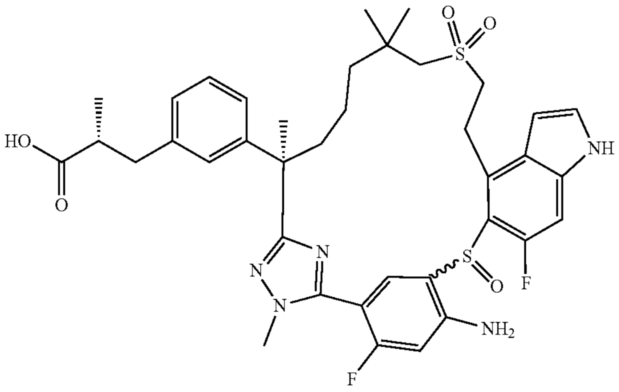 [SMILES: C[C@H](Cc1cccc([C@@]2(C)CCCC(C)(C)CS(=O)(=O)CCc3c(c(F)cc4[nH]ccc34)S(=O)c3cc(c(F)cc3N)-c3nc2nn3C)c1)C(=O)O] |
| 379C | 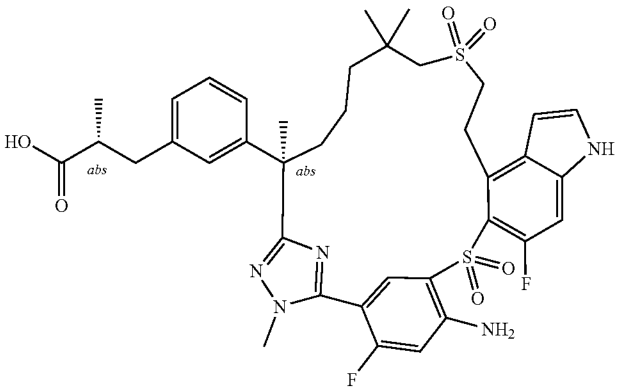 [SMILES: C[C@H](Cc1cccc([C@@]2(C)CCCC(C)(C)CS(=O)(=O)CCc3c(c(F)cc4[nH]ccc34)S(=O)(=O)c3cc(c(F)cc3N)-c3nc2nn3C)c1)C(=O)O] |
| 380 | 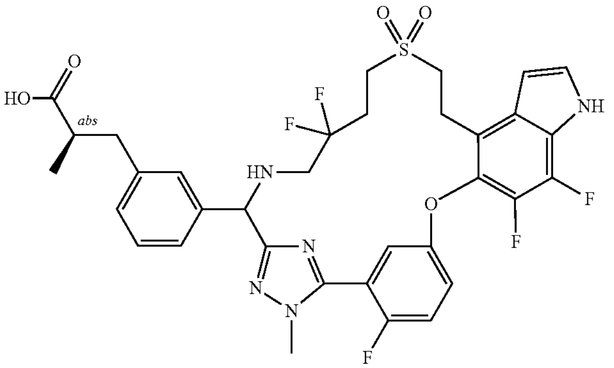 [SMILES: C[C@H](Cc1cccc(C2NCC(F)(F)CCS(=O)(=O)CCc3c(c(F)c(F)c4[nH]ccc34)Oc3ccc(F)c(c3)-c3nc2nn3C)c1)C(=O)O] |
| 381A | 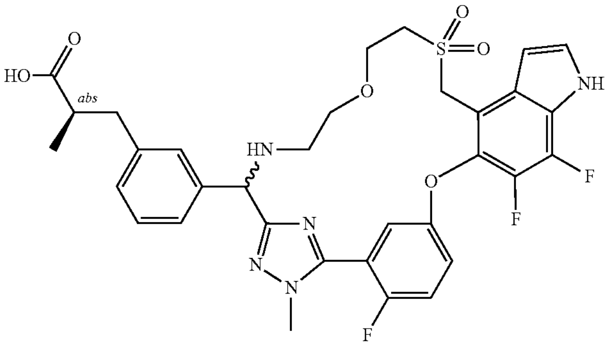 [SMILES: C[C@H](Cc1cccc(C2NCCOCCS(=O)(=O)Cc3c(c(F)c(F)c4[nH]ccc34)Oc3ccc(F)c(c3)-c3nc2nn3C)c1)C(=O)O] |

-continued
| Compound No. | Structures |
| --- | --- |
| 381B | 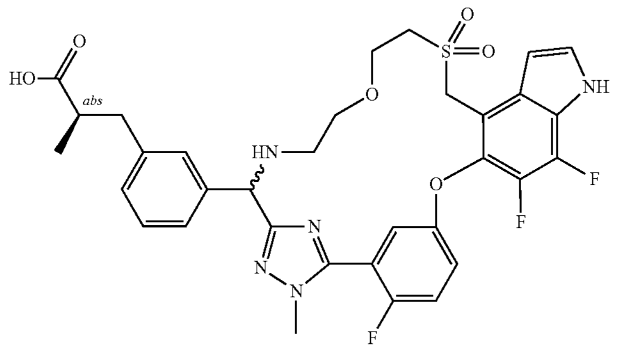 [SMILES: C[C@H](Cc1cccc(C2NCCOCCS(=O)(=O)Cc3c(c(F)c(F)c4[nH]ccc34)Oc3ccc(F)c(c3)-c3nc2nn3C)c1)C(=O)O] |
| 382 | 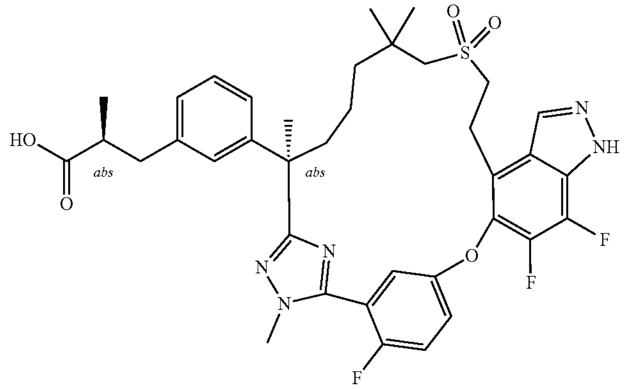 [SMILES: C[C@@H](Cc1cccc([C@@]2(C)CCCC(C)(C)CS(=O)(=O)CCc3c(c(F)c(F)c4[nH]ncc34)Oc3ccc(F)c(c3)-c3nc2nn3C)c1)C(=O)O] |
| 383 | 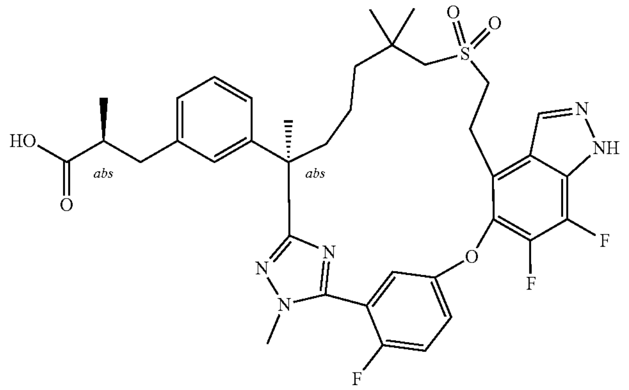 [SMILES: C[C@@H](Cc1cccc([C@@]2(C)CCCC(C)(C)CS(=O)(=O)CCc3c(c(F)c(F)c4[nH]ncc34)Oc3ccc(F)c(c3)-c3nc2nn3C)c1)C(=O)O] |
| 384 | 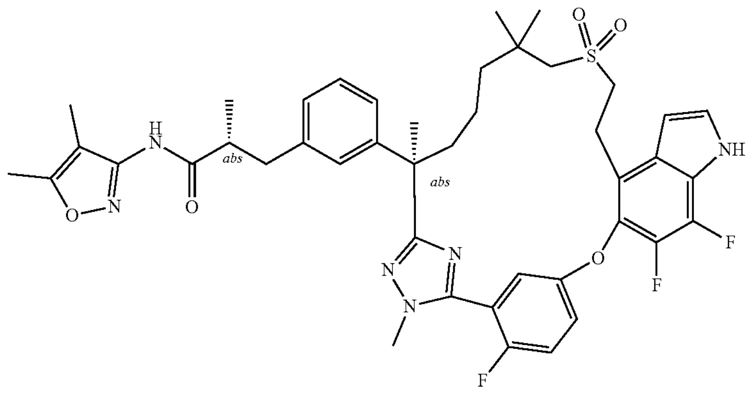 [SMILES: Cc1onc(NC(=O)[C@H](C)Cc2cccc([C@@]3(C)CCCC(C)(C)CS(=O)(=O)CCc4c(c(F)c(F)c5[nH]ccc45)Oc4ccc(F)c(c4)-c4nc3nn4C)c2)c1C] |

-continued

| Compound No. | Structures |
| --- | --- |
| 385A | 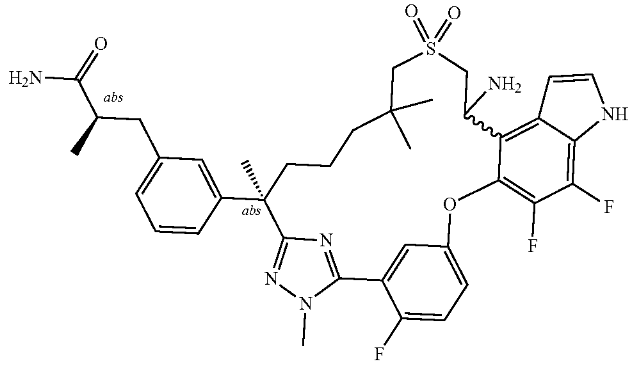 [SMILES: C[C@H](Cc1cccc([C@@]2(C)CCCC(C)(C)CS(=O)(=O)CC(N)c3c(c(F)c(F)c4[nH]ccc34)Oc3ccc(F)c(c3)-c3nc2nn3C)c1)C(N)=O] |
| 385B | 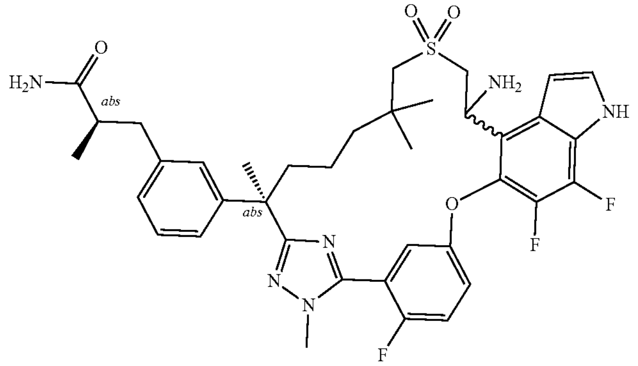 [SMILES: C[C@H](Cc1cccc([C@@]2(C)CCCC(C)(C)CS(=O)(=O)CC(N)c3c(c(F)c(F)c4[nH]ccc34)Oc3ccc(F)c(c3)-c3nc2nn3C)c1)C(N)=O] |

or a pharmaceutically acceptable salt thereof.

Definitions

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "haloaliphatic" refers to an aliphatic group that is substituted with one or more halogen atoms.

The term "haloalkyl" refers to a straight or branched alkyl group that is substituted with one or more halogen atoms.

The term "alkyl" as used herein is a branched or unbranched saturated hydrocarbon group having a specified number of carbon atoms. In some embodiments, alkyl refers to a branched or unbranched saturated hydrocarbon group having three carbon atoms ($C_3$). In some embodiments, alkyl refers to a branched or unbranched saturated hydrocarbon group having six carbon atoms ($C_6$). In some embodiments, the term "alkyl" includes, but is not limited to, methyl, ethyl, n-propyl, isopropyl, n-butyl, isobutyl, s-butyl, t-butyl, n-pentyl, isopentyl, s-pentyl, neopentyl, and hexyl.

As used herein, the term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group. The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in TV-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^{\circ}$; $—(CH_2)_{0-4}OR^{\circ}$; $—O(CH_2)_{0-4}R^{\circ}$, $—O—(CH_2)_{0-4}C(O)OR^{\circ}$; $—(CH_2)_{0-4}CH(OR^{\circ})_2$; $—(CH_2)_{0-4}SR^{\circ}$; $—(CH_2)_{0-4}Ph$, which may be substituted with R°; $—(CH_2)_{0-4}O(CH_2)_{0-1}Ph$ which may be substituted with R°; —CH═CHPh, which may be substituted with R°; $—(CH_2)_{0-4}O(CH_2)_{0-1}$-pyridyl which may be substituted with R°; $—NO_2$; —CN; $—N_3$; $—(CH_2)_{0-4}N(R^{\circ})_2$; $—(CH_2)_{0-4}N(R^{\circ})C(O)R^{\circ}$; $—N(R^{\circ})C(S)R^{\circ}$; $—(CH_2)_{0-4}N(R^{\circ})C(O)NR^{\circ}_2$; $—N(R^{\circ})C(S)NR^{\circ}_2$; $—(CH_2)_{0-4}$ $N(R^{\circ})C(O)OR^{\circ}$; $—N(R^{\circ})N(R^{\circ})C(O)R^{\circ}$; $—N(R^{\circ})N(R^{\circ})C(O)NR^{\circ}_2$; $—N(R^{\circ})N(R^{\circ})C(O)OR^{\circ}$; $—(CH_2)_{0-4}C(O)R^{\circ}$; $—C(S)R^{\circ}$; $—(CH_2)_{0-4}C(O)OR^{\circ}$; $—(CH_2)_{0-4}C(O)SR^{\circ}$; $—(CH_2)_{0-4}C(O)OSiR^{\circ}_3$; $—(CH_2)_{0-4}OC(O)R^{\circ}$; $—OC(O)(CH_2)_{0-4}SR^{\circ}$, $SC(S)SR^{\circ}$; $—(CH_2)_{0-4}SC(O)R^{\circ}$; $—(CH_2)_{0-4}C(O)NR^{\circ}_2$; $—C(S)NR^{\circ}_2$; $—C(S)SR^{\circ}$; $—SC(S)SR^{\circ}$, $—(CH_2)_{0-4}OC(O)NR^{\circ}_2$; $—C(O)N(OR^{\circ})R^{\circ}$;

—C(O)C(O)$R^\circ$; —C(O)$CH_2$C(O)$R^\circ$; —C(NO$R^\circ$)$R^\circ$; —$(CH_2)_{0-4}$SS$R^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —C(NH)$NR^\circ_2$; —$P(O)_2R^\circ$; —$P(O)R^\circ_2$; —$OP(O)R^\circ_2$; —$OP(O)(OR^\circ)_2$; $SiR^\circ_3$; —($C_{1-4}$ straight or branched alkylene)O—$N(R^\circ)_2$; or —($C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2$Ph, —$O(CH_2)_{0-1}$Ph, —$CH_2$—(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}$OH, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}$C(O)OH, —$(CH_2)_{0-2}C(O)OR^\bullet$, —$(CH_2)_{0-2}SR^\bullet$, —$(CH_2)_{0-2}$SH, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —C(O)$SR^\bullet$, —($C_{1-4}$ straight or branched alkylene)C(O)$OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =NNHC(O)$R^*$, =NNHC(O)$OR^*$, =$NNHS(O)_2R^*$, =$NR^*$, =$NOR^*$, —$O(C(R^*_2))_{2-3}$O—, or —$S(C(R^*_2))_{2-3}$S—, wherein each independent occurrence of $R^\bullet$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}$O—, wherein each independent occurrence of $R^\bullet$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^\bullet$ include halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —C(O)$R^\dagger$, —C(O)$OR^\dagger$, —C(O)C(O)$R^\dagger$, —C(O)$CH_2$C(O)$R^\dagger$, —$S(O)_2R^\dagger$, —$S(O)_2NR^\dagger_2$, —C(S)$NR^\dagger_2$, —C(NH)$NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof. Examples of such purposes include, but are not limited to, blood transfusion, organ transplantation, biological specimen storage, and biological assays.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat and/or diagnose the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a provided compound in a formulation to treat a disease, disorder, and/or condition is the amount that alleviates, ameliorates, relieves, reduces severity of and/or reduces incidence of one or more symptoms or features of the disease, disorder, and/or condition. In some embodiments, a "therapeutically effective amount" is at least a minimal amount of a provided compound, or composition containing a provided compound, which is sufficient for treating one or more symptoms of an CFTR-associated disease or disorder.

The terms "treat", "treatment" or "treating" mean to decrease, suppress, attenuate, diminish, arrest, or stabilize the development or progression of a disease (e.g., a disease or disorder delineated herein), lessen the severity of the disease or improve the symptoms associated with the disease. Treatment includes treating a symptom of a disease, disorder or condition. Without being bound by any theory, in some embodiments, treating includes augmenting deficient CFTR activity. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

The term "pharmaceutically acceptable carrier, adjuvant, or vehicle" refers to a non-toxic carrier, adjuvant, or vehicle that does not destroy the pharmacological activity of the compound(s) with which it is formulated. Pharmaceutically acceptable carriers, adjuvants or vehicles that may be used in the compositions of the compounds disclosed herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this disclosure that, upon administration to a recipient, is capable of providing, either directly or indirectly, a compound of this disclosure or an active metabolite or residue thereof.

The expression "dosage unit form" as used herein refers to a physically discrete unit of agent appropriate for the patient to be treated. It will be understood, however, that total daily usage of compounds and compositions of the present disclosure will be decided by the attending physician within the scope of sound medical judgment. Specific effective dose level for any particular patient or organism will depend upon a variety of factors including disorder being treated and severity of the disorder; activity of specific compound employed; specific composition employed; age, body weight, general health, sex and diet of the patient; time of administration, route of administration, and rate of excretion of a specific compound employed; duration of treatment; drugs used in combination or coincidental with a specific compound employed, and like factors well known in the medical arts.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

As used herein, "CFTR" means cystic fibrosis transmembrane conductance regulator. Defects in the function of the CFTR ion channel result from loss of function mutations of CFTR. Such mutations lead to exocrine gland dysfunction, abnormal mucociliary clearance, and cause cystic fibrosis. The most common CFTR mutation in Cystic Fibrosis (CF) patients leads to the specific deletion of three nucleotides of the codon for phenylalanine at position 508. This mutation, which is found in ~70% of CF patients worldwide, is referred to as "ΔF508". The ΔF508 mutation decreases the stability of the CFTR NBD1 domain and limits CFTR interdomain assembly. Since CF is an autosomal recessive disease, a CF patient harboring the ΔF508 CFTR mutation must also carry a second defective copy of CFTR. Approximately 2000 different CF-causing CFTR mutations have been identified in CF patients. CF patients harboring the ΔF508 CFTR mutation can be homozygous for that mutation (ΔF508/ΔF508). CF patients can also be ΔF508 heterozygous, if the second CFTR allele such patients carry instead contains a different CFTR loss of function mutation. Such CFTR mutations include, but are not limited to, G542X, G551D, N1303K, W1282X, R553X, R117H, R1162X, R347P, G85E, R560T, A455E, ΔI507, G178R, S549N, S549R, G551S, G970R, G1244E, S1251N, S1255P, and G1349D.

As used herein, the term "CFTR modulator" refers to a compound that increases the activity of CFTR. In certain aspects, a CFTR modulator is a CFTR corrector or a CFTR potentiator or a dual-acting compound having activities of a corrector and a potentiator.

As used herein, the term "CFTR corrector" refers to a compound that increases the amount of functional CFTR protein to the cell surface and thus enhances CFTR channel function. The CFTR correctors partially "rescue" misfolding of CFTR, thereby enabling the maturation and functional expression of CFTR protein harboring a CF causing mutation on the cell surface. Examples of correctors include, but are not limited to, VX-809, VX-661, VX-152, VX-440, VX-983, and GLPG2222. Such compounds may interact directly with CFTR protein, modifying its folding and conformational maturation during synthesis.

As used herein, the term "CFTR potentiator" refers to a compound that increases the ion channel activity of CFTR protein located at the cell surface, resulting in enhanced ion transport. CFTR potentiators repair the defective channel functions caused by mutations. Examples of potentiators include, but are not limited to, ivacaftor (VX770), deuterated ivacaftor (CPT 656), genistein and GLPG1837.

As used herein, the term "CFTR pharmacological chaperone" (PC) refers to compounds that stabilize the CFTR protein in its native state by binding directly to the protein.

As used herein, the term "CFTR proteostasis regulator" (PR) refers to compounds that enhance the protein folding efficiency within the cell. PRs can alter the activity of transcriptional, folding and/or membrane trafficking machinery, as well as impeding the degradation of partially folded, but functional, conformers at the endoplasmic reticulum (ER) or plasma membrane.

As used herein, "CFTR disease or condition" refers to a disease or condition associated with deficient CFTR activity, for example, cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, dry eye disease, protein C deficiency, A-beta.-lipoproteinemia, lysosomal storage disease, type 1 chylomicronemia, mild pulmonary disease, lipid processing deficiencies, type 1 hereditary angioedema, coagulation-fibrinolysis, hereditary hemochromatosis, CFTR-related metabolic syndrome, chronic bronchitis, constipation, pancreatic insufficiency, hereditary emphysema, and Sjogren's syndrome.

As used herein, the term "combination," "combined," and related terms refers to the simultaneous or sequential administration of therapeutic agents in accordance with this disclosure. For example, a compound of the present disclosure may be administered with another therapeutic agent simultaneously or sequentially in separate unit dosage forms or together in a single unit dosage form. Accordingly, the present disclosure provides a single unit dosage form comprising a provided compound, an additional therapeutic agent, and a pharmaceutically acceptable carrier, adjuvant, or vehicle.

ALTERNATIVE EMBODIMENTS

In an alternative embodiment, compounds described herein may also comprise one or more isotopic substitutions. For example, hydrogen may be $^{2}H$ (D or deuterium) or $^{3}H$ (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^{3}H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In some embodiments, the present disclosure provides a composition comprising a compound of Formula (A) and a pharmaceutically acceptable carrier, adjuvant, or vehicle. In some embodiments, the amount of compound in compositions contemplated herein is such that is effective to measurably modulate CFTR, or a mutant thereof, in a biological sample or in a patient. In certain embodiments, the amount of compound in compositions of this disclosure is such that is effective to measurably modulate CFTR, or a mutant thereof, in a biological sample or in a patient. In certain embodiments, a composition contemplated by this disclosure is formulated for administration to a patient in need of such composition. In some embodiments, a composition contemplated by this disclosure is formulated for oral administration to a patient.

In some embodiments, the amount of compound in compositions contemplated herein is such that is effective to measurably modulate a protein, particularly at CFTR, or a mutant thereof, in a biological sample or in a patient. In certain embodiments, the amount of compound in compositions of this disclosure is such that is effective to measurably modulate CFTR, or a mutant thereof, in a biological sample or in a patient.

In some embodiments, compositions of the present disclosure may be administered orally, parenterally, by inhalation spray, topically, rectally, nasally, buccally, vaginally or via an implanted reservoir. In some preferred embodiments, compositions are administered orally, intraperitoneally or intravenously. In some embodiments, sterile injectable forms of the compositions comprising one or more compounds of Formula (A) may be aqueous or oleaginous suspension. In some embodiments, suspensions may be formulated according to techniques known in the art using suitable dispersing or wetting agents and suspending agents. In some embodiments, sterile injectable preparation may also be a sterile injectable solution or suspension in a non-toxic parenterally acceptable diluent or solvent, for example as a solution in 1,3-butanediol. In some embodiments, among the acceptable vehicles and solvents that may be employed are water, Ringer's solution and isotonic sodium chloride solution. In some embodiments, additional examples include, but are not limited to, sterile, fixed oils are conventionally employed as a solvent or suspending medium.

The term "parenteral" as used herein includes subcutaneous, intravenous, intramuscular, intra-articular, intra-synovial, intrasternal, intrathecal, intrahepatic, intralesional and intracranial injection or infusion techniques.

Pharmaceutically acceptable compositions comprising one or more compounds of Formula (A) may be orally administered in any orally acceptable dosage form including, but not limited to, capsules, tablets, aqueous suspensions or solutions. In some embodiments, carriers used include lactose and corn starch. Lubricating agents, such as magnesium stearate, are also typically added. In some embodiments, useful diluents include lactose and dried cornstarch. In some embodiments, when aqueous suspensions are required for oral use, an active ingredient is combined with emulsifying and suspending agents. In some embodiments, certain sweetening, flavoring or coloring agents may also be added.

Alternatively, pharmaceutically acceptable compositions comprising a compound of Formula (A) may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions comprising a compound of Formula (A) may also be administered topically, especially when the target of treatment includes areas or organs readily accessible by topical application, including diseases of the eye, the skin, or the lower intestinal tract. Suitable topical formulations are readily prepared for each of these areas or organs. In some embodiments, pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions comprising a compound of Formula (A) may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, an amount of a compound of the present disclosure that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

Methods of Using Compounds of the Present Disclosure

As discussed above, CFTR is composed of two six membrane-spanning domains (MSD1 and MSD2), two nucleotide bind domains (NBD1 and NBD2), a regulatory region (R) and four cytosolic loops (CL1-4). CFTR protein is located primarily in the apical membrane of epithelial cells where it functions to conduct anions, including chloride, bicarbonate and thiocyanate into and out of the cell. The most frequent CFTR mutation is the in-frame deletion of phenylalanine at residue 508 (ΔF508) in the first nucleotide binding domain (NBD1). The mutation has several deleterious effects on the production of CFTR in the ER, its correct folding, its movement to the plasma membrane and its normal function as an ion channel for the cell.

One such negative effect is that the NBD1 domain is partially or mis-folded which is recognized within the cell as an aberrant protein and tagged for disposal by ER-associated degradation (ERAD) via the ubiquitin-proteasome system (UPS). Should a partially or mis-folded CFTR protein emerge from the ER, the protein must travel to the plasma membrane through complex glycosylation in the Golgi compartment and be functionally inserted. In wild-type CFTR, only 20-40% of CFTR reaches the plasma membrane, indicating that CFTR has energetic instability of individual NBDs, a slow domain assembly, and relatively fast ERAD kinetics which all contribute to inefficient folding and sensitize CFTR to structural perturbations by mutations.

In wild-type CFTR, the NBD1 domain folds co-translationally while other domains fold post-translationally. Mutated ΔF508 CFTR has impaired NBD1 folding but its backbone structure and thermodynamic stability are similar to wild-type CFTR. With delayed folding kinetics, mutated ΔF508 CFTR NBD1 has an increased folding activation energy. Lack of proper folding results in hydrophobic residues being exposed to the surface of NBD1 which causes aggregation with other CFTR proteins. Thus, the aggregation temperature of mutated CFTR drops from 41° C. to 33° C. This level of instability creates a greater percentage of mis-folded mutant CFTR at physiological temperature (37° C. in humans). Mutant CFTR suffers from both kinetic and thermodynamic folding defects. CFTR stabilizers can address these folding defects, but complete energetic correction of mutant NBD1 folding has been shown to not result in the CFTR biosynthetic processing, underscoring the need for interface stability as well.

The disclosed CFTR correctors can interact with the NBD domain to stabilize the correct folded position R, such that CFTR is not labeled for elimination from the cell. The preservation of correct folding enables CFTR to function as a chloride ion channel at wild-type levels. In some embodiments, disclosed CFTR correctors can enhance the performance of wild-type CFTR.

CFTR stabilizers can function in combination with other therapeutic agents such as CFTR correctors that promote Δ508 CFTR exit from the ER and accumulation in the plasma membrane. Increasing the amount of CFTR cell surface expression can result in improved chloride conductance following channel activation by both potentiators and a cAMP agonist. Thus, disclosed herein are combinations of CFTR stabilizers with CFTR correctors and potentiators, optionally with cAMP agonists or another therapeutic agent as described below.

Disclosed herein are methods of treating deficient CFTR activity in a cell, comprising contacting the cell with a compound of Formula (A), or a pharmaceutically acceptable salt thereof. In certain embodiments, contacting the cell occurs in a subject in need thereof, thereby treating a disease or disorder mediated by deficient CFTR activity.

Also, disclosed herein are methods of treating a disease or a disorder mediated by deficient CFTR activity comprising administering a compound of Formula (A) or a pharmaceutically acceptable salt thereof. In some embodiments, the subject is a mammal, preferably a human. In some embodiments, the disease is associated with the regulation of fluid volumes across epithelial membranes, particularly an obstructive airway disease such as CF or COPD.

Such diseases and conditions include, but are not limited to, cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear palsy, Pick's disease, several polyglutamine neurological disorders, Huntington's, spinocerebellar ataxia type I, spinal and bulbar muscular atrophy, dentatorubal pallidoluysian, myotonic dystrophy, spongiform encephalopathies, hereditary Creutzfeldt-Jakob disease, Fabry disease, Straussler-Scheinker syndrome, COPD, dry-eye disease, Sjogren's disease, Osteoporosis, Osteopenia, bone healing and bone growth, bone repair, bone regeneration, reducing bone resorption, increasing bone deposition, Gorham's Syndrome, chloride channelopathies, myotonia congenita, Bartter's syndrome type III, Dent's disease, hyperekplexia, epilepsy, hyperekplexia, lysosomal storage disease, Angelman syndrome, Primary Ciliary Dyskinesia (PCD), PCD with situs inversus, PCD without situs inversus and ciliary aplasia.

Such diseases and conditions include, but are not limited to, cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, Abetalipoproteinemia, lysosomal storage disease, type 1 chylomicronemia, mild pulmonary disease, lipid processing deficiencies, type 1 hereditary angioedema, coagulation-fibrinolysis, hereditary hemochromatosis, CFTR-related metabolic syndrome, chronic bronchitis, constipation, pancreatic insufficiency, hereditary emphysema, and Sjogren's syndrome. In some embodiments, the disease is cystic fibrosis.

Provided herein are methods of treating cystic fibrosis, comprising administering to a subject in need thereof, a compound as disclosed herein or a pharmaceutically acceptable salt thereof. Also provided herein are methods of lessening the severity of cystic fibrosis, comprising administering to a subject in need thereof, a compound as disclosed herein or a pharmaceutically acceptable salt thereof. In some embodiments, the subject is a human. In some embodiments, the subject is at risk of developing cystic fibrosis, and administration is carried out prior to the onset of symptoms of cystic fibrosis in the subject.

Provided herein are compounds as disclosed herein for use in treating a disease or condition mediated by deficient CFTR activity. Also provided herein are uses of a compound as disclosed herein for the manufacture of a medicament for treating a disease or condition mediated by deficient CFTR activity.

Provided herein are kits for use in measuring the activity of CFTR or a fragment thereof in a biological sample in vitro or in vivo. The kit can contain: (i) a compound as disclosed herein, or a pharmaceutical composition comprising the disclosed compound, and (ii) instructions for: a) contacting the compound or composition with the biological sample; and b) measuring activity of said CFTR or a fragment thereof. In some embodiments, the biological sample is biopsied material obtained from a mammal or extracts thereof; blood, saliva, urine, feces, semen, tears, other body fluids, or extracts thereof. In some embodiments, the mammal is a human.

Combination Treatments

As used herein, the term "combination therapy" means administering to a subject (e.g., human) two or more CFTR modulators, or a CFTR modulator and an agent such as antibiotics, ENaC inhibitors, GSNO (S-nitrosothiol, s-nitroglutathione) reductase inhibitors, and a CRISPR Cas correction therapy or system (as described in US 2007/0022507 and the like). In some embodiments, combination therapy includes administration of a compound described herein with a compound that modulates CFTR protein or ABC protein activities (e.g., as described in WO2018167690A1 and the like)

In certain embodiments, the method of treating a disease or condition mediated by deficient CFTR activity comprises administering a compound as disclosed herein conjointly with one or more other therapeutic agent(s). In some embodiments, one other therapeutic agent is administered. In other embodiments, at least two other therapeutic agents are administered.

In certain embodiments, the method of preventing a disease or condition mediated by deficient CFTR activity comprises administering a compound as disclosed herein conjointly with one or more other therapeutic agent(s). In some embodiments, one other therapeutic agent is administered. In other embodiments, at least two other therapeutic agents are administered.

Additional therapeutic agents include, for example, ENaC inhibitors, mucolytic agents, modulators of mucus rheology, bronchodilators, antibiotics, anti-infective agents, anti-inflammatory agents, ion channel modulating agents, therapeutic agents used in gene or mRNA therapy, agents that reduce airway surface liquid and/or reduce airway surface PH, CFTR correctors, and CFTR potentiators, or other agents that modulate CFTR activity. Other therapeutics include liposomal composition components such as those described in WO2012/170889, hybrid oligonucleotides that facilitate RNA cleavage such as those described in WO2016/130943, and single stranded oligonucleotides that modulate gene expression as described in WO2016/130929.

In some embodiments, at least one additional therapeutic agent is selected from one or more CFTR modulators, one or more CFTR correctors and one or more CFTR potentiators.

Non-limiting examples of additional therapeutics include VX-770 (Ivacaftor), VX-809 (Lumacaftor, 3-(6-(I-(2,2-5 difluorobenzo[d][1, 3]dioxol-5-yl)cyclopropanecarboxamido)-3-methylpyridin-2-yl) benzoic acid, VX-661 (Tezacaftor, I-(2,2-difluoro-1, 3-benzodioxol-5-yl)-N-[I-[(2R)-2,3-dihydroxypropyl]-6-fluoro-2-(2-hydroxy-1, I-dimethylethyl)-1H-indol-5-yl]-cyclopropanecarboxamide), VX-983, VX-152, VX-440, VX-445, VX-659, VX-371, Orkambi, Ataluren (PTC 124) (3-[5-(2-fluorophenyl)-1, 2,4-oxadiazol-3-yl]benzoic acid), PTI-130 (Proteostasis), PTI-801, PTI-808, PTI-428, N91115.74 (cavosonstat), QBW251 (Novartis) compounds described in WO2011113894, compounds N30 Pharmaceuticals (e.g., WO 2014/186704), deuterated ivacaftor (e.g., CTP-656 or VX-561), GLPG 2222, GLPG2451, GLPG3067, GLPG2851, GLPG2737, GLPG 1837 (N-(3-carbamoyl-5,5,7,7-tetramethyl-5,7-dihydro-4H-thieno[2,3-c]pyran-2-yl)-1H-pyrazole-5-carboxamide), GLPG 2665 (Galapagos), FDL 169 (Flatley Discovery lab), FDL 176, FDL438, FDL304, FD2052160, FD1881042, FD2027304, FD2035659, FD2033129, FD1860293, CFFT-Pot01, CFFT-Pot-02, P-1037, glycerol, phenylbutyrate, and the like.

Non-limiting examples of additional therapeutics include compounds disclosed in US Patent Application Nos. 62/944,141, 62/944,158 and 62/944,188, each of which is incorporated by reference in its entirety.

Non-limiting examples of anti-inflammatory agents are N6022 (3-(5-(4-(1H-imidazol-I-yl)10 phenyl)-I-(4-carbamoyl-2-methylphenyl)-'H-pyrrol-2-yl) propanoic acid), Ibuprofen, Lenabasum (anabasum), Acebilustat (CTX-4430), LAU-7b, POL6014, docosahexaenoic acid, alpha-1 anti-trypsin, sildenafil. Additional therapeutic agents also include, but are not limited to a mucolytic agent, a modifier of mucus rheology (such as hypertonic saline, mannitol, and oligosaccharide based therapy), a bronchodilator, an anti-infective (such as tazobactam, piperacillin, rifampin, meropenum, ceftazidime, aztreonam, tobramycin, fosfomycin, azithromycin, amitriptyline, vancomycin, gallium and colistin), an anti-infective agent, an anti-inflammatory agent, a CFTR modulator other than a compound of the present disclosure, and a nutritional agent. Additional therapeutic agents can include treatments for comorbid conditions of cystic fibrosis, such as exocrine pancreatic insufficiency which can be treated with Pancrelipase or Liprotamase.

Examples of CFTR potentiators include, but are not limited to, Ivacaftor (VX-770), CTP-656, NVS-QBW251, FD1860293, GLPG2451, GLPG1837, and N-(3-carbamoyl-5,5,7,7-tetramethyl-5,7-dihydro-4H-thieno[2,3-c]pyran-2-yl)-1H-pyrazole-5-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, and U.S. patent application Ser. Nos. 14/271,080, 14/451,619 and 15/164,317.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanec arboxamide (VX-661), VX-983, GLPG2222, GLPG2665, GLPG2737, VX-152, VX-440, FDL169, FDL304, FD2052160, and FD2035659. Examples of correctors are also disclosed in US20160095858A1, and U.S. application Ser. Nos. 14/925,649 and 14/926,727.

In certain embodiments, the additional therapeutic agent is a CFTR amplifier. CFTR amplifiers enhance the effect of known CFTR modulators, such as potentiators and correctors. Examples of CFTR amplifier include PTI130 and PTI-428. Examples of amplifiers are also disclosed in publications: WO2015138909 and WO2015138934.

In certain embodiments, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, AZD5634, and VX-371. Additional agents that reduce the activity of the epithelial sodium channel blocker (ENaC) can be found, for example, in PCT Publication No. WO2009074575 and WO2013043720; and U.S. Pat. No. 8,999,976.

In one embodiment, the ENaC inhibitor is VX-371.

In one embodiment, the ENaC inhibitor is SPX-101 (S18).

In certain embodiments, the combination of a compound of Formula (A), with a second therapeutic agent may have a synergistic effect in the treatment of cancer and other diseases or disorders mediated by adenosine. In other embodiments, the combination may have an additive effect.

EXEMPLIFICATION

Abbreviations

Boc: tert-butyloxycarbonyl

DEA: diethyl amine

DBU: 1,8-Diazabicyclo[5.4.0]undec-7-ene

DMSO: dimethyl sulfoxide dppf: 1,1'-Bis(diphenylphosphino)ferrocene

DTT: dithiothreitol

ESI: electron spray ionization

HATU: 1-[Bis(dimethylamino)methylene]-1H-1,2,3-triazolo[4,5-b]pyridinium 3-oxide hexafluorophosphate HPLC: high performance liquid chromatography LC-MS: liquid chromatography-mass spectrometry NIS: N-iodosuccinimide Pd/C: Palladium on carbon SFC: supercritical fluid chromatography TBS: tert-Butyldimethylsilyl TIPS: Triisopropylsilyl THF: tetrahydrofuran THP: tetrahydropyran Ts: tosyl

General Procedures

The compounds of the present disclosure can be better understood in connection with the following synthetic schemes and methods which illustrate a means by which the compounds of the Formula (A) can be prepared. The compounds of this disclosure can be prepared by a variety of synthetic procedures illustrated in Schemes I to VII.

Scheme I-1: Indole synthesis 1

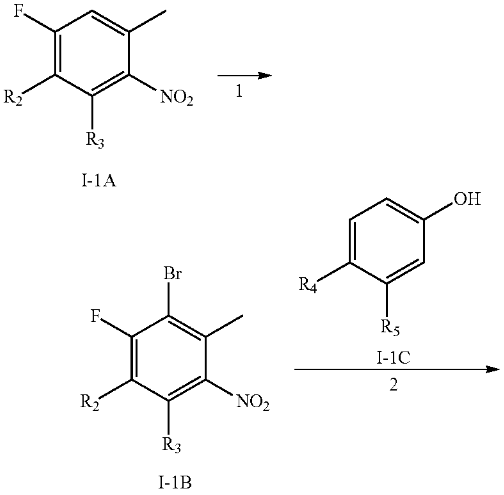

I-1A

I-1C

I-1B

-continued

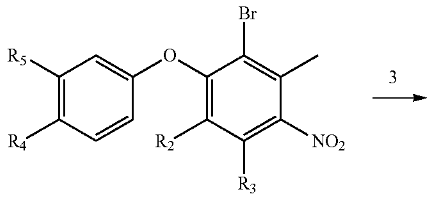

I-1D

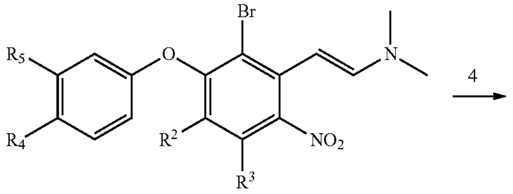

I-1E

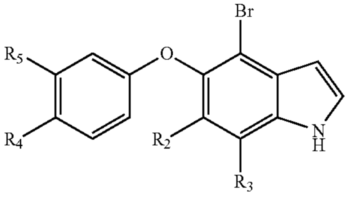

I-1F

The intermediate I-1F may be prepared as illustrated in Scheme I-1. Properly substituted methyl nitrobenzene (I-1A) is brominated (step 1) to give bromide I-1B. Compound I-1B is condensed with phenol I-1C (step 2) to give I-1D. Treatment of I-1D with N,N-dimethylformamide dimethyl acetal (step 3) forms I-1E, which is followed by reduction-cyclization (step 4) results in I-1F.

Scheme I-2: Indole Synthesis 2

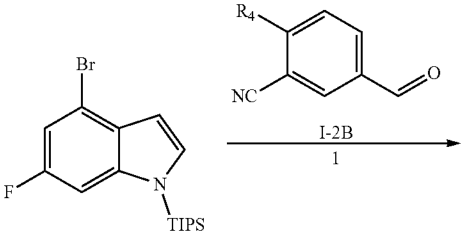

I-2A

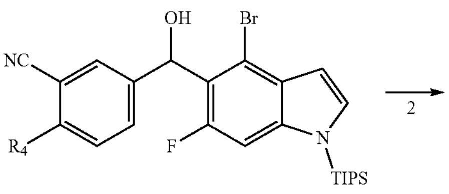

I-2C

-continued

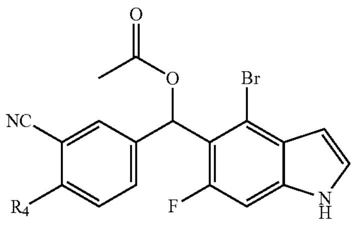

I-2D

The bromo indole intermediate I-2D can be synthesized according to Scheme I-2. Triisopropylsilyl protected indole I-2A is deprotonated with a strong base like lithium diisopropylamide or lithium bis(trimethylsilyl)amide, then treated with aldehyde I-2B (step 1) to form I-2C. Acetyl protection of alcohol I-2C gives I-2D.

Scheme I-3: Indole Synthesis 3

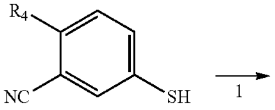

I-3A

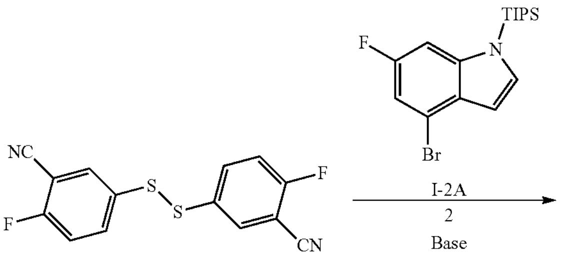

I-3B

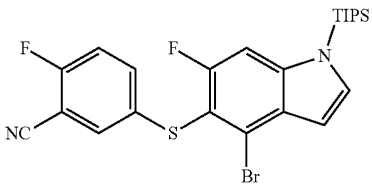

I-3C

A similar method is used to prepare intermediate I-3C. Thiol I-3A is oxidized to dithioether I-3B, which is then treated with a strong base for position-specific deprotonation of indole I-2A to afford I-3C.

Scheme I-4: Indole Synthesis 4

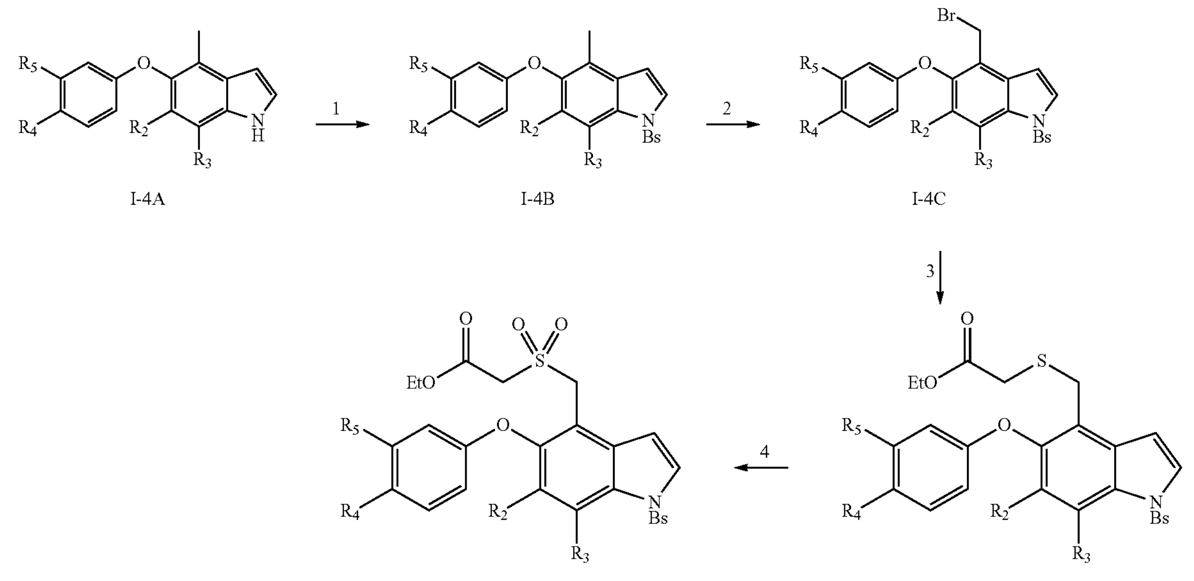

I-4A I-4B I-4C I-4D I-4E

The intermediate I-4E is prepared in a 4-step sequence as shown in Scheme I-4. Protection of the indole (Step 1), then bromination of the methyl group (step 2) to afford intermediate I-4C, which is treated with ethyl thioacetate (step 3) to form I-4D. Oxidation of I-4D affords I-4E.

Scheme I-5: Indole Synthesis 5

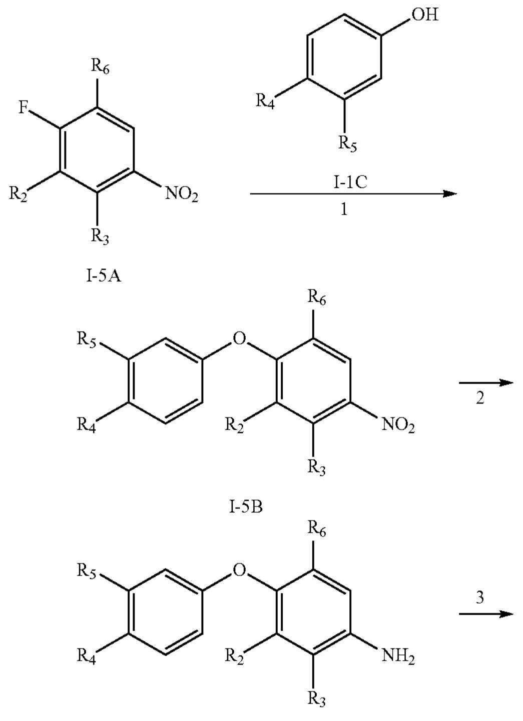

I-5A I-1C I-5B I-5C

-continued

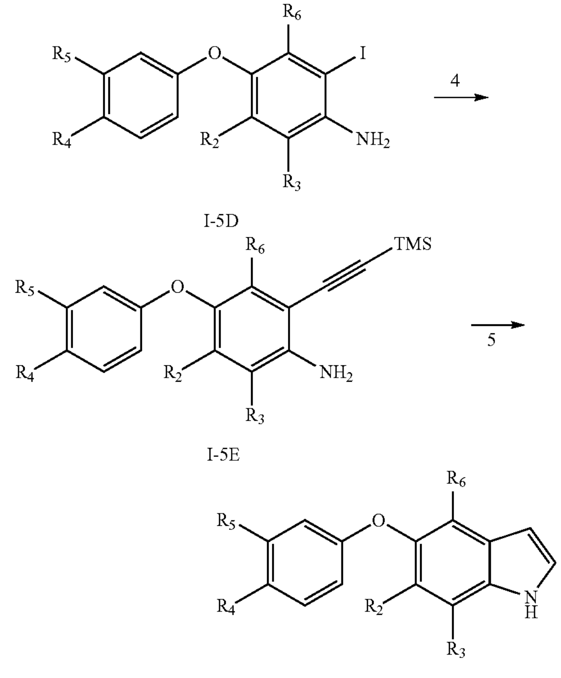

I-5D I-5E I-1F

Scheme I-5 describes an alternative method to prepare the intermediate I-1F. Intermediate I-5A is condensed with phenol I-1C (step 1) to yield intermediate I-5B. Reduction of the nitro group into amine (step 2) affords I-5C, to which iodine is introduced (step 3) to give intermediate I-5D. The intermediate 1-5D is then coupled with protected acetylene to yield intermediate I-5E (step 4). Cyclization of I-5E (step 5) yields the key intermediate I-1F.

Scheme II-1: Amidine, Thioamides and Methyl Imidothioate Synthesis
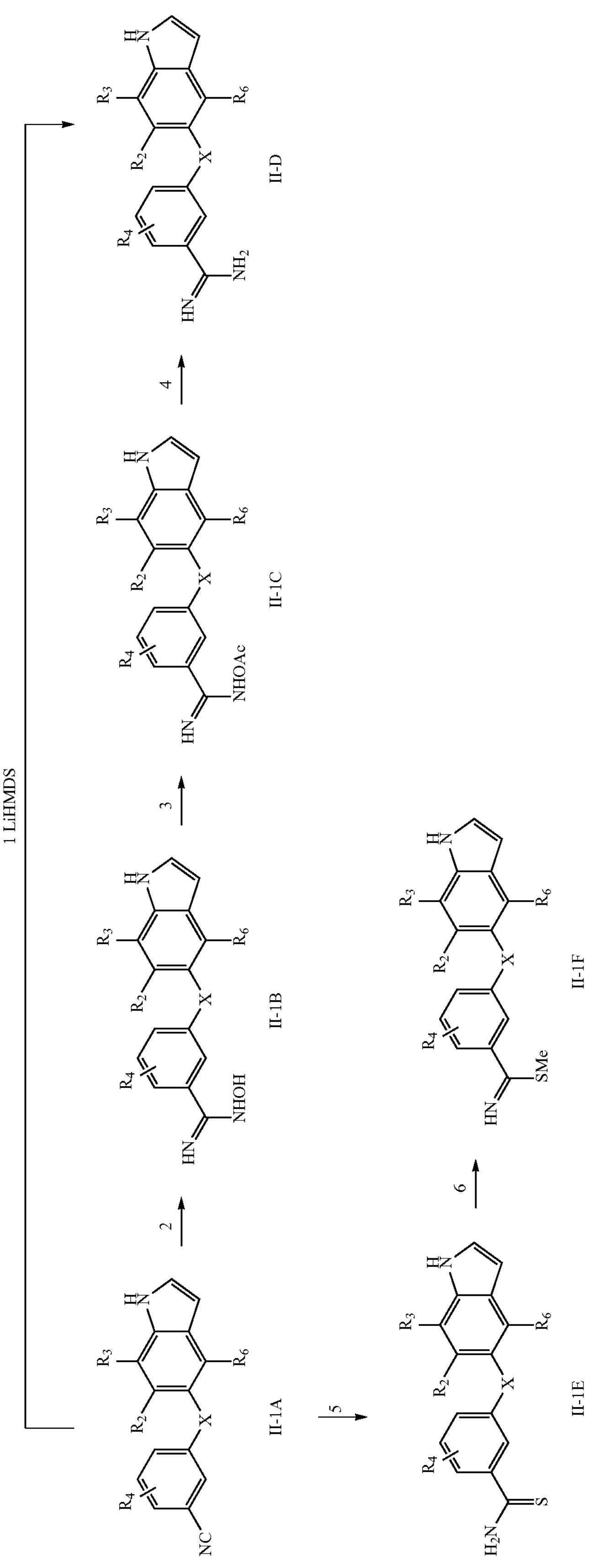
II-1A II-1B II-1C II-D II-1E II-1F Intermediate amidine II-1D can be prepared from corresponding nitrile II-1A in one step when treated with lithium bis(trimethylsilyl)amide (step 1). Alternatively, amidine II-1D can also be prepared from a three-step sequence. Addition of hydroxylamine to nitrile II-1A results in hydroxyamidine (step 2). Acetylation (step 3), followed by hydrogenation affords amidine II-1D. Nitrile can be alternatively converted to thioamide II-1E (step 5). Methyl benzimidothioate is formed (step 6) when thioamide is treated with an active methyl source such as iodomethane.

Scheme II-2: Synthesis of Pyrazole

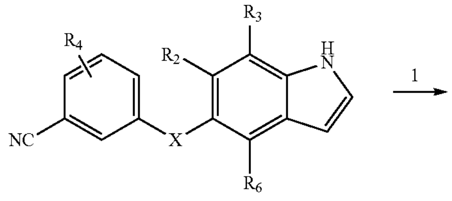

II-1A

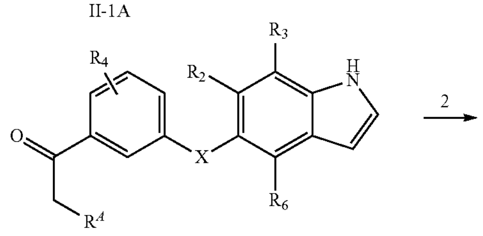

II-2A

-continued

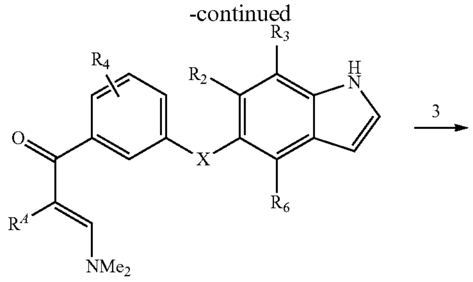

II-2B

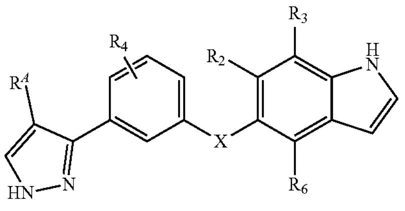

II-2C

Intermediate II-2C can be synthesized through a three-step sequence. Ketone II-2A, prepared from nitrile II-1A or another related precursor (step 1), is condensed with dimethylformamide dimethyl acetal (step 2). The resulting imine is cyclized with hydrazine (step 3) to form pyrazole II-2C.

Scheme III-1: Synthesis of quaternary carbon center containing sulfones

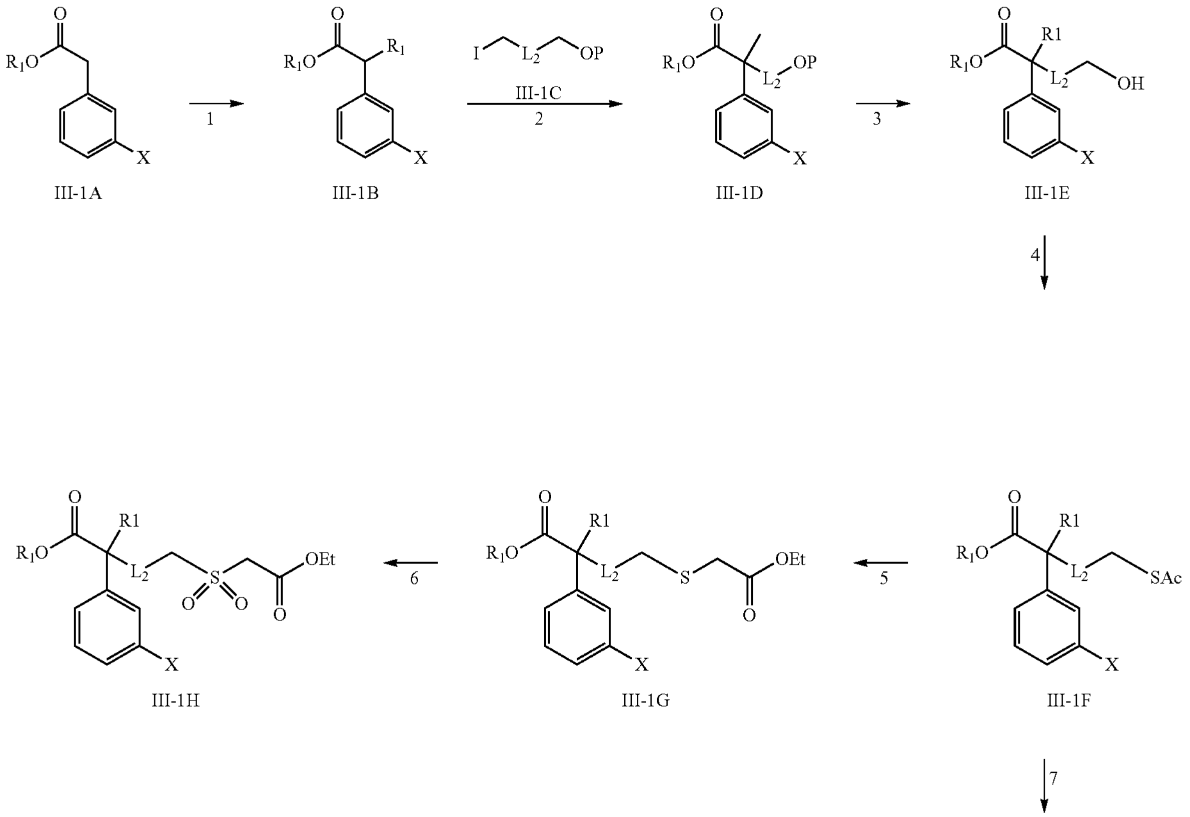

III-1A III-1B III-1D III-1E

III-1H III-1G III-1F

-continued

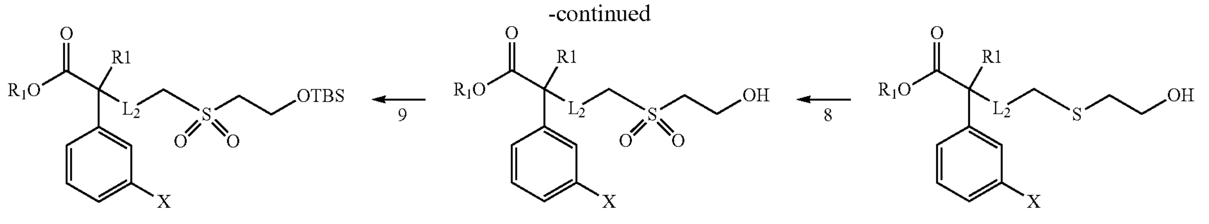

III-1L III-1K III-1J

The synthesis of intermediates III-1K, III-1L, III-1H are shown in Scheme III-1. Phenyl acetic acids are monosubstituted to form III-1B (Step 1). Substitution with proper iodides (intermediate III-1C, step 2) results in III-1D. Deprotection (step 3) followed by Mitsunobu reaction (step 4) affords III-1F. Generation of thiol in situ, followed by addition of corresponding nucleophiles (step 5) forms intermediates III-1G and III-1J. Oxidation by proper oxidants forms III-1H and III-1K, respectively. TBS protection of III-1K affords III-1L.

Scheme IV-1: Installation of alkyl or alkyloxy acid chain

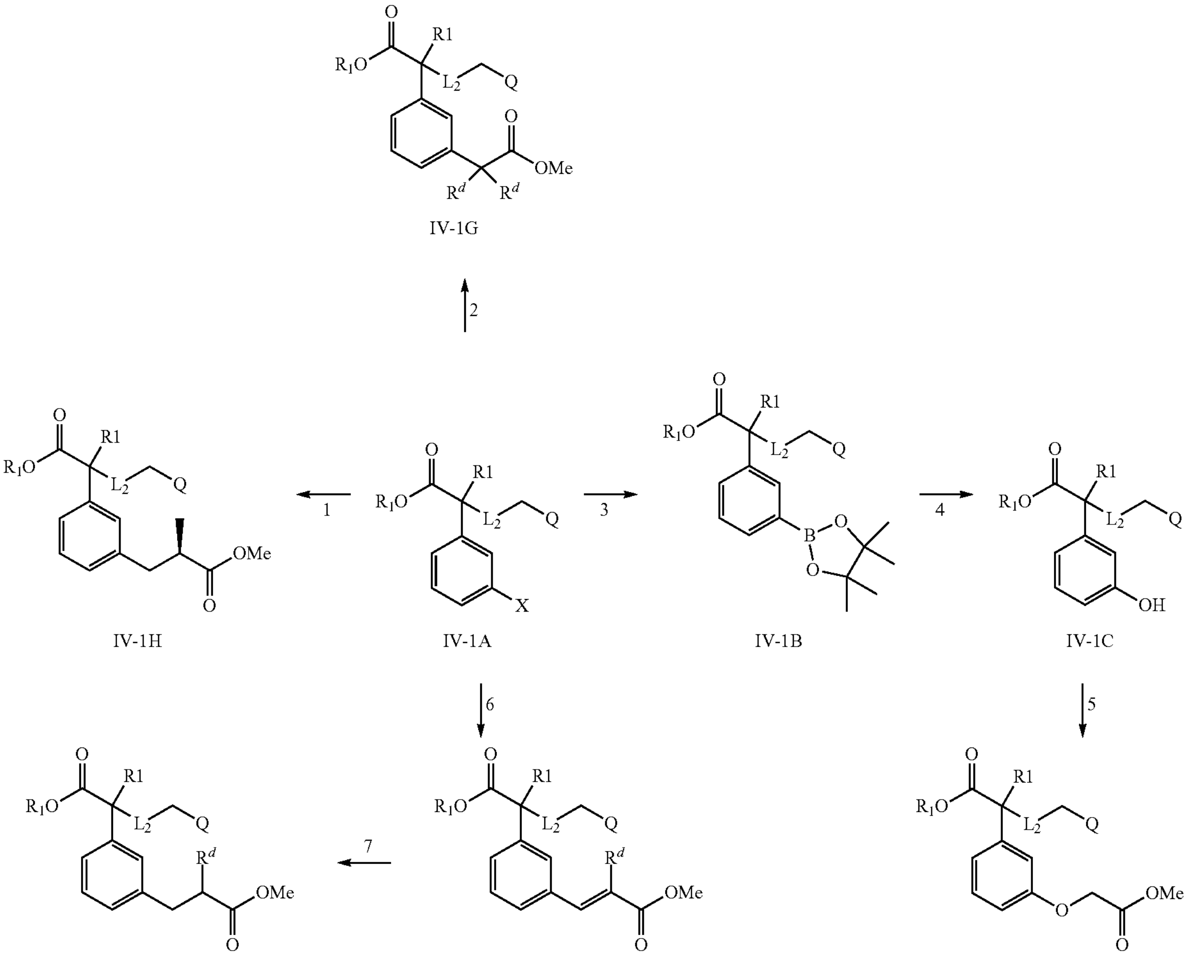

Q = OP or 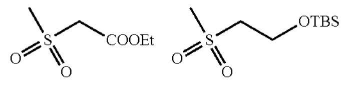

The installation of alkyl acid chains is illustrated in Scheme IV-1. Negishi coupling or other similar coupling reactions are used to form IV-1G (step 2) and IV-1H (step 1) from halide (IV-1A). Heck reaction (step 6) followed by hydrogenation (step 7) affords IV-1F. Alkyloxy analogue IV-1D is prepared from oxidation of boronic ester to phenol (step 4) and then alkylation (step 5).

Scheme V-1: Acid derivatives formation

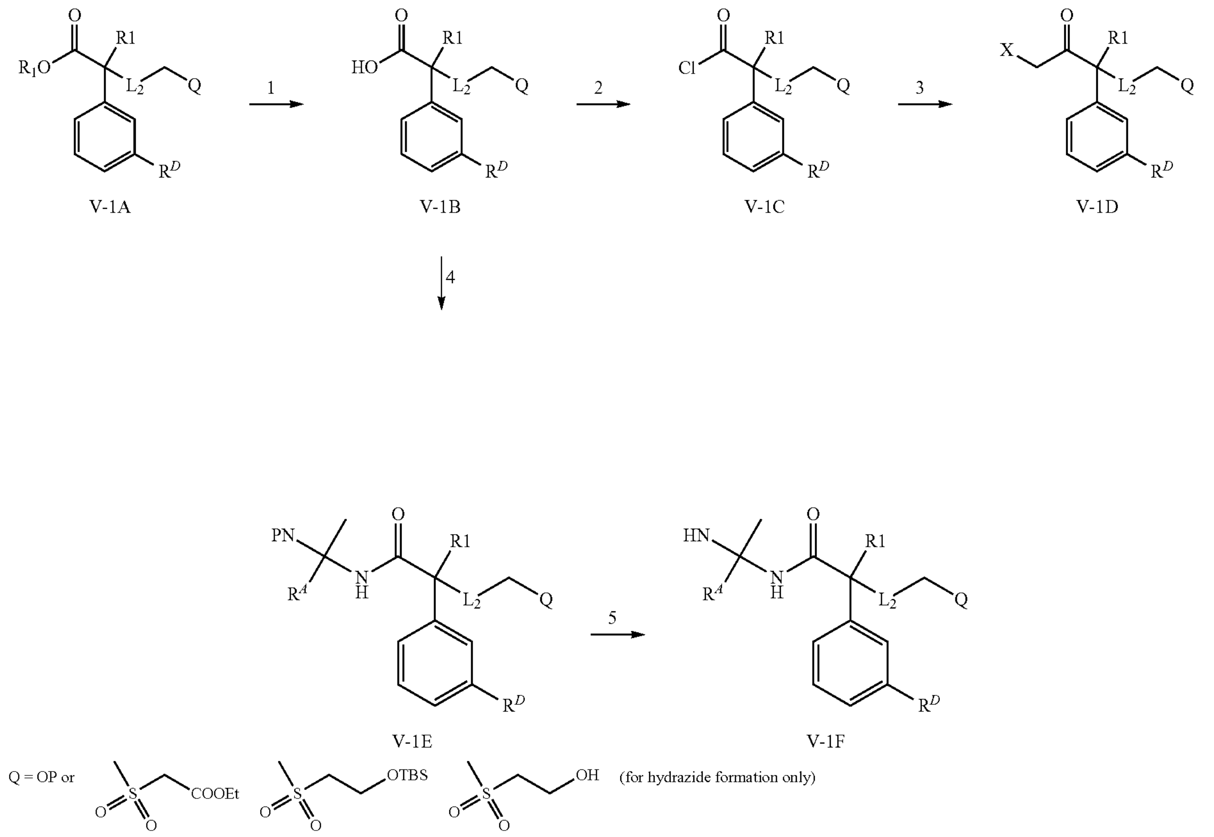

Acid V-1B is obtained from corresponding ester V-1A either from deprotection by a acid treatment (when R1 is tert-butyl), saponification (when R1 is alkyls like methyl or ethyl), or hydrogenation (when R1 is benzyl). Bromo or chloro ketone V-1D is prepared from corresponding acid (V-1B) via acyl chloride (step 2). The acyl chloride V-1C is treated with diazomethane, followed by reacting with either hydrogen chloride in 1,4-dioxane or hydrobromic acid in acetic acid to afford bromo or chloro ketone V-1D (step 3). The acid V-1B can also be directly converted to (monosubstituted) hydrazides by coupling with protected (monosubstituted) hydrazine (Step 4) followed by deprotection (step 5).

Scheme V-2: Alcohol/bromide intermediates

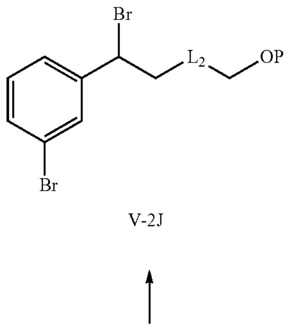

-continued

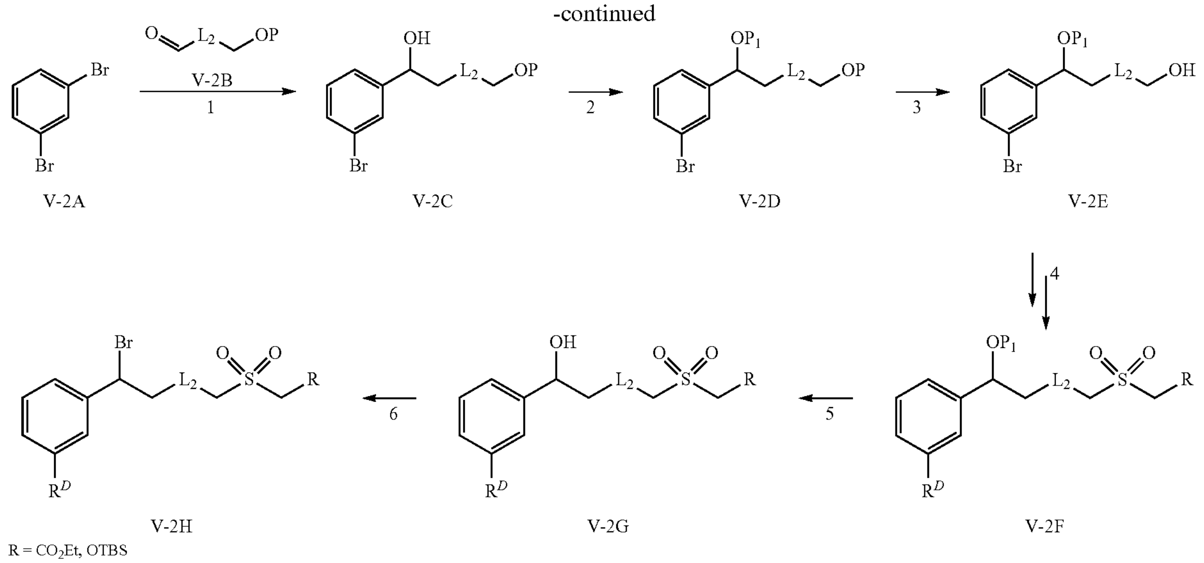

Intermediates V-2C, V-2J, V-2G and V-2H are used for the synthesis of corresponding pyrazole macrocyclic compounds. Scheme V-2 illustrates their preparation method. Mono metal-halogen exchange of V-2A followed by treatment with aldehyde V-2B (step 1) results in alcohol V-2C, which can be converted to bromide V-2J. Protection of secondary alcohol (step 2) and deprotection of primary alcohol (step 3) affords V-2E. Using a similar sequence as described in Scheme III, from 3-1E to 3-1H or 3-1E to 3-1L, V-2F is obtained. Deprotection of V-2F affords V-2G (step 5). Bromination of V-2G (step 6) results in bromide V-2H.

Scheme VI-1: Formation of B Rings 1
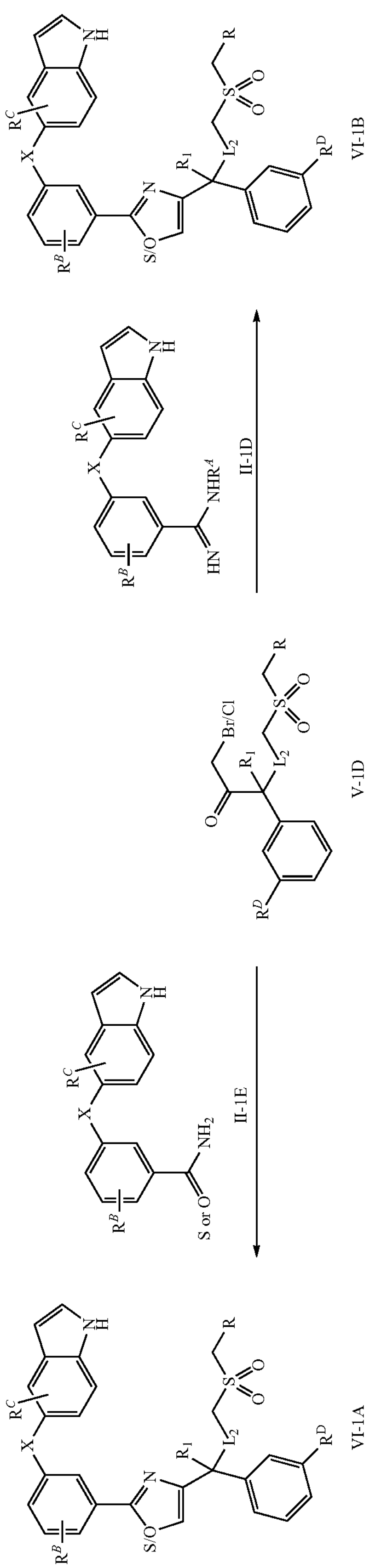

Scheme VI-1 demonstrates the preparation of the imidazole, oxazole, and thiazole ring systems of Ring B. Reaction of imidine II-1D with bromo or chloro ketone V-1D (Step 1) affords VI-1B. Reaction of thioamide/amide (II-1E) with bromo or chloro ketone V-1D followed by cyclization (step 2) gives oxazole or thiazole VI-1A.

Scheme VI-2: Formation of Triazoles

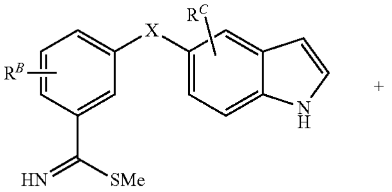

II-1F

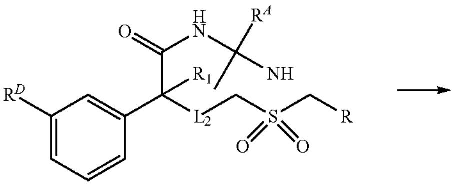

V-1F

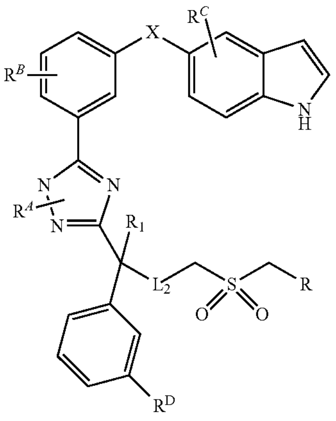

VI-2

The substituted or unsubstituted triazole intermediate VI-2 is prepared through the reaction of hydrazide V-1F with II-1F followed by cyclization in situ, as shown in Scheme VI-2.

Scheme VI-3: Formation of Pyrazoles

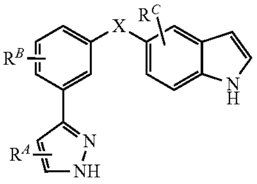

II-2C

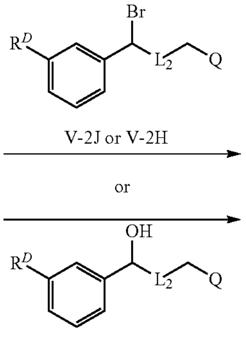

V-2C or V-2G

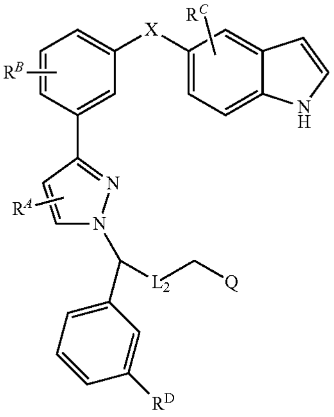

VI-3A

Q = OP

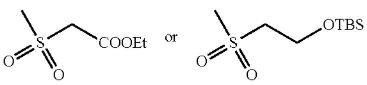

VI-3A can either be prepared from corresponding bromide V-2J or V-2H in the presence of base, or through Mitsunobu-type reaction through alcohol V-2C or V-2G, as shown in Scheme VI-3.

Scheme VII-1: Macrocyclization through condensation

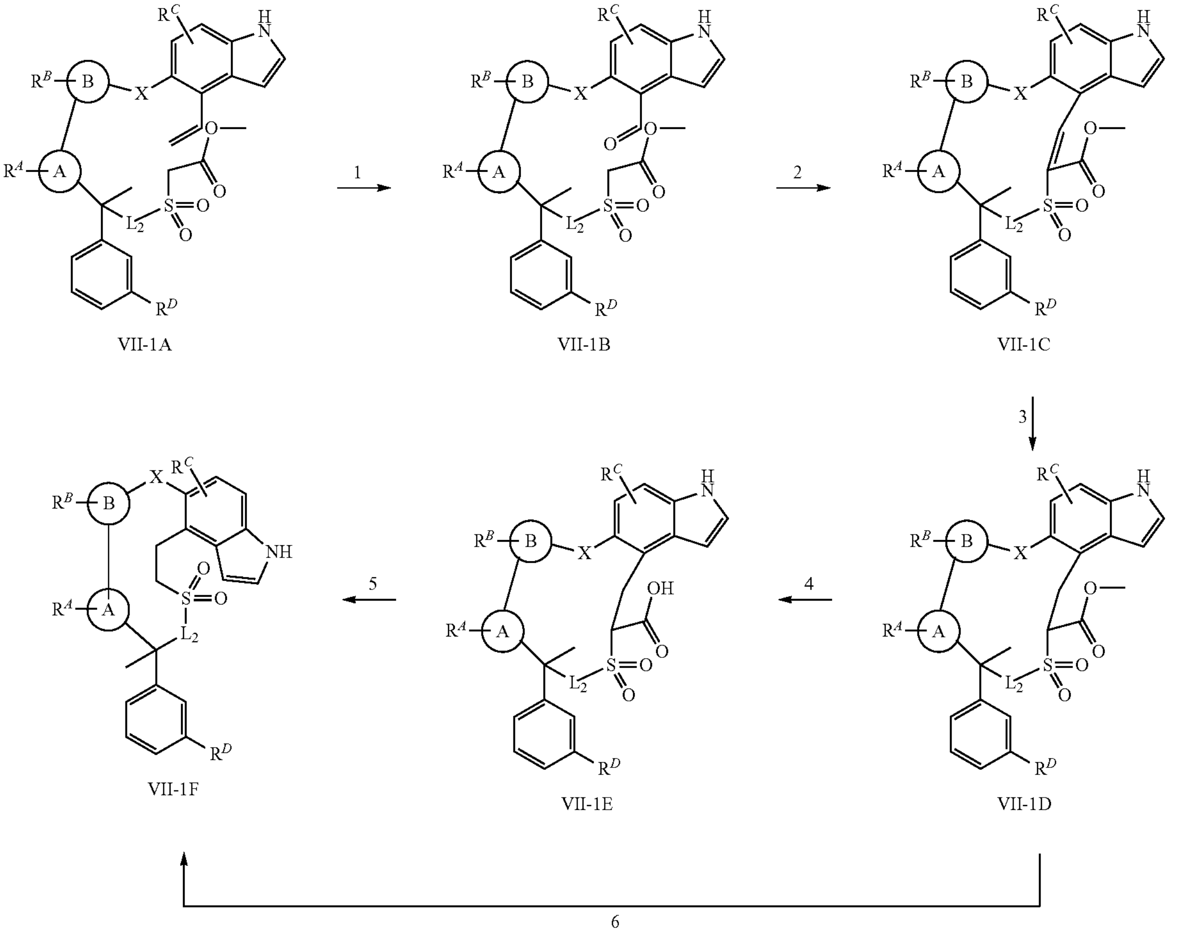

VII-1A VII-1B VII-1C

VII-1F VII-1E VII-1D

The macrocyclization can be achieved through aldehyde condensation as shown in Scheme VII-1. Vinyl indole VII-1A is oxidized to aldehyde in a two-step dihydroxylation-oxidation sequence (step 1). Intramolecular condensation of aldehyde VII-1B in the presence of a catalyst such as piperidine-acetic acid provides macrocyclic alkene VII-1C (step 2). Hydrogenation of alkene VII-1C (step 3) forms ester VII-1D. Saponification of ester VII-1D (step 4) affords acid VII-1E. Decarboxylation of VII-1E (step 5) forms VII-1F. Ester VII-1D can also be decarboxylated in one step (step 6) with a catalyst such as lithium chloride under standard reaction conditions to afford VII-1F. Scheme VII-2: Macrocyclization through condensation (II)

Scheme VII-2: Macrocyclization through condensation (II)

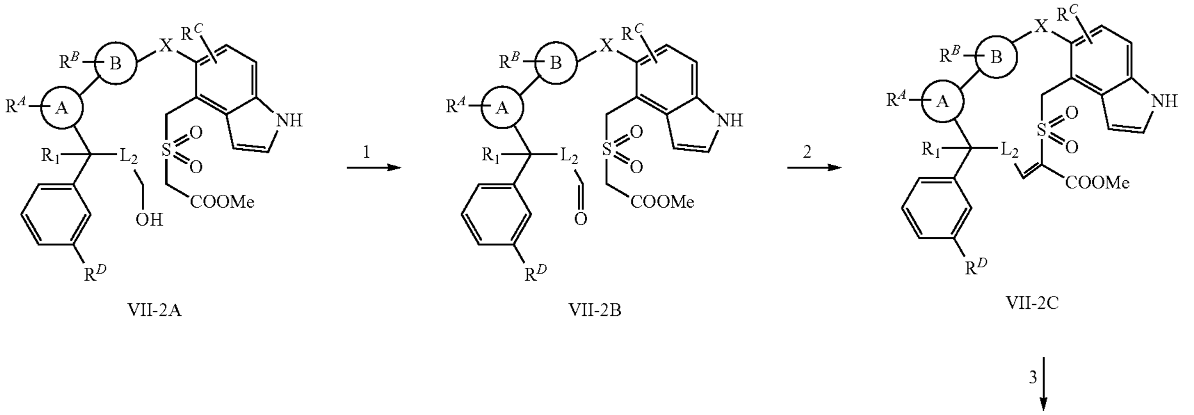

VII-2A VII-2B VII-2C

-continued

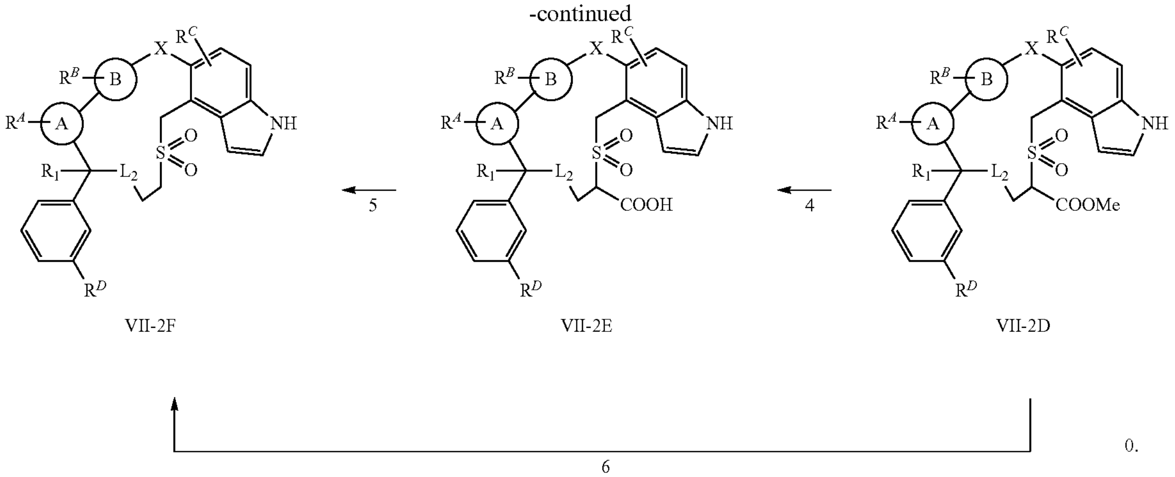

VII-2F VII-2E VII-2D

0.

An alternative version of macrocyclization through aldehyde condensation is shown in Scheme VII-2. The alcohol VII-2A is oxidized to aldehyde VII-2B using an oxidant like 2-iodoxybenzoic acid (step 1). Following the same sequence as in Scheme VII-1, the macrocycle VII-2F is obtained in 3 or 4 additional steps. Scheme VII-3: Macrocyclization Through Mitsunobu Reaction Scheme VII-3:Macrocyclization Through Mitsunobu Reaction

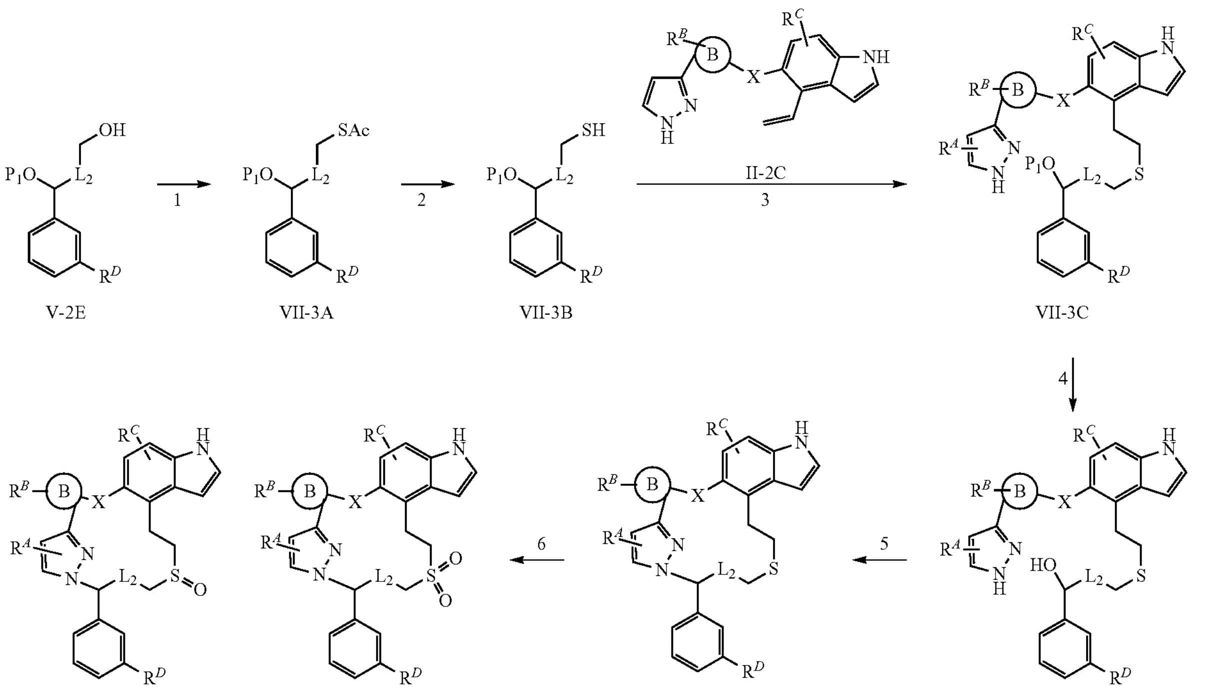

V-2E VII-3A VII-3B VII-3C

VII-3G VII-3F VII-3E VII-3D

For Pyrazoles and related macrocycles, Mitsunobu conditions can be used for the macrocyclization as shown in Scheme VII-3. Alcohol V-2E is converted to thioester VII-3A (step 1), either by Mitsunobu reaction, or by a two-step sequence, converting alcohol to a good leaving group like iodo, bromo, mesylate, then reacted with a nucleophile like sodium ethane thioate. Thiol VII-3B is formed by hydrolysis of thioester VII-3A. Treatment of thiol VII-3B with vinyl II-2C (step 3) forms thioether VII-3C. Deprotection of the alcohol VII-3C (step 4) forms alcohol VII-3D. Macrocyclization of alcohol VII-3D is facilitated by a suitable Mitsunobu reagent (step 5) to afford macrocyclic thioether VII-3E, which can be oxidized (step 6) to afford sulfone VII-3F or sulfoxide VII-3G.

Scheme VII-4: Macrocyclization through a Heck Reaction

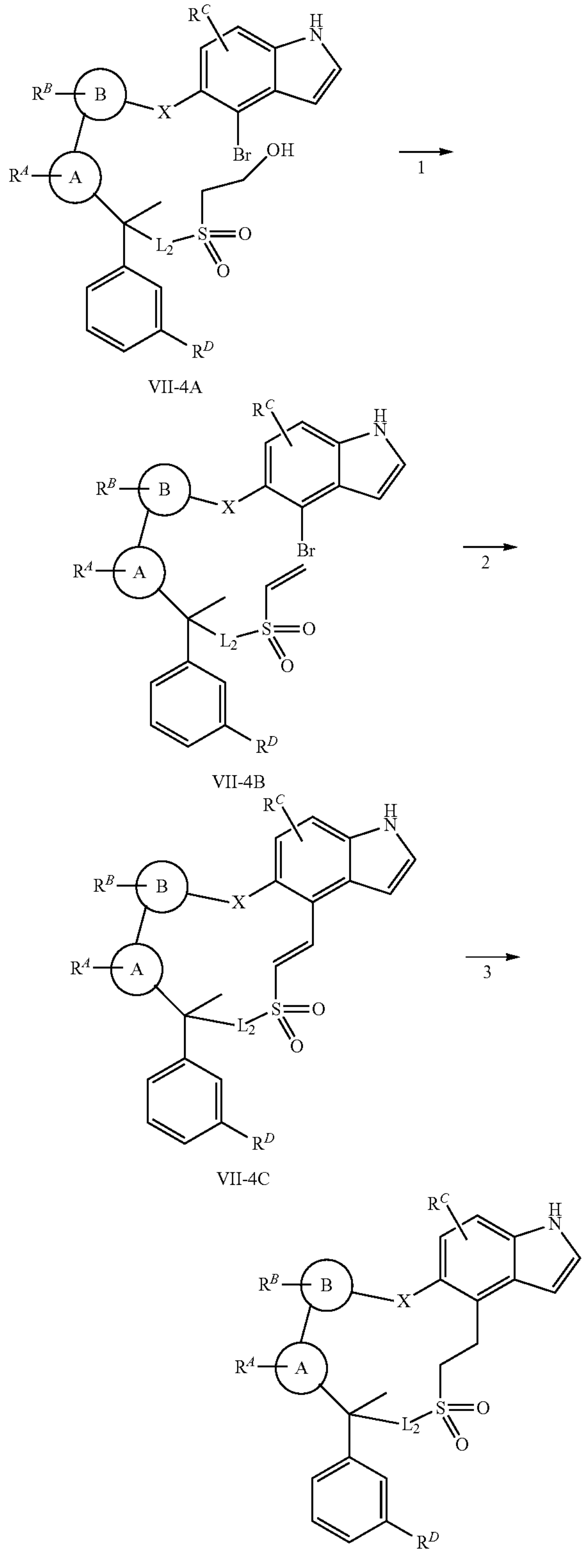

VII-4A

VII-4B

VII-4C

VII-4D

The macrocyclization can also be achieved through a Heck reaction as shown in Scheme VII-3. Alcohol sulfone VII-4A is dehydrated (step 1) through the formation of mesylate to form vinyl sulfone VII-4B. Heck reaction with a proper catalyst affords macrocyclic vinyl sulfone VII-4C (step 2). Hydrogenation of vinyl sulfone (step 3) affords sulfone VII-4D.

Analytical Methods:

Analytical Procedures $^{1}H$ NMR spectra were recorded with Bruker AC 400 MHz apparatus. Chemical shifts (δ) are quoted in parts per million (ppm) and coupling constants (J) in hertz (Hz).

The following liquid chromatography-Mass Spectrum (LC-MS) methods were used.

LC-MS Method 001:

Spectra were obtained with UPLC Acquity device of Waters for liquid chromatography part, coupling with mass spectrometer ZMD of Waters. This system was piloted by MassLynx v4.1 software. Detection was made in UV at 220 nm. Operational conditions for liquid chromatography part are the following: Column: Assentis Express C18 50×2.1 mm, 2.7μ Supelco Eluent: Way A: Water+0.02% trifluoroacetic acid; Way B: acetonitrile+0.014% trifluoroacetic acid; Gradient: TO min: 2% B, T1 min: 98% B, T1.3 min: 98% B, T1.33 min: 2% B, T1.5 min: following injection; Flow: 1 mL/min; Temperature: 55° C. SQD: ESI+ 30V UV: 220 nm Injection: 0.2 μl.

LC-MS Method 002:

Mobile Phase: A: water (0.01% trifluoroacetic acid) B: acetonitrile (0.01% trifluoroacetic acid). Gradient: 5% B increase to 95% B within 1.8 min, 95% B for 1.7 min. Flow Rate: 1.8 ml/min. Column: Chromolith Fast gradient RP-18e 50×3 mm. Column Temperature: 40° C. Detection: UV (214 nm, 254 nm) and MS (ESI, POS Mode, 110-1300 amu).

LC-MS Method 003:

Mobile Phase: A: water (0.01% trifluoroacetic acid), B: acetonitrile (0.01% trifluoroacetic acid); Gradient: 5% B increased to 95% B within 1.3 min, 95% B for 1.7 min, back to 5% B within 0.01 min; Flow Rate: 2 ml/min; Column: Sunfire, 50×4.6 mm, 3.5 um; Column Temperature: 50° C.; Detection: UV (214.4 nm) and MS (ESI, Pos mode, 110 to 1000 amu).

LC-MS Method 004:

Mobile Phase: A: water (0.01% trifluoroacetic acid), B: acetonitrile (0.01% trifluoroacetic acid); Gradient: 5% B increased to 95% B within 1.3 min, 95% B for 1.7 min, back to 5% B within 0.01 min; Flow Rate: 2 ml/min; Column: Sunfire, 50×4.6 mm, 3.5 um; Column Temperature: 45° C.; Detection: UV (214.4 nm) and MS (ESI, Pos mode, 110 to 1000 amu).

LC-MS Method 005:

Mobile Phase: A: water (0.01% trifluoroacetic acid), B: acetonitrile (0.01% trifluoroacetic acid); Gradient: 5% B increased to 95% B within 1.5 min, 95% B for 3.5 min, back to 5% B within 0.01 min; Flow Rate: 2 ml/min; Column: Sunfire, 50*4.6 mm, 3.5 um; Column Temperature: 45° C.; Detection: UV (214.4 nm) and MS (ESI, Pos mode, 110 to 1500 amu).

LC-MS Method 006:

LC-Mass Method: Mobile Phase: A: water (0.01% trifluoroacetic acid), B: acetonitrile (0.01% trifluoroacetic acid); Gradient: 5% B increased to 95% B within 2.2 min, 95% B for 2.8 min, back to 5% B within 0.01 min; Flow Rate: 2.2 ml/min; Column: Chromolith Fast gradient RP-18e, 50*3 mm; Column Temperature: 40° C.; Detection: UV (214, 4 nm) and MS (ESI, Pos mode, 110 to 1300 amu).

LC-MS Method 007:

LC-Mass Method: Mobile Phase: A: water (0.01% trifluoroacetic acid), B: acetonitrile (0.01% trifluoroacetic acid); Gradient: 10% B for 0.2 min, increased to 90% B within 1.3 min, 90% B for 1.5 min, back to 5% B within 0.01 min; Flow Rate: 2 mL/min; Column: Sunfire, 50*4.6 mm, 3.5 um; Column Temperature: 50° C.; Detection: UV (214.4 nm) and MS (ESI, Pos mode, 110 to 1000 amu).

LC-MS Method 008:

Mobile Phase: A: water (0.1% $NH_4HCO_3$) B: acetonitrile Gradient: 5% B increased to 95% B within 1.3 min, 95% B for 1.5 min, back to 5% B within 0.01 min. Flow Rate: 2 mL/min Column: Sunfire C18, 4.6*50 mm, 3.5 um LC-MS Method 009:

Mobile Phase: A: water (0.01% trifluoroacetic acid) B: acetonitrile (0.01% trifluoroacetic acid) Gradient: 5% B increase to 95% B within 2.2 min, 95% B for 2.8 min Flow Rate: 2.2 ml/min Column: Chromolith Fast gradient RP-18e 50 mm×3 mm LC-MS Method 010:

Mobile Phase: A: Water (10 mM ammonium bicarbonate) B: acetonitrile Gradient: 5% increased to 95% B within 2.0 min, 95% B for 3 min. Flow Rate: 1.8 ml/min, Column: XBridge C18, 4.6×50 mm, 3.5 um.

LC-MS Method 011:

Mobile Phase: A: water (0.01% trifluoroacetic acid), B: Acetonitrile (0.01% trifluoroacetic acid); Gradient: 5% B for 0.2 min, increased to 95% B within 1.3 min, 95% B for 1.5 min, back to 5% within 0.01 min; Flow Rate: 2 ml/min; Column: Sunfire, 50×4.6 mm, 3.5 um; Column Temperature: 50° C.

LC-MS Method 012:

Mobile Phase: A: water (0.1% formic acid) B: acetonitrile (0.1% formic acid), Gradient: 10% B for 0.2 min, increase to 90% B within 1.3 min, 90% B for 1.5 min; Flow Rate: 2 mL/min; Column: Sunfire C18, 4.6×50 mm, 3.5 um; Oven Temperature: 50° C.; Detection: UV (214.4 nm) and MS (ESI, Pos mode, 110 to 1000 amu).

LC-MS Method 013:

Mobile Phase: A: water (0.01% trifluoroacetic acid), B: acetonitrile (0.01% trifluoroacetic acid); Gradient: 5% B for 0.2 min, increased to 95% B within 1.3 min, 95% B for 1.5 min, back to 5% B within 0.01 min; Flow Rate: 1.8 ml/min; Column: Sunfire, 50*4.6 mm, 3.5 um; Column Temperature: 50° C.

LC-MS Method 014:

Mobile Phase: A: water (0.01% trifluoroacetic acid), B: acetonitrile (0.01% trifluoroacetic acid); Gradient: 5% B increase to 95% B within 1.2 min, 95% B for 0.8 min; Flow Rate: 1.8 ml/min; Column: Zorbox SB-C18 30*4.6 mm, 1.8 um; Column Temperature: 40° C., Detection: UV (214 nm, 4 nm) and MS (ESI, POS Mode, 110-1300 amu); LC-Mass method 015:

A: water (10 mM ammonium bicarbonate) B: acetonitrile; Gradient: 5% B increase to 95% B within 1.5 minutes, 95% B for 1.5 minutes, back to 5% B within 0.01 minutes. Flow Rate: 1.8 mL/minute; Column: XBridge, 3.5 μm, 50*4.6 mm; Oven Temperature: 50° C.

LC-Mass Method 016:

Mobile Phase: A: water (0.01% trifluoroacetic acid) B: acetonitrile (0.01% trifluoroacetic acid); Gradient: 5% B increase to 95% B within 1.5 minutes, 95% B for 1.5 minutes, back to 5% B within 0.01 minutes. Flow Rate: 1.8 mL/minute; Column: Sunfire C18, 4.6*50 mm, 3.5 μm; Oven Temperature: 50° C.

LC-Mass Method 017:

Mobile Phase: A: water (0.01% trifluoroacetic acid); B: acetonitrile (0.01% trifluoroacetic acid) Gradient: 5% B for 0.2 minutes, increase to 95% B within 1.5 minutes, 95% B for 1.5 minutes, back to 5% B within 0.01 minutes; Flow Rate: 2 mL/minute; Column: Sunfire, 50*4.6 mm, 3.5 μm; Column Temperature: 50° C.

LC-Mass Method 018:

Column: SunFire C18 (4.6×50 mm, 3.5 μm); Mobile phase: A: water (0.05% trifluoroacetic acid); B: acetonitrile (0.05% trifluoroacetic acid); Gradient from 5 to 100% of B in 1.3 minutes at 2 mL/minute; Temperature: 50° C.

LC-Mass Method 019:

Mobile phase: A=2.5 mM trifluoroacetic acid/water, B=2.5 mM trifluoroacetic acid/acetonitrile; Gradient: B=10%-95% in 1.0 minutes; Flow rate: 1.5 mL/minute; Column: Xbridge-C18, 30×4.6 mm, 2.5 μm.

LC-Mass Method 020:

Mobile phase: column: HALO C18 (4.6×30 mm, 2.7 μm); Mobile phase: water (0.01% trifluoroacetic acid) (A)/acetonitrile (0.01% trifluoroacetic acid) (B); Elution program: Gradient from 5 to 95% of B in 3 minutes, 95% of B two minutes; back within 0.01 minutes at 2.0 mL/minutes. Temperature: 50° C. Detection: UV: (214 and 254 nm) and MS (ESI, Positive mode, 110 to 1200 amu).

LC-Mass Method 021:

Mobile Phase: A: water (0.1% formic acid) B: Acetonitrile (0.1% formic acid) Gradient: 10% B increase to 90% B within 1.3 minutes, 90% B for 1.5 minutes, back to 5% B within 0.01 minutes. Flow Rate: 2 mL/minute; Column: Sunfire C18, 4.6*50 mm, 3.5 μm.

LC-Mass Method 022:

Mobile Phase: A: water (0.1% formic acid) B: Acetonitrile (0.1% formic acid) Gradient: 5% B increase to 95% B within 1.3 minutes, 95% B for 1.5 minutes, back to 5% B within 0.01 minutes; Flow Rate: 1.8 mL/minute; Column: XBridge C18, 4.6*50 mm, 3.5 μm.

LC-Mass Method 023:

Mobile Phase: A: water (0.01% trifluoroacetic acid), B: Acetonitrile (0.01% trifluoroacetic acid); Gradient: 5% increase to 95% B within 1.3 minutes, 95% B for 1.5 minutes, back to 5% B within 0.01 minutes; Flow Rate: 2 mL/minute; Column Temperature: 50° C.; Column: Sunfire C18, 4.6*50 mm, 3.5 μm.

LC-Mass Method 024:

Mobile Phase: A: water (10 mM ammonium bicarbonate), B: Acetonitrile; Gradient: 10% increase to 95% B within 1.5 minutes, 95% B for 1.5 minutes, back to 10% B within 0.01 minutes; Flow Rate: 1.5 mL/minutes; Column Temperature: 50° C.; Column: XBridge C18, 4.6*50 mm, 3.5 μm.

LCMS method 025:

Column: SunShell, C18 column, 2.6 μm, 4.6×30 mm; Mobile Phase: A: Water (0.01% trifluoroacetic acid) B: acetonitrile (0.01% trifluoroacetic acid); Gradient: 5% B increase to 95% B within 1.3 minutes, 95% B for 0.7 minutes; Flow Rate: 2.5 mL/minute; Oven Temperature: 50° C.; Mass Range: 110-1300.

LCMS method 026:

Column: XBridge, C18 column, (4.6×50 mm, 3.5 μm); Mobile phase: water (10 mM ammonium bicarbonate) (A)/acetonitrile (B); Elution program: Gradient from 10 to 95% of B in 1.5 minutes, 95% for 1.5 minutes and back to 10% of B in 0.01 minutes at 1.8 mL/minute; Temperature: 50° C.; Detection: UV (214 nm and 254 nm) and MS (ESI, POS mode, 70 to 900 amu).

LC-Mass Method 027:

Mobile phase: water (10 mM ammonium bicarbonate) (A)/acetonitrile (B); Gradient: B=5% B increase to 95% B within 1.4 minutes, 95% B for 1.6 minutes, back to 5% B within 0.01 minute; Flow rate: 1.8 mL/minute; Column: Xbridge-C18, 50×4.6 mm, 3.5 μm. Column Temperature: 50° C.

LC-Mass Method 028:

Mobile Phase: A: water (0.01% trifluoroacetic acid) B: acetonitrile (0.01% trifluoroacetic acid). Gradient: 5% B increase to 95% B within 1.8 minutes, 95% B for 1.7 minutes. Flow Rate: 1.8 mL/minute; Column: Zorbox SB-C18 30*4.6 mm, 1.8 μm. Column Temperature: 40° C. Detection: UV (214 nm, 4 nm) and MS (ESI, POS Mode, 110-1300 amu).

LC-Mass Method 029:

Mobile phase: water (0.1% trifluoroacetic acid) (A)/acetonitrile (B); Gradient: B=5% B increase to 95% B within 0.8 minutes, 95% B for 1.2 minutes, back to 5% B within 0.01 minutes; Flow rate: 1.8 mL/minute; Column: Xbridge-C18, 50×4.6 mm, 3.5 μm. Column Temperature: 50° C.

LC-Mass Method 030:

Mobile Phase: A: Water (10 mM ammonium bicarbonate); B: acetonitrile; Gradient: 5% increase to 95% B within 1.3 minutes, 95% B for 1.7 minutes; Flow Rate: 1.8 mL/minutes; Column: Xbridge C18, 3.5 μm, 4.6*50 mm, Column Temperature: 50° C., Detection: UV (214 nm, 4 nm) and MS (ESI, Pos mode, 110 to 1000 amu).

LC-Mass Method 031:

Mobile Phase: A: water (0.01% trifluoroacetic acid) B: acetonitrile (0.01% trifluoroacetic acid); Gradient: 5% B increase to 95% B within 1.3 minutes, 95% B for 0.7 minutes; Flow Rate: 1.8 mL/minute; Column: Chromolith Fast gradient RP-18e 50 mm*3 mm; Column Temperature: 40° C.; Detection: UV (214 nm, 4 nm) and MS (ESI, POS Mode, 110-1300 amu).

LC-Mass Method 032:

Mobile Phase: A: water (0.01% trifluoroacetic acid) B: acetonitrile (0.01% trifluoroacetic acid); Gradient: 5% increase to 95% B within 2.5 minutes, 95% B for 2.5 minutes. Flow Rate: 2.0 mL/minutes; Column: Sunfire C18, 4.6*50 mm, 3.5 μm; Column Temperature: 45° C.; Detection: UV (214 nm, 4 nm) and MS (ESI, Positive mode, 110 to 1500 amu).

LC-Mass Method 033:

Mobile phase: A: water (0.01% trifluoroacetic acid) B: acetonitrile (0.01% trifluoroacetic acid). Gradient: 5% B increase to 95% B within 1.3 minutes; 95% B for 1.2 minutes. Flow Rate: 2.2 mL/minutes; Column: Chromolith Fast Gradient RP-18e 3*50 mm. Column Temperature: 40° C.

LC-Mass Method 034:

Mobile Phase: A: water (0.01% trifluoroacetic acid) B: Acetonitrile (0.01% trifluoroacetic acid); Gradient: 5% increase to 95% B within 1.5 minutes, 95% B for 1.7 minutes; Flow Rate: 2.0 mL/minute; Column: Sunfire C18, 4.6*50 mm, 3.5 μm.

LC-Mass Method 35:

Mobile Phase: A: water (0.01% trifluoroacetic acid) B: Acetonitrile (0.01% trifluoroacetic acid) Gradient: 5% B increase to 95% B within 1.0 minute, 95% B for 1 minute; Flow Rate: 1.6 mL/minute; Column: Agilent Proshell 2.7 μm, 3.0 mm*30 mm Column Temperature: 50° C.; Detection: UV (214 nm, 4 nm) and MS (ESI, POS Mode, 110-1300 amu) LC-Mass Method 36:

Mobile Phase: A: water (0.01% trifluoroacetic acid) B: Acetonitrile (0.01% trifluoroacetic acid) Gradient: 5% B increase to 95% B within 1.3 minutes, 95% B for 1.78 min Flow Rate: 1.6 mL/minute; Column: Agilent Poroshell, 30*3.0 mm, 2.7 μm; Column Temperature: 50° C.; Detection: UV (214, 4 nm) and MS (ESI, Pos mode, 110 to 1000 amu) LC-Mass Method 37:

Mobile Phase: A: water (0.01% trifluoroacetic acid) B: Acetonitrile (0.01% trifluoroacetic acid); Gradient: 5% B increase to 95% B within 9 minutes, 95% B for 6 minutes; Flow Rate: 1 mL/minute; Column: Sunfire C18 150*4.6 mm, 3.5 μm; Column Temperature: 45° C.; Detection: UV (214 nm, 4 nm) and MS (ESI, POS Mode, 110-1300 amu).

LC-Mass Method 38:

Mobile Phase: A: water (0.01% trifluoroacetic acid) B: Acetonitrile (0.01% trifluoroacetic acid); Gradient: 5% B increase to 95% B within 2.5 minutes, 95% B for 2.5 minutes; Flow Rate: 2 mL/minute; Column: Agilent Proshell 2.7 μm, 3.0 mm*30 mm; Column Temperature: 50° C.; Detection: UV (214 nm, 4 nm) and MS (ESI, POS Mode, 110-1300 amu).

LC-Method Method 39:

Mobile Phase: A: water (0.01% trifluoroacetic acid) B: Acetonitrile (0.01% trifluoroacetic acid). Gradient: 20% B increase to 95% B within 2 min, 95% B 3 min. Flow Rate: 2 mL/minute. Column: Sunfire, 50*4.6 mm, 3.5 μm. Column Temperature: 50° C. Detection: UV (214, 4 nm) and MS (ESI, Positive mode, 110 to 1000 amu).

LC-Method Method 40:

Mobile phase: A: water (10 mM ammonium bicarbonate); B: Acetonitrile Gradient: 5% increase to 95% B within 1.4 minutes, 95% B to 2.90 minutes, back to 5% B within 0.1 minutes; Flow Rate: 2.0 mL/minute; Column: X-Bridge C18, 4.6*50 mm, 3.5 μm; Column Temperature: 50° C.; Detection: UV (214, 4 nm) and MS (ESI, Positive mod., 110 to 1300 amu).

LC-Mass Method 41:

Mobile Phase: A: water (0.01% trifluoroacetic acid) B: Acetonitrile (0.01% trifluoroacetic acid); Gradient: 5% B increase to 95% B within 1.0 minute, 95% B for 0.8 minutes; Flow Rate: 2.2 mL/minute; Column: Agilent Poroshell 120 EC-C18, 3.0*30 mm, 2.7 Micron; Column Temperature: 50° C.; Detection: UV (214, 4 nm) and MS (ESI, Positive mode, 110 to 1500 amu).

LC-Mass Method 42:

Column: SunFire C18 (4.6×50 mm, 3.5 μm); Mobile phase: A: water (0.01% trifluoroacetic acid) B: Acetonitrile (0.01% trifluoroacetic acid); Gradient: 10 to 95% of B in 1.4 minutes, 95% of B for 1.6 minutes; Flow rate: 2 mL/minute; Temperature: 50° C.; Detection: UV (214, 4 nm) and MS (ESI, Positive mode, 110 to 1000 amu).

LC-Mass Method 43:

Mobile phase: A: water (0.01% trifluoroacetic acid) B: Acetonitrile (0.01% trifluoroacetic acid); Gradient: 5% increase to 95% B within 1.4 minutes, 95% B for 2.95 minutes, back to 5% B within 0.05 minutes; Flow Rate: 2.0 mL/minute; Column: SunFire $C_{18\ 3.5}$ μm 4.6*50 mm; Column Temperature: 40° C.

LC-Mass Method 44:

Mobile Phase: water (0.01% trifluoroacetic acid) B: Acetonitrile (0.01% trifluoroacetic acid); Gradient: 5% increase to 95% B within 1.05 minutes, 95% B for 2.90 minutes, back to 5% B within 0.05 minutes; Flow Rate: 1.6 mL/minute; Column: Proshell 120 EC-C18, 30*3 mm, 2.7 μm; Oven Temperature: 50° C.; Detection: UV214, MASS 103-1000 amu.

LC-Mass Method 45:

Mobile Phase: A: water (10 mM ammonium bicarbonate); B: Acetonitrile; Gradient: 10% increase to 95% B within 1.3 minutes, 95% B for 1.5 minutes; Flow Rate: 2.2 ml/minute; Column: Kinetex 2.6 μm EVO C18 100A, 4.6*50 mm; Column Temperature: 50° C.; Detection: UV (214, 4 nm) and MS (ESI, Positive mode, 110 to 1500 amu).

LC-Mass Method 46:

Column: SUNFIRE C18 (4.6×50 mm, 3.5 μm); Mobile phase: A: water (0.01% trifluoroacetic acid)/B: acetonitrile (0.01% trifluoroacetic acid); Elution program: Gradient from 5 to 95% of B in 3 minutes, 95% for 2 minutes at 2.0 ml/minute.

LC-Mass Method 47:

Column: HALO C18 (4.6×30 mm, 3.7 μm); Mobile Phase: A: water (0.01% trifluoroacetic acid); B: Acetonitrile (0.01% trifluoroacetic acid); Elution program: Gradient from 5 to 95% of B in 1.5 minutes at 2 ml/minute; Temperature: 40° C.; Detection: UV (214 nm, 4 nm; 254, 4 nm) and MS (ESI, Positive mode, 110 to 1000 amu).

LC-Mass Method 48:

Mobile Phase: A: water (0.01% trifluoroacetic acid); B: Acetonitrile (0.01% trifluoroacetic acid); Gradient: 5% B increase to 95% B within 1.5 minutes, 95% B for 1.5 minutes; Flow Rate: 2 ml/minute; Column: Poroshell 120 EC-C18, 4.6*50 mm, 4 μm; Column Temperature: 50° C.; Detection: UV (214, 4 nm) and MS (ESI, Positive mode, 110 to 1500 amu).

LC-Mass Method 49:

Mobile Phase: A: water (0.01% trifluoroacetic acid); B: Acetonitrile (0.01% trifluoroacetic acid); Gradient: 5% B increase to 95% B within 9 minutes, 95% B for 6 minutes; Flow Rate: 1 ml/minute; Column: Sunfire C18 150*4.6 mm, 3.5 μm; Column Temperature: 45° C.; Detection: UV (214 nm, 4 nm) and MS (ESI, Positive mode, 110-1300 amu).

LC-Mass Method 50:

Column: XBRIDGE C18 (4.6×50 mm, 3.5 μm). Mobile phase: A: water (10 mmol ammonium bicarbonate)/B: acetonitrile. Elution program: Gradient from 10 to 95% of B in 2.5 minutes at 1.8 ml/minutes. 2.5 minutes 95% of B. Temperature: 50° C.

LC-Mass Method 51. Column: HALO C18 (4.6×30 mm, 2.7 μm). Mobile phase: A: water (0.01% trifluoroacetic acid)/B: acetonitrile (0.01% trifluoroacetic acid) (B). Elution program: Gradient from 5 to 95% of B in 1.4 minutes at 2.2 ml/minutes. 1.6 minutes 95% of B. Temperature: 50° C.; Detection: UV (214, 4 nm; 254, 4 nm) and MS (ESI, Positive mode, 110 to 1000 amu).

LC-Mass Method 52.

Column: XBRIDGE C18 (4.6×150 mm, 3.5 μm); Mobile phase: A: water (10 mmol ammonium bicarbonate)/B: acetonitrile. Elution program: Gradient from 5 to 95% of B in 8 minutes at 1.0 ml/minute; 7 minutes at 95% of B; 0.1 minutes back to 5% of B; Temperature: 40° C.; Detection: UV (214 nm, 4 nm) and MS (ESI, Positive mode, 50 to 1200 amu).

PREPARATION OF INTERMEDIATES

Intermediate 1: 5-((4-Bromo-6,7-difluoro-1H-indol-5-yl)oxy)-2-fluorobenzonitrile

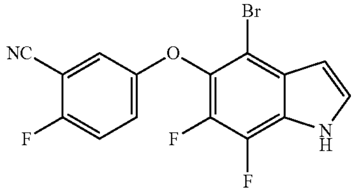 [SMILES: N#Cc1cc(Oc2c(F)c(F)c3[nH]ccc3c2Br)ccc1F]

To a solution of 5-(4-amino-2-bromo-5,6-difluoro-3-((trimethylsilyl)ethynyl)phenoxy)-2-fluorobenzonitrile (Intermediate 1E, 700 mg, 1.6 mmol) in N,N-dimethylformamide (7 mL) was added CuI (608 mg, 3.2 mmol) and stirred at 100° C. in a glove box for four hours. The reaction mixture was diluted with water and extracted with ethyl acetate (50 mL×3). The organic phase was washed with water, brine, dried with sodium sulfate, filtered, and concentrated. The residue was purified by flash chromatography over silica to give the title compound as a yellow solid (362 mg, 62%). $^1$H NMR (400 MHz, $CDCl_3$) δ 8.63 (s, 1H), 7.37-7.39 (m, 1H), 7.14-7.23 (m, 2H), 7.04-7.06 (m, 1H), 6.67-6.69 (m, 1H) ppm.

Intermediate 1A: 1-Bromo-2,3,4-trifluoro-5-nitrobenzene

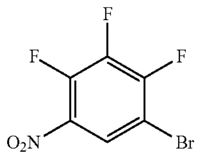 [SMILES: O=[N+]([O-])c1cc(Br)c(F)c(F)c1F]

To a solution of 1,2,3-trifluoro-4-nitrobenzene (30 g, 169.5 mmol) in concentrated sulfuric acid (150 mL) was added 1,3-dibromo-5,5-dimethylimidazolidine-2,4-dione (24 g, 84.7 mmol) at 0° C. and stirred at room temperature overnight. The mixture was slowly and carefully added to ice water (600 g ice and 100 mL water) to keep the temperature below 30° C. and extracted with heptane (300 mL×3). The combined organic extracts were washed with water and brine, dried over magnesium sulfate, filtered, and evaporated to dryness. The resulting residue was purified by flash chromatography (silica gel, heptane) to give the title compound (32 g, 75%) as yellow oil. $^1$H NMR (400 MHz, $CDCl_3$) δ 8.21 (td, J=7.2, 2.8 Hz, 1H) ppm.

Intermediate 1B: 5-(6-Bromo-2,3-difluoro-4-nitrophenoxy)-2-fluorobenzonitrile

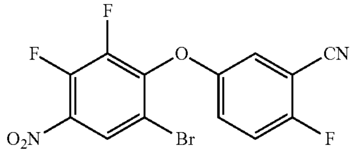 [SMILES: N#Cc1cc(Oc2c(Br)cc([N+](=O)[O-])c(F)c2F)ccc1F]

To a solution of 1-bromo-2,3,4-trifluoro-5-nitrobenzene (Intermediate 1A, 32 g, 125.5 mmol) in N,N-dimethylformamide (250 mL) were added 2-fluoro-5-hydroxybenzonitrile (18.9 g, 138.0 mmol) and potassium carbonate (26 g, 1.5 mmol) at room temperature and stirred for one hour. The reaction mixture was diluted with water (300 mL) and extracted with ethyl acetate (250 mL×3). The combined organic extracts were washed with water and brine, dried over magnesium sulfate, filtered, and concentrated. The residue was purified by flash chromatography (silica gel) to give the title compound as a yellow solid (15 g, 30%). MS: 373, 375 m/z $[M+H]^+$. $^1$H NMR (400 MHz, $CDCl_3$) δ 8.30 (dd, J=7.2, 2.4 Hz, 1H), 7.20-7.25 (m, 2H), 7.15-7.17 (m, 1H) ppm.

Intermediate 1C: 5-(4-Amino-6-bromo-2,3-difluoro-phenoxy)-2-fluorobenzonitrile

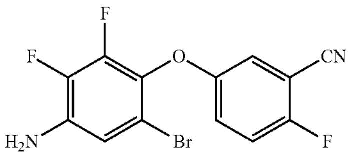

To a solution of 5-(6-bromo-2,3-difluoro-4-nitrophenoxy)-2-fluorobenzonitrile (Intermediate 1B, 5 g, 13.4 mmol) in ethanol (100 mL) and water (30 mL) were added iron powder (3 g, 53.6 mmol) and ammonium chloride (5.8 g, 107.5 mmol). The reaction mixture was stirred at 80° C. for four hours, cooled to room temperature, diluted with water (100 mL) and extracted with ethyl acetate (100 mL×3). The combined organic extracts were washed with water, brine, dried over magnesium sulfate, filtered, and evaporated to dryness. The residue was purified by flash chromatography (silica gel, heptane/ethyl acetate, v/v, 10/1) to give the title compound as a yellow solid (3 g, 65%). MS: 343, 345 m/z $[M+H]^+$.

Intermediate 1D: 5-(4-Amino-2-bromo-5,6-difluoro-3-iodophenoxy)-2-fluorobenzonitrile

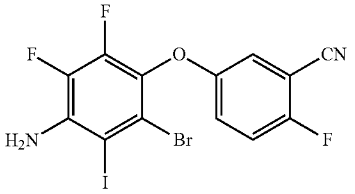 [SMILES: N#Cc1cc(Oc2c(F)c(F)c(N)c(I)c2Br)ccc1F]

To a solution of 5-(4-amino-6-bromo-2,3-difluorophenoxy)-2-fluorobenzonitrile (Intermediate 1C, 6.7 g, 19.6 mmol) in acetic acid (200 mL) was added NIS (4.4 g, 19.6 mmol). The mixture was stirred at room temperature for three hours, diluted with water (200 mL) and extracted with ethyl acetate (150 mL×3). The combined organic extracts were washed with water, brine, dried over magnesium sulfate, filtered, and evaporated to dryness. The residue was purified by flash chromatography over silica (petroleum ether/dichloromethane, v/v, 2/1) to give the title compound as a yellow solid (8.2 g, 89%). $^1H$ NMR (400 MHz, $CDCl_3$) δ 7.16-7.18 (m, 2H), 7.03-7.04 (m, 1H), 4.56 (s, 2H) ppm. MS: 469, 471 m/z $[M+H]^+$.

Intermediate 1E: 5-(4-Amino-2-bromo-5,6-difluoro-3-((trimethylsilyl)ethynyl)phenoxy)-2-fluorobenzonitrile

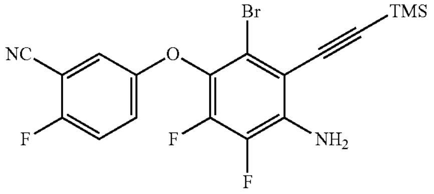 [SMILES: C[Si](C)(C)C#Cc1c(N)c(F)c(F)c(Oc2ccc(F)c(C#N)c2)c1Br]

To a solution of 5-(4-amino-2-bromo-5,6-difluoro-3-iodophenoxy)-2-fluorobenzonitrile (Intermediate 1D, 8.1 g, 17.3 mmol) in N, N-dimethylformamide (200 mL) were added trimethylsilylacetylene (3.4 g, 34.6 mmol), $Pd(Ph_3P)_2Cl_2$ (1.2 g, 1.7 mmol), CuI (323 mg, 1.7 mmol) and triethylamine (3.5 g, 34.6 mmol). The reaction mixture was stirred at 30° C. under nitrogen for three hours, diluted with water (300 mL) and extracted with ethyl acetate (250 mL×3). The combined organic extracts were washed with water, brine, dried with sodium sulfate, filtered, and concentrated. The residue was purified by flash chromatography (silica gel, petroleum ether/dichloromethane, v/v, 8/1) to give the title compound as a yellow solid (5 g, 64%). MS: 439, 441 m/z $[M+H]^+$.

The following intermediates were prepared utilizing the procedures described for Intermediate 1 and/or Intermediates 1A to 1E.

| Inter. No. | Structure | Name | LCMS-(m/z) |
|---|---|---|---|
| 1-1 | 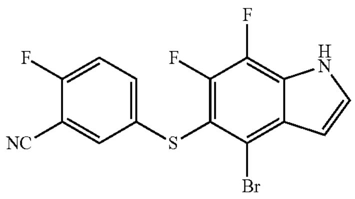 [SMILES: N#Cc1cc(Sc2c(F)c(F)c3[nH]ccc3c2Br)ccc1F] | 5-((4-bromo-6,7-difluoro-1H-indol-5-yl)thio)-2-fluorobenzonitrile | 383, 385 $[M + H]^+$; RT: 1.94 min. (LC-MS method 17) |
| 1-2 | 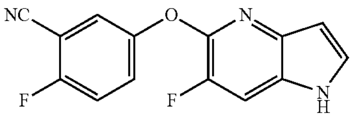 [SMILES: N#Cc1cc(Oc2nc3cc[nH]c3cc2F)ccc1F] | 2-fluoro-5-((6-fluoro-1H-pyrrolo[3,2-b]pyridin-5-yl)oxy)benzonitrile | 272 |

-continued

| Inter. No. | Structure | Name | LCMS-(m/z) |
|---|---|---|---|
| 1-3 | 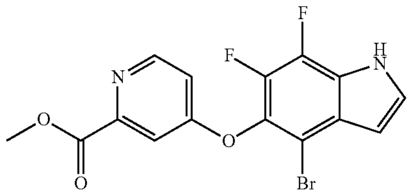 [SMILES: COC(=O)c1cc(Oc2c(F)c(F)c3[nH]ccc3c2Br)ccn1] | methyl 4-((4-bromo-6,7-difluoro-1H-indol-5-yl)oxy)picolinate | 383, 385 $[M + H]^+$; RT: 1.70 min. (LC-MS method 16) |
| 1-4 | 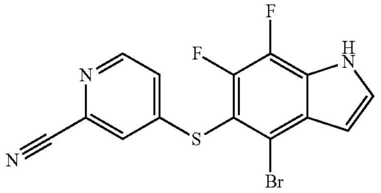 [SMILES: N#Cc1cc(Sc2c(F)c(F)c3[nH]ccc3c2Br)ccn1] | 4-((4-bromo-6,7-difluoro-1H-indol-5-yl)thio)picolinonitrile | 366, 368 $[M + H]^+$; RT: 2.02 min. (LC-MS method 021) |

Intermediate 2: 5-((4-Bromo-6-fluoro-1H-indol-5-yl)oxy)-2-fluorobenzonitrile

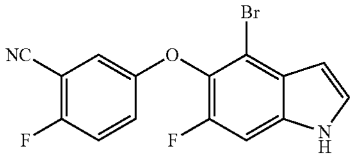 [SMILES: N#Cc1cc(Oc2c(F)cc3[nH]ccc3c2Br)ccc1F]

Step One: To a stirred solution of Intermediate 2B (124 g, 336 mmol) in N,N-dimethylformamide (1 L) was added N,N-dimethylformamide dimethyl acetal (178 mL, 159 g, 1.34 mol). Five identical reactions were executed in parallel. The six mixtures were each heated at 100° C. for six hours and then cooled to room temperature, combined, and poured into stirred ice water (20 L). After warming to near room temperature, the suspension was extracted with ethyl acetate (2×8 L). The combined organic layers were washed with water (1×10 L) and brine (1×10 L), dried over sodium sulfate and concentrated. The crude N,N-dimethyl enamine intermediate was afforded as a black oil (786 g, 92%), which was used without purification in the second step. $^1$H NMR (400 MHz $CDCl_3$) δ 7.38 (d, J=8.8 Hz, 1H), 7.19 (s, 1H), 7.10-7.12 (m, 2H), 6.44 (d, J=13.6 Hz, 1H), 4.96 (d, J=13.6 Hz, 1H), 2.80 (s, 6H) ppm.

Step Two: To a stirred solution of the crude enamine (100 g, 236 mmol) in a mixture of acetic acid (800 mL) and toluene (800 mL) was added silica gel (42.5 g). The suspension was warmed to 50° C. and treated with iron powder (132 g, 2.36 mol), portion-wise over 15 minutes. Following this addition, the mixture was heated at 100° C. for 12 hours and then cooled to room temperature and suction filtered through a bed of Celite. The filtering agent was rinsed with ethyl acetate (total, 5 L) and the combined filtrate was partitioned between water (10 L) and ethyl acetate (5 L). The organic layer was combined with a second extract (ethyl acetate, 1×5 L), washed with water (1×10 L) and brine (1×10 L), dried over sodium sulfate and concentrated under reduced pressure to give a dark brown oil. The resulting dark brown oil was purified by automated flash chromatography (1 kg silica gel column, 1-20% ethyl acetate in petroleum ether) to afford the title compound as a white solid (66.7 g, 74% overall, two steps). $^1$H NMR (400 MHz $CDCl_3$) δ 8.41 (s, 1H), 7.25-7.26 (m, 1H), 7.15-7.18 (m, 3H), 6.95-7.09 (m, 1H), 6.55 (t, J=2.8 Hz, 1H) ppm.

Intermediate 2A: 3-Bromo-1,2-difluoro-4-methyl-5-nitrobenzene

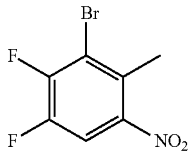

To a stirred solution of 1,2-difluoro-4-methyl-5-nitrobenzene (150 g, 866 mmol) in trifluoroacetic acid (800 mL) was added 1,3-dibromo-5,5-dimethylimidazolidine-2,4-dione (136 g, 476 mmol) and concentrated sulfuric acid (200 mL; over 3-4 minutes). Two additional bromination reactions, utilizing the same quantities of reactants and solvent, were run in parallel. After 10 hours at room temperature, the three reactions were combined and then slowly poured into a stirred slurry of crushed ice and water (5 L). When the ice had fully melted, the mixture was extracted with petroleum ether (2×4 L). The combined organic layers were washed with brine (1×5 L), dried over sodium sulfate and concentrated. The resulting oil was purified by automated flash chromatography (3 kg silica gel column, 100% petroleum ether) to afford the title compound as a yellow oil (417 g, 64%). $^1$H NMR (400 MHz $CDCl_3$) δ 7.68 (q, J=6.0 Hz, 1H), 2.55 (s, 3H) ppm.

Intermediate 2B: 5-(2-Bromo-6-fluoro-3-methyl-4-nitrophenoxy)-2-fluorobenzonitrile

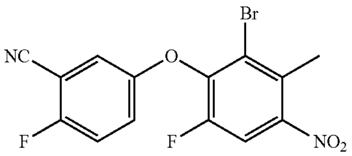 [SMILES: Cc1c([N+](=O)[O-])cc(F)c(Oc2ccc(F)c(C#N)c2)c1Br]

To a stirred solution of Intermediate 2A (207 g, 820 mmol) in N,N-dimethylformamide (1 L) was added 2-fluoro-5-hydroxybenzonitrile (118 g, 861 mmol) and potassium carbonate (227 g, 1.64 mol). A second, identical, reaction was run in parallel. Both mixtures were heated at 100° C. for one hour and then cooled to room temperature, combined, and poured into stirred ice water (7 L). After warming to room temperature, the resulting suspension was extracted with ethyl acetate (2×3 L). The combined organic layers were washed with water (1×5 L) and brine (1×3 L), dried over sodium sulfate and concentrated. The crude title compound, which was used without purification, was obtained as a yellow solid (585 g, 97%). $^1$H NMR (400 MHz $CDCl_3$) δ 7.68 (d, J=9.2 Hz, 1H), 7.10-7.14 (m, 2H), 7.01-7.02 (m, 1H), 2.58 (s, 3H).

The following intermediates were prepared utilizing the procedure described for Intermediate 2, and/or for Intermediates 2A and 2B.

| Inter. No. | Structure | Name | MS m/z $[M + H]^+$/$^1$H NMR |
|---|---|---|---|
| 2-1 | 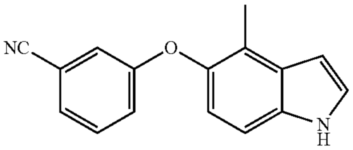 [SMILES: Cc1c(Oc2cccc(C#N)c2)ccc2[nH]ccc12] | 3-((4-methyl-1H-indol-5-yl)oxy)benzonitrile | 249 m/z $[M + H]^+$; (400 MHz, DMSO-$d_6$) d 7.52-7.44 (m, 2H), 7.42-7.40 (m, 1H), 7.31 (d, J = 8.4 Hz, 1H), 7.21-7.20 (m, 1H), 7.14-7.11 (m, 1H), 6.81 (d, J = 8.8 Hz, 1H), 6.52-6.51 (m, 1H), 2.26 (s, 3H) ppm. |
| 2-2 | 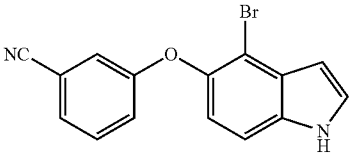 [SMILES: N#Cc1cccc(Oc2ccc3[nH]ccc3c2Br)c1] | 3-((4-bromo-1H-indol-5-yl)oxy)benzonitrile | 313, 315 m/z $[M + H]^+$; (400 MHz, $CDCl_3$) d 8.50 (s, 1H), 7.40-7.32 (m, 3H), 7.29 (d, J = 7.6 Hz, 1H), 7.17 (dd, J = 8.0, 2.4 Hz, 1H), 7.08-7.06 (m, 1H), 6.95 (d, J = 8.8 Hz, 1H), 6.65-6.40 (m, 1H) ppm. |
| 2-3 | 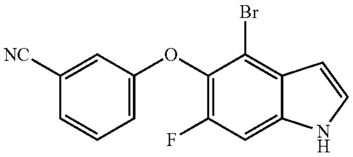 [SMILES: N#Cc1cccc(Oc2c(F)cc3[nH]ccc3c2Br)c1] | 3-((4-bromo-6-fluoro-1H-indol-5-yl)oxy)benzonitrile | 331, 333 m/z $[M + H]^+$ |
| 2-4 | 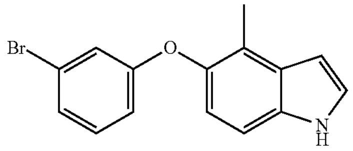 [SMILES: Cc1c(Oc2cccc(Br)c2)ccc2[nH]ccc12] | 5-(3-bromophenoxy)-4-methyl-1H-indole | 302, 304 m/z $[M + H]^+$; (400 MHz, DMSO-$d_6$) d 7.41-7.39 (m, 1H), 7.30 (d, J = 8.4 Hz, 1H), 7.27-7.23 (m, 1H), 7.18-7.16 (m, 1H), 6.91-6.90 (m, 1H), 6.84-6.79 (m, 2H), 6.51-6.50 (m, 1H), 2.26 (s, 3H) ppm. |
| 2-5 | 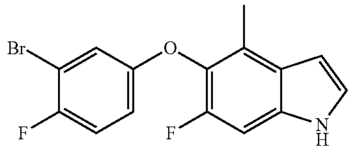 [SMILES: Cc1c(Oc2ccc(F)c(Br)c2)c(F)cc2[nH]ccc12] | 5-(3-bromo-4-fluorophenoxy)-6-fluoro-4-methyl-1H-indole | (400 MHz, $CDCl_3$) d 8.29 (s, 1H), 7.30-7.23 (m, 1H), 7.08 (d, J = 10.0 Hz, 1H), 7.04-6.99 (m, 2H), 6.84-6.77 (m, 1H), 6.57 (s, 1H), 2.39 (s, 3H) ppm. |
| 2-6 | 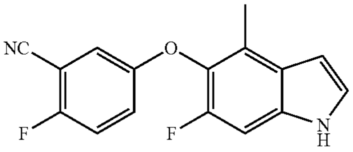 | 2-fluoro-5-((6-fluoro-4-methyl-1H-indol-5-yl)oxy)benzonitrile | 285 m/z $[M + H]^+$; (400 MHz, $CDCl_3$) d 8.28 (s, 1H), 7.27 (s, 1H), 7.20-7.07 (m, 3H), 6.98 (dd, J = 4.8, 2.8 Hz, 1H), 6.58 (s, 1H), 2.39 (s, 3H) ppm. |
| 2-7 | 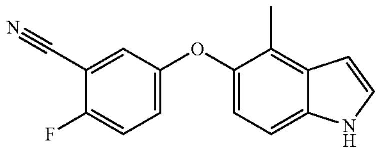 [SMILES: Cc1c(Oc2ccc(F)c(C#N)c2)ccc2[nH]ccc12] | 2-fluoro-5-((4-methyl-1H-indol-5-yl)oxy)benzonitrile | 267 m/z $[M + H]^+$ |

-continued

| Inter. No. | Structure | Name | MS m/z [M + H]$^+$/$^1$H NMR |
|---|---|---|---|
| 2-8 | 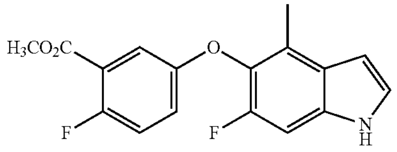 [SMILES: COC(=O)c1cc(Oc2c(F)cc3[nH]ccc3c2C)ccc1F] | methyl 2-fluoro-5-((6-fluoro-4-methyl-1H-indol-5-yl)oxy)benzoate | 318 m/z [M + H]$^+$ |
| 2-9 | 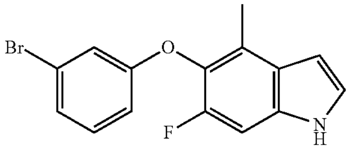 [SMILES: Cc1c(Oc2cccc(Br)c2)c(F)cc2[nH]ccc12] | 5-(3-bromophenoxy)-6-fluoro-4-methyl-1H-indole | 320, 322 m/z [M + H]$^+$ |
| 2-10 | 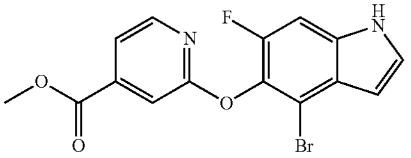 [SMILES: COC(=O)c1ccnc(Oc2c(F)cc3[nH]ccc3c2Br)c1] | methyl 2-((4-bromo-6-fluoro-1H-indol-5-yl)oxy)isonicotinate | 365, 367 m/z [M + H]$^+$ |
| 2-11 | 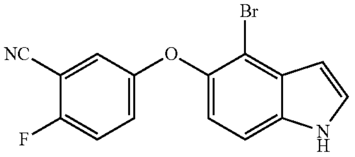 [SMILES: N#Cc1cc(Oc2ccc3[nH]ccc3c2Br)ccc1F] | 5-((4-bromo-1H-indol-5-yl)oxy)-2-fluorobenzonitrile | 331, 333 m/z [M + H]$^+$ |
| 2-12* | 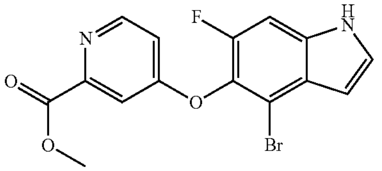 [SMILES: COC(=O)c1cc(Oc2c(F)cc3[nH]ccc3c2Br)ccn1] | methyl 4-((4-bromo-6-fluoro-1H-indol-5-yl)oxy)picolinate | 365, 367 m/z [M + H]$^+$ |
| 2-13 | 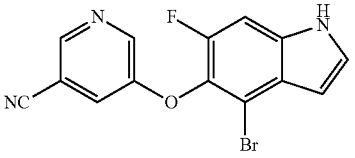 [SMILES: N#Cc1cncc(Oc2c(F)cc3[nH]ccc3c2Br)c1] | 5-((4-bromo-6-fluoro-1H-indol-5-yl)oxy)nicotinonitrile | 332, 334 [M + H]$^+$; RT: 1.88 min. (LC-MS Method 4) |
| 2-14 | 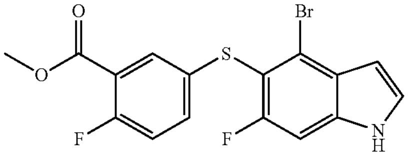 [SMILES: COC(=O)c1cc(Sc2c(F)cc3[nH]ccc3c2Br)ccc1F] | methyl 5-((4-bromo-6-fluoro-1H-indol-5-yl)thio)-2-fluorobenzoate | 398, 400 [M + H]$^+$; RT: 2.07 min. (LC-MS Method 4) |
| 2-15 | 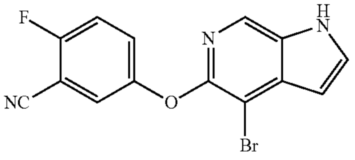 [SMILES: N#Cc1cc(Oc2ncc3[nH]ccc3c2Br)ccc1F] | 5-((4-bromo-1H-pyrrolo[2,3-c]pyridin-5-yl)oxy)-2-fluorobenzonitrile | 332, 334 [M + H]$^+$; RT: 1.76 min. (LC-MS Method 40) |

-continued

| Inter. No. | Structure | Name | MS m/z [M + H]$^+$/$^1$H NMR |
|---|---|---|---|
| 2-16 | 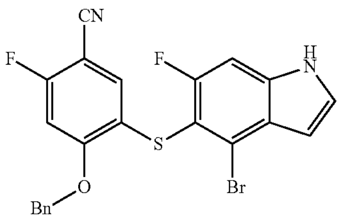 [SMILES: N#Cc1cc(Sc2c(F)cc3[nH]ccc3c2Br)c(OCc2ccccc2)cc1F] | 4-(benzyloxy)-5-((4-bromo-6-fluoro-1H-indol-5-yl)thio)-2-fluorobenzonitrile | 471, 473 [M + H]$^+$; RT: 2.46 min. (LC-MS Method 17) |

*Reduction of dimethylaminovinyl nitro intermediate to form indole (second part of procedure described for Intermediate 2) was realized by hydrazine/Nickle at room temperature.

Intermediate 3: 5-((4-Bromo-6-fluoro-1-tosyl-1H-indol-5-yl)oxy)-2-fluorobenzonitrile

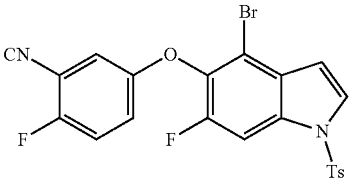

To a solution of 5-((4-bromo-6-fluoro-1H-indol-5-yl)oxy)-2-fluorobenzonitrile (Intermediate 2, 72 g, 264 mmol) in N,N-dimethylformamide (500 mL) was carefully added sodium hydride (12.7 g, 317 mmol, 60% purity) at room temperature. The reaction mixture was stirred for 30 minutes, 4-methylbenzenesulfonyl chloride (47.2 g, 247 mmol) was then added portion wise and continued stirring for 9.5 hours. The reaction was quenched with water (3 L) and extracted with ethyl acetate (2 L×2). The combined organic extracts were washed with brine (2 L), dried over sodium sulfate, filtered, and concentrated to afford the title compound as a white solid (144 g). $^1$H NMR: (400 MHz $CDCl_3$) δ 7.86 (d, J=10.4 Hz, 1H), 7.79 (d, J=8.0 Hz, 2H), 7.67 (d, J=2.8 Hz, 1H), 7.31 (d, J=8.0 Hz, 2H), 7.14 (d, J=6.8 Hz, 2H), 6.98 (s, 1H), 6.72 (d, J=2.8 Hz, 1H), 2.39 (s, 3H) ppm.

The following intermediates were prepared utilizing the procedures described for Intermediate 3.

| Inter No. | Structure | Name | MS m/z [M + H]$^+$/$^1$H NMR |
|---|---|---|---|
| 3-1 | 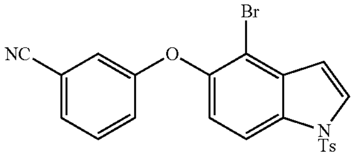 [SMILES: Cc1ccc(S(=O)(=O)n2ccc3c(Br)c(Oc4cccc(C#N)c4)ccc32)cc1] | 3-((4-bromo-1-tosyl-1H-indol-5-yl)oxy)benzonitrile | 467, 469 m/z [M + H]$^+$; $^1$H NMR (400 MHz, $CDCl_3$) d 7.97 (d, , J = 8.8 Hz, 1H), 7.80 (d, J = 8.2 Hz, 2H), 7.70 (d, J = 3.6 Hz, 1H), 7.42-7.26 (m, 4H), 7.16-7.12 (m, 1H), 7.06-7.03 (m, 2H), 6.77 (d, J = 3.6 Hz, 1H), 2.39 (s, 3H) ppm. |
| 3-2 | 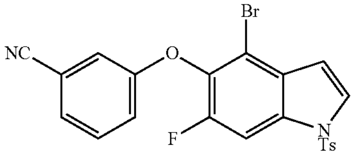 [SMILES: Cc1ccc(S(=O)(=O)n2ccc3c(Br)c(Oc4cccc(C#N)c4)c(F)cc32)cc1] | 3-((4-bromo-6-fluoro-1-tosyl-1H-indol-5-yl)oxy)benzonitrile | 485, 487 |
| 3-3 | 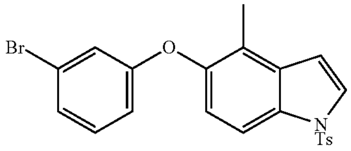 [SMILES: Cc1ccc(S(=O)(=O)n2ccc3c(C)c(Oc4cccc(Br)c4)ccc32)cc1] | 5-(3-bromphenoxy)-4-methyl-1-tosyl-1H-indole | 456, 458 |
| 3-4 | 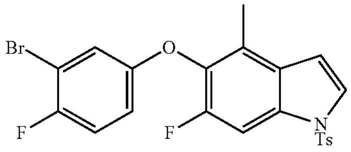 [SMILES: Cc1ccc(S(=O)(=O)n2ccc3c(C)c(Oc4ccc(F)c(Br)c4)c(F)cc32)cc1] | 5-(3-bromo-4-fluorophenoxy)-6-fluoro-4-methyl-1-tosyl-1H-indole | (400 MHz, $CDCl_3$) 7.79 (d, 2H), 7.71 (d, 1H), 7.59 (d, 1H), 7.29 (m, 2H), 6.96-6.03 (m, 2H), 6.73-6.33 (m, 1H), 6.66 (d, 1H), 2.39 (s, 3H), 2.30 (s, 3H) ppm. |

-continued

| Inter No. | Structure | Name | MS m/z [M + H]$^+$/$^1$H NMR |
|---|---|---|---|
| 3-5 | 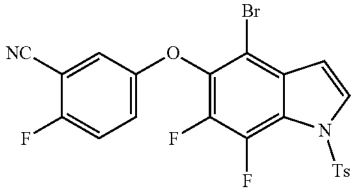 [SMILES: Cc1ccc(S(=O)(=O)n2ccc3c(Br)c(Oc4ccc(F)c(C#N)c4)c(F)c(F)c32)cc1] | 5-((4-bromo-6,7-difluoro-1-tosyl-1H-indol-5-yl)oxy)-2-fluorobenzonitrile | (400 MHz, $CD_3OD$) δ 7.91-7.90 (d, J = 4 Hz, 1H), 7.88-7.87 (d, J = 4 Hz, 1H), 7.36-7.34 (d, J = 8 Hz, 2H), 7.17-7.15 (m, 3H), 7.01-7.00 (m, 1H), 6.78-6.77 (m, 1H), 2.43 (s, 3H) ppm. |
| 3-6 | 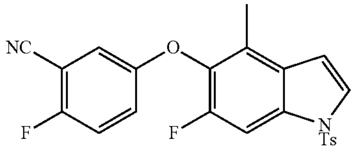 | 2-fluoro-5-((6-fluoro-4-methyl-1-tosyl-1H-indol-5-yl)oxy)benzonitrile | 461 m/z [M + Na]$^+$; $^1$H NMR (400 MHz, $CDCl_3$) δ 7.80 (d, J = 8.3 Hz, 2H), 7.72 (d, J = 10.4 Hz, 1H), 7.61 (d, J = 3.7 Hz, 1H), 7.29 (d, J = 8.1 Hz, 2H), 7.14-7.10 (m, 2H), 6.93 (d, J = 4.1 Hz, 1H), 6.67 (d, J = 3.7 Hz, 1H), 2.39 (s, 3H), 2.30 (s, 3H) ppm. |
| 3-7 | 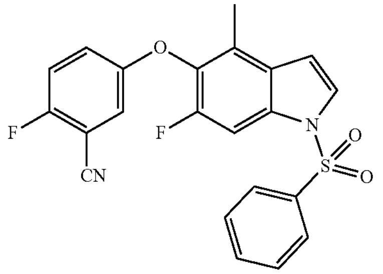 [SMILES: Cc1c(Oc2ccc(F)c(C#N)c2)c(F)cc2c1ccn2S(=O)(=O)c1ccccc1] | 2-fluoro-5-((6-fluoro-4-methyl-1-(phenylsulfonyl)-1H-indol-5-yl)oxy)benzonitrile | 425 |

Intermediate 4: 2-Fluoro-5-((6-fluoro-1-tosyl-4-vinyl-1H-indol-5-yl)oxy)benzonitrile

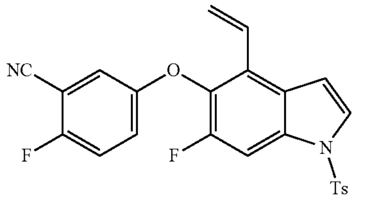 [SMILES: C=Cc1c(Oc2ccc(F)c(C#N)c2)c(F)cc2c1ccn2S(=O)(=O)c1ccc(C)cc1]

To a suspension of 5-((4-bromo-6-fluoro-1-tosyl-1H-indol-5-yl)oxy)-2-fluorobenzonitrile (Intermediate 3, 5.25 g, 10.5 mmol) in dioxane (120 mL) and water (40 mL) were added 4,4,5,5-tetramethyl-2-vinyl-1,3,2-dioxaborolane (3.2 g, 21 mmol), Pd(dppf)$Cl_2$ (384 mg, 0.5 mmol) and cesium carbonate (6.8 g, 21 mmol). The reaction mixture was stirred at 100° C. overnight, cooled to room temperature and extracted with ethyl acetate (150 mL×3). The combined organic extracts were washed with brine, dried over magnesium sulfate, and evaporated to dryness. The resulting residue was purified by flash chromatography (silica gel, petroleum ether/dichloromethane, v/v, 2/1) to afford the title compound as a yellow solid (4 g, 85%). MS: 473 m/z [M+Na]$^+$.

The following intermediate was prepared utilizing the procedures described for Intermediate 4.

| Inter. No. | Structure | Name | MS m/z [M + H]+ |
|---|---|---|---|
| 4-1 | 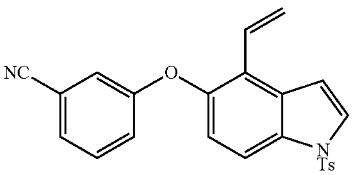 [SMILES: C=Cc1c(Oc2cccc(C#N)c2)ccc2c1ccn2S(=O)(=O)c1ccc(C)cc1] | 3-((1-tosyl-4-vinyl-1H-indol-5-yl)oxy)benzonitrile | 415 |
| 4-2 | 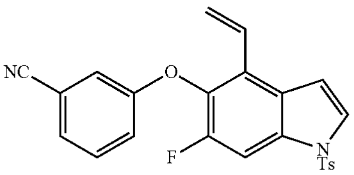 [SMILES: C=Cc1c(Oc2cccc(C#N)c2)c(F)cc2c1ccn2S(=O)(=O)c1ccc(C)cc1] | 3-((6-fluoro-1-tosyl-4-vinyl-1H-indol-5-yl)oxy)benzonitrile | 433 |

Intermediate 5: 2-Fluoro-5-((6-fluoro-4-formyl-1-tosyl-1H-indol-5-yl)oxy)benzonitrile

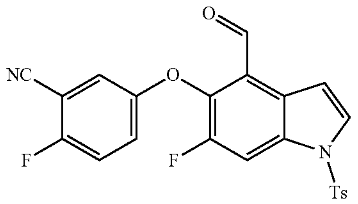 [SMILES: Cc1ccc(S(=O)(=O)n2ccc3c(C=O)c(Oc4ccc(F)c(C#N)c4)c(F)cc32)cc1]

To a solution of 2-fluoro-5-((6-fluoro-1-tosyl-4-vinyl-1H-indol-5-yl)oxy)benzonitrile (Intermediate 4, 4.6 g, 10.2 mmol) in tetrahydrofuran (90 mL) were added 2,6-lutidine (1.1 g, 10.2 mmol) and osmium tetroxide (2 mL saturated in water) at 0° C. The reaction mixture was stirred for three minutes and a solution of sodium periodate (8.8 g, 4.0 mmol) in water (30 mL) was added. The reaction mixture was stirred at room temperature overnight, acidified with 2 M hydrochloric acid (100 mL) and extracted with ethyl acetate (200 mL×3). The combined organic extracts were washed with water, brine, dried over magnesium sulfate and evaporated to dryness. The resulting residue was purified by flash chromatography (silica gel, petroleum ether/ethyl acetate, v/v, 10/1) to afford the title compound as a yellow solid (3.5 g, 75%). MS: 453 m/z $[M+H]^+$.

The following intermediate was prepared utilizing the procedures described for Intermediate 5.

| Inter. No. | Structure | Name | MS m/z $[M + H]^+$ |
|---|---|---|---|
| 5-1 | 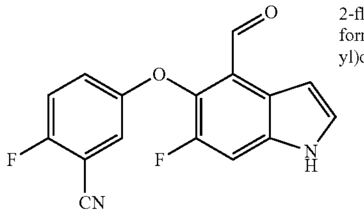 | 2-fluoro-5-((6-fluoro-4-formyl-1H-indol-5-yl)oxy)benzonitrile | 299 |

Intermediate 6: 3-((4-Vinyl-1H-indol-5-yl)oxy)benzonitrile

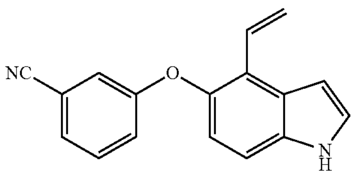 [SMILES: C=Cc1c(Oc2cccc(C#N)c2)ccc2[nH]ccc12]

A mixture of 3-((1-tosyl-4-vinyl-1H-indol-5-yl)oxy)benzonitrile (Intermediate 4-1, 3 g, 7.25 mmol) and potassium carbonate (3 g, 21.74 mmol) in methanol (30 mL) was refluxed for 1.5 hours, cooled to room temperature and concentrated. The resulting residue was diluted with ethyl acetate (100 mL), washed with water and brine, dried over sodium sulfate, filtered, and concentrated. The resulting residue was purified by flash chromatography (silica gel, petroleum ether/ethyl acetate, v/v, 10/1-5/1) to afford the title compound as alight-yellow oil (1.4 g, 74%). MS: 261 m/z $[M+H]^+$.

The following intermediate was prepared utilizing the procedure described for Intermediate 6.

| Inter. No. | Structure | Name | MS m/z [M + H]$^+$ |
|---|---|---|---|
| 6-1 | 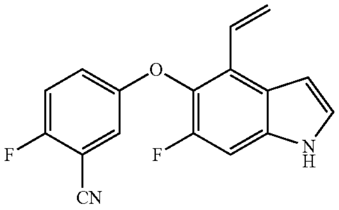 [SMILES: C=Cc1c(Oc2ccc(F)c(C#N)c2)c(F)cc2[nH]ccc12] | 2-fluoro-5-((6-fluoro-4-vinyl-1H-indol-5-yl)oxy)benzonitrile | 297 |
| 6-2 | 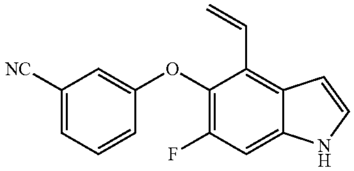 | 3-((6-fluoro-4-vinyl-1H-indol-5-yl)oxy)benzonitrile | 279 |

Intermediate 7: 3-((6-Fluoro-4-methyl-1H-indol-5-yl)oxy)benzonitrile

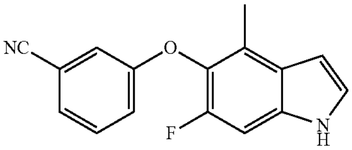 [SMILES: Cc1c(Oc2cccc(C#N)c2)c(F)cc2[nH]ccc12]

A mixture of 3-((4-bromo-6-fluoro-1H-indol-5-yl)oxy) benzonitrile (Intermediate 2-4, 600 mg, 1.82 mmol), methylboronic acid (1.1 g, 18.2 mmol), Pd(dppf)$Cl_2$ (300 mg, 0.46 mmol) and sodium bicarbonate (460 mg, 5.45 mmol) in dioxane (50 mL) and water (10 mL) was heated at 80° C. overnight. The reaction mixture was cooled to room temperature, diluted with dichloromethane (50 mL), washed with saturated sodium bicarbonate (10 mL×3) and brine, dried over sodium sulfate, filtered, and concentrated. The crude mixture was purified by flash chromatography (silica gel, petroleum ether/dichloromethane, v/v, 1:1) to give the title compound as a white solid (360 mg, 74%). MS: 267 m/z [M+H]$^+$.

Intermediate 8: Methyl 3-(3-(3-bromo-2-oxopropyl)phenyl)propanoate

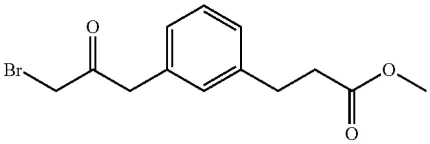 [SMILES: COC(=O)CCc1cccc(CC(=O)CBr)c1]

To a solution of 2-(3-(3-methoxy-3-oxopropyl)phenyl) acetic acid (Intermediate 8B, 1.4 g, 6.3 mmol) in dichloromethane (10 mL) was added oxalyl chloride (2 mL, 25.2 mmol) and 1 drop of DMF. The reaction mixture was stirred at room temperature for three hours and concentrated. To the residue was added 30 mL of heptane and re-evaporated again to remove any residual oxalyl chloride. The resulting residue was dissolved in 1:1 mixture of tetrahydrofuran and acetonitrile (10 mL), cooled to 0° C. Trimethylsilyl diazomethane (2 M, 12.6 mL, 25.2 mmol) was added dropwise over 10 minutes. After the addition was completed, the mixture was allowed to warm to room temperature overnight. The solvent was evaporated and the residue was dissolved in 5 mL of dichloromethane and cooled to 0° C. A solution of hydrogen bromide in acetic acid (2.3 g, 1.49 g/mL, 28.3 mmol) was added dropwise over 10 minutes (vigorous gas evolution noted), stirred for another 30 minutes and then diluted with brine (50 mL) and ethyl acetate (100 mL). The separated organic phase was dried over magnesium sulfate and concentrated. The resulting residue was purified by silica gel column chromatography (0-30% ethyl acetate in petroleum ether) to give the title compound as an oil (950 mg, 50%). MS: 321, 323 m/z [M+Na]$^+$.

Intermediate 8A: (E)-2-(3-(3-Methoxy-3-oxoprop-1-en-1-yl)phenyl)acetic Acid

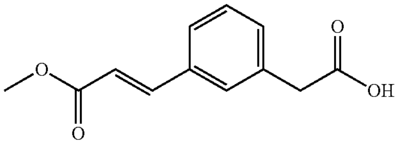 [SMILES: COC(=O)/C=C/c1cccc(CC(=O)O)c1]

To a stirred solution of 3-iodophenylacetic acid (2 g, 7.6 mmol), methyl acrylate (2 g, 22.8 mmol) and triethylamine (3.8 g, 38.0 mmol) in N,N-dimethylformamide (50 mL) was added tri(o-tolyl)phosphine (456 mg, 1.5 mmol), followed by palladium(II) acetate (170 mg, 0.76 mmol). The reaction mixture was heated at 110° C. overnight in a sealed tube, cooled to room temperature, diluted with ethyl acetate (100 mL) and washed with water (100 mL×2) and brine, dried over sodium sulfate and concentrated. The resulting residue was purified by flash silica gel column chromatography (0-40% ethyl acetate in petroleum ether) to give the title compound as a yellow oil (1.4 g, 80%). MS: 221 m/z [M+Na]$^+$.

Intermediate 8B:
2-(3-(3-Methoxy-3-oxopropyl)phenyl)acetic Acid

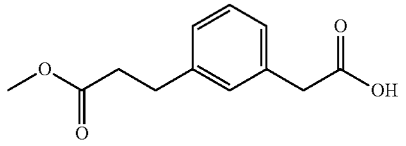 [SMILES: COC(=O)CCc1cccc(CC(=O)O)c1]

A suspension of (E)-2-(3-(3-methoxy-3-oxoprop-1-en-1-yl)phenyl)acetic acid (Intermediate 8A, 1.4 g, 6.3 mmol), Pd/C (140 mg, 5%) and tetrahydrofuran (10 mL) in a autoclave was placed under a hydrogen balloon and stirred for sixteen hours at room temperature. The catalyst was removed by filtration and washed with tetrahydrofuran (10 mL). The filtrate was concentrated to give the title compound as a yellow oil (1.4 g, 99%). MS: 240 m/z $[M+H_2O]^+$.

The following intermediates were prepared utilizing the procedures described for Intermediates 8, and/or for Intermediates 8A to 8B.

| Inter. No. | Structure | Name | MS m/z $[M + H]^+$ |
| --- | --- | --- | --- |
| 8-1* | 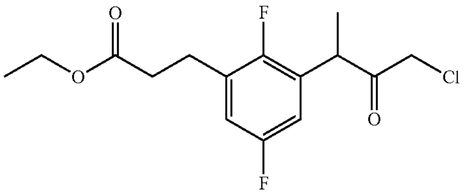 [SMILES: CCOC(=O)CCc1cc(F)cc(C(C)C(=O)CCl)c1F] | ethyl 3-(3-(4-chloro-3-oxobutan-2-yl)-2,5-difluorophenyl)propanoate | 319 |
| 8-2 | 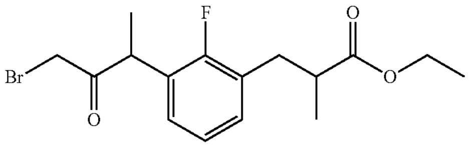 [SMILES: CCOC(=O)C(C)Cc1cccc(C(C)C(=O)CBr)c1F] | ethyl 3-(3-(4-bromo-3-oxobutan-2-yl)-2-fluorophenyl)-2-methylpropanoate | 381, 383 m/z $[M + Na]^+$ |
| 8-3* | 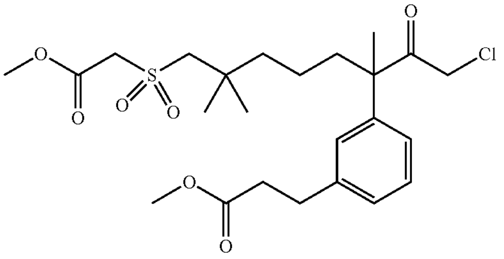 [SMILES: COC(=O)CCc1cccc(C(C)(CCCC(C)(C)CS(=O)(=O)CC(=O)OC)C(=O)CCl)c1] | Methyl 3-(3-(1-chloro-8-((2-methoxy-2-oxoethyl)sulfonyl)-3,7,7-trimethyl-2-oxooctan-3-yl)phenyl)propanoate | 503 |
| 8-4 | 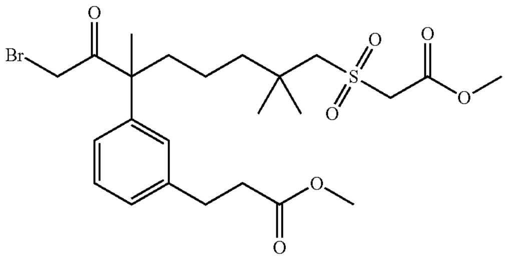 [SMILES: COC(=O)CCc1cccc(C(C)(CCCC(C)(C)CS(=O)(=O)CC(=O)OC)C(=O)CBr)c1] | methyl 3-(3-(1-bromo-8-((2-methoxy-2-oxoethyl)sulfonyl)-3,7,7-trimethyl-2-oxooctan-3-yl)phenyl)propanoate | 547, 549 |
| 8-5 | 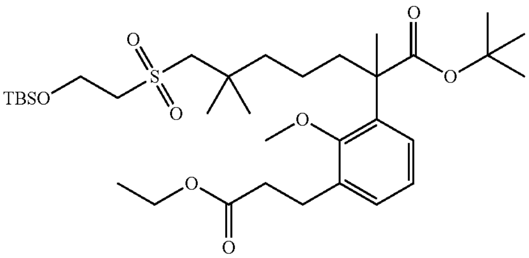 [SMILES: CCOC(=O)CCc1cccc(C(C)(CCCC(C)(C)CS(=O)(=O)CCO[Si](C)(C)C(C)(C)C)C(=O)OC(C)(C)C)c1OC] | tert-butyl 7-((2-((tert-butyldimethylsilyl)oxy)ethyl)sulfonyl)-2-(3-(3-ethoxy-3-oxopropyl)-2-methoxyphenyl)-2,6,6-trimethylheptanoate | 679 [M + Na]+; RT: 2.36 min.; (LC-MS Method: 026) |

*Replacing hydrogen bromide in acetic acid with 4N hydrogen chloride in 1,4-dioxane Intermediate 9: 1,2-Difluoro-3,4-dimethyl-5-nitrobenzene

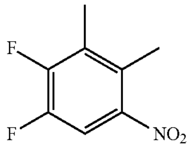

A mixture of 3-bromo-1,2-difluoro-4-methyl-5-nitrobenzene (Intermediate 2A, 10 g, 40 mmol), methylboronic acid (12 g, 200 mmol), $Pd(dppf)Cl_2$ (2.9 mg, 4.0 mmol) and sodium bicarbonate (10 g, 120 mmol) in 1,4-dioxane (160 mL) and water (40 mL) was stirred under nitrogen atmosphere at 80° C. for 3 days. The mixture was filtered and washed with ethyl acetate (300 mL). The organic phase was separated, washed with water (100 mL×2) and brine (50 mL), dried over sodium sulfate, filtered, and concentrated. The resulting residue was purified by flash chromatography (silica gel, petroleum ether: ethyl acetate, v/v, 12/1) to afford the title compound as a light-yellow oil (6.4 g, 85%). $^1H$ NMR (400 MHz, $CDCl_3$) δ 7.59 (t, J=8.4 Hz, 1H), 2.42 (s, 3H), 2.32 (d, J=2.4 Hz, 3H) ppm.

Intermediate 10: 2-Fluoro-5-((6-fluoro-1H-pyrrolo[3,2-b]pyridin-5-yl)oxy)benzimidamide

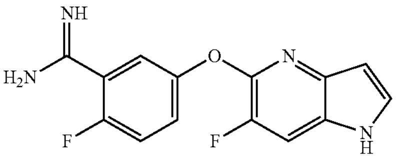 [SMILES: N=C(N)c1cc(Oc2nc3cc[nH]c3cc2F)ccc1F]

To a solution of 2-fluoro-5-((6-fluoro-1H-pyrrolo[3,2-b]pyridin-5-yl)oxy)benzonitrile (Intermediate 1-2, 380 mg, 1.12 mmol) in tetrahydrofuran (4 mL) was added a 1M solution of lithium bis(trimethylsilyl)amide in tetrahydrofuran (9 mL, 9 mmol). The reaction mixture was stirred at 25° C. for 18 hours, quenched with water (20 mL) and extracted with dichloromethane (30 mL×4). The combined organic phase was washed with brine (20 mL), dried over magnesium sulfate, and concentrated to afford the title compound as white solid (350 mg, 74%). MS: 289 m/z $[M+H]^+$.

The following intermediates were prepared utilizing similar procedures described for Intermediate 10.

| Inter. No. | Structure | Name | MS m/z $[M + H]^+$ |
| --- | --- | --- | --- |
| 10-1 | 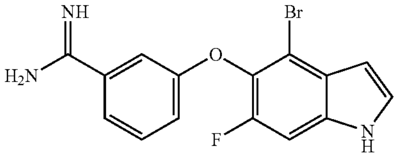 [SMILES: N=C(N)c1cccc(Oc2c(F)cc3[nH]ccc3c2Br)c1] | 3-((4-bromo-6-fluoro-1H-indol-5-yl)oxy)benzimidamide | 348/350 |
| 10-2 | 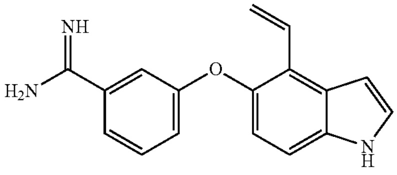 [SMILES: C=Cc1c(Oc2cccc(C(=N)N)c2)ccc2[nH]ccc12] | 3-((4-vinyl-1H-indol-5-yl)oxy)benzimidamide | 278 |
| 10-3 | 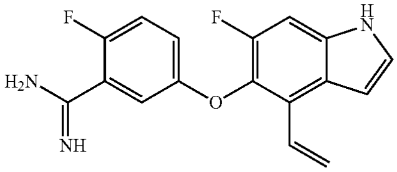 [SMILES: C=Cc1c(Oc2ccc(F)c(C(=N)N)c2)c(F)cc2[nH]ccc12] | 2-Fluoro-5-((6-fluoro-4-vinyl-1H-indol-5-yl)oxy)benzimidamide | 314 |
| 10-4 | 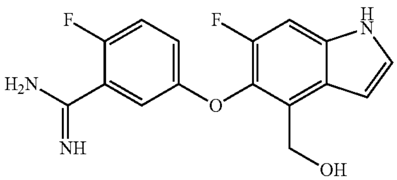 [SMILES: N=C(N)c1cc(Oc2c(F)cc3[nH]ccc3c2CO)ccc1F] | 2-fluoro-5-((6-fluoro-4-(hydroxymethyl)-1H-indol-5-yl)oxy)benzimidamide | 318 |
| 10-5 | 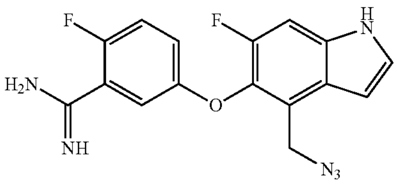 [SMILES: [N-]=[N+]=NCc1c(Oc2ccc(F)c(C(=N)N)c2)c(F)cc2[nH]ccc12] | 5-((4-(azidomethyl)-6-fluoro-1H-indol-5-yl)oxy)-2-fluorobenzimidamide | 343 |

-continued

| Inter. No. | Structure | Name | MS m/z [M + H]$^+$ |
|---|---|---|---|
| 10-6 | 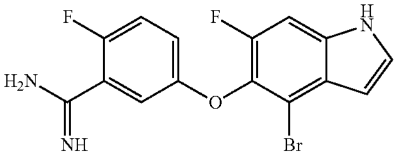 | 5-((4-bromo-6-fluoro-1H-indol-5-yl)oxy)-2-fluorobenzimidamide | 366, 368 |

Intermediate 11: 5-(3-(1H-Pyrazol-3-yl)phenoxy)-4-methyl-1-tosyl-1H-indole

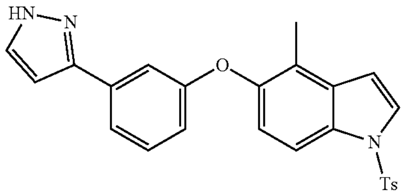 [SMILES: Cc1ccc(S(=O)(=O)n2ccc3c(C)c(Oc4cccc(-c5cc[nH]n5)c4)ccc32)cc1]

A mixture of 5-(3-bromophenoxy)-4-methyl-1-tosyl-1H-indole (Intermediate 3-3, 500 mg, 1.09 mmol), 3-(4,4,5,5-tetramethyl-1,3,2-dioxaborolan-2-yl)-1H-pyrazole (234 mg, 1.21 mmol), Pd(dtbpf)$Cl_2$ (71 mg, 0.11 mmol) and potassium carbonate (303 mg, 2.19 mmol) in dioxane (8 mL) and water (1 mL) was stirred at 90° C. under nitrogen atmosphere overnight. The reaction mixture was cooled to room temperature, filtered through Celite, and washed with ethyl acetate (30 mL×3). The combined organic phase was washed with brine (200 mL), dried over sodium sulfate, filtered, and concentrated. The resulting residue was purified by flash chromatography (silica gel, petroleum ether/ethyl acetate, v/v, 1/1) to afford the title compound as a yellow oil (300 mg, 61%). MS: 444 m/z [M+H]$^+$.

The following intermediates were prepared based on the procedures described for Intermediate 11.

| Inter. No. | Structure | Name | MS m/z [M + H]$^+$/$^1$H NMR |
|---|---|---|---|
| 11-1 | 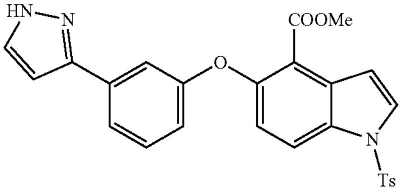 [SMILES: COC(=O)c1c(Oc2cccc(-c3cc[nH]n3)c2)ccc2c1ccn2S(=O)(=O)c1ccc(C)cc1] | methyl 5-(3-(1H-pyrazol-3-yl)phenoxy)-1-tosyl-1H-indole-4-carboxylate | 488 m/z [M + Na]$^+$; $^1$H NMR (400 MHz, $CDCl_3$) δ 9.06 (s, 1H), 8.11 (d, J = 8.2 Hz, 1H), 7.72 (dd, J = 30.4, 5.4 Hz, 3H), 7.55 (s, 1H), 7.36 (d, J = 19.3 Hz, 2H), 7.25 (d, J = 7.6 Hz, 2H), 7.10-7.02 (m, 2H), 6.88 (s, 1H), 6.67 (s, 1H), 3.81 (s, 3H), 2.36 (s, 3H) ppm. |
| 11-2 | 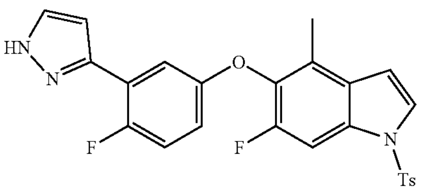 [SMILES: Cc1ccc(S(=O)(=O)n2ccc3c(C)c(Oc4ccc(F)c(-c5cc[nH]n5)c4)c(F)cc32)cc1] | 6-fluoro-5-(4-fluoro-3-(1H-pyrazol-3-yl)phenoxy)-4-methyl-1-tosyl-1H-indole | (400 MHz, DMSO-$d_6$). d 13.03 (s, 1H), 7.98 (d, 2H), 7.90 (d, 1H), 7.78-7.84 (m, 2H), 7.44 (d, 2H), 7.20-7.33 (m, 2H), 6.99 (d, 1H), 6.83-6.85 (m, 1H), 6.62 (d, 1H), 2.36 (s, 3H), 2.31 (s, 3H) ppm. |

Intermediate 12: 2-Fluoro-5-((6-fluoro-4-vinyl-1H-indol-5-yl)oxy)benzothioamide

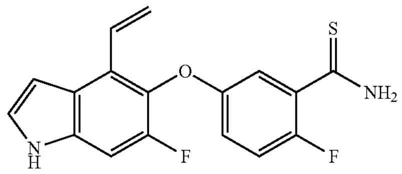 [SMILES: C=Cc1c(Oc2ccc(F)c(C(N)=S)c2)c(F)cc2[nH]ccc12]

To a stirred solution of 2-fluoro-5-((6-fluoro-4-vinyl-1H-indol-5-yl)oxy)benzonitrile (Intermediate 6-1, 8.9 g, 30 mmol) and sodium hydrosulfide (10.1 g, 180 mmol) in N,N-dimethylformamide (100 mL) was added magnesium chloride (8.58 g, 90.1 mmol) in water (20 mL). The mixture was stirred at room temperature for 1 hour, then quenched with water (300 mL). The mixture was extracted with ethyl acetate (2×200 mL). The combined organic phases were washed with brine, dried over sodium sulfate, filtered, and concentrated to give the title compound (9.5 g, yield: 96%) as a solid. MS: 331 m/z $[M+H]^+$.

The following intermediate was prepared based on the procedures described for Intermediate 12.

| Inter. No. | Structure | Name | MS m/z $[M + H]^+$ |
| --- | --- | --- | --- |
| 12-1 | 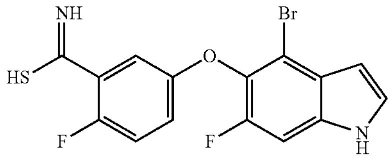 [SMILES: N=C(S)c1cc(Oc2c(F)cc3[nH]ccc3c2Br)ccc1F] | 5-((4-bromo-6-fluoro-1H-indol-5-yl)oxy)-2-fluoro-benzimidothioic acid | 383, 384 |
| 12-2 | 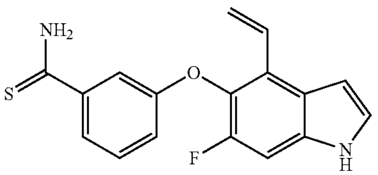 [SMILES: C=Cc1c(Oc2cccc(C(N)=S)c2)c(F)cc2[nH]ccc12] | 3-((6-fluoro-4-vinyl-1H-indol-5-yl)oxy)benzothioamide | 313 |
| 12-3 | 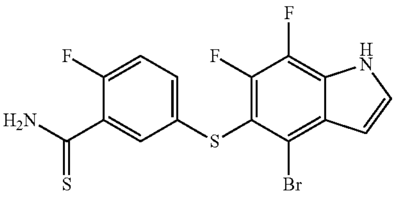 [SMILES: NC(=S)c1cc(Sc2c(F)c(F)c3[nH]ccc3c2Br)ccc1F] | 5-((4-bromo-6,7-difluoro-1H-indol-5-yl)thio)-2-fluoro-benzothioamide | 417, 419 $[M + H]^+$; RT: 1.92 min. (LC-MS method 27) |
| 12-4 | 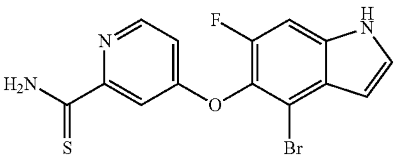 [SMILES: NC(=S)c1cc(Oc2c(F)cc3[nH]ccc3c2Br)ccn1] | 4-((4-bromo-6-fluoro-1H-indol-5-yl)oxy)pyridine-2-carbothioamide | 366, 368 $[M + H]^+$; RT: 1.80 min. (LC-MS method 4) |
| 12-5 | 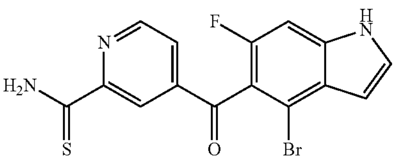 [SMILES: NC(=S)c1cc(C(=O)c2c(F)cc3[nH]ccc3c2Br)ccn1] | 4-(4-bromo-6-fluoro-1H-indole-5-carbonyl)pyridine-2-carbothioamide | 378, 380 $[M + H]^+$; RT: 1.69 min. (LC-MS method 17) |
| 12-6 | 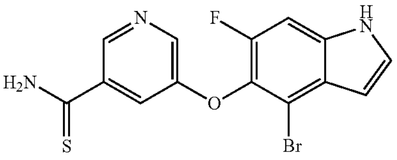 [SMILES: NC(=S)c1cncc(Oc2c(F)cc3[nH]ccc3c2Br)c1] | 5-((4-bromo-6-fluoro-1H-indol-5-yl)oxy)pyridine-3-carbothioamide | 366, 368 $[M + H]^+$; RT: 1.73 min. (LC-MS method 4) |
| 12-7 | 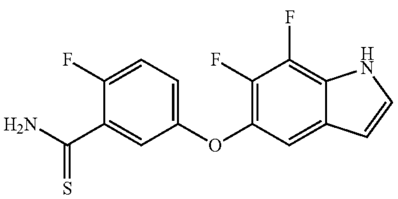 [SMILES: NC(=S)c1cc(Oc2cc3cc[nH]c3c(F)c2F)ccc1F] | 5-((6,7-difluoro-1H-indol-5-yl)oxy)-2-fluorobenzothioamide | 323 $[M + H]^+$; RT: 1.57 min. (LC-MS method 40) |

-continued

| Inter. No. | Structure | Name | MS m/z [M + H]$^+$ |
|---|---|---|---|
| 12-8 | 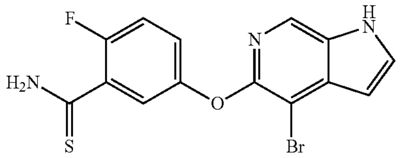 [SMILES: NC(=S)c1cc(Oc2ncc3[nH]ccc3c2Br)ccc1F] | 5-((4-bromo-1H-pyrrolo [2,3-c]pyridin-5-yl)oxy)-2-fluoro-benzothioamide | 366, 368 [M + H]$^+$; RT: 1.61 min. (LC-MS method 40) |
| 12-9 | 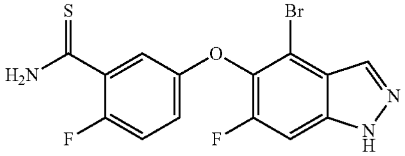 [SMILES: NC(=S)c1cc(Oc2c(F)cc3[nH]ncc3c2Br)ccc1F] | 5-((4-bromo-6-fluoro-1H-indazol-5-yl)oxy)-2-fluoro-benzothioamide | 384, 386 [M + H]$^+$; RT: 2.15 min. (LC-MS method 42) |
| 12-10 | 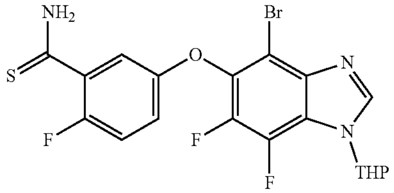 | 5-((4-bromo-6,7-difluoro-1-(tetrahydro-2H-pyran-2-yl)-1H-benzo[d]imidazol-5-yl)oxy)-2-fluoro-benzothioamide | 508, 510 [M + Na]$^+$; RT: 1.83 min. (LC-MS method 003) |

Intermediate 13: 5-((4-(Bromomethyl)-6-fluoro-1-(phenylsulfonyl)-1H-indol-5-yl)oxy)-2-fluorobenzonitrile

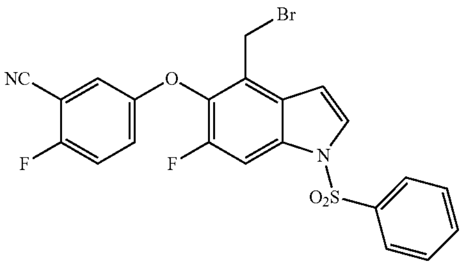 [SMILES: N#Cc1cc(Oc2c(F)cc3c(ccn3S(=O)(=O)c3ccccc3)c2CBr)ccc1F]

To a solution of 2-fluoro-5-((6-fluoro-4-methyl-1-(phenylsulfonyl)-1H-indol-5-yl)oxy)benzonitrile (Intermediate 3-7, 8 g, 18.8 mmol) in dry carbon tetrachloride (650 ml) were added N-bromosuccinimide (3.7 g, 20.7 mmol) and azobisisobutyronitrile (0.92 g, 5.6 mmol) at room temperature. The reaction mixture was stirred at 80° C. for five hours, quenched with saturated potassium carbonate solution (200 ml) and extracted with ethyl acetate (100 ml×3). The combined organic extracts were washed with brine, dried over sodium sulfate, filtered, and concentrated. The resulting residue was triturated with diethyl ether (50 mL), dried in vacuum to give the title compound as a brown solid (6.4 g, 68%). $^1$H NMR (400 MHz, $CDCl_3$) δ 7.94 (d, J=7.6 Hz, 2H), 7.86 (d, J=10.4 Hz, 1H), 7.72 (d, J=3.6 Hz, 1H), 7.64 (m, 1H), 7.55 (m, 2H), 7.19-7.16 (m, 1H), 7.13 (m, 1H), 7.08-7.04 (m, 1H), 6.82 (d, J=3.6 Hz, 1H), 4.64 (s, 2H) ppm.

The following intermediate was prepared based on the procedures described for Intermediate 13.

| Inter. No. | Structure | Name | MS m/z [M + H]$^+$ |
|---|---|---|---|
| 13-1 | 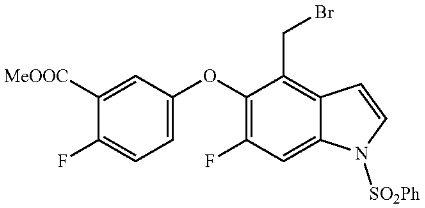 | Methyl 5-((4-(bromomethyl)-6-fluoro-1-(phenylsulfonyl)-1H-indol-5-yl)oxy)-2-fluorobenzoate | 558, 560 [M + Na]$^+$ |

Intermediate 14: Methyl 2-fluoro-5-((6-fluoro-4-vinyl-1H-indol-5-yl)oxy)benzimidothioate Hydroiodide

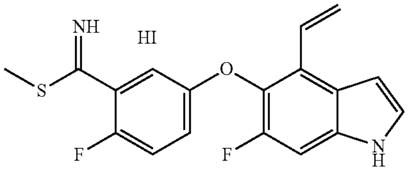

To a stirred solution of 2-fluoro-5-((6-fluoro-4-vinyl-1H-indol-5-yl)oxy)benzothioamide (Intermediate 12, 3.50 g, 10.6 mmol) in acetone (40 mL) was added iodomethane (3.30 mL, 7.52 g, 53.0 mmol). The mixture was heated to 40° C. and maintained at this temperature overnight. The reaction was then cooled to room temperature and concentrated. The crude title compound was obtained as a yellow solid (5.00 g, 100%), which was used without purification. MS (ESI): 345 m/z $[M+H]^+$.

The following intermediates were prepared based on the procedures described for Intermediate 14.

| Inter. No. | Structure | Name | MS m/z $[M + H]^+$ |
|---|---|---|---|
| 14-1 | 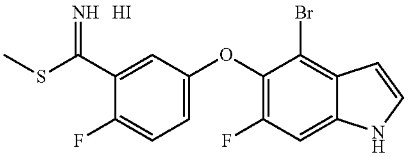 | methyl 5-((4-bromo-6-fluoro-1H-indol-5-yl)oxy)-2-fluorobenzimidothioate hydroiodide | 397, 399 |
| 14-2 | 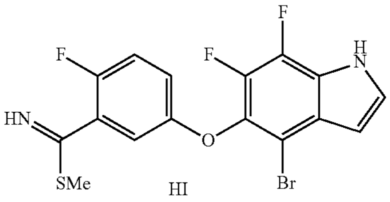 | methyl 5-((4-bromo-6,7-difluoro-1H-indol-5-yl)oxy)-2-fluorobenzimidothioate hydroiodide | 415, 417 |
| 14-3 | 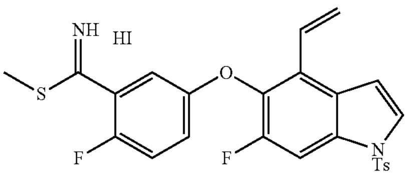 | methyl 2-fluoro-5-((6-fluoro-1-tosyl-4-vinyl-1H-indol-5-yl)oxy)benzimidothioate hydroiodide | 499 |
| 14-4 | 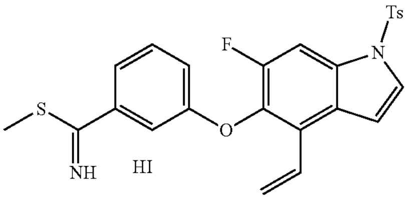 | methyl 3-((6-fluoro-1-tosyl-4-vinyl-1H-indol-5-yl)oxy)benzimidothioate hydroiodide | 481 |
| 14-5 | 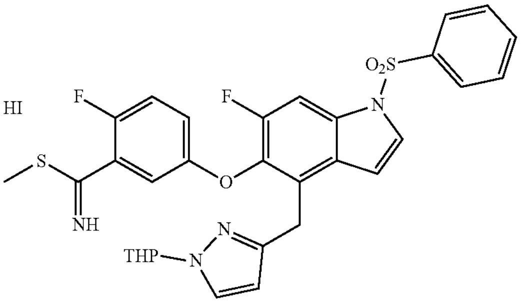 | methyl 2-fluoro-5-((6-fluoro-1-(phenylsulfonyl)-4-((1-(tetrahydro-2H-pyran-2-yl)-1H-pyrazol-3-yl)methyl)-1H-indol-5-yl)oxy)benzimidothioate hydroiodide | 623 |

-continued

| Inter. No. | Structure | Name | MS m/z [M + H]+ |
| --- | --- | --- | --- |
| 14-6 | 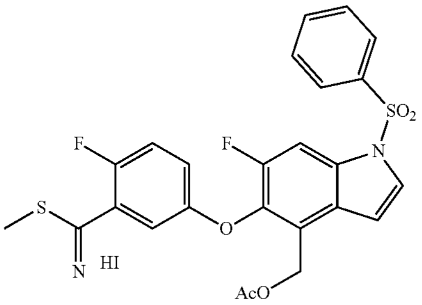 | (6-fluoro-5-(4-fluoro-3-(imino(methylthio)methyl)phenoxy)-1-(phenylsulfonyl)-1H-indol-4-yl)methyl acetate hydroiodide | 531 |
| 14-7 | 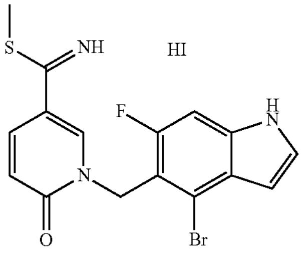 | methyl 1-((4-bromo-6-fluoro-1H-indol-5-yl)methyl)-6-oxo-1,6-dihydropyridine-3-carbimidothioate hydroiodide | 394, 396 |
| 14-8 | 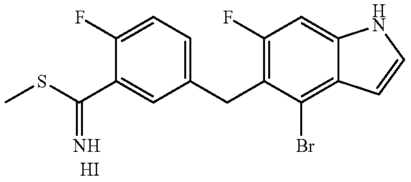 | methyl 5-((4-bromo-6-fluoro-1H-indol-5-yl)methyl)-2-fluorobenzimidothioate hydroiodide | 395, 397 |
| 14-9 | 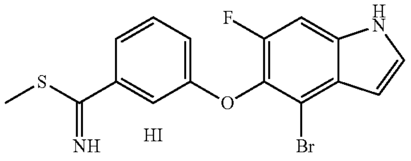 | methyl 3-((4-bromo-6-fluoro-1H-indol-5-yl)oxy)benzimidothioate hydroiodide | 379, 381 |
| 14-10 | 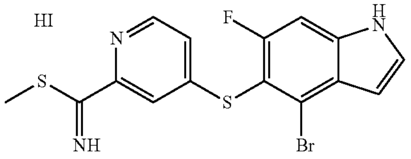 | methyl 4-((4-bromo-6-fluoro-1H-indol-5-yl)thio)pyridine-2-carbimidothioate hydroiodide | 396, 398 |
| 14-11 | 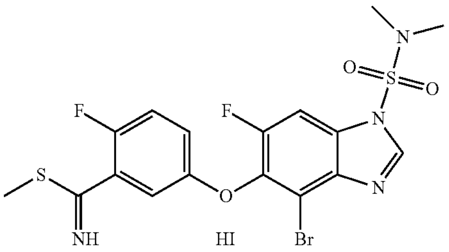 | methyl 5-((4-bromo-1-(N,N-dimethylsulfamoyl)-6-fluoro-1H-benzo[d]imidazol-5-yl)oxy)-2-fluorobenzimidothioate hydroiodide | 505, 507 |
| 14-12 | 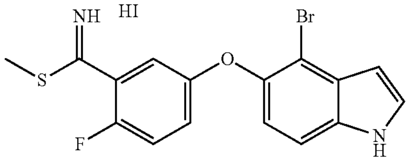 | methyl 5-((4-bromo-1H-indol-5-yl)oxy)-2-fluorobenzimidothioate hydroiodide | 379, 381 |

-continued

| Inter. No. | Structure | Name | MS m/z [M + H]+ |
|---|---|---|---|
| 14-13 | 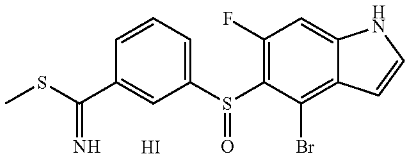 | methyl 3-((4-bromo-6-fluoro-1H-indol-5-yl)sulfinyl)benzimidothioate hydroiodide | 411, 413 |
| 14-14* | 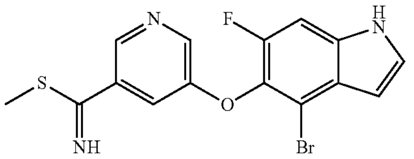 [SMILES: CSC(=N)c1cncc(Oc2c(F)cc3[nH]ccc3c2Br)c1] | methyl 5-((4-bromo-6-fluoro-1H-indol-5-yl)oxy)pyridine-3-carbimidothioate | 380, 382; RT: 1.83 min. (LC-MS method 27) |
| 14-15* | 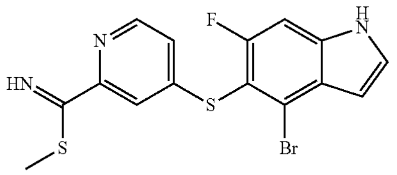 [SMILES: CSC(=N)c1cc(Sc2c(F)cc3[nH]ccc3c2Br)ccn1] | methyl 4-((4-bromo-6-fluoro-1H-indol-5-yl)thio)pyridine-2-carbimidothioate | 396, 398; RT: 1.59 min. (LC-MS Method 4) |
| 14-16 | 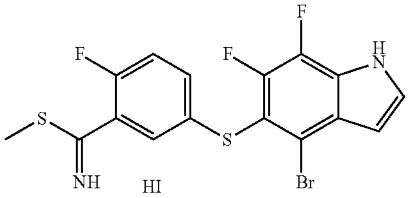 | methyl 5-((4-bromo-6,7-difluoro-1H-indol-5-yl)thio)-2-fluorobenzimidothioate hydroiodide | 431, 433; RT: 1.71 min. (LC-MS Method 4) |
| 14-17 | 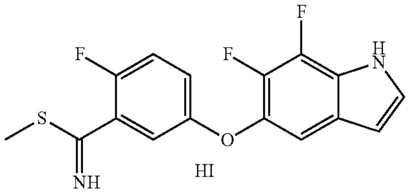 | methyl 5-((6,7-difluoro-1H-indol-5-yl)oxy)-2-fluorobenzimidothioate hydroiodide | 337; RT: 1.79 min. (LC-MS Method 40) |
| 14-18 | 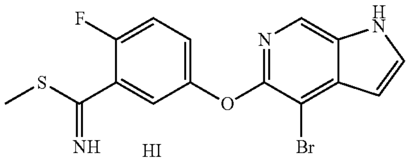 | methyl 5-((4-bromo-1H-pyrrolo[2,3-c]pyridin-5-yl)oxy)-2-fluorobenzimidothioate hydroiodide | 380, 382; RT: 1.15 min. (LC-MS Method 40) |
| 14-19 | 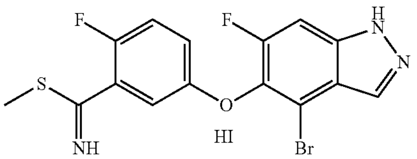 | methyl 5-((4-bromo-6-fluoro-1H-indazol-5-yl)oxy)-2-fluorobenzimidothioate hydroiodide | 398, 400; RT: 1.55 min. (LC-MS Method 42) |

*the methylation of thioamide was realized with iodomethane (5.0 eq)/sodium bicarbonate (5.0 eq)/acetone/room temperature, a slight modification from the procedure described for Intermediate 14.

Intermediate 15: tert-Butyl 2-G3-bromophenyl)propanoate

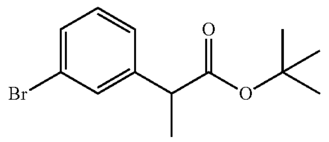 [SMILES: CC(C(=O)OC(C)(C)C)c1cccc(Br)c1]

To a stirred and cooled (−78° C.) 2.0 M solution of lithium diisopropylamide in tetrahydrofuran/heptane/ethylbenzene (10.0 mL, 20.0 mmol) was added dropwise over 10 minutes a solution of tert-butyl 2-(3-bromophenyl)acetate (4.34 g, 16.0 mmol) in tetrahydrofuran (5 mL). The mixture was maintained at −78° C. for 15 minutes and then treated with a solution of iodomethane (1.16 mL, 2.64 g, 18.6 mmol) in tetrahydrofuran (5 mL). After a final five minutes at −78° C., the reaction was quenched with the addition of aqueous ammonium chloride solution (150 mL) and warmed to room temperature. The resulting suspension was extracted with ethyl acetate (3×75 mL) and the combined organic layers were washed with brine (1×100 mL). The solution was then dried over sodium sulphate and concentrated to afford a crude oil which was purified by automated flash chromatography (25 g silica gel column, dichloromethane). The title compound was obtained as faint yellow oil (4.32 g, 95%). $^{1}$H NMR (400 MHz, $CDCl_3$) δ 7.44 (t, J=1.8 Hz, 1H), 7.39-7.33 (m, 1H), 7.24-7.15 (m, 3H), 3.57 (q, J=7.2 Hz, 1H), 1.43 (d, J=7.2 Hz, 3H), 1.40 (s, 9H) ppm.

Intermediate 16: Methyl 2-(3-bromophenyl)-4-((tert-butyldimethylsilyl)oxy)-2-methylbutanoate

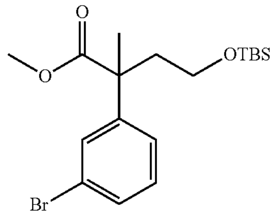 [SMILES: COC(=O)C(C)(CCO[Si](C)(C)C(C)(C)C)c1cccc(Br)c1]

To a stirred and cooled (−78° C.) solution of methyl 2-(3-bromophenyl)propanoate (20.5 g, 84.3 mmol) in tetrahydrofuran (103 mL) was added lithium diisopropylamide (2M in THF, 50.6 mL, 88.6 mmol). The reaction was stirred for 1 hour, then tert-butyl-(2-iodoethoxy)-dimethyl-silane (24.2 g, 84.5 mmol) was added dropwise at −78° C. The mixture was slowly warmed to room temperature and stirred under argon atmosphere for 16 hours, quenched with saturated ammonium chloride (103 mL), and extracted with ethyl acetate (150 mL×3). The combined organic phase was dried over sodium sulfate, filtered, and concentrated. The crude residue was purified by silica gel column chromatography (ethyl acetate in petroleum ether (1%)) to give the title compound as a yellow oil (27.6 g, 82.0%). $^{1}$H NMR (400 MHz, chloroform-d) δ 7.45 (s, 1H), 7.36 (d, J=8 Hz, 1H), 7.24-7.16 (m, 2H), 3.64 (s, 3H), 3.59-3.53 (m, 2H), 2.38-2.29 (m, 1H), 2.14-2.08 (m, 1H), 1.55 (s, 3H), 0.85 (s, 9H), 0.01 (s, 6H) ppm.

The following intermediates were prepared based on the procedures described for Intermediate 16.

| Inter. No. | Structure | Name | MS m/z $[M + H]^+$ and/ or $^{1}$H NMR |
|---|---|---|---|
| 16-1 | 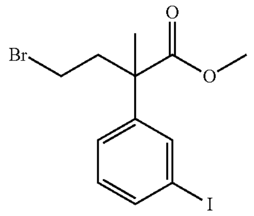 [SMILES: COC(=O)C(C)(CCBr)c1cccc(I)c1] | methyl 4-bromo-2-(3-iodophenyl)-2-methylbutanoate | 397, 399 m/z $[M + H]^+$ $^{1}$H NMR (400 MHz, $CDCl_3$) δ 7.32 (m, 4H), 3.68 (s, 3H), 3.23 (dd, 2H), 2.53 (m, 2H), 2.05 (s, 3H) |
| 16-2 | 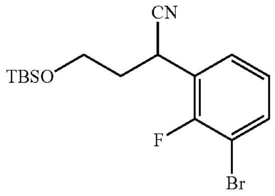 [SMILES: CC(C)(C)[Si](C)(C)OCCC(C#N)c1cccc(Br)c1F] | 2-(3-bromo-2-fluorophenyl)-4-((tert-butyldimethylsilyl)oxy) butanenitrile | 394, 396 (M + Na) |
| 16-3 | 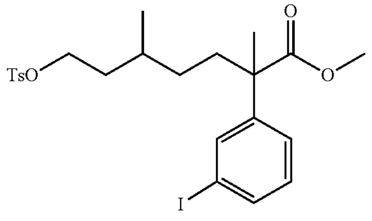 [SMILES: COC(=O)C(C)(CCC(C)CCOS(=O)(=O)c1ccc(C)cc1)c1cccc(I)c1] | methyl 2-(3-iodophenyl)-2,5-dimethyl-7-(tosyloxy)heptanoate | 567.2 $[M + Na]^+$ |

-continued

| Inter. No. | Structure | Name | MS m/z $[M + H]^+$ and/ or $^1H$ NMR |
|---|---|---|---|
| 16-4 | 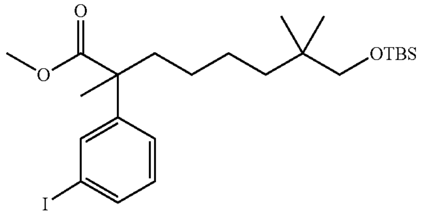 [SMILES: COC(=O)C(C)(CCCCC(C)(C)CO[Si](C)(C)C(C)(C)C)c1cccc(I)c1] | methyl 8-((tert-butyldimethylsilyl)oxy)-2-(3-iodophenyl)-2,7,7-trimethyloctanoate | 533 |
| 16-5 | 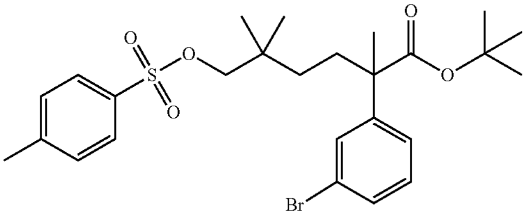 [SMILES: Cc1ccc(S(=O)(=O)OCC(C)(C)CCC(C)(C(=O)OC(C)(C)C)c2cccc(Br)c2)cc1] | tert-butyl 2-(3-bromophenyl)-2,5,5-trimethyl-6-(tosyloxy) hexanoate | 561 $[M + Na]^+$ |
| 16-6 | 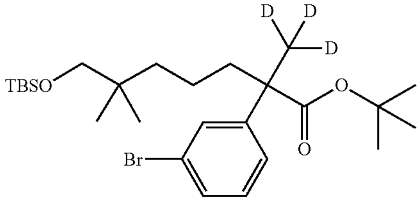 [SMILES: [2H]C([2H])([2H])C(CCCC(C)(C)CO[Si](C)(C)C(C)(C)C)(C(=O)OC(C)(C)C)c1cccc(Br)c1] | tert-butyl 2-(3-bromophenyl)-7-((tert-butyldimethylsilyl)oxy)-6,6-dimethyl-2-(methyl-d3)heptanoate | 516, 518 |
| 16-7 | 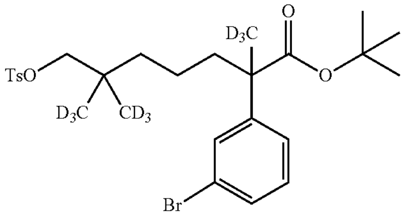 [SMILES: [2H]C([2H])([2H])C(CCCC(COS(=O)(=O)c1ccc(C)cc1)(C([2H])([2H])[2H])C([2H])([2H])[2H])(C(=O)OC(C)(C)C)c1cccc(Br)c1] | tert-butyl 2-(3-bromophenyl)-2,6-bis(methyl-d3)-6-((tosyloxy)methyl) heptanoate-7,7,7-d3 | 584, 586 $[M + Na]^+$ |
| 16-8 | 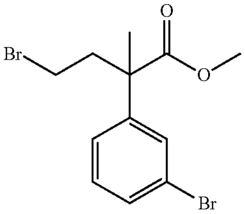 [SMILES: COC(=O)C(C)(CCBr)c1cccc(Br)c1] | methyl 5-bromo-2-(3-bromophenyl)-2-methylpentanoate | 365 |
| 16-9 | 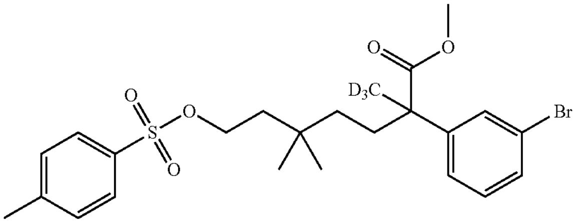 [SMILES: [2H]C([2H])([2H])C(CCC(C)(C)CCOS(=O)(=O)c1ccc(C)cc1)(C(=O)OC)c1cccc(Br)c1] | methyl 2-(3-bromophenyl)-5,5-dimethyl-2-(methyl-d3)-7-(tosyloxy)heptanoate | 536, 538 $[M + Na]^+$ |
| 16-10 | 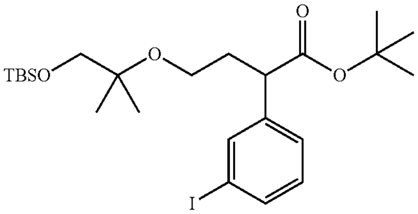 [SMILES: CC(C)(C)OC(=O)C(CCOC(C)(C)CO[Si](C)(C)C(C)(C)C)c1cccc(I)c1] | tert-butyl 4-((1-((tert-butyldimethylsilyl)oxy)-2-methylpropan-2-yl)oxy)-2-(3-iodophenyl)butanoate | 571 $[M + Na]^+$ |

-continued

| Inter. No. | Structure | Name | MS m/z [M + H]+ and/ or 1H NMR |
|---|---|---|---|
| 16-11 | 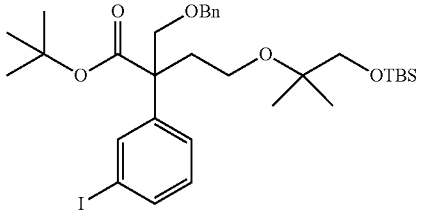 [SMILES: CC(C)(C)OC(=O)C(CCOC(C)(C)CO[Si](C)(C)C(C)(C)C)(COCc1ccccc1)c1cccc(I)c1] | tert-butyl 2-((benzyloxy) methyl)-4-((1-((tert-butyldimethylsilyl)oxy)-2-methylpropan-2-yl)oxy)-2-(3-iodophenyl)butanoate | 691 [M + Na]+ |
| 16-12 | 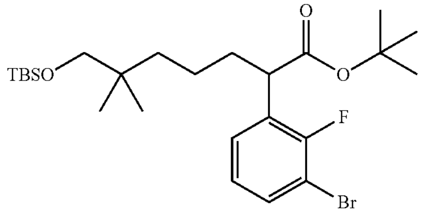 [SMILES: CC(C)(CCCC(C(=O)OC(C)(C)C)c1cccc(Br)c1F)CO[Si](C)(C)C(C)(C)C] | tert-butyl 2-(3-bromo-2-fluorophenyl)-7-((tert-butyldimethylsilyl) oxy)-6,6-dimethylheptanoate | 539, 541 [M + Na]+ |
| 16-13 | 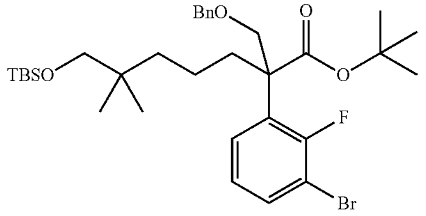 [SMILES: CC(C)(CCCC(COCc1ccccc1)(C(=O)OC(C)(C)C)c1cccc(Br)c1F)CO[Si](C)(C)C(C)(C)C] | tert-butyl 2-((benzyloxy)methyl)-2-(3-bromo-2-fluorophenyl)-7-((tert-butyldimethylsilyl)oxy)-6,6-dimethylheptanoate | 659, 661 [M + Na]+ |
| 16-14 | 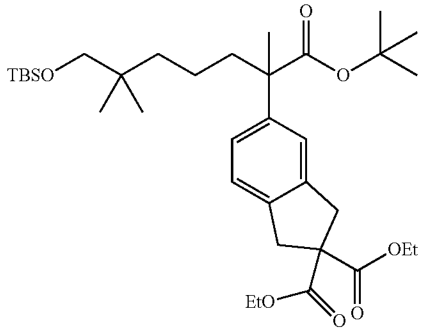 [SMILES: CCOC(=O)C1(C(=O)OCC)Cc2ccc(C(C)(CCCC(C)(C)CO[Si](C)(C)C(C)(C)C)C(=O)OC(C)(C)C)cc2C1] | diethyl 5-(1-(tert-butoxy)-7-((tert-butyldimethylsilyl)oxy)-2,6,6-trimethyl-1-oxoheptan-2-yl)-1,3-dihydro-2H-indene-2,2-dicarboxylate | 641 [M + Na]+ |
| 16-15 | 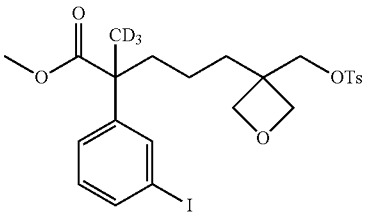 [SMILES: [2H]C([2H])([2H])C(CCCC1(COS(=O)(=O)c2ccc(C)cc2)COC1)(C(=O)OC)c1cccc(I)c1] | methyl 2-(3-iodophenyl)-2-(methyl-d3)-5-(3-((tosyloxy)methyl)oxetan-3-yl)pentanoate | 576 |
| 16-16 | 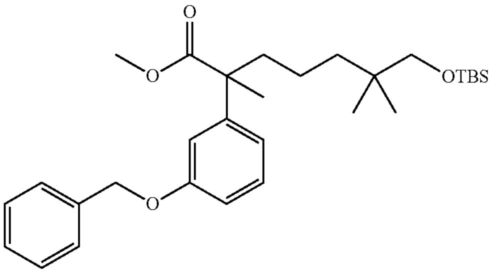 [SMILES: COC(=O)C(C)(CCCC(C)(C)CO[Si](C)(C)C(C)(C)C)c1cccc(OCc2ccccc2)c1] | methyl 2-(3-(benzyloxy) phenyl)-7-((tert-butyldimethylsilyl)oxy)-2,6,6-trimethylheptanoate | 521 [M + Na]+ |

-continued

| Inter. No. | Structure | Name | MS m/z [M + H]$^+$ and/ or $^1$H NMR |
|---|---|---|---|
| 16-17 | 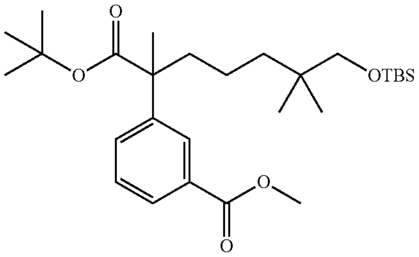 [SMILES: COC(=O)c1cccc(C(C)(CCCC(C)(C)CO[Si](C)(C)C(C)(C)C)C(=O)OC(C)(C)C)c1] | methyl 3-(1-(tert-butoxy)-7-((tert-butyldimethylsilyl)oxy)-2,6,6-trimethyl-1-oxoheptan-2-yl)benzoate | 515 [M + Na]$^+$ |
| 16-18 | 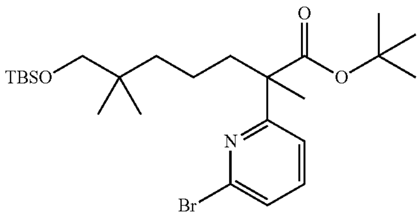 [SMILES: CC(C)(CCCC(C)(C(=O)OC(C)(C)C)c1cccc(Br)n1)CO[Si](C)(C)C(C)(C)C] | tert-butyl 2-(6-bromopyridin-2-yl)-7-((tert-butyldimethylsilyl) oxy)-2,6,6-trimethylheptanoate | 514, 516 |
| 16-19 | 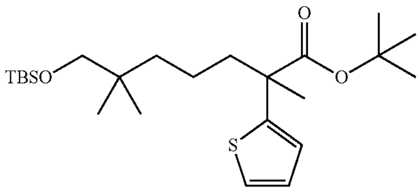 [SMILES: CC(C)(CCCC(C)(C(=O)OC(C)(C)C)c1cccs1)CO[Si](C)(C)C(C)(C)C] | tert-butyl 7-((tert-butyldimethylsilyl)oxy)-2,6,6-trimethyl-2-(thiophen-2-yl)heptanoate | 463 [M + Na]$^+$ |

Intermediate 17: 8-Bromo-6-(3-iodophenyl)-2,2,6-trimethyl-7-oxooctyl Acetate

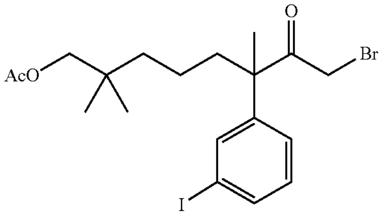 [SMILES: CC(=O)OCC(C)(C)CCCC(C)(C(=O)CBr)c1cccc(I)c1]

Exchanging 2-(3-(3-methoxy-3-oxopropyl)phenyl)acetic acid (intermediate 8B) for 7-acetoxy-2-(3-iodophenyl)-2,6,6-trimethylheptanoic acid (Intermediate 17C, 980 mg, 2.27 mmol), the reaction procedure described for Intermediate 8 was used to prepare the title compound as an oil (960 mg, 83%). MS (ESI): 531, 533 m/z [M+Na]$^+$.

Intermediate 17A: 7-((Tert-butyldimethylsilyl)oxy)-2-(3-iodophenyl)-2,6,6-trimethylheptanoic Acid

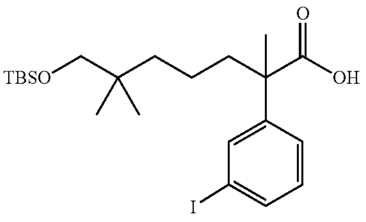 [SMILES: CC(C)(CCCC(C)(C(=O)O)c1cccc(I)c1)CO[Si](C)(C)C(C)(C)C]

To a stirred and cooled (−78° C.) solution of diisopropylamide (1.51 g, 15 mmol) in tetrahydrofuran was added n-butyllithium (2.5M in hexanes, 6 mL, 15 mmol). The reaction was stirred for 30 minutes at this temperature, then hexamethylphosphoramide was added (2.68 g, 15 mmol) and stirring continued for another 30 minutes. To this mixture was added 2-(3-iodophenyl)propanoic acid (1.66 g, 6 mmol) in 10 mL of tetrahydrofuran over 5 minutes. The resulting mixture was stirred at −78° C. for 30 minutes. Then tert-butyl((5-iodo-2,2-dimethylpentyl)oxy)dimethylsilane (Intermediate 29C-1, 5.33 g, 15 mmol) was added in one portion. The mixture was allowed to warm to room temperature and stirred for 2 hours. After confirming that the starting material was consumed by LC-MS, the reaction was quenched with a mixture of 1 M hydrochloric acid (20 ml) and saturated ammonium chloride solution (15 mL) and extracted with ethyl acetate (3×20 mL). The combined organic extracts were washed with brine (20 mL), dried over sodium sulfate and concentrated to give the crude title product (1.99 g, 65%). MS (ESI): 505 m/z [M+H]$^+$.

Intermediate 17B: 7-Hydroxy-2-(3-iodophenyl)-2,6,6-trimethylheptanoic Acid

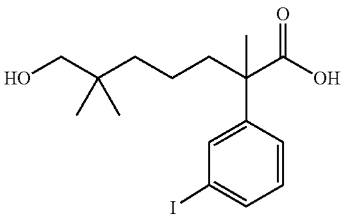 [SMILES: CC(C)(CO)CCCC(C)(C(=O)O)c1cccc(I)c1]

To a solution of 7-((tert-butyldimethylsilyl)oxy)-2-(3-iodophenyl)-2,6,6-trimethylheptanoic acid (Intermediate 17A, 4.8 mmol, 2.42 g) in tetrahydrofuran (5 mL) was added 1 M tetrabutylammonium fluoride (9.6 ml, 9.6 mmol). The reaction mixture was stirred at 60° C. for 16 hours. After confirming the starting material was consumed by LC-MS, the mixture was acidified with 10 mL 1 M hydrochloric acid and extracted with ethyl acetate (2×50 ml). The combined organic phases were washed with water, dried over sodium sulfate, and concentrated. The residue was purified by silica gel column chromatography to afford the title compound (1.03 g, 55%). MS (ESI): 413 m/z $[M+Na]^+$.

Intermediate 17C: 7-Acetoxy-2-(3-iodophenyl)-2,6,6-trimethylheptanoic Acid

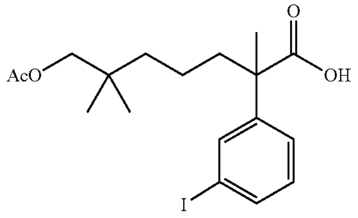 [SMILES: CC(=O)OCC(C)(C)CCCC(C)(C(=O)O)c1cccc(I)c1]

To a stirred solution of 7-hydroxy-2-(3-iodophenyl)-2,6,6-trimethylheptanoic acid (Intermediate 17B, 2.50 mmol, 970 mg) in acetic acid (15 mL) was added acetic anhydride (12.4 mmol, 1.27 g) and tosylic acid (42.8 mg, 0.25 mmol). The reaction was stirred at room temperature for 4 hours. After confirming the starting material was consumed by LC-MS analysis, the mixture was treated with 3 mL of water and stirred for 16 hours to hydrolyze anhydride, then diluted with 100 mL of water, extracted with ethyl acetate (3×50 mL). The combined organic extracts were washed with brine, dried over sodium sulfate, and concentrated. The residue was purified by silica gel column chromatography to afford the title compound (0.98 g, 90%). MS (ESI): 455 m/z $[M+Na]^+$.

The following intermediates were prepared based on the procedures described for Intermediate 17, and/or for Intermediates 17A to 17C.

| Inter. No. | Structure | Name | MS m/z $[M + H]^+$ |
|---|---|---|---|
| 17-1 | 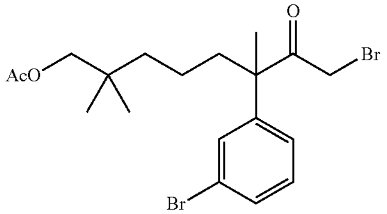 [SMILES: CC(=O)OCC(C)(C)CCCC(C)(C(=O)CBr)c1cccc(Br)c1] | 8-bromo-6-(3-bromophenyl)-2,2,6-trimethyl-7-oxooctyl acetate | 485 $[M + Na]^+$ |
| 17-2 | 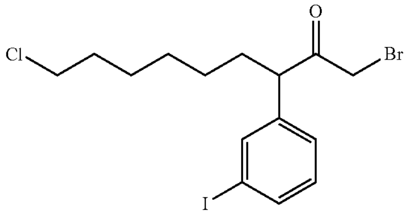 [SMILES: O=C(CBr)C(CCCCCCCl)c1cccc(I)c1] | 1-bromo-9-chloro-3-(3-iodophenyl)nonan-2-one | 457, 459 |
| 17-3 | 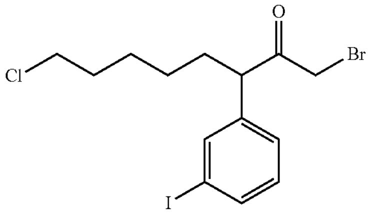 [SMILES: O=C(CBr)C(CCCCCCl)c1cccc(I)c1] | 1-bromo-8-chloro-3-(3-iodophenyl)octan-2-one | 443, 445 |
| 17-4 | 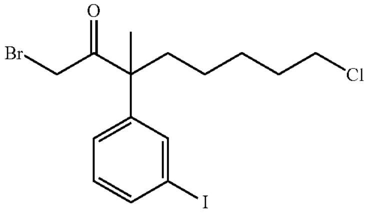 [SMILES: CC(CCCCCCl)(C(=O)CBr)c1cccc(I)c1] | 1-bromo-8-chloro-3-(3-iodophenyl)-3-methyloctan-2-one | 479, 481 $[M + Na]^+$ |

-continued

| Inter. No. | Structure | Name | MS m/z $[M + H]^+$ |
|---|---|---|---|
| 17-5 | 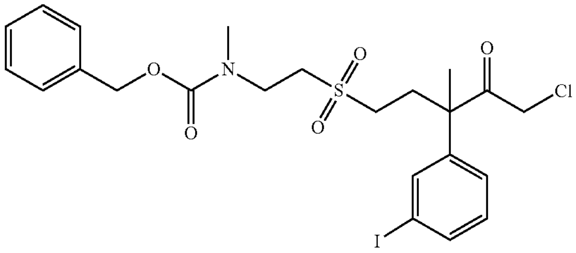 [SMILES: CN(CCS(=O)(=O)CCC(C)(C(=O)CCl)c1cccc(I)c1)C(=O)OCc1ccccc1] | benzyl (2-((5-chloro-3-(3-iodophenyl)-3-methyl-4-oxopentyl)sulfonyl)ethyl)(methyl)carbamate | 592 |
| 17-6 | 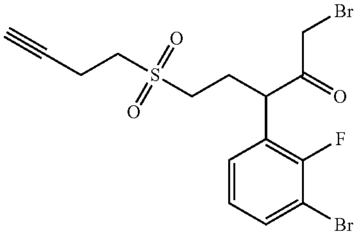 [SMILES: C#CCCS(=O)(=O)CCC(C(=O)CBr)c1cccc(Br)c1F] | 1-bromo-3-(3-bromo-2-fluorophenyl)-5-(but-3-yn-1-ylsulfonyl)pentan-2-one | 455 |
| 17-7 | 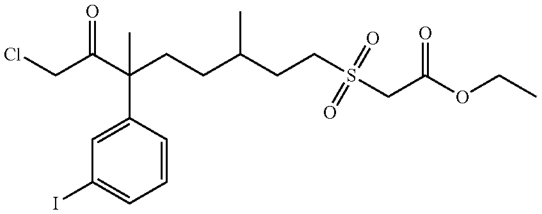 [SMILES: CCOC(=O)CS(=O)(=O)CCC(C)CCC(C)(C(=O)CCl)c1cccc(I)c1] | ethyl 2-((8-chloro-6-(3-iodophenyl)-3,6-dimethyl-7-oxooctyl)sulfonyl)acetate | 565, 567 $[M + Na]^+$ |
| 17-8 | 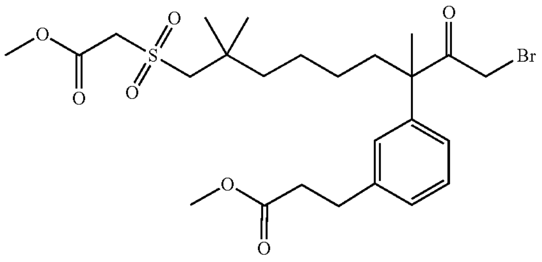 [SMILES: COC(=O)CCc1cccc(C(C)(CCCCC(C)(C)CS(=O)(=O)CC(=O)OC)C(=O)CBr)c1] | methyl 3-(3-(1-bromo-9-((2-methoxy-2-oxoethyl)sulfonyl)-3,8,8-trimethyl-2-oxononan-3-yl)phenyl)propanoate | 561, 563 |
| 17-9 | 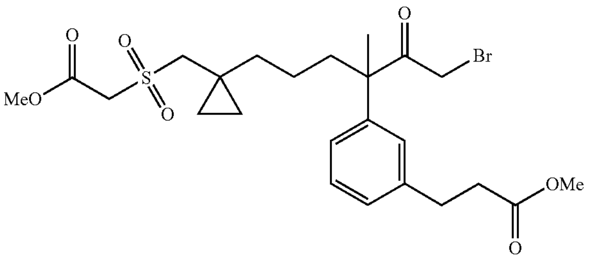 [SMILES: COC(=O)CCc1cccc(C(C)(CCCC2(CS(=O)(=O)CC(=O)OC)CC2)C(=O)CBr)c1] | methyl 3-(3-(1-bromo-6-(1-(((2-methoxy-2-oxoethyl)sulfonyl)methyl)cyclopropyl)-3-methyl-2-oxohexan-3-yl)phenyl)propanoate | 545, 547 |
| 17-10 | 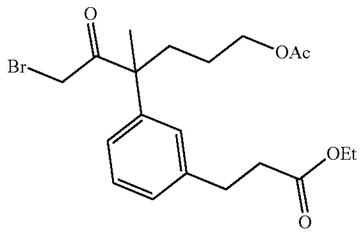 [SMILES: CCOC(=O)CCc1cccc(C(C)(CCCOC(C)=O)C(=O)CBr)c1] | ethyl 3-(3-(6-acetoxy-1-bromo-3-methyl-2-oxohexan-3-yl)phenyl)propanoate | 427, 429 |

-continued

| Inter. No. | Structure | Name | MS m/z $[M + H]^+$ |
|---|---|---|---|
| 17-11 | 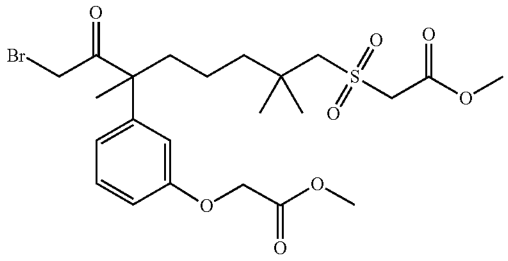 [SMILES: COC(=O)COc1cccc(C(C)(CCCC(C)(C)CS(=O)(=O)CC(=O)OC)C(=O)CBr)c1] | methyl 2-((8-bromo-6-(3-(2-methoxy-2-oxoethoxy)phenyl)-2,2,6-trimethyl-7-oxooctyl)sulfonyl)acetate | 549, 551 |
| 17-12 | 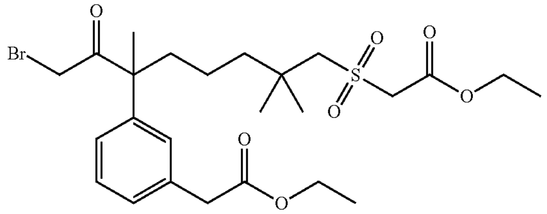 [SMILES: CCOC(=O)Cc1cccc(C(C)(CCCC(C)(C)CS(=O)(=O)CC(=O)OCC)C(=O)CBr)c1] | ethyl 2-((8-bromo-6-(3-(2-ethoxy-2-oxoethyl)phenyl)-2,2,6-trimethyl-7-oxooctyl)sulfonyl)acetate | 561, 563 |
| 17-13 | 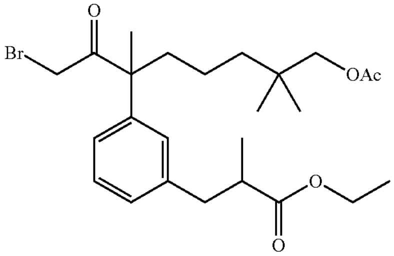 [SMILES: CCOC(=O)C(C)Cc1cccc(C(C)(CCCC(C)(C)COC(C)=O)C(=O)CBr)c1] | ethyl 3-(3-(8-acetoxy-1-bromo-3,7,7-trimethyl-2-oxooctan-3-yl)phenyl)-2-methylpropanoate | 497, 499 |
| 17-14 | 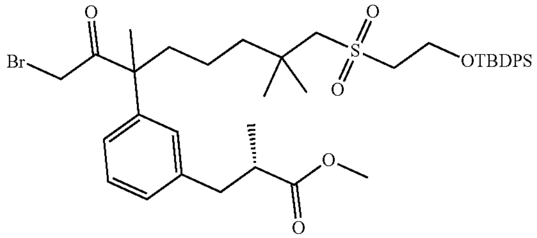 | methyl (2S)-3-(3-(1-bromo-8-((2-((tert-butyldiphenylsilyl)oxy)ethyl)sulfonyl)-3,7,7-trimethyl-2-oxooctan-3-yl)phenyl)-2-methylpropanoate | 793, 795 $[M + Na]^+$ |
| 17-15 | 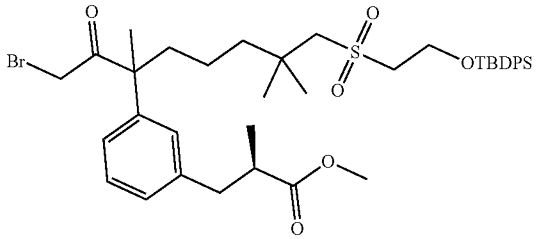 | methyl (2R)-3-(3-(1-bromo-8-((2-((tert-butyldiphenylsilyl)oxy)ethyl)sulfonyl)-3,7,7-trimethyl-2-oxooctan-3-yl)phenyl)-2-methylpropanoate | 793, 795 $[M + Na]^+$ |
| 17-16 | 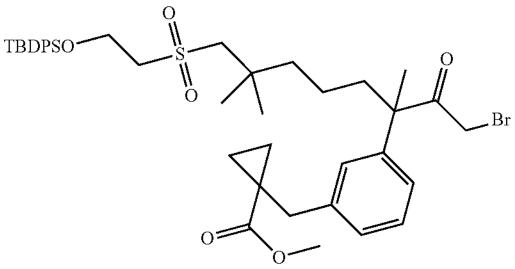 | methyl 1-(3-(1-bromo-8-((2-((tert-butyldiphenylsilyl)oxy)ethyl)sulfonyl)-3,7,7-trimethyl-2-oxooctan-3-yl)benzyl)cyclopropane-1-carboxylate | 805, 807 $[M + Na]^+$ |

-continued

| Inter. No. | Structure | Name | MS m/z [M + H]+ |
| --- | --- | --- | --- |
| 17-17 | 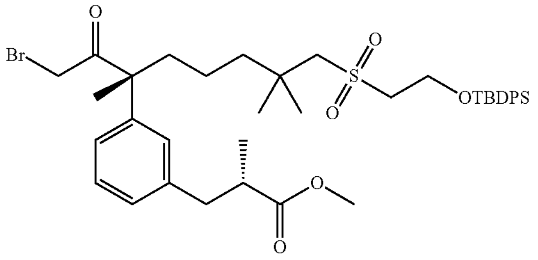 | methyl (S)-3-(3-((R)-1-bromo-8-((2-((tert-butyldiphenylsilyl)oxy)ethyl)sulfonyl)-3,7,7-trimethyl-2-oxooctan-3-yl)phenyl)-2-methylpropanoate | 793, 795 [M + Na]+ |

Intermediate 18: Ethyl 2-(((5-(3-carbamimidoyl-4-fluorophenoxy)-6-fluoro-1-(phenylsulfonyl)-1H-indol-4-yl)methyl)sulfonyl)acetate

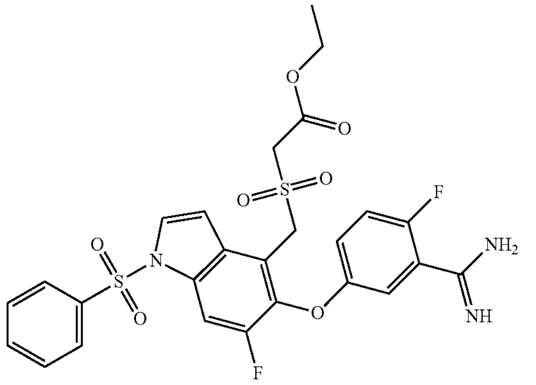 [SMILES: CCOC(=O)CS(=O)(=O)Cc1c(Oc2ccc(F)c(C(=N)N)c2)c(F)cc2c1ccn2S(=O)(=O)c1ccccc1]

A mixture of ethyl 2-(((5-(3-(N-acetoxycarbamimidoyl)-4-fluorophenoxy)-6-fluoro-1-(phenylsulfonyl)-1H-indol-4-yl)methyl)sulfonyl)acetate (Intermediate 18D, 1 g, 1.54 mmol) and Pd/C (0.3 g, 10%) in acetic acid (10 mL) was stirred under hydrogen balloon for 12 hours. The mixture was filtered, and the filter cake was washed with ethyl acetate (200 mL). The combined filtrate was washed with saturated sodium bicarbonate (100 mL), brine (50 mL), dried over sodium sulfate and concentrated. The residue was purified by silica gel column (10% methanol in dichloromethane) to give the title product as a yellow solid (0.7 g, 76.9%). MS (ESI): 592 m/z $[M+H]^+$.

Intermediate 18A: Ethyl 2-(((5-(3-cyano-4-fluorophenoxy)-6-fluoro-1-(phenylsulfonyl)-1H-indol-4-yl)methyl)thio)acetate

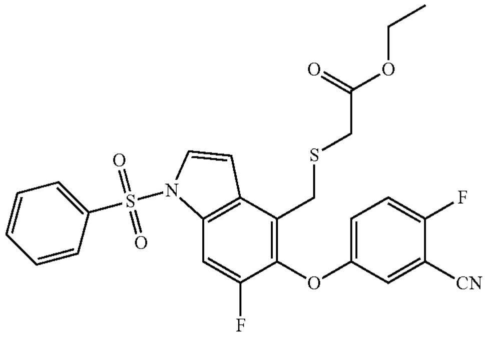 [SMILES: CCOC(=O)CSCc1c(Oc2ccc(F)c(C#N)c2)c(F)cc2c1ccn2S(=O)(=O)c1ccccc1]

To a stirred solution of 5-((4-(bromomethyl)-6-fluoro-1-(phenylsulfonyl)-1H-indol-5-yl)oxy)-2-fluorobenzonitrile (Intermediate 13, 10 g, 19.9 mmol) in acetone (200 mL) was added ethyl 2-sulfanylacetate (3.10 g, 25.8 mmol), potassium carbonate (5.49 g, 39.7 mmol) and sodium iodide (2.38 g, 15.9 mmol). The mixture was stirred for 20 hours at room temperature and then concentrated. The residue was purified by silica gel column chromatography (eluting with 20% ethyl acetate in petroleum ether) to afford the title product as a white solid (8 g, 87.8% yield). MS (ESI): 565 m/z $[M+23]^+$.

Intermediate 18B: Ethyl 2-(((5-(3-cyano-4-fluorophenoxy)-6-fluoro-1-(phenylsulfonyl)-1H-indol-4-yl)methyl)sulfonyl)acetate

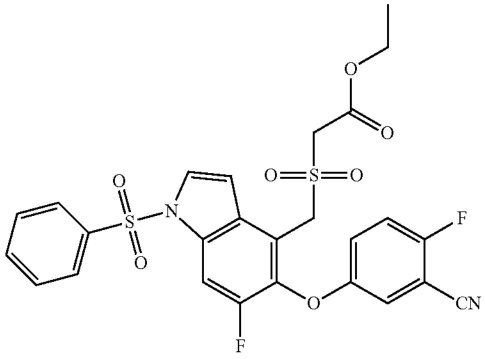 [SMILES: CCOC(=O)CS(=O)(=O)Cc1c(Oc2ccc(F)c(C#N)c2)c(F)cc2c1ccn2S(=O)(=O)c1ccccc1]

To a stirred solution of ethyl 2-(((5-(3-cyano-4-fluorophenoxy)-6-fluoro-1-(phenylsulfonyl)-1H-indol-4-yl)methyl)thio)acetate (Intermediate 18A, 10 g, 18.4 mmol) in dichloromethane (200 mL) was added 3-chlorobenzenecarboperoxoic acid (4.86 g, 24 mmol). The mixture was stirred at room temperature for 12 hours, then quenched with saturated sodium bicarbonate (50 mL). The separated organic layer was washed with saturated sodium sulfite (100 mL), brine (30 mL), dried over sodium sulfate and concentrated. The residue was purified by silica gel column chromatography (50% ethyl acetate in petroleum ether) to give the title product as a pale-yellow solid (9 g, 85% yield). MS (ESI): 597 m/z $[M+23]^+$.

Intermediate 18C: Ethyl 2-(((6-fluoro-5-(4-fluoro-3-(N-hydroxycarbamimidoyl)phenoxy)-1-(phenylsulfonyl)-1H-indol-4-yl)methyl)sulfonyl)acetate

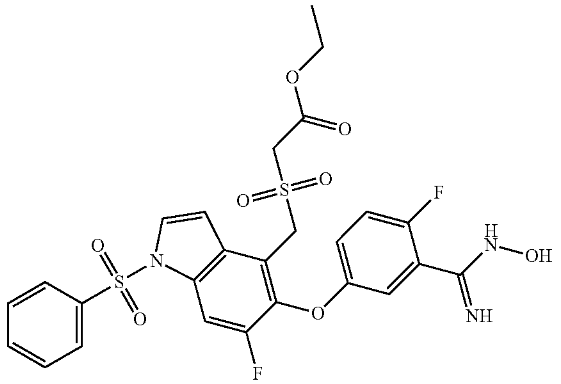 [SMILES: CCOC(=O)CS(=O)(=O)Cc1c(Oc2ccc(F)c(C(=N)NO)c2)c(F)cc2c1ccn2S(=O)(=O)c1ccccc1]

To a stirred solution of ethyl 2-(((5-(3-cyano-4-fluorophenoxy)-6-fluoro-1-(phenylsulfonyl)-1H-indol-4-yl)methyl)sulfonyl)acetate (Intermediate 18B, 3 g, 5.22 mmol) in ethanol (50 mL) was added hydroxylamine hydrochloride (1.09 g, 15.7 mmol) and triethylamine (3.17 g, 31.3 mmol). The mixture was stirred at 80° C. for 4 hours and then concentrated. The residue was partitioned between water (30 mL) and ethyl acetate (50 mL). The separated organic layer was combined with additional ethyl acetate extracts (2×50 mL), washed with brine (30 mL), dried over sodium sulfate and concentrated to give the title product as a yellow solid (3 g, crude). MS (ESI): 608 m/z [M+H]$^+$.

Intermediate 18D: Ethyl 2-(((5-(3-(N-acetoxycarbamimidoyl)-4-fluorophenoxy)-6-fluoro-1-(phenylsulfonyl)-1H-indol-4-yl)methyl)sulfonyl)acetate

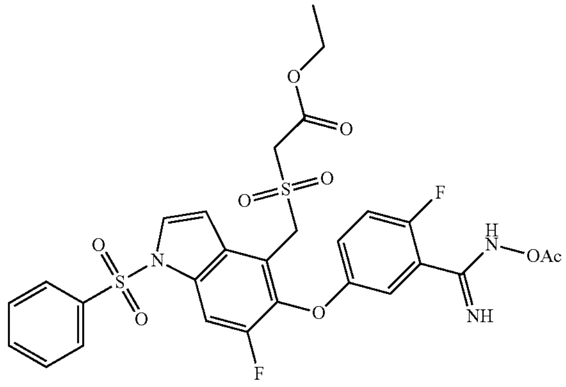 [SMILES: CCOC(=O)CS(=O)(=O)Cc1c(Oc2ccc(F)c(C(=N)NOC(C)=O)c2)c(F)cc2c1ccn2S(=O)(=O)c1ccccc1]

To a stirred solution of ethyl 2-(((6-fluoro-5-(4-fluoro-3-(N-hydroxycarbamimidoyl)phenoxy)-1-(phenylsulfonyl)-1H-indol-4-yl)methyl)sulfonyl)acetate (Intermediate 18C, 3 g, 4.94 mmol) in acetic acid (15 mL) was added acetic anhydride (0.76 g, 7.41 mmol). The reaction was stirred for 12 hours at room temperature, then quenched with water (100 mL). The mixture was extracted with ethyl acetate (3×100 mL). The combined organic extracts were washed with brine (50 mL), dried over sodium sulfate and concentrated. The residue was purified by silica gel column chromatography (50% ethyl acetate in petroleum ether) to give the title product as a white solid (1 g, 31.2%). MS (ESI): 650 m/z [M+H]$^+$.

Intermediate 19: Methyl 2-((6-bromo-4-(3-bromophenyl)-4-methyl-5-oxohexyl)oxy)-2-methylpropanoate

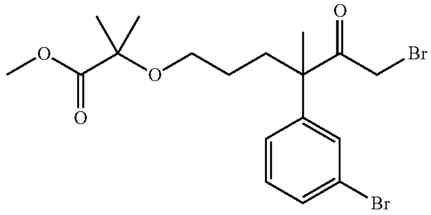 [SMILES: COC(=O)C(C)(C)OCCCC(C)(C(=O)CBr)c1cccc(Br)c1]

To a stirred solution of methyl 2-((4-(3-bromophenyl)-4-methyl-5-oxohexyl)oxy)-2-methylpropanoate (Intermediate 19L, 1.6 g, 0.0042 mol) in tetrahydrofuran (40 mL) was added pyridinium hydrobromide perbromide (1.2 g, 0.0037 mol). The reaction was heated at 50° C. for 4 hours and then concentrated. The residue was diluted with ethyl acetate (50 mL), washed with water, brine, dried over sodium sulfate and concentrated to give the title compound as yellow oil (1.6 g, 83%). MS (ESI): 465 m/z [M+H]$^+$.

Intermediate 19A: Ethyl 3-((2-methylbut-3-en-2-yl)oxy)propanoate

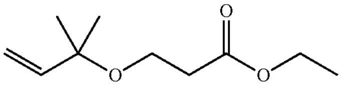

To a stirred and cooled (0° C.) solution of ethyl acrylate (50 g, 0.5 mol) and 2-methylbut-3-en-2-ol (86 g, 1 mol) in tetrahydrofuran (250 mL) was slowly added sodium hydride (2 g, 50 mmol, 60% in petroleum oil). The reaction was stirred at room temperature for 16 hours, then quenched with saturated ammonium chloride. The mixture was extracted with ethyl acetate (3×300 mL). The combined organic extracts were washed with brine, dried and concentrated. The crude product was purified by flash silica chromatography (0-20% ethyl acetate in petroleum ether) to give the title compound as a colorless oil (35.4 g, 38%).

Intermediate 19B: 3-((2-Methylbut-3-en-2-yl)oxy)propan-1-ol

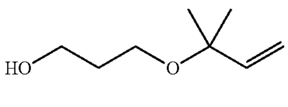

To a stirred and cooled (0° C.) solution of ethyl 3-((2-methylbut-3-en-2-yl)oxy)propanoate (Intermediate 19A, 35 g, 0.19 mol) in 100 mL of tetrahydrofuran was added lithium aluminum hydride (8.56 g, 0.23 mol). The reaction was stirred at room temperature for 1 hour, then cooled to 0° C., quenched carefully with water (10 mL), 15% sodium hydroxide (10 mL) and water (30 ml) dropwise, in that order, and stirred for 15 minutes. The mixture was filtered, and filtrate was concentrated. The residue was purified by flash chromatography (0-30% ethyl acetate in petroleum ether) to give the title compound as a colorless oil (14 g, 52%). $^1$HNMR (400 MHz, $CDCl_3$): 5.82 (dd, J=17.6, 10.8 Hz, 1H), 5.16-5.12 (m, 2H), 3.75 (q, J=5.2 Hz, 2H), 3.51 (t, J=6.0 Hz, 2H), 1.81-1.78 (m, 2H), 1.28 (s, 6H).

Intermediate 19C: 3-((2-Methylbut-3-en-2-yl)oxy) propyl 4-methylbenzenesulfonate

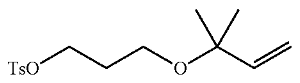 [SMILES: C=CC(C)(C)OCCCOS(=O)(=O)c1ccc(C)cc1]

To a stirred and cooled (0° C.) solution of 3-((2-methylbut-3-en-2-yl)oxy)propan-1-ol (Intermediate 19B, 3.5 g, 24.3 mmol) in 100 mL of dichloromethane was added 4-dimethylaminopyridine (297 mg, 2.43 mmol), 4-methylbenzenesulfonyl chloride (5.55 g, 29.1 mmol) and triethylamine (4 mL, 29.1 mmol). The reaction was stirred at room temperature for 16 hours, then quenched with 50 mL of water and extracted with ethyl acetate (3×30 mL). The combined organic extracts were washed with brine, dried over sodium sulfate, and concentrated. The residue was purified by flash chromatography (eluting with 0-15% ethyl acetate in petroleum ether) to give the title compound as a colorless oil (6 g, 82.8%). MS (ESI): 320 m/z [M+Na]$^+$.

Intermediate 19D: Methyl 2-(3-bromophenyl)-2-methyl-5-((2-methylbut-3-en-2-yl)oxy)pentanoate

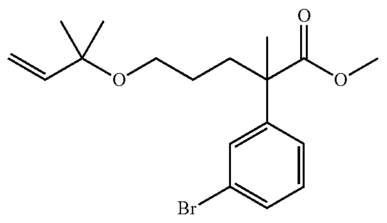 [SMILES: C=CC(C)(C)OCCCC(C)(C(=O)OC)c1cccc(Br)c1]

Exchanging tert-butyl-(2-iodoethoxy)-dimethyl-silane for 3-((2-methylbut-3-en-2-yl)oxy)propyl 4-methylbenzenesulfonate (intermediate 19C, 6.14 g, 20.6 mmol), the reaction procedure described for Intermediate 16 was used to prepare the title compound (5.4 g, 71%). MS (ESI): 391, 393 m/z [M+Na]$^+$.

Intermediate 19E: 2-(3-Bromophenyl)-2-methyl-5-((2-methylbut-3-en-2-yl)oxy)pentanoic Acid

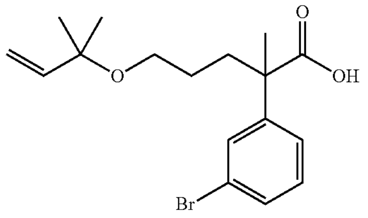 [SMILES: C=CC(C)(C)OCCCC(C)(C(=O)O)c1cccc(Br)c1]

To a stirred solution of methyl 2-(3-bromophenyl)-2-methyl-5-((2-methylbut-3-en-2-yl)oxy)pentanoate (Intermediate 19D, 20.4 g, 55.2 mmol) in 60 mL of tetrahydrofuran/methanol/water (3:1:1) was added lithium hydroxide monohydrate (23.2 g, 552 mmol). The reaction was stirred at 50° C. for 16 hours and then concentrated. The residue was dissolved in 100 mL of water, acidified to pH ~2 with concentrated hydrochloric acid (40 mL) followed by 1N hydrochloric acid (100 mL), and extracted with ethyl acetate (4×200 mL). The combined organic extracts were dried over sodium sulfate and concentrated. The residue was purified by flash chromatography (0-40% of ethyl acetate in petroleum ether) to give the title compound as a yellow oil (17 g, 86%). MS (ESI): 377, 379 m/z [M+Na]$^+$.

Intermediate 19F: 2-(3-Bromophenyl)-N-methoxy-N,2-dimethyl-5-((2-methylbut-3-en-2-yl)oxy)pentanamide

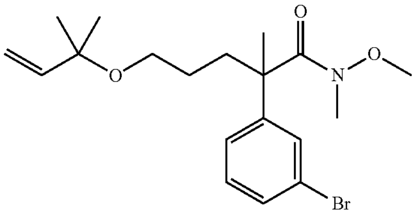 [SMILES: C=CC(C)(C)OCCCC(C)(C(=O)N(C)OC)c1cccc(Br)c1]

To a stirred solution of 2-(3-bromophenyl)-2-methyl-5-((2-methylbut-3-en-2-yl)oxy)pentanoic acid (Intermediate 19E, 20.6 g, 58 mmol) and N,O-dimethyl hydroxylamine hydrochloride (17 g, 174 mmol) in 200 mL of N,N-dimethylformamide was added HATU (33 g, 87 mmol) and triethylamine (2.35 mL, 174 mmol) at room temperature. The reaction was stirred at room temperature for 16 hours, then diluted with 50 mL of water and extracted with ethyl acetate (3×200 mL). The combined organic extracts were washed with brine, dried over sodium sulfate, and concentrated. The residue was purified by flash chromatography (0-20% of ethyl acetate in petroleum ether) to give the title compound as a colorless oil (21.3 g, 92%). MS (ESI): 420, 422 m/z [M+Na]$^+$.

Intermediate 19G: 2-(3-Bromophenyl)-2-methyl-5-((2-methylbut-3-en-2-yl)oxy)pentanal

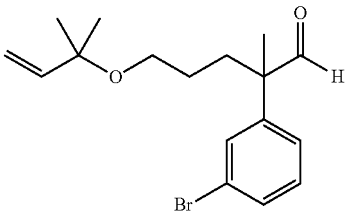 [SMILES: C=CC(C)(C)OCCCC(C)(C=O)c1cccc(Br)c1]

To a stirred and cooled (−78° C.) solution of 2-(3-bromophenyl)-N-methoxy-N,2-dimethyl-5-((2-methylbut-3-en-2-yl)oxy)pentanamide (Intermediate 19F, 21.3 g, 53.5 mmol) in 100 mL of tetrahydrofuran was added lithium aluminum hydride (4 g, 107 mmol). The reaction was stirred at 0° C. for 2 hours. After confirming the starting material was consumed by LCMS analysis, the reaction was diluted with 200 mL of ether, quenched carefully with 4 mL of water, 4 mL of 15% sodium hydroxide solution and 12 mL of water at 0° C. The mixture was filtered. The filter cake was washed with ethyl acetate (3×20 mL). The combined filtrate was dried and concentrated. The residue was purified by flash chromatography (0-20% of ethyl acetate in petroleum ether) to give the title compound as a colorless oil (15 g, 82%). MS (ESI): 361, 363 m/z $[M+Na]^+$.

Intermediate 19H: 3-(3-Bromophenyl)-3-methyl-6-((2-methylbut-3-en-2-yl)oxy)hexan-2-ol

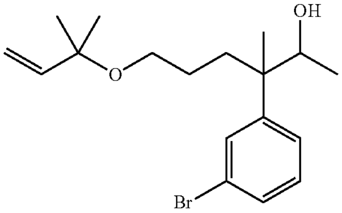 [SMILES: C=CC(C)(C)OCCCC(C)(c1cccc(Br)c1)C(C)O]

To a stirred and cooled (0° C.) solution of 2-(3-bromophenyl)-2-methyl-5-((2-methylbut-3-en-2-yl)oxy)pentanal (Intermediate 19G, 1.2 g, 3.54 mmol) in 10 mL of tetrahydrofuran was added methyl magnesium chloride (1.77 mL, 5.31 mmol, 3 M in tetrahydrofuran). The reaction was stirred at 0° C. for 1 hour, then quenched with 10 mL of water and extracted with ethyl acetate (3×20 mL). The combined organic extracts were dried over sodium sulfate and concentrated. The residue was purified by silica gel flash chromatography (0-30% of ethyl acetate in petroleum ether) to give the title compound as a colorless oil (1.07 g, 86%). $^1$H NMR (400 MHz, $CDCl_3$) δ: 7.50-7.17 (m, 4H), 5.80 (dd, J=11.2, 17.6 Hz, 1H), 5.11-5.07 (m, 2H), 3.88-3.84 (m, 1H), 3.23-3.19 (m, 2H), 1.84-1.36 (m, 4H), 1.28-1.23 (m, 9H), 1.08-0.94 (m, 3H) ppm.

Intermediate 19I: 3-(3-Bromophenyl)-3-methyl-6-((2-methylbut-3-en-2-yl)oxy)hexan-2-one

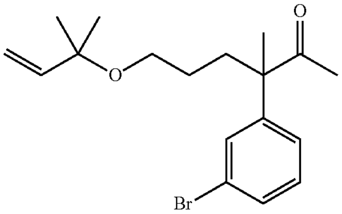 [SMILES: C=CC(C)(C)OCCCC(C)(C(C)=O)c1cccc(Br)c1]

To a stirred solution of 3-(3-bromophenyl)-3-methyl-6-((2-methylbut-3-en-2-yl)oxy)hexan-2-ol (Intermediate 19H, 9.8 g, 27.6 mmol) in 100 mL of dimethyl sulfoxide was added 2-iodoxybenzoic acid (23.2 g, 82.8 mmol). The reaction was stirred at room temperature for 3 hours, then diluted with 200 mL of water and extracted with ethyl acetate (3×200 mL). The combined organic extracts were washed with saturated sodium bicarbonate, dried over sodium sulfate, and concentrated. The residue was purified by silica gel flash chromatography (0-15% ethyl acetate in petroleum ether) to give the title compound as a yellow oil (7.1 g, 73%). MS (ESI): 375, 377 m/z $[M+Na]^+$.

The following intermediate was prepared based on the procedures described for Intermediate 19I.

| Inter. No. | Structure | Name | MS m/z $[M + H]^+$ |
|---|---|---|---|
| 19I-1 | 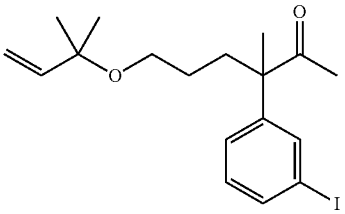 [SMILES: C=CC(C)(C)OCCCC(C)(C(C)=O)c1cccc(I)c1] | 3-(3-iodophenyl)-3-methyl-6-((2-methylbut-3-en-2-yl)oxy)hexan-2-one | 423 |

Intermediate 19J: 2-((4-(3-bromophenyl)-4-methyl-5-oxohexyl)oxy)-2-methylpropanal

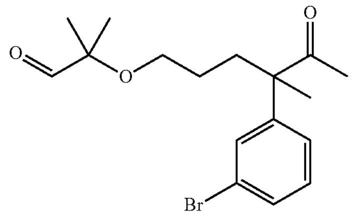 [SMILES: CC(=O)C(C)(CCCOC(C)(C)C=O)c1cccc(Br)c1]

To a stirred and cooled (−78° C.) solution of 3-(3-bromophenyl)-3-methyl-6-((2-methylbut-3-en-2-yl)oxy)hexan-2-one (Intermediate 19I, 5.0 g, 0.014 mol) in dichloromethane (150 mL) was bubbled ozone for 10 minutes. The reaction was quenched with dimethyl sulfite (4.40 g, 0.071 mol), warmed to room temperature, stirred for 16 hours, and concentrated to give the title compound as a yellow oil. MS (ESI): 377, 379 m/z $[M+Na]^+$.

Intermediate 19K: 2-((4-(3-Bromophenyl)-4-methyl-5-oxohexyl)oxy)-2-methylpropanoic acid

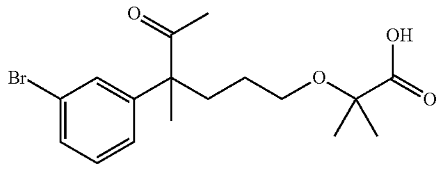 [SMILES: CC(=O)C(C)(CCCOC(C)(C)C(=O)O)c1cccc(Br)c1]

To a stirred mixture of 2-((4-(3-bromophenyl)-4-methyl-5-oxohexyl)oxy)-2-methylpropanal (Intermediate 19J, 5.0 g, 0.014 mol), sodium phosphate monobasic (5.07 g, 0.042 mol) in 75 mL of tert-butanol/tetrahydrofuran/water (1:1:1) was added sodium chlorite (3.8 g, 0.042 mol). The mixture was stirred at room temperature for 2 hours then extracted with ethyl acetate (3×100 mL). The combined organic extracts were dried over sodium sulfate and concentrated. The residue was purified by Prep-HPLC (0-90% acetonitrile in water with 1% 0.1M ammonium bicarbonate as modifier) to give the title compound as a yellow oil (5.0 g, crude). MS (ESI): 393, 395 m/z $[M+Na]^+$.

Intermediate 19L: Methyl 2-((4-(3-bromophenyl)-4-methyl-5-oxohexyl)oxy)-2-methylpropanoate

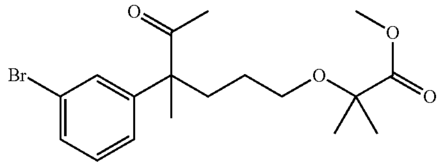 [SMILES: COC(=O)C(C)(C)OCCCC(C)(C(C)=O)c1cccc(Br)c1]

To a stirred and cooled (0° C.) solution of 2-((4-(3-bromophenyl)-4-methyl-5-oxohexyl)oxy)-2-methylpropanoic acid (Intermediate 19K, 3 g, 0.0081 mol) in dichloromethane (50 mL) was added a few drops of dimethylformamide and oxalyl chloride (3.08 g, 0.024 mol).

The reaction was stirred for 2 hours, then methanol (50 mL) was added and stirred for another 2 hours. The mixture was concentrated and purified by silica gel column chromatography (20% ethyl acetate in petroleum ether) to give the title compound as a yellow oil (2.9 g, 93%). MS (ESI): 407, 409 m/z $[M+Na]^+$.

Intermediate 20: 6-Fluoro-5-(4-fluoro-3-(4,4,5,5-tetramethyl-1,3,2-dioxaborolan-2-yl)phenoxy)-4-vinyl-1H-indole

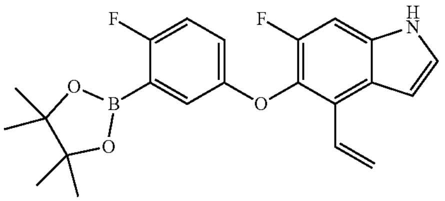 [SMILES: C=Cc1c(Oc2ccc(F)c(B3OC(C)(C)C(C)(C)O3)c2)c(F)cc2[nH]ccc12]

To a stirred solution of 5-(3-bromo-4-fluoro-phenoxy)-6-fluoro-4-vinyl-1H-indole (Intermediate 20D, 10.00 g, 28.6 mmol) in 1,4-dioxane (200 mL) was added 4,4,5,5-tetramethyl-2-(4,4,5,5-tetramethyl-1,3,2-dioxaborolan-2-yl)-1,3,2-dioxaborolane (10.90 g, 42.8 mmol), potassium acetate (5.61 g, 57.1 mmol) and $PdCl_2$(dppf) (2.33 g, 2.86 mmol). The reaction mixture was purged with argon and stirred at 85° C. for 16 hours. The reaction mixture was diluted with ethyl acetate (300 mL). The organic solution was washed with water (2×300 mL), dried over anhydrous sodium sulfate, filtered, and concentrated. The crude residue was purified by flash chromatography (120 g silica gel column, 0-15% ethyl acetate in petroleum ether) to give the title compound as a yellow solid (9.10 g, 80%). MS (ESI): 398 m/z $[M+H]^+$.

Intermediate 20A: 1,2-Difluoro-4-methyl-5-nitro-3-vinylbenzene

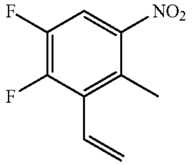

To a stirred solution of 3-bromo-1,2-difluoro-4-methyl-5-nitro-benzene (Intermediate 2A, 30.00 g, 119 mmol) in dioxane (400 mL) and water (100 mL) was added $PdCl_2$(dppf) (9.72 g, 11.9 mmol), cesium carbonate (77.6 g, 238.0 mmol) and 4,4,5,5-tetramethyl-2-vinyl-1,3,2-dioxaborolane (36.70 g, 238.0 mmol). The reaction mixture was purged with argon and stirred at 100° C. for 16 hours. The mixture was diluted with ethyl acetate (500 mL), washed with water (300 mL×2), dried over anhydrous sodium sulfate, filtered, and concentrated. The crude residue was purified by flash chromatography (330 g silica gel column, 0-10% ethyl acetate in petroleum ether) to afford the title compound (18.50 g, 78%). MS (ESI): 200 m/z $[M+H]^+$.

Intermediate 20B: 2-(3-Bromo-4-fluorophenoxy)-1-fluoro-4-methyl-5-nitro-3-vinylbenzene

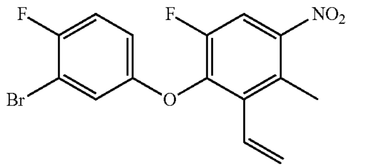 [SMILES: C=Cc1c(C)c([N+](=O)[O-])cc(F)c1Oc1ccc(F)c(Br)c1]

To a stirred solution of 1,2-difluoro-4-methyl-5-nitro-3-vinylbenzene (Intermediate 20A, 18.50 g, 92.9 mmol) in N,N-dimethylformamide (200 mL) was added 3-bromo-4-fluoro-phenol (17.70 g, 92.9 mmol) and potassium carbonate (25.70 g, 186.0 mmol). The reaction was stirred at 100° C. for 2 hours. The mixture was diluted with ethyl acetate (300 mL), washed with water (3×300 mL), dried over anhydrous magnesium sulfate and concentrated. The crude residue was purified by automated flash chromatography (330 g silica gel column, 0-10% ethyl acetate in petroleum) to give the title compound as an oil (28.00 g, 81%). MS (ESI): 370 m/z $[M+H]^+$.

The following intermediates were prepared based on the procedures described for Intermediates 20B.

| Inter. No. | Structure | Name | MS m/z $[M + H]^+$ |
| --- | --- | --- | --- |
| 20B-1 | 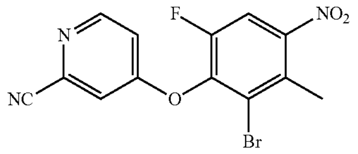 [SMILES: Cc1c([N+](=O)[O-])cc(F)c(Oc2ccnc(C#N)c2)c1Br] | 4-(2-bromo-6-fluoro-3-methyl-4-nitrophenoxy) picolinonitrile | 352, 354 [M + H]; RT 1.88 min. (LC-MS method 4) |
| 20B-2 | 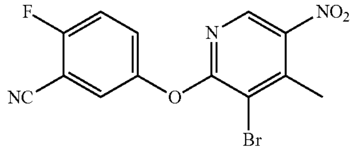 [SMILES: Cc1c([N+](=O)[O-])cnc(Oc2ccc(F)c(C#N)c2)c1Br] | 5-((3-bromo-4-methyl-5-nitropyridin-2-yl)oxy)-2-fluorobenzonitrile | Mass not observed. RT 1.75 min. (LC-MS method 40) |

Intermediate 20C: (E)-2-(3-(3-Bromo-4-fluorophenoxy)-4-fluoro-6-nitro-2-vinylphenyl)-N,N-dimethylethen-1-amine

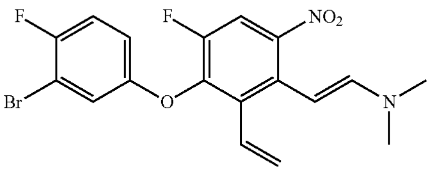 [SMILES: C=Cc1c(/C=C/N(C)C)c([N+](=O)[O-])cc(F)c1Oc1ccc(F)c(Br)c1]

To a stirred solution of 2-(3-bromo-4-fluoro-phenoxy)-1-fluoro-4-methyl-5-nitro-3-vinyl-benzene (Intermediate 20B, 28.00 g, 75.6 mmol) in N,N-dimethylformamide (200 mL) was added N,N-dimethylformamide dimethyl acetal (50.2 mL, 378 mmol) at room temperature. The reaction was stirred at 100° C. for 16 hours. The mixture was diluted with water and extracted with ethyl acetate (300 mL). The organic solution was washed with brine (300 mL×2), dried over anhydrous sodium sulfate and concentrated to give the crude title compound as an oil (31.0 g, 96%).

Intermediate 20D: 5-(3-Bromo-4-fluorophenoxy)-6-fluoro-4-vinyl-1H-indole

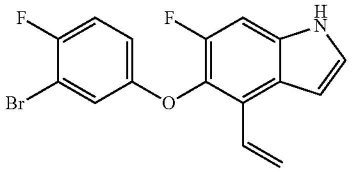 [SMILES: C=Cc1c(Oc2ccc(F)c(Br)c2)c(F)cc2[nH]ccc12]

To a stirred solution of (E)-2-(3-(3-bromo-4-fluorophenoxy)-4-fluoro-6-nitro-2-vinylphenyl)-N,N-dimethylethen-1-amine (Intermediate 20C, 31.00 g, 72.9 mmol) in toluene (150 mL) and acetic acid (150 mL) was added iron powder (40.70 g, 729 mmol). The reaction mixture was stirred for 16 hours at 100° C. The solid was removed by filtration and rinsed with ethyl acetate (200 mL). The filtrate was washed with water (3×300 mL). The organic solution was dried over anhydrous sodium sulfate and concentrated. The crude residue was purified by flash chromatography (330 g silica gel column, 0-15% ethyl acetate in petroleum ether) to give the title compound as an oil (15.50 g, 61%). MS (ESI): 350, 352 m/z $[M+H]^+$.

Intermediate 21: 6-Fluoro-5-(4-fluoro-3-(1H-pyrazol-3-yl)phenoxy)-1-tosyl-4-vinyl-1H-indole

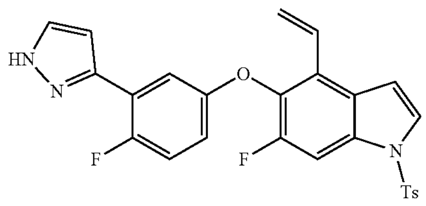 [SMILES: C=Cc1c(Oc2ccc(F)c(-c3cc[nH]n3)c2)c(F)cc2c1ccn2S(=O)(=O)c1ccc(C)cc1]

To a stirred solution of 4-bromo-6-fluoro-5-(4-fluoro-3-(1H-pyrazol-3-yl)phenoxy)-1-tosyl-1H-indole (Intermediate 21D, 9.00 g, 16.5 mmol) in dioxane/water (250 mL, 4/1 v/v) was added 4,4,5,5-tetramethyl-2-vinyl-1,3,2-dioxaborolane (5.09 g, 33 mmol), cesium carbonate (10.80 g, 33.0 mmol) and 1,1'-bis(diphenylphosphino)ferrocene-palladium (II)dichloride dichloromethane complex (1.35 g, 1.65 mmol) at room temperature. The reaction was stirred at 100° C. under nitrogen atmosphere overnight. The mixture was diluted with ethyl acetate, washed with water, dried over sodium sulfate, and concentrated. The crude residue was purified by silica gel column chromatography (80 g silica gel column, 0-60% ethyl acetate in petroleum ether) to give the title compound as a yellow solid (6.14 g, 69%). MS (ESI): 492 m/z $[M+H]^+$.

Intermediate 21A: 1-(5-((4-Bromo-6-fluoro-1H-indol-5-yl)oxy)-2-fluorophenyl)ethan-1-one

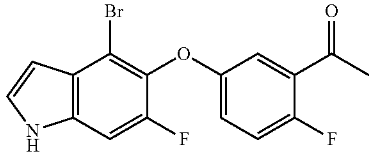 [SMILES: CC(=O)c1cc(Oc2c(F)cc3[nH]ccc3c2Br)ccc1F]

Methyl magnesium bromide (3.0 M in ether) (17.2 mL, 51.6 mmol) was added to a solution of 5-((4-bromo-6-fluoro-1H-indol-5-yl)oxy)-2-fluorobenzonitrile (Intermediate 2, 6.00 g, 17.2 mmol) in 132 mL of toluene and tetrahydrofuran (10:1). The mixture was heated to reflux and stirred for 10 minutes. The reaction was quenched with saturated aqueous ammonium chloride (50 mL) and extracted with ethyl acetate (2×100 mL). The combined organic extracts were washed with brine (50 mL), dried over sodium sulfate and concentrated. The crude residue was purified by flash chromatography (80 g silica gel column, 0-30% ethyl acetate in petroleum ether) to give the title compound as a solid (4.10 g, 59%). MS (ESI): 366 m/z $[M+H]^+$.

Intermediate 21B: 1-(5-((4-Bromo-6-fluoro-1-tosyl-1H-indol-5-yl)oxy)-2-fluorophenyl)ethan-1-one

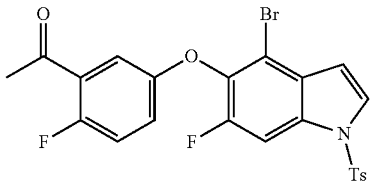 [SMILES: CC(=O)c1cc(Oc2c(F)cc3c(ccn3S(=O)(=O)c3ccc(C)cc3)c2Br)ccc1F]

To a stirred solution of 1-(5-((4-bromo-6-fluoro-1H-indol-5-yl)oxy)-2-fluorophenyl)ethan-1-one (Intermediate 21A, 12.8 g, 35 mmol) in 150 mL N,N-dimethylformamide was added 60% sodium hydride (2.10 g, 52.4 mmol). The mixture was stirred at 0° C. for 1 hour. Tosyl chloride (10.00 g, 52.4 mmoL) was added portion wise. The mixture was stirred at room temperature for 2 hours. After confirming that the starting material was consumed by LC-MS analysis, the reaction was quenched with saturated aqueous ammonium chloride (100 mL). The mixture was extracted with ethyl acetate (2×250 mL). The combined organic phases were washed with water (3×150 mL) and brine (100 mL), dried over sodium sulfate and concentrated. The crude residue was purified by silica gel column chromatography (120 g silica gel column, 0-20% ethyl acetate in petroleum ether) to afford the title compound as a solid (14.50 g, 79%). MS (ESI): 520, 522 m/z $[M+H]^+$.

The following intermediate was prepared based on the procedures described for Intermediate 21B.

| Inter. No. | Structure | Name | MS m/z $[M + H]^+$ |
|---|---|---|---|
| 21B-1 | 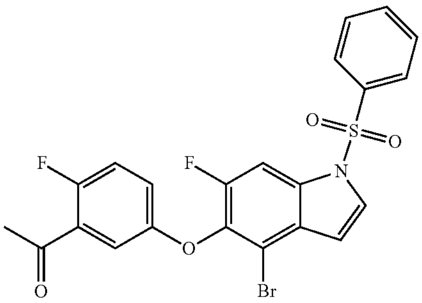 [SMILES: CC(=O)c1cc(Oc2c(F)cc3c(ccn3S(=O)(=O)c3ccccc3)c2Br)ccc1F] | 1-(5-((4-bromo-6-fluoro-1-(phenylsulfonyl)-1H-indol-5-yl)oxy)-2-fluorophenyl)ethan-1-one | 506, 508 [M + H]; RT 2.10 min. (LC-MS method 4) |
| 21B-2 | 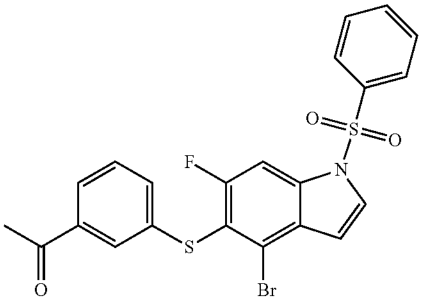 [SMILES: CC(=O)c1cccc(Sc2c(F)cc3c(ccn3S(=O)(=O)c3ccccc3)c2Br)c1] | 1-(3-((4-bromo-6-fluoro-1-(phenylsulfonyl)-1H-indol-5-yl)thio)phenyl)ethan-1-one | 504, 506 [M + H]; RT 2.10 min. (LC-MS method 4) |

Intermediate 21C: (E)-1-(5-((4-Bromo-6-fluoro-1-tosyl-1H-indol-5-yl)oxy)-2-fluorophenyl)-3-(dimethylamino)prop-2-en-1-one

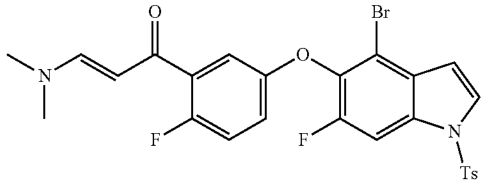 [SMILES: Cc1ccc(S(=O)(=O)n2ccc3c(Br)c(Oc4ccc(F)c(C(=O)/C=C/N(C)C)c4)c(F)cc32)cc1]

To a solution of 1-(5-((4-bromo-6-fluoro-1-tosyl-1H-indol-5-yl)oxy)-2-fluorophenyl)ethan-1-one (Intermediate 21B, 14.30 g, 27.5 mmol) in N,N-dimethylformamide (150 mL) was added 1,1-dimethoxy-N,N-dimethyl-methanamine (13.10 g, 110.0 mmol). The reaction was stirred at 90° C. overnight. The mixture was diluted with ethyl acetate (600 mL), washed with water (2×300 mL), brine (100 mL), dried over sodium sulfate and concentrated to give the crude title compound as a yellow solid (15.60 g, crude). MS (ESI): 575, 577 m/z $[M+H]^+$.

Intermediate 21D: 4-Bromo-6-fluoro-5-(4-fluoro-3-(1H-pyrazol-3-yl)phenoxy)-1-tosyl-1H-indole

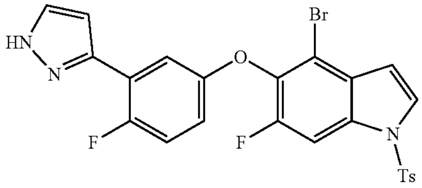 [SMILES: Cc1ccc(S(=O)(=O)n2ccc3c(Br)c(Oc4ccc(F)c(-c5cc[nH]n5)c4)c(F)cc32)cc1]

To a solution of (E)-1-(5-((4-bromo-6-fluoro-1-tosyl-1H-indol-5-yl)oxy)-2-fluorophenyl)-3-(dimethylamino)prop-2-en-1-one (Intermediate 21C, 15.60 g, 27.1 mmol) in ethanol (250 mL) and tetrahydrofuran (25 mL) was added hydrazine hydrate (5.26 mL, 108 mmol). The reaction was stirred at 50° C. for 3 hours. The mixture was diluted with ethyl acetate, washed with water, dried over sodium sulfate, and concentrated. The crude residue was purified by silica gel column chromatography (120 g silica gel column, 0-60% ethyl acetate in petroleum ether) to give the title compound as a yellow solid (9.65 g, 65%). MS (ESI): 544, 546 m/z $[M+H]^+$.

The following intermediates were prepared based on the procedures described for Intermediate 21.

| Inter. No. | Structure | Name | MS m/z $[M + H]^+$ |
|---|---|---|---|
| 21-1 | 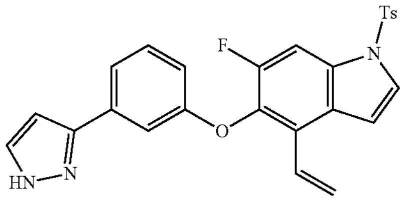 [SMILES: C=Cc1c(Oc2cccc(-c3cc[nH]n3)c2)c(F)cc2c1ccn2S(=O)(=O)c1ccc(C)cc1] | 5-(3-(1H-pyrazol-3-yl)phenoxy)-6-fluoro-1-tosyl-4-vinyl-1H-indole | 474 |
| 21-2 | 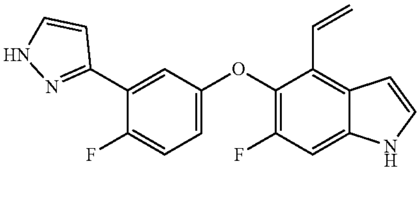 [SMILES: C=Cc1c(Oc2ccc(F)c(-c3cc[nH]n3)c2)c(F)cc2[nH]ccc12] | 6-Fluoro-5-(4-fluoro-3-(1H-pyrazol-3-yl)phenoxy)-4-vinyl-1H-indole | 338 |
| 21-3 | 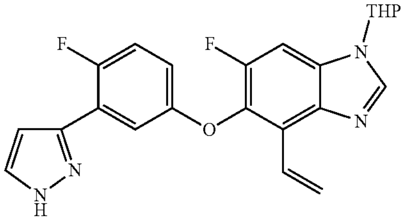 | 6-fluoro-5-(4-fluoro-3-(1H-pyrazol-3-yl)phenoxy)-1-(tetrahydro-2H-pyran-2-yl)-4-vinyl-1H-benzo[d]imidazole | MS: 423; $^1$H NMR (500 MHz, DMSO-$d_6$) δ 12.99 (br, 1H), 8.56 (s, 1H), 7.81 (s, 1H), 7.76 (d, J = 10.5 Hz, 1H), 7.32-7.30 (m, 1H), 7.26 (d, J = 10.0 Hz, 1H), 7.03-6.92 (m, 3H), 6.62 (s, 1H), 5.71 (dd, J = 10.5, 2.5 Hz, 1H), 5.66 (dd, J = 11.0, 3.5 Hz, 1H), 4.00 (d, J = 11.5 Hz, 1H), 3.78 (dt, J = 11.5, 3.5 Hz, 1H), 2.23-2.20 (m, 1H), 2.07-1.99 (m, 2H), 1.75-1.61 (m, 3H) ppm. |

Intermediate 22: 6-Fluoro-5-[3-(1H-pyrazol-3-yl)phenoxy]-4-vinyl-1H-indole

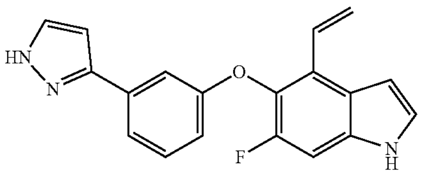 [SMILES: C=Cc1c(Oc2cccc(-c3cc[nH]n3)c2)c(F)cc2[nH]ccc12]

To a solution of 5-(3-(1H-pyrazol-3-yl)phenoxy)-4-bromo-6-fluoro-1H-indole (Intermediate 22D, 1.67 g, 4.49 mmol) in dioxane (60 mL) and water (15 mL) was added vinylboronic acid pinacol ester (1.38 g, 8.97 mmol), cesium carbonate (2.92 g, 8.97 mmol) and 1,1'-bis(diphenylphosphino)-ferrocene-palladium(II)dichloride dichloromethane complex (0.37 g, 0.045 mmol). The mixture was heated at 100° C. for 16 hours, then cooled to room temperature and diluted with water (100 mL). The mixture was extracted with ethyl acetate (4×50 mL). The combined ethyl acetate layers were washed with brine (100 mL), dried over sodium sulfate, filtered, and concentrated to afford the title compound (4.5 g, 82%). MS (ESI): 320 m/z $[M+H]^+$.

Intermediate 22A: 3-(1-(Tetrahydro-2H-pyran-2-yl)-1H-pyrazol-3-yl)phenol

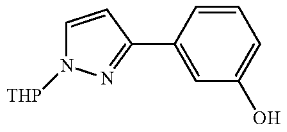

To the solution of 3-bromophenol (20.00 g, 120.0 mmol) in dioxane (120 mL) and water (30 mL) was added 1-tetrahydropyran-2-yl-3-(4,4,5,5-tetramethyl-1,3,2-dioxaborolan-2-yl)pyrazole (38.6 g, 140.0 mmol), $Pd(PPh_3)_2Cl_2$ (4.06 g, 5.08 mmol) and potassium phosphate (73.60 g, 350.0 mmol) under argon. The reaction mixture was stirred at 80° C. for 16 hours. The reaction mixture was diluted with water (50 mL) and extracted with ethyl acetate (4×100 mL). The combined organic extracts were washed with brine (100 mL), dried over sodium sulfate and concentrated. The crude residue was subjected to automated flash chromatography to afford the title compound (25.00 g, 83%). MS (ESI): 267 m/z $[M+Na]^+$.

Intermediate 22B: 3-(3-(2-Bromo-6-fluoro-3-methyl-4-nitrophenoxy)phenyl)-1-(tetrahydro-2H-pyran-2-yl-1H-pyrazole

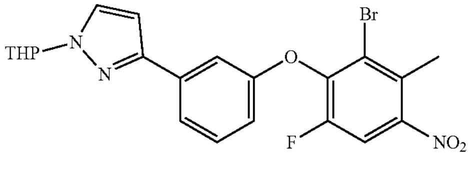

To the solution of 3-(1-tetrahydropyran-2-ylpyrazol-3-yl)phenol (Intermediate 22A, 7.60 g, 31.1 mmol) in N,N-dimethylformamide (30 mL) was added 3-bromo-1,2-difluoro-4-methyl-5-nitro-benzene (7.84 g, 31.1 mmol) and potassium carbonate (8.6 g, 62.2 mmol). The reaction mixture was stirred at 100° C. for 2 hours. Next, the reaction was cooled to room temperature, quenched with water (100 mL). The aqueous solution was extracted with ethyl acetate (100 mL×3). The extract was washed with water (3×50 mL) and brine (2×50 mL), dried over sodium sulfate and concentrated. The crude material was purified by automated flash chromatography to afford the title compound (34.00 g, 70%). $^1H$ NMR (400 MHz, DMSO-$d_6$) δ 8.29 (d, J=10.0 Hz, 1H), 7.58-7.50 (m, 2H), 7.31 (d, J=7.6 Hz, 1H), 7.18 (dd, J=8.0, 2.4 Hz, 1H), 7.03 (s, 1H), 6.48 (d, J=1.6 Hz, 1H), 5.09 (dd, J=9.6, 1.6 Hz, 1H), 3.77 (d, J=11.6 Hz, 1H), 3.29-3.20 (m, 1H), 2.52 (s, 3H), 2.42-2.27 (m, 1H), 1.99-1.91 (m, 1H), 1.75 (d, J=24.8 Hz, 1H), 1.53-1.49 (m, 3H) ppm.

Intermediate 22C: (E)-2-(2-Bromo-4-fluoro-6-nitro-3-(3-(1-(tetrahydro-2H-pyran-2-yl)-1H-pyrazol-3-yl)phenoxy)phenyl)-N,N-dimethylethen-1-amine

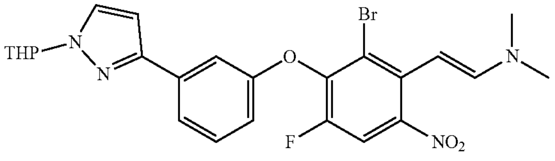

To a solution of 3-(3-(2-bromo-6-fluoro-3-methyl-4-nitrophenoxy)phenyl)-1-(tetrahydro-2H-pyran-2-yl)-1H-pyrazole (Intermediate 22B, 5.00 g, 10.5 mmol) in N,N-dimethylformamide (30 mL) was added N,N-dimethylformamide dimethyl acetal (6.25 g, 52.5 mmol). The reaction mixture was heated at 100° C. for 15 hours. The reaction mixture was diluted with water. The aqueous solution was extracted with ethyl acetate (4×100 mL). The combined ethyl acetate layer was washed with water (2×100 mL), followed by brine (100 mL), and then dried over sodium sulfate, filtered, and concentrated to afford the title compound (5.60 g, 100%). MS (ESI): not observed.

Intermediate 22D: 5-(3-(1H-Pyrazol-3-yl)phenoxy)-4-bromo-6-fluoro-1H-indole

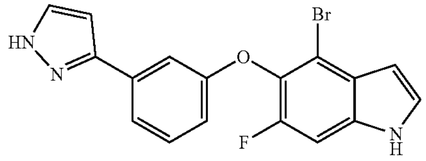 [SMILES: Fc1cc2[nH]ccc2c(Br)c1Oc1cccc(-c2cc[nH]n2)c1]

To a stirred solution of (E)-2-(2-bromo-4-fluoro-6-nitro-3-(3-(1-(tetrahydro-2H-pyran-2-yl)-1H-pyrazol-3-yl)phenoxy)phenyl)-N,N-dimethylethen-1-amine (Intermediate 22C, 32.00 g, 60.2 mmol) in acetic acid (150 mL) and toluene (150 mL) was added iron powder (5.90 g, 0.11 mol). The reaction mixture was stirred at 100° C. for 16 hours, then cooled to room temperature, diluted with water (100 mL) and ethyl acetate (100 mL). The mixture was filtered. The filter cake was washed with ethyl acetate (3×100 mL). The separated organic layer in the filtrate was combined with additional ethyl acetate extracts (2×200 mL) of the aqueous layer, washed with brine (100 mL), dried over sodium sulfate and concentrated. The crude residue was purified by automated flash chromatography to afford the title compound (4.44 g, 16%). MS (ESI): 372 m/z $[M+H]^+$.

Intermediate 23: 2-Fluoro-5-((6-fluoro-1-tosyl-4-vinyl-1H-indol-5-yl)oxy)benzamide

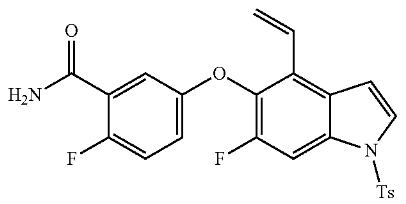 [SMILES: C=Cc1c(Oc2ccc(F)c(C(N)=O)c2)c(F)cc2c1ccn2S(=O)(=O)c1ccc(C)cc1]

To a stirred and cooled (0° C.) solution of 2-fluoro-5-((6-fluoro-4-vinyl-1H-indol-5-yl)oxy)benzamide (Intermediate 23A, 2.70 g, 8.59 mmol) in tetrahydrofuran (96 mL) was added sodium hydride (395 mg, 10.3 mmol). After 30 minutes, 4-methylbenzenesulfonyl chloride (2.46 g, 12.9 mmol) was added portion wise. The reaction was stirred at room temperature for 16 hours, then quenched with saturated aqueous ammonium chloride. The mixture was extracted with ethyl acetate (3×100 mL). The combined organic extracts were dried over sodium sulfate and concentrated. The crude residue was purified by silica gel column chromatography (petroleum ether: ethyl acetate=10:1) to give the title compound as a yellow solid (3.30 g, 75%). MS (ESI): 469 m/z $[M+H]^+$.

Intermediate 23A: 2-Fluoro-5-((6-fluoro-4-vinyl-1H-indol-5-yl)oxy)benzamide

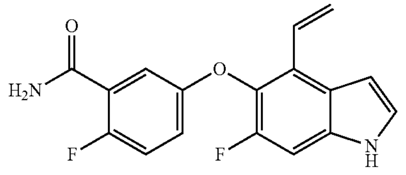 [SMILES: C=Cc1c(Oc2ccc(F)c(C(N)=O)c2)c(F)cc2[nH]ccc12]

To a stirred solution of 2-fluoro-5-((6-fluoro-4-vinyl-1H-indol-5-yl)oxy)benzonitrile (Intermediate 6-1, 3.10 g, 10.5 mmol) in ethanol (103 mL) and water (31 mL) was added hydrogen peroxide (8.3 g, 7.32 mmol) and sodium hydroxide (1.26 g, 3.14 mmol). The mixture was stirred at room temperature for 16 hours, then diluted with brine (100 mL). To this solution was added 1M hydrochloric acid (20 mL). The mixture was extracted with ethyl acetate (3×100 mL). The combined organic layers were washed with saturated aqueous sodium bicarbonate (100 mL), brine (100 mL), dried (sodium sulfate) and concentrated to give the crude title compound as a yellow solid (2.70 g, 74.5%). MS (ESI): 315 m/z $[M+H]^+$.

Intermediate 24: 6-Fluoro-5-(4-fluoro-3-(4-methyl-1H-pyrazol-3-yl)phenoxy)-1-tosyl-4-vinyl-1H-indole

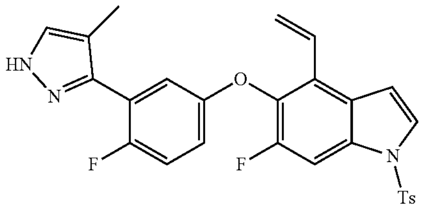 [SMILES: C=Cc1c(Oc2ccc(F)c(-c3n[nH]cc3C)c2)c(F)cc2c1ccn2S(=O)(=O)c1ccc(C)cc1]

To a stirred solution of 4-bromo-6-fluoro-5-(4-fluoro-3-(4-methyl-1H-pyrazol-3-yl)phenoxy)-1-tosyl-1H-indole (Intermediate 24D, 3.1 g, 5.55 mmol) in 1,4-dioxane (30 mL) and water (6 mL) were added 4,4,5-trimethyl-2-vinyl-1,3,2-dioxaborolane (1.17 g, 8.33 mmol), [1,1'-bis(diphenylphosphino)ferrocene]dichloropalladium(II) (406 mg, 0.555 mmol) and cesium carbonate (5.43 g, 16.7 mmol) under nitrogen. The reaction was stirred at 100° C. overnight, cooled to room temperature and diluted with water (80 mL). The mixture was then extracted with ethyl acetate (3×80 mL). The combined organic phases were washed with brine, dried over sodium sulfate, and concentrated. The crude material was purified by silica gel column chromatography (50% ethyl acetate in petroleum ether) to give the title compound as a yellow solid (2.30 g, 82.0%). MS (ESI): 506 m/z $[M+H]^+$.

Intermediate 24A: 1-(5-((4-Bromo-6-fluoro-1H-indol-5-yl)oxy)-2-fluorophenyl)propan-1-one

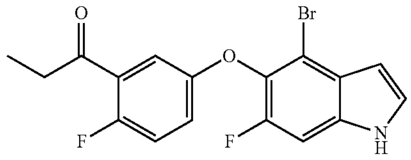 [SMILES: CCC(=O)c1cc(Oc2c(F)cc3[nH]ccc3c2Br)ccc1F]

To a stirred solution of 5-((4-bromo-6-fluoro-1H-indol-5-yl)oxy)-2-fluorobenzonitrile (Intermediate 2, 5.00 g, 14.3 mmol) in toluene (30 mL) and tetrahydrofuran (6 mL) was added ethyl magnesium bromide (1M in THF, 43 mL, 43 mmol) at 0° C. under nitrogen atmosphere. The mixture was then stirred at 120° C. for 30 minutes, cooled to room temperature and quenched with water (80 mL). The aqueous solution was extracted with ethyl acetate (3×80 mL). The combined organic phases were washed with brine, dried over sodium sulfate, and concentrated. The crude was purified by silica gel column chromatography (25% ethyl acetate in petroleum ether) to give the title compound as a yellow solid (2.60 g, 48%). MS (ESI): 380, 382 m/z $[M+H]^+$.

Intermediate 24B: 1-(5-((4-Bromo-6-fluoro-1-tosyl-1H-indol-5-yl)oxy)-2-fluorophenyl)propan-1-one

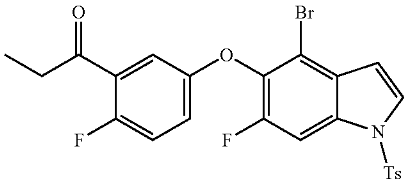 [SMILES: CCC(=O)c1cc(Oc2c(F)cc3c(ccn3S(=O)(=O)c3ccc(C)cc3)c2Br)ccc1F]

To a stirred and cooled (0° C.) solution of 1-(5-((4-bromo-6-fluoro-1H-indol-5-yl)oxy)-2-fluorophenyl)propan-1-one (Intermediate 24A, 4.70 g, 12.4 mmol) in N,N-dimethylformamide (40 mL) was added sodium hydride (0.445 g, 18.5 mmol). The reaction was stirred for 1 hour. Then 4-methylbenzenesulfonyl chloride (3.54 g, 18.5 mmol) was added and the mixture was stirred at room temperature overnight, then quenched with water (200 mL). The resulting solid was collected by filtration and the filter cake was washed with 15% ethyl acetate in petroleum ether to give the crude title compound as a yellow solid (5.40 g, 81.7%). MS (ESI): 556, 558 m/z $[M+Na]^+$.

Intermediate 24C: (E)-1-(5-((4-Bromo-6-fluoro-1-tosyl-1H-indol-5-yl)oxy)-2-fluorophenyl)-3-(dimethylamino)-2-methylprop-2-en-1-one

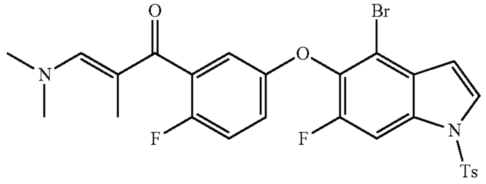 [SMILES: C/C(=C\N(C)C)C(=O)c1cc(Oc2c(F)cc3c(ccn3S(=O)(=O)c3ccc(C)cc3)c2Br)ccc1F]

To a stirred solution of 1-(5-((4-bromo-6-fluoro-1-tosyl-1H-indol-5-yl)oxy)-2-fluorophenyl)propan-1-one (Intermediate 24B, 4.40 g, 8.23 mmol) in N,N-dimethylformamide (25 mL) was added N,N-dimethylformamide dimethyl acetal (1.18 g, 9.88 mmol). The reaction was stirred at 90° C. overnight, cooled to room temperature and quenched with water (80 mL). The solid was collected by filtration to give the crude title compound as a yellow solid (4.75 g, 97.9%). MS (ESI): 589, 590 m/z $[M+H]^+$.

Intermediate 24D: 4-Bromo-6-fluoro-5-(4-fluoro-3-(4-methyl-1H-pyrazol-3-yl)phenoxy)-1-tosyl-1H-indole

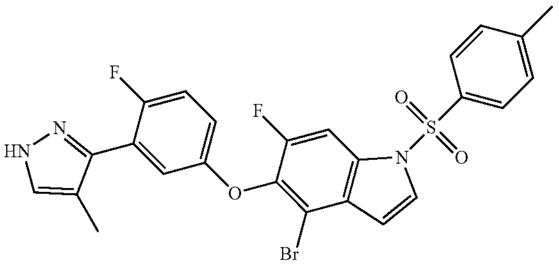 [SMILES: Cc1ccc(S(=O)(=O)n2ccc3c(Br)c(Oc4ccc(F)c(-c5n[nH]cc5C)c4)c(F)cc32)cc1]

To a stirred solution of (E)-1-(5-((4-bromo-6-fluoro-1-tosyl-1H-indol-5-yl)oxy)-2-fluorophenyl)-3-(dimethylamino)-2-methylprop-2-en-1-one (Intermediate 24C, 4.75 g, 8.06 mmol) in ethanol (25 mL) and tetrahydrofuran (25 mL) was added hydrazine hydrate (1.60 mL, 32.2 mmol). The reaction mixture was then stirred at 50° C. for 2 hours, cooled to room temperature and quenched with water (80 mL). This solution was then extracted with ethyl acetate (3×80 mL). The combined organic phases were washed with brine, dried over sodium sulfate, and concentrated. The crude was purified by silica gel column chromatography (25% ethyl acetate in petroleum ether) to give the title compound as a yellow solid (3.1 g, 68.9%). MS (ESI): 558, 560 m/z $[M+H]^+$.

Intermediate 25: 4-Bromo-6-fluoro-5-(2-fluoro-5-(4-fluoro-1-(4-methoxybenzyl)-1H-pyrazol-3-yl)phenoxy)-1-tosyl-1H-indole

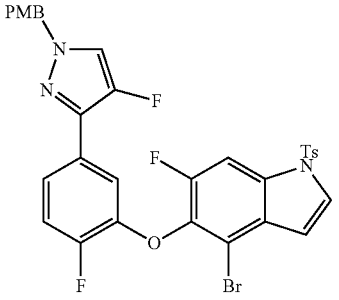

To a stirred and cooled (0° C.) solution of 4-bromo-6-fluoro-5-(2-fluoro-5-(4-fluoro-1-(4-methoxybenzyl)-1H-pyrazol-3-yl)phenoxy)-1H-indole (Intermediate 25E, 1.90 g, 3.42 mmol) in N,N-dimethylformamide (15 mL) was added sodium hydride (60% in mineral oil, 205 mg, 5.12 mmol). After 30 minutes, 4-methylbenzenesulfonyl chloride (905 mg, 4.75 mmol) was added portion wise. The reaction was stirred for an additional 2 hours, then poured into ice water (80 mL). The mixture was extracted with ethyl acetate (3×50 mL). The combined organic phases were washed with brine (100 mL), dried over anhydrous sodium sulfate, filtered, and evaporated. The crude residue was purified by silica gel column chromatography (20% ethyl acetate in petroleum ether) to afford the title compound as a light-yellow solid (1.80 g, 73%). MS (ESI) 682, 684 m/z $[M+H]^+$.

Intermediate 25A: 4-Fluoro-1-(4-methoxybenzyl)-1H-pyrazole

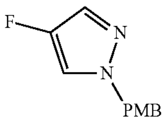

To a stirred and cooled (0° C.) solution of 4-fluoropyrazole (4.00 g, 46.5 mmol) in tetrahydrofuran (150 mL) was added sodium hydride (60% in mineral oil, 2.79 g, 69.7 mmol). After 10 minutes, para-methoxybenzyl chloride (8.68 g, 55.8 mmol) was added portion wise at 0° C. The reaction was allowed to warm to room temperature and stirred overnight, then quenched with water (200 mL) and extracted with ethyl acetate (3×150 mL). The combined organic phases were washed with brine (200 mL), dried over sodium sulfate. The crude residue was purified by silica gel column chromatography (20% ethyl acetate in petroleum ether) to afford the title compound as a light-yellow oil (4.50 g, 47%). $^1$H NMR (400 MHz, MeOD-d6) δ 7.35 (d, J=4.0 Hz, 4H), 7.19-7.16 (m, 3H), 6.90-6.87 (m, 2H), 5.13 (s, 2H), 3.80 (s, 1H) ppm.

Intermediate 25B: 3-Bromo-4-fluoro-1-(4-methoxybenzyl)-1H-pyrazole

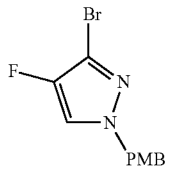

To a stirred and cooled (−78° C.) solution of 4-fluoro-1-(4-methoxybenzyl)-1H-pyrazole (Intermediate 25A, 4.42 g, 21.4 mmol) in tetrahydrofuran (90 mL) was added slowly a solution of n-butyl lithium (2.5 M, 12.8 mL, 32.2 mmol). The reaction was stirred for 20 minutes while maintaining the temperature below −65° C. A solution of 1,2-dibromo-tetrachloroethane (8.38 g, 25.7 mmol) in tetrahydrofuran (25 mL) was added. The resulting solution was stirred for an additional 2 hours. The reaction was quenched with water (200 mL) and extracted with ethyl acetate (3×120 mL). The organic phases were washed with brine (200 mL), dried over sodium sulfate and concentrated. The crude residue was purified by silica gel column chromatography (25% ethyl acetate in petroleum ether) to afford the title compound as a light-yellow solid (3.20 g, 52.4%). $^1$H NMR (400 MHz, CDCl3) δ 7.42 (d, J=4.8 Hz, 1H), 7.20-7.17 (m, 2H), 6.87-6.85 (m, 2H), 5.22 (s, 2H), 3.78 (s, 1H) ppm.

Intermediate 25C: 2-Fluoro-5-(4-fluoro-1-(4-methoxybenzyl)-1H-pyrazol-3-yl)phenol

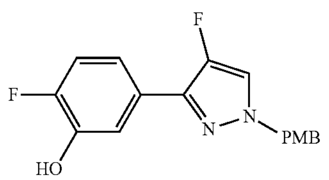

To a stirred solution of 3-bromo-4-fluoro-1-(4-methoxy-benzyl)-1H-pyrazole (Intermediate 25B, 3.11 g, 8.50 mmol) in 1,4-dioxane (45.00 ml) and water (15.00 mL) was added 2-fluoro-5-(4,4,5,5-tetramethyl-1,3,2-dioxaborolan-2-yl) phenol (2.12 g, 8.92 mmol), Pd(dppf)$Cl_2$ (311 mg, 0.424 mmol) and sodium carbonate (1.80 g, 17.0 mmol). The reaction mixture was then heated at 120° C. for 16 hours under argon. The mixture was poured into ice water, extracted with ethyl acetate (100 mL×3). The combined organic phase was dried over sodium sulfate and concentrated. The crude residue was purified by silica gel column chromatography (petroleum ether/ethyl acetate=3/1) to afford the title compound as a white solid (2.01 g, 58.3%). MS (ESI) 317 m/z [M+H]$^+$.

Intermediate 25D: 3-(3-(2-Bromo-6-fluoro-3-methyl-4-nitrophenoxy)-4-fluorophenyl)-4-fluoro-1-(4-methoxybenzyl)-1H-pyrazole

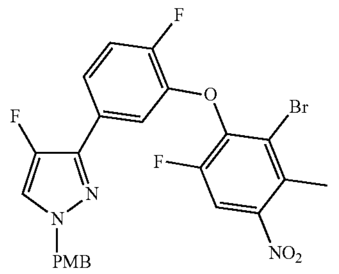

To a solution of 2-fluoro-5-(4-fluoro-1-(4-methoxybenzyl)-1H-pyrazol-3-yl)phenol (Intermediate 25C, 1.5 g, 4.98 mmol) in N,N-dimethylformamide (15.0 mL) was added 3-bromo-1,2-difluoro-4-methyl-5-nitro-benzene (1.25 g, 4.98 mmol) and cesium carbonate (3.09 g, 4.74 mmol), then the mixture was stirred at room temperature for 16 hours. The mixture was diluted with water (80 mL), extracted with ethyl acetate (50 mL×3). The combined organic phase was washed with brine (100 mL), dried over sodium sulfate and concentrated. The crude residue was purified by silica gel column chromatography (petroleum ether/ethyl acetate=4/1) to afford the title compound as a white solid (2.00 g, 77%). MS (ESI) 548 m/z [M+H]$^+$.

Intermediate 25E: 4-Bromo-6-fluoro-5-(2-fluoro-5-(4-fluoro-1-(4-methoxybenzyl)-1H-pyrazol-3-yl)phenoxy)-1H-indole

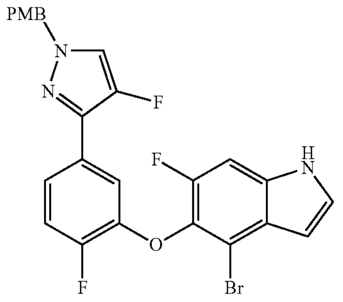

To a stirred solution of 3-(3-(2-bromo-6-fluoro-3-methyl-4-nitrophenoxy)-4-fluorophenyl)-4-fluoro-1-(4-methoxy-benzyl)-1H-pyrazole (Intermediate 25D, 2.30 g, 4.19 mmol) in N,N-dimethylformamide (20 mL) was added N,N-dimethylformamide dimethyl acetal (5.00 g, 41.9 mmol). The reaction was stirred at 120° C. for 2 hours, cooled to room temperature, poured into ice water (100 mL) and then extracted with ethyl acetate (3×60 mL). The combined organic phases were washed with brine (2×150 mL), dried over anhydrous sodium sulfate and concentrated to afford the intermediate (E)-2-[2-bromo-4-fluoro-3-[2-fluoro-5-[4-fluoro-1-[(4-methoxyphenyl)methyl]pyrazol-3-yl]phenoxy]-6-nitro-phenyl]-N,N-dimethyl-ethenamine as a light-yellow oil (2.3 g, 90%). The intermediate obtained above (2.30 g, 3.20 mmol) was dissolved in toluene (18 mL). To this solution was added iron powder (1.79 g, 32.8 mmol) and acetic acid (3.84 g, 64.0 mmol). The mixture was stirred at 100° C. under argon atmosphere overnight. The mixture was cooled to room temperature, poured into ice water. The pH was adjusted to 8 with aq. sodium carbonate, and then filtered. The filter cake was washed with ethyl acetate (3×100 mL). The combined filtrates were washed with water (2×200 ml), dried over anhydrous sodium sulfate and concentrated. The crude residue was purified by silica gel column chromatography (20% ethyl acetate in petroleum ether) to afford the title compound as a white solid (1.90 g, 92%). MS (ESI) 528, 530 m/z $[M+H]^+$.

Intermediate 26: 3-Iodo-1-(tetrahydro-2H-pyran-2-yl)-1H-pyrazole-4-carbonitrile

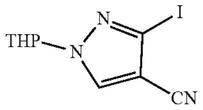

To a stirred solution of 3-iodo-1H-pyrazole-4-carbonitrile (Intermediate 26A, 12.00 g, 54.8 mmol) in tetrahydrofuran (120 mL) was added 3,4-dihydro-2H-pyran (15 mL, 164 mmol) and p-toluenesulfonic acid monohydrate (472 mg, 2.74 mmol). The reaction was stirred at 60° C. for 16 hours, then diluted with ethyl acetate (200 mL). The mixture was washed with water (3×200 mL), dried over anhydrous magnesium sulfate and concentrated. The crude residue was purified by flash chromatography (120 g silica gel column, 0-30% ethyl acetate in petroleum) to give the title compound as an oil (12.20 g, 74%). MS (ESI): 304 m/z $[M+H]^+$.

Intermediate 26A: 3-Iodo-1H-pyrazole-4-carbonitrile

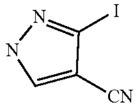

To a stirred and cooled (0° C.) solution of 3-amino-1H-pyrazole-4-carbonitrile (10.00 g, 92.5 mmol) in MeCN (100 mL) was added tert-butylnitrite (15.4 mL, 130 mmol) and diiodomethane (10.4 mL, 130 mmol). The reaction was stirred at 70° C. for 16 hours, then diluted with ethyl acetate (300 mL). The organic solution was washed with water (3×200 mL), dried over anhydrous magnesium sulfate and concentrated. The crude residue was purified by automated flash chromatography (120 g silica gel column, 0-50% ethyl acetate in petroleum) to give the title compound as a yellow solid (12.00 g, 59%). MS (ESI): 219 m/z $[M+H]^+$.

Intermediate 27: Methyl 2,2-dimethyl-4-(2-oxoethoxy)butanoate

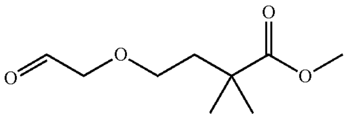

To a stirred and cooled (0° C.) solution of methyl 4-(2,3-dihydroxypropoxy)-2,2-dimethyl-butanoate (Intermediate 27C, 12.8 g, 58.1 mmol) in acetone (300 mL) and water (60 mL) was added sodium periodate (37.3 g, 174 mmol) portion wise. The mixture was stirred at room temperature for 3 hours, then quenched with water (500 mL) and extracted with ethyl acetate (3×200 mL). The combined organic phases were washed with brine, dried over sodium sulfate, and concentrated to afford the crude title compound as a light-yellow oil (8.90 g, 73%). $^1H$ NMR (400 MHz, $CDCl_3$): δ 9.69 (s, 1H), 4.03 (s, 2H), 3.66 (s, 3H), 3.58 (t, J=6.8 Hz, 2H), 1.93 (t, J=6.8 Hz, 2H), 1.22 (s, 6H) ppm.

Intermediate 27A: 3-(2-Bromoethoxy)prop-1-ene

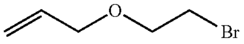

To a stirred and cooled (0° C.) solution of 2-allyloxyethanol (10 g, 97.9 mmol) in pyridine (1.7 mL, 21.5 mmol) was added phosphorus tribromide (3.7 mL, 39.2 mmol). The reaction mixture was stirred overnight at room temperature. The white precipitate was filtered. The filtrate was diluted with methyl tert-butyl ether (300 mL), washed with saturated sodium bicarbonate (200 mL) and brine (200 mL). The organic solution was then dried over sodium sulfate and concentrated. The crude residue was purified by automated silica gel flash chromatography (5% ethyl acetate in petroleum ether) to give the title compound as an oil (3.35 g, 21%). $^1H$ NMR (400 MHz, DMSO-$d_6$) δ 5.88 (dt, J=17.2, 10.6, 5.4 Hz, 1H), 5.32-5.12 (m, 2H), 4.02-3.96 (m, 2H), 3.71 (dd, J=8.3, 3.1 Hz, 2H), 3.60 (dd, J=8.4, 3.3 Hz, 2H) ppm.

Intermediate 27B: Methyl 4-(allyloxy)-2,2-dimethylbutanoate

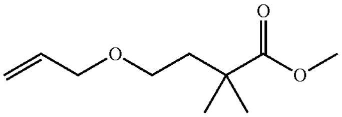

To a stirred and cooled (−78° C.) solution of methyl 2-methylpropanoate (10.9 g, 106 mmol, 1.3 eq.) in tetrahydrofuran (200 mL) was added lithium diisopropylamide (53.1 mL, 106 mmol, 1.3 eq.) slowly. The reaction was stirred at −20° C. for 2 hours, then 3-(2-bromoethoxy)prop-1-ene (Intermediate 27A, 14.2 g, 8.17 mmol) was added at −78° C. The mixture was stirred at room temperature overnight. The reaction was quenched with saturated aqueous ammonium chloride solution and extracted with ethyl acetate (2×200 mL). The combined organic layers were washed with brine, dried over sodium sulfate, and concentrated. The crude material was purified by automated flash chromatography (0-5% ethyl acetate in petroleum ether) to give the title compound as a colorless oil (12.00 g, 67%). $^1H$ NMR (400 MHz, $CDCl_3$) δ 5.93-5.83 (m, 1H), 5.27-5.13 (m, 2H), 3.86-3.84 (2H, m), 3.56 (s, 3H), 3.38 (t, J=7.2 Hz, 2H), 1.88 (t, J=6.4 Hz, 2H), 1.13 (s, 6H) ppm.

Intermediate 27C: Methyl 4-(2,3-dihydroxypropoxy)-2,2-dimethyl-butanoate

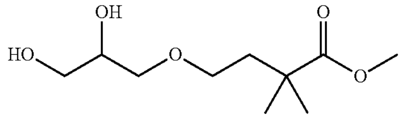

To a stirred solution of methyl 4-allyloxy-2,2-dimethyl-butanoate (Intermediate 27B, 12.00 g, 58 mmol) in acetone (400 mL) was added N-methylmorpholine N-oxide (15.7 mL, 75.4 mmol) and osmium tetroxide (147 mg, 0.58 mmol) in 74 mL of water. The mixture was stirred at room temperature overnight, then partitioned between water (200 mL) and ethyl acetate (100 mL). The separated organic layer was combined with two additional extracts, washed with brine, dried over sodium sulfate, and concentrated. The crude material was purified by automated flash chromatography (0-60% ethyl acetate in petroleum ether) to give the title compound as a colorless oil (8.3 g, 58%). $^1H$ NMR (400 MHz, $CDCl_3$) δ 3.81-3.78 (m, 1H), 3.67 (s, 3H), 3.65-3.39 (m, 5H), 3.01-3.00 (m, 1H), 2.28-2.26 (m, 1H), 1.93-1.74 (m, 2H), 1.21 (s, 6H) ppm.

Intermediate 28: Methyl 6-iodo-2,2-dimethylhexanoate

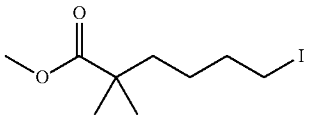

To a stirred solution of methyl 6-chloro-2,2-dimethyl-hexanoate (Intermediate 28A, 16.00 g, 0.083 mol) in acetone (200 mL) was added sodium iodide (31.10 g, 0.208 mol). The reaction was refluxed for 16 hours under nitrogen. After cooling to room temperature, the mixture was filtered. The filtrate was concentrated. The crude residue was dissolved in ethyl acetate (1000 mL), washed with water (200 mL), brine (200 mL), dried over sodium sulfate and concentrated. The crude residue was purified by flash silica gel chromatography (10% ethyl acetate in petroleum ether) to give the title compound as a color less oil (20.00 g, 85%). MS (ESI): 285 m/z $[M+H]^+$.

The following intermediate was prepared based on the procedures described for Intermediate 28.

| Inter. No. | Structure | Name | $^1H$ NMR |
|---|---|---|---|
| 28-1 | 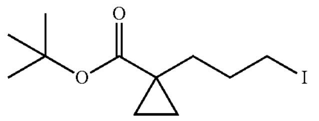 | tert-butyl 1-(3-iodopropyl) cyclopropane-1-carboxylate | $^1H$ NMR (500 MHz, $CDCl_3$) δ 3.19 (t, J = 6.5 Hz, 2H), 2.04-1.96 (m, 2H), 1.60-1.54 (m, 2H), 1.43 (s, 9H), 1.15-1.13 (m, 2H), 0.65-0.63 (m, 2H) ppm |

Intermediate 28A: Methyl 6-chloro-2,2-dimethyl-hexanoate

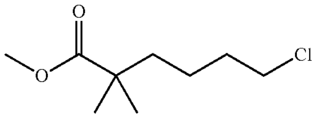

To a stirred and cooled (−78° C.) solution of methyl 2-methylpropanoate (10.30 g, 101 mmol) in tetrahydrofuran (200 mL) was added lithium diisopropylamide (50.4 mL, 101 mmol) drop wise. After stirring at −78° C. for 1 hour, 1-chloro-4-iodo-butane (20.00 g, 91.5 mmol) was added. The mixture was stirred at −78° C. for 1 hour and then allowed to warm to room temperature and stirred for an additional 16 hours. The reaction was quenched with 1M hydrochloric acid (200 mL) and extracted with ethyl acetate (2×200 mL). The combined organic phases were washed with water, brine, dried over sodium sulfate and concentrated. The crude residue was purified by flash silica gel chromatography (50% ethyl acetate in petroleum ether) to give the title compound as a light-yellow oil (16.00 g, 82.9%). MS (ESI): 193 m/z $[M+H]^+$.

Intermediate 29: 6-((tert-Butyldimethylsilyl)oxy)-5,5-dimethylhexanal

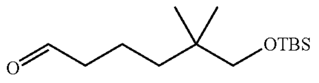 [SMILES: CC(C)(CCCC=O)CO[Si](C)(C)C(C)(C)C]

To a stirred and cooled (−78° C.) solution of oxalyl chloride (14.7 mL, 174.0 mmol) in dichloromethane (600 mL) was added dimethyl sulfoxide (24.7 mL, 347.0 mmol) in 50 mL of dichloromethane dropwise. After stirring for 15 minutes, a solution of 6-((tert-butyldimethylsilyl)oxy)-5,5-dimethylhexan-1-ol (Intermediate 29E, 22.60 g, 86.8 mmol) in dichloromethane (100 mL) was added drop wise at −78° C. The solution was stirred for an additional 30 minutes at −78° C. Next, triethylamine (72.6 mL, 521 mmol) was added. The mixture was warmed up to 0° C. over 30 minutes, then quenched with water (500 mL), extracted with ethyl acetate (2×500 mL). The combined organic extracts were washed with brine (2×500 mL), dried over anhydrous sodium sulfate and concentrated to give the title compound as an oil (22.00 g, 98%). $^1H$ NMR (400 MHz, $CDCl_3$) δ 9.74 (s, 1H), 3.22 (s, 2H), 2.38 (t, J=7.3 Hz, 2H), 1.57 (s, 2H), 1.22 (dd, J=8.5, 3.8 Hz, 2H), 0.87 (s, 9H), 0.82 (s, 6H), 0.00 (s, 6H).

Intermediate 29A: 6-chloro-2,2-dimethylhexan-1-ol

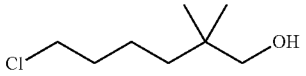

To a stirred and cooled (−78° C.) solution of methyl 6-chloro-2,2-dimethyl-hexanoate (Intermediate 28A, 24.00 g, 125 mmol) in tetrahydrofuran (200 mL) was added lithium aluminum hydride (7.09 g, 187 mmol) dropwise over 30 minutes. The mixture was stirred for 3 hours at −78° C., then quenched with 7 mL of water, warmed to 0° C., followed by 7 mL of 15% sodium hydroxide, and finally 21 mL of water. The mixture was stirred at room temperature for 15 minutes and then filtered. The filtrate was concentrated to give the title compound as an oil (18.00 g, 87.8%). H NMR (400 MHz, $CDCl_3$) δ 3.55 (t, J=6.7 Hz, 2H), 3.53 (s, 2H), 1.80-1.73 (m, 2H), 1.4-1.39 (m, 2H), 1.28-1.26 (m, 2H), 0.86 (s, 6H) ppm.

Intermediate 29B: Tert-Butyl-(6-chloro-2,2-dimethyl-hexoxy)-dimethyl-silane

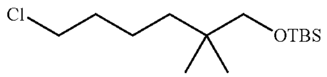 [SMILES: CC(C)(CCCCCl)CO[Si](C)(C)C(C)(C)C]

To a stirred solution of 6-chloro-2,2-dimethyl-hexan-1-ol (Intermediate 29A, 18.00 g, 109 mmol) in dichloromethane (300 mL) was added tert-butyldimethylsilyl chloride (19.80 g, 131 mmol) and imidazole (14.9 g, 219 mmol). The mixture was stirred at room temperature for 2 hours, then diluted with dichloromethane (200 mL). The solution was washed with water (2×100 mL), brine, dried over anhydrous sodium sulfate and concentrated. The crude residue was purified by flash chromatography (120 g silica gel column, petroleum ether) to give the title compound as an oil (27.00 g, 89%). $^1$H NMR (400 MHz, $CDCl_3$) δ 3.52 (t, J=6.7 Hz, 2H), 3.21 (s, 2H), 1.76-1.68 (m, 2H), 1.35 (dt, J=10.7, 7.9 Hz, 2H), 1.23-1.18 (m, 2H), 0.87 (s, 9H), 0.80 (d, J=5.8 Hz, 6H), −0.01 (d, J=6.6 Hz, 6H) ppm.

Intermediate 29C: Tert-Butyl((6-iodo-2,2-dimethylhexyl)oxy)dimethylsilane

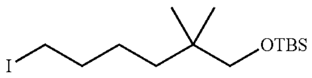 [SMILES: CC(C)(CCCCI)CO[Si](C)(C)C(C)(C)C]

To a stirred solution of tert-butyl((6-iodo-2,2-dimethylhexyl)oxy)dimethylsilane (Intermediate 29B, 27.00 g, 96.8 mmol) in acetone (300 mL) was added sodium iodide (43.50 g, 290 mmol) at room temperature. The mixture was stirred at 60° C. for 16 hours. The solvent was evaporated. The residue was dissolved in ethyl acetate (500 mL), washed with water (2×300 mL), dried over anhydrous sodium sulfate and concentrated. The crude residue was purified by flash chromatography (330 g silica gel column, petroleum ether) to give the title compound as a colorless oil (32.00 g, 89.3%). $^1$H NMR (400 MHz, $CDCl_3$) 3.25-3.13 (m, 4H), 1.80-1.68 (m, 2H), 1.39-1.27 (m, 2H), 1.23-1.16 (m, 2H), 0.87 (s, 9H), 0.80 (s, 6H), −0.01 (d, J=7.0 Hz, 6H).

The following intermediate was prepared based on the procedures described for Intermediate 29C.

| Inter. No. | Structure | Name | MS m/z $[M + H]^+$ |
|---|---|---|---|
| 29C-1 | 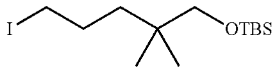 [SMILES: CC(C)(CCCI)CO[Si](C)(C)C(C)(C)C] | tert-butyl((5-iodo-2,2-dimethylpentyl)oxy)dimethylsilane | 357 |

Intermediate 29D: 6-((tert-Butyldimethylsilyl)oxy)-5,5-dimethylhexyl Acetate

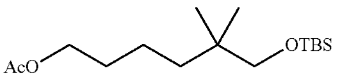 [SMILES: CC(=O)OCCCCC(C)(C)CO[Si](C)(C)C(C)(C)C]

To a stirred solution of tert-butyl((6-iodo-2,2-dimethylhexyl)oxy)dimethylsilane (Intermediate 29C, 35.00 g, 94.5 mmol) in N,N-dimethylformamide (300 mL) were added potassium acetate (27.80 g, 283.0 mmol) and 18-crown-6 (25.00 g, 94.5 mmol). The reaction mixture was stirred for 16 hours at 100° C. under argon atmosphere. The reaction mixture was diluted with ethyl acetate (500 mL), washed with water (2×500 mL), brine, dried over anhydrous sodium sulfate and concentrated to give the title compound as an oil (28.00 g, 97.9%). $^1$H NMR (400 MHz, $CDCl_3$) δ 4.04 (t, J=6.7 Hz, 2H), 3.20 (s, 2H), 2.03 (s, 3H), 1.30-1.19 (m, 6H), 0.87 (s, 9H), 0.80 (s, 6H), 0.00 (s, 6H) ppm.

Intermediate 29E: 6-((tert-Butyldimethylsilyl)oxy)-5,5-dimethylhexan-1-ol

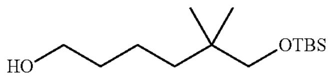 [SMILES: CC(C)(CCCCO)CO[Si](C)(C)C(C)(C)C]

To a stirred solution of 6-((tert-butyldimethylsilyl)oxy)-5,5-dimethylhexyl acetate (Intermediate 29D, 28.00 g, 92.6 mmol) in methanol (250 mL) was added potassium carbonate (25.60 g, 185 mmol). The reaction was stirred for 3 hours at room temperature under argon atmosphere, then diluted with ethyl acetate (500 mL). The solution was washed with water (2×500 mL), dried over anhydrous sodium sulfate and concentrated to give the title compound as an oil (22.60 g, 94%). $^1$H NMR (400 MHz, $CDCl_3$) δ 3.63 (s, 2H), 3.20 (d, J=6.2 Hz, 2H), 1.57-1.47 (m, 2H), 1.33-1.22 (m, 4H), 0.87 (s, 9H), 0.82-0.79 (m, 6H), 0.00 (s, 6H) ppm.

Intermediate 30: Methyl 2,2-dimethyl-6-oxohexanoate

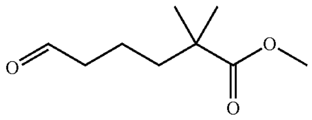

To a stirred and cooled (0° C.) solution of methyl 6-hydroxy-2,2-dimethylhexanoate (Intermediate 30B, 20.00 g, 115 mmol) in dichloromethane (40 mL) was added a mixture of pyridinium chlorochromate and silica gel (1:1, 49.5 g). The reaction was stirred at room temperature for 3 hours. The solvent was removed. The residue was diluted with petroleum ether (100 mL) and the solution was filtered through a pad of Celite. The filtrate was concentrated to obtain the title compound as a colorless oil (17.30 g, 88%). $^1$H NMR (400 MHz, $CDCl_3$) δ 9.66 (s, 1H), 3.57 (s, 3H), 2.34-2.32 (m, 2H), 1.51-1.41 (m, 4H), 1.08 (m, 6H) ppm.

Intermediate 30A: Methyl 6-((tert-butyldimethylsilyl)oxy)-2,2-dimethylhexanoate

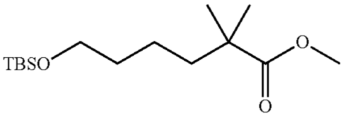 [SMILES: COC(=O)C(C)(C)CCCCO[Si](C)(C)C(C)(C)C]

To a stirred and cooled (0° C.) solution of methyl 2-methylpropanoate (17.20 g, 168.0 mmol) in tetrahydrofuran (180 mL) was added lithium diisopropylamide in tetrahydrofuran (2.0 M, 93 mL, 183 mmol) dropwise over 15 minutes. The mixture was stirred for 1 hour at −78° C., allowed to warm up to room temperature for 1 hour and then re-cooled to −78° C. To the solution was added tert-butyl(4-iodobutoxy)dimethylsilane (48.00 g, 153 mmol) dropwise at −78° C. After the addition, the reaction was allowed to warm up to room temperature and stirred overnight. The solvent was removed. The residue was partitioned between saturated ammonium chloride (100 mL) and ethyl acetate (200 mL). The separated organic phase was combined with two additional ethyl acetate extracts, washed with brine (100 mL), dried over anhydrous sodium sulfate and concentrated. The residue was purified by silica gel column chromatography (5% ethyl acetate in petroleum ether) to give the title compound as a colorless oil (43.60 g, 99%). $^1$H NMR (400 MHz, $CDCl_3$) δ 3.61 (s, 3H), 3.55 (t, J=6.4 Hz, 2H), 1.50-1.42 (m, 4H), 1.22-1.19 (m, 2H), 1.12 (s, 6H), 0.82 (s, 9H), 0.00 (s, 6H) ppm.

Intermediate 30B: Methyl 6-hydroxy-2,2-dimethylhexanoate

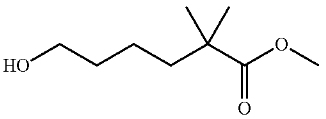

To a stirred solution of methyl 6-((tert-butyldimethylsilyl)oxy)-2,2-dimethylhexanoate (Intermediate 30A, 32.50 g, 113 mmol) in tetrahydrofuran (100 ml) was added 3M hydrochloric acid (188 mL, 563 mmol). The reaction was stirred at room temperature overnight. The mixture was quenched with water (100 mL) and extracted with ethyl acetate (200 mL×3). The combined organic layer was washed with brine and dried over sodium sulfate and filtered. The filtrate was concentrated. The residue was purified by flash chromatography (petroleum ether/ethyl acetate=20/1) to give the title compound as a yellow oil. (17.90 g, 91%). $^1$H NMR (400 MHz, $CDCl_3$) δ 3.56 (s, 3H), 3.54 (t, J=6.4 Hz, 2H), 1.62 (br s, 1H), 1.48-1.41 (m, 4H), 1.23-1.15 (m, 2H), 1.07 (s, 6H) ppm.

Intermediate 31: 3-(1,1-Dimethylallyloxy)propanal

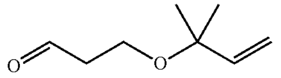

To a stirred and cooled (0° C.) solution of 3-(1,1-dimethylallyloxy)propan-1-ol (Intermediate 31B, 5.95 g, 41.3 mmol) in dichloromethane (60 mL) were added pyridinium chlorochromate (17.80 g, 82.5 mmol) and silica gel (17.8 g). The mixture was stirred at room temperature for 2 hours, then filtered. The filter cake was rinsed with dichloromethane. The filtrate was concentrated. The residue was purified by silica gel column chromatography (80 g silica gel column, 0-30% ethyl acetate in petroleum ether) to give the title compound as an oil (3.59 g, 61%). $^1$H NMR (400 MHz, $CDCl_3$) δ 9.77 (t, J=2.0 Hz, 1H), 5.81 (dd, J=18.0, 11.2 Hz, 1H), 5.16 (dd, J=6.8, 0.8 Hz, 1H), 5.12 (s, 1H), 3.65 (t, J=6.4 Hz, 2H), 2.59 (td, J=6.4, 2.0 Hz, 2H), 1.27 (s, 6H) ppm.

Intermediate 31A: Ethyl 3-(1,1-dimethylallyloxy)propanoate

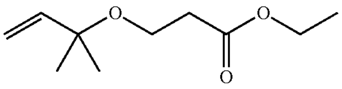

To a stirred and cooled (0° C.) solution of ethyl acrylate (50.00 g, 0.5 mol) and 2-methylbut-3-en-2-ol (86.00 g, 1.0 mol) in tetrahydrofuran (250 mL) was slowly added sodium hydride (2.00 g, 50.0 mmol). The reaction was stirred at room temperature for 16 hours, then quenched with saturated aqueous ammonium chloride solution (200 mL). The mixture was then extracted with ethyl acetate (3×300 mL). The combined organic phases were washed with brine, dried over sodium sulfate, and concentrated. The crude product was purified by flash chromatography (0-20% ethyl acetate in petroleum ether) to give the title compound as a colorless oil (35.40 g, 38%). $^1$H NMR (400 MHz, $CDCl_3$) δ 5.86-5.79 (m, 1H), 5.15-5.10 (m, 2H), 4.14 (q, J=7.2 Hz, 2H), 3.57 (t, J=6.4 Hz, 2H), 3.57 (t, J=6.8 Hz, 2H), 1.28-1.24 (m, 9H) ppm.

Intermediate 31B: 3-(1,1-Dimethylallyloxy)propan-1-ol

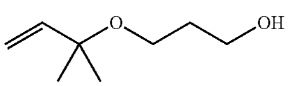

To a stirred and cooled (0° C.) solution of ethyl 3-(1,1-dimethylallyloxy)propanoate (Intermediate 31A, 35.00 g, 0.19 mol) in 100 mL of tetrahydrofuran was added lithium aluminum hydride (8.56 g, 0.23 mol). The reaction was stirred at room temperature for 1 hour, then carefully quenched at 0° C. through the dropwise addition of water (10 mL), followed by 15% sodium hydroxide (10 mL) and water (30 ml). The resulting mixture was filtered. The filtrate was concentrated. The crude residue was purified by automated flash chromatography (0-30% ethyl acetate in petroleum ether) to give the title compound as a colorless oil (14.00 g, 52%). $^1$H NMR (400 MHz, $CDCl_3$) δ 5.82 (dd, J=17.6, 10.8 Hz, 1H), 5.16-5.12 (m, 2H), 3.75 (q, J=5.2 Hz, 2H), 3.51 (t, J=6.0 Hz, 2H), 1.81-1.78 (m, 2H), 1.28 (s, 6H) ppm.

Intermediate 32: Methyl 2,2-dimethyl-3-(2-oxoethoxy)propanoate

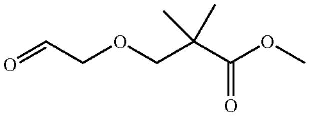

To a stirred solution of methyl 3-(2,3-dihydroxypropoxy)-2,2-dimethyl-propanoate (Intermediate 32C, 25.00 g, 109 mmol) in acetone (500 mL) and water (100 mL) was added sodium periodate (70.00 g, 327 mmol). The reaction was stirred at room temperature for 5 hours, diluted with water (1 L) and extracted with ethyl acetate (2×1 L). The combined organic phases were washed with brine (300 mL), dried over anhydrous sodium sulfate and concentrated. The crude residue was purified by automated flash chromatography (10-50% ethyl acetate in petroleum ether) to afford the title compound as a light-yellow oil (14.80 g, 70.1%). $^1$H NMR (400 MHz, $CDCl_3$) δ 9.72 (s, 1H), 4.05 (s, 2H), 3.70 (s, 3H), 3.57 (s, 2H), 1.23 (s, 6H) ppm.

Intermediate 32A: 3-(Chloromethoxy)prop-1-ene

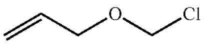

To a stirred solution of prop-2-en-1-ol (40 g, 689 mmol) and paraformaldehyde (27.2 g, 897 mmol) in dichloromethane (600 mL) was added trimethylsilyl chloride (150.0 g, 1.38 mol) at room temperature. The mixture was stirred at room temperature for 18 hours, dried with calcium chloride and then concentrated in vacuo to afford the crude title compound as a colorless oil (48.00 g, 52%). $^1$H NMR (400 MHz, $CDCl_3$): δ 5.88-5.78 (m, 1H), 5.45 (s, 2H), 5.32-5.21 (m, 2H), 4.16-4.14 (m, 2H) ppm.

Intermediate 32B: Methyl 3-allyloxy-2,2-dimethyl-propanoate

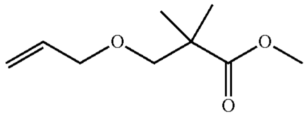

To a stirred and cooled (−78° C.) solution of methyl 2-methylpropanoate (59.3 mL, 517 mmol) in dry tetrahydrofuran (400 mL) was added lithium diisopropylamide (2.0 M, 259 mL, 517 mmol). The reaction was stirred for 1 hour, then added a solution of 3-(chloromethoxy)prop-1-ene (Intermediate 32A, 53 g, 398 mmol) in dry tetrahydrofuran (50 mL) and stirred at −78° C. for 1 hour. The mixture was warmed up to room temperature and stirred for an additional 16 hours, quenched with saturated aqueous ammonium chloride, and extracted with ethyl acetate (3×200 mL). The combined organic phases were washed with brine (100 mL), dried over sodium sulfate and concentrated. The crude residue was purified by automated flash chromatography (300 g silica gel column, 0-18% ethyl acetate in petroleum ether) to give the title compound as a colorless oil (38.60 g, 51%). $^1$H NMR (400 MHz, $CDCl_3$) δ 5.89-5.82 (m, 1H), 5.27-5.14 (m, 2H), 3.98 (d, J=5.6 Hz, 2H), 3.68 (s, 3H), 3.43 (s, 2H), 1.21 (s, 6H) ppm.

Intermediate 32C: Methyl 3-(2,3-dihydroxypropoxy)-2,2-dimethyl-propanoate

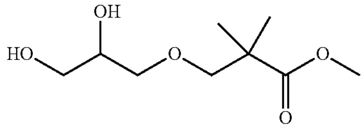

To a stirred solution of methyl 3-allyloxy-2,2-dimethyl-propanoate (Intermediate 32B, 38.60 g, 202 mmol) in acetone (900 mL) was added N-methylmorpholine N-oxide (67.2 mL, 323 mmol) and osmium tetroxide (513 mg, 2.02 mmol) in 1.6 mL of water. The reaction was stirred at room temperature overnight. The solvent was evaporated. The residue was dissolved in ethyl acetate (1 L), washed with brine, dried over sodium sulfate, and concentrated. The crude product was purified by automated flash chromatography (10-60% ethyl acetate in petroleum ether) to give the title compound as a colorless oil (25.00 g, 54%). $^1$H NMR (400 MHz, $CDCl_3$) δ 3.88-3.82 (m, 1H), 3.69 (s, 3H), 3.68-3.45 (m, 7H), 2.86 (t, J=6 Hz, 1H), 2.26-2.21 (m, 1H), 1.20 (s, 6H) ppm.

Intermediate 33: Ethyl 3-(3-(2-(3-mercapto-2,2-dimethylpropoxy)-1-((tetrahydro-2H-pyran-2-yl)oxy)ethyl)phenyl)propanoate

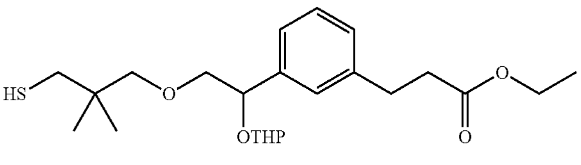

To a stirred solution of ethyl 3-(3-(2-(3-(acetylthio)-2,2-dimethylpropoxy)-1-((tetrahydro-2H-pyran-2-yl)oxy)ethyl)phenyl)propanoate (Intermediate 33F, 6.30 g, 13.2 mmol) in dry ethanol (100 mL) was added sodium ethoxide (1.08 g, 15.9 mmol) at room temperature under $N_2$. After stirring for 1 hour, the reaction was quenched with water (300 mL) under nitrogen. The mixture was extracted with dichloromethane (3×200 mL) under nitrogen. The combined dichloromethane solutions were washed with brine and dried over sodium sulfate. The solvent was evaporated to give the crude title compound as an oil (5.30 g, 89%). MS (ESI): 447 m/z $[M+Na]^+$.

The following intermediates were prepared based on the procedures described for Intermediate 33, and/or procedures for 33A to F.

C. for 1 hour. Then a solution of methyl 2,2-dimethyl-3-(2-oxoethoxy)propanoate (Intermediate 32, 14.8 g, 76.5 mmol) in 20 mL of tetrahydrofuran was added dropwise to the above solution. The mixture was allowed to warm to 0° C. with stirring for 1.5 hours, then quenched with saturated aqueous ammonium chloride (300 mL) and extracted with ethyl acetate (2×300 mL). The combined organic phases were dried over sodium sulfate and concentrated. The crude product was purified by chromatography (0-20% ethyl acetate in petroleum ether) to give the title compound as light-yellow oil (16.10 g, 55.3%). MS (ESI): 353 m/z $[M+Na]^+$.

| Inter. No. | Structure | Name | MS m/z $[M + H]^+$ |
|---|---|---|---|
| 33-1 | 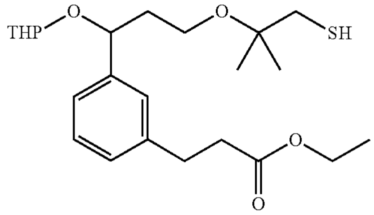 | ethyl 3-(3-(3-((1-mercapto-2-methylpropan-2-yl)oxy)-1-((tetrahydro-2H-pyran-2-yl)oxy)propyl)phenyl)propanoate | 447 $[M + Na]^+$ |
| 33-2 | 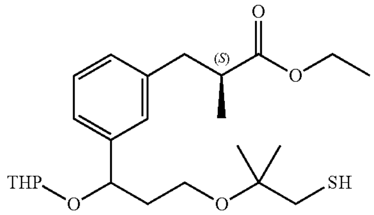 | ethyl (2S)-3-(3-(6-mercapto-5,5-dimethyl-1-((tetrahydro-2H-pyran-2-yl)oxy)hexyl)phenyl)-2-methylpropanoate | 459 $[M + Na]^+$ (mixture of diastereomers) |
| 33-3 | 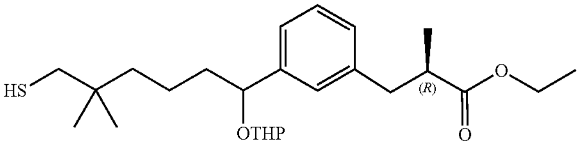 | ethyl (2R)-3-(3-(6-mercapto-5,5-dimethyl-1-((tetrahydro-2H-pyran-2-yl)oxy)hexyl)phenyl)-2-methylpropanoate | 459 $[M + Na]^+$ (mixture of diastereomers) |
| 33-4 | 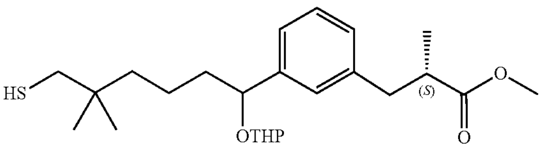 | methyl (2S)-3-(3-(6-mercapto-5,5-dimethyl-1-((tetrahydro-2H-pyran-2-yl)oxy)hexyl)phenyl)-2-methylpropanoate | 445 $[M + Na]^+$ (mixture of diastereomers) |

Intermediate 33A: Methyl 3-(2-(3-bromophenyl)-2-hydroxyethoxy)-2,2-dimethylpropanoate

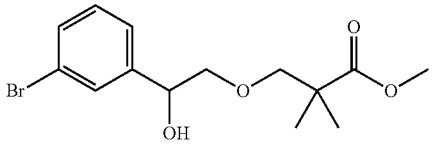 [SMILES: COC(=O)C(C)(C)COCC(O)c1cccc(Br)c1]

To a stirred and cooled (−40° C.) solution of 1-bromo-3-iodo-benzene (26.00 g, 91.8 mmol) in dry tetrahydrofuran (200 mL) was added dropwise isopropyl magnesium chloride (2 M in THF, 45.6 mL). The reaction was stirred at −40°

Intermediate 33B: Methyl 3-(2-(3-bromophenyl)-2-((tetrahydro-2H-pyran-2-yl)oxy)ethoxy)-2,2-dimethylpropanoate

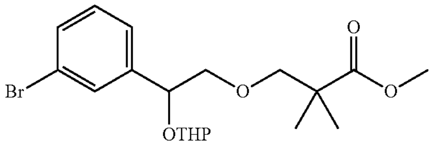

To a stirred solution of methyl 3-(2-(3-bromophenyl)-2-hydroxyethoxy)-2,2-dimethylpropanoate (Intermediate 33A, 16.10 g, 44.2 mmol) in dichloromethane (250 mL) was added 4-methylbenzenesulfonic acid (381 mg, 2.21 mmol), followed by 3,4-dihydro-2H-pyran (7.44 g, 88.5 mmol). The reaction was stirred at room temperature for 16 hours, then quenched with water (150 mL) and extracted with dichloromethane (2×300 mL). The combined organic extracts were dried over sodium sulfate and concentrated. The residue was purified by automated flash chromatography (0-8% ethyl acetate in petroleum ether) to give the title compound as a colorless oil (15.30 g, 82%). MS (ESI): 437 m/z [M+Na]+.

Intermediate 33C: 3-(2-(3-Bromophenyl)-2-((tetrahydro-2H-pyran-2-yl)oxy)ethoxy)-2,2-dimethylpropan-1-ol

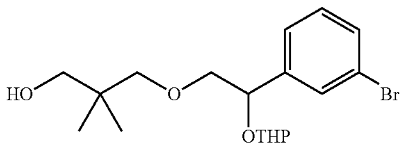

To a stirred and cooled (0° C.) solution of methyl 3-(2-(3-bromophenyl)-2-((tetrahydro-2H-pyran-2-yl)oxy) ethoxy)-2,2-dimethylpropanoate (Intermediate 33B, 15.30 g, 36.1 mmol) in tetrahydrofuran (200 mL) was added lithium aluminum hydride (1.37 g, 36.1 mmol) portion-wise under nitrogen. The reaction was warmed to room temperature and stirred for 2 hours. The mixture was then carefully quenched with 10 mL of water, followed by 15% sodium hydroxide and 30 mL of water at 0° C. The mixture was filtered, and the filtrate was concentrated. The residue was subjected to automated flash chromatography (0-20% ethyl acetate in petroleum ether) to give the title compound as a colorless oil (12.20 g, 82.9%). MS (ESI): 409, 411 m/z [M+Na]+.

Intermediate 33D: Ethyl (E)-3-(3-(2-(3-hydroxy-2,2-dimethylpropoxy)-1-((tetrahydro-2H-pyran-2-yl)ox)ethyl)phenyl)acrylate

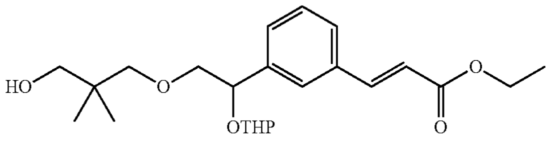

To a stirred and degassed solution of 3-(2-(3-bromophenyl)-2-((tetrahydro-2H-pyran-2-yl)oxy)ethoxy)-2,2-dimethylpropan-1-ol (Intermediate 33C, 3.20 g, 7.68 mmol) in N-Methyl-2-pyrrolidone (30 mL) were added tri-o-tolylphosphine (702 mg, 2.31 mmol), ethyl acrylate (4.18 mL, 38.4 mmol), triethylamine (5.4 mL, 38.4 mmol) and finally palladium (II) acetate (173 mg, 0.768 mmol). The reaction mixture was stirred at 120° C. for 16 hours under argon in a sealed tube. The reaction mixture was cooled to room temperature and diluted with ethyl acetate (150 mL). The solution was washed with water (30 mL), brine (30 mL), dried over sodium sulfate and concentrated. The residue was purified by silica gel column chromatography (1-20% ethyl acetate in petroleum ether) to give the title compound as a colorless oil (2.60 g, 81%). MS (ESI): 429 m/z [M+Na]+.

Intermediate 33E: Ethyl 3-(3-(2-(3-hydroxy-2,2-dimethylpropoxy)-1-((tetrahydro-2H-pyran-2-yl)oxy)ethyl)phenyl)propanoate

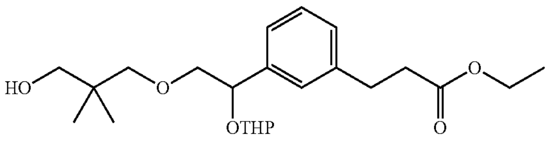

To a stirred solution of ethyl (E)-3-(3-(2-(3-hydroxy-2,2-dimethylpropoxy)-1-((tetrahydro-2H-pyran-2-yl)oxy)ethyl)phenyl)acrylate (Intermediate 33D, 7.90 g, 19.0 mmol) in ethanol (120 mL) was added Raney-Ni (3.00 g). The suspension was stirred at room temperature under a hydrogen balloon for 2 hours. The mixture was filtered through a pad of Celite. The filtrate was concentrated to give the crude title compound as a colorless oil (7.30 g, 91%). MS (ESI): 431 m/z [M+Na]+.

Intermediate 33F: Ethyl 3-(3-(2-(3-(acetylthio)-2,2-dimethylpropoxy)-1-((tetrahydro-2H-pyran-2-yl)oxy)ethyl)phenyl)propanoate

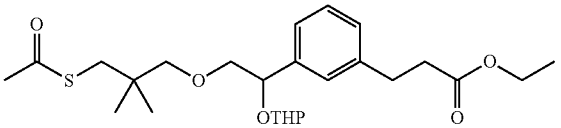

To a stirred and cooled (0° C.) solution of triphenyl phosphine (13.80 g, 52.5 mmol) in tetrahydrofuran (250 mL) was added diisopropyl azodicarboxylate (10.60 g, 52.5 mmol) dropwise. After stirring for 1 hour, ethyl 3-(3-(2-(3-hydroxy-2,2-dimethylpropoxy)-1-((tetrahydro-2H-pyran-2-yl)oxy)ethyl)phenyl)propanoate (Intermediate 33E, 7.30 g, 17.5 mmol) and thioacetic acid (4.00 g, 52.5 mmol) in tetrahydrofuran (50 mL) were added dropwise. The mixture was stirred at room temperature for 5 hours. The solvent was removed under vacuum. The residue was dissolved in 15% ethyl acetate in petroleum ether. The insoluble material was removed by filtration. The filtrate was concentrated and then purified by silica gel column chromatography (120 g silica gel column, 0-10% ethyl acetate in petroleum ether) to give the title compound as an oil (6.80 g, 77%). MS (ESI): 489 m/z [M+Na]+.

The following intermediate was prepared based on the procedures described for Intermediate 33F.

| Inter. No. | Structure | Name | MS m/z [M + H]$^+$ |
|---|---|---|---|
| 33F-1 | 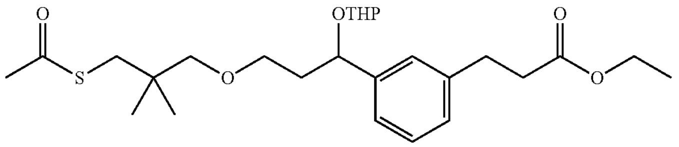 | ethyl 3-(3-(3-(3-(acetylthio)-2,2-dimethylpropoxy)-1-((tetrahydro-2H-pyran-2-yl)oxy)propyl)phenyl)propanoate | 503 [M + Na]$^+$ |

Intermediate 34: Methyl 6-bromo-6-(3-bromophenyl)-2,2-dimethylhexanoate

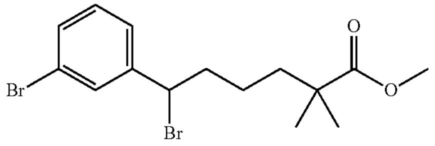 [SMILES: COC(=O)C(C)(C)CCCC(Br)c1cccc(Br)c1]

To a stirred and cooled (0° C.) solution of methyl 6-(3-bromophenyl)-6-hydroxy-2,2-dimethylhexanoate (Intermediate 34A, 3.5 g, 10.6 mmol) in dichloromethane (20 mL) was added N-bromosuccinimide (8.40 g, 32.0 mmol) and triphenylphosphine (5.7 g, 21.7 mmol). The reaction was stirred at room temperature for 2 hours. The mixture was concentrated in vacuo to give a crude residue, which was re-dissolved in ethyl acetate (3×30 mL). The combined organic phases were washed with brine (30 mL), dried over anhydrous sodium sulfate and concentrated in vacuo. The residue was purified by silica gel column chromatography (10% ethyl acetate in petroleum ether) to give the title compound as a yellow solid (2.80 g, 67%). $^1$H NMR (400 MHz, $CDCl_3$) δ 7.52 (s, 1H), 7.40 (d, J=8.0 Hz, 1H), 7.30 (d, J=7.6 Hz, 1H), 7.20 (t, J=7.6 Hz, 1H), 4.85 (dd, J=6.8 Hz & 8.0 Hz, 1H), 3.63 (s, 3H), 2.22-2.18 (m, 1H), 2.08-2.02 (m, 1H), 1.59-1.53 (m, 2H), 1.28-1.24 (m, 2H), 1.15 (s, 3H), 1.14 (s, 3H) ppm.

Intermediate 34A: Methyl 6-(3-bromophenyl)-6-hydroxy-2,2-dimethylhexanoate

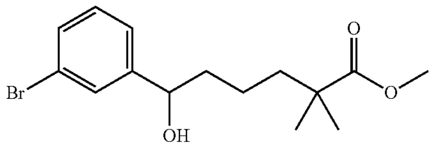 [SMILES: COC(=O)C(C)(C)CCCC(O)c1cccc(Br)c1]

To a stirred and cooled (−78° C.) solution of 1,3-dibromobenzene (19.50 g, 82.7 mmol) in tetrahydrofuran (50 mL) was added n-butyl lithium in THF/n-heptane/ethylbenzene (2.5 M, 32.5 mL, 82.7 mmol) dropwise over 15 minutes. The mixture was stirred for 2 hours at −78° C. and then added a solution of methyl 2,2-dimethyl-6-oxohexanoate (Intermediate 30, 13 g, 75.5 mmol) in tetrahydrofuran (20 mL) dropwise. The reaction was warmed up to room temperature and stirred for 1 hour, then quenched with water (60 mL) and concentrated to dryness. The residue was taken in ethyl acetate (60 mL). The solution was washed with brine (2×60 mL), dried over anhydrous sodium sulfate and concentrated. The residue was purified by automated flash chromatography (120 g silica gel column, 0-20% ethyl acetate in petroleum ether) to afford the title compound as an oil (8.00 g, 32.2%). MS (ESI): 311, 313 m/z [M−$H_2$O]$^+$.

Intermediate 35: 6-(3-Bromophenyl)-2,2-dimethyl-6-((tetrahydro-2H-pyran-2-yl)oxy)hexan-1-ol

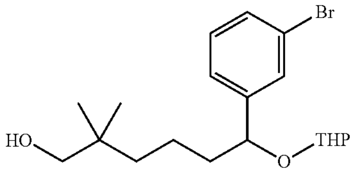

To a stirred solution of ((6-(3-bromophenyl)-2,2-dimethyl-6-((tetrahydro-2H-pyran-2-yl)oxy)hexyl)oxy)(tert-butyl)dimethylsilane (Intermediate 35B, 24.00 g, 48.0 mmol) in tetrahydrofuran (150 mL) was added tetrabutylammonium fluoride (144 mL, 144 mmol, 1M in THF). The reaction was stirred at room temperature for 16 hours, then quenched with water (300 mL) and concentrated. The crude residue was dissolved in ethyl acetate (300 mL), washed with brine (2×300 mL), dried over anhydrous sodium sulfate and concentrated. The residue was purified by automated flash chromatography (120 g silica gel column, 0-20% ethyl acetate in petroleum ether) to give the title compound as an oil (12.00 g, 65%). MS (ESI): 407, 409 m/z [M+Na]$^+$.

Intermediate 35A: 1-(3-Bromophenyl)-6-[tert-butyl(dimethyl)silyl]oxy-5,5-dimethyl-hexan-1-ol

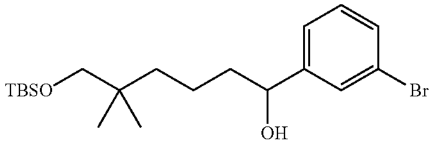 [SMILES: CC(C)(CCCC(O)c1cccc(Br)c1)CO[Si](C)(C)C(C)(C)C]

To a stirred and cooled (−78° C.) solution of 1,3-dibromobenzene (24.10 g, 102.0 mmol) in tetrahydrofuran (300 mL) was added n-butyl lithium (2.5 M in hexane, 40.9 mL, 102 mmol) dropwise over 15 minutes. The mixture was stirred at −78° C. for 2 hours, then treated with of solution of 6-((tert-butyldimethylsilyl)oxy)-5,5-dimethylhexanal (Intermediate 29, 20.00 g, 48.1 mmol) in tetrahydrofuran (10 mL) dropwise. The reaction was warmed up to room temperature and stirred for an additional hour, then quenched with water (500 mL). The solution was extracted with ethyl acetate (3×200 mL). The combined extracts were washed with brine (2×200 mL), dried over anhydrous sodium sulfate and concentrated. The residue was purified by flash chromatography (330 g silica gel column, 0-20% ethyl acetate in petroleum ether) to give the title compound as an oil (20.00 g, 56.6%). MS (ESI): 397, 399 m/z [M−$H_2$O+H]$^+$.

The following intermediate was prepared based on the procedures described for Intermediate 35A.

| Inter. No. | Structure | Name | MS m/z $[M + H]^+$ |
|---|---|---|---|
| 35A-1 | 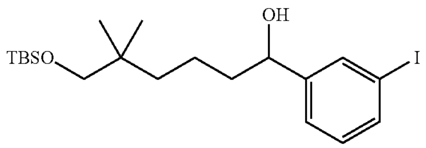 [SMILES: CC(C)(CCCC(O)c1cccc(I)c1)CO[Si](C)(C)C(C)(C)C] | 6-((tert-butyldimethylsilyl)oxy)-1-(3-iodophenyl)-5,5-dimethylhexan-1-ol | 485.0 $[M + Na]^+$ |

Intermediate 35B: ((6-(3-Bromophenyl)-2,2-dimethyl-6-((tetrahydro-2H-pyran-2-yl)oxy)hexyl)oxy)(tert-butyl)dimethylsilane

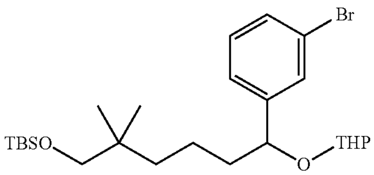

To a stirred solution of 1-(3-bromophenyl)-6-[tert-butyl(dimethyl)silyl]oxy-5,5-dimethyl-hexan-1-ol (Intermediate 35A, 20.00 g, 48.1 mmol) in dichloromethane (200 mL) was added 3,4-dihydro-2H-pyran (5.00 g, 60.2 mmol) and p-toluenesulfonic acid (332 mg, 1.93 mmol). The reaction was stirred for 1 hour at room temperature under argon atmosphere, then diluted with dichloromethane (200 mL). The solution was washed with brine (2×500 mL), dried over anhydrous magnesium sulfate and concentrated to afford the crude title compound as an oil (24.00 g, 99%). MS (ESI): 521, 523 m/z $[M+Na]^+$.

The following intermediate was prepared based on the procedures described for Intermediate 35B.

| Inter. No. | Structure | Name | MS m/z $[M + H]^+$ |
|---|---|---|---|
| 35B-1 | 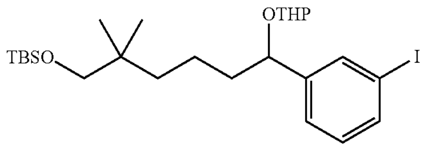 | tert-butyl((6-(3-iodophenyl)-2,2-dimethyl-6-((tetrahydro-2H-pyran-2-yl)oxy)hexyl)oxy)dimethylsilane | 569 $[M + Na]^+$ |

Intermediate 36: Ethyl 3-[3-(6-hydroxy-5,5-dimethyl-1-tetrahydropyran-2-yloxy-hexyl)phenyl]propanoate

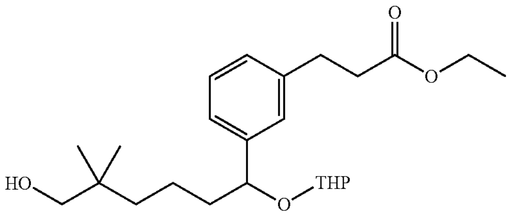

To a stirred solution of ethyl 3-(3-(6-hydroxy-5,5-dimethyl-1-((tetrahydro-2H-pyran-2-yl)oxy)hexyl)phenyl)acrylate (Intermediate 36A, 4.00 g, 9.89 mmol) in ethanol (40 mL) was added Raney Nickel (0.5 g). The reaction was stirred at room temperature under hydrogen for 3 hours. The mixture was filtered. The filtrate was concentrated to afford the crude title compound (8.00 g, 89%). MS (ESI): 429 m/z $[M+H]^+$.

Intermediate 36A: Ethyl 3-(3-(6-hydroxy-5,5-dimethyl-1-((tetrahydro-2H-pyran-2-yl)oxy)hexyl)phenyl)acrylate

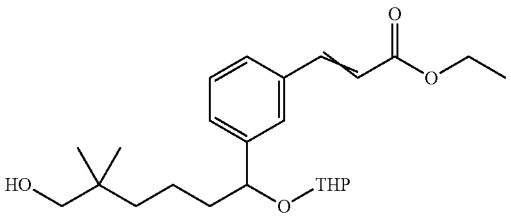

To a stirred and degassed solution of 6-(3-bromophenyl)-2,2-dimethyl-6-tetrahydropyran-2-yloxy-hexan-1-ol (Intermediate 35, 15.00 g, 38.9 mmol), ethyl acrylate (7.79 g, 77.9 mmol) and triethylamine (27.1 mL, 195 mmol) in N,N-dimethylformamide (300 mL) was added tri(o-tolyl)phosphine (4.74 g, 15.6 mmol), followed by palladium(II) acetate (1.31 g, 5.84 mmol). The reaction was stirred at 120° C. for 16 hours. The mixture was then cooled to room temperature, diluted with water (300 mL), and extracted with ethyl acetate (3×300 mL). The combined organic extracts were washed with water (3×200 mL), brine (200 mL), dried over anhydrous sodium sulfate and concentrated. The residue was purified by automated flash chromatography (120 g silica gel column, 0-50% ethyl acetate in petroleum ether) to give the title compound as an oil (8.90 g, 50%). MS (ESI): 427 m/z [M+H]+.

Intermediate 37: Ethyl 2-(3-(6-hydroxy-5,5-dimethyl-1-((tetrahydro-2H-pyran-2-yl)oxy)hexyl)phenyl)acetate

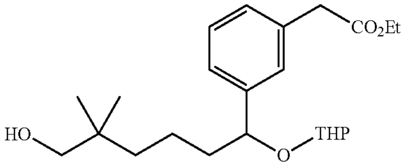

To a stirred solution of ethyl 2-(3-(6-((tert-butyldimethylsilyl)oxy)-5,5-dimethyl-1-((tetrahydro-2H-pyran-2-yl)oxy)hexyl)phenyl)acetate (Intermediate 37A, 3.50 g, 11.8 mmol) in tetrahydrofuran (20 mL) was added tetrabutylammonium fluoride (35.5 mL, 35.5 mmol, 1M in THF). The mixture was stirred at room temperature for 16 hours. After confirming the starting material was consumed by LC-MS analysis the reaction was quenched with water (100 mL), then extracted with ethyl acetate (3×150 mL). The combined organic layers were washed with brine (150 mL), dried over sodium sulfate and concentrated in vacuo. The residue was purified by silica gel column chromatography (5% ethyl acetate in petroleum ether) to give the title compound as a yellow oil (3.50 g, 75%). MS (ESI): 415 m/z [M+Na]+.

Intermediate 37A: Ethyl 2-(3-(6-((tert-butyldimethylsilyl)oxy)-5,5-dimethyl-1-((tetrahydro-2H-pyran-2-yl)oxy)hexyl)phenyl)acetate

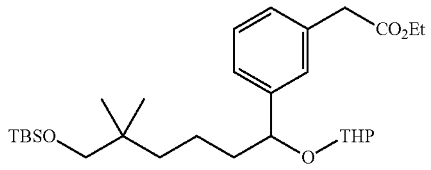

To a stirred solution of ((6-(3-Bromophenyl)-2,2-dimethyl-6-((tetrahydro-2H-pyran-2-yl)oxy)hexyl)oxy)(tert-butyl)dimethylsilane (Intermediate 35B) (10.00 g, 20.0 mmol) in mesitylene (120 mL) were added ethyl potassium malonate (5.11 g, 30 mmol), allylpalladium(II) chloride dimer (146 mg, 0.4 mmol), (R)-(+)-2,2'-bis(diphenylphosphino)-1,1'-binaphthyl (748 mg, 1.2 mmol) and 4-dimethylaminopyridine (245 mg, 2.0 mmol) under nitrogen. The mixture was stirred at 140° C. for 12 hours. After confirming by LC-MS analysis that the starting material was consumed, the mixture was concentrated. The residue was purified by silica gel column chromatography (5% ethyl acetate in petroleum ether) to give the title compound as a yellow oil (6.00 g, 59%). MS (ESI): 529 m/z [M+H]+.

Intermediate 38: Ethyl 3-[3-(6-hydroxy-5,5-dimethyl-1-tetrahydropyran-2-yloxy-hexyl)phenyl]-2-methyl-propanoate

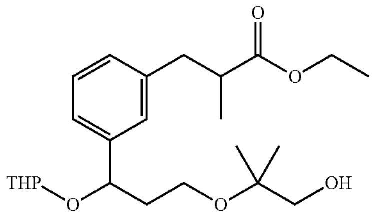

To a stirred solution of ethyl 3-(3-(6-hydroxy-5,5-dimethyl-1-((tetrahydro-2H-pyran-2-yl)oxy)hexyl)phenyl)-2-methylacrylate (Intermediate 38A, 31.50 g, 75.3 mmol) in ethanol (300 mL) was added Raney nickel (1 g). The reaction was stirred under hydrogen for 2 hours at room temperature. The mixture was filtered through a pad of Celite and washed with ethanol (300 mL). The filtrate was concentrated in vacuo to give the crude title compound as an oil (30.00 g, 94.8%). MS (ESI): 443 m/z [M+Na]+.

The following intermediates were prepared based on the procedures described for Intermediate 38, and/or procedures for 38A.

| Inter. No. | Structure | Name | MS m/z [M + H]+ |
| --- | --- | --- | --- |
| 38-1 | 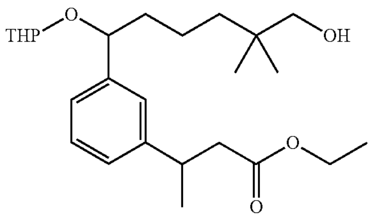 | ethyl 3-(3-(6-hydroxy-5,5-dimethyl-1-((tetrahydro-2H-pyran-2-yl)oxy)hexyl)phenyl)butanoate | 443 [M + Na]+ |

-continued

| Inter. No. | Structure | Name | MS m/z [M + H]+ |
|---|---|---|---|
| 38-2 | 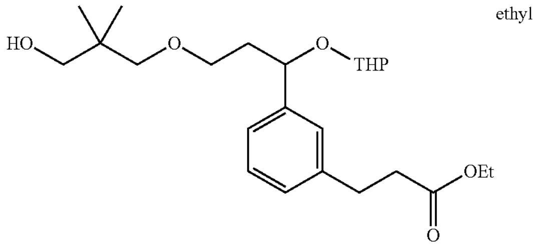 | ethyl 3-(3-(3-(3-hydroxy-2,2-dimethylpropoxy)-1-((tetrahydro-2H-pyran-2-yl)oxy)propyl)phenyl)propanoate | 445 [M + Na]+ |

Intermediate 38A: Ethyl 3-(3-(6-hydroxy-5,5-dimethyl-1-((tetrahydro-2H-pyran-2-yl)oxy)hexyl)phenyl)-2-methylacrylate

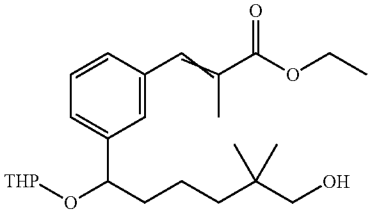

To a stirred solution of 6-(3-bromophenyl)-2,2-dimethyl-6-((tetrahydro-2H-pyran-2-yl)oxy)hexan-1-ol (Intermediate 35, 40 g, 104 mmol), ethyl methacrylate (23.7 g, 208 mmol) and triethylamine (43.4 mL, 311 mmol) in N,N-dimethylformamide (500 mL) was added tri(o-tolyl)phosphine (9.48 g, 31.1 mmol), followed by palladium(II) acetate (2.33 g, 10.4 mmol). The reaction was purged with nitrogen and stirred at 120° C. for 16 hours. The mixture was cooled to room temperature, diluted with ethyl acetate (500 mL). The solution was washed with water (2×500 mL), dried over anhydrous sodium sulfate and concentrated. The residue was purified by automated flash chromatography (330 g silica gel column, 0-40% ethyl acetate in petroleum ether) to give the title compound as an oil (31.50 g, 73%). MS (ESI): 441 m/z $[M+Na]^+$.

Intermediate 39: Ethyl 3-(3-(3-((1-hydroxy-2-methylpropan-2-yl)oxy)-1-((tetrahydro-2H-pyran-2-yl)oxy)propyl)phenyl)propanoate

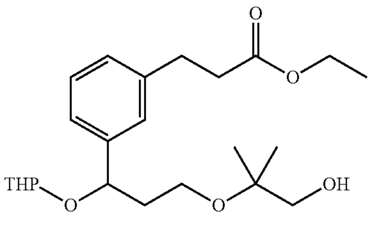

To a stirred solution of ethyl (E)-3-(3-(3-((1-hydroxy-2-methylpropan-2-yl)oxy)-1-((tetrahydro-2H-pyran-2-yl)oxy)propyl)phenyl)acrylate (Intermediate 39E, 9.10 g, 22.4 mmol) in ethanol (150 mL) was added Raney nickel (2.0 g). The reaction mixture was stirred under a hydrogen balloon for 2 hours at room temperature. The mixture was filtered through a pad of Celite and washed with ethanol (100 mL). The filtrate was then concentrated to give the title compound as an oil (8.2 Og, 92%). MS (ESI): 431 m/z $[M+Na]^+$.

Intermediate 39A: 1-(3-bromophenyl)-3-(1,1-dimethylallyloxy)propan-1-ol

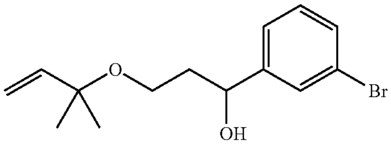 [SMILES: C=CC(C)(C)OCCC(O)c1cccc(Br)c1]

To a stirred and cooled (−78° C.) solution of 1-bromo-3-iodo-benzene (6.50 g, 23.0 mmol) in tetrahydrofuran (100 mL) was added dropwise isopropyl magnesium chloride-lithium chloride complex (1.3M in THF, 17.7 mL, 23 mmol). After stirring for 1 hour at this temperature, the reaction mixture was treated with a solution of 3-(1,1-dimethylallyloxy)propanal (Intermediate 31, 3.27 g, 23 mmol). The reaction was warmed up to room temperature and stirred for 1 hour, then quenched with water (100 mL) and concentrated to dryness. The residue was dissolved in ethyl acetate (200 mL), washed with brine (2×50 mL), dried over anhydrous sodium sulfate and concentrated. The crude was purified by automated silica gel column chromatography (80 g silica gel column, 0-50% ethyl acetate in petroleum ether) to give the title compound as an oil (3.90 g, 57%). $^1H$ NMR (400 MHz, $CDCl_3$) δ 7.54 (s, 1H), 7.37 (d, J=8.0 Hz, 1H), 7.28 (d, J=7.6 Hz, 1H), 7.19 (t, J=8.0 Hz, 1H), 5.82 (dd, J=17.6, 10.4 Hz, 1H), 5.15 (dd, J=14.2, 3.2 Hz, 2H), 4.89-4.86 (m, 1H), 4.24 (d, J=2.8 Hz, 1H), 3.53 (t, J=5.6 Hz, 2H), 1.92 (q, J=5.6 Hz, 2H), 1.3 (d, J=6.4 Hz, 6H) ppm.

Intermediate 39B: 2-(1-(3-Bromophenyl)-3-((2-methylbut-3-en-2-yl)oxy)propoxy)tetrahydro-2H-pyran

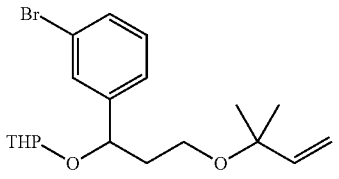

To a stirred solution of 1-(3-bromophenyl)-3-(1,1-dimethylallyloxy)propan-1-ol (Intermediate 39A, 21.00 g, 70.2 mmol) in dichloromethane (300 mL) was added 3,4-dihydro-2H-pyran (8 mL, 87.7 mmol) and p-toluenesulfonic acid (483 mg, 2.81 mmol). The mixture was stirred at room temperature for 1 hour, then quenched with water (300 mL), extracted with dichloromethane (200 mL). The combined organic extracts were washed with brine (2×300 mL), dried over anhydrous sodium sulfate and concentrated. The residue was purified by automated flash chromatography (330 g silica gel column, 0-10% ethyl acetate in petroleum ether) to give the title compound as an oil (21.00 g, 78.1%). MS (ESI): 405, 407 m/z $[M+Na]^+$.

Intermediate 39C: 2-(3-(3-Bromophenyl)-3-((tetrahydro-2H-pyran-2-yl)oxy)propoxy)-2-methylpropanal

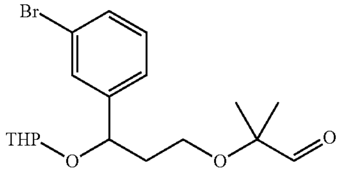

To a stirred and cooled (0° C.) solution of 2-(1-(3-bromophenyl)-3-((2-methylbut-3-en-2-yl)oxy)propoxy)tetrahydro-2H-pyran (Intermediate 39B) (20.00 g, 52.2 mmol) in tetrahydrofuran (400 mL) and water (200 mL) was added potassium osmate (VI) dihydrate (961 mg, 2.61 mmol) and 2,6-lutidine (6.08 mL, 5.59 mmol). The mixture was stirred at 0° C. for 10 minutes, then treated with sodium periodate (55.8 g, 261.0 mmol). The mixture was stirred at room temperature for 16 hours, then extracted with ethyl acetate (3×200 mL). The combined organic solution was washed with brine (200 mL), dried over anhydrous sodium sulfate and concentrated. The residue was purified by automated flash chromatography (330 g silica gel column, 0-20% ethyl acetate in petroleum ether) to afford the title compound as an oil (13.00 g, 64.7%). MS (ESI): 407, 409 m/z $[M+Na]^+$.

Intermediate 39D: 2-(3-(3-Bromophenyl)-3-((tetrahydro-2H-pyran-2-yl)oxy)propoxy)-2-methylpropan-1-ol

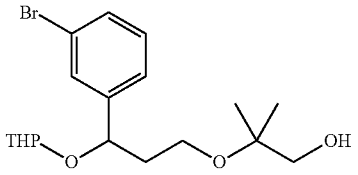

To a stirred solution of 2-(3-(3-bromophenyl)-3-((tetrahydro-2H-pyran-2-yl)oxy)propoxy)-2-methylpropanal (Intermediate 39C, 13.00 g, 33.7 mmol) in methanol (150 mL) was added sodium borohydride (1.28 g, 33.7 mmol). The reaction was stirred at room temperature for 1 hour, then quenched with water (200 mL). The mixture was extracted with ethyl acetate (3×150 mL). The combined organic extracts were washed with brine (2×200 mL), dried over anhydrous sodium sulfate and concentrated to give the crude title compound as an oil (12.00 g, crude). MS (ESI): 409, 411 m/z $[M+Na]^+$.

Intermediate 39E: Ethyl (E)-3-(3-(3-((1-hydroxy-2-methylpropan-2-yl)oxy)-1-((tetrahydro-2H-pyran-2-yl)oxy)propyl)phenyl)acrylate

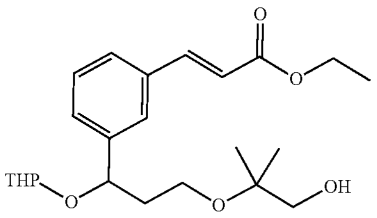

To a stirred solution of 2-(3-(3-bromophenyl)-3-((tetrahydro-2H-pyran-2-yl)oxy)propoxy)-2-methylpropan-1-ol (Intermediate 39D, 12.00 g, 31.0 mmol) in N,N-dimethylformamide (150 mL) were added ethyl acrylate (10.1 mL, 92.9 mmol), triethylamine (13.0 mL, 92.9 mmol), tri(o-tolyl)phosphine (2.83 g, 9.29 mmol) and palladium(II) acetate (696 mg, 3.1 mmol) sequentially. The reaction was purged with nitrogen and stirred at 120° C. for 16 hours. The mixture was cooled to room temperature and diluted with ethyl acetate (200 mL). The solution was washed with water (2×200 mL), dried over anhydrous sodium sulfate and concentrated. The residue was purified by automated flash chromatography (120 g silica gel column, 0-25% ethyl acetate in petroleum ether) to give the title compound as an oil (9.10 g, 72%). MS (ESI): 429 m/z $[M+Na]^+$.

Intermediate 40: 2-(3-Bromophenyl)-7-hydroxy-2,6,6-trimethylheptanoic Acid

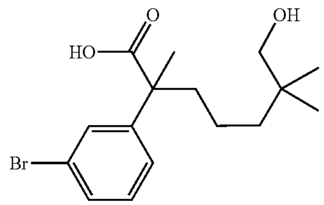 [SMILES: CC(C)(CO)CCCC(C)(C(=O)O)c1cccc(Br)c1]

To a stirred solution of methyl 2-(3-bromophenyl)-7-hydroxy-2,6,6-trimethylheptanoate (Intermediate 40B, 10.0 g, 28.0 mmol) in 3:1 tetrahydrofuran/methanol (320 mL) was added a 1.0 M aqueous solution of lithium hydroxide (84 mL, 84 mmol). The reaction was stirred overnight at room temperature and then analyzed by LCMS and found to be complete. After acidifying with the addition of 1.0 M hydrochloric acid (to approximately pH 4, by litmus paper), the mixture was extracted with ethyl acetate (1×300 mL). The organic layer was washed with brine (2×300 mL), dried over sodium sulfate and concentrated. The crude title compound, which was used without purification, was obtained as a colorless oil (8.80 g, 92%). MS (ESI): 365 m/z $[M+Na]^+$.

The following intermediate was prepared based on the procedures described for Intermediate 40, and/or for Intermediates 40A and 40B.

| Inter. No. | Structure | Name | MS m/z $[M + H]^+$ |
|---|---|---|---|
| 40-1 | 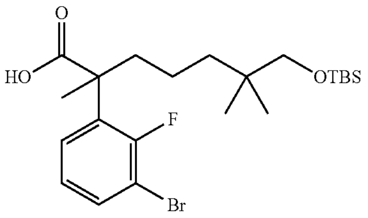 [SMILES: CC(C)(CCCC(C)(C(=O)O)c1cccc(Br)c1F)CO[Si](C)(C)C(C)(C)C] | 2-(3-bromo-2-fluorophenyl)-7-((tert-butyldimethylsilyl)oxy)-2,6,6-trimethylheptanoic acid | 475, 477 m/z $[M + H]^+$; RT: 3.03 min. (LC-MS method 39) |

Intermediate 40A: Methyl 2-(3-bromophenyl)-5-((tert-butyldimethylsilyl)oxy)-2-methylpentanoate

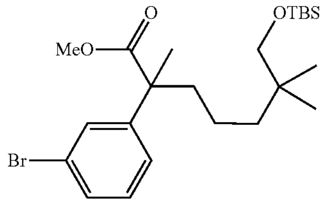 [SMILES: COC(=O)C(C)(CCCC(C)(C)CO[Si](C)(C)C(C)(C)C)c1cccc(Br)c1]

To a stirred and cooled (−65° C.) solution of methyl 2-(3-bromophenyl)propanoate (10.0 g, 41.1 mmol) in tetrahydrofuran (100 mL) was added, dropwise over 20 minutes, a 2.0 M solution of lithium diisopropylamide in tetrahydrofuran/heptane/ethylbenzene (24.7 mL, 49.4 mmol). The mixture was maintained at −65° C. for one hour before adding, dropwise over 20 minutes, tert-butyl((5-iodo-2,2-dimethylpentyl)oxy)dimethylsilane (Intermediate 29C-1, 17.6 g, 49.4 mmol). The reaction was then allowed to warm to room temperature and stirred for an additional two hours. After this time, the reaction was quenched by the slow addition of aqueous ammonium chloride solution (100 mL). The biphasic mixture was extracted with ethyl acetate (2×150 mL) and the combined organic layers were washed with brine (1×100 mL), dried over sodium sulfate and concentrated. The crude residue was purified by automated flash chromatography (330 g silica gel column, 5% ethyl acetate in petroleum ether) to afford the title compound as a yellow oil (13.3 g, 69%). $^1H$ NMR (400 MHz, $CDCl_3$) δ 7.46-7.45 (m, 1H), 7.39-7.36 (m, 1H), 7.25-7.17 (m, 2H), 3.66 (s, 3H), 3.18 (s, 2H), 2.03-1.78 (m, 2H), 1.54 (s, 3H), 1.27-1.09 (m, 4H), 0.88 (s, 9H), 0.78 (s, 6H), 0.02 (s, 6H) ppm.

The following intermediate was prepared based on the procedures described for Intermediate 40A.

| Inter. No. | Structure | Name | MS m/z [M + H]$^+$ |
|---|---|---|---|
| 40A-1 | 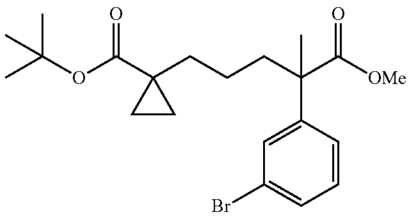 [SMILES: COC(=O)C(C)(CCCC1(C(=O)OC(C)(C)C)CC1)c1cccc(Br)c1] | tert-butyl 1-(4-(3-bromophenyl)-5-methoxy-4-methyl-5-oxopentyl)cyclopropane-1-carboxylate | 447, 449 m/z [M + Na]$^+$ |
| 40A-2 | 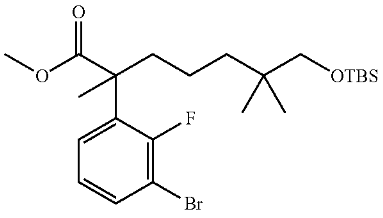 [SMILES: COC(=O)C(C)(CCCC(C)(C)CO[Si](C)(C)C(C)(C)C)c1cccc(Br)c1F] | methyl 2-(3-bromo-2-fluorophenyl)-7-((tert-butyldimethylsilyl)oxy)-2,6,6-trimethylheptanoate | 489, 491 m/z [M + H]$^+$; RT: 2.93 min. (LC-MS method 38) |

Intermediate 40B: Methyl 2-(3-bromophenyl)-7-hydroxy-2,6,6-trimethylheptanoate

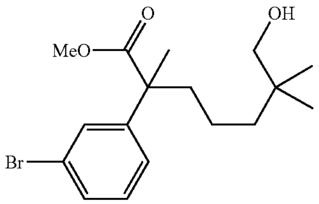 [SMILES: COC(=O)C(C)(CCCC(C)(C)CO)c1cccc(Br)c1]

To a stirred solution of methyl 2-(3-bromophenyl)-5-((tert-butyldimethylsilyl)oxy)-2-methylpentanoate (Intermediate 40A, 16.1 g, 34.1 mmol) in tetrahydrofuran (100 mL) was added a 1.0 M solution of tetrabutylammonium fluoride in tetrahydrofuran (102 mL, 102 mmol). The reaction was stirred overnight at room temperature and then concentrated. The resulting gummy solid was partitioned between ethyl acetate (100 mL) and brine (80 mL). The organic layer was combined with additional extracts (ethyl acetate, 2×100 mL), washed with 2.0N hydrochloric acid (1×150 mL), dried over sodium sulfate and concentrated. The crude residue was purified by automated flash chromatography (220 g silica gel column, 20% ethyl acetate in petroleum ether) to afford the title compound as a yellow oil (11.2 g, 92%). MS (ESI): 339 m/z $[M-OH^-]^+$.

The following intermediates were prepared based on the procedures described for Intermediate 40B.

| Inter. No. | Structure | Name | MS m/z [M + H]$^+$ |
|---|---|---|---|
| 40B-1 | 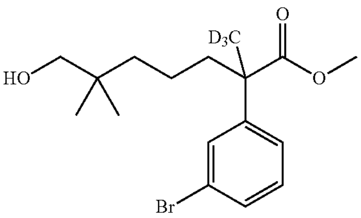 [SMILES: [2H]C([2H])([2H])C(CCCC(C)(C)CO)(C(=O)OC)c1cccc(Br)c1] | methyl 2-(3-bromophenyl)-7-hydroxy-6,6-dimethyl-2-(methyl-d3)heptanoate | 384, 382 [M + Na]$^+$ |
| 40B-2 | 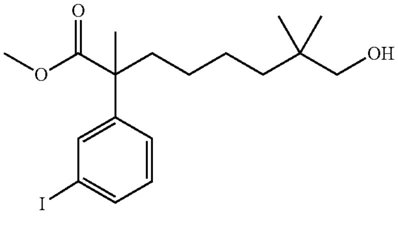 [SMILES: COC(=O)C(C)(CCCCC(C)(C)CO)c1cccc(I)c1] | methyl 8-hydroxy-2-(3-iodophenyl)-2,7,7-trimethyloctanoate | 441 [M + Na]$^+$ |

-continued

| Inter. No. | Structure | Name | MS m/z $[M + H]^+$ |
|---|---|---|---|
| 40B-3 | 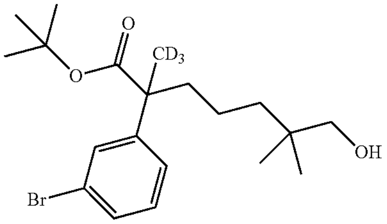 [SMILES: [2H]C([2H])([2H])C(CCCC(C)(C)CO)(C(=O)OC(C)(C)C)c1cccc(Br)c1] | tert-butyl 2-(3-bromophenyl)-7-hydroxy-6,6-dimethyl-2-(methyl-d3)heptanoate | 424, 426 $[M + Na]^+$ |
| 40B-4 | 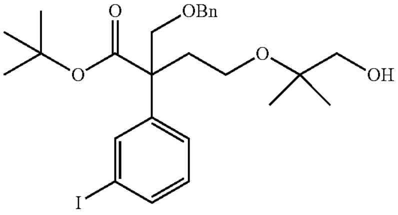 [SMILES: CC(C)(C)OC(=O)C(CCOC(C)(C)CO)(COCc1ccccc1)c1cccc(I)c1] | tert-butyl 2-((benzyloxy)methyl)-4-((1-hydroxy-2-methylpropan-2-yl)oxy)-2-(3-iodophenyl)butanoate | 577 $[M + Na]^+$ |
| 40B-5 | 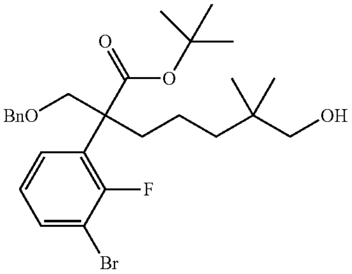 [SMILES: CC(C)(CO)CCCC(COCc1ccccc1)(C(=O)OC(C)(C)C)c1cccc(Br)c1F] | tert-butyl 2-((benzyloxy)methyl)-2-(3-bromo-2-fluorophenyl)-7-hydroxy-6,6-dimethylheptanoate | 545, 547 $[M + Na]^+$ |
| 40B-6 | 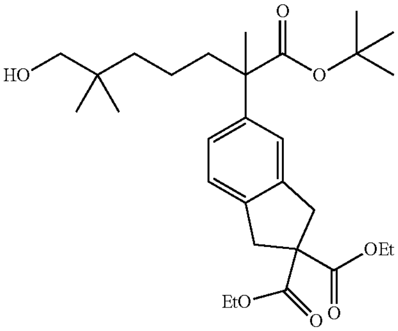 [SMILES: CCOC(=O)C1(C(=O)OCC)Cc2ccc(C(C)(CCCC(C)(C)CO)C(=O)OC(C)(C)C)cc2C1] | diethyl 5-(1-(tert-butoxy)-7-hydroxy-2,6,6-trimethyl-1-oxoheptan-2-yl)-1,3-dihydro-2H-indene-2,2-dicarboxylate | 527 $[M + Na]^+$ |
| 40B-7 | 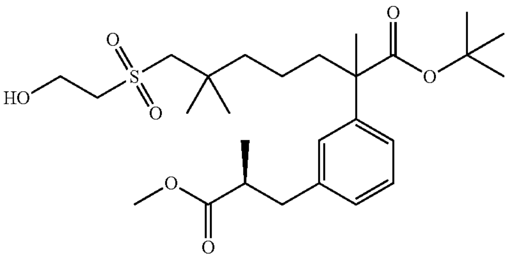 [SMILES: COC(=O)[C@@H](C)Cc1cccc(C(C)(CCCC(C)(C)CS(=O)(=O)CCO)C(=O)OC(C)(C)C)c1] | tert-butyl 7-((2-hydroxyethyl)sulfonyl)-2-(3-((S)-3-methoxy-2-methyl-3-oxopropyl)phenyl)-2,6,6-trimethylheptanoate | 535 $[M + Na]^+$ |

-continued

| Inter. No. | Structure | Name | MS m/z [M + H]$^+$ |
|---|---|---|---|
| 40B-8 | 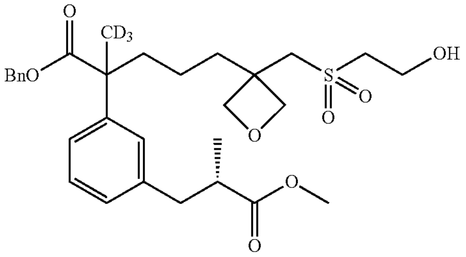 [SMILES: [2H]C([2H])([2H])C(CCCC1(CS(=O)(=O)CCO)COC1)(C(=O)OCc1ccccc1)c1cccc(C[C@H](C)C(=O)OC)c1] | benzyl 5-(3-(((2-hydroxyethyl)sulfonyl)methyl)oxetan-3-yl)-2-(3-((S)-3-methoxy-2-methyl-3-oxopropyl)phenyl)-2-(methyl-d3)pentanoate | 564 |
| 40B-9 | 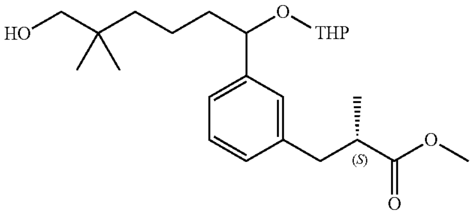 | methyl (2S)-3-(3-(6-hydroxy-5,5-dimethyl-1-((tetrahydro-2H-pyran-2-yl)oxy)hexyl)phenyl)-2-methylpropanoate | 429 (mixture of diastereomers) |
| 40B-10 | 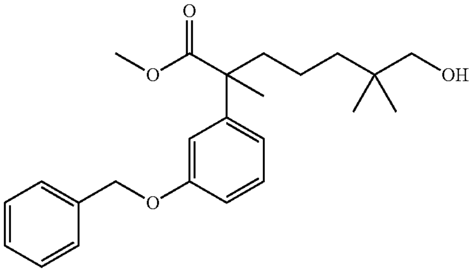 [SMILES: COC(=O)C(C)(CCCC(C)(C)CO)c1cccc(OCc2ccccc2)c1] | methyl 2-(3-(benzyloxy)phenyl)-7-hydroxy-2,6,6-trimethylheptanoate | 407 [M + Na]$^+$ |
| 40B-11 | 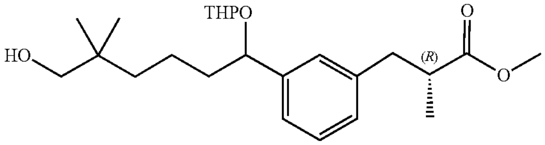 | methyl (2R)-3-(3-(6-hydroxy-5,5-dimethyl-1-((tetrahydro-2H-pyran-2-yl)oxy)hexyl)phenyl)-2-methylpropanoate | 429 [M + Na]$^+$ |
| 40B-12 | 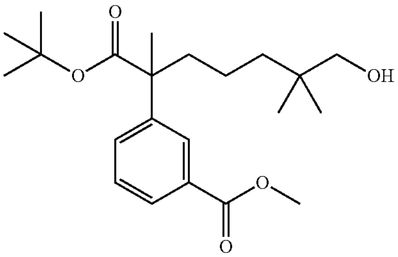 [SMILES: COC(=O)c1cccc(C(C)(CCCC(C)(C)CO)C(=O)OC(C)(C)C)c1] | methyl 3-(1-(tert-butoxy)-7-hydroxy-2,6,6-trimethyl-1-oxoheptan-2-yl)benzoate | 396 [M + $H_2O$]$^+$ |
| 40B-13 | 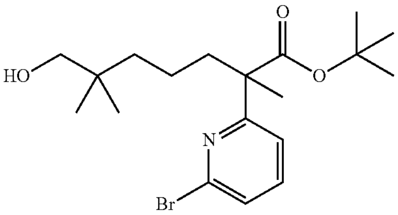 [SMILES: CC(C)(CO)CCCC(C)(C(=O)OC(C)(C)C)c1cccc(Br)n1] | tert-butyl 2-(6-bromopyridin-2-yl)-7-hydroxy-2,6,6-trimethylheptanoate | 400, 402 |

-continued

| Inter. No. | Structure | Name | MS m/z [M + H]+ |
|---|---|---|---|
| 40B-14 | 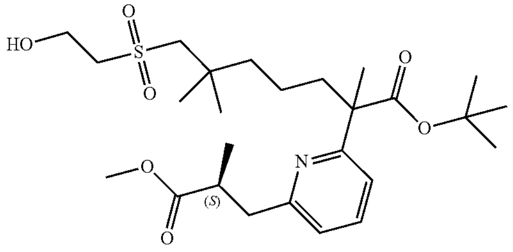 | tert-butyl 7-((2-hydroxyethyl)sulfonyl)-2-(6-((S)-3-methoxy-2-methyl-3-oxopropyl)pyridin-2-yl)-2,6,6-trimethylheptanoate | 514 |
| 40B-15 | 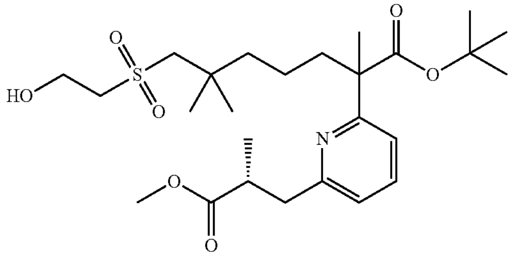 [SMILES: COC(=O)[C@H](C)Cc1cccc(C(C)(CCCC(C)(C)CS(=O)(=O)CCO)C(=O)OC(C)(C)C)n1] | tert-butyl 7-((2-hydroxyethyl)sulfonyl)-2-(6-((R)-3-methoxy-2-methyl-3-oxopropyl)pyridin-2-yl)-2,6,6-trimethylheptanoate | 514 |

Intermediate 41: Benzyl 2-(3-bromophenyl)-7-hydroxy-2,6,6-trimethylheptanoate

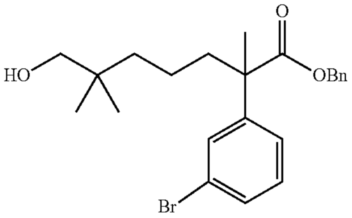 [SMILES: CC(C)(CO)CCCC(C)(C(=O)OCc1ccccc1)c1cccc(Br)c1]

To a stirred solution of 2-(3-bromophenyl)-7-hydroxy-2,6,6-trimethylheptanoic acid (Intermediate 40, 20.0 g, 58.3 mmol) in acetone (300 mL) was added benzyl bromide (8.30 mL, 11.9 g, 69.9 mmol) and potassium carbonate (16.1 g, 116 mmol). The reaction was heated overnight at 70° C. and then cooled to room temperature and concentrated. The residue was partitioned between ethyl acetate (200 mL) and water (200 mL). The organic layer was washed with a second portion of water (1×200 mL), dried over sodium sulfate and concentrated. The crude residue was purified by automated flash chromatography (330 g silica gel column, 0-30% ethyl acetate in petroleum ether) to afford the title compound as a colorless oil (22.0 g, 87%). MS (ESI): 455, 457 m/z $[M+Na]^+$.

The following intermediates were prepared based on the procedures described for Intermediate 41.

| Inter. No. | Structure | Name | MS m/z [M + H]+ |
|---|---|---|---|
| 41-1 | 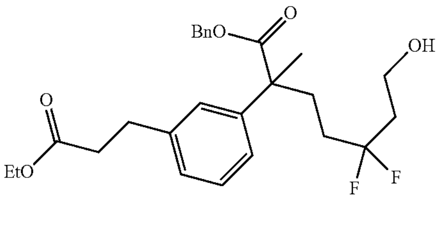 [SMILES: CCOC(=O)CCc1cccc(C(C)(CCC(F)(F)CCO)C(=O)OCc2ccccc2)c1] | Benzyl 2-(3-(3-ethoxy-3-oxopropyl)phenyl)-5,5-difluoro-7-hydroxy-2-methylheptanoate | 485 $[M + Na]^+$. |
| 41-2 | 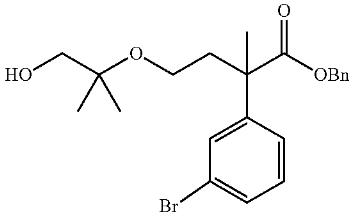 | Benzyl 2-(3-bromophenyl)-4-((1-hydroxy-2-methylpropan-2-yl)oxy)-2-methylbutanoate | 457, 459 $[M + Na]^+$. |

-continued

| Inter. No. | Structure | Name | MS m/z $[M + H]^+$ |
|---|---|---|---|
| 41-3 | 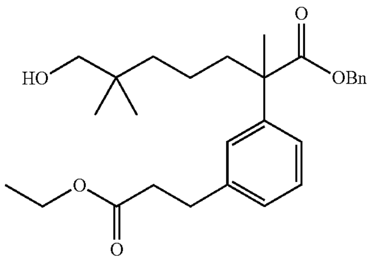 [SMILES: CCOC(=O)CCc1cccc(C(C)(CCCC(C)(C)CO)C(=O)OCc2ccccc2)c1] | Benzyl 2-(3-(3-ethoxy-3-oxopropyl)phenyl)-7-hydroxy-2,6,6-trimethylheptanoate | $^1$H NMR (400 MHz, $CDCl_3$) δ 7.36-7.27 (m, 3H), 7.23-7.20 (m, 3H), 7.13-7.05 (m, 3 H), 5.12 (q, J = 12.4 Hz, 2H), 4.14-4.09 (m, 2H), 3.22 (d, J = 6.0 Hz, 2 H), 2.89 (t, J = 8.0 Hz, 2H), 2.55 (t, J = 8.0 Hz, 2H), 2.01 (s, 2 H), 1.54 (s, 3 H), 1.27-1.19 (m, 7 H), 0.70 (s, 6H) ppm. |
| 41-4 | 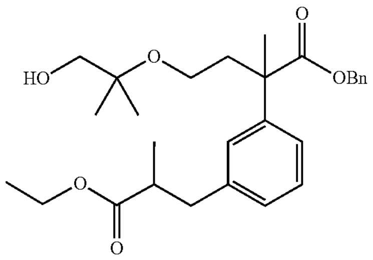 [SMILES: CCOC(=O)C(C)Cc1cccc(C(C)(CCOC(C)(C)CO)C(=O)OCc2ccccc2)c1] | benzyl 2-(3-(3-ethoxy-2-methyl-3-oxopropyl)phenyl)-4-((1-hydroxy-2-methylpropan-2-yl)oxy)-2-methylbutanoate | 471 |
| 41-5 | 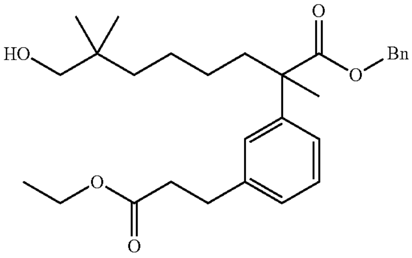 [SMILES: CCOC(=O)CCc1cccc(C(C)(CCCCC(C)(C)CO)C(=O)OCc2ccccc2)c1] | benzyl 2-(3-(3-ethoxy-3-oxopropyl)phenyl)-8-hydroxy-2,7,7-trimethyloctanoate | 469 |
| 41-6 | 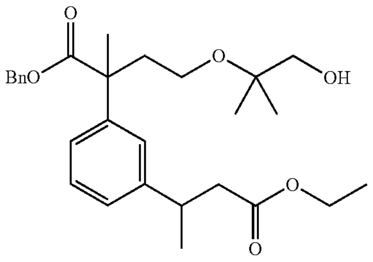 | benzyl 2-(3-(4-ethoxy-4-oxobutan-2-yl)phenyl)-4-((1-hydroxy-2-methylpropan-2-yl)oxy)-2-methylbutanoate | 493 $[M + Na]^+$. |
| 41-7 | 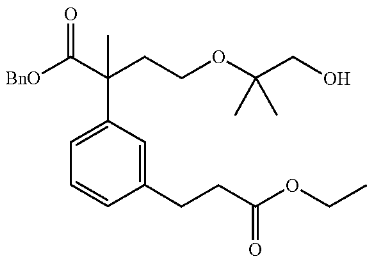 [SMILES: CCOC(=O)CCc1cccc(C(C)(CCOC(C)(C)CO)C(=O)OCc2ccccc2)c1] | benzyl 2-(3-(3-ethoxy-3-oxopropyl)phenyl)-4-((1-hydroxy-2-methylpropan-2-yl)oxy)-2-methylbutanoate | 457 |

-continued

| Inter. No. | Structure | Name | MS m/z [M + H]+ |
|---|---|---|---|
| 41-8 | 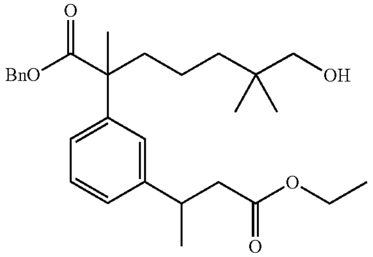 [SMILES: CCOC(=O)CC(C)c1cccc(C(C)(CCCC(C)(C)CO)C(=O)OCc2ccccc2)c1] | benzyl 2-(3-(4-ethoxy-4-oxobutan-2-yl)phenyl)-7-hydroxy-2,6,6-trimethylheptanoate | 469 |
| 41-9 | 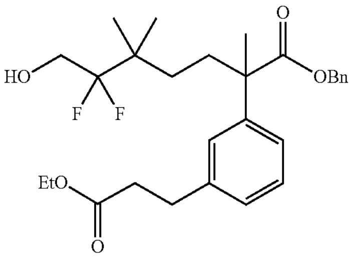 [SMILES: CCOC(=O)CCc1cccc(C(C)(CCC(C)(C)C(F)(F)CO)C(=O)OCc2ccccc2)c1] | benzyl 2-(3-(3-ethoxy-3-oxopropyl)phenyl)-6,6-difluoro-7-hydroxy-2,5,5-trimethylheptanoate | 513 [M + Na]+ |
| 41-10 | 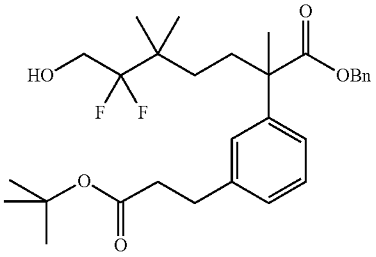 [SMILES: CC(C)(C)OC(=O)CCc1cccc(C(C)(CCC(C)(C)C(F)(F)CO)C(=O)OCc2ccccc2)c1] | benzyl 2-(3-(3-(tert-butoxy)-3-oxopropyl)phenyl)-6,6-difluoro-7-hydroxy-2,5,5-trimethylheptanoate | 541 [M + Na]+ |
| 41-11 | 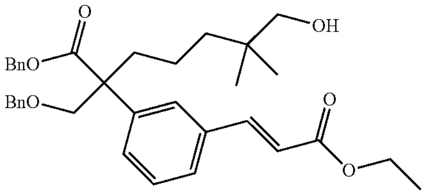 [SMILES: CCOC(=O)/C=C/c1cccc(C(CCCC(C)(C)CO)(COCc2ccccc2)C(=O)OCc2ccccc2)c1] | benzyl (E)-2-((benzyloxy)methyl)-2-(3-(3-ethoxy-3-oxoprop-1-en-1-yl)phenyl)-7-hydroxy-6,6-dimethylheptanoate | 559 |
| 41-12 | 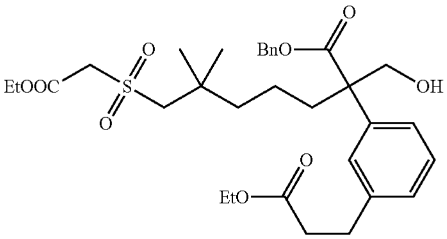 [SMILES: CCOC(=O)CCc1cccc(C(CO)(CCCC(C)(C)CS(=O)(=O)CC(=O)OCC)C(=O)OCc2ccccc2)c1] | benzyl 7-((2-ethoxy-2-oxoethyl)sulfonyl)-2-(3-(3-ethoxy-3-oxopropyl)phenyl)-2-(hydroxymethyl)-6,6-dimethylheptanoate | 627 [M + Na]+ |
| 41-13 | 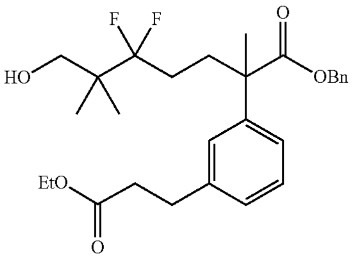 [SMILES: CCOC(=O)CCc1cccc(C(C)(CCC(F)(F)C(C)(C)CO)C(=O)OCc2ccccc2)c1] | benzyl 2-(3-(3-ethoxy-3-oxopropyl)phenyl)-5,5-difluoro-7-hydroxy-2,6,6-trimethylheptanoate | 513 [M + Na]+ |

-continued

| Inter. No. | Structure | Name | MS m/z [M + H]$^+$ |
|---|---|---|---|
| 41-14 | 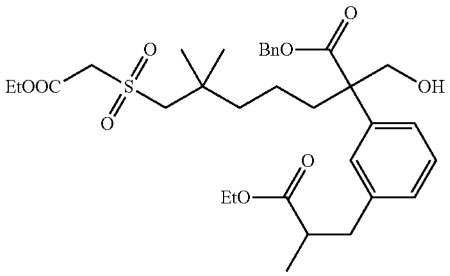 [SMILES: CCOC(=O)CS(=O)(=O)CC(C)(C)CCCC(CO)(C(=O)OCc1ccccc1)c1cccc(CC(C)C(=O)OCC)c1] | benzyl 2-(3-(3-ethoxy-2-methyl-3-oxopropyl)phenyl)-7-((2-ethoxy-2-oxoethyl)sulfonyl)-2-(hydroxymethyl)-6,6-dimethylheptanoate | 641 [M + Na]$^+$ |
| 41-15 | 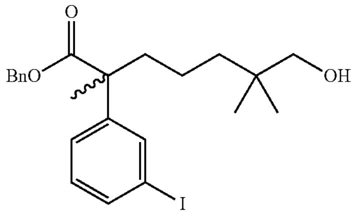 [SMILES: CC(C)(CO)CCCC(C)(C(=O)OCc1ccccc1)c1cccc(I)c1] | Enantiomer 1 of benzyl 7-hydroxy-2-(3-iodophenyl)-2,6,6-trimethylheptanoate | 503 [M + Na]$^+$ 98% ee |

Intermediate 42: Benzyl 2-(3-(2-ethoxy-2-oxoethoxy)phenyl)-7-hydroxy-2,6,6-trimethylheptanoate

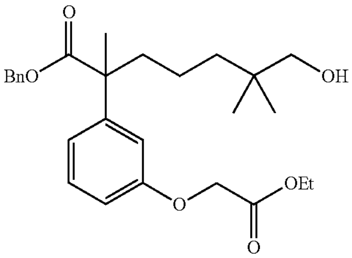 [SMILES: CCOC(=O)COc1cccc(C(C)(CCCC(C)(C)CO)C(=O)OCc2ccccc2)c1]

To a stirred solution of crude benzyl 7-hydroxy-2-(3-hydroxyphenyl)-2,6,6-trimethylheptanoate (Intermediate 42C, 16.0 g, 43.2 mmol) in N,N-dimethylformamide (150 mL) was added ethyl bromoacetate (9.6 mL, 14 g, 87 mmol) and potassium carbonate (14.9 g, 108 mmol). The reaction was stirred overnight at room temperature and then partitioned between ethyl acetate (500 mL) and water (500 mL). The organic layer was washed with additional portions of water (2×500 mL), dried over magnesium sulfate and concentrated. The crude residue was purified by automated flash chromatography (330 g silica gel column, 0-30% ethyl acetate in petroleum ether) to afford the title compound as a viscous oil (15.0 g, 76%). MS (ESI): 479 m/z [M+Na]$^+$.

The following intermediates were prepared based on the procedures described for Intermediate 42, and/or for Intermediates 42A-B.

| Inter. No. | Structure | Name | MS m/z [M + H]$^+$ |
|---|---|---|---|
| 42-1 | 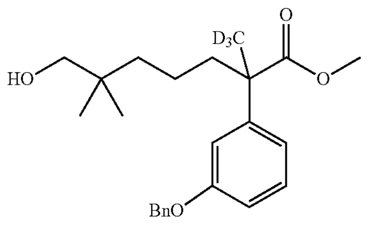 [SMILES: [2H]C([2H])([2H])C(CCCC(C)(C)CO)(C(=O)OC)c1cccc(OCc2ccccc2)c1] | methyl 2-(3-(benzyloxy)phenyl)-7-hydroxy-6,6-dimethyl-2-(methyl-d3)heptanoate | 410 |
| 42-2 | 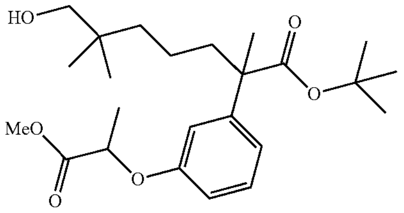 [SMILES: COC(=O)C(C)Oc1cccc(C(C)(CCCC(C)(C)CO)C(=O)OC(C)(C)C)c1] | tert-butyl 7-hydroxy-2-(3-((1-methoxy-1-oxopropan-2-yl)oxy)phenyl)-2,6,6-trimethylheptanoate | 445.3 [M + Na]$^+$ |
| 42-3 | 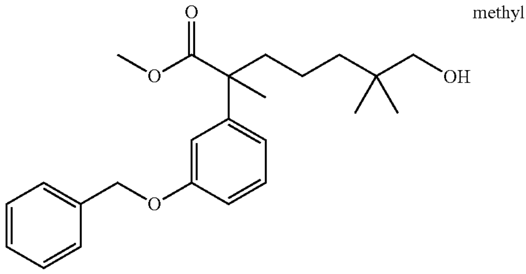 | methyl 2-(3-(benzyloxy)phenyl)-7-hydroxy-2,6,6-trimethylheptanoate | 407 [M + Na]$^+$ |

Intermediate 42A: Benzyl 7-hydroxy-2,6,6-trimethyl-2-(3-(4,4,5,5-tetramethyl-1,3,2-dioxaborolan-2-yl)phenyl)heptanoate

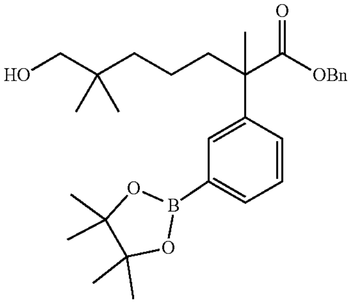 [SMILES: CC(C)(CO)CCCC(C)(C(=O)OCc1ccccc1)c1cccc(B2OC(C)(C)C(C)(C)O2)c1]

To a stirred solution of benzyl 2-(3-bromophenyl)-7-hydroxy-2,6,6-trimethylheptanoate (Intermediate 41, 20.0 g, 46.1 mmol) in 1,4-dioxane (200 mL) was added bis(pinacolato)diboron (17.6 g, 69.3 mol), potassium acetate (11.3 g, 115 mmol) and [1,1'-bis(diphenylphosphino)ferrocene]dichloropalladium(II) dichloromethane complex (3.77 g, 4.62 mmol). After purging with argon for 15 minutes, the mixture was heated overnight at 85° C. The reaction was cooled to room temperature and partitioned between ethyl acetate (500 mL) and water (500 mL). The organic layer was washed with a second portion of water (1×500 mL), dried over sodium sulfate and concentrated. The crude residue was purified by automated flash chromatography (330 g silica gel column, 0-30% ethyl acetate in petroleum ether) to afford the title compound as an oil (21.1 g, 95%). MS (ESI): 503 m/z [M+Na]$^+$.

The following intermediates were prepared based on the procedures described for Intermediate 42A.

| Inter. No. | Structure | Name | MS m/z [M + H]+ |
|---|---|---|---|
| 42A-1 | 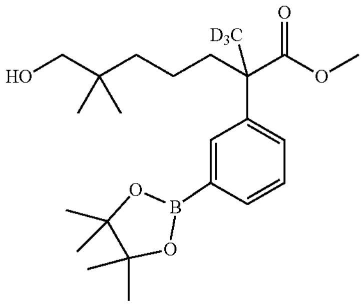 [SMILES: [2H]C([2H])([2H])C(CCCC(C)(C)CO)(C(=O)OC)c1cccc(B2OC(C)(C)C(C)(C)O2)c1] | methyl 7-hydroxy-6,6-dimethyl-2-(methyl-d3)-2-(3-(4,4,5,5-tetramethyl-1,3,2-dioxaborolan-2-yl)phenyl)heptanoate | 430 m/z [M + Na]+ |
| 42A-2 | 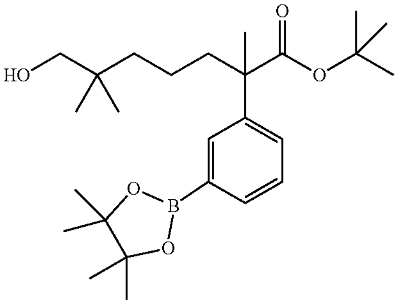 [SMILES: CC(C)(CO)CCCC(C)(C(=O)OC(C)(C)C)c1cccc(B2OC(C)(C)C(C)(C)O2)c1] | tert-butyl 7-hydroxy-2,6,6-trimethyl-2-(3-(4,4,5,5-tetramethyl-1,3,2-dioxaborolan-2-yl)phenyl)heptanoate | 469.3 [M + Na]+ |

Intermediate 42B: Benzyl 7-hydroxy-2-(3-hydroxyphenyl)-2,6,6-trimethylheptanoate

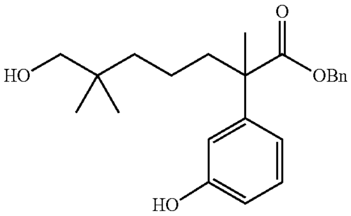 [SMILES: CC(C)(CO)CCCC(C)(C(=O)OCc1ccccc1)c1cccc(O)c1]

To a stirred solution of benzyl 7-hydroxy-2,6,6-trimethyl-2-(3-(4,4,5,5-tetramethyl-1,3,2-dioxaborolan-2-yl)phenyl) heptanoate (Intermediate 42A, 21.0 g, 43.7 mmol) in 2:1 tetrahydrofuran/water (600 mL) was added sodium perborate tetrahydrate (20.2 g, 131 mmol). The reaction was stirred at room temperature for one hour and then partitioned between ethyl acetate (300 mL) and water (300 mL). The organic layer was washed with additional portions of water (2×300 mL), dried over magnesium sulfate and concentrated. The crude title compound, which was used without purification, was obtained as a viscous oil (16.0 g, 99%). MS (ESI): 393 m/z $[M+Na]^+$.

The following intermediates were prepared based on the procedures described for Intermediate 42B.

| Inter. No. | Structure | Name | MS m/z [M + H]+ |
|---|---|---|---|
| 42B-1 | 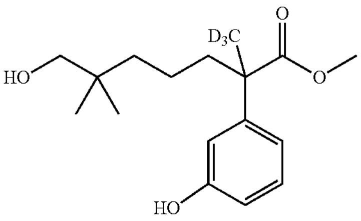 [SMILES: [2H]C([2H])([2H])C(CCCC(C)(C)CO)(C(=O)OC)c1cccc(O)c1] | methyl 7-hydroxy-2-(3-hydroxyphenyl)-6,6-dimethyl-2-(methyl-d3)heptanoate | 298 |
| 42B-2 | 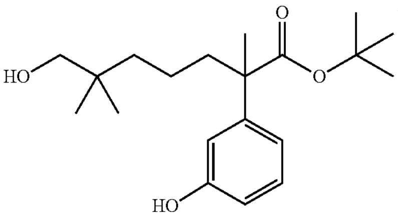 [SMILES: CC(C)(CO)CCCC(C)(C(=O)OC(C)(C)C)c1cccc(O)c1] | tert-butyl 7-hydroxy-2-(3-hydroxyphenyl)-2,6,6-trimethylheptanoate | 359.2 [M + Na]+ |

Intermediate 43: 2-(3-(2-Ethoxy-2-oxoethoxy)phenyl)-7-((2-ethoxy-2-oxoethyl)sulfonyl)-2,6,6-trimethylheptanoic Acid

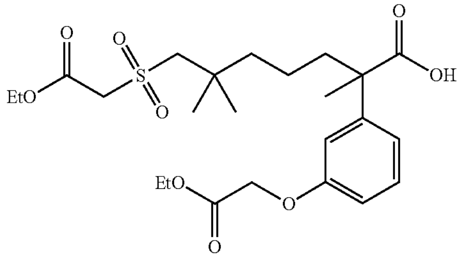 [SMILES: CCOC(=O)COc1cccc(C(C)(CCCC(C)(C)CS(=O)(=O)CC(=O)OCC)C(=O)O)c1]

A stirred suspension of benzyl 2-(3-(2-ethoxy-2-oxoethoxy)phenyl)-7-((2-ethoxy-2-oxoethyl)sulfonyl)-2,6,6-trimethylheptanoate (Intermediate 43C, 5.28 g, 8.94 mmol) and 10% palladium on carbon (1.00 g) in methanol (50 mL) was cycled between vacuum and a nitrogen atmosphere three times. After a final evacuation, the reaction vessel was backfilled with hydrogen (via balloon). The reaction was allowed to proceed for two hours before the hydrogen was evacuated and the vessel was opened to air. The catalyst was removed by suction filtration through a pad of Celite, which was subsequently rinsed with additional methanol (total, 150 mL). The combined filtrate was concentrated to afford the crude title compound, which was used without purification, as a pale amber oil (3.98 g, 89%). MS (ESI): 523 m/z $[M+Na]^+$.

The following intermediates were prepared based on the procedures described for Intermediate 43, and/or for Intermediates 43A to 43C.

| Inter. No. | Structure | Name | MS m/z $[M + H]^+$ |
|---|---|---|---|
| 43-1 | 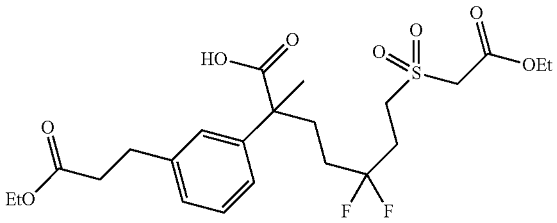 [SMILES: CCOC(=O)CCc1cccc(C(C)(CCC(F)(F)CCS(=O)(=O)CC(=O)OCC)C(=O)O)c1] | 7-((2-Ethoxy-2-oxoethyl)sulfonyl)-2-(3-(3-ethoxy-3-oxopropyl)phenyl)-5,5-difluoro-2-methylheptanoic acid | 507 |
| 43-2 | 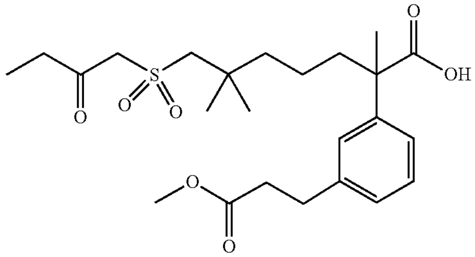 [SMILES: CCC(=O)CS(=O)(=O)CC(C)(C)CCCC(C)(C(=O)O)c1cccc(CCC(=O)OC)c1] | 7-((2-Methoxy-2-oxoethyl)sulfonyl)-2-(3-(3-methoxy-3-oxopropyl)phenyl)-2,6,6-trimethylheptanoic acid | $^1H$ NMR (400 MHz, DMSO-$d_6$) δ 12.29 (s, 1H), 7.25-7.07 (m, 4H), 4.05-4.00 (m, 2H), 3.69 (s, 3 H), 3.57 (s, 3H), 3.26 (s, 2 H), 2.84 (t, J = 7.6 Hz, 2 H), 2.60 (t, J = 7.2 Hz, 2 H), 1.98 (s, 3 H), 1.90-1.47 (m, 2H), 1.44-1.40 (m, 4H), 1.06 (s, 6H) ppm. |
| 43-3 | 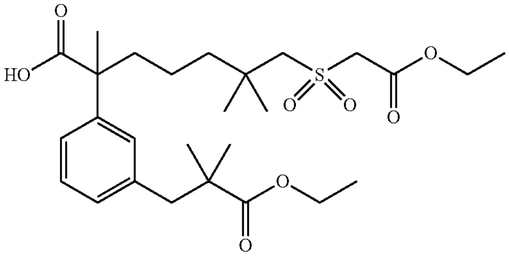 [SMILES: CCOC(=O)CS(=O)(=O)CC(C)(C)CCCC(C)(C(=O)O)c1cccc(CC(C)(C)C(=O)OCC)c1] | 2-(3-(3-ethoxy-2,2-dimethyl-3-oxopropyl)phenyl)-7-((2-ethoxy-2-oxoethyl)sulfonyl)-2,6,6-trimethylheptanoic acid | 549 $(M + Na)^+$ |
| 43-4 | 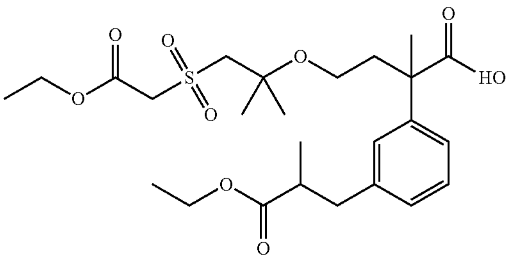 [SMILES: CCOC(=O)CS(=O)(=O)CC(C)(C)OCCC(C)(C(=O)O)c1cccc(CC(C)C(=O)OCC)c1] | 2-(3-bromophenyl)-4-((1-hydroxy-2-methylpropan-2-yl)oxy)-2-methylbutanoic acid | 537 |

-continued

| Inter. No. | Structure | Name | MS m/z [M + H]$^+$ |
|---|---|---|---|
| 43-5 | 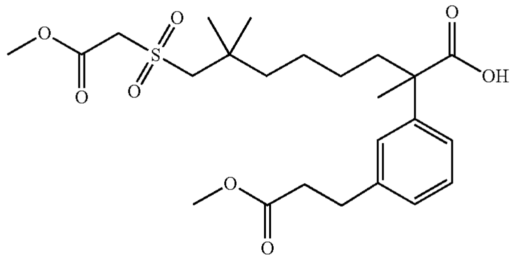 [SMILES: COC(=O)CCc1cccc(C(C)(CCCCC(C)(C)CS(=O)(=O)CC(=O)OC)C(=O)O)c1] | 8-((2-methoxy-2-oxoethyl)sulfonyl)-2-(3-(3-methoxy-3-oxopropyl)phenyl)-2,7,7-trimethyloctanoic acid | 507 [M + Na]$^+$ |
| 43-6 | 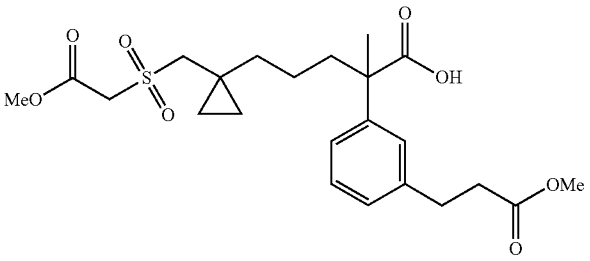 [SMILES: COC(=O)CCc1cccc(C(C)(CCCC2(CS(=O)(=O)CC(=O)OC)CC2)C(=O)O)c1] | 5-(1-(((2-methoxy-2-oxoethyl)sulfonyl)methyl) cyclopropyl)-2-(3-(3-methoxy-3-oxopropyl)phenyl)-2-methylpentanoic acid | 469 |
| 43-7 | 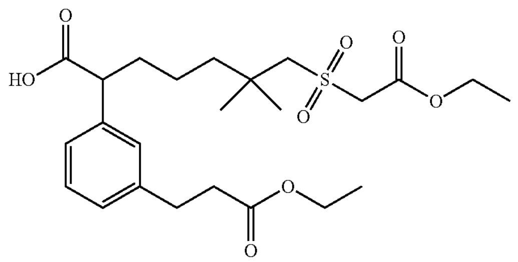 [SMILES: CCOC(=O)CCc1cccc(C(CCCC(C)(C)CS(=O)(=O)CC(=O)OCC)C(=O)O)c1] | 7-((2-ethoxy-2-oxoethyl)sulfonyl)-2-(3-(3-ethoxy-3-oxopropyl)phenyl)-6,6-dimethylheptanoic acid | 507 [M + Na]$^+$ |
| 43-8 | 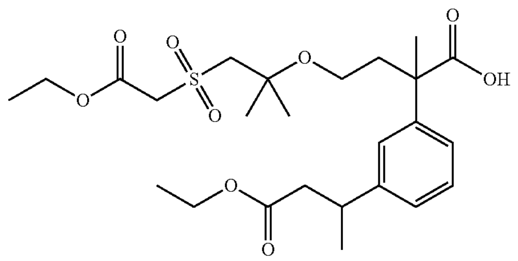 [SMILES: CCOC(=O)CC(C)c1cccc(C(C)(CCOC(C)(C)CS(=O)(=O)CC(=O)OCC)C(=O)O)c1] | 4-((1-((2-ethoxy-2-oxoethyl)sulfonyl)-2-methylpropan-2-yl)oxy)-2-(3-(4-ethoxy-4-oxobutan-2-yl)phenyl)-2-methylbutanoic acid | 537 [M + Na]$^+$ |
| 43-9 | 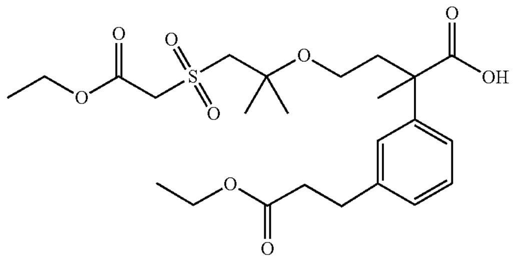 [SMILES: CCOC(=O)CCc1cccc(C(C)(CCOC(C)(C)CS(=O)(=O)CC(=O)OCC)C(=O)O)c1] | 4-((1-((2-ethoxy-2-oxoethyl)sulfonyl)-2-methylpropan-2-yl)oxy)-2-(3-(3-ethoxy-3-oxopropyl)phenyl)-2-methylbutanoic acid | 523 [M + Na]$^+$ |
| 43-10 | 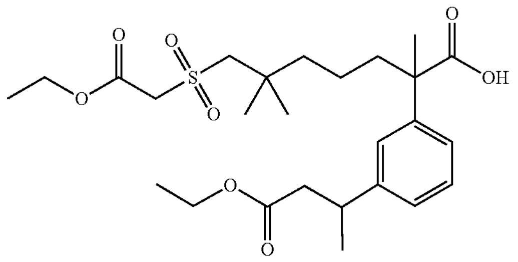 [SMILES: CCOC(=O)CC(C)c1cccc(C(C)(CCCC(C)(C)CS(=O)(=O)CC(=O)OCC)C(=O)O)c1] | 7-((2-ethoxy-2-oxoethyl)sulfonyl)-2-(3-(4-ethoxy-4-oxobutan-2-yl)phenyl)-2,6,6-trimethylheptanoic acid | 535 [M + Na]$^+$ |

-continued

| Inter. No. | Structure | Name | MS m/z [M + H]$^+$ |
|---|---|---|---|
| 43-11 | 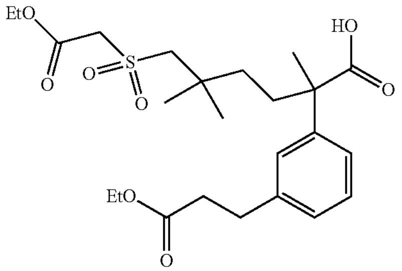 [SMILES: CCOC(=O)CCc1cccc(C(C)(CCC(C)(C)CS(=O)(=O)CC(=O)OCC)C(=O)O)c1] | 6-((2-ethoxy-2-oxoethyl)sulfonyl)-2-(3-(3-ethoxy-3-oxopropyl)phenyl)-2,5,5-trimethylhexanoic acid | 507 [M + Na]$^+$ |
| 43-12 | 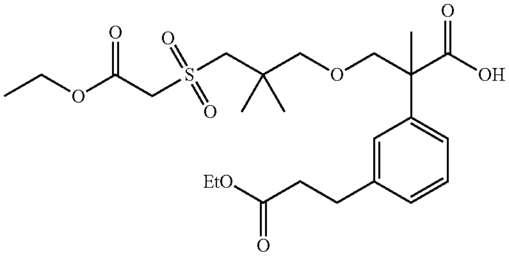 [SMILES: CCOC(=O)CCc1cccc(C(C)(COCC(C)(C)CS(=O)(=O)CC(=O)OCC)C(=O)O)c1] | 3-(3-((2-ethoxy-2-oxoethyl)sulfonyl)-2,2-dimethylpropoxy)-2-(3-(3-ethoxy-3-oxopropyl)phenyl)-2-methylpropanoic acid | 523 [M + Na]$^+$ |
| 43-13 | 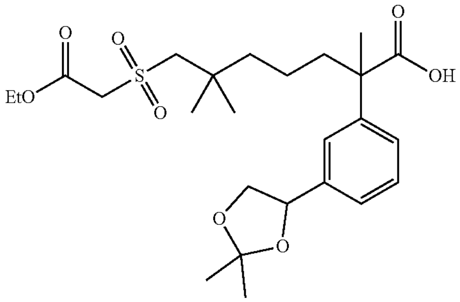 [SMILES: CCOC(=O)CS(=O)(=O)CC(C)(C)CCCC(C)(C(=O)O)c1cccc(C2COC(C)(C)O2)c1] | 2-(3-(2,2-dimethyl-1,3-dioxolan-4-yl)phenyl)-7-((2-ethoxy-2-oxoethyl)sulfonyl)-2,6,6-trimethylheptanoic acid | 521 [M + Na]$^+$ |
| 43-14 | 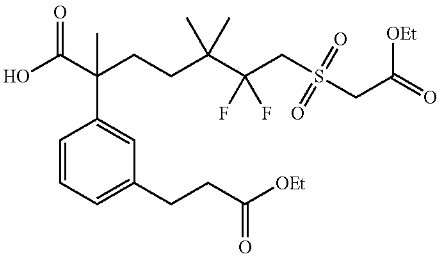 [SMILES: CCOC(=O)CCc1cccc(C(C)(CCC(C)(C)C(F)(F)CS(=O)(=O)CC(=O)OCC)C(=O)O)c1] | 7-((2-ethoxy-2-oxoethyl)sulfonyl)-2-(3-(3-ethoxy-3-oxopropyl)phenyl)-6,6-difluoro-2,5,5-trimethylheptanoic acid | 535 |
| 43-15 | 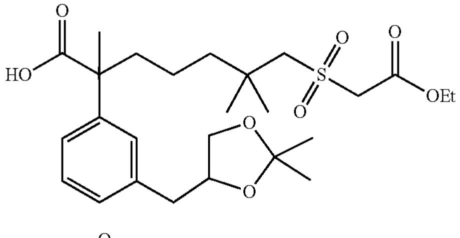 | 2-(3-((2,2-dimethyl-1,3-dioxolan-4-yl)methyl)phenyl)-7-((2-ethoxy-2-oxoethyl)sulfonyl)-2,6,6-trimethylheptanoic acid | 535 [M + Na]$^+$ |
| 43-16 | 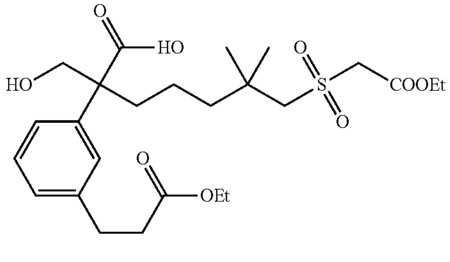 [SMILES: CCOC(=O)CCc1cccc(C(CO)(CCCC(C)(C)CS(=O)(=O)CC(=O)OCC)C(=O)O)c1] | 7-((2-ethoxy-2-oxoethyl)sulfonyl)-2-(3-(3-ethoxy-3-oxopropyl)phenyl)-2-(hydroxymethyl)-6,6-dimethylheptanoic acid | 537 [M + Na]$^+$ |

-continued

| Inter. No. | Structure | Name | MS m/z [M + H]$^+$ |
|---|---|---|---|
| 43-17 | 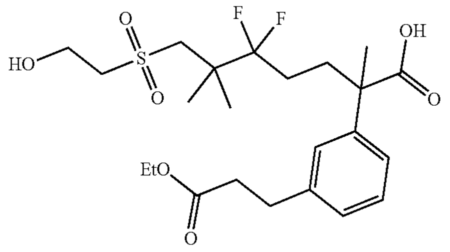 [SMILES: CCOC(=O)CCc1cccc(C(C)(CCC(F)(F)C(C)(C)CS(=O)(=O)CCO)C(=O)O)c1] | 2-(3-(3-ethoxy-3-oxopropyl)phenyl)-5,5-difluoro-7-((2-hydroxyethyl)sulfonyl)-2,6,6-trimethylheptanoic acid | 515 [M + Na]$^+$ |
| 43-18 | 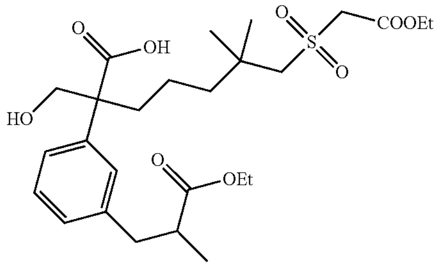 [SMILES: CCOC(=O)CS(=O)(=O)CC(C)(C)CCCC(CO)(C(=O)O)c1cccc(CC(C)C(=O)OCC)c1] | 2-(3-(3-ethoxy-2-methyl-3-oxopropyl)phenyl)-7-((2-ethoxy-2-oxoethyl)sulfonyl)-2-(hydroxymethyl)-6,6-dimethylheptanoic acid | 551 [M + Na]$^+$ |
| 43-19 | 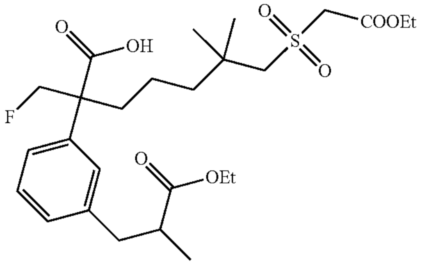 [SMILES: CCOC(=O)CS(=O)(=O)CC(C)(C)CCCC(CF)(C(=O)O)c1cccc(CC(C)C(=O)OCC)c1] | 2-(3-(3-ethoxy-2-methyl-3-oxopropyl)phenyl)-7-((2-ethoxy-2-oxoethyl)sulfonyl)-2-(fluoromethyl)-6,6-dimethylheptanoic acid | 531 |
| 43-20 | 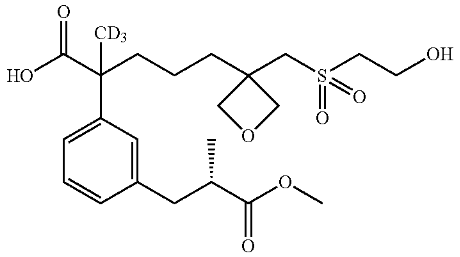 [SMILES: [2H]C([2H])([2H])C(CCCC1(CS(=O)(=O)CCO)COC1)(C(=O)O)c1cccc(C[C@H](C)C(=O)OC)c1] | 5-(3-(((2-hydroxyethyl)sulfonyl)methyl)oxetan-3-yl)-2-(3-((S)-3-methoxy-2-methyl-3-oxopropyl)phenyl)-2-(methyl-d3)pentanoic acid | 474 |
| 43-21 | 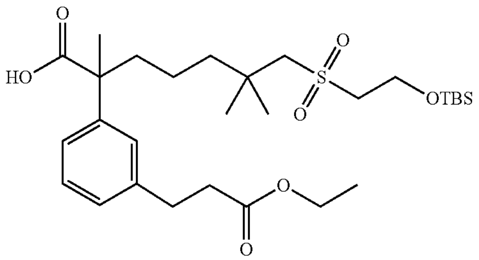 [SMILES: CCOC(=O)CCc1cccc(C(C)(CCCC(C)(C)CS(=O)(=O)CCO[Si](C)(C)C(C)(C)C)C(=O)O)c1] | 7-((2-((tert-butyldimethylsilyl)oxy)ethyl)sulfonyl)-2-(3-(3-ethoxy-3-oxopropyl)phenyl)-2,6,6-trimethylheptanoic acid | 593 [M + Na]$^+$ |

-continued

| Inter. No. | Structure | Name | MS m/z [M + H]$^+$ |
|---|---|---|---|
| 43-22 | 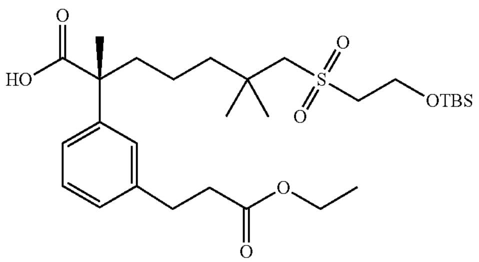 [SMILES: CCOC(=O)CCc1cccc([C@@](C)(CCCC(C)(C)CS(=O)(=O)CCO[Si](C)(C)C(C)(C)C)C(=O)O)c1] | (R)-7-((2-((tert-butyldimethylsilyl)oxy)ethyl) sulfonyl)-2-(3-(3-ethoxy-3-oxopropyl)phenyl)-2,6,6-trimethylheptanoic acid | 593 [M + Na]$^+$ |
| 43-23 | 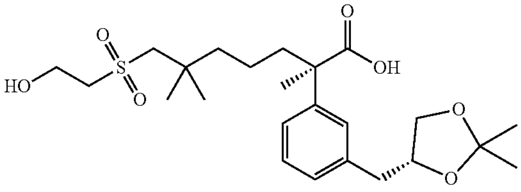 [SMILES: CC(C)(CCC[C@@](C)(C(=O)O)c1cccc(C[C@@H]2COC(C)(C)O2)c1)CS(=O)(=O)CCO] | (R)-2-(3-(((R)-2,2-dimethyl-1,3-dioxolan-4-yl)methyl)phenyl)-7-((2-hydroxyethyl)sulfonyl)-2,6,6-trimethylheptanoic acid (~7:3 R:S mixture at 1,3-dioxolane) | 493 [M + Na]$^+$; RT: 1.65 min. (LC-MS method 003) |
| 43-24 | 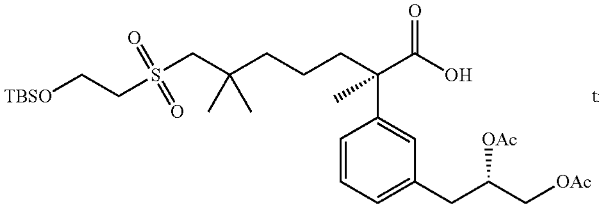 | (R)-7-((2-((tert-butyldimethylsilyl)oxy)ethyl) sulfonyl)-2-(3-((S)-2,3-diacetoxypropyl)phenyl)-2,6,6-trimethylheptanoic acid (~7:3 S:R mixture at diol position) | 651 [M + Na]$^+$; RT: 2.03 min. (LC-MS method 004) |
| 43-25 | 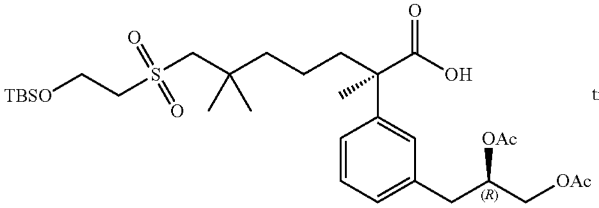 | (R)-7-((2-((tert-butyldimethylsilyl)oxy)ethyl) sulfonyl)-2-(3-((R)-2,3-diacetoxypropyl)phenyl)-2,6,6-trimethylheptanoic acid (~7:3 R:S mixture at diol position) | 651 [M + Na]$^+$; RT: 2.03 min. (LC-MS method 004) |
| 43-26 | 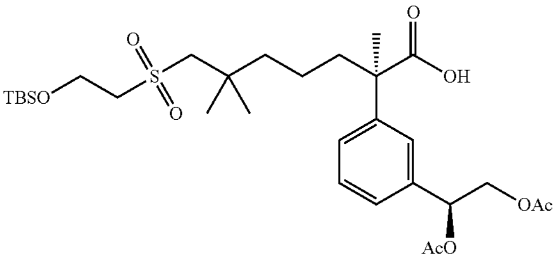 [SMILES: CC(=O)OC[C@@H](OC(C)=O)c1cccc([C@@](C)(CCCC(C)(C)CS(=O)(=O)CCO[Si](C)(C)C(C)(C)C)C(=O)O)c1] | (R)-7-((2-((tert-butyldimethylsilyl)oxy)ethyl) sulfonyl)-2-(3-((S)-1,2-diacetoxyethyl)phenyl)-2,6,6-trimethylheptanoic acid | 637 [M + Na]$^+$; RT: 2.03 min. (LC-MS method 003) |
| 43-27 | 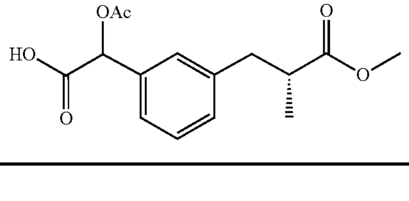 | 2-acetoxy-2-(3-((R)-3-methoxy-2-methyl-3-oxopropyl)phenyl)acetic acid | 317 [M + Na]$^+$; RT: 1.74 min. (LC-MS method 003) |

Intermediate 43A: Benzyl 7-(acetylthio)-2-(3-(2-ethoxy-2-oxoethoxy)phenyl)-2,6,6-trimethylheptanoate

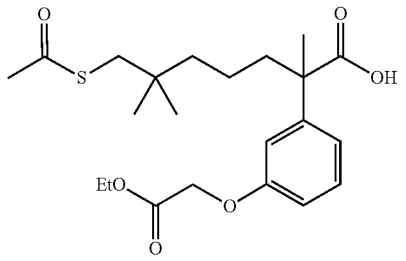 [SMILES: CCOC(=O)COc1cccc(C(C)(CCCC(C)(C)CSC(C)=O)C(=O)O)c1]

To a stirred and cooled (0° C.) solution of triphenylphosphine (13.8 g, 52.6 mmol) in tetrahydrofuran (300 mL) was added, dropwise over 10 minutes, diisopropyl azodicarboxylate (10.3 mL, 10.6 g, 52.3 mmol). The mixture maintained at 0° C. until the formation of a white solid was observed. At this time, a previously prepared solution of benzyl 2-(3-(2-ethoxy-2-oxoethoxy)phenyl)-7-hydroxy-2,6,6-trimethylheptanoate (Intermediate 42, 7.99 g, 17.5 mmol) and thioacetic acid (3.76 mL, 4.00 g, 52.6 mmol) in tetrahydrofuran (30 mL) was added, dropwise over 30 minutes. Following the addition, the reaction was stirred at 0° C. for one hour, allowed to warm to room temperature and stirred for another hour. The mixture was then concentrated, and the crude residue was subjected to automated flash chromatography (120 g silica gel column, 0-10% ethyl acetate in petroleum ether). The title compound was obtained as a viscous, pale amber oil (7.82 g, 87%). MS (ESI): 537 m/z $[M+Na]^+$.

Intermediate 43B: Benzyl 2-(3-(2-ethoxy-2-oxoethoxy)phenyl)-7-((2-ethoxy-2-oxoethyl)thio)-2,6,6-trimethylheptanoate

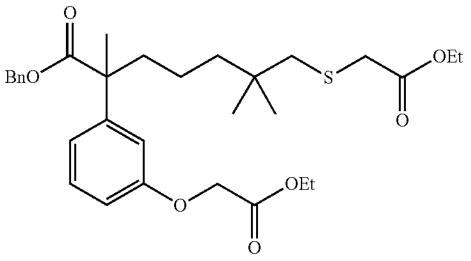 [SMILES: CCOC(=O)COc1cccc(C(C)(CCCC(C)(C)CSCC(=O)OCC)C(=O)OCc2ccccc2)c1]

To a stirred solution of benzyl 7-(acetylthio)-2-(3-(2-ethoxy-2-oxoethoxy)phenyl)-2,6,6-trimethylheptanoate (Intermediate 43A, 8.19 g, 15.9 mmol) in ethanol (150 mL) was added ethyl bromoacetate (2.3 mL, 3.5 g, 21 mmol) followed by solid sodium ethoxide (1.63 g, 24.0 mmol). After one hour at room temperature, the mixture was partitioned between ethyl acetate (200 mL) and water (200 mL). The organic layer was washed with additional portions of water (2×200 mL), dried over magnesium sulfate and concentrated. The crude residue was purified by automated flash chromatography (120 g silica gel column, 0-15% ethyl acetate in petroleum ether) to afford the title compound as an amber oil (6.69 g, 75%). MS (ESI): 581 m/z $[M+Na]^+$.

Intermediate 43C: Benzyl 2-(3-(2-ethoxy-2-oxoethoxy)phenyl)-7-((2-ethoxy-2-oxoethyl)sulfonyl)-2,6,6-trimethylheptanoate

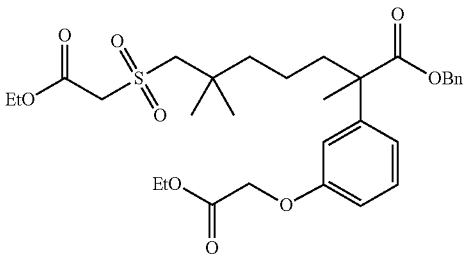 [SMILES: CCOC(=O)COc1cccc(C(C)(CCCC(C)(C)CS(=O)(=O)CC(=O)OCC)C(=O)OCc2ccccc2)c1]

To a stirred solution of benzyl 2-(3-(2-ethoxy-2-oxoethoxy)phenyl)-7-((2-ethoxy-2-oxoethyl)thio)-2,6,6-trimethylheptanoate (Intermediate 43B, 5.98 g, 10.7 mmol) in methanol (500 mL) was added a solution of ammonium molybdate tetrahydrate (6.61 g, 5.35 mmol) dissolved in 30% aqueous hydrogen peroxide solution (60 mL). The reaction was stirred at room temperature for two hours and then partitioned between ethyl acetate (500 mL) and water (500 mL). The organic layer was washed with additional portions of water (2×500 mL), dried over sodium sulfate and concentrated. The crude title compound, which was used without purification, was obtained as a foamy gum (5.28 g, 84%). MS (ESI): 613 m/z $[M+Na]^+$.

Intermediate 44: tert-Butyl 1-(methyl-d3)hydrazine-1-carboxylate

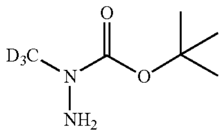

To a stirred solution of tert-butyl (1,3-dioxoisoindolin-2-yl)(methyl-$d_3$)carbamate (20.0 g, 71.6 mmol) in tetrahydrofuran (200 mL) was added hydrazine monohydrate (10.4 mL, 10.7 g, 214 mmol). The reaction was allowed to proceed overnight at room temperature. During this time, a white precipitate accumulated in the mixture (presumably, the 2,3-dihydrophthalazine-1,4-dione byproduct generated by phthalimide cleavage). This solid was filtered off and rinsed with additional tetrahydrofuran (3×20 mL). The combined filtrate was concentrated to afford the crude title compound, which was used without purification, as a colorless oil (9.71 g, 91%). $^1H$ NMR (400 MHz, DMSO-$d_6$) δ 4.50 (s, 2H), 1.40 (s, 9H) ppm.

The following intermediate was prepared based on the procedures described for Intermediate 44, and/or for Intermediate 44A.

| Inter. No. | Structure | Name | MS m/z [M + H]+ |
|---|---|---|---|
| 44-1 | 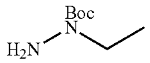 | tert-butyl 1-ethylhydrazine-1-carboxylate | $^1H$ NMR (400 MHz, $CD_3OD$) δ 4.39 (s, 2H), 3.26 (t, J = 6.8 Hz, 2H), 1.48 (s, 9H), 1.02 (t, J = 6.8 Hz, 3H). |

Intermediate 44A: tert-Butyl (1,3-dioxoisoindolin-2-yl)(methyl-d3)carbamate

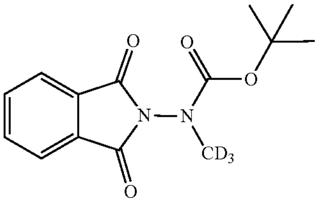 [SMILES: [2H]C([2H])([2H])N(C(=O)OC(C)(C)C)N1C(=O)c2ccccc2C1=O]

To a stirred and cooled (0° C.) solution of tert-butyl N-(1,3-dioxoisoindolin-2-yl)carbamate (20.0 g, 76.3 mmol), triphenylphosphine (30.0 g, 114 mmol) and methanol-$d_4$ (4.63 mL, 4.11 g, 114 mmol) in tetrahydrofuran (800 mL) was added, in one portion, diisopropyl azodicarboxylate (22.5 mL, 23.1 g, 114 mmol). Following the addition, the cooling bath was removed. The reaction was allowed to proceed at room temperature for two hours and then concentrated. The obtained residue was triturated with ethyl acetate and the resulting suspension was filtered free of white solid (triphenylphosphine oxide). The solids were rinsed with additional ethyl acetate (2×50 mL) and the combined filtrate was concentrated to a crude residue which was purified by automated flash chromatography (330 g silica gel column, 0-30% ethyl acetate in petroleum ether). The title compound was obtained as a white solid (20.0 g, 94%). MS (ESI): 302 m/z $[M+Na]^+$.

Intermediate 45: Ethyl 2-((6-(3-(2-ethoxy-2-oxoethoxy)phenyl)-2,2,6-trimethyl-7-(2-(methyl-d3)hydrazineyl)-7-oxoheptyl)sulfonyl)acetate

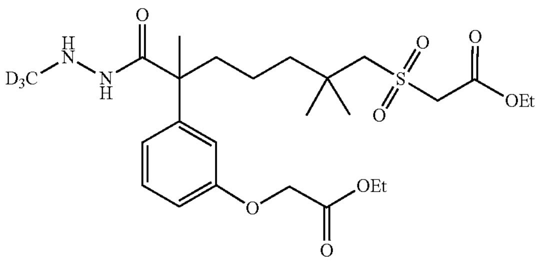 [SMILES: [2H]C([2H])([2H])NNC(=O)C(C)(CCCC(C)(C)CS(=O)(=O)CC(=O)OCC)c1cccc(OCC(=O)OCC)c1]

To a stirred solution of tert-butyl 2-(2-(3-(2-ethoxy-2-oxoethoxy)phenyl)-7-((2-ethoxy-2-oxoethyl)sulfonyl)-2,6,6-trimethylheptanoyl)-1-(methyl-d3)hydrazine-1-carboxylate (Intermediate 45A, 3.39 g, 5.37 mmol) in dichloromethane (50 mL) was added trifluoroacetic acid (2.0 mL, 3.0 g, 26 mmol). After four hours at room temperature, the reaction was analyzed by LCMS and found to be complete. Dilute aqueous sodium bicarbonate solution was slowly added to the mixture until a basic pH was achieved. The organic layer was removed and combined with a second extract of the aqueous phase (dichloromethane, 1×50 mL). The solution was washed with brine (2×100 mL), dried over sodium sulfate and concentrated. The crude title compound, which was used without purification, was obtained as a gum (2.50 g, 88%). MS (ESI): 532 m/z $[M+H]^+$.

The following intermediates were prepared based on the procedures described for Intermediate 45, and/or for Intermediate 45A.

| Inter. No. | Structure | Name | MS m/z [M + H]+ |
|---|---|---|---|
| 45-1 | 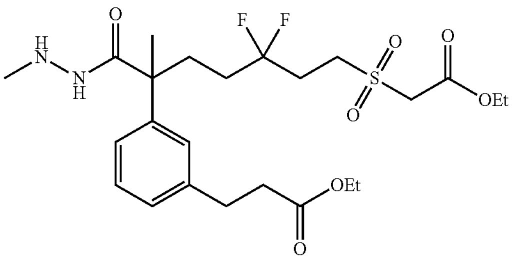 [SMILES: CCOC(=O)CCc1cccc(C(C)(CCC(F)(F)CCS(=O)(=O)CC(=O)OCC)C(=O)NNC)c1] | Ethyl 3-(3-(7-((2-ethoxy-2-oxoethyl)sulfonyl)-5,5-difluoro-2-methyl-1-(2-methylhydrazineyl)-1-oxoheptan-2-yl)phenyl)propanoate | 535 |
| 45-2 | 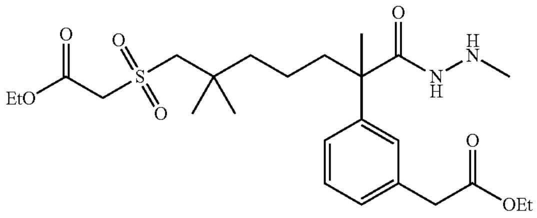 [SMILES: CCOC(=O)Cc1cccc(C(C)(CCCC(C)(C)CS(=O)(=O)CC(=O)OCC)C(=O)NNC)c1] | Ethyl 2-((6-(3-(2-ethoxy-2-oxoethyl)phenyl)-2,2,6-trimethyl-7-(2-methylhydrazineyl)-7-oxoheptyl)sulfonyl)acetate | 513 |

-continued

| Inter. No. | Structure | Name | MS m/z [M + H]+ |
|---|---|---|---|
| 45-3 | 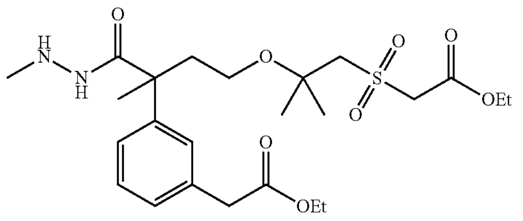 [SMILES: CCOC(=O)Cc1cccc(C(C)(CCOC(C)(C)CS(=O)(=O)CC(=O)OCC)C(=O)NNC)c1] | 2-(3-(2-Ethoxy-2-oxoethyl)phenyl)-4-((1-((2-ethoxy-2-oxoethyl)sulfonyl)-2-methylpropan-2-yl)oxy)-2-methylbutanoic acid | 515 |
| 45-4 | 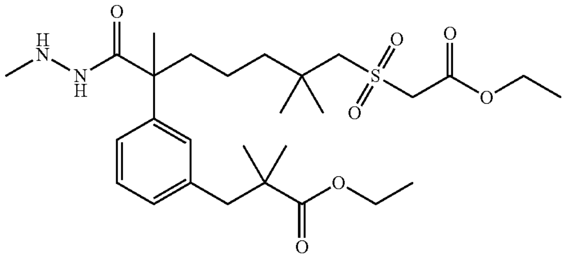 [SMILES: CCOC(=O)CS(=O)(=O)CC(C)(C)CCCC(C)(C(=O)NNC)c1cccc(CC(C)(C)C(=O)OCC)c1] | ethyl 3-(3-(7-((2-ethoxy-2-oxoethyl)sulfonyl)-2,6,6-trimethyl-1-(2-methylhydrazineyl)-1-oxoheptan-2-yl)phenyl)-2,2-dimethylpropanoate | 555 |
| 45-5 | 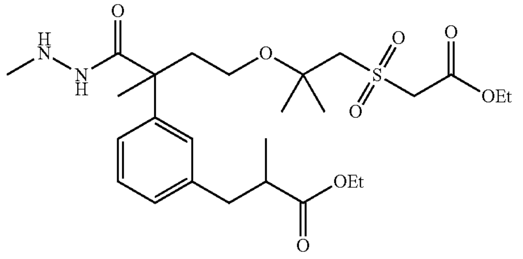 [SMILES: CCOC(=O)CS(=O)(=O)CC(C)(C)OCCC(C)(C(=O)NNC)c1cccc(CC(C)C(=O)OCC)c1] | ethyl 3-(3-(4-((1-((2-ethoxy-2-oxoethyl)sulfonyl)-2-methylpropan-2-yl)oxy)-2-methyl-1-(2-methylhydrazineyl)-1-oxobutan-2-yl)phenyl)-2-methylpropanoate | 543 |
| 45-6 | 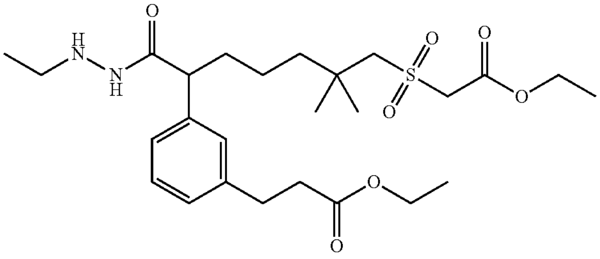 [SMILES: CCNNC(=O)C(CCCC(C)(C)CS(=O)(=O)CC(=O)OCC)c1cccc(CCC(=O)OCC)c1] | ethyl 3-(3-(7-((2-ethoxy-2-oxoethyl)sulfonyl)-1-(2-ethylhydrazineyl)-6,6-dimethyl-1-oxoheptan-2-yl)phenyl)propanoate | 549 [M + Na]+ |
| 45-7 | 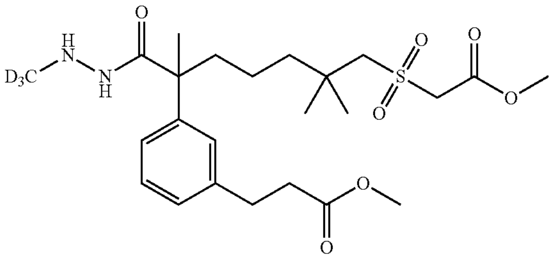 [SMILES: [2H]C([2H])([2H])NNC(=O)C(C)(CCCC(C)(C)CS(=O)(=O)CC(=O)OC)c1cccc(CCC(=O)OC)c1] | methyl 3-(3-(7-((2-methoxy-2-oxoethyl)sulfonyl)-2,6,6-trimethyl-1-(2-(methyl-d3)hydrazineyl)-1-oxoheptan-2-yl)phenyl)propanoate | 502 |
| 45-8 | 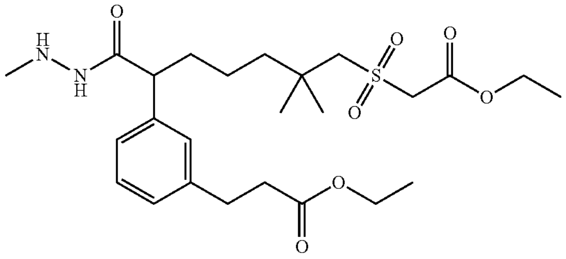 [SMILES: CCOC(=O)CCc1cccc(C(CCCC(C)(C)CS(=O)(=O)CC(=O)OCC)C(=O)NNC)c1] | ethyl 3-(3-(7-((2-ethoxy-2-oxoethyl)sulfonyl)-6,6-dimethyl-1-(2-methylhydrazineyl)-1-oxoheptan-2-yl)phenyl)propanoate | 513 |

-continued

| Inter. No. | Structure | Name | MS m/z [M + H]+ |
|---|---|---|---|
| 45-9 | 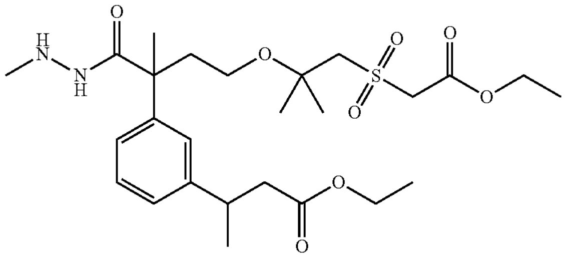 [SMILES: CCOC(=O)CC(C)c1cccc(C(C)(CCOC(C)(C)CS(=O)(=O)CC(=O)OCC)C(=O)NNC)c1] | ethyl 3-(3-(4-((1-((2-ethoxy-2-oxoethyl)sulfonyl)-2-methylpropan-2-yl)oxy)-2-methyl-1-(2-methylhydrazineyl)-1-oxobutan-2-yl)phenyl)butanoate | 543 |
| 45-10 | 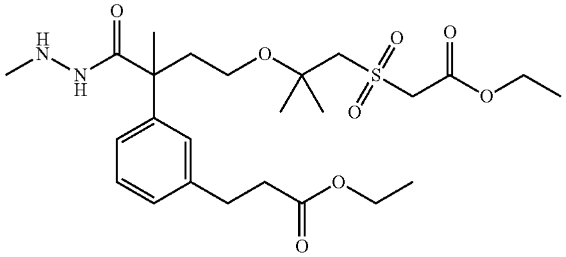 [SMILES: CCOC(=O)CCc1cccc(C(C)(CCOC(C)(C)CS(=O)(=O)CC(=O)OCC)C(=O)NNC)c1] | ethyl 3-(3-(4-((1-((2-ethoxy-2-oxoethyl)sulfonyl)-2-methylpropan-2-yl)oxy)-2-methyl-1-(2-methylhydrazineyl)-1-oxobutan-2-yl)phenyl)propanoate | 529 |
| 45-11 | 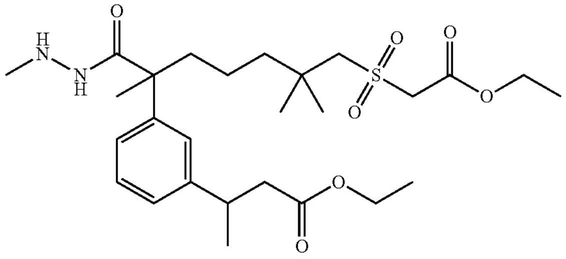 [SMILES: CCOC(=O)CC(C)c1cccc(C(C)(CCCC(C)(C)CS(=O)(=O)CC(=O)OCC)C(=O)NNC)c1] | ethyl 3-(3-(7-((2-ethoxy-2-oxoethyl)sulfonyl)-2,6,6-trimethyl-1-(2-methylhydrazineyl)-1-oxoheptan-2-yl)phenyl)butanoate | 541 |
| 45-12 | 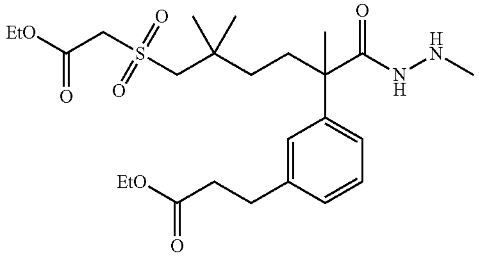 [SMILES: CCOC(=O)CCc1cccc(C(C)(CCC(C)(C)CS(=O)(=O)CC(=O)OCC)C(=O)NNC)c1] | ethyl 3-(3-(6-((2-ethoxy-2-oxoethyl)sulfonyl)-2,5,5-trimethyl-1-(2-methylhydrazineyl)-1-oxohexan-2-yl)phenyl)propanoate | 513 |
| 45-13 | 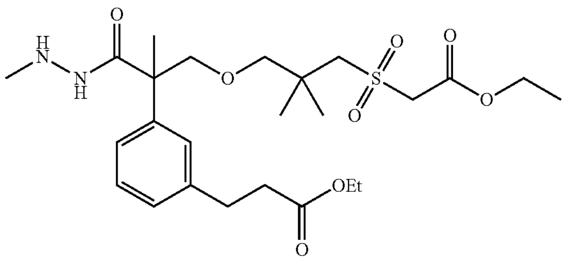 [SMILES: CCOC(=O)CCc1cccc(C(C)(COCC(C)(C)CS(=O)(=O)CC(=O)OCC)C(=O)NNC)c1] | ethyl 3-(3-(3-(3-((2-ethoxy-2-oxoethyl)sulfonyl)-2,2-dimethylpropoxy)-2-methyl-1-(2-methylhydrazineyl)-1-oxopropan-2-yl)phenyl)propanoate | 529 |

-continued

| Inter. No. | Structure | Name | MS m/z [M + H]+ |
|---|---|---|---|
| 45-14 | 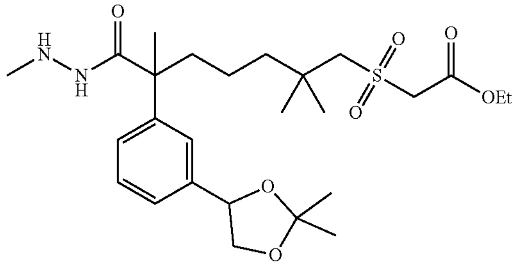 [SMILES: CCOC(=O)CS(=O)(=O)CC(C)(C)CCCC(C)(C(=O)NNC)c1cccc(C2COC(C)(C)O2)c1] | ethyl 2-((6-(3-(2,2-dimethyl-1,3-dioxolan-4-yl)phenyl)-2,2,6-trimethyl-7-(2-methylhydrazineyl)-7-oxoheptyl)sulfonyl)acetate | 527 |
| 45-15 | 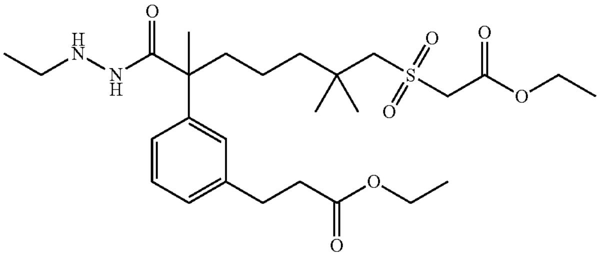 [SMILES: CCNNC(=O)C(C)(CCCC(C)(C)CS(=O)(=O)CC(=O)OCC)c1cccc(CCC(=O)OCC)c1] | ethyl 3-(3-(7-((2-ethoxy-2-oxoethyl)sulfonyl)-1-(2-ethylhydrazineyl)-2,6,6-trimethyl-1-oxoheptan-2-yl)phenyl)propanoate | 563 [M + Na]+ |
| 45-16 | 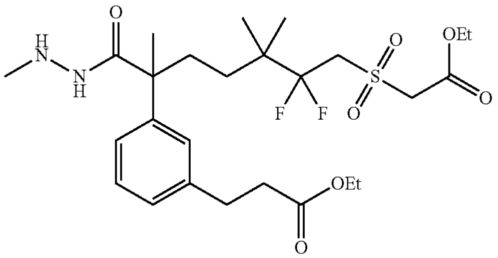 [SMILES: CCOC(=O)CCc1cccc(C(C)(CCC(C)(C)C(F)(F)CS(=O)(=O)CC(=O)OCC)C(=O)NNC)c1] | ethyl 3-(3-(7-((2-ethoxy-2-oxoethyl)sulfonyl)-6,6-difluoro-2,5,5-trimethyl-1-(2-methylhydrazineyl)-1-oxoheptan-2-yl)phenyl)propanoate | 563 |
| 45-17 | 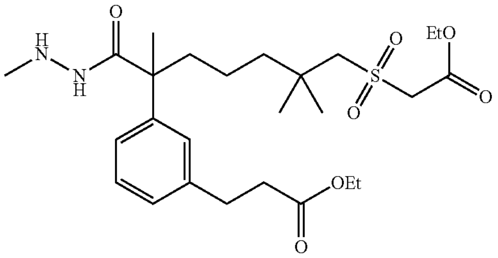 [SMILES: CCOC(=O)CCc1cccc(C(C)(CCCC(C)(C)CS(=O)(=O)CC(=O)OCC)C(=O)NNC)c1] | ethyl 3-(3-(7-((2-ethoxy-2-oxoethyl)sulfonyl)-2,6,6-trimethyl-1-(2-methylhydrazineyl)-1-oxoheptan-2-yl)phenyl)propanoate | 527 |
| 45-18 | 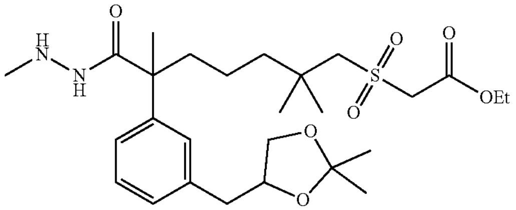 [SMILES: CCOC(=O)CS(=O)(=O)CC(C)(C)CCCC(C)(C(=O)NNC)c1cccc(CC2COC(C)(C)O2)c1] | ethyl 2-((6-(3-((2,2-dimethyl-1,3-dioxolan-4-yl)methyl)phenyl)-2,2,6-trimethyl-7-(2-methylhydrazineyl)-7-oxoheptyl)sulfonyl)acetate | 541 |
| 45-19 | 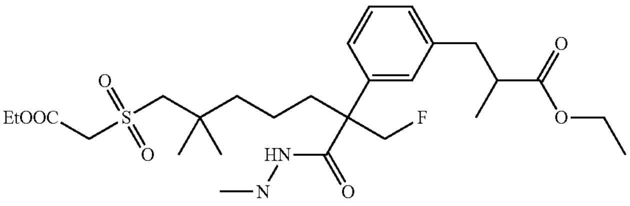 | ethyl 3-(3-(7-((2-ethoxy-2-oxoethyl)sulfonyl)-2-(fluoromethyl)-6,6-dimethyl-1-(2-methylhydrazineyl)-1-oxoheptan-2-yl)phenyl)-2-methylpropanoate | 559 |

-continued

| Inter. No. | Structure | Name | MS m/z $[M + H]^+$ |
|---|---|---|---|
| 45-20 | 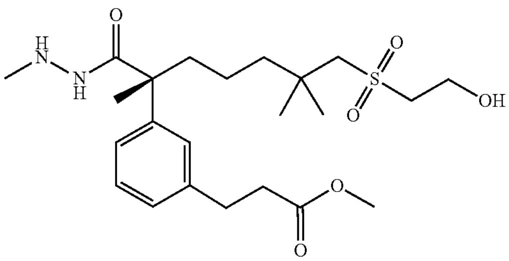 [SMILES: CNNC(=O)[C@](C)(CCCC(C)(C)CS(=O)(=O)CCO)c1cccc(CCC(=O)OC)c1] | methyl (R)-3-(3-(7-((2-hydroxyethyl)sulfonyl)-2,6,6-trimethyl-1-(2-methylhydrazineyl)-1-oxoheptan-2-yl)phenyl)propanoate | 471 |

Intermediate 45A: tert-Butyl 2-(2-(3-(2-ethoxy-2-oxoethoxy)phenyl)-7-((2-ethoxy-2-oxoethyl)sulfonyl)-2,6,6-trimethylheptanoyl)-1-(methyl-d3)hydrazine-1-carboxylate

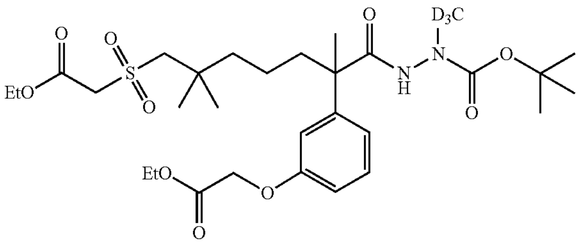 [SMILES: [2H]C([2H])([2H])N(NC(=O)C(C)(CCCC(C)(C)CS(=O)(=O)CC(=O)OCC)c1cccc(OCC(=O)OCC)c1)C(=O)OC(C)(C)C]

To a stirred solution of 2-(3-(2-Ethoxy-2-oxoethoxy)phenyl)-7-((2-ethoxy-2-oxoethyl)sulfonyl)-2,6,6-trimethylheptanoic acid (Intermediate 43, 4.00 g, 7.99 mmol) in acetonitrile (100 mL) was added, in order, crude tert-butyl 1-(methyl-d3)hydrazine-1-carboxylate (Intermediate 44, 1.43 g, 9.58 mmol), 1-methylimidazole (2.23 mL, 2.30 g, 28.0 mmol) and chloro-N,N,N',N'-tetramethylformamidinium hexafluorophosphate (2.24 g, 7.98 mmol). The reaction was stirred for one hour and then partitioned between ethyl acetate (100 mL) and water (100 mL). The organic layer was washed with a second portion of water (1×100 mL), dried over magnesium sulfate and concentrated. The crude residue was purified by automated flash chromatography (80 g silica gel column, 0-50% ethyl acetate in petroleum ether) to afford the title compound as a foamy gum (3.39 g, 67%). MS (ESI): 654 m/z $[M+Na]^+$.

Intermediate 46: 2-(3-(3-Ethoxy-3-oxopropyl)phenyl)-5,5-difluoro-7-hydroxy-2-methylheptanoic acid

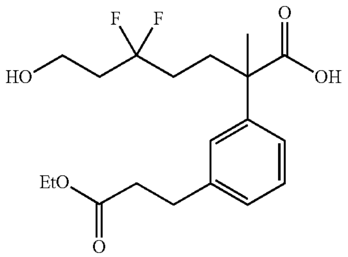 [SMILES: CCOC(=O)CCc1cccc(C(C)(CCC(F)(F)CCO)C(=O)O)c1]

A stirred suspension of 7-(benzyloxy)-2-(3-(3-ethoxy-3-oxoprop-1-en-1-yl)phenyl)-5,5-difluoro-2-methylheptanoic acid (Intermediate 46F, 2.99 g, 6.49 mmol) and 10% palladium on carbon (0.600 g) in ethanol (60 mL) was cycled between vacuum and a nitrogen atmosphere three times. After a final evacuation, the reaction vessel was backfilled with hydrogen (via balloon). The reaction was allowed to proceed overnight before the hydrogen was evacuated and the vessel was opened to air. The catalyst was removed by suction filtration through a pad of Celite, which was subsequently rinsed with additional ethanol (2×30 mL). The combined filtrate was concentrated to afford the crude title compound, which was used without purification, as a light-yellow solid (2.20 g, 91%). MS (ESI): 395 m/z $[M+Na]^+$.

Intermediate 46A: 2-(2-(2-(Benzyloxy)ethyl)-1,3-dithiolan-2-yl)ethan-1-ol

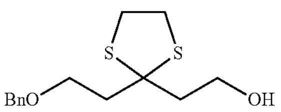 [SMILES: OCCC1(CCOCc2ccccc2)SCCS1]

To a stirred solution of 1,3-dithiolano-2,2-diethanol (Tsotinis, A. et al. *J. Med. Chem.* 2007, 50, 6436; 19.4 g, 99.8 mmol) in N,N-dimethylformamide (200 mL) was added, portion-wise over 15 minutes, a 60% dispersion of sodium hydride in mineral oil (4.39 g, 110 mmol). Following the addition, the frothy mixture was stirred at room temperature for an additional one hour before treating with benzyl bromide (13.1 mL, 18.8 g, 110 mmol). The reaction was left to stir overnight and then partitioned between water (300 mL) and ethyl acetate (100 mL). The organic layer was combined with additional extracts (ethyl acetate, 2×100 mL), washed with brine (1×100 mL) and dried over sodium sulfate. The solution was concentrated to afford the crude product which was subjected to automated flash chromatography (120 g silica gel column, 10-20% ethyl acetate in petroleum ether). The title compound was afforded as colorless gum (21.97 g, 77%). MS (ESI): 285 m/z $[M+H]^+$.

Intermediate 46B: 2-(2-(2-(Benzyloxy)ethyl)-1,3-dithiolan-2-yl)ethyl 4-methylbenzenesulfonate

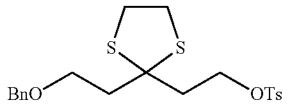 [SMILES: Cc1ccc(S(=O)(=O)OCCC2(CCOCc3ccccc3)SCCS2)cc1]

To a stirred and cooled (0° C.) solution of 2-(2-(2-(benzyloxy)ethyl)-1,3-dithiolan-2-yl)ethan-1-ol (Intermediate 46A, 21.97 g, 77.2 mmol) in pyridine (100 mL) was added, portion-wise over 15 minutes, p-toluenesulfonyl chloride (17.7 g, 92.8 mmol). The mixture was allowed to warm to room temperature and then stirred for an additional two hours before partitioning between water (300 mL) and ethyl acetate (100 mL). The organic layer was combined with additional extracts (ethyl acetate, 2×100 mL), washed with brine (1×100 mL) and dried over sodium sulfate. The solution was concentrated, and the resulting crude product was purified by automated flash chromatography (120 g silica gel column, 0-30% ethyl acetate in petroleum ether). The title compound was afforded as a pale amber solid (19.0 g, 77%). MS (ESI): 439 m/z $[M+H]^+$.

Intermediate 46C: Methyl 4-(1-(2-(benzyloxy)ethyl)cyclopentyl)-2-(3-bromophenyl)-2-methylbutanoate

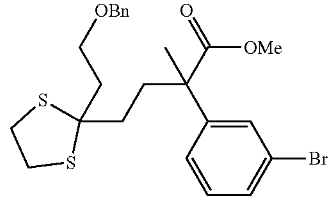 [SMILES: COC(=O)C(C)(CCC1(CCOCc2ccccc2)SCCS1)c1cccc(Br)c1]

To a stirred and cooled (0° C.) solution of methyl 2-(3-bromophenyl)propanoate (10.5 g, 43.2 mmol) and 2-(2-(2-(benzyloxy)ethyl)-1,3-dithiolan-2-yl)ethyl 4-methylbenzenesulfonate (Intermediate 46B, 19.0 g, 43.3 mmol) in tetrahydrofuran (100 mL) was added a 2.0 M solution of sodium bis(trimethylsilyl)amide in tetrahydrofuran (32.4 mL, 64.8 mmol). The cooling bath was removed, and the reaction was stirred overnight at room temperature. After this time, the mixture was diluted with aqueous ammonium chloride solution (300 mL). The biphasic mixture was extracted with ethyl acetate (3×100 mL) and the combined organic layers were washed with brine (1×150 mL), dried over sodium sulfate and concentrated. The crude residue was purified by automated flash chromatography (120 g silica gel column, 0-30% ethyl acetate in petroleum ether) to afford the title compound as a pale amber gum (13.0 g, 59%). MS (ESI): 509 m/z $[M+H]^+$.

Intermediate 46D: Methyl 7-(benzyloxy)-2-(3-bromophenyl)-5,5-difluoro-2-methylheptanoate

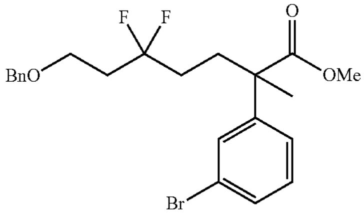 [SMILES: COC(=O)C(C)(CCC(F)(F)CCOCc1ccccc1)c1cccc(Br)c1]

Into a 1 L polyethylene bottle was loaded, 1,3-dibromo-5,5-dimethylhydantoin (18.2 g, 63.7 mmol), dichloromethane (200 mL) and a stir bar. The suspension was stirred vigorously and cooled to 0° C. In rapid succession, pyridinium poly(hydrogen fluoride) (70 wt % hydrogen fluoride; 13.3 mL, 10.2 g hydrogen fluoride, 512 mmol) and a premade solution of methyl 4-(1-(2-(benzyloxy)ethyl)cyclopentyl)-2-(3-bromophenyl)-2-methylbutanoate (Intermediate 46C, 13.0 g, 25.5 mmol) in dichloromethane (50 mL) were added. The red mixture was maintained at 0° C. for 30 minutes before diluting with hexane (300 mL) and addition of basic alumina (200 g). The resulting slurry was stirred for five minutes and then suction filtered. The alumina was rinsed with dichloromethane (total, ~250 mL) and the combined filtrate was concentrated. The crude residue was purified by automated flash chromatography (120 g silica gel column, 0-20% ethyl acetate in petroleum ether) to afford the title compound as a pale amber solid (4.41 g, 38%). MS (ESI): 477, 479 m/z $[M+Na]^+$.

Intermediate 46E: 7-(Benzyloxy)-2-(3-bromophenyl)-5,5-difluoro-2-methylheptanoic Acid

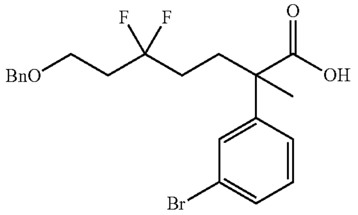 [SMILES: CC(CCC(F)(F)CCOCc1ccccc1)(C(=O)O)c1cccc(Br)c1]

To a stirred solution of methyl 7-(benzyloxy)-2-(3-bromophenyl)-5,5-difluoro-2-methylheptanoate (Intermediate 46D, 4.39 g, 9.64 mmol) in 5:1 methanol/water (60 mL) was added lithium hydroxide monohydrate (1.60 g, 38.1 mmol). The mixture was heated overnight at 60° C. and then cooled to room temperature. The stirred solution was diluted with water (20 mL) and treated with 1.0 N hydrochloric acid until an acidic pH was achieved (5-6 by litmus paper). The resulting suspension was extracted with ethyl acetate (3×100 mL) and the combined organic layers were washed with water (1×150 mL) and brine (1×150 mL). The solution was dried over sodium sulfate and concentrated, providing a crude residue which was purified by automated flash chromatography (120 g silica gel column, 0-70% ethyl acetate in petroleum ether). The title compound was obtained as a tan solid (3.70 g, 87%). MS (ESI): 463, 465 m/z $[M+Na]^+$.

Intermediate 46F: 7-(Benzyloxy)-2-(3-(3-ethoxy-3-oxoprop-1-en-1-yl)phenyl)-5,5-difluoro-2-methylheptanoic acid

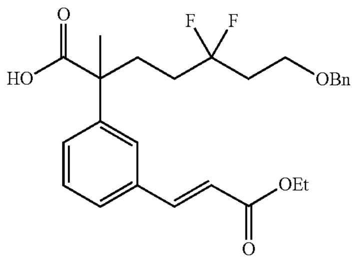 [SMILES: CCOC(=O)/C=C/c1cccc(C(C)(CCC(F)(F)CCOCc2ccccc2)C(=O)O)c1]

A microwave reaction vessel was loaded with 7-(benzyloxy)-2-(3-bromophenyl)-5,5-difluoro-2-methylheptanoic acid (Intermediate 46E, 3.50 g, 7.93 mmol), 1-methyl-2-pyrrolidinone (15 mL), ethyl acrylate (2.6 mL, 2.4 g, 24 mmol), palladium(II) acetate (0.365 g, 1.63 mmol), tri(o-tolyl)phosphine (1.68 g, 5.52 mmol) and triethylamine (5.5 mL, 4.0 g, 39 mmol). The stirred mixture was purged with nitrogen for approximately 10 minutes before the vessel was sealed and heated in a microwave reactor for two hours at 130° C. After this time, the reaction was cooled to room temperature and suction filtered. The collected solids were rinsed with ethyl acetate (total, ~100 mL) and the combined filtrate was washed with water (4×50 mL) and brine (2×50 mL). The organic solution was then dried over sodium sulfate and concentrated. The crude residue was purified by automated flash chromatography (120 g silica gel column, 0-5% methanol in dichloromethane) to afford the title compound as a light-yellow solid (2.99 g, 82%). MS (ESI): 461 m/z [M+H]$^+$.

Intermediate 47: 2-(3-(2-Ethoxy-2-oxoethyl)phenyl)-7-((2-ethoxy-2-oxoethyl)sulfonyl)-2-methylheptanoic Acid

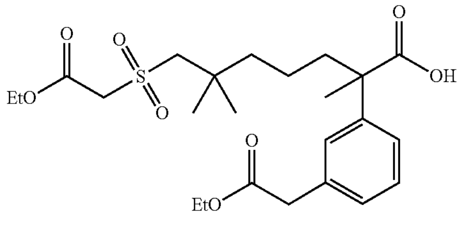 [SMILES: CCOC(=O)Cc1cccc(C(C)(CCCC(C)(C)CS(=O)(=O)CC(=O)OCC)C(=O)O)c1]

To a stirred solution of tert-butyl 2-(3-(2-ethoxy-2-oxoethyl)phenyl)-7-((2-ethoxy-2-oxoethyl)sulfonyl)-2,6,6-trimethylheptanoate (Intermediate 47F, 3.01 g, 5.57 mmol) in dichloromethane (10 mL) was added trifluoroacetic acid (10.0 mL, 14.9 g, 13.1 mmol). After one hour at room temperature, the reaction was concentrated and the residue was directly subjected to automated flash chromatography (40 g silica gel column, 0-50% ethyl acetate in petroleum ether). The title compound was afforded as colorless gum (2.31 g, 86%). MS (ESI): 507 m/z [M+Na]$^+$.

Intermediate 47A: tert-Butyl 2-(3-bromophenyl)-7-((tert-butyldimethylsilyl)oxy)-2,6,6-trimethylheptanoate

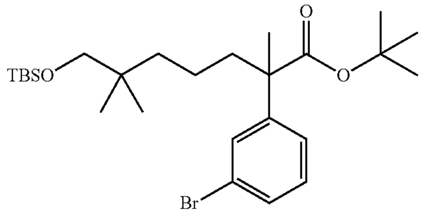 [SMILES: CC(C)(CCCC(C)(C(=O)OC(C)(C)C)c1cccc(Br)c1)CO[Si](C)(C)C(C)(C)C]

To a stirred and cooled (−78° C.) solution of tert-butyl 2-(3-bromophenyl)propanoate (Intermediate 15, 30.8 g, 108 mmol) in tetrahydrofuran (300 mL) was added, dropwise over 20 minutes, a 2.0 M solution of lithium diisopropylamide in tetrahydrofuran/heptane/ethylbenzene (92.6 mL, 185 mmol). The reaction was maintained at −78° C. for two hours and then treated with, dropwise over 15 minutes, tert-butyl((5-iodo-2,2-dimethylpentyl)oxy)dimethylsilane (Intermediate 29C-1, 42.5 g, 119 mmol). The cooling bath was removed, and the mixture was stirred overnight at room temperature. After quenching the reaction by the slow addition of aqueous ammonium chloride solution (50 mL), the mixture was concentrated to remove the organic solvent. The residue was partitioned between brine (200 mL) and ethyl acetate (300 mL) and the organic layer was combined with additional extracts (ethyl acetate, 2×300 mL), dried over sodium sulfate and concentrated. The crude material was purified by automated flash chromatography (330 g silica gel column, 0-20% ethyl acetate in petroleum ether) to afford the title compound as a near colorless oil (50.1 g, 90%). $^1$H NMR (400 MHz, $CD_3OD$) δ 7.43 (s, 1H), 7.37 (d, J=7.6 Hz, 1H), 7.29-7.21 (m, 2H), 3.23 (d, J=1.2 Hz, 2H), 1.94-1.86 (m, 1H), 1.82-1.74 (m, 1H), 1.45 (s, 3H), 1.39 (s, 9H), 1.27-1.17 (m, 4H), 0.88 (s, 9H), 0.80 (d, J=4.4 Hz, 6H), 0.02-0.00 (m, 6H) ppm.

The following intermediates were prepared based on the procedure described for Intermediate 47A.

| Inter. No. | Structure | Name | MS m/z [M + H]$^+$ |
|---|---|---|---|
| 47A-1 | 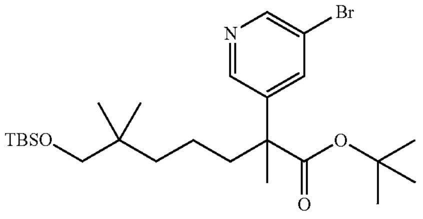 [SMILES: CC(C)(CCCC(C)(C(=O)OC(C)(C)C)c1cncc(Br)c1)CO[Si](C)(C)C(C)(C)C] | tert-butyl 2-(5-bromopyridin-3-yl)-7-((tert-butyldimethylsilyl)oxy)-2,6,6-trimethylheptanoate | MS: 514, 516; RT: 3.18 min. (LCMS Method 034) |
| 47A-2 | 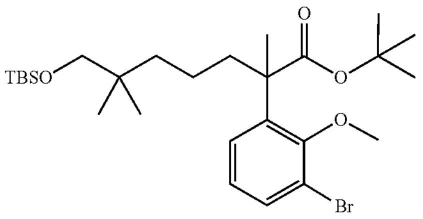 [SMILES: COc1c(Br)cccc1C(C)(CCCC(C)(C)CO[Si](C)(C)C(C)(C)C)C(=O)OC(C)(C)C] | tert-butyl 2-(3-bromo-2-methoxyphenyl)-7-((tert-butyldimethylsilyl)oxy)-2,6,6-trimethylheptanoate | MS: 565, 567 [M + Na]$^+$; RT: 4.44 min. (LC-MS Method 50) |

Intermediate 47B: tert-Butyl 7-((tert-butyldimethylsilyl)oxy)-2-(3-(2-ethoxy-2-oxoethyl)phenyl)-2,6,6-trimethylheptanoate

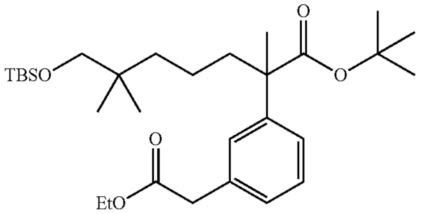 [SMILES: CCOC(=O)Cc1cccc(C(C)(CCCC(C)(C)CO[Si](C)(C)C(C)(C)C)C(=O)OC(C)(C)C)c1]

To a stirred solution of tert-butyl 2-(3-bromophenyl)-7-((tert-butyldimethylsilyl)oxy)-2,6,6-trimethylheptanoate (Intermediate 47A, 15.0 g, 29.2 mmol) in mesitylene (150 mL) was added ethyl potassium malonate (7.46 g, 43.8 mmol), allylpalladium(II) chloride dimer (0.214 g, 0.585 mmol), rac-2,2'-bis(diphenylphosphino)-1,1'-binapthyl (1.09 g, 1.75 mmol) and 4-(dimethylamino)pyridine (0.357 g, 2.92 mmol). The mixture was sparged with argon for 15 minutes and then heated overnight at 140° C. Following this time, the reaction was cooled to room temperature, concentrated to a dry residue, and partitioned between ethyl acetate (300 mL), and water (300 mL). The organic layer was washed with a second portion of water (1×300 mL), dried over sodium sulfate and concentrated. The crude material was purified by automated flash chromatography (330 g silica gel column, 0-30% ethyl acetate in petroleum ether) to afford the title compound as a tacky solid (5.99 g, 39%). MS (ESI): 543 m/z [M+Na]$^+$.

Intermediate 47C: tert-Butyl 2-(3-(2-ethoxy-2-oxoethyl)phenyl)-7-hydroxy-2,6,6-trimethylheptanoate

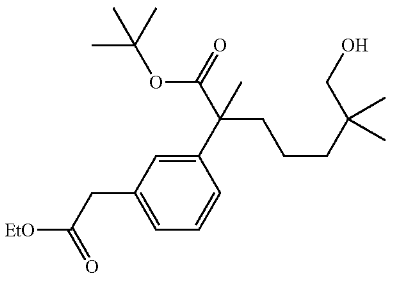 [SMILES: CCOC(=O)Cc1cccc(C(C)(CCCC(C)(C)CO)C(=O)OC(C)(C)C)c1]

To a stirred solution of tert-butyl 7-((tert-butyldimethylsilyl)oxy)-2-(3-(2-ethoxy-2-oxoethyl)phenyl)-2,6,6-trimethylheptanoate (Intermediate 47B, 5.99 g, 11.5 mmol) in tetrahydrofuran (30 mL) was added a 1.0 M solution of tetrabutylammonium fluoride in tetrahydrofuran (23.0 mL, 23.0 mmol). The reaction was stirred overnight at room temperature and then partitioned between ethyl acetate (100 mL) and water (100 mL). The organic layer was washed with additional portions of water (2×100 mL), dried over magnesium sulfate and concentrated. The crude residue was purified by automated flash chromatography (80 g silica gel column, 0-30% ethyl acetate in petroleum ether) to afford the title compound as a pale amber oil (3.30 g, 71%). MS (ESI): 429 m/z [M+Na]$^+$.

Intermediate 47D: tert-Butyl 7-(acetylthio)-2-(3-(2-ethoxy-2-oxoethyl)phenyl)-2-methylheptanoate

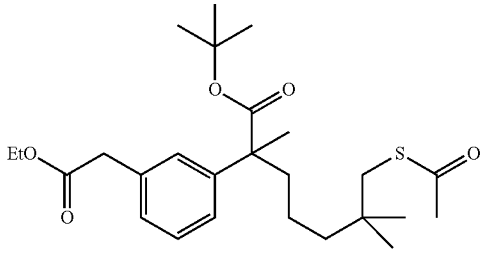 [SMILES: CCOC(=O)Cc1cccc(C(C)(CCCC(C)(C)CSC(C)=O)C(=O)OC(C)(C)C)c1]

To a stirred and cooled (0° C.) solution of triphenylphosphine (4.26 g, 16.2 mmol) in tetrahydrofuran (100 mL) was added, dropwise over 4-5 minutes, diisopropyl azodicarboxylate (3.20 mL, 3.29 g, 16.3 mmol). The mixture was maintained at 0° C. Upon the appearance of a white precipitate (approximately 30 minutes), a premade solution of tert-butyl 2-(3-(2-ethoxy-2-oxoethyl)phenyl)-7-hydroxy-2,6,6-trimethylheptanoate (Intermediate 47C, 3.30 g, 8.12 mmol) and thioacetic acid (1.16 mL, 1.24 g, 16.2 mmol) in tetrahydrofuran (20 mL) were added, dropwise over five minutes. The reaction was held at 0° C. for another hour, warmed to room temperature and then stirred for a final hour. After this time, the mixture concentrated to a dry residue which was directly subjected to automated flash chromatography (120 g silica gel column, 0-30% ethyl acetate in petroleum ether). The title compound was afforded as a viscous, amber oil (3.71 g, 98%). MS (ESI): 487 m/z $[M+Na]^+$.

Intermediate 47E: tert-Butyl 2-(3-(2-ethoxy-2-oxoethyl)phenyl)-7-((2-ethoxy-2-oxoethyl)thio)-2-methylheptanoate

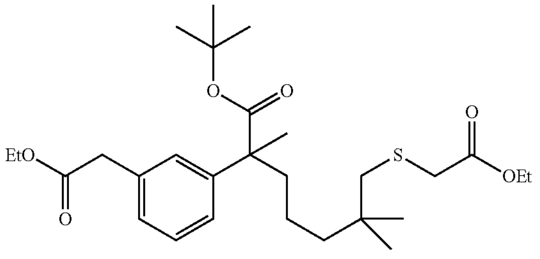 [SMILES: CCOC(=O)CSCC(C)(C)CCCC(C)(C(=O)OC(C)(C)C)c1cccc(CC(=O)OCC)c1]

To a stirred solution of tert-Butyl 7-(acetylthio)-2-(3-(2-ethoxy-2-oxoethyl)phenyl)-2-methylheptanoate (Intermediate 47D, 3.71 g, 7.98 mmol) in ethanol (50 mL) was added ethyl bromoacetate (1.15 mL, 1.73 g, 10.4 mmol) followed by solid sodium ethoxide (0.813 g, 11.9 mmol). After one hour at room temperature, the reaction was partitioned between ethyl acetate (100 mL) and water (100 mL). The organic layer was washed with additional portions of water (2×100 mL), dried over magnesium sulfate and concentrated. The crude residue was purified by automated flash chromatography (40 g silica gel column, 0-30% ethyl acetate in petroleum ether) to afford the title compound as a viscous oil (3.11 g, 77%). MS (ESI): 531 m/z $[M+Na]^+$.

Intermediate 47F: tert-Butyl 2-(3-(2-ethoxy-2-oxoethyl)phenyl)-7-((2-ethoxy-2-oxoethyl)sulfonyl)-2,6,6-trimethylheptanoate

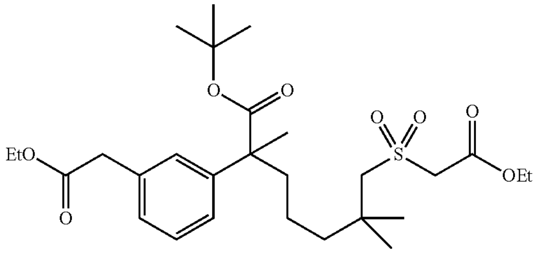 [SMILES: CCOC(=O)Cc1cccc(C(C)(CCCC(C)(C)CS(=O)(=O)CC(=O)OCC)C(=O)OC(C)(C)C)c1]

To a stirred and cooled (0° C.) solution of tert-butyl 2-(3-(2-ethoxy-2-oxoethyl)phenyl)-7-((2-ethoxy-2-oxoethyl)thio)-2-methylheptanoate (Intermediate 47E, 13.11 g, 6.11 mmol) in methanol (200 mL) was added a solution of ammonium molybdate tetrahydrate (6.20 g, 5.02 mmol) dissolved in 30% aqueous hydrogen peroxide solution (31 mL). Following the addition, the cooling bath was removed, and the reaction was stirred at room temperature for two hours before partitioning between ethyl acetate (500 mL) and water (500 mL). The organic layer was washed with additional portions of water (2×500 mL), dried over sodium sulfate and concentrated. The crude residue was purified by automated flash chromatography (40 g silica gel column, 0-50% ethyl acetate in petroleum ether) to afford the title compound as a gummy solid (3.01 g, 91%). MS (ESI): 563 m/z $[M+Na]^+$.

Intermediate 48: 2-(3-Bromophenyl)-4-((1-hydroxy-2-methylpropan-2-yl)oxy)-2-methylbutanoic Acid

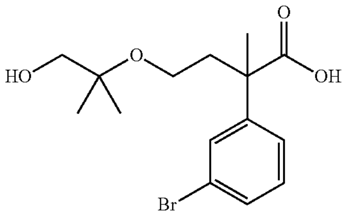 [SMILES: CC(C)(CO)OCCC(C)(C(=O)O)c1cccc(Br)c1]

To a stirred solution of methyl 2-(3-bromophenyl)-4-((1-hydroxy-2-methylpropan-2-yl)oxy)-2-methylbutanoate (Intermediate 48E, 50.0 g, 139 mmol) in a mixture of tetrahydrofuran (250 mL) and methanol (80 mL) was added a 5.0 M aqueous lithium hydroxide solution (83.5 mL, 418 mmol). The reaction was heated overnight at 60° C. and then cooled to room temperature and acidified (pH 4) with the addition of 1.0 N hydrochloric acid (~420 mL). The mixture was extracted with ethyl acetate (1×300 mL) and the organic layer was washed with brine (2×300 mL), dried over sodium sulfate and concentrated. The crude title compound, which was used without purification, was obtained as a colorless gum (43.0 g, 90%). MS (ESI): 367, 369 m/z $[M+Na]^+$.

Intermediate 48A: 2-(2-Chloroethoxy)-2-methylpropan-1-ol

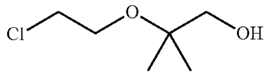

To a stirred solution of 1,1-dimethyloxirane (73.9 mL, 60.0 g, 832 mmol) in 2-chloroethanol (335 mL, 402 g, 5.00 mol) was added phosphotungstic acid hydrate (9.66 g, 3.35 mmol based on anhydrous molecular weight). The reaction was heated overnight at 45° C. and then cooled to room temperature and concentrated to remove the excess 2-chloroethanol. The crude residue was purified by automated flash chromatography (330 g silica gel column, 0-10% ethyl acetate in petroleum ether) to afford the title compound as a near-colorless, oil (51.0 g, 40%). $^1$H NMR (400 MHz, $CDCl_3$) δ 3.69-3.58 (m, 4H), 3.45 (d, J=6.4 Hz, 2H), 2.10 (t, J=6.4 Hz, 1H), 1.20 (s, 6H) ppm.

Intermediate 48B: tert-Butyl(2-(2-chloroethoxy)-2-methylpropoxy)dimethylsilane

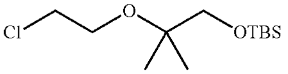 [SMILES: CC(C)(CO[Si](C)(C)C(C)(C)C)OCCCl]

To a stirred solution of 2-(2-chloroethoxy)-2-methylpropan-1-ol (Intermediate 48A, 51.0 g, 334 mmol) in dichloromethane (1 L) was added tert-butyldimethylsilyl chloride (60.4 g, 401 mmol) followed by imidazole (45.5 g, 668 mmol). The reaction was allowed to proceed overnight at room temperature and then washed with brine (2×500 mL), dried over sodium sulfate and concentrated. The crude residue was purified by automated flash chromatography (330 g silica gel column, 0-5% ethyl acetate in petroleum ether) to afford the title compound as a colorless oil (61.0 g, 68%). $^1$H NMR (400 MHz, $CDCl_3$) δ 3.70 (t, J=6.0 Hz, 2H), 3.56 (t, J=6.0 Hz, 2H), 3.45 (s, 2H), 1.17 (s, 6H), 0.90 (s, 9H), 0.05 (s, 6H) ppm.

Intermediate 48C: tert-Butyl(2-(2-iodoethoxy)-2-methylpropoxy)dimethylsilane

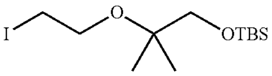 [SMILES: CC(C)(CO[Si](C)(C)C(C)(C)C)OCCI]

To a stirred solution of tert-butyl(2-(2-chloroethoxy)-2-methylpropoxy)dimethylsilane (Intermediate 48B, 22.0 g, 82.4 mmol) in acetone (500 mL) was added sodium iodide (37.1 g, 248 mmol). The mixture was heated at 75° C. for 48 hours and then cooled to room temperature and concentrated. The obtained residue was partitioned between ethyl acetate (200 mL) and water (200 mL). The organic layer was washed with additional portions of water (2×200 mL), dried over magnesium sulfate and concentrated. The resulting crude product was purified by automated flash chromatography (330 g silica gel column, 0-5% ethyl acetate in petroleum ether) to afford the title compound as a pale amber oil (25.0 g, 85%). MS (ESI): 381 m/z [M+Na]$^+$.

Intermediate 48D: Methyl 2-(3-bromophenyl)-4-((1-((tert-butyldimethylsilyl)oxy)-2-methylpropan-2-yl)oxy)-2-methylbutanoate

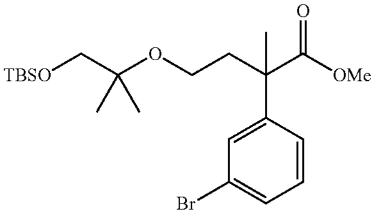 [SMILES: COC(=O)C(C)(CCOC(C)(C)CO[Si](C)(C)C(C)(C)C)c1cccc(Br)c1]

To a stirred and cooled (−78° C.) of methyl 2-(3-bromophenyl)propanoate (15 g, 61.7 mmol) in tetrahydrofuran (200 mL) was added, dropwise over 15 minutes, a 2.0 M solution of lithium diisopropylamide in tetrahydrofuran/heptane/ethylbenzene (37.0 mL, 74.0 mmol). The mixture was maintained at −78° C. for two hours before adding, dropwise over 15 minutes, tert-butyl(2-(2-iodoethoxy)-2-methylpropoxy)dimethylsilane (Intermediate 48C, 24.3 g, 67.8 mmol). Following the addition, the reaction was allowed to slowly warm to room temperature and stirred overnight. The mixture was then diluted (slowly, initially) with water (300 mL) and concentrated to remove the organic solvent. The resulting suspension of gummy solid was extracted with ethyl acetate (1×300 mL) and the organic layer was washed with brine (2×300 mL), dried over sodium sulfate and concentrated. The crude residue was purified by automated flash chromatography (330 g silica gel column, 0-20% ethyl acetate in petroleum ether) to afford the title compound as a faint amber gum (22.0 g, 75%). MS (ESI): 495, 497 m/z [M+Na]$^+$.

Intermediate 48E: Methyl 2-(3-bromophenyl)-4-((1-hydroxy-2-methylpropan-2-yl)oxy)-2-methylbutanoate

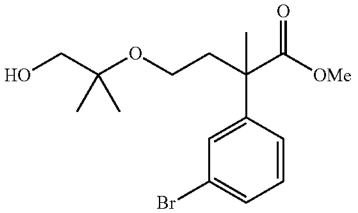 [SMILES: COC(=O)C(C)(CCOC(C)(C)CO)c1cccc(Br)c1]

To a stirred solution of methyl 2-(3-bromophenyl)-4-((1-((tert-butyldimethylsilyl)oxy)-2-methylpropan-2-yl)oxy)-2-methylbutanoate (Intermediate 48D, 22.0 g, 46.5 mmol) in tetrahydrofuran (140 mL) was added a 1.0 M solution of tetrabutylammonium fluoride in tetrahydrofuran (139 mL, 139 mmol). The reaction was allowed to proceed overnight at room temperature and then partitioned between ethyl acetate (300 mL) and water (300 mL). The organic layer was washed with additional portions of water (2×300 mL), dried over magnesium sulfate and concentrated. The crude residue was purified by automated flash chromatography (330 g silica gel column, 0-30% ethyl acetate in petroleum ether) to afford the title compound as a colorless, foamy gum (14.2 g, 85%). MS (ESI): 359, 361 m/z [M+H]$^+$.

Intermediate 49: Benzyl 2-(3-bromophenyl)-4-((1-((tert-butyldimethylsilyl)oxy)-2-methylpropan-2-yl)oxy)-2-methylbutanoate

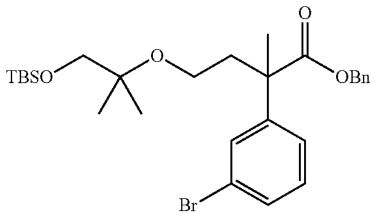 [SMILES: CC(C)(CO[Si](C)(C)C(C)(C)C)OCCC(C)(C(=O)OCc1ccccc1)c1cccc(Br)c1]

To a stirred solution of benzyl 2-(3-bromophenyl)-4-((1-hydroxy-2-methylpropan-2-yl)oxy)-2-methylbutanoate (Intermediate 41-2, 9.60 g, 22.1 mmol) in dichloromethane (200 mL) was added tert-butyldimethylsilyl chloride (3.99 g, 26.5 mmol) followed by imidazole (3.00 g, 44.1 mmol). The reaction was allowed to proceed overnight at room temperature and then diluted with dichloromethane (100 mL) and washed with brine (2×100 mL). The organic solution was dried over anhydrous sodium sulfate and concentrated to obtain the crude product. This material was purified by automated flash chromatography (120 g silica gel column, 0-5% ethyl acetate in petroleum ether) to afford the title compound as a colorless gum (11.4 g, 94%).

$^1$H NMR (400 MHz, $CDCl_3$) δ 7.46 (t, J=2.0 Hz, 1H), 7.38-7.27 (m, 4H), 7.24-7.19 (m, 3H), 7.15 (t, J=7.6 Hz, 1H), 5.10 (s, 2H), 3.43-3.29 (m, 4H), 2.41-2.32 (m, 1H), 2.17-2.08 (m, 1H), 1.57 (s, 3H), 1.05 (s, 6H), 0.87 (s, 9H), 0.01 (s, 6H) ppm.

Intermediate 50: Benzyl 4-((1-((tert-butyldimethylsilyl)oxy)-2-methylpropan-2-yl)oxy)-2-(3-(2-ethoxy-2-oxoethyl)phenyl)-2-methylbutanoate

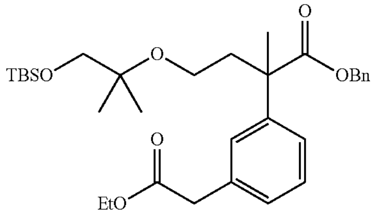 [SMILES: CCOC(=O)Cc1cccc(C(C)(CCOC(C)(C)CO[Si](C)(C)C(C)(C)C)C(=O)OCc2ccccc2)c1]

To a stirred solution of benzyl 2-(3-bromophenyl)-4-((1-((tert-butyldimethylsilyl)oxy)-2-methylpropan-2-yl)oxy)-2-methylbutanoate (intermediate 49, 11.1 g, 20.2 mmol) in mesitylene (110 mL) was added ethyl potassium malonate (5.11 g, 30.0 mmol), allylpalladium(II) chloride dimer (0.146 g, 0.399 mmol), rac-2,2'-bis(diphenylphosphino)-1,1'-binapthyl (0.750 g, 1.20 mmol) and 4-(dimethylamino)pyridine (0.250 g, 2.05 mmol). The mixture was sparged with argon for 15 minutes and then heated overnight at 140° C. Following this time, the reaction was cooled to room temperature, concentrated to a dry residue, and partitioned between ethyl acetate (300 mL), and water (150 mL). The organic layer was washed with a second portion of water (1×150 mL), dried over anhydrous sodium sulfate and concentrated. The crude material was purified by automated flash chromatography (120 g silica gel column, 0-30% ethyl acetate in petroleum ether) to afford the title compound as a pale amber solid (6.30 g, 56%). $^1$H NMR (400 MHz, $CDCl_3$) δ 7.32-7.26 (m, 3H), 7.26-7.14 (m, 6H), 5.09 (s, 2H), 4.14 (q, J=7.2 Hz, 1H), 3.55 (s, 2H), 3.47-3.30 (m, 4H), 2.46-2.37 (m, 1H), 2.18-2.09 (m, 1H), 1.58 (s, 3H), 1.23 (t, J=7.2 Hz, 1H), 1.05 (s, 6H), 0.87 (s, 9H), 0.01 (s, 6H) ppm.

Intermediate 51: Benzyl 2-(3-(2-ethoxy-2-oxoethyl)phenyl)-4-((1-hydroxy-2-methylpropan-2-yl)oxy)-2-methylbutanoate

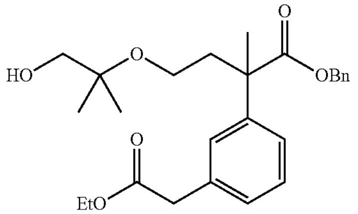 [SMILES: CCOC(=O)Cc1cccc(C(C)(CCOC(C)(C)CO)C(=O)OCc2ccccc2)c1]

To a stirred solution of benzyl 4-((1-((tert-butyldimethylsilyl)oxy)-2-methylpropan-2-yl)oxy)-2-(3-(2-ethoxy-2-oxoethyl)phenyl)-2-methylbutanoate (Intermediate 50, 6.30 g, 11.3 mmol) in tetrahydrofuran (25 mL) was added a 1.0M solution of tetrabutylammonium fluoride in tetrahydrofuran (22.6 mL, 22.6 mmol). The reaction was allowed to proceed overnight at room temperature and then partitioned between ethyl acetate (100 mL) and water (60 mL). The organic layer was washed with additional portions of water (2×60 mL), dried over sodium sulfate and concentrated. The crude residue was purified by automated flash chromatography (80 g silica gel column, 0-30% ethyl acetate in petroleum ether) to afford the title compound as a colorless, foamy gum (4.01 g, 80%). MS (ESI): 465 m/z [M+Na]$^+$.

Intermediate 52: 3-(2-Fluoro-5-((6-fluoro-4-vinyl-1H-indol-5-yl)oxy)phenyl)-1-(tetrahydro-2H-pyran-2-yl)-1H-pyrazole-4-carbonitrile

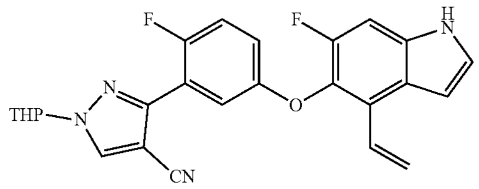

To a stirred solution of 6-fluoro-5-(4-fluoro-3-(4,4,5,5-tetramethyl-1,3,2-dioxaborolan-2-yl)phenoxy)-4-vinyl-1H-indole (Intermediate 20, 5.8 g, 14.6 mmol) in 1,4-dioxane (60 mL) and water (15 mL) was added 3-iodo-1-(tetrahydro-2H-pyran-2-yl)-1H-pyrazole-4-carbonitrile (Intermediate 26, 5.75 g, 19.0 mmol), cesium carbonate (9.51 g, 29.2 mmol) and $PdCl_2$(dppf) (1.46 g, 1.19 mmol). The reaction was purged with argon and stirred at 100° C. for 16 hours. The mixture was diluted with ethyl acetate (150 mL). The organic solution was washed with water (2×150 mL), dried over anhydrous sodium sulfate and concentrated. The residue was purified by flash chromatography (80 g silica gel column, 0-50% ethyl acetate in petroleum ether) to give the title compound as a yellow solid (4.2 g, 64%). MS (ESI): 447 m/z [M+H]$^+$.

The following intermediate was prepared based on the procedures described for Intermediate 52.

| Inter. No. | Structure | Name | MS m/z $[M + H]^+$ |
|---|---|---|---|
| 52-1 | 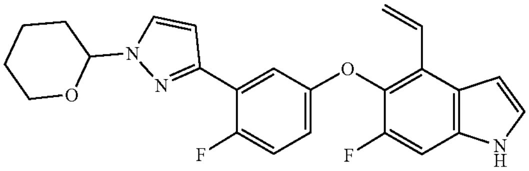 [SMILES: C=Cc1c(Oc2ccc(F)c(-c3ccn(C4CCCCO4)n3)c2)c(F)cc2[nH]ccc12] | 6-fluoro-5-(4-fluoro-3-(1-(tetrahydro-2H-pyran-2-yl)-1H-pyrazol-3-yl)phenoxy)-4-vinyl-1H-indole | 422 |

Intermediate 53: Ethyl 3-(3-(6-(acetylthio)-5,5-dimethyl-1-((tetrahydro-2H-pyran-2-yl)oxy)hexyl)phenyl)propanoate

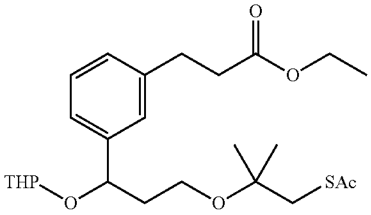

To a stirred solution of triphenylphosphine (16.50 g, 62.7 mmol) in tetrahydrofuran (300 mL) was added diisopropyl azodicarboxylate (12.3 mL, 62.7 mmol) dropwise at 0° C., and the resulting mixture was stirred at 0° C. until the formation of a white solid was observed. A solution of ethyl 3-(3-(6-hydroxy-5,5-dimethyl-1-((tetrahydro-2H-pyran-2-yl)oxy)hexyl)phenyl)propanoate (Intermediate 36, 8.50 g, 20.9 mmol) and thioacetic acid (4.48 mL, 62.7 mmol) in tetrahydrofuran was added dropwise at 0° C. followed by stirring at 0° C. for 1 hour and at 25° C. for 1 hour. The solvent was evaporated under reduced pressure and the residue was purified by flash chromatography (330 g silica gel column, 0-30% ethyl acetate in petroleum) to give the title compound as an oil (7.10 g, 73%). MS (ESI): 487 m/z $[M+Na]^+$.

Intermediate 54: Methyl 2-((6-bromo-6-(3-bromophenyl)-2,2-dimethylhexyl)thio)acetate

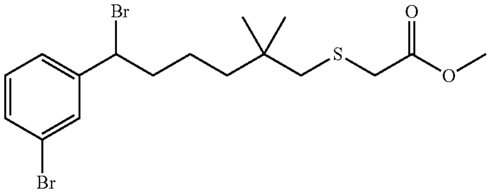 [SMILES: COC(=O)CSCC(C)(C)CCCC(Br)c1cccc(Br)c1]

To a solution of methyl 2-((6-(3-bromophenyl)-6-hydroxy-2,2-dimethylhexyl)thio)acetate (Intermediate 54D, 6.50 g, 16.7 mmol) in dichloromethane (150 mL) was added N-bromosuccinimide (4.46 g, 25.0 mmol), followed by triphenyl phosphine (6.57 g, 25.0 mmol). The reaction mixture was stirred at room temperature for 1 hour, then diluted with dichloromethane (100 mL). The solution was washed with water (2×100 mL), dried over anhydrous sodium sulfate and concentrated. The residue was purified by flash chromatography (80 g silica gel column, 0-10% ethyl acetate in petroleum ether) to give the title compound as an oil (5.20 g, 69%). $^1H$ NMR (400 MHz, $CDCl_3$) δ7.54 (s, 1H), 7.41 (d, J=7.9 Hz, 1H), 7.32 (d, J=7.8 Hz, 1H), 7.21 (t, J=7.8 Hz, 1H), 4.88 (dd, J=8.4, 6.6 Hz, 1H), 3.74 (d, J=3.7 Hz, 3H), 3.19 (s, 2H), 2.57 (s, 2H), 2.27-2.19 (m, 1H), 2.06 (dt, J=14.0, 5.8 Hz, 1H), 1.46 (td, J=9.9, 5.5 Hz, 1H), 1.36-1.26 (m, 3H), 0.94 (s, 6H) ppm.

The following intermediates were prepared based on the procedures described for Intermediate 54, and/or for Intermediate 54A-54D:

| Inter No. | Structure | Name | MS m/z $[M + H]^+$/$^1H$ NMR |
|---|---|---|---|
| 54-1 | 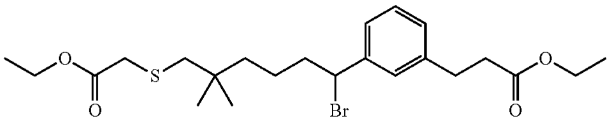 [SMILES: CCOC(=O)CCc1cccc(C(Br)CCCC(C)(C)CSCC(=O)OCC)c1] | Ethyl 3-(3-(1-bromo-6-((2-ethoxy-2-oxoethyl)thio)-5,5-dimethylhexyl)phenyl) propanoate | 509, 511 $[M + Na]^+$. |
| 54-2 | 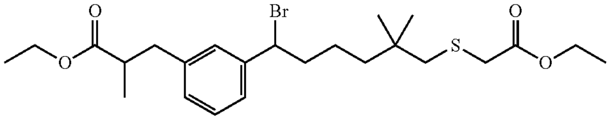 [SMILES: CCOC(=O)CSCC(C)(C)CCCC(Br)c1cccc(CC(C)C(=O)OCC)c1] | Ethyl 3-(3-(1-bromo-6-((2-ethoxy-2-oxoethyl)thio)-5,5-dimethylhexyl)phenyl)-2-methylpropanoate | 1H NMR (400 MHZ, $CDCl_3$) δ 7.25-7.22 (m, 2H), 7.19-7.17 (m, 1H), 7.10-7.06 (m, 1H), 4.93 (t, J = 7.6 Hz, 1H), 4.19 (q, J = 7.2 Hz, 2H), 4.09 (q, J = 7.2 Hz, 2H), 3.17 (s, 2H), 3.03-2.99 (m, 1H), 2.74-2.64 (m, 2H), 2.57 (s, 2H), 2.30-2.21 (m, 1H), 2.12-2.02 (m, 1H), 1.49-1.43 (m, 1H), 1.36-1.27 (m, 6H), 1.19 (t, J = 7.2 Hz, 3H), 1.15 (t, J = 7.2 Hz, 3H), 0.93 (s, 6H) ppm. |

-continued

| Inter No. | Structure | Name | MS m/z $[M + H]^+/^1H$ NMR |
|---|---|---|---|
| 54-3 | 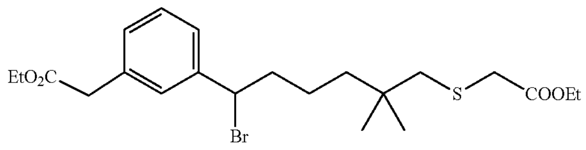 [SMILES: CCOC(=O)CSCC(C)(C)CCCC(Br)c1cccc(CC(=O)OCC)c1] | Ethyl 2-(3-(1-bromo-6-((2-ethoxy-2-oxoethyl)thio)-5,5-dimethylhexyl)phenyl) acetate | 495, 497 $[M + Na]^+$ |
| 54-4 | 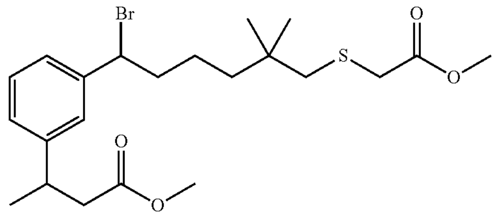 [SMILES: COC(=O)CSCC(C)(C)CCCC(Br)c1cccc(C(C)CC(=O)OC)c1] | methyl 3-(3-(1-bromo-6-((2-methoxy-2-oxoethyl)thio)-5,5-dimethylhexyl)phenyl) butanoate | 473, 475 |
| 54-5 | 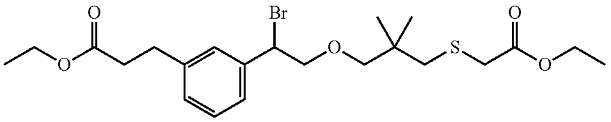 [SMILES: CCOC(=O)CCc1cccc(C(Br)COCC(C)(C)CSCC(=O)OCC)c1] | ethyl 3-(3-(1-bromo-2-(3-((2-ethoxy-2-oxoethyl)thio)-2,2-dimethylpropoxy)ethyl) phenyl)propanoate | MS: 489, 491; $^1H$ NMR (400 MHZ, $CDCl_3$) δ 7.26-7.23 (m, 3H), 7.16-7.13 (m, 1H), 5.03 (t, J = 6.8 Hz, 1H), 4.19 (q, J = 7.2 Hz, 2H), 4.12 (q, J = 7.2 Hz, 2H), 3.94 (dd, J = 10.8, 7.2 Hz, 1H), 3.85 (dd, J = 10.8, 6.4 Hz, 1H), 3.25 (dd, J = 22.0, 8.8 Hz, 2H), 3.16 (s, 2H), 2.95 (t, J = 7.6 Hz, 2H), 262 (t, J = 7.6 Hz, 2H), 2.61 (s, 2H), 1.29 (t, J = 7.2 Hz, 3H), 1.23 (t, J = 7.2 Hz, 3H), 0.93 (s, 3H), 0.92 (s, 3H) ppm. |
| 54-6 | 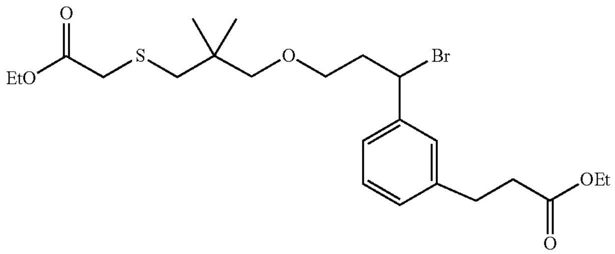 [SMILES: CCOC(=O)CCc1cccc(C(Br)CCOCC(C)(C)CSCC(=O)OCC)c1] | ethyl 3-(3-(1-bromo-3-(3-((2-ethoxy-2-oxoethyl)thio)-2,2-dimethylpropoxy) propyl)phenyl) propanoate | 525, 527 $[M + Na]^+$ |

Intermediate 54A: 6-(3-Bromophenyl)-2,2-dimethyl-6-((tetrahydro-2H-pyran-2-yl)oxy)hexyl methanesulfonate

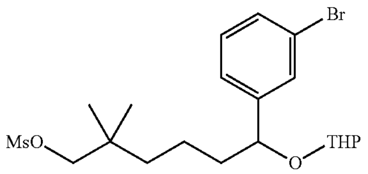

To a solution of 6-(3-bromophenyl)-2,2-dimethyl-6-tetrahydropyran-2-yloxy-hexan-1-ol (Intermediate 35, 12.00 g, 31.1 mmol) in dichloromethane (150 mL) were added methanesulfonyl chloride (3.6 mL, 46.7 mmol) and triethylamine (13.0 mL, 93.4 mmol) at 0° C. The reaction mixture was stirred at room temperature for 3 hours, then diluted with dichloromethane (100 mL). The solution was washed with brine (2×300 mL), dried over anhydrous magnesium sulfate and concentrated. The residue was purified by silica gel column chromatography (120 g silica gel column, 0-20% ethyl acetate in petroleum ether) to give the title compound as an oil (11.30 g, 78%). MS (ESI): 485, 487 m/z $[M+Na]^+$.

Intermediate 54B: S-(6-(3-Bromophenyl)-2,2-dimethyl-6-((tetrahydro-2H-pyran-2-yl)oxy)hexyl) ethanethioate

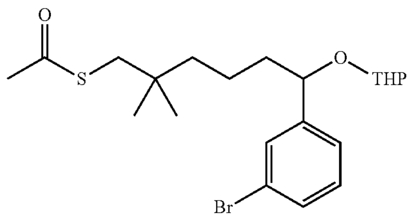

To a solution of 6-(3-bromophenyl)-2,2-dimethyl-6-((tetrahydro-2H-pyran-2-yl)oxy)hexyl methanesulfonate (Intermediate 54A, 11.30 g, 24.4 mmol) in N,N-dimethylformamide (150 mL) was added potassium thioacetate (13.90 g, 122.0 mmol). The reaction mixture was stirred at 80° C. under argon atmosphere for 16 hours, then diluted with ethyl acetate. The solution was washed with water, dried over anhydrous magnesium sulfate, and concentrated. The residue was purified by flash chromatography (120 g silica gel column, 0-15% ethyl acetate in petroleum) to give the title compound as an oil (9.20 g, 85%). MS (ESI): 465, 467 m/z $[M+Na]^+$.

Intermediate 54C: Methyl 2-((6-(3-bromophenyl)-2,2-dimethyl-6-((tetrahydro-2H-pyran-2-yl)oxy)hexyl)thio)acetate

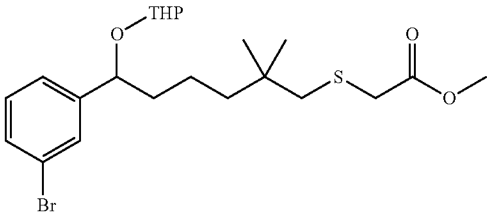

To a solution of S-(6-(3-bromophenyl)-2,2-dimethyl-6-((tetrahydro-2H-pyran-2-yl)oxy)hexyl) ethanethioate (Intermediate 54B, 9.2 g, 20.7 mmol) in methanol (150 mL) was added ethyl bromoacetate (4.5 mg, 27.0 mmol), sodium methoxide (5.7 mL, 31.1 mmol, 6 M in methanol). The reaction was stirred at room temperature for 3 hours, then diluted with ethyl acetate (200 mL). The solution was washed with water (3×200 mL), dried over anhydrous magnesium sulfate, filtered, and concentrated. The residue was purified by flash chromatography (120 g silica gel column, 0-30% ethyl acetate in petroleum) to give the title compound as an oil (8.80 g, 90%). MS (ESI): 495, 497 m/z $[M+H]^+$.

Intermediate 54D: Methyl 2-((6-(3-bromophenyl)-6-hydroxy-2,2-dimethylhexyl)thio)acetate

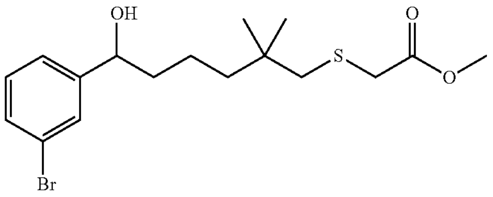 [SMILES: COC(=O)CSCC(C)(C)CCCC(O)c1cccc(Br)c1]

To a solution of methyl 2-((6-(3-bromophenyl)-2,2-dimethyl-6-((tetrahydro-2H-pyran-2-yl)oxy)hexyl)thio)acetate (Intermediate 54C, 8.80 g, 18.6 mmol) in methanol (100 mL) was added pyridinium p-toluenesulfonate (4.67 g, 18.6 mmol). The reaction mixture was stirred at room temperature for 16 hours, then diluted with ethyl acetate (200 mL). The solution was washed with water (2×200 mL), dried over anhydrous sodium sulfate and concentrated. The residue was purified by flash chromatography (80 g silica gel column, 0-30% ethyl acetate in petroleum ether) to give the title compound as an oil (6.50 g, 90%). MS (ESI): 411 m/z $[M+Na]^+$.

Intermediate 55: 2-(3-(3-Ethoxy-3-oxopropyl)phenyl)-7-hydroxy-2,6,6-trimethylheptanoic acid

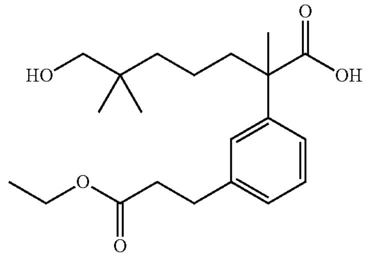 [SMILES: CCOC(=O)CCc1cccc(C(C)(CCCC(C)(C)CO)C(=O)O)c1]

To a stirred solution of (E)-2-(3-(3-Ethoxy-3-oxoprop-1-en-1-yl)phenyl)-7-hydroxy-2,6,6-trimethylheptanoic acid (Intermediate 55A, 42.9 g, 0.12 mol, 1.0 eq.) in methanol (100 mL) was added palladium on carbon (10%) (8.5 g). The reaction was stirred overnight at room temperature under a hydrogen balloon. The mixture was filtered through a pad of Celite. The filtrate was concentrated to afford the title compound (39.3 g, yield 91.2%) as yellow oil. MS (ESI): 365 m/z $[M+H]^+$.

Intermediate 55A: (E)-2-(3-(3-Ethoxy-3-oxoprop-1-en-1-yl)phenyl)-7-hydroxy-2,6,6-trimethylheptanoic Acid

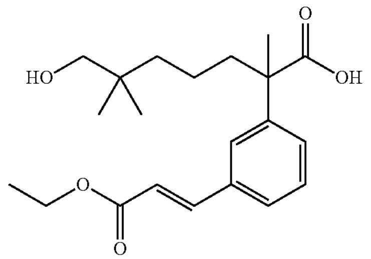 [SMILES: CCOC(=O)/C=C/c1cccc(C(C)(CCCC(C)(C)CO)C(=O)O)c1]

A stirred solution of 7-hydroxy-2-(3-iodophenyl)-2,6,6-trimethylheptanoic acid (65 g, 0.17 mol, 1.0 eq. Intermediate 17B), triethylamine (50.6 g, 0.50 mol, 3.0 eq.) in dimethyl formamide (100 mL) was purged with nitrogen for 20 minutes. Ethyl acrylate (50 g, 0.50 mol, 3.0 eq.), tri-ortho-tolyl phosphine (10.1 g, 33.3 mmol, 0.2 eq.) and palladium (II) acetate (3.75 g, 16.7 mmol, 0.1 eq.) were charged. The mixture was purged with nitrogen for another 10 minutes, then stirred at 120° C. overnight under nitrogen. The reaction was cooled, quenched with water, and extracted with ethyl acetate (4×300 mL). The combined organic extracts were washed with water, brine, and dried over anhydrous sodium sulfate. After removal of solvent, the residue was purified by silica gel flash column (petroleum ether:ethyl acetate=3:1) to afford the title compound (42.9 g, yield 71.1%) as a yellow oil. MS (ESI): 363 m/z $[M+H]^+$. RT: 1.95 min. (LC-MS method B). $^1H$ NMR (400 MHz, $CDCl_3$-d) 7.42 (d, J=16.0 Hz, 1H), 7.51 (s, 1H), 7.44-7.33 (m, 3H), 6.44 (d, J=16.0 Hz, 1H), 4.29-4.24 (m, 2H), 3.27 (s, 2H), 2.20-1.85 (m, 2H), 1.59 (s, 3H), 1.59-1.29 (m, 7H), 0.02 (s, 6H) ppm.

The following intermediate was prepared based on the procedures described for Intermediate 55A, starting from corresponding intermediate:

| Inter. No. | Structure | Name | MS m/z [M + H]+ |
|---|---|---|---|
| 55A-1 | 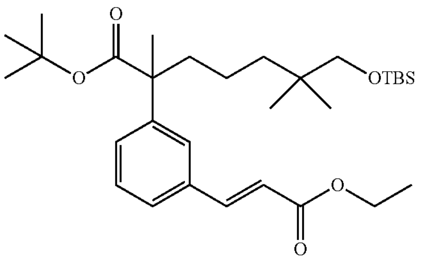 [SMILES: CCOC(=O)/C=C/c1cccc(C(C)(CCCC(C)(C)CO[Si](C)(C)C(C)(C)C)C(=O)OC(C)(C)C)c1] | tert-butyl (E)-7-((tert-butyldimethylsilyl)oxy)-2-(3-(3-ethoxy-3-oxoprop-1-en-1-yl)phenyl)-2,6,6-trimethylheptanoate | 555 [M + Na]+ |

Intermediate 56: tert-Butyl 2-(3-(3-ethoxy-2,2-dimethyl-3-oxopropyl)phenyl)-7-hydroxy-2,6,6-trimethylheptanoate

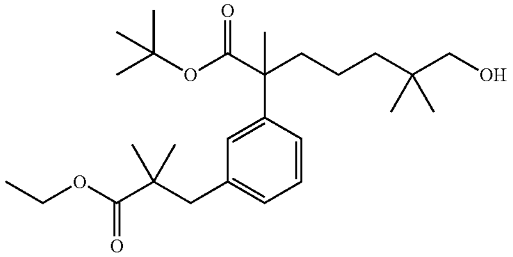 [SMILES: CCOC(=O)C(C)(C)Cc1cccc(C(C)(CCCC(C)(C)CO)C(=O)OC(C)(C)C)c1]

To a stirred solution of tert-butyl 7-[tert-butyl(dimethyl)silyl]oxy-2-[3-(3-ethoxy-2,2-dimethyl-3-oxo-propyl)phenyl]-2,6,6-trimethyl-heptanoate (Intermediate 56C, 12 g, 21.3 mmol) in tetrahydrofuran (50 mL) was added tetrabutylammonium fluoride (53.3 mL, 53.3 mmol). The reaction was stirred at room temperature overnight, then quenched with water (150 mL). The mixture was extracted with ethyl acetate (2×100 mL). The combined organic phase was washed with brine, dried over sodium sulfate, filtered, and concentrated. The residue was purified by automated silica gel column chromatography (120 g silica gel column, eluting with 0-30% ethyl acetate in petroleum ether) to give the title compound (3.5 g, yield: 36%) as an oil. MS (ESI): 471 $[M+Na]^+$.

Intermediate 56A: tert-butyl 7-((tert-butyldimethylsilyl)oxy)-2-(3-(3-ethoxy-3-oxopropyl)phenyl)-2,6,6-trimethylheptanoate

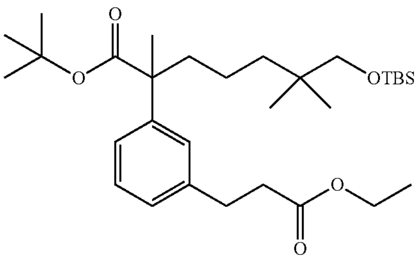 [SMILES: CCOC(=O)CCc1cccc(C(C)(CCCC(C)(C)CO[Si](C)(C)C(C)(C)C)C(=O)OC(C)(C)C)c1]

To a stirred solution of tert-butyl (E)-7-((tert-butyldimethylsilyl)oxy)-2-(3-(3-ethoxy-3-oxoprop-1-en-1-yl)phenyl)-2,6,6-trimethylheptanoate (Intermediate 55A-1, 15 g, 28.2 mmol) in ethanol (150 mL) was added palladium on active carbon (10%, 1.5 g). The flask was evacuated, backfilled with hydrogen and the reaction was stirred at room temperature under hydrogen balloon for 4 hours. The mixture was filtered through a pad of Celite. The filtrate was concentrated to afford the title compound (14 g, yield: 93%) as an oil. MS (ESI): 557 $[M+Na]^+$.

Intermediate 56B: tert-Butyl 7-((tert-butyldimethylsilyl)oxy)-2-(3-(3-ethoxy-2-methyl-3-oxopropyl)phenyl)-2,6,6-trimethylheptanoate

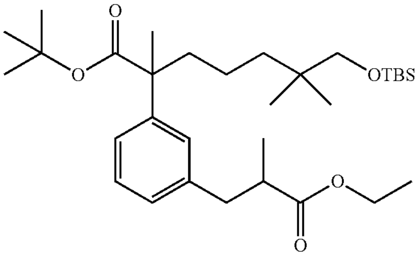 [SMILES: CCOC(=O)C(C)Cc1cccc(C(C)(CCCC(C)(C)CO[Si](C)(C)C(C)(C)C)C(=O)OC(C)(C)C)c1]

To a stirred and cooled (−78° C.) solution of tert-butyl 7-((tert-butyldimethylsilyl)oxy)-2-(3-(3-ethoxy-3-oxopropyl)phenyl)-2,6,6-trimethylheptanoate (Intermediate 56A, 12 g, 22.4 mmol) in tetrahydrofuran (120 mL) was added lithium diisopropylamide (16.8 mL, 33.7 mmol, 2N in tetrahydrofuran) under nitrogen. The mixture was treated with iodomethane (4.78 g, 33.7 mmol) and after 10 minutes at this temperature, the reaction was allowed to slowly warm to room temperature and stirred for 4 hours. The mixture was quenched with saturated ammonium chloride solution (aqueous) (200 mL), then extracted with ethyl acetate (2×100 mL). The combined organic phase was washed with brine, dried over sodium sulfate, filtered, and concentrated to give the title compound (12 g, crude product) as an oil. This oil was used for the next step without further purification.

Intermediate 56C: tert-Butyl 7-((tert-butyldimethylsilyl)oxy)-2-(3-(3-ethoxy-2,2-dimethyl-3-oxopropyl)phenyl)-2,6,6-trimethylheptanoate

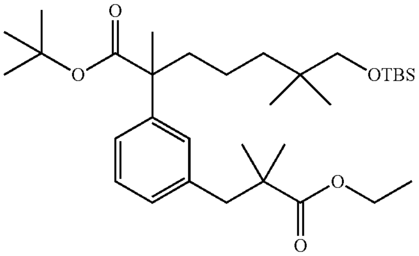 [SMILES: CCOC(=O)C(C)(C)Cc1cccc(C(C)(CCCC(C)(C)CO[Si](C)(C)C(C)(C)C)C(=O)OC(C)(C)C)c1]

To a stirred and cooled (−78° C.) solution of tert-butyl 7-((tert-butyldimethylsilyl)oxy)-2-(3-(3-ethoxy-2-methyl-3-oxopropyl)phenyl)-2,6,6-trimethylheptanoate (Intermediate 56B, 12 g, 21.9 mmol) in tetrahydrofuran (120 mL) was added lithium diisopropylamide (16.4 mL, 32.8 mmol, 2N in tetrahydrofuran) under nitrogen. The mixture was treated with iodomethane (4.65 g, 32.8 mmol) and after 10 minutes at this temperature, slowly allowed to warm to room temperature and stirred overnight. The mixture was quenched with saturated ammonium chloride solution (200 mL), then extracted with ethyl acetate (2×100 mL). The combined organic phase was washed with brine, dried over sodium sulfate, filtered, and concentrated to give the title compound (12 g, crude product) as an oil and used for next step without further purification.

Intermediate 57: (4-Bromo-6-fluoro-1H-indol-5-yl)(4-fluoro-3-(imino(methylthio)methyl)phenyl)methyl Acetate Hydroiodide

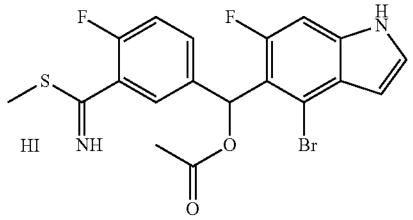

To a stirred solution of (4-bromo-6-fluoro-1H-indol-5-yl)(3-carbamothioyl-4-fluorophenyl)methyl acetate (Intermediate 57D, 1.17 g, 2.66 mmol) in acetone (20 mL) was added iodomethane (0.829 mL, 13.3 mmol). The mixture was stirred at 50° C. for 5 hours. The solvent was removed under vacuum. The obtained residue (title compound, 1.55 g, yield: 100%), was directly used for the next step without further purification. MS (ESI): 453, 455 $[M+H]^+$.

The following intermediate was prepared based on the procedures described for Intermediate 57, and/or for Intermediate 57A to 57D:

Intermediate 57A: 4-Bromo-6-fluoro-1-(triisopropylsilyl)-1H-indole

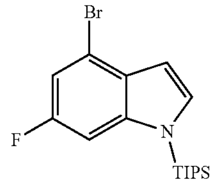

To a stirred and cooled (0° C.) solution of 4-bromo-6-fluoro-1H-indole (29 g, 0.1 mol) in tetrahydrofuran (300 mL) was slowly added sodium hydride (8.67 g, 130 mol). The mixture was stirred for 2 hours, then treated with chloro(triisopropyl)silane (25.5 mL, 0.119 mol) at 0° C. The reaction was stirred for another 2 hours at 0° C., quenched with 500 mL of water and extracted with ethyl acetate (3×200 mL). The combined organic phase was washed with brine, dried over sodium sulfate, and concentrated. The residue was purified by automated flash chromatography (330 g silica gel column, 0-10% ethyl acetate in petroleum ether, UV 254 nm) to give the title compound (34 g, yield: 80%) as a colorless oil. MS (ESI): 370, 372 (M+H)+.

Intermediate 57B: 5-((4-Bromo-6-fluoro-1-(triisopropylsilyl)-1H-indol-5-yl)(hydroxy)methyl)-2-fluorobenzonitrile

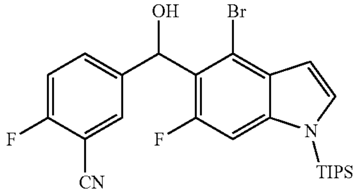

To a stirred and cooled (−78° C.) solution of 4-bromo-6-fluoro-1-(triisopropylsilyl)-1H-indole (Intermediate 57A, 11.1 g, 30 mmol) in 150 mL of tetrahydrofuran was added lithium diisopropylamide (18 mL, 36 mmol, 2N in tetrahydrofuran) dropwise. The reaction was stirred at −78° C. for 1 hour, then treated with 2-fluoro-5-formyl-benzonitrile (4.47 g, 30 mmol). The mixture was slowly warmed to room temperature and stirred for 10 hours, quenched with 300 mL of water, and extracted with ethyl acetate (3×150 mL). The combined organic phase was washed with brine, dried over sodium sulfate, and concentrated. The residue was purified by silica gel column chromatography (petroleum ether:ethyl acetate=5:1) to give the title compound (9.8 g, yield: 63%) as a yellow oil. MS (ESI): 519, 521 (M+H)+.

| Inter. No. | Structure | Name | MS m/z $[M + H]^+$ |
| --- | --- | --- | --- |
| 57-1 | 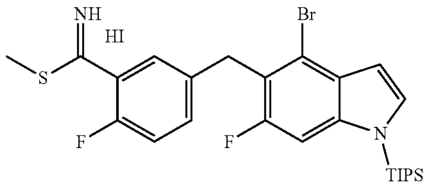 | methyl 5-((4-bromo-6-fluoro-1-(triisopropylsilyl)-1H-indol-5-yl)methyl)-2-fluorobenzimidothioate hydroiodide | 551, 553 |

The following intermediate was prepared based on the procedures described for Intermediate 57B.

| Inter. No. | Structure | Name | MS m/z $[M + H]^+$ |
|---|---|---|---|
| 57B-1 | 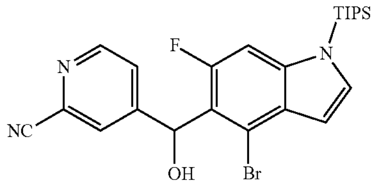 | 4-((4-bromo-6-fluoro-1-(triisopropylsilyl)-1H-indol-5-yl)(hydroxy)methyl)picolinonitrile | 502, 504 $[M + H]^+$; RT: 1.41 min. (LC-MS method 17) |

Intermediate 57C: (4-Bromo-6-fluoro-1H-indol-5-yl)(3-cyano-4-fluorophenyl)methyl acetate and Intermediate 57C-1: (4-bromo-6-fluoro-1-(triisopropylsilyl)-1H-indol-5-yl)(3-cyano-4-fluorophenyl) methyl Acetate

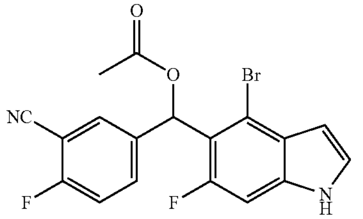

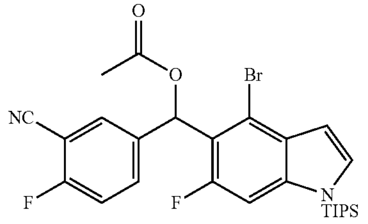

To a stirred solution of 5-((4-bromo-6-fluoro-1-(triisopropylsilyl)-1H-indol-5-yl)(hydroxy)methyl)-2-fluorobenzonitrile (Intermediate 57B, 6 g, 11.5 mmol) in dichloromethane (5 mL) was added acetic anhydride (1.64 mL, 17.3 mmol), N, N-dimethylpyridin-4-amine (138 mg) and triethylamine (4.83 mL, 34.6 mol). The reaction was stirred at room temperature for 2 hours, then diluted with ethyl acetate (50 mL). The mixture was washed with water, brine, dried over sodium sulfate, filtered, and concentrated. The residue was purified by automated flash chromatography (40 g silica gel column, 0-60% ethyl acetate in petroleum ether, UV 254 nm) to give the title compound (2 g, yield: 49%) as a solid and protected (4-bromo-6-fluoro-1-(triisopropylsilyl)-1H-indol-5-yl)(3-cyano-4-fluorophenyl) methyl acetate (3.2 g, yield: 42%) as a solid. The title compound: MS (ESI): 427, 429 (M+Na)+. (LC-MS method B). The TIPS protected by-product: MS (ESI): 561, 563 $[M+H]^+$.

The following intermediate was prepared based on the procedures described for Intermediate 57B.

| Inter. No. | Structure | Name | MS m/z $[M + H]^+$ |
|---|---|---|---|
| 57C-2 | 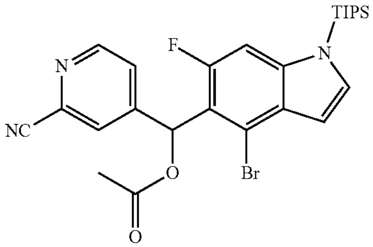 | (4-bromo-6-fluoro-1-(triisopropylsilyl)-1H-indol-5-yl)(2-cyanopyridin-4-yl)methyl acetate | 544 546 $[M + H]^+$; RT: 2.48 min. (LC-MS method 4) |

Intermediate 57D: (4-Bromo-6-fluoro-1H-indol-5-yl)(3-carbamothioyl-4-fluorophenyl)methyl Acetate

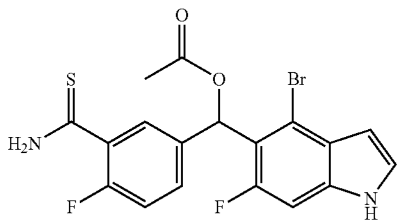 [SMILES: CC(=O)OC(c1ccc(F)c(C(N)=S)c1)c1c(F)cc2[nH]ccc2c1Br]

To a stirred solution of (4-bromo-6-fluoro-1H-indol-5-yl)(3-cyano-4-fluorophenyl)methyl acetate (Intermediate 57C, 2 g, 2.96 mmol) in N,N-dimethylformamide (12 mL) was added sodium hydrosulfide (1.66 g, 29.6 mmol), followed by magnesium chloride (1.41 g, 14.8 mmol) and water (1.07 mL, 59.2 mmol). The mixture was stirred at room temperature for 1 hour, quenched with water, and extracted with ethyl acetate. The organic phase was washed with brine, dried over sodium sulfate, filtered, and concentrated. The residue was purified by automated flash chromatography (40 g silica gel column, 0-70% ethyl acetate in petroleum ether, UV 254 nm) to give the title compound (1.17 g, yield: 74.8%) as a solid. MS (ESI): 461, 463 $[M+Na]^+$.

The following intermediates were prepared based on the procedures described for Intermediate 57D:

| Inter. No. | Structure | Name | MS m/z $[M + H]^+$ |
|---|---|---|---|
| 57D-1 | 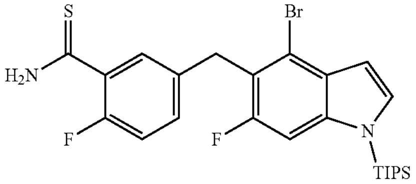 | 5-((4-bromo-6-fluoro-1-(triisopropylsilyl)-1H-indol-5-yl)methyl)-2-fluorobenzothioamide | 537, 539 |
| 57D-2 | 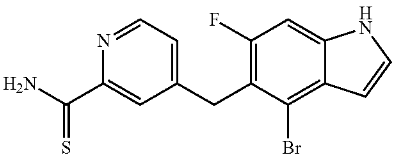 [SMILES: NC(=S)c1cc(Cc2c(F)cc3[nH]ccc3c2Br)ccn1] | 4-((4-bromo-6-fluoro-1H-indol-5-yl)methyl)pyridine-2-carbothioamide | 364, 366 $[M + H]^+$; RT: 1.91 min. (LC-MS method 4) |
| 57D-3 | 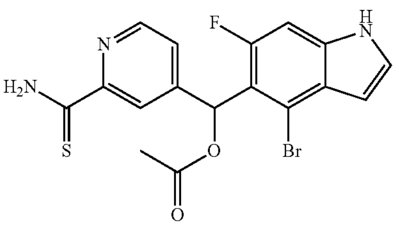 [SMILES: CC(=O)OC(c1ccnc(C(N)=S)c1)c1c(F)cc2[nH]ccc2c1Br] | (4-bromo-6-fluoro-1H-indol-5-yl)(2-carbamothioylpyridin-4-yl)methyl acetate | 422, 424 $[M + H]^+$; RT: 1.74 min. (LC-MS method 4) |

Intermediate 58: Ethyl 3-(3-(2-((3-((2-hydroxyethyl)sulfonyl)-2,2-dimethylpropoxy)methyl)-1-(2-methylhydrazineyl)-1-oxopropan-2-yl-3,3,3-d3)phenyl)-2-methylpropanoate

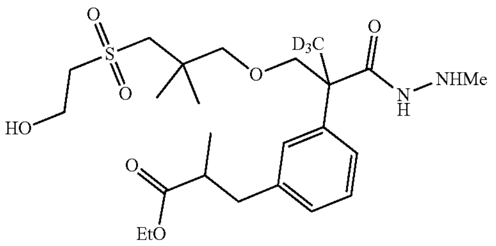 [SMILES: [2H]C([2H])([2H])C(COCC(C)(C)CS(=O)(=O)CCO)(C(=O)NNC)c1cccc(CC(C)C(=O)OCC)c1]

To a solution of tert-butyl 2-(2-(3-(3-ethoxy-2-methyl-3-oxopropyl)phenyl)-2-((3-((2-hydroxyethyl)sulfonyl)-2,2-dimethylpropoxy)methyl)propanoyl-3,3,3-$d_3$)-1-methylhydrazine-1-carboxylate (Intermediate 58-G, 4.6 g, 7.62 mmol) in dichloromethane (15 mL) was added trifluoroacetic acid (5.66 mL). The mixture was stirred at room temperature for 2 h. The mixture was diluted with saturated sodium bicarbonate aqueous solution (200 mL), extracted with ethyl acetate (3×100 mL). The combined organic layers were dried over anhydrous sodium sulfate, filtered, and concentrated to give the title compound (3.6 g, yield 94%) as a light-yellow oil. MS (ESI): 504 $[M+H]^+$.

The following intermediates were prepared based on procedures and or steps described for preparation of Intermediate 58, and/or for Intermediates 58A to 58G.

| Inter. No. | Structure | Name | MS m/z [M + H]+ |
|---|---|---|---|
| 58-1 | 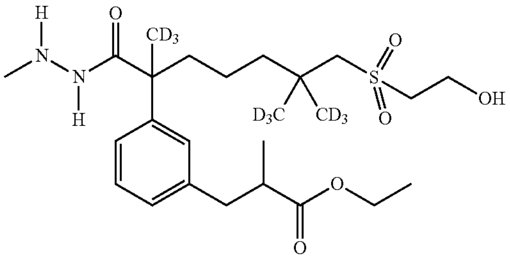 [SMILES: [2H]C([2H])([2H])C(CCCC(CS(=O)(=O)CCO)(C([2H])([2H])[2H])C([2H])([2H])[2H])(C(=O)NNC)c1cccc(CC(C)C(=O)OCC)c1] | ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)-2-methylpropanoate | 508 |
| 58-2 | 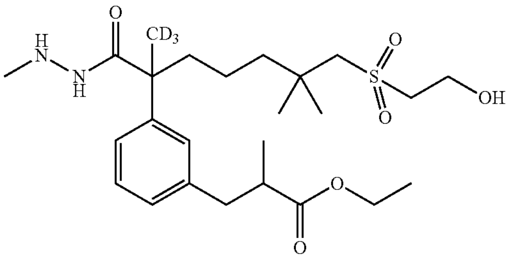 [SMILES: [2H]C([2H])([2H])C(CCCC(C)(C)CS(=O)(=O)CCO)(C(=O)NNC)c1cccc(CC(C)C(=O)OCC)c1] | ethyl 3-(3-(7-((2-hydroxyethyl)sulfonyl)-6,6-dimethyl-2-(2-methylhydrazine-1-carbonyl)heptan-2-yl-1,1,1-d3)phenyl)-2-methylpropanoate | 502 |
| 58-3 | 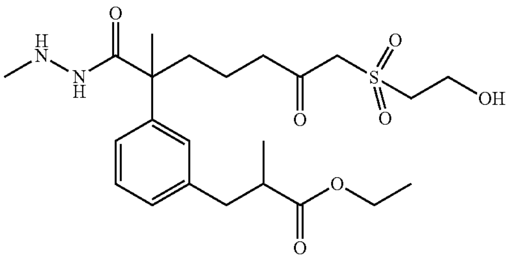 [SMILES: CCOC(=O)C(C)Cc1cccc(C(C)(CCCC(=O)CS(=O)(=O)CCO)C(=O)NNC)c1] | ethyl 3-(3-(7-((2-hydroxyethyl)sulfonyl)-2-methyl-1-(2-methylhydrazineyl)-1,6-dioxoheptan-2-yl)phenyl)-2-methylpropanoate | 507 [M + Na]+ |
| 58-4 | 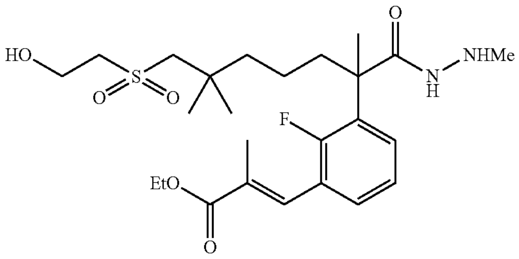 [SMILES: CCOC(=O)/C(C)=C/c1cccc(C(C)(CCCC(C)(C)CS(=O)(=O)CCO)C(=O)NNC)c1F] | ethyl (E)-3-(2-fluoro-3-(7-((2-hydroxyethyl)sulfonyl)-2,6,6-trimethyl-1-(2-methylhydrazineyl)-1-oxoheptan-2-yl)phenyl)-2-methylacrylate | 515 |
| 58-5 | 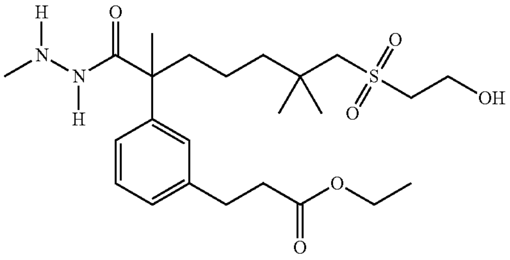 [SMILES: CCOC(=O)CCc1cccc(C(C)(CCCC(C)(C)CS(=O)(=O)CCO)C(=O)NNC)c1] | ethyl 3-(3-(7-((2-hydroxyethyl)sulfonyl)-2,6,6-trimethyl-1-(2-methylhydrazineyl)-1-oxoheptan-2-yl)phenyl)propanoate | 485 |
| 58-6 | 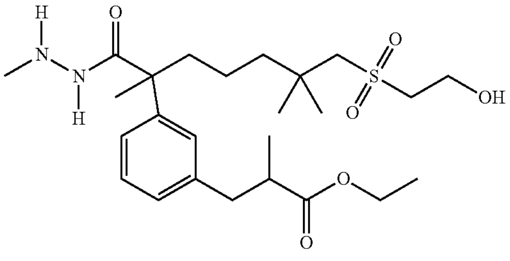 [SMILES: CCOC(=O)C(C)Cc1cccc(C(C)(CCCC(C)(C)CS(=O)(=O)CCO)C(=O)NNC)c1] | ethyl 3-(3-(7-((2-hydroxyethyl)sulfonyl)-2,6,6-trimethyl-1-(2-methylhydrazineyl)-1-oxoheptan-2-yl)phenyl)-2-methylpropanoate | 499 |

-continued

| Inter. No. | Structure | Name | MS m/z [M + H]+ |
| --- | --- | --- | --- |
| 58-7 | 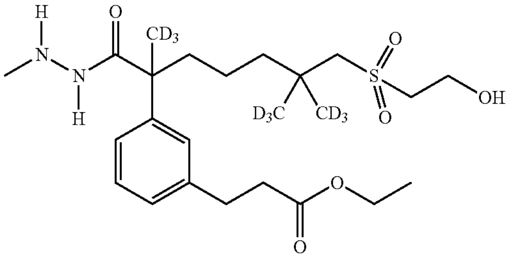 [SMILES: [2H]C([2H])([2H])C(CCCC(CS(=O)(=O)CCO)(C([2H])([2H])[2H])C([2H])([2H])[2H])(C(=O)NNC)c1cccc(CCC(=O)OCC)c1] | ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)propanoate | 494 |
| 58-8 | 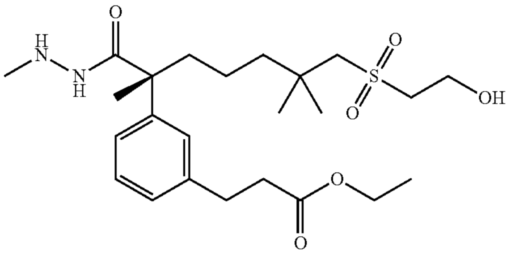 [SMILES: CCOC(=O)CCc1cccc([C@@](C)(CCCC(C)(C)CS(=O)(=O)CCO)C(=O)NNC)c1] | ethyl (R)-3-(3-(7-((2-hydroxyethyl)sulfonyl)-2,6,6-trimethyl-1-(2-methylhydrazineyl)-1-oxoheptan-2-yl)phenyl)propanoate | 485 |

Intermediate 58A: Methyl 2-((3-bromo-2,2-dimethylpropoxy)methyl)-2-(3-bromophenyl)propanoate-3,3,3-$d_3$

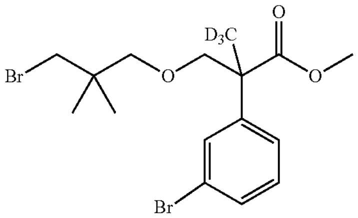 [SMILES: [2H]C([2H])([2H])C(COCC(C)(C)CBr)(C(=O)OC)c1cccc(Br)c1]

To a stirred and cooled (−78° C.) solution of methyl 2-(3-bromophenyl)propanoate-3,3,3-$d_3$ (15 g, 60.9 mmol) in tetrahydrofuran (150 mL) at was added dropwise lithium diisopropylamide (2.0 M, 39.6 mL, 79.2 mmol). The mixture was stirred for 2 h at this temperature and treated dropwise with 1-bromo-3-(chloromethoxy)-2,2-dimethylpropane (19.7 g, 91.4 mmol). The reaction mixture was slowly warmed up and stirred for 16 hours at room temperature, then quenched with water (200 mL). The mixture was extracted with ethyl acetate (3×100 mL), washed with brine (200 mL), dried over anhydrous sodium sulfate, filtered, and concentrated. The residue was purified by automated flash chromatography (120 g silica gel column, 0-20% ethyl acetate in petroleum ether for 30 min) to give the title compound (20 g, yield 77%) as a light-yellow oil. MS (ESI): 426 m/z $[M+H]^+$, RT: 2.02 min. (LC-MS method 2).

Intermediate 58B: Methyl 2-((3-(acetylthio)-2,2-dimethylpropoxy)methyl)-2-(3-bromophenyl)propanoate-3,3,3-$d_3$

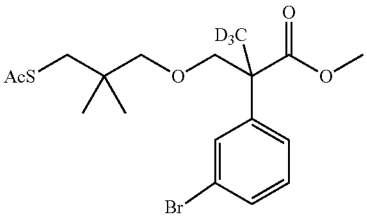

To a stirred solution of methyl 2-((3-bromo-2,2-dimethylpropoxy)methyl)-2-(3-bromophenyl)propanoate-3,3,3-$d_3$ (Intermediate 58A, 20 g, 47.0 mmol) in N,N-dimethylformamide (200 mL) was added potassium thioacetate (10.7 g, 94.1 mmol). The mixture was stirred at 70° C. for 16 hours, and then quenched with water (300 mL). The mixture was extracted with ethyl acetate (3×200 mL). The combined organic layer was washed with brine (2×300 mL), dried over anhydrous sodium sulfate and concentrated to afford the title compound (19 g) as a yellow oil, which was used in the next step without further purification. MS (ESI): 420, 422 $[M+H]^+$.

Intermediate 58C: 2-(3-Bromophenyl)-2-((3-((2-hydroxyethyl)thio)-2,2-dimethylpropoxy)methyl) propanoic-3,3,3-d3 acid

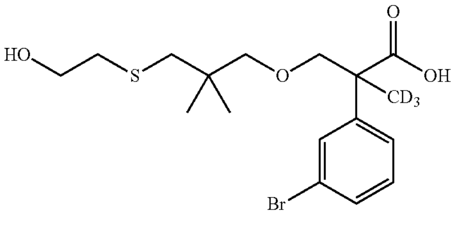 [SMILES: [2H]C([2H])([2H])C(COCC(C)(C)CSCCO)(C(=O)O)c1cccc(Br)c1]

To a stirred solution of methyl 2-(3-bromophenyl)-2-((3-((2-hydroxyethyl)thio)-2,2-dimethylpropoxy)methyl)propanoate-3,3,3-$d_3$ (Intermediate 58B, 18 g) in tetrahydrofuran (80 mL), methanol (80 mL) and water (40 mL) was added lithium hydroxide monohydrate (17.9 g, 426 mmol). The reaction was stirred at room temperature for 3 hours, then diluted with water (100 mL) and acidified with 1.0 M hydrochloric acid to pH ~6. The mixture was extracted with ethyl acetate (3×100 mL). The combined organic phases were washed with brine (2×200 mL), dried over anhydrous sodium sulfate, filtered, and concentrated. The residue was purified by automated flash chromatography (silica gel column, 0-50% ethyl acetate in petroleum ether) to give the title compound (13 g, yield 70% (3 steps)) as a light-yellow oil. MS (ESI): 430, 432 $[M+Na]^+$.

Intermediate 58D: tert-Butyl 2-(2-(3-bromophenyl)-2-((3-((2-hydroxyethyl)thio)-2,2-dimethylpropoxy) methyl)propanoyl-3,3,3-d3)-1-methylhydrazine-1-carboxylate

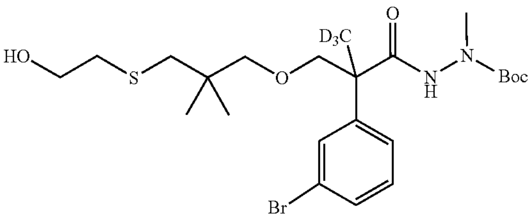 [SMILES: [2H]C([2H])([2H])C(COCC(C)(C)CSCCO)(C(=O)NN(C)C(=O)OC(C)(C)C)c1cccc(Br)c1]

To a stirred solution of 2-(3-bromophenyl)-2-((3-((2-hydroxyethyl)thio)-2,2-dimethylpropoxy)methyl)propanoic-3,3,3-$d_3$ acid (Intermediate 58C, 13 g, 31.8 mmol) in acetonitrile (130 mL) was added tert-butyl N-amino-N-methylcarbamate (5.58 g, 38.2 mmol), 1-methylimidazole (7.84 g, 95.5 mmol) and N,N,N',N'-tetramethylchloroformamidinium-hexafluorophosphate (9.38 g, 33.4 mmol). The reaction mixture was stirred at room temperature for 2 hours, then diluted with ethyl acetate (200 mL). The mixture was washed with water (2×100 mL), dried over anhydrous magnesium sulfate, filtered, and concentrated. The residue was purified by silica gel column chromatography (120 g silica gel column, 0-50% ethyl acetate in petroleum ether) to give the title compound (13 g, yield 76%) as a light-yellow oil. MS (ESI): 558, 560 $[M+Na]^+$.

Intermediate 58E: tert-Butyl 2-(2-(3-bromophenyl)-2-((3-((2-hydroxyethyl)sulfonyl)-2,2-dimethylpropoxy)methyl)propanoyl-3,3,3-d3)-1-methylhydrazine-1-carboxylate

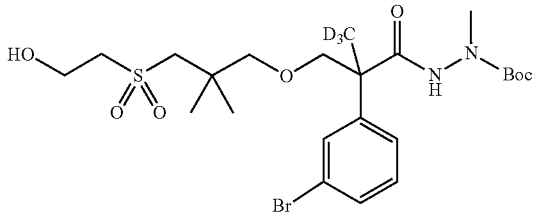 [SMILES: [2H]C([2H])([2H])C(COCC(C)(C)CS(=O)(=O)CCO)(C(=O)NN(C)C(=O)OC(C)(C)C)c1cccc(Br)c1]

To a solution of tert-butyl 2-(2-(3-bromophenyl)-2-((3-((2-hydroxyethyl)thio)-2,2-dimethylpropoxy)methyl)propanoyl-3,3,3-d3)-1-methylhydrazine-1-carboxylate (Intermediate 58D, 13 g, 24.2 mmol) in methanol (350 mL) was added dropwise a solution of ammonium molybdate tetrahydrate (13.5 g, 13.5 mmol) in hydrogen peroxide (30% in water, 35 mL) at 0° C., and then the mixture was stirred at room temperature for 2 h. The mixture was diluted with water (200 mL), extracted with ethyl acetate (200 mL×3). The combined organic phase was washed with brine (300 mL×5), dried over anhydrous sodium sulfate and concentrated to give the title compound (12 g, yield 87%) as a light-yellow oil. MS (ESI): 590, 592 $[M+Na]^+$.

Intermediate 58F: tert-Butyl 2-(2-(3-(3-ethoxy-2-methyl-3-oxoprop-1-en-1-yl)phenyl)-2-((3-((2-hydroxyethyl)sulfonyl)-2,2-dimethylpropoxy)methyl) propanoyl-3,3,3-d3)-1-methylhydrazine-1-carboxylate

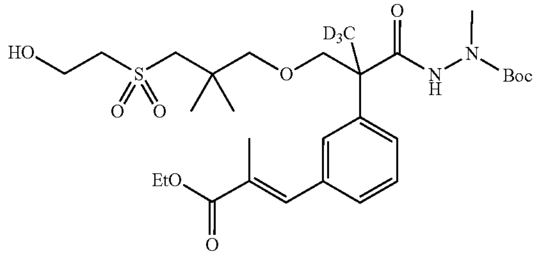 [SMILES: [2H]C([2H])([2H])C(COCC(C)(C)CS(=O)(=O)CCO)(C(=O)NN(C)C(=O)OC(C)(C)C)c1cccc(/C=C(\C)C(=O)OCC)c1]

To a stirred solution of tert-butyl 2-(2-(3-bromophenyl)-2-((3-((2-hydroxyethyl)sulfonyl)-2,2-dimethylpropoxy) methyl)propanoyl-3,3,3-d3)-1-methylhydrazine-1-carboxylate (Intermediate 58E, 3.61 g, 31.7 mmol) in N-methyl pyrrolidone (60 mL) was added triethylamine (5.34 g, 52.8 mmol), ethyl methacrylate (7.23 g, 63.4 mmol), palladium acetate (474 mg, 2.11 mmol) and tri(o-tolyl)phosphine (1.28 g, 4.22 mmol). The mixture was heated at 110° C. for 16 hours under argon, then diluted with water (200 mL). The mixture was extracted with ethyl acetate (3×100 mL). The combined organic phase was washed with brine (2×200 mL), dried over sodium sulfate, filtered, and concentrated. The residue was purified by automated flash chromatography (80 g silica gel column, 0-20% ethyl acetate in petroleum ether) to give the title compound (5.0 g, 78% yield) as a light-yellow oil. MS (ESI): 624 $[M+Na]^+$.

Intermediate 58G: tert-Butyl 2-(2-(3-(3-ethoxy-2-methyl-3-oxopropyl)phenyl)-2-((3-((2-hydroxyethyl)sulfonyl)-2,2-dimethylpropoxy)methyl)propanoyl-3,3,3-d3)-1-methylhydrazine-1-carboxylate

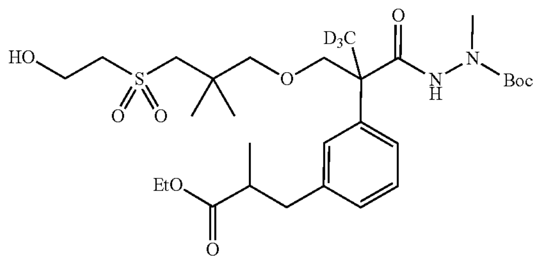 [SMILES: [2H]C([2H])([2H])C(COCC(C)(C)CS(=O)(=O)CCO)(C(=O)NN(C)C(=O)OC(C)(C)C)c1cccc(CC(C)C(=O)OCC)c1]

To a stirred solution of tert-butyl 2-(2-(3-(3-ethoxy-2-methyl-3-oxoprop-1-en-1-yl)phenyl)-2-((3-((2-hydroxyethyl)sulfonyl)-2,2-dimethylpropoxy)methyl)propanoyl-3,3,3-d3)-1-methylhydrazine-1-carboxylate (Intermediate 58F, 5 g, 8.31 mmol) in ethanol (50 mL) was added 10% palladium on carbon (wetted with ca. 55% Water, 1.7 g). The reaction mixture was stirred under hydrogen for 2 hours at 50° C. The catalyst was removed by filtration and washed with ethanol (3×30 mL). The filtrate was concentrated to give the title compound (4.6 g, yield 92%) as a colorless oil. MS (ESI): 626 $[M+Na]^+$.

Intermediate 59: tert-Butyl 2-(3-iodophenyl)propanoate

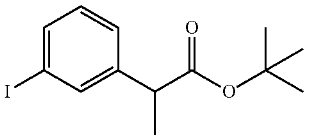 [SMILES: CC(C(=O)OC(C)(C)C)c1cccc(I)c1]

To a stirred and cooled (−78° C.) solution of tert-butyl 2-(3-iodophenyl)acetate (115 g, 361 mmol) in tetrahydrofuran (800 mL) was added, dropwise over 30 minutes, a 2.0 M solution of lithium diisopropylamide in tetrahydrofuran (217 mL, 434 mmol). The mixture was maintained at −78° C. for two hours before adding, dropwise over 10 minutes, iodomethane (23.6 mL, 53.8 g, 379 mmol). The reaction mixture was warmed to room temperature and stirred for an additional two hours. After this time, the reaction was quenched with the slow addition of water (800 mL) and then concentrated to remove the organic solvent. The remaining water/oil mixture was extracted with ethyl acetate (1×500 mL) and the organic layer was washed with brine (2×500 mL), dried over anhydrous sodium sulfate and concentrated. The residue was purified by automated flash chromatography (330 g silica gel column, 0-5% ethyl acetate in petroleum ether) to afford the title compound as a colorless oil (97.9 g, 82%). MS (ESI): 355 m/z $[M+Na]^+$.

The following intermediates were prepared based on the procedures described for Intermediate 59, starting from corresponding intermediate:

| Inter. No. | Structure | Name | MS m/z $[M + H]^+$ |
| --- | --- | --- | --- |
| 59-1 | 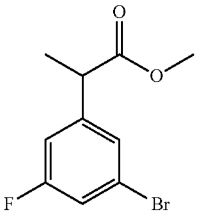 | methyl 2-(3-bromo-5-fluorophenyl)propanoate | 261, 263 |
| 59-2 | 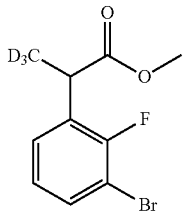 [SMILES: [2H]C([2H])([2H])C(C(=O)OC)c1cccc(Br)c1F] | methyl 2-(3-bromo-2-fluorophenyl)propanoate-3,3,3-d3 | 264, 266 |
| 59-3 | 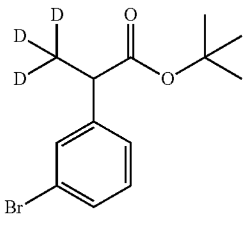 [SMILES: [2H]C([2H])([2H])C(C(=O)OC(C)(C)C)c1cccc(Br)c1] | tert-butyl 2-(3-bromophenyl)propanoate-3,3,3-d3 | 310, 312 $[M + Na]^+$ |

-continued

| Inter. No. | Structure | Name | MS m/z [M + H]$^+$ |
|---|---|---|---|
| 59-4 | 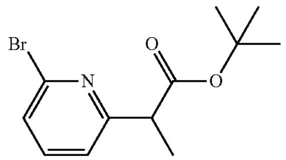 [SMILES: CC(C(=O)OC(C)(C)C)c1cccc(Br)n1] | tert-butyl 2-(6-bromopyridin-2-yl)propanoate | 286, 288 |
| 59-5 | 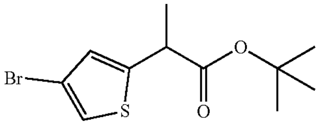 | tert-butyl 2-(4-bromothiophen-2-yl)propanoate | 235, 237 [M − t − butyl + H]$^+$ |
| 59-6 | 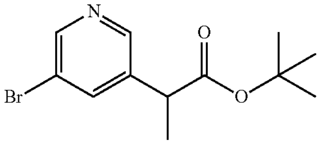 [SMILES: CC(C(=O)OC(C)(C)C)c1cncc(Br)c1] | tert-butyl 2-(5-bromopyridin-3-yl)propanoate | MS: 286, 288; RT: 2.00 min. (LC-MS method 034) |

Intermediate 60: tert-Butyl 7-hydroxy-2-(3-iodophenyl)-2,6,6-trimethylheptanoate

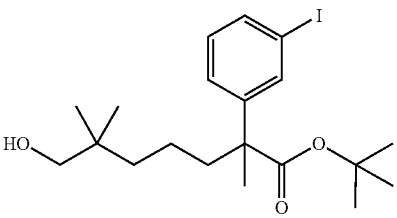 [SMILES: CC(C)(CO)CCCC(C)(C(=O)OC(C)(C)C)c1cccc(I)c1]

To a stirred and cooled (−78° C.) solution of tert-butyl 2-(3-iodophenyl)propanoate (Intermediate 59, 97.9 g, 295 mmol) in tetrahydrofuran (800 mL) was added, dropwise over 20 minutes, a 2.0 M solution of lithium diisopropylamide in tetrahydrofuran (177 mL, 354 mmol. The mixture was maintained at −78° C. for two hours before adding, dropwise over 20 minutes, tert-butyl((5-iodo-2,2-dimethylpentyl)oxy)dimethylsilane (Intermediate 29C-1, 110 g, 309 mmol). The reaction mixture was allowed to warm to room temperature and stirred overnight. After this time, the reaction was quenched with the slow addition of water (800 mL) and then concentrated to remove the organic solvent. The remaining water/oil mixture was extracted with ethyl acetate (1×500 mL) and the organic layer was washed with brine (2×500 mL), dried over anhydrous sodium sulfate and concentrated. The residue was purified by automated flash chromatography (330 g silica gel column, 0-5% ethyl acetate in petroleum ether) to afford the title compound as a pale amber oil (160 g, 97%). A portion of this material (100 g, 178 mmol) was taken up in tetrahydrofuran (400 mL), stirred at room temperature and treated with a 1.0 M solution of tetrabutylammonium fluoride in tetrahydrofuran (357 mL, 357 mmol). The mixture was stirred overnight at room temperature and then partitioned between ethyl acetate (500 mL) and water (800 mL). The organic layer was washed with additional portions of water (2×800 mL), dried over magnesium sulfate and concentrated. The residue was purified by automated flash chromatography (330 g silica gel column, 0-30% ethyl acetate in petroleum ether) to afford the title compound as a colorless oil (65.1 g, 79% overall, two steps). MS (ESI): 469 m/z [M+Na]$^+$.

The following intermediates were prepared based on the procedures described for Intermediate 60, starting from corresponding intermediate:

| Inter. No. | Structure | Name | MS m/z [M + H]$^+$ |
|---|---|---|---|
| 60-1 | 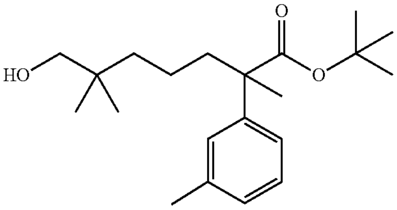 [SMILES: Cc1cccc(C(C)(CCCC(C)(C)CO)C(=O)OC(C)(C)C)c1] | tert-butyl 7-hydroxy-2,6,6-trimethyl-2-(m-tolyl)heptanoate | 357[M + Na]$^+$ |

-continued

| Inter. No. | Structure | Name | MS m/z [M + H]$^+$ |
| --- | --- | --- | --- |
| 60-2 | 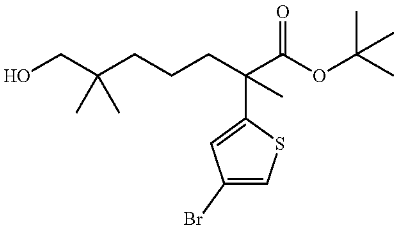 [SMILES: CC(C)(CO)CCCC(C)(C(=O)OC(C)(C)C)c1cc(Br)cs1] | tert-butyl 2-(4-bromothiophen-2-yl)-7-hydroxy-2,6,6-trimethylheptanoate | 427, 429 [M + Na]$^+$ |
| 60-3 | 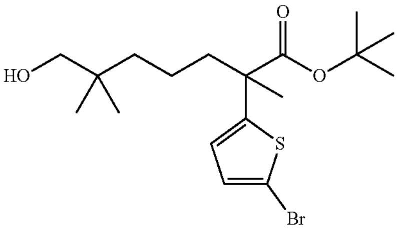 [SMILES: CC(C)(CO)CCCC(C)(C(=O)OC(C)(C)C)c1ccc(Br)s1] | tert-butyl 2-(5-bromothiophen-2-yl)-7-hydroxy-2,6,6-trimethylheptanoate | 427, 429 [M + Na]$^+$; RT: 2.25 min. (LC-MS method 33) |
| 60-4 | 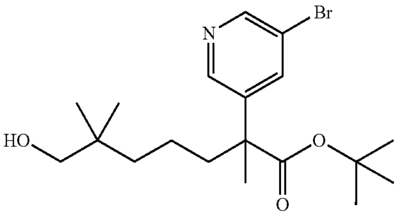 [SMILES: CC(C)(CO)CCCC(C)(C(=O)OC(C)(C)C)c1cncc(Br)c1] | tert-butyl 2-(5-bromopyridin-3-yl)-7-hydroxy-2,6,6-trimethylheptanoate | 400, 402; RT: 2.5 min (LC-MS Method 034) |
| 60-5 | 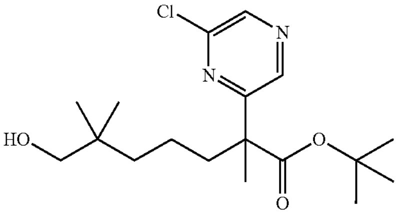 [SMILES: CC(C)(CO)CCCC(C)(C(=O)OC(C)(C)C)c1cncc(Cl)n1] | tert-butyl 2-(6-chloropyrazin-2-yl)-7-hydroxy-2,6,6-trimethylheptanoate | 357; RT: 1.98 min. (LC-MS Method 034) |
| 60-6 | 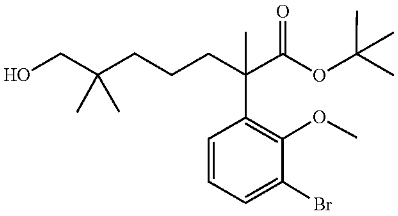 [SMILES: COc1c(Br)cccc1C(C)(CCCC(C)(C)CO)C(=O)OC(C)(C)C] | tert-butyl 2-(3-bromo-2-methoxyphenyl)-7-hydroxy-2,6,6-trimethylheptanoate | 451, 453 [M + Na]$^+$; RT: 2.32 min. (LC-MS method 24) |

Intermediate 61: tert-Butyl 7-(acetylthio)-2-(3-iodophenyl)-2,6,6-trimethylheptanoate

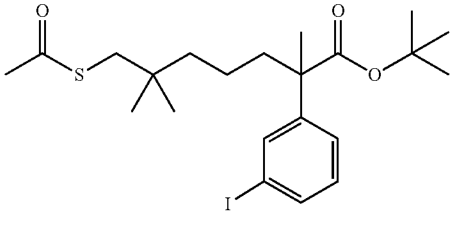 [SMILES: CC(=O)SCC(C)(C)CCCC(C)(C(=O)OC(C)(C)C)c1cccc(I)c1]

To a stirred and cooled (0° C.) solution of triphenylphosphine (115 g, 438 mmol) in tetrahydrofuran (800 mL) was added, dropwise over 10 minutes, diisopropyl azodicarboxylate (86.0 mL, 88.3 g, 437 mmol). The reaction was maintained at 0° C. and monitored for the appearance of a precipitate. Upon the observation of a white solid, a previously prepared solution of tert-butyl 7-hydroxy-2-(3-iodophenyl)-2,6,6-trimethylheptanoate (Intermediate 60, 65.0 g, 146 mmol) and thioacetic acid (31.2 mL, 33.2 g, 437 mmol) in tetrahydrofuran (200 mL) was added, dropwise over 30 minutes. Following the addition, the reaction was stirred at 0° C. for one hour, allowed to warm to room temperature and stirred for another one hour. The reaction was then concentrated, and the crude residue was subjected to automated flash chromatography (330 g silica gel column, 0-10% ethyl acetate in petroleum ether). The title compound was obtained as a viscous, pale amber oil (51.0 g, 69%). MS (ESI): 527 m/z [M+Na]$^+$.

The following intermediates were prepared based on the procedures described for Intermediate 61, starting from corresponding intermediate:

| Inter. No. | Structure | Name | MS m/z [M + H]$^+$ |
|---|---|---|---|
| 61-1 | 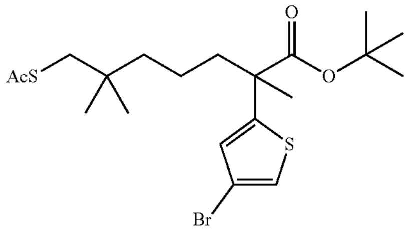 | tert-butyl 7-(acetylthio)-2-(4-bromothiophen-2-yl)-2,6,6-trimethylheptanoate | 485, 487 [M + Na]$^+$ |
| 61-2 | 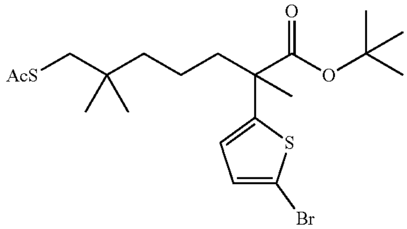 | tert-butyl 7-(acetylthio)-2-(5-bromothiophen-2-yl)-2,6,6-trimethylheptanoate | 485, 487 [M + Na]$^+$; RT: 2.86 min. (LC-MS method 33) |
| 61-3 | 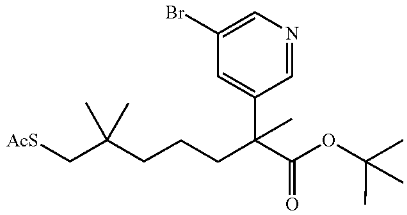 | tert-butyl 7-(acetylthio)-2-(5-bromopyridin-3-yl)-2,6,6-trimethylheptanoate | 458, 460; RT: 2.27 min (LC-MS Method 034) |
| 61-4 | 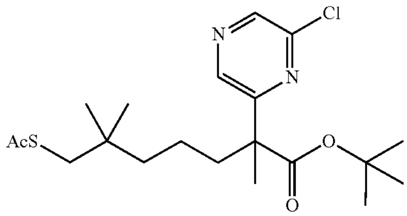 | tert-butyl 7-(acetylthio)-2-(6-chloropyrazin-2-yl)-2,6,6-trimethylheptanoate | 437 [M + Na]$^+$; RT: 2.56 min (LC-MS Method 017) |
| 61-5 | 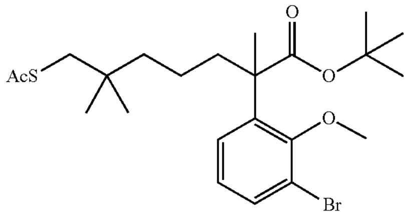 | tert-butyl 7-(acetylthio)-2-(3-bromo-2-methoxyphenyl)-2,6,6-trimethylheptanoate | 509, 511 [M + Na]$^+$; RT: 2.32 min (LC-MS Method 47) |

Intermediate 62: tert-Butyl 7-((2-hydroxyethyl)thio)-2-(3-iodophenyl)-2,6,6-trimethylheptanoate

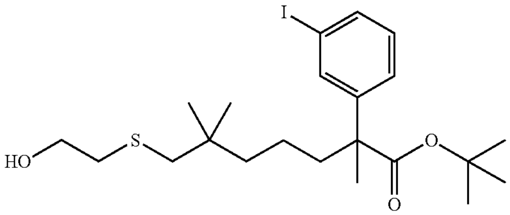 [SMILES: CC(C)(CCCC(C)(C(=O)OC(C)(C)C)c1cccc(I)c1)CSCCO]

To a stirred solution of tert-butyl 7-(acetylthio)-2-(3-iodophenyl)-2,6,6-trimethylheptanoate (Intermediate 61, 51.0 g, 101 mmol) in ethanol (300 mL) was added 2-bromoethanol (9.32 mL, 16.4 g, 131 mmol) followed by sodium ethoxide (10.3 g, 151 mmol). The reaction was stirred for one hour before partitioning between ethyl acetate (500 mL) and water (800 mL). The organic layer was washed with additional portions of water (2×800 mL), dried over magnesium sulfate and concentrated. The residue was purified by automated flash chromatography (330 g silica gel column, 0-20% ethyl acetate in petroleum) to afford the title compound as light amber gum (47.2 g, 92%). MS (ESI): 529 m/z [M+Na]$^+$.

The following intermediate was prepared based on the procedures described for Intermediate 62,

| Inter. No. | Structure | Name | MS m/z [M + H]$^+$ |
|---|---|---|---|
| 62-1 | 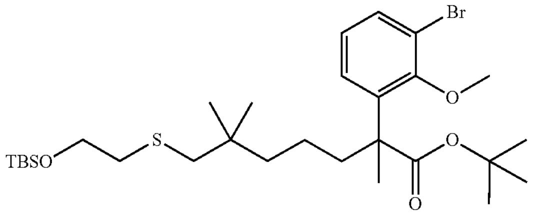 [SMILES: COc1c(Br)cccc1C(C)(CCCC(C)(C)CSCCO[Si](C)(C)C(C)(C)C)C(=O)OC(C)(C)C] | tert-butyl 2-(3-bromo-2-methoxyphenyl)-7-((2-((tert-butyldimethylsilyl)oxy)ethyl)thio)-2,6,6-trimethylheptanoate | 625, 627 [M + Na]$^+$; RT: 4.15 min. (LC-MS method 50) |

Intermediate 63: tert-Butyl 7-((2-hydroxyethyl) sulfonyl)-2-(3-iodophenyl)-2,6,6-trimethylheptanoate

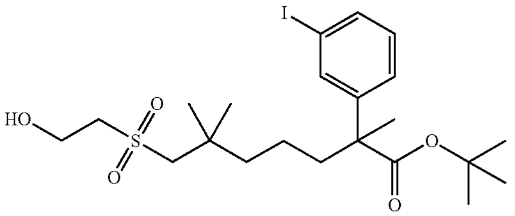 [SMILES: CC(C)(CCCC(C)(C(=O)OC(C)(C)C)c1cccc(I)c1)CS(=O)(=O)CCO]

To a stirred solution of tert-Butyl 7-((2-hydroxyethyl) thio)-2-(3-iodophenyl)-2,6,6-trimethylheptanoate (Intermediate 62, 34.0 g, 67.1 mmol) in methanol (1.2 L) was added a solution of ammonium molybdate tetrahydrate (34.0 g, 27.5 mmol) dissolved in 30% aqueous hydrogen peroxide solution (150 mL). After two hours at room temperature, the reaction was partitioned between ethyl acetate (1.5 L) and water (2 L). The organic layer was washed with a second portion of water (1×2 L), dried over sodium sulfate and concentrated. Crude title compound was afforded as a pale amber gum (32.8 g, 91%). MS (ESI): 561 m/z [M+Na]$^+$.

The following intermediates were prepared based on the procedures described for Intermediate 63, starting from corresponding intermediate:

| Inter. No | Structure | Name | MS m/z [M + H]$^+$ |
|---|---|---|---|
| 63-1 | 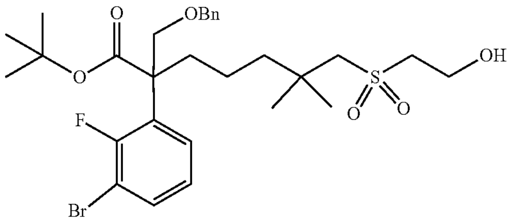 [SMILES: CC(C)(CCCC(COCc1ccccc1)(C(=O)OC(C)(C)C)c1cccc(Br)c1F)CS(=O)(=O)CCO] | tert-butyl 2-((benzyloxy)methyl)-2-(3-bromo-2-fluorophenyl)-7-((2-hydroxyethyl)sulfonyl)-6,6-dimethylheptanoate | 637, 639 [M + Na]$^+$ |
| 63-2 | 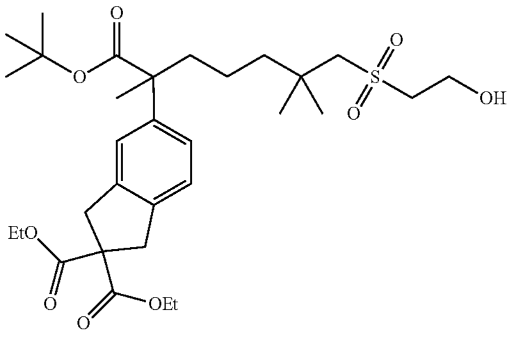 [SMILES: CCOC(=O)C1(C(=O)OCC)Cc2ccc(C(C)(CCCC(C)(C)CS(=O)(=O)CCO)C(=O)OC(C)(C)C)cc2C1] | diethyl 5-(1-(tert-butoxy)-7-((2-hydroxyethyl)sulfonyl)-2,6,6-trimethyl-1-oxoheptan-2-yl)-1,3-dihydro-2H-indene-2,2-dicarboxylate | 619 [M + Na]$^+$ |
| 63-3 | 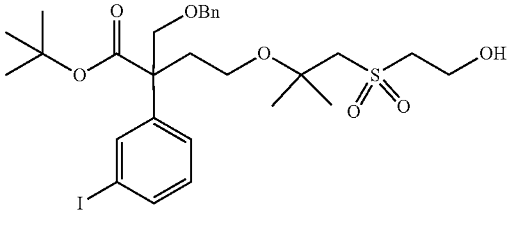 [SMILES: CC(C)(C)OC(=O)C(CCOC(C)(C)CS(=O)(=O)CCO)(COCc1ccccc1)c1cccc(I)c1] | tert-butyl 2-((benzyloxy)methyl)-4-((1-((2-hydroxyethyl)sulfonyl)-2-methylpropan-2-yl)oxy)-2-(3-iodophenyl)butanoate | 669 [M + Na]$^+$ |

-continued

| Inter. No | Structure | Name | MS m/z [M + H]$^+$ |
|---|---|---|---|
| 63-4 | 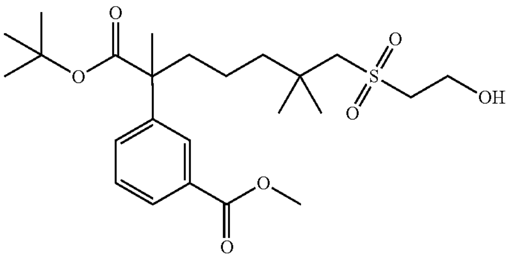 [SMILES: COC(=O)c1cccc(C(C)(CCCC(C)(C)CS(=O)(=O)CCO)C(=O)OC(C)(C)C)c1] | methyl 3-(1-(tert-butoxy)-7-((2-hydroxyethyl)sulfonyl)-2,6,6-trimethyl-1-oxoheptan-2-yl)benzoate | 493 [M + Na]$^+$ |
| 63-5 | 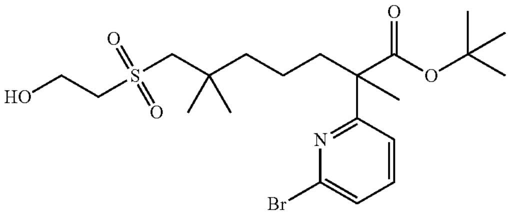 [SMILES: CC(C)(CCCC(C)(C(=O)OC(C)(C)C)c1cccc(Br)n1)CS(=O)(=O)CCO] | tert-butyl 2-(6-bromopyridin-2-yl)-7-((2-hydroxyethyl)sulfonyl)-2,6,6-trimethylheptanoate | 492, 494 |
| 63-6 | 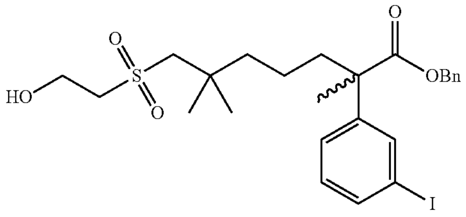 [SMILES: CC(C)(CCCC(C)(C(=O)OCc1ccccc1)c1cccc(I)c1)CS(=O)(=O)CCO] | Enantiomer 1 of benzyl 7-((2-hydroxyethyl)sulfonyl)-2-(3-iodophenyl)-2,6,6-trimethylheptanoate | 595 [M + Na]$^+$ 98% ee |
| 63-7 | 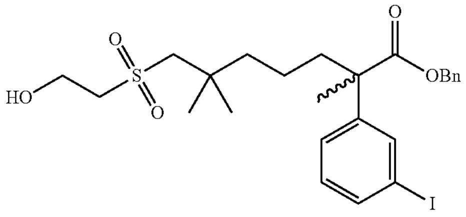 [SMILES: CC(C)(CCCC(C)(C(=O)OCc1ccccc1)c1cccc(I)c1)CS(=O)(=O)CCO] | Enantiomer 2 of benzyl 7-((2-hydroxyethyl)sulfonyl)-2-(3-iodophenyl)-2,6,6-trimethylheptanoate | 595 [M + Na]$^+$ 98% ee |
| 63-8 | 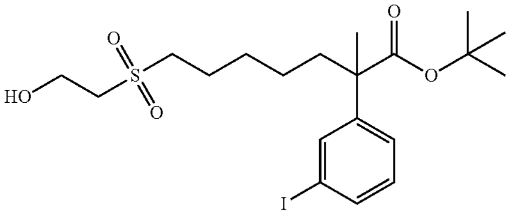 [SMILES: CC(C)(C)OC(=O)C(C)(CCCCCS(=O)(=O)CCO)c1cccc(I)c1] | tert-butyl 7-((2-hydroxyethyl)sulfonyl)-2-(3-iodophenyl)-2-methylheptanoate | 533 [M + Na]$^+$; RT: 1.97 min .; (LC-MS Method 003) |
| 63-9 | 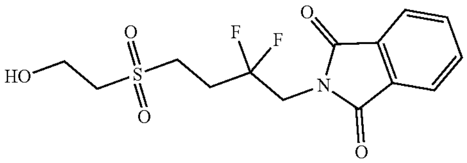 [SMILES: O=C1c2ccccc2C(=O)N1CC(F)(F)CCS(=O)(=O)CCO] | 2-(2,2-difluoro-4-((2-hydroxyethyl)sulfonyl)butyl)isoindoline-1,3-dione | 348 [M + H]$^+$; RT: 1.58 min .; (LC-MS Method 51) |

-continued

| Inter. No | Structure | Name | MS m/z [M + H]$^+$ |
|---|---|---|---|
| 63-10 | 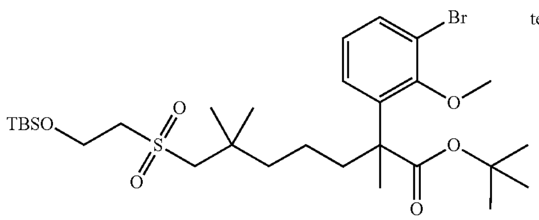 | tert-butyl 2-(3-bromo-2-methoxyphenyl)-7-((2-((tert-butyldimethylsilyl)oxy)ethyl)sulfonyl)-2,6,6-trimethylheptanoate | 657, 659 [M + Na]$^+$; RT: 2.68 min. (LC-MS method ) |

Intermediate 64: tert-Butyl 7-((2-((tert-butyldimethylsilyl)oxy)ethyl)sulfonyl)-2-(3-iodophenyl)-2,6,6-trimethylheptanoate

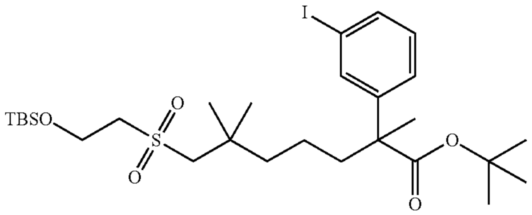 [SMILES: CC(C)(CCCC(C)(C(=O)OC(C)(C)C)c1cccc(I)c1)CS(=O)(=O)CCO[Si](C)(C)C(C)(C)C]

To a stirred solution of tert-butyl 7-((2-hydroxyethyl)sulfonyl)-2-(3-iodophenyl)-2,6,6-trimethylheptanoate (Intermediate 63, 32.0 g, 59.4 mmol) in dichloromethane (500 mL) was added imidazole (8.09 g, 119 mmol) and tert-butyldimethylsilyl chloride (10.7 g, 71.0 mmol). After two hours at room temperature, the reaction mixture was partitioned between dichloromethane (400 mL) and water (500 mL). The organic layer was washed with a second portion of water (1×500 mL), dried over magnesium sulfate and concentrated. The residue was purified by automated flash chromatography (330 g silica gel column, 0-20% ethyl acetate in petroleum ether) to afford the title compound as a faint amber gum (34.0 g, 88%). $^1$H NMR (400 MHz, $CDCl_3$) δ 7.64 (t, J=1.9 Hz, 1H), 7.55 (dt, J=7.8, 1.9 Hz, 1H), 7.28-7.26 (m, 1H), 7.04 (t, J=8.0 Hz, 1H), 4.04 (t, J=5.2 Hz, 2H), 3.09-3.05 (m, 4H), 1.99-1.92 (m, 1H), 1.83-1.75 (m, 1H), 1.54-1.50 (m, 2H), 1.45 (s, 3H), 1.39 (s, 9H), 1.28-1.23 (m, 2H), 1.17 (s, 3H), 1.15 (s, 3H), 0.90 (s, 9H), 0.09 (s, 6H) ppm.

The following intermediates were prepared based on the procedures described for Intermediate 64, starting from corresponding intermediate:

| Inter. No. | Structure | Name | MS m/z [M + H]$^+$ |
|---|---|---|---|
| 64-1 | 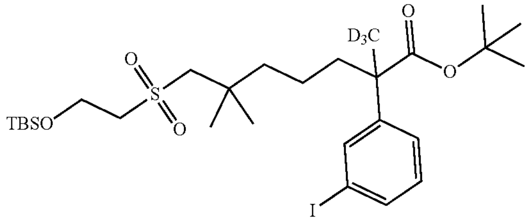 [SMILES: [2H]C([2H])([2H])C(CCCC(C)(C)CS(=O)(=O)CCO[Si](C)(C)C(C)(C)C)(C(=O)OC(C)(C)C)c1cccc(I)c1] | tert-butyl 7-((2-((tert-butyldimethylsilyl)oxy)ethyl)sulfonyl)-2-(3-iodophenyl)-6,6-dimethyl-2-(methyl-d3)heptanoate | 678 [M + Na]$^+$ |
| 64-2 | 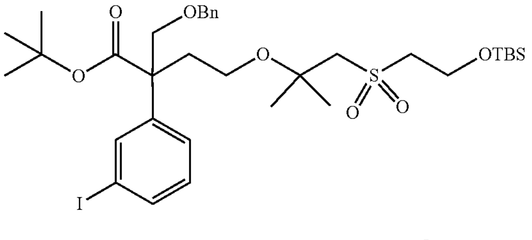 [SMILES: CC(C)(C)OC(=O)C(CCOC(C)(C)CS(=O)(=O)CCO[Si](C)(C)C(C)(C)C)(COCc1ccccc1)c1cccc(I)c1] | tert-butyl 2-((benzyloxy)methyl)-4-((1-((2-((tert-butyldimethylsilyl)oxy)ethyl)sulfonyl)-2-methylpropan-2-yl)oxy)-2-(3-iodophenyl)butanoate | 783 [M + Na]$^+$ |
| 64-3 | 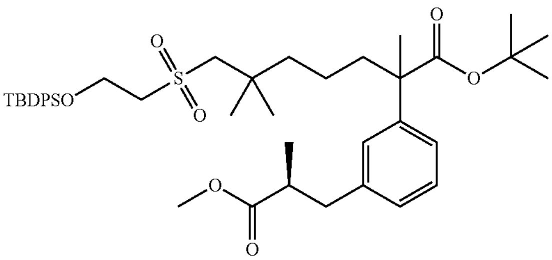 | tert-butyl 7-((2-((tert-butyldiphenylsilyl)oxy)ethyl)sulfonyl)-2-(3-((S)-3-methoxy-2-methyl-3-oxopropyl)phenyl)-2,6,6-trimethylheptanoate | 773 [M + Na]$^+$ |

-continued

| Inter. No. | Structure | Name | MS m/z [M + H]$^+$ |
|---|---|---|---|
| 64-4 | 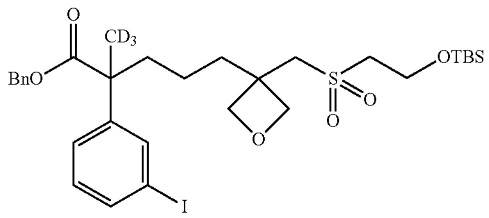 [SMILES: [2H]C([2H])([2H])C(CCCC1(CS(=O)(=O)CCO[Si](C)(C)C(C)(C)C)COC1)(C(=O)OCc1ccccc1)c1cccc(I)c1] | benzyl 5-(3-(((2-((tert-butyldimethylsilyl)oxy)ethyl)sulfonyl)methyl)oxetan-3-yl)-2-(3-iodophenyl)-2-(methyl-d3)pentanoate | 704 |
| 64-5 | 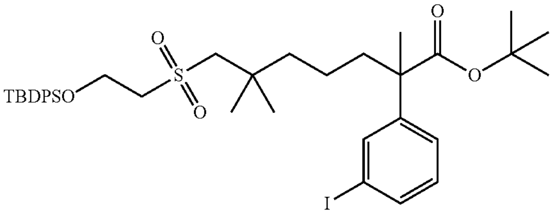 | tert-butyl 7-((2-((tert-butyldiphenylsilyl)oxy)ethyl)sulfonyl)-2-(3-iodophenyl)-2,6,6-trimethylheptanoate | 799 [M + Na]$^+$ |
| 64-6 | 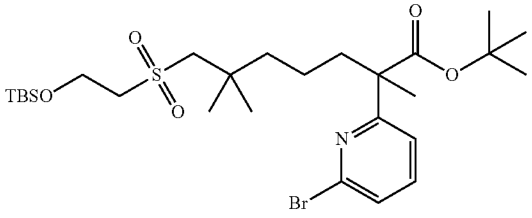 [SMILES: CC(C)(CCCC(C)(C(=O)OC(C)(C)C)c1cccc(Br)n1)CS(=O)(=O)CCO[Si](C)(C)C(C)(C)C] | tert-butyl 2-(6-bromopyridin-2-yl)-7-((2-((tert-butyldimethylsilyl)oxy)ethyl)sulfonyl)-2,6,6-trimethylheptanoate | 606, 608 |
| 64-7 | 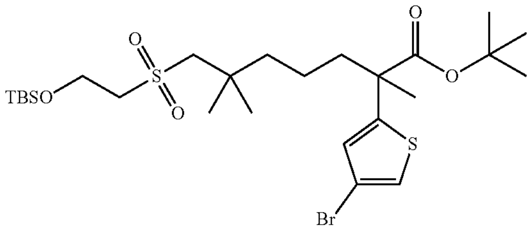 [SMILES: CC(C)(CCCC(C)(C(=O)OC(C)(C)C)c1cc(Br)cs1)CS(=O)(=O)CCO[Si](C)(C)C(C)(C)C] | tert-butyl 2-(4-bromothiophen-2-yl)-7-((2-((tert-butyldimethylsilyl)oxy)ethyl)sulfonyl)-2,6,6-trimethylheptanoate | 633, 635 [M + Na]$^+$ |
| 64-8 | 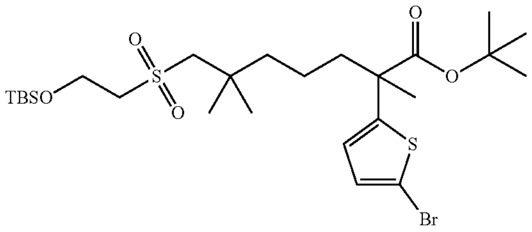 [SMILES: CC(C)(CCCC(C)(C(=O)OC(C)(C)C)c1ccc(Br)s1)CS(=O)(=O)CCO[Si](C)(C)C(C)(C)C] | tert-butyl 2-(5-bromothiophen-2-yl)-7-((2-((tert-butyldimethylsilyl)oxy)ethyl)sulfonyl)-2,6,6-trimethylheptanoate | 633, 635 [M + Na]$^+$; RT: 3.11 min. (LC-MS method 4) |
| 64-9 | 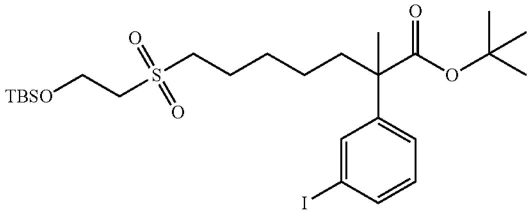 [SMILES: CC(C)(C)OC(=O)C(C)(CCCCCS(=O)(=O)CCO[Si](C)(C)C(C)(C)C)c1cccc(I)c1] | tert-butyl 7-((2-((tert-butyldimethylsilyl)oxy)ethyl)sulfonyl)-2-(3-iodophenyl)-2-methylheptanoate | 647 [M + Na]$^+$; RT: 2.53 min. (LC-MS method 3) |

-continued

| Inter. No. | Structure | Name | MS m/z [M + H]+ |
|---|---|---|---|
| 64-10 | 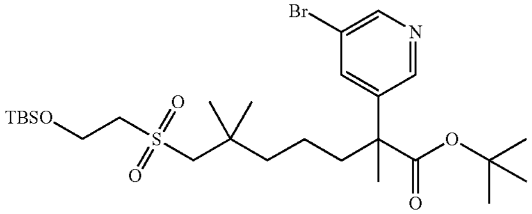 [SMILES: CC(C)(CCCC(C)(C(=O)OC(C)(C)C)c1cncc(Br)c1)CS(=O)(=O)CCO[Si](C)(C)C(C)(C)C] | tert-butyl 2-(5-bromopyridin-3-yl)-7-((2-((tert-butyldimethylsilyl)oxy)ethyl)sulfonyl)-2,6,6-trimethylheptanoate | 606, 608; RT: 2.66 (LC-MS Method 034) |
| 64-11 | 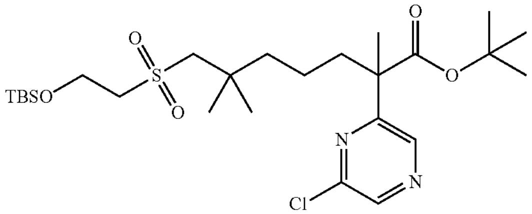 [SMILES: CC(C)(CCCC(C)(C(=O)OC(C)(C)C)c1cncc(Cl)n1)CS(=O)(=O)CCO[Si](C)(C)C(C)(C)C] | tert-butyl 7-((2-((tert-butyldimethylsilyl)oxy)ethyl)sulfonyl)-2-(6-chloropyrazin-2-yl)-2,6,6-trimethylheptanoate | 585 [M + Na]+; RT: 2.78 min. (LC-MS method 3) |
| 64-12 | 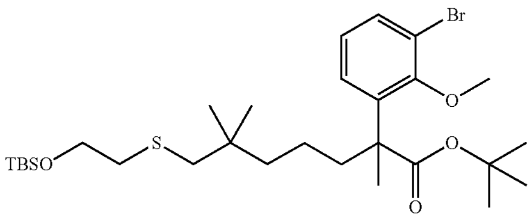 [SMILES: COc1c(Br)cccc1C(C)(CCCC(C)(C)CSCCO[Si](C)(C)C(C)(C)C)C(=O)OC(C)(C)C] | tert-butyl 2-(3-bromo-2-methoxyphenyl)-7-((2-((tert-butyldimethylsilyl)oxy)ethyl)thio)-2,6,6-trimethylheptanoate | 625, 627 [M + Na]+; RT: 4.15 min. (LC-MS method 50) |

Intermediate 65: tert-Butyl 7-((2-((tert-butyldimethylsilyl)oxy)ethyl)sulfonyl)-2-(3-((R)-3-methoxy-2-methyl-3-oxopropyl)phenyl)-2,6,6-trimethylheptanoate

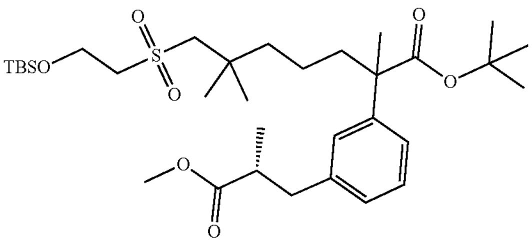 [SMILES: COC(=O)[C@H](C)Cc1cccc(C(C)(CCCC(C)(C)CS(=O)(=O)CCO[Si](C)(C)C(C)(C)C)C(=O)OC(C)(C)C)c1]

The reaction was carried out in a glove box under positive pressure with dry nitrogen. To a stirred suspension of zinc dust (12.0 g, 184 mmol) in N,N-dimethylformamide (200 mL) was added iodine (0.778 g, 3.07 mmol). After 40 minutes at room temperature, the mixture was treated with methyl (S)-3-iodo-2-methylpropanoate (14.0 g, 61.4 mmol). The organozinc iodide reagent was allowed another 40 minutes to form before adding, in order: SPhos (2-dicyclohexylphosphino-2',6'-dimethoxybiphenyl (1.26 g, 3.07 mmol), tris(dibenzylideneacetone)dipalladium(0) (1.40 g, 1.53 mmol) and tert-butyl 7-((2-((tert-butyldimethylsilyl)oxy)ethyl)sulfonyl)-2-(3-iodophenyl)-2,6,6-trimethylheptanoate (Intermediate 64, 20.0 g, 30.6 mmol). The reaction was left to stir overnight at room temperature. After this time, the mixture was removed from the glovebox and suction filtered through a plug of Celite. The filtering agent was rinsed with ethyl acetate (~200 mL) and the combined filtrate was partitioned between water (600 mL) and ethyl acetate (200 mL). The organic layer was combined with additional extracts (ethyl acetate, 2×200 mL), washed with brine (2×200 mL) and dried over sodium sulfate. The solution was then concentrated to afford a residue which was subjected to automated flash chromatography (330 g silica gel column, 0-20% ethyl acetate in petroleum ether). The title compound was obtained as a pale amber gum (16.0 g, yield 83%). MS (ESI): 649 m/z [M+Na]+.

The following intermediates were prepared based on the procedures described for Intermediate 65, starting from corresponding intermediate:

| Inter. No. | Structure | Name | MS m/z [M + H]$^+$ |
|---|---|---|---|
| 65-1 | 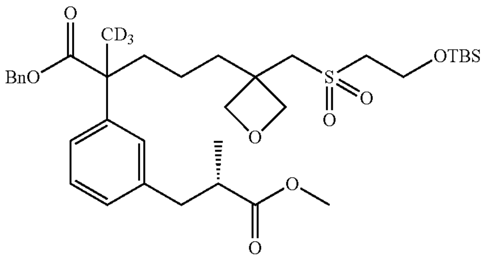 [SMILES: [2H]C([2H])([2H])C(CCCC1(CS(=O)(=O)CCO[Si](C)(C)C(C)(C)C)COC1)(C(=O)OCc1ccccc1)c1cccc(C[C@H](C)C(=O)OC)c1] | benzyl 5-(3-(((2-((tert-butyldimethylsilyl)oxy)ethyl)sulfonyl)methyl)oxetan-3-yl)-2-(3-((S)-3-methoxy-2-methyl-3-oxopropyl)phenyl)-2-(methyl-d3)pentanoate | 678 |
| 65-2 | 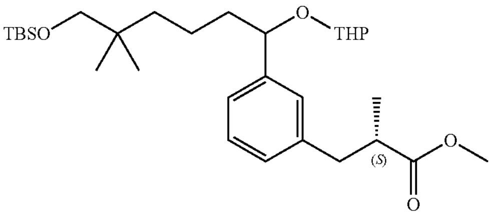 | methyl (2S)-3-(3-(6-((tert-butyldimethylsilyl)oxy)-5,5-dimethyl-1-((tetrahydro-2H-pyran-2-yl)oxy)hexyl)phenyl)-2-methylpropanoate | 543 (mixture of diaste-reomers) |
| 65-3 | 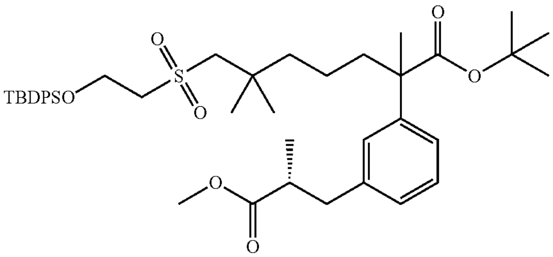 | tert-butyl 7-((2-((tert-butyldiphenylsilyl)oxy)ethyl)sulfonyl)-2-(3-((R)-3-methoxy-2-methyl-3-oxopropyl)phenyl)-2,6,6-trimethylheptanoate | 773 [M + Na]$^+$ |
| 65-4 | 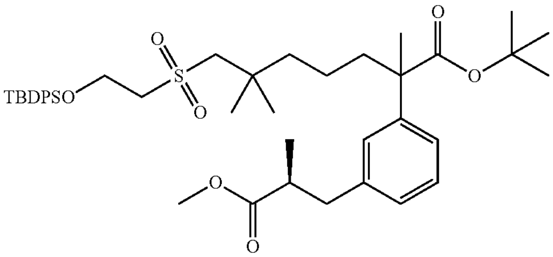 | tert-butyl 7-((2-((tert-butyldiphenylsilyl)oxy)ethyl)sulfonyl)-2-(3-((S)-3-methoxy-2-methyl-3-oxopropyl)phenyl)-2,6,6-trimethylheptanoate | 773 [M + Na]$^+$ |
| 65-5 | 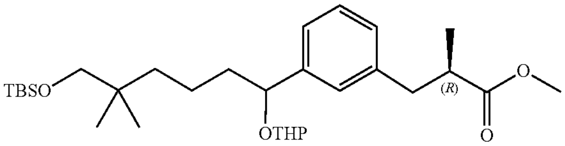 | methyl (2R)-3-(3-(6-((tert-butyldimethylsilyl)oxy)-5,5-dimethyl-1-((tetrahydro-2H-pyran-2-yl)oxy)hexyl)phenyl)-2-methylpropanoate | 543 [M + Na]$^+$ |
| 65-6 | 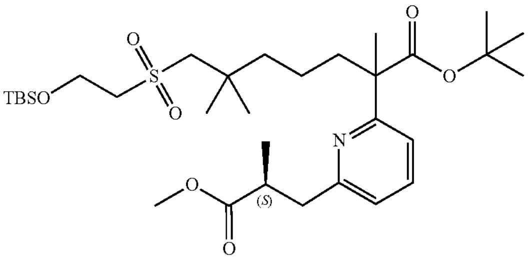 | tert-butyl 7-((2-((tert-butyldimethylsilyl)oxy)ethyl)sulfonyl)-2-(6-((S)-3-methoxy-2-methyl-3-oxopropyl)pyridin-2-yl)-2,6,6-trimethylheptanoate | 628 |

-continued

| Inter. No. | Structure | Name | MS m/z [M + H]+ |
|---|---|---|---|
| 65-7 | 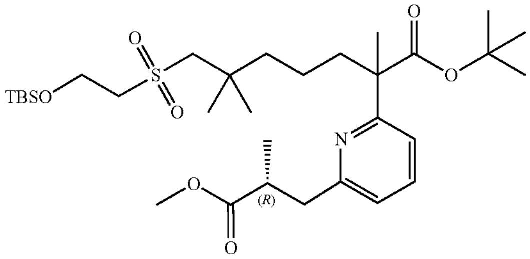 | tert-butyl 7-((2-((tert-butyldimethylsilyl)oxy)ethyl)sulfonyl)-2-(6-((R)-3-methoxy-2-methyl-3-oxopropyl)pyridin-2-yl)-2,6,6-trimethylheptanoate | 628 |
| 65-8 | 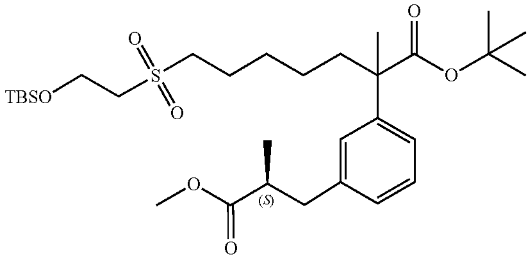 | tert-butyl 7-((2-((tert-butyldimethylsilyl)oxy)ethyl)sulfonyl)-2-(3-((S)-3-methoxy-2-methyl-3-oxopropyl)phenyl)-2-methylheptanoate | 621 [M + Na]+; RT: 2.35 min. (LC-MS method 3) |
| 65-9 | 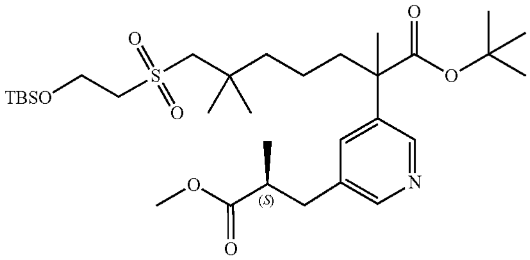 | tert-butyl 7-((2-((tert-butyldimethylsilyl)oxy)ethyl)sulfonyl)-2-(5-((S)-3-methoxy-2-methyl-3-oxopropyl)pyridin-3-yl)-2,6,6-trimethylheptanoate | 628; RT: 2.16 min (LC-MS method 034) |
| 65-10 | 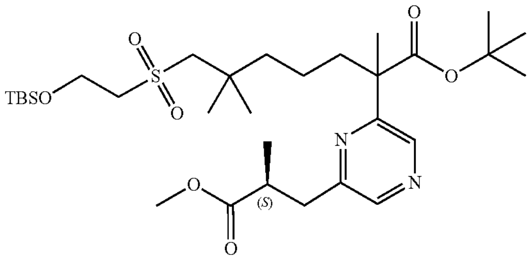 | tert-butyl 7-((2-((tert-butyldimethylsilyl)oxy)ethyl)sulfonyl)-2-(6-((S)-3-methoxy-2-methyl-3-oxopropyl)pyrazin-2-yl)-2,6,6-trimethylheptanoate | 629; RT: 2.30 min. (LC-MS method 003) |
| 65-11 | 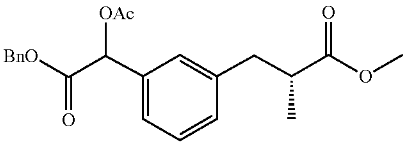 [SMILES: COC(=O)[C@H](C)Cc1cccc(C(OC(C)=O)C(=O)OCc2ccccc2)c1] | methyl (2R)-3-(3-(1-acetoxy-2-(benzyloxy)-2-oxoethyl)phenyl)-2-methylpropanoate | 407 [M + Na]+; RT: 1.96 min. (LC-MS method 51) |

Intermediate 66: tert-Butyl 7-((2-hydroxyethyl) sulfonyl)-2-(3-((R)-3-methoxy-2-methyl-3-oxopropyl)phenyl)-2,6,6-trimethylheptanoate

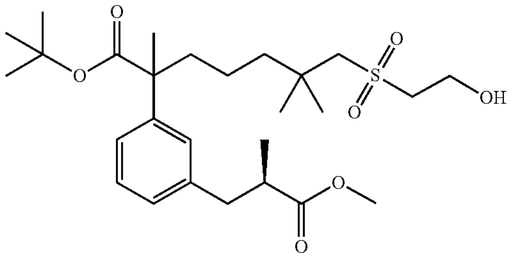 [SMILES: COC(=O)[C@H](C)Cc1cccc(C(C)(CCCC(C)(C)CS(=O)(=O)CCO)C(=O)OC(C)(C)C)c1]

To a stirred solution of tert-butyl 7-((2-((tert-butyldimethylsilyl)oxy)ethyl)sulfonyl)-2-(3-((R)-3-methoxy-2-methyl-3-oxopropyl)phenyl)-2,6,6-trimethylheptanoate (Intermediate 65, 16.0 g, 25.5 mmol) in 1,4-dioxane (100 mL) was added a 4 M solution of hydrogen chloride in 1,4-dioxane (63.8 mL, 255 mmol). After three hours at room temperature, the reaction was concentrated. The residue was purified by automated flash chromatography (120 g silica gel column, 0-40% ethyl acetate in petroleum ether) to afford the title compound as tacky solid (12.0 g, 92%). MS (ESI): 535 m/z $[M+Na]^+$.

Intermediate 67: 7-((2-Hydroxyethyl)sulfonyl)-2-(3-((R)-3-methoxy-2-methyl-3-oxopropyl)phenyl)-2,6,6-trimethylheptanoic Acid

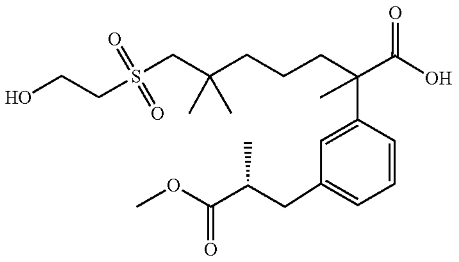 [SMILES: COC(=O)[C@H](C)Cc1cccc(C(C)(CCCC(C)(C)CS(=O)(=O)CCO)C(=O)O)c1]

To a stirred solution tert-butyl 7-((2-hydroxyethyl)sulfonyl)-2-(3-((R)-3-methoxy-2-methyl-3-oxopropyl)phenyl)-2,6,6-trimethylheptanoate (Intermediate 66, 12.0 g, 23.4 mmol) in dichloromethane (100 mL) was added trifluoroacetic acid (17.4 mL, 25.9 g, 227 mmol). After two hours at room temperature, the mixture was concentrated. The residue was subjected to automated flash chromatography (120 g silica gel column, 0-60% ethyl acetate in petroleum for 40 minutes). The title compound was obtained as a pale amber solid (9.11 g, 85%). MS (ESI): 479 m/z $[M+Na]^+$.

The following intermediates were prepared based on the procedures described for Intermediate 67, starting from corresponding intermediate:

| Inter. No. | Structure | Name | MS m/z $[M + H]^+$ |
|---|---|---|---|
| 67-1 | 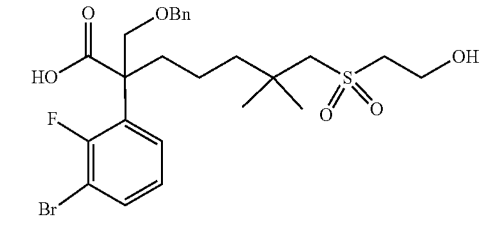 [SMILES: CC(C)(CCCC(COCc1ccccc1)(C(=O)O)c1cccc(Br)c1F)CS(=O)(=O)CCO] | 2-((benzyloxy)methyl)-2-(3-bromo-2-fluorophenyl)-7-((2-hydroxyethyl)sulfonyl)-6,6-dimethylheptanoic acid | 559, 561 |
| 67-2 | 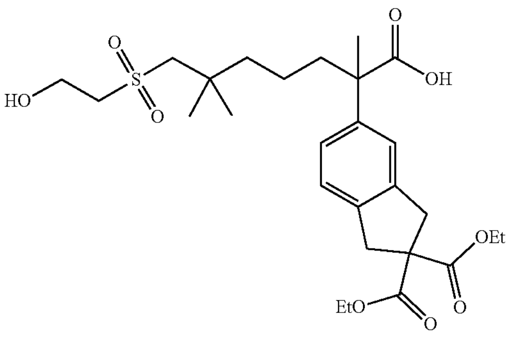 [SMILES: CCOC(=O)C1(C(=O)OCC)Cc2ccc(C(C)(CCCC(C)(C)CS(=O)(=O)CCO)C(=O)O)cc2C1] | 2-(2,2-bis(ethoxycarbonyl)-2,3-dihydro-1H-inden-5-yl)-7-((2-hydroxyethyl)sulfonyl)-2,6,6-trimethylheptanoic acid | 563 $[M + Na]^+$ |
| 67-3 | 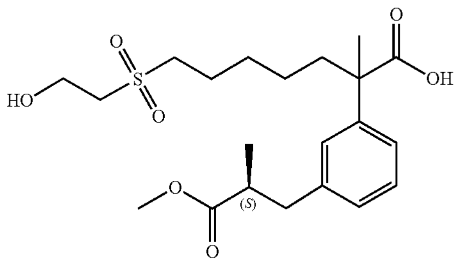 | 7-((2-hydroxyethyl)sulfonyl)-2-(3-((S)-3-methoxy-2-methyl-3-oxopropyl)phenyl)-2-methylheptanoic acid | 451 $[M + Na]^+$; RT: 0.95 min. (LC-MS method 3) |

-continued

| Inter. No. | Structure | Name | MS m/z [M + H]+ |
|---|---|---|---|
| 67-4 | 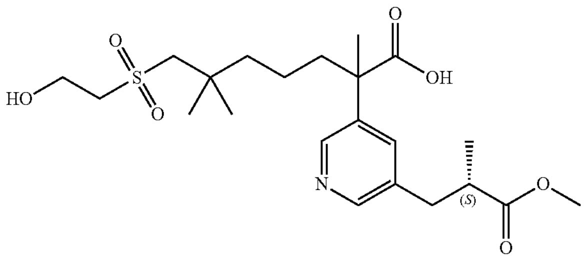 | 7-((2-hydroxyethyl)sulfonyl)-2-(5-((S)-3-methoxy-2-methyl-3-oxopropyl)pyridin-3-yl)-2,6,6-trimethylheptanoic acid | 458; RT: 1.10 min (LC-MS Method 023) |
| 67-5 | 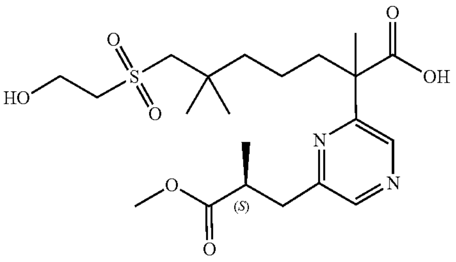 | 7-((2-hydroxyethyl)sulfonyl)-2-(6-((S)-3-methoxy-2-methyl-3-oxopropyl)pyrazin-2-yl)-2,6,6-trimethylheptanoic acid | 459; RT: 1.43 min (LC-MS Method 041) |

Intermediate 68: tert-Butyl 2-(7-((2-hydroxyethyl)sulfonyl)-2-(3-((R)-3-methoxy-2-methyl-3-oxopropyl)phenyl)-2,6,6-trimethylheptanoyl)-1-methylhydrazine-11-carboxylate

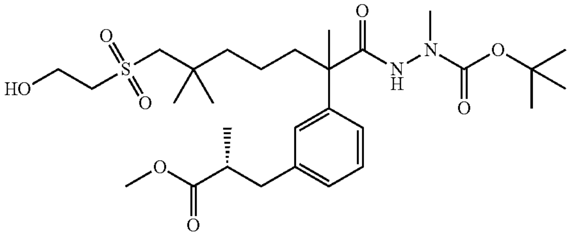 [SMILES: COC(=O)[C@H](C)Cc1cccc(C(C)(CCCC(C)(C)CS(=O)(=O)CCO)C(=O)NN(C)C(=O)OC(C)(C)C)c1]

To a stirred solution of 7-((2-hydroxyethyl)sulfonyl)-2-(3-((R)-3-methoxy-2-methyl-3-oxopropyl)phenyl)-2,6,6-trimethylheptanoic acid (Intermediate 67, 9.10 g, 19.9 mmol) and tert-butyl 1-methylhydrazine-carboxylate (3.25 mL, 3.20 g, 21.9 mmol) in acetonitrile (100 mL) was added 1-methylimidazole (5.73 g, 69.9 mmol) followed by chloro-N,N,N',N'-tetramethylformamidinium hexafluorophosphate (5.59 g, 19.9 mmol). After one hour at room temperature, the reaction was partitioned between ethyl acetate (200 mL) and water (300 mL). The organic layer was washed with an additional portion of water (1×300 mL), dried over magnesium sulfate and concentrated. The residue was purified by automated flash chromatography (120 g silica gel column, 0-60% ethyl acetate in petroleum ether) to afford the title compound as a light amber gum (10.0 g, yield 86%). MS (ESI): 607 m/z $[M+Na]^+$.

Intermediate 69: Methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate

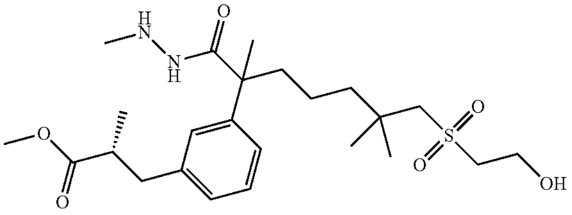 [SMILES: CNNC(=O)C(C)(CCCC(C)(C)CS(=O)(=O)CCO)c1cccc(C[C@@H](C)C(=O)OC)c1]

To a stirred solution of tert-butyl 2-(7-((2-hydroxyethyl)sulfonyl)-2-(3-((R)-3-methoxy-2-methyl-3-oxopropyl)phenyl)-2,6,6-trimethylheptanoyl)-1-methylhydrazine-1-carboxylate (Intermediate 68, 10.0 g, 17.1 mmol) in dichloromethane (100 mL) was added trifluoroacetic acid (12.4 mL, 18.5 mL, 162 mmol). After two hours at room temperature, the reaction mixture was concentrated. The residue was partitioned between ethyl acetate (200 mL) and aqueous sodium bicarbonate solution (200 mL). The organic layer was combined with additional extracts (ethyl acetate, 2×100 mL), dried over sodium sulfate and concentrated. The crude material was purified by automated flash chromatography (120 g silica gel column, 0-60% ethyl acetate in petroleum ether) to afford the title compound as a light amber solid (7.83 g, yield 94%). MS (ESI): 485 m/z $[M+H]^+$.

The following intermediates were prepared based on the procedures described for Intermediate 69 and/or for Intermediates 59-68.

| Inter. No. | Structure | Name | MS m/z [M + H]+ |
|---|---|---|---|
| 69-1 | 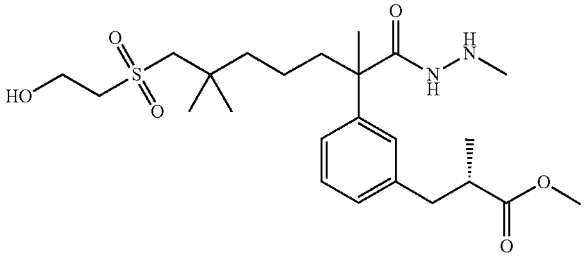 [SMILES: CNNC(=O)C(C)(CCCC(C)(C)CS(=O)(=O)CCO)c1cccc(C[C@H](C)C(=O)OC)c1] | methyl (2S)-3-(3-(7-((2-hydroxyethyl)sulfonyl)-2,6,6-trimethyl-1-(2-methylhydrazineyl)-1-oxoheptan-2-yl)phenyl)-2-methylpropanoate | 485 |
| 69-2 | 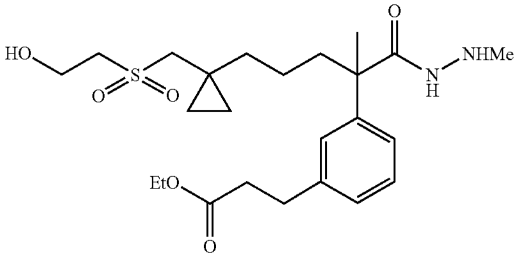 [SMILES: CCOC(=O)CCc1cccc(C(C)(CCCC2(CS(=O)(=O)CCO)CC2)C(=O)NNC)c1] | ethyl 3-(3-(5-(1-(((2-hydroxyethyl)sulfonyl)methyl) cyclopropyl)-2-methyl-1-(2-methylhydrazineyl)-1-oxopentan-2-yl)phenyl)propanoate | 483 |
| 69-3 | 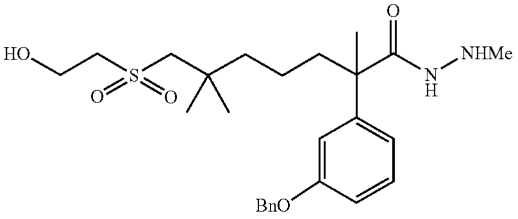 [SMILES: CNNC(=O)C(C)(CCCC(C)(C)CS(=O)(=O)CCO)c1cccc(OCc2ccccc2)c1] | 2-(3-(benzyloxy) phenyl)-7-((2-hydroxyethyl) sulfonyl)-N',2,6,6-tetramethyl-heptanehydrazide | 491 |
| 69-4 | 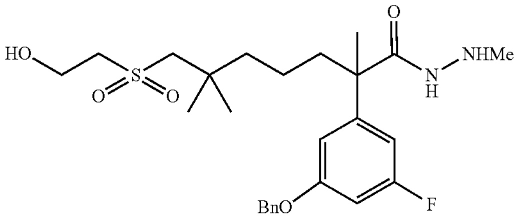 [SMILES: CNNC(=O)C(C)(CCCC(C)(C)CS(=O)(=O)CCO)c1cc(F)cc(OCc2ccccc2)c1] | 2-(3-(benzyloxy)-5-fluorophenyl)-7-((2-hydroxyethyl)sulfonyl)-N',2,6,6-tetramethylheptanehydrazide | 509 |
| 69-5 | 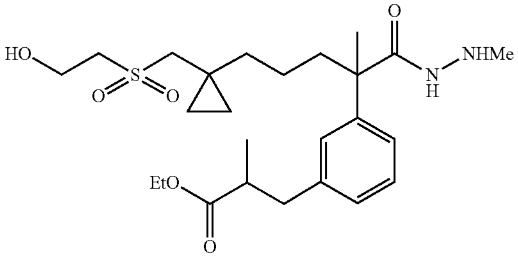 [SMILES: CCOC(=O)C(C)Cc1cccc(C(C)(CCCC2(CS(=O)(=O)CCO)CC2)C(=O)NNC)c1] | ethyl 3-(3-(5-(1-(((2-hydroxyethyl)sulfonyl)methyl) cyclopropyl)-2-methyl-1-(2-methylhydrazineyl)-1-oxopentan-2-yl) phenyl)-2-methylpropanoate | 497 |
| 69-6 | 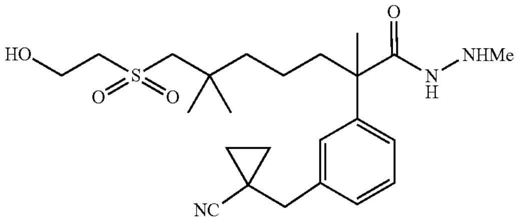 [SMILES: CNNC(=O)C(C)(CCCC(C)(C)CS(=O)(=O)CCO)c1cccc(CC2(C#N)CC2)c1] | 2-(3-((1-cyanocyclopropyl) methyl)phenyl)-7-((2-hydroxyethyl)sulfonyl)-N',2,6,6-tetramethylheptanehydrazide | 464 |

-continued

| Inter. No. | Structure | Name | MS m/z $[M + H]^+$ |
|---|---|---|---|
| 69-7 | 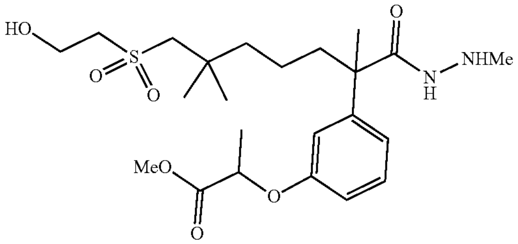 [SMILES: CNNC(=O)C(C)(CCCC(C)(C)CS(=O)(=O)CCO)c1cccc(OC(C)C(=O)OC)c1] | methyl 2-(3-(7-((2-hydroxyethyl)sulfonyl)-2,6,6-trimethyl-1-(2-methylhydrazineyl)-1-oxoheptan-2-yl)phenoxy)propanoate | 509 $[M + Na]^+$ |
| 69-8 | 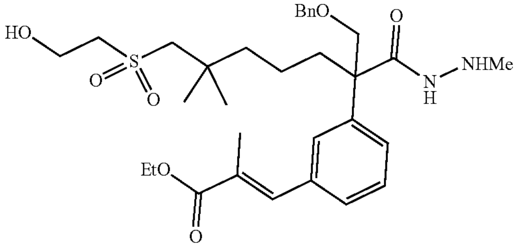 [SMILES: CCOC(=O)/C(C)=C/c1cccc(C(CCCC(C)(C)CS(=O)(=O)CCO)(COCc2ccccc2)C(=O)NNC)c1] | ethyl (E)-3-(3-(2-((benzyloxy)methyl)-7-((2-hydroxyethyl)sulfonyl)-6,6-dimethyl-1-(2-methylhydrazineyl)-1-oxoheptan-2-yl)phenyl)-2-methylacrylate | 603 |
| 69-9 | 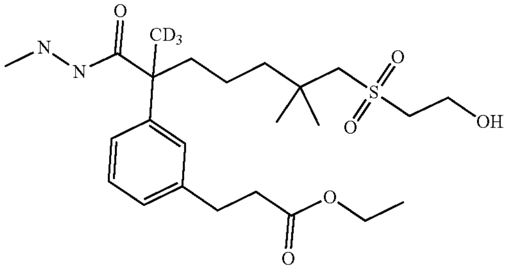 | ethyl 3-(3-(7-((2-hydroxyethyl)sulfonyl)-6,6-dimethyl-2-(2-methylhydrazine-1-carbonyl)heptan-2-yl-1,1,1-d3)phenyl)propanoate | 488 |
| 69-10 | 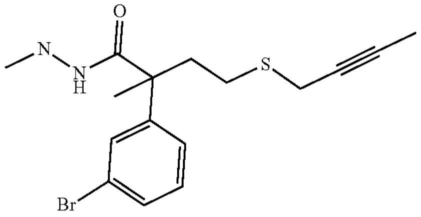 | 2-(3-bromophenyl)-4-(but-2-yn-1-ylthio)-N',2-dimethylbutanehydrazide | 369, 371 |
| 69-11 | 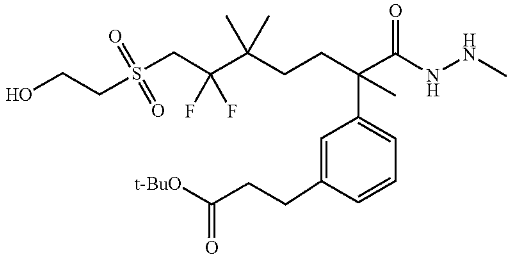 [SMILES: CNNC(=O)C(C)(CCC(C)(C)C(F)(F)CS(=O)(=O)CCO)c1cccc(CCC(=O)OC(C)(C)C)c1] | tert-butyl 3-(3-(6,6-difluoro-7-((2-hydroxyethyl)sulfonyl)-2,5,5-trimethyl-1-(2-methylhydrazineyl)-1-oxoheptan-2-yl)phenyl)propanoate | 549 |
| 69-12 | 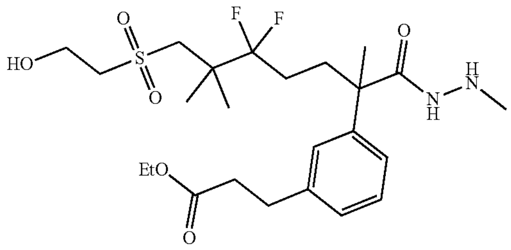 [SMILES: CCOC(=O)CCc1cccc(C(C)(CCC(F)(F)C(C)(C)CS(=O)(=O)CCO)C(=O)NNC)c1] | ethyl 3-(3-(5,5-difluoro-7-((2-hydroxyethyl)sulfonyl)-2,6,6-trimethyl-1-(2-methylhydrazineyl)-1-oxoheptan-2-yl)phenyl)propanoate | 521 |

-continued

| Inter. No. | Structure | Name | MS m/z [M + H]+ |
|---|---|---|---|
| 69-13 | 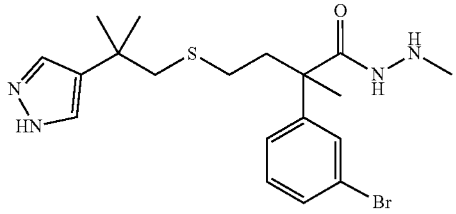 [SMILES: CNNC(=O)C(C)(CCSCC(C)(C)c1cn[nH]c1)c1cccc(Br)c1] | 2-(3-bromophenyl)-N',2-dimethyl-4-((2-methyl-2-(1H-pyrazol-4-yl)propyl)thio) butanehydrazide | 439 |
| 69-14 | 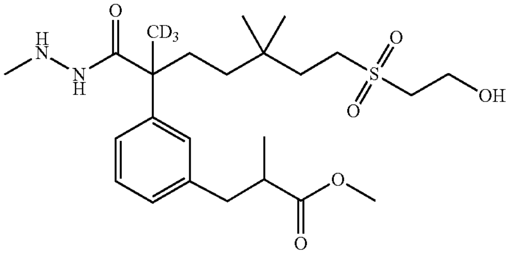 [SMILES: [2H]C([2H])([2H])C(CCC(C)(C)CCS(=O)(=O)CCO)(C(=O)NNC)c1cccc(CC(C)C(=O)OC)c1] | methyl 3-(3-(7-((2-hydroxyethyl)sulfonyl)-5,5-dimethyl-2-(2-methylhydrazine-1-carbonyl)heptan-2-yl-1,1,1-d3)phenyl)-2-methylpropanoate | 488 |
| 69-15 | 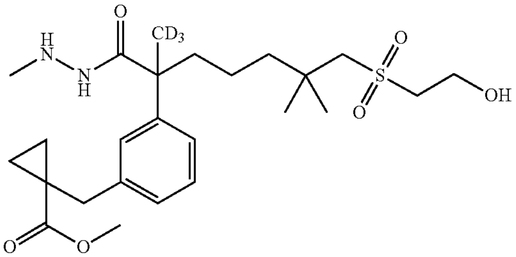 [SMILES: [2H]C([2H])([2H])C(CCCC(C)(C)CS(=O)(=O)CCO)(C(=O)NNC)c1cccc(CC2(C(=O)OC)CC2)c1] | methyl 1-(3-(7-((2-hydroxyethyl)sulfonyl)-6,6-dimethyl-2-(2-methylhydrazine-1-carbonyl)heptan-2-yl-1,1,1-d3)benzyl)cyclopropane-1-carboxylate | 500 [M + H]+ $^1$H NMR (400 MHz, $CD_3OD$) δ 7.28-7.22 (m, 3H), 7.16 (d, J = 6.8 Hz, 1H), 3.97 (t, J = 5.6 Hz, 2H), 3.64 (s, 3H), 3.19-3.14 (m, 4H), 3.05-3.00 (m, 5H), 1.97-1.85 (m, 2H), 1.54-1.50 (m, 4H), 1.24 (s, 2H), 1.14 (s, 6H), 0.90 (t, J = 10.8 Hz, 2H) ppm. |
| 69-16 | 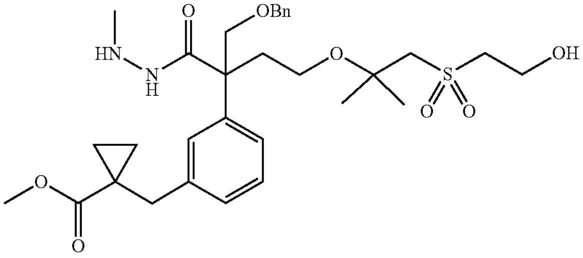 [SMILES: CNNC(=O)C(CCOC(C)(C)CS(=O)(=O)CCO)(COCc1ccccc1)c1cccc(CC2(C(=O)OC)CC2)c1] | methyl 1-(3-(2-((benzyloxy)methyl)-4-((1-((2-hydroxyethyl)sulfonyl)-2-methylpropan-2-yl)oxy)-1-(2-methylhydrazineyl)-1-oxobutan-2-yl)benzyl)cyclopropane-1-carboxylate | 605 |
| 69-17 | 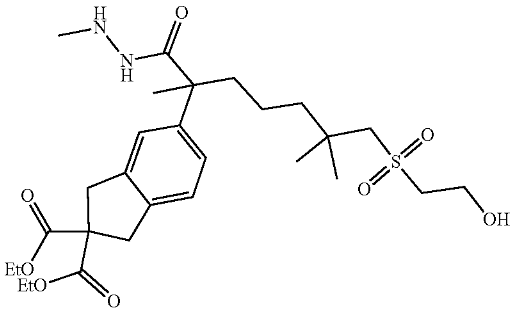 [SMILES: CCOC(=O)C1(C(=O)OCC)Cc2ccc(C(C)(CCCC(C)(C)CS(=O)(=O)CCO)C(=O)NNC)cc2C1] | diethyl 5-(7-((2-hydroxyethyl)sulfonyl)-2,6,6-trimethyl-1-(2-methylhydrazineyl)-1-oxoheptan-2-yl)-1,3-dihydro-2H-indene-2,2-dicarboxylate | 569 |

-continued

| Inter. No. | Structure | Name | MS m/z [M + H]+ |
| --- | --- | --- | --- |
| 69-18 | 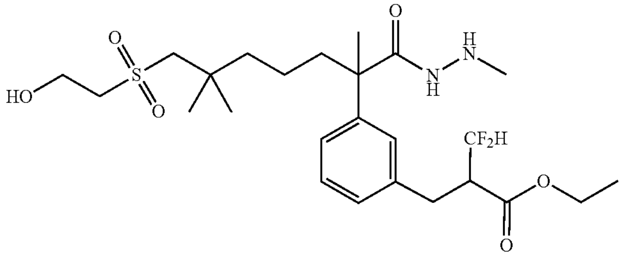 [SMILES: CCOC(=O)C(Cc1cccc(C(C)(CCCC(C)(C)CS(=O)(=O)CCO)C(=O)NNC)c1)C(F)F] | ethyl 3,3-difluoro-2-(3-(7-((2-hydroxyethyl)sulfonyl)-2,6,6-trimethyl-1-(2-methylhydrazineyl)-1-oxoheptan-2-yl)benzyl)-3l3-propanoate | 535 |
| 69-19 | 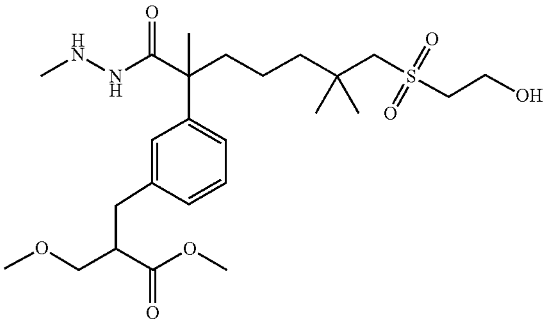 [SMILES: CNNC(=O)C(C)(CCCC(C)(C)CS(=O)(=O)CCO)c1cccc(CC(COC)C(=O)OC)c1] | methyl 2-(3-(7-((2-hydroxyethyl)sulfonyl)-2,6,6-trimethyl-1-(2-methylhydrazineyl)-1-oxoheptan-2-yl)benzyl)-3-methoxypropanoate | 515 |
| 69-20 | 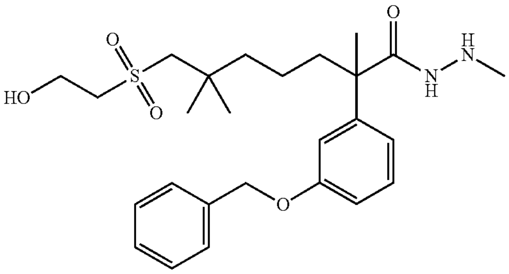 [SMILES: CNNC(=O)C(C)(CCCC(C)(C)CS(=O)(=O)CCO)c1cccc(OCc2ccccc2)c1] | 2-(3-(benzyloxy) phenyl)-7-((2-hydroxyethyl)sulfonyl)-N',2,6,6-tetramethyl-heptanehydrazide | 513.0 [M + Na]+ |
| 69-21 | 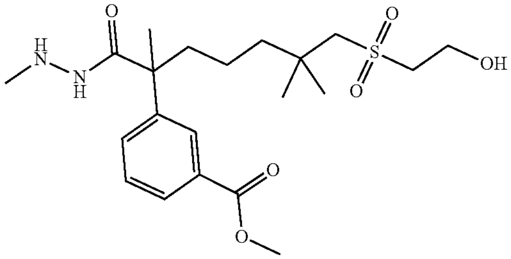 [SMILES: CNNC(=O)C(C)(CCCC(C)(C)CS(=O)(=O)CCO)c1cccc(C(=O)OC)c1] | methyl 3-(7-((2-hydroxyethyl)sulfonyl)-2,6,6-trimethyl-1-(2-methylhydrazineyl)-1-oxoheptan-2-yl)benzoate | 443 |
| 69-22 | 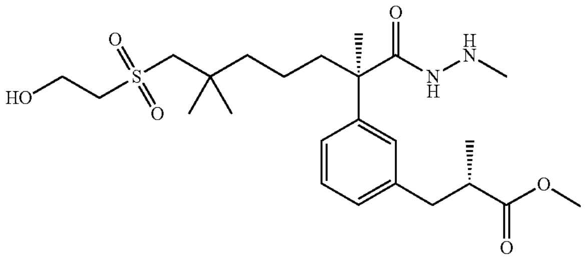 [SMILES: CNNC(=O)[C@](C)(CCCC(C)(C)CS(=O)(=O)CCO)c1cccc(C[C@H](C)C(=O)OC)c1] | methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate | 485 |

-continued

| Inter. No. | Structure | Name | MS m/z [M + H]+ |
|---|---|---|---|
| 69-23 | 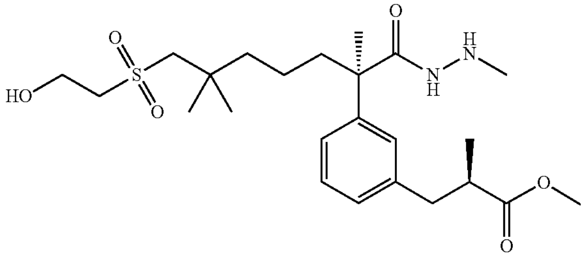 [SMILES: CNNC(=O)[C@](C)(CCCC(C)(C)CS(=O)(=O)CCO)c1cccc(C[C@@H](C)C(=O)OC)c1] | methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate | 485 |
| 69-24 | 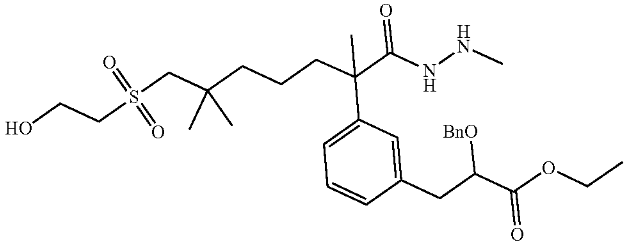 [SMILES: CCOC(=O)C(Cc1cccc(C(C)(CCCC(C)(C)CS(=O)(=O)CCO)C(=O)NNC)c1)OCc1ccccc1] | ethyl 2-(benzyloxy)-3-(3-(7-((2-hydroxy-ethyl)sulfonyl)-2,6,6-trimethyl-1-(2-methylhydrazineyl)-1-oxoheptan-2-yl)phenyl)propanoate | 591 |
| 69-25 | 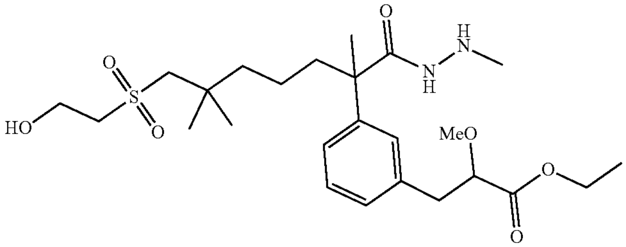 [SMILES: CCOC(=O)C(Cc1cccc(C(C)(CCCC(C)(C)CS(=O)(=O)CCO)C(=O)NNC)c1)OC] | ethyl 3-(3-(7-((2-hydroxyethyl)sulfonyl)-2,6,6-trimethyl-1-(2-methylhydrazineyl)-1-oxoheptan-2-yl)phenyl)-2-methoxypropanoate | 515 |
| 69-26 | 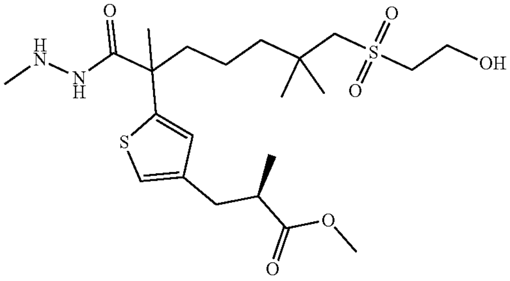 [SMILES: CNNC(=O)C(C)(CCCC(C)(C)CS(=O)(=O)CCO)c1cc(C[C@@H](C)C(=O)OC)cs1] | methyl (2R)-3-(5-(7-((2-hydroxyethyl)sulfonyl)-2,6,6-trimethyl-1-(2-methylhydrazineyl)-1-oxoheptan-2-yl)thiophen-3-yl)-2-methylpropanoate | 491 [M + H]+; RT 1.61 min. (LC-MS Method 4). |
| 69-27 | 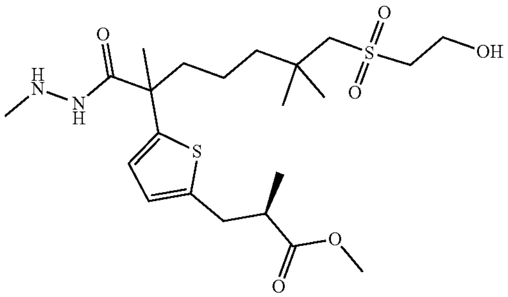 [SMILES: CNNC(=O)C(C)(CCCC(C)(C)CS(=O)(=O)CCO)c1ccc(C[C@@H](C)C(=O)OC)s1] | methyl (2R)-3-(5-(7-((2-hydroxyethyl)sulfonyl)-2,6,6-trimethyl-1-(2-methylhydrazineyl)-1-oxoheptan-2-yl)thiophen-2-yl)-2-methylpropanoate | 491 [M + H]+; RT 1.42 min. (LC-MS Method 4). |

-continued

| Inter. No. | Structure | Name | MS m/z $[M + H]^+$ |
|---|---|---|---|
| 69-28 | 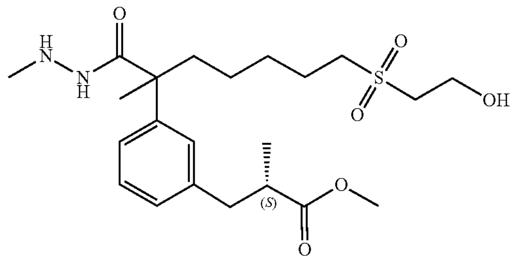 | methyl (2S)-3-(3-(7-((2-hydroxyethyl) sulfonyl)-2-methyl-1-(2-methylhydrazineyl)-1-oxoheptan-2-yl)phenyl)-2-methylpropanoate | 479 [M + Na]+; RT 1.40 min. (LC-MS Method 3). |
| 69-29 | 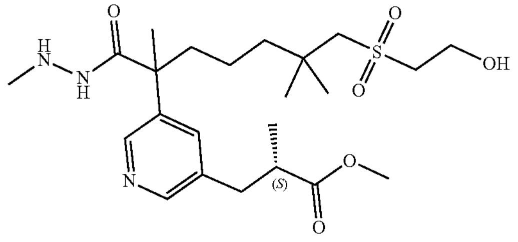 | methyl (2S)-3-(5-(7-((2-hydroxyethyl)sulfonyl)-2,6,6-trimethyl-1-(2-methylhydrazineyl)-1-oxoheptan-2-yl)pyridin-3-yl)-2-methylpropanoate | 486 $[M + H]^+$; RT: 1.30 min. (LC-MS Method 034) |
| 69-30 | 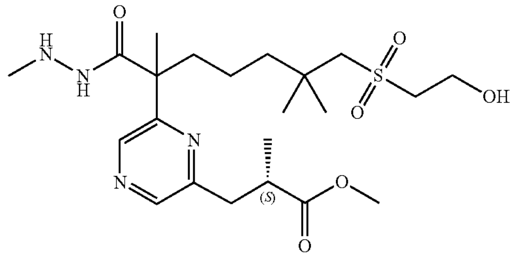 | methyl (2S)-3-(6-(7-((2-hydroxyethyl)sulfonyl)-2,6,6-trimethyl-1-(2-methylhydrazineyl)-1-oxoheptan-2-yl)pyrazin-2-yl)-2-methylpropanoate | 487 $[M + H]^+$; RT: 1.26 min. (LC-MS Method 041) |
| 69-31 | 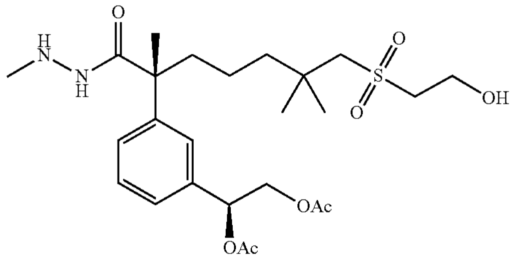 [SMILES: CNNC(=O)[C@](C)(CCCC(C)(C)CS(=O)(=O)CCO)c1cccc([C@@H](COC(C)=O)OC(C)=O)c1] | (S)-1-(3-((R)-7-((2-hydroxyethyl)sulfonyl)-2,6,6-trimethyl-1-(2-methylhydrazineyl)-1-oxoheptan-2-yl)phenyl)ethane-1,2-diyl diacetate | 529 $[M + H]^+$; RT: 1.42 min. (LC-MS Method 003) |
| 69-32 | 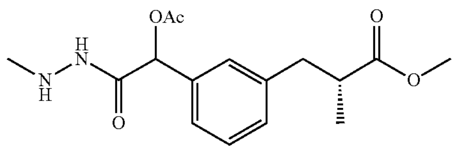 | methyl (2R)-3-(3-(1-acetoxy-2-(2-methylhydrazineyl)-2-oxoethyl)phenyl)-2-methylpropanoate | 323 $[M + H]^+$; RT: 1.60 min. (LC-MS Method 026) |

Intermediate 70: tert-Butyl 2-[3-(3-ethoxy-2-methyl-3-oxo-propyl)phenyl]-7-hydroxy-2,6,6-trimethyl-5-oxo-heptanoate

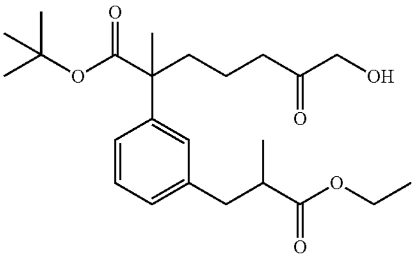 [SMILES: CCOC(=O)C(C)Cc1cccc(C(C)(CCCC(=O)CO)C(=O)OC(C)(C)C)c1]

To a stirred solution of tert-butyl 7-benzyloxy-2-[13-(3-ethoxy-2-methyl-3-oxo-prop-1-enyl)phenyl]-2,6,6-trimethyl-5-oxo-heptanoate (Intermediate 70B, 4 g, 7.45 mmol) in ethanol (80 mL) was added palladium on carbon (50% wet, 10%, 2 g). The mixture was stirred under hydrogen at 50° C. for 3 hours. The mixture was filtered through a pad of Celite and rinsed with ethanol (2×10 mL). The filtrate was concentrated to give the title product (3.22 g, yield 96%) as oil. MS (ESI): 421 m/z $[M+Na]^+$.

Intermediate 70A: Methyl 7-benzyloxy-2-(3-bromophenyl)-2,6,6-trimethyl-5-oxo-heptanoate

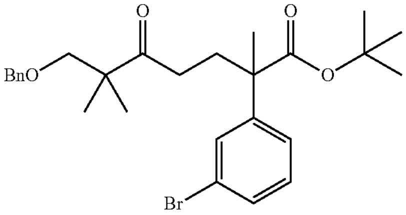 [SMILES: CC(C)(C)OC(=O)C(C)(CCC(=O)C(C)(C)COCc1ccccc1)c1cccc(Br)c1]

To a stirred and cooled (−78° C.) solution of tert-butyl 2-(3-bromophenyl)propanoate (31 g, 109 mmol) in tetrahydrofuran (400 mL) under argon was added lithium diisopropylamide (2M in tetrahydrofuran, 60 mL, 120 mmol). The mixture was stirred at this temperature for 1 hour. A solution of 5-benzyloxy-4,4-dimethyl-pent-1-en-3-one (28.2 g, 129 mmol) in tetrahydrofuran (50 mL) was added slowly. The mixture was slowly warmed up to room temperature and stirred overnight, quenched with saturated ammonium chloride (1000 mL), and extracted with ethyl acetate (3×400 mL). The combined organic extracts were washed with brine, dried over sodium sulfate, filtered, and concentrated. The residue was purified by flash chromatography (660 g silica gel column, 0-20% ethyl acetate in petroleum ether) to give the title product (20 g, 37%) as oil. MS (ESI): 525, 527 m/z $[M+Na]^+$.

Intermediate 70B: tert-Butyl 7-benzyloxy-2-[3-(3-ethoxy-2-methyl-3-oxo-prop-1-enyl)phenyl]-2,6,6-trimethyl-5-oxo-heptanoate

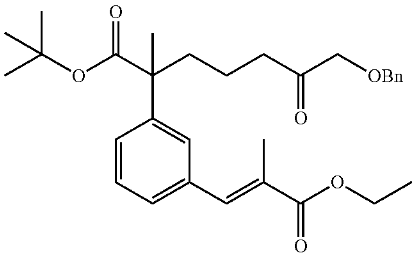 [SMILES: CCOC(=O)/C(C)=C/c1cccc(C(C)(CCCC(=O)COCc2ccccc2)C(=O)OC(C)(C)C)c1]

To a stirred solution of tert-butyl 7-benzyloxy-2-(3-bromophenyl)-2,6,6-trimethyl-5-oxo-heptanoate (Intermediate 70A, 5.5 g, 10.9 mmol) in N,N-dimethylformamide (70 mL) was added tris(o-tolyl)phosphine (997 mg, 3.28 mmol), palladium (II) acetate (245 mg, 1.09 mmol), ethyl 2-methylprop-2-enoate (3.22 mL, 32.8 mmol) and triethylamine (7.61 mL, 54.6 mmol). The mixture was purged with nitrogen and stirred at 120° C. overnight, then cooled to room temperature and quenched with water (250 mL). The mixture was extracted with ethyl acetate (3×100 mL). The combined extracts were washed with brine (2×50 mL), dried over sodium sulfate, filtered, and concentrated. The residue was purified by flash chromatography (120 g silica gel column, 0-30% ethyl acetate in petroleum ether) to give (4 g, yield 68%) as an oil. MS (ESI): 531 m/z $[M+Na]^+$.

Intermediate 71: Methyl 2-(3-bromophenyl)-5-(1-(hydroxymethyl)cyclopropyl)-2-methylpentanoate

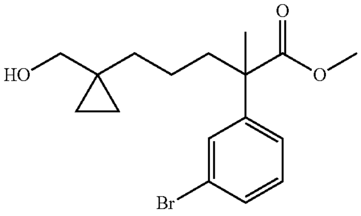 [SMILES: COC(=O)C(C)(CCCC1(CO)CC1)c1cccc(Br)c1]

To a stirred solution of 1-(4-(3-bromophenyl)-5-methoxy-4-methyl-5-oxopentyl)cyclopropane-1-carboxylic acid (Intermediate 71A, 19.2 g) was added borane-tetrahydrofuran complex (1M in THF, 61.6 mL) for 4 hours at room temperature. The mixture was quenched with water (70 mL), then extracted with ethyl acetate (3×100 mL). The combined organic extracts were dried over sodium sulfate, filtered and concentrated, to give methyl 2-(3-bromophenyl)-5-(1-(hydroxymethyl)cyclopropyl)-2-methylpentanoate (14 g, 77% yield), a transparent solid. MS (ESI): 377, 379 m/z $[M+Na]^+$.

Intermediate 71A: 1-(4-(3-Bromophenyl)-5-methoxy-4-methyl-5-oxopentyl)cyclopropane-1-carboxylic Acid

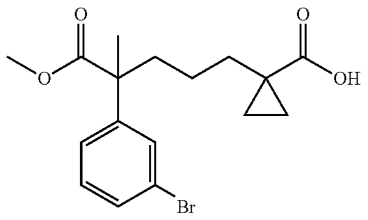 [SMILES: COC(=O)C(C)(CCCC1(C(=O)O)CC1)c1cccc(Br)c1]

tert-Butyl 1-(4-(3-bromophenyl)-5-methoxy-4-methyl-5-oxopentyl)cyclopropane-1-carboxylate (Intermediate 40A-1, 21 g) was treated with hydrogen chloride in 1,4-dioxane (4M, 300 mL) for 4 hours at room temperature. The solvent was removed and the title compound (19.2 g, yield 84%) was obtained as a transparent solid. The solid was used in the next step without further purification. MS (ESI): 391, 393 m/z $[M+Na]^+$.

Intermediate 72: 2-(3-(3-Ethoxy-3-oxopropyl)phenyl)-5-(1-(((2-hydroxyethyl)sulfonyl)methyl)cyclopropyl)-2-methylpentanoic acid

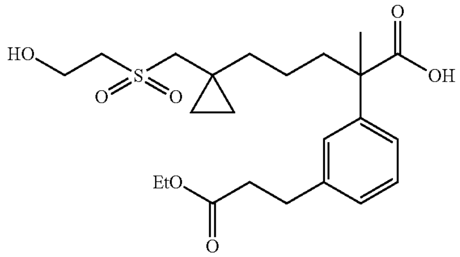 [SMILES: CCOC(=O)CCc1cccc(C(C)(CCCC2(CS(=O)(=O)CCO)CC2)C(=O)O)c1]

Exchanging (E)-2-(3-(3-Ethoxy-3-oxoprop-1-en-1-yl)phenyl)-7-hydroxy-2,6,6-trimethylheptanoic acid (Intermediate 55A) for (E)-2-(3-(3-ethoxy-3-oxoprop-1-en-1-yl)phenyl)-5-(1-(((2-hydroxyethyl)sulfonyl)methyl)cyclopropyl)-2-methylpentanoic acid (Intermediate 72E, 1.1 g), the procedure described for Intermediate 55 was used to prepare the title compound (1.0 g, 90% yield), a white solid. MS (ESI): 477 m/z $[M+Na]^+$.

The following intermediates were prepared based on the procedures described for Intermediate 72, and/or for Intermediates 72A to 72E.

| Inter. No. | Structure | Name | MS m/z $[M + H]^+$ |
|---|---|---|---|
| 72-1 | 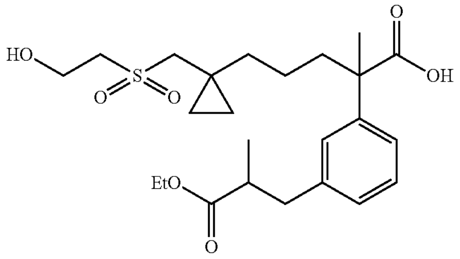 [SMILES: CCOC(=O)C(C)Cc1cccc(C(C)(CCCC2(CS(=O)(=O)CCO)CC2)C(=O)O)c1] | 2-(3-(3-ethoxy-2-methyl-3-oxopropyl)phenyl)-5-(1-(((2-hydroxyethyl)sulfonyl)methyl)cyclopropyl)-2-methylpentanoic acid | 491 $[M + Na]^+$ |
| 72-2 | 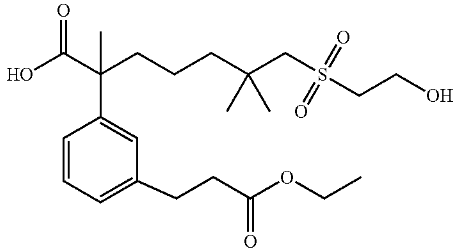 [SMILES: CCOC(=O)CCc1cccc(C(C)(CCCC(C)(C)CS(=O)(=O)CCO)C(=O)O)c1] | 2-(3-(3-ethoxy-3-oxopropyl)phenyl)-7-((2-hydroxyethyl)sulfonyl)-2,6,6-trimethylheptanoic acid | 479 $[M + Na]^+$ |
| 72-3 | 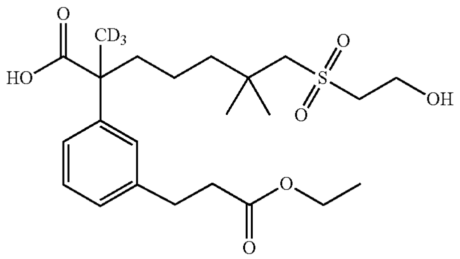 [SMILES: [2H]C([2H])([2H])C(CCCC(C)(C)CS(=O)(=O)CCO)(C(=O)O)c1cccc(CCC(=O)OCC)c1] | 2-(3-(3-ethoxy-3-oxopropyl)phenyl)-7-((2-hydroxyethyl)sulfonyl)-6,6-dimethyl-2-(methyl-d3)heptanoic acid | 482 $[M + Na]^+$ |

-continued

| Inter. No. | Structure | Name | MS m/z [M + H]+ |
|---|---|---|---|
| 72-4 | 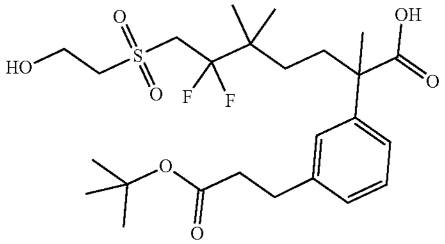 [SMILES: CC(C)(C)OC(=O)CCc1cccc(C(C)(CCC(C)(C)C(F)(F)CS(=O)(=O)CCO)C(=O)O)c1] | 2-(3-(3-(tert-butoxy)-3-oxopropyl)phenyl)-6,6-difluoro-7-((2-hydroxyethyl) sulfonyl)-2,5,5-trimethylheptanoic acid | 543 [M + Na]+ |
| 72-5 | 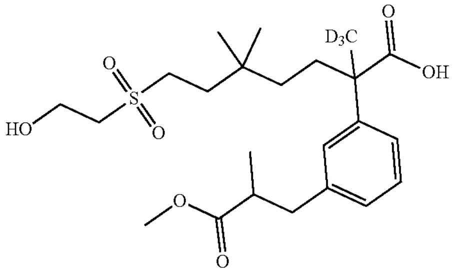 [SMILES: [2H]C([2H])([2H])C(CCC(C)(C)CCS(=O)(=O)CCO)(C(=O)O)c1cccc(CC(C)C(=O)OC)c1] | 7-((2-hydroxyethyl)sulfonyl)-2-(3-(3-methoxy-2-methyl-3-oxopropyl) phenyl)-5,5-dimethyl-2-(methyl-d3)heptanoic acid | 482 [M + Na]+ |
| 72-6 | 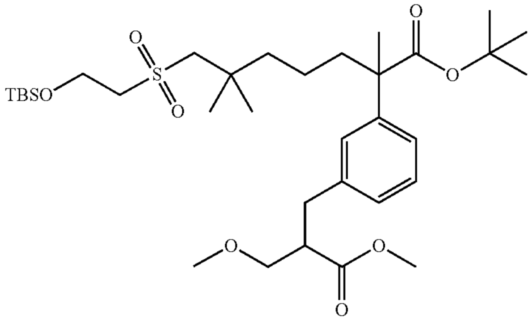 [SMILES: COCC(Cc1cccc(C(C)(CCCC(C)(C)CS(=O)(=O)CCO[Si](C)(C)C(C)(C)C)C(=O)OC(C)(C)C)c1)C(=O)OC] | tert-butyl 7-((2-((tert-butyldimethylsilyl)oxy) ethyl)sulfonyl)-2-(3-(3-methoxy-2-(methoxymethyl)-3-oxopropyl)phenyl)-2,6,6-trimethylheptanoate | 679 [M + Na]+ |

Intermediate 72A: Methyl 5-(1-((acetylthio)methyl) cyclopropyl)-2-(3-bromophenyl)-2-methylpentanoate

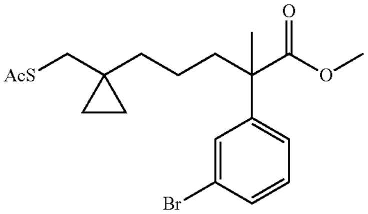

Exchanging tert-butyl 7-hydroxy-2-(3-iodophenyl)-2,6,6-trimethylheptanoate (Intermediate 60) for methyl 2-(3-bromophenyl)-5-(1-(hydroxymethyl)cyclopropyl)-2-methylpentanoate (Intermediate 61, 13 g), the procedure described for Intermediate 61 was used to prepare the title compound, isolated as an oil (11 g, 70%). MS (ESI): 413, 415 W/z $[M+H]^+$.

Intermediate 72B: Methyl 2-(3-bromophenyl)-5-(1-(((2-hydroxyethyl)thio)methyl)cyclopropyl)-2-methylpentanoate

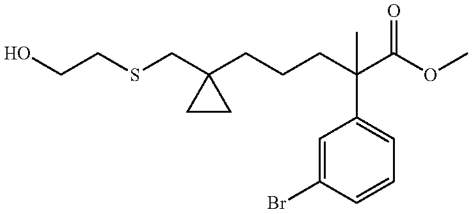 [SMILES: COC(=O)C(C)(CCCC1(CSCCO)CC1)c1cccc(Br)c1]

Exchanging tert-Butyl 7-(acetylthio)-2-(3-iodophenyl)-2,6,6-trimethylheptanoate (Intermediate 61) for methyl 5-(1-((acetylthio)methyl)cyclopropyl)-2-(3-bromophenyl)-2-methylpentanoate (Intermediate 72A, 9 g), the procedure described for Intermediate 62 was used to prepare the title compound, isolated as an oil (7 g, 77%). MS (ESI): 437, 439 m/z $[M+Na]^+$.

Intermediate 72C: Methyl 2-(3-bromophenyl)-5-(1-(((2-hydroxyethyl)sulfonyl)methyl)cyclopropyl)-2-methylpentanoate

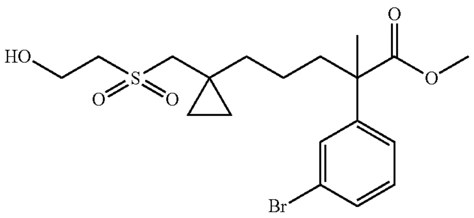 [SMILES: COC(=O)C(C)(CCCC1(CS(=O)(=O)CCO)CC1)c1cccc(Br)c1]

Exchanging tert-Butyl 7-((2-hydroxyethyl)thio)-2-(3-iodophenyl)-2,6,6-trimethylheptanoate (Intermediate 62) for methyl 2-(3-bromophenyl)-5-(1-(((2-hydroxyethyl)thio)methyl)cyclopropyl)-2-methylpentanoate, the procedure described for Intermediate 63 was used to prepare the title compound (7 g, 90% yield), isolated as a white solid. MS (ESI): 447, 449 m/z [M+H]$^+$.

Intermediate 72D: 2-(3-Bromophenyl)-5-(1-(((2-hydroxyethyl)sulfonyl)methyl)cyclopropyl)-2-methylpentanoic Acid

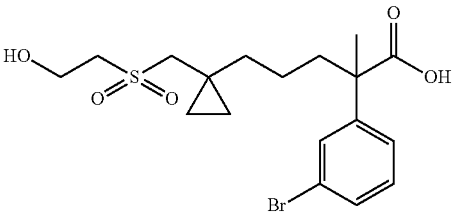 [SMILES: CC(CCCC1(CS(=O)(=O)CCO)CC1)(C(=O)O)c1cccc(Br)c1]

Exchanging methyl 2-(3-bromophenyl)-2-((3-((2-hydroxyethyl)thio)-2,2-dimethylpropoxy)methyl)propanoate-3,3,3-$d_3$ (Intermediate 58B) for methyl 2-(3-bromophenyl)-5-(1-(((2-hydroxyethyl)sulfonyl)methyl)cyclopropyl)-2-methylpentanoate (6.2 g), the procedure described for Intermediate 58C was used to prepare the title compound (5.5 g, 91% yield), isolated as a white solid. MS (ESI): 455, 457 m/z [M+Na]$^+$.

The following intermediates were prepared based on the procedures described for Intermediate 72D.

| Inter. No. | Structure | Name | MS m/z [M + H]$^+$ |
|---|---|---|---|
| 72D-1 | 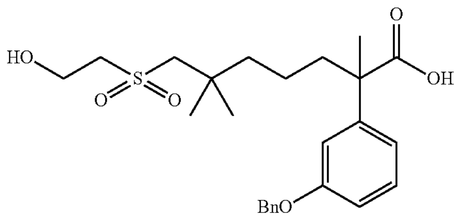 [SMILES: CC(C)(CCCC(C)(C(=O)O)c1cccc(OCc2ccccc2)c1)CS(=O)(=O)CCO] | 2-(3-(benzyloxy)phenyl)-7-((2-hydroxyethyl)sulfonyl)-2,6,6-trimethylheptanoic acid | 485 [M + Na]$^+$ |
| 72D-2 | 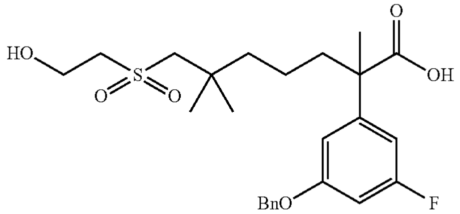 [SMILES: CC(C)(CCCC(C)(C(=O)O)c1cc(F)cc(OCc2ccccc2)c1)CS(=O)(=O)CCO] | 2-(3-(benzyloxy)-5-fluorophenyl)-7-((2-hydroxyethyl)sulfonyl)-2,6,6-trimethylheptanoic acid | 481 |
| 72D-3 | 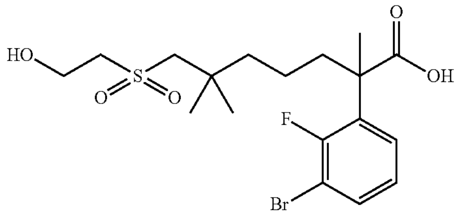 [SMILES: CC(C)(CCCC(C)(C(=O)O)c1cccc(Br)c1F)CS(=O)(=O)CCO] | 2-(3-bromo-2-fluorophenyl)-7-((2-hydroxyethyl)sulfonyl)-2,6,6-trimethylheptanoic acid | 475, 477 [M + Na]$^+$ |
| 72D-4 | 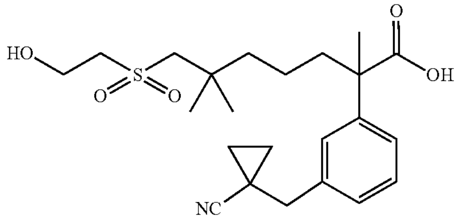 [SMILES: CC(C)(CCCC(C)(C(=O)O)c1cccc(CC2(C#N)CC2)c1)CS(=O)(=O)CCO] | 2-(3-((1-cyanocyclopropyl)methyl)phenyl)-7-((2-hydroxyethyl)sulfonyl)-2,6,6-trimethylheptanoic acid | 458.2 [M + Na]$^+$ |

-continued

| Inter. No. | Structure | Name | MS m/z [M + H]+ |
|---|---|---|---|
| 72D-5 | 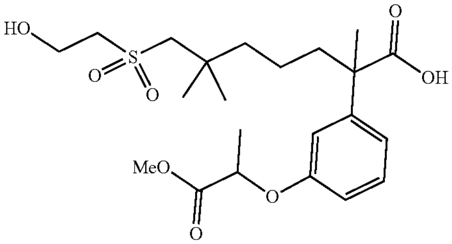 [SMILES: COC(=O)C(C)Oc1cccc(C(C)(CCCC(C)(C)CS(=O)(=O)CCO)C(=O)O)c1] | 7-((2-hydroxyethyl)sulfonyl)-2-(3-((1-methoxy-1-oxopropan-2-yl)oxy)phenyl)-2,6,6-trimethylheptanoic acid | 459 |
| 72D-6 | 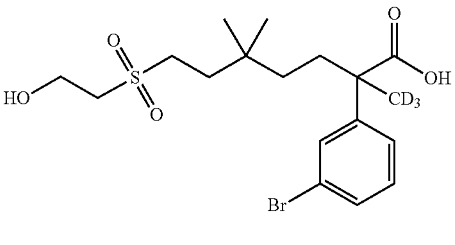 [SMILES: [2H]C([2H])([2H])C(CCC(C)(C)CCS(=O)(=O)CCO)(C(=O)O)c1cccc(Br)c1] | 2-(3-bromophenyl)-7-((2-hydroxyethyl)sulfonyl)-5,5-dimethyl-2-(methyl-d3)heptanoic acid | 460, 462 [M + Na]+ |
| 72D-7 | 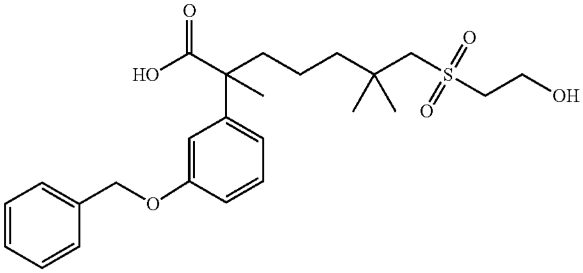 [SMILES: CC(C)(CCCC(C)(C(=O)O)c1cccc(OCc2ccccc2)c1)CS(=O)(=O)CCO] | 2-(3-(benzyloxy)phenyl)-7-((2-hydroxyethyl)sulfonyl)-2,6,6-trimethylheptanoic acid | 485 [M + Na]+ |

Intermediate 72E: (E)-2-(3-(3-ethoxy-3-oxoprop-1-en-1-yl)phenyl)-5-(1-(((2-hydroxyethyl)sulfonyl)methyl)cyclopropyl)-2-methylpentanoic Acid

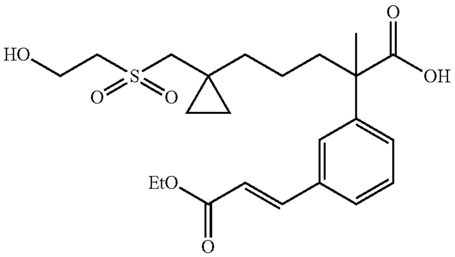 [SMILES: CCOC(=O)/C=C/c1cccc(C(C)(CCCC2(CS(=O)(=O)CCO)CC2)C(=O)O)c1]

Exchanging 7-hydroxy-2-(3-iodophenyl)-2,6,6-trimethylheptanoic acid (Intermediate 17B) for 2-(3-Bromophenyl)-5-(1-(((2-hydroxyethyl)sulfonyl)methyl)cyclopropyl)-2-methylpentanoic acid (1.9 g), the procedure described for Intermediate 55A was used to prepare the title compound (1.1 g, 65% yield) isolated as a bright yellow oil. MS (ESI): 453 m/z $[M+H]^+$.

The following intermediates were prepared based on the procedures described for Intermediate 72E.

| Inter. No. | Structure | Name | MS m/z [M + H]+ |
|---|---|---|---|
| 72E-1 | 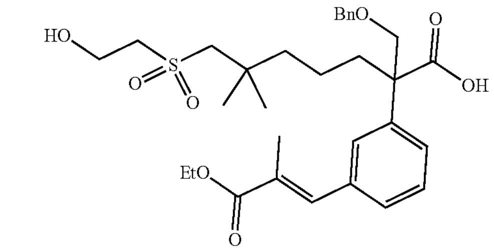 [SMILES: CCOC(=O)/C(C)=C/c1cccc(C(CCCC(C)(C)CS(=O)(=O)CCO)(COCc2ccccc2)C(=O)O)c1] | (E)-2-((benzyloxy)methyl)-2-(3-(3-ethoxy-2-methyl-3-oxoprop-1-en-1-yl)phenyl)-7-((2-hydroxyethyl)sulfonyl)-6,6-dimethylheptanoic acid | 497 [M + Na]+ |
| 72E-2 | 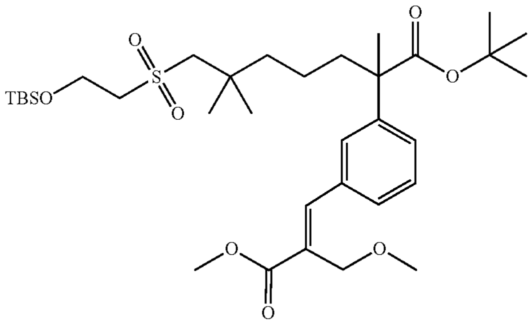 [SMILES: COC/C(=C\c1cccc(C(C)(CCCC(C)(C)CS(=O)(=O)CCO[Si](C)(C)C(C)(C)C)C(=O)OC(C)(C)C)c1)C(=O)OC] | tert-butyl (E)-7-((2-((tert-butyldimethylsilyl)oxy)ethyl)sulfonyl)-2-(3-(3-methoxy-2-(methoxymethyl)-3-oxoprop-1-en-1-yl)phenyl)-2,6,6-trimethylheptanoate | 677 [M + Na]+ |

Intermediate 73: tert-Butyl 2-(3-((1-cyanocyclopropyl)methyl)phenyl)-7-hydroxy-2,6,6-trimethylheptanoate

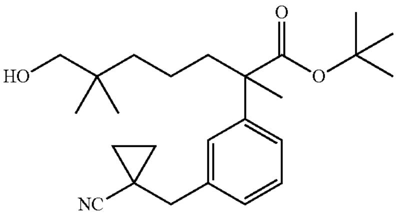 [SMILES: CC(C)(CO)CCCC(C)(C(=O)OC(C)(C)C)c1cccc(CC2(C#N)CC2)c1]

To a stirred and cooled (−78° C.) solution of cyclopropanecarbonitrile (6.7 g, 99.9 mmol) in tetrahydrofuran (100 mL) was added lithium diisopropylamide (2M in tetrahydrofuran) (49.9 mL, 99.9 mmol) dropwise over 15 minutes. The mixture was stirred for 2 hours at −78° C. and treated with tert-butyl 7-acetoxy-2-(3-(bromomethyl)phenyl)-2,6,6-trimethylheptanoate (Intermediate 73B, 13 g, 28.5 mmol). The reaction mixture was warmed up to room temperature and stirred for 16 hours, then quenched with water. The mixture was extracted with ethyl acetate (3×300 mL). The combined organic extracts were washed with brine, dried over anhydrous sodium sulfate, filtered, and concentrated. The residue was purified by flash chromatography (330 g silica gel column, 0-30% ethyl acetate in petroleum ether) to give the title compound (2.3 g, yield 13.4%) as light-yellow oil. MS(ESI): 422 m/z $[M+Na]^+$.

Intermediate 73A: tert-Butyl 7-acetoxy-2,6,6-trimethyl-2-(m-tolyl)heptanoate

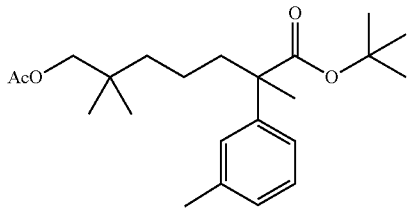 [SMILES: CC(=O)OCC(C)(C)CCCC(C)(C(=O)OC(C)(C)C)c1cccc(C)c1]

To a stirred solution of p-toluenesulfonic acid (796 mg, 4.19 mmol) in acetic anhydride (100 mL) at room temperature was added tert-butyl 7-hydroxy-2,6,6-trimethyl-2-(m-tolyl)heptanoate (Intermediate 60-1, 14 g, 41.9 mmol). The mixture was stirred at rt for 2 hours, then diluted with tetrahydrofuran (100 mL) and water (100 mL) and stirred overnight. The reaction mixture was neutralized to pH ~8 with saturated sodium bicarbonate, then extracted with ethyl acetate (3×200 mL). The combined organic phases were washed with brine (300 mL), dried over anhydrous sodium sulfate, filtered, and concentrated. The residue was purified by flash chromatography (120 g silica gel column, 0-10% ethyl acetate in petroleum ether) to give the title compound (15 g, yield 95%) as a colorless oil. MS(ESI): 399 m/z $[M+Na]^+$.

Intermediate 73B: tert-Butyl 7-acetoxy-2-(3-(bromomethyl)phenyl)-2,6,6-trimethylheptanoate

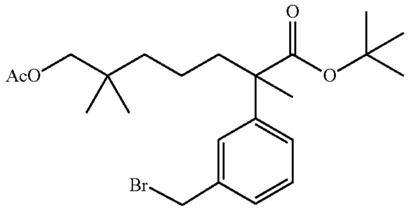 [SMILES: CC(=O)OCC(C)(C)CCCC(C)(C(=O)OC(C)(C)C)c1cccc(CBr)c1]

To a stirred solution of tert-butyl 7-acetoxy-2,6,6-trimethyl-2-(m-tolyl)heptanoate (Intermediate 73A, 1.5 g, 3.98 mmol) in carbon tetrachloride (120 mL) was added N-bromosuccinimide (709 mg, 3.98 mmol) and azodiisobutyronitrile (65.4 mg, 0.398 mmol). The reaction was refluxed for 2 hours under nitrogen atmosphere. The mixture was diluted with water (200 mL), extracted with dichloromethane (3×100 mL). The combined organic phases were washed with brine (200 mL), dried over anhydrous sodium sulfate, filtered, and concentrated. The residue was purified by flash chromatography (40 g silica gel column, eluting with 0-10% ethyl acetate in petroleum ether) to give the title compound (1.4 g, yield 77.4%) as a light-yellow oil. MS(ESI): 477 m/z $[M+Na]^+$.

Intermediate 74: 2-((Benzyloxy)methyl)-2-(3-bromophenyl)-7-hydroxy-6,6-dimethylheptanoic Acid

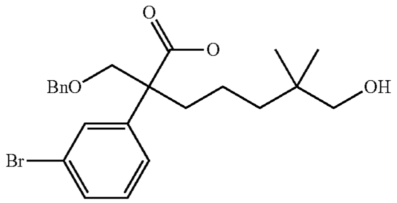 [SMILES: CC(C)(CO)CCCC(COCc1ccccc1)(C(=O)O)c1cccc(Br)c1]

To a solution of methyl 2-((benzyloxy)methyl)-2-(3-bromophenyl)-7-hydroxy-6,6-dimethylheptanoate (Intermediate 74C, 65 g, 140 mmol) in tetrahydrofuran (400 mL) and methanol (200 mL) was added aqueous lithium hydroxide monohydrate (140 mL, 420 mmol, 3M in water). The reaction was stirred at 60° C. for 30 hours. The mixture was acidified with 1M hydrochloric acid to pH=4, extracted with ethyl acetate (2×500 mL). The combined organic phases were washed with brine (500 mL×2), dried over anhydrous sodium sulfate, filtered, and concentrated to afford the title compound (60 g, yield 95.2%) as a light-yellow oil. MS(ESI): 449, 451 m/z $[M+H]^+$.

Intermediate 74A: Methyl 2-(3-bromophenyl)-7-((tert-butyldimethylsilyl)oxy)-6,6-dimethylheptanoate

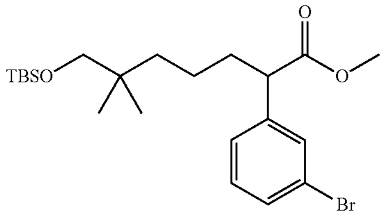 [SMILES: COC(=O)C(CCCC(C)(C)CO[Si](C)(C)C(C)(C)C)c1cccc(Br)c1]

To a stirred and cooled (−78° C.) solution of methyl 2-(3-bromophenyl)acetate (50 g, 218 mmol) in tetrahydrofuran (400 mL) was added lithium diisopropylamide (2.0 M, 131 mL, 262 mmol) dropwise. The mixture was stirred at −78° C. for 2 hours, then treated with tert-butyl((5-iodo-2,2-dimethylpentyl)oxy)dimethylsilane (Intermediate 29C-1, 81.7 g, 229 mmol) dropwise. The reaction mixture was warmed up to room temperature and stirred for 16 hours, then quenched with water (600 mL). The mixture was extracted with ethyl acetate (3×300 mL), washed with brine (2×500 mL), dried over anhydrous sodium sulfate, filtered, and concentrated. The residue was purified by flash chromatography (330 g silica gel column, 0-20% ethyl acetate in petroleum ether) to give the title compound (80 g, yield 80.1%) as a light-yellow oil. MS(ESI): 479 m/z $[M+Na]^+$.

Intermediate 74B: Methyl 2-((benzyloxy)methyl)-2-(3-bromophenyl)-7-((tert-butyldimethylsilyl)oxy)-6,6-dimethylheptanoate

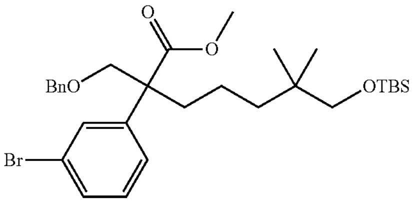 [SMILES: COC(=O)C(CCCC(C)(C)CO[Si](C)(C)C(C)(C)C)(COCc1ccccc1)c1cccc(Br)c1]

To a stirred and cooled (−78° C.) solution of methyl 2-(3-bromophenyl)-7-((tert-butyldimethylsilyl)oxy)-6,6-dimethylheptanoate (Intermediate 74A, 80 g, 175 mmol) in tetrahydrofuran (500 mL) was added lithium diisopropylamide (2.0 M, 105 mL, 210 mmol) dropwise over 15 minutes. The mixture was stirred for 2 hours at −78° C., then treated with benzyl chloromethyl ether (30.1 g, 192 mmol) dropwise. The reaction mixture was warmed up to room temperature and stirred for 16 hours, then quenched with water (500 mL) and concentrated to remove tetrahydrofuran. The residue was extracted with ethyl acetate (3×300 mL), washed with brine (500 mL), dried over anhydrous sodium sulfate, filtered, and concentrated. The residue was purified by flash chromatography (330 g silica gel column, 0-20% ethyl acetate in petroleum ether) to give the title compound (85 g, yield 84%) as a light-yellow oil. MS(ESI): 599 m/z $[M+Na]^+$.

Intermediate 74C: Methyl 2-((benzyloxy)methyl)-2-(3-bromophenyl)-7-hydroxy-6,6-dimethylheptanoate

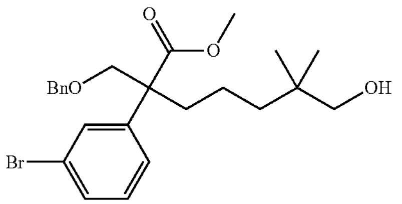 [SMILES: COC(=O)C(CCCC(C)(C)CO)(COCc1ccccc1)c1cccc(Br)c1]

To a solution of methyl 2-((benzyloxy)methyl)-2-(3-bromophenyl)-7-((tert-butyldimethylsilyl)oxy)-6,6-dimethylheptanoate (Intermediate 74B, 85 g, 147 mmol) in tetrahydrofuran (400 mL) was added tetra-n-butylammonium fluoride (441 mL, 441 mmol). The reaction was stirred at room temperature for 16 hours. The mixture was diluted with ethyl acetate (800 mL), washed with water (3×300 mL), dried over anhydrous magnesium sulfate, filtered, and concentrated. The residue was purified by flash chromatography (330 g silica gel column, 0-30% ethyl acetate in petroleum) to give the title compound (65 g, yield 95%) as a light-yellow oil. $^1$H NMR (400 MHz, $CDCl_3$) δ 7.39-7.37 (m, 2H), 7.34-7.27 (m, 3H), 7.23-7.14 (m, 4H), 4.94 (s, 2H), 3.95 (d, J=8.8 Hz, 1H), 3.83 (d, J=9.2 Hz, 1H), 3.66 (s, 3H), 3.24 (s, 2H), 2.10-2.06 (m, 2H), 1.26-1.18 (m, 2H), 1.13-0.95 (m, 2H), 0.79 (d, J=2.0 Hz, 6H) ppm.

Intermediate 75: 5-((4-Bromo-6-fluoro-1-(triisopropylsilyl)-1H-indol-5-yl)methyl)-2-fluorobenzonitrile

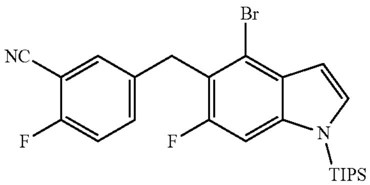

To a stirred solution of (4-bromo-6-fluoro-1-(triisopropylsilyl)-1H-indol-5-yl)(3-cyano-4-fluorophenyl)methyl acetate (Intermediate 57C-1, 7.5 g, 13.4 mmol) in chloroform (75 mL) was added indium(III) bromide (0.237 g, 0.67 mmol) and triethyl silane (8.53 mL, 53.4 mmol) under nitrogen atmosphere. The reaction mixture was stirred at 60° C. for 8 hours. The solution turned from colorless to yellow, then to orange. The mixture was diluted with ethyl acetate (300 mL), then washed with water, dried with sodium sulfate, filtered, and concentrated. The residue was purified by automated flash chromatography (120 g silica gel column, 0-20% ethyl acetate in petroleum ether) to give the title compound (2.25 g, yield: 33%) as a solid. MS(ESI): 503, 505 m/z [M+H]$^+$, RT: 3.38 minutes (LC-MS method 10).

Intermediate 76: Methyl 5-((4-bromo-6-fluoro-1H-indol-5-yl)thio)-2-fluorobenzimidothioate Hydroiodide

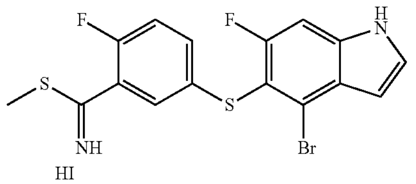

To a stirred solution of 5-((4-bromo-6-fluoro-1H-indol-5-yl)thio)-2-fluorobenzothioamide (Intermediate 76D, 2.6 g, 6.51 mmol) in acetone (30 mL) was added iodomethane (2.03 mL, 32.6 mmol). The mixture was refluxed for 2 hours, then concentrated to give the title compound (3.52 g, yield 100%) as a solid. The product was used without further purification. MS(ESI): 413 m/z [M+H]$^+$.

The following intermediate was prepared based on the procedures described for Intermediate 76.

| Inter. No. | Structure | Name | MS m/z [M + H]$^+$ |
|---|---|---|---|
| 76-1 | 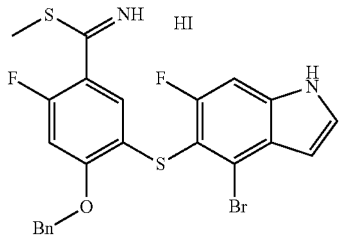 | methyl 4-(benzyloxy)-5-((4-bromo-6-fluoro-1H-indol-5-yl)thio)-2-fluoro-benzimidothioate hydroiodide | 519, 521; RT: 2.19 min. (LC-MS Method 040) |

Intermediate 76A: 2-fluoro-5-[(4-methoxyphenyl)methylsulfanyl]benzonitrile

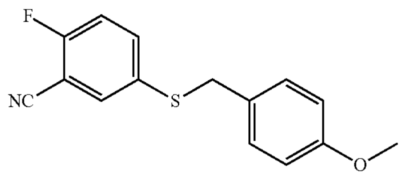 [SMILES: COc1ccc(CSc2ccc(F)c(C#N)c2)cc1]

To a stirred solution of 5-bromo-2-fluoro-benzonitrile (27 g, 135 mmol) and (4-methoxyphenyl)methanethiol (25 g, 162 mmol) in dioxane (300 mL) was added tris(dibenzylideneacetone)dipalladium (6.18 g, 6.75 mmol), Xantphos (7.81 g, 13.5 mmol) and N,N-diisopropylethylamine (46.2 mL, 270 mmol). The reaction was purged with nitrogen and stirred at 100° C. overnight. The mixture was concentrated, and the residue was purified by automated flash chromatography (2×330 g silica gel column, 0-10% ethyl acetate in petroleum ether) to give the title product (25 g, yield 67.8%) as a solid. $^1$H NMR (400 MHz, $CDCl_3$) δ 7.549-7.44 (m, 2H), 7.14 (d, J=8.8 Hz, 2H), 7.09 (t, J=8.8 Hz, 1H), 6.83 (d, J=8.8 Hz, 2H), 4.03 (s, 2H), 3.80 (s, 3H) ppm.

Intermediate 76B: 5-[(3-Cyano-4-fluoro-phenyl)disulfanyl]-2-fluoro-benzonitrile

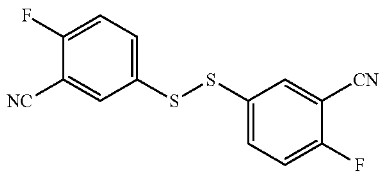 [SMILES: N#Cc1cc(SSc2ccc(F)c(C#N)c2)ccc1F]

To a stirred solution of 2-fluoro-5-[(4-methoxyphenyl)methylsulfanyl]benzonitrile (Intermediate 76A, 25 g, 91.5 mmol) in anisole (100 mL) was added trifluoroacetic acid (100 mL). The mixture was stirred at 50° C. overnight, then concentrated. To a stirred solution of the oil residue in dimethyl sulfoxide (13 mL) was added iodine (1.16 g, 4.57 mmol). The mixture was stirred at room temperature overnight, then diluted with ethyl acetate (150 mL). The mixture was washed with brine (3×50 mL), dried over sodium sulfate, filtered, and concentrated. The residue was purified by automated flash chromatography (330 g silica gel column, 0-20% ethyl acetate in petroleum ether) to give the title compound (8.8 g, 63.2%) as solid. MS(ESI): 327, 329 m/z $[M+Na]^+$.

Intermediate 76C: 5-((4-Bromo-6-fluoro-1-(triisopropylsilyl)-1H-indol-5-yl)thio)-2-fluorobenzonitrile

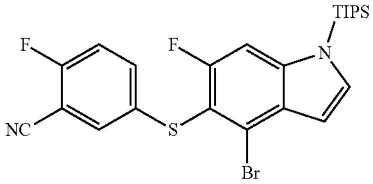

To a stirred and cooled (−78° C.) solution of 4-bromo-6-fluoro-1-(triisopropylsilyl)-1H-indole (Intermediate 57A, 4.8 g, 13 mmol) in tetrahydrofuran (65 mL) was added lithium diisopropylamide (2M in tetrahydrofuran, 13 mL, 26 mmol). The mixture was stirred at −78° C. for 2 hours, then treated with 5-[(3-cyano-4-fluoro-phenyl)disulfanyl]-2-fluoro-benzonitrile (Intermediate 76B, 5.92 g, 19.4 mmol). The mixture was stirred at −78° C. for 2 hours, then warmed to room temperature for 1 hour and quenched with saturated ammonium chloride (150 mL). The mixture was extracted with ethyl acetate (3×150 mL). The combined extract was washed with brine, dried over sodium sulfate, filtered, and concentrated. The residue was purified by automated flash chromatography (120 g silica gel column, 0-20% ethyl acetate in petroleum ether) to give the title compound (4.3 g, 63.6%) as a solid. MS(ESI): 521 m/z $[M+H]^+$.

Intermediate 76D: 5-((4-Bromo-6-fluoro-1H-indol-5-yl)thio)-2-fluorobenzothioamide

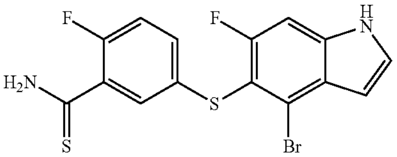 [SMILES: NC(=S)c1cc(Sc2c(F)cc3[nH]ccc3c2Br)ccc1F]

To a stirred solution of 5-((4-Bromo-6-fluoro-1-(triisopropylsilyl)-1H-indol-5-yl)thio)-2-fluorobenzonitrile (Intermediate 76C, 4.3 g, 8.24 mmol) in N,N-dimethylformamide (50 mL) was added magnesium chloride (2.35 g, 24.7 mmol), sodium hydrosulfide (2.77 g, 49.5 mmol) and water (1.78 g, 98.9 mmol). The mixture was stirred at room temperature for 1 hour, then diluted with water (150 mL). The mixture was extracted with ethyl acetate (3×150 mL). The combined extracts were washed with brine, dried over sodium sulfate, filtered, and concentrated. The residue was purified by automated flash chromatography (80 g silica gel column, 0-60% ethyl acetate in petroleum ether) to give the title compound (2.6 g, 79%) as solid. MS(ESI): 399 m/z $[M+H]^+$.

The following intermediates were prepared based on the procedures described for Intermediate 76D.

| Inter. No. | Structure | Name | MS m/z $[M + H]^+$ |
| --- | --- | --- | --- |
| 76D-1 | 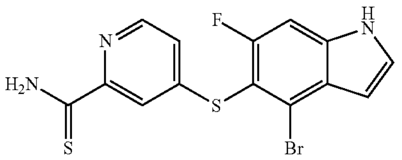 | 4-((4-bromo-6-fluoro-1H-indol-5-yl)thio)pyridine-2-carbothioamide | 382, 384 |

-continued

| Inter. No. | Structure | Name | MS m/z [M + H]$^+$ |
|---|---|---|---|
| 76D-2 | 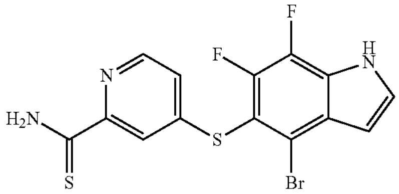 [SMILES: NC(=S)c1cc(Sc2c(F)c(F)c3[nH]ccc3c2Br)ccn1] | 4-((4-bromo-6,7-difluoro-1H-indol-5-yl)thio) pyridine-2-carbothioamide | 400, 402 [M + H]$^+$; RT: 1.93 minutes; (LC-MS Method 023) |
| 76D-3 | 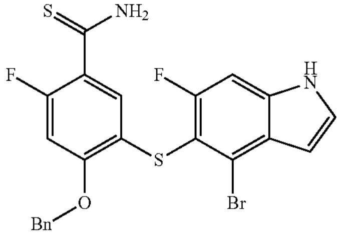 [SMILES: NC(=S)c1cc(Sc2c(F)cc3[nH]ccc3c2Br)c(OCc2ccccc2)cc1F] | 4-(benzyloxy)-5-((4-bromo-6-fluoro-1H-indol-5-yl)thio)-2-fluorobenzothioamide | 505, 507 [M + H]$^+$; RT: 2.30 minutes; (LC-MS Method 040) |

Intermediate 77: Ethyl 2-(5-(3-cyano-4-fluorophenoxy)-6-fluoro-1-tosyl-1H-indol-4-yl)acetate

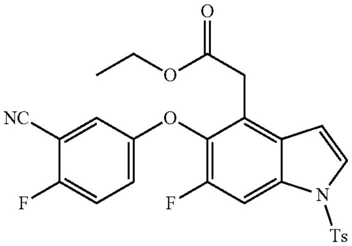 [SMILES: CCOC(=O)Cc1c(Oc2ccc(F)c(C#N)c2)c(F)cc2c1ccn2S(=O)(=O)c1ccc(C)cc1]

In a glove box, 5-((4-bromo-6-fluoro-1-tosyl-1H-indol-5-yl)oxy)-2-fluorobenzonitrile (Intermediate 3, 8 g, 16 mmol), ethyl 2-(tributylstannyl)acetate (intermediate 77A, 15.06 g, 40 mmol), zinc bromide (7.2 g, 32 mmol) and palladium (II) bis tri-O-tolylphosphine dichloride (1.26 g, 1.6 mmol) were dissolved in dry N,N-dimethylformamide (65 mL). The mixture was stirred at 100° C. overnight, quenched with water, and extracted with ethyl acetate (4×100 mL). The combined organic extracts were dried over sodium sulfate and concentrated. The crude product was purified by automated silica gel column chromatography (80 g silica gel column, 0-30% ethyl acetate in petroleum ether) to give the title compound as a yellow solid (4.6 g, 55%). MS (ESI): 511 m/z [M+H]$^+$.

Intermediate 77A: Ethyl 2-(tributylstannyl)acetate

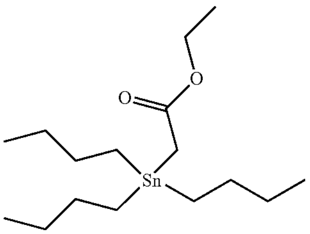 [SMILES: CCC[CH2][Sn]([CH2]CCC)([CH2]CCC)[CH2]C(=O)OCC]

To a stirred and cooled (−78° C.) solution of dicyclohexylamine (3.32 mL, 16.7 mmol) in tetrahydrofuran (83.5 mL) was added n-butyl lithium (6.7 mL, 16.7 mmol, 2.5M in tetrahydrofuran). The solution was stirred for 15 minutes, then ethyl acetate (1.64 mL, 16.7 mmol) was added. The mixture was stirred for another 30 minutes, treated with a solution of tri-n-butyltin chloride (5 g, 15.4 mmol) in tetrahydrofuran (33.4 mL), and stirred for an additional 1 hour at −78° C. The reaction mixture was then diluted with petroleum ether (1000 mL), washed with saturated citric acid (500 mL), water, brine, dried over sodium sulfate, and concentrated to give the crude title compound (6.26 g, 92%) as a light-yellow liquid. $^1$H NMR (400 MHz, $CDCl_3$) δ 4.05 (q, J=7.1 Hz, 2H), 1.92 (s, 2H), 1.60-1.45 (m, 6H), 1.31 (dd, J=14.8, 7.3 Hz, 7H), 1.23 (t, J=7.1 Hz, 3H), 1.04-0.93 (m, 5H), 0.90 (t, J=7.3 Hz, 9H) ppm.

Intermediate 78: Ethyl 2-(5-(3-carbamimidoyl-4-fluorophenoxy)-6-fluoro-1H-indol-4-yl)acetate

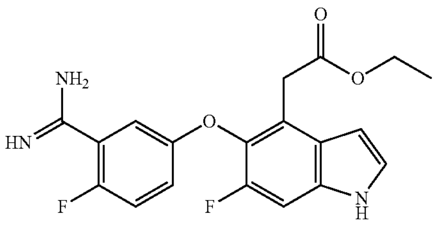 [SMILES: CCOC(=O)Cc1c(Oc2ccc(F)c(C(=N)N)c2)c(F)cc2[nH]ccc12]

To a stirred solution of ethyl 2-(5-(3-(N-acetoxycarbamimidoyl)-4-fluorophenoxy)-6-fluoro-1H-indol-4-yl)acetate (Intermediate 78C, 1.546 g, 3.59 mmol) in acetic acid (8 ml) was added 10% palladium on carbon (160 mg) and the mixture was stirred over night at room temperature under an atmosphere of hydrogen. The mixture was filtered through Celite and then concentrated. The residue was dissolved in ethyl acetate (50 mL) and washed with aqueous sodium bicarbonate solution (3×50 mL), dried over sodium sulfate, and concentrated to give a residue which was purified by silica gel column chromatography (10-20% methanol in dichloromethane) to give the title compound (0.87 g, 66%). MS (ESI): 374 m/z $[M+H]^+$.

Intermediate 78A: Ethyl 2-(5-(3-cyano-4-fluorophenoxy)-6-fluoro-1H-indol-4-yl)acetate

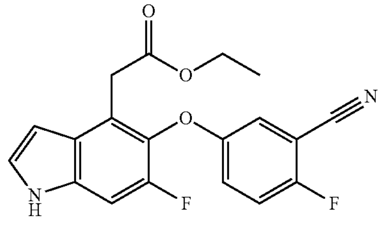 [SMILES: CCOC(=O)Cc1c(Oc2ccc(F)c(C#N)c2)c(F)cc2[nH]ccc12]

To a stirred solution of ethyl 2-(5-(3-cyano-4-fluorophenoxy)-6-fluoro-1-tosyl-1H-indol-4-yl)acetate (Intermediate 77, 2.7 g, 5.29 mmol) in tetrahydrofuran (27 ml) was slowly added a solution of tetrabutylammonium fluoride (1M) in tetrahydrofuran (32 ml, 32 mmol). During the addition, the color of the solution turned from yellow to green and then finally to brown. The brown mixture was stirred at 75° C. overnight under argon. Water was added and the mixture was extracted with ethyl acetate (3×60 ml). The combined organic phases were washed with water, dried over sodium sulfate, and concentrated. The residue was purified by silica gel column chromatography (0-25% ethyl acetate in petroleum ether) to give the title compound as a yellow solid (1.42 g, 76%). MS (ESI): 357 m/z $[M+H]^+$. $^1H$ NMR (400 MHz, $CDCl_3$) δ 8.34 (br s, 1H), 7.28 (dd, J=3.2, 2.4 Hz, 1H), 7.23-7.16 (m, 2H), 7.13-7.06 (m, 2H), 6.59-6.57 (m, 1H), 4.04 (q, J=7.2 Hz, 2H), 3.87 (s, 2H), 1.14 (t, J=7.2 Hz, 3H) ppm.

Intermediate 78B: Ethyl 2-(6-fluoro-5-(4-fluoro-3-(N-hydroxycarbamimidoyl)phenoxy)-1H-indol-4-yl)acetate

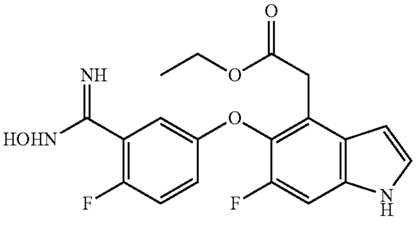

To a stirred solution of ethyl 2-(5-(3-cyano-4-fluorophenoxy)-6-fluoro-1H-indol-4-yl)acetate (Intermediate 78A, 1.42 g, 3.99 mmol) in methanol (15 ml) were added hydroxylamine hydrochloride (0.83 g, 11.97 mmol) and triethylamine (8.1 ml, 11.97 mmol). The yellow suspension was stirred at room temperature overnight under argon. The reaction mixture was concentrated and then partitioned between ethyl acetate (40 mL) and water (20 mL). The organic layer was dried with sodium sulfate and concentrated to give the title compound as a yellow solid (1.55 g, 100%). MS (ESI): 390 m/z $[M+H]^+$. $^1H$ NMR (400 MHz, $CDCl_3$) δ 8.46 (br s, 1H), 7.21 (dd, J=3.2, 2.4 Hz, 1H), 7.12 (dd, J=6.0, 3.2 Hz, 1H), 7.09 (d, J=10.4 Hz, 1H), 7.04-6.94 (m, 2H), 6.53-6.52 (m, 1H), 4.04 (q, J=7.2 Hz, 2H), 3.87 (s, 2H), 1.14 (t, J=7.2 Hz, 3H) ppm.

Intermediate 78C: Ethyl 2-(5-(3-(N-acetoxycarbamimidoyl)-4-fluorophenoxy)-6-fluoro-1H-indol-4-yl) acetate

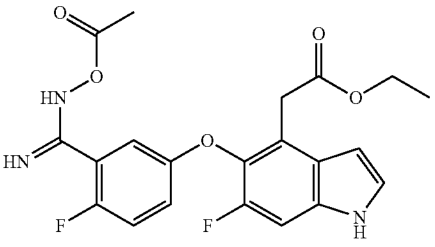 [SMILES: CCOC(=O)Cc1c(Oc2ccc(F)c(C(=N)NOC(C)=O)c2)c(F)cc2[nH]ccc12]

To a stirred solution of ethyl 2-(6-fluoro-5-(4-fluoro-3-(N-hydroxycarbamimidoyl)phenoxy)-1H-indol-4-yl)acetate (Intermediate 78B, 1.81 g, 4.64 mmol) in acetic acid (16 mL) was slowly added acetic anhydride (0.71 g, 6.96 mmol). The yellow-brownish solution was stirred at room temperature overnight under an atmosphere of argon. The mixture was concentrated. The residue was dissolved in ethyl acetate (30 ml), washed with saturated sodium bicarbonate solution (3×20 mL) and water (15 mL), dried over sodium sulfate, and concentrated to give the title compound as a solid (1.55 g, 90%). MS(ESI): 432 m/z $[M+H]^+$. $^1H$ NMR (400 MHz, $CDCl_3$) δ 8.29 (br s, 1H), 7.32-7.27 (m, 2H), 7.16 (d, J=9.6 Hz, 1H), 7.04-6.99 (m, 1H), 6.95-6.92 (m, 1H), 6.55-6.54 (m, 1H), 4.04 (q, J=7.2 Hz, 2H), 3.87 (s, 2H), 2.22 (s, 3H), 1.14 (t, J=7.2 Hz, 3H) ppm.

Intermediate 79: Methyl 4-((2-(((benzyloxy)carbonyl)(methyl)amino)ethyl)sulfonyl)-2-(3-iodophenyl)-2-methylbutanoate

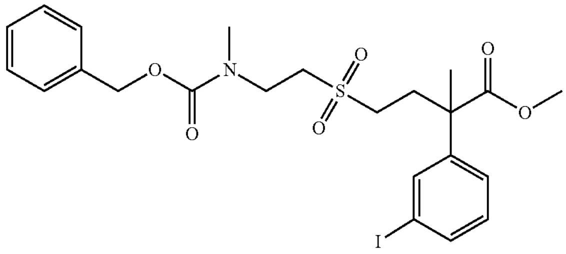 [SMILES: COC(=O)C(C)(CCS(=O)(=O)CCN(C)C(=O)OCc1ccccc1)c1cccc(I)c1]

To a stirred solution of methyl 4-((2-(((benzyloxy)carbonyl)(methyl)amino)ethyl)thio)-2-(3-iodophenyl)-2-methylbutanoate (Intermediate 79B, 4.1 g, 7.58 mmol) in dichloromethane (6 mL) was added 3-chlorobenzoperoxoic acid (3.27 g, 18.95 mmol). The mixture was stirred at room temperature for two hours, then diluted with ethyl acetate (50 ml). The solution was then washed with aqueous sodium bicarbonate (100 ml), water and brine. The separated organic layer was dried over sodium sulfate, filtered and concentrated to obtain the title compound (4.1 g, 94% yield) as a colorless oil. MS(ESI): 574 m/z $[M+H]^+$.

Intermediate 79A: S-(2-(((Benzyloxy)carbonyl)(methyl)amino)ethyl) ethanethioate

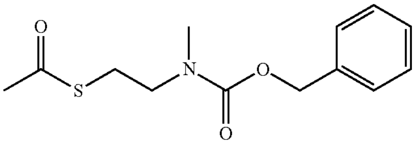 [SMILES: CC(=O)SCCN(C)C(=O)OCc1ccccc1]

To a stirred and cooled (0° C.) solution of 2-(((benzyloxy)carbonyl)(methyl)amino)ethyl methanesulfonate (27.7 g, 96.5 mmol) in N,N-dimethylformamide (200 ml) was added potassium thioacetate (22.05 g, 193 mmol) in water (100 mL). The mixture was stirred at room temperature overnight, then extracted with ethyl acetate (3×100 mL). The combined organic phases were washed with aqueous lithium chloride (3×50 ml), brine, dried over sodium sulfate, filtered, and concentrated to give the title compound (22.4 g, 87%) as a yellow oil. MS(ESI): 268 m/z $[M+H]^+$.

Intermediate 79B: Methyl 4-((2-(((benzyloxy)carbonyl)(methyl)amino)ethyl)thio)-2-(3-iodophenyl)-2-methylbutanoate

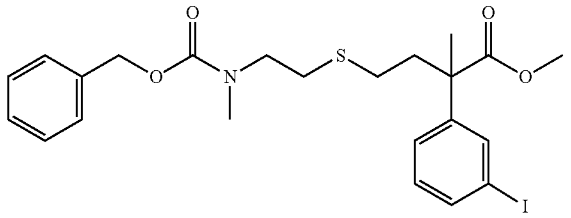 [SMILES: COC(=O)C(C)(CCSCCN(C)C(=O)OCc1ccccc1)c1cccc(I)c1]

A solution of methyl 4-bromo-2-(3-iodophenyl)-2-methylbutanoate (Intermediate 16-1, 4.1 g, 10.3 mmol) and S-(2-(((benzyloxy)carbonyl)(methyl)amino)ethyl) ethanethioate (Intermediate 79A, 4.1 g, 15.5 mmol) in dry methanol (30 ml) was flushed by argon for 10 minutes. Then sodium methoxide in methanol (5.5M, 2.87 ml, 15.5 mmol) was added dropwise at 0° C. The mixture was then stirred at room temperature overnight, quenched with saturated ammonium chloride, and concentrated to remove methanol. The aqueous residue was partitioned between ethyl acetate (200 ml) and water. The organic layer was washed with water and brine, dried over sodium sulfate, and concentrated. The residue was purified by silica gel column chromatography (ethyl acetate/petroleum ether=1/4) to obtain the title compound (3.9 g, 69.8% yield) as a colorless oil. MS(ESI): 542 m/z $[M+H]^+$.

Intermediate 80: Ethyl 3-(5-(3-carbamimidoyl-4-fluorophenoxy)-6-fluoro-1H-indol-4-yl)propanoate

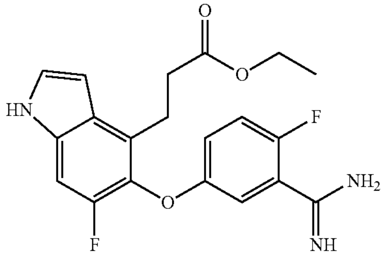 [SMILES: CCOC(=O)CCc1c(Oc2ccc(F)c(C(=N)N)c2)c(F)cc2[nH]ccc12]

To a stirred solution of ethyl (E)-3-(5-(3-carbamimidoyl-4-fluorophenoxy)-6-fluoro-1H-indol-4-yl)acrylate (Intermediate 80B, 1.39 g, 3.6 mmol) in tetrahydrofuran (25 mL) was added acetic acid (1 mL) and 10% palladium on carbon (0.3 g). The suspension was stirred under hydrogen atmosphere at room temperature for 16 hours. The mixture was filtered through a pad of Celite and rinsed with tetrahydrofuran (25 mL). The filtrate was concentrated. The residue was dissolved in ethyl acetate (150 mL), washed with saturated sodium bicarbonate, brine (30 mL), dried over sodium sulfate, and concentrated to give the title compound as a solid (1.3 g, 94%). MS (ESI): 388 m/z $[M+H]^+$.

Intermediate 80A: Ethyl (E)-3-(5-(3-Cyano-4-fluorophenoxy)-6-fluoro-1H-indol-4-yl)acrylate

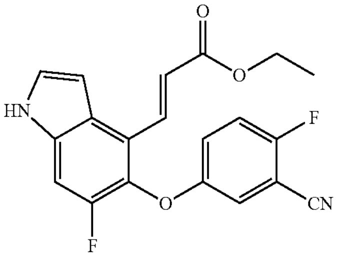 [SMILES: CCOC(=O)/C=C/c1c(Oc2ccc(F)c(C#N)c2)c(F)cc2[nH]ccc12]

To a stirred solution of 5-((4-bromo-6-fluoro-1H-indol-5-yl)oxy)-2-fluorobenzonitrile (Intermediate 6, 2.6 g, 7.47 mmol) in N,N-dimethylformamide (40 mL) was added, sequentially, ethyl acrylate (1.2 g, 14.94 mmol), tri(o-tolyl)phosphine (364 mg, 1.49 mmol), palladium(II) acetate (136 mg, 0.747 mmol) and triethylamine (4 mL, 37.35 mmol). The reaction was degassed by bubbling through nitrogen, then heated at 125° C. overnight. The mixture was diluted with ethyl acetate (200 mL), washed with water (3×50 mL), dried over sodium sulfate and concentrated. The residue was purified by automated flash chromatography (40 g silica gel column, 0-70% ethyl acetate in petroleum ether) to give the title compound (1.3 g, 47%) as a yellow solid. MS (ESI): 369 m/z $[M+H]^+$.

Intermediate 80B: Ethyl (E)-3-(5-(3-carbamimidoyl-4-fluorophenoxy)-6-fluoro-1H-indol-4-yl)acrylate

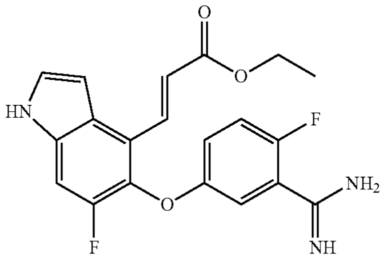 [SMILES: CCOC(=O)/C=C/c1c(Oc2ccc(F)c(C(=N)N)c2)c(F)cc2[nH]ccc12]

To a stirred and cooled (0° C.) solution of ethyl (E)-3-(5-(3-cyano-4-fluorophenoxy)-6-fluoro-1H-indol-4-yl)acrylate (Intermediate 80A, 2.02 g, 5.5 mmol) in tetrahydrofuran (55 mL) was added lithium bis(trimethylsilyl)amide (1M in tetrahydrofuran, 55 mL, 55 mmol). The reaction was stirred at room temperature overnight, then quenched with water (150 mL) and extracted with dichloromethane (2×150 mL). The combined organic layers were washed with brine (50 mL), dried over sodium sulfate, and concentrated to give the crude title compound as a solid (1.4 g, 66%). MS (ESI): 386 m/z $[M+H]^+$.

Intermediate 81: Methyl 2-(3-bromo-2-fluorophenyl)-4-(but-3-yn-1-ylsulfonyl)butanoate

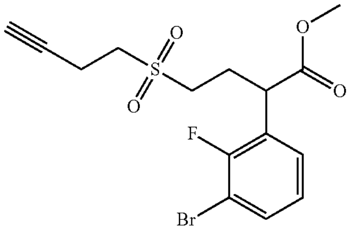 [SMILES: C#CCCS(=O)(=O)CCC(C(=O)OC)c1cccc(Br)c1F]

A mixture of 2-(3-bromo-2-fluoro-phenyl)-4-but-3-ynylsulfonyl-butanenitrile (Intermediate 81D, 2 g, 5.58 mmol), sulfuric acid (98%, 10 ml) and 50 mL of methanol was stirred at 80° C. for 48 hours. Methanol was removed by evaporation, and 15 mL of water was added. The mixture was extracted with ethyl acetate (3×100 mL). The combined organic phases were dried over sodium sulfate and concentrated. The residue was purified by automated flash chromatography (eluted with 0-40% ethyl acetate in petroleum ether) to give the title compound (1.62 g, 74%) as a colorless oil. MS (ESI): 391, 393 m/z $[M+H]^+$.

Intermediate 81A: 2-(3-Bromo-2-fluorophenyl)-4-hydroxybutanenitrile

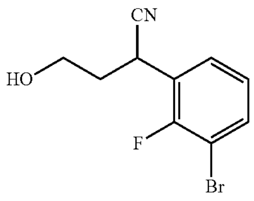 [SMILES: N#CC(CCO)c1cccc(Br)c1F]

A solution of 2-(3-bromo-2-fluoro-phenyl)-4-[tert-butyl(dimethyl)silyl]oxy-butanenitrile (Intermediate 16-2, 700 mg, 1.88 mmol) in 5 mL of hydrogen chloride in 1,4-dioxane (4N) was stirred at 0° C. for 30 minutes. The mixture was diluted with ethyl acetate (100 mL), washed with aqueous sodium bicarbonate, brine, dried over sodium sulfate, and concentrated. The residue was purified by automated flash chromatography (0-30% of ethyl acetate in petroleum ether) to give the title compound (319 mg, 66%) as a colorless oil. MS (ESI): 258, 260 m/z $[M+H]^+$.

Intermediate 81B: 3-(3-Bromo-2-fluorophenyl)-3-cyanopropyl methanesulfonate

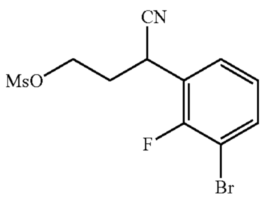 [SMILES: CS(=O)(=O)OCCC(C#N)c1cccc(Br)c1F]

To a stirred and cooled (0° C.) solution of 2-(3-bromo-2-fluorophenyl)-4-hydroxybutanenitrile (Intermediate 81A, 1.05 g, 4.07 mmol) in dichloromethane (30 mL) was added triethylamine (823 mg, 8.14 mmol) and methanesulfonyl chloride (699 mg, 6.1 mmol) dropwise. The mixture was stirred at 0° C. for 1 hour, then quenched with water (50 mL), and extracted with dichloromethane (3×20 mL). The combined organic extracts were dried over sodium sulfate and concentrated to give the title compound (1.36 g, 99%) as a colorless oil. MS (ESI): 358, 360 m/z $[M+Na]^+$.

Intermediate 81C: 2-(3-Bromo-2-fluorophenyl)-4-(but-3-yn-1-ylthio)butanenitrile

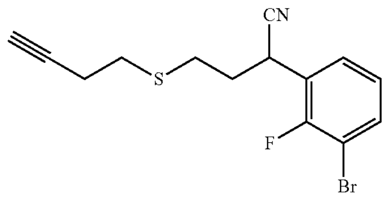 [SMILES: C#CCCSCCC(C#N)c1cccc(Br)c1F]

To a stirred solution of 3-(3-bromo-2-fluorophenyl)-3-cyanopropyl methanesulfonate (Intermediate 81B, 1.0 g, 0.3 mmol) and S-(but-3-yn-1-yl) ethanethioate (57.2 mg, 0.45 mmol) in 10 mL of methanol was bubbled with argon for 20 minutes, then treated with sodium methoxide (5.4 M in methanol, 0.1 mL, 0.54 mmol) dropwise. The mixture was stirred at room temperature for 16 hours, then quenched with saturated ammonium chloride and extracted with ethyl acetate (3×50 mL). The combined organic extracts were dried over sodium sulfate and concentrated. The residue was purified by automated flash silica gel column chromatography (0-30% of ethyl acetate in petroleum ether) to give the title compound (904 mg, 34.2%) as a yellow oil. MS (ESI): 326, 328 m/z $[M+H]^+$.

Intermediate 81D: 2-(3-Bromo-2-fluorophenyl)-4-(but-3-yn-1-ylsulfonyl)butanenitrile

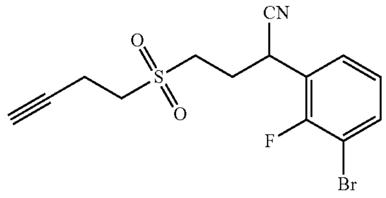 [SMILES: C#CCCS(=O)(=O)CCC(C#N)c1cccc(Br)c1F]

To a stirred and cooled (0° C.) solution of 2-(3-bromo-2-fluorophenyl)-4-(but-3-yn-1-ylthio)butanenitrile (Intermediate 81C, 5.48 g, 8.4 mmol) in dichloromethane (50 mL) was added meta-chloroperoxybenzoic acid (4.35 g, 25.2 mmol). The mixture was stirred at room temperature for 3 hours, then quenched with saturated sodium bisulfite (3 mL), and extracted with dichloromethane (3×30 mL). The combined organic extracts were dried over sodium sulfate and concentrated. The residue was purified by automated flash chromatography (0-50% ethyl acetate in petroleum ether) to give the title compound (3 g, 50%) as a yellow oil. MS (ESI): 358, 360 m/z $[M+H]^+$.

Intermediate 82: 5-((4-(Azidomethyl)-6-fluoro-1H-indol-5-yl)oxy)-2-fluorobenzonitrile

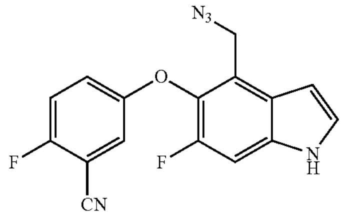 [SMILES: N#Cc1cc(Oc2c(F)cc3[nH]ccc3c2CN=[N+]=[N-])ccc1F]

To a stirred solution of 5-((4-(azidomethyl)-6-fluoro-1-(phenylsulfonyl)-1H-indol-5-yl)oxy)-2-fluorobenzonitrile (Intermediate 82A, 5.6 g, 2.614 mmol) in methanol (40 mL) was added potassium carbonate (3.22 g, 23.3 mmol). The reaction mixture was heated at 60° C. for 1 hour, then concentrated to remove the methanol. The residue was partitioned between ethyl acetate (50 mL) and water (50 mL). The organic layer and two additional ethyl acetate extracts (2×50 mL) were combined, dried over sodium sulfate, and concentrated. The residue was purified by automated silica gel chromatography (petroleum ether: ethyl acetate=10:0 to 1:1) to give the title compound (3.5 g, 96%). MS (ESI): 326 m/z [M+H]+.

Intermediate 82A: 5-((4-(azidomethyl)-6-fluoro-1-(phenylsulfonyl)-1H-indol-5-yl)oxy)-2-fluorobenzonitrile

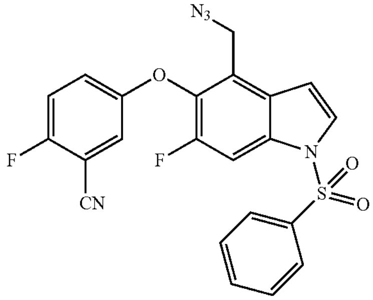 [SMILES: N#Cc1cc(Oc2c(F)cc3c(ccn3S(=O)(=O)c3ccccc3)c2CN=[N+]=[N-])ccc1F]

To a stirred solution of 5-((4-(bromomethyl)-6-fluoro-1-(phenylsulfonyl)-1H-indol-5-yl)oxy)-2-fluorobenzonitrile (Intermediate 13, 6.0 g, 11.628 mmol) in N,N-dimethylformamide (40 mL) was added sodium azide (732 mg, 23.256 mmol). The mixture was stirred at room temperature for 18 hours, quenched with water (40 mL), and extracted with ethyl acetate (40 mL×3). The organic layers were combined, dried over sodium sulfate, and concentrated to give the crude title compound (5.2 g), which was used for next step without further purification. MS (ESI): 466 m/z [M+H]+.

Intermediate 83: 7-((2-ethoxy-2-oxoethyl)sulfonyl)-2-(3-iodophenyl)-2,5-dimethylheptanoic acid

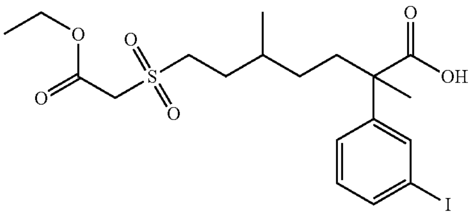 [SMILES: CCOC(=O)CS(=O)(=O)CCC(C)CCC(C)(C(=O)O)c1cccc(I)c1]

To a stirred solution of 7-((2-ethoxy-2-oxoethyl)thio)-2-(3-iodophenyl)-2,5-dimethylheptanoic acid (Intermediate 83B, 2.5 g, crude) in methanol (20 mL) was added ammonium molybdate tetrahydrate (1.5 g) and hydrogen peroxide (35% in water, 10 mL). The mixture was stirred at room temperature overnight, then quenched with water (40 mL), and extracted with ethyl acetate. The combined organic extracts were washed with saturated sodium thiosulfate, brine, dried over sodium sulfate and concentrated. The residue was purified by automated silica gel chromatography (petroleum ether/ethyl acetate=5/1-3/1) to give the title compound (1.72 g, 75% of 2 steps) as a yellow oil. MS (ESI): 511 m/z [M+H]+, retention time: 1.75 minutes. (LC-MS method 012)

Intermediate 83A: 2-(3-Iodophenyl)-2,5-dimethyl-7-(tosyloxy)heptanoic Acid

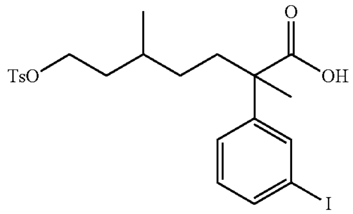 [SMILES: Cc1ccc(S(=O)(=O)OCCC(C)CCC(C)(C(=O)O)c2cccc(I)c2)cc1]

To a stirred solution of methyl 2-(3-iodophenyl)-2,5-dimethyl-7-(tosyloxy)heptanoate (Intermediate 16-3, 14.2 g, 26.1 mmol) in tetrahydrofuran/methanol (3/1, 100 mL) was added a solution of lithium hydroxide (2.51 g, 104 mmol) in water (10 mL). The mixture was stirred at 45° C. for 3 hours, then concentrated. The residue was partitioned between water (100 mL) and ethyl acetate (50 mL). The organic layer was combined with additional ethyl acetate extract (50 mL), washed with water, brine, dried over sodium sulfate and concentrated to recover the starting material, methyl 2-(3-iodophenyl)-2,5-dimethyl-7-(tosyloxy)heptanoate (Intermediate 16-3, 8 g) as a yellow oil. The aqueous phase was acidified with 1N hydrochloric acid to pH 5 and extracted with ethyl acetate (3×100 mL). The combined organic layers were washed with water, brine, dried over sodium sulfate and concentrated. The residue was purified by automated silica gel chromatography (petroleum ether/ethyl acetate=5/1-3/1) to give the title compound (3.9 g, 67%) as a yellow oil. MS (ESI): 531 m/z [M+H]+, retention time: 1.68 minutes. (LC-MS method 012)

Intermediate 83B: 7-((2-Ethoxy-2-oxoethyl)thio)-2-(3-iodophenyl)-2,5-dimethylheptanoic acid

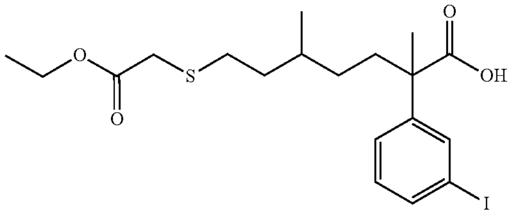 [SMILES: CCOC(=O)CSCCC(C)CCC(C)(C(=O)O)c1cccc(I)c1]

To a stirred solution of 2-(3-iodophenyl)-2,5-dimethyl-7-(tosyloxy)heptanoic acid (Intermediate 83A, 2.0 g, 3.77 mmol) and sodium ethoxide (0.77 g, 11.3 mmol) in ethanol (20 mL) was added ethyl 2-mercaptoacetate (0.54 g, 4.53 mmol). The mixture was stirred at 80° C. for 45 minutes under argon, then cooled to room temperature, and diluted with water. The aqueous phase was acidified with 1N hydrochloric acid to pH ~5 and extracted with ethyl acetate (3×50 mL). The combined organic extracts were washed with water, brine, dried over sodium sulfate and concentrated to give the crude title compound (2.5 g, crude), which was used for the next step without further purification. MS (ESI): 479 m/z [M+H]$^+$, retention time: 1.72 minutes. (LC-MS method 012)

Intermediate 84: 3-((6-Fluoro-4-vinyl-1H-indol-5-yl)oxy)benzoic Acid

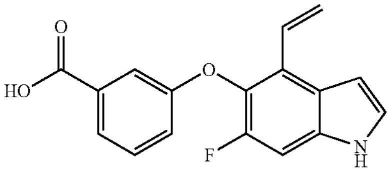 [SMILES: C=Cc1c(Oc2cccc(C(=O)O)c2)c(F)cc2[nH]ccc12]

To a solution of 3-((6-fluoro-4-vinyl-1H-indol-5-yl)oxy)benzonitrile (Intermediate 6-2, 6 g, 21.6 mmol) in ethanol (20 mL) was added aqueous potassium hydroxide (21.6 mL, 3 M in water). The mixture was refluxed for 18 hours, cooled to room temperature, and adjusted to pH~6 with 2N hydrochloric acid. The formed precipitate was collected by filtration to give the title compound (6 g, 94%) as a yellow solid. MS (ESI): 298 m/z [M+H]$^+$, retention time: 1.96 minutes. (LC-MS method 017)

The following intermediates were prepared based on the same procedures as described for Intermediate 84.

| Inter-mediate. No. | Structure | Name | MS m/z [M + H]$^+$ |
|---|---|---|---|
| 84-1 | 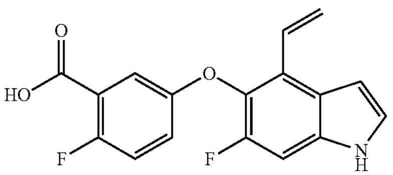 [SMILES: C=Cc1c(Oc2ccc(F)c(C(=O)O)c2)c(F)cc2[nH]ccc12] | 2-fluoro-5-((6-fluoro-4-vinyl-1H-indol-5-yl)oxy)benzoic acid | 316 |
| 84-2 | 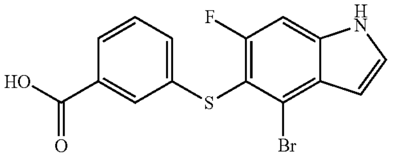 [SMILES: O=C(O)c1cccc(Sc2c(F)cc3[nH]ccc3c2Br)c1] | 3-((4-bromo-6-fluoro-1H-indol-5-yl)thio)benzoic acid | 366, 368 m/z [M + H]$^+$; RT: 1.19 min.; (LC-MS Method 27) |

Intermediate 85: 5-((4-bromo-6-fluoro-2,3-dihydro-1H-benzo[d]imidazol-5-yl)oxy)-2-fluorobenzonitrile

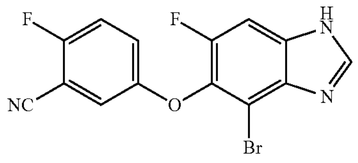 [SMILES: N#Cc1cc(Oc2c(F)cc3[nH]cnc3c2Br)ccc1F]

To a stirred solution of 5-(3-amino-2-bromo-6-fluoro-4-nitrophenoxy)-2-fluorobenzonitrile (Intermediate 85B, 15 g, 40.5 mmol) in iso-propyl alcohol (120 mL) was added iron (22.6 g, 405 mmol) followed by ammonium chloride (21.7 g, 405 mmol) and formic acid (60 mL). The mixture was stirred at 85° C. for 4 hours and concentrated. The residue partitioned between 100 mL of water and ethyl acetate (100 mL). The organic layer was combined with two additional ethyl acetate extracts (2×100 mL) and washed with brine, dried over sodium sulfate, and concentrated. The residue was crystallized from the mixture of ethyl acetate/petroleum ether (1/1) to give the title compound (11.3 g, 77% yield) as a yellow solid. MS (ESI): 350, 352 m/z [M+H]$^+$, retention time: 1.54 minutes. (LC-MS method 011)

Intermediate 85A: 2-bromo-3,4-difluoro-6-nitroaniline

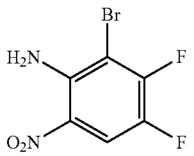 [SMILES: Nc1c([N+](=O)[O-])cc(F)c(F)c1Br]

To a stirred solution of 4,5-difluoro-2-nitro-aniline (17.4 g, 0.1 mol) in acetic acid (100 mL) was added bromine (32 g, 0.2 mol) dropwise. The mixture was stirred at 55° C. for 3 hours, then cooled to room temperature, diluted with water (500 mL), and filtered. The collected solid was dried to give the title compound (22 g, 87%) as a yellow solid. $^1$H NMR (500 MHz, DMSO-$d_6$) δ 8.26 (dd, J=11.0, 8.5 Hz, 1H), 7.42 (br, 2H) ppm.

Intermediate 85B: 5-(3-Amino-2-bromo-6-fluoro-4-nitrophenoxy)-2-fluorobenzonitrile

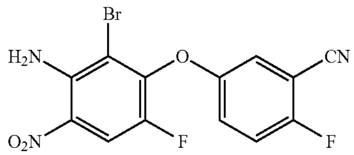 [SMILES: N#Cc1cc(Oc2c(F)cc([N+](=O)[O-])c(N)c2Br)ccc1F]

To a stirred solution of 2-bromo-3,4-difluoro-6-nitroaniline (Intermediate 85A, 25.3 g, 0.1 mol) in N,N-dimethylformamide (150 mL) was added 2-fluoro-5-hydroxy-benzonitrile (14.4 g, 0.105 mol) and potassium carbonate (27.6 g, 0.2 mol). The mixture was stirred at room temperature overnight, quenched with water (500 mL), and extracted with ethyl acetate (3×300 mL). The combined organic layers were washed with brine (3×100 mL), dried over sodium sulfate, and concentrated. The residue was crystallized with the mixture of ethyl acetate/petroleum ether (1/1) and the collected solid was dried to give the title compound (33.5 g, 88%) as a yellow solid. MS (ESI): 370, 372 m/z [M+H]$^+$, retention time: 1.77 minutes, purity: 97% (214 nm) (LC-MS method 011).

Intermediate 86: 5-((4-Bromo-6-fluoro-1-(tetrahydro-2H-pyran-2-yl)-1H-benzo[d]imidazol-5-yl)oxy)-2-fluorobenzonitrile

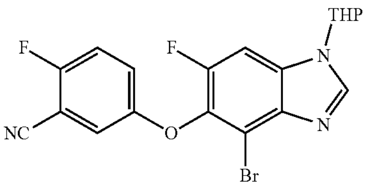

To a stirred solution of 5-((4-bromo-6-fluoro-2,3-dihydro-1H-benzo[d]imidazol-5-yl)oxy)-2-fluorobenzonitrile (Intermediate 85, 20 g, 55.2 mmol) in tetrahydrofuran (280 mL) was added 3,4-dihydro-2H-pyran (18.6 g, 221 mmol) followed by p-toluenesulfonic acid (476 mg, 2.76 mmol). The mixture was refluxed overnight, then concentrated. The residue was recrystallized in ethyl acetate/petroleum ether to give the title compound (21 g, yield 88%) as a light-yellow solid. MS (ESI): 434, 436 m/z [M+H]$^+$, retention time: 1.77 minutes, purity: >99% (214 nm) (LC-MS method 011).

Intermediate 87: 4-(Bromomethyl)-6-fluoro-5-(4-fluoro-3-(1-(tetrahydro-2H-pyran-2-yl)-1H-pyrazol-3-yl)phenoxy)-1-tosyl-1H-indole

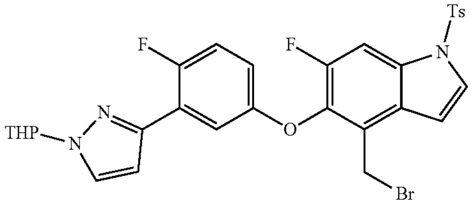

To a stirred solution of (6-fluoro-5-(4-fluoro-3-(1-(tetrahydro-2H-pyran-2-yl)-1H-pyrazol-3-yl)phenoxy)-1-tosyl-1H-indol-4-yl)methanol (Intermediate 87D, 400 mg, 0.69 mmol) in dichloromethane (8 mL) was added triphenylphosphine (1.5 eq., 266 mg) and N-bromosuccinimide (181 mg, 1.0 mmol). The reaction mixture was stirred at 0° C. for 1 hour, then quenched with saturated aqueous sodium sulfite solution (20 mL), diluted with water (20 mL), and extracted with dichloromethane (2×50 mL). The combined organic extracts were dried over sodium sulfate and concentrated. The residue was purified with automated flash column chromatography (12 g silica gel column, 20% to 50% of ethyl acetate in petroleum ether) to give the title compound (380 mg, 84%) as a colorless gum. MS (ESI): 642, 644 m/z [M+H]$^+$, retention time: 3.19 minutes, purity: >99% (214 nm) (LC-MS method 020).

Intermediate 87A: 4-Bromo-6-fluoro-5-(4-fluoro-3-(1-(tetrahydro-2H-pyran-2-yl)-1H-pyrazol-3-yl)phenoxy)-1-tosyl-1H-indole

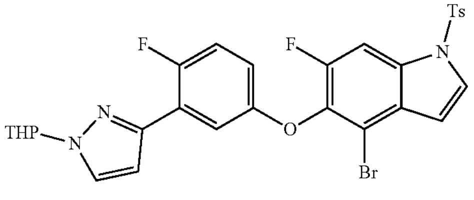

To a stirred solution of 4-bromo-6-fluoro-5-(4-fluoro-3-(1H-pyrazol-3-yl)phenoxy)-1-tosyl-1H-indole (Intermediate 21D, 4.0 g, 7.35 mmol) in dichloromethane (40 mL) was added p-toluenesulfonic acid (253 mg, 1.47 mmol) and 3,4-dihydro-2H-pyran (2.47 g, 29.4 mmol). The reaction was stirred at 40° C. for 3 hours, diluted with saturated sodium bicarbonate solution (50 mL) and extracted with dichloromethane (2×50 mL). The combined organic layers were dried over sodium sulfate and concentrated. The residue was purified by automated flash column chromatography [40 g silica gel column, petroleum ether/(ethyl acetate: dichloromethane=1:1)=1:0 to 10:1] to give the title compound (4.44 g, 96%) as a white solid. MS (ESI): 628, 630 m/z $[M+H]^+$, retention time: 3.25 minutes, purity: >99% (254 nm) (LC-MS method 020).

Intermediate 87B: 6-Fluoro-5-(4-fluoro-3-(1-(tetrahydro-2H-pyran-2-yl)-1H-pyrazol-3-yl)phenoxy)-1-tosyl-4-vinyl-1H-indole

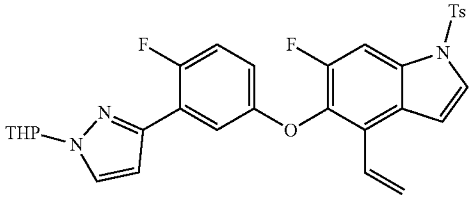

To a stirred solution of 4-bromo-6-fluoro-5-(4-fluoro-3-(1-(tetrahydro-2H-pyran-2-yl)-1H-pyrazol-3-yl)phenoxy)-1-tosyl-1H-indole (Intermediate 87A, 1.7 g, 2.7 mmol) in 1,4-dioxane (32 mL) and water (8 mL) was added 4,4,5,5-tetramethyl-2-vinyl-1,3,2-dioxaborolane (0.92 mL, 5.41 mmol), [1,1'-bis(diphenylphosphino)-ferrocene]dichloropalladium(II) (198 mg, 0.27 mmol) and cesium carbonate (1.76 g, 5.41 mmol). The mixture was stirred at 100° C. for 16 hours under nitrogen, cooled to the ambient temperature, diluted with water (50 mL), and extracted with ethyl acetate (2×100 mL). The combined organic layers were dried over sodium sulfate and concentrated. The residue was purified with automated flash chromatography [40 g silica gel column, petroleum ether/(ethyl acetate:dichloromethane=1:1)=1:0 to 20:1] to give the title product (1.4 g, 90%) as a white solid. MS (ESI): 576 m/z $[M+H]^+$.

Intermediate 87C: 6-Fluoro-5-(4-fluoro-3-(1-(tetrahydro-2H-pyran-2-yl)-1H-pyrazol-3-yl)phenoxy)-1-tosyl-1H-indole-4-carbaldehyde

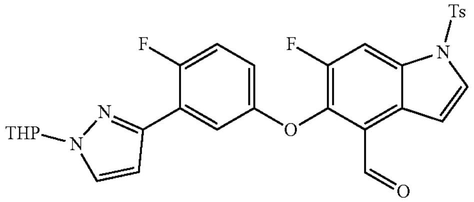

To a stirred and cooled (0° C.) solution of 6-fluoro-5-(4-fluoro-3-(1-(tetrahydro-2H-pyran-2-yl)-1H-pyrazol-3-yl)phenoxy)-1-tosyl-4-vinyl-1H-indole (Intermediate 87B, 1.65 g, 25.8 mmol) in acetone (22.5 mL) and water (7.5 mL) were added osmium tetroxide (32.8 mg, 0.13 mmol) and 4-methylmorpholine N-oxide (1.61 mL, 7.73 mmol). The mixture was stirred at room temperature overnight, quenched with saturated sodium sulfite (30 mL), and extracted with ethyl acetate (2×30 mL). The combined organic layers were dried over sodium sulfate and concentrated to give the crude product, 1-(6-fluoro-5-(4-fluoro-3-(1-(tetrahydro-2H-pyran-2-yl)-1H-pyrazol-3-yl)phenoxy)-1-tosyl-1H-indol-4-yl)ethane-1,2-diol (1.57 g, 2.32 mmol). This crude product was used for next step without further purification.

To a stirred solution of the above residue (1.57 g, 2.32 mmol) in acetone (30 mL) and water (10 mL) was added sodium periodate (1.66 g, 7.75 mmol). The reaction mixture was stirred at room temperature for 3 hours, quenched with sodium sulfite solution (50 mL), and extracted with ethyl acetate (3×50 mL). The combined organic layers were dried over anhydrous sodium sulfate and concentrated. The residue was purified with automated flash chromatography [40 g silica gel column, petroleum ether/(ethyl acetate:dichloromethane=1:1)=1:0 to 20:1] to give the title product (1.33 g, 99%) as a white solid. MS (ESI): 578 m/z $[M+H]^+$, retention time: 1.51 minutes, purity: 98% (254 nm) (LC-MS method 025). $^1H$ NMR (400 MHz, $CDCl_3$) δ 10.46 (s, 1H), 8.11 (d, J=10.2 Hz, 1H), 7.79 (d, J=8.4 Hz, 2H), 7.74 (d, J=3.6 Hz, 1H), 7.67 (dd, J=6.0, 3.2 Hz, 1H), 7.65 (d, J=2.4 Hz, 1H), 7.54 (d, J=3.6 Hz, 1H), 7.29 (d, J=8.4 Hz, 2H), 7.08-6.98 (m, 1H), 6.78-6.74 (m, 2H), 5.41 (dd, J=9.2, 3.2 Hz, 1H), 4.10-4.03 (m, 1H), 3.74-3.67 (m, 1H), 2.39 (s, 3H), 2.15-2.02 (m, 3H), 1.73-1.58 (m, 3H) ppm.

Intermediate 87D: (6-fluoro-5-(4-fluoro-3-(1-(tetrahydro-2H-pyran-2-yl)-1H-pyrazol-3-yl)phenoxy)-1-tosyl-1H-indol-4-yl)methanol

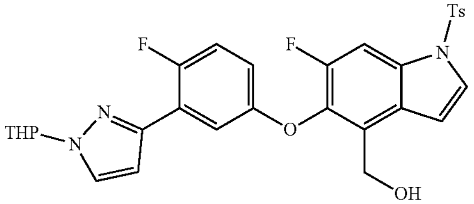

To a solution of 6-fluoro-5-(4-fluoro-3-(1-(tetrahydro-2H-pyran-2-yl)-1H-pyrazol-3-yl)phenoxy)-1-tosyl-1H-indole-4-carbaldehyde (Intermediate 87C, 1.33 g, 2.3 mmol) in ethanol (5 mL), tetrahydrofuran (5 mL) and dichloromethane (5 mL) was added sodium borohydride (175 mg, 4.6 mmol). The mixture was stirred at 25° C. for 1 hour, quenched with water (50 mL), and extracted with ethyl acetate (2×50 mL). The combined organic layers were dried over anhydrous sodium sulfate, filtered, and concentrated. The residue was purified by automated flash chromatography (25% to 50% of ethyl acetate in petroleum ether) to give the title compound (1.2 g, 90%) as a white solid. MS (ESI): 580 m/z $[M+H]^+$, retention time: 2.82 minutes, purity: 98% (254 nm) (LC-MS method 020).

Intermediate 88: 2-(2-Fluoro-5-((6-fluoro-4-vinyl-1H-indol-5-yl)oxy)phenyl)-1H-imidazole-4-carbaldehyde

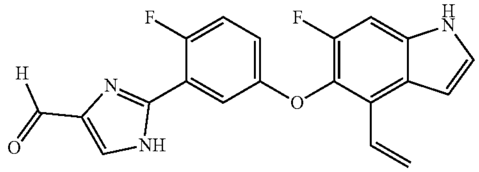 [SMILES: C=Cc1c(Oc2ccc(F)c(-c3nc(C=O)c[nH]3)c2)c(F)cc2[nH]ccc12]

To stirred solution of (2-(2-fluoro-5-((6-fluoro-4-vinyl-1H-indol-5-yl)oxy)phenyl)-1H-imidazol-4-yl)methanol (Intermediate 88B, 10 g, 27.2 mmol) in tetrahydrofuran (500 mL) was added manganese dioxide (23.7 g, 272 mmol). The mixture was stirred at 20° C. for 16 hours, filtered, and concentrated to give the title compound (9.5 g, 95.5%) as a yellow solid. MS (ESI): 366 m/z $[M+H]^+$.

Intermediate 88A: (2-(5-((4-Bromo-6-fluoro-1H-indol-5-yl)oxy)-2-fluorophenyl)-1H-imidazol-4-yl) methanol

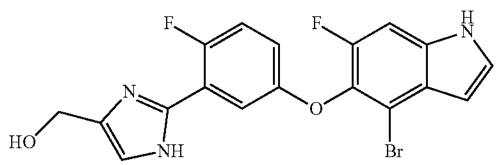 [SMILES: OCc1c[nH]c(-c2cc(Oc3c(F)cc4[nH]ccc4c3Br)ccc2F)n1]

To a stirred solution of 1,3-dihydroxypropan-2-one (11.6 g, 129 mmol) and 5-((4-bromo-6-fluoro-1H-indol-5-yl) oxy)-2-fluorobenzimidamide (Intermediate 10-6, 31.5 g, 86 mmol) in N-methyl-2-pyrrolidone (400 mL) was added ammonium chloride (23 g, 430 mmol) and ammonia (concentrated, 18 mol/L, 191 mL). The mixture was stirred at 80° C. for 2 hours, cooled to room temperature, diluted with water (500 mL), and extracted with ethyl acetate (3×500 mL). The combined organic layers were washed with 5% lithium chloride, brine, dried over magnesium sulfate, and concentrated to give the title compound (34 g, 94.1%) as a white solid, which was used for next step without further purification. MS (ESI): 420, 422 m/z $[M+H]^+$ Intermediate 88B: (2-(2-Fluoro-5-((6-fluoro-4-vinyl-1H-indol-5-yl)oxy)phenyl)-1H-imidazol-4-yl)methanol

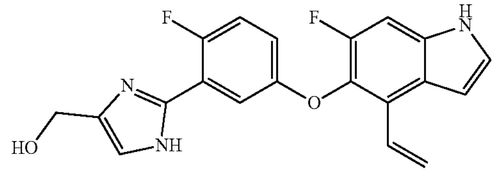 [SMILES: C=Cc1c(Oc2ccc(F)c(-c3nc(CO)c[nH]3)c2)c(F)cc2[nH]ccc12]

To a stirred solution of (2-(5-((4-bromo-6-fluoro-1H-indol-5-yl)oxy)-2-fluorophenyl)-1H-imidazol-4-yl)methanol (Intermediate 88A, 33 g, 78.5 mmol) in 1,4-dioxane (800 mL) and water (100 mL) were added 4,4,5,5-tetramethyl-2-vinyl-1,3,2-dioxaborolane (24.19 g, 157 mmol), cesium carbonate (51.3 g, 158 mmol) and 1,1'-bis(diphenylphosphino)ferrocene-palladium(II)-dichloride dichloromethane complex (5.13 g, 6.28 mmol). The reaction mixture was stirred at 100° C. for 16 hours under argon. After cooling to room temperature, the mixture was quenched with water (400 mL) and extracted with ethyl acetate (2×800 mL). The combined organic extracts were washed with brine, dried over magnesium sulfate, and concentrated. The residue was purified by automated silica gel column (hexane: ethyl acetate=5:1 to 1:1) to give the title compound (27 g, 93.6%) as a white solid. MS (ESI): 368 m/z $[M+H]^+$.

Intermediate 89: Ethyl 2-((2,2-dimethyl-5-oxopentyl)thio)acetate

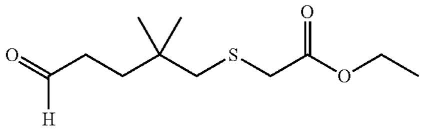

To a stirred and cooled (0° C.) solution of ethyl 2-(5-hydroxy-2,2-dimethyl-pentyl)sulfanylacetate (Intermediate 89C, 2 g, 8.53 mmol) in dichloromethane (60 mL) and dimethylsulfoxide (20 mL) was added triethylamine (2.59 g, 25.6 mmol) followed by sulfur trioxide pyridine complex (3.4 g, 21.3 mmol). The reaction mixture was stirred at room temperature for 2 hours, then quenched with saturated sodium bicarbonate (50 mL) and extracted with ethyl acetate (2×100 mL). The combined organic extracts were washed with brine, dried over magnesium sulfate, and concentrated to give the title compound (1.98 g, 99.9%) as a colorless oil, which was used in next step without further purification. $^1H$ NMR (400 MHz, $CDCl_3$) δ 9.79 (s, 1H), 4.19 (q, J=7.2 Hz, 2H), 3.20 (s, 2H), 2.45-2.39 (m, 2H), 1.67-1.61 (m, 4H), 1.36-1.21 (t, J=7.2 Hz, 3H), 0.97 (s, 6H).

Intermediate 89A: S-(5-(Benzyloxy)-2,2-dimethylpentyl) ethanethioate

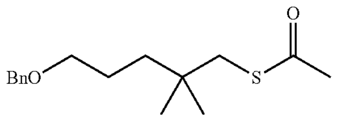 [SMILES: CC(=O)SCC(C)(C)CCCOCc1ccccc1]

To a stirred and cooled (0° C.) solution of 5-(benzyloxy)-2,2-dimethylpentan-1-ol (2 g, 9 mmol) and triethylamine (1.82 g, 18 mmol) in dichloromethane (60 mL) was added methanesulfonyl chloride (2.06 g, 18 mmol) dropwise. The reaction mixture was stirred at 20° C. for 3 hours, then quenched with cold water (20 mL), and extracted with dichloromethane (2×40 mL). The combined organic extracts were dried over magnesium sulfate and concentrated to give crude 5-(benzyloxy)-2,2-dimethylpentyl methanesulfonate (2.6 g, 98.7% yield) as a yellow oil, which was used for the next step without further purification.

To a stirred solution of The above 5-(benzyloxy)-2,2-dimethylpentyl methanesulfonate (2.6 g, 99%) in N,N-dimethylformamide (30 mL) was added potassium ethanethioate (5.13 g, 45 mmol). The reaction mixture was stirred at 90° C. for 16 hours, cooled to room temperature, diluted with water (40 mL), and extracted with ethyl acetate (3×200 mL). The combined organic extracts were washed with brine, dried over sodium sulfate, and concentrated to give the title compound (2.2 g, 87.2%, two steps) as a yellow oil. MS (ESI): 281 m/z $[M+H]^+$.

Intermediate 89B. Ethyl 2-((5-(benzyloxy)-2,2-dimethylpentyl)thio)acetate

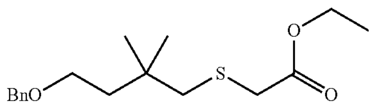 [SMILES: CCOC(=O)CSCC(C)(C)CCOCc1ccccc1]

To stirred and degassed solution of S-(5-benzyloxy-2,2-dimethyl-pentyl) ethanethioate (Intermediate 89A, 5 g, 17.8 mmol) in ethanol (100 mL) was added sodium ethoxide (1.82 g, 26.7 mol). The mixture was stirred at room temperature for 15 minutes, then treated with ethyl 2-bromoacetate (4.47 g, 26.7 mmol). After stirring at room temperature for 2 hours, the solvent was removed. The residue was dissolved in 200 mL of ethyl acetate. The solution was washed with water, brine, dried over sodium sulfate, and concentrated. The resulting residue was purified by flash column to give the title compound (5 g, 86.4%) as a yellow oil. MS (ESI): 325 m/z $[M+H]^+$.

Intermediate 89C. Ethyl 2-((5-hydroxy-2,2-dimethylpentyl)thio)acetate

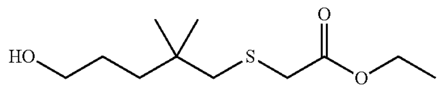

To a stirred and cooled (0° C.) solution of ethyl 2-((5-(benzyloxy)-2,2-dimethylpentyl)thio)acetate (Intermediate 89B, 4 g, 12.3 mmol) in dichloromethane (80 mL) was added trimethylsilyl iodide (4.93 g, 24.7 mmol). The reaction mixture was stirred at 0° C. for 2 hours, then quenched with saturated sodium bicarbonate (50 mL) and extracted with dichloromethane (2×100 mL). The combined organic extracts were washed with brine (100 mL), dried over magnesium sulfate, and concentrated to give ethyl 2-(5-hydroxy-2,2-dimethyl-pentyl)sulfanylacetate (2.34 g, 81% yield) as a colorless oil. $^1H$ NMR (400 MHz, $CDCl_3$) δ 4.35-4.09 (m, 2H), 3.76-3.52 (m, 2H), 3.20 (s, 2H), 2.62 (s, 2H), 1.62-1.47 (m, 2H), 1.44-1.32 (m, 3H), 1.29 (t, J=7.1 Hz, 3H), 0.98 (s, 6H).

Intermediate 90: 2-Fluoro-5-((6-fluoro-4-vinyl-1H-indol-5-yl)oxy)-N-methylbenzimidamide

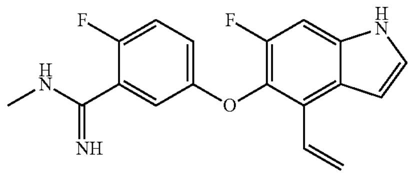 [SMILES: C=Cc1c(Oc2ccc(F)c(C(=N)NC)c2)c(F)cc2[nH]ccc12]

To a stirred and cooled (0° C.) solution of methylamine hydrochloride (30.1 g, 446 mmol) in toluene (200 mL) was added trimethylaluminum (2 M in hexane) (203 mL, 405 mmol) dropwise under argon. The mixture was stirred for 1 hour, then treated with 2-fluoro-5-((6-fluoro-4-vinyl-1H-indol-5-yl)oxy)benzonitrile (Intermediate 6-1, 6 g, 20.3 mmol) in toluene (100 mL). The mixture was stirred at 120° C. overnight, cooled to room temperature, quenched with water (1000 mL), and filtered through Celite to remove precipitate. The filtrate was extracted with ethyl acetate (2×600 mL). The combined organic extracts were washed with brine, dried over sodium sulfate, and concentrated. The residue was purified by automated silica gel column chromatography (80 g silica gel column, 0-10% methanol in dichloromethane (contain 0.5% concentrated ammonia) to give the title compound (4 g, 60%) as a solid. MS (ESI): 328 m/z $[M+H]^+$, retention time: 1.48 minutes, purity: 90% (214 nm) (LC-MS method 022).

Intermediate 91: Benzyl 3-(3-((2-ethoxy-2-oxoethyl)sulfonyl)-2,2-dimethylpropoxy)-2-(3-iodophenyl)-2-methylpropanoate

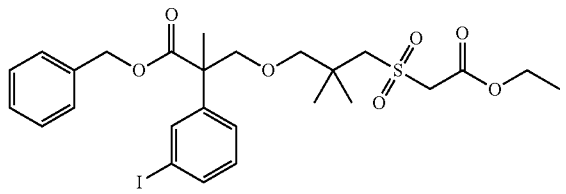 [SMILES: CCOC(=O)CS(=O)(=O)CC(C)(C)COCC(C)(C(=O)OCc1ccccc1)c1cccc(I)c1]

To a stirred and cooled (0° C.) solution of benzyl 3-(3-((2-ethoxy-2-oxoethyl)thio)-2,2-dimethylpropoxy)-2-(3-iodophenyl)-2-methylpropanoate (Intermediate 91E, 7.7 g, 13.2 mmol) in methanol (300 mL) was added ammonium molybdate tetrahydrate (15.4 g, 12.5 mmol) and hydrogen peroxide (30% in water, 77 mL). The mixture was stirred at 0° C. for 4 hours, quenched with water, and extracted with ethyl acetate (3×300 mL). The combined organic extracts were washed with sodium thiosulfate solution (100 mL), water, and brine. The solution was dried over sodium sulfate, filtered, and concentrated. The residue was purified by automated flash chromatography (12 g silica gel column, 0-100% ethyl acetate in petroleum ether) to give the title compound (7.8 g, 96% yield) as a colorless oil. MS (ESI): 639 m/z $[M+Na]^+$, retention time: 1.46 minutes, purity: 93% (214 nm) (LC-MS method 017).

Intermediate 91A: Methyl 3-(3-bromo-2,2-dimethylpropoxy)-2-(3-iodophenyl)-2-methylpropanoate

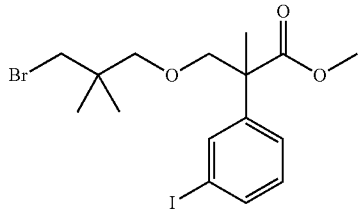 [SMILES: COC(=O)C(C)(COCC(C)(C)CBr)c1cccc(I)c1]

To a stirred and cooled (−78° C.) solution of methyl 2-(3-iodophenyl)propanoate (20.0 g, 68.9 mmol) in tetrahydrofuran (80 mL) was added lithium diisopropylamide (2M in tetrahydrofuran) (44.0 mL, 89.6 mmol) slowly under nitrogen. The mixture was stirred for 2 hours at −78° C., then treated with 1-bromo-3-(chloromethoxy)-2,2-dimethylpropane (22.3 g, 103 mol). The mixture was allowed to warm up to room temperature slowly and stirred overnight, quenched with saturated ammonium chloride, and extracted with ethyl acetate. The combined organic extracts were dried over sodium sulfate and concentrated. The residue was purified by automated silica gel column chromatography (petroleum ether/ethyl acetate=20:1) to give the title compound (28 g, 76%) as a yellow solid. MS (ESI): 469, 471 m/z $[M+H]^+$, retention time: 1.46 minutes, purity: 93% (214 nm) (LC-MS method 013).

Intermediate 91B: 3-(3-Bromo-2,2-dimethylpropoxy)-2-(3-iodophenyl)-2-methylpropanoic Acid

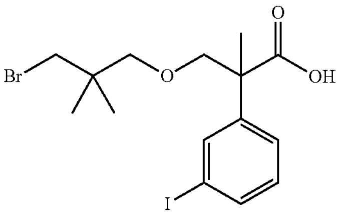 [SMILES: CC(C)(CBr)COCC(C)(C(=O)O)c1cccc(I)c1]

To a stirred and cooled (0° C.) solution of methyl 3-(3-bromo-2,2-dimethylpropoxy)-2-(3-iodophenyl)-2-methylpropanoate (Intermediate 91A, 15.9 g, 33.9 mmol) in tetrahydrofuran (40 mL), methanol (40 mL) and water (40 mL) was added lithium hydroxide (4.06 g, 169 mmol). The mixture was stirred at room temperature for 16 hours, then concentrated to remove tetrahydrofuran and methanol. The aqueous residue was acidified with 3N hydrochloric acid to adjust to the pH ~4, then extracted with ethyl acetate (3×200 mL). The combined organic extracts were dried over sodium sulfate and concentrated. The crude residue (15.8 g, a yellow oil) was used in the next step reaction without further purification. MS (ESI): 477, 479 m/z $[M+Na]^+$, retention time: 1.60 minutes, purity: 75% (214 nm) (LC-MS method 013).

Intermediate 91C: Benzyl 3-(3-bromo-2,2-dimethylpropoxy)-2-(3-iodophenyl)-2-methylpropanoate

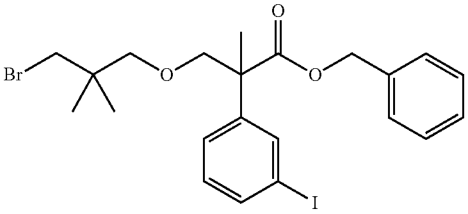 [SMILES: CC(C)(CBr)COCC(C)(C(=O)OCc1ccccc1)c1cccc(I)c1]

To a stirred solution of 3-(3-bromo-2,2-dimethylpropoxy)-2-(3-iodophenyl)-2-methylpropanoic acid (Intermediate 91B, 24 g, 52.7 mmol) in acetone (80 mL) was added potassium carbonate (10.9 g, 79.1 mmol) and benzyl bromide (10.8 g, 63.3 mmol). The mixture was stirred at 60° C. for 3 hours, then filtered, and concentrated. The residue was purified by automated silica gel column chromatography (petroleum ether/ethyl acetate=20:1) to give the title compound (25.7 g, 84%) as a yellow solid. MS (ESI): 545, 547 m/z $[M+H]^+$, retention time: 1.53 minutes, purity: 91% (214 nm) (LC-MS method 013).

Intermediate 91D: Benzyl 3-(3-(acetylthio)-2,2-dimethylpropoxy)-2-(3-iodophenyl)-2-methylpropanoate

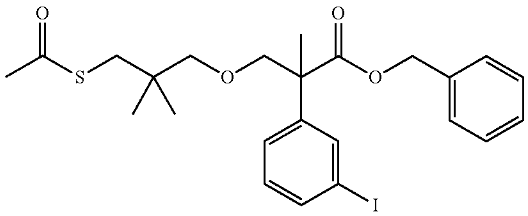 [SMILES: CC(=O)SCC(C)(C)COCC(C)(C(=O)OCc1ccccc1)c1cccc(I)c1]

To a stirred solution of benzyl 3-(3-bromo-2,2-dimethylpropoxy)-2-(3-iodophenyl)-2-methylpropanoate (Intermediate 91C, 15.0 g, 27.5 mmol) in N,N-dimethylformamide (45 mL) was added potassium thioacetate (9.43 g, 82.5 mmol). The mixture was stirred at 70° C. for 3 hours, then cooled, quenched with water (50 mL), and extracted with ethyl acetate (3×150 mL). The combined organic extracts were washed with brine, dried over sodium sulfate, and concentrated. The residue was purified by automated silica gel column chromatography (petroleum ether/ethyl acetate=20:1) to give the title compound (8.1 g, 48%) as a yellow oil. MS (ESI): 563 m/z $[M+Na]^+$, retention time: 2.53 minutes, purity: 98% (214 nm) (LC-MS method 013).

Intermediate 91E: Benzyl 3-(3-((2-ethoxy-2-oxoethyl)thio)-2,2-dimethylpropoxy)-2-(3-iodophenyl)-2-methylpropanoate

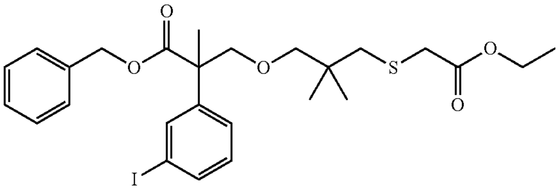 [SMILES: CCOC(=O)CSCC(C)(C)COCC(C)(C(=O)OCc1ccccc1)c1cccc(I)c1]

To a stirred solution of benzyl 3-(3-(acetylthio)-2,2-dimethylpropoxy)-2-(3-iodophenyl)-2-methylpropanoate (Intermediate 91D, 8 g, 14.8 mmol) in ethanol (30 mL) was added sodium ethoxide (1.51 g, 22.2 mmol) and ethyl bromoacetate (3.21 g, 19.2 mmol) under nitrogen. The mixture was stirred for 2 hours, quenched with water (30 mL), and extracted with ethyl acetate (3×150 mL). The combined organic extracts were washed with brine, dried over sodium sulfate, and concentrated. The residue was purified by automated silica gel column chromatography (petroleum ether/ethyl acetate=20:1) to give the title compound (7.7 g, 78.3%) as a yellow solid. MS (ESI): 607 m/z $[M+Na]^+$, retention time: 1.61 minutes, purity: 94% (214 nm) (LC-MS method 013).

The following intermediate was prepared based on the procedures described for Intermediate 91E.

| Inter. No. | Structure | Name | MS m/z [M + H]$^+$ |
|---|---|---|---|
| 91E-1 | 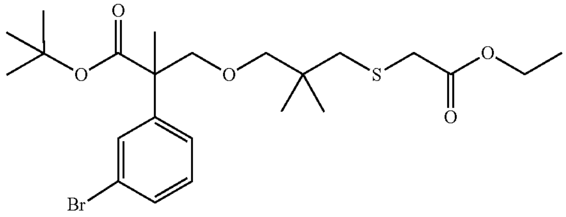 [SMILES: CCOC(=O)CSCC(C)(C)COCC(C)(C(=O)OC(C)(C)C)c1cccc(Br)c1] | tert-butyl 2-(3-bromo-phenyl)-3-(3-((2-ethoxy-2-oxoethyl)thio)-2,2-dimethylpropoxy)-2-methylpropanoate | 503, 505 |

Intermediate 92: Ethyl 2-((3-(2-(3-(2-ethoxy-2-oxoethyl)phenyl)-2-methyl-3-(2-methylhydrazineyl)-3-oxopropoxy)-2,2-dimethylpropyl)sulfonyl)acetate

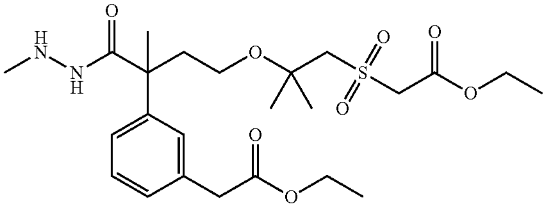 [SMILES: CCOC(=O)Cc1cccc(C(C)(CCOC(C)(C)CS(=O)(=O)CC(=O)OCC)C(=O)NNC)c1]

To a solution of tert-butyl 2-(2-(3-(cyanomethyl)phenyl)-3-(3-((2-ethoxy-2-oxoethyl)sulfonyl)-2,2-dimethylpropoxy)-2-methylpropanoyl)-1-methylhydrazine-1-carboxylate (Intermediate 92C, 2 g, 3.52 mmol) in ethanol (20 mL) was added chloro(trimethyl)silane (11.5 g, 0.11 mol). The mixture was heated at 60° C. overnight and concentrated. The residue was partitioned between saturated sodium bicarbonate (20 mL) and ethyl acetate (50 mL). The organic layer was combined with two additional ethyl acetate extracts (2×50 mL), dried over sodium sulfate and concentrated to give the crude title compound (1.6 g, 88.2%) as a yellow oil. The crude compound was used for the next step without further purification. MS (ESI): 515 m/z [M+H]$^+$, retention time: 1.20 minutes, purity: 99% (214 nm) (LC-MS method 013).

Intermediate 92A: Benzyl 2-(3-(cyanomethyl)phenyl)-3-(3-((2-ethoxy-2-oxoethyl)sulfonyl)-2,2-dimethylpropoxy)-2-methylpropanoate

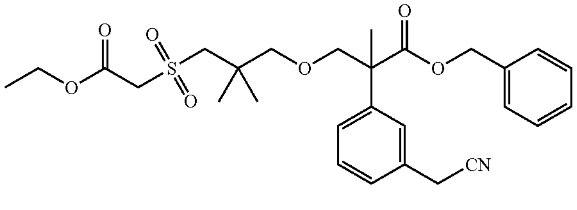 [SMILES: CCOC(=O)CS(=O)(=O)CC(C)(C)COCC(C)(C(=O)OCc1ccccc1)c1cccc(CC#N)c1]

To a degassed (nitrogen) solution of benzyl 3-(3-((2-ethoxy-2-oxoethyl)sulfonyl)-2,2-dimethylpropoxy)-2-(3-iodophenyl)-2-methylpropanoate (Intermediate 91, 6.2 g, 10.1 mmol) in dimethyl sulfoxide (60 mL) and water (20 mL) were added 4-(4,4,5,5-tetramethyl-1,3,2-dioxaborolan-2-yl)isoxazole (3.0 g, 15.2 mmol), potassium fluoride (1.75 g, 30.2 mmol), and [1,1'-bis(diphenylphosphino)ferrocene]dichloropalladium(II) (0.74 g, 1.01 mmol). The mixture was stirred at 80° C. for 2 hours, then 130° C. for 3 hours under nitrogen. After cooling to room temperature, the solution was partitioned between water (100 mL) and ethyl acetate (150 mL). The organic layer, combined with two additional ethyl acetate extracts (2×100 mL), was dried over sodium sulfate, and concentrated. The residue was purified with automated flash chromatography (petroleum ether:ethyl acetate=3:1 to 2:1) to give the title compound (3.0 g, 50%) as a yellow oil. MS (ESI): 530 m/z [M+H]$^+$, retention time: 2.13 minutes, purity: 89% (214 nm) (LC-MS method 013).

Intermediate 92B: 2-(3-(Cyanomethyl)phenyl)-3-(3-((2-ethoxy-2-oxoethyl)sulfonyl)-2,2-dimethylpropoxy)-2-methylpropanoic Acid

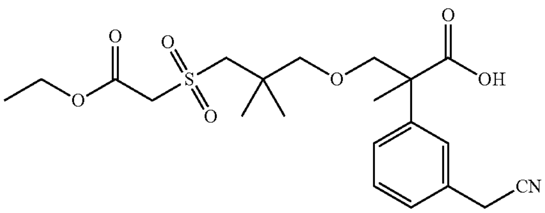 [SMILES: CCOC(=O)CS(=O)(=O)CC(C)(C)COCC(C)(C(=O)O)c1cccc(CC#N)c1]

To a stirred solution of benzyl 2-(3-(cyanomethyl)phenyl)-3-(3-((2-ethoxy-2-oxoethyl)sulfonyl)-2,2-dimethylpropoxy)-2-methylpropanoate (Intermediate 92A, 3.4 g, 6.42 mmol) in ethyl acetate (50 mL) was added palladium on carbon (10%, 1.9 g). The mixture was stirred at 40° C. for 5 hours under hydrogen balloon, then filtered through a pad of Celite. The filtrate was concentrated to give the crude title compound (2.8 g, 99%) as a colorless oil. The crude was used for the next step without further purification. MS (ESI): 462 m/z [M+Na]$^+$, retention time: 1.25 minutes, purity: 80% (214 nm) (LC-MS method 014).

The following intermediate was prepared based on the procedures described for Intermediate 92B.

| Inter. No. | Structure | Name | MS m/z [M + H]$^+$ |
|---|---|---|---|
| 92B-1 | 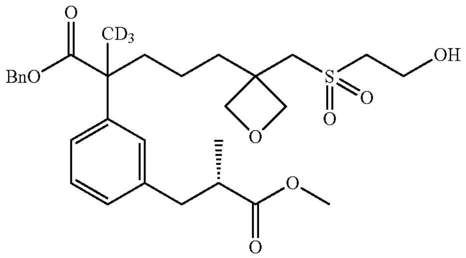 [SMILES: [2H]C([2H])([2H])C(CCCC1(CS(=O)(=O)CCO)COC1)(C(=O)OCc1ccccc1)c1cccc(C[C@H](C)C(=O)OC)c1] | benzyl 5-(3-(((2-hydroxyethyl)sulfonyl)methyl)oxetan-3-yl)-2-(3-((S)-3-methoxy-2-methyl-3-oxopropyl)phenyl)-2-(methyl-d3)pentanoate | 564 |

Intermediate 92C: Tert-Butyl 2-(2-(3-(cyanomethyl)phenyl)-3-(3-((2-ethoxy-2-oxoethyl)sulfonyl)-2,2-dimethylpropoxy)-2-methylpropanoyl)-1-methylhydrazine-1-carboxylate

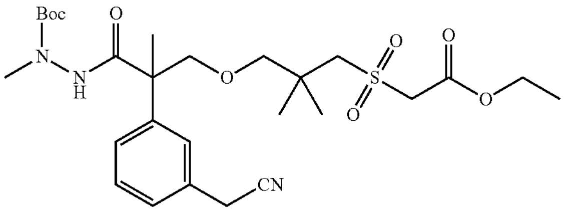 [SMILES: CCOC(=O)CS(=O)(=O)CC(C)(C)COCC(C)(C(=O)NN(C)C(=O)OC(C)(C)C)c1cccc(CC#N)c1]

To a stirred solution of 2-(3-(cyanomethyl)phenyl)-3-(3-((2-ethoxy-2-oxoethyl)sulfonyl)-2,2-dimethylpropoxy)-2-methylpropanoic acid (Intermediate 92B, 2.8 g, 6.37 mmol) in acetonitrile (30 mL) was added tert-butyl N-amino-N-methyl-carbamate (0.93 g, 6.37 mmol), 1-methylimidazole (1.83 g, 22.3 mmol), and chloro-N, N, N', N'-tetramethyl-formamidinium hexafluorophosphate (1.8 g, 6.37 mmol). The mixture was stirred at room temperature overnight, then diluted with 50 mL of ethyl acetate, and washed with saturated ammonium chloride (20 mL). The organic phase was dried over sodium sulfate and concentrated. The residue was purified by automated silica gel column chromatography (petroleum ether: ethyl acetate=3:1 to 2:1) to give the crude title compound (2 g, crude) as a yellow oil. This crude product was used in the step without further purification. MS (ESI): 590 m/z [M+Na]$^+$, retention time: 2.01 minutes, purity: 95% (214 nm) (LC-MS method 013).

Intermediate 93: 5-(3-(4-Chloro-1-(tetrahydro-2H-pyran-2-yl)-1H-pyrazol-3-yl)-4-fluorophenoxy)-6-fluoro-4-vinyl-1H-indole

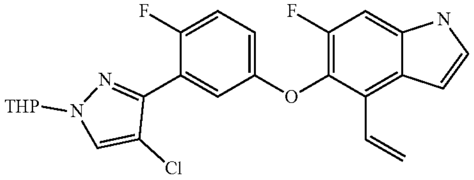

To a stirred solution of 5-(3-bromo-4-fluorophenoxy)-6-fluoro-4-vinyl-1H-indole (Intermediate 20D, 8.0 g, 22.8 mol) in tetrahydrofuran/water (100 mL/25 mL) was added 4-chloro-1-tetrahydropyran-2-yl-3-(4,4,5,5-tetramethyl-1,3,2-dioxaborolan-2-yl)pyrazole (10.7 g, 34.3 mmol), cesium carbonate (14.9 g, 45.7 mol) and [1,1'-bis(di-tert-butylphosphino)ferrocene]dichloropalladium(II) (1.49 g, 2.28 mmol). The mixture was heated at 50° C. for 12 hours under nitrogen, then partitioned between water (200 mL) and ethyl acetate (200 mL). The organic layer, combined with two additional ethyl acetate extracts (2×100 mL), was dried over sodium sulfate and concentrated. The residue was purified with automated flash chromatography (80 g silica gel column, eluted with 0-60% ethyl acetate in petroleum ether) to give the title compound (5.2 g, 50%) as a yellow oil. MS (ESI): 372 m/z [M−THP]$^+$, retention time: 2.20 minutes, purity: 93% (214 nm) (LC-MS method 017).

Intermediate 94: 3-(3-(3-Bromophenyl)-3-((tetrahydro-2H-pyran-2-yl)oxy)propoxy)-2,2-dimethylpropan-1-ol

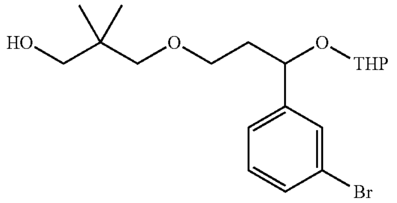

To a stirred solution of methyl 3-(3-(3-bromophenyl)-3-((tetrahydro-2H-pyran-2-yl)oxy)propoxy)-2,2-dimethylpropanoate (Intermediate 94B, 4.80 g, 0.0112 mol) in tetrahydrofuran (50 mL) was added lithium aluminum hydride (424 mg, 0.0112 mol) at −78° C. The mixture was stirred at this temperature for 1 hour. Then 5 mL of water was carefully added, followed by 5 mL of 15% sodium hydroxide, and 20 mL of water. The mixture was warmed to room temperature and filtered. The filtrate cake was washed with ethyl acetate (100 mL). The filtrate was dried over sodium sulfate and concentrated to give the crude title compound (4.10 g, 91%) as a colorless liquid. MS (ESI): 423, 425 m/z [M+Na]$^+$, retention time: 2.29 minutes, purity: 94% (214 nm) (LC-MS method 011).

Intermediate 94A: Methyl 3-(3-(3-bromophenyl)-3-hydroxypropoxy)-2,2-dimethylpropanoate

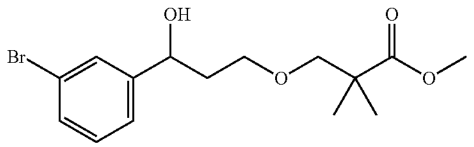 [SMILES: COC(=O)C(C)(C)COCCC(O)c1cccc(Br)c1]

To a stirred and cooled (−78° C.) solution of 1-bromo-3-iodo-benzene (7.21 g, 0.026 mol) in tetrahydrofuran (60 mL) was added isopropyl magnesium chloride-lithium chloride (19.6 mL, 0.026 mol) under nitrogen. The reaction was stirred for 1 hour, then treated with methyl 2,2-dimethyl-3-(3-oxopropoxy)propanoate (4.8 g, 0.026 mol) and stirred for an additional 2 hours. The mixture was quenched with water (100 mL) and extracted with ethyl acetate (3×100 mL). The combined organic extracts were washed with brine, dried over sodium sulfate, and concentrated. The residue was purified by silica gel column chromatography (petroleum ether: ethyl acetate=6:1) to give the title compound (4.8 g, 55%) as a colorless liquid. MS (ESI): 327, 329 m/z [M+H−OH]$^+$, retention time: 2.07 minutes, purity: 94% (254 nm) (LC-MS method 011).

Intermediate 94B: Methyl 3-(3-(3-bromophenyl)-3-((tetrahydro-2H-pyran-2-yl)oxy)propoxy)-2,2-dimethylpropanoate

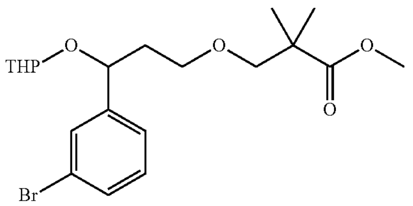

To a stirred solution of methyl 3-(3-(3-bromophenyl)-3-hydroxypropoxy)-2,2-dimethylpropanoate (Intermediate 94A, 6.80 g, 0.0197 mol) in dichloromethane (50 mL) was added 2,3-dihydro-4H-pyran (2.25 mL, 0.0246 mol) and p-toluenesulfonic acid (136 mg, 0.788 mmol). The reaction was stirred at room temperature for 2 hours, then quenched with water (80 mL), and extracted with dichloromethane (3×50 mL). The combined organic extracts were washed with brine, dried over sodium sulfate, and concentrated. The residue was purified by silica gel column chromatography (petroleum ether: ethyl acetate=5:1) to give the title compound (4.80 g, 57%) as a colorless liquid. MS (ESI): 451, 453 m/z [M+Na]$^+$, retention time: 2.39 minutes, purity: 95% (214 nm) (LC-MS method 011).

Intermediate 95: 3-(2-Fluoro-5-((6-fluoro-4-vinyl-1H-indol-5-yl)oxy)phenyl)-1-(tetrahydro-2H-pyran-2-yl)-1H-pyrazole-4-carbonitrile

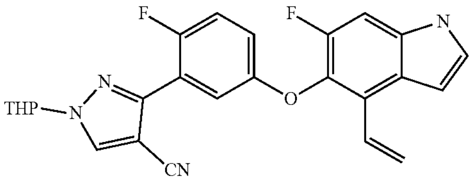

To a solution of 6-fluoro-5-[4-fluoro-3-(4,4,5,5-tetramethyl-1,3,2-dioxaborolan-2-yl)phenoxy]-4-vinyl-1H-indole (Intermediate 20, 5.8 g, 14.6 mmol) in 1,4-dioxane (60 mL) and water (15 mL) was added 4,4,5,5-tetramethyl-3-iodo-1-tetrahydropyran-2-yl-pyrazole-4-carbonitrile (5.75 g, 19.0 mol), cesium carbonate (9.51 g, 29.2 mmol) and dichloro[1,1'-bis(diphenylphosphino)-ferrocene]palladium(II) (1.46 g, 1.19 mmol). The reaction mixture was purged with argon and stirred at 100° C. for 16 hours. After cooling to room temperature, the mixture was diluted with ethyl acetate (150 mL), washed with water, dried over sodium sulfate, and concentrated. The residue was purified by automated flash chromatography (80 g silica gel column, eluted with 0-50% ethyl acetate in petroleum ether) to give the title compound (4.2 g, 64%) as a yellow solid. MS (ESI): 447 m/z [M+H]$^+$, retention time: 2.15 minutes, purity: 83% (214 nm) (LC-MS method 013).

Intermediate 96: 2-(2-Fluoro-5-((6-fluoro-1-tosyl-4-vinyl-1H-indol-5-yl)oxy)phenyl)-1H-imidazole-5-carbaldehyde

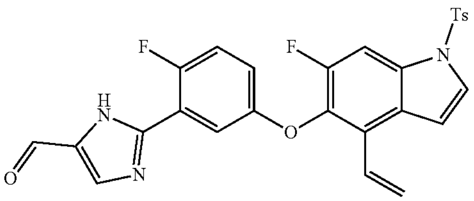 [SMILES: C=Cc1c(Oc2ccc(F)c(-c3ncc(C=O)[nH]3)c2)c(F)cc2c1ccn2S(=O)(=O)c1ccc(C)cc1]

To a stirred and cooled (0° C.) solution of 2-(2-fluoro-5-((6-fluoro-4-vinyl-1H-indol-5-yl)oxy)phenyl)-1H-imidazole-5-carbaldehyde (Intermediate 96B, 4.2 g, 0.0115 mol) in N,N-dimethylformamide (84 mL) was added sodium hydride (1.15 g, 0.0288 mmol, 60%) in one portion under nitrogen. The mixture was stirred at this temperature for 30 minutes, and treated with tosyl chloride (5.5 g, 0.029 mmol) portion-wise. The reaction mixture was stirred at room temperature for 16 hours, then quenched with saturated ammonium chloride (150 mL) and extracted with ethyl acetate (3×100 mL). The combined organic layers were washed with brine, dried over sodium sulfate, and concentrated. The residue was purified by column chromatography on silica gel (petroleum ether/ethyl acetate=1/1) to give the title product (4.4 g, 74%) as a pale-yellow solid. MS (ESI): 520 m/z [M+H]$^+$, retention time: 1.54 minutes, purity: 93% (214 nm) (LC-MS method 011).

Intermediate 96A: (2-(2-Fluoro-5-((6-fluoro-4-vinyl-1H-indol-5-yl)oxy)phenyl)-1H-imidazol-5-yl)methanol

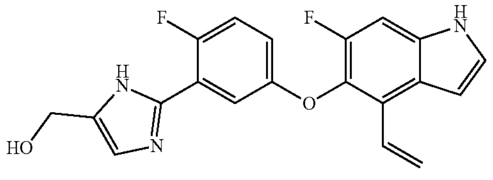 [SMILES: C=Cc1c(Oc2ccc(F)c(-c3ncc(CO)[nH]3)c2)c(F)cc2[nH]ccc12]

To a stirred solution of 2-fluoro-5-((6-fluoro-4-vinyl-1H-indol-5-yl)oxy)benzimidamide (Intermediate 10-3, 5.5 g, 0.0176 mol) in N-methyl pyrrolidinone (55 mL) were added ammonium chloride (3.73 g, 0.070 mol), concentrated ammonia (55 mL) and 1, 3-dihydroxypropan-2-one (2.37 g, 0.026 mol). The reaction mixture was stirred at 80° C. for 16 hours, then cooled to room temperature and partitioned between water (100 mL) and ethyl acetate (100 mL). The separated organic layer, combined with two additional ethyl acetate extracts (2×50 mL), was washed with brine, dried over sodium sulfate, and concentrated. The residue was purified with column chromatography on silica gel (petroleum ether/ethyl acetate: 1/2) to get the title compound (5.8 g, 90%) as a brown solid. MS (ESI): 368 m/z $[M+H]^+$, retention time: 1.01 minutes, purity: 92% (214 nm) (LC-MS method 011).

Intermediate 96B: 2-(2-Fluoro-5-((6-fluoro-4-vinyl-1H-indol-5-yl)oxy)phenyl)-1H-imidazole-5-carbaldehyde

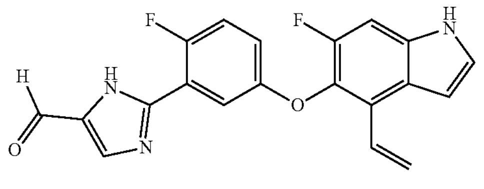 [SMILES: C=Cc1c(Oc2ccc(F)c(-c3ncc(C=O)[nH]3)c2)c(F)cc2[nH]ccc12]

To a stirred solution of (2-(2-fluoro-5-((6-fluoro-4-vinyl-1H-indol-5-yl)oxy)phenyl)-1H-imidazol-5-yl)methanol (Intermediate 96A, 4.4 g, 0.012 mol) in tetrahydrofuran (88 mL) was added manganese dioxide (10.44 g, 0.12 mol) under nitrogen. The reaction was stirred at 30° C. for 16 hours, then filtered. The filtrate was concentrated to give the title compound (3.8 g, 87%) as a brown solid, which was used in the next step without further purification. MS (ESI): 366 m/z $[M+H]^+$, retention time: 1.31 minutes, purity: 90% (214 nm) (LC-MS method 011).

Intermediate 97: (3-Bromophenyl)(2-(2-fluoro-5-((6-fluoro-1-tosyl-4-vinyl-1H-indol-5-yl)oxy)phenyl)-1H-imidazol-5-yl)methanone

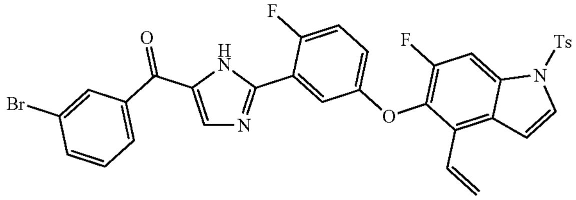 [SMILES: C=Cc1c(Oc2ccc(F)c(-c3ncc(C(=O)c4cccc(Br)c4)[nH]3)c2)c(F)cc2c1ccn2S(=O)(=O)c1ccc(C)cc1]

To a stirred solution of (3-bromophenyl)(2-(2-fluoro-5-((6-fluoro-1-tosyl-4-vinyl-1H-indol-5-yl)oxy)phenyl)-1H-imidazol-5-yl)methanol (Intermediate 97A, 3.75 g, 5.54 mmol) in dichloromethane (50 mL) was added manganese dioxide (4.82 g, 55.4 mmol) in one portion under nitrogen. The reaction was stirred at room temperature for 16 hours, then filtered and concentrated. The residue was purified by silica gel column chromatography (petroleum ether/ethyl acetate=1/1) to give the title compound (3.4 g, 91%) as a yellow solid. MS (ESI): 674, 676 m/z $[M+H]^+$, retention time: 2.51 minutes, purity: 94% (254 nm) (LC-MS method 011).

Intermediate 97A. (3-Bromophenyl)(2-(2-fluoro-5-((6-fluoro-1-tosyl-4-vinyl-1H-indol-5-yl)oxy)phenyl)-1H-imidazol-5-yl)methanol

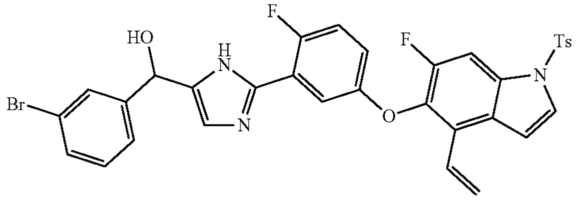 [SMILES: C=Cc1c(Oc2ccc(F)c(-c3ncc(C(O)c4cccc(Br)c4)[nH]3)c2)c(F)cc2c1ccn2S(=O)(=O)c1ccc(C)cc1]

To a stirred and cooled (−78° C.) solution of 1-bromo-3-iodo-benzene (10.9 g, 38.5 mmol) in tetrahydrofuran (40 mL) was added n-butyl lithium (15.4 mL, 38.5 mmol, 2.5M in hexane) dropwise under nitrogen. The reaction mixture was stirred for 20 minutes, then treated with 2-(2-fluoro-5-((6-fluoro-1-tosyl-4-vinyl-1H-indol-5-yl)oxy)phenyl)-1H-imidazole-5-carbaldehyde (Intermediate 96, 4.0 g, 7.7 mmol) in tetrahydrofuran (15 mL) dropwise at −78° C. After stirring at this temperature for 4 hours, the solution was quenched with saturated ammonium chloride solution (100 mL), warmed to room temperature, and extracted with ethyl acetate (3×100 mL). The combined organic layers were washed with brine, dried over sodium sulfate, and concentrated. The residue was purified by silica gel column chromatography (petroleum ether/ethyl acetate=1/1) to give the title compound (3.75 g, 72%) as a brown solid. MS (ESI): 676, 678 m/z $[M+H]^+$, retention time: 2.15 minutes, purity: 99% (254 nm) (LC-MS method 011).

Intermediate 98 (98B and 98C): Diastereomer 1 (intermediate 98B) and 2 (Intermediate 98C) of (R)—N-((3-bromophenyl)(2-(2-fluoro-5-((6-fluoro-1-tosyl-4-vinyl-1H-indol-5-yl)oxy)phenyl)-1H-imidazol-5-yl)methyl)-2-methylpropane-2-sulfinamide

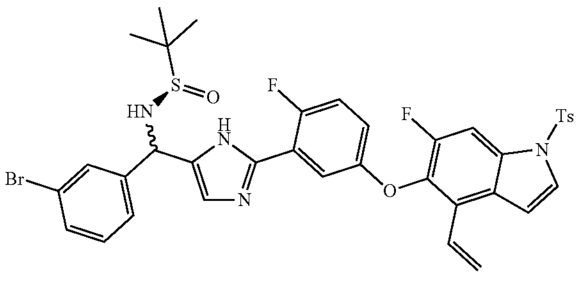 [SMILES: C=Cc1c(Oc2ccc(F)c(-c3ncc(C(N[S@](=O)C(C)(C)C)c4cccc(Br)c4)[nH]3)c2)c(F)cc2c1ccn2S(=O)(=O)c1ccc(C)cc1]

To a stirred solution of (R,E)-N-((3-bromophenyl)(2-(2-fluoro-5-((6-fluoro-1-tosyl-4-vinyl-1H-indol-5-yl)oxy)phenyl)-1H-imidazol-5-yl)methylene)-2-methylpropane-2-sulfinamide (Intermediate 98A, 4.0 g, 5.1 mmol) in methanol (50 mL) was added sodium borohydride (388 mg, 6.7 mmol). The mixture was stirred at room temperature for 2 hours, quenched with saturated ammonium chloride (60 mL), and extracted with ethyl acetate (3×100 mL). The combined organic layers were washed with brine (50 mL), dried over sodium sulfate and concentrated. The residue was purified with silica gel column chromatography (petroleum ether/ethyl acetate=3/1) to give the first eluent, designated as Intermediate 98B (800 mg, yield 20%) as a light-yellow solid; and the second eluent, designated as Intermediate 98C (600 mg, yield 15%) as a light-yellow solid.

Intermediate 98B: MS (ESI): 779, 781 m/z $[M+H]^+$, retention time: 2.31 minutes, purity: 99% (254 nm) (LC-MS method 011).

Intermediate 98C: MS (ESI): 779, 781 m/z $[M+H]^+$, retention time: 2.33 minutes, purity: 99% (254 nm) (LC-MS method 011).

Intermediate 98A: (R,E)-N-((3-bromophenyl)(2-(2-fluoro-5-((6-fluoro-1-tosyl-4-vinyl-1H-indol-5-yl)oxy)phenyl)-1H-imidazol-5-yl)methylene)-2-methylpropane-2-sulfinamide

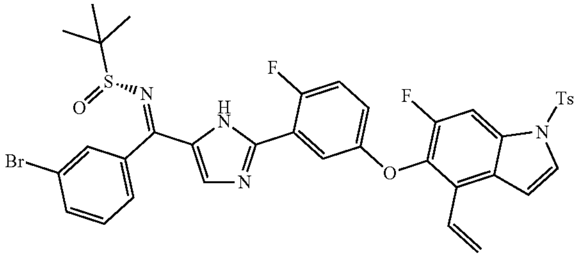 [SMILES: C=Cc1c(Oc2ccc(F)c(-c3ncc(/C(=N/[S@](=O)C(C)(C)C)c4cccc(Br)c4)[nH]3)c2)c(F)cc2c1ccn2S(=O)(=O)c1ccc(C)cc1]

To a stirred and cooled (0° C.) solution of (3-bromophenyl)(2-(2-fluoro-5-((6-fluoro-1-tosyl-4-vinyl-1H-indol-5-yl)oxy)phenyl)-1H-imidazol-5-yl)methanone (Intermediate 97, 4 g, 6 mmol) and (R)-2-methylpropane-2-sulfinamide (1.08 g, 9 mmol) in tetrahydrofuran (50 mL) was added tetraethoxy titanium (IV) (2.7 g, 12 mmol) dropwise. The reaction mixture was stirred at 70° C. for 40 hours, then poured into saturated ammonium chloride (200 mL) and extracted with ethyl acetate (2×100 mL). The combined organic layers were washed with brine (80 mL), dried over sodium sulfate, and concentrated to give the title compound (4.6 g, crude) as a yellow solid. The crude product was used in the next step without further purification. MS (ESI): 777 m/z $[M+H]^+$, retention time: 2.68 minutes, purity: 40% (254 nm) (LC-MS method 011).

Intermediate 99: Benzyl 2-(3-(2,2-dimethyl-1,3-dioxolan-4-yl)phenyl)-7-((2-ethoxy-2-oxoethyl) sulfonyl)-2,6,6-trimethylheptanoate

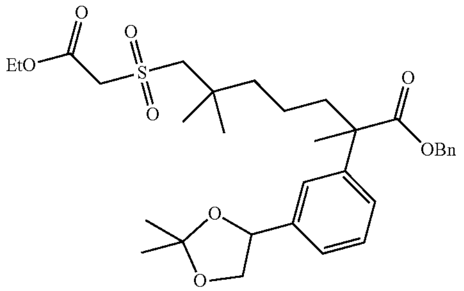 [SMILES: CCOC(=O)CS(=O)(=O)CC(C)(C)CCCC(C)(C(=O)OCc1ccccc1)c1cccc(C2COC(C)(C)O2)c1]

To a stirred solution of benzyl 2-(3-(1,2-dihydroxyethyl) phenyl)-7-((2-ethoxy-2-oxoethyl)sulfonyl)-2,6,6-trimethylheptanoate (Intermediate 99D, 4 g, 7.29 mmol) in acetone (20 mL) was added p-toluenesulfonic acid (0.126 g, 0.729 mmol). The mixture was stirred at room temperature for 2 hours, then partitioned between water (80 mL) and ethyl acetate (150 mL). The separated organic layer, combined with two additional ethyl acetate extracts (2×80 mL) was washed with brine, dried over sodium sulfate, and concentrated. The residue was purified by silica gel column chromatography (petroleum ether: ethyl acetate=4:1) to give the title compound (2.9 g, 68%) as a colorless liquid. MS (ESI): 611 m/z $[M+Na]^+$, retention time: 2.32 minutes, purity: 99% (254 nm) (LC-MS method 012).

The following intermediate was prepared based on the procedures described for Intermediate 99, and/or for Intermediate 99A to 99D.

| Inter. No. | Structure | Name | MS m/z [M + H]+ |
|---|---|---|---|
| 99-1 | 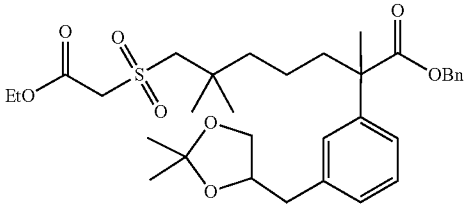 [SMILES: CCOC(=O)CS(=O)(=O)CC(C)(C)CCCC(C)(C(=O)OCc1ccccc1)c1cccc(CC2COC(C)(C)O2)c1] | benzyl 2-(3-((2,2-dimethyl-1,3-dioxolan-4-yl)methyl)phenyl)-7-((2-ethoxy-2-oxoethyl)sulfonyl)-2,6,6-trimethylheptanoate | 603 |

Intermediate 99A: Benzyl 7-(acetylthio)-2-(3-bromophenyl)-2,6,6-trimethylheptanoate

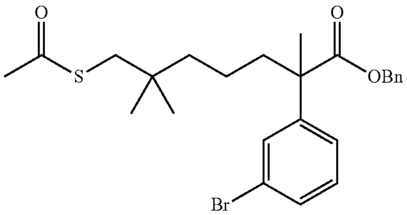 [SMILES: CC(=O)SCC(C)(C)CCCC(C)(C(=O)OCc1ccccc1)c1cccc(Br)c1]

To a stirred and cooled (0° C.) solution of triphenylphosphine (48.99 g, 0.187 mol) in tetrahydrofuran (50 mL) was added diisopropyl azodicarboxylate (32.8 mL, 0.187 mol) dropwise. The mixture was stirred at this temperature until the formation of a white solid. Then the reaction was treated with a solution of benzyl 2-(3-bromophenyl)-7-hydroxy-2,6,6-trimethylheptanoate (Intermediate 41, 27 g, 62.5 mmol) and thioacetic acid (14.25 g, 0.187 mol) in tetrahydrofuran (20 mL). The mixture was stirred at 0° C. for 1 hour, then at 25° C. for 1 hour, and quenched with water (200 mL). The solution was extracted with ethyl acetate (3×200 mL). The combined organic extracts were washed with brine, dried over sodium sulfate, and concentrated. The residue was purified by silica gel column chromatography (petroleum ether: ethyl acetate=8:1) to give the title compound (20 g, 88%) as a colorless liquid. MS (ESI): 513, 515 m/z $[M+Na]^+$, retention time: 2.59 minutes, purity: 99% (214 nm) (LC-MS method 011).

Intermediate 99B: Benzyl 2-(3-bromophenyl)-7-((2-ethoxy-2-oxoethyl)thio)-2,6,6-trimethylheptanoate

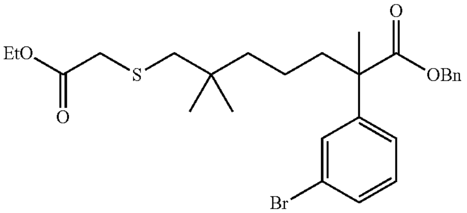 [SMILES: CCOC(=O)CSCC(C)(C)CCCC(C)(C(=O)OCc1ccccc1)c1cccc(Br)c1]

To a stirred and cooled (0° C.) solution of benzyl 7-(acetylthio)-2-(3-bromophenyl)-2,6,6-trimethylheptanoate (Intermediate 99A, 20 g, 40.82 mmol) in ethanol (100 mL) was added ethyl bromoacetate (10.22 g, 61.22 mmol) and sodium ethoxide (4.16 g, 61.22 mmol). The mixture was stirred at room temperature for 4 hours, then quenched with water (300 mL), and extracted with ethyl acetate (3×300 mL). The combined organic extracts were washed with brine, dried over sodium sulfate, and concentrated. The crude product was purified by silica gel column chromatography (petroleum ether: ethyl acetate=8:1) to give the title compound (19 g, 87%) as a colorless liquid. MS (ESI): 557, 559 m/z $[M+Na]^+$, retention time: 2.56 minutes, purity: 96% (214 nm) (LC-MS method 011).

Intermediate 99C: Benzyl 7-((2-ethoxy-2-oxoethyl)thio)-2,6,6-trimethyl-2-(3-vinylphenyl)heptanoate

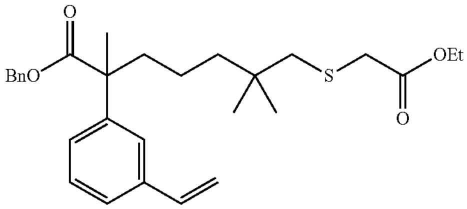 [SMILES: C=Cc1cccc(C(C)(CCCC(C)(C)CSCC(=O)OCC)C(=O)OCc2ccccc2)c1]

To a stirred and degassed solution of benzyl 2-(3-bromophenyl)-7-((2-ethoxy-2-oxoethyl)thio)-2,6,6-trimethylheptanoate (Intermediate 99B, 6 g, 11.2 mmol) in 1,4-dioxane (30 mL) and water (6 mL) was added 4,4,5-trimethyl-2-vinyl-1,3,2-dioxaborolane (2.35 g, 16.8 mmol), [1,1'-bis(diphenylphosphino)ferrocene]dichloropalladium (II) (820 mg, 1.12 mmol) and cesium carbonate (7.30 g, 22.4 mmol) under nitrogen. The mixture was stirred at 100° C. overnight. After cooling to room temperature, the solution was partitioned between water (100 mL) and ethyl acetate (150 mL). The separated organic layer, combined with two additional ethyl acetate extracts (2×50 mL), was washed with brine, dried over sodium sulfate, and concentrated. The residue was purified by silica gel column chromatography (petroleum ether: ethyl acetate=8:1) to give the title compound (4.00 g, 74.0%) as a colorless liquid. MS (ESI): 505 m/z $[M+Na]^+$, retention time: 2.50 minutes, purity: 87% (214 nm) (LC-MS method 011).

Intermediate 99D: Benzyl 2-(3-(1,2-dihydroxyethyl)phenyl)-7-((2-ethoxy-2-oxoethyl)sulfonyl)-2,6,6-trimethylheptanoate

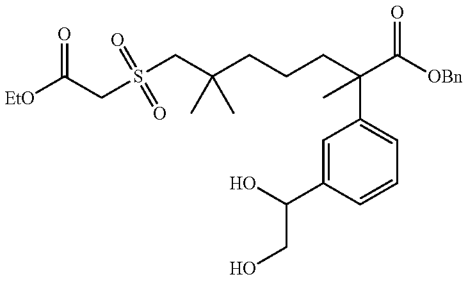 [SMILES: CCOC(=O)CS(=O)(=O)CC(C)(C)CCCC(C)(C(=O)OCc1ccccc1)c1cccc(C(O)CO)c1]

To a stirred and cooled (0° C.) solution of benzyl 7-((2-ethoxy-2-oxoethyl)thio)-2,6,6-trimethyl-2-(3-vinylphenyl)heptanoate (Intermediate 99C, 4 g, 8.29 mmol) in acetone (20 mL) was added osmium tetra-oxide dihydrate (122 mg, 0.331 mmol) and 4-methylmorpholine N-oxide (50% in water, 19.4 g, 0.0829 mol). The mixture was stirred at room temperature overnight, then partitioned between water (100 mL) and ethyl acetate (100 mL). The separated organic layer, combined with two additional ethyl acetate extracts (2×100 mL), was washed with brine, dried over sodium sulfate, and concentrated to give the title compound (4.0 g, 88.0%) as a colorless liquid. MS (ESI): 571 m/z $[M+Na]^+$, retention time: 2.00 minutes, purity: 50% (214 nm) (LC-MS method 011).

Intermediate 100: 7-(Benzyloxy)-2-(3-bromophenyl)-6,6-difluoro-2,5,5-trimethylheptanoic Acid

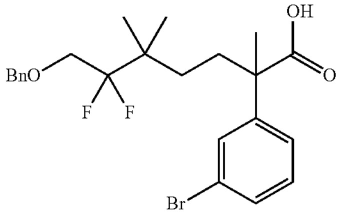 [SMILES: CC(CCC(C)(C)C(F)(F)COCc1ccccc1)(C(=O)O)c1cccc(Br)c1]

A mixture of methyl 7-(benzyloxy)-2-(3-bromophenyl)-6,6-difluoro-2,5,5-trimethylheptanoate (Intermediate 100F, 4.7 g, 9.72 mmol) in lithium hydroxide [0.2M in tetrahydrofuran/methanol/water (3:1:1), 250 mL] was stirred at 45° C. for 6 hours, then concentrated to remove methanol and tetrahydrofuran. The aqueous residue was acidified with 1N hydrochloric acid (100 mL) to pH~4 and extracted with ethyl acetate (3×100 mL). The combined organic extracts were washed with brine (3×50 mL), dried over sodium sulfate, and concentrated. The crude title compound (4.5 g, yield 98.6%) was obtained as an oil, which was used without further purification. MS (ESI): 491 m/z $[M+Na]^+$, retention time: 2.73 minutes, purity: 92% (214 nm) (LC-MS method 011).

Intermediate 100A: 2,2-Difluoro-3,3-dimethylpent-4-enoic Acid

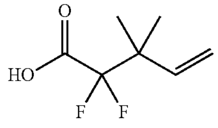

To a stirred and cooled (0° C.) solution of 2,2,2-trifluoro-1-methoxy-ethanol (15 g, 115 mmol) in tetrahydrofuran (200 mL) was added potassium carbonate (39.8 g, 288 mmol), tetrabutylammonium bromide (1.86 g, 5.77 mmol), and 1-bromo-3-methylbut-2-ene (14.6 mL, 127 mmol). The reaction was stirred at room temperature for 8 hours, then filtered. The filtrated was concentrated to give 3-methyl-1-(2,2,2-trifluoro-1-methoxyethoxy)but-2-ene (20 g).

To a stirred and cooled (−78° C.) solution of the above 3-methyl-1-(2,2,2-trifluoro-1-methoxyethoxy)but-2-ene (20 g, 101 mmol) in tetrahydrofuran (200 mL) was added n-butyllithium (2.5M in hexane, 101 mL, 252 mmol) dropwise. The reaction mixture was stirred at this temperature for 3 hours, then quenched with water (200 mL) and stirred at room temperature for an additional hour. The solution was treated with lithium hydroxide monohydrate (8.4 g, 200 mmol) and methanol (100 mL) and stirred for 3 hours. The mixture was concentrated to remove tetrahydrofuran and methanol. The aqueous residue was washed with petroleum ether (3×100 mL), then acidified with concentrated hydrochloric acid to pH 3 and extracted with ethyl acetate (3×100 mL). The combined ethyl acetate extracts were washed with brine, dried over sodium sulfate, and concentrated to give the crude title compound (9.5 g, yield 50% two steps) as an oil. This crude product was used in the next step without further purification. $^1H$ NMR (500 MHz, DMSO-$d_6$) δ 14.49 (s, 1H), 5.97-5.84 (m, 1H), 5.23-5.17 (m, 1H), 5.17-5.14 (m, 1H), 1.14 (s, 6H) ppm.

Intermediate 100B: 2,2-Difluoro-3,3-dimethylpent-4-en-1-ol

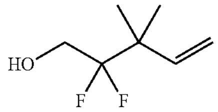

To a stirred solution of 2,2-difluoro-3,3-dimethylpent-4-enoic acid (Intermediate 100A, 9.5 g, 57.9 mmol) in tetrahydrofuran (220 mL) was added lithium aluminum hydride (4.4 g, 116 mmol) portion wise. The mixture was refluxed for 4 hours, then cooled with ice water, diluted with 300 mL of ethyl ether, and slowly treated with 80 g of sodium sulfate decahydrate. After the addition, the mixture was stirred at room temperature for 4 hours and filtered. The filtrate was dried over magnesium sulfate and concentrated to give the title compound (7.7 g, 80%) as an oil, which contained 10% tetrahydrofuran. No further purification was conducted due to the volatile of the compound. $^1H$ NMR (500 MHz, DMSO-$d_6$) δ 5.93 (dd, J=17.6, 10.8 Hz, 1H), 5.25 (t, J=6.4 Hz, 1H), 5.15 (d, J=17.6 Hz, 1H), 5.13 (d, J=10.8 Hz, 1H), 3.64 (dt, J=15.6, 6.4 Hz, 2H), 1.10 (s, 6H) ppm.

Intermediate 100C: (((2,2-Difluoro-3,3-dimethylpent-4-en-1-yl)oxy)methyl)benzene

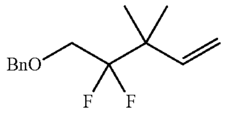 [SMILES: C=CC(C)(C)C(F)(F)COCc1ccccc1]

To a stirred and cooled (0° C.) solution of 2,2-difluoro-3,3-dimethylpent-4-en-1-ol (Intermediate 100B, 7.7 g, contains 10% tetrahydrofuran) in N,N-dimethylformamide (150 mL) was added sodium hydride (60% in mineral oil, 2.77 g). The mixture was stirred for 1 hour, then treated with benzyl bromide (8.8 mL). The reaction mixture was stirred at room temperature over the weekend, quenched with saturated ammonium chloride (500 mL), and extracted with petroleum ether (3×150 mL). The combined organic extracts were washed with brine, dried over sodium sulfate, and concentrated. The residue was purified by automated flash chromatography (330 g silica gel column, eluted with 0-10% ethyl acetate in petroleum ether) to give the title compound (10.5 g, purity 90% contained 10% of benzyl bromide, yield 85%) as an oil. $^1$H NMR (400 MHz, $CDCl_3$) δ 7.37-7.28 (m, 5H), 5.96 (dd, J=17.6, 10.8 Hz, 1H), 5.13 (d, J=18.0 Hz, 1H), 5.12 (d, J=10.4 Hz, 1H), 4.61 (s, 2H), 3.70 (t, J=14.4 Hz, 2H), 1.18 (s, 6H) ppm.

Intermediate 100D: 5-(Benzyloxy)-4,4-difluoro-3,3-dimethylpentan-1-ol

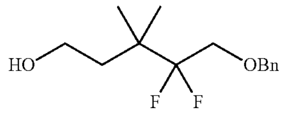 [SMILES: CC(C)(CCO)C(F)(F)COCc1ccccc1]

To a stirred and cooled (0° C.) solution of (((2,2-difluoro-3,3-dimethylpent-4-en-1-yl)oxy)methyl)benzene (Intermediate 100C, 10.5 g, purity 90%) in tetrahydrofuran (130 mL was added a solution of 9-BBN (0.5M in tetrahydrofuran, 236 mL) dropwise. The mixture was stirred at room temperature overnight, then cooled to 0° C., treated with 2M sodium hydroxide (177 mL), followed by 30% hydrogen peroxide (157 mL). The mixture was stirred at room temperature for 4 hours, diluted with water (100 mL) and extracted with ethyl acetate (4×150 mL). The combined extracts were washed with saturated sodium sulfite, brine, dried over sodium sulfate, and concentrated. The residue was purified by automated flash chromatography (330 g silica gel column, eluted with 0-10% methanol in dichloromethane) to give the title compound (9.52 g, 84%) as an oil. MS (ESI): 259 m/z [M+H]$^+$, retention time: 1.95 minutes, purity: 90% (254 nm) (LC-MS method 014).

Intermediate 100E: 5-(Benzyloxy)-4,4-difluoro-3,3-dimethylpentyl 4-methylbenzenesulfonate

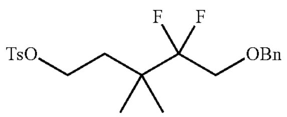 [SMILES: Cc1ccc(S(=O)(=O)OCCC(C)(C)C(F)(F)COCc2ccccc2)cc1]

To a stirred solution of 5-(benzyloxy)-4,4-difluoro-3,3-dimethylpentan-1-ol (Intermediate 100D, 9.52 g, 36.9 mmol) in dichloromethane (150 mL) was added tosyl chloride (10.5 g, 49.8 mmol), triethylamine (10.3 mL, 73.7 mmol) and 4-dimethylaminopyridine (450 mg, 3.69 mmol). The mixture was stirred at room temperature overnight, then washed with brine, dried over sodium sulfate, and concentrated. The residue was purified by flash chromatography (80 g silica gel column, eluted with 0-20% ethyl acetate in petroleum ether) to give the title compound (12 g, 79%) as an oil. MS (ESI): 435 m/z [M+Na]$^+$, retention time: 2.30 minutes, purity: 97% (214 nm) (LC-MS method 012).

Intermediate 100F: Methyl 7-(benzyloxy)-2-(3-bromophenyl)-6,6-difluoro-2,5,5-trimethylheptanoate

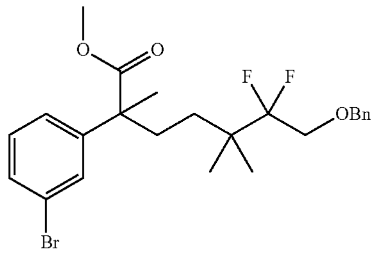 [SMILES: COC(=O)C(C)(CCC(C)(C)C(F)(F)COCc1ccccc1)c1cccc(Br)c1]

To a stirred and cooled (0° C.) solution of 5-(benzyloxy)-4,4-difluoro-3,3-dimethylpentyl 4-methylbenzenesulfonate (Intermediate 100E, 8.25 g, 20 mmol) and methyl 2-(3-bromophenyl)propanoate (5.35 g, 22 mmol) in tetrahydrofuran (60 mL) were added sodium bis(trimethylsilyl)amide (2M in tetrahydrofuran, 13 mL, 26 mmol) under argon. The mixture was stirred at room temperature overnight, quenched with saturated ammonium chloride (150 mL), and extracted with ethyl acetate (3×150 mL). The combined organic extracts were washed with brine, dried over sodium sulfate, filtered, and concentrated. The residue was purified by automated flash chromatography (120 g silica gel column, eluted with 0-15% ethyl acetate in petroleum ether) to give the title compound (4.7 g, 49%) as an oil. MS (ESI): 505, 507 m/z [M+Na]$^+$, retention time: 2.40 minutes, purity: >99% (254 nm) (LC-MS method 013).

Intermediate 101: 2,2-Bis(Methyl-$d_3$)pentane-1,5-diyl bis(4-methylbenzenesulfonate)

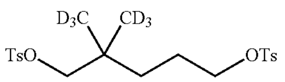

To a stirred and cooled (0° C.) solution of 2,2-bis(methyl-$d_3$)pentane-1,5-diol (Intermediate 101B, 4 g, 29 mmol) in pyridine (50 mL) was added 4-methylbenzenesulfonyl chloride (13.8 g, 72.3 mmol). The mixture was stirred at room temperature for 2 hours, then quenched with ice water (100 mL), and extracted with ethyl acetate (3×150 mL). The combined organic phase was washed with 1N hydrochloric acid (2×100 mL), brine, dried over sodium sulfate, and concentrated. The crude material was purified by automated flash chromatography (120 g silica gel column, eluted with 0-70% ethyl acetate in petroleum ether) to give the title compound (8 g, 62%). MS (ESI): 469 m/z $[M+Na]^+$, retention time: 1.57 minutes, purity: 90% (214 nm) (LC-MS method 014).

Intermediate 101A: 3,3-Bis(methyl-$d_3$)tetrahydro-2H-pyran-2-one

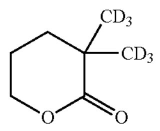 [SMILES: [2H]C([2H])([2H])C1(C([2H])([2H])[2H])CCCOC1=O]

To a stirred and cooled (−78° C.) solution of tetrahydro-2H-pyran-2-one (10 g, 100 mmol) and iodomethane-$d_3$ (43.4 g, 300 mmol) in tetrahydrofuran (200 mL) was added lithium hexamethyldisilazide (1.6 M in tetrahydrofuran, 187 mL, 300 mmol) dropwise. The mixture was stirred at room temperature for 16 hours, then treated with saturated ammonium chloride solution (200 mL) and extracted with ethyl acetate (3×150 mL). The combined organic extracts were washed with brine, dried over sodium sulfate, and concentrated. The crude material was purified with automated flash chromatography (120 g silica gel column, eluted with 0-10% ethyl acetate in petroleum ether) to give the title compound (6 g, 45%). $^1H$ NMR (400 MHz, $CDCl_3$) δ 4.2 (t, J=6.0 Hz, 2H), 1.76-1.71 (m, 2H), 1.51-1.43 (m, 2H) ppm.

Intermediate 101B: 2,2-Bis(methyl-$d_3$)pentane-1,5-diol

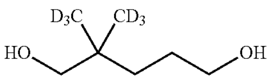

To a stirred and cooled (0° C.) solution 3,3-bis(methyl-$d_3$)tetrahydro-2H-pyran-2-one (Intermediate 101A, 6 g, 44.7 mmol) in tetrahydrofuran (100 mL) was added lithium aluminum hydride (2 g, 53.6 mmol) portion-wise. The mixture was allowed to warm to room temperature and stirred for 16 hours then cooled to 0° C. The solution was carefully treated with 2 mL of water, then 15% NaOH solution (2 mL), followed by 6 mL of water, and stirred for 15 minutes, and filtered. The filtrate was dried with magnesium sulfate and concentrated to give the title compound (4 g, 65%) as a crude product, which was used without further purification. $^1H$ NMR (400 MHz, $CDCl_3$) δ 3.63 (t, J=5.6 Hz, 2H), 3.32 (s, 2H), 1.55-1.49 (m, 2H), 1.33-1.28 (m, 2H) ppm.

Intermediate 102: 2-Fluoro-5-((6-fluoro-1-(phenylsulfonyl)-4-((1-(tetrahydro-2H-pyran-2-yl)-1H-pyrazol-3-yl)methyl)-1H-indol-5-yl)oxy)benzonitrile

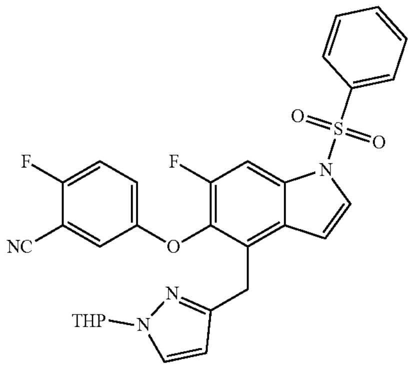

To a stirred and degassed solution of 5-((4-(bromomethyl)-6-fluoro-1-(phenylsulfonyl)-1H-indol-5-yl)oxy)-2-fluorobenzonitrile (Intermediate 13, 12 g, 23.8 mmol) in toluene/ethanol=5/2 (150 mL) was added 1-(tetrahydro-2H-pyran-2-yl)-5-(4,4,5,5-tetramethyl-1,3,2-dioxaborolan-2-yl)-1H-pyrazole (26.5 g, 96.4 mmol), tetrakis(triphenylphosphine)palladium(0) (2.76 g, 2.38 mmol), and sodium carbonate solution (7.5 g, 71.5 mmol, 20% in water). The mixture was stirred at 80° C. for 2 hours, then quenched with water (500 ml), and extracted with ethyl acetate (3×200 mL). The combined organic extracts were washed with saturated lithium chloride solution, brine, dried over sodium sulfate, and concentrated. The crude material was purified by flash chromatography to give the title compound (8.0 g, 58%). MS (ESI): 597 m/z $[M+Na]^+$, retention time: 2.26 minutes, purity: 95% (254 nm) (LC-MS method 012).

Intermediate 103: Ethyl 3-(3-(5,12,12,13,13-pentamethyl-4-oxo-11-oxa-8-thia-2,3-diaza-12-silatetradecan-5-yl)phenyl)propanoate

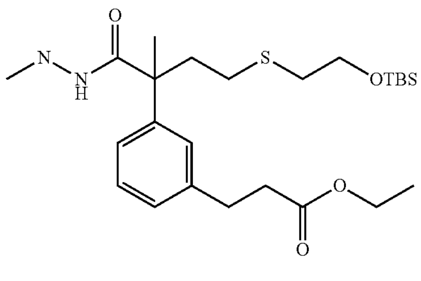 [SMILES: CCOC(=O)CCc1cccc(C(C)(CCSCCO[Si](C)(C)C(C)(C)C)C(=O)NNC)c1]

To a stirred solution of benzyl (E)-5-(3-(3-ethoxy-3-oxoprop-1-en-1-yl)phenyl)-2,5,12,12,13,13-hexamethyl-4-oxo-11-oxa-8-thia-2,3-diaza-12-silatetradecanoate (Intermediate 103E, 7.16 mmol, 4.5 g) in ethanol (50 mL) was added palladium on active carbon (10%, 1.0 g). The mixture was stirred at 45° C. for 4 hours under hydrogen balloon, then filtered through a pad of Celite. The filtrate was concentrated to give the title compound (3 g, 85%), which was used without further purification. MS (ESI): 497 m/z $[M+H]^+$, retention time: 2.43 minutes, purity: 85% (214 nm) (LC-MS method 012).

Intermediate 103A: Methyl 2-(3-bromophenyl)-4-chloro-2-methylbutanoate

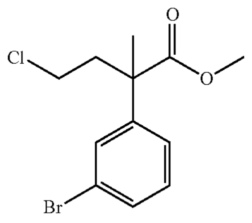 [SMILES: COC(=O)C(C)(CCCl)c1cccc(Br)c1]

To a stirred and cooled (−78° C.) solution of methyl 2-(3-bromophenyl)propanoate (25 g, 100 mmol) in tetrahydrofuran (200 mL) was added lithium diisopropylamide (49 mL, 2.5 M in tetrahydrofuran) dropwise. The mixture was stirred for 15 minutes, then treated with 1-bromo-2-chloroethane (14.7 g, 10.0 mmol). The solution was allowed to warm to room temperature and stirred for 16 hours, quenched with saturated ammonium chloride (100 mL), water (500 mL), and extracted with ethyl acetate (3×100 mL). The combined organic extracts were washed with saturated lithium chloride, brine, dried over sodium sulfate, and concentrated. The residue was purified by flash chromatography to give the title compound (28 g, 89%). MS (ESI): 307 m/z $[M+H]^+$, retention time: 2.24 minutes, purity: 62% (254 nm) (LC-MS method 012).

The following intermediate was prepared based on the procedures described for Intermediate 103A.

| Inter. No. | Structure | Name | MS m/z $[M + H]^+$ |
| --- | --- | --- | --- |
| 103A-1 | 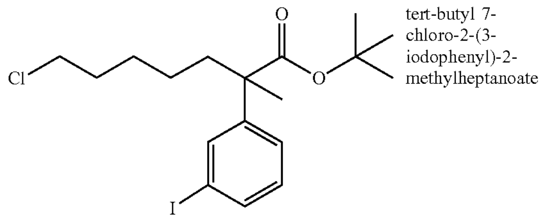 | tert-butyl 7-chloro-2-(3-iodophenyl)-2-methylheptanoate | 459 m/z $[M + H]^+$; RT: 2.64 min.; (LC-MS method 003) |

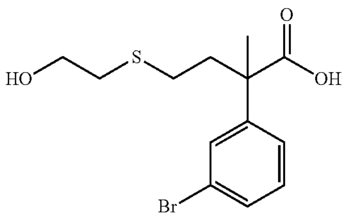 [SMILES: CC(CCSCCO)(C(=O)O)c1cccc(Br)c1]

To a stirred solution of methyl 2-(3-bromophenyl)-4-chloro-2-methylbutanoate (Intermediate 103A, 28 g, 91.6 mmol) in 300 mL of ethanol and 100 mL of water was added sodium hydroxide (8 g, 200 mmol) and 2-mercaptoethanol (21.5 g, 285 mmol). The mixture was stirred at 70° C. for 16 hours, then treated with another portion of sodium hydroxide solution (12 g, 300 mmol, in 100 mL of water). The solution was stirred at 70° C. for an additional hour, then concentrated to remove ethanol. The aqueous residue was acidified with 100 mL of 6 M hydrochloric acid to pH~2, then extracted with ethyl acetate (3×150 mL). The combined organic extracts were washed with brine, dried over sodium sulfate, and concentrated. The residue was purified with flash chromatograph to give the title compound (24 g, 80%). MS (ESI): 355, 357 m/z $[M+H]^+$, retention time: 1.80 minutes, purity: 90% (254 nm) (LC-MS method 012).

Intermediate 103C: (E)-2-(3-(3-Ethoxy-3-oxoprop-1-en-1-yl)phenyl)-4-((2-hydroxyethyl)thio)-2-methylbutanoic Acid

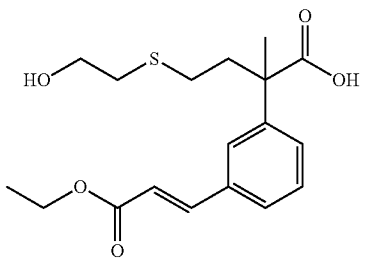 [SMILES: CCOC(=O)/C=C/c1cccc(C(C)(CCSCCO)C(=O)O)c1]

To a stirred and degassed solution of 2-(3-bromophenyl)-4-((2-hydroxyethyl)thio)-2-methylbutanoic acid (Intermediate 103B, 15.0 g, 45 mmol) in N-Methyl pyrrolidone (100 mL) was added ethyl acrylate (9 g, 90 mmol), palladium (II) acetate (1.0 g, 4.5 mmol), tri-o-tolylphosphane (4.11 g, 13.5 mmol) and triethylamine (22.8 g, 225 mmol). The mixture was stirred at 120° C. for 16 hours. After cooling to room temperature, the solution was quenched with 300 mL of 1 M hydrochloric acid and partitioned between water (200 mL) and ethyl acetate (200 mL). The separated organic layer, combined with two additional ethyl acetate extracts (2×200 mL), was washed with saturated lithium chloride, brine, dried over sodium sulfate, and concentrated. The residue was purified by flash chromatography to give the title compound (12 g, 80%). MS (ESI): 375 m/z $[M+Na]^+$, retention time: 1.82 minutes, purity: 80% (254 nm) (LC-MS method 012).

The following intermediate was prepared based on the procedures described for Intermediate 103B.

| Inter. No. | Structure | Name | MS m/z [M + H]$^+$ |
|---|---|---|---|
| 103B-1 | 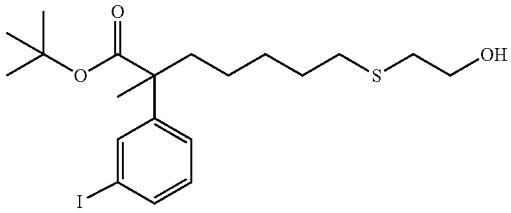 [SMILES: CC(C)(C)OC(=O)C(C)(CCCCCSCCO)c1cccc(I)c1] | tert-butyl 7-((2-hydroxyethyl)thio)-2-(3-iodophenyl)-2-methylheptanoate | 501 m/z [M + H]$^+$; RT: 2.18 min.; (LC-MS method 003) |

Intermediate 103D: (E)-4-((2-((tert-Butyldimethylsilyl)oxy)ethyl)thio)-2-(3-(3-ethoxy-3-oxoprop-1-en-1-yl)phenyl)-2-methylbutanoic Acid

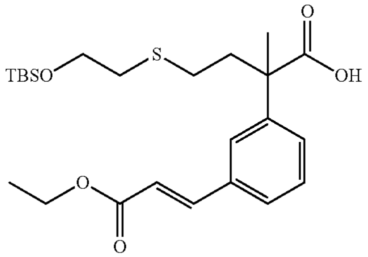 [SMILES: CCOC(=O)/C=C/c1cccc(C(C)(CCSCCO[Si](C)(C)C(C)(C)C)C(=O)O)c1]

To a stirred solution of (E)-2-(3-(3-ethoxy-3-oxoprop-1-en-1-yl)phenyl)-4-((2-hydroxyethyl)thio)-2-methylbutanoic acid (Intermediate 103C, 9.0 g, 25.5 mmol) in dichloromethane (100 mL) was added tert-butyldimethylsilyl chloride (15.4 g, 10 mmol) and triethylamine (15.5 g, 155 mmol). The mixture was stirred at room temperature for 48 hours, quenched with ethanol (100 mL) and water (20 mL) and stirred for an additional 0.5 hour. The solution was partitioned between water (1 L) and ethyl acetate (300 mL). The separated organic layer, combined with two additional ethyl acetate extracts (2×250 mL), was washed with saturated lithium chloride, brine, dried over sodium sulfate, and concentrated. The crude material was purified by flash chromatography to give the title compound (12 g, 75%). MS (ESI): 489 m/z [M+Na]$^+$, retention time: 2.49 minutes, purity: 95% (254 nm) (LC-MS method 012).

Intermediate 103E: Benzyl (E)-5-(3-(3-ethoxy-3-oxoprop-1-en-1-yl)phenyl)-2,5,12,12,13,13-hexamethyl-4-oxo-11-oxa-8-thia-2,3-diaza-12-silatetradecanoate

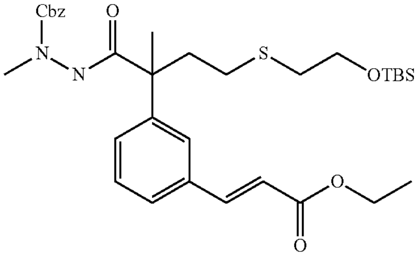 [SMILES: CCOC(=O)/C=C/c1cccc(C(C)(CCSCCO[Si](C)(C)C(C)(C)C)C(=O)NN(C)C(=O)OCc2ccccc2)c1]

To a stirred solution of (E)-4-((2-((tert-butyldimethylsilyl)oxy)ethyl)thio)-2-(3-(3-ethoxy-3-oxoprop-1-en-1-yl)phenyl)-2-methylbutanoic acid (Intermediate 103D, 6 g, 9.64 mmol) in acetonitrile (50 mL) were added benzyl N-amino-N-methyl-carbamate (2.61 g, 14.5 mmol), 1-methylimidazole (2.37 g, 28.9 mmol), and N,N,N',N'-tetramethylchloroformamidinium hexafluoro phosphate (2.71 g, 9.64 mmol). The mixture was stirred at room temperature overnight, then partitioned between water (200 mL) and ethyl acetate (150 mL). The separated organic layer, combined with two additional ethyl acetate extracts (2×100 mL), was washed with saturated lithium chloride, dried over sodium sulfate, and concentrated. The residue was purified by flash chromatography to give the title compound (4.5 g, 75%). MS (ESI): 651 m/z [M+Na]$^+$, retention time: 2.66 minutes, purity: 99% (254 nm) (LC-MS method 012).

Intermediate 104: 2-(3-Bromophenyl)-4-(but-2-yn-1-ylthio)-2-methylbutanoic Acid

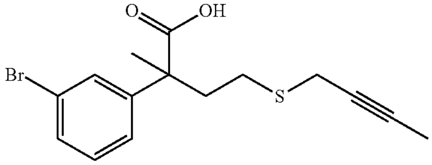 [SMILES: CC#CCSCCC(C)(C(=O)O)c1cccc(Br)c1]

To a stirred solution of methyl 2-(3-bromophenyl)-4-(but-2-yn-1-ylthio)-2-methylbutanoate (Intermediate 104B, 5 g, 13.8 mmol) in methanol (30 mL) and tetrahydrofuran (30 mL) was added a solution of lithium hydroxide monohydrate (1.74 g, 41.4 mmol) in water (15 mL). The mixture was stirred at 40° C. overnight. The solvent was removed. To the residue was added water (100 mL), acidified to pH~2 with 1 N hydrochloric acid, and extracted with ethyl acetate (3×50 mL). The combined organic phases were washed with brine, dried over sodium sulfate, and concentrated to give the crude title compound (4.37 g, 90%) as a light-yellow solid, which was used without further purification. MS (ESI): 363, 365 m/z [M+Na]$^+$, retention time: 2.49 minutes, purity: 95% (254 nm).

Intermediate 104A: Methyl 4-(acetylthio)-2-(3-bromophenyl)-2-methylbutanoate

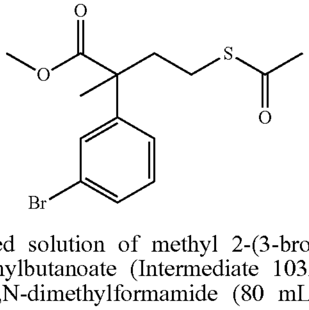

To a stirred solution of methyl 2-(3-bromophenyl)-4-chloro-2-methylbutanoate (Intermediate 103A, 7 g, 21.8 mmol) in N,N-dimethylformamide (80 mL) was added upotassium ethanethioate (5.02 g, 43.5 mmol). The mixture was stirred at room temperature overnight, then partitioned between water (500 mL) and ethyl acetate (200 mL). The separated organic layer, combined with two additional ethyl acetate extracts (2×150 mL), was washed with 5% lithium chloride solution (2×50 mL), brine, dried over sodium sulfate, and concentrated. The residue was purified by automated flash chromatography (0 to 5% ethyl acetate in petroleum ether) to give the title compound (5.9 g, 84%) as a light-yellow oil. MS (ESI): 345, 347 m/z $[M+H]^+$, retention time: 2.24 minutes, purity: 99% (214 nm). (LC-MS Method 012).

Intermediate 104B: Methyl 2-(3-bromophenyl)-4-(but-2-yn-1-ylthio)-2-methylbutanoate

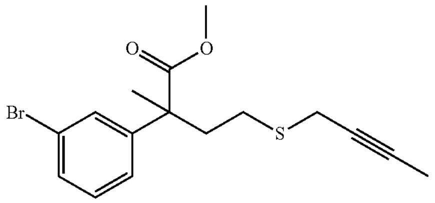 [SMILES: CC#CCSCCC(C)(C(=O)OC)c1cccc(Br)c1]

To a stirred solution of methyl 4-(acetylthio)-2-(3-bromophenyl)-2-methylbutanoate (Intermediate 104A, 5.9 g, 16.9 mmol) and 1-bromobut-2-yne (3.55 g, 25.4 mmol) in methanol (80 mL) was added a solution of sodium methoxide in methanol (6.77 mL, 33.8 mmol). The mixture was stirred at room temperature overnight, then quenched with ice water (300 mL), and extracted with ethyl acetate (3×150 mL). The combined organic extracts were washed with brine, dried over sodium sulfate, and concentrated. The residue was purified by automated flash chromatography (0-10% ethyl acetate in petroleum ether) to give the title compound (5 g, 82%) as a light-yellow oil. MS (ESI): 355, 357 m/z $[M+H]^+$, retention time: 2.24 minutes, purity: 98% (214 nm).

Intermediate 105: (5-(3-Cyano-4-fluorophenoxy)-6-fluoro-1-(phenylsulfonyl)-1H-indol-4-yl)methyl Acetate

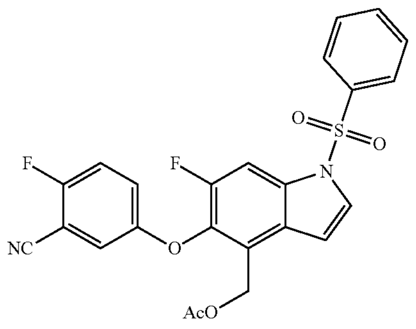 [SMILES: CC(=O)OCc1c(Oc2ccc(F)c(C#N)c2)c(F)cc2c1ccn2S(=O)(=O)c1ccccc1]

To a solution of 5-((4-(bromomethyl)-6-fluoro-1-(phenylsulfonyl)-1H-indol-5-yl)oxy)-2-fluorobenzonitrile (Intermediate 13, 7 g, 12.5 mmol) in dioxane (100 mL) was added potassium acetate (3.69 g, 37.6 mmol) at room temperature. The reaction mixture was stirred at 100° C. for 18 hours and cooled to room temperature. The mixture was partitioned between water (200 mL) and ethyl acetate (150 mL). The separated organic layer, combined with two additional ethyl acetate extracts (2×100 mL), was washed with brine, dried over sodium sulfate, and concentrated. The residue was purified by automated silica gel chromatography (0-30% ethyl acetate in petroleum ether) to give the title compound (4.1 g, 66%) as a light-yellow solid. MS (ESI): 505 m/z $[M+Na]^+$, retention time: 2.20 minutes, purity: 97% (214 nm). (LC-MS Method 012) Intermediate 106: 7-((2-Ethoxy-2-oxoethyl)sulfonyl)-2-(3-(3-ethoxy-3-oxopropyl)phenyl)-6,6-dimethyl-2-(((tetrahydro-2H-pyran-2-yl)oxy)methyl)heptanoic acid

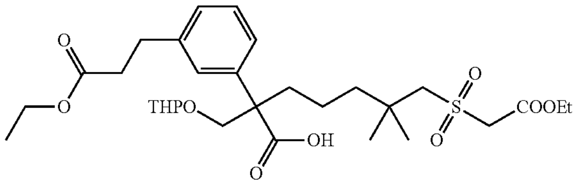

To a stirred solution of benzyl 7-((2-ethoxy-2-oxoethyl)sulfonyl)-2-(3-(3-ethoxy-3-oxopropyl)phenyl)-6,6-dimethyl-2-(((tetrahydro-2H-pyran-2-yl)oxy)methyl)heptanoate (Intermediate 106A, 505 mg, 0.733 mmol) in ethanol (10 mL) was added palladium on carbon (100 mg). The reaction mixture was stirred under hydrogen for 2 hours, then filtered through a pad of Celite. The filtrate was concentrated to give the title compound (410 mg, 93.4%) as an oil. MS (ESI): 621 m/z $[M+Na]^+$, retention time: 1.89 minutes, purity: 95% (254 nm). (LC-MS Method 023).

Intermediate 106A: Benzyl 7-((2-ethoxy-2-oxoethyl)sulfonyl)-2-(3-(3-ethoxy-3-oxopropyl)phenyl)-6,6-dimethyl-2-(((tetrahydro-2H-pyran-2-yl)oxy)methyl)heptanoate

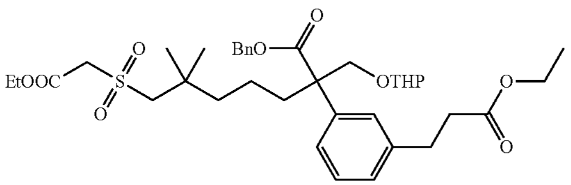

To a stirred solution of benzyl 7-((2-ethoxy-2-oxoethyl)sulfonyl)-2-(3-(3-ethoxy-3-oxopropyl)phenyl)-2-(hydroxymethyl)-6,6-dimethylheptanoate (Intermediate 41-12, 482 mg, 0.797 mmol) in dichloromethane (10 mL) was added 3,4-dihydro-2H-pyran (0.091 mL, 0.996 mmol) and p-toluenesulfonic acid (5.5 mg, 0.03 mmol). The mixture was stirred at room temperature for 1 hour. The solvent was removed. The residue was purified with automated flash chromatography (12 g silica gel column, eluted with 0-40% ethyl acetate in petroleum) to give the title compound (505 mg, 92.0%) as an oil. MS (ESI): 711 m/z $[M+Na]^+$, retention time: 2.15 minutes, purity: 95% (214 nm). (LC-MS Method 023).

Intermediate 107: Ethyl 3-(3-(7-((2-ethoxy-2-oxoethyl)sulfonyl)-6,6-dimethyl-1-(2-methylhydrazineyl)-1-oxo-2-(((tetrahydro-2H-pyran-2-yl)oxy)methyl)heptan-2-yl)phenyl)propanoate

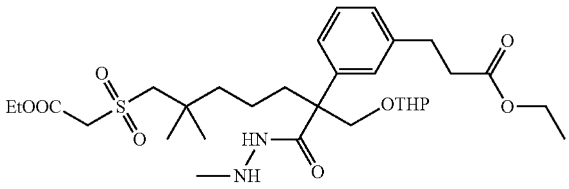

To a stirred solution of benzyl 2-(7-((2-ethoxy-2-oxoethyl)sulfonyl)-2-(3-(3-ethoxy-3-oxopropyl)phenyl)-6,6-dimethyl-2-(((tetrahydro-2H-pyran-2-yl)oxy)methyl)heptanoyl)-1-methylhydrazine-1-carboxylate (Intermediate 107A, 5.5 g, 7.23 mmol) in ethanol (100 mL) was added palladium on carbon (1 g, 10%). The reaction mixture was stirred under hydrogen for 2 hours, then filtered through a pad of Celite. The filtrate was concentrated to give the title compound (4.2 g, 92.7%) as an oil, which was used without further purification. MS (ESI): 627 m/z $[M+H]^+$, retention time: 2.15 minutes, purity: 95% (214 nm). (LC-MS Method 023).

The following intermediates were prepared based on the procedures described for Intermediate 107.

| Inter. No. | Structure | Name | MS m/z $[M + H]^+$ |
|---|---|---|---|
| 107-1 | 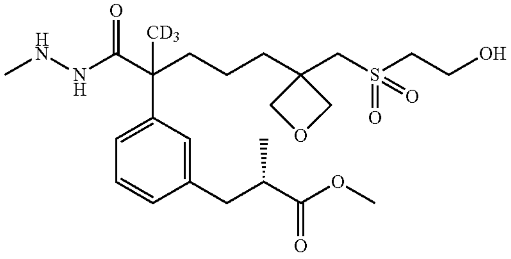 [SMILES: [2H]C([2H])([2H])C(CCCC1(CS(=O)(=O)CCO)COC1)(C(=O)NNC)c1cccc(C[C@H](C)C(=O)OC)c1] | methyl (2S)-3-(3-(5-(3-(((2-hydroxyethyl)sulfonyl)methyl)oxetan-3-yl)-2-(2-methylhydrazine-1-carbonyl)pentan-2-yl-1,1,1-d3)phenyl)-2-methylpropanoate | 502 |
| 107-2 | 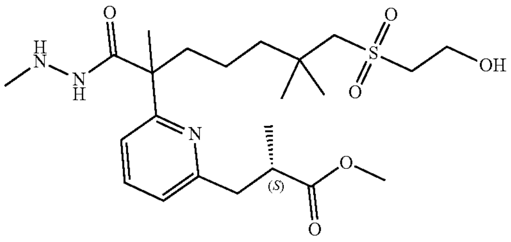 | methyl (2S)-3-(6-(7-((2-hydroxyethyl)sulfonyl)-2,6,6-trimethyl-1-(2-methylhydrazineyl)-1-oxoheptan-2-yl)pyridin-2-yl)-2-methylpropanoate | 486 |
| 107-3 | 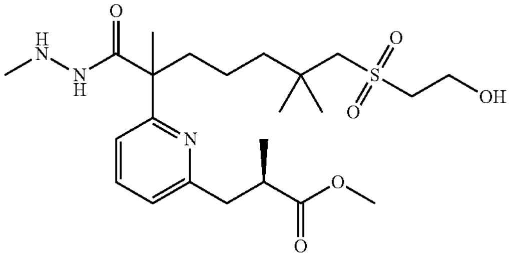 [SMILES: CNNC(=O)C(C)(CCCC(C)(C)CS(=O)(=O)CCO)c1cccc(C[C@@H](C)C(=O)OC)n1] | methyl (2R)-3-(6-(7-((2-hydroxyethyl)sulfonyl)-2,6,6-trimethyl-1-(2-methylhydrazineyl)-1-oxoheptan-2-yl)pyridin-2-yl)-2-methylpropanoate | 486 |
| 107-4 | 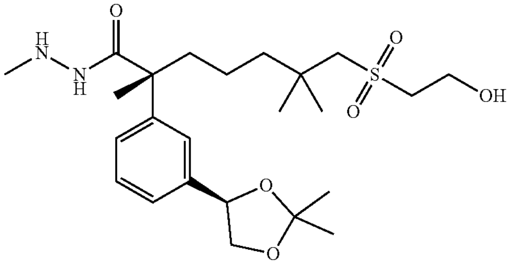 [SMILES: CNNC(=O)[C@](C)(CCCC(C)(C)CS(=O)(=O)CCO)c1cccc([C@@H]2COC(C)(C)O2)c1] | (R)-2-(3-((R)-2,2-dimethyl-1,3-dioxolan-4-yl)phenyl)-7-((2-hydroxyethyl)sulfonyl)-N',2,6,6-tetramethylheptanehydrazide | 485 [M + H] RT: 1.42 min. (LC-MS method 17) |

Intermediate 107A: Benzyl 2-(7-((2-ethoxy-2-oxoethyl)sulfonyl)-2-(3-(3-ethoxy-3-oxopropyl)phenyl)-6,6-dimethyl-2-(((tetrahydro-2H-pyran-2-yl)oxy)methyl)heptanoyl)-1-methylhydrazine-1-carboxylate

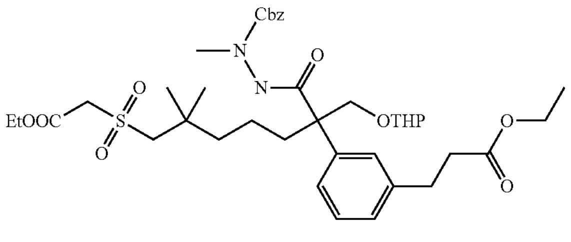

To a stirred solution of 7-((2-ethoxy-2-oxoethyl)sulfonyl)-2-(3-(3-ethoxy-3-oxopropyl)phenyl)-6,6-dimethyl-2-(((tetrahydro-2H-pyran-2-yl)oxy)methyl)heptanoic acid (Intermediate 106, 420 mg, 0.7 mmol) in acetonitrile (10 mL) was added benzyl N-amino-N-methyl-carbamate (139 mg, 0.77 mmol), 1-methylimidazole (202 mg, 2.46 mmol) and chloro-N,N,N',N'-tetramethylformamidinium hexafluorophosphate (197 mg, 0.7 mmol). The reaction mixture was stirred at room temperature for 1 hour, then diluted with ethyl acetate (30 mL). The solution was washed with water (2×30 mL), brine, dried over magnesium sulfate, and concentrated. The residue was purified by automated silica gel column chromatography (12 g silica gel column, eluted with 0-50% ethyl acetate in petroleum ether) to give the title compound (470 mg, 88.1%) as an oil. MS (ESI): 783 m/z $[M+Na]^+$, retention time: 2.02 minutes, purity: 96% (254 nm). (LC-MS Method 023).

Intermediate 108: 2-(3-(3-Ethoxy-3-oxopropyl)phenyl)-5,5-difluoro-7-hydroxy-2,6,6-trimethylheptanoic Acid

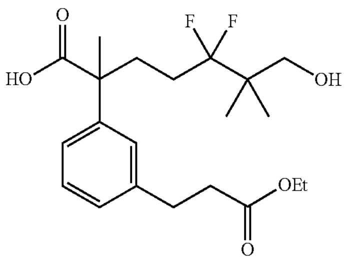 [SMILES: CCOC(=O)CCc1cccc(C(C)(CCC(F)(F)C(C)(C)CO)C(=O)O)c1]

To a stirred solution of (E)-7-(benzyloxy)-2-(3-(3-ethoxy-3-oxoprop-1-en-1-yl)phenyl)-5,5-difluoro-2,6,6-trimethylheptanoic acid (Intermediate 108G, 0.57 g, 1.17 mmol) in ethanol (20 mL) was added palladium on carbon (10%, 0.26 g). The mixture was stirred under hydrogen balloon at 50° C. overnight, then filtered through a pad of Celite. The filtrate was concentrated to give the title compound (0.37 g, 79%) as an oil. MS (ESI): 423 m/z $[M+Na]^+$, retention time: 1.23 minutes, purity: 37% (214 nm). (LC-MS Method 014).

Intermediate 108A: 5-(Benzyloxy)-4,4-dimethylpent-1-en-3-ol

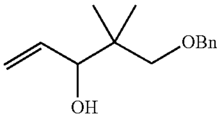 [SMILES: C=CC(O)C(C)(C)COCc1ccccc1]

To a stirred and cooled (0° C.) solution of 3-(benzyloxy)-2,2-dimethylpropanal (24 g, 125 mmol) in dry tetrahydrofuran (200 mL) was added vinyl magnesium bromide (1M in tetrahydrofuran, 162 mL, 162 mmol) dropwise. The mixture was stirred for 2 hours at this temperature, then quenched with saturated ammonium chloride (800 mL) and extracted with ethyl acetate (4×300 mL). The combined organic extracts were washed with brine, dried over sodium sulfate, and concentrated to give the title compound (26 g, 95%) as an oil. $^1H$ NMR (400 MHz, $CDCl_3$) δ 7.37-7.26 (m, 5H), 5.93-5.85 (m, 1H), 5.27 (d, J=17.2 Hz, 1H), 5.18 (d, J=12.0 Hz, 1H), 4.50 (s, 2H), 3.96 (t, J=5.2 Hz, 1H), 3.41 (d, J=8.8 Hz, 1H), 3.33 (d, J=6.0 Hz, 1H), 3.29 (d, J=8.8 Hz, 1H), 0.98 (s, 3H), 0.90 (s, 3H) ppm.

Intermediate 108B. 5-(Benzyloxy)-4,4-dimethylpent-1-en-3-one

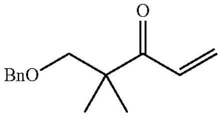 [SMILES: C=CC(=O)C(C)(C)COCc1ccccc1]

To a stirred and cooled (−78° C.) solution of oxalyl chloride (16.2 g, 127 mmol) in dichloromethane (200 mL) was added a solution of dimethyl sulfoxide (24 g, 255 mmol) in dichloromethane (50 mL) dropwise. The mixture was stirred at this temperature for 1 hour, then treated with a solution of 5-(benzyloxy)-4,4-dimethylpent-1-en-3-ol (Intermediate 108A, 20.8 g, 94.4 mmol) in dichloromethane (50 mL) dropwise. The mixture was stirred for another 2 hours, treated with triethylamine (38.2 g, 378 mmol) dropwise, and stirred for an additional 0.5 hours at −78° C. The reaction mixture was warmed to room temperature, stirred for 0.5 hours, quenched with water (100 mL), and extracted with dichloromethane (3×150 mL). The combined organic layers were washed with brine, dried over magnesium sulfate and concentrated. The residue was purified by automated flash chromatography (330 g silica gel column, eluted with 0-30% ethyl acetate in petroleum ether) to give the title compound (14.1 g, 68%) as an oil. MS (ESI): 219 m/z $[M+H]^+$, retention time: 1.35 minutes, purity: 86% (214 nm). (LC-MS Method 014).

Intermediate 108C: Methyl 7-(benzyloxy)-2-(3-bromophenyl)-2,6,6-trimethyl-5-oxoheptanoate

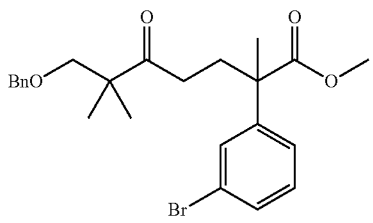 [SMILES: COC(=O)C(C)(CCC(=O)C(C)(C)COCc1ccccc1)c1cccc(Br)c1]

To a stirred and cooled (−78° C.) solution of methyl 2-(3-bromophenyl)propanoate (12 g, 49.4 mmol) in tetrahydrofuran (150 mL) was added lithium diisopropylamide (2 M in tetrahydrofuran, 27 mL, 54 mmol). The mixture was stirred at −78° C. for 1 hour, treated with a solution of 5-(benzyloxy)-4,4-dimethylpent-1-en-3-one (Intermediate 108B, 12.8 g, 58.6 mmol) in tetrahydrofuran (50 mL) dropwise, then slowly warmed up to room temperature, and stirred overnight. The reaction was quenched with saturated ammonium chloride (500 mL) and extracted with ethyl acetate (3×200 mL). The combined organic extracts were washed with brine, dried over sodium sulfate, and concentrated. The residue was purified by automated flash chromatography (330 g silica gel column, eluted with 0-30% ethyl acetate in petroleum ether) to give the title compound (10.5 g, 46%, mixture of methyl and ethyl ester) as an oil. MS (ESI): 461, 463 m/z $[M+H]^+$, retention time: 1.65 minutes, purity: 32% (214 nm) (LC-MS Method 014).

Intermediate 108D: Methyl 4-(2-(1-(benzyloxy)-2-methylpropan-2-yl)-1,3-dithiolan-2-yl)-2-(3-bromophenyl)-2-methylbutanoate

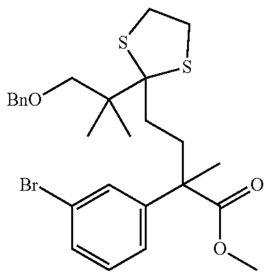 [SMILES: COC(=O)C(C)(CCC1(C(C)(C)COCc2ccccc2)SCCS1)c1cccc(Br)c1]

To a stirred solution of methyl 7-(benzyloxy)-2-(3-bromophenyl)-2,6,6-trimethyl-5-oxoheptanoate (Intermediate 108C, 9.5 g, 20.6 mmol, mixture of methyl and ethyl ester) and 1,2-ethanedithiol (5.18 mL, 61.8 mmol) in dichloromethane (250 mL) was added boron trifluoride etherate (6.86 mL, 55.6 mmol). The mixture was stirred at room temperature overnight, quenched with saturated sodium bicarbonate (150 mL), and extracted with dichloromethane (3×150 mL). The combined organic extracts were washed with saturated sodium bicarbonate, brine, dried over sodium sulfate, and concentrated. The residue was purified by automated flash chromatography (330 g silica gel column, eluted with 0-30% ethyl acetate in petroleum ether) to give the title compound (4.1 g, 37%) as an oil. MS (ESI) (methyl ester): 559, 561 m/z $[M+Na]^+$, retention time: 1.78 minutes, purity: 31% (214 nm) (LC-MS Method 014).

Intermediate 108E: Methyl 7-(benzyloxy)-2-(3-bromophenyl)-5,5-difluoro-2,6,6-trimethylheptanoate

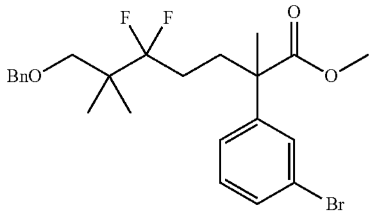 [SMILES: COC(=O)C(C)(CCC(F)(F)C(C)(C)COCc1ccccc1)c1cccc(Br)c1]

To a stirred and cooled (−30° C.) solution of N-iodosuccinimide (6.86 g, 30.5 mmol) in dichloromethane (120 mL) was added hydrogen fluoride-pyridine (8.25 mL, 91.5 mmol) under nitrogen. The mixture was stirred for 20 minutes at −30° C., then treated with a solution of methyl 4-(2-(1-(benzyloxy)-2-methylpropan-2-yl)-1,3-dithiolan-2-yl)-2-(3-bromophenyl)-2-methylbutanoate (Intermediate 108D, 4.1 g, 7.63 mmol) in dichloromethane (15 mL) dropwise and stirred at −30° C. for 4 hours. The reaction was quenched with saturated sodium bicarbonate (100 mL) and extracted with dichloromethane (3×100 mL). The combined organic extracts were washed with 10% sodium thiosulfate (2×30 mL), brine, dried over sodium sulfate, and concentrated. The crude mixture was purified by automated silica gel column chromatography (120 g column, 0-30% of ethyl acetate in petroleum) to give the title compound (960 mg, 26%) as oil. MS (ESI): 505 m/z $[M+Na]^+$, retention time: 1.71 minutes, purity: 19% (214 nm). (LC-MS Method 014).

Intermediate 108F: 7-(Benzyloxy)-2-(3-bromophenyl)-5,5-difluoro-2,6,6-trimethylheptanoic acid

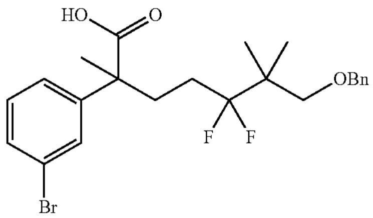 [SMILES: CC(CCC(F)(F)C(C)(C)COCc1ccccc1)(C(=O)O)c1cccc(Br)c1]

A mixture of methyl 7-(benzyloxy)-2-(3-bromophenyl)-5,5-difluoro-2,6,6-trimethylheptanoate (Intermediate 108E, 960 mg, 2 mmol) in a solution of lithium hydroxide (0.2 M in tetrahydrofuran/methanol/water (3:1:1), 50 mL) was stirred at 45° C. for 6 hours and concentrated. The residue was acidified with 1N hydrochloride (12 mL) to pH~2 and extracted with ethyl acetate (3×30 mL). The combined organic extracts were washed with brine, dried over sodium sulfate, and concentrated to give the crude title compound (905 mg, 97%) as oil. The crude product was used without further purification. MS (ESI): 491 m/z $[M+Na]^+$, retention time: 1.57 minutes, purity: 63% (214 nm). (LC-MS Method 014).

Intermediate 108G: (E)-7-(Benzyloxy)-2-(3-(3-ethoxy-3-oxoprop-1-en-1-yl)phenyl)-5,5-difluoro-2,6,6-trimethylheptanoic Acid

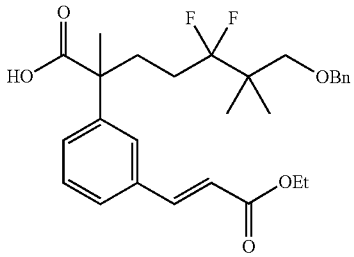 [SMILES: CCOC(=O)/C=C/c1cccc(C(C)(CCC(F)(F)C(C)(C)COCc2ccccc2)C(=O)O)c1]

To a stirred and degassed solution of 7-(benzyloxy)-2-(3-bromophenyl)-5,5-difluoro-2,6,6-trimethylheptanoic acid (Intermediate 108F, 905 mg, 1.93 mmol) in N,N-dimethylformamide (20 mL) was added tris(o-tolyl)phosphine (176 mg, 0.578 mmol), palladium (II) acetate (44 mg, 0.193 mmol), ethyl acrylate (1.26 mL, 11.56 mmol), and triethylamine (1.34 mL, 9.64 mmol). The reaction mixture was stirred at 120° C. overnight, cooled to room temperature, and quenched with 1 N hydrochloride (50 mL). The mixture was extracted with ethyl acetate (3×20 mL). The combined organic extracts were washed with brine, dried over sodium sulfate, and concentrated to give the crude title compound (0.57 g, 60%) as an oil. The crude product was used without further purification. MS (ESI): 511 m/z [M+Na]$^+$, retention time: 2.07 minutes, purity: 91% (214 nm). (LC-MS Method 011).

Intermediate 109: Benzyl 2-(3-(3-ethoxy-2-methyl-3-oxopropyl)phenyl)-7-((2-ethoxy-2-oxoethyl)sulfonyl)-2-(fluoromethyl)-6,6-dimethylheptanoate

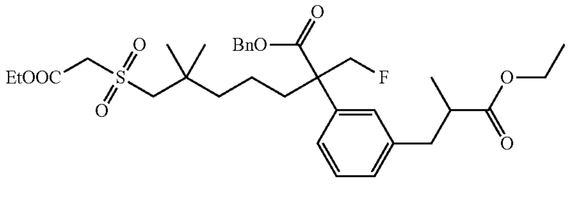 [SMILES: CCOC(=O)CS(=O)(=O)CC(C)(C)CCCC(CF)(C(=O)OCc1ccccc1)c1cccc(CC(C)C(=O)OCC)c1]

To a stirred and cooled (−78° C.) solution of benzyl 2-(3-(3-ethoxy-2-methyl-3-oxopropyl)phenyl)-7-((2-ethoxy-2-oxoethyl)sulfonyl)-2-(hydroxymethyl)-6,6-dimethylheptanoate (Intermediate 41-14, 5.0 g, 8.08 mmol) in dichloromethane (60 mL) was added diethylaminosulfur trifluoride (3.91 g, 24.2 mmol). The mixture was stirred at this temperature for 30 minutes, then warmed to 0° C. and stirred for an additional 30 minutes. The reaction was quenched with saturated sodium bicarbonate (100 mL) and extracted with dichloromethane (3×100 mL). The combined organic extracts were washed with brine, dried over sodium sulfate, and concentrated. The residue was purified by automated flash chromatography (40 g silica gel column, eluted with 0-30% ethyl acetate in petroleum) to give the title compound (3.0 g, 60%) as a colorless oil. MS (ESI): 621 m/z [M+H]$^+$, retention time: 1.93 minutes, purity: 90% (214 nm) (LC-MS Method 028).

Intermediate 110: 2-(3-Bromophenyl)-2-methyl-4-((2-methyl-2-(1H-pyrazol-4-yl)propyl)thio)butanoic Acid

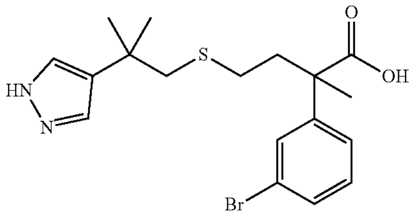 [SMILES: CC(C)(CSCCC(C)(C(=O)O)c1cccc(Br)c1)c1cn[nH]c1]

To a stirred solution of methyl 2-(3-bromophenyl)-2-methyl-4-((2-methyl-2-(1H-pyrazol-4-yl)propyl)thio)butanoate (Intermediate 110G, 2.9 g, 6.8 mmol) in methanol (30 mL) and water (6 mL) was added lithium hydroxide monohydrate (1.43 g, 34 mmol). The mixture was stirred at 50° C. for 16 hours, then diluted with water (100 mL), acidified to pH~5-6 with 1N hydrochloric acid, and extracted with ethyl acetate (3×100 mL). The combined organic extracts were washed with water, brine, dried over sodium sulfate, and concentrated. The residue was purified by automated flash chromatography (80 g silica gel column, eluted with 0-100% ethyl acetate in petroleum ether) to give the title compound (2.6 g, 93%). MS (ESI): 411, 413 m/z [M+H]$^+$, retention time: 1.23 minutes, purity: 73% (254 nm). (LC-MS Method 014).

Intermediate 110A: 2-(1-Tosyl-1H-pyrazol-4-yl)propan-2-ol

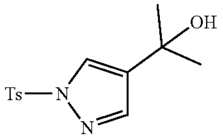 [SMILES: Cc1ccc(S(=O)(=O)n2cc(C(C)(C)O)cn2)cc1]

To a stirred and cooled (0° C.) solution of ethyl 1-tosyl-1H-pyrazole-4-carboxylate (45 g, 0.153 mol) in tetrahydrofuran (150 mL) was added methylmagnesium bromide (2 M in tetrahydrofuran, 153 mL, 0.459 mol) under nitrogen. The mixture was stirred for 2 hours, quenched with 300 mL of saturated ammonium chloride, and extracted with ethyl acetate (3×300 mL). The combined organic extracts were washed with brine, dried over sodium sulfate, and concentrated. The residue was purified by silica gel column chromatography (petroleum ether:ethyl acetate=1.5:1) to give the title compound (28 g, 65%) as a white solid. MS (ESI): 281 m/z [M+H]$^+$, retention time: 1.63 minutes, purity: 93% (214 nm). (LC-MS Method 014).

Intermediate 110B: 2-Methyl-2-(1-tosyl-1H-pyrazol-4-yl)propanenitrile

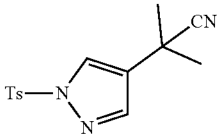 [SMILES: Cc1ccc(S(=O)(=O)n2cc(C(C)(C)C#N)cn2)cc1]

To a stirred solution of 2-(1-tosyl-1H-pyrazol-4-yl)propan-2-ol (Intermediate 110A, 28 g, 0.0999 mol) in dichloromethane (100 mL) were added indium (III) bromide (3.54 g, 9.99 mmol) and trimethylsilylcyanide (37.5 mL, 0.3 mol). The mixture was stirred at room temperature overnight, quenched with 200 mL of water and extracted with dichloromethane (3×200 mL). The combined organic extracts were washed with brine, dried over sodium sulfate, and concentrated. The residue was purified by silica gel column chromatography (petroleum ether:ethyl acetate=1:1) to give the title compound (18 g, 62.3%) as a white solid. MS (ESI): 290 m/z [M+H]$^+$, retention time: 1.78 minutes, purity: 91% (214 nm). (LC-MS Method 014).

Intermediate 110C: 2-Methyl-2-(1-tosyl-1H-pyrazol-4-yl)propanal

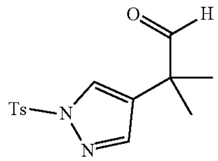 [SMILES: Cc1ccc(S(=O)(=O)n2cc(C(C)(C)C=O)cn2)cc1]

To a stirred and cooled (0° C.) solution of 2-methyl-2-(1-tosyl-1H-pyrazol-4-yl)propanenitrile (Intermediate 110B, 13 g, 0.045 mol) in dichloromethane (100 mL) was added diisobutyl aluminum hydride (1 M in hexane, 53.9 mL, 0.0539 mol). The mixture was stirred for 4 hours at 0° C., quenched with hydrochloric acid solution (1 M, 100 mL), and stirred for another 30 minutes. The solution was extracted with dichloromethane (3×200 mL). The combined organic extracts were washed with brine, dried over sodium sulfate, and concentrated to give the crude title compound (13 g, 99%) as a light-yellow solid. The crude product was used in the next step without further purification. MS (ESI): 293 m/z [M+H]$^+$, retention time: 1.79 minutes, purity: 60% (214 nm). (LC-MS Method 014).

Intermediate 110D: 2-Methyl-2-(1-tosyl-1H-pyrazol-4-yl)propan-1-ol

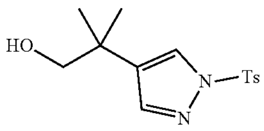 [SMILES: Cc1ccc(S(=O)(=O)n2cc(C(C)(C)CO)cn2)cc1]

To a stirred and cooled (0° C.) solution of 2-methyl-2-(1-tosyl-1H-pyrazol-4-yl)propanal (Intermediate 110C, 13 g, 44.5 mmol) in tetrahydrofuran (100 mL) was added sodium borohydride (1.68 g, 44.5 mmol). The mixture was stirred for 1 hour, then quenched with 200 mL of water, and extracted with ethyl acetate (3×200 mL). The combined organic extracts were washed with brine, dried over sodium sulfate, and concentrated. The residue was purified by silica gel column chromatography (petroleum ether:ethyl acetate=1.5:1) to give the title compound (8.5 g, 64.9%) as a white solid. MS (ESI): 295 m/z [M+H]$^+$, retention time: 1.68 minutes, purity: 95% (214 nm). (LC-MS Method 014).

Intermediate 110E. S-(2-Methyl-2-(1-tosyl-1H-pyrazol-4-yl)propyl) ethanethioate

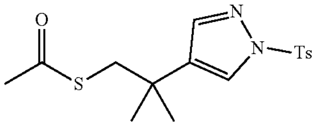 [SMILES: CC(=O)SCC(C)(C)c1cnn(S(=O)(=O)c2ccc(C)cc2)c1]

To a stirred and cooled (0° C.) solution of triphenylphosphine (10.7 g, 40.8 mmol) in tetrahydrofuran (200 mL) was added diisopropyl azodiformate (8.03 mL, 40.8 mmol) dropwise. The mixture was stirred at 0° C. until the formation of a white solid. To the white suspension was added a solution of 2-methyl-2-(1-tosyl-1H-pyrazol-4-yl)propan-1-ol (Intermediate 110D, 4 g, 13.6 mmol) and thiolacetic acid (2.9 mL, 40.8 mmol) in tetrahydrofuran (50 mL) dropwise. The solution was stirred at 0° C. for 1 hour, then warmed to 25° C. and stirred for an additional 1 hour. The reaction was quenched with 120 mL of water and extracted with ethyl acetate (3×120 mL). The combined organic extracts were washed with brine, dried over sodium sulfate, and concentrated. The residue was purified by silica gel column chromatography (petroleum ether:ethyl acetate=4:1) to give the title compound (3.5 g, 73%) as a yellow solid. MS (ESI): 353 m/z [M+H]$^+$, retention time: 1.91 minutes, purity: >99% (214 nm). (LC-MS Method 014).

Intermediate 110F: Methyl 2-(3-bromophenyl)-4-iodo-2-methylbutanoate

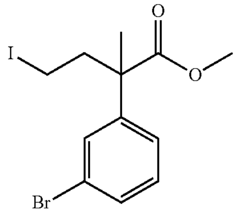 [SMILES: COC(=O)C(C)(CCI)c1cccc(Br)c1]

To a stirred solution of methyl 4-bromo-2-(3-bromophenyl)-2-methylbutanoate (700 mg, 2 mmol) in acetone (20 mL) was added sodium iodide (0.899 g, 6 mmol). The mixture was stirred at 70° C. overnight. The solvent was evaporated. The residue was dissolved in petroleum ether (100 mL) and dichloromethane (10 mL) and filtered. The filtrate was concentrated and purified by silica gel column chromatography (petroleum ether:ethyl acetate=9:1) to give the title compound (700 mg, 88.2%) as a yellow liquid. MS (ESI): 397, 399 m/z [M+H]$^+$, retention time: 2.09 minutes, purity: 80% (214 nm). (LC-MS Method 003).

Intermediate 110G: Methyl 2-(3-bromophenyl)-4-iodo-2-methylbutanoate

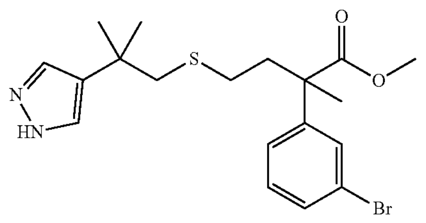 [SMILES: COC(=O)C(C)(CCSCC(C)(C)c1cn[nH]c1)c1cccc(Br)c1]

To a stirred solution of methyl 2-(3-bromophenyl)-4-iodo-2-methyl-butanoate (Intermediate 110F, 10.3 g, 26 mmol) in tetrahydrofuran (300 mL) was added S-(2-methyl-2-(1-tosyl-1H-pyrazol-4-yl)propyl) ethanethioate (Intermediate 110E, 7 g, 20 mmol) and potassium tert-butoxide (6.7 g, 60 mmol). The mixture was stirred at room temperature for 3 hours, quenched with saturated ammonium chloride (200 mL), and extracted with ethyl acetate (3×200 mL). The combined organic extracts were washed with water, brine, dried over sodium sulfate, and concentrated. The residue was purified by automated flash chromatography (120 g silica gel column, eluted with 0-100% ethyl acetate in petroleum ether) to give the title compound (2.9 g, 34%). MS (ESI): 425, 427 m/z $[M+H]^+$, retention time: 1.37 minutes, purity: 83% (214 nm). (LC-MS Method 014).

Intermediate 111: 2-(3-Bromophenyl)-2-methyl-5-((2-(1-((2-(trimethylsilyl)ethoxy)methyl)-1H-pyrazol-4-yl)propan-2-yl)sulfonyl)pentanoic Acid

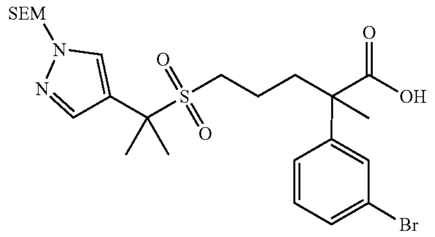 [SMILES: CC(CCCS(=O)(=O)C(C)(C)c1cnn(COCC[Si](C)(C)C)c1)(C(=O)O)c1cccc(Br)c1]

To a stirred solution of 2-(3-bromophenyl)-2-methyl-5-((2-(1-((2-(trimethylsilyl)ethoxy)methyl)-1H-pyrazol-4-yl)propan-2-yl)thio)pentanoic acid (Intermediate 111D, 16 g, 26.6 mmol) in methanol (200 mL) was added hydrogen peroxide (30% in water, 43 mL) and ammonium molybdate tetrahydrate (16 g). The mixture was stirred for 2 hours, then acidified with 200 mL of 1N hydrochloric acid and 100 mL of water. The solution was extracted with ethyl acetate (2×200 mL). The combined organic extracts were washed with water (100 mL), dried over sodium sulfate, and concentrated. The residue was purified with automated flash chromatography to give the title compound (13 g, 90%). MS (ESI): 573, 575 m/z $[M+H]^+$, retention time: 2.14 minutes, purity: 90% (214 nm) (LC-MS Method 022).

Intermediate 111A: 2-(1-((2-(Trimethylsilyl)ethoxy)methyl)-1H-pyrazol-4-yl)propan-2-ol

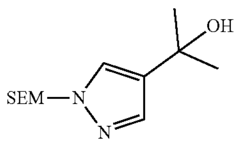 [SMILES: CC(C)(O)c1cnn(COCC[Si](C)(C)C)c1]

To a stirred solution of ethyl 1-((2-(trimethylsilyl)ethoxy)methyl)-1H-pyrazole-4-carboxylate (15 g, 55.5 mmol) in tetrahydrofuran (200 mL) at room temperature was added methylmagnesium bromide (2.5 M in tetrahydrofuran, 66.6 mL, 166.5 mmol). The mixture was stirred for 6 hours, then quenched with saturated ammonium chloride solution (100 mL) and extracted with ethyl acetate (3×100 mL). The combined organic extracts were washed with saturated lithium chloride, dried over sodium sulfate, and concentrated. The residue was purified by flash chromatography to give the title compound (10.2 g, 72%). MS (ESI): 257 m/z $[M+H]^+$, retention time: 1.92 minutes, purity: 90% (214 nm). (LC-MS Method 022).

Intermediate 111B: S-(2-(1-((2-(Trimethylsilyl)ethoxy)methyl)-1H-pyrazol-4-yl)propan-2-yl) ethanethioate

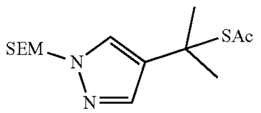

To a stirred solution of 2-(1-((2-(trimethylsilyl)ethoxy)methyl)-1H-pyrazol-4-yl)propan-2-ol (Intermediate 111A, 10.2 g, 39.8 mmol) and ethanethioic S-acid (9.07 g, 119 mmol) in dichloromethane (300 mL) was added boron trifluoride ethyl ether complex (5.65 g, 39.8 mmol). The mixture was stirred for 1 hour, then quenched with saturated sodium bicarbonate (100 mL) and extracted with dichloromethane (3×150 mL). The combined organic extracts were washed with water (100 mL), dried over sodium sulfate, and concentrated. The residue was purified by flash chromatography to give the crude title compound (12.5 g, 100%). The crude product was used in the next step without further purification. MS (ESI): 315 m/z $[M+H]^+$, retention time: 2.26 minutes, purity: 90% (214 nm). (LC-MS Method 022).

Intermediate 111C: Methyl 2-(3-bromophenyl)-2-methyl-5-((2-(1-((2-(trimethylsilyl)ethoxy)methyl)-1H-pyrazol-4-yl)propan-2-yl)thio)pentanoate

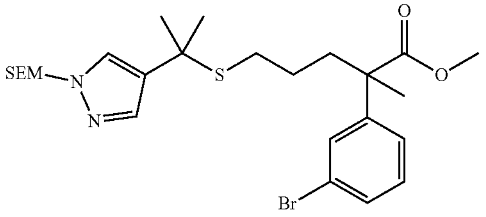 [SMILES: COC(=O)C(C)(CCCSC(C)(C)c1cnn(COCC[Si](C)(C)C)c1)c1cccc(Br)c1]

To a stirred and degassed solution of S-(2-(1-((2-(trimethylsilyl)ethoxy)methyl)-1H-pyrazol-4-yl)propan-2-yl) ethanethioate (Intermediate 111B, 13 g, 41.2 mmol) in 1 L of methanol was added potassium hydroxide (4.62 g, 82.4 mmol). The mixture was stirred for 15 minutes, then treated with methyl 5-bromo-2-(3-bromophenyl)-2-methyl-pentanoate (Intermediate 16-8, 15 g, 41.2 mmol). The solution was stirred for 16 hours at 35° C., quenched with saturated sodium hydrogen carbonate (1 L), and extracted with ethyl acetate (2×200 mL). The combined organic extracts were washed with water, dried over sodium sulfate, and concentrated to give the crude title compound (25 g). This crude product was used in the next step without further purification. MS (ESI): 555, 557 m/z $[M+H]^+$, retention time: 2.92 minutes, purity: 90% (214 nm). (LC-MS Method 010).

Intermediate 111D: 2-(3-Bromophenyl)-2-methyl-5-((2-(1-((2-(trimethylsilyl)ethoxy)methyl)-1H-pyrazol-4-yl)propan-2-yl)thio)pentanoic Acid

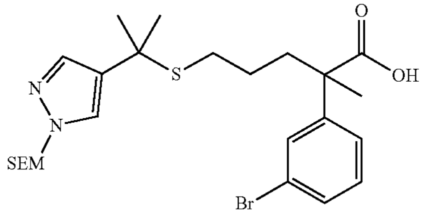 [SMILES: CC(C)(SCCCC(C)(C(=O)O)c1cccc(Br)c1)c1cnn(COCC[Si](C)(C)C)c1]

A mixture of methyl 2-(3-bromophenyl)-2-methyl-5-((2-(1-((2-(trimethylsilyl)ethoxy)methyl)-1H-pyrazol-4-yl)propan-2-yl)thio)pentanoate (Intermediate 111C, 25 g, crude) in 0.2 M lithium hydroxide (in tetrahydrofuran:methanol:water=3:1:1, 562 mL) was stirred at 45° C. for 4 days, cooled to room temperature and acidified with 150 mL of 1 N hydrochloric acid. The mixture was extracted with dichloromethane (3×200 mL). The combined organic extracts were washed with water (100 mL), dried over sodium sulfate, and concentrated. The residue was purified by flash chromatography to give the title compound (20 g, 70% for 2 steps). MS (ESI): 541, 543 m/z $[M+H]^+$, retention time: 2.37 minutes, purity: 90% (214 nm) (LC-MS Method 022).

Intermediate 112: Ethyl 3-(3-(2-methyl-1-(2-methylhydrazineyl)-1-oxo-5-((2-(1-((2-(trimethylsilyl)ethoxy)methyl)-1H-pyrazol-4-yl)propan-2-yl)sulfonyl)pentan-2-yl)phenyl)propanoate

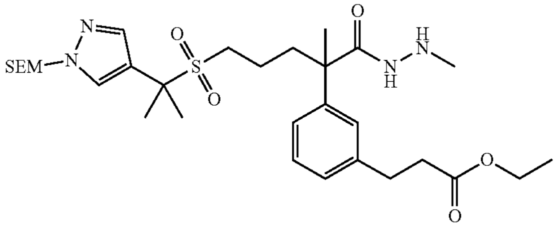 [SMILES: CCOC(=O)CCc1cccc(C(C)(CCCS(=O)(=O)C(C)(C)c2cnn(COCC[Si](C)(C)C)c2)C(=O)NNC)c1]

To a stirred solution of benzyl (E)-2-(2-(3-(3-ethoxy-3-oxoprop-1-en-1-yl)phenyl)-2-methyl-5-((2-(1-((2-(trimethylsilyl)ethoxy)methyl)-1H-pyrazol-4-yl)propan-2-yl)sulfonyl)pentanoyl)-1-methylhydrazine-1-carboxylate (Intermediate 112B, 7.0 g, 9.27 mmol) in ethanol (10 mL) was added palladium on active carbon (10%, 2.0 g). The mixture was stirred at 45° C. for 16 hours, then filtered through a pad of Celite. The filtrate was concentrated to give the crude title compound (5.0 g, 86%). The crude product was used in the next step without further purification. MS (ESI): 623 m/z $[M+H]^+$, retention time: 2.03 minutes, purity: 90% (214 nm). (LC-MS Method 022).

The following intermediate was prepared based on the procedures described for Intermediate 112.

| Inter. No. | Structure | Name | MS m/z $[M + H]^+$ |
|---|---|---|---|
| 112-1 | 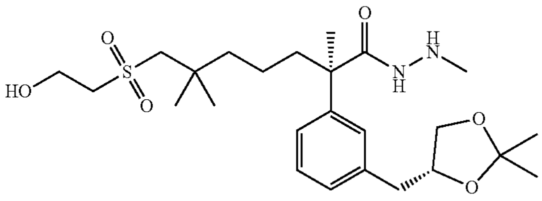 [SMILES: CNNC(=O)[C@](C)(CCCC(C)(C)CS(=O)(=O)CCO)c1cccc(C[C@@H]2COC(C)(C)O2)c1] | (R)-2-(3-(((R)-2,2-dimethyl-1,3-dioxolan-4-yl)methyl)phenyl)-7-((2-hydroxyethyl)sulfonyl)-N',2,6,6-tetramethylheptanehydrazide (diastereomixture~7:3 R:S on 1,3-dioxolane) | 499 $[M + H]^+$; RT: 1.42 min. (LC-MS Method 16) |

Intermediate 112A: (E)-2-(3-(3-Ethoxy-3-oxoprop-1-en-1-yl)phenyl)-2-methyl-5-((2-(1-((2-(trimethylsilyl)ethoxy)methyl)-1H-pyrazol-4-yl)propan-2-yl)sulfonyl)pentanoic Acid

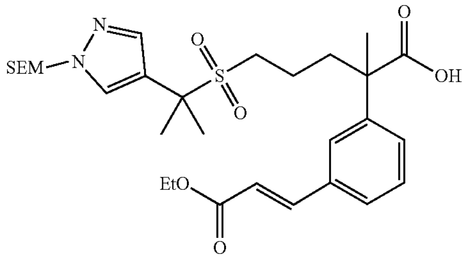 [SMILES: CCOC(=O)/C=C/c1cccc(C(C)(CCCS(=O)(=O)C(C)(C)c2cnn(COCC[Si](C)(C)C)c2)C(=O)O)c1]

To a stirred solution of (E)-2-(3-(3-ethoxy-3-oxoprop-1-en-1-yl)phenyl)-2-methyl-5-((2-(1-((2-(trimethylsilyl)ethoxy)methyl)-1H-pyrazol-4-yl)propan-2-yl)sulfonyl)pentanoic acid (Intermediate 112A, 6 g, 10 mmol) in acetonitrile (50 mL) was added 1-methylimidazole (2.49 g, 3 mmol), N,N,N',N'-tetramethylchloroformamidinium hexafluorophosphate (2.84 g, 10 mmol) and benzyl N-amino-N-methyl-carbamate (2.74 g, 15 mmol). The resulting mixture was stirred at room temperature for 4 hours, quenched with water (100 mL), and extracted with ethyl acetate (2×150 mL). The combined organic extracts were washed with water, dried over sodium sulfate, and concentrated to give the crude title compound (7.0 g, 92%). The crude product was used in the next step without further purification. MS (ESI): 755 m/z $[M+H]^+$, retention time: 2.23 minutes, purity: 90% (254 nm). (LC-MS Method 022).

The following intermediate was prepared based on the procedures described for Intermediate 112B.

| Inter. No. | Structure | Name | MS m/z $[M + H]^+$ |
|---|---|---|---|
| 112B-1 | 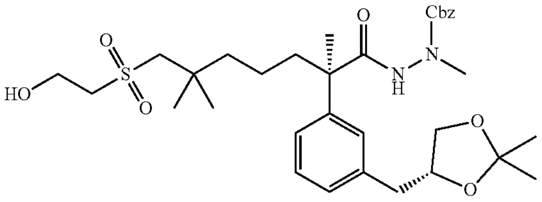 | benzyl 2-((R)-2-(3-(((R)-2,2-dimethyl-1,3-dioxolan-4-yl)methyl)phenyl)-7-((2-hydroxyethyl)sulfonyl)-2,6,6-trimethylheptanoyl)-1-methylhydrazine-1-carboxylate (diastereo-mixture~7:3 R:S on 1,3-dioxolane) | 655 $[M + Na]^+$; RT: 1.52 min. (LC-MS Method 16) |

To a stirred and degassed solution of 2-(3-bromophenyl)-2-methyl-5-((2-(1-((2-(trimethylsilyl)ethoxy)methyl)-1H-pyrazol-4-yl)propan-2-yl)sulfonyl)pentanoic acid (Intermediate 111, 15 g, 26.1 mmol) in 1,4-dioxane (100 mL) and water (25 ml) were added ethyl (E)-3-(4,4,5,5-tetramethyl-1,3,2-dioxaborolan-2-yl)prop-2-enoate (7.09 g, 31.4 mmol), [1,1'-bis(diphenylphosphino)ferrocene]dichloropalladium (II) (1.91 g, 2.61 mmol) and cesium carbonate (17 g, 52.3 mmol). The mixture was stirred at 100° C. for 16 hours, then cooled to room temperature, diluted with 300 mL of water, and extracted with ethyl acetate (2×100 mL). The combined organic extracts were washed with water, dried over sodium sulfate, and concentrated. The residue was purified with flash chromatography to give the title compound (13 g, 90%). MS (ESI): 593 m/z $[M+H]^+$, retention time: 2.14 minutes, purity: 90% (254 nm). (LC-MS Method 022).

Intermediate 112B: Benzyl (E)-2-(2-(3-(3-ethoxy-3-oxoprop-1-en-1-yl)phenyl)-2-methyl-5-((2-(1-((2-(trimethylsilyl)ethoxy)methyl)-1H-pyrazol-4-yl)propan-2-yl)sulfonyl)pentanoyl)-1-methylhydrazine-1-carboxylate

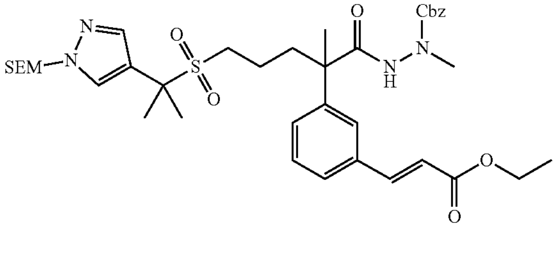 [SMILES: CCOC(=O)/C=C/c1cccc(C(C)(CCCS(=O)(=O)C(C)(C)c2cnn(COCC[Si](C)(C)C)c2)C(=O)NN(C)C(=O)OCc2ccccc2)c1]

Intermediate 113: 2-(3-Bromophenyl)-4-((2-((2-hydroxyethyl)thio)ethyl)thio)-2-methylbutanoic Acid

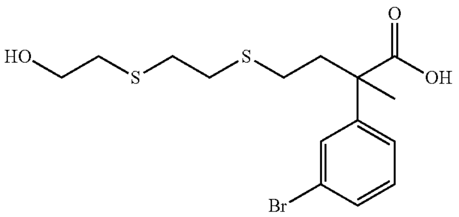 [SMILES: CC(CCSCCSCCO)(C(=O)O)c1cccc(Br)c1]

To a stirred solution of methyl 2-(3-bromophenyl)-4-((2-((2-hydroxyethyl)thio)ethyl)thio)-2-methylbutanoate (Intermediate 113C, 4.5 g, 11.0 mmol) in tetrahydrofuran (90 mL) and methanol (30 mL) was added lithium hydroxide (1 M in water) (33.1 mL, 33.1 mmol). The mixture was stirred at room temperature for 3 hours, then diluted with water (100 mL), acidified with 6 N hydrochloric acid (6 mL), and extracted with ethyl acetate (3×100 mL). The combined organic extracts were washed with brine (80 mL), dried over sodium sulfate, and concentrated to give the crude title compound (4.2 g, 97%). The crude product was used in the next step without further purification. MS (ESI): 415, 417 m/z $[M+Na]^+$, retention time: 1.68 minutes, purity: 81% (214 nm). (LC-MS Method 011).

Intermediate 113A: Methyl 2-(3-bromophenyl)-4-((2-hydroxyethyl)thio)-2-methylbutanoate

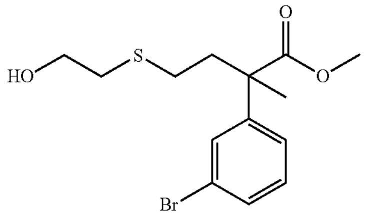 [SMILES: COC(=O)C(C)(CCSCCO)c1cccc(Br)c1]

To a stirred and cooled (0° C.) solution of methyl 4-(acetylthio)-2-(3-bromophenyl)-2-methylbutanoate (Intermediate 104A, 6 g, 17.4 mmol) in methanol (15 mL) was added 2-bromoethanol (6.52 g, 52.1 mmol), sodium methoxide (1.41 g, 26.1 mmol) under nitrogen. The mixture was stirred at room temperature for 2 hours, diluted with water (30 mL), and extracted with ethyl acetate (3×30 mL). The combined organic extracts were dried over sodium sulfate, and concentrated. The residue was purified by silica gel column chromatography (ethyl acetate in petroleum ether=0-50%) to give the title compound (4.8 g, 80%). MS (ESI): 369, 371 m/z $[M+Na]^+$, retention time: 1.78 minutes, purity: 93% (214 nm). (LC-MS Method 011).

Intermediate 113B: Methyl 4-((2-(acetylthio)ethyl)thio)-2-(3-bromophenyl)-2-methylbutanoate

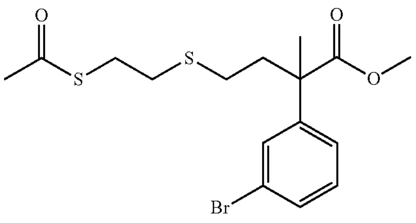 [SMILES: COC(=O)C(C)(CCSCCSC(C)=O)c1cccc(Br)c1]

To a stirred and cooled (0° C.) solution of triphenylphosphine (8.31 g, 31.7 mmol) in tetrahydrofuran (50 mL) was added diisopropyl azodicarboxylate (6.41 g, 31.7 mmol) under nitrogen. The reaction mixture was stirred at 0° C. for 0.5 hour, then treated with ethanethioic S-acid (2.89 g, 38.0 mmol) and methyl 2-(3-bromophenyl)-4-((2-hydroxyethyl)thio)-2-methylbutanoate (Intermediate 113A, 4.4 g, 12.7 mmol) in tetrahydrofuran (20 mL). The mixture was stirred at room temperature overnight and concentrated. The residue was triturated with mixed solvent (petroleum ether:ethyl acetate=10:1, 50 mL) and filtered. The filtrate was concentrated. The residue was purified by automated silica gel column chromatography (ethyl acetate in petroleum ether=0-20%) to give the title compound (4.9 g, 95%). MS (ESI): 427, 429 m/z $[M+Na]^+$, retention time: 2.03 minutes, purity: 95% (214 nm). (LC-MS Method 011).

Intermediate 113C: Methyl 2-(3-bromophenyl)-4-((2-((2-hydroxyethyl)thio)ethyl)thio)-2-methylbutanoate

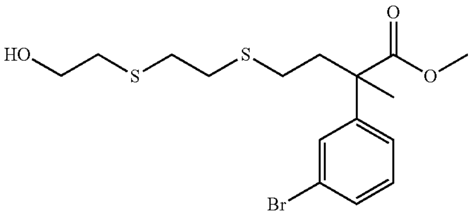 [SMILES: COC(=O)C(C)(CCSCCSCCO)c1cccc(Br)c1]

To a stirred and cooled (0° C.) solution of methyl 4-((2-(acetylthio)ethyl)thio)-2-(3-bromophenyl)-2-methylbutanoate (Intermediate 113B, 4.9 g, 12.1 mmol) in methanol (40 mL) was added 2-bromoethanol (4.53 g, 36.3 mmol) and sodium methoxide (0.98 g, 18.1 mmol). The mixture was stirred at room temperature for 1 hour, diluted with water (100 mL), and extracted with ethyl acetate (3×80 mL). The combined organic extracts were dried over sodium sulfate and concentrated. The residue was purified by automated silica gel column chromatography (ethyl acetate in petroleum ether=0-50%) to give the title compound (4.5 g, 91%). MS (ESI): 429, 431 m/z $[M+Na]^+$, retention time: 1.83 minutes, purity: 96% (214 nm) (LC-MS Method 011).

Intermediate 114: Ethyl (E)-3-(3-(4-((2-((2-hydroxyethyl)thio)ethyl)thio)-2-methyl-1-(2-methylhydrazineyl)-1-oxobutan-2-yl)phenyl)-2-methylacrylate

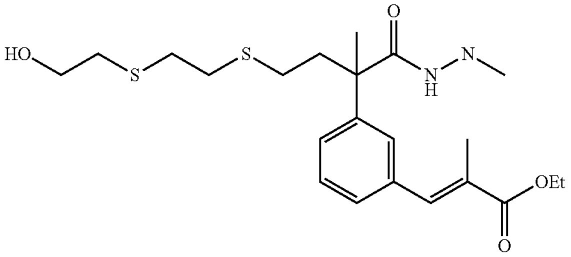 [SMILES: CCOC(=O)/C(C)=C/c1cccc(C(C)(CCSCCSCCO)C(=O)NNC)c1]

To a stirred solution of tert-butyl 2-(2-(3-(3-ethoxy-2-methyl-3-oxoprop-1-en-1-yl)phenyl)-4-((2-((2-hydroxyethyl)thio)ethyl)thio)-2-methylbutanoyl)-1-methylhydrazine-1-carboxylate (Intermediate 114B, 1 g, 1.8 mmol) in dichloromethane (10 mL) was added trifluoroacetic acid (2 mL). The mixture was stirred at room temperature for 2 hours and concentrated. The residue was dissolved in ethyl acetate (50 mL), washed with saturated sodium bicarbonate and brine, dried over sodium sulfate, and concentrated to give the title compound (0.815 g) as an oil. The compound was used in the next step without further purification. MS (ESI): 455 m/z $[M+H]^+$, retention time: 1.12 minutes, purity: 72% (214 nm). (LC-MS Method 014).

Intermediate 114A: Tert-Butyl 2-(2-(3-bromophenyl)-4-((2-((2-hydroxyethyl)thio)ethyl)thio)-2-methylbutanoyl)-1-methylhydrazine-1-carboxylate

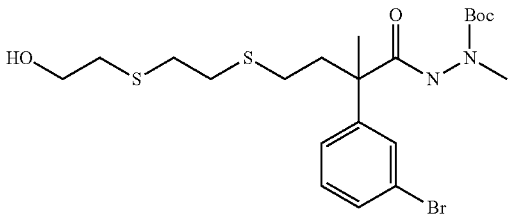

To a stirred solution of 2-(3-bromophenyl)-4-((2-((2-hydroxyethyl)thio)ethyl)thio)-2-methylbutanoic acid (Intermediate 113, 2.9 g, 7.37 mmol) in acetonitrile (50 mL) was added N,N,N',N'-tetramethylchloroformamidinium hexafluorophosphate (2.07 g, 7.37 mmol), 1-methylimidazole (2.12 g, 25.8 mmol) and tert-butyl 1-methylhydrazine-1-carboxylate (1.29 g, 8.85 mmol). The reaction mixture was stirred at room temperature for 2 hours. The mixture was then diluted with ethyl acetate (150 mL), washed with water, dried over magnesium sulfate, and concentrated. The residue was purified by silica gel column chromatography (80 g silica gel column, eluted with 0-10% methanol in dichloromethane) to give the title compound (3.05 g, 79%) as an oil. MS (ESI): 543, 545 m/z $[M+Na]^+$, retention time: 1.30 minutes, purity: 89% (214 nm) (LC-MS Method 014).

Intermediate 114B: Tert-Butyl (E)-2-(2-(3-(3-ethoxy-2-methyl-3-oxoprop-1-en-1-yl)phenyl)-4-((2-((2-hydroxyethyl)thio)ethyl)thio)-2-methylbutanoyl)-1-methylhydrazine-1-carboxylate

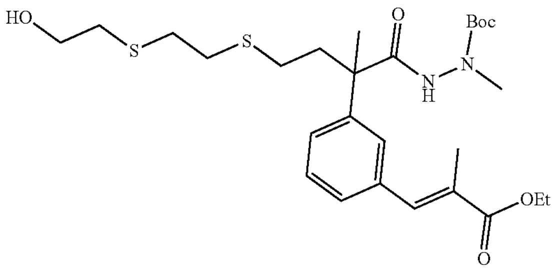 [SMILES: CCOC(=O)/C(C)=C/c1cccc(C(C)(CCSCCSCCO)C(=O)NN(C)C(=O)OC(C)(C)C)c1]

To a stirred solution of tert-butyl 2-(2-(3-bromophenyl)-4-((2-((2-hydroxyethyl)thio)ethyl)thio)-2-methylbutanoyl)-1-methylhydrazine-1-carboxylate (Intermediate 114A, 3.05 g, 5.85 mmol) in dioxane (56 mL) and water (14 mL) were added ethyl (E)-2-methyl-3-(4,4,5,5-tetramethyl-1,3,2-dioxaborolan-2-yl)prop-2-enoate (1.97 g, 8.19 mmol), cesium carbonate (3.80 g, 11.7 mmol), and 1,1'-bis(diphenylphosphino)ferrocene-palladium (II) dichloride dichloromethane complex (955 mg, 1.17 mmol). The mixture was stirred at 100° C. overnight, cooled to room temperature, diluted with water (150 mL) and extracted with ethyl acetate (3×150 mL). The combined organic layers were washed with brine, dried over sodium sulfate, and concentrated. The residue was purified by automated silica gel column chromatography (80 g silica gel column, eluted with 0-70% ethyl acetate in petroleum ether) to give the title compound (2.28 g, 70%) as an oil. MS (ESI): 577 m/z $[M+Na]^+$, retention time: 1.37 minutes, purity: 88% (214 nm). (LC-MS Method 014).

Intermediate 115: Ethyl 3-(3-(3-(3-((2-hydroxyethyl)sulfonyl)-2,2-dimethylpropoxy)-2-methyl-1-(2-methylhydrazineyl)-1-oxopropan-2-yl)phenyl)-2-methylpropanoate

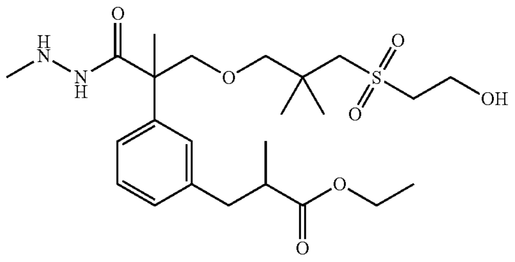 [SMILES: CCOC(=O)C(C)Cc1cccc(C(C)(COCC(C)(C)CS(=O)(=O)CCO)C(=O)NNC)c1]

To a stirred solution of tert-butyl 2-(2-(3-(3-ethoxy-2-methyl-3-oxopropyl)phenyl)-3-(3-((2-hydroxyethyl)sulfonyl)-2,2-dimethylpropoxy)-2-methylpropanoyl)-1-methylhydrazine-1-carboxylate (Intermediate 115F, 2.6 g, 4.33 mmol) in dichloromethane (20 mL) was added trifluoroacetic acid (3.2 mL, 43.3 mmol). The reaction was stirred at room temperature for 2 hours, then concentrated. The residue was dissolved in ethyl acetate (100 mL), washed with saturated sodium bicarbonate (100 mL), dried over magnesium sulfate, and concentrated to give the crude title compound (2 g, 92.3%) as an oil. This crude product was used in the next step without further purification. MS (ESI): 501 m/z $[M+H]^+$, retention time: 1.78 minutes, purity: 95% (254 nm). (LC-MS Method 022).

Intermediate 115A: 2-(3-Bromophenyl)-3-(3-((2-ethoxy-2-oxoethyl)thio)-2,2-dimethylpropoxy)-2-methylpropanoic Acid

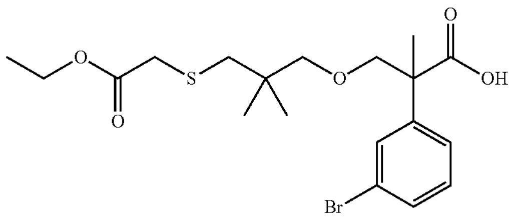 [SMILES: CCOC(=O)CSCC(C)(C)COCC(C)(C(=O)O)c1cccc(Br)c1]

To a stirred solution of tert-butyl 2-(3-bromophenyl)-3-(3-((2-ethoxy-2-oxoethyl)thio)-2,2-dimethylpropoxy)-2-methylpropanoate (Intermediate 91E-1, 9 g, 17.9 mmol) in dichloromethane (100 mL) was added trifluoroacetic acid (13.3 mL, 179 mmol). The reaction mixture was stirred at room temperature for 3 hours and concentrated. The residue was purified by automated flash chromatography (120 g silica gel column, eluted with 0-50% ethyl acetate in petroleum ether) to give the title compound (7.2 g, 90%) as an oil. MS (ESI): 469, 471 m/z $[M+Na]^+$, retention time: 2.20 minutes, purity: 92% (254 nm) (LC-MS Method 022).

Intermediate 115B: Tert-Butyl 2-(2-(3-bromophenyl)-3-(3-((2-ethoxy-2-oxoethyl)thio)-2,2-dimethylpropoxy)-2-methylpropanoyl)-1-methylhydrazine-1-carboxylate

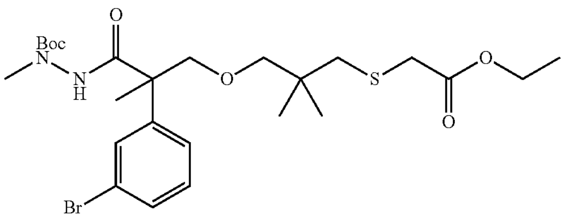 [SMILES: CCOC(=O)CSCC(C)(C)COCC(C)(C(=O)NN(C)C(=O)OC(C)(C)C)c1cccc(Br)c1]

To a stirred solution of 2-(3-bromophenyl)-3-(3-((2-ethoxy-2-oxoethyl)thio)-2,2-dimethylpropoxy)-2-methylpropanoic acid (Intermediate 115A, 7.2 g, 16.1 mmol) in acetonitrile (100 mL) was added tert-butyl N-amino-N-methyl-carbamate (2.59 g, 17.7 mmol), 1-methylimidazole (4.62 g, 56.3 mmol) and N,N,N',N'-tetramethylchloroformamidinium hexafluorophosphate (4.52 g, 16.1 mmol). The reaction mixture was stirred for 1 hour, then diluted with ethyl acetate (200 mL) and washed with water, dried over magnesium sulfate, and concentrated. The residue was purified by automated silica gel column chromatography (120 g silica gel column, eluted with 0-50% ethyl acetate in petroleum ether) to give the title compound (7 g, 76%) as an oil. MS (ESI): 597, 599 m/z $[M+Na]^+$, retention time: 2.32 minutes, purity: 90% (254 nm) (LC-MS Method 022).

Intermediate 115C: Tert-butyl 2-(2-(3-bromophenyl)-3-(3-((2-hydroxyethyl)thio)-2,2-dimethylpropoxy)-2-methylpropanoyl)-1-methylhydrazine-1-carboxylate

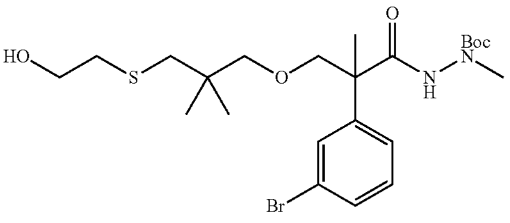 [SMILES: CN(NC(=O)C(C)(COCC(C)(C)CSCCO)c1cccc(Br)c1)C(=O)OC(C)(C)C]

To a stirred and cooled (0° C.) solution of tert-butyl 2-(2-(3-bromophenyl)-3-(3-((2-ethoxy-2-oxoethyl)thio)-2,2-dimethylpropoxy)-2-methylpropanoyl)-1-methylhydrazine-1-carboxylate (Intermediate 115B, 7 g, 12.2 mmol) in tetrahydrofuran (150 mL) was added lithium aluminum hydride (923 mg, 24.3 mmol). The reaction mixture was stirred at 0° C. for 2 hours, then treated with sodium sulfate decahydrate (10 g) carefully. After the addition, the mixture was diluted with 200 mL of ether and stirred for 30 minutes. The reaction mixture was filtered. The filtrate was concentrated. The residue was purified with automated silica gel column chromatography (80 g silica gel column, eluted with 0-50% ethyl acetate in petroleum ether) to give the title compound (3.5 g, 53.9%) as an oil. MS (ESI): 555, 557 m/z $[M+Na]^+$, retention time: 1.94 minutes, purity: 94% (254 nm) (LC-MS Method 022).

Intermediate 115D: Tert-Butyl 2-(2-(3-bromophenyl)-3-(3-((2-hydroxyethyl)sulfonyl)-2,2-dimethylpropoxy)-2-methylpropanoyl)-1-methylhydrazine-1-carboxylate

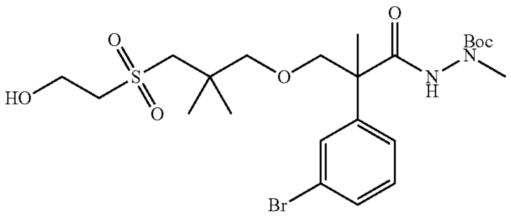 [SMILES: CN(NC(=O)C(C)(COCC(C)(C)CS(=O)(=O)CCO)c1cccc(Br)c1)C(=O)OC(C)(C)C]

To a stirred solution of tert-butyl 2-(2-(3-bromophenyl)-3-(3-((2-hydroxyethyl)thio)-2,2-dimethylpropoxy)-2-methylpropanoyl)-1-methylhydrazine-1-carboxylate (Intermediate 115C, 3.5 g, 6.56 mmol) in methanol (150 mL) was added a solution of 3.5 g ammonium molybdate tetrahydrate in 17.5 mL of hydrogen peroxide (30% in water). The reaction was stirred at room temperature for 2 hours, then diluted with ethyl acetate (200 mL) and washed with water, dried over sodium sulfate, and concentrated to give the title compound (3.6 g, 97.0%) as an oil. MS (ESI): 587, 589 m/z $[M+Na]^+$, retention time: 1.77 minutes, purity: 92% (254 nm) (LC-MS Method 022).

Intermediate 115E: Tert-Butyl (E)-2-(2-(3-(3-ethoxy-2-methyl-3-oxoprop-1-en-1-yl)phenyl)-3-(3-((2-hydroxyethyl)sulfonyl)-2,2-dimethylpropoxy)-2-methylpropanoyl)-1-methylhydrazine-1-carboxylate

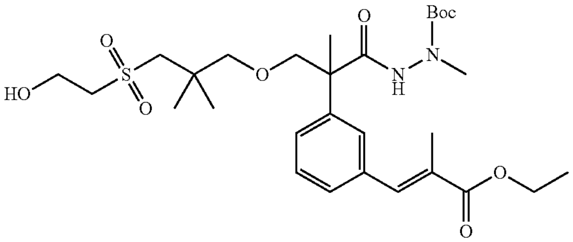 [SMILES: CCOC(=O)/C(C)=C/c1cccc(C(C)(COCC(C)(C)CS(=O)(=O)CCO)C(=O)NN(C)C(=O)OC(C)(C)C)c1]

To a stirred and degassed solution of tert-butyl 2-(2-(3-bromophenyl)-3-(3-((2-hydroxyethyl)sulfonyl)-2,2-dimethylpropoxy)-2-methylpropanoyl)-1-methylhydrazine-1-carboxylate (Intermediate 115D, 3.6 g, 6.37 mmol) in N,N-dimethylformamide (40 mL) was added ethyl methacrylate (2.38 mL, 19.1 mmol), triethylamine (2.66 mL, 19.1 mmol), tri(o-tolyl)phosphine (581 mg, 1.91 mmol), and palladium (II) acetate (143 mg, 0.637 mmol). The reaction mixture was stirred at 120° C. for 16 hours, cooled to room temperature, and diluted with ethyl acetate (100 mL). The solution was washed with water, dried over sodium sulfate, and concentrated. The residue was purified by automated flash chromatography (40 g silica gel column, eluted with 0-50% ethyl acetate in petroleum ether) to give the title compound (2.7 g, 73%) as an oil. MS (ESI): 621 m/z $[M+Na]^+$, retention time: 2.04 minutes, purity: 97% (254 nm) (LC-MS Method 022).

Intermediate 115F: Tert-Butyl 2-(2-(3-(3-ethoxy-2-methyl-3-oxopropyl)phenyl)-3-(3-((2-hydroxyethyl)sulfonyl)-2,2-dimethylpropoxy)-2-methylpropanoyl)-1-methylhydrazine-1-carboxylate

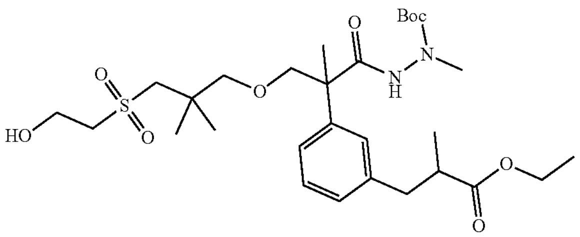 [SMILES: CCOC(=O)C(C)Cc1cccc(C(C)(COCC(C)(C)CS(=O)(=O)CCO)C(=O)NN(C)C(=O)OC(C)(C)C)c1]

To a solution of tert-butyl 2-(2-(3-(3-ethoxy-2-methyl-3-oxoprop-1-en-1-yl)phenyl)-3-(3-((2-hydroxyethyl)sulfonyl)-2,2-dimethylpropoxy)-2-methylpropanoyl)-1-methylhydrazine-1-carboxylate (Intermediate 1 I5E, 2.7 g, 4.51 mmol) in ethanol (50 mL) was added palladium on carbon (50% wet, 10%, 500 mg). The reaction mixture was stirred under hydrogen for 2 hours at 50° C., then filtered through a pad of Celite and washed the Celite cake with ethanol (2×50 mL). The combined filtrate was concentrated to give the title compound (2.6 g, 96%) as an oil. MS (ESI): 623 m/z $[M+Na]^+$, retention time: 2.14 minutes, purity: 95% (254 nm) (LC-MS Method 022).

Intermediate 116: 7-Acetoxy-2-(3-(3-ethoxy-2-methyl-3-oxopropyl)phenyl)-2,6,6-trimethylheptanoic Acid

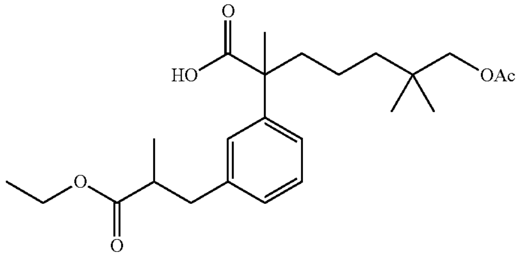 [SMILES: CCOC(=O)C(C)Cc1cccc(C(C)(CCCC(C)(C)COC(C)=O)C(=O)O)c1]

To a stirred solution of 7-acetoxy-2-(3-(3-ethoxy-2-methyl-3-oxoprop-1-en-1-yl)phenyl)-2,6,6-trimethylheptanoic acid (Intermediate 116A, 5.7 g, 13.63 mmol) in ethyl acetate (50 mL) was added palladium on carbon (10%, 570 mg, 50% wet). The mixture was stirred under hydrogen atmosphere at 55° C. overnight, cooled to room temperature and filtered through a pad of Celite. The filtrate was concentrated to give the title compound (5.5 g, 96%) as a yellow liquid. MS (ESI): 421 m/z $[M+H]^+$, retention time: 1.97 minutes, purity: 81% (254 nm). (LC-MS Method 003).

Intermediate 116A: 7-Acetoxy-2-(3-(3-ethoxy-2-methyl-3-oxoprop-1-en-1-yl)phenyl)-2,6,6-trimethylheptanoic Acid

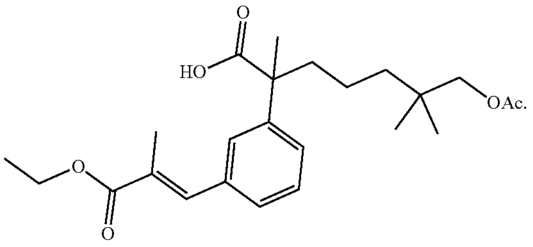 [SMILES: CCOC(=O)/C(C)=C/c1cccc(C(C)(CCCC(C)(C)COC(C)=O)C(=O)O)c1]

To a stirred and degassed solution of 7-acetoxy-2-(3-iodophenyl)-2,6,6-trimethylheptanoic acid (Intermediate 17C, 10 g, 26.04 mmol) in N,N-dimethylformamide (80 mL) was added ethyl methacrylate (5.94 g, 52.07 mmol), palladium (II) acetate (0.58 g, 2.60 mmol), tri-ortho-tolylphosphine (1.59 g, 5.21 mmol) and triethylamine (18 mL, 130.2 mmol). The mixture was stirred at 120° C. overnight. After cooling to room temperature, the solution was partitioned between 200 mL of water and 200 mL of ethyl acetate. The separated organic layer, combined with two additional ethyl acetate extracts (2×200 mL), was washed with brine, dried over sodium sulfate, and concentrated. The residue was purified with automated silica gel column chromatography (petroleum ether:ethyl acetate=2:1) to give the title compound (5.7 g, 52%) as a yellow liquid. MS (ESI): 419 m/z $[M+H]^+$, retention time: 1.99 minutes, purity: 90% (254 nm). (LC-MS Method 003).

Intermediate 117: 3-((4-Bromo-6-fluoro-1-tosyl-1H-indol-5-yl)oxy)-N-methylbenzimidamide

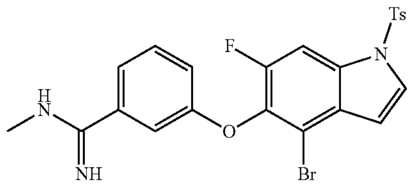 [SMILES: CNC(=N)c1cccc(Oc2c(F)cc3c(ccn3S(=O)(=O)c3ccc(C)cc3)c2Br)c1]

To a stirred and cooled (0° C.) suspension of methylamine hydrochloride (1.12 g, 16.53 mmol) in dry toluene (40 mL) was added cold trimethylaluminum (13 mL, 12.39 mmol, 0° C.) dropwise. The mixture was warmed to room temperature and stirred for 2 hours until methane evolution stopped, then treated with a solution of 3-((4-bromo-6-fluoro-1-tosyl-1H-indol-5-yl)oxy)benzonitrile (Intermediate 3-2, 2 g, 4.13 mmol) in 10 mL of tetrahydrofuran. The solution was heated at 100° C. under argon overnight. After cooling to room temperature, the mixture was partitioned between water (150 mL) and ethyl acetate (150 mL). The separated organic layer, combined with two additional ethyl acetate extracts (2×150 mL), was washed with brine, dried over sodium sulfate, and concentrated. The crude material was purified by silica gel column chromatography (dichloromethane: methanol=20:1) to give the title compound (1.9 g, 89%) as a white solid. MS (ESI): 516, 518 m/z $[M+H]^+$, retention time: 1.56 minutes, purity: 97% (214 nm). (LC-MS Method 003).

Intermediate 118: Methyl 1-(iodomethyl)cyclopropane-1-carboxylate

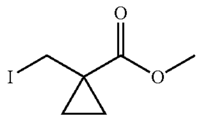

To a stirred and cooled (0° C.) solution of triphenyl phosphine (29 g, 0.111 mol) in dichloromethane (150 mL) was added imidazole (7.53 g, 0.111 mol) and iodine (28.1 g, 0.111 mmol. The mixture was stirred for 30 minutes, then treated with methyl 1-(hydroxymethyl)cyclopropane-1-carboxylate (7.20 g, 55.3 mmol). The solution was stirred at room temperature overnight and concentrated. The residue was diluted with 200 mL of petroleum ether and filtered. The filtrate was concentrated. The crude was purified by silica gel column chromatography (petroleum ether:ethyl acetate=15:1) to give the title compound (6.30 g, 47%) as a yellow liquid. $^1$H NMR (400 MHz, $CDCl_3$) δ 3.73 (s, 3H), 3.42 (s, 2H), 1.64 (q, J=4.4 Hz, 2H), 0.99 (q, J=4.4 Hz, 2H).

Intermediate 119: 7-((2-Hydroxyethyl)sulfonyl)-2-(3-((1-(methoxycarbonyl)cyclopropyl)methyl)phenyl)-6,6-dimethyl-2-(methyl-$d_3$)heptanoic Acid

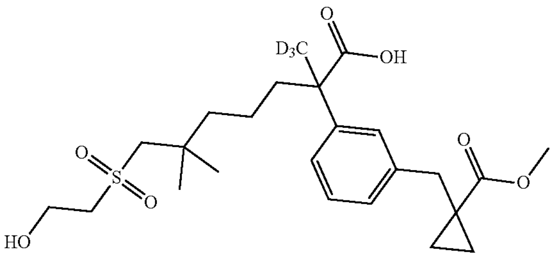 [SMILES: [2H]C([2H])([2H])C(CCCC(C)(C)CS(=O)(=O)CCO)(C(=O)O)c1cccc(CC2(C(=O)OC)CC2)c1]

To a stirred solution of methyl 1-(3-(2-(tert-butoxycarbonyl)-7-((2-((tert-butyldimethylsilyl)oxy)ethyl)sulfonyl)-6,6-dimethylheptan-2-yl-1,1,1-d3)benzyl)cyclopropane-1-carboxylate (Intermediate 119A, 2.80 g, 4.36 mmol) in dichloromethane (20 mL) was added trifluoroacetic acid (1.62 mL, 21.8 mmol) and stirred at room temperature overnight. The solvent was removed to give the title compound (1.40 g, 68%) as a brown liquid. MS (ESI): 494 m/z $[M+Na]^+$, retention time: 1.66 minutes, purity: 65% (214 nm). (LC-MS Method 003).

The following intermediates were prepared based on the procedures described for Intermediate 119, and/or for Intermediate 119A.

| Inter. No. | Structure | Name | MS m/z $[M + H]^+$ |
|---|---|---|---|
| 119-1 | 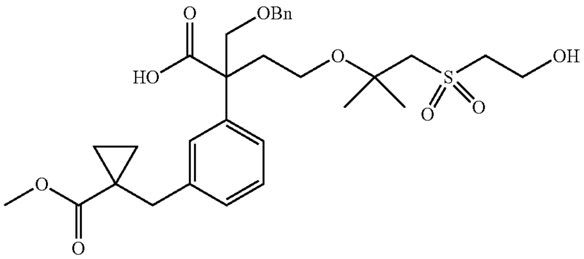 [SMILES: COC(=O)C1(Cc2cccc(C(CCOC(C)(C)CS(=O)(=O)CCO)(COCc3ccccc3)C(=O)O)c2)CC1] | 2-((benzyloxy)methyl)-4-((1-((2-hydroxyethyl)sulfonyl)-2-methylpropan-2-yl)oxy)-2-(3-((1-(methoxycarbonyl)cyclopropyl)methyl)phenyl) butanoic acid | 599 $[M + Na]^+$ |
| 119-2 | 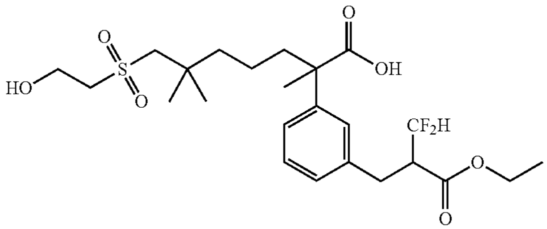 [SMILES: CCOC(=O)C(Cc1cccc(C(C)(CCCC(C)(C)CS(=O)(=O)CCO)C(=O)O)c1)C(F)F] | 2-(3-(2-(difluoromethyl)-3-ethoxy-3-oxopropyl)phenyl)-7-((2-hydroxyethyl)sulfonyl)-2,6,6-trimethylheptanoic acid | 529 $[M + Na]^+$ |
| 119-3 | 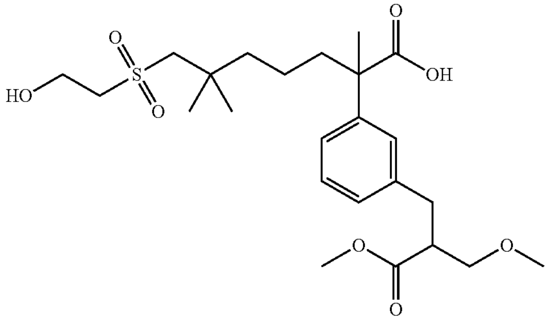 [SMILES: COCC(Cc1cccc(C(C)(CCCC(C)(C)CS(=O)(=O)CCO)C(=O)O)c1)C(=O)OC] | 7-((2-hydroxyethyl)sulfonyl)-2-(3-(3-methoxy-2-(methoxymethyl)-3-oxopropyl)phenyl)-2,6,6-trimethylheptanoic acid | 509 $[M + Na]^+$ |

-continued

| Inter. No. | Structure | Name | MS m/z [M + H]+ |
|---|---|---|---|
| 119-4 | 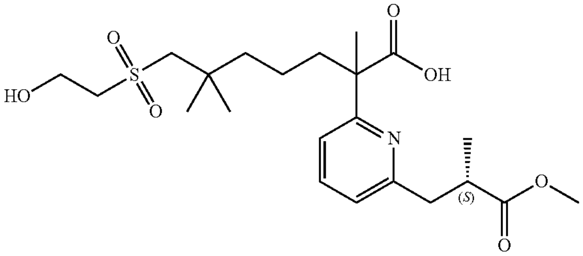 | 7-((2-hydroxyethyl)sulfonyl)-2-(6-((S)-3-methoxy-2-methyl-3-oxopropyl)pyridin-2-yl)-2,6,6-trimethylheptanoic acid | 458 |
| 119-5 | 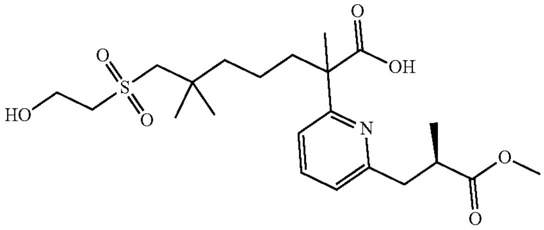 [SMILES: COC(=O)[C@H](C)Cc1cccc(C(C)(CCCC(C)(C)CS(=O)(=O)CCO)C(=O)O)n1] | 7-((2-hydroxyethyl)sulfonyl)-2-(6-((R)-3-methoxy-2-methyl-3-oxopropyl)pyridin-2-yl)-2,6,6-trimethylheptanoic acid | 458 |

Intermediate 119A: Methyl 1-(3-(2-(tert-butoxycarbonyl)-7-((2-((tert-butyldimethylsilyl)oxy)ethyl)sulfonyl)-6,6-dimethylheptan-2-yl-1,1,1-d3)benzyl)cyclopropane-1-carboxylate

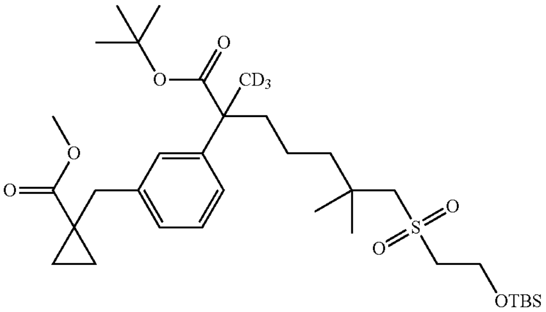 [SMILES: [2H]C([2H])([2H])C(CCCC(C)(C)CS(=O)(=O)CCO[Si](C)(C)C(C)(C)C)(C(=O)OC(C)(C)C)c1cccc(CC2(C(=O)OC)CC2)c1]

In glove box, to a stirred suspension of zinc (2.57 g, 0.0393 mol) in N,N-dimethylformamide (20 mL) was added iodine (166 mg, 0.656 mmol). The mixture was stirred at room temperature for 40 minutes, then treated with methyl 1-(iodomethyl)cyclopropane-1-carboxylate (Intermediate 118, 3.15 g, 0.0131 mol). The solution was stirred at room temperature for 40 minutes. To the stirred solution were added S-Phos (269 mg, 0.656 mmol) and tris(dibenzylideneacetone)dipalladium(0) (189 mg, 0.328 mmol), tert-butyl 7-((2-((tert-butyldimethylsilyl)oxy)ethyl)sulfonyl)-2-(3-iodophenyl)-6,6-dimethyl-2-(methyl-$d_3$)heptanoate (Intermediate 64-1, 4.3 g, 6.56 mmol). The reaction was stirred at room temperature overnight, then partitioned between water (50 mL) and ethyl acetate (80 mL). The separated organic layer, combined with two additional ethyl acetate extracts, was washed with brine, dried over sodium sulfate, and concentrated. The residue was purified by silica gel column chromatography (petroleum ether:ethyl acetate=4:1) to give the title compound (2.8 g, 67%) as a yellow liquid. MS (ESI): 664 m/z $[M+Na]^+$, retention time: 3.51 minutes, purity: 80% (214 nm). (LC-MS Method 032).

The following intermediate was prepared based on the procedures described for Intermediate 119A.

| Inter. No. | Structure | Name | MS m/z [M + H]+ |
|---|---|---|---|
| 119A-1 | 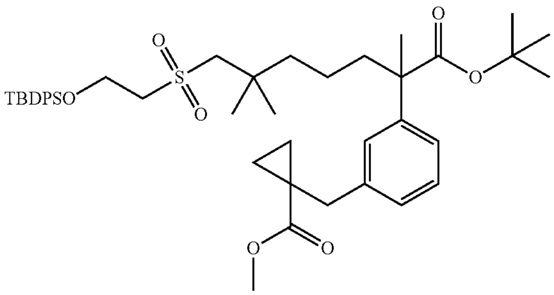 | methyl 1-(3-(1-(tert-butoxy)-7-((2-((tert-butyldiphenylsilyl)oxy)ethyl)sulfonyl)-2,6,6-trimethyl-1-oxoheptan-2-yl)benzyl)cyclopropane-1-carboxylate | 785 $[M + Na]^+$ |

Intermediate 120: Tert-Butyl 2-(2-((benzyloxy) methyl)-2-(3-bromo-2-fluorophenyl)-7-((2-hydroxy-ethyl)sulfonyl)-6,6-dimethylheptanoyl)-1-methylhy-drazine-1-carboxylate

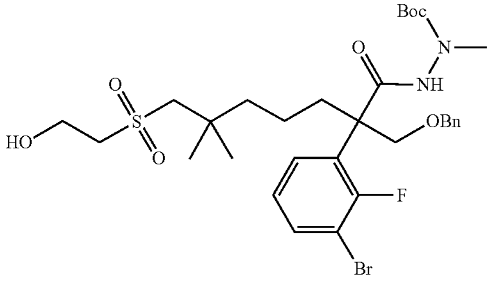 [SMILES: CN(NC(=O)C(CCCC(C)(C)CS(=O)(=O)CCO)(COCc1ccccc1)c1cccc(Br)c1F)C(=O)OC(C)(C)C]

To a stirred solution of 2-((benzyloxy)methyl)-2-(3-bromo-2-fluorophenyl)-7-((2-hydroxyethyl)sulfonyl)-6,6-dimethylheptanoic acid (Intermediate 67-1, 6.8 g, 12.2 mmol) in acetonitrile (50 mL) were added tert-butyl N-amino-N-methyl-carbamate (2.13 g, 14.6 mmol), 1-methylimidazole (2.99 g, 36.5 mmol) and N,N,N',N'-tetramethylchloroformamidinium hexafluorophosphate (3.58 g, 12.8 mmol). The reaction mixture was stirring at room temperature for 2 hours, then diluted with ethyl acetate (300 mL). The mixture was washed with water (2×200 mL), dried over magnesium sulfate, and concentrated. The residue was purified by automated silica gel column chromatography (80 g silica gel column, eluted with 0-50% ethyl acetate in petroleum ether) to give the title compound (7.0 g, 84%) as a light-yellow oil. MS (ESI): 709, 711 m/z $[M+Na]^+$, retention time: 1.91 minutes, purity: 94% (214 nm). (LC-MS Method 003).

Intermediate 121: Tert-Butyl (E)-2-(2-((benzyloxy) methyl)-2-(3-(3-ethoxy-2-methyl-3-oxoprop-1-en-1-yl)-2-fluorophenyl)-7-((2-hydroxyethyl)sulfonyl)-6, 6-dimethylheptanoyl)-1-methylhydrazine-1-carboxylate

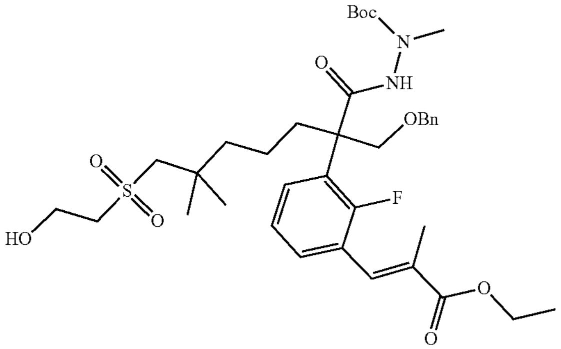 [SMILES: CCOC(=O)/C(C)=C/c1cccc(C(CCCC(C)(C)CS(=O)(=O)CCO)(COCc2ccccc2)C(=O)NN(C)C(=O)OC(C)(C)C)c1F]

To a stirred solution of tert-butyl 2-(2-((benzyloxy)methyl)-2-(3-bromo-2-fluorophenyl)-7-((2-hydroxyethyl)sulfonyl)-6,6-dimethylheptanoyl)-1-methylhydrazine-1-carboxylate (Intermediate 120, 3.5 g, 5.09 mmol) in 1,4-dioxane (60 mL) and water (10 mL) was added ethyl (E)-2-methyl-3-(4,4,5,5-tetramethyl-1,3,2-dioxaborolan-2-yl)acrylate (1.83 g, 7.63 mmol), 1,1'-bis(diphenylphosphino)ferrocene-palladium (II) dichloride dichloromethane complex (208 mg, 0.254 mmol) and cesium carbonate (3.32 g, 10.2 mmol) under argon. The mixture was stirred at 100° C. overnight, then cooled to room temperature, quenched with water (150 mL), and extracted with ethyl acetate (3×100 mL). The combined organic extracts were washed with brine, dried over sodium sulfate, and concentrated. The residue was purified by automated flash chromatography (80 g silica gel column, eluted with 0-50% ethyl acetate in petroleum ether) to give the title compound (2.6 g, 70%) as a light-yellow oil. MS (ESI): 743 m/z $[M+Na]^+$, retention time: 1.95 minutes, purity: 94% (254 nm). (LC-MS Method 009).

Intermediate 122: Ethyl (E)-3-(3-(2-((benzyloxy) methyl)-7-((2-hydroxyethyl)sulfonyl)-6,6-dimethyl-1-(2-methylhydrazineyl)-1-oxoheptan-2-yl)-2-fluorophenyl)-2-methylacrylate

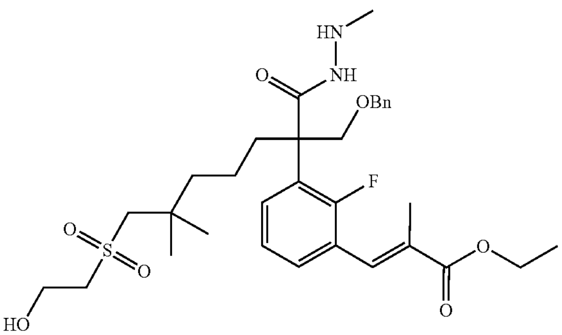 [SMILES: CCOC(=O)/C(C)=C/c1cccc(C(CCCC(C)(C)CS(=O)(=O)CCO)(COCc2ccccc2)C(=O)NNC)c1F]

To a stirred solution of tert-butyl (E)-2-(2-((benzyloxy)methyl)-2-(3-(3-ethoxy-2-methyl-3-oxoprop-1-en-1-yl)-2-fluorophenyl)-7-((2-hydroxyethyl)sulfonyl)-6,6-dimethylheptanoyl)-1-methylhydrazine-1-carboxylate (Intermediate 121, 2.6 g, 3.61 mmol) in dichloromethane (20 mL) was added trifluoroacetic acid (7.0 mL). The mixture was stirred at room temperature for 4 hours and evaporated. The residue was diluted with saturated sodium bicarbonate solution (100 mL) and extracted with ethyl acetate (3×100 mL). The combined organic layers were dried over sodium sulfate and concentrated to give the title compound (2.0 g, 89%) as a light-yellow oil. MS (ESI): 621 m/z $[M+H]^+$, retention time: 1.64 minutes, purity: 97% (214 nm). (LC-MS Method 009).

Intermediate 123: Diethyl 5-(1-(tert-butoxy)-1-oxo-propan-2-yl)-1,3-dihydro-2H-indene-2,2-dicarboxy-late

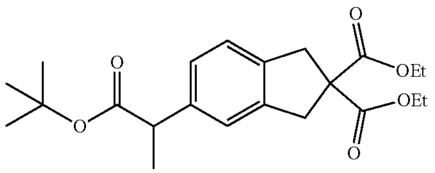 [SMILES: CCOC(=O)C1(C(=O)OCC)Cc2ccc(C(C)C(=O)OC(C)(C)C)cc2C1]

To a stirred solution of diethyl 5-(3-(tert-butoxy)-3-oxo-prop-1-en-2-yl)-1,3-dihydro-2H-indene-2,2-dicarboxylate (Intermediate 123B, 13.1 g, 33.76 mmol) in methanol (200 mL) was added palladium on active carbon (10%, 2 g). The mixture was stirred at room temperature under hydrogen balloon for 2 hours. The mixture was filtered through a pad of Celite. The filtrate was concentrated to give the title compound (12 g, 92%). MS (ESI): 413 m/z $[M+Na]^+$, retention time: 2.10 minutes, purity: 96% (214 nm). (LC-MS Method 003).

Intermediate 123A. Diethyl 5-bromo-1,3-dihydro-2H-indene-2,2-dicarboxylate

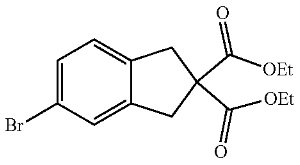 [SMILES: CCOC(=O)C1(C(=O)OCC)Cc2ccc(Br)cc2C1]

To a stirred solution of diethyl malonate (14.6 g, 91.2 mmol) in ethanol (100 mL) and diethyl ether (300 mL) was added sodium ethylate (16.5 g, 200.6 mmol) portion-wise. After the addition was complete, the solution was stirred for 15 minutes at room temperature, then treated with 4-bromo-1,2-bis(bromomethyl)benzene (31.0 g, 91.2 mmol). The mixture was stirred for 1 hour and filtered. The filtrate was concentrated. The residue was purified by automated silica gel column chromatography (ethyl acetate in petroleum ether from 0 to 10%) to give the title compound (17.3 g, 56%). MS (ESI): 341, 343 m/z $[M+H]^+$, retention time: 2.03 minutes, purity: 92% (214 nm). (LC-MS Method 003).

Intermediate 123B: Diethyl 5-(3-(tert-butoxy)-3-oxoprop-1-en-2-yl)-1,3-dihydro-2H-indene-2,2-dicarboxylate

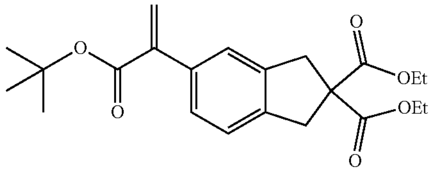 [SMILES: C=C(C(=O)OC(C)(C)C)c1ccc2c(c1)CC(C(=O)OCC)(C(=O)OCC)C2]

To a stirred and degassed solution of diethyl 5-bromo-1,3-dihydro-2H-indene-2,2-dicarboxylate (Intermediate 123A, 16 g, 47.06 mmol) in dimethyl sulfoxide (160 mL) was added anhydrous lithium chloride (11.86 g, 282.35 mmol), copper (I) chloride (23.29 g, 235.29 mmol). The mixture was stirred for 30 minutes, then treated with tert-butyl 2-(tributylstannyl)acrylate (23.6 g, 56.47 mmol) and bis(tri-t-butylphosphine)palladium (0) (1.25 g, 2.35 mmol). The reaction mixture was heated at 65° C. for 3 hours, then cooled to room temperature, and extracted with diethyl ether (4×100 mL). The combined organic phases were washed with water, brine, and dried over sodium sulfate. After removal of solvent, the residue was purified by automated silica gel column chromatography (ethyl acetate in petroleum ether from 0 to 10%) to give the title compound (13.1 g, 72%). MS (ESI): 411 m/z $[M+Na]^+$, retention time: 2.10 minutes, purity: 95% (214 nm). (LC-MS Method 003).

Intermediate 124: 2-(3-(2-(Difluoromethyl)-3-ethoxy-3-oxopropyl)phenyl)-7-((2-hydroxyethyl)sulfonyl)-2,6,6-trimethylheptanoic Acid

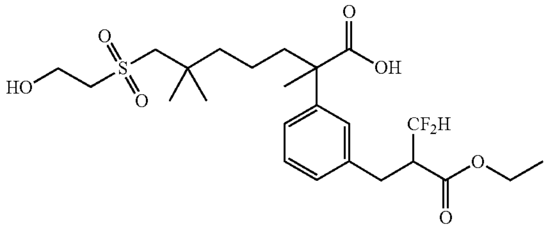 [SMILES: CCOC(=O)C(Cc1cccc(C(C)(CCCC(C)(C)CS(=O)(=O)CCO)C(=O)O)c1)C(F)F]

To a stirred solution of tert-butyl 7-((2-((tert-butyldimethylsilyl)oxy)ethyl)sulfonyl)-2-(3-(2-(difluoromethyl)-3-ethoxy-3-oxopropyl)phenyl)-2,6,6-trimethylheptanoate (Intermediate 124D, 1.2 g, 1.18 mmol) in dichloromethane (20 mL) was added trifluoroacetic acid (1.01 g, 8.87 mmol) and stirred at room temperature overnight. The solvent was evaporated. The residue was purified by silica gel column chromatography (dichloromethane:methanol=20:1) to give the title compound (890 mg, 99%) as a colorless liquid. MS (ESI): 529 m/z $[M+Na]^+$, retention time: 1.72 minutes, purity: 82% (214 nm). (LC-MS Method 003).

Intermediate 124A: Tert-Butyl 2-(3-(2-benzoyl-3-ethoxy-3-oxopropyl)phenyl)-7-((2-((tert-butyldimethylsilyl)oxy)ethyl)sulfonyl)-2,6,6-trimethylheptanoate

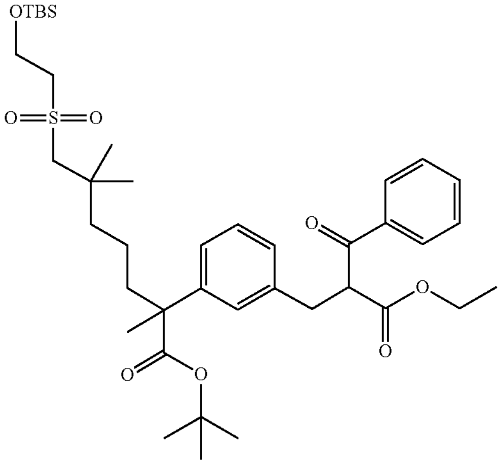 [SMILES: CCOC(=O)C(Cc1cccc(C(C)(CCCC(C)(C)CS(=O)(=O)CCO[Si](C)(C)C(C)(C)C)C(=O)OC(C)(C)C)c1)C(=O)c1ccccc1]

To a stirred solution of ethyl 2-(hydroxy(phenyl)methyl)acrylate (1.4 g, 6.79 mmol) in N,N-dimethylformamide (30 mL) were added tert-butyl 7-((2-((tert-butyldimethylsilyl)oxy)ethyl)sulfonyl)-2-(3-iodophenyl)-2,6,6-trimethylheptanoate (Intermediate 64, 4 g, 6.11 mmol) and palladium on active carbon (10%, 400 mg) under nitrogen. The mixture was stirred at 100° C. for 5 hours. After cooling to room temperature, the mixture was partitioned between 120 mL of water and 120 mL of ethyl acetate. The separated organic layer, combined with two additional ethyl acetate extracts (2×120 mL), was washed with brine, dried over sodium sulfate, and concentrated. The residue was purified by silica gel column chromatography (petroleum ether:ethyl acetate=4:1) to give the title compound (2.4 g, 54%) as a light-yellow liquid. MS (ESI): 753 m/z $[M+Na]^+$, retention time: 2.46 minutes, purity: 91% (214 nm). (LC-MS Method 003).

Intermediate 124B: Tert-Butyl 7-((2-((tert-butyldimethylsilyl)oxy)ethyl)sulfonyl)-2-(3-(2-diazo-3-ethoxy-3-oxopropyl)phenyl)-2,6,6-trimethylheptanoate

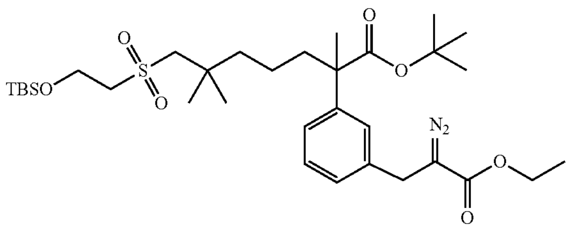

To a stirred solution of tert-butyl 2-(3-(2-benzoyl-3-ethoxy-3-oxopropyl)phenyl)-7-((2-((tert-butyldimethylsilyl)oxy)ethyl)sulfonyl)-2,6,6-trimethylheptanoate (Intermediate 124A, 2.4 g, 3.29 mmol) in acetonitrile (30 mL) were added p-toluenesulfonyl azide (778 mg, 3.94 mmol) and triethylamine (499 mg, 4.93 mmol). The mixture was stirred at room temperature overnight, then diluted with 120 mL of water, extracted with ethyl acetate (3×120 mL). The combined organic extracts were washed with brine, dried over sodium sulfate, and concentrated. The residue was purified by silica gel column chromatography (petroleum ether: ethyl acetate=4:1) to give the title compound (1.8 g, 84%) as a yellow liquid. MS (ESI): 675 m/z $[M+Na]^+$, retention time: 2.48 minutes, purity: >99% (214 nm). (LC-MS Method 003).

Intermediate 124C: Tert-Butyl 7-((2-((tert-butyldimethylsilyl)oxy)ethyl)sulfonyl)-2-(3-(2-(ethoxycarbonyl)-3,3-difluoroallyl)phenyl)-2,6,6-trimethylheptanoate

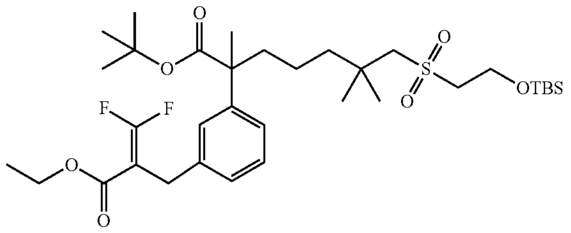 [SMILES: CCOC(=O)C(Cc1cccc(C(C)(CCCC(C)(C)CS(=O)(=O)CCO[Si](C)(C)C(C)(C)C)C(=O)OC(C)(C)C)c1)=C(F)F]

To a stirred solution of tert-butyl 7-((2-((tert-butyldimethylsilyl)oxy)ethyl)sulfonyl)-2-(3-(2-diazo-3-ethoxy-3-oxopropyl)phenyl)-2,6,6-trimethylheptanoate (Intermediate 124B, 1.8 g, 2.76 mmol) in tetrahydrofuran (30 mL) were added sodium iodide (910 mg, 6.07 mmol) and (trifluoromethyl)trimethylsilane (942 mg, 6.62 mmol). The mixture was stirred at 60° C. for 5 hours, then cooled to room temperature, diluted with 100 mL of water, and extracted with ethyl acetate (3×100 mL). The combined organic extracts were washed with brine, dried over sodium sulfate, and concentrated. The crude was purified by silica gel column chromatography (petroleum ether:ethyl acetate=4:1) to give the title compound (1.75 g, 95%) as a yellow liquid. MS (ESI): 675 m/z $[M+H]^+$, retention time: 2.54 minutes, purity: 94% (214 nm). (LC-MS Method 003).

Intermediate 124D. Tert-Butyl 7-((2-((tert-butyldimethylsilyl)oxy)ethyl)sulfonyl)-2-(3-(2-(difluoromethyl)-3-ethoxy-3-oxopropyl)phenyl)-2,6,6-trimethylheptanoate

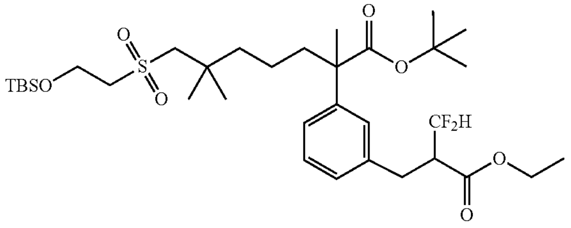 [SMILES: CCOC(=O)C(Cc1cccc(C(C)(CCCC(C)(C)CS(=O)(=O)CCO[Si](C)(C)C(C)(C)C)C(=O)OC(C)(C)C)c1)C(F)F]

To a stirred solution of tert-butyl 7-((2-((tert-butyldimethylsilyl)oxy)ethyl)sulfonyl)-2-(3-(2-(ethoxycarbonyl)-3,3-difluoroallyl)phenyl)-2,6,6-trimethylheptanoate (Intermediate 124C, 1.2 g, 1.19 mmol) in methanol (20 mL) was added palladium on carbon (120 mg). The mixture was stirred at room temperature overnight under hydrogen, then filtered through a pad of Celite. The filtrate was concentrated to give the title compound (1.2 g, 99%) as a colorless liquid. MS (ESI): 699 m/z $[M+Na]^+$, retention time: 2.41 minutes, purity: 90% (214 nm). (LC-MS Method 003).

Intermediate 125: 1-((4-Bromo-6-fluoro-1H-indol-5-yl)methyl)-6-oxo-1,6-dihydropyridine-3-carbonitrile

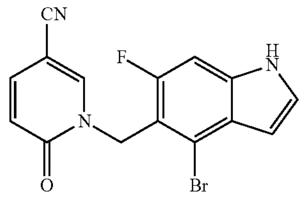 [SMILES: N#Cc1ccc(=O)n(Cc2c(F)cc3[nH]ccc3c2Br)c1]

To a stirred solution of 4-bromo-5-(bromomethyl)-6-fluoro-1-(triisopropylsilyl)-1H-indole (Intermediate 125C, 2.8 g, 6 mmol) in N,N-dimethylformamide (20 mL) was added 6-oxo-1,6-dihydropyridine-3-carbonitrile (730 mg, 6 mmol) and potassium carbonate (1 g, 7.2 mmol). The mixture was stirred at 70° C. for 1 hour, then cooled to room temperature, diluted with water (50 mL) and extracted with ethyl acetate (3×30 mL). The combined organic extracts were washed with brine, dried over sodium sulfate, and concentrated to give the title compound (1.4 g, 70%) as a light-yellow solid. MS (ESI): 368, 370 m/z $[M+Na]^+$, retention time: 1.71 minutes, purity: 90% (214 nm). (LC-MS Method 003).

Intermediate 125A: 4-Bromo-6-fluoro-1-(triisopropylsilyl)-1H-indole-5-carbaldehyde

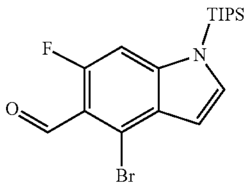

To a stirred and cooled (−78° C.) solution of 4-bromo-6-fluoro-1-(triisopropylsilyl)-1H-indole (12.7 g, 34.4 mmol) in tetrahydrofuran (150 mL) was added lithium diisopropylamide (34.4 mL, 2 M, 68.8 mmol). The mixture was stirred for 1 hour, then treated with N,N-dimethylformamide (3.7 g, 51.6 mmol), and stirred at −78° C. for additional 1 hour. The reaction mixture was quenched with water (100 mL), warmed to room temperature, and extracted with ethyl acetate (3×100 mL). The combined organic extracts were washed with brine, dried over sodium sulfate, and concentrated to give the title compound (5.0 g, 52%) as a light-yellow solid. MS (ESI): 398, 400 m/z $[M+H]^+$, retention time: 1.68 minutes, purity: 94% (214 nm). (LC-MS Method 033).

Intermediate 125B: (4-Bromo-6-fluoro-1-(triisopropylsilyl)-1H-indol-5-yl)methanol

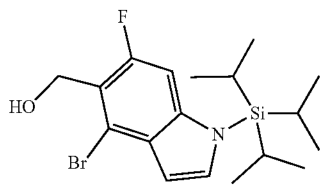 [SMILES: CC(C)[Si](C(C)C)(C(C)C)n1ccc2c(Br)c(CO)c(F)cc21]

To a stirred solution of 4-bromo-6-fluoro-1-(triisopropylsilyl)-1H-indole-5-carbaldehyde (Intermediate 125A, 5.2 g, 1.3 mmol) in methyl alcohol (20 mL) was added sodium borohydride (740 mg, 19.6 mmol). The mixture was stirred for 3 hours, then quenched with water (30 ml), and extracted with ethyl acetate (3×50 mL). The combined organic extracts were washed with brine, dried over sodium sulfate, and concentrated to give the title compound (4.8 g, 92%) as a light-yellow oil. MS (ESI): 400, 402 m/z $[M+H]^+$, retention time: 1.68 minutes, purity: 99% (214 nm) (LC-MS Method 033).

Intermediate 125C: 4-Bromo-5-(bromomethyl)-6-fluoro-1-(triisopropylsilyl)-1H-indole

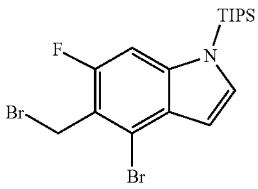

To a stirred and cooled (0° C.) solution of (4-bromo-6-fluoro-1-(triisopropylsilyl)-1H-indol-5-yl)methanol (Intermediate 125B, 3 g, 7.5 mmol) in dichloromethane (30 mL) was added phosphorus tribromide (3 g, 11.2 mmol). The mixture was stirred for 1 hour, then quenched with water (30 ml), and extracted with dichloromethane (3×50 mL). The combined organic extracts were washed with brine (2×30 mL), dried over sodium sulfate, and concentrated. The residue was purified by automated flash chromatography (40 g silica gel column, eluted with 0-30% ethyl acetate in petroleum ether) to give the title compound (2.4 g, 70%) as a light-yellow oil. MS (ESI): 486 m/z $[M+Na]^+$, retention time: 1.80 minutes, purity: 70% (214 nm). (LC-MS Method 033).

Intermediate 126: Ethyl (E)-2-methyl-3-(4,4,5,5-tetramethyl-1,3,2-dioxaborolan-2-yl)but-2-enoate

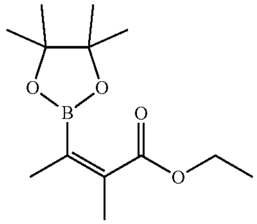 [SMILES: CCOC(=O)/C(C)=C(/C)B1OC(C)(C)C(C)(C)O1]

To a stirred solution of ethyl (Z)-2-methyl-3-(((trifluoromethyl)sulfonyl)oxy)but-2-enoate (Intermediate 126A, 6.9 g, 25 mmol) in dioxane (50 mL) was added bis(pinacolato)diboron (7.6 g, 30 mmol), [1,1'-bis(diphenylphosphino)ferrocene]dichloropalladium (II) (2 g, 2.5 mmol) and potassium acetate (7.4 g, 75 mmol). The mixture was stirred at 60° C. for 2 hours, then diluted with ethyl acetate (100 mL). The solution was washed with water (50 mL), brine (50 mL), dried over sodium sulfate, and concentrated to give the title compound (6 g, 95%) as a liquid. MS (ESI): 255 m/z $[M+H]^+$, retention time: 2.02 minutes, purity: 55% (214 nm). (LC-MS Method 034).

Intermediate 126A: Ethyl (Z)-2-methyl-3-(((trifluoromethyl)sulfonyl)oxy)but-2-enoate

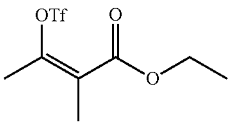 [SMILES: CCOC(=O)/C(C)=C(/C)OS(=O)(=O)C(F)(F)F]

To a stirred and cooled (−78° C.) solution of ethyl 2-methyl-3-oxobutanoate (7.2 g, 50 mmol) in dichloromethane (50 mL) was added N,N-diisopropylethylamine (12.9 g, 100 mmol) and trifluoromethanesulfonic anhydride (21 g, 75 mmol). The mixture was stirred at −78° C. for 2 hours, then warmed to room temperature and concentrated. The residue was dissolved in ethyl acetate (100 mL). The solution was washed with water, brine, dried over sodium sulfate, and concentrated. The residue was purified by flash chromatography (80 g silica gel column, eluted with 0-10% ethyl acetate in petroleum ether) to give the title compound (6.9 g, 50%) as a liquid. MS (ESI): 277 m/z $[M+H]^+$, retention time: 1.68 minutes, purity: 99% (214 nm). (LC-MS Method 034).

Intermediate 127: 7-((2-((Tert-Butyldiphenylsilyl)oxy)ethyl)sulfonyl)-2-(3-((S)-3-methoxy-2-methyl-3-oxopropyl)phenyl)-2,6,6-trimethylheptanoic Acid

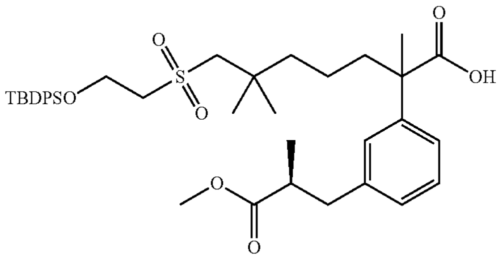

A solution of tert-butyl 7-((2-((tert-butyldiphenylsilyl)oxy)ethyl)sulfonyl)-2-(3-((S)-3-methoxy-2-methyl-3-oxopropyl)phenyl)-2,6,6-trimethylheptanoate (Intermediate 65-4, 32.8 g, 43.7 mmol) in 4 M hydrogen chloride in 1,4-dioxane (175 mL) was stirred at 40° C. for 2 hours and concentrated. The residue was purified with automated flash chromatography (330 g silica gel column, eluted with 0-50% ethyl acetate in petroleum) to give the title compound (24.8 g, 82%). MS (ESI): 717 m/z [M+Na]+, retention time: 1.75 minutes, purity: 95% (254 nm). (LC-MS Method 012).

| Inter. No. | Structure | Name | MS m/z [M + H]+ |
|---|---|---|---|
| 127-1 | 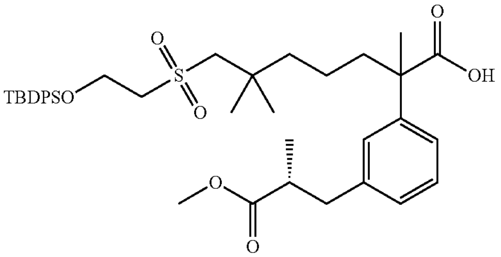 | 7-((2-((tert-butyldiphenylsilyl)oxy)ethyl)sulfonyl)-2-(3-((R)-3-methoxy-2-methyl-3-oxopropyl)phenyl)-2,6,6-trimethylheptanoic acid | 717 [M + Na]+ |
| 127-2 | 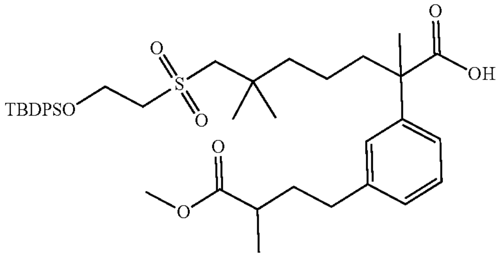 | 7-((2-((tert-butyldiphenylsilyl)oxy)ethyl)sulfonyl)-2-(3-(4-methoxy-3-methyl-4-oxobutyl)phenyl)-2,6,6-trimethylheptanoic acid | 731 [M + Na]+ |
| 127-3 | 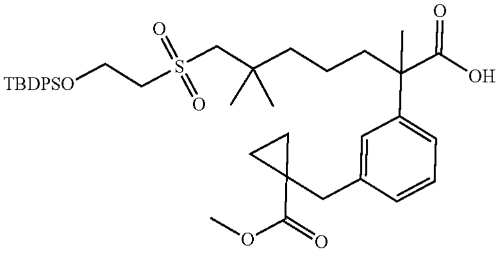 | 7-((2-((tert-butyldiphenylsilyl)oxy)ethyl)sulfonyl)-2-(3-((1-(methoxycarbonyl)cyclopropyl)methyl)phenyl)-2,6,6-trimethylheptanoic acid | 729 [M + Na]+ |
| 127-4 | 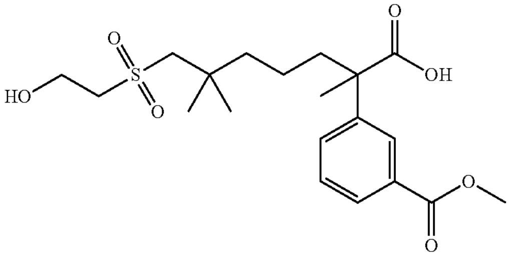 [SMILES: COC(=O)c1cccc(C(C)(CCCC(C)(C)CS(=O)(=O)CCO)C(=O)O)c1] | 7-((2-hydroxyethyl)sulfonyl)-2-(3-(methoxycarbonyl)phenyl)-2,6,6-trimethylheptanoic acid | 432 [M + $H_2O$]+ |
| 127-5 | 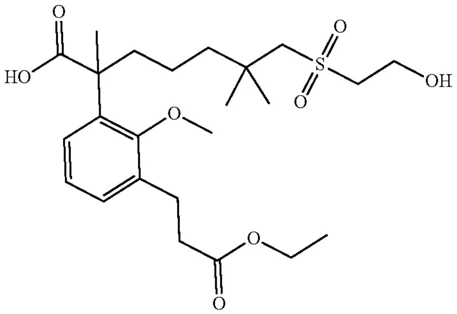 [SMILES: CCOC(=O)CCc1cccc(C(C)(CCCC(C)(C)CS(=O)(=O)CCO)C(=O)O)c1OC] | 2-(3-(3-ethoxy-3-oxopropyl)-2-methoxyphenyl)-7-((2-hydroxyethyl)sulfonyl)-2,6,6-trimethylheptanoic acid | 487 |

Intermediate 128: Tert-Butyl 7-((2-((tert-butyldiphenylsilyl)oxy)ethyl)sulfonyl)-2-(3-(4-methoxy-3-methyl-4-oxobutyl)phenyl)-2,6,6-trimethylheptanoate

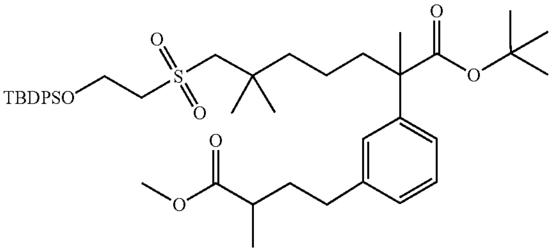

To a solution of tert-butyl 7-((2-((tert-butyldiphenylsilyl)oxy)ethyl)sulfonyl)-2-(3-(3-(methoxycarbonyl)but-3-en-1-yl)phenyl)-2,6,6-trimethylheptanoate (Intermediate 128A, 9.0 g, 11.8 mmol) in methanol (200 mL) was added 10% palladium on carbon (wetted with ca. 55% water, 3.0 g). The reaction mixture was stirred under hydrogen atmosphere for 16 hours at room temperature, then filtered through a pad of Celite. The filtrate was concentrated to give the title compound (9.0 g, 99%) as a white solid. MS (ESI): 787 m/z $[M+Na]^+$, retention time: 1.79 minutes, purity: 97% (254 nm) (LC-MS Method 009).

Intermediate 128A: Tert-butyl 7-((2-((tert-butyldiphenylsilyl)oxy)ethyl)sulfonyl)-2-(3-(3-(methoxycarbonyl)but-3-en-1-yl)phenyl)-2,6,6-trimethylheptanoate

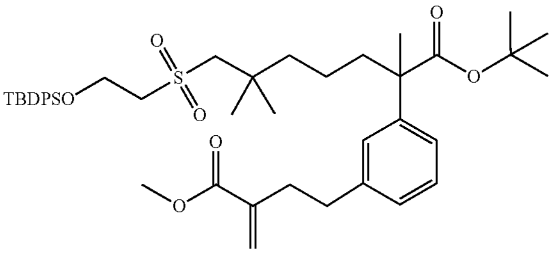

To a suspension of zinc (5.06 g, 77.4 mmol) in N,N-dimethylformamide (80 mL) was added iodine (327 mg, 1.29 mmol). The mixture was stirred at room temperature for 40 minutes, then treated with methyl 1-(iodomethyl)cyclopropanecarboxylate (Intermediate 118, 6.18 g, 25.7 mmol). The mixture was stirred at room temperature for 40 minutes. To this solution was added 2-dicyclohexylphosphino-2',6'-dimethoxybiphenyl (530 mg, 1.29 mmol), tris-(dibenzylideneacetone)dipalladium (591 mg, 0.645 mmol) and tert-butyl 7-((2-((tert-butyldiphenylsilyl)oxy)ethyl)sulfonyl)-2-(3-iodophenyl)-2,6,6-trimethylheptanoate (Intermediate 64-5, 10 g, 12.9 mmol). The reaction mixture was stirred at 50° C. for 16 hours, then filtered through a pad of Celite, and filter cake rinsed with ethyl acetate (150 mL). The filtrate was diluted with water (200 mL), extracted with ethyl acetate (3×100 mL). The combined organic extracts were washed with brine, dried over sodium sulfate, and concentrated. The residue was purified by automated flash chromatography (80 g silica gel column, eluted with 0-30% ethyl acetate in petroleum ether) to give the title compound (6.0 g, 61%) as a yellow oil. MS (ESI): 785 m/z $[M+Na]^+$, retention time: 1.78 minutes, purity: >99% (254 nm). (LC-MS Method 009).

Intermediate 129: Methyl 4-(3-(7-((2-((tert-butyldiphenylsilyl)oxy)ethyl)sulfonyl)-2,6,6-trimethyl-1-(2-methylhydrazineyl)-1-oxoheptan-2-yl)phenyl)-2-methylbutanoate

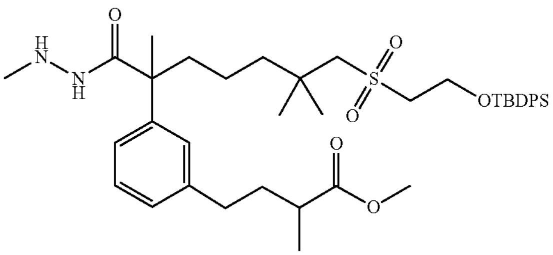

To a solution of tert-butyl 2-(7-((2-((tert-butyldiphenylsilyl)oxy)ethyl)sulfonyl)-2-(3-(4-methoxy-3-methyl-4-oxobutyl)phenyl)-2,6,6-trimethylheptanoyl)-1-methylhydrazine-1-carboxylate (Intermediate 129A, 6.0 g, 7.17 mmol) in 1,4-dioxane (10 mL) was added hydrogen chloride in 1,4-dioxane (4.0 M, 17.9 mL, 71.7 mmol). The mixture was stirred at 40° C. for 2.0 hours and concentrated. The residue was partitioned between saturated sodium bicarbonate aqueous solution (60 mL) and ethyl acetate (150 mL). The separated organic layer, combined with two additional ethyl acetate extracts (2×100 mL), was dried over sodium sulfate, and concentrated to give the title compound (5.0 g, 95%) as a light-yellow oil. MS (ESI): 737 m/z $[M+H]^+$, retention time: 1.50 minutes, purity: 88% (254 nm). (LC-MS Method 033).

The following intermediate was prepared based on the procedures described for Intermediate 129

| Inter. No. | Structure | Name | MS m/z [M + H]+ |
|---|---|---|---|
| 129-1 | 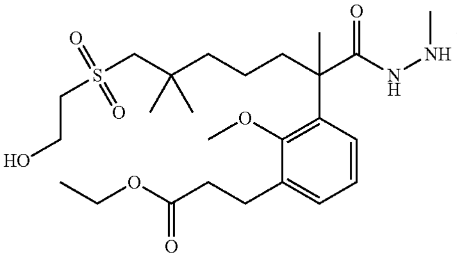 [SMILES: CCOC(=O)CCc1cccc(C(C)(CCCC(C)(C)CS(=O)(=O)CCO)C(=O)NNC)c1OC] | ethyl 3-(3-(7-((2-hydroxyethyl)sulfonyl)-2,6,6-trimethyl-1-(2-methylhydrazineyl)-1-oxoheptan-2-yl)-2-methoxyphenyl)propanoate | 515 |

Intermediate 129A: Tert-Butyl 2-(7-((2-((tert-butyldiphenylsilyl)oxy)ethyl)sulfonyl)-2-(3-(4-methoxy-3-methyl-4-oxobutyl)phenyl)-2,6,6-trimethylheptanoyl)-1-methylhydrazine-1-carboxylate

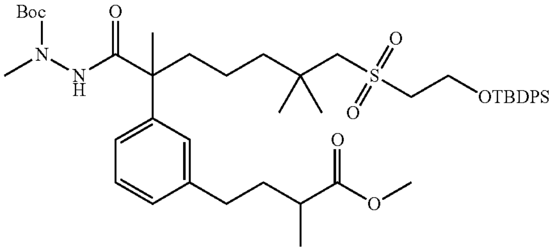

To a stirred solution of 7-((2-((tert-butyldiphenylsilyl)oxy)ethyl)sulfonyl)-2-(3-(4-methoxy-3-methyl-4-oxobutyl)phenyl)-2,6,6-trimethylheptanoic acid (Intermediate 127-2, 6.0 g, 8.46 mmol) in acetonitrile (50 mL) were added tert-butyl N-amino-N-methyl-carbamate (1.48 g, 10.2 mmol), N,N,N',N'-tetramethylchloroformamidinium hexafluorophosphate (2.37 g, 8.46 mmol) and 1-methylimidazole (2.43 g, 29.6 mmol). The reaction mixture was stirred at room temperature for 1 hour, then diluted with ethyl acetate (50 mL). The solution was washed with brine, dried over sodium sulfate, and concentrated. The residue was purified by automated silica gel column chromatography (120 g silica gel column, eluted with 0-65% ethyl acetate in petroleum ether) to give the title compound (6.0 g, 85%) as a light-yellow oil. MS (ESI): 859 m/z $[M+Na]^+$, retention time: 1.67 minutes, purity: 95% (214 nm). (LC-MS Method 033).

Intermediate 130: (6-Fluoro-4-vinyl-1H-indol-5-yl)(3-(1-(tetrahydro-2H-pyran-2-yl)-1H-pyrazol-5-yl)phenyl)methanone

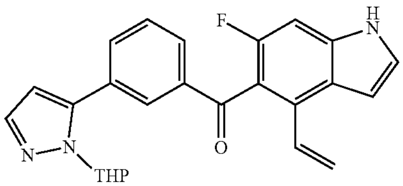

To a stirred solution of (6-fluoro-4-vinyl-1H-indol-5-yl)(3-(1-(tetrahydro-2H-pyran-2-yl)-1H-pyrazol-5-yl)phenyl)methanol (Intermediate 130D, 6.8 g, 16.30 mmol) in dimethyl sulfoxide (60 mL) was added 2-iodoxybenzoic acid (13.69 g, 48.90 mmol). The mixture was stirred at room temperature for 1 hour, then diluted with 200 mL of water, and extracted with ethyl acetate (3×200 mL). The combined organic phases were washed with brine, dried over sodium sulfate, and concentrated. The residue was purified by automated silica gel column chromatography (petroleum ether: ethyl acetate=4:1) to give the title compound (6.2 g, 92%) as a yellow solid. MS (ESI): 332 m/z $[M+H-THP]^+$, retention time: 1.89 minutes, purity: 95% (214 nm). (LC-MS Method 003).

| Inter. No. | Structure | Name | MS m/z [M + H]+ |
|---|---|---|---|
| 130-1 | 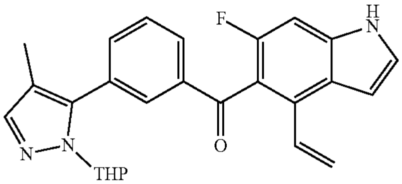 | (6-fluoro-4-vinyl-1H-indol-5-yl)(3-(4-methyl-1-(tetrahydro-2H-pyran-2-yl)-1H-pyrazol-5-yl)phenyl)methanone | 346 $[M + H - THP]^+$ |

Intermediate 130A: 3-(1-(Tetrahydro-2H-pyran-2-yl)-1H-pyrazol-5-yl)benzaldehyde

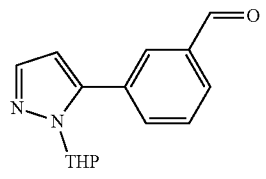

To a stirred solution of 3-bromobenzaldehyde (10 g, 54.36 mmol) in 1,4-Dioxane (80 mL) and water (16 mL) were added 1-(tetrahydro-2H-pyran-2-yl)-5-(4,4,5,5-tetramethyl-1,3,2-dioxaborolan-2-yl)-1H-pyrazole (22.7 g, 81.54 mmol), cesium carbonate (35.4 g, 108.7 mmol) and 1,1'-bis(diphenylphosphino)ferrocene-palladium (II) dichloride dichloromethane complex (2.2 g, 2.72 mmol). The mixture was stirred at 100° C. overnight. After cooling to room temperature, the mixture was partitioned between water (200 mL) and ethyl acetate (200 mL). The separated organic phase, combined with two additional ethyl acetate extracts (2×200 mL), was washed with brine, dried over sodium sulfate, and concentrated. The residue was purified by automated silica gel column chromatography (petroleum ether: ethyl acetate=4:1) to give the title compound (9.8 g, 70%) as a yellow solid. MS (ESI): 279 m/z $[M+Na]^+$, retention time: 1.71 minutes, purity: 98% (214 nm) (LC-MS Method 003).

Intermediate 130B: (4-Bromo-6-fluoro-1-(triisopropylsilyl)-1H-indol-5-yl)(3-(1-(tetrahydro-2H-pyran-2-yl)-1H-pyrazol-5-yl)phenyl)methanol

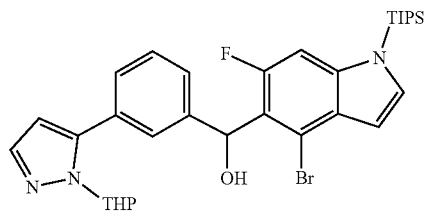

To a stirred and cooled (−78° C.) solution of 4-bromo-6-fluoro-1-(triisopropylsilyl)-1H-indole (12.36 g, 33.5 mmol) in tetrahydrofuran (80 mL) was added lithium diisopropylamide (30 mL, 60.9 mmol) under argon. The mixture was stirred for 1 hour at this temperature, then treated with 3-(1-(tetrahydro-2H-pyran-2-yl)-1H-pyrazol-5-yl)benzaldehyde (Intermediate 130A, 7.8 g, 30.45 mmol). The reaction was slowly warmed to room temperature and stirred overnight, then diluted with 150 mL of water, and extracted with ethyl acetate (3×150 mL). The combined organic phases were washed with brine, dried over sodium sulfate, and concentrated. The residue was purified by silica gel column chromatography (petroleum ether: ethyl acetate=4:1) to give the title compound (12.2 g, 60%) as a yellow solid. MS (ESI): 542, 544 m/z $[M+H-THP]^+$, retention time: 2.44 minutes, purity: 88% (214 nm). (LC-MS Method 003).

Intermediate 130C: (6-Fluoro-1-(triisopropylsilyl)-4-vinyl-1H-indol-5-yl)(3-(1-(tetrahydro-2H-pyran-2-yl)-1H-pyrazol-5-yl)phenyl)methanol

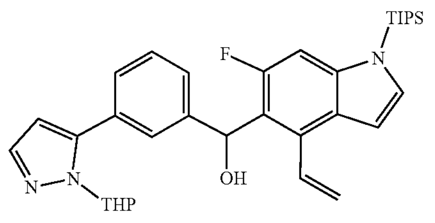

To a stirred solution of (4-bromo-6-fluoro-1-(triisopropylsilyl)-1H-indol-5-yl)(3-(1-(tetrahydro-2H-pyran-2-yl)-1H-pyrazol-5-yl)phenyl)methanol (Intermediate 130B, 12.2 g, 19.51 mmol) in 1,4-dioxane (100 mL) and water (20 mL) were added 4,4,5,5-tetramethyl-2-vinyl-1,3,2-dioxaborolane (4.5 g, 29.27 mmol), cesium carbonate (12.7 g, 39.02 mmol) and 1,1'-bis(diphenylphosphino)ferrocene-palladium (II) dichloride dichloromethane complex (797 mg, 0.98 mmol) under argon. The mixture was stirred at 100° C. overnight, diluted with 150 mL of water, and extracted with ethyl acetate (3×150 mL). The combined organic phases were washed with brine, dried over sodium sulfate, and concentrated. The crude was purified by silica gel column chromatography (petroleum ether:ethyl acetate=4:1) to give the title compound (10.3 g, 92%) as a yellow solid. MS (ESI): 490 m/z [M+H-THP]+, retention time: 2.41 minutes, purity: 95% (214 nm) (LC-MS Method 003).

| Inter. No. | Structure | Name | MS m/z $[M + H]^+$ |
|---|---|---|---|
| 130C-1 | 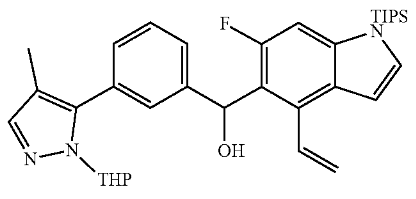 | (6-fluoro-1-(triisopropylsilyl)-4-vinyl-1H-indol-5-yl)(3-(4-methyl-1-(tetrahydro-2H-pyran-2-yl)-1H-pyrazol-5-yl)phenyl)methanol | 588 $[M + H]^+$ |

Intermediate 130D: (6-Fluoro-4-vinyl-1H-indol-5-yl)(3-(1-(tetrahydro-2H-pyran-2-yl)-1H-pyrazol-5-yl)phenyl)methanol

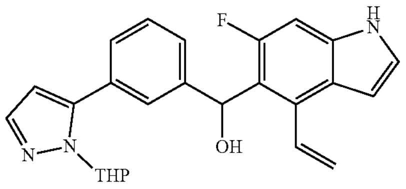

To a stirred solution of (6-fluoro-1-(triisopropylsilyl)-4-vinyl-1H-indol-5-yl)(3-(1-(tetrahydro-2H-pyran-2-yl)-1H-pyrazol-5-yl)phenyl)methanol (Intermediate 130C, 10.3 g, 17.97 mmol) in tetrahydrofuran (50 mL) was added tetrabutylammonium fluoride (36 mL, 35.93 mmol). The mixture was stirred at room temperature for 2 hours, then diluted with 150 mL of water, and extracted with ethyl acetate (3×150 mL). The combined organic phases were washed with brine, dried over sodium sulfate, and concentrated to give the title compound (6.8 g, 91%) as a yellow solid. MS (ESI): 334 m/z [M+H-THP]+, retention time: 1.79 minutes, purity: 93% (214 nm). (LC-MS Method 003).

Intermediate 131: (Z)-(2-Oxodihydrofuran-3(2H)-ylidene)methyl trifluoromethanesulfonate

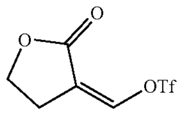 [SMILES: O=C1OCC/C1=C/OS(=O)(=O)C(F)(F)F]

To a stirred and degassed solution of dihydrofuran-2(3H)-one (11 mL, 139 mmol) in ether (200 mL) was added ethyl formate (17 mL, 209 mmol), sodium methoxide (15.06 g, 279 mmol) at room temperature. The mixture was purged with argon and stirred at room temperature overnight. The formed precipitate was collected by filtration to give sodium (Z)-(2-oxodihydrofuran-3(2H)-ylidene)methanolate (15.00 g, 79%) as a solid. This solid was used in the next step without further purification.

To a solution of the above filtrate cake (2.00 g, 14.7 mmol) in water (20 mL) was added concentrated hydrochloric acid (2.0 mL, 24.0 mmol). The mixture was stirred at room temperature for 1 hour, then extracted with ethyl acetate (2×50 mL). The combined organic phases were washed with brine, dried over sodium sulfate, and concentrated to give (Z)-3-(hydroxymethylene)dihydrofuran-2(3H)-one (0.70 g, 42%) as an oil. This oil was used in the next step without further purification.

To a stirred solution of the above oil (300 mg, 2.63 mmol) in dichloromethane (10 mL) were added N,N-diisopropylethylamine (0.92 mL, 5.26 mmol), and trifluoromethanesulfonic anhydride (0.67 mL, 3.94 mmol). The mixture was stirred at room temperature overnight, then poured into water (30 mL), and extracted with dichloromethane (2×20 mL). The combined organic layers were washed with brine, dried over sodium sulfate, and concentrated. The residue was purified by automated flash chromatography (25 g silica gel column, eluted with 0-15% ethyl acetate in petroleum ether) to give the title compound (230 mg, 36%) as an oil. MS (ESI): 247 m/z $[M+H]^+$, retention time: 1.67 minutes, purity: 98% (214 nm). (LC-MS Method 003).

Intermediate 132: 4-((4-Bromo-6-fluoro-1-(triisopropylsilyl)-1H-indol-5-yl)thio)picolinonitrile

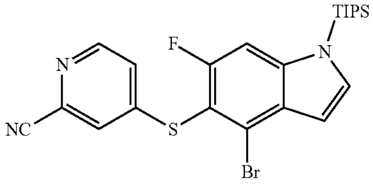

To a stirred and cooled (−78° C.) solution of 4-bromo-6-fluoro-1-(triisopropylsilyl)-1H-indole (1.97 g, 5.33 mmol) in tetrahydrofuran (30 mL) was added lithium diisopropylamide (2 M in tetrahydrofuran) (3.3 mL, 6.66 mmol) drop wise under argon. The mixture was stirred for 20 minutes at this temperature, then treated with 4,4'-disulfanediyldipicolinonitrile (Intermediate 132A, 1.20 g, 4.44 mmol) in tetrahydrofuran (5 mL). The reaction mixture was stirred at room temperature for 2 hours, quenched with water (50 mL), and extracted with ethyl acetate (2×30 mL). The combined organic extracts were washed with brine, dried over sodium sulfate, and concentrated. The residue was purified by automated flash chromatography (40 g silica gel column, eluted with 0-40% ethyl acetate in petroleum ether) to give the title compound (0.40 g, 18%) as a solid. MS (ESI): 504, 506 m/z $[M+H]^+$, retention time: 2.56 minutes, purity: 99% (214 nm) (LC-MS Method 003).

The following intermediate was prepared based on the procedures described for Intermediate 132.

| Inter. No. | Structure | Name | MS m/z $[M + H]^+$ |
|---|---|---|---|
| 132-1 | 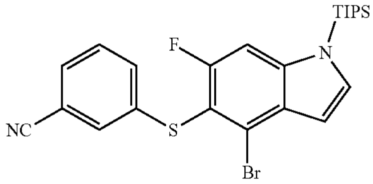 | 3-((4-bromo-6-fluoro-1-(triisopropylsilyl)-1H-indol-5-yl)thio)benzonitrile | 503, 505 |

Intermediate 132A: 4,4'-Disulfanediyldipicolinonitrile

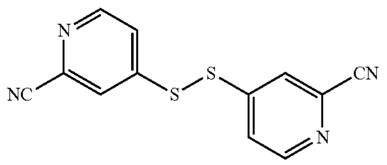 [SMILES: N#Cc1cc(SSc2ccnc(C#N)c2)ccn1]

To a stirred solution of 4-chloropicolinonitrile (15.00 g, 108 mmol) in N,N-dimethyl formamide (200 mL) was added potassium ethanethioate (24.73 g, 217 mmol). The mixture was stirred at room temperature overnight, then treated with iodine (13.74 g, 54.1 mmol), and stirred for an additional 16 hours. The reaction mixture was quenched with water (500 mL), extracted with ethyl acetate (2×200 mL). The combined organic phases were washed with brine, dried over sodium sulfate, and concentrated. The residue was purified by automated flash chromatography (120 g silica gel column, eluted with 0-20% ethyl acetate in petroleum ether) to give the title compound (1.20 g, 4.10%) as an oil. MS (ESI): 271 m/z $[M+H]^+$, retention time: 1.83 minutes, purity: 84% (214 nm) (LC-MS Method 003).

Intermediate 133: Methyl 2-((4-bromo-6-fluoro-1H-indol-5-yl)oxy)pyridine-4-carbimidothioate Hydroiodide

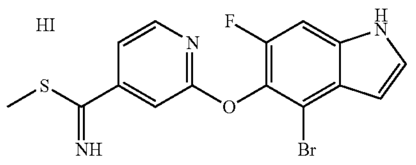

To a stirred solution of 2-((4-bromo-6-fluoro-1H-indol-5-yl)oxy)pyridine-4-carbothioamide (Intermediate 133C, 366 mg, 1.0 mmol) in acetone (6 mL) was added methyl iodide (0.31 mL, 5.00 mmol). The mixture was stirred at 60° C. for 4 hours and concentrated to give the title compound (0.48 g, 59%) as a yellow solid. MS (ESI): 380, 382 m/z $[M+H]^+$, retention time: 1.76 minutes, purity: 50% (214 nm) (LC-MS Method 003).

The following intermediate was prepared based on the procedures described for Intermediate 133.

| Inter. No. | Structure | Name | MS m/z $[M + H]^+$ |
|---|---|---|---|
| 133-1* | 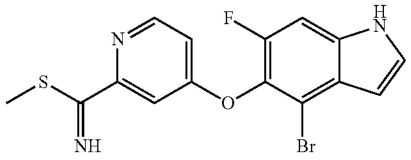 [SMILES: CSC(=N)c1cc(Oc2c(F)cc3[nH]ccc3c2Br)ccn1] | methyl 4-((4-bromo-6-fluoro-1H-indol-5-yl)oxy)pyridine-2-carbimidothioate | 380, 382 $[M + H]^+$; RT: 1.57 min. (LC-MS method 4) |

*The methylation of thioamide was realized in acetone/iodomethane (5.0 eq)/sodium bicarbonate (5.0 eq)/room temperature, slightly different from the procedure described for Intermediate 133.

Intermediate 133A: 2-((4-Bromo-6-fluoro-1H-indol-5-yl)oxy)isonicotinic Acid

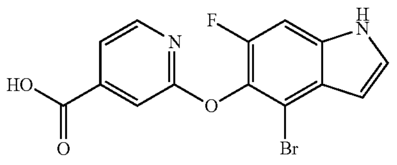 [SMILES: O=C(O)c1ccnc(Oc2c(F)cc3[nH]ccc3c2Br)c1]

To a stirred solution of methyl 2-((4-bromo-6-fluoro-1H-indol-5-yl)oxy)isonicotinate (Intermediate 2-10, 0.37 g, 1.00 mmol) in methanol (3 mL) and tetrahydrofuran (9 mL) was added lithium hydroxide (5M in water, 3.0 mL, 3.00 mmol). The mixture was stirred at room temperature for 16 hours, then acidified with 1 M hydrochloric acid to pH ~4 and diluted with ethyl acetate (50 mL). The solution was washed with water, brine, dried over sodium sulfate and concentrated to give the title compound (0.34 g, 91%) as a white solid. MS (ESI): 351, 353 m/z $[M+H]^+$, retention time: 1.73 minutes, purity: 94% (214 nm) (LC-MS Method 003).

The following intermediate was prepared based on the procedures described for Intermediate 133A.

| Inter. No. | Structure | Name | MS m/z [M + H]$^+$ |
|---|---|---|---|
| 133A-1 | 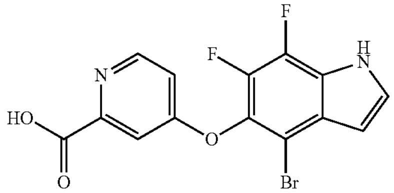 [SMILES: O=C(O)c1cc(Oc2c(F)c(F)c3[nH]ccc3c2Br)ccn1] | 4-((4-bromo-6,7-difluoro-1H-indol-5-yl)oxy)picolinic acid | 369, 371 [M + H]$^+$; RT: 1.41 min. (LC-MS method 27) |
| 133A-2 | 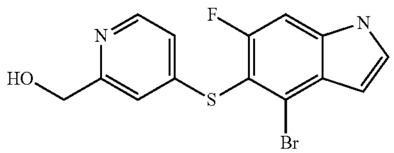 [SMILES: OCc1cc(Sc2c(F)cc3[nH]ccc3c2Br)ccn1] | 4-((4-bromo-6-fluoro-1H-indol-5-yl)thio)picolinic acid | 367, 369 [M + H]$^+$; RT: 1.50 min. (LC-MS method 21) |
| 133A-3 | 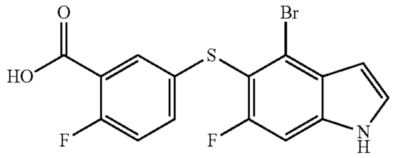 [SMILES: O=C(O)c1cc(Sc2c(F)cc3[nH]ccc3c2Br)ccc1F] | 5-((4-bromo-6-fluoro-1H-indol-5-yl)thio)-2-fluorobenzoic acid | 384, 386 [M + H]$^+$; RT: 1.50 min. (LC-MS method 4) |

Intermediate 133B: 2-((4-Bromo-6-fluoro-1H-indol-5-yl)oxy)isonicotinamide

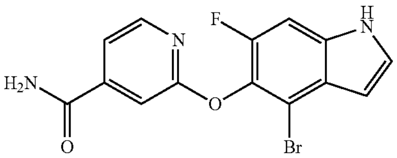 [SMILES: NC(=O)c1ccnc(Oc2c(F)cc3[nH]ccc3c2Br)c1]

To a stirred solution of 2-((4-bromo-6-fluoro-1H-indol-5-yl)oxy)isonicotinic acid (Intermediate 133A, 0.35 g, 1.00 mmol), ammonium chloride (214 mg, 4.0 mmol) and N,N-diisopropylethylamine (1.0 mL, 6.0 mmol) in N,N-dimethylformamide (10 mL) was added 2-(7-azabenzotriazol-1-yl)-N,N,N',N'-tetramethyluronium hexafluorophosphate (1.14 g, 3.0 mmol). The mixture was stirred at room temperature overnight, quenched with water (30 mL), and extracted with ethyl acetate (3×25 mL). The combined organic extracts were washed with saturated sodium bicarbonate, brine, dried over sodium sulfate, and concentrated to give the title compound (290 mg, 60% yield) as a solid. MS (ESI): 350, 352 m/z [M+H]$^+$, retention time: 1.64 minutes, purity: 72% (214 nm). (LC-MS Method 003).

The following intermediate was prepared based on the procedures described for Intermediate 133B.

| Inter. No. | Structure | Name | MS m/z [M + H]$^+$ |
|---|---|---|---|
| 133B-1 | 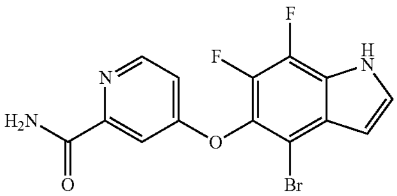 [SMILES: NC(=O)c1cc(Oc2c(F)c(F)c3[nH]ccc3c2Br)ccn1] | 4-((4-bromo-6,7-difluoro-1H-indol-5-yl)oxy)picolinamide | 368, 370 [M + H]$^+$; RT: 1.41 min. (LC-MS method 27) |

Intermediate 133C: 2-((4-Bromo-6-fluoro-1H-indol-1-yl)oxy)pyridine-4-carbothioamide

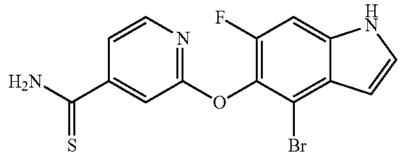 [SMILES: NC(=S)c1ccnc(Oc2c(F)cc3[nH]ccc3c2Br)c1]

To a stirred solution of 2-((4-bromo-6-fluoro-1H-indol-5-yl)oxy)isonicotinamide (Intermediate 133B, 175 mg, 0.5 mmol) in tetrahydrofuran (10 mL) was added Lawson's Reagent (243 mg, 0.6 mmol). The reaction mixture was stirred at room temperature for 16 hours. The solvent was removed via evaporation. The residue was partitioned between water (20 mL) and ethyl acetate (25 mL). The separated organic layer, combined with two additional ethyl acetate extracts (2×15 mL), was washed with saturated sodium bicarbonate (20 mL) and brine (20 mL), dried over sodium sulfate, and concentrated. The residue was purified by automated flash chromatography (40 g silica gel column, eluted with 0-30% ethyl acetate in petroleum ether) to give the title compound (170 mg, 87% yield) as a yellow solid. MS (ESI): 366, 368 m/z $[M+H]^+$, retention time: 1.78 minutes, purity: 95% (214 nm) (LC-MS Method 033).

The following intermediate was prepared based on the procedures described for Intermediate 133C.

| Inter. No. | Structure | Name | MS m/z $[M + H]^+$ |
|---|---|---|---|
| 133C-1 | 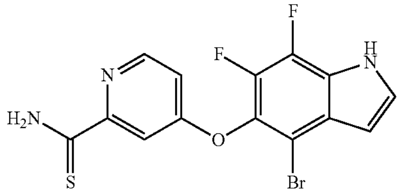 [SMILES: NC(=S)c1cc(Oc2c(F)c(F)c3[nH]ccc3c2Br)ccn1] | 4-((4-bromo-6,7-difluoro-1H-indol-5-yl)oxy)pyridine-2-carbothioamide | 384, 386 $[M + H]^+$; RT: 1.77 min. (LC-MS method 17) |

purified by silica gel column chromatography (dichloromethane:methanol=20:1) to give the title compound (630 mg, 29.3%) as a colorless liquid. MS (ESI): 585 m/z $[M+Na]^+$, retention time: 1.80 minutes, purity: 83% (214 nm) (LC-MS Method 003).

Intermediate 134A: Tert-Butyl 2-(3-(2-(benzyloxy)-3-ethoxy-3-oxopropyl)phenyl)-7-((2-((tert-butyldimethylsilyl)oxy)ethyl)sulfonyl)-2,6,6-trimethylheptanoate

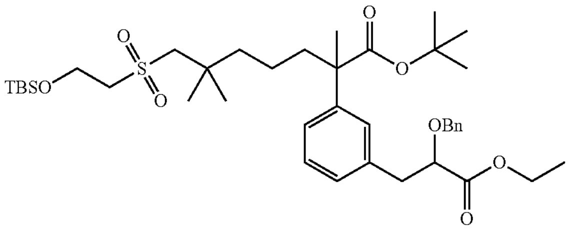

Intermediate 134: 2-(3-(2-(benzyloxy)-3-ethoxy-3-oxopropyl)phenyl)-7-((2-hydroxyethyl)sulfonyl)-2,6,6-trimethylheptanoic Acid

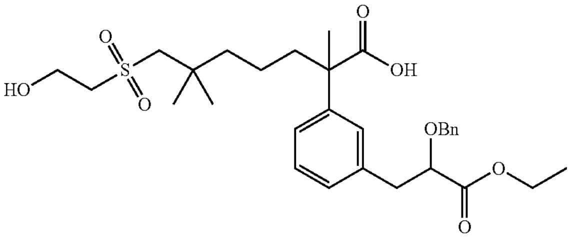 [SMILES: CCOC(=O)C(Cc1cccc(C(C)(CCCC(C)(C)CS(=O)(=O)CCO)C(=O)O)c1)OCc1ccccc1]

To a stirred solution of tert-butyl 2-(3-(2-(benzyloxy)-3-ethoxy-3-oxopropyl)phenyl)-7-((2-((tert-butyldimethylsilyl)oxy)ethyl)sulfonyl)-2,6,6-trimethylheptanoate (Intermediate 134A, 2.8 g, 3.82 mmol) in dichloromethane (20 mL) was added trifluoroacetic acid (2.2 g, 19.11 mmol). The mixture was stirred at room temperature overnight. The solvent was removed via evaporation, and the residue was To a stirred solution of tert-butyl 7-((2-((tert-butyldimethylsilyl)oxy)ethyl)sulfonyl)-2-(3-(2-diazo-3-ethoxy-3-oxopropyl)phenyl)-2,6,6-trimethylheptanoate (Intermediate 124B, 2.2 g, 3.37 mmol) in toluene (30 mL) were added rhodium(II) acetate dimer (150 mg, 0.34 mmol) and benzyl alcohol (1.82 g, 16.86 mmol). The mixture was stirred at 65° C. for 3 hours, then cooled to room temperature and partitioned between water (100 mL) and ethyl acetate (100 mL). The separated organic layer, combined with two additional ethyl acetate extracts (2×100 mL), was washed with brine, dried over sodium sulfate, and concentrated. The crude product was purified by silica gel column chromatography (petroleum ether:ethyl acetate=4:1) to give the title compound (2.8 g, 3.82 mmol) as a colorless liquid. MS (ESI): 755 m/z $[M+Na]^+$, retention time: 2.56 minutes, purity: 50% (214 nm) (LC-MS Method 003).

The same procedure was used to prepare the following intermediates.

| Inter. No. | Structure | Name | MS m/z [M + H]+ |
|---|---|---|---|
| 134-1 | 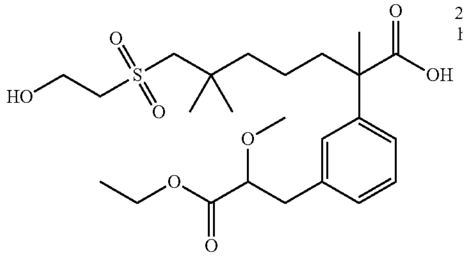 | 2-(3-(3-ethoxy-2-methoxy-3-oxopropyl)phenyl)-7-((2-hydroxyethyl)sulfonyl)-2,6,6-trimethylheptanoic acid | 509 $[M + Na]^+$ |

Intermediate 135: (R)-7-Hydroxy-2-(3-iodophenyl)-2,6,6-trimethylheptanoic Acid

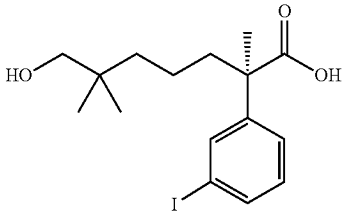 [SMILES: CC(C)(CO)CCC[C@@](C)(C(=O)O)c1cccc(I)c1]

A chiral salt of enantiomer 1 of (S)-1-(naphthalen-1-yl)ethan-1-aminium (R)-7-hydroxy-2-(3-iodophenyl)-2,6,6-trimethylheptanoate (Intermediate 135B, 233 g, 415 mmol) was suspended in ethyl acetate (1000 mL). The mixture was washed with 1N HCl (5×500 mL), brine, dried over anhydrous sodium sulfate, and concentrated to give the title compound (160.00 g, 99%) as a light-yellow oil. MS (ESI): 413 m/z $[M+Na]^+$, retention time: 1.98 minutes, purity: 89% (214 nm) (LC-MS Method 003).

Intermediate 135A: ~90% ee of (S)-1-(Naphthalen-1-yl)ethan-1-aminium (R)-7-hydroxy-2-(3-iodophenyl)-2,6,6-trimethylheptanoate

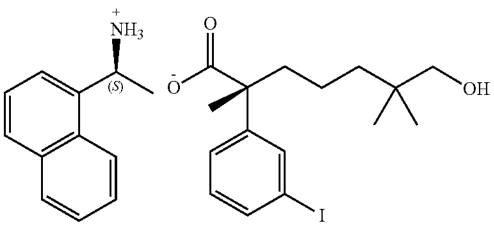

To a stirred solution of (S)-(−)-1-(1-naphthyl)ethylamine (127 mL, 705 mmol) in ethyl acetate (7.5 L) was added 7-hydroxy-2-(3-iodophenyl)-2,6,6-trimethyl-heptanoic acid (Intermediate 17B, 500.00 g, 1281 mmol). The reaction was stirred at room temperature overnight. The solid was collected by filtration and the filtrate cake was washed with ethyl acetate (800 mL). The wet solid was then suspended into EtOAc (1.7 L) and stirred at room temperature for 20 minutes. The mixture was filtered and washed with ethyl acetate (800 mL). The solid was collected and dried by air to give Enantiomer 1 of (S)-1-(naphthalen-1-yl)ethan-1-aminium 7-hydroxy-2-(3-iodophenyl)-2,6,6-trimethyl-heptanoate (288 g, 40%). Chiral purity: 95% (90% ee). (Chiral conditions: column: AD-H; Mobile phase: n-hexane (0.1% diethylamine): ethanol (0.1% diethylamine)=95:5; Column temperature: 40° C.; Flow rate: 1.0 mL/minute; Wavelength: 220 nm; Instrument: Shimadzu; Solid salt were de-salted with 1N hydrochloric acid in acetonitrile before injection)

Intermediate 135B: ~98% ee of (S)-1-(Naphthalen-1-yl)ethan-1-aminium (R)-7-hydroxy-2-(3-iodophenyl)-2,6,6-trimethylheptanoate

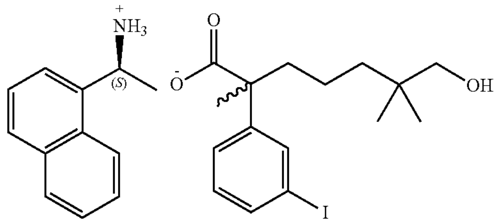

A solution of ~90% ee of Enantiomer 1 of (S)-1-(naphthalen-1-yl)ethan-1-aminium (R)-7-hydroxy-2-(3-iodophenyl)-2,6,6-trimethylheptanoate (Intermediate 135A, 186 g, 315 mmol) in acetonitrile (7.65 L) was refluxed for 5 hours and then stirred at room temperature overnight. The mixture was filtered and rinsed with acetonitrile (2×450 mL). The solid was collected and dried in vacuo to give the title compound (153 g, 86%). Chiral purity: 99% (98% ee, chiral method is the same as in Intermediate 135A). $^1H$ NMR (400 MHz, $CDCl_3$) δ 7.84 (t, J=6.7 Hz, 2H), 7.77 (d, J=8.2 Hz, 1H), 7.67 (t, J=1.6 Hz, 1H), 7.56 (d, J=7.1 Hz, 1H), 7.52-7.37 (m, 4H), 7.19 (d, J=8.5 Hz, 1H), 6.92 (t, J=7.9 Hz, 1H), 4.85 (q, J=6.6 Hz, 1H), 3.19 (dd, J=42.8, 10.4 Hz, 2H), 1.77-1.66 (m, 1H), 1.61-1.57 (m, 1H), 1.54 (d, J=6.7 Hz, 3H), 1.38 (s, 3H), 1.28-0.98 (m, 4H), 0.79 (s, 3H), 0.74 (s, 3H) ppm.

Intermediate 136: Methyl (S)-3-iodo-2-methylpropanoate

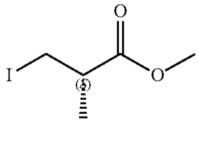

To a stirred and cooled (0° C.) solution of methyl (2R)-3-hydroxy-2-methyl-propanoate (100 g, 0.85 mol) in dichloromethane (1.5 L) was added triphenylphosphine (444 g, 1.69 mol), imidazole (115 g, 1.69 mol), followed by addition of iodine (430 g, 1.69 mol) portion wise. The reaction was warmed up to room temperature and stirred overnight. The mixture was filtered. The filtrate was concentrated. The residue was treated with 10% ethyl acetate in petroleum ether (1 L) and then filtered again. The filtrate was concentrated. The residue was purified by automated flash chromatography (330 g silica gel column, eluting with 0-5% ethyl acetate in petroleum ether) to afford the title compound (183 g, 94%) as an oil. $^1$H NMR (400 MHz, $CDCl_3$) δ 3.73 (s, 3H), 3.38 (dd, J=10.0, 6.4 Hz, 1H), 3.26 (dd, J=10.0, 6.4 Hz, 1H), 2.83-2.78 (m, 1H), 1.28 (d, J=6.8 Hz, 3H) ppm.

The following intermediates were prepared based on the procedures described for Intermediate 137 and/or Intermediates 136.

| Inter. No. | Structure | Name | MS m/z [M + H]$^+$ |
| --- | --- | --- | --- |
| 136-1 | 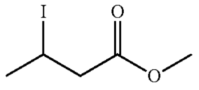 | methyl 3-iodobutanoate | $^1$H NMR (400 MHz, $CDCl_3$) δ 4.48-4.42 (m, 1H), 3.72 (s, 3H), 3.05-2.89 (m, 2H), 1.94 (d, J = 6.8 Hz, 3H) ppm. |

Intermediate 137: Methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate

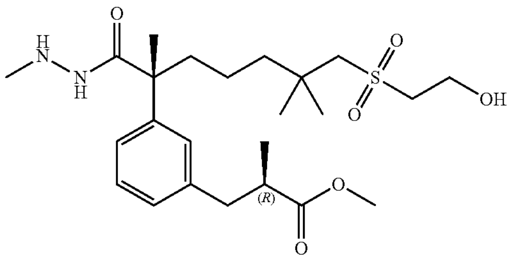

To a stirred solution of tert-butyl 2-((R)-7-((2-hydroxyethyl)sulfonyl)-2-(3-((R)-3-methoxy-2-methyl-3-oxopropyl)phenyl)-2,6,6-trimethylheptanoyl)-1-methylhydrazine-1-carboxylate (Intermediate 137I, 150.00 g, 257 mmol) in dichloromethane (800 mL) was added trifluoroacetic acid (200 mL). The mixture was stirred at room temperature for 4 hours and concentrated. The residue was diluted with water (1000 mL), neutralized with saturated sodium bicarbonate aqueous solution to pH-7, and extracted with ethyl acetate (2×800 mL). The combined organic layers were washed with water, brine, dried over sodium sulfate, filtered, and concentrated to give the title compound (120 g, 97%) as a light-yellow oil. MS (ESI): 485 m/z [M+H]$^+$; purity: 92% (214 nm); retention time: 1.47 minutes (LC-MS Method 4). Chiral-HPLC purity: 99.4% (>99% ee, 254 nm), RT=1.75 minutes (chiral SFC column conditions: Column: AD-3, 4.6×100 mm, 3 μm; mobile phase: carbon dioxide/methanol (0.2%7M ammonia in methanol)=80:20); Injection volume: 5.00 uL; Run time: 6.0 minutes; Flow rate: 3.0 mL/minute; Wavelength: 214 nm; Column temperature: 40° C.).

The following intermediates were prepared based on the procedures described for Intermediate 137 and/or Intermediates 137A to 137I.

| Inter. No. | Structure | Name | MS m/z [M + H]$^+$ |
| --- | --- | --- | --- |
| 137-1 | 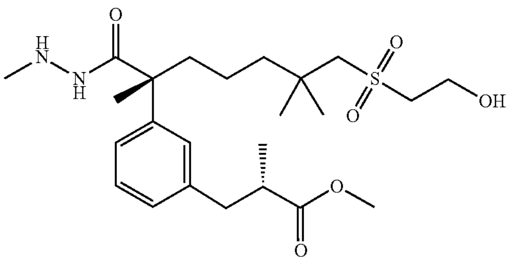 [SMILES: CNNC(=O)[C@](C)(CCCC(C)(C)CS(=O)(=O)CCO)c1cccc(C[C@H](C)C(=O)OC)c1] | methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate | 485 [M + H]; RT 1.47 min. (LC-MS method 4) |

-continued

| Inter. No. | Structure | Name | MS m/z [M + H]$^+$ |
| --- | --- | --- | --- |
| 137-2 | 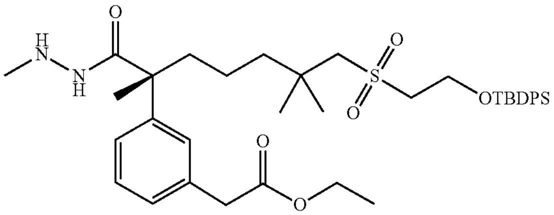 | ethyl (R)-2-(3-(7-((2-((tert-butyldiphenylsilyl)oxy)ethyl)sulfonyl)-2,6,6-trimethyl-1-(2-methylhydrazineyl)-1-oxoheptan-2-yl)phenyl)acetate | 709.0 [M + H]$^+$; RT: 2.11 min. (LC-MS method 27) |
| 137-3 | 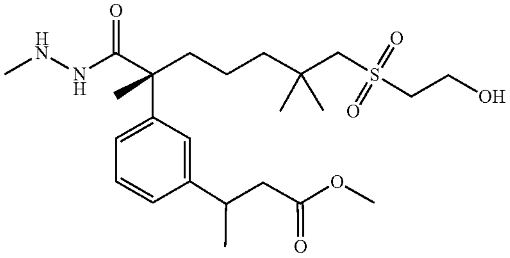 [SMILES: CNNC(=O)[C@](C)(CCCC(C)(C)CS(=O)(=O)CCO)c1cccc(C(C)CC(=O)OC)c1] | methyl 3-(3-((R)-7-((2-hydroxyethyl)sulfonyl)-2,6,6-trimethyl-1-(2-methylhydrazineyl)-1-oxoheptan-2-yl)phenyl)butanoate | 485 [M + H]$^+$; RT: 1.75 min. (LC-MS method 16) |
| 137-4 | 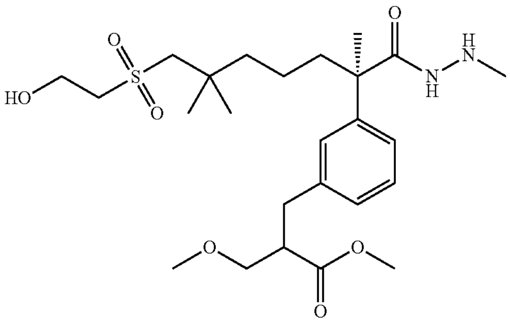 [SMILES: CNNC(=O)[C@](C)(CCCC(C)(C)CS(=O)(=O)CCO)c1cccc(CC(COC)C(=O)OC)c1] | methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate | 515 [M + H]$^+$; RT: 1.71 min. (LC-MS method 16) |
| 137-5 | 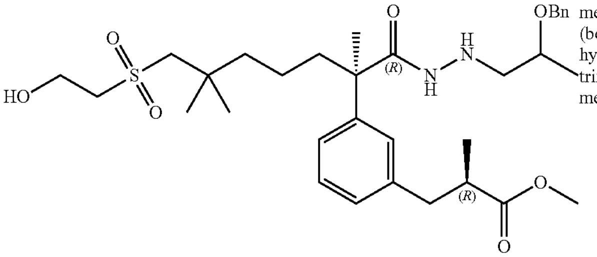 | methyl (2R)-3-(3-((2R)-1-(2-(2-(benzyloxy)propyl)hydrazineyl)-7-((2-hydroxyethyl)sulfonyl)-2,6,6-trimethyl-1-oxoheptan-2-yl)phenyl)-2-methylpropanoate | 619 [M + H]$^+$; RT: 1.81 min. (LC-MS method 16) |
| 137-6 | 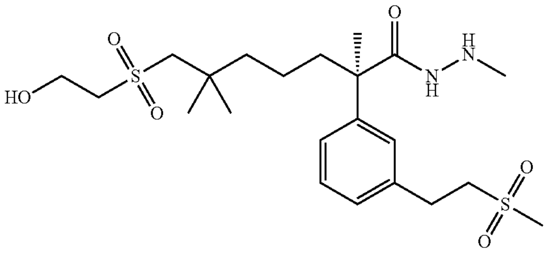 [SMILES: CNNC(=O)[C@](C)(CCCC(C)(C)CS(=O)(=O)CCO)c1cccc(CCS(C)(=O)=O)c1] | (R)-7-((2-hydroxyethyl)sulfonyl)-N',2,6,6-tetramethyl-2-(3-(2-(methylsulfonyl)ethyl)phenyl)heptane hydrazide | 491 [M + H]$^+$; RT: 1.37 min. (LC-MS method 16) |
| 137-7 | 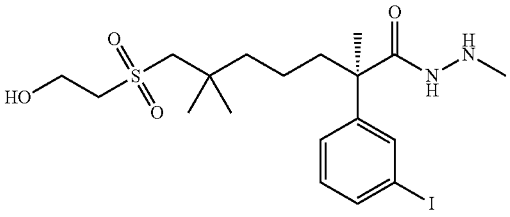 [SMILES: CNNC(=O)[C@](C)(CCCC(C)(C)CS(=O)(=O)CCO)c1cccc(I)c1] | (R)-7-((2-hydroxyethyl)sulfonyl)-2-(3-iodophenyl)-N',2,6,6-tetramethylheptanehydrazide | 511 [M + H]$^+$; RT: 1.59 min. (LC-MS method 4) |

-continued

| Inter. No. | Structure | Name | MS m/z [M + H]$^+$ |
| --- | --- | --- | --- |
| 137-8 | 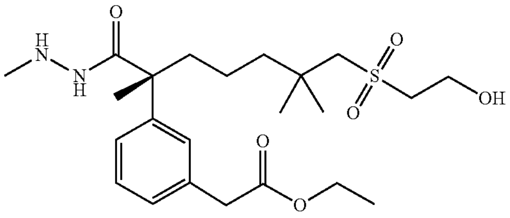 [SMILES: CCOC(=O)Cc1cccc([C@@](C)(CCCC(C)(C)CS(=O)(=O)CCO)C(=O)NNC)c1] | ethyl (R)-2-(3-(7-((2-hydroxyethyl)sulfonyl)-2,6,6-trimethyl-1-(2-methylhydrazineyl)-1-oxoheptan-2-yl)phenyl)acetate | 471 [M + H]$^+$; RT: 1.53 min. (LC-MS method 4) |
| 137-9 | 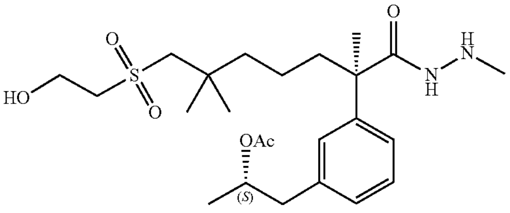 | (S)-1-(3-((R)-7-((2-hydroxyethyl)sulfonyl)-2,6,6-trimethyl-1-(2-methylhydrazineyl)-1-oxoheptan-2-yl)phenyl)propan-2-yl acetate | 485 [M + H]$^+$; RT: 1.48 min. (LC-MS method 4) |
| 137-10 | 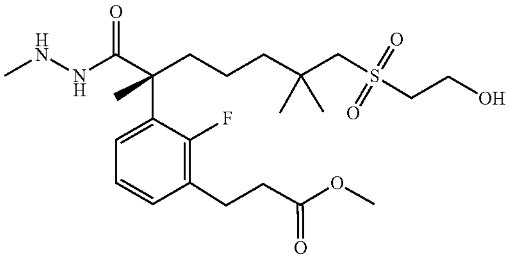 [SMILES: CNNC(=O)[C@](C)(CCCC(C)(C)CS(=O)(=O)CCO)c1cccc(CCC(=O)OC)c1F] | methyl (R)-3-(2-fluoro-3-(7-((2-hydroxyethyl)sulfonyl)-2,6,6-trimethyl-1-(2-methylhydrazineyl)-1-oxoheptan-2-yl)phenyl)propanoate | 489 [M + H]$^+$; RT: 1.46 min. (LC-MS method 3) |
| 137-11 | 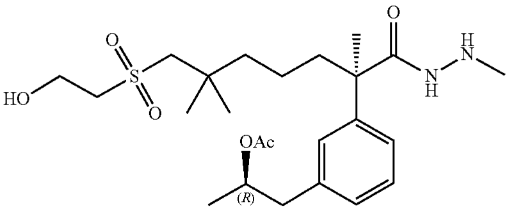 | (R)-1-(3-((R)-7-((2-hydroxyethyl)sulfonyl)-2,6,6-trimethyl-1-(2-methylhydrazineyl)-1-oxoheptan-2-yl)phenyl)propan-2-yl acetate | 485 [M + H]$^+$; RT: 1.48 min. (LC-MS method 3) |
| 137-12 | 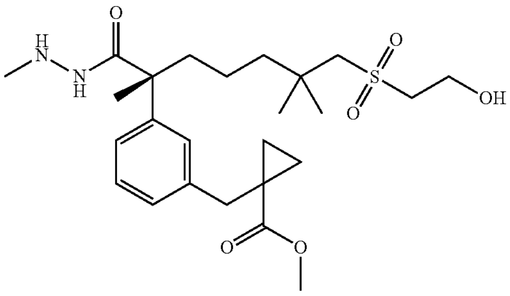 [SMILES: CNNC(=O)[C@](C)(CCCC(C)(C)CS(=O)(=O)CCO)c1cccc(CC2(C(=O)OC)CC2)c1] | methyl (R)-1-(3-(7-((2-hydroxyethyl)sulfonyl)-2,6,6-trimethyl-1-(2-methylhydrazineyl)-1-oxoheptan-2-yl)benzyl)cyclopropane-1-carboxylate | 497 [M + H]$^+$; RT: 1.70 min. (LC-MS method 027) |
| 137-13 | 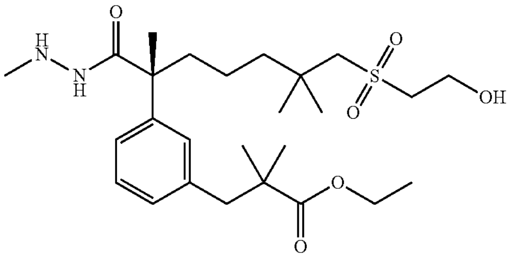 | methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate | 499 [M + H]$^+$; RT: 1.52 min. (LC-MS method 003) |

-continued

| Inter. No. | Structure | Name | MS m/z [M + H]$^+$ |
|---|---|---|---|
| 137-14 | 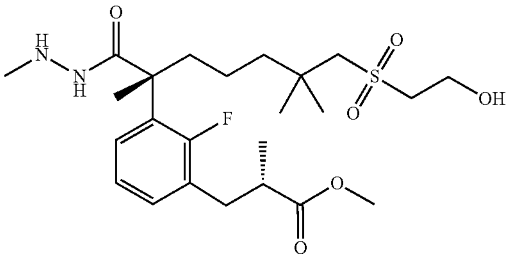 [SMILES: CNNC(=O)[C@](C)(CCCC(C)(C)CS(=O)(=O)CCO)c1cccc(C[C@H](C)C(=O)OC)c1F] | methyl (S)-3-(2-fluoro-3-((R)-7-((2-hydroxyethyl)sulfonyl)-2,6,6-trimethyl-1-(2-methylhydrazineyl)-1-oxoheptan-2-yl)phenyl)-2-methylpropanoate | 503 [M + H]$^+$; RT: 1.44 min. (LC-MS method 004) |
| 137-15 | 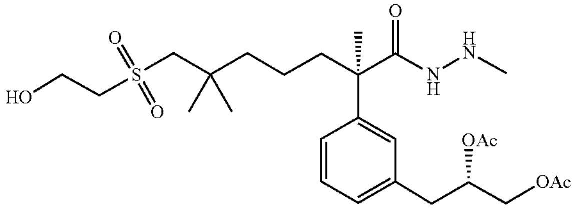 [SMILES: CNNC(=O)[C@](C)(CCCC(C)(C)CS(=O)(=O)CCO)c1cccc(C[C@@H](COC(C)=O)OC(C)=O)c1] | (S)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (~7:3 S:R at diol position) | 543 [M + H]$^+$; RT: 1.42 min. (LC-MS method 004) |
| 137-16 | 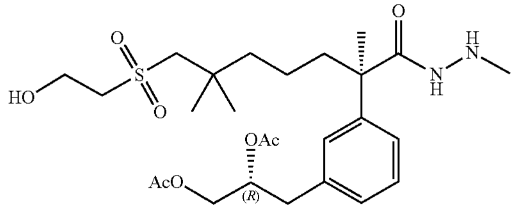 | (R)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (~7:3 R:S at diol position) | 543 [M + H]$^+$; RT: 1.42 min. (LC-MS method 004) |

Intermediate 137A: Benzyl (R)-7-hydroxy-2-(3-iodophenyl)-2,6,6-trimethylheptanoate

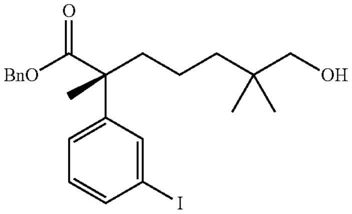 [SMILES: CC(C)(CO)CCC[C@@](C)(C(=O)OCc1ccccc1)c1cccc(I)c1]

To a stirred solution of (R)-7-hydroxy-2-(3-iodophenyl)-2,6,6-trimethylheptanoic acid (Intermediate 135, 160.00 g, 410 mmol) in N,N-dimethylformamide (800 mL) was added benzyl bromide (73.6 g, 430 mmol) and potassium carbonate (85.00 g, 615 mmol). The reaction was stirred at room temperature for 16 hours, then diluted with water (1.5 L), and extracted with ethyl acetate (3×800 mL). The combined organic phases were washed with brine, dried over sodium sulfate, and concentrated. The residue was purified by automated flash chromatography (330 g silica gel column, eluting with 0-25% ethyl acetate in petroleum) to give the title compound (190.00 g, 96%) as a light-yellow oil. $^1$H NMR (400 MHz, $CDCl_3$) δ 7.62 (t, J=1.7 Hz, 1H), 7.57 (d, J=7.8 Hz, 1H), 7.36-7.28 (m, 3H), 7.25-7.19 (m, 3H), 7.02 (t, J=7.9 Hz, 1H), 5.20-5.05 (m, 2H), 3.23 (d, J=4.4 Hz, 2H), 2.04-1.97 (m, 1H), 1.86-1.75 (m, 1H), 1.62 (s, 1H), 1.53 (s, 3H), 1.30-1.15 (m, 4H), 0.80-0.77 (m, 6H) ppm. MS (ESI): 503 m/z [M+Na]$^+$; Purity: 98% (214 nm); Retention time: 2.14 minutes (LC-MS Method 4). Chiral-HPLC: RT=1.630 min, 99% (98% ee) (chiral SFC column conditions: Column: OJ-3, 4.6×100 mm, 3 μm; mobile phase: carbon dioxide/methanol (0.2%7M ammonia in methanol) (90:10); injection volume: 3.00 uL; Run time: 6.0 minutes; Flow rate: 3.0 mL/minute; Back-pressure: 2000 psi; Column temperature: 40° C.)

Intermediate 137B: Benzyl (R)-7-(acetylthio)-2-(3-iodophenyl)-2,6,6-trimethylheptanoate

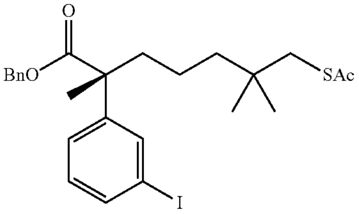

To a stirred and cooled (0° C.) solution of triphenylphosphine (207.48 g, 791 mmol) in tetrahydrofuran (1.5 L) was added diisopropyl azodicarboxylate (154 mL, 791 mmol) dropwise at 0° C. The mixture was stirred at 0° C. until the formation of a white solid was observed. A solution of benzyl (R)-7-hydroxy-2-(3-iodophenyl)-2,6,6-trimethylheptanoate (Intermediate 137A, 190.00 g, 396 mmol) and thio-acetic acid (2.00 eq, 57 mL, 791 mmol) in tetrahydrofuran (200 mL) was added dropwise at 0° C. After the addition, the mixture was stirred at 0° C. for 1 hour, then at room temperature for 16 hours, and concentrated. The residue was slurred with 10% ethyl acetate in petroleum ether (1.0 L) for 0.5 hours and filtered. the filtrate was concentrated. The residue was purified by automated flash chromatography (330 g silica gel column×2, eluting with 0-10% ethyl acetate in petroleum) to give the title compound (200.00 g, 94%) as light-yellow oil. MS (ESI): 561 m/z $[M+Na]^+$; purity: 91% (214 nm); Purity: 91% (214 nm); retention time: 2.39 minutes (LC-MS Method 4). Chiral-HPLC purity: RT=1.35 min, 99.3% (98.6% ee) (chiral SFC column conditions: Column: OJ-3, 4.6×100 mm, 3 μm; mobile phase: carbon dioxide/methanol (0.2%7M ammonia in methanol) (90:10); injection volume: 0.80 uL; Run time: 4.0 minutes; Flow rate: 3.0 mL/minute; Back-pressure: 2000 psi; Column temperature: 40° C.)

Intermediate 137C: Benzyl (R)-7-((2-hydroxyethyl)thio)-2-(3-iodophenyl)-2,6,6-trimethylheptanoate

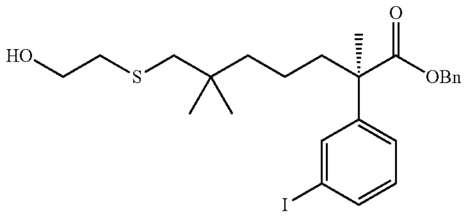 [SMILES: CC(C)(CCC[C@@](C)(C(=O)OCc1ccccc1)c1cccc(I)c1)CSCCO]

To a stirred and cooled (0° C.) solution of benzyl (R)-7-(acetylthio)-2-(3-iodophenyl)-2,6,6-trimethylheptanoate (Intermediate 137B, 200.00 g, 390 mmol) in ethanol (500 mL) was added 2-bromoethanol (34 mL, 483 mmol) and sodium ethoxide (20% in ethanol, 189.56 g, 557 mmol) dropwise. The mixture was stirred at 0° C. for 1.0 hour, quenched with water (1.0 L), and extracted with ethyl acetate (3×600 mL). The combined organic extracts were washed with brine, dried over sodium sulfate, filtered and concentrated. The residue was purified by automated flash chromatography (330 g silica gel column, eluting with 0-30% ethyl acetate in petroleum ether) to give the title compound (190 g, 95%) as light-yellow oil. MS (ESI): 563 m/z $[M+Na]^+$; purity: 86% (214 nm); (214 nm); retention time: 2.28 minutes (LC-MS Method 4). Chiral-HPLC purity: RT=2.10 min, 99.5% (99% ee) (chiral SFC column conditions: Column: OJ-3, 4.6×100 mm, 3 μm; mobile phase: carbon dioxide/methanol (0.2%7M ammonia in methanol) (90:10); injection volume: 5.00 uL; Run time: 6.0 minutes; Flow rate: 3.0 mL/minute; Back-pressure: 2000 psi; Column temperature: 40° C.) Intermediate 137D: Benzyl (R)-7-((2-hydroxyethyl)sulfonyl)-2-(3-iodophenyl)-2,6,6-trimethylheptanoate

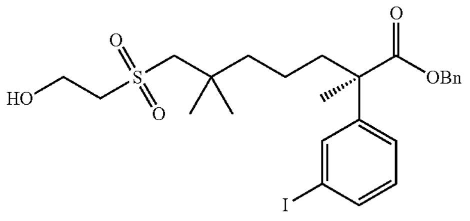 [SMILES: CC(C)(CCC[C@@](C)(C(=O)OCc1ccccc1)c1cccc(I)c1)CS(=O)(=O)CCO]

To a stirred and cooled (0° C.) solution of benzyl (R)-7-((2-hydroxyethyl)thio)-2-(3-iodophenyl)-2,6,6-trimethylheptanoate (Intermediate 137C, 190 g, 352 mmol) in methanol (800 mL) was added dropwise a solution of ammonium molybdate tetrahydrate (65.00 g, 52.6 mmol) in hydrogen peroxide (30% in water, 250 mL). The mixture was stirred at room temperature for 2 hours, then diluted with water (1200 mL) and extracted with ethyl acetate (3×500 mL). The combined organic extracts were washed with brine (5×500 mL), dried over sodium sulfate, and concentrated to give the title compound (190 g, 94%) as colorless oil. MS (ESI): 595 m/z $[M+Na]^+$; purity: >99% (214 nm); retention time: 2.00 minutes (LC-MS Method 4). Chiral-HPLC purity: RT=10.24 min, 99.0% (98% ee) (chiral column conditions: Column: AY-H, 4.6×250 mm, 5 μm; mobile phase: Hexanes (0.1% diethylamine):ethanol (0.1% diethylamine)=80:20); Injection volume: 10.00 uL; Run time: 30.0 minutes; Flow rate: 1.0 mL/minute; Instrument: Shimadzu; Wavelength: 214 nm and 254 nm).

The following intermediates were prepared based on the procedures described for Intermediate 137D.

| Inter. No. | Structure | Name | MS m/z $[M + H]^+$ |
|---|---|---|---|
| 137D-1 | 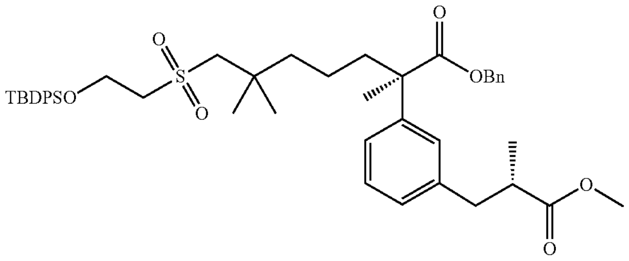 | benzyl (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoate | 807 m/z [M + Na] RT 2.54 min. (LC-MS method 4) |

Intermediate 137E: Benzyl (R)-7-((2-((tert-butyldimethylsilyl)oxy)ethyl)sulfonyl)-2-(3-iodophenyl)-2,6,6-trimethylheptanoate

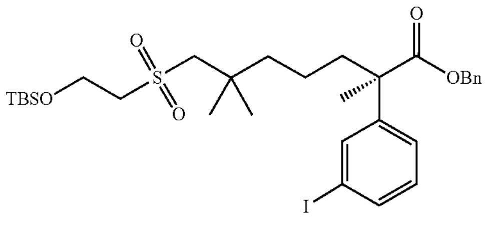 [SMILES: CC(C)(CCC[C@@](C)(C(=O)OCc1ccccc1)c1cccc(I)c1)CS(=O)(=O)CCO[Si](C)(C)C(C)(C)C]

To a stirred solution of benzyl (R)-7-((2-hydroxyethyl) sulfonyl)-2-(3-iodophenyl)-2,6,6-trimethylheptanoate (Intermediate 137D, 190 g, 332 mmol) in dichloromethane (1.0 L) was added tert-butyldimethylsilyl chloride (52.52 g, 348 mmol) and imidazole (33.89 g, 498 mmol). The mixture was stirred at room temperature for 16 hours and concentrated. The residue was purified by automated flash chromatography (330 g×2 silica gel column, eluting with 0-10% ethyl acetate in petroleum ether) to give the title compound (210.00 g, 92%) as a colorless oil. $^1$H NMR (400 MHz, $CDCl_3$) δ 7.54 (s, 1H), 7.48 (d, J=7.8 Hz, 1H), 7.28-7.12 (m, 6H), 6.93 (t, J=7.9 Hz, 1H), 5.06-4.94 (m, 2H), 3.99-3.90 (m, 2H), 3.00-2.86 (m, 4H), 1.98-1.90 (m, 1H), 1.83-1.70 (m, 1H), 1.50-1.34 (m, 5H), 1.10-0.95 (m, 8H), 0.81 (s, 9H), 0.00 (s, 6H) ppm. MS (ESI): 709 m/z $[M+Na]^+$; purity: 98% (214 nm); retention time: 2.48 minutes (LC-MS Method 4). Chiral-HPLC purity: RT=29.43 min, >99% (>99% ee) (chiral column conditions: Column: IC, 4.6×250 mm, 5 μm; mobile phase: Hexanes (0.1% diethylamine): isopropanol (0.1% diethylamine)=90:10); Injection volume: 10.00 uL; Run time: 45.0 minutes; Flow rate: 1.0 mL/minute; Instrument: Shimadzu; Wavelength: 214 nm; Column temperature: 40° C.).

Intermediate 137F: Benzyl (R)-7-((2-((tert-butyldimethylsilyl)oxy)ethyl)sulfonyl)-2-(3-((R)-3-methoxy-2-methyl-3-oxopropyl)phenyl)-2,6,6-trimethylheptanoate

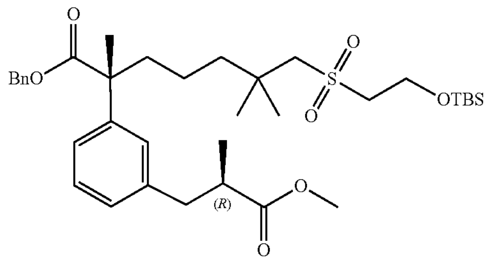

To a stirred suspension of zinc (119.95 g, 1835 mmol) in N,N-dimethylformamide (800 mL) was added iodine (7.76 g, 30.6 mmol) under argon. The reaction mixture was stirred at room temperature for 40 minutes, then treated with methyl (2S)-3-iodo-2-methyl-propanoate (Intermediate 136, 104.59 g, 459 mmol), and stirred for another 40 minutes. To this mixture was added 2-dicyclohexylphosphino-2',6'-dimethoxybiphenyl (12.55 g, 30.6 mmol), tris(dibenzylideneacetone)-dipalladium (14.00 g, 15.3 mmol), benzyl (R)-7-((2-((tert-butyldimethylsilyl)oxy)ethyl)sulfonyl)-2-(3-iodophenyl)-2,6,6-trimethylheptanoate (Intermediate 137E, 210.00 g, 306 mmol). The reaction mixture was stirred at room temperature for 16 hours, diluted with water (2000 mL) and ethyl acetate (1500 mL). The mixture was filtered. The filtrate was extracted with ethyl acetate (2×1000 mL). The combined organic layers were washed with brine, dried over sodium sulfate, filtered, and concentrated. The residue was purified by automated flash chromatography (2×330 g silica gel column, eluting with 0-30% ethyl acetate in petroleum ether) to give the title compound (186 g, 92%) as light-yellow oil. MS (ESI): 683 m/z $[M+Na]^+$; purity: 89% (214 nm); retention time: 2.35 minutes (LC-MS Method 4). Chiral-HPLC purity: >99% (>99% ee, 254 nm), RT=19.39 min, (chiral column conditions: Column: AY-H, 4.6×250 mm, 5 μm; mobile phase: Hexanes (0.1% diethylamine): ethanol (0.1% diethylamine)=95:5); Injection volume: 10.00 uL; Run time: 30.0 minutes; Flow rate: 1.0 mL/minute; Instrument: Shimadzu; Wavelength: 214 nm and 254 nm).

The following intermediates were prepared based on the procedures described for Intermediate 137F.

| Inter. No. | Structure | Name | MS m/z $[M + H]^+$ |
|---|---|---|---|
| 137F-1 | 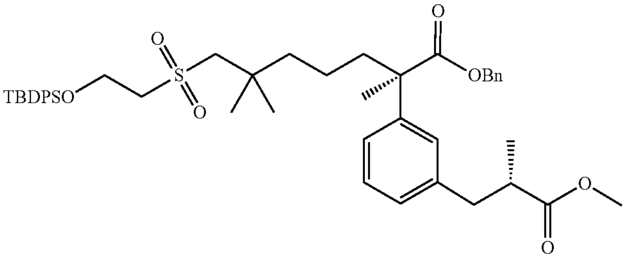 | benzyl (R)-7-((2-((tert-butyldiphenylsilyl)oxy)ethyl) sulfonyl)-2-(3-((S)-3-methoxy-2-methyl-3-oxopropyl)phenyl)-2,6,6-trimethylheptanoate | 807 m/z [M + Na] RT 2.54 min. (LC-MS method 4) |
| 137F-2 | 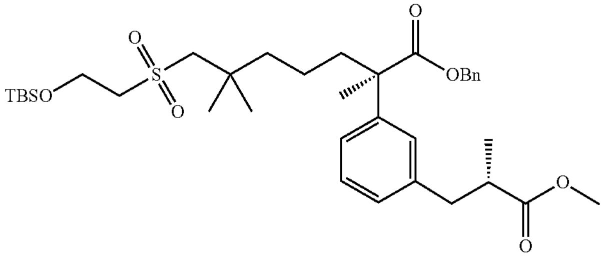 [SMILES: COC(=O)[C@@H](C)Cc1cccc([C@@](C)(CCCC(C)(C)CS(=O)(=O)CCO[Si](C)(C)C(C)(C)C)C(=O)OCc2ccccc2)c1] | benzyl (R)-7-((2-((tert-butyldimethylsilyl)oxy)ethyl) sulfonyl)-2-(3-((S)-3-methoxy-2-methyl-3-oxopropyl)phenyl)-2,6,6-trimethylheptanoate | 683 m/z [M + Na]; RT 2.43 min. (LC-MS method 4) |

-continued

| Inter. No. | Structure | Name | MS m/z $[M + H]^+$ |
|---|---|---|---|
| 137F-3 | 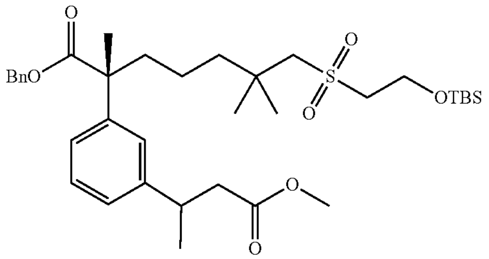 [SMILES: COC(=O)CC(C)c1cccc([C@@](C)(CCCC(C)(C)CS(=O)(=O)CCO[Si](C)(C)C(C)(C)C)C(=O)OCc2ccccc2)c1] | benzyl (2R)-7-((2-((tert-butyldimethylsilyl)oxy)ethyl) sulfonyl)-2-(3-(4-methoxy-4-oxobutan-2-yl)phenyl)-2,6,6-trimethylheptanoate | 683 m/z [M + Na]; RT 3.22 min. (LC-MS method 4) |
| 137F-4 | 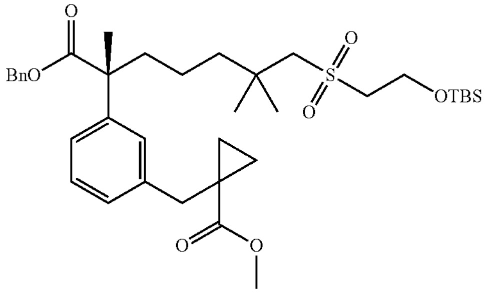 [SMILES: COC(=O)C1(Cc2cccc([C@@](C)(CCCC(C)(C)CS(=O)(=O)CCO[Si](C)(C)C(C)(C)C)C(=O)OCc3ccccc3)c2)CC1] | methyl (R)-1-(3-(1-(benzyloxy)-7-((2-((tert-butyldimethylsilyl)oxy)ethyl) sulfonyl)-2,6,6-trimethyl-1-oxoheptan-2-yl)benzyl)cyclopropane-1-carboxylate | 695 m/z [M + Na]; RT 2.46 min. (LC-MS method 4) |
| 137F-5 | 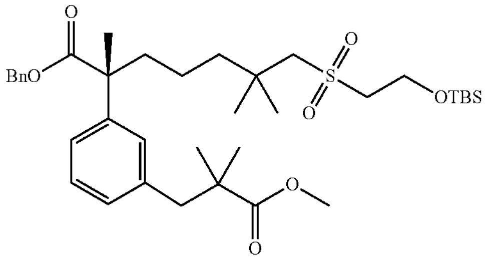 [SMILES: COC(=O)C(C)(C)Cc1cccc([C@@](C)(CCCC(C)(C)CS(=O)(=O)CCO[Si](C)(C)C(C)(C)C)C(=O)OCc2ccccc2)c1] | benzyl (R)-7-((2-((tert-butyldimethylsilyl)oxy)ethyl) sulfonyl)-2-(3-(3-methoxy-2,2-dimethyl-3-oxopropyl)phenyl)-2,6,6-trimethylheptanoate | 697 m/z [M + Na]; RT 2.47 min. (LC-MS method 3) |
| 137F-6 | 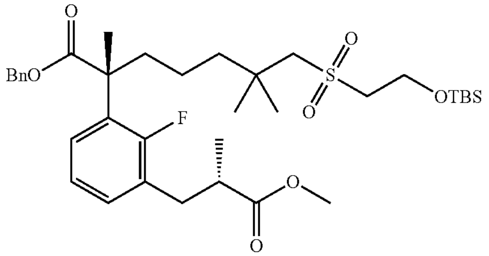 [SMILES: COC(=O)[C@@H](C)Cc1cccc([C@@](C)(CCCC(C)(C)CS(=O)(=O)CCO[Si](C)(C)C(C)(C)C)C(=O)OCc2ccccc2)c1F] | benzyl (R)-7-((2-((tert-butyldimethylsilyl)oxy)ethyl) sulfonyl)-2-(2-fluoro-3-((S)-3-methoxy-2-methyl-3-oxopropyl)phenyl)-2,6,6-trimethylheptanoate | 701 m/z [M + Na]; RT 2.35 min. (LC-MS method 4) |

Intermediate 137G: Benzyl (R)-7-((2-hydroxyethyl) sulfonyl)-2-(3-((R)-3-methoxy-2-methyl-3-oxopropyl)phenyl)-2,6,6-trimethylheptanoate

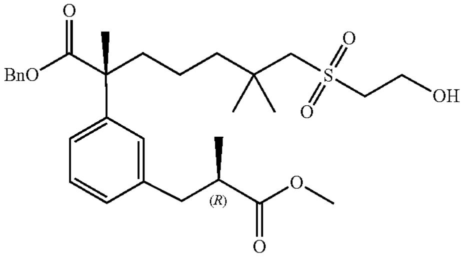

To a solution of benzyl (R)-7-((2-((tert-butyldimethylsilyl)oxy)ethyl)sulfonyl)-2-(3-((R)-3-methoxy-2-methyl-3-oxopropyl)phenyl)-2,6,6-trimethylheptanoate (Intermediate 137F, 186.00 g, 281 mmol) in tetrahydrofuran (200 mL) was added tetra-n-butylammonium fluoride (1 N in tetrahydrofuran, 422 mL, 422 mmol). The reaction mixture was stirred at room temperature for 2 hours, then diluted with ethyl acetate (1000 mL). The solution was washed with water, brine, dried over sodium sulfate, filtered, and concentrated. The residue was purified by automated flash chromatography (330 g silica gel column, eluting with 0-85% ethyl acetate in petroleum) to give the title compound (145 g, 94%) as light-yellow oil. MS (ESI): 569 m/z $[M+Na]^+$; purity: 97% (214 nm); retention time: 1.92 minutes (LC-MS Method 4). Chiral-HPLC purity: 99.4% (>99% ee, 214 nm), RT=11.99 minutes (chiral column conditions: Column: OJ-H, 4.6×250 mm, 5 μm; mobile phase: Hexanes (0.1% diethylamine): ethanol (0.1% diethylamine)=80:20); Injection volume: 10.00 uL; Run time: 30.0 minutes; Flow rate: 1.0 mL/minute; Instrument: Shimadzu; Wavelength: 214 nm and 254 nm).

The following intermediate was prepared based on the procedures described for intermediate 137G.

| Inter. No. | Structure | Name | MS m/z [M + H]+ |
|---|---|---|---|
| 137G-1 | 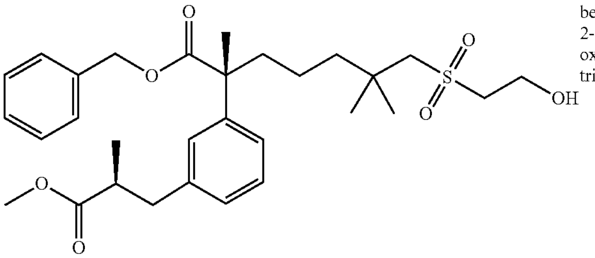 | benzyl (R)-7-((2-hydroxyethyl)sulfonyl)-2-(3-((S)-3-methoxy-2-methyl-3-oxopropyl)phenyl)-2,6,6-trimethylheptanoate | 569 [M + Na] RT 1.97 min. (LC-MS method 4) |
| 137G-2 | 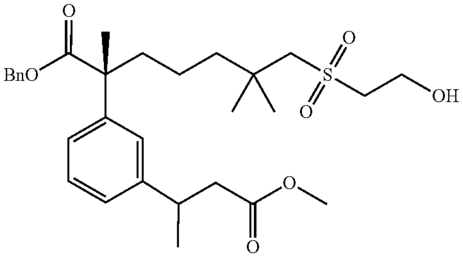 [SMILES: COC(=O)CC(C)c1cccc([C@@](C)(CCCC(C)(C)CS(=O)(=O)CCO)C(=O)OCc2ccccc2)c1] | benzyl (2R)-7-((2-hydroxyethyl)sulfonyl)-2-(3-(4-methoxy-4-oxobutan-2-yl)phenyl)-2,6,6-trimethylheptanoate | 569 [M + Na] RT 2.62 min. (LC-MS method 16) |
| 137G-3 | 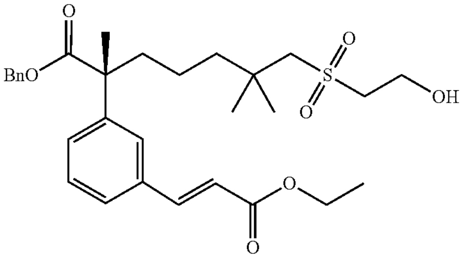 [SMILES: CCOC(=O)/C=C/c1cccc([C@@](C)(CCCC(C)(C)CS(=O)(=O)CCO)C(=O)OCc2ccccc2)c1] | benzyl (R,E)-2-(3-(3-ethoxy-3-oxoprop-1-en-1-yl)phenyl)-7-((2-hydroxyethyl)sulfonyl)-2,6,6-trimethylheptanoate | 545 [M + Na] RT 1.92 min. (LC-MS method 16) |
| 137G-4 | 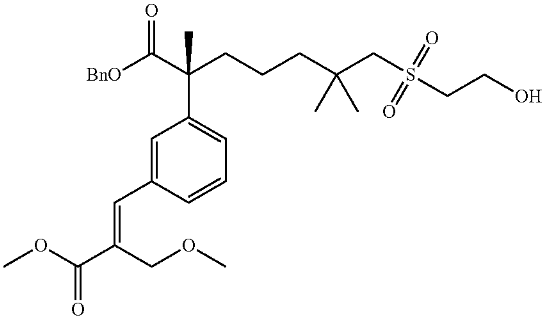 [SMILES: COC/C(=C\c1cccc([C@@](C)(CCCC(C)(C)CS(=O)(=O)CCO)C(=O)OCc2ccccc2)c1)C(=O)OC] | benzyl (R,E)-7-((2-hydroxyethyl)sulfonyl)-2-(3-(3-methoxy-2-(methoxymethyl)-3-oxoprop-1-en-1-yl)phenyl)-2,6,6-trimethylheptanoate | 597 [M + Na] RT 2.57 min. (LC-MS method 16) |
| 137G-5 | 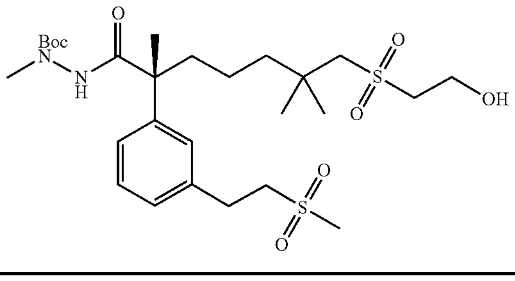 | tert-butyl (R)-2-(7-((2-hydroxyethyl)sulfonyl)-2,6,6-trimethyl-2-(3-(2-(methylsulfonyl)ethyl)phenyl)heptanoyl)-1-methylhydrazine-1-carboxylate | 613 [M + Na] RT 1.70 min. (LC-MS method 33) |

Intermediate 137H: (R)-7-((2-Hydroxyethyl)sulfonyl)-2-(3-((R)-3-methoxy-2-methyl-3-oxopropyl)phenyl)-2,6,6-trimethylheptanoic Acid

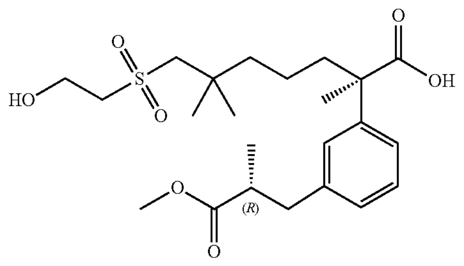

To a stirred solution of benzyl (R)-7-((2-hydroxyethyl)sulfonyl)-2-(3-((R)-3-methoxy-2-methyl-3-oxopropyl)phenyl)-2,6,6-trimethylheptanoate (Intermediate 137G, 145 g, 265 mmol) in methanol (1000 mL) was added 10% palladium on carbon (wetted with ca. 55% water, 20 g). The reaction mixture was stirred under hydrogen for 6 hours at 50° C., cooled to room temperature and filtered through a pad of Celite. The filtrate was concentrated to give the title compound (120 g, 99%) as colorless oil. MS (ESI): 479 m/z [M+Na]$^+$; purity: >99% (214 nm); retention time: 1.66 minutes (LC-MS Method 4). Chiral-HPLC purity: 99.5% (99% ee, 214 nm), RT=1.61 minutes (chiral SFC column conditions: Column: IG-3, 4.6×100 mm, 3 μm; mobile phase: carbon dioxide/methanol (0.2%7M ammonia in methanol)=65:35); Injection volume: 5.00 uL; Run time: 6.0 minutes; Flow rate: 3.0 mL/minute; Back pressure: 2000 psi; Wavelength: 214 nm; Column temperature: 40° C.).

The following intermediates were prepared based on the procedures described for intermediate 137H.

| Inter. No. | Structure | Name | MS m/z [M + H]$^+$ |
|---|---|---|---|
| 137H-1 | 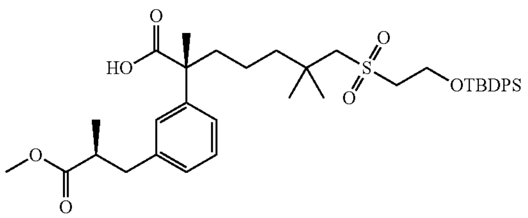 | (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoic acid | 717.0 [M + Na]; RT 2.28 min. (LC-MS method 4) |
| 137H-2 | 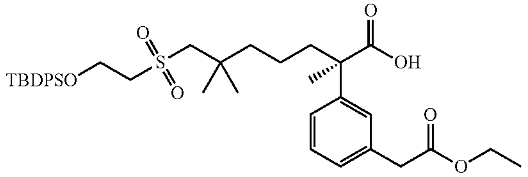 | (R)-7-((2-((tert-butyldiphenylsilyl)oxy)ethyl)sulfonyl)-2-(3-(2-methoxy-2-oxoethyl)phenyl)-2,6,6-trimethylheptanoic acid | 703 [M + H]; RT 2.49 min. (LC-MS method 4) |
| 137H-3 | 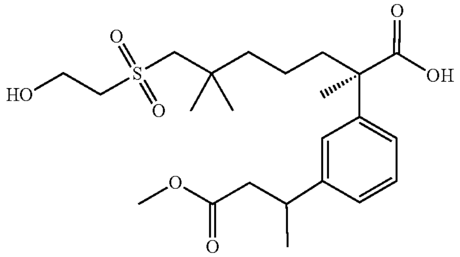 [SMILES: COC(=O)CC(C)c1cccc([C@@](C)(CCCC(C)(C)CS(=O)(=O)CCO)C(=O)O)c1] | (2R)-7-((2-hydroxyethyl)sulfonyl)-2-(3-(4-methoxy-4-oxobutan-2-yl)phenyl)-2,6,6-trimethylheptanoic acid | 479 [M + Na]; RT 2.14 min. (LC-MS method 16) |
| 137H-4 | 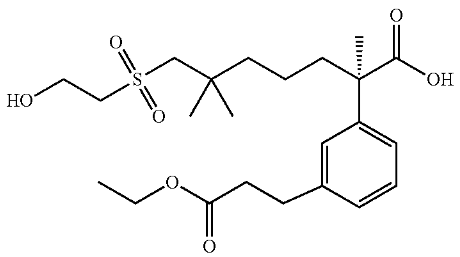 [SMILES: CCOC(=O)CCc1cccc([C@@](C)(CCCC(C)(C)CS(=O)(=O)CCO)C(=O)O)c1] | (R)-2-(3-(3-ethoxy-3-oxopropyl)phenyl)-7-((2-hydroxyethyl)sulfonyl)-2,6,6-trimethylheptanoic acid | 479 [M + Na]; RT 1.62 min. (LC-MS method 16) |

-continued

| Inter. No. | Structure | Name | MS m/z [M + H]+ |
|---|---|---|---|
| 137H-5 | 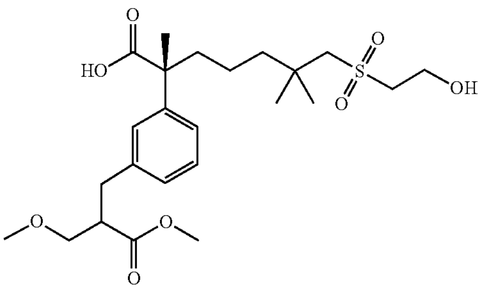 [SMILES: COCC(Cc1cccc([C@@](C)(CCCC(C)(C)CS(=O)(=O)CCO)C(=O)O)c1)C(=O)OC] | (2R)-7-((2-hydroxyethyl)sulfonyl)-2-(3-(3-methoxy-2-(methoxymethyl)-3-oxopropyl)phenyl)-2,6,6-trimethylheptanoic acid | 509 [M + Na]; RT 1.64 min. (LC-MS method 4) |
| 137H-6 | 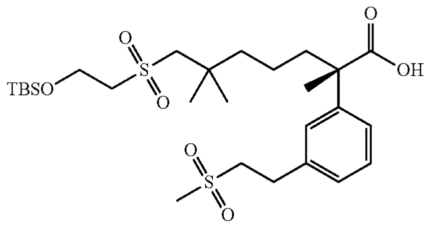 [SMILES: CC(C)(CCC[C@](C)(C(=O)O)c1cccc(CCS(C)(=O)=O)c1)CS(=O)(=O)CCO[Si](C)(C)C(C)(C)C] | (S)-7-((2-((tert-butyldimethylsilyl)oxy)ethyl) sulfonyl)-2,6,6-trimethyl-2-(3-(2-(methylsulfonyl)ethyl)phenyl) heptanoic acid | 577 [M + H]; RT 2.03 min. (LC-MS method 4) |
| 137H-7 | 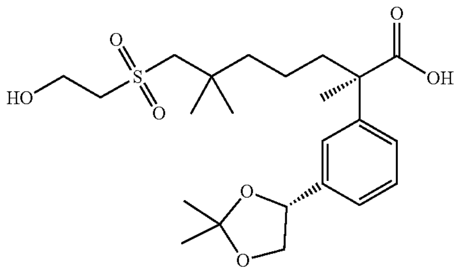 [SMILES: CC(C)(CCC[C@@](C)(C(=O)O)c1cccc([C@@H]2COC(C)(C)O2)c1)CS(=O)(=O)CCO] | (R)-2-(3-((R)-2,2-dimethyl-1,3-dioxolan-4-yl)phenyl)-7-((2-hydroxyethyl)sulfonyl)-2,6,6-trimethylheptanoic acid | 479 [M + Na]; RT 1.65 min. (LC-MS method 4) |
| 137H-8 | 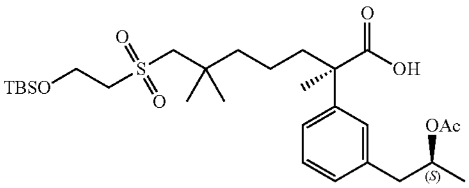 | (R)-2-(3-((S)-2-acetoxypropyl)phenyl)-7-((2-((tert-butyldimethylsilyl)oxy) ethyl)sulfonyl)-2,6,6-trimethylheptanoic acid | 593 [M + Na]; RT 2.10 min. (LC-MS method 4) |
| 137H-9 | 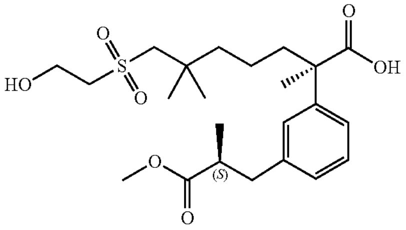 | (R)-7-((2-hydroxyethyl) sulfonyl)-2-(3-((S)-3-methoxy-2-methyl-3-oxopropyl)phenyl)-2,6,6-trimethylheptanoic acid | 479 [M + Na]; RT 1.88 min. (LC-MS method 33) |
| 137H-10 | 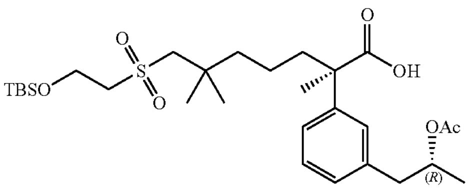 | (R)-2-(3-((R)-2-acetoxypropyl)phenyl)-7-((2-((tert-butyldimethylsilyl)oxy)ethyl) sulfonyl)-2,6,6-trimethylheptanoic acid | 593 [M + Na]; RT 2.10 min. (LC-MS method 003) |

-continued

| Inter. No. | Structure | Name | MS m/z [M + H]$^+$ |
|---|---|---|---|
| 137H-11 | 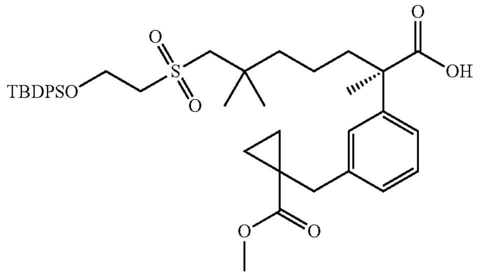 | (R)-7-((2-((tert-butyldimethylsilyl)oxy)ethyl) sulfonyl)-2-(3-((1-(methoxycarbonyl)cyclopropyl) methyl)phenyl)-2,6,6-trimethylheptanoic acid | 605 [M + Na]; RT 2.11 min. (LC-MS method 004) |
| 137H-12 | 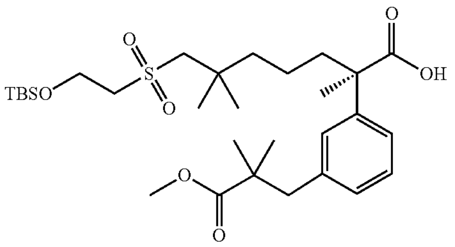 [SMILES: COC(=O)C(C)(C)Cc1cccc([C@@](C)(CCCC(C)(C)CS(=O)(=O)CCO[Si](C)(C)C(C)(C)C)C(=O)O)c1] | (R)-7-((2-((tert-butyldimethylsilyl) oxy)ethyl)sulfonyl)-2-(3-(3-methoxy-2,2-dimethyl-3-oxopropyl)phenyl)-2,6,6-trimethylheptanoic acid | 607 [M + Na]; RT 2.41 min. (LC-MS method 003) |
| 137H-13 | 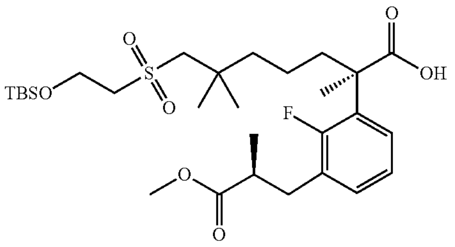 [SMILES: COC(=O)[C@@H](C)Cc1cccc([C@@](C)(CCCC(C)(C)CS(=O)(=O)CCO[Si](C)(C)C(C)(C)C)C(=O)O)c1F] | (R)-7-((2-((tert-butyldimethylsilyl) oxy)ethyl)sulfonyl)-2-(2-fluoro-3-((S)-3-methoxy-2-methyl-3-oxopropyl) phenyl)-2,6,6-trimethylheptanoic acid | 611 [M + Na]; RT 208 min. (LC-MS method 003) |

Intermediate 137I: Tert-butyl 2-((R)-7-((2-hydroxyethyl)sulfonyl)-2-(3-((R)-3-methoxy-2-methyl-3-oxopropyl)phenyl)-2,6,6-trimethylheptanoyl)-1-methylhydrazine-1-carboxylate

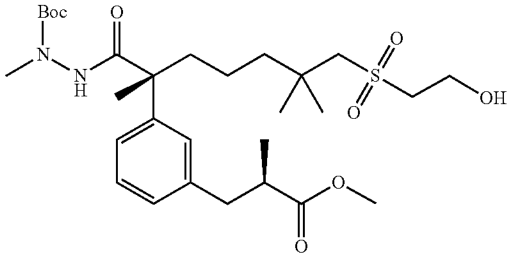 [SMILES: COC(=O)[C@H](C)Cc1cccc([C@@](C)(CCCC(C)(C)CS(=O)(=O)CCO)C(=O)NN(C)C(=O)OC(C)(C)C)c1]

To a stirred solution of (R)-7-((2-Hydroxyethyl)sulfonyl)-2-(3-((R)-3-methoxy-2-methyl-3-oxopropyl)phenyl)-2,6,6-trimethylheptanoic acid (Intermediate 137H, 120 g, 263 mmol) in acetonitrile (800 mL) was added tert-butyl N-amino-N-methyl-carbamate (40.34 g, 276 mmol), N,N,N',N'-tetramethylchloroformamidinium-hexafluorophosphate (73.72 g, 263 mmol) and 1-methylimidazole (73 mL, 920 mmol). The reaction mixture was stirring at room temperature for 1 hour, then diluted with ethyl acetate (1500 mL). The solution was washed with 0.5 N hydrochloric acid, water, saturated sodium bicarbonate solution, brine, dried over sodium sulfate, and concentrated to give the title compound (150 g, 98%) as a light-yellow oil. MS (ESI): 607 m/z [M+Na]$^+$; purity: 86% (214 nm); retention time: 1.76 minutes (LC-MS Method 4). Chiral-HPLC purity: 99.6% (>99% ee, 254 nm), RT=15.39 minutes (chiral column conditions: Column: AD-H, 4.6×250 mm, 5 μm; mobile phase: hexanes (0.1% diethylamine)/ethanol (0.1% diethylamine=90:10); Injection volume: 10.00 uL; Run time: 30.0 minutes; Flow rate: 1.0 mL/minute; Wavelength: 214 nm and 254 nm; Column temperature: 40° C.).

The following intermediate was prepared based on the procedures described for intermediate 137I.

| Inter. No. | Structure | Name | MS m/z [M + H]+ |
|---|---|---|---|
| 137I-1 | 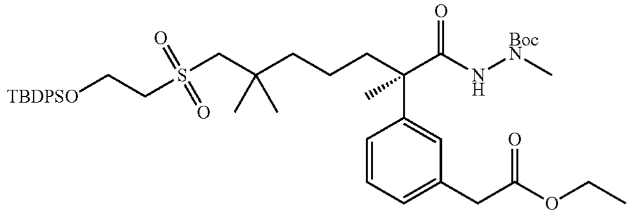 | tert-butyl (R)-2-(7-((2-((tert-butyldiphenylsilyl)oxy)ethyl)sulfonyl)-2-(3-(2-ethoxy-2-oxoethyl)phenyl)-2,6,6-trimethylheptanoyl)-1-methylhydrazine-1-carboxylate | 831.0 $[M + Na]^+$ RT: 2.33 min. (LC-MS method 4) |
| 137I-2 | 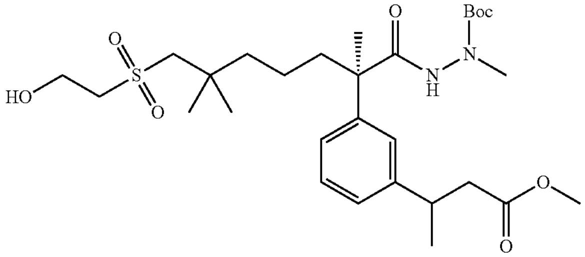 [SMILES: COC(=O)CC(C)c1cccc([C@@](C)(CCCC(C)(C)CS(=O)(=O)CCO)C(=O)NN(C)C(=O)OC(C)(C)C)c1] | tert-butyl 2-((2R)-7-((2-hydroxyethyl)sulfonyl)-2-(3-(4-methoxy-4-oxobutan-2-yl)phenyl)-2,6,6-trimethylheptanoyl)-1-methylhydrazine-1-carboxylate | 607.0 $[M + Na]^+$ RT: 2.34 min. (LC-MS method 16) |
| 137I-3 | 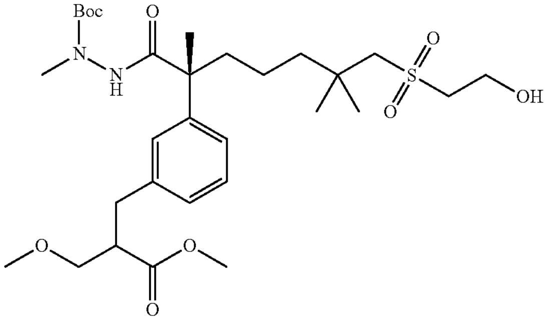 [SMILES: COCC(Cc1cccc([C@@](C)(CCCC(C)(C)CS(=O)(=O)CCO)C(=O)NN(C)C(=O)OC(C)(C)C)c1)C(=O)OC] | tert-butyl 2-((2R)-7-((2-hydroxyethyl)sulfonyl)-2-(3-(3-methoxy-2-(methoxymethyl)-3-oxopropyl)phenyl)-2,6,6-trimethylheptanoyl)-1-methylhydrazine-1-carboxylate | 637 $[M + Na]^+$ RT: 2.26 min. (LC-MS method 16) |
| 137I-4 | 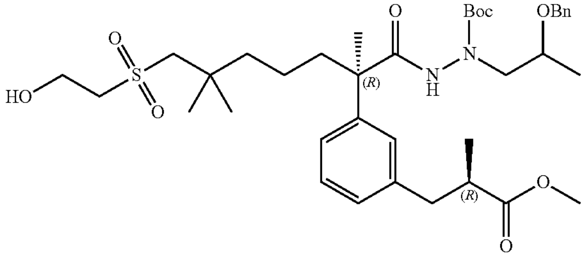 | tert-butyl 1-(2-(benzyloxy)propyl)-2-((R)-7-((2-hydroxyethyl)sulfonyl)-2-(3-((R)-3-methoxy-2-methyl-3-oxopropyl)phenyl)-2,6,6-trimethylheptanoyl)hydrazine-1-carboxylate | 741 $[M + Na]^+$ RT: 2.00 min. (LC-MS method 4) |
| 137I-5 | 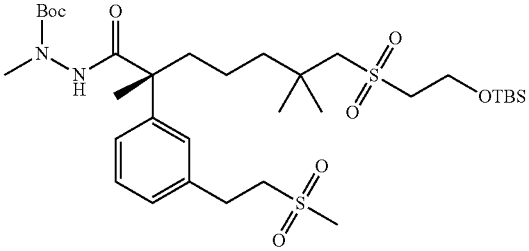 [SMILES: CN(NC(=O)[C@](C)(CCCC(C)(C)CS(=O)(=O)CCO[Si](C)(C)C(C)(C)C)c1cccc(CCS(C)(=O)=O)c1)C(=O)OC(C)(C)C] | tert-butyl (R)-2-(7-((2-((tert-butyldimethylsilyl)oxy)ethyl)sulfonyl)-2,6,6-trimethyl-2-(3-(2-(methylsulfonyl)ethyl)phenyl)heptanoyl)-1-methylhydrazine-1-carboxylate | 727 $[M + Na]^+$ RT: 2.13 min. (LC-MS method 4) |
| 137I-6 | 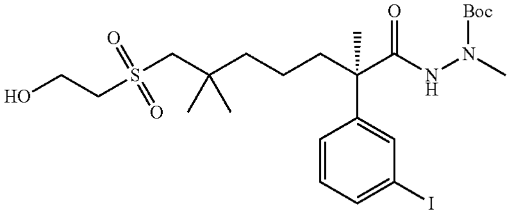 [SMILES: CN(NC(=O)[C@](C)(CCCC(C)(C)CS(=O)(=O)CCO)c1cccc(I)c1)C(=O)OC(C)(C)C] | tert-butyl (R)-2-(7-((2-hydroxyethyl)sulfonyl)-2-(3-iodophenyl)-2,6,6-trimethylheptanoyl)-1-methylhydrazine-1-carboxylate | 633 $[M + Na]^+$ RT: 1.94 min. (LC-MS method 4) |

-continued

| Inter. No. | Structure | Name | MS m/z [M + H]+ |
|---|---|---|---|
| 137I-7 | 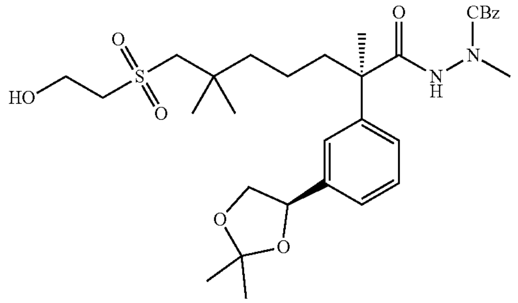 | benzyl 2-((R)-2-(3-((R)-2,2-dimethyl-1,3-dioxolan-4-yl)phenyl)-7-((2-hydroxyethyl)sulfonyl)-2,6,6-trimethylheptanoyl)-1-methylhydrazine-1-carboxylate | 641 [M + H]+ RT: 1.52 min. (LC-MS method 17) |
| 137I-8 | 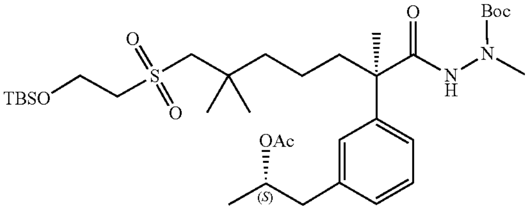 | tert-butyl 2-((R)-2-(3-((S)-2-acetoxypropyl) phenyl)-7-((2-((tert-butyldimethylsilyl) oxy)ethyl)sulfonyl)-2,6,6-trimethylheptanoyl)-1-methylhydrazine-1-carboxylate | 721 [M + Na]+ RT: 1.52 min. (LC-MS method 4) |
| 137I-9 | 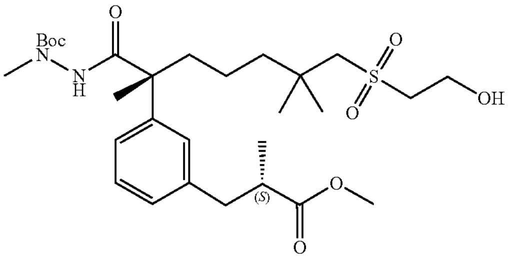 | tert-butyl 2-((R)-7-((2-hydroxyethyl)sulfonyl)-2-(3-((S)-3-methoxy-2-methyl-3-oxopropyl)phenyl)-2,6,6-trimethylheptanoyl)-1-methylhydrazine-1-carboxylate | 607 [M + Na]+ RT: 1.71 min. (LC-MS method 12) |
| 137I-10 | 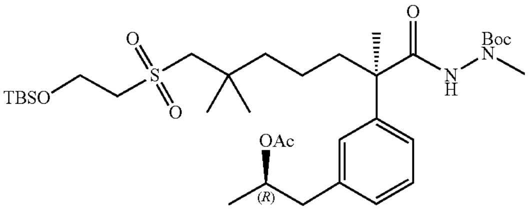 | tert-butyl 2-((R)-2-(3-((R)-2-acetoxypropyl)phenyl)-7-((2-((tert-butyldimethylsilyl)oxy) ethyl)sulfonyl)-2,6,6-trimethylheptanoyl)-1-methylhydrazine-1-carboxylate | 721 [M + Na]+ RT: 2.21 min. (LC-MS method 003) |
| 137I-11 | 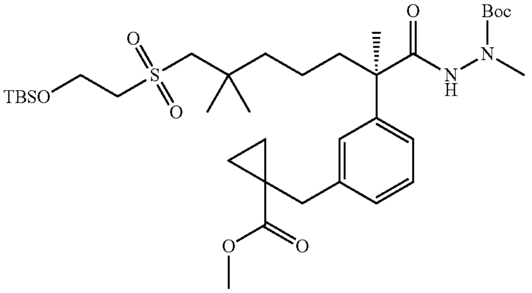 [SMILES: COC(=O)C1(Cc2cccc([C@@](C)(CCCC(C)(C)CS(=O)(=O)CCO[Si](C)(C)C(C)(C)C)C(=O)NN(C)C(=O)OC(C)(C)C)c2)CC1] | tert-butyl (R)-2-(7-((2-((tert-butyldimethylsilyl)oxy) ethyl)sulfonyl)-2-(3-((1-(methoxycarbonyl) cyclopropyl)methyl) phenyl)-2,6,6-trimethylheptanoyl)-1-methylhydrazine-1-carboxylate | 733 [M + Na]+ RT: 2.24 min. (LC-MS method 004) |
| 137I-12 | 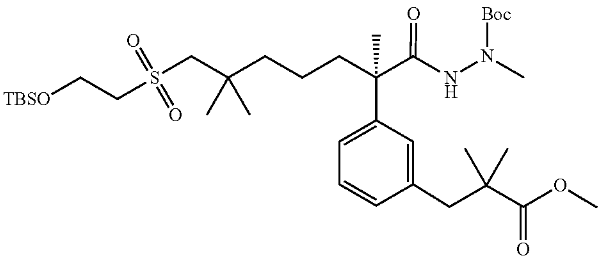 [SMILES: COC(=O)C(C)(C)Cc1cccc([C@@](C)(CCCC(C)(C)CS(=O)(=O)CCO[Si](C)(C)C(C)(C)C)C(=O)NN(C)C(=O)OC(C)(C)C)c1] | tert-butyl (R)-2-(7-((2-((tert-butyldimethylsilyl)oxy) ethyl)sulfonyl)-2-(3-(3-methoxy-2,2-dimethyl-3-oxopropyl)phenyl)-2,6,6-trimethylheptanoyl)-1-methylhydrazine-1-carboxylate | 735 [M + Na]+ RT: 2.24 min. (LC-MS method 004) |

-continued

| Inter. No. | Structure | Name | MS m/z [M + H]$^+$ |
|---|---|---|---|
| 137I-13 | 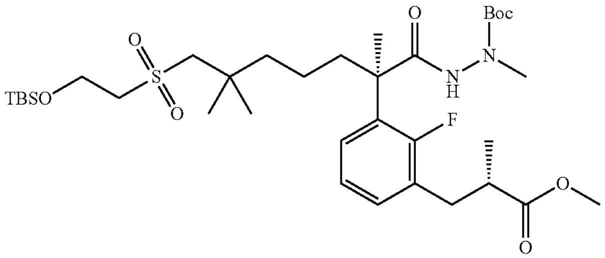 [SMILES: COC(=O)[C@@H](C)Cc1cccc([C@@](C)(CCCC(C)(C)CS(=O)(=O)CCO[Si](C)(C)C(C)(C)C)C(=O)NN(C)C(=O)OC(C)(C)C)c1F] | tert-butyl 2-((R)-7-((2-((tert-butyldimethylsilyl)oxy) ethyl)sulfonyl)-2-(2-fluoro-3-((S)-3-methoxy-2-methyl-3-oxopropyl)phenyl)-2,6,6-trimethylheptanoyl)-1-methylhydrazine-1-carboxylate | 739 [M + Na]$^+$ RT: 2.17 min. (LC-MS method 004) |
| 137I-14 | 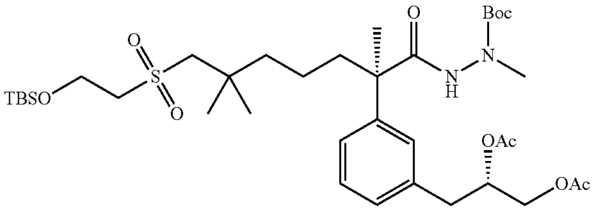 [SMILES: CC(=O)OC[C@H](Cc1cccc([C@@](C)(CCCC(C)(C)CS(=O)(=O)CCO[Si](C)(C)C(C)(C)C)C(=O)NN(C)C(=O)OC(C)(C)C)c1)OC(C)=O] | (S)-3-(3-((R)-1-(2-(tert-butoxycarbonyl)-2-methylhydrazineyl)-7-((2-((tert-butyldimethylsilyl) oxy)ethyl)sulfonyl)-2,6,6-trimethyl-1-oxoheptan-2-yl)phenyl)propane-1,2-diyl diacetate (~7:3 S:R at the diol position) | 779 [M + Na]$^+$ RT: 2.21 min. (LC-MS method 034) |
| 137-15 | 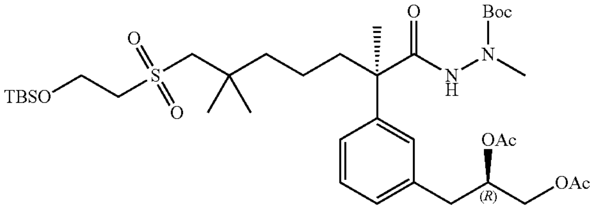 | (R)-3-(3-((R)-1-(2-(tert-butoxycarbonyl)-2-methylhydrazineyl)-7-((2-((tert-butyldimethylsilyl)oxy) ethyl)sulfonyl)-2,6,6-trimethyl-1-oxoheptan-2-yl)phenyl)propane-1,2-diyl diacetate (~7:3 R:S at the diol position) | 779 [M + Na]$^+$ RT: 2.21 min. (LC-MS method 034) |

Intermediate 138: Methyl (S)-3-(3-((R)-1-amino-7-((2-((tert-butyldiphenylsilyl)oxy)ethyl)sulfonyl)-2,6,6-trimethyl-1-oxoheptan-2-yl)phenyl)-2-methylpropanoate

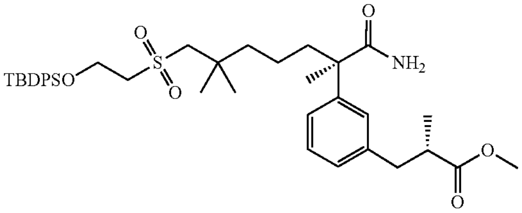

To a stirred solution of (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoic acid (Intermediate 137I H-1, 1.25 g, 1.8 mmol), ammonium chloride (385 mg, 7.19 mmol) and N'N-diisopropylethylamine (9 mL, 10.8 mmol) in dimethylformamide (15 mL) was added 2-(7-azabenzotriazol-1I-yl)-N,N,N',N'-tetramethyluronium hexafluorophosphate (2.05 g, 5.4 mmol). The mixture was stirred at room temperature overnight, then diluted with water (45 mL), and extracted with ethyl acetate (3×35 mL). The combined organic extracts were washed with water, brine, dried over sodium sulfate, filtered, and concentrated. The residue was purified by automated flash chromatography (40 g silica gel column, eluting with 0-100% ethyl acetate in petroleum ether) to give the title compound (1.01 g, 80%) as a solid. MS (ESI): 694 m/z [M+H]$^+$; purity: 92% (214 nm); retention time: 2.24 minutes (LC-MS Method 27).

Intermediate 139: Methyl (S)-3-(3-((R)-1-amino-7-((2-((tert-butyldiphenylsilyl)oxy)ethyl)sulfonyl)-2,6,6-trimethyl-1-thioxoheptan-2-yl)phenyl)-2-methylpropanoate

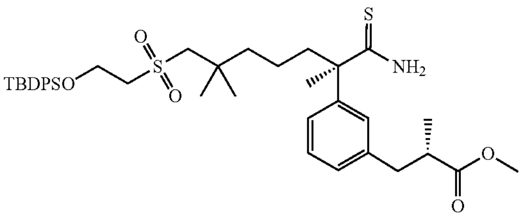

To a stirred solution of methyl (S)-3-(3-((R)-1-amino-7-((2-((tert-butyldiphenylsilyl)oxy)ethyl)sulfonyl)-2,6,6-trimethyl-1-oxoheptan-2-yl)phenyl)-2-methylpropanoate (Intermediate 138, 1.0 g, 1.44 mmol) in tetrahydrofuran (10 mL) was added Lawesson's Reagent (758 mg, 1.87 mmol). The reaction mixture was stirred at room temperature for 16 hours and concentrated. The residue was purified by automated flash chromatography (40 g silica gel column, eluting with 0-50% ethyl acetate in petroleum ether) to give the title compound (0.51 g, 49%) as a solid. MS (ESI): 710 m/z [M+H]$^+$; purity: 97% (214 nm); retention time: 2.30 minutes (LC-MS Method 33).

Intermediate 140: 2-Bromo-1-(5-((4-bromo-6-fluoro-1-(phenylsulfonyl)-1H-indol-5-yl)oxy)-2-fluorophenyl)ethan-1-one

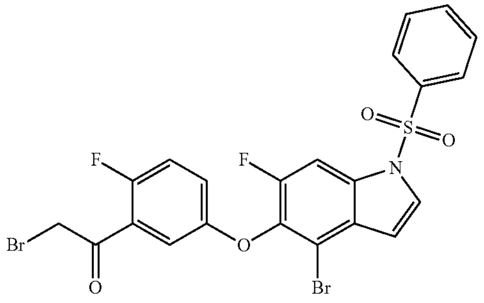 [SMILES: O=C(CBr)c1cc(Oc2c(F)cc3c(ccn3S(=O)(=O)c3ccccc3)c2Br)ccc1F]

To a stirred solution of 1-(5-((4-bromo-6-fluoro-1-(phenylsulfonyl)-1H-indol-5-yl)oxy)-2-fluorophenyl)ethan-1-one (Intermediate 21B-1, 1.00 g, 1.68 mmol) in tetrahydrofuran (20 mL) was added pyridinium tribromide (537 mg, 1.68 mmol). The mixture was stirred at room temperature for 2 hours, then diluted with 60 mL of water, and extracted with ethyl acetate (3×60 mL). The combined organic phases were washed with brine, dried over sodium sulfate, and concentrated. The residue was purified by silica gel column chromatography (eluting with petroleum ether:ethyl acetate=4:1) to give the title compound (650 mg, 56%) as a white solid. MS (ESI): 608 m/z [M+Na]$^+$; purity: 97% (214 nm); retention time: 2.11 minutes (LC-MS Method 4).

The following intermediates were prepared based on the procedures described for Intermediate 140.

| Inter. No. | Structure | Name | MS m/z [M + H]$^+$ |
|---|---|---|---|
| 140-1 | 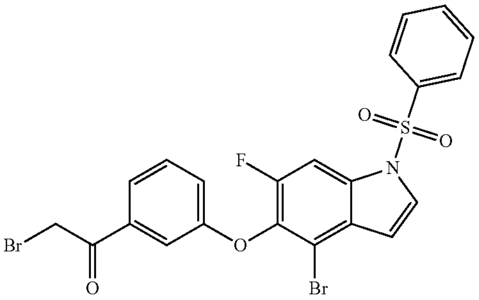 [SMILES: O=C(CBr)c1cccc(Oc2c(F)cc3c(ccn3S(=O)(=O)c3ccccc3)c2Br)c1] | 2-bromo-1-(3-((4-bromo-6-fluoro-1-(phenylsulfonyl)-1H-indol-5-yl)thio)phenyl)ethan-1-one | 606 m/z [M + Na]$^+$ RT 2.14 min. (LC-MS method 42) |

Intermediate 141: 1-(Benzyloxy)-3-(triphenyl-15-phosphanylidene)pyrrolidine-2,5-dione

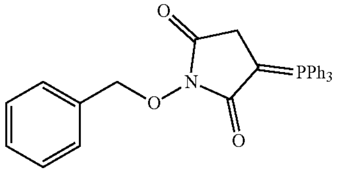

To a stirred solution of maleic anhydride (1 g, 10.5 mmol) and O-benzylhydroxylamine hydrochloride (1.75 g, 11.0 mmol) in dichloromethane (80 mL) was added dropwise a solution of triethylamine (1.12 g, 11.0 mmol) in dichloromethane (20 mL). The mixture was stirred at room temperature for 24 hours, then diluted with water, and extracted with dichloromethane (3×20 mL). The combined organic layers were washed with water, brine, dried over sodium sulphate, filtered, and concentrated to give crude (E)-4-((benzyloxy)amino)-4-oxobut-2-enoic acid.

The above crude (E)-4-((benzyloxy)amino)-4-oxobut-2-enoic acid was dissolved in acetic anhydride (4 mL) and sodium acetate (0.20 g, 2.48 mmol). The reaction mixture was stirred at 100° C. for 2 hours. Upon completion, the solution was poured into ice-cold water, and the mixture was allowed to warm to room temperature. The precipitate was collected by filtration to give crude 1-(benzyloxy)-1H-pyrrole-2,5-dione. To a stirred solution of the above crude 1-(benzyloxy)-1H-pyrrole-2,5-dione (0.5 g, 1.2 mmol) in acetic acid (10 mL) was added triphenylphosphine (0.32 g, 1.2 mmol). The mixture was heated at 100° C. for 5 hours and concentrated. The residue was purified by automated flash chromatography (12 g silica gel column, eluting with 0-65% ethyl acetate in petroleum ether) to give the title compound as a white solid (280 mg, 6% overall three steps). MS (ESI): 466 m/z [M+H]$^+$; purity: 95% (214 nm); retention time: 1.32 minutes (LC-MS Method 4).

Intermediate 142: 3-((4-Bromo-6-fluoro-1-(triisopropylsilyl)-1H-indol-5-yl)sulfinyl)benzonitrile

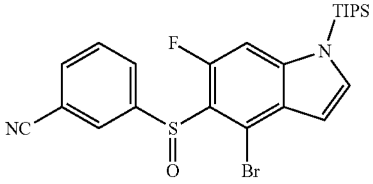

To a stirred and cooled (0° C.) solution of 3-((4-bromo-6-fluoro-1-(triisopropylsilyl)-1H-indol-5-yl)thio)benzonitrile (Intermediate 132-1, 1.30 g, 2.58 mmol) in dichloromethane (20 mL) was added 3-chloroperoxybenzoic acid (535 mg, 3.10 mmol). The mixture was stirred at 0° C. for 1 hour, then quenched with saturated sodium bicarbonate, and extracted with ethyl acetate (3×20 mL). The combined organic layers were washed with water, brine, dried over sodium sulfate, filtered, and concentrated. The residue was purified by automated flash chromatography (20 g silica gel column, eluting with 0-40% ethyl acetate in petroleum ether) to give the title compound (700 mg, 52%) as a solid. MS (ESI): 519, 521 m/z $[M+H]^+$; purity: >99% (214 nm); retention time: 2.40 minutes (LC-MS Method 4).

Intermediate 143: Tert-butyl 2-(5-bromothiophen-2-yl)-7-((tert-butyldimethylsilyl)oxy)-2,6,6-trimethylheptanoate

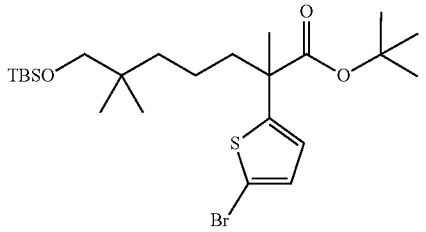 [SMILES: CC(C)(CCCC(C)(C(=O)OC(C)(C)C)c1ccc(Br)s1)CO[Si](C)(C)C(C)(C)C]

To a stirred solution of tert-butyl 7-((tert-butyldimethylsilyl)oxy)-2,6,6-trimethyl-2-(thiophen-2-yl)heptanoate (Intermediate 16-19, 10000 mg, 22.7 mmol) in dimethylformamide (80 mL) was added N-Bromo-succinimide (1.10 eq, 4442 mg, 25.0 mmol). The mixture was stirred at room temperature for 16 hours and concentrated. The residue was purified by silica gel flash chromatography (80 g silica gel column, eluting with 0-5% ethyl acetate in petroleum ether) to afford the title compound (10500 mg, 77%) as yellow oil. MS (ESI): 541, 543 m/z $[M+Na]^+$; purity: 87% (214 nm); retention time: 4.67 minutes (LC-MS Method 33).

Intermediate 144: (1-(Benzyloxy)-2-oxopyrrolidin-3-yl)triphenylphosphonium bromide

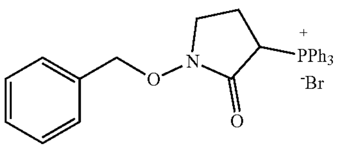

To a stirred solution of 1-(benzyloxy)-3-bromopyrrolidin-2-one (Intermediate 144A; 540 mg, 2.0 mmol) in tetrahydrofuran (2 mL) was added triphenylphosphine (524 mg, 5.0 mmol). The mixture was stirred at 60° C. for 30 hours, cooled to room temperature, and filtered. The filter cake was rinsed with tetrahydrofuran and dried to afford the title compound (645 mg, 60%) as a white solid. LC-MS: purity: 95% (214 nm); retention time: 1.10 minutes (LC-MS Method 4).

Intermediate 144A: 1-(Benzyloxy)-3-bromopyrrolidin-2-one

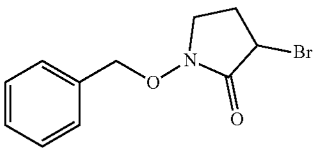 [SMILES: O=C1C(Br)CCN1OCc1ccccc1]

To a stirred and cooled (−20° C.) solution of 2,4-dibromobutyroyl chloride (1.32 g; 4.95 mmol) in dichloromethane (30 mL) was added a solution of O-benzylhydroxylamine (0.58 mL; 5.0 mmol) and triethylamine (0.70 mL; 5.0 mmol) in dichloromethane (20 mL). The mixture was stirred for 30 min, quenched with water (20 mL), and extracted with dichloromethane (2×20 mL). The combined organic extracts were dried over sodium sulfate and concentrated. The residue was dissolved in 20 mL of dichloromethane, treated with Amberlite IRA-400 (in $OH^-$ form) and 1.5 g of 50% NaOH solution under vigorous stirring. After stirring for 4 hours at room temperature, the mixture was filtered. The filtrate was washed with water. The combined organic phases were dried over sodium sulfate and concentrated. The residue was purified by silica gel flash chromatography (eluent 20% ethyl acetate in petroleum ether) to afford the title compound (800 mg, 60%) as a white solid. MS (ESI): 270, 272 m/z $[M+H]^+$; purity: 95% (214 nm); retention time: 1.77 minutes (LC-MS Method 4).

Intermediate 145: Benzyl (R)-7-((2-((tert-butyldiphenylsilyl)oxy)ethyl)sulfonyl)-2-(3-(2-ethoxy-2-oxoethyl)phenyl)-2,6,6-trimethylheptanoate

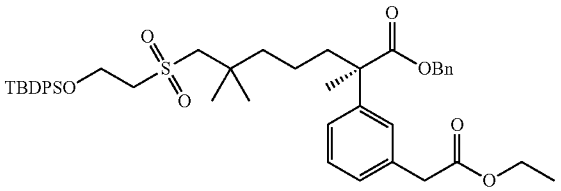

To a stirred suspension of zinc (2.90 g, 44.4 mmol) in tetrahydrofuran (120 mL) was added iodine (0.19 g, 0.74 mmol). The mixture was stirred at room temperature for 5 minutes, then treated with ethyl bromoacetate (2.5 mL, 22.2 mmol), and stirred at 50° C. for 5 minutes, followed by stirring at room temperature for 2 hours. The resulting solution was added drop wise to a stirred solution of bis(tri-t-butylphosphine)palladium (0) (0.19 g, 0.37 mmol) and benzyl (R)-7-((2-((tert-butyldimethylsilyl)oxy)ethyl)sulfonyl)-2-(3-iodophenyl)-2,6,6-trimethylheptanoate (Intermediate 137E, 6.00 g, 7.4 mmol) in N-methyl pyrrolidone (20 mL) and tetrahydrofuran (20 mL) under argon. The reaction mixture was stirred at 75° C. for 16 hours, cooled to room temperature, and filtered. The filtrate was diluted with water (200 mL), extracted with ethyl acetate (3×80 mL). The combined organic extracts were washed with brine, dried over sodium sulfate, filtered, and concentrated. The residue was purified by automated flash chromatography (120 g silica gel column, eluting with 0-60% ethyl acetate in petroleum ether) to give the title compound (2.40 g, 41%) as oil. MS (ESI): 793 m/z $[M+Na]^+$; purity: 95% (214 nm); retention time: 2.49 minutes (LC-MS Method 4).

Intermediate 146: Benzyl (R,E)-7-((2-((tert-butyldimethylsilyl)oxy)ethyl)sulfonyl)-2-(3-(3-ethoxy-3-oxoprop-1-en-1-yl)phenyl)-2,6,6-trimethylheptanoate

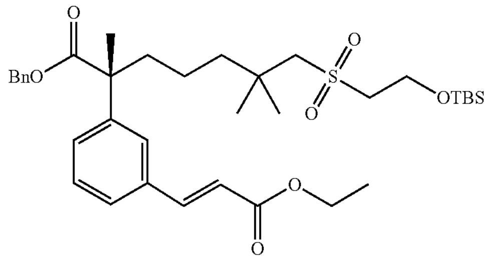 [SMILES: CCOC(=O)/C=C/c1cccc([C@@](C)(CCCC(C)(C)CS(=O)(=O)CCO[Si](C)(C)C(C)(C)C)C(=O)OCc2ccccc2)c1]

To a stirred solution of benzyl (R)-7-((2-((tert-butyldimethylsilyl)oxy)ethyl)sulfonyl)-2-(3-iodophenyl)-2,6,6-trimethylheptanoate (Intermediate 137E, 10.0 g, 14.6 mmol) in 1,4-dioxane (150 mL) was added ethyl (E)-3-(4,4,5,5-tetramethyl-1,3,2-dioxaborolan-2-yl)acrylate (6.58 g, 29.1 mmol), potassium carbonate (6.04 mg, 43.7 mmol) and [1,1'-Bis(diphenylphosphino)ferrocene]dichloropalladium (II), complex with dichloromethane (1.19 g, 1.46 mmol). The reaction mixture was stirred at 90° C. for 3 hours, cooled to room temperature, quenched with water (50 mL), and extracted with ethyl acetate (3×50 mL). The combined organic extracts were washed with brine, dried over sodium sulfate, filtered, and concentrated. The residue was purified by automated flash chromatography (120 g silica gel column, eluting with 0-30% ethyl acetate in petroleum ether) to give the title compound (8.00 g, 83%) as a yellowish oil. LC-MS: MS (ESI): 659 m/z $[M+H]^+$; purity: 86% (214 nm); retention time: 2.34 minutes (LC-MS Method 4).

The following intermediate was prepared based on the procedures described for Intermediate 146.

Intermediate 147. Benzyl (R,E)-7-((2-((tert-butyldimethylsilyl)oxy)ethyl)sulfonyl)-2-(3-(3-methoxy-2-(methoxymethyl)-3-oxoprop-1-en-1-yl)phenyl)-2,6,6-trimethylheptanoate

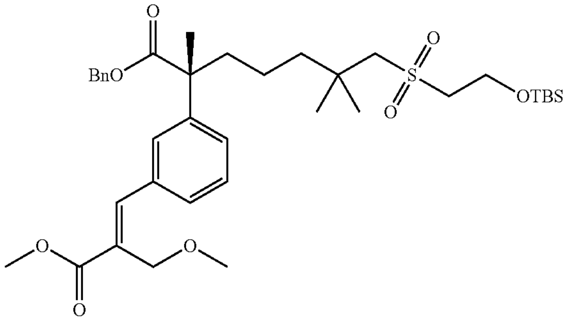 [SMILES: COC/C(=C\c1cccc([C@@](C)(CCCC(C)(C)CS(=O)(=O)CCO[Si](C)(C)C(C)(C)C)C(=O)OCc2ccccc2)c1)C(=O)OC]

To a stirred solution of benzyl (R)-7-((2-((tert-butyldimethylsilyl)oxy)ethyl)sulfonyl)-2-(3-iodophenyl)-2,6,6-trimethylheptanoate (Intermediate 137E, 5.00 g, 7.28 mmol), methyl 2-(methoxymethyl)prop-2-enoate (1.89 g, 14.6 mmol) and N,N-diisopropylethylamine (7.6 mL, 43.7 mmol) in N-Methyl-2-pyrrolidone (20 mL) was added palladium (II) acetate (0.16 g, 0.728 mmol) at room temperature. The reaction was stirred at 80° C. for 16 hours, cooled to room temperature, quenched with water (100 mL), and extracted with ethyl acetate (3×50 mL). The combined organic layer was washed with brine, dried over sodium sulfate, filtered, and concentrated. The residue was purified by automated flash chromatography (40 g silica gel column, eluting with 0-25% ethyl acetate in petroleum ether) to give the title compound (3.68 g, 5.27 mmol, 72%) as a yellow oil. LC-MS: MS (ESI): 711 m/z $[M+Na]^+$; purity: 98% (214 nm); retention time: 3.15 minutes (LC-MS Method 16).

Intermediate 148. Tert-butyl 1-(2-(benzyloxy)propyl)hydrazine-1-carboxylate

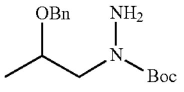 [SMILES: CC(CN(N)C(=O)OC(C)(C)C)OCc1ccccc1]

| Inter. No. | Structure | Name | MS m/z $[M + H]^+$ |
|---|---|---|---|
| 146-1 | 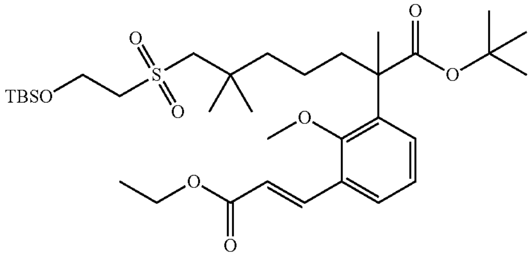 | tert-butyl (E)-7-((2-((tert-butyldimethylsilyl)oxy)ethyl)sulfonyl)-2-(3-(3-ethoxy-3-oxoprop-1-en-1-yl)-2-methoxyphenyl)-2,6,6-trimethylheptanoate | 677 [M + Na] RT: 2.32 min. (LC-MS method 26) |

To a stirred solution of tert-butyl N-(2-benzyloxypropyl)-N-(1,3-dioxoisoindolin-2-yl)carbamate (Intermediate 148A, 1.70 g, 4.14 mmol) in ethanol (20 mL) was added hydrazine hydrate (1.04 g, 20.7 mmol). The mixture was stirred at 80° C. for 1 hour and filtered. The filtrate was concentrated. The residue was purified by silica gel column chromatography (eluting with petroleum ether:ethyl acetate=2:1) to give the title compound (1.20 g, 3.85 mmol, 93%) as a colorless liquid. LC-MS: MS (ESI): 303 m/z $[M+Na]^+$; purity: 91% (214 nm); retention time: 1.80 minutes (LC-MS Method 4).

The following intermediate was prepared based on the procedures described for Intermediate 148.

| Inter. No. | Structure | Name | MS m/z $[M + H]^+$ |
|---|---|---|---|
| 148-1 | 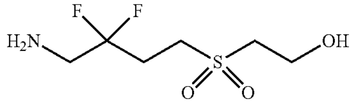 [SMILES: NCC(F)(F)CCS(=O)(=O)CCO] | 2-((4-amino-3,3-difluorobutyl)sulfonyl)ethan-1-ol | $^1H$ NMR (500 MHz, DMSO-$d_6$) δ 3.83-3.71 (m, 4H), 3.41-3.34 (m, 4H), 3.25 (t, J = 6.0 Hz, 2H), 2.66 (t, J = 6.0 Hz, 2H) ppm |

Intermediate 148A. Tert-Butyl (2-(benzyloxy)propyl)(1,3-dioxoisoindolin-2-yl)carbamate

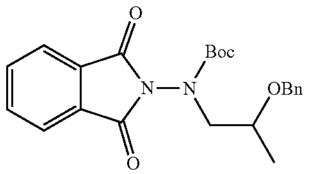 [SMILES: CC(CN(C(=O)OC(C)(C)C)N1C(=O)c2ccccc2C1=O)OCc1ccccc1]

To a stirred and cooled (0° solution of triphenylphosphine (3.31 g, 12.6 mmol) in tetrahydrofuran (50 mL) was added diisopropyl azodicarboxylate (2.5 mL, 12.6 mmol) at 0° C. The mixture was stirred for 30 minutes, then treated with 2-benzyloxypropan-1-ol (700 mg, 4.21 mmol) and tert-butyl N-(1,3-dioxoisoindolin-2-yl)carbamate (3.49 g, 12.6 mmol) in tetrahydrofuran (5 mL). The reaction mixture was stirred at room temperature overnight, then diluted with 100 mL of water, and extracted with ethyl acetate (3×100 mL). The combined organic phase was washed with brine, dried over sodium sulfate, and concentrated. The residue was purified by silica gel column chromatography (eluting with petroleum ether:ethyl acetate=4:1) to give the title compound (1.70 g, 3.93 mmol, 93%) as a colorless liquid. LC-MS: MS (ESI): 433 m/z $[M+Na]^+$; purity: 83% (214 nm); retention time: 2.05 minutes (LC-MS Method 4).

Intermediate 149. Benzyl (R,E)-7-((2-((tert-butyldimethylsilyl)oxy)ethyl)sulfonyl)-2,6,6-trimethyl-2-(3-(2-(methylsulfonyl)vinyl)phenyl)heptanoate

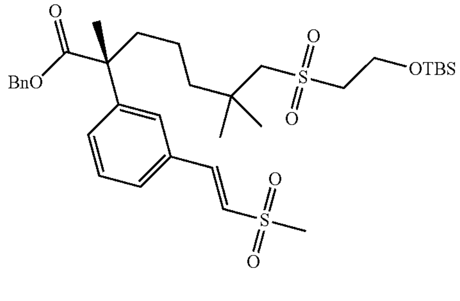 [SMILES: CC(C)(CCC[C@@](C)(C(=O)OCc1ccccc1)c1cccc(/C=C/S(C)(=O)=O)c1)CS(=O)(=O)CCO[Si](C)(C)C(C)(C)C]

To a stirred solution of benzyl (R)-7-((2-((tert-butyldimethylsilyl)oxy)ethyl)sulfonyl)-2-(3-iodophenyl)-2,6,6-trimethylheptanoate (Intermediate 137E, 4.12 g, 5.99 mmol) in toluene (40 mL) was added 1-methylsulfonylethylene (1.27 g, 12.0 mmol), triethylamine (1.6 mL, 11.5 mmol) and bis(tri-t-butylphosphine) palladium (0) (0.12 g, 0.23 mmol). The reaction mixture was heated at 120° C. for 16 hours and concentrated. The residue was purified by automated flash chromatography (80 g silica gel column, eluting with 0-100% ethyl acetate in petroleum ether) to give the title compound (2.60 g, 63%) as a solid. LC-MS: MS (ESI): 665 m/z $[M+H]^+$; purity: 97% (254 nm); retention time: 2.23 minutes (LC-MS Method 4).

Intermediate 150. Methyl 4-((4-bromo-6,7-difluoro-1H-indol-5-yl)oxy)pyridine-2-carbimidothioate

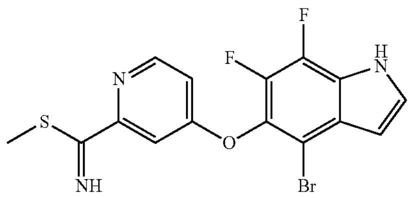

To a stirred solution of 4-((4-bromo-6,7-difluoro-1H-indol-5-yl)oxy)pyridine-2-carbothioamide (Intermediate 133C-1, 340 mg, 0.88 mmol) in acetone (20 mL) was added iodomethane (0.44 mL, 7.1 mmol) and sodium bicarbonate (595 mg, 7.1 mmol). The reaction mixture was stirred at room temperature overnight, quenched with water (20 mL), and extracted with DCM (2×20 mL). The combined organic extracts were washed with brine, dried over sodium sulfate, filtered, and concentrated to give the title compound as a solid (0.32 g, crude, used for next step without further purification). LC-MS: MS (ESI): 398, 400 m/z $[M+H]^+$; purity: 68% (214 nm); retention time: 1.57 minutes (LC-MS Method 17).

The following intermediates were prepared based on the procedures described for Intermediate 150.

| Inter. No. | Structure | Name | MS m/z [M + H]+ |
|---|---|---|---|
| 150-1 | 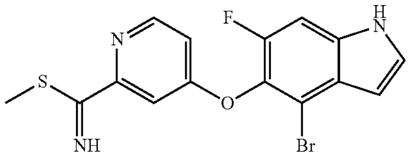 [SMILES: CSC(=N)c1cc(Oc2c(F)cc3[nH]ccc3c2Br)ccn1] | methyl 4-((4-bromo-6-fluoro-1H-indol-5-yl)oxy)pyridine-2-carbimidothioate | 380, 382 [M + H] RT: 1.58 min. (LC-MS method 4) |
| 150-2 | 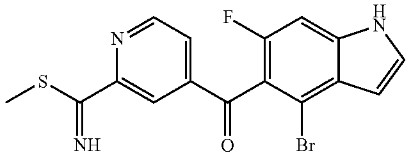 [SMILES: CSC(=N)c1cc(C(=O)c2c(F)cc3[nH]ccc3c2Br)ccn1] | methyl 4-(4-bromo-6-fluoro-1H-indole-5-carbonyl)pyridine-2-carbimidothioate | 392, 394 [M + H] RT: 1.50 min. (LC-MS method 17) |
| 150-3 | 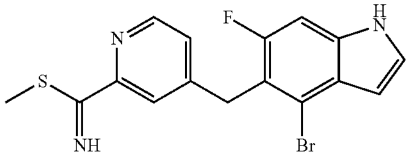 [SMILES: CSC(=N)c1cc(Cc2c(F)cc3[nH]ccc3c2Br)ccn1] | methyl 4-((4-bromo-6-fluoro-1H-indol-5-yl)methyl)pyridine-2-carbimidothioate | 378, 380 [M + H] RT: 1.59 min. (LC-MS method 4) |
| 150-4 | 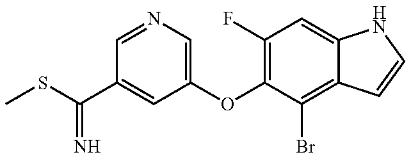 [SMILES: CSC(=N)c1cncc(Oc2c(F)cc3[nH]ccc3c2Br)c1] | methyl 5-((4-bromo-6-fluoro-1H-indol-5-yl)oxy)pyridine-3-carbimidothioate | 380, 382 [M + H] RT: 1.83 min. (LC-MS method 27) |
| 150-5 | 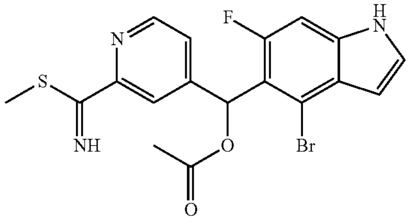 [SMILES: CSC(=N)c1cc(C(OC(C)=O)c2c(F)cc3[nH]ccc3c2Br)ccn1] | (4-bromo-6-fluoro-1H-indol-5-yl)(2-(imino(methylthio)methyl)pyridin-4-yl)methyl acetate | 436, 438 [M + H] RT: 1.51 min. (LC-MS method 4) |
| 150-6 | 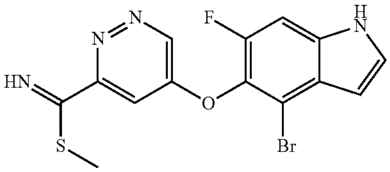 [SMILES: CSC(=N)c1cc(Oc2c(F)cc3[nH]ccc3c2Br)cnn1] | methyl 5-((4-bromo-6-fluoro-1H-indol-5-yl)oxy)pyridazine-3-carbimidothioate | 381, 383 [M + H] RT: 178 min. (LC-MS method 21) |
| 150-7 | 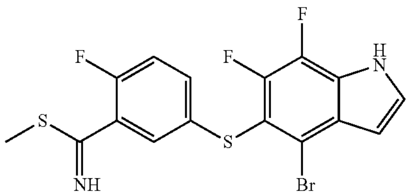 [SMILES: CSC(=N)c1cc(Sc2c(F)c(F)c3[nH]ccc3c2Br)ccc1F] | methyl 5-((4-bromo-6,7-difluoro-1H-indol-5-yl)thio)-2-fluorobenzimidothioate | 431, 433 [M + H] RT: 178 min. (LC-MS method 003) |
| 150-8 | 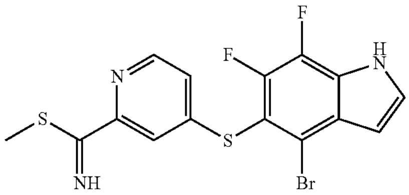 [SMILES: CSC(=N)c1cc(Sc2c(F)c(F)c3[nH]ccc3c2Br)ccn1] | methyl 4-((4-bromo-6,7-difluoro-1H-indol-5-yl)thio)pyridine-2-carbimidothioate | 414, 416 [M + H] RT: 1.48 min. (LC-MS method 22) |

-continued

| Inter. No. | Structure | Name | MS m/z $[M+H]^+$ |
|---|---|---|---|
| 150-9 | 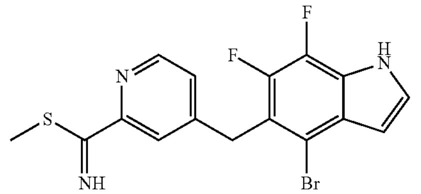 [SMILES: CSC(=N)c1cc(Cc2c(F)c(F)c3[nH]ccc3c2Br)ccn1] | methyl 4-((4-bromo-6,7-difluoro-1H-indol-5-yl)methyl)pyridine-2-carbimidothioate | 396, 398 [M + H] RT: 1.58 min. (LC-MS method 42) |
| 150-10 | 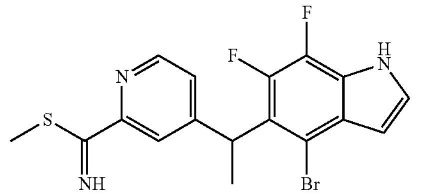 [SMILES: CSC(=N)c1cc(C(C)c2c(F)c(F)c3[nH]ccc3c2Br)ccn1] | methyl 4-(1-(4-bromo-6,7-difluoro-1H-indol-5-yl)ethyl)pyridine-2-carbimidothioate | 410, 412 [M + H] RT: 1.77 min. (LC-MS method 40) |
| 150-11 | 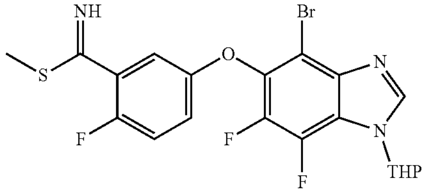 | methyl 5-((4-bromo-6,7-difluoro-1-(tetrahydro-2H-pyran-2-yl)-1H-benzo[d]imidazol-5-yl)oxy)-2-fluorobenzimidothioate | 500, 502 [M + H] RT: 1.77 min. (LC-MS method 43) |

Intermediate 151. (R)-7-((2-Hydroxyethyl)sulfonyl)-2-(3-iodophenyl)-2,6,6-trimethylheptanoic Acid

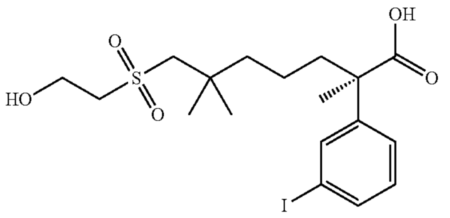 [SMILES: CC(C)(CCC[C@@](C)(C(=O)O)c1cccc(I)c1)CS(=O)(=O)CCO]

To a stirred solution of benzyl (R)-7-((2-((tert-butyldimethylsilyl)oxy)ethyl)sulfonyl)-2-(3-iodophenyl)-2,6,6-trimethylheptanoate (Intermediate 137E, 2.40 g, 3.49 mmol) in methanol (10 mL) and tetrahydrofuran (30 mL) was added 1 M lithium hydroxide (10 mL, 10 mmol). The mixture was stirred at 60° C. for 6 hours, cooled to room temperature, and acidified with 1 M hydrochloric acid to pH~4. The mixture was extracted with ethyl acetate (2×50 mL). The combined organic extracts were washed with water, brine, dried over sodium sulfate, filtered, and concentrated. The residue was purified by automated column chromatography (40 g silica gel column, eluting with 0 to 100% ethyl acetate in petroleum ether) to give the title compound (1.20 g, 71%) as a white solid. LC-MS: MS (ESI): 501 m/z [M+18]+; purity: >99% (254 nm); retention time: 1.38 minutes (LC-MS Method 4).

Intermediate 152. (R)-7-((2-Hydroxyethyl)sulfonyl)-N',2,6,6-tetramethyl-2-phenylheptanehydrazide

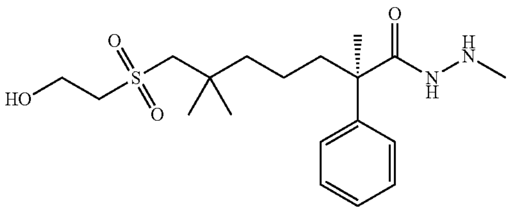 [SMILES: CNNC(=O)[C@](C)(CCCC(C)(C)CS(=O)(=O)CCO)c1ccccc1]

To a stirred solution of (2R)-7-(2-hydroxyethylsulfonyl)-2-(3-iodophenyl)-N',2,6,6-tetramethyl-heptanehydrazide (Intermediate 137-7, 1.20 g, 2.35 mmol) in methanol (20 mL) was added palladium on carbon (50% wet. 10%, 250 mg). The mixture was stirred under hydrogen balloon atmosphere for 6 hours, then filtered through a pad of Celite and the filter cake was rinsed with methanol. The filtrate was concentrated to give the title compound (0.66 g, 69%) as oil. LC-MS: MS (ESI): 385 m/z $[M+H]^+$; purity: 94% (214 nm); retention time: 1.46 minutes (LC-MS Method 4).

Intermediate 153. 4-((4-Bromo-6-fluoro-1H-indol-5-yl)thio)picolinonitrile

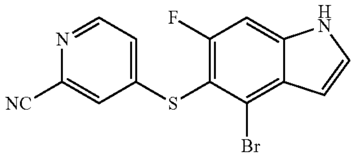 [SMILES: N#Cc1cc(Sc2c(F)cc3[nH]ccc3c2Br)ccn1]

To a stirred solution of 4-(2-bromo-6-fluoro-3-methyl-4-nitro-phenyl)sulfanylpyridine-2-carbonitrile (Intermediate 153B, 70.00 g, 190 mmol) in dimethylformamide (350 mL) was added N,N-dimethylformamide dimethyl acetal (76 mL, 570 mmol). The mixture was stirred at 100° C. for 4 hours and concentrated. The residue, a brown solid (75 g, (E)-4-((2-bromo-3-(2-(dimethylamino)vinyl)-6-fluoro-4-nitrophenyl)thio)picolinonitrile), was used for next step without further purification. LC-MS: MS (ESI): 396, 398 m/z $[M–NHMe_2+H_2O]^+$, retention time: 1.76 minutes, purity: 37% (254 nm) (LC-MS Method 26).

To a stirred solution of the above brown reside (75.0 g, 177 mmol) in methanol (200 mL) and tetrahydrofuran (200 mL) was added stannous chloride dihydrate (79.97 g, 354 mmol). The mixture was stirred at room temperature for 2 hours, diluted with 1000 mL of water and 1000 mL of ethyl acetate, alkalified with 1N sodium hydroxide solution to pH~8. The mixture was filtered, the filter cake was washed with ethyl acetate, and the filtrate was extracted with ethyl acetate (3×1000 mL). The combined organic phase was washed with brine, dried over sodium sulfate, and concentrated to give 4-(4-bromo-6-fluoro-1-hydroxy-indol-5-yl)sulfanylpyridine-2-carbonitrile (61.00 g, 167 mmol, 94.53% yield) as a brown solid, which was used for next step without further purification. LC-MS: MS (ESI): 364, 366 m/z $[M+H]^+$, retention time: 1.78 minutes, purity: 58% (254 nm) (LC-MS Method 3).

To a stirred solution of 2-bromo-1-phenyl-ethanone (33.3 g, 167 mmol) in tetrahydrofuran (150 mL) and methanol (150 mL) was added 4-(4-bromo-6-fluoro-1-hydroxy-indol-5-yl)sulfanylpyridine-2-carbonitrile (the above brown solid, 61.00 g, 167 mmol) and triethylamine (47 mL, 335 mmol). The mixture was stirred at room temperature for 3 hours, diluted with 1000 mL of water, extracted with ethyl acetate (3×1000 mL). The combined organic phase was washed with brine, dried over sodium sulfate and concentrated. The residue was purified by silica gel column chromatography (eluting with 0-50% of ethyl acetate in petroleum ether) to give 4-[(4-bromo-6-fluoro-1H-indol-5-yl)sulfanyl]pyridine-2-carbonitrile (25.00 g, 71.8 mmol, 43%3 steps) as a yellow solid. $^1$H NMR (400 MHz, $CDCl_3$) δ 8.43 (dd, J=4.8, 0.8 Hz, 1H), 7.3-7.37 (m, 1H), 7.29 (dd, J=8.4, 0.8 Hz, 1H), 7.16-7.14 (m, 2H), 6.71-6.69 (m, 1H).

The following intermediates were prepared based on the procedures described for Intermediate 153, and/or for Intermediate 153A to 153B.

Intermediate 153A. 2-Cyanopyridin-4-yl carbamimidothioate hydrochloride

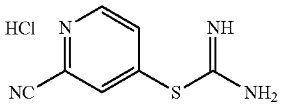

To a suspension of 4-chloropyridine-2-carbonitrile (100 g, 722 mmol) in ethanol (300 mL) was added thiourea (57.69 g, 758 mmol). The mixture was refluxed for 2 and half hours, cooled to room temperature. The formed precipitate was collected by filtration and rinsed with ethanol (2×200 mL), dried to give the title compound (134 g, 593 mmol, 82%) as a green solid. LC-MS: MS (ESI): 179 m/z $[M+H]^+$, retention time: 0.35 minutes, purity: >90% (214 nm) (LC-MS Method 3).

Intermediate 153B. 4-((2-Bromo-6-fluoro-3-methyl-4-nitrophenyl)thio)picolinonitrile

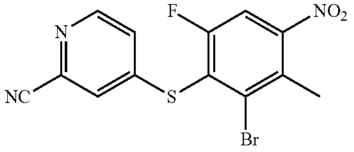

To a stirred solution of 2-(2-cyano-4-pyridyl)isothiourea hydrochloride (123 g, 573 mmol) in N,N-dimethylformamide (720 mL) was added sodium hydroxide (45.84 g, 1146 mmol) and water (574 g, 32 mol), the reaction mixture was stirred at room temperature for 15 minutes, then treated with 3-bromo-1,2-difluoro-4-methyl-5-nitro-benzene (151.61 g, 602 mmol), The mixture was stirred at room temperature for 2 hours, then filtered. The filter cake was rinsed with water (3×1L), then dissolved in ethyl acetate (1 L). This solution was washed with water, brine, dried over sodium sulfate, filtered, and concentrated. The residue was then slurred with petroleum ether (1 L) for 1 hour. The solid was collected by filtration to afford the title compound (200 g, 489 mmol,

| Inter. No. | Structure | Name | MS m/z $[M + H]^+$ |
|---|---|---|---|
| 153-1 | 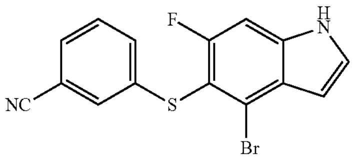 [SMILES: N#Cc1cccc(Sc2c(F)cc3[nH]ccc3c2Br)c1] | 3-((4-bromo-6-fluoro-1H-indol-5-yl)thio)benzonitrile | 347, 349 |
| 153-2 | 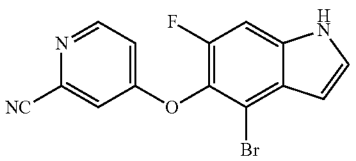 [SMILES: N#Cc1cc(Oc2c(F)cc3[nH]ccc3c2Br)ccn1] | 4-((4-bromo-6-fluoro-1H-indol-5-yl)oxy)picolinonitrile | 332, 334 [M + H] RT: 1.82 min. (LC-MS method 4) |

85%). LC-MS: MS (ESI): 368, 370 m/z [M+H]+, retention time: 1.76 minutes, purity: 91% (254 nm) (LC-MS Method 33).

Intermediate 154. 4-(4-Bromo-6-fluoro-1-(triisopropylsilyl)-1H-indole-5-carbonyl)picolinonitrile

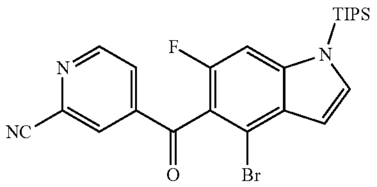

To a stirred solution of 4-[(4-bromo-6-fluoro-1-triisopropylsilyl-indol-5-yl)-hydroxy-methyl]pyridine-2-carbonitrile (Intermediate 57B-1, 5.00 g, 9.95 mmol) in dichloromethane (30 mL) and dimethylsulfoxide (30 mL) was added 1-hydroxy-1,2-benziodoxol-3(1h)-one 1-oxide (11.1 g, 39.8 mmol) at 0° C. The mixture was stirred at 0° C. for 3 hours, diluted with ethyl acetate (150 mL). The solution was washed with saturated sodium bicarbonate (3×50 mL), dried over sodium sulfate, filtered, and concentrated. The residue was purified by automated flash chromatography (25 g silica gel column, eluting with 0-40% ethyl acetate in petroleum ether) to give to the title compound (4.80 g, 96%) as a solid. LC-MS: MS (ESI): 500, 502 m/z [M+H]+, retention time: 2.35 minutes, purity: >99% (254 nm) (LC-MS Method 17).

Intermediate 155. 1,3-Dioxoisoindolin-2-yl 7-((2-((tert-butyldimethylsilyl)oxy)ethyl)sulfonyl)-2-(3-((R)-3-methoxy-2-methyl-3-oxopropyl)phenyl)-2,6,6-trimethylheptanoate

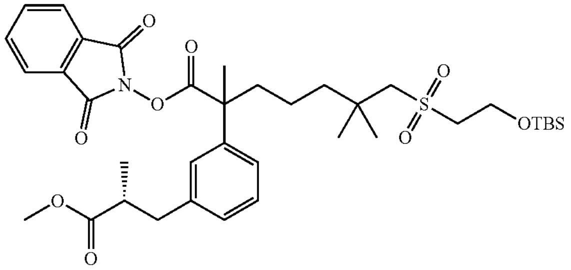 [SMILES: COC(=O)[C@H](C)Cc1cccc(C(C)(CCCC(C)(C)CS(=O)(=O)CCO[Si](C)(C)C(C)(C)C)C(=O)ON2C(=O)c3ccccc3C2=O)c1]

To a stirred solution of 1,3-dioxoisoindolin-2-yl 7-((2-hydroxyethyl)sulfonyl)-2-(3-((R)-3-methoxy-2-methyl-3-oxopropyl)phenyl)-2,6,6-trimethylheptanoate (Intermediate 155A, 3.00 g, 4.99 mmol) and imidazole (1.02 g, 15.0 mmol) in dichloromethane (40 mL) was added tert-butyldimethylchlorosilane (1.50 g, 9.97 mmol) and the whole mixture was stirred at room temperature for 3 hours. The reaction mixture was diluted with ethyl acetate (100 mL), washed with brine, dried over sodium sulfate, filtered, and concentrated. The residue was purified using automated flash chromatograph (eluant with ethyl acetate in petroleum ether 0 to 30%) to give the title compound (3.50 g, 4.64 mmol, 93%) as a color-less oil. LC-MS: MS (ESI): 738 m/z [M+Na]+, retention time: 2.68 minutes, purity: 74% (214 nm) (LC-MS Method 33).

Intermediate 155A: 1,3-Dioxoisoindolin-2-yl 7-((2-hydroxyethyl)sulfonyl)-2-(3-((R)-3-methoxy-2-methyl-3-oxopropyl)phenyl)-2,6,6-trimethylheptanoate

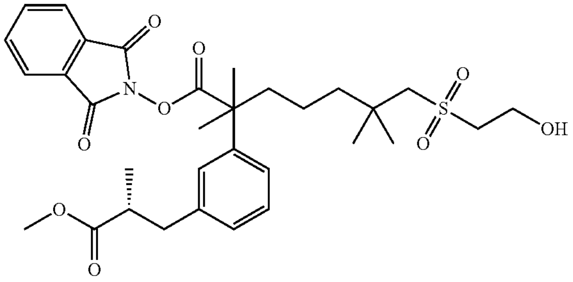

To a stirred solution of 7-(2-hydroxyethylsulfonyl)-2,6,6-trimethyl-2-[3-[rac-(2R)-3-methoxy-2-methyl-3-oxo-propyl]phenyl]heptanoic acid (Intermediate 76, 5.00 g, 11.0 mmol) in dichloromethane (100 mL) was added 2-hydroxyisoindoline-1,3-dione (1.88 g, 11.5 mmol), 4-dimethylaminopyridine (67 mg, 0.548 mmol) followed by N,N'-dicyclohexylcarbodiimide (2.71 g, 13.1 mmol) at room temperature under argon. The reaction mixture was stirring at room temperature for 5 hours and filtered. The filtrate was concentrated. The residue was purified using automated flash chromatography (eluting with ethyl acetate in petroleum ether 0 to 50%) to give the title compound (3.00 g, 3.49 mmol, 32%). LC-MS: MS (ESI): 602 m/z [M+H]+, retention time: 1.76 minutes, purity: 74% (214 nm) (LC-MS Method 33).

Intermediate 156: 4-((4-Bromo-6-fluoro-1-(triisopropylsilyl)-1H-indol-5-yl)methyl)picolinonitrile

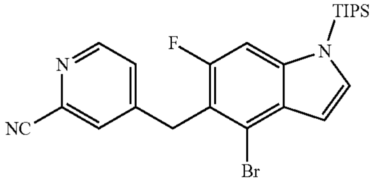

To a stirred solution of 4-((4-bromo-6-fluoro-1-(triisopropylsilyl)-1H-indol-5-yl)(hydroxy)methyl)picolinonitrile (Intermediate 57B-1, 2.00 g, 3.98 mmol) in tetrahydrofuran (16 mL) was added phosphorus tribromide (1.1 mL, 11.9 mmol). The mixture was stirred at 60° C. for 2 hours, quenched with water (50 ml) and basified with saturated sodium carbonate (1 mL) until pH=11. The mixture was extracted with ethyl acetate (2×60 mL). The combined organic layers were washed with brine, dried over sodium sulfate, filtered, and concentrated. The residue was purified by automated flash chromatography (40 g silica gel column, eluting with 0-14% ethyl acetate in petroleum ether) to give the title compound (1.80 g, 3.33 mmol, 84%) as a white solid. LC-MS: MS (ESI): 486, 488 m/z [M+H]+, retention time: 2.72 minutes, purity: >99% (214 nm) (LC-MS Method 4).

Intermediate 157. Benzyl (R)-2-(3-((R)-2,2-dimethyl-1,3-dioxolan-4-yl)phenyl)-7-((2-hydroxyethyl)sulfonyl)-2,6,6-trimethylheptanoate

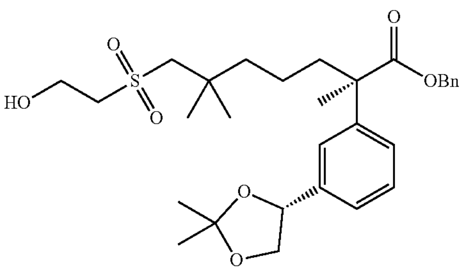 [SMILES: CC(C)(CCC[C@@](C)(C(=O)OCc1ccccc1)c1cccc([C@@H]2COC(C)(C)O2)c1)CS(=O)(=O)CCO]

To a stirred solution of benzyl (R)-7-((2-((tert-butyldimethylsilyl)oxy)ethyl)sulfonyl)-2-(3-((R)-1,2-dihydroxyethyl)phenyl)-2,6,6-trimethylheptanoate (Intermediate 155B, 330 mg, 0.531 mmol) in N,N-dimethylformamide (2 mL) was added 2,2-dimethoxypropane (2.0 mL), followed by p-toluenesulfonic acid monohydrate (20 mg, 0.106 mmol). The reaction mixture was stirred at room temperature for 16 hours. The reaction mixture was quenched with water (30 mL) and extracted with ethyl acetate (3×20 mL). The combined organic layer was washed with brine, dried over sodium sulfate, filtered, and concentrated to give the title compound (270 mg, 0.49 mmol, 93%) as light-yellow oil. LC-MS: MS (ESI): 569 m/z $[M+Na]^+$, retention time: 1.90 minutes, purity: 85% (214 nm) (LC-MS Method 17).

Intermediate 157A. Benzyl (R)-7-((2-((tert-butyldimethylsilyl)oxy)ethyl)sulfonyl)-2,6,6-trimethyl-2-(3-vinylphenyl)heptanoate

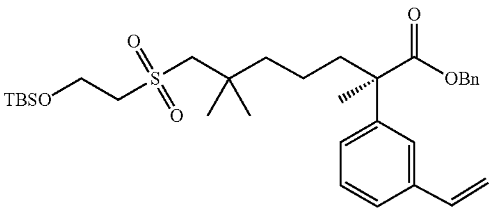 [SMILES: C=Cc1cccc([C@@](C)(CCCC(C)(C)CS(=O)(=O)CCO[Si](C)(C)C(C)(C)C)C(=O)OCc2ccccc2)c1]

To a stirred solution of benzyl (R)-7-((2-((tert-butyldimethylsilyl)oxy)ethyl)sulfonyl)-2-(3-iodophenyl)-2,6,6-trimethylheptanoate (1.00 g, 1.46 mmol) in 1,4-dioxane (15 mL) and water (1.5 mL) was added 4,4,5,5-tetramethyl-2-vinyl-1,3,2-dioxaborolane (0.45 g, 2.91 mmol), potassium carbonate (604 mg, 4.37 mmol) and $Pd(dppf)Cl_2$ (0.12 g, 0.146 mmol). The reaction mixture was stirred at 90° C. for 2 hours, quenched with water (30 mL), and extracted with ethyl acetate (3×20 mL). The combined organic extracts were washed with brine, dried over sodium sulfate, filtered, and concentrated. The residue was purified by automated flash chromatography (25 g silica gel column, eluting with 0-30% ethyl acetate in petroleum ether) to give the title compound (550 mg, 0.937 mmol, 64%) as colorless oil. LC-MS: MS (ESI): 609 m/z $[M+Na]^+$, retention time: 2.48 minutes, purity: 84% (214 nm) (LC-MS Method 4).

Intermediate 157B. Benzyl (R)-7-((2-((tert-butyldimethylsilyl)oxy)ethyl)sulfonyl)-2-(3-((R)-1,2-dihydroxyethyl)phenyl)-2,6,6-trimethylheptanoate

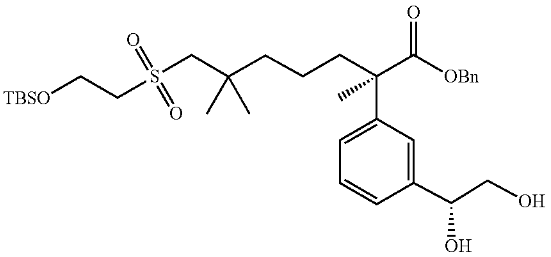 [SMILES: CC(C)(CCC[C@@](C)(C(=O)OCc1ccccc1)c1cccc([C@@H](O)CO)c1)CS(=O)(=O)CCO[Si](C)(C)C(C)(C)C]

To a stirred solution of benzyl (R)-7-((2-((tert-butyldimethylsilyl)oxy)ethyl)sulfonyl)-2,6,6-trimethyl-2-(3-vinylphenyl)heptanoate (Intermediate 157A, 350 mg, 0.596 mmol) in water (4 mL) and tert-butanol (4 mL) was added potassium carbonate (247 mg, 1.79 mmol), potassium ferricyanide (589 mg, 1.79 mmol), sodium bicarbonate (150 mg, 1.79 mmol), $(DHQD)_2PHAL$ (46 mg, 0.0596 mmol), potassium osmate (0.0500 eq, 11 mg, 0.0298 mmol), and methanesulfonamide (57 mg, 0.596 mmol). The reaction mixture was stirred at 0° C. for 18 hours, quenched with saturated sodium sulfite (30 mL), and extracted with ethyl acetate (3×20 mL). The combined organic layers were dried over sodium sulfate, filtered, and concentrated. The residue was purified by automated flash chromatography (12 g silica gel column, eluting with 0-40% ethyl acetate in petroleum ether) to give the title compound (270 mg, 0.435 mmol, 72%) as a light-yellow oil. LC-MS: MS (ESI): 643 m/z $[M+Na]^+$, retention time: 2.04 minutes, purity: 96% (214 nm) (LC-MS Method 17).

The following intermediate was prepared based on the procedures described for Intermediate 157B (AD-mix-a was used).

| Inter. No. | Structure | Name | MS m/z [M + H]+ |
|---|---|---|---|
| 157B-1-1 | 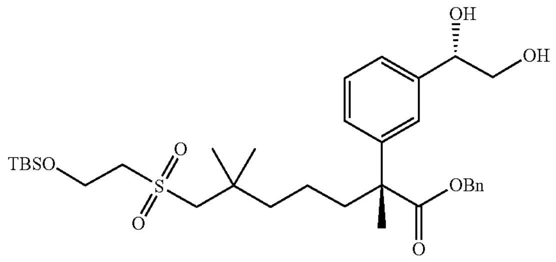 [SMILES: CC(C)(CCC[C@@](C)(C(=O)OCc1ccccc1)c1cccc([C@H](O)CO)c1)CS(=O)(=O)CCO[Si](C)(C)C(C)(C)C] | benzyl (R)-7-((2-((tert-butyldimethylsilyl)oxy)ethyl)sulfonyl)-2-(3-((S)-1,2-dihydroxyethyl)phenyl)-2,6,6-trimethylheptanoate | 643 [M + Na]+; RT: 2.04 min. (LC-MS Method 017) |

Intermediate 158. Benzyl (R)-2-(3-((S)-2-acetoxypropyl)phenyl)-7-((2-((tert-butyldimethylsilyl)oxy)ethyl)sulfonyl)-2,6,6-trimethylheptanoate

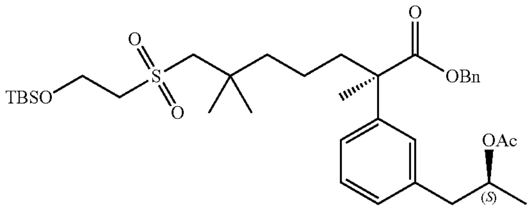

To a stirred solution of benzyl (R)-7-((2-((tert-butyldimethylsilyl)oxy)ethyl)sulfonyl)-2-(3-((S)-2-hydroxypropyl)phenyl)-2,6,6-trimethylheptanoate (Intermediate 158A, 1.20 g, 1.94 mmol) in dichloromethane (10 mL) was added triethylamine (0.82 mL, 5.82 mmol), 4-dimethylaminopyridine (0.024 g, 0.194 mmol) and acetic anhydride (0.276 mL, 2.90 mmol). The reaction mixture was stirred at room temperature for 2 hours, quenched with water (15 mL), and diluted with 30 mL of dichloromethane. The solution was washed with water, brine, dried over sodium sulfate, and concentrated. The residue was purified by flash column chromatography eluting with 0-20% ethyl acetate in petroleum ether to afford the title compound (1.12 g, 1.69 mmol, 87%) as a colorless oil. LC-MS: MS (ESI): 683 m/z $[M+Na]^+$, retention time: 2.41 minutes, purity: 95% (214 nm) (LC-MS Method 4).

Intermediate 158A. Benzyl (R)-7-((2-((tert-butyldimethylsilyl)oxy)ethyl)sulfonyl)-2-(3-((S)-2-hydroxypropyl)phenyl)-2,6,6-trimethylheptanoate

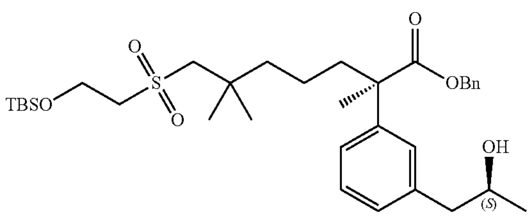

To a stirred solution of benzyl (R)-7-((2-((tert-butyldimethylsilyl)oxy)ethyl)sulfonyl)-2-(3-iodophenyl)-2,6,6-trimethylheptanoate (Intermediate 137E, 5 g, 7.28 mmol) in 1,3-dimethyl-3,4,5,6-tetrahydro-2(1H)-pyrimidinone (20 mL) was added zinc (950 mg, 14.6 mmol), sodium iodide (270 mg, 1.82 mmol), pyridine (0.12 mL, 1.46 mmol), nickel iodide (230 mg, 0.728 mmol), triethylamine hydrochloride (1 g, 7.28 mmol), 2,2'-bipyridine (110 mg, 0.728 mmol) and (S)-(−)-propylene oxide (0.77 mL, 10.9 mmol). The reaction mixture was stirred at room temperature overnight and quenched with water (30 mL). The formed solid was removed by filtration. The filtrate was extracted by ethyl acetate (2×50 mL). The combined organic extracts were washed with water, brine, dried over sodium sulfate and concentrated. The residue was purified by flash column chromatography eluting with 0-40% ethyl acetate in petroleum ether. The desired fractions were concentrated to give the title compound (1.20 g, 1.94 mmol, 27%) as a colorless oil. LC-MS: MS (ESI): 641 m/z $[M+Na]^+$, retention time: 2.26 minutes, purity: 96% (214 nm) (LC-MS Method 4). Chiral-HPLC purity: >99% ee. (Chiral HPLC conditions: Column: OJ-H (250*4.6 mm 5 μm); Mobile Phase: n-Hexane (0.1% diethylamine):ethanol (0.1% diethylamine)= 90:10; Temperature: 40° C.; Flow: 1.0 mL/minute; Wavelength: 220 nm. Inject Volume: 5 μl.

Intermediate 159. 4-Bromo-6-fluoro-1-(triisopropylsilyl)-1H-indol-5-ol

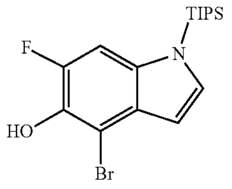

To a stirred solution of (4-bromo-6-fluoro-1-triisopropylsilyl-indol-5-yl)boronic acid (Intermediate 159A, 11.00 g, 15.9 mmol) in tetrahydrofuran (80 mL) and water (40 mL) was added sodium perborate tetrahydrate (7.36 g, 47.8 mmol). The mixture was stirred at room temperature for 16 hours. Then the mixture was quenched with water (150 mL) and extracted with ethyl acetate (3×150 mL). The combined organic extracts were washed with brine, dried over sodium sulfate, filtered and concentrated. The residue was purified by automated flash chromatography (120 g silica gel column, eluting with 0-15% ethyl acetate in petroleum ether) to give the title compound (6.00 g, 14.0 mmol, 88%) as a white solid. LC-MS: MS (ESI): 386, 388 m/z $[M+H]^+$, retention time: 2.05 minutes, purity: 90% (254 nm) (LC-MS Method 21).

Intermediate 159A. (4-Bromo-6-fluoro-1-(triisopropylsilyl)-1H-indol-5-yl)boronic Acid

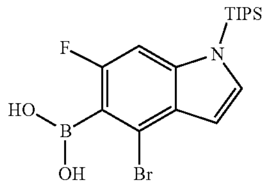

To a stirred and cooled (−78° C.) solution of (4-bromo-6-fluoro-indol-1-yl)-triisopropyl-silane (15.00 g, 40.5 mmol) in tetrahydrofuran (50 mL) was added lithium diisopropylamide (2.0 M in tetrahydrofuran/n-heptane ethylbenzene, 30.4 mL, 60.7 mmol). The mixture was stirred at −78° C. for 40 minutes, treated with triisopropyl borate (14 mL, 60.7 mmol), then warmed to room temperature and stirred for additional 2 hours. The reaction mixture was quenched with water (150 mL) and extracted with ethyl acetate (3×150 mL). The combined organic extracts were washed with brine, dried over sodium sulfate, filtered, and concentrated. The residue was purified by automated flash chromatography (120 g silica gel column, eluting with 0-20% ethyl acetate in petroleum ether) to give the title compound (10.00 g, 21.7 mmol, 54%) as a solid. LC-MS: MS (ESI): 414, 416 m/z $[M+H]^+$, retention time: 2.12 minutes, purity: 90% (254 nm) (LC-MS Method 21).

Intermediate 160. 5-((4-Bromo-6-fluoro-1H-indol-5-yl)oxy)pyridazine-3-carbothioamide

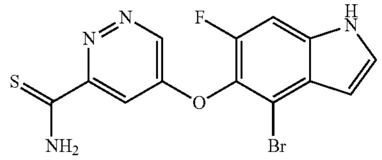 [SMILES: NC(=S)c1cc(Oc2c(F)cc3[nH]ccc3c2Br)cnn1]

To a stirred solution of 5-((4-bromo-6-fluoro-1H-indol-5-yl)oxy)pyridazine-3-carboxamide (Intermediate 160B, 1.20 g, 3.42 mmol) in tetrahydrofuran (25 mL) was added phosphorus pentasulfide (1.52 g, 6.84 mmol). The mixture was stirred at room temperature for 1 hour, then quenched with water (60 mL) and extracted with ethyl acetate (4×100 mL). The combined organic extracts were washed with brine (100 mL), dried over sodium sulfate, filtered, and concentrated. The residue was purified by automated flash chromatography (80 g silica gel column, eluting with 0-50% ethyl acetate in petroleum ether) to give the title compound (680 mg, 1.76 mmol, 52%) as a white solid. LC-MS: MS (ESI): 367, 369 m/z $[M+H]^+$, retention time: 1.57 minutes, purity: 95% (254 nm) (LC-MS Method 21).

Intermediate 160A. Methyl 5-((4-bromo-6-fluoro-1H-indol-5-yl)oxy)pyridazine-3-carboxylate

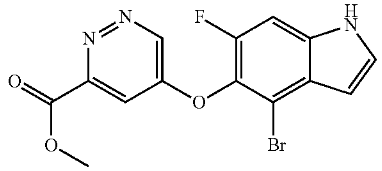 [SMILES: COC(=O)c1cc(Oc2c(F)cc3[nH]ccc3c2Br)cnn1]

To a stirred solution of methyl 5-chloropyridazine-3-carboxylate (2.30 g, 13.3 mmol) in N,N-dimethylformamide (50 mL) were added 4-bromo-6-fluoro-1-(triisopropylsilyl)-1H-indol-5-ol (5.15 g, 13.3 mmol) and cesium carbonate (6.51 g, 20.0 mmol). The mixture was stirred at room temperature for 6 hours, quenched with water (100 mL), and extracted with ethyl acetate (3×150 mL). The combined organic extracts were washed with brine, dried over sodium sulfate, filtered. and concentrated. The residue was purified by flash chromatography (80 g silica gel column, eluting with 0-80% ethyl acetate in petroleum ether) to give the title compound (4.10 mmol, 31%) as a white solid. LC-MS: MS (ESI): 366, 368 m/z $[M+H]^+$, retention time: 1.52 minutes, purity: 75% (254 nm) (LC-MS Method 21).

Intermediate 160B. 5-((4-Bromo-6-fluoro-1H-indol-5-yl)oxy)pyridazine-3-carboxamide

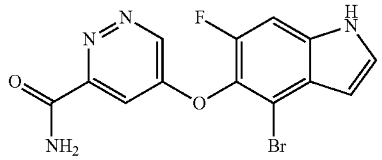 [SMILES: NC(=O)c1cc(Oc2c(F)cc3[nH]ccc3c2Br)cnn1]

To a stirred solution of methyl 5-((4-bromo-6-fluoro-1H-indol-5-yl)oxy)pyridazine-3-carboxylate (2.00 g, 4.10 mmol) in tetrahydrofuran (30 mL) were added ammonia solution (28% in water, 15 mL). The mixture was stirred at room temperature overnight, quenched with water (80 mL), and extracted with ethyl acetate (2×100 mL). The combined organic extracts were washed with brine, dried over sodium sulfate, filtered, and concentrated. The residue was purified by prep-HPLC to give the title compound (1.20 g, 3.25 mmol, 79%) as a white solid. LC-MS: MS (ESI): 351, 353 m/z $[M+H]^+$, retention time: 1.52 minutes, purity: 75% (254 nm) (LC-MS Method 21).

Intermediate 161. (R)-2-(3-Bromo-2-fluorophenyl)-7-hydroxy-2,6,6-trimethylheptanoic Acid

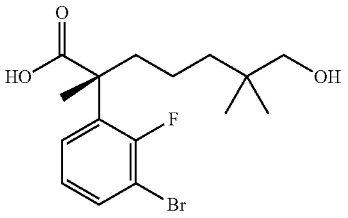 [SMILES: CC(C)(CO)CCC[C@@](C)(C(=O)O)c1cccc(Br)c1F]

A mixture of (S)-5-amino-5-carboxypentan-1-aminium (R)-2-(3-bromo-2-fluorophenyl)-7-((tert-butyldimethylsilyl)oxy)-2,6,6-trimethylheptanoate (Intermediate 161A, 32.70 g, 52.6 mmol) in hydrochloric acid/1,4-dioxane (4.0 M, 200 mL, 800 mmol) was stirred at room temperature for 2.0 hours and concentrated. The residue was purified by automated flash chromatography (120 g silica gel column, eluting with 0-35% ethyl acetate in petroleum) to give the title compound (18.00 g, 49.8 mmol, 95%) as a light-yellow oil. LC-MS: MS (ESI): 383, 385 m/z $[M+H]^+$, retention time: 1.06 minutes, purity: 95% (214 nm) (LC-MS Method 35).

Intermediate 161A. (S)-5-Amino-5-carboxypentan-1-aminium (R)-2-(3-bromo-2-fluorophenyl)-7-((tert-butyldimethylsilyl)oxy)-2,6,6-trimethylheptanoate

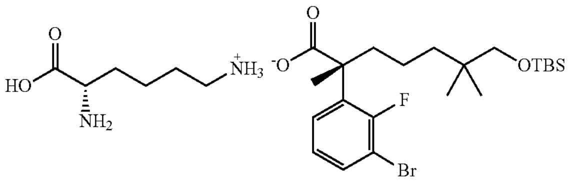

To a stirred solution of (2S)-2,6-diaminohexanoic acid (18.24 g, 125 mmol) in ethanol/$H_2O$ (v/v=9/1, 600 mL) was added a solution of 2-(3-bromo-2-fluorophenyl)-7-((tert-butyldimethylsilyl)oxy)-2,6,6-trimethylheptanoic acid (Intermediate 40-1, 56.50 g, 119 mmol) in ethanol/$H_2O$ (v/v=9/1, 600 mL). The mixture was stirred at 60° C. for 1 hour, then slowly cooled to room temperature, and stirred at room temperature for another 16 h. The solid was collected by filtration and washed with ethanol/water (v/v=9/1, 100 mL) and dried at 40° C. under vacuum for 2 hours to give the title compound (27.50 g, 44.2 mmol, 37%) as a white solid. LC-MS: MS (ESI): 475, 477 m/z $[M+H]^+$, retention time: 1.55 minutes, purity: 98% (214 nm) (LC-MS Method 35). Chiral HPLC method: Column: IC-3 4.6*100 mm 3 μm; Acquisition Method Set: IC 10% B2; Co-Solvent: EtOH[1% ammonia in MeOH (7M)]; Injection Volume: 5.00 μL; Channel Name: PDA Ch2 214 nm @4.8 nm; Run Time: 2.0 Minutes; Flowrate: 3.0 mL/minute; Back-Pressure: 2000 psi; Column Temperature: 40° C. Retention time=0.679 min, purity: >99% (214 nm).

Intermediate 162. Benzyl (R)-2-(3-((R)-2-acetoxypropyl)phenyl)-7-((2-((tert-butyldimethylsilyl)oxy)ethyl)sulfonyl)-2,6,6-trimethylheptanoate

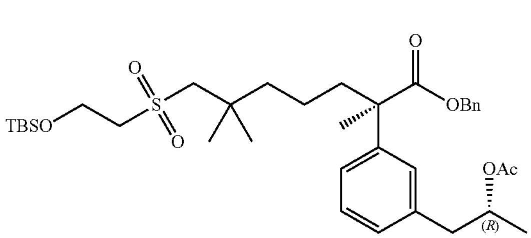

To a stirred solution of benzyl (R)-7-((2-((tert-butyldimethylsilyl)oxy)ethyl)sulfonyl)-2-(3-((R)-2-hydroxypropyl)phenyl)-2,6,6-trimethylheptanoate (Intermediate 162A, 1.20 g, 1.94 mmol) in dichloromethane (10 mL) was added triethylamine (0.82 mL, 5.82 mmol), 4-dimethylaminopyridine (0.024 g, 0.194 mmol) and acetic anhydride (0.276 mL, 2.90 mmol). The reaction mixture was stirred at room temperature for 2 hours, quenched with water (15 mL), and extracted with dichloromethane (2×50 mL). The combined organic extracts were washed with water, brine, dried over sodium sulfate, and concentrated. The residue was then purified by automated flash column chromatography eluting with 0-20% ethyl acetate in petroleum ether to afford the title compound (1.12 g, 1.69 mmol, 87%) as a colorless oil. LC-MS: MS (ESI): 683 m/z $[M+Na]^+$, retention time: 2.41 minutes, purity: 95% (214 nm) (LC-MS Method 003).

Intermediate 162A. Benzyl (R)-7-((2-((tert-butyldimethylsilyl)oxy)ethyl)sulfonyl)-2-(3-((R)-2-hydroxypropyl)phenyl)-2,6,6-trimethylheptanoate

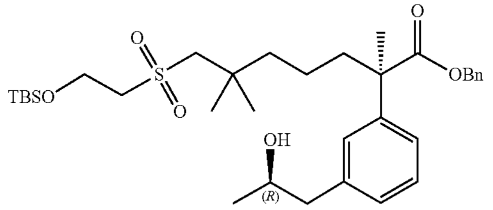

To a stirred solution of benzyl (R)-7-((2-((tert-butyldimethylsilyl)oxy)ethyl)sulfonyl)-2-(3-iodophenyl)-2,6,6-trimethylheptanoate (Intermediate 137E, 5.00 g, 7.28 mmol) in 1,3-dimethyl-3,4,5,6-tetrahydro-2(1H)-pyrimidinone (20 mL) was added zinc (950 mg, 14.6 mmol), sodium iodide (270 mg, 1.82 mmol), pyridine (0.12 mL, 1.46 mmol), Nickel iodide (230 mg, 0.728 mmol), triethylamine hydrochloride (1 g, 7.28 mmol), 2,2'-bipyridine (110 mg, 0.728 mmol) and (R)-(+)-propylene oxide (10.0 eq, 5.2 mL, 72.8 mmol). The reaction mixture was stirred at room temperature overnight and quenched with water (100 mL). The formed solid was removed by filtration. The filtrate was extracted by ethyl acetate (2×100 mL). The combined organic extracts were washed with water, brine, dried over sodium sulfate, and concentrated. The residue was purified by automated flash column chromatography eluting with 0-40% ethyl acetate in petroleum ether to afford the title compound (1.70 g, 2.75 mmol, 38%) as a colorless oil. LC-MS: MS (ESI): 641 m/z $[M+Na]^+$, retention time: 2.23 minutes, purity: 99% (214 nm) (LC-MS Method 003).

Intermediate 163. 4-((4-amino-2-bromo-5,6-difluoro-3-iodophenyl)thio)picolinonitrile

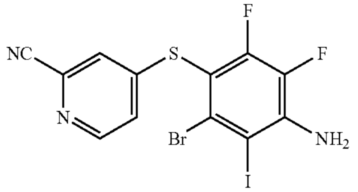 [SMILES: N#Cc1cc(Sc2c(F)c(F)c(N)c(I)c2Br)ccn1]

To a stirred solution of 4-(4-amino-6-bromo-2,3-difluorophenyl)sulfanylpyridine-2-carbonitrile (Intermediate 163C, 33.00 g, 96.4 mmol) in acetic acid (250 mL) was added N-iodosuccinimide (25.0 g, 111 mmol). The mixture was stirred at 50° C. for 3 hours and cooled to room temperature. The formed precipitate was collected by filtration, rinsed with sodium bicarbonate and dried to give the title compound (35.00 g, 74.8 mmol, 78%, yellow solid) as a pure single regio-isomer. LC-MS: MS (ESI): 468, 470 m/z $[M+H]^+$, retention time: 1.24 minutes, purity: 95% (254 nm) (LC-MS Method 022).

Intermediate 163A. 2-cyanopyridin-4-yl carbamimidothioate hydrochloride

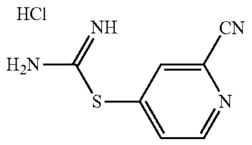 [SMILES: Cl ; N#Cc1cc(SC(=N)N)ccn1]

A suspension of 4-chloropyridine-2-carbonitrile (100.00 g, 722 mmol) and thiourea (57.69 g, 758 mmol) in ethanol (300 mL) was heated to reflux for 2 hours, cooled to room temperature. The formed precipitate was collected by filtration, rinsed with ethanol and dried in vacuum to afford the title compound (134.00 g, 593 mmol, 82%) as a green solid. LC-MS: MS (ESI): 179 m/z $[M+H]^+$, retention time: 0.35 minutes, purity: 95% (254 nm) (LC-MS Method 022).

Intermediate 163B. 4-((6-bromo-2,3-difluoro-4-nitrophenyl)thio)picolinonitrile

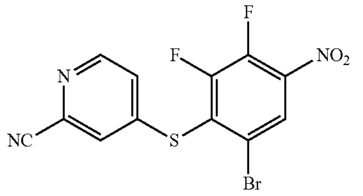 [SMILES: N#Cc1cc(Sc2c(Br)cc([N+](=O)[O-])c(F)c2F)ccn1]

To a stirred solution of 2-cyanopyridin-4-yl carbamimidothioate hydrochloride (Intermediate 163A, 50 g, 232.9 mmol) in N,N-dimethylformamide (1000 mL) was added sodium hydroxide (233 mL, 466 mmol) at room temperature. The reaction mixture was stirred at room temperature for 10 minutes, treated with 1-bromo-2,3,4-trifluoro-5-nitrobenzene (59.6 g, 233 mmol) at −60° C. and stirred at this temperature for 1 hour. The reaction mixture was diluted with ethyl acetate (1500 mL), washed with water, dried over magnesium sulfate, filtered, and concentrated. The residue was purified by automated silica gel column chromatography (330 g silica gel column, eluting with 0-15% ethyl acetate in petroleum ether) to give the title compound and its regio-isomer (40 g, 46%) as an inseparable solid. LC-MS: MS (ESI): 372, 374 m/z $[M+H]^+$, retention time: 1.85/1.91 minutes, purity: 90% (214 nm) (LC-MS Method 021).

Intermediate 163C. 4-((4-amino-6-bromo-2,3-difluorophenyl)thio)picolinonitrile

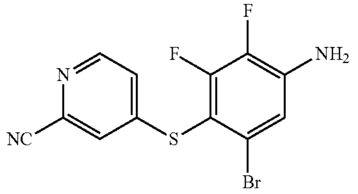 [SMILES: N#Cc1cc(Sc2c(Br)cc(N)c(F)c2F)ccn1]

To a stirred solution of 4-(6-bromo-2,3-difluoro-4-nitrophenyl)sulfanylpyridine-2-carbonitrile (Intermediate 163B, 67 g, 180.04 mmol) in acetic acid (670 mL) was added Fe (30 g, 540.12 mmol) at room temperature. The reaction mixture was stirring at room temperature for 1 hour and concentrated. The residue was diluted with ethyl acetate (500 mL), washed with water, dried over magnesium sulfate, filtered, and concentrated. The residue was purified by automated silica gel column chromatography (330 g silica gel column, eluting with 0-30% ethyl acetate in petroleum ether) to give the title compound and its regio-isomer as an inseparable mixture (51 g, 80%). LC-MS: MS (ESI): 342, 344 m/z $[M+H]^+$, retention time: 1.92 minutes, purity: 85% (254 nm) (LC-MS Method 003).

Intermediate 164. Benzyl (R)-7-((2-((tert-butyldimethylsilyl)oxy)ethyl)sulfonyl)-2-(2-fluoro-3-iodophenyl)-2,6,6-trimethylheptanoate

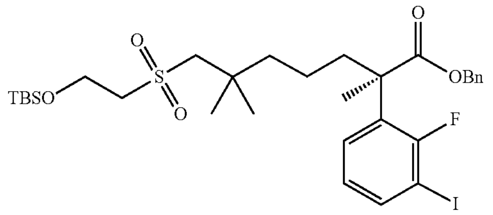 [SMILES: CC(C)(CCC[C@@](C)(C(=O)OCc1ccccc1)c1cccc(I)c1F)CS(=O)(=O)CCO[Si](C)(C)C(C)(C)C]

To a stirred solution of benzyl (2R)-2-(3-bromo-2-fluorophenyl)-7-[2-[tert-butyl(dimethyl)silyl]oxyethylsulfonyl]-2,6,6-trimethyl-heptanoate (Intermediate 164A, 1.50 g, 2.28 mmol) and N,N'-dimethyl-cyclohexane-1,2-diamine (0.2000 eq, 64 mg, 0.456 mmol) in 1,4-Dioxane (15 mL) was added copper(I) iodide (44 mg, 0.228 mmol) and sodium iodide (684 mg, 4.56 mmol). The mixture was stirred at 110° C. overnight, cooled to room temperature, filtered. The filter cake was washed with 1,4-dioxane (10 mL). The combined filtrate was concentrated. The residue was purified by automated flash chromatography (25 g silica gel column, eluting with 15-40% ethyl acetate in petroleum ether) to afford the title compound (1.20 g, 1.70 mmol, 75%) as a yellow solid. LC-MS: MS (ESI): 705 m/z $[M+H]^+$, retention time: 2.46 minutes, purity: 97% (214 nm) (LC-MS Method 004).

Intermediate 164A: Benzyl (R)-2-(3-bromo-2-fluorophenyl)-7-((2-((tert-butyldimethylsilyl)oxy)ethyl)sulfonyl)-2,6,6-trimethylheptanoate

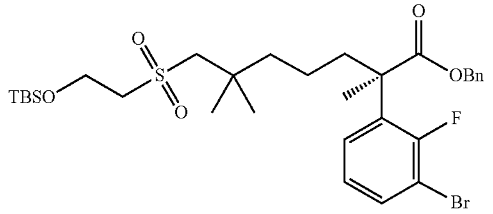 [SMILES: CC(C)(CCC[C@@](C)(C(=O)OCc1ccccc1)c1cccc(Br)c1F)CS(=O)(=O)CCO[Si](C)(C)C(C)(C)C]

To a stirred and cooled (0° C.) solution of benzyl (2R)-2-(3-bromo-2-fluoro-phenyl)-7-[2-[tert-butyl(dimethyl)silyl]oxyethylsulfanyl]-2,6,6-trimethyl-heptanoate (14.50 g, 23.2 mmol) in methanol (200 mL) was added dropwise a solution of ammonium molybdate tetrahydrate (0.200 eq, 5.73 g, 4.63 mmol) in hydrogen peroxide (30% in water, 20 mL). The mixture was stirred at room temperature for 2 hours, diluted with water (400 mL), and extracted with ethyl acetate (3×200 mL). The combined organic extracts were washed with brine, dried over sodium sulfate and concentrated to the title compound (15.00 g, 22.8 mmol, 98%) as colorless oil. LC-MS: MS (ESI): 679 m/z $[M+H]^+$, retention time: 2.49 minutes, purity: 89% (214 nm) (LC-MS Method 003).

Intermediate 165A (Diastereomer 1) and 165B (Diastereomer 2). Diastereomer 1 and 2 of methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate

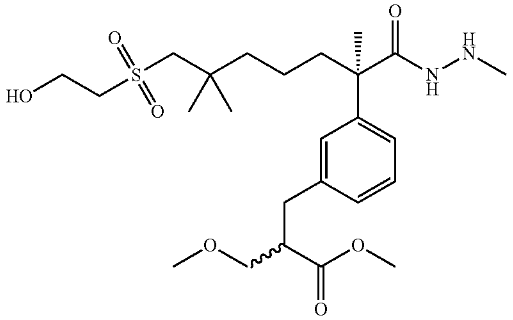 [SMILES: CNNC(=O)[C@](C)(CCCC(C)(C)CS(=O)(=O)CCO)c1cccc(CC(COC)C(=O)OC)c1]

The two diastereomeric mixture of methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate (Intermediate 137-4, 2.40 g, 4.66 mmol) was subject to SFC chiral separation under the following conditions: Instrument: SFC-150 (Thar, Waters); Column: AD 20*250 mm, 10 µm, Column temperature: 35° C.; Mobile phase: carbon dioxide/ethanol (additive: 0.5% ammonia in methanol (7M))= 60/40, Flow rate: 100 g/min; Back pressure: 100 bar; Detection wavelength: 214 nm; Cycle time: 3.6 minutes; Sample solution: 2400 mg dissolved in 40 mL of methanol, Injection volume: 1.0 mL. The first eluent (1.0 g, 1.94 mmol, 42%, ee: >99%) was designated as Intermediate 165A; The second eluent (1.1 g, 2.1 mmol, 46%, ee: >99%) was designated as Intermediate 165B. Chiral HPLC conditions: Column Name: AD-H 4.6*100 mm, 5 µm; Mobile Phase: carbon dioxide/EtOH[additive: 1% ammonia in methanol (7M)]; Injection Volume: 5.00 µL; Channel Name: PDA Ch1 214 nm @4.8 nm; Run Time: 4.0 Minutes; Flowrate: 3.0 mL/minute; Back Pressure: 2000 psi. Retention time: Intermediate 165A: 1.49 minutes; Intermediate 165B: 2.17 minutes.

Intermediate 166. Benzyl (R)-2-(3-(((R)-2,2-dimethyl-1,3-dioxolan-4-yl)methyl)phenyl)-7-((2-hydroxyethyl)sulfonyl)-2,6,6-trimethylheptanoate

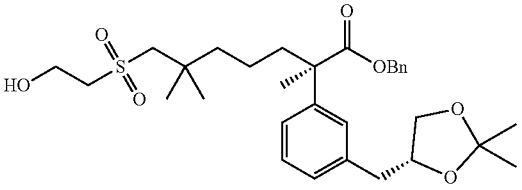

To a stirred solution of Intermediate 166B (500 mg, 0.787 mmol) in N,N-dimethylformamide (3 mL) was added 2,2-dimethoxypropane (3.0 mL) and p-toluenesulfonic acid monohydrate (30 mg, 0.157 mmol). The reaction mixture was stirred at room temperature for 16 hours, quenched with water (30 mL), and extracted with ethyl acetate (3×20 mL). The combined organic layers were washed with brine (3×40 mL), dried over sodium sulfate, filtered, and concentrated to give the title compound (400 mg, 0.708 mmol, 90%, ~7:3 mixture of R and S at 1,3-dioxolane) as light-yellow oil. LC-MS: MS (ESI): 583 m/z $[M+Na]^+$, retention time: 1.90 minutes, purity: 95% (214 nm) (LC-MS Method 017).

Intermediate 166A. benzyl (R)-2-(3-allylphenyl)-7-((2-((tert-butyldimethylsilyl)oxy)ethyl)sulfonyl)-2,6,6-trimethylheptanoate

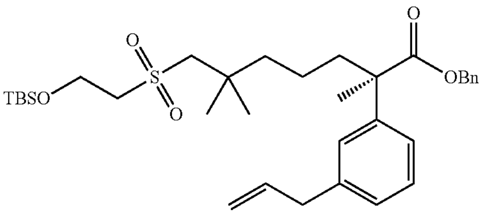 [SMILES: C=CCc1cccc([C@@](C)(CCCC(C)(C)CS(=O)(=O)CCO[Si](C)(C)C(C)(C)C)C(=O)OCc2ccccc2)c1]

To a stirred solution of benzyl (R)-7-((2-((tert-butyldimethylsilyl)oxy)ethyl)sulfonyl)-2-(3-iodophenyl)-2,6,6-trimethylheptanoate (Intermediate 137E, 1.00 g, 1.46 mmol) in tetrahydrofuran (15 mL) was added 2-allyl-4,4,5,5-tetramethyl-1,3,2-dioxaborolane (0.49 g, 2.91 mmol), CsF (887 mg, 5.84 mmol) and palladium tetrakis(triphenylphosphine (0.17 g, 0.146 mmol). The reaction mixture was stirred at reflux for 16 hours, cooled to room temperature, quenched with water (30 mL), and extracted with ethyl acetate (3×20 mL). The combined organic extracts were washed with brine, dried over sodium sulfate, filtered, and concentrated. The residue was purified by automated flash chromatography (25 g silica gel column, eluting with 0-30% ethyl acetate in petroleum ether) to give the title compound (600 mg, 0.937 mmol, 68%) as colorless oil. LC-MS: MS (ESI): 623 m/z [M+Na]$^+$, retention time: 2.48 minutes, purity: 90% (214 nm) (LC-MS Method 004).

Intermediate 166B. Benzyl (R)-7-((2-((tert-butyldimethylsilyl)oxy)ethyl)sulfonyl)-2-(3-((R)-2,3-dihydroxypropyl)phenyl)-2,6,6-trimethylheptanoate

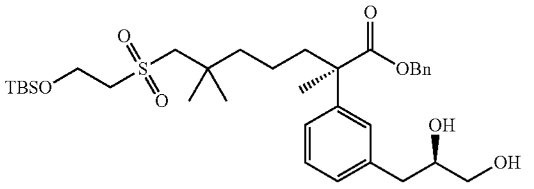 [SMILES: CC(C)(CCC[C@@](C)(C(=O)OCc1ccccc1)c1cccc(C[C@@H](O)CO)c1)CS(=O)(=O)CCO[Si](C)(C)C(C)(C)C]

To a stirred solution of Intermediate 166A (500 mg, 0.833 mmol) in water (5.6 mL) and tert-butanol (5.6 mL) was added potassium carbonate (346 mg, 2.86 mmol), potassium ferricyanide (3.00 eq, 825 mg, 2.506 mmol), sodium bicarbonate (210 mg, 2.506 mmol), $(DHQD)_2PHAL$ (65 mg, 0.0833 mmol), potassium osmate dihydrate (015.4 mg, 0.042 mmol), and methanesulfonamide (80 mg, 0.833 mmol). The reaction mixture was stirred at 0° C. for 18 hours, quenched with aqueous sodium sulfite (30 mL), and extracted with ethyl acetate (3×20 mL). The combined organic layers were dried over anhydrous sodium sulfate, filtered, and concentrated. The residue was purified by automated flash chromatography (12 g silica gel column, eluting with 0-40% ethyl acetate in petroleum ether) to give the title compound (500 mg, 0.787 mmol, 94%, ~7:3 mixture of R and S at diol position) as a light-yellow oil. LC-MS: MS (ESI): 657 m/z [M+Na]$^+$, retention time: 2.04 minutes, purity: 95% (214 nm) (LC-MS Method 017). Chiral HPLC conditions: Column: OJ-H (250*4.6 mm 5 μm); Mobile Phase: n-Hexane (0.1% diethylamine):ethanol (0.1% diethylamine)=90:10; Temperature: 40° C.; Flow: 1.0 mL/min; Detector wavelength: 214 nm & 254 nm; Instrument: SHIMADZU; Inject Volume: 8 μL. Retention time: 9.45 minutes (vs. S isomer: 7.26 minutes)

The following intermediate was prepared based on the procedures described for Intermediate 166B.

Intermediate 167. (S)-3-(3-((R)-1-(Benzyloxy)-7-((2-((tert-butyldimethylsilyl)oxy)ethyl)sulfonyl)-2,6,6-trimethyl-1-oxoheptan-2-yl)phenyl)propane-1,2-diyl diacetate

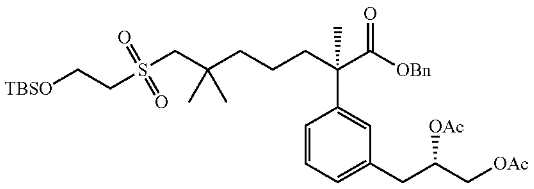

To a stirred solution of benzyl (R)-7-((2-((tert-butyldimethylsilyl)oxy)ethyl)sulfonyl)-2-(3-((S)-2,3-dihydroxypropyl)phenyl)-2,6,6-trimethylheptanoate (Intermediate 166B-1, 32.3 g, 50.9 mmol) in dichloromethane (500 mL) was added triethylamine (42 mL, 305.4 mmol), 4-dimethylaminopyridine (1.25 g, 10.1 mmol) and acetic anhydride (14.5 mL, 151 mmol). The reaction was stirred at room temperature for 2 hours, quenched with water (500 mL), and extracted with ethyl acetate (3×300 mL). The combined organic layers were dried over sodium sulfate, filtered, and concentrated. The residue was purified by automated flash chromatography (120.0 g silica gel column, eluting with 0-30% ethyl acetate in petroleum ether) to give the title compound (33.7 g, 46.9 mmol, 93%) as an oil. LC-MS: MS (ESI): 741 m/z [M+Na]$^+$, retention time: 2.26 minutes, purity: >99% (214 nm) (LC-MS Method 004).

The following intermediate was prepared based on the procedures described for Intermediate 167.

| Inter. No. | Structure | Name | MS m/z [M + H]$^+$ |
|---|---|---|---|
| 166B-1* | 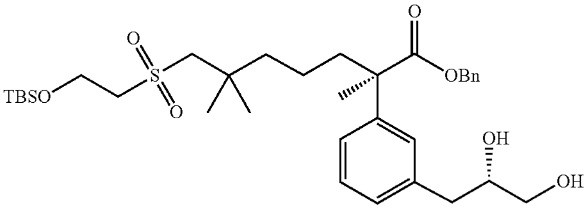 [SMILES: CC(C)(CCC[C@@](C)(C(=O)OCc1ccccc1)c1cccc(C[C@H](O)CO)c1)CS(=O)(=O)CCO[Si](C)(C)C(C)(C)C] | benzyl (R)-7-((2-((tert-butyldimethylsilyl)oxy) ethyl)sulfonyl)-2-(3-((S)-2,3-dihydroxypropyl)phenyl)-2,6,6-trimethylheptanoate (~7:3 S:R at the diol position) | 657 [M + Na]$^+$ RT: 2.09 min. (LC-MS method 4) |

*Note:
(DHQ)2PHAL was used.

| Inter. No. | Structure | Name | MS m/z [M + H]$^+$ |
|---|---|---|---|
| 167-1 | 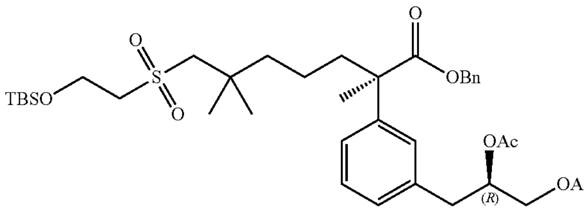 | (R)-3-(3-((R)-1-(benzyloxy)-7-((2-((tert-butyldimethylsilyl)oxy)ethyl)sulfonyl)-2,6,6-trimethyl-1-oxoheptan-2-yl)phenyl)propane-1,2-diyl diacetate (~7:3 S:R at the diol position) | 741 [M + Na]$^+$ RT: 2.26 min. (LC-MS method 4) |
| 167-2 | 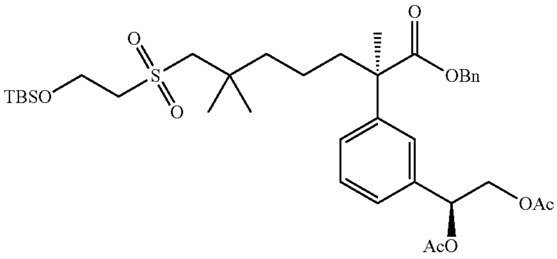 | (S)-1-(3-((R)-1-(benzyloxy)-7-((2-((tert-butyldimethylsilyl)oxy)ethyl)sulfonyl)-2,6,6-trimethyl-1-oxoheptan-2-yl)phenyl)ethane-1,2-diyl diacetate | 727 [M + Na]$^+$ RT: 2.26 min. (LC-MS method 003) |

Intermediate 168. 2-(3-(3-((Tert-butyldimethylsilyl)oxy)propyl)phenyl)acetonitrile

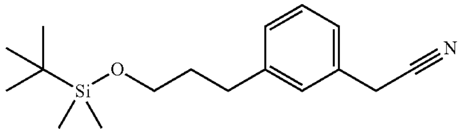 [SMILES: CC(C)(C)[Si](C)(C)OCCCc1cccc(CC#N)c1]

To a stirred solution of (3-(3-((tert-butyldimethylsilyl)oxy)propyl)phenyl)boronic acid (Intermediate 168B, 5 g, 16.99 mmol) in toluene (36 mL) and water (1.8 mL) were slowly added 2-aminoacetonitrile hydrochloride (3.14 g, 33.98 mmol) and sodium nitrite (2.93 g, 42.48 mmol). The mixture was heated to 75° C. and stirred for 8 hours, cooled to room temperature, poured into 100 mL of water, and extracted with ethyl acetate (3×60 mL). The combined organic extracts were washed with brine, dried over sodium sulfate, filtered, and concentrated. The residue was purified by flash chromatography (100-200 mesh silica gel, gradient: 50-100% ethyl acetate in heptane) to afford 4.4 g (90%) of the title compound. LC-MS: MS (ESI): 290 m/z [M+H]$^+$, purity: >99% (220 nm). retention time: 3.09 minutes (LC-MS method 045). $^1$H NMR (400.23 MHz, DMSO-$d_6$) δ 7.27 (t, J=7.6 Hz, 1H), 7.13 (m, 3H), 3.96 (s, 2H), 3.56 (t, J=6.2 Hz, 2H), 2.63-2.58 (m, 2H), 1.75-1.70 (m, 2H), 0.85 (s, 9H), 0.03 (s, 6H) ppm.

Intermediate 168A. Tert-butyldimethyl(3-(3-(4,4,5,5-tetramethyl-1,3,2-dioxaborolan-2-yl)phenyl)propoxy)silane

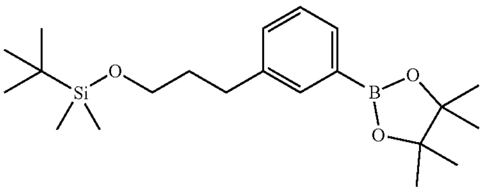 [SMILES: CC1(C)OB(c2cccc(CCCO[Si](C)(C)C(C)(C)C)c2)OC1(C)C]

To a stirred solution of (3-(3-bromophenyl) propoxy)(tert-butyl)dimethylsilane (30 g, 0.091 mol) in 1,4-dioxane (600 mL) were added 4,4,4',4',5,5,5',5'-octamethyl-2,2'-bi(1,3,2-dioxaborolane) (34.69 g, 0.136 mol), potassium acetate (13.4 g, 0.13 mol, 1.5 eq) and [1,1'-Bis (diphenylphosphino) ferrocene]palladium (II) dichloride (3.3 g, 0.004 mol, 0.05 eq) at room temperature under argon. The reaction mixture was heated to 80° C. and stirred for 16 hours, quenched with water (300 mL), and extracted with ethyl acetate (3×300 mL). The combined organic extracts were washed with brine, dried over sodium sulfate, filtered, and concentrated. The residue was purified by column chromatography (100-200 mesh silica gel) eluting with 5% ethyl acetate in heptane to afford 29.4 g (86%) of the title compound as colorless liquid. LC-MS: MS (ESI): 377 m/z [M+H]$^+$, purity: 97% (220 nm). retention time: 3.66 minutes (LC-MS method 045). $^1$H NMR (400 MHz, DMSO-$d_6$): δ 7.51 (s, 1H), 7.50-7.45 (m, 1H), 7.33-7.24 (m, 2H), 3.55 (t, J=6.2 Hz, 2H), 2.62 (t, J=7.6 Hz, 2H), 1.77-1.68 (m, 2H), 1.28 (s, 12H), 0.87 (s, 9H), 0.02 (s, 6H).

Intermediate 168B. (3-(3-((Tert-butyldimethylsilyl)oxy)propyl)phenyl)boronic Acid

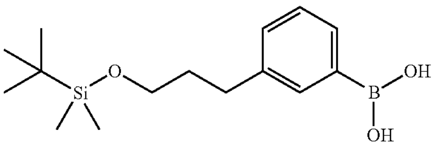 [SMILES: CC(C)(C)[Si](C)(C)OCCCc1cccc(B(O)O)c1]

To a stirred solution of ((3-(3-bromophenyl) propoxy)(tert-butyl)dimethylsilane (10 g, 30.36 mmol), hypodiboric acid (4.08 g, 45.54 mol) and potassium acetate (7.45 g, 75.91 mmol) in tetrahydrofuran (50 mL) and methanol (50 mL) was added 1,1'-Bis (diphenylphosphino)ferrocene-palladium(II)dichloride dichloromethane (1.24 g, 1.52 mmol). The reaction mixture was heated to 80° C. and stirred for 2 hours, quenched with brine/water (1:1) and extracted with ethyl acetate (2×100 mL). The combined organic extracts were washed with brine, dried over sodium sulfate, filtered, and concentrated. The residue was purified by flash chromatography (100-200 mesh silica gel, gradient: 50-100% ethyl acetate in heptane) to afford 6.2 g (69%) of the title compound. LC-MS: MS (ESI): 295 m/z $[M+H]^+$, purity: >99% (220 nm). retention time: 2.74 minutes (LC-MS method 045).

Intermediate 169. [5-(3-benzyloxyphenyl)-1-methyl-1,2,4-triazol-3-yl]-[3-[3-[tert-butyl(dimethyl)silyl]oxypropyl]phenyl]methanol

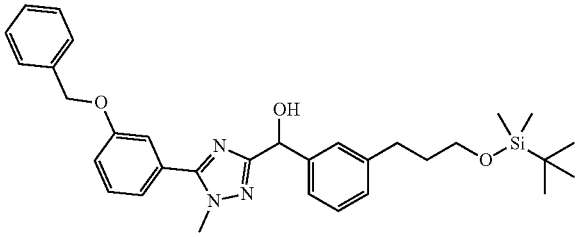 [SMILES: Cn1nc(C(O)c2cccc(CCCO[Si](C)(C)C(C)(C)C)c2)nc1-c1cccc(OCc2ccccc2)c1]

To a stirred and cooled (0° C.) solution of 5-(3-benzyloxyphenyl)-3-bromo-1-methyl-1,2,4-triazole (200 mg, 0.58 mmol) in 3 mL tetrahydrofuran was added isopropyl-magnesium chloride-lithium chloride (1.04 mmol; 0.8 ml 1.3 M solution in tetrahydrofuran). The mixture was stirred for 15 min at 0° C., and 1 hour at room temperature, then treated with 3-(3-((tert-butyldimethylsilyl)oxy)propyl)benzaldehyde (200 mg, 1.24 mmol) in 3 ml tetrahydrofuran. The mixture was stirred for 3 hours at room temperature, quenched with saturated aqueous ammonium chloride, and extracted with ethyl acetate (3×15 mL). The combined organic extracts were washed with brine, dried over sodium sulfate, filtered, and concentrated. The residue was purified by flash chromatography (silica gel column, ethyl acetate/n-heptane=1:1) to afford 316 mg (65%) of the title compound. LC-MS: MS (ESI): 544 m/z $[M+H]^+$; purity: 96% (220 nm); retention time: 3.26 minutes (LC-MS method 045). $^1H$ NMR (400.23 MHz, DMSO-$d_6$) δ: 7.43-7.31 (m, 10H), 7.122-7.16 (m, 2H), 7.05 (d, J=7.5 Hz, 1H), 5.88 (d, J=5.0 Hz, 1H), 5.68 (d, J=5.1 Hz, 1H), 5.17 (s, 2H), 3.86 (s, 3H), 3.58 (t, J=6.3 Hz, 2H), 2.63-2.57 (m, 2H), 1.76-1.70 (m, 2H), 0.85 (s, 9H), 0.03 (s, 6H) ppm.

The following intermediates were prepared utilizing similar procedures described for Intermediate 169.

| Inter. No. | Structure | Name | MS m/z $[M + H]^+$ |
|---|---|---|---|
| 169-1 | 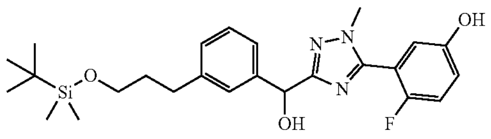 [SMILES: Cn1nc(C(O)c2cccc(CCCO[Si](C)(C)C(C)(C)C)c2)nc1-c1cc(O)ccc1F] | 3-(3-((3-(3-((tert-butyl-dimethylsilyl)oxy)propyl)phenyl)(hydroxy)methyl)-1-methyl-1H-1,2,4-triazol-5-yl)-4-fluorophenol | 472 $[M + H]^+$; RT: 2.74 (LC-MS Method 45). $^1H$ NMR (400.23 MHz, DMSO-$d_6$) δ 9.75 (s, 1H), 7.25-7.21 (m, 4H), 7.05 (d, J = 7.5 Hz, 1H), 6.93-6.90 (m, 2H), 5.91 (d, J = 5.0 Hz, 1H), 5.68 (d, J = 5.0 Hz, 1H), 3.71 (d, J = 1.8 Hz, 3H), 3.58 (t, J = 6.3 Hz, 2H), 2.59 (t, J = 7.6 Hz, 2H), 1.75-1.71 (m, 2H), 0.85 (s, 9H) 0.3 (s, 6H) ppm. |
| 169-2 | 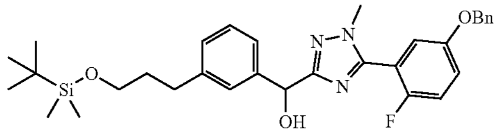 [SMILES: Cn1nc(C(O)c2cccc(CCCO[Si](C)(C)C(C)(C)C)c2)nc1-c1cc(OCc2ccccc2)ccc1F] | (5-(5-(benzyloxy)-2-fluorophenyl)-1-methyl-1H-1,2,4-triazol-3-yl)(3-(3-((tert-butyl-dimethylsilyl)oxy)propyl)phenyl)methanol | 562 $[M + H]^+$; RT: 3.25 (LC-MS Method 45) |

Intermediate 170. [5-[3-(5-bromo-2-methyl-1,2,4-triazol-3-yl)-4-fluoro-phenoxy]-6-fluoro-1-(2-trimethylsilylethoxymethyl)indol-4-yl]methyl Acetate

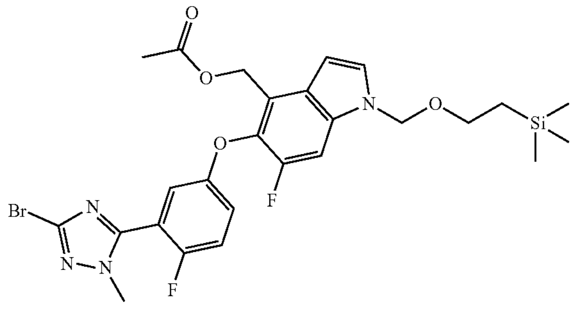 [SMILES: CC(=O)OCc1c(Oc2ccc(F)c(-c3nc(Br)nn3C)c2)c(F)cc2c1ccn2COCC[Si](C)(C)C]

To a stirred cooled (0° C.) solution of (5-(3-(3-bromo-1-methyl-1H-1,2,4-triazol-5-yl)-4-fluorophenoxy)-6-fluoro-1-((2-(trimethylsilyl)ethoxy)methyl)-1H-indol-4-yl)methanol (10.3 g, 18.21 mmol) and N,N-diisopropylethylamine (4.9 g, 36.7 mmol) in dichloromethane (100 mL) was added acetyl chloride (2.2 g, 27.75 mmol) dropwise. After the addition, the mixture was stirred for 30 minutes at room temperature, diluted with ethyl acetate (100 mL), then subsequently washed with 0.1M hydrochloric acid, aqueous sodium bicarbonate and brine. The separated organic layer was filtrated through silica gel, washed with additional ethyl acetate (50 mL). The filtrate was concentrated to afford 10.75 g (97%) of the title compound. LC-MS: MS (ESI): 607, 609 m/z $[M+H]^+$; purity: 96% (220 nm); retention time: 3.01 minutes (LC-MS method 045). $^1H$ NMR (400.23 MHz, DMSO-$d^6$) δ 7.81 (d, J=11.2 Hz, 1H), 7.72 (d, J=3.6 Hz, 1H), 7.55 (t, J=9.3 Hz, 1H), 7.30 (dt, J=9.0, 3.7 Hz, 1H), 7.13 (dd, J=5.5, 3.2 Hz, 1H), 6.79 (d, J=3.2 Hz, 1H), 5.67 (s, 2H), 5.45-5.41 (m, 2H), 3.86 (d, J=1.6 Hz, 3H), 3.58 (t, J=8.0 Hz, 2H), 1.95 (s, 3H), 0.92 (t, J=8.0 Hz, 2H), 0.05 (m, 9H) ppm.

Intermediate 171. Tert-Butyl 2-(6-chloropyrazin-2-yl)propanoate

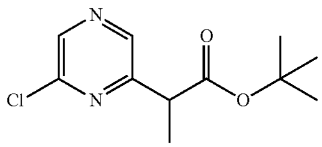 [SMILES: CC(C(=O)OC(C)(C)C)c1cncc(Cl)n1]

To a stirred and cooled (−10° C.) solution of lithium bis(trimethylsilyl)amide (1M in tetrahydrofuran, 201 mL, 201 mmol) in tetrahydrofuran (60 mL) was added tert-butyl propionate (10 mL, 67.1 mmol) in tetrahydrofuran (20 mL) under a nitrogen atmosphere. The reaction was stirred at −10° C. for 40 minutes. To the reaction mixture was added dropwise 2,6-dichloropyrazine (10.00 g, 67.1 mmol) in tetrahydrofuran (20 mL). The reaction was stirred at room temperature for 16 hours, then quenched with saturated ammonium chloride aqueous solution (100 mL) and extracted with ethyl acetate (3×100 mL). The combined organic extracts were washed with brine (3×100 mL), dried over anhydrous sodium sulfate, filtered, and concentrated. The residue was purified by automated flash chromatography (120 g silica gel column, eluting with 0-10% ethyl acetate in petroleum ether) to give the title compound (9.50 g, 58%) as a yellow oil. LC-MS: MS (ESI): 243 m/z $[M+H]^+$, purity: 97% (214 nm). retention time: 1.89 minutes (LC-MS method 003).

Intermediate 172. 4-((4-Bromo-6,7-difluoro-1H-indol-5-yl)methyl)pyridine-2-carbothioamide

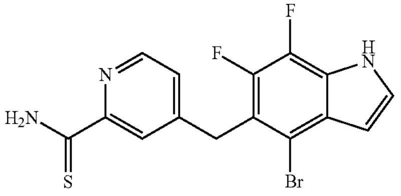

To a stirred solution of 4-((4-bromo-6,7-difluoro-1-(triisopropylsilyl)-1H-indol-5-yl)methyl)picolinonitrile (Intermediate 172D, 0.55 g, 1.09 mmol) in dimethylformamide (6 mL) and water (0.6 mL) were added sodium hydrosulfide (0.37 g, 6.54 mmol) and magnesium chloride (0.31 g, 3.27 mmol) at room temperature. The reaction was stirred for 2 hours, diluted with water (20 mL) and extracted with ethyl acetate (3×40 mL). The combined organic layers were washed with brine (30 mL), dried over sodium sulfate, filtered, and concentrated. The residue was purified by automated flash chromatography (40 g silica gel column, eluting with 0-45% ethyl acetate in petroleum ether) to give the title compound (0.35 g, 84%) as a light yellow solid. LC-MS: MS (ESI): 382, 384 m/z $[M+H]^+$, purity: >99% (254 nm). retention time: 1.95 minutes (LC-MS method 43).

The following intermediate was prepared utilizing similar procedures described for Intermediate 172.

| Inter. No. | Structure | Name | MS m/z $[M + H]^+$ |
|---|---|---|---|
| 172-1 | 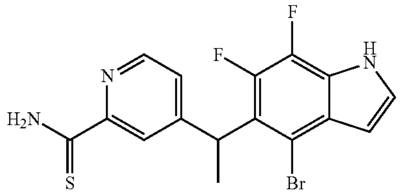 [SMILES: CC(c1ccnc(C(N)=S)c1)c1c(F)c(F)c2[nH]ccc2c1Br] | 4-(1-(4-bromo-6,7-difluoro-1H-indol-5-yl)ethyl)pyridine-2-carbothioamide | 396, 398 $[M + H]^+$; RT: 1.70 (LC-MS Method 40). |

Intermediate 172A. 4-Bromo-6,7-difluoro-1H-indole

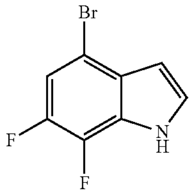 [SMILES: Fc1cc(Br)c2cc[nH]c2c1F]

To a stirred and cooled (−50° C.) solution of 5-bromo-1,2-difluoro-3-nitrobenzene (20.00 g, 84.0 mmol) in tetrahydrofuran (200 mL) was added dropwise a solution of vinyl magnesium bromide (1M in tetrahydrofuran, 210 mL, 210 mmol) ( ). The reaction mixture was stirred at −50° C. for 1 hour, then quenched with saturated ammonium chloride (300 mL) and extracted with ethyl acetate (3×200 mL). The combined organic extracts were washed with brine (80 mL), dried over sodium sulfate, filtered, and concentrated. The residue was purified by automated flash chromatography (120 g silica gel column, eluting with 0-3% ethyl acetate in petroleum ether) to give the title compound (3.20 g, 16%) as an oil. $^1$H NMR (400 MHz, $CDCl_3$) δ 8.52 (bs, 1H), 7.28-7.26 (m, 1H), 7.19-7.16 (m, 1H), 6.59-6.56 (m, 1H) ppm.

Intermediate 172B. 4-Bromo-6,7-difluoro-1-(triisopropylsilyl)-1H-indole

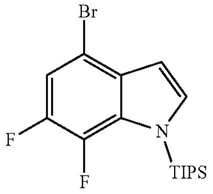

To a stirred and cooled (0° C.) solution of 4-bromo-6,7-difluoro-1H-indole (Intermediate 172A, 5.00 g, 21.5 mmol) in tetrahydrofuran (60 mL) was added sodium hydride (0.90 g, 22.6 mmol). The mixture was stirred for 30 minutes at this temperature, then treated with chlorotriisopropylsilane (4.57 g, 23.7 mmol). The reaction solution was stirred at room temperature for 1 hour, quenched with water (50 mL), and extracted with ethyl acetate (3×40 mL). The combined organic extracts were washed with brine (30 mL), dried over sodium sulfate, filtered, and concentrated. The residue was purified by automated flash chromatography (80 g silica gel column, eluting with 0-1% ethyl acetate in petroleum ether) to give the title compound (5.85 g, 70%) as a light-yellow solid. $^1$H NMR (400 MHz, $CDCl_3$) δ 7.35 (d, J=2.8 Hz, 1H), 7.19 (dd, J=10.0, 6.0 Hz, 1H), 6.63 (t, J=2.8 Hz, 1H), 1.74-1.59 (m, 3H), 1.14 (d, J=7.6 Hz, 18H) ppm.

Intermediate 172C. 4-((4-Bromo-6,7-difluoro-1-(triisopropylsilyl)-1H-indol-5-yl)(hydroxy)methyl)picolinonitrile

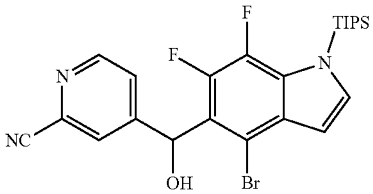

To a stirred and cooled (−78° C.) solution of 4-bromo-6,7-difluoro-1-(triisopropylsilyl)-1H-indole (Intermediate 172B, 1.80 g, 4.63 mmol) in tetrahydrofuran (30 mL) was added lithium diisopropylamide (2M in tetrahydrofuran, 2.8 mL, 5.56 mmol). The mixture was stirred at −78° C. for 1 hour, then treated with 4-formylpyridine-2-carbonitrile (0.67 g, 5.10 mmol), and stirred at −78° C. for another 2 hours. The reaction solution was quenched with saturated aqueous ammonium chloride (20 mL) and extracted with ethyl acetate (3×40 mL). The combined organic extracts were washed with brine (20 mL), dried over sodium sulfate, filtered, and concentrated. The residue was purified by flash chromatography (40 g silica gel column, eluting with 0-40% ethyl acetate in petroleum ether) to give the title compound (1.80 g, 73%) as a solid. LC-MS: MS (ESI): 520, 522 m/z $[M+H]^+$, purity: 98% (214 nm). retention time: 2.01 minutes (LC-MS method 40).

Intermediate 172D. 4-((4-Bromo-6,7-difluoro-1-(triisopropylsilyl)-1H-indol-5-yl)methyl)picolinonitrile

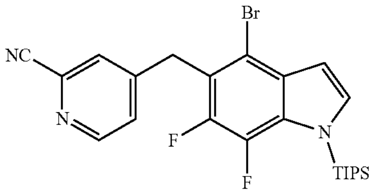

To a stirred solution of 4-((4-bromo-6,7-difluoro-1-(triisopropylsilyl)-1H-indol-5-yl)(hydroxy)methyl)picolinonitrile (Intermediate 172C, 1.80 g, 3.46 mmol) in tetrahydrofuran (30 mL) was added phosphorus tribromide (2.0 mL, 20.8 mmol) under argon. The mixture was stirred at 60° C. for 40 hours, quenched with water (45 mL) and basified with aqueous sodium carbonate until pH~11, followed by extraction with ethyl acetate (2×50 mL). The combined organic extracts were washed with brine (20 mL), dried over sodium sulfate, filtered, and concentrated. The residue was purified by automated flash chromatography (40 g silica gel column, eluting with 0-14% ethyl acetate in petroleum ether) to give the title compound (0.94 g, 45%, LC-MS: MS (ESI): 504 m/z $[M+H]^+$, purity: 84% (214 nm). retention time: 2.33 minutes (LC-MS method 40)) as an oil and 4-((4-bromo-6,7-difluoro-1H-indol-5-yl)methyl)picolinonitrile (270 mg, 17%, LC-MS: MS (ESI): 504, 506 m/z $[M+H]^+$, purity: 76% (214 nm). retention time: 1.61 minutes (LC-MS method 40)) as a white solid.

Intermediate 173. 4-(1-(4-Bromo-6,7-difluoro-1-(triisopropylsilyl)-1H-indol-5-yl)ethyl)picolinonitrile

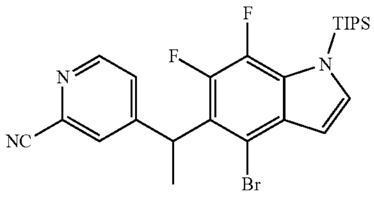

To a stirred solution of 4-((4-bromo-6,7-difluoro-1-(triisopropylsilyl)-1H-indol-5-yl)methyl)picolinonitrile (Intermediate 172D, 2.60 g, 5.15 mmol) in dry tetrahydrofuran (15 mL) was added lithium diisopropylamide (3.6 mL, 7.22 mmol) dropwise at −78° C. The mixture was stirred at 0° C. for 0.5 hours, cooled to −78° C., and treated with methyl iodide (0.45 mL, 7.22 mmol). The reaction was stirred at room temperature for 3 hours, then quenched with water, acidified with 1 M hydrochloric acid to pH~5, and extracted with ethyl acetate (2×40 mL). The combined organic extracts were washed with brine (50 mL), dried over sodium sulfate, filtered, and concentrated to afford the title compound (2.50 g, 96%) as a brown oil. LC-MS: MS (ESI): 518, 520 m/z $[M+H]^+$, purity: 86% (214 nm). retention time: 2.75 minutes (LC-MS method 40).

Intermediate 174. 5-((6,7-difluoro-1H-indol-5-yl)oxy)-2-fluorobenzonitrile

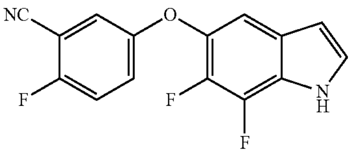 [SMILES: N#Cc1cc(Oc2cc3cc[nH]c3c(F)c2F)ccc1F]

To a stirred solution of 5-((4-bromo-6,7-difluoro-1H-indol-5-yl)oxy)-2-fluorobenzonitrile (Intermediate 1, 1.10 g, 3.00 mmol) in methanol (15 mL) was added palladium on carbon (10%, ~50% wet, 319 mg) and sodium bicarbonate (503 mg, 5.99 mmol). The mixture was stirred under hydrogen at room temperature and pressure for 1 hour, then filtered through a pad of Celite. The filtrate was concentrated to give the title compound (700 mg, 79%) as a white solid. LC-MS: MS (ESI): 289 m/z $[M+H]^+$, purity: 97% (214 nm). retention time: 1.84 minutes (LC-MS method 40).

Intermediate 175. 5-((4-Bromo-6-fluoro-1H-indazol-5-yl)oxy)-2-fluorobenzonitrile

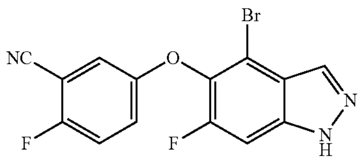 [SMILES: N#Cc1cc(Oc2c(F)cc3[nH]ncc3c2Br)ccc1F]

To a stirred and cooled (0° C.) solution of 5-(4-amino-2-bromo-6-fluoro-3-methylphenoxy)-2-fluorobenzonitrile (Intermediate 175A, 5.5 g, 16.2 mmol) in acetic acid (250 mL) was added sodium nitrite (1.2 g, 16.2 mmol). The reaction was stirred at room temperature for 3 hours, quenched with water (250 mL), and extracted with ethyl acetate (2×250 mL). The combined organic extracts were washed with brine, dried over sodium sulfate, filtered, and concentrated. The residue was purified by automated flash chromatography (40 g silica gel column, eluting with 0-80% ethyl acetate in petroleum ether) to give the title compound (5 g, 88%) as a solid. LC-MS: MS (ESI): 350, 352 m/z $[M+H]^+$, purity: 92% (254 nm). retention time: 1.55 minutes (LC-MS method 42).

Intermediate 175A. 5-(4-Amino-2-bromo-6-fluoro-3-methylphenoxy)-2-fluorobenzonitrile

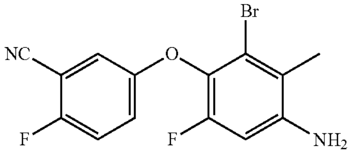

To a stirred solution of 5-(2-bromo-6-fluoro-3-methyl-4-nitrophenoxy)-2-fluorobenzonitrile (Intermediate 2B, 30.00 g, 81.3 mmol) in acetic acid (180 mL) was added iron powder (13.62 g, 244 mmol). The reaction mixture was stirred at room temperature for 3 hours. The mixture was filtered and concentrated. The residue was taken up in ethyl acetate (500 mL). The resulting solution was washed with water, brine, dried over sodium sulfate, filtered, and concentrated. The residue was triturated with 10% ethyl acetate in petroleum ether to give the title compound (29.00 g, 85.5 mmol). LC-MS: MS (ESI): 339, 341 m/z $[M+H]^+$, purity: >99% (214 nm). retention time: 1.95 minutes (LC-MS method 42).

Intermediate 176. Tert-butyl 2-(3-bromo-2-methoxyphenyl)acetate

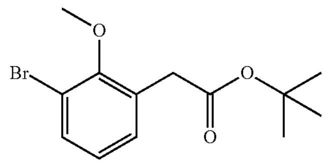 [SMILES: COc1c(Br)cccc1CC(=O)OC(C)(C)C]

To a stirred solution of 2-(3-bromo-2-methoxy-phenyl)acetic acid (23.00 g, 97.9 mmol) in tetrahydrofuran (200 mL) and tert-butanol (100 mL) were added di-tert-butyl dicarbonate (1.50 eq, 34 mL, 147 mmol) and 4-dimethylaminopyridine (3.59 g, 29.4 mmol). The mixture was stirred at room temperature for 5 hours, quenched with 200 ml of water, and extracted with ethyl acetate (2×200 ml). The combined organic phase was washed with brine, dried over sodium sulfate, filtered, and concentrated. The residue was purified by reverse-phase chromatography (eluting with 30:70 water: acetonitrile) to afford the title compound (9.01 g, 62%). LC-MS: MS (ESI): 301, 303 m/z $[M+H]^+$, purity: >99% (254 nm). retention time: 1.97 minutes (LC-MS method 40).

Intermediate 177. 4-(Benzyloxy)-2-fluoro-5-mercaptobenzonitrile

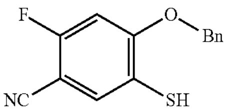 [SMILES: N#Cc1cc(S)c(OCc2ccccc2)cc1F]

To a stirred solution of 4-(benzyloxy)-2-fluoro-5-((4-methoxybenzyl)thio)benzonitrile (Intermediate 177C, 40 g, 105 mmol) in trifluoroacetic acid (80 ml) was added anisole (8 ml). The reaction was stirred at 50° C. for 4 hours under argon and concentrated to give the crude title compound (50.00 g, 70%), which was used in the next step without further purification. LC-MS: MS (ESI): 260 m/z $[M+H]^+$, purity: 38% (254 nm). retention time: 2.30 minutes (LC-MS method 40).

Intermediate 177A. 5-Bromo-2-fluoro-4-hydroxybenzonitrile

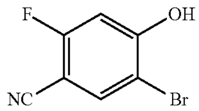 [SMILES: N#Cc1cc(Br)c(O)cc1F]

To a stirred solution of 2-fluoro-4-hydroxy-benzonitrile (90 g, 656 mmol) in acetonitrile (600 ml) was added N-bromo-succinimide (116.8 g, 656 mmol) and trifluoromethanesulfonic acid (60 ml, 676 mmol). The reaction was stirred at room temperature for 16 hours and diluted with ethyl acetate (1500 ml). The mixture was washed with water, brine, dried over magnesium sulfate, filtered, and concentrated. The residue was purified by automated flash chromatography (330 g silica gel column, eluting with 0-60% ethyl acetate in petroleum ether) to give the title compound (35.00 g, 25%) as a white solid. LC-MS: MS (ESI): 216, 218 m/z $[M+H]^+$, purity: 86% (254 nm). retention time: 1.33 minutes (LC-MS method 40).

Intermediate 177B. 2-Fluoro-4-hydroxy-5-((4-methoxybenzyl)thio)benzonitrile

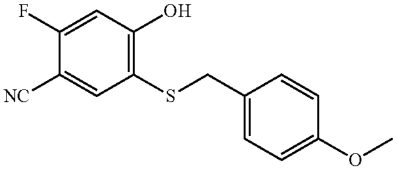 [SMILES: COc1ccc(CSc2cc(C#N)c(F)cc2O)cc1]

To a stirred solution of 5-bromo-2-fluoro-4-hydroxybenzonitrile (Intermediate 177A, 35.00 g, 162 mmol), Xantphos (9.38 g, 16.2 mmol), 4-methoxybenzyl mercaptan (2.00 eq, 45 mL, 324 mmol) and tris(dibenzylideneacetone)dipalladium(0) (7.42 g, 8.10 mmol) in 1,4-dioxane (600 ml) was added N,N-diisopropylethylamine (56 ml, 324 mmol). The reaction was stirred at 100° C. for 16 hours under argon. The resulting mixture was taken up in ethyl acetate (1000 ml), washed with water, brine, dried over magnesium sulfate, filtered, and concentrated. The residue was purified by automated flash chromatography (330 g silica gel column, eluting with 0-60% ethyl acetate in petroleum ether) to give the title compound (30.00 g, 64%). LC-MS: MS (ESI): 288 m/z [M−H]+, purity: 51% (214 nm). retention time: 1.84 minutes (LC-MS method 40).

Intermediate 177C. 4-(Benzyloxy)-2-fluoro-5-((4-methoxybenzyl)thio)benzonitrile

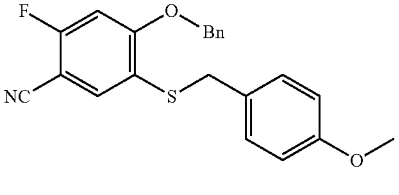 [SMILES: COc1ccc(CSc2cc(C#N)c(F)cc2OCc2ccccc2)cc1]

To a stirred solution of 2-fluoro-4-hydroxy-5-((4-methoxybenzyl)thio)benzonitrile (Intermediate 177B, 46.88 g, 162 mmol) and benzyl bromide (39 ml, 324 mmol) in acetone (600 ml) was added potassium carbonate (44.79 g, 324 mmol). The reaction was stirred at room temperature for 16 hours under argon. The resulting mixture was taken up in ethyl acetate (1000 ml), washed with water, brine, dried over magnesium sulfate, filtered, and concentrated. The residue was purified by automated flash chromatography (330 g silica gel column, eluting with 0-60% ethyl acetate in petroleum ether) to give the title compound (40.00 g, 65%). LC-MS: MS (ESI): 402 m/z $[M+Na]^+$, purity: >99% (214 nm). retention time: 2.18 minutes (LC-MS method 40).

Intermediate 178. 2-(2,2-Difluoro-4-((2-hydroxyethyl)thio)butyl)isoindoline-1,3-dione

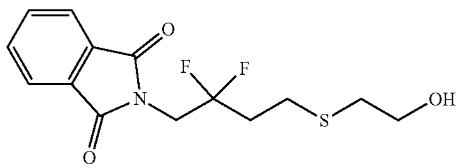 [SMILES: O=C1c2ccccc2C(=O)N1CC(F)(F)CCSCCO]

To a stirred solution of 2-(2,2-difluoro-4-iodobutyl)isoindoline-1,3-dione (Intermediate 178F, 7.40 g, 20.3 mmol) and potassium carbonate (3.04 g, 22.0 mmol) in dichloromethane (100 mL) was added 2-mercaptoethanol (2.6 mL, 36.6 mmol). The reaction was stirred at room temperature for 8 hours under a nitrogen atmosphere. The mixture was diluted with dichloromethane (200 mL), washed with water, brine, dried over magnesium sulfate, filtered, and concentrated. The residue was purified by automated flash chromatography (80 g silica gel column, eluting with 20-30% ethyl acetate in petroleum ether) to afford the title compound (5.70 g, 84%). LC-MS: MS (ESI): 338 m/z $[M+Na]^+$, purity: 94% (214 nm), retention time: 1.70 minutes (LC-MS method 51).

Intermediate 178A. 2-(Oxiran-2-yl)ethyl Acetate

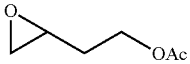

To a stirred solution of but-3-en-1-yl acetate (60.00 g, 526 mmol) in dry dichloromethane (1000 mL) was added 3-chloroperoxybenzoic acid (181.3 g, 1052 mmol). The reaction was stirred at room temperature for 8 hours and filtered through a pad of Celite. The filter cake was washed with saturated sodium carbonate (500 mL×2), dried over sodium sulfate, filtered, and concentrated. The residue was purified by flash chromatography (eluting with 10:1 petroleum ether: ethyl acetate) to give the title compound (45.00 g, 46%). LC-MS: MS (ESI): 131 m/z $[M+H]^+$, retention time: 1.29 minutes (LC-MS method 004).

Intermediate 178B. 4-(1,3-Dioxoisoindolin-2-yl)-3-hydroxybutyl Acetate

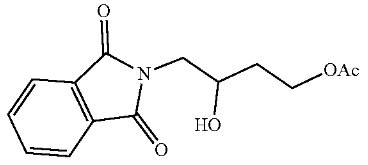 [SMILES: CC(=O)OCCC(O)CN1C(=O)c2ccccc2C1=O]

To a stirred solution of 2-(oxiran-2-yl)ethyl acetate (Intermediate 178A, 40.00 g, 307 mmol) in dry 2-propanol (1500 mL) was added phthalimide (49.74 g, 460.5 mmol) and pyridine (5.0 mL, 61.5 mmol). The mixture was then heated at 80° C. for 8 hours and concentrated. The residue was dissolved in ethyl acetate (600 mL), filtered, and concentrated to give the title compound (68.50 g, 78%), which was used in the next step without further purification. LC-MS: MS (ESI): 278 m/z $[M+H]^+$, purity: 69% (254 nm). retention time: 1.52 minutes (LC-MS method 003).

Intermediate 178C. 4-(1,3-Dioxoisoindolin-2-yl)-3-oxobutyl Acetate

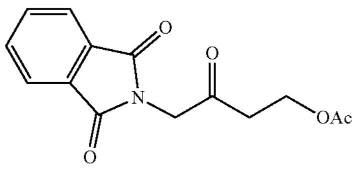 [SMILES: CC(=O)OCCC(=O)CN1C(=O)c2ccccc2C1=O]

To a stirred solution of 4-(1,3-dioxoisoindolin-2-yl)-3-hydroxybutyl acetate (Intermediate 178B, 68.50 g, 247 mmol) in dry dichloromethane (1000 mL) was added 1,1,1-tris(acetyloxy)-1,1-dihydro-1,2-benzodioxol-3-(1h)-one (157.18 g, 371 mmol). The reaction was stirred at room temperature for 4 hours and the solids were filtered off. The filtrate was washed with saturated sodium sulfite, brine, dried over sodium sulfate, filtered, and concentrated. The residue was purified by automated flash chromatography (120 g silica gel column, eluting with 0-50% ethyl acetate in petroleum ether) to give the title compound (45.00 g, 63%). LC-MS: MS (ESI): 276 m/z $[M+H]^+$, purity: 95% (254 nm). retention time: 1.59 minutes (LC-MS method 51).

Intermediate 178D. 4-(1,3-Dioxoisoindolin-2-yl)-3,3-difluorobutyl Acetate

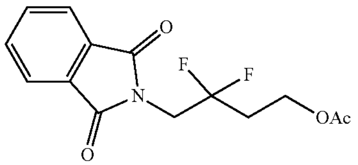 [SMILES: CC(=O)OCCC(F)(F)CN1C(=O)c2ccccc2C1=O]

To a stirred solution of 4-(1,3-dioxoisoindolin-2-yl)-3-oxobutyl acetate (Intermediate 178C, 65.00 g, 236 mmol) in dry dichloroethane (1000 mL) was added [bis(2-methoxyethyl)amino]sulfur trifluoride (305 mL, 1653 mmol). The reaction was stirred at 50° C. for 16 hours, quenched with water (1000 mL), and extracted with ethyl acetate (2×1000 mL). The combined organic extracts were washed with brine, dried over sodium sulfate, filtered, and concentrated. The residue was purified by automated flash chromatography (120 g silica gel column, eluting with 0-60% ethyl acetate in petroleum ether) to give the title compound (51.00 g, 171 mmol). LC-MS: MS (ESI): 298 m/z $[M+H]^+$, purity: 95% (214 nm), retention time: 1.79 minutes (LC-MS method 51).

Intermediate 178E. 2-(2,2-Difluoro-4-hydroxybutyl) isoindoline-1,3-dione

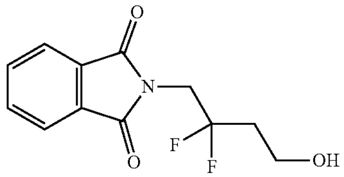 [SMILES: O=C1c2ccccc2C(=O)N1CC(F)(F)CCO]

To a stirred solution of 4-(1,3-dioxoisoindolin-2-yl)-3,3-difluorobutyl acetate (Intermediate 178D, 41.00 g, 138 mmol) in dichloromethane (40 mL) and methanol (200 mL) was added acetyl chloride (4.9 mL, 68.9 mmol). The reaction was stirred at room temperature for 16 hours under a nitrogen atmosphere. The resulting mixture was diluted with ethyl acetate (200 mL), washed with water, brine, dried over magnesium sulfate, filtered, and concentrated. The residue was purified by automated flash chromatography (120 g silica gel column, eluting with 20-40% ethyl acetate in petroleum ether) to give the title compound (21 g, 42% over 2 steps) as a solid. LC-MS: MS (ESI): 256 m/z $[M+H]^+$, purity: 70% (254 nm), retention time: 1.60 minutes (LC-MS method 51).

Intermediate 178F. 2-(2,2-Difluoro-4-iodobutyl)isoindoline-1,3-dione

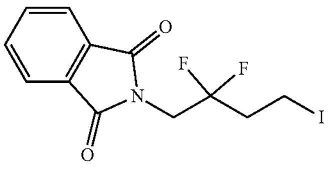 [SMILES: O=C1c2ccccc2C(=O)N1CC(F)(F)CCI]

To a stirred solution of 2-(2,2-difluoro-4-hydroxybutyl) isoindoline-1,3-dione (Intermediate 178E, 8.00 g, 31.3 mmol) in tetrahydrofuran (100 mL) were added imidazole (1.60 g, 23.5 mmol) and triphenylphosphine (6.17 g, 23.5 mmol). The mixture was stirred at 0° C. for 20 minutes, then treated with iodine (4.50 g, 17.7 mmol), and stirred at room temperature for 2 hours. The mixture was diluted with ethyl acetate (200 mL), washed with water, brine, dried over magnesium sulfate, filtered, and concentrated. The residue was purified by automated flash chromatography (120 g silica gel column, eluting with 0-10% ethyl acetate in petroleum ether) to give the title compound (7.40 g, 60%). LC-MS: MS (ESI): 366 m/z $[M+H]^+$, purity: 92% (254 nm), retention time: 1.96 minutes (LC-MS method 51).

Intermediate 179. 5-((4-Bromo-6,7-difluoro-1-(tetrahydro-2H-pyran-2-yl)-1H-indazol-5-yl)oxy)-2-fluorobenzonitrile

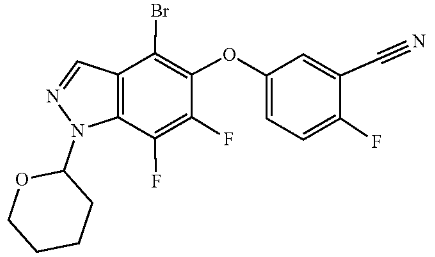 [SMILES: N#Cc1cc(Oc2c(F)c(F)c3c(cnn3C3CCCCO3)c2Br)ccc1F]

To a stirred solution of (3-cyano-4-fluorophenyl)(2,4,6-trimethoxyphenyl)-13-iodaneyl 4-methylbenzenesulfonate (Intermediate 179C, 1.10 g, 1.88 mmol) in acetone (25 mL) were added 4-bromo-6,7-difluoro-1-(tetrahydro-2H-pyran-2-yl)-1H-indazol-5-ol (Intermediate 179B, 0.69 g, 2.07 mmol) and potassium carbonate (0.78 g, 5.64 mmol). The mixture was stirred at 50° C. overnight and filtered. The filtrate was washed with 2N aqueous sodium hydroxide (2×20 mL). The combined organic extracts were washed with brine, dried over sodium sulfate, filtered, and concentrated. The residue was purified by automated flash chromatography (40 g silica gel column, eluting with 0-25% ethyl acetate in petroleum ether) to give the title compound (0.38 g, 45%) as a solid. LC-MS: MS (ESI): 474, 476 m/z $[M+Na]^+$, purity: 92% (214 nm), retention time: 2.67 minutes (LC-MS method 32).

Intermediate 179A. (4-Bromo-6,7-difluoro-1-(tetrahydro-2H-pyran-2-yl)-1H-indazol-5-yl)boronic Acid

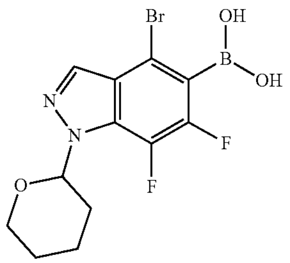 [SMILES: OB(O)c1c(F)c(F)c2c(cnn2C2CCCCO2)c1Br]

To a stirred solution of 4-bromo-6,7-difluoro-1-(tetrahydro-2H-pyran-2-yl)-1H-indazole (5.00 g, 15.8 mmol) in tetrahydrofuran (75 mL) at −78° C. was added lithium diisopropylamide (9.5 mL, 18.9 mmol). The mixture was stirred at −78° C. for 0.5 hours and then treated with trimethyl borate (5.3 mL, 47.3 mmol). The mixture was stirred at −78° C. for 15 minutes, quenched with saturated ammonium chloride (50 mL), and extracted with ethyl acetate (3×100 mL). The combined organic extracts were washed with brine, dried over sodium sulfate, filtered, and concentrated. The residue was purified by automated flash chromatography (30 g silica gel column, eluting with 0-15% ethyl acetate in petroleum ether) to give the title compound (3.82 g, 67%) as solid. $^1H$ NMR (500 MHz, DMSO-$d_6$) δ 8.83 (s, 2H), 8.14 (d, J=1.5 Hz, 1H), 5.92-5.69 (m, 1H), 3.93-3.85 (m, 1H), 3.73-3.61 (m, 1H), 2.46-2.36 (m, 1H), 2.14-2.04 (m, 2H), 2.12-1.73 (m, 1H), 1.62-1.51 (m, 2H) ppm.

Intermediate 179B. 4-Bromo-6,7-difluoro-1-(tetrahydro-2H-pyran-2-yl)-1H-indazol-5-ol

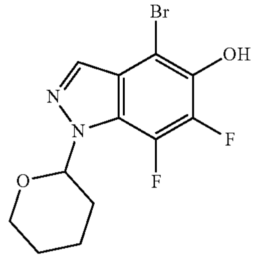 [SMILES: Oc1c(F)c(F)c2c(cnn2C2CCCCO2)c1Br]

To a stirred solution of (4-bromo-6,7-difluoro-1-(tetrahydro-2H-pyran-2-yl)-1H-indazol-5-yl)boronic acid (Intermediate 179A, 200 mg, 0.554 mmol) in ethanol (6 mL) was added hydrogen peroxide (0.15 mL, 4.99 mmol). The mixture was stirred overnight at room temperature and extracted with ethyl acetate (3×20 m). The combined organic extracts were washed with brine, dried over sodium sulfate, filtered, and concentrated. The residue was purified by automated flash chromatography (20 g silica gel column, eluting with 0-25% ethyl acetate in petroleum ether) to give the title compound (123 mg, 67%) as a solid. LC-MS: MS (ESI): 331, 333 m/z [M−H]+, purity: >99% (214 nm), retention time: 1.58 minutes (LC-MS method 51).

Intermediate 179C. (3-Cyano-4-fluorophenyl)(2,4,6-trimethoxyphenyl)-l3-iodaneyl 4-methylbenzenesulfonate

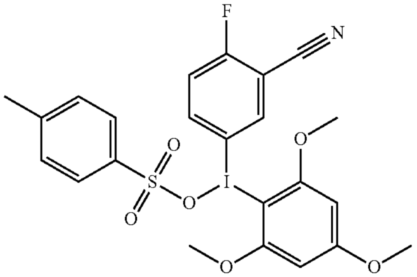

To a stirred solution of 2-fluoro-5-iodobenzonitrile (2.00 g, 8.10 mmol) in acetonitrile (20 mL) were added p-toluenesulfonic acid monohydrate (1.56 g, 8.18 mmol) and 3-chloroperoxybenzoic acid (1.41 g, 8.18 mmol). The reaction was stirred at 55° C. for 30 minutes, then treated with 1,3,5-trimethoxybenzene (1.42 g, 8.42 mmol). The mixture was stirred at 55° C. for another 30 minutes and concentrated. The residue was triturated with methyl tert-butyl ether. The precipitate was collected by filtration, triturated with methyl tert-butyl ether and dried to afford the title compound (1.87 g, 39%) as a solid. LC-MS: MS (ESI): 416 m/z [M−OTs]$^+$, purity: 92% (214 nm), retention time: 1.46 minutes (LC-MS method 32).

Intermediate 180. 5-((4-Bromo-6,7-difluoro-1-(tetrahydro-2H-pyran-2-yl)-1H-benzo[d]imidazol-5-yl)oxy)-2-fluorobenzonitrile

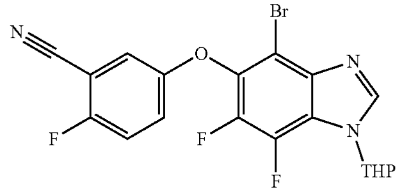

To a stirred solution of 5-((4-bromo-6,7-difluoro-1H-benzo[d]imidazol-5-yl)oxy)-2-fluorobenzonitrile (Intermediate 180D, 1.88 g, 5.11 mmol) in acetonitrile (300 mL) were added 3,4-dihydro-2H-pyran (2.3 mL, 25.5 mmol) and pyridinium p-toluenesulfonate (128 mg, 0.511 mmol). The mixture was stirred at room temperature for 16 hours, then heated at 40° C. for 2 hours, and concentrated. The residue was purified by automated flash chromatography (40 g silica gel column, eluting with 0-50% ethyl acetate in petroleum ether) to give the title compound (2.20 g, 95%) as a yellow solid. LC-MS: MS (ESI): 474, 476 m/z [M+Na]$^+$, purity: 93% (214 nm), retention time: 2.05 minutes (LC-MS method 43).

Intermediate 180A. 2-Bromo-3,4,5-trifluoro-6-nitroaniline

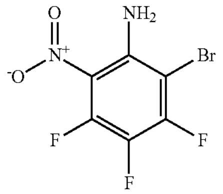

To a stirred solution of 3,4,5-trifluoro-2-nitroaniline (2.00 g, 10.4 mmol) in acetic acid (15 mL) was added dropwise at room temperature bromine (0.64 mL, 12.5 mmol). The reaction mixture was stirred for 2 hours, poured into ice water (80 ml), and stood overnight. The formed yellow solid was collected by filtration, washed with water, and dried to afford 2-bromo-3,4,5-trifluoro-6-nitro-aniline (2.00 g, 71%) as a yellow solid. LC-MS: MS (ESI): 271, 273 m/z [M+H]$^+$, purity: 89% (254 nm), retention time: 1.93 minutes (LC-MS method 43).

Intermediate 180B. 5-(3-Amino-2-bromo-5,6-difluoro-4-nitrophenoxy)-2-fluorobenzonitrile

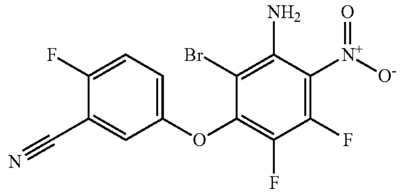 [SMILES: N#Cc1cc(Oc2c(F)c(F)c([N+](=O)[O-])c(N)c2Br)ccc1F]

To a solution of 2-bromo-3,4,5-trifluoro-6-nitroaniline (Intermediate 180A, 20.00 g, 73.8 mmol) in dimethylformamide (200 mL) were added at 0° C. 2-fluoro-5-hydroxybenzonitrile (9.1 g, 66.4 mmol) and potassium carbonate (115.3 g, 111 mmol). The mixture was stirred at 0° C. for 2 hours, diluted with water (400 mL), and extracted with ethyl acetate (3×200 mL). The combined organic extracts were washed with brine, dried over sodium sulfate, filtered, and concentrated. The residue was purified by automated flash chromatography (120 g silica gel column×2, and eluted with 0-80% dichloromethane in petroleum ether) to give the title compound (20.00 g, 70%) as a light-yellow solid. LC-MS: MS (ESI): 388, 390 m/z [M+H]$^+$, purity: 98% (214 nm), retention time: 1.94 minutes (LC-MS method 003).

Intermediate 180C. 5-(3,4-Diamino-2-bromo-5,6-difluorophenoxy)-2-fluorobenzonitrile

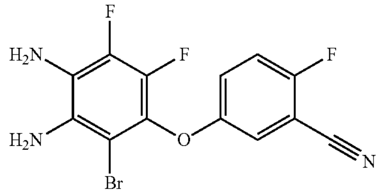 [SMILES: N#Cc1cc(Oc2c(F)c(F)c(N)c(N)c2Br)ccc1F]

To a stirred solution of 5-(3-amino-2-bromo-5,6-difluoro-4-nitrophenoxy)-2-fluorobenzonitrile (Intermediate 180B, 21.00 g, 54.1 mmol) in acetic acid (400 mL) was added iron powder (9.07 g, 162 mmol). The mixture was stirred at room temperature for 3 hours, diluted with water (800 mL) and ethyl acetate (400 mL) and filtered to remove the solids. The filtrate was extracted with ethyl acetate (5×300 mL). The combined organic extracts were washed with saturated aqueous sodium bicarbonate solution, dried over sodium sulfate, filtered, and concentrated to give the title compound (16.00 g, 83%) as a light-yellow solid. LC-MS: MS (ESI): 358, 360 m/z [M+H]$^+$, purity: 95% (254 nm), retention time: 1.92 minutes (LC-MS method 43).

Intermediate 180D. 5-((4-Bromo-6,7-difluoro-1H-benzo[d]imidazol-5-yl)oxy)-2-fluorobenzonitrile

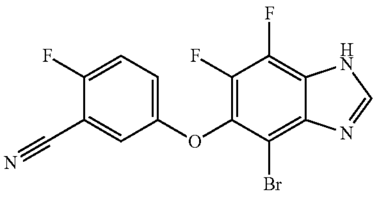 [SMILES: N#Cc1cc(Oc2c(F)c(F)c3[nH]cnc3c2Br)ccc1F]

To a stirred solution of 5-(3,4-diamino-2-bromo-5,6-difluorophenoxy)-2-fluorobenzonitrile (Intermediate 180C, 2.00 g, 5.58 mmol) in dimethylformamide (8 mL) were added trimethyl orthoformate (1.2 mL, 11.2 mmol) and a 4.0 M hydrogen chloride solution in 1,4-dioxane (1.0 mL). The mixture was stirred at room temperature for 4 hours, then poured into water (100 mL). The formed yellow solid was collected by filtration. The filter cake was washed with water (3×5.0 mL) and dried to give the title compound (2.00 g, 97%) as a light-yellow solid. LC-MS: MS (ESI): 368, 370 m/z $[M+H]^+$, purity: 94% (254 nm), retention time: 1.84 minutes (LC-MS method 43).

PREPARATION OF EXEMPLIFIED COMPOUNDS

Example 1. Enantiomers of 2-[3-[22,28-Difluoro-6,10,10-trimethyl-12,12-dioxo-3-(trideuteriomethyl)-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl]phenoxy]acetic Acid

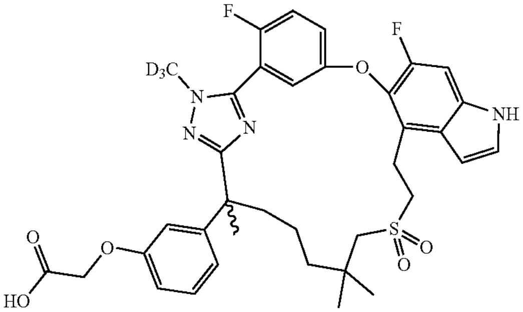 [SMILES: [2H]C([2H])([2H])n1nc2nc1-c1cc(ccc1F)Oc1c(F)cc3[nH]ccc3c1CCS(=O)(=O)CC(C)(C)CCCC2(C)c1cccc(OCC(=O)O)c1]

Ethyl 2-((6-(3-(2-ethoxy-2-oxoethoxy)phenyl)-6-(5-(2-fluoro-5-((6-fluoro-4-vinyl-1H-indol-5-yl)oxy)phenyl)-1-(methyl-d$_3$)-1H-1,2,4-triazol-3-yl)-2,2-dimethylheptyl)sulfonyl)acetate

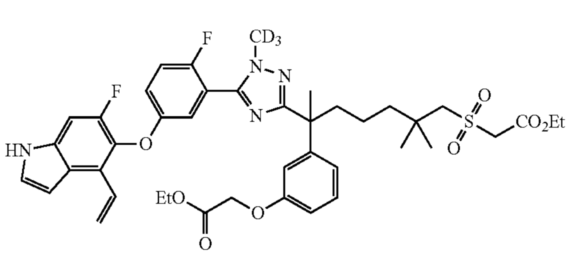 [SMILES: [2H]C([2H])([2H])n1nc(C(C)(CCCC(C)(C)CS(=O)(=O)CC(=O)OCC)c2cccc(OCC(=O)OCC)c2)nc1-c1cc(Oc2c(F)cc3[nH]ccc3c2C=C)ccc1F]

Step A: To a stirred solution of ethyl 2-((6-(3-(2-ethoxy-2-oxoethoxy)phenyl)-2,2,6-trimethyl-7-(2-(methyl-d$_3$)hydrazineyl)-7-oxoheptyl)sulfonyl)acetate (Intermediate 45, 2.50 g, 4.70 mmol) in pyridine (30 mL) was added methyl 2-fluoro-5-((6-fluoro-4-vinyl-1H-indol-5-yl)oxy)benzimidothioate hydroiodide (Intermediate 14, 2.66 g, 5.63 mmol). The reaction was heated overnight at 80° C. and then cooled to room temperature and partitioned between 1.0 N hydrochloric acid (100 mL) and ethyl acetate (100 mL). The organic layer was washed with brine (2×100 mL), dried over sodium sulfate and concentrated. The crude residue was purified by automated flash chromatography (80 g silica gel column, 0-50% ethyl acetate in petroleum ether) to afford the title compound as an off-white solid (1.51 g, 40%). MS (ESI): 810 m/z $[M+H]^+$.

Ethyl 2-((6-(5-(5-((4-(1,2-dihydroxyethyl)-6-fluoro-1H-indol-5-yl)oxy)-2-fluorophenyl)-1-(methyl-d$_3$)-1H-1,2,4-triazol-3-yl)-6-(3-(2-ethoxy-2-oxoethoxy)phenyl)-2,2-dimethylheptyl)sulfonyl)acetate

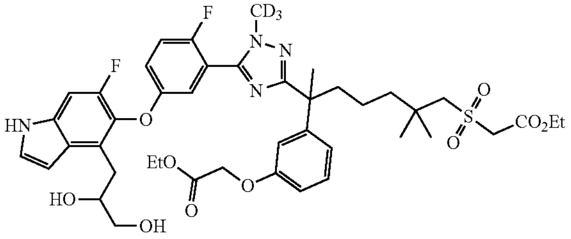 [SMILES: [2H]C([2H])([2H])n1nc(C(C)(CCCC(C)(C)CS(=O)(=O)CC(=O)OCC)c2cccc(OCC(=O)OCC)c2)nc1-c1cc(Oc2c(F)cc3[nH]ccc3c2CC(O)CO)ccc1F]

Step B: To a stirred solution of ethyl 2-((6-(3-(2-ethoxy-2-oxoethoxy)phenyl)-6-(5-(2-fluoro-5-((6-fluoro-4-vinyl-1H-indol-5-yl)oxy)phenyl)-1-(methyl-d$_3$)-1H-1,2,4-triazol-3-yl)-2,2-dimethylheptyl)sulfonyl)acetate (Step A product, 1.51 g, 1.86 mmol) in acetone (60 mL) was added a 10% aqueous solution of 4-methylmorpholine-N-oxide (0.617 mL, 2.98 mmol) and a 0.2% aqueous solution of osmium tetroxide (10.0 mL, 20.0 mg, 0.079 mmol). The reaction was allowed to proceed overnight at room temperature and then partitioned between ethyl acetate (100 mL) and brine (100 mL). The organic layer was washed a second time (brine, 1×100 mL), dried over sodium sulfate and concentrated. The crude residue was purified by automated flash chromatography (20 g silica gel column, 0-70% ethyl acetate in petroleum ether) to afford the title compound as a brown solid (0.970 g, 62%). MS (ESI): 844 m/z $[M+H]^+$.

Ethyl 2-((6-(3-(2-ethoxy-2-oxoethoxy)phenyl)-6-(5-(2-fluoro-5-((6-fluoro-4-formyl-1H-indol-5-yl)oxy)phenyl)-1-(methyl-d$_3$)-1H-1,2,4-triazol-3-yl)-2,2-dimethylheptyl)sulfonyl)acetate

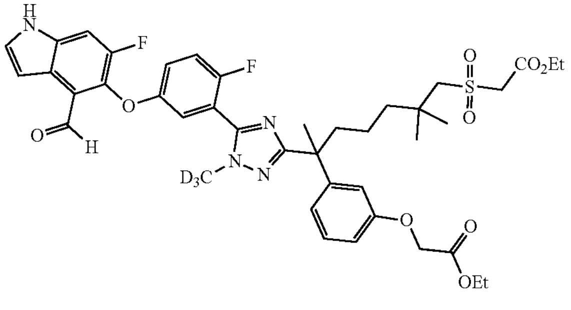 [SMILES: [2H]C([2H])([2H])n1nc(C(C)(CCCC(C)(C)CS(=O)(=O)CC(=O)OCC)c2cccc(OCC(=O)OCC)c2)nc1-c1cc(Oc2c(F)cc3[nH]ccc3c2C=O)ccc1F]

Step C: To a stirred solution of Ethyl 2-((6-(5-(5-((4-(1,2-dihydroxyethyl)-6-fluoro-1H-indol-5-yl)oxy)-2-fluoro-phenyl)-1-(methyl-$d_3$)-1H-1,2,4-triazol-3-yl)-6-(3-(2-ethoxy-2-oxoethoxy)phenyl)-2,2-dimethylheptyl)sulfonyl) acetate (Step B product, 0.970 g, 1.15 mmol) in 3:1 acetone/water (40 mL) was added sodium periodate (0.738 g, 3.45 mmol). The reaction was allowed to proceed overnight at room temperature and then partitioned between ethyl acetate (100 mL) and water (100 mL). The organic layer was washed a second time (water, 1×100 mL), dried over sodium sulfate and concentrated. The crude title compound, which was used without purification, was afforded as a yellow solid (0.850 g, 91%). MS (ESI): 812 m/z $[M+H]^+$.

Ethyl 6-[3-(2-ethoxy-2-oxoethoxy)phenyl]-22,28-difluoro-6-methyl-12,12-dioxo-3-(trideuteriomethyl)-24-oxa-12λ$^6$-thia-3,4,19,30-tetrazapentacyclo[23.3.1.1$^{2,5}$.0$^{15,23}$.0$^{16,20}$]triaconta-1(29),2(30),4,13,15,17,20,22,25,27-decaene-13-carboxylate

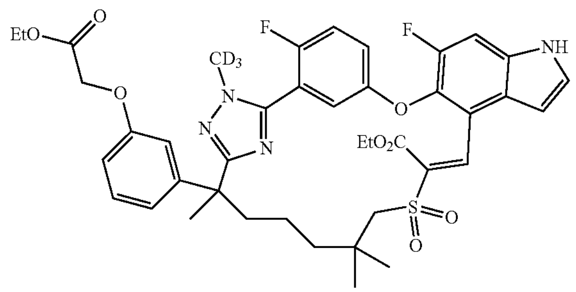 [SMILES: [2H]C([2H])([2H])n1nc2nc1-c1cc(ccc1F)Oc1c(F)cc3[nH]ccc3c1/C=C(\C(=O)OCC)S(=O)(=O)CC(C)(C)CCCC2(C)c1cccc(OCC(=O)OCC)c1]

Step D: To a stirred solution of crude step C product (0.850 g, 1.05 mmol) in toluene (400 mL) was added piperidine (517 μL, 0.446 g, 5.23 mmol) and acetic acid (60.1 μL, 63.0 mg, 1.05 mmol). The reaction was brought to 110° C. and maintained at this temperature for 24 hours. Following this heating period, the mixture was cooled to room temperature and concentrated. The obtained residue was dissolved in ethyl acetate (50 mL) and the solution was washed with water (2×50 mL), dried over sodium sulfate and concentrated. The crude material was purified by automated flash chromatography (20 g silica gel column, 0-60% ethyl acetate in petroleum ether) to afford the title compound as a yellow solid (0.430 g, 52%). MS (ESI): 794 m/z $[M+H]^+$.

Ethyl 6-[3-(2-ethoxy-2-oxo-ethoxy)phenyl]-22,28-difluoro-6,10,10-trimethyl-12,12-dioxo-3-(trideuteriomethyl)-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaene-13-carboxylate

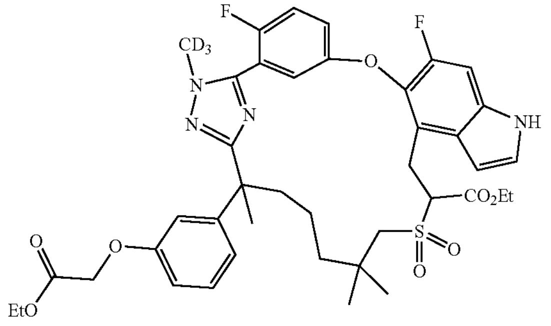 [SMILES: [2H]C([2H])([2H])n1nc2nc1-c1cc(ccc1F)Oc1c(F)cc3[nH]ccc3c1CC(C(=O)OCC)S(=O)(=O)CC(C)(C)CCCC2(C)c1cccc(OCC(=O)OCC)c1]

Step E: A stirred suspension of step D product (0.430 g, 0.542 mmol) and 10% palladium on carbon (0.200 g) in ethanol (30 mL) was cycled between vacuum and a nitrogen atmosphere three times. After a final evacuation, the reaction vessel was backfilled with hydrogen (via balloon). The reaction was allowed to proceed overnight before the hydrogen was evacuated and the vessel was opened to air. The catalyst was removed by suction filtration through a pad of Celite, which was subsequently rinsed with additional ethanol (total, 50 mL). The combined filtrate was concentrated to afford the crude title compound, which was used without purification, as a white solid (0.360 g, 83%). MS (ESI): 796 m/z $[M+H]^+$.

6-[3-(Carboxymethoxy)phenyl]-22,28-difluoro-6,10,10-trimethyl-12,12-dioxo-3-(trideuteriomethyl)-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaene-13-carboxylic Acid

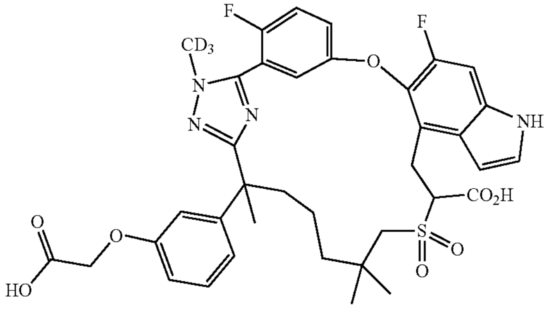 [SMILES: [2H]C([2H])([2H])n1nc2nc1-c1cc(ccc1F)Oc1c(F)cc3[nH]ccc3c1CC(C(=O)O)S(=O)(=O)CC(C)(C)CCCC2(C)c1cccc(OCC(=O)O)c1]

Step F: To a stirred solution of crude step E product (0.360 g, 0.452 mmol) in 3:1 tetrahydrofuran/methanol (8 mL) was added a 1.0 M aqueous lithium hydroxide solution (2.3 mL, 2.3 mmol). The reaction was continued overnight at room temperature and then analyzed by LCMS and found to be complete. After acidifying with the addition of 1.0 M hydrochloric acid (to approximately pH 4, by litmus paper), the mixture was extracted with ethyl acetate (1×30 mL). The organic layer was washed with brine (2×30 mL), dried over sodium sulfate and concentrated. The crude title compound, which was used without purification, was obtained as a white solid (0.288 g, 86%). MS (ESI): 740 m/z $[M+H]^+$.

2-[3-[22,28-Difluoro-6,10,10-trimethyl-12,12-dioxo-3-(trideuteriomethyl)-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl]phenoxy]acetic Acid

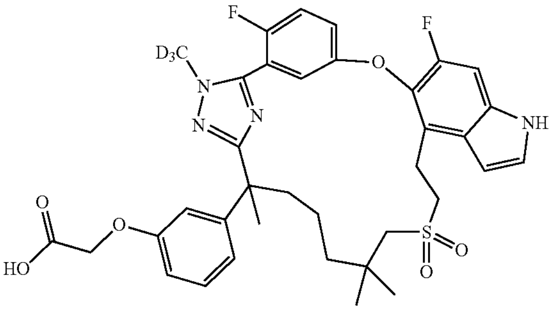 [SMILES: [2H]C([2H])([2H])n1nc2nc1-c1cc(ccc1F)Oc1c(F)cc3[nH]ccc3c1CCS(=O)(=O)CC(C)(C)CCCC2(C)c1cccc(OCC(=O)O)c1]

Step G: To a stirred solution crude step F product (0.288 g, 0.389 mmol) in N,N-dimethylformamide (10 mL) was added triethylamine (271 μL, 0.197 g, 1.94 mmol) at room temperature. The reaction was heated at 90° C. for three hours and then cooled to room temperature and partitioned between 1.0 N hydrochloric acid (50 mL) and ethyl acetate (100 mL). The organic layer was washed with brine (2×100 mL), dried over sodium sulfate and concentrated. The crude material was purified by automated flash chromatography (20 g silica gel column, 0-10% methanol in dichloromethane) to afford the title compound as a white solid (0.210 g, 77%). MS (ESI): 696 m/z $[M+H]^+$.

Compounds 1A and 1B (Enantiomers of 2-[3-[22,28-Difluoro-6,10,10-trimethyl-12,12-dioxo-3-(trideuteriomethyl)-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl]phenoxy]acetic Acid)

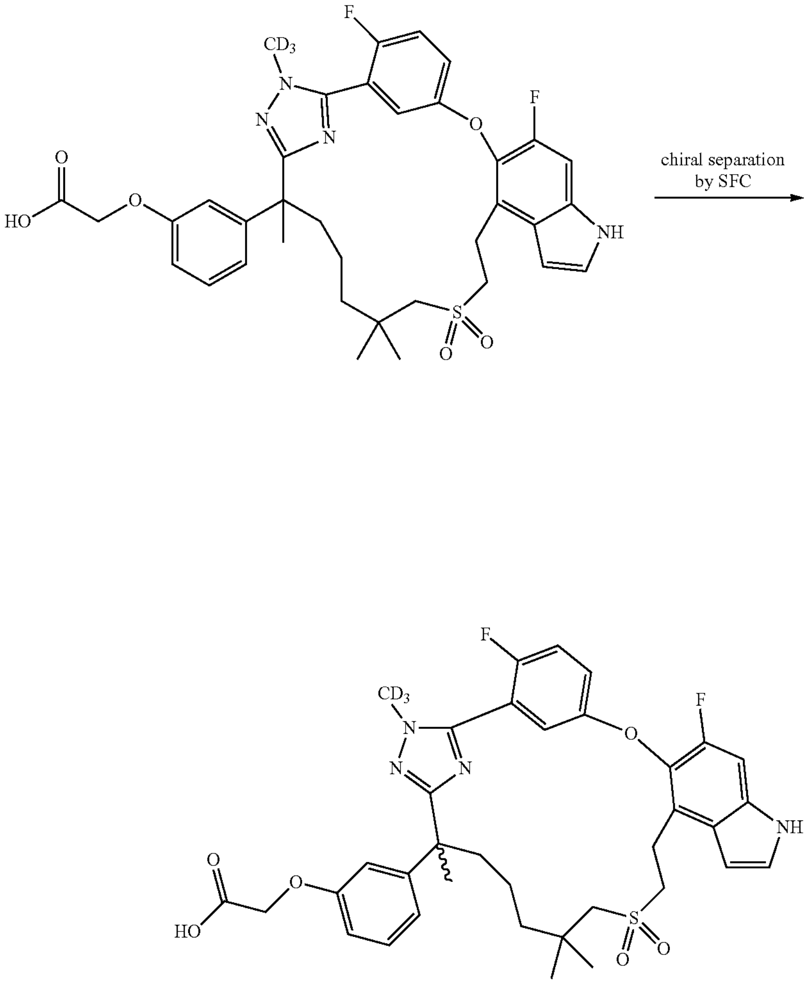

First eluent: Enantiomer 1
Second eluent: Enantiomer 2
(absolute configurations unknown)

Step H: The racemic product of step G (0.210 g, 0.301 mmol) was subjected to chiral SFC using a Thar SFC-80 instrument and the following separation conditions: Column: 20×250 mm×10 μm Chiralpak AD; sample solution: 210 mg dissolved in methanol (25 mL); injection volume: 1.0 mL; eluant: 70:30 $CO_2$/methanol with 1% ammonia/methanol additive; flow rate: 80 mL/min; column temperature: 35° C.; back pressure: 100 bar; detection wavelength: 214 nm. The first eluting isomer, designated 1A, was obtained as a white solid (74.9 mg, 36%). The second eluting isomer, designated 1B, was also obtained as a white solid (81.2 mg, 39%).

Compound 1A: $^1$H NMR (400 MHz, $CD_3OD$) δ 7.37-7.33 (m, 3H), 7.26-7.15 (m, 3H), 6.83-6.76 (m, 2H), 6.74 (dd, J=7.6, 2.0 Hz, 1H), 6.63 (dd, J=3.2, 0.8 Hz, 1H), 4.49 (s, 2H), 3.42-3.37 (m, 2H), 3.30-3.20 (m, 2H), 2.96 (d, J=13.6 Hz, 1H), 2.80 (d, J=13.6 Hz, 1H), 2.18-2.11 (m, 1H), 1.87-1.80 (m, 1H), 1.69 (s, 3H), 1.69-1.52 (m, 1H), 1.37-1.28 (m, 2H), 1.25-1.12 (m, 1H), 1.08 (s, 3H) ppm, 1.06 (s, 3H) ppm. MS (ESI): 696 m/z $[M+H]^+$. LC $R_t$, purity (LC-MS Method 01): 1.34 minutes, 91.8%/93.6% (210/254 nm).

Compound 1B: $^1$H NMR (400 MHz, $CD_3OD$) δ 7.36-7.33 (m, 3H), 7.26-7.15 (m, 3H), 6.83-6.76 (m, 1H), 6.74 (dd, J=7.6, 2.0 Hz, 1H), 6.63 (dd, J=3.2, 0.8 Hz, 1H), 4.49 (s, 2H), 3.42-3.37 (m, 2H), 3.30-3.20 (m, 2H), 2.96 (d, J=13.6 Hz, 1H), 2.80 (d, J=13.6 Hz, 1H), 2.18-2.11 (m, 1H), 1.87-1.80 (m, 1H), 1.69 (s, 3H), 1.69-1.52 (m, 1H), 1.37-1.28 (m, 2H), 1.25-1.12 (m, 1H), 1.08 (s, 3H) ppm, 1.06 (s, 3H) ppm. MS (ESI): 696 m/z $[M+H]^+$. LC $R_t$, purity (LC-MS Method 01): 1.34 minutes, 97.6%/98.6% (210/254 nm).

Example 2. Enantiomers of 3-[3-(9,9,22,28-Tetrafluoro-3,6-dimethyl-12,12-dioxo-24-oxa-12$\lambda^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]propanoic Acid

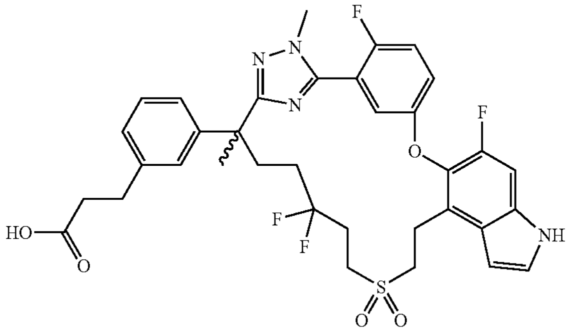 [SMILES: Cn1nc2nc1-c1cc(ccc1F)Oc1c(F)cc3[nH]ccc3c1CCS(=O)(=O)CCC(F)(F)CCC2(C)c1cccc(CCC(=O)O)c1]

Ethyl 3-(3-(7-((2-ethoxy-2-oxoethyl)sulfonyl)-5,5-difluoro-2-(5-(2-fluoro-5-((6-fluoro-4-vinyl-1H-indol-5-yl)oxy)phenyl)-1-methyl-1H-1,2,4-triazol-3-yl)heptan-2-yl)phenyl)propanoate

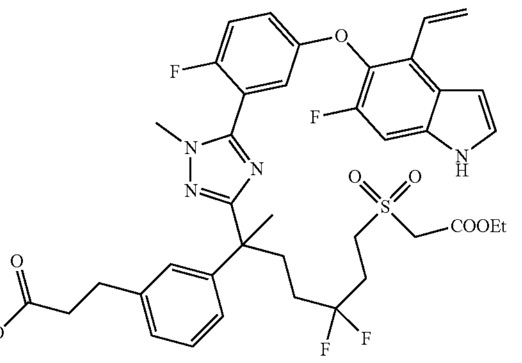

Step A: To a stirred solution of methyl 2-fluoro-5-((6-fluoro-4-vinyl-1H-indol-5-yl)oxy)benzimidothioate hydroiodide (Intermediate 14, 0.900 g, 1.91 mmol) in pyridine (10 mL) was added ethyl 3-(3-(7-((2-ethoxy-2-oxoethyl)sulfonyl)-5,5-difluoro-2-methyl-1-(2-methylhydrazineyl)-1-oxoheptan-2-yl)phenyl)propanoate (Intermediate 45-1, 1.02 g, 1.91 mmol) and magnesium sulfate (0.900 g, 7.48 mmol). The mixture was brought to 80° C. and maintained at this temperature for four hours. After cooling to room temperature, the reaction was partitioned between water (150 mL) and ethyl acetate (50 mL). The organic layer was combined with additional extracts (ethyl acetate, 2×50 mL) and washed with 1.0 N hydrochloric acid (2×50 mL) and brine (1×50 mL). The solution was then dried over sodium sulfate and concentrated. The resulting crude material was purified by automated flash chromatography (80 g silica gel column, 0-70% ethyl acetate in petroleum ether) to afford the title compound as light brown solid (0.901 g, 58% yield). MS (ESI): 813 m/z $[M+H]^+$.

Ethyl 3-(3-(2-(5-(5-((4-(1,2-dihydroxyethyl)-6-fluoro-1H-indol-5-yl)oxy)-2-fluorophenyl)-1-methyl-1H-1,2,4-triazol-3-yl)-7-((2-ethoxy-2-oxoethyl)sulfonyl)-5,5-difluoroheptan-2-yl)phenyl)propanoate

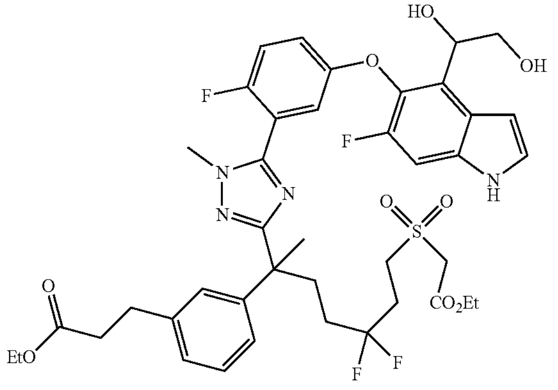 [SMILES: CCOC(=O)CCc1cccc(C(C)(CCC(F)(F)CCS(=O)(=O)CC(=O)OCC)c2nc(-c3cc(Oc4c(F)cc5[nH]ccc5c4C(O)CO)ccc3F)n(C)n2)c1]

Step B: To a stirred solution of ethyl 3-(3-(7-((2-ethoxy-2-oxoethyl)sulfonyl)-5,5-difluoro-2-(5-(2-fluoro-5-((6-fluoro-4-vinyl-1H-indol-5-yl)oxy)phenyl)-1-methyl-1H-1,2,4-triazol-3-yl)heptan-2-yl)phenyl)propanoate (Step A product, 0.900 g, 1.11 mmol) in 3:1 acetone/water (20 mL) was added a 4.0 M aqueous solution of 4-methylmorpholine-N-oxide (0.83 mL, 3.3 mmol) and a 0.2% aqueous solution of osmium tetroxide (0.60 mL, 12 mg, 47 μmol). After six hours at room temperature, the reaction was partitioned between ethyl acetate (20 mL) and water (50 mL). The organic layer was combined with additional extracts (ethyl acetate, 2×20 mL) and washed with brine (1×20 mL). The solution was then dried over sodium sulfate and concentrated to afford the crude title compound, which was used without purification, as a foamy solid (0.798 g, 85% yield). MS (ESI): 847 m/z $[M+H]^+$.

Ethyl 3-(3-(7-((2-ethoxy-2-oxoethyl)sulfonyl)-5,5-difluoro-2-(5-(2-fluoro-5-((6-fluoro-4-formyl-1H-indol-5-yl)oxy)phenyl)-1-methyl-1H-1,2,4-triazol-3-yl)heptan-2-yl)phenyl)propanoate

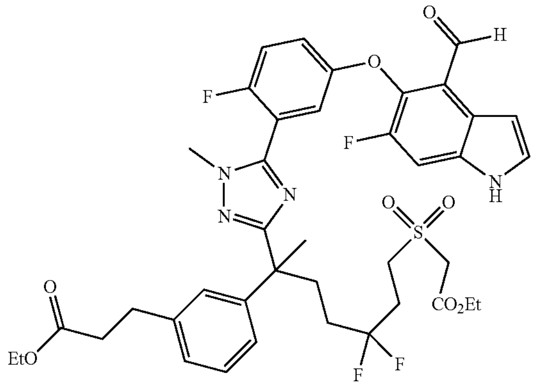 [SMILES: CCOC(=O)CCc1cccc(C(C)(CCC(F)(F)CCS(=O)(=O)CC(=O)OCC)c2nc(-c3cc(Oc4c(F)cc5[nH]ccc5c4C=O)ccc3F)n(C)n2)c1]

Step C: To a stirred and cooled (0° C.) solution of crude ethyl 3-(3-(2-(5-(5-((4-(1,2-dihydroxyethyl)-6-fluoro-1H-indol-5-yl)oxy)-2-fluorophenyl)-1-methyl-1H-1,2,4-triazol-3-yl)-7-((2-ethoxy-2-oxoethyl)sulfonyl)-5,5-difluoroheptan-2-yl)phenyl)propanoate (Step B product, 0.798 g, 0.982 mmol) in 3:1 acetone/water (20 mL) was added sodium periodate (0.420 g, 1.96 mmol). The reaction was allowed to warm to room temperature and stirred for an additional two hours before partitioning between water (100 mL) and ethyl acetate (30 mL). The organic layer was combined with additional extracts (ethyl acetate, 2×30 mL) and washed with brine (1×30 mL). The solution was then dried over sodium sulfate and concentrated. The crude residue was purified by automated flash chromatography (40 g silica gel column, 0-70% ethyl acetate in petroleum ether) to afford the title compound as an off-white solid (0.624 g, 78% yield). MS(ESI): 815 m/z $[M+H]^+$.

Ethyl 6-[3-(3-ethoxy-3-oxopropyl)phenyl]-9,9,22,28-tetrafluoro-3,6-dimethyl-12,12-dioxo-24-oxa-12$\lambda^6$-thia-3,4,19,30-tetrazapentacyclo[23.3.1.$1^{2,5}$.$0^{15,23}$.$0^{16,20}$]triaconta-1(29),2(30),4,13,15,17,20,22,25,27-decaene-13-carboxylate

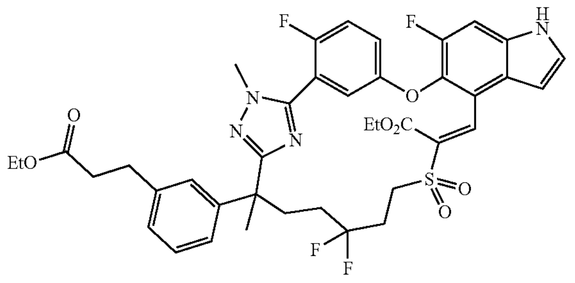 [SMILES: CCOC(=O)CCc1cccc(C2(C)CCC(F)(F)CCS(=O)(=O)/C(C(=O)OCC)=C/c3c(c(F)cc4[nH]ccc34)Oc3ccc(F)c(c3)-c3nc2nn3C)c1]

Step D: To a stirred solution of ethyl 3-(3-(7-((2-ethoxy-2-oxoethyl)sulfonyl)-5,5-difluoro-2-(5-(2-fluoro-5-((6-fluoro-4-formyl-1H-indol-5-yl)oxy)phenyl)-1-methyl-1H-1,2,4-triazol-3-yl)heptan-2-yl)phenyl)propanoate (Step C product, 0.624 g, 0.766 mmol) in toluene (500 mL) was added piperidine (75.7 μL, 65.3 mg, 0.766 mmol) and acetic acid (219 μL, 0.230 g, 3.83 mmol). The reaction was heated overnight at 110° C. and then cooled to room temperature and concentrated. The crude residue was subjected to automated flash chromatography (40 g silica gel column, 0-70% ethyl acetate in petroleum ether) to afford the title compound as a tan solid (0.366 g, 60%). MS(ESI): 797 m/z $[M+H]^+$.

Ethyl 6-[3-(3-ethoxy-3-oxopropyl)phenyl]-9,9,22,28-tetrafluoro-3,6-dimethyl-12,12-dioxo-24-oxa-12$\lambda^6$-thia-3,4,19,30-tetrazapentacyclo[23.3.1.$1^{2,5}$.$0^{15,23}$.$0^{16,20}$]triaconta-1(29),2(30),4,15,17,20,22,25,27-nonaene-13-carboxylate

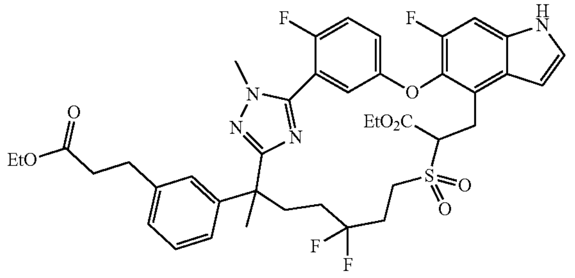 [SMILES: CCOC(=O)CCc1cccc(C2(C)CCC(F)(F)CCS(=O)(=O)C(C(=O)OCC)Cc3c(c(F)cc4[nH]ccc34)Oc3ccc(F)c(c3)-c3nc2nn3C)c1]

Step E: A stirred suspension of ethyl 6-[3-(3-ethoxy-3-oxopropyl)phenyl]-9,9,22,28-tetrafluoro-3,6-dimethyl-12,12-dioxo-24-oxa-12$\lambda^6$-thia-3,4,19,30-tetrazapentacyclo[23.3.1.$1^{2,5}$.$0^{15,23}$.$0^{16,20}$]triaconta-1(29),2(30),4,13,15,17,20,22,25,27-decaene-13-carboxylate (Step D product, 0.366 g, 0.459 mmol) and 10% palladium on carbon (0.350 g) in ethyl acetate (10 mL) was cycled between vacuum and a nitrogen atmosphere three times. After a final evacuation, the reaction vessel was backfilled with hydrogen (via balloon). The reaction was allowed to proceed overnight before the hydrogen was evacuated and the vessel was opened to air. The catalyst was removed by suction filtration through a pad of Celite, which was subsequently rinsed with methanol (2×20 mL). The combined filtrate was concentrated to afford the crude title compound, which was used without purification, as a white solid (0.334 g, 91%). MS (ESI): 799 m/z $[M+H]^+$.

6-[3-(2-Carboxyethyl)phenyl]-9,9,22,28-tetrafluoro-3,6-dimethyl-12,12-dioxo-24-oxa-12$\lambda^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaene-13-carboxylic Acid

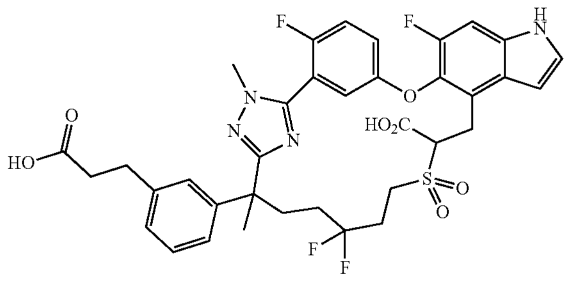 [SMILES: Cn1nc2nc1-c1cc(ccc1F)Oc1c(F)cc3[nH]ccc3c1CC(C(=O)O)S(=O)(=O)CCC(F)(F)CCC2(C)c1cccc(CCC(=O)O)c1]

Step F: To a stirred solution of crude ethyl 6-[3-(3-ethoxy-3-oxopropyl)phenyl]-9,9,22,28-tetrafluoro-3,6-dimethyl-12,12-dioxo-24-oxa-12$\lambda^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaene-13-carboxylate (Step E product, 0.334 g, 0.418 mmol) in 3:1:1 tetrahydrofuran/methanol/water (10 mL) was added lithium hydroxide monohydrate (87.7 mg, 2.09 mmol). After three hours at room temperature, the mixture was diluted with water (20 mL) and made acidic (pH 5-6) by the dropwise addition of 1.0 N hydrochloric acid. The resulting suspension was extracted with ethyl acetate (3×20 mL) and the combined organic layers were washed with water (1×40 mL) and brine (1×40 mL). The solution was then dried over sodium sulfate and concentrated. The crude residue was purified by automated flash chromatography (40 g silica gel column, 0-100% ethyl acetate in petroleum ether) to afford the title compound as a foamy solid (0.292 g, 94%). MS(ESI): 743 m/z [M+H]$^+$.

3-[3-(9,9,22,28-Tetrafluoro-3,6-dimethyl-12,12-dioxo-24-oxa-12$\lambda^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]propanoic Acid

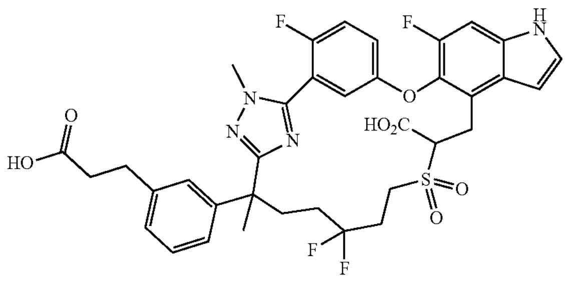 [SMILES: Cn1nc2nc1-c1cc(ccc1F)Oc1c(F)cc3[nH]ccc3c1CC(C(=O)O)S(=O)(=O)CCC(F)(F)CCC2(C)c1cccc(CCC(=O)O)c1]

Step G: To a stirred solution of 6-[3-(2-Carboxyethyl)phenyl]-9,9,22,28-tetrafluoro-3,6-dimethyl-12,12-dioxo-24-oxa-12$\lambda^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaene-13-carboxylic acid (Step F product, 0.280 g, 0.377 mmol) in N,N-dimethylformamide (5 mL) was added triethylamine (263 μL, 0.191 g, 1.89 mmol). The reaction was heated at 80° C. for six hours and then cooled to room temperature and partitioned between water (50 mL) and ethyl acetate (20 mL). The organic layer was combined with additional extracts (ethyl acetate, 2×20 mL), washed with brine (1×20 mL), dried over sodium sulfate and concentrated. The crude material was purified by automated flash chromatography (20 g silica gel column, 0-100% ethyl acetate in petroleum ether) to afford the title compound as an off-white solid (0.200 g, 76%). MS(ESI): 699 m/z [M+H]$^+$.

Compounds 2A and 2B (Enantiomers of 3-[3-(9,9,22,28-Tetrafluoro-3,6-dimethyl-12,12-dioxo-24-oxa-12$\lambda^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]propanoic Acid)

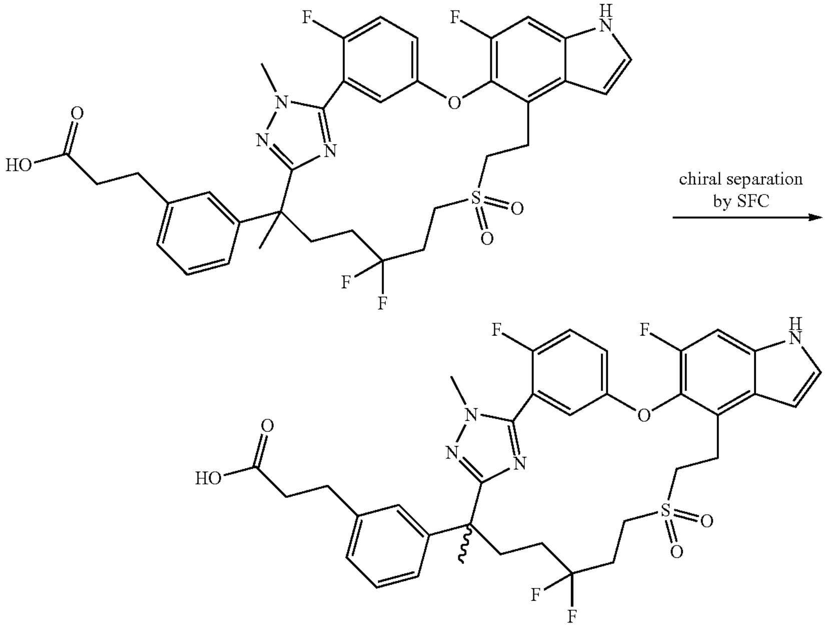

Enantiomer 1 (2A)
Enantiomer 2 (2B)
(absolute configurations unknown)

Step H: The racemic product of 3-[3-(9,9,22,28-tetrafluoro-3,6-dimethyl-12,12-dioxo-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]propanoic acid (Step G product, 0.200 g, 0.286 mmol) was subjected to chiral SFC using a Thar SFC-150 instrument and the following separation conditions. Column: 20×250 mm×10 μm Chiralpak AD; sample solution: 200 mg dissolved in methanol (25 mL); injection volume: 1.0 mL; eluant: 70:30 $CO_2$/isopropanol with 0.1% trifluoroacetic acid additive; flow rate: 100 mL/min; column temperature: 35° C.; back pressure: 100 bar; detection wavelength: 214 nm. The first eluting isomer, designated 2A, was obtained as a white solid (80 mg, 40%). The second eluting isomer, designated 2B, was also obtained as a white solid (80 mg, 40%).

Compound 2A: $^1$H NMR (400 MHz, $CD_3OD$) δ 7.45-7.39 (m, 2H), 7.36 (d, J=3.2 Hz, 1H), 7.26 (d, J=10.4 Hz, 1H), 7.15 (t, J=8.0 Hz, 1H), 7.07-7.02 (m, 2H), 7.00-6.96 (m, 1H), 6.94-6.91 (m, 1H), 6.68 (dd, J=3.2, 0.8 Hz, 1H), 3.86 (d, J=2.8 Hz, 3H), 3.53-3.43 (m, 2H), 3.39-3.30 (m, 1H), 3.23-3.12 (m, 2H), 2.94-2.82 (m, 1H), 2.79 (t, J=7.4 Hz, 2H), 2.49 (t, J=7.4 Hz, 2H), 2.37-2.15 (m, 3H), 2.12-1.88 (m, 2H), 1.73 (s, 3H), 1.60-1.42 (s, 1H) ppm. MS(ESI): 699 m/z [M+H]$^+$. LC $R_t$, purity (LC-MS Method 01): 1.33 minutes, >99.9%/96.0% (210/254 nm).

Compound 2B: $^1$H NMR (400 MHz, $CD_3OD$) δ 7.45-7.39 (m, 2H), 7.36 (d, J=3.2 Hz, 1H), 7.26 (d, J=10.4 Hz, 1H), 7.15 (t, J=8.0 Hz, 1H), 7.07-7.02 (m, 2H), 7.00-6.96 (m, 1H), 6.94-6.91 (m, 1H), 6.68 (dd, J=3.2, 0.8 Hz, 1H), 3.86 (d, J=2.8 Hz, 3H), 3.53-3.43 (m, 2H), 3.39-3.30 (m, 1H), 3.22-3.11 (m, 2H), 2.94-2.81 (m, 1H), 2.79 (t, J=7.4 Hz, 2H), 2.49 (t, J=7.4 Hz, 2H), 2.37-2.15 (m, 3H), 2.12-1.88 (m, 2H), 1.73 (s, 3H), 1.59-1.41 (s, 1H) ppm. MS(ESI): 699 m/z [M+H]$^+$. LC $R_t$, purity (LC-MS Method 01): 1.33 minutes, >99.9%/>99.9% (210/254 nm).

Example 3. 2-[3-(22,28-Difluoro-3,6,10,10-tetramethyl-12,12-dioxo-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]acetic Acid

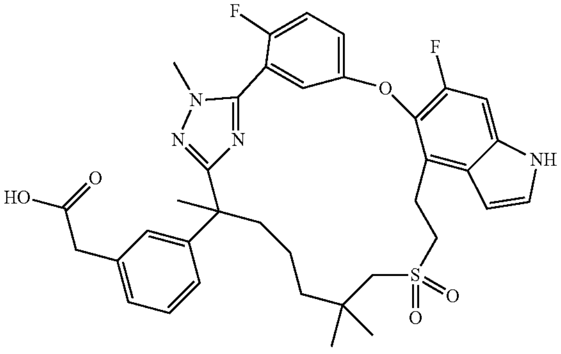 [SMILES: Cn1nc2nc1-c1cc(ccc1F)Oc1c(F)cc3[nH]ccc3c1CCS(=O)(=O)CC(C)(C)CCCC2(C)c1cccc(CC(=O)O)c1]

Exchanging ethyl 2-((6-(3-(2-ethoxy-2-oxoethoxy)phenyl)-2,2,6-trimethyl-7-(2-(methyl-d$_3$)hydrazineyl)-7-oxoheptyl)sulfonyl)acetate (Intermediate 45) for ethyl 2-((6-(3-(2-ethoxy-2-oxoethyl)phenyl)-2,2,6-trimethyl-7-(2-methylhydrazineyl)-7-oxoheptyl)sulfonyl)acetate (intermediate 45-2, 2.12 g, 4.14 mmol), the reaction procedure sequence described for Example 1 (Steps A-G) was used to prepare the title compound (Compound 3) (0.199 g, 0.23 mmol) as a white solid.

Compound 3: $^1$H NMR (400 MHz, DMSO-d$_6$) δ 11.4 (s, 1H), 7.46-7.35 (m, 2H), 7.33 (d, J=2.8 Hz, 1H), 7.31-7.24 (m, 2H), 7.17-7.12 (m, 2H), 7.07-7.04 (m, 1H), 6.99-6.97 (m, 1H), 6.51 (s, 1H), 3.78 (d, J=1.6 Hz, 3H), 3.41 (s, 2H), 3.27-3.11 (m, 4H), 2.94 (d, J=14 Hz, 1H), 2.82 (d, J=14 Hz, 1H), 2.13-2.08 (m, 1H), 1.72-1.66 (m, 1H), 1.62 (s, 3H), 1.50-1.44 (m, 1H), 1.26-1.20 (m, 1H), 1.03 (s, 3H), 0.99 (s, 3H) ppm. MS (ESI): 677 m/z [M+H]$^+$. LC $R_t$, purity (LC-MS Method 01): 1.35 minutes, >99.9%/>99.9% (210/254 nm).

Example 4. Enantiomers of 2-[3-(22,28-Difluoro-3,6,10,10-tetramethyl-12,12-dioxo-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]ethanol

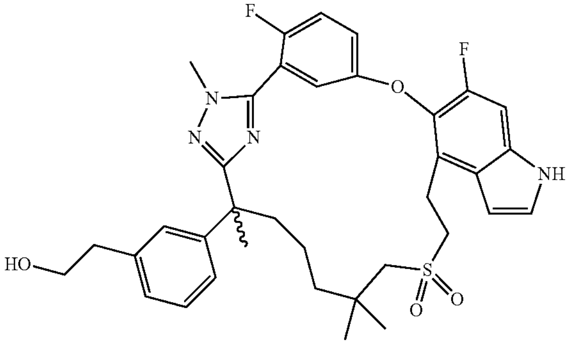 [SMILES: Cn1nc2nc1-c1cc(ccc1F)Oc1c(F)cc3[nH]ccc3c1CCS(=O)(=O)CC(C)(C)CCCC2(C)c1cccc(CCO)c1]

Methyl 2-[3-(22,28-difluoro-3,6,10,10-tetramethyl-12,12-dioxo-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]Acetate

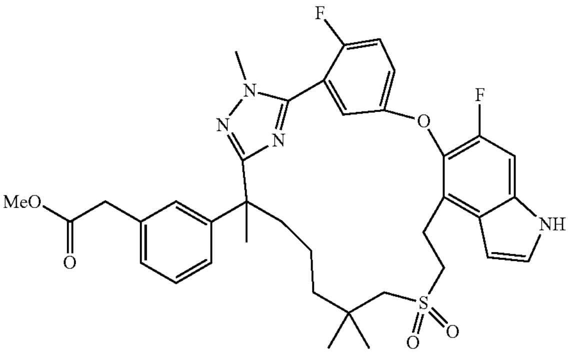 [SMILES: COC(=O)Cc1cccc(C2(C)CCCC(C)(C)CS(=O)(=O)CCc3c(c(F)cc4[nH]ccc34)Oc3ccc(F)c(c3)-c3nc2nn3C)c1]

Step A: To a stirred solution of Compound 3 (0.200 g, 0.296 mmol) in methanol (6 mL) was added 1-2 drops (50-100 μL) of concentrated sulfuric acid. The reaction was allowed to proceed at room temperature for six hours and then partitioned between water (30 mL) and ethyl acetate (30 mL). The organic layer was combined with a second extract (ethyl acetate, 1×30 mL), washed with brine (1×30 mL), dried over sodium sulfate and concentrated. The crude title compound, which was used without purification, was obtained as an off-white solid (0.200 g, 98%). MS(ESI): 691 m/z $[M+H]^+$.

2-[3-(22,28-Difluoro-3,6,10,10-tetramethyl-12,12-dioxo-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]ethanol

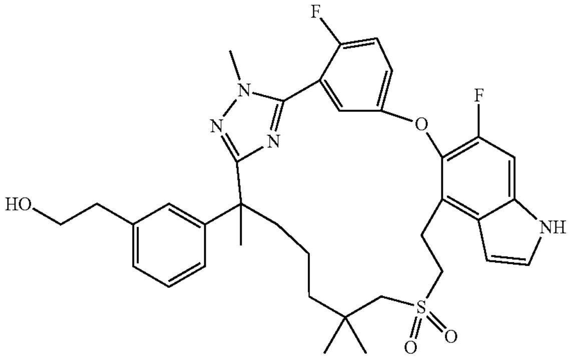 [SMILES: Cn1nc2nc1-c1cc(ccc1F)Oc1c(F)cc3[nH]ccc3c1CCS(=O)(=O)CC(C)(C)CCCC2(C)c1cccc(CCO)c1]

Step B: To a stirred solution of crude step A product (0.200 g, 0.290 mmol) in tetrahydrofuran (6 mL) was added lithium borohydride (0.126 g, 5.79 mmol). The reaction was allowed to proceed overnight at room temperature and then partitioned between water (40 mL) and ethyl acetate (30 mL). The organic layer was combined with a second extract (ethyl acetate, 1×30 mL) and washed with brine (1×30 mL). The solution was then dried over sodium sulfate and concentrated to provide a crude residue which was subjected to automated flash chromatography (25 g silica gel column, 0-70% ethyl acetate in petroleum ether). The title compound was obtained as a white solid (0.170 g, 8%). MS(ESI): 663 m/z $[M+H]^+$.

Compounds 4A and 4B (Enantiomers of 2-[3-(22,28-Difluoro-3,6,10,10-tetramethyl-12,12-dioxo-24-oxa-12 6-thia-3,4,19,30-tetrazapentacyclo[23.3.1.12,5.015,23.016,20]triaconta-1(29),2(30),4,15,17,20,22,25,27-nonaen-6-yl)phenyl]ethanol)

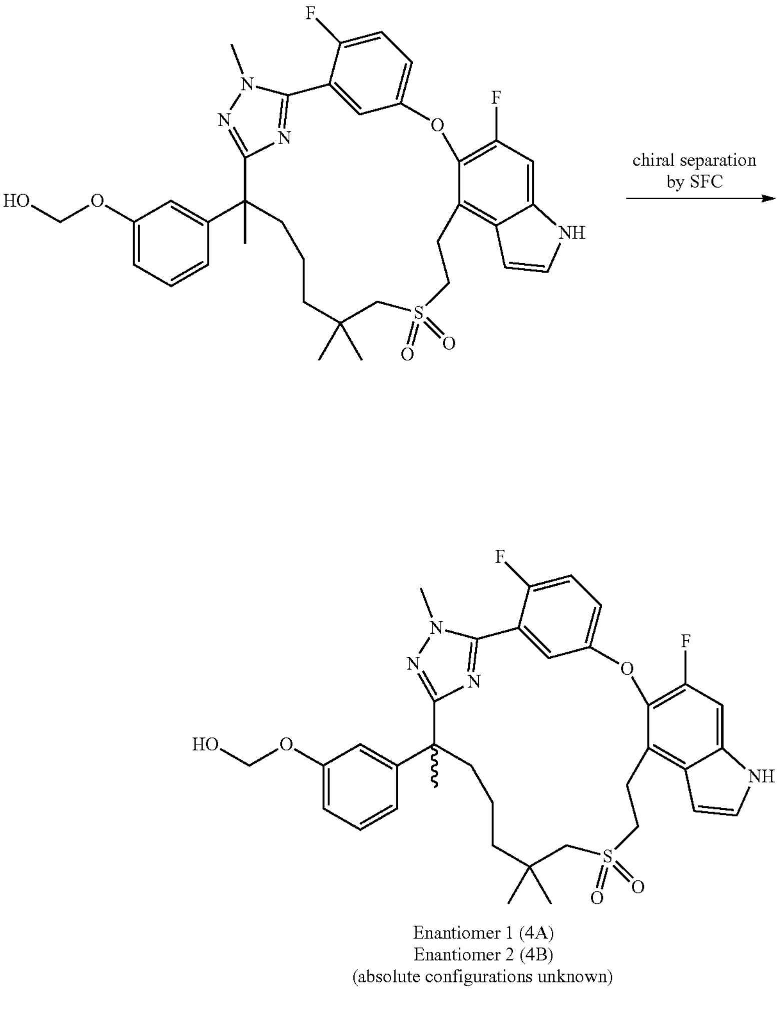

Enantiomer 1 (4A)
Enantiomer 2 (4B)
(absolute configurations unknown)

Step C: The racemic product of step B (0.170 g, 0.256 mmol) was subjected to chiral HPLC using a Gilson GX-281 liquid handler system and the following separation conditions: Column: 20×250 mm×10 μm Chiralpak AD; sample solution: 170 mg dissolved in methanol (8 mL); injection volume: 0.7 mL; eluant: 80:20 hexane/ethanol with a modifier of 0.1% diethylamine; flow rate: 50 mL/min; detection wavelength: 214 nm. The first eluting isomer, designated 4A, was obtained as a white solid (37 mg, 22%). The second eluting isomer, designated 4B, was also obtained as a white solid (45 mg, 26%).

Compound 4A: $^1$H NMR (400 MHz, $CD_3OD$) δ 7.42-7.31 (m, 3H), 7.27-7.16 (m, 3H), 7.12-6.99 (m, 3H), 6.64 (d, J=3.2 Hz, 1H), 3.87 (d, J=2.0 Hz, 3H), 3.68 (t, J=7.2 Hz, 2H), 3.46-3.26 (m, 3H), 3.26-3.13 (m, 1H), 2.92 (d, J=13.6 Hz, 1H), 2.85-2.68 (m, 3H), 2.17 (td, J=10.8, 4.4 Hz, 1H), 1.84 (td, J=10.8, 4.4 Hz, 1H), 1.69 (s, 3H), 1.67-1.49 (m, 1H), 1.43-1.27 (m, 1H), 1.26-1.13 (m, 1H), 1.11 (s, 3H), 1.00 (s, 3H), 0.96-0.86 (m, 1H) ppm. MS (ESI): 663 m/z $[M+H]^+$. LC $R_t$, purity (LC-MS Method 01): 1.40 minutes, >99.9%/>99.9% (210/254 nm).

Compound 4B: $^1$H NMR (400 MHz, $CD_3OD$) δ 7.42-7.31 (m, 3H), 7.27-7.16 (m, 3H), 7.12-6.99 (m, 3H), 6.64 (d, J=3.2 Hz, 1H), 3.87 (d, J=2.0 Hz, 3H), 3.68 (t, J=7.2 Hz, 2H), 3.46-3.27 (m, 3H), 3.26-3.13 (m, 1H), 2.92 (d, J=13.6 Hz, 1H), 2.85-2.68 (m, 3H), 2.17 (td, J=10.8, 4.4 Hz, 1H), 1.84 (td, J=10.8, 4.4 Hz, 1H), 1.69 (s, 3H), 1.66-1.50 (m, 1H), 1.40-1.27 (m, 1H), 1.25-1.14 (m, 1H), 1.11 (s, 3H), 1.00 (s, 3H), 0.96-0.87 (m, 1H) ppm. MS (ESI): 663 m/z $[M+H]^+$. LC $R_t$, purity (LC-MS Method 01): 1.40 min, 99.1%/98.7% (210/254 nm).

Example 5. Enantiomers of 2-[3-(22,28-Difluoro-3,6,10,10-tetramethyl-12,12-dioxo-9,24-dioxa-12λ$^6$-thia-3,4,19,30-tetrazapentacyclo[23.3.1.12,5.015,23.016,20]triaconta-1(29),2(30),4,15,17,20,22,25,27-nonaen-6-yl)phenyl]acetic Acid

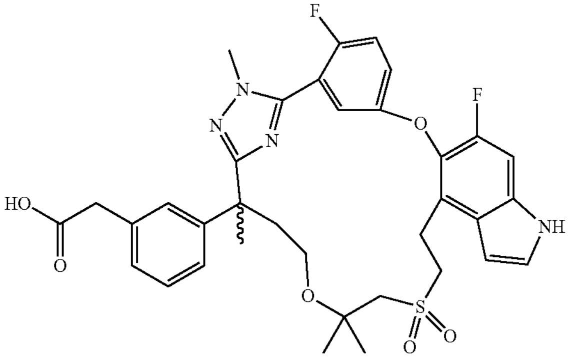 [SMILES: Cn1nc2nc1-c1cc(ccc1F)Oc1c(F)cc3[nH]ccc3c1CCS(=O)(=O)CC(C)(C)OCCC2(C)c1cccc(CC(=O)O)c1]

2-[3-(22,28-Difluoro-3,6,10,10-tetramethyl-12,12-dioxo-9,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]acetic acid Step A: Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) for ethyl 2-((2-(3-(3-(2-ethoxy-2-oxoethyl)phenyl)-3-methyl-4-(2-methylhydrazineyl)-4-oxobutoxy)-2-methylpropyl)sulfonyl)acetate (intermediate 45-3, 1.92 g, 3.73 mmol), the reaction procedure sequence described in Example 1 (Steps A-G) was used to prepare the title compound (0.201 g, 0.30 mmol) as a white solid.

Compound 5A and 5B (Enantiomers of 2-[3-(22,28-Difluoro-3,6,10,10-tetramethyl-12,12-dioxo-9,24-dioxa-12 6-thia-3,4,19,30-tetrazapentacyclo[23.3.1.12,5.015,23.016,20]triaconta-1(29),2(30),4,15,17,20,22,25,27-nonaen-6-yl)phenyl]acetic Acid)

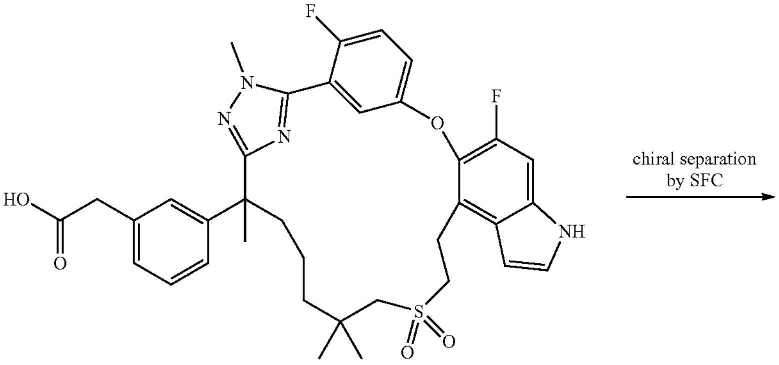

-continued

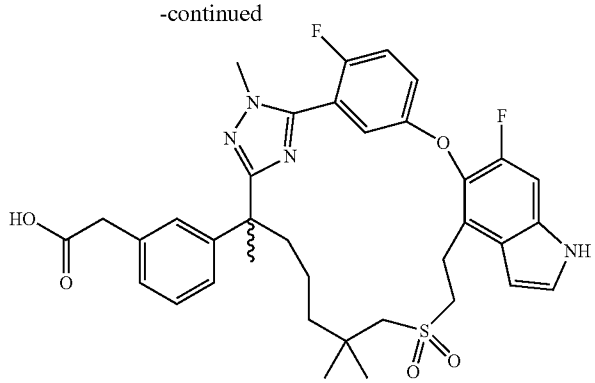

Enantiomer 1 (5A)
Enantiomer 2 (5B)
(absolute configurations unknown)

Step B: The racemic product of step A above (0.190 g, 0.286 mmol) was subjected to chiral SFC using a Thar SFC-150 instrument and the following separation conditions. Column: Regis 20×250 mm×10 μm (S,S)-Whelk-O 1; sample solution: 200 mg dissolved in methanol (20 mL); injection volume: 2.0 mL; eluant: 45:55 $CO_2$/isopropanol with 0.2% trifluoroacetic acid additive; flow rate: 80 mL/min; column temperature: 35° C.; back pressure: 100 bar; detection wavelength: 214 nm. The first eluting isomer, designated enantiomer 1 (Compound 5A), was obtained as a white solid (36.0 mg, 19%). The second eluting isomer, designated enantiomer 2 (Compound 5B), was also obtained as a white solid (40.3 mg, 21%).

Compound 5A: $^1$H NMR (400 MHz, $CD_3OD$) δ 7.44-7.33 (m, 3H), 7.25 (d, J=10.8 Hz, 1H), 7.20 (t, J=8.0 Hz, 1H), 7.15-7.08 (m, 3H), 7.02 (d, J=8.0 Hz, 1H), 6.62 (d, J=3.2 Hz, 1H), 3.89 (d, J=3.2 Hz, 3H), 3.75-3.66 (m, 1H), 3.51 (d, J=2.0 Hz, 2H), 3.48-3.32 (m, partially obscured by $CD_2HOD$ resonance, 4H), 3.21-3.05 (m, 3H), 2.40-2.28 (m, 1H), 2.16-2.04 (m, 1H), 1.68 (s, 3H), 1.30 (s, 3H), 1.24 (s, 3H) ppm. MS (ESI): 679 m/z $[M+H]^+$. LC $R_t$, purity (LC-MS Method 01): 1.26 minutes, >99.9%/>99.9% (210/254 nm).

Compound 5B: $^1$H NMR (400 MHz, $CD_3OD$) δ 7.43-7.33 (m, 3H), 7.25 (d, J=10.8 Hz, 1H), 7.20 (t, J=8.0 Hz, 1H), 7.15-7.08 (m, 3H), 7.02 (d, J=8.0 Hz, 1H), 6.62 (d, J=3.2 Hz, 1H), 3.89 (d, J=3.2 Hz, 3H), 3.75-3.66 (m, 1H), 3.51 (d, J=2.0 Hz, 2H), 3.48-3.31 (m, partially obscured by $CD_2HOD$ resonance, 4H), 3.21-3.05 (m, 3H), 2.40-2.29 (m, 1H), 2.16-2.04 (m, 1H), 1.68 (s, 3H), 1.30 (s, 3H), 1.24 (s, 3H) ppm. MS (ESI): 679 m/z $[M+H]^+$. LC $R_t$, purity (LC-MS Method 01): 1.26 minutes, >99.9%/>99.9% (210/254 nm).

Example 6. Diastereomers of (2R)-3-[3-(22,28-difluoro-3,6,10,10-tetramethyl-12,12-dioxo-24-oxa-12λ$^6$-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

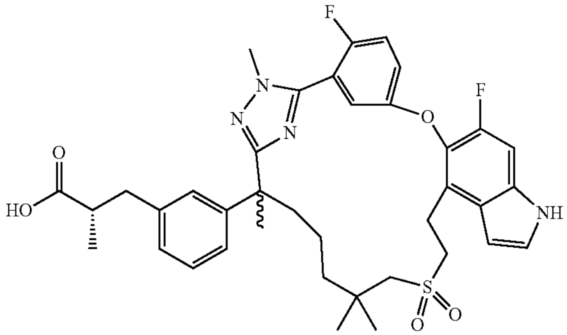 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

Methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate

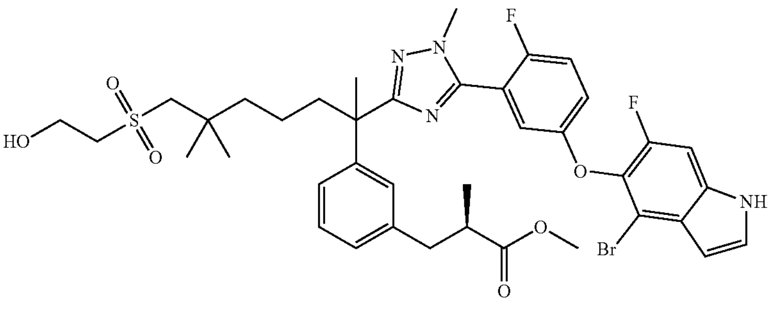 [SMILES: COC(=O)[C@H](C)Cc1cccc(C(C)(CCCC(C)(C)CS(=O)(=O)CCO)c2nc(-c3cc(Oc4c(F)cc5[nH]ccc5c4Br)ccc3F)n(C)n2)c1]

Step A: To a stirred solution of methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69, 7.81 g, 16.1 mmol) in pyridine (100 mL) was added methyl 5-((4-bromo-6-fluoro-1H-indol-5-yl)oxy)-2-fluorobenzimidothioate hydroiodide (Intermediate 14-1, 9.30 g, 17.7 mmol). The mixture was heated at 80° C. for four hours and then cooled to room temperature and partitioned between 1.0 M hydrochloric acid (200 mL) and ethyl acetate (300 mL). The organic layer was washed with brine (2×300 mL), dried over sodium sulfate, and concentrated to afford a solid which was subjected to automated flash chromatography (80 g silica gel column, 0-60% ethyl acetate in petroleum ether). The title compound was obtained as a tan solid (7.92 g, 60%). MS(ESI): 815, 817 m/z $[M+H]^+$.

Methyl (2R)-3-(3-(2-(5-(5-((4-bromo-6-fluoro-1H-indol-5-yl)oxy)-2-fluorophenyl)-1-methyl-1H-1,2,4-triazol-3-yl)-6,6-dimethyl-7-(vinylsulfonyl)heptan-2-yl)phenyl)-2-methylpropanoate

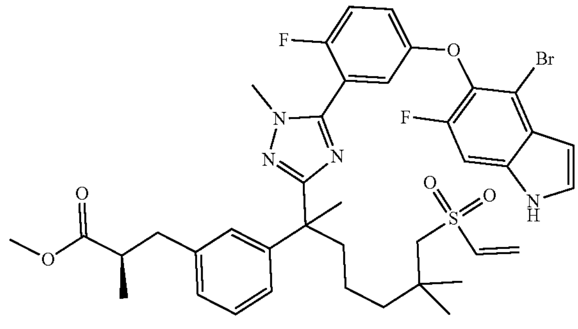 [SMILES: C=CS(=O)(=O)CC(C)(C)CCCC(C)(c1cccc(C[C@@H](C)C(=O)OC)c1)c1nc(-c2cc(Oc3c(F)cc4[nH]ccc4c3Br)ccc2F)n(C)n1]

Step B: To a stirred solution of step A product (7.90 g, 9.68 mmol) in dichloromethane (100 mL) was added triethylamine (4.05 mL, 2.94 g, 29.1 mmol) followed by methanesulfonyl chloride (0.825 μL, 1.22 g, 10.7 mmol). After two hours at room temperature, the mixture was partitioned between additional dichloromethane (150 mL) and brine (200 mL). The organic layer was washed with a second portion of brine (1×200 mL), dried over sodium sulfate and concentrated. The residue was purified by automated flash chromatography (120 g silica gel column, 0-50% ethyl acetate in petroleum ether) to afford the title compound as tan solid (6.50 g, 84%). MS(ESI): 797, 799 m/z $[M+H]^+$. Methyl (2R)-3-[3-[22,28-difluoro-3,6,10,10-tetramethyl-12,12-dioxo-24-oxa-12 6-thia-3,4,19,30-tetrazapentacyclo [23.3.1.12,5.015,23.016,20]triaconta-1(29),2(30),4,13,15,17,20,22,25,27-decaen-6-yl]phenyl]-2-methyl-propanoate

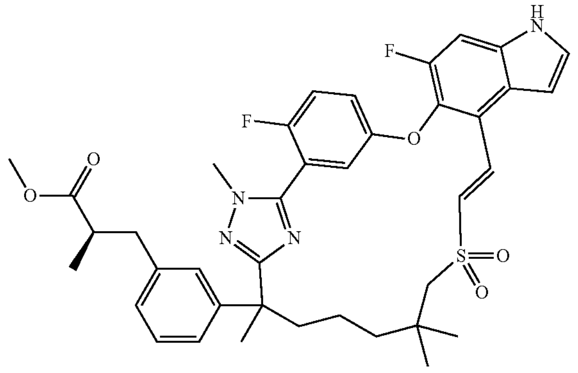 [SMILES: COC(=O)[C@H](C)Cc1cccc(C2(C)CCCC(C)(C)CS(=O)(=O)/C=C/c3c(c(F)cc4[nH]ccc34)Oc3ccc(F)c(c3)-c3nc2nn3C)c1]

Step C: The reaction was carried out in a glove box under a positive pressure of dry nitrogen. To a stirred solution of step B product (6.50 g, 8.15 mmol) in toluene (1 L) was added bis(tri-tert-butylphosphine)palladium(O) (0.833 g, 1.63 mmol) and triethylamine (11.4 mL, 8.28 g, 81.8 mmol). The mixture was heated at 100° C. for two hours and then cooled to room temperature and concentrated. The residue was partitioned between ethyl acetate (200 mL) and water (200 mL). The organic layer was washed with a second portion of water (1×200 mL), dried over sodium sulfate and concentrated to afford a brown solid. This crude material was subjected to automated flash chromatography (80 g silica gel column, 0-50% ethyl acetate in petroleum ether). The title compound was obtained as a pale amber solid (2.81 g, 48%). MS (ESI): 717 m/z $[M+H]^+$.

Methyl (2R)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl) phenyl]-2-methyl-propanoate

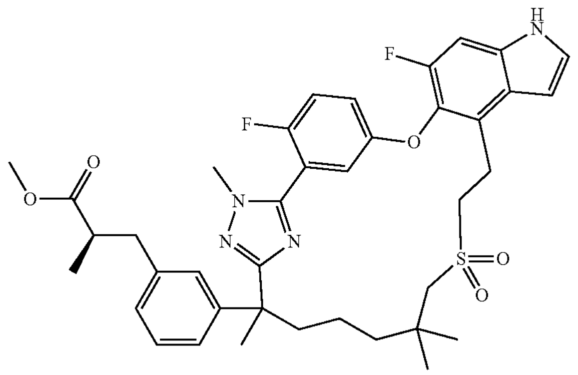 [SMILES: COC(=O)[C@H](C)Cc1cccc(C2(C)CCCC(C)(C)CS(=O)(=O)CCc3c(c(F)cc4[nH]ccc34)Oc3ccc(F)c(c3)-c3nc2nn3C)c1]

Step D: A stirred suspension of step C product (2.80 g, 3.91 mmol) and 10% palladium on carbon (0.800 g of a 50% aqueous dispersion) in ethanol (50 mL) was cycled between vacuum and a nitrogen atmosphere three times. After a final evacuation, the reaction vessel was backfilled with hydrogen (via balloon). The mixture was heated at 50° C. for two hours and then cooled to room temperature and opened to air. The catalyst was removed by suction filtration through a pad of Celite, which was subsequently rinsed with ethanol (2×30 mL). The combined filtrate was concentrated to afford the crude title compound, which was used without purification, as a white solid (2.62 g, 93%). MS (ESI): 719 m/z $[M+H]^+$.

Diastereomer 1 and 2 of Methyl (2R)-3-[3-(22,28-difluoro-3,6,10,10-tetramethyl-12,12-dioxo-24-oxa-12 6-thia-3,4,19,30-tetrazapentacyclo[23.3.1.12, 5.015,23.016,20]triaconta-1(29),2(30),4,15,17,20,22, 25,27-nonaen-6-yl)phenyl]-2-methyl-propanoate

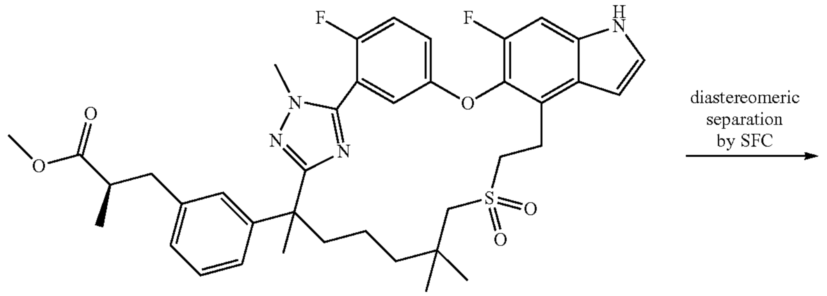

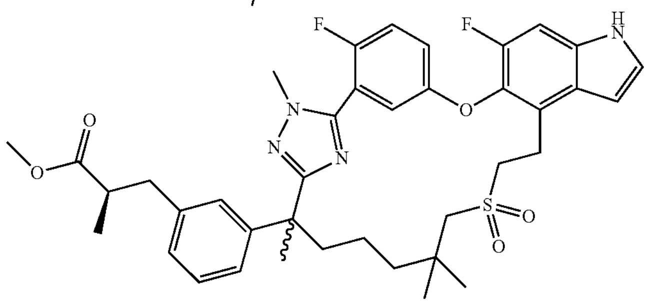

Diastereomer 1 (first eluting isomer)
Diastereomer 2 (second eluting isomer)
(absolute configuration of quaternary chiral center unknown)

Step E: Step D product was separated into its two constituent diastereomers by SFC using a Thar SFC-200 instrument and the following separation conditions. Column: 20×250 mm×10 μm CHIRALPAK AD; sample solution: 2.50 g dissolved in methanol (140 mL); injection volume: 1.5 mL; eluant: 85:15 $CO_2$/methanol with 0.2% ammonia/methanol additive; flow rate: 130 mL/min; column temperature: 35° C.; back pressure: 100 bar; detection wavelength: 214 nm. The first eluting isomer was designated Diastereomer 1 (1.16 g, 46%) and the second eluting isomer, Diastereomer 2 (1.07 g, 43%). Both were obtained as white solids.

Diastereomer 1: $^1$H NMR (400 MHz, $CD_3OD$) δ 7.40-7.30 (m, 3H), 7.26-7.14 (m, 3H), 7.07-7.02 (m, 1H), 7.00-6.93 (m, 2H), 6.63 (dd, J=3.2, 0.7 Hz, 1H), 3.87 (d, J=2.3 Hz, 3H), 3.56 (s, 3H), 3.43-3.35 (m, 2H), 3.31-3.17 (m, 2H), 2.97 (d, J=13.5 Hz, 1H), 2.89-2.78 (m, 2H), 2.71-2.60 (m, 2H), 2.20-2.09 (m, 1H), 1.88-1.79 (m, 1H), 1.69 (s, 3H), 1.67-1.52 (m, 1H), 1.39-1.17 (m, 3H), 1.11-1.01 (m, 9H) ppm.

Diastereomer 2: $^1$H NMR (400 MHz, $CD_3OD$) δ 7.40-7.31 (m, 3H), 7.26-7.14 (m, 3H), 7.05-7.00 (m, 1H), 7.00-6.94 (m, 2H), 6.63 (dd, J=3.2, 0.7 Hz, 1H), 3.88 (d, J=2.3 Hz, 3H), 3.55 (s, 3H), 3.43-3.35 (m, 2H), 3.32-3.16 (m, 2H), 2.95 (d, J=13.6 Hz, 1H), 2.91-2.83 (m, 1H), 2.80 (d, J=13.6 Hz, 1H), 2.71-2.60 (m, 2H), 2.21-2.10 (m, 1H), 1.87-1.77 (m, 1H), 1.68 (s, 3H), 1.67-1.55 (m, 1H), 1.39-1.28 (m, 1H), 1.25-1.16 (m, 1H), 1.13-0.98 (m, 10H) ppm.

Compound 6A (Diastereomer 1 of (2R)-3-[3-(22, 28-Difluoro-3,6,10,10-tetramethyl-12,12-dioxo-24-oxa-12 6-thia-3,4,19,30-tetrazapentacyclo[23.3.1.12, 5.015,23.016,20]triaconta-1(29),2(30),4,15,17,20,22, 25,27-nonaen-6-yl)phenyl]-2-methyl-propanoic acid

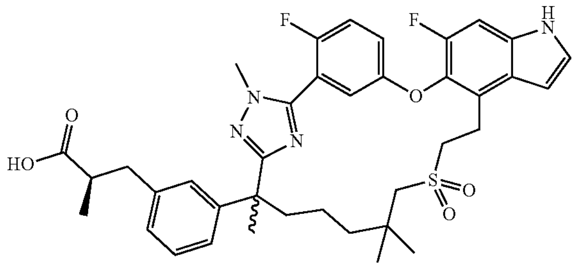

6A (from step E Diastereomer 1)
(absolute configuration of quaternary chiral center unknown)

Step F: To a stirred solution of the Diastereomer 1 product of step E (1.10 g, 1.53 mmol) in 3:1 tetrahydrofuran/methanol (20 mL) was added a 1.0 M aqueous lithium hydroxide solution (4.6 mL, 4.6 mmol). After four hours at room temperature, the reaction was acidified with the addition of 1.0 M hydrochloric acid (10 mL). The resulting suspension was extracted with ethyl acetate (1×50 mL) and the organic layer was washed with brine (2×20 mL), dried over sodium sulfate and concentrated. The crude product was purified by automated flash chromatography (12 g silica gel column, 0-70% ethyl acetate in petroleum ether) to afford 6A as a white solid (0.902 g, 84%). To confirm that the propanoic acid chiral center of the molecule had not epimerized following its incorporation into the molecule (Intermediate 65; Negishi coupling reaction with (S)-3-methoxy-2-methyl-3-oxopropylzinc iodide), the compound was examined by chiral HPLC using a method capable of analytically resolving 6A from its enantiomer and its propanoic chiral center inverted epimer. These isomers were obtained by repeating the synthetic route with a stereo-inverted, Negishi reagent precursor, (S)-3-hydroxy-2-methyl-propanoate, converted to corresponding iodo precursor and used in Intermediate 65. Chiral purity was determined to be >97.4%, with 1.6% contamination from the α-carbonyl epimerized isomer and 1% or less from the enantiomer. Given the stated purity of the methyl (R)-3-hydroxy-2-methylpropionate starting material (99%) used to prepare the zinc iodide reagent (steps A and H), this result indicated minimal erosion of chiral purity induced by subsequent synthetic steps. The chiral analysis was carried out using an Agilent 1200 HPLC system and the following separation conditions. Column: 4.6×250 mm×5 μm Chiralpak AD-H; sample solution: 1.0 mg/mL; injection volume: 10 μL; eluant: 85:15 heptane/isopropanol with 0.1% trifluoroacetic acid; flow rate: 1.0 mL/min; column temperature: 23° C.; detection wavelength: 254 nm. Observed retention times: 6A, 16.75 minutes; epimer, 12.81 minutes; enantiomer, 20.56 minutes.

Compound 6A: $^1$H NMR (400 MHz, $CD_3OD$) δ 7.39-7.30 (m, 3H), 7.25-7.13 (m, 3H), 7.07-6.97 (m, 3H), 6.63 (d, J=3.2 Hz, 1H), 3.87 (d, J=2.1 Hz, 3H), 3.44-3.37 (m, 2H), 3.36-3.27 (m, 1H), 3.26-3.16 (m, 1H), 2.99-2.88 (m, 2H), 2.81 (d, J=13.6 Hz, 1H), 2.68-2.55 (m, 2H), 2.16 (dt, J=12.8, 3.6 Hz, 1H), 1.84 (dt, J=12.8, 4.4 Hz, 1H), 1.75-1.51 (m, 4H), 1.40-1.28 (m, 1H), 1.28-1.14 (m, 1H), 1.14-0.95 (m, 10H) ppm. MS (ESI): 705 m/z [M+H]$^+$. LC $R_t$, purity (LC-MS Method 01): 1.44 minutes, >99.9%/96.8% (210/254 nm).

Compound 6B (Diastereomer 2 of (2R)-3-[3-(22,28-Difluoro-3,6,10,10-tetramethyl-12,12-dioxo-24-oxa-12 6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

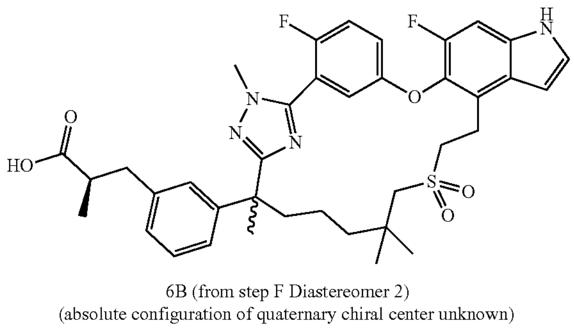 [SMILES: C[C@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

6B (from step F Diastereomer 2)
(absolute configuration of quaternary chiral center unknown)

Step G: Using a procedure identical to that described in step F, Diastereomer 2 product of step E (1.00 g, 1.39 mmol) was hydrolyzed to afford the title compound as a white solid (0.846 g, 86%).

Compound 6B: $^1$H NMR (400 MHz, $CD_3OD$) δ 7.40-7.29 (m, 3H), 7.27-7.12 (m, 3H), 7.09-6.94 (m, 3H), 6.63 (d, J=3.1 Hz, 1H), 3.87 (d, J=2.0 Hz, 3H), 3.47-3.35 (m, 2H), 3.33-3.16 (m, 2H), 3.02-2.88 (m, 2H), 2.82 (d, J=13.6 Hz, 1H), 2.69-2.53 (m, 2H), 2.16 (dt, J=12.7, 3.2 Hz, 1H), 1.83 (dt, J=12.7, 4.2 Hz, 1H), 1.76-1.52 (m, 4H), 1.41-1.27 (m, 1H), 1.27-1.14 (m, 1H), 1.14-0.95 (m, 10H) ppm. MS (ESI): 705 m/z [M+H]$^+$. LC $R_t$, purity (LC-MS Method 01): 1.44 minutes, >99.9%/>99.9% (210/254 nm).

Example 7. (Diastereomer 1) of (2S)-3-[3-(22,28-Difluoro-3,6,10,10-tetramethyl-12,12-dioxo-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic Acid

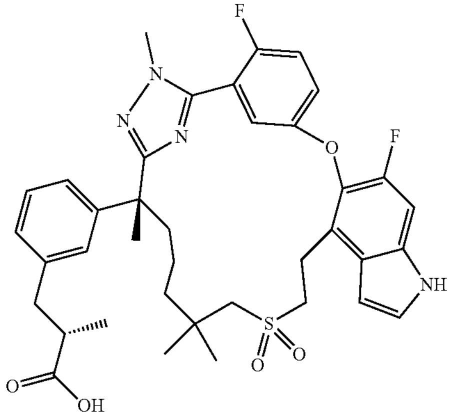 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3nc2nn3C)c1)C(=O)O]

Exchanging of methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with methyl (2S)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69-1) in Step A, the title compound was prepared following the reaction sequence (Steps A-F) as described for Example 6. The first eluting peak in Step E was used.

Compound 7: $^1$H NMR (400 MHz, Methanol-d4) δ 7.38-7.26 (m, 3H), 7.25-7.17 (m, 2H), 7.14 (t, J=7.7 Hz, 1H), 7.10-6.93 (m, 3H), 6.61 (dd, J=3.3, 0.9 Hz, 1H), 3.85 (d, J=2.2 Hz, 3H), 3.39-3.35 (m, 2H), 3.28-3.12 (m, 2H), 2.98-2.86 (m, 2H), 2.79 (d, J=13.6 Hz, 1H), 2.67-2.52 (m, 2H), 2.20-2.07 (m, 1H), 1.84-1.77 (m, 1H), 1.67 (s, 3H), 1.63-1.53 (m, 1H), 1.37-1.14 (m, 3H), 1.08-0.95 (m, 9H). MS (ESI): 705 m/z [M+H]$^+$. 1.44 minutes LC $R_t$, purity (LC-MS Method 01): 1.44 minutes, >99.9%/96.8% (210/254 nm).

Example 8. 3-[3-[22,28-Difluoro-3,10,10-trimethyl-12,12-dioxo-6-(trideuteriomethyl)-8,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

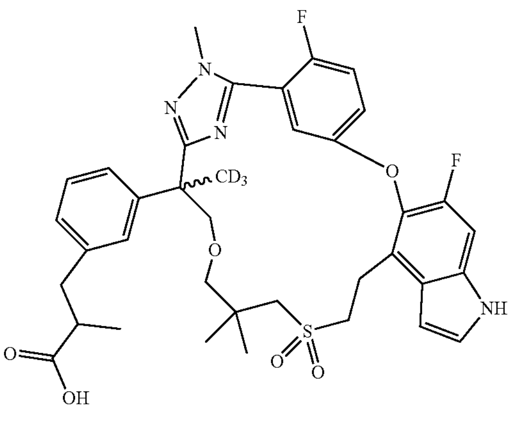 [SMILES: [2H]C([2H])([2H])C1(c2cccc(CC(C)C(=O)O)c2)COCC(C)(C)CS(=O)(=O)CCc2c(c(F)cc3[nH]ccc23)Oc2ccc(F)c(c2)-c2nc1nn2C]

Ethyl 3-[3-[22,28-difluoro-3,10,10-trimethyl-12,12-dioxo-6-(trideuteriomethyl)-8,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

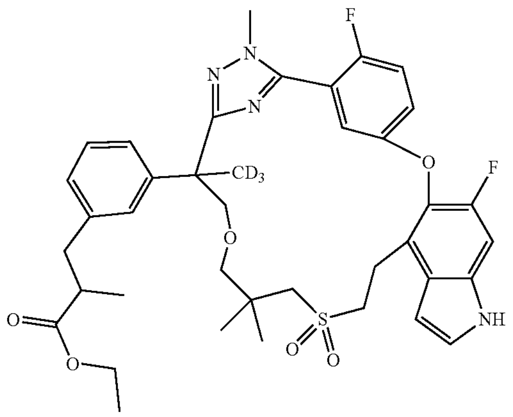 [SMILES: [2H]C([2H])([2H])C1(c2cccc(CC(C)C(=O)OCC)c2)COCC(C)(C)CS(=O)(=O)CCc2c(c(F)cc3[nH]ccc23)Oc2ccc(F)c(c2)-c2nc1nn2C]

Step A: Exchanging of methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with ethyl 3-(3-(2-((3-((2-hydroxyethyl)sulfonyl)-2,2-dimethylpropoxy)methyl)-1-(2-methylhydrazineyl)-1-oxopropan-2-yl-3,3,3-d3)phenyl)-2-methylpropanoate (intermediate 58) in Step A, the title compound was prepared following the reaction sequence (Steps A-D) as described in Example 6. MS (ESI): 738 m/z [M+H]$^{+}$. LC R (LC-MS Method 01): 1.98 minutes, Diastereomers 1 and 2 of ethyl 3-[3-[22,28-difluoro-3,10,10-trimethyl-12,12-dioxo-6-(trideuteriomethyl)-8,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

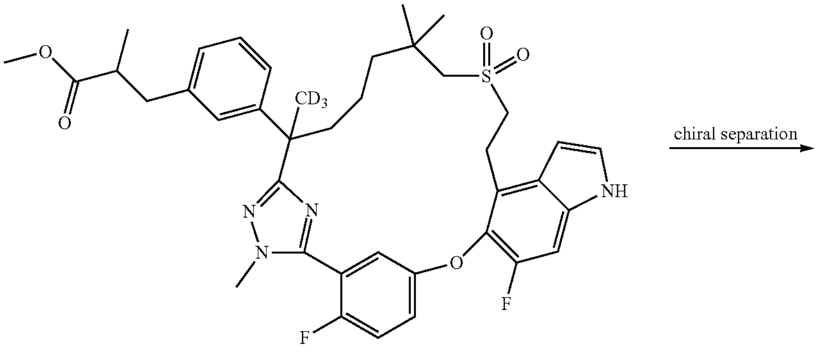

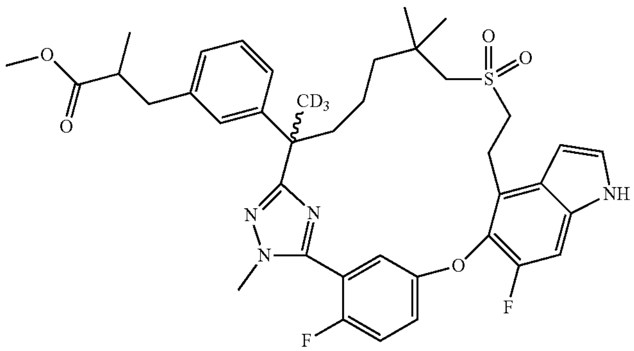

First eluent, enantiomer 1
Second eluent, enantiomer 2
Absolute configuration unknown Step B: Step A product was separated into its two constituent diastereomers by SFC using a Thar SFC-80 instrument and the following separation conditions. Column: 20×250 mm×10 μm Chiralpak AD; sample solution: 0.50 g dissolved in methanol (40 mL); injection volume: 1.0 mL; eluant: 75:25 $CO_2$/methanol with 0.5% ammonia/methanol additive; flow rate: 80 g/min; column temperature: 35° C.; back pressure: 100 bar; detection wavelength: 214 nm. Cycle time: 3.5 minutes. The first eluting isomer was designated Diastereomer 1 (0.18 g, 36%) and the second eluting isomer, Diastereomer 2 (0.18 g, 36%). Both were obtained as white solids.

Diastereomer 1, first eluent: MS (ESI): 724 m/z $[M+H]^+$. Retention time: 1.99 minutes LC R (LC-MS Method 01): 1.99 minutes.

Diastereomer 2, second eluent: MS (ESI): 724 m/z $[M+H]^+$. LC R 1.99 minutes. (LC-MS Method 01):

Compound 8A: diastereomer 1 of 3-[3-[22,28-difluoro-3,10,10-trimethyl-12,12-dioxo-6-(trideuterimethyl)-8,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid

8A

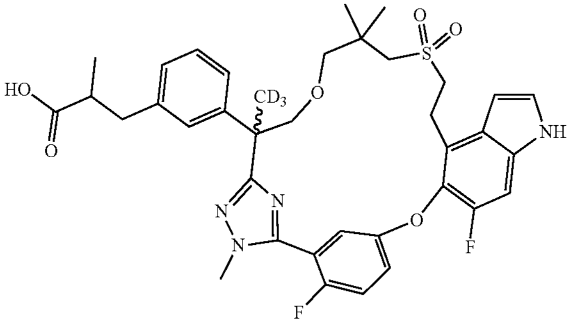

Absolute configuration unknown

Step C: Using a procedure identical to that described in step F, Example 6, the Diastereomer 1 product of step B (0.18 g, 0.25 mmol) was hydrolyzed to afford the title compound (absolute configuration unknown, 157 mg, yield 89%) as a white solid. The alpha-methyl acid is racemic.

Compound 8A: MS (ESI): 710 m/z $[M+H]^+$. LC R (LC-MS Method 06): 1.82 minutes, $^1H$ NMR (400 MHz, $CD_3OD$) δ 7.49-7.43 (m, 1H), 7.41 (t, J=9.2 Hz, 1H), 7.34 (d, J=2.8 Hz, 1H), 7.25 (d, J=10.8 Hz, 1H), 7.17 (t, J=7.6 Hz, 1H), 7.06-6.98 (m, 4H), 6.70 (d, J=3.2 Hz, 1H), 4.03 (d, J=8.0 Hz, 1H), 3.83 (d, J=1.6 Hz, 3H), 3.57 (dd, J=8.4, 3.6 Hz, 1H), 3.52-3.43 (m, 2H), 3.17 (t, J=6.8 Hz, 2H), 3.02 (d, J=8.8 Hz, 1H), 2.95-2.91 (m, 2H), 2.66-2.56 (m, 4H), 1.07 (dd, J=6.4, 2.4 Hz, 3H), 0.97 (s, 3H), 0.96 (s, 3H) ppm.

Compound 8B: diastereomer 2 of 3-[3-[22,28-difluoro-3,10,10-trimethyl-12,12-dioxo-6-(trideuterimethyl)-8,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

8B

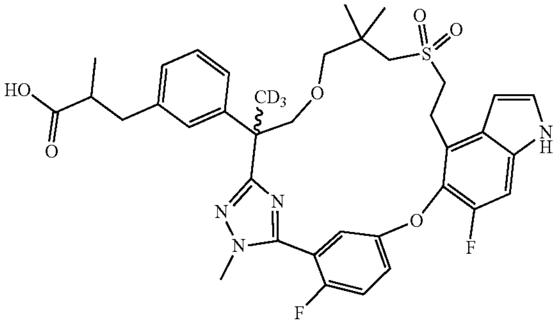

Absolute configuration unknown

Step D: Using a procedure identical to that described in step F, Example 6, the Diastereomer 2 product of step B (0.18 g, 0.25 mmol) was hydrolyzed to afford the title compound (absolute configuration unknown, 151 mg, yield 86%) as a white solid. Compound 8B: MS (ESI): 710 m/z $[M+H]^+$. LC R (LC-MS Method 01): 1.81 minutes, $^1H$ NMR (400 MHz, $CD_3OD$) δ 7.49-7.43 (m, 1H), 7.42 (t, J=9.2 Hz, 1H), 7.34 (d, J=3.6 Hz, 1H), 7.25 (d, J=10.8 Hz, 1H), 7.18 (t, J=7.6 Hz, 1H), 7.05-7.01 (m, 4H), 6.69 (d, J=2.8 Hz, 1H), 4.04 (d, J=8.4 Hz, 1H), 3.85 (d, J=1.6 Hz, 3H), 3.58 (dd, J=8.4, 4.0 Hz, 1H), 3.51-3.42 (m, 2H), 3.18 (t, J=6.8 Hz, 2H), 3.05 (d, J=8.8 Hz, 1H), 2.97-2.89 (m, 2H), 2.69-2.59 (m, 4H), 1.07 (dd, J=7.2, 3.2 Hz, 3H), 0.97 (s, 6H) ppm.

Example 9. Enantiomers 1 and 2 of 3-[3-[22,28-difluoro-3-methyl-12,12-dioxo-6,10,10-tris(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

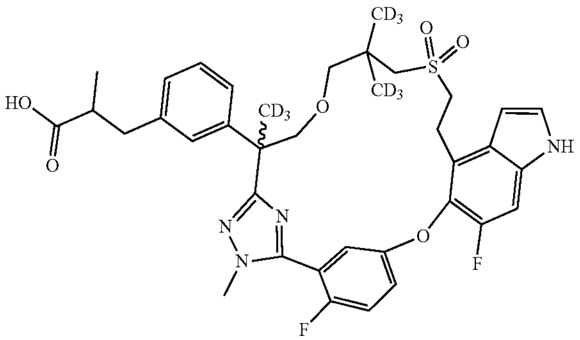 [SMILES: [2H]C([2H])([2H])C1(c2cccc(CC(C)C(=O)O)c2)COCC(C([2H])([2H])[2H])(C([2H])([2H])[2H])CS(=O)(=O)CCc2c(c(F)cc3[nH]ccc23)Oc2ccc(F)c(c2)-c2nc1nn2C]

Ethyl 3-[3-[22,28-difluoro-3-methyl-12,12-dioxo-6,10,10-tris(trideuteriomethyl)-24-oxa-12lambda6-thia-3,4,19,30-tetrazapentacyclo[23.3.1.12,5.015,23.016,20]triaconta-1(29),2(30),4,15,17,20,2225,27-nonaen-6-yl]phenyl]-2-methyl-propanoate

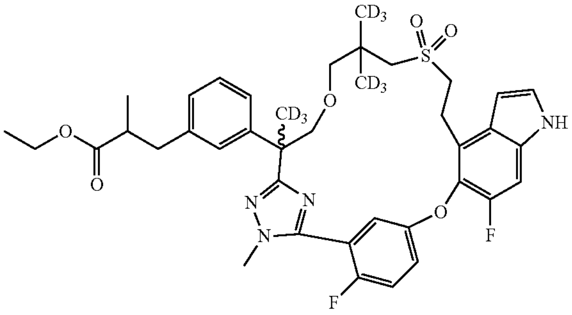 [SMILES: [2H]C([2H])([2H])C1(c2cccc(CC(C)C(=O)OCC)c2)COCC(C([2H])([2H])[2H])(C([2H])([2H])[2H])CS(=O)(=O)CCc2c(c(F)cc3[nH]ccc23)Oc2ccc(F)c(c2)-c2nc1nn2C]

Step A: Exchanging of methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)-2-methylpropanoate (intermediate 58-1) in Step A, the title compound (1.2 g) was prepared following the reaction sequence (Steps A-D) as described for Example 6. MS (ESI): 742 m/z $[M+H]^+$. LC R (LC-MS Method 07): 2.30 minutes.

3-[3-[22,28-Difluoro-3-methyl-12,12-dioxo-6,10,10-tris(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid

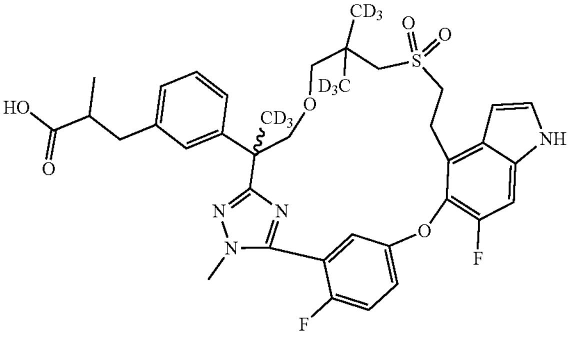 [SMILES: [2H]C([2H])([2H])C1(c2cccc(CC(C)C(=O)O)c2)COCC(C([2H])([2H])[2H])(C([2H])([2H])[2H])CS(=O)(=O)CCc2c(c(F)cc3[nH]ccc23)Oc2ccc(F)c(c2)-c2nc1nn2C]

Step B: To a solution of ethyl 3-[3-[22,28-difluoro-3-methyl-12,12-dioxo-6,10,10-tris(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step A product, 1 g, 1.35 mmol) in methanol (10 mL) and water (2 mL) was added lithium hydroxide monohydrate (170 mg, 4 mmol). The mixture was stirred at room temperature for 16 hours, then diluted with water (20 mL) and acidified with 1N hydrochloric acid to pH ~5-6. The mixture was extracted with ethyl acetate (3×20 mL). The combined organic phase was washed with water, brine, dried over sodium sulfate, filtered, and concentrated. The residue was purified by automated flash chromatography (40 g silica gel column, 0-100% ethyl acetate in petroleum ether) to afford the title compound (700 mg, 73%) as a white solid. MS (ESI): 714 m/z $[M+H]^+$. LC R (LC-MS Method 07): 2.12 minutes.

Compounds 9A and 9B: Diastereomers 1 and 2 of 3-[3-[22,28-difluoro-3-methyl-12,12-dioxo-6,10,10-tris(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

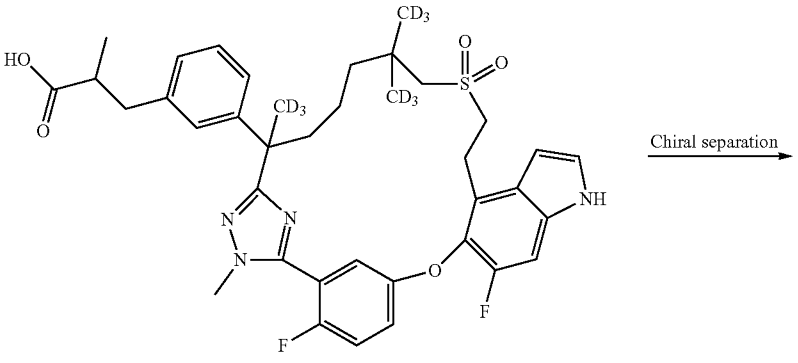

-continued

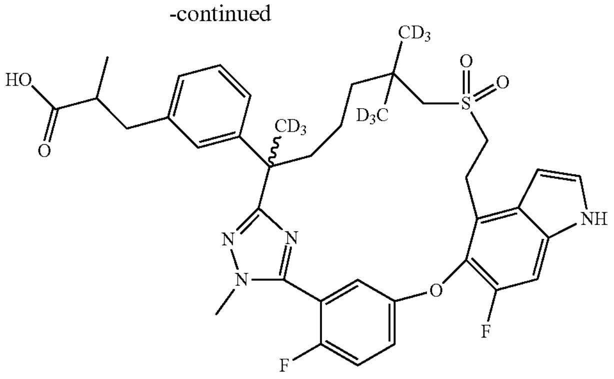

First eluent, diastereomer 1, 9A
Second eluent, diastereomer 2, 9B
Absolute configuration unknown Step C: Step B product was separated into its two constituent diastereomers by chiral column using a Gilson-281 instrument and the following separation conditions: Column: 20×250 mm×10 μm CHIRALPAK IG; sample solution: 0.70 g dissolved in methanol (20 mL); injection volume: 0.5 mL; eluant: 75:25 n-hexane (0.1% formic acid): ethanol with 0.1% formic acid; flow rate: 30 g/min; column temperature: 35° C.; detection wavelength: 214 nm. Cycle time: 20 minutes. The first eluting isomer was designated Diastereomer 1 (0.200 g, 29%) and the second eluting isomer, Diastereomer 2 (0.20 g, 29%). Both were obtained as white solids.

Compound 9A: first eluent, diastereomer 1, MS (ESI): 714 m/z $[M+H]^+$. LC R (LC-MS Method 07): 2.12 minutes. $^1H$ NMR (400 MHz, $CD_3OD$) δ 7.38-7.32 (m, 3H), 7.24-7.20 (m, 2H), 7.17 (t, J=7.6 Hz, 1H), 7.06-7.04 (m, 1H), 7.02-7.00 (m, 2H), 6.63 (d, J=3.2 Hz, 1H), 3.88 (d, J=2.0 Hz, 3H), 3.43-3.35 (m, 2H), 3.32-3.16 (m, 2H), 2.97-2.93 (m, 2H), 2.81 (d, J=13.6 Hz, 1H), 2.68-2.54 (m, 2H), 2.13 (dt, J=3.2, 12.4 Hz, 1H), 1.86-1.79 (m, 1H), 1.64-1.56 (m, 1H), 1.41-1.33 (m, 2H), 1.23-1.14 (m, 1H), 1.06 (t, J=7.2 Hz, 3H) ppm.

Compound 9B: second eluent, diastereomer 2, MS (ESI): 714 m/z $[M+H]^+$. LC R (LC-MS Method 07): 2.12 minutes. $^1H$ NMR (400 MHz, $CD_3OD$) δ 7.38-7.32 (m, 3H), 7.24-7.20 (m, 2H), 7.17 (t, J=7.6 Hz, 1H), 7.06-7.04 (m, 1H), 7.02-7.00 (m, 2H), 6.63 (d, J=3.2 Hz, 1H), 3.88 (d, J=2.0 Hz, 3H), 3.43-3.35 (m, 2H), 3.32-3.16 (m, 2H), 2.97-2.93 (m, 2H), 2.81 (d, J=13.6 Hz, 1H), 2.68-2.54 (m, 2H), 2.13 (dt, J=3.2, 12.4 Hz, 1H), 1.86-1.79 (m, 1H), 1.64-1.56 (m, 1H), 1.41-1.33 (m, 2H), 1.23-1.14 (m, 1H), 1.06 (t, J=7.2 Hz, 3H) ppm.

Example 10. Diastereomers 1 and 2 of 3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

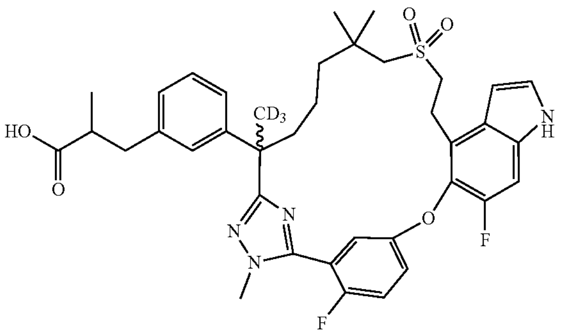

First eluent, diastereomer 1, 10A
Second eluent, diastereomer 2, 10B
Absolute configuration unknown Exchanging ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)-2-methylpropanoate (intermediate 58-1) with ethyl 3-(3-(7-((2-hydroxyethyl)sulfonyl)-6,6-dimethyl-2-(2-methylhydrazine-1-carbonyl)heptan-2-yl-1,1,1-d3)phenyl)-2-methylpropanoate (intermediate 58-2) in Step A, the title compounds were prepared following the reaction sequence (Steps A-C) as described for Example 9.

Compound 10A: first eluent, diastereomer 1 (120 mg), MS (ESI): 708 m/z $[M+H]^+$. LC R ((LC-MS Method 07): 2.12 minutes. $^1H$ NMR (400 MHz, $CD_3OD$) δ 7.39-7.30 (m, 3H), 7.24-7.15 (m, 3H), 7.07-6.96 (m, 3H), 6.63 (d, J=3.2 Hz, 1H), 3.87 (d, J=2.0 Hz, 3H), 3.45-3.35 (m, 2H), 3.30-3.17 (m, 2H), 2.97-2.91 (m, 2H), 2.81 (d, J=13.6 Hz, 1H), 2.68-2.53 (m, 2H), 2.15 (dt, J=3.6, 12.4 Hz, 1H), 1.87-1.79 (m, 1H), 1.64-1.50 (m, 1H), 1.37-1.31 (m, 2H), 1.24-1.15 (m, 1H), 1.08-1.04 (m, 9H) ppm.

Compound 10B: second eluent, diastereomer 2 (120 mg), MS (ESI): 708 m/z $[M+H]^+$. LC R ((LC-MS Method 07):

2.12 minutes. $^1H$ NMR (400 MHz, $CD_3OD$) δ 7.39-7.30 (m, 3H), 7.24-7.15 (m, 3H), 7.07-6.96 (m, 3H), 6.63 (d, J=3.2 Hz, 1H), 3.87 (d, J=2.0 Hz, 3H), 3.45-3.35 (m, 2H), 3.30-3.17 (m, 2H), 2.97-2.91 (m, 2H), 2.81 (d, J=13.6 Hz, 1H), 2.68-2.53 (m, 2H), 2.15 (dt, J=3.6, 12.4 Hz, 1H), 1.87-1.79 (m, 1H), 1.64-1.50 (m, 1H), 1.37-1.31 (m, 2H), 1.24-1.15 (m, 1H), 1.08-1.04 (m, 9H) ppm.

Example 11. Diastereomers 1 and 2 of 3-[3-[22,28-difluoro-3,6,10,10-tetramethyl-9,12,12-trioxo-24-oxa-12lambda6-thia-3,4,19,30-tetrazapentacyclo [23.3.1.12,5.015,23.016,20]triaconta-1(29),2(30),4,15,17,20,22,25,27-nonaen-6-yl]phenyl]-2-methyl-propanoic Acid

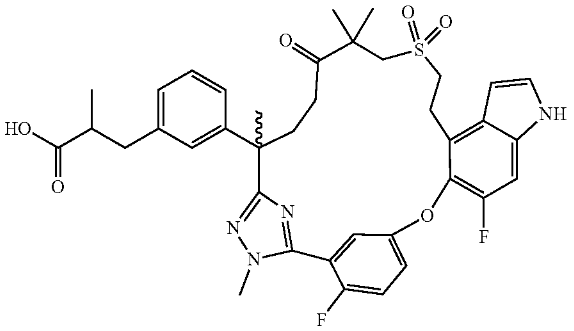 [SMILES: CC(Cc1cccc(C2(C)CCC(=O)C(C)(C)CS(=O)(=O)CCc3c(c(F)cc4[nH]ccc34)Oc3ccc(F)c(c3)-c3nc2nn3C)c1)C(=O)O]

Ethyl 3-[3-(22,28-difluoro-3,6,10,10-tetramethyl-9,12,12-trioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate

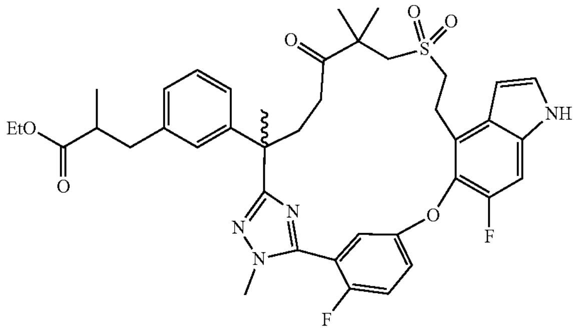 [SMILES: CC(Cc1cccc(C2(C)CCC(=O)C(C)(C)CS(=O)(=O)CCc3c(c(F)cc4[nH]ccc34)Oc3ccc(F)c(c3)-c3nc2nn3C)c1)C(=O)O]

Step A: Exchanging of methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with ethyl 3-(3-(7-((2-hydroxyethyl)sulfonyl)-2,6,6-trimethyl-1-(2-methylhydrazineyl)-1,5-dioxoheptan-2-yl)phenyl)-2-methylpropanoate in Step A, the title compound (0.2 g) was prepared following the reaction sequence (Steps A-D) as described for Example 6. MS (ESI): 747 m/z [M+H]$^+$. LC R (LC-MS Method 014): 1.48 minutes.

Diastereomers 1 and 2 of ethyl 3-[3-(22,28-difluoro-3,6,10,10-tetramethyl-9,12,12-trioxo-24-oxa-12lambda6-thia-3,4,19,30-tetrazapentacyclo [23.3.1.12,5.015,23.016,20]triaconta-1(29),2(30),4,15,17,20,22,25,27-nonaen-6-yl)phenyl]-2-methyl-propanoate

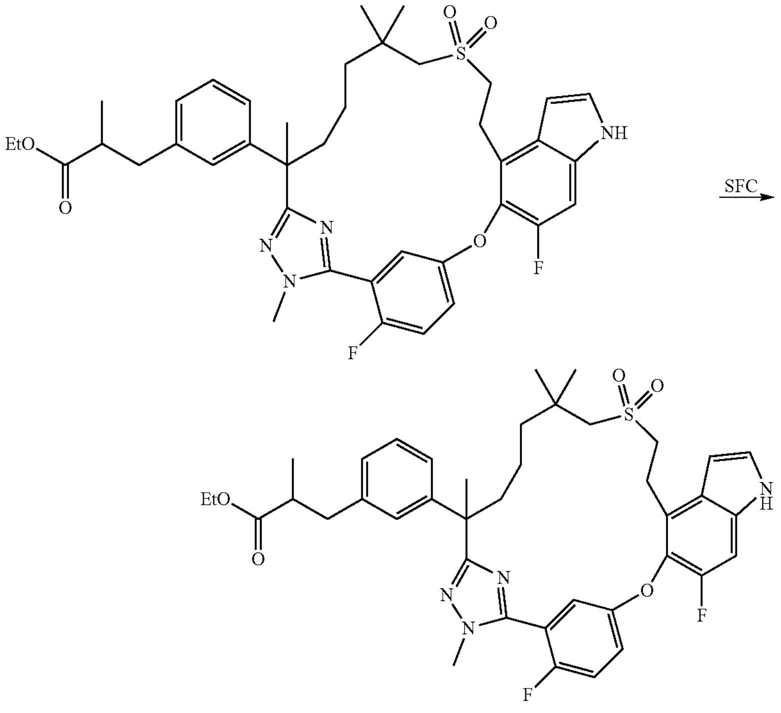

First eluent, diastereomer 1
Second eluent, diastereomer 2
Absolute configuration unknown Step B: Step A product was separated into its two constituent diastereomers by SFC using a Thar 80 instrument and the following separation conditions: Column: 20×250 mm×10 μm OZ; sample solution: 0.32 g dissolved in methanol (40 mL); injection volume: 2.0 mL; eluant: 55:45 carbon dioxide/ethanol (0.5% methanol ammonia as modifier); flow rate: 80 g/min; back pressure: 100 bar; column temperature: 35° C.; detection wavelength: 214 nM. Cycle time: 20 minutes. The first eluting isomer was designated Diastereomer 1 (0.110 g, 32%) and the second eluting isomer, Diastereomer 2 (0.110 g, 32%). Both isomers were obtained as white solids.

Diastereomer 1: MS (ESI): 747 m/z $[M+H]^+$. LC R (LC-MS Method 013): 1.98 minutes. Chiral HPLC: 100%.

Diastereomer 2: MS (ESI): 747 m/z $[M+H]^+$. LC R (LC-MS Method 013): 1.98 minutes. Chiral HPLC: 98%.

Compound HA: diastereomer 1 of 3-[3-[22,28-difluoro-3,6,10,10-tetramethyl-9,12,12-trioxo-24-oxa-12lambda6-thia-3,4,19,30-tetrazapentacyclo [23.3.1.12,5.015,23.016,20]triaconta-1(29),2(30),4,15,17,20,22,25,27-nonaen-6-yl]phenyl]-2-methyl-propanoic acid

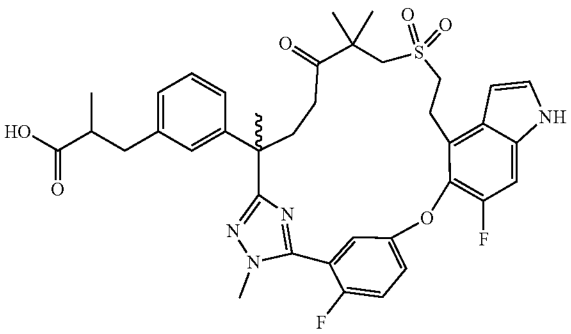

Step C: Using a procedure identical to that described in step B, Example 9, the Diastereomer 1 product of step B (0.11 g, 0.25 mmol) was hydrolyzed to afford the title compound (absolute configuration unknown, 95.7 mg, yield 90%) as a white solid.

Compound 11A: MS (ESI): 719 m/z $[M+H]^+$. LC R (LC-MS method 01): 1.31 minutes. $^1$H NMR (400 MHz, $CD_3OD$) δ 7.34-7.28 (m, 3H), 7.26 (t, J=4.0 Hz, 1H), 7.25-7.17 (m, 2H), 7.06-6.98 (m, 3H), 6.59 (d, J=3.2 Hz, 1H), 3.87 (d, J=2.4 Hz, 3H), 3.62 (d, J=14.0 Hz, 1H), 3.40-3.36 (m, 4H), 3.26 (d, J=14.2 Hz, 1H), 3.06-2.90 (m, 2H), 2.64-2.53 (m, 4H), 2.18-2.12 (m, 1H), 1.72 (s, 3H), 1.31 (s, 3H), 1.21 (s, 3H), 1.08 (dd, J=6.4, 3.2 Hz, 3H) ppm.

Compound 11B: diastereomer 2 of 3-[3-[22,28-difluoro-3,6,10,10-tetramethyl-9,12,12-trioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

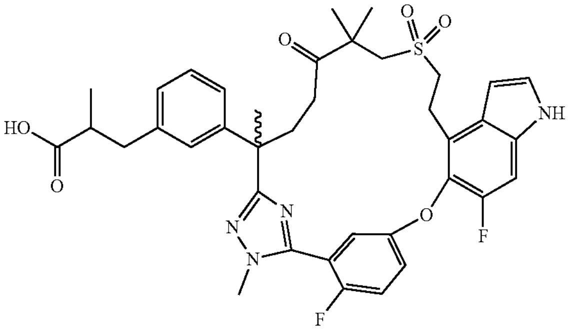 [SMILES: CC(Cc1cccc(C2(C)CCC(=O)C(C)(C)CS(=O)(=O)CCc3c(c(F)cc4[nH]ccc34)Oc3ccc(F)c(c3)-c3nc2nn3C)c1)C(=O)O]

Step D: Using a procedure identical to that described in step B, Example 9, the Diastereomer 2 product of step B (0.10 g, 0.13 mmol) was hydrolyzed to afford the title compound (absolute configuration unknown, 88.9 mg, yield 92%) as a white solid.

Compound 11B: MS (ESI): 719 m/z $[M+H]^+$. LC R (LC-MS Method 01): 1.31 minutes. $^1$H NMR (400 MHz, $CD_3OD$) δ 7.34-7.28 (m, 3H), 7.26 (t, J=3.6 Hz, 1H), 7.23-7.18 (m, 2H), 7.06-6.98 (m, 3H), 6.59 (d, J=3.2 Hz, 1H), 3.87 (d, J=2.4 Hz, 3H), 3.62 (d, J=14.0 Hz, 1H), 3.39-3.36 (m, 4H), 3.26 (d, J=14.0 Hz, 2H), 3.07-2.90 (m, 2H), 2.65-2.44 (m, 4H), 2.19-2.11 (m, 1H), 1.72 (s, 3H), 1.31 (s, 3H), 1.21 (s, 3H), 1.08 (dd, J=6.4, 3.2 Hz, 3H) ppm.

Example 12. Enantiomers 1 and 2 of 3-[3-[22,28-difluoro-3,6-dimethyl-12,12-dioxo-spiro[24-oxa-12lambda6-thia-3,4,19,30-tetrazapentacyclo [23.3.1.12,5.015,23.016,20]triaconta-1(29),2(30),4,15,17,20,22,25,27-nonaene-10,1'-cyclopropane]-6-yl]phenyl]propanoic Acid

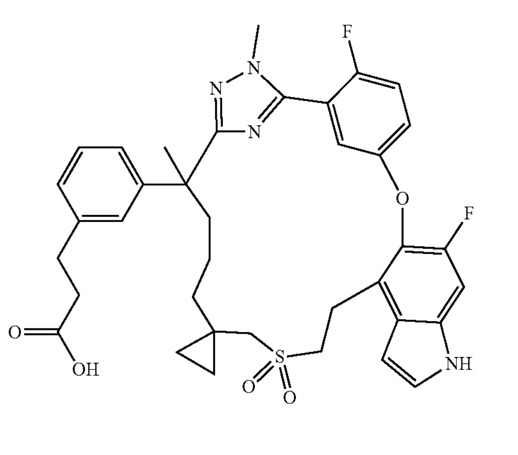 [SMILES: Cn1nc2nc1-c1cc(ccc1F)Oc1c(F)cc3[nH]ccc3c1CCS(=O)(=O)CC1(CCCC2(C)c2cccc(CCC(=O)O)c2)CC1]

Ethyl 3-[3-(22,28-difluoro-3,6-dimethyl-12,12-dioxo-spiro[24-oxa-12lambda6-thia-3,4,19,30-tetrazapentacyclo[23.3.1.12,5.015,23.016,20]triaconta-1(29),2(30),4,15,17,20,22,25,27-nonaene-10,1'-cyclopropane]-6-yl)phenyl]propanoate

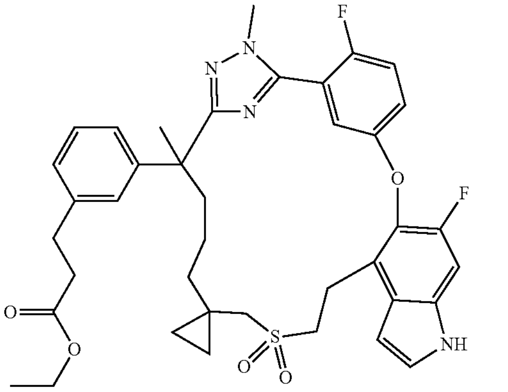 [SMILES: CCOC(=O)CCc1cccc(C2(C)CCCC3(CC3)CS(=O)(=O)CCc3c(c(F)cc4[nH]ccc34)Oc3ccc(F)c(c3)-c3nc2nn3C)c1]

Step A: Exchanging ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)-2-methylpropanoate (intermediate 58-1) with ethyl 3-(3-(5-(1-(((2-hydroxyethyl)sulfonyl)methyl)cyclopropyl)-2-methyl-1-(2-methylhydrazineyl)-1-oxopentan-2-yl)phenyl)propanoate (intermediate 69-2, 1.2 g) in Step A, the title compound (0.28 g) was prepared following the reaction sequence (Step A) as described for Example 9. MS (ESI): 717 m/z [M+H]$^+$. LC R (LC-MS Method 010): 2.06 minutes.

Enantiomers 1 and 2 of ethyl 3-[3-(22,28-difluoro-3,6-dimethyl-12,12-dioxo-spiro[24-oxa-12lambda6-thia-3,4,19,30-tetrazapentacyclo[23.3.1.12,5.015,23.016,20]triaconta-1(29),2(30),4,15,17,20,22,25,27-nonaene-10,1'-cyclopropane]-6-yl)phenyl]propanoate

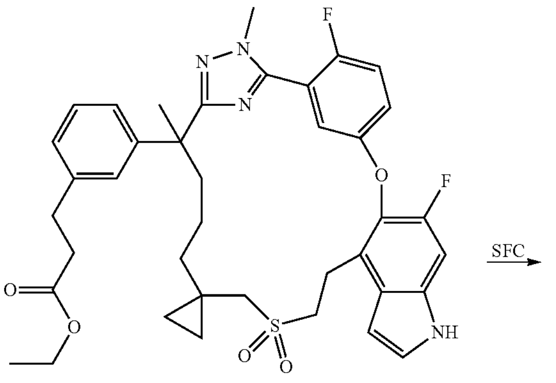

-continued

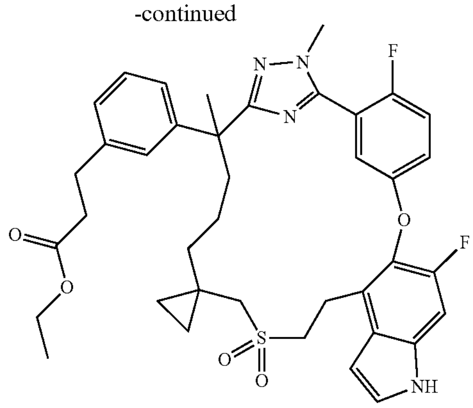

First eluent, enantiomer 1
Second eluent, enantiomer 2
Absolute configuration unknown Step B: Step A product was separated into its two constituent diastereomers by SFC using a Thar 80 instrument and the following separation conditions: Column: AD 20×250 mm, 10 μm; sample solution: 0.28 g dissolved in methanol (30 mL); injection volume: 1.0 mL; eluant: 70:30 carbon dioxide/isopropanol (0.2% methanol ammonia as modifier); flow rate: 80 g/min; back pressure: 100 bar. Column temperature: 35° C.; detection wavelength: 214 nm. Cycle time: 4.5 minutes. The first eluting isomer was designated Enantiomer 1 (0.110 g, 32%) and the second eluting isomer, Enantiomer 2 (0.100 g, 32%). Both were obtained as white solids.

Enantiomer 1: MS (ESI): 717 m/z [M+H]$^+$. LC R (LC-MS Method 012): 2.22 minutes. Chiral HPLC: 100%.

Enantiomer 2: MS (ESI): 717 m/z [M+H]$^+$. LC R (LC-MS Method 012): 2.22 minutes. Chiral HPLC: 100%.

Compound 12A: Enantiomer 1 of 3-[3-(22,28-difluoro-3,6-dimethyl-12,12-dioxo-spiro[24-oxa-12lambda6-thia-3,4,19,30-tetrazapentacyclo[23.3.1.12,5.015,23.016,20]triaconta-1(29),2(30),4,15,17,20,22,25,27-nonaene-10,1'-cyclopropane]-6-yl)phenyl]propanoic Acid

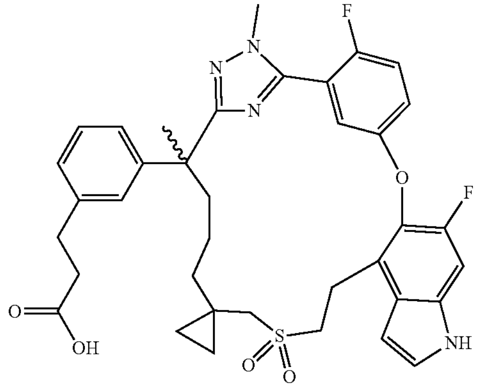 [SMILES: Cn1nc2nc1-c1cc(ccc1F)Oc1c(F)cc3[nH]ccc3c1CCS(=O)(=O)CC1(CCCC2(C)c2cccc(CCC(=O)O)c2)CC1]

Step C: Using a procedure identical to that described in step B, Example 9, the enantiomer 1 product of step B (0.110 g, 0.15 mmol) was hydrolyzed to afford the title compound (absolute configuration unknown, 102 mg, 96% yield) as a white solid.

Compound 12A: MS (ESI): 689 m/z $[M+H]^+$. LC R (LC-MS Method 01): 1.33 minutes. 1H NMR (500 MHz, $CD_3OD$) δ 7.45-7.39 (m, 2H), 7.34 (d, J=3.5 Hz, 1H), 7.24 (d, J=10.5 Hz, 1H), 7.16 (t, J=7.5 Hz, 1H), 7.09 (dd, J=5.0, 3.0 Hz, 1H), 7.04 (d, J=8.0 Hz, 1H), 7.02 (s, 1H), 6.94 (d, J=8.0 Hz, 1H), 6.64 (d, J=3.0 Hz, 1H), 3.87 (d, J=2.5 Hz, 3H), 3.54-3.41 (m, 2H), 3.15-3.02 (m, 2H), 2.93 (d, J=14.0 Hz, 1H), 2.86 (t, J=8.0 Hz, 2H), 2.76 (d, J=14.0 Hz, 1H), 2.54 (t, J=8.0 Hz, 2H), 2.20-2.14 (m, 1H), 1.90-1.84 (m, 1H), 1.77-1.71 (m, 1H), 1.69 (s, 3H), 1.61-1.52 (m, 1H), 1.31-1.21 (m, 2H), 0.41-0.31 (m, 4H) ppm.

Compound 12B: Enantiomer 2 of 3-[3-(22,28-difluoro-3,6-dimethyl-12,12-dioxo-spiro[24-oxa-12lambda6-thia-3,4,19,30-tetrazapentacyclo[23.3.1.12,5.015,23.016,20]triaconta-1(29),2(30),4,15,17,20,22,25,27-nonaene-10,1'-cyclopropane]-6-yl)phenyl]propanoic acid

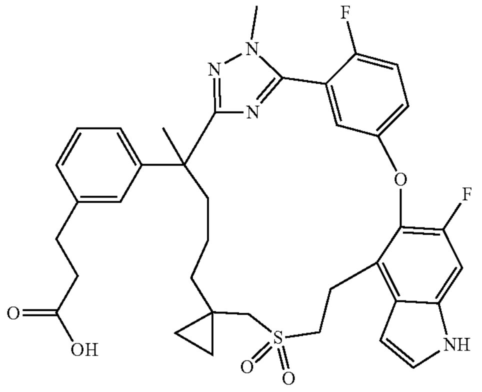 [SMILES: Cn1nc2nc1-c1cc(ccc1F)Oc1c(F)cc3[nH]ccc3c1CCS(=O)(=O)CC1(CCCC2(C)c2cccc(CCC(=O)O)c2)CC1]

Step D: Using a procedure identical to that described in step B, Example 9, the Enantiomer 1 product of step B (0.100 g, 0.14 mmol) was hydrolyzed to afford the title compound (absolute configuration unknown, 89.5 mg, 93% yield) as a white solid.

Compound 12B: MS (ESI): 689 m/z $[M+H]^+$. LC R (LC-MS Method 01): 1.33 minutes. $^1H$ NMR (500 MHz, $CD_3OD$) δ 7.45-7.39 (m, 2H), 7.34 (d, J=3.5 Hz, 1H), 7.24 (d, J=10.5 Hz, 1H), 7.16 (t, J=7.5 Hz, 1H), 7.09 (dd, J=5.0, 3.0 Hz, 1H), 7.04 (d, J=8.0 Hz, 1H), 7.02 (s, 1H), 6.94 (d, J=8.0 Hz, 1H), 6.64 (d, J=3.5 Hz, 1H), 3.87 (d, J=2.5 Hz, 3H), 3.54-3.41 (m, 2H), 3.15-3.02 (m, 2H), 2.93 (d, J=14.0 Hz, 1H), 2.86 (t, J=8.0 Hz, 2H), 2.76 (d, J=14.0 Hz, 1H), 2.54 (t, J=8.0 Hz, 2H), 2.20-2.14 (m, 1H), 1.90-1.84 (m, 1H), 1.76-1.71 (m, 1H), 1.69 (s, 3H), 1.59-1.53 (m, 1H), 1.28-1.22 (m, 2H), 0.42-0.31 (m, 4H) ppm.

Example 13. Diastereomers 1 and 2 of 3-[3-(22,28-difluoro-3,6-dimethyl-12,12-dioxo-spiro[24-oxa-12lambda6-thia-3,4,19,30-tetrazapentacyclo[23.3.1.12,5.015,23.016,20]triaconta-1(29),2(30),4,15,17,20,22,25,27-nonaene-10,1'-cyclopropane]-6-yl)phenyl]-2-methyl-propanic Acid

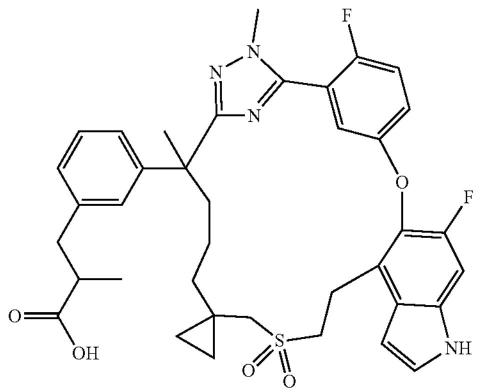 [SMILES: CC(Cc1cccc(C2(C)CCCC3(CC3)CS(=O)(=O)CCc3c(c(F)cc4[nH]ccc34)Oc3ccc(F)c(c3)-c3nc2nn3C)c1)C(=O)O]

Exchanging ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)-2-methylpropanoate (intermediate 58-1) with ethyl 3-(3-(5-(1-(((2-hydroxyethyl)sulfonyl)methyl)cyclopropyl)-2-methyl-1-(2-methylhydrazineyl)-1-oxopentan-2-yl)phenyl)-2-methylpropanoate (intermediate 69-5, 1.4 g, 4.23 mmol) in Step A, the title compounds were prepared following the reaction sequence (Steps A-C) as described for Example 9.

Compound 13A: Diastereomer 1 (75 mg), hydrolyzed product of the first eluent of separated chiral ester, MS (ESI): 703 m/z $[M+H]^+$. LC R (LC-MS Method 01): 1.37 minutes. $^1H$ NMR (500 MHz, $CD_3OD$) δ 7.46-7.39 (m, 2H), 7.33 (d, J=3.0 Hz, 1H), 7.24 (d, J=11.0 Hz, 1H), 7.16 (dt, J=7.5, 2.5 Hz, 1H), 7.09 (dd, J=5.0, 2.5 Hz, 1H), 7.01-6.93 (m, 3H), 6.65 (d, J=3.5 Hz, 1H), 3.86 (d, J=2.5 Hz, 3H), 3.54-3.42 (m, 2H), 3.14-3.03 (m, 2H), 2.98-2.92 (m, 2H), 2.75 (t, J=14.0 Hz, 1H), 2.65-2.57 (m, 2H), 2.20-2.13 (m, 1H), 1.91-1.82 (m, 1H), 1.77-1.72 (m, 1H), 1.69 (s, 3H), 1.62-1.54 (m, 1H), 1.28-1.21 (m, 2H), 1.08 (dd, J=6.5, 2.5 Hz, 3H), 0.44-0.33 (m, 4H) ppm.

Compound 13B: Diastereomer 2 (83 mg), hydrolyzed product of the second eluent of separated chiral ester. MS (ESI): 703 m/z $[M+H]^+$. LC R (LC-MS Method 01): 1.37 minutes.

$^1H$ NMR (500 MHz, $CD_3OD$) δ 7.46-7.39 (m, 2H), 7.33 (d, J=3.0 Hz, 1H), 7.24 (d, J=10.5 Hz, 1H), 7.16 (dt, J=7.5, 2.5 Hz, 1H), 7.09 (dd, J=5.0, 3.0 Hz, 1H), 7.01-6.93 (m, 3H), 6.65 (d, J=3.0 Hz, 1H), 3.86 (d, J=2.5 Hz, 3H), 3.54-3.42 (m, 2H), 3.14-3.03 (m, 2H), 2.98-2.92 (m, 2H), 2.75 (t, J=14.0 Hz, 1H), 2.65-2.56 (m, 2H), 2.20-2.13 (m, 1H), 1.91-1.82 (m, 1H), 1.77-1.71 (m, 1H), 1.69 (s, 3H), 1.62-1.54 (m, 1H), 1.28-1.21 (m, 2H), 1.08 (dd, J=6.5, 2.5 Hz, 3H), 0.44-0.33 (m, 4H) ppm.

Example 14. 1-[[3-(22,28-difluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]methyl]cyclopropanecarboxylic Acid

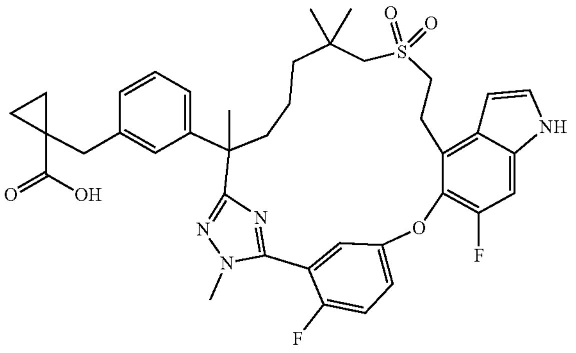 [SMILES: Cn1nc2nc1-c1cc(ccc1F)Oc1c(F)cc3[nH]ccc3c1CCS(=O)(=O)CC(C)(C)CCCC2(C)c1cccc(CC2(C(=O)O)CC2)c1]

1-[[3-(22,28-difluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]methyl]cyclopropanecarbonitrile

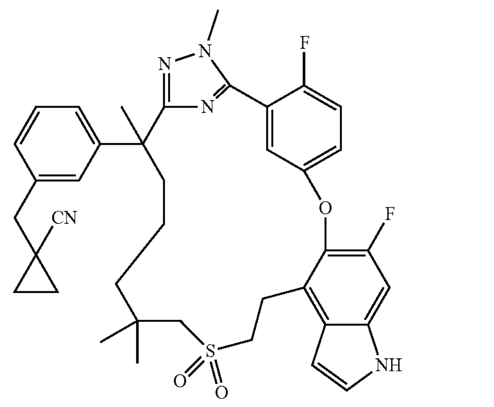 [SMILES: Cn1nc2nc1-c1cc(ccc1F)Oc1c(F)cc3[nH]ccc3c1CCS(=O)(=O)CC(C)(C)CCCC2(C)c1cccc(CC2(C#N)CC2)c1]

Step A: Exchanging ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)-2-methylpropanoate (intermediate 58-1) with 2-[3-[(1-cyano cyclopropyl)methyl]phenyl]-7-(2-hydroxyethylsulfonyl)-N',2,6,6-tetramethyl-heptanehydrazide (intermediate 69-6, 0.48 g, 0.85 mmol) in Step A, the title compounds were prepared following the reaction sequence (Steps A-C) as described for Example 9. MS (ESI): 698 m/z $[M+H]^+$. LC R (LC-MS 013): 1.98 minutes. Compound 14: 1-[[3-(22,28-difluoro-3,6,10,10-tetramethyl-12,12-dioxo-24-oxa-121 ambda6-thia-3,4,19,30-tetrazapentacyclo[23.3.1.12,5.015,23.016,20]triaconta-1(29),2(30),4,15,17,20,22,25,27-nonaen-6-yl)phenyl]methyl]cyclopropanecarboxylic Acid

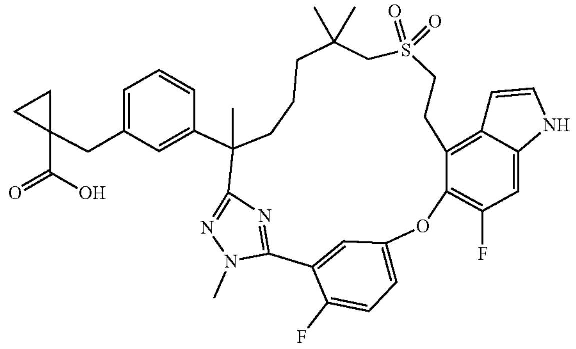 [SMILES: Cn1nc2nc1-c1cc(ccc1F)Oc1c(F)cc3[nH]ccc3c1CCS(=O)(=O)CC(C)(C)CCCC2(C)c1cccc(CC2(C(=O)O)CC2)c1]

Step B: To a stirred solution of Step A product (70 mg, 0.1 mmol) in 4 mL of ethanol was added 6M potassium hydroxide (4 mL). The mixture was stirred at 90° C. overnight, then acidified with hydrochloride (1M in water) to pH-4. The mixture was extracted with ethyl acetate (50 mL). The separated organic layer was washed with water (2×10 mL) and brine (10 mL), dried over sodium sulfate, filtered, and concentrated. The residue was purified by Prep-HPLC to give the title compound (2.8 mg, 15% yield) as a white solid.

Compound 14: MS (ESI): 717 m/z $[M+H]^+$. LC R (LC-MS Method 01): 1.47 minutes. $^1H$ NMR (400 MHz, $CD_3OD$) δ 7.38-7.32 (m, 3H), 7.23 (d, J=10.4 Hz, 1H), 7.20-7.19 (m, 1H), 7.15 (t, J=8.0 Hz, 1H), 7.06-7.04 (m, 2H), 7.00 (d, J=7.6 Hz, 1H), 6.63 (d, J=2.8 Hz, 1H), 3.87 (d, J=1.6 Hz, 3H), 3.41-3.36 (m, 2H), 3.24-3.18 (m, 2H), 3.00 (d, J=6.4 Hz, 1H), 2.96-2.82 (m, 3H), 2.18-2.11 (m, 1H), 1.85-1.79 (m, 1H) 1.69 (s, 3H), 1.63-1.58 (m, 1H), 1.38-1.30 (m, 2H), 1.24-1.14 (m, 1H), 1.08-1.02 (m, 8H), 0.66 (s, 2H) ppm.

Example 15. Enantiomers 1 and 2 of (E)-3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]prop-2-enoic acid

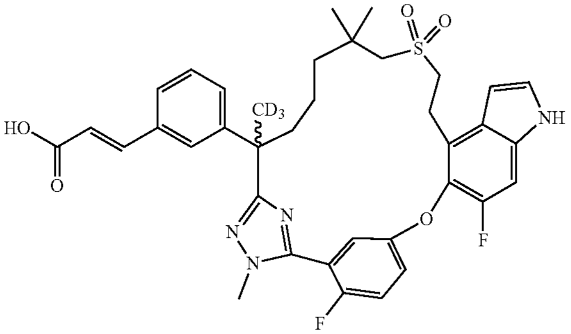 [SMILES: [2H]C([2H])([2H])C1(c2cccc(/C=C/C(=O)O)c2)CCCC(C)(C)CS(=O)(=O)CCc2c(c(F)cc3[nH]ccc23)Oc2ccc(F)c(c2)-c2nc1nn2C]

3-[22,28-Difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenol

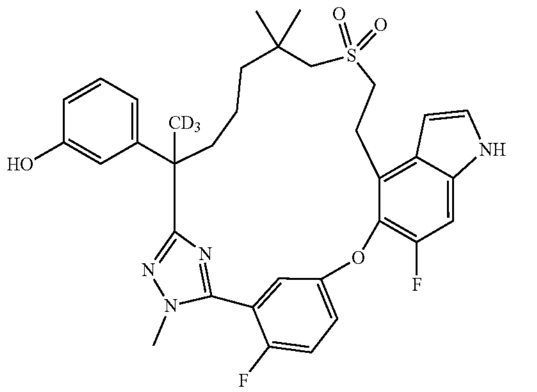 [SMILES: [2H]C([2H])([2H])C1(c2cccc(O)c2)CCCC(C)(C)CS(=O)(=O)CCc2c(c(F)cc3[nH]ccc23)Oc2ccc(F)c(c2)-c2nc1nn2C]

Step A: Exchanging ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)-2-methylpropanoate (intermediate 58-1) with 2-(3-(benzyloxy)phenyl)-7-((2-hydroxyethyl)sulfonyl)-N',2,6,6-tetramethylheptanehydrazide (intermediate 69-3, 2.75 g, 5.57 mmol) in Step A, the title compound (0.61 g) was prepared following the reaction sequence (Steps A-C) as described for Example 9. MS (ESI): 638 m/z $[M+H]^+$. LC R (LC-MS Method 014): 1.35 minutes.

[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]trifluoromethanesulfonate

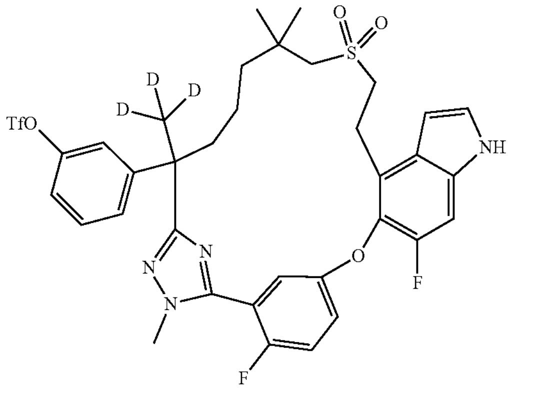 [SMILES: [2H]C([2H])([2H])C1(c2cccc(OS(=O)(=O)C(F)(F)F)c2)CCCC(C)(C)CS(=O)(=O)CCc2c(c(F)cc3[nH]ccc23)Oc2ccc(F)c(c2)-c2nc1nn2C]

Step B: To a stirred and cooled (0° C.) solution of 3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenol (Step A product, 610 mg, 0.956 mmol) in dichloromethane (30 mL) was added triethylamine (187 μL, 1.34 mmol) followed by trifluoromethanesulfonic anhydride (193 μL, 1.15 mmol). The mixture was stirred at 0° C. for 1 hour, then quenched with saturated sodium bicarbonate (30 mL). The mixture was extracted with dichloromethane (3×20 mL) and the combined organic extracts were washed with brine (20 mL), dried over sodium sulfate, filtered, and concentrated. The residue was purified by automated flash chromatography (25 g silica gel column, 0-70% ethyl acetate in petroleum ether) to give the title compound (580 mg, yield 78.8%) as a solid. MS (ESI): 770 m/z $[M+H]^+$. LC R (LC-MS Method 014): 1.53 minutes.

Ethyl (E)-3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]prop-2-enoate

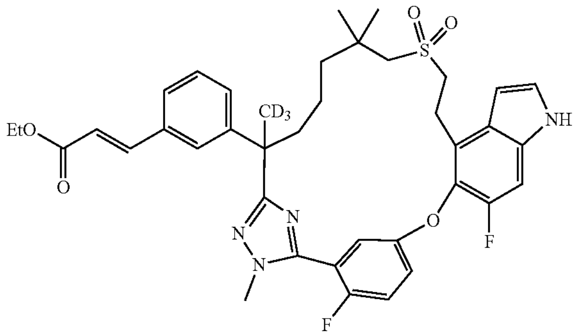 [SMILES: [2H]C([2H])([2H])C1(c2cccc(/C=C/C(=O)OCC)c2)CCCC(C)(C)CS(=O)(=O)CCc2c(c(F)cc3[nH]ccc23)Oc2ccc(F)c(c2)-c2nc1nn2C]

Step C: To a stirred solution of Step B product (120 mg, 0.156 mmol) and ethyl (E)-3-(4,4,5,5-tetramethyl-1,3,2-dioxaborolan-2-yl)prop-2-enoate (53 mg, 0.234 mmol) in DMF (6 mL) was added cesium carbonate (101 mg, 0.312 mmol) and Pd(dppf)$Cl_2$ dichloromethane complex (20 mg, 0.0234 mmol). The resulting mixture was stirred at 100° C. for 2 hours, then quenched with water (50 mL). The mixture was extracted with ethyl acetate (3×20 mL). The combined extracts were washed with brine (3×20 mL), dried over sodium sulfate, filtered, and concentrated. The residue was purified by automated flash chromatography (25 g silica gel column, 0-60% ethyl acetate in petroleum ether) to give the title compound (80 mg, 71% yield) as a solid. MS (ESI): 720 m/z $[M+H]^+$. LC R (LC-MS Method 014): 1.51 minutes.

Enantiomers 1 and 2 of ethyl (E)-3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]prop-2-enoate

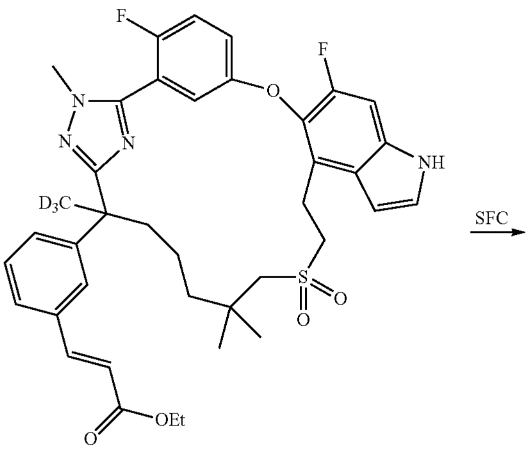

-continued

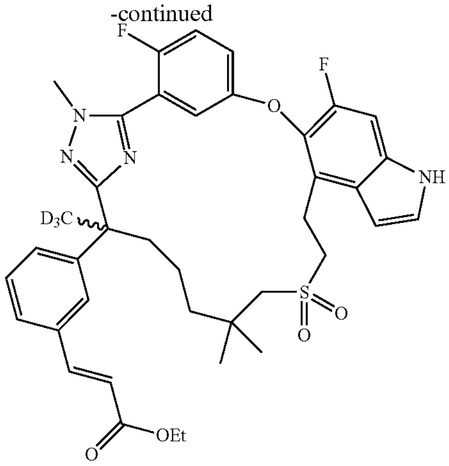

First eluent, Enantiomer 1, (15A)
Second eluent, enantiomer 2, (15B)
Absolute configuration unknown Step D: Step A product was separated into its two constituent diastereomers by SFC using an SFC-150 instrument and the following separation conditions: Column: AD 20×250 mm, 10 μm; sample solution: 0.15 g dissolved in methanol (15 mL); injection volume: 1.0 mL; eluant: 60:40 carbon dioxide/isopropanol (0.2% methanol ammonia as modifier); flow rate: 100 g/min; backpressure: 100 bar. Column temperature: 35° C.; detection wavelength: 214 nm. Cycle time: 3 minutes. The first eluting isomer was designated Diastereomer 1 (0.50 g, 33%) and the second eluting isomer, Enantiomer 2 (0.050 g, 33%). Both were obtained as white solids.

Enantiomer 1: MS (ESI): 720 m/z $[M+H]^+$. LC R (LC-MS Method 013): 2.1 minutes. Chiral HPLC: 100%.

Enantiomer 2: MS (ESI): 720 m/z $[M+H]^+$. LC R (LC-MS Method 013): 2.1 minutes. Chiral HPLC: 100%.

Compound 15A: Enantiomer 1 of (E)-3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]prop-2-enoic Acid

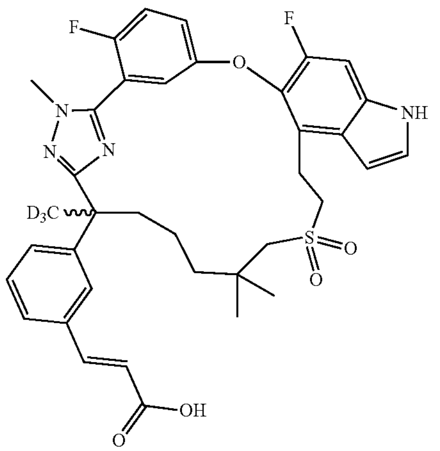 [SMILES: [2H]C([2H])([2H])C1(c2cccc(/C=C/C(=O)O)c2)CCCC(C)(C)CS(=O)(=O)CCc2c(c(F)cc3[nH]ccc23)Oc2ccc(F)c(c2)-c2nc1nn2C]

Step E: Using a procedure identical to that described in step B, Example 9, the Enantiomer 1 product of step D (0.050 g, 0.07 mmol) was hydrolyzed to afford the title compound (absolute configuration unknown, 40.8 mg, 85% yield) as a white solid.

Compound 15A: MS (ESI): 692 m/z $[M+H]^+$. LC R (LC-MS Method 04): 1.85 minutes. $^1H$ NMR (400 MHz, $CD_3OD$) δ 7.63 (d, J=15.6 Hz, 1H), 7.45-7.41 (m, 2H), 7.39-7.31 (m, 4H), 7.27-7.22 (m, 3H), 6.64 (d, J=2.8 Hz, 1H), 6.42 (d, J=16.0 Hz, 1H), 3.89 (d, J=2.4 Hz, 3H), 3.42-3.38 (m, 2H), 3.29-3.19 (m, 2H), 2.91 (d, J=13.6 Hz, 1H), 2.79 (d, J=13.6 Hz, 1H), 2.23-2.16 (m, 1H), 1.91-1.83 (m, 1H), 1.68-1.56 (m, 1H), 1.36-1.19 (m, 3H), 1.08 (s, 3H), 1.07 (s, 3H) ppm. Chiral HPLC: 100%.

Compound 15B: Enantiomer 2 of (E)-3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]prop-2-enoic Acid

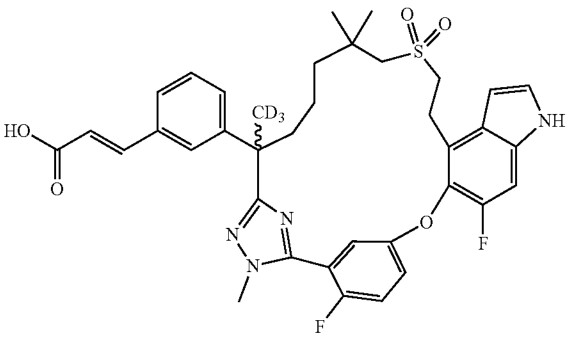 [SMILES: [2H]C([2H])([2H])C1(c2cccc(/C=C/C(=O)O)c2)CCCC(C)(C)CS(=O)(=O)CCc2c(c(F)cc3[nH]ccc23)Oc2ccc(F)c(c2)-c2nc1nn2C]

Step F: Using a procedure identical to that described in step B, Example 9, the Enantiomer 2 product of step D (0.050 g, 0.07 mmol) was hydrolyzed to afford the title compound (absolute configuration unknown, 40 mg, 85% yield) as a white solid.

Compound 15B: MS (ESI): 692 m/z $[M+H]^+$. LC (LC-MS Method 04): 1.85 minutes. $^1H$ NMR (400 MHz, $CD_3OD$) δ 7.62 (d, J=16.0 Hz, 1H), 7.45-7.41 (m, 2H), 7.37-7.31 (m, 4H), 7.26-7.22 (m, 3H), 6.64 (d, J=3.2 Hz, 1H), 6.42 (d, J=16.0 Hz, 1H), 3.89 (d, J=2.0 Hz, 3H), 3.42-3.37 (m, 2H), 3.29-3.18 (m, 2H), 2.91 (d, J=13.6 Hz, 1H), 2.79 (d, J=13.6 Hz, 1H), 2.24-2.15 (m, 1H), 1.91-1.83 (m, 1H), 1.66-1.54 (m, 1H), 1.39-1.19 (m, 3H), 1.08 (s, 3H), 1.07 (s, 3H) ppm. Chiral HPLC: 100%

Example 16. Enantiomers 1 and 2 of (E)-3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-prop-2-enoic acid

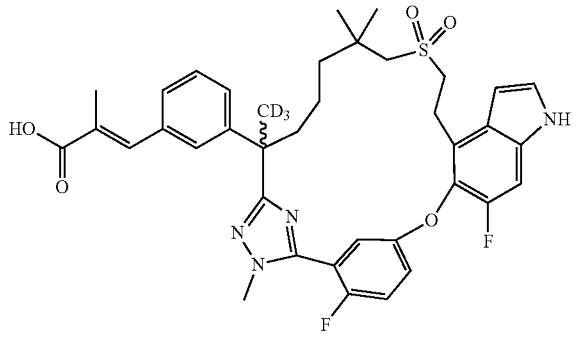 [SMILES: [2H]C([2H])([2H])C1(c2cccc(/C=C(\C)C(=O)O)c2)CCCC(C)(C)CS(=O)(=O)CCc2c(c(F)cc3[nH]ccc23)Oc2ccc(F)c(c2)-c2nc1nn2C]

Exchanging ethyl (E)-3-(4,4,5,5-tetramethyl-1,3,2-dioxaborolan-2-yl)prop-2-enoate for ethyl (E)-2-methyl-3-(4,4,5,5-tetramethyl-1,3,2-dioxaborolan-2-yl)prop-2-enoate (164 mg, 0.682 mmol) in Step C of Example 15, the title compounds were prepared following the reaction sequence (Steps C-F) as described for Example 15.

Compound 16A: Enantiomer 1, first eluent of (E)-3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-prop-2-enoic acid (105.7 mg) MS (ESI): 706 m/z $[M+H]^+$. LC R (LC-MS method 04): 1.89 minutes. $^1H$ NMR (400 MHz, $CD_3OD$) δ 7.64 (s, 1H), 7.39-7.32 (m, 4H), 7.24-7.18 (m, 5H), 6.63 (d, J=3.2 Hz, 1H), 3.88 (d, J=2.0 Hz, 3H), 3.42-3.35 (m, 2H), 3.30-3.17 (m, 2H), 2.94 (d, J=13.6 Hz, 1H), 2.81 (d, J=13.6 Hz, 1H), 2.22-2.15 (m, 1H), 1.95 (d, J=1.2 Hz, 3H), 1.90-1.83 (m, 1H), 1.70-1.57 (m, 1H), 1.39-1.28 (m, 2H), 1.24-1.17 (m, 1H), 1.08 (s, 3H), 1.06 (s, 3H) ppm. Chiral HPLC: 100%.

Compound 16B: Enantiomer 2, second eluent of (E)-3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-prop-2-enoic acid (101 mg) MS (ESI): 706 m/z $[M+H]^+$. LC R (LC-MS method 04): 1.89 minutes. $^1H$ NMR (400 MHz, $CD_3OD$) δ 7.62 (s, 1H), 7.37-7.32 (m, 4H), 7.25-7.18 (m, 5H), 6.63 (d, J=2.8 Hz, 1H), 3.88 (d, J=2.4 Hz, 3H), 3.42-3.38 (m, 2H), 3.28-3.13 (m, 2H), 2.94 (d, J=13.6 Hz, 1H), 2.81 (d, J=13.6 Hz, 1H), 2.212-2.15 (m, 1H), 1.95 (d, J=1.2 Hz, 3H), 1.91-1.84 (m, 1H), 1.69-1.56 (m, 1H), 1.37-1.31 (m, 2H), 1.26-1.20 (m, 1H), 1.08 (s, 3H), 1.07 (s, 3H) ppm. Chiral HPLC: 100%

Example 17. Enantiomer 1 and 2 of (E)-3-(3-fluoro-5-((Z)-26,46,47-trifluoro-11,9,9,13-tetramethyl-7,7-dioxido-11H,41H-3-oxa-7-thia-4(5,4)-indola-1(5,3)-triazola-2(1,3)-benzenacyclotridecaphane-13-yl)phenyl)-2-methylacrylic Acid

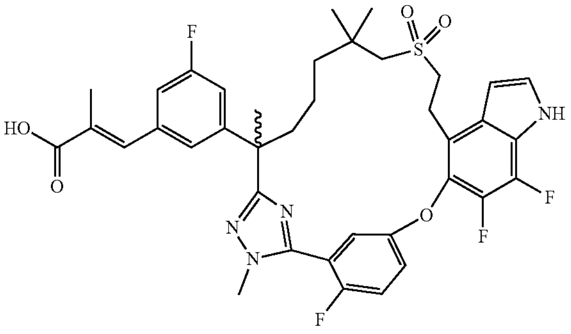 [SMILES: C/C(=C\c1cc(F)cc(C2(C)CCCC(C)(C)CS(=O)(=O)CCc3c(c(F)c(F)c4[nH]ccc34)Oc3ccc(F)c(c3)-c3nc2nn3C)c1)C(=O)O]

Exchanging 2-(3-(benzyloxy)phenyl)-7-((2-hydroxyethyl)sulfonyl)-N',2,6,6-tetramethylheptanehydrazide (intermediate 69-3) for 2-(3-(benzyloxy)-5-fluorophenyl)-7-((2-hydroxyethyl)sulfonyl)-N',2,6,6-tetramethylheptanehydrazide (intermediate 69-4, 1.21 g, 2.21 mmol), and methyl 5-((4-bromo-6-fluoro-1H-indol-5-yl)oxy)-2-fluorobenzimidothioate hydroiodide (Intermediate 14-1) for methyl 5-((4-bromo-6,7-difluoro-1H-indol-5-yl)oxy)-2-fluorobenzimidothioate hydroiodide (Intermediate 14-2, 1.2 g, 2.21 mmol) in Step A, the title compounds (17A, 54 mg and 17B, 40 mg) were prepared following the reaction sequence (Steps A-F) as described for Example 15.

Compound 17A: Enantiomer 1, product of first eluent of SFC separated ester enantiomers, of (E)-3-(3-fluoro-5-((Z)-26,46,47-trifluoro-11,9,9,13-tetramethyl-7,7-dioxido-11H,41H-3-oxa-7-thia-4(5,4)-indola-1(5,3)-triazola-2(1,3)-benzenacyclotridecaphane-13-yl)phenyl)-2-methylacrylic acid (54 mg). MS (ESI): 739 m/z $[M+H]^+$. LC R (LC-MS Method 013): 2.26 minutes. $^1H$ NMR (400 MHz, $CD_3OD$) δ 7.60 (s, 1H), 7.40-7.38 (m, 3H), 7.27-7.26 (m, 1H), 7.00 (d, J=3.6 Hz, 2H), 6.97 (s, 1H), 6.71 (t, J=2.8 Hz, 1H), 3.89 (d, J=1.6 Hz, 3H), 3.41-3.34 (m, 2H), 3.30-3.28 (m, 1H), 3.25-3.17 (m, 1H), 2.98 (d, J=13.6 Hz, 1H), 2.83 (d, J=13.6 Hz, 1H), 2.22-2.14 (m, 1H), 1.96 (s, 3H), 1.91-1.83 (m, 1H), 1.73 (s, 3H), 1.65-1.62 (m, 1H), 1.42-1.23 (m, 3H), 1.09 (s, 3H), 1.08 (s, 3H) ppm. ee %: 100%.

Compound 17B: Enantiomer 2, product of second eluent of SFC separated ester enantiomers, of (E)-3-(3-fluoro-5-((Z)-26,46,47-trifluoro-11,9,9,13-tetramethyl-7,7-dioxido-11H,41H-3-oxa-7-thia-4(5,4)-indola-1(5,3)-triazola-2(1,3)-benzenacyclotridecaphane-13-yl)phenyl)-2-methylacrylic acid (40 mg). MS (ESI): 739 m/z $[M+H]^+$. LC R (LC-MS Method 013): 2.26 minutes. $^1H$ NMR (400 MHz, $CD_3OD$) δ 7.60 (s, 1H), 7.40-7.38 (m, 3H), 7.27-7.26 (m, 1H), 7.00 (d, J=3.6 Hz, 2H), 6.97 (s, 1H), 6.71 (t, J=2.8 Hz, 1H), 3.89 (s, 3H), 3.41-3.34 (m, 2H), 3.30-3.28 (m, 1H), 3.25-3.17 (m, 1H), 2.98 (d, J=13.6 Hz, 1H), 2.83 (d, J=13.6 Hz, 1H), 2.22-2.14 (m, 1H), 1.96 (s, 3H), 1.91-1.83 (m, 1H), 1.73 (s, 3H), 1.65-1.62 (m, 1H), 1.42-1.23 (m, 3H), 1.09 (s, 3H), 1.08 (s, 3H) ppm. ee %: 98.1%

Example 18. Diastereomers 1 and 2 of 3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]-2-fluoro-phenyl]-2-methyl-propanoic Acid

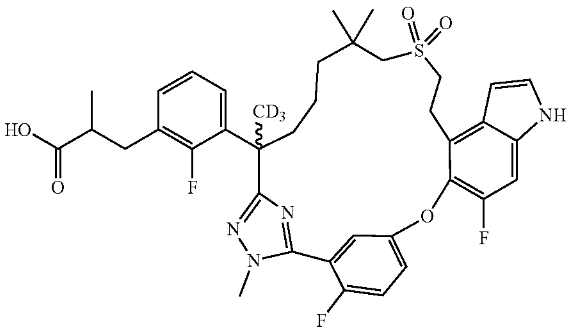 [SMILES: [2H]C([2H])([2H])C1(c2cccc(CC(C)C(=O)O)c2F)CCCC(C)(C)CS(=O)(=O)CCc2c(c(F)cc3[nH]ccc23)Oc2ccc(F)c(c2)-c2nc1nn2C]

Exchanging ethyl 3-(3-(6-(((2-hydroxyethyl)sulfonyl)methyl)-6-(methyl-d3)-2-(2-methylhydrazine-1-carbonyl)heptan-2-yl-1,1,1,7,7,7-d6)phenyl)-2-methylpropanoate (intermediate 58-1) with ethyl (E)-3-(2-fluoro-3-(7-((2-hydroxyethyl)sulfonyl)-2,6,6-trimethyl-1-(2-methylhydrazineyl)-1-oxoheptan-2-yl)phenyl)-2-methylacrylate (intermediate 58-4, 0.9 g, 1.74 mmol) in Step A, the title compounds (18A, 26 mg and 18B, 20 mg) were prepared following the reaction sequence (Steps A-C) as described for Example 9.

The racemic ester obtained in corresponding Step A of Example 9 (methyl 3-[3-[22,28-difluoro-3,10,10-trimethyl-12,12-dioxo-6-(trideuteriomethyl)-24-oxa-12lambda6-thia-3,4,19,30-tetrazapentacyclol[23.3.1.12,5.015,23.016,20]triaconta-1(29),2(30),4,15,17,20,22,25,27-nonaen-6-yl]-2-fluoro-phenyl]-2-methyl-propanate, not shown) was separated into its two constituent diastereomers by chiral separation using Gilson-281 instrument under the following conditions: column: Chiralpak IG 20×250 mm, 10 micron; column temperature: 35° C.; mobile phase: n-hexane (0.1% formic acid): isopropanol (0.1% formic acid)=80:20; Flow rate: 50 mL/min; detection wavelength: 214 nm; cycle time: 18 minutes; sample solution: 150 mg dissolved in 10 mL methanol; injection volume: 0.5 mL. The first eluting isomer was designated Diastereomer 1 (41 mg) and the second eluting isomer, Diastereomer 2 (40 mg). Both were further hydrolyzed to give corresponding title compounds, following the conditions described in Step B of Example 9.

Compound 18A, diastereomer 1 of 3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]-2-fluoro-phenyl]-2-methyl-propanoic acid (26 mg): MS (ESI): 726 m/z $[M+H]^+$. LC R (LC-MS Method 04): 1.88 minutes. $^1$H NMR (400 MHz, $CD_3OD$) δ 7.37-7.30 (m, 3H), 7.29-7.26 (m, 1H), 7.23 (d, J=10.4 Hz, 1H), 7.13 (t, J=7.6 Hz, 1H), 7.03-6.92 (m, 2H), 6.63 (d, J=3.2 Hz, 1H), 3.86 (s, 3H), 3.41-3.37 (m, 2H), 3.27-3.19 (m, 2H), 3.02-2.95 (m, 1H), 2.91 (d, J=14.0 Hz, 1H), 2.85 (d, J=14.0 Hz, 1H), 2.71-2.65 (m, 2H), 2.23-2.15 (m, 1H), 1.92-1.84 (m, 1H), 1.66-1.58 (m, 1H), 1.38-1.24 (m, 2H), 1.22-1.18 (m, 1H), 1.12-1.06 (m, 9H) ppm.

Compound 18B, diastereomer 2 of 3-[3-[22,28-difluoro-3,10,10-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]-2-fluoro-phenyl]-2-methyl-propanoic acid (20 mg): MS (ESI): 726 m/z $[M+H]^+$. LC R (LC-MS Method 04): 1.88 minutes. $^1$H NMR (400 MHz, $CD_3OD$) δ 7.37-7.30 (m, 3H), 7.28-7.25 (m, 1H), 7.23 (d, J=10.4 Hz, 1H), 7.13 (t, J=7.6 Hz, 1H), 7.03-6.94 (m, 2H), 6.63 (d, J=3.2 Hz, 1H), 3.86 (s, 3H), 3.40-3.37 (m, 2H), 3.27-3.20 (m, 2H), 3.01-2.93 (m, 1H), 2.91 (d, J=13.2 Hz, 1H), 2.85 (d, J=14.0 Hz, 1H), 2.72-2.65 (m, 2H), 2.23-2.14 (m, 1H), 1.92-1.83 (m, 1H), 1.67-1.58 (m, 1H), 1.36-1.24 (m, 2H), 1.22-1.18 (m, 1H), 1.12-1.06 (m, 9H) ppm.

Example 19. Diastereomers 1 and 2 of 2-[3-[22,28-Difluoro-3,6,10,10-tetramethyl-12,12-dioxo-24-oxa-12λ$^6$-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl]phenoxy]propanoic Acid

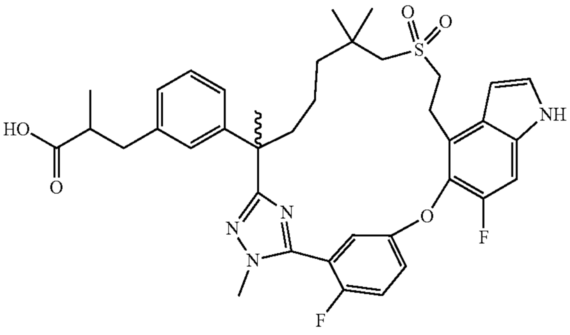 [SMILES: CC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

Ethyl 2-[3-[22,28-Difluoro-3,6,10,10-tetramethyl-12,12-dioxo-24-oxa-12 6-thia-3,4,19,30-tetrazapentacyclo[23.3.1.12,5.015,23.016,20]triaconta-1(29),2(30),4,15,17,20,22,25,27-nonaen-6-yl]phenoxy]propanoate

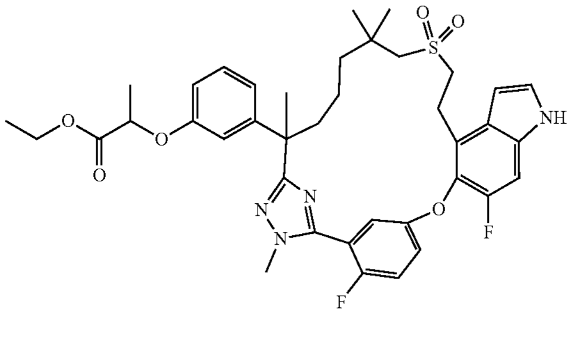 [SMILES: CCOC(=O)C(C)Oc1cccc(C2(C)CCCC(C)(C)CS(=O)(=O)CCc3c(c(F)cc4[nH]ccc34)Oc3ccc(F)c(c3)-c3nc2nn3C)c1]

Step A: Exchanging of methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with ethyl 2-(3-(7-((2-hydroxyethyl)sulfonyl)-2,6,6-trimethyl-1-(2-methylhydrazineyl)-1-oxoheptan-2-yl)phenoxy)propanoate (intermediate 69-7, 2.5 g, 4.99 mmol) in Step A, the title compound was prepared following the reaction sequence (Steps A-D) as described for Example 6. MS (ESI): 735 m/z $[M+H]^+$. LC R (LC-MS Method 04): 2.02 minutes.

Diastereomers 1 and 2 of ethyl 2-[3-[22,28-difluoro-3,6,10,10-tetramethyl-12,12-dioxo-24-oxa-12 6-thia-3,4,19,30-tetrazapentacyclo[23.3.1.12,5.015,23.016,20]triaconta-1(29),2(30),4,15,17,20,22,25,27-nonaen-6-yl]phenoxy]propanoate

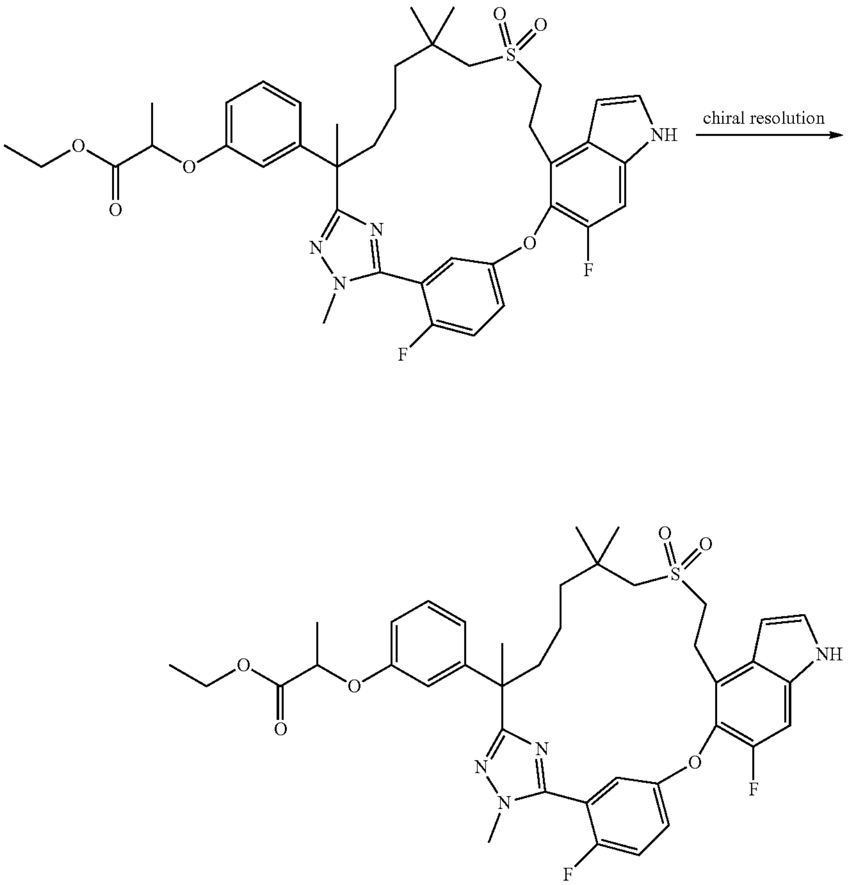

First eluent, diastereomer 1
Second eluent, diastereomer 2
Absolute configuration unknown Step B: Step A product was separated into its two constituent diastereomers by SFC using an SFC-200 instrument and the following separation conditions: Column: IC 20×250 mm, 10 μm; sample solution: 0.65 g dissolved in methanol (25 mL); injection volume: 1.2 mL; eluant: 75:25 carbon dioxide/methanol (0.2% methanol ammonia as modifier); flow rate: 130 g/min; back pressure: 100 bar. Column temperature: 35° C.; detection wavelength: 214 nm. Cycle time: 6.2 minutes. The first eluting isomer was designated Diastereomer 1 (0.27 g, 42%) and the second eluting isomer, Diastereomer 2 (0.27 g, 42%). Both were obtained as white solids.

Diastereomer 1: MS (ESI): 735 m/z $[M+H]^+$. LC R (LC-MS Method 04): 2.03 minutes. Chiral HPLC: 100%.

Diastereomer 2: MS (ESI): 735 m/z $[M+H]^+$. LC R (LC-MS Method 04): 2.03 minutes. Chiral HPLC: 100%.

Compound 19A: Diastereomer 1 of 2-[3-[22,28-difluoro-3,6,10,10-tetramethyl-12,12-dioxo-24-oxa-12 6-thia-3,4,19,30-tetrazapentacyclo[23.3.1.12,5.015,23.016,20]triaconta-1(29),2(30),4,15,17,20,22,25,27-nonaen-6-yl]phenoxy]propanoic Acid

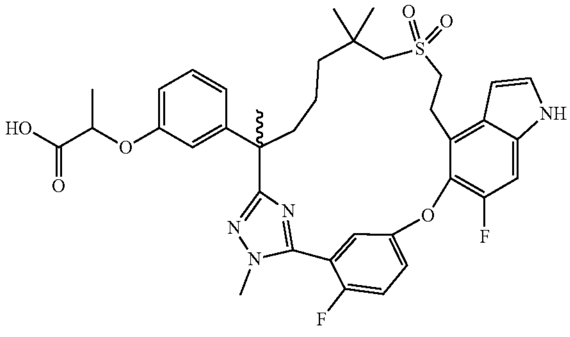 [SMILES: CC(Oc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

Step C: Using a procedure identical to that described in step B, Example 9, the Diastereomer 1 product of step B (0.27 g) was hydrolyzed to afford the title compound (absolute configuration unknown, 250 mg, 96% yield) as a white solid.

Compound 19A: MS (ESI): 707 m/z $[M+H]^+$. Retention time: 1.40 minutes (LC-MS Method 01). $^1H$ NMR (400 MHz, $CD_3OD$) δ 7.38-7.30 (m, 3H), 7.24-7.22 (m, 2H), 7.17 (td, J=8.0 Hz, 0.4 Hz 1H), 6.82 (t, J=7.6 Hz, 1H), 6.75-6.64 (m, 2H), 6.63 (d, J=2.8 Hz, 1H), 4.60-4.48 (m, 1H), 3.87 (d, J=2.0 Hz, 3H), 3.43-3.35 (m, 2H), 3.31-3.15 (m, 2H), 2.97 (d, J=13.6 Hz, 1H), 2.82 (dd, J=13.6, 6.0 Hz, 1H), 2.13 (td, J=12.8, 3.2 Hz 1H), 1.87-1.78 (m, 1H), 1.69 (s, 3H), 1.64-1.57 (m, 1H), 1.52 (dd, J=11.2, 6.8 Hz, 3H), 1.38-1.29 (m, 1H), 1.23-1.13 (m, 1H), 1.08-1.02 (m, 7H) ppm.

Compound 19B: Diastereomer 2 of 2-[3-[22,28-difluoro-3,6,10,10-tetramethyl-12,12-dioxo-24-oxa-12 6-thia-3,4,19,30-tetrazapentacyclo[23.3.1.12,5.015,23.016,20]triaconta-1(29),2(30),4,15,17,20,22,25,27-nonaen-6-yl]phenoxy] propanoic Acid

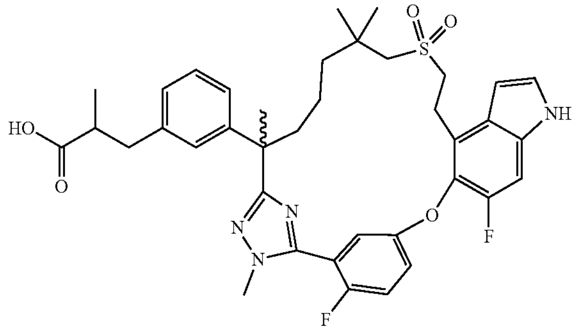 [SMILES: CC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

Step D: Using a procedure identical to that described in step B, Example 9, the Diastereomer 2 product of step B (0.27 g) was hydrolyzed to afford the title compound (absolute configuration unknown, 248 mg, 95% yield) as a white solid.

Compound 19B: MS (ESI): 707 m/z $[M+H]^+$. Retention time: 1.4 minutes (LC-MS Method 01). $^1H$ NMR (400 MHz, $CD_3OD$) δ 7.26-7.20 (m, 3H), 7.12-7.10 (m, 2H), 7.05 (td, J=8.0, 0.8 Hz 1H), 6.69 (t, J=7.6 Hz, 1H), 6.63-6.52 (m, 2H), 6.51 (d, J=2.4 Hz, 1H), 4.58-4.46 (m, 1H), 3.75 (d, J=2.0 Hz, 3H), 3.29-3.23 (m, 2H), 3.19-3.09 (m, 2H), 2.85 (d, J=13.6 Hz, 1H), 2.74-2.66 (m, 1H), 2.05-1.95 (m, 1H), 1.75-1.66 (m, 1H), 1.57 (s, 3H), 1.52-1.45 (m, 1H), 1.44-1.36 (m, 3H), 1.25-1.17 (m, 1H), 1.11-1.04 (m, 1H), 0.96-0.86 (m, 7H) ppm.

Example 20. Diastereomer 1 and 2 of 3-[3-(6-cyano-22,28-difluoro-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

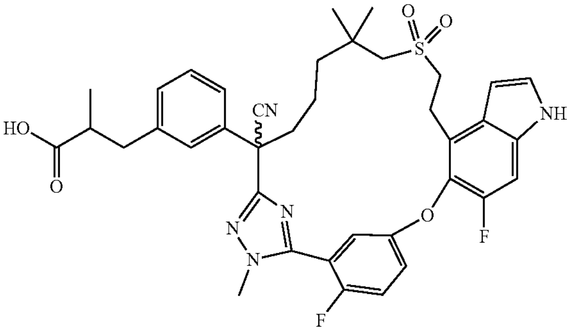 [SMILES: CC(Cc1cccc(C2(C#N)CCCC(C)(C)CS(=O)(=O)CCc3c(c(F)cc4[nH]ccc34)Oc3ccc(F)c(c3)-c3nc2nn3C)c1)C(=O)O]

Ethyl 3-[3-[22,28-difluoro-6-(hydroxymethyl)-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

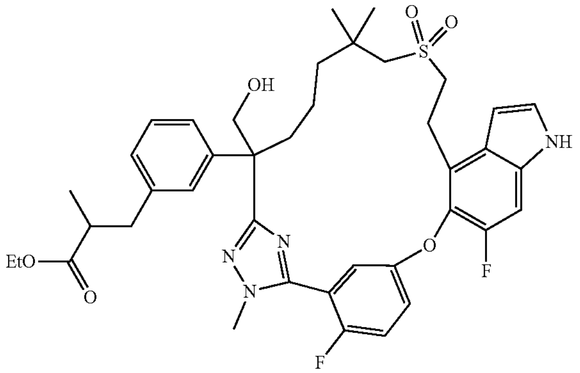 [SMILES: CCOC(=O)C(C)Cc1cccc(C2(CO)CCCC(C)(C)CS(=O)(=O)CCc3c(c(F)cc4[nH]ccc34)Oc3ccc(F)c(c3)-c3nc2nn3C)c1]

Step A: Exchanging of methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with ethyl (E)-3-(3-(2-((benzyloxy)methyl)-7-((2-hydroxyethyl)sulfonyl)-6,6-dimethyl-1-(2-methylhydrazineyl)-1-oxoheptan-2-yl)phenyl)-2-methylacrylate (intermediate 69-8, 4.0 g, 6.64 mmol) in Step A, the title compound was prepared following the reaction sequence (Steps A-D) as described for Example 6. MS (ESI): 749 m/z $[M+H]^+$. LC R (LC-MS Method 002): 1.75 minutes.

Ethyl 3-[3-(22,28-difluoro-6-formyl-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate

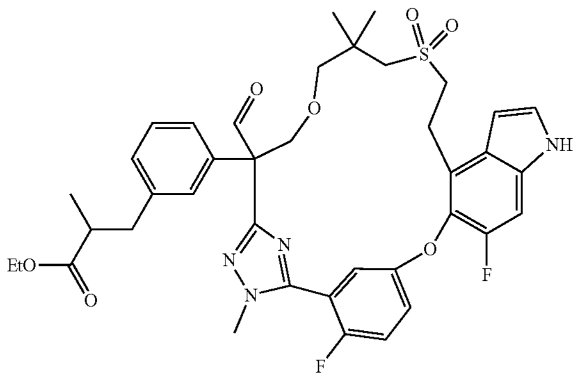 [SMILES: CCOC(=O)C(C)Cc1cccc(C2(C=O)COCC(C)(C)CS(=O)(=O)CCc3c(c(F)cc4[nH]ccc34)Oc3ccc(F)c(c3)-c3nc2nn3C)c1]

Step B: To a stirred solution of Step A product (500 mg, 0.668 mmol) in dimethyl sulfoxide (5 mL) was added 2-iodoxybenzoic acid (46%, 561 mg, 0.921 mmol). The mixture was stirred at room temperature for 16 hours, then quenched with saturated sodium bicarbonate aqueous solution (20 mL), and the mixture was extracted with ethyl acetate (3×20 mL). The combined organic layers were washed with saturated sodium bicarbonate aqueous solution (4×30 mL), brine (30 mL), dried over anhydrous sodium sulfate, filtered, and concentrated to give the title compound (490 mg, 98% yield) as a light-yellow solid. MS (ESI): 747 m/z [M+H]$^+$. LC R (LC-MS Method 002): 1.87 minutes.

Ethyl 3-[3-[22,28-difluoro-6-(hydroxyiminomethyl)-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

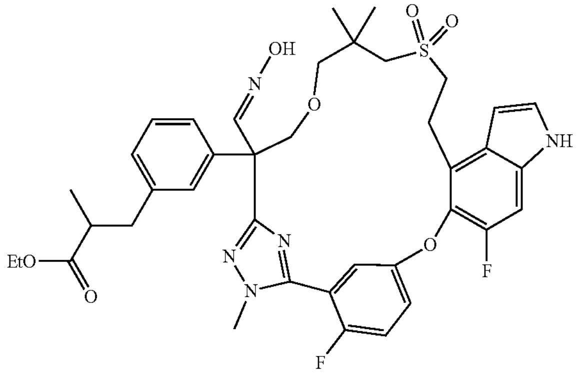 [SMILES: CCOC(=O)C(C)Cc1cccc(C2(C=NO)COCC(C)(C)CS(=O)(=O)CCc3c(c(F)cc4[nH]ccc34)Oc3ccc(F)c(c3)-c3nc2nn3C)c1]

Step C: To a stirred solution of Step B product (460 mg, 0.616 mmol) in ethanol (10 mL) was added hydroxylamine (203 mg, 3.08 mmol, 50% in water). The reaction was stirred at 85° C. for 1 hour, then diluted with water (100 mL). The mixture was extracted with dichloroethane (3×50 mL), washed with brine (2×80 mL), dried over anhydrous sodium sulfate, filtered, and concentrated to give the title compound (460 mg, 98% yield) as light-yellow solid. MS (ESI): 762 m/z [M+H]$^+$. LC R (LC-MS Method 002): 1.91 minutes.

Ethyl 3-[3-(6-cyano-22,28-difluoro-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate

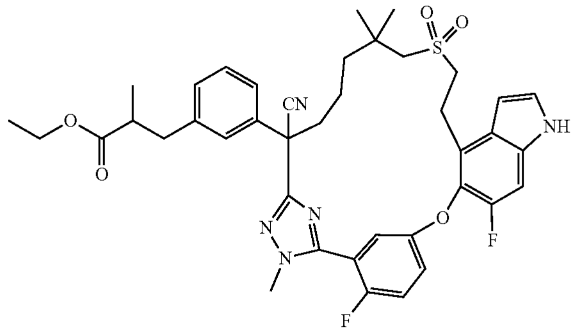 [SMILES: CCOC(=O)C(C)Cc1cccc(C2(C#N)CCCC(C)(C)CS(=O)(=O)CCc3c(c(F)cc4[nH]ccc34)Oc3ccc(F)c(c3)-c3nc2nn3C)c1]

Step D: To a stirred solution of Step C product (460 mg, 0.604 mmol) in N,N-dimethylformamide (10 mL) was added n-propylphosphonic cyclic anhydride (1.92 g, 3.02 mmol, 50% in ethyl acetate) at room temperature. The mixture was stirred at 100° C. for 2 hours, then diluted with water (60 mL). The mixture was extracted with ethyl acetate (3×40 mL). The combined organic layers were dried over anhydrous sodium sulfate, filtered, and concentrated. The residue was purified by flash chromatography (10 g silica gel column, 0-60% ethyl acetate in petroleum ether) to give the title compound (300 mg, yield 67%) as a white solid. MS (ESI): 744 m/z [M+H]$^+$. LC R (LC-MS Method 003): 1.98 minutes.

Diastereomers 1 and 2 of ethyl 3-[3-(6-cyano-22,28-difluoro-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate

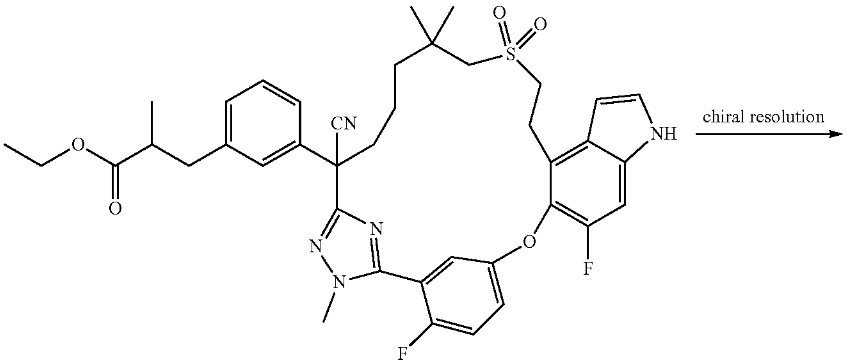

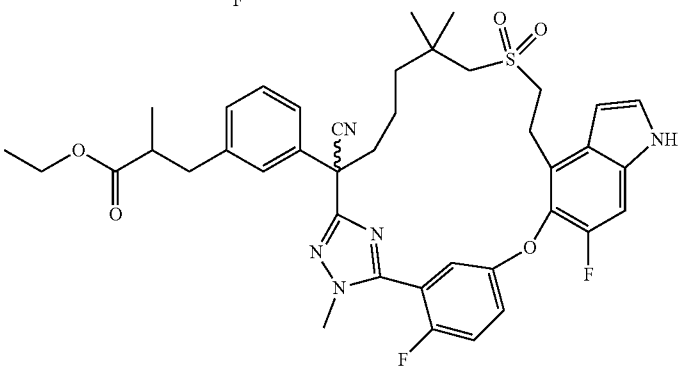

First eluent: Diastereomer 1
Second eluent: Diastereomer 2
Absolute configuration unknown Step E: Step D product was separated into its two constituent diastereomers by SFC using an SFC-80 instrument and the following separation conditions: Column: QZ 20×250 mm, 10 μm; sample solution: 0.30 g dissolved in methanol (25 mL); injection volume: 0.6 mL; eluant: 55:45 carbon dioxide/methanol (0.2% methanol ammonia as modifier); flow rate: 80 g/min; back pressure: 100 bar. Column temperature: 35° C.; detection wavelength: 214 nm. Cycle time: 4.0 minutes. The first eluting isomer was designated Diastereomer 1 (0.12 g, 42%) and the second eluting isomer, Diastereomer 2 (0.10 g, 42%). Both were obtained as white solids.

Diastereomer 1: MS (ESI): 744 m/z $[M+H]^+$. LC R (LC-MS Method 002): 1.85 minutes. Chiral HPLC: 100%.

Diastereomer 2: MS (ESI): 744 m/z $[M+H]^+$. LC R (LC-MS Method 002): 1.85 minutes. Chiral HPLC: 100%.

Compound 20A, Diastereomer 1 of 3-[3-[6-cyano-22,28-difluoro-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

20A

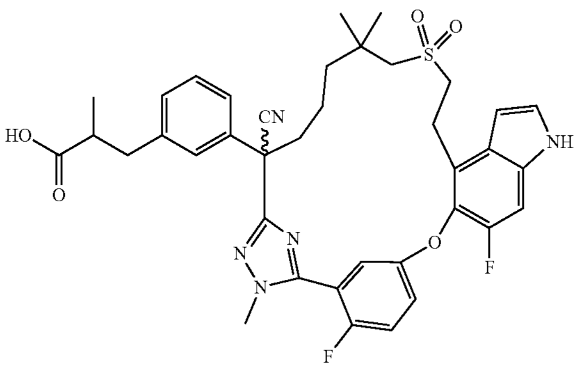

Absolute configuration unknown

Step F: Using a procedure identical to that described in step B, Example 9, the Diastereomer 1 product of step E (0.12 g) was hydrolyzed to afford the title compound (absolute configuration unknown, 105 mg, 90% yield) as a white solid.

Compound 20A: MS (ESI): 716 m/z $[M+H]^+$. Retention time: 1.37 minutes (LC-MS Method 01). $^1H$ NMR (400 MHz, $CD_3OD$) δ 7.39-7.38 (m, 2H), 7.34 (d, J=3.2 Hz, 1H), 7.30-7.23 (m, 5H), 7.19-7.17 (m, 1H), 6.65 (d, J=2.8 Hz, 1H), 3.88 (dd, J=2.0, 1.2 Hz, 3H), 3.43-3.38 (m, 3H), 3.30-3.25 (m, 1H), 3.02-2.89 (m, 3H), 2.68-2.63 (m, 2H), 2.52 (t, J=12 Hz, 1H), 2.15-2.06 (m, 1H), 1.74-1.66 (m, 1H), 1.46-1.25 (m, 3H), 1.17 (s, 3H), 1.08 (dd, J=6.4, 2.4 Hz, 3H), 1.03 (s, 3H) ppm.

Compound 20B, Diastereomer 2 of 3-[3-[6-cyano-22,28-difluoro-3,10,10-trimethyl-12,12-dioxo-24-oxa-12lambda6-thia-3,4,19,30-tetrazapentacyclo [23.3.1.12,5.015,23.016,20]triaconta-1(29),2(30),4,15,17,20,22,25,27-nonaen-6-yl]phenyl]-2-methyl-propanoic acid

20B

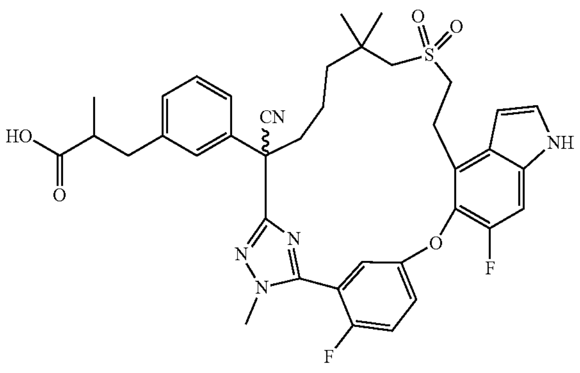

Absolute configuration unknown

Step G: Using a procedure identical to that described in step B, Example 9, the Diastereomer 2 product of step E (0.10 g) was hydrolyzed to afford the title compound (absolute configuration unknown, 61 mg, 63% yield) as a white solid.

Compound 20B: MS (ESI): 716 m/z $[M+H]^+$. Retention time: 1.38 minutes (LC-MS Method 01). $^1H$ NMR (400 MHz, $CD_3OD$) δ 7.39-7.38 (m, 2H), 7.34 (d, J=3.2 Hz, 1H), 7.30-7.23 (m, 5H), 7.20-7.17 (m, 1H), 6.65 (d, J=3.2 Hz, 1H), 3.88 (dd, J=1.6, 0.8 Hz, 3H), 3.43-3.37 (m, 3H), 3.30-3.26 (m, 1H), 3.02-2.89 (m, 3H), 2.68-2.64 (m, 2H), 2.52 (t, J=12.4 Hz, 1H), 2.14-2.05 (m, 1H), 1.76-1.69 (m, 1H), 1.48-1.35 (m, 3H), 1.17 (s, 3H), 1.08 (dd, J=6.4, 2.4 Hz, 3H), 1.02 (s, 3H) ppm.

Example 21. 3-[3-(22,28-Difluoro-6,10,10-trimethyl-13,13-dioxo-24-oxa-13lambda6-thia-3,19,30-triazapentacyclo[23.3.1.12,5.015,23.016,20]triaconta-1(29),2,4,15(23),16(20),17,21,25,27-nonaen-6-yl)phenyl]propanoic Acid

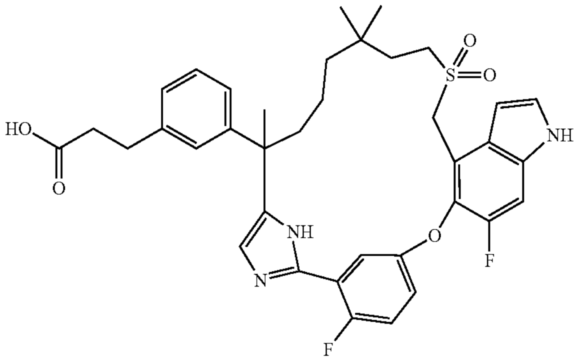 [SMILES: CC1(C)CCCC(C)(c2cccc(CCC(=O)O)c2)c2cnc([nH]2)-c2cc(ccc2F)Oc2c(F)cc3[nH]ccc3c2CS(=O)(=O)CC1]

Ethyl 2-(((5-(3-(5-(7-acetoxy-2-(3-iodophenyl)-6,6-dimethylheptan-2-yl)-1H-imidazol-2-yl)-4-fluorophenoxy)-6-fluoro-1-(phenylsulfonyl)-1H-indol-4-yl)methyl)sulfonyl)acetate

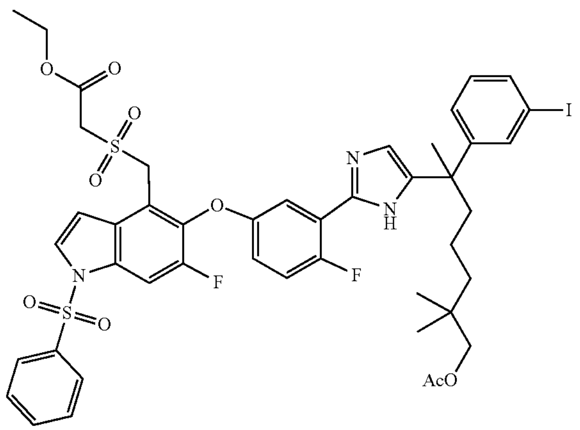 [SMILES: CCOC(=O)CS(=O)(=O)Cc1c(Oc2ccc(F)c(-c3ncc(C(C)(CCCC(C)(C)COC(C)=O)c4cccc(I)c4)[nH]3)c2)c(F)cc2c1ccn2S(=O)(=O)c1ccccc1]

Step A: To a stirred solution of 8-bromo-6-(3-iodophenyl)-2,2,6-trimethyl-7-oxooctyl acetate (Intermediate 17, 1.29 g, 2.54 mmol) in N,N-dimethylformamide (25 mL) was added ethyl 2-(((5-(3-carbamimidoyl-4-fluorophenoxy)-6-fluoro-1-(phenylsulfonyl)-1H-indol-4-yl)methyl)sulfonyl) acetate (Intermediate 18, 1.5 g, 2.54 mmol) and sodium bicarbonate (0.426 g, 5.07 mmol). The reaction was stirred at 75° C. for 12 hours, cooled to room temperature and then quenched with water (30 ml). The mixture was extracted with ethyl acetate (50 mL×3). The combined organic extracts were washed with brine (30 mL), dried over sodium sulfate and concentrated. The residue was purified by silica gel column (50% ethyl acetate in petroleum ether) to give the title product as a yellow solid (1.5 g, 59%). MS (ESI): 1002 m/z $[M+H]^+$.

2-(((6-Fluoro-5-(4-fluoro-3-(5-(7-hydroxy-2-(3-iodophenyl)-6,6-dimethylheptan-2-yl)-1H-imidazol-2-yl)phenoxy)-1H-indol-4-yl)methyl)sulfonyl)acetic Acid

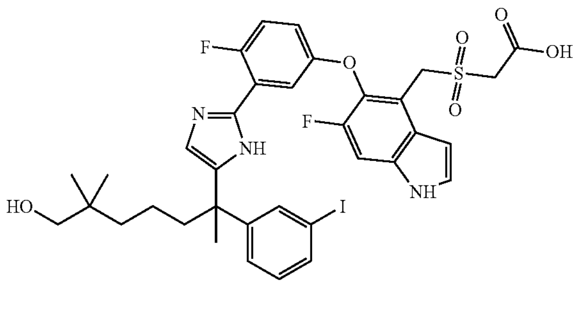 [SMILES: CC(C)(CO)CCCC(C)(c1cccc(I)c1)c1cnc(-c2cc(Oc3c(F)cc4[nH]ccc4c3CS(=O)(=O)CC(=O)O)ccc2F)[nH]1]

Step B: To a stirred solution of ethyl 2-(((5-(3-(5-(7-acetoxy-2-(3-iodophenyl)-6,6-dimethylheptan-2-yl)-1H-imidazol-2-yl)-4-fluorophenoxy)-6-fluoro-1-(phenylsulfonyl)-1H-indol-4-yl)methyl)sulfonyl)acetate (Step A product, 4 g, 3.99 mmol) in ethanol (40 mL) was added a solution of sodium hydroxide (0.8 g, 20 mmol) in water (10 mL). The mixture was stirred at room temperature for 12 hours and concentrated. The residue was acidified to pH ~3 with 1 N hydrochloric acid and extracted with ethyl acetate (3×100 mL). The combined organic layers were washed with brine (50 mL), dried over sodium sulfate, and concentrated to give the title product as a yellow solid (2.5 g, crude). MS (ESI): 792 m/z $[M+H]^+$.

Ethyl 2-(((6-fluoro-5-(4-fluoro-3-(5-(7-hydroxy-2-(3-iodophenyl)-6,6-dimethylheptan-2-yl)-1H-imidazol-2-yl)phenoxy)-1H-indol-4-yl)methyl)sulfonyl) acetate

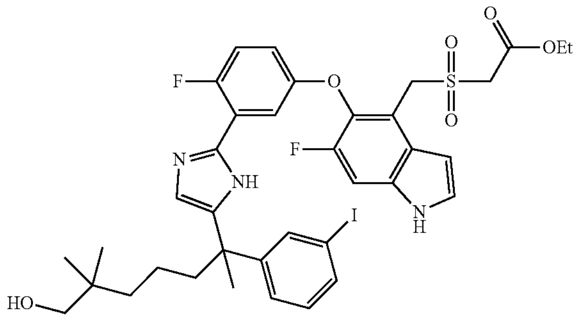 [SMILES: CCOC(=O)CS(=O)(=O)Cc1c(Oc2ccc(F)c(-c3ncc(C(C)(CCCC(C)(C)CO)c4cccc(I)c4)[nH]3)c2)c(F)cc2[nH]ccc12]

Step C: To a stirred solution of 2-(((6-fluoro-5-(4-fluoro-3-(5-(7-hydroxy-2-(3-iodophenyl)-6,6-dimethylheptan-2-yl)-1H-imidazol-2-yl)phenoxy)-1H-indol-4-yl)methyl) sulfonyl)acetic acid (Step B product, 2.5 g, 3.16 mmol) in ethanol (100 mL) was added concentrated sulfuric acid (1 mL). The mixture was stirred at 70° C. for 12 hours and then concentrated. The residue was neutralized with saturated sodium bicarbonate and then extracted with ethyl acetate (3×100 mL). The combined organic layers were washed with brine (30 mL), dried over sodium sulfate and concentrated. The residue was purified by silica gel column (eluting with 50% ethyl acetate in petroleum ether) to give the title product as a white solid (2.59 g, 57.9%). MS (ESI): 820 m/z $[M+H]^+$.

Ethyl 2-(((6-fluoro-5-(4-fluoro-3-(5-(2-(3-iodophenyl)-6,6-dimethyl-7-oxoheptan-2-yl)-1H-imidazol-2-yl)phenoxy)-1H-indol-4-yl)methyl)sulfonyl)acetate

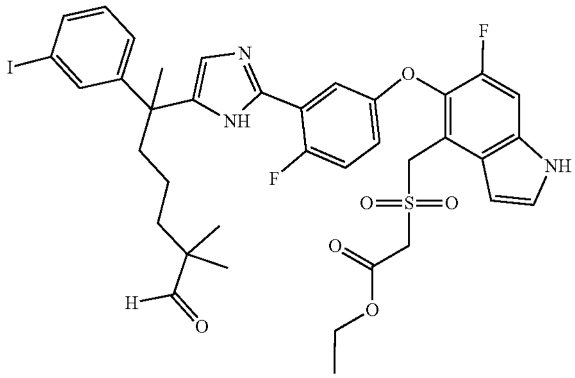 [SMILES: CCOC(=O)CS(=O)(=O)Cc1c(Oc2ccc(F)c(-c3ncc(C(C)(CCCC(C)(C)C=O)c4cccc(I)c4)[nH]3)c2)c(F)cc2[nH]ccc12]

Step D: To a stirred solution of ethyl 2-(((6-fluoro-5-(4-fluoro-3-(5-(7-hydroxy-2-(3-iodophenyl)-6,6-dimethylheptan-2-yl)-1H-imidazol-2-yl)phenoxy)-1H-indol-4-yl) methyl)sulfonyl)acetate (Step C product, 1.5 g, 1.83 mmol) in dimethyl sulfoxide (10 mL) was added 2-iodoxybenzoic acid (1.6 g, 2.74 mmol). The mixture was stirred at room temperature for 4 hours, then diluted with 100 mL of water. The mixture was extracted with ethyl acetate (3×100 mL). The combined organic layers were washed with brine (30 mL), dried over sodium sulfate and concentrated. The residue was purified by silica gel column chromatography (eluting with 50% ethyl acetate in petroleum ether) to give the title product as a white solid (1.2 g, 80%). MS (ESI): 818 m/z $[M+H]^+$.

Ethyl (11E)-22,28-difluoro-6-(3-iodophenyl)-6,10,10-trimethyl-13,13-dioxo-24-oxa-13lambda6-thia-3,19,30-triazapentacyclo[23.3.1.12,5.015,23.016,20]triaconta-1(29),2,4,11,15(23),16(20),17,21,25,27-decaene-12-carboxylate

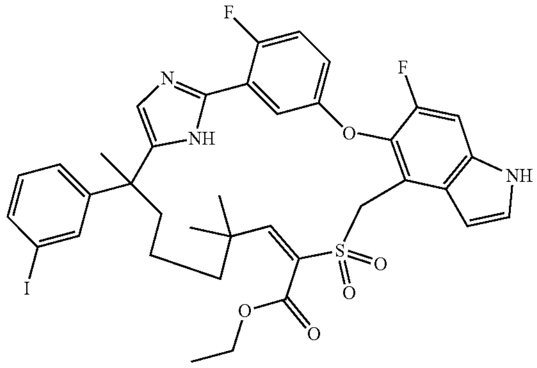

Step E: To a stirred solution of ethyl 2-(((6-fluoro-5-(4-fluoro-3-(5-(2-(3-iodophenyl)-6,6-dimethyl-7-oxoheptan-2-yl)-1H-imidazol-2-yl)phenoxy)-1H-indol-4-yl)methyl) sulfonyl)acetate (Step D product, 1.2 g, 1.47 mmol) in ethanol (1L) was added ammonium acetate (1.13 g, 14.7 mmol). The mixture was stirred at 50° C. for 12 hours and then concentrated. The residue was purified by automated flash chromatography (40 g silica gel column, 0-50% ethyl acetate in petroleum ether) to give the title product as a white solid (0.3 g, 25.6%). MS (ESI): 800 m/z $[M+H]^+$.

Ethyl (11E)-6-[3-[(E)-3-ethoxy-3-oxo-prop-1-enyl]phenyl]-22,28-difluoro-6,10,10-trimethyl-13,13-dioxo-24-oxa-13lambda6-thia-3,19,30-triazapentacyclo[23.3.1.12,5.015,23.016,20]triaconta-1(29),2,4,11,15(23),16(20),17,21,25,27-decaene-12-carboxylate

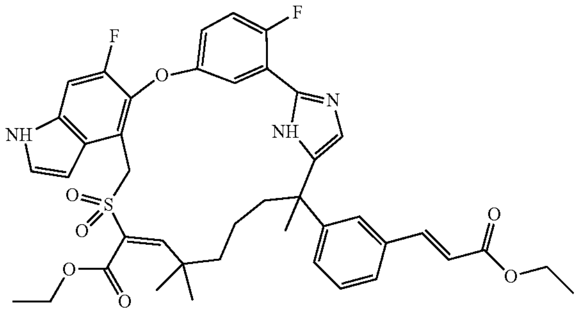 [SMILES: CCOC(=O)/C=C/c1cccc(C2(C)CCCC(C)(C)/C=C(\C(=O)OCC)S(=O)(=O)Cc3c(c(F)cc4[nH]ccc34)Oc3ccc(F)c(c3)-c3ncc2[nH]3)c1]

Step F: To a stirred solution of ethyl (11E)-22,28-difluoro-6-(3-iodophenyl)-6,10,10-trimethyl-13,13-dioxo-24-oxa-13lambda6-thia-3,19,30-triazapentacyclo[23.3.1.12,5.015,23.016,20]triaconta-1(29),2,4,11,15(23),16(20),17,21,25,27-decaene-12-carboxylate (Step E product, 0.3 g, 0.38 mmol) in N,N-dimethylformamide (4 mL) was added ethyl prop-2-enoate (0.113 g, 1.13 mmol), triethylamine (0.19 g, 1.88 mmol), palladium (II) acetate (16.8 mg, 0.076 mmol) and tris(o-tolyl) phosphine (11.4 mg, 0.038 mmol). The mixture was stirred at 120° C. for 12 hours. The mixture was cooled to room temperature and extracted with ethyl acetate (3×50 mL). The combined organic layers were washed with brine (30 mL), dried over sodium sulfate and concentrated. The residue was purified by silica gel column chromatography (eluting with 50% ethyl acetate in petroleum ether) to give the title product as a white solid (0.15 g, 51.8%). MS (ESI): 772 m/z [M+H]+.

Ethyl 6-[3-(3-ethoxy-3-oxo-propyl)phenyl]-22,28-difluoro-6,10,10-trimethyl-13,13-dioxo-24-oxa-13lambda6-thia-3,19,30-triazapentacyclo[23.3.1.12,5.015,23.016,20]triaconta-1(29),2,4,15(23),16(20),17,21,25,27-nonaene-12-carboxylate

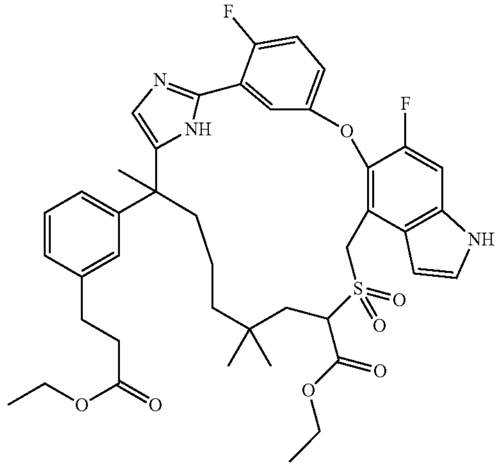 [SMILES: CCOC(=O)CCc1cccc(C2(C)CCCC(C)(C)CC(C(=O)OCC)S(=O)(=O)Cc3c(c(F)cc4[nH]ccc34)Oc3ccc(F)c(c3)-c3ncc2[nH]3)c1]

Step G: To a stirred solution of ethyl (11E)-6-[3-[(E)-3-ethoxy-3-oxo-prop-1-enyl]phenyl]-22,28-difluoro-6,10,10-trimethyl-13,13-dioxo-24-oxa-13lambda6-thia-3,19,30-triazapentacyclo[23.3.1.12,5.015,23.016,20]triaconta-1(29),2,4,11,15(23),16(20),17,21,25,27-decaene-12-carboxylate (Step F product, 150 mg, 0.2 mmol) in ethanol (20 mL) was added Raney nickel (150 mg). The mixture was stirred under hydrogen balloon for 2 hours at room temperature. The catalyst was removed by filtration through a pad of Celite, and the filter cake was washed with ethanol (50 mL). The filtrate was concentrated in vacuo to give the crude title product as a white solid (100 mg, 66.3%). MS (ESI): 776 m/z [M+H]+.

6-[3-(2-Carboxyethyl)phenyl]-22,28-difluoro-6,10,10-trimethyl-13,13-dioxo-24-oxa-13lambda6-thia-3,19,30-triazapentacyclo[23.3.1.12,5.015,23.016,20]triaconta-1(29),2,4,15(23),16(20),17,21,25,27-nonaene-12-carboxylic Acid

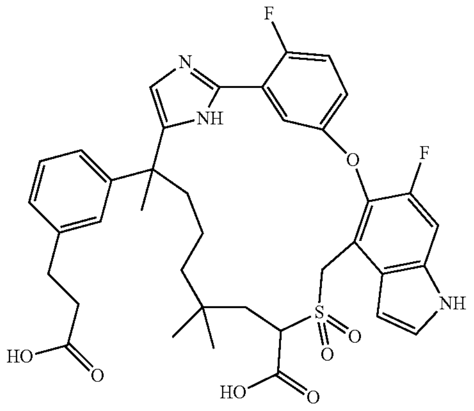 [SMILES: CC1(C)CCCC(C)(c2cccc(CCC(=O)O)c2)c2cnc([nH]2)-c2cc(ccc2F)Oc2c(F)cc3[nH]ccc3c2CS(=O)(=O)C(C(=O)O)C1]

Step H: To a stirred solution of ethyl 6-[3-(3-ethoxy-3-oxo-propyl)phenyl]-22,28-difluoro-6,10,10-trimethyl-13,13-dioxo-24-oxa-13lambda6-thia-3,19,30-triazapentacyclo[23.3.1.12,5.015,23.016,20]triaconta-1(29),2,4,15(23),16(20),17,21,25,27-nonaene-12-carboxylate (Step G product, 100 mg, 0.13 mmol) in tetrahydrofuran (5 mL) was added lithium hydroxide monohydrate (16 mg, in 0.4 mL water). The reaction was stirred at room temperature for 16 hours. After confirming the starting material was consumed by LC-MS, the mixture was acidified with 1M hydrochloric acid to pH ~4 and extracted with ethyl acetate (2×30 mL). The combined organic extracts were washed with brine (2×30 mL), dried over anhydrous sodium sulfate, filtered, and concentrated to give the title product as a white solid (80 mg, 86.2%). MS (ESI): 720 m/z [M+H]+.

Compound 21: 3-[3-(22,28-Difluoro-6,10,10-trimethyl-13,13-dioxo-24-oxa-13lambda6-thia-3,19,30-triazapentacyclo[23.3.1.12,5.015,23.016,20]triaconta-1(29),2,4,15(23),16(20),17,21,25,27-nonaen-6-yl)phenyl]propanoic Acid

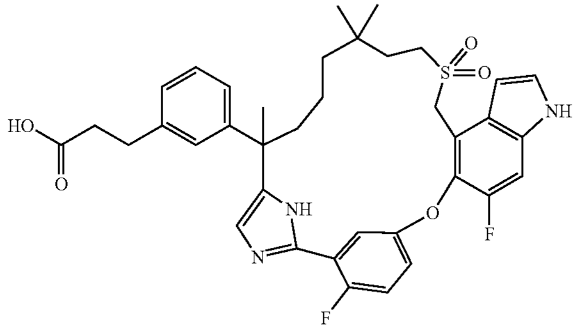 [SMILES: CC1(C)CCCC(C)(c2cccc(CCC(=O)O)c2)c2cnc([nH]2)-c2cc(ccc2F)Oc2c(F)cc3[nH]ccc3c2CS(=O)(=O)CC1]

Step I: To a stirred solution of 6-[3-(2-carboxyethyl)phenyl]-22,28-difluoro-6,10,10-trimethyl-13,13-dioxo-24-oxa-13lambda6-thia-3,19,30-triazapentacyclo[23.3.1.12,5.015,23.016,20]triaconta-1(29),2,4,15(23),16(20),17,21,25,27-nonaene-12-carboxylic acid (Step H product, 80 mg, 0.11 mmol) in dimethyl sulfoxide (10 mL) was added water (0.2 mL) and lithium chloride (14 mg, 0.33 mmol) at room temperature. The reaction was stirred at 120° C. for 16 hours, then cooled to room temperature and diluted with ethyl acetate (20 mL). The mixture was washed with water (2×20 mL), dried over sodium sulfate, filtered, and concentrated. The residue was purified by automated flash chromatography (12 g silica gel column, 0-10% methanol in dichloromethane) to give the title product as a white solid (23.4 mg, 31.2%).

Compound 21: $^{1}$H NMR (400 MHz, $CD_3OD$) δ 7.43-7.41 (m, 2H), 7.35 (d, J=10.7 Hz, 1H), 7.22-7.09 (m, 4H), 7.03-6.98 (m, 3H), 6.74 (d, J=3.2 Hz, 1H), 4.82 (d, J=14.0 Hz, 1H), 4.79 (d, J=14.0 Hz, 1H), 3.00-2.94 (m, 1H), 2.85 (t, J=7.7 Hz, 2H), 2.80-2.73 (m, 1H), 2.53 (t, J=7.7 Hz, 2H), 2.10-2.00 (m, 1H), 1.86-1.79 (m, 1H), 1.54 (s, 3H), 1.46-1.28 (m, 3H), 1.20-1.10 (m, 1H), 1.02-0.98 (m, 1H), 0.82-0.78 (m, 1H), 0.77 (s, 3H), 0.73 (s, 3H). MS (ESI): 676 m/z $[M+H]^+$. Retention time: 0.98 minutes (LC-MS Method 001).

Example 22. Enantiomer 1 and 2 of 3-[3-[3-cyano-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl]phenyl]propanoic acid and 3-[3-(3-cyano-23,29-difluoro-11,11-dimethyl-13,13-dioxo-25-oxa-13lambda6-thia-5,6,20-triazapentacyclo[24.3.1.02,6.016,24.017,21]triaconta-1(30),2,4,16,18,21,23,26,28-nonaen-7-yl)phenyl]propanoic Acid

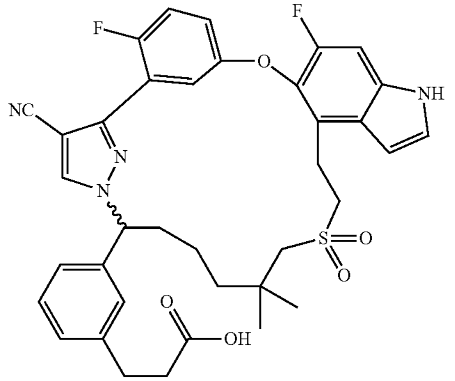

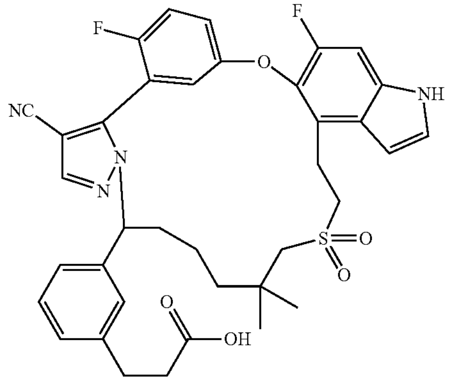

Ethyl 3-(3-(6-mercapto-5,5-dimethyl-1-((tetrahydro-2H-pyran-2-yl)oxy)hexyl)phenyl)propanoate

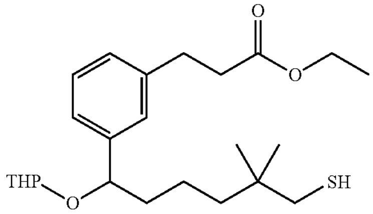

Step A: To a solution of ethyl 3-(3-(6-(acetylthio)-5,5-dimethyl-1-((tetrahydro-2H-pyran-2-yl)oxy)hexyl)phenyl)propanoate (Intermediate 53, 7.10 g, 15.3 mmol) in ethanol (100 mL) was added sodium ethoxide (1.56 g, 22.9 mmol) at room temperature. The mixture was stirred at room temperature for 1 hour. The mixture was extracted with ethyl acetate (300 mL), washed with brine (2×300 mL), dried over anhydrous sodium sulfate, filtered, and concentrated. The residue was purified by flash chromatography (80 g silica gel column, 0-20% ethyl acetate in petroleum ether) to give the title compound as an oil (4.80 g, 74%). MS (ESI): 445 m/z $[M+Na]^+$.

Ethyl 3-(3-(6-((2-(5-(3-(4-cyano-1-(tetrahydro-2H-pyran-2-yl)-1H-pyrazol-3-yl)-4-fluorophenoxy)-6-fluoro-1H-indol-4-yl)ethyl)thio)-5,5-dimethyl-1-((tetrahydro-2H-pyran-2-yl)oxy)hexyl)phenyl)propanoate

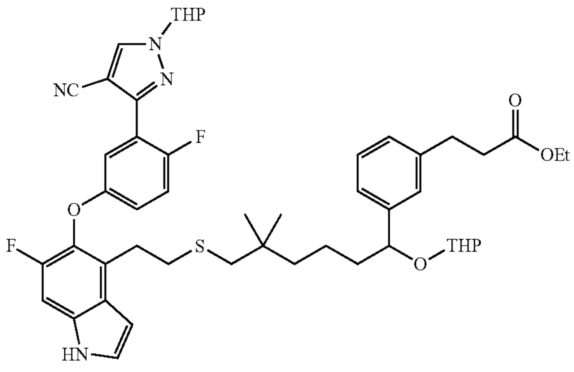

Step B: To a stirred solution of 3-(2-fluoro-5-((6-fluoro-4-vinyl-1H-indol-5-yl)oxy)phenyl)-1-(tetrahydro-2H-pyran-2-yl)-1H-pyrazole-4-carbonitrile (Intermediate 52, 3.50 g, 7.84 mmol) in tetrahydrofuran (80 mL) was added ethyl 3-(3-(6-mercapto-5,5-dimethyl-1-((tetrahydro-2H-pyran-2-yl)oxy)hexyl)phenyl)propanoate (Step A product, 3.98 g, 9.41 mmol) and azobisisobutyronitrile (257 mg, 1.57 mmol) at room temperature. The reaction mixture was refluxed for 16 hours and then diluted with ethyl acetate (150 mL), washed with water (2×200 mL), dried over anhydrous magnesium sulfate, filtered and concentrated. The residue was purified by silica gel column chromatography (80 g silica gel column, 0-40% ethyl acetate in petroleum ether) to give the title compound as an oil (4.50 g, 66%). MS (ESI): 891 m/z $[M+Na]^+$.

Ethyl 3-(3-(6-((2-(5-(3-(4-cyano-1H-pyrazol-3-yl)-4-fluorophenoxy)-6-fluoro-1H-indol-4-yl)ethyl)thio)-1-hydroxy-5,5-dimethylhexyl)phenyl)propanoate

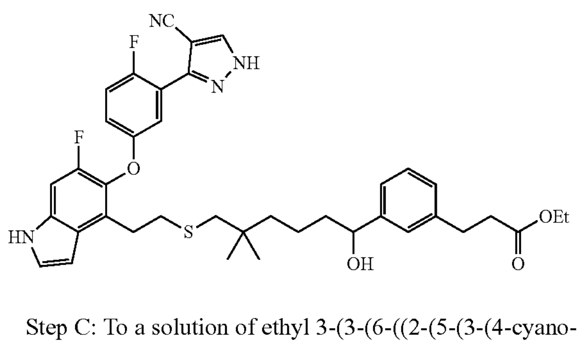

Step C: To a solution of ethyl 3-(3-(6-((2-(5-(3-(4-cyano-1-(tetrahydro-2H-pyran-2-yl)-1H-pyrazol-3-yl)-4-fluorophenoxy)-6-fluoro-1H-indol-4-yl)ethyl)thio)-5,5-dimethyl-1-((tetrahydro-2H-pyran-2-yl)oxy)hexyl)phenyl)propanoate (Step B product, 4.50 g, 5.18 mmol) in methanol (50 mL) was added pyridinium p-toluenesulfonate (5.20 g, 20.7 mmol). The reaction mixture was stirred at 60° C. for 4 hours and then diluted with ethyl acetate (150 mL), washed with water (2×150 mL), dried over anhydrous sodium sulfate, filtered and concentrated. The residue was purified by flash chromatography (80 g silica gel column, 0-50% ethyl acetate in petroleum ether) to give the title compound as a white solid. MS (ESI): 723 m/z $[M+Na]^+$.

Ethyl 3-[3-(3-cyano-22,28-difluoro-10,10-dimethyl-24-oxa-12-thia-5,19,30-triazapentacyclo[23.3.1.12,5.015,23.016,20]triaconta-1(29),2(30),3,15,17,20,22,25,27-nonaen-6-yl)phenyl]propanoate and ethyl 3-[3-(3-cyano-23,29-difluoro-11,11-dimethyl-25-oxa-13-thia-5,6,20-triazapentacyclo[24.3.1.02,6.016,24.017,21]triaconta-1(30),2,4,16,18,21,23,26,28-nonaen-7-yl)phenyl]propanoate, inseparable mixture

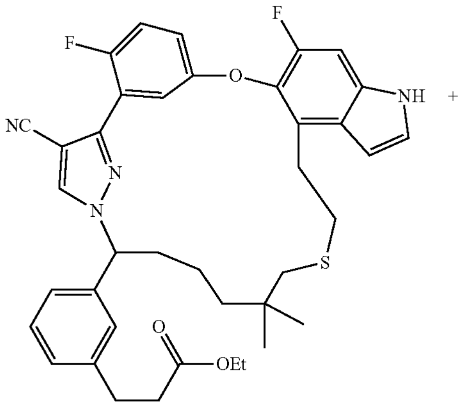

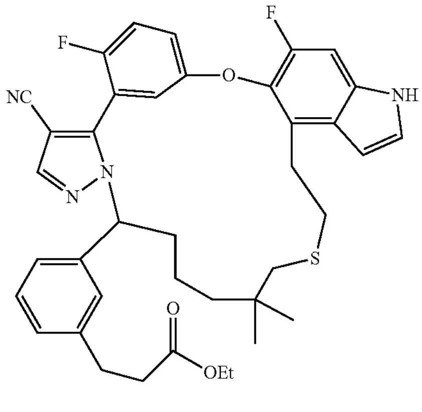

Step D: To a solution of ethyl 3-(3-(6-((2-(5-(3-(4-cyano-1H-pyrazol-3-yl)-4-fluorophenoxy)-6-fluoro-1H-indol-4-yl)ethyl)thio)-1-hydroxy-5,5-dimethylhexyl)phenyl)propanoate (Step C product, 1 g, 1.43 mmol) in 1,4-dioxane (35 mL) was added cyanomethylenetributylphosphorane (CAS: 157141-27-01, 1.72 g, 7.13 mmol). The reaction mixture was stirred in microwave oven at 150° C. for 40 minutes, then concentrated. The residue was purified by automated flash chromatography (20 g silica gel column, 0-30% ethyl acetate in petroleum ether) to give the title compounds, an inseparable mixture of isomers as a white solid (450 mg, 46%). MS (ESI): 683 m/z $[M+H]^+$.

Ethyl 3-[3-(3-cyano-22,28-difluoro-10,10-dimethyl-12,12-dioxo-24-oxa-12lambda6-thia-5,19,30-triaza-pentacyclo[23.3.1.12,5.015,23.016,20]triaconta-1(29),2(30),3,15,17,20,22,25,27-nonaen-6-yl)phenyl]propanoate and ethyl 3-[3-(3-cyano-23,29-difluoro-11,11-dimethyl-13,13-dioxo-25-oxa-13lambda6-thia-5,6,20-triazapentacyclo[24.3.1.02,6.016,24.017,21]triaconta-1(30),2,4,16,18,21,23,26,28-nonaen-7-yl)phenyl]propanoate, an inseparable regio isomeric mixture

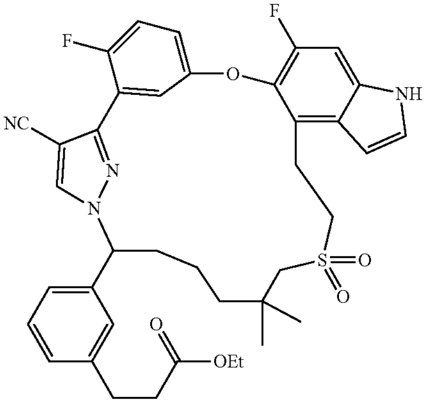

+

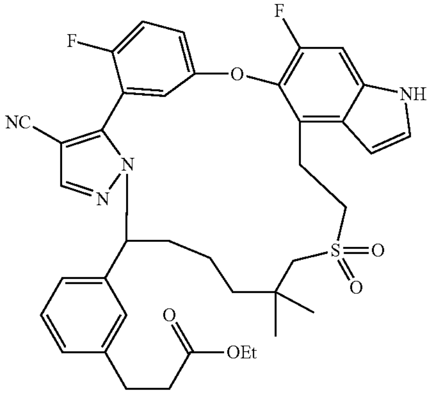

Step E: To a solution of the Step D product (an inseparable regio isomeric mixture, 450 mg, 0.659 mmol) in methanol (45 mL) was added a solution of 900 mg of ammonium molybdate tetrahydrate in 4.5 mL of hydrogen peroxide (30% in water) at 0° C. The reaction was stirred at room temperature for 3 hours. The mixture was diluted with ethyl acetate (100 mL), washed with water (3×100 mL), dried over anhydrous sodium sulphate and concentrated. The residue was purified by automated flash chromatography (20 g silica gel column, 0-40% ethyl acetate in petroleum ether) to give the title regio isomeric mixture as a white solid (240 mg, 51%). MS (ESI): 715 m/z $[M+H]^+$.

3-[3-(3-Cyano-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl)phenyl]propanoic acid and Compound 22A: 3-[3-(3-cyano-23,29-difluoro-11,11-dimethyl-13,13-dioxo-25-oxa-13lambda6-thia-5,6,20-triazapentacyclo[24.3.1.02,6.016,24.017,21]triaconta-1(30),2,4,16,18,21,23,26,28-nonaen-7-yl)phenyl]propanoic Acid

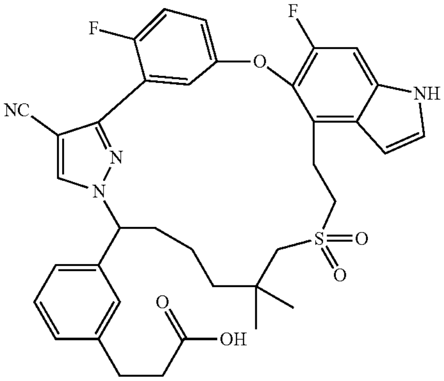

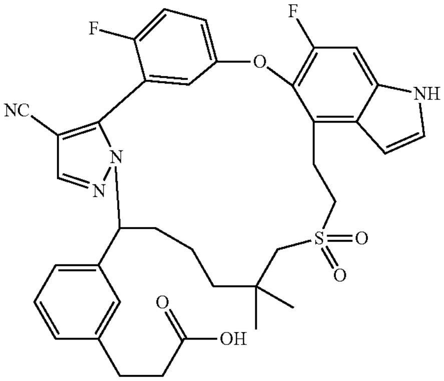

Step F: To a solution of the Step E product, an inseparable regio isomeric mixture (260 mg, 0.364 mmol) in tetrahydrofuran (3 mL) and methanol (1 mL) was added lithium hydroxide monohydrate (1 mL, 1M in water). The reaction was stirred at room temperature for 16 hours. After confirming the starting material was consumed by LC-MS analysis, the mixture was acidified with 1M hydrochloric acid to pH ~4, extracted with ethyl acetate (2×50 mL). The combined organic extracts were washed with brine, dried over anhydrous sodium sulfate, and concentrated. The residue was purified by Prep-HPLC to afford racemic mixture of 3-[3-(3-cyano-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl)phenyl]propanoic acid (22B/22C, 90 mg, yield 36.0%) and the racemic regio-isomer biproduct 3-[3-(3-cyano-23,29-difluoro-11,11-dimethyl-13,13-dioxo-25-oxa-13lambda6-thia-5,6,20-triazapentacyclo[24.3.1.02,6.016,24.017,21]triaconta-1(30),2,4,16,18,21,23,26,28-nonaen-7-yl)phenyl]propanoic acid (22A, 75 mg, yield 30%), both as white solids.

22B/22C: MS (ESI): 687 m/z $[M+H]^+$, Retention time: 1.57 minutes (LC-MS Method 08).

Compound 22A: 3-[3-(3-cyano-23,29-difluoro-11,11-dimethyl-13,13-dioxo-25-oxa-13lambda6-thia-5,6,20-triazapentacyclo[24.3.1.02,6.016,24.017,21]triaconta-1(30),2,4,16,18,21,23,26,28-nonaen-7-yl)phenyl]propanoic acid: MS (ESI): 687 m/z $[M+H]^+$, Retention time: 1.56 minutes (LC-MS Method 08). $^1H$ NMR (400 MHz, $CD_3OD$) δ 8.11 (s, 1H), 7.40-7.19 (m, 8H), 6.97-6.91 (m, 1H), 6.62 (d, J=2.8 Hz, 1H), 5.19-5.13 (m, 1H), 3.51-3.43 (m, 1H), 3.30-3.22 (m, 2H), 3.19-3.11 (m, 1H), 3.07-2.90 (m, 4H), 2.57 (t, J=8.0 Hz, 2H), 2.46-2.33 (m, 1H), 2.05-1.95 (m, 1H), 1.64-1.53 (m, 1H), 1.33-1.24 (m, 1H), 1.18 (s, 3H), 1.05-0.95 (m, 4H), 0.93-0.82 (m, 1H) ppm.

Compound 22B, Enantiomer 1 and Compound 22C, enantiomer 2 of 3-[3-[3-cyano-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl]phenyl]propanoic Acid

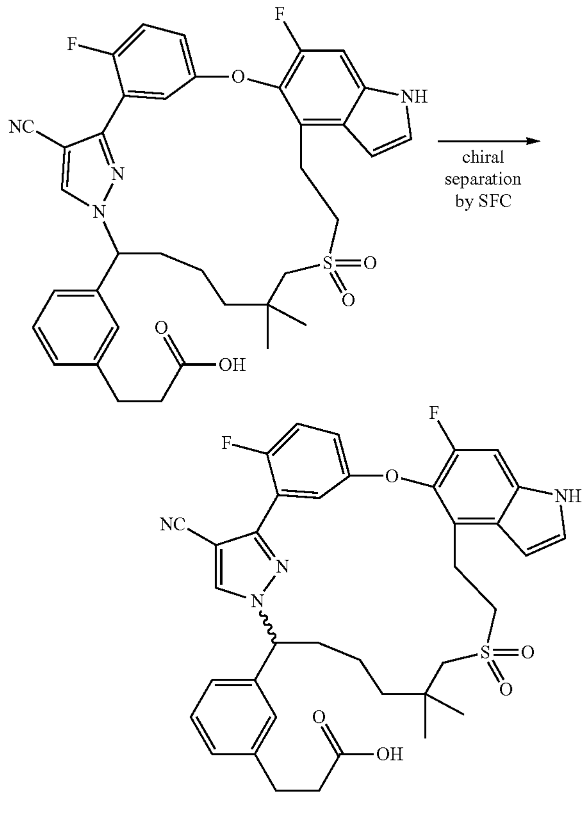

Enantiomer 1 and 2
(absolute configurations unknown)

Step G: The product obtained from step F (170 mg) was subjected to chiral SFC using a Thar SFC-80 instrument and the following separation conditions. Column: 20×250 mm×10 μm Chiralpak AD; sample solution: 170 mg dissolved in methanol (25 mL); injection volume: 1.0 mL; eluant: 70:30 $CO_2$/methanol with 1% ammonia/methanol additive; flow rate: 80 mL/min; column temperature: 35° C.; back pressure: 100 bar; detection wavelength: 214 nm. The first eluting isomer was designated as Compound 22B (54 mg, 32%). The second eluting isomer was designated Compound 22C (54 mg, 32%). The absolute stereochemistry is unknown.

Compound 22B: Enantiomer 1 of 3-[3-[3-cyano-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl]phenyl]propanoic acid: MS (ESI): 687 m/z $[M+H]^+$. LCMS: retention time=1.37 minutes. (LC-MS method: 01). $^1H$ NMR (500 MHz, $CD_3OD$) δ 8.25 (s, 1H), 7.35-7.34 (m, 2H), 7.31-7.26 (m, 3H), 7.22-7.20 (m, 3H), 7.13 (d, J=7.5 Hz, 1H), 6.66 (d, J=3.5 Hz, 1H), 5.45 (dd, J=11.5, 3.0 Hz, 1H), 3.47-3.40 (m, 2H), 3.25-3.15 (m, 2H), 2.90 (t, J=8.0 Hz, 2H), 2.72 (s, 2H), 2.59 (t, J=8.0 Hz, 2H), 2.38-2.30 (m, 1H), 1.95-1.87 (m, 1H), 1.47-1.29 (m, 4H), 1.11 (s, 3H), 1.01 (s, 3H) ppm.

Compound 22C: Enantiomer 2 of 3-[3-[3-cyano-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl]phenyl]propanoic acid: MS (ESI): 687 m/z $[M+H]^+$. LCMS: retention time=1.37 minutes. (LC-MS method: 01). $^1H$ NMR (500 MHz, $CD_3OD$) δ 8.25 (s, 1H), 7.35-7.34 (m, 2H), 7.31-7.26 (m, 3H), 7.22-7.20 (m, 3H), 7.13 (d, J=7.5 Hz, 1H), 6.67 (d, J=3.0 Hz, 1H), 5.45 (dd, J=11.0, 2.5 Hz, 1H), 3.47-3.40 (m, 2H), 3.25-3.15 (m, 2H), 2.90 (t, J=7.5 Hz, 2H), 2.72 (s, 2H), 2.59 (t, J=7.5 Hz, 2H), 2.38-2.30 (m, 1H), 1.96-1.87 (m, 1H), 1.47-1.31 (m, 4H), 1.11 (s, 3H), 1.01 (s, 3H) ppm.

Example 23. 3-[3-(22-Fluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl)phenyl]propanoic Acid

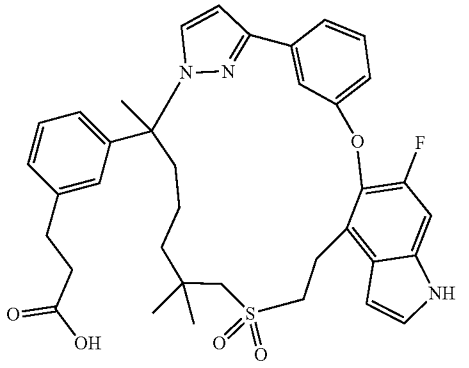 [SMILES: CC1(C)CCCC(C)(c2cccc(CCC(=O)O)c2)n2ccc(n2)-c2cccc(c2)Oc2c(F)cc3[nH]ccc3c2CCS(=O)(=O)C1]

Methyl 2-((6-(3-bromophenyl)-6-(3-(3-((6-fluoro-1-tosyl-4-vinyl-1H-indol-5-yl)oxy)phenyl)-1H-pyrazol-1-yl)-2,2-dimethylhexyl)thio)acetate

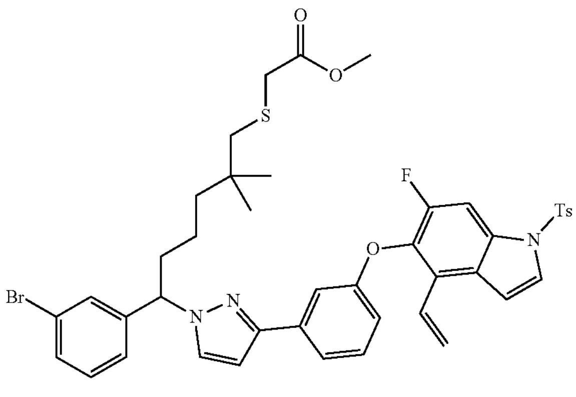 [SMILES: C=Cc1c(Oc2cccc(-c3ccn(C(CCCC(C)(C)CSCC(=O)OC)c4cccc(Br)c4)n3)c2)c(F)cc2c1ccn2S(=O)(=O)c1ccc(C)cc1]

Step A: To a solution of methyl 2-((6-bromo-6-(3-bromophenyl)-2,2-dimethylhexyl)thio)acetate (Intermediate 54, 3.00 g, 6.63 mmol) in N,N-dimethylformamide (50 mL)

were added 5-(3-(1H-pyrazol-3-yl)phenoxy)-6-fluoro-1-tosyl-4-vinyl-1H-indole (Intermediate 21-1) (3.14 g, 6.63 mmol) and cesium carbonate (4.32 g, 13.3 mmol). The reaction was stirred at room temperature for 96 hours, then diluted with ethyl acetate (150 mL). The solution was washed with water (2×150 mL), dried over anhydrous sodium sulfate and concentrated. The residue was purified by flash chromatography (80 g silica gel column, 0-50% ethyl acetate in petroleum ether) to give the title compound as an oil (3.60 g, 64%). MS (ESI): 844, 846 m/z [M+H]+.

Methyl 2-((6-(3-bromophenyl)-6-(3-(3-((6-fluoro-4-vinyl-1H-indol-5-yl)oxy)phenyl)-1H-pyrazol-1-yl)-2,2-dimethylhexyl)thio)acetate

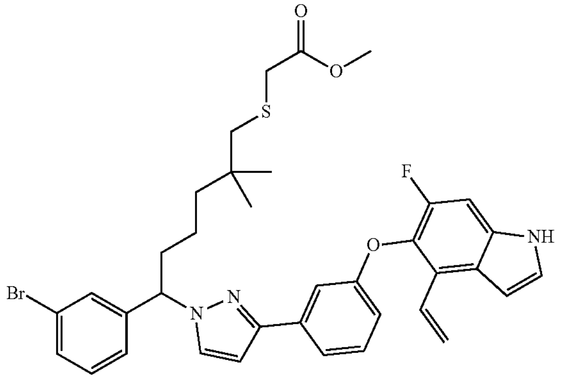 [SMILES: C=Cc1c(Oc2cccc(-c3ccn(C(CCCC(C)(C)CSCC(=O)OC)c4cccc(Br)c4)n3)c2)c(F)cc2[nH]ccc12]

Step B: To a solution of methyl 2-((6-(3-bromophenyl)-6-(3-(3-((6-fluoro-1-tosyl-4-vinyl-1H-indol-5-yl)oxy)phenyl)-1H-pyrazol-1-yl)-2,2-dimethylhexyl)thio)acetate (Step A product, 3.60 g, 4.26 mmol) in tetrahydrofuran (50 mL) was added tetrabutylammonium fluoride (43.0 mL, 42.6 mmol). The reaction was stirred at room temperature overnight, then diluted with ethyl acetate (150 mL). The solution was washed with water (2×150 mL), dried over anhydrous sodium sulfate, filtered, and concentrated. The residue was purified by flash chromatography (40 g silica gel column, 0-50% ethyl acetate in petroleum ether) to give the title compound as an oil (2.50 g, 85%). MS (ESI): 690, 692 m/z [M+H]+.

Methyl 2-((6-(3-bromophenyl)-6-(3-(3-((6-fluoro-4-vinyl-1H-indol-5-yl)oxy)phenyl)-1H-pyrazol-1-yl)-2,2-dimethylhexyl)sulfonyl)acetate

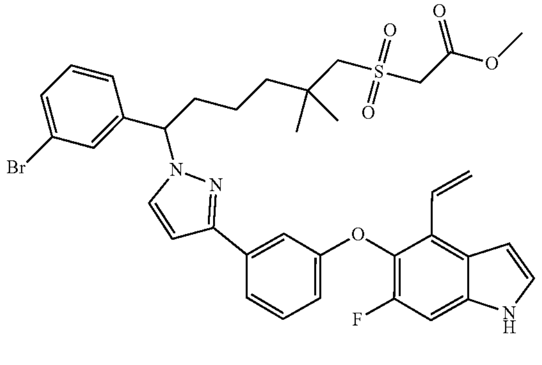 [SMILES: C=Cc1c(Oc2cccc(-c3ccn(C(CCCC(C)(C)CS(=O)(=O)CC(=O)OC)c4cccc(Br)c4)n3)c2)c(F)cc2[nH]ccc12]

Step C: To a solution of methyl 2-((6-(3-bromophenyl)-6-(3-(3-((6-fluoro-4-vinyl-1H-indol-5-yl)oxy)phenyl)-1H-pyrazol-1-yl)-2,2-dimethylhexyl)thio)acetate (Step B product, 1.8 g, 2.61 mmol) in methanol (100 mL) was added a mixture of 3.60 g of ammonium molybdate tetrahydrate in 18 mL of hydrogen peroxide (30% in water) at 0° C. The reaction was stirred at room temperature for 6 hours, then diluted with ethyl acetate (200 mL). The solution was washed with water (3×200 mL), dried over anhydrous sodium sulfate and concentrated. The residue was purified by flash chromatography (20 g silica gel column, 0-50% ethyl acetate in petroleum ether) to give the title compound as an oil (850.0 mg, 45%). MS (ESI): 722, 724 m/z [M+H]+.

Methyl 2-((6-(3-bromophenyl)-6-(3-(3-((6-fluoro-4-formyl-1H-indol-5-yl)oxy)phenyl)-1H-pyrazol-1-yl)-2,2-dimethylhexyl)sulfonyl)acetate

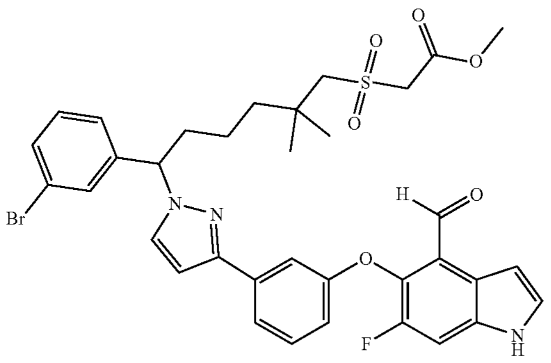 [SMILES: COC(=O)CS(=O)(=O)CC(C)(C)CCCC(c1cccc(Br)c1)n1ccc(-c2cccc(Oc3c(F)cc4[nH]ccc4c3C=O)c2)n1]

Step D: To a solution of methyl 2-((6-(3-bromophenyl)-6-(3-(3-((6-fluoro-4-vinyl-1H-indol-5-yl)oxy)phenyl)-1H-pyrazol-1-yl)-2,2-dimethylhexyl)sulfonyl)acetate (Step C product, 850 mg, 1.18 mmol) in tetrahydrofuran (40 mL) and water (20 mL) were added sodium periodate (755 mg, 3.53 mmol) and osmium tetroxide (8.3 mg in 4 mL of water, 0.03 mmol). The reaction was stirred at room temperature for 16 hours, then diluted with ethyl acetate (100 mL). The solution was washed with water (2×100 mL), dried over anhydrous sodium sulfate, filtered, and concentrated. The residue was purified by flash chromatography (12 g silica gel column, 0-60% ethyl acetate in petroleum ether) to give the title compound as an oil (380 mg, 45%). MS (ESI): 724, 726 m/z [M+H]+.

Methyl (13E)-6-(3-bromophenyl)-22-fluoro-10,10-dimethyl-12,12-dioxo-24-oxa-12lambda6-thia-5,19,30-triazapentacyclo[23.3.1.12,5.015,23.016,20]triaconta-1(29),2(30),3,13,15,17,20,22,25,27-decaene-13-carboxylate

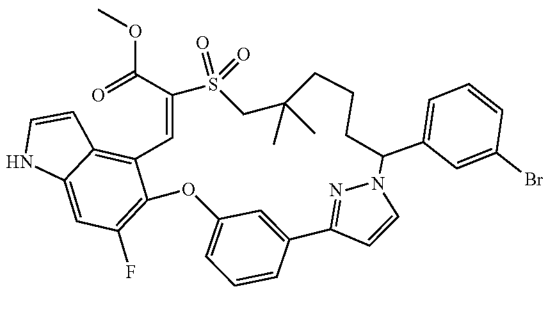 [SMILES: COC(=O)/C1=C\c2c(c(F)cc3[nH]ccc23)Oc2cccc(c2)-c2ccn(n2)[C@@H](c2cccc(Br)c2)CCCC(C)(C)CS1(=O)=O]

Step E: To a solution of Methyl 2-((6-(3-bromophenyl)-6-(3-(3-((6-fluoro-4-formyl-1H-indol-5-yl)oxy)phenyl)-1H-pyrazol-1-yl)-2,2-dimethylhexyl)sulfonyl)acetate (Step D product, 380.0 mg, 0.52 mmol) in toluene (150 mL) was added piperidine (223 mg, 2.62 mmol) and acetic acid (48.0 mg, 0.52 mmol) at room temperature. The mixture was stirred at 100° C. for 16 hours and the solvent evaporated. The residue was dissolved in ethyl acetate (50 mL). The solution was washed with water (2×50 mL), dried over anhydrous sodium sulfate and concentrated. The residue was purified by flash chromatography (12 g silica gel column, 0-60% ethyl acetate in petroleum) to give the title compound as a yellow solid (160.0 mg, 43%). MS (ESI): 706, 708 m/z $[M+H]^+$.

Methyl (13E)-6-[3-[(E)-3-ethoxy-3-oxo-prop-1-enyl]phenyl]-22-fluoro-10,10-dimethyl-12,12-dioxo-24-oxa-12lambda6-thia-5,19,30-triazapentacyclo[23.3.1.12,5.015,23.016,20]triaconta-1(29),2(30),3,13,15,17,20,22,25,27-decaene-13-carboxylate

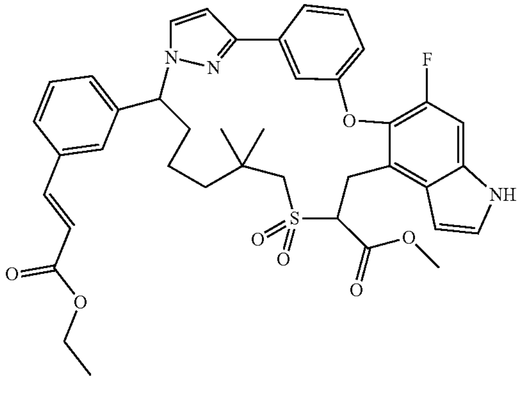 [SMILES: CCOC(=O)/C=C/c1cccc([C@H]2CCCC(C)(C)CS(=O)(=O)C(C(=O)OC)Cc3c(c(F)cc4[nH]ccc34)Oc3cccc(c3)-c3ccn2n3)c1]

Step F: To a solution of the Step E product (160.0 mg, 0.22 mmol) in N,N-dimethylformamide (5 mL) were added ethyl acrylate (68.0 mg, 0.66 mmol), triethylamine (0.15 mL, 1.13 mmol), tri(o-tolyl)phosphine (20.0 mg, 0.06 mmol), and palladium(II) acetate (5.0 mg, 0.02 mmol). The reaction mixture was purged with nitrogen and stirred at 120° C. for 16 hours. The reaction mixture was cooled to room temperature, diluted with ethyl acetate (50 mL), washed with water (2×50 mL), dried over anhydrous sodium sulfate, filtered and concentrated. The residue was purified by flash chromatography (12 g silica gel column, 0-40% ethyl acetate in petroleum ether) to give the title compound as an oil (100.0 mg, 61%). MS (ESI): 726 m/z $[M+H]^+$.

Methyl 6-[3-(3-ethoxy-3-oxopropyl)phenyl]-22-fluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaene-13-carboxylate

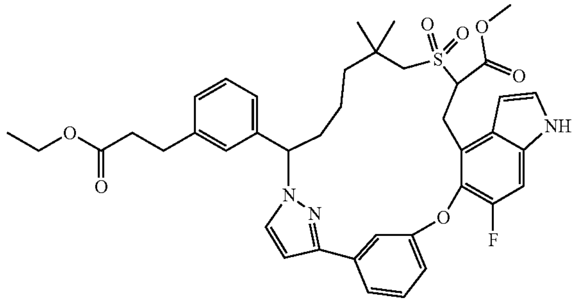 [SMILES: CCOC(=O)CCc1cccc(C2CCCC(C)(C)CS(=O)(=O)C(C(=O)OC)Cc3c(c(F)cc4[nH]ccc34)Oc3cccc(c3)-c3ccn2n3)c1]

Step G: To a solution of the Step F product (100.0 mg, 0.13 mmol) in ethanol (20 mL) was added Raney nickel (20.0 mg). The reaction mixture was stirred under hydrogen atmosphere at room temperature for 2 hours. The catalyst was removed by filtration through a pad of Celite and the filter cake was washed with ethanol (50 mL). The filtrate was concentrated to give the crude title compound as a white solid (90.0 mg, crude). MS (ESI): 730 m/z $[M+H]^+$.

6-[3-(2-Carboxyethyl)phenyl]-22-fluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaene-13-carboxylic Acid

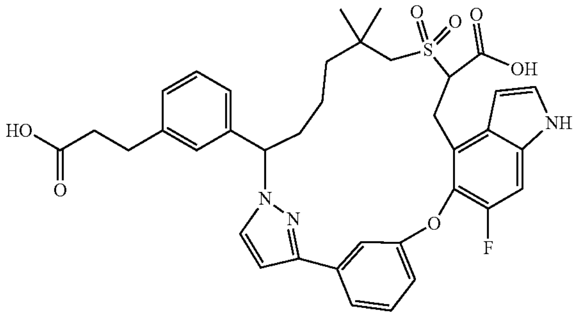 [SMILES: CC1(C)CCCC(c2cccc(CCC(=O)O)c2)n2ccc(n2)-c2cccc(c2)Oc2c(F)cc3[nH]ccc3c2CC(C(=O)O)S(=O)(=O)C1]

Step H: To a solution of the Step G product (90.0 mg, 0.12 mmol) in tetrahydrofuran (3 mL) and methanol (1 mL) was added lithium hydroxide monohydrate (0.7 mL, 1M in water). The reaction was stirred at room temperature for 16 hours, then acidified with 1M hydrochloric acid to pH-4, extracted with ethyl acetate (30 mL), washed with brine (2×30 mL), dried over anhydrous sodium sulfate and concentrated to give the title compound as a white solid (72 mg, 85%). MS (ESI): 688 m/z $[M+H]^+$.

2Compound 23: 3-[3-(22-Fluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl)phenyl]propanoic Acid

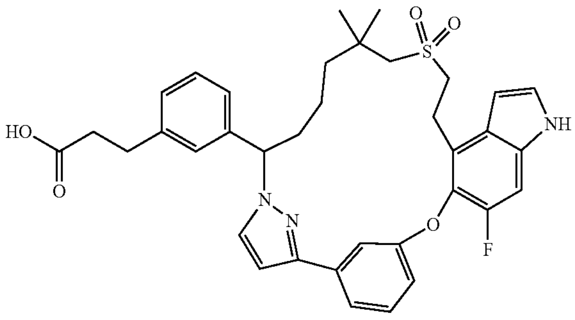 [SMILES: CC1(C)CCCC(c2cccc(CCC(=O)O)c2)n2ccc(n2)-c2cccc(c2)Oc2c(F)cc3[nH]ccc3c2CCS(=O)(=O)C1]

Step I To a solution of 6-[3-(2-carboxyethyl)phenyl]-22-fluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaene-13-carboxylic acid (Step H product, 70.0 mg, 0.10 mmol) in dimethyl sulfoxide (4 mL) was added water (0.2 mL) and lithium chloride (14 mg, 0.30 mmol) at room temperature. The mixture was stirred at 120° C. for 16 hours, then cooled to room temperature and diluted with ethyl acetate (20 mL). The solution was washed with water (2×20 mL), dried over anhydrous sodium sulfate and concentrated. The residue was purified by flash chromatography (12 g silica gel column, 0-10% methanol in dichloromethane) to give the title compound (Compound 23) as a white solid (20.3 mg, 30%).

Compound 23: MS (ESI): 644 m/z $[M+H]^+$. Retention time: 1.44 minutes (LC-MS method: 01). $^1H$ NMR (400 MHz, $CD_3OD$) δ 7.59 (s, 1H), 7.49 (d, J=2.8 Hz, 1H), 7.41-7.39 (m, 2H), 7.34-7.11 (m, 6H), 7.03-7.01 (m, 1H), 6.69-6.66 (m, 2H), 5.35 (dd, J=12.2 Hz, 3 Hz, 1H), 3.48, 3.43 (m, 2H), 3.10-2.95 (m, 2H), 2.90 (t, J=7.6 Hz, 2H), 2.58 (t, J=7.6 Hz, 2H), 2.55 (s, 2H), 2.33-2.23 (m, 1H), 1.93-1.85 (m, 1H), 1.45-1.30 (m, 3H), 1.20-1.10 (m, 1H), 1.10 (s, 3H), 0.93 (s, 3H).

Example 24. Enantiomers 1 and 2 of 3-[3-[22,28-Difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl]phenyl]propanoic Acid

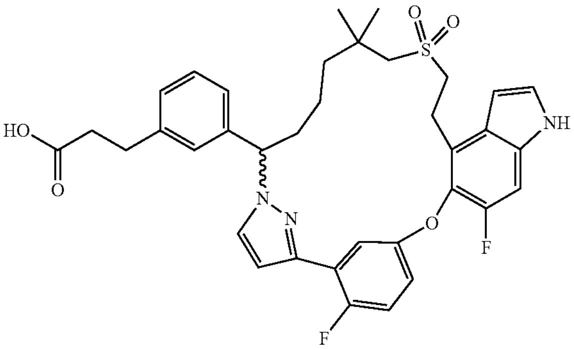 [SMILES: CC1(C)CCCC(c2cccc(CCC(=O)O)c2)n2ccc(n2)-c2cc(ccc2F)Oc2c(F)cc3[nH]ccc3c2CCS(=O)(=O)C1]

Ethyl 3-(3-(6-((2-ethoxy-2-oxoethyl)thio)-1-(3-(2-fluoro-5-((6-fluoro-1-tosyl-4-vinyl-1H-indol-5-yl)oxy)phenyl)-1H-pyrazol-1-yl)-5,5-dimethylhexyl)phenyl)propanoate

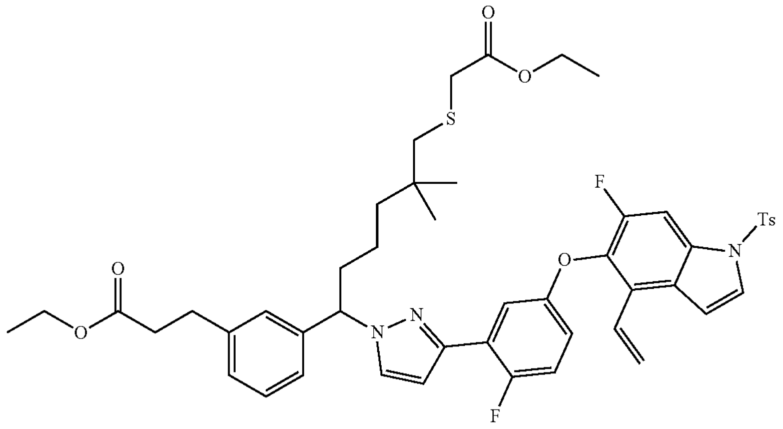 [SMILES: C=Cc1c(Oc2ccc(F)c(-c3ccn(C(CCCC(C)(C)CSCC(=O)OCC)c4cccc(CCC(=O)OCC)c4)n3)c2)c(F)cc2c1ccn2S(=O)(=O)c1ccc(C)cc1]

Step A: To a solution of 6-fluoro-5-(4-fluoro-3-(1H-pyrazol-3-yl)phenoxy)-1-tosyl-4-vinyl-1H-indole (Intermediate 21, 3.60 g, 7.3 mmol) in N,N-dimethylformamide (60 mL) was added ethyl 3-(3-(1-bromo-6-((2-ethoxy-2-oxoethyl)thio)-5,5-dimethylhexyl)phenyl)propanoate (Intermediate 54-1, 5.36 g, 11 mmol) and cesium carbonate (7.16 g, 22.0 mmol). The reaction was stirred at room temperature for 16 hours, then diluted with ethyl acetate (200 mL). The organic solution was washed with water (2×60 mL), dried over sodium sulfate and concentrated. The crude residue was purified by flash chromatography (120 g silica gel column, 0-40% ethyl acetate in petroleum ether) to give the title compound as an oil (4.70 g, 71%). MS (ESI): 920 m/z $[M+Na]^+$. Ethyl 3-(3-(6-((2-ethoxy-2-oxoethyl)thio)-1-(3-(2-fluoro-5-((6-fluoro-4-vinyl-1H-indol-5-yl)oxy)phenyl)-1H-pyrazol-1-yl)-5,5-dimethylhexyl)phenyl)propanoate

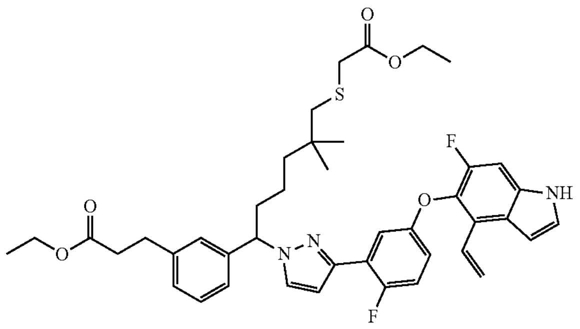 [SMILES: C=Cc1c(Oc2ccc(F)c(-c3ccn(C(CCCC(C)(C)CSCC(=O)OCC)c4cccc(CCC(=O)OCC)c4)n3)c2)c(F)cc2[nH]ccc12]

Step B: To a solution of ethyl 3-(3-(6-((2-ethoxy-2-oxoethyl)thio)-1-(3-(2-fluoro-5-((6-fluoro-1-tosyl-4-vinyl-1H-indol-5-yl)oxy)phenyl)-1H-pyrazol-1-yl)-5,5-dimethylhexyl)phenyl)propanoate (Step A product, 4.70 g, 5.23 mmol) in tetrahydrofuran (25 mL) was added tetrabutylammonium fluoride (1M in THF, 52 mL, 52 mmol). The reaction was stirred at room temperature overnight, then diluted with ethyl acetate (200 mL). The organic solution was then washed with water (2×100 mL), dried over sodium sulfate and concentrated. The crude residue was purified by flash chromatography (120 g silica gel column, 0-50% ethyl acetate in petroleum ether) to give the title compound as an oil (1.80 g, 43%). MS (ESI): 744 m/z $[M+H]^+$.

Ethyl 3-(3-(6-((2-ethoxy-2-oxoethyl)sulfonyl)-1-(3-(2-fluoro-5-((6-fluoro-4-vinyl-1H-indol-5-yl)oxy)phenyl)-1H-pyrazol-1-yl)-5,5-dimethylhexyl)phenyl)propanoate

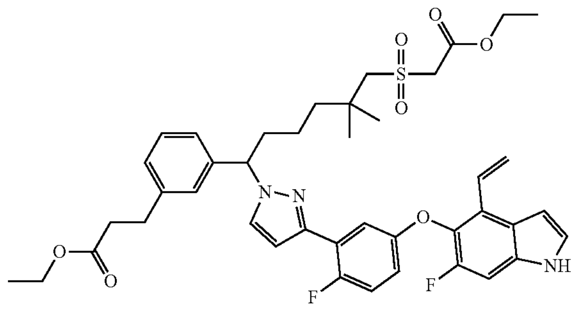 [SMILES: C=Cc1c(Oc2ccc(F)c(-c3ccn(C(CCCC(C)(C)CS(=O)(=O)CC(=O)OCC)c4cccc(CCC(=O)OCC)c4)n3)c2)c(F)cc2[nH]ccc12]

Step C: To a solution of ethyl 3-(3-(6-((2-ethoxy-2-oxoethyl)thio)-1-(3-(2-fluoro-5-((6-fluoro-4-vinyl-1H-indol-5-yl)oxy)phenyl)-1H-pyrazol-1-yl)-5,5-dimethylhexyl)phenyl)propanoate (Step B product, 1.80 g, 2.53 mmol) in methanol (180 mL) was added a solution of ammonium molybdate tetrahydrate (3.60 g) in hydrogen peroxide (30% in water, 10 mL) at 0° C. The reaction was stirred at room temperature for 6 hours, then concentrated to remove methanol. The residue was dissolved in ethyl acetate (200 mL). The solution was washed with water (3×200 mL), dried over anhydrous sodium sulfate and concentrated. The crude residue was purified by flash chromatography (40 g silica gel column, 0-50% ethyl acetate in petroleum ether) to give the title compound as an oil (1.30 g, 69%). MS (ESI): 776 m/z $[M+H]^+$.

Ethyl 3-(3-(6-((2-ethoxy-2-oxoethyl)sulfonyl)-1-(3-(2-fluoro-5-((6-fluoro-4-formyl-1H-indol-5-yl)oxy)phenyl)-1H-pyrazol-1-yl)-5,5-dimethylhexyl)phenyl)propanoate

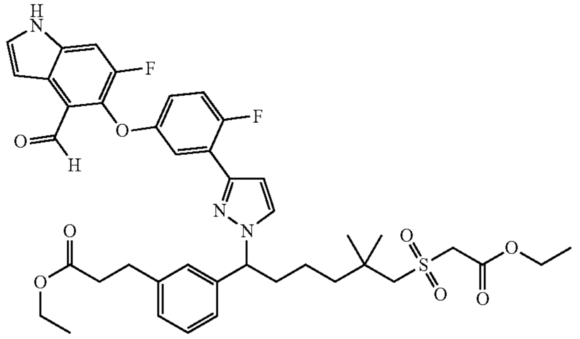 [SMILES: CCOC(=O)CCc1cccc(C(CCCC(C)(C)CS(=O)(=O)CC(=O)OCC)n2ccc(-c3cc(Oc4c(F)cc5[nH]ccc5c4C=O)ccc3F)n2)c1]

Step D: To a solution of ethyl 3-(3-(6-((2-ethoxy-2-oxoethyl)sulfonyl)-1-(3-(2-fluoro-5-((6-fluoro-4-vinyl-1H-indol-5-yl)oxy)phenyl)-1H-pyrazol-1-yl)-5,5-dimethylhexyl)phenyl)propanoate (Step C product, 1.10 g, 0.14 mmol) in acetone (10 mL) and water (2 mL) was added osmium tetroxide (0.35 mg, 0.001 mmol) and N-methylmorpholine N-oxide (0.4 mL, 0.18 mmol). The reaction was stirred at room temperature for 16 hours, then diluted with ethyl acetate (100 mL). The organic solution was then washed with water (2×30 mL), dried over anhydrous sodium sulfate and concentrated. The crude residue was purified by flash chromatography (40 g silica gel column, 0-80% ethyl acetate in petroleum ether) to give ethyl 3-(3-(1-(3-(5-((4-(1,2-dihydroxyethyl)-6-fluoro-1H-indol-5-yl)oxy)-2-fluorophenyl)-1H-pyrazol-1-yl)-6-((2-ethoxy-2-oxoethyl)sulfonyl)-5,5-dimethylhexyl)phenyl)propanoate as an oil (0.60 g, 52%). MS (ESI): 810 m/z $[M+Na]^+$.

To the solution of the intermediate obtained above (0.58 g, 0.71 mmol) in tetrahydrofuran (24 mL) and water (8 mL) was added sodium periodate (0.46 g, 2.1 mmol). The reaction was stirred at room temperature for 16 hours, then diluted with ethyl acetate (100 mL). The solution was washed with water (2×100 mL), dried over anhydrous sodium sulfate and concentrated to give the title compound as an oil (0.48 g, 86%). MS (ESI): 778 m/z $[M+H]^+$.

Ethyl (13E)-6-[3-(3-ethoxy-3-oxo-propyl)phenyl]-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,13,15,17,20,22,25,27-decaene-13-carboxylate

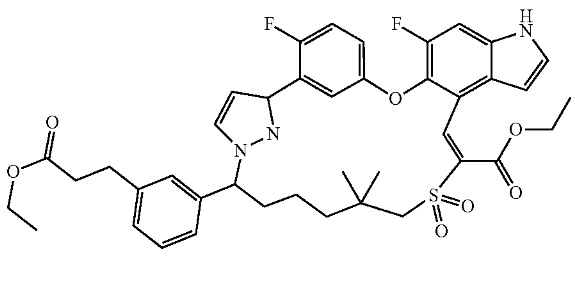

Step E: To a solution of ethyl 3-(3-(6-((2-ethoxy-2-oxoethyl)sulfonyl)-1-(3-(2-fluoro-5-((6-fluoro-4-formyl-1H-indol-5-yl)oxy)phenyl)-1H-pyrazol-1-yl)-5,5-dimethylhexyl)phenyl)propanoate (Step D product, 0.50 g, 0.64 mmol) in toluene (250 mL) was added piperidine (274.0 mg, 3.2 mmol) and acetic acid (38.6 mg, 0.64 mmol) at room temperature. The mixture was stirred at 100° C. for 16 hours, then concentrated. The crude residue was diluted with ethyl acetate (100 mL), washed with water (2×50 mL), dried over sodium sulfate and concentrated. The crude residue was purified by flash chromatography (25 g silica gel column, 0-60% ethyl acetate in petroleum) to give the title compound as a yellow solid (0.29 g, 58%). MS (ESI): 760 m/z $[M+H]^+$.

Ethyl 6-[3-(3-ethoxy-3-oxo-propyl)phenyl]-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaene-13-carboxylate

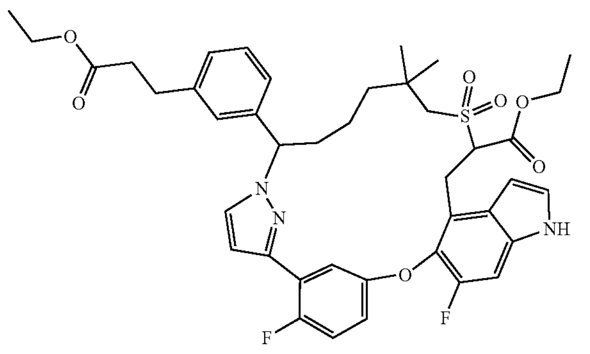 [SMILES: CCOC(=O)CCc1cccc(C2CCCC(C)(C)CS(=O)(=O)C(C(=O)OCC)Cc3c(c(F)cc4[nH]ccc34)Oc3ccc(F)c(c3)-c3ccn2n3)c1]

Step F: To a solution of the product of Step E (275.0 mg; 0.36 mmol) in ethanol (15 mL) was added Raney nickel (80.0 mg). The reaction mixture was stirred under hydrogen at room temperature for 3 hours. The catalyst was removed by filtration through a pad of Celite and washed with ethanol (50 mL). The filtrate was concentrated in vacuo to give the crude title compound as a white solid (0.25 g, crude). MS (ESI): 762 m/z $[M+H]^+$. 6-[3-(2-Carboxyethyl)phenyl]-22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaene-13-carboxylic acid

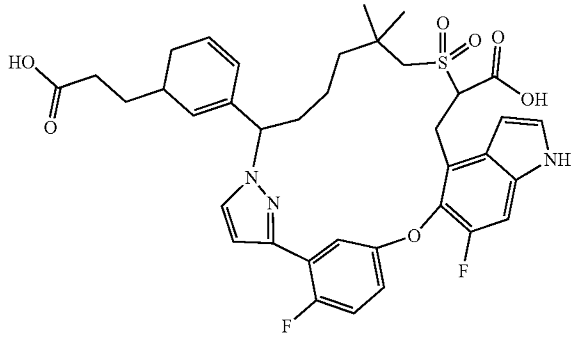 [SMILES: CC1(C)CCCC(C2=CC(CCC(=O)O)CC=C2)n2ccc(n2)-c2cc(ccc2F)Oc2c(F)cc3[nH]ccc3c2CC(C(=O)O)S(=O)(=O)C1]

Step G: To a solution of the Step F product (250.0 mg, 0.33 mmol) in tetrahydrofuran (12 mL) and methanol (4 mL) was added lithium hydroxide monohydrate (2 mL, 2 mmol, 1M in water). The reaction was stirred at room temperature for 3 hours, then concentrated to remove organic solvent. The residue was dissolved in 3 mL of water and then acidified with 1M hydrochloric acid to pH~4.0. The aqueous solution was then extracted with ethyl acetate (2×60 mL). The organic solution was washed with brine (2×30 mL), dried over sodium sulfate and concentrated to give the crude title compound as a white solid (0.22 g, crude) MS (ESI): 706 m/z $[M+H]^+$.

3-[3-[22,28-difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl]phenyl]propanoic Acid

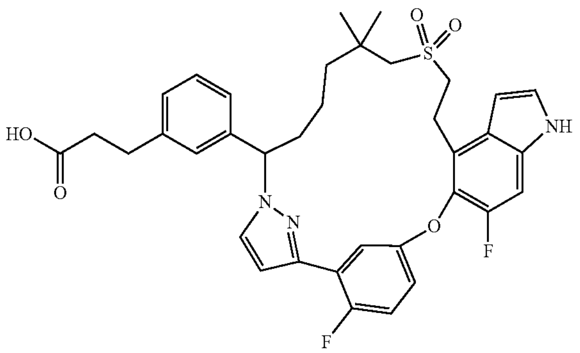 [SMILES: CC1(C)CCCC(c2cccc(CCC(=O)O)c2)n2ccc(n2)-c2cc(ccc2F)Oc2c(F)cc3[nH]ccc3c2CCS(=O)(=O)C1]

Step H: To a solution of the product of Step G (0.21 g, 0.3 mmol) in 20 mL N,N-dimethylformamide was added trimethylamine (0.15 g, 1.5 mmol). The reaction was stirred at 80° C. for 4 hours, then quenched with 1M hydrochloric acid (5 mL) and water (30 mL). The mixture was extracted with ethyl acetate (3×30 mL). The combined organic phases were washed with brine (20 mL), dried over anhydrous sodium sulfate and concentrated. The crude residue was purified by automated flash chromatography (12 g silica gel column, 0-60% ethyl acetate in petroleum) to give the title compound as white solid (152.0 mg, 77%). MS (ESI): 662 m/z $[M+H]^+$. $^1H$ NMR (400 MHz, $CD_3OD$) d 7.63 (dd, J=6.0, 3.2 Hz, 1H), 7.51 (d, J=2.0 Hz, 1H), 7.33 (d, J=3.2 Hz, 1H), 7.30 (d, J=10.8 Hz, 1H), 7.24-7.13 (m, 4H), 7.07 (d, J=7.6 Hz, 1H), 7.02-6.99 (m, 1H), 6.73-6.70 (m, 1H), 6.65 (d, J=3.2 Hz, 1H), 5.36-5.31 (m, 1H), 3.48-3.41 (m, 2H), 3.13-2.99 (m, 2H), 2.87 (t, J=7.6 Hz, 2H), 2.60-2.56 (m, 2H), 2.56 (t, J=7.6 Hz, 2H), 2.33-2.19 (m, 1H), 1.87-1.83 (m, 1H), 1.42-1.36 (m, 1H), 1.18-1.09 (m, 2H), 1.09 (s, 3H), 1.02-0.99 (m, 1H), 0.95 (s, 3H) ppm.

Enantiomer 1 and 2 of Methyl 3-[3-[(6S)-22,28-difluoro-10,10-dimethyl-12,12-dioxo-24-oxa-12lambda6-thia-5,19,30-triazapentacyclo[23.3.1.12, 5.015,23.016,20]triaconta-1(29),2(30),3,15,17,20,22, 25,27-nonaen-6-yl]phenyl]propanoate

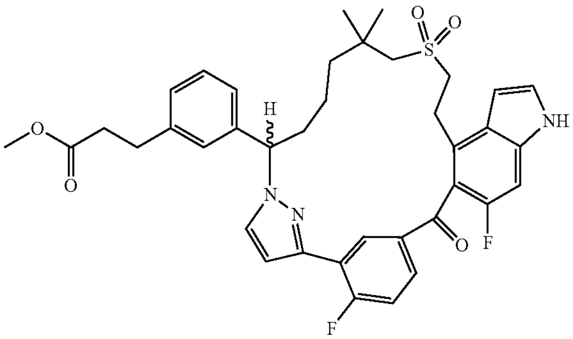

absolute configuration unknown

Step I: To a solution of the Step H product (145 mg, 0.22 mmol) in methanol (15 mL) was added sulfuric acid (0.27 mL). The reaction was stirred at 60° C. for 4 hours then concentrated. The crude residue was taken in ice-water (30 mL) and extracted with ethyl acetate (3×25 mL). The combined organic phases were washed with aq. sodium bicarbonate (2×5 mL), brine, dried over sodium sulfate and concentrated. The crude residue was purified with chiral HPLC. The condition is the following: Instrument: Gilson-281; Column: AD 20*250, 10 um; Mobile Phase: Hexane (0.1% DEA):EtOH (0.1% DEA)=70:30; run time per injection: 14 min; Injection: 1 mL. The first eluent, enantiomer 1 (56.0 mg, 37%): LCMS: MS (ESI): 676 m/z $[M+H]^+$. The second eluent, enantiomer 2 (53.0 mg, 35%): LCMS: MS (ESI): 676 m/z $[M+H]^+$.

Compound 24A, Enantiomer 1 of 3-[3-[22,28-difluoro-10,10-dimethyl-12,12-dioxo-24-oxa-12lambda6-thia-5,19,30-triazapentacyclo[23.3.1.12, 5.015,23.016,20]triaconta-1(29),2(30),3,15,17,20,22, 25,27-nonaen-6-yl]phenyl]propanoic Acid

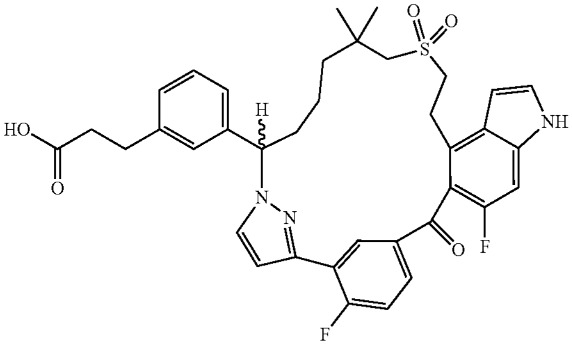

absolute configuration unknown

Step J: To a stirred solution of the first eluent obtain in Step I (50.0 mg, 0.074 mmol) in tetrahydrofuran (6 mL) and methanol (2 mL) was added a solution of 1M lithium hydroxide monohydrate (0.2 mL), the reaction was stirred at room temperature for 3 hours. The aqueous solution was acidified to pH~4.0 with 1 M hydrochloric acid. The aqueous solution was extracted with ethyl acetate (60 mL). The ethyl acetate solution was washed with water, brine, dried with sodium sulfate and concentrated to give the title compound as white solid (38 mg, 78%).

Compound 24A: MS (ESI): 662 m/z $[M+H]^+$. Retention time: 1.48 minutes (LC-MS method: 01). $^1H$ NMR (400 MHz, $CD_3OD$) d 7.63 (dd, J=6.0, 3.2 Hz, 1H), 7.51 (d, J=2.4 Hz, 1H), 7.33 (d, J=3.2 Hz, 1H), 7.30 (d, J=10.8 Hz, 1H), 7.24-7.13 (m, 4H), 7.07 (d, J=7.6 Hz, 1H), 7.02-6.99 (m, 1H), 6.73-6.70 (m, 1H), 6.65 (d, J=3.2 Hz, 1H), 5.36-5.30 (m, 1H), 3.48-3.41 (m, 2H), 3.13-2.99 (m, 2H), 2.87 (t, J=7.6 Hz, 2H), 2.60-2.56 (m, 2H), 2.56 (t, J=7.6 Hz, 2H), 2.33-2.19 (m, 1H), 1.87-1.83 (m, 1H), 1.42-1.36 (m, 1H), 1.18-1.09 (m, 2H), 1.09 (s, 3H), 1.02-0.99 (m, 1H), 0.95 (s, 3H) ppm.

Compound 24B, Enantiomer 2 of 3-[3-[22,28-difluoro-10,10-dimethyl-12,12-dioxo-24-oxa-12lambda6-thia-5,19,30-triazapentacyclo[23.3.1.12, 5.015,23.016,20]triaconta-1(29),2(30),3,15,17,20,22, 25,27-nonaen-6-yl]phenyl]propanoic Acid

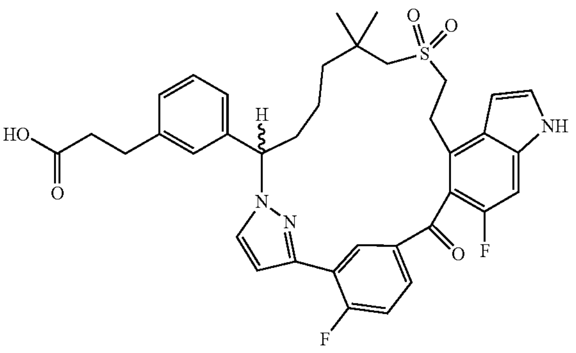

absolute configuration unknown

Step K: Using an identical procedure to Step J, the second eluent product of step I was hydrolyzed to afford the title compound as a white solid (37.0 mg, 77%).

Compound 24B: MS (ESI): 662 m/z $[M+H]^+$, Retention time: 1.48 minutes (LC-MS method: 01). $^1H$ NMR (400 MHz, $CD_3OD$) d 7.63 (dd, J=6.0, 3.2 Hz, 1H), 7.51 (d, J=2.4 Hz, 1H), 7.33 (d, J=3.2 Hz, 1H), 7.30 (d, J=10.8 Hz, 1H), 7.24-7.13 (m, 4H), 7.07 (d, J=7.6 Hz, 1H), 7.02-6.99 (m, 1H), 6.73-6.70 (m, 1H), 6.65 (d, J=3.2 Hz, 1H), 5.34 (dd, J=12.0, 3.2 Hz, 1H), 3.48-3.41 (m, 2H), 3.13-2.99 (m, 2H), 2.87 (t, J=7.6 Hz, 2H), 2.60-2.56 (m, 2H), 2.56 (t, J=7.6 Hz, 2H), 2.33-2.19 (m, 1H), 1.87-1.83 (m, 1H), 1.42-1.36 (m, 1H), 1.18-1.09 (m, 2H), 1.09 (s, 3H), 1.02-0.99 (m 1H), 0.95 (s, 3H) ppm.

The absolute stereochemistry is unknown.

Example 25. 3-[3-(22-Fluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl)phenyl]-2-methylpropanoic Acid

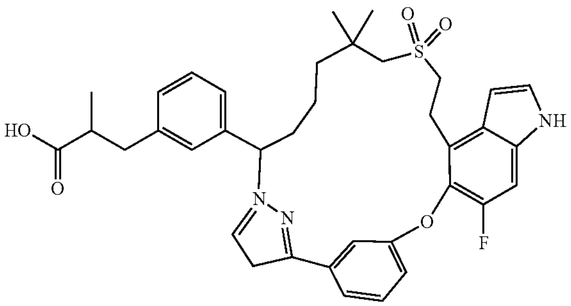

Exchanging ethyl 3-(3-(1-bromo-6-((2-ethoxy-2-oxoethyl)thio)-5,5-dimethylhexyl)phenyl)propanoate (Intermediate 54-1) for Ethyl 3-(3-(1-bromo-6-((2-ethoxy-2-oxoethyl)thio)-5,5-dimethylhexyl)phenyl)-2-methylpropanoate (intermediate 54-2, 10.6 g, 21.1 mmol), the reaction procedure sequence described for Example 24 (Steps A-H) was used to prepare the title compound, Compound 25, (0.216 g, 0.33 mmol) as a white solid.

Compound 25: MS (ESI): 658 m/z $[M+H]^+$. Retention time: 1.52 minutes (LC-MS method 01). $^1H$ NMR (400 MHz, $CD_3OD$) δ 7.60-7.59 (m, 1H), 7.48 (d, J=1.6 Hz, 1H), 7.41-7.38 (m, 2H), 7.34 (d, J=3.2 Hz, 1H), 7.32-7.29 (m, 1H), 7.25 (t, J=7.6 Hz, 1H), 7.18-7.13 (m, 2H), 7.03-7.00 (m, 1H), 6.68 (d, J=2.4 Hz, 1H), 6.66 (dd, J=3.6, 0.8 Hz, 2H), 5.36 (dd, J=11.2, 2.4 Hz, 1H), 3.50-3.41 (m, 2H), 3.07-2.94 (m, 3H), 2.71-2.63 (m, 2H), 2.55 (s, 2H), 2.34-2.24 (m, 1H), 1.95-1.86 (m, 1H), 1.47-1.38 (m, 1H), 1.31-1.10 (m, 8H), 0.97-0.93 (m, 4H) ppm.

Example 26. 2-[3-(22,28-Difluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl)phenyl]acetic Acid

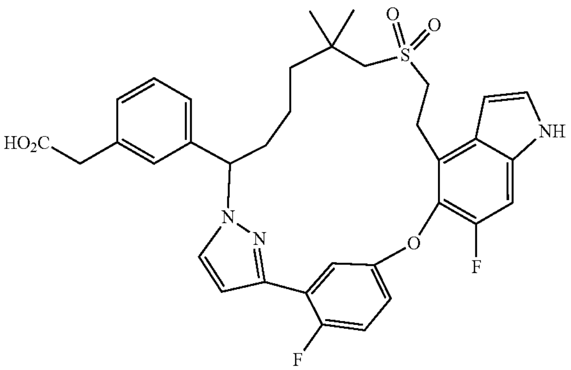 [SMILES: CC1(C)CCCC(c2cccc(CC(=O)O)c2)n2ccc(n2)-c2cc(ccc2F)Oc2c(F)cc3[nH]ccc3c2CCS(=O)(=O)C1]

Exchanging ethyl 3-(3-(1-bromo-6-((2-ethoxy-2-oxoethyl)thio)-5,5-dimethylhexyl)phenyl)propanoate (Intermediate 54-1) for ethyl 2-(3-(1-bromo-6-((2-ethoxy-2-oxoethyl)thio)-5,5-dimethylhexyl)phenyl)acetate (intermediate 54-3, 1.62 g, 3.29 mmol), the reaction procedure sequence described for Example 24 (Steps A-H) was used to prepare Compound 26 (0.0062 g, 0.010 mmol) as a white solid.

Compound 26: MS (ESI): 648 m/z $[M+H]^+$. Retention time: 1.44 minutes (LC-MS method: 01). $^1H$ NMR (400 MHz, $CD_3OD$) δ 8.45 (brs, 1H), 7.67-7.65 (m, 1H), 7.53 (d, J=2.4 Hz, 1H), 7.34 (d, J=3.2 Hz, 1H), 7.31 (d, J=10.8 Hz, 1H), 7.27-7.21 (m, 3H), 7.20-7.16 (m, 1H), 7.14 (d, J=7.6 Hz, 1H), 7.02-6.98 (m, 1H), 6.74-6.72 (m, 1H), 6.66 (d, J=3.2 Hz, 1H), 5.39-5.35 (m, 1H), 3.56 (s, 2H), 3.50-3.44 (m, 2H), 3.13-3.01 (m, 2H), 2.60 (s, 2H), 2.31-2.27 (m, 1H), 1.90-1.87 (m, 1H), 1.64-1.60 (m, 1H), 1.45-1.40 (m, 1H), 1.23-1.14 (m, 2H), 1.10 (s, 3H), 0.97 (s, 3H) ppm.

Example 27. Enantiomer 1 and 2 of 3-[3-(22,28-Difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenyl]propanoic Acid

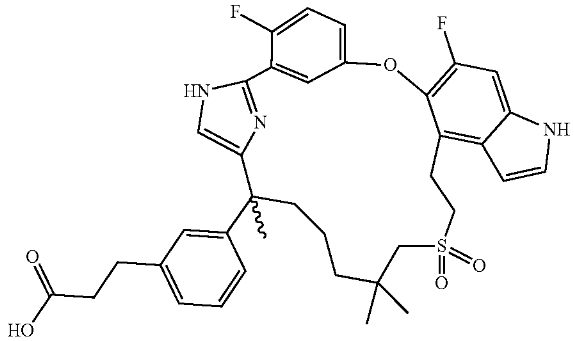 [SMILES: CC1(C)CCCC(C)(c2cccc(CCC(=O)O)c2)c2c[nH]c(n2)-c2cc(ccc2F)Oc2c(F)cc3[nH]ccc3c2CCS(=O)(=O)C1]

Methyl 3-(3-(2-(2-(2-fluoro-5-((6-fluoro-4-vinyl-1H-indol-5-yl)oxy)phenyl)-1H-imidazol-5-yl)-7-((2-methoxy-2-oxoethyl)sulfonyl)-6,6-dimethylheptan-2-yl)phenyl)propanoate

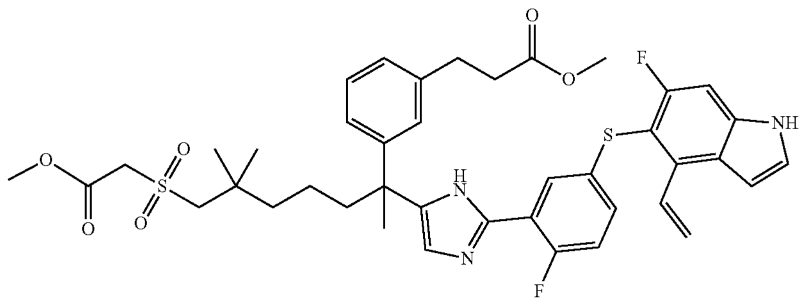 [SMILES: C=Cc1c(Sc2ccc(F)c(-c3ncc(C(C)(CCCC(C)(C)CS(=O)(=O)CC(=O)OC)c4cccc(CCC(=O)OC)c4)[nH]3)c2)c(F)cc2[nH]ccc12]

Step A: To a stirred solution of methyl 3-(3-(1-chloro-8-((2-methoxy-2-oxoethyl)sulfonyl)-3,7,7-trimethyl-2-oxooctan-3-yl)phenyl)propanoate (Intermediate 8-3, 7.8 g, 14.2 mmol) in dimethylformamide (150 mL) was added 2-fluoro-5-((6-fluoro-4-vinyl-1H-indol-5-yl)oxy)benzimidamide (intermediate 10-3, 4.91 g, 15.7 mmol), sodium bicarbonate (2.39 g, 28.5 mmol). The reaction was stirred at 80° C. overnight, then cooled to room temperature and diluted with ethyl acetate (250 mL). The separated organic layer was washed with water (2×250 mL), brine, dried over anhydrous sodium sulfate and concentrated. The residue was purified by automated flash chromatography (80 g silica gel column, 0-70% ethyl acetate in petroleum ether) to give the title compound (8.2 g, 76%) as a yellow solid. MS (ESI): 762 m/z $[M+H]^+$. RT: 1.85 min (LC-MS method 008).

Methyl 3-(3-(2-(2-(2-fluoro-5-((6-fluoro-4-formyl-1H-indol-5-yl)oxy)phenyl)-1H-imidazol-5-yl)-7-((2-methoxy-2-oxoethyl)sulfonyl)-6,6-dimethylheptan-2-yl)phenyl)propanoate

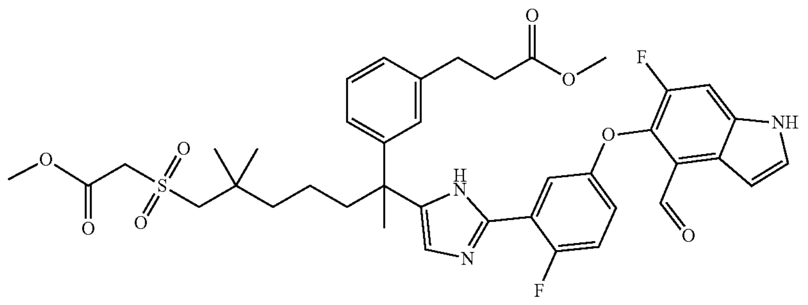 [SMILES: COC(=O)CCc1cccc(C(C)(CCCC(C)(C)CS(=O)(=O)CC(=O)OC)c2cnc(-c3cc(Oc4c(F)cc5[nH]ccc5c4C=O)ccc3F)[nH]2)c1]

Step B: To a stirred solution of methyl 3-(3-(2-(2-(2-fluoro-5-((6-fluoro-4-vinyl-1H-indol-5-yl)oxy)phenyl)-1H-imidazol-5-yl)-7-((2-methoxy-2-oxoethyl)sulfonyl)-6,6-dimethylheptan-2-yl)phenyl)propanoate (Step A product, 3.00 g, 3.94 mmol) in tetrahydrofuran (150 mL) and water (75 mL) was added sodium periodate (2.53 g, 11.8 mmol), osmium tetroxide (1 g/mL in water, 30 mL, 0.12 mmol). The reaction was stirred at room temperature for 16 hours, then diluted with ethyl acetate (300 mL). The mixture was washed with water (2×300 mL), brine, dried over anhydrous sodium sulfate and concentrated. The residue was purified by automated flash chromatography (40 g silica gel column, 0-60% ethyl acetate in petroleum ether) to give the title compound (2.1 g, 70% yield) as an oil. MS (ESI): 764 m/z $[M+H]^+$. RT: 1.73 min (LC-MS method 008).

Methyl (13E)-22,28-difluoro-6-[3-(3-methoxy-3-oxo-propyl)phenyl]-6,10,10-trimethyl-12,12-dioxo-24-oxa-12lambda6-thia-3,19,30-triazapentacyclo[23.3.1.12,5.015,23.016,20]triaconta-1(29),2,4,13,15,17,20,22,25,27-decaene-13-carboxylate

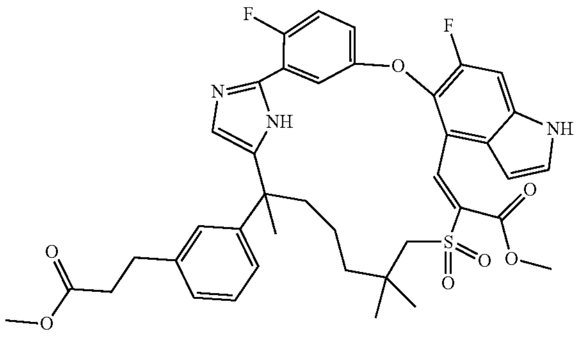 [SMILES: COC(=O)CCc1cccc(C2(C)CCCC(C)(C)CS(=O)(=O)/C(C(=O)OC)=C/c3c(c(F)cc4[nH]ccc34)Oc3ccc(F)c(c3)-c3ncc2[nH]3)c1]

Step C: To a stirred solution of methyl 3-(3-(2-(2-(2-fluoro-5-((6-fluoro-4-formyl-1H-indol-5-yl)oxy)phenyl)-1H-imidazol-5-yl)-7-((2-methoxy-2-oxoethyl)sulfonyl)-6,6-dimethylheptan-2-yl)phenyl)propanoate (Step B product, 2.1 g, 2.75 mmol) in toluene (400 mL) was added piperidine (1.17 g, 13.7 mmol) and acetic acid (0.15 mL, 2.75 mmol). The mixture was stirred at 110° C. for 16 hours, then concentrated. The mixture was diluted with ethyl acetate (100 mL), washed with water (2×50 mL), brine, dried over sodium sulfate. The solvent was removed, and the residue was purified by automated flash chromatography (40 g silica gel column, 0-60% ethyl acetate in petroleum) to give the title compound (980 mg, 48% yield) as a yellow solid. MS (ESI): 746 m/z $[M+H]^+$. RT: 1.94 min (LC-MS method 008).

Methyl 22,28-difluoro-6-[3-(3-methoxy-3-oxo-propyl)phenyl]-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaene-13-carboxylate

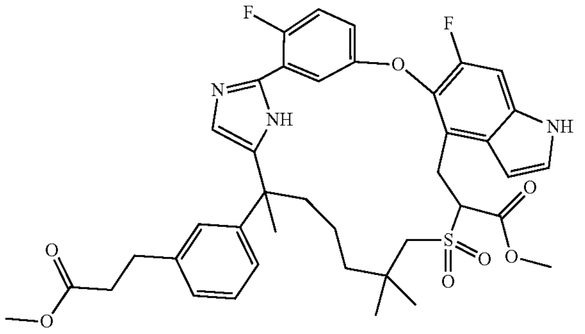 [SMILES: COC(=O)CCc1cccc(C2(C)CCCC(C)(C)CS(=O)(=O)C(C(=O)OC)Cc3c(c(F)cc4[nH]ccc34)Oc3ccc(F)c(c3)-c3ncc2[nH]3)c1]

Step D: To a stirred solution of methyl (13E)-22,28-difluoro-6-[3-(3-methoxy-3-oxo-propyl)phenyl]-6,10,10-trimethyl-12,12-dioxo-24-oxa-12lambda6-thia-3,19,30-triazapentacyclo[23.3.1.12,5.015,23.016,20]triaconta-1(29),2,4,13,15,17,20,22,25,27-decaene-13-carboxylate (Step C product, 980 mg, 1.31 mmol) in tetrahydrofuran (30 mL) was added palladium on carbon (10%) (200 mg). The reaction was stirred under hydrogen balloon for 16 hours at room temperature. The mixture was filtered through a pad of Celite and washed with tetrahydrofuran (50 mL). The filtrate was concentrated in vacuo to give the title compound (902 mg, 91% yield) as a white solid. MS (ESI): 748 m/z $[M+H]^+$. RT: 1.92 min (LC-MS method 008).

6-[3-(2-Carboxyethyl)phenyl]-22,28-difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaene-13-carboxylic Acid

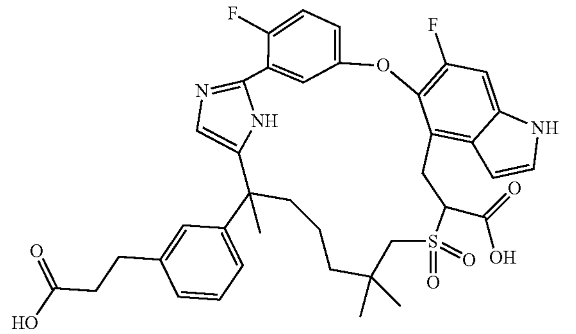 [SMILES: CC1(C)CCCC(C)(c2cccc(CCC(=O)O)c2)c2cnc([nH]2)-c2cc(ccc2F)Oc2c(F)cc3[nH]ccc3c2CC(C(=O)O)S(=O)(=O)C1]

Step E: To a stirred solution of methyl 22,28-difluoro-6-[3-(3-methoxy-3-oxo-propyl)phenyl]-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaene-13-carboxylate (Step D product, 902 mg, 1.21 mmol) in tetrahydrofuran (30 mL) was added lithium hydroxide monohydrate (1 M in water, 6 mL). The reaction was stirred at RT for 16 hours, then treated with 1 M HCl to pH-4. The mixture was extracted with ethyl acetate (2×30 mL). The combined organic extracts were washed with brine, dried over sodium sulfate, and concentrated to afford the title compound (800 mg, 92% yield) as a white solid. MS (ESI): 720 m/z $[M+H]^+$. RT: 1.71 min (LC-MS method 008).

3-[3-(22,28-Difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenyl]propanoic Acid

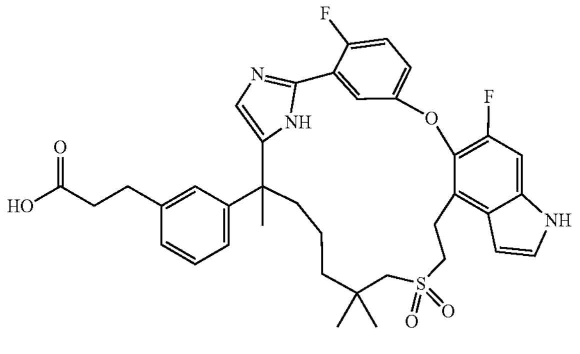 [SMILES: CC1(C)CCCC(C)(c2cccc(CCC(=O)O)c2)c2cnc([nH]2)-c2cc(ccc2F)Oc2c(F)cc3[nH]ccc3c2CCS(=O)(=O)C1]

Step F: To a stirred solution of 6-[3-(2-carboxyethyl)phenyl]-22,28-difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27- nonaene-13-carboxylic acid (Step E product, 1.2 g, 1.67 mmol) in DMSO (30 mL) was added lithium chloride (212 mg, 5.0 mmol) and water (2.0 mL, 66.6 mmol). The reaction mixture was stirred at 120° C. for 24 hours, then cooled to room temperature and acidified with 1 M HCl to pH-4. The mixture was extracted with ethyl acetate (100 mL), washed with brine (100 mL×2), dried over sodium sulfate and concentrated. The residue was purified by automated flash chromatography (20 g silica gel column, 10% methanol in dichloromethane) to give the title compound (860 mg, yield 76%) as a white solid. MS (ESI): 676 m/z [M+H]$^+$. RT: 1.75 min (LC-MS method 008).

Compounds 27A and 27B: Enantiomers 1 and 2 of 3-[3-(22,28-difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenyl]propanoic Acid

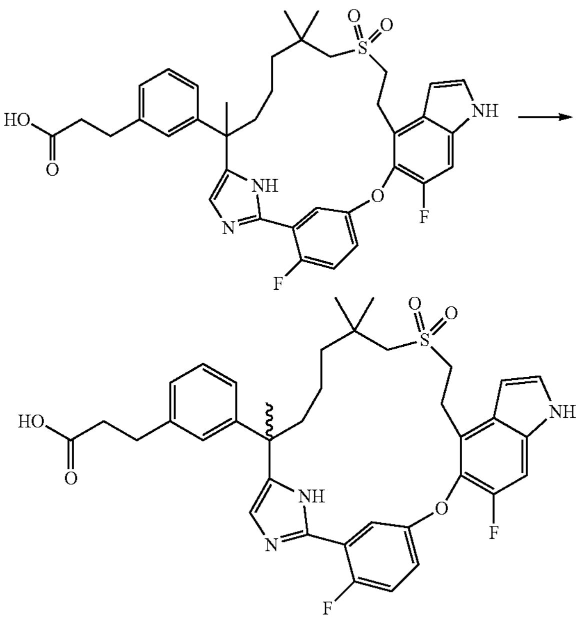

Enantiomer 1, first eluting isomer (27A)
Enantiomer 2, secon eluting isomer (27B)
(absolute configurations unknown)

Step G: The racemic, crude product of step F (1.38 g, 2.04 mmol) was subjected to chiral SFC using a Thar SFC-80 instrument and the following separation conditions: Column: 20×250 mm×10 μm Whelk CHIRALCEL OD; sample solution: 1.38 g dissolved in methanol (40 mL); injection volume: 0.8 mL; eluant: 50:50 $CO_2$/ethanol with 1% ammonia/methanol additive; flow rate: 80 g/min; column temperature: 35° C.; back pressure: 100 bar; detection wavelength: 214 nm; Cycle time: 4 min. The first eluting isomer was designated Enantiomer 1 (507.9 mg, yield: 37%) and the second eluting isomer, Enantiomer 2 (539.7 mg, yield: 39%).

Compound 27A: Enantiomer 1 of 3-[3-(22,28-difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenyl]propanoic acid: $^1$H NMR (400 MHz, $CD_3OD$) δ 7.43 (dd, J=5.8, 3.1 Hz, 1H), 7.20 (d, J=3.2 Hz, 1H), 7.17-7.09 (m, 2H), 7.06-6.95 (m, 3H), 6.94-6.88 (m, 3H), 6.51 (d, J=3.2 Hz, 1H), 3.33-3.22 (m, 2H), 3.13-2.91 (m, 2H), 2.74 (t, J=7.7 Hz, 2H), 2.56 (s, 2H), 2.42 (t, J=7.7 Hz, 2H), 1.94-1.83 (m, 2H), 1.45 (s, 3H), 1.26-1.11 (m, 2H), 1.06-0.95 (m, 4H), 0.89-0.77 (m, 4H). MS (ESI): 676 m/z [M+H]$^+$. RT: 1.03 min (LC-MS method 01).

Compound 27B: Enantiomer 2 of 3-[3-(22,28-difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenyl]propanoic acid: $^1$H NMR (400 MHz, $CD_3OD$) δ 7.43 (dd, J=5.8, 3.1 Hz, 1H), 7.20 (d, J=3.2 Hz, 1H), 7.17-7.09 (m, 2H), 7.06-6.95 (m, 3H), 6.94-6.88 (m, 3H), 6.51 (d, J=3.2 Hz, 1H), 3.32-2.24 (m, 2H), 3.13-2.91 (m, 2H), 2.74 (t, J=7.7 Hz, 2H), 2.56 (s, 2H), 2.42 (t, J=7.7 Hz, 2H), 1.895-1.83 (m, 2H), 1.45 (s, 3H), 1.26-1.11 (m, 2H), 1.06-0.95 (m, 4H), 0.89-0.77 (m, 4H). MS (ESI): 676 m/z [M+H]$^+$. RT: 1.03 min (LC-MS method 01).

Example 28. 3-[3-(22,28-Difluoro-3,6,10,10-tetramethyl-12,12-dioxo-9,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

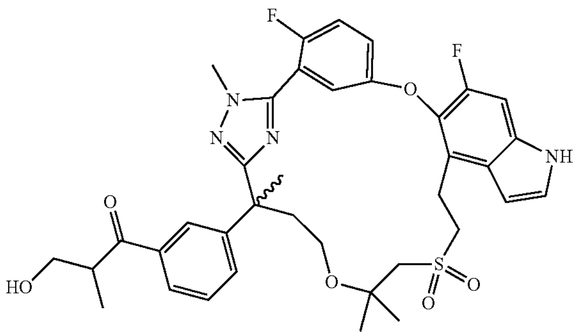 [SMILES: CC(CO)C(=O)c1cccc(C2(C)CCOC(C)(C)CS(=O)(=O)CCc3c(c(F)cc4[nH]ccc34)Oc3ccc(F)c(c3)-c3nc2nn3C)c1]

3-[3-(22,28-difluoro-3,6,10,10-tetramethyl-12,12-dioxo-9,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic acid Step A: Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) for ethyl 3-(3-(4-((1-((2-ethoxy-2-oxoethyl)sulfonyl)-2-methylpropan-2-yl)oxy)-2-methyl-1-(2-methylhydrazineyl)-1-oxobutan-2-yl)phenyl)-2-methylpropanoate (intermediate 45-5), the reaction procedure sequence described for Example 1 (Steps A-G) was used to prepare the title compound (0.85 g, 1.2 mmol) as a white solid. MS (ESI): 707 m/z [M+H]$^+$. RT: 2.03 min (LC-MS method 008).

Compounds 28A and 28B: Isomers 1 and 2 of 3-[3-(22,28-difluoro-3,6,10,10-tetramethyl-12,12-dioxo-9,24-dioxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

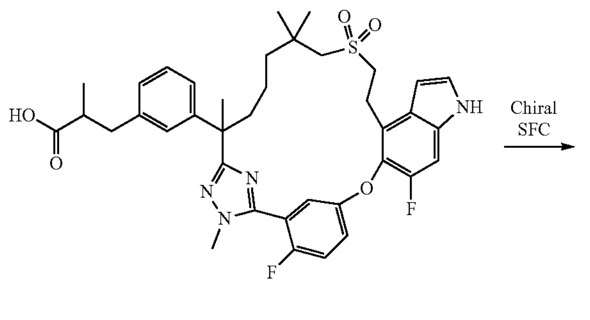

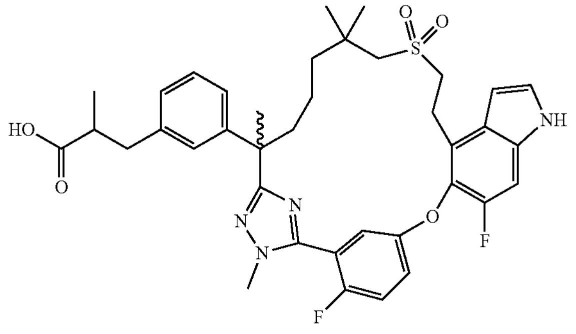

Isomer 1, first eluting isomer (28A)
Isomer 2, second eluting isomer (28B)
absolute structure unknown Step B: The racemic, crude product of step A (850 mg, 1.2 mmol) was subjected to chiral SFC using a Thar SFC-80 instrument and the following separation conditions: Column: 20×250 mm×10 µm Whelk CHIRALCEL AD; sample solution: 850 mg dissolved in methanol (40 mL); injection volume: 0.8 mL; eluant: 75:25 carbon dioxide/isopropyl alcohol with 0.1% trifluoroacetic acid additive; flow rate: 80 g/min; column temperature: 35° C.; back pressure: 100 bar; detection wavelength: 214 nm; Cycle time: 5.5 minutes. The first eluting isomer was designated Enantiomer 1 (Compound 28A) (302 mg, yield 36%) and the second eluting isomer, Enantiomer 2 (Compound 28B) (271 mg, yield 32%).

Compound 28A: $^1$H NMR (400 MHz, $CD_3OD$) δ 7.42-7.37 (m, 2H), 7.35-7.34 (m, 1H), 7.24 (d, J=10.8 Hz, 1H), 7.15 (t, J=7.2 Hz, 1H), 7.13-7.10 (m, 1H), 7.00 (d, J=7.6 Hz, 1H), 6.98-6.93 (m, 2H), 6.62 (d, J=2.8 Hz, 1H), 3.88 (d, J=2.8 Hz, 3H), 3.72-3.66 (m, 1H), 3.45-3.36 (m, 4H), 3.16-3.11 (m, 3H), 2.94-2.87 (m, 1H), 2.63-2.56 (m, 2H), 2.36-2.29 (m, 1H), 2.13-2.08 (m, 1H), 1.67 (s, 3H), 1.30 (s, 3H), 1.24 (s, 3H), 1.05 (dd, J=6.8, 1.6 Hz, 3H) ppm. MS (ESI): 707 m/z $[M+H]^+$. RT: 1.33 min (LC-MS method 01). Chiral HPLC: 100%.

Compound 28B: $^1$H NMR (400 MHz, $CD_3OD$) δ 7.40-7.38 (m, 2H), 7.35-7.34 (m, 1H), 7.24 (d, J=10.8 Hz, 1H), 7.14 (t, J=7.6 Hz, 1H), 7.11-7.10 (m, 1H), 7.00 (d, J=8.0 Hz, 1H), 6.98-6.93 (m, 2H), 6.62 (d, J=2.8 Hz, 1H), 3.88 (d, J=2.8 Hz, 3H), 3.72-3.66 (m, 1H), 3.45-3.36 (m, 4H), 3.16-3.11 (m, 3H), 2.94-2.86 (m, 1H), 2.64-2.54 (m, 2H), 2.36-2.29 (m, 1H), 2.13-2.08 (m, 1H), 1.67 (s, 3H), 1.30 (s, 3H), 1.24 (s, 3H), 1.05 (dd, J=6.8, 1.6 Hz, 3H) ppm. MS (ESI): 707 m/z $[M+H]^+$. RT: 1.33 min (LC-MS method 01). Chiral HPLC: 100%.

Example 29. Enantiomers 1 and 2 of 3-[3-(22,28-difluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2,2-dimethyl-propanoic Acid

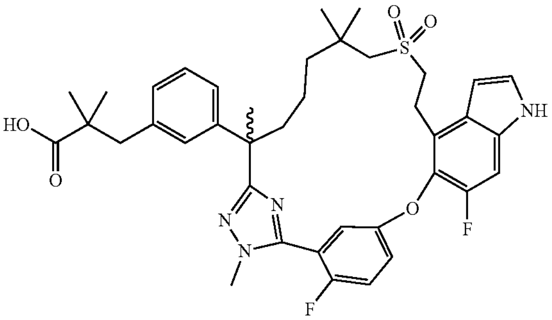 [SMILES: Cn1nc2nc1-c1cc(ccc1F)Oc1c(F)cc3[nH]ccc3c1CCS(=O)(=O)CC(C)(C)CCCC2(C)c1cccc(CC(C)(C)C(=O)O)c1]

3-[3-(22,28-Difluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2,2-dimethyl-propanoic acid Step A: Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) for ethyl 3-(3-(7-((2-ethoxy-2-oxoethyl)sulfonyl)-2,6,6-trimethyl-1-(2-methylhydrazineyl)-1-oxoheptan-2-yl)phenyl)-2,2-dimethylpropanoate (intermediate 45-4, 1.8 g, 3.24 mmol), the reaction procedure sequence described for Example 1 (Steps A-G) was used to prepare the title compound (0.200 g, 0.28 mmol) as a white solid. MS (ESI): 719 m/z $[M+H]^+$. RT: 1.95 min (LC-MS method 008).

Compounds 29A and 29B, enantiomers 1 and 2 of 3-[3-(22,28-Difluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2,2-dimethyl-propanoic acid

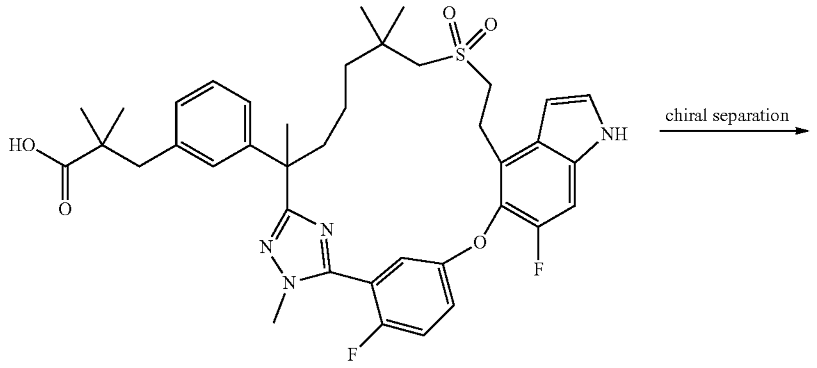

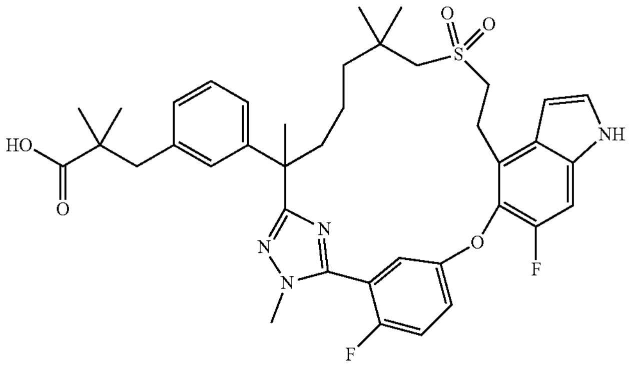

First Eluent, enantiomer 1 (29A)
Second eluent: Enantiomer 2 (29B)
Absolute configuration unknown Step B: The racemic product of step A (200 mg, 0.28 mmol) was subjected to chiral SFC using a Thar SFC-80 instrument and the following separation conditions: Column: 20×250 mm×10 μm IG; sample solution: 200 mg dissolved in methanol (25 mL); injection volume: 1.9 mL; mobile phase: 75:25 carbon dioxide/isopropyl alcohol with 0.1% trifluoroacetic acid additive; flow rate: 80 g/min; column temperature: 35° C.; back pressure: 100 bar; detection wavelength: 214 nm; cycle time: 4.2 minutes. The first eluting isomer was designated Enantiomer 1 (Compound 29A) (40.8 mg, yield 20%) and the second eluting isomer, Enantiomer 2 (Compound 29B) (44.2 mg, 22%).

Compound 29A: $^1$H NMR (400 MHz, $CD_3OD$) δ 7.39-7.30 (m, 3H), 7.23 (d, J=10.8 Hz, 1H), 7.21-7.17 (m, 1H), 7.15 (t, J=8.0 Hz, 1H), 7.04-6.94 (m, 3H), 6.63 (dd, J=3.2, 0.8 Hz, 1H), 3.87 (d, J=2.2 Hz, 3H), 3.42-3.35 (m, 3H), 3.25-3.20 (m, 1H), 2.99 (d, J=13.6 Hz, 1H), 2.83 (d, J=13.6 Hz, 1H), 2.79 (s, 2H), 2.15 (dt, J=12.8, 3.6 Hz, 1H), 1.82 (dt, J=12.8, 3.6 Hz, 1H), 1.69 (s, 3H), 1.64-1.57 (m, 1H), 1.41-1.30 (m, 2H), 1.24-1.18 (m, 1H), 1.08 (s, 3H), 1.07 (s, 3H), 1.06 (s, 6H) ppm. MS (ESI): 719 m/z $[M+H]^+$. RT: 1.50 min (LC-MS method 01). Chiral HPLC: 100%.

Compound 29B: $^1$H NMR (400 MHz, $CD_3OD$) δ 7.39-7.30 (m, 3H), 7.23 (d, J=10.8 Hz, 1H), 7.21-7.17 (m, 1H), 7.15 (t, J=8.0 Hz, 1H), 7.04-6.94 (m, 3H), 6.63 (dd, J=3.2, 0.8 Hz, 1H), 3.87 (d, J=2.2 Hz, 3H), 3.42-3.35 (m, 3H), 3.25-3.20 (m, 1H), 2.99 (d, J=13.6 Hz, 1H), 2.83 (d, J=13.6 Hz, 1H), 2.79 (s, 2H), 2.15 (dt, J=12.8, 3.6 Hz, 1H), 1.82 (dt, J=12.8, 3.6 Hz, 1H), 1.69 (s, 3H), 1.64-1.57 (m, 1H), 1.41-1.30 (m, 2H), 1.24-1.18 (m, 1H), 1.08 (s, 3H), 1.07 (s, 3H), 1.06 (s, 6H) ppm. MS (ESI): 719 m/z $[M+H]^+$. RT: 1.50 min (LC-MS method 01). Chiral HPLC: 100%.

Example 30. Diastereomers 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic acid

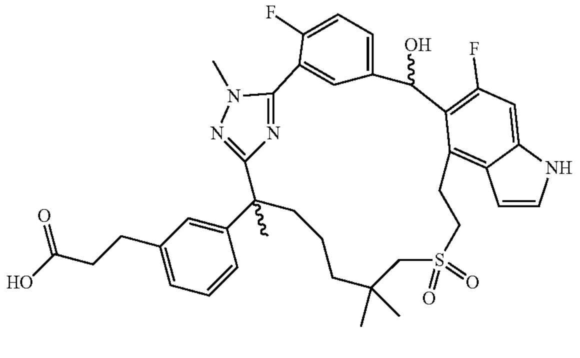 [SMILES: Cn1nc2nc1-c1cc(ccc1F)C(O)c1c(F)cc3[nH]ccc3c1CCS(=O)(=O)CC(C)(C)CCCC2(C)c1cccc(CCC(=O)O)c1]

Ethyl 3-[3-[(6R)-22,28-difluoro-3,6-dimethyl-12,12-dioxo-spiro[24-oxa-12lambda6-thia-3,4,19,30-tetrazapentacyclo[23.3.1.12,5.015, 23.016,20]triaconta-1(29),2(30),4,15,17,20,22,25,27-nonaene-10,1'-cyclopropane]-6-yl]phenyl]-2-methyl-propanoate

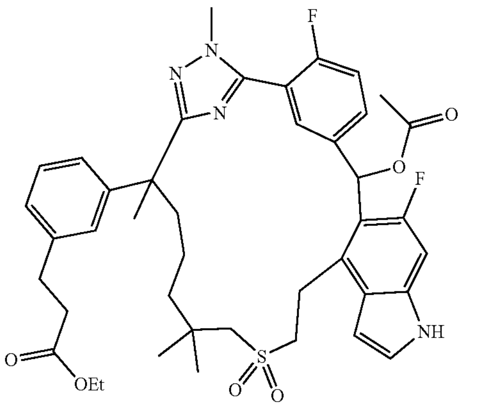 [SMILES: CCOC(=O)CCc1cccc(C2(C)CCCC(C)(C)CS(=O)(=O)CCc3c(c(F)cc4[nH]ccc34)C(OC(C)=O)c3ccc(F)c(c3)-c3nc2nn3C)c1]

Step A: Exchanging methyl 5-((4-bromo-6-fluoro-1H-indol-5-yl)oxy)-2-fluorobenzimidothioate hydroiodide (Intermediate 14-1) for (4-bromo-6-fluoro-1H-indol-5-yl)(4-fluoro-3-(imino(methylthio)methyl)phenyl)methyl acetate hydroiodide (Intermediate 57, 1.55 g, 2.67 mmol), the reaction procedure sequence described for Example 6 (Steps A-D) was used to prepare the title compound (1.3 g, 1.68 mmol) as a white solid. MS (ESI): 775 m/z $[M+H]^+$. RT: 1.51 min (LC-MS method 22). Methyl 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoate

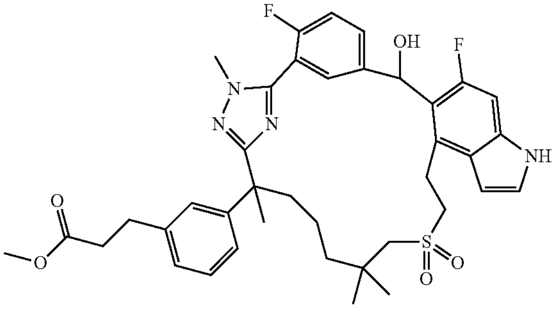 [SMILES: COC(=O)CCc1cccc(C2(C)CCCC(C)(C)CS(=O)(=O)CCc3c(c(F)cc4[nH]ccc34)C(O)c3ccc(F)c(c3)-c3nc2nn3C)c1]

Step B: To a stirred solution of the Step A product (1.3 g, 1.68 mmol) in methanol (20 mL) was added potassium carbonate (0.464 g, 3.36 mmol). The reaction was stirred at room temperature for 1 hour. The solvent was evaporated. The residue was acidified with 1N HCl to pH ~4, then diluted with ethyl acetate (100 mL). The mixture was washed with water, brine, dried over anhydrous sodium sulfate, filtered, and concentrated. The residue was purified by automated flash chromatography (40 g silica gel column, 0-10% methanol in dichloromethane) to give a mixture of 4 diastereomers (the title compound) (1.1 g, yield 91.2%) as a solid. MS (ESI): 719 m/z $[M+H]^+$, RT: 1.41 minutes (LC-MS method 22).

Diastereomers 1 and 2 of methyl 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoate

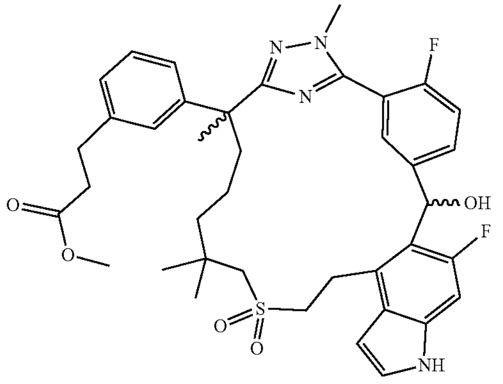

+

First eluent, Diastereomer 1
Second eluent, Diastereomer 2
Relative configuration unknown Step C: The 4 diastereomeric mixture (0.60 g, 0.84 mmol) of the Step B product was carefully purified again by automated flash chromatography (40 g silica gel column, 0-10% methanol in dichloromethane) to give the first eluent, diastereomer 1 (0.3 g, yield 50%) and the second eluent, diastereomer 2 (0.25 g, yield 41.7%), both as white solid. Diastereomer 1 of methyl 3-[3-(22,28-difluoro-24-hydroxy-3,6,10,10-tetramethyl-12,12-dioxo-12lambda6-thia-3,4,19,30-tetrazapentacyclo [23.3.1.12,5.015,23.016,20]triaconta-1(29),2(30),4,15,17,20,22,25,27-nonaen-6-yl)phenyl] propanoate: MS (ESI): 719 m/z $[M+H]^+$. RT: 1.45 min (LC-MS method 22).

Diastereomer 2 of methyl 3-[3-(22,28-difluoro-24-hydroxy-3,6,10,10-tetramethyl-12,12-dioxo-12lambda6-thia-3,4,19,30-tetrazapentacyclo [23.3.1.12,5.015,23.016,20] triaconta-1(29),2(30),4,15,17,20,22,25,27-nonaen-6-yl) phenyl]propanoate: MS (ESI): 719 m/z $[M+H]^+$. RT: 1.41 min (LC-MS method 22).

Diastereomer 1 of 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid (Relative Configuration Unknown)

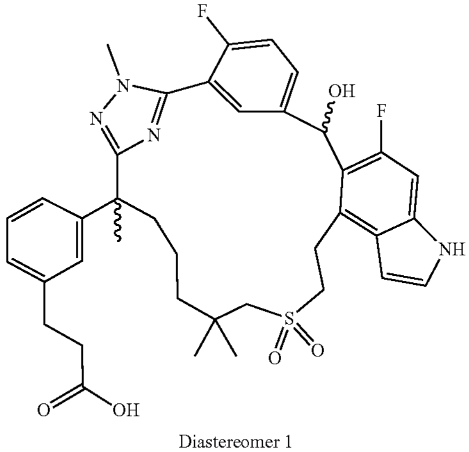

Diastereomer 1
Relative configuration unknown

Step D: A solution of diastereomer 1 from Step C product (210 mg, 0.29 mmol) in 7.3 mL of lithium hydroxide (0.2 M in tetrahydrofuran/methanol/water (3:1:1) was stirred at room temperature for 2 hours. The mixture was acidified with 1N hydrochloride to pH ~4, diluted with ethyl acetate (50 mL), washed with water (2×20 mL), brine (2×20 mL), dried over anhydrous sodium sulfate, filtered, and concentrated. The residue was purified by automated flash chromatography (40 g silica gel column, 0-10% methanol in dichloromethane) to give the title compound (absolute configuration unknown) (160 mg, yield 77%) as solid. MS (ESI): 705 m/z [M+H]$^+$. RT: 1.30 min (LC-MS method 22).

Diastereomer 2 of 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid (Absolute Configuration Unknown)

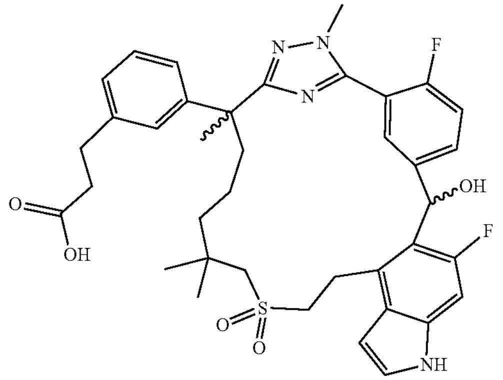

Diastereomer 2
relative configuration unknown

Step E: Using a procedure identical to that described in step D, the Diastereomer 2 product of step C (0.22 g, 0.31 mmol) was hydrolyzed to afford the title compound as a white solid (0.14 g, 86%). MS (ESI): 705 m/z [M+H]$^+$. RT: 1.27 min (LC-MS method 22).

Compounds 30A and 30B Enantiomers 1 and 2 of 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic acid

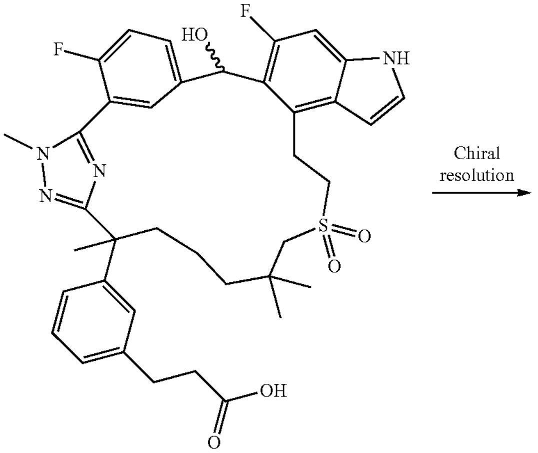

Diastereomer 1
Relative configuration unknown

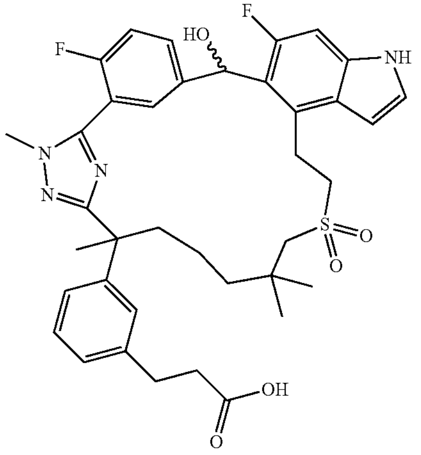

First eluent, Enantiomer 1 (30A)
Second eluent, Enantiomer 2 (30B)
Absolute and relative configuration unknown Step F: The racemic diastereomer 1 of Step D product (160 mg, 0.23 mmol) was subjected to chiral SFC using a Thar SFC-80 (Waters) instrument and the following separation conditions. Column: 20×250 mm×10 μm Whelk CHIRALCEL AD; sample solution: 160 mg dissolved in methanol (28 mL); injection volume: 1.0 mL; eluant: 75:25 carbon dioxide/isopropyl alcohol with 0.2% methanol ammonia additive; flow rate: 80 g/min; column temperature: 35° C.; back pressure: 100 bar; detection wavelength: 214 nm; Cycle time: 4.6 minutes. The first eluting isomer was designated Enantiomer 1, an impure product. This impure enantiomer 1 was further purified by automated flash chromatography (12 g silica gel column, eluting with 0-10% methanol in dichloromethane) to give pure Enantiomer 1 (absolute and relative configuration unknown, 38.1 mg, yield 23%) as a white solid.

The second eluting isomer was designated as Enantiomer 2, an impure product. This impure enantiomer 2 was purified using identical conditions as above, to give pure Enantiomer 2 (absolute and relative configuration unknown, 25.8 mg, yield 16%) as a white solid.

Compound 30A, Enantiomer 1 of 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016, 20]triaconta-1(29),2(30),4,15,17,20,22,25,27-nonaen-6-yl) phenyl]propanoic acid: MS (ESI): 705 m/z $[M+H]^+$. RT: 1.78 min (LC-MS method 13). $^1$H NMR (400 MHz, $CD_3OD$) δ 8.10 (d, J=6.0 Hz, 1H), 7.39-7.35 (m, 1H), 7.27-7.23 (m, 2H), 7.23-7.17 (m, 1H), 7.16 (d, J=8.0 Hz, 1H), 7.12 (d, J=11.6 Hz, 1H), 7.08-7.03 (m, 2H), 6.52 (s, 1H), 6.45 (d, J=3.2 Hz, 1H), 3.91 (d, J=3.2 Hz, 3H), 3.60 (t, J=13.2 Hz, 1H), 3.49-3.43 (m, 1H), 3.18-3.08 (m, 2H), 3.04-2.95 (m, 2H), 2.89 (t, J=7.6 Hz, 2H), 2.57 (t, J=7.6 Hz, 2H), 2.40-2.34 (m, 1H), 2.16-2.08 (m, 1H), 1.75 (s, 3H), 1.57-1.37 (m, 3H), 1.32 (s, 3H), 1.22 (s, 3H), 1.09-1.01 (m, 1H) ppm. ee %: 100%.

Compound 30B, Enantiomer 2 of 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016, 20]triaconta-1(29),2(30),4,15,17,20,22,25,27-nonaen-6-yl) phenyl]propanoic acid: MS (ESI): 705 m/z $[M+H]^+$. RT: 1.78 min (LC-MS method 13). $^1$H NMR (400 MHz, $CD_3OD$) δ 8.10 (d, J=6.0 Hz, 1H), 7.39-7.35 (m, 1H), 7.27-7.24 (m, 2H), 7.23-7.15 (m, 1H), 7.17 (d, J=7.6 Hz, 1H), 7.13 (d, J=11.2 Hz, 1H), 7.08-7.03 (m, 2H), 6.52 (s, 1H), 6.45 (d, J=3.2 Hz, 1H), 3.91 (d, J=3.2 Hz, 3H), 3.61 (t, J=13.2 Hz, 1H), 3.49-3.43 (m, 1H), 3.18-3.08 (m, 2H), 3.05-2.95 (m, 2H), 2.89 (t, J=7.6 Hz, 2H), 2.57 (t, J=7.6 Hz, 2H), 2.40-2.33 (m, 1H), 2.16-2.08 (m, 1H), 1.75 (s, 3H), 1.58-1.39 (m, 3H), 1.32 (s, 3H), 1.22 (s, 3H), 1.09-1.03 (m, 1H) ppm. ee %: 96.58%.

Compounds 30C and 30D: Enantiomers 3 and 4 of 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016,20]triaconta-1 (29),2(30),4,15,17,20,22,25,27-nonaen-6-yl)phenyl] propanoic Acid

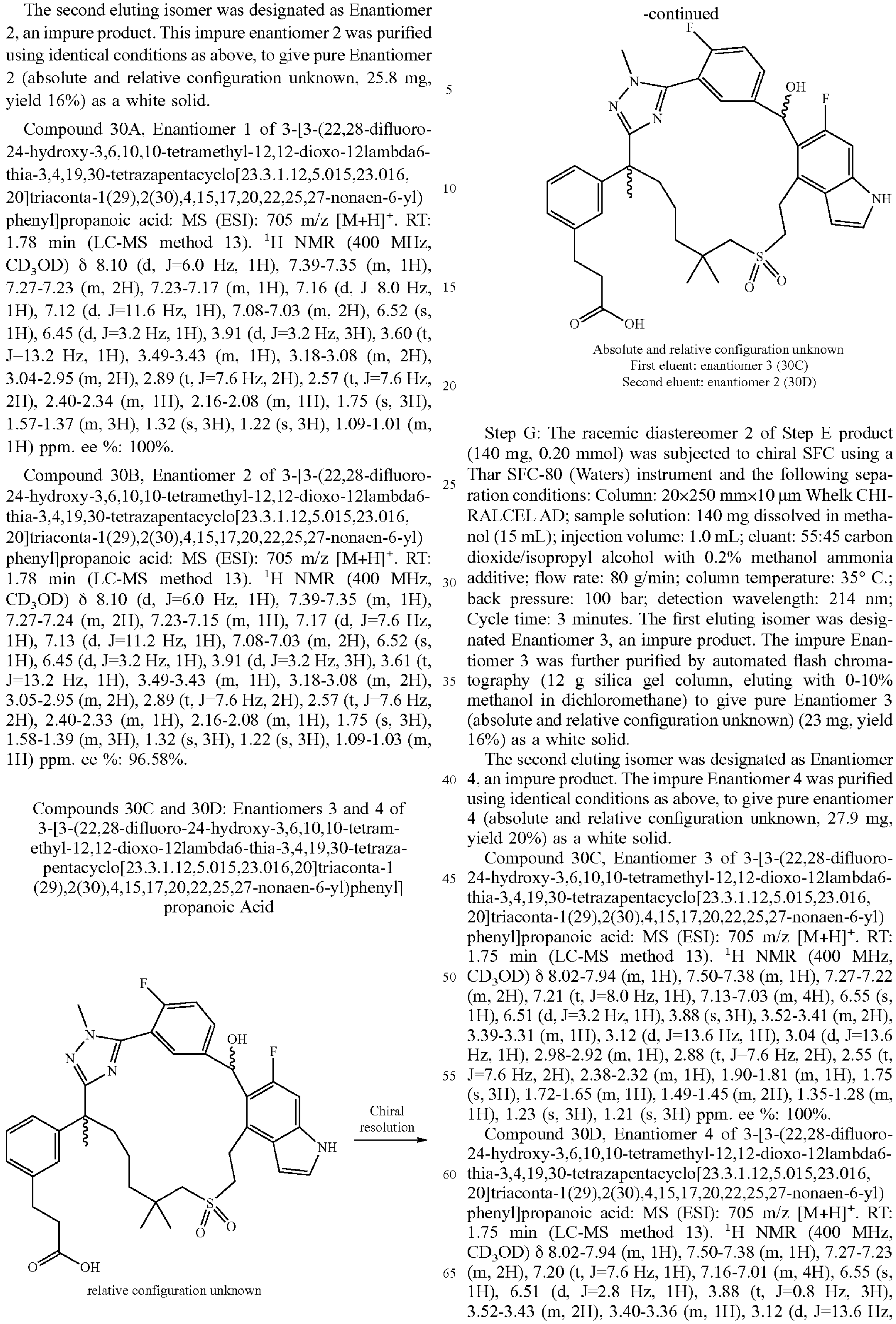

relative configuration unknown

-continued

Absolute and relative configuration unknown
First eluent: enantiomer 3 (30C)
Second eluent: enantiomer 2 (30D)

Step G: The racemic diastereomer 2 of Step E product (140 mg, 0.20 mmol) was subjected to chiral SFC using a Thar SFC-80 (Waters) instrument and the following separation conditions: Column: 20×250 mm×10 μm Whelk CHIRALCEL AD; sample solution: 140 mg dissolved in methanol (15 mL); injection volume: 1.0 mL; eluant: 55:45 carbon dioxide/isopropyl alcohol with 0.2% methanol ammonia additive; flow rate: 80 g/min; column temperature: 35° C.; back pressure: 100 bar; detection wavelength: 214 nm; Cycle time: 3 minutes. The first eluting isomer was designated Enantiomer 3, an impure product. The impure Enantiomer 3 was further purified by automated flash chromatography (12 g silica gel column, eluting with 0-10% methanol in dichloromethane) to give pure Enantiomer 3 (absolute and relative configuration unknown) (23 mg, yield 16%) as a white solid.

The second eluting isomer was designated as Enantiomer 4, an impure product. The impure Enantiomer 4 was purified using identical conditions as above, to give pure enantiomer 4 (absolute and relative configuration unknown, 27.9 mg, yield 20%) as a white solid.

Compound 30C, Enantiomer 3 of 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016, 20]triaconta-1(29),2(30),4,15,17,20,22,25,27-nonaen-6-yl) phenyl]propanoic acid: MS (ESI): 705 m/z $[M+H]^+$. RT: 1.75 min (LC-MS method 13). $^1$H NMR (400 MHz, $CD_3OD$) δ 8.02-7.94 (m, 1H), 7.50-7.38 (m, 1H), 7.27-7.22 (m, 2H), 7.21 (t, J=8.0 Hz, 1H), 7.13-7.03 (m, 4H), 6.55 (s, 1H), 6.51 (d, J=3.2 Hz, 1H), 3.88 (s, 3H), 3.52-3.41 (m, 2H), 3.39-3.31 (m, 1H), 3.12 (d, J=13.6 Hz, 1H), 3.04 (d, J=13.6 Hz, 1H), 2.98-2.92 (m, 1H), 2.88 (t, J=7.6 Hz, 2H), 2.55 (t, J=7.6 Hz, 2H), 2.38-2.32 (m, 1H), 1.90-1.81 (m, 1H), 1.75 (s, 3H), 1.72-1.65 (m, 1H), 1.49-1.45 (m, 2H), 1.35-1.28 (m, 1H), 1.23 (s, 3H), 1.21 (s, 3H) ppm. ee %: 100%.

Compound 30D, Enantiomer 4 of 3-[3-(22,28-difluoro-24-hydroxy-3,6,10,10-tetramethyl-12,12-dioxo-12lambda6-thia-3,4,19,30-tetrazapentacyclo[23.3.1.12,5.015,23.016, 20]triaconta-1(29),2(30),4,15,17,20,22,25,27-nonaen-6-yl) phenyl]propanoic acid: MS (ESI): 705 m/z $[M+H]^+$. RT: 1.75 min (LC-MS method 13). $^1$H NMR (400 MHz, $CD_3OD$) δ 8.02-7.94 (m, 1H), 7.50-7.38 (m, 1H), 7.27-7.23 (m, 2H), 7.20 (t, J=7.6 Hz, 1H), 7.16-7.01 (m, 4H), 6.55 (s, 1H), 6.51 (d, J=2.8 Hz, 1H), 3.88 (t, J=0.8 Hz, 3H), 3.52-3.43 (m, 2H), 3.40-3.36 (m, 1H), 3.12 (d, J=13.6 Hz, 1H), 3.04 (d, J=13.6 Hz, 1H), 2.98-3.90 (m, 1H), 2.88 (t, J=7.6 Hz, 2H), 2.54 (t, J=7.6 Hz, 2H), 2.40-2.31 (m, 1H), 1.89-1.81 (m, 1H), 1.75 (s, 3H), 1.72-1.65 (m, 1H), 1.49-1.45 (m, 2H), 1.35-1.28 (s, 1H), 1.23 (s, 3H), 1.21 (s, 3H) ppm. ee %: 98.1%.

Example 31. Enantiomer 1 and 2 of 3-[3-[22,28-difluoro-3,6,10,10-tetramethyl-12,12,24-trioxo-12lambda6-thia-3,4,19,30-tetrazapentacyclo [23.3.1.12,5.015,23.016,20]triaconta-1(29),2(30),4,15,17,20,22,25,27-nonaen-6-yl]phenyl]propanoic Acid

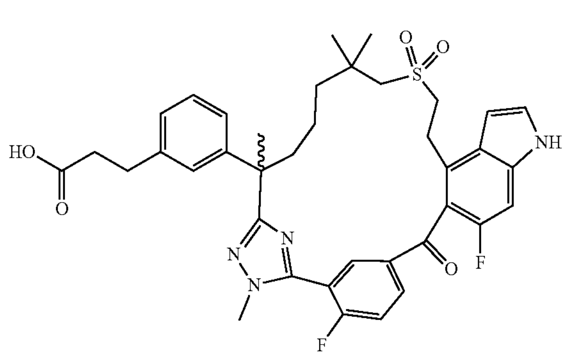

Methyl 3-[3-(22,28-difluoro-3,6,10,10-tetramethyl-12,12,24-trioxo-12lambda6-thia-3,4,19,30-tetraza-pentacyclo[23.3.1.12,5.015,23.016,20]triaconta-1(29),2(30),4,15,17,20,22,25,27-nonaen-6-yl)phenyl] propanoate

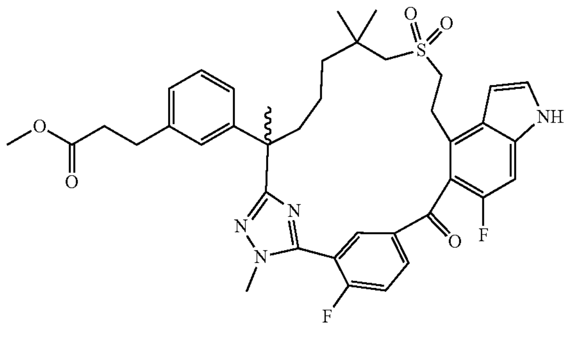 [SMILES: COC(=O)CCc1cccc(C2(C)CCCC(C)(C)CS(=O)(=O)CCc3c(c(F)cc4[nH]ccc34)C(=O)c3ccc(F)c(c3)-c3nc2nn3C)c1]

Step A: To a stirred solution of 4 diastereomeric mixture of methyl 3-[3-(22,28-difluoro-24-hydroxy-3,6,10,10-tetramethyl-12,12-dioxo-12lambda6-thia-3,4,19,30-tetraza-pentacyclo[23.3.1.12,5.015,23.016,20]triaconta-1(29),2(30),4,15,17,20,22,25,27-nonaen-6-yl)phenyl]propanoate (Step B product of Example 30, 400 mg, 0.56 mmol) in dimethyl sulfoxide (6 mL) was added 2-iodoxybenzoic acid (IBX) (0.467 g, 1.67 mmol). The reaction was stirred at room temperature for 2 hours, then diluted with ethyl acetate (100 mL). The mixture was washed with saturated sodium bicarbonate, dried over anhydrous sodium sulfate, filtered, and concentrated. The residue was purified by automated flash chromatography (12 g silica gel column, 0-5% methanol in dichloromethane) to give the product methyl 3-[3-(22,28-difluoro-3,6,10,10-tetramethyl-12,12,24-trioxo-12lambda6-thia-3,4,19,30-tetrazapentacyclo [23.3.1.12,5.015,23.016,20]triaconta-1(29),2(30),4,15,17,20,22,25,27-nonaen-6-yl)phenyl]propanoate (230 mg, yield 58%) as solid. MS (ESI): 717 m/z $[M+H]^+$. RT: 1.45 min (LC-MS method 22).

Compounds 31A and 31B: Enantiomers 1 and 2 of methyl 3-[3-[22,28-difluoro-3,6,10,10-tetramethyl-12,12,24-trioxo-12lambda6-thia-3,4,19,30-tetraza-pentacyclo[23.3.1.12,5.015,23.016,20]triaconta-1(29),2(30),4,15,17,20,22,25,27-nonaen-6-yl]phenyl] propanoate

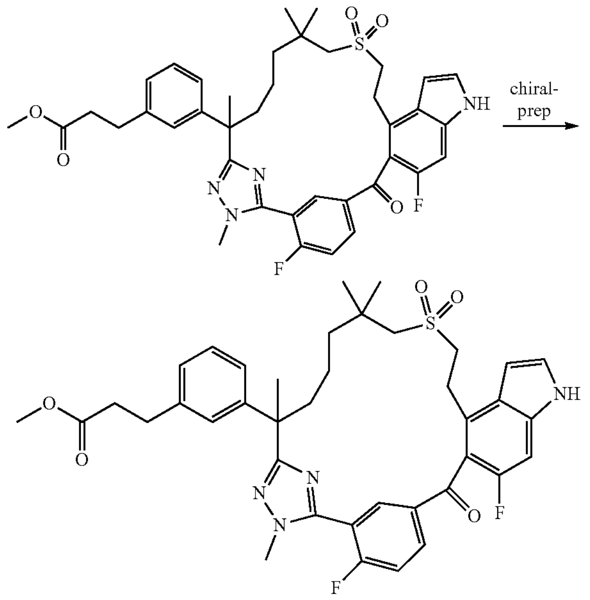

First eluent, enantiomer 1 (31A)
Second eluent, enantiomer 2 (31B)
Absolute configuration unknown Step B: The racemic mixture of Step A product (230 mg, 0.32 mmol) was subjected to chiral SFC using a Thar SFC-80 (Waters) instrument and the following separation conditions: Column: 20×250 mm×10 μm IC; sample solution: 230 mg dissolved in methanol (15 mL); injection volume: 1.9 mL; eluant: 45:55 carbon dioxide/methanol with 0.2% methanol ammonia additive; flow rate: 80 g/min; column temperature: 35° C.; back pressure: 100 bar; detection wavelength: 214 nm; Cycle time: 7.3 minutes. The first eluting isomer was designated Enantiomer 1 (Compound 31A) (absolute configuration unknown) (89 mg, yield 39%) as a white solid. The second eluting isomer was designated as Enantiomer 2 (Compound 31B) (85 mg, yield 37%) as solid.

Compound 31A: MS (ESI): 717 m/z $[M+H]^+$. RT: 1.46 min (LC-MS method 22). $^1H$ NMR (400 MHz, $CD_3OD$) δ 8.31-8.27 (m, 1H), 7.94-7.92 (m, 1H), 7.62-7.58 (m, 1H), 7.39 (d, J=3.2 Hz, 1H), 7.17-7.13 (m, 2H), 7.07-6.96 (m, 3H), 6.76-6.74 (m, 1H), 3.87 (d, J=2.4 Hz, 3H), 3.55 (s, 3H), 3.51-3.46 (m, 2H), 3.39-3.23 (m, 2H), 2.97 (d, J=13.6 Hz, 1H), 2.78-2.67 (m, 2H), 2.53 (d, J=13.6 Hz, 1H), 2.47 (t, J=7.6 Hz, 2H), 2.15 (dt, J=12.8, 3.6 Hz, 1H), 1.76 (dt, J=12.8, 5.8 Hz, 1H), 1.67 (s, 3H), 1.50-1.42 (m, 1H), 1.31-1.19 (m, 1H), 1.09 (m, 1H), 0.97 (s, 3H), 0.96 (s, 3H), 0.92-0.86 (m, 1H) ppm. ee %: 100%.

Compound 31B: MS (ESI): 717 m/z $[M+H]^+$. RT: 1.46 min (LC-MS method 22). $^1H$ NMR (400 MHz, $CD_3OD$) δ 8.32-8.27 (m, 1H), 7.96-7.94 (m, 1H), 7.62-7.58 (m, 1H), 7.39 (d, J=3.6 Hz, 1H), 7.17-7.13 (m, 2H), 7.06-6.97 (m, 3H), 6.76-6.73 (m, 1H), 3.87 (d, J=2.4 Hz, 3H), 3.55 (s, 3H), 3.51-3.46 (m, 2H), 3.39-3.23 (m, 2H), 2.97 (d, J=13.6 Hz, 1H), 2.78-2.69 (m, 2H), 2.53 (d, J=13.6 Hz, 1H), 2.47 (t, J=7.6 Hz, 2H), 2.16 (dt, J=12.8, 3.2 Hz, 1H), 1.76 (dt, J=12.8, 5.2 Hz, 1H), 1.67 (s, 3H), 1.54-1.41 (m, 1H), 1.26-1.19 (m, 1H), 1.05-1.00 (m, 1H), 0.97 (s, 3H), 0.96 (s, 3H), 0.92-0.86 (m, 1H) ppm. ee %: 100%.

Compound 31C: diastereomer 1 of 3-[3-[22,28-difluoro-3,6,10,10-tetramethyl-12,12,24-trioxo-12lambda6-thia-3,4,19,30-tetrazapentacyclo [23.3.1.12,5.015,23.016,20]triaconta-1(29),2(30),4,15,17,20,22,25,27-nonaen-6-yl]phenyl]propanoic Acid (Absolute Configuration Unknown)

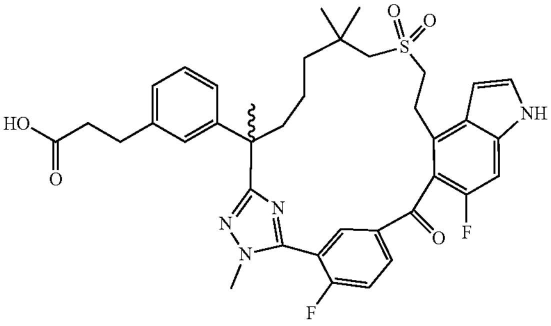

Absolute configuration unknown

Step C: A stirred solution of diastereomer 1 of Step B compound (65 mg, 0.09 mmol) in lithium hydroxide (0.2M in tetrahydrofuran/methanol/water (3:1:1), 2.27 mL) solution was stirred for 1 hour. The mixture was acidified with 1N hydrochloride to pH ~4, diluted with ethyl acetate (50 mL). The mixture was washed with water (2×20 mL), brine (2×20 mL), dried over anhydrous sodium sulfate, filtered, and concentrated. The residue was purified by prep-HPLC to give the title compound (30.7 mg, yield: 48%) as solid.

Compound 31C: MS (ESI): 703 m/z $[M+H]^+$, Retention time: 1.81 minutes. (LC-MS method 13). $^1H$ NMR (400 MHz, $CD_3OD$) δ 8.30-8.26 (m, 1H), 7.90-7.87 (m, 1H), 7.60 (t, J=9.6 Hz, 1H), 7.38 (d, J=3.2 Hz, 1H), 7.18-7.12 (m, 2H), 7.09 (s, 1H), 7.03-6.97 (m, 2H), 6.75 (d, J=2.8 Hz, 1H), 3.88 (d, J=2.4 Hz, 3H), 3.50 (t, J=7.2 Hz, 2H), 3.31-3.22 (m, 2H), 2.88 (d, J=13.6 Hz, 1H), 2.77 (t, J=7.2 Hz, 2H), 2.50-2.42 (m, 3H), 2.18-2.10 (m, 1H), 1.79 (dt, J=12.8, 4.8 Hz, 1H), 1.67 (s, 3H), 1.53-1.39 (m, 1H), 1.28-1.18 (m, 1H), 1.03-0.84 (m, 8H) ppm. ee %: 98.1%.

Compound 31D: diastereomer 2 of 3-[3-[22,28-difluoro-3,6,10,10-tetramethyl-12,12,24-trioxo-12lambda6-thia-3,4,19,30-tetrazapentacyclo[23.3.1.12,5.015,23.016,20]triaconta-1(29),2(30),4,15,17,20,22,25,27-nonaen-6-yl]phenyl] propanoic acid (absolute configuration unknown)

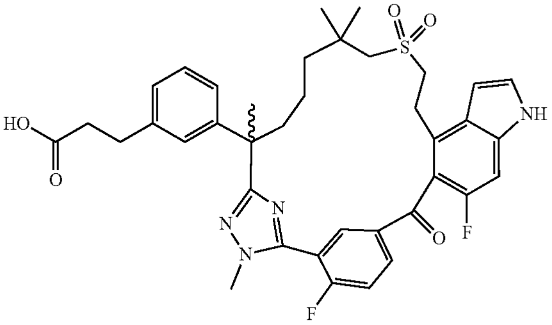

Absolute configuration unknown

Step D: Using a procedure identical to that described in step C, the Diastereomer 2 product of step B (56 mg, 0.08 mmol) was hydrolyzed to afford the title compound (26 mg yield: 47%) as solid (absolute configuration unknown).

Compound 31D: MS (ESI): 703 m/z $[M+H]^+$. Retention time: 1.81 minutes. (LC-MS method 13). $^1H$ NMR (400 MHz, $CD_3OD$) δ 8.30-8.26 (m, 1H), 7.91-7.88 (m, 1H), 7.60 (t, J=9.6 Hz, 1H), 7.38 (d, J=3.2 Hz, 1H), 7.17-7.12 (m, 2H), 7.08 (s, 1H), 7.02-6.97 (m, 2H), 6.75 (d, J=2.8 Hz, 1H), 3.88 (d, J=2.4 Hz, 3H), 3.50 (t, J=7.2 Hz, 2H), 3.31-3.15 (m, 2H), 2.88 (d, J=13.6 Hz, 1H), 2.77 (d, J=13.6 Hz, 1H), 2.49-2.42 (m, 3H), 2.18-2.10 (m, 1H), 1.79 (dt, J=12.8, 4.8 Hz, 1H), 1.67 (s, 3H), 1.53-1.40 (m, 1H), 1.26-1.18 (m, 1H), 1.03-0.84 (m, 8H) ppm. ee %: 98.1%.

Example 32. Enantiomers 1 and 2 of 3-[3-(22,28-Difluoro-3,6,10,10-tetramethyl-12,12-dioxo-12lambda6-thia-3,4,19,30-tetrazapentacyclo [23.3.1.12,5.015,23.016,20]triaconta-1(29),2(30),4,15,17,20,22,25,27-nonaen-6-yl)phenyl]propanoic acid

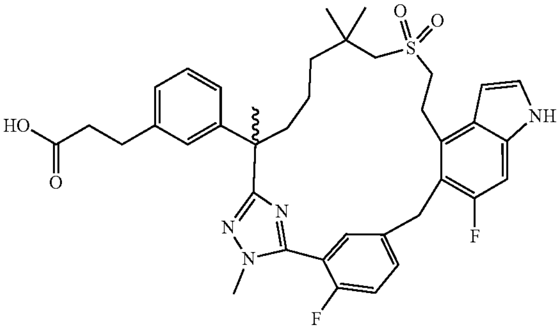

Ethyl 3-(3-(2-(5-(5-((4-bromo-6-fluoro-1-(triisopropylsilyl)-1H-indol-5-yl)methyl)-2-fluorophenyl)-1-methyl-1H-1,2,4-triazol-3-yl)-7-((2-hydroxyethyl)sulfonyl)-6,6-dimethylheptan-2-yl)phenyl)propanoate

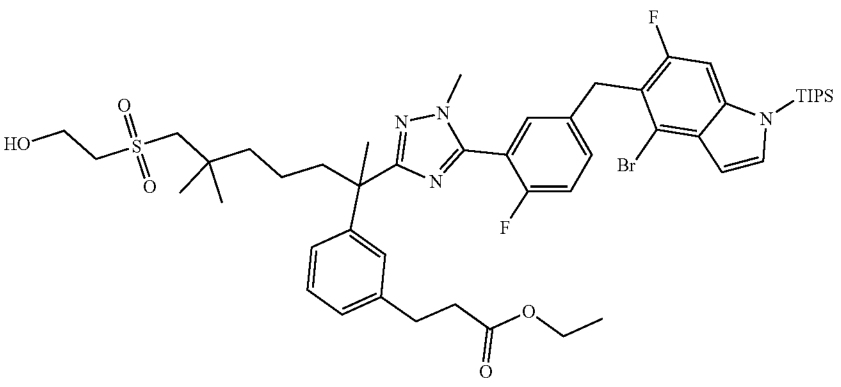

Step A: Exchanging methyl 5-((4-bromo-6-fluoro-1H-indol-5-yl)oxy)-2-fluorobenzimidothioate hydroiodide (Intermediate 14-1) for methyl 5-((4-bromo-6-fluoro-1-(triisopropylsilyl)-1H-indol-5-yl)methyl)-2-fluorobenzimidothioate hydroiodide (Intermediate 57-1, 1.64 g, 2.9 mmol), and methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) for ethyl 3-(3-(7-((2-hydroxyethyl)sulfonyl)-2,6,6-trimethyl-1-(2-methylhydrazineyl)-1-oxoheptan-2-yl)phenyl)propanoate (Intermediate 58-5), the reaction procedure sequence described for methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate, in Example 6 (Step A) was used to prepare the title compound (1.1 g, 47%) as a white solid. MS (ESI): 969, 971 m/z $[M+H]^+$. Retention time: 2.59 minutes. (LC-MS Method 09).

Ethyl 3-(3-(2-(5-(5-((4-bromo-6-fluoro-1H-indol-5-yl)methyl)-2-fluorophenyl)-1-methyl-1H-1,2,4-triazol-3-yl)-7-((2-hydroxyethyl)sulfonyl)-6,6-dimethylheptan-2-yl)phenyl)propanoate Step B: To a stirred solution of ethyl 3-(3-(2-(5-(5-((4-bromo-6-fluoro-1-(triisopropylsilyl)-1H-indol-5-yl)methyl)-2-fluorophenyl)-1-methyl-1H-1,2,4-triazol-3-yl)-7-((2-hydroxyethyl)sulfonyl)-6,6-dimethylheptan-2-yl)phenyl)propanoate (Step A, 1.1 g, 1.13 mmol) in 10 mL of tetrahydrofuran was added 1M tetra-n-butyl ammonium fluoride in tetrahydrofuran (12 mL, 12 mmol) at room temperature. The mixture was stirred for 3 hours, then concentrated. The residue was dissolved in ethyl acetate (50 mL), washed with water (50 mL). The aqueous layer was back extracted with ethyl acetate (2×50 mL), the combined organic layers were dried over sodium sulfate, filtered, and concentrated. The residue was purified by automated flash chromatography (40 g silica gel column, 0-100% ethyl acetate in petroleum ether) to give the title compound (0.7 g, 75%) as solid. MS (ESI): 813, 815 m/z $[M+H]^+$. Retention time: 2.03 minutes. (LC-MS Method 09).

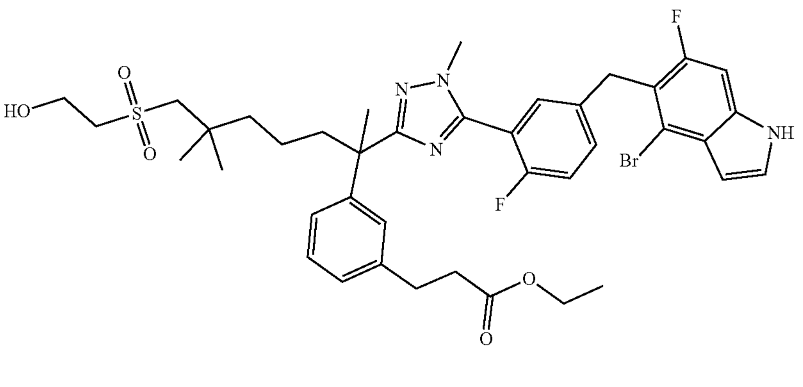 [SMILES: CCOC(=O)CCc1cccc(C(C)(CCCC(C)(C)CS(=O)(=O)CCO)c2nc(-c3cc(Cc4c(F)cc5[nH]ccc5c4Br)ccc3F)n(C)n2)c1]

Ethyl 3-[3-(22,28-difluoro-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoate

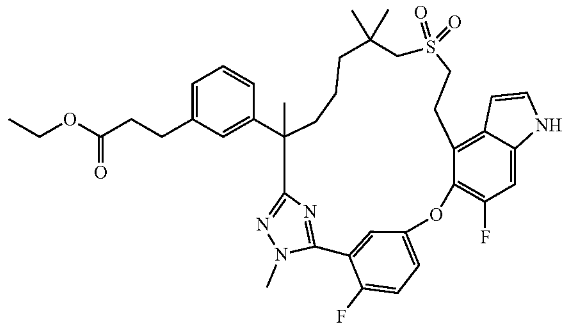 [SMILES: CCOC(=O)CCc1cccc(C2(C)CCCC(C)(C)CS(=O)(=O)CCc3c(c(F)cc4[nH]ccc34)Oc3ccc(F)c(c3)-c3nc2nn3C)c1]

Step C: Exchanging methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A, Example 6) for ethyl 3-(3-(2-(5-(5-((4-bromo-6-fluoro-1H-indol-5-yl)methyl)-2-fluorophenyl)-1-methyl-1H-1,2,4-triazol-3-yl)-7-((2-hydroxyethyl)sulfonyl)-6,6-dimethylheptan-2-yl)phenyl)propanoate (Step B product above, 1 g, 1.17 mmol), the reaction procedure sequence described for Example 6 (Step B to D, and Step F) was used to prepare the title compound (0.45 g, 41% (3 steps overall)) as a white solid. MS (ESI): 717 m/z $[M+H]^+$. Rt 2.64 minutes. (LC-MS method 010).

Enantiomers 1 and 2 of ethyl 3-[3-(22,28-difluoro-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoate

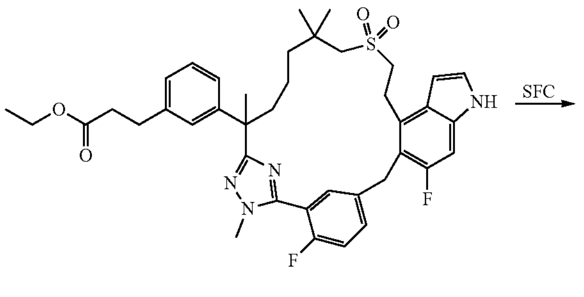

-continued

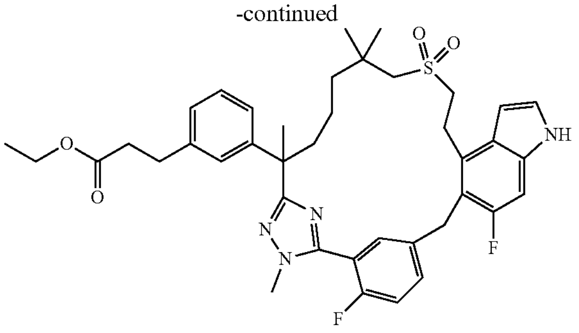

First Eluent, enantiomer 1
Second Eluent, enantiomer 2
Absolute configuration unknown Step D: The racemic mixture of Step C product (450 mg, 0.73 mmol) was subjected to chiral SFC using a Thar SFC-150 (Waters) instrument and the following separation conditions: Column: 20×250 mm×10 μm IH; sample solution: 450 mg dissolved in methanol (20 mL); injection volume: 1.5 mL; eluant: 65:35 carbon dioxide/methanol with 0.2% methanol ammonia additive; flow rate: 120 g/min; column temperature: 35° C.; back pressure: 100 bar; detection wavelength: 214 nm; cycle time: 4.6 minutes. The first eluting isomer was designated Enantiomer 1 (absolute configuration unknown) (140 mg, 31%) as a white solid. The second eluting isomer was designated as Enantiomer 2 (160 mg, yield 35%) as solid.

Diastereomer 1 of ethyl 3-[3-(22,28-difluoro-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoate: MS (ESI): 717 m/z $[M+H]^+$, Rt, 2.06 min. (LC-MS Method 013), ee %=100%.

Diastereomer 2 of ethyl 3-[3-(22,28-difluoro-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoate: MS (ESI): 717 m/z $[M+H]^+$, Rt, 2.06 min. (LC-MS method 013), ee %=97.8%.

Compound 32A, Enantiomer 1 of 3-[3-(22,28-Difluoro-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

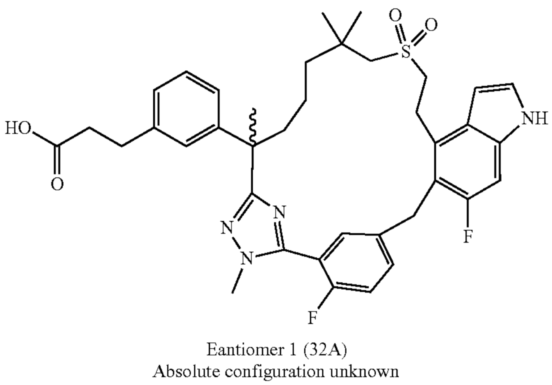 [SMILES: Cn1nc2nc1-c1cc(ccc1F)Cc1c(F)cc3[nH]ccc3c1CCS(=O)(=O)CC(C)(C)CCCC2(C)c1cccc(CCC(=O)O)c1]

Eantiomer 1 (32A)
Absolute configuration unknown

Step E: A solution of enantiomer 1 of Step D compound (140 mg, 0.19 mmol) in lithium hydroxide (0.2 M in tetrahydrofuran/methanol/water (3:1:1), 2.27 mL) solution was stirred for 1 hour. The mixture was acidified with 1N hydrochloride to pH ~4, diluted with ethyl acetate (50 mL). The mixture was washed with water (2×20 mL), brine (2×20 mL), dried over anhydrous sodium sulfate, filtered, and concentrated. The residue was purified by prep-HPLC to give the title compound (110 mg, 82%) as solid.

Compound 32A: MS (ESI): 689 m/z $[M+H]^+$, Rt 1.87 minutes (LC-MS Method 013). $^1H$ NMR (400 MHz, $CD_3OD$) δ 7.61 (dd, J=6.8, 2.4 Hz, 1H), 7.51-7.47 (m, 1H), 7.15-7.05 (m, 3H), 7.03-6.97 (m, 2H), 6.96-6.90 (m, 2H), 6.36 (d, J=3.2 Hz, 1H), 4.12 (d, J=15.2 Hz, 1H), 4.22 (d, J=14.4 Hz, 1H), 3.73 (d, J=1.6 Hz, 3H), 3.36-3.28 (m, 2H), 3.08-2.99 (m, 4H), 2.75 (t, J=7.6 Hz, 2H), 2.43 (t, J=7.6 Hz, 2H), 2.23 (td, J=12.8, 3.6 Hz, 1H), 1.80 (td, J=12.8, 3.6 Hz, 1H), 1.61 (s, 3H), 1.55-1.46 (m, 1H), 1.43-1.38 (m, 2H), 1.15-1.02 (m, 7H) ppm. ee %=98.9%.

Compound 32B, diastereomer 2 of 3-[3-(22,28-Difluoro-3,6,10,10-tetramethyl-12,12-dioxo-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

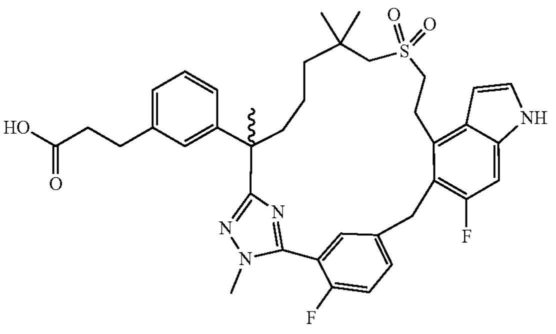

Eantiomer 2 (32B)
Absolute configuration unknown

Step F: Using a procedure identical to that described in step E, the Diastereomer 2 product of step D (160 mg, 0.22 mmol) was hydrolyzed to afford the title compound (143 mg, 92%) as a solid. (Absolute configuration unknown).

Compound 32B: MS (ESI): 689 m/z $[M+H]^+$, Rt 1.87 minutes (LC-MS Method 013). $^1H$ NMR (400 MHz, $CD_3OD$) δ 7.61 (dd, J=6.8, 2.4 Hz, 1H), 7.51-7.47 (m, 1H), 7.15-7.09 (m, 2H), 7.08 (t, J=7.6 Hz, 1H), 7.01-6.97 (m, 2H), 6.95-6.90 (m, 2H), 6.36 (d, J=3.2 Hz, 1H), 4.12 (d, J=14.8 Hz, 1H), 4.22 (d, J=15.2 Hz, 1H), 3.73 (d, J=1.6 Hz, 3H), 3.37-3.29 (m, 2H), 3.06-2.98 (m, 4H), 2.75 (t, J=7.6 Hz, 2H), 2.43 (t, J=7.6 Hz, 2H), 2.23 (td, J=12.8, 3.6 Hz, 1H), 1.80 (td, J=12.8, 3.6 Hz, 1H), 1.61 (s, 3H), 1.55-1.47 (m, 1H), 1.43-1.38 m, 2H), 1.11-1.04 (m, 7H) ppm. ee %=100%.

Example 33. Diastereomers 1 and 2 of 3-[3-(22,28-difluoro-3,6,10,10-tetramethyl-12,12-dioxo-12lambda6,24-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

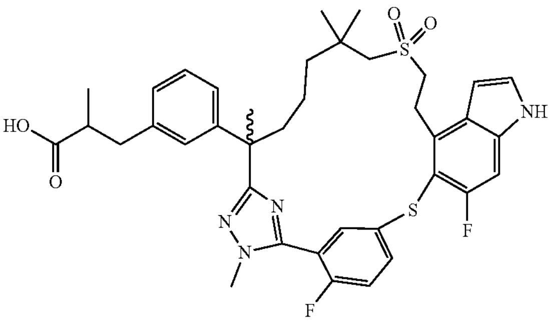 [SMILES: CC(Cc1cccc(C2(C)CCCC(C)(C)CS(=O)(=O)CCc3c(c(F)cc4[nH]ccc34)Sc3ccc(F)c(c3)-c3nc2nn3C)c1)C(=O)O]

Ethyl 3-[3-(22,28-difluoro-3,6,10,10-tetramethyl-12,12-dioxo-12lambda6,24-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate

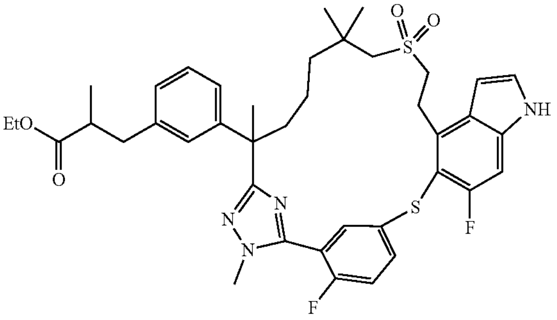 [SMILES: CCOC(=O)C(C)Cc1cccc(C2(C)CCCC(C)(C)CS(=O)(=O)CCc3c(c(F)cc4[nH]ccc34)Sc3ccc(F)c(c3)-c3nc2nn3C)c1]

Step A: Exchanging methyl 5-((4-bromo-6-fluoro-1H-indol-5-yl)oxy)-2-fluorobenzimidothioate hydroiodide (Intermediate 14-1) for methyl 5-((4-bromo-6-fluoro-1H-indol-5-yl)thio)-2-fluorobenzimidothioate hydroiodide (Intermediate 76, 3.2 g, 5.91 mmol), and methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) for ethyl 3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 58-6, 3.4 g, 6.82 mmol), the reaction procedure sequence (Step A-D) described for Example 6 was used to prepare the title compound (1.47 g, 36%4 steps overall) as a white solid. MS (ESI): 749 m/z $[M+H]^+$, Rt 2.11 minutes (LC-MS method 013).

Diastereomers 1 and 2 of ethyl 3-[3-(22,28-difluoro-3,6,10,10-tetramethyl-12,12-dioxo-12lambda6,24-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate

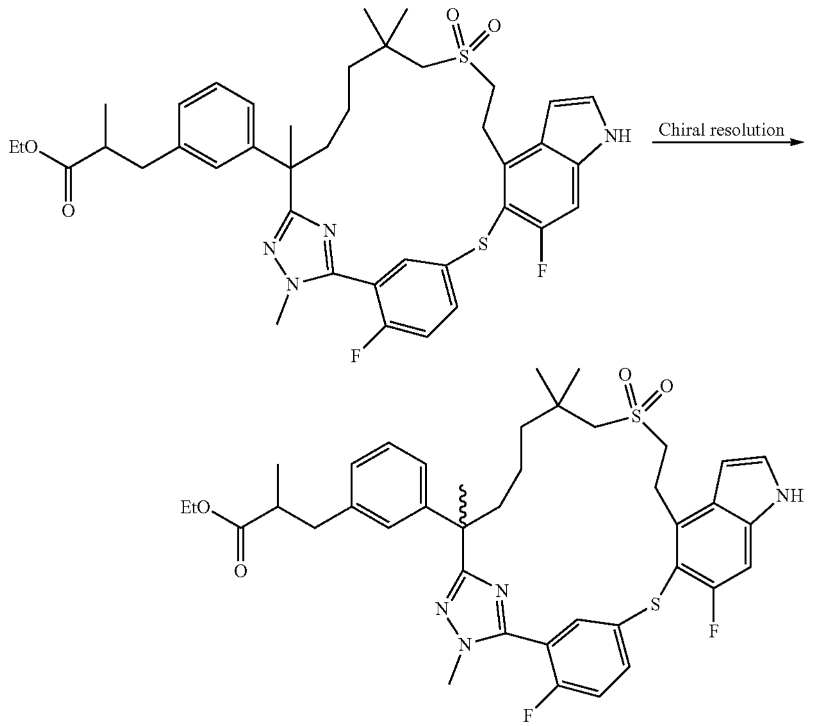

First eluent, Diastereomer 1
Second eluent, Diastereomer 2

Step B: The racemic mixture of Step A product (300 mg) was subjected to chiral SFC using a Thar SFC-150 (Waters) instrument and the following separation conditions: Column: 20×250 mm×10 μm IG; sample solution: 300 mg dissolved in methanol (35 mL); injection volume: 1.0 mL; eluant: 70:30 carbon dioxide/isopropanol with 0.2% methanol ammonia additive; flow rate: 120 g/min; column temperature: 35° C.; back pressure: 100 bar; detection wavelength: 214 nm; cycle time: 4.2 minutes. The first eluting isomer was designated diastereomer 1 (absolute configuration unknown) (70 mg, 23%) as a white solid. The second eluting isomer was designated as diastereomer 2 (93 mg, yield 31%) as a solid.

Diastereomer 1 of ethyl 3-[3-(22,28-difluoro-3,6,10,10-tetramethyl-12,12-dioxo-12lambda6,24-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate: MS (ESI): 749 m/z $[M+H]^+$, Rt 2.11 minutes (LC-MS Method 013). ee %=100%.

Diastereomer 2 of ethyl 3-[3-(22,28-difluoro-3,6,10,10-tetramethyl-12,12-dioxo-12lambda6,24-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate: MS (ESI): 749 m/z $[M+H]^+$, Rt 2.11 minutes (LC-MS Method 013). ee %=99%.

Compound 33A: Diastereomer 1 of 3-[3-(22,28-difluoro-3,6,10,10-tetramethyl-12,12-dioxo-12lambda6,24-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

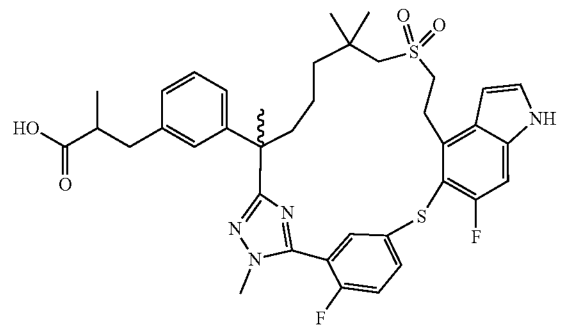

Absolute configuration unknown

Step E: The diastereomer 1 of Step B product (70 mg, 93.6 μmol) was treated with lithium hydroxide (0.2 M in tetrahydrofuran/methanol/water=3:1:1) (10 mL) at room temperature for 2 hours. The reaction mixture was acidified with 1 N hydrogen chloride to pH ~4, diluted with water (30 mL). The mixture was extracted with ethyl acetate (3×20 mL). The combined extract was washed with brine, dried over sodium sulfate, filtered, and concentrated. The residue was lyophilized to give the title product (absolute configuration unknown, 59.7 mg, 89%) as solid.

Compound 33A: MS (ESI): 721 m/z $[M+H]^+$. Rt 1.93 minutes (LC-MS method 013). $^1H$ NMR (400 MHz, $CD_3OD$) δ 7.85-7.78 (m, 1H), 7.75-7.71 (m, 1H), 7.34-7.29 (m, 2H), 7.20-7.13 (m, 2H), 7.08-7.07 (m, 1H), 7.03-6.99 (m, 2H), 6.61 (d, J=3.2 Hz, 1H), 3.80 (d, J=1.6 Hz, 3H), 3.78-3.69 (m, 2H), 3.29-3.23 (m, 2H), 3.01-2.90 (m, 3H), 2.66-2.57 (m, 2H), 2.32-2.24 (m, 1H), 1.92-1.86 (m, 1H), 1.70 (s, 3H), 1.63-1.42 (m, 4H), 1.19 (s, 3H), 1.15 (s, 3H), 1.08 (dd, J=6.4, 5.2 Hz, 3H) ppm. Chiral HPLC: 100%

Compound 33B diastereomer 2 of 3-[3-(22,28-difluoro-3,6,10,10-tetramethyl-12,12-dioxo-12lambda6,24-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

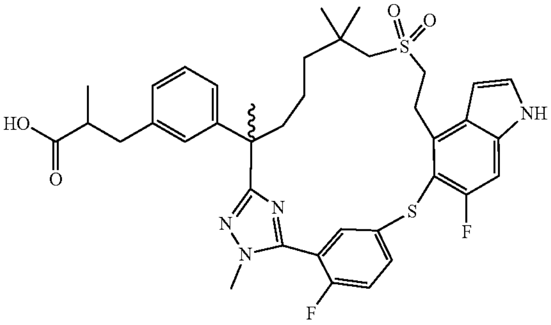

Absolute configuration unknown

Step F: Using a procedure identical to that described in step C, the Diastereomer 2 product of step B (93 mg, 0.12 mmol) was hydrolyzed to afford the title product (80.5 mg, 90%) as solid (absolute configuration unknown).

Compound 33B: MS (ESI): 721 m/z $[M+H]^+$, Rt 1.93 minutes (LC-MS method 013). $^1H$ NMR (400 MHz, $CD_3OD$) δ 7.85-7.79 (m, 1H), 7.75-7.71 (m, 1H), 7.34-7.30 (m, 2H), 7.21-7.15 (m, 2H), 7.08-7.07 (m, 1H), 7.03-6.99 (m, 2H), 6.61 (d, J=3.2 Hz, 1H), 3.80 (d, J=1.6 Hz, 3H), 3.78-3.70 (m, 2H), 3.29-3.22 (m, 2H), 3.01-2.93 (m, 3H), 2.66-2.57 (m, 2H), 2.28-2.24 (m, 1H), 1.92-1.86 (m, 1H), 1.70 (s, 3H), 1.64-1.42 (m, 4H), 1.19 (s, 3H), 1.15 (s, 3H), 1.08 (dd, J=6.8, 5.2 Hz, 3H) ppm.

Chiral HPLC: 100%.

Example 34. Diastereomers 1 and 2 of 3-[3-(22,28-difluoro-3,6,10,10-tetramethyl-12,12,24,24-tetraoxo-12lambda6,24lambda6-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

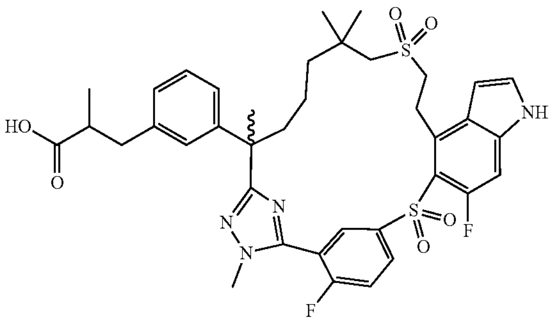 [SMILES: CC(Cc1cccc(C2(C)CCCC(C)(C)CS(=O)(=O)CCc3c(c(F)cc4[nH]ccc34)S(=O)(=O)c3ccc(F)c(c3)-c3nc2nn3C)c1)C(=O)O]

Ethyl 3-[3-[22,28-difluoro-3,6,10,10-tetramethyl-12,12-dioxo-19-(p-tolylsulfonyl)-12lambda6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

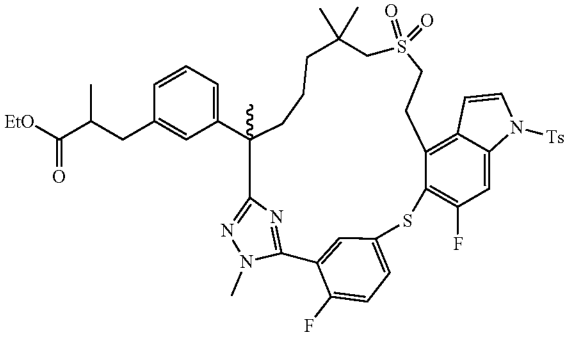 [SMILES: CCOC(=O)C(C)Cc1cccc(C2(C)CCCC(C)(C)CS(=O)(=O)CCc3c(c(F)cc4c3ccn4S(=O)(=O)c3ccc(C)cc3)Sc3ccc(F)c(c3)-c3nc2nn3C)c1]

Step A: To a stirred solution of ethyl 3-[3-(22,28-difluoro-3,6,10,10-tetramethyl-12,12-dioxo-12lambda6,24-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate (Step A product of Example 33, 400 mg, 535 μmol) in acetonitrile (10 mL) was added 1-[(4-methylphenyl)sulfonyl]-1H-imidazole (143 mg, 642 μmol) and DBU (48 μL, 321 μmol). The mixture was stirred at room temperature overnight, then diluted with water (30 mL). The mixture was extracted with ethyl acetate (3×20 mL). The combined extract was washed with brine (3×20 mL), dried over sodium sulfate, filtered, and concentrated. The residue was purified by automated flash chromatography (20 g silica gel column, 0-80% ethyl acetate in petroleum ether) to give the title product (410 mg, yield 85%) as solid. MS (ESI): 903 m/z $[M+H]^+$, Rt: 2.30 minutes (LC-MS Method 013).

Ethyl 3-[3-[22,28-difluoro-3,6,10,10-tetramethyl-12,12-dioxo-19-(p-tolylsulfonyl)-12lambda6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

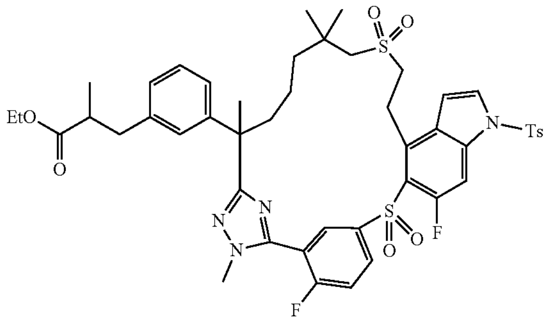 [SMILES: CCOC(=O)C(C)Cc1cccc(C2(C)CCCC(C)(C)CS(=O)(=O)CCc3c(c(F)cc4c3ccn4S(=O)(=O)c3ccc(C)cc3)S(=O)(=O)c3ccc(F)c(c3)-c3nc2nn3C)c1]

Step B: To a stirred solution of the Step A product (410 mg, 455 μmol) in dichloromethane (20 mL) was added meta-chloroperoxybenzoic acid (235 mg, 1.36 mmol). The mixture was stirred at room temperature overnight. The solvent was removed. The residue was purified by automated flash chromatography (12 g silica gel column, 0-70% ethyl acetate in petroleum ether) to give the title compound (360 mg, yield 85%) as solid. MS (ESI): 935 m/z [M+H]$^+$, Rt: 2.32 minutes (LC-MS Method 011).

Diastereomers 1 and 2 of ethyl 3-[3-[22,28-difluoro-3,6,10,10-tetramethyl-12,12-dioxo-19-(p-tolylsulfonyl)-12lambda6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

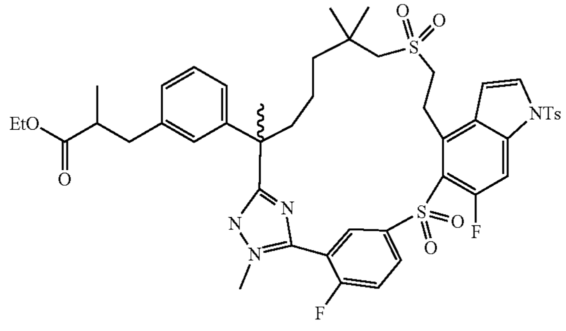

First eluent, Diastereomer 1
second eluent, Diastereomer 2
Absolute configuration unknown Step C: The racemic mixture of Step B product (410 mg) was subjected to chiral SFC using a Thar SFC-80 (Waters) instrument and the following separation conditions: Column: 20×250 mm×10 μm AD; sample solution: 410 mg dissolved in methanol (25 mL); injection volume: 0.6 mL; eluant: 65:35 carbon dioxide/isopropanol with 0.2% methanol ammonia additive; flow rate: 80 g/min; column temperature: 35° C.; back pressure: 100 bar; detection wavelength: 214 nm; Cycle time: 3.6 minutes. The first eluting isomer was designated diastereomer 1 (absolute configuration unknown) (140 mg, 34%) as a white solid. The second eluting isomer was designated as diastereomer 2, (140 mg, yield 34%) as a solid.

Diastereomer 1 of ethyl 3-[3-[22,28-difluoro-3,6,10,10-tetramethyl-12,12-dioxo-19-(p-tolylsulfonyl)-12lambda6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate: MS (ESI): 935 m/z [M+H]$^+$, 2.19 minutes, (LC-MS Method 013). ee %=100%.

Diastereomer 2 of ethyl 3-[3-[22,28-difluoro-3,6,10,10-tetramethyl-12,12-dioxo-19-(p-tolylsulfonyl)-12lambda6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate: MS (ESI): 935 m/z [M+H]$^+$. 2.19 minutes, (LC-MS Method 013), ee %, 99%.

Compound 34A: Diastereomer 1 of 3-[3-(22,28-difluoro-3,6,10,10-tetramethyl-12,12,24,24-tetraoxo-12lambda6,24lambda6-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

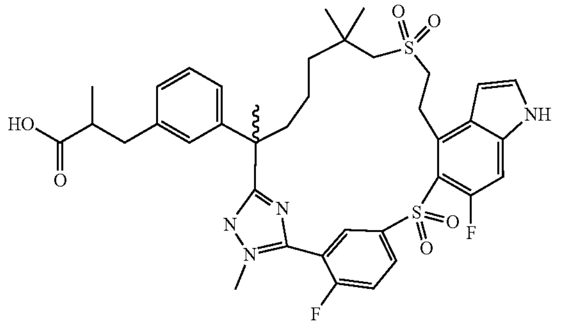

Absolute configuration unknown

Step D: To a stirred solution of separated diastereomer 1 of Step C product (absolute configuration unknown, 140 mg, 150 μmol) in tetrahydrofuran (12 mL) was added lithium hydroxide (1M in water) (6 mL). The mixture was stirred at room temperature for 3 days, then acidified with 1 N hydrogen chloride to pH ~4 and diluted with water (30 mL). The mixture was extracted with ethyl acetate (3×20 mL). The combined organic extracts were washed with brine, dried over sodium sulfate, filtered, and concentrated. The residue was purified by automated flash chromatography (40 g silica gel column, 0-100% ethyl acetate in petroleum ether) to give the title compound (absolute configuration unknown, 56.5 mg, yield 50%) as a solid.

Compound 34A: MS (ESI): 753 m/z [M+H]$^+$, Rt: 1.84 minutes (LC-MS Method 013). $^1$H NMR (400 MHz, $CD_3OD$) δ 8.41-8.36 (m, 1H), 8.33 (dt, J=6.0, 2.0 Hz, 1H), 7.64 (t, J=9.2 Hz, 1H), 7.42 (d, J=3.6 Hz, 1H), 7.21 (d, J=12.4 Hz, 1H), 7.17 (t, J=8.0 Hz, 1H), 7.10 (bs, 1H), 7.03-7.00 (m, 2H), 6.74 (d, J=3.6 Hz, 1H), 3.94-3.78 (m, 2H), 3.85 (d, J=2.4 Hz, 3H), 3.61-3.41 (m, 2H), 3.19 (d, J=14.4 Hz, 1H), 3.13 (d, J=14.4 Hz, 1H), 3.02-2.91 (m, 1H), 2.64-2.58 (m, 2H), 2.42-2.37 (m, 1H), 1.90 (t, J=12.8 Hz, 1H), 1.74 (s, 3H), 1.65-1.40 (m, 4H), 1.30 (s, 3H), 1.23 (s, 3H), 1.08 (d, J=6.0 Hz, 1.5H), 1.07 (d, J=6.0 Hz, 1.5H) ppm. (1:1 mixture of two diastereomers)

Compound 34B Diastereomer 2 of 3-[3-(22,28-difluoro-3,6,10,10-tetramethyl-12,12,24,24-tetraoxo-12lambda6,24lambda6-dithia-3,4,19,30-tetrazapentacyclo[23.3.1.12, 5.015,23.016,20]triaconta-1(29),2(30),4,15,17,20,22,25,27-nonaen-6-yl)phenyl]-2-methyl-propanoic Acid

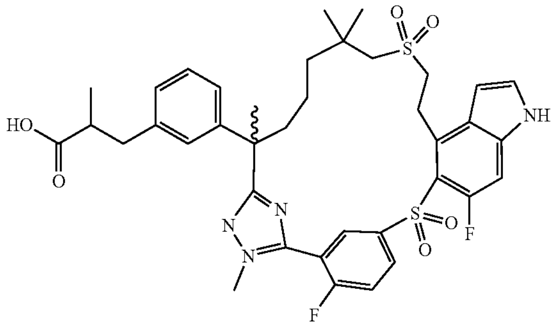

Absolute configuration unknown

Step E: Using a procedure identical to that described in step D, separated diastereomer 2 of Step C product (140 mg, 0.15 mmol) was hydrolyzed and deprotected to afford the title compound (48.8 mg, 43%) as solid (absolute configuration unknown).

Compound 34B: MS (ESI): 753 m/z $[M+H]^+$, Rt: 1.84 minutes (LC-MS method 013). $^1H$ NMR (400 MHz, $CD_3OD$) δ 8.41-8.36 (m, 1H), 8.33 (dt, J=6.0, 2.0 Hz, 1H), 7.64 (t, J=9.2 Hz, 1H), 7.42 (d, J=3.6 Hz, 1H), 7.21 (d, J=12.4 Hz, 1H), 7.17 (t, J=8.0 Hz, 1H), 7.10 (s, 1H), 7.03-7.00 (m, 2H), 6.74 (d, J=3.6 Hz, 1H), 3.94-3.78 (m, 2H), 3.85 (d, J=2.4 Hz, 3H), 3.61-3.41 (m, 2H), 3.19 (d, J=14.4 Hz, 1H), 3.13 (d, J=14.0 Hz, 1H), 3.02-2.91 (m, 1H), 2.64-2.58 (m, 2H), 2.42-2.37 (m, 1H), 1.94-1.85 (m, 1H), 1.74 (s, 3H), 1.65-1.40 (m, 4H), 1.30 (s, 3H), 1.23 (s, 3H), 1.08 (d, J=6.0 Hz, 1.5H), 1.07 (d, J=6.0 Hz, 1.5H) ppm. (1:1 mixture of two diastereomers).

Example 35. 3-[3-(23,29-Difluoro-13,13-dioxo-25-oxa-13λ6-thia-3,20,31-triazapentacyclo[24.3.1.12, 5.016,24.017,21]hentriaconta-1(30),2,4,16,18,21,23,26,28-nonaen-6-yl)phenyl]propanoic Acid

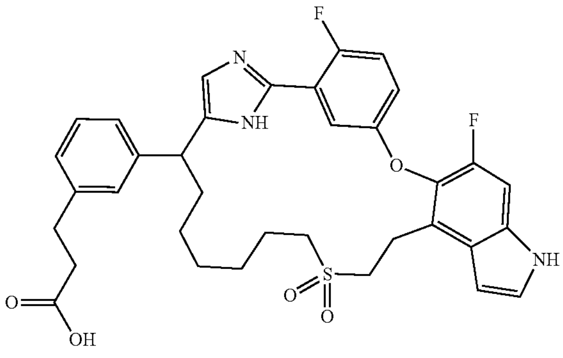 [SMILES: O=C(O)CCc1cccc(C2CCCCCCS(=O)(=O)CCc3c(c(F)cc4[nH]ccc34)Oc3ccc(F)c(c3)-c3ncc2[nH]3)c1]

(5-(3-(5-(7-Chloro-1-(3-iodophenyl)heptyl)-1H-imidazol-2-yl)-4-fluorophenoxy)-6-fluoro-1H-indol-4-yl)methanol

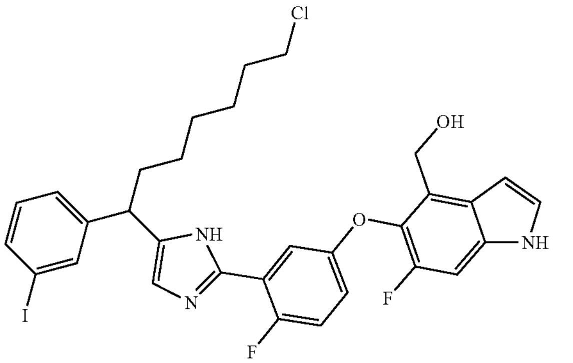 [SMILES: OCc1c(Oc2ccc(F)c(-c3ncc(C(CCCCCCCl)c4cccc(I)c4)[nH]3)c2)c(F)cc2[nH]ccc12]

Step A: Exchanging 8-bromo-6-(3-iodophenyl)-2,2,6-trimethyl-7-oxooctyl acetate (Intermediate 17) with 1-bromo-9-chloro-3-(3-iodophenyl)nonan-2-one (Intermediate 17-2, 1.4 g, 2.93 mmol) and replacing ethyl 2-(((5-(3-carbamimidoyl-4-fluorophenoxy)-6-fluoro-1-(phenylsulfonyl)-1H-indol-4-yl)methyl)sulfonyl)acetate (Intermediate 18) with 2-fluoro-5-((6-fluoro-4-(hydroxymethyl)-1H-indol-5-yl)oxy)benzimidamide (Intermediate 10-4, 1.12 g, 3.51 mmol) in Step A, the title compound (950 mg, 35%, a yellow solid) was prepared following the procedure as described for Example 21, Step A. MS (ESI): 676 m/z $[M+H]^+$. 2-((7-(2-(2-fluoro-5-((6-fluoro-4-(hydroxymethyl)-1H-indol-5-yl)oxy)phenyl)-1H-imidazol-5-yl)-7-(3-iodophenyl)heptyl)thio)acetic Acid

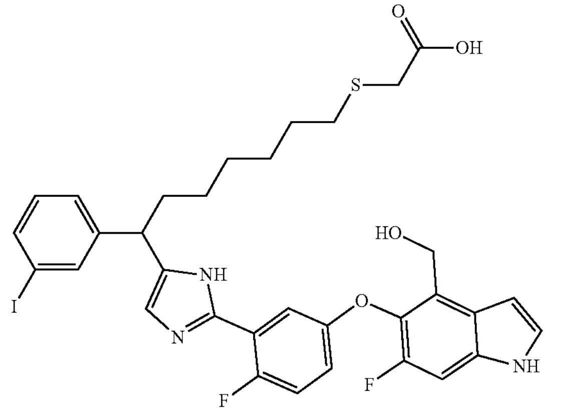 [SMILES: O=C(O)CSCCCCCCC(c1cccc(I)c1)c1cnc(-c2cc(Oc3c(F)cc4[nH]ccc4c3CO)ccc2F)[nH]1]

Step B: To a stirred and cooled (0° C.) solution of 2-mercaptoacetic acid (195 mg, 2.12 mmol) in methanol (2 mL) was added a solution of potassium hydroxide (274 mg, 4.89 mmol) in methanol (2 mL). The mixture was stirred at room temperature for 1 hour, then treated with a solution of Step A product (1.1 g, 1.63 mmol) in methanol (6 mL) at 0° C. After the addition, the reaction mixture was stirred at 60° C. overnight and concentrated. The residue was dissolved in water (80 mL), acidified with 1 N hydrochloric acid to pH ~6 and extracted with ethyl acetate (2×80 mL). The combined organic layers were washed with brine, dried over sodium sulfate, and concentrated. The residue was purified by reverse phase chromatography to give the title compound (920 mg, 77%) as a yellow solid. MS (ESI): 754 m/z [M+Na]+.

2-((7-(2-(2-Fluoro-5-((6-fluoro-4-formyl-1H-indol-5-yl)oxy)phenyl)-1H-imidazol-5-yl)-7-(3-iodophenyl)heptyl)thio)acetic acid

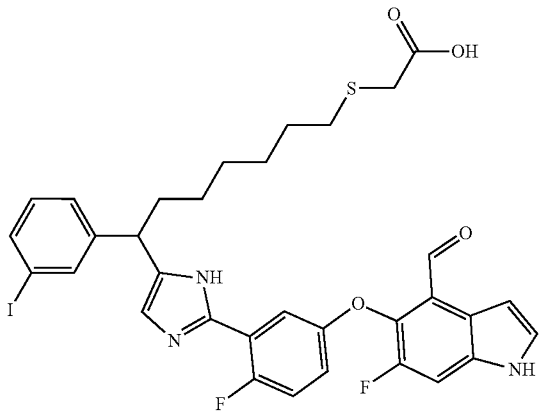 [SMILES: O=Cc1c(Oc2ccc(F)c(-c3ncc(C(CCCCCCSCC(=O)O)c4cccc(I)c4)[nH]3)c2)c(F)cc2[nH]ccc12]

Step C: To a stirred solution of Step B product (910 mg, 1.24 mmol) in tetrahydrofuran (10 mL) was added manganese dioxide (1.08 g, 12.4 mmol). The mixture was stirred at room temperature overnight, then filtered through a pad of Celite. The filtrate was concentrated to give the title compound (625 mg, 70%), which was used for the next step without further purification. MS (ESI): 730 m/z [M+H]+.

2-((7-(2-(2-Fluoro-5-((6-fluoro-4-formyl-1H-indol-5-yl)oxy)phenyl)-1H-imidazol-5-yl)-7-(3-iodophenyl)heptyl)sulfonyl)acetic Acid

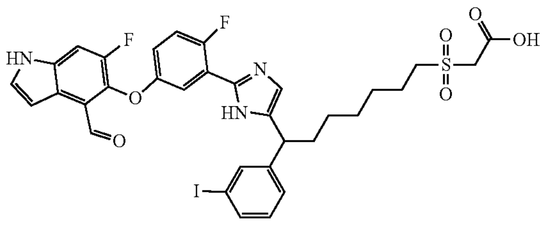 [SMILES: O=Cc1c(Oc2ccc(F)c(-c3ncc(C(CCCCCCS(=O)(=O)CC(=O)O)c4cccc(I)c4)[nH]3)c2)c(F)cc2[nH]ccc12]

Step D: To a stirred solution of Step C product (760 mg, 1.04 mmol) in methanol (10 mL) was added a mixture of 700 mg ammonium molybdate tetrahydrate in 7 mL of hydrogen peroxide (30% in water). The reaction was stirred at room temperature for 10 minutes, then diluted with water and extracted with ethyl acetate (3×20 mL). The combined organic layers were washed with saturated sodium sulfite, brine, dried over sodium sulfate, and concentrated. The residue was purified by reverse phase chromatography to give the title compound (310 mg, 39%) as a pale white solid. MS (ESI): 762 m/z [M+H]+.

(14E)-23,29-Difluoro-6-(3-iodophenyl)-25-oxa-13 6-thia-3,20,31-triazapentacyclo[24.3.1.12,5.016,24.017,21]hentriaconta-1(30),2,4,14,16,18,21,23,26,28-decaene 13,13-dioxide

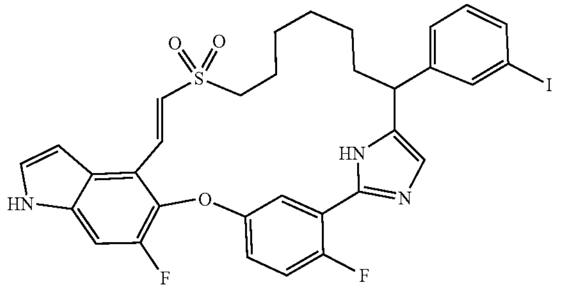 [SMILES: O=S1(=O)/C=C/c2c(c(F)cc3[nH]ccc23)Oc2ccc(F)c(c2)-c2ncc([nH]2)C(c2cccc(I)c2)CCCCCC1]

Step E: To a stirred solution of piperidine (5 mL) and acetic acid (0.5 mL) in toluene (100 mL) was added Step D product (220 mg, 0.29 mmol). The mixture was stirred at 100° C. overnight and concentrated. The residue was purified by preparative thin-layer chromatography (eluted with petroleum ether/dichloromethane/ethyl acetate=3/2/2) to give the title compound (20 mg, 10%) as a pale white solid. MS (ESI): 700 m/z [M+H]+.

Ethyl (E)-3-[3-[(14E)-23,29-difluoro-13,13-dioxo-25-oxa-13 6-thia-3,20,31-triazapentacyclo[24.3.1.12,5.016,24.017,21]hentriaconta-1(30),2,4,14,16,18,21,23,26,28-decaen-6-yl]phenyl]prop-2-enoate

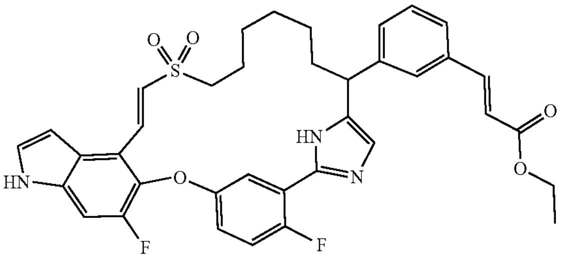 [SMILES: CCOC(=O)/C=C/c1cccc(C2CCCCCCS(=O)(=O)/C=C/c3c(c(F)cc4[nH]ccc34)Oc3ccc(F)c(c3)-c3ncc2[nH]3)c1]

Step F: To a stirred and degassed solution of Step E product (20 mg, 0.03 mmol) in N,N-dimethylformamide (2 mL) was added ethyl acrylate (6 mg, 0.06 mmol), palladium acetate (1 mg, 0.004 mmol), tri-ortho-toluene-phosphine (4 mg, 0.01 mmol) and triethylamine (9 mg, 0.09 mmol) in a sealed tube under nitrogen atmosphere. The mixture was stirred at 100° C. for 1 hour, cooled to room temperature and diluted with ethyl acetate (30 mL). The solution was washed with water (4×20 mL), brine (2×10 mL), dried over sodium sulfate, and concentrated. The residue was purified by preparative thin-layer chromatography (eluted with petroleum ether/dichloromethane/ethyl acetate=3/2/2) to give the title compound (15 mg, 78%) as a light-yellow solid. MS (ESI): 672 m/z [M+H]+.

Ethyl 3-[3-(23,29-difluoro-13,13-dioxo-25-oxa-13 6-thia-3,20,31-triazapentacyclo[24.3.1.12,5.016,24.017,21]hentriaconta-1(30),2,4,16,18,21,23,26,28-nonaen-6-yl)phenyl]propanoate

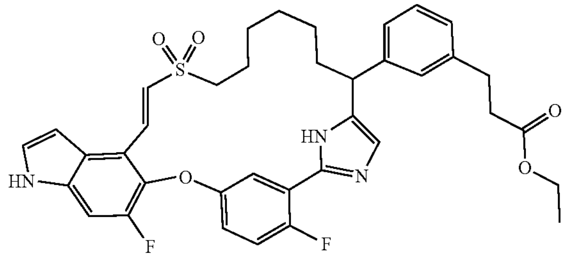 [SMILES: CCOC(=O)CCc1cccc(C2CCCCCCS(=O)(=O)/C=C/c3c(c(F)cc4[nH]ccc34)Oc3ccc(F)c(c3)-c3ncc2[nH]3)c1]

Step G: To a stirred solution of Step F product (15 mg, 0.02 mmol) in tetrahydrofuran (2 mL) was added 10% palladium on active carbon (15 mg). The mixture was stirred at room temperature under hydrogen atmosphere overnight, then filtered through a pad of Celite. The filtrate was concentrated. The residue was purified by preparative thin-layer chromatography (petroleum ether/dichloromethane/ethyl acetate=3/2/2) to give the title compound (6 mg, 40%) as a light-yellow solid. MS (ESI): 676 m/z $[M+H]^+$.

Compound 35: 3-[3-(23,29-Difluoro-13,13-dioxo-25-oxa-13 6-thia-3,20,31-triazapentacyclo[24.3.1.12,5.016,24.017,21]hentriaconta-1(30),2,4,16,18,21,23,26,28-nonaen-6-yl)phenyl]propanoic Acid

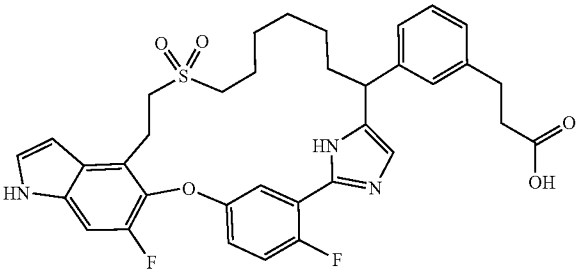 [SMILES: O=C(O)CCc1cccc(C2CCCCCCS(=O)(=O)CCc3c(c(F)cc4[nH]ccc34)Oc3ccc(F)c(c3)-c3ncc2[nH]3)c1]

Step H: To a stirred solution of Step G product (6 mg, 0.009 mmol) in tetrahydrofuran (2 mL) was added a solution of lithium hydroxide (1 mg, 0.04 mmol) in water (0.9 mL). The solution was stirred at room temperature overnight, then concentrated to remove the solvent. The residue was re-dissolved in water (1 mL), acidified to pH ~3 with 1 N hydrochloric acid. The formed precipitate was collected by filtration and dried to give the title compound (2.8 mg, 47%) as a white solid. $^1H$ NMR (400 MHz, $CD_3OD$) δ 7.61-7.56 (m, 1H), 7.36 (d, J=3.2 Hz, 1H), 7.30-7.15 (m, 5H), 7.10-6.87 (m, 3H), 6.61 (d, J=3.2 Hz, 1H), 4.04-3.97 (m, 1H), 3.32-3.25 (m, 2H), 2.97 (dd, J=10.0 Hz, 6.1 Hz, 2H), 2.89 (t, J=7.6 Hz, 2H), 2.58 (t, J=7.6 Hz, 2H), 2.21-2.07 (m, 1H), 1.95-1.85 (m, 1H), 1.64-1.55 (m, 2H), 1.51-1.20 (m, 8H) ppm. MS (ESI): 648 m/z $[M+H]^+$.

Example 36. 3-[3-(22,28-Difluoro-12,12-dioxo-24-oxa-12λ6-thia-3,19,30-triazapentacyclo[23.3.1.12,5.015,23.016,20]triaconta-1(29),2,4,15,17,20,22,25,27-nonaen-6-yl)phenyl]propanoic Acid

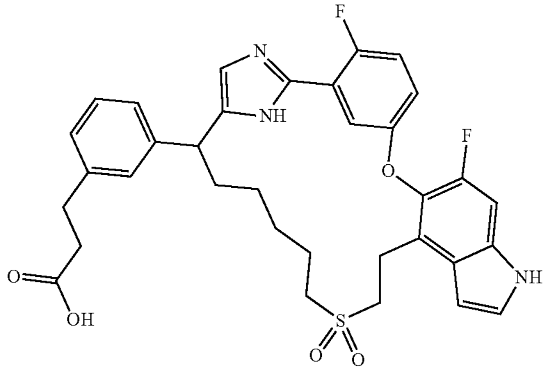 [SMILES: O=C(O)CCc1cccc(C2CCCCCS(=O)(=O)CCc3c(c(F)cc4[nH]ccc34)Oc3ccc(F)c(c3)-c3ncc2[nH]3)c1]

Exchanging 1-bromo-9-chloro-3-(3-iodophenyl)nonan-2-one (Intermediate 17-2) with 1-bromo-8-chloro-3-(3-iodophenyl)octan-2-one (Intermediate 17-3, 1.0 g, 2.27 mmol) in Step A, the reaction sequence (Steps A to Step H) described for Example 35 was used to prepare the title compound as a white solid (16 mg). MS (ESI): 634 m/z $[M+H]^+$. $^1H$ NMR (400 MHz, $CD_3OD$) δ 7.55 (dd, J=6.0 Hz, 3.2 Hz, 1H), 7.37 (d, J=3.2 Hz, 1H), 7.30-7.22 (m, 2H), 7.19-6.99 (m, 5H), 6.81 (s, 1H), 6.65 (dd, J=3.2 Hz, 0.8 Hz, 1H), 3.90 (dd, J=11.6 Hz, 3.2 Hz, 1H), 3.54-3.34 (m, 3H), 2.94-2.75 (m, 4H), 2.54 (t, J=7.6 Hz, 2H), 2.16-2.01 (m, 1H), 1.84-1.61 (m, 3H), 1.55-1.43 (m, 1H), 1.39-1.33 (m, 4H) ppm.

Example 37. 3-[3-(22,28-Difluoro-6-methyl-12,12-dioxo-24-oxa-12λ6-thia-3,19,30-triazapentacyclo[23.3.1.12,5.015,23.016,20]triaconta-1(29),2,4,15,17,20,22,25,27-nonaen-6-yl)phenyl]propanoic Acid

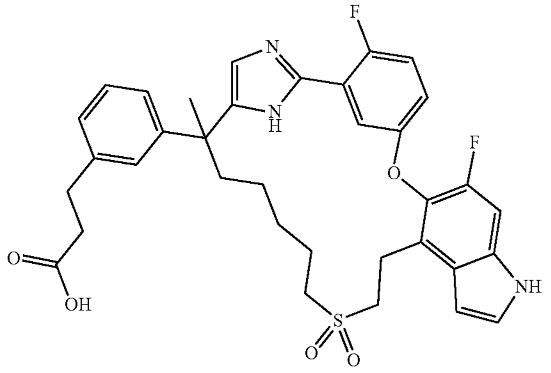 [SMILES: CC1(c2cccc(CCC(=O)O)c2)CCCCCS(=O)(=O)CCc2c(c(F)cc3[nH]ccc23)Oc2ccc(F)c(c2)-c2ncc1[nH]2]

Ethyl 6-[3-(3-ethoxy-3-oxo-propyl)phenyl]-22,28-difluoro-6-methyl-12,12-dioxo-24-oxa-12lambda6-thia-3,19,30-triazapentacyclo[23.3.1.12,5.015,23.016,20]triaconta-1(29),2,4,15,17,20,22,25,27-nonaene-13-carboxylate

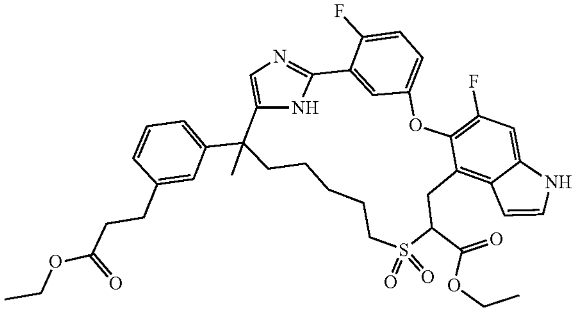 [SMILES: CCOC(=O)CCc1cccc(C2(C)CCCCCS(=O)(=O)C(C(=O)OCC)Cc3c(c(F)cc4[nH]ccc34)Oc3ccc(F)c(c3)-c3ncc2[nH]3)c1]

Step A: Replacing 1-bromo-9-chloro-3-(3-iodophenyl) nonan-2-one (Intermediate 17-2) with 1-bromo-8-chloro-3-(3-iodophenyl)-3-methyl-octan-2-one (Intermediate 17-4, 2.4 g, 4.72 mmol) in Step A of Example 35, and replacing 2-mercaptoacetic acid and methanol/sodium methoxide with ethyl 2-mercaptoacetate (132 mg, 1.1 mmol) and ethanol (20 mL)/sodium ethoxide (172 mg, 2.5 mmol) in Step B of Example 35, the reaction procedure sequence (Steps A to Step G) described for Example 35 was followed to prepare the title compound as a yellow oil (65 mg). MS (ESI): 748 m/z [M+H]+, retention time: 1.89 minutes (LC-MS Method 012).

6-[3-(2-carboxyethyl)phenyl]-22,28-difluoro-6-methyl-12,12-dioxo-24-oxa-12lambda6-thia-3,19,30-triazapentacyclo[23.3.1.12,5.015,23.016,20]triaconta-1(29),2,4,15,17,20,22,25,27-nonaene-13-carboxylic Acid

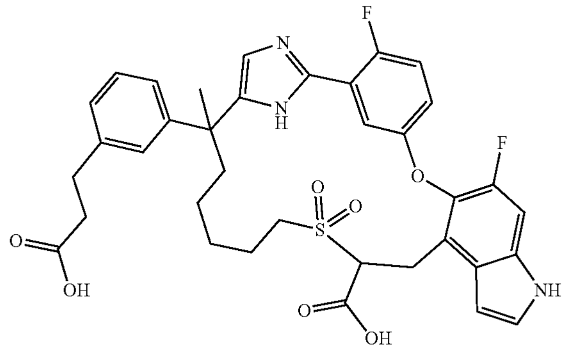 [SMILES: CC1(c2cccc(CCC(=O)O)c2)CCCCCS(=O)(=O)C(C(=O)O)Cc2c(c(F)cc3[nH]ccc23)Oc2ccc(F)c(c2)-c2ncc1[nH]2]

Step B: To a stirred solution of product (65 mg, 0.07 mmol) in tetrahydrofuran (10 mL) was added lithium hydroxide monohydrate (15.5 mg, in 2 mL water). The reaction was stirred at room temperature for 16 hours. The mixture was acidified with 1 M hydrochloric acid to pH ~4, then extracted with ethyl acetate (3×20 mL). The combined organic extracts were washed with brine, dried over anhydrous sodium sulfate, and concentrated to give the title compound (60 mg, 89%) as a white solid. MS (ESI): 692 m/z [M+H]+, retention time: 1.66 minutes (LC-MS Method 012).

3-[3-(22,28-Difluoro-6-methyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenyl]propanoic Acid

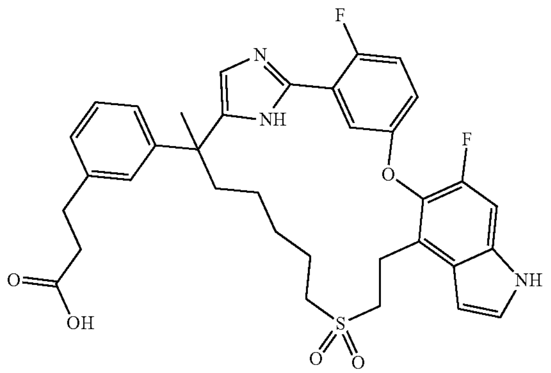 [SMILES: CC1(c2cccc(CCC(=O)O)c2)CCCCCS(=O)(=O)CCc2c(c(F)cc3[nH]ccc23)Oc2ccc(F)c(c2)-c2ncc1[nH]2]

Step C: To a stirred solution of Step H product (60 mg, 0.06 mmol) in dimethyl sulfoxide (5 mL) was added lithium chloride (8.3 mg, 0.19 mmol). The reaction mixture was stirred at 120° C. for 40 hours, then cooled to room temperature and diluted with ethyl acetate (30 mL). The solution was washed with brine (2×30 mL), dried over anhydrous sodium sulfate, and concentrated. The crude product was purified by Prep-HPLC to give the title compound (17.2 mg, 40%) as a white solid. MS (ESI): 648 m/z [M+H]+, retention time: 1.40 minutes (LC-MS Method 012).

Example 38. 3-[3-(22,28-Difluoro-6,12-dimethyl-9,9,13-trioxo-24-oxa-9λ6-thia-3,12,19,30-tetrazapentacyclo[23.3.1.12,5.015,23.016,20]triaconta-1(29),2,4,15,17,20,22,25,27-nonaen-6-yl)phenyl]propanoic Acid

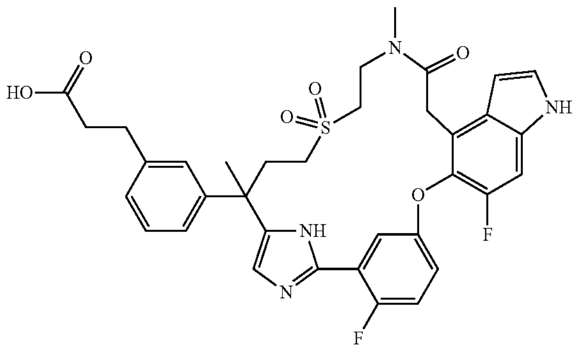 [SMILES: CN1CCS(=O)(=O)CCC(C)(c2cccc(CCC(=O)O)c2)c2cnc([nH]2)-c2cc(ccc2F)Oc2c(F)cc3[nH]ccc3c2CC1=O]

Ethyl 2-(5-(3-(5-(4-((2-(((benzyloxy)carbonyl)(methyl)amino)ethyl)sulfonyl)-2-(3-iodophenyl)butan-2-yl)-1H-imidazol-2-yl)-4-fluorophenoxy)-6-fluoro-1H-indol-4-yl)acetate

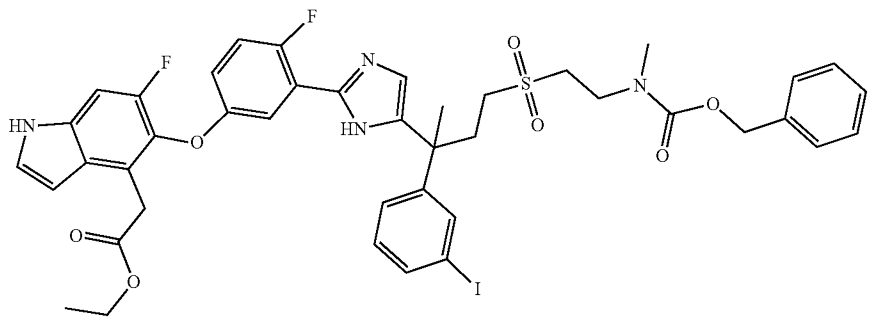 [SMILES: CCOC(=O)Cc1c(Oc2ccc(F)c(-c3ncc(C(C)(CCS(=O)(=O)CCN(C)C(=O)OCc4ccccc4)c4cccc(I)c4)[nH]3)c2)c(F)cc2[nH]ccc12]

Step A: Exchanging 8-bromo-6-(3-iodophenyl)-2,2,6-trimethyl-7-oxooctyl acetate (Intermediate 17) with benzyl (2-((5-chloro-3-(3-iodophenyl)-3-methyl-4-oxopentyl)sulfonyl)ethyl)(methyl)carbamate (Intermediate 17-5, 0.86 g, 1.455 mmol), and ethyl 2-(((5-(3-carbamimidoyl-4-fluorophenoxy)-6-fluoro-1-(phenylsulfonyl)-1H-indol-4-yl)methyl)sulfonyl)acetate (Intermediate 18) with ethyl 2-(5-(3-carbamimidoyl-4-fluorophenoxy)-6-fluoro-1H-indol-4-yl)acetate (Intermediate 78, 0.65 g, 1.746 mmol) in Step A, the title compound (1.0 g, 75%, pale yellow oil) was prepared following the procedure described for Example 21, Step A. MS (ESI): 911 m/z $[M+H]^+$. 2-(5-(3-(5-(4-((2-(((Benzyloxy)carbonyl)(methyl)amino)ethyl)sulfonyl)-2-(3-iodophenyl)butan-2-yl)-1H-imidazol-2-yl)-4-fluorophenoxy)-6-fluoro-1H-indol-4-yl)acetic Acid

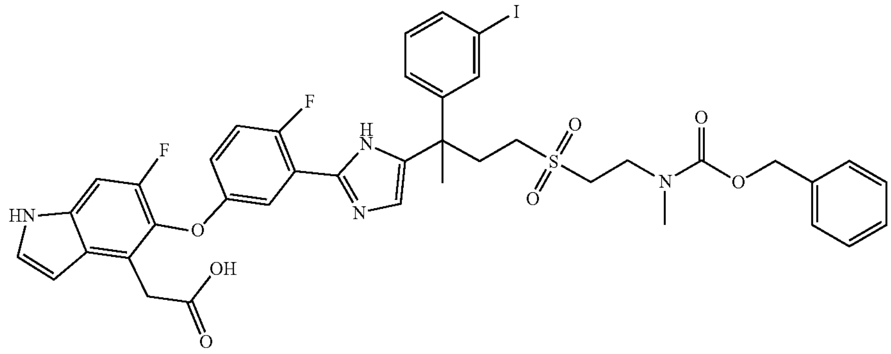 [SMILES: CN(CCS(=O)(=O)CCC(C)(c1cccc(I)c1)c1cnc(-c2cc(Oc3c(F)cc4[nH]ccc4c3CC(=O)O)ccc2F)[nH]1)C(=O)OCc1ccccc1]

Step B: To a stirred solution of Step A product (1.0 g, 1.21 mmol) in tetrahydrofuran/water/methanol (9/3/1, 13 mL) was added lithium hydroxide monohydrate (0.254 g, 6.04 mmol). The solution was stirred at room temperature overnight, acidified to pH 3-4 with 1 N hydrochloric acid, and extracted with ethyl acetate (3×20 mL). The combined organic phase was washed with water, brine, dried over sodium sulfate and concentrated to give the title compound (0.967 g, 90%) as a yellow solid. MS (ESI): 883 m/z $[M+H]^+$. (E)-2-(5-(3-(5-(4-((2-(((Benzyloxy)carbonyl)(methyl)amino)ethyl)sulfonyl)-2-(3-(3-ethoxy-3-oxoprop-1-en-1-yl)phenyl)butan-2-yl)-1H-imidazol-2-yl)-4-fluorophenoxy)-6-fluoro-1H-indol-4-yl)acetic acid

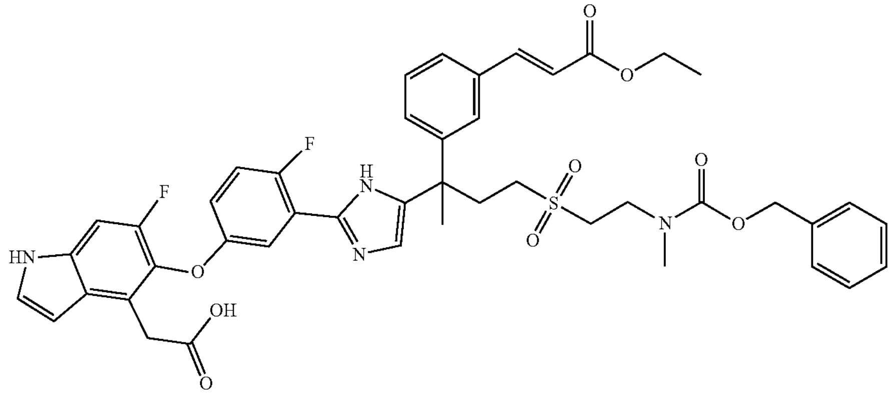 [SMILES: CCOC(=O)/C=C/c1cccc(C(C)(CCS(=O)(=O)CCN(C)C(=O)OCc2ccccc2)c2cnc(-c3cc(Oc4c(F)cc5[nH]ccc5c4CC(=O)O)ccc3F)[nH]2)c1]

Step C: To a stirred solution of Step B product (0.328 g, 0.057 mmol) in N,N-dimethylformamide (3 mL) were added tri(o-tolyl)phosphine (0.0083 g, 0.2 mmol), palladium (II) acetate (0.0226 g, 0.1 mmol), triethylamine (0.293 mL, 5 mmol). After flushing with nitrogen for 10 minutes, ethyl acrylate (0.074 g, 2 mmol) was added. The reaction mixture was heated at 120° C. under microwave for 2 hours. After cooling to room temperature, the mixture was partitioned between water (50 mL) and ethyl acetate (50 mL). The separated organic layer, combined with two additional ethyl acetate extracts (2×25 mL), was washed with saturated lithium chloride (3×15 mL), water, brine, dried over sodium sulfate, and concentrated. The residue was purified by silica gel column chromatography (dichloromethane/methanol=10/1) to give the title compound (0.394 g, 81%) as a yellow solid. MS (ESI): 855 m/z [M+H]+.

2-(5-(3-(5-(2-(3-(3-Ethoxy-3-oxopropyl)phenyl)-4-((2-(methylamino)ethyl)sulfonyl)butan-2-yl)-1H-imidazol-2-yl)-4-fluorophenoxy)-6-fluoro-1H-indol-4-yl)acetic Acid

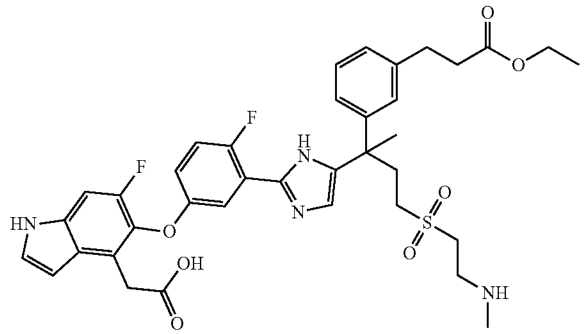 [SMILES: CCOC(=O)CCc1cccc(C(C)(CCS(=O)(=O)CCNC)c2cnc(-c3cc(Oc4c(F)cc5[nH]ccc5c4CC(=O)O)ccc3F)[nH]2)c1]

Step D: To a stirred solution of Step C product (0.198 g, 0.232 mmol) in ethyl acetate (4 mL) was added palladium on carbon (5%, 0.257 g). The mixture was stirred at room temperature overnight under hydrogen, then filtered through a pad of Celite. The filtrate was concentrated to give the title compound (0.164 g, 98%). MS (ESI): 723 m/z [M+H]+.

Ethyl 3-[3-(22,28-difluoro-6,12-dimethyl-9,9,13-trioxo-24-oxa-9 6-thia-3,12,19,30-tetrazapentacyclo [23.3.1.12,5.015,23.016,20]triaconta-1(29),2,4,15,17,20,22,25,27-nonaen-6-yl)phenyl]propanoate

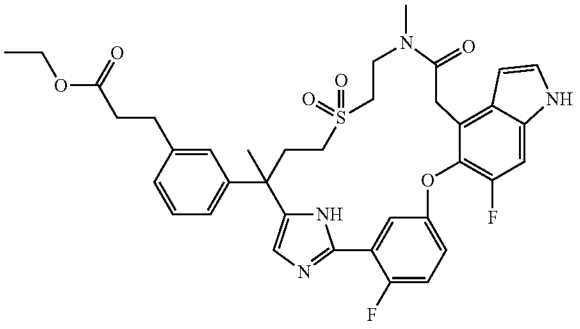 [SMILES: CCOC(=O)CCc1cccc(C2(C)CCS(=O)(=O)CCN(C)C(=O)Cc3c(c(F)cc4[nH]ccc34)Oc3ccc(F)c(c3)-c3ncc2[nH]3)c1]

Step E: To a stirred solution of Step D product (0.164 g, 0.227 mmol) in tetrahydrofuran/N,N-dimethylformamide (21 mL/7 mL) was added 1-ethyl-3-(3-dimethylaminopropyl)carbodiimide hydrochloride (0.0117 g, 0.061 mmol) and 1-hydroxybenzotriazole (0.0082 g, 0.061 g). The suspension was then stirred at room temperature overnight, then quenched with water (50 mL). The mixture was extracted with ethyl acetate (3×20 mL). The combined organic layers were washed with aqueous lithium chloride solution (30 mL), sodium bicarbonate solution (30 mL), brine, dried over sodium sulfate and concentrated. The residue was purified by preparative thin-layer chromatography (ethyl acetate/dichloromethane=2/1) to give the title compound (0.076 g, 48%) as a white solid. MS (ESI): 705 m/z [M+H]+.

Compound 38: 3-[3-(22,28-Difluoro-6,12-dimethyl-9,9,13-trioxo-24-oxa-9 6-thia-3,12,19,30-tetrazapentacyclo [23.3.1.12,5.015,23.016,20]triaconta-1(29),2,4,15,17,20,22,25,27-nonaen-6-yl)phenyl]propanoic Acid

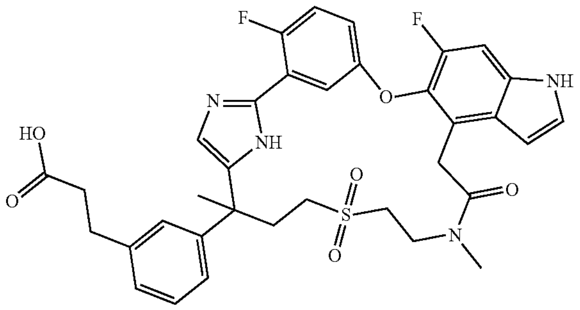 [SMILES: CN1CCS(=O)(=O)CCC(C)(c2cccc(CCC(=O)O)c2)c2cnc([nH]2)-c2cc(ccc2F)Oc2c(F)cc3[nH]ccc3c2CC1=O]

Step F: To a stirred solution of Step E product (0.076 g, 0.108 mmol) in tetrahydrofuran/methanol (1:1, 6 mL) was added lithium hydroxide (1 M in water, 2 mL). The mixture was stirred at room temperature for two hours, then diluted with water (20 mL) and acidified with 1N hydrochloric acid to pH ~4. The mixture was extracted with ethyl acetate (3×20 mL). The combined organic extracts were dried over sodium sulfate and concentrated. The residue was purified by preparative thin-layer chromatography (ethyl acetate/dichloromethane=2/1) to give the title compound (0.057 g, 78%) as a white solid. MS (ESI): 677 m/z [M+H]+. Retention time: 1.63 minutes (LC-MS Method 011).

Example 39. 3-[3-(23,29-Difluoro-6,12-dimethyl-9,9,13-trioxo-25-oxa-9λ6-thia-3,12,20,31-tetrazapentacyclo[24.3.1.12,5.016,24.017,21]hentriaconta-1(30),2,4,16,18,21,23,26,28-nonaen-6-yl)phenyl]propanoic Acid

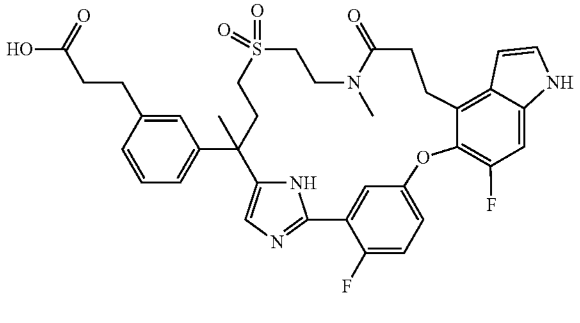 [SMILES: CN1CCS(=O)(=O)CCC(C)(c2cccc(CCC(=O)O)c2)c2cnc([nH]2)-c2cc(ccc2F)Oc2c(F)cc3[nH]ccc3c2CCC1=O]

Ethyl (E)-3-(5-(3-(5-(4-((2-(((benzyloxy)carbonyl)(methyl)amino)ethyl)sulfonyl)-2-(3-iodophenyl)butan-2-yl)-1H-imidazol-2-yl)-4-fluorophenoxy)-6-fluoro-1H-indol-4-yl)acrylate

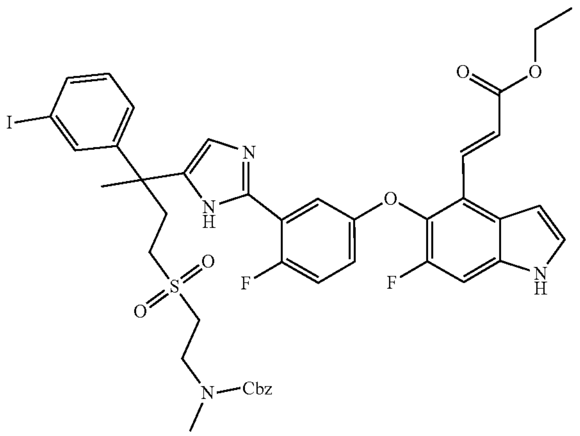 [SMILES: CCOC(=O)/C=C/c1c(Oc2ccc(F)c(-c3ncc(C(C)(CCS(=O)(=O)CCN(C)C(=O)OCc4ccccc4)c4cccc(I)c4)[nH]3)c2)c(F)cc2[nH]ccc12]

Step A, To a stirred solution of benzyl (2-((5-chloro-3-(3-iodophenyl)-3-methyl-4-oxopentyl)sulfonyl)ethyl)(methyl)carbamate (Intermediate 17-5, 1.1 g, 1.862 mmol) and ethyl (E)-3-(5-(3-carbamimidoyl-4-fluorophenoxy)-6-fluoro-1H-indol-4-yl)acrylate (Intermediate 80B, 733 mg, 2.047 mmol) in N,N-dimethylformamide (10 mL) was added sodium bicarbonate (815 mg, 9.702 mmol). The reaction mixture was stirred at 60° C. for 18 hours under nitrogen, then quenched with water (30 mL) and extracted with ethyl acetate (3×50 mL). The combined organic layers were dried over sodium sulfate and concentrated. The residue was purified by automated silica gel chromatography (petroleum ether: ethyl acetate=10:1 to 2:1) to give the title compound (1.1 g, 55%). MS (ESI): 923 m/z [M+H]+.

(E)-3-(6-Fluoro-5-(4-fluoro-3-(5-(2-(3-iodophenyl)-4-((2-(methylamino)ethyl)sulfonyl)butan-2-yl)-1H-imidazol-2-yl)phenoxy)-1H-indol-4-yl)acrylic Acid

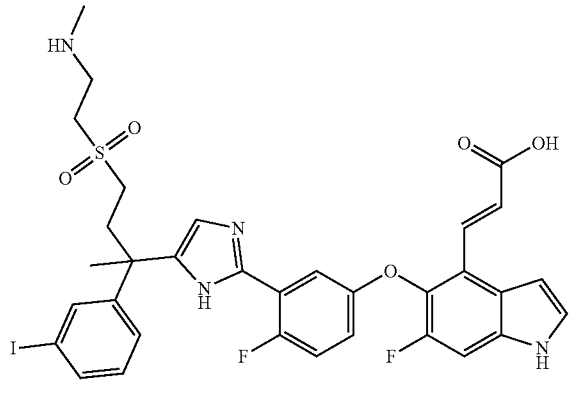 [SMILES: CNCCS(=O)(=O)CCC(C)(c1cccc(I)c1)c1cnc(-c2cc(Oc3c(F)cc4[nH]ccc4c3/C=C/C(=O)O)ccc2F)[nH]1]

Step B: To a stirred solution of Step A product (1.1 g, 1.192 mmol) in tetrahydrofuran/methanol (4/1, 20 mL) was added 20 M sodium hydroxide (1.0 mL). The reaction mixture was stirred at 60° C. for 18 hours under nitrogen, then cooled to room temperature and acidified with concentrated hydrochloric acid to pH ~2. The mixture was concentrated. The residue was purified by reverse phase chromatography (acetonitrile/water=0 to 20%) to give the title compound (100 mg, 11%). MS (ESI): 761 m/z $[M+H]^+$.

(14E)-23,29-Difluoro-6-(3-iodophenyl)-6,12-dimethyl-9,9-dioxo-25-oxa-9 6-thia-3,12,20,31-tetrazapentacyclo[24.3.1.12,5.016,24.017,21]hentriaconta-1(30),2,4,14,16,18,21,23,26,28-decaen-13-one

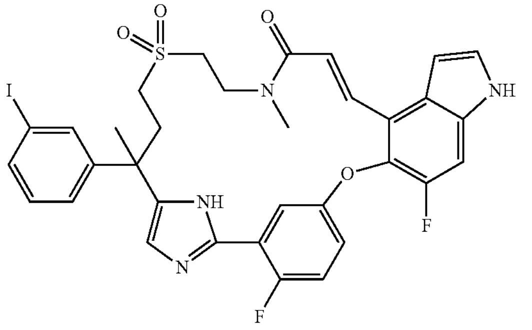 [SMILES: CN1CCS(=O)(=O)CCC(C)(c2cccc(I)c2)c2cnc([nH]2)-c2cc(ccc2F)Oc2c(F)cc3[nH]ccc3c2/C=C/C1=O]

Step C: To a stirred solution of Step B product (100 mg, 0.132 mmol) in tetrahydrofuran/N,N-dimethylformamide (3/1, 5 mL) was added 1-ethyl-3-(3-dimethylaminopropyl) carbodiimide hydrochloride (76 mg, 0.395 mmol) and 1-hydroxybenzyltriazole (53 mg, 0.395 mmol). The mixture was stirred at room temperature for 48 hours, then quenched with water (20 mL) and extracted with ethyl acetate (3×30 mL). The combined organic layers were dried over sodium sulfate and concentrated. The residue was purified by automated silica gel flash chromatograph (petroleum ether: ethyl acetate=10:0 to 1:1) to give the title compound (34 mg, 34%). MS (ESI): 743 m/z $[M+H]^+$. Retention time: 1.85 minutes (LC-MS Method 015).

Compound 39: 3-[3-(23,29-Difluoro-6,12-dimethyl-9,9,13-trioxo-25-oxa-9 6-thia-3,12,20,31-tetrazapentacyclo[24.3.1.12,5.016,24.017,21]hentriaconta-1(30),2,4,16,18,21,23,26,28-nonaen-6-yl)phenyl] propanoic Acid

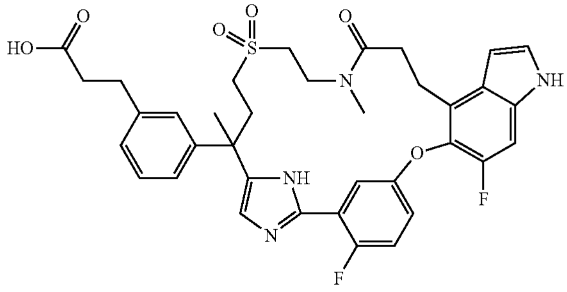 [SMILES: CN1CCS(=O)(=O)CCC(C)(c2cccc(CCC(=O)O)c2)c2cnc([nH]2)-c2cc(ccc2F)Oc2c(F)cc3[nH]ccc3c2CCC1=O]

Step D: Exchanging (14E)-23,29-difluoro-6-(3-iodophenyl)-25-oxa-13λ6-thia-3,20,31-triazapentacyclo[24.3.1.12,5.016,24.017,21]hentriaconta-1(30),2,4,14,16,18,21,23,26,28-decaene 13,13-dioxide (Step E product of Example 35) with Step C product (34 mg, 0.046 mmol) of this example, the reaction sequence (from Steps F to Step H) described for Example 35 was used to prepare the title compound as a white solid (2.1 mg). MS (ESI): 691 m/z $[M+H]^+$, retention time: 1.64 minutes (LC-MS Method 016).

Example 40. 3-[3-(24,30-Difluoro-9,9-dioxo-26-oxa-9λ6-thia-3,13,14,15,21,33-hexazahexacyclo[25.3.1.12,5.112,15.017,25.018,22]tritriaconta-1(31),2,4,12(32),13,17,19,22,24,27,29-undecaen-6-yl)-2-fluoro-phenyl]propanoic Acid

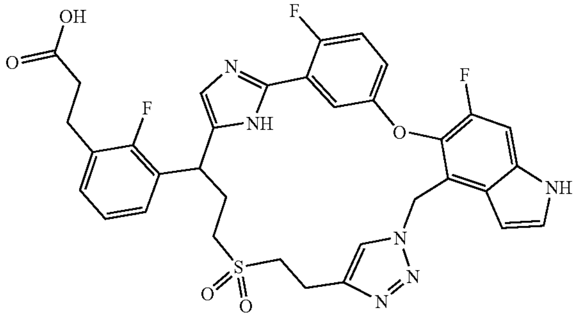 [SMILES: O=C(O)CCc1cccc(C2CCS(=O)(=O)CCc3cn(nn3)Cc3c(c(F)cc4[nH]ccc34)Oc3ccc(F)c(c3)-c3ncc2[nH]3)c1F]

and

Example 41. 24,30-Difluoro-6-(2-fluorophenyl)-26-oxa-9λ6-thia-3,13,14,15,21,33-hexazahexacyclo[25.3.1.12,5.112,15.017,25.018,22]tritriaconta-1(31),2,4,12(32),13,17,19,22,24,27,29-undecaene 9,9-dioxide

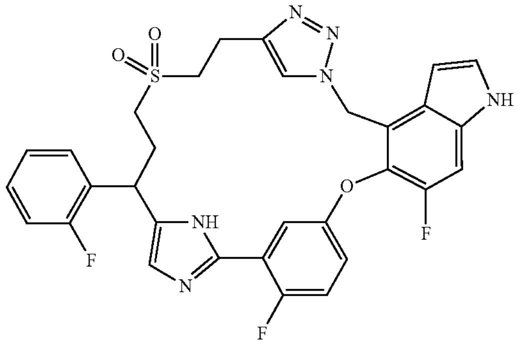 [SMILES: O=S1(=O)CCc2cn(nn2)Cc2c(c(F)cc3[nH]ccc23)Oc2ccc(F)c(c2)-c2ncc([nH]2)C(c2ccccc2F)CC1]

4-(Azidomethyl)-5-(3-(5-(1-(3-bromo-2-fluorophenyl)-3-(but-3-yn-1-ylsulfonyl)propyl)-1H-imidazol-2-yl)-4-fluorophenoxy)-6-fluoro-1H-indole

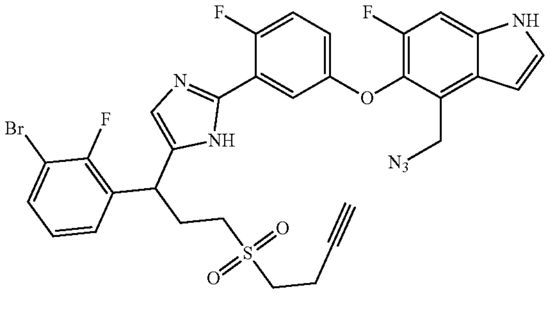 [SMILES: C#CCCS(=O)(=O)CCC(c1cnc(-c2cc(Oc3c(F)cc4[nH]ccc4c3CN=[N+]=[N-])ccc2F)[nH]1)c1cccc(Br)c1F]

Step A: To a stirred and cooled (0° C.) solution of 1-bromo-3-(3-bromo-2-fluorophenyl)-5-(but-3-yn-1-ylsulfonyl)pentan-2-one (Intermediate 17-6, 100 mg, 0.22 mmol) in N,N-dimethylformamide (20 mL) was added 5-((4-(azidomethyl)-6-fluoro-1H-indol-5-yl)oxy)-2-fluorobenzimidamide (Intermediate 10-5, 75.4 mg, 0.22 mmol) and sodium bicarbonate (18.5 mg, 0.04 mmol). The mixture was heated at 80° C. for 2 hours, then cooled to room temperature, diluted with ethyl acetate (100 mL). The solution was washed with water, brine, dried over sodium sulfate, and concentrated. The residue was purified by silica gel chromatography (50% ethyl acetate in petroleum ether) to give the title compound (77 mg, 50%) as a yellow oil. MS (ESI): 697, 699 m/z $[M+H]^+$, retention time: 1.84 minutes (LC-MS Method 017).

6-(3-Bromo-2-fluoro-phenyl)-24,30-difluoro-26-oxa-9lambda6-thia-3,13,14,15,21,33-hexazahexacyclo[25.3.1.12,5.112,15.017,25.018,22]tritriaconta-1(31),2,4,12(32),13,17,19,22,24,27,29-undecaene 9,9-dioxide

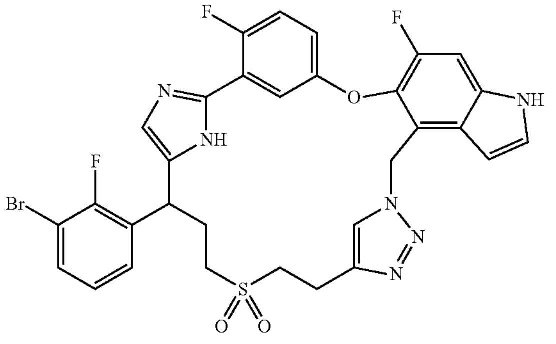 [SMILES: O=S1(=O)CCc2cn(nn2)Cc2c(c(F)cc3[nH]ccc23)Oc2ccc(F)c(c2)-c2ncc([nH]2)C(c2cccc(Br)c2F)CC1]

Step B: To a stirred solution of Step A product (330 mg, 0.47 mmol) in dichloromethane (30 mL) was added tetrakis (acetonitrile)copper (I) tetrafluoroborate (15 mg, 0.047 mmol) and N,N,N-Tris[(1-benzyl-1H-1,2,3-triazol-4-yl) methyl]amine (25 mg, 0.047 mmol). The mixture was stirred at 40° C. for 16 hours. After removing the solvent, the residue was purified by automated flash chromatography (0-5% of methanol in dichloromethane) to give the title compound (140 mg, 42%) as a white solid. MS (ESI): 697, 699 m/z $[M+H]^+$.

Compound 40: 3-[3-(24,30-Difluoro-9,9-dioxo-26-oxa-9lambda6-thia-3,13,14,15,21,33-hexazahexacyclo[25.3.1.12,5.112,15.017,25.018,22]tritriaconta-1(31),2,4,12(32),13,17,19,22,24,27,29-undecaen-6-yl)-2-fluoro-phenyl]propanoic Acid

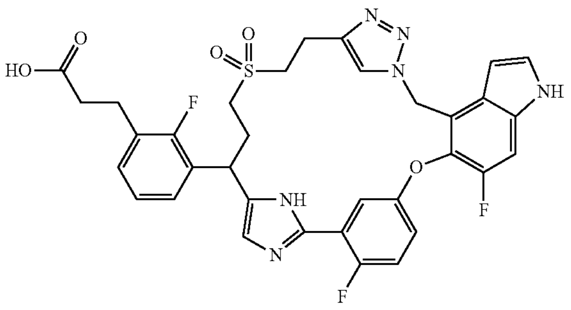 [SMILES: O=C(O)CCc1cccc(C2CCS(=O)(=O)CCc3cn(nn3)Cc3c(c(F)cc4[nH]ccc34)Oc3ccc(F)c(c3)-c3ncc2[nH]3)c1F]

Compound 41: 24,30-Difluoro-6-(2-fluorophenyl)-26-oxa-9lambda6-thia-3,13,14,15,21,33-hexazahexacyclo[25.3.1.12,5.112,15.017,25.018,22]-tritriaconta-1(31),2,4,12(32),13,17,19,22,24,27,29-undecaene 9,9-dioxide

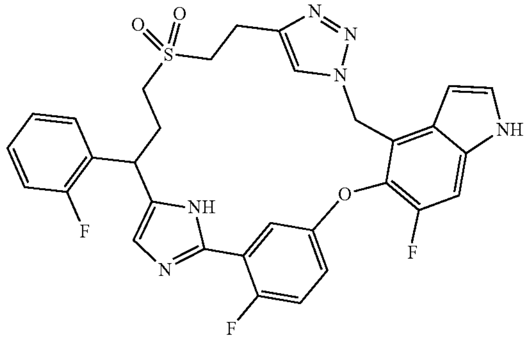 [SMILES: O=S1(=O)CCc2cn(nn2)Cc2c(c(F)cc3[nH]ccc23)Oc2ccc(F)c(c2)-c2ncc([nH]2)C(c2ccccc2F)CC1]

Step C: Exchanging (14E)-23,29-Difluoro-6-(3-iodophenyl)-25-oxa-13λ6-thia-3,20,31-triazapentacyclo[24.3.1.12,5.016,24.017,21]hentriaconta-1(30),2,4,14,16,18,21,23,26,28-decaene 13,13-dioxide (Step E product of Example 35) with Step B product (77 mg, 0.11 mmol) mmol) in this example, the reaction sequence (from Step F to Step H) described for Example 35 was used to prepare the title compounds as a white solid. The mixture was further separated by Prep-HPLC (additive: ammonium bicarbonate) to give the first eluent as 40 (21 mg) and the second eluent as 41 (3.2 mg), both as white solids.

Compound 40 MS (ESI): 691 m/z $[M+H]^+$, retention time: 1.68 minutes (LC-MS Method 007). $^1$HNMR (400 MHz, $CD_3OD$) d 7.68 (s, 1H), 7.45 (d, J=2.8 Hz, 1H), 7.39 (d, J=10.4 Hz, 1H), 7.22-7.13 (m, 4H), 7.08 (s, 1H), 6.98 (t, J=7.6 Hz, 1H), 6.93-6.88 (m, 1H), 6.71 (d, J=2.8 Hz, 1H), 5.99-5.80 (m, 2H), 4.41-4.37 (m, 1H), 3.41-3.37 (m, 1H), 3.19-3.12 (m, 2H), 2.98-2.92 (m, 3H), 2.84-2.67 (m, 2H), 2.60-2.47 (m, 3H), 2.40-2.29 (m, 1H) ppm.

Compound 41: MS (ESI): 619 m/z $[M+H]^+$, retention time: 1.74 minutes (LC-MS Method 007). $^1$HNMR (400 MHz, $CD_3OD$) d 7.69 (s, 1H), 7.44 (d, J=3.2 Hz, 1H), 7.39 (d, J=10.4 Hz, 1H), 7.31-7.03 (m, 7H), 6.96 (q, J=2.4 Hz, 1H), 6.71 (d, J=2.8 Hz, 1H), 6.01-5.79 (m, 2H), 4.41-4.37 (m, 1H), 3.38-3.37 (m, 1H), 3.23-3.12 (m, 2H), 2.98-2.96 (m, 1H), 2.82-2.72 (m, 2H), 2.55-2.50 (m, 1H), 2.36-2.33 (m, 1H) ppm.

Example 42. 3-[3-(22,28-Difluoro-6,9-dimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenyl]propanoic Acid

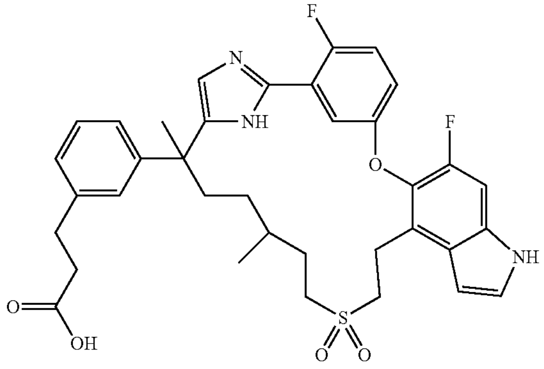 [SMILES: CC1CCC(C)(c2cccc(CCC(=O)O)c2)c2cnc([nH]2)-c2cc(ccc2F)Oc2c(F)cc3[nH]ccc3c2CCS(=O)(=O)CC1]

Exchanging 1-bromo-8-chloro-3-(3-iodophenyl)-3-methyl-octan-2-one (Intermediate 17-4, 2.4 g, 4.72 mmol) with ethyl 2-((8-chloro-6-(3-iodophenyl)-3,6-dimethyl-7-oxooctyl)sulfonyl)acetate (Intermediate 17-7, 780 mg, 1.4 mmol) in Step A, the reaction sequence (Steps A to Step C) described for Example 37 was used to prepare the title compound (30 mg) as a white solid. MS (ESI): 662 m/z $[M+H]^+$, retention time: 1.40 minutes (LC-MS Method 018). $^1H$ NMR (400 MHz, $CD_3OD$) δ 7.47-7.40 (m, 1H), 7.34-7.25 (m, 2H), 7.23-7.11 (m, 2H), 7.10-7.06 (m, 3H), 7.00-6.94 (m, 2H), 6.60 (dd, J=12.8, 3.2 Hz, 1H), 3.53-3.42 (m, 1H), 3.42-3.35 (m, 1H), 2.89-2.75 (m, 3H), 2.65-2.62 (m, 1H), 2.53-2.44 (m, 2H), 2.21-2.18 (m, 1H), 2.08-1.84 (m, 2H), 1.72-1.62 (m, 1H), 1.52 (d, J=12.8 Hz, 4H), 1.33-1.31 (m, 3H), 0.83 (d, J=6.4 Hz, 2H), 0.75 (d, J=6.8 Hz, 2H) ppm.

Example 43. Enantiomers 1 (Compound 43A) and 2 (Compound 43B) of 3-[3-(23,29-difluoro-6,11,11-trimethyl-13,13-dioxo-25-oxa-13lambda6-thia-3,20,31-triazapentacyclo[24.3.1.12,5.016,24.017,21]hentriaconta-1(30),2,4,16,18,21,23,26,28-nonaen-6-yl)phenyl]propanoic Acid

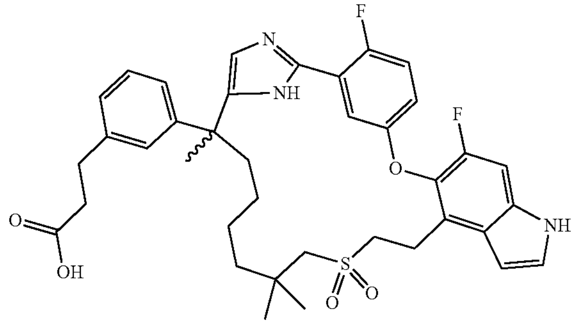 [SMILES: CC1(C)CCCCC(C)(c2cccc(CCC(=O)O)c2)c2cnc([nH]2)-c2cc(ccc2F)Oc2c(F)cc3[nH]ccc3c2CCS(=O)(=O)C1]

3-[3-(23,29-Difluoro-6,11,11-trimethyl-13,13-dioxo-25-oxa-13lambda6-thia-3,20,31-triazapentacyclo[24.3.1.12,5.016,24.017,21]hentriaconta-1(30),2,4,16,18,21,23,26,28-nonaen-6-yl)phenyl]propanoic Acid

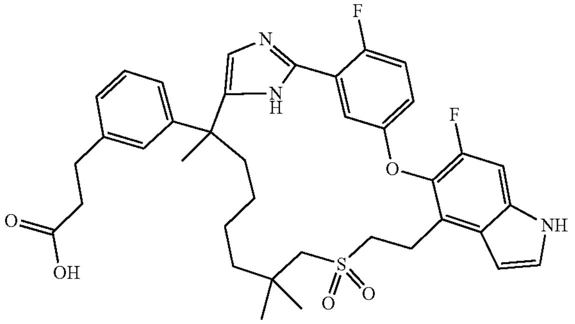 [SMILES: CC1(C)CCCCC(C)(c2cccc(CCC(=O)O)c2)c2cnc([nH]2)-c2cc(ccc2F)Oc2c(F)cc3[nH]ccc3c2CCS(=O)(=O)C1]

Step A: Exchanging 1-bromo-8-chloro-3-(3-iodophenyl)-3-methyl-octan-2-one (Intermediate 17-4) with methyl 3-(3-(1-bromo-9-((2-methoxy-2-oxoethyl)sulfonyl)-3,8,8-trimethyl-2-oxononan-3-yl)phenyl)propanoate (Intermediate 17-8, 2.9 g, 5.16 mmol), the reaction sequence (Steps A to Step C) described for Example 37 was used to prepare the title compounds (306 mg) as a white solid. MS (ESI): 690 m/z $[M+H]^+$, retention time: 1.79 minutes (LC-MS Method 012).

Enantiomers 1 and 2 of 3-[3-(23,29-Difluoro-6,11,11-trimethyl-13,13-dioxo-25-oxa-13lambda6-thia-3,20,31-triazapentacyclo[24.3.1.12,5.016,24.017,21]hentriaconta-1(30),2,4,16,18,21,23,26,28-nonaen-6-yl)phenyl]propanoic Acid

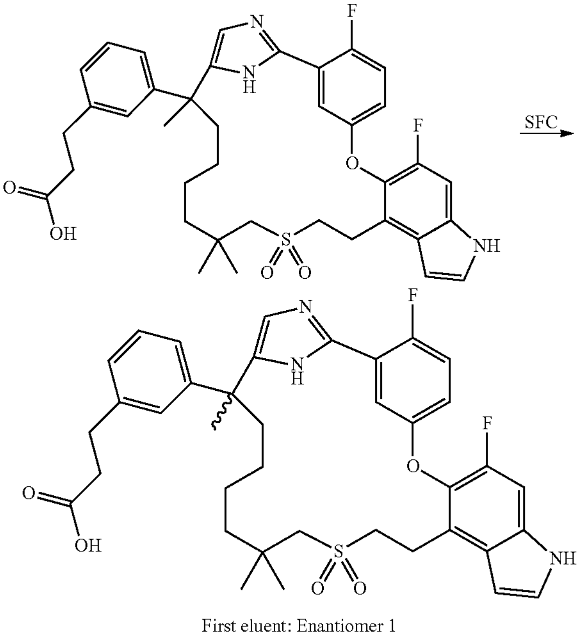

First eluent: Enantiomer 1
Second eluent: Enantiomer 2

Step B: The racemic mixture of Step A product (306 mg, 0.44 mmol) was subjected to chiral SFC separation using a SFC-80 instrument (Thar, Waters); Column: SSWHELK 20*250 mm, 10 μm; Column temperature: 35° C.; Mobile phase: carbon dioxide/methanol (0.2% Methanol Ammonia)= 30/70; Flow rate: 80 g/minutes; Back pressure: 100 bar; Detection wavelength: 214 nm; Cycle time: 4.8 minutes; Sample solution: 5.3 g dissolved in 200 ml methanol; Injection volume: 1 mL. The first eluting isomer, designated as Compound 43A, was obtained as a white solid (99.9 mg, 33%); The second eluting isomer, designated as Compound 43B, was also obtained as a white solid (84.5 mg, 28%).

Compound 43A: 1H NMR (400 MHz, $CD_3OD$) δ 7.92 (s, 1H), 7.33 (d, J=3.2 Hz, 1H), 7.18 (ddd, J=35.1, 16.1, 11.3 Hz, 6H), 7.04 (d, J=6.9 Hz, 1H), 6.65 (s, 1H), 6.55 (d, J=3.2 Hz, 1H), 3.44-3.37 (m, 1H), 3.21-3.10 (m, 3H), 3.02 (s, 2H), 2.89 (t, J=7.8 Hz, 2H), 2.57 (t, J=7.8 Hz, 2H), 2.39 (d, J=10.1 Hz, 1H), 2.22 (s, 1H), 1.58 (s, 3H), 1.50 (s, 2H), 1.26 (d, J=62.2 Hz, 3H), 1.14 (d, J=8.7 Hz, 6H), 0.95 (s, 1H). MS (ESI): 690 m/z $[M+H]^+$, retention time: 1.79 minutes (LC-MS Method 012) ppm.

Compound 43B: 1H NMR (400 MHz, $CD_3OD$) δ 7.92 (s, 1H), 7.33 (d, J=3.2 Hz, 1H), 7.18 (ddd, J=35.1, 16.1, 11.3 Hz, 6H), 7.04 (d, J=6.9 Hz, 1H), 6.65 (s, 1H), 6.55 (d, J=3.2 Hz, 1H), 3.44-3.37 (m, 1H), 3.21-3.10 (m, 3H), 3.02 (s, 2H), 2.89 (t, J=7.8 Hz, 2H), 2.57 (t, J=7.8 Hz, 2H), 2.39 (d, J=10.1 Hz, 1H), 2.22 (s, 1H), 1.58 (s, 3H), 1.50 (s, 2H), 1.26 (d, J=62.2 Hz, 3H), 1.14 (d, J=8.7 Hz, 6H), 0.95 (s, 1H) ppm. 690 m/z $[M+H]^+$, retention time: 1.79 minutes; purity: 98% (254 nm) (LC-MS Method 012) ppm.

Example 44. 3-[3-(22,28-Difluoro-6,10,10-trimethyl-12,12-dioxo-3,24-dioxa-12lambda6-thia-19,30-diazapentacyclo[23.3.1.12,5.015,23.016,20]triaconta-1(29),2(30),4,15,17,20,22,25,27-nonaen-6-yl)phenyl]propanoic acid

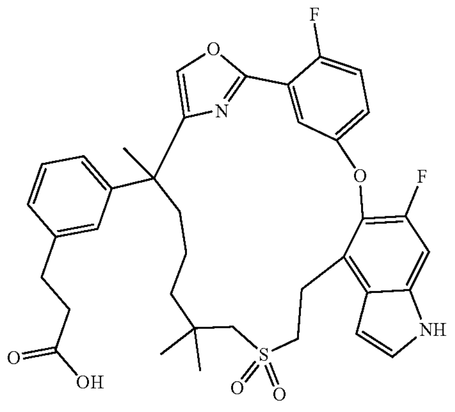 [SMILES: CC1(C)CCCC(C)(c2cccc(CCC(=O)O)c2)c2coc(n2)-c2cc(ccc2F)Oc2c(F)cc3[nH]ccc3c2CCS(=O)(=O)C1]

8-((2-Methoxy-2-oxoethyl)sulfonyl)-3-(3-(3-methoxy-3-oxopropyl)phenyl)-3,7,7-trimethyl-2-oxooctyl 2-fluoro-5-((6-fluoro-4-vinyl-1H-indol-5-yl)oxy)benzoate

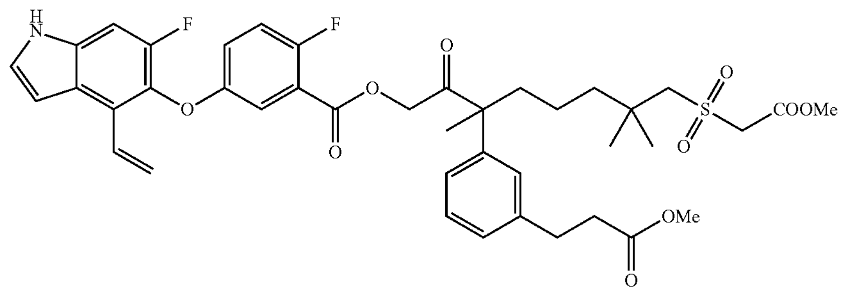 [SMILES: C=Cc1c(Oc2ccc(F)c(C(=O)OCC(=O)C(C)(CCCC(C)(C)CS(=O)(=O)CC(=O)OC)c3cccc(CCC(=O)OC)c3)c2)c(F)cc2[nH]ccc12]

Step A: To a stirred solution of methyl 3-(3-(1-bromo-8-((2-methoxy-2-oxoethyl)sulfonyl)-3,7,7-trimethyl-2-oxooctan-3-yl)phenyl)propanoate (Intermediate 8-3, 1.8 g, 3.29 mmol) in N,N-dimethylformamide (10 mL) was added 2-fluoro-5-((6-fluoro-4-vinyl-1H-indol-5-yl)oxy)benzoic acid (Intermediate 84-1, 1.04 g, 3.29 mmol) and sodium bicarbonate (690 mg, 8.22 mmol). The mixture was stirred at room temperature for 3 hours, then poured into water (50 mL). The mixture was extracted with ethyl acetate (2×60 mL). The combined organic extracts were dried over sodium sulfate and concentrated. The residue was purified by column chromatography on silica gel (dichloromethane/ethyl acetate=8/1) to give the title compound (1.8 g, 70.0%) as a yellow oil. MS (ESI): 782 m/z $[M+H]^+$, retention time: 2.26 minutes (LC-MS Method 011), purity (214 nm) >99%.

Methyl 3-(3-(2-(2-(2-fluoro-5-((6-fluoro-4-vinyl-1H-indol-5-yl)oxy)phenyl)oxazol-4-yl)-7-((2-methoxy-2-oxoethyl)sulfonyl)-6,6-dimethylheptan-2-yl)phenyl)propanoate

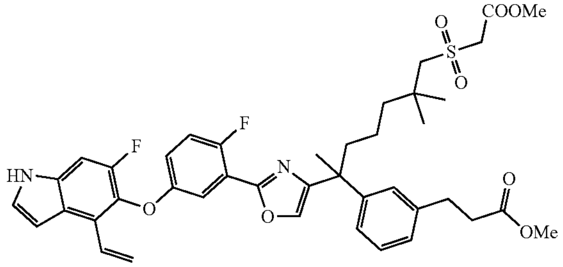 [SMILES: C=Cc1c(Oc2ccc(F)c(-c3nc(C(C)(CCCC(C)(C)CS(=O)(=O)CC(=O)OC)c4cccc(CCC(=O)OC)c4)co3)c2)c(F)cc2[nH]ccc12]

Step B: To a solution of Step A product (2 g, 2.56 mmol) in acetic acid (15 mL) was added ammonium acetate (3.94 g, 51.2 mmol). The mixture was heated at 115° C. for 12 hours, then the solvent was removed. The residue was suspended in water (40 mL), then extracted with ethyl acetate (2×50 mL). The combined organic extracts were dried over sodium sulfate and concentrated. The residue was purified by column chromatography on silica gel (25% ethyl acetate in petroleum ether) to give the title compound (0.58 g, 30%) as a yellow oil. MS (ESI): 763 m/z $[M+H]^+$, retention time: 2.35 minutes (LC-MS Method 011), purity (214 nm) 99%.

Compound 44: 3-[3-(22,28-Difluoro-6,10,10-trimethyl-12,12-dioxo-3,24-dioxa-12lambda6-thia-19,30-diazapentacyclo[23.3.1.12,5.015,23.016,20]triaconta-1(29),2(30),4,15,17,20,22,25,27-nonaen-6-yl)phenyl]propanoic Acid

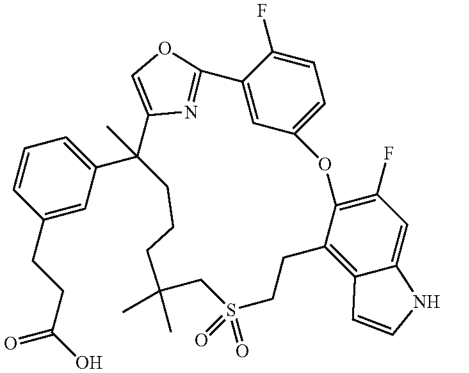 [SMILES: CC1(C)CCCC(C)(c2cccc(CCC(=O)O)c2)c2coc(n2)-c2cc(ccc2F)Oc2c(F)cc3[nH]ccc3c2CCS(=O)(=O)C1]

Step C: Exchanging ethyl 3-(3-(7-((2-ethoxy-2-oxoethyl)sulfonyl)-5,5-difluoro-2-(5-(2-fluoro-5-((6-fluoro-4-vinyl-1H-indol-5-yl)oxy)phenyl)-1-methyl-1H-1,2,4-triazol-3-yl)heptan-2-yl)phenyl)propanoate (Step A product of Example 2) with methyl 3-(3-(2-(2-(2-fluoro-5-((6-fluoro-4-vinyl-1H-indol-5-yl)oxy)phenyl)oxazol-4-yl)-7-((2-methoxy-2-oxoethyl)sulfonyl)-6,6-dimethylheptan-2-yl)phenyl)propanoate (Step B product in this example, 0.6 g, 0.787 mmol) in Step B, the reaction sequence (Steps B to Step G) described for Example 2 was used to prepare the title compound (14.2 mg) as a white solid. MS (ESI): 677 m/z $[M+H]^+$, retention time: 1.85 minutes, purity: 96% (254 nm) (LC-MS Method 011).

$^1H$ NMR (400 MHz, $CD_3OD$) δ 7.82 (s, 1H), 7.64 (s, 1H), 7.34 (d, J=3.1 Hz, 1H), 7.30-2.16 (m, 5H), 7.06 (t, J=7.5 Hz, 2H), 6.64 (d, J=3.1 Hz, 1H), 3.39 (d, J=5.2 Hz, 2H), 3.27-3.21 (m, 1H), 3.14-3.06 (m, 1H), 2.87 (t, J=7.6 Hz, 2H), 2.68 (d, J=6.2 Hz, 2H), 2.54 (t, J=7.7 Hz, 2H), 2.13-2.05 (m, 1H), 1.82-1.76 (m, 1H), 1.59 (s, 3H), 1.47-1.42 (m, 1H), 1.33-1.27 (m, 1H), 1.11-1.03 (m, 8H) ppm.

Example 45. Enantiomer 1 (Compound 45B) and 2 (Compound 45A) of 3-[3-(22,28-difluoro-6-methyl-12,12-dioxo-spiro [24-oxa-12lambda6-thia-3,19,30-triazapentacyclo[23.3.1.12, 5.015,23.016,20]triaconta-1(29),2,4,15,17,20,22,25,27-nonaene-10,1'-cyclopropane]-6-yl)phenyl]propanoic acid

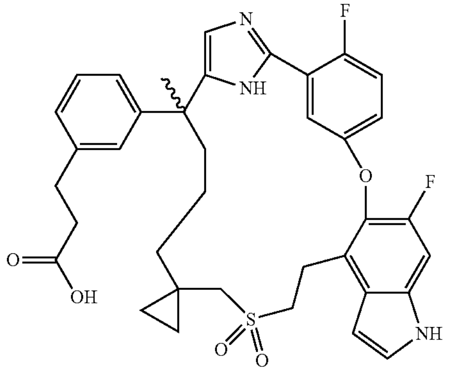 [SMILES: CC1(c2cccc(CCC(=O)O)c2)CCCC2(CC2)CS(=O)(=O)CCc2c(c(F)cc3[nH]ccc23)Oc2ccc(F)c(c2)-c2ncc1[nH]2]

3-[3-(22,28-Difluoro-6-methyl-12,12-dioxo-spiro [24-oxa-12lambda6-thia-3,19,30-triazapentacyclo [23.3.1.12, 5.015,23.016,20]triaconta-1(29),2,4,15, 17,20,22,25,27-nonaene-10,1'-cyclopropane]-6-yl) phenyl]propanoic Acid

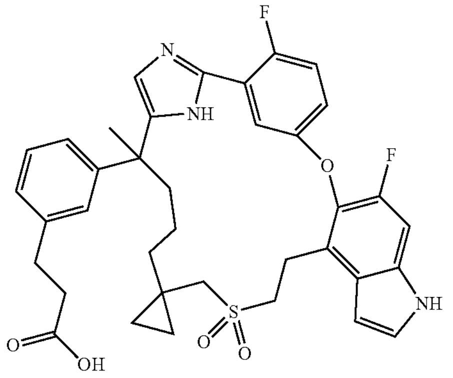 [SMILES: CC1(c2cccc(CCC(=O)O)c2)CCCC2(CC2)CS(=O)(=O)CCc2c(c(F)cc3[nH]ccc23)Oc2ccc(F)c(c2)-c2ncc1[nH]2]

Step A: Exchanging methyl 3-(3-(1-chloro-8-((2-methoxy-2-oxoethyl)sulfonyl)-3,7,7-trimethyl-2-oxooctan-3-yl)phenyl)propanoate (Intermediate 8-3) with methyl 3-(3-(1-bromo-6-(1-(((2-methoxy-2-oxoethyl)sulfonyl) methyl)cyclopropyl)-3-methyl-2-oxohexan-3-yl)phenyl) propanoate (Intermediate 17-8, 3.6 g, 6.6 mmol) in Step A, the reaction sequence (Steps A to Step F) described for Example 27 was used to prepare the title compound (0.27 g) as a white solid. MS (ESI): 674 m/z $[M+H]^+$, retention time: 1.66 minutes, purity: >99% (214 nm) (LC-MS Method 019). $^1H$ NMR (400 MHz, $CD_3OD$) δ 7.47-7.44 (m, 1H), 7.34-7.29 (m, 2H), 7.25-7.22 (m, 2H), 7.13-7.08 (m, 2H), 7.03 (s, 1H), 7.00-6.96 (m, 2H), 6.63 (d, 1H), 3.46-3.36 (m, 2H), 3.09-3.07 (m, 2H), 3.02 (d, 1H), 2.83 (t, 2H), 2.51 (t, 2H), 2.34-2.27 (m, 1H), 2.00-1.92 (m, 2H), 1.75-1.69m (m, 1H), 1.53 (s, 3H), 1.44-1.35 (m, 1H), 1.17-1.14 (m, 1H), 0.89-0.83 (m, 1H), 0.71-0.68 (m, 1H), 0.28-0.22 (m, 2H),−0.23-0.27 (m, 1H) ppm.

Enantiomer 1 and 2 of 3-[3-(22,28-Difluoro-6-methyl-12,12-dioxo-spiro[24-oxa-12lambda6-thia-3,19,30-triazapentacyclo[23.3.1.12, 5.015,23.016,20]triaconta-1(29),2,4,15,17,20,22,25,27-nonaene-10,1'-cyclopropane]-6-yl)phenyl]propanoic acid

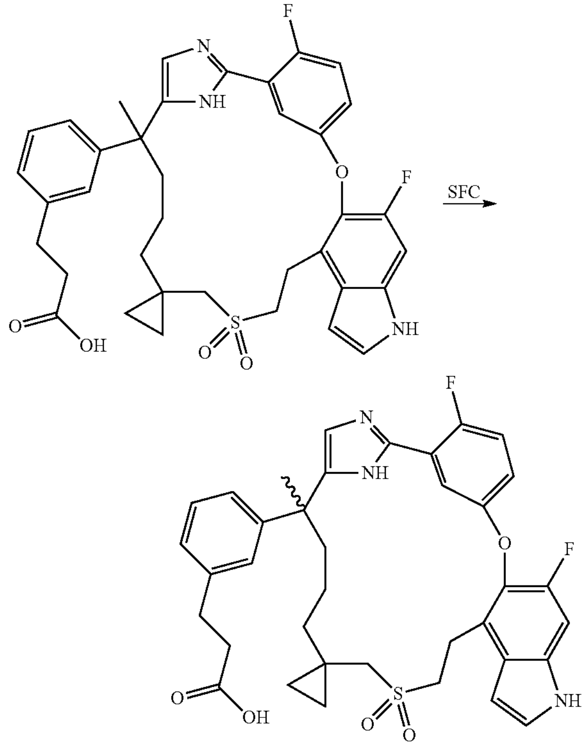

First Eluent, Enantiomer 1
Second Eluent, Enantiomer 2

Step B: The racemic, crude product of step A (0.33 g, 0.45 mmol) was subjected to chiral SFC using a Thar SFC-80 instrument and the following separation conditions: Column: 20×250 mm×10 μm IC; sample solution: 0.33 g dissolved in methanol (25 mL); injection volume: 1.0 mL; eluant: 55:45 $CO_2$/methanol with 0.2% ammonia/methanol additive; flow rate: 80 g/min; column temperature: 35° C.; back pressure: 100 bar; detection wavelength: 214 nM; Cycle time: 3.5 minutes. The first eluting isomer was designated Enantiomer 1, Compound 45B (98 mg, 33%) and the second eluting isomer, Enantiomer 2, Compound 45A (100 mg, 33%).

Compound 45B: $^1$H NMR (400 MHz, $CD_3OD$) δ 7.47-7.44 (m, 1H), 7.34-7.29 (m, 2H), 7.25-7.22 (m, 2H), 7.13-7.08 (m, 2H), 7.03 (s, 1H), 7.00-6.96 (m, 2H), 6.63 (d, 1H), 3.46-3.36 (m, 2H), 3.09-3.07 (m, 2H), 3.02 (d, 1H), 2.83 (t, 2H), 2.51 (t, 2H), 2.34-2.27 (m, 1H), 2.00-1.92 (m, 2H), 1.75-1.69 (m, 1H), 1.53 (s, 3H), 1.44-1.35 (m, 1H), 1.17-1.14 (m, 1H), 0.89-0.83 (m, 1H), 0.71-0.68 (m, 1H), 0.28-0.22 (m, 2H),−0.23-0.27 (m, 1H) ppm. MS (ESI): 674 m/z $[M+H]^+$, retention time: 1.66 minutes, purity: >99% (214 nm) (LC-MS Method 019). Chiral purity: >99% (chiral analytical method: Column: Cellulose-SC 4.6*100 mm 5um; Mobile Phase: methanol (0.2% Methanol Ammonia); Column Temperature: 40° C.; Flow: 4.0 mL/minutes; Wavelength: 214 nm & 359 nm; Instrument: SHIMADZU; Inject Volume: 8 uL.

Compound 45A: $^1$H NMR (400 MHz, $CD_3OD$) δ 7.47-7.43 (m, 1H), 7.34-7.29 (m, 2H), 7.25-7.22 (m, 2H), 7.13-7.08 (m, 2H), 7.03 (s, 1H), 7.00-6.96 (m, 2H), 6.63 (d, 1H), 3.46-3.36 (m, 2H), 3.09-3.07 (m, 2H), 3.02 (d, 1H), 2.83 (t, 2H), 2.51 (t, 2H), 2.34-2.27 (m, 1H), 2.00-1.92 (m, 2H), 1.75-1.69 (m, 1H), 1.53 (s, 3H), 1.44-1.35 (m, 1H), 1.17-1.14 (m, 1H), 0.89-0.83 (m, 1H), 0.71-0.68 (m, 1H), 0.28-0.22 (m, 2H),−0.23-0.27 (m, 1H) ppm. MS (ESI): 674 m/z $[M+H]^+$, retention time: 1.66 minutes, purity: >99% (214 nm) (LC-MS Method 019). Chiral purity: >99%.

Example 46. 3-[3-(22,28-Difluoro-6,11,11-trimethyl-10,24-dioxa-13-thia-3,19,30-triazapentacyclo[23.3.1.12,5.015,23.016,20]triaconta-1(29),2(30),4,15,17,20,22,25,27-nonaen-6-yl)phenyl]propanoic acid

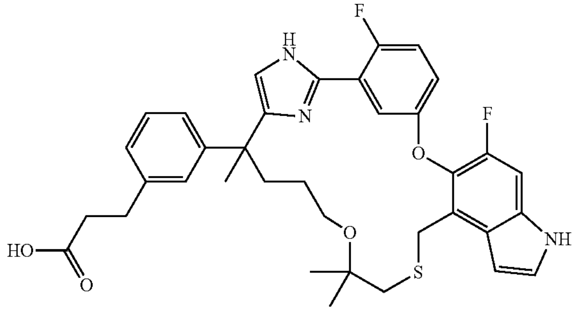 [SMILES: CC1(C)CSCc2c(c(F)cc3[nH]ccc23)Oc2ccc(F)c(c2)-c2nc(c[nH]2)C(C)(c2cccc(CCC(=O)O)c2)CCCO1]

S-((5-(3-Cyano-4-fluorophenoxy)-6-fluoro-1-(phenylsulfonyl)-1H-indol-4-yl)methyl) ethanethioate

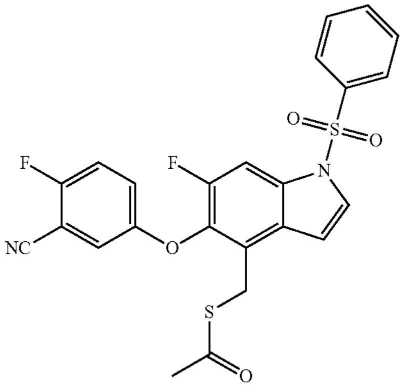 [SMILES: CC(=O)SCc1c(Oc2ccc(F)c(C#N)c2)c(F)cc2c1ccn2S(=O)(=O)c1ccccc1]

Step A: To a stirred solution of 5-((4-(bromomethyl)-6-fluoro-1-(phenylsulfonyl)-1H-indol-5-yl)oxy)-2-fluorobenzonitrile (Intermediate 13, 5 g, 9.93 mmol) in N,N-dimethylformamide (80 mL) was added potassium thioacetate (5.67 g, 49.7 mmol). The mixture was stirred at room temperature for 1 hour, then quenched with water and extracted with ethyl acetate (3×20 mL). The combined organic extracts were washed with water, brine, dried over sodium sulfate and concentrated. The residue was purified by automated silica gel column chromatography (80 g silica gel column, 0-40% ethyl acetate in petroleum ether) to give the title compound (3.55 g, 70%) as a solid. MS (ESI): 521 m/z $[M+Na]^+$, retention time: 2.3 minutes, purity: 94% (214 nm) (LC-MS Method 011).

2-Fluoro-5-((6-fluoro-4-(((2-methylallyl)thio)methyl)-1-(phenylsulfonyl)-1H-indol-5-yl)oxy)benzonitrile

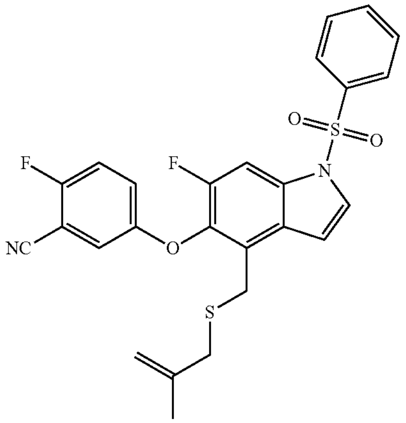 [SMILES: C=C(C)CSCc1c(Oc2ccc(F)c(C#N)c2)c(F)cc2c1ccn2S(=O)(=O)c1ccccc1]

Step B: To a stirred solution of Step A product (0.67 g, 1.34 mmol) and 3-chloro-2-methyl-prop-1-ene (0.158 g, 1.75 mmol) in methanol (50 mL) and tetrahydrofuran (50 mL) was added sodium methoxide (5.4 M in methanol, 0.381 mL, 2.02 mmol). The mixture was stirred at room temperature for 0.5 hour, then quenched with water (100 mL) and extracted with ethyl acetate (3×30 mL). The combined organic extracts were washed with brine, dried over sodium sulfate, and concentrated. The residue was purified by automated flash chromatography (80 g silica gel column, eluted with 0-80% ethyl acetate in petroleum ether) to give the title compound (2.2 g, 61%) as oil. MS (ESI): 533 m/z $[M+Na]^+$, retention time: 2.9 minutes, purity: >99% (254 nm) (LC-MS Method 020).

2-Fluoro-5-((6-fluoro-4-(((2-methylallyl)thio)methyl)-1H-indol-5-yl)oxy)benzonitrile

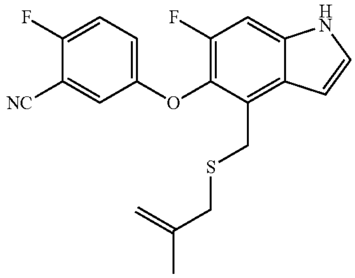 [SMILES: C=C(C)CSCc1c(Oc2ccc(F)c(C#N)c2)c(F)cc2[nH]ccc12]

Step C: A stirred solution of Step B product (2.2 g, 4.31 mmol) in tetrabutylammonium fluoride (1 M in tetrahydrofuran) (43 mL) was stirred at room temperature for 3 hours, then quenched with water, and extracted with ethyl acetate (3×50 mL). The combined organic extracts were washed with brine, dried over sodium sulfate, and concentrated. The residue was purified by automated flash chromatography (40 g silica gel column, eluted with 0-40% ethyl acetate in petroleum ether) to give the title compound (1.25 g, 78%) as an oil. MS (ESI): 393 m/z $[M+Na]^+$, retention time: 2.2 minutes, purity: 84% (214 nm) (LC-MS Method 021).

2-Fluoro-5-((6-fluoro-4-(((2-methylallyl)thio)methyl)-1H-indol-5-yl)oxy)benzimidamide

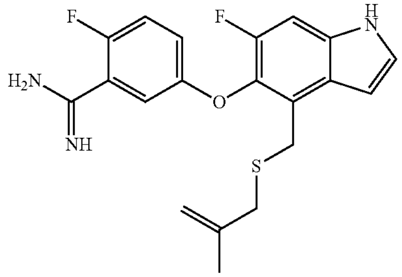 [SMILES: C=C(C)CSCc1c(Oc2ccc(F)c(C(=N)N)c2)c(F)cc2[nH]ccc12]

Step D: To a stirred and cooled (0° C.) solution of Step C product (1.25 g, 3.37 mmol) in tetrahydrofuran (31 mL) was added to lithium bis(trimethylsilyl)amide (1 M in tetrahydrofuran, 31 mL). The mixture was stirred at room temperature for 1 hour, then quenched with water (30 mL), and extracted with dichloromethane (5×20 mL). The combined organic extracts were washed with brine (60 mL), dried over sodium sulfate, and concentrated. The residue was purified by automated flash chromatography (20 g silica gel column, eluted with 0-10% methanol (with 10%7M ammonia in methanol)/dichloromethane to give the title compound (0.85 g, 65%) as a solid. MS (ESI): 388 m/z $[M+H]^+$, retention time: 1.52 minutes, purity: 98% (214 nm) (LC-MS Method 021).

Ethyl 3-(3-(5-acetoxy-2-(2-(2-fluoro-5-((6-fluoro-4-(((2-methylallyl)thio)methyl)-1H-indol-5-yl)oxy)phenyl)-1H-imidazol-5-yl)pentan-2-yl)phenyl)propanoate

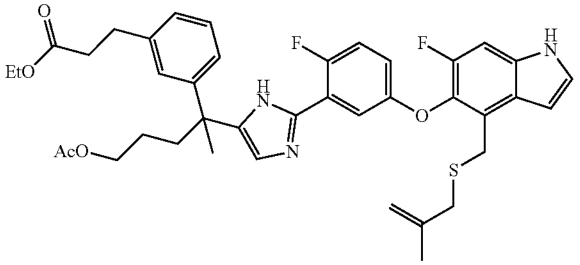 [SMILES: C=C(C)CSCc1c(Oc2ccc(F)c(-c3ncc(C(C)(CCCOC(C)=O)c4cccc(CCC(=O)OCC)c4)[nH]3)c2)c(F)cc2[nH]ccc12]

Step E: To a stirred solution of Step D product (0.63 g, 1.47 mmol) and ethyl 3-(3-(6-acetoxy-1-bromo-3-methyl-2-oxohexan-3-yl)phenyl)propanoate (Intermediate 17-10, 0.6 g, 1.55 mmol) in N,N-dimethylformamide (20 mL) was added sodium bicarbonate (0.33 g, 3.96 mmol). The mixture was stirred at 75° C. overnight, then quenched with water (100 mL), and extracted with ethyl acetate (3×50 mL). The combined organic extracts were washed with brine, dried over sodium sulfate, and concentrated. The residue was purified by automated flash chromatography (40 g silica gel column, eluted with 0-60% ethyl acetate in petroleum ether) to give the title compound (0.6 g, 54%) as a solid. MS (ESI): 716 m/z $[M+H]^+$, retention time: 1.89 minutes, purity: 80% (214 nm) (LC-MS Method 011).

Ethyl 3-(3-(2-(2-(2-fluoro-5-((6-fluoro-4-(((2-methylallyl)thio)methyl)-1H-indol-5-yl)oxy)phenyl)-1H-imidazol-5-yl)-5-hydroxypentan-2-yl)phenyl)propanoate

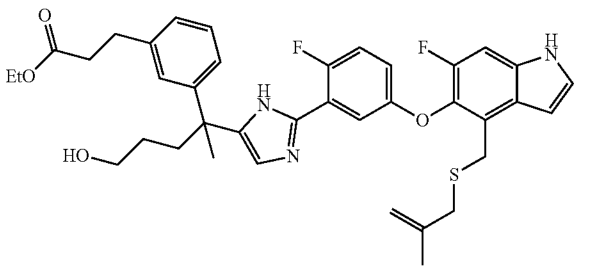 [SMILES: C=C(C)CSCc1c(Oc2ccc(F)c(-c3ncc(C(C)(CCCO)c4cccc(CCC(=O)OCC)c4)[nH]3)c2)c(F)cc2[nH]ccc12]

Step F: To a stirred solution of Step E product (0.6 g, 0.84 mmol) in methanol (20 mL) was added potassium carbonate (0.23 g, 1.68 mmol). The reaction was stirred at room temperature for 2 hours, then diluted with ethyl acetate. The mixture was washed with water (3×40 mL), brine (40 mL), dried over sodium sulfate, and concentrated. The residue was purified by automated flash chromatography (20 g silica gel column, eluted with 0-10% methanol in dichloromethane) to give the title compound (480 mg, 87%) as a solid. MS (ESI): 674 m/z $[M+H]^+$, retention time: 1.80 minutes, purity: >99% (214 nm) (LC-MS Method 011).

Ethyl 3-[3-(22,28-Difluoro-6,11,11-trimethyl-10,24-dioxa-13-thia-3,19,30-triazapentacyclo[23.3.1.12,5.015,23.016,20]triaconta-1(29),2(30),4,15,17,20,22,25,27-nonaen-6-yl)phenyl]propanoate

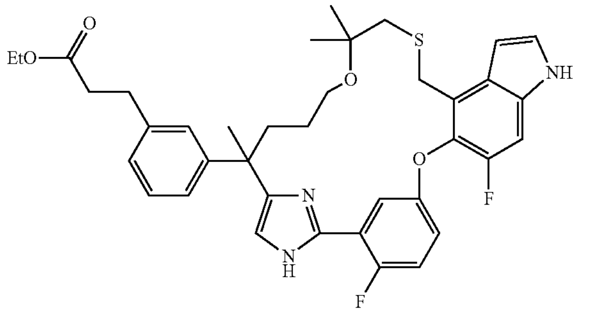 [SMILES: CCOC(=O)CCc1cccc(C2(C)CCCOC(C)(C)CSCc3c(c(F)cc4[nH]ccc34)Oc3ccc(F)c(c3)-c3nc2c[nH]3)c1]

Step G: To a stirred solution of Step F product (480 mg, 0.72 mmol) in dry dichloromethane (48 mL) was added magnesium sulfate (613 mg, 5.19 mmol) and p-toluenesulfonic acid (346 mg, 1.82 mmol). The reaction was stirred at room temperature overnight, then filtered. The filtrate was diluted with ethyl acetate (90 mL), washed with saturated sodium bicarbonate (3×20 mL), brine, dried over sodium sulfate, and concentrated. The residue was purified by flash chromatography (12 g silica gel column, eluted with 0-100% ethyl acetate in petroleum ether) to give the title compound (23 mg, 5%) as a solid. MS (ESI): 674 m/z $[M+H]^+$.

Compound 46: 3-[3-(22,28-difluoro-6,11,11-trimethyl-10,24-dioxa-13-thia-3,19,30-triazapentacyclo [23.3.1.12,5.015,23.016,20]triaconta-1(29),2(30),4,15,17,20,22,25,27-nonaen-6-yl)phenyl]propanoic Acid

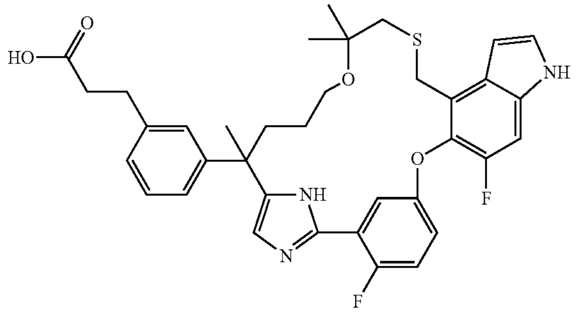 [SMILES: CC1(C)CSCc2c(c(F)cc3[nH]ccc23)Oc2ccc(F)c(c2)-c2ncc([nH]2)C(C)(c2cccc(CCC(=O)O)c2)CCCO1]

Step H: To a stirred solution of Step G product (23 mg, 0.034 mmol) in tetrahydrofuran/water/methanol (3 mL/1 mL/1 mL) was added lithium hydroxide monohydrate (14.6 mg, 0.34 mmol). The reaction was stirred at room temperature for 2 hours, then acidified with 1 M hydrochloric acid to pH ~4. The mixture was diluted with ethyl acetate (30 mL), washed with brine (10 mL), dried over sodium sulfate, and concentrated. The residue was purified by Prep-HPLC to give the title compound (9 mg, 40%). MS (ESI): 646 m/z $[M+H]^+$, retention time: 1.82 minutes, purity: 98% (214 nm) (LC-MS Method 017). $^1H$ NMR (400 MHz, $CD_3OD$) δ 7.53-7.51 (m, 1H), 7.27-7.22 (m, 3H), 7.13-7.08 (m, 3H), 6.99-6.97 (m, 3H), 6.67 (d, J=2.8 Hz, 1H), 4.30-4.20 (m, 1H), 4.00-4.10 (m, 1H), 3.23 (d, J=4.8 Hz, 1H), 3.12-3.04 (m, 1H), 2.96 (d, J=11.5 Hz, 1H), 2.85-2.70 (m, 3H), 2.47 (t, J=7.8 Hz, 2H), 2.20-1.88 (m, 2H), 1.52 (s, 4H), 1.21 (s, 3H), 1.16 (s, 3H), 1.07 (s, 1H) ppm.

Example 47. 3-[3-(22,28-Difluoro-6,11,11-trimethyl-13-oxo-10,24-dioxa-13M-thia-3,19,30-triazapentacyclo[23.3.1.12,5.015,23.016,20]triaconta-1(29),2,4,15,17,20,22,25,27-nonaen-6-yl)phenyl] propanoic Acid

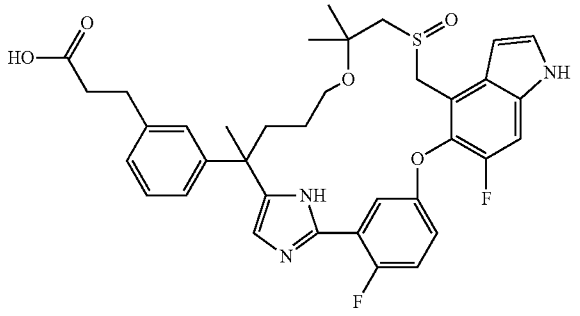 [SMILES: CC1(C)CS(=O)Cc2c(c(F)cc3[nH]ccc23)Oc2ccc(F)c(c2)-c2ncc([nH]2)C(C)(c2cccc(CCC(=O)O)c2)CCCO1]

To a stirred and cooled (0° C.) solution of 3-[3-(22,28-difluoro-6,11,11-trimethyl-10,24-dioxa-13-thia-3,19,30-triazapentacyclo [23.3.1.12,5.015,23.016,20]triaconta-1(29),2(30),4,15,17,20,22,25,27-nonaen-6-yl)phenyl]propanoic acid (Example 46) (5.6 mg) in methanol (1 mL) was added 0.1 mL of a stock solution of ammonium molybdate tetrahydrate (0.2 g) in hydrogen peroxide (30% in water, 1 mL).

The reaction mixture was stirred at 0° C. for 15 minutes, then diluted with ethyl acetate (20 mL). The solution was washed with water (3×10 mL) and brine, dried over sodium sulfate and concentrated. The residue was purified by Prep-HPLC to give the title compound (2 mg, 35%) as a solid. MS (ESI): 662 m/z $[M+H]^+$, retention time: 1.76 minutes, purity: >99% (214 nm) (LC-MS Method 017). $^1H$ NMR (400 MHz, $CD_3OD$) δ 7.59-7.57 (m, 1H), 7.41-7.36 (m, 1H), 7.29-7.21 (m, 3H), 7.19-6.87 (m, 5H), 6.70 (t, J=2.7 Hz, 1H), 4.61-4.47 (m, 2H), 2.95-2.91 (m, 2H), 2.85-2.81 (m, 3H), 2.76-2.72 (m, 3H), 2.21-1.73 (m, 2H), 1.52-1.45 (m, 4H), 1.33-1.20 (m, 6H), 1.14-0.98 (m, 1H) ppm.

Example 48. 3-[3-(22,28-Difluoro-6,11,11-trimethyl-13,13-dioxo-10,24-dioxa-13λ6-thia-3,19,30-triazapentacyclo[23.3.1.12,5.015,23.016,20]triaconta-1(29),2,4,15,17,20,22,25,27-nonaen-6-yl)phenyl]propanoic Acid

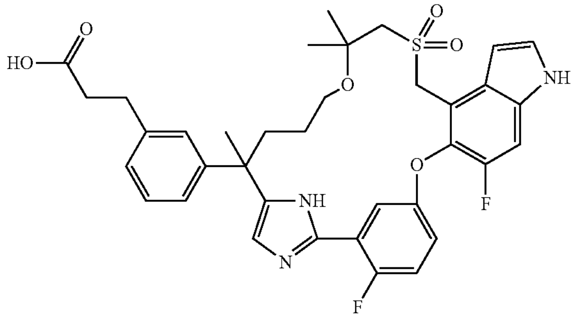

Methyl 3-[3-(22,28-Difluoro-6,11,11-trimethyl-13,13-dioxo-10,24-dioxa-13 6-thia-3,19,30-triazapentacyclo[23.3.1.12,5.015,23.016,20]triaconta-1(29),2,4,15,17,20,22,25,27-nonaen-6-yl)phenyl]propanoate

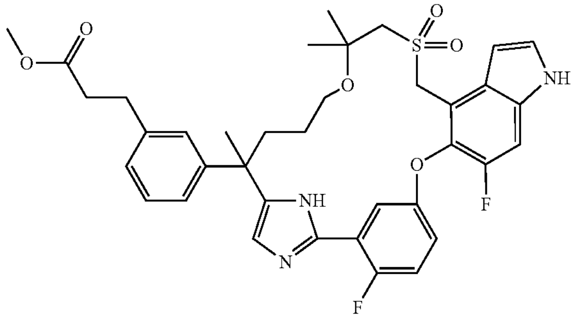 [SMILES: COC(=O)CCc1cccc(C2(C)CCCOC(C)(C)CS(=O)(=O)Cc3c(c(F)cc4[nH]ccc34)Oc3ccc(F)c(c3)-c3ncc2[nH]3)c1]

Step A: To a stirred and cooled (0° C.) solution of ethyl 3-[3-(22,28-difluoro-6,11,11-trimethyl-10,24-dioxa-13-thia-3,19,30-triazapentacyclo [23.3.1.12,5.015,23.016,20] triaconta-1(29),2(30),4,15,17,20,22,25,27-nonaen-6-yl)phenyl]propanoate (Step G product of Example 46) (22 mg) in methanol (2.2 mL) was added 0.22 mL of a stock solution of ammonium molybdate tetrahydrate (0.2 g) in hydrogen peroxide (30% in water, 1 mL). The reaction mixture was stirred at room temperature for 4 hours, then diluted with ethyl acetate (20 mL). The solution was washed with water (3×10 mL), brine, dried over sodium sulfate, and concentrated. The residue was purified by automated silica gel flash column chromatography (12 g silica gel column, eluted with 0-100% ethyl acetate in petroleum ether) to give the title compound (23 mg, 99%) as a solid. MS (ESI): 692 m/z $[M+H]^+$.

Compound 48: 3-[3-(22,28-difluoro-6,11,11-trimethyl-13,13-dioxo-10,24-dioxa-13 6-thia-3,19,30-triazapentacyclo[23.3.1.12,5.015,23.016,20]triaconta-1(29),2,4,15,17,20,22,25,27-nonaen-6-yl)phenyl]propanoic Acid

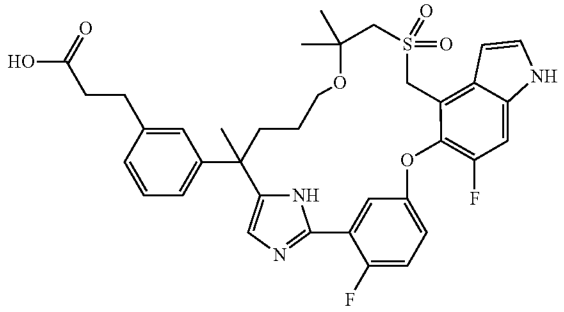 [SMILES: CC1(C)CS(=O)(=O)Cc2c(c(F)cc3[nH]ccc23)Oc2ccc(F)c(c2)-c2ncc([nH]2)C(C)(c2cccc(CCC(=O)O)c2)CCCO1]

Step B: To a stirred solution of Step A product (23 mg, 0.033 mmol) in tetrahydrofuran/water/methanol (3 mL/1 mL/1 mL) was added lithium hydroxide monohydrate (14 mg, 0.33 mmol). The reaction was stirred at room temperature for 2 hours, then acidified with 1 M hydrochloric acid to pH ~4 and diluted with ethyl acetate (30 mL). The mixture was washed with brine, dried over sodium sulfate, filtered, and concentrated. The residue was purified by Prep-HPLC to give the title compound (1.4 mg, yield: 16%) as a solid. MS (ESI): 678 m/z $[M+H]^+$, retention time: 1.66 minutes, purity: >99% (214 nm) (LC-MS Method 017). $^1H$ NMR (400 MHz, $CD_3OD$) δ 7.57-7.52 (m, 1H), 7.26 (d, J=3.2 Hz, 1H), 7.18 (d, J=11.2 Hz, 1H), 7.13-7.09 (m, 2H), 6.98-6.85 (m, 5H), 6.63 (d, J=3.6 Hz, 1H), 4.74-4.49 (m, 2H), 3.26-2.95 (m, 4H), 2.65 (t, J=7.6 Hz, 2H), 2.30 (t, J=7.6 Hz, 2H), 2.17-1.71 (m, 2H), 1.43 (s, 3H), 1.43-1.37 (m, 1H), 1.22 (d, J=6.4 Hz, 6H), 1.10-0.99 (m, 1H) ppm.

Example 49. 3-[3-(22,28-Difluoro-6,10,10-trimethyl-12,12-dioxo-24-oxa-3,12lambda6-dithia-19,30-diazapentacyclo[23.3.1.12,5.015,23.016,20]triaconta-1(29),2(30),4,15,17,20,22,25,27-nonaen-6-yl)phenyl]propanoic Acid

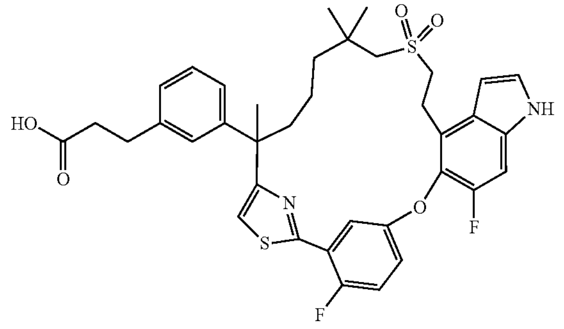 [SMILES: CC1(C)CCCC(C)(c2cccc(CCC(=O)O)c2)c2csc(n2)-c2cc(ccc2F)Oc2c(F)cc3[nH]ccc3c2CCS(=O)(=O)C1]

Methyl 3-(3-(2-(2-(2-fluoro-5-((6-fluoro-4-vinyl-1H-indol-5-yl)oxy)phenyl)thiazol-4-yl)-7-((2-methoxy-2-oxoethyl)sulfonyl)-6,6-dimethylheptan-2-yl)phenyl)propanoate

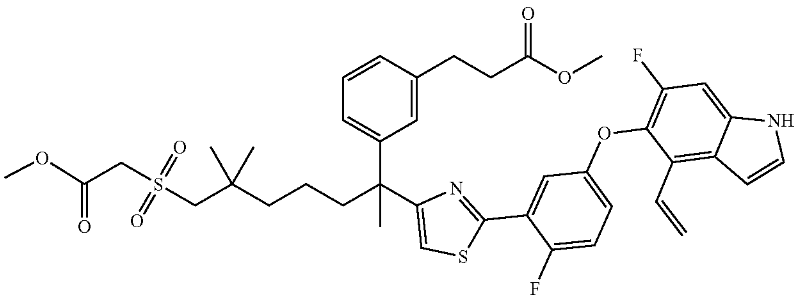 [SMILES: C=Cc1c(Oc2ccc(F)c(-c3nc(C(C)(CCCC(C)(C)CS(=O)(=O)CC(=O)OC)c4cccc(CCC(=O)OC)c4)cs3)c2)c(F)cc2[nH]ccc12]

Step A: To a stirred solution of methyl 3-[3-[1-(2-bromo-acetyl)-6-(2-methoxy-2-oxo-ethyl)sulfonyl-1,5,5-trimethyl-hexyl]phenyl]propanoate (Intermediate 8-3, 3.4 g, 6.21 mmol) in N,N-dimethylformamide (30 mL) was added 2-fluoro-5-((6-fluoro-4-vinyl-1H-indol-5-yl)oxy)benzothioamide (Intermediate 12, 2.05 g, 6.21 mmol). The reaction was heated at 80° C. for 12 hours, then cooled to room temperature, poured into water (50 mL), and extracted with ethyl acetate (2×80 mL). The combined organic extracts were dried over anhydrous sodium sulfate, filtered, and concentrated. The residue was purified by automated silica gel column chromatography (80 g silica gel column, eluted with 0-25% ethyl acetate in petroleum ether) to give the title compound (4.25 g, 88%) as a yellow oil. MS (ESI): 779 m/z $[M+H]^+$, retention time: 2.44 minutes, purity: 88% (214 nm) (LC-MS Method 021).

Compound 49: 3-[3-(22,28-Difluoro-6,10,10-trimethyl-12,12-dioxo-24-oxa-3,12lambda6-dithia-19,30-diazapentacyclo[23.3.1.12,5.015,23.016,20]triaconta-1(29),2(30),4,15,17,20,22,25,27-nonaen-6-yl)phenyl]propanoic acid

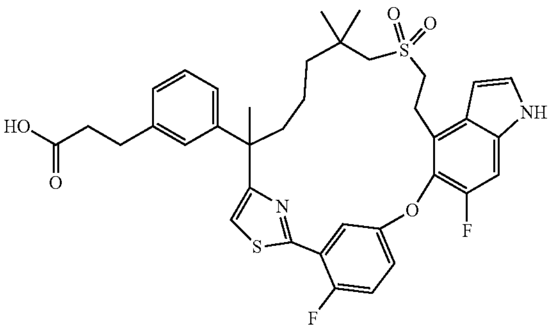 [SMILES: CC1(C)CCCC(C)(c2cccc(CCC(=O)O)c2)c2csc(n2)-c2cc(ccc2F)Oc2c(F)cc3[nH]ccc3c2CCS(=O)(=O)C1]

Step B: Exchanging methyl 3-(3-(2-(2-(2-fluoro-5-((6-fluoro-4-vinyl-1H-indol-5-yl)oxy)phenyl)-1H-imidazol-5-yl)-7-((2-methoxy-2-oxoethyl)sulfonyl)-6,6-dimethylheptan-2-yl)phenyl)propanoate (Step A product of Example 27) with methyl 3-(3-(2-(2-(2-fluoro-5-((6-fluoro-4-vinyl-1H-indol-5-yl)oxy)phenyl)thiazol-4-yl)-7-((2-methoxy-2-oxoethyl)sulfonyl)-6,6-dimethylheptan-2-yl)phenyl)propanoate (Step A product of this example, 3.5 g, 4.49 mmol), the reaction sequence (Steps B to Step F) described for Example 27 was used to prepare the title compound (11 mg) as a white solid. MS (ESI): 693 m/z $[M+H]^+$, retention time: 2.25 minutes, purity: >99% (214 nm) (LC-MS Method 017). $^1H$ NMR (400 MHz, $CD_3OD$) δ 7.79-7.77 (m, 1H), 7.38-7.28 (m, 4H), 7.17-6.94 (m, 5H), 6.66 (s, 1H), 3.43-3.38 (t, J=7.2 Hz, 2H), 3.20-3.08 (m, 2H), 2.88-2.84 (t, J=7.2 Hz, 2H), 2.68-2.60 (m, 2H), 2.55-2.51 (t, J=8.4 Hz, 2H), 2.18-2.17 (m, 1H), 1.70-1.66 (m, 4H), 1.25-1.18 (m, 2H), 1.10 (s, 3H), 1.00-0.94 (m, 5H).

Example 50. 3-[3-(22-Fluoro-6,10,10-trimethyl-12,12-dioxo-24-oxa-3,12λ6-dithia-19,30-diazapentacyclo[23.3.1.12,5.015,23.016,20]triaconta-1(29),2(30),4,15,17,20,22,25,27-nonaen-6-yl)phenyl]propanoic Acid

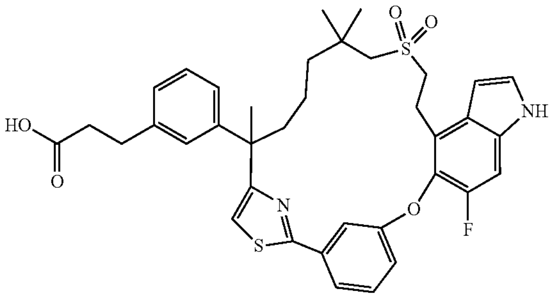 [SMILES: CC1(C)CCCC(C)(c2cccc(CCC(=O)O)c2)c2csc(n2)-c2cccc(c2)Oc2c(F)cc3[nH]ccc3c2CCS(=O)(=O)C1]

Exchanging 2-fluoro-5-((6-fluoro-4-vinyl-1H-indol-5-yl)oxy)benzothioamide (Intermediate 12) with 3-((6-fluoro-4-vinyl-1H-indol-5-yl)oxy)benzothioamide (Intermediate 12-2, 1.70 g, 5.44 mmol) in Step A, the reaction sequence (Step A to Step B) described for Example 49 was followed to prepare the title compound (41 mg) as a light-yellow solid. MS (ESI): 675 m/z $[M+H]^+$, retention time: 2.25 minutes, purity: 99% (214 nm) (LC-MS Method 017). $^1H$ NMR (400 MHz, $CD_3OD$) δ 7.53 (s, 1H), 7.42 (d, J=7.8 Hz, 1H), 7.34 (t, J=7.9 Hz, 1H), 7.23 (d, J=3.2 Hz, 1H), 7.17 (m, 1H), 7.09 (s, 1H), 7.02 (m, 3H), 6.89 (m, 2H), 6.53 (d, J=3.2 Hz, 1H), 3.29 (t, J=7.3 Hz, 2H), 3.04-2.90 (m, 2H), 2.74 (t, J=7.7 Hz, 2H), 2.49-2.37 (m, 4H), 2.09-2.00 (m, 1H), 1.67-1.61 (m, 1H), 1.55 (s, 3H), 1.19 (m, 4H), 0.94 (s, 3H), 0.85 (m, 3H).

Example 51. 3-[3-(22-Fluoro-6,10,10-trimethyl-12,12-dioxo-3,24-dioxa-12λ6-thia-19,30-diazapentacyclo[23.3.1.12,5.015,23.016,20]triaconta-1(29),2(30),4,15,17,20,22,25,27-nonaen-6-yl)phenyl]propanoic Acid

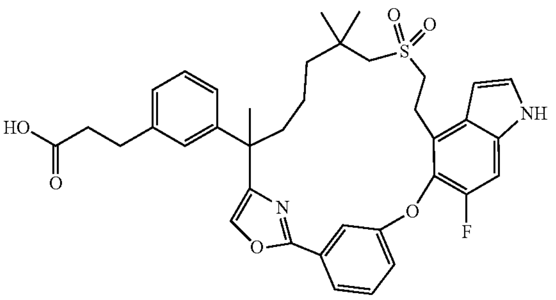 [SMILES: CC1(C)CCCC(C)(c2cccc(CCC(=O)O)c2)c2coc(n2)-c2cccc(c2)Oc2c(F)cc3[nH]ccc3c2CCS(=O)(=O)C1]

Exchanging 2-fluoro-5-((6-fluoro-4-vinyl-1H-indol-5-yl)oxy)benzoic acid (Intermediate 84-1) with 3-((6-fluoro-4-vinyl-1H-indol-5-yl)oxy)benzoic acid (Intermediate 84, 4 g, 13.5 mmol), the reaction sequence (Step A to Step C) described for Example 44 was followed to prepare the title compound (32 mg) as a white solid. MS (ESI): 659 m/z $[M+H]^+$, retention time: 2.23 minutes, purity: >99% (214 nm) (LC-MS Method 017). $^1H$ NMR (400 MHz, $CD_3OD$) δ 7.76 (s, 1H), 7.69-7.65 (m, 2H), 7.51 (d, J=8.0 Hz, 1H), 7.33 (d, J=3.2 Hz, 1H), 7.28-7.17 (m, 4H), 7.09-7.04 (m, 2H), 6.63 (d, J=3.2 Hz, 1H), 3.42-3.33 (m, 2H), 3.17-3.13 (m, 1H), 3.03-2.99 (m, 1H), 2.87 (t, J=7.6 Hz, 2H), 2.64 (s, 2H), 2.56-2.55 (m, 2H), 2.07-2.04 (m, 1H), 1.81-1.80 (m, 1H), 1.57 (s, 3H), 1.44-1.25 (m, 2H), 1.21-1.01 (m, 8H) ppm.

Example 52. 3-[3-(22-Fluoro-10,10-dimethyl-12,12-dioxo-24-oxa-12lambda6-thia-5,19,30-triazapentacyclo[23.3.1.12,5.015,23.016,20]triaconta-1(29),2(30),3,15,17,20,22,25,27-nonaen-6-yl)phenyl]butanoic Acid

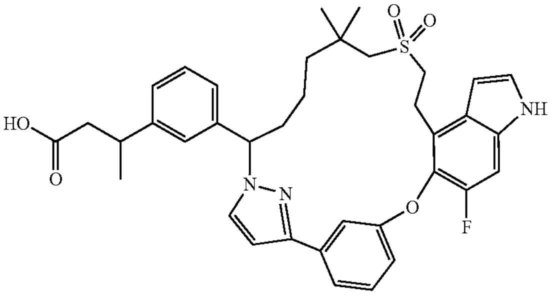 [SMILES: CC(CC(=O)O)c1cccc(C2CCCC(C)(C)CS(=O)(=O)CCc3c(c(F)cc4[nH]ccc34)Oc3cccc(c3)-c3ccn2n3)c1]

Example 53. 3-[3-(23-Fluoro-11,11-dimethyl-13,13-dioxo-25-oxa-13lambda6-thia-5,6,20-triazapentacyclo[24.3.1.02,6.016,24.017,21]triaconta-1(30),2,4,16,18,21,23,26,28-nonaen-7-yl)phenyl]butanoic acid

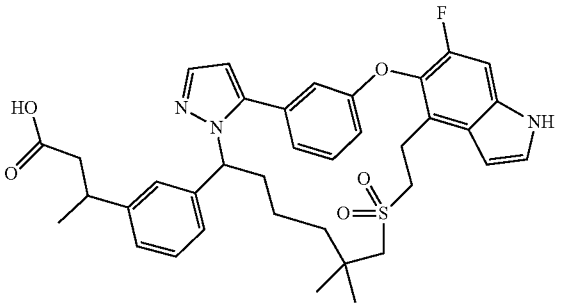 [SMILES: CC(CC(=O)O)c1cccc(C2CCCC(C)(C)CS(=O)(=O)CCc3c(c(F)cc4[nH]ccc34)Oc3cccc(c3)-c3ccnn32)c1]

Exchanging ethyl 3-(3-(1-bromo-6-((2-ethoxy-2-oxoethyl)thio)-5,5-dimethylhexyl)phenyl)-propanoate (Intermediate 54-1) with methyl 3-(3-(1-bromo-6-((2-methoxy-2-oxoethyl)thio)-5,5-dimethylhexyl)phenyl)butanoate (Intermediate 54-4, 3.0 g, 6.34 mmol) in Step A, the reaction procedure sequence described for Example 24 (Steps A-H) was used to prepare the title compounds (130 mg) as a white solid. This mixture, which was not separable by flash chromatography, and was further purified by prep-HPLC to give the first eluent, Compound 52 (38 mg, 31%) and the second eluent, Compound 53 (5.4 mg, 4%), both as white solids.

Compound 52: MS (ESI): 658 m/z $[M+H]^+$, retention time: 2.25 minutes, purity: >99% (254 nm) (LC-MS Method 012). $^1H$ NMR (400 MHz, $CD_3OD$) δ 7.59 (s, 1H), 7.50 (d, J=2.2 Hz, 1H), 7.41-7.39 (m, 2H), 7.34 (d, J=3.2 Hz, 1H), 7.31 (d, J=10.6 Hz, 1H), 7.28-7.23 (m, 2H), 7.18 (d, J=7.6 Hz, 1H), 7.13 (d, J=7.6 Hz, 1H), 7.04-7.01 (m, 1H), 6.68-6.66 (m, 2H), 5.35 (dd, $J_1$=2.8 Hz, $J_2$=12.4 Hz, 1H), 3.48-3.43 (m, 2H), 3.24-3.19 (m, 1H), 3.07-2.99 (m, 2H), 2.56-2.51 (m, 4H), 2.35-2.25 (m, 1H), 1.93-1.86 (m, 1H), 1.45-1.38 (m, 1H), 1.26 (dd, J=6.8, 2.4 Hz, 3H), 1.19-1.05 (m, 2H), 1.09 (s, 3H), 1.06-0.93 (m, 1H), 0.97 (s, 3H) ppm.

Compound 53: MS (ESI): 658 m/z $[M+H]^+$, retention time: 2.11 minutes, purity: 96% (254 nm) (LC-MS Method 012). $^1H$ NMR (400 MHz, $CD_3OD$) δ 7.66 (s, 1H), 7.44-7.40 (m, 1H), 7.37 (d, J=3.2 Hz, 1H), 7.30-7.21 (m, 6H), 7.01 (d, J=6.8 Hz, 1H), 6.77 (d, J=7.6 Hz, 1H), 6.61 (d, J=3.2 Hz, 1H), 6.45 (s, 1H), 5.36 (dd, $J_1$=3.6 Hz, $J_2$=11.2 Hz, 1H), 3.40-3.20 (m, 4H), 3.13-3.07 (m, 1H), 2.92 (q, J=14 Hz, 2H), 2.53-2.41 (m, 3H), 2.00-1.91 (m, 1H), 1.52-1.43 (m, 1H), 1.29 (d, J=5.6 Hz, 3H), 1.22-1.20 (m, 1H), 1.16 (s, 3H), 0.96 (s, 3H), 0.93-0.86 (m, 2H) ppm.

Example 54. Enantiomers 1 (Compound 54B) and 2 (Compound 54A) of 2-[3-(22,28-difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenoxy]acetic acid

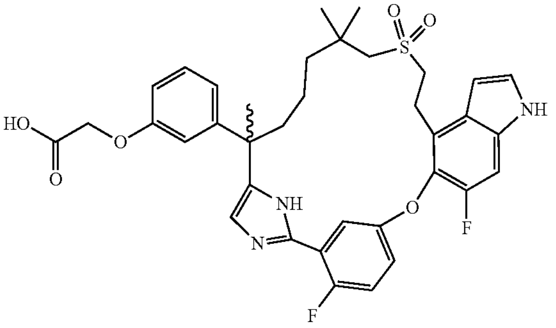

2-[3-(22,28-difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenoxy]acetic Acid

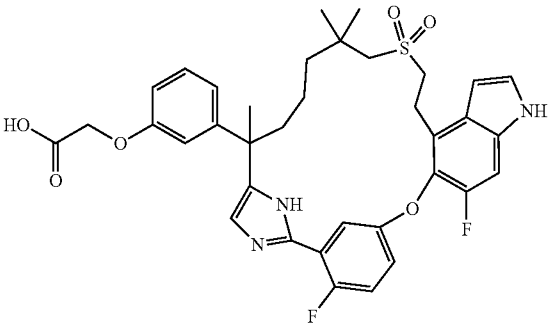 [SMILES: CC1(C)CCCC(C)(c2cccc(OCC(=O)O)c2)c2cnc([nH]2)-c2cc(ccc2F)Oc2c(F)cc3[nH]ccc3c2CCS(=O)(=O)C1]

Step A: Exchanging methyl 3-(3-(1-chloro-8-((2-methoxy-2-oxoethyl)sulfonyl)-3,7,7-trimethyl-2-oxooctan-3-yl)phenyl)propanoate (Intermediate 8-3) with methyl 2-((8-bromo-6-(3-(2-methoxy-2-oxoethoxy)phenyl)-2,2,6-trimethyl-7-oxooctyl)sulfonyl)acetate (intermediate 17-11, 1.05 g, 1.91 mmol) in Step A, the reaction procedure sequence (Steps A to F) described for Example 27 was used to make the title compound (racemic, 115 mg) as a white solid. MS (ESI): 678 m/z $[M+H]^+$, retention time: 1.75 minutes, purity: 80% (254 nm) (LC-MS Method 022).

Enantiomers 1 and 2 of 2-[3-(22,28-difluoro-6,10,10-trimethyl-12,12-dioxo-24-oxa-12lambda6-thia-3,19,30-triazapentacyclo[23.3.1.12,5.015,23.016,20]triaconta-1(29),2,4,15,17,20,22,25,27-nonaen-6-yl)phenoxy]acetic Acid

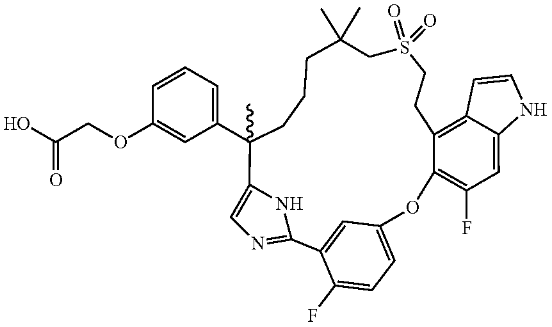 [SMILES: CC1(C)CCCC(C)(c2cccc(OCC(=O)O)c2)c2cnc([nH]2)-c2cc(ccc2F)Oc2c(F)cc3[nH]ccc3c2CCS(=O)(=O)C1]

First eluent: Enantiomer 1
Second eluent: Enantiomer 2

Step B: The racemic, crude product of step A (0.14 g, 0.21 mmol) was subjected to chiral SFC using a Thar SFC-80 instrument and the following separation conditions: Column: 20×250 mm×10 μm SSWHELK; Sample solution: 0.14 g dissolved in methanol (8 mL); injection volume: 1.0 mL; eluant: 50:50 carbon dioxide/ethanol with 0.5% methylethylamine additive; flow rate: 80 g/minute; column temperature: 35° C.; back pressure: 100 bar; detection wavelength: 214 nm; Cycle time: 4 minutes. The first eluting isomer, enantiomer 1, was designated as Compound 54B (40 mg, 28%) and the second eluting isomer, enantiomer 2, was designated as Compound 54A (40 mg, 28%).

Compound 54A: MS (ESI): 678 m/z $[M+H]^+$, retention time: 1.76 minutes, purity: 95% (254 nm) (LC-MS Method 022). $^1H$ NMR (400 MHz, $CD_3OD$) δ 7.44 (dd, J=5.8, 3.2 Hz, 1H), 7.23-7.00 (m, 6H), 6.72-6.71 (m, 2H), 6.61 (dd, J=8.8, 5.6 Hz, 1H), 6.52 (dd, J=3.2, 0.8 Hz, 1H), 4.33 (s, 2H), 3.34-3.25 (m, 2H), 3.16-3.09 (m, 1H), 3.02-2.85 (m, 1H), 2.60 (s, 2H), 2.03-1.95 (m, 1H), 1.83-1.74 (m, 1H), 1.46 (s, 3H), 1.25-1.11 (m, 3H), 1.01 (s, 3H), 0.84 (s, 3H), 0.79-0.70 (m, 1H) ppm.

Compound 54B: MS (ESI): 678 m/z $[M+H]^+$, retention time: 1.76 minutes, purity: 95% (254 nm) (LC-MS Method 022). $^1H$ NMR (400 MHz, $CD_3OD$) δ 7.44 (dd, J=5.8, 3.1 Hz, 1H), 7.23-7.00 (m, 6H), 6.71-6.72 (m, 2H), 6.61 (d, J=9.1 Hz, 1H), 6.51-6.52 (m, 1H), 4.33 (s, 2H), 3.34-3.25 (m, 2H), 3.16-3.09 (m, 1H), 3.02-2.85 (m, 1H), 2.60 (s, 2H), 2.03-1.95 (m, 1H), 1.83-1.74 (m, 1H), 1.46 (s, 3H), 1.25-1.11 (m, 3H), 1.01 (s, 3H), 0.84 (s, 3H), 0.79-0.70 (m, 1H) ppm.

Example 55. Enantiomers 1 and 2 of 3-[3-(22,28-difluoro-4,6,10,10-tetramethyl-12,12-dioxo-24-oxa-12 lambda6-thia-3,4,19,30-tetrazapentacyclo[23.3.1.12,5.015,23.016,20]triaconta-1(29),2,5(30),15,17,20,22,25,27-nonaen-6yl)phenyl]propanoic Acid

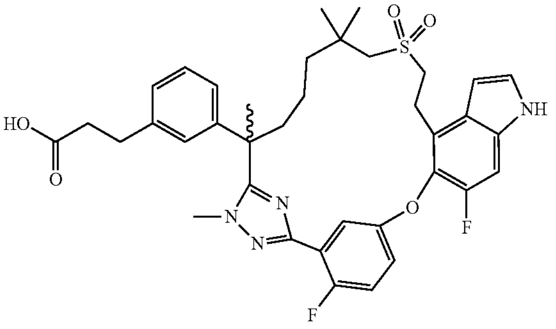

First Eluent: Enantiomer 1
Second Eluent: Enantiomer 2

Example 56. 3-[3-(22,28-Difluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic acid

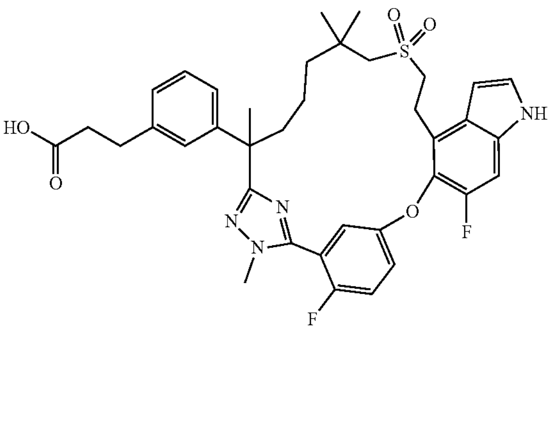 [SMILES: Cn1nc2nc1-c1cc(ccc1F)Oc1c(F)cc3[nH]ccc3c1CCS(=O)(=O)CC(C)(C)CCCC2(C)c1cccc(CCC(=O)O)c1]

Methyl 3-(3-(2-(3-(2-fluoro-5-((6-fluoro-4-vinyl-1H-indol-5-yl)oxy)phenyl)-1-methyl-1H-1,2,4-triazol-5-yl)-7-((2-methoxy-2-oxoethyl)sulfonyl)-6,6-dimethylheptan-2-yl)phenyl)propanoate and methyl 3-(3-(2-(5-(2-fluoro-5-((6-fluoro-4-vinyl-1H-indol-5-yl)oxy)phenyl)-1-methyl-1H-1,2,4-triazol-3-yl)-7-((2-methoxy-2-oxoethyl)sulfonyl)-6,6-dimethylheptan-2-yl)phenyl)propanoate

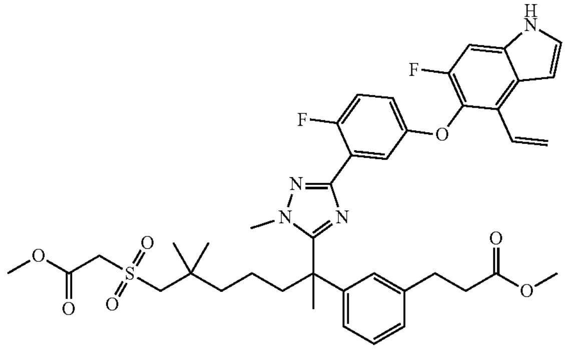

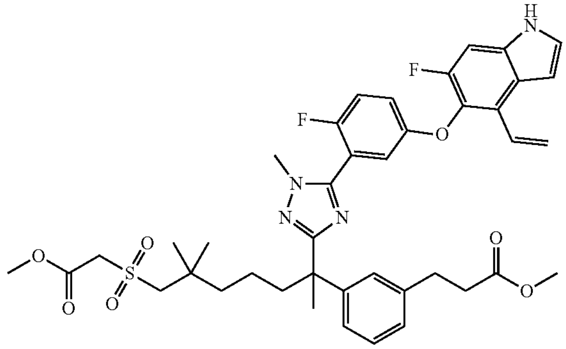

Step A: To a stirred solution of 7-((2-methoxy-2-oxoethyl)sulfonyl)-2-(3-(3-methoxy-3-oxopropyl)phenyl)-2,6,6-trimethylheptanoic acid (Intermediate 43-2, 2.70 g, 5.74 mmol) in N,N-dimethylformamide (50 mL) was added 2-fluoro-5-((6-fluoro-4-vinyl-1H-indol-5-yl)oxy)-benzimidamide (Intermediate 10-3, 1.8 g, 5.74 mmol), N-[(dimethylamino)-1H-1,2,3-triazolo-[4,5,b]pyridin-1-ylmethylene]-N-methylmethanaminium hexafluorophosphate N-oxide (3.27 g, 8.64 mmol) and diisopropylethylamine (2.22 g, 17.2 mmol). The mixture was stirred at room temperature for 2 hours, then treated with methylhydrazine sulfuric acid (8.61 mmol, 1.24 g) and acetic acid (1.64 ml). The reaction mixture was heated at 80° C. for 3 hours, cooled to room temperature, and quenched with water (300 mL). The solution was extracted with ethyl acetate (3×50 mL). The combined organic extracts were washed with saturated sodium bicarbonate, brine, dried over sodium sulfate, and concentrated. The crude material was purified by flash chromatography to give the title compounds as an inseparable mixture (2.97 g, 66%). MS (ESI): 777 m/z $[M+H]^+$, retention time: 2.30 minutes, purity: 90% (254 nm) (LC-MS Method 022).

Compounds 55A and 55B: Enantiomer 1 and Enantiomer 2 of 3-[3-(22,28-difluoro-4,6,10,10-tetramethyl-12,12-dioxo-24-oxa-12 lambda6-thia-3,4,19,30-tetrazapentacyclo[23.3.1.12,5.015,23.016,20]triaconta-1(29),2,5(30),15,17,20,22,25,27-nonaen-6yl)phenyl]propanoic Acid

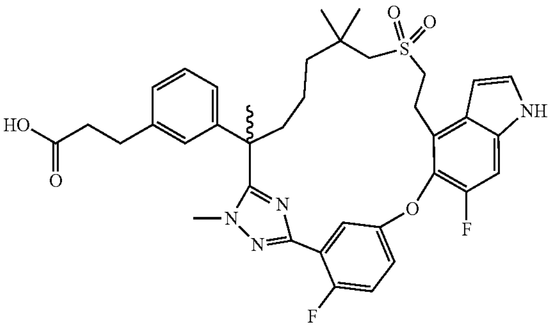

First Eluent: Enantiomer 1
Second Eluent: Enantiomer 2

Compound 56: 3-[3-(22,28-difluoro-3,6,10,10-tetramethyl-12,12-dioxo-24-oxa-12lambda6-thia-3,4,19,30-tetrazapentacyclo[23.3.1.12,5.015,23.016,20]-triaconta-1(29),2(30),4,15,17,20,22,25,27-nonaen-6-yl)phenyl]propanoic Acid

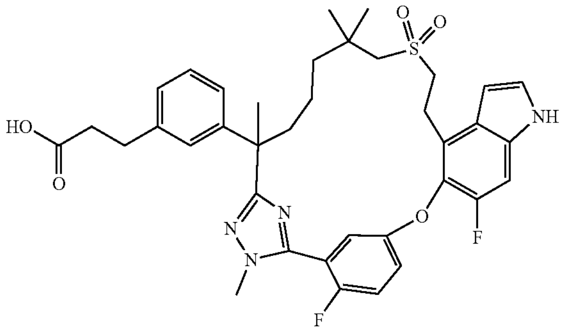

Step B: Exchanging ethyl 3-(3-(6-((2-ethoxy-2-oxoethyl)thio)-1-(3-(2-fluoro-5-((6-fluoro-1-tosyl-4-vinyl-1H-indol-5-yl)oxy)phenyl)-1H-pyrazol-1-yl)-5,5-dimethylhexyl)phenyl)propanoate (Step A product in Example 24) with the mixture of methyl 3-(3-(2-(3-(2-fluoro-5-((6-fluoro-4-vinyl-1H-indol-5-yl)oxy)phenyl)-1-methyl-1H-1,2,4-triazol-5-yl)-7-((2-methoxy-2-oxoethyl)sulfonyl)-6,6-dimethylheptan-2-yl)phenyl)propanoate and methyl 3-(3-(2-(5-(2-fluoro-5-((6-fluoro-4-vinyl-1H-indol-5-yl)oxy)phenyl)-1-methyl-1H-1,2,4-triazol-3-yl)-7-((2-methoxy-2-oxoethyl)sulfonyl)-6,6-dimethylheptan-2-yl)phenyl)propanoate (Step A of this Example, 2.2 g, 2.83 mmol), the reaction procedure sequence (Steps B to K) described for Example 24 was used to make the title compounds. The racemic methyl ester (700 mg), obtained from corresponding Step H of Example 24, was subject to the following chiral SFC separation condition: Instrument: SFC-80 (Thar, waters); Column, IG 20×250 mm, 10 μm; Column temperature: 35° C.; Mobile phase: carbon dioxide/isopropanol (0.2% ammonia in methanol as additive)=40/60; Flow rate: 80 g/minutes; Back pressure: 100 bar; Detection wavelength: 214 nm; Cycle time: 4.3 minutes; Sample solution: 700 mg dissolved in 25 mL methanol; Injection volume: 1 mL. The first eluent (173 mg), enantiomer 1, was further hydrolyzed to Compound 55A (118 mg, 70%); The second eluent (176 mg), enantiomer 2, was further hydrolyzed to Compound 55B (147 mg, 85%); The third eluent (60 mg), a regio-isomer and racemic mixture, was further hydrolyzed to Compound 56 (48.8 mg, 83%), followed the procedures described in Step J or Step K of Example 24.

Compound 55A: MS (ESI): 691 m/z $[M+H]^+$, retention time: 2.12 minutes, purity: >99% (254 nm) (LC-MS Method 022). $^1H$ NMR (400 MHz, $CD_3OD$) δ 7.72 (dd, J=3.2, 4.8 Hz, 1H), 7.31 (d, J=3.2 Hz, 1H), 7.28-7.19 (m, 3H), 7.14-7.11 (m, 2H), 6.97 (s, 1H), 6.90 (d, J=7.6 Hz, 1H), 6.66 (d, J=2.8 Hz, 1H), 3.46 (t, J=6.8 Hz, 2H), 3.34 (s, 3H), 3.22-3.16 (m, 2H), 2.88 (t, J=7.2 Hz, 2H), 2.71 (s, 2H), 2.55 (t, J=7.3 Hz, 2H), 1.86-1.82 (m, 1H), 1.78-1.74 (m, 1H), 1.71 (s, 3H), 1.60-1.53 (m, 1H), 1.30-1.25 (m, 1H), 1.03-0.84 (m, 8H) ppm.

Compound 55B: MS (ESI): 691 m/z $[M+H]^+$, retention time: 2.12 minutes, purity: >99% (254 nm) (LC-MS Method 022). $^1H$ NMR (400 MHz, $CD_3OD$) δ 7.72 (dd, J=3.2, 5.2 Hz, 1H), 7.32 (d, J=3.2 Hz, 1H), 7.30-7.21 (m, 3H), 7.18-7.13 (m, 2H), 6.97 (s, 1H), 6.90 (d, J=7.6 Hz, 1H), 6.66 (d, J=2.8 Hz, 1H), 3.46 (t, J=6.8 Hz, 2H), 3.34 (s, 3H), 3.22-3.16 (m, 2H), 2.88 (t, J=7.2 Hz, 2H), 2.71 (s, 2H), 2.55 (t, J=7.3 Hz, 2H), 1.87 (dt, J=3.6, 12.0 Hz, 1H), 1.80 (dt, J=3.6, 12.0 Hz, 1H), 1.71 (s, 3H), 1.60-1.53 (m, 1H), 1.30-1.25 (m, 1H), 1.03-0.84 (m, 8H) ppm.

Compound 56: MS (ESI): 691 m/z $[M+H]^+$, retention time: 2.10 minutes, purity: >99% (254 nm) (LC-MS Method 022). $^1H$ NMR (400 MHz, $CD_3OD$) δ 7.39-7.29 (m, 3H), 7.25-7.18 (m, 2H), 7.15 (d, J=7.6 Hz, 1H), 7.09 (s, 1H), 7.04-6.99 (m, 2H), 6.63 (d, J=2.8 Hz, 1H), 3.86 (d, J=2.0 Hz, 3H), 3.40-3.35 (m, 3H), 3.27-3.16 (m, 1H), 2.98 (d, J=13.6 Hz, 1H), 2.86-2.79 (m, 3H), 2.50 (t, J=7.6 Hz, 2H), 2.16 (dt, J=3.6, 12.8 Hz, 1H), 1.82 (dt, J=3.6, 12.8 Hz, 1H), 1.69 (s, 3H), 1.63-1.55 (m, 1H), 1.37-1.30 (m, 2H), 1.25-1.18 (m, 1H), 1.07 (s, 6H) ppm.

Example 57. 3-[3-(22,28-Difluoro-10,10-dimethyl-12,12-dioxo-24-oxa-12λ6-thia-5,17,19,30-tetrazapentacyclo[23.3.1.12,5.015,23.016,20]triaconta-1(29),2(30),3,15,17,20,22,25,27-nonaen-6-yl)phenyl]propanoic Acid

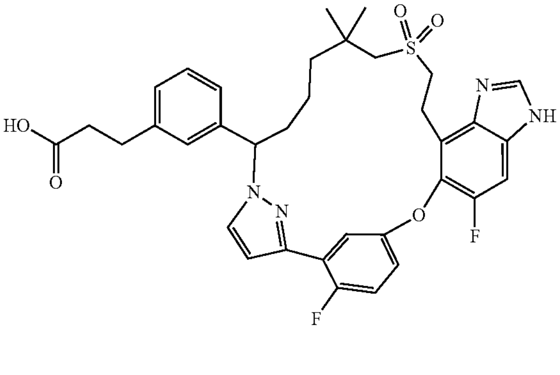 [SMILES: CC1(C)CCCC(c2cccc(CCC(=O)O)c2)n2ccc(n2)-c2cc(ccc2F)Oc2c(F)cc3[nH]cnc3c2CCS(=O)(=O)C1]

Ethyl 3-(3-(6-((2-ethoxy-2-oxoethyl)thio)-1-(3-(2-fluoro-5-((6-fluoro-1-(tetrahydro-2H-pyran-2-yl)-4-vinyl-1H-benzo[d]imidazol-5-yl)oxy)phenyl)-1H-pyrazol-1-yl)-5,5-dimethylhexyl)phenyl)propanoate

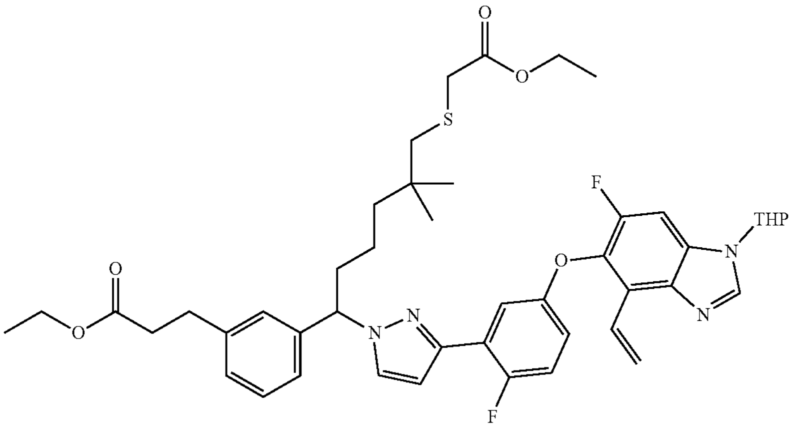

Step A: To a stirred solution of 6-fluoro-5-(4-fluoro-3-(1H-pyrazol-3-yl)phenoxy)-1-(tetrahydro-2H-pyran-2-yl)-4-vinyl-1H-benzo[d]imidazole (Intermediate 21-3, 1.2 g, 2.84 mmol) in N,N-dimethylformamide (40 mL) was added ethyl 3-(3-(1-bromo-6-((2-ethoxy-2-oxoethyl)thio)-5,5-dimethylhexyl)phenyl)propanoate (Intermediate 54-1, 1.69 g, 3.12 mmol) and cesium carbonate (1.85 g, 5.68 mmol). The mixture was stirred at room temperature for 16 hours, then diluted with ethyl acetate (100 mL). The solution was washed with water (2×50 mL), dried over sodium sulfate, and concentrated. The residue was purified by automated silica gel chromatography (petroleum ether/ethyl acetate=2/1 to 1/1) to give the title compound (1.7 g, 72%) as a colorless oil. MS (ESI): 829 m/z $[M+H]^+$, retention time: 2.40 minutes, purity: >99% (254 nm) (LC-MS Method 023).

Ethyl 3-(3-(6-((2-ethoxy-2-oxoethyl)thio)-1-(3-(2-fluoro-5-((6-fluoro-4-vinyl-1H-benzo[d]imidazol-5-yl)oxy)phenyl)-1H-pyrazol-1-yl)-5,5-dimethylhexyl)phenyl)propanoate

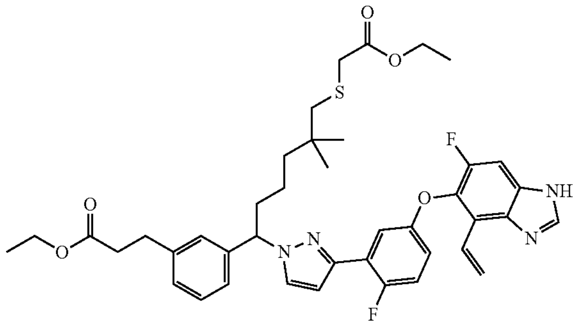 [SMILES: C=Cc1c(Oc2ccc(F)c(-c3ccn(C(CCCC(C)(C)CSCC(=O)OCC)c4cccc(CCC(=O)OCC)c4)n3)c2)c(F)cc2[nH]cnc12]

Step B: To a stirred solution of Step A product (1.0 g, 1.21 mmol) in methanol (40 mL) was added pyridinium 4-toluenesulfonate (909 mg, 3.62 mmol). The reaction mixture was stirred at 40° C. for 2 days. The solvent was removed, and the residue was purified by automated silica gel chromatography eluted with petroleum ether/ethyl acetate=2/1 to 1/2 to give the title compound (830 mg, 92%) as a colorless oil. MS (ESI): 745 m/z $[M+H]^+$, retention time: 2.13 minutes, purity: >99% (254 nm) (LC-MS Method 023).

Ethyl 3-(3-(6-((2-ethoxy-2-oxoethyl)sulfonyl)-1-(3-(2-fluoro-5-((6-fluoro-4-formyl-1H-benzo[d]imidazol-5-yl)oxy)phenyl)-1H-pyrazol-1-yl)-5,5-dimethylhexyl)phenyl)propanoate

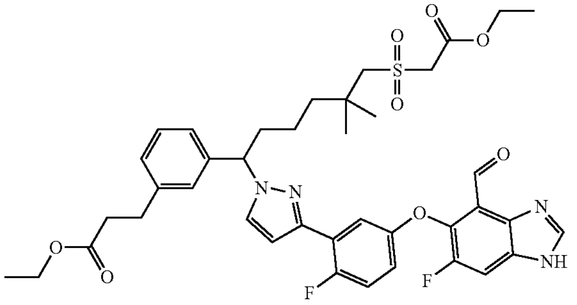 [SMILES: CCOC(=O)CCc1cccc(C(CCCC(C)(C)CS(=O)(=O)CC(=O)OCC)n2ccc(-c3cc(Oc4c(F)cc5[nH]cnc5c4C=O)ccc3F)n2)c1]

Step C: Exchanging ethyl 3-(3-(6-((2-ethoxy-2-oxoethyl)thio)-1-(3-(2-fluoro-5-((6-fluoro-4-vinyl-1H-indol-5-yl)oxy)phenyl)-1H-pyrazol-1-yl)-5,5-dimethylhexyl)phenyl)propanoate (Step B product of Example 24) with ethyl 3-(3-(6-((2-ethoxy-2-oxoethyl)thio)-1-(3-(2-fluoro-5-((6-fluoro-4-vinyl-1H-benzo [d]imidazol-5-yl)oxy)phenyl)-1H-pyrazol-1-yl)-5,5-dimethylhexyl)-phenyl)propanoate (Step B product, 810 mg, 1.0 mmol), the procedure sequence (Steps C and D) described for Example 24 was used to prepare the title compound (480 mg) as a colorless oil. MS (ESI): 779 m/z $[M+H]^+$, retention time: 2.08 minutes, purity: 91% (254 nm) (LC-MS Method 023).

O19-Tert-Butyl O13-ethyl (13E)-6-[3-(3-ethoxy-3-oxo-propyl)phenyl]-22,28-difluoro-10,10-dimethyl-12,12-dioxo-24-oxa-12λ6-thia-5,17,19,30-tetraza-pentacyclo-[23.3.1.12,5.015,23.016,20]triaconta-1(29),2(30),3,13,15,17,20,22,25,27-decaene-13,19-dicarboxylate

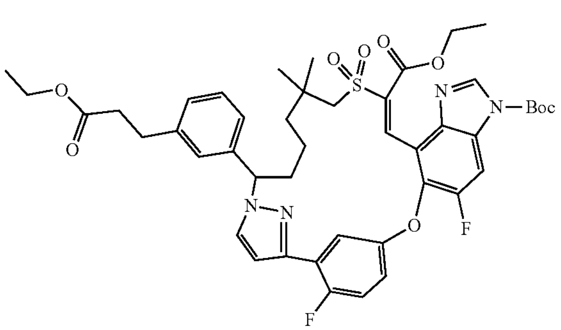 [SMILES: CCOC(=O)CCc1cccc(C2CCCC(C)(C)CS(=O)(=O)/C(C(=O)OCC)=C/c3c(c(F)cc4c3ncn4C(=O)OC(C)(C)C)Oc3ccc(F)c(c3)-c3ccn2n3)c1]

Step D: To a stirred solution of Step C product (114 mg, 0.133 mmol) in dichloromethane (15 mL) was added di-tert-butyl dicarbonate (145 mg, 0.666 mmol) and N,N-dimethylaminopyridine (16.3 mg, 0.133 mmol). The mixture was stirred at room temperature overnight and concentrated. The residue was purified by prep-TLC (petroleum ether/ethyl acetate=2/1) to give the title compound (46 mg, 37%) as a colorless oil. MS (ESI): 861 m/z $[M+H]^+$, retention time: 2.51 minutes, purity: 91% (254 nm) (LC-MS Method 023).

Compound 57: 3-[3-(22,28-Difluoro-10,10-dimethyl-12,12-dioxo-24-oxa-12λ6-thia-5,17,19,30-tetrazapentacyclo[23.3.1.12,5.015,23.016,20]triaconta-1(29),2(30),3,15,17,20,22,25,27-nonaen-6-yl)phenyl]propanoic Acid

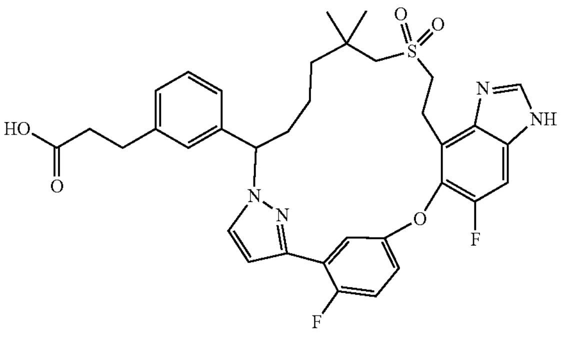 [SMILES: CC1(C)CCCC(c2cccc(CCC(=O)O)c2)n2ccc(n2)-c2cc(ccc2F)Oc2c(F)cc3[nH]cnc3c2CCS(=O)(=O)C1]

Step E: Exchanging ethyl (13E)-6-[3-(3-ethoxy-3-oxo-propyl)phenyl]-22,28-difluoro-10,10-dimethyl-12,12-dioxo-24-oxa-12lambda6-thia-5,19,30-triazapentacyclo-[23.3.1.12,5.015,23.016,20]triaconta-1(29),2(30),3,13,15,17,20,22,25,27-decaene-13-carboxylate (Step E product of Example 24) with O19-tert-butyl O13-ethyl (13E)-6-[3-(3-ethoxy-3-oxo-propyl)phenyl]-22,28-difluoro-10,10-dimethyl-12,12-dioxo-24-oxa-12λ6-thia-5,17,19,30-tetrazapentacyclo[23.3.1.12,5.015,23.016,20]triaconta-1(29),2(30),3,13,15,17,20,22,25,27-decaene-13,19-dicarboxylate (Step D product of this example, 76 mg, 0.08 mmol), the reaction procedure sequence (Steps F-H) described for Example 24 was used to prepare the title compound (3 mg) as a white solid. MS (ESI): 663 m/z $[M+H]^+$, retention time: 1.76 minutes, purity: >99% (254 nm) (LC-MS Method 024). $^1H$ NMR (400 MHz, $CD_3OD$) δ 8.26 (s, 1H), 7.72 (dd, J=5.6, 3.2 Hz, 1H), 7.55-7.52 (m, 2H), 7.23-7.16 (m, 4H), 7.09 (d, J=7.6 Hz, 1H), 7.05-6.99 (m, 1H), 6.73 (dd, J=4.4, 2.4 Hz, 1H), 5.39-5.35 (m, 1H), 3.55 (t, J=7.6 Hz, 2H), 3.23-3.20 (m, 2H), 2.88 (t, J=7.6 Hz, 2H), 2.70-2.68 (m, 2H), 2.50 (t, J=7.6 Hz, 2H), 2.38-2.33 (m, 1H), 1.92-1.87 (m, 1H), 1.50-1.22 (m, 4H), 1.13 (s, 3H), 0.95 (s, 3H) ppm.

Example 58. 3-[3-(22,28-Difluoro-10,10-dimethyl-12,12-dioxo-8,24-dioxa-12λ6-thia-5,19,30-triaza-pentacyclo[23.3.1.12,5.015,23.016,20]triaconta-1(29),2(30),3,15,17,20,22,25,27-nonaen-6-yl)phenyl]propanoic Acid

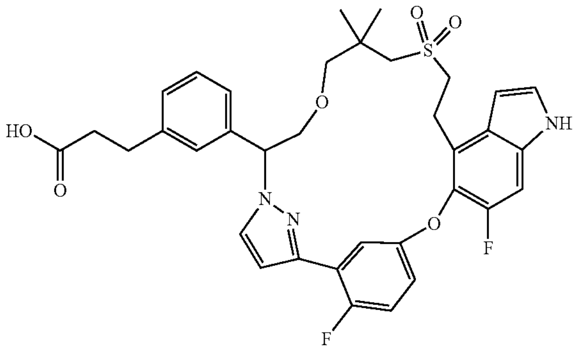 [SMILES: CC1(C)COCC(c2cccc(CCC(=O)O)c2)n2ccc(n2)-c2cc(ccc2F)Oc2c(F)cc3[nH]ccc3c2CCS(=O)(=O)C1]

Exchanging ethyl 3-(3-(1-bromo-6-((2-ethoxy-2-oxoethyl)thio)-5,5-dimethylhexyl)phenyl)-propanoate (Intermediate 54-1) with ethyl 3-(3-(1-bromo-2-(3-((2-ethoxy-2-oxoethyl)thio)-2,2-dimethylpropoxy)ethyl)phenyl)propanoate (Intermediate 54-5, 0.58 g, 1.18 mmol), the reaction procedure sequence (Steps A to H) described for Example 24 was used to prepare the title compound (9 mg) as a white solid. MS (ESI): 664 m/z $[M+H]^+$, retention time: 1.8 minutes, purity: >99% (214 nm) (LC-MS Method 024). $^1H$ NMR (400 MHz, $CD_3OD$) δ 7.59 (dd, J=5.6, 3.2 Hz, 1H), 7.55 (d, J=2.4 Hz, 1H), 7.35 (d, J=3.2 Hz, 1H), 7.32 (d, J=10.4 Hz, 1H), 7.26-7.14 (m, 4H), 7.12-7.03 (m, 2H), 6.72 (dd, J=4.4, 2.4 Hz, 1H), 6.68 (d, J=2.8 Hz, 1H), 5.56 (dd, J=10.4, 3.6 Hz, 1H), 4.11 (t, J=10.0 Hz, 1H), 3.73 (dd, J=9.6, 3.6 Hz, 1H), 3.47 (td, J=7.6, 2.4 Hz, 2H), 3.13 (d, J=8.8 Hz, 1H), 3.05 (t, J=7.2 Hz, 2H), 2.88 (t, J=7.6 Hz, 2H), 2.78 (d, J=9.2 Hz, 1H), 2.67 (d, J=13.6 Hz, 1H), 2.58-2.52 (m, 3H), 1.34-1.30 (m, 2H), 1.01 (s, 3H), 0.99 (s, 3H) ppm.

Example 59. 3-[3-(22,28-Difluoro-11,11-dimethyl-13,13-dioxo-9,24-dioxa-13λ6-thia-5,19,30-triaza-pentacyclo[23.3.1.12,5.015,23.016,20]triaconta-1(29),2(30),3,15,17,20,22,25,27-nonaen-6-yl)phenyl]propanoic Acid

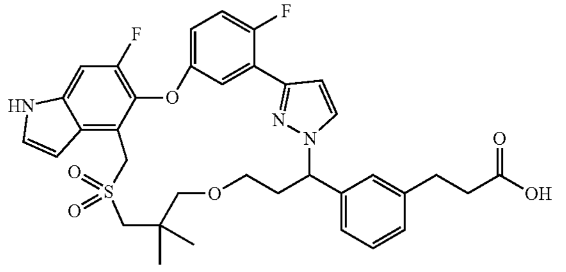 [SMILES: CC1(C)COCCC(c2cccc(CCC(=O)O)c2)n2ccc(n2)-c2cc(ccc2F)Oc2c(F)cc3[nH]ccc3c2CS(=O)(=O)C1]

and

Example 60. 3-[3-(23,29-Difluoro-12,12-dimethyl-14,14-dioxo-10,25-dioxa-14λ6-thia-5,6,20-triaza-pentacyclo[24.3.1.02,6.016,24.017,21]triaconta-1(30),2,4,16,18,21,23,26,28-nonaen-7-yl)phenyl]propanoic Acid

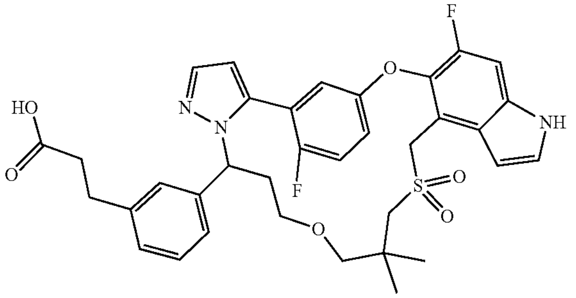 [SMILES: CC1(C)COCCC(c2cccc(CCC(=O)O)c2)n2nccc2-c2cc(ccc2F)Oc2c(F)cc3[nH]ccc3c2CS(=O)(=O)C1]

Ethyl 3-(3-(3-(3-(((6-fluoro-5-(4-fluoro-3-(1-(tetrahydro-2H-pyran-2-yl)-1H-pyrazol-3-yl)phenoxy)-1-tosyl-1H-indol-4-yl)methyl)thio)-2,2-dimethylpropoxy)-1-((tetrahydro-2H-pyran-2-yl)oxy)propyl)phenyl)propanoate

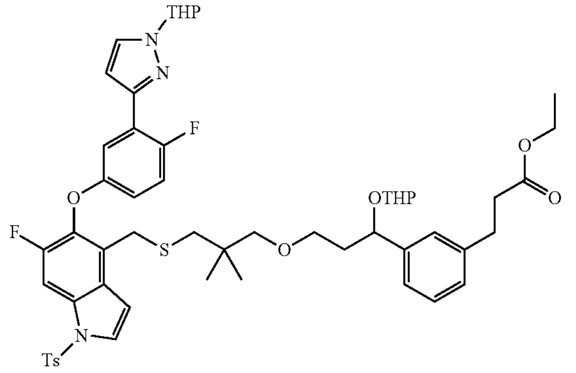

Step A: To a stirred solution of ethyl 3-(3-(3-(3-(acetylthio)-2,2-dimethylpropoxy)-1-((tetrahydro-2H-pyran-2-yl)oxy)propyl)phenyl)propanoate (Intermediate 33F-1, 190 mg, 0.395 mmol) and 4-(bromomethyl)-6-fluoro-5-(4-fluoro-3-(1-(tetrahydro-2H-pyran-2-yl)-1H-pyrazol-3-yl)phenoxy)-1-tosyl-1H-indole (Intermediate 87, 290 mg, 0.433 mmol) in ethanol (4 mL) and tetrahydrofuran (4 mL) was added sodium ethoxide (40.3 mg, 0.59 mmol). The mixture was stirred at 20° C. for 3 hours, then quenched with water (50 mL) and extracted with ethyl acetate (2×50 mL). The combined organic layers were dried over anhydrous sodium sulfate and concentrated. The residue was purified with automated flash chromatography (12 g silica gel column, 20% to 50% of ethyl acetate in petroleum ether) to give the title compound (390 mg, 94%) as a colorless gum. MS (ESI): 1022 m/z $[M+Na]^+$, retention time: 3.73 minutes, purity: >95% (214 nm) (LC-MS Method 020).

Ethyl 3-(3-(3-(3-(((6-fluoro-5-(4-fluoro-3-(1H-pyrazol-3-yl)phenoxy)-1-tosyl-1H-indol-4-yl)methyl)thio)-2,2-dimethylpropoxy)-1-hydroxypropyl)phenyl)propanoate

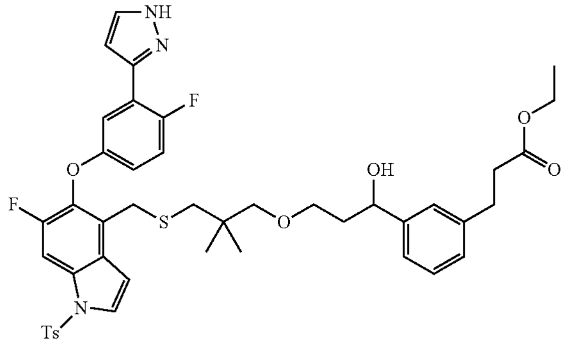 [SMILES: CCOC(=O)CCc1cccc(C(O)CCOCC(C)(C)CSCc2c(Oc3ccc(F)c(-c4cc[nH]n4)c3)c(F)cc3c2ccn3S(=O)(=O)c2ccc(C)cc2)c1]

Step B: To a stirred solution of Step A product (390 mg, 0.38 mmol) in ethanol (10 mL) was added p-toluenesulfonic acid (400 mg, 2.33 mmol). The mixture was stirred at 50° C. for 42 hours, quenched with saturated aqueous sodium bicarbonate solution (20 mL), and extracted with ethyl acetate (2×30 mL). The combined organic layers were dried over anhydrous sodium sulfate and concentrated. The residue was purified with automated flash chromatography (25% to 45% of ethyl acetate in petroleum ether) to give the tile compound (260 mg, 82%) as a colorless gum. MS (ESI): 832 m/z $[M+H]^+$, retention time: 3.17 minutes, purity: >99% (214 nm) (LC-MS Method 020). $^1H$ NMR (400 MHz, $CDCl_3$): δ 7.72 (d, J=8.0 Hz, 2H), 7.70-7.64 (m, 1H), 7.53 (t, J=3.6 Hz, 1H), 7.48 (d, J=1.6 Hz, 1H), 7.39-7.36 (m, 1H), 7.21 (d, J=8.4 Hz, 2H), 7.18-7.14 (m, 1H), 7.14-7.05 (m, 2H), 7.01 (d, J=7.2 Hz, 1H), 6.95 (t, J=9.6 Hz, 1H), 6.76 (d, J=3.6 Hz, 1H), 6.69-6.62 (m, 1H), 6.60 (s, 1H), 4.79 (dd, J=8.0, 3.6 Hz, 1H), 4.14-3.97 (m, 2H), 3.84 (s, 2H), 3.49-3.29 (m, 2H), 3.03 (s, 2H), 2.86 (t, J=7.6 Hz, 2H), 2.53 (t, J=7.6 Hz, 2H), 2.45 (s, 2H), 2.31 (s, 3H), 1.92-1.75 (m, 2H), 1.29-1.13 (m, 3H), 0.78 (s, 3H), 0.76 (s, 3H) ppm.

Ethyl 3-[3-[23,29-difluoro-12,12-dimethyl-20-(p-tolylsulfonyl)-10,25-dioxa-14-thia-5,6,20-triazapentacyclo[24.3.1.02,6.016,24.017,21]triaconta-1(30),2,4,16,18,21,23,26,28-nonaen-7-yl]phenyl]propanoate (Step C-P2) and ethyl 3-[3-[22,28-difluoro-11,11-dimethyl-19-(p-tolylsulfonyl)-9,24-dioxa-]3-thia-5,19,30-triazapentacyclo[23.3.1.12,5.015,23.016,20]triaconta-1(29),2(30),3,15,17,20,22,25,27-nonaen-6-yl]phenyl]propanoate (Step C-P3)

Step C-P1

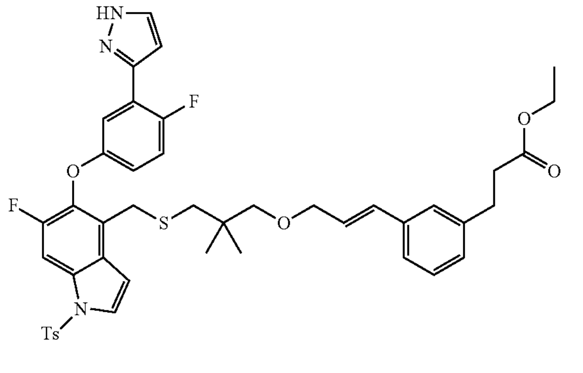

-continued

Step C-P2

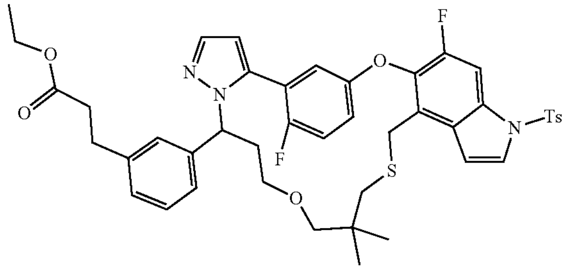

Step C-P3

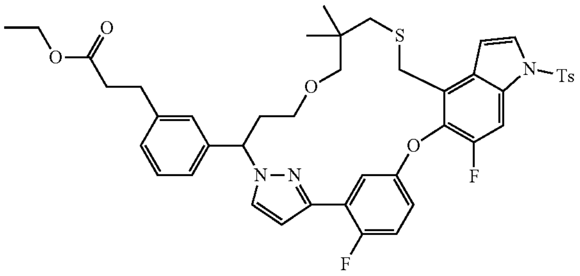

Step C: To a stirred solution of Step B product (260 mg, 0.313 mmol) in anhydrous dioxane (12 mL) was added 2-(tributyl-lambda5-phosphanylidene)acetonitrile (377 mg, 1.56 mmol) in a glove box. The mixture was stirred at 145° C. under microwave irradiation for 40 minutes. The reaction mixture was partitioned between water (20 mL) and ethyl acetate (20 mL). The separated organic layer, combined with two additional ethyl acetate extracts (2×10 mL), was dried over sodium sulfate, and concentrated. The residue was purified with prep-HPLC (Instrument: Gilson 281 (PHG012); Column: Xtimate C18 21.2×250 mm, 10 μm; Mobile Phase: A: water (10 mM ammonium bicarbonate & 0.025% ammonia), B: acetonitrile; Gradient: 80% B for 1 minutes, then 95% B in 7 minutes, stop at 15 minutes; Flow Rate: 30 mL/minute; Detective Wavelength: 214/254 nm; Injection Number: 19). The first eluent was designated as Step C-P1 (10 mg, 4%); The second eluent was designated as Step C-P2 (40 mg, 16%). The third eluent was designated as Step C-P3, (30 mg, 12%); all are white solids.

C-P1: Ethyl (E)-3-(3-(3-(3-(((6-fluoro-5-(4-fluoro-3-(1H-pyrazol-3-yl)phenoxy)-1-tosyl-1H-indol-4-yl)methyl)thio)-2,2-dimethylpropoxy)prop-1-en-1-yl)phenyl)propanoate (de-hydration product). MS (ESI): 814 m/z $[M+H]^+$, retention time: 3.39 minutes, purity: 84% (214 nm) (LC-MS Method 020). $^1H$ NMR (400 MHz, $CDCl_3$): δ 7.71 (d, J=8.4 Hz, 2H), 7.67 (d, J=10.6 Hz, 1H), 7.55-7.48 (m, 2H), 7.33-7.27 (m, 1H), 7.20 (d, J=8.0 Hz, 2H), 7.17-7.09 (m, 3H), 7.00 (brd, J=7.2 Hz, 1H), 6.95 (dd, J=10.2, 9.2 Hz, 1H), 6.75 (d, J=3.6 Hz, 1H), 6.69 (dt, J=8.8, 3.6 Hz, 1H), 6.59 (t, J=2.0 Hz, 1H), 6.39 (d, J=16.0 Hz, 1H), 6.09 (dt, J=16.0, 5.6 Hz, 1H), 4.05 (q, J=7.2 Hz, 2H), 3.89 (dd, J=5.6, 1.2 Hz, 2H), 3.83 (s, 2H), 3.05 (s, 2H), 2.85 (t, J=8.0 Hz, 2H), 2.54 (t, J=8.0 Hz, 2H), 2.46 (s, 2H), 2.30 (s, 3H), 1.14 (t, J=7.2 Hz, 3H), 0.77 (s, 6H) ppm.

C-P2: Ethyl 3-[3-[23,29-difluoro-12,12-dimethyl-20-(p-tolylsulfonyl)-10,25-dioxa-14-thia-5,6,20-triazapentacyclo[24.3.1.02,6.016,24.017,21]triaconta-1(30),2,4,16,18,21,23,26,28-nonaen-7-yl]phenyl]propanoate. MS (ESI): 814 m/z $[M+H]^+$, retention time: 3.50 minutes, purity: >99% (214 nm) (LC-MS Method 020). $^1H$ NMR (400 MHz, $CDCl_3$): δ 7.74 (d, J=8.4 Hz, 2H), 7.66 (d, J=10.0 Hz, 1H), 7.58 (d, J=2.0 Hz, 1H), 7.55 (d, J=3.6 Hz, 1H), 7.23 (d, J=8.0 Hz, 2H), 7.05-6.96 (m, 3H), 6.96-6.88 (m, 3H), 6.74-6.69 (m, 2H), 6.34-6.30 (m, 1H), 5.50-5.46 (m, 1H), 4.03 (q, J=7.2 Hz, 2H), 3.91 (d, J=13.2 Hz, 1H), 3.74 (d, J=13.2 Hz, 1H), 3.18-3.01 (m, 2H), 2.94 (d, J=8.8 Hz, 1H), 2.85-2.78 (m, 3H), 2.51-2.41 (m, 4H), 2.35-2.26 (m, 5H), 1.14 (t, J=7.2 Hz, 3H), 0.80 (s, 3H), 0.74 (s, 3H) ppm.

C-P3: Ethyl 3-[3-[22,28-difluoro-11,11-dimethyl-19-(p-tolylsulfonyl)-9,24-dioxa-13-thia-5,19,30-triazapentacyclo[23.3.1.12,5.015,23.016,20]triaconta-1(29),2(30),3,15,17,20,22,25,27-nonaen-6-yl]phenyl]propanoate. MS (ESI): 814 m/z $[M+H]^+$, retention time: 3.55 minutes, purity: >99% (214 nm) (LC-MS Method 020). $^1H$ NMR (400 MHz, $CDCl_3$): δ 7.84-7.77 (m, 1H), 7.69 (d, J=8.4 Hz, 2H), 7.66 (d, J=10.8 Hz, 1H), 7.52 (d, J=3.6 Hz, 1H), 7.19 (t, J=8.0 Hz, 1H), 7.17-7.12 (m, 3H), 7.10-7.05 (m, 3H), 7.02-6.98 (m, 2H), 6.77 (d, J=3.6 Hz, 1H), 6.67 (dd, J=4.4, 2.4 Hz, 1H), 5.56-5.47 (m, 1H), 4.02 (q, J=7.2 Hz, 2H), 3.96 (d, J=13.6 Hz, 1H), 3.84 (d, J=13.6 Hz, 1H), 3.36-3.26 (m, 1H), 2.93 (d, J=8.8 Hz, 1H), 2.88-2.83 (m, 3H), 2.80-2.72 (m, 1H), 2.60 (d, J=12.8 Hz, 1H), 2.52 (t, J=8.0 Hz, 2H), 2.43 (d, J=12.8 Hz, 1H), 2.34-2.24 (m, 2H), 2.22 (s, 3H), 1.13 (t, J=7.2 Hz, 3H), 0.75 (s, 3H), 0.59 (s, 3H) ppm.

Ethyl 3-[3-[23,29-difluoro-12,12-dimethyl-14,14-dioxo-20-(p-tolylsulfonyl)-10,25-dioxa-14lambda6-thia-5,6,20-triazapentacyclo[24.3.1.02,6.016,24.017,21]triaconta-1(30),2,4,16,18,21,23,26,28-nonaen-7-yl]phenyl]propanoate

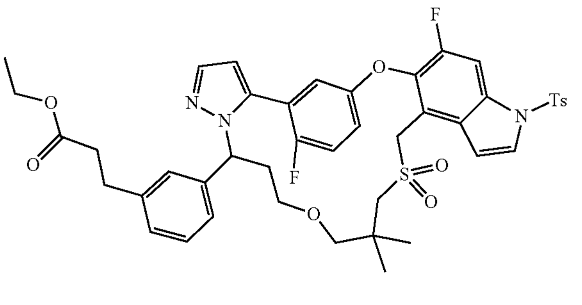 [SMILES: CCOC(=O)CCc1cccc(C2CCOCC(C)(C)CS(=O)(=O)Cc3c(c(F)cc4c3ccn4S(=O)(=O)c3ccc(C)cc3)Oc3ccc(F)c(c3)-c3ccnn32)c1]

Step D: To a stirred and cooled (0° C.) solution of Step C-P2 of Step C product (90 mg) in methanol (9 mL) was added a solution of ammonium molybdate (180 mg) in hydrogen peroxide aqueous solution (30%, 0.9 mL). The mixture was stirred at this temperature for 16 hours, then diluted with water (20 mL), and extracted with ethyl acetate (2×20 mL). The combined organic layers were washed with saturated sodium sulfite, brine, dried over sodium sulfate, and concentrated to give the tile product (90 mg, 94%) as a colorless gum. MS (ESI): 846 m/z $[M+H]^+$, retention time: 3.24 minutes, purity: 98% (214 nm) (LC-MS Method 020).

Compound 60: 3-[3-(23,29-difluoro-12,12-dimethyl-14,14-dioxo-10,25-dioxa-14 6-thia-5,6,20-triazapentacyclo[24.3.1.02,6.016,24.017,21]triaconta-1(30),2,4,16,18,21,23,26,28-nonaen-7-yl)phenyl]propanoic Acid

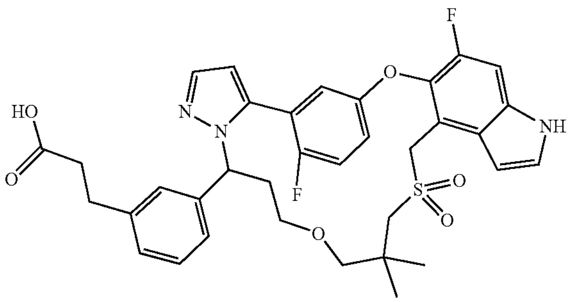 [SMILES: CC1(C)COCCC(c2cccc(CCC(=O)O)c2)n2nccc2-c2cc(ccc2F)Oc2c(F)cc3[nH]ccc3c2CS(=O)(=O)C1]

Step E: To a stirred solution of Step D product (100 mg, 0.12 mmol) in methanol (2 mL) and tetrahydrofuran (2 mL) was added a solution of lithium hydroxide (22.2 mg, 1.0 mmol) in water (2 mL). The mixture was stirred at 25° C. for 16 hours, diluted with water (10 mL), and acidified with hydrochloric acid (1 M) to pH ~5. The mixture was extracted with ethyl acetate (2×20 mL). The combined organic layers were dried over sodium sulfate and concentrated. The residue was purified with prep-HPLC (Instrument: Gilson 281 (PHG012); Column: Xtimate C18 21.2×250 mm, 10 μm; Mobile Phase: A: water (10 mM ammonium bicarbonate & 0.025% ammonia), B: acetonitrile; Gradient: 32% to 45% B in 8 minutes, stop at 15 minutes; Flow Rate: 30 mL/minute; Detective Wavelength: 214/254 nm; Retention Time: 14 minutes; Injection Number: 6. The title compound (35.2 mg, 46%) was obtained as a white solid. MS (ESI): 664 m/z $[M+H]^+$, retention time: 1.81 minutes, purity: >99% (214 nm) (LC-MS Method 026). $^1$H NMR (400 MHz, DMSO-d6): δ 11.50 (s, 1H), 7.66 (d, J=2.0 Hz, 1H), 7.51-7.45 (m, 2H), 7.25 (t, J=9.2 Hz, 1H), 7.15 (dd, J=5.6, 3.2 Hz, 1H), 7.12-7.05 (m, 3H), 6.96-6.80 (m, 2H), 6.66 (brs, 1H), 6.47 (brs, 1H), 5.55 (t, J=7.2 Hz, 1H), 4.76-4.64 (m, 2H), 3.26-3.16 (m, 4H), 3.07-2.94 (m, 2H), 2.74 (t, J=7.6 Hz, 2H), 2.49-2.30 (m, 4H), 1.02 (s, 3H), 0.98 (s, 3H) ppm.

Compound 59: 3-[3-(22,28-difluoro-11,11-dimethyl-13,13-dioxo-9,24-dioxa-13 6-thia-5,19,30-triazapentacyclo[23.3.1.12,5.015,23.016,20]triaconta-1(29),2(30),3,15,17,20,22,25,27-nonaen-6-yl)phenyl]propanoic Acid

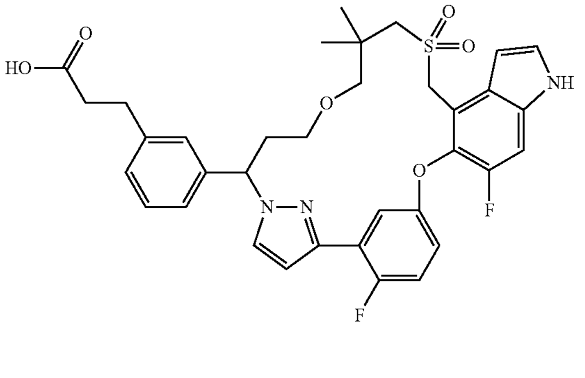 [SMILES: CC1(C)COCCC(c2cccc(CCC(=O)O)c2)n2ccc(n2)-c2cc(ccc2F)Oc2c(F)cc3[nH]ccc3c2CS(=O)(=O)C1]

Step F: Step C-P3 of Step C product (70 mg, 0.083 mmol) was converted to the title compound (36.2 mg, 58%) Utilizing identical conditions described in Step D oxidation followed by Step E hydrolysis. MS (ESI): 664 m/z $[M+H]^+$, retention time: 1.62 minutes, purity: >99% (214 nm) (LC-MS Method 020). $^1$H NMR (400 MHz, DMSO-d6): δ 11.48 (s, 1H), 7.82 (dd, J=6.4, 3.2 Hz, 1H), 7.77 (d, J=2.4 Hz, 1H), 7.49-7.46 (m, 1H), 7.43 (d, J=11.2 Hz, 1H), 7.25-7.18 (m, 2H), 7.17-7.10 (m, 2H), 7.03 (dt, J=8.8, 3.6 Hz, 1H), 6.96 (d, J=7.6 Hz, 1H), 6.80 (brs, 1H), 6.60 (dd, J=4.4, 2.4 Hz, 1H), 5.40 (d, J=9.6 Hz, 1H), 4.78 (d, J=14.0 Hz, 1H), 4.56 (d, J=14.0 Hz, 1H), 3.42-3.25 (m, 4H), 3.13 (d, J=9.2 Hz, 1H), 3.08-3.00 (m, 2H), 2.97-2.88 (m, 1H), 2.78 (t, J=7.7 Hz, 2H), 2.63-2.54 (m, 1H), 2.12-2.00 (m, 1H), 1.03 (s, 3H), 0.93 (s, 3H) ppm.

Example 61. 2-[3-(22,28-Difluoro-3,6,10,10-tetramethyl-12,12-dioxo-24-oxa-12lambda6-thia-3,19,30-triazapentacyclo[23.3.1.12,5.015,23.016,20]triaconta-1(29),2(30),4,15,17,20,22,25,27-nonaen-6-yl)phenyl]acetic Acid

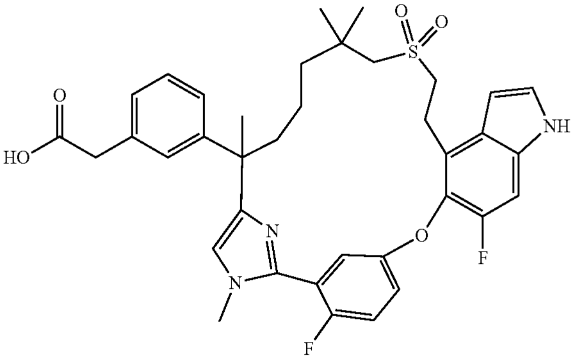 [SMILES: Cn1cc2nc1-c1cc(ccc1F)Oc1c(F)cc3[nH]ccc3c1CCS(=O)(=O)CC(C)(C)CCCC2(C)c1cccc(CC(=O)O)c1]

Exchanging methyl 3-(3-(1-chloro-8-((2-methoxy-2-oxoethyl)sulfonyl)-3,7,7-trimethyl-2-oxooctan-3-yl)phenyl)propanoate (Intermediate 8-3) with ethyl 2-((8-bromo-6-(3-(2-ethoxy-2-oxoethyl)phenyl)-2,2,6-trimethyl-7-oxooctyl)sulfonyl)acetate (Intermediate 17-12, 4 g, 7.12 mmol) and 2-fluoro-5-((6-fluoro-4-vinyl-1H-indol-5-yl)oxy)benzimidamide (Intermediate 10-3) with 2-fluoro-5-((6-fluoro-4-vinyl-1H-indol-5-yl)oxy)-N-methylbenzimidamide (Intermediate 90, 2.33 g, 7.12 mmol), the reaction procedure sequence (Steps A to F) described for Example 27 was used to prepare the title compound (205 mg) as a solid. MS (ESI): 676 m/z $[M+H]^+$, retention time: 1.71 minutes; purity: 95% (214 nm) (LC-MS method 022). $^1$H NMR (400 MHz, $CD_3OD$) δ 7.29 (d, J=3.4 Hz, 1H), 7.28-7.22 (m, 2H), 7.22-7.20 (m, 1H), 7.20-7.15 (m, 2H), 7.13-7.09 (m, 2H), 7.09-7.04 (m, 2H), 6.61 (d, J=3.2 Hz, 1H), 3.63 (s, 3H), 3.49 (s, 2H), 3.39-3.34 (m, 2H), 3.27-3.18 (m, 2H), 2.86 (d, J=13.2 Hz, 1H), 2.76 (d, J=13.2 Hz, 1H), 2.13-2.07 (m, 1H), 1.83-1.76 (m, 1H), 1.56 (s, 3H), 1.49-1.43 (m, 1H), 1.31-1.24 (m, 3H), 1.05 (s, 6H).

Example 62. 3-[3-(3-Ethyl-22,28-difluoro-10,10-dimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

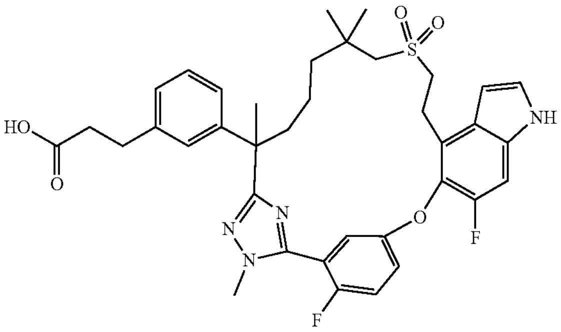

Exchanging ethyl 2-((6-(3-(2-ethoxy-2-oxoethoxy)phenyl)-2,2,6-trimethyl-7-(2-(methyl-$d_3$)-hydrazineyl)-7-oxoheptyl)sulfonyl)acetate (Intermediate 45) with ethyl 3-(3-(7-((2-ethoxy-2-oxoethyl)sulfonyl)-1-(2-ethylhydrazineyl)-6,6-dimethyl-1-oxoheptan-2-yl)phenyl)propanoate (Intermediate 45-6, 3.0 g, 5.7 mmol), the reaction procedure sequence (Steps A to G) described for Example 1 was used to prepare the title compound (300 mg) as a white solid. MS (ESI): 691 m/z $[M+H]^+$, retention time: 2.02 minutes; purity: 93% (214 nm) (LC-MS method 022). $^1$H NMR (400 MHz, $CD_3OD$) 7.37-7.33 (m, 2H), 7.32 (d, J=3.2 Hz, 1H), 7.23-7.10 (m, 5H), 7.05 (d, J=7.2 Hz, 1H), 6.63 (d, J=3.2 Hz, 1H), 4.10-4.05 (m, 3H), 3.40-3.36 (m, 2H), 3.34-3.28 (m, 2H), 2.94 (d, J=13.2 Hz, 1H), 2.88-2.80 (m, 2H), 2.53 (t, J=7.7 Hz, 2H), 2.13-2.01 (m, 1H), 1.85-1.74 (m, 1H), 1.40-1.20 (m, 8H), 1.11 (s, 3H), 1.02 (s, 3H).

Example 63. Enantiomers 1 and 2 of 3-[3-[22,28-difluoro-6,10,10-trimethyl-12,12-dioxo-3-(trideuteriomethyl)-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

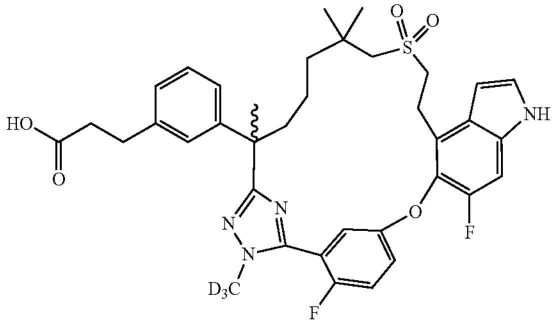

First Eluent: enantiomer 1
Second Eluent: enantiomer 2

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with methyl 3-(3-(7-((2-methoxy-2-oxoethyl)sulfonyl)-2,6,6-trimethyl-1-(2-(methyl-d3)hydrazineyl)-1-oxoheptan-2-yl)phenyl)propanoate (Intermediate 45-7, 3.2 g, 6.38 mmol) in Step A, the reaction procedure sequences (Steps A to H) described for Example 1 was used to prepare the title compounds. The racemic acid, obtained from corresponding Step G of Example 1, was subject to chiral SFC separation under the following condition: Instrument: SFC-80 (Thar, Waters); Column: IG 20*250 mm, 10 μm; Mobile phase: carbon dioxide/isopropanol (0.1% trifluoracetic acid)=65/35; Flow rate: 80 g/minutes; Back pressure: 100 bar; Detection wavelength: 214 nm; Cycle time: 4.5 minutes; Sample solution: 300 mg dissolved in 20 mL methanol. Injection volume: 1 mL. The first eluent, enantiomer 1, is designated as Compound 67A (40.7 mg, 14%); the second eluent, enantiomer 2, is designated as Compound 67B (95.6 mg, 32%).

Compound 67A: MS (ESI): 694 m/z $[M+H]^+$, retention time: 2.10 minutes; purity: 95% (254 nm) (LC-MS method 011). 1H NMR (400 MHz, $CD_3OD$) δ 7.39-7.33 (m, 3H), 7.27-7.16 (m, 3H), 7.11 (s, 1H), 7.07-7.00 (m, 2H), 6.65 (dd, J=3.4 Hz, 0.8 Hz, 1H), 3.46-3.36 (m, 3H), 3.29-3.20 (m, 1H), 3.00 (d, J=13.6 Hz, 1H), 2.86-2.80 (m, 3H), 2.53 (t, J=7.6 Hz, 2H), 2.20 (dt, J=4.6, 12.7 Hz, 1H), 1.84 (dt, J=4.6, 12.7 Hz, 1H), 1.71 (s, 3H), 1.66-1.57 (m, 1H), 1.37-1.30 (m, 2H), 1.26-1.19 (m, 1H), 1.09 (s, 6H) ppm.

Compound 67B: MS (ESI): 694 m/z $[M+H]^+$, retention time: 2.10 minutes; purity: 98% (254 nm) (LC-MS method 011). 1H NMR (400 MHz, $CD_3OD$) δ 7.39-7.33 (m, 3H), 7.27-7.16 (m, 3H), 7.11 (s, 1H), 7.07-7.00 (m, 2H), 6.65 (dd, J=3.4 Hz, 0.8 Hz, 1H), 3.46-3.36 (m, 3H), 3.29-3.20 (m, 1H), 3.00 (d, J=13.6 Hz, 1H), 2.85-2.80 (m, 3H), 2.53 (t, J=7.6 Hz, 2H), 2.20 (dt, J=4.6, 12.7 Hz, 1H), 1.84 (dt, J=4.6, 12.7 Hz, 1H), 1.71 (s, 3H), 1.66-1.56 (m, 1H), 1.36-1.30 (m, 2H), 1.26-1.19 (m, 1H), 1.09 (s, 6H) ppm.

Example 64. Enantiomers 1 and 2 of 3-[3-(22,28-difluoro-6,10,10-trimethyl-12,12-dioxo-24-oxa-12λ6-thia-3,4,19,30-tetrazapentacyclo[23.3.1.12,5.015,23.016,20]triaconta-1(29),2,5(30),15,17,20,22,25,27-nonaen-6-yl)phenyl]propanoic Acid

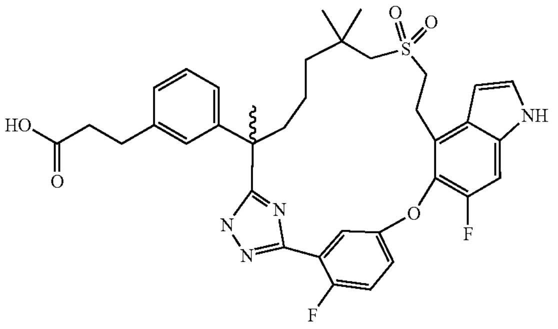

First eluent: enantiomer 1
Second eluent: enantiomer 2

Ethyl 3-(3-(7-((2-ethoxy-2-oxoethyl)sulfonyl)-2-(3-(2-fluoro-5-((6-fluoro-4-vinyl-1H-indol-5-yl)oxy)phenyl)-1H-1,2,4-triazol-5-yl)-6,6-dimethylheptan-2-yl)phenyl)propanoate

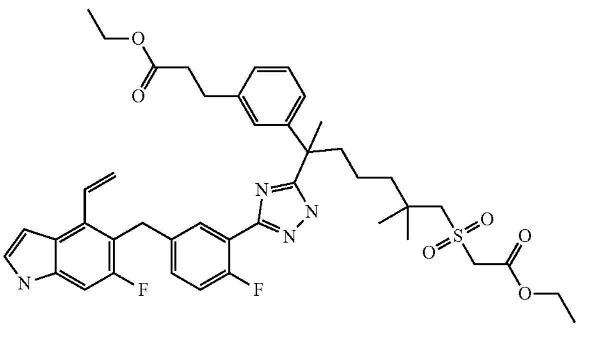 [SMILES: C=Cc1c(Cc2ccc(F)c(-c3n[nH]c(C(C)(CCCC(C)(C)CS(=O)(=O)CC(=O)OCC)c4cccc(CCC(=O)OCC)c4)n3)c2)c(F)cc2[nH]ccc12]

Step A: To a stirred solution of 7-((2-ethoxy-2-oxoethyl)sulfonyl)-2-(3-(3-ethoxy-3-oxopropyl)phenyl)-2,6,6-trimethylheptanoic acid (Intermediate 43-2, 2.3 g, 4.6 mmol) in N,N-dimethylformamide (30 mL) was added 2-fluoro-5-((6-fluoro-4-vinyl-1H-indol-5-yl)oxy)benzimidamide (Intermediate 10-3, 1.58 g, 5.05 mmol), 1-[bis(dimethylamino)methylene]-1H-1,2,3-triazolo[4,5-b]pyridinium 3-oxide hexafluoro-phosphate (HATU, 1.92 g, 5.05 mmol) and diisopropylethylamine (1.78 g, 13.8 mmol) at room temperature. The mixture was stirred at room temperature for 2 hours, then treated with a solution of hydrazine sulfate (0.90 g, 6.9 mmol) and acetic acid (1.05 g, 18.4 mmol). The reaction solution was stirred at 80° C. for an additional 3 hours, cooled to room temperature, and was diluted with ethyl acetate (160 mL). The mixture was washed with water (3×45 mL), brine, dried over sodium sulfate, and concentrated. The residue was purified by automated flash chromatography (40 g silica gel column, 0-50% ethyl acetate in petroleum) to give the title compound (2.15 g, 59%) as a white solid. MS (ESI): 791 m/z $[M+H]^+$, retention time: 2.26 minutes; purity: 95% (254 nm) (LC-MS method 011).

Enantiomers 1 and 2 of 3-[3-(22,28-difluoro-6,10,10-trimethyl-12,12-dioxo-24-oxa-12λ6-thia-3,4,19,30-tetrazapentacyclo[23.3.1.12,5.015,23.016,20]triaconta-1(29),2,5(30),15,17,20,22,25,27-nonaen-6-yl)phenyl]propanoic Acid

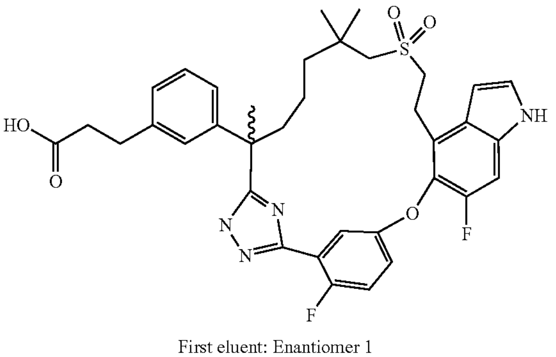

First eluent: Enantiomer 1
Second eluent: Enantiomer 2

Step B: Exchanging ethyl 2-((6-(3-(2-ethoxy-2-oxoethoxy)phenyl)-6-(5-(2-fluoro-5-((6-fluoro-4-vinyl-1H-indol-5-yl)oxy)phenyl)-1-(methyl-$d_3$)-1H-1,2,4-triazol-3-yl)-2,2-dimethylheptyl)sulfonyl)acetate (Step A product in Example 1) with ethyl 3-(3-(7-((2-ethoxy-2-oxoethyl)sulfonyl)-2-(3-(2-fluoro-5-((6-fluoro-4-vinyl-1H-indol-5-yl)oxy)phenyl)-1H-1,2,4-triazol-5-yl)-6,6-dimethylheptan-2-yl)phenyl)propanoate (Step A product of this example, 1.0 g, 1.26 mmol), the reaction procedure sequence (Steps B to H) described for Example 1 is used to prepare the title compounds. The racemic mixture (160 mg), obtained in corresponding Step G of Example 1, was subjected to chiral SFC using a Thar SFC-80 instrument and the following separation conditions: Column: 20×250 mm×10 μm AS; Sample solution: 160 mg dissolved in methanol (15 mL); injection volume: 1.0 mL; eluant: 70:30 carbon dioxide/methanol with 0.2% ammonia/methanol additive; flow rate: 80 mL/minute; column temperature: 35° C.; back pressure: 100 bar; detection wavelength: 214 nm. The first eluent, enantiomer 1, designated as Compound 63A, was obtained as a white solid (30.5 mg, 19%). The second eluent, enantiomer 2, designated as Compound 63B, was also obtained as a white solid (33.3 mg, 21%).

Compound 63A: MS (ESI): 677 m/z $[M+H]^+$, retention time: 1.95 minutes; purity: >99% (254 nm) (LC-MS method 011). $^1H$ NMR (400 MHz, $CD_3OD$) d 7.67-7.65 (m, 1H), 7.32 (d, J=3.6 Hz, 1H), 7.30-7.24 (m, 2H), 7.21-7.15 (m, 2H), 7.06-7.04 (m, 2H), 6.91 (d, J=8.0 Hz, 1H), 6.64 (dd, J=3.2, 0.4 Hz, 1H), 3.43 (t, J=7.2 Hz, 2H), 3.25-3.09 (m, 2H), 2.84 (t, J=7.6 Hz, 2H), 2.70-2.62 (m, 2H), 2.51 (t, J=7.6 Hz, 2H), 2.07-2.01 (m, 1H), 1.84-1.77 (m, 1H), 1.71 (s, 3H), 1.53-1.42 (m, 1H), 1.24-1.17 (m, 1H), 1.04-0.97 (m, 2H), 1.01 (s, 3H), 0.99 (s, 3H) ppm.

Compound 63B: MS (ESI): 677 m/z $[M+H]^+$, retention time: 1.95 minutes; purity: >99% (254 nm) (LC-MS method 011). $^1H$ NMR (400 MHz, $CD_3OD$) d 7.67-7.65 (m, 1H), 7.31 (d, J=3.2 Hz, 1H), 7.30-7.24 (m, 2H), 7.21-7.15 (m, 2H), 7.06-7.04 (m, 2H), 6.91 (d, J=8.0 Hz, 1H), 6.64 (dd, J=3.2, 0.4 Hz, 1H), 3.43 (t, J=7.2 Hz, 2H), 3.25-3.10 (m, 2H), 2.84 (t, J=7.6 Hz, 2H), 2.70-2.62 (m, 2H), 2.52 (t, J=7.6 Hz, 2H), 2.06-2.01 (m, 1H), 1.84-1.77 (m, 1H), 1.71 (s, 3H), 1.53-1.42 (m, 1H), 1.24-1.17 (m, 1H), 1.04-0.97 (m, 2H), 1.01 (s, 3H), 1.00 (s, 3H) ppm.

Example 65. 3-[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]propan-1-ol

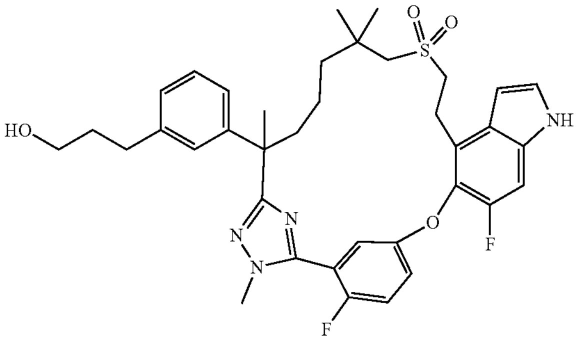 [SMILES: Cn1nc2nc1-c1cc(ccc1F)Oc1c(F)cc3[nH]ccc3c1CCS(=O)(=O)CC(C)(C)CCCC2(C)c1cccc(CCCO)c1]

To a stirred solution of methyl 3-[3-(22,28-difluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl] propanoate (methyl ester of Example 56, 140 mg, 0.20 mol) in tetrahydrofuran (10 mL) was added lithium borohydride (140 mg, 6.43 mmol) and a drop of methanol. The mixture was stirred at room temperature for 16 hours, then quenched with 20 mL of saturated ammonium chloride solution. The solution was extracted twice with ethyl acetate (2×10 mL). The combined organic extracts were washed with brine, dried over sodium sulfate, and concentrated. The residue was purified with automated flash chromatograph to give the title compound (79.2 mg, 60%). MS (ESI): 677 m/z $[M+H]^+$, retention time: 2.13 minutes; purity: >99% (254 nm) (LC-MS method 011). $^1H$ NMR (400 MHz, $CD_3OD$) δ 7.29-7.17 (m, 3H), 7.12-7.03 (m, 3H), 6.98-6.83 (m, 3H), 6.52 (dd, J=3.2, 0.8 Hz, 1H), 3.77-3.75 (m, 3H), 3.42 (t, J=6.4 Hz, 2H), 3.30-3.26 (m, 2H), 3.20-3.16 (m, 1H), 3.13-3.08 (m, 1H), 2.82 (d, J=13.6 Hz, 1H), 2.68 (d, J=13.6 Hz, 1H), 2.50 (t, J=7.6 Hz, 2H), 2.05 (td, J=12.9, 3.7 Hz, 1H), 1.78-1.61 (m, 3H), 1.58 (s, 3H), 1.54-1.42 (m, 1H), 1.28-1.16 (m, 2H), 1.14-1.04 (m, 1H), 0.97 (s, 3H), 0.95 (s, 3H) ppm.

Example 66. Enantiomer 1 and 2 of 3-[3-(23,29-Difluoro-3,11,11-trimethyl-13,13-dioxo-25-oxa-13λ6-thia-5,6,20-triazapentacyclo[24.3.1.02,6.016,24.017,21]triaconta-1(30),2,4,16,18,21,23,26,28-nonaen-7-yl)phenyl]propanoic acid

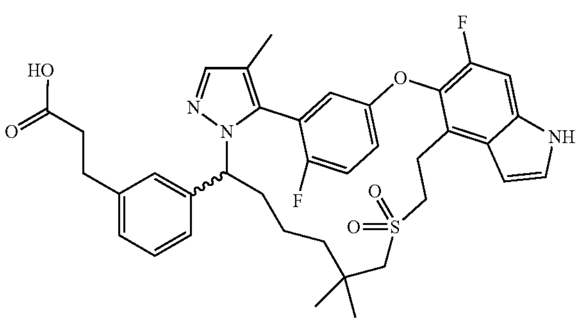

First eluent: enantiomer 1
Second eluent: Enantiomer 2

Example 67. 3-[3-(22,28-Difluoro-3,10,10-trimethyl-12,12-dioxo-24-oxa-12λ6-thia-5,19,30-triazapentacyclo[23.3.1.12,5.015,23.016,20]triaconta-1(29),2(30),3,15,17,20,22,25,27-nonaen-6-yl)phenyl]propanoic Acid

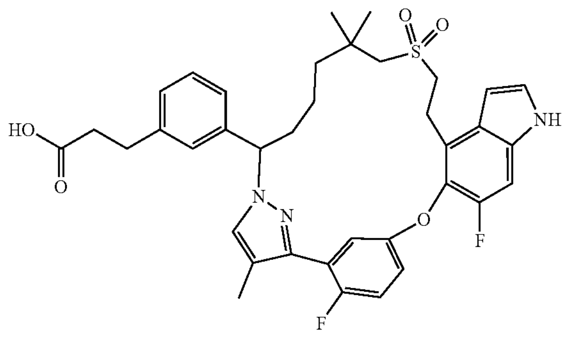 [SMILES: Cc1cn2nc1-c1cc(ccc1F)Oc1c(F)cc3[nH]ccc3c1CCS(=O)(=O)CC(C)(C)CCCC2c1cccc(CCC(=O)O)c1]

Exchanging 3-(2-fluoro-5-((6-fluoro-4-vinyl-1H-indol-5-yl)oxy)phenyl)-1-(tetrahydro-2H-pyran-2-yl)-1H-pyrazole-4-carbonitrile (Intermediate 52) with 6-fluoro-5-[4-fluoro-3-(4-methyl-1H-pyrazol-3-yl)phenoxy]-1-(p-tolylsulfonyl)-4-vinyl-indole (Intermediate 24, 2 g, 4 mmol) in Step B, the reaction procedure sequence (Steps B to F) described for Example 22 was used to prepare the title compounds. The two regio-isomers were separated at corresponding Step D of Example 22, by automated flash chromatography (silica gel column). The first eluent (150 mg), ethyl 3-[3-[22,28-difluoro-3,10,10-trimethyl-19-(p-tolylsulfonyl)-24-oxa-12-thia-5,19,30-triazapentacyclo-[23.3.1.12,5.015,23.016,20]triaconta-1(29),2(30),3,15,17,20,22,25,27-nonaen-6-yl]phenyl]-propanoate, as a racemic, was first oxidized to sulfone, then further hydrolyzed to Compound 66 (40 mg), following conditions described in corresponding Steps E and F of Example 22.

The second eluent (200 mg), ethyl 3-[3-[23,29-difluoro-3,11,11-trimethyl-20-(p-tolylsulfonyl)-25-oxa-13-thia-5,6,20-triazapentacyclo[24.3.1.02,6.016,24.017,21]triaconta-1(30),2,4,16,18,21,23,26,28-nonaen-7-yl]phenyl]propanoate, was first oxidized to sulfone, then further hydrolyzed to racemic acid (120 mg). This racemic mixture was subject to chiral SFC separation under the following condition: Instrument: SFC-80 (Thar, Waters); Column: IG 20*250 mm, 10 μm. Column temperature: 35° C.; Mobile phase: carbon dioxide/ethanol (0.5% methanol ammonia as additive)=50/50; Flow rate: 80 g/minute. Back pressure: 100 bar; Detection wavelength: 214 nm; Cycle time: 3.2 minutes; Sample solution: 120 mg dissolved in 15 mL of methanol; Injection volume: 2 mL. The first eluent, enantiomer 1, is designated as Compound 65A (40 mg, 33%) and the second eluent, enantiomer 2, is designated as Compound 65B (40 mg, 33%).

Compound 65A: MS (ESI): 676 m/z $[M+H]^+$, retention time: 1.59 minutes; purity: 95% (214 nm) (LC-MS method 027). $^1H$ NMR (400 MHz, $CD_3OD$) δ 7.54 (s, 1H), 7.38 (d, J=3.2 Hz, 1H), 7.30 (d, J=10.4 Hz, 1H), 7.27-7.20 (m, 4H), 7.18-7.14 (m, 2H), 6.85-6.80 (dt, J=2.4, 7.2 Hz, 1H), 6.62 (d, J=3.2 Hz, 1H), 5.05 (dd, J=10.8, 4.0 Hz, 1H), 3.49-3.38 (m, 1H), 3.32-3.25 (m, 2H), 3.20-3.10 (m, 1H), 3.00 (d, J=14.4 Hz, 1H), 2.95-2.87 (m, 3H), 2.58 (t, J=7.6 Hz, 2H), 2.33-2.25 (m, 1H), 2.09 (s, 3H), 2.06-1.97 (m, 1H), 1.64 (dt, J=4.4, 13.2 Hz, 1H), 1.24 (dt, J=4.4, 12.8 Hz, 1H), 1.19 (s, 3H), 0.97 (s, 3H), 0.96-0.80 (m, 2H) ppm.

Compound 65B: MS (ESI): 676 m/z $[M+H]^+$, retention time: 1.59 minutes; purity: 97% (214 nm) (LC-MS method 027). $^1$H NMR (400 MHz, $CD_3OD$) δ 7.54 (s, 1H), 7.38 (d, J=3.2 Hz, 1H), 7.30 (d, J=10.4 Hz, 1H), 7.27-7.20 (m, 4H), 7.18-7.14 (m, 2H), 6.85-6.80 (m, 1H), 6.62 (d, J=3.2 Hz, 1H), 5.05 (dd, J=10.8, 4.0 Hz, 1H), 3.49-3.38 (m, 1H), 3.32-3.25 (m, 2H), 3.20-3.10 (m, 1H), 3.00 (d, J=14.4 Hz, 1H), 2.95-2.87 (m, 3H), 2.58 (t, J=7.6 Hz, 2H), 2.33-2.25 (m, 1H), 2.09 (s, 3H), 2.06-1.97 (m, 1H), 1.64 (dt, J=4.4, 13.2 Hz, 1H), 1.24 (dt, J=4.4, 12.8 Hz, 1H), 1.19 (s, 3H), 0.97 (s, 3H), 0.96-0.80 (m, 2H) ppm.

Compound 66: MS (ESI): 676 m/z $[M+H]^+$, retention time: 1.93 minutes; purity: 97% (254 nm) (LC-MS method 011). $^1$H NMR (400 MHz, $CD_3OD$) δ 7.35-7.33 (m, 2H), 7.30-7.20 (m, 3H), 7.19-7.15 (m, 2H), 7.12-7.09 (m, 3H), 6.64 (d, J=2.8 Hz, 1H), 5.28 (dd, J=2.8, 8.8 Hz, 1H), 3.44-3.39 (m, 2H), 3.29-3.15 (m, 2H), 2.88 (t, J=7.6 Hz, 2H), 2.70 (s, 2H), 2.54 (t, J=7.6 Hz, 2H), 2.32-2.21 (m, 1H), 2.05 (d, J=3.0 Hz, 3H), 1.93-1.85 (m, 1H), 1.44-1.32 (m, 2H), 1.15-1.10 (m, 2H), 1.09 (s, 3H), 1.00 (s, 3H) ppm.

Example 68. 3-[3-(22,28-Difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

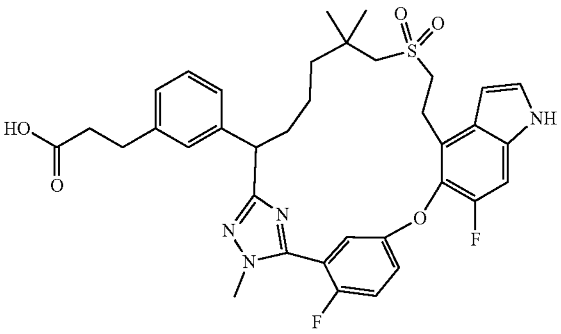 [SMILES: Cn1nc2nc1-c1cc(ccc1F)Oc1c(F)cc3[nH]ccc3c1CCS(=O)(=O)CC(C)(C)CCCC2c1cccc(CCC(=O)O)c1]

Exchanging ethyl 2-((6-(3-(2-ethoxy-2-oxoethoxy)phenyl)-2,2,6-trimethyl-7-(2-(methyl-$d_3$)-hydrazineyl)-7-oxoheptyl)sulfonyl)acetate (Intermediate 45) with ethyl 3-(3-(7-((2-ethoxy-2-oxoethyl)sulfonyl)-6,6-dimethyl-1-(2-methylhydrazineyl)-1-oxoheptan-2-yl)phenyl)propanoate (Intermediate 45-8, 0.98 g, 1.78 mmol) in Step A, the reaction procedure sequence (Steps A to F) described for Example 1 was used to prepare the title compound (80 mg) as a white solid. MS (ESI): 677 m/z $[M+H]^+$, retention time: 2.00 minutes; purity: 97% (254 nm) (LC-MS method 012). $^1$H NMR (400 MHz, DMSO-$d_6$) δ 11.37 (s, 1H), 7.47-7.42 (m, 2H), 7.34-7.27 (m, 3H), 7.17-7.14 (m, 2H), 7.09-7.01 (m, 2H), 6.52 (s, 1H), 3.99 (dd, J=2.8 Hz, J=11.2 Hz, 1H), 3.71 (d, J=2 Hz, 3H), 3.34-3.18 (m, 4H), 3.00-2.92 (m, 2H), 2.75 (t, J=7.2 Hz, 2H), 2.46 (t, J=7.6 Hz, 2H), 2.02-1.99 (m, 1H), 1.66-1.63 (m, 1H), 1.28-1.21 (m, 4H), 1.08 (s, 3H), 0.97 (s, 3H) ppm.

Example 69. 2-[3-(22,28-Difluoro-3,6,10,10-tetramethyl-12,12-dioxo-8,24-dioxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]acetic Acid

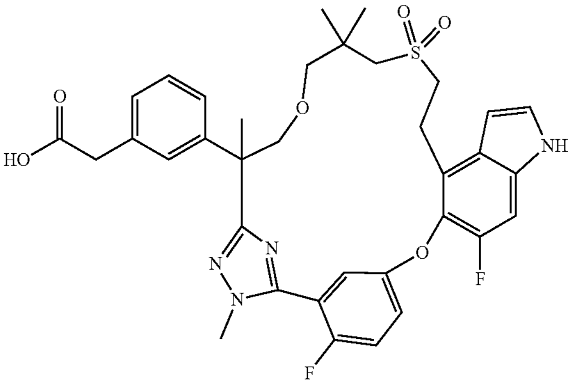 [SMILES: Cn1nc2nc1-c1cc(ccc1F)Oc1c(F)cc3[nH]ccc3c1CCS(=O)(=O)CC(C)(C)COCC2(C)c1cccc(CC(=O)O)c1]

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 2-((3-(2-(3-(2-ethoxy-2-oxoethyl)phenyl)-2-methyl-3-(2-methylhydrazineyl)-3-oxopropoxy)-2,2-dimethylpropyl)sulfonyl)acetate (Intermediate 92, 1.7 g, 3.3 mmol) and methyl 2-fluoro-5-((6-fluoro-4-vinyl-1H-indol-5-yl)oxy)benzimidothioate hydroiodide (Intermediate 14) with methyl 2-fluoro-5-((6-fluoro-1-tosyl-4-vinyl-1H-indol-5-yl)oxy)benzimidothioate hydroiodide (Intermediate 14-3, 1.8 g, 3.6 mmol) in Step A, the reaction procedure sequence (Steps A to G) described for Example 1 was used to prepare the title compound (98 mg) as a white solid. MS (ESI): 679 m/z $[M+H]^+$, retention time: 1.98 minutes; purity: 98% (254 nm) (LC-MS method 017). $^1$H NMR (400 MHz, $CD_3OD$) d 7.49-7.39 (m, 2H), 7.34 (d, J=3.2 Hz, 1H), 7.26-7.12 (m, 4H), 7.09 (d, J=8.0 Hz, 1H), 6.98 (dd, J=5.2, 3.2 Hz, 1H), 6.69 (d, J=3.2 Hz, 1H), 4.03 (d, J=8.0 Hz, 1H), 3.83 (d, J=2.0 Hz, 3H), 3.59 (d, J=8.0 Hz, 1H), 3.51 (s, 2H), 3.50-3.45 (m, 1H), 3.17 (t, J=6.8 Hz, 2H), 3.02 (d, J=8.8 Hz, 1H), 2.91 (d, J=8.8 Hz, 2H), 2.61 (dd, J=19.6, 13.2 Hz, 2H), 1.74 (s, 3H), 0.97 (s, 3H), 0.96 (s, 3H) ppm.

Example 70. 3-[3-(3-Chloro-22,28-difluoro-10,10-dimethyl-12,12-dioxo-24-oxa-12λ6-thia-5,19,30-triazapentacyclo[23.3.1.12,5.015,23.016,20]triaconta-1(29),2(30),3,15,17,20,22,25,27-nonaen-6-yl)phenyl]propanoic Acid

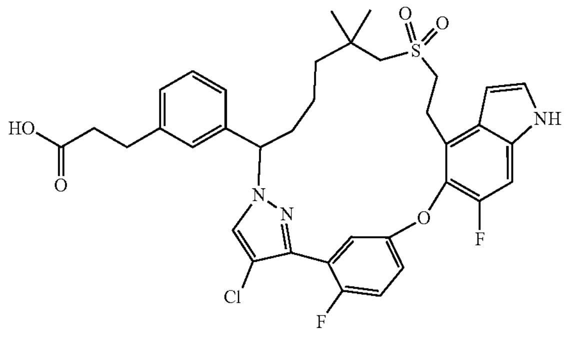 [SMILES: CC1(C)CCCC(c2cccc(CCC(=O)O)c2)n2cc(Cl)c(n2)-c2cc(ccc2F)Oc2c(F)cc3[nH]ccc3c2CCS(=O)(=O)C1]

Example 71. 3-[3-(3-Chloro-23,29-difluoro-11,11-dimethyl-13,13-dioxo-25-oxa-13λ6-thia-5,6,20-tri-azapentacyclo[24.3.1.02,6.016,24.017,21]triaconta-1(30),2,4,16,18,21,23,26,28-nonaen-7-yl)phenyl] propanoic Acid

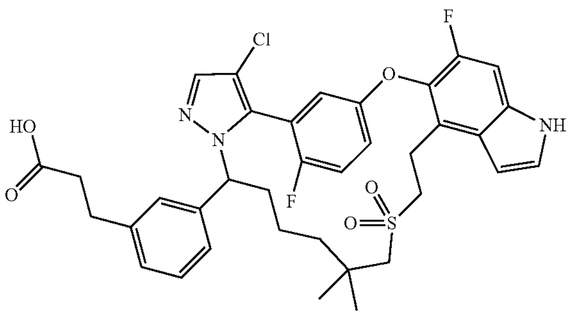 [SMILES: CC1(C)CCCC(c2cccc(CCC(=O)O)c2)n2ncc(Cl)c2-c2cc(ccc2F)Oc2c(F)cc3[nH]ccc3c2CCS(=O)(=O)C1]

Exchanging 3-(2-fluoro-5-((6-fluoro-4-vinyl-1H-indol-5-yl)oxy)phenyl)-1-(tetrahydro-2H-pyran-2-yl)-1H-pyrazole-4-carbonitrile (Intermediate 52) with 5-(3-(4-chloro-1-(tetrahydro-2H-pyran-2-yl)-1H-pyrazol-3-yl)-4-fluorophenoxy)-6-fluoro-4-vinyl-1H-indole (Intermediate 93, 1.6 g, 3.79 mmol) in Step B, The reaction procedure sequence (Steps B to F) described for Example 22 was used to prepare the title compounds as a mixture, which was separated at the last step using prep-HPLC. The first eluent was designated as Compound 70 (11 mg, white solid). The second eluent was designated as Compound 71 (4 mg, white solid).

Compound 70: MS (ESI): 696 m/z $[M+H]^+$, retention time: 2.13 minutes; purity: >99% (214 nm) (LC-MS method 017). $^1$H NMR (400 MHz, $CD_3OD$) δ 7.66 (s, 1H), 7.34 (d, J=3.2 Hz, 1H), 7.28-7.24 (m, 2H), 7.23-7.18 (m, 3H), 7.15-7.12 (m, 3H), 6.64 (d, J=3.2 Hz, 1H), 5.34 (dd, J=2.8 Hz, 12.0 Hz, 1H), 3.41 (t, J=7.6 Hz, 2H), 3.22-3.15 (m, 2H), 2.90 (t, J=7.6 Hz, 2H), 2.76 (s, 2H), 2.57 (t, J=7.6 Hz, 2H), 2.35-2.30 (m, 1H), 1.94-1.88 (m, 1H), 1.44-1.32 (m, 3H), 1.24-1.14 (m, 2H), 1.12 (s, 3H), 1.02 (s, 3H) ppm.

Compound 71: MS (ESI): 696 m/z $[M+H]^+$, retention time: 2.11 minutes; purity: >99% (214 nm) (LC-MS method 017). $^1$H NMR (400 MHz, $CD_3OD$) δ 7.58 (s, 1H), 7.26 (d, J=3.6 Hz, 1H), 7.20-7.11 (m, 6H), 7.06 (d, J=7.6 Hz, 1H), 6.76-6.73 (m, 1H), 6.50 (d, J=3.6 Hz, 1H), 4.95 (q, J=4.0 Hz, 10.8 Hz, 1H), 3.37-3.24 (m, 2H), 3.18-2.99 (m, 2H), 2.91 (d, J=14.4 Hz, 1H), 2.82 (d, J=14.4 Hz, 1H), 2.80 (t, J=7.6 Hz, 2H), 2.46 (t, J=7.6 Hz, 2H), 2.25-2.19 (m, 1H), 1.89-1.83 (m, 1H), 1.53-1.46 (m, 1H), 1.24-1.10 (m, 5H), 1.07 (s, 3H), 0.9 (s, 3H) ppm.

Example 72. Enantiomers 1 and 2 of 3-[3-(22,28-difluoro-3,6,10,10-tetramethyl-12,12-dioxo-9,24-dioxa-12lambda6-thia-3,4,19,30-tetrazapentacyclo-[23.3.1.12,5.015,23.016,20]triaconta-1(29),2(30),4,15,17,20,22,25,27-nonaen-6-yl)phenyl]-butanoic Acid

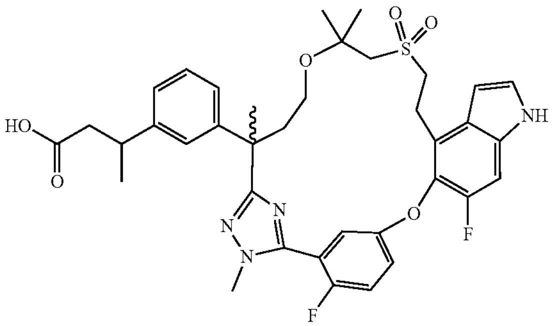

First Eluent: Enantiomer 1
Second Eluent: Enantiomer 2

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(4-((1-((2-ethoxy-2-oxoethyl)sulfonyl)-2-methylpropan-2-yl)oxy)-2-methyl-1-(2-methylhydrazineyl)-1-oxobutan-2-yl)phenyl)butanoate (Intermediate 45-9, 3.97 g, 8.4 mmol) in Step A of Example 1, the reaction procedure sequence (Steps A to H) described in Example 1 was used to prepare the title compounds. The racemic acid mixture (690 mg), obtained in corresponding Step G of Example 1, was subject to chiral SFC using a Thar SFC-80 instrument and the following separation conditions: Column: 20×250 mm×10 μm Chiralpak AD; Sample solution: 690 mg dissolved in methanol (40 mL); Injection volume: 1.2 mL; Mobile phase: 70:30 carbon dioxide/isopropyl alcohol (0.1% trifluoracetic acid as additive); Flow rate: 80 g/min; Column temperature: 35° C.; Back pressure: 100 bar; Detection wavelength: 214 nm; Cycle time: 4.5 minutes. The first eluting isomer, enantiomer 1, was designated as Compound 72A (270 mg, 40%, white solid). The second eluting isomer, enantiomer 2, was designated as Compound 72B (263 mg, 38%, white solid).

Compound 72A: MS (ESI): 707 m/z $[M+H]^+$, retention time: 2.02 minutes; purity: >99% (214 nm) (LC-MS method 012). $^1$H NMR (400 MHz, $CD_3OD$) δ 7.43-7.38 (m, 2H), 7.35 (d, J=3.6 Hz, 1H), 7.25 (d, J=10.4 Hz, 1H), 7.16 (t, J=7.6 Hz, 1H), 7.12-7.10 (m, 1H), 7.05-6.95 (m, 3H), 6.62 (d, J=3.2 Hz, 1H), 3.88 (dd, J=3.2, 1.6 Hz, 3H), 3.71-3.65 (m, 1H), 3.49-3.30 (m, 4H), 3.22-3.09 (m, 4H), 2.43 (t, J=8.0 Hz, 2H), 2.39-2.32 (m, 1H), 2.11-2.06 (m, 1H), 1.68 (s, 3H), 1.30 (s, 3H), 1.26 (d, J=0.8 Hz, 3H), 1.20-1.15 (m, 3H) ppm. Chiral HPLC: 100%.

Compound 72B: MS (ESI): 707 m/z $[M+H]^+$, retention time: 2.02 minutes; purity: >99% (214 nm) (LC-MS method 012). $^1$H NMR (400 MHz, $CD_3OD$) δ 7.43-7.38 (m, 2H), 7.35 (d, J=3.2 Hz, 1H), 7.25 (d, J=10.4 Hz, 1H), 7.16 (t, J=7.6 Hz, 1H), 7.12-7.09 (m, 1H), 7.05-6.95 (m, 3H), 6.62 (d, J=3.2 Hz, 1H), 3.88 (dd, J=3.2, 1.6 Hz, 3H), 3.71-3.65 (m, 1H), 3.49-3.30 (m, 4H), 3.22-3.09 (m, 4H), 2.43 (t, J=8.0 Hz, 2H), 2.39-2.32 (m, 1H), 2.11-2.06 (m, 1H), 1.68 (s, 3H), 1.30 (s, 3H), 1.26 (d, J=0.8 Hz, 3H), 1.20-1.15 (m, 3H) ppm. Chiral HPLC: 100%

Example 73. Enantiomer 1 and 2 of 3-[3-(22,28-difluoro-3,6,10,10-tetramethyl-12,12-dioxo-9,24-dioxa-12lambda6-thia-3,4,19,30-tetrazapentacyclo-[23.3.1.12,5.015,23.016,20]triaconta-1(29),2(30),4,15,17,20,22,25,27-nonaen-6-yl)phenyl]-propanoic Acid

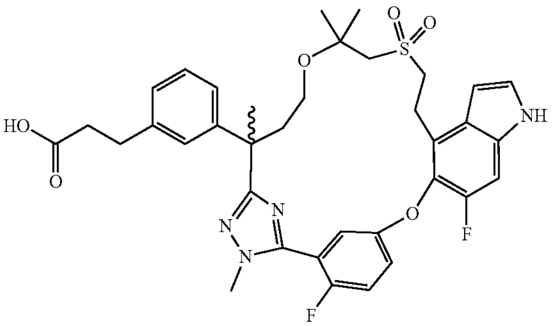

First Eluent: enantiomer 1
Second Eluent: enantiomer 2

Exchanging ethyl 2-((6-(3-(2-ethoxy-2-oxoethoxy)phenyl)-2,2,6-trimethyl-7-(2-(methyl-$d_3$)-hydrazineyl)-7-oxoheptyl)sulfonyl)acetate (Intermediate 45) with ethyl 3-(3-(4-((1-((2-ethoxy-2-oxoethyl)sulfonyl)-2-methylpropan-2-yl)oxy)-2-methyl-1-(2-methylhydrazineyl)-1-oxobutan-2-yl)phenyl)propanoate (Intermediate 45-10, 2.3 g, 4.35 mmol) in Step A, the reaction procedure sequence (Steps A to G) described for Example 1 was used to prepare the title compounds. The racemic mixture was subjected to chiral SFC separation using SFC-80 (Thar, Waters) and the following conditions: Column: 20×250 mm×10 μm Chiralpak AD; sample solution: 360 mg dissolved in methanol (15 mL); injection volume: 0.6 mL; eluant: 70:30 $CO_2$/isopropanol (0.1% trifluoroacetic acid as additive); flow rate: 80 g/min; column temperature: 35° C.; back pressure: 100 bar; detection wavelength: 280 nm; Cycle time: 3.0 minutes. The first eluting isomer, enantiomer 1, was designated as Compound 73A (71.1 mg, 20%, white solid). The second eluting isomer, enantiomer 2, was designated as Compound 73B (81.2 mg, 22%, white solid).

Compound 73A: MS (ESI): 693 m/z $[M+H]^+$, retention time: 1.78 minutes; purity: 98% (254 nm) (LC-MS method 021). Chiral HPLC: 100%. $^1H$ NMR (400 MHz, $CD_3OD$) δ 7.40-7.38 (m, 2H), 7.35 (d, J=2.8 Hz, 1H), 7.25 (d, J=10.4 Hz, 1H), 7.15 (t, J=7.6 Hz, 1H), 7.11-7.10 (m, 1H), 7.04-7.01 (m, 2H), 6.95 (d, J=8.0 Hz, 1H), 6.62 (d, J=2.8 Hz, 1H), 3.89 (d, J=3.2 Hz, 3H), 3.71-3.65 (m, 1H), 3.45-3.36 (m, 4H), 3.19-3.07 (m, 3H), 2.81 (t, J=7.6 Hz, 2H), 2.51 (t, J=7.6 Hz, 2H), 2.38-2.31 (m, 1H), 2.12-2.05 (m, 1H), 1.68 (s, 3H), 1.29 (s, 3H), 1.25 (s, 3H) ppm.

Compound 73B: MS (ESI): 693 m/z $[M+H]^+$, retention time: 1.80 minutes; purity: 97% (254 nm) (LC-MS method 021). Chiral HPLC: 100%. VL-1-HO1053-P2: $^1H$ NMR (400 MHz, $CD_3OD$) δ 7.41-7.37 (m, 2H), 7.35 (d, J=3.2 Hz, 1H), 7.25 (d, J=10.4 Hz, 1H), 7.15 (t, J=7.6 Hz, 1H), 7.12-7.09 (m, 1H), 7.04-7.01 (m, 2H), 6.95 (d, J=8.0 Hz, 1H), 6.62 (d, J=2.4 Hz, 1H), 3.89 (d, J=3.2 Hz, 3H), 3.71-3.65 (m, 1H), 3.45-3.36 (m, 4H), 3.19-3.07 (m, 3H), 2.81 (t, J=7.6 Hz, 2H), 2.51 (t, J=7.6 Hz, 2H), 2.38-2.31 (m, 1H), 2.12-2.05 (m, 1H), 1.68 (s, 3H), 1.29 (s, 3H), 1.25 (s, 3H) ppm.

Example 74. 3-[3-(22,28-Difluoro-4-isopropyl-6,10,10-trimethyl-12,12-dioxo-24-oxa-12λ6-thia-3,4,19,30-tetrazapentacyclo-[23.3.1.12,5.015,23.016,20]triaconta-1(29),2,5(30),15,17,20,22,25,27-nonaen-6-yl)phenyl]propanoic acid and Example 75. 3-[3-(22,28-difluoro-3-isopropyl-6,10,10-trimethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl)phenyl]propanoic Acid

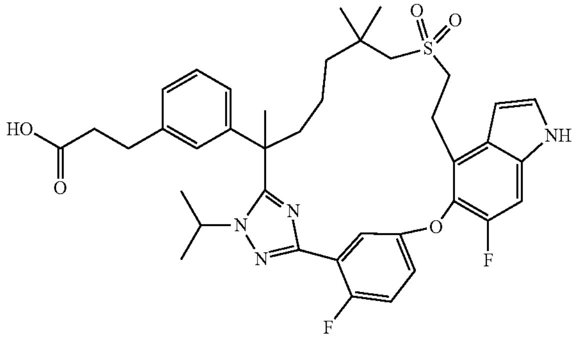

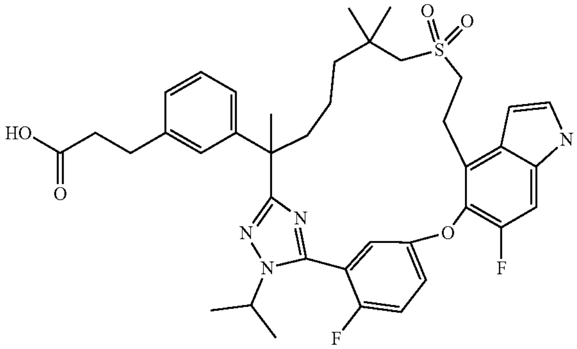

To a stirred solution of methyl 3-[3-(22,28-difluoro-6,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoate (methyl ester of mixture of Compound 63A and Compound 63B, 90 mg, 0.13 mmol) in dry N,N-dimethylformamide (5 mL) was added potassium tert-butoxide (15 mg, 13 mg) under nitrogen. The mixture was stirred at room temperature for 2 hours, then treated with 2-iodopropane (13 μL) and stirred overnight. To the solution was added another 20 μL of 2-iodopropane and stirred at room temperature for two more days, then quenched with saturated ammonium chloride, and extracted with ethyl acetate (2×20 mL). The combined organic extracts were washed with brine (2×20 mL), dried over sodium sulfate, and concentrated. The residue was purified by automated flash chromatography (12 g silica gel column, eluted with 0-50% ethyl acetate in petroleum ether) to give a regio-isomer methyl ester mixture (56 mg). The methyl ester mixture was separated by Prep-HPLC. The first eluent (15 mg, 16%) was further hydrolyzed to Compound 74 (13.2 mg, 90%). The second eluent (18 mg, 19%) was further hydrolyzed to Compound 75 (16 mg, 90%). Both utilized the identical conditions described in Step F of Example 6.

Compound 74: MS (ESI): 719 m/z $[M+H]^+$, retention time: 2.24 minutes; purity: >99% (254 nm) (LC-MS method 012). $^1$H NMR (400 MHz, $CD_3OD$) δ 7.68 (dd, J=5.2, 3.2 Hz, 1H), 7.34 (d, J=3.2 Hz, 1H), 7.30-7.21 (m, 3H), 7.16-7.11 (m, 2H), 7.04 (s, 1H), 6.94 (d, J=7.6 Hz, 1H), 6.66 (d, J=3.2 Hz, 1H), 3.99-3.93 (m, 1H), 3.47 (t, J=7.2 Hz, 2H), 3.20 (t, J=7.2 Hz, 2H), 2.91 (t, J=7.2 Hz, 2H)), 2.78-2.71 (m, 2H), 2.57 (t, J=7.2 Hz, 2H), 1.89-1.79 (m, 1H), 1.75 (s, 3H), 1.62-1.50 (m, 1H), 1.37-1.24 (m, 4H), 1.08-0.98 (m, 12H) ppm.

Compound 75: MS (ESI): 719 m/z [M+H]$^+$, retention time: 2.24 minutes; purity: >99% (254 nm) (LC-MS method 012). $^1$H NMR (400 MHz, $CD_3OD$) δ 7.37-7.31 (m, 3H), 7.22 (d, J=10.8 Hz, 1H), 7.17 (t, J=7.6 Hz, 1H), 7.16-7.12 (m, 1H), 7.07 (s, 1H), 7.03 (d, J=7.6 Hz, 1H), 6.99 (d, J=8.0 Hz, 1H), 6.63 (d, J=3.2 Hz, 1H), 4.52-4.45 (m, 1H), 3.41-3.37 (m, 2H), 3.30-3.15 (m, 2H), 2.94-2.77 (m, 4H), 2.52 (t, J=7.6 Hz, 2H), 2.16-2.10 (m, 1H), 1.87-1.80 (m, 1H), 1.70 (s, 3H), 1.62-1.55 (m, 1H), 1.51 (d, J=6.8 Hz, 3H), 1.42 (d, J=6.4 Hz, 3H), 1.38-1.31 (m, 2H), 1.22-1.16 (m, 1H), 1.09 (s, 3H), 1.07 (s, 3H) ppm.

Example 76. 3-[3-(23,29-Difluoro-3,11,11-trimethyl-13,13-dioxo-9,25-dioxa-13λ6-thia-5,20,31-triazapentacyclo[24.3.1.12,5.016,24.017,21]hentriaconta-1(30),2(31),3,16,18,21,23,26,28-nonaen-6-yl)phenyl]propanoic Acid

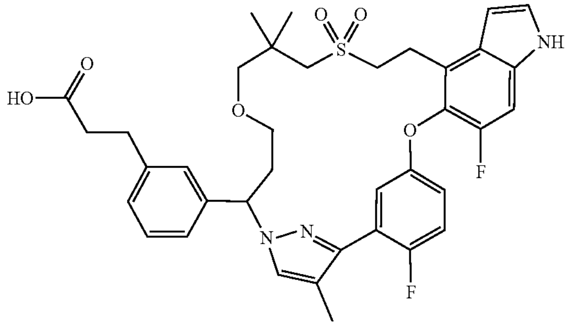 [SMILES: Cc1cn2nc1-c1cc(ccc1F)Oc1c(F)cc3[nH]ccc3c1CCS(=O)(=O)CC(C)(C)COCCC2c1cccc(CCC(=O)O)c1]

Exchanging ethyl 3-(3-(1-bromo-6-((2-ethoxy-2-oxoethyl)thio)-5,5-dimethylhexyl)phenyl)-propanoate (Intermediate 54-1) with ethyl 3-(3-(1-bromo-3-(3-((2-ethoxy-2-oxoethyl)thio)-2,2-dimethylpropoxy)propyl)phenyl) propanoate (Intermediate 54-6, 1.4 g, 2.78 mmol) and 6-fluoro-5-(4-fluoro-3-(1H-pyrazol-3-yl)phenoxy)-1-tosyl-4-vinyl-1H-indole (Intermediate 21) with 6-fluoro-5-(4-fluoro-3-(4-methyl-1H-pyrazol-3-yl)phenoxy)-1-tosyl-4-vinyl-1H-indole (Intermediate 24, 1.4 g, 2.78 mmol) in Step A, the reaction procedure sequence (Steps A to H) described for Example 24 was used to prepare the title compound (35.3 mg) as a white solid. MS (ESI): 692 m/z [M+H]$^+$, retention time: 2.12 minutes; purity: >99% (214 nm) (LC-MS method 017). $^1$H NMR (400 MHz, $CD_3OD$) δ 7.41 (s, 1H), 7.35 (d, J=3.2 Hz, 1H), 7.25-7.11 (m, 7H), 6.95 (dd, J=5.6, 3.2 Hz, 1H), 6.64 (d, J=3.2 Hz, 1H), 5.58 (dd, J=11.6, 3.2 Hz, 1H), 3.50-3.44 (m, 1H), 3.40-3.35 (m, 4H), 3.19-3.14 (m, 1H), 3.11-3.06 (m, 2H), 2.94 (d, J=9.2 Hz, 1H), 2.90-2.82 (m, 3H), 2.66-2.53 (m, 3H), 2.33-2.28 (m, 1H), 2.03 (d, J=2.4 Hz, 3H), 1.13 (s, 3H), 1.03 (s, 3H) ppm.

Example 77. 3-[3-(22,28-Difluoro-3,6,10,10-tetramethyl-12,12-dioxo-24-oxa-12λ6-thia-3,19,30-triazapentacyclo[23.3.1.12,5.015,23.016,20]triaconta-1(29),2(30),4,15,17,20,22,25,27-nonaen-6-yl)phenyl]propanoic Acid

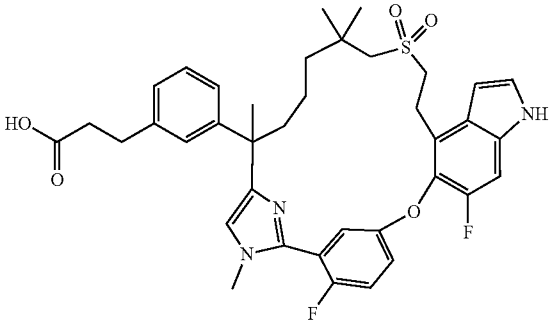 [SMILES: Cn1cc2nc1-c1cc(ccc1F)Oc1c(F)cc3[nH]ccc3c1CCS(=O)(=O)CC(C)(C)CCCC2(C)c1cccc(CCC(=O)O)c1]

Exchanging 2-fluoro-5-((6-fluoro-4-vinyl-1H-indol-5-yl)oxy)benzimidamide (intermediate 10-3) with 2-fluoro-5-((6-fluoro-4-vinyl-1H-indol-5-yl)oxy)-N-methylbenzimidamide (Intermediate 90, 2.2 g, 6.72 mmol), the reaction procedure sequence (Steps A to F) described for Example 27 was used to prepare the title compound (260 mg) as a solid. MS (ESI): 690 m/z [M+H]$^+$, retention time: 1.49 minutes; purity: 97% (214 nm) (LC-MS method 012). $^1$H NMR (400 MHz, $CD_3OD$) d 7.56 (s, 1H), 7.41-7.39 (m, 2H), 7.37-7.36 (m, 1H), 7.33 (d, J=3.2 Hz, 1H), 7.27 (t, J=7.2 Hz, 1H), 7.14 (d, J=10.8 Hz, 1H), 7.15-7.12 (m, 3H), 6.60 (d, J=2.4 Hz, 1H), 3.79 (s, 3H), 3.47-3.34 (m, 2H), 3.33-3.26 (m, 2H), 3.02 (q, J=14.0 Hz, 2H), 2.90 (t, J=7.6 Hz, 2H), 2.58 (t, J=7.6 Hz, 2H), 2.18-2.03 (m, 2H), 1.65 (s, 3H), 1.63-1.59 (m, 1H), 1.46-1.24 (m, 3H), 1.21 (s, 3H), 1.07 (s, 3H) ppm.

Example 78. 2-[3-(22,28-Difluoro-3,6,10,10-tetramethyl-12,12-dioxo-9,24-dioxa-12lambda6-thia-3,4,19,30-tetrazapentacyclo-[23.3.1.12,5.015,23.016,20]triaconta-1(29),2(30),4,15,17,20,22,25,27-nonaen-6-yl)phenyl]-ethanol

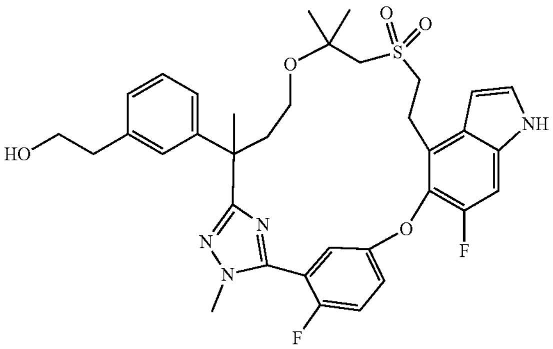 [SMILES: Cn1nc2nc1-c1cc(ccc1F)Oc1c(F)cc3[nH]ccc3c1CCS(=O)(=O)CC(C)(C)OCCC2(C)c1cccc(CCO)c1]

To a stirred solution of borane-tetrahydrofuran (1 M, 5 mL, 5 mmol) was added 2-[3-(22,28-difluoro-3,6,10,10-tetramethyl-12,12-dioxo-9,24-dioxa-12lambda6-thia-3,4,19,30-tetrazapentacyclo-[23.3.1.12,5.015,23.016,20]triaconta-1(29),2(30),4,15,17,20,22,25,27-nonaen-6-yl)phenyl]acetic acid (Example 5, 50 mg, 73 μmol). The mixture was stirred at room temperature for 1 hour, then quenched with water (25 mL), and extracted with ethyl acetate (3×20 mL). The combined organic extracts were washed with brine, dried over sodium sulfate, and concentrated. The residue was purified by automated flash chromatography (20 g silica gel column, eluted with 0-100% ethyl acetate in petroleum ether) to give the title compound, contaminated with over-reduced indoline product. The impure product was further purified by Prep-HPLC to give the title compound (20.2 mg, 41%) as a white solid. MS (ESI): 665 m/z $[M+H]^+$. Room temperature: 2.00 min (LC-MS method 013). $^1H$ NMR (400 MHz, $CD_3OD$) δ 7.42-7.38 (m, 2H), 7.35 (d, J=3.2 Hz, 1H), 7.25 (d, J=10.8 Hz, 1H), 7.16 (t, J=7.6 Hz, 1H), 7.11-7.09 (m, 1H), 7.04-6.96 (m, 3H), 6.63 (dd, J=3.2, 0.4 Hz, 1H), 3.89 (d, J=2.8 Hz, 3H), 3.71-3.65 (m, 3H), 3.44-3.37 (m, 3H), 3.30-3.27 (m, 1H), 3.19-3.13 (m, 1H), 3.09 (d, J=2.8 Hz, 2H), 2.73 (t, J=7.2 Hz, 2H), 2.39-2.32 (m, 1H), 2.13-2.03 (m, 1H), 1.68 (s, 3H), 1.29 (s, 3H), 1.25 (s, 3H) ppm.

Example 79. Enantiomers 1 and 2 of 3-[3-(22,28-difluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]butanoic Acid

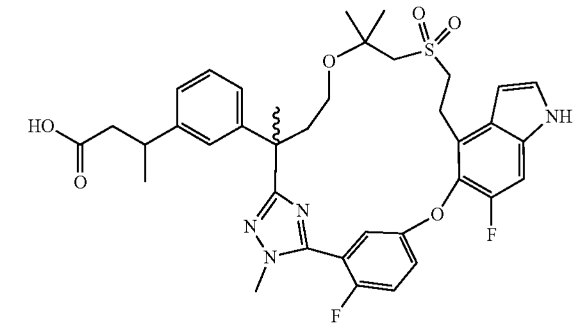 [SMILES: CC(CC(=O)O)c1cccc(C2(C)CCOC(C)(C)CS(=O)(=O)CCc3c(c(F)cc4[nH]ccc34)Oc3ccc(F)c(c3)-c3nc2nn3C)c1]

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(7-((2-ethoxy-2-oxoethyl)sulfonyl)-2,6,6-trimethyl-1-(2-methylhydrazineyl)-1-oxoheptan-2-yl)phenyl)butanoate (Intermediate 45-11, 2.9 g, 5.36 mmol) in Step A, the reaction procedure sequence (Steps A to H) described for Example 1 was used to prepare the title compounds as a white solid. The racemic acid mixture (480 mg), obtained from corresponding Step F of Example 1, was subjected to chiral SFC using instrument SFC-80 (Thar, Waters) with the following conditions: Column: AD 20*250 mm, 10 μm; Column temperature: 35° C.; Mobile phase: carbon dioxide/isopropanol (0.2% Methanol Ammonia)=75/25; Flow rate: 80 g/minutes; Back pressure: 100 bar; Detection wavelength: 230 nm; Cycle time: 6.5 minutes; Sample solution: 480 mg dissolved in 35 mL Methanol; Injection volume: 1.9 mL. The first eluent, Enantiomer 1, was designated as Compound 79A (116 mg, 24%). The second eluent, Enantiomer 2, was designated as Compound 79B (154 mg, 32%).

Compound 79A: MS (ESI): 705 m/z $[M+H]^+$; Retention time: 1.91 minutes; purity: 99% (LC-MS method 021); $^1H$ NMR (400 MHz, $CD_3OD$) δ 7.37-7.35 (m, 2H), 7.33 (d, J=3.2 Hz, 1H), 7.23 (d, J=10.8 Hz, 1H), 7.20-7.16 (m, 2H), 7.10 (d, J=6.4 Hz, 1H), 7.05-7.02 (m, 2H), 6.63 (d, J=3.2 Hz, 1H), 3.86 (s, 3H), 3.44-3.38 (m, 4H), 3.13-3.07 (m, 2H), 2.86 (dd, J=13.6, 6.4 Hz, 1H), 2.44-2.37 (m, 2H), 2.23-2.16 (m, 1H), 1.81-1.76 (m, 1H), 1.70 (s, 3H), 1.63-1.56 (m, 1H), 1.39-1.30 (m, 2H), 1.25-1.20 (m, 1H), 1.16 (d, J=6.8 Hz, 3H), 1.08 (d, J=4.0 Hz, 6H) ppm.

Compound 79B: MS (ESI): 705 m/z $[M+H]^+$; Retention time: 1.91 minutes; purity: 98% (LC-MS method 021); $^1H$ NMR (400 MHz, $CD_3OD$) δ 7.37-7.35 (m, 2H), 7.33 (d, J=3.2 Hz, 1H), 7.23 (d, J=10.4 Hz, 1H), 7.20-7.16 (m, 2H), 7.10 (d, J=6.4 Hz, 1H), 7.04-7.02 (m, 2H), 6.63 (d, J=3.2 Hz, 1H), 3.86 (s, 3H), 3.44-3.35 (m, 4H), 3.13-3.07 (m, 2H), 2.86 (dd, J=13.6, 6.4 Hz, 1H), 2.44-2.35 (m, 2H), 2.23-2.16 (m, 1H), 1.85-1.78 (m, 1H), 1.70 (s, 3H), 1.63-1.56 (m, 1H), 1.39-1.30 (m, 2H), 1.26-1.20 (m, 1H), 1.16 (d, J=7.2 Hz, 3H), 1.08 (d, J=3.6 Hz, 6H) ppm.

Example 80. Enantiomer 1 of 3-[3-[22,28-difluoro-8,12,12-trioxo-24-oxa-12lambda6-thia-3,7,19,30-tetrazapentacyclo[23.3.1.12,5.015,23.016,20]-triaconta-1(29),2,4,15,17,20,22,25,27-nonaen-6-yl]phenyl]propanoic acid and

Example 81. Enantiomer 1 of 22,28-difluoro-12,12-dioxo-6-phenyl-24-oxa-12lambda6-thia-3,7,19,30 tetrazapentacyclo[23.3.1.12,5.015,23.016,20]-triaconta-1(29),2,4,15,17,20,22,25,27-nonaen-8-one

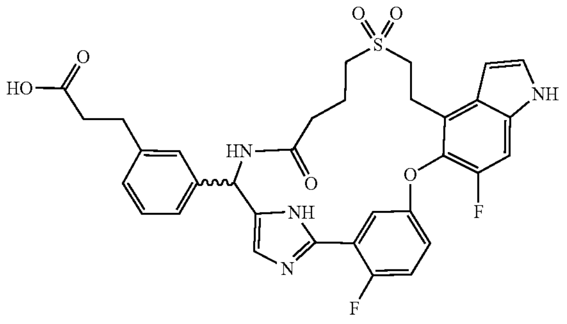

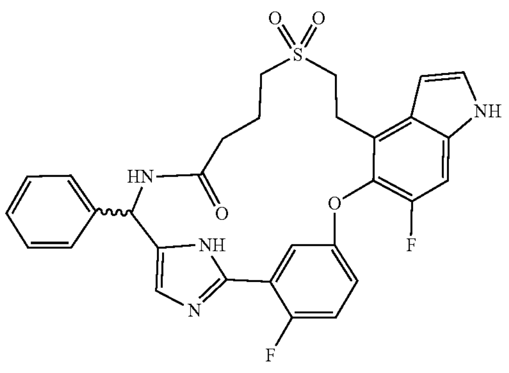

From Diastereomer 1 of Intermediate 98B

Diastereomer 1 of Methyl 4-((2-(5-(3-(5-((R)-(3-bromophenyl)(((R)-tert-butylsulfinyl)amino)-methyl)-1H-imidazol-2-yl)-4-fluorophenoxy)-6-fluoro-1-tosyl-1H-indol-4-yl)ethyl)thio)butanoate (from Diastereomer 1 of Intermediate 98B)

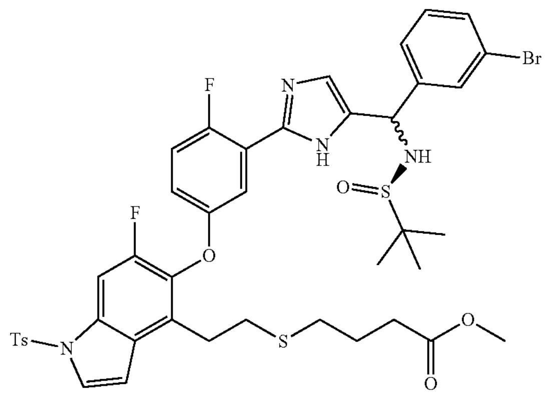 [SMILES: COC(=O)CCCSCCc1c(Oc2ccc(F)c(-c3ncc(C(N[S@](=O)C(C)(C)C)c4cccc(Br)c4)[nH]3)c2)c(F)cc2c1ccn2S(=O)(=O)c1ccc(C)cc1]

Step A: To a stirred solution of Diastereomer 1 of (R)—N-((3-bromophenyl)(2-(2-fluoro-5-((6-fluoro-1-tosyl-4-vinyl-1H-indol-5-yl)oxy)phenyl)-1H-imidazol-5-yl)methyl)-2-methylpropane-2-sulfinamide (Intermediate 98B, 800 mg, 1.03 mmol) and azobisisobutyronitrile (50 mg, 0.3 mmol) in tetrahydrofuran (10 mL) was added methyl 4-mercaptobutanoate (415 mg, 3.1 mmol) under nitrogen. The mixture was stirred at 50° C. for 12 hours, then concentrated. The residue was purified by silica gel column chromatography (petroleum ether/ethyl acetate=2/1 to 1/3) to give the title compound (421 mg, 45%) as a yellow solid. MS (ESI): 913 m/z $[M+H]^+$; Retention time: 2.03 minutes; purity: >99% (LC-MS method 011).

Enantiomer 1 of methyl 4-((2-(5-(3-(5-(amino(3-bromophenyl)methyl)-1H-imidazol-2-yl)-4-fluorophenoxy)-6-fluoro-1-tosyl-1H-indol-4-yl)ethyl)thio) butanoate

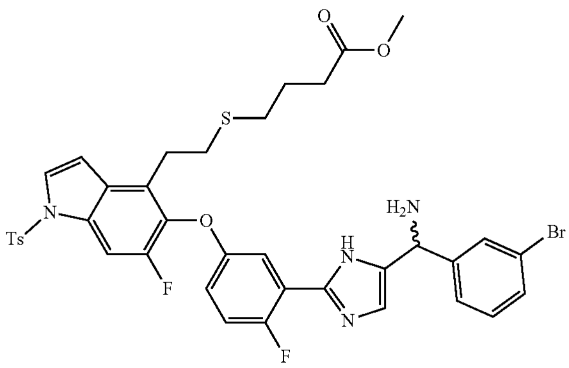 [SMILES: COC(=O)CCCSCCc1c(Oc2ccc(F)c(-c3ncc(C(N)c4cccc(Br)c4)[nH]3)c2)c(F)cc2c1ccn2S(=O)(=O)c1ccc(C)cc1]

Step B: To a stirred solution of Step A product (420 mg, 0.46 mmol) in methanol (6.00 mL) was added hydrogen chloride in 1,4-dioxane (4 M, 0.69 mL, 2.8 mmol). The mixture was stirred at room temperature for 3 hours, then concentrated to give the title compound (375 mg, crude) as a yellow solid. MS (ESI): 809, 811 m/z $[M+H]^+$; Retention time: 1.77 minutes; purity: 83% (LC-MS method 011).

Enantiomer 1 of 4-((2-(5-(3-(5-(amino(3-bromophenyl)methyl)-1H-imidazol-2-yl)-4-fluorophenoxy)-6-fluoro-1H-indol-4-yl)ethyl)thio)butanoic Acid

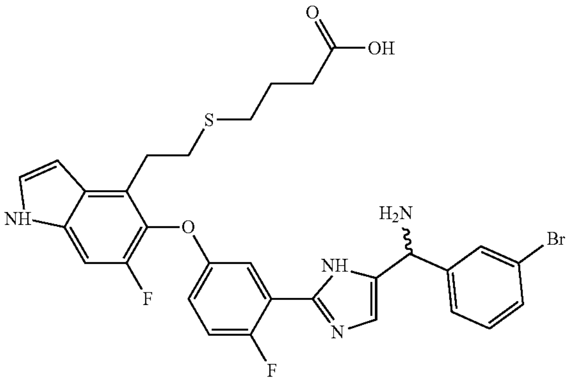 [SMILES: NC(c1cccc(Br)c1)c1cnc(-c2cc(Oc3c(F)cc4[nH]ccc4c3CCSCCCC(=O)O)ccc2F)[nH]1]

Step C: To a stirred solution of Step B product (375 mg, 0.29 mmol) in methanol/water (3/1, 5 mL) was added lithium hydroxide monohydrate (195 mg). The mixture was stirred at 50° C. for 6 hours, then cooled to room temperature, acidified with 1 N hydrochloric acid to pH 4, and extracted with ethyl acetate (2×20 mL). The combined organic extracts were washed with water, brine, dried over sodium sulfate, and concentrated to give the title compound (280 mg, 78%) as a yellow solid. MS (ESI): 641 m/z $[M+H]^+$; Retention time: 1.14 minutes; purity: 83% (LC-MS method 011).

Enantiomer 1 of 6-(3-Bromophenyl)-22,28-difluoro-24-oxa-12-thia-3,7,19,30-tetrazapentacyclo [23.3.1.12,5.015,23.016,20]triaconta-1(29),2,4,15, 17,20,22,25,27-nonaen-8-one

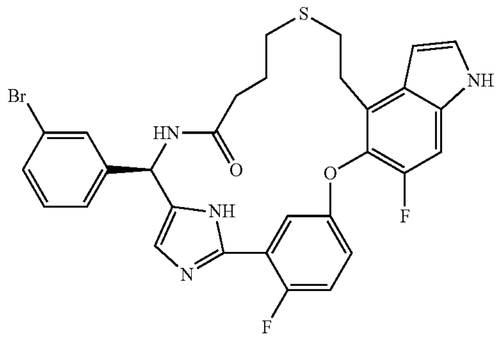 [SMILES: O=C1CCCSCCc2c(c(F)cc3[nH]ccc23)Oc2ccc(F)c(c2)-c2ncc([nH]2)[C@@H](c2cccc(Br)c2)N1]

Step D: To a stirred solution of Step C product (270 mg, 0.4 mmol) in N,N-dimethylformamide (80 mL) was added 1-ethyl-3-(3-dimethylaminopropyl)carbodiimide (323 mg, 1.7 mmol) and hydroxybenzotriazole (227 mg, 1.7 mmol). The reaction mixture was stirred at room temperature for 15 hours, then diluted with water (100 mL), and extracted with ethyl acetate (3×100 mL). The combined organic extracts were washed with brine, dried over sodium sulfate, and concentrated. The residue was purified with silica gel chromatography (petroleum ether/ethyl acetate=1/10) to give the title compound (145 mg, 55%) as a yellow solid. MS (ESI): 623, 625 m/z $[M+H]^+$; Retention time: 1.92 minutes; purity: 83% (LC-MS method 011).

Enantiomer 1 of 6-(3-bromophenyl)-22,28-difluoro-12,12-dioxo-24-oxa-12lambda6-thia-3,7,19,30-tetrazapentacyclo[23.3.1.12,5.015,23.016,20]triaconta-1(29),2,4,15,17,20,22,25,27-nonaen-8-one

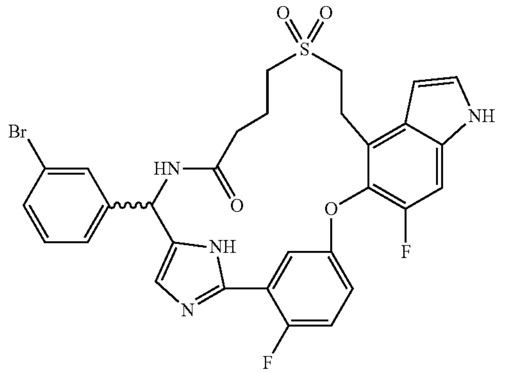 [SMILES: O=C1CCCS(=O)(=O)CCc2c(c(F)cc3[nH]ccc23)Oc2ccc(F)c(c2)-c2ncc([nH]2)C(c2cccc(Br)c2)N1]

Step E: To a stirred and cooled (0° C.) solution of Step D product (145 mg, 0.23 mmol) in methanol (14.5 mL) was added a mixture of ammonium molybdate tetrahydrate (287 mg, 0.23 mmol) in hydrogen peroxide (30% in water, 1.45 mL). The reaction was stirred at 0° C. for 0.5 hours, then diluted with ethyl acetate (100 mL), washed with water, brine, dried over sodium sulfate, and concentrated to give the title compound (110 mg, 72%) as a light-yellow solid. MS (ESI): 655, 657 m/z $[M+H]^+$; Retention time: 1.83 minutes; purity: 79% (LC-MS method 011).

Enantiomer 1 of Ethyl (E)-3-[3-(22,28-difluoro-8,12,12-trioxo-24-oxa-12lambda6-thia-3,7,19,30-tetrazapentacyclo[23.3.1.12,5.015,23.016,20]triaconta-1(29),2,4,15,17,20,22,25,27-nonaen-6-yl)phenyl]prop-2-enoate And inseparable debromination product Enantiomer 1 of 22,28-difluoro-12,12-dioxo-6-phenyl-24-oxa-12lambda6-thia-3,7,19,30 tetrazapentacyclo[23.3.1.12,5.015,23.016,20]triaconta-1(29),2,4,15,17,20,22,25,27-nonaen-8-one

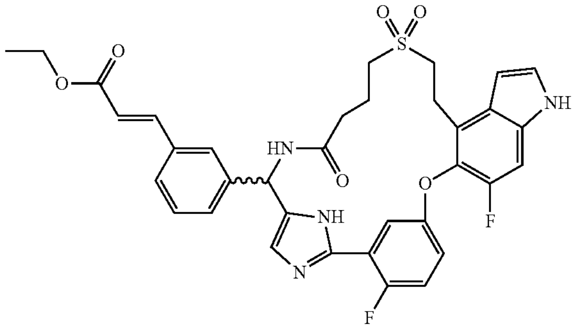

-continued

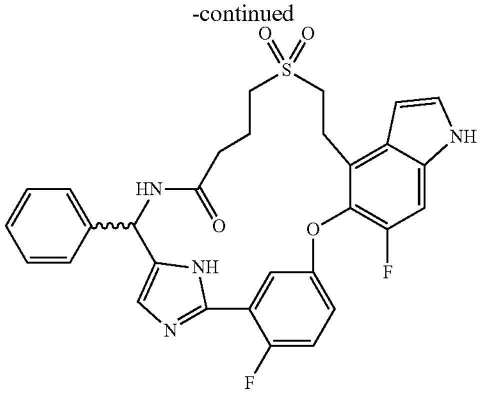

Step F: To a stirred and degassed solution of Step E product (110 mg, 0.17 mmol) and triethylamine (52 mg, 0.51 mmol) in N-methyl pyrrolidinone (3 mL) was added ethyl acrylate (51 mg, 0.51 mmol), palladium (II) acetate (4 mg, 0.2 mmol) and tri(2-methylphenyl)phosphine (11 mg, 0.2 mmol). The mixture was heated at 110° C. under argon for 16 hours, then diluted with water (10 mL), and extracted with ethyl acetate (25 mL). The organic layer was washed with water, brine (10 mL), dried over sodium sulfate, and concentrated. The residue was purified with automated silica gel column chromatography (petroleum ether/ethyl acetate=1/12) to give the title compounds as an inseparable mixture (80 mg, yellow solid). MS (ESI): 675 m/z $[M+H]^+$; Retention time: 1.89 minutes; purity: 47% (LC-MS method 011) (Heck coupling product); MS (ESI): 577 m/z $[M+H]^+$; Retention time: 1.58 minutes; purity: 47% (LC-MS method 011) (debromination product).

Enantiomer 1 of ethyl 3-[3-(22,28-difluoro-8,12,12-trioxo-24-oxa-12lambda6-thia-3,7,19,30 tetrazapentacyclo[23. 3.1.12, 5.015,23.016,20]triaconta-1(29),2,4,15,17,20,22,25,27-nonaen 6-yl)phenyl]propanoate and inseparable debromination product enantiomer 1 of 22,28-difluoro-12,12-dioxo-6-phenyl-24-oxa-12lambda6-thia-3,7,19,30 tetrazapentacyclo-[23.3.1.12,5.015,23.016,20]triaconta-1(29),2,4,15,17,20,22,25,27-nonaen-8-one

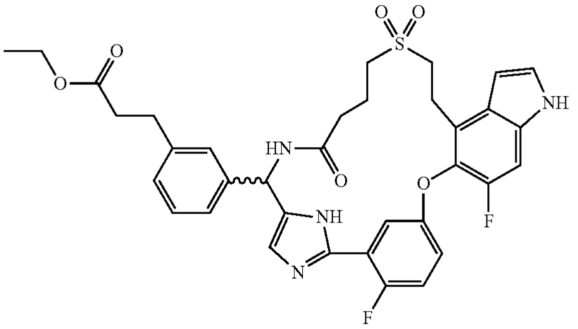

-continued

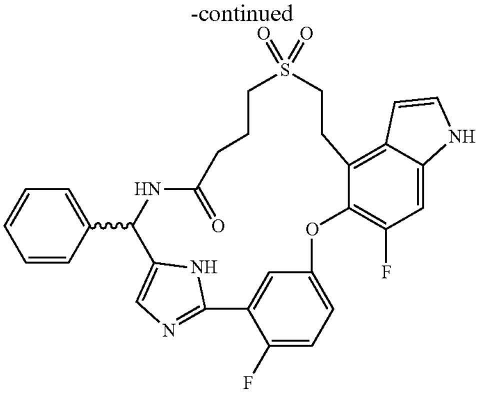

Step G: To a stirred solution of Step F product (80 mg, crude) in ethanol (3.0 mL) was added 10% palladium on carbon (10 mg). The mixture was stirred at room temperature under hydrogen for 2 hours, then filtered through a pad of celite. The filtrate was concentrated to give the crude title mixture (50 mg, crude) as a yellow solid. MS (ESI): 677 m/z $[M+H]^+$; Retention time: 1.78 minutes; purity: 40% (LC-MS method 011) (Heck coupling product).

Compound 80: enantiomer 1 of 3-[3-[22,28-difluoro-8,12,12-trioxo-24-oxa-12lambda6-thia-3,7,19,30-tetrazapentacyclo[23.3.1.12,5.015,23.016,20]triaconta-1(29),2,4,15,17,20,22,25,27-nonaen-6-yl]phenyl]propanoic acid and Compound 81: enantiomer 1 of 22,28-difluoro-12,12-dioxo-6-phenyl-24-oxa-12lambda6-thia-3,7,19,30 tetrazapentacyclo[23.3.1.12,5.015,23.016,20]triaconta-1(29),2,4,15,17,20,22,25,27-nonaen-8-one

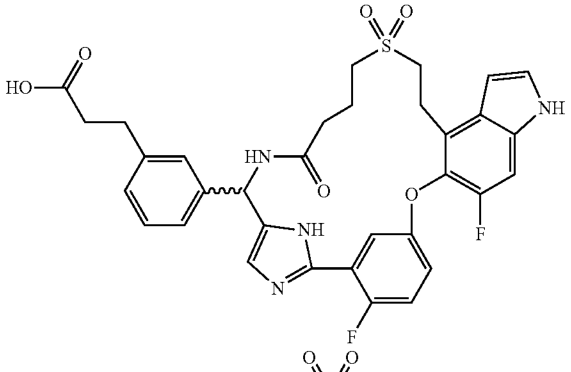

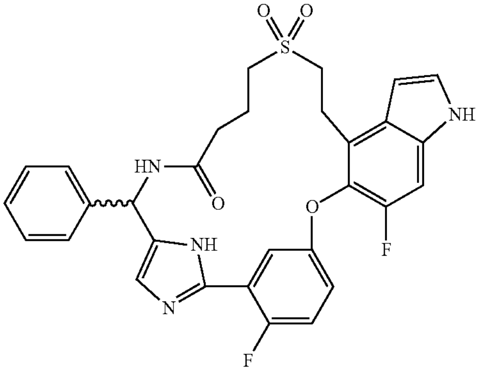

Step H: To a stirred solution of Step G product (50 mg, crude) in methanol/water (3/1, 2.00 mL) was added lithium hydroxide (16 mg, 0.4 mmol). The mixture was stirred at 25° C. for 6 hours, then acidified to pH ~7 with 1M hydrochloric acid, diluted with water (8 mL), and extracted with ethyl acetate (3×10 mL). The combined organic extracts were washed with brine, dried over sodium sulfate, and concentrated. The residue was purified by Prep-HPLC to afford the title compounds. The first eluent, the Heck coupling product, was designated as Compound 80 (18 mg, 38%, white solid). The second eluent, the debromination product from Step F, was designated as Compound 81 (8.5 mg, 19%, white solid).

Compound 80: MS (ESI): 649 m/z $[M+H]^+$; Retention time: 1.58 minutes; purity: >99% (LC-MS method 017). $^1H$ NMR (400 MHz, $CD_3OD$) δ 7.46 (dd, J=6.0 Hz, J=3.2 Hz, 1H), 7.39-7.34 (m, 2H), 7.29-7.17 (m, 7H), 6.69 (d, J=3.2 Hz, 1H), 6.61 (s, 1H), 6.10 (s, 1H), 3.52-3.36 (m, 4H), 3.03-2.95 (m, 2H), 2.91 (t, J=7.6 Hz, 2H), 2.57 (t, J=7.6 Hz, 2H), 2.29 (t, J=6.4 Hz, 2H), 2.20-2.00 (m, 2H) ppm.

Compound 81: MS (ESI): 577 m/z $[M+H]^+$; Retention time: 1.76 minutes; purity: >99% (214 nm); (LC-MS method 017). $^1H$ NMR (400 MHz, $CD_3OD$) δ 7.47 (dd, J=6.0 Hz, J=3.2 Hz, 1H), 7.37-7.34 (m, 5H), 7.32-7.19 (m, 4H), 6.69 (d, J=2.8 Hz, 1H), 6.61 (s, 1H), 6.12 (s, 1H), 3.55-3.36 (m, 4H), 3.03-2.88 (m, 2H), 2.29 (t, J=5.6 Hz, 2H), 2.20-2.01 (m, 2H) ppm.

Example 82. Enantiomer 2 of 3-[3-[22,28-difluoro-8,12,12-trioxo-24-oxa-12lambda6-thia-3,7,19,30-tetrazapentacyclo [23.3.1.12,5.015,23.016,20]-triaconta-1(29),2,4,15,17,20,22,25,27-nonaen-6-yl] phenyl]propanoic acid and Example 83. Enantiomer 2 of 22,28-difluoro-12,12-dioxo-6-phenyl-24-oxa-12lambda6-thia-3,7,19,30-tetrazapentacyclo [23.3.1.12,5.015,23.016,20]-triaconta-1(29),2,4,15,17,20,22,25,27-nonaen-8-one

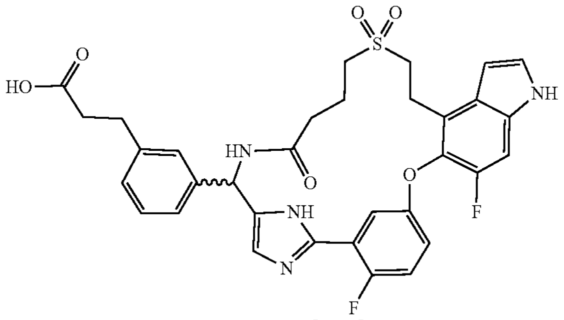

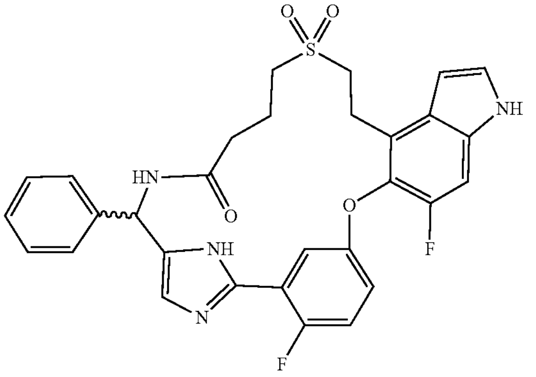

From Diastereomer 2 of Intermediate 98C

Exchanging diastereomer 1 of (R)—N-((3-bromophenyl)(2-(2-fluoro-5-((6-fluoro-1-tosyl-4-vinyl-1H-indol-5-yl)oxy)phenyl)-1H-imidazol-5-yl)methyl)-2-methylpropane-2-sulfinamide (intermediate 98B) with diastereomer 2 (Intermediate 98C) in Step A, the reaction procedure sequence (Steps A to H) described for Example 80 was used to prepare the title compounds. The first eluent from prep-HPLC of Step H, enantiomer 2, the Heck coupling product, is designated as Compound 82 (21.2 mg, white solid). The second eluent, enantiomer 2 of de-bromination product, is designated as Compound 83 (17.6 mg, white solid).

Compound 82: MS (ESI): 649 m/z [M+H]$^+$; Retention time: 1.49 minutes; purity: 95% (214 nm); (LC-MS method 017). $^1$H NMR (400 MHz, $CD_3OD$) δ 7.41-7.15 (m, 9H), 6.67 (d, J=2.8 Hz, 1H), 6.62 (d, J=12.0 Hz, 1H), 6.11 (d, J=12.4 Hz, 1H), 4.45 (t, J=6.0 Hz, 1H), 3.47-3.31 (m, 4H), 2.91-2.76 (m, 4H), 2.56 (t, J=8.0 Hz, 2H), 2.28-2.25 (m, 2H), 2.22-1.98 (m, 2H) ppm.

Compound 83: MS (ESI): 577 m/z [M+H]$^+$; Retention time: 1.76 minutes; purity: >99% (214 nm); (LC-MS method 017). $^1$H NMR (400 MHz, $CD_3OD$) δ 7.50-7.46 (m, 1H), 7.39-7.27 (m, 9H), 6.71 (s, 1H), 6.63 (s, 1H), 6.15 (s, 1H), 3.51-3.35 (m, 4H), 3.01-2.93 (m, 2H), 2.31 (t, J=5.6 Hz, 2H), 2.20-2.08 (m, 2H) ppm.

Example 84. Enantiomer 1 and 2 of 3-[3-(22,28-difluoro-3,10,10-trimethyl-12,12-dioxo-8,24-dioxa-12lambda6-thia-5,19,30-triazapentacyclo[23.3.1.12,5.015,23.016,20]triaconta-1(29),2(30),3,15,17,20,22,25,27-nonaen-6-yl)phenyl]propanoic acid and Example 85. 3-[3-(23,29-difluoro-3,11,11-trimethyl-13,13-dioxo-9,25-dioxa-13λ6-thia-5,6,20-triazapentacyclo[24.3.1.02,6.016,24.017,21]triaconta-1(30),2,4,16,18,21,23,26,28-nonaen-7-yl)phenyl]propanoic Acid

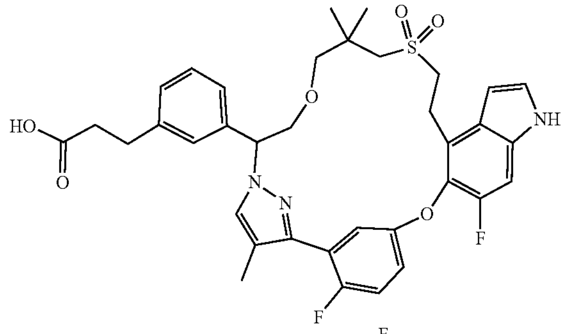

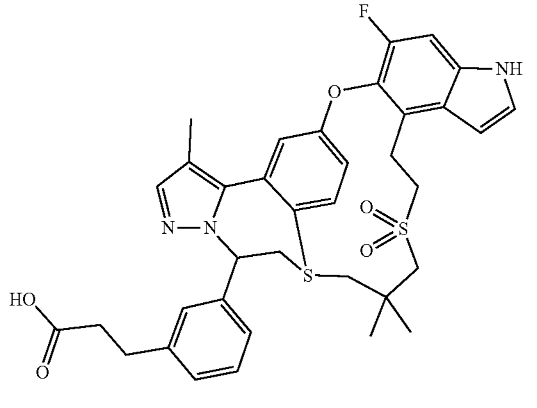

Exchanging 3-(2-fluoro-5-((6-fluoro-4-vinyl-1H-indol-5-yl)oxy)phenyl)-1-(tetrahydro-2H-pyran-2-yl)-1H-pyrazole-4-carbonitrile (Intermediate 52) with 6-fluoro-5-(4-fluoro-3-(4-methyl-1H-pyrazol-3-yl)phenoxy)-1-tosyl-4-vinyl-1H-indole (Intermediate 24, 3.3 g 5.87 mmol) and ethyl 3-(3-(6-mercapto-5,5-dimethyl-1-((tetrahydro-2H-pyran-2-yl)oxy)hexyl)phenyl)propanoate (Step A product in Example 22) with ethyl 3-(3-(2-(3-mercapto-2,2-dimethylpropoxy)-1-((tetrahydro-2H-pyran-2-yl)oxy)ethyl)phenyl)propanoate (Intermediate 33, 6.56 g, 14.7 mmol) in Step B, the reaction procedure sequence (Step B to Step G) described for Example 22 was used to prepare the title compounds. The two regio-isomers are separated in Step F using reverse phase prep-HPLC. The second peak (136 mg) is designated as Compound 85. The first peak is a racemic mixture (150 mg), which was subject to chiral SFC separation conditions as in Step G, Example 22. The first eluent, enantiomer 1, is designated as Compound 84A (34.7 mg, 23%). The second eluent, enantiomer 2, is designated as Compound 84B (34.3 mg, 23%).

Compound 85: MS (ESI): 678 m/z [M+H]$^+$; Retention time: 2.04 minutes; purity: 99% (214 nm); (LC-MS method 017). $^1$HNMR (400 MHz, DMSO-d6): δ11.43 (s, 1H), 8.39 (s, 1H), 7.50 (s, 1H), 7.46 (t, J=2.8 Hz, 1H), 7.40 (d, J=10.8 Hz, 1H), 7.36 (t, J=9.2 Hz, 1H), 7.25 (s, 1H), 7.23-7.15 (m, 4H), 6.83-6.80 (m, 1H), 6.57 (s, 1H), 5.10 (dd, J=4.0, 9.2 Hz, 1H), 4.10 (t, J=9.2 Hz, 1H), 3.82-3.78 (m, 1H), 3.38-2.99 (m, 7H), 2.94 (d, J=8.4 Hz, 1H), 2.78 (t, J=8.0 Hz, 2H), 2.44 (t, J=7.6 Hz, 2H), 1.96 (s, 3H), 1.02 (s, 3H), 0.83 (s, 3H) ppm.

Compound 84A: MS (ESI): 678 m/z [M+H]$^+$; Retention time: 2.08 minutes; purity: 99% (214 nm); (LC-MS method 017). $^1$H NMR (400 MHz, DMSO-$d_6$) δ 12.17 (brs, 1H), 11.38 (s, 1H), 7.55 (s, 1H), 7.45 (t, J=2.8 Hz, 1H), 7.37-7.31 (m, 2H), 7.21-7.14 (m, 4H), 7.09-7.07 (m, 1H), 6.93 (dt, J=3.2, 5.6 Hz, 1H), 6.54 (s, 1H), 5.55 (dd, J=2.8 Hz, J=9.6 Hz, 1H), 4.09 (t, J=10.4 Hz, 1H), 3.72 (dd, J=3.2 Hz, J=9.6 Hz, 1H), 3.33-3.29 (m, 3H), 3.12 (d, J=9.2 Hz, 1H), 3.06 (t, J=6.8 Hz, 2H), 2.88 (d, J=9.2 Hz, 1H), 2.77 (t, J=7.6 Hz, 2H), 2.69 (d, J=13.6 Hz, 1H), 2.50-2.45 (m, 2H), 1.94 (d, J=2.8 Hz, 3H), 0.91 (s, 3H), 0.83 (s, 3H) ppm.

Compound 84B: MS (ESI): 678 m/z [M+H]$^+$; Retention time: 2.08 minutes; purity: 99% (214 nm); (LC-MS method 017). $^1$H NMR (VL-1-HJ1127-Me-P1) (400 MHz, DMSO-$d_6$) δ 12.17 (brs, 1H), 11.38 (s, 1H), 7.55 (s, 1H), 7.45 (t, J=2.8 Hz, 1H), 7.37-7.31 (m, 2H), 7.21-7.14 (m, 4H), 7.09-7.07 (m, 1H), 6.93 (dt, J=3.2, 5.6 Hz, 1H), 6.54 (s, 1H), 5.55 (dd, J=2.8 Hz, J=9.6 Hz, 1H), 4.09 (t, J=10.4 Hz, 1H), 3.72 (dd, J=3.2 Hz, J=9.6 Hz, 1H), 3.33-3.29 (m, 3H), 3.12 (d, J=9.2 Hz, 1H), 3.06 (t, J=6.8 Hz, 2H), 2.88 (d, J=9.2 Hz, 1H), 2.77 (t, J=7.6 Hz, 2H), 2.69 (d, J=13.6 Hz, 1H), 2.50-2.45 (m, 2H), 1.94 (d, J=2.8 Hz, 3H), 0.91 (s, 3H), 0.83 (s, 3H) ppm.

Example 86. Enantiomers 1 and 2 of 3-[3-(21,27-difluoro-3,6,9,9-tetramethyl-11,11-dioxo-23-oxa-11λ6-thia-3,4,18,29-tetrazapentacyclo[22.3.1.12,5.014,22.015,19]nonacosa-1(28),2(29),4,14,16,19,21,24,26-nonaen-6-yl)phenyl]propanoic Acid

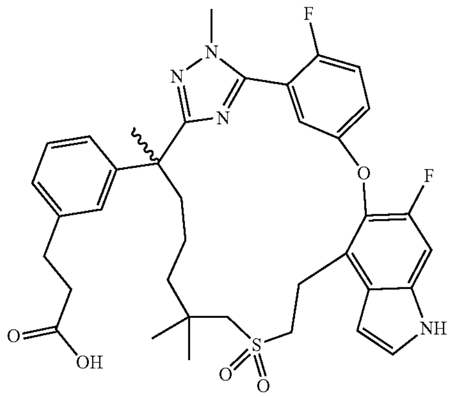 [SMILES: Cn1nc2nc1-c1cc(ccc1F)Oc1c(F)cc3[nH]ccc3c1CCS(=O)(=O)CC(C)(C)CCCC2(C)c1cccc(CCC(=O)O)c1]

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(6-((2-ethoxy-2-oxoethyl)sulfonyl)-2,5,5-trimethyl-1-(2-methylhydrazineyl)-1-oxohexan-2-yl)phenyl)propanoate (Intermediate 45-12, 7.19 g, 15.2 mmol) in Step A, the reaction procedure sequence (Steps A to H) described for Example 1 was used to prepare the title compounds. The first eluent, enantiomer 1, from chiral SFC, as described in Step H of Example 1, is designated as Compound 86A and the second eluent is designated as Compound 86B.

Compound 86A: MS (ESI): 677 m/z $[M+H]^+$; Retention time: 1.74 minutes; purity: 99% (214 nm); (LC-MS method 028). $^1$H NMR (400 MHz, $CD_3OD$) δ 7.33-7.29 (m, 1H), 7.24 (t, J=8.8 Hz, 1H), 7.22-7.19 (m, 1H), 7.18 (d, J=3.2 Hz, 1H), 7.10 (d, J=10.8 Hz, 1H), 7.04 (t, J=7.6 Hz, 1H), 6.97 (s, 1H), 6.90 (t, J=7.2 Hz, 2H), 6.55 (dd, J=3.6 Hz, 0.8 Hz, 1H), 3.77 (d, J=2.4 Hz, 3H), 3.44-3.42 (m, 1H), 3.36-3.22 (m, 2H), 3.19-3.09 (m, 2H), 2.80 (d, J=11.6 Hz, 1H), 2.72 (t, J=7.6 Hz, 2H), 2.40 (t, J=7.6 Hz, 2H), 2.12 (dt, J=12.4 Hz, 2.0 Hz, 1H), 1.80 (dt, J=12.0 Hz, 6.0 Hz, 1H), 1.56 (s, 3H), 1.27-1.19 (m, 1H), 0.97-0.91 (m, 1H), 0.94 (s, 3H), 0.91 (s, 3H) ppm.

Compound 86B: MS (ESI): 677 m/z $[M+H]^+$; Retention time: 1.74 minutes; purity: 95% (214 nm); (LC-MS method 028). $^1$H NMR (400 MHz, $CD_3OD$) δ 7.46-7.42 (m, 1H), 7.36 (t, J=9.2 Hz, 1H), 7.34-7.32 (m, 1H), 7.30 (d, J=3.2 Hz, 1H), 7.22 (d, J=10.8 Hz, 1H), 7.16 (t, J=7.6 Hz, 1H), 7.09 (s, 1H), 7.02 (t, J=7.6 Hz, 2H), 6.67 (dd, J=3.2 Hz, 0.8 Hz, 1H), 3.89 (d, J=2.4 Hz, 3H), 3.58-3.51 (m, 1H), 3.48-3.37 (m, 2H), 3.31-3.21 (m, 2H), 2.90 (d, J=14.0 Hz, 1H), 2.84 (t, J=7.2 Hz, 2H), 2.53 (t, J=7.6 Hz, 2H), 2.24 (dt, J=11.6 Hz, 2.4 Hz, 1H), 1.92 (dt, J=12.4 Hz, 6.0 Hz, 1H), 1.68 (s, 3H), 1.42-1.31 (m, 1H), 1.11-0.99 (m, 1H), 1.06 (s, 3H), 1.04 (s, 3H) ppm.

Example 87. Enantiomers 1 and 2 of 3-[3-(22,28-difluoro-10,10-dimethyl-12,12-dioxo-9,24-dioxa-12lambda6-thia-5,19,30-triazapentacyclo[23.3.1.12,5.015,23.016,20]-triaconta-1(29),2(30),3,15,17,20,22,25,27-nonaen-6-yl)phenyl]propanoic acid and Example 88. 3-[3-(23,29-Difluoro-11,11-dimethyl-13,13-dioxo-10,25-dioxa-13λ6-thia-5,6,20-triazapentacyclo[24.3.1.02,6.016,24.017,21]triaconta-1(30),2,4,16,18,21,23,26,28-nonaen-7-yl)phenyl]propanoic Acid

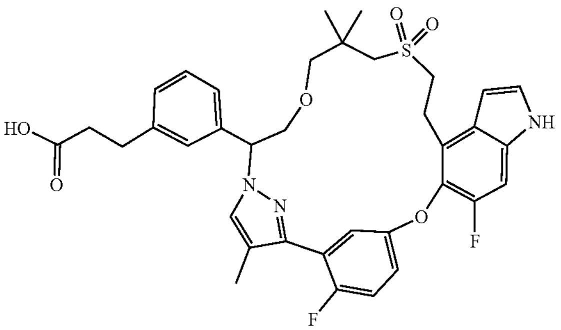

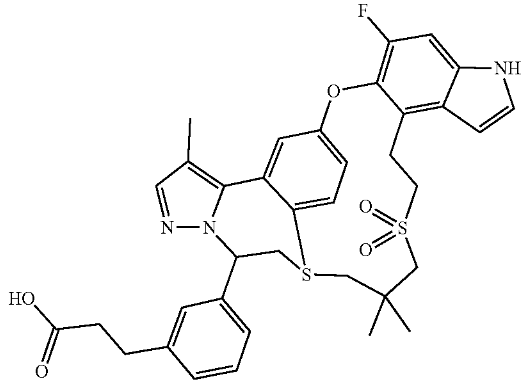

Exchanging ethyl 3-(3-(6-mercapto-5,5-dimethyl-1-((tetrahydro-2H-pyran-2-yl)oxy)hexyl)-phenyl)propanoate (Step A product of Example 22) with ethyl 3-(3-(3-((1-mercapto-2-methylpropan-2-yl)oxy)-1-((tetrahydro-2H-pyran-2-yl)oxy)propyl)phenyl)propanoate (Intermediate 33-1, 1.3 g, 3.06 mmol) and 3-(2-fluoro-5-((6-fluoro-4-vinyl-1H-indol-5-yl)oxy)phenyl)-1-(tetrahydro-2H-pyran-2-yl)-1H-pyrazole-4-carbonitrile (Intermediate 52) with 6-fluoro-5-(4-fluoro-3-(1-(tetrahydro-2H-pyran-2-yl)-1H-pyrazol-3-yl)phenoxy)-4-vinyl-1H-indole (Intermediate 52-1, 1.3 g, 3.06 mmol) in Step B of Example 22, the reaction procedure sequence (Step A to G) described for Example 22 was used to prepare the title compounds. The regio-isomers, as ethyl ester, were separable at corresponding Step D of Example 22 with silica gel column chromatography. The second peak (98 mg), was further hydrolyzed to Compound 88 (36 mg, white solid), as described in corresponding Step F of Example 22. The first peak (140 mg), as a racemic mixture, was first hydrolyzed to corresponding acid (96 mg), then subjected to chiral SFC separation, as described in Steps F and G of Example 22. The chiral SFC separation used an SFC-150 (Waters) instrument and the following separation conditions: Column: AD 20*250 mm, 10 μm; Column temperature: 35° C.; Mobile phase: carbon dioxide/isopropyl alcohol (0.1% trifluoroacetic acid as additive)=65/35; Flow rate: 100 g/minutes; Back pressure: 100 bar; Detection wavelength: 214 nm; Cycle time: 3.5 minutes; Sample solution: 96 mg dissolved in 15 mL methanol. The first eluent, enantiomer 1, is designated as Compound 87A (27.8 mg). The second eluent, enantiomer 2, is designated as Compound 87B (24.3 mg).

Compound 88: MS (ESI): 664 m/z $[M+H]^+$; Retention time: 1.80 minutes; purity: >99% (254 nm); (LC-MS method 012). $^1H$ NMR (400 MHz, $CD_3OD$) δ 7.66 (d, J=1.6 Hz, 1H), 7.43-7.33 (m, 3H), 7.03 (d, J=8.0 Hz, 1H), 6.94 (d, J=10.8 Hz, 1H), 6.70-6.66 (m, 2H), 6.58 (dd, J=3.2, 0.4 Hz, 1H), 6.56 (t, J=2.4 Hz, 1H), 6.46-6.43 (m, 1H), 6.07 (d, J=7.8 Hz, 1H), 5.28 (dd, J=9.6, 4.8 Hz, 1H), 3.52-3.45 (m, 1H), 3.31-3.25 (m, 3H), 3.02 (d, J=15.2 Hz, 1H), 2.91-2.72 (m, 5H), 2.50-2.46 (m, 2H), 2.43-2.37 (m, 1H), 2.25-2.16 (m, 1H), 1.20 (s, 3H), 1.04 (s, 3H) ppm.

Compound 87A: MS (ESI): 664 m/z $[M+H]^+$; Retention time: 1.87 minutes; purity: 99% (254 nm); (LC-MS method 012). $^1H$ NMR (400 MHz, $CD_3OD$) δ 7.58-7.53 (m, 2H), 7.36 (d, J=3.2 Hz, 1H), 7.32 (d, J=10.0 Hz, 1H), 7.21-7.16 (m, 2H), 7.14-7.10 (m, 2H), 7.06 (s, 1H), 6.99 (d, J=7.8 Hz, 1H), 6.69 (dd, J=4.0, 2.4 Hz, 1H), 6.63 (dd, J=3.2, 0.4 Hz, 1H), 5.35 (dd, J=12.0, 2.4 Hz, 1H), 3.52-3.35 (m, 4H), 3.19-3.10 (m, 2H), 3.04 (d, J=14.8 Hz, 1H), 2.97 (d, J=14.8 Hz, 1H), 2.84 (t, J=7.6 Hz, 2H), 2.55-2.47 (m, 3H), 2.10-2.02 (m, 1H), 1.37 (s, 3H), 1.20 (s, 3H) ppm.

Compound 87B: MS (ESI): 664 m/z $[M+H]^+$; Retention time: 1.87 minutes; purity: 99% (254 nm); (LC-MS method 012): $^1H$ NMR (400 MHz, $CD_3OD$) δ 7.55-7.53 (m, 2H), 7.36 (d, J=3.6 Hz, 1H), 7.32 (d, J=10.8 Hz, 1H), 7.21-7.17 (m, 2H), 7.14-7.10 (m, 2H), 7.06 (s, 1H), 6.99 (d, J=7.8 Hz, 1H), 6.69 (dd, J=4.0, 2.0 Hz, 1H), 6.63 (dd, J=3.2, 0.8 Hz, 1H), 5.35 (dd, J=12.4, 2.4 Hz, 1H), 3.52-3.37 (m, 4H), 3.19-3.10 (m, 2H), 3.04 (d, J=14.8 Hz, 1H), 2.97 (d, J=14.8 Hz, 1H), 2.84 (t, J=7.6 Hz, 2H), 2.55-2.48 (m, 3H), 2.09-2.01 (m, 1H), 1.37 (s, 3H), 1.20 (s, 3H) ppm.

Example 89. Enantiomer 1 and 2 of 3-[3-(22,28-difluoro-3,6,10,10-tetramethyl-12,12-dioxo-8,24-dioxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

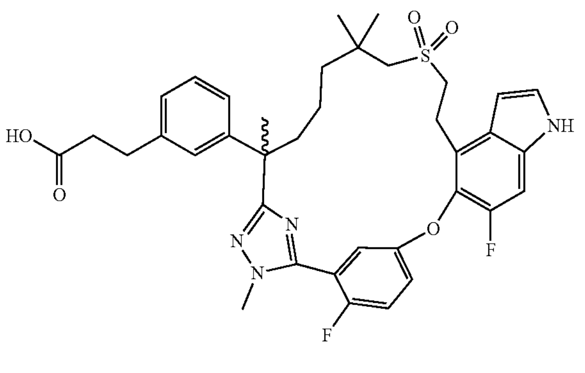

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(3-(3-((2-ethoxy-2-oxoethyl)sulfonyl)-2,2-dimethylpropoxy)-2-methyl-1-(2-methylhydrazineyl)-1-oxopropan-2-yl)phenyl)propanoate (Intermediate 45-13, 3.3 g, 6.24 mmol) in Step A, the reaction procedure sequence (Steps A to H) described for Example 1 was used to prepare the title compounds. The racemic mixture (500 mg), obtained from corresponding Step G of Example 1, was subject to chiral prep-HPLC using Gilson-281 and the following separation conditions: Column: IG 30*250, 5 μm; Mobile phase: n-Hexane (0.1% formic acid): ethanol (0.1% formic acid)=80:20; Flow Rate: 50 mL/minutes; Run time per injection: 6.3 minutes; Injection: 0.4 mL; Sample solution: 500 mg in 30 mL methanol. The first eluent, enantiomer 1, was designated as Compound 89A (150 mg); The second eluent, enantiomer 2, was designated as Compound 89B (110 mg).

Compound 89A: MS (ESI): 693 m/z $[M+H]^+$; Retention time: 2.00 minutes; purity: >99% (214 nm); (LC-MS method 012): $^1H$ NMR (400 MHz, $CD_3OD$) d 7.47-7.45 (m, 1H), 7.41 (t, J=7.6 Hz, 1H), 7.34 (d, J=2.8 Hz, 1H), 7.25 (d, J=8.8 Hz, 1H), 7.17 (t, J=6.0 Hz, 1H), 7.09 (s, 1H), 7.06 (d, J=6.0 Hz, 1H), 7.02 (d, J=6.4 Hz, 1H), 6.99 (dd, J=4.0, 2.4 Hz, 1H), 6.70 (d, J=2.4 Hz, 1H), 4.03 (d, J=6.4 Hz, 1H), 3.83 (d, J=1.6 Hz, 3H), 3.58 (d, J=6.8 Hz, 1H), 3.50-3.44 (m, 2H), 3.17 (t, J=5.6 Hz, 2H), 3.03 (d, J=7.2 Hz, 1H), 2.93 (d, J=7.2 Hz, 1H), 2.84 (t, J=6.4 Hz, 2H), 2.67-2.59 (m, 2H), 2.52 (t, J=6.0 Hz, 2H), 1.73 (s, 3H), 0.97 (s, 6H) ppm.

Compound 89B: MS (ESI): 693 m/z $[M+H]^+$; Retention time: 2.00 minutes; purity: >99% (214 nm); $^1H$ NMR (400 MHz, $CD_3OD$) d 7.48-7.45 (m, 1H), 7.41 (t, J=7.2 Hz, 1H), 7.34 (d, J=2.4 Hz, 1H), 7.25 (d, J=8.8 Hz, 1H), 7.17 (t, J=6.0 Hz, 1H), 7.09 (s, 1H), 7.06 (d, J=6.0 Hz, 1H), 7.02 (d, J=6.4 Hz, 1H), 6.99 (dd, J=4.4, 2.4 Hz, 1H), 6.70 (d, J=2.4 Hz, 1H), 4.03 (d, J=6.4 Hz, 1H), 3.83 (d, J=2.0 Hz, 3H), 3.58 (d, J=6.4 Hz, 1H), 3.50-3.44 (m, 2H), 3.17 (t, J=5.6 Hz, 2H), 3.03 (d, J=7.2 Hz, 1H), 2.93 (d, J=7.2 Hz, 1H), 2.84 (t, J=6.0 Hz, 2H), 2.67-2.59 (m, 2H), 2.52 (t, J=6.0 Hz, 2H), 1.74 (s, 3H), 0.97 (s, 6H) ppm.

Example 90. Diastereomers 1 and 2 of 1-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]ethane-1,2-diol

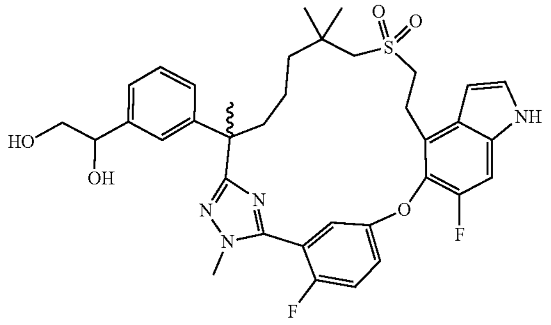 [SMILES: Cn1nc2nc1-c1cc(ccc1F)Oc1c(F)cc3[nH]ccc3c1CCS(=O)(=O)CC(C)(C)CCCC2(C)c1cccc(C(O)CO)c1]

6-[3-(2,2-Dimethyl-1,3-dioxolan-4-yl)phenyl]-22,28-difluoro-3,6,10,10-tetramethyl-24-oxa-12 6-thia-3,4,19,30-tetrazapentacyclo[23.3.1.12,5.015,23.016,20]triaconta-1(29),2(30),4,15,17,20,22,25,27-nonaene 12,12-dioxide

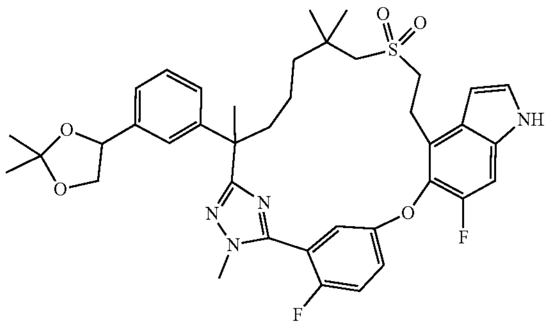 [SMILES: Cn1nc2nc1-c1cc(ccc1F)Oc1c(F)cc3[nH]ccc3c1CCS(=O)(=O)CC(C)(C)CCCC2(C)c1cccc(C2COC(C)(C)O2)c1]

Step A: Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 2-((6-(3-(2,2-dimethyl-1,3-dioxolan-4-yl)phenyl)-2,2,6-trimethyl-7-(2-methylhydrazineyl)-7-oxoheptyl)sulfonyl) acetate (Intermediate 45-14, 1.5 g, 2.85 mmol), the reaction procedure sequence (Steps A to G) described for Example 1 was used to prepare the title compound (280 mg) as a white solid. MS (ESI): 719 m/z $[M+H]^+$; Retention time: 2.00 minutes; purity: 99% (214 nm); (LC-MS method 011).

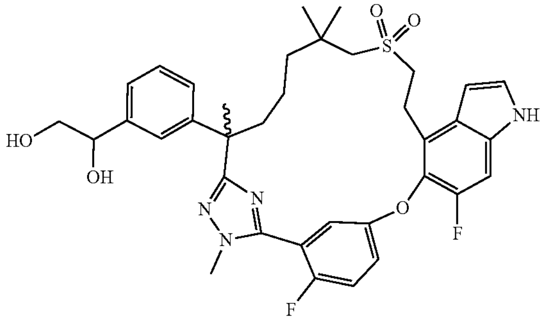 [SMILES: Cn1nc2nc1-c1cc(ccc1F)Oc1c(F)cc3[nH]ccc3c1CCS(=O)(=O)CC(C)(C)CCCC2(C)c1cccc(C(O)CO)c1]

Step B: To a stirred solution of Step A product (260 mg, 0.362 mmol) in methanol (15 mL) was added hydrochloric acid (1 M, 1.81 mL, 1.81 mmol) and stirred at room temperature overnight. The methanol was removed. The aqueous residue was diluted with water (10 mL). The white precipitate formed was collected by filtration and dried to afford the title compound (180 mg, 73.3%). MS (ESI): 679 m/z $[M+H]^+$; Retention time: 1.94 minutes; purity: 96% (214 nm); (LC-MS method 011).

The racemic mixture (180 mg) from above was subjected to chiral prep-HPLC using a Gilson-281 and the following separation conditions: Column: AD 20*250, 10 μm; Mobile phase: n-Hexane (0.1% diethylamine): ethanol (0.1% diethylamine)=80:20; Flow Rate: 50 mL/minute; Run time per injection: 25 minutes; Injection: 1 ml; Sample solution: 180 mg in 15 mL methanol. The first eluent, enantiomer 1, was designated as Compound 90A (41 mg, 23%); The second eluent, enantiomer 2, was designated as Compound 90B (36 mg, 20%).

Compound 90A: MS (ESI): 679 m/z $[M+H]^+$; Retention time: 1.94 minutes; purity: 97% (214 nm); (LC-MS method 11): $^1H$ NMR (400 MHz, $CD_3OD$) δ 7.34-7.32 (m, 3H), 7.26-7.18 (m, 5H), 7.11-7.08 (m, 1H), 6.64 (dd, J=3.2 Hz, 0.8 Hz, 1H), 4.63 (t, J=12.0 Hz, 1H), 3.87 (d, J=2.4 Hz, 3H), 3.57-3.55 (m, 2H), 3.42-3.37 (m, 2H), 3.30-3.17 (m, 2H), 2.92 (d, J=14.0 Hz, 1H), 2.79 (d, J=13.6 Hz, 1H), 2.18 (t, J=11.6 Hz, 1H), 1.90-1.82 (m, 1H), 1.70 (s, 3H), 1.62-1.55 (m, 1H), 1.36-1.30 (m, 1H), 1.22-1.17 (m, 1H), 1.09 (s, 3H), 1.07 (s, 3H), 0.95-0.90 (m, 1H) ppm.

Compound 90B: MS (ESI): 679 m/z $[M+H]^+$; Retention time: 1.94 minutes; purity: 97% (214 nm); (LC-MS method 011). $^1H$ NMR (400 MHz, $CD_3OD$) δ 7.34-7.32 (m, 3H), 7.26-7.18 (m, 5H), 7.11-7.08 (m, 1H), 6.64 (dd, J=3.2 Hz, 0.8 Hz, 1H), 4.64 (t, J=12.0 Hz, 1H), 3.87 (d, J=2.4 Hz, 3H), 3.57-3.55 (m, 2H), 3.42-3.37 (m, 2H), 3.30-3.17 (m, 2H), 2.92 (d, J=14.0 Hz, 1H), 2.80 (d, J=13.6 Hz, 1H), 2.20 (t, J=11.6 Hz, 1H), 1.90-1.82 (m, 1H), 1.70 (s, 3H), 1.62-1.55 (m, 1H), 1.36-1.30 (m, 1H), 1.22-1.17 (m, 1H), 1.09 (s, 3H), 1.07 (s, 3H), 0.95-0.90 (m, 1H) ppm.

Example 91. Enantiomers 1 and 2 of 3-[3-(3-ethyl-22,28-difluoro-6,10,10-trimethyl-12,12-dioxo-24-oxa-12lambda6-thia-3,4,19,30-tetrazapentacyclo [23.3.1.12,5.015,23.016,20]triaconta-1(29),2(30),4,15,17,20,22,25,27-nonaen-6-yl)phenyl]propanoic Acid

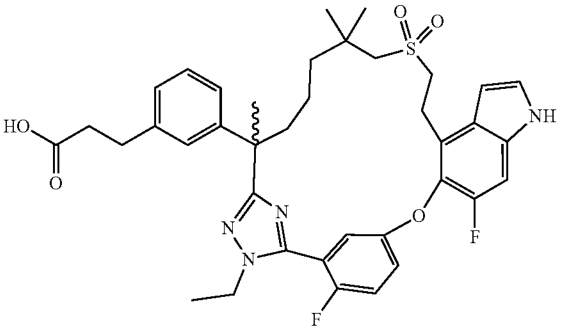 [SMILES: CCn1nc2nc1-c1cc(ccc1F)Oc1c(F)cc3[nH]ccc3c1CCS(=O)(=O)CC(C)(C)CCCC2(C)c1cccc(CCC(=O)O)c1]

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(7-((2-ethoxy-2-oxoethyl)sulfonyl)-1-(2-ethylhydrazineyl)-2,6,6-trimethyl-1-oxoheptan-2-yl)phenyl)propanoate (Intermediate 45-15, 1.576 g, 3.2 mmol) in Step A, the reaction procedure sequence (Steps A to H) described for Example 1 was used to prepare the racemic title compound (223 mg) as a white solid. This racemic mixture (223 mg) was subject to chiral prep-HPLC using Gilson-281 and the following separation conditions: Column: IG 20*250, 10 μm; Mobile Phase: n-hexane (0.1% formic acid): ethanol (0.1% formic acid)=85:15; Flow rate: 40 ml/min; Run time per injection: 25 minutes; Injection: 0.6 ml; Sample solution: 223 mg in 15 mL methanol. Since the final product is acid sensitive, the collected fractions were basified with triethylamine before concentration. After concentration, triethylamine was removed by acid wash, followed by thorough wash with water. The first eluent, enantiomer 1, was designated as Compound 91A (40 mg, 23%); The second eluent, enantiomer 2, was designated as Compound 91B (35 mg, 20%).

Compound 91A: MS (ESI): 705 m/z $[M+H]^+$; Retention time: 1.91 minutes; purity: 98% (214 nm); (LC-MS method 011). Chiral-HPLC purity: 100%. $^1H$ NMR (500 MHz, $CD_3OD$) δ 7.38-7.33 (m, 3H), 7.23 (d, J=11.0 Hz, 1H), 7.18 (t, J=8.0 Hz, 1H), 7.15 (dd, J=5.5, 3.0 Hz, 1H), 7.08 (s, 1H), 7.04 (d, J=8.0 Hz, 1H), 7.01 (d, J=7.5 Hz, 1H), 6.63 (d, J=3.0 Hz, 1H), 4.16 (q, J=7.5 Hz, 2H), 3.42-3.38 (m, 2H), 3.24-3.19 (m, 2H), 2.96 (d, J=13.5 Hz, 1H), 2.85-2.81 (m, 3H), 2.52 (t, J=7.5 Hz, 2H), 2.19-2.14 (m, 1H), 1.86-1.80 (m, 1H), 1.70 (s, 3H), 1.62-1.54 (m, 1H), 1.41 (t, J=7.5 Hz, 3H), 1.36-1.31 (m, 1H), 1.25-1.19 (m, 1H), 1.09 (s, 3H), 1.07 (s, 3H) ppm.

Compound 91B: MS (ESI): 705 m/z $[M+H]^+$; Retention time: 1.91 minutes; purity: 97% (214 nm); (LC-MS method 011). Chiral-HPLC purity: 98%. $^1H$ NMR (500 MHz, $CD_3OD$) δ 7.38-7.33 (m, 3H), 7.23 (d, J=10.5 Hz, 1H), 7.18 (t, J=7.5 Hz, 1H), 7.15 (dd, J=5.5, 3.0 Hz, 1H), 7.08 (s, 1H), 7.04 (d, J=7.5 Hz, 1H), 7.01 (d, J=8.5 Hz, 1H), 6.63 (d, J=3.0 Hz, 1H), 4.16 (q, J=7.5 Hz, 2H), 3.42-3.38 (m, 2H), 3.24-3.19 (m, 2H), 2.96 (d, J=14.0 Hz, 1H), 2.85-2.80 (m, 3H), 2.52 (t, J=7.5 Hz, 2H), 2.19-2.14 (m, 1H), 1.86-1.80 (m, 1H), 1.70 (s, 3H), 1.62-1.54 (m, 1H), 1.41 (t, J=7.5 Hz, 3H), 1.36-1.31 (m, 1H), 1.25-1.19 (m, 1H), 1.09 (s, 3H), 1.07 (s, 3H) ppm.

Example 92. Ethyl 3-[3-(22,28-difluoro-9,9,12,12-tetraoxo-24-oxa-9lambda6,12lambda6-dithia-5,19,30-triazapentacyclo[23.3.1.12,5.015,23.016,20]-triaconta-1(29),2(30),3,15,17,20,22,25,27-nonaen-6-yl)phenyl]propanoate

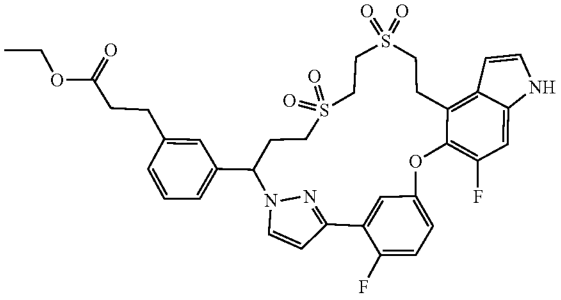 [SMILES: CCOC(=O)CCc1cccc(C2CCS(=O)(=O)CCS(=O)(=O)CCc3c(c(F)cc4[nH]ccc34)Oc3ccc(F)c(c3)-c3ccn2n3)c1]

Example 93. 3-[3-(22,28-Difluoro-9,9,12,12-tetraoxo-24-oxa-9lambda6,12lambda6-dithia-5,19,30 triazapentacyclo[23.3.1.12,5.015,23.016,20]triaconta-1(29),2(30), 3,15,17,20,22,25,27-nonaen-6-yl) phenyl]propanoic acid

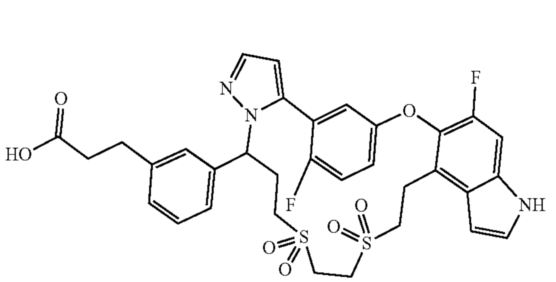 [SMILES: O=C(O)CCc1cccc(C2CCS(=O)(=O)CCS(=O)(=O)CCc3c(c(F)cc4[nH]ccc34)Oc3ccc(F)c(c3)-c3ccnn32)c1]

2-((2-(6-Fluoro-5-(4-fluoro-3-(1-(tetrahydro-2H-pyran-2-yl)-1H-pyrazol-3-yl)phenoxy)-1-tosyl-1H-indol-4-yl)ethyl)thio)ethan-1-ol

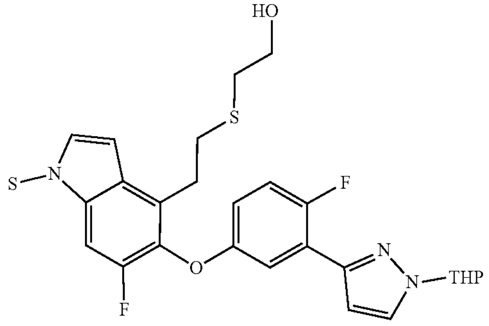

Step A: To a stirred solution of 6-fluoro-5-(4-fluoro-3-(1-(tetrahydro-2H-pyran-2-yl)-1H-pyrazol-3-yl)phenoxy)-1-tosyl-4-vinyl-1H-indole (Intermediate 87B, 4 g, 6.95 mmol) and azobisisobutyronitrile (228 mg, 1.4 mmol) in tetrahydrofuran (30 mL) was added 2-sulfanylethanol (1.63 g, 21 mmol) under nitrogen. The mixture was stirred at 50° C. for 5 hours, then concentrated. The residue was purified by silica gel column chromatography (petroleum ether/ethyl acetate=1/2) to give the title compound (3.8 g, 83%) as a yellow oil. MS (ESI): 654 m/z $[M+H]^+$; Retention time: 2.26 minutes; purity: 85% (214 nm); (LC-MS method 011).

S-(2-((2-(6-Fluoro-5-(4-fluoro-3-(1-(tetrahydro-2H-pyran-2-yl)-1H-pyrazol-3-yl)phenoxy)-1-tosyl-1H-indol-4-yl)ethyl)thio)ethyl) ethanethioate

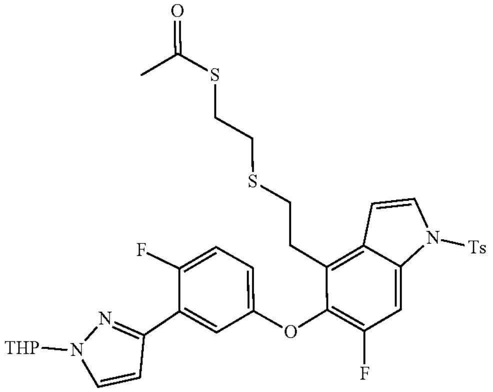

Step B: To a stirred and cooled (0° C.) solution of triphenylphosphine (4.57 g, 17.4 mmol) and diisopropyl azodicarboxylate (3.53 g, 17.4 mmol) in tetrahydrofuran (40 mL) was added a solution of Step A product (3.8 g, 5.8 mmol) and ethanethioic S-acid (1.33 g, 17.4 mmol) in tetrahydrofuran (10 mL). The mixture was stirred at room temperature for 3 hours, then concentrated. The residue was purified with flash column chromatography on silica gel (petroleum ether/ethyl acetate=9/1 to 3/1) to afford the title compound (3.6 g, 87%) as a white solid. MS (ESI): 712 m/z $[M+H]^+$; Retention time: 1.79 minutes; purity: 95% (214 nm) (LC-MS method 011).

2-((2-(6-Fluoro-5-(4-fluoro-3-(1-(tetrahydro-2H-pyran-2-yl)-1H-pyrazol-3-yl)phenoxy)-1-tosyl-1H-indol-4-yl)ethyl)thio)ethane-1-thiol

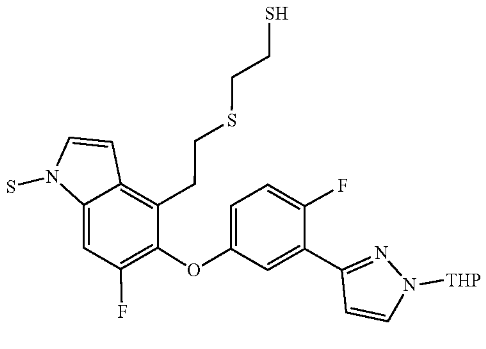

Step C: To a stirred solution of Step B product (3.6 g, 5.1 mmol) in methanol was added sodium methoxide (0.82 g, 15 mmol). The reaction mixture was stirred at room temperature overnight, then concentrated. The residue was purified with silica gel chromatography (petroleum ether/ethyl acetate=5/1 to 1/2) to give the title compound (3.3 g, 97%) as a white solid. MS (ESI): 670 m/z $[M+H]^+$; Retention time: 2.34 minutes; purity: 77% (214 nm) (LC-MS method 011).

1-(3-Bromophenyl)-3-((2-((2-(6-fluoro-5-(4-fluoro-3-(1-(tetrahydro-2H-pyran-2-yl)-1H-pyrazol-3-yl)phenoxy)-1-tosyl-1H-indol-4-yl)ethyl)thio)ethyl)thio)propan-1-one

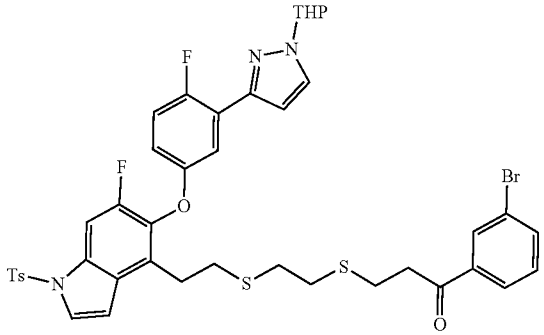

Step D: To a stirred solution of Step C product (3.7 g, 5.5 mmol) in acetone (30 mL, containing 0.5 mL water) was added 1-(3-bromophenyl)prop-2-en-1-one (2.33 g, 11 mmol) and tri-n-butylphosphine (1.12 g, 5.5 mmol). The mixture was stirred at room temperature for 4 hours, then concentrated. The residue was dissolved in 150 mL of ethyl acetate, washed with water, brine, dried over sodium sulfate, and concentrated. The obtained crude title compound (3.8 g, yellow oil) was used in the next step without further purification. MS (ESI): 880, 882 m/z $[M+H]^+$; Retention time: 2.82 minutes; purity: 20% (214 nm) (LC-MS method 011).

1-(3-Bromophenyl)-3-((2-((2-(6-fluoro-5-(4-fluoro-3-(1-(tetrahydro-2H-pyran-2-yl)-1H-pyrazol-3-yl)phenoxy)-1-tosyl-1H-indol-4-yl)ethyl)thio)ethyl)thio)propan-1-ol

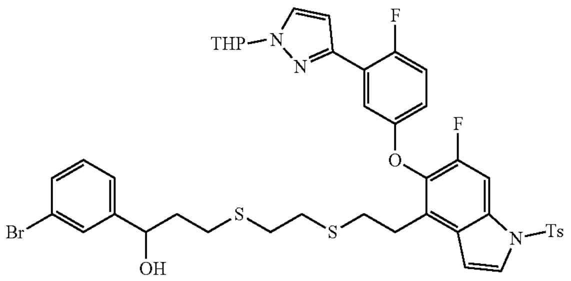

Step E: To a stirred and cooled (0° C.) solution of Step D product (3.3 g, crude) in methanol (50 mL) was added sodium borohydride (356 mg, 9.4 mmol). The mixture was stirred at 0° C. for 2 hours, then quenched with saturated ammonium chloride (100 mL) and extracted with dichloromethane (3×100 mL). The combined organic extracts were dried over sodium sulfate, concentrated to afford the title compound (3.4 g, crude) as a yellow oil, which was used in the next step without further purification. MS (ESI): 882, 884 m/z $[M+H]^+$; Retention time: 1.84 minutes; purity: 18% (214 nm); (LC-MS method 011).

1-(3-Bromophenyl)-3-((2-((2-(6-fluoro-5-(4-fluoro-3-(1-(tetrahydro-2H-pyran-2-yl)-1H-pyrazol-3-yl)phenoxy)-1H-indol-4-yl)ethyl)thio)ethyl)thio)propan-1-ol

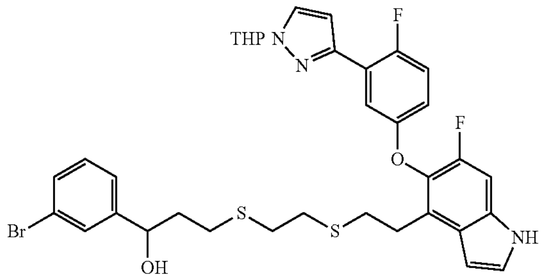 [SMILES: OC(CCSCCSCCc1c(Oc2ccc(F)c(-c3cc[nH]n3)c2)c(F)cc2[nH]ccc12)c1cccc(Br)c1 ; "THP"]

Step F: To a stirred solution of Step E product (3.4 g, crude) in methanol (30 mL) was added lithium hydroxide monohydrate (810 mg, 20 mmol) at room temperature, the mixture was stirred for 15 hours, then poured into water (150 mL), and extracted with ethyl acetate (3×100 mL). The combined organic layers were dried over sodium sulfate, and concentrated. The residue was purified with silica gel column chromatography (petroleum ether/ethyl acetate=21) to afford the title compound (660 mg, 17% of 3 steps) as a yellow oil. MS (ESI): 728, 730 m/z $[M+H]^+$; Retention time: 2.11 minutes; purity: 87% (214 nm) (LC-MS method 011).

1-(3-Bromophenyl)-3-((2-((2-(6-fluoro-5-(4-fluoro-3-(1H-pyrazol-3-yl)phenoxy)-1H-indol-4-yl)ethyl)thio)ethyl)thio)propan-1-ol

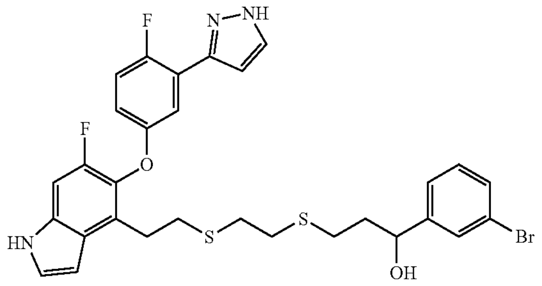 [SMILES: OC(CCSCCSCCc1c(Oc2ccc(F)c(-c3cc[nH]n3)c2)c(F)cc2[nH]ccc12)c1cccc(Br)c1]

Step G: To a stirred solution of Step F product (600 mg, 0.82 mmol) in ethanol (15 mL) was added pyridinium p-toluenesulfonate (425 mg, 2.5 mmol) at room temperature. The mixture was stirred at 60° C. for 3 hours, and then poured into water and extracted with ethyl acetate (3×30 mL). The combined organic layers were dried over sodium sulfate and concentrated. The residue was purified with silica gel column chromatography (petroleum ether/ethyl acetate=2/1) to give the title compound (370 mg, 70%) as a light-yellow solid. MS (ESI): 644, 646 m/z $[M+H]^+$; Retention time: 1.99 minutes; purity: 83% (214 nm); (LC-MS method 011).

Isomer A: 6-(3-bromophenyl)-22,28-difluoro-24-oxa-9,12-dithia-5,19,30-triazapentacyclo[23.3.1.12,5.015,23.016,20]triaconta-1(29),2(30),3,15,17,20,22,25,27-nonaene and Isomer B: 7-(3-bromophenyl)-23,29-difluoro-25-oxa-10,13-dithia-5,6,20-triazapentacyclo[24.3.1.02,6.016,24.017,21]triaconta-1(30),2,4,16,18,21,23,26,28-nonaene

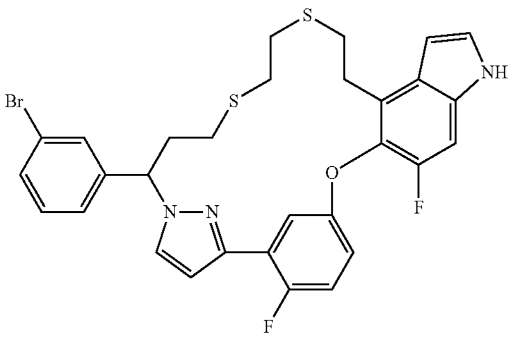

Isomer A

-continued

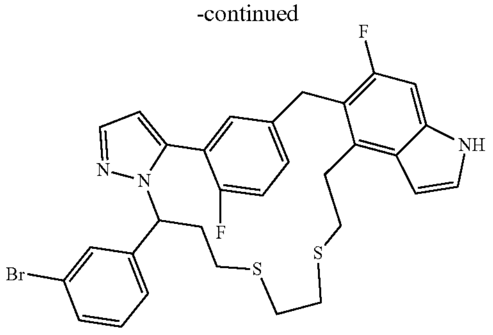

Isomer B

Step H: To a stirred solution of Step G product (370 mg, 0.57 mmol) in 1,4-dioxane (15 mL) was added (tributylphosphoranylidene)acetonitrile (693 mg, 2.9 mmol). The reaction mixture was heated at 150° C. in a microwave reactor for 40 minutes and concentrated. The residue was purified with flash chromatography (0-40% ethyl acetate in petroleum ether) to give the first eluent, isomer A (120 mg, yellow solid). MS (ESI): 626, 628 m/z $[M+H]^+$; Retention time: 2.31 minutes; purity: 79% (254 nm); (LC-MS method 012). Its regio-isomer, the second eluent, Isomer B (80 mg), was also separated as a yellow solid. MS (ESI): 626, 628 m/z $[M+H]^+$; Retention time: 2.27 minutes; purity: 36% (254 nm) (LC-MS method 012).

Ethyl (E)-3-[3-(22,28-difluoro-24-oxa-9,12-dithia-5,19,30-triazapentacyclo-[23.3.1.12,5.015,23.016,20]triaconta-1(29),2(30),3,15,17,20,22,25,27-nonaen-6-yl)phenyl]prop-2-enoate

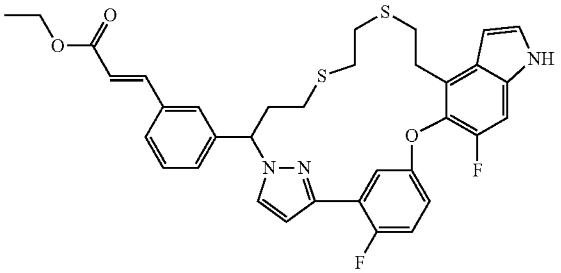 [SMILES: CCOC(=O)/C=C/c1cccc(C2CCSCCSCCc3c(c(F)cc4[nH]ccc34)Oc3ccc(F)c(c3)-c3ccn2n3)c1]

Step I: To a stirred and degassed solution of Isomer A of Step H product (120 mg, 0.2 mmol) in dioxane (4 mL) and water (1 mL) was added ethyl (E)-3-(4,4,5,5-tetramethyl-1,3,2-dioxaborolan-2-yl)acrylate (55 mg, 0.24 mmol), cesium carbonate (124 mg, 0.38 mmol) and [1,1'-Bis-(diphenylphosphino)ferrocene]dichloropalladium (II) (16 mg, 0.02 mmol). The mixture was stirred at 100° C. for 5 hours, then cooled to room temperature, and partitioned between water (5 mL) and ethyl acetate (20 mL). The separated organic layer, combined with two additional ethyl acetate extracts (2×10 mL), was washed with brine, dried over sodium sulfate, and concentrated. The residue was purified with silica gel column chromatography (petroleum ether/ethyl acetate=2/1) to give the title compound (77 mg, 62%) as a light-yellow solid. MS (ESI): 646 m/z $[M+H]^+$; Retention time: 2.26 minutes; purity: 95% (254 nm) (LC-MS method 011).

Ethyl (E)-3-[3-(22,28-difluoro-9,9,12,12-tetraoxo-24-oxa-9 6,12 6-dithia-5,19,30-triazapentacyclo [23.3.1.12,5.015,23.016,20]triaconta-1(29),2(30),3,15,17,20,22,25,27-nonaen-6-yl)phenyl]prop-2-enoate

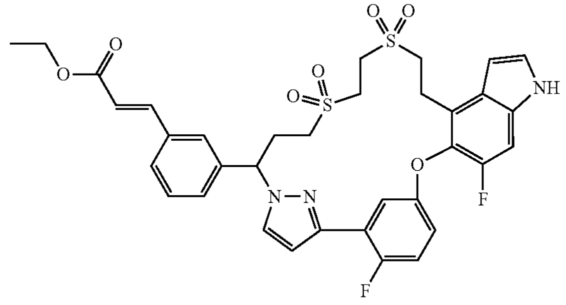 [SMILES: CCOC(=O)/C=C/c1cccc(C2CCS(=O)(=O)CCS(=O)(=O)CCc3c(c(F)cc4[nH]ccc34)Oc3ccc(F)c(c3)-c3ccn2n3)c1]

Step J: To a stirred and cooled solution of Step I product (77 mg, 0.12 mmol) in methanol (8 mL) was added a mixture of ammonium molybdate (154 mg, 0.13 mmol) in hydrogen peroxide (30% in water, 0.78 mL). The mixture was stirred at 0° C. for 1 hour, then diluted with ethyl acetate (15 mL), washed with water (15 mL), dried over sodium sulfate, and concentrated to give the title compound (66 mg, 79%) as a light-yellow solid. MS (ESI): 710 m/z $[M+H]^+$; Retention time: 1.99 minutes; purity: 99% (254 nm) (LC-MS method 011).

Compound 92: Ethyl 3-[3-(22,28-difluoro-9,9,12,12-tetraoxo-24-oxa-9lambda6,12lambda6-dithia-5,19,30-triazapentacyclo[23.3.1.12,5.015,23.016,20]triaconta-1(29),2(30),3,15,17,20,22,25,27-nonaen-6-yl)phenyl]propanoate

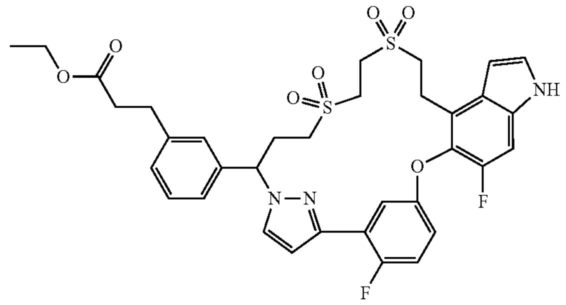 [SMILES: CCOC(=O)CCc1cccc(C2CCS(=O)(=O)CCS(=O)(=O)CCc3c(c(F)cc4[nH]ccc34)Oc3ccc(F)c(c3)-c3ccn2n3)c1]

Step K. To a stirred solution of Step J product (66 mg, 0.093 mmol) in ethanol (5.0 mL) was added 10% palladium on carbon (30 mg). The mixture was stirred at room temperature under hydrogen for 1.5 hours, then filtered through a pad of Celite. The filtrate was concentrated to afford the title compound (57 mg, 86%) as a light-yellow solid. MS (ESI): 712 m/z $[M+H]^+$; Retention time: 1.99 minutes; purity: 95% (254 nm) (LC-MS method 011). $^1H$ NMR (400 MHz, $CDCl_3$) δ 8.53 (s, 1H), 7.41 (dd, J=5.6 Hz, 2.8 Hz, 1H), 7.33-7.31 (m, 2H), 7.28-7.21 (m, 2H), 7.17-7.11 (m, 2H), 6.98 (dt, J=14.4 Hz, 3.2 Hz, 1H), 6.90-6.93 (m, 2H), 6.77 (dd, J=4.0 Hz, 2.4 Hz, 1H), 6.72 (t, J=2.0 Hz, 1H), 5.39 (dd, J=10.0 Hz, 2.4 Hz, 1H), 4.14 (q, J=7.2 Hz, 2H), 3.52 (t, J=6.8 Hz, 2H), 3.34-3.02 (m, 8H), 2.88 (t, J=7.6 Hz, 2H), 2.77-2.69 (m, 1H), 2.59-2.50 (m, 3H), 1.23 (t, J=7.2 Hz, 3H) ppm. The regio-chemistry was confirmed by NOESY $^1H$ NMR.

Ethyl (E)-3-[3-(23,29-difluoro-25-oxa-10,13-dithia-5,6,20-triazapentacyclo-[24.3.1.02,6.016,24.017,21]triaconta-1(30),2,4,16,18,21,23,26,28-nonaen-7-yl)phenyl]prop-2-enoate

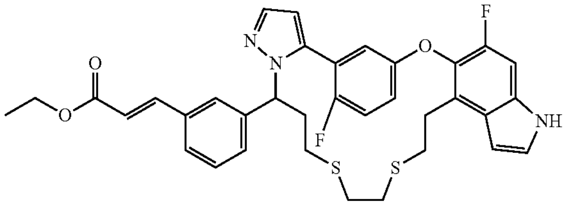 [SMILES: CCOC(=O)/C=C/c1cccc(C2CCSCCSCCc3c(c(F)cc4[nH]ccc34)Oc3ccc(F)c(c3)-c3ccnn32)c1]

Step L. To a stirred and degassed solution of Isomer B of Step H product (80 mg, 0.13 mmol) in dioxane (2 mL) and water (0.5 mL) was added ethyl (E)-3-(4,4,5,5-tetramethyl-1,3,2-dioxaborolan-2-yl)acrylate (35 mg, 0.16 mmol), cesium carbonate (83 mg, 0.25 mmol) and [1,1'-bis(diphenylphosphino)ferrocene]dichloropalladium (II) (10 mg, 0.013 mmol). The mixture was stirred at 100° C. for 5 hours, then cooled to room temperature, and partitioned between water (5 mL) and ethyl acetate (20 mL). The separated organic layer, combined with two additional ethyl acetate extracts (2×10 mL), was washed with brine, dried over sodium sulfate, and concentrated. The residue was purified with silica gel column chromatography (petroleum ether/ethyl acetate=2/1) to give the title compound (50 mg) as a light-yellow solid. MS (ESI): 646 m/z $[M+H]^+$; Retention time: 2.15 minutes; purity: 43% (254 nm) (LC-MS method 011).

(E)-3-[3-(23,29-Difluoro-25-oxa-10,13-dithia-5,6,20-triazapentacyclo-[24.3.1.02,6.016,24.017,21]triaconta-1(30),2,4,16,18,21,23,26,28-nonaen-7-yl)phenyl]prop-2-enoic Acid

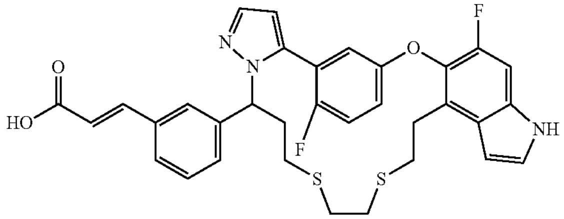 [SMILES: O=C(O)/C=C/c1cccc(C2CCSCCSCCc3c(c(F)cc4[nH]ccc34)Oc3ccc(F)c(c3)-c3ccnn32)c1]

Step M. To a stirred solution of Step L product (50 mg, crude) in methanol/water (3/1, 2.00 mL) was added lithium hydroxide (16 mg, 0.39 mmol). The mixture was stirred at 25° C. for 1 hour, then acidified to pH ~4 with 1 M hydrochloric acid. The suspension was diluted with water (6 mL) and extracted with ethyl acetate (3×10 mL). The combined organic extracts were washed with brine (6 mL), dried over sodium sulfate, and concentrated to give the title compound (44 mg, crude) as a light-yellow solid. MS (ESI): 618 m/z $[M+H]^+$; Retention time: 1.92 minutes; purity: 57% (254 nm) (LC-MS method 011).

Compound 93: 3-[3-(22,28-Difluoro-9,9,12,12-tetraoxo-24-oxa-9lambda6, 12lambda6-dithia-5,19,30 triazapentacyclo[23.3.1.12,5.015,23.016,20]triaconta-1(29),2(30), 3,15,17,20,22,25,27-nonaen-6-yl) phenyl]propanoic Acid

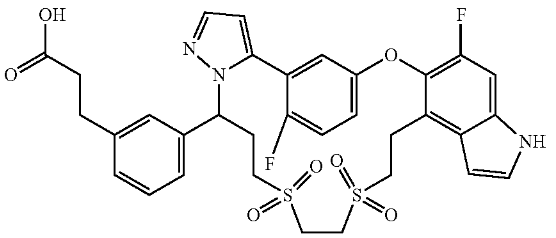 [SMILES: O=C(O)CCc1cccc(C2CCS(=O)(=O)CCS(=O)(=O)CCc3c(c(F)cc4[nH]ccc34)Oc3ccc(F)c(c3)-c3ccnn32)c1]

Step N. Utilizing the identical conditions as described in Steps J and K, the Step M product (44 mg, 0.07 mmol) was converted to the title compound (8 mg) as a white solid. MS (ESI): 684 m/z $[M+H]^+$; Retention time: 1.67 minutes; purity: 95% (254 nm); (LC-MS method 017). $^1H$ NMR (400 MHz, DMSO-$d_6$) δ 11.40 (s, 1H), 7.64 (d, J=2.0 Hz, 1H), 7.45 (t, J=2.8 Hz, 1H), 7.39-7.25 (m, 5H), 7.19-7.11 (m, 2H), 7.05 (dd, J=5.6 Hz, 3.2 Hz, 1H), 6.53 (s, 1H), 6.29 (d, J=2.0 Hz, 1H), 5.20 (t, J=6.4 Hz, 1H), 3.80-3.74 (m, 2H), 3.61-3.18 (m, 8H), 2.91-2.73 (m, 4H), 2.60-2.54 (m, 1H), 2.39-2.30 (m, 1H) ppm. The regio-chemistry was confirmed by NOESY $^1H$ NMR.

Example 94. 3-[3-[(10Z)-10,22,28-Trifluoro-3,6,9,9-tetramethyl-12,12-dioxo-24-oxa-12lambda6-thia-3,4,19,30-tetrazapentacyclo-[23.3.1.12,5.015,23.016,20] triaconta-1(29),2(30),4,10,15,17,20,22,25,27-decaen-6-yl]phenyl]propanoic Acid

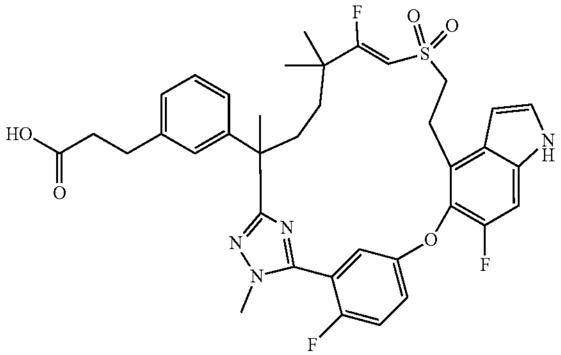 [SMILES: Cn1nc2nc1-c1cc(ccc1F)Oc1c(F)cc3[nH]ccc3c1CCS(=O)(=O)/C=C(\F)C(C)(C)CCC2(C)c1cccc(CCC(=O)O)c1]

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(7-((2-ethoxy-2-oxoethyl)sulfonyl)-6,6-difluoro-2,5,5-trimethyl-1-(2-methylhydrazineyl)-1-oxoheptan-2-yl) phenyl)propanoate (Intermediate 45-16, 1.15 g, 2.04 mmol) in Step A, the reaction procedure sequence (Steps A to G) described for Example 1 was used to prepare the racemic title compound (11 mg) as a white solid. The de-hydrofluorination started at step D, macrocyclization. Throughout, any step that used base, eventually only de-hydrofluorination product was obtained.

Compound 94: MS (ESI): 707 m/z $[M+H]^+$; Retention time: 1.86 minutes; purity: >99% (254 nm); (LC-MS method 013). $^1H$ NMR (400 MHz, $CD_3OD$) δ 7.54-7.50 (m, 1H), 7.43-7.37 (m, 2H), 7.23 (d, J=10.4 Hz, 1H), 7.04 (d, J=7.6 Hz, 1H), 7.00 (s, 1H), 6.88 (d, J=7.2 Hz, 1H), 6.83 (t, J=7.2 Hz, 1H), 6.69 (dd, J=5.2, 3.2 Hz, 1H), 6.65 (d, J=2.4 Hz, 1H), 6.14 (d, J=34.0 Hz, 1H), 3.81 (d, J=2.8 Hz, 3H), 3.78-3.65 (m, 2H), 3.44-3.40 (m, 2H), 2.51-2.46 (m, 1H), 2.33-2.17 (m, 4H), 1.75-1.72 (m, 1H), 1.68 (s, 3H), 1.38-1.25 (m, 2H), 1.08 (s, 3H), 1.04 (s, 3H) ppm.

Example 95. Enantiomers 1 and 2 of 3-[3-(22-fluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

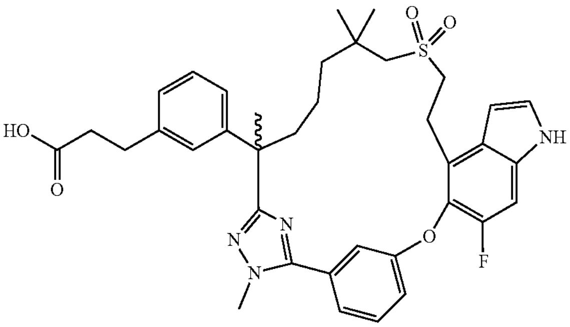 [SMILES: Cn1nc2nc1-c1cccc(c1)Oc1c(F)cc3[nH]ccc3c1CCS(=O)(=O)CC(C)(C)CCCC2(C)c1cccc(CCC(=O)O)c1]

Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(7-((2-ethoxy-2-oxoethyl)sulfonyl)-2,6,6-trimethyl-1-(2-methylhydrazineyl)-1-oxoheptan-2-yl)phenyl)-propanoate (Intermediate 45-17, 2.0 g, 4.0 mmol) and methyl 2-fluoro-5-((6-fluoro-4-vinyl-1H-indol-5-yl)oxy)benzimidothioate hydroiodide (Intermediate 14) with methyl 3-((6-fluoro-1-tosyl-4-vinyl-1H-indol-5-yl)oxy)benzimidothioate (Intermediate 14-4, 1.3 g, 4 mmol) in Step A, the reaction procedure sequence (Steps A to H) described for Example 1 was used to prepare the racemic title compounds. The racemic acid mixture (150 mg), obtained from corresponding Step G of Example 1, was subject to chiral SFC using SFC-80 (Thar, Waters) under the following separation conditions: Column: AS-H 20*250, 10 μm; Mobile Phase: carbon dioxide/ethanol (0.5% Methanol Ammonia as additive)=45/55; Flow Rate: 80 g/minutes; Back pressure: 100 bar; Detection wavelength: 214 nm; Cycle time: 6.2 minutes; Injection: 3.0 ml; Sample solution: 150 mg in 35 mL methanol. The first eluent, enantiomer 1, was designated as Compound 95A (38 mg, 25%); the second eluent, enantiomer 2, was designated as Compound 95B (42 mg, 28%).

Compound 95A: MS (ESI): 673 m/z $[M+H]^+$; Retention time: 2.06 minutes; purity: >99% (214 nm); (LC-MS method 011). Chiral-HPLC purity: 100%. $^1H$ NMR (400 MHz, $CD_3OD$) δ 7.56 (t, J=7.6 Hz, 1H), 7.48 (d, J=7.6 Hz, 1H), 7.35 (s, 1H), 7.33 (d, J=2.8 Hz, 1H), 7.30-7.23 (m, 2H), 7.16 (t, J=7.6 Hz, 1H), 7.10 (s, 1H), 7.08-7.01 (m, 2H), 6.64 (d, J=2.8 Hz, 1H), 4.00 (s, 3H), 3.44-3.38 (m, 2H), 3.20-3.12 (m, 2H), 2.84 (t, J=7.6 Hz, 2H), 2.74 (d, J=13.6 Hz, 1H), 2.64 (d, J=13.6 Hz, 1H), 2.52 (t, J=7.6 Hz, 2H), 2.13 (td, J=10.4, 1.6 Hz, 1H), 1.83 (td, J=11.2, 1.6 Hz, 1H), 1.67 (s, 3H), 1.56-1.45 (m, 1H), 1.31-1.24 (m, 1H), 1.15-1.07 (m, 1H), 1.04 (s, 3H), 1.03 (s, 3H), 0.99-0.90 (m, 1H) ppm.

Compound 95B: MS (ESI): 673 m/z $[M+H]^+$; Retention time: 2.06 minutes; purity: >99% (214 nm); (LC-MS method 011); $^1$H NMR (400 MHz, $CD_3OD$) δ 7.56 (t, J=7.6 Hz, 1H), 7.48 (d, J=7.6 Hz, 1H), 7.35 (s, 1H), 7.33 (d, J=2.8 Hz, 1H), 7.30-7.23 (m, 2H), 7.16 (t, J=7.6 Hz, 1H), 7.10 (s, 1H), 7.08-7.01 (m, 2H), 6.64 (d, J=2.8 Hz, 1H), 4.00 (s, 3H), 3.44-3.38 (m, 2H), 3.20-3.12 (m, 2H), 2.84 (t, J=7.6 Hz, 2H), 2.74 (d, J=13.6 Hz, 1H), 2.64 (d, J=13.6 Hz, 1H), 2.52 (t, J=7.6 Hz, 2H), 2.13 (td, J=10.4, 1.6 Hz, 1H), 1.83 (td, J=11.2, 1.6 Hz, 1H), 1.67 (s, 3H), 1.56-1.45 (m, 1H), 1.31-1.24 (m, 1H), 1.15-1.07 (m, 1H), 1.04 (s, 3H), 1.03 (s, 3H), 0.99-0.90 (m, 1H) ppm.

Example 96. Enantiomer 1 and 2 of 3-[3-[22,28-difluoro-3,10,10-trimethyl-12,12-dioxo-6-(trideuteriomethyl)-24-oxa-12lambda6-thia-3,4,19,30-tetrazapentacyclo-[23.3.1.12,5.015,23.016,20]triaconta-1(29),2(30),4,15,17,20,22,25,27-nonaen-6-yl]phenyl]propanoic Acid

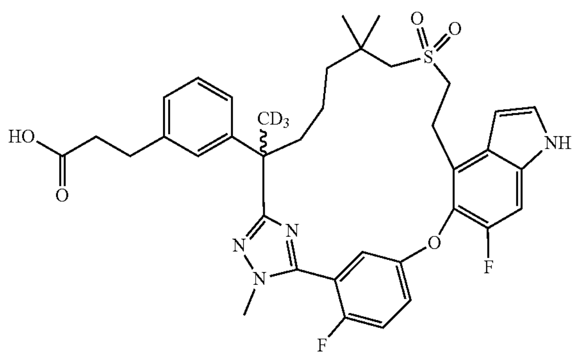 [SMILES: [2H]C([2H])([2H])C1(c2cccc(CCC(=O)O)c2)CCCC(C)(C)CS(=O)(=O)CCc2c(c(F)cc3[nH]ccc23)Oc2ccc(F)c(c2)-c2nc1nn2C]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with ethyl 3-(3-(7-((2-hydroxyethyl)sulfonyl)-6,6-dimethyl-2-(2-methylhydrazine-1-carbonyl)heptan-2-yl-1,1,1-d3)phenyl) propanoate (Intermediate 69-9, 2.0 g, 4.1 mmol) in Step A, the title compound was prepared following the reaction sequence (Steps A-F) as described for Example 6, with change of order of chiral separation and ester hydrolysis. Instead of separating racemic esters in Step E of Example 6, the current racemic ester mixture (450 mg, 0.62 mmol) from corresponding Step D of Example 6 was first hydrolyzed to corresponding acid (400 mg, 93%) as described in Step F. The resulting racemic acid (400 mg) was then subject to chiral prep-HPLC using Gilson-281 under the following separation condition: Column: IG 20*250 mm, 10 μm; Mobile Phase: n-Hexane (0.1% formic acid): isopropanol (0.1% formic acid)=7:3; Flow Rate: 15 mL/minutes; Run time per injection: 26 minutes; Injection: 0.6 mL; Sample solution: 300 mg in 25 mL methanol. The first eluent, enantiomer 1, is designated as Compound 96A (70 mg, 23%). The second eluent, enantiomer 2, is designated as Compound 96B (90 mg, 30%).

Compound 96A: MS (ESI): 694 m/z $[M+H]^+$; Retention time: 2.08 minutes; purity: >99% (214 nm); (LC-MS method 012). Chiral-HPLC purity: 100%; $^1$H NMR (400 MHz, $CD_3OD$) δ 7.31-7.28 (m, 2H), 7.26 (d, J=3.2 Hz, 1H), 7.20-7.15 (m, 2H), 7.13 (t, J=7.6 Hz, 1H), 7.06 (s, 1H), 7.01-6.95 (m, 2H), 6.60 (dd, J=0.8, 3.2 Hz, 1H), 3.82 (d, J=2.4 Hz, 3H) 3.39-3.25 (m, 2H), 3.31-3.27 (m, 1H), 3.24-3.13 (m, 1H), 2.94 (d, J=13.6 Hz, 1H), 2.83-2.70 (m, 3H), 2.47 (t, J=7.6 Hz, 2H), 2.11 (td, J=11.6, 3.2 Hz, 1H), 1.78 (td, J=11.6, 3.6 Hz, 1H), 1.64-1.48 (m, 1H), 1.34-1.24 (m, 3H), 1.04 (s, 3H), 1.03 (s, 3H) ppm.

Compound 96B: MS (ESI): 694 m/z $[M+H]^+$; Retention time: 2.08 minutes; purity: 99% (214 nm); (LC-MS method 012). $^1$H NMR (400 MHz, $CD_3OD$) δ 7.31-7.28 (m, 2H), 7.26 (d, J=3.2 Hz, 1H), 7.20-7.15 (m, 2H), 7.13 (t, J=7.6 Hz, 1H), 7.06 (s, 1H), 7.01-6.95 (m, 2H), 6.60 (dd, J=0.8, 3.2 Hz, 1H), 3.82 (d, J=2.4 Hz, 3H) 3.39-3.30 (m, 2H), 3.31-3.27 (m, 1H), 3.24-3.13 (m, 1H), 2.94 (d, J=13.6 Hz, 1H), 2.83-2.70 (m, 3H), 2.47 (t, J=7.6 Hz, 2H), 2.11 (td, J=11.6, 3.2 Hz, 1H), 1.78 (td, J=11.6, 3.6 Hz, 1H), 1.64-1.48 (m, 1H), 1.34-1.24 (m, 3H), 1.04 (s, 3H), 1.03 (s, 3H) ppm.

Example 97. Enantiomer 1 and 2 of 3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]propane-1,2-diol

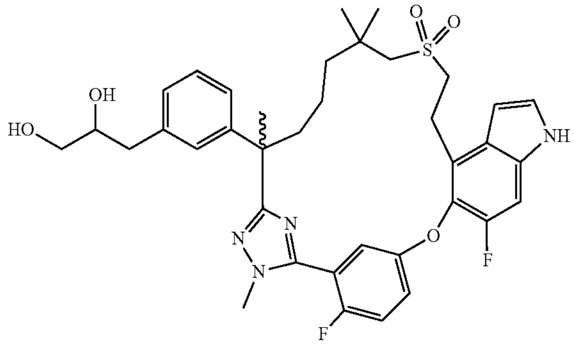 [SMILES: Cn1nc2nc1-c1cc(ccc1F)Oc1c(F)cc3[nH]ccc3c1CCS(=O)(=O)CC(C)(C)CCCC2(C)c1cccc(CC(O)CO)c1]

Exchanging ethyl 2-((6-(3-(2,2-dimethyl-1,3-dioxolan-4-yl)phenyl)-2,2,6-trimethyl-7-(2-methylhydrazineyl)-7-oxoheptyl)sulfonyl)acetate (Intermediate 45-14) with ethyl 2-((6-(3-((2,2-dimethyl-1,3-dioxolan-4-yl)methyl)phenyl)-2,2,6-trimethyl-7-(2-methylhydrazineyl)-7-oxoheptyl)sulfonyl)acetate (Intermediate 45-18, 3.8 g, 7.03 mmol) in Step A, the reaction procedure sequence (Steps A to B) described for Example 90 was used to prepare the racemic title compounds (500 mg) in Step B, which was then subjected to chiral prep-HPLC separation using Gilson-281 and the following separation conditions: Column: AD 20*250, 10 μm; Mobile Phase: n-Hexane (0.1% diethylamine): ethanol (0.1% diethylamine)=80:20; Flow Rate: 50 ml/min; Run time per injection: 23 minutes; Injection: 0.6 ml; Sample solution: 500 mg in 25 mL methanol. The first eluent, enantiomer 1, was designated as Compound 97A (78 mg, 16%). The second eluent, enantiomer 2, was designated as Compound 97B (98 mg, 20%).

Compound 97A: MS (ESI): 693 m/z $[M+H]^+$; Retention time: 1.77 minutes; purity: 96% (214 nm); (LC-MS method 012). $^1$H NMR (400 MHz, $CD_3OD$) d 7.36-7.32 (m, 3H), 7.23-7.16 (m, 3H), 7.10 (d, J=1.2 Hz, 1H), 7.06 (d, J=8.4 Hz, 1H), 7.01 (d, J=8.0 Hz, 1H), 6.63 (dd, J=3.2, 0.8 Hz, 1H), 3.87 (d, J=2.0 Hz, 3H), 3.78-3.75 (m, 1H), 3.50-3.38 (m, 4H), 3.30-3.19 (m, 2H), 1.85 (dd, J=13.6, 1.6 Hz, 1H), 2.80-2.76 (m, 2H), 2.66-2.63 (m, 1H), 2.16 (td, J=13.2, 3.6 Hz, 1H), 2.90 (td, J=12.8, 3.6 Hz, 1H), 1.69 (s, 3H), 1.59-1.57 (m, 1H), 1.36-1.28 (m, 1H), 1.22-1.17 (m, 1H), 1.07 (s, 3H), 1.06 (s, 3H), 1.06-1.02 (m, 1H) ppm.

Compound 97B: MS (ESI): 693 m/z $[M+H]^+$; Retention time: 1.77 minutes; purity: >99% (214 nm); (LC-MS method 012). $^1$H NMR (400 MHz, $CD_3OD$) d 7.36-7.32 (m, 3H), 7.23-7.16 (m, 3H), 7.10 (d, J=1.2 Hz, 1H), 7.06 (d, J=8.4 Hz, 1H), 7.01 (d, J=8.0 Hz, 1H), 6.63 (dd, J=3.2, 0.8 Hz, 1H), 3.87 (d, J=2.0 Hz, 3H), 3.78-3.75 (m, 1H), 3.50-3.38 (m, 4H), 3.30-3.19 (m, 2H), 1.85 (dd, J=13.6, 1.6 Hz, 1H), 2.80-2.76 (m, 2H), 2.66-2.63 (m, 1H), 2.16 (td, J=13.2, 3.6 Hz, 1H), 2.90 (td, J=12.8, 3.6 Hz, 1H), 1.69 (s, 3H), 1.59-1.57 (m, 1H), 1.36-1.28 (m, 1H), 1.22-1.17 (m, 1H), 1.07 (s, 3H), 1.06 (s, 3H), 1.06-1.02 (m, 1H) ppm.

Example 98. Enantiomer 1 and 2 of 3-[3-[22,28-difluoro-3-methyl-12,12-dioxo-6,10,10-tris(trideuteriomethyl)-24-oxa-12lambda6-thia-3,4,19,30-tetrazapentacyclo-[23.3.1.12,5.015,23.016,20]triaconta-1(29),2(30),4,15,17,20,22,25,27-nonaen-6-yl]phenyl]propanoic acid

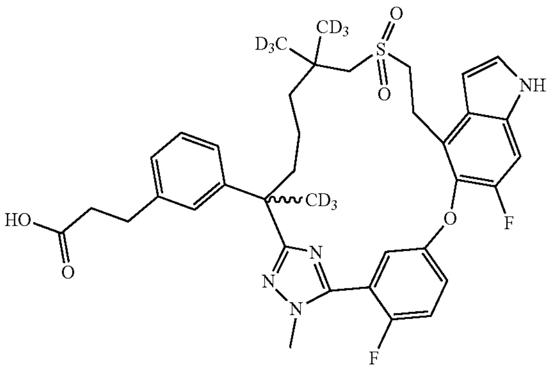 [SMILES: [2H]C([2H])([2H])C1(c2cccc(CCC(=O)O)c2)CCCC(C([2H])([2H])[2H])(C([2H])([2H])[2H])CS(=O)(=O)CCc2c(c(F)cc3[nH]ccc23)Oc2ccc(F)c(c2)-c2nc1nn2C]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with ethyl 3-(3-(6-(((2-hydroxyethyl)sulfonyl)methyl)-6-(methyl-d3)-2-(2-methylhydrazine-1-carbonyl)-heptan-2-yl-1,1,1,7,7,7-d6)phenyl)propanoate (Intermediate 58-7, 1.3 g, 2.6 mmol) in Step A, the title compounds was prepared following the reaction sequence (Steps A-F) as described for Example 6, with slight adjustment of the order of reactions. The racemic ester mixture (600 mg), obtained from corresponding Step D, was hydrolyzed to racemic acid (400 mg, 0.57 mmol), as described in Step G of Example 6. The racemic acid was subject to chiral prep-HPLC using Gilson-281 under the following separation condition: Column: IG 20*250 mm, 10 μm; Mobile phase: n-Hexane (0.1% formic acid): isopropanol (0.1% formic acid)=7:3; Flow Rate: 15 mL/minutes; Run time per injection: 26 minutes; Injection: 1.5 mL; Sample solution: 400 mg in 40 mL methanol. The first eluent, enantiomer 1, is designated as Compound 98A (120 mg, 30%). The second eluent, enantiomer 2, is designated as Compound 98B (120 mg, 30%).

Compound 98A: MS (ESI): 700 m/z $[M+H]^+$; Retention time: 1.38 minutes; purity: 99% (214 nm); (LC-MS method 014). Chiral-HPLC purity: >99%; $^1$H NMR (400 MHz, $CD_3OD$) δ 7.38-7.31 (m, 3H), 7.23 (d, J=10.8 Hz, 1H), 7.21-7.19 (m, 1H), 7.16 (t, J=7.6 Hz, 1H), 7.09 (s, 1H), 7.05-6.99 (m, 2H), 6.63 (dd, J=0.8, 3.2 Hz, 1H), 3.87 (d, J=2.0 Hz, 3H), 3.44-3.33 (m, 3H), 3.26-3.18 (m, 1H), 2.98 (d, J=13.6 Hz, 1H), 2.85-2.75 (m, 3H), 2.51 (t, J=7.6 Hz, 2H), 2.16 (dt, J=13.2, 3.6 Hz, 1H), 1.81 (dt, J=12.8, 4.0 Hz, 1H), 1.64-1.53 (m, 1H), 1.40-1.29 (m, 1H), 1.24-1.15 (m, 1H), 1.08-0.97 (m, 1H) ppm.

Compound 98B: MS (ESI): 700 m/z $[M+H]^+$; Retention time: 1.38 minutes; purity: 99% (214 nm); (LC-MS method 014). Chiral-HPLC purity: >99%; $^1$H NMR (400 MHz, $CD_3OD$) δ 7.38-7.31 (m, 3H), 7.23 (d, J=10.8 Hz, 1H), 7.21-7.19 (m, 1H), 7.16 (t, J=7.6 Hz, 1H), 7.09 (s, 1H), 7.05-6.99 (m, 2H), 6.63 (dd, J=0.8, 3.2 Hz, 1H), 3.87 (d, J=2.0 Hz, 3H), 3.44-3.33 (m, 3H), 3.26-3.18 (m, 1H), 2.98 (d, J=13.6 Hz, 1H), 2.85-2.75 (m, 3H), 2.51 (t, J=7.6 Hz, 2H), 2.16 (dt, J=13.2, 3.6 Hz, 1H), 1.81 (dt, J=12.8, 4.0 Hz, 1H), 1.64-1.53 (m, 1H), 1.40-1.29 (m, 1H), 1.24-1.15 (m, 1H), 1.08-0.97 (m, 1H) ppm.

Example 99. 3-[3-(25,31-Difluoro-3,6-dimethyl-9,9-dioxo-27-oxa-9λ6-thia-3,4,12,13,22,33-hexazahexacyclo[26.3.1.12,5.012,16.018,26.019,23]tritriaconta-1(32),2(33),4,13,15,18,20,23,25,28,30-undecaen-6-yl)phenyl]propanoic Acid

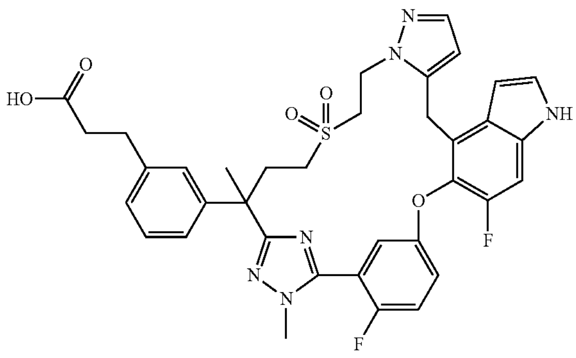 [SMILES: Cn1nc2nc1-c1cc(ccc1F)Oc1c(F)cc3[nH]ccc3c1Cc1ccnn1CCS(=O)(=O)CCC2(C)c1cccc(CCC(=O)O)c1]

and

Example 100. Enantiomers 1 and 2 of 3-[3-(24,30-difluoro-3,6-dimethyl-9,9-dioxo-26-oxa-9λ6-thia-3,4,12,21,32,33-hexazahexacyclo[25.3.1.12,5.112,15.017,25.018,22]tritriaconta-1(31),2(33),4,13,15(32),17,19,22,24,27,29-undecaen-6-yl)phenyl]propanoic Acid

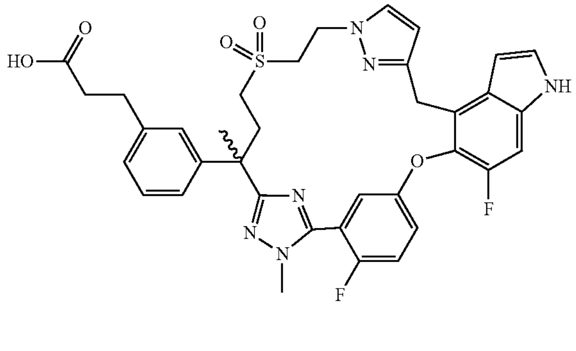 [SMILES: Cn1nc2nc1-c1cc(ccc1F)Oc1c(F)cc3[nH]ccc3c1Cc1ccn(n1)CCS(=O)(=O)CCC2(C)c1cccc(CCC(=O)O)c1]

Ethyl 3-(3-(4-((2-((tert-butyldimethylsilyl)oxy)ethyl)thio)-2-(5-(2-fluoro-5-((6-fluoro-1-(phenylsulfonyl)-4-((1-(tetrahydro-2H-pyran-2-yl)-1H-pyrazol-3-yl)methyl)-1H-indol-5-yl)oxy)phenyl)-1-methyl-1H-1,2,4-triazol-3-yl)butan-2-yl)phenyl)propanoate

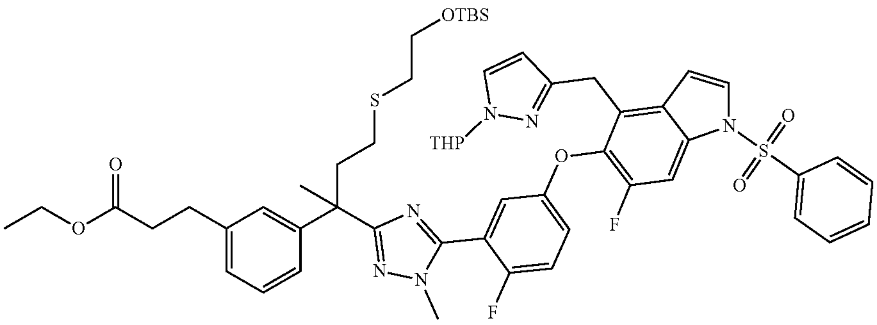

Step A: To a stirred solution of methyl 2-fluoro-5-((6-fluoro-1-(phenylsulfonyl)-4-((1-(tetrahydro-2H-pyran-2-yl)-1H-pyrazol-3-yl)methyl)-1H-indol-5-yl)oxy)benzimidothioate hydroiodide (Intermediate 14-5, 2.5 g, 4 mmol) in pyridine (40 mL) was added ethyl 3-(3-(5,12,12,13,13-pentamethyl-4-oxo-11-oxa-8-thia-2,3-diaza-12-silatetradecan-5-yl)phenyl)propanoate (Intermediate 103, 2.0 g, 4 mmol). The mixture was stirred at 80° C. overnight, then cooled to room temperature, quenched with water (100 mL), and extracted with ethyl acetate (3×100 mL). The combined organic extracts were washed with saturated sodium bicarbonate, dried over sodium sulfate, and concentrated to give the title compound (5.0 g), which was used for the next step without further purification. MS (ESI): 1053 m/z $[M+H]^+$; Retention time: 3.31 minutes; purity: 90% (254 nm).

Ethyl 3-(3-(2-(5-(5-((4-((1H-pyrazol-3-yl)methyl)-6-fluoro-1-(phenylsulfonyl)-1H-indol-5-yl)oxy)-2-fluorophenyl)-1-methyl-1H-1,2,4-triazol-3-yl)-4-((2-hydroxyethyl)thio)butan-2-yl)phenyl)propanoate

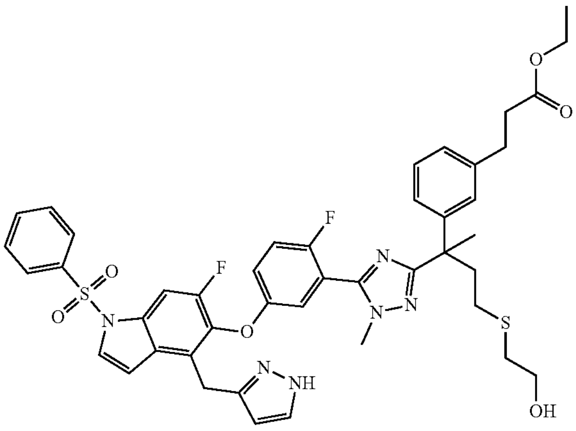 [SMILES: CCOC(=O)CCc1cccc(C(C)(CCSCCO)c2nc(-c3cc(Oc4c(F)cc5c(ccn5S(=O)(=O)c5ccccc5)c4Cc4cc[nH]n4)ccc3F)n(C)n2)c1]

Step B: To a stirred solution of Step A product (5.0 g, crude) in dichloromethane (20 mL) was added trifluoroacetic acid (4.87 g, 42.7 mmol). The mixture was stirred at room temperature overnight, then concentrated. The residue was re-dissolved in ethanol (40 mL), then treated with sodium carbonate (4.53 g, 42.7 mmol). The mixture was stirred at room temperature for 2 hours and concentrated. The residue was diluted with water (100 mL), extracted with ethyl acetate (2×100 mL). The combined organic extracts were washed with saturated sodium bicarbonate, dried over sodium sulfate, and concentrated. The crude material was purified by flash chromatography to give the title compound (1.0 g, 27% two steps). MS (ESI): 855 m/z $[M+H]^+$; Retention time: 2.18 minutes; purity: 90% (254 nm) (LC-MS method 022).

Mixture of ethyl 3-[3-[21-(benzenesulfonyl)-24,30-difluoro-3,6-dimethyl-26-oxa-9-thia-3,4,12,21,32,33-hexazahexacyclo[25.3.1.12,5.112,15.017,25.018,22]tritriaconta-1(31),2(33),4,13,15(32),17,19,22,24,27,29-undecaen-6-yl]phenyl]propanoate and its regio-isomer ethyl 3-[3-[22-(benzenesulfonyl)-25,31-difluoro-3,6-dimethyl-27-oxa-9-thia-3,4,12,13,22,33-hexazahexacyclo[26.3.1.12,5.012,16.018,26.019,23]tritriaconta-1(32),2(33),4,13,15,18,20,23,25,28,30-undecaen-6-yl]phenyl]propanoate

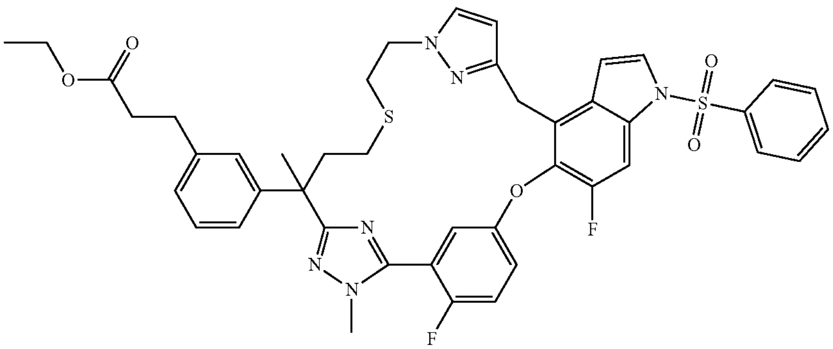

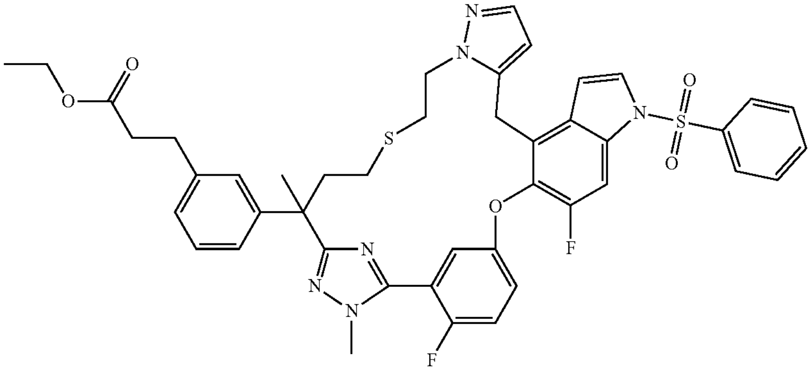

Step C: To a degassed solution of Step B product (300 mg, 0.035 mmol) in dioxane (20 mL) in a sealing tube was added cyanomethyl(triphenyl)phosphonium bromide (1.05 mmol, 317 mg). The resulting mixture was heated at 150° C. by microwave for 50 minutes. The solvent was removed, the residue was purified with flash chromatography to give the title compounds as an inseparable mixture (100 mg, 34%). MS (ESI): 837 m/z $[M+H]^+$; Retention time: 2.46 minutes; purity: >99% (254 nm); (LC-MS method 022).

Mixture of ethyl 3-[3-[21-(benzenesulfonyl)-24,30-difluoro-3, 6-dimethyl-9,9-dioxo-26-oxa-9 6-thia-3, 4,12,21,32,33-hexazahexacyclo[25.3.1.12,5.112, 15.017,25.018,22]tritriaconta-1(31),2(33),4,13,15 (32),17,19,22,24,27,29-undecaen-6-yl]phenyl] propanoate and its regio-isomer ethyl 3-[3-[22-(benzenesulfonyl)-25,31-difluoro-3,6-dimethyl-9,9-dioxo-27-oxa-9 6-thia-3,4,12,13,22,33-hexazahexacyclo[26.3.1.12,5.012,16.018,26.019,23] tritriaconta-1(32),2(33),4,13,15,18,20,23,25,28,30-undecaen-6-yl]phenyl]propanoate

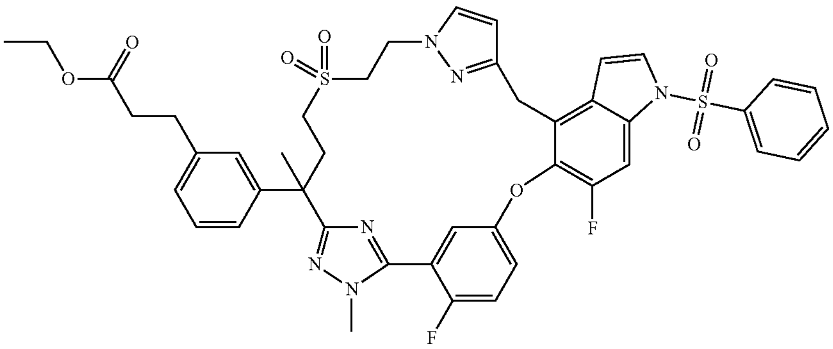

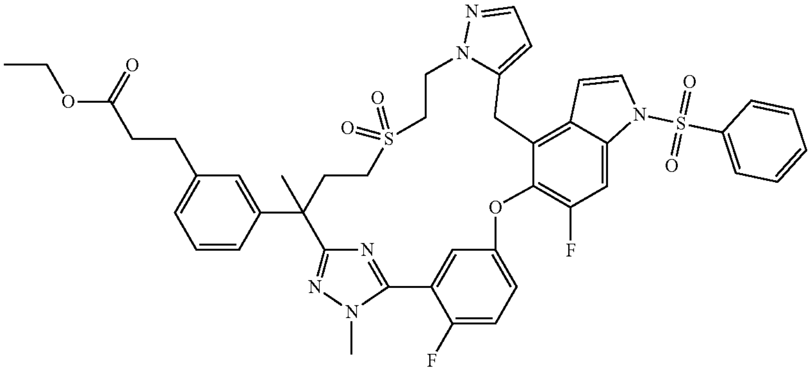

Step D: To a stirred solution of Step C product (300 mg, 0.358 mmol) in methanol (10 mL) was added a mixture of ammonium molybdate tetrahydrate (783 mg, 0.72 mmol) in hydrogen peroxide (30%, 1 mL). The mixture was stirred at room temperature for 4 hours, then quenched with water (50 mL), and extracted with ethyl acetate (3×25 mL). The combined organic extracts were washed with saturated sodium sulfite (2×10 mL), brine, dried over sodium sulfate, and concentrated. The residue was purified with silica gel column chromatography to give the title compounds (270 mg, 88%) as an inseparable mixture. MS (ESI): 869 m/z $[M+H]^+$. Retention time: 2.31 minutes; purity: 90% (254 nm) (LC-MS method 022).

Compound 99: 3-[3-(25,31-Difluoro-3,6-dimethyl-9,9-dioxo-27-oxa-9λ6-thia-3,4,12,13,22,33-hexazahexacyclo[26.3.1.12,5.012,16.018,26.019,23]-tritriaconta-1(32),2(33),4,13,15,18,20,23,25,28,30-undecaen-6-yl)phenyl]propanoic acid and Compounds 100A and 100B: Enantiomers 1 and 2 of 3-[3-(24,30-difluoro-3,6-dimethyl-9,9-dioxo-26-oxa-9 6-thia-3,4,12,21,32,33-hexazahexacyclo[25.3.1.12,5.112,15.017,25.018,22]tritriaconta-1(31),2(33),4,13,15(32),17,19,22,24,27,29-undecaen-6-yl)phenyl]propanoic Acid

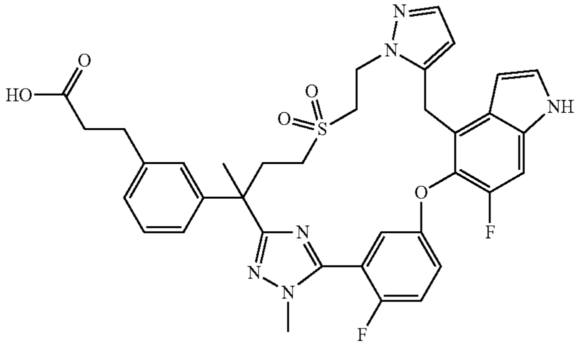

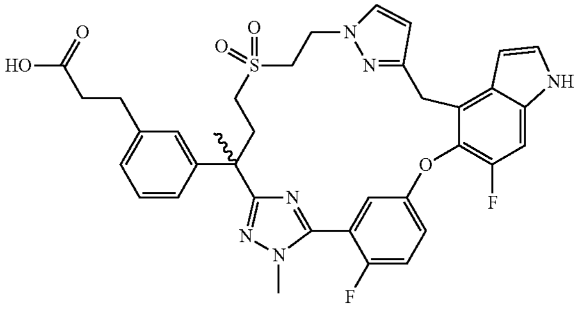

First Eluent: Enantiomer 1
Second Eluent: Enantiomer 2

Step E: A mixture of Step D product (0.31 mmol, 270 mg) and 0.2 M lithium hydroxide solution (in methanol:water: tetrahydrofuran=1:1:3, 10 mL) was stirred at room temperature for 4 hours. The clear solution was acidified with 15 mL of 1 N hydrochloric acid solution to pH ~4 and extracted with ethyl acetate (3×25 mL). The combined organic extracts were washed with brine, dried over sodium sulfate, and concentrated. The residue was purified with preparative thin layer chromatography. The smaller band, which is less polar, is designated as Compound 99 (25.1 mg, 11.5%). The majorband, which is more polar, is another racemic regio-isomer (100 mg, 50%). This regio-isomer was subjected to chiral SFC using SFC-150 (Thar, Waters) and the following separation condition: Column: (R,R)-Whelk-O1 20*250 mm, 10 μm (Regis); Column temperature: 35° C.; Mobile phase: carbon dioxide/methanol (0.2% Ammonia in Methanol as additive)=50/50; Flow rate: 120 g/minutes; Back pressure: 100 bar; Detection wavelength: 214 nm; Cycle time: 7.0 minutes; Sample solution: 100 mg dissolved in 6 ml Methanol. Injection: 1.0 mL. The first eluent, enantiomer 1, is designated as Compound 100A (26 mg, 26%); the second eluent, enantiomer 2, is designated as Compound 100B (22 mg, 22%).

Compound 99: MS (ESI): 701 m/z $[M+H]^+$; Retention time: 1.95 minutes; purity: >99% (254 nm); (LC-MS method 022). $^1$H NMR (400 MHz, $CD_3OD$) δ 7.32 (d, J=3.2 Hz, 1H), 7.28 (d, J=10.4 Hz, 1H), 7.25-7.05 (m, 6H), 6.99 (d, J=7.6 Hz, 1H), 6.89 (s, 1H), 6.45 (d, J=2.8 Hz, 1H), 5.76 (s, 1H), 4.59-4.42 (m, 2H), 4.38 (s, 2H), 3.83 (d, J=2.0 Hz, 3H), 3.61-3.38 (m, 3H), 2.89 (t, J=7.6 Hz, 2H), 2.84-2.74 (m, 1H), 2.60-2.55 (m, 3H), 2.47-2.37 (m, 1H), 1.75 (s, 3H) ppm.

Compound 100A: MS (ESI): 701 m/z $[M+H]^+$; Retention time: 1.96 minutes; purity: >99% (254 nm); (LC-MS method 022). $^1$H NMR (400 MHz, $CD_3OD$) δ 7.21 (d, J=3.2 Hz, 1H), 7.15 (d, J=2.0 Hz, 1H), 7.16-7.06 (m, 2H), 7.00-6.95 (m, 4H), 6.88-6.82 (m, 2H), 6.50 (d, J=3.2 Hz, 1H), 5.74 (d, J=2.0 Hz, 1H), 4.38-4.30 (m, 1H), 4.26-4.19 (m, 1H), 4.15 (d, J=15.2 Hz, 1H), 4.08 (d, J=15.2 Hz, 1H), 3.70 (d, J=2.0 Hz, 3H), 3.54-3.43 (m, 2H), 3.20-3.16 (m, 1H), 2.74 (t, J=7.6 Hz, 2H), 2.69-2.61 (m, 2H), 2.41 (t, J=7.6 Hz, 2H), 2.33-2.26 (m, 1H), 1.63 (s, 3H) ppm.

Compound 100B: MS (ESI): 701 m/z $[M+H]^+$; Retention time: 1.96 minutes; purity: >99% (254 nm); (LC-MS method 022). $^1$H NMR (400 MHz, $CD_3OD$) δ 7.21 (d, J=3.2 Hz, 1H), 7.15 (d, J=2.0 Hz, 1H), 7.16-7.05 (m, 2H), 7.00-6.95 (m, 4H), 6.88-6.82 (m, 2H), 6.50 (d, J=3.2 Hz, 1H), 5.74 (d, J=2.0 Hz, 1H), 4.38-4.30 (m, 1H), 4.26-4.18 (m, 1H), 4.15 (d, J=15.2 Hz, 1H), 4.08 (d, J=15.2 Hz, 1H), 3.70 (d, J=2.0 Hz, 3H), 3.54-3.43 (m, 2H), 3.20-3.16 (m, 1H), 2.74 (t, J=7.6 Hz, 2H), 2.69-2.60 (m, 2H), 2.41 (t, J=7.6 Hz, 2H), 2.34-2.25 (m, 1H), 1.63 (s, 3H) ppm.

Example 101. Enantiomers 1 and 2 of 3-[3-(23,29-difluoro-3,6,31-trimethyl-9,9-dioxo-25-oxa-9lambda6-thia-3,4,12,13,14,20,32-heptazahexacyclo-[24.3.1.12,5.111,14.016,24.017,21]dotriaconta-1(30),2(32),4,11(31),12,16,18,21,23,26,28-undecaen-6-yl)phenyl]propanoic Acid

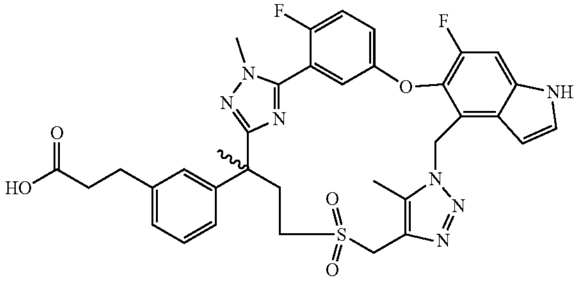 [SMILES: Cc1c2nnn1Cc1c(c(F)cc3[nH]ccc13)Oc1ccc(F)c(c1)-c1nc(nn1C)C(C)(c1cccc(CCC(=O)O)c1)CCS(=O)(=O)C2]

(5-(3-(3-(2-(3-Bromophenyl)-4-(but-2-yn-1-ylthio)butan-2-yl)-1-methyl-1H-1,2,4-triazol-5-yl)-4-fluorophenoxy)-6-fluoro-1-(phenylsulfonyl)-1H-indol-4-yl)methyl Acetate

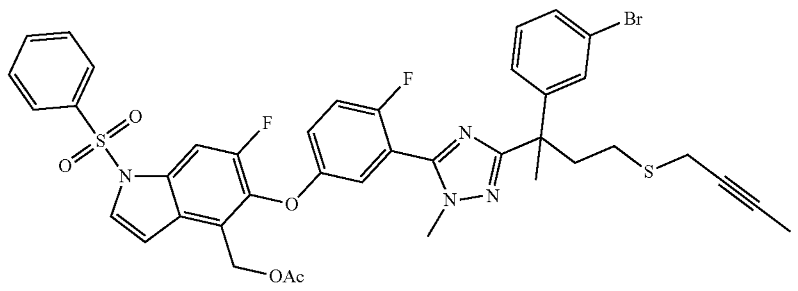 [SMILES: CC#CCSCCC(C)(c1cccc(Br)c1)c1nc(-c2cc(Oc3c(F)cc4c(ccn4S(=O)(=O)c4ccccc4)c3COC(C)=O)ccc2F)n(C)n1]

Step A: To a stirred solution of (6-fluoro-5-(4-fluoro-3-(imino(methylthio)methyl)phenoxy)-1-(phenylsulfonyl)-1H-indol-4-yl)methyl acetate hydroiodide (Intermediate 14-6, 4.78 g, 6.17 mmol) in anhydrous pyridine (50 mL) was added 2-(3-bromophenyl)-4-(but-2-yn-1-ylthio)-N',2-dimethylbutanehydrazide (Intermediate 69-10, 2.4 g, 6.17 mmol) and magnesium sulfate (3 g). The reaction mixture was stirred at 80° C. overnight, then cooled to room temperature. The solution was acidified with 0.5 N hydrochloric acid to adjust pH ~5 and extracted with ethyl acetate (3×100 mL). The combined organic extracts were washed with brine (50 mL), dried over sodium sulfate, and concentrated. The residue was purified by automated flash chromatography (80 g silica gel column, eluted with 0-45% ethyl acetate in petroleum ether) to give the title compound (3.7 g, 64%) as a light-yellow solid. MS (ESI): 833, 835 m/z $[M+H]^+$; Retention time: 2.22 minutes; purity: 89% (214 nm) (LC-MS method 003).

(5-(3-(3-(2-(3-Bromophenyl)-4-(but-2-yn-1-ylthio)butan-2-yl)-1-methyl-1H-1,2,4-triazol-5-yl)-4-fluorophenoxy)-6-fluoro-1-(phenylsulfonyl)-1H-indol-4-yl)methanol

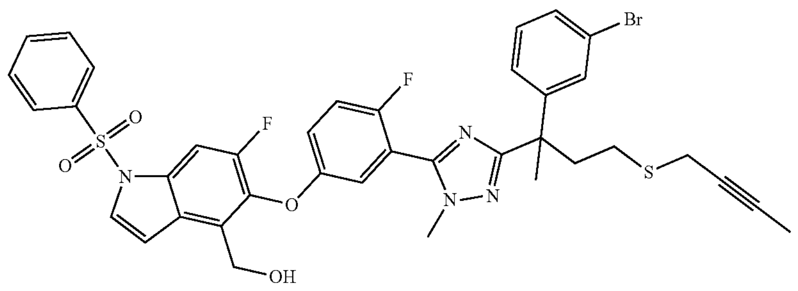 [SMILES: CC#CCSCCC(C)(c1cccc(Br)c1)c1nc(-c2cc(Oc3c(F)cc4c(ccn4S(=O)(=O)c4ccccc4)c3CO)ccc2F)n(C)n1]

Step B: To a stirred solution of Step A product (3.7 g, 3.95 mmol) in ethanol (50 mL) and tetrahydrofuran (20 mL) was added potassium carbonate (1.64 g, 11.8 mmol). The reaction mixture was stirred at room temperature for 4 hours. The reaction mixture was poured into water (150 mL) and extracted with ethyl acetate (3×150 mL). The combined organic phases were washed with brine (30 mL), dried over sodium sulfate and concentrated. The residue was purified by automated silica gel column chromatography (eluted with 0 to 45% ethyl acetate in petroleum ether) to give the title compound (3.0 g, 77%) as a yellow solid. MS (ESI): 791, 793 m/z $[M+H]^+$; Retention time: 2.40 minutes; purity: 85% (214 nm) (LC-MS method 012).

4-(Azidomethyl)-5-(3-(3-(2-(3-bromophenyl)-4-(but-2-yn-1-ylthio)butan-2-yl)-1-methyl-1H-1,2,4-triazol-5-yl)-4-fluorophenoxy)-6-fluoro-1-(phenylsulfonyl)-1H-indole

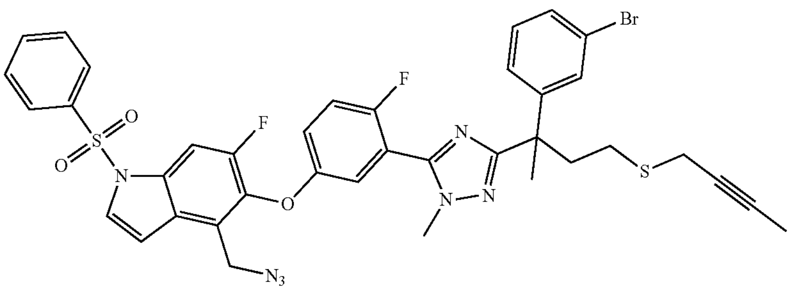 [SMILES: CC#CCSCCC(C)(c1cccc(Br)c1)c1nc(-c2cc(Oc3c(F)cc4c(ccn4S(=O)(=O)c4ccccc4)c3CN=[N+]=[N-])ccc2F)n(C)n1]

Step C: To a stirred solution of Step B product (3 g, 3.22 mmol) in tetrahydrofuran (50 mL) was added 1,8-diazabicyclo[5.4.0]undec-7-ene (981 mg, 6.44 mmol) and diphenylphosphoryl azide (2.66 g, 9.66 mmol). The reaction mixture was heated to reflux and stirred for 16 hours, poured into saturated ammonium chloride (50 mL), and extracted with ethyl acetate (3×50 mL). The combined organic phases were washed with brine (30 mL), dried over sodium sulfate, and concentrated. The residue was purified with automated silica gel column chromatography (eluted with 0-25% ethyl acetate in petroleum ether) to give the title compound (2.6 g, 91%) as a yellow solid. MS (ESI): 816, 818 m/z $[M+H]^+$; Retention time: 2.58 minutes; purity: 98% (214 nm) (LC-MS method 012).

20-(Benzenesulfonyl)-6-(3-bromophenyl)-23,29-difluoro-3,6,31-trimethyl-25-oxa-9-thia-3,4,12,13,14,20,32-heptazahexacyclo[24.3.1.12,5.111,14.016,24.017,21]dotriaconta-1(30),2(32),4,11(31),12,16,18,21,23,26,28-undecaene

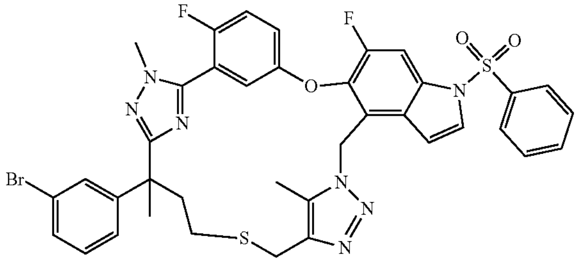 [SMILES: Cc1c2nnn1Cc1c(c(F)cc3c1ccn3S(=O)(=O)c1ccccc1)Oc1ccc(F)c(c1)-c1nc(nn1C)C(C)(c1cccc(Br)c1)CCSC2]

Step D: To a stirred solution of Step C product (2.6 g, 2.93 mmol) in toluene (350 mL) was added chloro(1,5-cyclooctadiene)(pentamethylcyclopentadienyl)ruthenium (223 mg, 0.586 mmol). The reaction mixture was heated to 65° C. under nitrogen and stirred for 16 hours, then concentrated. The residue was purified by automated silica gel column chromatography eluted with 0-65% ethyl acetate in petroleum ether to give the title compound (1.3 g, 52%) as a yellow solid. MS (ESI): 816, 818 m/z $[M+H]^+$; Retention time: 2.38 minutes; purity: 95% (214 nm) (LC-MS method 012). 20-(Benzenesulfonyl)-6-(3-bromophenyl)-23,29-difluoro-3,6,31-trimethyl-25-oxa-9lambda6-thia-3,4,12,13,14,20,32-heptazahexacyclo[24.3.1.12,5.111,14.016,24.017,21]dotriaconta-1(30),2(32),4,11(31),12,16,18,21,23,26,28-undecaene 9,9-dioxide

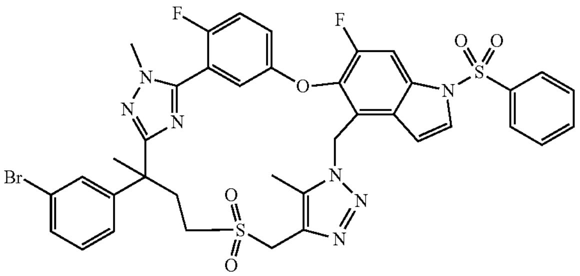 [SMILES: Cc1c2nnn1Cc1c(c(F)cc3c1ccn3S(=O)(=O)c1ccccc1)Oc1ccc(F)c(c1)-c1nc(nn1C)C(C)(c1cccc(Br)c1)CCS(=O)(=O)C2]

Step E: To a stirred and cooled (0° C.) solution of Step D product (1.2 g, 1.4 mmol) in methanol (120 mL) was added a solution of ammonium molybdate tetrahydrate (2.4 g, 19.4 mmol) in 12 mL of hydrogen peroxide (30% in water). The reaction was stirred at room temperature for 3 hours and concentrated. The residue was diluted with water (100 mL) and extracted with ethyl acetate (3×100 mL). The combined organic extracts were washed with brine (50 mL), dried over sodium sulfate, and concentrated to give the title compound (1.1 g, 87%) as a light-yellow solid. MS (ESI): 848, 850 m/z $[M+H]^+$; Retention time: 2.25 minutes; purity: 92% (214 nm) (LC-MS method 012). 6-(3-Bromophenyl)-23,29-difluoro-3,6,31-trimethyl-25-oxa-9lambda6-thia-3,4,12,13,14,20,32-heptazahexacyclo[24.3.1.12,5.111,14.016,24.017,21]dotriaconta-1(30),2(32),4,11(31),12,16,18,21,23,26,28-undecaene 9,9-dioxide

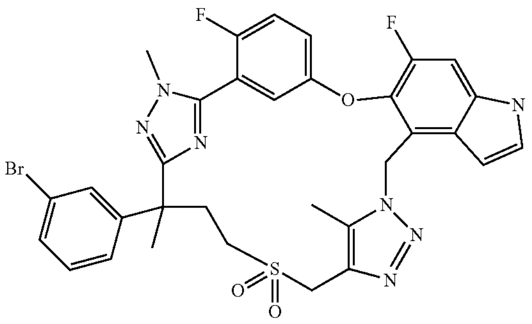 [SMILES: Cc1c2nnn1Cc1c(c(F)cc3[nH]ccc13)Oc1ccc(F)c(c1)-c1nc(nn1C)C(C)(c1cccc(Br)c1)CCS(=O)(=O)C2]

Step F: To a stirred solution of Step E product (1.1 g, 0.139 mmol) in methanol (15 mL) and tetrahydrofuran (5 mL) was added sodium hydroxide (146 mg, 3.65 mmol). The reaction was stirred at room temperature for 15 hours.

The solvent was removed. The residue was diluted with water (30 mL), extracted with ethyl acetate (3×20 mL). The combined organic extracts were washed with brine, dried over sodium sulfate, and concentrated to give the crude title compound (830 mg, 87%) as light-yellow solid, which was used in the next step without further purification. MS (ESI): 708, 710 m/z [M+H]$^+$; Retention time: 2.08 minutes; purity: 90% (214 nm) (LC-MS method 012).

Ethyl (E)-3-[3-(23,29-difluoro-3,6,31-trimethyl-9,9-dioxo-25-oxa-9lambda6-thia-3,4,12,13,14,20,32-heptazahexacyclo[24.3.1.12,5.111,14.016,24.017,21]dotriaconta-1(30),2(32),4,11(31),12,16,18,21,23,26,28-undecaen-6-yl)phenyl]prop-2-enoate

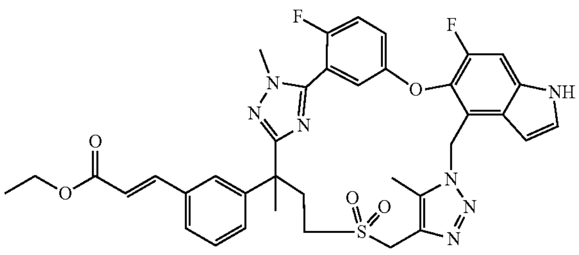 [SMILES: CCOC(=O)/C=C/c1cccc(C2(C)CCS(=O)(=O)Cc3nnn(c3C)Cc3c(c(F)cc4[nH]ccc34)Oc3ccc(F)c(c3)-c3nc2nn3C)c1]

Step G: To a stirred and degassed solution of Step F product (830 mg, 1.05 mmol) in 1,4-dioxane (16 mL) and water (4 mL) was added ethyl (E)-3-(4,4,5,5-tetramethyl-1,3,2-dioxaborolan-2-yl)prop-2-enoate (304 mg, 1.27 mmol), cesium carbonate (687 mg, 2.11 mmol) and 1,1'-bis(diphenylphosphino)ferrocene-palladium (II) dichloride dichloromethane complex (86.1 mg, 0.105 mmol). The mixture was stirred at 100° C. for 4 hours, then cooled to room temperature, diluted with water (50 mL), and extracted with ethyl acetate (3×30 mL). The combined organic extracts were washed with brine, dried over sodium sulfate, and concentrated. The residue was purified with automated flash chromatography (5-90% ethyl acetate in petroleum ether) to give the title compound (516 mg, 60%) as a light-yellow solid. MS (ESI): 728 m/z [M+H]$^+$; Retention time: 2.07 minutes; purity: 89% (214 nm); (LC-MS method 012).

Ethyl 3-[3-(23,29-difluoro-3,6,31-trimethyl-9,9-dioxo-25-oxa-9lambda6-thia-3,4,12,13,14,20,32-heptazahexacyclo[24.3.1.12,5.111,14.016,24.017,21]dotriaconta-1(30),2(32),4,11(31),12,16,18,21,23,26,28-undecaen-6-yl)phenyl]propanoate

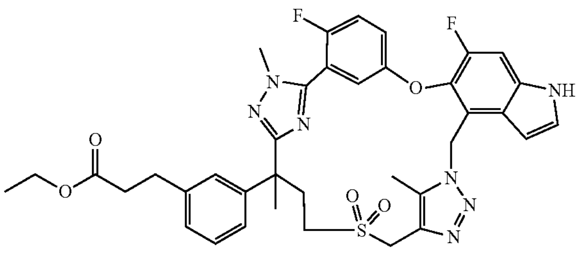 [SMILES: CCOC(=O)CCc1cccc(C2(C)CCS(=O)(=O)Cc3nnn(c3C)Cc3c(c(F)cc4[nH]ccc34)Oc3ccc(F)c(c3)-c3nc2nn3C)c1]

Step H: To a stirred solution of Step G product (516 mg, 0.631 mmol) in methanol (20 mL) was added palladium on active carbon (10%, 80 mg). The reaction mixture was stirred under hydrogen for 4 hours, then filtered through a pad of Celite. The filtrate was concentrated to give the title compound (490 mg, 95%) as a light-yellow solid. MS (ESI): 730 m/z [M+H]$^+$; Retention time: 1.82 minutes; purity: 89% (214 nm); (LC-MS method 003).

Enantiomer 1 and 2 of ethyl 3-[3-(23,29-difluoro-3,6,31-trimethyl-9,9-dioxo-25-oxa-9lambda6-thia-3,4,12,13,14,20,32-heptazahexacyclo[24.3.1.12,5.111,14.016,24.017,21]dotriaconta-1(30),2(32),4,11(31),12,16,18,21,23,26,28-undecaen-6-yl)phenyl]propanoate

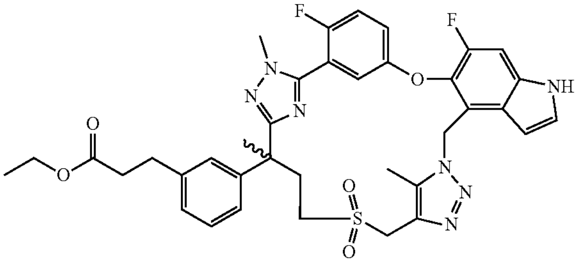

First eluent, enantiomer 1
Second eluent, Enantiomer 2

Step I: The racemic Step H product (520 mg, 0.63 mmol) was subject to chiral SFC using SFC-80 (Thar, Waters) under the following separation conditions: Column: WHELK 20*250 mm, 10 μm; Column temperature: 35° C.; Mobile phase: carbon dioxide/methanol (0.2% methanol ammonia as additive)=45/55; Flow rate: 80 g/min; Back pressure: 100 bar; Detection wavelength: 214 nm; Cycle time: 11.0 minutes; Sample solution: 520 mg dissolved in 25 mL methanol; Injection volume: 1.9 mL. The first eluent is designated as enantiomer 1 (150 mg, 31%). MS (ESI): 730 m/z [M+H]$^+$; Retention time: 2.04 minutes; purity: 98% (214 nm) (LC-MS method 012). The second eluent is designated as enantiomer 2 (130 mg, 27%). MS (ESI): 730 m/z [M+H]$^+$; Retention time: 2.04 minutes; purity: 98% (214 nm) (LC-MS method 012).

Compound 101A: Enantiomer 1 of 3-[3-(23,29-difluoro-3,6,31-trimethyl-9,9-dioxo-25-oxa-9lambda6-thia-3,4,12,13,14,20,32-heptazahexacyclo[24.3.1.12,5.111,14.016,24.017,21]-dotriaconta-1(30),2(32),4,11(31),12,16,18,21,23,26,28-undecaen-6-yl)phenyl]propanoic Acid

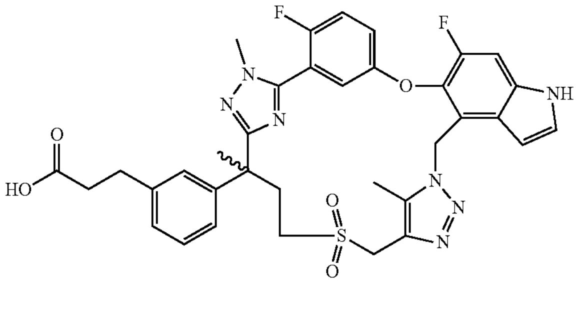 [SMILES: Cc1c2nnn1Cc1c(c(F)cc3[nH]ccc13)Oc1ccc(F)c(c1)-c1nc(nn1C)C(C)(c1cccc(CCC(=O)O)c1)CCS(=O)(=O)C2]

Step J: To a stirred solution of enantiomer 1 of Step I product (First eluent, 130 mg, 0.175 mmol) in methanol (4 mL) and tetrahydrofuran (4 mL) was added a solution of lithium hydroxide monohydrate (22 mg, 0.524 mmol) in water (1 mL). The mixture was stirred at room temperature for 8 hours, then concentrated. The residue was dissolved in water (20 mL), acidified with 1N hydrochloric acid to pH ~4, and extracted with ethyl acetate (3×15 mL). The combined organic extracts were washed with brine, dried over sodium sulfate, and concentrated to give the title compound (110 mg, 85%) as a light-yellow solid. MS (ESI): 702 m/z $[M+H]^+$; Retention time: 1.86 minutes; purity: 95% (214 nm); (LC-MS method 012). $^1H$ NMR (400 MHz, DMSO-$d_6$) δ 12.10 (brs, 1H), 11.38 (s, 1H), 7.56 (dt, J=4.0, 8.8 Hz, 1H), 7.47 (t, J=8.8 Hz, 1H), 7.42-7.39 (m, 2H), 7.19 (t, J=7.6 Hz, 1H), 7.06 (d, J=8.0 Hz, 1H), 7.00 (s, 1H), 6.85 (d, J=7.6 Hz, 1H), 6.74 (dd, J=2.8, 5.2 Hz, 1H), 6.45 (brs, 1H), 5.80-5.65 (m, 2H), 4.60-4.40 (m, 2H), 3.64 (s, 3H), 3.55-3.45 (m, 1H), 2.82-2.78 (m, 1H), 2.77 (t, J=7.2 Hz, 2H), 2.49-2.45 (m, 3H), 2.40 (s, 3H), 2.24-2.16 (m, 1H), 1.65 (s, 3H) ppm.

Compound 101B: Enantiomer 2 of 3-[3-(23,29-difluoro-3,6,31-trimethyl-9,9-dioxo-25-oxa-9lambda6-thia-3,4,12,13,14,20,32-heptazahexacyclo [24.3.1.12,5.111,14.016,24.017,21]-dotriaconta-1 (30),2(32),4,11(31),12,16,18,21,23,26,28-undecaen-6-yl)phenyl]propanoic Acid

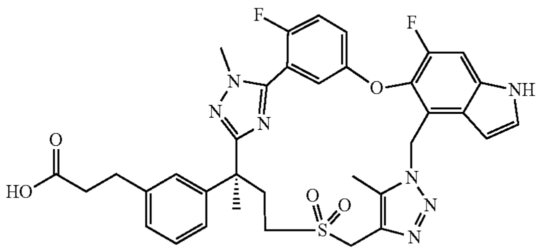 [SMILES: Cc1c2nnn1Cc1c(c(F)cc3[nH]ccc13)Oc1ccc(F)c(c1)-c1nc(nn1C)[C@](C)(c1cccc(CCC(=O)O)c1)CCS(=O)(=O)C2]

Step K. The Enantiomer 2 of Step I product (130 mg, 0.175 mmol) was subjected to an identical procedure for Enantiomer 1 as described in Step J. The title compound (110 mg, 85%) was obtained as a light-yellow solid. MS (ESI): 702 m/z $[M+H]^+$; Retention time: 1.86 minutes; purity: 96% (214 nm); (LC-MS method 012). $^1H$ NMR (400 MHz, DMSO-$d_6$) δ 12.10 (brs, 1H), 11.38 (s, 1H), 7.56 (dt, J=4.0, 8.8 Hz, 1H), 7.47 (t, J=8.8 Hz, 1H), 7.42-7.39 (m, 2H), 7.19 (t, J=7.6 Hz, 1H), 7.06 (d, J=8.0 Hz, 1H), 7.00 (s, 1H), 6.85 (d, J=7.6 Hz, 1H), 6.74 (dd, J=2.8, 5.2 Hz, 1H), 6.45 (brs, 1H), 5.81-5.68 (m, 2H), 4.60-4.46 (m, 2H), 3.64 (s, 3H), 3.55-3.45 (m, 1H), 2.82-2.78 (m, 1H), 2.77 (t, J=7.2 Hz, 2H), 2.49-2.45 (m, 3H), 2.40 (s, 3H), 2.24-2.16 (m, 1H), 1.65 (s, 3H) ppm.

Example 102. Enantiomers 1 and 2 of 3-[3-(10,10,22,28-tetrafluoro-3,6,9,9-tetramethyl-12,12-dioxo-24-oxa-12λ6-thia-3,4,19,30-tetrazapentacyclo [23.3.1.12,5.015,23.016,20]triaconta-1(29),2(30),4,15,17,20,22,25,27-nonaen-6-yl)phenyl]propanoic Acid

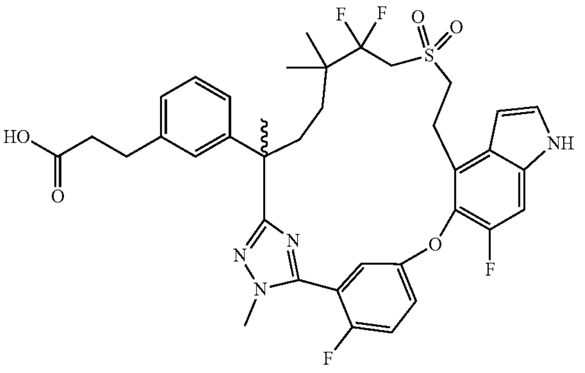 [SMILES: Cn1nc2nc1-c1cc(ccc1F)Oc1c(F)cc3[nH]ccc3c1CCS(=O)(=O)CC(F)(F)C(C)(C)CCC2(C)c1cccc(CCC(=O)O)c1]

Enantiomers 1 and 2 of tert-butyl 3-[3-[10,10,22,28-tetrafluoro-3,6,9,9-tetramethyl-12,12-dioxo-24-oxa-12lambda6-thia-3,4,19,30-tetrazapentacyclo [23.3.1.12,5.015,23.016,20]triaconta-1(29),2(30),4,15,17,20,22,25,27-nonaen-6-yl]phenyl]propanoate

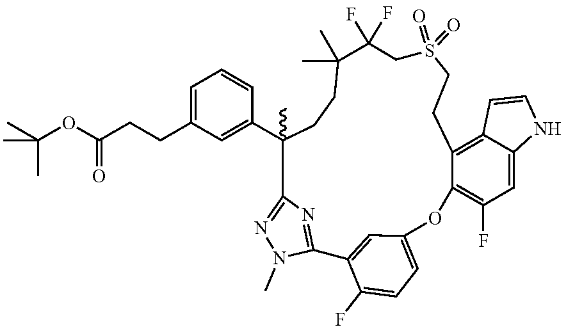 [SMILES: Cn1nc2nc1-c1cc(ccc1F)Oc1c(F)cc3[nH]ccc3c1CCS(=O)(=O)CC(F)(F)C(C)(C)CCC2(C)c1cccc(CCC(=O)OC(C)(C)C)c1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with tert-butyl 3-(3-(6,6-difluoro-7-((2-hydroxyethyl) sulfonyl)-2,5,5-trimethyl-1-(2-methylhydrazineyl)-1-oxoheptan-2-yl)phenyl)propanoate (Intermediate 69-11, 0.5 g, 0.91 mmol) in Step A, the reaction sequence (Steps A-D) described for Example 6 was used to prepare the title compounds (125 mg, 0.16 mmol) as a racemic mixture. This mixture was subject to chiral SFC separation using SFC-80 (Waters) under the following separation condition: Column: AS 20*250 mm, 10 μm; Column temperature: 35° C.; Mobile phase: carbon dioxide/methanol (0.2% Methanol Ammonia as additive)=70/30; Flow rate: 80 g/minutes; Back pressure: 100 bar; Detection wavelength: 214 nm; Cycle time: 7.0 minutes; Sample solution: 130 mg dissolved in 20 ml methanol; Injection volume: 1.9 mL. The first eluent is designated as enantiomer 1 (40 mg, 30%). The second eluent is designated as enantiomer 2 (30 mg, 23%).

Enantiomer 1: MS (ESI): 783 m/z $[M+H]^+$; Retention time: 2.06 minutes; purity: 98% (214 nm); (LC-MS method 011). Chiral-HPLC purity: >99%.

Enantiomer 2: MS (ESI): 783 m/z $[M+H]^+$; Retention time: 2.06 minutes; purity: 98% (214 nm); (LC-MS method 011). Chiral-HPLC purity: >99%.

Compound 102A, enantiomer 1 of 3-[3-[10,10,22,28-tetrafluoro-3,6,9,9-tetramethyl-12,12-dioxo-24-oxa-12lambda6-thia-3,4,19,30-tetrazapentacyclo[23.3.1.12,5.015,23.016,20]-triaconta-1(29),2(30),4,15,17,20,22,25,27-nonaen-6-yl]phenyl]propanoic Acid

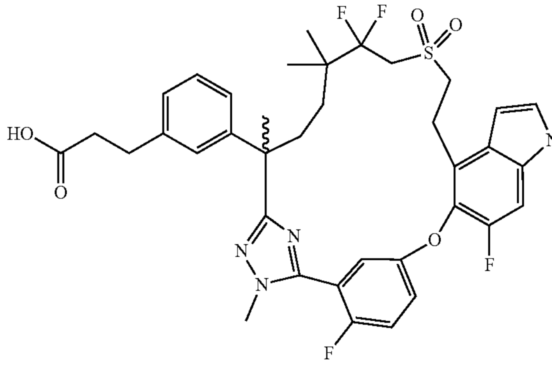

Step B: To a stirred solution of Enantiomer 1 of Step A product (first eluent of Step A, 40 mg) in dichloromethane (2 mL) was added trifluoroacetic acid (0.4 mL). The mixture was stirred at room temperature for 2 hours and concentrated. The residue was purified by automated flash chromatography (12 g silica gel column, eluted with 0-10% methanol in dichloromethane) to give the title compound (33.4 mg, 90%) as a solid. MS (ESI): 727 m/z $[M+H]^+$; Retention time: 1.83 minutes; purity: 95% (214 nm) (LC-MS method 011). Chiral-HPLC purity: >99%. $^1$H NMR (500 MHz, $CD_3OD$) δ 7.51 (dt, J=9.0, 3.5 Hz, 1H), 7.41 (t, J=9.5 Hz, 1H), 7.38 (d, J=3.5 Hz, 1H), 7.27 (d, J=10.5 Hz, 1H), 7.02-6.95 (m, 4H), 6.70 (dd, J=5.0, 3.0 Hz, 1H), 6.66 (d, J=3.0, 1H), 3.95 (dd, J=32.5, 15.5 Hz, 1H), 3.82 (d, J=3.0 Hz, 3H), 3.75-3.68 (m, 1H), 3.57-3.40 (m, 4H), 2.70-2.64 (m, 1H), 2.55-2.49 (m, 1H), 2.41 (t, J=7.5 Hz, 2H), 2.33-2.27 (m, 1H), 1.74-1.66 (m, 1H), 1.69 (s, 3H), 1.42-1.36 (m, 1H), 1.14-1.08 (m, 1H), 0.89 (s, 3H), 0.74 (s, 3H) ppm.

Compound 102B. Enantiomer 2 of 3-[3-[10,10,22,28-tetrafluoro-3,6,9,9-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]propanoic acid

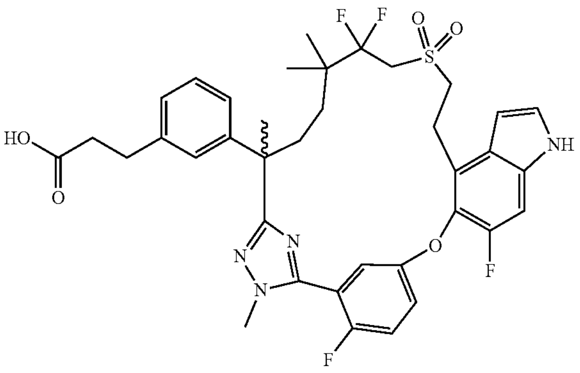 [SMILES: Cn1nc2nc1-c1cc(ccc1F)Oc1c(F)cc3[nH]ccc3c1CCS(=O)(=O)CC(F)(F)C(C)(C)CCC2(C)c1cccc(CCC(=O)O)c1]

Step C: Utilizing identical conditions to Step B, the title compound (23 mg, 84%) was prepared from Enantiomer 2 of Step A product (Second eluent of Step A, 40 mg) as a white solid. MS (ESI): 727 m/z $[M+H]^+$; Retention time: 1.83 minutes; purity: 95% (214 nm); (LC-MS method 011). Chiral-HPLC purity: >99%. $^1$H NMR (500 MHz, $CD_3OD$) δ 7.51 (dt, J=9.0, 3.5 Hz, 1H), 7.41 (t, J=9.5 Hz, 1H), 7.38 (d, J=3.5 Hz, 1H), 7.27 (d, J=10.5 Hz, 1H), 7.02-6.95 (m, 4H), 6.70 (dd, J=5.0, 3.0 Hz, 1H), 6.66 (dd, J=3.0, 0.5 Hz, 1H), 3.95 (dd, J=32.5, 15.5 Hz, 1H), 3.82 (d, J=3.0 Hz, 3H), 3.75-3.69 (m, 1H), 3.56-3.40 (m, 4H), 2.70-2.64 (m, 1H), 2.55-2.49 (m, 1H), 2.41 (t, J=7.5 Hz, 2H), 2.33-2.28 (m, 1H), 1.72-1.66 (m, 1H), 1.69 (s, 3H), 1.43-1.36 (m, 1H), 1.14-1.04 (m, 1H), 0.89 (s, 3H), 0.74 (s, 3H) ppm.

Example 103. 3-[3-[22,28-Difluoro-6-(hydroxymethyl)-3,10,10-trimethyl-12,12-dioxo-24-oxa-12lambda6-thia-3,4,19,30-tetrazapentacyclo-[23.3.1.12,5.015,23.016,20]triaconta-1(29),2(30),4,15,17,20,22,25,27-nonaen-6-yl]phenyl]propanoic Acid

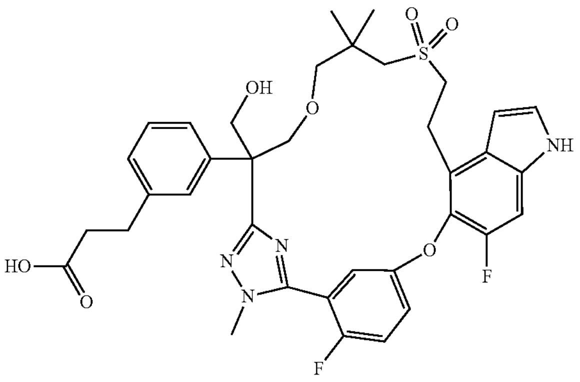 [SMILES: Cn1nc2nc1-c1cc(ccc1F)Oc1c(F)cc3[nH]ccc3c1CCS(=O)(=O)CC(C)(C)COCC2(CO)c1cccc(CCC(=O)O)c1]

3-[3-[22,28-Difluoro-3,10,10-trimethyl-12,12-dioxo-6-(tetrahydropyran-2-yloxymethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

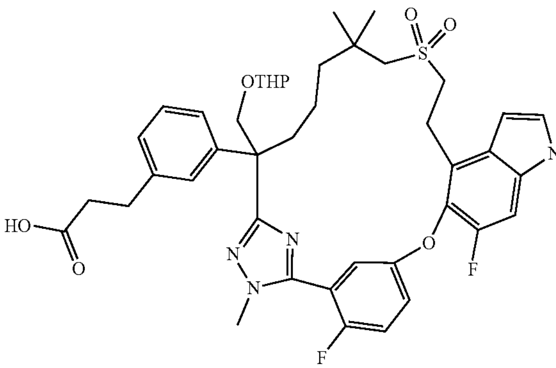

Step A: Exchanging ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(7-((2-ethoxy-2-oxoethyl)sulfonyl)-6,6-dimethyl-1-(2-methylhydrazineyl)-1-oxo-2-(((tetrahydro-2H-pyran-2-yl)oxy)methyl)heptan-2-yl)phenyl)propanoate (Intermediate 107, 4.2 g, 6.7 mmol) in Step A, the reaction procedure sequence (Steps A to G) described for Example 1 was used to prepare the title compound (630 mg) as a white solid. MS (ESI): 791 m/z $[M+H]^+$; Retention time: 2.14 minutes; purity: 85% (214 nm) (LC-MS method 023).

Compound 103: 3-[3-[22,28-Difluoro-6-(hydroxymethyl)-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

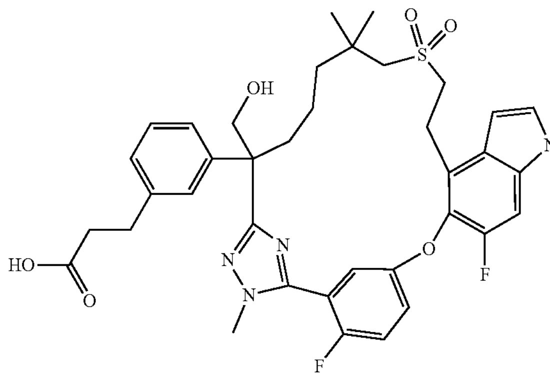

Step B: To a stirred solution of Step A product (630 mg, 0.797 mmol) in tetrahydrofuran (20 mL) and methanol (20 mL) was added pyridinium p-toluenesulfonate (601 mg, 2.39 mmol). The mixture was stirred at room temperature for 16 hours, then diluted with ethyl acetate (100 mL). The solution was washed with water, brine, dried over sodium sulfate, and concentrated. The residue was purified by automated flash chromatography (20 g, silica gel column, eluted with 0-10% methanol in dichloromethane) to give the title compound (420 mg, 75%) as a yellow solid. MS (ESI): 707 m/z $[M+H]^+$; Retention time: 1.74 minutes; purity: >99% (214 nm) (LC-MS method 023). $^1H$ NMR (400 MHz, $CD_3OD$) δ 7.37-7.32 (m, 3H), 7.24-7.18 (m, 3H), 7.09-7.06 (m, 2H), 7.01 (d, J=7.2 Hz, 1H), 6.63 (dd, J=3.2, 0.8 Hz, 1H), 4.11, 4.07 (ABq, J=11.2 Hz, 2H), 3.91 (d, J=2.0 Hz, 3H), 3.42-3.37 (m, 2H), 3.26-3.22 (m, 2H), 2.95-2.80 (m, 4H), 2.54 (t, J=7.6 Hz, 2H), 2.13-2.05 (m, 2H), 1.77-1.68 (m, 1H), 1.43-1.36 (m, 1H), 1.23-1.17 (m, 1H), 1.12 (s, 3H), 1.07-0.99 (m, 1H), 1.02 (s, 3H) ppm.

Example 104. 3-[3-(6-Cyano-22,28-difluoro-3,10,10-trimethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]propanoic acid

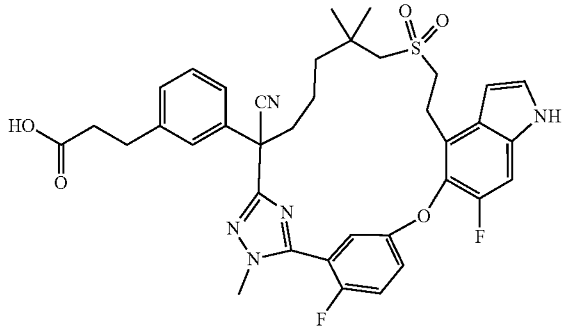 [SMILES: Cn1nc2nc1-c1cc(ccc1F)Oc1c(F)cc3[nH]ccc3c1CCS(=O)(=O)CC(C)(C)CCCC2(C#N)c1cccc(CCC(=O)O)c1]

3-[3-(22,28-Difluoro-6-formyl-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

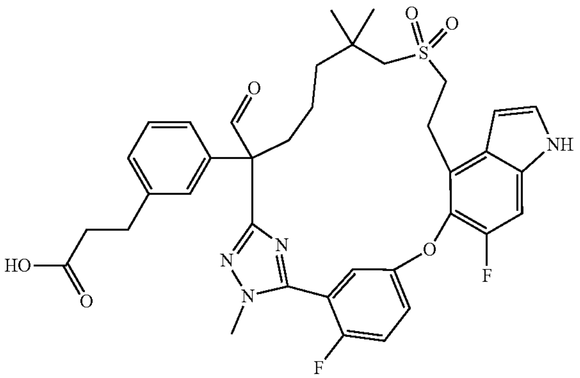 [SMILES: Cn1nc2nc1-c1cc(ccc1F)Oc1c(F)cc3[nH]ccc3c1CCS(=O)(=O)CC(C)(C)CCCC2(C=O)c1cccc(CCC(=O)O)c1]

Step A: To a stirred solution of 3-[3-[22,28-difluoro-6-(hydroxymethyl)-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]propanoic acid (Example 103, 22 mg, 0.03 mmol) in dimethyl sulfoxide (5 mL) was added 2-iodoxybenzoic acid (46%, 26.1 mg, 0.09 mmol). The mixture was stirred at room temperature for 16 hours, then quenched with sodium bicarbonate (20 mL), and extracted with dichloromethane (2×20 mL). The combined organic extracts were washed with brine, dried over sodium sulfate, and concentrated to give the title compound (20 mg, 91%) as oil. MS (ESI): 705 m/z $[M+H]^+$; Retention time: 1.84 minutes; purity: 80% (214 nm) (LC-MS method 023).

3-[3-[22,28-Difluoro-6-[(E)-hydroxyiminomethyl]-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

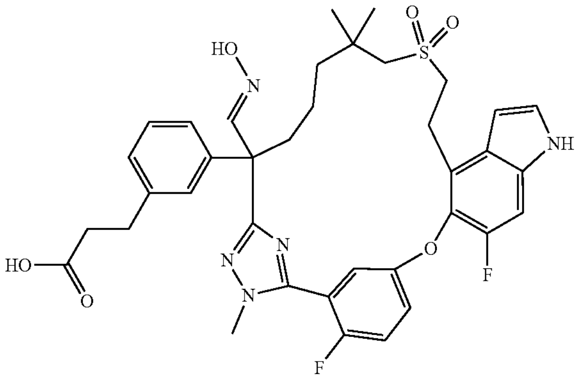 [SMILES: Cn1nc2nc1-c1cc(ccc1F)Oc1c(F)cc3[nH]ccc3c1CCS(=O)(=O)CC(C)(C)CCCC2(/C=N/O)c1cccc(CCC(=O)O)c1]

Step B: To a stirred solution of Step A product (20 mg, 0.028 mmol) in ethanol (5 mL) was added hydroxylamine (0.009 mL, 50% in water). The reaction was stirred at 85° C. for 1 hour. The mixture was acidified with 1M hydrochloric acid to pH ~4 at room temperature, then extracted with dichloromethane (2×20 mL). The combined organic extracts were washed with brine, dried over sodium sulfate, and concentrated to give the title compound (20 mg, 98%) as oil. MS (ESI): 720 m/z $[M+H]^+$; Retention time: 1.74 minutes; purity: 80% (214 nm) (LC-MS method 023).

Compound 104: 3-[3-(6-Cyano-22,28-difluoro-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

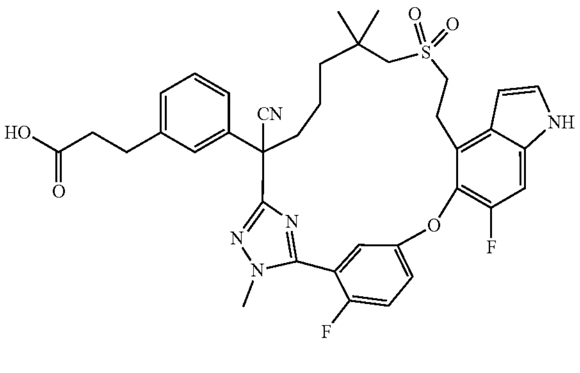 [SMILES: Cn1nc2nc1-c1cc(ccc1F)Oc1c(F)cc3[nH]ccc3c1CCS(=O)(=O)CC(C)(C)CCCC2(C#N)c1cccc(CCC(=O)O)c1]

Step C: To a stirred solution of Step B product (20 mg, 0.027 mmol) in N,N-dimethylformamide (3 mL) was added propylphosphonic anhydride (50% in ethyl acetate, 44 mg, 0.139 mmol) at room temperature. The mixture was stirred at 100° C. for 2 hours, cooled to room temperature and diluted with ethyl acetate (20 mL). The solution was washed with brine, dried over sodium sulfate, and concentrated. The residue was purified by Prep-HPLC to give the title compound (5.2 mg, 27%) as a white solid. MS (ESI): 702 m/z $[M+H]^+$; Retention time: 1.80 minutes; purity: >99% (254 nm) (LC-MS method 023). $^1H$ NMR (400 MHz, $CD_3OD$) δ 7.43-7.38 (m, 2H), 7.35-7.33 (m, 2H), 7.29-7.20 (m, 5H), 6.65 (d, J=3.2 Hz, 1H), 3.88 (d, J=2.0 Hz, 3H), 3.70-3.67 (m, 2H), 3.44-3.40 (m, 2H), 3.02 (d, J=13.6 Hz, 1H), 2.93-2.84 (d, J=13.6 Hz, 3H), 2.53-2.48 (m, 2H), 2.14-2.07 (m, 1H), 1.72-1.63 (m, 2H), 1.45-1.31 (m, 3H), 1.17 (s, 3H), 1.02 (s, 3H) ppm.

Example 105. 3-[3-[22,28-Difluoro-6-(fluoromethyl)-3,10,10-trimethyl-12,12-dioxo-24-oxa-12lambda6-thia-3,4,19,30-tetrazapentacyclo-[23.3.1.12,5.015,23.016,20]triaconta-1(29),2(30),4,15,17,20,22,25,27-nonaen-6-yl]phenyl]propanoic acid

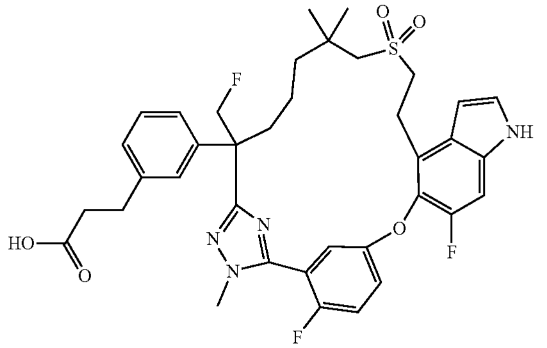 [SMILES: Cn1nc2nc1-c1cc(ccc1F)Oc1c(F)cc3[nH]ccc3c1CCS(=O)(=O)CC(C)(C)CCCC2(CF)c1cccc(CCC(=O)O)c1]

To a stirred and cooled (−78° C.) solution of 3-[3-[22,28-difluoro-6-(hydroxymethyl)-3,10,10-trimethyl-12,12-dioxo-24-oxa-12lambda6-thia-3,4,19,30-tetrazapentacyclo-[23.3.1.12,5.015,23.016,20]triaconta-1(29),2(30),4,15,17,20,22,25,27-nonaen-6-yl]phenyl]-propanoic acid (Example 103, 280 mg, 0.396 mmol) in dichloromethane (30 mL) was added diethylaminosulfur trifluoride (0.262 mL, 1.98 mmol). The mixture was stirred at this temperature for 2 hours, quenched with sodium bicarbonate (50 mL), and extracted with dichloromethane (2×50 mL). The combined organic extracts were washed with brine, dried over sodium sulfate, and concentrated. The residue was purified by Prep-HPLC to give the title compound (58 mg, 21%) as a white solid. MS (ESI): 709 m/z $[M+H]^+$; Retention time: 1.83 minutes; purity: 95% (214 nm); (LC-MS method 023). $^1H$ NMR (400 MHz, $CD_3OD$) δ 7.41-7.37 (m, 3H), 7.26 (d, J=10.8 Hz, 1H), 7.06 (dd, J=6.4, 2.8 Hz, 1H), 6.99 (t, J=7.6 Hz, 1H), 6.92-6.87 (d, J=9.6 Hz, 2H), 6.77 (d, J=7.6 Hz, 1H), 6.64 (dd, J=3.2, 0.4 Hz, 1H), 3.86 (d, J=2.0 Hz, 3H), 3.39-3.36 (m, 2H), 3.28-3.11 (m, 4H), 3.03 (d, J=13.6 Hz, 1H), 2.91 (d, J=13.6 Hz, 1H), 2.75 (t, J=7.6 Hz, 2H), 2.47 (t, J=7.6 Hz, 2H), 1.96-1.87 (m, 2H), 1.50-1.44 (m, 1H), 1.30-1.25 (m, 3H), 1.14 (s, 3H), 1.00 (s, 3H) ppm.

Example 106. 3-[3-(9,9,22,28-Tetrafluoro-3,6,10,10-tetramethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

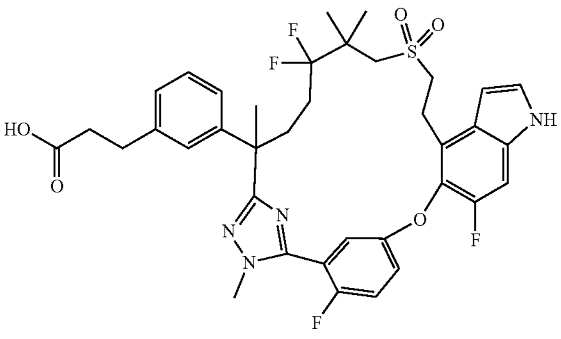 [SMILES: Cn1nc2nc1-c1cc(ccc1F)Oc1c(F)cc3[nH]ccc3c1CCS(=O)(=O)CC(C)(C)C(F)(F)CCC2(C)c1cccc(CCC(=O)O)c1]

Example 107. 3-[3-[(8Z)-9,22,28-Trifluoro-3,6,10,10-tetramethyl-12,12-dioxo-24-oxa-12lambda6-thia-3,4,19,30-tetrazapentacyclo-[23.3.1.12,5.015,23.016,20]triaconta-1(29),2(30),4,8,15,17,20,22,25,27-decaen-6-yl]phenyl]propanoic acid

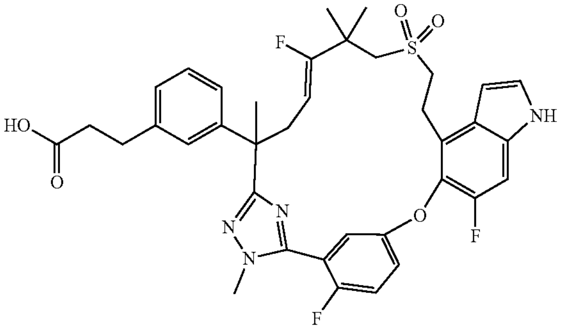 [SMILES: Cn1nc2nc1-c1cc(ccc1F)Oc1c(F)cc3[nH]ccc3c1CCS(=O)(=O)CC(C)(C)/C(F)=C/CC2(C)c1cccc(CCC(=O)O)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with ethyl 3-(3-(6,6-difluoro-7-((2-hydroxyethyl)sulfonyl)-2,5,5-trimethyl-1-(2-methylhydrazineyl)-1-oxoheptan-2-yl)phenyl)propanoate (Intermediate 69-12, 0.05 g, 0.096 mmol) in Step A, the reaction procedure sequence (Steps A, B, C, D and F) described for Example 6 was used to prepare the title compounds as a mixture after hydrolysis. The acid mixture was purified by prep-HPLC at corresponding Step F of Example 6. The first eluent, the major product, Compound 106 (13.4 mg), was obtained as a white solid. The second eluent, the minor product, Compound 107 (2 mg), was also obtained as a white solid.

Compound 106: MS (ESI): 727 m/z $[M+H]^+$, retention time: 1.89 minutes, purity: 98% (214 nm). (LC-MS Method 011). $^1$H NMR (400 MHz, $CD_3OD$) δ 7.39-7.28 (m, 3H), 7.25 (d, J=10.8 Hz, 1H), 7.21-7.17 (m, 2H), 7.07-7.03 (m, 2H), 6.95 (d, J=7.6 Hz, 1H), 6.63 (dd, J=3.2, 0.8 Hz, 1H), 3.91 (d, J=2.4 Hz, 3H), 3.41-3.15 (m, 4H), 3.06 (s, 2H), 2.82 (t, J=7.6 Hz, 2H), 2.49 (t, J=7.6 Hz, 2H), 2.47-2.35 (m, 2H), 2.07-1.99 (m, 1H), 1.81-1.65 (m, 1H), 1.74 (s, 3H), 1.22 (s, 3H), 1.17 (s, 3H) ppm.

Compound 107: MS (ESI): 707 m/z $[M+H]^+$, retention time: 1.84 minutes, purity: 96% (214 nm) (LC-MS Method 011). $^1$H NMR (400 MHz, $CD_3OD$) δ 7.38-7.33 (m, 2H), 7.29-7.19 (m, 3H), 7.14-7.06 (m, 3H), 7.01-6.99 (m, 1H), 6.64 (d, J=3.2 Hz, 1H), 3.86 (d, J=2.0 Hz, 3H), 3.50-3.37 (m, 2H), 3.15-3.06 (m, 4H), 2.91-2.81 (m, 4H), 2.62-2.50 (m, 4H), 1.73 (s, 3H), 1.21 (s, 3H), 1.10 (s, 3H) ppm.

Example 108. Enantiomers 1 and 2 of 3-[3-[22,28-difluoro-6-(fluoromethyl)-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methylpropanoic acid

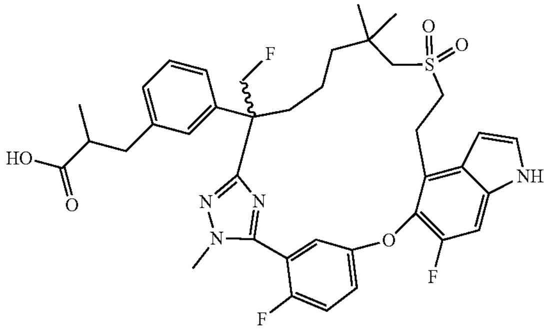 [SMILES: CC(Cc1cccc(C2(CF)CCCC(C)(C)CS(=O)(=O)CCc3c(c(F)cc4[nH]ccc34)Oc3ccc(F)c(c3)-c3nc2nn3C)c1)C(=O)O]

Exchange ethyl 2-((6-(3-(2-ethoxy-2-oxoethoxy)phenyl)-2,2,6-trimethyl-7-(2-(methyl-$d_3$)hydrazineyl)-7-oxoheptyl)sulfonyl)acetate (Intermediate 45) with ethyl 3-(3-(7-((2-ethoxy-2-oxoethyl)sulfonyl)-2-(fluoromethyl)-6,6-dimethyl-1-(2-methylhydrazineyl)-1-oxoheptan-2-yl)phenyl)-2-methylpropanoate (Intermediate 45-19, 1.80 g, 3.22 mmol) in Step A, the reaction procedure sequence (Step A to Step H) described in Example 1 was used to prepare the title compounds. The racemic acid (150 mg), obtained from corresponding Step F of Example 1, was subject to chiral SFC separation using Thar SFC-80 (Thar, Waters) under following conditions: Column: 20×250 mm×10 μm Chiralpak AD; sample solution: 150 mg dissolved in methanol (20 mL); injection volume: 1.9 mL; eluant: 75:25 carbon dioxide/isopropanol with 0.2% methanol ammonia additive; flow rate: 80 mL/minutes; column temperature: 35° C.; back pressure: 100 bar; detection wavelength: 214 nm. The first eluting isomer, enantiomer 1, was designated as Compound 108A (37 mg, 25%, white solid). The second eluting isomer, enantiomer 2, was designated as Compound 108B (38 mg, 25%, white solid).

Compound 108A: MS (ESI): 723 m/z $[M+H]^+$, retention time: 1.66 minutes, purity: >99% (214 nm) (LC-MS Method 028). $^1$H NMR (400 MHz, $CD_3OD$) δ 7.31-7.22 (m, 3H), 7.14 (d, J=10.8 Hz, 1H), 6.98-6.93 (m, 1H), 6.87 (q, J=7.2 Hz, 1H), 6.81 (t, J=6.8 Hz, 1H), 6.74 (s, 1H), 6.64 (dd, J=12.8, 7.2 Hz, 1H), 6.51 (d, J=2.8 Hz, 1H), 3.73 (t, J=2.4 Hz, 3H), 3.30-3.23 (m, 2H), 3.19-2.98 (m, 3H), 2.92-2.72 (m, 4H), 2.49-2.33 (m, 2H), 1.84-1.75 (m, 2H), 1.39-1.28 (m, 1H), 1.17-1.14 (m, 3H), 1.02 (s, 3H), 0.94-0/92 (m, 3H), 0.88 (s, 3H) ppm.

Compound 108B: MS (ESI): 723 m/z $[M+H]^+$, retention time: 1.66 minutes, purity: >99% (214 nm) (LC-MS Method 028). $^1$H NMR (400 MHz, $CD_3OD$) δ 7.30-7.21 (m, 3H), 7.13 (d, J=10.8 Hz, 1H), 6.96-6.93 (m, 1H), 6.87 (q, J=7.2 Hz, 1H), 6.80 (t, J=6.8 Hz, 1H), 6.74 (s, 1H), 6.64 (dd, J=11.6, 7.6 Hz, 1H), 6.51 (d, J=3.2 Hz, 1H), 3.73 (t, J=2.4 Hz, 3H), 3.29-3.23 (m, 2H), 3.19-2.72 (m, 7H), 2.47-2.32 (m, 2H), 1.84-1.75 (m, 2H), 1.39-1.28 (m, 1H), 1.16-1.12 (m, 3H), 1.01 (s, 3H), 0.94-0.92 (m, 3H), 0.87 (s, 3H) ppm.

Example 109. Enantiomer 1 and 2 of 3-[3-(24,30-difluoro-3,6,11,11-tetramethyl-9,9-dioxo-26-oxa-9λ6-thia-3,4,14,15,21,33-hexazahexacyclo [25.3.1.12,5.112,15.017,25.018,22]tritriaconta-1(31), 2(33),4,12(32),13,17,19,22,24,27,29-undecaen-6-yl) phenyl]propanoic Acid

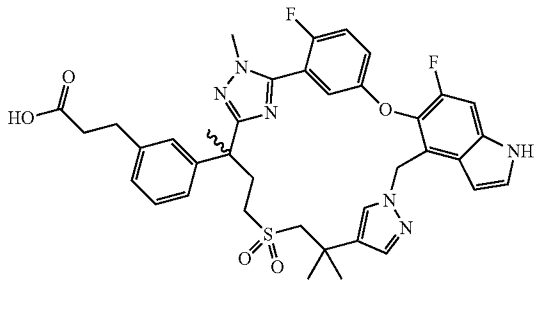 [SMILES: Cn1nc2nc1-c1cc(ccc1F)Oc1c(F)cc3[nH]ccc3c1Cn1cc(cn1)C(C)(C)CS(=O)(=O)CCC2(C)c1cccc(CCC(=O)O)c1]

(5-(3-(3-(2-(3-Bromophenyl)-4-((2-methyl-2-(1H-pyrazol-4-yl)propyl)thio)butan-2-yl)-1-methyl-1H-1,2,4-triazol-5-yl)-4-fluorophenoxy)-6-fluoro-1-(phenylsulfonyl)-1H-indol-4-yl)methyl Acetate

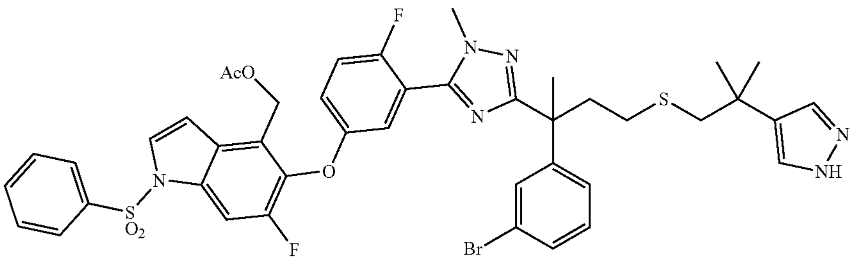 [SMILES: Cn1nc(C(C)(CCSCC(C)(C)c2cn[nH]c2)c2cccc(Br)c2)nc1-c1cc(Oc2c(F)cc3c(ccn3S(=O)(=O)c3ccccc3)c2CO)ccc1F]

Step A: To a stirred solution of 2-(3-bromophenyl)-N',2-dimethyl-4-((2-methyl-2-(1H-pyrazol-4-yl)propyl)thio)butanehydrazide (Intermediate 69-13, 1.6 g, 3.64 mmol) in pyridine (20 mL) was added (6-fluoro-5-(4-fluoro-3-(imino (methylthio)methyl)phenoxy)-1-(phenylsulfonyl)-1H-indol-4-yl)methyl acetate hydroiodide (Intermediate 14-6, 2.64 g, 4.01 mmol) and magnesium sulfate (1.6 g). The mixture was heated to 80° C. and stirred for 4 hours, then cooled to room temperature. The solution was partitioned between water (50 mL) and ethyl acetate (50 mL). The separated organic layer, combined with two additional ethyl acetate (2×50 mL) extracts, was washed with 1 N hydrochloric acid (2×50 mL), brine, dried over sodium sulfate, and concentrated. The residue was purified by automated flash chromatography (80 g silica gel column, eluted with 0-100% ethyl acetate in petroleum ether) to give the title compound (1.6 g, 49%) as a solid. MS (ESI): 903, 905 m/z $[M+H]^+$, retention time: 1.59 minutes, purity: 83% (214 nm) (LC-MS Method 029).

(5-(3-(3-(2-(3-Bromophenyl)-4-((2-methyl-2-(1H-pyrazol-4-yl)propyl)thio)butan-2-yl)-1-methyl-1H-1,2,4-triazol-5-yl)-4-fluorophenoxy)-6-fluoro-1-(phenylsulfonyl)-1H-indol-4-yl)methanol

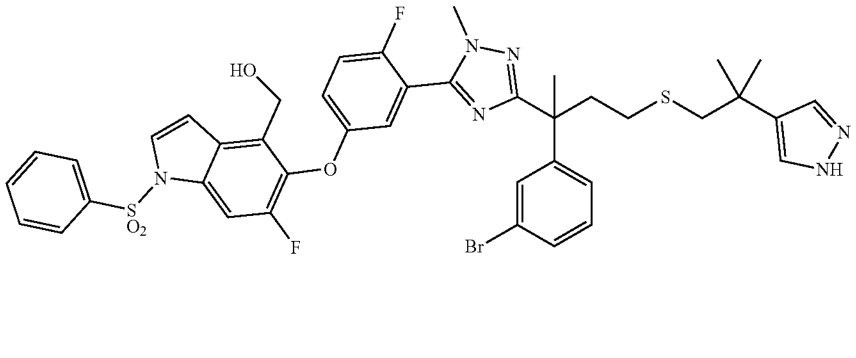

Step B: To a solution of Step A product (1.6 g, 1.77 mmol) in ethanol (20 mL) was added potassium carbonate (0.49 g, 3.54 mmol). The mixture was stirred at room temperature for 4 hours. The solution was partitioned between water (50 mL) and ethyl acetate (50 mL). The separated organic layer, combined with two additional ethyl acetate extracts (2×50 mL), was washed with 1 N hydrochloric acid (50 mL), brine, dried over sodium sulfate, and concentrated. The residue was purified by automated flash chromatography (80 g silica gel column, eluted with 0-100% ethyl acetate in petroleum ether) to give the title product as solid (1.2 g, 79%). MS (ESI): 861, 863 m/z $[M+H]^+$, retention time: 1.52 minutes, purity: 83% (214 nm) (LC-MS Method 029).

21-(Benzenesulfonyl)-6-(3-bromophenyl)-24,30-difluoro-3,6,11,11-tetramethyl-26-oxa-9-thia-3,4,14,15,21,33-hexazahexacyclo[25.3.1.12,5.112,15.017,25.018,22]tritriaconta-1(31),2(33),4,12(32),13,17,19,22,24,27,29-undecaene

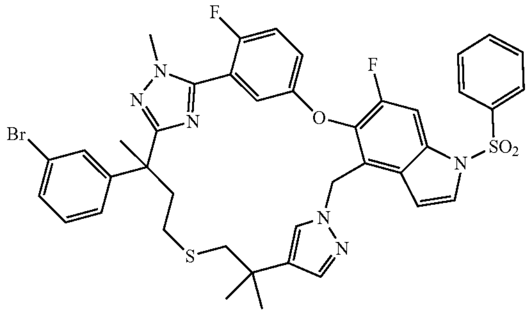 [SMILES: Cn1nc2nc1-c1cc(ccc1F)Oc1c(F)cc3c(ccn3S(=O)(=O)c3ccccc3)c1Cn1cc(cn1)C(C)(C)CSCCC2(C)c1cccc(Br)c1]

Step C: To a stirred solution of Step B product (1.2 g, 1.4 mmol) in toluene (100 mL) was added cyanomethylenetributylphosphorane (1.68 g, 7 mmol). The mixture was stirred at 110° C. for 4 hours and concentrated. The residue was purified by automated flash chromatography (40 g silica gel column, eluted with 0-50% ethyl acetate in petroleum ether) to give the title compound (430 mg, 37%) as a solid. MS (ESI): 843, 845 m/z $[M+H]^+$, retention time: 2.62 minutes, purity: 94% (254 nm) (LC-MS Method 012).

21-(Benzenesulfonyl)-6-(3-bromophenyl)-24,30-difluoro-3,6,11,11-tetramethyl-26-oxa-9lambda6-thia-3,4,14,15,21,33-hexazahexacyclo[25.3.1.12,5.112,15.017,25.018,22]tritriaconta-1(31),2(33),4,12(32),13,17,19,22,24,27,29-undecaene 9,9-dioxide

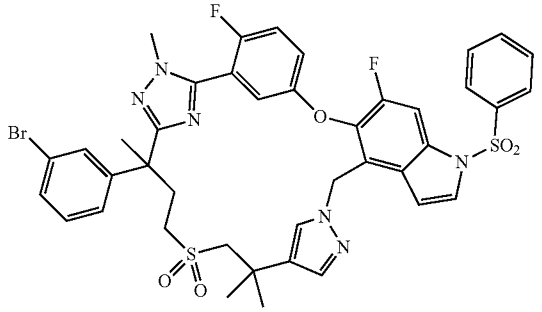 [SMILES: Cn1nc2nc1-c1cc(ccc1F)Oc1c(F)cc3c(ccn3S(=O)(=O)c3ccccc3)c1Cn1cc(cn1)C(C)(C)CS(=O)(=O)CCC2(C)c1cccc(Br)c1]

Step D: To a stirred and cooled (0° C.) solution of Step C product (0.43 g, 0.5 mmol) in methanol (20 mL) was added a solution of ammonium molybdate tetrahydrate (0.2 g) in hydrogen peroxide (2 mL, 30% in water). The mixture was stirred at room temperature for 4 hours, quenched with water, and extracted with ethyl acetate (3×50 mL). The combined organic extracts were washed with brine (50 mL), dried over sodium sulfate, and concentrated. The residue was purified by automated flash chromatography (40 g silica gel column, eluted with 0-70% ethyl acetate in petroleum ether) to give the title compound (0.36 g, 81%) as a solid. MS (ESI): 875, 877 m/z $[M+H]^+$, retention time: 2.33 minutes, purity: 87% (254 nm) (LC-MS Method 012).

6-(3-Bromophenyl)-24,30-difluoro-3,6,11,11-tetramethyl-26-oxa-9lambda6-thia-3,4,14,15,21,33-hexazahexacyclo[25.3.1.12,5.112,15.017,25.018,22]tritriaconta-1(31),2(33),4,12(32),13,17,19,22,24,27,29-undecaene 9,9-dioxide

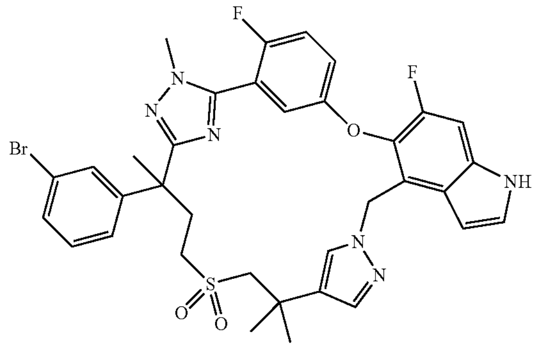 [SMILES: Cn1nc2nc1-c1cc(ccc1F)Oc1c(F)cc3[nH]ccc3c1Cn1cc(cn1)C(C)(C)CS(=O)(=O)CCC2(C)c1cccc(Br)c1]

Step E: To a stirred solution of Step D product (360 mg, 0.41 mmol) in methanol (5 mL) was added lithium hydroxide monohydrate (51.7 mg, 1.23 mmol). The mixture was stirred at room temperature for 16 hours, then diluted with water (20 mL), adjusted the pH to 5-6 with 1 N hydrochloric acid. The mixture was extracted with ethyl acetate (3×20 mL). The combined organic extracts were washed with water, brine, dried over sodium sulfate, and concentrated. The residue was purified by automated flash chromatography (12 g silica gel column, eluted with 0-100% ethyl acetate in petroleum ether) to give the title compound (230 mg, 76%). MS (ESI): 735, 737 m/z $[M+H]^+$, retention time: 1.43 minutes, purity: 99% (214 nm) (LC-MS Method 014).

Ethyl (E)-3-[3-(24,30-difluoro-3,6,11,11-tetramethyl-9,9-dioxo-26-oxa-9lambda6-thia-3,4,14,15,21,33-hexazahexacyclo[25.3.1.12,5.112,15.017,25.018,22]tritriaconta-1(31),2(33),4,12(32),13,17,19,22,24,27,29-undecaen-6-yl)phenyl]prop-2-enoate

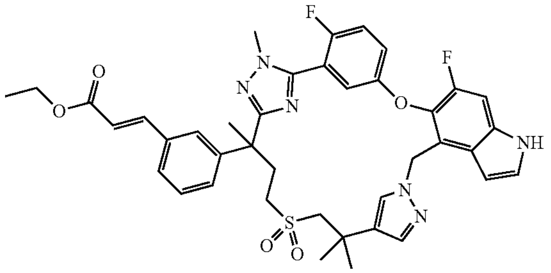 [SMILES: CCOC(=O)/C=C/c1cccc(C2(C)CCS(=O)(=O)CC(C)(C)c3cnn(c3)Cc3c(c(F)cc4[nH]ccc34)Oc3ccc(F)c(c3)-c3nc2nn3C)c1]

Step F: To a stirred and degassed solution of Step E product (150 mg, 0.2 mmol) in dioxane (5 mL) and water (1 mL) was added ethyl (E)-3-(4,4,5,5-tetramethyl-1,3,2-dioxaborolan-2-yl)prop-2-enoate (92 mg, 0.4 mmol), cesium carbonate (133 mg, 0.4 mmol) and [1,1'-bis-(diphenylphosphino)ferrocene]dichloropalladium (II) (15 mg, 0.02 mmol). The mixture was stirred at 100° C. for 3 hours, then cooled to room temperature, diluted with water (10 mL), and extracted with ethyl acetate (3×20 mL). The combined organic extracts were washed with water, brine, dried over sodium sulfate, and concentrated. The residue was purified by automated flash chromatography (12 g silica gel column, eluted with 0-100% ethyl acetate in petroleum ether) to give the title compound (120 mg, 78%). MS (ESI): 755 m/z $[M+H]^+$, retention time: 1.43 minutes, purity: 73% (214 nm) (LC-MS Method 014).

Ethyl 3-[3-(24,30-difluoro-3,6,11,11-tetramethyl-9,9-dioxo-26-oxa-9lambda6-thia-3,4,14,15,21,33-hexazahexacyclo[25.3.1.12,5.112,15.017,25.018,22]tritriaconta-1(31),2(33),4,12(32),13,17,19,22,24,27,29-undecaen-6-yl)phenyl]propanoate

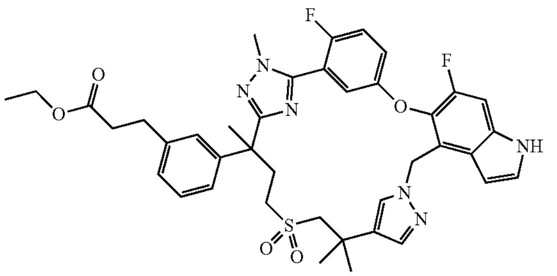 [SMILES: CCOC(=O)CCc1cccc(C2(C)CCS(=O)(=O)CC(C)(C)c3cnn(c3)Cc3c(c(F)cc4[nH]ccc34)Oc3ccc(F)c(c3)-c3nc2nn3C)c1]

Step G: To a stirred solution of Step F product (120 mg, 0.15 mmol) in ethanol (5 mL) was added palladium on active carbon (10%, 100 mg). The mixture was stirred at room temperature under hydrogen balloon for 16 hours, then filtered through a pad of Celite. The filtrate was concentrated to give the title compound (120 mg, 99%) as a light-yellow solid. MS (ESI): 757 m/z $[M+H]^+$, retention time: 1.41 minutes, purity: 88% (214 nm) (LC-MS Method 014). 3-[3-(24,30-Difluoro-3,6,11,11-tetramethyl-9,9-dioxo-26-oxa-9lambda6-thia-3,4,14,15,21,33-hexazahexacyclo[25.3.1.12,5.112,15.017,25.018,22]tritriaconta-1(31),2(33),4,12(32),13,17,19,22,24,27,29-undecaen-6-yl)phenyl]propanoic Acid

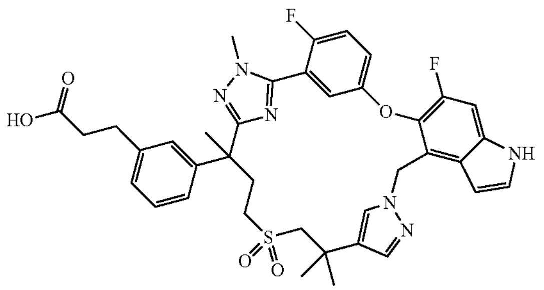 [SMILES: Cn1nc2nc1-c1cc(ccc1F)Oc1c(F)cc3[nH]ccc3c1Cn1cc(cn1)C(C)(C)CS(=O)(=O)CCC2(C)c1cccc(CCC(=O)O)c1]

Step H: To a stirred solution of Step G product (120 mg, 0.15 mmol) in methanol (2 mL) and water (0.5 mL) was added lithium hydroxide monohydrate (18 mg, 0.4 mmol). The mixture was stirred at room temperature for 4 hours. The reaction solution was diluted with water (20 mL) and adjusted the pH to 5-6 with 1 N hydrochloric acid. The suspension was extracted with ethyl acetate (3×20 mL). The combined organic extracts were washed with water, brine, dried over sodium sulfate, and concentrated. The residue was purified by automated flash chromatography (12 g silica gel column, eluted with 0-100% ethyl acetate in petroleum ether) to give the title compound (100 mg, 85%). MS (ESI): 729 m/z $[M+H]^+$, retention time: 1.27 minutes, purity: 91% (214 nm) (LC-MS Method 014).

Compounds 109A and 109B: Enantiomers 1 and 2 of 3-[3-(24,30-difluoro-3,6,11,11-tetramethyl-9,9-dioxo-26-oxa-9lambda6-thia-3,4,14,15,21,33-hexazahexacyclo[25.3.1.12,5.112,15.017,25.018,22]tritriaconta-1(31),2(33),4,12(32),13,17,19,22,24,27,29-undecaen-6-yl)phenyl]propanoic Acid

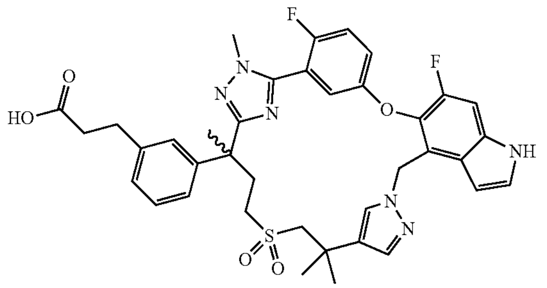 [SMILES: Cn1nc2nc1-c1cc(ccc1F)Oc1c(F)cc3[nH]ccc3c1Cn1cc(cn1)C(C)(C)CS(=O)(=O)CCC2(C)c1cccc(CCC(=O)O)c1]

Step I: The racemic Step H product (100 mg) was subject to chiral SFC separation using SFC-150 (Thar, Waters) under the following separation conditions: Column: R'R WHELK 20*250 mm, 10 μm; Column temperature: 35° C.; Mobile phase: Carbon dioxide/methanol (0.2% methanol ammonia as additive)=40/60; Flow rate: 120 g/minute; Back pressure: 100 bar; Detection wavelength: 214 nm; Cycle time: 6.5 minutes; Sample solution: 100 mg dissolved in 20 ml Methanol; Injection volume: 1.9 mL. The first eluent, enantiomer 1, was designated as Compound 109A (35 mg, 35%). The second eluent, enantiomer 2, was designated as Compound 109B (35 mg, 35%).

Compound 109A: MS (ESI): 729 m/z $[M+H]^+$, retention time: 1.25 minutes, purity: 99% (214 nm). (LC-MS Method 014). $^1$H NMR (400 MHz, $CD_3OD$) δ 7.28-7.21 (m, 2H), 7.16 (d, J=1.6 Hz, 1H), 7.13-7.14 (m, 1H), 7.04-7.09 (m, 3H), 6.98-6.86 (m, 3H), 6.63 (d, J=4.8 Hz, 1H), 6.55 (d, J=3.2 Hz, 1H), 5.49, 5.45-5.35 (m, 2H), 3.68 (d, J=2.4 Hz, 3H), 3.22-3.26 (m, 1H), 3.07 (d, J=14.2, 1H), 3.04-2.91 (m, 1H), 2.70 (t, J=7.2 Hz, 2H), 2.50-2.60 (m, 2H), 2.33-2.41 (m, 2H), 2.19-2.26 (m, 1H), 1.56 (s, 3H), 1.30 (s, 3H), 1.22 (s, 3H) ppm.

Compound 109B: MS (ESI): 729 m/z $[M+H]^+$, retention time: 1.25 minutes, purity: 99% (214 nm). (LC-MS Method 14). $^1$H NMR (400 MHz, $CD_3OD$) δ 7.28-7.21 (m, 2H), 7.16 (d, J=1.6 Hz, 1H), 7.13-7.14 (m, 1H), 7.04-7.09 (m, 3H), 6.98-6.86 (m, 3H), 6.63 (d, J=4.8 Hz, 1H), 6.55 (d, J=3.2 Hz, 1H), 5.49, 5.45-5.35 (m, 2H), 3.68 (d, J=2.4 Hz, 3H), 3.22-3.26 (m, 1H), 3.07 (d, J=14.2, 1H), 3.04-2.91 (m, 1H), 2.70 (t, J=7.2 Hz, 2H), 2.50-2.60 (m, 2H), 2.33-2.41 (m, 2H), 2.19-2.26 (m, 1H), 1.56 (s, 3H), 1.30 (s, 3H), 1.22 (s, 3H) ppm.

Example 110. 3-[3-(24,30-Difluoro-3,6,11,11-tetramethyl-9,9-dioxo-26-oxa-9lambda6-thia-3,4,14,15,21,33-hexazahexacyclo-[25.3.1.12,5.112,15.017,25.018,22]tritriaconta-1(31),2(33),4,12(32),13,17,19,22,24,27,29-undecaen-6-yl)phenyl]-2-methylpropanoic Acid

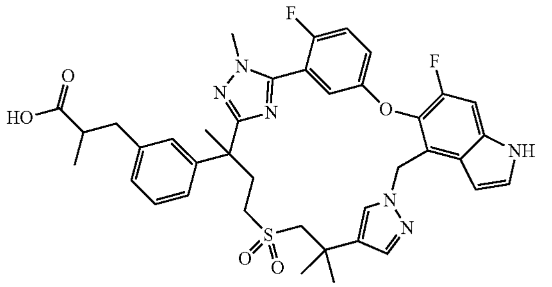 [SMILES: CC(Cc1cccc(C2(C)CCS(=O)(=O)CC(C)(C)c3cnn(c3)Cc3c(c(F)cc4[nH]ccc34)Oc3ccc(F)c(c3)-c3nc2nn3C)c1)C(=O)O]

Exchanging ethyl (E)-3-(4,4,5,5-tetramethyl-1,3,2-dioxaborolan-2-yl)prop-2-enoate with ethyl (E)-2-methyl-3-(4,4,5,5-tetramethyl-1,3,2-dioxaborolan-2-yl)prop-2-enoate (50 mg, 0.2 mmol) in Step E, the reaction procedure sequence (Steps A to H) described for Example 109A and 109B was used to prepare the title compound 110 (10 mg).

Compound 110: MS (ESI): 743 m/z $[M+H]^+$, retention time: 1.56 minutes, purity: 99% (214 nm). (LC-MS Method 030). $^1H$ NMR (400 MHz, $CD_3OD$) δ 7.27 (d, J=3.2 Hz, 1H), 7.23 (dd, J=10.8, 4.0 Hz, 1H), 7.20-7.14 (m, 2H), 7.06-7.11 (m, 3H), 6.97-6.87 (m, 3H), 6.63-6.66 (m, 1H), 6.56-5.68 (m, 1H), 5.40-5.52 (m, 2H), 3.70 (d, J=1.6 Hz, 3H), 3.30-3.23 (m, 1H), 3.08 (d, J=14.8 Hz, 1H), 2.97-3.04 (m, 1H), 2.80-2.86 (m, 1H), 2.47-2.60 (m, 4H), 2.25-2.33 (m, 1H), 1.58 (s, 3H), 1.34 (s, 3H), 1.26 (s, 3H), 0.96 (t, J=6.0 Hz, 3H) ppm.

Example 111. 3-[3-(24,30-Difluoro-3,6,11,11-tetramethyl-10,10-dioxo-26-oxa-10λ6-thia-3,4,14,15,21,33-hexazahexacyclo[25.3.1.12,5.112,15.017,25.018,22]-tritriaconta-1(31),2(33),4,12(32),13,17,19,22,24,27,29-undecaen-6-yl)phenyl]propanoic Acid

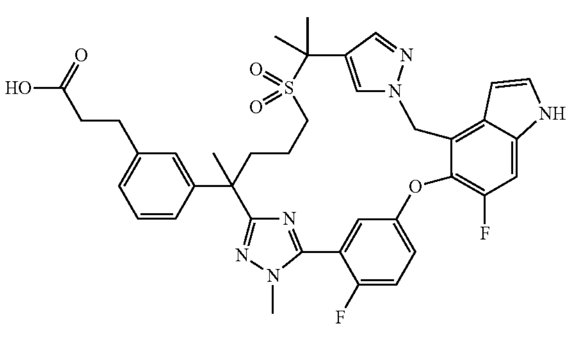 [SMILES: Cn1nc2nc1-c1cc(ccc1F)Oc1c(F)cc3[nH]ccc3c1Cn1cc(cn1)C(C)(C)S(=O)(=O)CCCC2(C)c1cccc(CCC(=O)O)c1]

Ethyl 3-(3-(2-(5-(2-fluoro-5-((6-fluoro-1-tosyl-4-vinyl-1H-indol-5-yl)oxy)phenyl)-1-methyl-1H-1,2,4-triazol-3-yl)-5-((2-(1-((2-(trimethylsilyl)ethoxy)methyl)-1H-pyrazol-4-yl)propan-2-yl)sulfonyl)pentan-2-yl)phenyl)propanoate

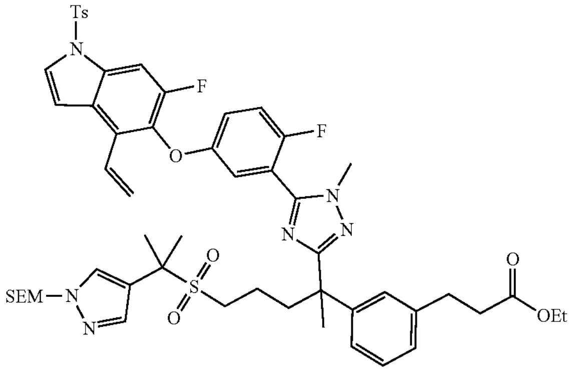 [SMILES: C=Cc1c(Oc2ccc(F)c(-c3nc(C(C)(CCCS(=O)(=O)C(C)(C)c4cnn(COCC[Si](C)(C)C)c4)c4cccc(CCC(=O)OCC)c4)nn3C)c2)c(F)cc2c1ccn2S(=O)(=O)c1ccc(C)cc1]

Step A: To a stirred solution of ethyl 3-(3-(2-methyl-1-(2-methylhydrazineyl)-1-oxo-5-((2-(1-((2-(trimethylsilyl)ethoxy)methyl)-1H-pyrazol-4-yl)propan-2-yl)sulfonyl)pentan-2-yl)phenyl)-propanoate (Intermediate 112, 5.43 g, 6 mmol) in pyridine (50 mL) was added methyl 2-fluoro-5-((6-fluoro-1-tosyl-4-vinyl-1H-indol-5-yl)oxy)benzimidothioate hydroiodide (Intermediate 14-3, 3.0 g, 6 mmol). The mixture was stirred at 75° C. for 3 hours, then diluted with water (150 mL), and extracted with ethyl acetate (3×100 mL). The combined organic extracts were washed with hydrochloric acid (1 M, 2×100 mL), brine, dried over sodium sulfate, and concentrated. The residue was purified by automated silica gel column chromatography (40 g silica gel column, eluted with 0-60% ethyl acetate in petroleum ether) to give the title compound (2.4 g, 40%) as a solid. MS (ESI): 1055 m/z $[M+H]^+$, retention time: 2.56 minutes, purity: 90% (214 nm) (LC-MS Method 022).

Ethyl 3-(3-(2-(5-(2-fluoro-5-((6-fluoro-4-formyl-1-tosyl-1H-indol-5-yl)oxy)phenyl)-1-methyl-1H-1,2,4-triazol-3-yl)-5-((2-(1-((2-(trimethylsilyl)ethoxy)methyl)-1H-pyrazol-4-yl)propan-2-yl)sulfonyl)pentan-2-yl)phenyl)propanoate

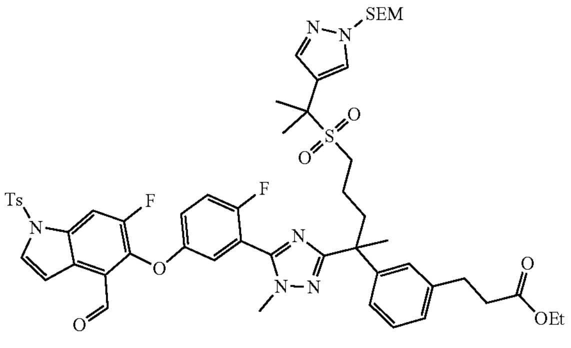 [SMILES: CCOC(=O)CCc1cccc(C(C)(CCCS(=O)(=O)C(C)(C)c2cnn(COCC[Si](C)(C)C)c2)c2nc(-c3cc(Oc4c(F)cc5c(ccn5S(=O)(=O)c5ccc(C)cc5)c4C=O)ccc3F)n(C)n2)c1]

Step B: To a stirred solution of Step A product (150 mg, 0.15 mmol) in 6 mL of acetone and 2 mL of water was added osmium tetra-oxide (0.14 mL, 0.04 M in water) and sodium periodate (60 mg, 0.28 mmol). The mixture was stirred at room temperature for 16 hours, diluted with water, and extracted with ethyl acetate (3×10 mL). The combined organic extracts were washed with brine, dried over sodium sulfate, and concentrated to give the crude title compound (150 mg). MS (ESI): 1057 m/z [M+H]+, retention time: 1.73 minutes, purity: 88% (214 nm) (LC-MS Method 014).

Ethyl 3-(3-(2-(5-(2-fluoro-5-((6-fluoro-4-(hydroxymethyl)-1-tosyl-1H-indol-5-yl)oxy)phenyl)-1-methyl-1H-1,2,4-triazol-3-yl)-5-((2-(1-((2-(trimethylsilyl)ethoxy)methyl)-1H-pyrazol-4-yl)propan-2-yl)sulfonyl)pentan-2-yl)phenyl)propanoate

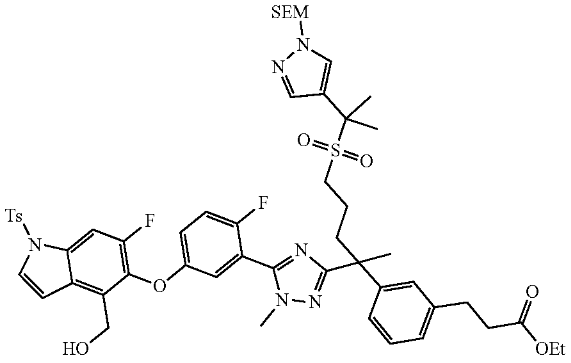 [SMILES: CCOC(=O)CCc1cccc(C(C)(CCCS(=O)(=O)C(C)(C)c2cnn(COCC[Si](C)(C)C)c2)c2nc(-c3cc(Oc4c(F)cc5c(ccn5S(=O)(=O)c5ccc(C)cc5)c4CO)ccc3F)n(C)n2)c1]

Step C: To a stirred solution of Step B product (1.8 g, 1.7 mmol) in tetrahydrofuran (30 mL) was added a drop of methanol, followed by sodium borohydride (129 mg, 3.4 mmol). The mixture was stirred at room temperature for 16 hours, quenched with saturated ammonium chloride (20 mL), and extracted with ethyl acetate (2×100 mL). The combined organic extracts were washed with brine, dried over sodium sulfate, and concentrated. The residue was purified by silica gel column chromatography to give the title compound (605 mg, 35% for 2 steps). MS (ESI): 1059 m/z [M+H]+, retention time: 2.14 minutes, purity: 90% (214 nm). (LC-MS Method 031).

Ethyl 3-(3-(5-((2-(1H-pyrazol-4-yl)propan-2-yl)sulfonyl)-2-(5-(2-fluoro-5-((6-fluoro-4-(hydroxymethyl)-1-tosyl-1H-indol-5-yl)oxy)phenyl)-1-methyl-1H-1,2,4-triazol-3-yl)pentan-2-yl)phenyl)propanoate

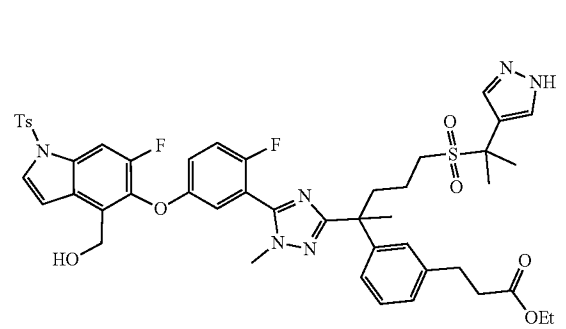 [SMILES: CCOC(=O)CCc1cccc(C(C)(CCCS(=O)(=O)C(C)(C)c2cn[nH]c2)c2nc(-c3cc(Oc4c(F)cc5c(ccn5S(=O)(=O)c5ccc(C)cc5)c4CO)ccc3F)n(C)n2)c1]

Step D: To a stirred solution of Step C product (650 mg, 0.61 mmol) in dichloromethane (20 mL) was added ethyl ether-boron trifluoride complex (10 drops) at room temperature. The mixture was stirred at room temperature for 1 hour, quenched with saturated sodium bicarbonate (5 mL), and extracted with ethyl acetate (2×20 mL). The combined organic phase was washed with brine (10 mL), dried over sodium sulfate, and concentrated. The residue was purified by flash chromatography to give the title compound as a solid (350 mg, 60%). MS (ESI): 929 m/z [M+H]+, retention time: 2.12 minutes, purity: 87% (214 nm) (LC-MS Method 022).

Ethyl 3-[3-[24,30-difluoro-3,6,11,11-tetramethyl-10,10-dioxo-21-(p-tolylsulfonyl)-26-oxa-10lambda6-thia-3,4,14,15,21,33-hexazahexacyclo[25.3.1.12,5.112,15.017,25.018,22]-tritriaconta-1(31),2(33),4,12(32),13,17,19,22,24,27,29-undecaen-6-yl]phenyl]propanoate

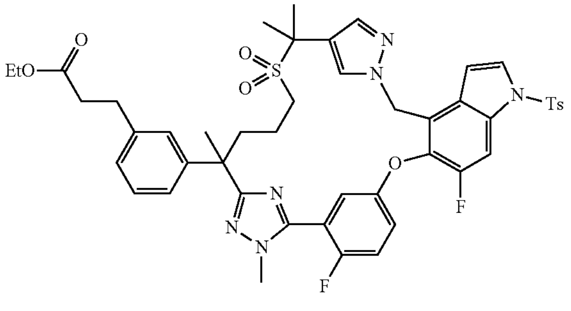 [SMILES: CCOC(=O)CCc1cccc(C2(C)CCCS(=O)(=O)C(C)(C)c3cnn(c3)Cc3c(c(F)cc4c3ccn4S(=O)(=O)c3ccc(C)cc3)Oc3ccc(F)c(c3)-c3nc2nn3C)c1]

Step E: To a stirred solution of Step D product (200 mg, 0.22 mmol) in toluene (20 mL) was added 2-(triphenyl-15-phosphanylidene)acetonitrile (0.65 mmol, 200 mg) in a 25 mL microwave reaction vial. The mixture was heated at 150° C. in a microwave reactor for 50 minutes. The solvent was removed via evaporation. The residue was purified by flash chromatography to give the title compound as a solid (40 mg, 25%). MS (ESI): 911 m/z [M+H]+, retention time: 2.15 minutes, purity: 60% (214 nm) (LC-MS Method 022).

Compound 111: 3-[3-(24,30-Difluoro-3,6,11,11-tetramethyl-10,10-dioxo-26-oxa-106-thia-3,4,14,15,21,33-hexazahexacyclo[25.3.1.12,5.112,15.017,25.018,22]-tritriaconta-1(31),2(33),4,12(32),13,17,19,22,24,27,29-undecaen-6-yl)phenyl]propanoic Acid

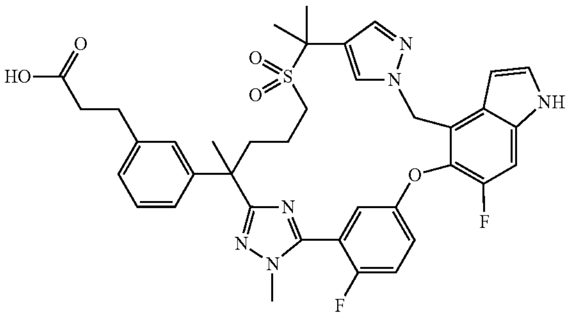 [SMILES: Cn1nc2nc1-c1cc(ccc1F)Oc1c(F)cc3[nH]ccc3c1Cn1cc(cn1)C(C)(C)S(=O)(=O)CCCC2(C)c1cccc(CCC(=O)O)c1]

Step F: A mixture of Step E product (85 mg, 0.1 mmol) and 0.2 M lithium hydroxide (methanol:water:tetrahydrofuran=1:1:3, 2 mL) was stirred at 45° C. for 16 hours, then cooled to room temperature and acidified with 14 mL of 1 N hydrochloric acid. The mixture was extracted with ethyl acetate (3×15 mL). The combined organic extracts were washed with brine, dried over sodium sulfate, and concentrated. The residue was purified by preparative-thin layer chromatography to give the title compound (30.2 mg, 44%) as a white solid. MS (ESI): 729 m/z $[M+H]^+$, retention time: 1.26 minutes, purity: >99% (254 nm) (LC-MS Method 031). $^1H$ NMR (400 MHz, $CD_3OD$) δ 7.74 (s, 1H), 7.47 (s, 1H), 7.46-7.33 (m, 4H), 7.19 (t, J=7.6 Hz, 1H), 7.12-7.02 (m, 3H), 6.86 (dd, J=5.2, 2.8 Hz, 1H), 6.77 (d, J=2.8 Hz, 1H), 5.64 (s, 2H), 3.88 (d, J=2.0 Hz, 3H), 2.88 (t, J=7.6 Hz, 2H), 2.68 (td, J=12.4, 4.8 Hz, 1H), 2.56 (t, J=7.6 Hz, 2H), 2.55-2.48 (m, 1H), 2.25-2.19 (m, 1H), 2.16-2.10 (m, 1H), 1.93-1.86 (m, 1H), 1.70 (s, 3H), 1.66 (s, 3H), 1.55 (s, 3H), 1.51-1.44 (m, 1H) ppm.

Example 112. 3-[3-(22,28-Difluoro-3,6-dimethyl-9,9,12,12-tetraoxo-24-oxa-9lambda6,12lambda6-dithia-3,4,19,30-tetrazapentacyclo-[23.3.1.12,5.015,23.016,20]triaconta-1(29),2(30),4,15,17,20,22,25,27-nonaen-6-yl)phenyl]-2-methyl-propanoic Acid

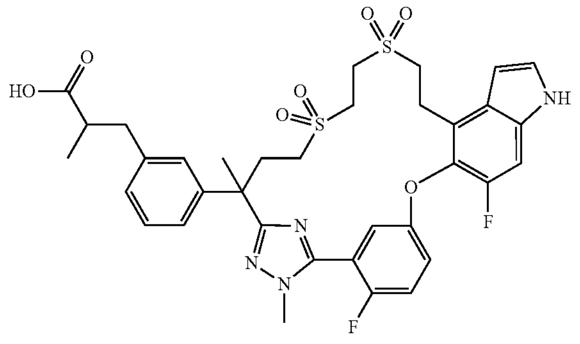 [SMILES: CC(Cc1cccc(C2(C)CCS(=O)(=O)CCS(=O)(=O)CCc3c(c(F)cc4[nH]ccc34)Oc3ccc(F)c(c3)-c3nc2nn3C)c1)C(=O)O]

Ethyl (E)-3-(3-(2-(5-(5-((4-bromo-6-fluoro-1H-indol-5-yl)oxy)-2-fluorophenyl)-1-methyl-1H-1,2,4-triazol-3-yl)-4-((2-((2-hydroxyethyl)thio)ethyl)thio)butan-2-yl)phenyl)-2-methylacrylate

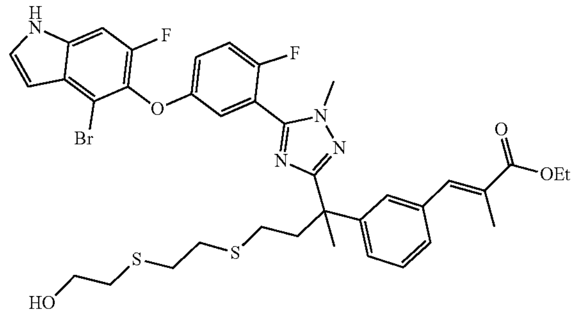 [SMILES: CCOC(=O)/C(C)=C/c1cccc(C(C)(CCSCCSCCO)c2nc(-c3cc(Oc4c(F)cc5[nH]ccc5c4Br)ccc3F)n(C)n2)c1]

Step A: To a stirred solution of ethyl (E)-3-(3-(4-((2-((2-hydroxyethyl)thio)ethyl)thio)-2-methyl-1-(2-methylhydrazineyl)-1-oxobutan-2-yl)phenyl)-2-methylacrylate (Intermediate 114, 0.815 g, 1.79 mmol) in pyridine (30 mL) was added methyl 5-((4-bromo-6-fluoro-1H-indol-5-yl)oxy)-2-fluorobenzimidothioate hydroiodide (Intermediate 14-1, 1.13 g, 2.15 mmol) and magnesium sulfate (2 g). The mixture was stirred at 85° C. overnight and cooled to room temperature. The solution was partitioned between water (100 mL) and ethyl acetate (100 mL). The separated organic layer, combined with two additional ethyl acetate extracts (2×50 mL), was washed with brine, dried over sodium sulfate, and concentrated. The residue was purified by automated flash chromatography (40 g silica gel column, eluted with 0-80% ethyl acetate in petroleum ether) to give the title compound (0.9 g, 64%) as oil. MS (ESI): 785, 787 m/z $[M+H]^+$, retention time: 1.56 minutes, purity: 72% (254 nm) (LC-MS Method 014).

(E)-3-(3-(2-(5-(5-((4-Bromo-6-fluoro-1H-indol-5-yl)oxy)-2-fluorophenyl)-1-methyl-1H-1,2,4-triazol-3-yl)-4-((2-((2-hydroxyethyl)thio)ethyl)thio)butan-2-yl)phenyl)-2-methylacrylic Acid

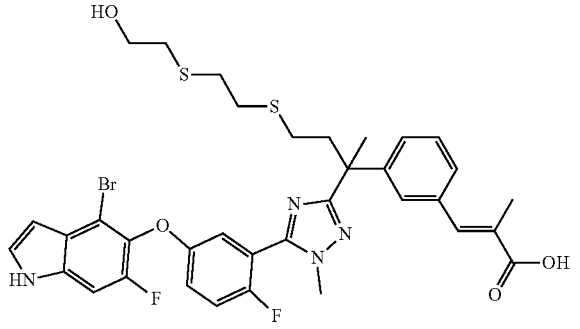 [SMILES: C/C(=C\c1cccc(C(C)(CCSCCSCCO)c2nc(-c3cc(Oc4c(F)cc5[nH]ccc5c4Br)ccc3F)n(C)n2)c1)C(=O)O]

Step B: A mixture of Step A product (0.9 g, 1.15 mmol) and lithium hydroxide (0.2 M in tetrahydrofuran/methanol/water (3:1:1)) (9 mL) was stirred at room temperature for 2 hours. The clear solution was acidified with 1 N hydrochloric acid and extracted with ethyl acetate (3×50 mL). The combined organic extracts were washed with brine, dried over sodium sulfate, and concentrated. The residue was purified by automated flash chromatography (40 g silica gel column, eluted with 0-10% methanol in dichloromethane) to give the title compound (410 mg, 47%) as a solid. MS (ESI): 757 m/z $[M+H]^+$, retention time: 1.39 minutes, purity: 93% (214 nm) (LC-MS Method 014).

Benzyl (E)-3-(3-(2-(5-(5-((4-bromo-6-fluoro-1H-indol-5-yl)oxy)-2-fluorophenyl)-1-methyl-1H-1,2,4-triazol-3-yl)-4-((2-((2-hydroxyethyl)thio)ethyl)thio)butan-2-yl)phenyl)-2-methylacrylate

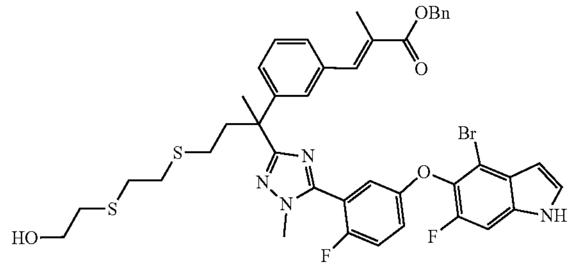 [SMILES: C/C(=C\c1cccc(C(C)(CCSCCSCCO)c2nc(-c3cc(Oc4c(F)cc5[nH]ccc5c4Br)ccc3F)n(C)n2)c1)C(=O)OCc1ccccc1]

Step C: To a stirred solution of Step B product (410 mg, 0.541 mmol) and benzyl bromide (111 mg, 0.649 mmol) in acetone (10 mL) was added potassium carbonate (150 mg, 1.08 mmol). The mixture was refluxed for 2 hours, cooled to room temperature, and diluted with ethyl acetate (100 mL).

The solution was washed with water, brine, dried over sodium sulfate, and concentrated. The residue was purified by automated flash chromatography (25 g silica gel column, eluted with 0-80% ethyl acetate in petroleum ether) to give the title compound (0.25 g, 54%) as solid. MS (ESI): 847 m/z $[M+H]^+$, retention time: 1.63 minutes, purity: 82% (214 nm) (LC-MS Method 014).

Benzyl (E)-3-(3-(2-(5-(5-((4-bromo-6-fluoro-1H-indol-5-yl)oxy)-2-fluorophenyl)-1-methyl-1H-1,2,4-triazol-3-yl)-4-((2-((2-hydroxyethyl)sulfonyl)ethyl)sulfonyl)butan-2-yl)phenyl)-2-methylacrylate

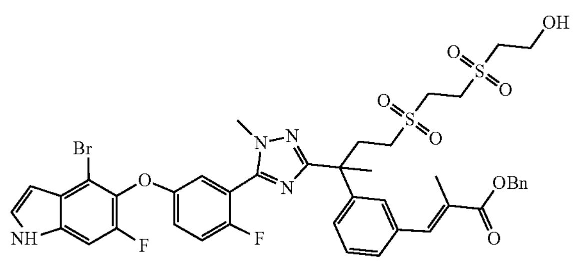 [SMILES: C/C(=C\c1cccc(C(C)(CCS(=O)(=O)CCS(=O)(=O)CCO)c2nc(-c3cc(Oc4c(F)cc5[nH]ccc5c4Br)ccc3F)n(C)n2)c1)C(=O)OCc1ccccc1]

Step D: To a stirred solution of Step C product (250 mg, 0.295 mmol) in methanol (20 mL) was added a solution of ammonium molybdate tetrahydrate (0.4 g, 0.324 mmol) in hydrogen peroxide (30% in water, 2 mL). The reaction was stirred at room temperature for 15 minutes, then diluted with ethyl acetate (80 mL). The solution was washed with water, brine, dried over sodium sulfate, and concentrated to give the title compound (240 mg, 89%) as an oil. MS (ESI): 911 m/z $[M+H]^+$, retention time: 2.18 minutes, purity: 89% (214 nm) (LC-MS Method 014).

Compound 112: 3-[3-(22,28-Difluoro-3,6-dimethyl-9,9,12,12-tetraoxo-24-oxa-9lambda6,12lambda6-dithia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

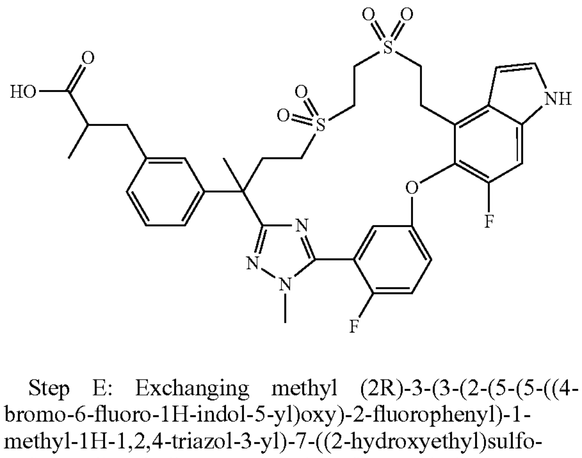

Step E: Exchanging methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 6) with benzyl 3-(3-(2-(5-(5-((4-bromo-6-fluoro-1H-indol-5-yl)oxy)-2-fluorophenyl)-1-methyl-1H-1,2,4-triazol-3-yl)-4-((2-((2-hydroxyethyl)sulfonyl)ethyl)sulfonyl)butan-2-yl)phenyl)-2-methylacrylate (Step D product of this Example, 170 mg, 0.186 mmol), the reaction procedure sequence (Step B to D and Step F) described for Example 6 was used to prepare the title compound (4.2 mg) as a white solid. MS (ESI): 727 m/z $[M+H]^+$, retention time: 1.74 minutes, purity: >99% (254 nm) (LC-MS Method 011). $^1H$ NMR (400 MHz, $CD_3OD$) δ 7.43-7.36 (m, 2H), 7.35 (d, J=3.2 Hz, 1H), 7.27 (d, J=10.8 Hz, 1H), 7.16 (t, J=7.6 Hz, 1H), 7.06 (d, J=7.6 Hz, 1H), 7.03-6.96 (m, 3H), 6.63 (d, J=3.2 Hz, 1H), 3.88 (dd, J=2.4, 1.2 Hz, 3H), 3.51-3.37 (m, 6H), 3.25-3.15 (m, 2H), 2.95-2.76 (m, 3H), 2.58-2.49 (m, 3H), 2.40-2.31 (m, 1H), 1.77 (s, 3H), 1.01 (t, J=6.4 Hz, 3H) ppm.

Example 113. Enantiomer 1 and 2 of 3-[3-[(6R)-22,28-difluoro-3,6,10,10-tetramethyl-12,12-dioxo-8,24-dioxa-12lambda6-thia-3,4,19,30-tetrazapentacyclo-[23.3.1.12,5.015,23.016,20]triaconta-1(29),2(30),4,15,17,20,22,25,27-nonaen-6-yl]phenyl]-2-methyl-propanoic Acid

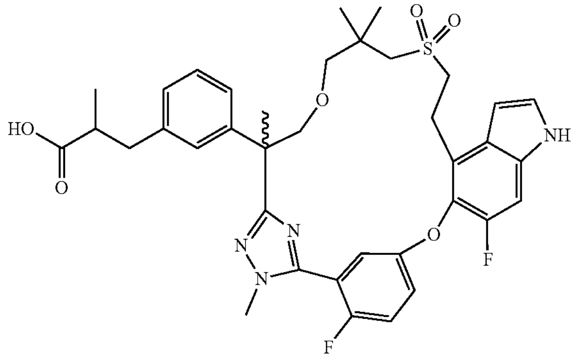 [SMILES: CC(Cc1cccc(C2(C)COCC(C)(C)CS(=O)(=O)CCc3c(c(F)cc4[nH]ccc34)Oc3ccc(F)c(c3)-c3nc2nn3C)c1)C(=O)O]

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with ethyl 3-(3-(3-(3-((2-hydroxyethyl)sulfonyl)-2,2-dimethylpropoxy)-2-methyl-1-(2-methylhydrazineyl)-1-oxo-propan-2-yl)phenyl)-2-methylpropanoate (Intermediate 115, 1.2 g, 2.4 mmol), the reaction procedure sequence (Step A to G) described for Example 6 was used to prepare the title compounds. The racemic ethyl ester (450 mg, 0.612 mmol), obtained from corresponding Step D of Example 6, was subject to chiral SFC conditions under the following condition: Instrument: SFC-200 (Thar, Waters); Column: AD 20*250 mm, 10 μm; Column temperature: 35° C.; Mobile phase: carbon dioxide/methanol (0.2% methanol ammonia as additive)=75/25; Flow rate: 120 g/minutes; Back pressure: 100 bar; Detection wavelength: 214 nm; Cycle time: 4.3 minutes; Sample solution: 450 mg dissolved in 20 mL methanol; Injection volume: 1 mL. The first eluent, enantiomer 1 (130 mg, 29%, white solid), was further hydrolyzed to Compound 113A (102 mg, 82%, white solid). The second eluent, enantiomer 2 (125 mg, 28%, white solid), was further hydrolyzed to Compound 113B (99.6 mg, 83%, white solid), utilizing the conditions described in Step F of Example 6.

Compound 113A: MS (ESI): 707 m/z $[M+H]^+$, retention time: 1.84 minutes, purity: >99% (254 nm). (LC-MS Method 022). $^1H$ NMR (400 MHz, $CD_3OD$) δ 7.49-7.46 (m, 1H), 7.42 (t, J=9.2 Hz, 1H), 7.34 (d, J=3.2 Hz, 1H), 7.25 (d, J=10.8 Hz, 1H), 7.17 (t, J=7.6 Hz, 1H), 7.06-6.98 (m, 4H), 6.70 (d, J=3.2 Hz, 1H), 4.03 (d, J=8.4 Hz, 1H), 3.84 (d, J=2.0 Hz, 3H), 3.58 (dd, J=8.4, 3.6 Hz, 1H), 3.52-3.43 (m, 2H), 3.17 (t, J=7.2 Hz, 2H), 3.03 (d, J=9.2 Hz, 1H), 2.98-2.91 (m, 2H), 2.67-2.56 (m, 4H), 1.73 (s, 3H), 1.07 (dd, J=6.8, 2.8 Hz, 3H), 0.97 (s, 6H) ppm.

Compound 113B: MS (ESI): 707 m/z $[M+H]^+$, retention time: 1.84 minutes, purity: 99% (254 nm). (LC-MS Method 022). $^1$H NMR (400 MHz, $CD_3OD$) δ 7.49-7.46 (m, 1H), 7.42 (t, J=9.2 Hz, 1H), 7.34 (d, J=3.2 Hz, 1H), 7.25 (d, J=10.8 Hz, 1H), 7.17 (t, J=7.6 Hz, 1H), 7.06-6.98 (m, 4H), 6.70 (d, J=3.2 Hz, 1H), 4.03 (d, J=8.4 Hz, 1H), 3.84 (d, J=2.0 Hz, 3H), 3.58 (dd, J=8.4, 3.6 Hz, 1H), 3.52-3.43 (m, 2H), 3.17 (t, J=6.8 Hz, 2H), 3.03 (d, J=9.2 Hz, 1H), 2.98-2.90 (m, 2H), 2.65-2.56 (m, 4H), 1.73 (s, 3H), 1.07 (dd, J=6.4, 2.4 Hz, 3H), 0.97 (s, 6H) ppm.

Example 114. 3-[3-(22,28-Difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl) phenyl]-2-methyl-propanoic Acid

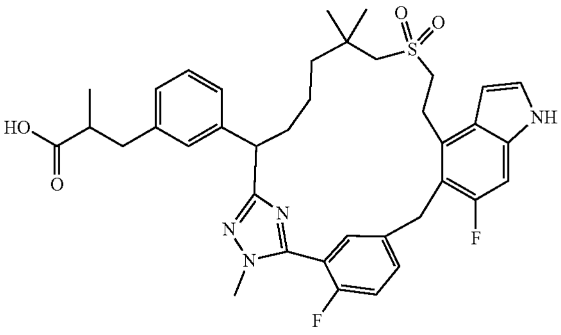 [SMILES: CC(Cc1cccc(C2CCCC(C)(C)CS(=O)(=O)CCc3c(c(F)cc4[nH]ccc34)Cc3ccc(F)c(c3)-c3nc2nn3C)c1)C(=O)O]

To a stirred solution of ethyl 3-[3-(22,28-difluoro-6-formyl-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl) phenyl]-2-methyl-propanoate (Step B product of Example 20, 50 mg, 0.0669 mmol) in tetrahydrofuran (1.0 mL), methanol (1.0 mL) and water (0.5 mL) was added lithium hydroxide monohydrate (28.1 mg, 0.669 mmol). The reaction was stirred at room temperature for 3 hours, diluted with water (10 mL), and acidified with 1.0 M hydrochloric acid to pH ~6. The mixture was extracted with ethyl acetate (3×10 mL). The combined organic extracts were washed with brine, dried over sodium sulfate, and concentrated. The residue was purified by automated flash chromatography (4.0 g silica gel column, eluted with 0-60% ethyl acetate in petroleum ether) to give the title compound (15 mg, 32%) as a white solid. MS (ESI): 691 m/z $[M+H]^+$, retention time: 1.64 minutes, purity: >99% (214 nm) (LC-MS Method 028). $^1$H NMR (400 MHz, DMSO-$d_6$) δ 11.96 (bs, 1H), 11.35 (s, 1H), 7.47-7.42 (m, 2H), 7.35-7.27 (m, 3H), 7.18-7.08 (m, 3H), 6.99 (d, J=7.6 Hz, 1H), 6.52 (s, 1H), 3.98 (dd, J=11.6, 2.8 Hz, 1H), 3.71 (s, 3H), 3.26-3.18 (m, 3H), 3.00-2.92 (m, 2H), 2.85-2.79 (m, 1H), 2.67-2.54 (m, 2H), 2.02-1.98 (m, 2H), 1.67-1.63 (m, 1H), 1.30-1.24 (m, 4H), 1.08 (s, 3H), 1.00-0.98 (m, 6H) ppm.

Example 115. 3-[3-[6-(1,3-Dithiolan-2-yl)-22,28-difluoro-3,10,10-trimethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl]phenyl]-2-methyl-propanoic Acid

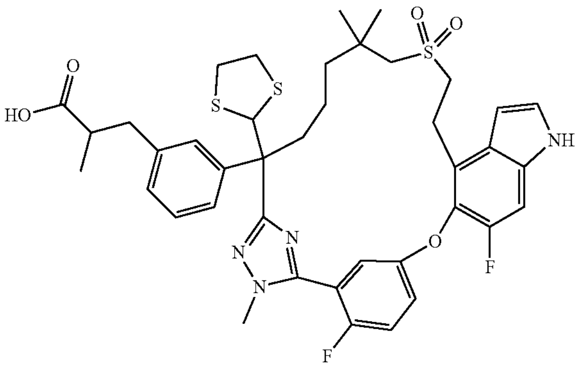 [SMILES: CC(Cc1cccc(C2(C3SCCS3)CCCC(C)(C)CS(=O)(=O)CCc3c(c(F)cc4[nH]ccc34)Oc3ccc(F)c(c3)-c3nc2nn3C)c1)C(=O)O]

Ethyl 3-[3-[6-(1,3-dithiolan-2-yl)-22,28-difluoro-3,10,10-trimethyl-12,12-dioxo-24-oxa-12 6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

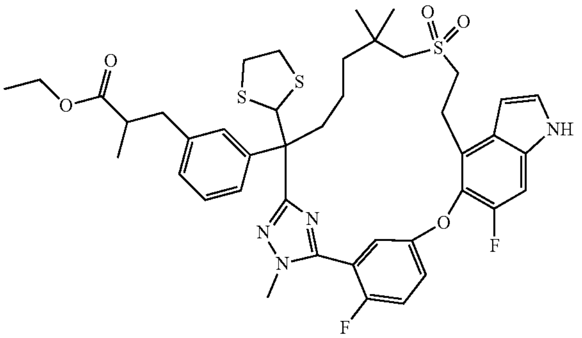 [SMILES: CCOC(=O)C(C)Cc1cccc(C2(C3SCCS3)CCCC(C)(C)CS(=O)(=O)CCc3c(c(F)cc4[nH]ccc34)Oc3ccc(F)c(c3)-c3nc2nn3C)c1]

Step A: To a stirred solution of ethyl 3-[3-(22,28-difluoro-6-formyl-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate (Step B product of Example 20, 100 mg, 0.134 mmol) and 1,2-ethanedithiol (0.0337 mL, 0.402 mmol) in dichloromethane (2.0 mL) was added boron trifluoride etherate (0.0446 mL, 0.362 mmol). The mixture was stirred at room temperature overnight, quenched with saturated sodium bicarbonate (150 mL), and extracted with dichloromethane (3×50 mL). The combined organic extracts were washed with saturated sodium bicarbonate, brine, dried over sodium sulfate, and concentrated. The residue was purified by automated flash chromatography (4.0 g silica gel column, eluted with 0-30% ethyl acetate in petroleum ether) to give the title compound (60 mg, 54%) as a white solid. MS (ESI): 823 m/z $[M+H]^+$, retention time: 2.14 minutes, purity: 96% (214 nm). (LC-MS Method 003).

Compound 115: 3-[3-[6-(1,3-Dithiolan-2-yl)-22,28-difluoro-3,10,10-trimethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl]phenyl]-2-methyl-propanoic acid

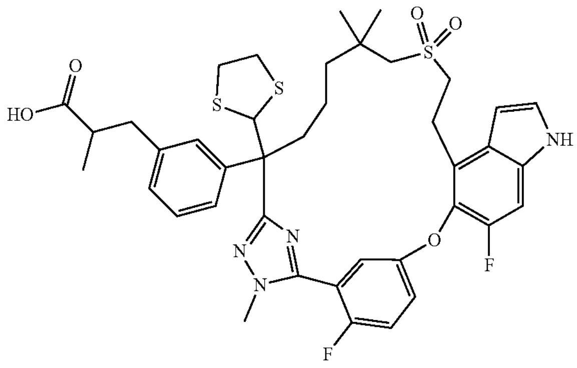 [SMILES: CC(Cc1cccc(C2(C3SCCS3)CCCC(C)(C)CS(=O)(=O)CCc3c(c(F)cc4[nH]ccc34)Oc3ccc(F)c(c3)-c3nc2nn3C)c1)C(=O)O]

Step B: To a stirred solution of Step A product (60 mg, 0.0729 mmol) in tetrahydrofuran (1.0 mL), methanol (1.0 mL) and water (0.5 mL) was added lithium hydroxide monohydrate (30.6 mg, 0.729 mmol). The reaction was stirred at room temperature for 3 hours, then diluted with water (10 mL), and acidified with 1.0 M hydrochloric acid to pH ~6. The suspension was extracted with ethyl acetate (3×10 mL). The combined organic phases were washed with brine (2×20 mL), dried over sodium sulfate, and concentrated to give the title compound (50 mg, 86%) as a white solid. MS (ESI): 795 m/z $[M+H]^+$, retention time: 1.76 minutes, purity: 98% (214 nm). (LC-MS Method 028). $^1$H NMR (400 MHz, $CD_3OD$) δ 7.35-7.16 (m, 8H), 7.12-7.10 (m, 1H), 6.60 (d, J=2.8 Hz, 1H), 5.55 (d, J=1.2 Hz, 1H), 3.89 (s, 3H), 3.41-3.36 (m, 1H), 3.31-3.09 (m, 3H), 3.01-2.97 (m, 1H), 2.87-2.74 (m, 4H), 2.67-2.59 (m, 2H), 2.45-2.36 (m, 1H), 2.29-2.18 (m, 1H), 2.13-2.04 (m, 1H), 2.02-1.93 (m, 1H), 1.50-1.38 (m, 2H), 1.16-1.11 (m, 8H), 1.01 (s, 3H) ppm.

Example 116. 3-[3-(22,28-Difluoro-3,6,10,10-tetramethyl-12,12-dioxo-24-oxa-12λ6-thia-3,4,17,19,30-pentazapentacyclo[23.3.1.12,5.015,23.016,20]triaconta-1(29),2(30),4,15,17,20,22,25,27-nonaen-6-yl)phenyl]propanoic Acid

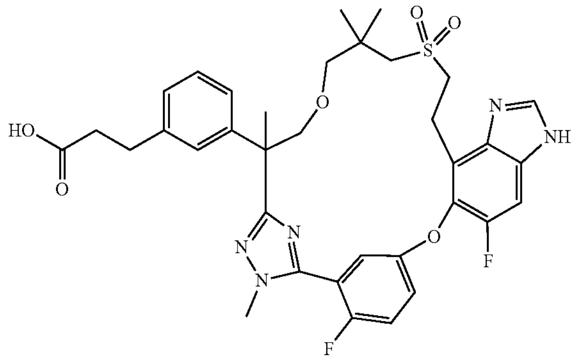 [SMILES: Cn1nc2nc1-c1cc(ccc1F)Oc1c(F)cc3[nH]cnc3c1CCS(=O)(=O)CC(C)(C)COCC2(C)c1cccc(CCC(=O)O)c1]

Ethyl 3-[3-[19-(dimethylsulfamoyl)-22,28-difluoro-3,6,10,10-tetramethyl-12,12-dioxo-24-oxa-12λ6-thia-3,4,17,19,30-pentazapentacyclo[23.3.1.12,5.015,23.016,20]triaconta-1(29),2(30),4,15,17,20,22,25,27-nonaen-6-yl]phenyl]propanoate

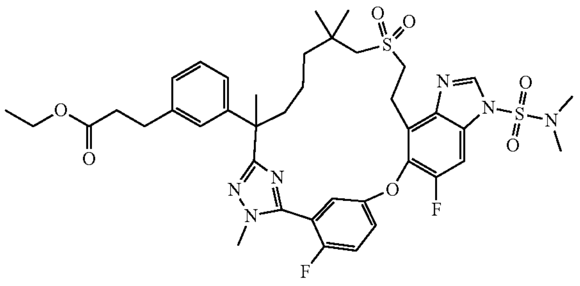 [SMILES: CCOC(=O)CCc1cccc(C2(C)CCCC(C)(C)CS(=O)(=O)CCc3c(c(F)cc4c3ncn4S(=O)(=O)N(C)C)Oc3ccc(F)c(c3)-c3nc2nn3C)c1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with ethyl 3-(3-(7-((2-hydroxyethyl)-sulfonyl)-2,6,6-trimethyl-1-(2-methylhydrazineyl)-1-oxoheptan-2-yl)phenyl)propanoate (Intermediate 58-5, 0.45 g, 0.722 mmol) and methyl 5-((4-bromo-6-fluoro-1H-indol-5-yl)oxy)-2-fluorobenzimidothioate hydroiodide (Intermediate 14-1) with methyl 5-((4-bromo-1-(N,N-dimethylsulfamoyl)-6-fluoro-1H-benzo[d]imidazol-5-yl)oxy)-2-fluorobenzimidothioate hydroiodide (Intermediate 14-11, 0.844 g, 0.866 mmol) in Step A, the reaction procedure sequence (Steps A to D) as described in Example 6 was used to prepare the title compound (20 mg). MS (ESI): 827 m/z $[M+H]^+$, retention time: 2.06 minutes, purity: 70% (214 nm) (LC-MS Method 012).

Ethyl 3-[3-(22,28-difluoro-3,6,10,10-tetramethyl-12,12-dioxo-24-oxa-12λ6-thia-3,4,17,19,30-pentazapentacyclo[23.3.1.12,5.015,23.016,20]triaconta-1(29),2(30),4,15,17,20,22,25,27-nonaen-6-yl)phenyl]propanoate

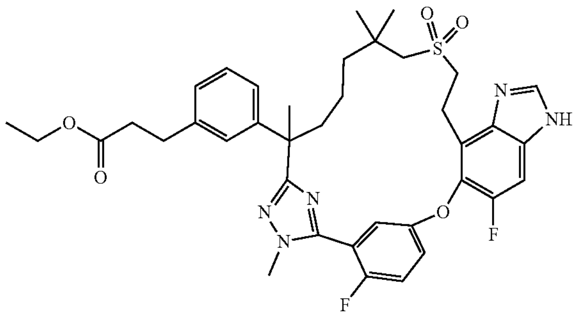 [SMILES: CCOC(=O)CCc1cccc(C2(C)CCCC(C)(C)CS(=O)(=O)CCc3c(c(F)cc4[nH]cnc34)Oc3ccc(F)c(c3)-c3nc2nn3C)c1]

Step B: To a stirred solution of Step A product (20 mg, 0.0153 mmol) in ethanol (5 mL) was added concentrated hydrochloric acid (0.1 mL). The reaction mixture was stirred at 40° C. for 4 hours and cooled to room temperature. The solution was partitioned between (10 mL) and ethyl acetate (20 mL). The separated organic phase, combined with two additional ethyl acetate extracts, was washed with brine (5 mL), dried over anhydrous sodium sulfate, and concentrated to give the title compound (15 mg, 79%) as a yellow solid.

MS (ESI): 720 m/z $[M+H]^+$, retention time: 1.74 minutes, purity: 58% (214 nm) (LC-MS Method 012).

Compound 116: 3-[3-(22,28-Difluoro-3,6,10,10-tetramethyl-12,12-dioxo-24-oxa-1216-thia-3,4,17,19,30-pentazapentacyclo[23.3.1.12,5.015,23.016,20]triaconta-1(29),2(30),4,15,17,20,22,25,27-nonaen-6-yl)phenyl]propanoic Acid

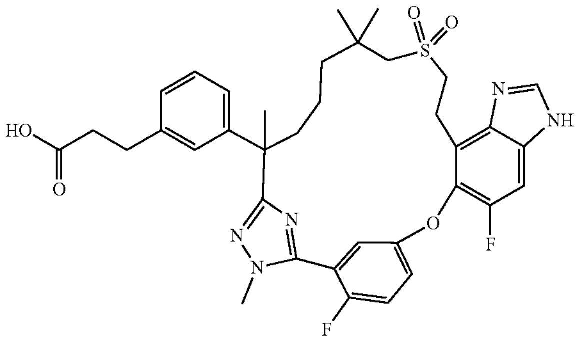 [SMILES: Cn1nc2nc1-c1cc(ccc1F)Oc1c(F)cc3[nH]cnc3c1CCS(=O)(=O)CC(C)(C)CCCC2(C)c1cccc(CCC(=O)O)c1]

Step C: To a stirred solution of Step B product (15 mg, 0.0121 mmol) in methanol (1 mL) and tetrahydrofuran (1 mL) was added a solution of lithium hydroxide monohydrate (1.52 mg, 0.0363 mmol) in water (0.5 mL). The mixture was stirred at room temperature for 5 hours. The mixture was neutralized with 1 M hydrochloric acid to pH ~4 and concentrated. The residue was purified by Prep-HPLC to give the title compound (0.7 mg, 8%) as white solid. MS (ESI): 692 m/z $[M+H]^+$, retention time: 1.59 minutes, purity: 99% (214 nm) (LC-MS Method 012). $^1$H NMR (400 MHz, $CD_3OD$) δ 8.40 (bs, 1H) 8.24 (s, 1H), 7.44-7.35 (m, 3H), 7.26-7.24 (m, 1H), 7.18 (t, J=6.0 Hz, 1H), 7.08 (s, 1H), 7.04-7.00 (m, 2H), 3.84 (d, J=0.8 Hz, 3H), 3.50-3.36 (m, 2H), 3.09 (d, J=11.2 Hz, 1H), 2.90-2.80 (m, 3H), 2.53 (t, J=6.0 Hz, 2H), 2.22-2.19 (m, 2H), 2.05-2.04 (m, 1H), 1.86-1.79 (m, 1H), 1.68 (s, 3H), 1.62-1.56 (m, 2H), 1.40-1.35 (m, 2H), 1.07 (s, 3H), 1.02 (s, 3H) ppm.

Example 117. 3-[3-(22-Fluoro-3,6,10,10-tetramethyl-12,12-dioxo-24-oxa-12λ6-thia-3,19,30-triazapentacyclo[23.3.1.12,5.015,23.016,20]triaconta-1(29),2(30),4,15,17,20,22,25,27-nonaen-6-yl)phenyl]-2-methyl-propanoic Acid

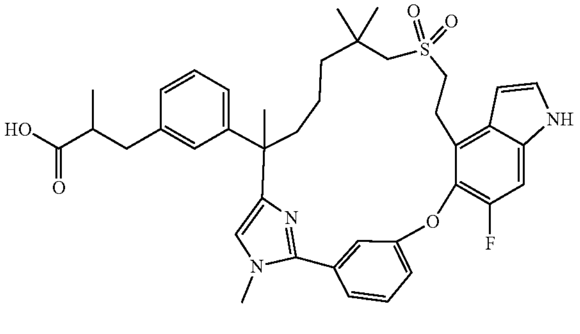 [SMILES: CC(Cc1cccc(C2(C)CCCC(C)(C)CS(=O)(=O)CCc3c(c(F)cc4[nH]ccc34)Oc3cccc(c3)-c3nc2cn3C)c1)C(=O)O]

Ethyl 3-(3-(7-acetoxy-2-(2-(3-((4-bromo-6-fluoro-1-tosyl-1H-indol-5-yl)oxy)phenyl)-1-methyl-1H-imidazol-4-yl)-6,6-dimethylheptan-2-yl)phenyl)-2-methylpropanoate

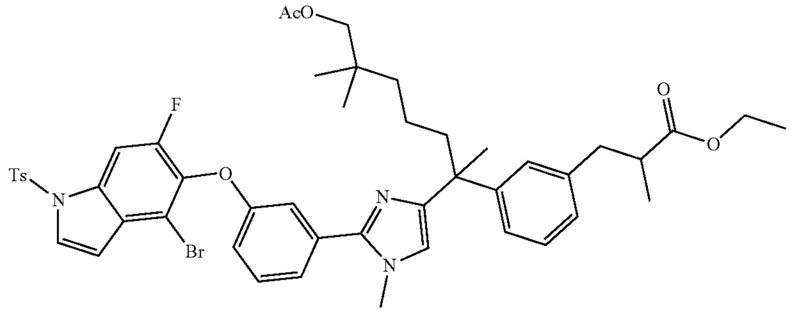 [SMILES: CCOC(=O)C(C)Cc1cccc(C(C)(CCCC(C)(C)COC(C)=O)c2cn(C)c(-c3cccc(Oc4c(F)cc5c(ccn5S(=O)(=O)c5ccc(C)cc5)c4Br)c3)n2)c1]

Step A: To a stirred solution of 3-((4-bromo-6-fluoro-1-tosyl-1H-indol-5-yl)oxy)-N-methylbenzimidamide (Intermediate 117, 1.9 g, 3.69 mmol) in N,N-dimethylformamide (30 mL) was added ethyl 3-(3-(8-acetoxy-1-bromo-3,7,7-trimethyl-2-oxooctan-3-yl)phenyl)-2-methylpropanoate (Intermediate 17-13, 1.8 g, 3.69 mmol) and sodium bicarbonate (0.62 g, 7.38 mmol). The mixture was stirred at 45° C. for 48 hours, then increased to 80° C. for 16 hours. The solution was cooled to room temperature and partitioned between 120 mL of water and ethyl acetate (120 mL). The separated organic layer, combined with two additional ethyl acetate extracts, was washed with brine, dried over sodium sulfate, and concentrated. The residue was purified by silica gel column chromatography (petroleum ether: ethyl acetate=2:1) to give the title compound (1.2 g, 36%) as a yellow solid. MS (ESI): 914 m/z $[M+H]^+$, retention time: 1.83 minutes, purity: 95% (214 nm) (LC-MS Method 003).

Ethyl 3-(3-(2-(2-(3-((4-bromo-6-fluoro-1H-indol-5-yl)oxy)phenyl)-1-methyl-1H-imidazol-4-yl)-7-hydroxy-6,6-dimethylheptan-2-yl)phenyl)-2-methylpropanoate

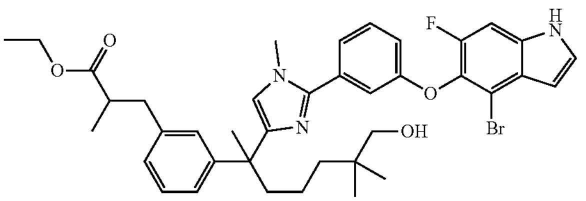 [SMILES: CCOC(=O)C(C)Cc1cccc(C(C)(CCCC(C)(C)CO)c2cn(C)c(-c3cccc(Oc4c(F)cc5[nH]ccc5c4Br)c3)n2)c1]

Step B: To a stirred solution of Step A product (1.2 g, 1.31 mmol) in methanol (25 mL) was added potassium carbonate (0.73 g, 5.26 mmol). The mixture was stirred at room temperature overnight, then poured into 200 mL of water. The formed precipitate was collected by filtration to give the title compound (0.84 g, 89%) as a light-yellow solid. MS (ESI): 718 m/z $[M+H]^+$, retention time: 1.65 minutes, purity: 89% (214 nm) (LC-MS Method 003).

Ethyl 3-(3-(7-(acetylthio)-2-(2-(3-((4-bromo-6-fluoro-1H-indol-5-yl)oxy)phenyl)-1-methyl-1H-imidazol-4-yl)-6,6-dimethylheptan-2-yl)phenyl)-2-methylpropanoate

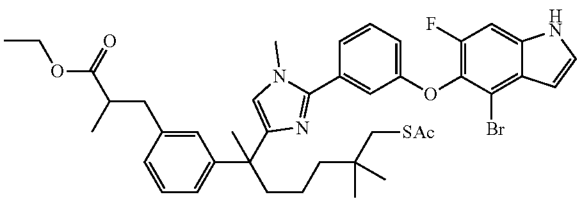

Step C: To a stirred and cooled (0° C.) solution of triphenylphosphine (920 mg, 3.51 mmol) in tetrahydrofuran (30 mL) was added diisopropyl azodiformate (706 g, 3.51 mmol) dropwise. The mixture was stirred at 0° C. until the formation of a white solid was observed (15-30 minutes), then treated with a solution of Step B product (0.84 g, 1.17 mmol) and thioacetic acid (267 mg, 3.51 mmol) in tetrahydrofuran (10 mL). The mixture was stirred at 0° C. for 1 hour, then warmed to room temperature for 1 hour, and quenched with 150 mL of water. The solution was extracted with ethyl acetate (3×150 mL). The combined organic extracts were washed with brine, dried over sodium sulfate, and concentrated. The residue was purified by silica gel column chromatography (petroleum ether: ethyl acetate=1: 1) to give the title compound (710 mg, 78%) as a yellow solid. MS (ESI): 776 m/z $[M+H]^+$, retention time: 1.77 minutes, purity: 80% (214 nm) (LC-MS Method 003).

Ethyl 3-(3-(2-(2-(3-((4-bromo-6-fluoro-1H-indol-5-yl)oxy)phenyl)-1-methyl-1H-imidazol-4-yl)-7-((2-hydroxyethyl)thio)-6,6-dimethylheptan-2-yl)phenyl)-2-methylpropanoate

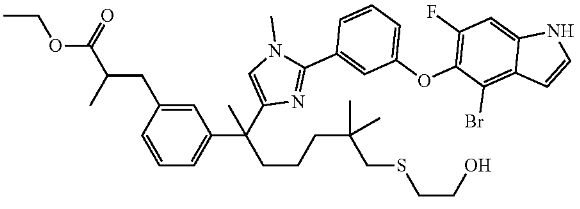 [SMILES: CCOC(=O)C(C)Cc1cccc(C(C)(CCCC(C)(C)CSCCO)c2cn(C)c(-c3cccc(Oc4c(F)cc5[nH]ccc5c4Br)c3)n2)c1]

Step D: To a stirred solution of Step C product (0.75 g, 0.967 mmol) in ethanol (30 mL) was added 2-bromoethan-1-ol (240 mg, 1.93 mmol) and sodium ethoxide (132 mg, 1.93 mmol). The mixture was stirred at room temperature overnight, then quenched with 100 mL of water, and extracted with ethyl acetate (3×100 mL). The combined organic extracts were washed with brine, dried over sodium sulfate, and concentrated. The residue was purified by silica gel column chromatography (dichloromethane:methanol=20:1) to give the title compound (480 mg, 64%) as a white solid. MS (ESI): 778 m/z $[M+H]^+$, retention time: 1.68 minutes, purity: 88% (254 nm) (LC-MS Method 003).

Ethyl 3-(3-(2-(2-(3-((4-bromo-6-fluoro-1H-indol-5-yl)oxy)phenyl)-1-methyl-1H-imidazol-4-yl)-7-((2-hydroxyethyl)sulfonyl)-6,6-dimethylheptan-2-yl) phenyl)-2-methylpropanoate

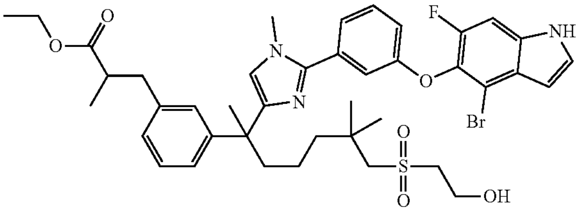 [SMILES: CCOC(=O)C(C)Cc1cccc(C(C)(CCCC(C)(C)CS(=O)(=O)CCO)c2cn(C)c(-c3cccc(Oc4c(F)cc5[nH]ccc5c4Br)c3)n2)c1]

Step E: To a stirred and cooled (0° C.) solution of Step D product (480 mg, 0.618 mmol) in methanol (25 mL) was added ammonium molybdate tetrahydrate (960 mg, 4.90 mmol) and hydrogen peroxide (30% in water, 4.8 mL). The mixture was stirred at 0° C. for 1 hour, then poured into water (80 mL) and filtered. The collected precipitate was purified by silica gel column chromatography (dichloromethane:methanol=30:1) to give the title compound (320 mg, 64%) as a white solid. MS (ESI): 810 m/z $[M+H]^+$, retention time: 1.62 minutes, purity: 77% (214 nm). (LC-MS Method 003).

Compound 117: 3-[3-(22-Fluoro-3,6,10,10-tetramethyl-12,12-dioxo-24-oxa-12λ6-thia-3,19,30-triazapentacyclo[23.3.1.12,5.015,23.016,20]triaconta-1(29),2(30),4,15,17,20,22,25,27-nonaen-6-yl)phenyl]-2-methyl-propanoic Acid

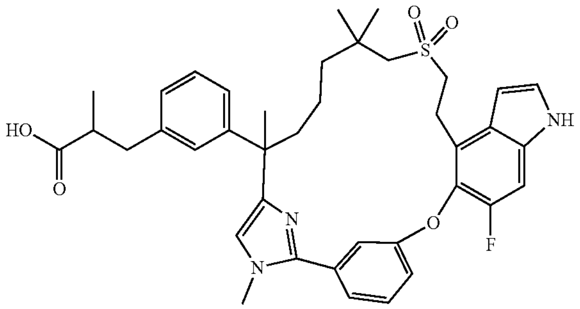 [SMILES: CC(Cc1cccc(C2(C)CCCC(C)(C)CS(=O)(=O)CCc3c(c(F)cc4[nH]ccc34)Oc3cccc(c3)-c3nc2cn3C)c1)C(=O)O]

Step F: Exchanging methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 6) with ethyl 3-(3-(2-(2-(3-((4-bromo-6-fluoro-1H-indol-5-yl)oxy)phenyl)-1-methyl-1H-imidazol-4-yl)-7-((2-hydroxyethyl)-sulfonyl)-6,6-dimethyl-heptan-2-yl)phenyl)-2-methylpropanoate (Step E product of this example, 320 mg, 0.395 mmol), the reaction procedure sequence (Steps B to D and F) described for Example 6 was used to prepare the title compound (45.2 mg) as a light-yellow solid. MS (ESI): 686 m/z $[M+H]^+$, retention time: 1.66 minutes, purity: 97% (214 nm) (LC-MS Method 003). $^1$H NMR (400 MHz, DMSO-d6) δ 11.51-11.48 (m, 1H), 7.48-7.34 (m, 5H), 7.06-6.93 (m, 6H), 6.51 (s, 1H), 3.78 (s, 3H), 3.23-3.21 (m, 2H), 3.12-3.05 (m, 2H), 2.95-2.90 (m, 1H), 2.66 (s, 2H), 2.50-2.33 (m, 3H), 2.02 (dt, J=10.0, 2.0 Hz, 1H), 1.61 (dt, J=12.4, 2.4 Hz, 1H), 1.48 (s, 3H), 1.27-1.11 (m, 3H), 1.04-0.92 (m, 9H) ppm.

Example 118. Enantiomers 1 and 2 of 2-methyl-3-[3-[21,22,28-trifluoro-3,10,10-trimethyl-12,12-dioxo-6-(trideuteriomethyl)-8,24-dioxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic acid

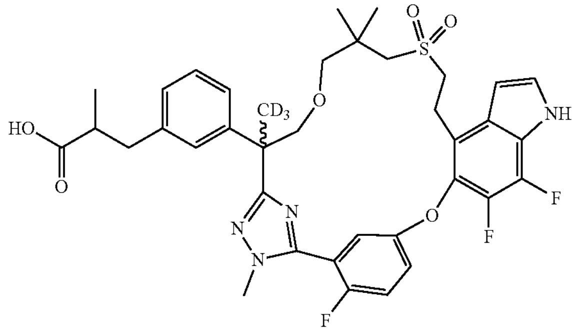 [SMILES: [2H]C([2H])([2H])C1(c2cccc(CC(C)C(=O)O)c2)COCC(C)(C)CS(=O)(=O)CCc2c(c(F)c(F)c3[nH]ccc23)Oc2ccc(F)c(c2)-c2nc1nn2C]

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with ethyl 3-(3-(2-((3-((2-hydroxyethyl)sulfonyl)-2,2-dimethylpropoxy)methyl)-1-(2-methylhydrazineyl)-1-oxo-propan-2-yl-3,3,3-d3)phenyl)-2-methylpropanoate (Intermediate 58, 1.26 g, 2.50 mmol) and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)oxy)-2-fluoro-benzimidothioate hydroiodide (Intermediate 14-2, 1.45 g, 2.66 mmol), the reaction procedure sequence (Steps A to G) described for Example 6 was used to prepare the title compounds. The first eluent of corresponding Step E was hydrolyzed to provide Compound 118A (141 mg, 90%). The second eluent of corresponding Step E was hydrolyzed to provide Compound 118B (150 mg, 93%).

Compound 118A: MS (ESI): 728 m/z $[M+H]^+$, retention time: 1.84 minutes, purity: >99% (214 nm). (LC-MS Method 009). $^1$H NMR (400 MHz, $CD_3OD$) δ 11.36 (s, 1H), 7.40-7.35 (m, 1H), 7.33-7.27 (m, 2H), 7.05 (t, J=7.6 Hz, 1H), 6.94-6.90 (m, 4H), 6.65-6.63 (m, 1H), 3.92 (d, J=8.0 Hz, 1H), 3.72 (d, J=2.0 Hz, 3H), 3.47 (dd, J=8.4, 2.8 Hz, 1H), 3.37-3.25 (m, 2H), 3.08-2.98 (m, 2H), 2.93 (d, J=8.8 Hz, 1H), 2.84 (d, J=8.8 Hz, 1H), 2.82-2.77 (m, 1H), 2.54 (s, 2H), 2.53-2.45 (m, 2H), 0.95 (dd, J=6.8, 3.2 Hz, 3H), 0.88 (s, 3H), 0.87 (s, 3H) ppm.

Compound 118B: MS (ESI): 728 m/z $[M+H]^+$, retention time: 1.84 minutes, purity: >99% (214 nm). (LC-MS Method 009). $^1$H NMR (400 MHz, $CD_3OD$) δ 7.40-7.36 (m, 1H), 7.34-7.28 (m, 2H), 7.05 (t, J=7.6 Hz, 1H), 6.94-6.90 (m, 4H), 6.64 (t, J=3.2 Hz, 1H), 3.92 (d, J=8.4 Hz, 1H), 3.72 (d, J=2.0 Hz, 3H), 3.47 (dd, J=8.4, 2.4 Hz, 1H), 3.36-3.27 (m, 2H), 3.06-3.02 (m, 2H), 2.92 (d, J=9.2 Hz, 1H), 2.83 (d, J=8.8 Hz, 1H), 2.81-2.78 (m, 1H), 2.54 (s, 2H), 2.51-2.44 (m, 2H), 0.95 (dd, J=6.8, 3.2 Hz, 3H), 0.88 (s, 3H), 0.87 (s, 3H) ppm.

Example 119. Enantiomers 1 and 2 of 3-[3-[22,28-difluoro-3,9,9-trimethyl-12,12-dioxo-6-(trideuteriomethyl)-24-oxa-12lambda6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid

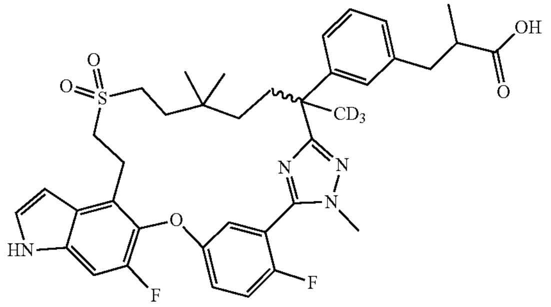 [SMILES: [2H]C([2H])([2H])C1(c2cccc(CC(C)C(=O)O)c2)CCC(C)(C)CCS(=O)(=O)CCc2c(c(F)cc3[nH]ccc23)Oc2ccc(F)c(c2)-c2nc1nn2C]

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with methyl 3-(3-(7-((2-hydroxyethyl)sulfonyl)-5,5-dimethyl-2-(2-methylhydrazine-1-carbonyl)heptan-2-yl-1,1,1-d3)phenyl)-2-methylpropanoate (Intermediate 69-14, 1.3 g, 2.67 mmol), the reaction procedure sequence (Steps A to G) described for Example 6 was used to prepare the title compounds. The chiral SFC conditions in corresponding Step E was as following: Column: IH 20*250 mm, 10 μm; Column temperature: 35° C.; Mobile phase: carbon dioxide/methanol (0.2% methanol ammonia)=70/30; Flow rate: 100 g/min; Back pressure: 100 bar; Detection wavelength: 214 nm; Cycle time: 5 minutes; Sample solution: 400 mg dissolved in 20 mL of methanol and dichloromethane; Injection volume: 2 mL. The first eluent, enantiomer 1 (96 mg), was hydrolyzed to provide acid Compound 119A (85 mg, 90%), as described in corresponding Step F. The second eluent, enantiomer 2 (91 mg), was hydrolyzed to provide Compound 119B (82 mg, 92%), as described in corresponding Step G.

Compound 119A: MS (ESI): 708 m/z [M+H]$^+$, retention time: 2.15 minutes, purity: 99% (214 nm). (LC-MS Method 003). $^1$H NMR (400 MHz, $CD_3OD$) δ 7.53-7.49 (m, 1H), 7.47 (t, J=9.2 Hz, 1H), 7.35 (d, J=3.2 Hz, 1H), 7.27 (d, J=10.4 Hz, 1H), 7.11 (t, J=7.6 Hz, 1H), 7.02 (s, 1H), 6.98-6.96 (m, 2H), 6.76 (d, J=3.2 Hz, 1H), 6.73-6.71 (m, 1H), 3.84 (d, J=2.4 Hz, 3H), 3.54 (t, J=8.8 Hz, 2H), 3.29-3.26 (m, 1H), 3.20-3.13 (m, 1H), 3.08-3.02 (m, 1H), 2.94-2.84 (m, 1H), 2.63-2.25 (m, 2H), 2.45-2.38 (m, 1H), 2.11 (t, J=12.8 Hz, 1H), 1.63 (t, J=13.2 Hz, 2H), 1.45-1.38 (m, 1H), 1.11-1.05 (m, 1H), 1.04 (d, J=6.4 Hz, 3H), 0.77-0.70 (m, 1H), 0.70 (s, 3H), 0.31 (s, 3H) ppm.

Compound 119B: MS (ESI): 708 m/z [M+H]$^+$, retention time: 2.14 minutes, purity: 99% (214 nm). (LC-MS Method 003). $^1$H NMR (400 MHz, $CD_3OD$) δ 7.51-7.47 (m, 1H), 7.45 (t, J=9.2 Hz, 1H), 7.33 (d, J=3.2 Hz, 1H), 7.25 (d, J=10.8 Hz, 1H), 7.10 (t, J=7.6 Hz, 1H), 7.00 (s, 1H), 6.97-6.94 (m, 2H), 6.74 (d, J=3.2 Hz, 1H), 6.72-6.70 (m, 1H), 3.82 (d, J=2.8 Hz, 3H), 3.52 (t, J=5.6 Hz, 2H), 3.28-3.25 (m, 1H), 3.18-3.13 (m, 1H), 3.06-3.00 (m, 1H), 2.90-2.85 (m, 1H), 2.60-2.52 (m, 2H), 2.42 (t, J=11.2 Hz, 1H), 2.10 (t, J=13.2 Hz, 1H), 1.65-1.59 (m, 2H), 1.43-1.35 (m, 1H), 1.09-1.06 (m, 1H), 1.05 (d, J=6.4 Hz, 3H), 0.77-0.70 (m, 1H), 0.68 (s, 3H), 0.29 (s, 3H) ppm.

Example 120. Enantiomers 1 and 2 of 1-[[3-[22,28-difluoro-3,10,10-trimethyl-12,12-dioxo-6-(trideuteriomethyl)-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]methyl]cyclopropanecarboxylic Acid

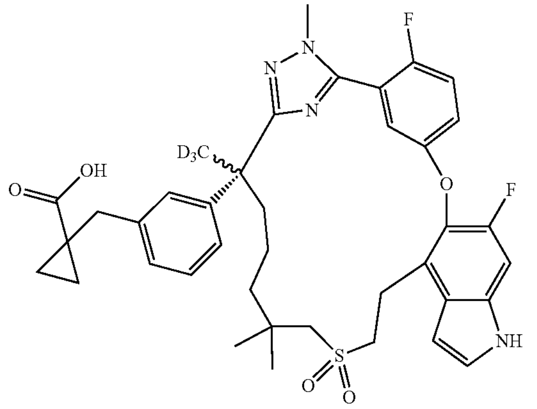

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with methyl 1-(3-(7-((2-hydroxyethyl)sulfonyl)-6,6-dimethyl-2-(2-methylhydrazine-1-carbonyl)heptan-2-yl-1,1,1-d3)benzyl)cyclopropane-1-carboxylate (Intermediate 69-15, 0.47 g, 0.94 mmol), the reaction procedure sequence (Steps A to G) described for Example 6 was used to prepare the title compounds. The chiral SFC conditions in corresponding Step E was as following: Instrument: SFC-80 (Thar, Waters); Column: AD 20*250 mm, 10 μm; Column temperature: 35° C.; Mobile phase: carbon dioxide/isopropanol (0.2% methanol ammonia)=70/30; Flow rate: 80 g/min; Back pressure: 100 bar; Detection wavelength: 214 nm; Cycle time: 2.8 minutes; Sample solution: 240 mg dissolved in 25 mL of methanol; Injection volume: 0.8 mL. The first eluent, enantiomer 1 (89 mg), was hydrolyzed to provide acid Compound 120A (63 mg, 73%), as described in corresponding Step F. The second eluent, enantiomer 2 (95 mg), was hydrolyzed to provide Compound 120B (64 mg, 68%), as described in corresponding Step G.

Compound 120A: MS (ESI): 720 m/z [M+H]$^+$, retention time: 1.93 minutes, purity: 96% (214 nm). (LC-MS Method 003). $^1$H NMR (400 MHz, $CD_3OD$) δ 7.39-7.32 (m, 3H), 7.24-7.17 (m, 2H), 7.15 (t, J=7.6 Hz, 1H), 7.05-7.00 (m, 3H), 6.63 (d, J=3.2 Hz, 1H), 3.84 (d, J=2.4 Hz, 3H), 3.41-3.36 (m, 3H), 3.26-3.21 (m, 1H), 3.01 (d, J=13.6 Hz, 1H), 2.89-2.82 (m, 3H), 2.18 (dt, J=12.8, 3.6 Hz, 1H), 1.86 (dt, J=12.4, 4.4 Hz, 1H), 1.64-1.59 (m, 1H), 1.38-1.33 (m, 2H), 1.26-1.20 (m, 1H), 1.16-1.10 (m, 2H), 1.08 (s, 3H), 1.07 (s, 3H), 0.73-0.67 (m, 2H) ppm.

Compound 120B: MS (ESI): 720 m/z [M+H]$^+$, retention time: 1.95 minutes, purity: 99% (214 nm). (LC-MS Method 003). $^1$H NMR (400 MHz, $CD_3OD$) δ 7.36-7.32 (m, 3H), 7.24-7.20 (m, 2H), 7.16 (t, J=7.6 Hz, 1H), 7.05-7.00 (m, 3H), 6.63 (d, J=3.2 Hz, 1H), 3.84 (d, J=2.4 Hz, 3H), 3.41-3.38 (m, 3H), 3.26-3.23 (m, 1H), 3.01 (d, J=13.6 Hz, 1H), 2.89-2.82 (m, 3H), 2.16 (dt, J=12.8, 3.2 Hz, 1H), 1.83 (dt, J=12.4, 4.4 Hz, 1H), 1.63-1.60 (m, 1H), 1.35-1.31 (m, 2H), 1.26-1.20 (m, 1H), 1.14-1.11 (m, 2H), 1.08 (s, 3H), 1.07 (s, 3H), 0.72-0.69 (m, 2H) ppm.

Example 121. Enantiomers 1 and 2 of 1-[[3-(6-cyano-21,22,28-trifluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]cyclopropanecarboxylic Acid

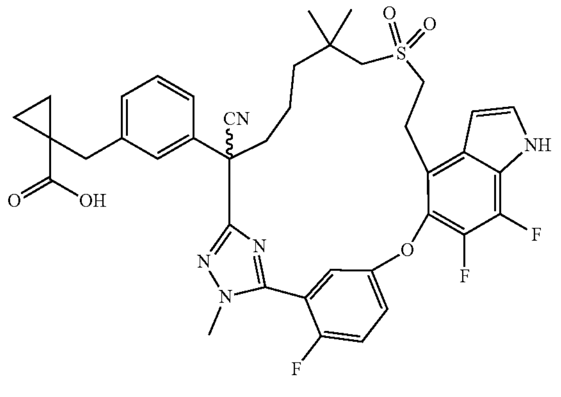 [SMILES: Cn1nc2nc1-c1cc(ccc1F)Oc1c(F)c(F)c3[nH]ccc3c1CCS(=O)(=O)CC(C)(C)CCCC2(C#N)c1cccc(CC2(C(=O)O)CC2)c1]

Exchanging ethyl (E)-3-(3-(2-((benzyloxy)methyl)-7-((2-hydroxyethyl)sulfonyl)-6,6-dimethyl-1-(2-methylhydrazineyl)-1-oxoheptan-2-yl)phenyl)-2-methylacrylate (intermediate 69-8) with methyl 1-(3-(2-((benzyloxy)methyl)-7-((2-hydroxyethyl)sulfonyl)-6,6-dimethyl-1-(2-methylhydrazineyl)-1-oxoheptan-2-yl)benzyl)cyclopropane-1-carboxylate (Intermediate 69-15, 700 mg, 1.16 mmol), and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)oxy)-2-fluorobenzimidothioate hydroiodide (Intermediate 14-2, 757 mg, 1.39 mmol), the reaction procedure sequence (Steps A to G) described for Example 20 was used to prepare the title compounds. The racemic ethyl ester (240 mg), obtained in corresponding Step D of Example 20, was subjected to the following chiral SFC separation conditions: Instrument: SFC-80 (Thar, Waters); Column: OX 20*250 mm, 10 μm; Column temperature: 35° C.; Mobile phase: carbon dioxide/isopropanol (0.2% methanol ammonia)=45/55; Flow rate: 80 g/min; Back pressure: 100 bar; Detection wavelength: 214 nm; Cycle time: 10.5 minutes; Sample solution: 250 mg dissolved in 30 mL of methanol; Injection volume: 1.9 mL. The first eluent, enantiomer 1 (60 mg), was hydrolyzed to provide acid Compound 121A (50 mg, 84%), as described in corresponding Step F. The second eluent, enantiomer 2 (60 mg), was hydrolyzed to provide Compound 121B (49 mg, 84%), as described in corresponding Step G of Example 20.

Compound 121A: MS (ESI): 746 m/z $[M+H]^+$, retention time: 1.88 minutes, purity: 99% (214 nm). (LC-MS Method 003). Chiral purity: 98.8% at 2.44 minutes (e.e. %=97.6%, AS-H 20% methanol (0.2% methanol ammonia as additive); Flow: 4 mL/minutes; Temperature: 40° C.; PB: 120 bar). $^1H$ NMR (400 MHz, $CD_3OD$) δ 7.45-7.36 (m, 3H), 7.30-7.19 (m, 5H), 6.68 (t, J=3.2 Hz, 1H), 3.86 (d, J=2.0 Hz, 3H), 3.48-3.34 (m, 3H), 3.27-3.24 (m, 1H), 3.13 (d, J=13.6 Hz, 1H), 2.96 (d, J=13.6 Hz, 1H), 2.86 (d, J=15.6 Hz, 1H), 2.76 (d, J=15.2 Hz, 1H), 2.50 (t, J=12.0 Hz, 1H), 2.12-2.01 (m, 1H), 1.76-1.69 (m, 1H), 1.47-1.36 (m, 3H), 1.16 (s, 3H), 1.11-1.05 (m, 2H), 1.01 (s, 3H), 0.75-0.65 (m, 2H) ppm.

Compound 121B: MS (ESI): 746 m/z $[M+H]^+$, retention time: 1.88 minutes, purity: >99% (214 nm). (LC-MS Method 003). Chiral purity: 99.75% at 1.59 minutes (e.e. %=99.5%, AS-H 20% methanol (0.2% methanol ammonia as additive); Flow: 4 mL/minutes; Temperature: 40° C.; PB: 120 bar). $^1H$ NMR (400 MHz, $CD_3OD$) δ 7.45-7.36 (m, 3H), 7.31-7.18 (m, 5H), 6.68 (t, J=3.2 Hz, 1H), 3.86 (d, J=2.0 Hz, 3H), 3.48-3.34 (m, 3H), 3.27-3.24 (m, 1H), 3.14 (d, J=13.6 Hz, 1H), 2.96 (d, J=13.6 Hz, 1H), 2.86 (d, J=15.6 Hz, 1H), 2.76 (d, J=15.2 Hz, 1H), 2.50 (t, J=11.6 Hz, 1H) 2.11-2.03 (m, 1H), 1.74-1.68 (m, 1H), 1.47-1.36 (m, 3H), 1.16 (s, 3H), 1.09-1.05 (m, 2H), 1.01 (s, 3H), 0.76-0.65 (m, 2H) ppm.

Example 122. Enantiomers 1 and 2 of 1-[[3-(6-cyano-22,28-difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]cyclopropanecarboxylic Acid

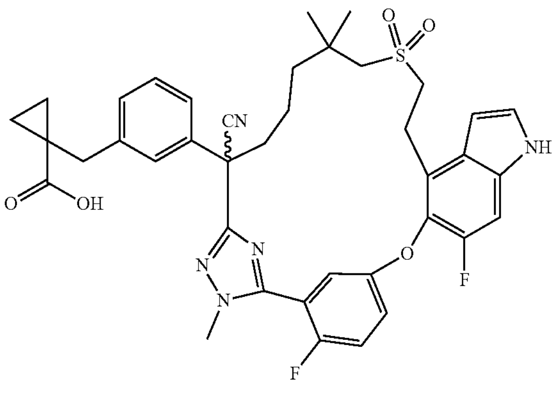 [SMILES: Cn1nc2nc1-c1cc(ccc1F)Oc1c(F)cc3[nH]ccc3c1CCS(=O)(=O)CC(C)(C)CCCC2(C#N)c1cccc(CC2(C(=O)O)CC2)c1]

Exchanging ethyl (E)-3-(3-(2-((benzyloxy)methyl)-7-((2-hydroxyethyl)sulfonyl)-6,6-dimethyl-1-(2-methylhydrazineyl)-1-oxoheptan-2-yl)phenyl)-2-methylacrylate (intermediate 69-8) with methyl 1-(3-(2-((benzyloxy)methyl)-7-((2-hydroxyethyl)sulfonyl)-6,6-dimethyl-1-(2-methylhydrazineyl)-1-oxoheptan-2-yl)benzyl)cyclopropane-1-carboxylate (Intermediate 69-15, 1.0 g, 1.66 mmol), the reaction procedure sequence (Steps A to G) described for Example 20 was used to prepare the title compounds. The racemic methyl ester (300 mg), obtained in corresponding Step D, was subjected to the following chiral SFC separation conditions: Instrument: SFC-80 (Thar, Waters); Column: OZ 20*250 mm, 10 μm; Column temperature: 35° C.; Mobile phase: carbon dioxide/methanol (0.2% methanol ammonia)=45/55; Flow rate: 80 g/min; Back pressure: 100 bar; Detection wavelength: 214 nm; Cycle time: 4 minutes; Sample solution: 300 mg dissolved in 20 mL of methanol; Injection volume: 0.8 mL. The first eluent, enantiomer 1 (120 mg, Chiral purity: 100% at 1.027 minutes, e.e. %=100%; Acq. Method Set: OZ 45% methanol (0.2% methanol ammonia as additive); Run Time: 3.0 Minutes PDA 286.0 nm), was hydrolyzed to provide acid Compound 122A (114 mg, 96%), as described in corresponding Step F. The second eluent, enantiomer 2 (120 mg, Chiral purity: 99.1% at 1.47 min; e.e. %=98.2%), was hydrolyzed to provide Compound 122B (112 mg, 95%), as described in corresponding Step G.

Compound 122A: MS (ESI): 728 m/z $[M+H]^+$, retention time: 1.97 minutes, purity: 97% (214 nm). (LC-MS Method 003). $^1H$ NMR (400 MHz, $CD_3OD$) δ 7.42-7.39 (m, 2H), 7.34 (d, J=3.2 Hz, 1H), 7.31-7.22 (m, 6H), 6.64 (d, J=3.2 Hz, 1H), 3.88 (d, J=2.0 Hz, 3H), 3.50-3.39 (m, 3H), 3.31-3.26 (m, 1H), 3.08 (d, J=13.2 Hz, 1H), 2.95-2.79 (m, 3H), 2.51 (d, J=12.0 Hz, 1H) 2.13-2.06 (m, 1H), 1.73-1.70 (m, 1H), 1.46-1.36 (m, 3H), 1.17 (s, 3H), 1.16-1.11 (m, 2H), 1.03 (s, 3H), 0.79-0.71 (m, 2H) ppm.

Compound 122B: MS (ESI): 728 m/z $[M+H]^+$, retention time: 1.97 minutes, purity: 95% (214 nm). (LC-MS Method 003). $^1H$ NMR (400 MHz, $CD_3OD$) δ 7.43-7.37 (m, 2H), 7.34 (d, J=3.2 Hz, 1H), 7.30-7.21 (m, 6H), 6.64 (d, J=3.2 Hz, 1H), 3.88 (d, J=2.4 Hz, 3H), 3.49-3.38 (m, 3H), 3.31-3.26 (m, 1H), 3.08 (d, J=13.2 Hz, 1H), 2.95-2.79 (m, 3H), 2.51 (d, J=11.6 Hz, 1H) 2.13-2.05 (m, 1H), 1.75-1.69 (m, 1H), 1.46-1.36 (m, 3H), 1.17 (s, 3H), 1.14-1.10 (m, 2H), 1.02 (s, 3H), 0.78-0.71 (m, 2H) ppm.

Example 123. Enantiomer 1 and 2 of 1-[[3-(6-cyano-22,28-difluoro-3,10,10-trimethyl-12,12-dioxo-9,24-dioxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]cyclopropanecarboxylic Acid

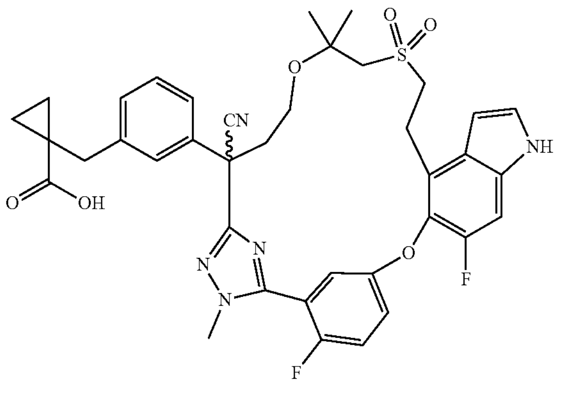 [SMILES: Cn1nc2nc1-c1cc(ccc1F)Oc1c(F)cc3[nH]ccc3c1CCS(=O)(=O)CC(C)(C)OCCC2(C#N)c1cccc(CC2(C(=O)O)CC2)c1]

Exchanging ethyl (E)-3-(3-(2-((benzyloxy)methyl)-7-((2-hydroxyethyl)sulfonyl)-6,6-dimethyl-1-(2-methylhydrazineyl)-1-oxoheptan-2-yl)phenyl)-2-methylacrylate (intermediate 69-8) with methyl 1-(3-(2-((benzyloxy)methyl)-4-((1-((2-hydroxyethyl)sulfonyl)-2-methylpropan-2-yl)oxy)-1-(2-methylhydrazineyl)-1-oxobutan-2-yl)benzyl) cyclopropane-1-carboxylate (Intermediate 69-16, 1.35 g, 2.57 mmol), the reaction procedure sequence (Steps A to G) described for Example 20 was used to prepare the title compounds. The racemic methyl ester (300 mg), obtained in corresponding Step D, was subjected to the following chiral SFC separation conditions: Instrument: SFC-80 (Thar, Waters); Column: IH 20*250 mm, 10 μm; Column temperature: 35° C.; Mobile phase: carbon dioxide/methanol (0.2% methanol ammonia)=55/45; Flow rate: 80 g/min; Back pressure: 100 bar; Detection wavelength: 214 nm; Cycle time: 4 minutes; Sample solution: 300 mg dissolved in 25 mL of methanol; Injection volume: 1.9 mL. The first eluent, enantiomer 1 (80 mg), was hydrolyzed to provide acid Compound 123A (30 mg, 38% yield), as described in corresponding Step F. The second eluent, enantiomer 2 (70 mg), was hydrolyzed to provide Compound 123B (13 mg, 20%), as described in corresponding Step G of Example 20.

Compound 123A: MS (ESI): 730 m/z $[M+H]^+$, retention time: 1.82 minutes, purity: 99% (214 nm). (LC-MS Method 003). $^1H$ NMR (400 MHz, $CD_3OD$) δ 7.48-7.38 (m, 2H), 7.36 (d, J=3.2 Hz, 1H), 7.31-7.19 (m, 5H), 7.16 (dd, J=5.6, 3.2 Hz, 1H), 6.63 (d, J=3.2 Hz, 1H), 3.91 (d, J=3.2 Hz, 3H), 3.75-3.69 (m, 1H), 3.59-3.48 (m, 2H), 3.46-3.38 (m, 3H), 3.11 (s, 2H), 2.93 (d, J=15.2 Hz, 1H), 2.84 (d, J=15.2 Hz, 1H), 2.77-2.70 (m, 1H), 2.35-2.28 (m, 1H), 1.33 (s, 3H), 1.26 (s, 3H), 1.17-1.09 (m, 2H), 0.77-0.66 (m, 2H) ppm.

Compound 123B: MS (ESI): 730 m/z $[M+H]^+$, retention time: 1.82 minutes, purity: 99% (214 nm). (LC-MS Method 003). $^1H$ NMR (400 MHz, $CD_3OD$) δ 7.49-7.38 (m, 2H), 7.36 (d, J=3.2 Hz, 1H), 7.31-7.19 (m, 5H), 7.16 (dd, J=5.2, 3.2 Hz, 1H), 6.63 (d, J=2.8 Hz, 1H), 3.91 (d, J=3.2 Hz, 3H), 3.75-3.69 (m, 1H), 3.59-3.48 (m, 2H), 3.46-3.38 (m, 3H), 3.11 (s, 2H), 2.93 (d, J=15.2 Hz, 1H), 2.84 (d, J=15.2 Hz, 1H), 2.77-2.70 (m, 1H), 2.35-2.28 (m, 1H), 1.33 (s, 3H), 1.26 (s, 3H), 1.17-1.09 (m, 2H), 0.77-0.66 (m, 2H) ppm.

Example 124. Enantiomers 1 and 2 of 3-[3-(6-cyano-22,28-difluoro-3,10,10-trimethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl)-2-fluoro-phenyl]-2-methyl-propanoic Acid

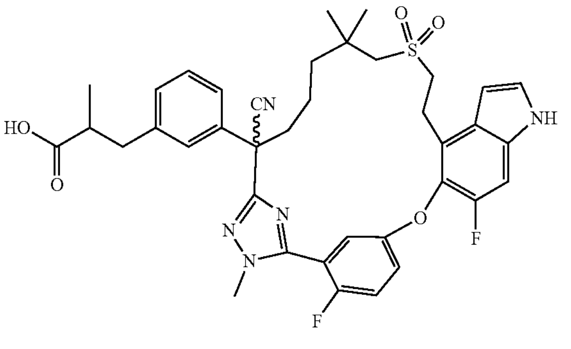 [SMILES: CC(Cc1cccc(C2(C#N)CCCC(C)(C)CS(=O)(=O)CCc3c(c(F)cc4[nH]ccc34)Oc3ccc(F)c(c3)-c3nc2nn3C)c1)C(=O)O]

Exchanging ethyl (E)-3-(3-(2-((benzyloxy)methyl)-7-((2-hydroxyethyl)sulfonyl)-6,6-dimethyl-1-(2-methylhydrazineyl)-1-oxoheptan-2-yl)phenyl)-2-methylacrylate (intermediate 69-8) with ethyl (E)-3-(3-(2-((benzyloxy)methyl)-7-((2-hydroxyethyl)sulfonyl)-6,6-dimethyl-1-(2-methylhydrazineyl)-1-oxoheptan-2-yl)-2-fluorophenyl)-2-methylacrylate (Intermediate 122, 2.0 g, 3.22 mmol), the reaction procedure sequence (Steps A to G) described for Example 20 was used to prepare the title compounds. The racemic ethyl ester (200 mg), obtained in corresponding Step D, was subjected to the following chiral SFC separation conditions: Instrument: SFC-80 (Thar, Waters); Column: OX 20*250 mm, 10 μm; Column temperature: 35° C.; Mobile phase: carbon dioxide/methanol (0.2% methanol ammonia)=60/40; Flow rate: 80 g/min; Back pressure: 100 bar; Detection wavelength: 214 nm; Cycle time: 7 minutes; Sample solution: 200 mg dissolved in 15 mL of methanol; Injection volume: 0.6 mL. The first eluent, enantiomer 1 (80 mg, chiral HPLC purity: e.e. %100% (Column: IH; Mobile phase: 80% carbon dioxide/20% methanol (0.2% methanol ammonia); Flow: 4 mL/min; Temperature: 40° C.; Back Pressure: 120 bar), was hydrolyzed to provide acid Compound 124A (60.9 mg, 79%), as described in corresponding Step F. The second eluent, enantiomer 2 (80 mg, Chiral HPLC purity: e.e. %96.8%), was hydrolyzed to provide Compound 124B (53.8 mg, 70%), as described in corresponding Step G of Example 20.

Compound 124A: MS (ESI): 734 m/z $[M+H]^+$, retention time: 1.96 minutes, purity: 99% (214 nm). (LC-MS Method 003). $^1H$ NMR (400 MHz, $CD_3OD$) δ 7.40-7.30 (m, 5H), 7.24 (d, J=10.8 Hz, 1H), 7.14-7.11 (m, 2H), 6.63 (d, J=2.4 Hz, 1H), 3.89 (s, 3H), 3.44-3.38 (m, 3H), 3.28-3.22 (m, 1H), 3.04-2.92 (m, 3H), 2.82-2.69 (m, 2H), 2.52-2.44 (m, 1H), 2.32-2.24 (m, 1H), 1.78-1.73 (m, 1H), 1.60-1.34 (m, 3H), 1.17 (s, 3H), 1.14 (d, J=6.8 Hz, 3H), 1.08 (s, 3H) ppm.

Compound 124B: MS (ESI): 734 m/z $[M+H]^+$, retention time: 1.96 minutes, purity: 98% (214 nm). (LC-MS Method 003). $^1H$ NMR (400 MHz, $CD_3OD$) δ 7.40-7.29 (m, 5H), 7.24 (d, J=10.4 Hz, 1H), 7.14-7.09 (m, 2H), 6.63 (d, J=2.8 Hz, 1H), 3.89 (d, J=1.6 Hz, 3H), 3.41-3.36 (m, 3H), 3.29-3.21 (m, 1H), 3.04-2.92 (m, 3H), 2.82-2.69 (m, 2H), 2.52-2.45 (m, 1H), 2.32-2.26 (m, 1H), 1.79-1.76 (m, 1H), 1.56-1.31 (m, 3H), 1.17 (s, 3H), 1.14 (d, J=6.8 Hz, 3H), 1.08 (s, 3H) ppm.

Example 125. Enantiomers 1 and 2 of (2S)-3-[3-(22,28-difluoro-3,6,10,10-tetramethyl-12,12,24-trioxo-12λ6-thia-3,4,19,30-tetrazapentacyclo-[23.3.1.12,5.015,23.016,20]triaconta-1(29),2(30),4,15,17,20,22,25,27-nonaen-6-yl)phenyl]-2-methylpropanoic acid

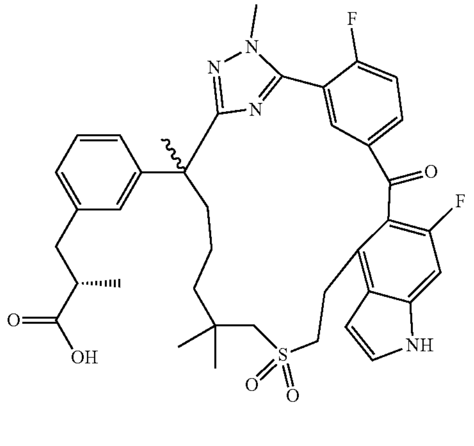 [SMILES: C[C@@H](Cc1cccc(C2(C)CCCC(C)(C)CS(=O)(=O)CCc3c(c(F)cc4[nH]ccc34)C(=O)c3ccc(F)c(c3)-c3nc2nn3C)c1)C(=O)O]

Exchanging ethyl 3-(3-(7-((2-hydroxyethyl)sulfonyl)-2,6,6-trimethyl-1-(2-methylhydrazineyl)-1-oxoheptan-2-yl) phenyl)propanoate (intermediate 58-5) with methyl (2S)-3-

(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69, 1.2 g, 2.48 mmol), the reaction procedure sequence (Steps A to B) described for Example 30A and 30B, followed by Step A to C for Example 31C and 31D, with that order, were used to prepare the title compounds. The racemic methyl ester (300 mg) obtained in corresponding Step A for Example 31C and 31D, was subjected to the following chiral SFC separation conditions: Instrument: SFC-150 (Thar, Waters); Column: IC 20*250 mm, 10 μm; Column temperature: 35° C.; Mobile phase: carbon dioxide/methanol (0.2% methanol ammonia)=45/55; Flow rate: 120 g/min; Back pressure: 100 bar; Detection wavelength: 214 nm; Cycle time: 5 minutes; Sample solution: 300 mg dissolved in 40 mL of methanol; Injection volume: 3 mL. The first eluent, enantiomer 1 (110 mg, 37%), was hydrolyzed to provide acid Compound 125A (85 mg, 79% yield), as described in corresponding Step C for Example 31C. The second eluent, enantiomer 2 (120 mg, 40%), was hydrolyzed to provide Compound 125B (78 mg, 67%), as described in corresponding Step C for Example 31D.

Compound 125A: MS (ESI): 717 m/z $[M+H]^+$, retention time: 1.86 minutes, purity: >99% (254 nm). (LC-MS Method 012). $^1H$ NMR (400 MHz, $CD_3OD$) δ 8.29-8.25 (m, 1H), 7.88 (dd, J=6.8, 2.0 Hz, 1H), 7.60 (t, J=9.6, 1H), 7.38 (d, J=3.2, 1H), 7.17-7.13 (m, 2H), 7.03-6.98 (m, 3H), 6.76 (d, J=3.2 Hz, 1H), 3.88 (d, J=2.4 Hz, 3H), 3.53-5.50 (m, 2H), 3.28-3.18 (m, 2H), 2.96-2.88 (m, 1H), 2.79 (d, J=14.0, 1H), 2.60-2.54 (m, 2H), 2.46 (d, J=13.6, 1H), 2.17-2.09 (m, 1H), 1.84-1.76 (m, 1H), 1.67 (s, 3H), 1.55-1.45 (m, 1H), 1.26-1.18 (m, 1H), 1.04 (d, J=6.8 Hz, 3H), 1.02-1.00 (m, 1H), 0.96 (s, 3H), 0.94 (s, 3H), 0.94-0.88 (m, 1H) ppm.

Compound 125B: MS (ESI): 717 m/z $[M+H]^+$, retention time: 1.86 minutes, purity: >99% (254 nm). (LC-MS Method 012). $^1H$ NMR (400 MHz, $CD_3OD$) δ 8.29-8.25 (m, 1H), 7.88 (dd, J=6.8, 2.4 Hz, 1H), 7.60 (t, J=9.6, 1H), 7.38 (d, J=3.6, 1H), 7.16-7.13 (m, 2H), 7.02-6.98 (m, 3H), 6.76 (d, J=2.4 Hz, 1H), 3.88 (d, J=2.4 Hz, 3H), 3.53-5.50 (m, 2H), 3.28-3.19 (m, 2H), 2.92-2.88 (m, 1H), 2.79 (d, J=14.0, 1H) 0.60-2.54 (m, 2H), 2.46 (d, J=13.6, 1H), 2.17-2.09 (m, 1H), 1.84-1.77 (m, 1H), 1.67 (s, 3H), 1.55-1.43 (m, 1H), 1.26-1.18 (m, 1H), 1.04 (d, J=6.8 Hz, 3H), 1.02-1.00 (m, 1H), 0.96 (s, 3H), 0.94 (s, 3H), 0.94-0.88 (m, 1H). ppm.

Example 126. Enantiomers 1 and 2 of (2R)-3-[3-(22,28-difluoro-3,6,10,10-tetramethyl-12,12,24-trioxo-12λ6-thia-3,4,19,30-tetrazapentacyclo-[23.3.1.12,5.015,23.016,20]triaconta-1(29),2(30),4,15,17,20,22,25,27-nonaen-6-yl)phenyl]-2-methylpropanoic Acid

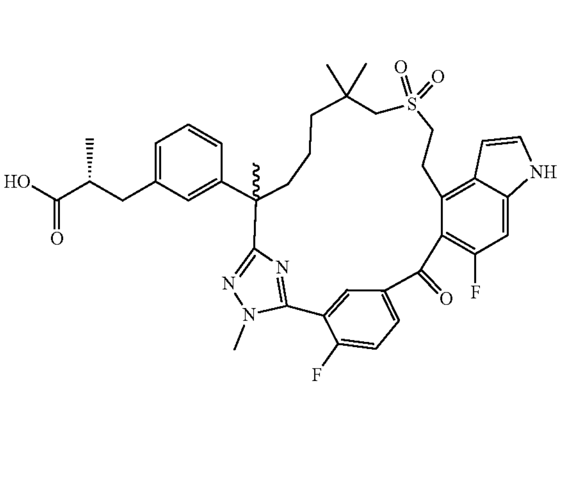 [SMILES: C[C@H](Cc1cccc(C2(C)CCCC(C)(C)CS(=O)(=O)CCc3c(c(F)cc4[nH]ccc34)C(=O)c3ccc(F)c(c3)-c3nc2nn3C)c1)C(=O)O]

and

Example 127. Enantiomers 1 and 2 of (2R)-3-[3-(22-fluoro-28-methoxy-3,6,10,10-tetramethyl-12,12,24-trioxo-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methylpropanoic Acid

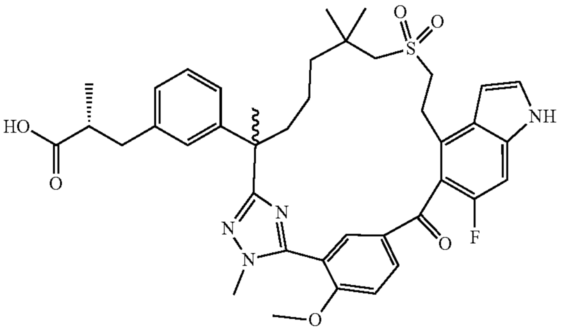 [SMILES: COc1ccc2cc1-c1nc(nn1C)C(C)(c1cccc(C[C@@H](C)C(=O)O)c1)CCCC(C)(C)CS(=O)(=O)CCc1c(c(F)cc3[nH]ccc13)C2=O]

Exchanging ethyl 3-(3-(7-((2-hydroxyethyl)sulfonyl)-2,6,6-trimethyl-1-(2-methylhydrazineyl)-1-oxoheptan-2-yl)phenyl)propanoate (intermediate 58-5) with methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69-1, 1.2 g, 2.48 mmol), the reaction procedure sequences (Steps A to B) described for Example 30A and 30B, followed by Steps A to C for Example 31C and 31D, in that order, were used to prepare the title compounds. The racemic methyl ester (210 mg), obtained in corresponding Step A for Example 31C and 31D, was subjected to the following chiral SFC separation conditions: Instrument: SFC-150 (Thar, Waters); Column: IC 20*250 mm, 10 μm; Column temperature: 35° C.; Mobile phase: carbon dioxide/methanol (0.2% methanol ammonia) =55/45; Flow rate: 120 g/min; Back pressure: 100 bar; Detection wavelength: 214 nm; Cycle time: 7.6 minutes; Sample solution: 200 mg dissolved in 20 mL of methanol; Injection volume: 2 mL. The first eluent, enantiomer 1 (70 mg, 33%), was hydrolyzed to provide acid Compound 126B (11.3 mg, 16%), and by product Compound 126A (33 mg, 48%) (formed by replacement of one fluoro group with methoxy group in the hydrolysis condition, two products were separated by prep-HPLC in this step), as described in corresponding Step C for Example 31C. The second eluent, enantiomer 2 (65 mg, 40%), was hydrolyzed to provide Compound 126B (10.2 mg, 31%) and by product Compound 126A (36.3 mg, 56%) (those two products were separated by prep-HPLC), as described in corresponding Step C for Example 31D.

Compound 126A: MS (ESI): 717 m/z $[M+H]^+$, retention time: 1.87 minutes, purity: >99% (254 nm). (LC-MS Method 012). $^1H$ NMR (400 MHz, $CD_3OD$) δ 8.29-8.25 (m, 1H), 7.88 (dd, J=6.4, 2.0 Hz, 1H), 7.60 (t, J=9.2, 1H), 7.38 (d, J=3.2, 1H), 7.17-7.12 (m, 2H), 7.03-6.97 (m, 3H), 6.76 (d, J=2.8 Hz, 1H), 3.88 (d, J=2.4 Hz, 3H), 3.54-3.50 (m, 2H), 3.28-3.21 (m, 2H), 2.96-2.90 (m, 1H), 2.79 (d, J=13.6 Hz, 1H), 2.61-2.52 (m, 2H), 2.46 (d, J=14.0 Hz, 1H), 2.17-2.09 (m, 1H), 1.84-1.76 (m, 1H), 1.66 (s, 3H), 1.53-1.45 (m, 1H), 1.24-1.17 (m, 1H), 1.04 (d, J=6.8 Hz, 3H), 1.03-1.00 (m, 1H), 0.96 (s, 3H), 0.94 (s, 3H), 0.94-0.84 (m, 1H) ppm.

Compound 127A: MS (ESI): 729 m/z $[M+H]^+$, retention time: 1.82 minutes, purity: >99% (254 nm). (LC-MS Method 012). $^1H$ NMR (400 MHz, $CD_3OD$) δ 8.26 (dd, J=8.8, 2.4 Hz, 1H), 7.70 (d, J=2.0, 1H), 7.45 (d, J=9.2, 1H), 7.36 (d, J=3.2 Hz, 1H), 7.15-7.12 (m, 2H), 7.00-6.97 (m, 3H), 6.73 (d, J=2.8 Hz, 1H), 4.08 (s, 3H), 3.79 (s, 3H), 3.48-3.45 (m, 2H), 3.28-3.16 (m, 2H), 2.95-2.86 (m, 1H), 2.79 (d, J=13.6, 1H), 2.60-2.51 (m, 3H), 2.15-2.08 (m, 1H), 1.80-1.73 (m, 1H), 1.66 (s, 3H), 1.57-1.48 (m, 1H), 1.22-1.18 (m, 1H), 1.03 (d, J=6.4 Hz, 3H), 1.06-0.92 (m, 2H), 0.96 (s, 3H), 0.95 (s, 3H) ppm.

Compound 126B: MS (ESI): 717 m/z $[M+H]^+$, retention time: 1.87 minutes, purity: >99% (254 nm). (LC-MS Method 012). $^1H$ NMR (400 MHz, $CD_3OD$) δ 8.29-8.25 (m, 1H), 7.88 (dd, J=6.4, 2.0 Hz, 1H), 7.60 (t, J=9.2, 1H), 7.38 (d, J=3.2, 1H), 7.17-7.13 (m, 2H), 7.03-6.97 (m, 3H), 6.76 (d, J=2.8 Hz, 1H), 3.88 (d, J=2.4 Hz, 3H), 3.53-3.50 (m, 2H), 3.28-3.21 (m, 2H), 2.96-2.90 (m, 1H), 2.79 (d, J=13.6, 1H), 2.61-2.52 (m, 2H), 2.46 (d, J=14.0, 1H), 2.17-2.09 (m, 1H), 1.84-1.76 (m, 1H), 1.66 (s, 3H), 1.53-1.45 (m, 1H), 1.24-1.17 (m, 1H), 1.04 (d, J=6.8 Hz, 3H), 1.03-1.00 (m, 1H), 0.96 (s, 3H), 0.94 (s, 3H), 0.94-0.84 (m, 1H) ppm.

Compound 127B: MS (ESI): 729 m/z $[M+H]^+$, retention time: 1.82 minutes, purity: >99% (254 nm). (LC-MS Method 012). $^1H$ NMR (400 MHz, $CD_3OD$) δ 8.26 (dd, J=8.8, 2.4 Hz, 1H), 7.70 (d, J=2.0, 1H), 7.45 (d, J=9.2, 1H), 7.36 (d, J=3.2 Hz, 1H), 7.15-7.12 (m, 2H), 7.00-6.97 (m, 3H), 6.73 (d, J=2.8 Hz, 1H), 4.08 (s, 3H), 3.79 (s, 3H), 3.48-3.44 (m, 2H), 3.28-3.16 (m, 2H), 2.91-2.81 (m, 2H), 2.58-2.51 (m, 3H), 2.15-2.08 (m, 1H), 1.81-1.74 (m, 1H), 1.66 (s, 3H), 1.57-1.48 (m, 1H), 1.22-1.18 (m, 1H), 1.04 (d, J=6.8 Hz, 3H), 1.03-1.00 (m, 1H), 0.96 (s, 3H), 0.94 (s, 3H), 0.94-0.84 (m, 1H) ppm.

Example 128. 5-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)indane-2-carboxylic Acid

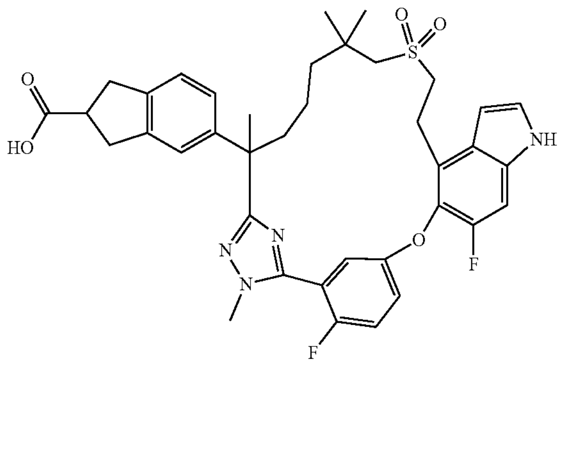 [SMILES: Cn1nc2nc1-c1cc(ccc1F)Oc1c(F)cc3[nH]ccc3c1CCS(=O)(=O)CC(C)(C)CCCC2(C)c1ccc2c(c1)CC(C(=O)O)C2]

5-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)indane-2,2-dicarboxylic Acid

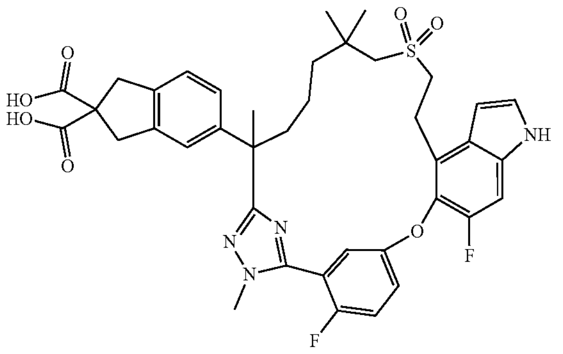 [SMILES: Cn1nc2nc1-c1cc(ccc1F)Oc1c(F)cc3[nH]ccc3c1CCS(=O)(=O)CC(C)(C)CCCC2(C)c1ccc2c(c1)CC(C(=O)O)(C(=O)O)C2]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with diethyl 5-(7-((2-hydroxyethyl)sulfonyl)-2,6,6-trimethyl-1-(2-methylhydrazineyl)-1-oxoheptan-2-yl)-1,3-dihydro-2H-indene-2,2-dicarboxylate (Intermediate 69-17, 169 mg, 0.298 mmol), the reaction procedure sequence (Steps A to D and Step F) described for Example 6 was used to prepare the title compound (43 mg) as a light-yellow solid. MS (ESI): 747 m/z $[M+Na]^+$, retention time: 2.10 minutes, purity: 90% (214 nm). (LC-MS Method 021).

Compound 128: 5-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)indane-2-carboxylic acid

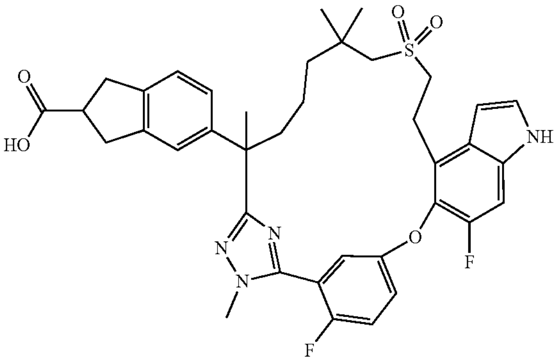 [SMILES: Cn1nc2nc1-c1cc(ccc1F)Oc1c(F)cc3[nH]ccc3c1CCS(=O)(=O)CC(C)(C)CCCC2(C)c1ccc2c(c1)CC(C(=O)O)C2]

Step B: To a stirred solution of Step A product (43 mg, 0.058 mmol) in N,N-dimethylformamide (2 mL) was added triethylamine (23 mg, 0.23 mmol). The mixture was heated at 90° C. for 15 hours and concentrated. The residue was purified by Pre-HPLC to give the title compound (13.5 mg, 33%) as white solid. MS (ESI): 703 m/z $[M+H]^+$, retention time: 1.88 minutes, purity: 99% (214 nm) (LC-MS Method 003). $^1H$ NMR (400 MHz, DMSO-$d_6$) δ 12.19 (brs, 1H), 11.34 (s, 1H), 7.45-7.41 (m, 2H), 7.33 (d, J=8.8 Hz, 1H), 7.27-7.23 (m, 2H), 7.05-7.01 (m, 2H), 6.92 (d, J=6 Hz, 1H), 6.51 (s, 1H), 3.77 (s, 3H), 3.27-3.10 (m, 5H), 3.08-3.00 (m, 4H), 2.96-2.91 (m, 1H), 2.82-2.79 (m, 1H), 2.11 (t, J=9.2 Hz, 1H), 1.70-1.64 (m, 1H), 1.59 (s, 3H), 1.49-1.43 (m, 1H), 1.23-1.14 (m, 3H), 1.02 (s, 3H), 0.97 (s, 3H) ppm.

Example 129. Enantiomer 1 and 2 of (2S)-3-[3-(22,28-difluoro-6,10,10-trimethyl-12,12-dioxo-24-oxa-12λ6-thia-3,19,30-triazapentacyclo-[23.3.1.12,5.015,23.016,20]triaconta-1(29),2(30),4,15,17,20,22,25,27-nonaen-6-yl)phenyl]-2-methyl-propanoic Acid

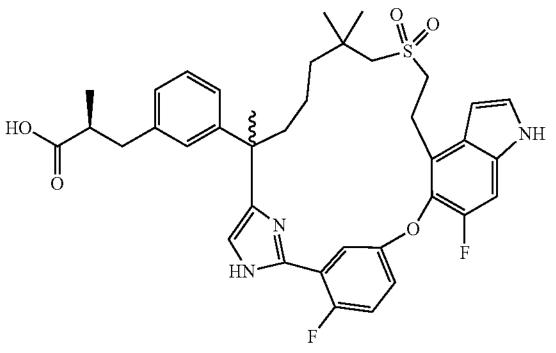 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2c[nH]3)c1)C(=O)O]

Methyl (2S)-3-(3-(2-(2-(5-((4-bromo-6-fluoro-1H-indol-5-yl)oxy)-2-fluorophenyl)-1H-imidazol-4-yl)-7-((2-((tert-butyldiphenylsilyl)oxy)ethyl)sulfonyl)-6,6-dimethylheptan-2-yl)phenyl)-2-methylpropanoate

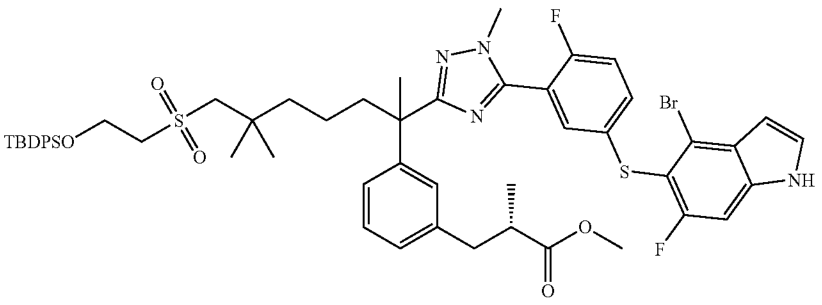

Step A: To a stirred solution of methyl (2S)-3-(3-(1-bromo-8-((2-((tert-butyldiphenylsilyl)oxy)-ethyl)sulfonyl)-3,7,7-trimethyl-2-oxooctan-3-yl)phenyl)-2-methylpropanoate (Intermediate 17-14, 22.5 g, 29.1 mmol) in N,N-dimethylformamide (300 mL) was added 5-((4-bromo-6-fluoro-1H-indol-5-yl)oxy)-2-fluorobenzimidamide (Intermediate 10-6, 11.8 g, 35.0 mmol) and sodium bicarbonate (4.9 g, 58.2 mmol). The reaction mixture was heated at 75° C. for 3 hours, then cooled to room temperature and diluted with ethyl acetate (300 mL). The mixture was washed with water, brine, dried over sodium sulfate, and concentrated. The residue was purified by automated flash chromatography (330 g silica gel column, eluted with 0-40% ethyl acetate in petroleum ether) to give the title compound (20.9 g, 69%) as a yellow solid. MS (ESI): 1038, 1040 m/z $[M+H]^+$, retention time: 1.78 minutes, purity: 90% (254 nm) (LC-MS Method 022).

Methyl (2S)-3-(3-(2-(2-(5-((4-bromo-6-fluoro-1H-indol-5-yl)oxy)-2-fluorophenyl)-1H-imidazol-4-yl)-7-((2-hydroxyethyl)sulfonyl)-6,6-dimethylheptan-2-yl)phenyl)-2-methylpropanoate

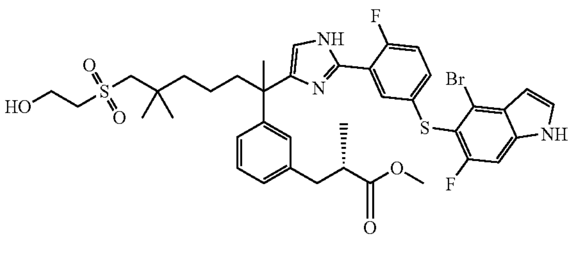 [SMILES: COC(=O)[C@@H](C)Cc1cccc(C(C)(CCCC(C)(C)CS(=O)(=O)CCO)c2c[nH]c(-c3cc(Sc4c(F)cc5[nH]ccc5c4Br)ccc3F)n2)c1]

Step B: To a stirred solution of Step A product (20.9 g, 20.1 mmol) in tetrahydrofuran (50 mL) was added tetrabutylammonium fluoride (40.2 mL, 1M in tetrahydrofuran, 40.2 mmol). The reaction was stirred at room temperature for 2 hours, then diluted with ethyl acetate (200 mL). The solution was washed with water, brine, dried over magnesium sulfate, and concentrated. The residue was purified by automated flash chromatography (330 g silica gel column, eluted with 0-80% ethyl acetate in petroleum) to give the title compound (14.8 g, 92%) as a solid. MS (ESI): 800, 802 m/z $[M+H]^+$, retention time: 1.56 minutes, purity: 93% (254 nm). (LC-MS Method 022).

Compounds 129A and 129B: Enantiomer 1 and 2 of (2S)-3-[3-(22,28-difluoro-6,10,10-trimethyl-12,12-dioxo-24-oxa-12λ6-thia-3,19,30-triazapentacyclo-[23.3.1.12,5.015,23.016,20]triaconta-1(29),2(30),4,15,17,20,22,25,27-nonaen-6-yl)phenyl]-2-methyl-propanoic Acid

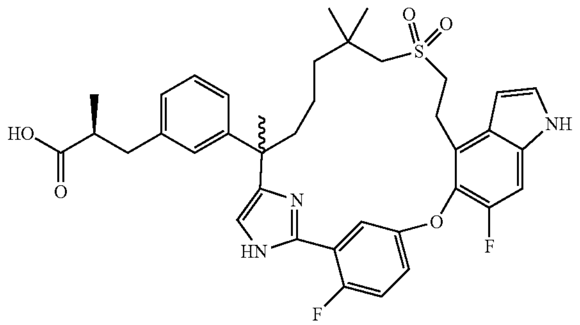 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2c[nH]3)c1)C(=O)O]

Step C: Exchanging methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 6) with methyl (2S)-3-(3-(2-(2-(5-((4-bromo-6-fluoro-1H-indol-5-yl)oxy)-2-fluorophenyl)-1H-imidazol-4-yl)-7-((2-hydroxyethyl)sulfonyl)-6,6-dimethylheptan-2-yl)phenyl)-2-methylpropanoate (Step B product of this example, 9 g, 11.3 mmol), the reaction procedure sequence (Steps B to G) described for Example 6 was used to prepare the title compounds. The racemic methyl ester (1.6 g), obtained in corresponding Step D of Example 6, was subject to chiral SFC separation using instrument SFC-80 (Thar, Waters) under the following conditions: Column: IH 20*250 mm, 10 μm; Column temperature: 35° C.; Mobile phase: carbon dioxide/methanol (0.2% methanol ammonia as additive)=45/55; Flow rate: 80 g/minutes; Back pressure: 100 bar; Detection wavelength: 214 nm; Cycle time: 9.0 minutes; Sample solution: 1500 mg dissolved in 60 mL of methanol; Injection volume: 1.9 mL. The first eluent (580 mg, 36%), enantiomer 1, was further hydrolyzed to Compound 129A (413 mg, 73%), as described in corresponding Step F, Example 6. The second eluent (610 mg, 38%), enantiomer 2, was further hydrolyzed to Compound 129B (481.4 mg, 80%), as described in corresponding Step F, Example 6.

Compound 129A: MS (ESI): 690 m/z $[M+H]^+$, retention time: 1.55 minutes, purity: 98% (254 nm). (LC-MS Method 022). $^1$H NMR (400 MHz, $CD_3OD$) δ 7.53 (dd, J=5.6, 3.2 Hz, 1H), 7.30 (d, J=3.2 Hz, 1H), 7.26-7.20 (m, 2H), 7.13 (t, J=7.6 Hz, 1H), 7.09-7.05 (m, 2H), 7.02-7.01 (m, 2H), 6.97 (d, J=7.2 Hz, 1H), 6.60 (d, J=3.2 Hz, 1H), 3.41-3.34 (m, 2H), 3.31-3.17 (m, 1H), 3.08-3.01 (m, 1H), 2.96-2.91 (m, 1H), 2.66 (s, 2H), 2.64-2.56 (m, 2H), 2.11-2.04 (m, 1H), 1.90-1.83 (m, 1H), 1.55 (s, 3H), 1.38-1.25 (m, 2H), 1.14-1.11 (m, 1H), 1.08-1.07 (m, 6H), 0.97 (s, 3H), 0.93-0.87 (m, 1H) ppm.

Compound 129B: MS (ESI): 690 m/z $[M+H]^+$, retention time: 1.55 minutes, purity: 97% (254 nm). (LC-MS Method 022). $^1$H NMR (400 MHz, $CD_3OD$) δ 7.53 (dd, J=6.0, 3.2 Hz, 1H), 7.30 (d, J=3.2 Hz, 1H), 7.26-7.20 (m, 2H), 7.13 (t, J=8.0 Hz, 1H), 7.09-7.06 (m, 2H), 7.03-7.01 (m, 2H), 6.97 (d, J=7.2 Hz, 1H), 6.60 (dd, J=3.2, 0.8 Hz, 1H), 3.41-3.34 (m, 2H), 3.31-3.13 (m, 1H), 3.08-3.01 (m, 1H), 2.96-2.89 (m, 1H), 2.66 (s, 2H), 2.64-2.55 (m, 2H), 2.11-2.05 (m, 1H), 1.90-1.83 (m, 1H), 1.55 (s, 3H), 1.35-1.25 (m, 2H), 1.14-1.11 (m, 1H), 1.08-1.06 (m, 6H), 0.97 (s, 3H), 0.92-0.87 (m, 1H) ppm.

Example 130. (2S)-3-[3-[22,28-Difluoro-3-methyl-12,12-dioxo-6-(trideuteriomethyl)spiro[24-oxa-12λ6-thia-3,4,19,30-tetrazapentacyclo-[23.3.1.25,5.015,23.016,20]triaconta-1(29),2(30),4,15,17,20,22,25,27-nonaene-10,3'-oxetane]-6-yl]phenyl]-2-methyl-propanoic Acid

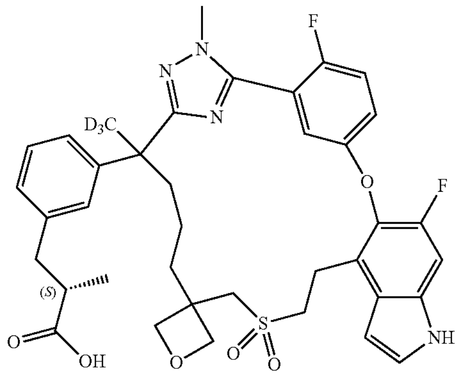

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with methyl (2S)-3-(3-(5-(3-(((2-hydroxyethyl)sulfonyl)methyl)oxetan-3-yl)-2-(2-methylhydrazine-1-carbonyl)-pentan-2-yl-1,1,1-d3)phenyl)-2-methylpropanoate (Intermediate 107-1, 513 mg, 1.02 mmol) in Step A, the reaction procedure sequence (Steps A to F, with the order of Step E (chiral separation) and Step F (ester hydrolysis) switched so the chiral separation was performed on acids) described for Example 6 was used to prepare the title compounds. The racemic acid (180 mg), obtained in corresponding Step F of Example 6, was subject to chiral SFC separation, as described in corresponding Step E in Example 6, using instrument SFC-80 (Thar, Waters) under the following conditions: Column: AD 20*250 mm, 10 μm; Column temperature: 35° C.; Mobile phase: carbon dioxide/isopropanol (0.2% methanol ammonia as additive)=70/30; Flow rate: 80 g/minutes; Back pressure: 100 bar; Detection wavelength: 214 nm; Cycle time: 4.5 minutes; Sample solution: 180 mg dissolved in 20 ml methanol; Injection volume: 0.8 mL. The first eluent (31.1 mg, 17%), enantiomer 1, was designated as Compound 130A; The second eluent (33.4 mg, 19%), enantiomer 2, was designated as Compound 130B.

Compound 130A: MS (ESI): 722 m/z $[M+H]^+$, retention time: 1.78 minutes, purity: 97% (254 nm) (LC-MS Method 022). $^1$H NMR (400 MHz, $CD_3OD$) δ 7.39-7.32 (m, 2H), 7.28 (d, J=3.2 Hz, 1H), 7.21-7.13 (m, 3H), 7.00-6.94 (m, 3H), 6.62 (dd, J=3.2, 0.4 Hz, 1H), 4.73 (d, J=6.0 Hz, 1H), 4.51 (d, J=6.0 Hz, 1H), 4.37 (dd, J=6.0, 2.8 Hz, 2H), 3.80 (d, J=1.2 Hz, 3H), 3.60-3.34 (m, 5H), 3.17-3.11 (m, 1H), 2.95-2.90 (m, 1H), 2.64-2.55 (m, 2H), 2.06-1.92 (m, 4H), 1.80-1.74 (m, 1H), 1.20-1.14 (m, 1H), 1.06 (d, J=6.8 Hz, 3H) ppm.

Compound 130A: MS (ESI): 722 m/z $[M+H]^+$, retention time: 1.78 minutes, purity: 99% (254 nm) (LC-MS Method 022). $^1$H NMR (400 MHz, $CD_3OD$) δ 7.39-7.32 (m, 2H), 7.28 (d, J=3.6 Hz, 1H), 7.20-7.12 (m, 3H), 7.00-6.93 (m, 3H), 6.62 (dd, J=3.2, 0.4 Hz, 1H), 4.73 (d, J=6.4 Hz, 1H), 4.51 (d, J=6.0 Hz, 1H), 4.37 (dd, J=6.0, 1.6 Hz, 2H), 3.80 (d, J=1.2 Hz, 3H), 3.60-3.38 (m, 5H), 3.17-3.10 (m, 1H), 2.96-2.90 (m, 1H), 2.64-2.56 (m, 2H), 2.04-1.92 (m, 4H), 1.80-1.74 (m, 1H), 1.23-1.13 (m, 1H), 1.06 (d, J=6.8 Hz, 3H) ppm.

Example 131. Ethyl 2-[[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]-3,3-difluoro-propanoate

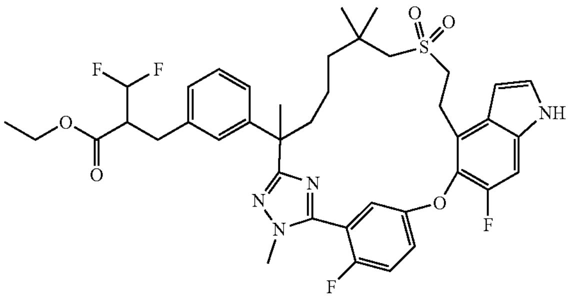 [SMILES: CCOC(=O)C(Cc1cccc(C2(C)CCCC(C)(C)CS(=O)(=O)CCc3c(c(F)cc4[nH]ccc34)Oc3ccc(F)c(c3)-c3nc2nn3C)c1)C(F)F]

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with ethyl 3,3-difluoro-2-(3-(7-((2-hydroxyethyl)sulfonyl)-2,6,6-trimethyl-1-(2-methylhydrazineyl)-1-oxoheptan-2-yl)benzyl)propanoate (Intermediate 69-18, 750 mg, 1.40 mmol) in Step A, the reaction procedure sequence (Steps A to D) described for Example 6 was used to prepare the title compound (84.5 mg).

Compound 131: MS (ESI): 769 m/z $[M+H]^+$, retention time: 2.06 minutes, purity: >99% (254 nm). (LC-MS Method 022). $^1$H NMR (400 MHz, DMSO) δ 11.38 (s, 1H), 7.47-7.43 (m, 2H), 7.34-7.26 (m, 3H), 7.18 (t, J=7.6 Hz, 1H), 7.02-6.98 (m, 3H), 6.51 (s, 1H), 6.34-6.01 (m, 1H), 3.95-3.87 (m, 2H), 3.79 (s, 3H), 3.26-3.12 (m, 5H), 2.97-2.90 (m, 2H), 2.87-2.79 (m, 2H), 2.11-2.05 (m, 1H), 1.72-1.66 (m, 1H), 1.60 (s, 3H), 1.52-1.48 (m, 1H), 1.27-1.17 (m, 3H), 1.02-0.91 (m, 10H) ppm.

Example 132. Diastereomers 1 and 2 of 3-[3-(22-fluoro-3,6,10,10-tetramethyl-12,12,26-trioxo-12λ6-thia-3,4,19,25,30-pentazapentacyclo-[23.3.1.12,5.015,23.016,20]triaconta-1(29),2(30),4,15,17,20,22,27-octaen-6-yl)phenyl]-2-methyl-propanoic Acid

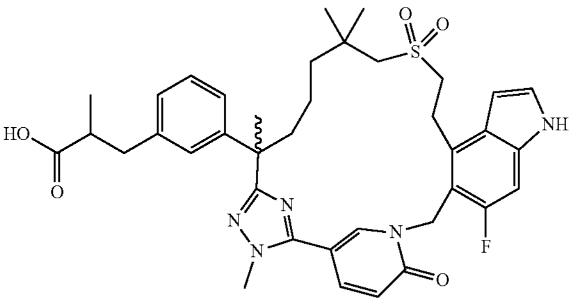 [SMILES: CC(Cc1cccc(C2(C)CCCC(C)(C)CS(=O)(=O)CCc3c(c(F)cc4[nH]ccc34)Cn3cc(ccc3=O)-c3nc2nn3C)c1)C(=O)O]

Exchanging methyl 5-((4-bromo-6-fluoro-1H-indol-5-yl)oxy)-2-fluorobenzimidothioate hydroiodide (Intermediate 14-1) with methyl 1-((4-bromo-6-fluoro-1H-indol-5-yl)methyl)-6-oxo-1,6-dihydropyridine-3-carbimidothioate (Intermediate 14-7, 790 mg, 2.0 mmol), and methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with ethyl 3-(3-(7-((2-hydroxyethyl)sulfonyl)-2,6,6-trimethyl-1-(2-methylhydrazineyl)-1-oxo-heptan-2-yl)phenyl)-2-methylpropanoate (Intermediate 58-6, 1.0 g, 2.0 mmol) in Step A, the reaction procedure sequence (Steps A to G) described for Example 6 was used to prepare the title compounds. The racemic ethyl ester (130 mg), obtained in corresponding Step D of Example 6, was subject to chiral SFC separation, as described in corresponding Step E in Example 6, using instrument SFC-150 (Thar, Waters) under the following conditions: Column: IH 20*250 mm, 10 μm; Column temperature: 35° C.; Mobile phase: carbon dioxide/methanol (0.2% methanol ammonia as additive)=75/25; Flow rate: 140 g/minutes; Back pressure: 100 bar; Detection wavelength: 214 nm; Cycle time: 4.6 minutes; Sample solution: 130 mg dissolved in 20 ml methanol and dichloromethane; Injection volume: 1.6 mL. The first eluent (48 mg, 37%), enantiomer 1, was further hydrolyzed to Compound 132A (37 mg, 77%) as described in Step F, Example 6. The second eluent (50 mg, 38%), enantiomer 2, was further hydrolyzed to Compound 132B (28 mg, 60%), as described in Step G, Example 6.

Compound 132A: MS (ESI): 702 m/z $[M+H]^+$, retention time: 1.71 minutes, purity: >99% (214 nm). (LC-MS Method 033). $^1$H NMR (400 MHz, $CD_3OD$) δ 8.01 (d, J=2.3 Hz, 1H), 7.90-7.77 (m, 1H), 7.29 (d, J=3.3 Hz, 1H), 7.14-7.11 (m, 2H), 7.07-6.94 (m, 3H), 6.66 (d, J=9.4 Hz, 1H), 6.63 (d, J=2.7 Hz, 1H), 5.41 (s, 2H), 3.78 (s, 3H), 3.53-3.42 (m, 2H), 3.36-3.30 (m, 2H), 3.24-3.17 (m, 1H), 2.92 (s, 3H), 2.63-2.55 (m, 2H), 2.17-2.13 (m, 1H), 1.86-1.77 (m, 1H), 1.62 (s, 3H), 1.45-1.30 (m, 2H), 1.10 (s, 3H), 1.09-1.04 (m, 4H), 1.03 (s, 3H) ppm.

Compound 132B: MS (ESI): 702 m/z $[M+H]^+$, retention time: 1.71 minutes, purity: >99% (214 nm). (LC-MS Method 033). $^1$H NMR (400 MHz, $CD_3OD$) δ 8.01 (d, J=2.3 Hz, 1H), 7.90-7.77 (m, 1H), 7.29 (d, J=3.3 Hz, 1H), 7.13 (t, J=7.7 Hz, 2H), 7.07-6.94 (m, 3H), 6.66 (d, J=9.4 Hz, 1H), 6.63 (d, J=2.7 Hz, 1H), 5.41 (s, 2H), 3.78 (s, 3H), 3.48 (dd, J=16.2, 8.1 Hz, 2H), 3.35 (m, 2H), 3.24-3.17 (m, 1H), 2.92

(s, 3H), 2.63-2.55 (m, 2H), 2.15 (m, 1H), 1.82 (m, 1H), 1.62 (s, 3H), 1.45-1.30 (m, 2H), 1.10 (s, 3H), 1.09-1.04 (m, 4H), 1.03 (s, 3H) ppm.

Example 133. Enantiomers 1 and 2 of 3-[3-[22,28-difluoro-3,10,10-trimethyl-12,12-dioxo-6-[(2,2,2-trifluoroethylamino)methyl]-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

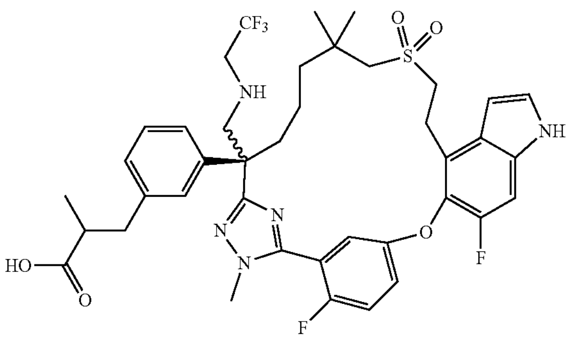

Ethyl 3-[3-[22,28-difluoro-3,10,10-trimethyl-12,12-dioxo-6-[(2,2,2-trifluoroethylamino)methyl]-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate and Isopropyl 3-[3-[22,28-difluoro-3,10,10-trimethyl-12,12-dioxo-6-[(2,2,2-trifluoroethylamino)-methyl]-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

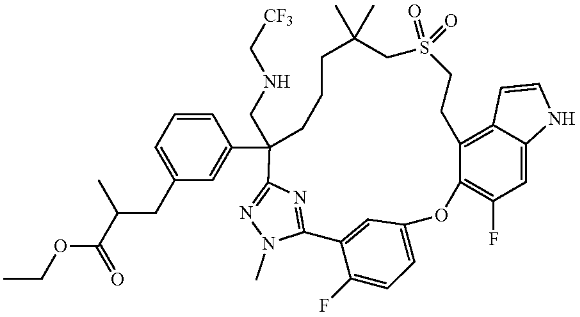

-continued

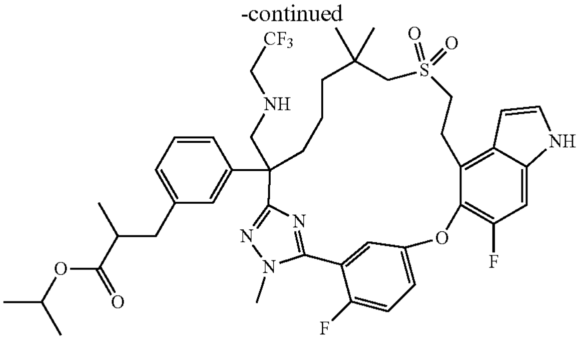

Step A: To a stirred solution of ethyl 3-[3-(22,28-difluoro-6-formyl-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate (Step B product of Example 20, 500 mg, 0.669 mmol) in 1,2-dichloroethane (10 mL) was added titanium (IV) isopropoxide (761 mg, 2.68 mmol) and 2,2,2-trifluoroethan-1-amine (199 mg, 2.01 mmol). The mixture was stirred at room temperature for 16 hours, then treated with sodium cyanoborohydride (84 mg, 1.34 mmol), and stirred for an additional 2 hours. The mixture was then poured into water (25 ml) and filtered to remove inorganic precipitate. The filtrate was extracted with ethyl acetate (3×20 mL). The combined organic phases were washed with brine, dried over sodium sulfate, and concentrated. The residue was purified by automated flash chromatography (12 g silica gel column, eluted with 0-35% ethyl acetate in petroleum ether) to give a mixture of the title compounds (total 350 mg) as a light-yellow solid. MS (ESI) (ethyl ester): 830 m/z $[M+H]^+$, retention time: 2.34 minutes, purity: 76% (214 nm); MS (ESI) (isopropyl ester): 844 m/z $[M+H]^+$, retention time: 2.39 minutes, purity: 23% (214 nm) (LC-MS Method 012).

3-[3-[22,28-Difluoro-3,10,10-trimethyl-12,12-dioxo-6-[(2,2,2-trifluoroethylamino)methyl]-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

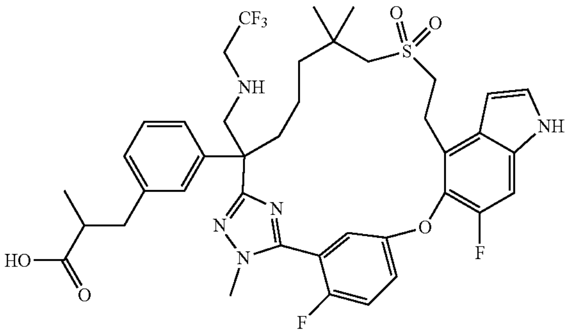 [SMILES: CC(Cc1cccc(C2(CNCC(F)(F)F)CCCC(C)(C)CS(=O)(=O)CCc3c(c(F)cc4[nH]ccc34)Oc3ccc(F)c(c3)-c3nc2nn3C)c1)C(=O)O]

Step B: To a stirred solution of Step A product mixture (330 mg, 0.398 mmol) in tetrahydrofuran/methanol/water (V/V/V=2/2/1, 5.0 mL) was added lithium hydroxide monohydrate (334 mg, 7.95 mmol). The reaction was stirred at room temperature for 6 hours, then acidified with 1.0 M hydrochloric acid to pH ~6 and extracted with ethyl acetate (3×10 mL). The combined organic phases were washed with brine, dried over sodium sulfate, and concentrated to give the title compound (300 mg, 56%2 steps) as a white solid. MS (ESI): 802 m/z $[M+H]^+$, retention time: 1.82 minutes, purity: 94% (214 nm) (LC-MS Method 012).

Compound 133A and 133B: Enantiomers 1 and 2 of 3-[3-[22,28-difluoro-3,10,10-trimethyl-12,12-dioxo-6-[(2,2,2-trifluoroethylamino)methyl]-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

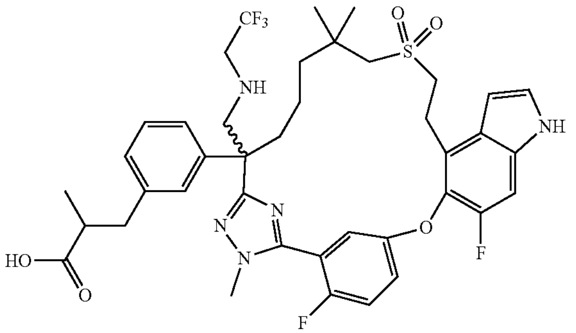 [SMILES: CC(Cc1cccc(C2(CNCC(F)(F)F)CCCC(C)(C)CS(=O)(=O)CCc3c(c(F)cc4[nH]ccc34)Oc3ccc(F)c(c3)-c3nc2nn3C)c1)C(=O)O]

Step C: The racemic Step B product (300 mg) was subject to chiral SFC under the following condition: Instrument: SFC-150 (Thar, Waters); Column: IG 20*250 mm, 10 μm; Column temperature: 35° C.; Mobile phase: carbon dioxide/isopropanol (0.2% methanol ammonia)=75/25; Flow rate: 100 g/minutes; Back pressure: 100 bar; Detection wavelength: 214 nm; Cycle time: 4 minutes; Sample solution: 300 mg dissolved in 32 mL methanol and dichloromethane; Injection volume: 0.7 mL. The first eluent (126.8 mg, 42%), enantiomer 1, is designated as Compound 133A; The second eluent (121.2 mg, 40%), enantiomer 2, is designated as Compound 133B. Both are white solids.

Compound 133A: MS (ESI): 802 m/z $[M+H]^+$, retention time: 1.89 minutes, purity: 97% (214 nm) (LC-MS Method 003). Chiral purity: 100% (100% ee; Retention time: 1.78 minutes; Chiral-HPLC method: Column: IG-3 4.6*100 mm 3 μm Processing; Acq. Method Set: IG 20% B3; Cosolvent: carbon dioxide/isopropyl alcohol [1% ammonia (7 M in methanol) as additive]; Injection Volume: 7.00 μL; Run Time: 6.0 Minutes; Flowrate: 3.0 mL/minute; Back pressure: 2000 psi; Column Temperature: 40° C.). $^1H$ NMR (400 MHz, $CD_3OD$) δ 7.34-7.29 (m, 3H), 7.21-7.17 (m, 3H), 7.07-6.98 (m, 3H), 6.60 (t, J=2.8 Hz, 1H), 3.88 (d, J=2.0 Hz, 3H), 3.39-3.34 (m, 4H), 3.27-3.16 (m, 2H), 3.05-2.92 (m, 3H), 2.89-2.85 (m, 1H), 2.80-2.76 (m, 1H), 2.66-2.58 (m, 2H), 2.12-2.03 (m, 2H), 1.69-1.57 (m, 1H), 1.39-1.28 (m, 1H), 1.22-1.12 (m, 1H), 1.08-1.05 (m, 6H), 0.99-0.90 (m, 4H) ppm.

Compound 133B: MS (ESI): 802 m/z $[M+H]^+$, retention time: 2.12 minutes, purity: 99% (214 nm) (LC-MS Method 012). Chiral purity: 99% (98% ee; Retention time: 2.1 minutes). $^1H$ NMR (400 MHz, $CD_3OD$) δ 7.35-7.29 (m, 3H), 7.21-7.17 (m, 3H), 7.05-7.00 (m, 3H), 6.60 (t, J=3.2 Hz, 1H), 3.88 (d, J=1.6 Hz, 3H), 3.39-3.35 (m, 4H), 3.27-3.16 (m, 2H), 3.04-2.92 (m, 3H), 2.89-2.85 (m, 1H), 2.80-2.76 (m, 1H), 2.66-2.58 (m, 2H), 2.15-2.00 (m, 2H), 1.67-1.58 (m, 1H), 1.39-1.29 (m, 1H), 1.19-1.12 (m, 1H), 1.08-1.05 (m, 6H), 1.00-0.90 (m, 4H) ppm.

Example 134. Diastereomers 1 and 2 of 3-[3-(22,28-Difluoro-3,6,10,10-tetramethyl-12,12-dioxo-24-oxa-12λ6-thia-3,4,19,30-tetrazapentacyclo-[23.3.1.12,5.015,23.016,20]-triaconta-1(29),2(30),4,15,17,20,22,25,27-nonaen-6-yl)phenyl]-2-hydroxy-propanoic Acid

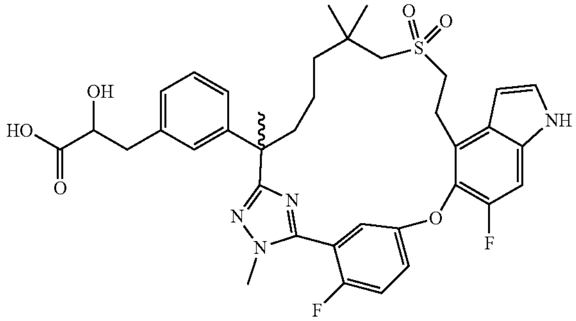 [SMILES: Cn1nc2nc1-c1cc(ccc1F)Oc1c(F)cc3[nH]ccc3c1CCS(=O)(=O)CC(C)(C)CCCC2(C)c1cccc(CC(O)C(=O)O)c1]

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with ethyl 2-(benzyloxy)-3-(3-(7-((2-hydroxyethyl)sulfonyl)-2,6,6-trimethyl-1-(2-methylhydrazineyl)-1-oxoheptan-2-yl)phenyl)propanoate (Intermediate 69-24, 450 mg, 0.76 mmol) in Step A, the reaction procedure sequence (Steps A to G) described for Example 6 was used to prepare the title compounds. The racemic ethyl ester (188 mg), obtained in corresponding Step D of Example 6, was subject to chiral SFC separation, as described in corresponding Step E in Example 6, using instrument SFC-80 (Thar, Waters) under the following conditions: Column: IC 20*250 mm, 10 μm; Column temperature: 35° C.; Mobile phase: carbon dioxide/methanol (0.2% methanol ammonia as additive)=60/40; Flow rate: 120 g/minutes; Back pressure: 100 bar; Detection wavelength: 214 nm; Cycle time: 4.0 minutes; Sample solution: 188 mg dissolved in 20 ml methanol and dichloromethane; Injection volume: 0.6 mL. The first eluent (75 mg, 40%), enantiomer 1, was further hydrolyzed to Compound 134A (48.9 mg, 69%, white solid) as described in Step F, Example 6. The second eluent (73 mg, 39%), enantiomer 2, was further hydrolyzed to Compound 134B (64.9 mg, 92%, white solid), as described in Step G, Example 6.

Compound 134A: MS (ESI): 707 m/z $[M+H]^+$, retention time: 1.80 minutes, purity: >99% (214 nm) (LC-MS Method 003). $^1H$ NMR (400 MHz, $CD_3OD$) δ 7.35-7.32 (m, 3H), 7.24-7.15 (m, 4H), 7.10 (d, J=7.6 Hz, 1H), 7.05 (t, J=7.6 Hz, 1H), 6.64 (d, J=2.8 Hz, 1H), 4.27 (s, 1H), 3.87 (d, J=1.2 Hz, 3H), 3.39-3.38 (m, 2H), 3.30-3.21 (m, 2H), 3.08-3.03 (m, 1H), 2.94-2.84 (m, 1H), 2.83-2.77 (m, 2H), 2.20-2.14 (m, 1H), 1.87-1.81 (m, 1H), 1.69 (s, 3H), 1.62-1.55 (m, 1H), 1.35-1.24 (m, 2H), 1.20-1.17 (m, 1H), 1.07 (s, 6H) ppm.

Compound 134B: MS (ESI): 707 m/z $[M+H]^+$, retention time: 1.80 minutes, purity: >99% (214 nm) (LC-MS Method 003). $^1H$ NMR (400 MHz, $CD_3OD$) δ 7.38-7.32 (m, 3H), 7.24-7.14 (m, 4H), 7.10 (d, J=5.6 Hz, 1H), 7.04 (t, J=6.0 Hz, 1H), 6.64 (d, J=2.8 Hz, 1H), 4.28-4.24 (m, 1H), 3.87 (d, J=2.0 Hz, 3H), 3.42-3.33 (m, 2H), 3.28-3.19 (m, 2H), 3.07-3.02 (m, 1H), 2.95-2.90 (m, 1H), 2.86-2.77 (m, 2H), 2.20-2.13 (m, 1H), 1.89-1.81 (m, 1H), 1.70 (s, 3H), 1.61-1.53 (m, 1H), 1.37-1.31 (m, 2H), 1.28-1.17 (m, 1H), 1.07 (s, 6H) ppm.

Example 135. 3-[3-(22,28-Difluoro-3,6,10,10-tetramethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl)phenyl]-2-methoxy-propanoic Acid

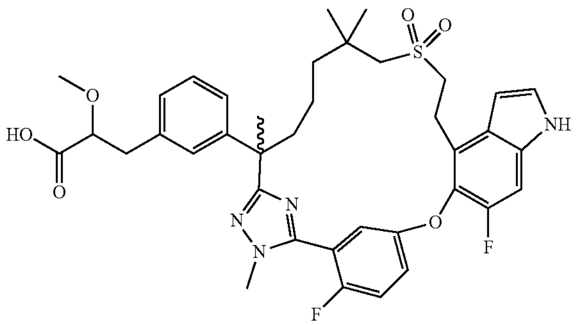 [SMILES: COC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (Intermediate 69) with ethyl 3-(3-(7-((2-hydroxyethyl)sulfonyl)-2,6,6-trimethyl-1-(2-methylhydrazineyl)-1-oxoheptan-2-yl)phenyl)-2-methoxypropanoate (Intermediate 69-25, 810 mg, 1.58 mmol) in Step A, the reaction procedure sequence (Steps A to G) described for Example 6 was used to prepare the title compounds. The racemic ethyl ester (328 mg), obtained in corresponding Step D of Example 6, was subject to chiral SFC separation, as described in corresponding Step E in Example 6, using instrument SFC-150 (Thar, Waters) under the following conditions: Column: IH 20*250 mm, 10 μm; Column temperature: 35° C.; Mobile phase: carbon dioxide/methanol (0.2% methanol ammonia as additive)=80/20; Flow rate: 140 g/minutes; Back pressure: 100 bar; Detection wavelength: 214 nm; Cycle time: 3.1 minutes; Sample solution: 328 mg dissolved in 31 mL methanol and dichloromethane; Injection volume: 1.3 mL. The first eluent (151 mg, 46%), enantiomer 1, was further hydrolyzed to Compound 135A (135.4 mg, 94%, white solid) as described in Step F of Example 6. The second eluent (144 mg, 44%), enantiomer 2, was further hydrolyzed to Compound 135B (124.3 mg, 91%, white solid), as described in Step G of Example 6.

Compound 135A: MS (ESI): 721 m/z $[M+H]^+$, retention time: 1.86 minutes, purity: >99% (214 nm) (LC-MS Method 003). $^1H$ NMR (400 MHz, $CD_3OD$) δ 7.38-7.31 (m, 3H), 7.24-7.15 (m, 3H), 7.14-7.00 (m, 3H), 6.64 (d, J=3.2 Hz, 1H), 3.88-3.84 (m, 4H), 3.42-3.38 (m, 2H), 3.30-3.20 (m, 5H), 3.03-2.91 (m, 2H), 2.87-2.78 (m, 2H), 2.19-2.14 (m, 1H), 1.88-1.81 (m, 1H), 1.69 (s, 3H), 1.63-1.57 (m, 1H), 1.37-1.31 (m, 2H), 1.24-1.15 (m, 1H), 1.07 (s, 6H) ppm.

Compound 135B: MS (ESI): 721 m/z $[M+H]^+$, retention time: 1.86 minutes, purity: >99% (214 nm) (LC-MS Method 003). $^1H$ NMR (400 MHz, $CD_3OD$) δ 7.38-7.32 (m, 3H), 7.24-7.17 (m, 3H), 7.14-7.00 (m, 3H), 6.64 (d, J=3.2 Hz, 1H), 3.89-3.87 (m, 4H), 3.43-3.34 (m, 2H), 3.29-3.18 (m, 5H), 3.03-2.92 (m, 2H), 2.88-2.79 (m, 2H), 2.20-2.13 (m, 1H), 1.88-1.81 (m, 1H), 1.69 (s, 3H), 1.65-1.55 (m, 1H), 1.37-1.30 (m, 2H), 1.24-1.16 (m, 1H), 1.07 (s, 6H) ppm Example 136. Diastereomers 1 and 2 of 3-[3-[6-(aminomethyl)-22,28-difluoro-3,10,10-trimethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl]phenyl]-2-methyl-propanoic Acid

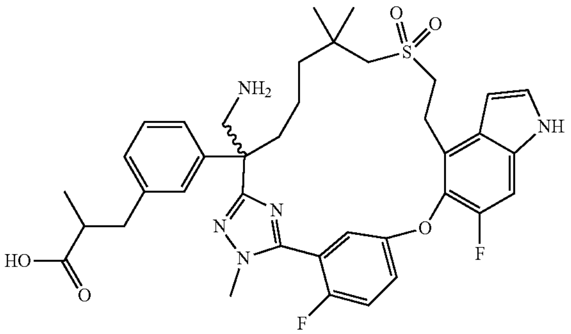 [SMILES: CC(Cc1cccc(C2(CN)CCCC(C)(C)CS(=O)(=O)CCc3c(c(F)cc4[nH]ccc34)Oc3ccc(F)c(c3)-c3nc2nn3C)c1)C(=O)O]

Ethyl 3-[3-[6-(aminomethyl)-22,28-difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

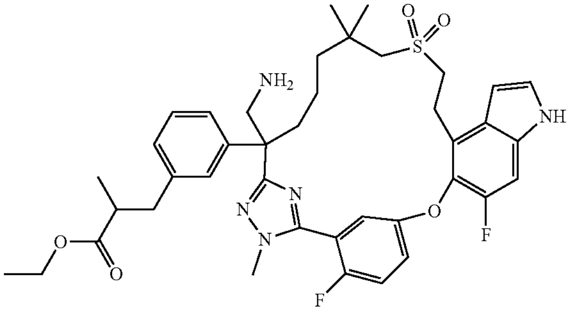 [SMILES: CCOC(=O)C(C)Cc1cccc(C2(CN)CCCC(C)(C)CS(=O)(=O)CCc3c(c(F)cc4[nH]ccc34)Oc3ccc(F)c(c3)-c3nc2nn3C)c1]

Step A: To a stirred solution of ethyl 3-[3-(22,28-difluoro-6-formyl-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate (Step B product of Example 20, 200 mg, 0.268 mmol) was added titanium (IV) isopropoxide (152 mg, 0.536 mmol) and a 7.0 M $NH_3$ solution in methanol (8.0 ml) under argon. The mixture was stirred at room temperature for 6 hours, then treated with solid sodium borohydride (20.3 mg, 0.536 mmol) and stirred for an additional 16 hours. The reaction mixture was poured into water (20 ml) and filtered to remove the inorganic precipitate. The filtrate was extracted with ethyl acetate (3×10 mL). The combined organic phases were washed with brine, dried over sodium sulfate, and concentrated. The residue was purified by automated flash chromatography (4.0 g silica gel column, eluted with 0-65% ethyl acetate in petroleum ether) to give the title compound (100 mg, 50%) as a light-yellow solid. MS (ESI): 748 m/z $[M+H]^+$, retention time: 1.59 minutes, purity: 82% (214 nm) (LC-MS Method 004).

Compounds 136A and 136B: Diastereomers 1 and 2 of 3-[3-[6-(aminomethyl)-22,28-difluoro-3,10,10-trimethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl]phenyl]-2-methyl-propanoic Acid

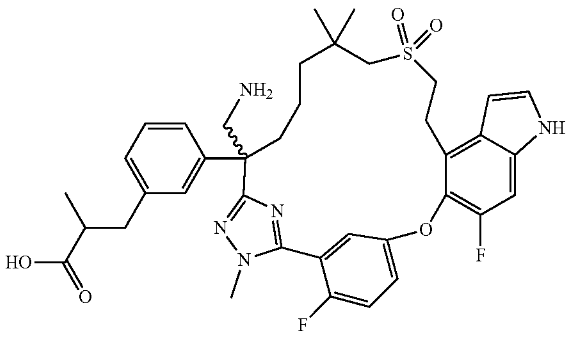 [SMILES: CC(Cc1cccc(C2(CN)CCCC(C)(C)CS(=O)(=O)CCc3c(c(F)cc4[nH]ccc34)Oc3ccc(F)c(c3)-c3nc2nn3C)c1)C(=O)O]

Step B: Racemic Step A product (200 mg) was subject to chiral SFC separation under the following separation condition: Instrument: SFC-80 (Thar, Waters); Column: IH 20*250 mm, 10 μm; Column temperature: 35° C.; Mobile phase: carbon dioxide/ethanol (0.5% methanol ammonia as additive)=60/40; Flow rate: 80 g/minutes; Back pressure: 100 bar; Detection wavelength: 214 nm; Cycle time: 8.0 minutes; Sample solution: 200 mg dissolved in 20 ml methanol; Injection volume: 1.0 ml. The first eluent is diastereomer 1 (70 mg, 35%, white solid); its chiral purity is 96.8% (e.e. %). (Chiral HPLC condition: Column: AS-3 4.6*100 mm 3 μm; Mobile phase: carbon dioxide/ethanol (1% ammonia, 7M ammonia in methanol as additive)=75/25; Injection volume: 7.5 μL; Run Time: 6.0 Minutes; Flow rate: 3.0 mL/min; CST Back Pressure: 2000 psi; CST Column Temperature: 40° C. retention time: 2.44 minutes). This diastereomer 1 is further hydrolyzed to Compound 136A (63.1 mg, 94%, white solid), using conditions described in Step B of Example 133. The second eluent, diastereomer 2 (70 mg, 35%, white solid; Chiral purity: ee >99%; retention time: 4.21 minutes), is further hydrolyzed to Compound 136B (39.5 mg, 59%, white solid), using conditions described in Step B of Example 133.

Compound 136A: MS (ESI): 720 m/z $[M+H]^+$, retention time: 1.54 minutes, purity: 99% (214 nm) (LC-MS Method 004). $^1H$ NMR (400 MHz, $CD_3OD$) δ 7.38-7.24 (m, 5H), 7.19 (d, J=10.8 Hz, 1H), 7.16-7.14 (m, 1H), 7.06-7.04 (m, 1H), 6.98-6.90 (m, 1H), 6.61 (d, J=3.2 Hz, 1H), 3.94 (d, J=2.0 Hz, 3H), 3.62-3.51 (m, 2H), 3.40-3.35 (m, 2H), 3.24-3.20 (m, 2H), 2.98-2.92 (m, 2H), 2.84-2.79 (m, 1H), 2.69-2.63 (m, 2H), 2.15-2.09 (m, 1H), 1.96-1.86 (m, 2H), 1.48-1.40 (m, 1H), 1.29-1.22 (m, 1H), 1.13 (s, 3H), 1.11-1.08 (m, 3H), 1.05-0.95 (m, 1H), 0.92 (s, 3H) ppm. Chiral purity: e.e. >99%. (chiral HPLC conditions: Column: AS-3 4.6*100 mm 3 μm; Mobile: Carbon dioxide/methanol [0.2% ammonia (7M in methanol) as additive]=80:20; Injection volume: 7.50 μl; Run time: 6.0 minutes; Flow rate: 3.0 mL/minutes; Back pressure: 2000 psi; Column temperature: 40° C.; retention time=2.29 minutes).

Compound 136B: MS (ESI): 720 m/z $[M+H]^+$, retention time: 1.55 minutes, purity: 99% (214 nm) (LC-MS Method 004). $^1H$ NMR (400 MHz, $CD_3OD$) δ 7.38-7.25 (m, 5H), 7.19 (d, J=10.8 Hz, 1H), 7.16-7.14 (m, 1H), 7.06-7.05 (m, 1H), 6.98-6.90 (m, 1H), 6.61 (d, J=3.2 Hz, 1H), 3.94 (d, J=2.0 Hz, 3H), 3.62-3.51 (m, 2H), 3.40-3.35 (m, 2H), 3.24-3.20 (m, 2H), 2.97-2.91 (m, 2H), 2.83-2.79 (m, 1H), 2.69-2.61 (m, 2H), 2.15-2.09 (m, 1H), 1.96-1.86 (m, 2H), 1.48-1.42 (m, 1H), 1.29-1.25 (m, 1H), 1.12 (s, 3H), 1.11-1.08 (m, 3H), 1.01-0.97 (m, 1H), 0.92 (s, 3H) ppm. Chiral HPLC purity: e.e. >99%, retention time: 3.62 minutes.

Example 137. Diastereomers 1 and 2 of 3-[3-[6-[(2,2-difluoroethylamino)methyl]-22,28-difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

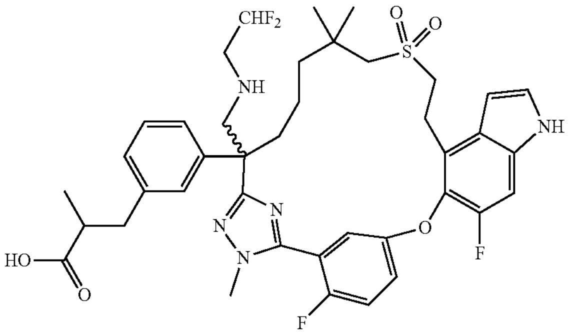 [SMILES: CC(Cc1cccc(C2(CNCC(F)F)CCCC(C)(C)CS(=O)(=O)CCc3c(c(F)cc4[nH]ccc34)Oc3ccc(F)c(c3)-c3nc2nn3C)c1)C(=O)O]

Exchanging 7.0 M $NH_3$ solution in methanol with 2,2-difluoroethan-1-amine (271 mg, 3.35 mmol), the reaction procedure sequence (Steps A to B) described for Example 136A and 136B was used to prepare the title compounds. The racemic ethyl ester (280 mg), obtained from corresponding Step A of Example 136A and 136B, was subject to chiral HPLC purification using the following conditions: Column: Chiralpak IC; Column size: 50 mm I.D.×250 mm L, 10 μm; Sample solution: 1.1 mg/mL in Mobile phase; Injection: 5 mL; Mobile phase: Hexane/dichloromethane/isopropyl alcohol=75/15/10 (V/V/V); Flow rate: 60 mL/minutes; Wave length: UV 214 nm; Temperature: 38° C. The first eluent, enantiomer 1 (120 mg, 43%), was further hydrolyzed to Compound 137A (86.6 mg, 75%), as described in Step B of Example 136A and 136B. The second eluent, enantiomer 2 (120 mg), was further hydrolyzed to 137B (56 mg, 48%).

Compound 137A: MS (ESI): 784 m/z $[M+H]^+$, retention time: 1.65 minutes, purity: 96% (214 nm) (LC-MS Method 004). $^1H$ NMR (400 MHz, $CD_3OD$) δ 7.35-7.28 (m, 3H), 7.22-7.18 (m, 3H), 7.07-7.05 (m, 2H), 6.98 (t, J=8.0 Hz, 1H), 6.60 (d, J=3.2 Hz, 1H), 5.98-5.67 (m, 1H), 3.89 (d, J=2.0 Hz, 3H), 3.40-3.31 (m, 4H), 3.23-3.18 (m, 2H), 2.96-2.77 (m, 5H), 2.63-2.59 (m, 2H), 2.08-2.04 (m, 2H), 1.74-1.64 (m, 1H), 1.40-1.32 (m, 1H), 1.18-1.14 (m, 1H), 1.10-1.05 (m, 6H), 0.98 (s, 3H), 0.91-0.85 (m, 1H) ppm. Chiral purity: ee %>99%. (Chiral-HPLC conditions: Analysis Method: Column: IG (4.6*250 mm 5 μm); Mobile phase: n-Hexane (0.1% trifluoracetic acid): IPA (0.1% trifluoroacetic acid)=80:20; Wavelength: 290 nm; Flow rate: 1 mL/minute; Temperature: 40° C. Retention time=10.38 min, 100% (290 nm).

Compound 137B: MS (ESI): 784 m/z $[M+H]^+$, retention time: 1.66 minutes, purity: >99% (214 nm) (LC-MS Method 004). $^1H$ NMR (400 MHz, CD3OD) δ 7.35-7.28 (m, 3H), 7.21-7.18 (m, 3H), 7.07-7.04 (m, 2H), 6.98 (t, J=7.6 Hz, 1H), 6.60 (d, J=3.2 Hz, 1H), 5.95-5.64 (m, 1H), 3.88 (d, J=2.0 Hz, 3H), 3.38-3.31 (m, 4H), 3.23-3.18 (m, 2H), 2.98-2.77 (m, 5H), 2.66-2.59 (m, 2H), 2.08-2.02 (m, 2H), 1.72-1.61 (m, 1H), 1.40-1.33 (m, 1H), 1.18-1.14 (m, 1H), 1.09-1.05 (m, 6H), 0.97 (s, 3H), 0.94-0.87 (m, 1H) ppm. Chiral purity: e.e. %>99% (Chiral-HPLC conditions: Analysis Method: Column: IG (4.6*250 mm 5 μm); Mobile phase: n-Hexane (0.1% TFA): IPA (0.1% TFA)=80:20; Wavelength: 290 nm; Flowrate: 1 ml/min; Temperature: 40° C. RT=12.85 min, 100% (290 nm).

Example 138. 3-[3-(6-Amino-22,28-difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

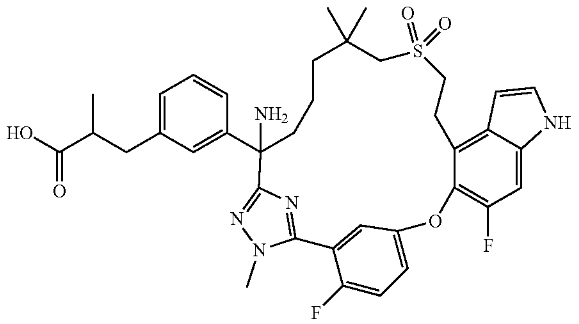 [SMILES: CC(Cc1cccc(C2(N)CCCC(C)(C)CS(=O)(=O)CCc3c(c(F)cc4[nH]ccc34)Oc3ccc(F)c(c3)-c3nc2nn3C)c1)C(=O)O]

6-[3-(3-Ethoxy-2-methyl-3-oxo-propyl)phenyl]-22,28-difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaene-6-carboxylic Acid

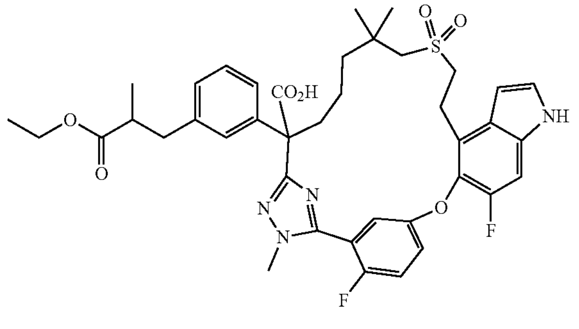 [SMILES: CCOC(=O)C(C)Cc1cccc(C2(C(=O)O)CCCC(C)(C)CS(=O)(=O)CCc3c(c(F)cc4[nH]ccc34)Oc3ccc(F)c(c3)-c3nc2nn3C)c1]

Step A: To a stirred solution of ethyl 3-[3-(22,28-difluoro-6-formyl-3,10,10-trimethyl-12,12-dioxo-24-oxa-12lambda6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate (Step B product of Example 20, 100 mg, 0.134 mmol) in 1,4-dioxane (2 mL) and water (1.0 mL) were added potassium dihydrogen phosphate (72.9 mg, 0.536 mmol), sodium chlorite (60.6 mg, 0.67 mmol) and 2-methyl-2-butene (0.5 mL). The mixture was stirred at room temperature for 5 hours, then diluted with water (20 mL), and extracted with ethyl acetate (3×10 mL). The combined organic phases were washed with brine, dried over sodium sulfate, and concentrated. The residue was purified by automated flash chromatography (12 g silica gel column, eluted with 0-65% ethyl acetate in petroleum ether) to give the title compound (50 mg, 49%) as a light-yellow solid. MS (ESI): 763 m/z [M+H]$^+$, retention time: 1.98 minutes, purity: 69% (214 nm) (LC-MS Method 004).

Ethyl 3-[3-[6-(benzyloxycarbonylamino)-22,28-difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

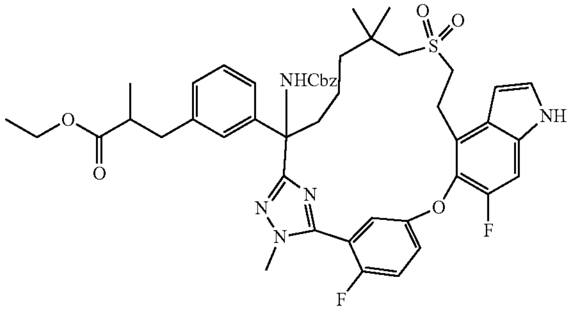 [SMILES: CCOC(=O)C(C)Cc1cccc(C2(NC(=O)OCc3ccccc3)CCCC(C)(C)CS(=O)(=O)CCc3c(c(F)cc4[nH]ccc34)Oc3ccc(F)c(c3)-c3nc2nn3C)c1]

Step B: To a stirred solution of Step A product (50 mg, 0.0655 mmol) in toluene (4.0 mL) was added triethylamine (20 mg, 0.197 mmol) and diphenyl azidophosphate (27 mg, 0.0983 mmol). The mixture was stirred at 110° C. for 2 hours, then treated with benzyl alcohol (35.4 mg, 0.328 mmol) and stirred at 110° C. for an additional 2 hours. The mixture was cooled to room temperature, diluted with water (20 mL), and extracted with ethyl acetate (3×10 mL). The combined organic phases were washed with brine, dried over sodium sulfate, filtered, and concentrated. The residue was purified by automated flash chromatography (4.0 g silica gel column, eluted with 0-65% ethyl acetate in petroleum ether) to give the title compound (10 mg, 18%) as a light-yellow solid. MS (ESI): 868 m/z [M+H]$^+$, retention time: 2.08 minutes, purity: 55% (214 nm) (LC-MS Method 004).

Ethyl 3-[3-(6-amino-22,28-difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate

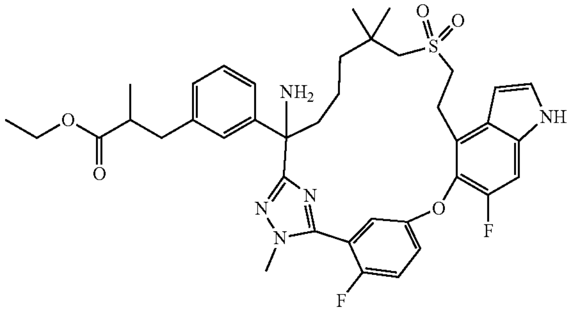 [SMILES: CCOC(=O)C(C)Cc1cccc(C2(N)CCCC(C)(C)CS(=O)(=O)CCc3c(c(F)cc4[nH]ccc34)Oc3ccc(F)c(c3)-c3nc2nn3C)c1]

Step C: To a stirred solution of Step B product (10 mg, 0.0115 mmol) in ethanol (1.0 mL) was added 10% palladium on carbon (wetted with ca. 55% water, 5.0 mg). The reaction mixture was stirred under hydrogen for 4 hours at room temperature. The mixture was filtered through a pad of Celite. The filtrate was concentrated to give the title compound (9.0 mg, crude) as a light-yellow solid. MS (ESI): 734 m/z $[M+H]^+$, retention time: 1.66 minutes, purity: 71% (214 nm) (LC-MS Method 004).

Compound 138: 3-[3-(6-Amino-22,28-difluoro-3,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic Acid

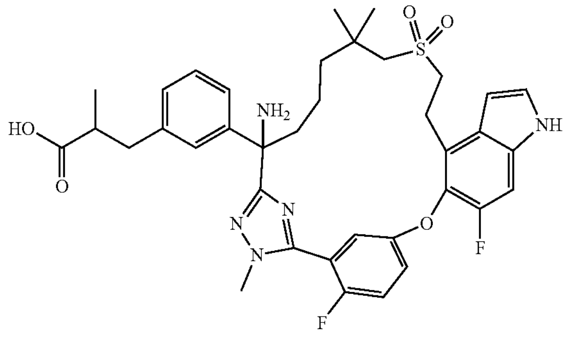 [SMILES: CC(Cc1cccc(C2(N)CCCC(C)(C)CS(=O)(=O)CCc3c(c(F)cc4[nH]ccc34)Oc3ccc(F)c(c3)-c3nc2nn3C)c1)C(=O)O]

Step D: To a stirred solution of Step C product (9.0 mg, 0.0123 mmol) in tetrahydrofuran/methanol/water (V/V/V=2/2/1, 1.0 mL) was added lithium hydroxide monohydrate (10.3 mg, 0.245 mmol). The reaction was stirred at room temperature for 6 hours, then acidified with 1.0 M hydrochloric acid to pH ~6 and extracted with ethyl acetate (3×10 mL). The combined organic phases were washed with brine, dried over sodium sulfate, and concentrated. The residue was purified by Prep-HPLC to give the title compound (1.5 mg, 19% 2 steps) as a white solid. MS (ESI): 706 m/z $[M+H]^+$, retention time: 1.55 minutes, purity: 96% (214 nm) (LC-MS Method 004). $^1H$ NMR (400 MHz, $CD_3OD$) δ 7.39-7.35 (m, 2H), 7.30 (d, J=2.8 Hz, 1H), 7.28-7.19 (m, 5H), 7.04-6.93 (m, 1H), 6.62 (d, J=3.2 Hz, 1H), 3.92 (t, J=2.0 Hz, 3H), 3.48-3.37 (m, 2H), 3.27-3.22 (m, 2H), 2.99-2.86 (m, 2H), 2.83-2.80 (m, 1H), 2.63-2.50 (m, 2H), 2.39-2.30 (m, 1H), 2.15-2.07 (m, 1H), 1.84-1.78 (m, 1H), 1.42-1.38 (m, 1H), 1.29-1.21 (m, 1H), 1.10-1.04 (m, 7H), 0.99 (d, J=2.0 Hz, 3H) ppm.

Example 139. Diastereomer 1 of isopropyl (2S)-3-[3-(22,28-difluoro-3,6,10,10-tetramethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl)phenyl]-2-methyl-propanoate

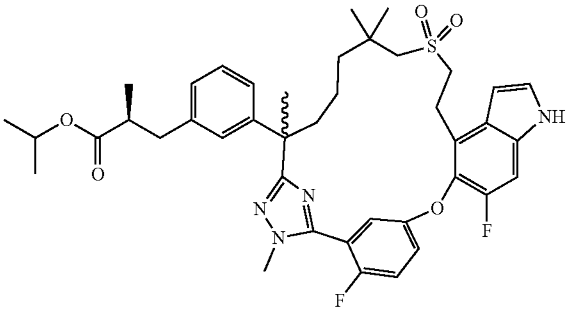 [SMILES: CC(C)OC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1]

To a stirred solution of diastereomer 1 of (2S)-3-[3-(22,28-Difluoro-3,6,10,10-tetramethyl-12,12-dioxo-24-oxa-12λ6-thia-3,4,19,30-tetrazapentacyclo[$23.3.1.1^{2,5}.0^{15,}$ $_{23}.0^{16,20}$]triaconta-1(29),2(30),4,15,17,20,22,25,27-nonaen-6-yl)phenyl]-2-methyl-propanoic acid (Example 7, 140.8 mg, 0.2 mmol) in iso-propanol (10 mL) was added concentrated sulfuric acid (0.2 mL). The reaction mixture was heated at 70° C. for 16 hours, then concentrated. The residue was dissolved with ethyl acetate (60 mL), washed with brine (10 mL), dried over sodium sulfate, and concentrated. The residue was purified by automated silica gel chromatography column (20 g silica gel column; eluted with ethyl acetate in petroleum ether 0-70%) to give the title compound (133.4 mg; yield 89%) as a white solid. MS (ESI): 747 m/z $[M+H]^+$, retention time: 2.24 minutes, purity: 99% (254 nm) (LC-MS Method 027). $^1H$ NMR (400 MHz, $CD_3OD$). δ 7.34-7.30 (m, 3H), 7.22-7.19 (m, 2H), 7.15 (t, J=8.0 Hz, 1H), 7.02 (d, J=8.0 Hz, 1H), 6.97-6.95 (m, 2H), 6.61 (d, J=3.2 Hz, 1H), 4.82-4.78 (m, 1H), 3.87 (d, J=2.0 Hz, 3H), 3.38-3.34 (m, 2H), 3.24-3.19 (m, 1H), 2.95 (d, J=13.6 Hz, 1H), 2.82-2.77 (m, 2H), 2.64-2.58 (m, 2H), 2.14 (td, J=12.4, 3.6 Hz, 1H), 1.80 (td, J=12.8, 4.8 Hz, 1H), 1.67 (s, 3H), 1.61-1.57 (m, 1H), 1.35-1.30 (m, 1H), 1.21-1.18 (m, 1H), 1.12 (d, J=6.4 Hz, 3H), 1.06-1.03 (m, 13H), 0.90-0.86 (m, 1H) ppm.

Example 140. Diastereomer 1 of 2-Hydroxyethyl (2S)-3-[3-(22,28-difluoro-3,6,10,10-tetramethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl)phenyl]-2-methyl-propanoate

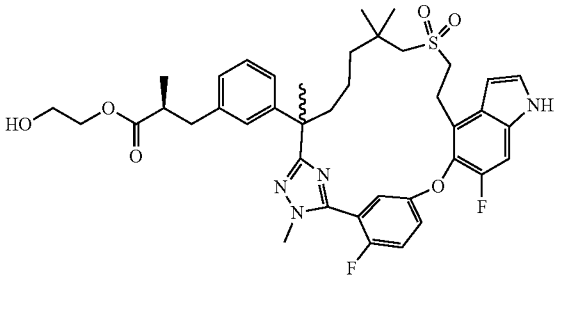 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCCO]

To a stirred solution of diastereomer 1 of (2S)-3-[3-(22,28-Difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic acid (Example 7, 147 mg, 0.21 mmol) and ethane-1,2-diol (261 mg, 4.2 mmol) in dichloromethane (10 mL) was added N-(3-dimethylamino-propyl)-N'-ethylcarbodiimide hydrochloride (60 mg, 0.3 mmol) and 4-dimethylaminopyridine (2.4 mg, 0.02 mmol). The mixture was stirred at room temperature overnight, diluted with water (15 mL), and extracted with ethyl acetate (3×15 mL). The extracts were washed with brine (10 mL), dried over sodium sulfate, and concentrated. The residue was purified by automated flash chromatography (12 g silica gel column, eluted with 0-25% ethyl acetate in petroleum ether) concentrated and lyophilized to give the title compound (100.5 mg; yield 64%) as white solid. MS (ESI): 749 m/z [M+H]$^+$, retention time: 2.01 minutes, purity: 99% (214 nm) (LC-MS Method 003). $^1$H NMR (400 MHz, $CD_3OD$). δ 7.34-7.30 (m, 3H), 7.22-7.14 (m, 3H), 7.03 (d, J=8.0 Hz, 1H), 6.98-6.96 (m, 2H), 6.61 (d, J=3.2 Hz, 1H), 4.02-3.98 (m, 2H), 3.85 (d, J=2.0 Hz, 3H), 3.59-3.56 (m, 2H), 3.38-3.33 (m, 4H), 3.24-3.18 (m, 1H), 2.95 (d, J=13.6 Hz, 1H), 2.88-2.85 (m, 1H), 2.80 (d, J=13.6 Hz, 1H), 2.73-2.61 (m, 2H), 2.14 (td, J=12.4, 3.6 Hz, 1H), 1.81 (td, J=12.8, 4.8 Hz, 1H), 1.67 (s, 3H), 1.62-1.56 (m, 1H), 1.33-1.29 (m, 1H), 1.22-1.18 (m, 1H), 1.06-1.05 (m, 9H) ppm.

Example 141. Diastereomer 1 of 2,3-Dihydroxypropyl (2S)-3-[3-(22,28-Difluoro-3,6,10,10-tetramethyl-12,12-dioxo-24-oxa-12λ6-thia-3,4,19,30-tetrazapentacyclo-[23.3.1.1$^{2,5}$.0$^{15,23}$.0$^{16,20}$]triaconta-1(29),2(30),4,15,17,20,22,25,27-nonaen-6-yl)phenyl]-2-methyl-propanoate

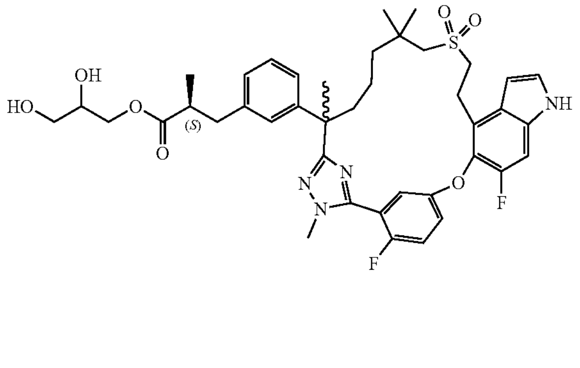

Diastereomer 1 of (2,2-Dimethyl-1,3-dioxolan-4-yl) methyl (2S)-3-[3-(22,28-Difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoate

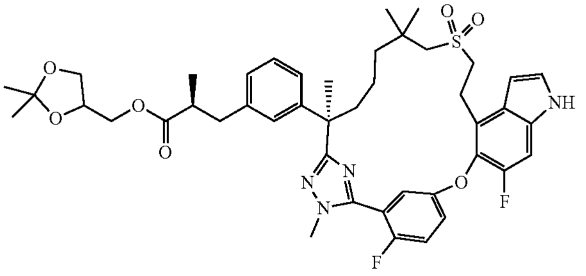 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3nc2nn3C)c1)C(=O)OCC1COC(C)(C)O1]

Step A: To a stirred solution of Diastereomer 1 of (2S)-3-[3-(22,28-Difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic acid (Example 7, 141 mg, 0.2 mmol) and (2,2-dimethyl-1,3-dioxolan-4-yl) methanol (132 mg, 1.0 mmol) in dichloromethane (10 mL) was added 4-dimethylaminopyridine (2.4 mg, 0.02 mmol) and N-(3-dimethylaminopropyl)-N'-ethylcarbodiimide hydrochloride (57 mg, 0.3 mmol). The mixture was stirred at room temperature for 16 hours, then quenched with water (30 mL), and extracted with ethyl acetate (3×25 mL). The extracts were washed with brine (20 mL), dried over sodium sulfate, and concentrated to give the title compound (150 mg, yield 92%) as solid. MS (ESI): 819 m/z [M+H]$^+$, retention time: 2.16 minutes, purity: 54% (214 nm) (LC-MS Method 017).

Compound 141: Diastereomer 1 of 2,3-Dihydroxypropyl (2S)-3-[3-(22,28-Difluoro-3,6,10,10-tetramethyl-12,12-dioxo-24-oxa-12λ6-thia-3,4,19,30-tetrazapentacyclo-[23.3.1.1$^{2,5}$.0$^{15,23}$.0$^{16,20}$]triaconta-1(29),2(30),4,15,17,20,22,25,27-nonaen-6-yl)phenyl]-2-methyl-propanoate

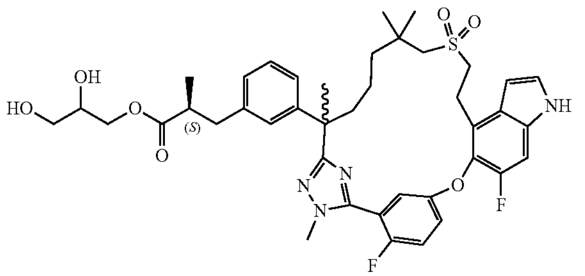

Step B: To a stirred solution of Step A product (150 mg, 0.18 mmol) in acetone (10 mL) was added 5 N hydrochloric acid (1 mL). The mixture was stirred at room temperature for 6 hours, then diluted with ethyl acetate (60 mL). The solution was washed with water, brine, dried over sodium sulfate, and concentrated. The residue was purified by automated silica gel column chromatography (20 g silica gel column; eluted with 0-100% ethyl acetate in petroleum ether) to give the title compound (55.1 mg; 39%) as a white solid. MS (ESI): 779 m/z [M+H]$^+$, retention time: 1.94 minutes, purity: 99% (214 nm) (LC-MS Method 003). $^1$H NMR (400 MHz, $CD_3OD$). δ 7.36-7.30 (m, 3H), 7.22-7.14 (m, 3H), 7.03-6.97 (m, 3H), 6.61 (d, J=3.2 Hz, 1H), 4.06-4.00 (m, 1H), 3.98-3.93 (m, 1H), 3.85 (d, J=2.0 Hz, 3H), 3.70-3.67 (m, 1H), 3.48-3.35 (m, 5H), 3.24-3.19 (m, 1H), 2.95 (d, J=13.6 Hz, 1H), 2.89-2.84 (m, 1H), 2.81 (d, J=13.6 Hz, 1H), 2.72-2.60 (m, 2H), 2.14 (td, J=12.8, 3.2 Hz, 1H), 1.81 (td, J=12.8, 3.6 Hz, 1H), 1.67 (s, 3H), 1.60-1.56 (m, 1H), 1.36-1.29 (m, 1H), 1.22-1.18 (m, 1H), 1.06-1.04 (m, 10H) ppm.

Example 142. Diastereomer 1 of 2-Morpholinoethyl (2S)-3-[3-(22,28-Difluoro-3,6,10,10-tetramethyl-12,12-dioxo-24-oxa-12λ6-thia-3,4,19,30-tetrazapentacyclo-[23.3.1.1$^{2,5}$.0$^{15,23}$.0$^{16,20}$]triaconta-1(29),2(30),4,15,17,20,22,25,27-nonaen-6-yl)phenyl]-2-methyl-propanoate

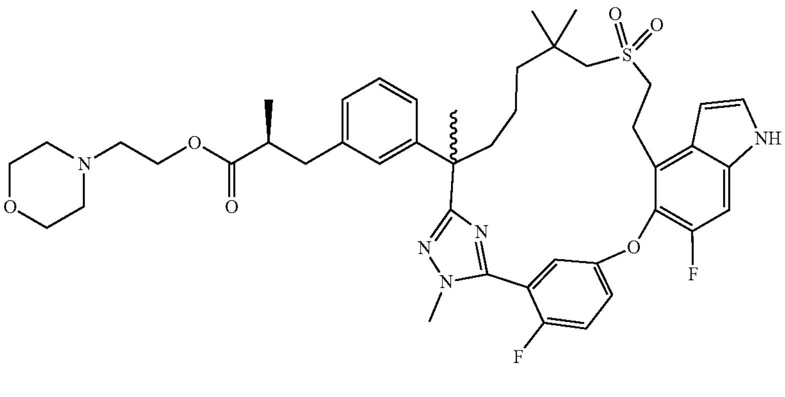 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCCN1CCOCC1]

To a stirred solution of diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic acid (Example 7, 147 mg, 0.21 mmol) and 2-morpholinoethan-1-ol (82.5 mg, 0.63 mmol) in dichloromethane (10 mL) were added N-(3-dimethylaminopropyl)-N'-ethylcarbodiimide hydrochloride (60 mg, 0.33 mmol) and 4-dimethylaminopyridine (2.4 mg, 0.02 mmol). The mixture was stirred at room temperature for 16 hours. The mixture was diluted with water (15 mL), extracted with ethyl acetate (3×15 mL). The combined organic extracts were washed with brine, dried over sodium sulfate, filtered, and concentrated. The residue was purified by automated flash chromatography (12 g silica gel column, eluted with 0-25% ethyl acetate in petroleum ether) to give the title compound (102.7 mg; yield 64%) as a white solid. MS (ESI): 818 m/z [M+H]$^+$, retention time: 1.66 minutes, purity: 99% (214 nm) (LC-MS Method 003). $^1$H NMR (400 MHz, $CD_3OD$). δ 7.35-7.31 (m, 3H), 7.22-7.20 (m, 2H), 7.15 (t, J=8.0 Hz, 1H), 7.03 (d, J=8.0 Hz, 1H), 6.98-6.96 (m, 2H), 6.61 (d, J=3.2 Hz, 1H), 4.10-4.03 (m, 2H), 3.86 (d, J=2.4 Hz, 3H), 3.62-3.60 (m, 4H), 3.38-3.35 (m, 2H), 3.25-3.20 (m, 1H), 2.95 (d, J=13.6 Hz, 1H), 2.82-2.79 (m, 2H), 2.70-2.62 (m, 2H), 2.51-2.46 (m, 2H), 2.3-2.37 (m, 4H), 2.14 (td, J=12.4, 3.2 Hz, 1H), 1.81 (td, J=12.4, 4.0 Hz, 1H), 1.67 (s, 3H), 1.62-1.56 (m, 1H), 1.35-1.27 (m, 2H), 1.22-1.16 (m, 1H), 1.06-1.05 (m, 10H) ppm.

Example 143. Diastereomer 1 of 2-(4-methylpiperazin-1-yl)ethyl (2S)-3-[3-(22,28-Difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoate

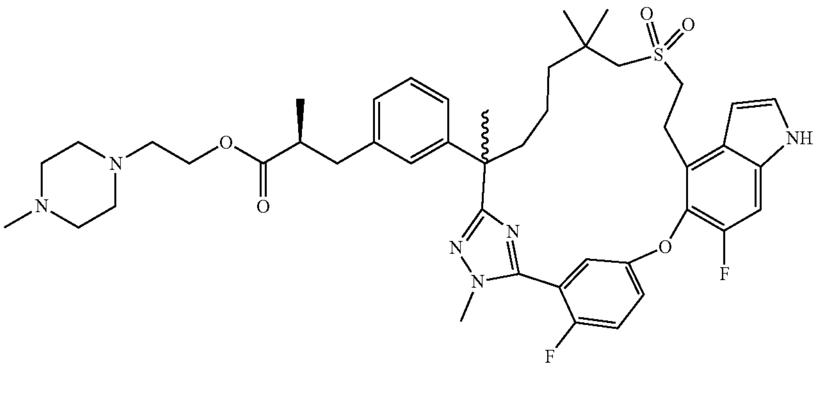 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCCN1CCN(C)CC1]

To a stirred solution of diastereomer 1 of (2S-3-[3-(22,28-Difluoro-3,6,10,10-tetramethyl-12,12-dioxo-24-oxa-12λ6-thia-3,4,19,30-tetrazapentacyclo[$23.3.1.1^{2,5}.0^{15,23}.0^{16,20}$]triaconta-1(29),2(30),4,15,17,20,22,25,27-nonaen-6-yl)phenyl]-2-methyl-propanoic acid (Example 7, 150 mg, 0.213 mmol) in dichloromethane (1.5 mL) was added 2-(4-methylpiperazin-1-yl)ethan-1-ol (37 mg, 0.26 mmol), N-(3-dimethylaminopropyl)-N'-ethylcarbodiimide hydrochloride (45 mg, 0.234 mmol), and 4-dimethylaminopyridine (2.6 mg, 0.0213 mmol). The resulting mixture was stirred at room temperature for 12 hours, then quenched with water (10 mL), and extracted with ethyl acetate (3×10 mL). The combined organic phases were washed with brine (30 mL), dried over sodium sulfate, filtered, and concentrated. The residue was purified by automated silica gel column chromatography (40 g silica gel column, eluted with 0 to 10% methanol in dichloromethane to give the title compound (108 mg, 60.5%). MS (ESI): 831 m/z $[M+H]^+$, retention time: 1.64 minutes, purity: >99% (214 nm) (LC-MS Method 003). $^1H$ NMR (400 MHz, $CD_3OD$) δ 7.37-7.28 (m, 3H), 7.22-7.13 (m, 3H), 7.03 (d, J=7.7 Hz, 1H), 6.97-6.95 (m, 2H), 6.61 (d, J=3.2 Hz, 1H), 4.10-4.00 (m, 2H), 3.85 (d, J=2.2 Hz, 3H), 3.40-3.20 (m, 2H), 3.28-3.19 (m, 2H), 2.94 (d, J=13.6 Hz, 1H), 2.85-2.78 (m, 2H), 2.70-2.60 (m, 2H), 2.60-2.40 (m, 6H), 2.40-2.29 (m, 4H), 2.20-2.10 (m, 1H), 1.82-1.78 (m, 1H), 1.66 (s, 3H), 1.63-1.50 (m, 1H), 1.40-1.25 (m, 4H), 1.26-1.15 (m, 2H), 1.06-1.03 (m, 10H) ppm.

Example 144. Diastereomer 1 of (2-Oxo-1,3-dioxol-4-yl)methyl (2S)-3-[3-(22,28-Difluoro-3,6,10,10-tetramethyl-12,12-dioxo-24-oxa-12λ6-thia-3,4,19,30-tetrazapentacyclo[$23.3.1.1^{2,5}.0^{15,23}.0^{16,20}$]triaconta-1(29),2(30),4,15,17,20,22,25,27-nonaen-6-yl)phenyl]-2-methyl-propanoate

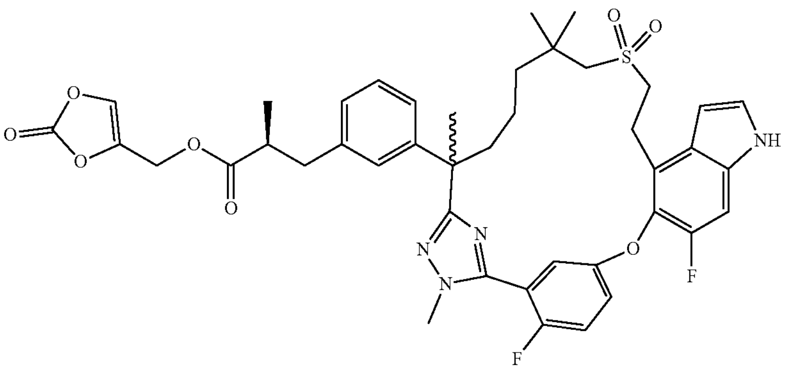 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCc1coc(=O)o1]

To a stirred solution of diastereomer 1 of (2S)-3-[3-(22,28-difluoro-3,6,10,10-tetramethyl-12,12-dioxo-24-oxa-12λ6-thia-3,4,19,30-tetrazapentacyclo[$23.3.1.1^{2,5}.0^{15,23}.0^{16,20}$]triaconta-1(29),2(30),4,15,17,20,22,25,27-nonaen-6-yl)phenyl]-2-methyl-propanoic acid (Example 7, 100 mg, 0.142 mmol) in acetone (5 mL) was added 4-(bromomethyl)-1,3-dioxol-2-one (30 mg, 0.168 mmol) and potassium carbonate (29 mg, 0.210 mmol) under argon. The mixture was stirred at room temperature for 24 hours, then quenched with sodium bicarbonate (10 mL), and extracted with ethyl acetate (2×10 mL). The combined organic extracts were washed with brine, dried over sodium sulfate, and concentrated. The residue was purified by silica gel chromatography (eluted with ethyl acetate in petroleum ether 0-60%) to give the title compound (67 mg, 58% yield) as a white solid. MS (ESI): 803 m/z $[M+H]^+$, retention time: 1.98 minutes, purity: 98% (214 nm) (LC-MS Method 034). $^1H$ NMR (500 MHz, DMSO-$d_6$) δ 11.34 (s, 1H), 7.76 (s, 1H), 7.48-7.39 (m, 2H), 7.32 (d, J=10.7 Hz, 1H), 7.29-7.23 (m, 2H), 7.11 (t, J=7.7 Hz, 1H), 7.00 (s, 1H), 6.94 (dd, J=11.9, 7.9 Hz, 2H), 6.51 (s, 1H), 4.88-4.83 (m, 2H), 3.78 (d, J=1.8 Hz, 3H), 3.31-3.27 (m, 1H), 3.25-3.08 (m, 3H), 2.98 (d, J=13.7 Hz, 1H), 2.82 (d, J=13.6 Hz, 1H), 2.80-2.75 (m, 1H), 2.73-2.65 (m, 1H), 2.62-2.50 (m, 1H), 2.10-2.05 (m, 1H), 1.73-1.64 (m, 1H), 1.61 (s, 3H), 1.55-1.45 (m, 1H), 1.29-1.13 (m, 2H), 1.02-0.96 (m, 10H) ppm.

Example 145. Diastereomer 1 of (Pivaloyloxy)methyl (2S)-3-[3-(22,28-Difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoate

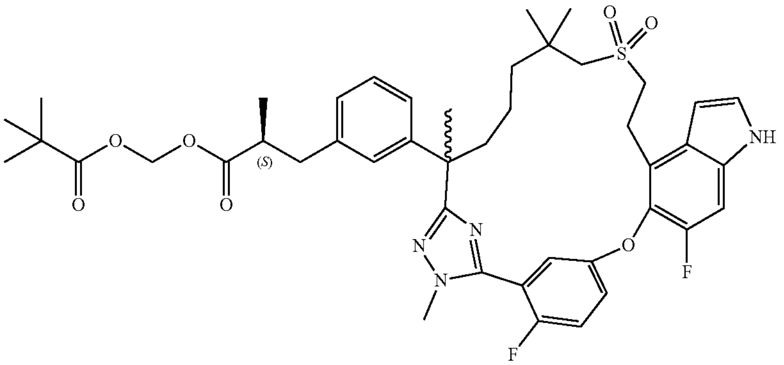

To the solution of Diastereomer 1 of (2S)-3-[3-(22,28-Difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic acid (Example 7, 1.00 eq, 100 mg, 0.142 mmol) in acetone (5 mL) was added chloromethyl pivalate (0.025 mL, 0.173 mmol), triethylamine (0.023 mL, 0.168 mmol) and potassium iodide (2.0 mg, 0.0120 mmol). The mixture was stirred at room temperature for 2 days, then quenched with saturated sodium bicarbonate (10 mL) and extracted with ethyl acetate (2×10 mL). The combined organic extracts were washed with brine, dried over sodium sulfate. The solvent was removed via evaporation. The residue was purified by silica gel column chromatography eluted with ethyl acetate in petroleum ether 0-60% to give the title compound (31 mg, 25.6%) as a white solid. MS (ESI): 819 m/z $[M+H]^+$, retention time: 2.14 minutes, purity: 98% (214 nm) (LC-MS Method 034). $^1$H NMR (500 MHz, $CD_3OD$) δ 7.34-7.31 (m, 3H), 7.23-7.18 (m, 2H), 7.15 (t, J=8.0 Hz, 1H), 7.03 (d, J=8.1 Hz, 1H), 7.00-6.97 (m, 2H), 6.61 (d, J=3.0 Hz, 1H), 5.67 (d, J=5.6 Hz, 1H), 5.61 (d, J=5.6 Hz, 1H), 3.85 (s, 3H), 3.41-3.33 (m, 2H), 3.27-3.14 (m, 2H), 2.95 (d, J=13.5 Hz, 1H), 2.90-2.86 (m, 1H), 2.80 (d, J=13.5 Hz, 1H), 2.70-2.60 (m, 2H), 2.16-2.07 (m, 1H), 1.86-1.79 (m, 1H), 1.67 (s, 3H), 1.62-1.52 (m, 1H), 1.37-1.24 (m, 2H), 1.16 (s, 9H), 1.08-1.06 (m, 10H) ppm.

Example 146. Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]-2-methyl-N-methylsulfonyl-propanamide

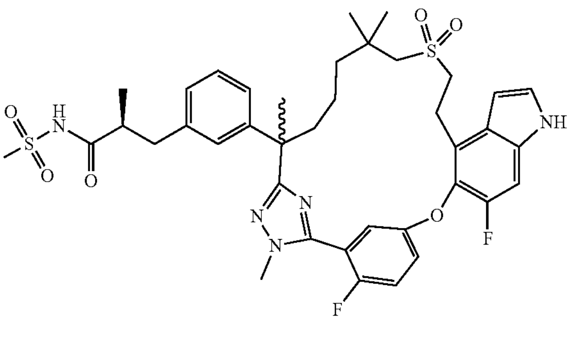 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NS(C)(=O)=O]

To a stirred solution of Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic acid (Example 7, 100 mg, 0.14 mmol) in dichloromethane (10 mL) were added triethylamine (28.3 mg, 0.28 mmol), methane sulfonamide (20 mg, 0.21 mmol), 1-ethyl-3-(3-dimethylaminopropyl)carbodiimide hydrochloride (26 mg, 0.17 mmol), and 4-dimethylaminopyridine (5.1 mg, 0.04 mmol). The reaction mixture was stirred at room temperature overnight. The solvent was removed. The residue was purified by Prep-HPLC to give the title compound (37 mg, 37%) as a solid. MS (ESI): 782 m/z $[M+H]^+$, retention time: 1.89 minutes, purity: 98% (214 nm) (LC-MS Method 003). $^1$H NMR (400 MHz, $CD_3OD$) δ 7.36-7.34 (m, 2H), 7.30 (d, 1H), 7.22-7.16 (m, 3H), 7.07-6.98 (m, 3H), 6.61 (d, J=4.0 Hz, 1H), 3.86 (d, J=4.0 Hz, 3H), 3.38-3.34 (m, 2H), 3.27-3.23 (m, 1H), 2.95 (s, 3H), 2.91 (d, J=12.0 Hz, 1H), 2.85-2.76 (m, 2H), 2.66-2.61 (m, 2H), 2.15-2.10 (m, 1H), 1.88-1.81 (m, 1H), 1.67 (s, 3H), 1.50-1.43 (m, 1H), 1.34-1.19 (m, 3H), 1.09 (d, J=8.0 Hz, 3H), 1.05 (s, 3H), 1.04 (s, 3H), 0.98-0.93 (m, 1H) ppm.

Example 147. Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17 20,22,25,27-nonaen-6-yl)phenyl]-N-methoxy-2-methyl-propanamide

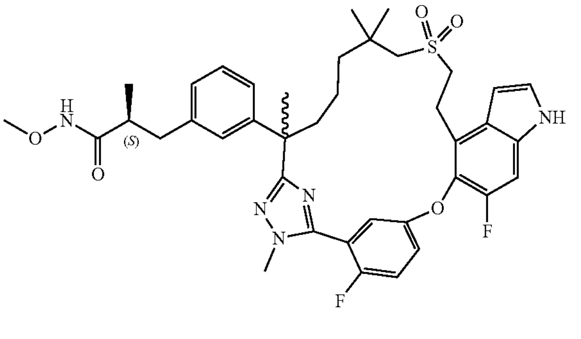

To the stirred solution of Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.$1^{2,5}$.$0^{15,23}$.$0^{16,20}$]triaconta-1(29),2(30),4,15,17,20,22,25,27-nonaen-6-yl)phenyl]-2-methyl-propanoic acid (Example 7, 150 mg, 0.213 mmol) in dichloromethane (10 mL) were added 1-(3-dimethylaminopropyl)-3-ethylcarbodiimide hydrochloride (49 mg, 0.256 mmol), 1-hydroxybenzotriazole (28 mg, 0.207 mmol), O-methylhydroxylamine hydrochloride (35 mg, 0.419 mmol), N,N-diisopropylethylamine (0.0040 mL, 0.0232 mmol), 4-dimethylaminopyridine (81 mg, 0.663 mmol). The mixture was stirred at room temperature for 1 hour, then quenched with sodium bicarbonate solution (10 mL). The mixture was extracted with dichloromethane (3×10 mL). The combined extracts were washed with brine, dried over sodium sulfate, filtered, and concentrated. The residue was purified with prep-HPLC to give the title compound (74 mg, 47%) as a white solid. MS (ESI): 734 m/z $[M+H]^+$, retention time: 1.93 minutes, purity: 98% (214 nm) (LC-MS Method 003). $^1H$ NMR (400 MHz, $CD_3OD$) δ 7.39-7.30 (m, 3H), 7.25-7.13 (m, 3H), 7.05 (d, J=8.1 Hz, 1H), 7.01-6.95 (m, 2H), 6.63 (d, J=3.2 Hz, 1H), 3.87 (d, J=1.9 Hz, 3H), 3.46 (s, 3H), 3.42-3.36 (m, 2H), 3.31-3.16 (m, 2H), 2.89 (d, J=13.6 Hz, 1H), 2.83-2.74 (m, 2H), 2.63-2.57 (m, 1H), 2.37-2.26 (m, 1H), 2.20-2.12 (m, 1H), 1.90-1.80 (m, 1H), 1.69 (s, 3H), 1.62-1.47 (m, 1H), 1.37-1.18 (m, 2H), 1.11 (d, J=6.8 Hz, 3H), 1.09-0.94 (m, 7H) ppm.

Example 148. Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]-N-(2,3-dihydroxypropoxy)-2-methyl-propanamide

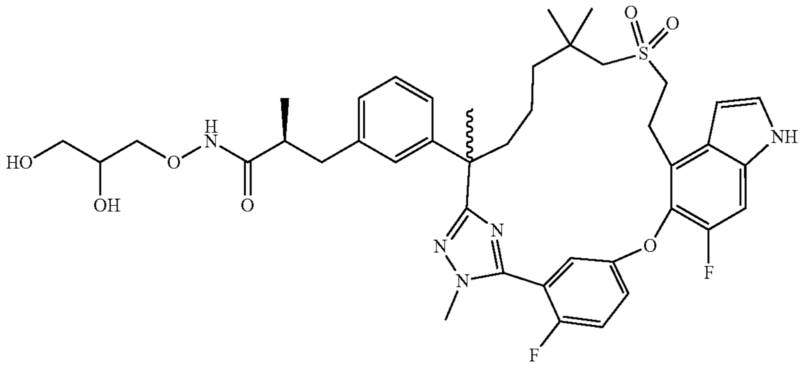 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NOCC(O)CO]

Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-N-[(2,2-dimethyl-1,3-dioxolan-4-yl)methoxy]-2-methyl-propanamide

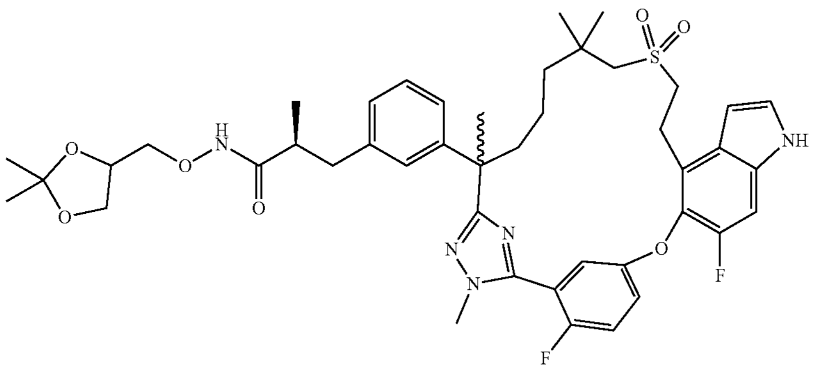 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NOCC1COC(C)(C)O1]

To a stirred solution of Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic acid (Example 7, 100 mg, 0.15 mmol) in dichloromethane (10 mL) was added O-((2,2-dimethyl-1,3-dioxolan-4-yl)methyl)hydroxylamine (110 mg, 0.75 mmol), N,N-diisopropylethylamine (59 mg, 0.45 mmol), N-(3-dimethylaminopropyl)-N'-ethylcarbodiimide hydrochloride (43 mg, 0.25 mmol) and 1-hydroxybenzotriazole (33 mg, 0.25 mmol). The mixture was stirred at room temperature for 16 hours, then quenched with water (30 mL), and extracted with ethyl acetate (3×25 mL). The combined organic extracts were washed with sodium bicarbonate, brine, dried over sodium sulfate, filtered, and concentrated to give the title compound (115 mg, 92%) as a solid. MS (ESI): 834 m/z [M+H]$^+$, retention time: 2.00 minutes, purity: 91% (214 nm) (LC-MS Method 003).

Compound 148: Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]-N-(2,3-dihydroxypropoxy)-2-methyl-propanamide

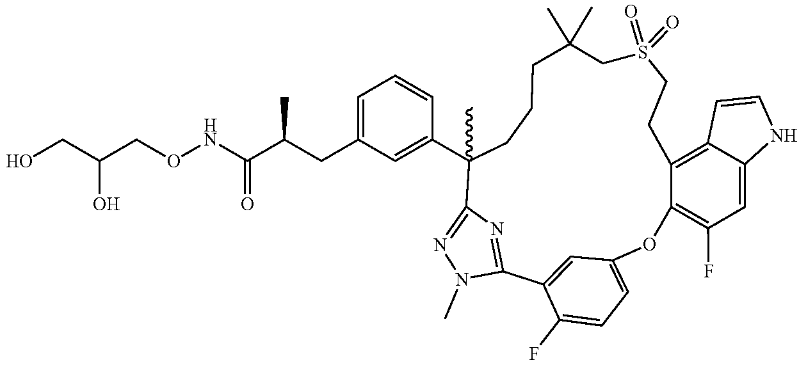 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NOCC(O)CO]

To a stirred solution of (2S)-3-[3-(22,28-difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic acid (Example 7, 108 mg, 0.013 mmol) in acetone (5 mL) was added 5N hydrochloric acid (1 mL). The mixture was stirred at room temperature for 2 hours, then diluted with ethyl acetate (60 mL). The solution was washed with water, brine, dried over sodium sulfate, filtered, and concentrated. The residue was purified by automated silica gel column chromatography (20 g silica gel column; eluted with 0-100% ethyl acetate in petroleum ether) to give the title compound (33 mg; yield 32%) as a white solid. MS (ESI): 794 m/z [M+H]$^+$, retention time: 1.82 minutes, purity: >99% (214 nm) (LC-MS Method 027). $^1$H NMR (400 MHz, $CD_3OD$). δ 7.38-7.31 (m, 3H), 7.23-7.14 (m, 3H), 7.03 (d, J=7.2 Hz, 1H), 6.97-6.96 (m, 2H), 6.61 (d, J=3.2 Hz, 1H), 3.85 (d, J=2.0 Hz, 3H), 3.71-3.65 (m, 2H), 3.62-3.57 (m, 1H), 3.50-3.47 (m, 2H), 3.38-3.36 (m, 2H), 3.24-3.17 (m, 1H), 2.89 (d, J=13.6 Hz, 1H), 2.81-2.76 (m, 2H), 2.64-2.57 (m, 1H), 2.38-2.30 (m, 1H), 2.17-2.11 (m, 1H), 1.86-1.80 (m, 1H), 1.67 (s, 3H), 1.55-1.51 (m, 1H), 1.29-1.20 (m, 3H), 1.11-1.00 (m, 10H) ppm.

Example 149. Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]-N,2-dimethyl-propanamide

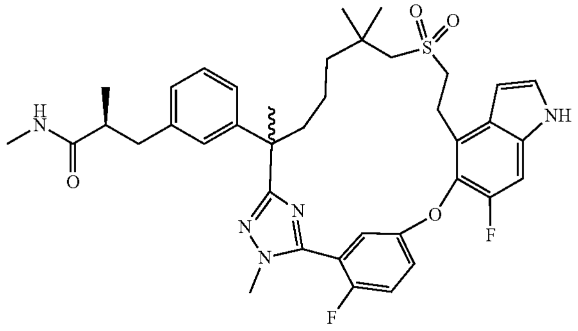 [SMILES: CNC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1]

To a stirred solution of Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.1$^{2,5}$.0$^{15,23}$.0$^{16,20}$]triaconta-1(29),2(30),4,15,17,20,22,25,27-nonaen-6-yl)phenyl]-2-methyl-propanoic acid (Example 7, 150 mg, 0.213 mmol) in dichloromethane (10 mL) were added 1-(3-dimethylaminopropyl)-3-ethylcarbodiimide hydrochloride (49 mg, 0.256 mmol), 1-hydroxybenzotriazole (28 mg, 0.207 mmol), methylamine hydrochloride (28 mg, 0.415 mmol), N,N-diisopropylethylamine (0.0040 mL, 0.0232 mmol), and 4-dimethylaminopyridine (81 mg, 0.663 mmol). The mixture was stirred at room temperature for 1 hour, then quenched with saturated sodium bicarbonate (10 mL) and extracted with dichloromethane (3×10 mL). The combined organic extracts were washed with brine, dried over sodium sulfate. After removal of solvent, the residue was purified by prep-HPLC to give the title compound (97 mg, 63%) as a white solid. MS (ESI): 718 m/z [M+H]$^+$, retention time: 1.93 minutes, purity: 98% (214 nm) (LC-MS Method 034). $^1$H NMR (400 MHz, $CD_3OD$) δ 7.39-7.30 (m, 3H), 7.26-7.13 (m, 3H), 7.05-6.94 (m, 3H), 6.64 (d, J=3.2 Hz, 1H), 3.87 (d, J=1.4 Hz, 3H), 3.44-3.36 (m, 2H), 3.31-3.13 (m, 2H), 2.93-2.71 (m, 3H), 2.60 (s, 3H), 2.58-2.41 (m, 2H), 2.25-2.08 (m, 1H), 1.90-1.80 (m, 1H), 1.68 (s, 3H), 1.62-1.48 (m, 1H), 1.37-1.19 (m, 2H), 1.09-1.00 (m, 10H) ppm.

Example 150. Diastereomer 1 of (2S)—N-cyclopropylsulfonyl-3-[3-(22,28-difluoro-3,6,10,10-tetramethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl) phenyl]-2-methyl-propanamide

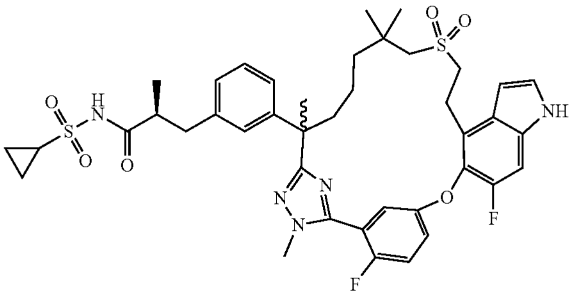 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NS(=O)(=O)C1CC1]

To a stirred solution of (2S)-3-[3-(22,28-difluoro-3,6,10,10-tetramethyl-12,12-dioxo-24-oxa-12λ6-thia-3,4,19,30-tetrazapentacyclo[23.3.1.$1^{2,5}$.$0^{15,23}$.$0^{16,20}$]triaconta-1(29),2(30),4,15,17,20,22,25,27-nonaen-6-yl)phenyl]-2-methyl-propanoic acid (Example 7, 150 mg, 0.213 mmol) in dichloromethane (5 mL) was added cyclopropane sulfonamide (31 mg, 0.255 mmol) triethylamine (0.059 mL, 0.426 mmol), 4-dimethylaminopyridine (7.8 mg, 0.0638 mmol) and 1-(3-dimethylaminopropyl)-3-ethylcarbodiimide hydrochloride (49 mg, 0.255 mmol). The mixture was stirred at room temperature overnight. The solvent was evaporated, and the residue was purified by prep-HPLC to give the title compound (94 mg, 0.116 mmol, yield 54.67%) as a solid. MS (ESI): 808 m/z $[M+H]^+$, retention time: 1.93 minutes, purity: 98% (214 nm) (LC-MS Method 034). $^1H$ NMR (400 MHz, $CD_3OD$) δ 7.36-7.32 (m, 2H), 7.30 (d, J=3.2 Hz, 1H), 7.23-7.15 (m, 3H), 7.08-7.02 (m, 2H), 6.99 (d, J=7.6 Hz, 1H), 6.61 (d, J=3.2 Hz, 1H), 3.85 (d, J=2.0 Hz, 3H), 3.42-3.33 (m, 2H), 3.26-3.19 (m, 1H), 2.92 (d, J=13.6 Hz, 1H), 2.85-2.71 (m, 3H), 2.66-2.58 (m, 2H), 2.18-2.09 (m, 1H), 1.89-1.79 (m, 1H), 1.67 (s, 3H), 1.53-1.45 (m, 1H), 1.38-1.11 (m, 4H), 1.09 (d, J=6.8 Hz, 3H), 1.06 (s, 3H), 1.04 (s, 3H), 1.01-0.94 (m, 3H), 0.89-0.83 (m, 1H) ppm.

Example 151. (2S)-3-[3-(3-Cyano-23,29-difluoro-11,11-dimethyl-13,13-dioxo-25-oxa-13λ6-thia-5,6,20-triazapentacyclo[24.3.1.02,6.016,24.017,21]triaconta-1(30),2,4,16,18,21,23,26,28-nonaen-7-yl) phenyl]-2-methyl-propanoic Acid

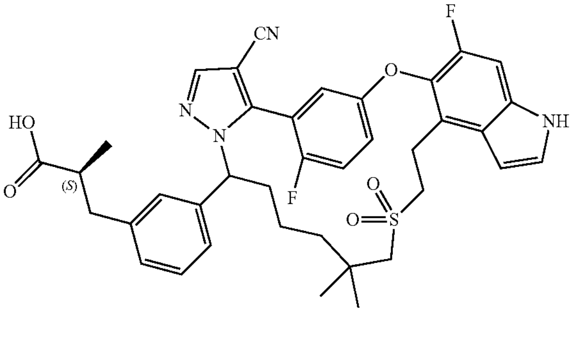

and

Example 152. (2S)-3-[3-(3-Cyano-22,28-difluoro-10,10-dimethyl-12,12-dioxo-24-oxa-12λ6-thia-5,19,30-triazapentacyclo[23.3.1.12,5.015,23.016,20]triaconta-1(29),2(30),3,15,17,20,22,25,27-nonaen-6-yl) phenyl]-2-methyl-propanoic Acid

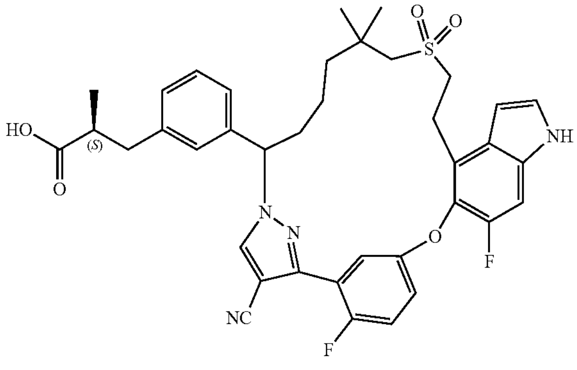

Exchanging ethyl 3-(3-(6-mercapto-5,5-dimethyl-1-((tetrahydro-2H-pyran-2-yl)oxy)hexyl)phenyl)propanoate (Step A product of Example 22) with ethyl (2S)-3-(3-(6-mercapto-5,5-dimethyl-1-((tetrahydro-2H-pyran-2-yl)oxy)hexyl)phenyl)-2-methylpropanoate (Intermediate 33-2, 2 g, 4.58 mmol), the reaction procedure sequence (Steps B to F) described for Example 22 was used to prepare the title compounds. The two regio-isomers were separated by prep-HPLC in Step F. The first eluent, a mixture of diastereomers, is designated as Compound 151 (15.6 mg); The second eluent, a mixture of diastereomers, is designated as Compound 152 (25.2 mg).

Compound 151: MS (ESI): 701 m/z $[M+H]^+$, retention time: 1.87 minutes, purity: >99% (214 nm) (LC-MS Method 003). $^1H$ NMR (400 MHz, $CD_3OD$) δ 8.08 (s, 1H), 7.40-7.20 (m, 7H), 7.16-7.13 (m, 1H), 7.00-6.89 (m, 1H), 6.60 (d, J=2.8 Hz, 1H), 5.16-5.11 (m, 1H), 3.48-3.21 (m, 3H), 3.19-3.10 (m, 1H), 3.04-2.91 (m, 3H), 2.72-2.61 (m, 2H), 2.43-2.28 (m, 1H), 2.04-1.91 (m, 1H), 1.61-1.50 (m, 1H), 1.33-1.23 (m, 1H), 1.20-0.94 (m, 10H), 0.90-0.78 (m, 1H) ppm.

Compound 152: MS (ESI): 701 m/z $[M+H]^+$, retention time: 1.87 minutes, purity: >99% (214 nm) (LC-MS Method 003). $^1H$ NMR (400 MHz, $CD_3OD$) δ 8.22 (s, 1H), 7.34-7.31 (m, 2H), 7.30-7.23 (m, 3H), 7.21-7.14 (m, 3H), 7.16-7.11 (m, 1H), 6.64-6.63 (m, 1H), 5.43 (d, J=11.2 Hz, 1H), 3.44-3.40 (m, 2H), 3.20-3.13 (m, 2H), 2.99-2.91 (m, 1H), 2.70-2.62 (m, 4H), 2.35-2.25 (m, 1H), 1.94-1.87 (m, 1H), 1.43-1.31 (m, 2H), 1.15-1.08 (m, 8H), 0.99 (s, 3H) ppm.

Example 153. Diastereomers 1, 2, and 3 of 2-[[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]-3-methoxy-propanoic Acid

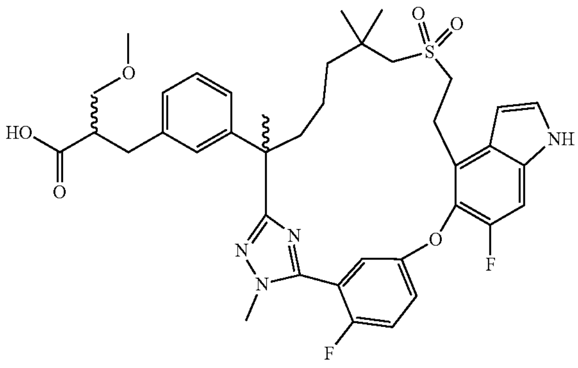 [SMILES: COCC(Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl 2-(3-(7-((2-hydroxyethyl)sulfonyl)-2,6,6-trimethyl-1-(2-methylhydrazineyl)-1-oxoheptan-2-yl)benzyl)-3-methoxypropanoate (Intermediate 69-19, 1.6 g, 3.1 mmol) in Step A, the reaction procedure sequence (Steps A to G) described for Example 6 was used to prepare the title compounds. The racemic ester (240 mg), obtained in corresponding Step D of Example 6, was subject to chiral separation, as described in corresponding Step E in Example 6, using chiral prep-HPLC under the following conditions: Column: Chiralpak IC 50*250 mm, 10 μm; Column temperature: 38° C.; Mobile phase: hexane/ethanol=80/20 (V/V); Flow rate: 30 mL/minutes; Detection wavelength: 254 nm; Sample solution: 0.5 mg/mL in mobile phase; Injection volume: 20 mL. The first eluent (90 mg, 38%), diastereomer 1 (most likely a mixture of two diastereomers), was further hydrolyzed to Compound 153A (77.4 mg, 88%). The second eluent (45 mg, 19%), enantiomer 2, was further hydrolyzed to Compound 153B (40 mg, 90%). The third eluent (45 mg, 19%), enantiomer 3, was further hydrolyzed to Compound 153C (40 mg, 90%), as described in corresponding Step F of Example 6.

Compound 153A: MS (ESI): 735 m/z $[M+H]^+$, retention time: 1.88 minutes, purity: 99% (214 nm). (LC-MS Method 003). $^1$H NMR (400 MHz, $CD_3OD$) δ 7.36-7.28 (m, 3H), 7.23-7.13 (m, 3H), 7.06-6.97 (m, 3H), 6.61 (d, J=3.2 Hz, 1H), 3.85 (d, J=1.6 Hz, 3H), 3.49-3.35 (m, 4H), 3.28-3.14 (m, 5H), 2.92-2.72 (m, 5H), 2.17-2.09 (m, 1H), 1.86-1.78 (m, 1H), 1.67 (s, 3H), 1.61-1.53 (m, 1H), 1.35-1.29 (m, 2H), 1.22-1.15 (m, 1H), 1.05 (s, 3H), 1.04 (s, 3H) ppm.

Compound 153B: MS (ESI): 735 m/z $[M+H]^+$, retention time: 1.88 minutes, purity: 99% (214 nm). (LC-MS Method 003). $^1$H NMR (400 MHz, CD3OD) δ 7.35-7.28 (m, 3H), 7.23-7.13 (m, 3H), 7.07-6.97 (m, 3H), 6.61 (d, J=2.4 Hz, 1H), 3.85 (d, J=1.6 Hz, 3H), 3.49-3.35 (m, 4H), 3.28-3.14 (m, 5H), 2.92-2.72 (m, 5H), 2.17-2.09 (m, 1H), 1.86-1.78 (m, 1H), 1.67 (s, 3H), 1.61-1.53 (m, 1H), 1.35-1.29 (m, 2H), 1.22-1.15 (m, 1H), 1.05 (s, 3H), 1.04 (s, 3H) ppm.

Compound 153C: MS (ESI): 735 m/z $[M+H]^+$, retention time: 1.88 minutes, purity: 99% (214 nm). (LC-MS Method 003). $^1$H NMR (400 MHz, CD3OD) δ 7.35-7.28 (m, 3H), 7.23-7.14 (m, 3H), 7.07-6.97 (m, 3H), 6.61 (d, J=3.6 Hz, 1H), 3.85 (d, J=2.0 Hz, 3H), 3.50-3.35 (m, 4H), 3.27-3.14 (m, 5H), 2.92-2.72 (m, 5H), 2.17-2.09 (m, 1H), 1.86-1.78 (m, 1H), 1.67 (s, 3H), 1.61-1.53 (m, 1H), 1.35-1.29 (m, 2H), 1.22-1.15 (m, 1H), 1.05 (s, 3H), 1.04 (s, 3H) ppm.

Example 154. 3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenol

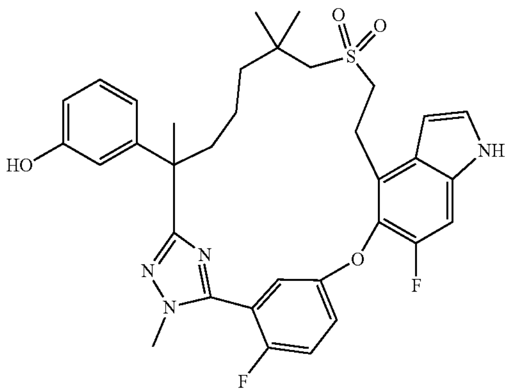

Exchanging methyl (2R)-3-(3-(7-((2-hydroxyethyl)sulfonyl)-2,6,6-trimethyl-1-(2-methyl-hydrazineyl)-1-oxoheptan-2-yl)phenyl)-2-methylpropanoate (intermediate 69) with 2-(3-(benzyloxy)phenyl)-7-((2-hydroxyethyl)sulfonyl)-N',2,6,6-tetramethylheptanehydrazide (intermediate 69-20, 6.5 g, 13.2 mmol) in Step A, the title compound (2.2 g) was prepared following the reaction sequence (Steps A-D) as described for Example 6. MS (ESI): 635 m/z $[M+H]^+$, retention time: 1.85 minutes, purity: >99% (214 nm). (LC-MS Method 034). $^1$H NMR (400 MHz, $CD_3OD$) δ 7.35-7.28 (m, 3H), 7.22-7.18 (m, 2H), 7.05 (t, J=8.0 Hz, 1H), 6.67-6.55 (m, 4H), 3.85 (d, J=2.3 Hz, 3H), 3.40-3.36 (m, 2H), 3.27-3.15 (m, 2H), 2.87 (d, J=13.6 Hz, 1H), 2.76 (d, J=13.6 Hz, 1H), 2.14-2.07 (m, 1H), 1.84-1.76 (m, 1H), 1.65 (s, 3H), 1.63-1.52 (m, 1H), 1.35-1.10 (m, 3H), 1.05 (s, 3H), 1.04 (s, 3H) ppm.

Example 155. (E)-3-[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-but-2-enoic Acid

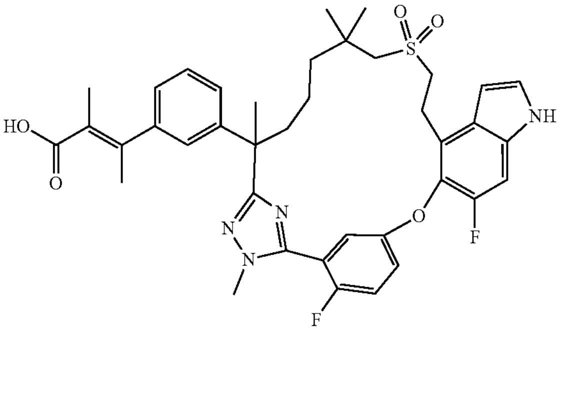

[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl] trifluoromethanesulfonate

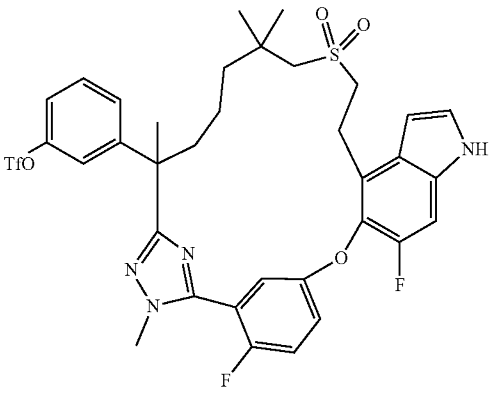 [SMILES: Cn1nc2nc1-c1cc(ccc1F)Oc1c(F)cc3[nH]ccc3c1CCS(=O)(=O)CC(C)(C)CCCC2(C)c1cccc(OS(=O)(=O)C(F)(F)F)c1]

Step A: To a stirred solution of Example 154 (2 g, 13.9 mmol) in dichloromethane (20 mL) was added N,N-diisopropylethylamine (5 mL, 27.8 mmol) and trifluoromethanesulfonic anhydride (2.3 mL, 21 mmol). The reaction mixture was stirred at room temperature for 5 hours, then quenched with water (20 mL), and extracted with dichloromethane (2×30 mL). The combined organic extracts were washed with brine (100 mL), dried over sodium sulfate, filtered, and concentrated. The residue was purified by flash chromatography (25 g silica gel column, eluted with 0-30% ethyl acetate in petroleum ether) to give the title compound (1.4 g, 53%) as an oil. MS (ESI): 767 m/z $[M+H]^+$, retention time: 2.08 minutes, purity: 93% (214 nm). (LC-MS Method 034).

Ethyl (E)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-but-2-enoate

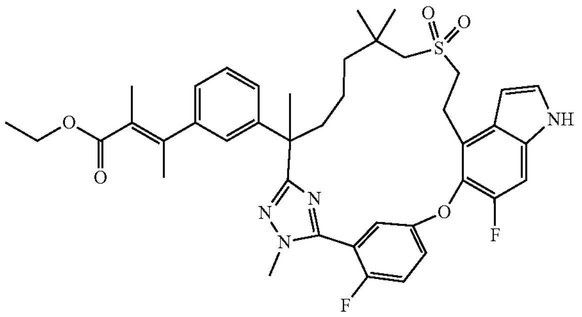 [SMILES: CCOC(=O)/C(C)=C(\C)c1cccc(C2(C)CCCC(C)(C)CS(=O)(=O)CCc3c(c(F)cc4[nH]ccc34)Oc3ccc(F)c(c3)-c3nc2nn3C)c1]

Step B: To a stirred solution of Step A product (1.2 g, 1.6 mmol) in dimethylformamide (10 mL) was added ethyl (E)-2-methyl-3-(4,4,5,5-tetramethyl-1,3,2-dioxaborolan-2-yl)but-2-enoate (Intermediate 126, 0.6 g, 2.3 mmol) and 1,1'-bis(diphenylphosphino)ferrocene-palladium(II)dichloride dichloromethane complex (0.25 g, 0.32 mmol). The reaction mixture was stirred at 100° C. for 5 hours. The mixture was diluted with ethyl acetate (50 mL), washed with water, brine, dried over sodium sulfate, and concentrated. The residue was purified by automated flash chromatography (25 g silica gel column, eluted with 0-30% ethyl acetate in petroleum) to give the title compound (730 mg, 73%) as a white solid. MS (ESI): 745 m/z $[M+H]^+$, retention time: 2.12 minutes, purity: 93% (214 nm) (LC-MS Method 034).

Compound 155. (E)-3-[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-but-2-enoic Acid

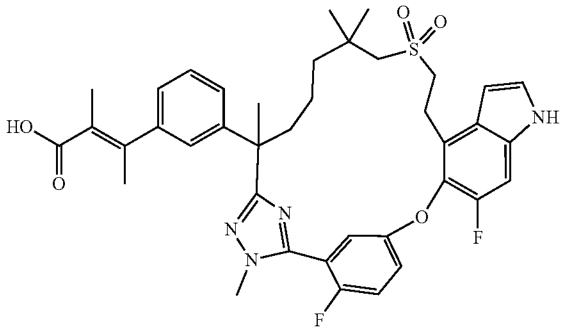 [SMILES: C/C(C(=O)O)=C(/C)c1cccc(C2(C)CCCC(C)(C)CS(=O)(=O)CCc3c(c(F)cc4[nH]ccc34)Oc3ccc(F)c(c3)-c3nc2nn3C)c1]

Step C: To a stirred solution of Step B product (50 mg, 0.07 mmol) in methanol (0.6 mL), water (0.2 mL) and tetrahydrofuran (0.2 mL) was added lithium hydroxide monohydrate (8.4 mg, 0.2 mmol). The reaction mixture was stirred at room temperature for 5 hours, then diluted with water (10 mL), and acidified to pH ~5 with 1N hydrochloric acid. The mixture was extracted with ethyl acetate (3×10 mL). The combined organic extracts were washed with brine, dried over sodium sulfate, filtered, and concentrated. The residue was purified by prep-HPLC to give the title compound (35 mg, yield: 73%) as solid. MS (ESI): 717 m/z $[M+H]^+$, retention time: 1.94 minutes, purity: 97% (214 nm). (LC-MS Method 034). $^1H$ NMR (400 MHz, $CD_3OD$) δ 7.36-7.26 (m, 4H), 7.22-7.16 (m, 2H), 7.15-7.11 (m, 1H), 6.99-6.95 (m, 1H), 6.93-6.90 (m, 1H), 6.61 (d, J=2.7 Hz, 1H), 3.87 (d, J=2.0 Hz, 3H), 3.40-3.25 (m, 3H), 3.23-3.15 (m, 1H), 2.94 (d, J=13.6 Hz, 1H), 2.81 (m, J=13.6 Hz, 1H), 2.20-2.10 (m, 4H), 1.90-1.82 (m, 1H), 1.69 (s, 3H), 1.64-1.54 (m, 4H), 1.40-1.28 (m, 1H), 1.26-1.20 (m, 2H), 1.051 (s, 3H), 1.055 (s, 3H) ppm.

Example 156. 3-[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-butanoic Acid

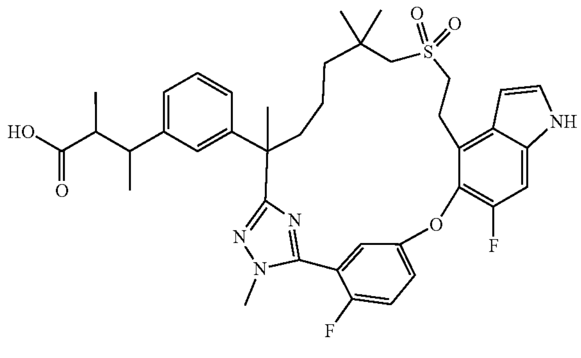 [SMILES: CC(C(=O)O)C(C)c1cccc(C2(C)CCCC(C)(C)CS(=O)(=O)CCc3c(c(F)cc4[nH]ccc34)Oc3ccc(F)c(c3)-c3nc2nn3C)c1]

Ethyl 3-[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-butanoate

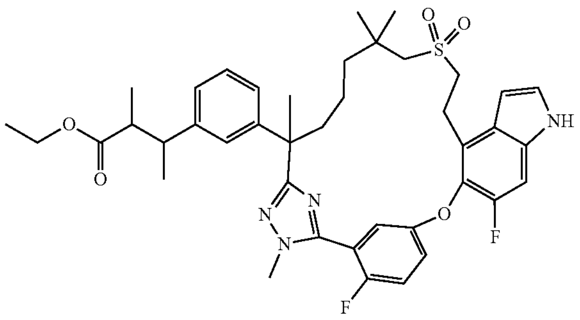

Step A: To a stirred solution of Step B product of Example 155 (360 mg, 0.483 mmol) in ethanol (20 mL) was added palladium on carbon (50% wet, 10%, 100 mg). The reaction mixture was stirred under hydrogen at 50° C. for 4 hours. The mixture was filtered through a pad of Celite and washed with ethanol (10 mL). The filtrate was concentrated to give the title compound (315 mg, yield: 88%) as a solid. MS (ESI): 747 m/z $[M+H]^+$, retention time: 2.11 minutes, purity: 98% (214 nm) (LC-MS Method 034).

Compound 156: 3-[3-(22,28-Difluoro-3,6,10,10-tetramethyl-12,12-dioxo-24-oxa-1216-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-butanoic acid

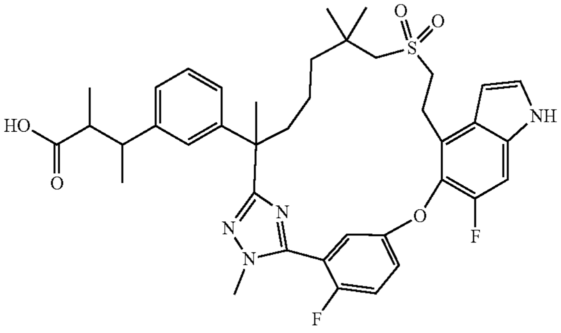 [SMILES: CC(C(=O)O)C(C)c1cccc(C2(C)CCCC(C)(C)CS(=O)(=O)CCc3c(c(F)cc4[nH]ccc34)Oc3ccc(F)c(c3)-c3nc2nn3C)c1]

Step B: To a stirred solution of Step B product (15 mg, 0.02 mmol) in tetrahydrofuran/methanol/water (V/V/V=3/1/1, 1 mL) was added lithium hydroxide monohydrate (4.2 mg, 0.1 mmol). The reaction was stirred at room temperature overnight, then acidified with 1.0 M hydrochloric acid to pH ~5. The mixture was extracted with ethyl acetate (3×10 mL). The combined organic phases were washed with brine, dried over sodium sulfate, and concentrated. The residue was purified by prep-HPLC to give the title compound (7 mg, 48%) as a white solid. MS (ESI): 719 m/z $[M+H]^+$, retention time: 1.94 minutes, purity: 97% (214 nm). (LC-MS Method 003). $^1H$ NMR (400 MHz, CD3OD) δ 7.36-7.29 (m, 3H), 7.22-7.11 (m, 3H), 7.07-6.94 (m, 3H), 6.60 (d, J=3.2 Hz, 1H), 3.89-3.80 (s, 3H), 3.39-3.34 (m, 2H), 3.24-3.16 (m, 1H), 3.01-2.92 (m, 2H), 2.88-2.71 (m, 2H), 2.59-2.49 (m, 1H), 2.18-2.10 (m, 1H), 1.83-1.74 (m, 1H), 1.67 (s, 3H), 1.62-1.56 (m, 1H), 1.38-1.28 (m, 4H), 1.19-1.14 (m, 2H), 1.09-0.99 (m, 9H) ppm.

Example 157. Diastereomer 1 and 2 of (2R)-3-[3-(22,28-difluoro-6,10,10-trimethyl-12,12-dioxo-24-oxa-12λ6-thia-3,19,30-triazapentacyclo-[23.3.1.12,5.015,23.016,20]triaconta-1(29),2(30),4,15,17,20,22,25,27-nonaen-6-yl)phenyl]-2-methyl-propanoic Acid

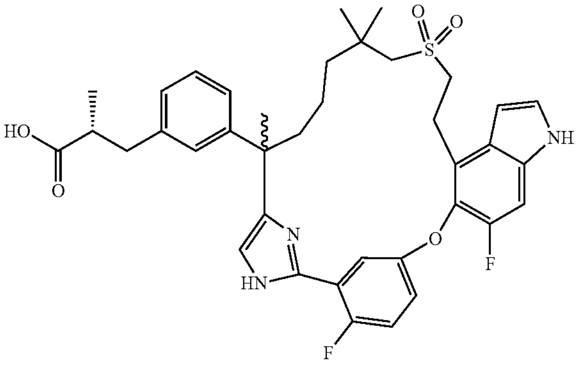 [SMILES: C[C@H](Cc1cccc(C2(C)CCCC(C)(C)CS(=O)(=O)CCc3c(c(F)cc4[nH]ccc34)Oc3ccc(F)c(c3)-c3nc2c[nH]3)c1)C(=O)O]

Exchanging methyl (2S)-3-(3-(1-bromo-8-((2-((tert-butyldiphenylsilyl)oxy)ethyl)sulfonyl)-3,7,7-trimethyl-2-oxooctan-3-yl)phenyl)-2-methylpropanoate (Intermediate 17-14) with methyl (2R)-3-(3-(1-bromo-8-((2-((tert-butyldiphenylsilyl)oxy)ethyl)sulfonyl)-3,7,7-trimethyl-2-oxooctan-3-yl)phenyl)-2-methylpropanoate (Intermediate 17-15, 22 g, 28.5 mmol), the reaction sequence procedure (Steps A to C) described for Example 129 was used to prepare the title compounds. The corresponding SFC chiral separation conditions are as follow: Instrument: SFC-80 (Thar, Waters); Column: AD 20*250 mm, 10 μm; Column temperature: 35° C.; Mobile phase: carbon dioxide/isopropanol (0.2% methanol ammonia as additive)=60/40; Flow rate: 80 g/minute; Back pressure: 100 bar; Detection wavelength: 214 nm; Cycle time: 5.5 minutes; Sample solution: 1400 mg methyl ester dissolved in 65 ml methanol; Injection volume: 1.9 mL. The first eluent, enantiomer 1 (490 mg, 35%), was further hydrolyzed to Compound 157A (476.6 mg, 99%); The second eluent, enantiomer 2 (500 mg, 36%), was further hydrolyzed to Compound 157B (480.7 mg, 98%).

Compound 157A: MS (ESI): 690 m/z $[M+H]^+$, retention time: 1.63 minutes, purity: 98% (214 nm). (LC-MS Method 003). $^1H$ NMR (500 MHz, $CD_3OD$) δ 7.53 (dd, J=5.5, 3.0 Hz, 1H), 7.34-7.29 (m, 2H), 7.26-7.24 (m, 2H), 7.19-7.16 (m, 2H), 7.08 (s, 1H), 7.04-7.01 (m, 2H), 6.62 (d, J=3.0 Hz, 1H), 3.45-3.32 (m, 3H), 3.13-3.07 (m, 1H), 2.95-2.90 (m, 1H), 2.90-2.74 (m, 2H), 2.65-2.59 (m, 2H), 2.14-2.09 (m, 1H), 1.99-1.94 (m, 1H), 1.58 (s, 3H), 1.42-1.28 (m, 3H), 1.15 (s, 3H), 1.08 (d, J=6.5 Hz, 3H), 0.95 (s, 3H), 0.87-0.79 (m, 1H) ppm. Chiral purity: e.e. %=99.4% (Chiral-HPLC Method: Column: (R,R) Whelk-O1 4.6*100 mm 3.5 μm; Mobile: carbon dioxide/methanol [0.2% ammonia (7 M in methanol) as additive]; Injection volume: 5.00 uL; Channel name: PDA Ch2 254 nm @4.8 nm; Run time: 3.0 minutes; Flow rate: 3.0 mL/minutes; Back pressure: 2000 psi; Column Temperature: 40° C. Retention time=1.730 minutes, 99.7% (254 nm)).

Compound 157B: MS (ESI): 690 m/z $[M+H]^+$, retention time: 1.63 minutes, purity: 97% (214 nm). (LC-MS Method 003). $^1$H NMR (500 MHz, $CD_3OD$) δ 7.54 (dd, J=5.0, 3.0 Hz, 1H), 7.41-7.35 (m, 3H), 7.29 (d, J=3.5 Hz, 1H), 7.22-7.16 (m, 2H), 7.08 (s, 1H), 7.05-7.02 (m, 2H), 6.63 (d, J=3.5 Hz, 1H), 3.47-3.31 (m, 3H), 3.16-3.11 (m, 1H), 2.96-2.80 (m, 3H), 2.67-2.62 (m, 2H), 2.18-2.12 (m, 1H), 2.05-1.99 (m, 1H), 1.59 (s, 3H), 1.57-1.52 (m, 1H), 1.37-1.27 (m, 2H), 1.19 (s, 3H), 1.10 (d, J=6.0 Hz, 3H), 0.94 (s, 3H), 0.83-0.77 (m, 1H) ppm. Chiral purity: e.e. %=99.4% (retention time: 1.49 minutes; same method as Compound 157A) Example 158. Diastereomer 1 of (2S)-3-[3-(22,28-Difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]-2-methyl-propanamide

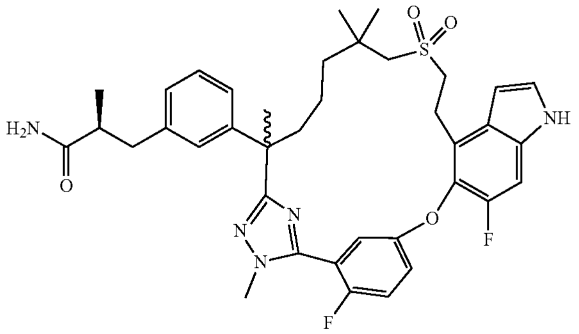 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(N)=O]

To a stirred solution of Diastereomer 1 of (2S)-3-[3-(22,28-Difluoro-3,6,10,10-tetramethyl-12,12-dioxo-24-oxa-12λ6-thia-3,4,19,30-tetrazapentacyclo[$23.3.1.1^{2,5}.0^{15,23}.0^{16,20}$]triaconta-1(29),2(30),4,15,17,20,22,25,27-nonaen-6-yl)phenyl]-2-methyl-propanoic acid (Example 7, 100 mg, 0.14 mmol) in N,N-dimethylformamide (2 mL) was added ammonium chloride (38 mg, 0.709 mmol), 1-(3-dimethylaminopropyl)-3-ethylcarbodiimide hydrochloride (33 mg, 0.170 mmol) and 1-hydroxybenzotriazole (23 mg, 0.170 mmol), N,N-diisopropylethylamine (0.049 mL, 0.284 mmol). The mixture was stirred at room temperature overnight. The mixture was purified by prep-HPLC to give the title compound (60 mg, 60%) as a solid. MS (ESI): 704 m/z $[M+H]^+$, retention time: 1.83 minutes, purity: 98% (214 nm) (LC-MS Method 034). $^1$H NMR (400 MHz, $CD_3OD$) δ 7.36-7.28 (m, 3H), 7.23-7.11 (m, 3H), 7.03-6.95 (m, 3H), 6.61 (d, J=3.2 Hz, 1H), 3.85 (d, J=2.4 Hz, 3H), 3.41-3.34 (m, 2H), 3.27-3.13 (m, 2H), 2.91-2.75 (m, 3H), 2.60-2.51 (m, 2H), 2.17-2.09 (m, 1H), 1.87-1.78 (m, 1H), 1.67 (s, 3H), 1.60-1.51 (m, 1H), 1.29-1.26 (m, 1H), 1.23-1.16 (m, 1H), 1.10-0.96 (m, 10H) ppm.

Example 159. Methyl 4-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-butanoate

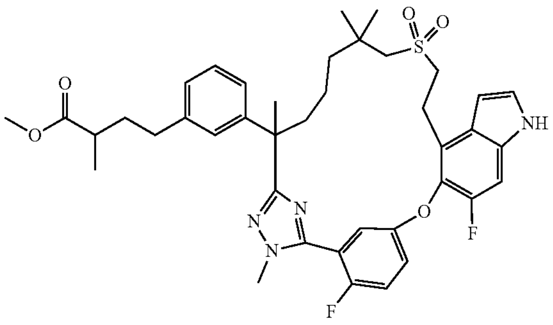 [SMILES: COC(=O)C(C)CCc1cccc(C2(C)CCCC(C)(C)CS(=O)(=O)CCc3c(c(F)cc4[nH]ccc34)Oc3ccc(F)c(c3)-c3nc2nn3C)c1]

Methyl 4-(3-(2-(5-(5-((4-bromo-6-fluoro-1H-indol-5-yl)oxy)-2-fluorophenyl)-1-methyl-1H-1,2,4-triazol-3-yl)-7-((2-((tert-butyldiphenylsilyl)oxy)ethyl)sulfonyl)-6,6-dimethylheptan-2-yl)phenyl)-2-methylbutanoate

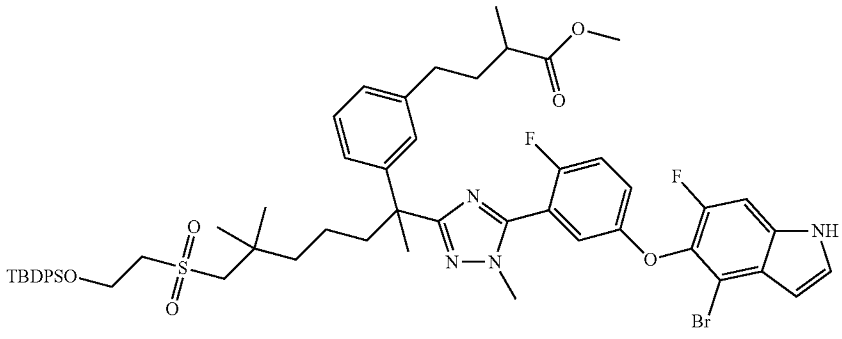

Step A: To a stirred solution of methyl 4-(3-(7-((2-((tert-butyldiphenylsilyl)oxy)ethyl)sulfonyl)-2,6,6-trimethyl-1-(2-methylhydrazineyl)-1-oxoheptan-2-yl)phenyl)-2-methylbutanoate (Intermediate 129, 5.0 g, 6.78 mmol) and methyl 5-((4-bromo-6-fluoro-1H-indol-5-yl)oxy)-2-fluorobenzimidothioate hydroiodide (Intermediate 14-1, 4.27 g, 8.14 mmol) in pyridine (40 mL) was added magnesium sulphate (3.26 g, 27.1 mmol). The mixture was stirred at 80° C. for 16 hours, cooled to room temperature, poured into 100 mL of water, and extracted with ethyl acetate (3×150 mL). The combined organic phases were washed with 1 N hydrochloric acid, brine, dried over sodium sulfate, and concentrated. The residue was purified by automated flash chromatography (120 g silica gel column, eluted with 0-65% ethyl acetate in petroleum ether) to give the title compound (5.0 g, 69%) as a light-yellow solid. MS (ESI): 1067, 1069 m/z [M+H]$^+$, retention time: 1.73 minutes, purity: 96% (214 nm) (LC-MS Method 033).

Methyl 4-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylbutanoate

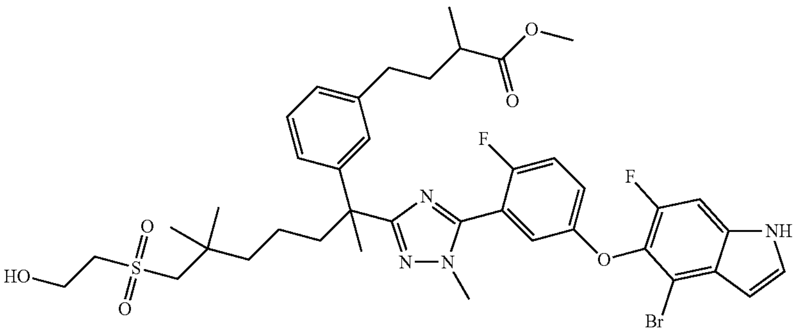 [SMILES: COC(=O)C(C)CCc1cccc(C(C)(CCCC(C)(C)CS(=O)(=O)CCO)c2nc(-c3cc(Oc4c(F)cc5[nH]ccc5c4Br)ccc3F)n(C)n2)c1]

Step B: To a stirred solution of Step A product (5.0 g, 4.68 mmol) in tetrahydrofuran (15 mL) was added tetra-n-butylammonium fluoride (1.0 M in tetrahydrofuran, 18.7 mL, 18.7 mmol). The reaction was stirred at room temperature for 2 hours, then diluted with ethyl acetate (50 mL). The solution was washed with water, dried over sodium sulfate, and concentrated. The residue was purified by automated flash chromatography (80 g silica gel column, eluted with 0-85% ethyl acetate in petroleum) to give the title compound (3.2 g, 93%) as a light-yellow oil. MS (ESI): 829, 831 m/z [M+H]$^+$, retention time: 2.09 minutes, purity: 93% (214 nm) (LC-MS Method 003).

Compound 159: Methyl 4-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-butanoate

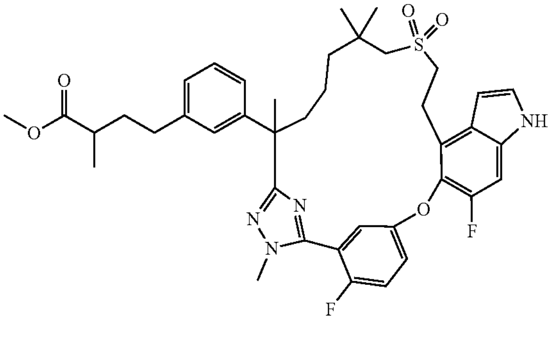 [SMILES: COC(=O)C(C)CCc1cccc(C2(C)CCCC(C)(C)CS(=O)(=O)CCc3c(c(F)cc4[nH]ccc34)Oc3ccc(F)c(c3)-c3nc2nn3C)c1]

Step C: Exchanging Methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 6) with methyl 4-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylbutanoate (Step B product of this example, 3.2 g, 3.86 mmol), the reaction procedure sequence (Steps B to D) described for Example 6 was used to prepare the title compound (1.8 g). MS (ESI): 733 m/z [M+H]$^+$, retention time: 2.08 minutes, purity: >99% (214 nm). (LC-MS Method 003). $^1$H NMR (500 MHz, $CD_3OD$) δ 7.35-7.29 (m, 3H), 7.22-7.18 (m, 2H), 7.17-7.12 (m, 1H), 7.00-6.96 (m, 3H), 6.60 (d, J=3.0 Hz, 1H), 3.85 (d, J=2.0 Hz, 3H), 3.60 (d, J=3.0 Hz, 3H), 3.39-3.33 (m, 2H), 3.28-3.17 (m, 2H), 2.95-2.91 (m, 1H), 2.80 (t, J=13.0 Hz, 1H), 2.53-2.50 (m, 2H), 2.41-2.35 (m, 1H), 2.16-2.10 (m, 1H), 1.90-1.78 (m, 2H), 1.67 (s, 3H), 1.64-1.57 (m, 2H), 1.34-1.29 (m, 1H), 1.21-1.15 (m, 1H), 1.11-0.99 (m, 10H).

Example 160. 4-[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-butanoic Acid

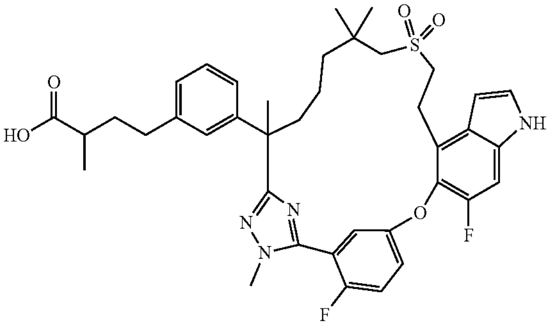 [SMILES: CC(CCc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

To a solution of Example 159 (100 mg, 0.136 mmol) in tetrahydrofuran (1.0 mL), methanol (1.0 mL) and water (0.5 mL) was added lithium hydroxide monohydrate (114 mg, 2.73 mmol). The reaction was stirred at room temperature for 3 hours, then acidified with 1.0 M hydrochloric acid to pH ~6. The mixture was extracted with ethyl acetate (3×10 mL). The combined organic phases were washed with brine, dried over sodium sulfate, filtered, and concentrated to give the title compound (80 mg, 80%) as a white solid. MS (ESI):

719 m/z $[M+H]^+$, retention time: 2.02 minutes, purity: 96% (214 nm). (LC-MS Method 003). $^1H$ NMR (500 MHz, $CD_3OD$) δ 7.34-7.28 (m, 3H), 7.21-7.17 (m, 2H), 7.15 (t, J=7.5 Hz, 1H), 7.03-6.92 (m, 3H), 6.60 (d, J=3.0 Hz, 1H), 3.85 (d, J=1.5 Hz, 3H), 3.40-3.33 (m, 2H), 3.28-3.15 (m, 2H), 2.94-2.90 (m, 1H), 2.81-2.77 (m, 1H), 2.57-2.53 (m, 2H), 2.37-2.32 (m, 1H), 2.17-2.11 (m, 1H), 1.92-1.79 (m, 2H), 1.67 (s, 3H), 1.63-1.55 (m, 2H), 1.35-1.28 (m, 1H), 1.21-1.15 (m, 1H), 1.11-1.00 (m, 10H) ppm.

Example 161. Ethyl (2S)-3-[3-(22-fluoro-10,10-dimethyl-12,12,24-trioxo-12λ6-thia-5,19,30-triaza-pentacyclo[23.3.1.12,5.015,23.016,20]triaconta-1(29),2(30),3,15,17,20,22,25,27-nonaen-6-yl)phenyl]-2-methyl-propanoate

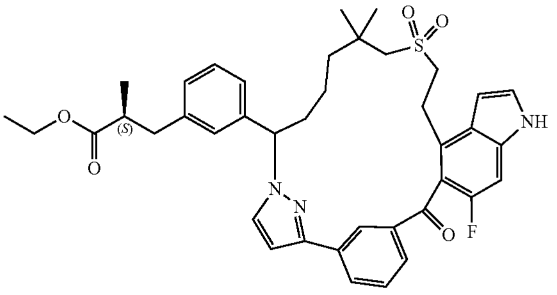

and

Example 162. Ethyl (2S)-3-[3-(23-fluoro-11,11-dimethyl-13,13,25-trioxo-13λ6-thia-5,6,20-triaza-pentacyclo[24.3.1.02,6.016,24.017,21]triaconta-1(30),2,4,16,18,21,23,26,28-nonaen-7-yl)phenyl]-2-methyl-propanoate

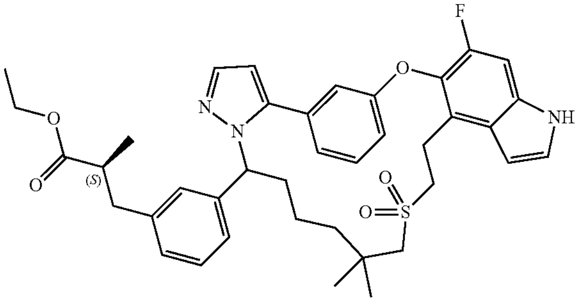

and

Example 163. (2S)-3-[3-(22-Fluoro-10,10-dimethyl-12,12,24-trioxo-12λ6-thia-5,19,30-triazapentacyclo[23.3.1.12,5.015,23.016,20]triaconta-1(29),2(30),3,15,17,20,22,25,27-nonaen-6-yl)phenyl]-2-methyl-propanoic Acid

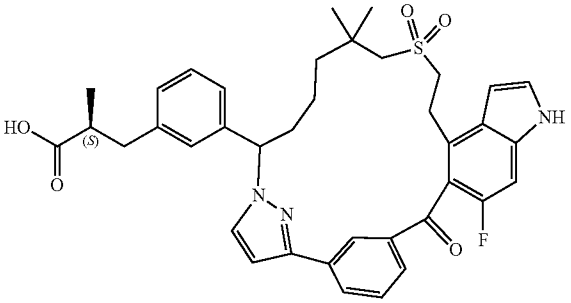

Exchanging 3-(2-fluoro-5-((6-fluoro-4-vinyl-1H-indol-5-yl)oxy)phenyl)-1-(tetrahydro-2H-pyran-2-yl)-1H-pyrazole-4-carbonitrile (Intermediate 52) with (6-fluoro-1-(triisopropylsilyl)-4-vinyl-1H-indol-5-yl)(3-(1-(tetrahydro-2H-pyran-2-yl)-1H-pyrazol-5-yl)phenyl)methanone (Intermediate 130, 1.2 g, 2.13 mmol) and ethyl 3-(3-(6-mercapto-5,5-dimethyl-1-((tetrahydro-2H-pyran-2-yl)oxy)hexyl)phenyl)propanoate (Step A product of Example 22) with ethyl (2S)-3-(3-(6-mercapto-5,5-dimethyl-1-((tetrahydro-2H-pyran-2-yl)oxy)hexyl)phenyl)-2-methylpropanoate (Intermediate 33-2, 0.99 g, 2.13 mmol), the reaction procedure sequence (Steps B to F) described for Example 22 was used to prepare the title compounds, with a change of reaction order. The new reaction order is: First step: Step B (thiol addition) condition of Example 22 was used; Second Step: Step E (thioether oxidation) condition of Example 22; Third Step: Step C (tetrahydropyran deprotection) condition of Example 22; Fourth Step: Step D (macrocyclization) condition of Example 22; Fifth Step: Step F (hydrolysis) condition of Example 22 was used. The two regio-isomers, Compound 161 (11 mg, first eluent), Compound 162 (13 mg, second eluent), are separated at fourth Step (Step D condition of Example 22) by prep-HPLC. Compound 161 (98 mg) was further hydrolyzed to Compound 163 (7.5 mg, 8%) as described in Step F of Example 22.

Compound 161: MS (ESI): 698 m/z $[M+H]^+$, retention time: 2.07 minutes, purity: >99% (214 nm). (LC-MS Method 003). $^1H$ NMR (400 MHz, $CD_3OD$) δ 8.38 (s, 1H), 8.04 (t, J=8.0 Hz, 2H), 7.67 (t, J=8.0 Hz, 1H), 7.54 (s, 1H), 7.38 (d, J=3.2 Hz, 1H), 7.28-7.20 (m, 2H), 7.09-7.03 (m, 3H), 6.77 (d, J=3.2 Hz, 1H), 6.72 (d, J=2.4 Hz, 1H), 5.32-5.28 (m, 1H), 4.02-3.95 (m, 2H), 3.55-3.42 (m, 2H), 3.11-3.08 (m, 2H), 2.88-2.84 (m, 1H), 2.72-2.67 (m, 2H), 2.42 (d, J=2.0 Hz, 2H), 2.26-2.19 (m, 1H), 1.83-1.82 (m, 1H), 1.31-1.24 (m, 4H), 1.12-1.02 (m, 9H), 0.90 (s, 3H) ppm.

Compound 162: MS (ESI): 698 m/z $[M+H]^+$, retention time: 2.08 minutes, purity: 95% (214 nm). (LC-MS Method 003). $^1H$ NMR (400 MHz, $CD_3OD$) δ 8.04 (s, 1H), 7.96 (d, J=5.6 Hz, 1H), 7.67-7.63 (m, 2H), 7.57 (t, J=8.0 Hz, 1H), 7.48 (d, J=7.2 Hz, 1H), 7.36 (d, J=3.2 Hz, 1H), 7.24 (d, J=10.0 Hz, 1H), 7.16-7.14 (m, 2H), 7.12 (d, J=6.0 Hz, 1H), 6.70 (d, J=3.2 Hz, 1H), 6.46 (d, J=1.6 Hz, 1H), 5.21-5.17 (m, 1H), 4.05-3.98 (m, 2H), 3.48-3.46 (m, 1H), 3.27-3.18 (m, 3H), 2.93-2.89 (m, 1H), 2.77-2.69 (m, 4H), 2.39-2.35 (m, 1H), 2.04-2.00 (m, 1H), 1.35-1.26 (m, 3H), 1.18-1.14 (m, 4H), 1.14-1.09 (m, 3H), 1.07 (d, J=2.0 Hz, 3H), 0.84 (d, J=2.8 Hz, 3H) ppm.

Compound 163: MS (ESI): 670 m/z $[M+H]^+$, retention time: 1.87 minutes, purity: >99% (214 nm). (LC-MS Method 003). $^1$H NMR (400 MHz, $CD_3OD$) δ 8.28 (s, 1H), 8.08 (d, J=7.2 Hz, 1H), 7.78 (d, J=7.6 Hz, 1H), 7.68-7.66 (m, 1H), 7.59 (t, J=7.6 Hz, 1H), 7.42 (d, J=3.2 Hz, 1H), 7.18-7.17 (m, 3H), 7.04-7.02 (m, 1H), 6.72-6.70 (m, 2H), 6.37 (d, J=15.6 Hz, 1H), 6.23-6.17 (m, 1H), 3.42-3.38 (m, 4H), 3.29-3.28 (m, 2H), 3.07 (s, 2H), 3.02-2.95 (m, 1H), 2.72-2.61 (m, 2H), 2.20-2.14 (m, 2H), 1.63-1.59 (m, 2H), 1.19 (s, 6H), 1.14 (d, J=6.8 Hz, 3H) ppm.

Example 164. (2R)-3-[3-(22-Fluoro-10,10-dimethyl-12,12,24-trioxo-12λ6-thia-5,19,30-triazapentacyclo[23.3.1.12,5.015,23.016,20]triaconta-1(29),2(30),3,15,17,20,22,25,27-nonaen-6-yl)phenyl]-2-methyl-propanoic acid

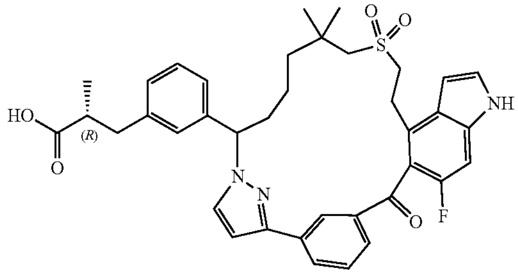

Exchanging ethyl (2S)-3-(3-(6-mercapto-5,5-dimethyl-1-((tetrahydro-2H-pyran-2-yl)oxy)hexyl)phenyl)-2-methyl-propanoate (Intermediate 33-2) with ethyl (2R)-3-(3-(6-mercapto-5,5-dimethyl-1-((tetrahydro-2H-pyran-2-yl)oxy)hexyl)phenyl)-2-methylpropanoate (Intermediate 33-3, 1.1 g, 2.52 mmol), the reaction procedure sequence (from first to fifth steps) described for Example 163 was used to prepare the title compound (19.7 mg) as a light-yellow solid. MS (ESI): 670 m/z $[M+H]^+$, retention time: 1.86 minutes, purity: >99% (214 nm). (LC-MS Method 003). $^1$H NMR (400 MHz, $CD_3OD$) δ 8.28 (s, 1H), 8.08-8.06 (m, 1H), 7.78 (d, J=7.6 Hz, 1H), 7.66 (d, J=2.4 Hz, 1H), 7.59 (t, J=7.6 Hz, 1H), 7.42 (d, J=3.6 Hz, 1H), 7.19-7.14 (m, 3H), 7.04 (d, J=6.8 Hz, 1H), 6.72-6.69 (m, 2H), 6.37 (d, J=16.0 Hz, 1H), 6.22-6.17 (m, 1H), 3.42-3.38 (m, 4H), 3.33-3.01 (m, 2H), 3.06 (s, 2H), 3.01-2.96 (m, 1H), 2.70-2.59 (m, 2H), 2.19-2.14 (m, 2H), 1.63-1.59 (m, 2H), 1.18 (s, 6H), 1.13 (d, J=6.8 Hz, 3H) ppm.

Example 165. Diastereomer 1 of 2-[2-(2-Methoxy-ethoxy)ethoxy]ethyl (2S)-3-[3-[22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

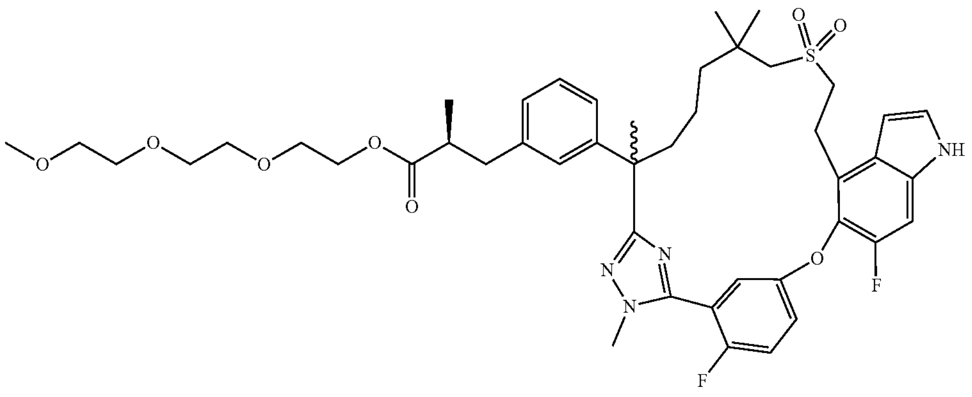 [SMILES: COCCOCCOCCOC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1]

To a stirred solution of Diastereomer 1 of ethyl (2S)-3-[3-[(6R)-22,28-difluoro-3,6,10,10-tetramethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl]phenyl]-2-methyl-propanoic acid (Example 7, 100 mg, 0.142 mmol) in dichloromethane (1.5 mL) was added N-(3-dimethylaminopropyl)-N'-ethylcarbodiimide hydrochloride (30 mg, 0.156 mmol), 2-(2-(2-methoxy-ethoxy)ethoxy)ethan-1-ol (35 mg, 0.21 mmol), and 4-dimethylaminopyridine (1.7 mg, 0.0142 mmol). The mixture was stirred at room temperature for 6 hours, then quenched with water (10 mL), and extracted with ethyl acetate (3×10 mL). The organic phases were washed with brine, dried over sodium sulfate, and concentrated. The residue was purified by automated silica gel column chromatography (40 g silica gel column, eluted with 0 to 10% methanol in dichloromethane to give the title compound (58 mg, 47%) as a white solid. MS (ESI): 851 m/z $[M+H]^+$, retention time: 2.0 minutes, purity: >99% (214 nm) (LC-MS Method 003). $^1$H NMR (400 MHz, $CD_3OD$) δ 7.35-7.28 (m, 3H), 7.22-7.11 (m, 3H), 7.02 (d, J=7.9 Hz, 1H), 9.98-6.94 (m, 2H), 6.60 (d, J=3.0 Hz, 1H), 4.10-4.03 (m, 2H), 3.84 (d, J=2.1 Hz, 3H), 3.60-3.53 (m, 8H), 3.52-3.48 (m, 2H), 3.42-3.26 (m, 6H), 3.24-3.20 (m, 1H), 2.94 (d, J=13.6 Hz, 1H), 2.87-2.76 (m, 2H), 2.70-2.56 (m, 2H), 2.18-2.09 (m, 1H), 1.84-1.70 (m, 1H), 1.66 (s, 3H), 1.67-1.50 (m, 1H), 1.34-1.15 (m, 3H), 1.04-0.90 (m, 9H) ppm.

Example 166. Enantiomers 1 and 2 of (E)-3-[3-(22,28-difluoro-3,6,10,10-tetramethyl-12,12-dioxo-12λ6-thia-3,4,19,30-tetrazapentacyclo-[23.3.1.12,5.015,23.016,20]triaconta-1(29),2(30),4,15,17,20,22,25,27-nonaen-6-yl)phenyl]-2-methyl-prop-2-enoic Acid

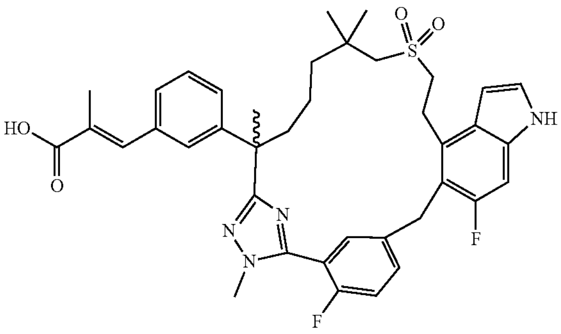 [SMILES: C/C(=C\c1cccc(C2(C)CCCC(C)(C)CS(=O)(=O)CCc3c(c(F)cc4[nH]ccc34)Cc3ccc(F)c(c3)-c3nc2nn3C)c1)C(=O)O]

3-(22,28-Difluoro-3,6,10,10-tetramethyl-12,12-dioxo-12λ6-thia-3,4,19,30-tetrazapentacyclo-[23.3.1.12,5.015,23.016,20]triaconta-1(29),2(30),4,15,17,20,22,25,27-nonaen-6-yl)phenol

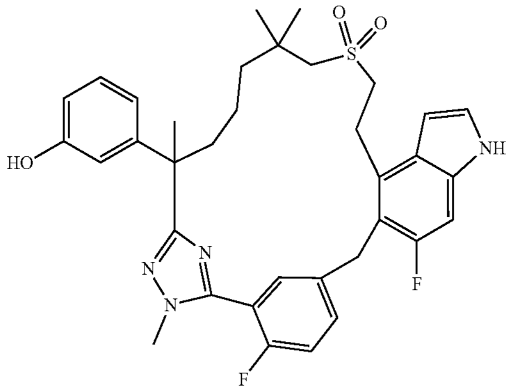

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with 2-(3-(benzyloxy)phenyl)-7-((2-hydroxyethyl)sulfonyl)-N',2,6,6-tetramethylheptanehydrazide (Intermediate 69-20, 1.08 g, 2.2 mmol), and methyl 5-((4-bromo-6-fluoro-1H-indol-5-yl)oxy)-2-fluorobenzimidothioate hydroiodide (Intermediate 14-1) with methyl 5-((4-bromo-6-fluoro-1H-indol-5-yl)methyl)-2-fluorobenzimidothioate hydroiodide (Intermediate 14-8, 1.2 g, 2.2 mmol) in Step A of Example 6, the title compound (0.25 g) was prepared following the reaction sequence (Steps A-D) as described for Example 6. MS (ESI): 633 m/z $[M+H]^+$, retention time: 1.90 minutes, purity: 88% (214 nm) (LC-MS Method 009). Compounds 166A and 166B: Enantiomers 1 and 2 of (E)-3-[3-(22,28-difluoro-3,6,10,10-tetramethyl-12,12-dioxo-12λ6-thia-3,4,19,30-tetrazapentacyclo-[23.3.1.12,5.015,23.016,20]triaconta-1(29),2(30),4,15,17,20,22,25,27-nonaen-6-yl)phenyl]-2-methyl-prop-2-enoic Acid

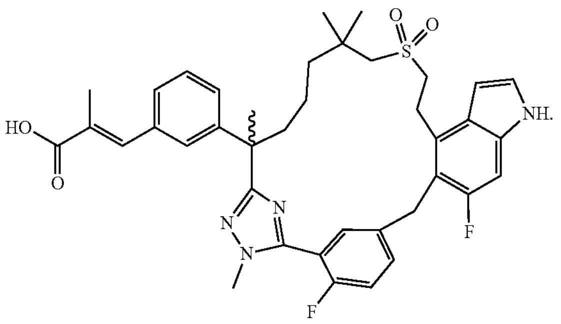 [SMILES: C/C(=C\c1cccc(C2(C)CCCC(C)(C)CS(=O)(=O)CCc3c(c(F)cc4[nH]ccc34)Cc3ccc(F)c(c3)-c3nc2nn3C)c1)C(=O)O]

Step B: Exchanging Example 154 with Step A product of this example (420 mg, 0.66 mmol) in Step A of Example 155, and ethyl (E)-3-(4,4,5,5-tetramethyl-1,3,2-dioxaborolan-2-yl)prop-2-enoate (Intermediate 126) with ethyl (E)-2-methyl-3-(4,4,5,5-tetramethyl-1,3,2-dioxaborolan-2-yl)acrylate (77 mg, 0.32 mmol) in Step B of Example 155, the reaction sequence procedures (Steps A to C) described for Example 155 was used to prepare the title compounds. The racemic ethyl mixture (135 mg) obtained from corresponding Step B of Example 155 was subject to the following chiral SFC separation: Instrument: SFC-80 (Thar, Waters); Column: AD 20*250 mm, 10 μm; Column temperature: 35° C.; Mobile phase: carbon dioxide/methanol (0.2% methanol ammonia as additive)=60/40; Flow rate: 80 g/minutes; Back pressure: 100 bar; Detection wavelength: 214 nm; Cycle time: 5.8 minutes; Sample solution: 135 mg dissolved in 25 mL methanol; Injection volume: 1.9 mL. The first eluent, enantiomer 1 (58 mg, 46%), was further hydrolyzed to Compound 166A (35.3 mg, 63%, white solid). The second eluent, enantiomer 2 (57 mg, 46%), was further hydrolyzed to Compound 166B (40.1 mg, 73%, white solid), as described in Step C of Example 155.

Compound 166A: MS (ESI): 701 m/z $[M+H]^+$, retention time: 2.00 minutes, purity: 99% (214 nm). (LC-MS Method 003). $^1$H NMR (400 MHz, $CD_3OD$) δ 7.70 (dd, J=6.6, 2.2 Hz, 1H), 7.64 (s, 1H), 7.62-7.58 (m, 1H), 7.36-7.22 (m, 6H), 7.09 (d, J=10.7, 1H), 6.47 (d, J=3.0, 1H), 4.24-4.11 (m, 2H), 3.83 (s, 3H), 3.48-3.40 (m, 2H), 3.20-3.11 (m, 2H), 3.09 (s, 2H), 2.39-2.32 (m, 1H), 1.96-1.91 (m, 4H), 1.75 (s, 3H), 1.68-1.63 (m, 1H), 1.54-1.50 (m, 2H), 1.32-1.26 (m, 1H), 1.21 (s, 3H), 1.19 (s, 3H) ppm.

Compound 166B: MS (ESI): 701 m/z $[M+H]^+$, retention time: 2.00 minutes, purity: >99% (214 nm). (LC-MS Method 003). $^1$H NMR (400 MHz, $CD_3OD$) δ 7.70 (dd, J=6.6, 2.2 Hz, 1H), 7.61-7.58 (m, 2H), 7.35-7.20 (m, 6H), 7.09 (d, J=10.7, 1H), 6.47 (d, J=3.0, 1H), 4.24-4.11 (m, 2H), 3.83 (d, J=1.7, 3H), 3.49-3.39 (m, 2H), 3.21-3.11 (m, 2H), 3.09 (s, 2H), 2.39-2.32 (m, 1H), 1.97-1.90 (m, 4H), 1.74 (s, 3H), 1.69-1.62 (m, 1H), 1.54-1.49 (m, 2H), 1.32-1.26 (m, 1H), 1.21 (s, 3H), 1.19 (s, 3H) ppm.

Example 167. (E)-3-[3-(22,28-Difluoro-3,6,10,10-tetramethyl-12,12-dioxo-12λ6-thia-3,4,19,30-tetrazapentacyclo[23.3.1.12,5.015,23.016,20]triaconta-1(29),2(30),4,15,17,20,22,25,27-nonaen-6-yl)phenyl]prop-2-enoic Acid

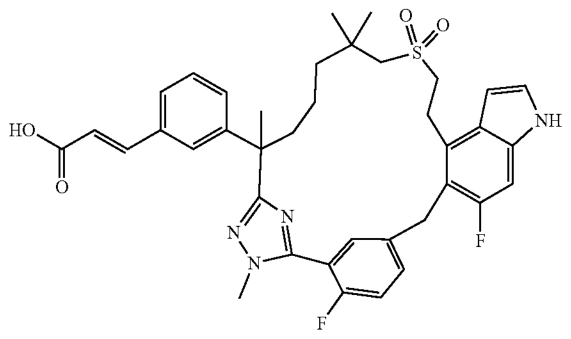 [SMILES: Cn1nc2nc1-c1cc(ccc1F)Cc1c(F)cc3[nH]ccc3c1CCS(=O)(=O)CC(C)(C)CCCC2(C)c1cccc(/C=C/C(=O)O)c1]

Exchanging ethyl (E)-2-methyl-3-(4,4,5,5-tetramethyl-1,3,2-dioxaborolan-2-yl)acrylate with ethyl (E)-3-(4,4,5,5-tetramethyl-1,3,2-dioxaborolan-2-yl)prop-2-enoate (51 mg, 0.225 mmol) in Step B, the reaction procedure sequence (Steps A and B) described for Example 166A and 166B was used to prepare the title compound (34.5 mg) as a racemic mixture. MS (ESI): 687 m/z $[M+H]^+$, retention time: 1.95 minutes, purity: >99% (214 nm) (LC-MS Method 003). $^1H$ NMR (400 MHz, $CD_3OD$) δ 7.71 (dd, J=6.6, 2.2 Hz, 1H), 7.64-7.57 (m, 2H), 7.45-7.41 (m, 2H), 7.36-7.20 (m, 4H), 7.09 (d, J=10.7 Hz, 1H), 6.47 (d, J=3.3 Hz, 1H), 6.40 (d, J=16.1 Hz, 1H), 4.24-4.11 (m, 2H), 3.84 (d, J=1.8 Hz, 3H), 3.49-3.39 (m, 2H), 3.18-3.05 (m, 4H), 2.39-2.32 (m, 1H), 1.97-1.89 (m, 1H), 1.76 (s, 3H), 1.68-1.58 (m, 1H), 1.54-1.50 (m, 2H), 1.36-1.29 (m, 1H), 1.21 (s, 3H), 1.19 (s, 3H) ppm.

Example 168. 2-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]-3,3,3-trifluoro-propanoic acid

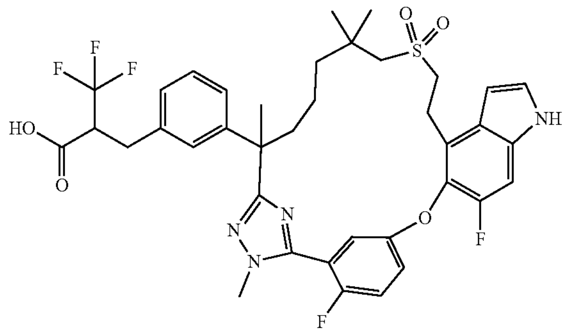 [SMILES: Cn1nc2nc1-c1cc(ccc1F)Oc1c(F)cc3[nH]ccc3c1CCS(=O)(=O)CC(C)(C)CCCC2(C)c1cccc(CC(C(=O)O)C(F)(F)F)c1]

22,28-Difluoro-3,6,10,10-tetramethyl-6-[3-(4,4,5,5-tetramethyl-1,3,2-dioxaborolan-2-yl)phenyl]-24-oxa-12λ6-thia-3,4,19,30-tetrazapentacyclo[23.3.1.12,5.015,23.016,20]triaconta-1(29),2(30),4,15,17,20,22,25,27-nonaene 12,12-dioxide

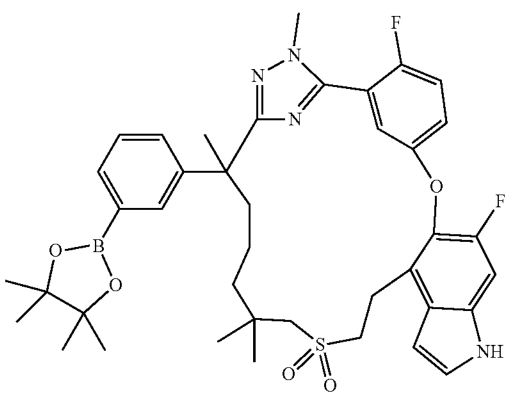 [SMILES: Cn1nc2nc1-c1cc(ccc1F)Oc1c(F)cc3[nH]ccc3c1CCS(=O)(=O)CC(C)(C)CCCC2(C)c1cccc(B2OC(C)(C)C(C)(C)O2)c1]

Step A: To a stirred and degassed solution of [3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]trifluoromethanesulfonate (Step A product of Example 155, 1.00 g, 1.30 mmol) in N,N-dimethylformamide (20 mL) was added potassium acetate (0.38 g, 3.91 mmol) and bis(pinacolato)diboron (0.40 g, 1.56 mmol), 1,1'-bis(diphenylphosphino)ferrocene-palladium(ii)dichloride dichloromethane complex (0.11 g, 0.130 mmol). The mixture was purged with Argon, and stirred at 105° C. for 5 hours, then cooled to room temperature, quenched with water (80 mL), and extracted with ethyl acetate (2×80 mL). The combined organic phases were washed with brine, dried over sodium sulfate, and concentrated. The residue was purified by automated flash chromatography (40 g silica gel column, eluted with 0-60% ethyl acetate in petroleum) to give the title compound (0.70 g, 72.08%) as a solid. MS (ESI): 745 m/z $[M+H]^+$, retention time: 2.14 minutes, purity: 94% (214 nm) (LC-MS Method 034).

Compound 168: 2-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]-3,3,3-trifluoro-propanoic acid

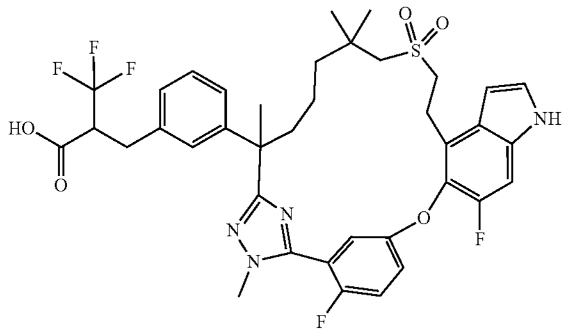 [SMILES: Cn1nc2nc1-c1cc(ccc1F)Oc1c(F)cc3[nH]ccc3c1CCS(=O)(=O)CC(C)(C)CCCC2(C)c1cccc(CC(C(=O)O)C(F)(F)F)c1]

Step B: To a stirred and degassed solution of Step A product (100 mg, 0.134 mmol) in 2-methyl-2-butanol (5 mL) were added silver hexafluoroantimonate (4.6 mg, 0.0134 mmol), silver(I) oxide (31 mg, 0.134 mmol) and 2-(trifluoromethyl)prop-2-enoic acid (28 mg, 0.201 mmol), bis-[(pentamethylcyclopentadienyl)dichloro-rhodium](8.3 mg, 0.0134 mmol). The mixture was purged with argon and stirred at 90° C. overnight, then cooled to room temperature, diluted with ethyl acetate (20 mL). The solution was washed with water, dried over magnesium sulfate, filtered, and concentrated. The residue was purified by prep-HPLC to give the title compound (20 mg, 20%) as a solid. LC-MS: MS (ESI): 759 m/z $[M+H]^+$, retention time: 1.95 minutes, purity: >99% (214 nm). (LC-MS Method 004). $^1H$ NMR (500 MHz, $CD_3OD$) δ 7.35-7.28 (m, 3H), 7.24-7.09 (m, 4H), 7.05 (d, J=6.0 Hz, 1H), 7.03-6.96 (m, 1H), 6.61 (d, J=2.8 Hz, 1H), 3.85 (d, J=1.2 Hz, 3H), 3.44-3.34 (m, 3H), 3.27-3.15 (m, 2H), 3.12-2.98 (m, 2H), 2.90 (dd, J=10.8, 2.8 Hz, 1H), 2.77 (dd, J=10.8, 2.8 Hz, 1H), 2.15-2.09 (m, 1H), 1.86-1.78 (m, 1H), 1.67 (s, 3H), 1.60-1.53 (m, 1H), 1.33-1.28 (m, 1H), 1.21-1.15 (m, 1H), 1.08-0.95 (m, 7H) ppm.

Example 169. (2R)-3-[3-(22,28-Difluoro-3,6,10,10-tetramethyl-12,12-dioxo-12λ6-thia-3,4,19,30-tetrazapentacyclo[23.3.1.12,5.015,23.016,20]-triaconta-1(29),2(30),4,15,17,20,22,25,27-nonaen-6-yl) phenyl]-2-methyl-propanoic Acid

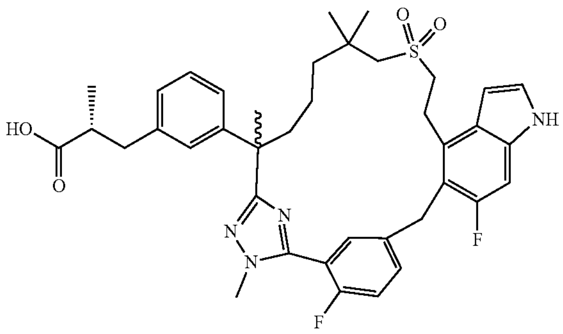 [SMILES: C[C@H](Cc1cccc(C2(C)CCCC(C)(C)CS(=O)(=O)CCc3c(c(F)cc4[nH]ccc34)Cc3ccc(F)c(c3)-c3nc2nn3C)c1)C(=O)O]

Exchanging methyl 5-((4-bromo-6-fluoro-1H-indol-5-yl) oxy)-2-fluorobenzimidothioate hydroiodide (Intermediate 14-1) with methyl 5-((4-bromo-6-fluoro-1H-indol-5-yl) methyl)-2-fluorobenzimidothioate hydroiodide (Intermediate 14-8, 0.99 g, 1.9 mmol), the reaction procedure sequence (Steps A to G) described for Example 6 was used to prepare the title compounds. The racemic methyl ester (270 mg), obtained in corresponding Step D of Example 6, was subject to chiral SFC separation under the following conditions: Instrument: SFC-80 (Thar, Waters); Column: OD 20*250 mm, 10 μm; Column temperature: 35° C.; Mobile phase: carbon dioxide/methanol (0.2% methanol ammonia as additive)=55/45; Flow rate: 80 g/minutes; Back pressure: 100 bar; Detection wavelength: 214 nm; Cycle time: 3.5 minutes; Sample solution: 270 mg dissolved in 25 mL methanol; Injection volume: 1 mL. The first eluent, enantiomer 1 (116 mg, 43%), was further hydrolyzed to Compound 169A (87.7 mg, 77%, white solid); The second eluent, enantiomer 2 (123 mg. 46%), was further hydrolyzed to Compound 169B (99.9 mg, 82%, white solid), as described in corresponding Steps F and G in Example 6.

Compound 169A: MS (ESI): 703 m/z $[M+H]^+$, retention time: 1.92 minutes, purity: >99% (214 nm). (LC-MS Method 003). $^1H$ NMR (400 MHz, $CD_3OD$) δ 7.70 (dd, J=6.6, 2.0 Hz, 1H), 7.60-7.55 (m, 1H), 7.26-7.13 (m, 3H), 7.11-7.05 (m, 2H), 7.04-6.97 (m, 2H), 6.46 (d, J=2.0 Hz, 1H), 4.26-4.07 (m, 2H), 3.83 (s, 3H), 3.49-3.36 (m, 2H), 3.19-3.03 (m, 4H), 3.00-2.89 (m, 1H), 2.67-2.54 (m, 2H), 2.36-2.26 (m, 1H), 1.92-1.83 (m, 1H), 1.76-1.57 (m, 4H), 1.52-1.47 (m, 2H), 1.26-1.14 (m, 7H), 1.08 (d, J=6.6 Hz, 3H) ppm.

Compound 169B: MS (ESI): 703 m/z $[M+H]^+$, retention time: 2.00 minutes, purity: 98% (214 nm). (LC-MS Method 003). $^1H$ NMR (400 MHz, $CD_3OD$) δ 7.69 (dd, J=6.6, 2.0 Hz, 1H), 7.60-7.55 (m, 1H), 7.26-7.13 (m, 3H), 7.12-7.05 (m, 2H), 7.04-6.97 (m, 2H), 6.46 (d, J=2.0 Hz, 1H), 4.26-4.07 (m, 2H), 3.83 (d, J=2 Hz, 3H), 3.49-3.36 (m, 2H), 3.19-3.04 (m, 4H), 3.00-2.89 (m, 1H), 2.67-2.54 (m, 2H), 2.36-2.26 (m, 1H), 1.92-1.85 (m, 1H), 1.71 (s, 3H), 1.66-1.56 (m, 1H), 1.52-1.47 (m, 2H), 1.26-1.14 (m, 7H), 1.06 (d, J=6.6 Hz, 3H) ppm.

Example 170. (2S)-3-[3-(22-Fluoro-3,10,10-trimethyl-12,12,24-trioxo-12λ6-thia-5,19,30-triazapentacyclo[23.3.1.12,5.015,23.016,20]triaconta-1(29),2 (30),3,15,17,20,22,25,27-nonaen-6-yl)phenyl]-2-methyl-propanoic Acid

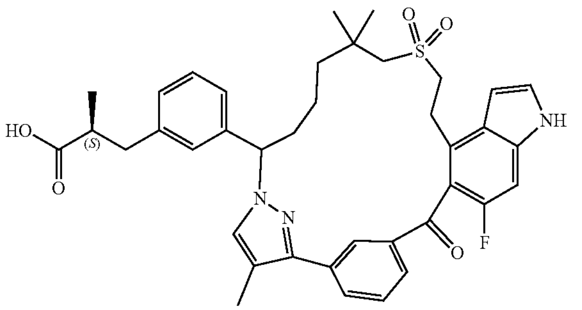

Exchanging (6-fluoro-1-(triisopropylsilyl)-4-vinyl-1H-indol-5-yl)(3-(1-(tetrahydro-2H-pyran-2-yl)-1H-pyrazol-5-yl)phenyl)methanone (Intermediate 130) with (6-fluoro-4-vinyl-1H-indol-5-yl)(3-(4-methyl-1-(tetrahydro-2H-pyran-2-yl)-1H-pyrazol-5-yl)phenyl)methanone (Intermediate 130-1, 1.10 g, 2.60 mmol), the reaction procedure sequence (from first to fifth steps) described for Compound 163 was used to prepare the title compound (10 mg).

Compound 170: MS (ESI): 684 m/z $[M+H]^+$, retention time: 1.90 minutes, purity: >99% (214 nm) (LC-MS Method 003). $^1H$ NMR (400 MHz, $CD_3OD$) δ 8.07 (s, 1H), 7.93 (d, J=8.0 Hz, 1H), 7.85 (d, J=8.0 Hz, 1H), 7.63 (t, J=7.6 Hz, 1H), 7.49-7.47 (m, 1H), 7.41 (d, J=3.6 Hz, 1H), 7.19-7.16 (m, 3H), 7.04 (d, J=6.4 Hz, 1H), 6.71 (d, J=2.8 Hz, 1H), 6.37-6.33 (m, 1H), 6.23-6.17 (m, 1H), 3.42-3.38 (m, 2H), 3.34-3.28 (m, 2H), 3.07 (s, 2H), 3.00-2.95 (m, 1H), 2.68-2.59 (m, 2H), 2.23-2.14 (m, 5H), 1.63-1.59 (m, 2H), 1.33-1.30 (m, 1H), 1.21-1.18 (m, 6H), 1.15-1.09 (m, 4H) ppm.

Example 171. Diastereomers 1 and 2 of 1-[[3-(22,28-difluoro-6,10,10-trimethyl-12,12-dioxo-24-oxa-12λ6-thia-3,19,30-triazapentacyclo[23.3.1.12,5.015,23.016,20]triaconta-1(29),2(30),4,15,17,20,22,25,27-nonaen-6-yl)phenyl]methyl]cyclopropanecarboxylic Acid

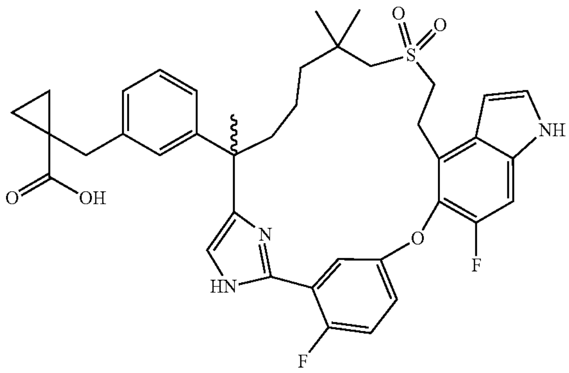 [SMILES: CC1(C)CCCC(C)(c2cccc(CC3(C(=O)O)CC3)c2)c2c[nH]c(n2)-c2cc(ccc2F)Oc2c(F)cc3[nH]ccc3c2CCS(=O)(=O)C1]

Exchanging methyl (2S)-3-(3-(1-bromo-8-((2-((tert-butyldiphenylsilyl)oxy)ethyl)sulfonyl)-3,7,7-trimethyl-2-oxooctan-3-yl)phenyl)-2-methylpropanoate (Intermediate 17-14) with methyl 1-(3-(1-bromo-8-((2-((tert-butyldiphenylsilyl)oxy)ethyl)sulfonyl)-3,7,7-trimethyl-2-oxooctan-3-yl)benzyl)cyclopropane-1-carboxylate (Intermediate 17-16, 3.2 g, 4.08 mmol) in Step A, the reaction procedure sequence (Steps A to C) described for Example 129 was used for the preparation of the title compounds. The racemic methyl ester (570 mg) was not separable. Instead, chiral SFC separation was performed on racemic acid (550 mg), after ester hydrolysis, under the following condition: Instrument: SFC-150 (Waters); Column: AS 20*250 mm, 10 μm; Column temperature: 35° C.; Mobile phase: carbon dioxide/methanol (0.2% methanol ammonia as additive)=40/60; Flow rate: 120 g/minutes; Back pressure: 100 bar; Detection wavelength: 214 nm; Cycle time: 6 minutes; Sample solution: 550 mg dissolved in 40 mL methanol; Injection volume: 2 mL. The first eluent, enantiomer 1, was designated as Compound 171A (170 mg, 31%); The second eluent, enantiomer 2, was designated as Compound 171B (160 mg, 29%).

Compound 171A: MS (ESI): 702 m/z $[M+H]^+$, retention time: 1.67 minutes, purity: 95% (214 nm) (LC-MS Method 003). $^1H$ NMR (500 MHz, $CD_3OD$) δ 7.54 (dd, J=6.0, 3.2 Hz, 1H), 7.30 (d, J=3.2 Hz, 1H), 7.25-7.20 (m, 2H), 7.13-7.10 (m, 2H), 7.08-6.98 (m, 4H), 6.60 (dd, J=3.6, 0.8 Hz, 1H), 3.40-3.34 (m, 2H), 3.24-3.16 (m, 1H), 3.08-3.00 (m, 1H), 2.90 (s, 2H), 2.66 (s, 2H), 2.11-2.03 (m, 1H), 1.90-1.80 (m, 1H), 1.54 (s, 3H), 1.39-1.18 (m, 2H), 1.16-1.10 (m, 3H), 1.08 (s, 3H), 0.97 (s, 3H), 0.95-0.87 (m, 1H), 0.74-0.71 (m, 2H) ppm. Chiral purity: e.e. %=100% (Chiral-HPLC Method Info: AS-H 40% methanol [0.2% ammonia (7M in methanol) as additive]; Flow rate: 4 mL/minutes; Temperature: 40° C.; Back Pressure: 120 bar; Retention time=0.85 minutes).

Compound 171B: MS (ESI): 702 m/z $[M+H]^+$, retention time: 1.67 minutes, purity: 95% (214 nm). (LC-MS Method 003). $^1H$ NMR (500 MHz, $CD_3OD$) δ 7.54 (dd, J=6.0, 3.2 Hz, 1H), 7.30 (d, J=3.2 Hz, 1H), 7.25-7.20 (m, 2H), 7.13-7.09 (m, 2H), 7.07-6.98 (m, 4H), 6.60 (dd, J=3.2, 0.4 Hz, 1H), 3.40-3.34 (m, 2H), 3.23-3.17 (m, 1H), 3.08-3.00 (m, 1H), 2.90 (s, 2H), 2.66 (s, 2H), 2.11-2.03 (m, 1H), 1.90-1.80 (m, 1H), 1.54 (s, 3H), 1.37-1.22 (m, 2H), 1.15-1.12 (m, 3H), 1.07 (s, 3H), 0.97 (s, 3H), 0.94-0.88 (m, 1H), 0.71-0.69 (m, 2H) ppm. Chiral purity: ee %=98.9% (retention time: 2.29 minutes).

Example 172. (3E)-3-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methylene]tetrahydrofuran-2-one

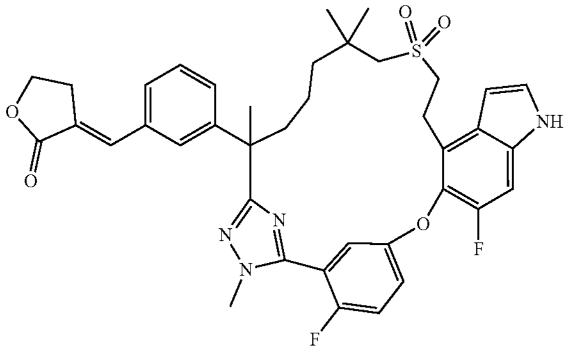 [SMILES: Cn1nc2nc1-c1cc(ccc1F)Oc1c(F)cc3[nH]ccc3c1CCS(=O)(=O)CC(C)(C)CCCC2(C)c1cccc(/C=C2\CCOC2=O)c1]

To a stirred and degassed solution of 22,28-difluoro-3,6,10,10-tetramethyl-6-[3-(4,4,5,5-tetramethyl-1,3,2-dioxaborolan-2-yl)phenyl]-24-oxa-12λ6-thia-3,4,19,30-tetrazapentacyclo-[23.3.1.12,5.015,23.016,20]triaconta-1(29),2(30),4,15,17,20,22,25,27-nonaene 12,12-dioxide (Step A product of Example 168, 100 mg, 0.134 mmol) in N,N-dimethylformamide (3 mL) were added potassium carbonate (37 mg, 0.269 mmol) and 1,1'-bis(diphenylphosphino)-ferrocene-palladium(II)dichloride dichloromethane complex (11 mg, 0.0134 mmol), (Z)-(2-oxodihydrofuran-3(2H)-ylidene)methyl trifluoromethanesulfonate (99 mg, 0.403 mmol) at room temperature. The mixture was purged with argon and stirred at 100° C. for 5 hours, cooled to room temperature, and quenched with water (20 mL). The solution was extracted with ethyl acetate (2×20 mL). The combined organic phases were washed with brine, dried over sodium sulfate, and concentrated. The residue was purified by prep-HPLC to give the title compound (16 mg, 17%) as a solid. MS (ESI): 715 m/z $[M+H]^+$, retention time: 1.95 minutes, purity: 99% (214 nm). (LC-MS Method 003). $^1H$ NMR (400 MHz, DMSO-$d_6$) δ 11.34 (s, 1H), 7.48-7.39 (m, 4H), 7.38-7.33 (m, 3H), 7.31-7.25 (m, 3H), 6.51 (s, 1H), 4.39-4.34 (m, 2H), 3.80 (d, J=2.0 Hz, 3H), 3.28-3.14 (m, 4H), 3.09-3.04 (m, 2H), 2.94-2.91 (m, 1H), 2.85-2.80 (m, 1H), 2.13-2.08 (m, 1H), 1.78-1.73 (m, 1H), 1.66 (s, 3H), 1.59-1.53 (m, 1H), 1.25-1.16 (m, 3H), 1.01 (s, 3H), 1.00 (s, 3H) ppm.

Example 173. 3-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]tetrahydrofuran-2-one

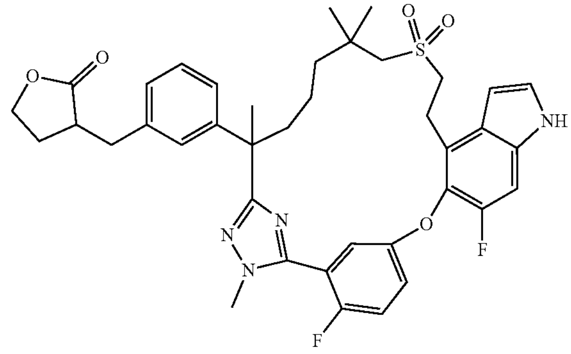 [SMILES: Cn1nc2nc1-c1cc(ccc1F)Oc1c(F)cc3[nH]ccc3c1CCS(=O)(=O)CC(C)(C)CCCC2(C)c1cccc(CC2CCOC2=O)c1]

To a stirred solution of (3E)-3-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methylene]tetrahydrofuran-2-one (Example 172, 14 mg, 0.0196 mmol) in tetrahydrofuran (5 mL) was added palladium on carbon (wet, 10%, 5 mg). The reaction mixture was stirred under hydrogen at 50° C. for 2 hours, then cooled to room temperature, and filtered through a pad of Celite. The filtrate was concentrated. The residue was purified by prep-HPLC to give the title compound (4.0 mg, 29%) as a solid. MS (ESI): 717 m/z $[M+H]^+$, retention time: 1.94 minutes, purity: 99% (214 nm) (LC-MS Method 003). $^1$H NMR (400 MHz, DMSO-$d_6$) δ 11.34 (s, 1H), 7.48-7.39 (m, 2H), 7.33 (d, J=10.0 Hz, 1H), 7.29-7.21 (m, 2H), 7.16 (t, J=7.6 Hz, 1H), 7.09-7.05 (m, 1H), 7.02-6.93 (m, 2H), 6.51 (s, 1H), 4.13-4.00 (m, 2H), 3.78 (s, 3H), 3.29-3.10 (m, 4H), 3.00-2.80 (m, 4H), 2.65-2.59 (m, 1H), 2.12-1.95 (m, 3H), 1.83-1.77 (m, 1H), 1.62 (s, 3H), 1.53-1.47 (m, 1H), 1.24-1.14 (m, 3H), 1.02 (s, 3H), 0.99 (s, 3H) ppm.

Example 174. (5Z)-5-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]methylene]imidazolidine-2,4-dione

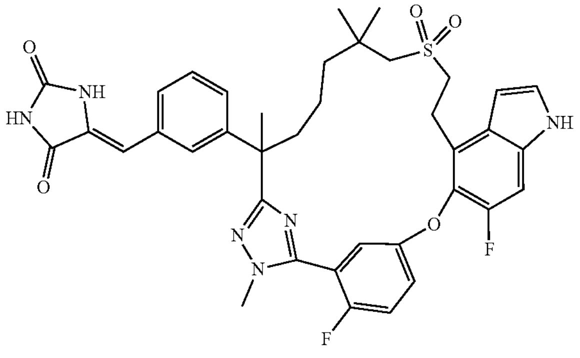 [SMILES: Cn1nc2nc1-c1cc(ccc1F)Oc1c(F)cc3[nH]ccc3c1CCS(=O)(=O)CC(C)(C)CCCC2(C)c1cccc(/C=C2\NC(=O)NC2=O)c1]

Methyl 3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)benzoate

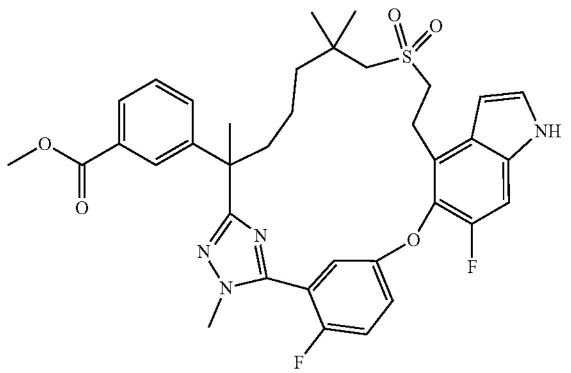 [SMILES: COC(=O)c1cccc(C2(C)CCCC(C)(C)CS(=O)(=O)CCc3c(c(F)cc4[nH]ccc34)Oc3ccc(F)c(c3)-c3nc2nn3C)c1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl 3-(7-((2-hydroxyethyl)sulfonyl)-2,6,6-trimethyl-1-(2-methylhydrazineyl)-1-oxoheptan-2-yl)benzoate (Intermediate 69-21, 1.34 g, 2.8 mmol) in Step A, the reaction procedure sequenced (Steps A to D) described for Example 6 was used to prepare the title compound (510 mg) as a racemic mixture. MS (ESI): 677 m/z $[M+H]^+$, retention time: 2.07 minutes, purity: 93% (214 nm). (LC-MS Method 003).

[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methanol

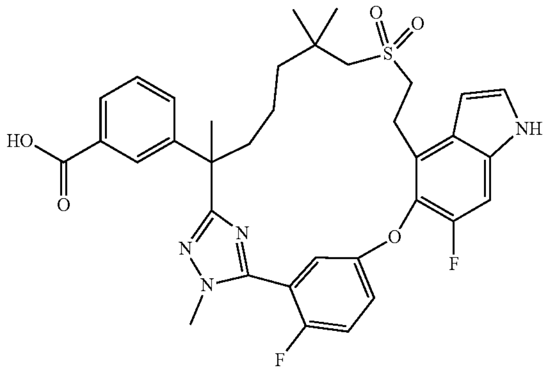 [SMILES: Cn1nc2nc1-c1cc(ccc1F)Oc1c(F)cc3[nH]ccc3c1CCS(=O)(=O)CC(C)(C)CCCC2(C)c1cccc(C(=O)O)c1]

Step B: To a stirred solution of Step A product (430 mg, 0.64 mmol) in tetrahydrofuran (10 mL) was added lithium borohydride (1.3 mL, 2.5 mmol). The reaction mixture was stirred at room temperature for 16 hours, then quenched with methanol (15 mL), and diluted with ethyl acetate (80 mL). The solution was washed with water, dried over sodium sulfate, and concentrated to give the title compound (400 mg, 97%) as solid. MS (ESI): 649 m/z $[M+H]^+$, retention time: 1.92 minutes, purity: >99% (214 nm) (LC-MS Method 027). 3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)benzaldehyde

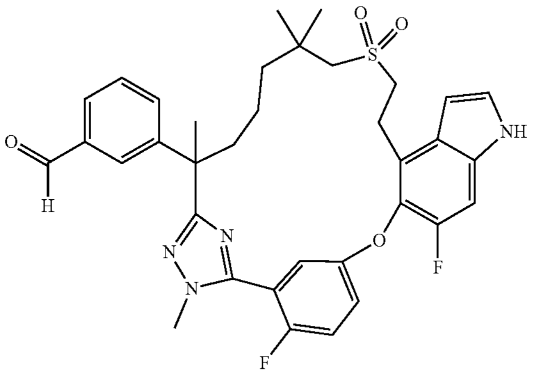 [SMILES: Cn1nc2nc1-c1cc(ccc1F)Oc1c(F)cc3[nH]ccc3c1CCS(=O)(=O)CC(C)(C)CCCC2(C)c1cccc(C=O)c1]

Step C: To a stirred solution of Step B product (395 mg, 0.61 mmol) in tetrahydrofuran (15 mL) was added manganese (IV) dioxide (1.06 g, 12.2 mmol). The mixture was stirred at room temperature for 16 hours, then filtered through a pad of Celite. The filtrate was concentrated to give the title compound (387 mg, 96%) as a solid. MS (ESI): 647 m/z $[M+H]^+$, retention time: 2.02 minutes, purity: 97% (214 nm). (LC-MS Method 027).

Compound 174: (5Z)-5-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]methylene]imidazolidine-2,4-dione

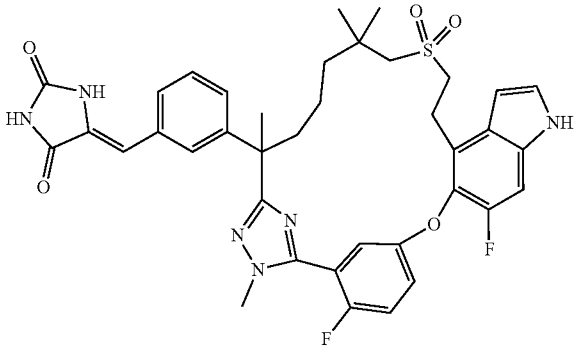 [SMILES: Cn1nc2nc1-c1cc(ccc1F)Oc1c(F)cc3[nH]ccc3c1CCS(=O)(=O)CC(C)(C)CCCC2(C)c1cccc(/C=C2\NC(=O)NC2=O)c1]

Step D: A solution of hydantoin (23 mg, 0.23 mmol) in water (2.0 mL) was heated at 70° C. until complete dissolution, then the pH adjusted to ~7.0 with saturated sodium bicarbonate, followed by addition of 2-aminoethan-1-ol (18.1 mg, 0.3 mmol). To the above stirred and heated (90° C.) mixture was added dropwise a solution of the product from Step C (97 mg, 0.15 mmol) in ethanol (2 mL). After the addition, the mixture was stirred for 16 hours at 100° C., then cooled to room temperature, diluted with ethyl acetate (60 mL). The solution was washed with water, brine, dried over sodium sulfate, and concentrated. The residue was purified by automated silica gel column chromatography (5 g silica gel column; eluted with ethyl acetate in petroleum ether 0-100%) to give the title compound (30 mg, 27%) as a white solid. MS (ESI): 729 m/z $[M+H]^+$, retention time: 1.91 minutes, purity: >99% (214 nm). (LC-MS Method 003). $^1H$ NMR (400 MHz, $CD_3OD$). δ 7.37-7.29 (m, 6H), 7.23-7.18 (m, 3H), 6.61 (d, J=2.8 Hz, 1H), 6.51 (s, 1H), 3.86 (d, J=2.4 Hz, 3H), 3.40-3.36 (m, 2H), 3.26-3.17 (m, 2H), 2.86 (d, J=13.6 Hz, 1H), 2.75 (d, J=13.6 Hz, 1H), 2.22-2.18 (m, 1H), 1.93-1.82 (m, 1H), 1.71 (s, 3H), 1.60-1.45 (m, 1H), 1.34-1.27 (m, 1H), 1.25-1.18 (m, 1H), 1.05-0.98 (m, 7H) ppm.

Example 175. 5-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]imidazolidine-2,4-dione

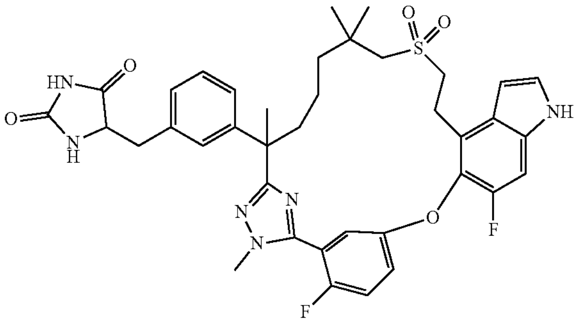 [SMILES: Cn1nc2nc1-c1cc(ccc1F)Oc1c(F)cc3[nH]ccc3c1CCS(=O)(=O)CC(C)(C)CCCC2(C)c1cccc(CC2NC(=O)NC2=O)c1]

To a stirred solution of (5Z)-5-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]methylene]imidazolidine-2,4-dione (Example 174) (21.8 mg, 0.03 mmol) in tetrahydrofuran (2 mL) was added palladium on carbon (10%, 50% wet, 5 mg). The mixture was stirred at room temperature under hydrogen atmosphere for 16 hours, then filtered through a pad of Celite. The filtrate was concentrated. The residue was purified by Prep-HPLC to give the title compound (6.0 mg, 27%) as a solid. MS (ESI): 731 m/z $[M+H]^+$, retention time: 1.83 minutes, purity: >99% (214 nm). (LC-MS Method 027). $^1H$ NMR (400 MHz, $CD_3OD$). δ 7.34-7.31 (m, 3H), 7.25-7.14 (m, 3H), 7.09-7.00 (m, 3H), 6.61 (d, J=3.2 Hz, 1H), 4.30-4.23 (m, 1H), 3.86-3.84 (m, 3H), 3.40-3.35 (m, 2H), 3.29-3.25 (m, 1H), 3.07-2.90 (m, 2H), 2.87-2.79 (m, 2H), 2.20-2.10 (m, 1H), 1.85-1.75 (m, 1H), 1.67 (d, J=2.4 Hz, 3H), 1.59-1.49 (m, 1H), 1.34-1.17 (m, 3H), 1.07-0.99 (m, 7H) ppm.

Example 176. 5-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-hydroxy-methyl]imidazolidine-2,4-dione

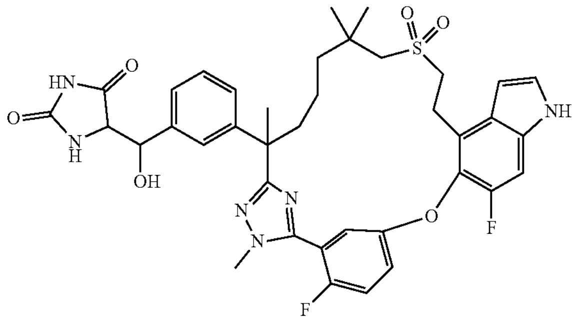 [SMILES: Cn1nc2nc1-c1cc(ccc1F)Oc1c(F)cc3[nH]ccc3c1CCS(=O)(=O)CC(C)(C)CCCC2(C)c1cccc(C(O)C2NC(=O)NC2=O)c1]

To a stirred solution of 3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2

(30),4,15,17,20,22,25,27-nonaen-6-yl)benzaldehyde (Step C product of Example 174, 194 mg, 0.3 mmol) in methanol (1.2 mL) and water (0.8 mL) were added hydantoin (45 mg, 0.45 mmol), trimethylamine (88 mg, 0.45 mmol). The reaction mixture was stirred at 70° C. for 24 hours, then cooled to room temperature, and diluted with ethyl acetate (50 mL). The solution was washed with water, brine, dried over sodium sulfate, and concentrated. The residue was purified by Prep-HPLC to give the title compound (47 mg, 20%) as a white solid. MS (ESI): 747 m/z $[M+H]^+$, retention time: 1.76 minutes, purity: 99% (254 nm) (LC-MS Method 027).

$^1$H NMR (400 MHz, $CD_3OD$). δ 7.37-7.18 (m, 8H), 7.11-7.08 (m, 1H), 6.63-6.60 (m, 1H), 5.09-4.91 (m, 1H), 4.37-4.24 (m, 1H), 3.86-3.83 (m, 3H), 3.40-3.36 (m, 2H), 3.30-2.67 (m, 4H), 2.21-2.11 (m, 1H), 1.95-1.75 (m, 1H), 1.69-1.67 (m, 3H), 1.60-1.48 (m, 1H), 1.34-1.27 (m, 1H), 1.23-1.15 (m, 1H), 1.05-1.02 (m, 7H) ppm. (As diastereomer mixtures).

Example 177. Ethyl 3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]-3-hydroxy-propanoate

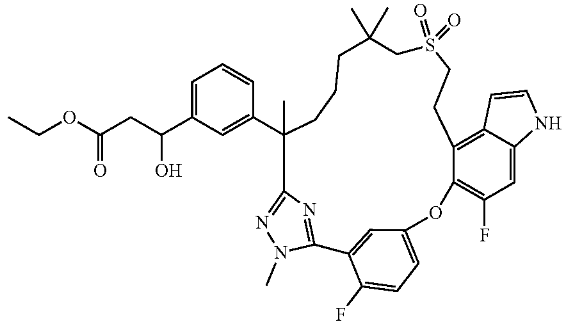 [SMILES: CCOC(=O)CC(O)c1cccc(C2(C)CCCC(C)(C)CS(=O)(=O)CCc3c(c(F)cc4[nH]ccc34)Oc3ccc(F)c(c3)-c3nc2nn3C)c1]

To a stirred and cooled (−78° C.) solution of ethyl acetate (97 mg, 1.1 mmol) in tetrahydrofuran (10 mL) was added lithium diisopropylamide (2M in tetrahydrofuran) (0.5 mL, 1.0 mmol). The mixture was stirred at the −78° C. for 1 hour, then treated with 3-(22,28-difluoro-3,6,10,10-tetramethyl-12,12-dioxo-24-oxa-12λ6-thia-3,4,19,30-tetrazapentacyclo-[23.3.1.12,5.015,23.016,20]triaconta-1(29),2(30),4,15,17,20,22,25,27-nonaen-6-yl)benzaldehyde (Step C product of Example 174, 0.32 g, 0.5 mmol), and stirred at −78° C. for additional 6 hours. The solution was quenched with water, adjusted pH to 5-6 with 2 N hydrochloric acid and extracted with ethyl acetate (2×20 mL). The combined organic extracts were washed with brine, dried over sodium sulfate, and concentrated. The residue was purified by automated silica gel column chromatography (25 g silica gel column; eluted with ethyl acetate in petroleum ether 0-95%) to give the title compound (175 mg, 47%) as a white solid. MS (ESI): 735 m/z $[M+H]^+$, retention time: 1.99 minutes, purity: >99% (214 nm). (LC-MS Method 027). $^1$H NMR (400 MHz, $CD_3OD$). δ 7.37-7.31 (m, 3H), 7.24-7.16 (m, 5H), 7.10-7.07 (m, 1H), 6.61 (d, J=3.2 Hz, 1H), 5.00-4.96 (m, 1H), 4.08-4.03 (m, 2H), 3.85 (d, J=1.6 Hz, 3H), 3.40-3.35 (m, 2H), 3.23-3.20 (m, 1H), 2.95 (d, J=13.6 Hz, 1H), 2.89 (d, J=13.6 Hz, 1H), 2.67-2.53 (m, 2H), 2.20-2.11 (m, 1H), 1.86-1.77 (m, 1H), 1.68 (s, 3H), 1.62-1.53 (m, 1H), 1.38-1.26 (m, 2H), 1.18-1.15 (m, 4H), 1.05-1.00 (m, 7H) ppm (mixture of diastereomers).

Example 178. 3-[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-3-hydroxy-propanoic Acid

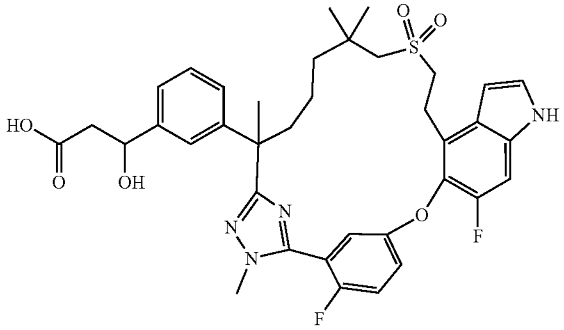 [SMILES: Cn1nc2nc1-c1cc(ccc1F)Oc1c(F)cc3[nH]ccc3c1CCS(=O)(=O)CC(C)(C)CCCC2(C)c1cccc(C(O)CC(=O)O)c1]

To a stirred solution of ethyl 3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]-3-hydroxy-propanoate (Example 177, 44 mg, 0.06 mmol) in methanol (0.6 mL) and tetrahydrofuran (1.8 mL) was added lithium hydroxide (1M in water, 0.6 mL). The mixture was stirred at room temperature for 16 hours, then acidified with 1 M hydrochloric acid to pH ~4 and diluted with ethyl acetate (60 mL). The solution was washed with water, brine, dried over sodium sulfate, and concentrated to give the title compound (20 mg, 46%) as a solid. MS (ESI): 707 m/z $[M+H]^+$, retention time: 1.58 minutes, purity: >99% (214 nm). (LC-MS Method 027). $^1$H NMR (400 MHz, $CD_3OD$). δ 7.36-7.30 (m, 3H), 7.27-7.17 (m, 5H), 7.07-7.04 (m, 1H), 6.61 (d, J=2.8 Hz, 1H), 5.09-4.97 (m, 1H), 3.85 (d, J=2.0 Hz, 3H), 3.40-3.26 (m, 3H), 3.23-3.16 (m, 1H), 2.95-2.90 (m, 1H), 2.80-2.75 (m, 1H), 2.63-2.51 (m, 2H), 2.20-2.11 (m, 1H), 1.86-1.80 (m, 1H), 1.68 (s, 3H), 1.62-1.51 (m, 1H), 1.35-1.29 (m, 1H), 1.21-1.15 (m, 1H), 1.05-1.02 (m, 7H) ppm. (mixture of diastereomers)

Example 179. Diastereomers 1, 2, 3 and 4 of (2S)-3-[6-(22,28-difluoro-3,6,10,10-tetramethyl-12,12,24-trioxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl)-2-pyridyl]-2-methyl-propanoic Acid

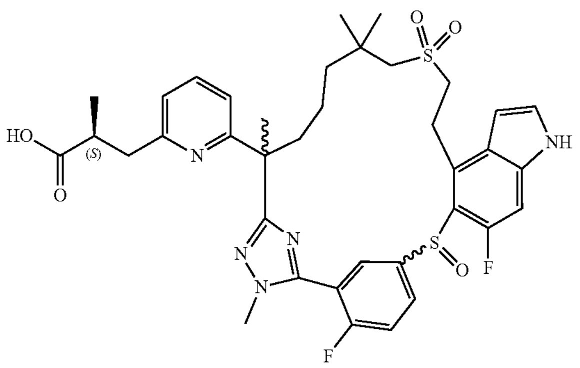

and

Example 180. Diastereomers 1,2 of (2S)-3-[6-(22,28-difluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl)-2-pyridyl]-2-methyl-propanoic Acid (Each Mixture of Two Diastereomers)

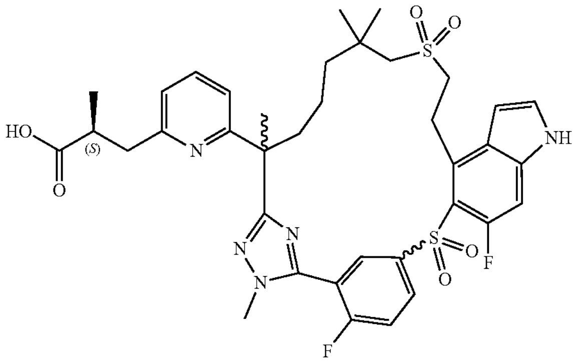

Methyl (2S)-3-[6-(22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl)-2-pyridyl]-2-methyl-propanoate

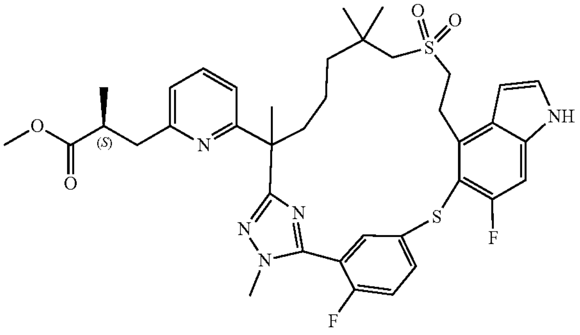

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2S)-3-(6-(7-((2-hydroxyethyl)sulfonyl)-2,6,6-trimethyl-1-(2-methylhydrazineyl)-1-oxoheptan-2-yl)pyridin-2-yl)-2-methylpropanoate (Intermediate 107-2, 1.3 g, 2.67 mmol), and methyl 5-((4-bromo-6-fluoro-1H-indol-5-yl)oxy)-2-fluorobenzimidothioate hydroiodide (Intermediate 14-1) with methyl 5-((4-bromo-6-fluoro-1H-indol-5-yl)thio)-2-fluorobenzimidothioate hydroiodide (Intermediate 76, 1.7 g, 3.2 mmol), the reaction procedure sequence (Steps A to D) described for Example 6 was used to prepare the title compound (528 mg). MS (ESI): 736 m/z [M+H]$^+$, retention time: 1.83 minutes, purity: 85% (214 nm) (LC-MS Method 021).

Methyl (2S)-3-[6-[22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]-2-pyridyl]-2-methyl-propanoate

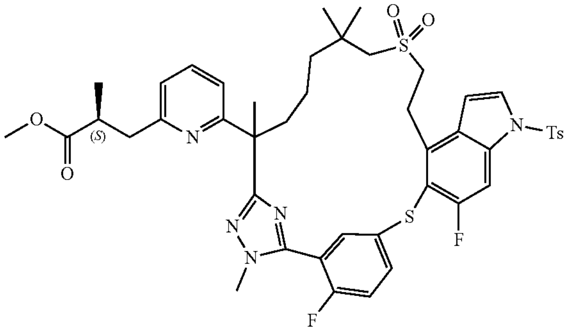

Step B: To a solution of Step A product (528 mg, 0.7 mmol) in acetonitrile (10 mL) was added 1-(p-tolylsulfonyl)imidazole (191.4 mg, 0.86 mmol) and 1,8-diazabicyclo[5,4,0]undec-7-ene (109.2 mg, 152.2 mmol). The mixture was stirred at room temperature overnight, then diluted with water (30 mL), and extracted with ethyl acetate (3×20 mL). The combined organic extracts were washed with brine, dried over magnesium sulfate, and concentrated. The residue was purified by automated flash chromatography (20 g silica gel column, eluted with 0-80% ethyl acetate in petroleum ether) to give the title compound (520 mg, 85%) as a solid. MS (ESI): 890 m/z [M+H]$^+$, retention time: 2.04 minutes, purity: 81% (214 nm) (LC-MS Method 011).

The first Eluent: Methyl rac-(2S)-3-[6-[22,28-difluoro-3,6,10,10-tetramethyl-12,12,24-trioxo-19-(p-tolylsulfonyl)-12λ6,24)14-dithia-3,4,19,30-tetrazapentacyclo[23.3.1.12,5.015,23.016,20]-triaconta-1(29),2(30),4,15,17,20,22,25,27-nonaen-6-yl]-2-pyridyl]-2-methyl-propanoate

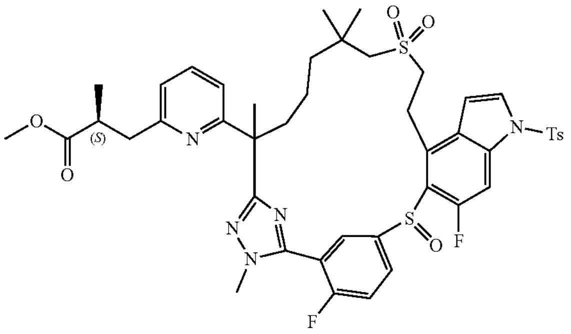

And the second eluent: methyl (2S)-3-[6-[22,28-difluoro-3,6,10,10-tetramethyl-12,12,24,24-tetraoxo-19-(p-tolylsulfonyl)-12λ6,24 6-dithia-3,4,19,30-tetrazapentacyclo-[23.3.1.12,5.015,23.016,20] triaconta-1(29),2(30),4,15,17,20,22,25,27-nonaen-6-yl]-2-pyridyl]-2-methyl-propanoate

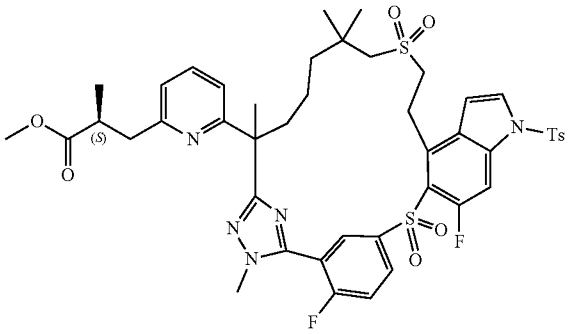

Step C: To a stirred and cooled (0° C.) solution of Step B product (520 mg, 0.58 mmol) in methanol (10 mL) was added a solution of ammonium molybdate tetrahydrate (722 mg) in hydrogen peroxide (30% in water, 3.6 mL). The reaction was stirred at 0° C. for 1 hour, then diluted with ethyl acetate (50 mL). The solution was washed with water, dried over sodium sulfate, and concentrated. The residue was purified by automated silica gel column chromatography (25 g silica gel column, eluted with 0-60% ethyl acetate in petroleum ether). The first eluent (300 mg, 57%) was obtained as a solid. MS (ESI): 906 m/z $[M+H]^+$, retention time: 1.90 minutes, purity: 95% (254 nm) (LC-MS Method 021).

The second eluent (104 mg, 19%), the over oxidation product, was also obtained as a solid. MS (ESI): 922 m/z $[M+H]^+$, retention time: 1.94 minutes, purity: 92% (254 nm) (LC-MS Method 021).

Diastereomer mixtures A and B of methyl (2S)-3-[6-(22,28-difluoro-3,6,10,10-tetramethyl-12,12,24-trioxo-12λ6,24λ4-dithia-3,4,19,30-tetrazapentacyclo [23.3.1.12,5.015,23.016,20]-triaconta-1(29),2(30),4,15,17,20,22,25,27-nonaen-6-yl)-2-pyridyl]-2-methyl-propanoate (from First Eluent of Step C Product)

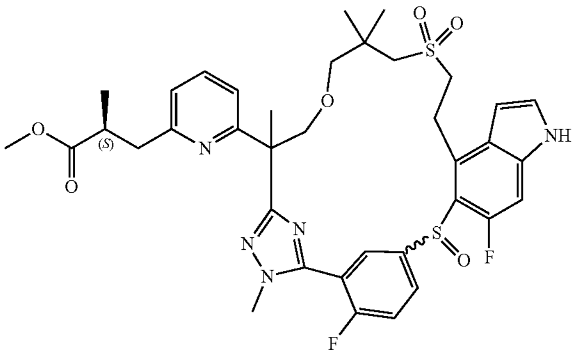

Step D: To a solution of the first eluent of Step C product (300 mg, 0.33 mmol) in methanol (10 mL) was added potassium carbonate (91.5 mg, 0.66 mmol). The reaction was stirred at room temperature for 1 hour, then diluted with ethyl acetate (80 mL). The mixture was washed with brine, dried over sodium sulfate, filtered, and concentrated. The residue was purified by prep-HPLC to give two eluents, two pairs of diastereomer mixtures of the title compound. The first peak, Diastereomer A, is the first pair of diastereomer mixtures (124 mg, 50%) as solid. MS (ESI): 752 m/z $[M+H]^+$, retention time: 1.69 minutes, purity: 96% (254 nm). (LC-MS Method 021).

The second peak, Diastereomer B, is the second pair of diastereomer mixtures (74 mg, 30%) as solid. MS (ESI): 752 m/z $[M+H]^+$, retention time: 1.71 minutes, purity: 94% (254 nm) (LC-MS Method 021).

Compounds 179A and 179B: Diastereomers 1 and 2 of (2S)-3-[6-(22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl)-2-pyridyl]-2-methyl-propanoic Acid (from Diastereomer Mixture A of Step D Product)

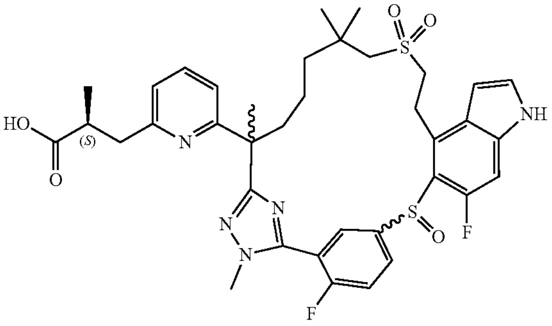

Diastereomer 1
Diastereomer 2

Step E: The diastereomer mixture A of Step D products (124 mg, 0.165 mmol) was subjected to chiral SFC separation under the following condition: Instrument: SFC-150 (Waters); Column: AS 20*250 mm, 10 μm; Column temperature: 35° C.; Mobile phase: carbon dioxide/methanol (0.2% ammonia (7M ammonia in methanol) as additive) =65/35; Flow rate: 100 g/minutes; Back pressure: 100 bar; Detection wavelength: 214 nm; Cycle time: 3.3 minutes; Sample solution: 124 mg dissolved in 18 mL methanol and dichloromethane; Injection volume: 1.5 mL. The first eluent, Diastereomer 1 (50 mg, 40%, white solid); was further hydrolyzed (simultaneous deprotection) to Example Compound 179A (29.3 mg, 60%, white solid). The second eluent, Diastereomer 2 (48 mg, 39%, white solid), was further hydrolyzed (simultaneous deprotection) to Compound 179B (25.3 mg, 54%, white solid), following the procedure described in Step F of example 6, with only tetrahydrofuran and water (no methanol) as reaction solvents.

Compound 179A, Diastereomer 1: MS (ESI): 738 m/z $[M+H]^+$, retention time: 1.55 minutes, purity: >99% (254 nm) (LC-MS Method 021). $^1H$ NMR (400 MHz, $CD_3OD$) δ 8.38-7.90 (m, 2H), 7.63-7.50 (m, 2H), 7.37 (d, J=3.2 Hz, 1H), 7.20-7.10 (m, 1H), 7.02 (d, J=7.2 Hz, 1H), 6.83 (d, J=8.0 Hz, 1H), 6.68 (brs, 1H), 4.18-3.96 (m, 1H), 3.80 (s, 3H), 3.66-3.41 (m, 2H), 3.18-2.98 (m, 4H), 2.86-2.81 (m, 1H), 2.53-2.44 (m, 1H), 1.97-1.87 (m, 1H), 1.79-1.49 (m, 5H), 1.43-1.34 (m, 1H), 1.29-0.91 (m, 11H) ppm.

Compound 179B, Diastereomer 2: MS (ESI): 738 m/z $[M+H]^+$, retention time: 1.56 minutes, purity: >99% (254 nm) (LC-MS Method 021). $^1H$ NMR (400 MHz, $CD_3OD$) δ 8.30-7.93 (m, 2H), 7.63-7.52 (m, 2H), 7.37 (d, J=3.6 Hz, 1H), 7.21-7.12 (m, 1H), 7.03 (d, J=7.6 Hz, 1H), 6.88 (d, J=7.6 Hz, 1H), 6.68 (brs, 1H), 4.22-4.00 (m, 1H), 3.80 (s, 3H), 3.66-3.41 (m, 2H), 3.17-2.94 (m, 4H), 2.86-2.79 (m, 1H), 2.48-2.41 (m, 1H), 1.97-1.86 (m, 1H), 1.73-1.42 (m, 5H), 1.39-1.33 (m, 1H), 1.29-0.96 (m, 11H) ppm.

Compounds 179C and 179D: Diastereomers 3 and 4 of (2S)-3-[6-(22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl)-2-pyridyl]-2-methyl-propanoic Acid (from Diastereomer Mixture B of Step D Product)

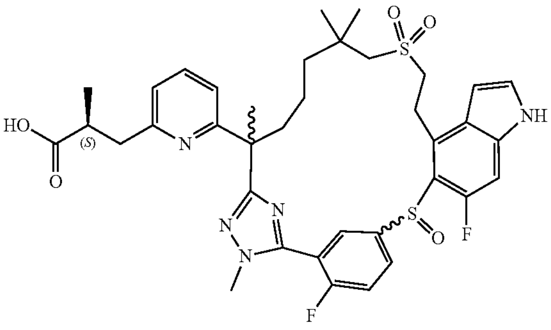

Diastereomer 3
Diastereomer 4

Step F: The diastereomer mixture B of Step D products (74 mg, 0.098 mmol) was subject to chiral SFC separation under the following condition: Instrument: SFC-150 (Waters); Column: AD 20*250 mm, 10 μm; Column temperature: 35° C.; Mobile phase: carbon dioxide/isopropanol (0.5% ammonia (7M ammonia in methanol) as additive) =65/35; Flow rate: 100 g/minutes; Back pressure: 100 bar; Detection wavelength: 214 nm; Cycle time: 2.73 minutes; Sample solution: 74 mg dissolved in 15 mL methanol; Injection volume: 1 mL. The first eluent, Diastereomer 3 (25 mg, 34%), was further hydrolyzed (simultaneous deprotection) to Compound 179C (20.9 mg, 84%, white solid). The second eluent, Diastereomer 4 (31 mg, 42%), was further hydrolyzed (simultaneous deprotection) to Compound 179D (26 mg, 85%, white solid), following the procedure described in Step F of Example 6, with only tetrahydrofuran and water (no methanol) as reaction solvents.

Compound 179C, Diastereomer 3: MS (ESI): 738 m/z $[M+H]^+$, retention time: 1.63 minutes, purity: >99% (254 nm). (LC-MS Method 021). $^1H$ NMR (400 MHz, $CD_3OD$) δ 8.17-8.09 (m, 1H), 7.97-7.85 (m, 1H), 7.59-7.50 (m, 2H), 7.37 (d, J=3.2 Hz, 1H), 7.16 (d, J=10.4 Hz, 1H), 7.01 (d, J=7.6 Hz, 1H), 6.91 (d, J=7.6 Hz, 1H), 6.67 (brs, 1H), 3.93-3.83 (m, 4H), 3.70-3.61 (m, 1H), 3.52-3.45 (m, 1H), 3.16-2.93 (m, 5H), 2.85-2.79 (m, 1H), 2.31-2.24 (m, 1H), 2.13-2.05 (m, 1H), 1.74 (s, 3H), 1.43-1.39 (m, 2H), 1.19-1.03 (m, 11H) ppm.

Compound 179D, Diastereomer 4: MS (ESI): 738 m/z $[M+H]^+$, retention time: 1.63 minutes, purity: >99% (254 nm). (LC-MS Method 021). $^1H$ NMR (400 MHz, $CD_3OD$) δ 8.17-8.09 (m, 1H), 7.97-7.85 (m, 1H), 7.59-7.50 (m, 2H), 7.37 (d, J=3.2 Hz, 1H), 7.16 (d, J=10.4 Hz, 1H), 7.01 (d, J=7.6 Hz, 1H), 6.91 (d, J=7.6 Hz, 1H), 6.67 (brs, 1H), 3.93-3.83 (m, 4H), 3.70-3.61 (m, 1H), 3.52-3.45 (m, 1H), 3.16-2.93 (m, 5H), 2.85-2.79 (m, 1H), 2.31-2.24 (m, 1H), 2.13-2.05 (m, 1H), 1.74 (s, 3H), 1.43-1.39 (m, 2H), 1.19-1.03 (m, 11H) ppm.

Compounds 180A and 180B: Diastereomers 1 and 2 of (2S)-3-[6-(22,28-difluoro-3,6,10,10-tetramethyl-12,12,24,24-tetraoxo-12λ6,24 6-dithia-3,4,19,30-tetrazapentacyclo[23.3.1.12,5.015,23.016,20]triaconta-1(29),2(30),4,15,17,20,22,25,27-nonaen-6-yl)-2-pyridyl]-2-methyl-propanoic Acid

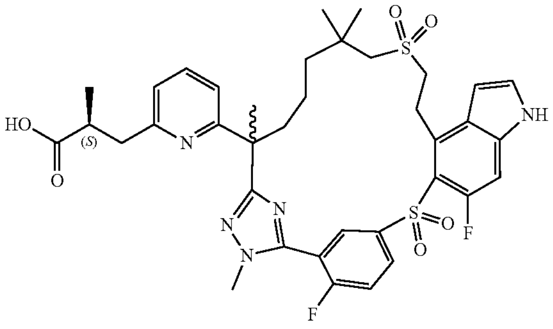

Diastereomer 1
Diastereomer 2

Step G: The second eluent of Step C product (124 mg, 0.165 mmol) was subject to chiral SFC separation under the following condition: Instrument: SFC-200 (Waters); Column: IG 20*250 mm, 10 μm; Column temperature: 35° C.; Mobile phase: carbon dioxide/methanol (0.2% ammonia (7M ammonia in methanol) as additive)=45/55; Flow rate: 100 g/minutes; Back pressure: 100 bar; Detection wavelength: 214 nm; Cycle time: 6.5 minutes; Sample solution: 100 mg dissolved in 15 mL methanol; Injection volume: 1 mL. The first eluent, Diastereomer 1 (35 mg, 34%), was further hydrolyzed, and simultaneously deprotected as Compound 180A (11 mg, 38%). The second eluent, Diastereomer 2, was further hydrolyzed, and simultaneously deprotected to 180B (30 mg, 29%) as white solids, following the procedure described in Step F of Example 6, with only tetrahydrofuran and water (no methanol) as reaction solvents.

Compound 180A, Diastereomer 1: MS (ESI): 754 m/z $[M+H]^+$, retention time: 1.63 minutes, purity: >99% (254 nm) (LC-MS Method 021). $^1H$ NMR (400 MHz, $CD_3OD$) δ 8.39-8.30 (m, 2H), 7.62 (t, J=9.2 Hz, 1H), 7.51 (t, J=8.0 Hz, 1H), 7.40 (d, J=3.2 Hz, 1H), 7.20 (d, J=12.0 Hz, 1H), 7.02 (d, J=7.6 Hz, 1H), 6.86 (d, J=8.0 Hz, 1H), 6.73 (d, J=3.2 Hz, 1H), 3.94-3.75 (m, 4H), 3.54-3.41 (m, 2H), 3.17-3.12 (m, 3H), 3.01-2.94 (m, 1H), 2.85-2.80 (m, 1H), 2.49-2.39 (m, 1H), 2.01-1.94 (m, 1H), 1.74 (s, 3H), 1.56-1.43 (m, 3H), 1.32-1.21 (m, 8H), 1.12 (d, J=7.2 Hz, 3H) ppm.

Compound 180B, Diastereomer 2: MS (ESI): 754 m/z $[M+H]^+$, retention time: 1.63 minutes, purity: >99% (254 nm). (LC-MS Method 021). $^1H$ NMR (400 MHz, $CD_3OD$) δ 8.39-8.30 (m, 2H), 7.62 (t, J=9.2 Hz, 1H), 7.51 (t, J=8.0

Hz, 1H), 7.40 (d, J=3.2 Hz, 1H), 7.20 (d, J=12.0 Hz, 1H), 7.02 (d, J=7.6 Hz, 1H), 6.91 (d, J=8.0 Hz, 1H), 6.73 (d, J=3.2 Hz, 1H), 3.94-3.75 (m, 4H), 3.54-3.41 (m, 2H), 3.16-3.09 (m, 3H), 3.01-2.90 (m, 1H), 2.85-2.76 (m, 1H), 2.49-2.39 (m, 1H), 2.01-1.94 (m, 1H), 1.74 (s, 3H), 1.56-1.43 (m, 3H), 1.32-1.21 (m, 8H), 1.13 (d, J=7.2 Hz, 3H) ppm.

Example 181. Diastereomers 1, 2, 3 and 4 of (2R)-3-[6-(22,28-difluoro-3,6,10,10-tetramethyl-12,12,24-trioxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl)-2-pyridyl]-2-methyl-propanoic Acid

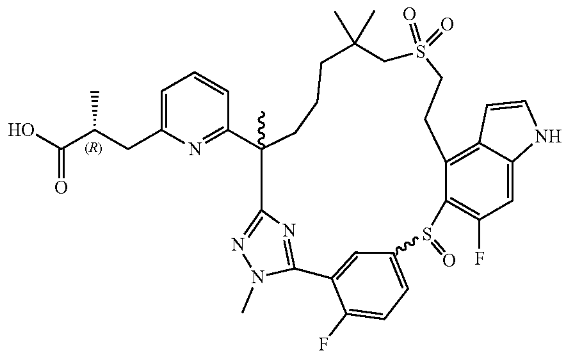

Diastereomer 1; Diastereomer 2; Diastereomer 3; Diastereomer 4.

Methyl (2R)-3-[6-[22,28-difluoro-3,6,10,10-tetramethyl-12,12,24-trioxo-19-(p-tolylsulfonyl)-12λ6,24λ4-dithia-3,4,19,30-tetrazapentacyclo[23.3.1.12,5.015,23.016,20]-triaconta-1(29),2(30),4,15,17,20,22,25,27-nonaen-6-yl]-2-pyridyl]-2-methyl-propanoate

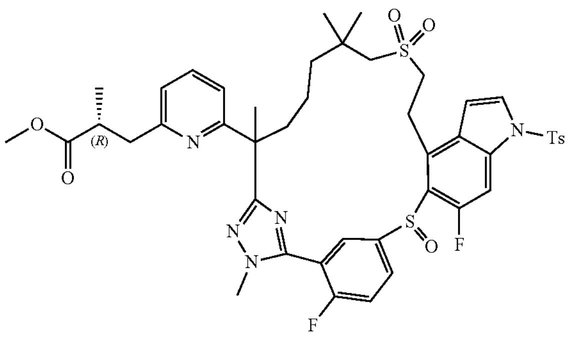

Step A: Exchanging methyl (2S)-3-(6-(7-((2-hydroxyethyl)sulfonyl)-2,6,6-trimethyl-1-(2-methylhydrazineyl)-1-oxoheptan-2-yl)pyridin-2-yl)-2-methylpropanoate (Intermediate 107-2) with methyl (2R)-3-(6-(7-((2-hydroxyethyl)sulfonyl)-2,6,6-trimethyl-1-(2-methylhydrazineyl)-1-oxoheptan-2-yl)pyridin-2-yl)-2-methylpropanoate (Intermediate 107-3, 580 mg, 1.19 mmol), the reaction procedure sequence (Steps A to C), as described in the Example 179A and 179B, was used to prepare the title compound (200 mg). MS (ESI): 906 m/z $[M+H]^+$, retention time: 1.81 minutes, purity: >99% (214 nm) (LC-MS Method 021).

Diastereomers A (mixture of 1 and 2) of Methyl (2R)-3-[6-[22,28-difluoro-3,6,10,10-tetramethyl-12,12,24-trioxo-19-(p-tolylsulfonyl)-12λ6,24λ4-dithia-3,4,19,30-tetrazapentacyclo-[23.3.1.12,5.015,23.016,20]triaconta-1(29),2(30),4,15,17,20,22,25,27-nonaen-6-yl]-2-pyridyl]-2-methyl-propanoate

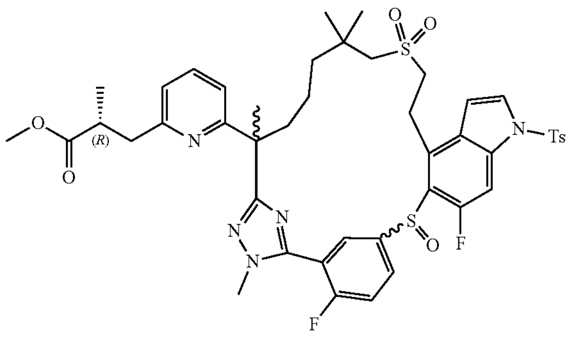

First Eluent: Diastereomers 1 and 2

And compounds 181C and 181D: Diastereomers 3 and 4 of (2R)-3-[6-(22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl)-2-pyridyl]-2-methyl-propanoic Acid

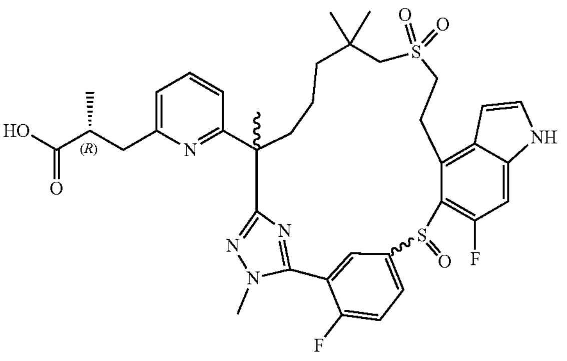

Second Eluent: Diastereomer 3
Third Eluent: Diastereomer 4

Step B: The Step A product was subject to chiral SFC purification under the following condition: Instrument: SFC-80 (Thar, Waters); Column: IH 20*250 mm, 10 μm; Column temperature: 35° C.; Mobile phase: carbon dioxide/methanol (0.2% ammonia (7 M ammonia in methanol) as additive)= 55/45; Flow rate: 80 g/minutes; Back pressure: 100 bar; Detection wavelength: 214 nm; Cycle time: 6.5 minutes; Sample solution: 200 mg dissolved in 20 mL methanol; Injection volume: 1.0 mL. The four diastereomers were separated to three different eluents. The first eluent, a mixture of diastereomers 1 and 2, was designated as Diastereomer A (80 mg, 40%). The second eluent, diastereomer 3 (33 mg, 16%), was further hydrolyzed, and simultaneously deprotected to Compound 181C. The third eluent, Diastereomer 4 (30 mg, 15%), was further hydrolyzed, and simultaneously deprotected to Compound 181D. Diastereomer A: MS (ESI): 906 m/z $[M+H]^+$, retention time: 1.99 minutes, purity: 99% (214 nm). (LC-MS Method 003). Chiral-HPLC: 100%.

Compound 181C, Diastereomer 3: MS (ESI): 738 m/z $[M+H]^+$, retention time: 1.49 minutes, purity: 99% (214 nm). (LC-MS Method 027). $^1H$ NMR (400 MHz, $CD_3OD$) δ 8.67-7.80 (m, 2H), 7.65-7.50 (m, 2H), 7.37 (d, J=3.2 Hz, 1H), 7.20-7.12 (m, 1H), 7.02 (d, J=7.6 Hz, 1H), 6.83 (d, J=7.6 Hz, 1H), 6.68 (s, 1H), 4.22-3.47 (m, 6H), 3.18-2.97 (m, 4H), 2.86-2.78 (m, 1H), 2.51-2.43 (m, 1H), 1.99-1.80 (m, 1H), 1.77-1.49 (m, 5H), 1.45-1.33 (m, 1H), 1.29-1.04 (m, 11H) ppm. Chiral-HPLC: 100% (chiral HPLC method: Column: IG-3, 4.6*100 mm, 3 μm; Mobile phase: carbon dioxide/ethanol (1% ammonia (7 M ammonia in methanol) as additive); Run time: 6 minutes; Flow rate: 3.0 mL/minutes; Back pressure: 2000 psi. retention time: 2.93 minutes).

Compound 181D, Diastereomer 4: MS (ESI): 738 m/z $[M+H]^+$, retention time: 1.49 minutes, purity: 99% (214 nm) (LC-MS Method 027). $^1H$ NMR (400 MHz, $CD_3OD$)δ 8.20-7.80 (m, 2H), 7.61-7.48 (m, 2H), 7.37 (d, J=3.6 Hz, 1H), 7.19-7.15 (m, 1H), 7.02 (d, J=7.6 Hz, 1H), 6.91 (d, J=8.0 Hz, 1H), 6.67 (s, 1H), 3.99-3.79 (m, 4H), 3.70-3.62 (m, 1H), 3.57-3.42 (m, 1H), 3.16-2.91 (m, 4H), 2.83-2.77 (m, 1H), 2.32-2.22 (m, 1H), 2.15-2.04 (m, 1H), 1.73 (s, 3H), 1.52-1.36 (m, 3H), 1.29-0.96 (m, 11H) ppm. Chiral HPLC: 99.8% (Chiral method same as Compound 181C, retention time: 2.26).

Compounds 181A, and 181B: Diastereomers 1 and 2 of (2R)-3-[6-[22,28-difluoro-3,6,10,10-tetramethyl-12,12,24-trioxo-12λ6,24λ4-dithia-3,4,19,30-tetrazapentacyclo-[23.3.1.12,5.015,23.016,20]triaconta-1(29),2(30),4,15,17,20,22,25,27-nonaen-6-yl]-2-pyridyl]-2-methyl-propanoic acid

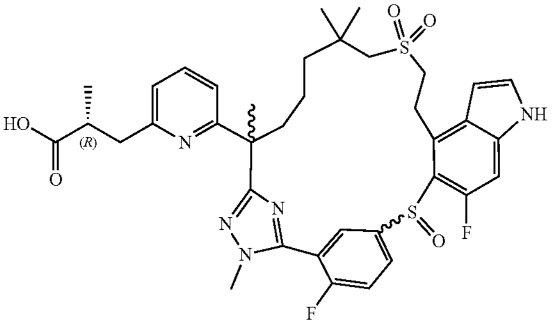

First Fraction from Diasteromer A: Diastereomer 1
Second Fraction from Diasteromer A: Diastereomer 2

Step C: To a solution of Diastereomer A of Step B product (80 mg, 0.09 mmol) in tetrahydrofuran/water (6 mL/2 mL/) was added lithium hydroxide monohydrate (19 mg, 0.44 mmol). The reaction was stirred at room temperature for 1 hour, then acidified with 1 N hydrochloric acid to pH ~4 and diluted with ethyl acetate. The mixture was washed with brine, dried over sodium sulphate, and concentrated. The residue was purified with prep-HPLC to give two fractions. The first fraction, enantiomer 1, was designated as Compound 181A (18 mg, 27%, white solid). The second fraction, enantiomer 2, was designated as Compound 181B (12 mg, 19%, white solid).

Compound 181A: MS (ESI): 738 m/z $[M+H]^+$, retention time: 1.49 minutes, purity: 98% (214 nm). (LC-MS Method 027). Chiral-HPLC: 99.7%. $^1H$ NMR (400 MHz, $CD_3OD$)6 8.43-7.84 (m, 2H), 7.65-7.51 (m, 2H), 7.37 (d, J=3.6 Hz, 1H), 7.22-7.15 (m, 1H), 7.03 (d, J=7.6 Hz, 1H), 6.89 (d, J=7.6 Hz, 1H), 6.68 (s, 1H), 4.22-3.69 (m, 4H), 3.65-3.37 (m, 2H), 3.18-2.89 (m, 4H), 2.83-2.79 (m, 1H), 2.50-2.38 (m, 1H), 1.97-1.90 (m, 1H), 1.87-1.52 (m, 5H), 1.42-1.33 (m, 1H), 1.29-1.03 (m, 11H) ppm.

Compound 181B: MS (ESI): 738 m/z $[M+H]^+$, retention time: 1.50 minutes, purity: 99% (214 nm). (LC-MS Method 027). Chiral-HPLC: 99.5%. $^1H$ NMR (400 MHz, $CD_3OD$) δ 8.12-7.77 (m, 2H), 7.61-7.47 (m, 2H), 7.37 (d, J=3.2 Hz, 1H), 7.20-7.12 (m, 1H), 7.01 (d, J=7.2 Hz, 1H), 6.88 (d, J=8.0 Hz, 1H), 6.67 (s, 1H), 3.97-3.74 (m, 4H), 3.75-3.63 (m, 1H), 3.55-3.40 (m, 1H), 3.16-2.90 (m, 4H), 2.85-2.77 (m, 1H), 2.33-2.45 (m, 1H), 2.13-2.06 (m, 1H), 1.73 (s, 3H), 1.51-1.38 (m, 3H), 1.30-1.00 (m, 11H) ppm.

Example 182. Diastereomer 1 of 2-(4-methylpiperazin-1-yl)ethyl (2R)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate

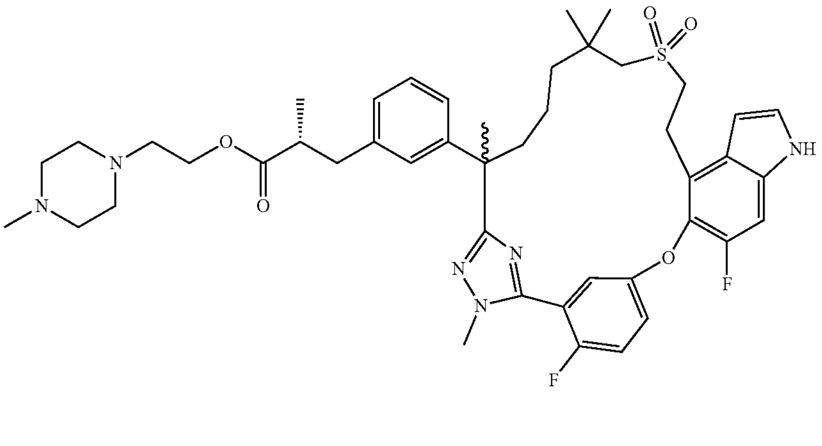 [SMILES: C[C@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)OCCN1CCN(C)CC1]

To a solution of Diastereomer 1 of (2R)-3-[3-[22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid (Diastereomer 1 of Example 6, 150 mg, 0.213 mmol) in dichloromethane (1.5 mL) was added 2-(4-methylpiperazin-1-yl)ethan-1-ol ((37 mg, 0.255 mmol), N-(3-dimethylaminopropyl)-N'-ethylcarbodiimide hydrochloride (45 mg, 0.234 mmol) and 4-dimethylaminopyridine (2.6 mg, 0.0213 mmol). The mixture was stirred at room temperature for 12 hours, then quenched with water (10 mL) and extracted with ethyl acetate (3×10 mL). The organic phase was washed with brine (30 mL), dried over sodium sulfate, and concentrated. The residue was purified by silica gel column chromatography (40 g silica gel column, eluted with 0 to 10% methanol in dichloromethane to give the title compound (84 mg, 47.50%) as a white solid. MS (ESI): 831 m/z $[M+H]^+$, retention time: 1.64 minutes, purity: >99% (214 nm) (LC-MS Method 003). $^1H$ NMR (400 MHz, $CD_3OD$) δ 7.46-7.41 (m, 2H), 7.32 (d, J=10.7 Hz, 1H), 7.29-7.25 (m, 2H), 7.12 (t, J=7.6 Hz, 1H), 7.00-6.91 (m, 3H), 6.50 (s, 1H), 4.02-3.95 (m, 2H), 3.78 (d, J=1.6 Hz, 3H), 3.24-3.09 (m, 4H), 2.96 (d, J=13.6 Hz, 1H), 2.85-2.72 (m, 2H), 2.65-2.55 (m, 3H), 2.39 (t, J=5.8 Hz, 3H), 2.30-2.20 (m, 6H), 2.10 (s, 3H), 1.73-1.43 (m, 5H), 1.25-1.10 (m, 4H), 1.05-0.95 (m, 9H) ppm.

Example 183. Diastereomers 1 and 2 of (2R)-3-[3-(22-fluoro-3,6,10,10-tetramethyl-12,12-dioxo-24-oxa-12λ6-thia-3,4,19,30-tetrazapentacyclo-[23.3.1.12,5.015,23.016,20]triaconta-1(29),2(30),4,15(23),16(20),17,21,25,27-nonaen-6-yl)phenyl]-2-methyl-propanoic Acid

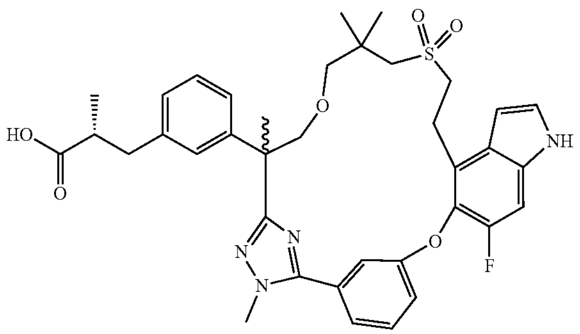 [SMILES: C[C@H](Cc1cccc(C2(C)COCC(C)(C)CS(=O)(=O)CCc3c(c(F)cc4[nH]ccc34)Oc3cccc(c3)-c3nc2nn3C)c1)C(=O)O]

Exchanging methyl 5-((4-bromo-6-fluoro-1H-indol-5-yl)oxy)-2-fluorobenzimidothioate hydroiodide (Intermediate 14-1) with methyl 3-((4-bromo-6-fluoro-1H-indol-5-yl)oxy)-benzimidothioate hydroiodide (Intermediate 14-9, 0.80 g, 1.86 mmol), the reaction procedure sequence (Steps A to G) described for Example 6 was used to prepare the title compounds. The racemic methyl ester (141 mg), obtained from corresponding Step D of Example 6, was subject to chiral SFC separation under the following condition: Instrument: SFC-80 (Thar, Waters); Column: IH 20*250 mm, 10 μm; Column temperature: 35° C.; Mobile phase: carbon dioxide/methanol (0.2% ammonia (7 N ammonia in methanol) as additive)=65/35; Flow rate: 80 g/minute; Back pressure: 100 bar; Detection wavelength: 214 nm; Cycle time: 4.0 minutes; Sample solution: 141 mg dissolved in 20 mL methanol; Injection volume: 1.0 mL. The first eluent, diastereomer 1 (58 mg, 41%), was further hydrolyzed to Compound 183A (40 mg, 69%). The second eluent, diastereomer 2 (48 mg, 33%), was further hydrolyzed to Compound 183B (35 mg, 73%), as described in corresponding Steps F and G of Example 6.

Compound 183A: MS (ESI): 687 m/z $[M+H]^+$, retention time: 1.88 minutes, purity: >99% (214 nm). (LC-MS Method 003). $^1H$ NMR (400 MHz, $CD_3OD$) δ 7.60 (t, J=8.0 Hz, 1H), 7.50 (d, J=7.2 Hz, 1H), 7.36 (s, 1H), 7.34 (d, J=3.2 Hz, 1H), 7.29-7.24 (m, 2H), 7.19 (t, J=7.6 Hz, 1H), 7.06-7.00 (m, 3H), 6.65 (d, J=3.2 Hz, 1H), 4.02 (s, 3H), 3.42-3.37 (m, 2H), 3.19-3.14 (m, 2H), 2.96-2.92 (m, 1H), 2.75-2.58 (m, 4H), 2.12-2.08 (m, 1H), 1.89-1.82 (m, 1H), 1.67 (s, 3H), 1.52-1.48 (m, 1H), 1.31-1.23 (m, 2H), 1.09 (d, J=6.4 Hz, 3H), 1.04 (s, 6H), 0.94-0.88 (m, 1H) ppm.

Compound 183B: MS (ESI): 687 m/z $[M+H]^+$, retention time: 1.88 minutes, purity: 99% (214 nm). (LC-MS Method 003). $^1H$ NMR (400 MHz, $CD_3OD$) δ 7.59 (t, J=8.0 Hz, 1H), 7.50 (d, J=7.6 Hz, 1H), 7.36 (s, 1H), 7.33 (d, J=3.2 Hz, 1H), 7.29-7.24 (m, 2H), 7.18 (t, J=7.6 Hz, 1H), 7.07 (s, 1H), 7.04-7.00 (m, 2H), 6.65 (d, J=3.2 Hz, 1H), 4.01 (s, 3H), 3.44-3.35 (m, 2H), 3.20-3.12 (m, 2H), 2.98-2.92 (m, 1H), 2.75-2.58 (m, 4H), 2.16-2.09 (m, 1H), 1.91-1.81 (m, 1H), 1.67 (s, 3H), 1.52-1.48 (m, 1H), 1.31-1.24 (m, 2H), 1.10 (d, J=6.4 Hz, 3H), 1.04 (s, 6H), 0.94-0.88 (m, 1H) ppm.

Example 184. Diastereomer 1 of (2R)-3-[3-(22-fluoro-3,6,10,10-tetramethyl-12,12-dioxo-24-oxa-12λ6-thia-3,4,19,26,30-pentazapentacyclo[23.3.1.12,5.015,23.016,20]triaconta-1(29),2(30),4,15,17,20,22,25,27-nonaen-6-yl)phenyl]-2-methyl-propanoic acid

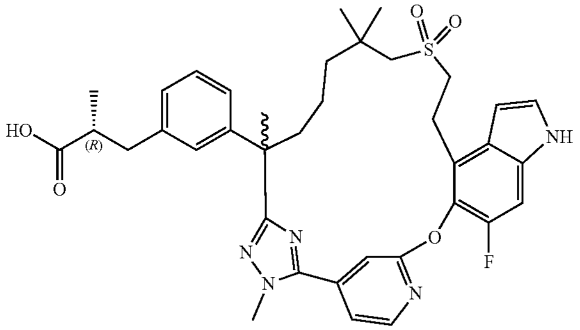

Exchanging methyl 5-((4-bromo-6-fluoro-1H-indol-5-yl)oxy)-2-fluorobenzimidothioate hydroiodide (Intermediate 14-1) with methyl 2-((4-bromo-6-fluoro-1H-indol-5-yl)oxy)pyridine-4-carbimidothioate hydroiodide (Intermediate 133, 0.46 g, 0.90 mmol), and methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with Diastereomer 1 of methyl (R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69-23, 0.33 g, 0.689 mmol), the reaction procedure sequence (steps A to D, F) described for Example 6 was used to prepare the title compound (11.9 mg). MS (ESI): 688 m/z $[M+H]^+$, retention time: 2.00 minutes, purity: 98% (214 nm). (LC-MS Method 027). $^1H$ NMR (400 MHz, $CD_3OD$) δ 8.16 (d, J=4.0 Hz, 1H), 7.45 (s, 1H), 7.38 (dd, J=0.8, 4.0 Hz, 1H), 7.33 (d, J=2.4 Hz, 1H), 7.18 (d, J=7.6 Hz, 1H), 7.16-7.13 (m, 2H), 7.10-7.08 (m, 1H), 7.01-6.99 (m, 1H), 6.58 (d, J=2.4 Hz, 1H), 4.06 (s, 3H), 3.28-3.27 (m, 2H), 3.23-3.21 (m, 2H), 2.96-2.90 (m, 1H), 2.87-2.80 (m, 2H), 2.66-2.59 (m, 2H), 2.24-2.18 (m, 1H), 2.10-2.06 (m, 1H), 1.73 (s, 3H), 1.48-1.34 (m, 2H), 1.22-1.15 (m, 2H), 1.07 (d, J=5.2 Hz, 3H), 1.01 (s, 3H), 0.98 (s, 3H) ppm.

Example 185. Diastereomer 1 of (2S)-3-[3-(22,28-Difluoro-3,6,10,10-tetramethyl-12,12-dioxo-24-oxa-12λ6-thia-3,4,19,30-tetrazapentacyclo-[23.3.1.12,5.015,23.016,20]-triaconta-1(29),2(30),4,15,17,20,22,25,27-nonaen-6-yl)phenyl]-2-methyl-propanehydroxamic Acid

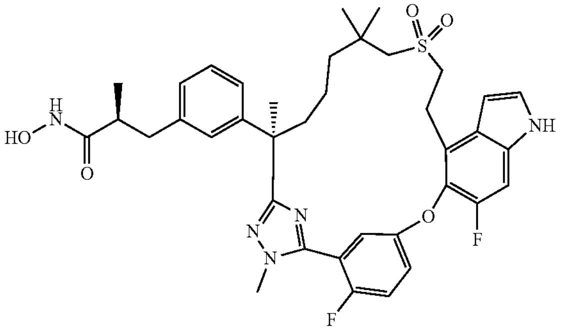 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3nc2nn3C)c1)C(=O)NO]

To a stirred solution of Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic acid (Example 7A, Diastereomer 1) (50 mg, 0.0709 mmol) in dry tetrahydrofuran (1.0 mL) was added N,N'-carbonyldiimidazole (23 mg, 0.142 mmol). The reaction mixture was stirred for 1 hour, treated with hydroxylamine hydrochloride (12 mg, 0.177 mmol). The mixture was stirred for 2 days, then diluted with water (5.0 mL), and extracted with ethyl acetate (2×15.0 mL). The combined organic phases were washed with brine, dried over sodium sulfate, and concentrated. The residue was purified by Prep-HPLC to give the title compound (20 mg, 39.36%) as a white solid. MS (ESI): 720 m/z $[M+H]^+$, retention time: 1.88 minutes, purity: 97% (214 nm) (LC-MS Method 003). $^1H$ NMR (400 MHz, DMSO-d6) δ 11.36 (s, 1H), 10.40 (s, 1H), 8.69 (bs, 1H), 7.46-7.42 (m, 2H), 7.32 (d, J=10.8 Hz, 1H), 7.28-7.24 (m, 2H), 7.11 (t, J=8.0 Hz, 1H), 7.03 (s, 1H), 6.95-6.89 (m, 2H), 6.51-6.50 (m, 1H), 3.78 (d, J=2.0 Hz, 3H), 3.31-3.09 (m, 4H), 2.95-2.92 (m, 1H), 2.83-2.77 (m, 2H), 2.45-2.31 (m, 2H), 2.11-2.04 (m, 1H), 1.74-1.67 (m, 1H), 1.61 (s, 3H), 1.52-1.44 (m, 1H), 1.26-1.16 (m, 2H), 1.02 (s, 3H), 0.98 (s, 3H), 1.02-0.98 (m, 1H), 0.90 (d, J=6.8 Hz, 3H) ppm.

Example 186. Diastereomer 1 of [[(2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]-triaconta-1(29),2(30),4,15,17,20,22,25,27-nonaen-6-yl)phenyl]-2-methyl-propanoyl]amino]N-hydroxycarbamate

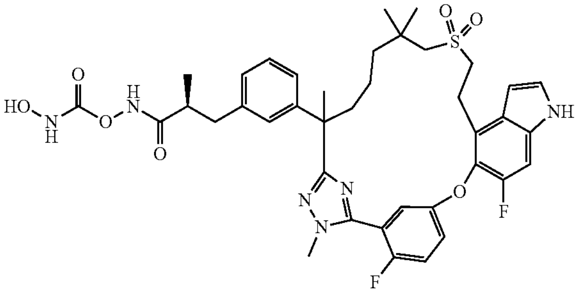 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)NOC(=O)NO]

To a stirred solution of Diastereomer 1 of (2S)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoic acid (Example 7, Diastereomer 1) (50 mg, 0.0709 mmol) in dry tetrahydrofuran (1.0 mL) was added N,N'-carbonyldiimidazole (23 mg, 0.142 mmol). The reaction mixture was stirred for 1 hour, treated with hydroxylamine hydrochloride (12 mg, 0.177 mmol). The mixture was stirred overnight, then additional N,N'-carbonyldiimidazole (23 mg, 0.142 mmol) and hydroxylamine hydrochloride (12 mg, 0.177 mmol) were added. The mixture was stirred for 1 hour at 40° C., then quenched with water (5.0 mL), and extracted with ethyl acetate (2×15.0 mL). The combined organic phases were washed with brine, dried over sodium sulfate, and concentrated. The residue was purified by Prep-HPLC to give the title compound (12 mg, 22%) as a white solid. MS (ESI): 779 m/z $[M+H]^+$, retention time: 1.86 minutes, purity: 96% (214 nm) (LC-MS Method 003). $^1H$ NMR (400 MHz, $DMSO-d_6$) δ 11.49 (s, 1H), 11.35 (s, 1H), 10.25 (s, 1H), 9.09 (s, 1H), 7.46-7.42 (m, 2H), 7.33 (d, J=10.8 Hz, 1H), 7.28-7.22 (m, 2H), 7.14-7.09 (m, 1H), 7.05-7.03 (m, 1H), 6.97-6.91 (m, 2H), 6.51 (s, 1H), 3.78 (d, J=1.6 Hz, 3H), 3.32-3.10 (m, 4H), 2.96-2.92 (m, 1H), 2.84-2.81 (m, 2H), 2.42-2.33 (m, 2H), 2.12-2.04 (m, 1H), 1.74-1.69 (m, 1H), 1.61 (s, 3H), 1.51-1.45 (m, 1H), 1.24-1.17 (m, 2H), 1.02-0.90 (m, 10H) ppm.

Example 187. Diastereomer 1 of (2S)-3-[3-(22,28-Difluoro-3,6,10,10-tetramethyl-12,12-dioxo-24-oxa-12λ6-thia-3,4,19,30-tetrazapentacyclo[23.3.1.12, 5.015,23.016,20]-triaconta-1(29),2(30),4,15,17,20, 22,25,27-nonaen-6-yl)phenyl]-N-hydroxy-N,2-dimethyl-propanamide

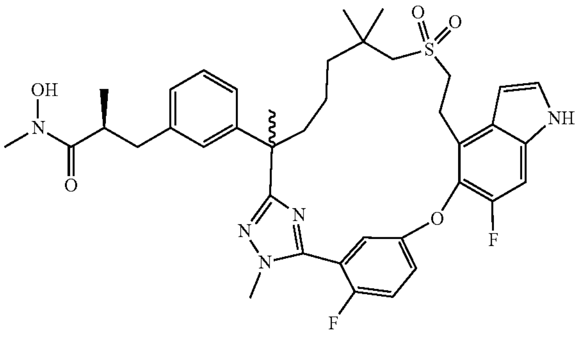 [SMILES: C[C@@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)N(C)O]

To a stirred solution of Diastereomer 1 of (2S)-3-[3-(22, 28-difluoro-3,6,10,10-tetramethyl-12,12-dioxo-24-oxa-12λ6-thia-3,4,19,30-tetrazapentacyclo[23.3.1.12,5.015, 23.016,20]triaconta-1(29),2(30),4,15,17,20,22,25,27-nonaen-6-yl)phenyl]-2-methyl-propanoic acid (Example 7A, Diastereomer 1) (50 mg, 0.0709 mmol) in dry tetrahydrofuran (1.0 mL) was added N,N'-carbonyldiimidazole (35 mg, 0.213 mmol). The reaction mixture was stirred for 1 hour, treated with N-methylhydroxylamine hydrochloride (12 mg, 0.142 mmol). The mixture was stirred overnight, then diluted with water (5.0 mL), and extracted with ethyl acetate (2×15.0 mL). The combined organic phases were washed with brine, dried over sodium sulfate, and concentrated. The residue was purified by Prep-HPLC to give the title compound (15 mg, 29%) as a white solid. MS (ESI): 734 m/z $[M+H]^+$, retention time: 1.95 minutes, purity: >99% (214 nm) (LC-MS Method 003). $^1H$ NMR (400 MHz, $CDCl_3$) δ 8.47 (s, 1H), 7.50-7.48 (m, 1H), 7.17-7.10 (m, 5H), 7.03-7.01 (m, 1H), 6.96-6.94 (m, 1H), 6.90 (s, 1H), 6.72 (s, 1H), 3.88 (d, J=2.0 Hz, 3H), 3.50-3.39 (m, 2H), 3.21-3.16 (m, 2H), 2.95-2.83 (m, 2H), 2.68-2.56 (m, 6H), 2.13-2.07 (m, 1H), 1.77-1.60 (m, 5H), 1.36-1.26 (m, 1H), 1.16-1.06 (m, 11H) ppm.

Example 188. Diastereomer 1 of (2S)-3-[3-(22,28-Difluoro-3,6,10,10-tetramethyl-12,12-dioxo-24-oxa-12λ6-thia-3,4,19,30-Tetrazapentacyclo[23.3.1.12, 5.015,23.016,20]-triaconta-1(29),2(30),4,15,17,20, 22,25,27-nonaen-6-yl)phenyl]-N-ethoxy-2-methyl-propanamide

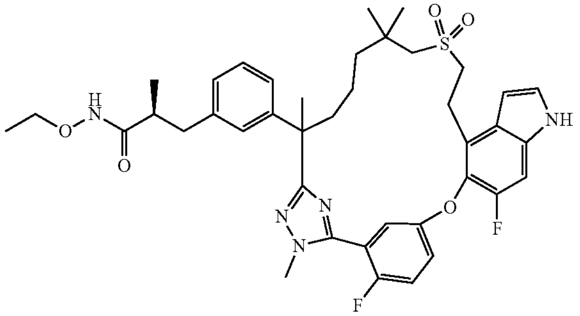 [SMILES: CCONC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1]

To a stirred solution of Diastereomer 1 of ethyl (2S)-3-[3-(22,28-difluoro-3,6,10,10-tetramethyl-12,12-dioxo-24-oxa-12λ6-thia-3,4,19,30-tetrazapentacyclo[23.3.1.12,5.015, 23.016,20]triaconta-1(29),2(30),4,15,17,20,22,25,27-nonaen-6-yl)phenyl]-2-methyl-propanoic acid (50 mg, 0.071 mmol) (Example 7, diastereomer 1) in dichloromethane (1 mL) was added 1-hydroxybenzotriazole (24 mg, 0.18 mmol), 1-(3-dimethylaminopropyl)-3-ethylcarbodiimide hydrochloride (34 mg, 0.18 mmol), O-ethylhydroxylamine hydrochloride (14 mg, 0.14 mmol) and triethylamine (40 μL, 0.28 mmol). The mixture was stirred at room temperature overnight, quenched with water (10 mL), and extracted with ethyl acetate (3×10 mL). The combined organic phases were washed with brine (10 mL), dried over sodium sulfate, and concentrated. The residue was purified by Prep-HPLC to give the title compound (24 mg, 45%) as a white solid. MS (ESI): 748 m/z $[M+H]^+$, retention time: 1.97 minutes, purity: >99% (214 nm). (LC-MS Method 003). $^1H$ NMR (400 MHz, $CD_3OD$) δ 7.38-7.31 (m, 2H), 7.31 (d, J=3.2 Hz, 1H), 7.22-7.12 (m, 3H), 7.02 (d, J=8.4 Hz, 1H), 6.90-6.97 (m, 2H), 6.61 (d, J=2.4 Hz, 1H), 3.85 (d, J=2.0 Hz, 3H), 3.70-3.53 (m, 2H), 3.42-3.31 (m, 3H), 3.24-3.17 (m, 1H), 2.88 (d, J=13.6 Hz, 1H), 2.78-2.73 (m, 2H), 2.62-2.57 (m, 1H), 2.36-2.30 (m, 1H), 2.17-2.09 (m, 1H), 1.84-1.74 (m, 1H), 1.66 (s, 3H), 1.57-1.46 (m, 1H), 1.32-1.23 (m, 2H), 1.10 (d, J=6.8 Hz, 3H), 1.07-0.96 (m, 10H) ppm.

Example 189. Diastereomer 1 of (2S)-3-[3-(22,28-Difluoro-3,6,10,10-tetramethyl-12,12-dioxo-24-oxa-12λ6-thia-3,4,19,30-tetrazapentacyclo[23.3.1.12, 5.015,23.016,20]-triaconta-1(29),2(30),4,15,17,20, 22,25,27-nonaen-6-yl)phenyl]-N-isopropoxy-2-methyl-propanamide

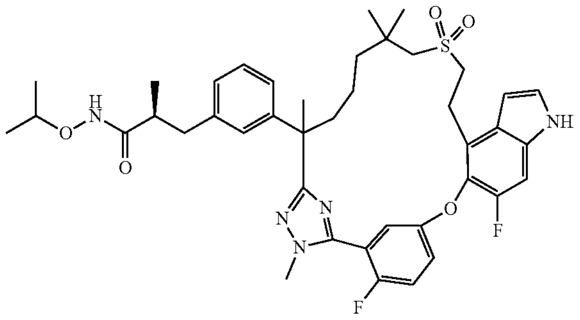 [SMILES: CC(C)ONC(=O)[C@@H](C)Cc1cccc(C2(C)CCCC(C)(C)CS(=O)(=O)CCc3c(c(F)cc4[nH]ccc34)Oc3ccc(F)c(c3)-c3nc2nn3C)c1]

To a stirred solution of Diastereomer 1 of ethyl (2S)-3-[3-(22,28-difluoro-3,6,10,10-tetramethyl-12,12-dioxo-24-oxa-12λ6-thia-3,4,19,30-tetrazapentacyclo[23.3.1.12,5.015, 23.016,20]triaconta-1(29),2(30),4,15,17,20,22,25,27-nonaen-6-yl)phenyl]-2-methyl-propanoic acid (Example 7A, diastereomer 1, 50 mg, 0.071 mmol) in dichloromethane (1 mL) was added 1-hydroxybenzotriazole (19 mg, 0.142 mmol), 1-(3-dimethylaminopropyl)-3-ethylcarboodiimide hydrochloride (27 mg, 0.14 mmol), 0-isopropyl hydroxylamine hydrochloride (12 mg, 0.11 mmol) and triethylamine (30 μL, 0.21 mmol). The mixture was stirred at room temperature for 2 hours, quenched with water (10 mL), and extracted with ethyl acetate (3×10 mL). The combined organic phases were washed with brine, dried over sodium sulfate, filtered, and concentrated. The residue was purified by Prep-HPLC to give the title compound (24 mg, 45%) as a white solid. MS (ESI): 762 m/z $[M+H]^+$, retention time: 2.00 minutes, purity: >99% (214 nm) (LC-MS Method 003). $^1H$ NMR (400 MHz, $CD_3OD$) δ 7.38-7.33 (m, 2H), 7.31 (d, J=3.2 Hz, 1H), 7.22-7.12 (m, 3H), 7.02 (d, J=8.4 Hz, 1H), 6.98-6.94 (m, 2H), 6.62 (dd, J=3.2, 0.8 Hz, 1H), 3.85 (d, J=2.0 Hz, 3H), 3.82-3.75 (m, 1H), 3.42-3.34 (m, 3H), 3.24-3.17 (m, 1H), 2.87 (d, J=13.6 Hz, 1H), 2.80-2.70 (m, 2H), 2.62-2.57 (m, 1H), 2.42-2.35 (m, 1H), 2.18-2.08 (m, 1H), 1.84-1.77 (m, 1H), 1.67 (s, 3H), 1.55-1.43 (m, 1H), 1.31-1.18 (m, 2H), 1.11 (d, J=6.8 Hz, 3H), 1.05-0.96 (m, 10H), 0.91 (d, J=6.0 Hz, 3H) ppm.

Example 190. (2R)-3-[3-[(6R)-28-fluoro-3,6,10,10-tetramethyl-12,12-dioxo-24-oxa-12λ6-thia-3,4,19, 30-tetrazapentacyclo[23.3.1.12,5.015,23.016,20] triaconta-1(29),2(30),4,15,17,20,22,25,27-nonaen-6-yl]phenyl]-2-methyl-propanoic Acid

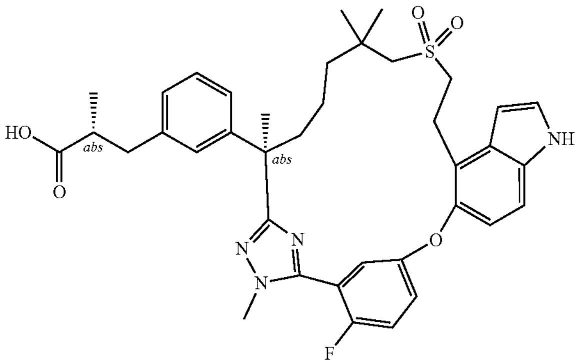 [SMILES: C[C@H](Cc1cccc([C@@]2(C)CCCC(C)(C)CS(=O)(=O)CCc3c(ccc4[nH]ccc34)Oc3ccc(F)c(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 511 mg, 1.05 mmol), and methyl 5-((4-bromo-6-fluoro-1H-indol-5-yl)oxy)-2-fluorobenzimidothioate hydroiodide (Intermediate 14-1) with methyl 5-((4-bromo-1H-indol-5-yl)oxy)-2-fluorobenzimidothioate hydroiodide (Intermediate 14-12, 500 mg, 1.05 mmol) in Step A, the reaction procedure sequence (Steps A-D and Step F) described for Example 6 was used to prepare the title compound (white solid, 49 mg). MS (ESI): 687 m/z $[M+H]^+$, retention time: 1.64 minutes; purity: >99% (214 nm) (LC-MS method 30). $^1H$ NMR (400 MHz, $CD_3OD$). $^1H$ NMR (500 MHz, $CD_3OD$) δ 7.40-7.30 (m, 4H), 7.18-7.10 (m, 2H), 7.05 (s, 1H), 7.02-6.95 (m, 2H), 6.89 (d, J=8.8 Hz, 1H), 6.64 (d, J=3.2 Hz, 1H), 3.85 (d, J=2.4 Hz, 3H), 3.42-3.34 (m, 2H), 3.27-3.17 (m, 2H), 2.98-2.88 (m, 1H), 2.77 (d, J=13.6 Hz, 1H), 2.64-2.49 (m, 3H), 2.20-2.09 (m, 1H), 1.89-1.77 (m, 1H), 1.65 (s, 3H), 1.57-1.45 (m, 1H), 1.28-1.17 (m, 1H), 1.12-1.01 (m, 4H), 1.00 (s, 3H), 0.95 (s, 3H), 0.94-0.84 (m, 1H) ppm.

Example 191. (2S)-3-[3-[(6R)-22,28-Difluoro-6,10, 10-trimethyl-12,12-dioxo-24-oxa-4,12λ6-dithia-19, 30-diazapentacyclo[23.3.1.12,5.015,23.016,20]triaconta-1(29),2,5(30),15,17,20,22,25,27-nonaen-6-yl] phenyl]-2-methyl-propanoic Acid

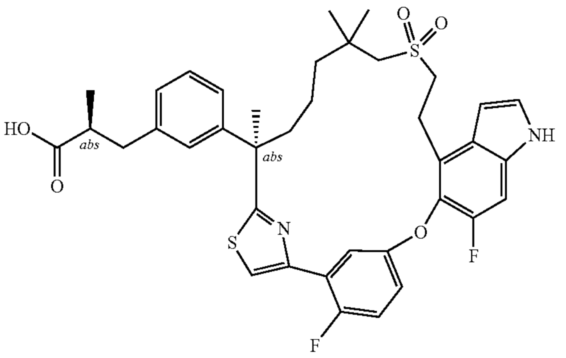 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3csc2n3)c1)C(=O)O]

Exchanging 2-fluoro-5-((6-fluoro-4-vinyl-1H-indol-5-yl)oxy)benzothioamide (Intermediate 12) with methyl (S)-3-(3-((R)-1-amino-7-((2-((tert-butyldiphenylsilyl)oxy)ethyl)sulfonyl)-2,6,6-trimethyl-1-thioxoheptan-2-yl)phenyl)-2-methylpropanoate (Intermediate 139, 496 mg, 0.7 mmol), and methyl 3-(3-(1-bromo-8-((2-methoxy-2-oxoethyl)sulfonyl)-3,7,7-trimethyl-2-oxooctan-3-yl)phenyl)propanoate (Intermediate 8-4) with 2-bromo-1-(5-((4-bromo-6-fluoro-1-(phenylsulfonyl)-1H-indol-5-yl)oxy)-2-fluorophenyl) ethan-1-one (Intermediate 140, 491 mg, 0.84 mmol) in Step A, the reaction procedure sequence (Step A of Example 49, followed by Steps B, C, D and F of Example 6) was used to prepare the title compound (89 mg) as a white solid. MS (ESI): 707 m/z $[M+H]^+$, retention time: 2.16 minutes, purity: 99% (214 nm) (LC-MS Method 4). $^1H$ NMR (400 MHz, $CD_3OD$) δ 7.88-7.85 (m, 1H), 7.82 (d, J=2.0 Hz, 1H), 7.32 (d, J=3.6 Hz, 1H), 7.28 (d, J=10.8 Hz, 1H), 7.20-7.16 (m, 2H), 7.09-7.04 (m, 3H), 6.94-6.90 (m, 1H), 6.61 (d, J=3.2 Hz, 1H), 3.41-3.36 (m, 2H), 3.18-3.14 (m, 2H), 2.96-2.92 (m, 1H), 2.72 (s, 2H), 2.67-2.59 (m, 2H), 2.13-2.07 (m, 1H), 1.81 (s, 3H), 1.75-1.68 (m, 1H), 1.55-1.47 (m, 1H), 1.33-1.17 (m, 2H), 1.08-0.97 (m, 10H) ppm.

Example 192. (2S)-3-[3-[(6R)-22,28-difluoro-6,10,10-trimethyl-12,12-dioxo-4,24-dioxa-12λ6-thia-19,30-diazapentacyclo[23.3.1.12,5.015,23.016,20]triaconta-1(29),2,5(30),15,17,20,22,25,27-nonaen-6-yl]phenyl]-2-methyl-propanoic Acid

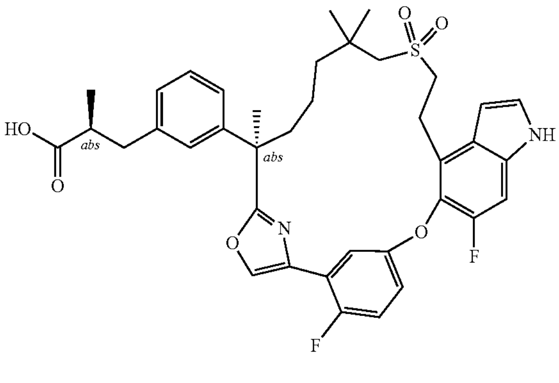 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3coc2n3)c1)C(=O)O]

2-(5-((4-Bromo-6-fluoro-1-(phenylsulfonyl)-1H-indol-5-yl)oxy)-2-fluorophenyl)-2-oxoethyl (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoate

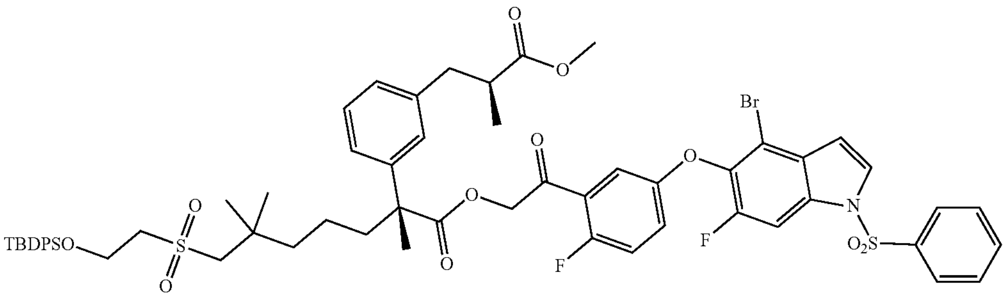

Step A: To a stirred solution of (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoic acid (Intermediate 137H-1, 1.81 g, 2.6 mmol) and 2-bromo-1-(5-((4-bromo-6-fluoro-1-(phenylsulfonyl)-1H-indol-5-yl)oxy)-2-fluorophenyl)ethan-1-one (Intermediate 140, 1.83 g, 3.13 mmol) in dimethylformamide (30 mL) was added sodium bicarbonate (0.66 g, 7.8 mmol). The mixture was stirred for 16 hours at room temperature, then diluted with water (100 mL), and extracted with ethyl acetate (2×50 mL). The combined organic extracts were washed with water, brine, dried over sodium sulfate, and concentrated. The residue was purified by automated flash chromatography (40 g silica gel column, eluting with 0-50% ethyl acetate in petroleum ether) to give the title compound (2.34 g, 69%) as a colorless oil. MS (ESI): 1215, 1217 m/z $[M+H_2O]+$, retention time: 2.79 minutes, purity: 89% (254 nm) (LC-MS Method 4).

Methyl (S)-3-(3-((R)-2-(4-(5-((4-bromo-6-fluoro-1-(phenylsulfonyl)-1H-indol-5-yl)oxy)-2-fluorophenyl)oxazol-2-yl)-7-((2-((tert-butyldiphenylsilyl)oxy)ethyl)sulfonyl)-6,6-dimethylheptan-2-yl)phenyl)-2-methylpropanoate

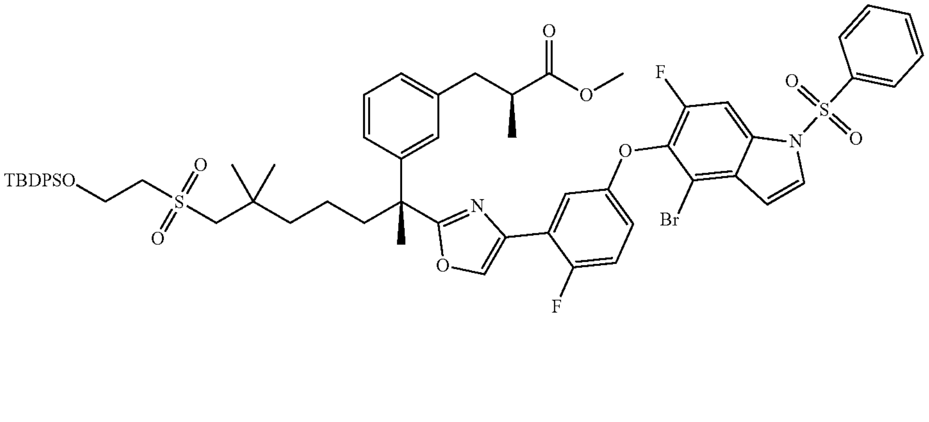

Step B: To a stirred solution of Step A product (2.34 g, 1.95 mmol) in acetic acid (30 mL) was added ammonium acetate (0.45 g, 5.85 mmol). The reaction was stirred at 110° C. for 16 hours, cooled to room temperature, and quenched with water (50 mL). The solution was extracted with ethyl acetate (3×30 mL). The combined organic layers were washed with saturated sodium bicarbonate, brine, dried over sodium sulphate, and concentrated. The residue was purified by automated flash chromatography (40 g silica gel column, eluting with 0-50% ethyl acetate in petroleum ether) to give the title compound (0.95 g, 40%) as a solid. MS (ESI): 1179, 1181 m/z $[M+H]^+$, retention time: 3.01 minutes, purity: 89% (254 nm) (LC-MS Method 4).

Methyl (S)-3-(3-((R)-2-(4-(5-((4-bromo-6-fluoro-1-(phenylsulfonyl)-1H-indol-5-yl)oxy)-2-fluorophenyl)oxazol-2-yl)-7-((2-hydroxyethyl)sulfonyl)-6,6-dimethylheptan-2-yl)phenyl)-2-methylpropanoate

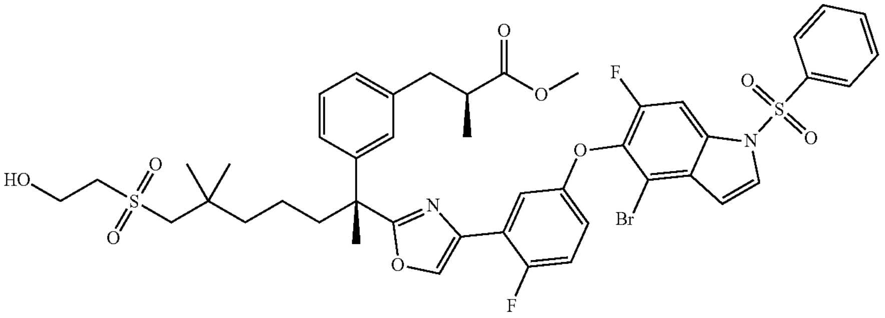 [SMILES: COC(=O)[C@@H](C)Cc1cccc([C@@](C)(CCCC(C)(C)CS(=O)(=O)CCO)c2nc(-c3cc(Oc4c(F)cc5c(ccn5S(=O)(=O)c5ccccc5)c4Br)ccc3F)co2)c1]

Step C: To a stirred solution of Step B product (950 mg, 0.80 mmol) in tetrahydrofuran (15 mL) was added tetrabutylammonium fluoride (3.2 mL, 3.2 mmol)) and acetic acid (0.18 mL, 3.2 mmol). The mixture was stirred at room temperature for 16 hours, then diluted with water (60 mL), and extracted with ethyl acetate (3×35 mL). The combined organic layers were washed with brine (20 mL), dried over sodium sulfate, and concentrated. The residue was purified by automated flash chromatography (25 g silica gel column, eluting with 0-65% ethyl acetate in petroleum ether) to give the title compound (650 mg, 81%) as an oil. MS (ESI): 941, 943 m/z $[M+H]^+$, retention time: 2.31 minutes, purity: 94% (254 nm) (LC-MS Method 33).

Compound 192: (2S)-3-[3-[(6R)-22,28-difluoro-6,10,10-trimethyl-12,12-dioxo-4,24-dioxa-12 6-thia-19,30-diazapentacyclo[23.3.1.12,5.015,23.016,20]triaconta-1(29),2,5(30),15,17,20,22,25,27-nonaen-6-yl]phenyl]-2-methyl-propanoic Acid

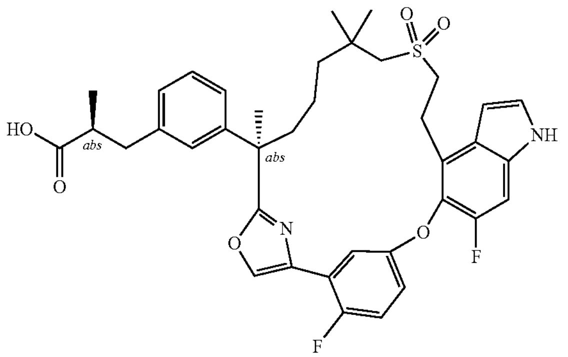 [SMILES: C[C@@H](Cc1cccc([C@@]2(C)CCCC(C)(C)CS(=O)(=O)CCc3c(c(F)cc4[nH]ccc34)Oc3ccc(F)c(c3)-c3coc2n3)c1)C(=O)O]

Step D: Exchanging methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 6) with methyl (S)-3-(3-((R)-2-(4-(5-((4-bromo-6-fluoro-1-(phenylsulfonyl)-1H-indol-5-yl)oxy)-2-fluorophenyl)oxazol-2-yl)-7-((2-hydroxyethyl)sulfonyl)-6,6-dimethylheptan-2-yl)phenyl)-2-methylpropanoate (Step C product of this example, 620 mg, 0.66 mmol) in Step B of Example 6, the reaction procedure sequence (Steps B, C, D and F) described for Example 6 was followed to prepare the title compound (69 mg) as a white solid. MS (ESI): 691 m/z $[M+H]^+$, retention time: 2.11 minutes, purity: 99% (254 nm) (LC-MS Method 4). $^1H$ NMR (400 MHz, $CD_3OD$) δ 8.15 (d, J=4.0 Hz, 1H), 7.62-7.59 (m, 1H), 7.32 (d, J=3.2 Hz, 1H), 7.27-7.15 (m, 3H), 7.09-7.02 (m, 2H), 6.91 (s, 1H), 6.85 (d, J=8.0 Hz, 1H), 6.67 (d, J=2.4 Hz, 1H), 3.49-3.44 (m, 2H), 3.24-3.13 (m, 2H), 2.96-2.90 (m, 1H), 2.67-2.58 (m, 4H), 1.94-1.88 (m, 1H), 1.77-1.73 (m, 1H), 1.70 (s, 3H), 1.57-1.51 (m, 1H), 1.22-1.07 (m, 5H), 1.07-0.99 (m, 7H) ppm.

Example 193. Methyl (2R)-3-[5-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)-3-thienyl]-2-methyl-propanoate

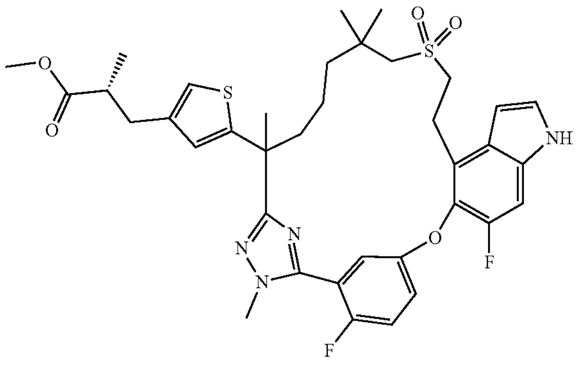 [SMILES: COC(=O)[C@H](C)Cc1csc(C2(C)CCCC(C)(C)CS(=O)(=O)CCc3c(c(F)cc4[nH]ccc34)Oc3ccc(F)c(c3)-c3nc2nn3C)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with methyl (2R)-3-(5-(7-((2-hydroxyethyl)sulfonyl)-2,6,6-trimethyl-1-(2-methylhydrazineyl)-1-oxoheptan-2-yl)thiophen-3-yl)-2-methylpropanoate (intermediate 69-26, 64 mg, 0.104 mmol) in Step A, the title compound (white solid, 50 mg) was prepared following the reaction sequence (Steps A-D and Step F) as described for Example 6. MS (ESI): 725 m/z $[M+H]^+$, retention time: 2.12 minutes; purity: 92% (214 nm) (LC-MS method 4).

Example 194. (2R)-3-[3-[(6R)-22,28-difluoro-6,10,10-trimethyl-12,12-dioxo-24-oxa-12λ6,30-dithia-3,4,19-triazapentacyclo[23.3.1.12,5.015,23.016,20]triaconta-1(29),2,4,15,17,20,22,25,27-nonaen-6-yl]phenyl]-2-methyl-propanoic Acid

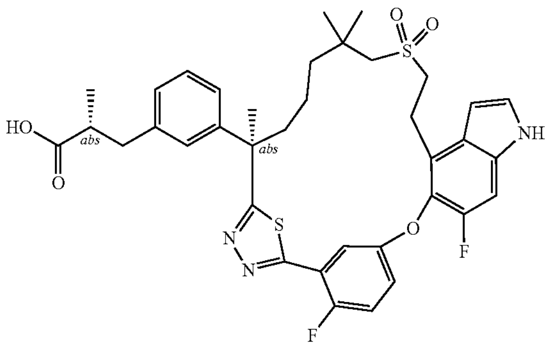 [SMILES: C[C@H](Cc1cccc([C@@]2(C)CCCC(C)(C)CS(=O)(=O)CCc3c(c(F)cc4[nH]ccc34)Oc3ccc(F)c(c3)C3=NN=C2S3)c1)C(=O)O]

Methyl (R)-3-(3-((R)-1-(2-(5-((4-bromo-6-fluoro-1H-indol-5-yl)oxy)-2-fluorobenzoyl)hydrazineyl)-7-((2-hydroxyethyl)sulfonyl)-2,6,6-trimethyl-1-oxoheptan-2-yl)phenyl)-2-methylpropanoate

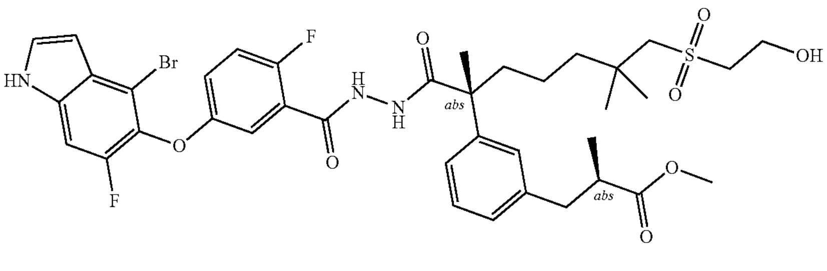 [SMILES: COC(=O)[C@H](C)Cc1cccc([C@@](C)(CCCC(C)(C)CS(=O)(=O)CCO)C(=O)NNC(=O)c2cc(Oc3c(F)cc4[nH]ccc4c3Br)ccc2F)c1]

Step A: To a stirred solution of methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 900 mg, 1.91 mmol) in acetonitrile (10 mL) was added 5-((4-bromo-6-fluoro-1H-indol-5-yl)oxy)-2-fluorobenzoic acid (704 mg, 1.91 mmol), N,N,N',N'-tetramethylchloroformamidinium-hexafluorophosphate (536 mg, 1.91 mmol) and 1-methylimidazole (0.53 mL, 6.69 mmol). The reaction mixture was stirring at room temperature for 1 hour, then diluted with ethyl acetate (20 mL). The solution was washed with 0.5 M hydrochloric acid, saturated sodium bicarbonate, brine, dried over sodium sulfate, and concentrated. The residue was purified by automated flash chromatography (4.0 g silica gel column, eluting with 0-80% ethyl acetate in petroleum ether) to give the title compound (450 mg, 29%) as light-yellow oil. MS (ESI): 820, 822 m/z $[M+H]^+$, retention time: 1.94 minutes; purity: 86% (214 nm) (LC-MS method 4).

Methyl (R)-3-(3-((R)-2-(5-(5-((4-bromo-6-fluoro-1H-indol-5-yl)oxy)-2-fluorophenyl)-1,3,4-thiadiazol-2-yl)-7-((2-hydroxyethyl)sulfonyl)-6,6-dimethylheptan-2-yl)phenyl)-2-methylpropanoate

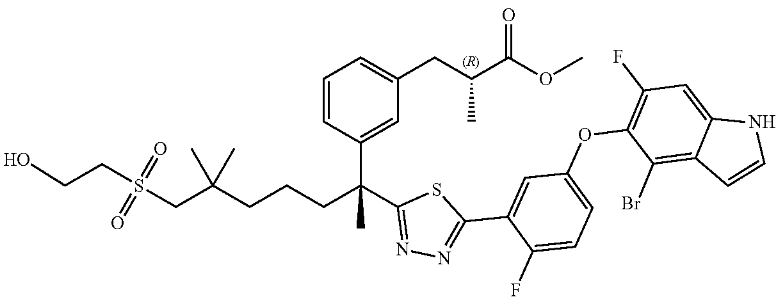

Step B: To a stirred solution of Step A product (140 mg, 0.171 mmol) in toluene (5 mL) was added 2,4-bis(4-methoxyphenyl)-1,3-dithia-2,4-diphosphetane-2,4-disulfide (138 mg, 0.341 mmol). The mixture was stirred at 60° C. for 16 hours and concentrated. The residue was purified by automated flash chromatography (4.0 g silica gel column, eluting with 0-65% ethyl acetate in petroleum ether) to afford the title compound (50 mg, 36%) as light-yellow oil. MS (ESI): 818, 820 m/z $[M+H]^+$, retention time: 2.11 minutes; purity: 86% (254 nm) (LC-MS method 4).

Compound 194: (2R)-3-[3-[(6R)-22,28-difluoro-6,10,10-trimethyl-12,12-dioxo-24-oxa-12λ6,30-dithia-3,4,19-triazapentacyclo[23.3.1.12,5.015,23.016,20]triaconta-1(29),2,4,15,17,20,22,25,27-nonaen-6-yl]phenyl]-2-methyl-propanoic Acid

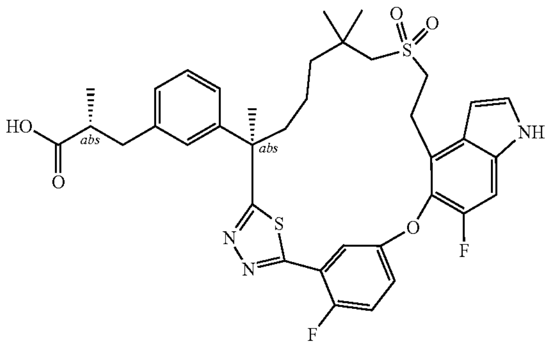 [SMILES: C[C@H](Cc1cccc([C@@]2(C)CCCC(C)(C)CS(=O)(=O)CCc3c(c(F)cc4[nH]ccc34)Oc3ccc(F)c(c3)C3=NN=C2S3)c1)C(=O)O]

Exchanging methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 6) with methyl (R)-3-(3-((R)-2-(5-(5-((4-bromo-6-fluoro-1H-indol-5-yl)oxy)-2-fluorophenyl)-1,3,4-thiadiazol-2-yl)-7-((2-hydroxyethyl)sulfonyl)-6,6-dimethylheptan-2-yl)phenyl)-2-methylpropanoate (Step B product of this example, 50 mg, 0.0611 mmol) in Step B, the reaction procedure sequence (Steps B-D and Step F) described for Example 6 was followed to prepare the title compound (3.2 mg) as a white solid. MS (ESI): 708 m/z $[M+H]^+$, retention time: 2.01 minutes; purity: 98% (214 nm) (LC-MS method 4). $^1$H NMR (400 MHz, $CD_3OD$) δ 7.39-7.21 (m, 8H), 7.13 (d, J=7.2 Hz, 1H), 6.58 (d, J=2.8 Hz, 1H), 3.58-3.51 (m, 1H), 3.24 (t, J=8.0 Hz, 2H), 3.09-2.94 (m, 2H), 2.83-2.65 (m, 4H), 2.33-2.25 (m, 1H), 2.02-1.97 (m, 1H), 1.78 (s, 3H), 1.40-1.20 (m, 4H), 1.15 (s, 3H), 1.11 (d, J=6.8 Hz, 3H), 0.98 (s, 3H) ppm.

Example 195. Diastereomers 1 and 2 of 3-[[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]-1-hydroxy-pyrrolidine-2,5-dione

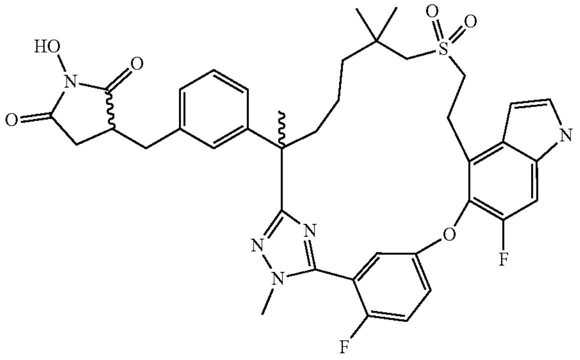 [SMILES: Cn1nc2nc1-c1cc(ccc1F)Oc1c(F)cc3[nH]ccc3c1CCS(=O)(=O)CC(C)(C)CCCC2(C)c1cccc(CC2CC(=O)N(O)C2=O)c1]

(3Z)-1-benzyloxy-3-[[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methylene]pyrrolidine-2,5-dione

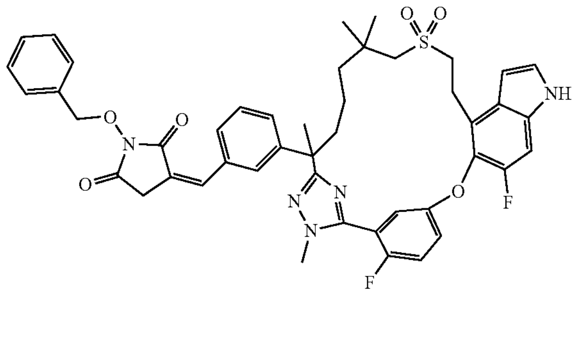 [SMILES: Cn1nc2nc1-c1cc(ccc1F)Oc1c(F)cc3[nH]ccc3c1CCS(=O)(=O)CC(C)(C)CCCC2(C)c1cccc(/C=C2/CC(=O)N(OCc3ccccc3)C2=O)c1]

Step A: To a stirred solution of 1-(benzyloxy)-3-(triphenyl-15-phosphaneylidene)pyrrolidine-2,5-dione (Intermediate 141, 87 mg, 0.187 mmol) in methanol (3 mL) was added 3-(22,28-difluoro-3,6,10,10-tetramethyl-12,12-dioxo-24-oxa-12λ6-thia-3,4,19,30-tetrazapentacyclo [23.3.1.12,5.015,23.016,20]triaconta-1(29),2(30),4,15,17,20,22,25,27-nonaen-6-yl)benzaldehyde (Step C product of Example 174, 120 mg, 0.187 mmol). The mixture was heated to reflux for 1.5 hours, then cooled to room temperature and diluted with water. The solution was extracted with ethyl acetate (3×20 mL). The combined organic layers were washed with water, brine, dried over sodium sulphate, filtered, and concentrate. The residue was purified by automated flash chromatography (12 g silica gel column, eluting with 0-65% ethyl acetate in petroleum ether) to give the title compound (140 mg, 90%) as a light-yellow solid. MS (ESI): 834 m/z $[M+H]^+$, retention time: 2.10 minutes; purity: 95% (214 nm) (LC-MS method 4).

Compounds 195A and 195B. Diastereomers 1 and 2 of 3-[[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]-1-hydroxy-pyrrolidine-2,5-dione

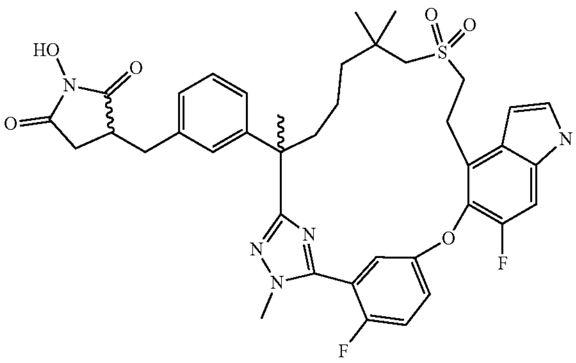 [SMILES: Cn1nc2nc1-c1cc(ccc1F)Oc1c(F)cc3[nH]ccc3c1CCS(=O)(=O)CC(C)(C)CCCC2(C)c1cccc(CC2CC(=O)N(O)C2=O)c1]

Step B: To a stirred solution of Step A product (140 mg, 0.168 mmol) in ethanol (5.0 mL) was added 10% palladium on carbon (wetted with ca. 55% Water, 50 mg). The reaction mixture was stirred under hydrogen for 16 hours at room temperature and filtered through a pad of Celite. The filtrate was concentrated to give a mixture of four diastereomers (70 mg, originated from 2 chiral center) as a white solid. This diastereomer mixture was separated by prep-HPLC. The first eluent, diastereomer 1 (23 mg), was designated as Compound 195A. The second eluent, diastereomer 2 (27 mg), was designated as Compound 195B.

Compound 195A: MS (ESI): 746 m/z $[M+H]^+$, retention time: 1.82 minutes; purity: >99% (214 nm) (LC-MS method 4).

Compound 195B: MS (ESI): 746 m/z $[M+H]^+$, retention time: 1.84 minutes; purity: >99% (214 nm) (LC-MS method 4).

Example 196. Diastereomers 1 and 2 of 3-[[3-(22,28-difluoro-3,6,10,10-tetramethyl-12,12-dioxo-24-oxa-12λ6-thia-3,4,19,30-tetrazapentacyclo [23.3.1.12,5.015,23.016,20]triaconta-1(29),2(30),4,15,17,20,22,25,27-nonaen-6-yl)phenyl]methyl] pyrrolidine-2,5-dione

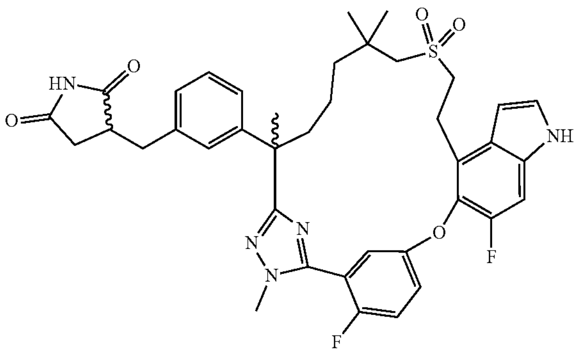 [SMILES: Cn1nc2nc1-c1cc(ccc1F)Oc1c(F)cc3[nH]ccc3c1CCS(=O)(=O)CC(C)(C)CCCC2(C)c1cccc(CC2CC(=O)NC2=O)c1]

(3Z)-3-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl] methylene]pyrrolidine-2,5-dione

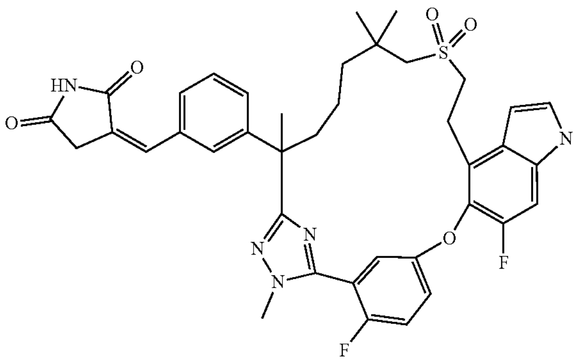 [SMILES: Cn1nc2nc1-c1cc(ccc1F)Oc1c(F)cc3[nH]ccc3c1CCS(=O)(=O)CC(C)(C)CCCC2(C)c1cccc(/C=C2/CC(=O)NC2=O)c1]

Step A: To a stirred solution of 3-(triphenyl-15-phosphaneylidene)pyrrolidine-2,5-dione (56 mg, 0.156 mmol) in methanol (3 mL) was added 3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)benzaldehyde (Step C product of Example 174, 100 mg, 0.156 mmol, 1.0 eq). The mixture was heated to reflux for 1.5 hours, cooled to room temperature, and diluted with water (10 mL). The solution was extracted with ethyl acetate (2×20 mL). The combined organic layers were washed with water, brine, dried over sodium sulphate, filtered, and concentrated. The residue was purified by automated flash chromatography (12 g silica gel column, eluting with 0-65% ethyl acetate in petroleum ether) to give the title compound (80 mg, 72%) as a light-yellow solid. MS (ESI): 728 m/z $[M+H]^+$, retention time: 2.10 minutes; purity: 95% (214 nm) (LC-MS method 4). Compounds 196A and 196B: Diastereomers 1 and 2 of 3-[[3-(22,28-difluoro-3,6,10,10-tetramethyl-12,12-dioxo- 24-oxa-12λ6-thia-3,4,19,30-tetrazapentacyclo[23.3.1.12, 5.015,23.016,20]triaconta-1(29),2(30),4,15,17,20,22,25,27-nonaen-6-yl)phenyl]methyl]pyrrolidine-2,5-dione

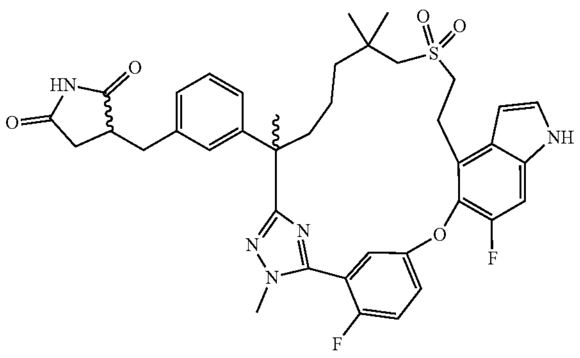 [SMILES: Cn1nc2nc1-c1cc(ccc1F)Oc1c(F)cc3[nH]ccc3c1CCS(=O)(=O)CC(C)(C)CCCC2(C)c1cccc(CC2CC(=O)NC2=O)c1]

Step B: To a stirred solution of Step A product (80 mg, 0.11 mmol) in ethanol (5.0 mL) was added 10% palladium on carbon (wetted with ca. 55% water, 50 mg). The reaction mixture was stirred under hydrogen for 16 hours, then filtered through a pad of Celite. The filtrate was concentrated to give the four diastereomeric mixture of title compound (71.4 mg, 89%) as a white solid. This mixture was subjected to chiral SFC separation using SFC-150 (Waters) under the following conditions: Column: AD 20×250 mm, 10 μm; Column temperature: 35° C.; Mobile phase: carbon dioxide/ethanol (0.2%7M ammonia in methanol)=70/30; Flow rate: 100 g/minute; Back pressure: 100 bar; Detection wavelength: 214 nm; Cycle time: 4.3 minutes; Sample solution: 68.9 mg dissolved in 15 mL of methanol; Injection volume: 0.5 mL. The first eluent, Diastereomer 1 (13.3 mg), is designated as Compound 196A; The second eluent, Diastereomer 2 (9.2 mg), is designated as Compound 196B; Also collected are mixtures of those two eluents (19.2 mg), which are not well separated.

Compound 196A: MS (ESI): 730 m/z $[M+H]^+$, retention time: 1.84 minutes; purity: >99% (214 nm) (LC-MS method 4). Chiral separation purity: 98.3% (Retention time: 7.03 minutes; Chiral column conditions: Column: AD-H 4.6×250 mm, 5 μm; Mobile phase: Hexanes (0.1% diethylamine): ethanol (0.1% diethylamine)=70:30; Column temperature: 40° C.; Flow Rate: 1 mL/minute; Instrument: Shimazu; Injection volume: 10 μL.) Compound 196B: MS (ESI): 730 m/z $[M+H]^+$, retention time: 1.84 minutes; purity: >99% (214 nm) (LC-MS method 4). Chiral Separation Purity: 95.5% (Retention time: 9.57 minutes; Chiral column conditions: same as Compound 196A.)

Example 197. (2R)-3-[3-[(6R)-22-Fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

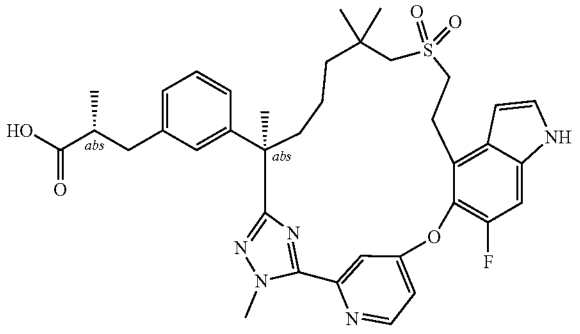

Methyl (R)-3-(3-((R)-2-(5-(4-((4-bromo-6-fluoro-1H-indol-5-yl)oxy)pyridin-2-yl)-1-methyl-1H-1,2,4-triazol-3-yl)-7-((2-hydroxyethyl)sulfonyl)-6,6-dimethylheptan-2-yl)phenyl)-2-methylpropanoate

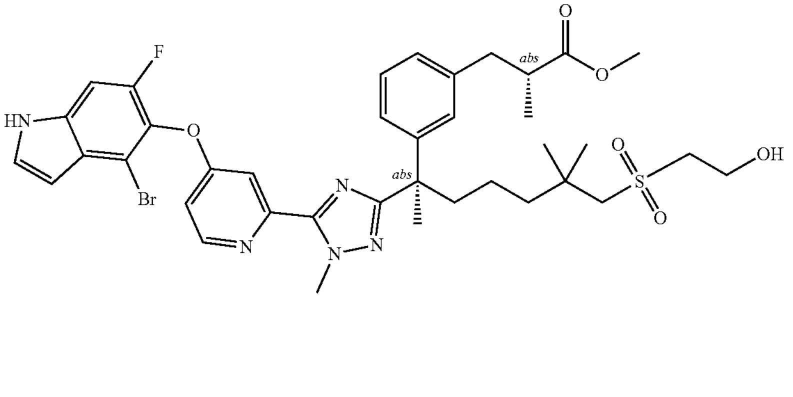 [SMILES: COC(=O)[C@H](C)Cc1cccc([C@@](C)(CCCC(C)(C)CS(=O)(=O)CCO)c2nc(-c3cc(Oc4c(F)cc5[nH]ccc5c4Br)ccn3)n(C)n2)c1]

Step A: To a stirred solution of methyl 4-((4-bromo-6-fluoro-1H-indol-5-yl)oxy)pyridine-2-carbimidothioate (Intermediate 133-1, 530 mg, 1.39 mmol) in pyridine (5 mL) was added magnesium sulfate (200 mg, 1.66 mmol) and methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 676 mg, 1.39 mmol). The reaction mixture was stirred at 80° C. overnight, cooled to room temperature and quenched with water (20 mL). The solution was extracted with ethyl acetate (3×25 mL). The combined organic extracts were washed with water, brine, dried over magnesium sulfate and concentrated. The residue was purified by automated flash column chromatography eluting with 0-80% ethyl acetate in petroleum ether to afford the title compound (530 mg, 48%) as a yellow solid. MS (ESI): 798, 800 m/z $[M+H]^+$, purity: 98% (214 nm); retention time: 2.01 minutes (LC-MS Method 4).

Methyl (2R)-3-[3-[(1R)-1-[5-[4-[(4-bromo-6-fluoro-1H-indol-5-yl)oxy]-2-pyridyl]-1-methyl-1,2,4-triazol-3-yl]-1,5,5-trimethyl-6-vinylsulfonyl-hexyl]phenyl]-2-methyl-propanoate

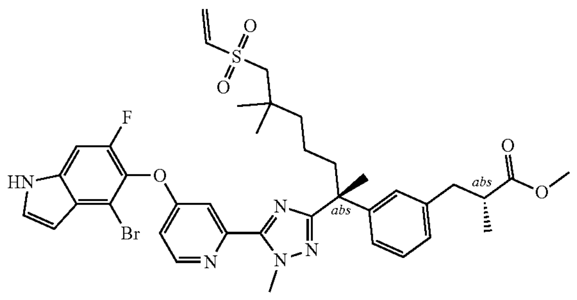 [SMILES: C=CS(=O)(=O)CC(C)(C)CCC[C@](C)(c1cccc(C[C@@H](C)C(=O)OC)c1)c1nc(-c2cc(Oc3c(F)cc4[nH]ccc4c3Br)ccn2)n(C)n1]

Step B: To a stirred solution of Step A product (220 mg, 0.275 mmol) in dichloromethane (3 mL) was added methane sulfonyl chloride (0.028 mL, 0.358 mmol) and triethylamine (0.12 mL, 0.826 mmol) at 0° C. The reaction mixture was stirred at room temperature for 4 hours and concentrated. The residue was purified by automated flash column chromatography eluting with 0-65% ethyl acetate in petroleum ether to afford the title compound (150 mg, 70%) as a solid. MS (ESI): 780, 782 m/z $[M+H]^+$, purity: 95% (214 nm); retention time: 2.14 minutes (LC-MS Method 4).

Methyl (2R)-3-[3-[(6R,13E)-22-fluoro-3,6,10,10-tetramethyl-12,12-dioxo-24-oxa-1216-thia-3,4,19,28,30-pentazapentacyclo[23.3.1.12,5.015,23.016,20]triaconta-1(29),2(30),4,13,15,17,20,22,25,27-decaen-6-yl]phenyl]-2-methyl-propanoate

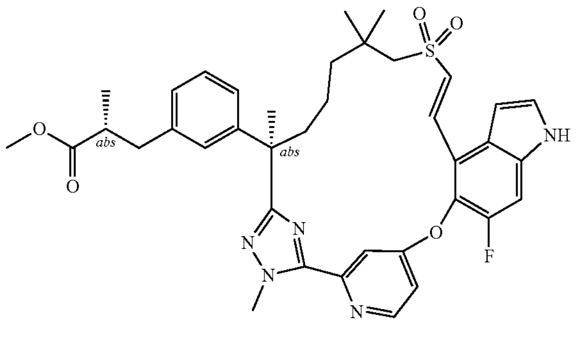 [SMILES: COC(=O)[C@H](C)Cc1cccc([C@@]2(C)CCCC(C)(C)CS(=O)(=O)/C=C/c3c(c(F)cc4[nH]ccc34)Oc3ccnc(c3)-c3nc2nn3C)c1]

Step C: To a stirred and degassed solution of Step B product (150 mg, 0.192 mmol) in toluene (70 mL) was added triethylamine (0.080 mL, 0.576 mmol) and bis(tri-t-butylphosphine)palladium (0) (20 mg, 0.0384 mmol). The reaction mixture was stirred at 120° C. for 4 hours and concentrated. The residue was then purified by flash column chromatography eluting with ethyl acetate in petroleum ether to afford the title compound (90 mg, 64%) as solid. MS (ESI): 700 m/z $[M+H]^+$, purity: 95% (214 nm); retention time: 2.14 minutes (LC-MS Method 4).

Methyl (2R)-3-[3-[(6R)-22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

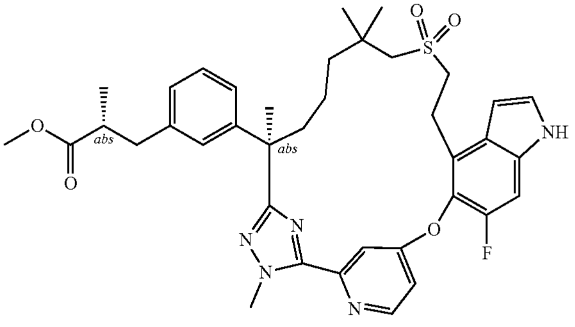 [SMILES: COC(=O)[C@H](C)Cc1cccc([C@@]2(C)CCCC(C)(C)CS(=O)(=O)CCc3c(c(F)cc4[nH]ccc34)Oc3ccnc(c3)-c3nc2nn3C)c1]

Step D: To a stirred solution of Step C product (90 mg, 0.129 mmol) in ethanol (5 mL) was added palladium on carbon (20 mg, 10%, 50% wet). The reaction mixture was stirred under hydrogen at 50° C. overnight, cooled to room temperature and filtered through a pad of Celite. The filtration was concentrated. The residue was purified by prep-HPLC to afford the title compound (80 mg, 89%) as solid. MS (ESI): 702 m/z $[M+H]^+$, purity: 95% (214 nm); retention time: 2.14 minutes (LC-MS Method 4).

Example 197, (2R)-3-[3-[(6R)-22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

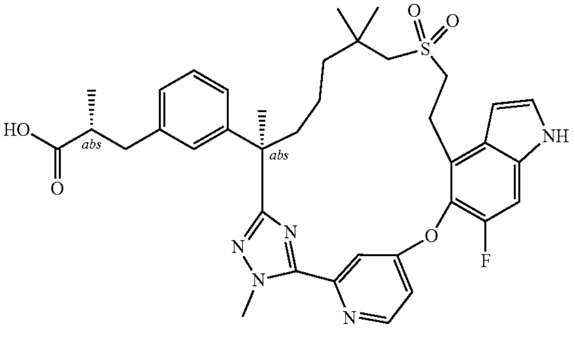

Step E: To a stirred solution of Step D product (80 mg, 0.114 mmol) in tetrahydrofuran (3 mL) and methanol (1 mL) was added a solution of lithium hydroxide (8.2 mg, 0.342 mmol) in water (1 mL). The reaction mixture was stirred at room temperature for 4 hours, then diluted with water (10 mL), and adjusted the pH to 5-6 with 1N hydrogen chloride. The mixture was extracted with ethyl acetate (2×25 mL). The combined organic extracts were washed with brine, dried over sodium sulfate, and concentrated. The residue was purified by flash column chromatography eluting with 80% ethyl acetate in petroleum ether to give the title compound (55 mg, 67%) as a white solid. LC-MS: MS (ESI): 688 m/z $[M+H]^+$, purity: >99%; retention time: 1.93 minutes (LC-MS Method 4). $^1H$ NMR (400 MHz, $CD_3OD$) δ 8.64 (d, J=5.6 Hz, 1H), 7.65 (d, J=2 Hz, 1H), 7.34 (d, J=3.2 Hz, 1H), 7.28 (d, J=10.4 Hz, 1H), 7.25-7.23 (m, 1H), 7.12 (t, J=8.0 Hz, 1H), 7.02 (s, 1H), 6.98-6.90 (m, 2H), 6.69 (d, J=2.0 Hz, 1H), 4.34 (s, 3H), 3.45-3.39 (m, 2H), 3.20-2.95 (m, 2H), 2.95-2.86 (m, 1H), 2.63-2.49 (m, 4H), 2.07-1.97 (m, 1H), 1.80-1.70 (m, 1H), 1.64 (s, 3H), 1.45-0.90 (m, 13H) ppm.

Example 198. (2R)-3-[5-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)-2-thienyl]-2-methyl-propanoic Acid

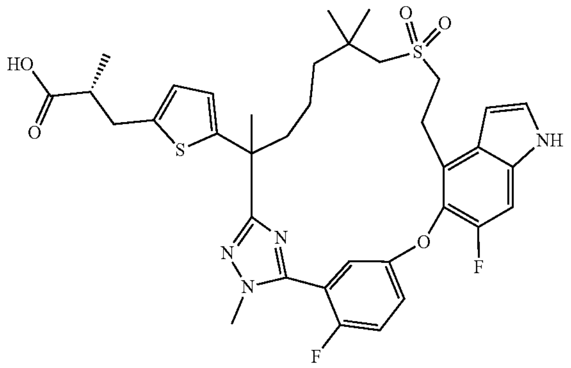 [SMILES: C[C@H](Cc1ccc(C2(C)CCCC(C)(C)CS(=O)(=O)CCc3c(c(F)cc4[nH]ccc34)Oc3ccc(F)c(c3)-c3nc2nn3C)s1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with methyl (2R)-3-(5-(7-((2-hydroxyethyl)sulfonyl)-2,6,6-trimethyl-1-(2-methylhydrazineyl)-1-oxoheptan-2-yl)thiophen-2-yl)-2-methylpropanoate (intermediate 69-27, 700 mg, 1.43 mmol) in Step A, the reaction procedure sequence (Steps A-D and Step F) described for Example 6 was followed to prepare the title compound (40 mg) as a white solid. MS (ESI): 711 m/z $[M+H]^+$, retention time: 1.67 minutes; purity: 98% (214 nm) (LC-MS method 4). $^1H$ NMR (400 MHz, $CDCl_3$) δ 7.35-7.30 (m, 3H), 7.22 (d, J=10.8 Hz, 1H), 7.16-7.15 (m, 1H), 6.63 (d, J=3.6 Hz, 1H), 1H), 6.57 (d, J=3.6 Hz, 1H), 6.54 (d, J=3.6 Hz, 1H), 3.82 (d, J=2.0 Hz, 3H), 3.39-3.33 (m, 2H), 3.28-3.21 (m, 1H), 3.09-3.02 (m, 1H), 2.93 (d, J=13.6 Hz, 1H), 2.80 (d, J=13.6 Hz, 1H), 2.78-2.74 (m, 1H), 2.66-2.59 (m, 1H), 2.20-2.10 (m, 1H), 1.87-1.77 (m, 1H), 1.72 (s, 3H), 1.58-1.49 (m, 1H), 1.41-1.38 (m, 1H), 1.32-1.17 (m, 3H), 1.13 (d, J=7.2 Hz, 3H), 1.05 (s, 3H), 1.03 (s, 3H) ppm.

Example 199. 3-[[3-(22,28-Difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methyl]-1-hydroxy-pyrrolidin-2-one

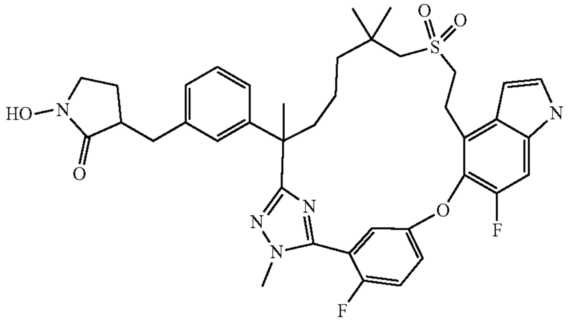 [SMILES: Cn1nc2nc1-c1cc(ccc1F)Oc1c(F)cc3[nH]ccc3c1CCS(=O)(=O)CC(C)(C)CCCC2(C)c1cccc(CC2CCN(O)C2=O)c1]

(3Z)-1-benzyloxy-3-[[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]methylene]pyrrolidin-2-one

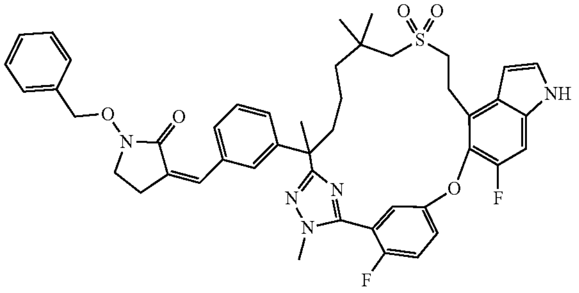 [SMILES: Cn1nc2nc1-c1cc(ccc1F)Oc1c(F)cc3[nH]ccc3c1CCS(=O)(=O)CC(C)(C)CCCC2(C)c1cccc(/C=C2/CCN(OCc3ccccc3)C2=O)c1]

Step A: To a stirred solution of (1-(benzyloxy)-2-oxopyrrolidin-3-yl)triphenylphosphonium bromide (Intermediate 114, 124 mg, 0.232 mmol) in ethanol (5 mL) was added 3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)benzaldehyde (Step C product of Example 174, 150 mg, 0.232 mmol) and triethylamine (71 mg, 0.696 mmol). The mixture was heated at 85° C. for 4 hours, cooled to room temperature, and quenched with water (10 mL). The solution was extracted with ethyl acetate (2×20 mL). The combined organic layers were washed with water (10 mL), brine (10 mL), dried over sodium sulphate, filtered, and concentrated. The residue was purified by flash chromatography (12 g silica gel column, eluting with 0-65% ethyl acetate in petroleum ether) to give the title compound (160 mg, 84%) as a light-yellow solid. MS (ESI): 820 m/z $[M+H]^+$, retention time: 2.10 minutes; purity: 95% (214 nm) (LC-MS method 4).

Compound 199. 3-[[3-(22,28-Difluoro-3,6,10,10-tetramethyl-12,12-dioxo-24-oxa-1216-thia-3,4,19,30-tetrazapentacyclo[23.3.1.12,5.015,23.016,20]triaconta-1(29),2(30),4,15,17,20,22,25,27-nonaen-6-yl)phenyl]methyl]-1-hydroxy-pyrrolidin-2-one

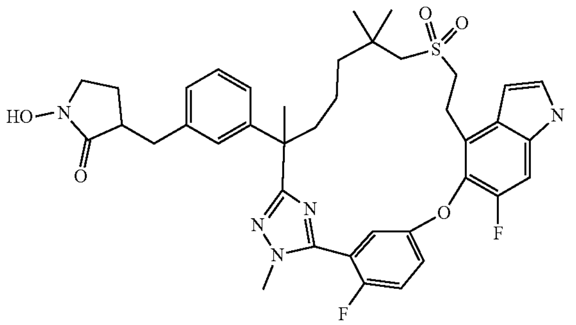 [SMILES: Cn1nc2nc1-c1cc(ccc1F)Oc1c(F)cc3[nH]ccc3c1CCS(=O)(=O)CC(C)(C)CCCC2(C)c1cccc(CC2CCN(O)C2=O)c1]

Step B: To a stirred solution of Step A product (160 mg, 0.195 mmol) in ethanol (5.0 mL) was added 10% palladium on carbon (wetted with ca. 55% water, 50 mg). The reaction mixture was stirred under hydrogen for 16 hours and filtered through a pad of Celite. The filtrate was concentrated. The residue was purified by prep-HPLC to give the title compound (64 mg, 45%) as a white solid. MS (ESI): 732 m/z $[M+H]^+$, retention time: 1.83 minutes; purity: >99% (214 nm) (LC-MS method 4) (Mixture of 4 equal diastereomers).

Example 200. (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

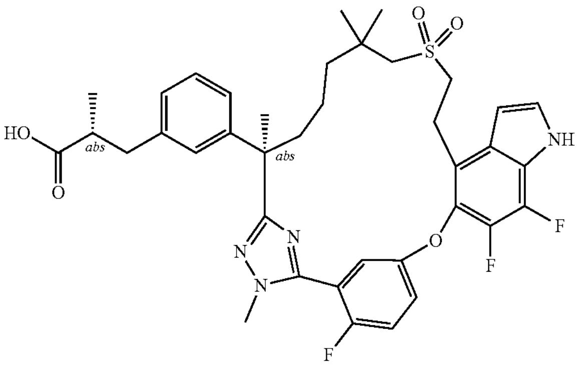

Methyl (R)-3-(3-((R)-2-(5-(5-((4-bromo-6,7-difluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate

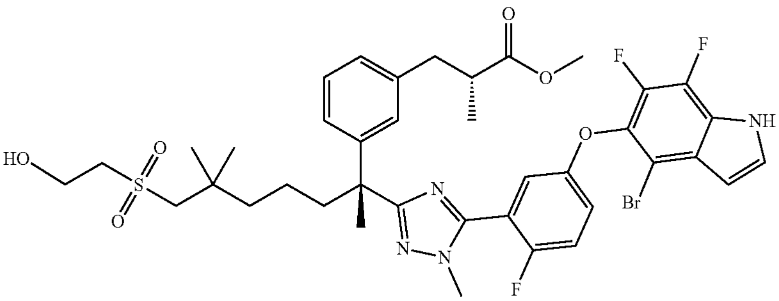 [SMILES: COC(=O)[C@H](C)Cc1cccc([C@@](C)(CCCC(C)(C)CS(=O)(=O)CCO)c2nc(-c3cc(Oc4c(F)c(F)c5[nH]ccc5c4Br)ccc3F)n(C)n2)c1]

Step A: To a stirred solution of methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 6.60 g, 13.6 mmol) and methyl 5-((4-bromo-6,7-difluoro-1H-indol-5-yl)oxy)-2-fluorobenzimidothioate hydroiodide (Intermediate 14-2, 7.77 g, 14.3 mmol) in pyridine (80 mL) was added magnesium sulphate (6.0 g). The reaction mixture was stirred at 80° C. overnight. The reaction mixture was quenched with water (400 mL) and extracted with ethyl acetate (3×200 mL). The combined organic extracts were washed with brine (400 mL), dried over sodium sulfate, filtered, and concentrated. The residue was purified by automated flash chromatography (120 g silica gel column, eluting with 0-65% ethyl acetate in petroleum ether) to give the title compound (7.00 g, 62%) as a solid. LC-MS: MS (ESI): 833, 835 m/z $[M+H]^+$, retention time: 1.92 minutes; purity: 97% (214 nm) (LC-MS method 016).

Methyl (R)-3-(3-((R)-2-(5-(5-((4-bromo-6,7-difluoro-1H-indol-5-yl)oxy)-2-fluorophenyl)-1-methyl-1H-1,2,4-triazol-3-yl)-6,6-dimethyl-7-(vinylsulfonyl)heptan-2-yl)phenyl)-2-methylpropanoate

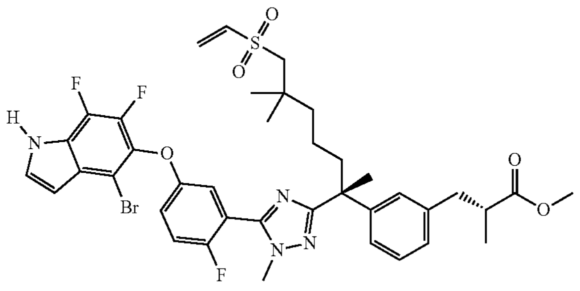 [SMILES: C=CS(=O)(=O)CC(C)(C)CCC[C@](C)(c1cccc(C[C@@H](C)C(=O)OC)c1)c1nc(-c2cc(Oc3c(F)c(F)c4[nH]ccc4c3Br)ccc2F)n(C)n1]

Step B: To a stirred solution of the product from Step A (7.00 g, 8.40 mmol) in dichloromethane (80 mL) was added triethylamine (3.5 mL, 25.2 mmol), followed by methanesulfonyl chloride (0.72 mL, 9.24 mmol). The mixture was stirred at room temperature for 2.0 hours and concentrated. The residue was purified by automated flash chromatography (120 g silica gel column, eluting with 0-65% ethyl acetate in petroleum ether) to afford the title compound (6.20 g, 91%) as a light-yellow solid. LC-MS: MS (ESI): 815, 817 m/z $[M+H]^+$, retention time: 2.01 minutes; purity: 99% (214 nm) (LC-MS method 016)

Methyl (2R)-2-methyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanoate

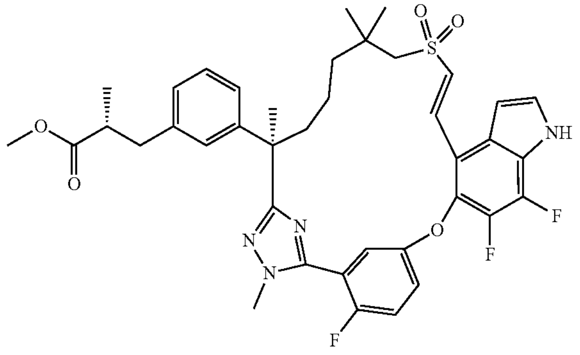 [SMILES: COC(=O)[C@H](C)Cc1cccc([C@@]2(C)CCCC(C)(C)CS(=O)(=O)/C=C/c3c(c(F)c(F)c4[nH]ccc34)Oc3ccc(F)c(c3)-c3nc2nn3C)c1]

Step C: To a stirred and heated (120° C.) solution of triethylamine (9.7 mL, 69.9 mmol) and bis(tri-t-butylphosphine)palladium(0) (1.07 g, 2.10 mmol) in toluene (600 mL), kept under an argon atmosphere, was added dropwise over 1.5 hours a solution of the product from Step B (5.70 g, 6.99 mmol) in toluene (50 mL). The mixture was stirred at 120° C. for 2 hours and concentrated. The residue was purified by automated flash chromatography (330 g silica gel column, eluting with 0-50% ethyl acetate in petroleum ether) to give the title compound (3.50 g, 68%) as a light-yellow solid. LC-MS: MS (ESI): 735 m/z $[M+H]^+$, retention time: 2.06 minutes; purity: >99% (214 nm) (LC-MS method 004).

Methyl (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoate

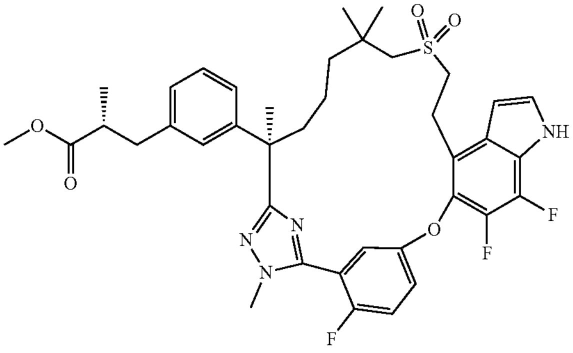

Step D: To a stirred solution of the product from Step C (3.80 g, 5.17 mmol) in ethanol (100 mL) was added 10% palladium on carbon (wetted with ca. 55% Water, 800 mg). The reaction mixture was stirred under a hydrogen balloon for 4 hours at 50° C. The catalyst was removed by filtration and the solids washed with ethanol (30 mL×3). The combined filtrates were concentrated to give the title compound (3.70 g, 97%) as a white solid. LC-MS: MS (ESI): 737 m/z $[M+H]^+$, retention time: 2.04 minutes; purity: 98% (254 nm) (LC-MS method 004).

Compound 200: (2R)-2-Methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic acid

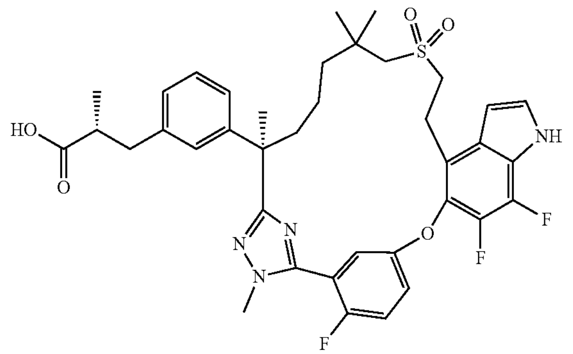 [SMILES: C[C@H](Cc1cccc([C@@]2(C)CCCC(C)(C)CS(=O)(=O)CCc3c(c(F)c(F)c4[nH]ccc34)Oc3ccc(F)c(c3)-c3nc2nn3C)c1)C(=O)O]

Step E: To a stirred solution of the product from Step D (3.70 g, 5.02 mmol) in tetrahydrofuran (10 mL), methanol (10 mL) and water (10 mL) was added lithium hydroxide monohydrate (421 mg, 10.0 mmol). The reaction was stirred at room temperature for 3 hours, then acidified with 1.0 M hydrochloric acid to pH ~6 and extracted with ethyl acetate (3×100 mL). The combined organic extracts were washed with brine, dried over sodium sulfate, filtered, and concentrated. The residue was purified by automated flash chromatography (120 g silica gel column, eluting with 0-40% acetone in petroleum ether) to give the title compound (3.00 g, 83%) as a white solid. LC-MS: MS (ESI): 723 m/z $[M+H]^+$, retention time: 2.01 minutes; purity: 98% (254 nm) (LC-MS method 004). $^1$H NMR (400 MHz, $CD_3OD$) δ 7.38-7.34 (m, 3H), 7.24-7.22 (m, 1H), 7.14 (t, J=8.0 Hz, 1H), 7.02-6.96 (m, 3H), 6.67 (t, J=3.2 Hz, 1H), 3.85 (d, J=2.0 Hz, 3H), 3.35-3.30 (m, 2H), 3.29-3.25 (m, 1H), 3.21-3.15 (m, 1H), 2.99-2.88 (m, 2H), 2.83-2.79 (m, 1H), 2.63-2.54 (m, 2H), 2.20-2.10 (m, 1H), 1.87-1.77 (m, 1H), 1.67 (s, 3H), 1.64-1.55 (m, 1H), 1.39-1.27 (m, 1H), 1.24-1.17 (m, 1H), 1.07-0.98 (m, 10H) ppm.

Example 201. (2S)-3-[3-[(6R)-22-Fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

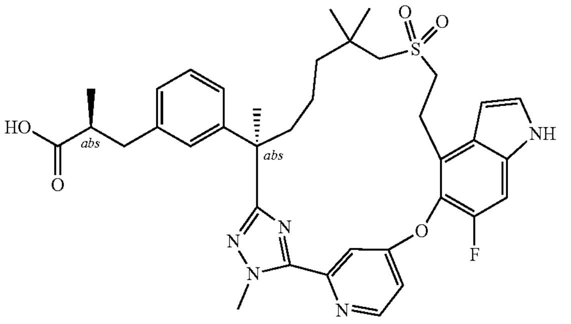 [SMILES: C[C@@H](Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O]

Exchanging methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 612 mg, 1.26 mmol) in Step A, the reaction procedure sequence (Steps A to E) described for Example 197 was followed to afford the title compound as a mixture of two diastereomers (45 mg) as a white solid. LC-MS: MS (ESI): 688 m/z $[M+H]^+$, purity: 99% (214 nm); retention time: 1.93 minutes (LC-MS Method 4). $^1$H NMR (400 MHz, $CD_3OD$) δ 8.65 (d, J=4.4 Hz, 1H), 7.66 (d, J=1.6 Hz, 1H), 7.34 (d, J=2.4 Hz, 1H), 7.29-7.25 (m, 2H), 7.13 (t, J=6.0 Hz, 1H), 7.01 (s, 1H), 6.98-6.90 (m, 2H), 6.69 (d, J=2.4 Hz, 1H), 4.34 (s, 3H), 3.45-3.39 (m, 2H), 3.20-2.95 (m, 2H), 2.94-2.86 (m, 1H), 2.63-2.51 (m, 4H), 2.07-1.97 (m, 1H), 1.81-1.75 (m, 1H), 1.64 (s, 3H), 1.45-1.35 (m, 1H), 1.20-1.15 (m, 1H), 1.07-1.02 (m, 3H), 0.98-0.90 (m, 8H) ppm.

Example 202. (2R)-3-[3-[(6R)-22-fluoro-3,6,10,10-tetramethyl-12,12-dioxo-24-oxa-12λ6-thia-3,4,19,27,30-pentazapentacyclo[23.3.1.12,5.015,23.016,20]triaconta-1(29),2(30),4,15,17,20,22,25,27-nonaen-6-yl]phenyl]-2-methyl-propanoic Acid

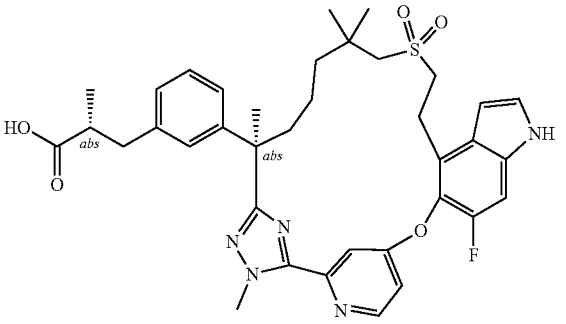 [SMILES: C[C@H](Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O]

Exchanging methyl 4-((4-bromo-6-fluoro-1H-indol-5-yl)oxy)pyridine-2-carbimidothioate (Intermediate 133-1) with methyl 5-((4-bromo-6-fluoro-1H-indol-5-yl)oxy)pyridine-3-carbimidothioate (Intermediate 14-14, 0.52 g, 1.36 mmol) in Step A, the reaction procedure sequence (Steps A to E) described for Example 197 was followed to afford the title compound (35 mg) as a white solid. MS (ESI): 688 m/z $[M+H]^+$, purity: 99% (254 nm); retention time: 1.89 minutes (LC-MS Method 27). $^1$H NMR (400 MHz, $CD_3OD$) δ 8.70 (d, J=1.2 Hz, 1H), 8.62 (d, J=2.4 Hz, 1H), 7.71 (s, 1H), 7.33 (d, J=2.8 Hz, 1H), 7.25 (d, J=8.8 Hz, 1H), 7.13 (t, J=6.0 Hz, 1H), 7.05-7.02 (m, 1H), 7.03-6.97 (m, 2H), 6.66 (d, J=2.0 Hz, 1H), 4.04 (s, 3H), 3.45-3.40 (m, 2H), 3.21-3.16 (m, 2H), 2.93-2.89 (m, 1H), 2.79-2.57 (m, 4H), 2.12-2.06 (m, 1H), 1.83-1.78 (m, 1H), 1.64 (s, 3H), 1.48-1.44 (m, 1H), 1.30-1.20 (m, 2H), 1.11-1.05 (m, 4H), 1.00 (s, 3H), 0.99 (s, 3H) ppm.

Example 204. Diastereomer 2 of (2S)-3-[3-[(6R)-22,28-difluoro-3,6,10,10-tetramethyl-12,12,24-trioxo-12λ6,24 M-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid

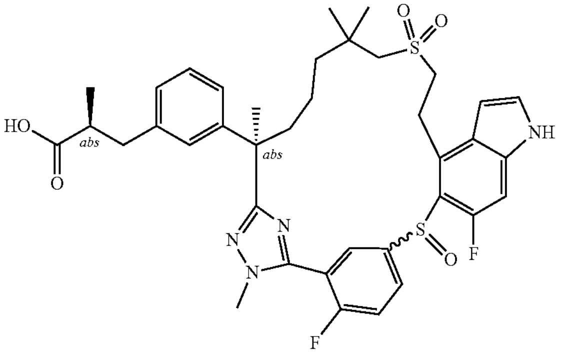 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O]

Methyl (2S)-2-methyl-3-[3-[(1R)-1-[5-[5-[(4-bromo-6-fluoro-1H-indol-5-yl)sulfanyl]-2-fluoro-phenyl]-1-methyl-1,2,4-triazol-3-yl]-6-(2-hydroxyethylsulfonyl)-1,5,5-trimethyl-hexyl]phenyl]propanoate

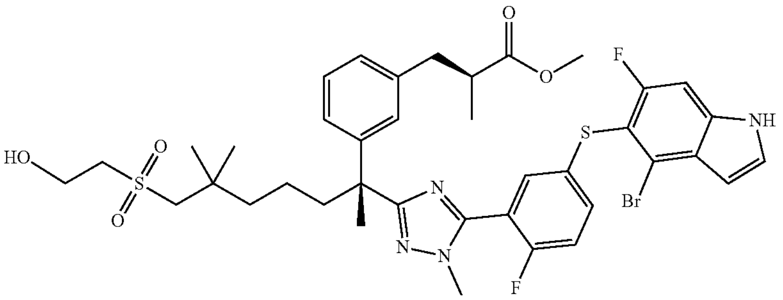 [SMILES: COC(=O)[C@@H](C)Cc1cccc([C@@](C)(CCCC(C)(C)CS(=O)(=O)CCO)c2nc(-c3cc(Sc4c(F)cc5[nH]ccc5c4Br)ccc3F)n(C)n2)c1]

Step A: To a stirred solution of methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 18.00 g, 37.1 mmol) and methyl 5-((4-bromo-6-fluoro-1H-indol-5-yl)thio)-2-fluorobenzimidothioate hydroiodide (Intermediate 76, 20.10 g, 37.1 mmol) in pyridine (150 mL) was added magnesium sulfate (17.88 g, 149 mmol). The mixture was stirred for 16 hours at 80° C., cooled to room temperature, and poured into 400 mL of water. The solution was extracted with ethyl acetate (2×200 mL). The combined organic phases were washed with 1 N hydrochloric acid and brine (300 mL), dried over sodium sulphate, filtered, and concentrated. The residue was purified by flash chromatography (330 g silica gel column, eluting with 0-70% ethyl acetate in petroleum ether) to give the title compound (19.00 g, 62%) as a yellow solid. MS (ESI): 831, 833 m/z $[M+H]^+$, retention time: 2.02 minutes; purity: 87% (214 nm) (LC-MS method 4).

Methyl (2S)-3-[3-[(1R)-1-[5-[5-[(4-bromo-6-fluoro-1H-indol-5-yl)sulfanyl]-2-fluoro-phenyl]-1-methyl-1,2,4-triazol-3-yl]-1,5,5-trimethyl-6-vinylsulfonyl-hexyl]phenyl]-2-methyl-propanoate

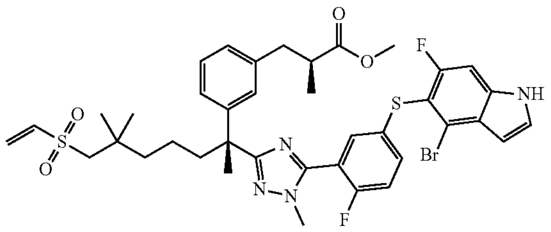 [SMILES: C=CS(=O)(=O)CC(C)(C)CCC[C@](C)(c1cccc(C[C@H](C)C(=O)OC)c1)c1nc(-c2cc(Sc3c(F)cc4[nH]ccc4c3Br)ccc2F)n(C)n1]

Step B: To a solution of Step A product (18.80 g, 22.6 mmol) in dichloromethane (150 mL) was added triethylamine (9.5 mL, 67.8 mmol) and methane sulfonyl chloride (1.10 eq, 1.9 mL, 24.9 mmol). The mixture was stirred at room temperature for 2.0 hours and concentrated. The residue was purified by automated flash chromatography (330 silica gel column, eluting with 0-50% ethyl acetate in petroleum ether) to afford the title compound (16.00 g, 87%) as a light-yellow solid. MS (ESI): 813, 815 m/z $[M+H]^+$, retention time: 2.13 minutes; purity: 96% (214 nm) (LC-MS method 4).

Methyl (2S)-3-[3-[(6R,13E)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,13,15,17,20,22,25,27-decaen-6-yl]phenyl]-2-methyl-propanoate

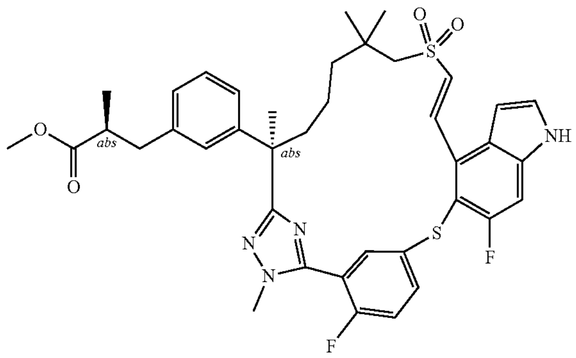 [SMILES: COC(=O)[C@@H](C)Cc1cccc([C@@]2(C)CCCC(C)(C)CS(=O)(=O)/C=C/c3c(c(F)cc4[nH]ccc34)Sc3ccc(F)c(c3)-c3nc2nn3C)c1]

Step C: To a stirred solution of triethylamine (27 mL, 194 mmol) and bis(tri-t-butylphosphine)palladium(0) (1.98 g, 3.88 mmol) in toluene (700 mL) was added dropwise a solution of Step B product (15.80 g, 19.4 mmol) in toluene (50 mL) over 2 hours under argon at 120° C. The mixture was stirred at 120° C. for another 0.5 hours and concentrated. The residue was purified by automated flash chromatography (330 g silica gel column, eluting with 0-50% ethyl acetate in petroleum ether) to give the title compound (9.80 g, 69%) as a yellow solid. MS (ESI): 733 m/z [M+H]+, retention time: 2.10 minutes; purity: 96% (214 nm) (LC-MS method 4).

Methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

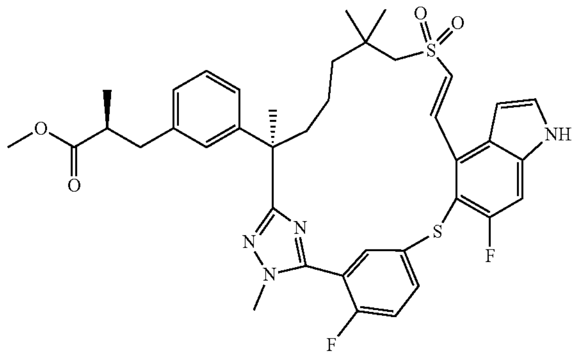 [SMILES: COC(=O)[C@@H](C)Cc1cccc([C@@]2(C)CCCC(C)(C)CS(=O)(=O)/C=C/c3c(c(F)cc4[nH]ccc34)Sc3ccc(F)c(c3)-c3nc2nn3C)c1]

Step D: To a stirred solution of Step C product (9.65 g, 13.2 mmol) in ethanol (150 mL) was added 10% palladium on carbon (wetted with ca. 55% water, 2 g). The reaction mixture was stirred under hydrogen for 4 hours at 50° C., cooled to room temperature, and filtered through a pad of Celite. The filtrate was concentrated to give the title compound (8.90 g, 92%) as a solid. MS (ESI): 735 m/z [M+H]+, retention time: 2.09 minutes; purity: 84% (214 nm) (LC-MS method 4).

Methyl (2S)-3-[3-[(6R)-22,28-difluoro-3,6,10,10-tetramethyl-12,12-dioxo-19-(p-tolylsulfonyl)-1226,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

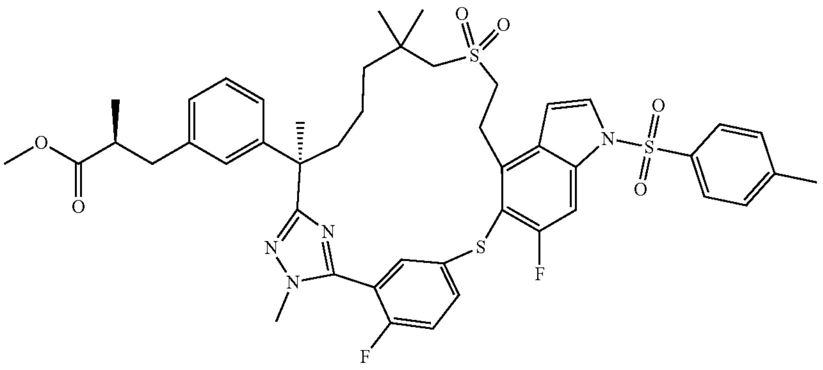

Step E: To a stirred solution of Step D product (8.75 g, 11.9 mmol) in acetonitrile (100 mL) was added 1-(p-tolylsulfonyl)imidazole (5.29 g, 23.8 mmol) and 1,8-diazabicyclo[5.4.0]undec-7-ene (3.6 mL, 23.8 mmol). The mixture was stirred at room temperature overnight, diluted with water (200 mL), and extracted with ethyl acetate (2×150 mL). The combined organic phases were washed with brine, dried over sodium sulfate, filtered, and concentrated. The residue was purified by automated silica gel column chromatography (120 g silica gel column, eluting with 0-50% ethyl acetate in petroleum ether) to give the title compound (8.30 g, 78%) as a solid. MS (ESI): 889 m/z [M+H]+, retention time: 2.27 minutes; purity: 90% (214 nm) (LC-MS method 34).

Diastereomer 2 of Methyl (2S)-3-[3-[(6R)-22,28-difluoro-3,6,10,10-tetramethyl-12,12,24-trioxo-19-(p-tolylsulfonyl)-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

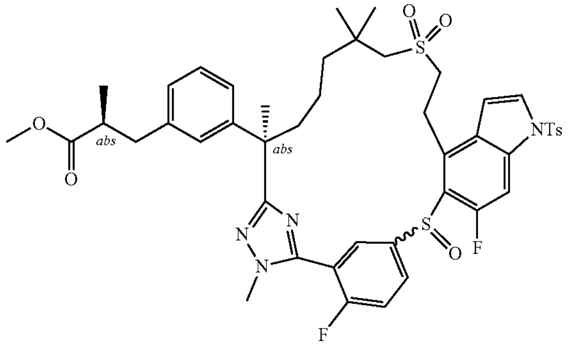 [SMILES: COC(=O)[C@@H](C)Cc1cccc([C@@]2(C)CCCC(C)(C)CS(=O)(=O)CCc3c(c(F)cc4c3ccn4S(=O)(=O)c3ccc(C)cc3)S(=O)c3ccc(F)c(c3)-c3nc2nn3C)c1]

Step F: To a stirred solution of Step E product (5.00 g, 5.62 mmol) in acetonitrile (100 mL) was added (S,S)-hydrobenzoin (6.02 g, 28.1 mmol), titanium(IV) isopropoxide (4.9 mL, 16.9 mmol) and tert-butyl hydroperoxide (1.52 g, 16.9 mmol). The mixture was stirred at room temperature overnight, poured into 200 mL of water, and extracted with ethyl acetate (2×150 mL). The combined organic phases were washed with brine (300 mL), dried over sodium sulphate, filtered, and concentrated. The residue was purified by automated flash chromatography (80 g silica gel column, eluting with 0-60% ethyl acetate in petroleum ether) to give the title compound (4.10 g, 81%) as a solid. MS (ESI): 905 m/z [M+H]+, retention time: 2.15 minutes; purity: 91% (214 nm) (LC-MS method 34).

Diastereomer 2 of methyl (2S)-3-[3-[(6R)-22,28-difluoro-3,6,10,10-tetramethyl-12,12,24-trioxo-12λ6,24λ4-dithia-3,4,19,30-tetrazapentacyclo [23.3.1.12,5.015,23.016,20]triaconta-1(29),2(30),4,15,17,20,22,25,27-nonaen-6-yl]phenyl]-2-methyl-propanoate

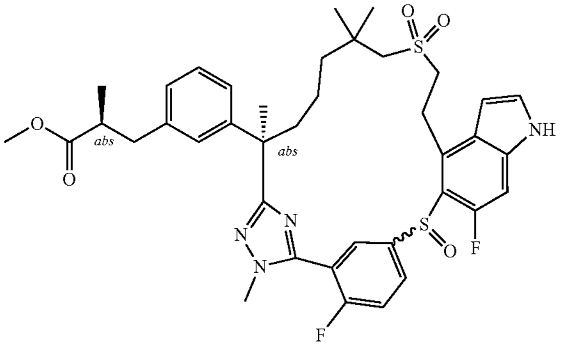 [SMILES: COC(=O)[C@@H](C)Cc1cccc([C@@]2(C)CCCC(C)(C)CS(=O)(=O)CCc3c(c(F)cc4[nH]ccc34)S(=O)c3ccc(F)c(c3)-c3nc2nn3C)c1]

Step G: To a stirred solution of Step F product (1.50 g, 1.66 mmol) in methanol (20 mL) was added potassium carbonate (0.46 g, 3.31 mmol). The mixture was stirred at room temperature for 3 hours, poured into 80 mL of water, and extracted with ethyl acetate (2×50 mL). The combined organic phases were washed with brine, dried over sodium sulphate, filtered, and concentrated. The residue was purified by automated flash chromatography (40 g silica gel column, eluting with 0-80% ethyl acetate in petroleum ether) to give the title compound (1.10 g, 88%) as a solid. MS (ESI): 751 m/z [M+H]+, retention time: 1.99 minutes; purity: 97% (214 nm) (LC-MS method 34).

Compound 204: Diastereomer 2 of (2S)-3-[3-[(6R)-22,28-difluoro-3,6,10,10-tetramethyl-12,12,24-tri-oxo-12λ6,24λ4-dithia-3,4,19,30-tetrazapentacyclo [23.3.1.12,5.015,23.016,20]triaconta-1(29),2(30),4,15,17,20,22,25,27-nonaen-6-yl]phenyl]-2-methyl-propanoic Acid

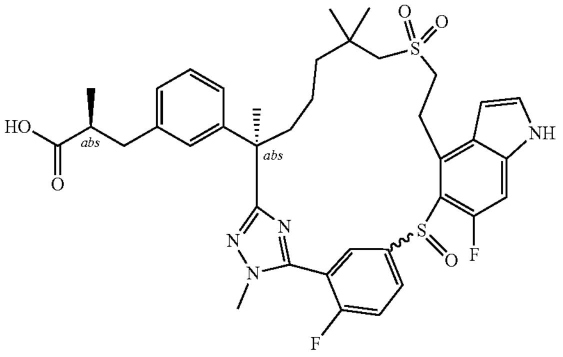 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O]

Step H: To a stirred solution of Step G product (1100 mg, 1.46 mmol) in tetrahydrofuran (16 mL) was added lithium hydroxide monohydrate (8.0 mL, 8.00 mmol) (1 M in water). The mixture was stirred at room temperature for 24 hours, then acidified with 1.0 M hydrochloric acid to pH ~6 and extracted with ethyl acetate (3×40 mL). The combined organic phases were washed with brine, dried over sodium sulfate, filtered, and concentrated. The residue was purified by automated flash chromatography (40 g silica gel column, eluting with 0-100% ethyl acetate in petroleum ether) to give a white solid. This white solid was triturated with acetonitrile to afford the title compound (700 mg, 65%) as a white solid. MS (ESI): 737 m/z [M+H]+, retention time: 2.37 minutes; purity: 99% (214 nm) (LC-MS method 17). $^{1}$H NMR (400 MHz, $CD_3OD$) δ 8.20-8.10 (m, 1H), 8.00-7.85 (m, 1H), 7.60-7.53 (m, 1H), 7.37 (d, J=3.2 Hz, 1H), 7.19-6.97 (m, 5H), 6.67 (s, 1H), 3.98-3.80 (m, 4H), 3.71-3.64 (m, 1H), 3.56-3.44 (m, 1H), 3.25-3.00 (m, 3H), 2.96-2.88 (m, 1H), 2.64-2.56 (m, 2H), 2.32-2.20 (m, 1H), 2.00-1.90 (m, 1H), 1.71 (s, 3H), 1.50-1.35 (m, 3H), 1.21 (s, 3H), 1.14 (s, 3H), 1.07-1.04 (m, 4H) ppm.

Example 205. Diastereomer 1 of (2S)-3-[3-[(6R)-22,28-difluoro-3,6,10,10-tetramethyl-12,12,24-tri-oxo-12λ6,24λ4-dithia-3,4,19,30-tetrazapentacyclo [23.3.1.12,5.015,23.016,20]triaconta-1(29),2(30),4,15,17,20,22,25,27-nonaen-6-yl]phenyl]-2-methyl-propanoic acid

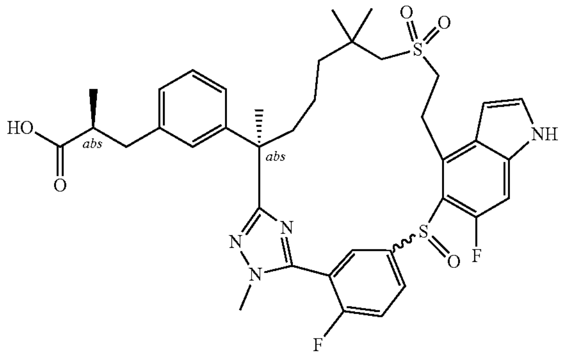 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O]

Mixture of Diastereomers 1 and 2 of methyl (2S)-3-[3-[(6R)-22,28-difluoro-3,6,10,10-tetramethyl-12,12,24-trioxo-19-(p-tolylsulfonyl)-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

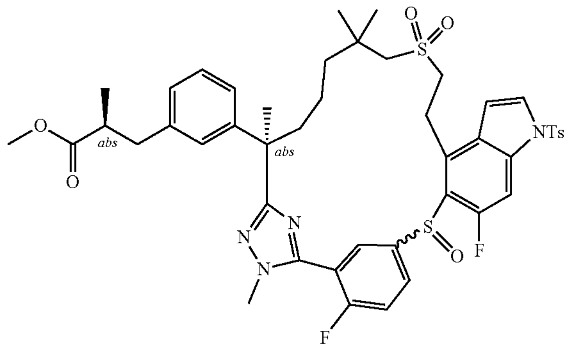 [SMILES: COC(=O)[C@@H](C)Cc1cccc([C@@]2(C)CCCC(C)(C)CS(=O)(=O)CCc3c(c(F)cc4c3ccn4S(=O)(=O)c3ccc(C)cc3)S(=O)c3ccc(F)c(c3)-c3nc2nn3C)c1]

Step A: To a stirred solution of methyl (2S)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step E product of Compound 204, 1000 mg, 1.12 mmol) in acetonitrile (20 mL) was added (2R,3R)-diethyl 2,3-dihydroxysuccinate (2319 mg, 11.2 mmol), titanium(IV) isopropoxide (1.6 mL, 5.62 mmol) and tert-butyl hydroperoxide (507 mg, 5.62 mmol). The mixture was stirred at 40° C. overnight, cooled to room temperature, and poured into 100 mL of water. The solution was extracted with ethyl acetate (2×80 mL). The combined organic phases were washed with brine (150 mL), dried over sodium sulphate, filtered, and concentrated. The residue was purified by automated flash chromatography (25 g silica gel column, eluting with 0-60% ethyl acetate in petroleum ether) to give the title compound (700 mg, 69%, Diastereomer 1: Diastereomer 2=35:61) as a solid. MS (ESI): 905 m/z [M+H]+, retention time: 2.12 minutes (diastereomer 1, 35% purity (214 nm)); 2.16 minutes (Diastereomer 2, 61% purity, 214 nm) (LC-MS method 17).

Compound 205A: Diastereomer 1 of (2S)-3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid

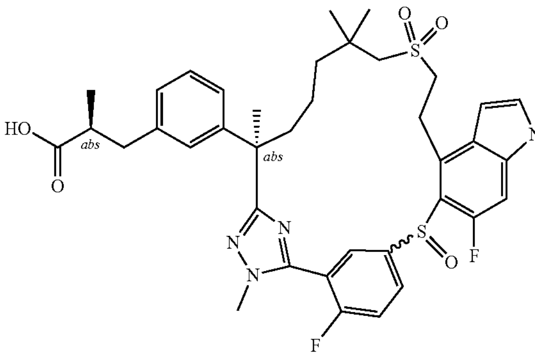

Step B: To a stirred solution of Step A product (318 mg, 0.351 mmol) in tetrahydrofuran (2 mL) and water (2 mL) was added lithium hydroxide monohydrate (74 mg, 1.76 mmol). The mixture was stirred at room temperature overnight, then acidified with 1.0 M hydrochloric acid to pH~6 and extracted with ethyl acetate (3×10 mL). The combined organic phases were washed with brine, dried over sodium sulfate, filtered, and concentrated. The residue (260) mg was subject to chiral SFC separation using SFC-150 (Thar, Waters) instrument under the following condition: Column: AS 20×250 mm, 10 μm; Column temperature: 35° C.; Mobile phase: carbon dioxide/methanol (0.2%7M ammonia in methanol)=55/45; Flow rate: 100 g/minute; Back pressure: 100 bar; Detection wavelength: 214 nm; Cycle time: 3.03 minutes; Sample solution: 260 mg dissolved in 21 mL of methanol; Injection volume: 1 mL. The first eluent, Diastereomer 1, was designated as Compound 205 (80 mg); The second eluent, Diastereomer 2, was designated as Compound 204 (112 mg). Compound 205: MS (ESI): 737 m/z [M+H]+, retention time: 1.79 minutes, purity: >99% (214 nm) (LC-MS method 4).

Example 206. Diastereomers 1 and 2 of (2R)-3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

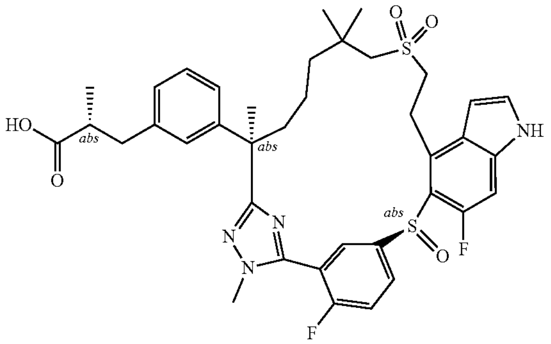 [SMILES: C[C@H](Cc1cccc([C@@]2(C)CCCC(C)(C)CS(=O)(=O)CCc3c(c(F)cc4[nH]ccc34)[S@@](=O)c3ccc(F)c(c3)-c3nc2nn3C)c1)C(=O)O]

Methyl (2R)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

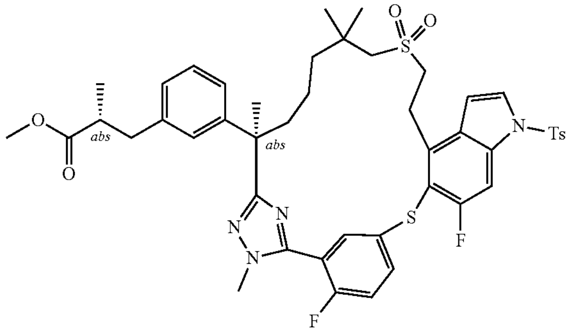

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 16.6 g, 33.7 mmol) in Step A, the reaction procedure sequence (Steps A to E) described for Example 204 was used to prepare the title compound (1.5 g) as an oil. MS (ESI): 889 m/z $[M+H]^+$, retention time: 1.62 minutes; Purity: 91% (214 nm) (LC-MS Method 33).

Methyl (2R)-3-[3-[(6R)-22,28-difluoro-3,6,10,10-tetramethyl-12,12,24-trioxo-19-(p-tolylsulfonyl)-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

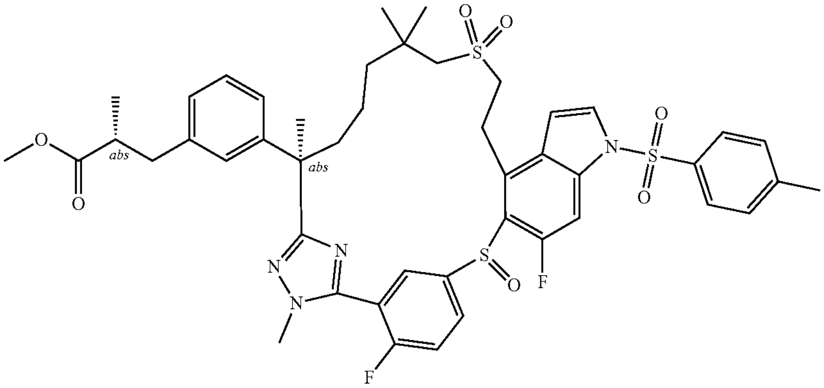

Step B: To a stirred solution of Step A product (3.3 g, 3.7 mmol) in acetonitrile (33 mL) was added hydrogen peroxide (30% in water 11 mL) and toluene sulfonic acid (33 mg) at 30° C. The mixture was stirred at 30° C. for 24 hours, quenched with water (50 mL), and extracted with ethyl acetate (2×50 mL). The combined organic phases were washed with brine, dried over sodium sulfate, filtered, and concentrated. The residue was purified by automated flash column chromatography (80 g silica gel column, eluting with 0-50% ethyl acetate in petroleum ether) to give the title compound (1.7 g, 52%, mixture of two diastereomers) as a solid. MS (ESI): 905 m/z $[M+H]^+$, retention time: 2.06 minutes (purity: 45%, 214 nm), 2.11 minutes (purity: 55%, 214 nm) (LC-MS method 34).

Example 206A and 206B: Diastereomer 1 and 2 of (2R)-3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

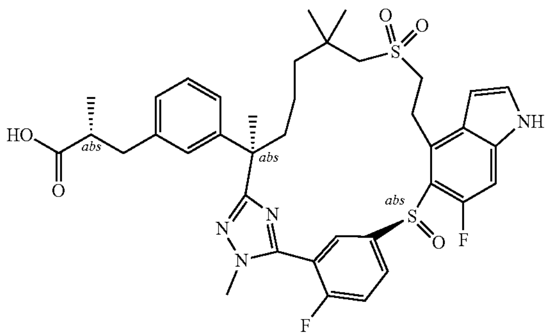 [SMILES: C[C@H](Cc1cccc([C@@]2(C)CCCC(C)(C)CS(=O)(=O)CCc3c(c(F)cc4[nH]ccc34)[S@@](=O)c3ccc(F)c(c3)-c3nc2nn3C)c1)C(=O)O]

Step C: To a stirred solution of Step B product (1.7 g, 1.88 mmol) in tetrahydrofuran (15 mL) and water (5 mL) was added lithium hydroxide monohydrate (160 mg, 3.76 mmol). The reaction mixture was stirred at room temperature overnight, then diluted with water (10 mL), and acidified to pH ~5-6 with 1 N hydrochloric acid. The mixture was extracted with ethyl acetate (2×50 mL). The combined organic phases were washed with brine, dried over sodium sulfate, filtered, and concentrated. The residue was purified by prep-HPLC. The first eluent, diastereomer 1, was designated as Compound 206B (450 mg, 33%) as solid. The second eluent, Diastereomer 2, was designated as Compound 206A (520 mg, 38%).

Compound 206A: MS (ESI): 737 m/z $[M+H]^+$, retention time: 1.82 minutes; Purity: 95%, 214 nm) (LC-MS method 34). $^1$H NMR (400 MHz, $CD_3OD$) δ 8.20-8.07 (m, 1H), 7.98-7.82 (m, 1H), 7.60-7.53 (m, 1H), 7.38 (d, J=3.3 Hz, 1H), 7.24-7.08 (m, 3H), 7.06-6.94 (m, 2H), 6.66 (s, 1H), 3.85 (d, J=2.6 Hz, 3H), 3.72-3.42 (m, 3H), 3.14-2.88 (m, 4H), 2.66-2.55 (m, 2H), 2.34-2.23 (m, 1H), 2.00-1.90 (m, 1H), 1.71 (s, 3H), 1.51-1.27 (m, 4H), 1.21 (s, 3H), 1.16-1.02 (m, 6H) ppm.

Compound 206B: MS (ESI): 737 m/z $[M+H]^+$, retention time: 1.78 minutes; Purity: 95%, 214 nm) (LC-MS method 34). $^1$H NMR (400 MHz, $CD_3OD$) δ 8.15-7.95 (m, 2H), 7.62-7.55 (m, 1H), 7.37 (d, J=3.2 Hz, 1H), 7.20-7.12 (m, 2H), 7.07 (s, 1H), 7.00-6.95 (m, 2H), 6.68 (s, 1H), 3.79 (s, 3H), 3.64-3.35 (m, 3H), 3.12-2.94 (m, 4H), 2.66-2.56 (m, 2H), 2.41-2.34 (m, 1H), 1.87-1.69 (m, 1H), 1.69 (s, 3H), 1.42-1.06 (m, 13H) ppm.

Example 209. 2-[3-[(6R)-22,28-difluoro-3,6,10,10-tetramethyl-12,12,24-trioxo-12λ6,24M-dithia-3,4,19,30-tetrazapentacyclo[23.3.1.12,5.015,23.016,20]triaconta-1(29),2(30),4,15,17,20,22,25,27-nonaen-6-yl]phenyl]acetic acid

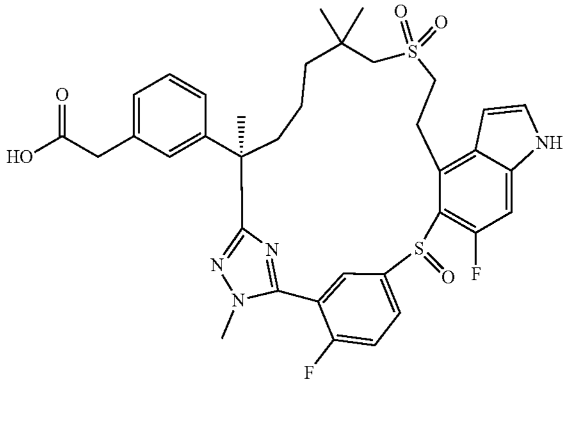 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CC(=O)O)c1]

Ethyl (R)-2-(3-(2-(5-(5-((4-bromo-6-fluoro-1H-indol-5-yl)thio)-2-fluorophenyl)-1-methyl-1H-1,2,4-triazol-3-yl)-7-((2-((tert-butyldiphenylsilyl)oxy)ethyl)sulfonyl)-6,6-dimethylheptan-2-yl)phenyl)acetate

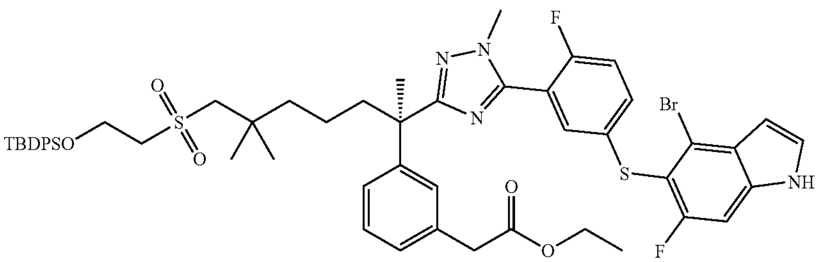

Step A: To a stirred solution of ethyl (R)-2-(3-(7-((2-((tert-butyldiphenylsilyl)oxy)ethyl)sulfonyl)-2,6,6-trimethyl-1-(2-methylhydrazineyl)-1-oxoheptan-2-yl)phenyl) acetate (Intermediate 137-2, 1.20 g, 1.69 mmol) in pyridine (15 mL) was added methyl 5-((4-bromo-6-fluoro-1H-indol-5-yl)thio)-2-fluorobenzimidothioate hydroiodide (Intermediate 76, 1.1 g, 2.03 mmol). The mixture was stirred at 85° C. for 16 hours and concentrated. The residue was diluted with water (40 mL) and 1N HCl (15 mL), extracted with ethyl acetate (3×30 mL). The combined organic extracts were washed with water (15 mL), dried over sodium sulfate, filtered, and concentrated. The residue was purified by automated column chromatography (40 g silica gel column; eluting with 0-50% ethyl acetate in petroleum ether) to give the title compound (1.50 g, 44%) as a solid. MS (ESI): 1055, 1057 m/z $[M+H]^+$, retention time: 2.52 minutes; Purity: 52%, 254 nm) (LC-MS method 4).

Ethyl (R)-2-(3-(2-(5-(5-((4-bromo-6-fluoro-1H-indol-5-yl)thio)-2-fluorophenyl)-1-methyl-1H-1,2,4-triazol-3-yl)-7-((2-hydroxyethyl)sulfonyl)-6,6-dimethylheptan-2-yl)phenyl)acetate

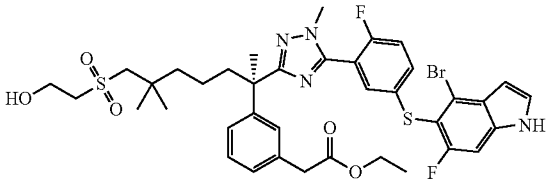 [SMILES: CCOC(=O)Cc1cccc([C@@](C)(CCCC(C)(C)CS(=O)(=O)CCO)c2nc(-c3cc(Sc4c(F)cc5[nH]ccc5c4Br)ccc3F)n(C)n2)c1]

Step B: To a stirred solution of Step A product (1.5 g, 1.4 mmol) in tetrahydrofuran (21 mL) was added tetra-n-butylammonium fluoride (1M in tetrahydrofuran, 7.1 mL, 7.1 mmol). The mixture was stirred at room temperature for 16 hours, diluted with water (40 mL), and extracted with ethyl acetate (3×45 mL). The combined organic layers were washed with brine (30 mL), dried over sodium sulfate, filtered, and concentrated. The residue was purified by automated column chromatography (40 g silica gel column; eluting with 0-70% ethyl acetate in petroleum ether) to give the title compound (0.8 g, 67%) as a solid. MS (ESI): 817, 819 m/z $[M+H]^+$, retention time: 2.06 minutes; Purity: 98% (254 nm) (LC-MS method 33).

Compounds 209A and 209B: 2-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]acetic Acid

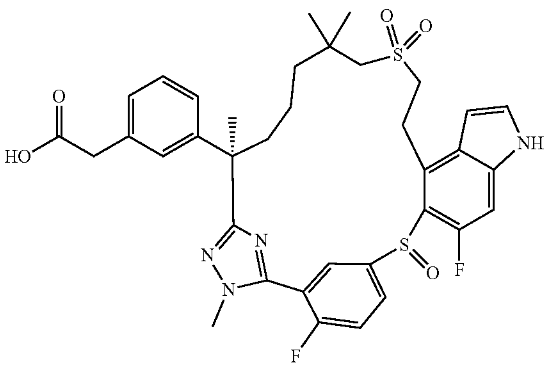 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CC(=O)O)c1]

Step C: Exchanging methyl (2S)-2-methyl-3-[3-[(1R)-1-[5-[5-[(4-bromo-6-fluoro-1H-indol-5-yl)sulfanyl]-2-fluoro-phenyl]-1-methyl-1,2,4-triazol-3-yl]-6-(2-hydroxyethyl-sulfonyl)-1,5,5-trimethyl-hexyl]phenyl]propanoate (Step A product of Example 204) with ethyl (R)-2-(3-(2-(5-(5-((4-bromo-6-fluoro-1H-indol-5-yl)thio)-2-fluorophenyl)-1-methyl-1H-1,2,4-triazol-3-yl)-7-((2-hydroxyethyl)sulfonyl)-6,6-dimethylheptan-2-yl)phenyl)acetate (Step B product of this Example, 0.8 g, 0.978 mmol), the reaction procedure sequence (Steps B to E of Example 204, followed by Steps B and C of Example 205) was used to prepare the title compounds. The two diastereomeric acid mixture, obtained from indole-deprotection/ester hydrolysis at the corresponding Step C of Example 206, was subjected to chiral prep-HPLC separation. The first eluent, Diastereomer 1, was Compound 209A (12 mg, white solid). The second eluent, Diastereomer 2, Compound 209B (22 mg, white solid).

Compound 209A: MS (ESI): 709 m/z $[M+H]^+$, retention time: 1.78 minutes; Purity: 99%, 214 nm) (LC-MS method 4).

Compound 209B: MS (ESI): 709 m/z $[M+H]^+$, retention time: 1.80 minutes; Purity: 97%, 214 nm) (LC-MS method 4).

Example 210. Diastereomers 1, 2, 3, and 4 of (E)-3-[3-(22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl)phenyl]prop-2-enoic Acid

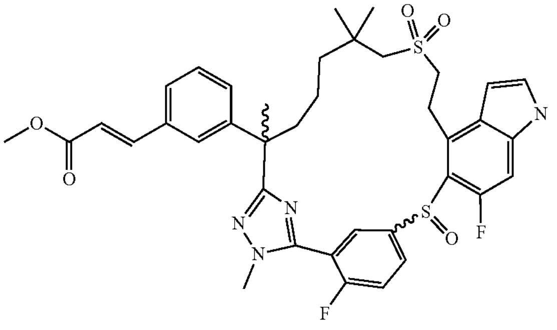 [SMILES: COC(=O)/C=C/c1cccc(C2(C)CCCC(C)(C)CS(=O)(=O)CCc3c(c(F)cc4[nH]ccc34)S(=O)c3ccc(F)c(c3)-c3nc2nn3C)c1]

6-(3-Benzyloxyphenyl)-22,28-difluoro-3,6,10,10-tetramethyl-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaene 12,12-dioxide

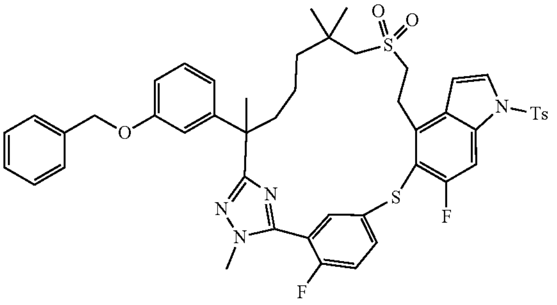 [SMILES: Cc1ccc(S(=O)(=O)n2ccc3c4c(c(F)cc32)Sc2ccc(F)c(c2)-c2nc(nn2C)C(C)(c2cccc(OCc3ccccc3)c2)CCCC(C)(C)CS(=O)(=O)CC4)cc1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with 2-(3-(benzyloxy)phenyl)-7-((2-hydroxyethyl)sulfonyl)-N',2,6,6-tetramethylheptanehydrazide (Intermediate 69-3, 3.10 g, 6.32 mmol), the reaction procedure sequence (Steps A to E) described for Example 204 was followed to prepare the title compound as a white solid (750 mg). MS (ESI): 895 m/z $[M+H]^+$, retention time: 2.27 minutes; Purity: >99% (214 nm) (LC-MS method 17).

3-(22,28-Difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl)phenol

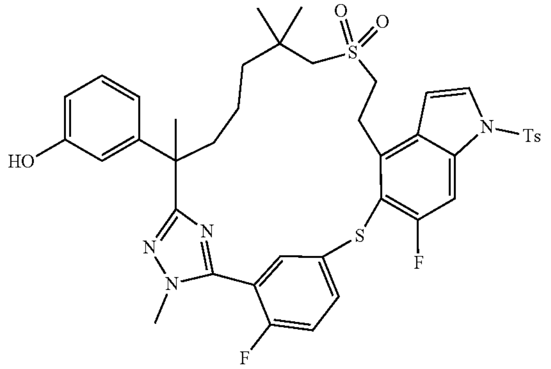 [SMILES: Cc1ccc(S(=O)(=O)n2ccc3c4c(c(F)cc32)Sc2ccc(F)c(c2)-c2nc(nn2C)C(C)(c2cccc(O)c2)CCCC(C)(C)CS(=O)(=O)CC4)cc1]

Step B: To a stirred and cooled (0° C.) solution of Step A product (750 mg, 0.838 mmol) in dichloromethane (30 mL) was added boron tribromide (17% in dichloromethane) (1.5 mL). The reaction mixture was stirred at 0° C. for 20 minutes, quenched with saturated sodium bicarbonate (10 mL), and extracted with ethyl acetate (2×50 mL). The combined organic layers were washed with water, brine, dried over sodium sulfate, filtered, and concentrated. The residue was purified by automated flash chromatography (25 g silica gel column, eluting with 0-80% ethyl acetate in petroleum ether) to give the title compound (580 mg, 86%) as a solid. MS (ESI): 805 m/z $[M+H]^+$, retention time: 2.01 minutes; Purity: 86% (214 nm) (LC-MS method 17).

[3-[22,28-Difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]trifluoromethanesulfonate

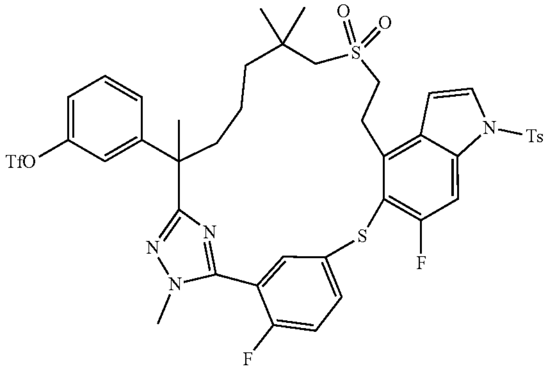 [SMILES: Cc1ccc(S(=O)(=O)n2ccc3c4c(c(F)cc32)Sc2ccc(F)c(c2)-c2nc(nn2C)C(C)(c2cccc(OS(=O)(=O)C(F)(F)F)c2)CCCC(C)(C)CS(=O)(=O)CC4)cc1]

Step C: To a stirred and cooled (0° C.) solution of Step B product (580 mg, 0.721 mmol) in dichloromethane (20 mL) was added triethylamine (0.30 mL, 2.16 mmol) and trifluoromethanesulfonic anhydride (20.24 mL, 1.44 mmol). The reaction mixture was stirred at 0° C. for 20 minutes, quenched with water (30 mL), and extracted with dichloromethane (2×50 mL). The combined organic layers were washed with water, brine, dried over sodium sulfate, filtered, and concentrated. The residue was purified by flash chromatography (25 g silica gel column, eluting with 0-60% ethyl acetate in petroleum ether) to give the title compound (580 mg, 86%) as a solid. MS (ESI): 937 m/z $[M+H]^+$, retention time: 2.24 minutes; Purity: 93% (214 nm) (LC-MS method 17).

Ethyl (E)-3-[3-[22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]prop-2-enoate

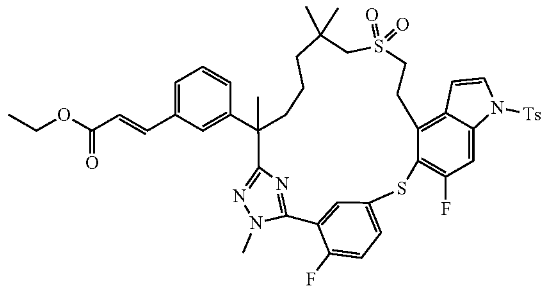 [SMILES: CCOC(=O)/C=C/c1cccc(C2(C)CCCC(C)(C)CS(=O)(=O)CCc3c(c(F)cc4c3ccn4S(=O)(=O)c3ccc(C)cc3)Sc3ccc(F)c(c3)-c3nc2nn3C)c1]

Step D: To a stirred and degassed solution of Step C product (330 mg, 0.35 mmol) in N,N-dimethylformamide (20 mL) was added triethylamine (0.098 mL, 0.70 mmol), ethyl acrylate (71 mg, 0.70 mmol), bis(triphenylphosphine) palladium(II) chloride (25 mg, 0.035 mmol). The mixture was stirred at 100° C. for 5 hours, cooled to room temperature, and quenched with water (100 mL). The solution was extracted with ethyl acetate (2×50 mL). The combined organic layers were washed with brine, dried over sodium sulfate, filtered, and concentrated. The residue was purified by automated flash chromatography (25 g silica gel column, eluting with 0-90% ethyl acetate in petroleum ether) to give the title compound (140 mg, 45%) as a solid. MS (ESI): 887 m/z $[M+H]^+$, retention time: 2.30 minutes; Purity: 92% (214 nm) (LC-MS method 4).

Compounds 210A, 210B, 210C, and 210D Diastereomers 1, 2, 3, and 4 of (E)-3-[3-(22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl)phenyl]prop-2-enoic Acid

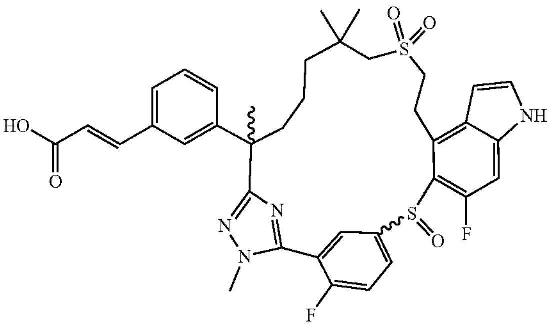 [SMILES: Cn1nc2nc1-c1cc(ccc1F)S(=O)c1c(F)cc3[nH]ccc3c1CCS(=O)(=O)CC(C)(C)CCCC2(C)c1cccc(/C=C/C(=O)O)c1]

Step E: Exchanging methyl (2R)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step A product of Example 206) with ethyl (E)-3-[3-[22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]prop-2-enoate (Step D product of this Example, the reaction procedure sequence (Steps B and C) described for Example 206 was followed to prepare a mixture of 4 diastereomers of the title compounds (80 mg, originated from 2 chiral center). This mixture was subject to prep-HPLC separation to give 19 mg of first eluent (29% yield, mixture of two diastereomers) and 18 mg of second eluent (28% yield, mixture of another two diastereomers). The first eluent was subjected to chiral SFC purification under the following conditions: Instrument: SFC-150 (Waters); Column: AS 20×250 mm, 10 μm; Column temperature: 35° C.; Mobile phase: carbon dioxide/methanol (0.2%7M ammonia in methanol)=50/50; Flow rate: 100 g/minute; Back pressure: 100 bar; Detection wavelength: 214 nm; Cycle time: 3 minutes; Sample solution: 15 mg dissolved in 20 mL of methanol and dichloromethane; Injection volume: 2 mL. The first fraction is Compound 210A (3 mg, 19%), the Second fraction is Compound 210B (4.9 mg, 32%).

The second effluent was also subject to the same SFC conditions as above. The first fraction of the second effluent is Compound 210C (6.5 mg, 41%), the second fraction of the second effluent is Compound 210D (4.8 mg, 31%).

Compound 210A: MS (ESI): 721 m/z $[M+H]^+$, retention time: 1.74 minutes; Purity: 99% (214 nm) (LC-MS method 4). Chiral purity: >99% (Retention time: 1.10 minutes; chiral column condition: Column: AS-H; Mobile phase: carbon dioxide/methanol (0.2%7M ammonia in methanol)=65:35; Flow rate: 4 mL/minute; Column temperature: 40° C.; back pressure: 120 bar).

Compound 210B: MS (ESI): 721 m/z $[M+H]^+$, retention time: 1.74 minutes; Purity: 99% (214 nm) (LC-MS method 4). Chiral purity: 99.2% (ee: 98.4%) (Retention time: 2.09 minutes; Same chiral column condition as Compound 210A)

Compound 210C: MS (ESI): 721 m/z $[M+H]^+$, retention time: 1.77 minutes; Purity: 99% (214 nm) (LC-MS method 4). Chiral purity: >99% (ee:>99%; Retention time: 1.20 minutes; chiral column condition: Same as Compound 210A).

Compound 210D: MS (ESI): 721 m/z $[M+H]^+$, retention time: 1.77 minutes; Purity: 99% (214 nm) (LC-MS method 4). Chiral purity: 99.1% (ee: 98.2%; Retention time: 2.21 minutes; chiral column condition: Same as Compound 210A).

Example 211. Diastereomers 1 and 2 of (2S)-3-[3-[(6R)-22-fluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

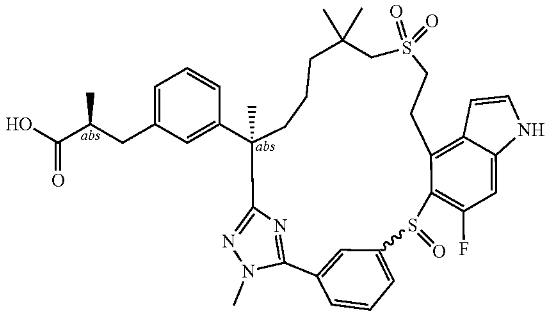 [SMILES: C[C@@H](Cc1cccc([C@@]2(C)CCCC(C)(C)CS(=O)(=O)CCc3c(c(F)cc4[nH]ccc34)S(=O)c3cccc(c3)-c3nc2nn3C)c1)C(=O)O]

Exchanging methyl 5-((4-bromo-6-fluoro-1H-indol-5-yl)thio)-2-fluorobenzimidothioate hydroiodide (Intermediate 76) with methyl 3-((4-bromo-6-fluoro-1H-indol-5-yl)sulfinyl)benzimidothioate hydroiodide (Intermediate 14-13, 897 mg, 1.66 mmol) in Step A, the reaction procedure sequence (Steps A, B, C, D, and Step H) described for Example 204 was used to prepare the two diastereomeric mixture of the title compound. Those two diastereomers were separated by prep-HPLC. The first eluent, Diastereomer 1 (white solid, 17 mg), was designated as Compound 211A; The second eluent, Diastereomer 2 (white solid, 19 mg), was designated as Compound 211B.

Compound 211A: MS (ESI): 719 m/z $[M+H]^+$, retention time: 1.85 minutes; purity: 97% (254 nm) (LC-MS method 4). $^1H$ NMR (400 MHz, $CD_3OD$).

Compound 211B: MS (ESI): 719 m/z $[M+H]^+$, retention time: 1.88 minutes; purity: >99% (254 nm) (LC-MS method 4).

Example 215. Compound 215A and Compound 215B. Stereoisomer 1 and 2 of 3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

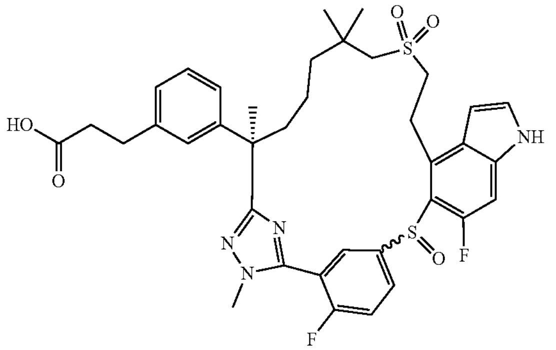 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCC(=O)O)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with ethyl (R)-3-(3-(7-((2-hydroxyethyl)sulfonyl)-2,6,6-trimethyl-1-(2-methylhydrazineyl)-1-oxoheptan-2-yl)phenyl)propanoate (Intermediate 45-20, 1.50 g, 3.10 mmol), the reaction procedure sequence (Steps A, B, C, D, E) as described in Example 204, followed by Step A in Example 205, then Step G and H of Example 204, in this order, was used to prepare the title compounds. The two diastereomers originated from the formation of sulfoxide, was separated by prep-HPLC at the last step. The first eluent (7.6 mg), Diastereomer 1, was designated as 215A; The second eluent (11 mg), Diastereomer 2, was designated as 215B. Both are white solid.

Compound 215A: LC-MS: MS (ESI): 723 m/z $[M+H]^+$, retention time: 1.74 minutes; purity: 98% (214 nm) (LC-MS method 3). $^1H$ NMR (500 MHz, $CD_3OD$) δ 8.44-7.72 (m, 2H), 7.65-7.53 (m, 1H), 7.37 (d, J=3.0 Hz, 1H), 7.16 (t, J=8.0 Hz, 2H), 7.09 (s, 1H), 7.02 (d, J=8.0 Hz, 1H), 6.99 (d, J=8.0 Hz, 1H), 6.68 (s, 1H), 3.79 (s, 3H), 3.67-3.37 (m, 2H), 3.26-2.98 (m, 4H), 2.85 (t, J=8.0 Hz, 2H), 2.52 (t, J=8.0 Hz, 2H), 2.43-2.29 (m, 1H), 1.91-1.79 (m, 1H), 1.70 (s, 3H), 1.63-1.48 (m, 1H), 1.43-0.97 (m, 9H) ppm.

Compound 215B: LC-MS: MS (ESI): 723 m/z $[M+H]^+$, retention time: 1.77 minutes; purity: 98% (214 nm) (LC-MS method 3). $^1H$ NMR (500 MHz, $CD_3OD$) δ 8.22-7.77 (m, 2H), 7.56 (t, J=9.0 Hz, 1H), 7.38 (d, J=3.5 Hz, 1H), 7.23-7.10 (m, 3H), 7.02 (t, J=8.0 Hz, 2H), 6.66 (s, 1H), 4.00-3.79 (m, 4H), 3.72-3.62 (m, 1H), 3.55-3.40 (m, 1H), 3.25-2.96 (m, 3H), 2.84 (t, J=8.0 Hz, 2H), 2.52 (t, J=8.0 Hz, 2H), 2.35-2.23 (m, 1H), 2.00-1.88 (m, 1H), 1.71 (s, 3H), 1.50-1.32 (m, 3H), 1.21 (s, 3H), 1.14 (s, 3H), 1.10-0.96 (m, 1H) ppm.

Example 216. Compound 216A and Compound 216B. Diastereomers 1 and 2 of 2-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]ethanol

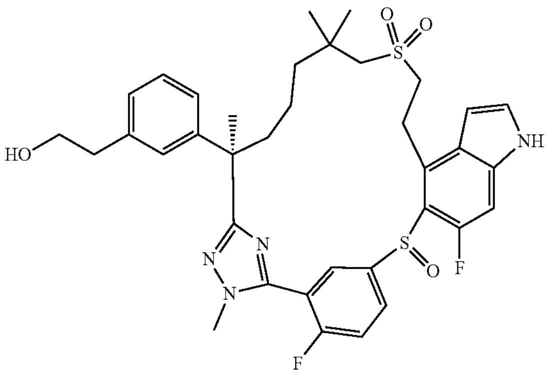 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCO)c1]

Ethyl 2-[3-[(6R)-22,28-difluoro-3,6,10,10-tetramethyl-12,12,24-trioxo-19-(p-tolylsulfonyl)-12λ6, 24λ4-dithia-3,4,19,30-tetrazapentacyclo[23.3.1.12, 5.015,23.016,20]triaconta-1(29),2(30),4,15,17,20,22, 25,27-nonaen-6-yl]phenyl]Acetate

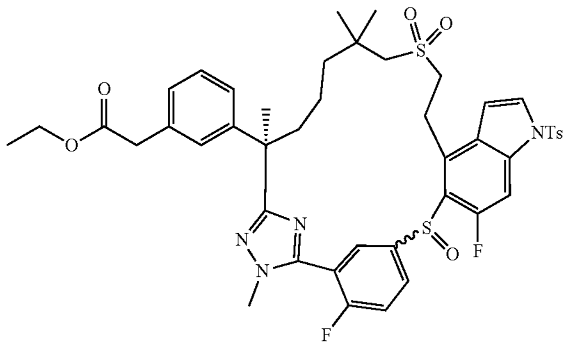 [SMILES: CCOC(=O)Cc1cccc([C@@]2(C)CCCC(C)(C)CS(=O)(=O)CCc3c(c(F)cc4c3ccn4S(=O)(=O)c3ccc(C)cc3)S(=O)c3ccc(F)c(c3)-c3nc2nn3C)c1]

Step A: Exchanging methyl (2S)-2-methyl-3-[3-[(1R)-1-[5-[5-[(4-bromo-6-fluoro-1H-indol-5-yl)sulfanyl]-2-fluoro-phenyl]-1-methyl-1,2,4-triazol-3-yl]-6-(2-hydroxyethyl-sulfonyl)-1,5,5-trimethyl-hexyl]phenyl]propanoate (Step A product of Example 204) with ethyl (R)-2-(3-(2-(5-(5-((4-bromo-6-fluoro-1H-indol-5-yl)thio)-2-fluorophenyl)-1-methyl-1H-1,2,4-triazol-3-yl)-7-((2-hydroxyethyl)sulfonyl)-6,6-dimethylheptan-2-yl)phenyl)acetate (Step B product of Example 209, 0.8 g, 0.978 mmol), the reaction procedure sequence (Steps B to E of Example 204, followed by Step A of Example 205) was used to prepare the title compound (305 mg, pale yellow solid, mixture of two diastereomers originated from sulfoxide formation). LC-MS: MS (ESI): 891 m/z $[M+H]^+$, retention time: 2.17 and 2.22 minutes; purity: 43%+57%% (214 nm) (LC-MS method 3).

2-[3-[(6R)-22,28-Difluoro-3,6,10,10-tetramethyl-12, 12,24-trioxo-19-(p-tolylsulfonyl)-12λ6,24λ4-dithia-3,4,19,30-tetrazapentacyclo[23.3.1.12,5.015,23.016, 20]triaconta-1(29),2(30),4,15,17,20,22,25,27-nonaen-6-yl]phenyl]ethanol

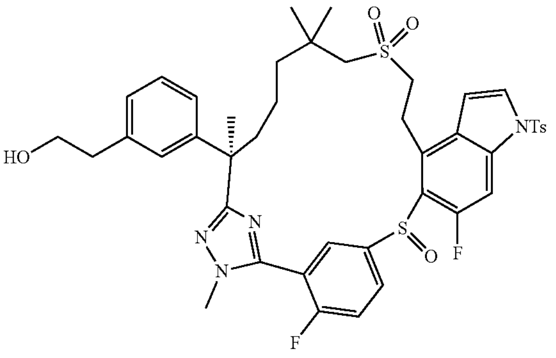 [SMILES: Cc1ccc(S(=O)(=O)n2ccc3c4c(c(F)cc32)S(=O)c2ccc(F)c(c2)-c2nc(nn2C)[C@@](C)(c2cccc(CCO)c2)CCCC(C)(C)CS(=O)(=O)CC4)cc1]

Step B: To a stirred solution of Step A product (100 mg, 0.112 mmol) in tetrahydrofuran (6 mL) was added lithium borohydride (12 mg, 0.56 mmol). The mixture was stirred at room temperature for 48 hours, quenched with water (3 mL), and extracted with ethyl acetate (2×10 mL). The combined organic layers were washed with water, brine, dried over sodium sulfate, filtered, and concentrated to give the title compound (80 mg, 77%) as a white solid. LC-MS: MS (ESI): 849 m/z $[M+H]^+$, retention time: 2.04 minutes; purity: 34+59% (214 nm) (LC-MS method 34).

Compounds 216A and 216B. Diastereomers 1 and 2 of 2-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl] phenyl]ethanol

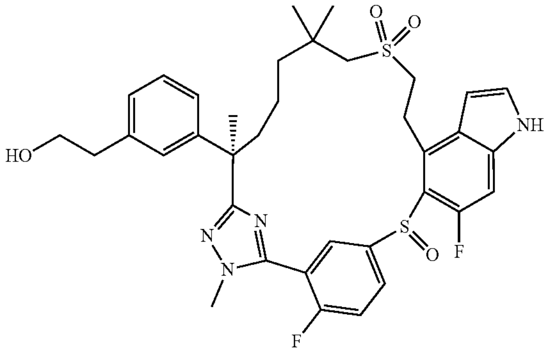 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCO)c1]

Step C: To a stirred solution of (0.08 g, 0.094 mmol) in methanol (5 mL) was added potassium carbonate (26 mg, 0.188 mmol). The reaction was stirred at room temperature for 3 hours, then diluted with water (15 mL) and extracted with ethyl acetate (2×20 mL). The combined extracts were washed with brine, dried over sodium sulfate, filtered, and concentrated. The residue was purified by reverse phase Prep-HPLC. The first eluent (7.7 mg; 12%, white solid), Diastereomer 1, was designated as 216A. The second eluent (22 mg; 33%, white solid), Diastereomer 2, was designated as 216B.

Compound 216A: LC-MS: MS (ESI): 695 m/z $[M+H]^+$, retention time: 1.82 minutes; purity: >99% (214 nm) (LC-MS method 4). $^1$H NMR (500 MHz, DMSO-$d_6$) δ 11.62 (s, 1H), 8.35-8.21 (m, 1H), 7.86-7.69 (m, 1H), 7.62-7.56 (m, 1H), 7.50 (t, J=3.0 Hz, 1H), 7.27-7.19 (m, 1H), 7.13 (t, J=8.0 Hz, 1H), 7.07 (s, 1H), 6.99-6.95 (m, 2H), 6.62 (s, 1H), 4.08-3.69 (m, 5H), 3.52 (t, J=7.0 Hz, 2H), 3.26-2.98 (m, 4H), 2.64 (t, J=7.0 Hz, 2H), 2.36-2.30 (m, 1H), 1.88-1.65 (m, 2H), 1.64 (s, 3H), 1.34-1.19 (m, 6H), 0.98 (s, 3H) ppm.

Compound 216B: LC-MS: MS (ESI): 695 m/z $[M+H]^+$, retention time: 1.85 minutes; purity: 99% (254 nm) (LC-MS method 4). $^1$H NMR (500 MHz, $CD_3OD$) δ 11.18 (s, 1H), 8.12-7.80 (m, 2H), 7.59-7.56 (m, 1H), 7.38-7.36 (m, 1H), 7.18-7.14 (m, 2H), 7.12-6.98 (m, 3H), 6.68 (s, 1H), 3.92-3.86 (m, 4H), 3.71-3.66 (m, 3H), 3.55-3.40 (m, 1H), 3.26-3.16 (m, 1H), 3.10-3.00 (m, 2H), 2.74 (t, J=6.0 Hz, 2H), 2.33-2.24 (m, 1H), 1.97-1.91 (m, 1H), 1.71 (s, 3H), 1.47-1.37 (m, 3H), 1.22 (s, 3H), 1.13 (s, 3H), 1.07-1.00 (m, 1H) ppm.

Example 217. Compound 217A and Compound 217B. Diastereomer Mixture 1 and 2 of 3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]butanoic Acid

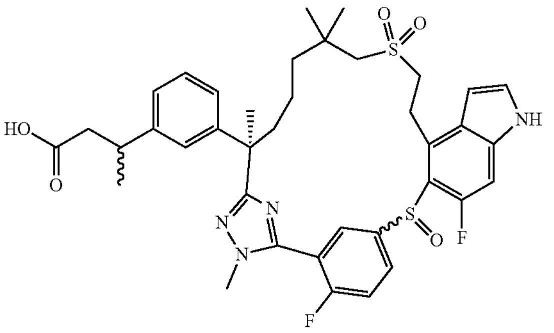 [SMILES: CC(CC(=O)O)c1cccc([C@@]2(C)CCCC(C)(C)CS(=O)(=O)CCc3c(c(F)cc4[nH]ccc34)S(=O)c3ccc(F)c(c3)-c3nc2nn3C)c1]

Methyl 3-[3-[(6R)-22,28-difluoro-3,6,10,10-tetramethyl-12,12,24-trioxo-19-(p-tolylsulfonyl)-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]butanoate

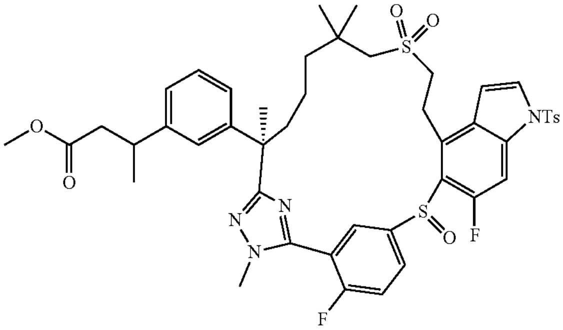 [SMILES: COC(=O)CC(C)c1cccc([C@@]2(C)CCCC(C)(C)CS(=O)(=O)CCc3c(c(F)cc4c3ccn4S(=O)(=O)c3ccc(C)cc3)S(=O)c3ccc(F)c(c3)-c3nc2nn3C)c1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl 3-(3-((R)-7-((2-hydroxyethyl)sulfonyl)-2,6,6-trimethyl-1-(2-methylhydrazineyl)-1-oxoheptan-2-yl)phenyl)butanoate (intermediate 137-3, 940 mg, 1.94 mmol), the reaction procedure sequence (Steps A to E described for Example 204, followed by Steps A described for Example 205) was used to prepare the title compound (43 mg, 0.048 mmol, 84%) as a white solid. LC-MS: MS (ESI): 905 m/z $[M+H]^+$, retention time: 2.89 and 2.94 minutes (LC-MS method 16).

Methyl 3-[3-[(6R)-22,28-difluoro-3,6,10,10-tetramethyl-12,12,24-trioxo-12λ6,2414-dithia-3,4,19,30-tetrazapentacyclo[23.3.1.12,5.015,23.016,20]triaconta-1(29),2(30),4,15,17,20,22,25,27-nonaen-6-yl]phenyl]butanoate

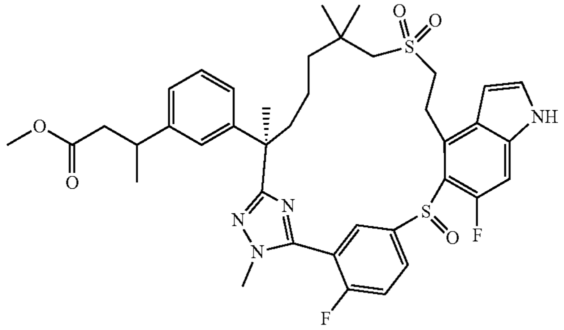 [SMILES: COC(=O)CC(C)c1cccc([C@@]2(C)CCCC(C)(C)CS(=O)(=O)CCc3c(c(F)cc4[nH]ccc34)S(=O)c3ccc(F)c(c3)-c3nc2nn3C)c1]

Step B: To a solution of Step A product (43 mg, 0.0475 mmol) in methanol (4.5 mL) was added potassium carbonate (33 mg, 0.238 mmol). The reaction was stirred at room temperature for 4 hours, quenched with water (10 mL), and extracted with ethyl acetate (3×10 mL). The combined organic layer was washed with brine, dried over sodium sulfate, filtered and concentrated. The residue was purified by flash chromatography (12 g silica gel column, eluting with 0-40% ethyl acetate in petroleum ether) to give the title compound (34 mg, 0.045 mmol, 95%) as a white solid. LC-MS: MS (ESI): 751 m/z $[M+H]^+$, retention time: 2.57 and 2.63 minutes (LC-MS method 16).

Compounds 217A and 217B. Diastereomer Mixture 1 and 2 of 3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]butanoic Acid

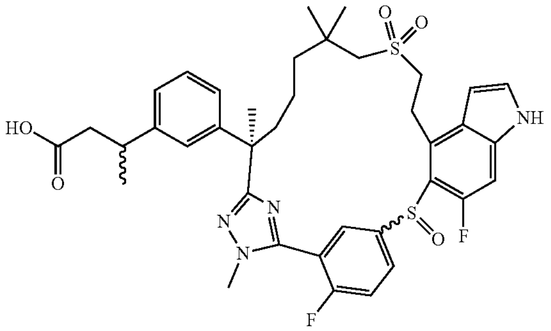 [SMILES: CC(CC(=O)O)c1cccc([C@@]2(C)CCCC(C)(C)CS(=O)(=O)CCc3c(c(F)cc4[nH]ccc34)S(=O)c3ccc(F)c(c3)-c3nc2nn3C)c1]

Step C: To a stirred solution of Step B product (34 mg, 0.0453 mmol) in tetrahydrofuran (2 mL) and water (2 mL) was added lithium hydroxide monohydrate (38 mg, 0.906 mmol) at 30° C. The reaction was stirred at 30° C. under nitrogen atmosphere for 60 hours, diluted with water, and acidified with 1N hydrochloric acid to pH-4. The solution was extracted with ethyl acetate (3×10 mL). The combined organic layer was washed with brine (10 mL), dried over sodium sulfate, filtered, and concentrated. The residue was purified by reverse phase Prep-HPLC. The first eluent (7.2 mg, 0.0098 mmol, 22%, a white solid), was designated as Compound 217A. The second eluent (8.1 mg, 0.011 mmol, 24%, a white solid), was designated as Compound 217A.

Compound 217A: LC-MS: MS (ESI): 737 m/z $[M+H]^+$, retention time: 2.32 minutes; purity: >99% (LC-MS method 16). $^1$H NMR (400 MHz, $CD_3OD$) δ 11.2 (s, 1H), 8.50-7.81 (m, 2H), 7.65-7.50 (m, 1H), 7.37 (d, J=3.2 Hz, 1H), 7.21-7.12 (m, 2H), 7.09 (s, 1H), 7.05 (d, J=7.2 Hz, 1H), 6.99 (d, J=7.6 Hz, 1H), 6.68 (s, 1H), 3.90-3.75 (m, 4H), 3.70-3.50 (m, 1H), 3.20-3.11 (m, 2H), 3.10-3.00 (m, 2H), 2.55-2.46 (m, 2H), 2.40-2.30 (m, 1H), 1.90-1.82 (m, 1H), 1.70 (s, 3H), 1.65-1.25 (m, 4H), 1.24-1.15 (m, 7H), 1.14-1.05 (m, 3H) ppm.

Compound 217B: LC-MS: MS (ESI): 737 m/z $[M+H]^+$, retention time: 2.37 minutes; purity: >99% (LC-MS method 16). $^1$H NMR (400 MHz, $CD_3OD$) δ 11.2 (s, 1H), 8.20-8.14 (m, 1H), 7.97-7.89 (m, 1H), 7.57 (t, J=9.2 Hz, 1H), 7.38 (d, J=3.2 Hz, 1H), 7.19-7.12 (m, 3H), 7.05-7.02 (m, 2H), 6.67 (s, 1H), 4.00-3.85 (m, 4H), 3.68-3.62 (m, 1H), 3.60-3.27 (m, 1H), 3.20-2.99 (m, 4H), 2.55-2.42 (m, 2H), 2.25-2.20 (m, 1H), 2.00-1.85 (m, 1H), 1.70 (s, 3H), 1.50-1.25 (m, 3H), 1.13-1.08 (s, 6H), 1.06 (m, 3H), 1.05-1.00 (m, 1H) ppm.

Example 218. Compound 218A and Compound 2 218B. Diastereomers 1 and 2 of 2-[[3-[(6R)-22,28-difluoro-3,6,10,10-tetramethyl-12,12,24-trioxo-12λ6,24λ4-dithia-3,4,19,30-tetrazapentacyclo [23.3.1.12,5.015,23.016,20]triaconta-1(29),2(30),4,15,17,20,22,25,27-nonaen-6-yl]phenyl]methyl]-3-methoxy-propanoic acid

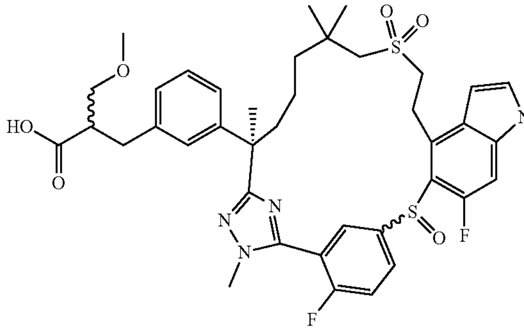

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate (intermediate 137-4, 2.09 g, 4.06 mmol), the reaction procedure sequence (Steps A to E described for Example 204, followed by Steps A described for Example 205, and Steps B and C for Examples 217A and 217B) was used to prepare the title compounds. The first eluent from reverse prep-HPLC, Diastereomer 1 (a mixture of two diastereomers, 6.2 mg, 0.0081 mmol, a white solid), was designated as Compound 218A. The second eluent, Diastereomer 2 (16 mg, 0.021 mmol, a white solid), was designated as Compound 218B.

Compound 218A: LC-MS: MS (ESI): 767 m/z $[M+H]^+$, purity: >99% (214 nm). retention time: 1.76 minutes (LC-MS method 4). $^1$H NMR (400 MHz, $CD_3OD$) δ 11.2 (s, 1H), 8.50-7.90 (m, 2H), 7.70-7.52 (m, 1H), 7.37 (d, J=3.2 Hz, 1H), 7.22-7.12 (m, 2H), 7.07 (d, J=8.8 Hz, 1H), 7.03-6.96 (m, 2H), 6.69-6.67 (m, 1H), 3.85-3.55 (m, 4H), 3.50-3.40 (m, 3H), 3.25-3.17 (m, 3H), 3.16-2.97 (m, 2H), 2.90-2.65 (m, 4H), 2.45-2.38 (m, 1H), 2.06-2.00 (m, 1H), 1.90-1.80 (m, 1H), 1.70 (s, 3H), 1.40-1.20 (m, 9H), 1.15-1.05 (m, 1H) ppm.

Compound 218B: LC-MS: MS (ESI): 767 m/z $[M+H]^+$, purity: >99% (214 nm). retention time: 1.79 minutes (LC-MS method 4). $^1$H NMR (400 MHz, $CD_3OD$) δ 8.14 (s, 1H), 8.00-7.75 (m, 1H), 7.60-7.51 (m, 1H), 7.38-7.35 (m, 1H), 7.20-7.12 (m, 2H), 7.10-7.02 (m, 2H), 6.99 (d, J=7.60 Hz, 1H), 6.67 (s, 1H), 3.97-3.84 (m, 4H), 3.74-3.62 (m, 1H), 3.50-3.36 (m, 3H), 3.25-3.20 (m, 3H), 3.16-2.98 (m, 2H), 2.90-2.70 (m, 4H), 2.35-2.20 (m, 1H), 2.00-1.90 (m, 1H), 1.71 (s, 3H), 1.50-1.25 (m, 4H), 1.24 (s, 3H), 1.14 (s, 3H), 1.10-1.02 (m, 1H) ppm.

Example 219. Compound 219. (2R)-3-[3-[(6R)-22,28-Difluoro-3-(2-hydroxypropyl)-6,10,10-trimethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid

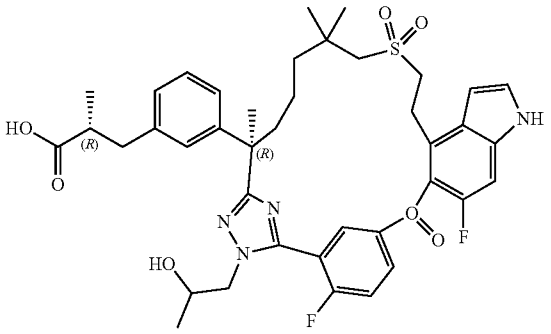

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2R)-3-(3-((2R)-1-(2-(2-(benzyloxy)propyl)hydrazineyl)-7-((2-hydroxyethyl)sulfonyl)-2,6,6-trimethyl-1-oxoheptan-2-yl)phenyl)-2-methylpropanoate (Intermediate 137-5, 180 mg, 0.291 mmol), the reaction procedure sequence (Steps A to D, and Step F) described for Example 6 was used to prepare the title compound (4.8 mg, 0.0064 mmol, mixture of two diastereomers) as a white solid. LC-MS: MS (ESI): 749 m/z $[M+H]^+$, purity: >99% (214 nm). retention time: 2.02 minutes (LC-MS method 4). $^1$H NMR (400 MHz, $CD_3OD$) δ 7.35-7.32 (m, 3H), 7.25 (d, J=10.8 Hz, 1H), 7.19-7.07 (m, 4H), 7.01-6.99 (m, 1H), 6.63 (d, J=2.8 Hz, 1H), 3.87 (d, J=1.6 Hz, 2H), 3.76-3.72 (m, 1H), 3.44-3.37 (m, 2H), 3.24-3.20 (m, 4H), 3.07-2.90 (m, 4H), 2.82-2.77 (m, 2H), 2.18-2.12 (m, 1H), 1.89-1.81 (m, 1H), 1.69 (s, 3H), 1.60-1.53 (m, 1H), 1.32-1.29 (m, 5H), 1.22-1.15 (m, 1H), 1.07 (d, J=3.2 Hz, 6H) ppm.

Example 220. Compound 220A and Compound 220B. Diastereomer 1 and 2 of (6R)-22,28-difluoro-3,6,10,10-tetramethyl-6-[3-(2-methylsulfonylethyl)phenyl]-12λ6,24M-dithia-3,4,19,30-tetrazapentacyclo[23.3.1.12,5.015,23.016,20]triaconta-1(29),2(30),4,15,17,20,22,25,27-nonaene 12,12,24-trioxide

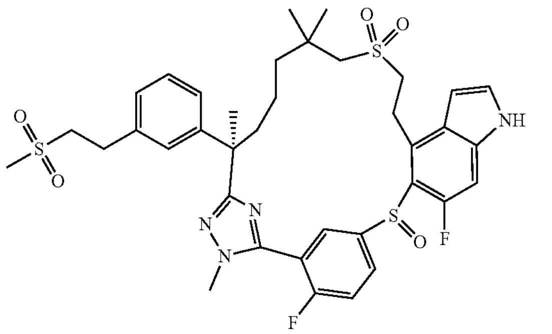 [SMILES: Cn1nc2nc1-c1cc(ccc1F)S(=O)c1c(F)cc3[nH]ccc3c1CCS(=O)(=O)CC(C)(C)CCC[C@]2(C)c1cccc(CCS(C)(=O)=O)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-7-((2-hydroxyethyl)sulfonyl)-N',2,6,6-tetra methyl-2-(3-(2-(methylsulfonyl)ethyl)phenyl)heptanehydrazide (intermediate 137-6, 0.34 g, 0.68 mmol), the reaction procedure sequence (Steps A to E described for Example 204, followed by Steps A described for Example 205, and Steps B for Examples 217A and 217B) was used to prepare the title compounds. The final compounds were separated by reverse phase prep-HPLC. The first eluent, Diastereomer 1 (6.0 mg, a white solid), was designated as Compound 220A. The second eluent, Diastereomer 2 (16.6 mg, a white solid), was designated as Compound 220B.

Compound 220A: LC-MS: MS (ESI): 757 m/z $[M+H]^+$, purity: 97% (254 nm). retention time: 1.81 minutes (LC-MS method 4). $^1$H NMR (400 MHz, DMSO-$d_6$) δ 11.62 (s, 1H), 8.35-8.19 (m, 1H), 7.90-7.72 (m, 2H), 7.50-7.49 (m, 1H), 7.21-7.16 (m, 3H), 7.07 (d, J=6.0 Hz, 1H), 6.98 (d, J=6.0 Hz, 1H), 6.62 (s, 1H), 3.85-3.72 (m, 5H), 3.48-3.42 (m, 1H), 3.38-3.36 (m, 2H), 3.30-3.22 (m, 1H), 3.14-3.12 (m, 1H), 3.01-2.94 (m, 6H), 1.92-1.66 (m, 5H), 1.38-1.19 (m, 6H), 0.98 (s, 3H) ppm.

Compound 220B: LC-MS: MS (ESI): 757 m/z $[M+H]^+$, purity: 98% (254 nm). retention time: 1.84 minutes (LC-MS method 4). $^1$H NMR (400 MHz, $CD_3OD$) δ 8.14-7.94 (m, 2H), 7.57 (t, J=9.2 Hz, 1H), 7.37 (d, J=3.6 Hz, 1H), 7.23-7.15 (m, 3H), 7.12-7.08 (m, 2H), 6.68 (s, 1H), 3.92-3.86 (m, 4H), 3.73-3.67 (m, 1H), 3.58-3.44 (m, 1H), 3.35-3.30 (m, 3H), 3.11-3.02 (m, 4H), 2.83 (s, 3H), 2.33-2.26 (m, 1H), 1.97-1.91 (m, 1H), 1.72 (s, 3H), 1.49-1.36 (m, 2H), 1.22 (s, 3H), 1.13 (s, 3H), 1.07-1.00 (m, 1H) ppm.

Example 221. Compound 221. (2R)-3-[3-[(6R)-21,22-difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methylpropanoic Acid

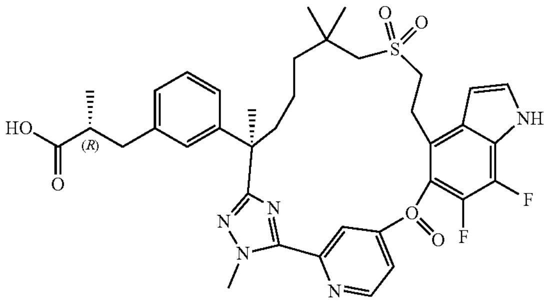

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 0.39 g, 0.804 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)oxy)pyridine-2-carbimidothioate (Intermediate 150, 320 mg, 0.80 mmol), the reaction procedure sequence (Steps A to D, and Step F) described for Example 6 was used to prepare the title compound (12 mg) as a white solid. LC-MS: MS (ESI): 706 m/z $[M+H]^+$, purity: >99% (214 nm). retention time: 1.71 minutes (LC-MS method 27). $^1$H NMR (500 MHz, $CD_3OD$) δ 8.67 (d, J=5.5 Hz, 1H), 7.67 (d, J=2.0 Hz, 1H), 7.41 (d, J=3.5 Hz, 1H), 7.27 (dd, J=5.5, 2.0 Hz, 1H), 7.12 (t, J=7.5 Hz, 1H), 7.03 (s, 1H), 6.96 (dd, J=12.5, 7.5 Hz, 2H), 6.75 (t, J=3.0 Hz, 1H), 4.35 (s, 3H), 3.40-3.33 (m, 2H), 3.19-3.07 (m, 2H), 2.95-2.85 (m, 1H), 2.67 (d, J=14.0 Hz, 1H), 260-2.56 (m, 3H), 2.11-2.01 (m, 1H), 1.85-1.76 (m, 1H), 1.64 (s, 3H), 1.48-1.37 (m, 1H), 1.27-1.17 (m, 1H), 1.10-1.04 (m, 4H), 1.01 (s, 3H), 0.96-0.87 (m, 4H) ppm.

Example 222. Compound 222A and Compound 222B. Diastereomer 1 and 2 of (2S)-3-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methylpropanoic Acid

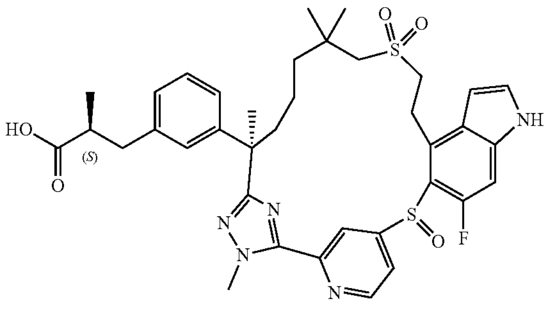

Diastereomer 1 and 2 of Methyl (2S)-3-[3-[(6R)-22-fluoro-3,6,10,10-tetramethyl-12,12,24-trioxo-19-(p-tolylsulfonyl)-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

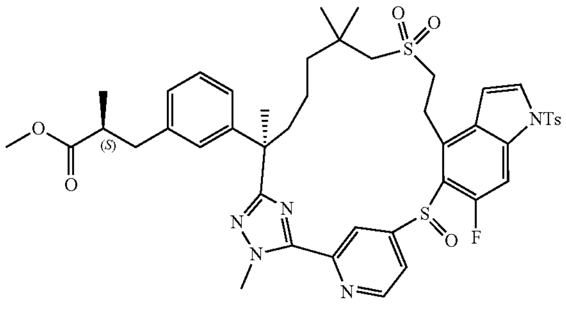

Step A: Exchanging methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 1.5 g, 3.78 mmol), the reaction procedure sequence (Steps A to E described for Example 204, followed by Steps B described for Example 206) was used to prepare the title compound (152 mg) as a mixture of two diastereomers. LC-MS: MS (ESI): 888 m/z $[M+H]^+$, purity: 91% (254 nm). retention time: 2.24 minutes (LC-MS method 7).

This mixture was then subject to chiral SFC separation under the following conditions: Instrument: SFC-150 (Waters); Column: AS 20*250 mm, 10 μm; Column temperature: 35° C.; Mobile phase: carbon dioxide/methanol (0.2%7M ammonia in methanol)=50/50; Flow rate: 120 g/minutes; Back pressure: 100 bar; Detection wavelength: 214 nm; Cycle time: 4.2 minutes; Sample solution: 150 mg dissolved in 30 mL of methanol and dichloromethane (1:1); Injection volume: 2 mL. The first eluent (30 mg, 20%) was designated as Diastereomer 1. The second eluent (92 mg, 61%) was designated as Diastereomer 2.

Compound 222A. Diastereomer 1 of (2S)-3-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

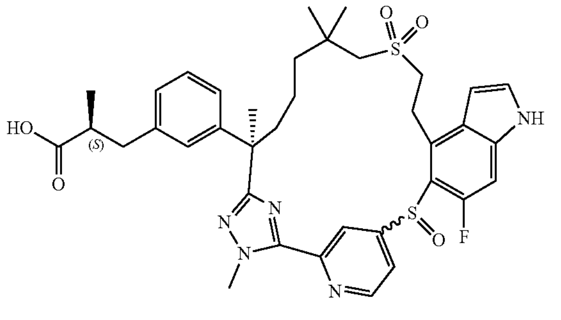

Step B: To a stirred solution of Diastereomer 1 of Step A product (30 mg, 0.033 mmol) in tetrahydrofuran (1 mL) was added lithium hydroxide monohydrate (0.169 mL, 1M in water). The reaction was stirred at room temperature for 48 hours, then diluted with 2 mL of water and acidified with 1M hydrochloric acid to pH ~4. The solution was extracted with ethyl acetate (2×15 mL). The combined organic layers were washed with brine, dried over sodium sulfate, filtered, and concentrated. The residue was purified by prep-HPLC to give the title compound (8.1 mg, 33%) as a white solid. LC-MS: MS (ESI): 720 m/z $[M+H]^+$, purity: >99% (254 nm). retention time: 1.88 minutes (LC-MS method 12). $^1H$ NMR (400 MHz, $CD_3OD$) δ 9.00-8.68 (m, 2H), 7.40 (d, J=3.2 Hz, 1H), 7.30-7.12 (m, 3H), 7.06-6.94 (m, 3H), 6.72-6.61 (m, 1H), 4.27 (s, 3H), 3.71-3.47 (m, 2H), 3.25-2.92 (m, 4H), 2.66-2.57 (m, 2H), 2.27-1.79 (m, 4H), 1.72 (s, 3H), 1.53-1.38 (m, 2H), 1.28-0.96 (m, 10H) ppm.

Compound 222B. Diastereomer 2 of (2S)-3-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic acid

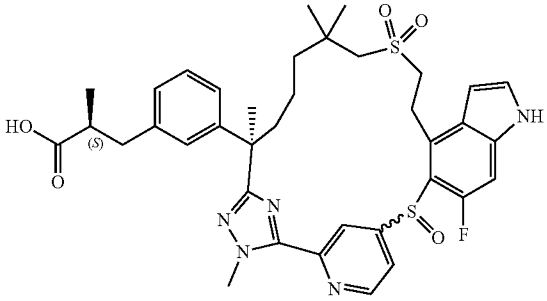

Step C: Utilizing identical procedure described in Step B, Diastereomer 2 of Step A product (92 mg, 0.1 mmol) was hydrolyzed to the title compound (48 mg, 65%) as a white solid. LC-MS: MS (ESI): 720 m/z $[M+H]^+$, purity: >99% (254 nm). retention time: 1.89 minutes (LC-MS method 12). $^1H$ NMR (400 MHz, $CD_3OD$) δ 8.93 (brs, 1H), 8.69 (brs, 1H), 7.39 (d, J=3.2 Hz, 1H), 7.34-6.93 (m, 6H), 6.65-6.50 (m, 1H), 4.32 (s, 3H), 3.67-3.60 (m, 1H), 3.58-3.38 (m, 1H), 3.22-2.79 (m, 5H), 2.68-2.54 (m, 2H), 2.51-2.37 (m, 1H), 1.84-1.68 (m, 4H), 1.61-1.43 (m, 3H), 1.38-0.98 (m, 10H) ppm.

Example 223. Compound 223A and Compound 223B. Diastereomer 1 and 2 of (6R)-22,28-difluoro-3,6,10,10-tetramethyl-6-phenyl-12λ6,24λ4-dithia-3,4,19,30-tetrazapentacyclo[23.3.1.12,5.015,23.016,20]triaconta-1(29),2(30),4,15,17,20,22,25,27-nonaene 12,12,24-trioxide

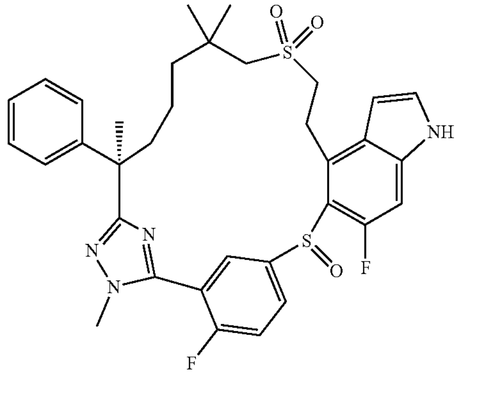 [SMILES: Cn1nc2nc1-c1cc(ccc1F)S(=O)c1c(F)cc3[nH]ccc3c1CCS(=O)(=O)CC(C)(C)CCC[C@]2(C)c1ccccc1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-7-((2-Hydroxyethyl)sulfonyl)-N',2,6,6-tetramethyl-2-phenylheptanehydrazide (Intermediate 152, 0.43 g, 1.11 mmol), the reaction procedure sequence (Steps A to E described for Example 204, followed by Steps B described for Example 206, and Steps B for Examples 217A and 217B) was used to prepare the title compound (55 mg) as a mixture of two diastereomers. This mixture was separated by reverse phase prep-HPLC. The first eluent (6 mg), Diastereomer 1, was designated as 223A. The second eluent (17 mg), Diastereomer 2, was designated as 223B.

Compound 223A: LC-MS: MS (ESI): 651 m/z $[M+H]^+$, purity: >99% (254 nm). retention time: 2.11 minutes (LC-MS method 12). $^1$H NMR (400 MHz, DMSO-d6) δ 11.62 (s, 1H), 8.32-7.70 (m, 3H), 7.51-7.48 (m, 1H), 7.26-7.11 (m, 6H), 6.62 (s, 1H), 3.73-3.70 (m, 5H), 3.49-3.43 (m, 1H), 3.30-3.21 (m, 1H), 3.15-3.12 (m, 1H), 2.99 (d, J=14 Hz, 1H), 2.34-2.28 (m, 1H), 1.82-1.66 (m, 5H), 1.24-0.99 (s, 9H) ppm.

Compound 223B: LC-MS: MS (ESI): 651 m/z $[M+H]^+$, purity: >99% (254 nm). retention time: 2.17 minutes (LC-MS method 12). $^1$H NMR (400 MHz, $CD_3OD$) δ 11.17 (s, 1H), 8.16-8.12 (m, 1H), 7.97-7.85 (m, 1H), 7.57 (t, J=9.2 Hz, 1H), 7.37 (d, J=3.2 Hz, 1H), 7.23-7.13 (m, 6H), 6.67 (s, 1H), 3.93-3.86 (m, 4H), 3.72-3.66 (m, 1H), 3.51-3.45 (m, 1H), 3.25-3.19 (m, 1H), 3.11-3.01 (m, 2H), 2.33-2.24 (m, 1H), 1.99-1.93 (m, 1H), 1.72 (s, 3H), 1.45-1.35 (m, 3H), 1.22 (s, 3H), 1.14 (s, 3H), 1.06-1.00 (m, 1H) ppm.

Example 224. Compound 224. Diastereomer 2 of 3-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propanoic Acid

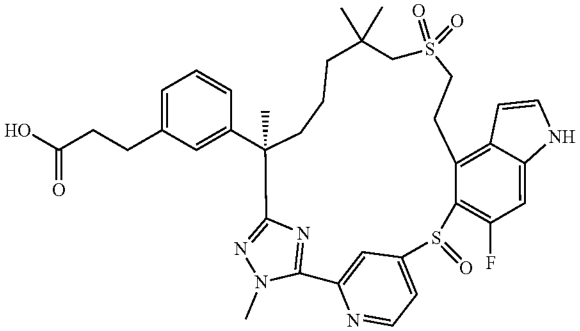 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCC(=O)O)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-(7-((2-hydroxyethyl)sulfonyl)-2,6,6-trimethyl-1-(2-methylhydrazineyl)-1-oxoheptan-2-yl)phenyl)propanoate (Intermediate 45-20, 610 mg, 1.25 mmol), and methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 600 mg, 1.51 mmol), the reaction procedure sequence (Steps A to F and H described for Example 204) was used to prepare the title compound (55 mg) as a single diastereomer (63.1 mg, 57%) as a white solid. LC-MS: MS (ESI): 706 m/z $[M+H]^+$, purity: >99% (254 nm). retention time: 1.89 minutes (LC-MS method 12). $^1$H NMR (400 MHz, DMSO-$d_6$) δ 11.69 (s, 1H), 8.78-8.72 (m, 1H), 7.52 (t, J=2.4 Hz, 1H), 7.46-7.36 (m, 1H), 7.25-6.93 (m, 5H), 6.44 (brs, 1H), 4.25 (s, 3H), 3.60-3.47 (m, 1H), 3.20-3.09 (m, 2H), 3.06-2.95 (m, 2H), 2.80-2.71 (m, 2H), 2.44-2.33 (m, 2H), 1.81-1.58 (m, 5H), 1.53-1.34 (m, 4H), 1.31-1.20 (m, 3H), 1.15-1.04 (m, 4H) ppm.

Example 225. Compound 225A and 225B. Diastereomer 1 and 2 of (2S)-2-methyl-3-[3-[(6R)-21,22,28-trifluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

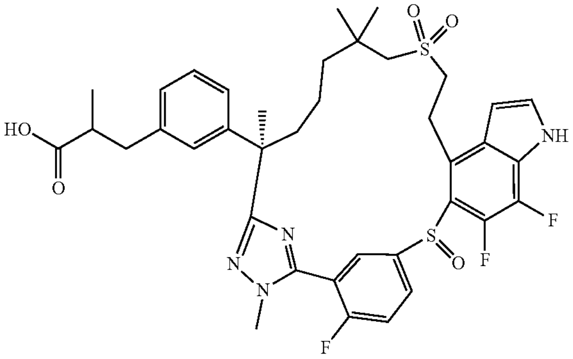 [SMILES: CC(Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O]

Methyl (S)-3-(3-((R)-2-(5-(5-((4-bromo-6,7-difluoro-1H-indol-5-yl)thio)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate

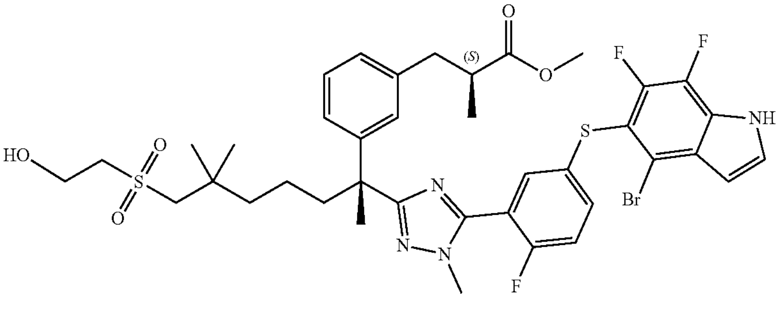

Step A: To a stirred solution of methyl (2S)-3-[3-[(1R)-6-(2-hydroxyethylsulfonyl)-1,5,5-trimethyl-1-(methylaminocarbamoyl)hexyl]phenyl]-2-methyl-propanoate (Intermediate 137-1, 3.20 g, 8.66 mmol) and methyl 5-((4-bromo-6,7-difluoro-1H-indol-5-yl)thio)-2-fluorobenzimidothioate hydroiodide (Intermediate 14-16, 2.80 g, 5.01 mmol) in pyridine (30 mL) was added magnesium sulphate (5 g). The reaction mixture was stirred at 80° C. overnight, quenched with water (50 mL), and extracted with ethyl acetate (2×50 mL). The combined organic extracts were washed with brine, dried over sodium sulfate, filtered, and concentrated. The residue was purified by automated flash chromatography (20 g silica gel column, eluting with 0-90% ethyl acetate in petroleum ether) to give the title compound (3.80 g, 68%) as a solid. LC-MS: MS (ESI): 849, 851 m/z $[M+H]^+$, purity: 98% (214 nm), retention time: 2.01 minutes (LC-MS method 4).

Methyl (S)-3-(3-((R)-2-(5-(5-((4-bromo-6,7-difluoro-1H-indol-5-yl)thio)-2-fluorophenyl)-1-methyl-1H-1,2,4-triazol-3-yl)-6,6-dimethyl-7-(vinylsulfonyl)heptan-2-yl)phenyl)-2-methylpropanoate

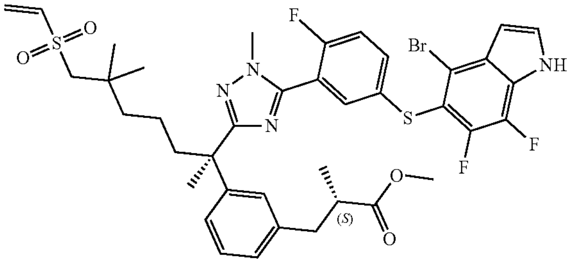

Step B: To a stirred solution of the product from Step A (3.80 g, 4.47 mmol) in dichloromethane (40 mL) was added at room temperature triethylamine (1.9 mL, 13.4 mmol) and methanesulfonyl chloride (0.45 mL, 5.81 mmol). The reaction mixture was stirred at room temperature for 2 hours and diluted with dichloromethane (40 mL). The mixture was washed with brine, dried over sodium sulfate, filtered, and concentrated. The residue was purified by automated flash chromatography (20 g silica gel column, eluting with 0-80% ethyl acetate in petroleum ether) to give the title compound (3.40 g, 91%) as a solid. LC-MS: MS (ESI): 831, 833 m/z $[M+H]^+$, purity: 81% (214 nm). retention time: 2.11 minutes (LC-MS method 4).

Methyl (2S)-2-methyl-3-[3-[(6R,13E)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,13,15,17,20,22,25,27-decaen-6-yl]phenyl]propanoate

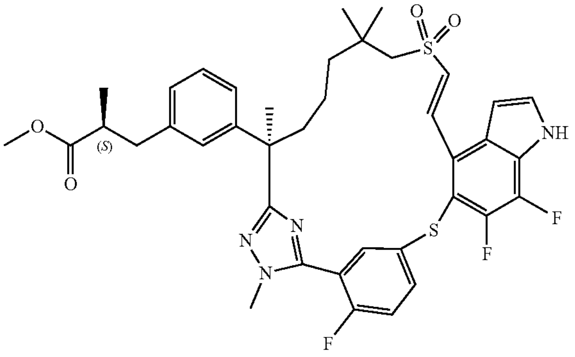

Step C: A solution of triethylamine (0.96 mL, 6.61 mmol) and bis(tri-tert-butylphosphine)palladium(0) (0.42 g, 0.818 mmol) in toluene (400 mL) was degassed with argon for 15 minutes at room temperature. To this solution was added dropwise the product from Step B (3.40 g, 4.09 mmol) in toluene (20 mL) over 2 hours at 120° C. After the addition, the mixture was stirred at 100° C. for 2 hours and concentrated. The residue was purified by automated flash chromatography (20 g silica gel column, eluting with 0-65% ethyl acetate in petroleum ether) to give the title compound (2.40 g, 80%) as solid. LC-MS: MS (ESI): 751 m/z $[M+H]^+$, purity: 96% (214 nm). retention time: 2.07 minutes (LC-MS method 4).

Methyl (2S)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate

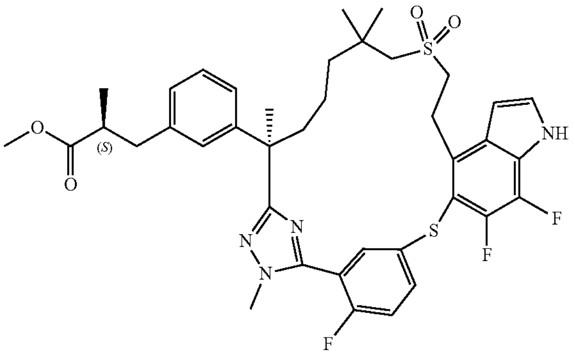

Step D: To a stirred solution of the product from Step C (2.40 g, 3.60 mmol) in ethanol (40 mL) was added 10% palladium on carbon (wetted with ca. 55% Water, 1 g). The reaction mixture was stirred under hydrogen at 50° C. for 2 hours. The mixture was filtered through a pad of Celite. The filtrate cake was washed with ethanol (3×50 mL). The filtrate was concentrated. The residue was purified by automated flash chromatography (20 g silica gel column, eluting with 0-65% ethyl acetate in petroleum ether) to give the title compound (2.3 g, 85%) as a solid. LC-MS: MS (ESI): 753 m/z $[M+H]^+$, purity: 98% (214 nm). retention time: 2.10 minutes (LC-MS method 4).

Methyl (2S)-2-methyl-3-[3-[(6R)-21,22,28-trifluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate

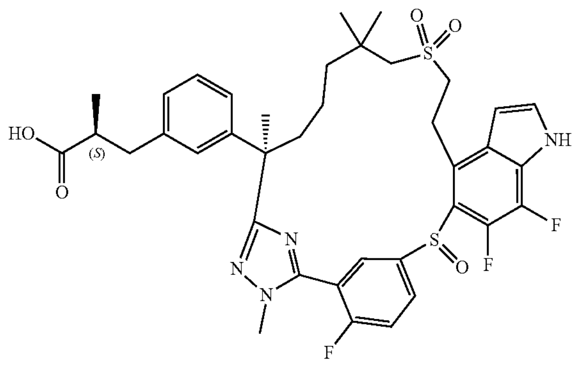

Step E: To a stirred solution of the product from Step D (1.50 g, 1.99 mmol) in acetonitrile (20 mL) was added 1-tosyl-1H-imidazole (1.78 g, 7.96 mmol) and 1,8-diazabicyclo[5.4.0]undec-7-ene (1.2 mL, 7.96 mmol). The reaction mixture was stirred at room temperature for 3 days, quenched with water (20 mL), and extracted with ethyl acetate (2×50 mL). The combined organic extracts were washed with water, brine, dried over sodium sulfate, filtered, and concentrated. The residue was purified by automated flash chromatography (20 g silica gel column, eluting with 0-80% ethyl acetate in petroleum ether) to give the title compound (900 mg, 49%) as a solid. LC-MS: MS (ESI): 906 m/z $[M+H]^+$, purity: >99% (214 nm). retention time: 2.25 minutes (LC-MS method 4).

Methyl (2S)-2-methyl-3-[3-[(6R)-21,22,28-trifluoro-3,6,10,10-tetramethyl-12,12,24-trioxo-19-(p-tolylsulfonyl)-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propanoate

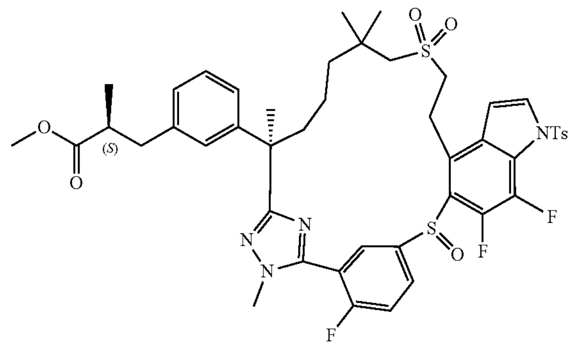

Step F: To a stirred solution of the product from Step E (900 mg, 0.992 mmol) in acetonitrile (20 mL) was added (S,S)-hydrobenzoin (1.06 g, 4.96 mmol), titanium(iv) isopropoxide (0.87 mL, 2.98 mmol) and tert-butyl hydroperoxide (0.27 g, 2.98 mmol). The mixture was stirred at room temperature for 4 days, poured into 20 mL of water, and extracted with ethyl acetate (2×15 mL). The combined organic phases were washed with brine, dried over sodium sulphate, filtered, and concentrated. The residue was purified by automated silica gel chromatography (20 g silica gel column, eluting with 0-90% ethyl acetate in petroleum ether) to give the title compound (820 mg, 89%) as a yellow solid. LC-MS: MS (ESI): 923 m/z $[M+H]^+$, purity: 89% (214 nm). retention time: 2.17 minutes (LC-MS method 4).

Methyl (2S)-2-methyl-3-[3-[rac-(6R)-21,22,28-trifluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propanoate

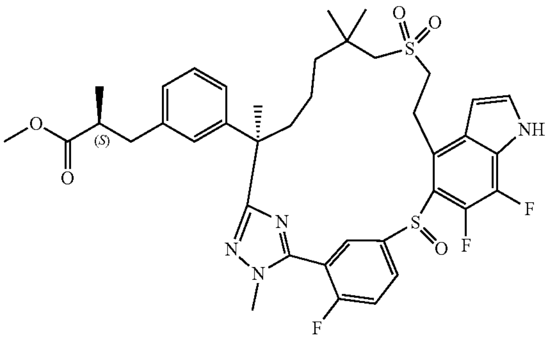

Step G: To a stirred solution of the product from Step F (820 mg, 0.888 mmol) in tetrahydrofuran (20 mL) was added tetrabutylammonium fluoride (5 ml, 1 M in tetrahydrofuran). The mixture was stirred at room temperature overnight, poured into 20 mL of water, and extracted with ethyl acetate (2×15 mL). The combined organic phases were washed brine, dried over sodium sulphate, filtered, and concentrated. The residue was purified by automated silica gel chromatography (20 g silica gel column, eluting with 0-90% ethyl acetate in petroleum ether) to give the title compound (570 mg, 83%) as a solid. LC-MS: MS (ESI): 769 m/z $[M+H]^+$, purity: 92% (214 nm). retention time: 1.98 minutes (LC-MS method 4).

(2S)-2-Methyl-3-[3-[(6R)-21,22,28-trifluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

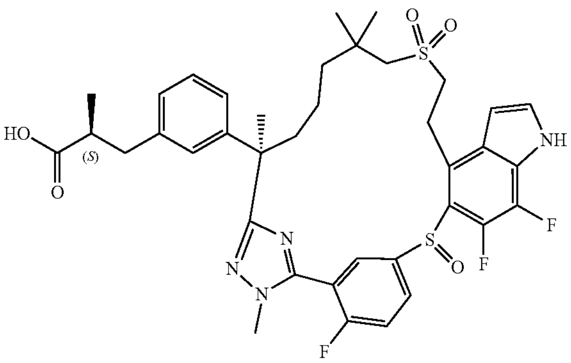

Step H: To a stirred solution of Step G product (570 mg, 0.741 mmol) in tetrahydrofuran (2 mL) and water (2 mL) was added lithium hydroxide monohydrate (159 mg, 0.380 mmol). The reaction was stirred at room temperature overnight, acidified with 1N hydrochloric acid to pH ~4, and diluted with ethyl acetate (20 mL), The mixture was washed with brine, dried over sodium sulphate, filtered, and concentrated. The residue was purified by prep-HPLC to give the title compound (335 mg, 60%, Diastereomer 2) as a solid. LC-MS: MS (ESI): 755 m/z $[M+H]^+$, purity: >99% (214 nm). retention time: 8.97 minutes (LC-MS method 49). $^1$H NMR (500 MHz, $CD_3OD$) δ 8.24-7.82 (m, 2H), 7.61 (d, J=9.0 Hz, 1H), 7.44 (d, J=3.5 Hz, 1H), 7.13 (t, J=7.5 Hz, 1H), 7.06 (s, 1H), 7.04-6.94 (m, 2H), 6.76 (s, 1H), 4.02-3.87 (m, 1H), 3.85 (d, J=2.5 Hz, 3H), 3.72-3.61 (m, 1H), 3.58-3.44 (m, 1H), 3.25-3.21 (m, 1H), 3.12-2.96 (m, 2H), 2.95-2.87 (m, 1H), 2.65-2.53 (m, 2H), 2.31-2.21 (m, 1H), 1.97-1.87 (m, 1H), 1.69 (s, 3H), 1.52-1.34 (m, 3H), 1.19 (s, 3H), 1.11 (s, 3H), 1.06-0.94 (m, 4H) ppm.

Example 226. Compound 226. 2-[3-[(6R)-22-Fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]acetic Acid

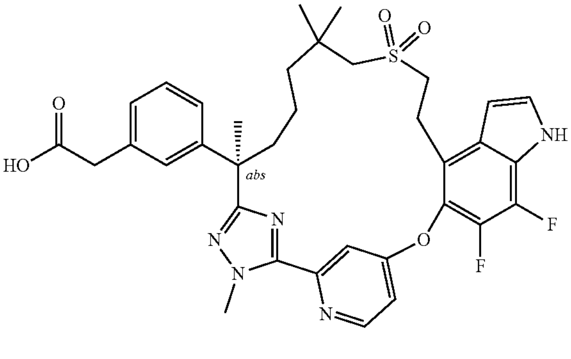 [SMILES: Cn1nc2nc1-c1cc(ccn1)Oc1c(F)c(F)c3[nH]ccc3c1CCS(=O)(=O)CC(C)(C)CCC[C@]2(C)c1cccc(CC(=O)O)c1]

Exchanging methyl (2R)-3-(3-(7-((2-hydroxyethyl)sulfonyl)-2,6,6-trimethyl-1-(2-methylhydrazineyl)-1-oxoheptan- 2-yl)phenyl)-2-methylpropanoate (Intermediate 69) with ethyl (R)-2-(3-(7-((2-hydroxyethyl)sulfonyl)-2,6,6-trimethyl-1-(2-methylhydrazineyl)-1-oxoheptan-2-yl)phenyl) acetate (Intermediate 137-8, 0.80 g, 1.7 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 133-1, 0.71 g, 1.87 mmol), the reaction procedure sequence (Steps A to D, and Step F) described for Example 6 was used to prepare the title compound (35 mg) as a white solid. LC-MS: MS (ESI): 660 m/z $[M+H]^+$, purity: >99% (214 nm). retention time: 2.06 minutes (LC-MS method 21). $^1$H NMR (400 MHz, $CD_3OD$). δ 8.64 (d, J=5.6 Hz, 1H), 7.65 (d, J=2.4 Hz, 1H), 7.34 (d, J=3.2 Hz, 1H), 7.28 (d, J=10.8 Hz, 1H), 7.23 (dd, J=2.4, 5.6 Hz, 1H), 7.16 (t, J=7.6 Hz, 1H), 7.12-7.10 (m, 1H), 7.07 (d, J=7.2 Hz, 1H), 7.02 (d, J=8.0 Hz, 1H), 6.69 (d, J=3.2 Hz, 1H), 4.34 (s, 3H), 3.49 (s, 2H), 3.44-3.40 (m, 2H), 3.20-3.04 (m, 2H), 2.61 (d, J=13.6 Hz, 1H), 2.49 (d, J=13.6 Hz, 1H), 2.06-2.01 (m, 1H), 1.80-1.74 (m, 1H), 1.65 (s, 3H), 1.42-1.37 (m, 1H), 1.22-1.15 (m, 1H), 0.99-0.93 (m, 8H) ppm.

Example 227. Compound 227. 2-[3-[(6R)-22-Fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]ethanol

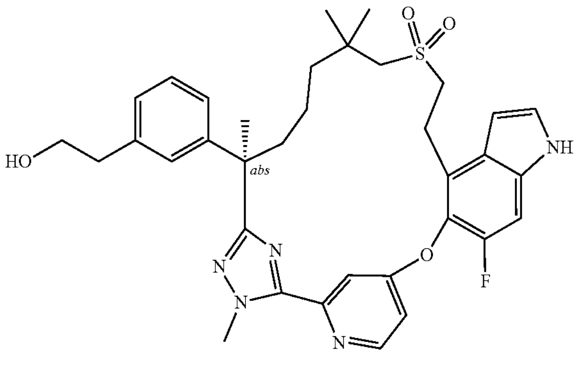 [SMILES: Cn1nc2nc1-c1cc(ccn1)Oc1c(F)cc3[nH]ccc3c1CCS(=O)(=O)CC(C)(C)CCC[C@]2(C)c1cccc(CCO)c1]

Ethyl 2-[3-[(6R)-22-Fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]ethanol

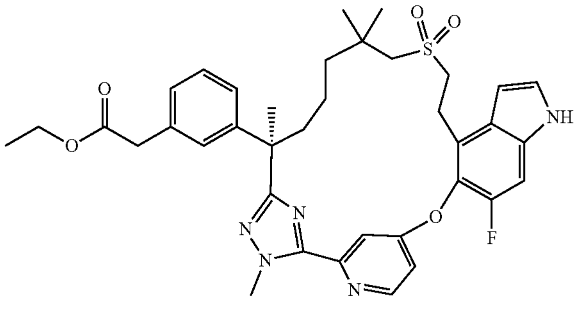 [SMILES: CCOC(=O)Cc1cccc([C@@]2(C)CCCC(C)(C)CS(=O)(=O)CCc3c(c(F)cc4[nH]ccc34)Oc3ccnc(c3)-c3nc2nn3C)c1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with ethyl (R)-2-(3-(7-((2-hydroxyethyl)sulfonyl)-2,6,6-trimethyl-1-(2-methylhydrazineyl)-1-oxoheptan-2-yl)phenyl)acetate (Intermediate 137-8, 0.80 g, 1.7 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 133-1, 0.71 g, 1.87 mmol), the reaction procedure sequence (Steps A to D) described for Example 6 was used to prepare the title compound (160 mg) as a white solid. LC-MS: MS (ESI): 688 m/z $[M+H]^+$, purity: >99% (214 nm). retention time: 2.11 minutes (LC-MS method 4).

Compound 227. 2-[3-[(6R)-22-Fluoro-3,6,10,10-tetramethyl-12,12-dioxo-24-oxa-1216-thia-3,4,19,28,30-pentazapentacyclo[23.3.1.12,5.015,23.016,20]triaconta-1(29),2(30),4,15,17,20,22,25,27-nonaen-6-yl]phenyl]ethanol

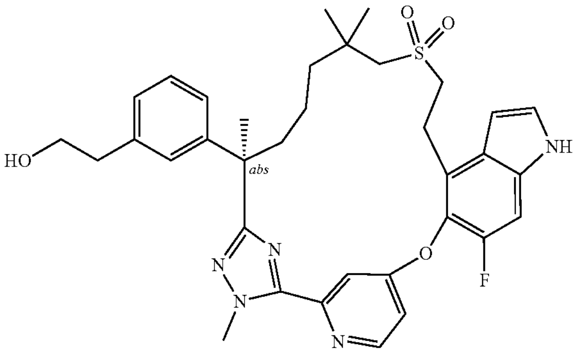 [SMILES: Cn1nc2nc1-c1cc(ccn1)Oc1c(F)cc3[nH]ccc3c1CCS(=O)(=O)CC(C)(C)CCC[C@]2(C)c1cccc(CCO)c1]

Step B: To a stirred solution of Step A product (85 mg, 0.12 mmol) in tetrahydrofuran (6 mL) was added lithium borohydride (13 mg, 0.618 mmol). The mixture was stirred at room temperature for 48 hours, quenched with water (10 mL), and extracted with ethyl acetate (2×10 mL). The combined organic layers were washed with brine, dried over sodium sulfate, filtered, and concentrated. The residue was purified by Prep HPLC to give the title compound (38.7 mg, yield 49%) as white solid. LC-MS: MS (ESI): 646 m/z $[M+H]^+$, purity: >99% (214 nm). retention time: 1.95 minutes (LC-MS method 34). $^1H$ NMR (400 MHz, $CD_3OD$) δ 8.64 (d, J=5.6 Hz, 1H), 7.65 (d, J=2.4 Hz, 1H), 7.34 (d, J=3.2 Hz, 1H), 7.28 (d, J=10.8 Hz, 1H), 7.24 (dd, J=2.4, 5.6 Hz, 1H), 7.14 (t, J=7.6 Hz, 1H), 7.02-6.96 (m, 3H), 6.69 (d, J=2.8 Hz, 1H), 4.35 (s, 3H), 3.66 (t, J=7.2 Hz, 2H), 3.47-3.36 (m, 2H), 3.20-3.04 (m, 2H), 2.72 (t, J=7.2 Hz, 2H), 2.60 (d, J=13.6 Hz, 1H), 2.51 (d, J=13.6 Hz, 1H), 2.07-2.01 (m, 1H), 1.82-1.74 (m, 1H), 1.64 (s, 3H), 1.42-1.37 (m, 1H), 1.22-1.14 (m, 1H), 1.02-0.93 (m, 8H) ppm.

Example 228. Compound 228. 3-[3-[rac-(6R)-22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]propanoic acid

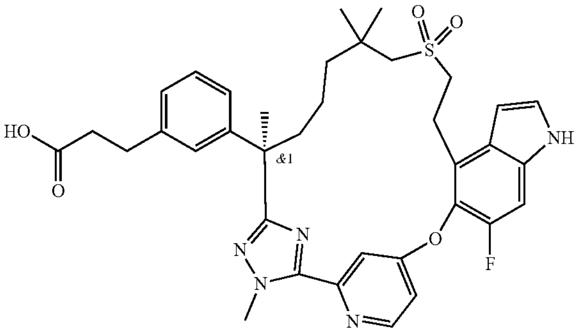 [SMILES: Cn1nc2nc1-c1cc(ccn1)Oc1c(F)cc3[nH]ccc3c1CCS(=O)(=O)CC(C)(C)CCC[C@]2(C)c1cccc(CCC(=O)O)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with ethyl (R)-3-(3-(7-((2-hydroxyethyl)sulfonyl)-2,6,6-trimethyl-1-(2-methylhydrazineyl)-1-oxoheptan-2-yl)phenyl)propanoate (Intermediate 58-8, 0.83 g, 1.71 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 133-1, 0.65 g, 1.71 mmol), the reaction procedure sequence (Steps A to D, and Step F) described for Example 6 was used to prepare the title compound (13 mg) as a white solid. LC-MS: MS (ESI): 674 m/z $[M+H]^+$, purity: >99% (214 nm). retention time: 1.87 minutes (LC-MS method 4). $^1H$ NMR (400 MHz, $CD_3OD$) δ 8.3-8.05 (m, 1H), 7.84 (d, J=6.0 Hz, 1H), 7.75-7.65 (m, 1H), 7.37 (d, J=3.2 Hz, 1H), 7.25-7.14 (m, 2H), 7.10-6.95 (m, 3H), 6.70-6.60 (m, 1H), 4.34 (s, 3H), 3.45-3.38 (m, 2H), 3.22-3.11 (m, 2H), 2.82 (t, J=7.6 Hz, 2H), 2.62 (d, J=13.6 Hz, 1H), 2.55-2.46 (m, 3H), 2.09-1.97 (m, 1H), 1.82-1.71 (m, 1H), 1.64 (s, 3H), 1.48-1.37 (m, 1H), 1.22-1.11 (m, 1H), 1.01-0.85 (m, 8H) ppm.

Example 229. Compound 229. (2S)-3-[3-[(6R)-22-Fluoro-6,10,10-trimethyl-12,12,24-trioxo-3-oxa-12λ6,24λ4-dithia-19,28,30-triazapentacyclo[23.3.1.12,5.015,23.016,20]triaconta-1(29),2(30),4,15,17,20,22,25,27-nonaen-6-yl]phenyl]-2-methylpropanoic Acid

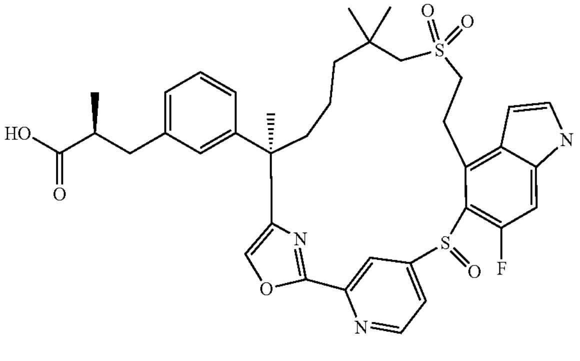 [SMILES: C[C@@H](Cc1cccc([C@@]2(C)CCCC(C)(C)CS(=O)(=O)CCc3c(c(F)cc4[nH]ccc34)S(=O)c3ccnc(c3)-c3nc2co3)c1)C(=O)O]

Exchanging (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoic acid (Intermediate 137H-1) with 4-((4-bromo-6-fluoro-1H-indol-5-yl)thio)picolinic acid (Intermediate 133A-2, 1.90 g, 2.46 mmol), and 2-bromo-1-(5-((4-bromo-6-fluoro-1-(phenylsulfonyl)-1H-indol-5-yl)oxy)-2-fluorophenyl)ethan-1-one (Intermediate 140) with methyl (S)-3-(3-((R)-1-bromo-8-((2-((tert-butyldiphenylsilyl)oxy)ethyl)sulfonyl)-3,7,7-trimethyl-2-oxooctan-3-yl)phenyl)-2-methylpropanoate (Intermediate 17-17, 903.8 mg, 2.46 mmol), the reaction procedure sequence (Steps A to C described for Example 192, followed by Steps B, C, D, F, and G described for Example 204) was used to prepare the title compound (1.9 mg) as a white solid. LC-MS: MS (ESI): 706 m/z $[M+H]^+$, purity: >99% (254 nm). retention time: 1.49 minutes (LC-MS method 21). $^1H$ NMR (400 MHz, $CD_3OD$) δ 8.93 (brs, 1H), 8.63 (brs, 1H), 7.99 (brs, 1H), 7.39 (d, J=2.8 Hz, 1H), 7.33-6.97 (m, 5H), 6.61 (brs, 1H), 5.4 (s, 1H), 3.62-3.53 (m, 1H), 3.48-3.38 (m, 1H), 3.04 (s, 2H), 2.97-2.89 (m, 1H), 2.70-2.56 (m, 2H), 2.49-2.35 (m, 1H), 2.10-1.98 (m, 1H), 1.83-1.72 (m, 1H), 1.68-1.56 (m, 3H), 1.54-1.42 (m, 2H), 1.38-1.24 (m, 7H), 1.21-1.00 (m, 5H) ppm.

Example 230. Compound 230. (2R)-3-[3-(22,28-difluoro-6,10,10-trimethyl-12,12-dioxo-24-oxa-12λ6-thia-5,19,30-triazapentacyclo[23.3.1.12,5.015,23.016,20]triaconta-1(29),2(30),3,15,17,20,22,25,27-nonaen-6-yl)phenyl]-2-methyl-propanoic Acid

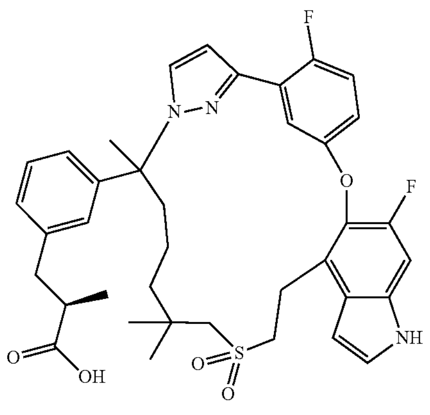 [SMILES: C[C@H](Cc1cccc(C2(C)CCCC(C)(C)CS(=O)(=O)CCc3c(c(F)cc4[nH]ccc34)Oc3ccc(F)c(c3)-c3ccn2n3)c1)C(=O)O]

Mixture of methyl (2R)-3-(3-(2-(3-(5-((4-bromo-6-fluoro-1-tosyl-1H-indol-5-yl)oxy)-2-fluorophenyl)-1H-pyrazol-1-yl)-7-((2-((tert-butyldimethylsilyl)oxy)ethyl)sulfonyl)-6,6-dimethylheptan-2-yl)phenyl)-2-methylpropanoate and methyl (R)-3-(3-((R)-2-(5-(5-((4-bromo-6-fluoro-1-tosyl-1H-indol-5-yl)oxy)-2-fluorophenyl)-1H-pyrazol-1-yl)-7-((2-((tert-butyldimethylsilyl)oxy)ethyl)sulfonyl)-6,6-dimethylheptan-2-yl)phenyl)-2-methylpropanoate

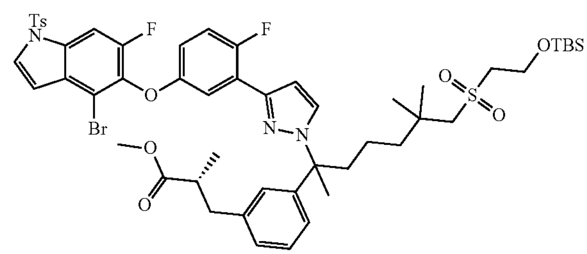

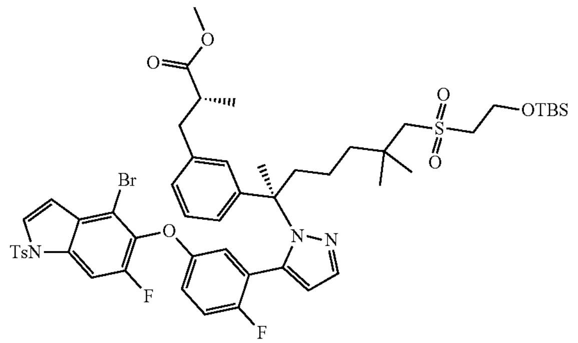

Step A: To a stirred solution of 4-bromo-6-fluoro-5-(4-fluoro-3-(1H-pyrazol-3-yl)phenoxy)-1-tosyl-1H-indole (Intermediate 21D, 800 mg, 1.47 mmol) and 1,3-dioxoisoindolin-2-yl 7-((2-((tert-butyldimethylsilyl)oxy)ethyl)sulfonyl)-2-(3-((R)-3-methoxy-2-methyl-3-oxopropyl)phenyl)-2,6,6-trimethylheptanoate (Intermediate 155, 3.00 g, 4.36 mmol) in dichloromethane (30 mL) was added 12-phenylbenzo[b]phenothiazine (PTH1) (24 mg, 0.0735 mmol) and tetrafluoroboron-2,4,6-trimethylpyridin-1-ium (614 mg, 2.94 mmol). The mixture was stirred and irradiated with 40W LED (450 nm) at room temperature (cooling with fan) under Ar for 72 hours. The solid was removed by filtration. The filtrate was concentrated. The residue was purified by automated flash chromatograph (eluting with 0-30% ethyl acetate in petroleum ether) to give the title mixture (2.7 g, 88%) as a color-less oil. LC-MS: MS (ESI): 1068, 1070 m/z $[M+H]^+$, purity: 22%+29% (214 nm). retention time: 3.38 and 3.50 minutes (LC-MS method 21).

Mixture of methyl (2R)-3-(3-(2-(3-(5-((4-bromo-6-fluoro-1-tosyl-1H-indol-5-yl)oxy)-2-fluorophenyl)-1H-pyrazol-1-yl)-7-((2-hydroxyethyl)sulfonyl)-6,6-dimethylheptan-2-yl)phenyl)-2-methylpropanoate and methyl (R)-3-(3-((R)-2-(5-(5-((4-bromo-6-fluoro-1-tosyl-1H-indol-5-yl)oxy)-2-fluorophenyl)-1H-pyrazol-1-yl)-7-((2-hydroxyethyl)sulfonyl)-6,6-dimethylheptan-2-yl)phenyl)-2-methylpropanoate

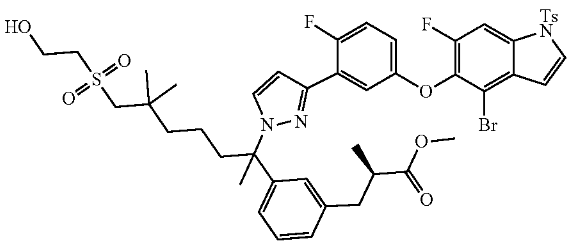

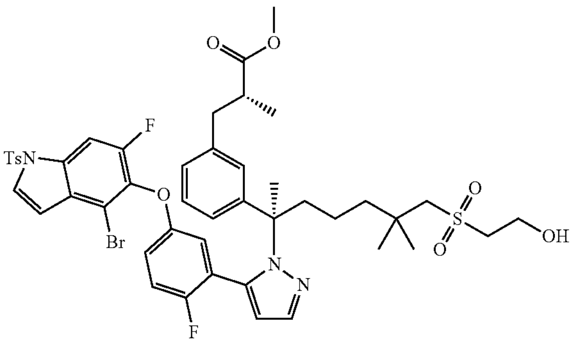

Step B: To a stirred solution of tetrabutylammonium fluoride (4.0 mL, 4.00 mmol) was added acetic acid (1.0 mL, 17.5 mmol). The solution was then treated with a solution of Step A mixture (2.70 g, 0.556 mmol) in tetrahydrofuran (10 mL) at room temperature and stirred for 2 hours. The mixture was diluted with water (20 mL) and extracted with ethyl acetate (2×20 mL). The combined organic extracts were washed with saturated ammonium chloride solution (20 mL), brine (20 mL), dried over sodium sulfate and concentrated. The residue was purified using automated flash chromatograph (eluting with 0 to 30% ethyl acetate in petroleum ether) to give a mixture of the title compound (2.0 g, 99%) as yellow oil. LC-MS: MS (ESI): 954, 956 m/z $[M+H]^+$, purity: 33%+28% (214 nm). retention time: 2.30 and 2.37 minutes (LC-MS method 21).

Methyl (2R)-3-(3-(2-(3-(5-((4-bromo-6-fluoro-1-tosyl-1H-indol-5-yl)oxy)-2-fluorophenyl)-1H-pyrazol-1-yl)-6,6-dimethyl-7-(vinylsulfonyl)heptan-2-yl)phenyl)-2-methylpropanoate and methyl (2R)-3-(3-(2-(5-(5-((4-bromo-6-fluoro-1-tosyl-1H-indol-5-yl)oxy)-2-fluorophenyl)-1H-pyrazol-1-yl)-6,6-dimethyl-7-(vinylsulfonyl)heptan-2-yl)phenyl)-2-methylpropanoate

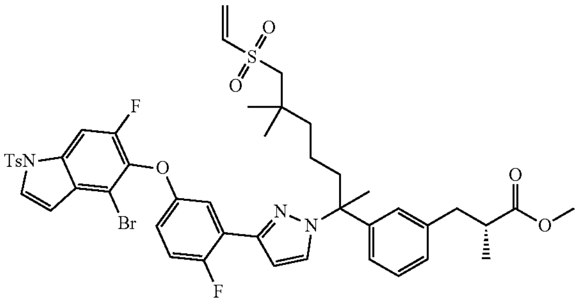

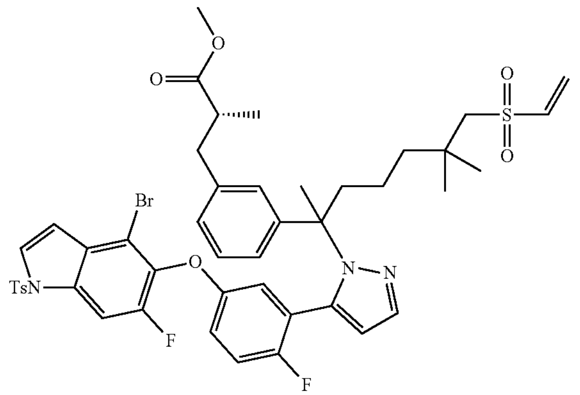

Step C: To a stirred solution of Step B mixture (2.00 g, 0.69 mmol) in dichloromethane (20 mL) was added triethylamine (0.88 mL, 6.32 mmol) followed by methanesulfonyl chloride (5.36 eq, 0.24 mL, 3.14 mmol) at room temperature. The mixture was stirred for 2 hours and concentrated. The residue was purified, first, using reverse phase flash chromatography (eluting with 10 to 80% acetonitrile in water (0.3% trifluoroacetic acid), then automated silica gel flash chromatography (eluting with 0 to 30% ethyl acetate in petroleum ether) to give the title mixture (700 mg, 0.35 mmol, 50%) as a white solid. LC-MS: MS (ESI): 936, 938 m/z $[M+H]^+$, purity: 41%+47% (214 nm). retention time: 2.38 and 2.46 minutes (LC-MS method 21).

Regio-isomer 1, methyl (2R)-3-[3-[(13E)-22,28-difluoro-6,10,10-trimethyl-12,12-dioxo-19-(p-tolylsulfonyl)-24-oxa-12λ6-thia-5,19,30-triazapentacyclo[23.3.1.12,5.015,23.016,20]triaconta-1(29),2(30),3,13,15,17,20,22,25,27-decaen-6-yl]phenyl]-2-methyl-propanoate

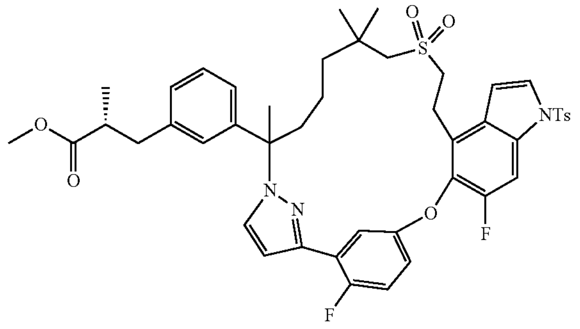 [SMILES: COC(=O)[C@H](C)Cc1cccc(C2(C)CCCC(C)(C)CS(=O)(=O)CCc3c(c(F)cc4c3ccn4S(=O)(=O)c3ccc(C)cc3)Oc3ccc(F)c(c3)-c3ccn2n3)c1]

And regio-isomer 2, methyl (2R)-3-[3-[(14E)-23,29-difluoro-7,11,11-trimethyl-13,13-dioxo-20-(p-tolylsulfonyl)-25-oxa-13 6-thia-5,6,20-triazapentacyclo[24.3.1.02,6.016,24.017,21]triaconta-1(30),2,4,14,16,18,21,23,26,28-decaen-7-yl]phenyl]-2-methyl-propanoate

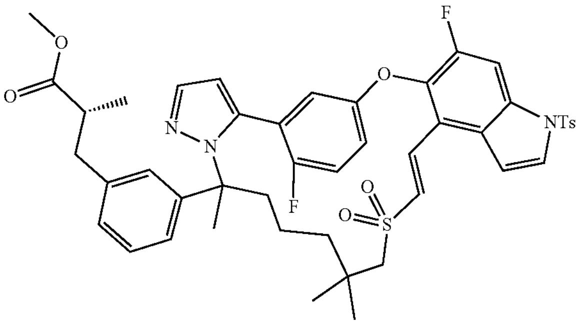 [SMILES: COC(=O)[C@H](C)Cc1cccc(C2(C)CCCC(C)(C)CS(=O)(=O)/C=C/c3c(c(F)cc4c3ccn4S(=O)(=O)c3ccc(C)cc3)Oc3ccc(F)c(c3)-c3ccnn32)c1]

Step D: To a stirred solution of bis(tri-tert-butylphosphine)palladium (131 mg, 0.255 mmol) and triethylamine (1.2 mL, 8.54 mmol) in toluene (100 mL) was added a solution of Step C mixture (150 mg, 0.066 mmol) in toluene (2 mL) at 100° C. under argon over 30 minutes. The mixture was refluxed for 16 hours and concentrated. The residue was purified using automated flash chromatography (eluting with 0 to 50% ethyl acetate in petroleum ether) to give the first eluent, Regio-isomer 1 (25 mg, 0.029 mmol, 11%) and the second eluent, Regio-isomer 2 (50 mg, 0.058 mmol, 23%), both as colorless oil.

Regio Isomer 1: LC-MS: MS (ESI): 856 m/z $[M+H]^+$, purity: >99% (214 nm). retention time: 2.68 minutes (LC-MS method 33).

Regio Isomer 2: LC-MS: MS (ESI): 856 m/z $[M+H]^+$, purity: 50% (214 nm). retention time: 2.46 minutes (LC-MS method 33).

Methyl (2R)-3-[3-[(13E)-22,28-difluoro-6,10,10-trimethyl-12,12-dioxo-24-oxa-12λ6-thia-5,19,30-triazapentacyclo[23.3.1.12,5.015,23.016,20]triaconta-1(29),2(30),3,13,15,17,20,22,25,27-decaen-6-yl]phenyl]-2-methyl-propanoate

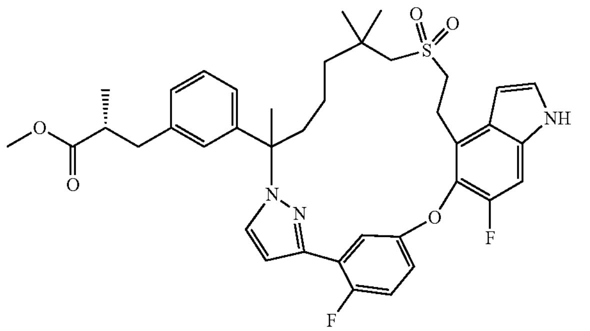 [SMILES: COC(=O)[C@H](C)Cc1cccc(C2(C)CCCC(C)(C)CS(=O)(=O)CCc3c(c(F)cc4[nH]ccc34)Oc3ccc(F)c(c3)-c3ccn2n3)c1]

Step E. To a solution of Regio-isomer 1 of Step D product (25 mg, 0.0292 mmol) was added potassium carbonate (10 mg, 0.0724 mmol) in methanol (10 mL). The mixture was stirred at room temperature for 16 hours, neutralized with 1 N hydrochloric acid, and concentrated. The residue was purified using automated silica gel flash chromatography (eluting with 0 to 80% ethyl acetate in petroleum ether) to give the title compound (7 mg, 0.01 mmol, 34%). LC-MS: MS (ESI): 702 m/z $[M+H]^+$, purity: 74% (214 nm). retention time: 2.36 minutes (LC-MS method 33).

Methyl (2R)-3-[3-(22,28-difluoro-6,10,10-trimethyl-12,12-dioxo-24-oxa-12λ6-thia-5,19,30-triazapentacyclo[23.3.1.12,5.015,23.016,20]triaconta-1(29),2(30),3,15,17,20,22,25,27-nonaen-6-yl)phenyl]-2-methyl-propanoate

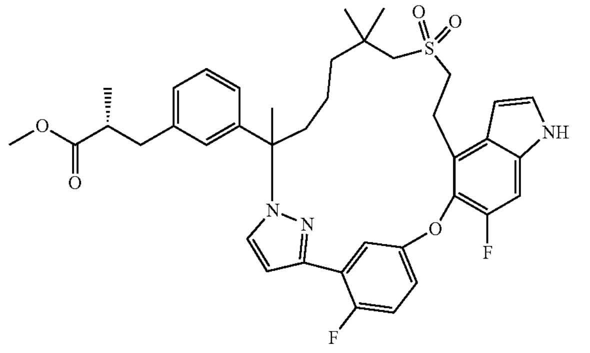 [SMILES: COC(=O)[C@H](C)Cc1cccc(C2(C)CCCC(C)(C)CS(=O)(=O)CCc3c(c(F)cc4[nH]ccc34)Oc3ccc(F)c(c3)-c3ccn2n3)c1]

Step F: To a stirred solution of Step E product (7.0 mg, 0.01 mmol) and palladium on carbon (7.0 mg, 10%, 50% wet) in ethanol (3 mL) was stirred at 50° C. for 2 hours under hydrogen, cooled to room temperature and filtered through a pad of Celite. The filtrate was concentrated to give the crude title compound (7 mg, 0.01 mmol, 95%) as a color-less oil, which was used for next step without further purification. LC-MS: MS (ESI): 704 m/z $[M+H]^+$, purity: 95% (214 nm). retention time: 2.41 minutes (LC-MS method 33).

Compound 230. (2R)-3-[3-(22,28-Difluoro-6,10,10-trimethyl-12,12-dioxo-24-oxa-12λ6-thia-5,19,30-triazapentacyclo[23.3.1.12,5.015,23.016,20]triaconta-1(29),2(30),3,15,17,20,22,25,27-nonaen-6-yl)phenyl]-2-methyl-propanoic Acid

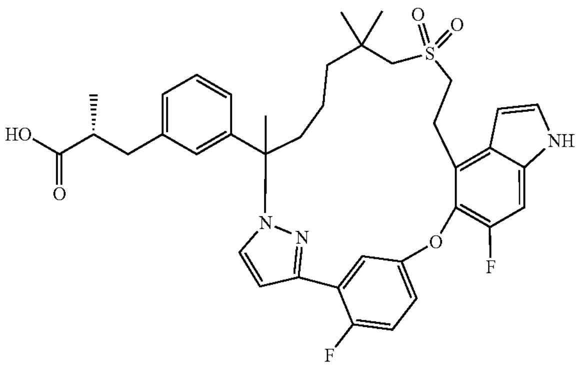 [SMILES: C[C@H](Cc1cccc(C2(C)CCCC(C)(C)CS(=O)(=O)CCc3c(c(F)cc4[nH]ccc34)Oc3ccc(F)c(c3)-c3ccn2n3)c1)C(=O)O]

Step G: To a stirred solution of Step F product (7.0 mg, 0.01 mmol) and lithium hydroxide monohydrate (4.2 mg, 0.1 mmol) in tetrahydrofuran (2 mL) and water (1 mL) was stirred at room temperature for 16 hours, then neutralized with hydrochloric acid (1M) to pH 7 and extracted with ethyl acetate (2×3 mL). The combined organic extracts were dried over sodium sulfate, filtered, and concentrated. The residue was purified using prep-HPLC to give the title compound (5.0 mg, 0.007 mmol, 73%) as a white solid. LC-MS: MS (ESI): 690 m/z $[M+H]^+$, purity: 99% (254 nm). retention time: 2.24 minutes (LC-MS method 21).

$^1H$ NMR (400 MHz, $CD_3OD$) δ 8.32 (s, 1H), 7.71 (d, J=2.3 Hz, 1H), 7.55 (d, J=5.9 Hz, 1H), 7.31 (d, J=3.2 Hz, 1H), 7.23 (d, J=9.7 Hz, 1H), 7.20-7.13 (m, 1H), 7.05 (d, J=7.2 Hz, 1H), 7.00-6.94 (m, 1H), 6.84-6.76 (m, 2H), 6.70 (t, J=7.2 Hz, 1H), 6.62 (d, J=3.2 Hz, 1H), 3.41 (t, J=7.1 Hz, 2H), 3.20-3.00 (m, 2H), 3.00-2.90 (m, 1H), 2.64-2.48 (m, 4H), 2.31-2.21 (m, 1H), 2.05-1.93 (m, 1H), 1.88 (s, 2H), 1.45-1.17 (m, 4H), 1.09-0.81 (m, 10H) ppm.

Example 231. Compound 231. (2R)-3-[3-[(6R)-22-Fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

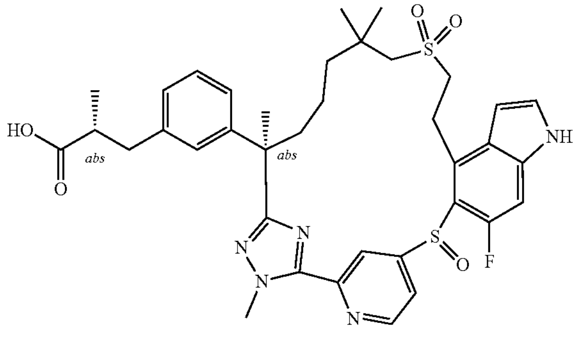 [SMILES: C[C@H](Cc1cccc([C@@]2(C)CCCC(C)(C)CS(=O)(=O)CCc3c(c(F)cc4[nH]ccc34)S(=O)c3ccnc(c3)-c3nc2nn3C)c1)C(=O)O]

Methyl (2R)-3-[3-[(6R)-22-fluoro-3,6,10,10-tetramethyl-12,12,24-trioxo-12λ6,2414-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

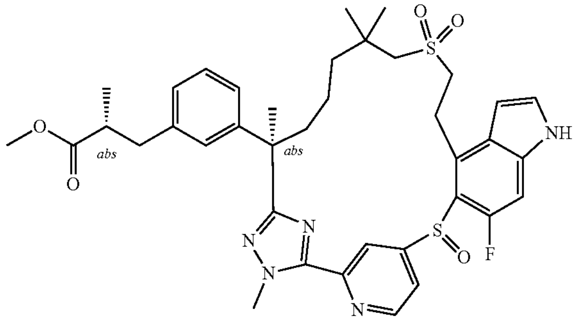 [SMILES: COC(=O)[C@H](C)Cc1cccc([C@@]2(C)CCCC(C)(C)CS(=O)(=O)CCc3c(c(F)cc4[nH]ccc34)S(=O)c3ccnc(c3)-c3nc2nn3C)c1]

Step A: Exchanging methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 6.87 g, 17.33 mmol), and methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-((R)-7-((2-hydro xyethyl)sulfonyl)-2,6,6-trimethyl-1-(2-methylhydrazineyl)-1-oxoheptan-2-yl)phenyl)-2-methylpropanoate (Intermediate 137, 7 g, 14.44 mmol), the reaction procedure sequence (Steps A to F described for Example 204, followed by Step B described for Examples 217A and 217B) was used to prepare the title compound (1.4 g), with about ~5% of another diastereomer. To remove the impure diastereomer, the methyl ester was subject to chiral SFC separation under the following conditions: Instrument: SFC-200 (Thar, Waters); Column: AS 20*250 mm, 10 μm; Column temperature: 35° C.; Mobile phase: carbon dioxide/methanol (0.2%7M ammonia in methanol)=65/35; Flow rate: 100 g/minute; Back pressure: 100 bar; Detection wavelength: 214 nm; Cycle time: 6.2 minutes; Sample solution: 650 mg dissolved in 70 ml Methanol; Injection volume: 1.5 mL. 510 mg of the title methyl ester obtained. LC-MS: MS (ESI): 734 m/z $[M+H]^+$, purity: 98% (214 nm). retention time: 2.04 minutes (LC-MS method 21).

Compound 231. (2R)-3-[3-[(6R)-22-Fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

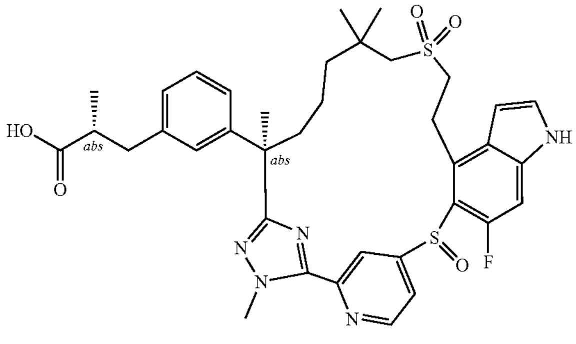 [SMILES: C[C@H](Cc1cccc([C@@]2(C)CCCC(C)(C)CS(=O)(=O)CCc3c(c(F)cc4[nH]ccc34)S(=O)c3ccnc(c3)-c3nc2nn3C)c1)C(=O)O]

Step B: To a stirred solution of Step A product (510 mg, 0.69 mmol) in tetrahydrofuran (6 mL) was added lithium hydroxide monohydrate (2 mL, 1M in water). The reaction mixture was stirred at room temperature for 16 hours, then acidified with 1M hydrochloric acid to pH ~4 and extracted with ethyl acetate (2×25 mL). The combined organic extracts were washed with brine, dried over sodium sulfate, filtered, and concentrated. The residue was purified by prep-HPLC to give the title compound (321.3 mg, 64%) as a white solid. LC-MS: MS (ESI): 720 m/z $[M+H]^+$, purity: >99% (254 nm). retention time: 1.87 minutes (LC-MS method 21). $^1H$ NMR (400 MHz, $CD_3OD$) δ 8.94 (brs, 1H), 8.71 (brs, 1H), 7.39 (d, J=3.2 Hz, 1H), 7.31-6.97 (m, 6H), 6.57 (brs, 1H), 4.32 (s, 3H), 3.68-3.61 (m, 1H), 3.52-3.44 (m, 1H), 3.18-2.86 (m, 4H), 2.67-2.57 (m, 2H), 2.50-2.41 (m, 1H), 1.83-1.70 (m, 4H), 1.59-1.40 (m, 4H), 1.36-1.00 (m, 10H) ppm.

Example 233. Compound 233. (2S)-3-[3-[(6R)-22-Fluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

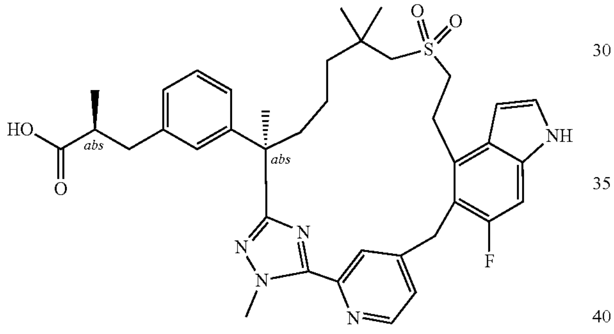

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 200 mg, 0.413 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)methyl)pyridine-2-carbimidothioate (Intermediate 150-3, 172 mg, 0.454 mmol), the reaction procedure sequence (Steps A to D, and Step F) described for Example 6 was used to prepare the title compound (9.5 mg, 0.014 mmol) as a white solid. LC-MS: MS (ESI): 686 m/z $[M+H]^+$, purity: >99% (254 nm). retention time: 2.03 minutes (LC-MS method 21). $^1H$ NMR (400 MHz, $CD_3OD$) δ 8.54 (d, J=5.2 Hz, 1H), 8.30 (s, 1H), 7.37 (d, J=5.2 Hz, 1H), 7.23 (d, J=3.2 Hz, 1H), 7.17-7.10 (m, 3H), 7.05-6.99 (m, 2H), 6.47 (d, J=2.8 Hz, 1H), 4.32 (d, J=14.8 Hz, 1H), 4.28 (s, 3H), 4.14 (d, J=14.8 Hz, 1H), 3.50-3.29 (m, 2H), 3.18-3.07 (m, 2H), 2.97-2.88 (m, 3H), 2.66-2.56 (m, 2H), 2.40-2.35 (m, 1H), 1.94-1.89 (m, 1H), 1.72 (s, 3H), 1.63-1.54 (m, 2H), 1.48-1.42 (m, 1H), 1.25 (s, 3H), 1.21-1.12 (m, 1H), 1.09-1.06 (m, 6H) ppm.

Example 234. Compound 234. (2R)-3-[3-[(6R)-22-fluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

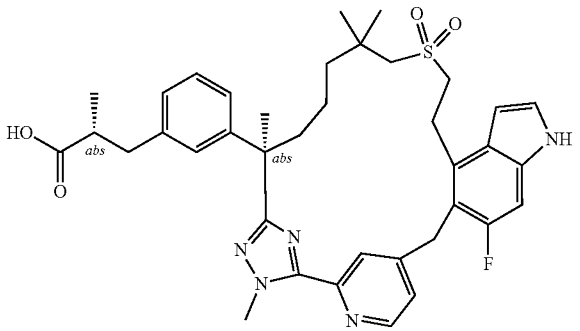

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 300 mg, 0.619 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)methyl)pyridine-2-carbimidothioate (Intermediate 150-3, 258 mg, 0.681 mmol), the reaction procedure sequence (Steps A to D, and Step F) described for Example 6 was used to prepare the title compound (6.7 mg, 0.01 mmol) as a white solid. LC-MS: MS (ESI): 686 m/z $[M+H]^+$, purity: >99% (254 nm). retention time: 2.03 minutes (LC-MS method 21). $^1H$ NMR (400 MHz, $CD_3OD$) δ 8.55 (d, J=4.0 Hz, 1H), 8.30 (s, 1H), 7.38 (s, 1H), 7.24 (d, J=2.4 Hz, 1H), 7.17-7.10 (m, 3H), 7.05-6.99 (m, 2H), 6.47 (s 1H), 4.32 (d, J=14.8 Hz, 1H), 4.28 (s, 3H), 4.14 (d, J=14.8 Hz, 1H), 3.50-3.29 (m, 2H), 3.18-3.07 (m, 2H), 2.97-2.88 (m, 3H), 2.66-2.56 (m, 2H), 2.40-2.35 (m, 1H), 1.94-1.89 (m, 1H), 1.72 (s, 3H), 1.63-1.54 (m, 2H), 1.48-1.42 (m, 1H), 1.25 (s, 3H), 1.21-1.12 (m, 1H), 1.10-1.08 (m, 6H) ppm.

Example 235. Compound 235A and Compound 235B. Diastereomers 1 and 2 of (2R)-3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propane-1,2-diol

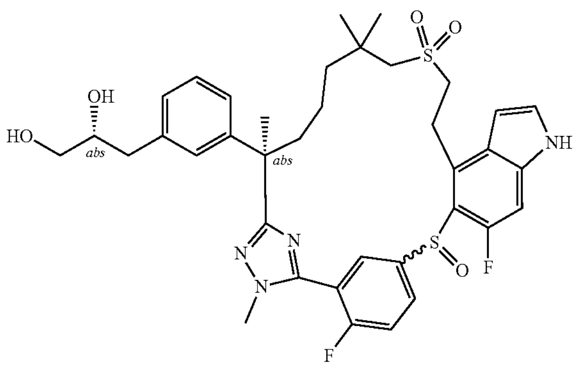 [SMILES: Cn1nc2nc1-c1cc(ccc1F)S(=O)c1c(F)cc3[nH]ccc3c1CCS(=O)(=O)CC(C)(C)CCC[C@]2(C)c1cccc(C[C@@H](O)CO)c1]

(6R)-6-[3-[[(4R)-2,2-dimethyl-1,3-dioxolan-4-yl] methyl]phenyl]-22,28-difluoro-3,6,10,10-tetramethyl-19-(p-tolylsulfonyl)-12λ6,24λ4-dithia-3,4,19,30-tetrazapentacyclo[23.3.1.12,5.015,23.016,20] triaconta-1(29),2(30),4,15,17,20,22,25,27-nonaene 12,12,24-trioxide

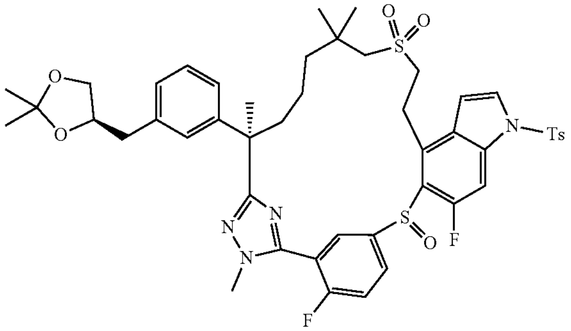 [SMILES: Cc1ccc(S(=O)(=O)n2ccc3c4c(c(F)cc32)S(=O)c2ccc(F)c(c2)-c2nc(nn2C)[C@@](C)(c2cccc(C[C@@H]3COC(C)(C)O3)c2)CCCC(C)(C)CS(=O)(=O)CC4)cc1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-2-(3-(((R)-2,2-dimethyl-1,3-dioxolan-4-yl) methyl)phenyl)-7-((2-hydroxyethyl)sulfonyl)-N',2,6,6-tetramethylheptanehydrazide (Intermediate 112-1, 310 mg, 0.622 mmol), the reaction procedure sequence (Steps A to F) described for Example 204 was followed to prepare the title compound. (40 mg, 0.044 mmol) as a light-yellow oil. LC-MS: MS (ESI): 919 m/z $[M+H]^+$, purity: 90% (214 nm). retention time: 2.12 minutes (LC-MS method 004).

Compound 235A and 235B. Diastereomers 1 and 2 of (2R)-3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl] phenyl]propane-1,2-diol

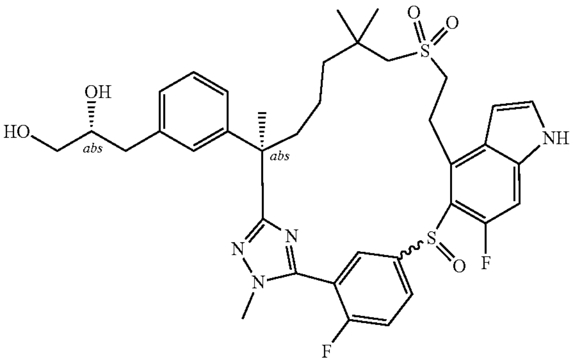 [SMILES: Cn1nc2nc1-c1cc(ccc1F)S(=O)c1c(F)cc3[nH]ccc3c1CCS(=O)(=O)CC(C)(C)CCC[C@]2(C)c1cccc(C[C@@H](O)CO)c1]

Step B: To a stirred solution of Step A product (40 mg, 0.044 mmol) in methanol (3 mL) was added p-toluenesulfonic acid monohydrate (4.2 mg, 0.022 mmol). The mixture was stirred at room temperature for 4 hours. Then treated with potassium carbonate (30 mg, 0.22 mmol). The mixture was stirred at room temperature for another 2 hours, quenched with water (20 mL), and extracted with ethyl acetate (3×15 mL). The combined organic extracts were washed with brine (20 mL), dried over sodium sulfate, filtered, and concentrated. The residue was purified by Prep-HPLC. The first eluent was designated as 235A (STEREOISOMER 1) (3.9 mg, 0.00539 mmol, 12%, ~7:3R and S mixture at di-alcohol position); The second eluent was designated as 235B (STEREOISOMER 2) (5.7 mg, 0.00787 mmol, 18%, ~7:3R and S mixture at di-alcohol position) as white solids.

235A: LC-MS: MS (ESI): 725 m/z $[M+H]^+$, purity: >99% (214 nm). retention time: 1.72 minutes (LC-MS method 003). $^1H$ NMR (500 MHz, $CD_3OD$) δ: 8.37 (s, 1H), 8.04 (s, 1H), 7.58 (s, 1H), 7.38 (d, J=3.3 Hz, 1H), 7.22-7.08 (m, 3H), 7.06-6.99 (m, 2H), 6.68 (s, 1H), 3.83-3.72 (m, 4H), 3.66-3.50 (m, 2H), 3.48-3.38 (m, 3H), 3.18-3.00 (m, 3H), 2.79-2.75 (m, 1H), 2.65-2.59 (m, 1H), 2.42-2.37 (m, 1H), 1.89-1.83 (m, 1H), 1.71 (s, 3H), 1.60-1.45 (m, 1H), 1.45-1.26 (m, 3H), 1.24 (s, 3H), 1.10 (s, 3H) ppm.

235B: LC-MS: MS (ESI): 725 m/z $[M+H]^+$, purity: >99% (214 nm). retention time: 1.75 minutes (LC-MS method 003). $^1H$ NMR (500 MHz, $CD_3OD$) δ: 8.12 (s, 1H), 7.91 (s, 1H), 7.56 (t, J=9.1 Hz, 1H), 7.38 (d, J=3.3 Hz, 1H), 7.23-7.10 (m, 3H), 7.06-7.02 (m, 2H), 6.67 (s, 1H), 3.97-3.81 (m, 4H), 3.75-3.65 (m, 2H), 3.49-3.36 (m, 3H), 3.18-2.96 (m, 3H), 2.80-2.72 (m, 1H), 2.62-2.57 (m, 1H), 2.32-2.26 (m, 1H), 1.98-1.91 (m, 1H), 1.71 (s, 3H), 1.49-1.28 (m, 4H), 1.21 (s, 3H), 1.13 (s, 3H) ppm.

Example 236. Compound 236A and Compound 236B. Diastereomer 1 and 2 of (1R)-1-[3-[(6R)-22,28-difluoro-3,6,10,10-tetramethyl-12,12,24-trioxo-12λ6,24λ4-dithia-3,4,19,30-tetrazapentacyclo [23.3.1.12,5.015,23.016,20]triaconta-1(29),2(30),4,15,17,20,22,25,27-nonaen-6-yl]phenyl]ethane-1,2-diol

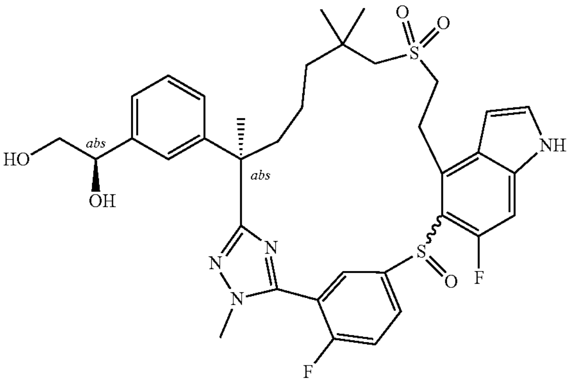 [SMILES: Cn1nc2nc1-c1cc(ccc1F)S(=O)c1c(F)cc3[nH]ccc3c1CCS(=O)(=O)CC(C)(C)CCC[C@]2(C)c1cccc([C@@H](O)CO)c1]

(6R)-6-[3-[(4R)-2,2-Dimethyl-1,3-dioxolan-4-yl] phenyl]-22,28-difluoro-3,6,10,10-tetramethyl-19-(p-tolylsulfonyl)-12λ6,24λ4-dithia-3,4,19,30-tetrazapentacyclo[23.3.1.12,5.015,23.016,20]triaconta-1 (29),2(30),4,15,17,20,22,25,27-nonaene 12,12,24-trioxide

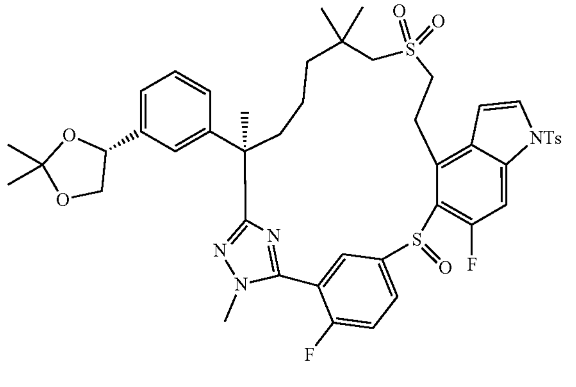 [SMILES: Cc1ccc(S(=O)(=O)n2ccc3c4c(c(F)cc32)S(=O)c2ccc(F)c(c2)-c2nc(nn2C)[C@@](C)(c2cccc([C@@H]3COC(C)(C)O3)c2)CCCC(C)(C)CS(=O)(=O)CC4)cc1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-2-(3-((R)-2,2-dimethyl-1,3-dioxolan-4-yl) phenyl)-7-((2-hydroxyethyl)sulfonyl)-N',2,6,6-tetramethylheptanehydrazide (Intermediate 107-4, 185 mg, 0.382 mmol), the reaction procedure sequence (Steps A to F described for Example 204) was used to prepare the title compound (60 mg, 0.066 mmol), a mixture of tow diastereomers as a white solid. LC-MS: MS (ESI): 905 m/z $[M+H]^+$, purity: >99% (254 nm). retention time: 2.12 and 2.17 minutes (LC-MS method 4).

Compound 236A and 236B. Diastereomer 1 and 2 of (1R)-1-[3-[(6R)-22,28-difluoro-3,6,10,10-tetramethyl-12,12,24-trioxo-12λ6,24λ4-dithia-3,4,19,30-tetrazapentacyclo [23.3.1.12,5.015,23.016,20]triaconta-1(29),2(30),4,15,17,20,22,25,27-nonaen-6-yl]phenyl]ethane-1,2-diol

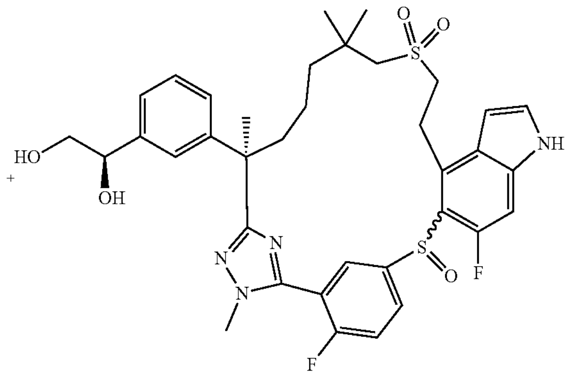 [SMILES: Cn1nc2nc1-c1cc(ccc1F)S(=O)c1c(F)cc3[nH]ccc3c1CCS(=O)(=O)CC(C)(C)CCC[C@]2(C)c1cccc([C@@H](O)CO)c1]

To a stirred solution of Step A product (70 mg, 0.077 mmol) in methanol (3 mL) was added p-toluenesulfonic acid monohydrate (7.4 mg, 0.039 mmol). The mixture was stirred at room temperature for 4 hours, then treated with potassium carbonate (53 mg, 0.39 mmol) and stirred for another 2 hours. The mixture was quenched with water (20 mL) and extracted with ethyl acetate (3×15 mL). The combined organic extracts were washed with brine (20 mL), dried over sodium sulfate, filtered, and concentrated. The residue was purified by reverse phase Prep-HPLC. The first eluent (2.1 mg, 0.003 mmol, 3.8%, white solid), Diastereomer 1, was designated as 236A. The second eluent (4.8 mg, 0.0068 mmol, 8.7%, white solid), was designated as 236B.

Compound 236A: LC-MS: MS (ESI): 711 m/z $[M+H]^+$, purity: >99% (254 nm). retention time: 1.69 minutes (LC-MS method 4). $^1H$ NMR (400 MHz, $CD_3OD$) δ 8.05 (s, 1H), 7.80-7.72 (m, 1H), 7.64-7.53 (m, 1H), 7.37 (d, J=3.6 Hz, 1H), 7.25-7.08 (m, 5H), 6.68-6.67 (m, 1H), 4.85-4.80 (m, 1H), 4.61 (t, J=6.0 Hz, 1H), 3.79-3.76 (m, 3H), 3.57-3.52 (m, 2H), 3.49-1.47 (m, 1H), 3.14-3.00 (m, 3H), 2.88-2.66 (m, 2H), 2.46-2.36 (m, 1H), 1.92-1.83 (m, 1H), 1.71 (s, 3H), 1.36-1.21 (m, 8H), 1.14-1.07 (m, 1H) ppm.

Compound 236B: LC-MS: MS (ESI): 711 m/z $[M+H]^+$, purity: 98% (214 nm). retention time: 1.71 minutes (LC-MS method 4). $^1H$ NMR (400 MHz, $CD_3OD$) δ 11.2 (s, 1H), 8.16 (s, 1H), 8.11-7.86 (m, 1H), 7.59 (t, J=9.6 Hz, 1H), 7.40 (d, J=3.2 Hz, 1H), 7.30 (s, 1H), 7.26-7.14 (m, 4H), 6.70 (s, 1H), 4.63 (t, J=6.0 Hz, 1H), 3.96-3.87 (m, 4H), 3.74-3.67 (m, 1H), 3.56 (d, J=6.0 Hz, 2H), 3.52-3.47 (m, 1H), 3.28-3.03 (m, 3H), 2.35-2.30 (m, 1H), 2.00-1.94 (m, 1H), 1.74 (s, 3H), 1.50-1.35 (m, 3H), 1.24 (s, 3H), 1.16 (s, 3H), 1.08-1.00 (m, 1H) ppm.

Example 237. Compound 237A and Compound 237B. Diastereomer 1 and 2 of (2S)-1-[3-[(6R)-22,28-difluoro-3,6,10,10-tetramethyl-12,12,24-trioxo-12λ6,24λ4-dithia-3,4,19,30-tetrazapentacyclo [23.3.1.12,5.015,23.016,20]triaconta-1(29),2(30),4,15,17,20,22,25,27-nonaen-6-yl]phenyl]propan-2-ol

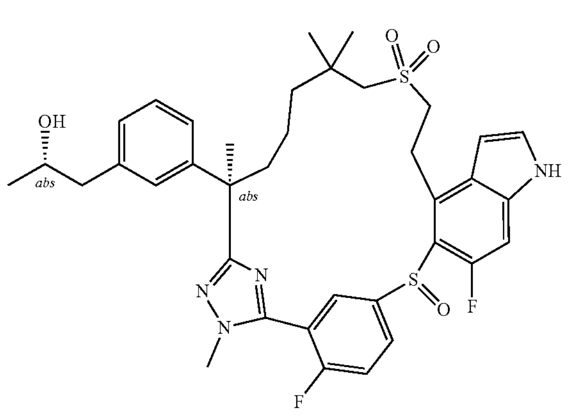 [SMILES: C[C@H](O)Cc1cccc([C@@]2(C)CCCC(C)(C)CS(=O)(=O)CCc3c(c(F)cc4[nH]ccc34)S(=O)c3ccc(F)c(c3)-c3nc2nn3C)c1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (S)-1-(3-((R)-7-((2-hydroxyethyl)sulfonyl)-2,6,6-trimethyl-1-(2-methylhydrazineyl)-1-oxoheptan-2-yl) phenyl)propan-2-yl acetate (Intermediate 137-8, 540 mg, 1.11 mmol), the reaction procedure sequence (Steps A to F described for Example 204, followed by Step B described for Examples 217A and 217B) was used to prepare the title compounds as a mixture. This mixture was separated by reverse phase prep-HPLC. The first eluent (10 mg, 0.0144 mmol, white solid), Diastereomer 1, was designated as 237A; The second eluent (17 mg, 0.0236 mmol, white solid), Diastereomer 2, was designated as 237B. LC-Mass Method: Mobile Phase: A: water (0.01% TFA) B: Acetonitrile (0.01% TFA) Gradient: 5% increase to 95% B within 1.5 min, 95% B for 1.7 min. Flow Rate: 2.0 mL/min Column: Sunfire C18, 4.6*50 mm, 3.5 um. LC purity: 100% (214 nm); Mass: find peak 709.0 (M+H)+ at 1.77 min for P1 and 709.8 (M+ H)+ at 1.81 min for P2.

Compound 237A: LC-MS: MS (ESI): 709 m/z $[M+H]^+$, purity: >99% (214 nm). retention time: 1.77 minutes (LC-MS method 34). $^1H$ NMR (400 MHz, $CD_3OD$) δ 8.2-7.8 (m, 2H), 7.57 (brs, 1H), 7.37 (d, J=3.2 Hz, 1H), 7.19-7.14 (m, 2H), 7.05-6.99 (m, 3H), 6.67 (s, 1H), 3.95-3.70 (m, 5H), 3.65-3.40 (m, 2H), 3.27-3.20 (m, 1H), 3.12-3.00 (m, 2H), 2.80-2.69 (m, 1H), 2.61-2.56 (m, 1H), 2.45-2.35 (m, 1H), 1.89-1.82 (m, 1H), 1.69 (s, 3H), 1.45-1.15 (m, 6H), 1.14-1.00 (m, 7H) ppm.

Compound 237B: LC-MS: MS (ESI): 709 m/z $[M+H]^+$, purity: >99% (214 nm). retention time: 1.81 minutes (LC-MS method 34). $^1H$ NMR (400 MHz, $CD_3OD$) δ 8.12 (s, 1H), 7.92 (s, 1H), 7.55 (t, J=9.2 Hz, 1H), 7.53 (d, J=3.6 Hz, 1H), 7.18-6.98 (m, 5H), 6.67 (s, 1H), 3.85-3.82 (m, 5H), 3.68-3.64 (m, 1H), 3.50-3.47 (m, 1H), 3.24-3.19 (m, 1H), 3.09-2.99 (m, 2H), 2.72-2.55 (m, 2H), 2.29 (m, 1H), 1.97-1.91 (m, 1H), 1.70 (s, 3H), 1.46-1.27 (m, 4H), 1.21-1.06 (m, 9H) ppm.

Example 238. Compound 238. 3-[3-[(6R)-22-fluoro-3,6,10,10-tetramethyl-12,12,24-trioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]propanoic acid

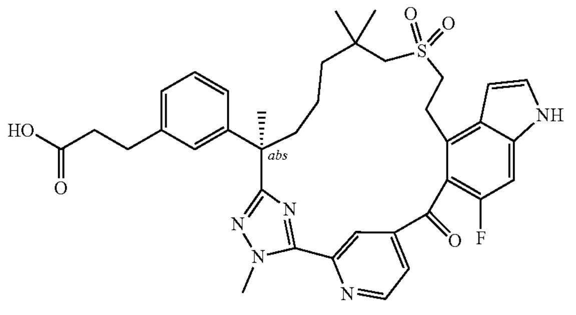 [SMILES: Cn1nc2nc1-c1cc(ccn1)C(=O)c1c(F)cc3[nH]ccc3c1CCS(=O)(=O)CC(C)(C)CCC[C@]2(C)c1cccc(CCC(=O)O)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with ethyl (R)-3-(3-(7-((2-hydroxyethyl)sulfonyl)-2,6,6-trimethyl-1-(2-methylhydrazineyl)-1-oxoheptan-2-yl)phenyl) propanoate (Intermediate 58-8, 0.54 g, 1.12 mmol), and methyl 5-((4-bromo-6-fluoro-1H-indol-5-yl)oxy)-2-fluorobenzimidothioate hydroiodide (Intermediate 14-1) with methyl 4-(4-bromo-6-fluoro-1H-indole-5-carbonyl)pyridine-2-carbimidothioate (Intermediate 150-2, 0.44 g, 1.12 mmol), the reaction procedure sequence (Steps A to D, and Step F) described for Example 6 was used to prepare the title compound (8.7 mg) as a white solid. LC-MS: MS (ESI): 686 m/z $[M+H]^+$, purity: >99% (214 nm). retention time: 1.63 minutes (LC-MS method 17). $^1H$ NMR (500 MHz, $CD_3OD$) δ 8.96 (d, J=5.0 Hz, 1H), 8.36 (s, 1H), 7.92 (dd, J=5.0, 1.5 Hz, 1H), 7.38 (d, J=3.5 Hz, 1H), 7.17 (d, J=11.0 Hz, 1H), 7.12 (t, J=8.0 Hz, 1H), 7.04 (s, 1H), 7.00 (d, J=8.0 Hz, 1H), 6.94 (d, J=8.0 Hz, 1H), 6.79 (d, J=3.0 Hz, 1H), 4.34 (s, 3H), 3.69-3.57 (m, 2H), 3.27-3.21 (m, 1H), 3.14-3.30 (m, 1H), 2.82 (t, J=7.5 Hz, 2H), 2.52-2.48 (m, 3H), 2.30 (d, J=14.0 Hz, 1H), 2.09-1.97 (m, 1H), 1.80-1.68 (m, 1H), 1.65 (s, 3H), 1.44-1.30 (m, 1H), 1.14-1.06 (m, 1H), 1.02-0.82 (m, 8H) ppm.

Example 239. Compound 239A and Compound 239B. Diastereomers 1 and 2 of (2S)-3-[3-[(6R)-22-fluoro-6,10,10-trimethyl-12,12,24-trioxo-3,12λ6,24 m-trithia-19,28,30-triazapentacyclo[23.3.1.12,5.015,23.016,20]triaconta-1(29),2(30),4,15,17,20,22,25,27-nonaen-6-yl]phenyl]-2-methyl-propanoic Acid

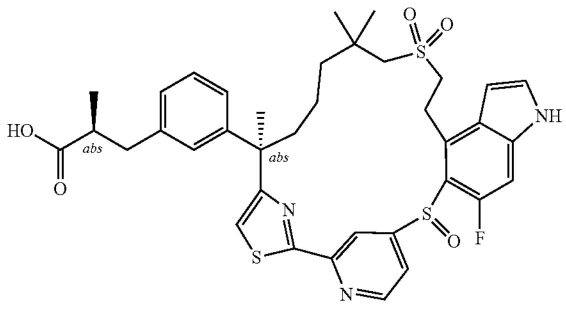 [SMILES: C[C@@H](Cc1cccc([C@@]2(C)CCCC(C)(C)CS(=O)(=O)CCc3c(c(F)cc4[nH]ccc34)S(=O)c3ccnc(c3)-c3nc2cs3)c1)C(=O)O]

Methyl (S)-3-(3-((R)-2-(2-(4-((4-bromo-6-fluoro-1H-indol-5-yl)thio)pyridin-2-yl)thiazol-4-yl)-7-((2-((tert-butyldiphenylsilyl)oxy)ethyl)sulfonyl)-6,6-dimethylheptan-2-yl)phenyl)-2-methylpropanoate

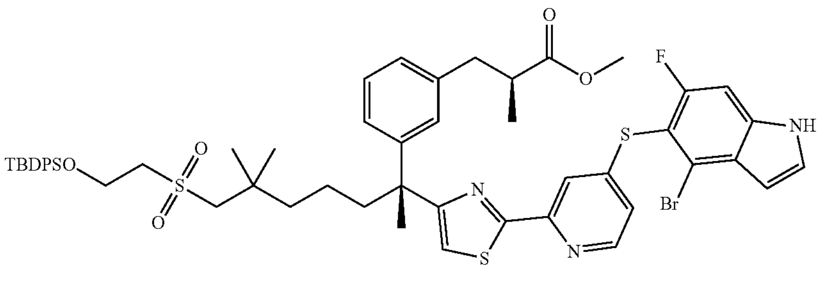

Step A: To a stirred solution of 4-((4-bromo-6-fluoro-1H-indol-5-yl)thio)pyridine-2-carbothioamide (Intermediate 76D-1, 297 mg, 0.777 mmol) in N,N-dimethylformamide (20 mL) was added methyl (S)-3-(3-((R)-1-bromo-8-((2-((tert-butyldiphenylsilyl)oxy)ethyl)sulfonyl)-3,7,7-trimethyl-2-oxooctan-3-yl)phenyl)-2-methylpropanoate (Intermediate 17-17, 600 mg, 0.78 mmol). The reaction mixture was stirred at 80° C. overnight, cooled to room temperature, and quenched with 100 mL of water. The solution was extracted with ethyl acetate (3×100 mL). The combined organic phase was washed with brine, dried over sodium sulfate and concentrated to give the crude title compound as a yellow solid (810 mg, 0.614 mmol, 79%). This solid was used for next step without further purification. LC-MS: MS (ESI): 1054, 1056 m/z $[M+H]^+$, purity: 50% (214 nm). retention time: 3.08 minutes (LC-MS method 4).

Methyl (S)-3-(3-((R)-2-(2-(4-((4-bromo-6-fluoro-1H-indol-5-yl)thio)pyridin-2-yl)thiazol-4-yl)-7-((2-hydroxyethyl)sulfonyl)-6,6-dimethylheptan-2-yl)phenyl)-2-methylpropanoate

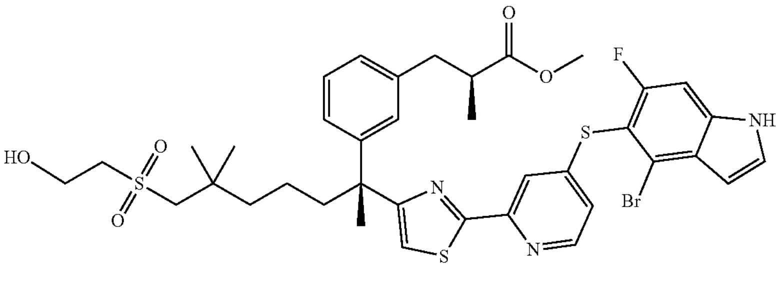 [SMILES: COC(=O)[C@@H](C)Cc1cccc([C@@](C)(CCCC(C)(C)CS(=O)(=O)CCO)c2csc(-c3cc(Sc4c(F)cc5[nH]ccc5c4Br)ccn3)n2)c1]

Step B: To a stirred solution of crude Step A product (810 mg, 0.614 mmol) in tetrahydrofuran (15 mL) was added tetra-n-butylammonium fluoride (1.23 mL, 1M in tetrahydrofuran, 1.23 mmol). The mixture was stirred at room temperature for 2 hours and concentrated. The residue was purified by silica gel column chromatography (eluting with petroleum ether: ethyl acetate=1:1) to give the title compound (480 mg, 0.529 mmol, 86%) as a yellow solid. LC-MS: MS (ESI): 816, 818 m/z $[M+H]^+$, purity: 81% (214 nm). retention time: 2.12 minutes (LC-MS method 4).

Compound 239A and 239B. Diastereomers 1 and 2 of (2S)-3-[3-[(6R)-22-fluoro-6,10,10-trimethyl-12,12,24-trioxo-3,12 6,24λ4-trithia-19,28,30-triazapentacyclo[23.3.1.12,5.015,23.016,20]triaconta-1(29),2(30),4,15,17,20,22,25,27-nonaen-6-yl]phenyl]-2-methyl-propanoic Acid

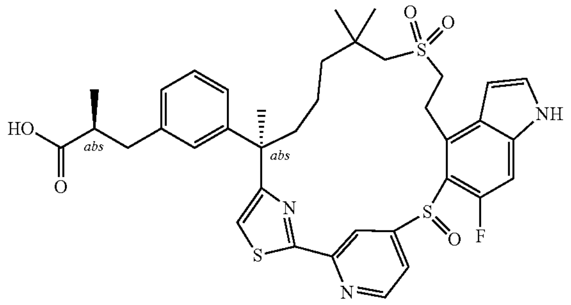 [SMILES: C[C@@H](Cc1cccc([C@@]2(C)CCCC(C)(C)CS(=O)(=O)CCc3c(c(F)cc4[nH]ccc34)S(=O)c3ccnc(c3)-c3nc2cs3)c1)C(=O)O]

Exchanging methyl (2S)-2-methyl-3-[3-[(1R)-1-[5-[5-[(4-bromo-6-fluoro-1H-indol-5-yl)sulfanyl]-2-fluoro-phenyl]-1-methyl-1,2,4-triazol-3-yl]-6-(2-hydroxyethylsulfonyl)-1,5,5-trimethyl-hexyl]phenyl]propanoate (Step A product of Example 204) with methyl (S)-3-(3-((R)-2-(2-(4-((4-bromo-6-fluoro-1H-indol-5-yl)thio)pyridin-2-yl)thiazol-4-yl)-7-((2-hydroxyethyl)sulfonyl)-6,6-dimethylheptan-2-yl)phenyl)-2-methylpropanoate (Step B product of this example, 480 mg, 0.53 mmol), the reaction procedure sequence (Steps B, C, D, E, F described for Example 204, followed by Steps B and C of Example 217A and 217B) was used to prepare the title compounds as a mixture. This mixture was separated by reverse phase prep-HPLC. The first eluent (7.9 mg, 0.011 mmol, a white solid), Diastereomer 1, was designated as 239A. The second eluent (8.8 mg, 0.0121 mmol), Diastereomer 2, was designated as Compound 239B.

Compound 239A: LC-MS: MS (ESI): 722 m/z $[M+H]^+$, purity: >99% (214 nm). retention time: 1.99 minutes (LC-MS method 4). $^1H$ NMR (400 MHz, DMSO-$d_6$) δ 11.76 (s, 1H), 8.68-8.58 (m, 2H), 7.74 (s, 1H), 7.54 (s, 1H), 7.45-7.42 (m, 1H), 7.13-6.89 (m, 5H), 6.47 (s, 1H), 3.06-2.92 (m, 3H), 2.88-2.83 (m, 1H), 2.75-2.68 (m, 1H), 1.77-1.61 (m, 5H), 1.46 (s, 3H), 1.24-1.12 (m, 8H), 1.06-0.98 (m, 6H) ppm.

Compound 239B: LC-MS: MS (ESI): 722 m/z $[M+H]^+$, purity: >99% (214 nm). retention time: 2.07 minutes (LC-MS method 4). $^1H$ NMR (400 MHz, DMSO-$d_6$) δ 11.76 (s, 1H), 8.68-8.58 (m, 2H), 7.74 (s, 1H), 7.54 (s, 1H), 7.45-7.42 (m, 1H), 7.13-6.89 (m, 5H), 6.47 (d, J=6.4 Hz, 1H), 3.06-2.97 (m, 3H), 2.87-2.86 (m, 1H), 2.76-2.73 (m, 1H), 1.75-1.64 (m, 5H), 1.46 (s, 3H), 1.29-1.13 (m, 8H), 1.06-0.99 (m, 6H) ppm.

Example 240. Compound 240. (2S)-3-[3-[(6R)-22,28-difluoro-6,10,10-trimethyl-12,12-dioxo-3,12λ6,24-trithia-19,30-diazapentacyclo[23.3.1.12,5.015,23.016,20]triaconta-1(29),2(30),4,15,17,20,22,25,27-nonaen-6-yl]phenyl]-2-methyl-propanoic Acid

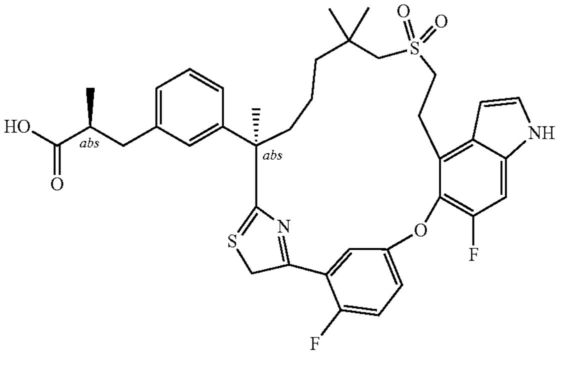

Methyl (2S)-3-[3-[(6R)-22,28-difluoro-6,10,10-trimethyl-12,12-dioxo-19-(p-tolylsulfonyl)-3,12 6,24-trithia-19,30-diazapentacyclo[23.3.1.12,5.015, 23.016,20]triaconta-1(29),2(30),4,15,17,20,22,25,27-nonaen-6-yl]phenyl]-2-methyl-propanoate

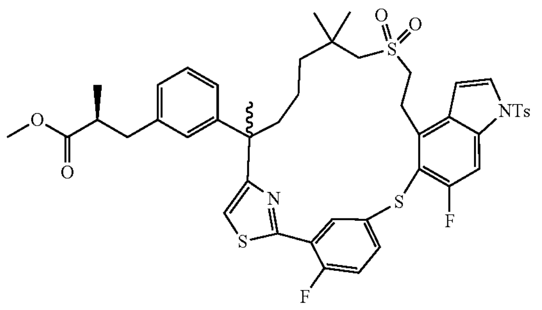 [SMILES: COC(=O)[C@@H](C)Cc1cccc(C2(C)CCCC(C)(C)CS(=O)(=O)CCc3c(c(F)cc4c3ccn4S(=O)(=O)c3ccc(C)cc3)Sc3ccc(F)c(c3)-c3nc2cs3)c1]

Step A: Exchanging 4-((4-bromo-6-fluoro-1H-indol-5-yl)thio)pyridine-2-carbothioamide (Intermediate 76D-1) with 5-((4-bromo-6-fluoro-1H-indol-5-yl)thio)-2-fluorobenzothioamide (Intermediate 76D, 336 mg, 0.842 mmol), the reaction procedure sequence (Steps A to B of Example 239A and 239B, followed by Steps B, C, D and E described for Example 204) was used to prepare the title compound (240 mg, 0.269 mmol). LC-MS: MS (ESI): 891 m/z $[M+H]^+$, purity: 85% (214 nm). retention time: 2.59 minutes (LC-MS method 34).

Compound 240. (2S)-3-[3-[(6R)-22,28-Difluoro-6,10,10-trimethyl-12,12-dioxo-3,12 6,24-trithia-19,30-diazapentacyclo[23.3.1.12,5.015,23.016,20]triaconta-1(29),2(30),4,15,17,20,22,25,27-nonaen-6-yl]phenyl]-2-methyl-propanoic Acid

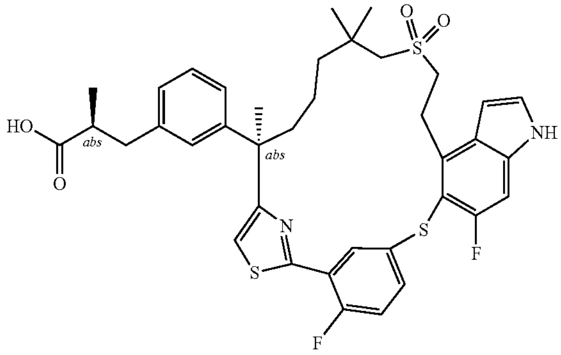 [SMILES: C[C@@H](Cc1cccc([C@@]2(C)CCCC(C)(C)CS(=O)(=O)CCc3c(c(F)cc4[nH]ccc34)Sc3ccc(F)c(c3)-c3nc2cs3)c1)C(=O)O]

Step B: To a stirred solution of Step A product (40 mg, 0.0449 mmol) in tetrahydrofuran (1.5 mL) and methanol (0.50 mL) was added lithium hydroxide monohydrate (0.50 mL, 0.50 mmol, 1 M in water). The mixture was stirred at room temperature for 16 hours, then acidified with 1.0 M hydrochloric acid to pH ~6 and extracted with ethyl acetate (3×10 mL). The combined organic phases were washed with brine, dried over sodium sulfate, filtered, and concentrated. The residue was purified by prep-HPLC to give the title compound (18.5 mg, 0.026 mmol, 57%) as a solid. LC-MS: MS (ESI): 723 m/z $[M+H]^+$, purity: 95% (214 nm), retention time: 2.10 minutes (LC-MS method 4). $^1$H NMR (500 MHz, $CD_3OD$) δ 8.04 (s, 1H), 7.36-7.29 (m, 3H), 7.24-7.13 (m, 3H), 7.03-6.97 (m, 2H), 6.92 (d, J=8.0 Hz, 1H), 6.60 (d, J=2.5 Hz, 1H), 3.68 (t, J=8.0 Hz, 2H), 3.13-3.02 (m, 2H), 2.96-2.87 (m, 2H), 2.76 (d, J=14.5 Hz, 1H), 2.65-2.58 (m, 2H), 2.28-2.20 (m, 1H), 1.75-1.70 (m, 1H), 1.67 (s, 3H), 1.38-1.27 (m, 3H), 1.19 (s, 3H), 1.05 (d, J=6.5 Hz, 3H), 1.01-0.91 (m, 4H) ppm.

Example 241. Compound 241A, Compound 241B. Diastereomers 1 and 2 of (2S)-3-[3-[(6R)-22,28-difluoro-6,10,10-trimethyl-12,12,24-trioxo-3,12λ6, 24M-trithia-19,30-diazapentacyclo[23.3.1.12,5.015, 23.016,20]triaconta-1(29),2(30),4,15,17,20,22,25,27-nonaen-6-yl]phenyl]-2-methyl-propanoic Acid

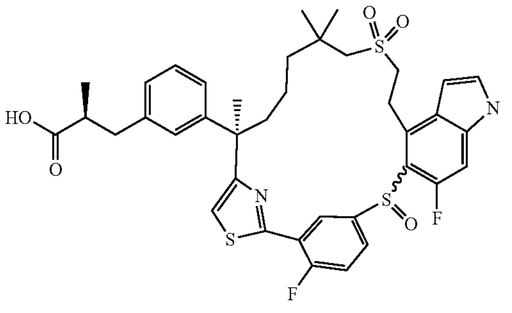 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2cs3)c1)C(=O)O]

Exchanging Methyl (2S)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015, 23.016,20]triaconta-1(29),2(30),4,15,17,20,22,25,27-nonaen-6-yl]phenyl]-2-methyl-propanoate (Step E product of Example 204) with Methyl (2S)-3-[3-[(6R)-22,28-difluoro-6,10,10-trimethyl-12,12-dioxo-19-(p-tolylsulfonyl)-3, 12λ6,24-trithia-19,30-diazapentacyclo[23.3.1.12,5.015, 23.016,20]triaconta-1(29),2(30),4,15,17,20,22,25,27-nonaen-6-yl]phenyl]-2-methyl-propanoate (Step A product of Example 240, 240 mg, 0.269 mmol), the reaction procedure sequence (Step A described for Example 205, followed by Steps B and C of Example 217A and 217B, in this order) was used to prepare the title compounds as a mixture of two diastereomers. Those two diastereomers were separated by reverse phase prep-HPLC. The first eluent (10.7 mg, 0.0145 mmol), Diastereomer 1, was designated as 241A; The second eluent (7.5 mg, 0.0101 mmol), Diastereomer 2, was designated as 241B.

Compound 241A: LC-MS: MS (ESI): 739 m/z $[M+H]^+$, purity: 98% (214 nm), retention time: 2.13 minutes (LC-MS method 34). $^1$H NMR (400 MHz, $CD_3OD$) δ 8.94-8.83 (m, 1H), 7.53 (s, 1H), 7.46-7.19 (m, 4H), 7.13 (t, J=7.6 Hz, 1H), 7.02 (s, 1H), 6.98-6.94 (m, 2H), 6.57 (d, J=2.4 Hz, 1H), 3.57-3.46 (m, 2H), 3.20-3.04 (m, 3H), 2.96-2.85 (m, 2H), 2.66-2.54 (m, 3H), 1.86-1.72 (m, 4H), 1.65-1.41 (m, 4H), 1.29 (s, 3H), 1.16 (s, 3H), 1.05 (d, J=6.4 Hz, 3H) ppm.

Compound 241B: LC-MS: MS (ESI): 739 m/z $[M+H]^+$, purity: 97% (214 nm), retention time: 2.17 minutes (LC-MS method 34). $^1$H NMR (400 MHz, $CD_3OD$) δ 8.91 (s, 1H), 7.45-7.34 (m, 3H), 7.30-7.24 (m, 2H), 7.18 (d, J=7.6 Hz, 1H), 7.15-7.11 (m, 2H), 7.07 (d, J=7.6 Hz, 1H), 6.59 (d, J=2.7 Hz, 1H), 3.72-3.65 (m, 1H), 3.56-3.49 (m, 1H), 3.17-3.10 (m, 2H), 3.04-2.89 (m, 3H), 2.66-2.59 (m, 2H), 2.34-2.28 (m, 2H), 1.97-1.90 (m, 1H), 1.77-1.60 (m, 4H), 1.50-1.38 (m, 2H), 1.21 (s, 3H), 1.11-1.03 (m, 6H) ppm.

Example 242. Compound 242. (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

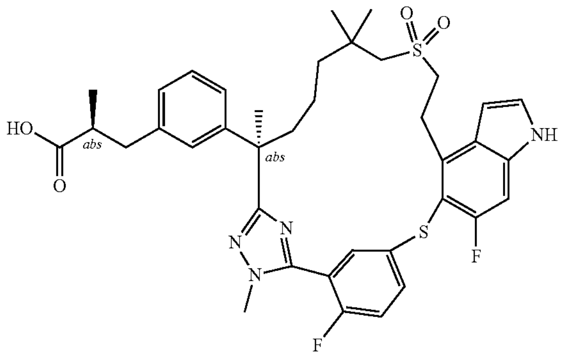 [SMILES: C[C@@H](Cc1cccc([C@@]2(C)CCCC(C)(C)CS(=O)(=O)CCc3c(c(F)cc4[nH]ccc34)Sc3ccc(F)c(c3)-c3nc2nn3C)c1)C(=O)O]

Methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204, 150 mg, 0.204 mmol) was subjected to Step G described for Example 204 and hydrolyzed to afford the title compound (113 mg, 0.16 mmol, 77%) as a white solid. LC-MS: MS (ESI): 721 m/z $[M+H]^+$, purity: 99% (214 nm), retention time: 1.93 minutes (LC-MS method 4). $^1H$ NMR (400 MHz, $CD_3OD$) δ 7.82-7.76 (m, 1H), 7.71 (dd, J=6.4, 2.4 Hz, 1H), 7.32-7.25 (m, 2H), 7.20-7.12 (m, 2H), 7.04 (s, 1H), 7.02-6.97 (m, 2H), 6.58 (d, J=3.2 Hz, 1H), 3.84-3.65 (m, 5H), 3.30-3.20 (m, 2H), 2.98-2.91 (m, 3H), 2.64-2.55 (m, 2H), 2.28-2.21 (m, 1H), 1.90-1.83 (m, 1H), 1.68 (s, 3H), 1.58-1.51 (m, 1H), 1.43-1.39 (m, 2H), 1.20-1.00 (m, 10H) ppm.

Example 243. Compound 243A and Compound 243B. Diastereomers 1 and 2 of (6R)-22-fluoro-3,6,10,10-tetramethyl-6-[3-(2-methylsulfonylethyl)phenyl]-12λ6,24λ4-dithia-3,4,19,28,30-pentazapentacyclo[23.3.1.12,5.015,23.016,20]triaconta-1(29),2(30),4,15,17,20,22,25,27-nonaene 12,12,24-trioxide

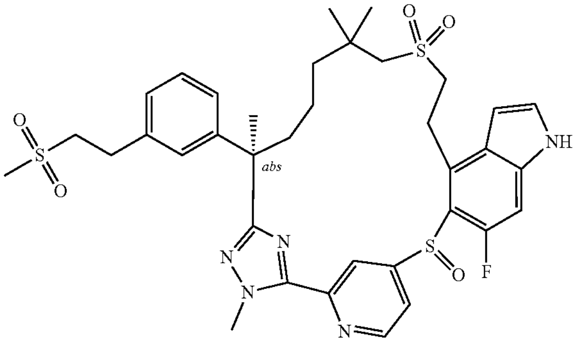 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCS(C)(=O)=O)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-7-((2-hydroxyethyl)sulfonyl)-N',2,6,6-tetramethyl-2-(3-(2-(methylsulfonyl)ethyl)phenyl)heptanehydrazide (Intermediate 137-6, 0.5 g, 1.02 mmol), and methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 0.403 g, 1.02 mmol), the reaction procedure sequence (Steps A to E described for Example 204, followed by Step A described for Example 205, and Step B described for Example 217A and 217B, in this order) was used to prepare the title compounds as a diastereomer mixture. The mixture was separated by reverse phase prep-HPLC. The first eluent (3.7 mg), Diastereomer 1, was designated as Compound 243A. The second eluent (12 mg), Diastereomer 2, was designated as Compound 243B.

Compound 243A: LC-MS: MS (ESI): 740 m/z $[M+H]^+$, purity: 98% (214 nm), retention time: 1.90 minutes (LC-MS method 4). $^1H$ NMR (500 MHz, $CD_3OD$) δ 9.35-8.30 (m, 3H), 7.40 (d, J=3.2 Hz, 1H), 7.29-7.05 (m, 5H), 6.65 (s, 1H), 4.27 (s, 3H), 3.72-3.50 (m, 2H), 3.45-3.33 (m, 3H), 3.28-3.13 (m, 2H), 3.12-3.00 (m, 3H), 2.86 (s, 3H), 2.20-1.94 (m, 2H), 1.74 (s, 3H), 1.56-1.42 (m, 2H), 1.37-1.21 (m, 2H), 1.19-0.87 (m, 6H) ppm.

Compound 243B: LC-MS: MS (ESI): 740 m/z $[M+H]^+$, purity: >99% (214 nm), retention time: 1.90 minutes (LC-MS method 4). $^1H$ NMR (500 MHz, DMSO-$d_6$) δ 8.79-8.71 (m, 1H), 8.04 (bs, 1H), 7.53 (s, 1H), 7.42 (s, 1H), 7.27-7.00 (m, 5H), 6.44 (s, 1H), 4.25 (s, 3H), 3.62-3.37 (m, 5H), 3.25-3.09 (m, 2H), 3.03-2.91 (m, 6H), 2.77 (s, 1H), 2.46-2.34 (m, 1H), 1.72 (s, 3H), 1.66-1.59 (m, 1H), 1.51-1.37 (m, 3H), 1.31-1.21 (m, 3H), 1.10 (s, 3H) ppm.

Example 244. Compound 244. (2S)-3-[3-[(6R)-22-fluoro-3,6,10,10-tetramethyl-12,12-dioxo-24-oxa-12λ6-thia-3,4,19,27,30-pentazapentacyclo[23.3.1.12,5.015,23.016,20]triaconta-1(29),2(30),4,15(23),16(20),17,21,25,27-nonaen-6-yl]phenyl]-2-methyl-propanoic Acid

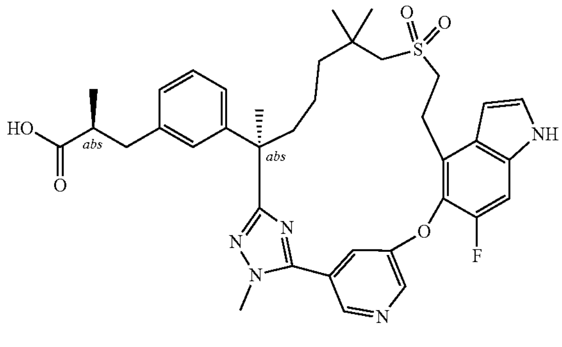 [SMILES: C[C@@H](Cc1cccc([C@@]2(C)CCCC(C)(C)CS(=O)(=O)CCc3c(c(F)cc4[nH]ccc34)Oc3cncc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 2.14 g, 4.42 mmol), and methyl 5-((4-bromo-6-fluoro-1H-indol-5-yl)oxy)-2-fluorobenzimidothioate hydroiodide (Intermediate 14-1) with methyl 5-((4-bromo-6-fluoro-1H-indol-5-yl)oxy)pyridine-3-carbimidothioate (Intermediate 150-4, 2.1 g (53% purity), 2.93 mmol), the reaction procedure sequence (Steps A to D, and Step F) described for Example 6 was used to prepare the title compound (237.5 mg) as a white solid. LC-MS: MS (ESI): 688 m/z $[M+H]^+$, purity: >99% (214 nm). retention time: 1.81 minutes (LC-MS method 27). $^1H$ NMR (400 MHz, $CD_3OD$) δ 8.70 (d, J=1.4 Hz, 1H), 8.62 (d, J=2.8 Hz, 1H), 7.72 (s, 1H), 7.32 (d, J=3.2 Hz, 1H), 7.24 (d, J=10.7 Hz, 1H), 7.13 (t, J=7.6 Hz, 1H), 7.04-6.95 (m, 3H), 6.66 (d, J=3.2 Hz, 1H), 4.03 (s, 3H), 3.44-3.39 (m, 2H), 3.24-3.13 (m, 2H), 2.92-2.86 (m, 1H), 2.77 (d, J=13.7 Hz, 1H), 2.66-2.54 (m, 3H), 2.13-2.05 (m, 1H), 1.85-1.77 (m, 1H), 1.64 (s, 3H), 1.51-1.41 (m, 1H), 1.28-1.18 (m, 1H), 1.14-0.86 (m, 11H) ppm.

Example 245. Compound 245. (2S)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

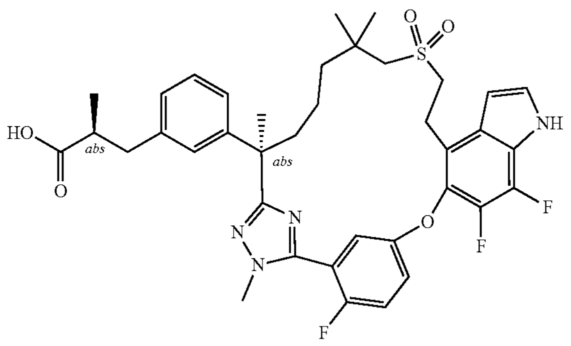 [SMILES: C[C@@H](Cc1cccc([C@@]2(C)CCCC(C)(C)CS(=O)(=O)CCc3c(c(F)c(F)c4[nH]ccc34)Oc3ccc(F)c(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 0.60 g, 1.24 mmol), and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)oxy)-2-fluorobenzimidothioate hydroiodide (Intermediate 14-2, 670 mg, 1.23 mmol), the reaction procedure sequence (Steps A to D, and Step F) described for Example 6 was used to prepare the title compound (71 mg) as a white solid. LC-MS: MS (ESI): 723 m/z $[M+H]^+$, purity: 99% (214 nm). retention time: 1.93 minutes (LC-MS method 4). $^1H$ NMR (500 MHz, $CD_3OD$) δ 7.37-7.34 (m, 3H), 7.23-7.20 (m, 1H), 7.14 (t, J=8.0 Hz, 1H), 7.03-6.96 (m, 3H), 6.68 (d, J=3.0 Hz, 1H), 3.85 (s, 3H), 3.39-3.27 (m, 2H), 3.24-3.22 (m, 1H), 3.20-3.14 (m, 1H), 2.98 (d, J=14.0 Hz, 1H), 2.94-2.85 (m, 1H), 2.81 (d, J=14.0 Hz, 1H), 2.65-2.53 (m, 2H), 2.19-2.10 (m, 1H), 1.86-1.79 (m, 1H), 1.67 (s, 3H), 1.64-1.51 (m, 1H), 1.4-1.28 (m, 1H), 1.26-1.15 (m, 1H), 1.09-0.96 (m, 10H) ppm.

Example 246. Compound 246A & Compound 246B. (2R)-3-[5-[(6R)-22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]-2-thienyl]-2-methyl-propanoic Acid

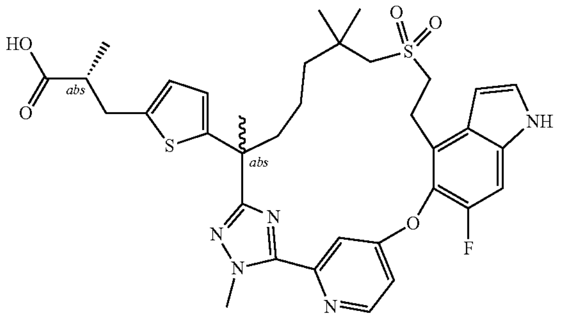 [SMILES: C[C@H](Cc1ccc(C2(C)CCCC(C)(C)CS(=O)(=O)CCc3c(c(F)cc4[nH]ccc34)Oc3ccnc(c3)-c3nc2nn3C)s1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2R)-3-(5-(7-((2-hydroxyethyl)sulfonyl)-2,6,6-trimethyl-1-(2-methylhydrazineyl)-1-oxoheptan-2-yl)thiophen-2-yl)-2-methylpropanoate (Intermediate 69-27, 550 mg, 1.12 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate hydroiodide (Intermediate 133, 683 mg, 1.35 mmol), the reaction procedure sequence (Steps A to F) described for Example 6 was used to prepare the title compounds. The two diastereomer mixture (250 mg) from corresponding Step D was separated to two diastereomeric esters in Step E by chiral reverse phase HPLC. The first eluent (87 mg), Diastereomer 1, was further hydrolyzed to 246A (51 mg, 0.071 mmol). The second eluent (87 mg), Diastereomer 2, was further hydrolyzed to 246B (50 mg, 0.071 mmol) as a white solid.

Compound 246A: LC-MS: MS (ESI): 694 m/z $[M+H]^+$, purity: 99% (214 nm). retention time: 1.58 minutes (LC-MS method 30). $^1H$ NMR (400 MHz, $CD_3OD$) δ 8.64 (d, J=5.6 Hz, 1H), 7.63 (s, 1H), 7.36 (d, J=3.2 Hz, 1H), 7.31 (d, J=10.8 Hz, 1H), 1H), 7.25-7.23 (m, 1H), 6.70 (d, J=3.2 Hz, 1H), 6.55 (d, J=3.2 Hz, 1H), 6.48 (d, J=3.2 Hz, 1H), 4.33 (s, 3H), 3.45-3.40 (m, 2H), 3.17-3.02 (m, 3H), 2.80-2.74 (m, 1H), 2.65-2.55 (m, 2H), 2.49 (d, J=13.6 Hz, 1H), 2.11-2.06 (m, 1H), 1.82-1.74 (m, 1H), 1.67 (s, 3H), 1.38-1.33 (m, 1H), 1.19-1.13 (m, 1H), 1.13 (d, J=7.2 Hz, 3H), 1.00-0.89 (m, 8H) ppm.

Compound 246B: LC-MS: MS (ESI): 694 m/z $[M+H]^+$, purity: 99% (214 nm). retention time: 1.58 minutes (LC-MS method 30). $^1H$ NMR (400 MHz, methanol-d4) δ 8.64 (d, J=5.6 Hz, 1H), 7.63 (s, 1H), 7.35 (d, J=3.2 Hz, 1H), 7.31 (d, J=10.4 Hz, 1H), 1H), 7.25-7.23 (m, 1H), 6.70 (d, J=3.2 Hz, 1H), 6.55 (d, J=3.2 Hz, 1H), 6.48 (d, J=3.2 Hz, 1H), 4.33 (s, 3H), 3.45-3.40 (m, 2H), 3.17-3.02 (m, 3H), 2.80-2.74 (m, 1H), 2.62-2.56 (m, 2H), 2.49 (d, J=13.6 Hz, 1H), 2.12-2.05 (m, 1H), 1.81-1.74 (m, 1H), 1.67 (s, 3H), 1.38-1.32 (m, 1H), 1.19-1.13 (m, 1H), 1.13 (d, J=7.2 Hz, 3H), 1.00-0.85 (m, 8H) ppm.

Example 247. Compound 247. 2-[3-[(6R)-22-fluoro-3,6,10,10-tetramethyl-12,12,24-trioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]acetic Acid

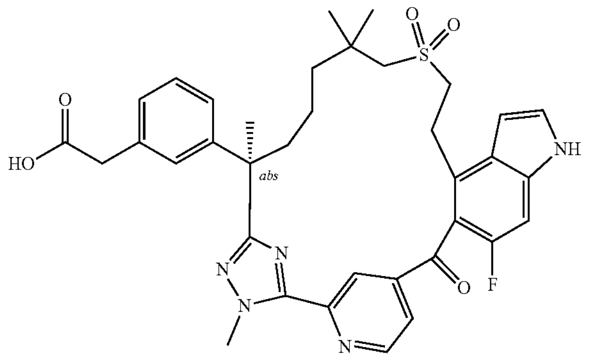 [SMILES: Cn1nc2nc1-c1cc(ccn1)C(=O)c1c(F)cc3[nH]ccc3c1CCS(=O)(=O)CC(C)(C)CCC[C@]2(C)c1cccc(CC(=O)O)c1]

Ethyl 2-[3-[(6R)-24-acetoxy-22-fluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]Acetate

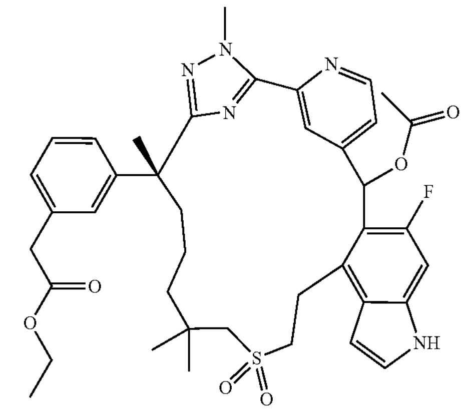 [SMILES: CCOC(=O)Cc1cccc([C@@]2(C)CCCC(C)(C)CS(=O)(=O)CCc3c(c(F)cc4[nH]ccc34)C(OC(C)=O)c3ccnc(c3)-c3nc2nn3C)c1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with ethyl (R)-2-(3-(7-((2-((tert-butyldiphenylsilyl)oxy)ethyl)sulfonyl)-2,6,6-trimethyl-1-(2-methylhydrazineyl)-1-oxoheptan-2-yl)phenyl)acetate (Intermediate 137-2, 0.64 g, 1.46 mmol), and methyl 5-((4-bromo-6-fluoro-1H-indol-5-yl)oxy)-2-fluorobenzimidothioate hydroiodide (Intermediate 14-1) with (4-bromo-6-fluoro-1H-indol-5-yl)(2-(imino(methylthio)methyl)pyridin-4-yl)methyl acetate (Intermediate 150-5, 1.30 g, 1.83 mmol), the reaction procedure sequence (Step A described for Example 6, followed by Step C of Example 192, then Step B, C, D described for Example 6) was used to prepare the title compound (380 mg) as a yellow solid. LC-MS: MS (ESI): 744 m/z $[M+H]^+$, purity: 34+58% (214 nm). retention time: 2.00+2.03 minutes (LC-MS method 4).

Ethyl 2-[3-[(6R)-22-fluoro-24-hydroxy-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]Acetate

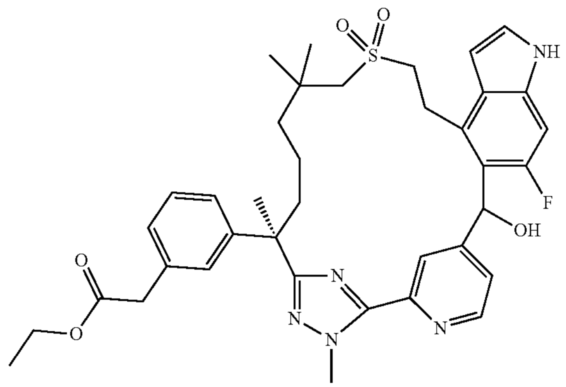 [SMILES: CCOC(=O)Cc1cccc([C@@]2(C)CCCC(C)(C)CS(=O)(=O)CCc3c(c(F)cc4[nH]ccc34)C(O)c3ccnc(c3)-c3nc2nn3C)c1]

Step B: To a stirred solution of Step A product (381 mg, 0.51 mmol) in methanol (20 mL) was added potassium carbonate (142 mg, 1.02 mmol). The reaction mixture was stirred at room temperature for 2 hours, quenched with water (50 mL), and extracted with ethyl acetate (2×40 mL). The solution was washed with brine, dried over sodium sulfate, filtered, and concentrated. The residue was purified by automated flash chromatography (40 g silica gel column, eluting with 0-60% acetone in petroleum ether) to give the title compound (300 mg, 83%) as a solid. LC-MS: MS (ESI): 702 m/z $[M+H]^+$, purity: 37+53% (214 nm). retention time: 1.95+2.00 minutes (LC-MS method 4).

Ethyl 2-[3-[(6R)-22-fluoro-3,6,10,10-tetramethyl-12,12,24-trioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]acetate

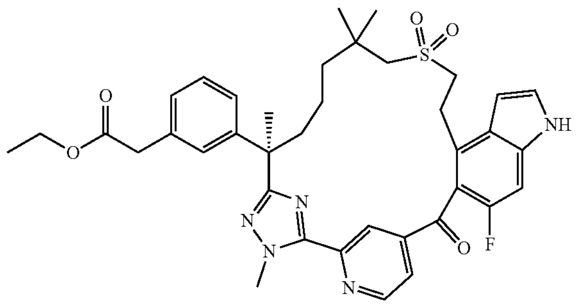 [SMILES: CCOC(=O)Cc1cccc([C@@]2(C)CCCC(C)(C)CS(=O)(=O)CCc3c(c(F)cc4[nH]ccc34)C(=O)c3ccnc(c3)-c3nc2nn3C)c1]

Step C: To a stirred solution of Step B product (300 mg, 0.43 mmol) was added 1-hydroxy-1,2-benziodoxol-3(1h)-one 1-oxide (359 mg, 1.28 mmol) in dimethyl sulfoxide (6 mL) and dichloromethane (6 mL) at 0° C. The mixture was stirred at 0° C. for 3 hours and diluted with ethyl acetate (50 mL). The solution was washed with saturated sodium bicarbonate (30 mL), brine (20 mL), dried over sodium sulfate, filtered, and concentrated. The residue was purified by automated flash chromatography (25 g silica gel column, eluting with 0-60% ethyl acetate in petroleum ether) to give the title compound (0.21 g, 70%) as a solid. LC-MS: MS (ESI): 700 m/z $[M+H]^+$, purity: 85% (214 nm). retention time: 2.00 minutes (LC-MS method 17).

2-[3-[(6R)-22-Fluoro-3,6,10,10-tetramethyl-12,12,24-trioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]acetic Acid

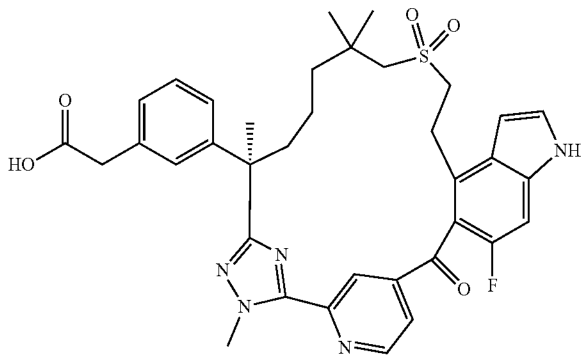 [SMILES: Cn1nc2nc1-c1cc(ccn1)C(=O)c1c(F)cc3[nH]ccc3c1CCS(=O)(=O)CC(C)(C)CCC[C@]2(C)c1cccc(CC(=O)O)c1]

Step D: To a stirred solution of Step C product (210 mg, 0.30 mmol) in tetrahydrofuran (6 mL) and water (2 mL) was added lithium hydroxide monohydrate (63 mg, 1.50 mmol). The reaction was stirred at room temperature overnight, then acidified with 1N hydrochloric acid to pH ~4, and diluted with ethyl acetate (20 mL). The solution was washed with brine (2×10 mL), dried over sodium sulphate, filtered, and concentrated. The residue was purified by reverse phase prep-HPLC to give the title compound (151 mg, 75%) as a solid. LC-MS: MS (ESI): 672 m/z $[M+H]^+$, purity: >99% (214 nm). retention time: 2.16 minutes (LC-MS method 27). $^1$H NMR (500 MHz, $CD_3OD$) δ 8.96 (d, J=5.0 Hz, 1H), 8.35 (s, 1H), 7.92 (d, J=5.0 Hz, 1H), 7.38 (d, J=3.0 Hz, 1H), 7.20-7.13 (m, 2H), 7.11 (s, 1H), 7.07 (d, J=8.0 Hz, 1H), 7.01 (d, J=8.0 Hz, 1H), 6.79 (d, J=3.0 Hz, 1H), 4.34 (s, 3H), 3.70-3.57 (m, 2H), 3.53-3.42 (m, 2H), 3.25-3.16 (m, 1H), 3.15-3.04 (m, 1H), 2.49 (d, J=14.0 Hz, 1H), 2.27 (d, J=14.0 Hz, 1H), 2.11-2.00 (m, 1H), 1.79-1.70 (m, 1H), 1.66 (s, 3H), 1.44-1.31 (m, 1H), 1.15-0.96 (m, 2H), 0.95-0.91 (m, 1H), 0.88 (s, 6H) ppm.

Example 248. Compound 248A & Compound 248B. (2S)-3-[3-[(6R)-22,28-difluoro-6,10,10-trimethyl-12,12,24-trioxo-3-oxa-12λ6,24λ4-dithia-19,30-diazapentacyclo[23.3.1.12,5.015,23.016,20]triaconta-1(29),2(30),4,15,17,20,22,25,27-nonaen-6-yl]phenyl]-2-methyl-propanoic Acid

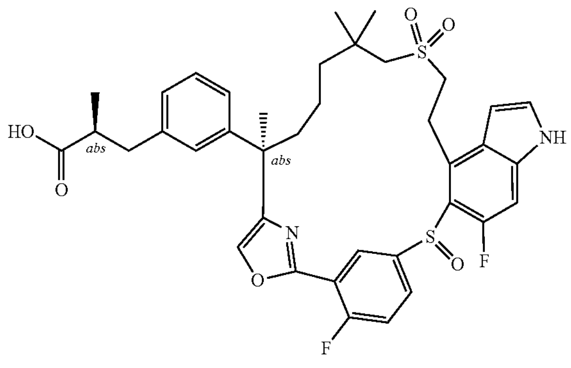 [SMILES: C[C@@H](Cc1cccc([C@@]2(C)CCCC(C)(C)CS(=O)(=O)CCc3c(c(F)cc4[nH]ccc34)S(=O)c3ccc(F)c(c3)-c3nc2co3)c1)C(=O)O]

Exchanging (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoic acid (Intermediate 137H-1) with 5-((4-bromo-6-fluoro-1H-indol-5-yl)thio)-2-fluorobenzoic acid (Intermediate 133A-3, 1.05 g, 2.72 mmol), and 2-bromo-1-(5-((4-bromo-6-fluoro-1-(phenylsulfonyl)-1H-indol-5-yl)oxy)-2-fluorophenyl)ethan-1-one (Intermediate 140) with (S)-3-(3-((R)-1-bromo-8-((2-((tert-butyldiphenylsilyl)oxy)ethyl)sulfonyl)-3,7,7-trimethyl-2-oxooctan-3-yl)phenyl)-2-methylpropanoate (Intermediate 17-17, 2.10 g, 2.72 mmol), the reaction procedure sequence (Steps A to C described for Example 192, followed by steps B to E described for Example 204, then Step A described for Example 205, and Step G and H described for Example 204) was used to prepare the title compounds. The two diastereomeric mixture generated from corresponding Step A of Example 205 was separated at corresponding Step G of Example 204 by reverse phase chiral prep-HPLC. The first eluent (28 mg), Diastereomer 1, was further hydrolyzed to Compound 248A (22 mg, 86%); The second eluent (12 mg), Diastereomer 2, was further hydrolyzed to Compound 248B (7.8 mg, 64%) following the procedure (Step H) described for Example 204.

Compound 248A: LC-MS: MS (ESI): 723 m/z $[M+H]^+$, purity: 99% (214 nm). retention time: 2.03 minutes (LC-MS method 4). $^1$H NMR (400 MHz, DMSO-$d_6$) δ 12.13 (brs, 1H), 11.66 (s, 1H), 8.59 (brs, 1H), 8.22 (s, 1H), 7.56-7.50 (m, 2H), 7.47-7.43 (m, 2H), 7.18-7.14 (m, 2H), 7.03-6.98 (m, 2H), 6.50 (s, 1H), 3.46-3.43 (m, 3H), 3.06 (d, J=14.0 Hz, 1H), 2.97 (d, J=14.0 Hz, 1H), 2.90-2.83 (m, 2H), 2.58-2.55 (m, 2H), 2.33-2.22 (m, 1H), 1.75-1.70 (m, 1H), 1.58 (s, 3H), 1.44-1.38 (m, 3H), 1.23-1.19 (m, 1H), 1.18 (s, 3H), 1.05 (s, 3H), 1.04-0.99 (m, 3H) ppm.

Compound 248B: LC-MS: MS (ESI): 723 m/z $[M+H]^+$, purity: 99% (214 nm). retention time: 2.03 minutes (LC-MS method 4). $^1$H NMR (400 MHz, $CD_3OD$). δ 8.55 (s, 1H), 7.82-7.63 (m, 2H), 7.45 (t, J=5.2 Hz, 1H), 7.38 (d, J=3.2 Hz, 1H), 7.25-7.13 (m, 4H), 7.06 (d, J=7.2 Hz, 1H), 6.64 (d, J=2.4 Hz, 1H), 3.84-3.71 (m, 1H), 3.53-3.45 (m, 2H), 3.13-2.93 (m, 4H), 2.70-2.65 (m, 2H), 2.13-1.96 (m, 2H), 1.68-1.60 (m, 4H), 1.47-1.41 (m, 2H), 1.36-1.25 (m, 1H), 1.18 (s, 3H), 1.12-1.10 (m, 6H) ppm.

Example 249. Compound 249A, Compound 249B. Diastereomers 1 and 2 of 2-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]acetic Acid

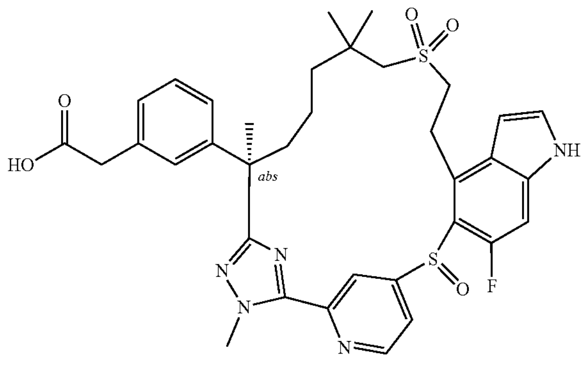 [SMILES: Cn1nc2nc1-c1cc(ccn1)S(=O)c1c(F)cc3[nH]ccc3c1CCS(=O)(=O)CC(C)(C)CCC[C@]2(C)c1cccc(CC(=O)O)c1]

Diastereomer 1 and 2 of methyl 2-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]Acetate

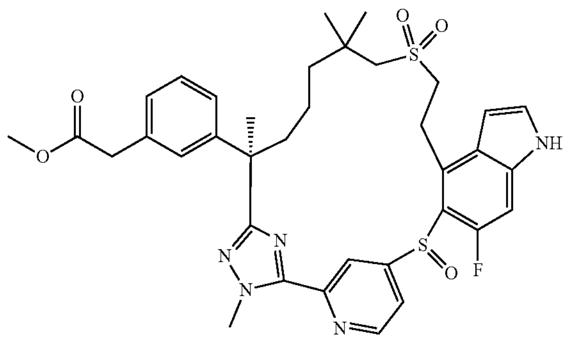 [SMILES: COC(=O)Cc1cccc([C@@]2(C)CCCC(C)(C)CS(=O)(=O)CCc3c(c(F)cc4[nH]ccc34)S(=O)c3ccnc(c3)-c3nc2nn3C)c1]

Step A: Exchanging methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 1.19 g, 3.0 mmol), and methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with ethyl (R)-2-(3-(7-((2-((tert-butyldiphenylsilyl)oxy)ethyl)sulfonyl)-2,6,6-trimethyl-1-(2-methylhydrazineyl)-1-oxoheptan-2-yl)phenyl)acetate (Intermediate 137-2, 1.77 g, 2.50 mmol), the reaction procedure sequence (Steps A described for Example 204, followed by Step B for Example 192, then Step B to E for Example 204, and Step A for Example 205, and Step G for Example 204, in this order) was used to prepare the title compounds. A diastereomer mixture was separated by automated silica gel column chromatograph at corresponding Step A of Example 205. The first eluent (110 mg), Diastereomer 1, was subject to corresponding Step G described for Example 204 to afford Diastereomer 1 (60 mg) of the title compound; The second eluent (34 mg), Diastereomer 2, was subject to corresponding Step G described for Example 204 to afford Diastereomer 2 (22 mg) of the title compound.

Diastereomer 1 of the title compound: LC-MS: MS (ESI): 706 m/z $[M+H]^+$, purity: 99% (214 nm). retention time: 2.03 minutes (LC-MS method 4).

Diastereomer 2: LC-MS: MS (ESI): 706 m/z $[M+H]^+$, purity: >99% (214 nm). retention time: 2.03 minutes (LC-MS method 4).

Diastereomer 1 of 2-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]acetic Acid

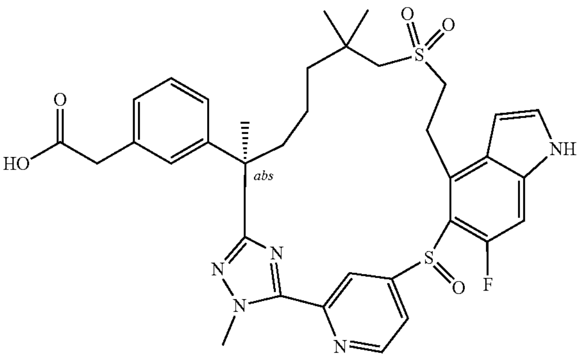 [SMILES: Cn1nc2nc1-c1cc(ccn1)S(=O)c1c(F)cc3[nH]ccc3c1CCS(=O)(=O)CC(C)(C)CCC[C@]2(C)c1cccc(CC(=O)O)c1]

Step B: Exchanging Diastereomer 2 of Methyl (2S)-3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step G product of Example 204) with Diastereomer 1 of Step A product (30 mg), the reaction procedure sequence (Step H described for Example 204) was used to prepare the title compound (16 mg) as a white solid. LC-MS: MS (ESI): 692 m/z $[M+H]^+$, purity: >99% (214 nm). retention time: 1.93 minutes (LC-MS method 4). $^1$H NMR (400 MHz, DMSO-d6) δ 11.71 (s, 1H), 9.00-8.70 (m, 2H), 7.53 (s, 1H), 7.46-7.42 (m, 1H), 7.20-7.06 (m, 6H), 6.50 (s, 1H), 4.25-4.20 (m, 3H), 3.53-3.48 (m, 2H), 3.16-2.99 (m, 4H), 2.82-2.73 (m, 1H), 2.44-2.33 (m, 1H), 1.72-1.60 (m, 5H), 1.47-1.42 (m, 4H), 1.27 (s, 3H), 1.10 (s, 3H) ppm.

Diastereomer 2 of 2-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]acetic acid

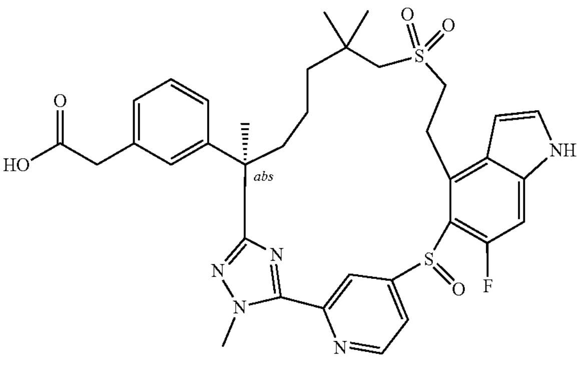 [SMILES: Cn1nc2nc1-c1cc(ccn1)S(=O)c1c(F)cc3[nH]ccc3c1CCS(=O)(=O)CC(C)(C)CCC[C@]2(C)c1cccc(CC(=O)O)c1]

Step C: Exchanging Diastereomer 2 of methyl (2S)-3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step G product of Example 204) with Diastereomer 2 of Step A product (22 mg), the reaction procedure sequence (Steps H described for Example 204) was used to prepare the title compound (8.4 mg) as a white solid. LC-MS: MS (ESI): 692 m/z $[M+H]^+$, purity: >99% (214 nm). retention time: 1.52 minutes (LC-MS method 27). $^1H$ NMR (400 MHz, DMSO-$d_6$). δ 11.68 (s, 1H), 8.99-8.74 (m, 2H), 8.20-8.11 (m, 1H), 7.52 (s, 1H), 7.24-6.97 (m, 6H), 6.67-6.50 (m, 1H), 4.29-4.14 (m, 4H), 3.50 (s, 3H), 3.14 (d, J=14 Hz, 2H), 3.02-2.90 (m, 1H), 2.44-2.38 (m, 1H), 1.72-1.60 (m, 5H), 1.30-1.20 (m, 3H), 1.23 (s, 3H), 1.06-1.00 (m, 4H) ppm.

Example 250. Compound 250. Diastereomer 1 of 2-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]ethanol

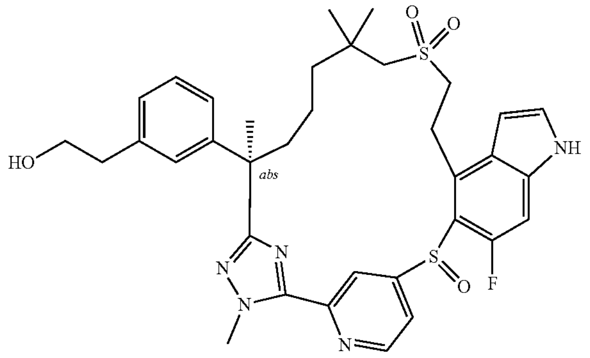 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCO)c1]

To a stirred solution of methyl 2-(3-((13R,Z)-$4^6$-fluoro-$1^1$,9,9,13-tetramethyl-3,7,7-trioxido-$1^1$H,$4^1$H-3,7-dithia-4(5,4)-indola-2(2,4)-pyridina-1(5,3)-triazolacyclotridecaphane-13-yl)phenyl)acetate (Diastereomer 1 of step A product of Example 249A, 249B) (22 mg, 0.032 mmol) in tetrahydrofuran (3 mL) was added lithium borohydride (3.5 mg, 0.16 mmol). The mixture was stirred at room temperature for 48 hours, then quenched with water (3 mL), and extracted with ethyl acetate (2×6 mL). The combined organic extracts were washed with water (5 mL), brine (5 mL), dried over sodium sulfate, filtered, and concentrated. The residue was purified by Prep HPLC to give the title compound (14 mg, 64%) as a white solid. LC-MS: MS (ESI): 678 m/z $[M+H]^+$, purity: 98% (214 nm). Retention time: 1.40 minutes (LC-MS method 4).

$^1H$ NMR (400 MHz, DMSO-$d_6$) δ 11.71 (s, 1H), 8.74 (m, 2H), 7.55-7.51 (m, 1H), 7.45-7.40 (m, 1H), 7.23 (s, 1H), 7.16-7.00 (m, 4H), 6.44 (s, 1H), 4.61-4.57 (m, 1H), 4.25 (s, 3H), 3.57-3.48 (m, 4H), 3.20-3.12 (m, 2H), 3.02-2.99 (m, 1H), 2.67-2.62 (m, 2H), 2.40-2.38 (m, 1H), 1.71-1.61 (m, 4H), 1.51-1.37 (m, 4H), 1.27-1.00 (s, 6H) ppm.

Example 251. Compound 251. 2-[3-[(6R)-22-Fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]acetic Acid

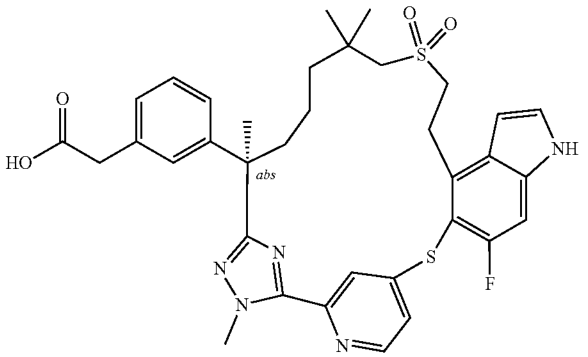 [SMILES: Cn1nc2nc1-c1cc(ccn1)Sc1c(F)cc3[nH]ccc3c1CCS(=O)(=O)CC(C)(C)CCC[C@]2(C)c1cccc(CC(=O)O)c1]

Step A: Exchanging methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 1.19 g, 3.0 mmol), and methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with ethyl (R)-2-(3-(7-((2-((tert-butyldiphenylsilyl)oxy)ethyl)sulfonyl)-2,6,6-trimethyl-1-(2-methylhydrazineyl)-1-oxoheptan-2-yl)phenyl)acetate (Intermediate 137-2, 1.77 g, 2.50 mmol), the reaction procedure sequence (Steps A to E and H described for Example 204) was used to prepare the title compound (8.7 mg). (Notice: only 26 mg out of 250 mg product obtained from corresponding Step D of Example 204 was used for this analogues). LC-MS: MS (ESI): 676 m/z $[M+H]^+$, purity: 98% (214 nm). Retention time: 1.97 minutes (LC-MS method 12). $^1H$ NMR (400 MHz, $CD_3OD$) δ 8.49 (d, J=5.6 Hz, 1H), 7.69 (s, 1H), 7.41 (d, J=5.6 Hz, 1H), 7.38 (d, J=3.6 Hz, 1H), 7.31 (d, J=9.2 Hz, 1H), 7.15 (t, J=7.2 Hz, 1H), 7.13-7.09 (m, 2H), 6.98 (d, J=7.6 Hz, 1H), 6.72 (d, J=3.2 Hz, 1H), 4.27 (s, 3H), 3.76-3.68 (m, 2H), 3.42 (s, 2H), 3.20-3.16 (m, 2H), 2.60-2.55 (m, 2H), 2.06-2.00 (m, 1H), 1.71-1.60 (m, 3H), 1.33-1.30 (m, 1H), 1.21-1.10 (m, 5H), 1.04-1.02 (m, 1H), 0.95-0.90 (m, 4H) ppm.

Example 252. Compound 252. 3-[3-[(6R)-22-Fluoro-3,6,10,10-tetramethyl-12,12-dioxo-24-oxa-12λ6-thia-3,4,19,27,30-pentazapentacyclo[23.3.1.12,5.015,23.016,20]triaconta-1(29),2(30),4,15(23),16(20),17,21,25,27-nonaen-6-yl]phenyl]propanoic Acid

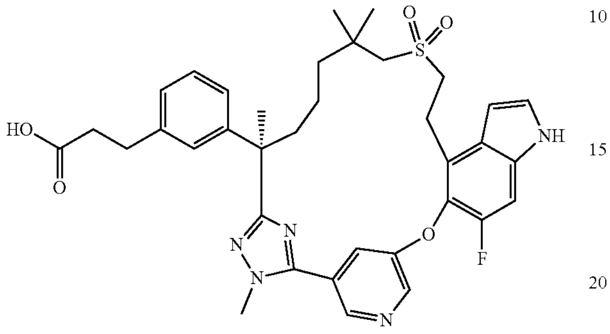

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with ethyl (R)-3-(3-(7-((2-hydroxyethyl)sulfonyl)-2,6,6-trimethyl-1-(2-methylhydrazineyl)-1-oxoheptan-2-yl)phenyl) propanoate (Intermediate 45-20, 1 g, 2 mmol), and methyl 5-((4-bromo-6-fluoro-1H-indol-5-yl)oxy)-2-fluorobenzimidothioate hydroiodide (Intermediate 14-1) with methyl 5-((4-bromo-6-fluoro-1H-indol-5-yl)oxy)pyridine-3-carbimidothioate (Intermediate 150-4, 1 g, 2.72 mmol), the reaction procedure sequence (Steps A to D, and Step F) described for Example 6 was used to prepare the title compound (168 mg) as a white solid. LC-MS: MS (ESI): 674 m/z $[M+H]^+$, purity: >99% (214 nm). retention time: 1.85 minutes (LC-MS method 4). $^1H$ NMR (500 MHz, $CD_3OD$) δ 8.70 (s, 1H), 8.62 (d, J=2.6 Hz, 1H), 7.71 (s, 1H), 7.33 (d, J=3.2 Hz, 1H), 7.25 (d, J=10.7 Hz, 1H), 7.13 (t, J=7.7 Hz, 1H), 7.07 (s, 1H), 7.01-6.98 (m, 2H), 6.66 (d, J=3.2 Hz, 1H), 4.03 (s, 3H), 3.46-3.38 (m, 2H), 3.25-3.15 (m, 2H), 2.83-2.76 (m, 3H), 2.64 (d, J=13.6 Hz, 1H), 2.48 (t, J=7.6 Hz, 2H), 2.14-2.07 (m, 1H), 1.85-1.75 (m, 1H), 1.64 (s, 3H), 1.49-1.41 (m, 1H), 1.28-1.20 (m, 1H), 1.12-1.04 (m, 1H), 1.03-0.97 (m, 6H), 0.94-0.86 (m, 1H) ppm.

Example 253. Compound 253. (2S)-3-[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

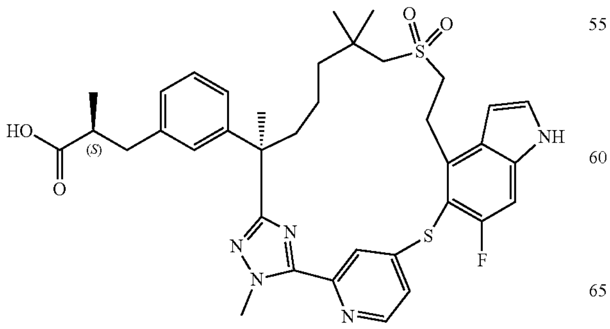

Exchanging methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 19.6 g, 49.52 mmol), the reaction procedure sequence (Steps A to E, and Step H described for Example 204) was used to prepare the title compound (27 mg, white solid). (Note: only 100 mg out of 3.6 g of corresponding Step E product of Example 204 was used). LC-MS: MS (ESI): 704 m/z $[M+H]^+$, purity: >99% (214 nm). retention time: 1.97 minutes (LC-MS method 21). $^1H$ NMR (400 MHz, $CD_3OD$) δ 8.50 (d, J=5.2 Hz, 1H), 7.72-7.64 (m, 1H), 7.42 (dd, J=5.2, 1.6 Hz, 1H), 7.38 (d, J=3.6 Hz, 1H), 7.31-7.28 (m, 1H), 7.11 (t, J=7.6 Hz, 1H), 6.99-6.92 (m, 3H), 6.73 (d, J=3.2 Hz, 1H), 4.27 (s, 3H), 3.78-3.65 (m, 2H), 3.22-3.15 (m, 2H), 2.95-2.88 (m, 1H), 2.64-2.55 (m, 4H), 2.03-1.96 (m, 1H), 1.70-1.64 (m, 4H), 1.35-1.28 (m, 1H), 1.22-1.16 (m, 1H), 1.12-1.02 (m, 7H), 0.97-0.90 (m, 4H) ppm.

Example 254. Compound 254. (2S)-2-Methyl-3-[3-[rac-(6R)-22-fluoro-3,6,10,10-tetramethyl-12,12,24-trioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]propanoic Acid

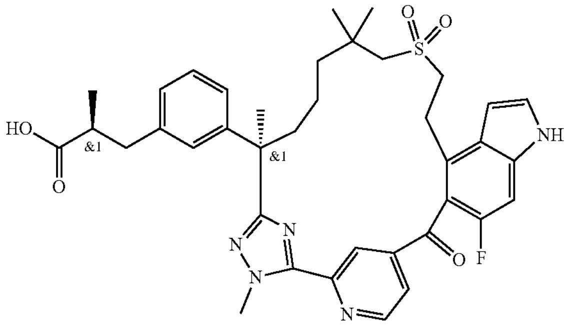 [SMILES: C[C@@H](Cc1cccc([C@@]2(C)CCCC(C)(C)CS(=O)(=O)CCc3c(c(F)cc4[nH]ccc34)C(=O)c3ccnc(c3)-c3nc2nn3C)c1)C(=O)O]

Methyl (2S)-3-[3-[(6R)-24-acetoxy-22-fluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

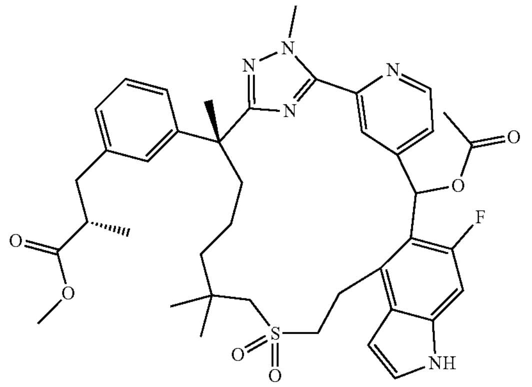 [SMILES: COC(=O)[C@@H](C)Cc1cccc([C@@]2(C)CCCC(C)(C)CS(=O)(=O)CCc3c(c(F)cc4[nH]ccc34)C(OC(C)=O)c3ccnc(c3)-c3nc2nn3C)c1]

Step A: Exchanging methyl (2R)-3-(3-(7-((2-hydroxyethyl)sulfonyl)-2,6,6-trimethyl-1-(2-methylhydrazineyl)-1- oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl) phenyl)-2-methylpropanoate (Intermediate 137-1, 5.40 g, 11.1 mmol), and methyl 5-((4-bromo-6-fluoro-1H-indol-5-yl)oxy)-2-fluorobenzimidothioate hydroiodide (Intermediate 14-1) with (4-bromo-6-fluoro-1H-indol-5-yl)(2-(imino (methylthio)methyl)pyridin-4-yl)methyl acetate (Intermediate 150-5, 6.32 g, 14.5 mmol), the reaction procedure sequence (Step A to D described for Example 6) was used to prepare the title compound (3.3 g) as a yellow solid. LC-MS: MS (ESI): 758 m/z $[M+H]^+$, purity: 42+48% (214 nm). retention time: 1.35+1.37 minutes (LC-MS method 35). Methyl (2S)-3-[3-[(6R)-22-fluoro-24-hydroxy-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

2

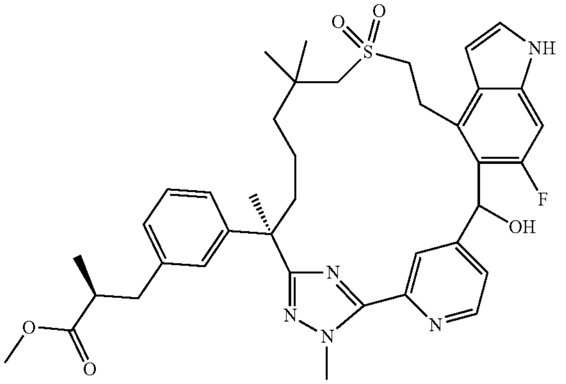 [SMILES: COC(=O)[C@@H](C)Cc1cccc([C@@]2(C)CCCC(C)(C)CS(=O)(=O)CCc3c(c(F)cc4[nH]ccc34)C(O)c3ccnc(c3)-c3nc2nn3C)c1]

Step B: To a stirred solution of Step A product (3.30 g, 4.35 mmol) in methanol (30 mL) was added potassium carbonate (1.20 g, 8.71 mmol). The reaction mixture was stirred at room temperature for 2 hours, quenched with water (50 mL), and extracted with ethyl acetate (2×40 mL). The combined organic extracts were washed with brine, dried over sodium sulfate, filtered, and concentrated. The residue was purified by automated flash chromatography (40 g silica gel column, eluting with 0-60% acetone in petroleum ether) to give the title compound (2.80 g, 90%) as a white solid. LC-MS: MS (ESI): 716 m/z $[M+H]^+$, purity: 46+54% (214 nm). retention time: 1.58+1.60 minutes (LC-MS method 35).

Methyl (2S)-3-[3-[(6R)-22-fluoro-3,6,10,10-tetramethyl-12,12,24-trioxo-12λ6-thia-3,4,19,28,30-pentazapentacyclo[23.3.1.12,5.015,23.016,20]triaconta-1(29),2(30),4,15,17,20,22,25,27-nonaen-6-yl] phenyl]-2-methyl-propanoate

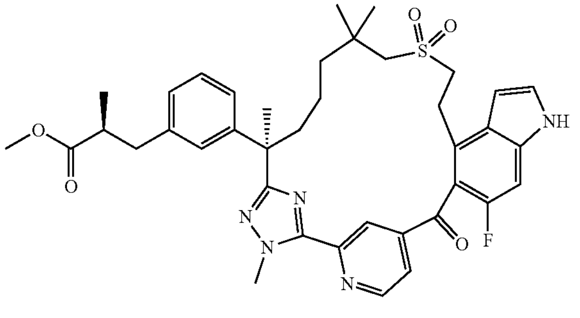 [SMILES: COC(=O)[C@@H](C)Cc1cccc([C@@]2(C)CCCC(C)(C)CS(=O)(=O)CCc3c(c(F)cc4[nH]ccc34)C(=O)c3ccnc(c3)-c3nc2nn3C)c1]

Step C: To a stirred solution of Step B product (2.80 g, 3.91 mmol) was added 1-hydroxy-1,2-benziodoxol-3(1h)-one 1-oxide (3.29 g, 11.7 mmol) in dimethyl sulfoxide (20 mL) and dichloromethane (10 mL) at 0° C. The mixture was stirred at 0° C. for 3 hours, then diluted with ethyl acetate (80 mL). The mixture was washed with saturated sodium bicarbonate, brine, dried over sodium sulfate, filtered, and concentrated. The residue was purified by automated flash chromatography (80 g silica gel column, eluting with 0-60% ethyl acetate in petroleum ether) to give the title compound (1.90 g, 68%) as a white solid. LC-MS: MS (ESI): 714 m/z $[M+H]^+$, purity: >99% (214 nm). retention time: 2.04 minutes (LC-MS method 4).

Compound 254 (2S)-3-[3-[(6R)-22-fluoro-3,6,10,10-tetramethyl-12,12,24-trioxo-12λ6-thia-3,4,19,28,30-pentazapentacyclo[23.3.1.12,5.015,23.016,20] triaconta-1(29),2(30),4,15,17,20,22,25,27-nonaen-6-yl]phenyl]-2-methyl-propanoic Acid

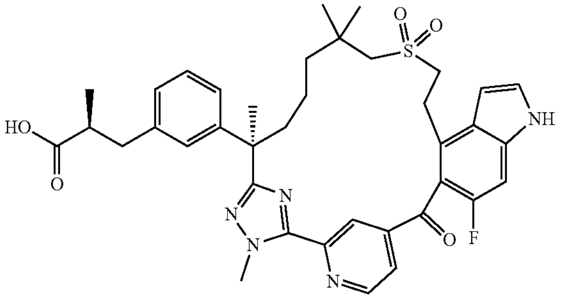 [SMILES: C[C@@H](Cc1cccc([C@@]2(C)CCCC(C)(C)CS(=O)(=O)CCc3c(c(F)cc4[nH]ccc34)C(=O)c3ccnc(c3)-c3nc2nn3C)c1)C(=O)O]

Step D: To a stirred solution of Step C product (1.90 g, 2.66 mmol) in tetrahydrofuran (30 mL) and water (30 mL) was added lithium hydroxide monohydrate (558 mg, 13.3 mmol). The reaction was stirred at room temperature overnight, acidified with 1N hydrochloric acid to pH ~4, and diluted with ethyl acetate (80 mL). The solution was washed with brine, dried over sodium sulphate, filtered, and concentrated. The residue was purified by automated flash chromatography (120 g silica gel column, eluting with 0-60% acetone in petroleum ether) to give the title compound (1.88 g, 98%) as a white solid. LC-MS: MS (ESI): 700 m/z $[M+H]^+$, purity: >99% (214 nm). retention time: 1.96 minutes (LC-MS method 4). $^1H$ NMR (500 MHz, $CD_3OD$) δ 11.06 (s, 1H), 8.96 (d, J=5.0 Hz, 1H), 8.36 (s, 1H), 7.92 (d, J=4.5 Hz, 1H), 7.38 (s, 1H), 7.17 (d, J=11.0 Hz, 1H), 7.15-7.09 (m, 1H), 7.01 (s, 1H), 6.98-6.93 (m, 2H), 6.81-6.78 (m, 1H), 4.34 (s, 3H), 3.70-3.60 (m, 2H), 3.27-3.17 (m, 1H), 3.14-3.04 (m, 1H), 2.96-2.86 (m, 1H), 2.64-2.52 (m, 2H), 2.48 (d, J=14.0 Hz, 1H), 2.31 (d, J=14.0 Hz, 1H), 2.06-1.97 (m, 1H), 1.79-1.69 (m, 1H), 1.66 (s, 3H), 1.44-1.32 (m, 1H), 1.15-1.02 (m, 4H), 1.02-0.91 (m, 2H), 0.91-0.87 (m, 6H) ppm.

Example 255. Compound 255A, Compound 255B. Diastereomer 1 and 2 of (2S)-3-[3-[(6R)-22-fluoro-24-hydroxy-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

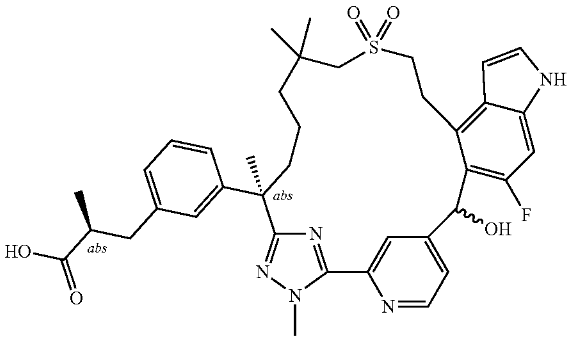 [SMILES: C[C@@H](Cc1cccc([C@@]2(C)CCCC(C)(C)CS(=O)(=O)CCc3c(c(F)cc4[nH]ccc34)C(O)c3ccnc(c3)-c3nc2nn3C)c1)C(=O)O]

To a stirred solution of methyl (2S)-3-[3-[(6R)-22-fluoro-24-hydroxy-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate (Step B product of Example 254, 0.080 g, 0.112 mmol) in tetrahydrofuran (5 mL) and water (5 mL) was added lithium hydroxide monohydrate (23 mg, 0.559 mmol). The reaction was stirred at room temperature overnight, acidified with 1N hydrochloric acid to pH ~4, and diluted with ethyl acetate (20 mL). The solution was washed with brine, dried over sodium sulphate, filtered, and concentrated. The residue was purified by prep-HPLC. The first eluent (11 mg, 14%), Diastereomer 1, was designated as 255A; The second eluent, diastereomer 2 (33 mg, 42%), was designated as 255B, both as white solid.

Compound 255A: LC-MS: MS (ESI): 702 m/z $[M+H]^+$, purity: >99% (214 nm). retention time: 1.40 minutes (LC-MS method 35). $^1$H NMR (500 MHz, $CD_3OD$) δ 8.66 (s, 1H), 8.54 (d, J=5.0 Hz, 1H), 7.26 (d, J=3.5 Hz, 1H), 7.25-7.16 (m, 2H), 7.14 (d, J=11.0 Hz, 1H), 7.07 (s, 1H), 7.05-7.01 (m, 2H), 6.53 (s, 1H), 6.46 (d, J=3.0 Hz, 1H), 4.27 (s, 3H), 3.64-3.50 (m, 1H), 3.47-3.38 (m, 1H), 3.24-3.12 (m, 2H), 3.10-3.03 (m, 1H), 2.99-2.91 (m, 2H), 2.68-2.59 (m, 2H), 2.20-2.08 (m, 1H), 2.01-1.81 (m, 2H), 1.75 (s, 3H), 1.58-1.46 (m, 1H), 1.40-1.30 (m, 1H), 1.25 (s, 3H), 1.16-0.99 (m, 7H) ppm.

Compound 255B: LC-MS: MS (ESI): 702 m/z $[M+H]^+$, purity: >99% (214 nm). retention time: 1.46 minutes (LC-MS method 35). $^1$H NMR (500 MHz, $CD^3OD$) δ 8.66 (s, 1H), 8.54 (d, J=5.0 Hz, 1H), 7.25 (d, J=3.0 Hz, 1H), 7.22-7.15 (m, 2H), 7.14 (d, J=11 Hz, 1H), 7.07 (s, 1H), 7.04-7.02 (m, 2H), 6.53 (s, 1H), 6.43 (d, J=2.5 Hz, 1H), 4.31 (s, 3H), 3.63-3.53 (m, 1H), 3.47-3.38 (m, 1H), 3.22-3.16 (m, 2H), 3.03 (d, J=14.0 Hz, 1H), 2.99-2.92 (m, 2H), 2.67-2.56 (m, 2H), 2.20-2.09 (m, 1H), 2.01-1.90 (m, 1H), 1.75 (s, 3H), 1.53-1.47 (m, 1H), 1.38-1.31 (m, 1H), 1.24 (s, 3H), 1.09-0.98 (m, 6H) ppm.

Example 256. Compound 256. (2S)-3-[3-[(6R)-22-Fluoro-3,6,10,10-tetramethyl-12,12-dioxo-24-oxa-12λ6-thia-3,4,19,27,28,30-hexazapentacyclo[23.3.1.12,5.015,23.016,20]triaconta-1(29),2(30),4,15,17,20,22,25,27-nonaen-6-yl]phenyl]-2-methyl-propanoic Acid

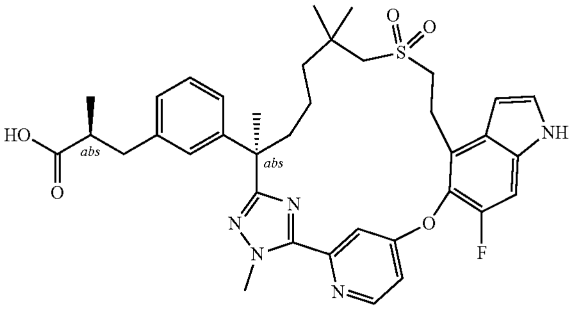 [SMILES: C[C@@H](Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 191 mg, 0.393 mmol), and methyl 5-((4-bromo-6-fluoro-1H-indol-5-yl)oxy)-2-fluorobenzimidothioate hydroiodide (Intermediate 14-1) with methyl 5-((4-bromo-6-fluoro-1H-indol-5-yl)oxy)pyridazine-3-carbimidothioate (Intermediate 150-6, 250 mg, 0.393 mmol), the reaction procedure sequence (Steps A to D and F) described for Example 6 was used to prepare the title compound (19 mg, 0.0265 mmol, 64%) as a white solid. LC-MS: MS (ESI): 689 m/z $[M+H]^+$, purity: 95% (254 nm). retention time: 1.98 minutes (LC-MS method 21). $^1$H NMR (400 MHz, $CD_3OD$) δ 9.30 (d, J=2.8 Hz, 1H), 7.71 (d, J=2.8 Hz, 1H), 7.35 (d, J=2.8 Hz, 1H), 7.29 (d, J=10.8 Hz, 1H), 7.10 (t, J=7.6 Hz, 1H), 7.00 (s, 1H), 6.95 (t, J=7.6 Hz, 2H), 6.73 (d, J=2.8 Hz, 1H), 4.41 (s, 3H), 3.48-3.43 (m, 2H), 3.18-3.15 (m, 2H), 2.92-2.85 (m, 1H), 2.65-2.49 (m, 4H), 2.07-1.99 (m, 1H), 1.80-1.73 (m, 1H), 1.64 (s, 3H), 1.34-1.28 (m, 1H), 1.16-1.11 (m, 1H), 1.08-1.05 (m, 1H), 1.02 (d, J=6.4 Hz, 3H), 0.96 (s, 3H), 0.92-0.90 (m, 1H), 0.89 (s, 3H) ppm.

Example 257. Compound 257. 2-[3-[(6R)-21,22-difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]acetic Acid

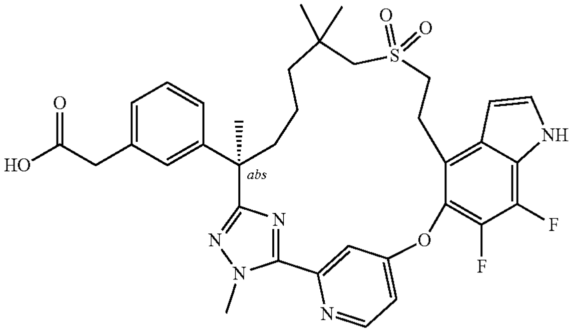 [SMILES: Cn1nc2nc1-c1cc(ccn1)Oc1c(F)c(F)c3[nH]ccc3c1CCS(=O)(=O)CC(C)(C)CCC[C@]2(C)c1cccc(CC(=O)O)c1]

Ethyl (R)-2-(3-(2-(5-(4-((4-bromo-6,7-difluoro-1H-indol-5-yl)oxy)pyridin-2-yl)-1-methyl-1H-1,2,4-triazol-3-yl)-7-((2-((tert-butyldiphenylsilyl)oxy)ethyl)sulfonyl)-6,6-dimethylheptan-2-yl)phenyl)acetate

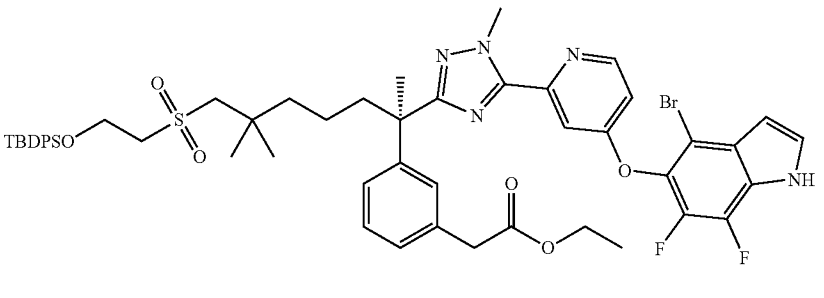

Step A: To a stirred solution of ethyl (R)-2-(3-(7-((2-((tert-butyldiphenylsilyl)oxy)ethyl)sulfonyl)-2,6,6-trimethyl-1-(2-methylhydrazineyl)-1-oxoheptan-2-yl)phenyl) acetate (Intermediate 137-2, 1.05 g, 1.48 mmol) in pyridine (20 mL) was added methyl 4-((4-bromo-6,7-difluoro-1H-indol-5-yl)oxy)pyridine-2-carbimidothioate (Intermediate 150, 0.71 g, 1.78 mmol) and magnesium sulphate (2 g). The reaction was stirred at 80° C. for 16 hours and concentrated. The residue was diluted with water (60 mL) and 1N hydrochloric acid (10 mL), extracted with ethyl acetate (3×60 mL). The combined organic extracts were washed with water, brine, dried over sodium sulfate, filtered, and concentrated to give the crude title compound (1.50 g, 97%) as solid, which was used for the next step without further purification. LC-MS: MS (ESI): 1040, 1042 m/z $[M+H]^+$, purity: 95% (254 nm). retention time: 1.98 minutes (LC-MS method 003).

Ethyl (R)-2-(3-(2-(5-(4-((4-bromo-6,7-difluoro-1H-indol-5-yl)oxy)pyridin-2-yl)-1-methyl-1H-1,2,4-triazol-3-yl)-7-((2-hydroxyethyl)sulfonyl)-6,6-dimethylheptan-2-yl)phenyl)acetate

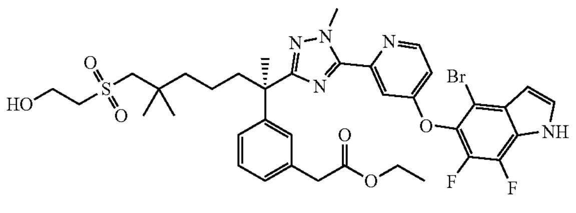 [SMILES: CCOC(=O)Cc1cccc([C@@](C)(CCCC(C)(C)CS(=O)(=O)CCO)c2nc(-c3cc(Oc4c(F)c(F)c5[nH]ccc5c4Br)ccn3)n(C)n2)c1]

Step B: To a stirred solution of Step A product (1.50 g, 1.44 mmol) in tetrahydrofuran (10 mL) was added tetra-n-butylammonium fluoride (7.2 mL, 7.2 mmol). Then the mixture was stirred at room temperature for 2 hours, diluted with water (40 mL), and extracted with ethyl acetate (3×45 mL). The combined organic layers were washed with brine, dried over sodium sulfate, filtered, and concentrated. The residue was purified by automated column chromatography (40 g silica gel column; eluting with 0-65% ethyl acetate in petroleum ether) to give the title compound (550 mg, 32%) as solid. LC-MS: MS (ESI): 802, 804 m/z $[M+H]^+$, purity: 95% (254 nm). retention time: 1.85 minutes (LC-MS method 033).

Ethyl 2-[3-[(6R)-21,22-difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]Acetate

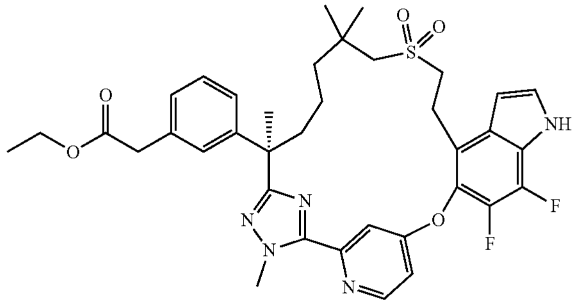 [SMILES: CCOC(=O)Cc1cccc([C@@]2(C)CCCC(C)(C)CS(=O)(=O)CCc3c(c(F)c(F)c4[nH]ccc34)Oc3ccnc(c3)-c3nc2nn3C)c1]

Step C: Exchanging methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 6) with ethyl (R)-2-(3-(2-(5-(4-((4-bromo-6,7-difluoro-1H-indol-5-yl)oxy)pyridin-2-yl)-1-methyl-1H-1,2,4-triazol-3-yl)-7-((2-hydroxyethyl)sulfonyl)-6,6-dimethylheptan-2-yl)phenyl)acetate (Step B product of this example, 0.55 g, 0.68 mmol), the reaction procedure sequence (Steps B to D) described for Example 6 was used to prepare the title compound (180 mg, 89%) as a solid. LC-MS: MS (ESI): 706 m/z $[M+H]^+$, purity: 97% (254 nm). retention time: 2.14 minutes (LC-MS method 027).

Compound 257. 2-[3-[(6R)-21,22-difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]acetic Acid

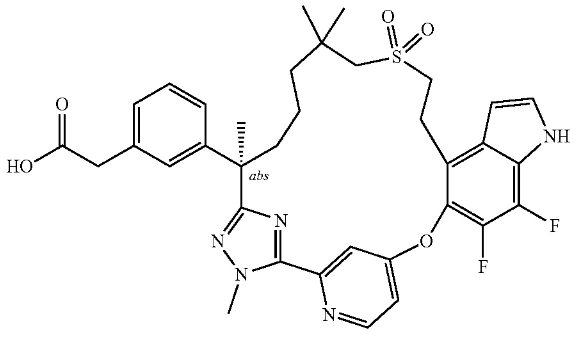 [SMILES: Cn1nc2nc1-c1cc(ccn1)Oc1c(F)c(F)c3[nH]ccc3c1CCS(=O)(=O)CC(C)(C)CCC[C@]2(C)c1cccc(CC(=O)O)c1]

Step D: Exchanging Methyl (2R)-3-[3-(22,28-difluoro-3,6,10,10-tetramethyl-12,12-dioxo-24-oxa-126-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate (Step D product of Example 6) with Ethyl 2-[3-[(6R)-21,22-difluoro-3,6,10,10-tetramethyl-12,12-dioxo-24-oxa-126-thia-3,4,19,28,30-pentazapentacyclo[23.3.1.12,5.015,23.016,20]triaconta-1(29),2(30),4,15,17,20,22,25,27-nonaen-6-yl]phenyl]acetate (Step C product of this example, 78 mg, 0.11 mmol), the reaction procedure (Step F) described for Example 6 was used to prepare the title compound (42 mg, 57%) as white solid. LC-MS: MS (ESI): 678 m/z $[M+H]^+$, purity: 95% (254 nm). retention time: 1.62 minutes (LC-MS method 027). $^1H$ NMR (400 MHz, $CD_3OD$) δ 8.67 (d, J=4.8 Hz, 1H), 7.67 (d, J=1.6 Hz, 1H), 7.41 (d, J=2.4 Hz, 1H), 7.27 (dd, J=4.8, 2.0 Hz, 1H), 7.18-7.15 (m, 1H), 7.12-7.10 (m, 1H), 7.07 (d, J=6.0 Hz, 1H), 7.07 (d, J=6.0 Hz, 1H), 6.76 (t, J=2.4 Hz, 1H), 4.36 (s, 3H), 3.49 (s, 2H), 3.42-3.35 (m, 2H), 3.16-3.07 (m, 2H), 2.66 (d, J=11.2 Hz, 1H), 2.57 (d, J=11.2 Hz, 1H), 2.10-2.06 (m, 1H), 1.84-1.80 (m, 1H), 1.65 (s, 3H), 1.43-1.37 (m, 1H), 1.26-1.20 (m, 1H), 1.10-1.05 (m, 1H), 1.02 (s, 3H), 0.95 (s, 3H), 0.94-0.89 (m, 1H) ppm.

Example 258. Compound 258. 2-[3-[(6R)-21,22-Difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]ethanol

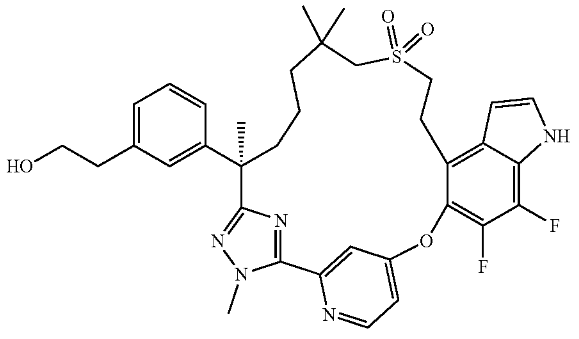 [SMILES: Cn1nc2nc1-c1cc(ccn1)Oc1c(F)c(F)c3[nH]ccc3c1CCS(=O)(=O)CC(C)(C)CCC[C@]2(C)c1cccc(CCO)c1]

To a stirred solution of ethyl 2-[3-[(6R)-21,22-difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]acetate (Step C product of Example 257) (78 mg, 0.11 mmol) in tetrahydrofuran (3 mL) was added lithium borohydride (12 mg, 0.55 mmol). The mixture was stirred at room temperature for 48 hours, quenched with water (6 mL), and extracted with ethyl acetate (2×10 mL). The combined organic layers were washed with water, brine, dried over sodium sulfate, filtered, and concentrated. The residue was purified by Prep HPLC to give the title compound (40 mg, 55%) as white solid. LC-MS: MS (ESI): 664 m/z $[M+H]^+$, purity: >99% (214 nm). retention time: 1.98 minutes (LC-MS method 027). $^1H$ NMR (400 MHz, $CD_3OD$) δ 8.67 (d, J=4.8 Hz, 1H), 7.67 (d, J=2.0 Hz, 1H), 7.41 (d, J=2.8 Hz, 1H), 7.29-7.26 (m, 1H), 7.14 (t, J=6.0 Hz, 1H), 7.02-6.97 (m, 3H), 6.76 (t, J=2.4 Hz, 1H), 4.36 (s, 3H), 3.67 (t, J=5.6 Hz, 2H), 3.42-3.32 (m, 2H), 3.19-3.07 (m, 2H), 2.72 (t, J=5.6 Hz, 2H), 2.66 (d, J=11.2 Hz, 1H), 2.51 (d, J=11.2 Hz, 1H), 2.10-2.05 (m, 1H), 1.84-1.79 (m, 1H), 1.65 (s, 3H), 1.43-1.37 (m, 1H), 1.25-1.19 (m, 1H), 1.10-1.05 (m, 1H), 1.02 (s, 3H), 0.94 (s, 3H), 0.94-0.89 (m, 1H) ppm.

Example 259. Compound 259. (2S)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

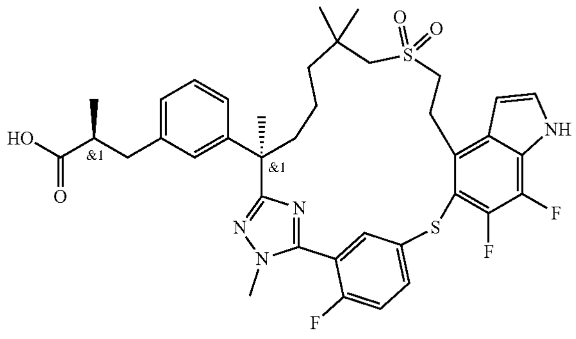 [SMILES: C[C@@H](Cc1cccc([C@@]2(C)CCCC(C)(C)CS(=O)(=O)CCc3c(c(F)c(F)c4[nH]ccc34)Sc3ccc(F)c(c3)-c3nc2nn3C)c1)C(=O)O]

Methyl (2S)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanate

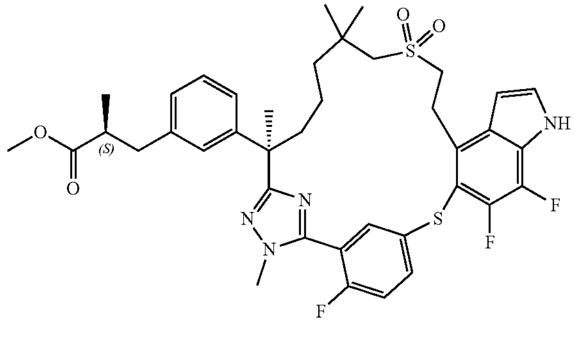

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl) phenyl)-2-methylpropanoate (Intermediate 137-1, 3.20 g, 8.66 mmol), and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)thio)-2-fluorobenzimidothioate (Intermediate 150-7, 2.80 g, 5.01 mmol), the reaction procedure sequence (Steps A to D) described for Example 6 was used to prepare the title compound (2.3 g, 3.32 mmol, 85%) as a white solid. LC-MS: MS (ESI): 753 m/z $[M+H]^+$, purity: 98% (214 nm). retention time: 2.10 minutes (LC-MS method 003).

Compound 259. (2S)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

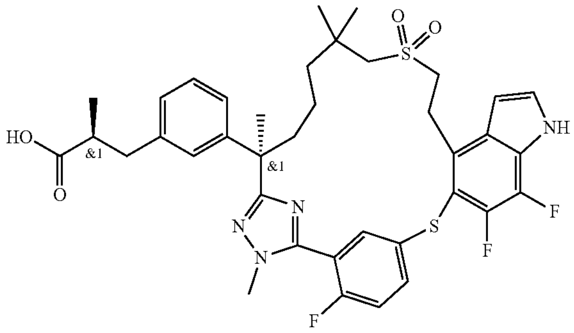 [SMILES: C[C@@H](Cc1cccc([C@@]2(C)CCCC(C)(C)CS(=O)(=O)CCc3c(c(F)c(F)c4[nH]ccc34)Sc3ccc(F)c(c3)-c3nc2nn3C)c1)C(=O)O]

Step B. Exchanging Diastereomer 1 of methyl (2R)-3-[3-(22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]-2-methyl-propanoate (Step E product of Example 6) with methyl (2S)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl] phenyl]propanate (Step A product of this Example, 70 mg, 0.0930 mmol), the reaction procedure (Step F) described for Example 6 was used to prepare the title compound (25 mg, 0.034 mmol, 36%) as white solid. LC-MS: MS (ESI): 739 m/z $[M+H]^+$, purity: >99% (214 nm). retention time: 1.94 minutes (LC-MS method 003). $^1H$ NMR (500 MHz, $CD_3OD$) δ: 7.86-7.80 (m, 1H), 7.77 (dd, J=6.0, 2.0 Hz, 1H), 7.37-7.30 (m, 2H), 7.15 (t, J=7.5 Hz, 1H), 7.04 (s, 1H), 6.99 (d, J=7.5 Hz, 2H), 6.65 (t, J=6.5 Hz, 1H), 3.80-3.60 (m, 5H), 3.28-3.22 (m, 1H), 3.02-2.91 (m, 3H), 2.65-2.55 (m, 2H), 2.29-2.23 (m, 1H), 1.90-1.84 (m, 1H), 1.68 (s, 3H), 1.65-1.32 (m, 3H), 1.31-1.18 (m, 1H), 1.17 (s, 3H), 1.13 (s, 3H), 1.09-1.03 (m, 4H) ppm.

Example 260. Compound 260A and Compound 260B. Diastereomer 1 and 2 of 3-[2-fluoro-3-[(6R)-22-fluoro-3,6,10,10-tetramethyl-12,12,24-trioxo-12λ6,24λ4-dithia-3,4,19,28,30-pentazapentacyclo [23.3.1.12,5.015,23.016,20]triaconta-1(29),2(30),4,15,17,20,22,25,27-nonaen-6-yl]phenyl]propanoic Acid

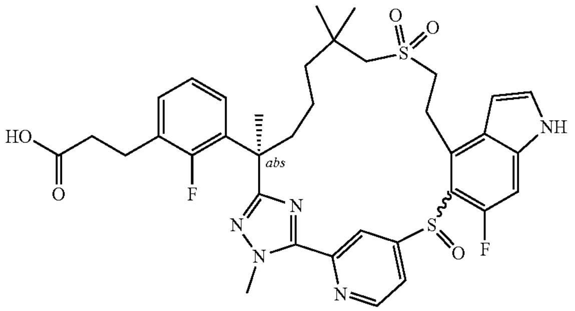 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCC(=O)O)c1F]

Diastereomers 1 and 2 of ethyl 3-[2-fluoro-3-[(6R)-22-fluoro-3,6,10,10-tetramethyl-12,12,24-trioxo-19-(p-tolylsulfonyl)-12λ6,24λ4-dithia-3,4,19,28,30-pentazapentacyclo[23.3.1.12,5.015,23.016,20] triaconta-1(29),2(30),4,15,17,20,22,25,27-nonaen-6-yl]phenyl]propanoate

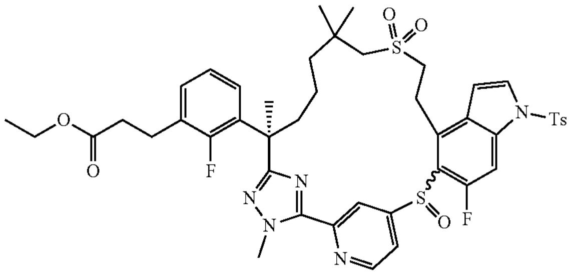 [SMILES: CCOC(=O)CCc1cccc([C@@]2(C)CCCC(C)(C)CS(=O)(=O)CCc3c(c(F)cc4c3ccn4S(=O)(=O)c3ccc(C)cc3)S(=O)c3ccnc(c3)-c3nc2nn3C)c1F]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with ethyl (R)-3-(2-fluoro-3-(7-((2-hydroxyethyl) sulfonyl)-2,6,6-trimethyl-1-(2-methylhydrazineyl)-1-oxo-heptan-2-yl)phenyl)propanoate (Intermediate 137-10, 0.85 g, 1.69 mmol), and methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl) thio)pyridine-2-carbimidothioate (Intermediate 14-15, 737 mg, 1.86 mmol), the reaction procedure sequence (Steps A to F) described for Example 204 was used to prepare the title compounds. In the corresponding Step F, the oxidation of thioether to sulfoxide, two diastereomers were formed and separated by Prep-HPLC. The first eluent was designated as Diastereomer 1 (20 mg, 0.022 mmol) and the second eluent was designated as Diastereomer 2 (18 mg, 0.020 mmol).

Diastereomer 1: LC-MS: MS (ESI): 906 m/z $[M+H]^+$, purity: >99% (214 nm). retention time: 1.48 minutes (LC-MS method 035).

Diastereomer 2: LC-MS: MS (ESI): 906 m/z $[M+H]^+$, purity: >99% (214 nm). retention time: 1.49 minutes (LC-MS method 035).

Diastereomer 1 of ethyl 3-[2-fluoro-3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propanoate

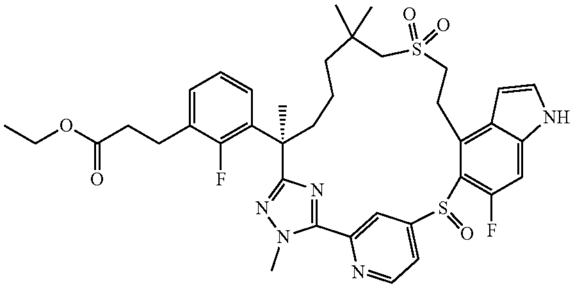 [SMILES: CCOC(=O)CCc1cccc([C@@]2(C)CCCC(C)(C)CS(=O)(=O)CCc3c(c(F)cc4[nH]ccc34)S(=O)c3ccnc(c3)-c3nc2nn3C)c1F]

Step B: To a stirred solution of Diastereomer 1 of Step A product (20 mg, 0.022 mmol) in tetrahydrofuran (1.0 mL) was added tetra-n-butylammonium fluoride (0.50 mL, 0.500 mmol). The reaction was stirred at room temperature for 4 hours, then diluted with ethyl acetate (20 mL). The mixture was washed with water, dried over sodium sulfate, filtered, and concentrated. The residue was purified by automated flash chromatography (4.0 g silica gel column, eluting with 0-75% ethyl acetate in petroleum) to give the title compound (10 mg, 0.013 mmol, 60%) as a light-yellow oil. LC-MS: MS (ESI): 752 m/z $[M+H]^+$, purity: 60% (214 nm). retention time: 1.35 minutes (LC-MS method 035).

Compound 260A. Diastereomer 1 of 3-[2-fluoro-3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propanoic Acid

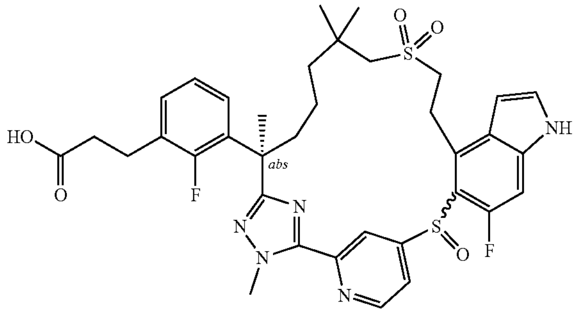 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCC(=O)O)c1F]

Step C: To a stirred solution of Step B product (10 mg, 0.013 mmol) in tetrahydrofuran (0.5 mL) and water (0.5 mL) was added lithium hydroxide monohydrate (20.0 eq, 11 mg, 0.266 mmol). The reaction was stirred at room temperature overnight, then acidified with 1.0 M hydrochloric acid to pH~6, and extracted with ethyl acetate (3×10 mL). The combined organic phases were washed with brine, dried over sodium sulfate, filtered, and concentrated. The residue was purified by Prep-HPLC to afford the title compound (1.7 mg, 0.0024 mmol, 18%) as a white solid. LC-MS: MS (ESI): 724 m/z $[M+H]^+$, purity: >99% (214 nm). retention time: 1.71 minutes (LC-MS method 036). $^1H$ NMR (400 MHz, $CD_3OD$): δ 8.97-8.68 (m, 2H), 7.39 (d, J=3.6 Hz, 1H), 7.31-7.10 (m, 3H), 6.98-6.91 (m, 1H), 6.84-6.79 (m, 1H), 6.68-6.56 (m, 1H), 4.32 (s, 3H), 3.68-3.62 (m, 1H), 3.13-3.03 (m, 3H), 2.89-2.77 (m, 3H), 2.53-2.40 (m, 3H), 1.91-1.86 (m, 1H), 1.79 (s, 3H), 1.60-1.56 (m, 1H), 1.47-1.45 (m, 2H), 1.28-0.97 (m, 8H) ppm.

Compound 260B. Diastereomer 2 of 3-[2-fluoro-3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propanoic acid

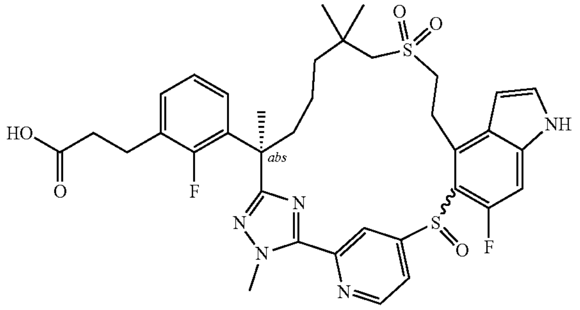 [SMILES: Cn1nc2nc1-c1cc(ccn1)S(=O)c1c(F)cc3[nH]ccc3c1CCS(=O)(=O)CC(C)(C)CCC[C@]2(C)c1cccc(CCC(=O)O)c1F]

Step D: Exchanging Diastereomer 1 with Diastereomer 2 (18, mg, 0.020 mmol) of Step A product, the reaction procedure sequence (Step B and Step C of this Example) was followed to prepare the title compound (4.0 mg, 0.0055 mmol) as a white solid. LC-MS: MS (ESI): 724 m/z $[M+H]^+$, purity: 97% (214 nm). retention time: 1.83 minutes (LC-MS method 003). $^1H$ NMR (400 MHz, $CD_3OD$): δ 8.87-8.72 (m, 2H), 7.39 (d, J=3.2 Hz, 1H), 7.30-7.05 (m, 3H), 6.98 (t, J=7.6 Hz, 1H), 6.86-6.82 (m, 1H), 6.69-6.65 (m, 1H), 4.27 (s, 3H), 3.74-3.59 (m, 2H), 3.16-3.10 (m, 2H), 2.90 (t, J=7.6 Hz, 1H), 2.54 (t, J=7.6 Hz, 1H), 2.09-2.03 (m, 2H), 1.95-1.86 (m, 1H), 1.77 (s, 3H), 1.53-1.00 (m, 12H) ppm.

Example 261. Compound 261A and Compound 261B. Diastereomer 1 and 2 of (2S)-3-[3-(22-fluoro-3,6-dimethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl)phenyl]-2-methyl-propanoic Acid

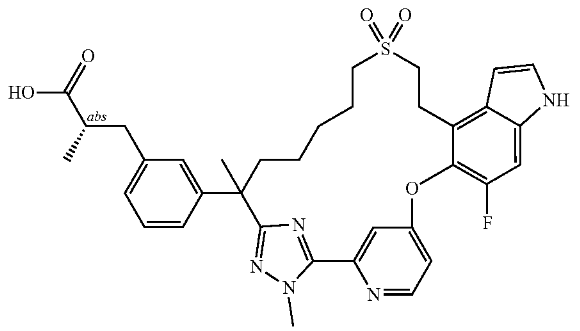 [SMILES: C[C@@H](Cc1cccc(C2(C)CCCCCS(=O)(=O)CCc3c(c(F)cc4[nH]ccc34)Oc3ccnc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2S)-3-(3-(7-((2-hydroxyethyl)sulfonyl)-2-methyl-1-(2-methylhydrazineyl)-1-oxoheptan-2-yl)phenyl)-2-methylpropanoate (Intermediate 69-28, 1.00 g, 2.19 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 150-1, 1.00 g, 2.63 mmol), the reaction procedure sequence (Steps A to F) described for Example 6 was followed to prepare the title compound as a white solid. The chiral separation condition in corresponding Step E was as follow: Instrument: SFC-150 (Waters); Column: IC 20*250 mm, 10 μm; Column temperature: 35° C. Mobile phase: Carbon dioxide/isopropanol[Additive: 0.5% ammonia in methanol (7M)]=60/40. Flow rate: 100 g/minute. Back pressure: 100 bar; Detection wavelength: 214 nm; Cycle time: 2.9 minute; Sample solution: 300 mg dissolved in 70 ml Methanol. Injection volume: 1 mL. The first eluent (125 mg, 0.185 mmol), Diastereomer 1, was further hydrolyzed to 261A (99 mg, 0.15 mmol) as a white solid; The second eluent (140 mg, 0.208 mmol), Diastereomer 2, was further hydrolyzed to 261B (96 mg, 0.15 mmol) as a white solid. 261A: LC-MS: MS (ESI): 660 m/z $[M+H]^+$, purity: >99% (214 nm). retention time: 1.84 minutes (LC-MS method 003). $^1H$ NMR (500 MHz, $CD_3OD$) δ 8.65 (d, J=5.5 Hz, 1H), 7.40-7.38 (m, 1H), 7.35-7.33 (m, 1H), 7.32-7.30 (m, 1H), 7.20 (d, J=10.5 Hz, 1H), 7.08 (t, J=7.5 Hz, 1H), 6.96 (s, 1H), 6.94-6.90 (m, 2H), 6.61 (d, J=3.0 Hz, 1H), 4.33 (s, 3H), 3.42-3.37 (m, 2H), 3.20-3.16 (m, 1H), 2.86-2.81 (m, 2H), 2.73-2.70 (m, 1H), 2.55-2.49 (m, 2H), 2.18 (t, J=12.0 Hz, 1H), 1.88-1.84 (m, 1H), 1.75-1.71 (m, 1H), 1.62-1.52 (m, 4H), 1.45-1.40 (m, 2H), 1.31-1.26 (m, 1H), 1.23-1.19 (m, 1H), 1.00 (d, J=6.5 Hz, 3H), 0.72-0.65 (m, 1H) ppm. 261B: LC-MS: MS (ESI): 660 m/z $[M+H]^+$, purity: >99% (214 nm). retention time: 1.84 minutes (LC-MS method 003). $^1H$ NMR (500 MHz, $CD_3OD$) δ 8.65 (d, J=5.5 Hz, 1H), 7.39-7.37 (m, 1H), 7.35-7.30 (m, 2H), 7.21 (d, J=10.5 Hz, 1H), 7.07 (t, J=7.5 Hz, 1H), 6.99 (s, 1H), 6.94-6.90 (m, 2H), 6.62 (d, J=3.0 Hz, 1H), 4.33 (s, 3H), 3.43-3.36 (m, 2H), 3.23-3.19 (m, 1H), 2.86-2.81 (m, 2H), 2.73-2.69 (m, 1H), 2.55-2.49 (m, 2H), 2.20-2.15 (m, 1H), 1.87-1.84 (m, 1H), 1.75-1.71 (m, 1H), 1.60-1.55 (m, 4H), 1.46-1.39 (m, 2H), 1.30-1.26 (m, 1H), 1.23-1.19 (m, 1H), 1.00 (d, J=6.5 Hz, 3H), 0.71-0.65 (m, 1H) ppm.

Example 262. Compound 262. (2S)-3-[3-[(6R)-21,22-Difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methylpropanoic Acid

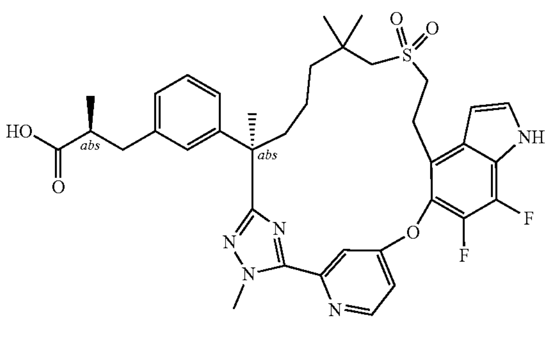

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 9.98 g, 20.6 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)oxy)pyridine-2-carbimidothioate (Intermediate 150, 8.20 g, 20.6 mmol), the reaction procedure sequence (Steps A to D and Step F) described for Example 6 was followed to prepare the title compound (2.57 g, 3.64 mmol, 82%) as a white solid. LC-MS: MS (ESI): 706 m/z $[M+H]^+$, purity: >99% (214 nm). retention time: 9.72 minutes (LC-MS method 037). $^1H$ NMR (400 MHz, $CD_3OD$) δ 8.66 (d, J=5.6 Hz, 1H), 7.67 (d, J=2.8 Hz, 1H), 7.40 (d, J=2.8 Hz, 1H), 7.27 (dd, J=6.0, 2.8 Hz, 1H), 7.12 (t, J=8.0 Hz, 1H), 7.01 (s, 1H), 6.97-6.93 (m, 2H), 6.75 (t, J=2.8 Hz, 1H), 4.35 (s, 3H), 3.42-3.34 (m, 2H), 3.19-3.05 (m, 2H), 2.93-2.86 (m, 1H), 2.68-2.54 (m, 4H), 2.09-2.02 (m, 1H), 1.84-1.76 (m, 1H), 1.64 (s, 3H), 1.46-1.38 (m, 1H), 1.25-1.17 (m, 1H), 1.10-1.00 (m, 7H), 0.97-0.88 (m, 4H) ppm.

Example 263. Compound 263. (2R)-1-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propan-2-ol

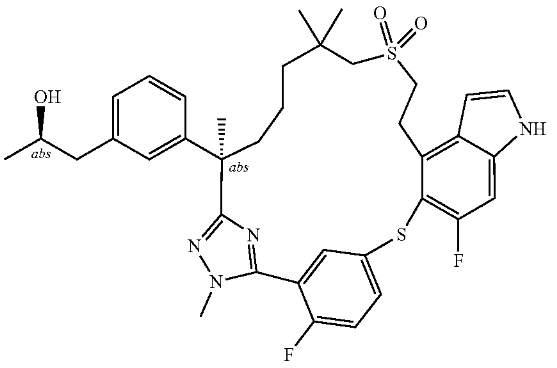 [SMILES: C[C@@H](O)Cc1cccc([C@@]2(C)CCCC(C)(C)CS(=O)(=O)CCc3c(c(F)cc4[nH]ccc34)Sc3ccc(F)c(c3)-c3nc2nn3C)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-1-(3-((R)-7-((2-hydroxyethyl)sulfonyl)-2,6,6-trimethyl-1-(2-methylhydrazineyl)-1-oxoheptan-2-yl)phenyl)propan-2-yl acetate (Intermediate 137-11, 540 mg, 1.11 mmol), the reaction procedure sequence (Steps A to D and Step G) described for Example 204 was followed to prepare the title compound (37 mg, 0.0534 mmol) as a white solid. LC-MS: MS (ESI): 693 m/z $[M+H]^+$, purity: >99% (214 nm). retention time: 1.92 minutes (LC-MS method 034). $^1H$ NMR (500 MHz, $CD_3OD$) δ 7.72-7.78 (m, 1H), 7.73-7.70 (m, 1H), 7.31-7.27 (m, 2H), 7.17-7.14 (m, 2H), 7.05 (s, 1H), 7.01-6.99 (m, 2H), 6.59 (d, J=3.0 Hz, 1H), 3.90-3.85 (m, 1H), 3.78-3.67 (m, 5H), 2.98-2.91 (m, 2H), 2.75-2.70 (m, 1H), 2.60-2.55 (m, 1H), 2.29-2.23 (m, 1H), 1.90-1.83 (m, 1H), 1.68 (s, 3H), 1.54-1.51 (m, 1H), 1.43-1.39 (m, 2H), 1.16 (s, 3H), 1.12 (s, 3H), 1.08 (d, J=6 Hz, 3H), 0.90-0.86 (m, 3H).

Example 264. Compound 264. Diastereomer 2 of (2R)-1-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propan-2-ol

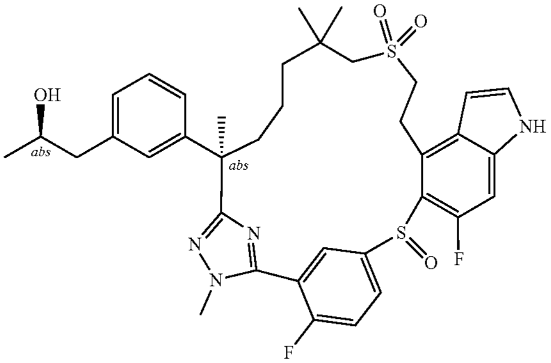 [SMILES: C[C@@H](O)Cc1cccc([C@@]2(C)CCCC(C)(C)CS(=O)(=O)CCc3c(c(F)cc4[nH]ccc34)S(=O)c3ccc(F)c(c3)-c3nc2nn3C)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-1-(3-((R)-7-((2-hydroxyethyl)sulfonyl)-2,6,6-trimethyl-1-(2-methylhydrazineyl)-1-oxoheptan-2-yl)phenyl)propan-2-yl acetate (Intermediate 137-11, 540 mg, 1.11 mmol), the reaction procedure sequence (Steps A to Step G) described for Example 204 was followed to prepare the title compound (17 mg, 0.024 mmol) as a white solid. LC-MS: MS (ESI): 709 m/z $[M+H]^+$, purity: >99% (214 nm), retention time: 1.81 minutes (LC-MS method 034). $^1H$ NMR (400 MHz, $CD_3OD$) δ 8.02 (s, 2H), 7.57 (s, 1H), 7.37 (d, J=3.2 Hz, 1H), 7.17 (t, J=7.6 Hz, 2H), 7.05-6.99 (m, 3H), 6.67 (s, 1H), 4.08-3.78 (m, 5H), 3.59 (m, 1H), 3.51-3.38 (m, 1H), 3.27-3.20 (m, 1H), 3.12-3.00 (m, 2H), 2.65 (m, 2H), 2.39 (t, J=11.6 Hz, 1H), 1.89-1.82 (m, 1H), 1.69 (s, 3H), 1.37-1.06 (m, 13H) ppm.

Example 265. Compound 265. Methyl (2R)-3-[3-[(6R)-22-fluoro-3,6,10,10-tetramethyl-12,12-dioxo-24-oxa-12λ6-thia-3,4,19,27,28,30-hexazapentacyclo[23.3.1.12,5.015,23.016,20]triaconta-1(29),2(30),4,15,17,20,22,25,27-nonaen-6-yl]phenyl]-2-methyl-propanoate

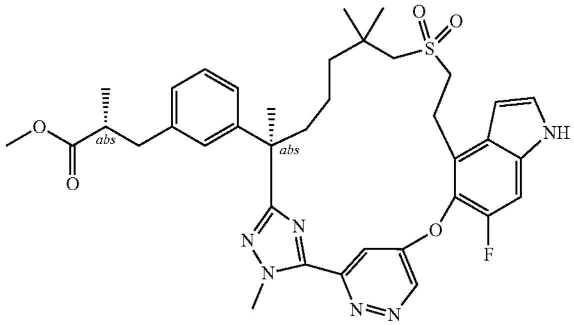 [SMILES: COC(=O)[C@H](C)Cc1cccc([C@@]2(C)CCCC(C)(C)CS(=O)(=O)CCc3c(c(F)cc4[nH]ccc34)Oc3cnnc(c3)-c3nc2nn3C)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 191 mg, 0.393 mmol), and methyl 5-((4-bromo-6-fluoro-1H-indol-5-yl)oxy)-2-fluorobenzimidothioate hydroiodide (Intermediate 14-1) with methyl 5-((4-bromo-6-fluoro-1H-indol-5-yl)oxy)pyridazine-3-carbimidothioate (Intermediate 150-6, 250 mg, 0.393 mmol), the reaction procedure sequences (Steps A to D) described for Example 6 was used to prepare the title compound (1.3 mg, white solid). LC-MS: MS (ESI): 703 m/z $[M+H]^+$, purity: 94% (214 nm), 98% (254 nm). retention time: 1.83 minutes (LC-MS method 36). $^1H$ NMR (400 MHz, $CD_3OD$) δ 9.30 (d, J=2.8 Hz, 1H), 7.71 (d, J=2.8 Hz, 1H), 7.36 (d, J=2.8 Hz, 1H), 7.29 (d, J=8.8 Hz, 1H), 7.11 (t, J=7.6 Hz, 1H), 6.99 (d, J=7.6 Hz, 1H), 6.92 (d, J=7.6 Hz, 1H), 6.89 (s, 1H), 6.74 (d, J=2.8 Hz, 1H), 4.41 (s, 3H), 3.49-3.42 (m, 5H), 3.18-3.15 (m, 2H), 2.81-2.77 (m, 1H), 2.66-2.61 (m, 3H), 2.53-2.49 (m, 1H), 2.04-2.01 (m, 1H), 1.78-1.72 (m, 1H), 1.65-1.58 (m, 4H), 1.34-1.28 (m, 1H), 1.16-1.11 (m, 1H), 1.05 (d, J=5.2 Hz, 3H), 0.96 (s, 3H), 0.92-0.88 (m, 4H) ppm.

Example 266. Compound 266A and Compound 266B. Diastereomers 1 and 2 of (2S)-3-[6-(22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl)-2-pyridyl]-2-methyl-propanoic Acid

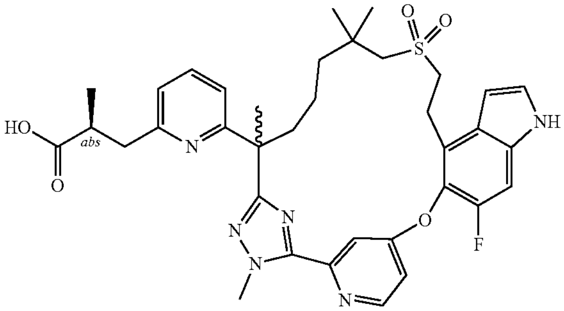 [SMILES: C[C@@H](Cc1cccc(C2(C)CCCC(C)(C)CS(=O)(=O)CCc3c(c(F)cc4[nH]ccc34)Oc3ccnc(c3)-c3nc2nn3C)n1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2S)-3-(6-(7-((2-hydroxyethyl)sulfonyl)-2,6,6-trimethyl-1-(2-methylhydrazineyl)-1-oxoheptan-2-yl)pyridin-2-yl)-2-methylpropanoate (Intermediate 107-2, 798 mg, 1.57 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 150-1, 500 mg, 1.31 mmol), the reaction procedure sequence (Steps A to D, F and E, in this order) described for Example 6 was followed to prepare the title compounds. The diastereomeric mixture of acid (275 mg, 0.399 mmol) obtained at corresponding Step F was subject to following Chiral SFC separation condition: Instrument: SFC-80 (Thar, Waters); Column: IH 20*250 mm, 10 μm; Column temperature: 35° C.; Mobile phase: Carbon dioxide/methanol (additive: 0.2% Ammonia in methanol (7M))=65/35; Flow rate: 100 g/minute; Back pressure: 100 bar; Detection wavelength: 214 nm; Cycle time: 4.5 minutes; Sample solution: 380 mg dissolved in 40 mL of methanol; Injection volume: 0.75 mL. The first eluent, Diastereomer 1, is designated as 266A (90 mg, 0.130 mmol); The second eluent, Diastereomer 1, is designated as 266B (99 mg, 0.143 mmol).

Compound 266A: LC-MS: MS (ESI): 689 m/z $[M+H]^+$, purity: 94% (214 nm), 98% (254 nm). retention time: 1.71 minutes (LC-MS method 003). $^1H$ NMR (500 MHz, DMSO-$d_6$) δ 12.03 (bs, 1H), 11.43 (s, 1H), 8.69 (d, J=5.5 Hz, 1H), 7.61 (d, J=2.5 Hz, 1H), 7.57-7.41 (m, 2H), 7.39 (d, J=10.5 Hz, 1H), 7.32 (dd, J=5.5, 2.5 Hz, 1H), 7.01 (t, J=7.5 Hz, 1H), 6.65-6.56 (m, 2H), 4.31 (s, 3H), 3.34-3.21 (m, 3H), 3.06-3.00 (m, 2H), 2.89-2.84 (m, 1H), 2.76-2.71 (m, 1H), 2.66-2.60 (m, 2H), 1.97-1.93 (m, 1H), 1.83-1.78 (m, 1H), 1.59 (s, 3H), 1.36-1.32 (m, 1H), 1.17-1.11 (m, 2H), 1.04-1.03 (m, 3H), 0.96-0.89 (m, 4H), 0.85 (s, 3H) ppm.

Compound 266B: LC-MS: MS (ESI): 689 m/z $[M+H]^+$, purity: >99% (214 nm), retention time: 1.69 minutes (LC-MS method 003). $^1H$ NMR (500 MHz, DMSO-$d_6$) δ 12.02 (s, 1H), 11.43 (s, 1H), 8.69 (d, J=5.5 Hz, 1H), 7.61 (d, J=2.5 Hz, 1H), 7.48-7.46 (m, 2H), 7.39 (d, J=10.5 Hz, 1H), 7.32 (dd, J=5.5, 2.5 Hz, 1H), 7.01 (t, J=7.5 Hz, 1H), 6.63-6.0 (m, 2H), 4.31 (s, 3H), 3.34-3.21 (m, 3H), 3.07-3.00 (m, 2H), 2.91-2.87 (m, 1H), 2.76-2.71 (m, 1H), 2.65 (s, 2H), 1.99-1.95 (m, 1H), 1.84-1.78 (m, 1H), 1.59 (s, 3H), 1.40-1.35 (m, 1H), 1.17-1.11 (m, 2H), 1.04 (d, J=7 Hz, 3H), 0.96-0.89 (m, 4H), 0.85 (s, 3H) ppm.

Example 267. Compound 267. (2S)-3-[3-[(6R)-21,22-Difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

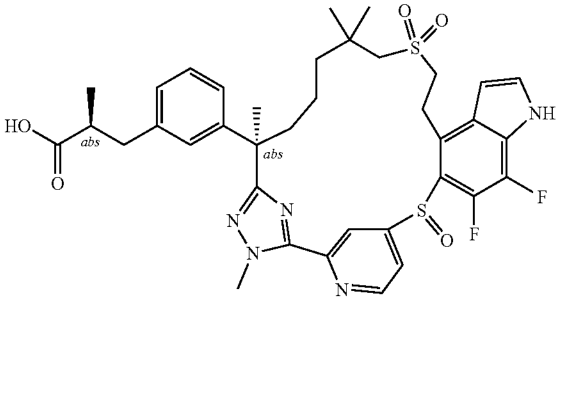 [SMILES: C[C@@H](Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O]

Methyl (2S)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

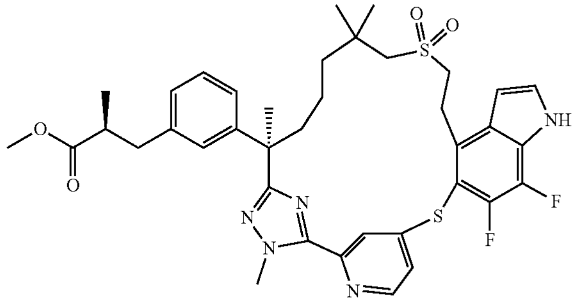 [SMILES: COC(=O)[C@@H](C)Cc1cccc([C@@]2(C)CCCC(C)(C)CS(=O)(=O)CCc3c(c(F)c(F)c4[nH]ccc34)Sc3ccnc(c3)-c3nc2nn3C)c1]

Step A: Exchanging methyl 5-((4-bromo-6-fluoro-1H-indol-5-yl)thio)-2-fluorobenzimidothioate hydroiodide (Intermediate 76) with methyl 4-((4-bromo-6,7-difluoro-1H-indol-5-yl)thio)pyridine-2-carbimidothioate (Intermediate 150-8, 4.1 g, 9.9 mmol), the reaction procedure sequence (Steps A to D) described for Example 204 was followed to prepare the title compound (1.7 g). LC-MS: MS (ESI): 736 m/z $[M+H]^+$, purity: 94% (254 nm), retention time: 2.11 minutes (LC-MS method 022).

Compound 267. (2S)-3-[3-[(6R)-21,22-Difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

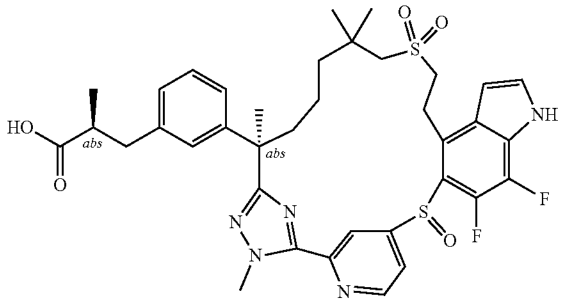 [SMILES: C[C@@H](Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O]

Step B: Exchanging methyl (2S)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step E product of Example 204) with methyl (2S)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate (Step A product of this Example, 500 mg, 0.68 mmol), the reaction procedure sequence (Steps F and H) described for Example 204 was followed to prepare the title compound. The two diastereomer mixture (350 mg), formed at corresponding F, the oxidation of thioether to sulfoxide, was separated by the following SFC conditions: Instrument: SFC-80 (Waters); Column: OD 20*250 mm, 10 μm; Column temperature: 35° C.; Mobile phase: Carbon dioxide/methanol[Additive: 0.2% ammonia in methanol (7M)]=65/35; Flow rate: 80 g/minute; Back pressure: 100 bar; Detection wavelength: 214 nm; Cycle time: 6.1 minutes; Sample solution: 350 mg dissolved in 20 mL of methanol; Injection volume: 1 mL. The first eluent, the unwanted diastereomer was removed. The second eluent was further hydrolyzed to Compound 267 (202 mg), as described in Step H of Example 204. LC-MS: MS (ESI): 738 m/z $[M+H]^+$, purity: 98% (254 nm), retention time: 1.89 minutes (LC-MS method 022). $^1H$ NMR (500 MHz, $CD_3OD$) δ 9.01-8.80 (m, 1H), 8.80-8.60 (m, 1H), 7.45 (d, J=3.5 Hz, 1H), 7.30-6.60 (m, 6H), 4.31 (s, 3H), 3.65-3.59 (m, 1H), 3.52-3.38 (m, 1H), 3.19-2.74 (m, 5H), 2.66-2.54 (m, 2H), 2.51-2.34 (m, 1H), 1.81-1.68 (m, 4H), 1.59-1.37 (m, 3H), 1.34-1.05 (m, 10H) ppm.

Example 268. Compound 268. (2S)-3-[3-[(6R)-21,22-Difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

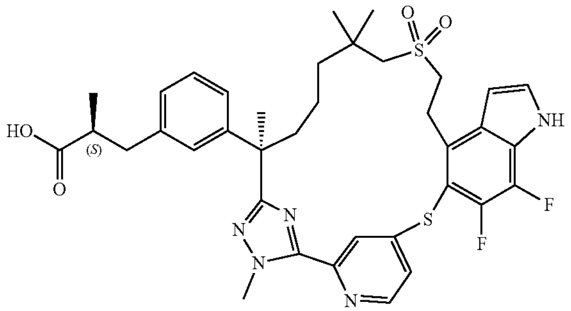

To a stirred solution of methyl (2S)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate (Step A product of Example 267, 1.2 g, 1.63 mmol) in tetrahydrofuran (15 mL) was added lithium hydroxide (4.89 mL, 1M in water). The reaction was stirred at room temperature for 3 hours, then acidified with 1 M hydrochloric acid to pH 4, extracted with ethyl acetate (2×100 mL). The combined organic extracts were washed with brine, dried over sodium sulfate, filtered, and concentrated. The residue was purified by prep-HPLC to give the title compound (345.7 mg, 29%) as a white solid. LC-MS: MS (ESI): 722 m/z $[M+H]^+$, purity: >99% (254 nm), retention time: 1.97 minutes (LC-MS method 022). $^1H$ NMR (400 MHz, $CD_3OD$) δ 8.53 (d, J=5.6 Hz, 1H), 7.70 (brs, 1H), 7.46-7.44 (m, 2H), 7.11 (t, J=7.6 Hz, 1H), 6.99-6.91 (m, 3H), 6.78 (t, J=3.2 Hz, 1H), 4.28 (s, 3H), 3.73-3.63 (m, 2H), 3.21-3.13 (m, 2H), 2.92-2.86 (m, 1H), 2.74-2.56 (m, 4H), 2.08-2.00 (m, 1H), 1.72-1.64 (m, 4H), 1.36-1.17 (m, 3H), 1.13 (s, 3H), 1.06-1.04 (m, 3H), 0.95 (s, 3H), 0.90-0.86 (m, 1H) ppm.

Example 269. Compound 269. Diastereomer 2 of (2R)-3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

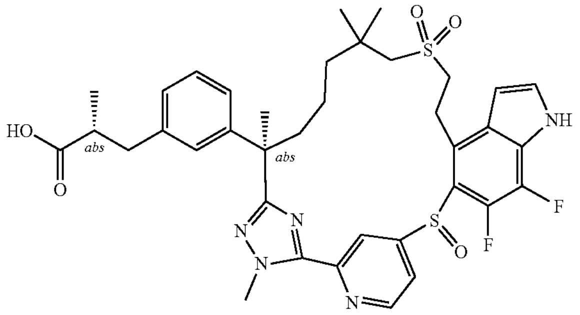 [SMILES: C[C@H](Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O]

Methyl (R)-3-(3-((R)-2-(5-(4-((4-bromo-6,7-difluoro-1H-indol-5-yl)thio)pyridin-2-yl)-1-methyl-1H-1,2,4-triazol-3-yl)-7-((2-hydroxyethyl)sulfonyl)-6,6-dimethylheptan-2-yl)phenyl)-2-methylpropanoate

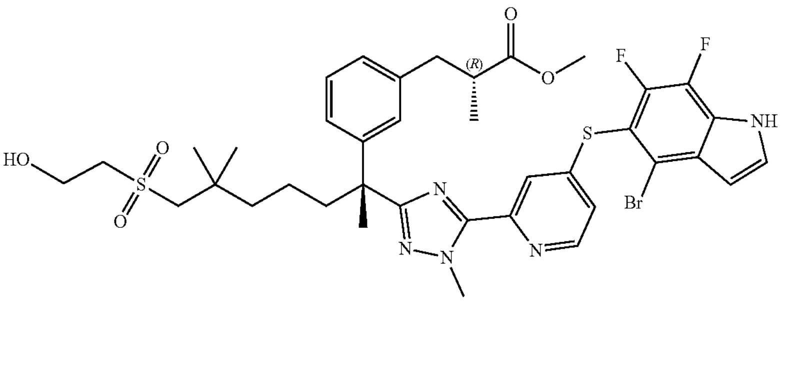

Step A: To a stirred solution of methyl (2R)-3-[3-[(1R)-6-(2-hydroxyethylsulfonyl)-1,5,5-trimethyl-1-(methylaminocarbamoyl)hexyl]phenyl]-2-methyl-propanoate (Intermediate 137, 12.28 g, 25.3 mmol) in dichloroethane (100 mL) were added methyl 4-((4-bromo-6,7-difluoro-1H-indol-5-yl)thio)pyridine-2-carbimidothioate (Intermediate 150-8, 10.50 g, 25.3 mmol), pyridine (10 mL, 127 mmol) and magnesium sulfate (30.51 g, 253 mmol). The reaction was stirred at 80° C. for 5 hours, cooled to room temperature, diluted with 300 mL of water, and extracted with ethyl acetate (300 mL×3). The combined organic phases were washed with brine, dried over sodium sulfate, filtered, and concentrated. The residue was purified by automated silica gel column chromatography (300 g silica gel column, eluting with 0-70% of ethyl acetate in petroleum ether) to give the title compound (10.50 g, 50%) as a yellow solid. LC-MS: MS (ESI): 832, 834 m/z $[M+H]^+$, purity: 95% (214 nm), retention time: 1.75 minutes (LC-MS method 040).

Methyl (R)-3-(3-((R)-2-(5-(4-((4-bromo-6,7-difluoro-1H-indol-5-yl)thio)pyridin-2-yl)-1-methyl-1H-1,2,4-triazol-3-yl)-6,6-dimethyl-7-(vinylsulfonyl)heptan-2-yl)phenyl)-2-methylpropanoate

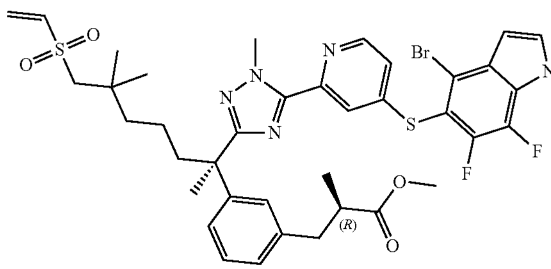

Step B: To a stirred solution of the product from Step A (10.50 g, 12.6 mmol) in dichloromethane (100 mL) were added methanesulfonyl chloride (1.1 mL, 13.9 mmol) and triethylamine (5.3 mL, 37.8 mmol). The reaction was stirred at room temperature for 2 hours, diluted with 300 mL of water, and extracted with dichloromethane (3×300 mL). The combined organic extracts were washed with brine, dried over sodium sulfate, filtered, and concentrated. The residue was purified by silica gel column chromatography (eluting with 0-50% of ethyl acetate in petroleum ether) to give the title compound (9.50 g, 93%) as a yellow solid. LC-MS: MS (ESI): 814, 816 m/z $[M+H]^+$, purity: 98% (214 nm), retention time: 1.98 minutes (LC-MS method 045).

Methyl (2R)-3-[3-[(6R,13E)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,13,15,17,20,22,25,27-decaen-6-yl]phenyl]-2-methyl-propanoate

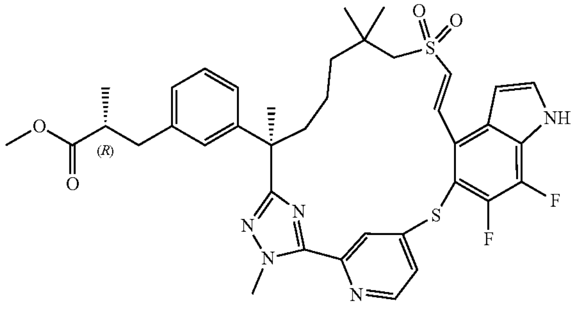 [SMILES: COC(=O)[C@H](C)Cc1cccc([C@@]2(C)CCCC(C)(C)CS(=O)(=O)/C=C/c3c(c(F)c(F)c4[nH]ccc34)Sc3ccnc(c3)-c3nc2nn3C)c1]

Step C: To a stirred solution of bis(tri-t-butylphosphine) palladium(0) (1192 mg, 2.33 mmol) and triethylamine (16 mL, 117 mmol) in toluene (500 mL) was added dropwise, at 120° C. under argon, and over 1.5 hours a solution of the product from Step B (9.50 g, 11.7 mmol) in toluene (50 mL). After the addition, the reaction was stirred at 120° C. for 1 hour and concentrated. The residue was purified by automated silica gel column chromatography (120 g silica gel column, eluting with 0-50% of ethyl acetate in petroleum ether) to give the title compound (4.80 g, 56%) as a light-yellow solid. LC-MS: MS (ESI): 734 m/z $[M+H]^+$, purity: 84% (214 nm), retention time: 2.27 minutes (LC-MS method 045).

Methyl (2R)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

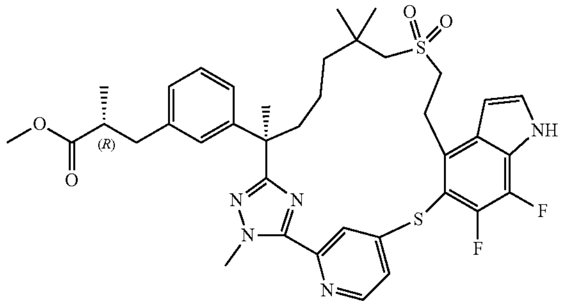 [SMILES: COC(=O)[C@H](C)Cc1cccc([C@@]2(C)CCCC(C)(C)CS(=O)(=O)CCc3c(c(F)c(F)c4[nH]ccc34)Sc3ccnc(c3)-c3nc2nn3C)c1]

Step D: To a stirred solution of the product from Step C (4.80 g, 6.54 mmol) in toluene (100 mL) was added p-toluene sulfonyl hydrazide (12.18 g, 65.4 mmol). The reaction was stirred at 110° C. for 2 hours, cooled to room temperature, diluted with 300 mL of water, and extracted with ethyl acetate (3×300 mL). The combined organic extracts were washed with brine, dried over sodium sulfate, filtered, and concentrated. The residue was purified by silica gel column chromatography (eluting with 0-50% of ethyl acetate in petroleum ether) to give the title compound (3.90 g, 81%) as a white solid. LC-MS: MS (ESI): 736 m/z $[M+H]^+$, purity: 96% (214 nm), retention time: 2.10 minutes (LC-MS method 045).

Methyl (2R)-3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

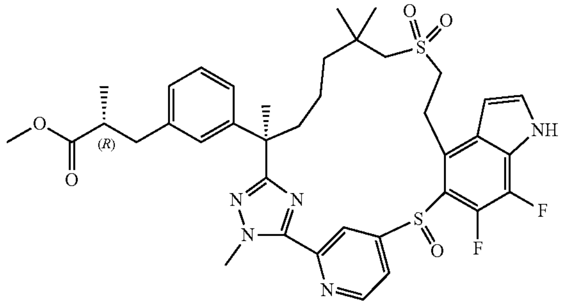 [SMILES: COC(=O)[C@H](C)Cc1cccc([C@@]2(C)CCCC(C)(C)CS(=O)(=O)CCc3c(c(F)c(F)c4[nH]ccc34)S(=O)c3ccnc(c3)-c3nc2nn3C)c1]

Step E: To a stirred solution of the product from Step D (3.90 g, 5.30 mmol) in acetonitrile (30 mL) were added (1S,2S)-1,2-diphenylethane-1,2-diol (5.68 g, 26.5 mmol), titanium(iv) isopropoxide (4.7 mL, 15.9 mmol) and tert-butyl hydroperoxide (2.2 mL, 15.9 mmol). The reaction was stirred at room temperature for 16 hours, then diluted with 150 mL of water, and extracted with ethyl acetate (3×150 mL). The combined organic extracts were washed with brine, dried over sodium sulfate, filtered, and concentrated. The residue was purified by silica gel column chromatography (eluting with 0-50% of ethyl acetate in petroleum ether) to give the title compound (3.30 g, 83%) as a yellow solid. LC-MS: MS (ESI): 752 m/z $[M+H]^+$, purity: 79% (214 nm), retention time: 2.03 minutes (LC-MS method 045).

Diastereomer 2 of methyl (2R)-3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

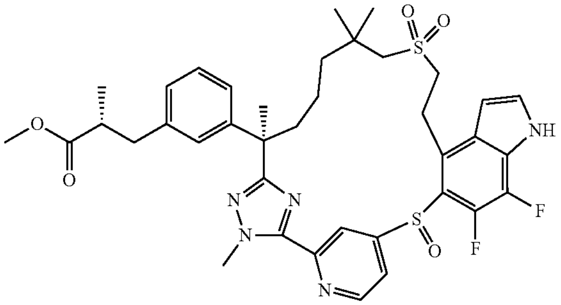 [SMILES: COC(=O)[C@H](C)Cc1cccc([C@@]2(C)CCCC(C)(C)CS(=O)(=O)CCc3c(c(F)c(F)c4[nH]ccc34)S(=O)c3ccnc(c3)-c3nc2nn3C)c1]

Step F: The diastereomeric mixture of products from Step E (3.30 g, 4.39 mmol) was subjected to chiral SFC separation under the following conditions: Instrument: SFC-150 (Waters); Column: IH 20*250 mm, 10 μm; Column temperature: 35° C.; Mobile phase: carbon dioxide/methanol [0.2% ammonia (7M in methanol)]=60/40; Flow rate: 100 g/minute; Back pressure: 100 bar; Detection wavelength: 214 nm; Cycle time: 4.58 minutes; Sample solution: 2700 mg dissolved in 350 ml methanol; Injection volume: 4.5 ml. The major isomer of the title compound (2.10 g, 64%) was obtained as a white solid.

Diastereomer 2 of (2R)-3-[3-[(6R)-21,22-Difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

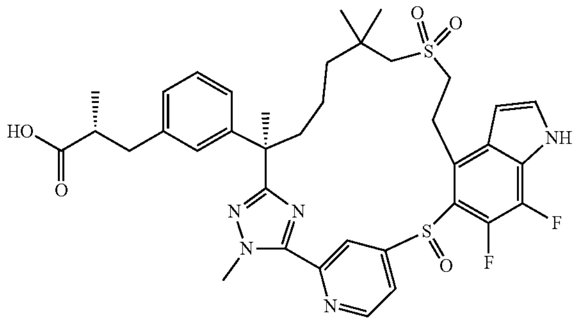 [SMILES: C[C@H](Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O]

Step G: To a solution of the product from Step F (2.10 g, 2.79 mmol) in tetrahydrofuran (30 mL) and water (15 mL) was added lithium hydroxide monohydrate (586 mg, 14.0 mmol). The reaction was stirred at room temperature for 16 hours, then diluted with 100 mL of water, acidified with hydrochloric acid solution to pH ~5, and extracted with ethyl acetate (3×150 mL). The combined organic extracts were washed with water, brine, dried over sodium sulfate, filtered, and concentrated. The residue was lyophilized to give (2R)-3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic acid (1.52 g, 74%) as a white solid. LC-MS: MS (ESI): 738 m/z $[M+H]^+$, purity: >99% (214 nm), retention time: 1.40 minutes (LC-MS method 040). $^1H$ NMR (400 MHz, $CD_3OD$) δ 8.93-8.10 (m, 2H), 7.45 (s, 1H), 7.12-6.63 (m, 6H), 4.31 (s, 3H), 3.62-3.48 (m, 2H), 3.09-2.91 (m, 4H), 2.60-2.45 (m, 3H), 1.74 (s, 4H), 1.53-0.89 (m, 14H) ppm.

Example 270. Compound 270. (2R)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

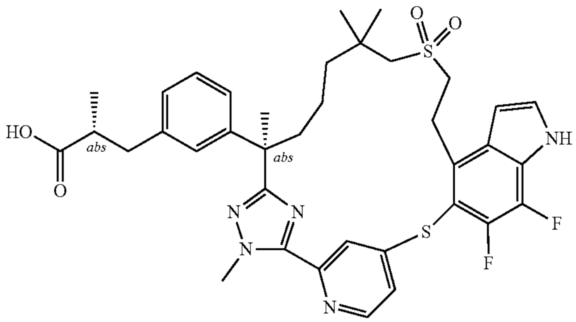 [SMILES: C[C@H](Cc1cccc([C@@]2(C)CCCC(C)(C)CS(=O)(=O)CCc3c(c(F)c(F)c4[nH]ccc34)Sc3ccnc(c3)-c3nc2nn3C)c1)C(=O)O]

To a stirred solution of methyl (2R)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate (Step A product of Example 269, 1.3 g, 1.76 mmol) in tetrahydrofuran (15 mL) was added lithium hydroxide (5.3 mL, 1M in water). The reaction was stirred at room temperature for 3 hours, then acidified with 1M hydrochloric acid to pH-4. The mixture was extracted with ethyl acetate (2×50 mL). The combined organic extracts were washed with brine, dried over sodium sulfate, filtered, and concentrated. The residue was purified by prep-HPLC to give the title compound (384.8 mg, 30%) as a white solid. LC-MS: MS (ESI): 722 m/z $[M+H]^+$, purity: >99% (214 nm), retention time: 1.97 minutes (LC- MS method 022). $^1$H NMR (400 MHz, $CD_3OD$) δ 8.53 (d, J=5.2 Hz, 1H), 7.70 (brs, 1H), 7.47-7.44 (m, 2H), 7.10 (t, J=8.0 Hz, 1H), 7.01-6.90 (m, 3H), 6.78 (t, J=2.8 Hz, 1H), 4.28 (s, 3H), 3.72-3.62 (m, 2H), 3.22-3.14 (m, 2H), 2.96-2.88 (m, 1H), 2.74-2.56 (m, 4H), 2.08-1.99 (m, 1H), 1.74-1.64 (m, 4H), 1.37-1.17 (m, 3H), 1.13 (s, 3H), 1.06 (d, J=6.4 Hz, 3H), 0.95 (s, 3H), 0.90-0.86 (m, 1H) ppm.

Example 271. Compound 271. 1-[[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic acid

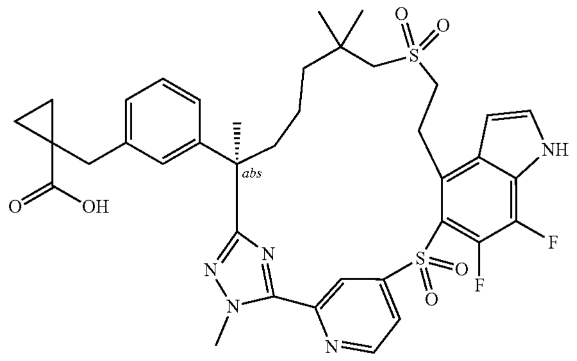 [SMILES: Cn1nc2nc1-c1cc(ccn1)S(=O)(=O)c1c(F)c(F)c3[nH]ccc3c1CCS(=O)(=O)CC(C)(C)CCC[C@]2(C)c1cccc(CC2(C(=O)O)CC2)c1]

Methyl 1-[[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylate

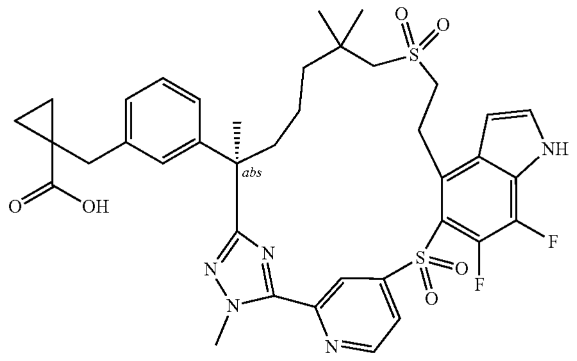 [SMILES: Cn1nc2nc1-c1cc(ccn1)S(=O)(=O)c1c(F)c(F)c3[nH]ccc3c1CCS(=O)(=O)CC(C)(C)CCC[C@]2(C)c1cccc(CC2(C(=O)O)CC2)c1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-1-(3-(7-((2-hydroxyethyl)sulfonyl)-2,6,6-trimethyl-1-(2-methylhydrazineyl)-1-oxoheptan-2-yl)benzyl)cyclopropane-1-carboxylate (Intermediate 137-12, 310 mg, 0.624 mmol), and methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 247 mg, 0.624 mmol), the reaction procedure sequence (Steps A to D) described for Example 204 was followed to give the title compound (139 mg, 0.190 mmol) as a white solid. LC-MS: MS (ESI): 730 m/z $[M+H]^+$, purity: 89% (254 nm). retention time: 2.09 minutes (LC-MS method 003).

Compound 271. 1-[[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic Acid

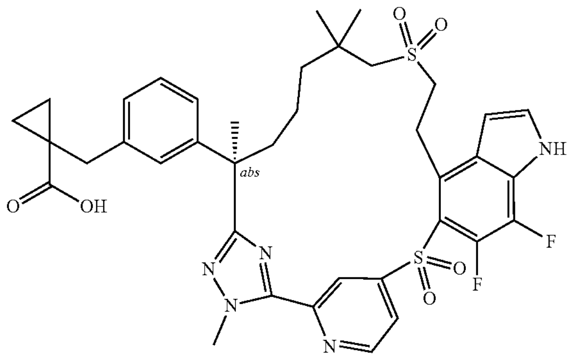 [SMILES: Cn1nc2nc1-c1cc(ccn1)S(=O)(=O)c1c(F)c(F)c3[nH]ccc3c1CCS(=O)(=O)CC(C)(C)CCC[C@]2(C)c1cccc(CC2(C(=O)O)CC2)c1]

Step B: Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with methyl 1-[[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylate (Step A product of this Example, 100 mg, 0.137 mmol), the reaction procedure sequence (Steps E to H) described for Example 204 was followed to afford the title compound. The two diastereomer mixture from Step G (68 mg) was subject to chiral SFC purification under the following conditions: Instrument: SFC-150 (Waters); Column: AS 20*250 mm, 10 μm; Column temperature: 35° C.; Mobile phase: Carbon dioxide/methanol [additive: 0.5% ammonia in methanol (7M)]=60/40; Flow rate: 110 g/min; Back pressure: 100 bar; Detection wavelength: 214 nm; Cycle time: 10.0 min; Sample solution: 65 mg dissolved in 15 ml Methanol; Injection volume: 3.0 mL. The first eluent, the unwanted diastereomer, was removed. The second eluent (35 mg), Diastereomer 2, was further hydrolyzed to 271 (12.3 mg, 0.0168 mmol, white solid), following the conditions described in Step H of Example 204. LC-MS:

MS (ESI): 732 m/z $[M+H]^+$, purity: >99% (254 nm). retention time: 1.34 minutes (LC-MS method 40). $^1$H NMR (400 MHz, DMSO-$d_6$) δ 8.81-8.65 (m, 2H), 7.52-7.50 (m, 1H), 749-7.42 (m, 1H), 7.21-6.98 (m, 5H), 6.46-6.40 (m, 1H), 4.25 (s, 3H), 3.05-2.98 (m, 1H), 2.82-2.77 (m, 3H), 2.02-1.97 (m, 1H), 1.69-1.59 (m, 4H), 1.44-1.37 (m, 4H), 1.27-1.23 (m, 5H), 1.12-1.00 (m, 6H), 0.88-0.80 (m, 1H), 0.75-0.68 (m, 2H) ppm.

Example 272. Compound 272. 1-[[3-[(6R)-22-Fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic Acid

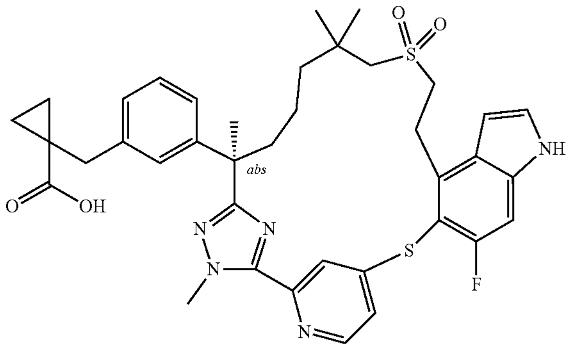 [SMILES: Cn1nc2nc1-c1cc(ccn1)Sc1c(F)cc3[nH]ccc3c1CCS(=O)(=O)CC(C)(C)CCC[C@]2(C)c1cccc(CC2(C(=O)O)CC2)c1]

To a stirred solution of methyl 1-[[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylate (Step A product of Example 271, 40 mg, 0.0548 mmol) in tetrahydrofuran (2 mL) and water (1 mL) was added lithium hydroxide monohydrate (11 mg, 0.274 mmol). The reaction was stirred at room temperature for 16 hours, diluted with 20 mL of water, acidified with 1 N hydrochloric acid to pH-6, and extracted with ethyl acetate (3×20 mL). The combined organic phases were washed with brine, dried over sodium sulfate and concentrated. The residue was purified by Prep-TLC (eluting with dichloromethane:methanol=30:1) to give the title compound (10 mg, 0.0145 mmol) as a white solid. LC-MS: MS (ESI): 716 m/z $[M+H]^+$, purity: >99% (254 nm). retention time: 1.36 minutes (LC-MS method 40). $^1$H NMR (400 MHz, $CD_3OD$) δ 8.52 (d, J=5.2 Hz, 1H), 7.70 (brs, 1H), 7.45-7.44 (m, 1H), 7.40 (d, J=3.2 Hz, 1H), 7.31 (d, J=8.8 Hz, 1H), 7.12 (t, J=8.0 Hz, 1H), 7.04-7.02 (m, 2H), 6.95 (d, J=8.0 Hz, 1H), 6.74 (d, J=2.8 Hz, 1H), 4.29 (s, 3H), 3.78-3.69 (m, 2H), 3.22-3.15 (m, 2H), 2.96-2.83 (m, 2H), 2.63-2.57 (m, 1H), 2.04-1.97 (m, 1H), 1.65 (s, 3H), 1.35-1.30 (m, 6H), 1.17-1.12 (m, 5H), 0.96-0.89 (m, 5H) ppm.

Example 273. Compound 273. 3-[3-[(6R)-22-Fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

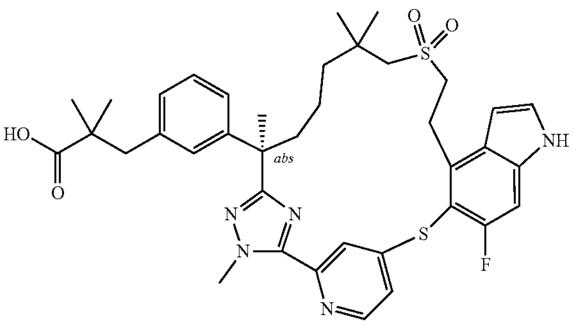 [SMILES: Cn1nc2nc1-c1cc(ccn1)Sc1c(F)cc3[nH]ccc3c1CCS(=O)(=O)CC(C)(C)CCC[C@]2(C)c1cccc(CC(C)(C)C(=O)O)c1]

Methyl 3-[3-[(6R)-22-Fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoate

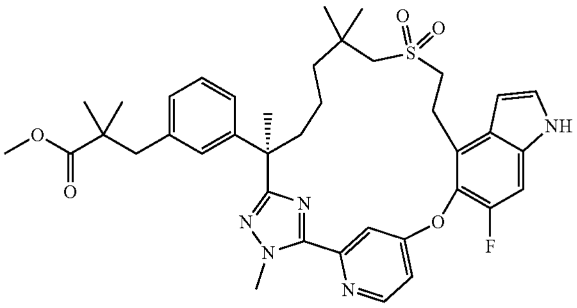 [SMILES: COC(=O)C(C)(C)Cc1cccc([C@@]2(C)CCCC(C)(C)CS(=O)(=O)CCc3c(c(F)cc4[nH]ccc34)Oc3ccnc(c3)-c3nc2nn3C)c1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 900 mg, 1.80 mmol), and methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 715 mg, 1.80 mmol), the reaction procedure sequence (Steps A to D) described for Example 204 was followed to prepare the title compound (240 mg, 0.328 mmol) as a white solid. LC-MS: MS (ESI): 732 m/z $[M+H]^+$, purity: >99% (254 nm). retention time: 2.13 minutes (LC-MS method 003).

Compound 273. 3-[3-[(6R)-22-Fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

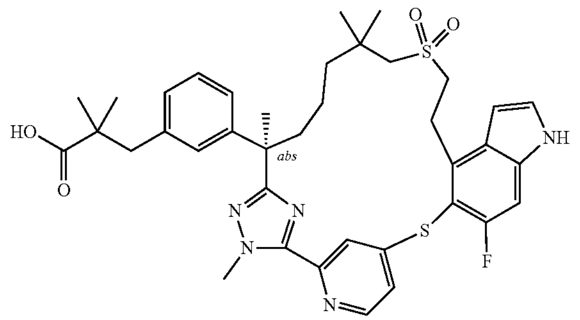 [SMILES: Cn1nc2nc1-c1cc(ccn1)Sc1c(F)cc3[nH]ccc3c1CCS(=O)(=O)CC(C)(C)CCC[C@]2(C)c1cccc(CC(C)(C)C(=O)O)c1]

Step B: To a stirred solution of Step A product (40 mg, 0.0546 mmol) in tetrahydrofuran (1 mL) and methanol (0.3 mL) was added lithium hydroxide monohydrate (0.30 mL, 0.300 mmol)(1 M in water). The reaction was stirred at room temperature for 48 hours, acidified with 1.0 M hydrochloric acid to pH ~6, and extracted with ethyl acetate (3×10 mL). The combined organic phases were washed with brine, dried over sodium sulfate, filtered, and concentrated to give the title compound (33 mg, 0.0464 mmol, 85%) as a white solid. LC-MS: MS (ESI): 718 m/z $[M+H]^+$, purity: >99% (214 nm). retention time: 1.99 minutes (LC-MS method 034). $^1H$ NMR (500 MHz, $CD_3OD$) δ 8.50 (d, J=3.0 Hz, 1H), 7.67 (s, 1H), 7.43 (d, J=4.5 Hz, 1H), 7.38 (s, 1H), 7.30 (d, J=9.0 Hz, 1H), 7.09 (t, J=7.5 Hz, 1H), 6.96-6.93 (m, 3H), 6.73 (s, 1H), 4.27 (s, 3H), 3.78-3.67 (m, 2H), 3.20-3.18 (m, 2H), 2.80-2.74 (m, 2H), 2.64-2.55 (m, 2H), 2.01-1.95 (m, 1H), 1.65-1.60 (m, 4H), 1.35-1.26 (m, 1H), 1.22-1.16 (m, 1H), 1.10 (s, 3H), 1.06-1.04 (m, 7H), 0.94-0.88 (m, 4H) ppm.

Example 274. Compound 274. 3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic acid

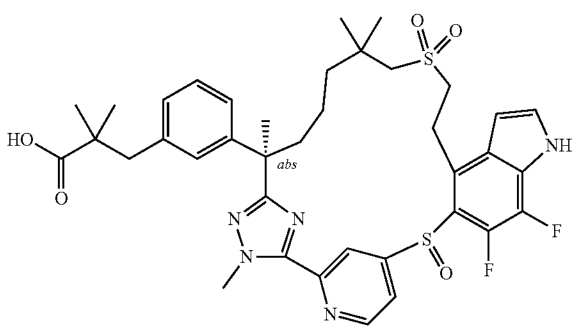 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(CC(C)(C)C(=O)O)c1]

Methyl 3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoate

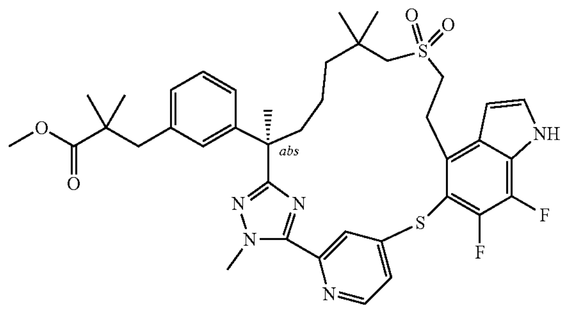 [SMILES: COC(=O)C(C)(C)Cc1cccc([C@@]2(C)CCCC(C)(C)CS(=O)(=O)CCc3c(c(F)c(F)c4[nH]ccc34)Sc3ccnc(c3)-c3nc2nn3C)c1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 600 mg, 1.20 mmol), and methyl 5-((4-bromo-6-fluoro-1H-indol-5-yl)thio)-2-fluorobenzimidothioate hydroiodide (Intermediate 76) with methyl 4-((4-bromo-6,7-difluoro-1H-indol-5-yl)thio)pyridine-2-carbimidothioate (Intermediate 150-8, 498 mg, 1.20 mmol), the reaction procedure sequence (Steps A to D) described for Example 205 was followed to prepare the title compound (120 mg, 0.160 mmol) as a white solid. LC-MS: MS (ESI): 750 m/z $[M+H]^+$, purity: >99% (214 nm). retention time: 2.16 minutes (LC-MS method 003).

Compound 274. 3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

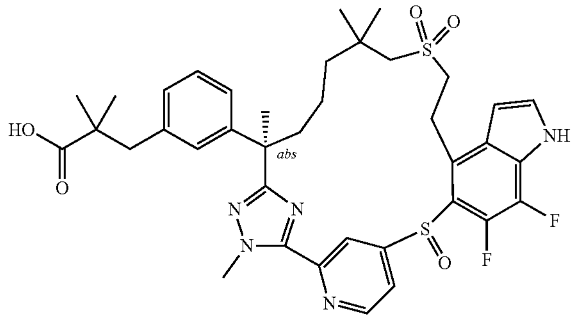 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(CC(C)(C)C(=O)O)c1]

Step B: Exchanging Methyl (2S)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (step E product of Example 204) with Methyl 3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2,2- dimethyl-propanoate (Step A product of this Example (80 mg, 0.107 mmol), the reaction procedure sequence (Steps F and H) described for Example 204 was followed to prepare the title compound. The two diastereomeric mixture, generated from corresponding Step F, oxidation of thioether to sulfoxide, was subject to SFC chiral purification under the following conditions: Instrument: SFC-150 (Waters); Column: AS 20*250 mm, 10 μm; Column temperature: 35° C.; Mobile phase: Carbon dioxide/methanol [additive: 0.5% ammonia in methanol (7M)]=60/40; Flow rate: 110 g/min; Back pressure: 100 bar; Detection wavelength: 214 nm; Cycle time: 10.0 min; Sample solution: 50 mg dissolved in 15 ml Methanol; Injection volume: 2.0 mL. The first eluent, the unwanted diastereomer, was removed. The second eluent (35 mg), Diastereomer 2, was further hydrolyzed to 274 (31 mg, 0.041 mmol, white solid), following the conditions described in Step H of Example 204. LC-MS: MS (ESI): 752 m/z $[M+H]^+$, purity: >99% (214 nm). retention time: 1.95 minutes (LC-MS method 004). $^1H$ NMR (500 MHz, DMSO-$d_6$) δ 12.41 (s, 1H), 8.78-8.73 (m, 2H), 7.63 (s, 1H), 7.33 (s, 1H), 7.09-6.92 (m, 5H), 6.51 (s, 1H), 4.24 (s, 3H), 3.14-3.00 (m, 4H), 2.73-2.67 (m, 2H), 1.72-1.63 (m, 5H), 1.47-1.37 (m, 4H), 1.28-1.22 (m, 3H), 1.10-0.91 (m, 11H) ppm.

Example 275. Compound 275. 3-[3-[(6R)-21,22-Difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

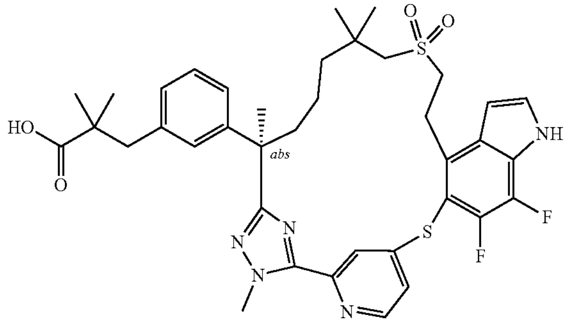 [SMILES: Cn1nc2nc1-c1cc(ccn1)Sc1c(F)c(F)c3[nH]ccc3c1CCS(=O)(=O)CC(C)(C)CCC[C@]2(C)c1cccc(CC(C)(C)C(=O)O)c1]

To a stirred solution of methyl 3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoate (Step A product of Example 274, 40 mg, 0.0533 mmol) in tetrahydrofuran (1 mL) and methanol (0.3 mL) was added lithium hydroxide monohydrate (0.27 mL, 0.27 mmol)(1 M in water). The mixture was stirred at room temperature for 48 hours, acidified with 1.0 M hydrochloric acid to pH ~6, and extracted with ethyl acetate (3×10 mL). The combined organic phases were washed with brine, dried over sodium sulfate, filtered, and concentrated to the title compound (30 mg, 0.0408 mmol, 76%) as a white solid. LC-MS: MS (ESI): 736 m/z $[M+H]^+$, purity: >99% (214 nm). retention time: 1.99 minutes (LC-MS method 034). $^1H$ NMR (500 MHz, $CD_3OD$) δ 8.53 (d, J=5.5 Hz, 1H), 7.69 (s, 1H), 7.46-7.44 (m, 2H), 7.08 (t, J=7.5 Hz, 1H), 6.97-6.92 (m, 3H), 6.78 (s, 1H), 4.27 (s, 3H), 3.72-3.63 (m, 2H), 3.18-3.17 (m, 2H), 2.79-2.63 (m, 4H), 2.05-1.99 (m, 1H), 1.70-1.64 (m, 4H), 1.37-1.15 (m, 4H), 1.12 (s, 3H), 1.07 (s, 3H), 1.03 (s, 3H), 0.95 (s, 3H) ppm.

Example 276. Compound 276. 3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propanoic Acid

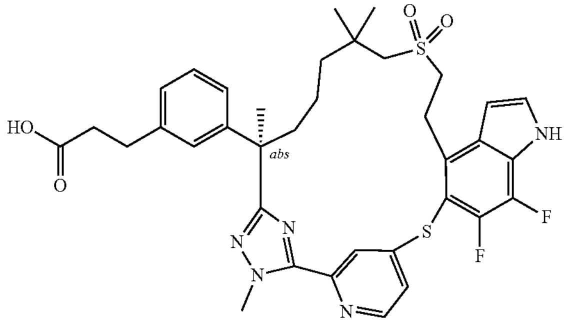 [SMILES: Cn1nc2nc1-c1cc(ccn1)Sc1c(F)c(F)c3[nH]ccc3c1CCS(=O)(=O)CC(C)(C)CCC[C@]2(C)c1cccc(CCC(=O)O)c1]

Ethyl 3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propanoate

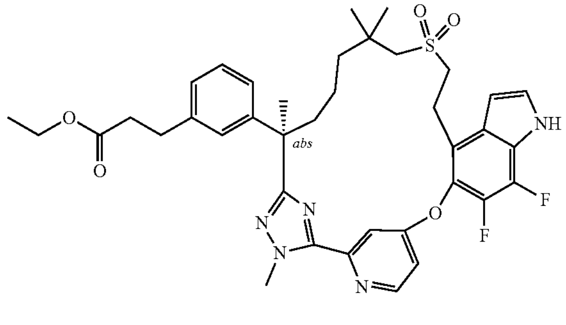 [SMILES: CCOC(=O)CCc1cccc([C@@]2(C)CCCC(C)(C)CS(=O)(=O)CCc3c(c(F)c(F)c4[nH]ccc34)Oc3ccnc(c3)-c3nc2nn3C)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with ethyl (R)-3-(3-(7-((2-hydroxyethyl)sulfonyl)-2,6,6-trimethyl-1-(2-methylhydrazineyl)-1-oxoheptan-2-yl)phenyl)propanoate (Intermediate 58-8, 679 mg, 1.40 mmol) and methyl 5-((4-bromo-6-fluoro-1H-indol-5-yl)thio)-2-fluorobenzimidothioate hydroiodide (Intermediate 76) with methyl 4-((4-bromo-6,7-difluoro-1H-indol-5-yl)thio)pyridine-2-carbimidothioate (Intermediate 150-8, 580 mg, 1.40 mmol), the reaction procedure sequence (Steps A to D) described in Example 204 was followed to prepare the title compound (90 mg, 0.122 mmol) as a white solid. LC-MS: MS (ESI): 736 m/z $[M+H]^+$, purity: 98% (254 nm). retention time: 2.12 minutes (LC-MS method 003).

Compound 276. 3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propanoic Acid

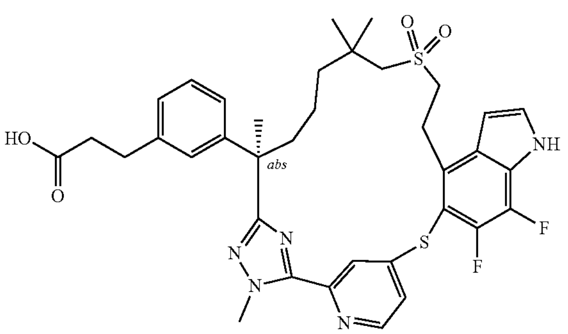 [SMILES: Cn1nc2nc1-c1cc(ccn1)Sc1c(F)c(F)c3[nH]ccc3c1CCS(=O)(=O)CC(C)(C)CCC[C@]2(C)c1cccc(CCC(=O)O)c1]

To a stirred solution of Step A product (90 mg, 0.122 mmol) in tetrahydrofuran (10 mL) and water (5 mL) was added lithium hydroxide monohydrate (26 mg, 0.611 mmol). The reaction was stirred at room temperature for 16 hours, diluted with 20 mL of water, acidified with 1 N hydrochloric acid to pH ~6, and extracted with ethyl acetate (3×30 mL). The combined organic phases were washed with brine, dried over sodium sulfate and concentrated. The residue was purified by Prep-HPLC to give the title compound (23 mg, 0.0326 mmol, 27%) as a white solid. LC-MS: MS (ESI): 708 m/z $[M+H]^+$, purity: >99% (214 nm). retention time: 1.93 minutes (LC-MS method 004). $^1H$ NMR (400 MHz, $CD_3OD$) δ 8.56 (d, J=5.2 Hz, 1H), 7.71-7.69 (m, 1H), 7.50-7.46 (m, 2H), 7.15 (t, J=7.6 Hz, 1H), 7.06 (s, 1H), 7.03 (d, J=7.6 Hz, 1H), 6.95 (d, J=7.2 Hz, 1H), 6.81 (s, 1H), 4.30 (s, 3H), 3.72-3.68 (m, 2H), 3.22-3.19 (m, 2H), 2.87-2.82 (m, 2H), 2.80-2.66 (m, 2H), 2.55 (t, J=7.6 Hz, 2H), 2.11-2.04 (m, 1H), 1.74-1.67 (m, 4H), 1.37-1.19 (m, 4H), 1.16 (s, 3H), 0.97 (s, 3H) ppm.

Example 277. Compound 277. (2S)-3-[2-fluoro-3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic acid

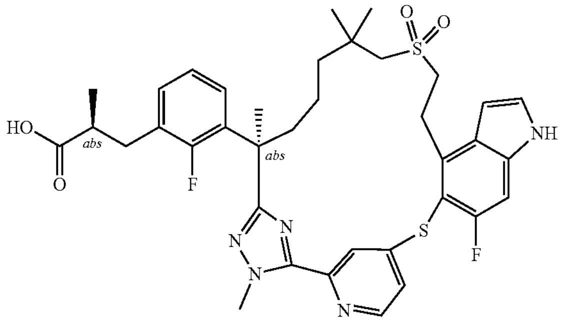 [SMILES: C[C@@H](Cc1cccc([C@@]2(C)CCCC(C)(C)CS(=O)(=O)CCc3c(c(F)cc4[nH]ccc34)Sc3ccnc(c3)-c3nc2nn3C)c1F)C(=O)O]

Methyl (2S)-3-[2-fluoro-3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

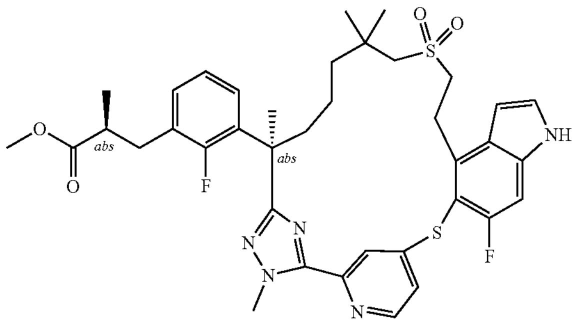 [SMILES: COC(=O)[C@@H](C)Cc1cccc([C@@]2(C)CCCC(C)(C)CS(=O)(=O)CCc3c(c(F)cc4[nH]ccc34)Sc3ccnc(c3)-c3nc2nn3C)c1F]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (S)-3-(2-fluoro-3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-14, 900 mg, 1.79 mmol) and methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 900 mg, 1.79 mmol), the reaction procedure sequence (Steps A to D) described in Example 204 was followed to prepare the title compound (180 mg, 0.245 mmol) as a white solid. LC-MS: MS (ESI): 736 m/z $[M+H]^+$, purity: 77% (254 nm). retention time: 1.39 minutes (LC-MS method 41) Compound 277. (2S)-3-[2-fluoro-3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

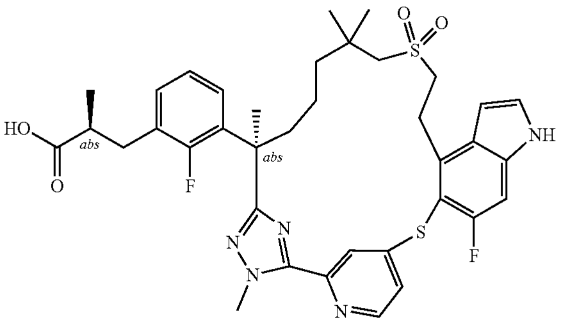 [SMILES: C[C@@H](Cc1cccc([C@@]2(C)CCCC(C)(C)CS(=O)(=O)CCc3c(c(F)cc4[nH]ccc34)Sc3ccnc(c3)-c3nc2nn3C)c1F)C(=O)O]

Step B: To a stirred solution of Step A product (59 mg, 0.0798 mmol) in tetrahydrofuran (1.6 mL), methanol (1.6 mL) and water (1.6 mL) was added lithium hydroxide monohydrate (67 mg, 1.60 mmol). The reaction was stirred at room temperature for 5 hours, acidified with 1.0 M hydrochloric acid to pH ~6, and extracted with ethyl acetate (3×10 mL). The combined organic phases were washed with brine, dried over sodium sulfate, filtered, and concentrated. The residue was purified by Prep-HPLC to afford the title compound (25 mg, 0.0348 mmol, 44%) as a white solid. LC-MS: MS (ESI): 722 m/z $[M+H]^+$, purity: >99% (254 nm). retention time: 1.29 minutes (LC-MS method 41). $^1H$ NMR (400 MHz, $CD_3OD$): δ 8.50 (d, J=5.2 Hz, 1H), 7.66 (s, 1H), 7.42 (dd, J=5.6, 2.0 Hz, 1H), 7.37 (d, J=3.2 Hz, 1H), 7.25 (d, J=8.8 Hz, 1H), 7.09 (t, J=6.4 Hz, 1H), 6.93 (t, J=7.6 Hz, 1H), 6.78-6.70 (m, 2H), 4.26 (s, 3H), 3.73-3.68 (m, 2H), 3.23-3.10 (m, 2H), 2.96-2.91 (m, 1H), 2.68-2.50 (m, 4H), 2.04-1.95 (m, 1H), 1.90-1.82 (m, 1H), 1.68 (s, 3H), 1.36-1.29 (m, 1H), 1.16-1.07 (m, 1H), 1.07-0.94 (m, 1H), 1.06 (d, J=6.8 Hz, 3H), 1.04 (s, 3H), 0.98 (s, 3H), 0.94-0.88 (m, 1H) ppm.

Example 278. Compound 278. 3-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

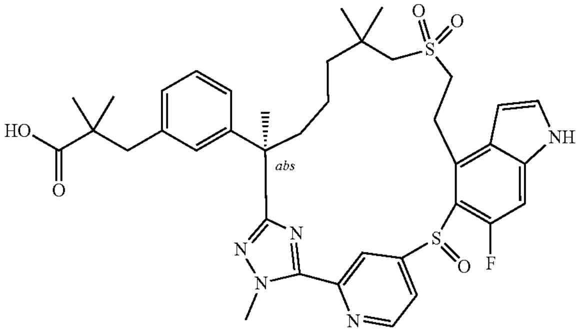 [SMILES: Cn1nc2nc1-c1cc(ccn1)S(=O)c1c(F)cc3[nH]ccc3c1CCS(=O)(=O)CC(C)(C)CCC[C@]2(C)c1cccc(CC(C)(C)C(=O)O)c1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with Methyl 3-[3-[(6R)-22-Fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoate (Step A product of Example 278273, 100 mg, 0.137 mmol), the reaction procedure sequence (Steps E, F, G and H) described for Example 204 was followed to prepare the title compound (46 mg) as a white solid. LC-MS: MS (ESI): 734 m/z $[M+H]^+$, purity: 97% (214 nm). retention time: 2.06 minutes (LC-MS method 40). $^1H$ NMR (400 MHz, DMSO-$d_6$) δ 12.11 (s, 1H), 11.71 (s, 1H), 8.80-8.70 (m, 1H), 7.55-7.50 (m, 1H), 7.48-7.32 (m, 1H), 7.25-6.85 (m, 6H), 6.52-6.40 (m, 1H), 4.28-4.15 (m, 3H), 3.61-3.42 (m, 2H), 3.21-2.97 (m, 3H), 2.81-2.67 (m, 3H), 1.72-1.60 (m, 4H), 1.49-1.36 (m, 3H), 1.29-0.93 (m, 14H) ppm.

Example 279. Compound 279. 2,2-Dimethyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

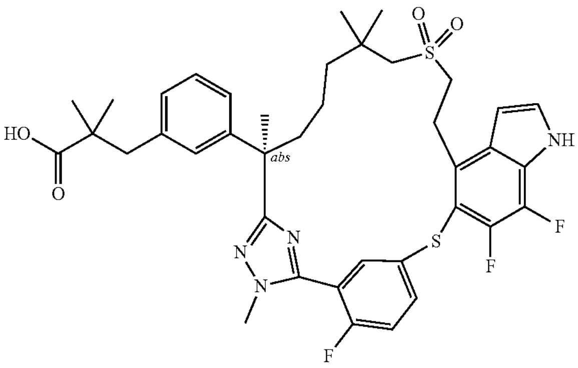 [SMILES: Cn1nc2nc1-c1cc(ccc1F)Sc1c(F)c(F)c3[nH]ccc3c1CCS(=O)(=O)CC(C)(C)CCC[C@]2(C)c1cccc(CC(C)(C)C(=O)O)c1]

Methyl 2,2-dimethyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate

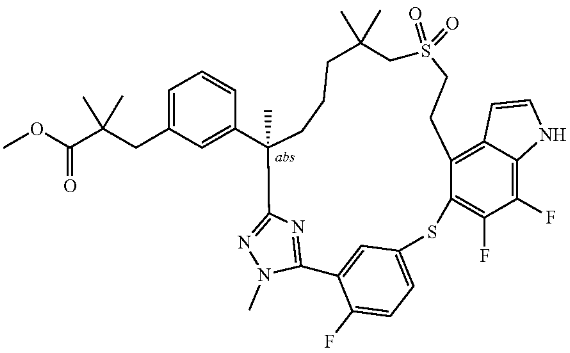 [SMILES: COC(=O)C(C)(C)Cc1cccc([C@@]2(C)CCCC(C)(C)CS(=O)(=O)CCc3c(c(F)c(F)c4[nH]ccc34)Sc3ccc(F)c(c3)-c3nc2nn3C)c1]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 2.00 g, 4.64 mmol) and methyl 5-((4-bromo-6-fluoro-1H-indol-5-yl)thio)-2-fluorobenzimidothioate hydroiodide (Intermediate 76) with methyl 5-((4-bromo-6,7-difluoro-1H-indol-5-yl)thio)-2-fluorobenzimidothioate (Intermediate 150-7, 2.59 g, 4.64 mmol), the reaction procedure sequence (Steps A to D) described in Example 204 was followed to prepare the title compound (590 mg, 0.769 mmol) as a white solid. LC-MS: MS (ESI): 767 m/z $[M+H]^+$, purity: 98% (214 nm). retention time: 2.14 minutes (LC-MS method 004).

Compound 279. 2,2-dimethyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoic acid

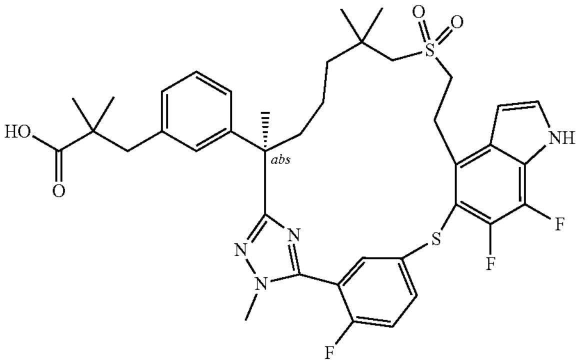 [SMILES: Cn1nc2nc1-c1cc(ccc1F)Sc1c(F)c(F)c3[nH]ccc3c1CCS(=O)(=O)CC(C)(C)CCC[C@]2(C)c1cccc(CC(C)(C)C(=O)O)c1]

Step B: To a stirred suspension of Step A product (60 mg, 0.0782 mmol) in tetrahydrofuran (3 mL), methanol (1 mL) and water (1 mL) was added lithium hydroxide monohydrate (6.6 mg, 0.156 mmol). The reaction mixture was stirred at room temperature for 2 days, then diluted with water (10 mL), acidified with 1.0 M hydrochloric acid to pH ~6, and extracted with ethyl acetate (3×10 mL). The combined organic phases were washed with brine, dried over sodium sulfate, filtered, and concentrated. The residue was purified by prep-HPLC to afford the title compound (31 mg, 0.0406 mmol, 51%) as a white solid. LC-MS: MS (ESI): 753 m/z $[M+H]^+$, purity: 99% (214 nm). retention time: 1.97 minutes (LC-MS method 004). $^1H$ NMR (400 MHz, $CD_3OD$) δ 7.85-7.79 (m, 1H), 7.76 (dd, J=6.4, 2.4 Hz, 1H), 7.37-7.29 (m, 2H), 7.12 (t, J=7.6 Hz, 1H), 7.03-6.94 (m, 3H), 6.65 (t, J=3.2 Hz, 1H), 3.79-3.65 (m, 5H), 3.28-3.22 (m, 1H), 3.02-2.93 (m, 2H), 2.79 (s, 2H), 2.29-2.22 (m, 1H), 1.91-1.82 (m, 1H), 1.68 (s, 3H), 1.60-1.35 (m, 3H), 1.17-1.06 (m, 14H) ppm.

Example 280. Compound 280. 2,2-dimethyl-3-[3-[(6R)-21,22,28-trifluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

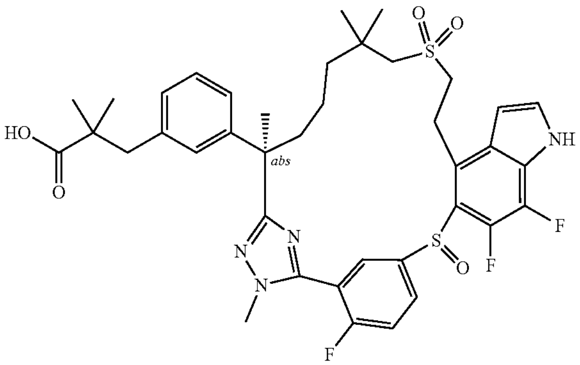 [SMILES: Cn1nc2nc1-c1cc(ccc1F)S(=O)c1c(F)c(F)c3[nH]ccc3c1CCS(=O)(=O)CC(C)(C)CCC[C@]2(C)c1cccc(CC(C)(C)C(=O)O)c1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with Methyl 2,2-dimethyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product of Example 279, 200 mg, 0.261 mmol), the reaction procedure sequence (Steps F and H) described for Example 204 was followed to prepare the title compound (53 mg, 0.0683 mmol) as a white solid. LC-MS: MS (ESI): 769 m/z $[M+H]^+$, purity: 98% (214 nm). retention time: 1.99 minutes (LC-MS method 040). $^1H$ NMR (400 MHz, $CD_3OD$) δ 8.20-7.95 (m, 2H), 7.60 (t, J=9.6 Hz, 1H), 7.44 (d, J=3.2 Hz, 1H), 7.11 (t, J=7.6 Hz, 1H), 7.04-7.02 (m, 2H), 6.95 (d, J=7.2 Hz, 1H), 6.76 (s, 1H), 4.00-3.80 (m, 4H), 3.68-3.62 (m, 1H), 3.55-3.45 (m, 1H), 3.11-2.98 (m, 2H), 2.77 (s, 2H), 2.29-2.21 (m, 1H), 1.96-1.86 (m, 1H), 1.69 (s, 3H), 1.51-1.27 (m, 4H), 1.18 (s, 3H), 1.11 (s, 3H), 1.06 (s, 7H) ppm.

Example 281. Compound 281. 3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propanoic Acid

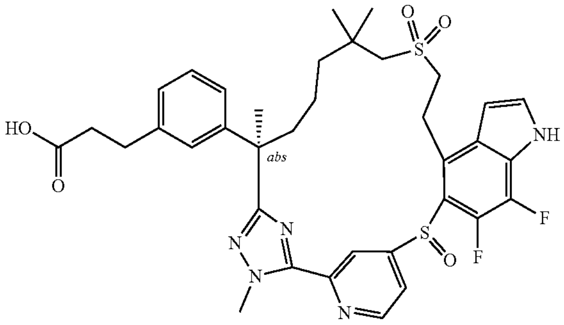 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(CCC(=O)O)c1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with ethyl 3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propanoate (Step A product of Example 276, 100 mg, 0.136 mmol), the reaction procedure sequence (Steps F and H) described for Example 204 was followed to prepare the title compound. The two diastereomer mixture (170 mg), originated from corresponding Step F, the oxidation of thioether to sulfoxide, was subject to chiral SFC separation under the following conditions: Instrument: SFC-80 (Waters); Column: IH 20*250 mm, 10 μm; Column temperature: 35° C.; Mobile phase: carbon dioxide/methanol [additive: 0.2% ammonia in methanol (7M)]=60/40; Flow rate: 80 g/minute; Back pressure: 100 bar; Detection wavelength: 214 nm; Cycle time: 5.4 minutes; Sample solution: 170 mg dissolved in 20 mL of methanol; Injection volume: 1.5 mL. The first eluent, the unwanted diastereomer, was removed. The second eluent (90 mg, 0.120 mmol, 53%), was further hydrolyzed to 280 (51 mg, 0.0699 mmol, 58%) as a white solid, following the conditions described in Step H of Example 204. LC-MS: MS (ESI): 724 m/z [M+H]+, purity: 98% (214 nm). retention time: 1.27 minutes (LC-MS method 027). $^1$H NMR (400 MHz, DMSO-$d_6$) δ 8.78-8.65 (m, 2H), 7.62 (s, 1H), 7.35-7.32 (m, 1H), 7.12-6.93 (m, 5H), 6.53-6.52 (m, 1H), 4.24-4.15 (m, 4H), 3.14-3.10 (m, 1H), 3.02-2.99 (m, 1H), 2.80-2.70 (s, 3H), 1.65-1.60 (m, 5H), 1.49-1.39 (m, 4H), 1.35-1.23 (m, 6H), 1.19-1.09 (m, 4H) ppm.

Example 282. Compound 282. (2R)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

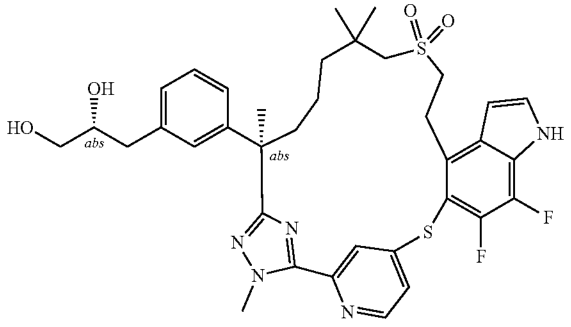 [SMILES: Cn1nc2nc1-c1cc(ccn1)Sc1c(F)c(F)c3[nH]ccc3c1CCS(=O)(=O)CC(C)(C)CCC[C@]2(C)c1cccc(C[C@@H](O)CO)c1]

[(2R)-2-acetoxy-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]Acetate

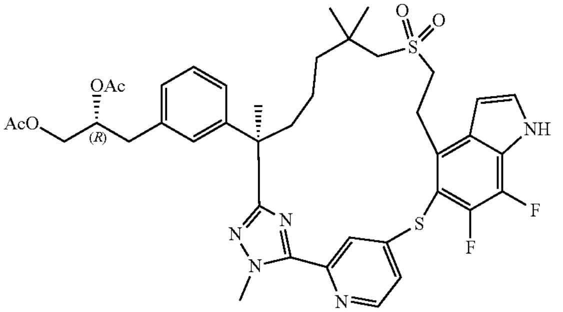

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (Intermediate 137-16, 1.50 g, 2.76 mmol), and methyl 5-((4-bromo-6-fluoro-1H-indol-5-yl)thio)-2-fluorobenzimidothioate hydroiodide (Intermediate 76) with methyl 4-((4-bromo-6,7-difluoro-1H-indol-5-yl)thio)pyridine-2-carbimidothioate (Intermediate 150-8, 1.50 g, 3.62 mmol), the reaction procedure sequence (Steps A to D) described for Example 204 was followed to prepare the title compound (435 mg, 0.548 mmol) as a white solid. LC-MS: MS (ESI): 794 m/z [M+H]+, purity: 94% (214 nm). retention time: 2.04 minutes (LC-MS method 004).

Compound 282. (2R)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

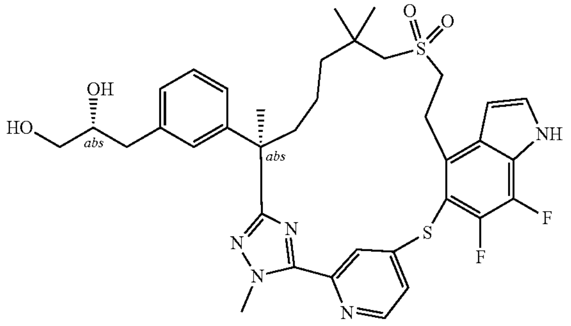 [SMILES: Cn1nc2nc1-c1cc(ccn1)Sc1c(F)c(F)c3[nH]ccc3c1CCS(=O)(=O)CC(C)(C)CCC[C@]2(C)c1cccc(C[C@@H](O)CO)c1]

Step B: To a stirred solution of Step A product (40 mg, 0.0504 mmol) in tetrahydrofuran (5 mL) and methanol (5 mL) was added potassium carbonate (21 mg, 0.151 mmol). The reaction was stirred at room temperature for 2 days, quenched with water (15 mL), and extract with ethyl acetate (3×30 mL). The combined organic layers were washed with brine, dried over sodium sulfate, filtered, and concentrated to give the title compound (3.0 mg, 0.00423 mmol, 8%) as a white solid. LC-MS: MS (ESI): 710 m/z [M+H]+, purity: 99% (214 nm). retention time: 1.96 minutes (LC-MS method 043). $^1$H NMR (400 MHz, $CD_3OD$) δ 8.52 (d, J=5.2 Hz, 1H), 7.69 (brs, 1H), 7.44 (d, J=3.2 Hz, 2H), 7.12 (t, J=7.6 Hz, 1H), 7.04-7.00 (m, 2H), 6.93 (d, J=7.6 Hz, 1H), 6.79-6.76 (m, 1H), 4.28 (s, 3H), 3.72-3.67 (m, 3H), 3.48-3.40 (m, 2H), 3.19-3.15 (m, 2H), 2.78-2.54 (m, 4H), 2.07-2.02 (m, 1H), 1.74-1.68 (m, 1H), 1.64 (s, 3H), 1.33-1.30 (m, 2H), 1.26-1.21 (m, 2H), 1.14 (s, 3H), 0.94 (s, 3H) ppm.

Example 283. Compound 283. (2S)-3-[2-fluoro-3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

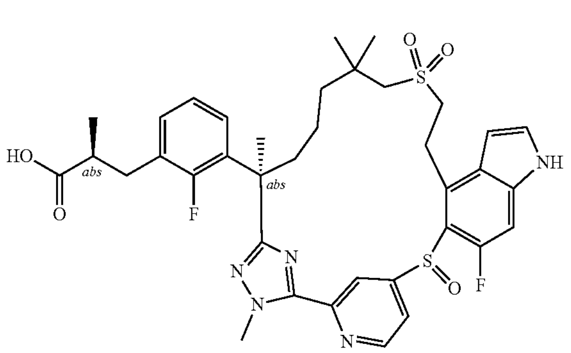 [SMILES: C[C@@H](Cc1cccc([C@@]2(C)CCCC(C)(C)CS(=O)(=O)CCc3c(c(F)cc4[nH]ccc34)S(=O)c3ccnc(c3)-c3nc2nn3C)c1F)C(=O)O]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with methyl (2S)-3-[2-fluoro-3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate (Step A product of Example 277, 120 mg, 0.163 mmol), the reaction procedure sequence (Steps E to H) described for Example 204 was followed to prepare the title compound (8 mg) as a white solid. LC-MS: MS (ESI): 738 m/z $[M+H]^+$, purity: 99% (214 nm). retention time: 1.27 minutes (LC-MS method 40). $^1H$ NMR (400 MHz, $CD_3OD$) δ 8.94-8.73 (m, 2H), 7.39 (d, J=3.6 Hz, 1H), 7.26-6.95 (m, 4H), 6.86-6.81 (m, 1H), 6.63-6.60 (m, 1H), 4.32 (s, 3H), 3.69-3.62 (m, 1H), 3.12-3.04 (m, 2H), 3.03-2.95 (m, 2H), 2.69-2.58 (m, 2H), 2.47-2.38 (m, 1H), 1.90-1.84 (m, 1H), 1.79 (s, 3H), 1.64-1.55 (m, 2H), 1.50-1.39 (m, 3H), 1.32-1.23 (m, 3H), 1.18 (s, 3H), 1.08-1.03 (m, 4H) ppm.

Example 284. Compound 284. Diastereomers 1 of 2-[[3-[(6R)-22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]methyl]-3-methoxy-propanoic Acid

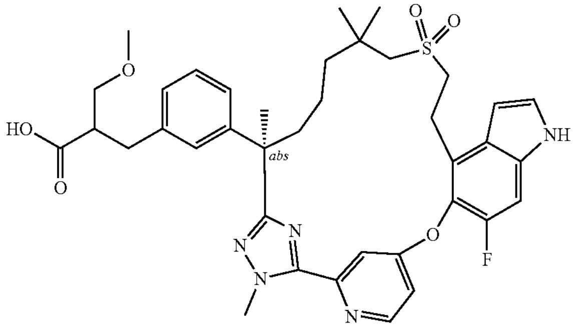 [SMILES: COCC(Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with Diastereomer 1 of methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate (Intermediate 165A, 900 mg, 1.75 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 150-1, 798 mg, 2.10 mmol), the reaction procedure sequence (Step A to D and Step F) described for Example 6 was followed to prepare the title compound (19 mg, 0.0267 mmol) as a white solid. LC-MS: MS (ESI): 718 m/z $[M+H]^+$, purity: 96% (214 nm). retention time: 1.93 minutes (LC-MS method 42). $^1H$ NMR (400 MHz, $CD_3OD$) δ 8.64 (d, J=5.6 Hz, 1H), 7.65 (s, 1H), 7.34 (d, J=3.2 Hz, 1H), 7.35-7.22 (m, 2H), 7.15-7.10 (m, 1H), 7.05-6.95 (m, 3H), 6.69 (d, J=3.2 Hz, 1H), 4.35 (s, 3H), 3.47-3.36 (m, 4H), 3.25-3.21 (m, 3H), 3.20-3.02 (m, 2H), 2.87-2.70 (m, 3H), 2.64-2.55 (m, 1H), 2.52-2.46 (m, 1H), 2.10-1.96 (m, 1H), 1.82-1.71 (m, 1H), 1.51 (s, 3H), 1.47-1.35 (m, 1H), 1.25-1.12 (m, 1H), 1.02-0.86 (m, 8H) ppm.

Example 285. Compound 285. Diastereomers 2 of 2-[[3-[(6R)-22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]methyl]-3-methoxy-propanoic Acid

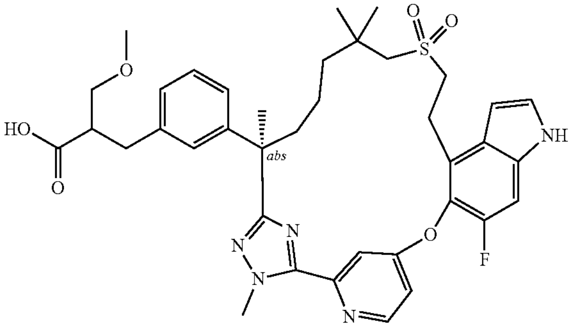 [SMILES: COCC(Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with Diastereomer 2 of methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate (Intermediate 165B, 500 mg, 0.971 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 150-1, 508 mg, 1.07 mmol), the reaction procedure sequence (Step A to D and Step F) described for Example 6 was followed to prepare the title compound (15 mg, 0.0212 mmol) as a white solid. LC-MS: MS (ESI): 718 m/z $[M+H]^+$, purity: 95% (214 nm). retention time: 1.94 minutes (LC-MS method 42). $^1H$ NMR (400 MHz, $CD_3OD$) δ 8.65 (d, J=6.0 Hz, 1H), 7.65 (s, 1H), 7.35 (d, J=3.2 Hz, 1H), 7.31-7.20 (m, 2H), 7.15-7.11 (m, 1H), 7.08-6.95 (m, 3H), 6.69 (d, J=3.2 Hz, 1H), 4.36 (s, 3H), 3.48-3.36 (m, 4H), 3.28-3.21 (m, 3H), 3.20-3.07 (m, 2H), 2.86-2.71 (m, 3H), 2.64-2.55 (m, 1H), 2.52-2.46 (m, 1H), 2.05-1.95 (m, 1H), 1.85-1.70 (m, 1H), 1.65 (s, 3H), 1.42-1.25 (m, 1H), 1.22-1.05 (m, 1H), 1.04-0.90 (m, 8H) ppm.

Example 286. Compound 286. (2S)-3-[3-[(6R)-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propane-1,2-diol (~7:3 Diastereomer Mixture on Diol Position)

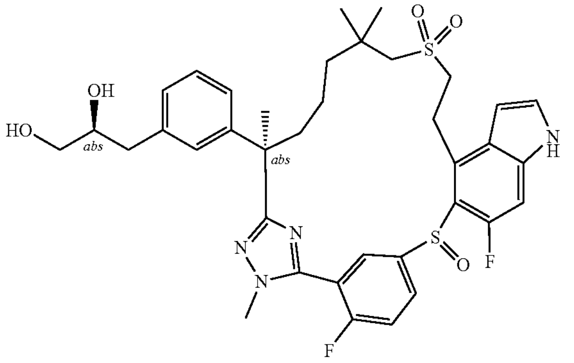 [SMILES: Cn1nc2nc1-c1cc(ccc1F)S(=O)c1c(F)cc3[nH]ccc3c1CCS(=O)(=O)CC(C)(C)CCC[C@]2(C)c1cccc(C[C@H](O)CO)c1]

(S)-3-(3-((R,Z)-26,46-difluoro-11,9,9,13-tetramethyl-7,7-dioxido-11H,41H-3,7-dithia-4(5,4)-indola-1(5,3)-triazola-2(1,3)-benzenacyclotridecaphane-13-yl)phenyl)propane-1,2-diyl diacetate (~7:3 S:R Mixture at Diol Position)

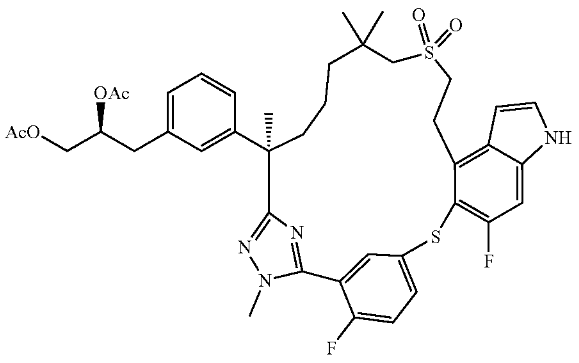 [SMILES: CC(=O)OC[C@H](Cc1cccc([C@@]2(C)CCCC(C)(C)CS(=O)(=O)CCc3c(c(F)cc4[nH]ccc34)Sc3ccc(F)c(c3)-c3nc2nn3C)c1)OC(C)=O]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (S)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (~7:3 S:R at diol position) (Intermediate 137-15, 3 g, 5.52 mmol), the reaction procedure sequence (Steps A to D) described for Example 204 was followed to prepare the title compound (640 mg, 0.808 mmol) as a white solid. LC-MS: MS (ESI): 793 m/z $[M+H]^+$, purity: 93% (214 nm). retention time: 2.08 minutes (LC-MS method 004).

Compound 286. (2S)-3-[3-[(6R)-22,28-Difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propane-1,2-diol (~7:3 Diastereomer Mixture on Diol Position)

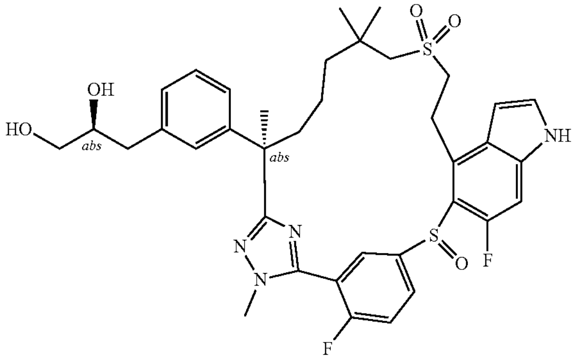 [SMILES: Cn1nc2nc1-c1cc(ccc1F)S(=O)c1c(F)cc3[nH]ccc3c1CCS(=O)(=O)CC(C)(C)CCC[C@]2(C)c1cccc(C[C@H](O)CO)c1]

Step B: Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with (S)-3-(3-((R,Z)-26,46-difluoro-11,9,9,13-tetramethyl-7,7-dioxido-11H,41H-3,7-dithia-4(5,4)-indola-1(5,3)-triazola-2(1,3)-benzenacyclotridecaphane-13-yl)phenyl)propane-1,2-diyl diacetate (~7:3 S:R mixture at diol position) (Step A product of this Example, 540 mg, 0.682 mmol), the reaction procedure sequence (Step E described for Example 204, Step A of Example 205, and Step G of Example 204, in this order) was followed to prepare the title compound (88 mg, 0.122 mmol) as a white solid. LC-MS: MS (ESI): 725 m/z $[M+H]^+$, purity: >99% (214 nm). retention time: 1.15 minutes (LC-MS method 004). $^1H$ NMR (400 MHz, $CD_3OD$) δ 8.13 (brs, 1H), 7.88 (brs, 1H), 7.55 (t, J=9.1 Hz, 1H), 7.37 (d, J=3.3 Hz, 1H), 7.22-7.11 (m, 3H), 7.06-7.01 (m, 2H), 6.67 (s, 1H), 4.00-3.80 (m, 4H), 3.76-3.64 (m, 2H), 3.49-3.35 (m, 3H), 3.27-3.16 (m, 1H), 3.12-2.98 (m, 2H), 2.80-2.73 (m, 1H), 2.62-2.58 (m, 1H), 2.35-2.25 (m, 1H), 2.00-1.87 (m, 1H), 1.71 (s, 3H), 1.50-1.34 (m, 3H), 1.21 (s, 3H), 1.13 (s, 3H), 1.08-0.98 (m, 1H) ppm.

Example 287. Compound 287. (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propane-1,2-diol (~7:3 Mixture of S:R at Diol Position)

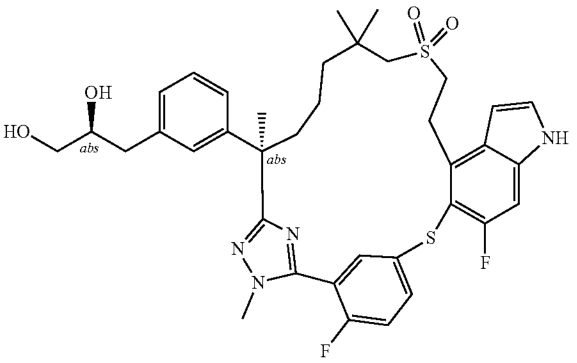 [SMILES: Cn1nc2nc1-c1cc(ccc1F)Sc1c(F)cc3[nH]ccc3c1CCS(=O)(=O)CC(C)(C)CCC[C@]2(C)c1cccc(C[C@H](O)CO)c1]

To a stirred solution of (S)-3-(3-((R,Z)-26,46-difluoro-11,9,9,13-tetramethyl-7,7-dioxido-11H,41H-3,7-dithia-4(5,4)-indola-1(5,3)-triazola-2(1,3)-benzenacyclotridecaphane-13-yl)phenyl)propane-1,2-diyl diacetate (~7:3 S:R mixture at diol position) (Step A product of Example 286, 100 mg, 0.126 mmol) in methanol (2 mL) and tetrahydrofuran (2 mL) was added potassium carbonate (87 mg, 0.63 mmol). The reaction was stirred at room temperature for 6 hours, diluted with water (10 mL), and extracted with ethyl acetate (3×10 mL). The combined organic layers were washed with brine, dried over sodium sulfate, filtered, and concentrated. The residue was purified by automated flash chromatography (25 g silica gel column, eluting with 0-4% methanol in dichloromethane) to give the title compound (28.5 mg, 0.04 mmol, 32%, ~7:3 mixture of S:R at diol position) as a white solid. LC-MS: MS (ESI): 709 m/z $[M+H]^+$, purity: >99% (214 nm). retention time: 1.72 minutes (LC-MS method 044). $^1H$ NMR (400 MHz, $CD_3OD$) δ 7.82-7.77 (m, 1H), 7.71 (dd, J=6.5, 2.3 Hz, 1H), 7.31-7.26 (m, 2H), 7.18-7.13 (m, 2H), 7.11 (s, 1H), 7.05-6.98 (m, 2H), 6.58 (d, J=3.2 Hz, 1H), 3.78-3.64 (m, 4H), 3.47-3.40 (m, 3H), 3.27-3.21 (m, 1H), 2.93 (s, 2H), 2.82 (s, 2H), 2.79-2.74 (m, 1H), 2.64-2.58 (m, 1H), 2.38-2.32 (m, 1H), 2.30-2.22 (m, 1H), 2.06-2.00 (m, 1H), 1.91-1.82 (m, 1H), 1.68 (s, 3H), 1.56-1.47 (m, 1H), 1.44-1.39 (m, 1H), 1.17 (s, 3H), 1.11 (s, 3H) ppm.

Example 288. Compound 288. 1-[[3-[(6R)-22,28-difluoro-3,6,10,10-tetramethyl-12,12-dioxo-24-oxa-12λ6-thia-3,4,19,30-tetrazapentacyclo[23.3.1.12, 5.015,23.016,20]triaconta-1(29),2(30),4,15,17,20,22, 25,27-nonaen-6-yl]phenyl]methyl] cyclopropanecarboxylic Acid

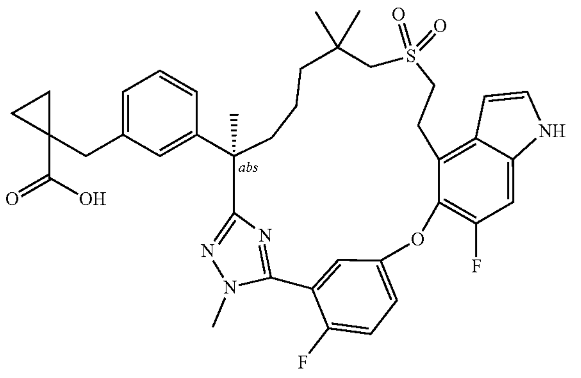 [SMILES: Cn1nc2nc1-c1cc(ccc1F)Oc1c(F)cc3[nH]ccc3c1CCS(=O)(=O)CC(C)(C)CCC[C@]2(C)c1cccc(CC2(C(=O)O)CC2)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-1-(3-(7-((2-hydroxyethyl)sulfonyl)-2,6,6-trimethyl-1-(2-methylhydrazineyl)-1-oxoheptan-2-yl)benzyl) cyclopropane-1-carboxylate (Intermediate 137-12, 200 mg, 0.403 mmol), the reaction procedure sequence (Steps A to D and F) described for Example 6 was followed to prepare the title compound (2.1 mg, 0.00293 mmol) as a white solid. LC-MS: MS (ESI): 717 m/z $[M+H]^+$, retention time: 1.34 minutes; purity: >99% (254 nm) (LC-MS method 41). $^1H$ NMR (400 MHz, $CD_3OD$) δ 7.36-7.30 (m, 3H), 7.22-7.17 (m, 2H), 7.13 (t, J=7.6 Hz, 1H), 7.03-6.98 (m, 3H), 6.60 (d, J=3.2 Hz, 1H), 3.85 (d, J=2.4 Hz, 3H), 3.41-3.35 (m, 2H), 3.26-3.12 (m, 2H), 3.00-2.80 (m, 4H), 2.17-2.08 (m, 1H), 1.85-1.77 (m, 1H), 1.67 (s, 3H), 1.37-1.27 (m, 4H), 1.22-1.00 (m, 8H), 0.71-0.65 (m, 2H) ppm.

Example 289. Compound 289. 3-[3-[(6R)-22,28-difluoro-3,6,10,10-tetramethyl-12,12-dioxo-24-oxa-12λ6-thia-3,4,19,30-tetrazapentacyclo[23.3.1.12, 5.015,23.016,20]triaconta-1(29),2(30),4,15,17,20,22, 25,27-nonaen-6-yl]phenyl]-2,2-dimethyl-propanoic Acid

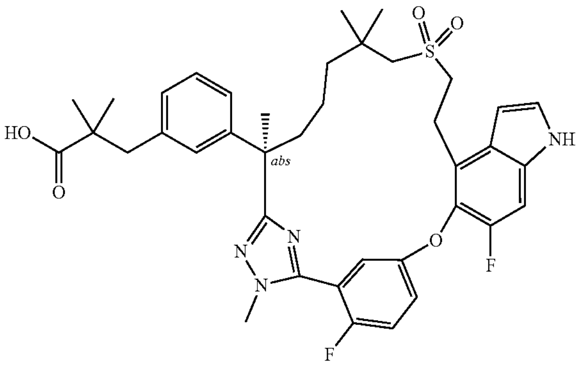 [SMILES: Cn1nc2nc1-c1cc(ccc1F)Oc1c(F)cc3[nH]ccc3c1CCS(=O)(=O)CC(C)(C)CCC[C@]2(C)c1cccc(CC(C)(C)C(=O)O)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 1.31 g, 2.63 mmol), the reaction procedure sequence (Steps A to D and F) described for Example 6 was followed to prepare the title compound (208 mg, 0.289 mmol) as a white solid. LC-MS: MS (ESI): 719 m/z $[M+H]^+$, retention time: 2.07 minutes; purity: >99% (254 nm) (LC-MS method 43). $^1H$ NMR (400 MHz, $CD_3OD$): δ 7.36-7.29 (m, 3H), 7.21-7.10 (m, 3H), 7.00-6.94 (m, 3H), 6.60 (dd, J=3.2, 0.8 Hz, 1H), 3.84 (d J=2.4 Hz, 3H), 3.39-3.32 (m, 2H), 3.30-3.26 (m, 1H), 3.22-3.14 (m, 1H), 2.96 (d, J=13.6 Hz, 1H), 2.80 (d, J=13.6 Hz, 1H), 2.76 (s, 2H), 2.18-2.09 (m, 1H), 1.84-1.76 (m, 1H), 1.66 (s, 3H), 1.63-1.55 (m, 1H), 1.36-1.28 (m, 2H), 1.22-1.16 (m, 1H), 1.05-1.03 (m, 12H) ppm.

Example 290. Compound 290. 1-[[3-[(6R)-22-fluoro-3,6,10,10-tetramethyl-12,12-dioxo-24-oxa-12λ6-thia-3,4,19,28,30-pentazapentacyclo[23.3.1.12, 5.015,23.016,20]triaconta-1(29),2(30),4,15,17,20,22, 25,27-nonaen-6-yl]phenyl]methyl] cyclopropanecarboxylic Acid

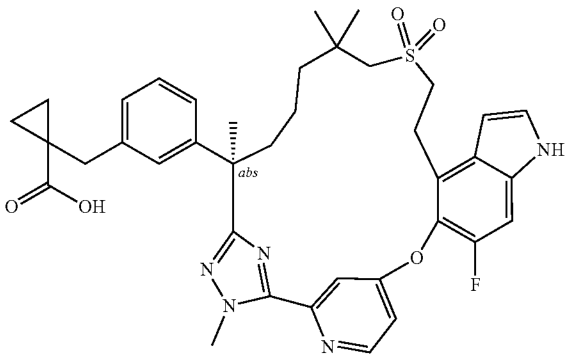 [SMILES: Cn1nc2nc1-c1cc(ccn1)Oc1c(F)cc3[nH]ccc3c1CCS(=O)(=O)CC(C)(C)CCC[C@]2(C)c1cccc(CC2(C(=O)O)CC2)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-1-(3-(7-((2-hydroxyethyl)sulfonyl)-2,6,6-trimethyl-1-(2-methylhydrazineyl)-1-oxoheptan-2-yl)benzyl) cyclopropane-1-carboxylate (Intermediate 137-12, 200 mg, 0.403 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl) oxy)pyridine-2-carbimidothioate (Intermediate 150-1, 199 mg, 0.523 mmol), the reaction procedure sequence (Steps A to D and F) described for Example 6 was followed to prepare the title compound (5.8 mg, 0.00829 mmol) as a white solid. LC-MS: MS (ESI): 700 m/z $[M+H]^+$, retention time: 1.40 minutes; purity: 99% (214 nm) (LC-MS method 40). $^1H$ NMR (400 MHz, $CD_3OD$) δ 8.64 (d, J=5.6 Hz, 1H), 7.65 (d, J=2.0 Hz, 1H), 7.35 (d, J=3.2 Hz, 1H), 7.28 (d, J=10.8 Hz, 1H), 7.24 (dd, J=5.6 Hz, 2.4 Hz, 1H), 7.11 (t, J=7.6 Hz, 1H), 7.04-6.94 (m, 3H), 6.69 (d, J=3.2 Hz, 1H), 4.34 (s, 3H), 3.45-3.39 (m, 2H), 3.20-3.09 (m, 2H), 2.87 (s, 2H), 2.64-2.50 (m, 2H), 2.06-1.98 (m, 1H), 1.78-1.71 (m, 1H), 1.64 (s, 3H), 1.49-1.34 (m, 2H), 1.23-1.06 (m, 4H), 0.98 (s, 3H), 0.94 (s, 3H), 0.71-0.65 (m, 2H) ppm.

Example 291. Compound 291. 3-[3-[(6R)-22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

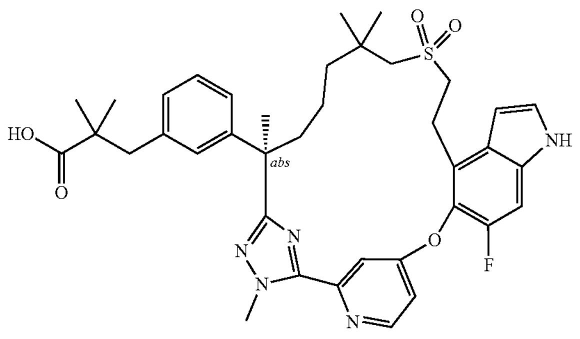 [SMILES: Cn1nc2nc1-c1cc(ccn1)Oc1c(F)cc3[nH]ccc3c1CCS(=O)(=O)CC(C)(C)CCC[C@]2(C)c1cccc(CC(C)(C)C(=O)O)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 1.31 g, 2.63 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 150-1, 1.0 g, 2.63 mmol), the reaction procedure sequence (Steps A to D and F) described for Example 6 was followed to prepare the title compound (160 mg, 0.228 mmol) as a white solid. LC-MS: MS (ESI): 702 m/z $[M+H]^+$, retention time: 2.09 minutes; purity: 99% (214 nm) (LC-MS method 43). $^1H$ NMR (400 MHz, $CD_3OD$): δ 8.64 (d, J=5.6 Hz, 1H), 7.64 (d, J=2.4 Hz, 1H), 7.34 (d, J=3.2 Hz, 1H), 7.28 (d, J=10.8 Hz, 1H), 7.24 (dd, J=6.0, 2.4 Hz, 1H), 7.10 (t, J=7.6 Hz, 1H), 6.98-6.93 (m, 3H), 6.69 (d, J=2.4 Hz, 1H), 4.34 (s, 3H), 3.45-3.39 (m, 2H), 3.19-3.07 (m, 2H), 2.80-2.70 (m, 2H), 2.64-2.51 (m, 2H), 2.05-1.98 (m, 1H), 1.78-1.69 (m, 1H), 1.64 (s, 3H), 1.46-1.38 (m, 1H), 1.36-1.26 (m, 2H), 1.18-1.12 (m, 1H), 1.06-1.04 (m, 6H), 0.97 (s, 3H), 0.94 (s, 3H) ppm.

Example 292. Compound 292. (2R)-3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol (~7:3 R:S Mixture at 2-Diol Position)

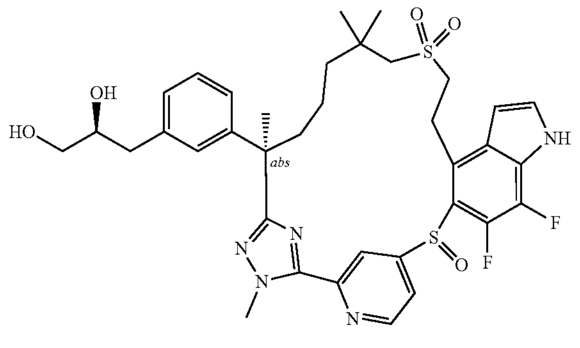 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(C[C@H](O)CO)c1]

[(2R)-2-acetoxy-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (~7:3 R:S Mixture at 2-Diol Position)

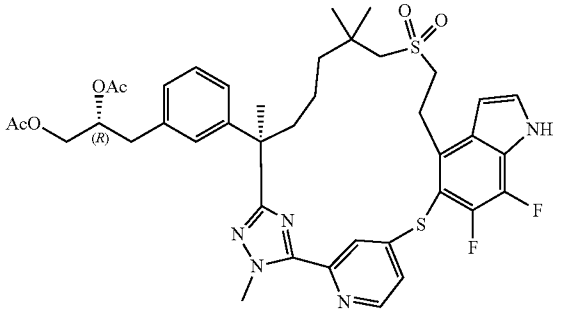

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (R)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (Intermediate 137-16, 1.50 g, 2.76 mmol), and methyl 5-((4-bromo-6-fluoro-1H-indol-5-yl)thio)-2-fluorobenzimidothioate hydroiodide (Intermediate 76) with methyl 4-((4-bromo-6,7-difluoro-1H-indol-5-yl)thio)pyridine-2-carbimidothioate (Intermediate 150-8, 1.50 g, 3.62 mmol), the reaction procedure sequence (Steps A to D) described for Example 204 was followed to prepare the title compound (435 mg, 0.548 mmol) as a white solid. LC-MS: MS (ESI): 794 m/z $[M+H]^+$, purity: 94% (214 nm). retention time: 2.04 minutes (LC-MS method 004).

Compound 292. (2R)-3-[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol (~7:3 R:S Mixture at 2-Diol Position)

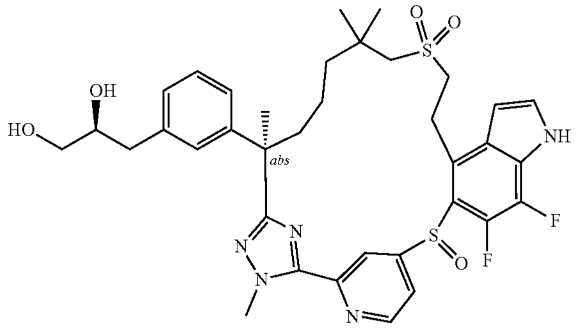 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(C[C@H](O)CO)c1]

Exchanging methyl (2S)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step E product of Example 204) with [(2R)-2-acetoxy-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (Step A product of Example 282, 85 mg, 0.107 mmol, ~7:3 R:S mixture at 2-diol position), the reaction procedure sequence (Steps F and G) described for example 204 was followed to prepare the title compound (46 mg, 0.0628 mmol) as a white solid. LC-MS: MS (ESI): 726 m/z $[M+H]^+$, purity: >99% (214 nm). retention time: 1.78 minutes (LC-MS method 004). $^1$H NMR (400 MHz, $CD_3OD$) δ 9.04-8.56 (m, 2H), 7.45 (d, J=3.2 Hz, 1H), 7.24-6.95 (m, 5H), 6.75-6.55 (m, 1H), 4.30 (s, 3H), 3.77-3.58 (m, 3H), 3.49-3.36 (m, 3H), 3.17-3.03 (m, 3H), 2.80-2.71 (m, 1H), 2.64-2.54 (m, 1H), 1.75 (s, 3H), 1.60-1.03 (m, 12H) ppm.

Example 293. Compound 293. (2S)-3-[3-[(6R)-22-fluoro-6,10,10-trimethyl-12,12-dioxo-3-oxa-12λ6, 24-dithia-19,30-diazapentacyclo[23.3.1.12,5.015, 23.016,20]triaconta-1(29),2(30),4,15,17,20,22,25,27-nonaen-6-yl]phenyl]-2-methyl-propanoic Acid

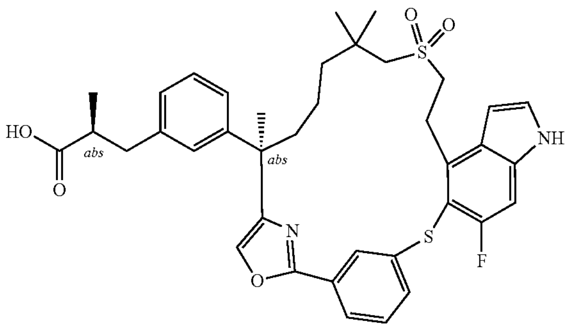 [SMILES: C[C@@H](Cc1cccc([C@@]2(C)CCCC(C)(C)CS(=O)(=O)CCc3c(c(F)cc4[nH]ccc34)Sc3cccc(c3)-c3nc2co3)c1)C(=O)O]

Exchanging (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoic acid (Intermediate 137H-1) with 3-((4-bromo-6-fluoro-1H-indol-5-yl)thio)benzoic acid (Intermediate 84-2, 1.05 g, 2.87 mmol), and 2-bromo-1-(5-((4-bromo-6-fluoro-1-(phenylsulfonyl)-1H-indol-5-yl)oxy)-2-fluorophenyl)ethan-1-one (Intermediate 140) with methyl (S)-3-(3-((R)-1-bromo-8-((2-((tert-butyldiphenylsilyl)oxy)ethyl)sulfonyl)-3,7,7-trimethyl-2-oxooctan-3-yl)phenyl)-2-methylpropanoate (Intermediate 17-17, 2.21 g, 2.87 mmol), the reaction procedure sequence (Steps A, B, C described for Example 209, followed by Steps B, C, D and H described for Example 204, by this order) was followed to prepare the title compound (8 mg) as a white solid. LC-MS: MS (ESI): 689 m/z $[M+H]^+$, purity: >99% (214 nm). retention time: 1.52 minutes (LC-MS method 40). $^1$H NMR (400 MHz, $CD_3OD$) δ 8.07 (s, 1H), 7.78-7.73 (s, 2H), 7.48-7.38 (m, 2H), 7.32 (d, J=3.2 Hz, 1H), 7.25 (d, J=8.8 Hz, 1H), 7.20-7.15 (m, 2H), 7.12-7.00 (m, 2H), 6.60 (d, J=3.2 Hz, 1H), 3.85-3.78 (m, 1H), 3.69-3.62 (m, 1H), 3.03-2.86 (m, 4H), 2.78-2.62 (m, 3H), 2.19-2.11 (m, 1H), 1.86-1.80 (m, 1H), 1.58 (s, 3H), 1.34-1.28 (m, 3H), 1.18 (s, 3H), 1.09-1.02 (s, 7H) ppm.

Example 294. Compound 294. (2S)-3-[3-[(6R)-22-fluoro-6,10,10-trimethyl-12,12,24-trioxo-3-oxa-12λ6,24λ4-dithia-19,30-diazapentacyclo[23.3.1.12, 5.015,23.016,20]triaconta-1(29),2(30),4,15,17,20,22, 25,27-nonaen-6-yl]phenyl]-2-methyl-propanoic Acid

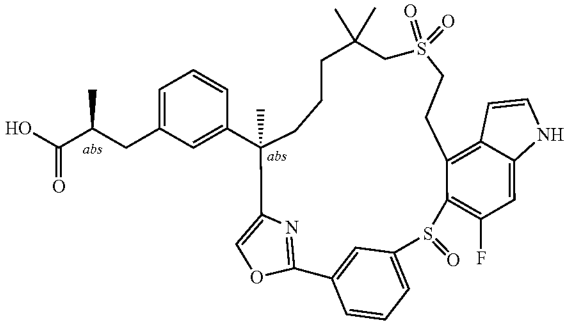 [SMILES: C[C@@H](Cc1cccc([C@@]2(C)CCCC(C)(C)CS(=O)(=O)CCc3c(c(F)cc4[nH]ccc34)S(=O)c3cccc(c3)-c3nc2co3)c1)C(=O)O]

Exchanging (R)-7-((2-((tert-butyldiphenylsilyl)oxy)ethyl)sulfonyl)-2-(3-((S)-3-methoxy-2-methyl-3-oxopropyl)phenyl)-2,6,6-trimethylheptanoic acid (Intermediate 137H-1) with 3-((4-bromo-6-fluoro-1H-indol-5-yl)thio)benzoic acid (Intermediate 84-2, 1.05 g, 2.87 mmol), and 2-bromo-1-(5-((4-bromo-6-fluoro-1-(phenylsulfonyl)-1H-indol-5-yl)oxy)-2-fluorophenyl)ethan-1-one (Intermediate 140) with methyl (S)-3-(3-((R)-1-bromo-8-((2-((tert-butyldiphenylsilyl)oxy)ethyl)sulfonyl)-3,7,7-trimethyl-2-oxooctan-3-yl)phenyl)-2-methylpropanoate (Intermediate 17-17, 2.21 g, 2.87 mmol), the reaction procedure sequence (Steps A, B, C described for Example 209, followed by Steps B, C, D, E and F H described for Example 204, by this order) was followed to prepare the title compound (19 mg) as a white solid. LC-MS: MS (ESI): 705 m/z $[M+H]^+$, purity: >99% (254 nm). retention time: 2.00 minutes (LC-MS method 003). $^1$H NMR (400 MHz, $CD_3OD$) δ 8.77 (s, 1H), 8.07 (d, J=7.2 Hz, 1H), 7.89 (s, 1H), 7.60 (t, J=8.8 Hz, 1H), 7.38 (d, J=3.6 Hz, 1H), 7.28-7.12 (m, 5H), 7.01 (d, J=7.2 Hz, 1H), 6.59 (s, 1H), 3.53-3.42 (m, 3H), 3.02 (s, 2H), 2.99-2.93 (m, 1H), 2.68-2.59 (m, 2H), 2.40-2.34 (m, 1H), 1.85-1.77 (m, 1H), 1.66-1.60 (m, 4H), 1.50-1.44 (m, 2H), 1.33-1.26 (m, 5H), 1.15 (s, 3H), 1.09 (d, J=6.0 Hz, 3H) ppm.

Example 295. Compound 295. 2,2-dimethyl-3-[3-[rac-(6R)-22-fluoro-3,6,10,10-tetramethyl-12,12-dioxo-12λ6-thia-3,4,19,28,30-pentazapentacyclo [23.3.1.12,5.015,23.016,20]triaconta-1(29),2(30),4, 15,17,20,22,25,27-nonaen-6-yl]phenyl]propanoic Acid

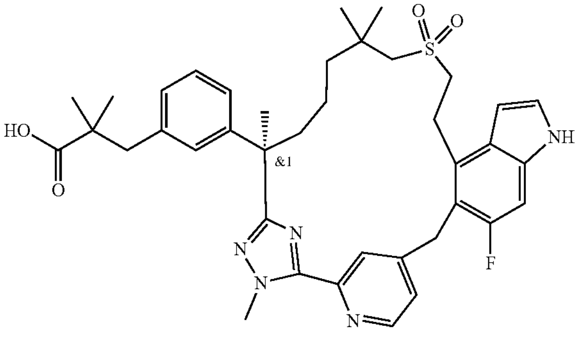 [SMILES: Cn1nc2nc1-c1cc(ccn1)Cc1c(F)cc3[nH]ccc3c1CCS(=O)(=O)CC(C)(C)CCC[C@]2(C)c1cccc(CC(C)(C)C(=O)O)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 422 mg, 0.85 mmol), and methyl 5-((4-bromo-6-fluoro-1H-indol-5-yl) oxy)-2-fluorobenzimidothioate hydroiodide (Intermediate 14-1) with methyl 4-((4-bromo-6-fluoro-1H-indol-5-yl) methyl)pyridine-2-carbimidothioate (Intermediate 150-3, 320 mg, 0.85 mmol), the reaction procedure sequence (Steps A to D and F) described for Example 6 was followed to prepare the title compound (9.5 mg, 0.0136 mmol) as a white solid. LC-MS: MS (ESI): 700 m/z $[M+H]^+$, purity: >99% (254 nm). retention time: 2.03 minutes (LC-MS method 022). $^1H$ NMR (400 MHz, $CD_3OD$) δ 8.55 (d, J=5.2 Hz, 1H), 8.30 (s, 1H), 7.39 (d, J=5.2 Hz, 1H), 7.24 (d, J=3.2 Hz, 1H), 7.16-7.02 (m, 4H), 6.97 (d, J=7.6 Hz, 1H), 6.47 (d, J=2.8 Hz, 1H), 4.33 (d, J=14.8 Hz, 1H), 4.28 (s, 3H), 4.16 (d, J=14.8 Hz, 1H), 3.50-3.35 (m, 2H), 3.18-3.07 (m, 2H), 2.99-2.89 (m, 2H), 2.80 (s, 2H), 2.40-2.33 (m, 1H), 1.95-1.87 (m, 1H), 1.72 (s, 3H), 1.63-1.54 (m, 2H), 1.48-1.42 (m, 1H), 1.24 (s, 3H), 1.21-1.12 (m, 1H), 1.11-1.06 (m, 9H) ppm.

Example 296. Compound 296. 3-[3-(22,28-Difluoro-3-methyl-12,12-dioxo-7,24-dioxa-12lambda6-thia-3,4,19,30-tetrazapentacyclo[23.3.1.$^{12,5}$.0$^{15,23}$.0$^{16,20}$]triaconta-1(29),2(30),4,15(23),16(20),17,21,25,27-nonaen-6-yl)phenyl]propan-1-ol

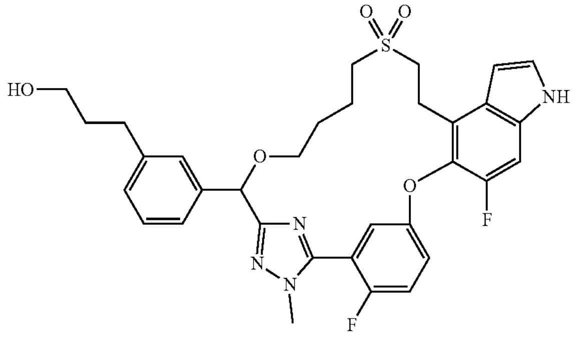 [SMILES: Cn1nc2nc1-c1cc(ccc1F)Oc1c(F)cc3[nH]ccc3c1CCS(=O)(=O)CCCCOC2c1cccc(CCCO)c1]

5-(5-(Benzyloxy)-2-fluorophenyl)-3-((3-(3-((tert-butyldimethylsilyl)oxy)propyl)phenyl)(4-(methylsulfonyl)butoxy)methyl)-1-methyl-1H-1,2,4-triazole

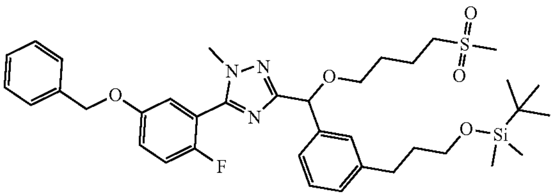 [SMILES: Cn1nc(C(OCCCCS(C)(=O)=O)c2cccc(CCCO[Si](C)(C)C(C)(C)C)c2)nc1-c1cc(OCc2ccccc2)ccc1F]

Step A: To a stirred solution of (5-(5-(benzyloxy)-2-fluorophenyl)-1-methyl-1H-1,2,4-triazol-3-yl)(3-(3-((tert-butyldimethylsilyl)oxy)propyl)phenyl)methanol (Intermediate 169-2, 512 mg, 0.91 mmol) in N,N-dimethyl-formamide (20 mL) was added sodium hydride (44 mg, 1.82 mmol) and 1-iodo-4-methylsulfonyl-butane (478 mg, 1.82 mmol). The mixture was stirred for 60 min at room temperature, diluted with ethyl acetate (50 mL), and quenched with water (5 mL). The mixture was filtered over silica gel. The organic filtrate was concentrated. The residue purified by flash chromatography (silica gel column, n-heptane/ethyl acetate=2:1 to 1:1) to afford 569 mg (88%) of the title compound.

3-(3-((1-(3-(3-((tert-Butyldimethylsilyl)oxy)propyl)phenyl)-4-(methylsulfonyl)butoxy)methyl)-1-methyl-1H-1,2,4-triazol-5-yl)-4-fluorophenol

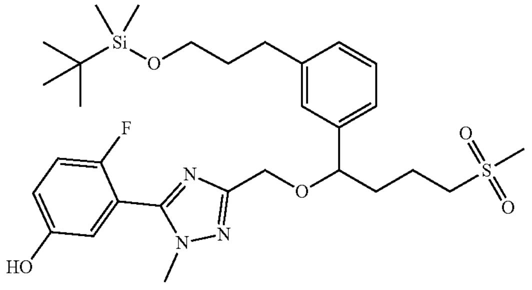 [SMILES: Cn1nc(COC(CCCS(C)(=O)=O)c2cccc(CCCO[Si](C)(C)C(C)(C)C)c2)nc1-c1cc(O)ccc1F]

Step B: To a stirred solution of step A product (1.17 g, 1.68 mmol) in 1 5 mL of ethyl acetate was added palladium on carbon (10%, 50% wet) (300 mg, 0.282 mmol), The mixture was stirred under hydrogen atmosphere (1 bar) at room temperature for 48 hours, filtered through a pad of Celite. The filtrate was concentrated to afford 1.01 g (99%) of the title compound. LC-MS: MS (ESI): 606 m/z $[M+H]^+$; purity: 79% (220 nm); retention time: 2.86 minutes (LC-MS method 045).

1-((Benzyloxy)methyl)-5-(3-(3-((3-(3-((tert-butyldimethylsilyl)oxy)propyl)phenyl)(4-(methylsulfonyl)butoxy)methyl)-1-methyl-1H-1,2,4-triazol-5-yl)-4-fluorophenoxy)-6-fluoro-1H-indole-4-carbaldehyde (product C1) and 1-((benzyloxy)methyl)-6-fluoro-5-(4-fluoro-3-(3-((3-(3-hydroxypropyl)phenyl)(4-(methylsulfonyl)butoxy)methyl)-1-methyl-1H-1,2,4-triazol-5-yl)phenoxy)-1H-indole-4-carbaldehyde (Product C2)

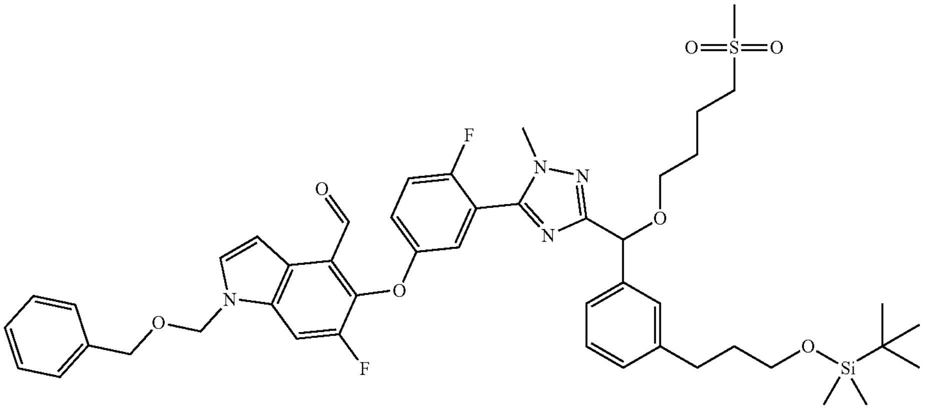

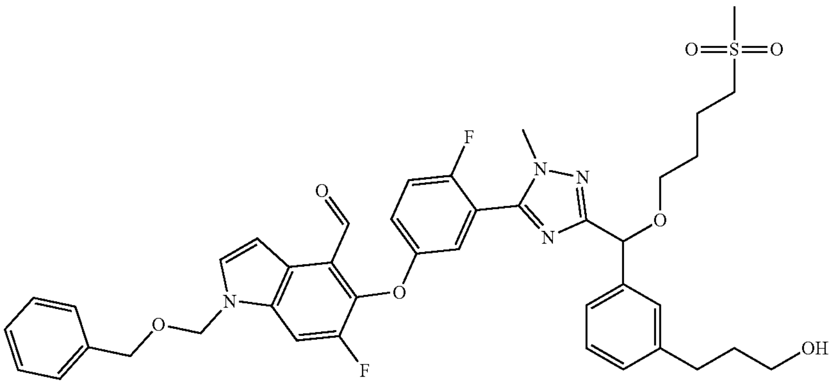

Step C: To a stirred solution of step B product (100 mg, 165 μmol) in N,N-dimethylformamide (5 mL) was added cesium carbonate (161 mg, 495 μmol) and 1-(benzyloxymethyl)-5,6-difluoro-indole-4-carbaldehyde (54.7 mg, 182 μmol). The reaction was heated at 100° C. for 1 hour, cooled to room temperature, and diluted with ethyl acetate. The mixture was washed with water. The organic layer was filtered through a pad of silica gel. The filtrate was concentrated. The residue was purified by flash chromatography (silica gel column, n-heptane/ethyl acetate=2:1 to 1:1) to afford 35 mg (24%) of the title compound C1. LC-MS: MS (ESI): 887 m/z $[M+H]^+$; purity: >99% (220 nm) (LC-MS method 045). Another 40 mg (31%) of the title compound C2 was also obtained. LC-MS: MS (ESI): 773 m/z $[M+H]^+$; purity: >99% (220 nm); retention time: 2.50 minutes (LC-MS method 045).

3-[3-[(13E)-19-(Benzyloxymethyl)-22,28-difluoro-3-methyl-12,12-dioxo-7,24-dioxa-12λ6-thia-3,4,19,30-tetrazapentacyclo[23.3.1.12,5.015,23.016,20]triaconta-1(29),2(30),4,13,15(23),16(20),17,21,25,27-decaen-6-yl]phenyl]propan-1-ol

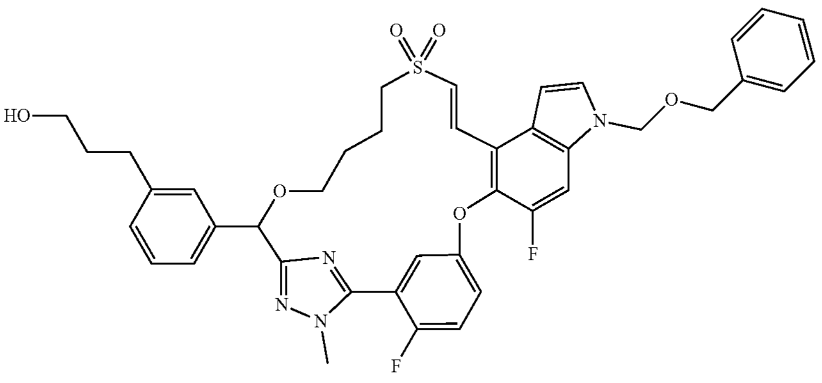 [SMILES: Cn1nc2nc1-c1cc(ccc1F)Oc1c(F)cc3c(ccn3COCc3ccccc3)c1/C=C/S(=O)(=O)CCCCOC2c1cccc(CCCO)c1]

Step D: To a stirred solution of product C2 of Step C (150 mg, 194 μmol) in dimethylformamide (10 mL) was added sodium hydride (6 mg, 250 μmol). The mixture was stirred for 1 hour at room temperature, then diluted with ethyl acetate (50 mL), and quenched with water (30 mL). The separated organic layer was washed with water, dried over sodium sulfate, filtered, and concentrated. The residue was purified by flash chromatography (silica gel column, n-heptane/ethyl acetate=2:1 to 1:1) to afford 38 mg (26%) of the product. LC-MS: MS (ESI): 799 m/z [M−H+Formic acid]$^-$; purity: 94% (220 nm); retention time: 2.63 minutes (LC-MS method 045).

Compound 296, 3-[3-(22,28-difluoro-3-methyl-12,12-dioxo-7,24-dioxa-12λ6-thia-3,4,19,30-tetrazapentacyclo[23.3.1.12,5.015,23.016,20]triaconta-1(29),2(30),4,15(23),16(20),17,21,25,27-nonaen-6-yl)phenyl]propan-1-ol

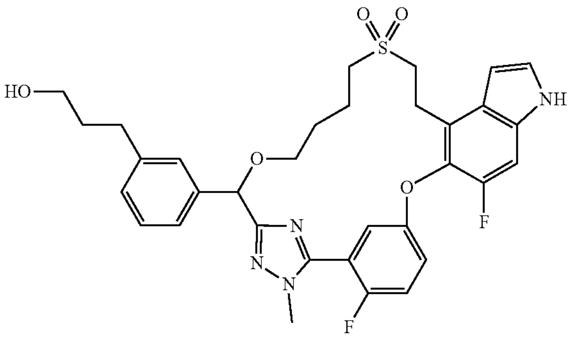 [SMILES: Cn1nc2nc1-c1cc(ccc1F)Oc1c(F)cc3[nH]ccc3c1CCS(=O)(=O)CCCCOC2c1cccc(CCCO)c1]

Step E. To a stirred solution of step D product (22 mg, 29.1 μmol) in ethanol (5 mL) was added palladium on carbon (10%) (3.1 mg, 2.9 μmol). The mixture was stirred under hydrogen atmosphere (1 bar) at room temperature for 3 days, filtered through a pad of Celite*, and concentrated. The residue was dissolved in 3 mL of methanol, treated with potassium carbonate (5.5 mg, 39.6 μmol), stirred at room temperature for 1 hour, then poured into saturated ammonium chloride, and extracted with ethyl acetate (3×10 mL). The combined organic layers were dried over sodium sulfate, filtered, and concentrated. The residue was submitted to automated reversed phase chromatography to afford 4 mg (19%) of the title compound. LC-MS: MS (ESI): 637 m/z [M+H]$^+$; purity: >99% (220 nm); retention time: 2.17 minutes (LC-MS method 045). $^1$H NMR (400.23 MHz, DMSO-$d_6$) δ 11.40 (s, 1H), 7.53-7.48 (m, 3H), 7.32 (d, J=10.6 Hz, 1H), 7.10-7.05 (m, 4H), 6.76 (d, J=5.5 Hz, 1H), 6.61-5.55 (m, 1H), 5.41 (s, 1H), 4.40 (t, J=5.1, 1H), 3.73 (d, J=2.57 Hz, 3H), 3.53-3.48 (m, 2H), 3.38-3.32 (m, 2H), 3.26-3.20 (m, 6H), 2.47-3.43 (m, 2H), 1.85-1.80 (m, 2H), 1.66-1.62 (m, 3H), 1.50-1.46 (m, 1H) ppm.

Example 297. Compound 297. 3-[3-(22,28-Difluoro-3-methyl-12,12-dioxo-7,24-dioxa-1206-thia-3,4,19,30-tetrazapentacyclo[23.3.1.12,5.015,23.016,20]triaconta-1(29),2(30),4,15(23),16(20),17,21,25,27-nonaen-6-yl)phenyl]propanoic acid

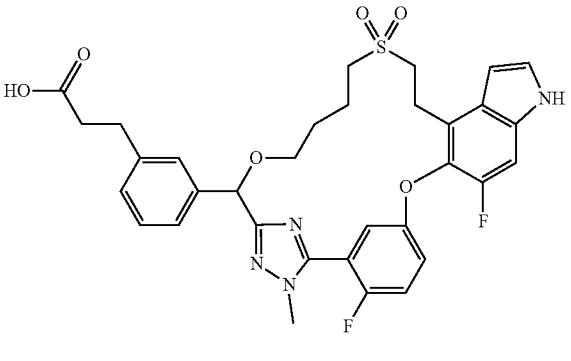 [SMILES: Cn1nc2nc1-c1cc(ccc1F)Oc1c(F)cc3[nH]ccc3c1CCS(=O)(=O)CCCCOC2c1cccc(CCC(=O)O)c1]

3-[3-[(13E)-19-(Benzyloxymethyl)-22,28-difluoro-3-methyl-12,12-dioxo-7,24-dioxa-12λ6-thia-3,4,19,30-tetrazapentacyclo[23.3.1.12,5.015,23.016,20]triaconta-1(29),2(30),4,13,15(23),16(20),17,21,25,27-decaen-6-yl]phenyl]propanoic Acid

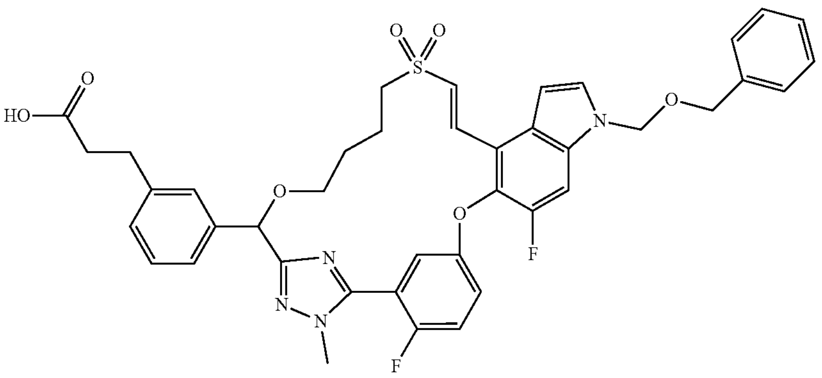 [SMILES: Cn1nc2nc1-c1cc(ccc1F)Oc1c(F)cc3c(ccn3COCc3ccccc3)c1/C=C/S(=O)(=O)CCCCOC2c1cccc(CCC(=O)O)c1]

Step A: To a stirred solution of 3-[3-[(13E)-19-(benzyloxymethyl)-22,28-difluoro-3-methyl-12,12-dioxo-7,24-dioxa-12λ6-thia-3,4,19,30-tetrazapentacyclo[23.3.1.12,5.015,23.016,20]triaconta-1(29),2(30),4,13,15(23),16(20),17,21,25,27-decaen-6-yl]phenyl]propan-1-ol (step D product of Example 296 (28 mg, 37.1 μmol)) in dichloromethane (10 mL) was added 3-oxo-115-benzo[d][1,2]iodaoxole-1,1,1(3H)-triyl triacetate (17.3 mg, 40.8 μmol). The mixture was stirred for 1 hour at room temperature, diluted with diethyl ether (25 mL), and quenched 5 mL of saturated aqueous sodium bicarbonate solution containing 45 mg (285 μmol) of sodium thiosulfate. The mixture was extracted with diethyl ether (3×25 mL). The combined organic layers were dried over sodium sulfate, filtered, and concentrated. The residue was dissolved in 5 mL of tert-butanol/1.2 mL 2-methylbut-2-en/2 mL water, treated with potassium dihydrogen phosphate (30.7 mg, 256 μmol), sodium chlorite (30.9 mg, 341 μmol). The mixture was stirred for 2 hours at room temperature, then diluted with ethyl acetate, and washed with aqueous ammonium chloride (10%) and brine, and concentrated. The residue was purified by automated reverse phase chromatography, yielding 28.5 mg (70%) of the title compound. LC-MS: MS (ESI): 769 m/z $[M+H]^+$; purity: >99% (220 nm); retention time: 2.60 minutes (LC-MS method 045).

Step B: To a stirred solution of step A product (10 mg, 13 μmol) in ethanol (5 mL) was added palladium on carbon (10%) (10 mg, 2.9 μmol). The mixture stirred under hydrogen atmosphere (1 bar) at room temperature for 1 day, filtered through a pad of Celite*, and concentrated. The residue was dissolved in 2 mL of methanol, treated with potassium carbonate (4 mg, 28.9 μmol), stirred for 1 hour, and poured into saturated aqueous ammonium chloride. The mixture was extracted three times with ethyl acetate (10 mL). The combined organic layers were dried over sodium sulfate and concentrated. The residue was submitted to automated reversed phase chromatography, yielding 2.3 mg (20%) of the title compound. LC-MS: MS (ESI): 651 m/z $[M+H]^+$; purity: >99% (220 nm); retention time: 2.14 minutes (LC-MS method 45). $^1H$ NMR (400.23 MHz, DMSO-$d_6$) δ 11.96 (br s, 1H), 11.32 (s, 1H), 7.43 (m, 3H), 7.25 (m, 1H), 7.12 (s, 1H), 7.05 (br d, J=6.2, 1H), 7.00-6.96 (m, 2H), 6.73-6.68 (m, 1H), 6.51 (br s, 1H), 5.33 (s, 1H), 3.66 (s, 3H), 3.47-3.41 (m, 2H), 3.17-3.12 (m, 4H), 2.57-2.51 (m, 2H), 2.35-1.30 (m, 2H), 1.79-1.75 (m, 2H), 1.63-1.58 (m, 2H) 1.38-1.33 (m, 2H) ppm.

3-[3-(22,28-Difluoro-3-methyl-12,12-dioxo-7,24-dioxa-12λ6-thia-3,4,19,30-tetrazapentacyclo[23.3.1.12,5.015,23.016,20]triaconta-1(29),2(30),4,15(23),16(20),17,21,25,27-nonaen-6-yl)phenyl]propanoic Acid

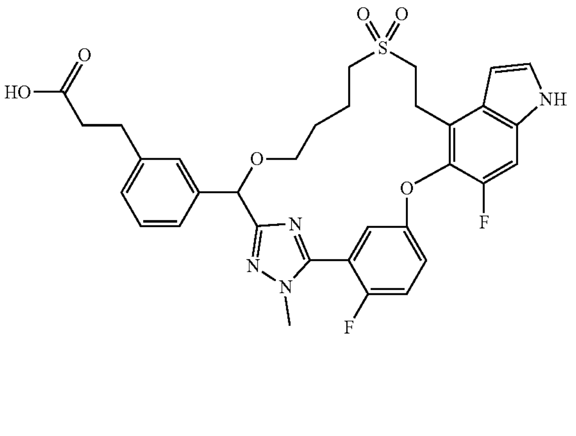 [SMILES: Cn1nc2nc1-c1cc(ccc1F)Oc1c(F)cc3[nH]ccc3c1CCS(=O)(=O)CCCCOC2c1cccc(CCC(=O)O)c1]

Example 299. Diastereomer 1 and 2 of (2S)-3-[5-(22-fluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl)-3-pyridyl]-2-methyl-propanoic Acid

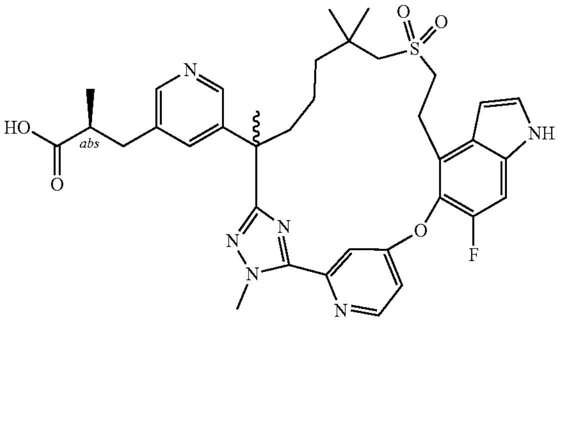 [SMILES: C[C@@H](Cc1cncc(C2(C)CCCC(C)(C)CS(=O)(=O)CCc3c(c(F)cc4[nH]ccc34)Oc3ccnc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2S)-3-(5-(7-((2-hydroxyethyl)sulfonyl)-2,6,6-trimethyl-1-(2-methylhydrazineyl)-1-oxoheptan-2-yl)pyridin-3-yl)-2-methylpropanoate (Intermediate 69-29, 431 mg, 1.13 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)oxy)pyridine-2-carbimidothioate (Intermediate 150-1, 500 mg, 1.03 mmol), and by lowering the reaction temperature down to 50° C. for 16 hours at the first step, the reaction procedure sequence (Steps A to G) described for Example 6 was followed to prepare the title compounds. The diastereomeric mixture from the corresponding Step D was subject to chiral SFC separation under the following condition: Instrument: SFC-150 (Waters); Column: IG 20*250 mm, 10 μm; Column temperature: 35° C.; Mobile phase: carbon dioxide/methanol=60/40; Flow rate: 100 g/minute; Back pressure: 100 bar; Detection wavelength: 214 nm; Cycle time: 5.58 minutes; Sample solution: 120 mg dissolved in 30 mL of methanol; Injection volume: 2 mL. The first eluent, after hydrolysis following conditions in the corresponding Step F, was designated as Compound 299A (Diastereomer 1, 6.7 mg, white solid); The second eluent, after hydrolysis following conditions described in the corresponding Step G, was designated as Compound 299B (Diastereomer 2, 24 mg, white solid).

Compound 299A: $^1$H NMR (400 MHz, $CD_3OD$) δ 8.65 (d, J=5.2 Hz, 1H), 8.20 (s, 1H), 8.16 (s, 1H), 7.68-7.67 (d, J=2 Hz, 1H), 7.57 (s, 1H), 7.37-7.35 (m, 1H), 7.29-7.26 (m, 2H), 6.69 (d, J=2.4 Hz, 1H), 4.37 (s, 3H), 3.47-3.40 (m, 2H), 3.21-3.10 (m, 2H), 2.93-2.90 (m, 1H), 2.68-2.66 (m, 2H), 2.64-2.53 (m, 2H), 2.05-2.02 (m, 1H), 1.87-1.81 (m, 1H), 1.70 (s, 3H), 1.45-1.42 (m, 1H), 1.35-1.30 (m, 2H), 1.20-1.12 (m, 3H), 1.01-0.95 (m, 4H), 0.93 (s, 3H) ppm. LC-MS: MS (ESI): 689 m/z $[M+H]^+$, purity: 96% (214 nm), 98% (254 nm). retention time: 1.25 minutes (LC-MS method 40).

Compound 299B: $^1$H NMR (400 MHz, $CD_3OD$) δ 8.67 (d, J=5.2 Hz, 1H), 8.20 (s, 1H), 8.15 (s, 1H), 7.68 (d, J=2 Hz, 1H), 7.58 (s, 1H), 7.37-7.35 (m, 1H), 7.30-7.26 (m, 2H), 6.71 (d, J=2.4 Hz, 1H), 4.37 (s, 3H), 3.47-3.42 (m, 2H), 3.21-3.10 (m, 2H), 2.93-2.90 (m, 1H), 2.73-2.66 (m, 2H), 2.64-2.53 (m, 2H), 2.05-2.02 (m, 1H), 1.83-1.82 (m, 1H), 1.70 (s, 3H), 1.45-1.42 (m, 1H), 1.35-1.30 (m, 2H), 1.20-1.12 (m, 3H), 1.01-0.95 (m, 4H), 0.93 (s, 3H) ppm. LC-MS: MS (ESI): 689 m/z $[M+H]^+$, purity: 97% (214 nm), 96% (254 nm). retention time: 1.25 minutes (LC-MS method 40).

Example 300. Diastereomer 1 and 2 of (2S)-3-[6-(21,22-difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl)pyrazin-2-yl]-2-methyl-propanoic Acid

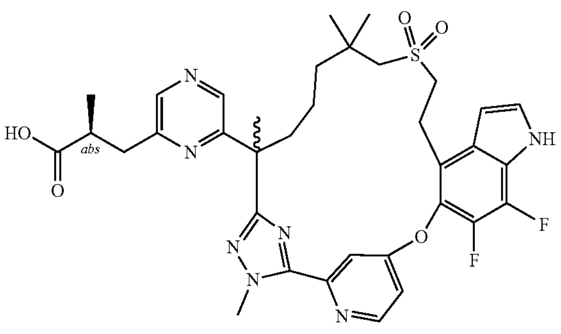 [SMILES: C[C@@H](Cc1cncc(C2(C)CCCC(C)(C)CS(=O)(=O)CCc3c(c(F)c(F)c4[nH]ccc34)Oc3ccnc(c3)-c3nc2nn3C)n1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2S)-3-(6-(7-((2-hydroxyethyl)sulfonyl)-2,6,6-trimethyl-1-(2-methylhydrazineyl)-1-oxoheptan-2-yl)pyrazin-2-yl)-2-methylpropanoate (Intermediate 69-30, 415 mg, 0.853 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)oxy)pyridine-2-carbimidothioate (Intermediate 150, 467 mg, 0.938 mmol), the reaction procedure sequence (Steps A to G) described for Example 6 was followed to prepare the title compounds. The mixture of diastereomers (25 mg) from the corresponding Step D was subject to chiral SFC separation under the following conditions: Instrument: SFC-150 (Waters); Column: IC 20*250 mm, 10 μm; Column temperature: 35° C.; Mobile phase: carbon dioxide/isopropanol (+0.5%7M ammonia in methanol)=45/55; Flow rate: 100 g/minute; Back pressure: 100 bar; Detection wavelength: 214 nm; Cycle time: 3.61 minutes; Sample solution: 25 mg dissolved in 25 mL of methanol; Injection volume: 4.5 mL. The first eluent (10 mg), after hydrolysis following conditions described in the corresponding Step F, was designated as Compound 300A (Diastereomer 1, 6.8 mg, white solid); The second eluent (8.8 mg), after hydrolysis following conditions described in the corresponding Step G, was designated as Compound 300B (Diastereomer 2, 5.8 mg, white solid).

Compound 300A (Diastereomer 1): $^1$H NMR (400 MHz, $CD_3OD$) δ 8.78 (d, J=5.6 Hz, 1H), 8.43-8.38 (m, 2H), 7.81 (s, 1H), 7.48 (dd, J=6.0, 2.0 Hz, 1H), 7.42 (d, J=3.2 Hz, 1H), 6.82-6.80 (m, 1H), 4.39 (s, 3H), 3.48-3.40 (m, 1H), 3.19-3.15 (m, 2H), 3.03-2.88 (m, 3H), 2.80-2.76 (m, 1H), 2.20-2.13 (m, 1H), 2.09-2.03 (m, 1H), 1.78 (s, 3H), 1.61-1.59 (m, 1H), 1.38-1.34 (m, 4H), 1.20 (d, J=6.8 Hz, 2H), 1.09 (s, 3H), 0.93-0.83 (m, 5H) ppm. LC-MS: MS (ESI): 708 m/z $[M+H]^+$, purity: >99% (214 nm), >99% (254 nm). retention time: 1.36 minutes (LC-MS method 40).

Compound 300B (Diastereomer 2): $^1$H NMR (400 MHz, $CD_3OD$) δ 8.80 (d, J=4.2 Hz, 1H), 8.44-8.35 (m, 2H), 7.80 (s, 1H), 7.49 (s, 1H), 7.42 (d, J=2.8 Hz, 1H), 6.81-6.80 (m, 1H), 4.39 (s, 3H), 3.46-3.42 (m, 1H), 3.24-3.17 (m, 2H), 3.15-2.95 (m, 2H), 2.89-2.86 (m, 1H), 2.85-2.75 (m, 1H), 2.20-2.14 (m, 1H), 2.10-2.03 (m, 1H), 1.77 (s, 3H), 1.61-1.59 (m, 1H), 1.38-1.34 (m, 4H), 1.20 (d, J=6.8 Hz, 2H), 1.09 (s, 3H), 0.98-0.83 (m, 5H) ppm. LC-MS: MS (ESI): 708 m/z $[M+H]^+$, purity: >99% (214 nm), >99% (254 nm). retention time: 1.36 minutes (LC-MS method 40).

Example 301. (2R)-3-[3-[(6R)-21,22-difluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

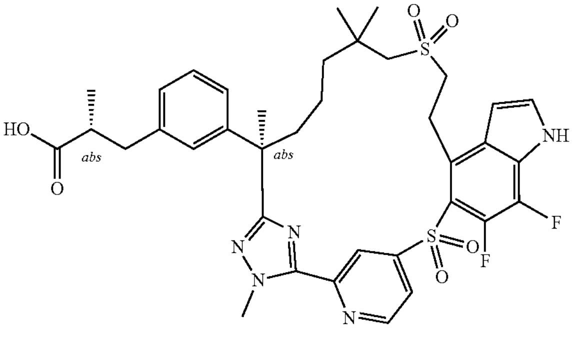 [SMILES: C[C@H](Cc1cccc([C@@]2(C)CCCC(C)(C)CS(=O)(=O)CCc3c(c(F)c(F)c4[nH]ccc34)S(=O)(=O)c3ccnc(c3)-c3nc2nn3C)c1)C(=O)O]

Methyl (2R)-3-[3-[(6R,13E)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,13,15,17,20,22,25,27-decaen-6-yl]phenyl]-2-methyl-propanoate

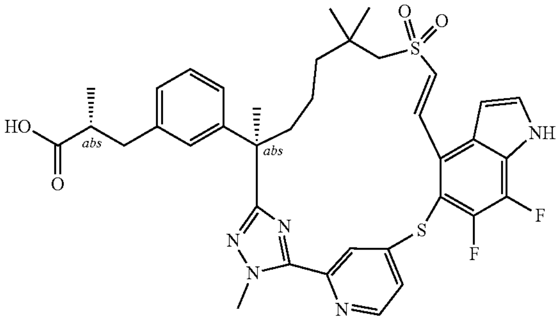 [SMILES: C[C@H](Cc1cccc([C@@]2(C)CCCC(C)(C)CS(=O)(=O)/C=C/c3c(c(F)c(F)c4[nH]ccc34)Sc3ccnc(c3)-c3nc2nn3C)c1)C(=O)O]

Step A: Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 110 g, 226.97 mmol), and methyl 5-((4-bromo-6-fluoro-1H-indol-5-yl)thio)-2-fluorobenzimidothioate hydroiodide (Intermediate 76) with methyl 4-((4-bromo-6,7-difluoro-1H-indol-5-yl)thio)pyridine-2-carbimidothioate (Intermediate 150-8, 112 g, 272.36 mmol), the reaction procedure sequence (Steps A to C) described for Example 204 was followed to prepare the title compound (Compound 301, 45 g) as a white solid. LC-MS: MS (ESI): 734 m/z $[M+H]^+$, purity: 95% (254 nm), retention time: 2.17 minutes (LC-MS method 003).

Methyl (2R)-3-[3-[(6R)-21,22-Difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate

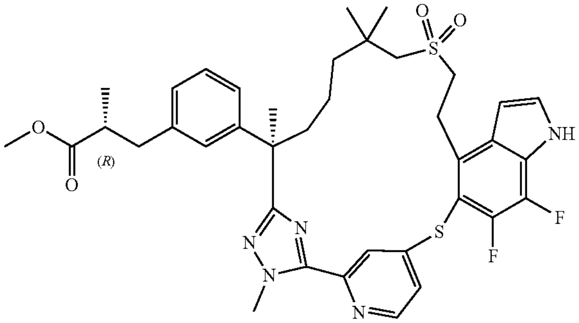 [SMILES: COC(=O)[C@H](C)Cc1cccc([C@@]2(C)CCCC(C)(C)CS(=O)(=O)CCc3c(c(F)c(F)c4[nH]ccc34)Sc3ccnc(c3)-c3nc2nn3C)c1]

Step B: To a stirred solution of the product from Step A (44 g, 59.9 mmol) in toluene (500 mL) was added tosyl hydrazine (111.6 g, 599.5 mmol). The reaction was stirred at 110° C. for 2 hours and concentrated. The residue was quenched with 1M hydrochloric acid (1000 mL), and extracted with ethyl acetate (1000 mL). The organic extract was washed with brine (1000 mL×2), dried over anhydrous sodium sulfate, filtered, and concentrated. The crude product was purified by flash chromatography (330 g silica gel column, eluting with 0-60% ethyl acetate in petroleum ether) to give the title compound (40 g, 91%) as a white solid. LC-MS: MS (ESI): 736 m/z $[M+H]^+$, purity: 94% (254 nm), retention time: 2.17 minutes (LC-MS method 003).

Compound 301: (2R)-3-[3-[(6R)-21,22-difluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

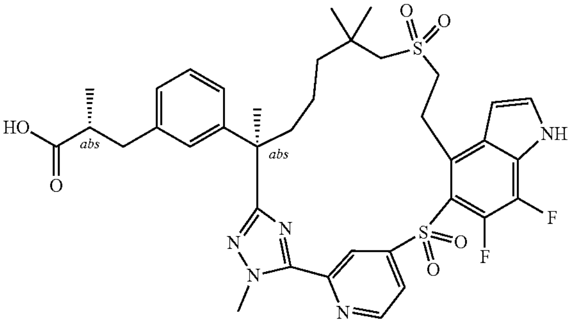 [SMILES: C[C@H](Cc1cccc([C@@]2(C)CCCC(C)(C)CS(=O)(=O)CCc3c(c(F)c(F)c4[nH]ccc34)S(=O)(=O)c3ccnc(c3)-c3nc2nn3C)c1)C(=O)O]

Step C: The title compound was prepared by following the reaction conditions described for Step B of Example 269 using (2R)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic acid (Step B product of this Example, 40 g, 54.3 mmol). The formed mixture (20 g) after the oxidation of the thioether to the sulfoxide, was separated by the following SFC conditions: Instrument: SFC-150 (Waters); Column: OD 20*250 mm, 10 μm; Column temperature: 35° C.; Mobile phase: Carbon dioxide/methanol[Additive: 0.2% ammonia in methanol (7M)]=60/40; Flow rate: 100 g/minute; Back pressure: 100 bar; Detection wavelength: 214 nm; Cycle time: 2.7 minutes; Sample solution: 418 mg dissolved in 30 mL of methanol; Injection volume: 1 mL. The first eluent (4 g, Diastereomer 1), the unwanted diastereomer was removed. The second eluent (13 g) was further hydrolyzed to Compound 269 (10.9 g, Diastereomer 2, white solid). 22 mg of the third eluent (0.874 g total separated from this reaction) was further hydrolyzed to the title compound (Compound 301, 20 mg, white solid).

Compound 301: LC-MS: MS (ESI): 754 m/z $[M+H]^+$, purity: >99% (214 nm), retention time: 1.43 minutes (LC-MS method 008). $^1H$ NMR (500 MHz, $CD_3OD$)$^1H$ NMR (400 MHz, $CD_3OD$) δ 9.02 (d, J=4.8 Hz, 1H), 8.74 (s, 1H), 8.06 (d, J=4.8 Hz, 1H), 7.51 (d, J=3.2 Hz, 1H), 7.18-7.14 (m, 1H), 7.09-7.07 (m, 1H), 7.02-6.97 (m, 2H), 6.81 (t, J=3.2 Hz, 1H), 4.29 (s, 3H), 3.85-3.79 (m, 1H), 3.71-3.64 (m, 1H), 3.56-3.48 (m, 1H), 3.25-3.15 (m, 3H), 2.97-2.92 (m, 1H), 2.65-2.57 (m, 2H), 2.33-2.28 (m, 1H), 1.93-1.87 (m, 1H), 1.76 (s, 3H), 1.60-1.45 (m, 2H), 1.36-1.31 (m, 2H), 1.25 (s, 3H), 1.21 (s, 3H), 1.09 (d, J=6.8 Hz, 3H) ppm.

Example 302. Compound 302A. (1S)-1-[3-[(6R)-22,28-Difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]ethane-1,2-diol

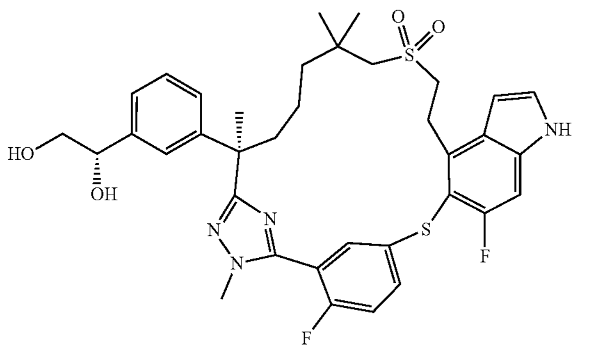 [SMILES: Cn1nc2nc1-c1cc(ccc1F)Sc1c(F)cc3[nH]ccc3c1CCS(=O)(=O)CC(C)(C)CCC[C@]2(C)c1cccc([C@H](O)CO)c1]

Compound 302B. Diastereomer 2 of (1S)-1-[3-[(6R)-22,28-Difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]ethane-1,2-diol

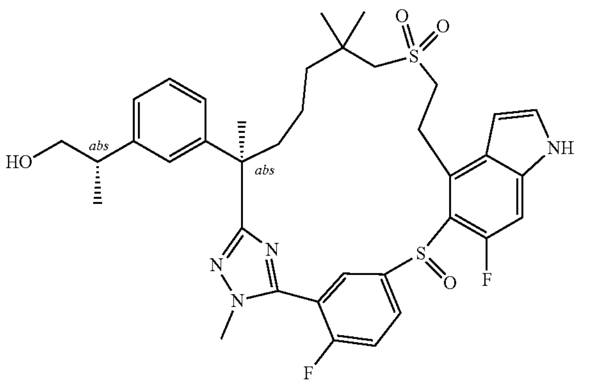 [SMILES: C[C@H](CO)c1cccc([C@@]2(C)CCCC(C)(C)CS(=O)(=O)CCc3c(c(F)cc4[nH]ccc34)S(=O)c3ccc(F)c(c3)-c3nc2nn3C)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with (S)-1-(3-((R)-2-(5-(5-((4-bromo-6-fluoro-1H-indol-5-yl)thio)-2-fluorophenyl)-1-methyl-1H-1,2,4-triazol-3-yl)-7-((2-hydroxyethyl)sulfonyl)-6,6-dimethylheptan-2-yl)phenyl)ethane-1,2-diyl diacetate (2.5 g, 4.73 mmol), the following reaction procedure sequence, Steps A to C described for Example 204, Step B of Example 301 (for double bond reduction), Step E and F of Example 204 (for indole protection and sulfide enantio-selective oxidation), and lastly, Step G and H of Example 204 (removal of protection group Ts and acetate ester hydrolysis), was carried out to give the title compound (Compound 302B, 46.6 mg) as a white solid. Compound 302A (33.7 mg) was the hydrolysis product (following conditions of Step H of Example 204) of the intermediate from the corresponding Step B of Example 301 (100 mg of this intermediate was used).

Compound 302A: LC-MS: MS (ESI): 695 m/z $[M+H]^+$, purity: >99% (214 nm), retention time: 1.69 minutes (LC-MS method 004). $^1H$ NMR (400 MHz, $CD_3OD$) δ 7.83-7.76 (m, 1H), 7.72 (dd, J=6.5, 2.3 Hz, 1H), 7.33-7.25 (m, 3H), 7.24-7.14 (m, 3H), 7.07 (d, J=7.6 Hz, 1H), 6.59 (d, J=3.2 Hz, 1H), 4.64-4.58 (m, 1H), 3.77 (d, J=1.7 Hz, 3H), 3.73-3.63 (m, 1H), 3.56-3.54 (m, 1H), 3.44 (t, J=7.1 Hz, 1H), 3.27-3.22 (m, 1H), 2.96-2.90 (m, 2H), 2.82 (s, 2H), 2.35 (t, J=8.1 Hz, 1H), 2.30-2.23 (m, 1H), 2.06-2.00 (m, 1H), 1.92-1.83 (m, 1H), 1.69 (s, 3H), 1.55-1.47 (m, 1H), 1.44-1.39 (m, 1H), 1.17 (s, 3H), 1.12 (s, 3H) ppm.

Compound 302B: LC-MS: MS (ESI): 711 m/z $[M+H]^+$, purity: >99% (214 nm), retention time: 1.13 minutes (LC-MS method 004). $^1H$ NMR (400 MHz, $CD_3OD$) δ 8.13 (bs, 1H), 7.91 (bs, 1H), 7.56 (t, J=9.2 Hz, 1H), 7.37 (d, J=3.3 Hz, 1H), 7.30 (s, 1H), 7.25-7.07 (m, 4H), 6.67 (s, 1H), 4.63-4.57 (m, 1H), 4.00-3.88 (m, 1H), 3.85 (d, J=2.2 Hz, 3H), 3.72-3.63 (m, 1H), 3.60-3.44 (m, 3H), 3.39-3.32 (m, 1H), 3.13-2.99 (m, 2H), 2.35-2.25 (m, 1H), 1.99-1.88 (m, 1H), 1.72 (s, 3H), 1.50-1.34 (m, 3H), 1.22 (s, 3H), 1.13 (s, 3H), 1.08-0.99 (m, 1H) ppm.

Example 303. Compound 303A. 1-[[3-[(6R)-21,22,28-Trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]methyl]cyclopropanecarboxylic acid

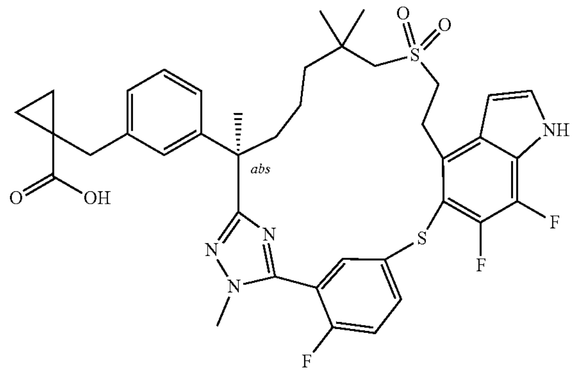 [SMILES: Cn1nc2nc1-c1cc(ccc1F)Sc1c(F)c(F)c3[nH]ccc3c1CCS(=O)(=O)CC(C)(C)CCC[C@]2(C)c1cccc(CC2(C(=O)O)CC2)c1]

Compound 303B. Diastereomer 2 of 1-[[3-[(6R)-21,22,28-Trifluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]methyl]cyclopropanecarboxylic Acid

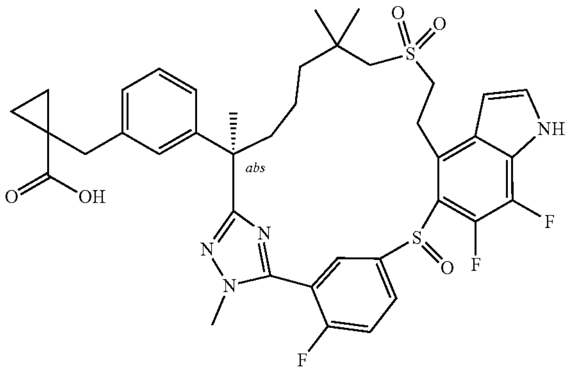 [SMILES: Cn1nc2nc1-c1cc(ccc1F)S(=O)c1c(F)c(F)c3[nH]ccc3c1CCS(=O)(=O)CC(C)(C)CCC[C@]2(C)c1cccc(CC2(C(=O)O)CC2)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-1-(3-(7-((2-hydroxyethyl)sulfonyl)-2,6,6-trimethyl-1-(2-methylhydrazineyl)-1-oxoheptan-2-yl)benzyl)cyclopropane-1-carboxylate (Intermediate 137-12, 380 mg, 0.765 mmol), the reaction sequence, Steps A to D, F, and H described for Example 204, was followed to give the title compound (Compound 303B, 8.2 mg) as a white solid. Compound 303A (7.3 mg) was the hydrolysis product (following conditions of Step H of Example 204) of the intermediate from the corresponding Step D of Example 204 (30 mg of this intermediate was used).

Compound 303A: LC-MS: MS (ESI): 751 m/z $[M+H]^+$, purity: >99% (214 nm), retention time: 1.54 minutes (LC-MS method 45). $^1$H NMR (400 MHz, $CD_3OD$) δ 7.86-7.82 (m, 1H), 7.79 (dd, J=6.4, 2.0 Hz, 1H), 7.38-7.31 (m, 2H), 7.17-7.13 (m, 1H), 7.09-6.98 (m, 3H), 6.68-6.66 (m, 1H), 3.80 (d, J=1.6 Hz, 3H), 3.76-3.67 (m, 2H), 3.29-3.24 (m, 1H), 3.04-2.95 (m, 2H), 2.91 (s, 2H), 2.30-2.25 (m, 1H), 1.91-1.86 (m, 1H), 1.69 (s, 3H), 1.47-1.41 (m, 2H), 1.35-1.30 (m, 2H), 1.19-1.15 (m, 8H), 0.93-0.90 (m, 1H), 0.76-0.72 (m, 2H) ppm.

Compound 303B: LC-MS: MS (ESI): 767 m/z $[M+H]^+$, purity: 99% (214 nm), retention time: 1.28 minutes (LC-MS method 45). $^1$H NMR (400 MHz, DMSO-$d_6$) δ 7.78-7.74 (m, 2H), 7.54-7.53 (m, 1H), 7.47-7.43 (m, 1H), 7.13-7.08 (m, 2H), 7.02 (d, J=7.6 Hz, 1H), 6.96 (d, J=7.6 Hz, 1H), 6.61 (s, 1H), 3.71 (d, J=2.0 Hz, 3H), 3.01 (s, 2H), 2.84-2.79 (m, 2H), 2.21-2.15 (m, 2H), 2.00-1.97 (m, 1H), 1.72-1.67 (m, 1H), 1.62 (s, 3H), 1.47-1.38 (m, 1H), 1.31-1.23 (m, 3H), 1.02 (s, 3H), 0.98 (s, 6H), 0.88-0.83 (m, 1H), 0.71-0.68 (m, 2H) ppm.

Example 304. (2S)-3-[3-[(6R)-21,22-Difluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

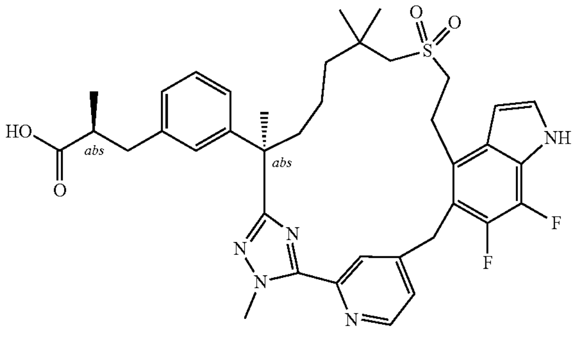 [SMILES: C[C@@H](Cc1cccc([C@@]2(C)CCCC(C)(C)CS(=O)(=O)CCc3c(c(F)c(F)c4[nH]ccc34)Cc3ccnc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 0.18 g, 0.371 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)methyl)pyridine-2-carbimidothioate (Intermediate 150-9, 0.15 g, 0.37 mmol), the reaction procedure sequence, Steps A to D and F described for Example 6, was followed to give the title compound (Compound 304, 25 mg) as a white solid. LC-MS: MS (ESI): 704 m/z $[M+H]^+$, purity: >99% (214 nm), retention time: 1.40 minutes (LC-MS method 40). $^1$H NMR (400 MHz, $CD_3OD$) δ 8.57 (d, J=5.2 Hz, 1H), 8.32 (s, 1H), 7.37 (d, J=5.2 Hz, 1H), 7.30 (d, J=3.2 Hz, 1H), 7.16 (t, J=7.6 Hz, 1H), 7.11-7.09 (m, 1H), 7.05-6.99 (m, 2H), 6.53 (t, J=2.8 Hz, 1H), 4.37-4.32 (m, 1H), 4.29 (s, 3H), 4.21-4.17 (m, 1H), 3.48-3.36 (m, 2H), 3.17-3.08 (m, 2H), 2.98-2.88 (m, 3H), 2.67-2.58 (m, 2H), 2.41-2.36 (m, 1H), 1.95-1.86 (m, 1H), 1.72 (s, 3H), 1.65-1.43 (m, 3H), 1.25 (s, 3H), 1.25-1.19 (m, 1H), 1.09-1.07 (m, 6H) ppm.

Example 305. (2R)-3-[3-[(6R)-21,22-Difluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic acid

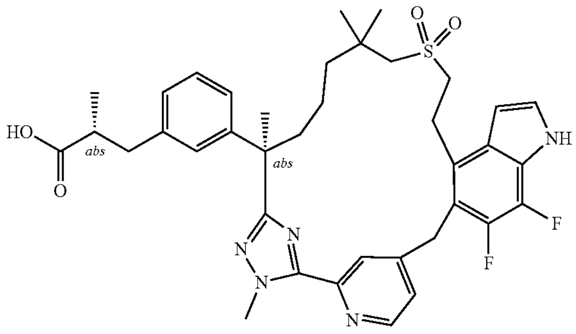 [SMILES: C[C@H](Cc1cccc([C@@]2(C)CCCC(C)(C)CS(=O)(=O)CCc3c(c(F)c(F)c4[nH]ccc34)Cc3ccnc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 489 mg, 1.01 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)methyl)pyridine-2-carbimidothioate (Intermediate 150-9, 400 mg, 1.01 mmol), the reaction procedure sequence, Steps A to D and F described for Example 6, was followed to give the title compound (Compound 305, 53 mg) as a white solid. LC-MS: MS (ESI): 704 m/z $[M+H]^+$, purity: >99% (214 nm), retention time: 1.47 minutes (LC-MS method 45). $^1$H NMR (400 MHz, $CD_3OD$) δ 8.59 (d, J=4.4 Hz, 1H), 8.34 (s, 1H), 7.40 (d, J=4.8 Hz, 1H), 7.33 (d, J=3.2 Hz, 1H), 7.17 (t, J=7.6 Hz, 1H), 7.13 (s, 1H), 7.05-7.02 (m, 2H), 6.55 (t, J=3.2 Hz, 1H), 4.38-4.19 (m, 5H), 3.49-3.39 (m, 2H), 3.19-3.08 (m, 2H), 3.00-2.90 (m, 3H), 2.65-2.57 (m, 2H), 2.43-2.38 (m, 1H), 1.97-1.90 (m, 1H), 1.74 (s, 3H), 1.66-1.56 (m, 2H), 1.51-1.43 (m, 1H), 1.37-1.21 (m, 4H), 1.11-1.09 (m, 6H) ppm 2Example 306. 1-[[3-[(6R)-21,22-Difluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic Acid

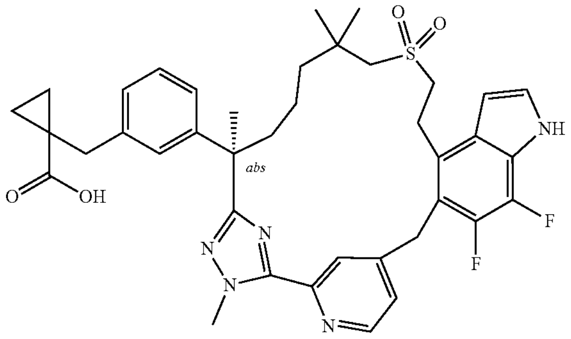 [SMILES: Cn1nc2nc1-c1cc(ccn1)Cc1c(F)c(F)c3[nH]ccc3c1CCS(=O)(=O)CC(C)(C)CCC[C@]2(C)c1cccc(CC2(C(=O)O)CC2)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-1-(3-(7-((2-hydroxyethyl)sulfonyl)-2,6,6-trimethyl-1-(2-methylhydrazineyl)-1-oxoheptan-2-yl)benzyl) cyclopropane-1-carboxylate (Intermediate 137-12, 160 mg, 0.322 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)methyl)pyridine-2-carbimidothioate (Intermediate 150-9, 128 mg, 0.322 mmol), the reaction procedure sequence, Steps A to D and F described for Example 6, was followed to give the title compound (Compound 306, 3.6 mg) as a white solid. LC-MS: MS (ESI): 716 m/z [M+H]$^+$, purity: 99% (214 nm), retention time: 1.46 minutes (LC-MS method 45). $^1$H NMR (400 MHz, $CD_3OD$) δ 8.60 (d, J=5.2 Hz, 1H), 8.34 (s, 1H), 7.40 (d, J=5.2 Hz, 1H), 7.33 (d, J=3.6 Hz, 1H), 7.18-7.14 (m, 2H), 7.08-7.04 (m, 2H), 6.55 (t, J=3.2 Hz, 1H), 4.38-4.19 (m, 5H), 3.17-3.11 (m, 2H), 3.01-2.91 (m, 4H), 2.40-2.37 (m, 1H), 2.05-2.03 (m, 1H), 1.97-1.91 (m, 1H), 1.73 (s, 3H), 1.63-1.56 (m, 2H), 1.35-1.27 (m, 5H), 1.18-1.11 (m, 5H), 0.93-0.87 (m, 1H), 0.72-0.71 (m, 2H) ppm.

Example 307. 3-[3-[(6R)-21,22-Difluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

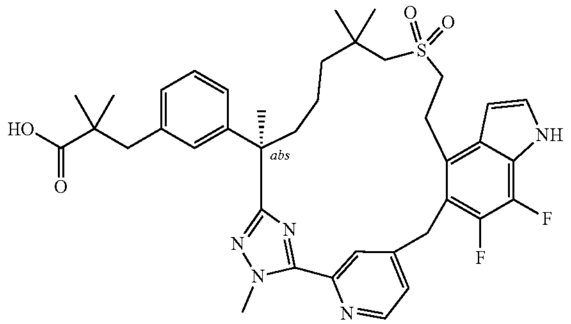

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 0.20 g, 0.404 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)methyl)pyridine-2-carbimidothioate (Intermediate 150-9, 0.16 g, 0.404 mmol), the reaction procedure sequence, Steps A to D and F described for Example 6, was followed to give the title compound (Compound 307, 29 mg) as a white solid. LC-MS: MS (ESI): 718 m/z [M+H]$^+$, purity: 96% (214 nm), retention time: 1.51 minutes (LC-MS method 45). $^1$H NMR (400 MHz, $CD_3OD$) δ 8.58 (d, J=5.2 Hz, 1H), 8.32 (s, 1H), 7.38 (d, J=4.8 Hz, 1H), 7.31 (d, J=3.2 Hz, 1H), 7.14 (t, J=7.6 Hz, 1H), 7.10-7.07 (m, 1H), 7.04 (d, J=8.0 Hz, 1H), 6.98 (d, J=7.6 Hz, 1H), 6.53 (t, J=3.2 Hz, 1H), 4.35 (d, J=14.4 Hz, 1H), 4.29 (s, 3H), 4.20 (d, J=14.4 Hz, 1H), 3.48-3.40 (m, 2H), 3.16-3.08 (m, 2H), 2.99-2.94 (m, 2H), 2.81 (s, 2H), 2.41-2.36 (m, 1H), 1.95-1.89 (m, 1H), 1.72 (s, 3H), 1.61-1.58 (m, 2H), 1.49-1.44 (m, 1H), 1.35-1.22 (m, 1H), 1.25 (s, 3H), 1.10 (s, 9H) ppm.

Example 308. 1-[[3-[(6R)-21,22-Difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic Acid

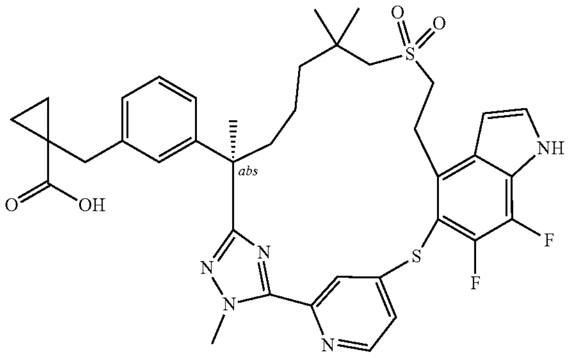 [SMILES: Cn1nc2nc1-c1cc(ccn1)Sc1c(F)c(F)c3[nH]ccc3c1CCS(=O)(=O)CC(C)(C)CCC[C@]2(C)c1cccc(CC2(C(=O)O)CC2)c1]

Methyl 1-[[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylate

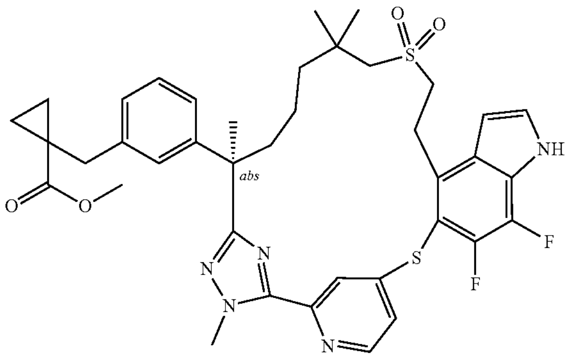 [SMILES: COC(=O)C1(Cc2cccc([C@@]3(C)CCCC(C)(C)CS(=O)(=O)CCc4c(c(F)c(F)c5[nH]ccc45)Sc4ccnc(c4)-c4nc3nn4C)c2)CC1]

Step A. Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-1-(3-(7-((2-hydroxyethyl)sulfonyl)-2,6,6-trimethyl-1-(2-methylhydrazineyl)-1-oxoheptan-2-yl)benzyl)cyclopropane-1-carboxylate (Intermediate 137-12, 400 mg, 0.805 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)thio)pyridine-2-carbimidothioate (Intermediate 150-8, 500 mg, 1.2 mmol), the reaction procedure sequence, Steps A to D) described for Example 6, was followed to give the title compound (120 mg) as a white solid. LC-MS: MS (ESI): 748 m/z $[M+H]^+$, purity: 98% (214 nm), retention time: 1.90 minutes (LC-MS method 021).

Compound 308. 1-[[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic acid

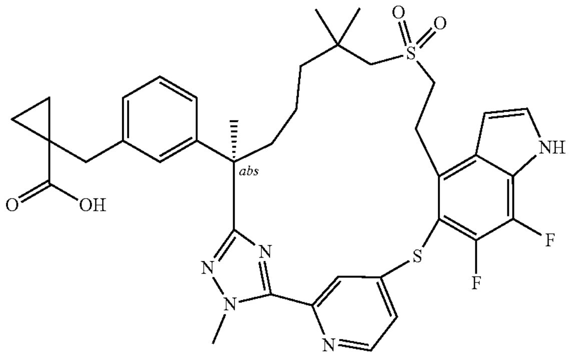

Step B. The product of Step A (10 mg, 0.013 mmol) was subjected to the conditions described for Step F of Example 6 to give the title compound as a white solid (5.2 mg, 53%). LC-MS: MS (ESI): 734 m/z $[M+H]^+$, purity: >99% (214 nm), retention time: 1.53 minutes (LC-MS method 40). $^1H$ NMR (400 MHz, $CD_3OD$) δ 8.53 (d, J=5.2 Hz, 1H), 7.71 (s, 1H), 7.47-7.44 (m, 2H), 7.10 (d, J=8.0 Hz, 1H), 7.02-7.00 (m, 2H), 6.93 (d, J=6.8 Hz, 1H), 6.78 (t, J=2.8 Hz, 1H), 4.28 (s, 3H), 3.72-3.65 (m, 2H), 3.21-3.17 (m, 2H), 2.92 (d, J=15.2 Hz, 1H), 2.81 (d, J=15.2 Hz, 1H), 2.75 (d, J=14.8 Hz, 1H), 2.66 (d, J=14.8 Hz, 1H), 2.07-1.99 (m, 1H), 1.72-1.60 (m, 1H), 1.65 (s, 3H), 1.34-1.09 (m, 8H), 1.00-0.90 (m, 1H), 0.96 (s, 3H), 0.74-0.64 (m, 2H) ppm.

Example 309. Diastereomer 2 of 1-[[3-[(6R)-21,22-Difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic Acid

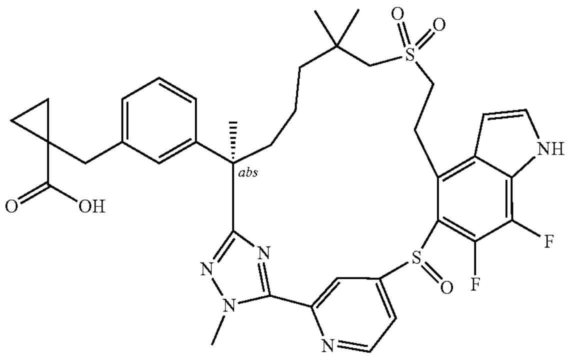 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(CC2(C(=O)O)CC2)c1]

The product from Step A of Example 308 (110 mg, 0.147 mmol) was subjected to the conditions described for Step F of Example 204 to afford the methyl ester of the title compound (60 mg). 15 mg of this methyl ester was then hydrolyzed, based on conditions described in Step H of Example 204, to afford the title compound (Compound 309, 6.1 mg) as a white solid. LC-MS: MS (ESI): 750 m/z $[M+H]^+$, purity: 98% (214 nm), retention time: 1.97 minutes (LC-MS method 40). $^1H$ NMR (400 MHz, $CD_3OD$) δ 8.94-8.57 (m, 2H), 7.44 (d, J=3.0 Hz, 1H), 7.26-6.54 (m, 6H), 4.31 (s, 3H), 3.65-3.57 (m, 1H), 3.21-3.00 (m, 3H), 2.94-2.82 (m, 2H), 2.51-2.22 (m, 1H), 1.78-1.69 (m, 4H), 1.55-1.25 (m, 8H), 1.09-1.01 (m, 6H), 0.65 (m, 2H) ppm.

Example 310. 1-[[3-[(6R)-21,22-Difluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic Acid

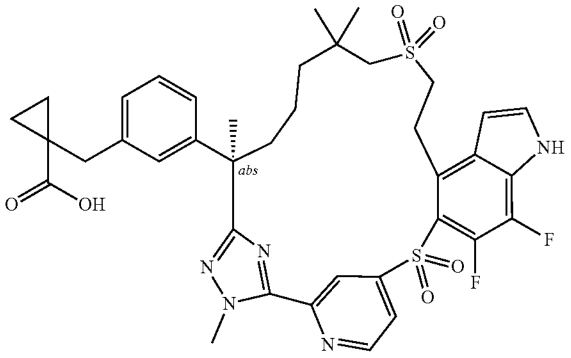 [SMILES: Cn1nc2nc1-c1cc(ccn1)S(=O)(=O)c1c(F)c(F)c3[nH]ccc3c1CCS(=O)(=O)CC(C)(C)CCC[C@]2(C)c1cccc(CC2(C(=O)O)CC2)c1]

Methyl 1-[[3-[(6R)-21,22-difluoro-3,6,10,10-tetramethyl-19-methylsulfonyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylate

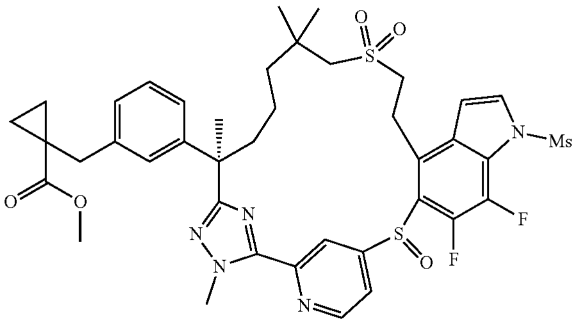 [SMILES: COC(=O)C1(Cc2cccc([C@@]3(C)CCCC(C)(C)CS(=O)(=O)CCc4c(c(F)c(F)c5c4ccn5S(C)(=O)=O)S(=O)c4ccnc(c4)-c4nc3nn4C)c2)CC1]

Step A: To a stirred solution of methyl 1-[[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylate (methyl ester of Example 309, 40 mg, 0.052 mmol) in dichloromethane (10 mL) was added at room temperature triethylamine (0.036 mL, 0.26 mmol) and methanesulfonyl chloride (0.0081 mL, 0.11 mmol). The reaction was stirred at room temperature for 3 hours, then diluted with dichloromethane (20 mL). The mixture was washed with brine (2×20 mL), dried over sodium sulfate, filtered, and concentrated. The residue was purified by flash column chromatography (20 g silica gel column, eluting with 0-60% ethyl acetate in petroleum ether) to give the title compound (36 mg, 82%) as a white solid. LC-MS: MS (ESI): 842 m/z $[M+H]^+$, purity: >99% (254 nm), retention time: 3.33 minutes (LC-MS method 46).

Compound 310: 1-[[3-[(6R)-21,22-difluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic acid

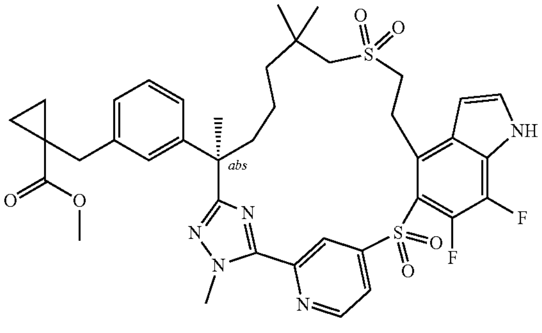 [SMILES: COC(=O)C1(Cc2cccc([C@@]3(C)CCCC(C)(C)CS(=O)(=O)CCc4c(c(F)c(F)c5[nH]ccc45)S(=O)(=O)c4ccnc(c4)-c4nc3nn4C)c2)CC1]

Step B: The product from step A (34 mg, 0.04 mmol) was submitted to the reaction conditions described in Step C of Example 180, followed by conditions described in Step D of Example 34 to afford the title compound (2.1 mg) as a white solid. LC-MS: MS (ESI): 766 m/z $[M+H]^+$, purity: >99% (214 nm), retention time: 2.01 minutes (LC-MS method 46). $^1$H NMR (400 MHz, DMSO-$d_6$) δ 12.58 (s, 1H), 11.92 (brs, 1H), 9.04 (d, J=5.2 Hz, 1H), 8.62 (s, 1H), 8.02 (d, J=5.6 Hz, 1H), 7.69 (d, J=3.2 Hz, 1H), 7.15-7.05 (m, 2H), 7.02 (d, J=7.6 Hz, 1H), 6.95 (d, J=7.6 Hz, 1H), 6.74-6.70 (m, 1H), 4.19 (s, 3H), 3.79-3.67 (m, 1H), 3.58-3.51 (m, 1H), 3.19-3.07 (m, 2H), 2.33-2.22 (m, 1H), 2.04-1.93 (m, 1H), 1.81-1.56 (m, 6H), 1.52-1.33 (m, 4H), 1.21 (s, 3H), 1.12-0.96 (m, 6H), 0.74-0.66 (m, 2H) ppm.

Example 311. (2R)-3-[3-[(6R)-22-Fluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

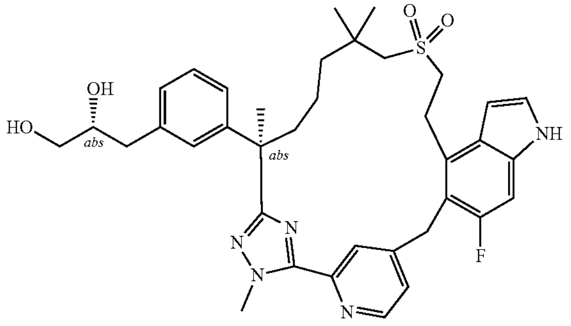 [SMILES: Cn1nc2nc1-c1cc(ccn1)Cc1c(F)cc3[nH]ccc3c1CCS(=O)(=O)CC(C)(C)CCC[C@]2(C)c1cccc(C[C@@H](O)CO)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with (R)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (Intermediate 137-16, 220 mg, 0.405 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)methyl)pyridine-2-carbimidothioate (Intermediate 150-3, 153 mg, 0.405 mmol), the reaction procedure sequence. Steps A to D described for Example 6, followed by Step G for Example 204, was followed to give the title compound (Compound 311, 7.8 mg) as a white solid. LC-MS: MS (ESI): 674 m/z $[M+H]^+$, purity: 99% (214 nm), retention time: 1.57 minutes (LC-MS method 004). $^1$H NMR (400 MHz, $CD_3OD$) δ 8.55 (d, J=5.2 Hz, 1H), 8.31 (s, 1H), 7.39 (d, J=5.2 Hz, 1H), 7.24 (d, J=3.2 Hz, 1H), 7.20-7.13 (m, 3H), 7.10-7.04 (m, 2H), 6.48 (d, J=3.2 Hz, 1H), 4.37-4.26 (m, 4H), 4.20-4/12 (m, 1H), 3.76-3.73 (m, 1H), 3.47-3.38 (m, 4H), 3.17-3.07 (m, 2H), 2.97-2.92 (m, 2H), 2.80-2.75 (m, 1H), 2.64-2.58 (m, 1H), 2.42-2.37 (m, 1H), 1.95-1.89 (m, 1H), 1.73 (s, 3H), 1.61-1.42 (m, 3H), 1.230-1.20 (m, 4H), 1.08 (s, 3H) ppm.

Example 312. (2S)-3-[3-[(6R)-22-Fluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

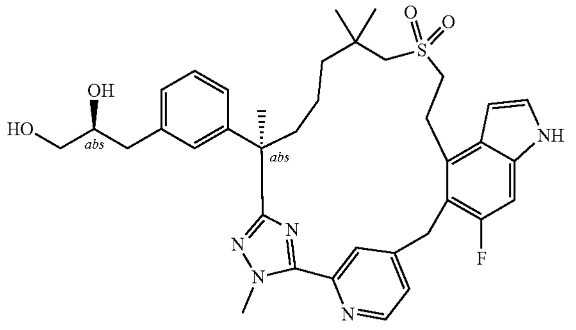 [SMILES: Cn1nc2nc1-c1cc(ccn1)Cc1c(F)cc3[nH]ccc3c1CCS(=O)(=O)CC(C)(C)CCC[C@]2(C)c1cccc(C[C@H](O)CO)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with (S)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (Intermediate 137-15, 260 mg, 0.479 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)methyl)pyridine-2-carbimidothioate (Intermediate 150-3, 237 mg, 0.628 mmol), the reaction procedure sequence, Steps A to D described for Example 6, followed by Step G for Example 204, was followed to give the title compound (Compound 312, 54 mg) as a white solid. LC-MS: MS (ESI): 674 m/z $[M+H]^+$, purity: 99% (214 nm), retention time: 1.85 minutes (LC-MS method 004). $^1$H NMR (400 MHz, $CD_3OD$) δ 8.55 (d, J=5.2 Hz, 1H), 8.31 (s, 1H), 7.39 (d, J=5.2 Hz, 1H), 7.24 (d, J=3.2 Hz, 1H), 7.20-7.12 (m, 3H), 7.08-7.04 (m, 2H), 6.49-6.46 (m, 1H), 4.34-4.31 (d, J=14.8 Hz, 1H), 4.27 (s, 3H), 4.15-4.11 (m, 1H), 3.78-3.72 (m, 1H), 3.47-3.42 (m, 4H), 3.14-3.06 (m, 2H), 2.97-2.92 (m, 2H), 2.80-2.75 (m, 1H), 2.64-2.58 (m, 1H), 2.42-2.37 (m, 1H), 1.96-1.89 (m, 1H), 1.73 (s, 3H), 1.62-1.38 (m, 4H), 1.25 (s, 3H), 1.08 (s, 3H) ppm.

Example 313. 1-[[3-[(6R)-22-Fluoro-3,6,10,10-tetramethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylic acid

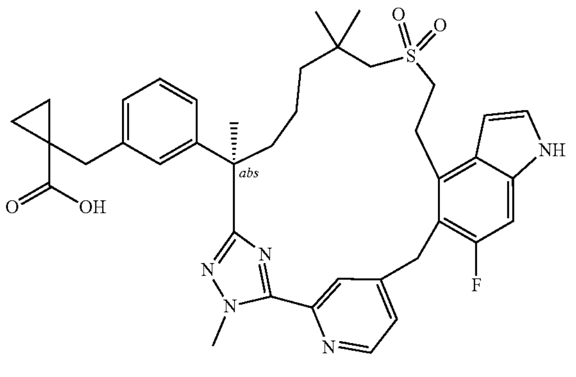 [SMILES: Cn1nc2nc1-c1cc(ccn1)Cc1c(F)cc3[nH]ccc3c1CCS(=O)(=O)CC(C)(C)CCC[C@]2(C)c1cccc(CC2(C(=O)O)CC2)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-1-(3-(7-((2-hydroxyethyl)sulfonyl)-2,6,6-trimethyl-1-(2-methylhydrazineyl)-1-oxoheptan-2-yl)benzyl)cyclopropane-1-carboxylate (Intermediate 137-12, 230 mg, 0.463 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)methyl)pyridine-2-carbimidothioate (Intermediate 150-3, 228 mg, 0.602 mmol), the reaction procedure sequence, Steps A to D described for Example 6, followed by Step G for Example 204, was followed to give the title compound (Compound 313, 35 mg) as a white solid. LC-MS: MS (ESI): 698 m/z $[M+H]^+$, purity: 99% (214 nm), retention time: 1.92 minutes (LC-MS method 004). $^1$H NMR (400 MHz, $CD_3OD$) δ 8.56 (d, J=4.8 Hz, 1H), 8.30 (s, 1H), 7.39 (d, J=8.0 Hz, 1H), 7.24 (d, J=3.2 Hz, 1H), 7.16-7.13 (m, 3H), 7.05-7.03 (m, 2H), 6.47 (d, J=3.2 Hz, 1H), 4.35 (d, J=15.6 Hz, 1H), 4.28 (s, 3H), 4.18-4.13 (m, 1H), 3.50-3.40 (m, 2H), 3.18-3.08 (m, 2H), 2.98-2.88 (m, 4H), 2.39-2.34 (m, 1H), 1.95-1.88 (m, 1H), 1.71 (s, 3H), 1.59-1.54 (m, 2H), 1.47-1.42 (m, 1H), 1.28-1.23 (m, 4H), 1.16-1.14 (m, 2H), 1.09 (s, 3H), 0.75 (d, J=2.4 Hz, 2H) ppm.

Example 314. Diastereomers 1 and 2 of (2S)-3-[6-(22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl)-2-pyridyl]-2-methyl-propanoic Acid

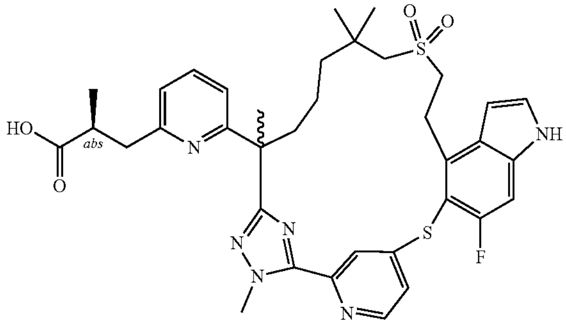

Methyl 3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl)-2-pyridyl]-2-methyl-propanoate

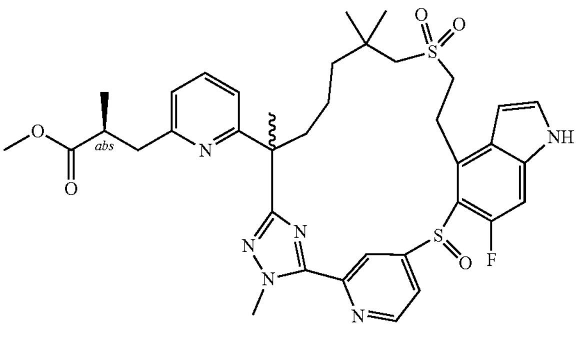 [SMILES: COC(=O)[C@@H](C)Cc1cccc(C2(C)CCCC(C)(C)CS(=O)(=O)CCc3c(c(F)cc4[nH]ccc34)S(=O)c3ccnc(c3)-c3nc2nn3C)n1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2S)-3-(6-(7-((2-hydroxyethyl)sulfonyl)-2,6,6-trimethyl-1-(2-methylhydrazineyl)-1-oxoheptan-2-yl)pyridin-2-yl)-2-methylpropanoate (Intermediate 107-2, 950 mg, 1.96 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)thio)pyridine-2-carbimidothioate (Intermediate 150-3, 853 mg, 2.15 mmol), the reaction procedure sequence, Steps A to D described for Example 6, was followed to give the title compound (230 mg) as a white solid. LC-MS: MS (ESI): 719 m/z $[M+H]^+$, purity: 76% (214 nm), retention time: 1.89 minutes (LC-MS method 022).

Compounds 314A and 314B: Diastereomers 1 and 2 of (2S)-3-[6-(22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl)-2-pyridyl]-2-methyl-propanoic Acid

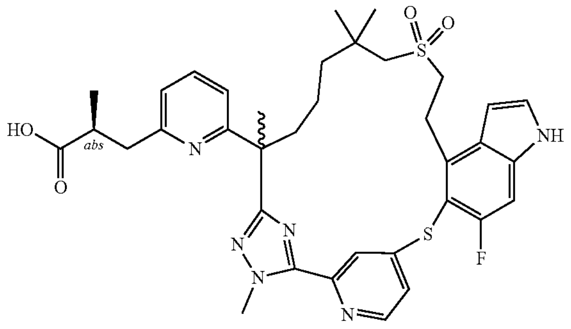

Step B: The product from Step A (50 mg, 0.070 mmol) was submitted to the reaction conditions described in Step G of Example 204 to afford a mixture of diastereomers of the title compound (25 mg, 51%). This mixture was subjected to chiral SFC separation under the following conditions: Instrument: SFC-150 (Waters); Column: IH 20*250 mm, 10 μm; Column temperature: 35° C.; Mobile phase: carbon dioxide/methanol (+0.2%7M ammonia in methanol)=55/45; Flow rate: 100 g/minute; Back pressure: 100 bar; Detection wavelength: 214 nm; Cycle time: 5.64 minutes; Sample solution: 100 mg dissolved in 35 ml of methanol; Injection volume: 4.5 ml. The first eluent (1.9 mg, 8%) was designated as Compound 314A; The second eluent (4.3 mg, 17%) was designated as Compound 314B.

Compound 314A: LC-MS: MS (ESI): 705 m/z $[M+H]^+$, purity: >99% (214 nm), retention time: 1.32 minutes (LC-MS method 003). $^1H$ NMR (400 MHz, $CD_3OD$) δ 8.52 (d, J=5.6 Hz, 1H), 7.66 (s, 1H), 7.50-7.42 (m, 2H), 7.37 (d, J=3.2 Hz, 1H), 7.28 (d, J=8.8 Hz, 1H), 7.00 (d, J=7.6 Hz, 1H), 6.75-6.70 (m, 2H), 4.29 (s, 3H), 3.75-3.70 (m, 2H), 3.20-3.15 (m, 3H), 3.06-2.92 (m, 1H), 2.87-2.80 (m, 1H), 2.60-2.54 (m, 2H), 2.10-2.03 (m, 1H), 1.90-1.82 (m, 1H), 1.66 (s, 3H), 1.40-1.28 (m, 4H), 1.13 (d, J=6.8 Hz, 3H), 1.07 (s, 3H), 0.96 (s, 3H) ppm.

Compound 314B: LC-MS: MS (ESI): 705 m/z $[M+H]^+$, purity: >99% (214 nm), retention time: 1.38 minutes (LC-MS method 003). $^1H$ NMR (400 MHz, $CD_3OD$) δ 8.51 (d, J=5.6 Hz, 1H), 7.67 (s, 1H), 7.50-7.44 (m, 2H), 7.37 (d, J=3.2 Hz, 1H), 7.28 (d, J=9.2 Hz, 1H), 7.00 (d, J=7.6 Hz, 1H), 6.77-6.69 (m, 2H), 4.29 (s, 3H), 3.75-3.70 (m, 2H), 3.21-3.08 (m, 3H), 3.07-2.90 (m, 1H), 2.87-2.80 (m, 1H), 2.60-2.56 (m, 2H), 2.10-2.00 (m, 1H), 1.88-1.79 (m, 1H), 1.66 (s, 3H), 1.40-1.28 (m, 4H), 1.14 (d, J=6.8 Hz, 3H), 1.07 (s, 3H), 0.96 (s, 3H) ppm.

Example 315. Compounds 315A and 315B Diastereomers 1, 2, 3 and 4 of (2S)-3-[6-(22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl)-2-pyridyl]-2-methyl-propanoic Acid

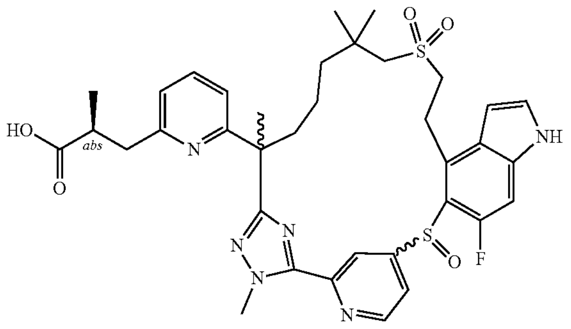 [SMILES: C[C@@H](Cc1cccc(C2(C)CCCC(C)(C)CS(=O)(=O)CCc3c(c(F)cc4[nH]ccc34)S(=O)c3ccnc(c3)-c3nc2nn3C)n1)C(=O)O]

and

Compound 315E (2S)-3-[6-(22-fluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl)-2-pyridyl]-2-methyl-propanoic Acid

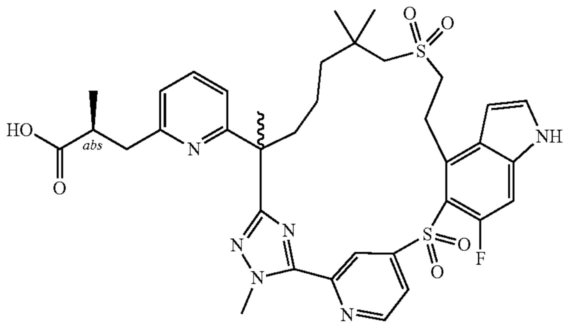 [SMILES: C[C@@H](Cc1cccc(C2(C)CCCC(C)(C)CS(=O)(=O)CCc3c(c(F)cc4[nH]ccc34)S(=O)(=O)c3ccnc(c3)-c3nc2nn3C)n1)C(=O)O]

The product from Step A of Example 314 (150 mg, 0.2 mmol, purity: 76%) was subjected to chiral SFC separation under the following conditions: Instrument: SFC-150 (Waters); Column: IH 20*250 mm, 10 μm; Column temperature: 35° C.; Mobile phase: carbon dioxide/methanol (0.2%7M ammonia in methanol)=50/50; Flow rate: 100 g/minute; Back pressure: 100 bar; Detection wavelength: 214 nm; Cycle time: 4.86 minutes; Sample solution: 40 mg dissolved in 35 ml methanol; Injection volume: 4.5 ml. The first eluent (41 mg, 36%) was submitted to the conditions described for Steps E, F, and Step G of Example 204, in this order, to afford a mixture. This mixture was then separated by reverse phase chiral preparative HPLC to give Compound 315E (first (fastest eluting) peak, 0.8 mg, white solid), Compound 315A (second peak, 3.0 mg, white solid) and Compound 315B (third peak, 3.1 mg, white solid).

The second eluent (48 mg, 33%) from SFC chiral separation was submitted to the conditions described for Steps E, F and Step G of Example 204, in this order, to afford a mixture. This mixture was then separated by reverse phase preparative HPLC to give Compounds 315C (1.0 mg, white solid) and 315D (5 mg, white solid).

Compound 315A: LC-MS: MS (ESI): 721 m/z $[M+H]^+$, purity: >99% (254 nm), retention time: 1.66 minutes (LC-MS method 021). $^1$H NMR (400 MHz, $CD_3OD$) δ 8.81 (s, 1H), 7.53 (t, J=7.2 Hz, 1H), 7.45-7.35 (m, 1H), 7.25 (s, 1H), 7.06 (d, J=7.6 Hz, 1H), 6.90-6.83 (m, 1H), 6.69-6.61 (m, 1H), 4.29 (s, 3H), 3.65-3.60 (m, 1H), 3.22-3.07 (m, 3H), 3.04-2.87 (m, 2H), 2.15-2.12 (m, 3H), 1.77 (s, 3H), 1.65-1.30 (m, 5H), 1.16 (d, J=7.0 Hz, 6H), 1.04-1.01 (m, 4H) ppm.

Compound 315B: LC-MS: MS (ESI): 721 m/z $[M+H]^+$, purity: >99% (254 nm), retention time: 1.67 minutes (LC-MS method 021). $^1$H NMR (400 MHz, DMSO-$d_6$) δ 11.74 (s, 1H), 8.83-8.76 (m, 1H), 7.52-7.45 (m, 3H), 7.26-7.24 (m, 1H), 7.04-7.02 (m, 1H), 6.76-6.71 (m, 1H), 6.50-6.42 (m, 1H), 4.27 (s, 3H), 3.54-3.51 (m, 2H), 3.13-2.96 (m, 4H), 2.89-2.54 (m, 3H), 2.01-1.92 (m, 1H), 1.71 (s, 3H), 1.50-1.20 (m, 8H), 0.86-0.83 (m, 5H), 0.90-0.80 (m, 1H) ppm.

Compound 315C: LC-MS: MS (ESI): 721 m/z $[M+H]^+$, purity: >99% (254 nm), retention time: 1.41 minutes (LC-MS method 43). $^1$H NMR (400 MHz, $CD_3OD$) δ 8.82 (brs, 1H), 7.52 (t, J=7.6 Hz, 1H), 7.40 (d, J=3.2 Hz, 1H), 7.30-7.20 (m, 1H), 7.05 (d, J=7.6 Hz, 1H), 6.90-6.80 (m, 1H), 6.75-6.60 (m, 1H), 4.28 (s, 3H), 3.70-3.60 (s, 1H), 3.23-3.07 (m, 3H), 3.05-2.98 (m, 1H), 2.91-2.84 (m, 1H), 2.23-2.15 (m, 2H), 2.03-1.84 (m, 1H), 1.76 (s, 3H), 1.65-1/45 (m, 2H), 1.40-1.30 (m, 3H), 1.21-1.15 (m, 4H), 1.07-1.00 (m, 5H), 0.95-0.89 (m, 1H) ppm.

Compound 315D: LC-MS: MS (ESI): 721 m/z $[M+H]^+$, purity: >99% (254 nm), retention time: 1.41 minutes (LC-MS method 43). $^1$H NMR (400 MHz, $CD_3OD$) δ 8.96 (s, 1H), 8.82 (s, 1H), 7.48 (s, 1H), 7.38-7.15 (m, 2H), 7.01 (s, 1H), 6.85-6.78 (m, 1H), 6.65-6.55 (m, 1H), 4.33 (s, 3H), 3.64-3.51 (m, 1H), 3.20-2.91 (m, 5H), 2.90-2.80 (m, 2H), 2.55-2.45 (m, 1H), 1.95-1.89 (s, 1H), 1.76 (s, 3H), 1.64-1.58 (m, 1H), 1.55-1.44 (m, 3H), 1.35-1.17 (m, 4H), 1.16-1.03 (m, 5H), 0.93-0.88 (m, 1H) ppm.

Compound 315E: LC-MS: MS (ESI): 737 m/z $[M+H]^+$, purity: 95% (254 nm), retention time: 1.72 minutes (LC-MS method 021). $^1$H NMR (400 MHz, $CD_3OD$) δ 8.98 (d, J=4.8 Hz, 1H), 8.72 (d, J=1.2 Hz, 1H), 8.04 (d, J=5.2 Hz, 1H), 7.50 (t, J=7.6 Hz, 1H), 7.43 (d, J=3.2 Hz, 1H), 7.26 (d, J=12.4 Hz, 1H), 7.03 (d, J=7.6 Hz, 1H), 6.80 (d, J=7.6 Hz, 1H), 6.73 (d, J=2.8 Hz, 1H), 4.3 (s, 3H), 3.89-3.80 (m, 1H), 3.75-3.70 (m, 1H), 3.20-3.15 (m, 2H), 2.98-2.90 (m, 1H), 2.90-2.83 (m, 1H), 2.40-2.30 (m, 1H), 2.24-2.16 (m, 2H), 2.10-1.95 (m, 2H), 1.78 (s, 3H), 1.67-1.58 (m, 1H), 1.55-1.49 (m, 1H), 1.31-1.24 (m, 1H), 1.25-1.20 (m, 6H), 1.14 (d, J=7.2 Hz, 3H), 0.93-0.89 (m, 1H) ppm.

Example 316. Diastereomers 1 and 2 of (2S)-3-[3-[(6R)-21,22-difluoro-3,6,10,10,24-pentamethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methylpropanoic Acid

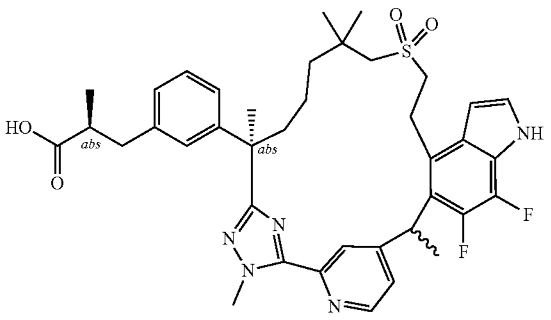 [SMILES: CC1c2ccnc(c2)-c2nc(nn2C)[C@@](C)(c2cccc(C[C@H](C)C(=O)O)c2)CCCC(C)(C)CS(=O)(=O)CCc2c1c(F)c(F)c1[nH]ccc21]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 425 mg, 0.877 mmol), and methyl 5-((4-bromo-6-fluoro-1H-indol-5-yl)oxy)-2-fluorobenzimidothioate hydroiodide (Intermediate 14-1) with methyl 4-(1-(4-bromo-6,7-difluoro-1H-indol-5-yl)ethyl)pyridine-2-carbimidothioate (Intermediate 150-10, 360 mg, 0.877 mmol), the reaction procedure sequence, Steps A to D and F described for Example 6, was followed to give a mixture of the title compounds. This mixture was then subjected to chiral SFC separation under the following conditions: Instrument: SFC-150 (Waters); Column: OZ 20*250 mm, 10 μm; Column temperature: 35° C.; Mobile phase: carbon dioxide/methanol (+0.2%7M ammonia in methanol)=55/45; Flow rate: 100 g/minute; Back pressure: 100 bar; Detection wavelength: 214 nm; Cycle time: 6.15 minutes; Sample solution: 130 mg dissolved in 35 ml of methanol; Injection volume: 3 ml. The first eluent (38 mg, white solid) was designated as Compound 316A, and the second eluent (48 mg, white solid) was designated as Compound 316B.

Compound 316A: LC-MS: MS (ESI): 718 m/z $[M+H]^+$, purity: 97% (214 nm), retention time: 1.47 minutes (LC-MS method 040). $^1H$ NMR (400 MHz, $CD_3OD$) δ 8.69 (d, J=5.6 Hz, 1H), 8.07 (s, 1H), 7.58 (s, 1H), 7.32 (d, J=2.8 Hz, 1H), 7.13-7.10 (m, 1H), 7.04 (s, 1H), 6.99-6.97 (m, 2H), 6.66-6.65 (m, 1H), 4.76-4.74 (m, 1H), 4.29 (s, 3H), 3.46-3.43 (m, 2H), 3.21-3.17 (m, 2H), 2.92-2.78 (m, 3H), 2.63-2.55 (m, 2H), 2.21-2.17 (m, 1H), 1.90-1.82 (m, 4H), 1.70 (s, 3H), 1.52-1.37 (m, 2H), 1.33-1.21 (m, 2H), 1.10-1.03 (m, 9H) ppm.

Compound 316B: LC-MS: MS (ESI): 718 m/z $[M+H]^+$, purity: 99% (214 nm), retention time: 1.47 minutes (LC-MS method 040). $^1H$ NMR (400 MHz, $CD_3OD$) δ 8.69 (d, J=5.6 Hz, 1H), 8.15 (s, 1H), 7.74 (d, J=4.8 Hz, 1H), 7.33 (d, J=3.2 Hz, 1H), 7.17-7.14 (m, 1H), 7. 10 (s, 1H), 7.04-7.00 (m, 2H), 6.60-6.59 (m, 1H), 4.77-4.74 (m, 1H), 4.25 (s, 3H), 3.61-3.54 (m, 1H), 3.46-3.38 (m, 1H), 3.13-3.10 (m, 1H), 3.05-2.87 (m, 3H), 2.67-2.59 (m, 2H), 2.42-2.37 (m, 1H), 1.94-1.87 (m, 1H), 1.84 (d, J=5.2 Hz, 3H), 1.79-1.72 (m, 4H), 1.41-1.34 (m, 3H), 1.30-1.22 (m, 4H), 1.07 (d, J=6.4 Hz, 3H), 1.00 (s, 3H) ppm.

Example 317. Diastereomer 1 and 2 of (2R)-3-[3-[(6R)-21,22-difluoro-3,6,10,10,24-pentamethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

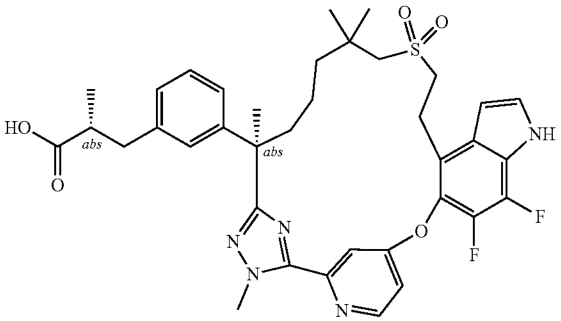 [SMILES: C[C@H](Cc1cccc([C@@]2(C)CCCC(C)(C)CS(=O)(=O)CCc3c(c(F)c(F)c4[nH]ccc34)Oc3ccnc(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 0.17 g, 0.34 mmol), and methyl 5-((4-bromo-6-fluoro-1H-indol-5-yl)oxy)-2-fluorobenzimidothioate hydroiodide (Intermediate 14-1) with methyl 4-(1-(4-bromo-6,7-difluoro-1H-indol-5-yl)ethyl)pyridine-2-carbimidothioate (Intermediate 150-10, 0.15 g, 0.366 mmol), the reaction procedure sequence, Steps A to D and F described for Example 6, was followed to give a mixture of the title compounds. This mixture was then separated by preparative reverse phase HPLC. The first eluent (21 mg, white solid) was designated as Compound 317A, and the second eluent (17 mg, white solid) was designated as Compound 317B.

Compound 317A: LC-MS: MS (ESI): 718 m/z $[M+H]^+$, purity: 98% (214 nm), retention time: 1.49 minutes (LC-MS method 040). $^1H$ NMR (400 MHz, $CD_3OD$) δ 8.66 (d, J=5.2 Hz, 1H), 8.06 (s, 1H), 7.57 (s, 1H), 7.30 (d, J=3.2 Hz, 1H), 7.12 (t, J=7.2 Hz, 1H), 7.05 (s, 1H), 6.99-6.95 (m, 2H) 6.64 (t, J=2.8 Hz, 1H), 4.77-4.71 (m, 1H), 4.27 (s, 3H), 3.46-3.40 (m, 2H), 3.24-3.18 (m, 2H), 2.93-2.87 (m, 2H), 2.78 (d, J=14.0 Hz, 1H), 2.60-2.50 (m, 2H), 2.23-2.15 (m, 1H), 1.89-1.75 (m, 4H), 1.69 (s, 3H), 1.49-1.38 (m, 2H), 1.29-1.22 (m, 2H), 1.10-1.04 (m, 9H) ppm.

Compound 317B: LC-MS: MS (ESI): 718 m/z $[M+H]^+$, purity: 99% (214 nm), retention time: 1.48 minutes (LC-MS method 040). $^1H$ NMR (400 MHz, $CD_3OD$) δ 8.66 (d, J=5.2 Hz, 1H), 8.14 (s, 1H), 7.71 (d, J=4.8 Hz, 1H), 7.31 (d, J=3.2 Hz, 1H), 7.16-7.13 (m, 1H), 7.09 (s, 1H), 7.01-7.00 (m, 2H), 6.58 (t, J=2.8 Hz, 1H), 4.78-4.72 (m, 1H), 4.24 (s, 3H), 3.59-3.40 (m, 3H), 3.11 (d, J=13.2 Hz, 1H), 3.00-2.95 (m, 2H), 2.88 (d, J=13.2 Hz, 1H), 2.62-2.54 (m, 2H), 2.38 (t, J=10.4 Hz, 1H), 1.93-1.81 (m, 4H), 1.71 (s, 3H), 1.39-1.29 (m, 4H), 1.24 (s, 3H), 1.06 (d, J=6.0 Hz, 3H), 1.01 (s, 3H) ppm.

Example 318. Diastereomers 1 and 2 of 3-[3-[(6R)-21,22-difluoro-3,6,10,10,24-pentamethyl-12,12-dioxo-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

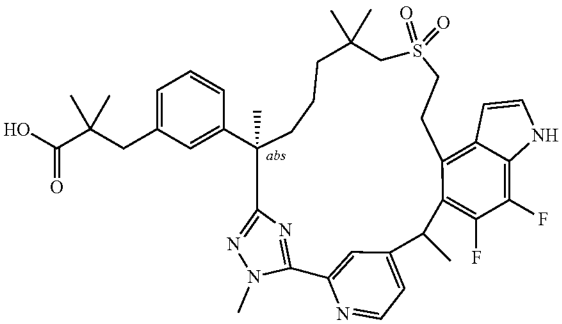 [SMILES: CC1c2ccnc(c2)-c2nc(nn2C)[C@@](C)(c2cccc(CC(C)(C)C(=O)O)c2)CCCC(C)(C)CS(=O)(=O)CCc2c1c(F)c(F)c1[nH]ccc21]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 0.36 g, 0.722 mmol), and methyl 5-((4-bromo-6-fluoro-1H-indol-5-yl)oxy)-2-fluorobenzimidothioate hydroiodide (Intermediate 14-1) with methyl 4-(1-(4-bromo-6,7-difluoro-1H-indol-5-yl)ethyl)pyridine-2-carbimidothioate (Intermediate 150-10, 0.32 g, 0.78 mmol) in Step A of Example 6, the reaction procedure sequence (Steps A to D and F described for Example 6) was followed to give a diastereomeric mixture of the title compounds. This mixture was then subjected to chiral SFC separation under the following conditions: Instrument: SFC-150 (Waters); Column: OZ 20*250 mm, 10 μm; Column temperature: 35° C.; Mobile phase: carbon dioxide/methanol (+0.2%7M ammonia in methanol)=55/45; Flow rate: 100 g/minute; Back pressure: 100 bar; Detection wavelength: 214 nm; Cycle time: 6.15 minutes; Sample solution: 130 mg dissolved in 35 ml of methanol; Injection volume: 3 ml. The first eluent (43 mg, white solid) was designated as Compound 318A, and the second eluent (37 mg, white solid) was designated as Compound 318B.

Compound 318A: LC-MS: MS (ESI): 732 m/z $[M+H]^+$, purity: 95% (214 nm), retention time: 1.56 minutes (LC-MS method 040). $^1H$ NMR (400 MHz, $CD_3OD$) δ 8.66 (d, J=5.2

Hz, 1H), 8.06 (s, 1H), 7.58 (s, 1H), 7.30 (d, J=3.2 Hz, 1H), 7.10 (t, J=7.2 Hz, 1H), 7.00-6.93 (m, 3H), 6.64 (t, J=2.8 Hz, 1H), 4.77-4.71 (m, 1H), 4.27 (s, 3H), 3.44 (t, J=5.6 Hz, 2H), 3.21 (t, J=6.8 Hz, 2H), 2.90 (d, J=13.6 Hz, 1H), 2.79 (d, J=13.6 Hz, 1H), 2.76 (s, 2H), 2.20-2.15 (m, 1H), 1.87-1.81 (m, 4H), 1.69 (s, 3H), 1.54-1.45 (m, 1H), 1.42-1.38 (m, 1H), 1.24-1.17 (m, 1H), 1.09-1.04 (m, 13H) ppm.

Compound 318B: LC-MS: MS (ESI): 732 m/z $[M+H]^+$, purity: 95% (214 nm), retention time: 1.56 minutes (LC-MS method 040). $^1H$ NMR (400 MHz, $CD_3OD$) δ 8.66 (d, J=5.2 Hz, 1H), 8.06 (s, 1H), 7.58 (d, J=4.8 Hz, 1H), 7.30 (d, J=3.2 Hz, 1H), 7.10 (t, J=7.2 Hz, 1H), 7.00-6.93 (m, 3H), 6.64 (t, J=2.8 Hz, 1H), 4.77-4.71 (m, 1H), 4.27 (s, 3H), 3.60-3.52 (m, 1H), 3.40-3.32 (m, 1H), 3.12 (d, J=13.6 Hz, 1H), 3.05-2.95 (m, 1H), 2.88 (d, J=13.6 Hz, 1H), 2.80 (s, 2H), 2.40-2.30 (m, 1H), 1.95-1.81 (m, 4H), 1.75-1.69 (m, 4H), 1.54-1.45 (m, 1H), 1.42-1.22 (m, 6H), 1.10-1.09 (m, 6H), 1.00 (s, 3H) ppm.

Example 319. Diastereomer 2 of (2R)-2-Methyl-3-[3-[(6R)-21,22,28-trifluoro-3,6,10,10-tetramethyl-12,12,24-trioxo-12λ6,24λ4-dithia-3,4,19,30-tetraza-pentacyclo[23.3.1.12,5.015,23.016,20]triaconta-1(29),2(30),4,15,17,20,22,25,27-nonaen-6-yl]phenyl]propanoic Acid

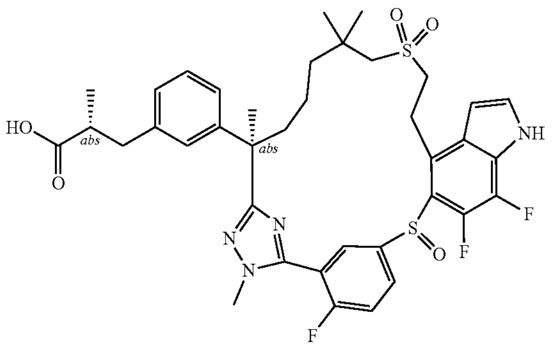 [SMILES: C[C@H](Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O]

Methyl (2R)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate

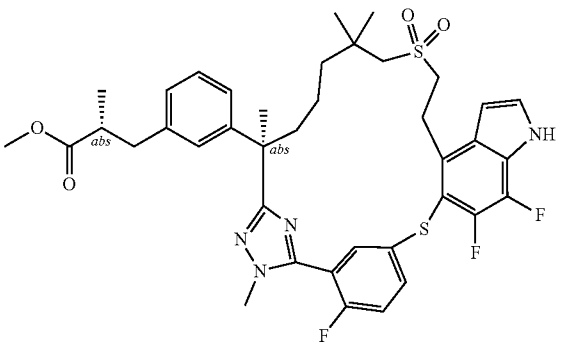 [SMILES: COC(=O)[C@H](C)Cc1cccc([C@@]2(C)CCCC(C)(C)CS(=O)(=O)CCc3c(c(F)c(F)c4[nH]ccc34)Sc3ccc(F)c(c3)-c3nc2nn3C)c1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 3.60 g, 7.42 mmol), and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)thio)-2-fluorobenzimidothioate (Intermediate 150-7, 3.20 g, 7.42 mmol), the reaction procedure sequence, Steps A to C described for Example 6, then Step B of Example 301, was followed to give the title compound (1.2 g) as a yellowish solid. LC-MS: MS (ESI): 753 m/z $[M+H]^+$, purity: 87% (214 nm), retention time: 2.24 minutes (LC-MS method 43).

Compound 319 Diastereomer 2 of (2R)-2-methyl-3-[3-[(6R)-21,22,28-trifluoro-3,6,10,10-tetramethyl-12,12,24-trioxo-12λ6,24λ4-dithia-3,4,19,30-tetraza-pentacyclo[23.3.1.12,5.015,23.016,20]triaconta-1(29),2(30),4,15,17,20,22,25,27-nonaen-6-yl]phenyl]propanoic Acid

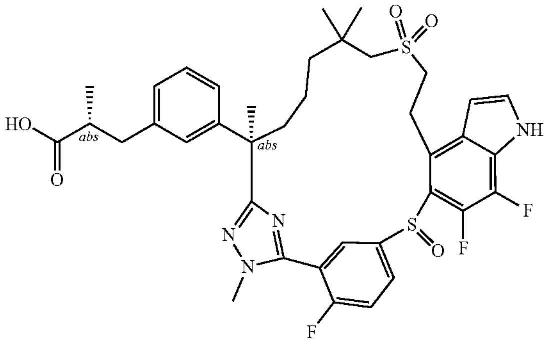 [SMILES: C[C@H](Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O]

Step B: Exchanging methyl (2S)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step E product of Example 204) with Step A product (1.20 g, 1.59 mmol) in Step F of Example 204, the reaction procedure sequence, Steps F and H of Example 204, was followed to give the title compound (322 mg) as a white solid. LC-MS: MS (ESI): 755 m/z $[M+H]^+$, purity: >99% (214 nm), retention time: 1.35 minutes (LC-MS method 40). $^1H$ NMR (400 MHz, $CD_3OD$) δ 8.12-7.96 (m, 2H), 7.64-7.60 (m, 1H), 7.45 (d, J=3.2 Hz, 1H), 7.14 (t, J=7.6 Hz, 1H), 7.09 (s, 1H), 7.03-6.98 (m, 2H), 6.78 (s, 1H), 3.92-3.86 (m, 4H), 3.71-3.64 (m, 1H), 3.59-3.43 (m, 1H), 3.15-3.00 (m, 2H), 2.97-2.89 (m, 1H), 2.67-2.57 (m, 2H), 2.29-2.25 (m, 1H), 1.95-1.87 (m, 1H), 1.71 (s, 3H), 1.55-1.30 (m, 4H), 1.21 (s, 3H), 1.13-1.04 (m, 7H) ppm.

Example 320. (2R)-2-Methyl-3-[3-[(6R)-21,22,28-trifluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

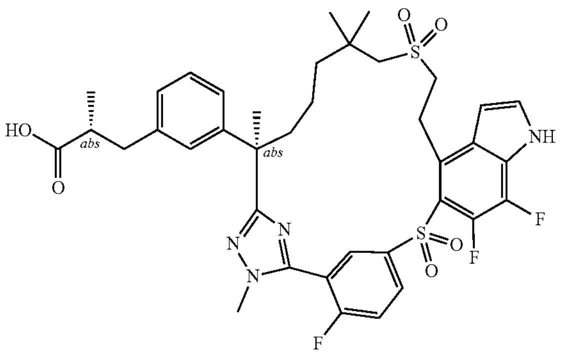 [SMILES: C[C@H](Cc1cccc([C@@]2(C)CCCC(C)(C)CS(=O)(=O)CCc3c(c(F)c(F)c4[nH]ccc34)S(=O)(=O)c3ccc(F)c(c3)-c3nc2nn3C)c1)C(=O)O]

Methyl (2R)-2-methyl-3-[3-[(6R)-21,22,28-trifluoro-3,6,10,10-tetramethyl-19-methylsulfonyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate

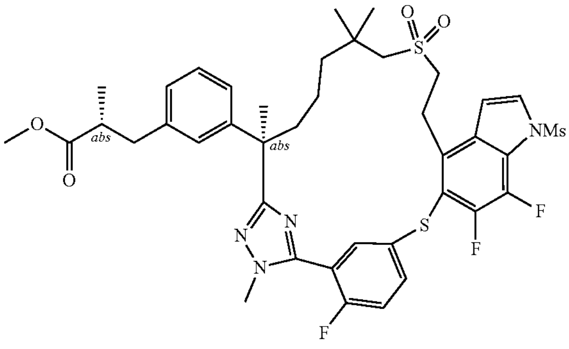

Step A. To a stirred and cooled (0° C.) solution of methyl (2R)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate (product from Step A of Example 319, 220 mg, 0.292 mmol) in dichloromethane (5 mL) was added triethylamine (0.20 mL, 1.46 mmol) and methanesulfonyl chloride (0.046 mL, 0.584 mmol). The reaction was stirred at room temperature for 1 hour, quenched with water (25 mL), and diluted with ethyl acetate (30 mL). The separated organic layer was washed with water (2×30 mL), brine (2×30 mL), dried over sodium sulfate and concentrated. Since large amount of starting material remained, this washing procedure was repeated 4 times until all starting material disappeared. The crude was then purified by flash column chromatography (eluting with 0-45% ethyl acetate in petroleum ether) to give the title compound (200 mg, 82%) as a yellow solid. LC-MS: MS (ESI): 831 m/z [M+H]$^+$, purity: 94% (214 nm), retention time: 2.14 minutes (LC-MS method 42).

Methyl (2R)-2-methyl-3-[3-[(6R)-21,22,28-trifluoro-3,6,10,10-tetramethyl-19-methylsulfonyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]propanoate

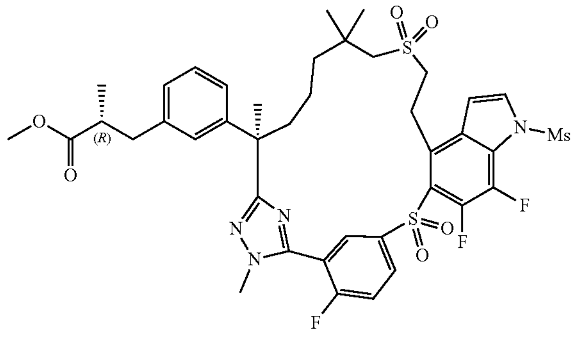

Step B: To a stirred solution of the product from Step A (200 mg, 0.241 mmol) in dichloromethane (10 mL) was added 3-chloroperoxybenzoic acid (104 mg, 0.602 mmol). The reaction mixture was stirred at room temperature for 2 days, quenched with water (20 mL), and diluted with ethyl acetate (30 mL). The separated organic layer was washed with water, brine, dried over sodium sulfate and concentrated. The residue was purified by automated flash column chromatography (eluting with 0-50% ethyl acetate in petroleum ether) to afford the title compound (120 mg, 58%) as a solid. LC-MS: MS (ESI): 863 m/z [M+H]$^+$, purity: 98% (214 nm), retention time: 2.08 minutes (LC-MS method 42).

Compound 320: (2R)-2-Methyl-3-[3-[(6R)-21,22,28-trifluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]propanoic acid

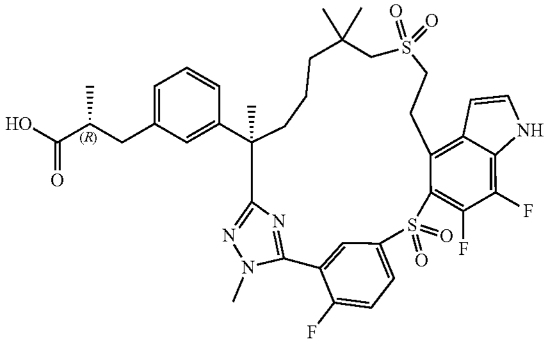

Step C: To a stirred solution of the product from Step B (120 mg, 0.139 mmol) in tetrahydrofuran (6 mL) was added a solution of lithium hydroxide (10 mg, 0.417 mmol) in water (2 mL). The reaction was stirred at room temperature for 2 days, quenched with water (20 mL), and extracted with ethyl acetate (20 mL). The separated organic layer was washed with water, then brine, dried over sodium sulfate and concentrated. The residue was purified by reverse phase prep-HPLC to give the title compound (50 mg, 47%) as white solid. LC-MS: MS (ESI): 771 m/z [M+H]$^+$, purity: 98% (214 nm), retention time: 1.92 minutes (LC-MS method 42). $^1H$ NMR (400 MHz, $CD_3OD$) δ 8.36-8.30 (m, 2H), 7.64 (t, J=9.2 Hz, 1H), 7.47 (d, J=3.2 Hz, 1H), 7.15 (t, J=7.6 Hz, 1H), 7.07 (s, 1H), 6.98 (t, J=6.8 Hz, 2H), 6.78 (t, J=3.2 Hz, 1H), 3.83 (d, J=2.4 Hz, 3H), 3.78-3.70 (m, 2H), 3.55-3.48 (m, 1H), 3.41-3.36 (m, 1H), 3.17-3.08 (m, 2H), 2.95-2.90 (m, 1H), 2.64-2.55 (m, 2H), 2.39-2.33 (m, 1H), 1.89-1.83 (m, 1H), 1.71 (s, 3H), 1.58-1.51 (m, 2H), 1.45-1.39 (m, 1H), 1.30-1.25 (m, 4H), 1.19 (s, 3H), 1.05 (d, J=6.4 Hz, 3H) ppm.

Example 321. (2R)-2-Methyl-3-[3-[(6R)-21,22,28-trifluoro-3,6,10,10,17-pentamethyl-12,12-dioxo-24-oxa-12λ6-thia-3,4,19,30-tetrazapentacyclo [23.3.1.12,5.015,23.016,20]triaconta-1(29),2(30),4,15,17,20,22,25,27-nonaen-6-yl]phenyl]propanoic Acid

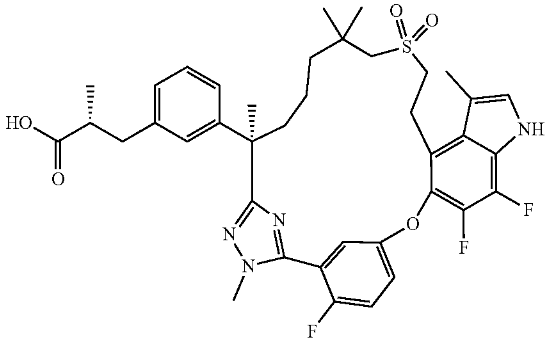

Methyl (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoate

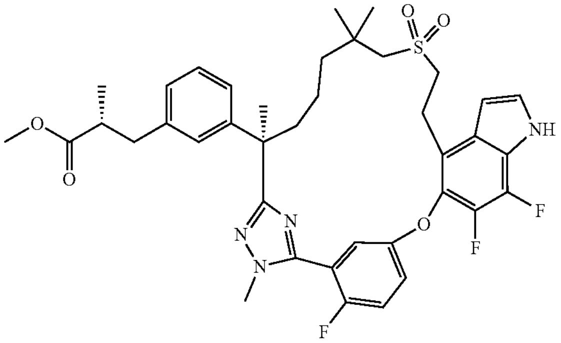 [SMILES: COC(=O)[C@H](C)Cc1cccc([C@@]2(C)CCCC(C)(C)CS(=O)(=O)CCc3c(c(F)c(F)c4[nH]ccc34)Oc3ccc(F)c(c3)-c3nc2nn3C)c1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 0.50 g, 1.03 mmol) and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)oxy)-2-fluorobenzimidothioate (Intermediate 14-2, 728 mg, 1.34 mmol) in Step A, the reaction procedure sequence (Steps A-D) described for Example 6 was followed to prepare the title compound (128 mg) as a white solid. MS (ESI): 737 m/z [M+H]$^+$, retention time: 2.66 minutes; purity: 99% (214 nm) (LC-MS method 032).

Methyl (2R)-2-methyl-3-[3-[(6R)-21,22,28-trifluoro-17-formyl-3,6,10,10-tetramethyl-12,12-dioxo-24-oxa-12λ6-thia-3,4,19,30-tetrazapentacyclo [23.3.1.12,5.015,23.016,20]triaconta-1(29),2(30),4,15,17,20,22,25,27-nonaen-6-yl]phenyl]propanoate

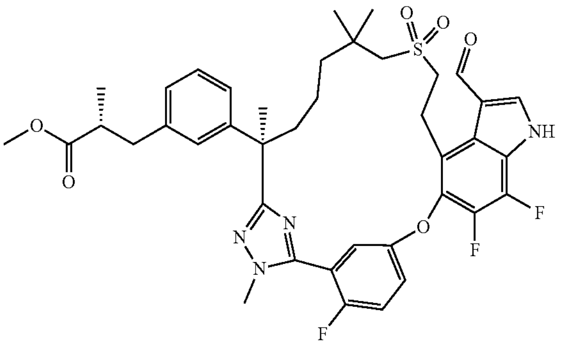 [SMILES: COC(=O)[C@H](C)Cc1cccc([C@@]2(C)CCCC(C)(C)CS(=O)(=O)CCc3c(c(F)c(F)c4[nH]cc(C=O)c34)Oc3ccc(F)c(c3)-c3nc2nn3C)c1]

Step B: Phosphorus oxychloride (0.32 mL, 3.39 mmol) was added dropwise to dimethylformamide (50 mL) at 0° C. The solution was then treated with methyl (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo [23.3.1.12,5.015,23.016,20]triaconta-1(29),2(30),4,15,17,20,22,25,27-nonaen-6-yl]phenyl]propanoate (Step A product, 500 mg, 0.679 mmol) at 0° C. The reaction was stirred at room temperature for 1 hour. The mixture was quenched with 200 mL of water and extracted with ethyl acetate (3×100 mL). The combined organic extracts were washed with brine (100 mL×3), dried over sodium sulfate, filtered, and concentrated. The residue was purified by automated silica gel column chromatography (eluting with 0-80% of ethyl acetate in petroleum ether) to give the title compound (410 mg, 79%) as a light-yellow solid. LC-MS: MS (ESI): 765 m/z [M+H]$^+$, purity: 71% (214 nm), retention time: 1.83 minutes (LC-MS method 45).

Methyl (2R)-2-methyl-3-[3-[(6R)-21,22,28-trifluoro-3,6,10,10,17-pentamethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoate

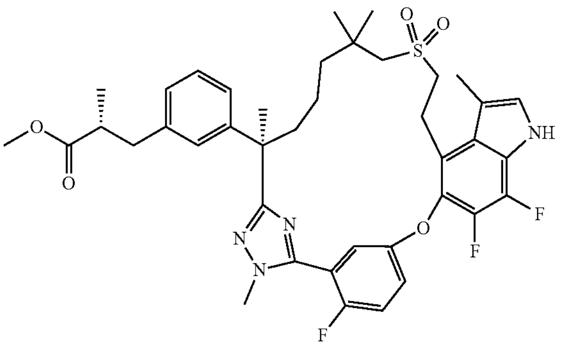 [SMILES: COC(=O)[C@H](C)Cc1cccc([C@@]2(C)CCCC(C)(C)CS(=O)(=O)CCc3c(c(F)c(F)c4[nH]cc(C)c34)Oc3ccc(F)c(c3)-c3nc2nn3C)c1]

Step C: To a stirred solution of Step B product (410 mg, 0.536 mmol) in tetrahydrofuran (20 mL) was added palladium on carbon (57 mg). The reaction was stirred at room temperature for 4 hours under a hydrogen atmosphere. The mixture was filtered, and the filtrate was concentrated. The residue was purified by automated silica gel column chromatography (eluting with 0-50% of ethyl acetate in petroleum ether) to give the title compound (350 mg, 87%) as a white solid. LC-MS: MS (ESI): 751 m/z $[M+H]^+$, purity: 97% (214 nm), retention time: 1.95 minutes (LC-MS method 45).

Compound 321: (2R)-2-Methyl-3-[3-[(6R)-21,22,28-trifluoro-3,6,10,10,17-pentamethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

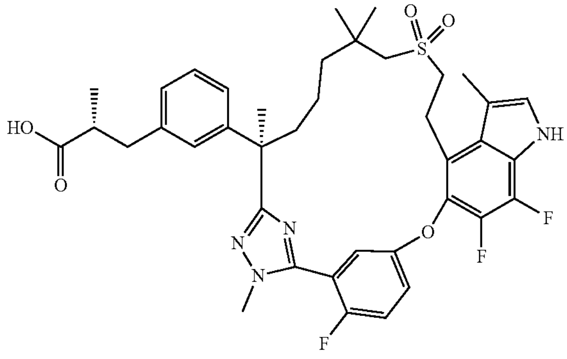 [SMILES: Cc1c[nH]c2c(F)c(F)c3c(c12)CCS(=O)(=O)CC(C)(C)CCC[C@](C)(c1cccc(C[C@@H](C)C(=O)O)c1)c1nc(n(C)n1)-c1cc(ccc1F)O3]

Step D: To a stirred solution of the product from Step C (350 mg, 0.466 mmol) in methanol (20 mL), tetrahydrofuran (10 mL) and water (10 mL) was added lithium hydroxide monohydrate (98 mg, 2.33 mmol). The reaction was stirred at room temperature for 16 hours, diluted with 100 mL of water, acidified with 1N hydrochloric acid to pH ~5, and extracted with ethyl acetate (100 mL×3). The combined organic phase was washed with brine, dried over sodium sulfate, filtered, and concentrated. The residue was purified by reverse phase Prep-HPLC to give the title compound (153 mg, 44%) as a white solid. LC-MS: MS (ESI): 737 m/z $[M+H]^+$, purity: >99% (214 nm), retention time: 1.51 minutes (LC-MS method 45). $^1H$ NMR (400 MHz, $CD_3OD$) δ 7.48-7.46 (m, 1H), 7.36-7.31 (m, 1H), 7.22-7.16 (m, 2H), 7.13 (d, J=0.8 Hz, 1H), 7.07 (s, 1H), 7.03-7.01 (m, 2H), 3.91 (d, J=2.0 Hz, 3H), 3.49-3.42 (m, 3H), 3.19-3.09 (m, 2H), 3.03-2.91 (m, 2H), 2.66-2.58 (m, 2H), 2.49 (s, 3H), 2.23-2.17 (m, 1H), 1.90-1.82 (m, 1H), 1.73-1.69 (m, 4H), 1.44-1.38 (m, 1H), 1.33-1.26 (m, 1H), 1.16-1.07 (m, 11H) ppm.

Example 322. (2R)-3-[3-[(6R)-17-Cyano-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

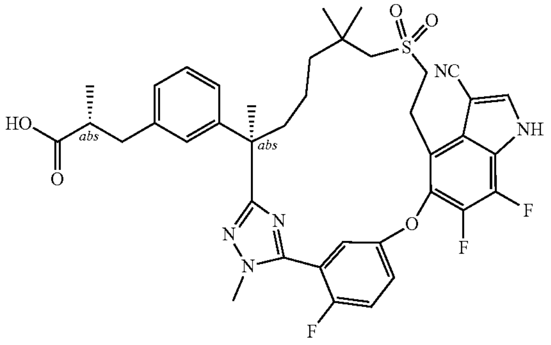 [SMILES: C[C@H](Cc1cccc([C@@]2(C)CCCC(C)(C)CS(=O)(=O)CCc3c(c(F)c(F)c4[nH]cc(C#N)c34)Oc3ccc(F)c(c3)-c3nc2nn3C)c1)C(=O)O]

Methyl (2R)-3-[3-[(6R)-17-cyano-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

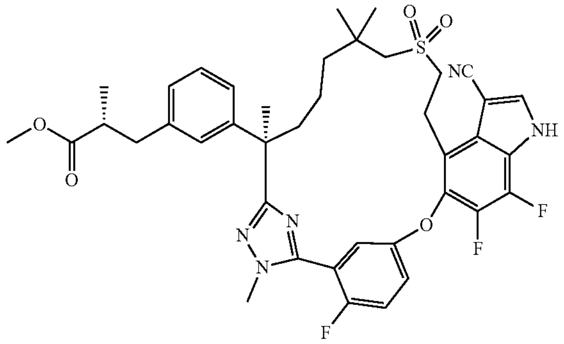 [SMILES: COC(=O)[C@H](C)Cc1cccc([C@@]2(C)CCCC(C)(C)CS(=O)(=O)CCc3c(c(F)c(F)c4[nH]cc(C#N)c34)Oc3ccc(F)c(c3)-c3nc2nn3C)c1]

Step A: To a stirred and cooled (−50° C.) solution of methyl (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product from Example 321, 250 mg, 0.339 mmol) in dimethyl formamide (20 mL) was added chlorosulfonyl isocyanate (0.059 mL, 0.679 mmol). The reaction was stirred at −20° C. for 2 hours, quenched with 100 mL of water, and extracted with ethyl acetate (3×100 mL). The combined organic extracts were washed with brine (2×100 mL), dried over sodium sulfate, filtered, and concentrated. The residue was purified by silica gel column chromatography (eluting with 0-75% of Ethyl acetate in Petroleum ether) to give the title compound (110 mg, 43%) as a colorless liquid. LC-MS: MS (ESI): 762 m/z $[M+H]^+$, purity: 98% (254 nm), retention time: 1.86 minutes (LC-MS method 44).

Compound 322. (2R)-3-[3-[(6R)-17-Cyano-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

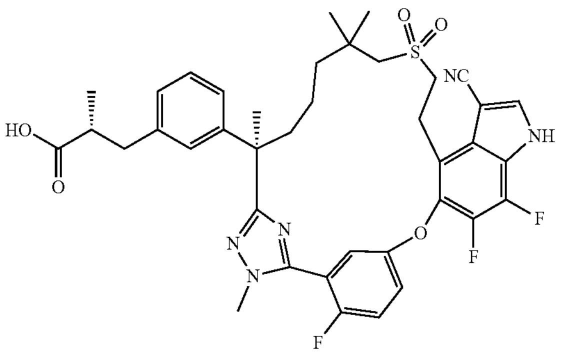 [SMILES: C[C@H](Cc1cccc([C@@]2(C)CCCC(C)(C)CS(=O)(=O)CCc3c(c(F)c(F)c4[nH]cc(C#N)c34)Oc3ccc(F)c(c3)-c3nc2nn3C)c1)C(=O)O]

Step B: To a stirred solution of Step A product (130 mg, 0.171 mmol) in tetrahydrofuran (10 mL), methanol (5 mL) and water (5 mL) was added lithium hydroxide monohydrate (36 mg, 0.853 mmol). The reaction was stirred at room temperature for 4 hours, diluted with 60 mL of water, acidified with hydrochloric acid solution to pH ~5, and extracted with ethyl acetate (3×80 mL). The combined organic phase was washed with brine, dried over sodium sulfate, filtered, and concentrated. The residue was purified by reverse phase Prep-HPLC to give the title compound (96 mg, 75%) as a white solid. LC-MS: MS (ESI): 748 m/z $[M+H]^+$, purity: >99% (214 nm), retention time: 1.42 minutes (LC-MS method 44). $^1H$ NMR (400 MHz, $CD_3OD$) δ 8.14 (s, 1H), 7.43-7.37 (m, 3H), 7.16 (t, J=7.6 Hz, 1H), 7.04-6.99 (m, 3H), 3.88 (d, J=1.6 Hz, 3H), 3.61-3.58 (m, 2H), 3.50-3.36 (m, 2H), 3.20 (d, J=13.6 Hz, 1H), 2.97-2.89 (m, 2H), 2.62-2.55 (m, 2H), 2.25-2.17 (m, 1H), 1.89-1.82 (m, 1H), 1.71-1.65 (m, 4H), 1.48-1.40 (m, 1H), 1.37-1.30 (m, 1H), 1.10-1.05 (m, 10H) ppm.

Example 323. 3-[3-[(6R)-21,22-Difluoro-3,6,10,10-tetramethyl-12,12-dioxo-24-oxa-12λ6-thia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

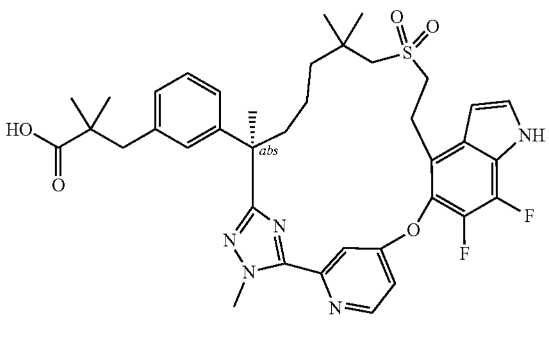 [SMILES: Cn1nc2nc1-c1cc(ccn1)Oc1c(F)c(F)c3[nH]ccc3c1CCS(=O)(=O)CC(C)(C)CCC[C@]2(C)c1cccc(CC(C)(C)C(=O)O)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (intermediate 137-13, 2.75 g, 5.52 mmol) and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)oxy)pyridine-2-carbimidothioate (Intermediate 150, 2.20 g, 5.52 mmol) in Step A, the reaction procedure sequence (Steps A-D, and Step F) described for Example 6 was followed to prepare the title compound (Compound 323, 78 mg) as a white solid. LC-MS: MS (ESI): 720 m/z $[M+H]^+$, retention time: 2.05 minutes; purity: 99% (214 nm) (LC-MS method 42). $^1H$ NMR (400 MHz, $CD_3OD$) δ 8.66 (d, J=5.6 Hz, 1H), 7.66 (d, J=2.4 Hz, 1H), 7.40 (d, J=3.2 Hz, 1H), 7.27 (dd, J=5.6, 2.4 Hz, 1H), 7.09 (t, J=7.6 Hz, 1H), 7.00-6.91 (m, 3H), 6.75 (t, J=3.2 Hz, 1H), 4.34 (s, 3H), 3.40-3.33 (m, 2H), 3.17-3.10 (m, 2H), 2.78-2.71 (m, 2H), 2.71-2.60 (m, 2H), 2.06-1.99 (m, 1H), 1.81-1.75 (m, 1H), 1.64 (s, 3H), 1.41-1.28 (m, 2H), 1.28-1.18 (m, 2H), 1.06-1.00 (m, 9H), 0.94 (s, 3H) ppm Example 324. 2,2-Dimethyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

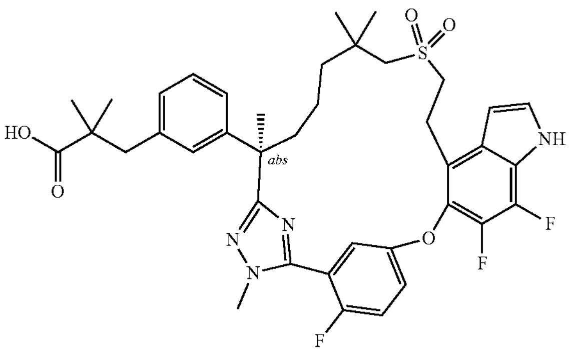 [SMILES: Cn1nc2nc1-c1cc(ccc1F)Oc1c(F)c(F)c3[nH]ccc3c1CCS(=O)(=O)CC(C)(C)CCC[C@]2(C)c1cccc(CC(C)(C)C(=O)O)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (intermediate 137-13, 600 mg, 1.20 mmol) and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)oxy)-2-fluorobenzimidothioate hydroiodide (Intermediate 14-2, 500 mg, 1.20 mmol) in Step A, the reaction procedure sequence (Steps A-D, and Step F) described for Example 6 was followed to prepare the title compound (Compound 324, 40 mg) as a white solid. MS (ESI): 737 m/z $[M+H]^+$, retention time: 1.97 minutes; purity: 99% (254 nm) (LC-MS method 003). $^1H$ NMR (400 MHz, $CD_3OD$) δ 7.40-7.35 (m, 3H), 7.25-7.17 (m, 1H), 7.12 (t, J=7.9 Hz, 1H), 7.05-6.90 (m, 3H), 6.71-6.59 (m, 1H), 3.85 (d, J=2.1 Hz, 3H), 3.40-3.32 (m, 3H), 3.25-3.13 (m, 1H), 3.07-2.98 (m, 1H), 2.87-2.79 (m, 1H), 2.76 (s, 2H), 2.19-2.09 (m, 1H), 1.87-1.77 (m, 1H), 1.67 (s, 3H), 1.63-1.51 (m, 1H), 1.41-1.28 (m, 1H), 1.26-1.17 (m, 1H), 1.08-1.00 (m, 13H) ppm.

Example 325. 2-[(6R)-21,22,28-Trifluoro-3,6,10,10-tetramethyl-12,12-dioxo-6-phenyl-12λ6,24-dithia-3,4,19,30-tetrazapentacyclo[23.3.1.12,5.015,23.016,20]triaconta-1(29),2(30),4,15,17,20,22,25,27-nonaen-17-yl]acetic Acid

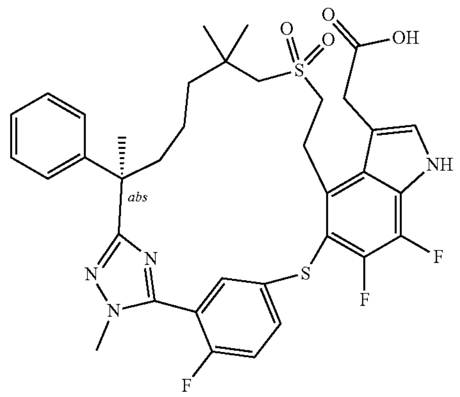 [SMILES: Cn1nc2nc1-c1cc(ccc1F)Sc1c(F)c(F)c3[nH]cc(CC(=O)O)c3c1CCS(=O)(=O)CC(C)(C)CCC[C@]2(C)c1ccccc1]

(6R)-21,22,28-trifluoro-3,6,10,10-tetramethyl-6-phenyl-12λ6,24-dithia-3,4,19,30-tetrazapentacyclo[23.3.1.12,5.015,23.016,20]triaconta-1(29),2(30),4,15,17,20,22,25,27-nonaene 12,12-dioxide

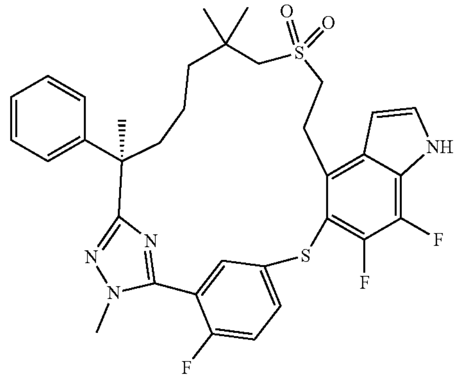 [SMILES: Cn1nc2nc1-c1cc(ccc1F)Sc1c(F)c(F)c3[nH]ccc3c1CCS(=O)(=O)CC(C)(C)CCC[C@]2(C)c1ccccc1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with (R)-7-((2-hydroxyethyl)sulfonyl)-N',2,6,6-tetramethyl-2-phenylheptanehydrazide (Intermediate 152, 1.16 g, 3.01 mmol) and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)thio)-2-fluorobenzimidothioate (Intermediate 150-7, 1.30 g, 3.01 mmol) in Step A, the reaction procedure sequence (Steps A-D) described for Example 6 was followed to prepare the title compound (Compound 325, 300 mg) as a white solid. LC-MS: MS (ESI): 653 m/z $[M+H]^+$, retention time: 1.89 minutes; purity: 83% (254 nm) (LC-MS method 45).

Ethyl 2-[(6R)-21,22,28-trifluoro-3,6,10,10-tetramethyl-12,12-dioxo-6-phenyl-12λ6,24-dithia-3,4,19,30-tetrazapentacyclo[23.3.1.12,5.015,23.016,20]triaconta-1(29),2(30),4,15,17,20,22,25,27-nonaen-17-yl]Acetate

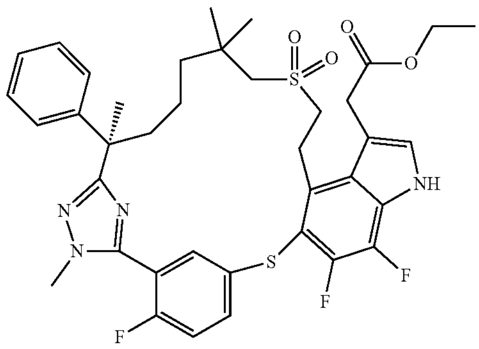 [SMILES: CCOC(=O)Cc1c[nH]c2c(F)c(F)c3c(c12)CCS(=O)(=O)CC(C)(C)CCC[C@](C)(c1ccccc1)c1nc(n(C)n1)-c1cc(ccc1F)S3]

Step B: To a stirred solution of Step A product ((30 mg, 0.0460 mmol) in dichloromethane (3 mL) was added ethyl diazoacetate (0.0095 mL, 0.092 mmol) and copper(ii) trifluoromethanesulfonate (1.7 mg, 0.0046 mmol). The reaction was stirred at room temperature overnight, quenched with 20 mL of water, and extracted with ethyl acetate (3×20 mL). The combined organic phases were washed with brine, dried over sodium sulfate, filtered, and concentrated. The residue was purified by reverse phase Prep-HPLC to give the title compound (5.3 mg, 16%) as a white solid. LC-MS: MS (ESI): 739 m/z $[M+H]^+$, retention time: 1.95 minutes; purity: >99% (254 nm) (LC-MS method 45).

Compound 325. 2-[(6R)-21,22,28-Trifluoro-3,6,10,10-tetramethyl-12,12-dioxo-6-phenyl-12λ6,24-dithia-3,4,19,30-tetrazapentacyclo[23.3.1.12,5.015,23.016,20]triaconta-1(29),2(30),4,15,17,20,22,25,27-nonaen-17-yl]acetic Acid

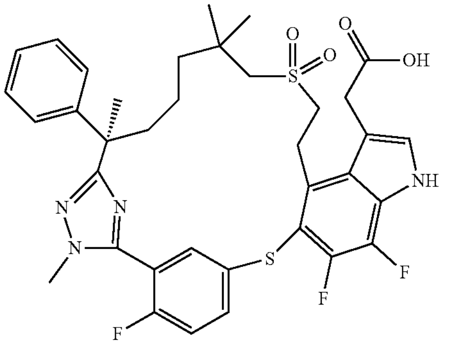 [SMILES: Cn1nc2nc1-c1cc(ccc1F)Sc1c(F)c(F)c3[nH]cc(CC(=O)O)c3c1CCS(=O)(=O)CC(C)(C)CCC[C@]2(C)c1ccccc1]

Step C: To a stirred solution of Step B product (5.3 mg, 0.0072 mmol) in tetrahydrofuran (1 mL) and water (0.5 mL) was added lithium hydroxide monohydrate (1.5 mg, 0.036 mmol). The reaction was stirred at room temperature for 16 hours, diluted with 20 mL of water, acidified with 1N hydrochloric acid to pH ~6, and extracted with ethyl acetate (3×20 mL). The combined organic phase was washed with brine, dried over sodium sulfate, filtered, and concentrated. The residue was purified by Prep-TLC (eluting with 30:1 dichloromethane:methanol) to give the title compound (3.3 mg, 65%) as a white solid. LC-MS: MS (ESI): 711 m/z $[M+H]^+$, retention time: 2.03 minutes; purity: >99% (254 nm) (LC-MS method 42). $^1H$ NMR (400 MHz, $CD_3OD$) δ 7.39-7.36 (m, 3H), 7.25-7.24 (m, 1H), 7.16 (t, J=7.6 Hz, 1H), 7.04 (s, 1H), 7.01-6.97 (m, 2H), 6.69 (t, J=3.2 Hz, 1H), 3.87 (d, J=2.4 Hz, 3H), 3.24-3.19 (m, 1H), 3.01-2.90 (m, 2H), 2.84 (d, J=13.6 Hz, 1H), 2.62-2.55 (m, 2H), 2.22-2.13 (m, 1H), 2.05-1.99 (m, 1H), 1.87-1.79 (m, 1H), 1.69 (s, 3H), 1.65-1.60 (m, 1H), 1.41-1.30 (m, 3H), 1.09-1.05 (m, 6H), 0.93-0.90 (m, 1H) ppm.

Example 326. Diastereomer 2 of 2-[(6R)-21,22,28-Trifluoro-3,6,10,10-tetramethyl-12,12,24-trioxo-6-phenyl-12λ6,24λ4-dithia-3,4,19,30-tetrazapentacyclo[23.3.1.12,5.015,23.016,20]triaconta-1(29),2(30),4,15,17,20,22,25,27-nonaen-17-yl]acetic Acid

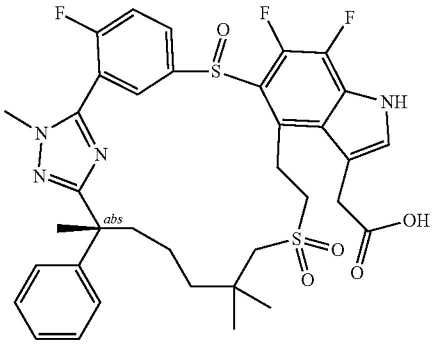 [SMILES: Cn1nc2nc1-c1cc(ccc1F)S(=O)c1c(F)c(F)c3[nH]cc(CC(=O)O)c3c1CCS(=O)(=O)CC(C)(C)CCC[C@]2(C)c1ccccc1]

(6R,13E)-21,22,28-Trifluoro-3,6,10,10-tetramethyl-6-phenyl-12λ6,24-dithia-3,4,19,30-tetrazapentacyclo[23.3.1.12,5.015,23.016,20]triaconta-1(29),2(30),4,13,15,17,20,22,25,27-decaene 12,12-dioxide

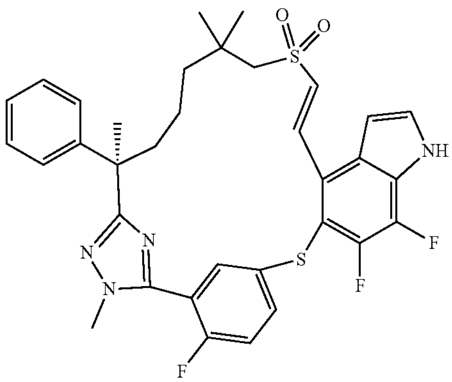 [SMILES: Cn1nc2nc1-c1cc(ccc1F)Sc1c(F)c(F)c3[nH]ccc3c1/C=C/S(=O)(=O)CC(C)(C)CCC[C@]2(C)c1ccccc1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with (R)-7-((2-hydroxyethyl)sulfonyl)-N',2,6,6-tetramethyl-2-phenylheptanehydrazide (Intermediate 152, 3.57 g, 9.28 mmol) and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)thio)-2-fluorobenzimidothioate (Intermediate 150-7, 4.00 g, 9.28 mmol) in Step A, the reaction procedure sequence (Steps A-C) described for Example 6 was followed to prepare the title compound (1.6 g) as a yellow solid. LC-MS: MS (ESI): 651 m/z $[M+H]^+$, retention time: 2.03 minutes; purity: 95% (254 nm) (LC-MS method 030).

Ethyl 2-hydroxy-2-[(6R,13E)-21,22,28-trifluoro-3,6,10,10-tetramethyl-12,12-dioxo-6-phenyl-12λ6,24-dithia-3,4,19,30-tetrazapentacyclo[23.3.1.12,5.015,23.016,20]triaconta-1(29),2(30),4,13,15,17,20,22,25,27-decaen-17-yl]Acetate

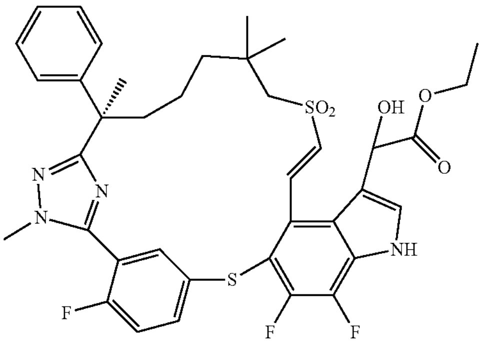 [SMILES: CCOC(=O)C(O)c1c[nH]c2c(F)c(F)c3c(c12)/C=C/S(=O)(=O)CC(C)(C)CCC[C@](C)(c1ccccc1)c1nc(n(C)n1)-c1cc(ccc1F)S3]

Step B: To a stirred solution of the product from Step A (1.35 g, 2.07 mmol) in dichloromethane (10 mL) was added ethyl 2-oxoacetate (50% in toluene) (1 mL) and magnesium iodide (58 mg, 0.207 mmol). The reaction was stirred at 40° C. for 4 days. The mixture was diluted with ethyl acetate (50 mL), washed with water, brine (2×50 mL), dried over sodium sulfate, and concentrated. The residue was purified by automated flash chromatography (40 g silica gel column, eluting with 0-50% ethyl acetate in petroleum ether) to give the title compound (850 mg, 55%) as a solid. LC-MS: MS (ESI): 753 m/z $[M+H]^+$, retention time: 1.41 minutes; purity: 99% (254 nm) (LC-MS method 041).

Ethyl 2-hydroxy-2-[(6R)-21,22,28-trifluoro-3,6,10,10-tetramethyl-12,12-dioxo-6-phenyl-12λ6,24-dithia-3,4,19,30-tetrazapentacyclo[23.3.1.12,5.015,23.016,20]triaconta-1(29),2(30),4,15,17,20,22,25,27-nonaen-17-yl]Acetate

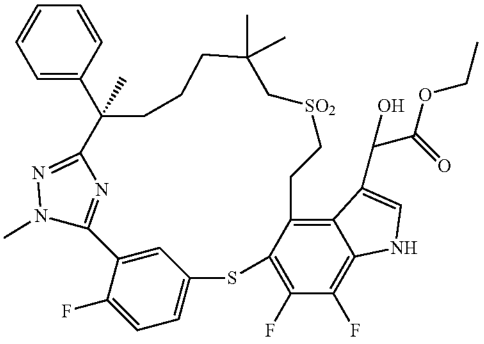 [SMILES: CCOC(=O)C(O)c1c[nH]c2c(F)c(F)c3c(c12)CCS(=O)(=O)CC(C)(C)CCC[C@](C)(c1ccccc1)c1nc(n(C)n1)-c1cc(ccc1F)S3]

Step C: To a stirred solution of the product from Step B (850 mg, 1.13 mmol) in ethanol (15 mL) was added palladium on carbon (250 mg). The reaction was stirred at 50° C. for 7 hours under a hydrogen atmosphere. The mixture was filtered, and the filtrate was concentrated to give the title compound (370 mg, 43%) as a white solid. LC-MS: MS (ESI): 755 m/z [M+H]$^+$, retention time: 1.39 minutes; purity: 87% (214 nm) (LC-MS method 030).

Ethyl 2-[(6R)-21,22,28-trifluoro-3,6,10,10-tetramethyl-12,12-dioxo-6-phenyl-12λ6,24-dithia-3,4,19,30-tetrazapentacyclo[23.3.1.12,5.015,23.016,20]triaconta-1(29),2(30),4,15,17,20,22,25,27-nonaen-17-yl]acetate

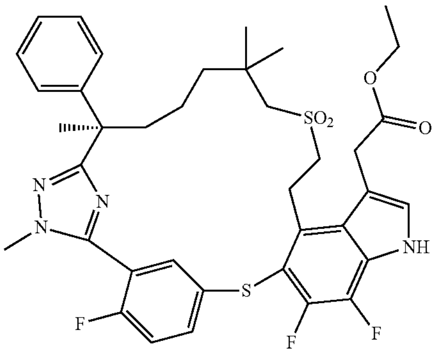 [SMILES: CCOC(=O)Cc1c[nH]c2c(F)c(F)c3c(c12)CCS(=O)(=O)CC(C)(C)CCC[C@](C)(c1ccccc1)c1nc(n(C)n1)-c1cc(ccc1F)S3]

Step D. To a stirred solution of Step C product (370 mg, 0.490 mmol) in dichloromethane (5 mL) was added diphosphorus tetraiodide (647 mg, 0.980 mmol). The reaction was stirred at room temperature overnight under an argon atmosphere, quenched with saturated sodium bisulfite (10 mL), and diluted with dichloromethane (10 mL) and saturated sodium bicarbonate (10 mL). The separated organic layer was washed with ethyl acetate, dried over sodium sulfate, filtered, and concentrated to give the title compound (325 mg, 90%) as a solid. LC-MS: MS (ESI): 739 m/z [M+H]$^+$, retention time: 2.21 minutes; purity: 71% (214 nm) (LC-MS method 030).

Compound 326: Diastereomer 2 of 2-[(6R)-21,22,28-trifluoro-3,6,10,10-tetramethyl-12,12,24-trioxo-6-phenyl-12λ6,24λ4-dithia-3,4,19,30-tetrazapentacyclo[23.3.1.12,5.015,23.016,20]triaconta-1(29),2(30),4,15,17,20,22,25,27-nonaen-17-yl]acetic Acid

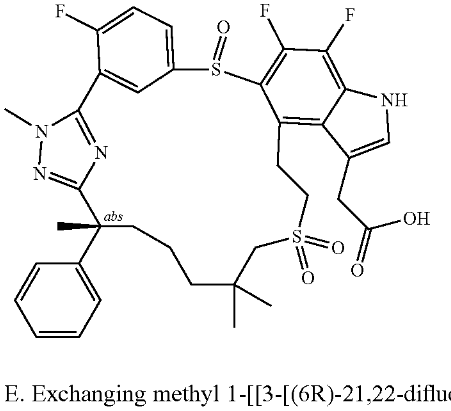

Step E. Exchanging methyl 1-[[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]methyl]cyclopropanecarboxylate (methyl ester of Example 309) with the product from Step D (370 mg, 0.5 mmol), the reaction procedure sequence, Step A of Example 310, followed by Step F and Step H of Example 204, was followed to afford the title compound (1.0 mg) as a white solid. LC-MS: MS (ESI): 727 m/z [M+H]$^+$, retention time: 2.11 minutes; purity: 97% (214 nm) (LC-MS method 47).

Example 327. 2R)-3-[3-[(6R)-17-Chloro-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid

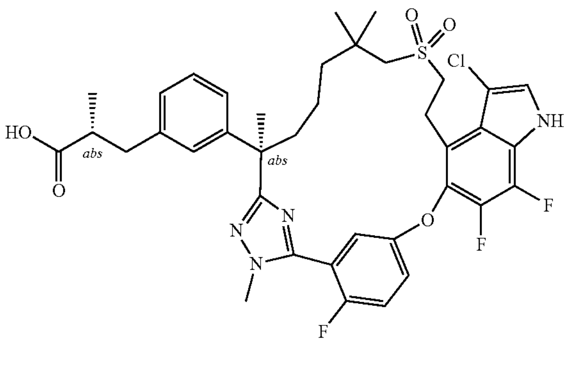 [SMILES: C[C@H](Cc1cccc([C@@]2(C)CCCC(C)(C)CS(=O)(=O)CCc3c(c(F)c(F)c4[nH]cc(Cl)c34)Oc3ccc(F)c(c3)-c3nc2nn3C)c1)C(=O)O]

To a stirred solution of methyl (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product of Example 321, 100 mg, 0.136 mmol) in 1,4-dioxane (5 mL) and tetrahydrofuran (2.5 mL) was added 1,3-dichloro-5,5-dimethylhydantoin (15 mg, 0.0746 mmol). The reaction was stirred at room temperature for 16 hours and concentrated. The residue was taken up in ethyl acetate (20 mL), washed with water, brine, dried over sodium sulfate, filtered, and concentrated to give the crude methyl (2R)-3-[3-[(6R)-17-chloro-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (70 mg), which was used in the next step without further purification.

To a solution of the above crude product (70 mg, 0.0908 mmol) in tetrahydrofuran (1.5 mL), methanol (0.5 mL), and water (0.5 mL) was added lithium hydroxide (11 mg, 0.454 mmol). The reaction was stirred at room temperature for 16 hours, quenched with 5 mL of water, acidified to pH ~5-6 with hydrochloride acid (1 M) and extracted with ethyl acetate (3×10 mL). The combined organic phase was dried over magnesium sulfate, filtered, and concentrated. The residue was purified by prep-HPLC to give the title compound (Compound 327, 25 mg, 25% two steps) as a white solid. LC-MS: MS (ESI): 757 m/z [M+H]$^+$, retention time: 1.53 minutes; purity: >99% (254 nm) (LC-MS method 40). $^1$H NMR (400 MHz, $CD_3OD$) δ 7.41 (s, 1H), 7.38-7.24 (m, 3H), 7.16-7.13 (m, 1H), 7.02-6.97 (m, 3H), 3.88 (s, 3H), 3.36-3.35 (m, 2H), 3.40-3.34 (m, 2H), 3.24-3.17 (m, 2H), 3.04-3.01 (m, 1H), 2.90-2.86 (m, 1H), 2.61-2.54 (m, 2H), 2.24-2.16 (m, 1H), 1.87-1.80 (m, 1H), 1.69 (s, 3H), 1.33-1.28 (m, 3H), 1.15-1.10 (m, 6H), 1.04 (d, J=4.0 Hz, 3H) ppm.

Example 328. (2R)—N-Cyclopropylsulfonyl-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propenamide

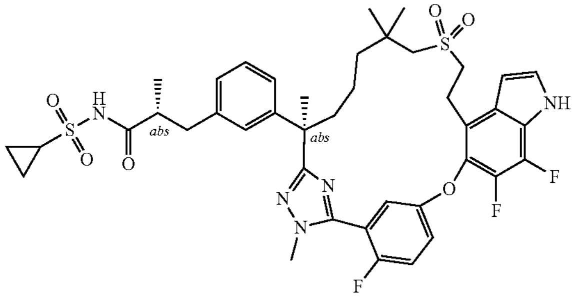 [SMILES: C[C@H](Cc1cccc([C@@]2(C)CCCC(C)(C)CS(=O)(=O)CCc3c(c(F)c(F)c4[nH]ccc34)Oc3ccc(F)c(c3)-c3nc2nn3C)c1)C(=O)NS(=O)(=O)C1CC1]

To a stirred solution of (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic acid (Example 200, 200 mg, 0.277 mmol) and 1-(3-dimethylaminopropyl)-3-ethylcarbodiimide hydrochloride (530 mg, 2.77 mmol) in dimethylformamide (6 mL) was added 4-dimethylaminopyridine (254 mg, 2.08 mmol) and cyclopropane sulfonamide (502 mg, 4.16 mmol). The reaction was stirred at room temperature under a nitrogen atmosphere for 16 hours, quenched with water (80 mL), and extracted with ethyl acetate (3×80 mL). The combined organic extracts were washed with brine, dried over sodium sulfate, filtered, and concentrated. The residue was purified by automated flash chromatography (12 g silica gel column, eluting with 0-60% ethyl acetate in petroleum ether) to give a crude product (110 mg) which was further purified by Prep-HPLC to give the title compound (Compound 328, 42 mg, 18%) as a white solid. LC-MS: MS (ESI): 826 m/z $[M+H]^+$, retention time: 1.98 minutes; purity: 97% (254 nm) (LC-MS method 42). $^1H$ NMR (400 MHz, $CD_3OD$) δ 7.38-7.32 (m, 3H), 7.24-7.20 (m, 1H), 7.15 (t, J=7.6 Hz, 1H), 7.07 (s, 1H), 7.02-6.98 (m, 2H), 6.68 (t, J=3.2 Hz, 1H), 3.85 (d, J=2.4 Hz, 3H), 3.30-3.18 (m, 1H), 3.00-2.95 (m, 1H), 2.92-2.76 (m, 3H), 2.68-2.57 (m, 2H), 2.22-2.12 (m, 1H), 1.87-1.80 (m, 1H), 1.68 (s, 3H), 1.63-1.52 (m, 1H), 1.38-1.21 (m, 3H), 1.18-1.11 (m, 6H), 1.10-1.03 (m, 6H), 1.02-0.90 (m, 4H) ppm Example 329. (2S)-3-[3-[(6R)-22,28-Difluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

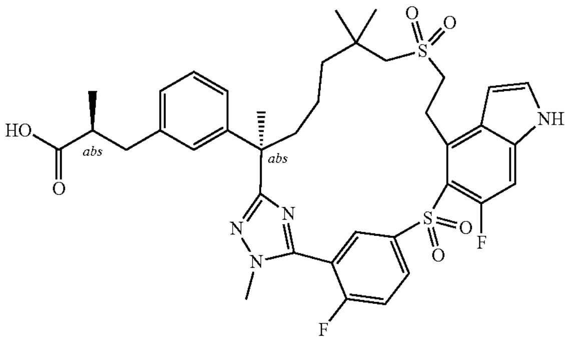 [SMILES: C[C@@H](Cc1cccc([C@@]2(C)CCCC(C)(C)CS(=O)(=O)CCc3c(c(F)cc4[nH]ccc34)S(=O)(=O)c3ccc(F)c(c3)-c3nc2nn3C)c1)C(=O)O]

Exchanging methyl (2R)-2-methyl-3-[3-[(6R)-21,22,28-trifluoro-3,6,10,10-tetramethyl-19-methylsulfonyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product of Example 320) with Diastereomer 2 of methyl (2S)-3-[3-[(6R)-22,28-difluoro-3,6,10,10-tetramethyl-12,12,24-trioxo-19-(p-tolylsulfonyl)-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step F product of Example 204, 900 mg, 0.98 mmol), the reaction procedure sequence (Steps B and C) described for Example 320 was followed to afford the title compound (Compound 329, 241 mg) as a white solid. LC-MS: MS (ESI): 753 m/z $[M+H]^+$, retention time: 1.90 minutes; purity: >99% (254 nm) (LC-MS method 42). $^1H$ NMR (400 MHz, $CD_3OD$): δ 8.37-8.34 (m, 1H), 8.30 (dd, J=6.4, 2.0 Hz, 1H), 7.62 (t, J=9.2 Hz, 1H), 7.40 (d, J=3.6 Hz, 1H), 7.20 (d, J=12 Hz, 1H), 7.15 (t, J=7.6 Hz, 1H), 7.07 (s, 1H), 6.99 (t, J=8.4 Hz, 1H), 6.72 (d, J=3.2 Hz, 1H), 3.91-3.76 (m, 5H), 3.59-3.38 (m, 2H), 3.18-3.09 (m, 2H), 2.95-2.90 (m, 1H), 2.64-2.56 (m, 2H), 2.40-2.34 (m, 1H), 1.93-1.85 (m, 1H), 1.72 (s, 3H), 1.61-1.41 (m, 3H), 1.30-1.24 (m, 4H), 1.20 (s, 3H), 1.06-1.04 (m, 3H) ppm.

Example 330. (2S)-3-[3-[(6R)-22-Fluoro-6,10,10-trimethyl-12,12,24-trioxo-4-oxa-12λ6,24λ4-dithia-19,30-diazapentacyclo[23.3.1.12,5.015,23.016,20]triaconta-1(29),2,5(30),15,17,20,22,25,27-nonaen-6-yl]phenyl]-2-methyl-propanoic Acid

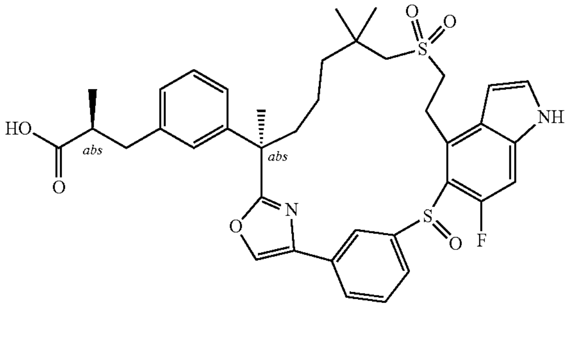 [SMILES: C[C@@H](Cc1cccc([C@@]2(C)CCCC(C)(C)CS(=O)(=O)CCc3c(c(F)cc4[nH]ccc34)S(=O)c3cccc(c3)-c3coc2n3)c1)C(=O)O]

Diastereomer 2 of Methyl (2S)-3-(3-((13R,Z)-4$^6$-fluoro-9,9,13-trimethyl-3,7,7-trioxido-4'-(phenylsulfonyl)-4'H-3,7-dithia-1(4,2)-oxazola-4(5,4)-indola-2(1,3)-benzenacyclotridecaphane-13-yl)phenyl)-2-methylpropanoate

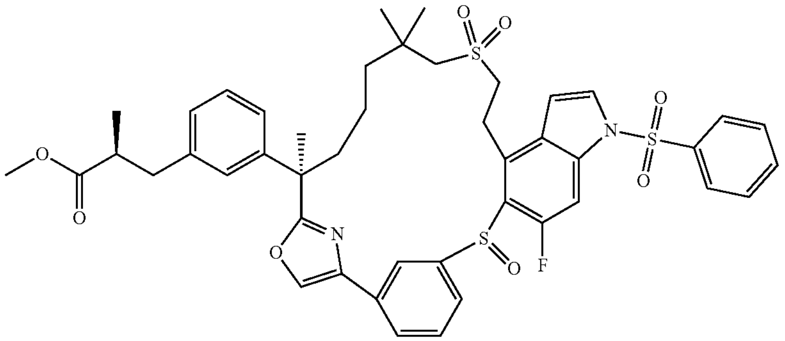 [SMILES: COC(=O)[C@@H](C)Cc1cccc([C@@]2(C)CCCC(C)(C)CS(=O)(=O)CCc3c(c(F)cc4c3ccn4S(=O)(=O)c3ccccc3)S(=O)c3cccc(c3)-c3coc2n3)c1]

Step A: Exchanging 2-bromo-1-(5-((4-bromo-6-fluoro-1-(phenylsulfonyl)-1H-indol-5-yl)oxy)-2-fluorophenyl)ethan-1-one (Intermediate 140) with 2-bromo-1-(3-((4-bromo-6-fluoro-1-(phenylsulfonyl)-1H-indol-5-yl)thio)phenyl)ethan-1-one (3.05 g, 5.24 mmol) in Step A of Example 192, the reaction procedure sequence, Steps A, B, C of Example 192, followed by Steps B, C, D of Example 6, then Step F of Example 204, was followed to prepare the title compound (210 mg) as a white solid. LC-MS: MS (ESI): 859 m/z [M+H]$^+$, retention time: 2.26 minutes; purity: 96% (254 nm) (LC-MS method 42).

Compound 330. (S012978, REQ-00819). Diastereomer 2 of (2S)-3-[3-[(6R)-22-fluoro-6,10,10-trimethyl-12,12,24-trioxo-4-oxa-12λ6,24λ4-dithia-19,30-diazapentacyclo[23.3.1.12,5.015,23.016,20]triaconta-1(29),2,5(30),15,17,20,22,25,27-nonaen-6-yl]phenyl]-2-methyl-propanoic Acid

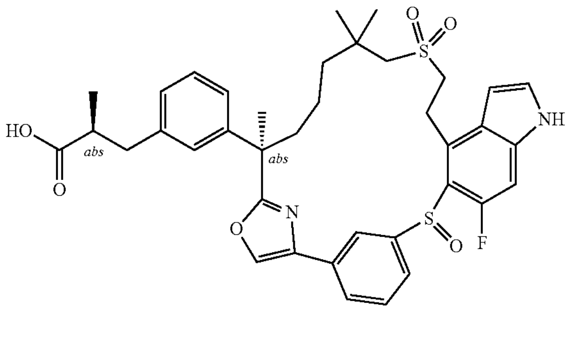 [SMILES: C[C@@H](Cc1cccc([C@@]2(C)CCCC(C)(C)CS(=O)(=O)CCc3c(c(F)cc4[nH]ccc34)S(=O)c3cccc(c3)-c3coc2n3)c1)C(=O)O]

Step B: The product from the above Step A (170 mg, 0.2 mmol) was submitted to deprotection and hydrolysis following the conditions described in Step C and Step H of Example 46 (in this order) to afford the title compound (26 mg) as a white solid. LC-MS: MS (ESI): 705 m/z [M+H]$^+$, retention time: 1.48 minutes; purity: >99% (254 nm) (LC-MS method 40). $^1$H NMR (400 MHz, DMSO-$d_6$) δ 12.01 (s, 1H), 11.68 (s, 1H), 8.65-8.63 (m, 2H), 7.86 (d, J=7.2 Hz, 1H), 7.52-7.50 (m, 2H), 7.40-7.35 (m 1H), 7.21-7.19 (m, 1H), 7.06-7.03 (m, 3H), 6.92-6.90 (s, 1H), 6.46-6.42 (m, 1H), 3.60-3.50 (m, 2H), 3.32-3.00 (m, 3H), 2.88-2.81 (m, 1H), 2.68-2.50 (m, 2H), 2.30-2.20 (m, 1H), 1.85-1.77 (m, 1H), 1.80-1.70 (m, 5H), 1.50-1.39 (m, 3H), 1.26 (s, 3H), 1.15 (s, 3H), 1.09 (d, J=6.0 Hz, 3H) ppm.

Example 331. (2S)-3-[3-[(6R)-22-Fluoro-6,10,10-trimethyl-12,12,24,24-tetraoxo-4-oxa-12λ6,24λ6-dithia-19,30-diazapentacyclo[23.3.1.12,5.015,23.016,20]triaconta-1(29),2,5(30),15,17,20,22,25,27-nonaen-6-yl]phenyl]-2-methyl-propanoic acid

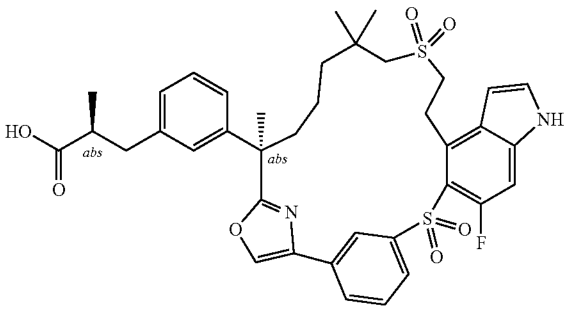 [SMILES: C[C@@H](Cc1cccc([C@@]2(C)CCCC(C)(C)CS(=O)(=O)CCc3c(c(F)cc4[nH]ccc34)S(=O)(=O)c3cccc(c3)-c3coc2n3)c1)C(=O)O]

Methyl (2S)-3-(3-((13R,Z)-4$^6$-fluoro-9,9,13-trimethyl-3,7,7-trioxido-4$^1$-(phenyl-sulfonyl)-4$^1$H-3,7-dithia-1(4,2)-oxazola-4(5,4)-indola-2(1,3)-benzenacyclotridecaphane-13-yl)phenyl)-2-methylpropanoate (Step A product of Example 330, 40 mg) was submitted to the reaction conditions described in Step B of Example 320, followed by conditions described in Steps C and F of Example 46 (in this order) to afford the title compound (Compound 331, 0.9 mg) as a white solid. LC-MS: MS (ESI): 721 m/z [M+H]$^+$, retention time: 1.49 minutes; purity: >99% (254 nm) (LC-MS method 40).

Example 332. (2S)-2-Acetoxy-3-[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]Acetate

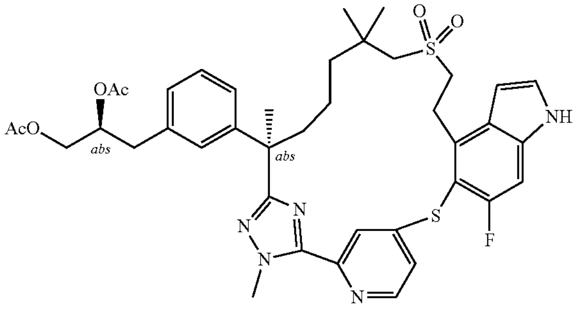 [SMILES: CC(=O)OC[C@H](Cc1cccc([C@@]2(C)CCCC(C)(C)CS(=O)(=O)CCc3c(c(F)cc4[nH]ccc34)Sc3ccnc(c3)-c3nc2nn3C)c1)OC(C)=O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with (R)-7-((2-hydroxyethyl)sulfonyl)-N',2,6,6-tetramethyl-2-phenylheptanehydrazide (intermediate 137-15, 2 g, 3.68 mmol) and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)thio)pyridine-2-carbimidothioate (Intermediate 14-15, 1.75 g, 4.42 mmol) in Step A, the reaction procedure sequence, Steps A-C described for Example 6, followed by Step B of Example 301, was followed to prepare the title compound (Compound 332, 360 mg) as a white solid. LC-MS: MS (ESI): 776 m/z $[M+H]^+$, retention time: 1.81 minutes; purity: >99% (254 nm) (LC-MS method 012). $^1H$ NMR (400 MHz, $CD_3OD$) δ 8.52 (d, J=5.2 Hz, 1H), 7.69 (s, 1H), 7.45-7.43 (m, 1H), 7.40 (d, J=3.2 Hz, 1H), 7.33 (d, J=9.2 Hz, 1H), 7.19-7.15 (m, 1H), 7.03-7.01 (m, 2H), 6.97 (s, 1H), 6.75 (d, J=2.8 Hz, 1H), 5.18-5.12 (m, 1H), 4.30 (s, 3H), 4.22-4.18 (m, 1H), 3.96-3.91 (m, 1H), 3.77-3.71 (m, 2H), 3.22-3.19 (m, 2H), 2.84 (d, J=6.8 Hz, 2H), 2.62-2.55 (m, 2H), 2.03-1.97 (m, 4H), 1.91 (s, 3H), 1.72-1.65 (m, 4H), 1.39-1.15 (m, 4H), 1.11 (s, 3H), 0.96 (s, 3H) ppm.

Example 333. (2S)-3-[3-[(6R)-22-Fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

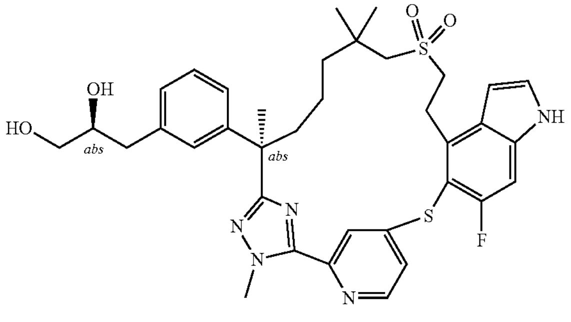 [SMILES: Cn1nc2nc1-c1cc(ccn1)Sc1c(F)cc3[nH]ccc3c1CCS(=O)(=O)CC(C)(C)CCC[C@]2(C)c1cccc(C[C@H](O)CO)c1]

To a stirred solution of [(2S)-2-acetoxy-3-[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (Example 332, 15 mg, 0.0193 mmol) in tetrahydrofuran (0.5 mL) was added lithium hydroxide (0.1 mL, 0.1 mmol, 1 M in water). The reaction was stirred at room temperature for 4 hours, acidified with 1M hydrochloric acid to pH ~4, and extracted with ethyl acetate (2×30 mL). The combined organic extracts were washed with brine (2×30 mL), dried over sodium sulfate, filtered, and concentrated. The residue was purified by prep-HPLC to give the title compound (Compound 333, 9.6 mg, 72%) as a white solid. LC-MS: MS (ESI): 692 m/z $[M+H]^+$, retention time: 1.90 minutes; purity: 99% (254 nm) (LC-MS method 012). $^1H$ NMR (400 MHz, $CD_3OD$) δ 8.50 (d, J=5.6 Hz, 1H), 7.64 (s, 1H), 7.42 (d, J=4.4 Hz, 1H), 7.38 (d, J=3.2 Hz, 1H), 7.33 (d, J=9.2 Hz, 1H), 7.12 (t, J=8 Hz, 1H), 7.03-7.01 (m, 2H), 6.95-6.93 (m, 1H), 6.73 (d, J=3.2 Hz, 1H), 4.27 (s, 3H), 3.77-3.66 (m, 3H), 3.47-3.40 (m, 2H), 3.19-3.15 (m, 2H), 2.75-2.71 (m, 1H), 2.64-2.54 (m, 3H), 2.04-1.95 (m, 1H), 1.71-1.63 (m, 4H), 1.34-1.17 (m, 4H), 1.11 (s, 3H), 0.93 (s, 3H) ppm.

Example 334. Diastereomer 2 of (2S)-3-[3-[(6R)-22-Fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

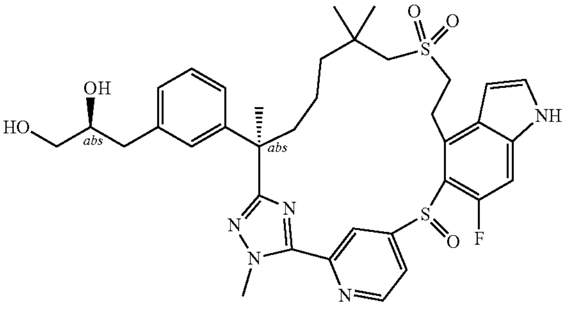 [SMILES: Cn1nc2nc1-c1cc(ccn1)S(=O)c1c(F)cc3[nH]ccc3c1CCS(=O)(=O)CC(C)(C)CCC[C@]2(C)c1cccc(C[C@H](O)CO)c1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with [(2S)-2-acetoxy-3-[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (Example 332, 100 mg, 0.129 mmol) in Step E of Example 204, the reaction procedure sequence, Steps E, F, and H of Example 204, were followed to afford the title compound (Compound 334, 5.3 mg) as a white solid. Chiral SFC separation was added to product purification in Step F under the following conditions: Instrument: SFC-150 (Waters); Column: IH 20*250 mm, 10 μm; Column temperature: 35° C.; Mobile phase: carbon dioxide/methanol (+0.2%7M ammonia in methanol)=55/45; Flow rate: 100 g/minute; Back pressure: 100 bar; Detection wavelength: 214 nm; Cycle time: 7 minutes; Sample solution: 40 mg dissolved in 20 ml methanol; Injection volume: 3 ml. LC-MS: MS (ESI): 708 m/z $[M+H]^+$, retention time: 1.77 minutes; purity: >99% (254 nm) (LC-MS method 012). $^1H$ NMR (400 MHz, $CD_3OD$) δ 8.99-8.60 (m, 2H), 7.40 (d, J=3.2 Hz, 1H), 7.28-7.04 (m, 6H), 6.58-6.52 (m, 1H), 4.31 (s, 3H), 3.77-3.58 (m, 3H), 3.48-3.40 (m, 3H), 3.19-3.03 (m, 2H), 2.85-2.71 (m, 1H), 2.65-2.44 (m, 2H), 1.87-1.67 (m, 4H), 1.60-1.40 (m, 4H), 1.38-1.06 (m, 7H) ppm Example 335. (2S)-3-[3-[(6R)-22-Fluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

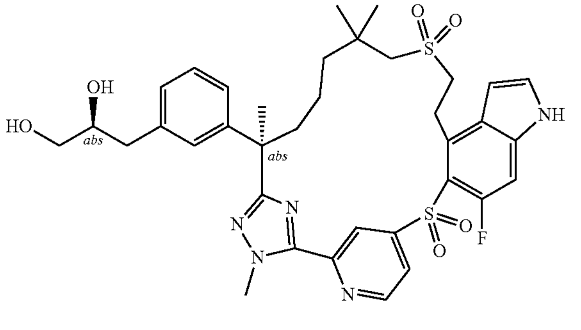 [SMILES: Cn1nc2nc1-c1cc(ccn1)S(=O)(=O)c1c(F)cc3[nH]ccc3c1CCS(=O)(=O)CC(C)(C)CCC[C@]2(C)c1cccc(C[C@H](O)CO)c1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with [(2S)-2-acetoxy-3-[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (Example 332, 100 mg, 0.129 mmol) in Step E of Example 204, the reaction procedure sequence, Step E of Example 204, then Step C of Example 180, and Step F of Example 6, was followed to afford the title compound (Compound 335, 4.1 mg) as a white solid. LC-MS: MS (ESI): 724 m/z $[M+H]^+$, retention time: 1.82 minutes; purity: 97% (254 nm) (LC-MS method 012). $^1H$ NMR (400 MHz, $CD_3OD$) δ 8.98 (d, J=5.2 Hz, 1H), 8.70 (s, 1H), 8.04 (d, J=5.2 Hz, 1H), 7.42 (d, J=3.2 Hz, 1H), 7.27 (d, J=12 Hz, 1H), 7.16 (t, J=7.6 Hz, 1H), 7.07-6.99 (m, 3H), 6.73 (d, J=2.8 Hz, 1H), 4.26 (s, 3H), 3.94-3.86 (m, 1H), 3.74-3.70 (m, 2H), 3.55-3.39 (m, 4H), 320-3.10 (m, 2H), 2.78-2.74 (m, 1H), 2.61-2.56 (m, 1H), 2.37-2.29 (m, 1H), 1.92-1.84 (m, 1H), 1.74 (s, 3H), 1.67-1.55 (m, 2H), 1.50-1.40 (m, 2H), 1.24 (s, 3H), 1.17 (s, 3H) ppm.

Example 336. Compound 336A [(2R)-2-Acetoxy-3-[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl] Acetate

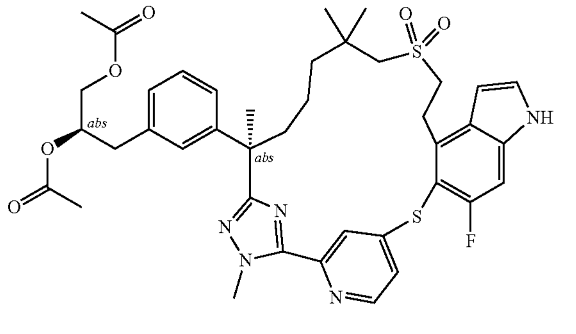 [SMILES: CC(=O)OC[C@@H](Cc1cccc([C@@]2(C)CCCC(C)(C)CS(=O)(=O)CCc3c(c(F)cc4[nH]ccc34)Sc3ccnc(c3)-c3nc2nn3C)c1)OC(C)=O]

and

Compound 336B. (2R)-3-[3-[(6R)-22-Fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

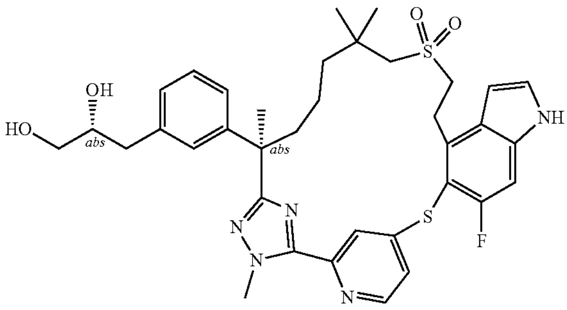 [SMILES: Cn1nc2nc1-c1cc(ccn1)Sc1c(F)cc3[nH]ccc3c1CCS(=O)(=O)CC(C)(C)CCC[C@]2(C)c1cccc(C[C@@H](O)CO)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with (R)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (intermediate 137-16, 3 g, 5.52 mmol) and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)thio)pyridine-2-carbimidothioate (Intermediate 14-15, 3.9 g, 7.24 mmol) in Step A, the reaction procedure sequence, Steps A-C described for Example 6, followed by Step B of Example 301, was followed to afford Compound 336A (337 mg, white solid) and Compound 336B (19 mg, white solid). The compound 336B originated from deprotection caused by tosyl hydrazine in the corresponding Step B of Example 301.

Compound 336A: LC-MS: MS (ESI): 776 m/z $[M+H]^+$, retention time: 2.18 minutes; purity: >99% (254 nm) (LC-MS method 004). $^1H$ NMR (400 MHz, $CD_3OD$) δ 8.50 (d, J=5.3 Hz, 1H), 7.68 (brs, 1H), 7.42 (d, J=3.8 Hz, 1H), 7.38 (d, J=3.3 Hz, 1H), 7.30 (d, J=9.1 Hz, 1H), 7.15 (t, J=7.7 Hz, 1H), 7.05-6.92 (m, 3H), 6.72 (d, J=3.0 Hz, 1H), 5.20-5.10 (m, 1H), 4.28 (s, 3H), 4.19 (dd, J=11.9, 3.4 Hz, 1H), 3.92 (dd, J=11.9, 6.4 Hz, 1H), 3.79-3.65 (m, 2H), 3.24-3.11 (m, 2H), 2.89-2.73 (m, 2H), 2.65-2.51 (m, 2H), 2.05-1.96 (m, 4H), 1.88 (s, 3H), 1.73-1.62 (m, 4H), 1.36-1.28 (m, 1H), 1.23-1.15 (m, 1H), 1.09 (s, 3H), 1.05-0.98 (m, 1H), 0.94 (s, 3H), 0.91-0.82 (m, 1H) ppm.

Compound 336B: LC-MS: MS (ESI): 692 m/z $[M+H]^+$, retention time: 2.00 minutes; purity: >99% (254 nm) (LC-MS method 004). $^1H$ NMR (400 MHz, $CD_3OD$) δ 8.50 (d, J=5.4 Hz, 1H), 7.66 (brs, 1H), 7.43 (d, J=3.8 Hz, 1H), 7.39 (d, J=3.3 Hz, 1H), 7.31 (d, J=9.0 Hz, 1H), 7.12 (t, J=7.8 Hz, 1H), 7.07-6.99 (m, 2H), 6.94 (d, J=7.7 Hz, 1H), 6.73 (d, J=3.1 Hz, 1H), 4.28 (s, 3H), 3.77-3.68 (m, 2H), 3.48-3.39 (m, 2H), 3.21-3.12 (m, 2H), 2.75 (dd, J=13.6, 5.4 Hz, 1H), 2.65-2.51 (m, 3H), 2.03-1.96 (m, 1H), 1.74-1.62 (m, 4H), 1.35-1.15 (m, 4H), 1.11 (s, 3H), 0.94 (s, 3H), 0.90-0.83 (m, 1H) ppm.

Example 337. Diastereomer 2 of (2R)-3-[3-[(6R)-22-Fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

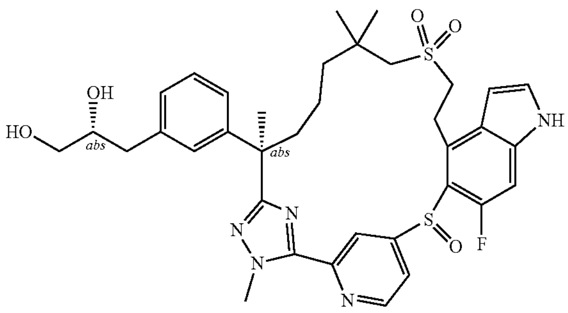 [SMILES: Cn1nc2nc1-c1cc(ccn1)S(=O)c1c(F)cc3[nH]ccc3c1CCS(=O)(=O)CC(C)(C)CCC[C@]2(C)c1cccc(C[C@@H](O)CO)c1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (product of Step D from Example 204) with [(2R)-2-acetoxy-3-[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl] acetate (Example 336A, 370 mg, 0.477 mmol) in Step E of Example 204, the reaction procedure sequence, Steps E, F, and H of Example 204, was followed to afford the title compound (Compound 337, 2.3 mg) as a white solid. Chiral SFC separation was added to the purification stage of Step F under the following conditions: Instrument: SFC-150 (Waters); Column: IH 20*250 mm, 10 μm; Column temperature: 35° C.; Mobile phase: carbon dioxide/methanol (+0.2%7M ammonia in methanol)=50/50; Flow rate: 100 g/minute; Back pressure: 100 bar; Detection wavelength: 214 nm; Cycle time: 5.6 minutes; Sample solution: 100 mg dissolved in 30 ml methanol; Injection volume: 2 ml. LC-MS: MS (ESI): 708 m/z $[M+H]^+$, retention time: 1.88 minutes; purity: >99% (254 nm) (LC-MS method 003). $^1H$ NMR (400 MHz, $CD_3OD$) δ 9.00-8.49 (m, 3H), 7.42 (d, J=3.2 Hz, 1H), 7.35-7.00 (m, 5H), 6.62-6.56 (m, 1H), 4.32 (s, 3H), 3.83-3.36 (m, 6H), 3.19-3.00 (m, 2H), 2.90-2.37 (m, 3H), 1.85-1.70 (m, 4H), 1.59-0.96 (m, 11H) ppm.

Example 338. (2R)-3-[3-[(6R)-22-Fluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

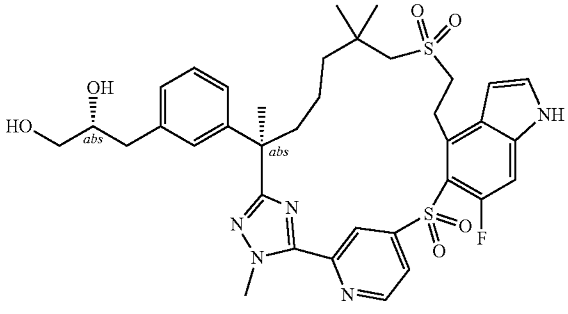 [SMILES: Cn1nc2nc1-c1cc(ccn1)S(=O)(=O)c1c(F)cc3[nH]ccc3c1CCS(=O)(=O)CC(C)(C)CCC[C@]2(C)c1cccc(C[C@@H](O)CO)c1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with [(2S)-2-acetoxy-3-[3-[(6R)-22-fluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (Example 336A, 370 mg, 0.477 mmol) in Step E of Example 204, the reaction procedure sequence, Steps E of Example 204, then Step C of Example 180, and Step F of Example 6, was followed to afford the title compound (Compound 338, 2.1 mg) as a white solid. LC-MS: MS (ESI): 724 m/z $[M+H]^+$, retention time: 1.92 minutes; purity: 90% (254 nm) (LC-MS method 003). $^1H$ NMR (400 MHz, $CD_3OD$) δ 8.98 (d, J=5.2 Hz, 1H), 8.70 (s, 1H), 8.03 (d, J=5.2 Hz, 1H), 7.42 (d, J=3.3 Hz, 1H), 7.26 (d, J=12.0 Hz, 1H), 7.18-7.14 (m, 1H), 7.09-6.98 (m, 3H) (m, 3H), 6.72 (d, J=3.1 Hz, 1H), 4.26 (s, 3H), 3.94-3.84 (m, 1H), 3.76-3.65 (m, 2H), 3.60-3.35 (m, 4H), 3.20-3.16 (m, 2H), 2.76 (dd, J=13.6, 5.5 Hz, 1H), 2.59 (dd, J=13.6, 7.7 Hz, 1H), 2.40-2.30 (m, 1H), 1.92-1.82 (m, 1H), 1.75 (s, 3H), 1.69-1.38 (m, 4H), 1.24 (s, 3H), 1.18 (s, 3H) ppm.

Example 339. [(2S)-2-acetoxy-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]Acetate

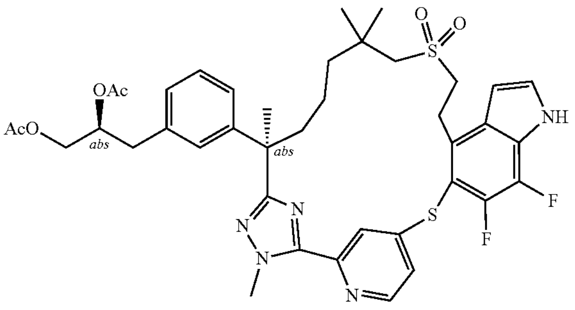 [SMILES: CC(=O)OC[C@H](Cc1cccc([C@@]2(C)CCCC(C)(C)CS(=O)(=O)CCc3c(c(F)c(F)c4[nH]ccc34)Sc3ccnc(c3)-c3nc2nn3C)c1)OC(C)=O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with (S)-3-(3-((R)-7-((2-hydroxyethyl)sulfonyl)-2,6,6-trimethyl-1-(2-methylhydrazineyl)-1-oxoheptan-2-yl)phenyl)propane-1,2-diyl diacetate (intermediate 137-15, 2 g, 3.68 mmol) and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)thio)pyridine-2-carbimidothioate (Intermediate 150-8, 1.83 g, 4.42 mmol) in Step A, the reaction procedure sequence, Steps A-C described for Example 6, followed by Step B of Example 301, was followed to afford the title compound (Compound 339, 450 mg, white solid). LC-MS: MS (ESI): 794 m/z $[M+H]^+$, retention time: 2.10 minutes; purity: 97% (254 nm) (LC-MS method 004). $^1H$ NMR (400 MHz, $CD_3OD$) δ 8.53 (d, J=5.2 Hz, 1H), 7.77-7.65 (m, 1H), 7.45-7.43 (m, 2H), 7.15 (t, J=7.6 Hz, 1H), 7.01-6.95 (m, 3H), 6.78 (t, J=6.4 Hz, 1H), 5.15-5.11 (m, 1H), 4.28 (s, 3H), 4.19-4.15 (m, 1H), 3.93-3.89 (m, 1H), 3.72-3.63 (m, 2H), 3.20-3.15 (m, 2H), 2.82 (d, J=6.8 Hz, 2H), 2.69-2.62 (m, 2H), 2.07-1.96 (m, 4H), 1.89-1.87 (m, 3H), 1.73-1.62 (m, 4H), 1.32-1.16 (m, 4H), 1.12 (s, 3H), 0.94 (s, 3H) ppm.

Example 340. (2S)-3-[3-[(6R)-21,22-Difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

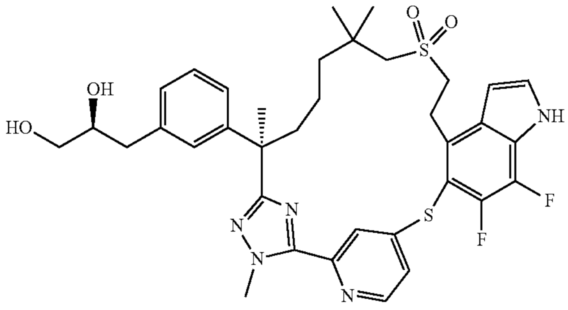 [SMILES: Cn1nc2nc1-c1cc(ccn1)Sc1c(F)c(F)c3[nH]ccc3c1CCS(=O)(=O)CC(C)(C)CCC[C@]2(C)c1cccc(C[C@H](O)CO)c1]

To a solution of [(2S)-2-acetoxy-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (Example 339, 15 mg, 0.0189 mmol) in tetrahydrofuran (0.5 mL) was added lithium hydroxide (0.1 mL, 1 M in $H_2O$). The reaction was stirred at room temperature for 4 hours. The mixture was acidified with 1M hydrochloric acid to pH ~4 and extracted with ethyl acetate (30 mL). The separated organic phase was washed with brine (2×30 mL), dried over sodium sulfate, filtered, and concentrated. The residue was purified by prep-HPLC to give the title compound (Compound 340, 9.2 mg, 69%) as a white solid. LC-MS: MS (ESI): 710 m/z $[M+H]^+$, retention time: 1.92 minutes; purity: 98% (254 nm) (LC-MS method 012). $^1H$ NMR (400 MHz, $CD_3OD$) δ 8.53 (d, J=5.2 Hz, 1H), 7.68 (brs, 1H), 7.448-7.42 (m, 2H), 7.12 (t, J=16 Hz, 1H), 7.03-7.01 (m, 2H), 6.94 (d, J=8.4 Hz, 1H), 6.78 (t, J=6 Hz, 1H), 4.28 (s, 3H), 3.75-3.65 (m, 3H), 3.48-3.37 (m, 2H), 3.18-3.15 (m, 2H), 2.76-2.70 (m, 2H), 2.65-2.55 (m, 2H), 2.08-2.02 (m, 1H), 1.75-1.67 (m, 1H), 1.64 (s, 3H), 1.28-1.19 (m, 4H), 1.14 (s, 3H), 0.94 (s, 3H) ppm.

Example 341. Diastereomer 2 of (2S)-3-[3-[(6R)-21,22-Difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

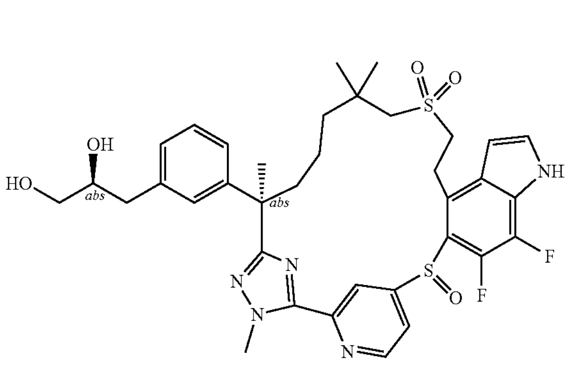 [SMILES: Cn1nc2nc1-c1cc(ccn1)S(=O)c1c(F)c(F)c3[nH]ccc3c1CCS(=O)(=O)CC(C)(C)CCC[C@]2(C)c1cccc(C[C@H](O)CO)c1]

Exchanging methyl (2S)-3-[3-[(6R)-22,28-difluoro-3,6,10,10-tetramethyl-12,12-dioxo-19-(p-tolylsulfonyl)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step E product of Example 204) with [(2S)-2-acetoxy-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (Example 339, 370 mg, 0.477 mmol) in Step F of Example 204, the reaction procedure sequence, Steps F and H of Example 204, was followed to afford the title compound (Compound 341, 2.3 mg) as a white solid. Chiral SFC separation was added to the purification stage in Step F under the following conditions: Instrument: SFC-150 (Waters); Column: AS 20*250 mm, 10 μm; Column temperature: 35° C.; Mobile phase: carbon dioxide/methanol (+0.2%7M ammonia in methanol)=70/30; Flow rate: 100 g/minute; Back pressure: 100 bar; Detection wavelength: 214 nm; Cycle time: 4.7 minutes; Sample solution: 35 mg dissolved in 15 ml of methanol; Injection volume: 1 ml. LC-MS: MS (ESI): 726 m/z $[M+H]^+$, retention time: 1.80 minutes; purity: 97% (254 nm) (LC-MS method 012). $^1H$ NMR (400 MHz, $CD_3OD$) δ 8.95-8.70 (m, 2H), 7.44 (d, J=3.2 Hz, 1H), 7.26-6.88 (m, 5H), 6.62 (s, 1H), 4.30 (s, 3H), 3.79-3.56 (m, 3H), 3.48-3.37 (m, 3H), 3.17-3.05 (m, 2H), 2.78-2.72 (m, 1H), 2.62-2.37 (m, 2H), 1.82-1.68 (m, 4H), 1.63-1.38 (m, 4H), 1.35-1.00 (m, 7H) ppm.

Example 342. 2S)-3-[3-[(6R)-21,22-Difluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]propane-1,2-diol

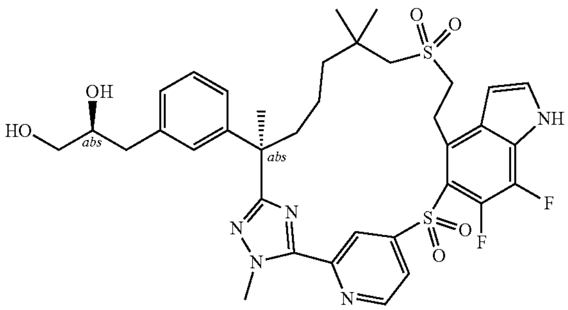 [SMILES: Cn1nc2nc1-c1cc(ccn1)S(=O)(=O)c1c(F)c(F)c3[nH]ccc3c1CCS(=O)(=O)CC(C)(C)CCC[C@]2(C)c1cccc(C[C@H](O)CO)c1]

Exchanging methyl (2R)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product of Example 319) with [(2S)-2-acetoxy-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]propyl]acetate (Example 339, 120 mg, 0.15 mmol) in Step A of Example 320, the reaction procedure sequence, Step A of Example 320, followed by Steps C and E of example 180, was followed to afford the title compound (Compound 342, 10.1 mg) as a white solid. LC-MS: MS (ESI): 742 m/z $[M+H]^+$, retention time: 1.85 minutes; purity: >99% (254 nm) (LC-MS method 012). $^1H$ NMR (400 MHz, DMSO-$d_6$) δ 12.57 (s, 1H), 9.04 (d, J=5.2 Hz, 1H), 8.61 (s, 1H), 8.02 (d, J=5.6 Hz, 1H), 7.69 (t, J=5.6 Hz, 1H), 7.13-7.09 (m, 2H), 7.01 (d, J=7.6 Hz, 2H), 6.93 (d, J=8 Hz, 1H), 6.72 (d, J=2 Hz, 1H), 4.18 (s, 3H), 3.77-3.70 (m, 1H), 3.57-3.39 (m, 3H), 3.30-3.02 (m, 4H), 2.72-2.68 (m, 1H), 2.46-2.42 (m, 1H), 2.35-2.29 (m, 1H), 1.77-1.58 (m, 5H), 1.50-1.30 (m, 4H), 1.21 (s, 3H), 1.06 (s, 3H) ppm.

Example 345. (2R)-2-Methyl-3-[3-[(6R)-17,21,22,28-tetrafluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

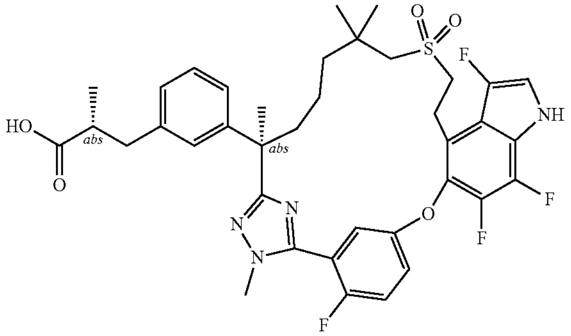 [SMILES: C[C@H](Cc1cccc([C@@]2(C)CCCC(C)(C)CS(=O)(=O)CCc3c(c(F)c(F)c4[nH]cc(F)c34)Oc3ccc(F)c(c3)-c3nc2nn3C)c1)C(=O)O]

Methyl (2R)-2-Methyl-3-[3-[(6R)-17,21,22,28-tetrafluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoate

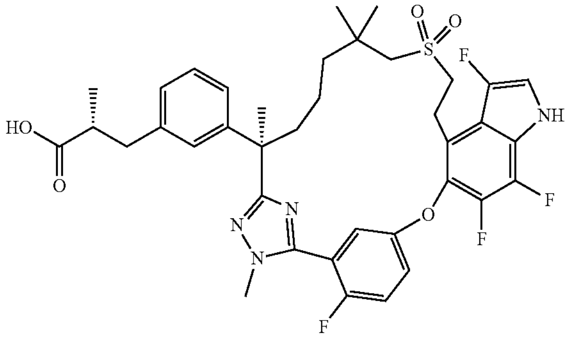 [SMILES: C[C@H](Cc1cccc([C@@]2(C)CCCC(C)(C)CS(=O)(=O)CCc3c(c(F)c(F)c4[nH]cc(F)c34)Oc3ccc(F)c(c3)-c3nc2nn3C)c1)C(=O)O]

Step A: To a stirred and cooled (0° C.) solution of methyl (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product of Example 321, 400 mg, 0.54 mmol) in acetonitrile (8 mL) and pyridine (4 mL) was added Selectfluor™ (385 mg, 1.09 mmol). The reaction was stirred at 0° C. for 1 hour, quenched with water (20 ml), and extracted with ethyl acetate (3×20 ml). The combined organic layer was washed with 1 N hydrochloric acid (10 ml), brine, dried over sodium sulfate, filtered, and concentrated. The residue was purified by flash chromatography (25 g silica gel column, eluting with 0-60% ethyl acetate in petroleum ether), followed by preparative chiral SFC purification to give the title compound (27 mg, 6.6%) as a solid. LC-MS: MS (ESI): 755 m/z $[M+H]^+$, retention time: 2.09 minutes; purity: 99% (254 nm) (LC-MS method 47).

SFC purification conditions: Instrument: SFC-150 (Waters); Column: (R,R)-WHELK 20*250 mm, 10 μm; Column temperature: 35° C.; Mobile phase: carbon dioxide/ethanol (+0.2% 7M ammonia in methanol)=75/25; Flow rate: 120 g/minute; Back pressure: 100 bar; Detection wavelength: 214 nm; Cycle time: 8.94 minutes; Sample solution: 100 mg dissolved in 30 ml ethanol. Injection volume: 4.5 ml.

Compound 345. (2R)-2-Methyl-3-[3-[(6R)-17,21,22,28-tetrafluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

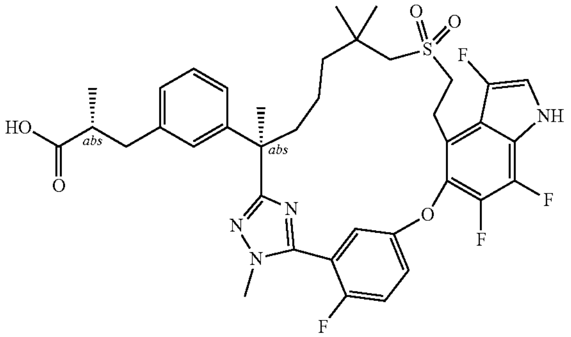 [SMILES: C[C@H](Cc1cccc([C@@]2(C)CCCC(C)(C)CS(=O)(=O)CCc3c(c(F)c(F)c4[nH]cc(F)c34)Oc3ccc(F)c(c3)-c3nc2nn3C)c1)C(=O)O]

Step B: To a stirred solution of the product from Step A (27 mg, 0.0358 mmol) in tetrahydrofuran (0.9 mL), methanol (0.3 mL), and water (0.3 mL) was added lithium hydroxide monohydrate (7.5 mg, 0.18 mmol). The reaction was stirred at room temperature for 1 hour, acidified with 1.0 M hydrochloric acid to pH ~6, and extracted with ethyl acetate (3×20 mL). The combined organic phases were washed with water and concentrated. The residue was freeze-dried to give the title compound (15 mg, 57%) as a white solid. LC-MS: MS (ESI): 741 m/z $[M+H]^+$, retention time: 1.65 minutes; purity: >99% (214 nm) (LC-MS method 030). $^1H$ NMR (400 MHz, $CD_3OD$) δ 7.40-7.30 (m, 3H), 7.24 (d, J=2.6 Hz, 1H), 7.14 (t, J=7.7 Hz, 1H), 7.04-6.97 (m, 3H), 3.85 (d, J=1.9 Hz, 3H), 3.40-3.23 (m, 4H), 3.14-3.11 (m, 1H), 2.98-2.90 (m, 2H), 2.55-2.50 (m, 2H), 2.13-2.08 (m, 1H), 1.89-1.80 (m, 1H), 1.68 (s, 3H), 1.41-1.27 (m, 3H), 1.13-1.06 (m, 7H), 1.03 (d, J=6.5 Hz, 3H) ppm.

Example 346. (2S)-3-[3-[(6R)-21,22-Difluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

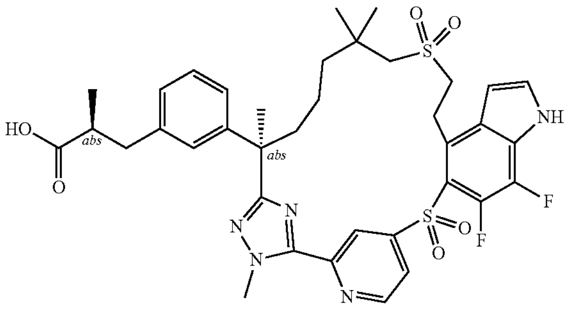 [SMILES: C[C@@H](Cc1cccc([C@@]2(C)CCCC(C)(C)CS(=O)(=O)CCc3c(c(F)c(F)c4[nH]ccc34)S(=O)(=O)c3ccnc(c3)-c3nc2nn3C)c1)C(=O)O]

Exchanging methyl (2R)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product of Example 319) with methyl (2S)-3-[3-[(6R)-21,22-difluoro-3,6,10,10-tetramethyl-12,12-dioxo-12λ6,24-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate (Step A product of Example 267, 200 mg, 0.272 mmol) in Step A of Example 320, the reaction procedure sequence, Step A of Example 320, followed by Steps C and E of example 180, was followed to afford the title compound (Compound 346, 18 mg) as a white solid. LC-MS: MS (ESI): 754 m/z $[M+H]^+$, retention time: 1.99 minutes; purity: 99% (214 nm) (LC-MS method 42). $^1H$ NMR (400 MHz, DMSO-$d_6$) δ 9.04 (d, J=5.6 Hz, 1H), 8.61 (s, 1H), 8.02 (d, J=5.2 Hz, 1H), 7.69 (d, J=3.2 Hz, 1H), 7.15-7.07 (m, 2H), 6.99-6.90 (m, 2H), 6.72 (t, J=3.2 Hz, 1H), 4.19 (s, 3H), 3.78-3.69 (m, 1H), 3.55-3.42 (m, 2H), 3.20-3.07 (m, 3H), 2.90-2.82 (m, 1H), 2.58-2.53 (m, 2H), 2.33-2.25 (m, 1H), 1.78-1.67 (m, 4H), 1.63-1.56 (m, 1H), 1.47-1.33 (m, 3H), 1.20 (s, 3H), 1.07 (s, 3H), 0.98 (d, J=6.8 Hz, 3H) ppm.

Example 347. (2S)-3-[3-[(6R)-22-Fluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

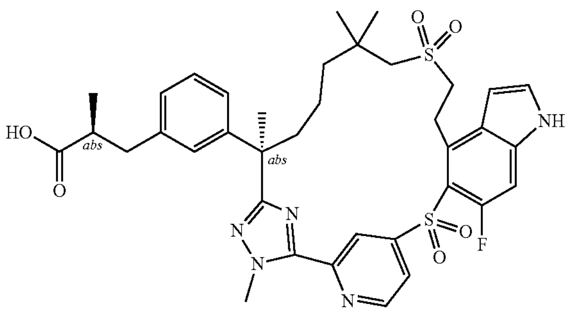 [SMILES: C[C@@H](Cc1cccc([C@@]2(C)CCCC(C)(C)CS(=O)(=O)CCc3c(c(F)cc4[nH]ccc34)S(=O)(=O)c3ccnc(c3)-c3nc2nn3C)c1)C(=O)O]

Exchanging methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 19.6 g, 49.52 mmol) in Step A of Example 204, the reaction procedure sequence, Steps A to E described for Example 204, followed by Steps C and E of Example 180, was used to prepare the title compound (Compound 347, 0.74 g, white solid). (Note: only 2.78 g of corresponding Step E product of Example 204 was used). LC-MS: MS (ESI): 736 m/z $[M+H]^+$, purity: 99% (214 nm). retention time: 1.96 minutes (LC-MS method 42). $^1H$ NMR (400 MHz, DMSO-$d_6$) δ 12.10 (brs, 1H), 11.84 (s, 1H), 9.04 (d, J=5.2 Hz, 1H), 8.56 (s, 1H), 8.01 (d, J=5.2 Hz, 1H), 7.59 (d, J=2.8 Hz, 1H), 7.41 (d, J=12.0 Hz, 1H), 7.12 (t, J=7.6 Hz, 1H), 7.08 (s, 1H), 6.97 (d, J=7.6 Hz, 1H), 6.91 (d, J=8.0 Hz, 1H), 6.64 (s, 1H), 4.18 (s, 3H), 3.89-3.75 (m, 1H), 3.65-3.52 (m, 1H), 3.52-2.43 (m, 1H), 3.24-3.12 (m, 3H), 2.93-2.79 (m, 1H), 2.67-2.52 (m, 2H), 2.35-2.24 (m, 1H), 1.83-1.68 (m, 4H), 1.61-1.46 (m, 2H), 1.42-1.28 (m, 2H), 1.19 (s, 3H), 1.07 (s, 3H), 0.98 (d, J=6.4 Hz, 3H) ppm.

Example 348. Compound 348A. 3-[3-[(6R)-22,28-Difluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2,2-dimethyl-propanoic Acid

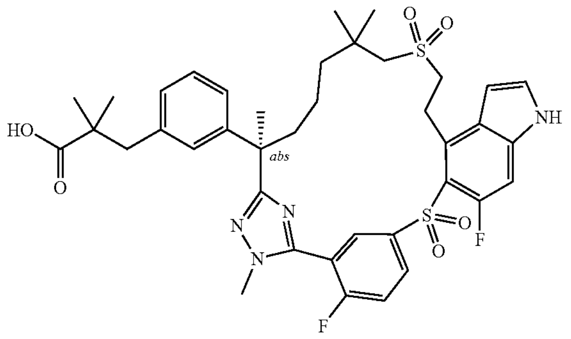 [SMILES: Cn1nc2nc1-c1cc(ccc1F)S(=O)(=O)c1c(F)cc3[nH]ccc3c1CCS(=O)(=O)CC(C)(C)CCC[C@]2(C)c1cccc(CC(C)(C)C(=O)O)c1]

Compound 348B. 3-[3-[(6R)-17-Chloro-22,28-difluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2,2-dimethyl-propanoic Acid

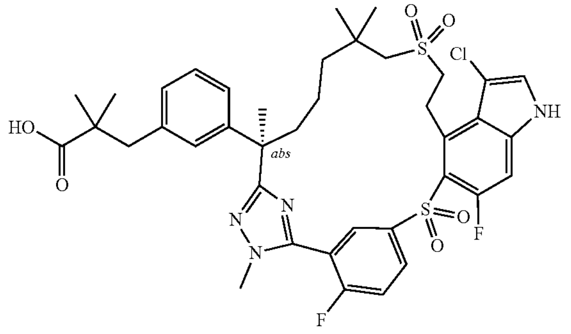 [SMILES: Cn1nc2nc1-c1cc(ccc1F)S(=O)(=O)c1c(F)cc3[nH]cc(Cl)c3c1CCS(=O)(=O)CC(C)(C)CCC[C@]2(C)c1cccc(CC(C)(C)C(=O)O)c1]

Exchanging methyl (S)-3-(3-((R)-7-((2-hydroxyethyl)sulfonyl)-2,6,6-trimethyl-1-(2-methylhydrazineyl)-1-oxo-heptan-2-yl)phenyl)-2-methylpropanoate (Intermediate 137-1) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 6.70 g, 13.4 mmol) in Step A of Example 204, the reaction procedure sequence, Steps A to E described for Example 204, followed by Steps B and C of Example 320, was followed to afford Compound 348A (6.6 mg, white solid) and Compound 348B (5.8 mg, white solid).

Compound 348A: LC-MS: MS (ESI): 767 m/z $[M+H]^+$, purity: >99% (214 nm). retention time: 1.96 minutes (LC-MS method 42). $^1H$ NMR (400 MHz, $CD_3OD$): δ 8.37-8.34 (m, 1H), 8.30 (dd, J=6.4, 2.0 Hz, 1H), 7.62 (t, J=9.2 Hz, 1H), 7.40 (d, J=3.6 Hz, 1H), 7.20 (d, J=12 Hz, 1H), 7.15 (t, J=7.6 Hz, 1H), 7.05-6.95 (m, 3H), 6.73 (d, J=3.2 Hz, 1H), 3.90-3.80 (m, 5H), 3.56-3.39 (m, 2H), 3.19-3.09 (m, 2H), 2.79 (s, 2H), 2.37-2.40 (m, 1H), 1.90-1.84 (m, 1H), 1.72 (s, 3H), 1.59-1.40 (m, 3H), 1.31-1.20 (m, 7H), 1.08-1.06 (m, 6H) ppm.

Compound 348B: LC-MS: MS (ESI): 801 m/z $[M+H]^+$, purity: >99% (214 nm). retention time: 2.00 minutes (LC-MS method 42). $^1$H NMR (400 MHz, $CD_3OD$): δ 8.41-8.34 (m, 2H), 7.63 (t, J=9.2 Hz, 1H), 7.45 (s, 1H), 7.25 (d, J=12 Hz, 1H), 7.13 (t, J=7.6 Hz, 1H), 7.07-6.97 (m, 3H), 4.26-3.84 (m, 2H), 3.84 (d, J=2.4 Hz, 3H), 3.48-3.39 (m, 2H), 3.26-3.13 (m, 2H), 2.79 (s, 2H), 2.41-2.38 (m, 1H), 1.90-1.88 (m, 1H), 1.73 (s, 3H), 1.63-1.45 (m, 3H), 1.33-1.22 (m, 7H), 1.08-1.06 (m, 6H) ppm.

Example 349. (2R)-3-[3-[(6R)-22-Fluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoic Acid

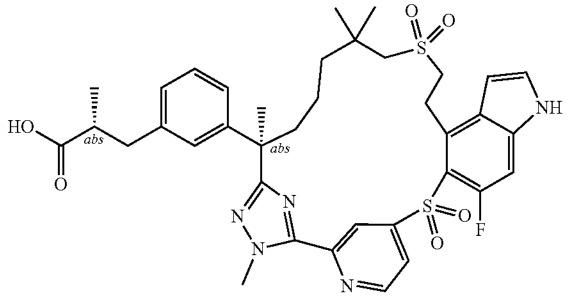 [SMILES: C[C@H](Cc1cccc([C@@]2(C)CCCC(C)(C)CS(=O)(=O)CCc3c(c(F)cc4[nH]ccc34)S(=O)(=O)c3ccnc(c3)-c3nc2nn3C)c1)C(=O)O]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with methyl (2R)-3-[3-[(6R)-22-fluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]-2-methyl-propanoate (Step A product of Example 231, 0.38 g, 0.52 mmol) in Step E of Example 204, the reaction procedure sequence, Step E of Example 204, followed by steps C and F of Example 180, was followed to afford Compound 349 (35 mg, white solid). LC-MS: MS (ESI): 736 m/z $[M+H]^+$, purity: 99% (214 nm). retention time: 2.07 minutes (LC-MS method 016). $^1$H NMR (400 MHz, $CD_3OD$) δ 8.98 (d, J=5.2 Hz, 1H), 8.71 (s, 1H), 8.03 (d, J=5.2 Hz, 1H), 7.42 (d, J=3.4 Hz, 1H), 7.26 (d, J=12.1 Hz, 1H), 7.14 (t, J=7.7 Hz, 1H), 7.08-6.92 (m, 3H), 6.72 (d, J=3.1 Hz, 1H), 4.28 (s, 3H), 3.94-3.80 (m, 1H), 3.78-3.67 (m, 1H), 3.54-3.38 (m, 2H), 3.17 (s, 2H), 2.96-2.87 (m, 1H), 2.68-2.54 (m, 2H), 2.35-2.22 (m, 1H), 1.96-1.82 (m, 1H), 1.74 (s, 4H), 1.58-1.35 (m, 3H), 1.23-1.19 (m, 6H), 1.07 (d, J=6.6 Hz, 3H) ppm.

Example 350. 3-[3-[(6R)-22-Fluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

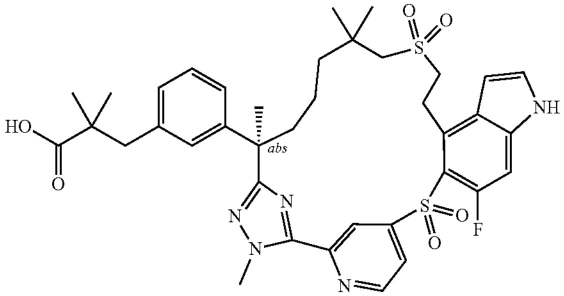 [SMILES: Cn1nc2nc1-c1cc(ccn1)S(=O)(=O)c1c(F)cc3[nH]ccc3c1CCS(=O)(=O)CC(C)(C)CCC[C@]2(C)c1cccc(CC(C)(C)C(=O)O)c1]

Exchanging methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 2.00 g, 4.01 mmol), and methyl 5-((4-bromo-6-fluoro-1H-indol-5-yl)thio)-2-fluorobenzimidothioate hydroiodide (Intermediate 76) with methyl 4-((4-bromo-6-fluoro-1H-indol-5-yl)thio)pyridine-2-carbimidothioate (Intermediate 14-15, 1.91 g, 4.81 mmol) in Step A of Example 204, the reaction procedure sequence, Steps A to C described for Example 204, then Step B of Example 301, Step E of Example 204, and lastly, Steps B and C of Example 320, was followed to afford the title compound (Compound 350, 64 mg, white solid). LC-MS: MS (ESI): 750 m/z $[M+H]^+$, purity: >99% (214 nm). retention time: 2.00 minutes (LC-MS method 42). $^1$H NMR (400 MHz, DMSO-$d_6$) δ 12.15 (brs, 1H), 11.84 (brs, 1H), 9.04 (d, J=5.2 Hz, 1H), 8.56 (s, 1H), 8.01 (d, J=5.2 Hz, 1H), 7.61-7.56 (m, 1H), 7.41 (d, J=12.0 Hz, 1H), 7.10 (t, J=8.0 Hz, 1H), 7.03 (s, 1H), 6.95-6.90 (m, 2H), 6.64 (s, 1H), 4.18 (s, 3H), 3.89-3.73 (m, 1H), 3.64-3.51 (m, 1H), 3.50-3.43 (m, 1H), 3.25-3.19 (m, 1H), 3.19-3.06 (m, 2H), 2.72 (s, 2H), 2.28-2.17 (m, 1H), 1.81-1.62 (m, 4H), 1.60-1.42 (m, 2H), 1.40-1.27 (m, 2H), 1.18 (s, 3H), 1.08 (s, 3H), 1.03-0.98 (m, 6H) ppm.

Example 351. (2S)-2-Methyl-3-[3-[(6R)-21,22,28-trifluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

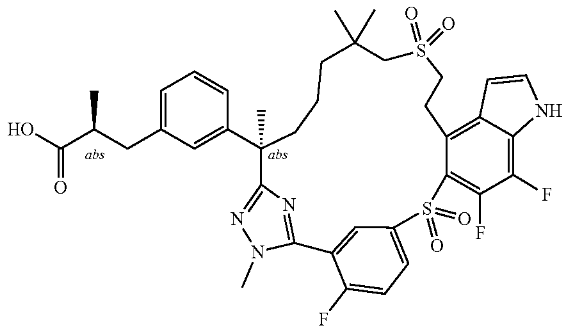 [SMILES: C[C@@H](Cc1cccc([C@@]2(C)CCCC(C)(C)CS(=O)(=O)CCc3c(c(F)c(F)c4[nH]ccc34)S(=O)(=O)c3ccc(F)c(c3)-c3nc2nn3C)c1)C(=O)O]

Exchanging methyl 5-((4-bromo-6-fluoro-1H-indol-5-yl)thio)-2-fluorobenzimidothioate hydroiodide (Intermediate 76) with methyl 5-((4-bromo-6,7-difluoro-1H-indol-5-yl)thio)-2-fluorobenzimidothioate hydroiodide (Intermediate 14-16, 1.00 g, 1.79 mmol) in Step A of Example 204, the reaction procedure sequence, Steps A to D described for Example 204, followed by Steps A, B and C of Example 320, was followed to afford the title compound (30 mg, white solid). LC-MS: MS (ESI): 771 m/z $[M+H]^+$, purity: 99% (214 nm). retention time: 1.92 minutes (LC-MS method 42). $^1H$ NMR (400 MHz, $CH_3OD$) δ 8.39-8.30 (m, 2H), 7.64 (t, J=9.2 Hz, 1H), 7.47 (d, J=3.2 Hz, 1H), 7.15 (t, J=7.6 Hz, 1H), 7.07 (s, 1H), 7.02-6.98 (m, 2H), 6.81 (t, J=3.2 Hz, 1H), 3.85-3.73 (m, 5H), 3.54-3.45 (m, 2H), 3.18-3.08 (m, 2H), 2.96-2.90 (m, 1H), 2.64-2.55 (m, 2H), 2.41-2.33 (m, 1H), 1.90-1.84 (m, 1H), 1.72 (s, 3H), 1.62-1.53 (m, 2H), 1.52-1.40 (m, 2H), 1.27 (s, 3H), 1.20 (s, 3H), 1.05 (d, J=6.6 Hz, 3H) ppm Example 352. 3-[3-[(6R)-21,22-Difluoro-3,6,10,10-tetramethyl-12,12,24,24-tetraoxo-12λ6,24λ6-dithia-3,4,19,28,30-pentazapentacyclo[23.3.1.12,5.015,23.016,20]triaconta-1(29),2(30),4,15,17,20,22,25,27-nonaen-6-yl]phenyl]-2,2-dimethyl-propanoic Acid

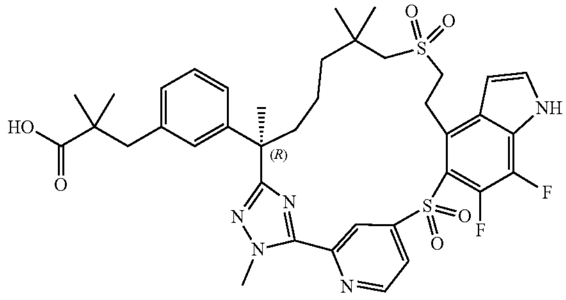

Exchanging methyl (S)-3-(3-((R)-7-(2-hydroxyethyl)sulfonyl)-2,6,6-trimethyl-1-(2-methylhydrazineyl)-1-oxoheptan-2-yl)phenyl)-2-methylpropanoate (Intermediate 137-1) with methyl (R)-3-(3-(7-((2-hydroxyethyl)sulfonyl)-2,6,6-trimethyl-1-(2-methylhydrazineyl)-1-oxoheptan-2-yl)phenyl)-2,2-dimethylpropanoate (Intermediate 137-13, 1.30 g, 2.61 mmol), and methyl 5-((4-bromo-6-fluoro-1H-indol- 5-yl)thio)-2-fluorobenzimidothioate hydroiodide (Intermediate 76) with methyl 4-((4-bromo-6,7-difluoro-1H-indol-5-yl)thio)pyridine-2-carbimidothioate (Intermediate 150-9, 1.4 g, 3.39 mmol) in Step A of Example 204, the reaction procedure sequence, Steps A to C described for Example 204, then Step B of Example 301, Step C of Example 180, and finally, Step F of Example 6 (for hydrolysis of ester and deprotection of methanesulfonyl indole), was followed to afford the title compound (Compound 352, 9 mg, white solid). The mesylate protection of indole was simultaneously complete at the corresponding Step B of Example 204 by using 2.4 equivalents of methanesulfonyl chloride. LC-MS: MS (ESI): 768 m/z $[M+H]^+$, purity: 96% (214 nm). retention time: 2.04 minutes (LC-MS method 42). $^1H$ NMR (400 MHz, DMSO-$d_6$) δ 9.01 (d, J=5.6 Hz, 1H), 8.54 (s, 1H), 7.98 (d, J=5.6 Hz, 1H), 7.59 (d, J=2.4 Hz, 1H), 7.04 (t, J=7.6 Hz, 1H), 7.00-6.97 (m, 2H), 6.87 (d, J=8.0 Hz, 1H), 6.57 (s, 1H), 4.17 (s, 3H), 3.71-3.66 (m, 2H), 3.19-3.10 (m, 2H), 2.62 (s, 2H), 2.33-2.21 (m, 1H), 2.00-1.97 (m, 1H), 1.67 (s, 3H), 1.45-1.35 (m, 2H), 1.35-1.20 (m, 4H), 1.18 (s, 3H), 1.11 (s, 3H), 0.94-0.88 (m, 6H) ppm.

Example 353. (2S)-2-Methyl-3-[3-[(12R)-6,25,26-trifluoro-9,12,16,16-tetramethyl-18,18-dioxo-2-oxa-18λ6-thia-9,10,23,29-tetrazapentacyclo[19.5.2.13,7.18,11.024,28]triaconta-1(26),3,5,7(30),8(29),10,21,24,27-nonaen-12-yl]phenyl]propanoic Acid

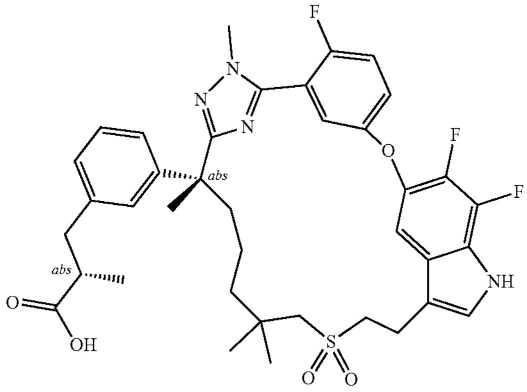 [SMILES: C[C@@H](Cc1cccc([C@@]2(C)CCCC(C)(C)CS(=O)(=O)CCc3c[nH]c4c(F)c(F)c(cc34)Oc3ccc(F)c(c3)-c3nc2nn3C)c1)C(=O)O]

Methyl (S)-3-(3-((R)-2-(5-(5-((6,7-difluoro-1H-indol-5-yl)oxy)-2-fluorophenyl)-1-methyl-1H-1,2,4-triazol-3-yl)-6,6-dimethyl-7-(vinylsulfonyl)heptan-2-yl)phenyl)-2-methylpropanoate

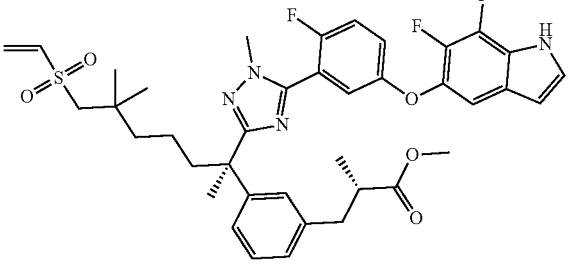

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 0.70 g, 1.44 mmol), and methyl 5-((4-bromo-6-fluoro-1H-indol-5-yl)oxy)-2-fluorobenzimidothioate hydroiodide (Intermediate 14-1) with methyl 5-((6,7-difluoro-1H-indol-5-yl)oxy)-2-fluorobenzimidothioate hydroiodide (Intermediate 14-17, 0.74 g, 1.59 mmol) in Step A of Example 6, the reaction procedure sequence (Steps A to B) described for Example 6 was followed to afford the title compound (0.69 g) as a white solid. LC-MS: MS (ESI): 737 m/z $[M+H]^+$, purity: 97% (214 nm), retention time: 1.92 minutes (LC-MS method 040).

Methyl (2S)-2-methyl-3-[3-[(12R,19E)-6,25,26-trifluoro-9,12,16,16-tetramethyl-18,18-dioxo-2-oxa-18 6-thia-9,10,23,29-tetrazapentacyclo[19.5.2.13,7.18,11.024,28]triaconta-1(26),3,5,7(30),8(29),10,19,21,24,27-decaen-12-yl]phenyl]propanoate

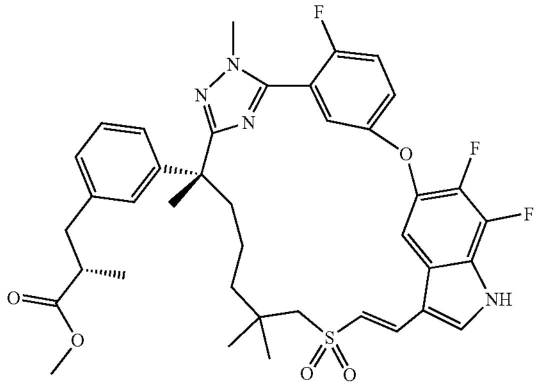 [SMILES: COC(=O)[C@@H](C)Cc1cccc([C@@]2(C)CCCC(C)(C)CS(=O)(=O)/C=C/c3c[nH]c4c(F)c(F)c(cc34)Oc3ccc(F)c(c3)-c3nc2nn3C)c1]

Step B: To a stirred solution of the product from Step A (350 mg, 0.475 mmol) in dimethylformamide (315 mL) and dimethyl sulfoxide (35 mL) was added copper(II) acetate (156 mg, 0.86 mmol) and palladium(II) acetate (21 mg, 0.095 mmol). The mixture was stirred at 70° C. for 16 hours, cooled to room temperature, diluted with ethyl acetate (300 mL), washed with water, brine, dried over sodium sulfate, filtered, and concentrated. The residue was purified by automated flash chromatography (24 g silica gel column, eluting with 0-60% ethyl acetate in petroleum ether) to give the title compound (75 mg, 20%) as a solid. LC-MS: MS (ESI): 735 m/z $[M+H]^+$, purity: 92% (254 nm), retention time: 1.86 minutes (LC-MS method 003).

Compound 353: (2S)-2-Methyl-3-[3-[(12R)-6,25,26-trifluoro-9,12,16,16-tetramethyl-18,18-dioxo-2-oxa-18 6-thia-9,10,23,29-tetrazapentacyclo[19.5.2.13,7.18,11.024,28]triaconta-1(26),3,5,7(30),8(29),10,21,24,27-nonaen-12-yl]phenyl]propanoic Acid

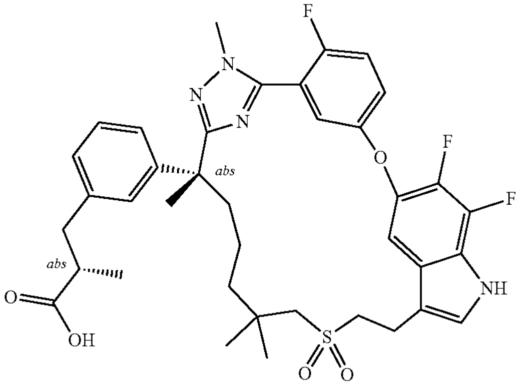 [SMILES: C[C@@H](Cc1cccc([C@@]2(C)CCCC(C)(C)CS(=O)(=O)CCc3c[nH]c4c(F)c(F)c(cc34)Oc3ccc(F)c(c3)-c3nc2nn3C)c1)C(=O)O]

Step C: Exchanging methyl (2R)-3-[3-[22,28-difluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]-2-methyl-propanoate (Step C product of Example 6) with the product from Step B of this Example, the reaction procedure sequence (Steps D and F) described in Example 6 was followed to afford the title compound (50 mg) as a white solid. LC-MS: MS (ESI): 723 m/z $[M+H]^+$, purity: 96% (254 nm), retention time: 1.93 minutes (LC-MS method 040). $^1H$ NMR (400 MHz, $CD_3OD$) δ 7.51-7.44 (m, 1H), 7.38 (t, J=9.2 Hz, 1H), 7.32 (dd, J=6.4, 1.2 Hz, 1H), 7.25 (s, 1H), 7.12 (t, J=7.8 Hz, 1H),7.03-6.97 (m, 3H), 6.80 (dd, J=5.2, 3.2 Hz, 1H), 3.81 (d, J=2.4 Hz, 3H), 3.50-3.38 (m, 1H), 3.30-3.15 (d, m, 3H), 2.98-2.89 (m, 1H), 2.63-2.50 (m, 2H), 2.40 (d, J=13.6 Hz, 1H), 2.22-2.13 (m, 1H), 1.98-1.91 (m, 1H), 1.89-1.80 (m, 1H), 1.63 (s, 3H), 1.30-1.20 (m, 1H), 1.16-0.98 (m, 11H), 0.89-0.67 (m, 1H) ppm.

Example 354. Methyl (2S)-3-[3-[(12R)-6,26-difluoro-9,12,16,16-tetramethyl-18,18-dioxo-2,18λ6-dithia-9,10,23,29-tetrazapentacyclo[19.5.2.13,7.18,11.024,28]triaconta-1(26),3,5,7(30),8(29),10,21,24,27-nonaen-12-yl]phenyl]-2-methyl-propanoate

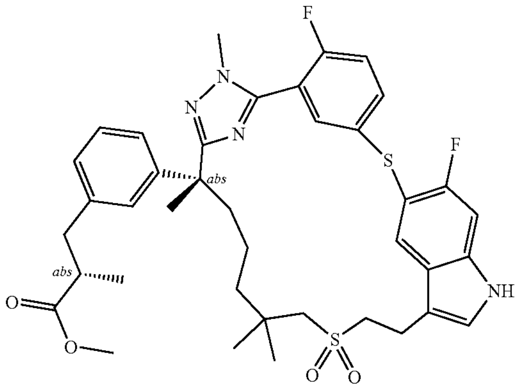 [SMILES: COC(=O)[C@@H](C)Cc1cccc([C@@]2(C)CCCC(C)(C)CS(=O)(=O)CCc3c[nH]c4cc(F)c(cc34)Sc3ccc(F)c(c3)-c3nc2nn3C)c1]

Methyl (S)-3-(3-((R)-2-(5-(2-fluoro-5-((6-fluoro-1H-indol-5-yl)thio)phenyl)-1-methyl-1H-1,2,4-triazol-3-yl)-7-((2-hydroxyethyl)sulfonyl)-6,6-dimethylheptan-2-yl)phenyl)-2-methylpropanoate

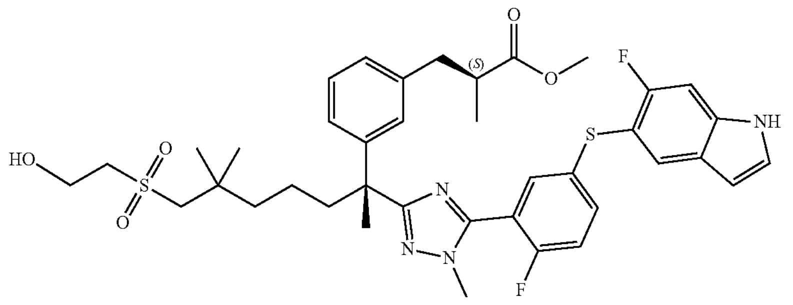

Step A: To a stirred solution of methyl (S)-3-(3-((R)-2-(5-(5-((4-bromo-6-fluoro-1H-indol-5-yl)thio)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 204, 1.50 g, 1.80 mmol) in ethanol (20 mL) was added palladium on carbon (10%, 50% wet, 500 mg). The mixture was stirred at 60° C. for 24 hours under hydrogen, then filtered through a pad of Celite, and the filter cake washed with methanol (15 mL). The combined filtrates were concentrated to give the title compound (1.10 g, 66%) as a white solid. LC-MS: MS (ESI): 753 m/z $[M+H]^+$, purity: 99% (214 nm). retention time: 2.01 minutes (LC-MS method 34).

Compound 354. Methyl (2S)-3-[3-[(12R)-6,26-difluoro-9,12,16,16-tetramethyl-18,18-dioxo-2,18λ6-dithia-9,10,23,29-tetrazapentacyclo[19.5.2.13,7.18,11.024,28]triaconta-1(26),3,5,7(30),8(29),10,21,24,27-nonaen-12-yl]phenyl]-2-methyl-propanoate

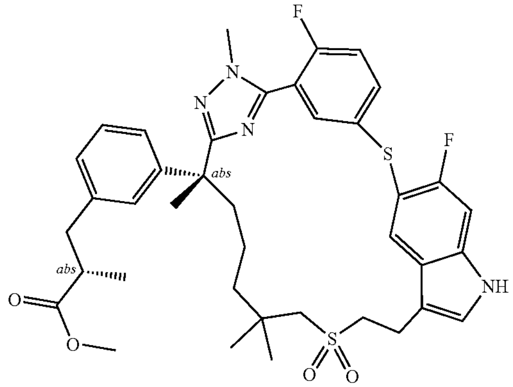 [SMILES: COC(=O)[C@@H](C)Cc1cccc([C@@]2(C)CCCC(C)(C)CS(=O)(=O)CCc3c[nH]c4cc(F)c(cc34)Sc3ccc(F)c(c3)-c3nc2nn3C)c1]

Step B: Exchanging methyl (S)-3-(3-((R)-2-(5-(5-((4-bromo-6-fluoro-1H-indol-5-yl)thio)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 204) with the product of Step A of this Example (1100 mg, 1.46 mmol) in Step B of Example 204, the reaction procedure sequence, Step B of Example 204, followed by Step B of Example 353, then Step D of Example 204, was followed to give the title compound (35 mg) as a white solid. LC-MS: MS (ESI): 735 m/z $[M+H]^+$, purity: 99% (214 nm). retention time: 1.81 minutes (LC-MS method 43). $^1$H NMR (400 MHz, $CD_3OD$) δ 7.85 (d, J=6.8 Hz, 1H), 7.74-7.66 (m, 1H), 7.34-7.26 (m, 1H), 7.19 (t, J=4.8 Hz, 2H), 7.17-7.10 (m, 2H), 7.00 (d, J=8.0 Hz, 1H), 6.96-6.92 (m, 2H), 3.75 (d, J=2.0 Hz, 3H), 3.55 (s, 3H), 3.28-3.23 (m, 3H), 2.90-2.80 (m, 1H), 2.70-2.60 (m, 2H), 2.47 (d, J=14.0 Hz, 1H), 2.22-2.09 (m, 2H), 1.89-1.79 (m, 1H), 1.62 (s, 3H), 1.37-1.21 (m, 3H), 1.18-1.00 (m, 11H) ppm.

Example 355. Diastereomer 2 of (2S)-3-[3-[(12R)-6,26-Difluoro-9,12,16,16-tetramethyl-2,18,18-trioxo-2λ4,18λ6-dithia-9,10,23,29-tetrazapentacyclo[19.5.2.13,7.18,11.024,28]triaconta-1(26),3,5,7(30),8(29),10,21,24,27-nonaen-12-yl]phenyl]-2-methyl-propanoic Acid

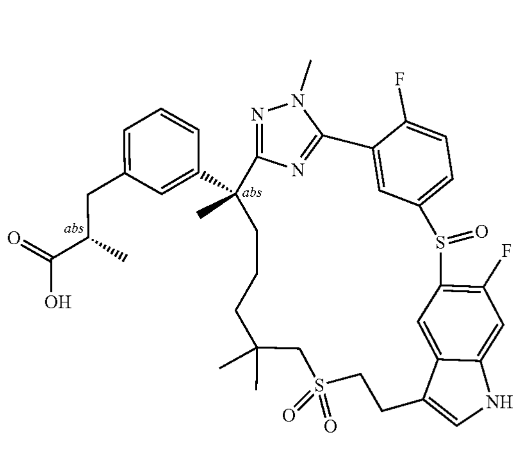 [SMILES: C[C@@H](Cc1cccc([C@@]2(C)CCCC(C)(C)CS(=O)(=O)CCc3c[nH]c4cc(F)c(cc34)S(=O)c3ccc(F)c(c3)-c3nc2nn3C)c1)C(=O)O]

and Compound 355B. (2S)-3-[3-[(12R)-6,26-Difluoro-9,12,16,16-tetramethyl-2,2,18,18-tetraoxo-2λ6,18λ6-dithia-9,10,23,29-tetrazapentacyclo[19.5.2.13,7.18,11.024,28]triaconta-1(26),3,5,7(30),8(29),10,21,24,27-nonaen-12-yl]phenyl]-2-methyl-propanoic Acid

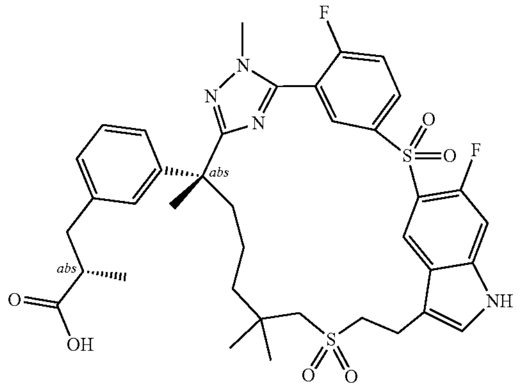 [SMILES: C[C@@H](Cc1cccc([C@@]2(C)CCCC(C)(C)CS(=O)(=O)CCc3c[nH]c4cc(F)c(cc34)S(=O)(=O)c3ccc(F)c(c3)-c3nc2nn3C)c1)C(=O)O]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with methyl (2S)-3-[3-[(12R)-6,26-difluoro-9,12,16,16-tetramethyl-18,18-dioxo-2,18λ6-dithia-9,10,23,29-tetrazapentacyclo[19.5.2.13,7.18,11.024,28]triaconta-1(26),3,5,7(30),8(29),10,21,24,27-nonaen-12-yl]phenyl]-2-methyl-propanoate (Example 354, 32 mg, 0.0435 mmol) in Step E of Example 204, the reaction procedure sequence, Steps E, F and H described for Example 204, was followed to give a mixture of the two title compounds. This mixture was separated by reverse phase preparative HPLC to give the first eluent, Compound 355A (12 mg, white solid), and the second eluent, Compound 355B (2.5 mg, white solid).

Compound 355A: LC-MS: MS (ESI): 737 m/z $[M+H]^+$, purity: >99% (214 nm). retention time: 1.50 minutes (LC-MS method 15). $^1$H NMR (400 MHz, $CD_3OD$) δ 8.04 (t, J=5.6 Hz, 1H), 7.99-7.90 (m, 2H), 7.58-7.50 (m, 1H), 7.26 (s, 1H), 7.21-7.09 (m, 2H), 7.10-6.97 (m, 3H), 3.79 (d, J=5.2 Hz, 3H), 3.38 (m, 1H), 3.28-3.18 (m, 3H), 2.97-2.78 (m, 2H), 2.68-2.52 (m, 3H), 2.31-2.17 (m, 1H), 1.97-1.89 (m, 1H), 1.69 (s, 3H), 1.45-1.28 (m, 4H), 1.21-1.09 (m, 7H), 1.10-1.04 (m, 4H) ppm.

Compound 355B: LC-MS: MS (ESI): 753 m/z $[M+H]^+$, purity: 99% (214 nm). retention time: 1.53 minutes (LC-MS method 24). $^1$H NMR (400 MHz, $CD_3OD$) δ 8.47-8.42 (m, 1H), 8.34 (d, J=6.8 Hz, 1H), 7.99 (dd, J=6.4, 2.4 Hz, 1H), 7.61 (t, J=9.2 Hz, 1H), 7.31 (s, 1H), 7.17 (d, J=11.2 Hz, 1H), 7.12 (t, J=7.6 Hz, 1H), 7.04-6.96 (m, 3H), 3.79 (s, 3H), 3.45-3.35 (m, 3H), 3.00-2.90 (m, 2H), 2.79 (d, J=14.0 Hz, 1H), 2.62-2.54 (m, 2H), 2.33-2.06 (m, 1H), 1.92-1.86 (m, 1H), 1.67 (s, 3H), 1.51-1.42 (m, 1H), 1.40-1.29 (m, 4H), 1.20-1.15 (7H), 1.10-1.00 (m, 4H) ppm.

Example 356. (2R)-3-[3-[(6R)-28-Fluoro-3,6,10,10-tetramethyl-12,12-dioxo-24-oxa-12λ6-thia-3,4,19,22,30-pentazapentacyclo[23.3.1.12,5.015,23.016,20]triaconta-1(29),2(30),4,15,17,20,22,25,27-nonaen-6-yl]phenyl]-2-methyl-propanoic acid

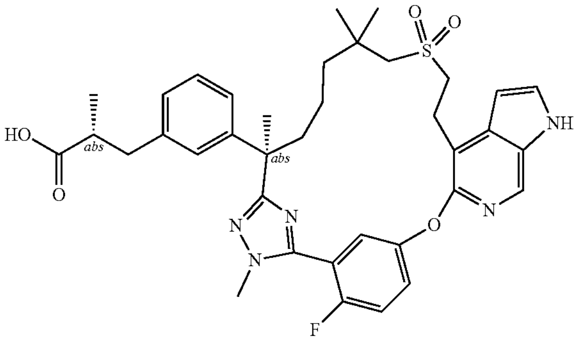 [SMILES: C[C@H](Cc1cccc([C@@]2(C)CCCC(C)(C)CS(=O)(=O)CCc3c(ncc4[nH]ccc34)Oc3ccc(F)c(c3)-c3nc2nn3C)c1)C(=O)O]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 1.53 g, 3.16 mmol), and methyl 5-((4-bromo-6-fluoro-1H-indol-5-yl)oxy)-2-fluorobenzimidothioate hydroiodide (Intermediate 14-1) with methyl 5-((4-bromo-1H-pyrrolo[2,3-c]pyridin-5-yl)oxy)-2-fluorobenzimidothioate hydroiodide (Intermediate 14-18, 1.20 g, 3.16 mmol) in Step A of Example 6, the reaction procedure sequence, Steps A to D and F described for Example 6, was followed to afford the title compound (Compound 356, 29 mg) as a white solid. LC-MS: MS (ESI): 688 m/z $[M+H]^+$, purity: >99% (214 nm), retention time: 1.44 minutes (LC-MS method 004). $^1$H NMR (400 MHz, $CD_3OD$) δ 8.31 (s, 1H), 7.61-7.58 (m, 1H), 7.39 (t, J=9.2 Hz, 1H), 7.19-7.08 (m, 3H), 7.05 (s, 1H), 7.01 (d, J=7.6 Hz, 1H), 6.97 (d, J=7.6 Hz, 1H), 6.74 (d, J=2.8 Hz, 1H), 3.87-3.85 (m, 3H), 3.49-3.46 (m, 2H), 3.41-3.37 (m, 2H), 2.97-2.92 (m, 2H), 2.72-2.56 (m, 3H), 2.20-2.14 (m, 1H), 1.80-1.74 (m, 1H), 1.67 (s, 3H), 1.61-1.55 (m, 1H), 1.40-1.29 (m, 1H), 1.25-1.16 (m, 2H), 1.08-1.07 (m, 6H), 1.01 (s, 3H) ppm.

Example 357. (2S)-3-[3-[(6R)-22-Fluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

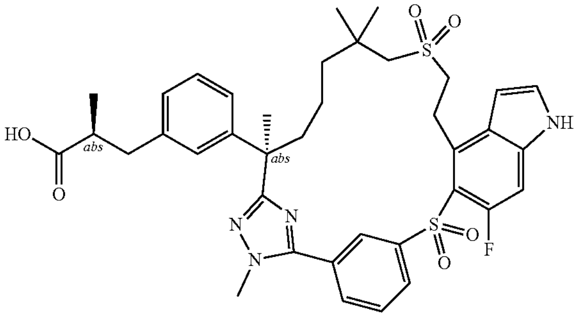 [SMILES: C[C@@H](Cc1cccc([C@@]2(C)CCCC(C)(C)CS(=O)(=O)CCc3c(c(F)cc4[nH]ccc34)S(=O)(=O)c3cccc(c3)-c3nc2nn3C)c1)C(=O)O]

Exchanging methyl 5-((4-bromo-6-fluoro-1H-indol-5-yl)thio)-2-fluorobenzimidothioate hydroiodide (Intermediate 76) with methyl 3-((4-bromo-6-fluoro-1H-indol-5-yl)sulfinyl)benzimidothioate hydroiodide (Intermediate 14-13, 897 mg, 1.66 mmol) in Step A of Example 6, the reaction procedure sequence, Steps A, B, C, D, E of Example 204, followed by Step B of Example 320, then Step G and H of Example 204, was followed to afford the title compound (Compound 357, 14 mg) as a white solid. LC-MS: MS (ESI): 735 m/z $[M+H]^+$, purity: >99% (214 nm), retention time: 1.52 minutes (LC-MS method 034). $^1H$ NMR (400 MHz, $CD_3OD$) δ 8.45 (s, 1H), 8.28 (d, J=7.6 Hz, 1H), 8.10 (d, J=8.0 Hz, 1H), 7.86-7.82 (m, 1H), 7.42 (d, J=3.6 Hz, 1H), 7.24 (d, J=12.0 Hz, 1H), 7.18-7.14 (m, 1H), 7.10 (s, 1H), 7.06 (d, J=7.6 Hz, 1H), 7.01 (d, J=7.6 Hz, 1H), 6.72 (d, J=3.2 Hz, 1H), 3.97 (s, 3H), 3.84-3.78 (m, 2H), 3.59-3.54 (m, 1H), 3.42-3.38 (m, 1H), 3.22-3.14 (m, 2H), 2.96-2.92 (m, 1H), 2.67-2.58 (m, 2H), 2.41-2.36 (m, 1H), 1.93-1.87 (m, 1H), 1.74 (s, 3H), 1.62-1.55 (m, 2H), 1.49-1.42 (m, 1H), 1.33-1.30 (m, 4H), 1.23 (s, 3H), 1.09 (d, J=6.8 Hz, 3H) ppm.

Example 358. 2,2-Dimethyl-3-[3-[(6R)-21,22,28-trifluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

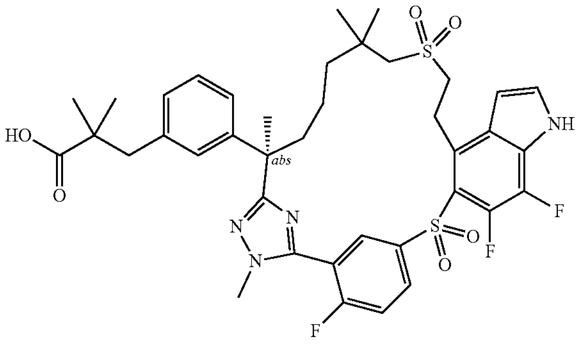 [SMILES: Cn1nc2nc1-c1cc(ccc1F)S(=O)(=O)c1c(F)c(F)c3[nH]ccc3c1CCS(=O)(=O)CC(C)(C)CCC[C@]2(C)c1cccc(CC(C)(C)C(=O)O)c1]

Exchanging methyl (2R)-2-methyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product of Example 319) with methyl 2,2-dimethyl-3-[3-[(6R)-21,22,28-trifluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]propanoate (Step A product of Example 279, 280 mg, 0.365 mmol) in Step A of Example 320, the reaction procedure sequence (Steps A, B and C) described for Example 320 was followed to prepare the title compound (Compound 358, 35 mg) as a white solid. LC-MS: MS (ESI): 785 m/z $[M+H]^+$, purity: >99% (214 nm). retention time: 1.87 minutes (LC-MS method 003). $^1H$ NMR (400 MHz, $CD_3OD$) δ 8.40-8.30 (m, 2H), 7.66 (t, J=9.6 Hz, 1H), 7.46 (s, 1H), 7.12 (t, J=7.6 Hz, 1H), 7.04-7.01 (m, 2H), 6.96 (d, J=8.0 Hz, 1H), 6.80 (s, 1H), 3.85-3.70 (m, 5H), 3.56-3.40 (m, 2H), 3.19-3.07 (m, 2H), 2.78 (s, 2H), 2.39-2.34 (m, 1H), 1.86 (t, J=13.2 Hz, 1H), 1.71 (s, 3H), 1.60-1.50 (m, 2H), 1.46-1.40 (m, 1H), 1.32-1.25 (m, 4H), 1.20 (s, 3H), 1.07 (s, 6H) ppm.

Example 359. (2S)-3-[3-[(6R)-22,28-Difluoro-3,6,10,10-tetramethyl-12,12-dioxo-24-oxa-12λ6-thia-3,4,18,19,30-pentazapentacyclo[23.3.1.12,5.015,23.016,20]triaconta-1(29),2(30),4,15,17,20,22,25,27-nonaen-6-yl]phenyl]-2-methyl-propanoic Acid

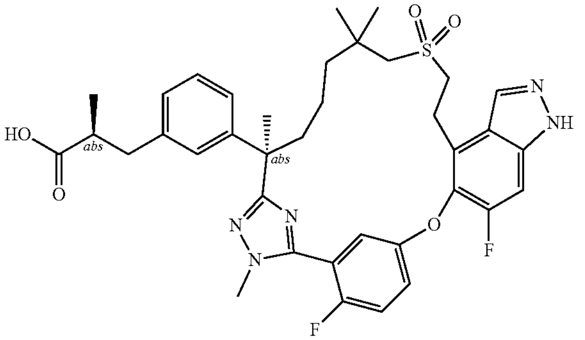 [SMILES: C[C@@H](Cc1cccc([C@@]2(C)CCCC(C)(C)CS(=O)(=O)CCc3c(c(F)cc4[nH]ncc34)Oc3ccc(F)c(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (intermediate 137-1, 0.8 g, 1.65 mmol) and methyl 5-((4-bromo-6-fluoro-1H-indol-5-yl)oxy)-2-fluorobenzimidothioate hydroiodide (Intermediate 14-1) with methyl 5-((4-bromo-6-fluoro-1H-indazol-5-yl)oxy)-2-fluorobenzimidothioate hydroiodide (Intermediate 14-19, 0.6 g, 1.65 mmol) in Step A, the reaction procedure sequence (Steps A-D, and Step F) described for Example 6 was followed to prepare the title compound (Compound 359, 3 mg) as a white solid. LC-MS: MS (ESI): 706 m/z $[M+H]^+$, retention time: 1.34 minutes; purity: 96% (254 nm) (LC-MS method 40). $^1H$ NMR (400 MHz, $CD_3OD$) δ 8.25 (s, 1H), 7.46-7.27 (m, 3H), 7.18-7.09 (m, 2H), 7.03-6.91 (m, 3H), 3.82 (s, 3H), 3.53-3.43 (m, 2H), 3.02-2.87 (m, 2H), 2.71 (d, J=13.6 Hz, 1H), 2.64-2.49 (m, 2H), 2.20-2.07 (m, 1H), 1.83-1.73 (m, 1H), 1.64 (s, 3H), 1.41-1.24 (m, 3H), 1.21-1.11 (m, 2H), 1.09-0.97 (m, 10H) ppm.

Example 360. Compound 360A. Methyl (2R)-2-methyl-3-[3-[(6R)-21,22,28-trifluoro-3,6,10,10-tetramethyl-14-(methylamino)-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoate

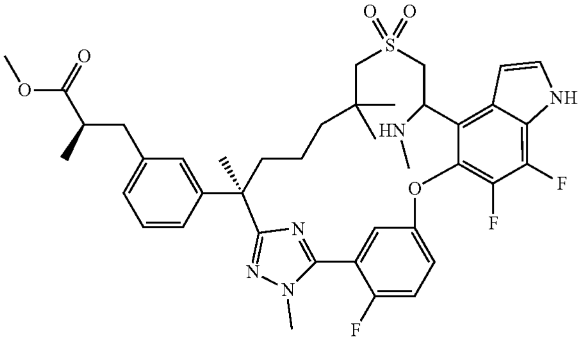 [SMILES: CNC1CS(=O)(=O)CC(C)(C)CCC[C@](C)(c2cccc(C[C@@H](C)C(=O)OC)c2)c2nc(n(C)n2)-c2cc(ccc2F)Oc2c(F)c(F)c3[nH]ccc3c21]

and 360B, 360C, Diastereomers 1 and 2 of (2R)—N,2-dimethyl-3-[3-[(6R)-21,22,28-trifluoro-3,6,10,10-tetramethyl-14-(methylamino)-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propenamide

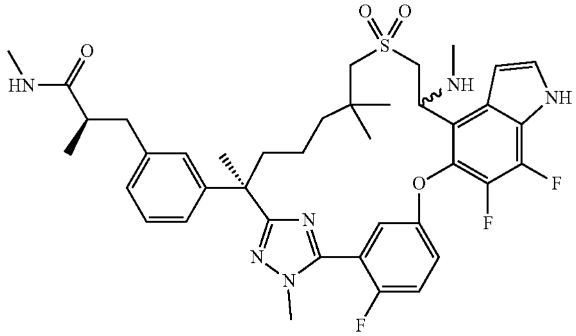 [SMILES: CNC(=O)[C@H](C)Cc1cccc([C@@]2(C)CCCC(C)(C)CS(=O)(=O)CC(NC)c3c(c(F)c(F)c4[nH]ccc34)Oc3ccc(F)c(c3)-c3nc2nn3C)c1]

and 360D. (2R)-2-Methyl-3-[3-[(6R)-21,22,28-trifluoro-3,6,10,10-tetramethyl-14-(methylamino)-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic Acid

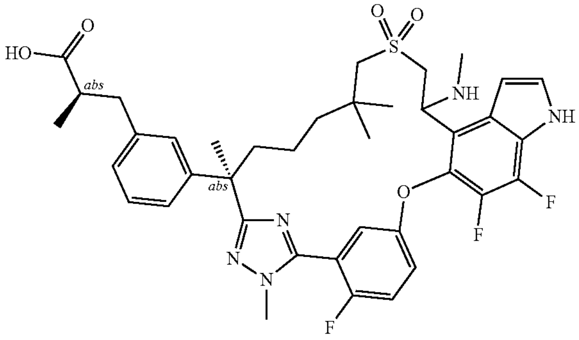 [SMILES: CNC1CS(=O)(=O)CC(C)(C)CCC[C@](C)(c2cccc(C[C@@H](C)C(=O)O)c2)c2nc(n(C)n2)-c2cc(ccc2F)Oc2c(F)c(F)c3[nH]ccc3c21]

To a stirred solution of methyl (2R)-2-methyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanoate (Step C product of Example 200, 100 mg, 0.131 mmol) in tetrahydrofuran (5 mL) was added an aqueous solution of methylamine (40 wt. % in water) (15 mL). The reaction was stirred at room temperature for 2 days and concentrated. The residue was taken up in ethyl acetate (20 mL), washed with water, brine, dried over sodium sulfate and concentrated. The residue was purified and separated by reverse phase preparative HPLC. The first eluent was designated as Compound 360D (10 mg, 10%, white solid), the second eluent was Compound 360B (5.0 mg, 5%, white solid), The third eluent was Compound 360C (4.8 mg, 4.8%) and the fourth eluent was Compound 360A (10 mg, 10%, white solid).

Compound 360D: LC-MS: MS (ESI): 752 m/z $[M+H]^+$, retention time: 1.49 minutes; purity: 95% (154 nm) (LC-MS method 44). $^1$H NMR (400 MHz, $CD_3OD$) δ 7.56-7.52 (m, 1H), 7.45-7.35 (m, 2H), 7.12-7.04 (m, 2H), 6.97-6.95 (m, 2H), 6.91 (d, J=6.8 Hz, 1H), 6.83 (s, 1H), 3.81-3.79 (m, 3H), 3.74-3.71 (m, 1H), 3.56-3.35 (m, 2H), 3.24-3.19 (m, 1H), 2.93-2.86 (m, 2H), 2.58-2.46 (m, 2H), 2.32 (s, 3H), 2.16-2.10 (m, 1H), 1.79-1.75 (m, 1H), 1.63 (s, 3H), 1.45-1.35 (m, 2H), 1.20-1.11 (m, 2H), 1.08-0.98 (m, 9H) ppm.

Compound 360B: LC-MS: MS (ESI): 765 m/z $[M+H]^+$, retention time: 1.16 minutes; purity: 97% (214 nm) (LC-MS method 004). $^1$H NMR (400 MHz, $CD_3OD$) δ 7.59-52 (m, 1H), 7.43-7.38 (m, 2H), 7.18 (s, 1H), 7.12-7.06 (m, 2H), 6.97-6.91 (m, 2H), 6.80 (t, J=3.2 Hz, 1H), 3.79-3.75 (m, 4H), 3.63-3.57 (m, 1H), 3.44-3.39 (m, 1H), 3.25-3.19 (m, 1H), 2.82-2.77 (m, 2H), 2.59-2.46 (m, 6H), 2.38 (s, 3H), 2.18-2.13 (m, 1H), 1.88-1.83 (m, 1H), 1.61 (s, 3H), 1.33-1.28 (m, 2H), 1.21-1.14 (m, 2H), 1.09-1.06 (m, 6H), 0.96 (s, 3H) ppm.

Compound 360C: LC-MS: MS (ESI): 765 m/z $[M+H]^+$, retention time: 1.16 minutes; purity: 94% (214 nm) (LC-MS method 004). $^1$H NMR (400 MHz, $CD_3OD$) δ 7.55-7.50 (m, 1H), 7.43-7.38 (m, 2H), 7.11-7.07 (m, 2H), 6.98-6.87 (m, 3H), 6.83 (m, 1H), 3.80 (d, J=2.0 Hz, 3H), 3.73-7.69 (m, 1H), 3.59-3.55 (m, 1H), 3.13-3.10 (m, 1H), 2.89 (d, J=14.0 Hz, 1H), 2.82-2.77 (m, 1H), 2.55 (s, 3H), 2.50-2.44 (m, 3H), 2.33 (s, 3H), 2.15-2.11 (m, 1H), 1.80-1.75 (m, 1H), 1.68-1.61 (m, 4H), 1.38-1.28 (m, 2H), 1.17-1.15 (m, 2H), 1.03-0.97 (m, 9H) ppm.

Compound 360A: LC-MS: MS (ESI): 766 m/z $[M+H]^+$, retention time: 1.59 minutes; purity: 95% (214 nm) (LC-MS method 44). $^1$H NMR (400 MHz, $CD_3OD$) δ 7.55-7.50 (m, 1H), 7.44-7.36 (m, 2H), 7.14-7.05 (m, 2H), 6.96-6.84 (m, 4H), 3.81 (d, J=2.0 Hz, 3H), 3.74-3.71 (m, 1H), 3.55-3.46 (m, 4H), 3.26-3.15 (m, 1H), 2.91 (d, J=13.2 Hz, 1H), 2.81-2.76 (m, 1H), 2.62-2.53 (m, 2H), 2.31 (s, 3H), 2.15-2.09 (m, 1H), 1.78-1.60 (m, 5H), 1.44-1.39 (m, 2H), 1.16-1.13 (m, 2H), 1.03-0.98 (m, 9H) ppm.

Example 361. 2-[(6R)-21,22,28-Trifluoro-3,6,10,10-tetramethyl-12,12-dioxo-6-phenyl-24-oxa-12λ6-thia-3,4,19,30-tetrazapentacyclo[23.3.1.12,5.015,23.016,20]triaconta-1(29),2(30),4,15,17,20,22,25,27-nonaen-17-yl]acetic Acid

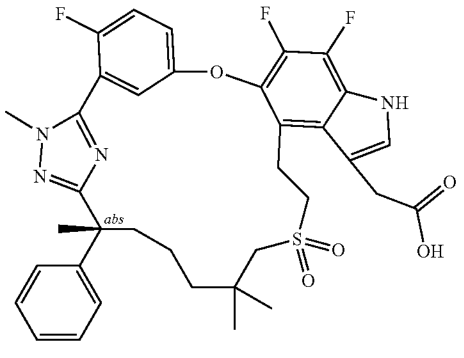 [SMILES: Cn1nc2nc1-c1cc(ccc1F)Oc1c(F)c(F)c3[nH]cc(CC(=O)O)c3c1CCS(=O)(=O)CC(C)(C)CCC[C@]2(C)c1ccccc1]

(6R,13E)-21,22,28-Trifluoro-3,6,10,10-tetramethyl-6-phenyl-24-oxa-12λ6-thia-3,4,19,30-tetrazapentacyclo[23.3.1.12,5.015,23.016,20]triaconta-1(29),2(30),4,13,15,17,20,22,25,27-decaene 12,12-dioxide

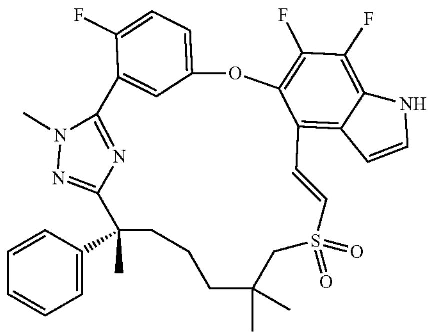 [SMILES: Cn1nc2nc1-c1cc(ccc1F)Oc1c(F)c(F)c3[nH]ccc3c1/C=C/S(=O)(=O)CC(C)(C)CCC[C@]2(C)c1ccccc1]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with (R)-7-((2-hydroxyethyl)sulfonyl)-N',2,6,6-tetramethyl-2-phenylheptanehydrazide (Intermediate 152, 1.70 g, 4.42 mmol), and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)oxy)-2-fluorobenzimidothioate hydroiodide (Intermediate 14-2, 2.64 g, 4.86 mmol) in Step A of Example 6, the reaction procedure sequence (Steps A to C) described for Example 6 was followed to afford the title compound (0.97 g) as a white solid. LC-MS: MS (ESI): 635 m/z [M+H]$^+$, purity: 97% (214 nm), retention time: 2.12 minutes (LC-MS method 004).

Ethyl 2-hydroxy-2-[(6R,13E)-21,22,28-trifluoro-3,6,10,10-tetramethyl-12,12-dioxo-6-phenyl-24-oxa-12λ6-thia-3,4,19,30-tetrazapentacyclo[23.3.1.12,5.015,23.016,20]triaconta-1(29),2(30),4,13,15,17,20,22,25,27-decaen-17-yl]Acetate

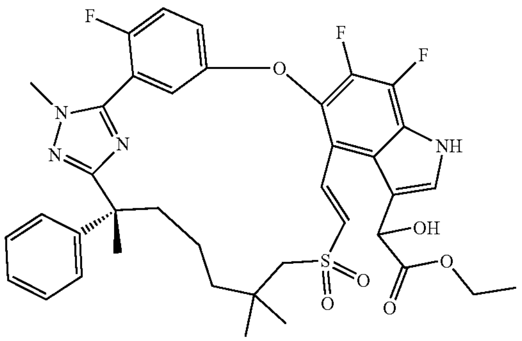 [SMILES: CCOC(=O)C(O)c1c[nH]c2c(F)c(F)c3c(c12)/C=C/S(=O)(=O)CC(C)(C)CCC[C@](C)(c1ccccc1)c1nc(n(C)n1)-c1cc(ccc1F)O3]

Step B: To a stirred solution of product from Step A (400 mg, 0.544 mmol) in dichloromethane (6 mL) was added ethyl 2-oxoacetate (50% in toluene) (2 mL) and magnesium iodide (7.5 mg, 0.027 mmol). The reaction was stirred at 40° C. for 4 days and then diluted with ethyl acetate (20 mL). The mixture was washed with water, brine, dried over sodium sulfate and concentrated. The residue was purified by automated flash chromatography (10 g silica gel column, eluting with 0-50% ethyl acetate in petroleum ether) to give the title compound (170 mg, 42%) as a solid. LC-MS: MS (ESI): 737 m/z [M+H]$^+$, purity: 91% (214 nm), retention time: 1.73 minutes (LC-MS method 004)

Ethyl 2-[(6R)-21,22,28-trifluoro-3,6,10,10-tetramethyl-12,12-dioxo-6-phenyl-24-oxa-12λ6-thia-3,4,19,30-tetrazapentacyclo[23.3.1.12,5.015,23.016,20]triaconta-1(29),2(30),4,15,17,20,22,25,27-nonaen-17-yl]Acetate

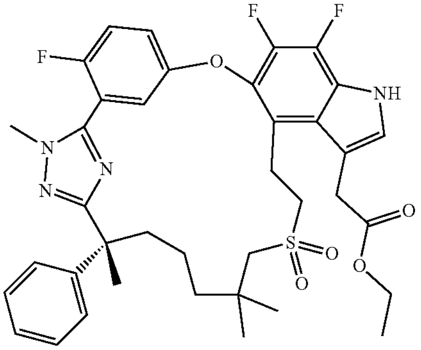 [SMILES: CCOC(=O)Cc1c[nH]c2c(F)c(F)c3c(c12)CCS(=O)(=O)CC(C)(C)CCC[C@](C)(c1ccccc1)c1nc(n(C)n1)-c1cc(ccc1F)O3]

Step C: To a stirred solution of the product from Step B (150 mg, 0.204 mmol) in tetrahydrofuran (4 mL) and ethanol (4 mL) was added palladium on carbon (50 mg). The reaction was stirred at 50° C. under a hydrogen atmosphere for 2 hours and filtered through a pad of Celite. The filtrate was concentrated. The residue was purified by automated flash chromatography (10 g silica gel column, eluting with 0-80% ethyl acetate in petroleum ether) to give the title compound (15 mg, 10%) as a solid. LC-MS: MS (ESI): 723 m/z [M+H]$^+$, purity: 99% (214 nm), retention time: 1.78 minutes (LC-MS method 004).

Compound 361. 2-[(6R)-21,22,28-Trifluoro-3,6,10,10-tetramethyl-12,12-dioxo-6-phenyl-24-oxa-12λ6-thia-3,4,19,30-tetrazapentacyclo[23.3.1.12,5.015,23.016,20]triaconta-1(29),2(30),4,15,17,20,22,25,27-nonaen-17-yl]acetic Acid

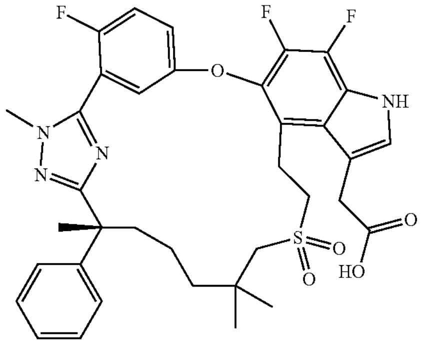 [SMILES: Cn1nc2nc1-c1cc(ccc1F)Oc1c(F)c(F)c3[nH]cc(CC(=O)O)c3c1CCS(=O)(=O)CC(C)(C)CCC[C@]2(C)c1ccccc1]

Step D: To a stirred solution of the product from Step C (15 mg, 0.021 mmol) in tetrahydrofuran (1.5 mL), methanol (0.5 mL) and water (0.5 mL) was added lithium hydroxide monohydrate (4.4 mg, 0.1 mmol). The reaction was stirred at room temperature for 16 hours, then acidified with 1N hydrochloric acid to pH ~4 and diluted with ethyl acetate (20 mL). The mixture was washed with brine, dried over sodium sulphate, filtered, and concentrated. The residue was purified by automated flash chromatography (10 g silica gel column, eluting with 0-10% methanol in dichloromethane) to give the title compound (6.1 mg, 42%) as a white solid. LC-MS: MS (ESI): 695 m/z $[M+H]^+$, purity: 98% (214 nm), retention time: 2.01 minutes (LC-MS method 004). $^1H$ NMR (400 MHz, $CD_3OD$) δ 7.50 (dd, J=5.6, 3.2 Hz, 1H), 7.24-7.10 (m, 8H), 3.96 (s, 2H), 3.89 (d, J=2.0 Hz, 3H), 3.43-3.36 (m, 3H), 3.23-3.14 (m, 1H), 3.05-1.95 (m, 2H), 2.25-2.12 (d, 1H), 1.92-1.80 (m, 1H), 1.72-1.64 (m, 4H), 1.40-1.33 (m, 3H), 1.14 (s, 3H), 1.09 (s, 3H) ppm.

Example 362. 2-[(6R)-22-Fluoro-3,6,10,10-tetramethyl-12,12-dioxo-6-phenyl-12λ6,24-dithia-3,4,19,28,30-pentazapentacyclo[23.3.1.12,5.015,23.016,20]triaconta-1(29),2(30),4,15,17,20,22,25,27-nonaen-17-yl]acetic Acid

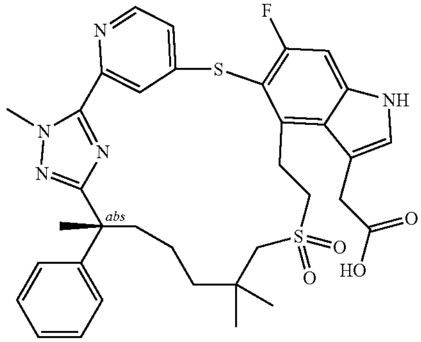 [SMILES: Cn1nc2nc1-c1cc(ccn1)Sc1c(F)cc3[nH]cc(CC(=O)O)c3c1CCS(=O)(=O)CC(C)(C)CCC[C@]2(C)c1ccccc1]

Ethyl 2-[(6R)-22-fluoro-3,6,10,10-tetramethyl-12,12-dioxo-6-phenyl-12λ6,24-dithia-3,4,19,28,30-pentazapentacyclo[23.3.1.12,5.015,23.016,20]triaconta-1(29),2(30),4,15,17,20,22,25,27-nonaen-17-yl]-2-hydroxy-acetate

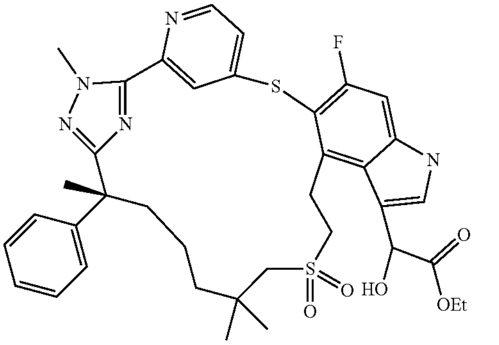 [SMILES: CCOC(=O)C(O)c1c[nH]c2cc(F)c3c(c12)CCS(=O)(=O)CC(C)(C)CCC[C@](C)(c1ccccc1)c1nc(n(C)n1)-c1cc(ccn1)S3]

Step A: Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with (R)-7-((2-hydroxyethyl)sulfonyl)-N',2,6,6-tetramethyl-2-phenylheptanehydrazide (Intermediate 152, 5.00 g, 13.0 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)thio)pyridine-2-carbimidothioate (Intermediate 14-15, 6.18 g, 15.6 mmol) in Step A of Example 6, the reaction procedure sequence, Steps A to C of Example 6, then Step B of Example 301, Step B of Example 361, was followed to afford the title compound (0.20 g) as a white solid. LC-MS: MS (ESI): 720 m/z $[M+H]^+$, purity: 93% (254 nm), retention time: 1.75 minutes (LC-MS method 003).

Ethyl 2-[(6R)-22-fluoro-3,6,10,10-tetramethyl-12,12-dioxo-6-phenyl-12λ6,24-dithia-3,4,19,28,30-pentazapentacyclo[23.3.1.12,5.015,23.016,20]triaconta-1(29),2(30),4,15,17,20,22,25,27-nonaen-17-yl]acetate

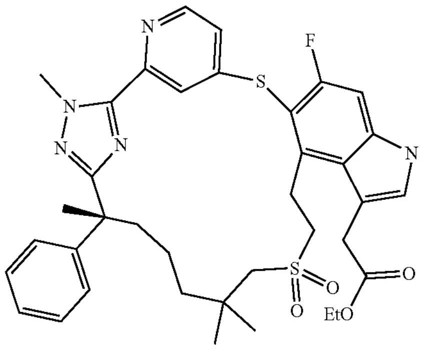

Step B: To a stirred solution of product from Step A (100 mg, 0.139 mmol) in dichloromethane (10 mL) was added diiodophosphanyl(diiodo)phosphane (158 mg, 0.278 mmol). The reaction was stirred at room temperature for 16 hours under argon, quenched with saturated aqueous sodium sulfite, and diluted with ethyl acetate (30 mL). The mixture was washed with water, brine, dried over sodium sulfate, and concentrated. The residue was purified by automated flash chromatography (25 g silica gel column, eluting with 0-60% ethyl acetate in petroleum ether) to give the title compound (19 mg, 19%) as a solid. LC-MS: MS (ESI): 704 m/z $[M+H]^+$, purity: 61% (254 nm), retention time: 1.83 minutes (LC-MS method 003).

Compound 362: 2-[(6R)-22-Fluoro-3,6,10,10-tetramethyl-12,12-dioxo-6-phenyl-12λ6,24-dithia-3,4,19,28,30-pentazapentacyclo[23.3.1.12,5.015,23.016,20]triaconta-1(29),2(30),4,15,17,20,22,25,27-nonaen-17-yl]acetic Acid

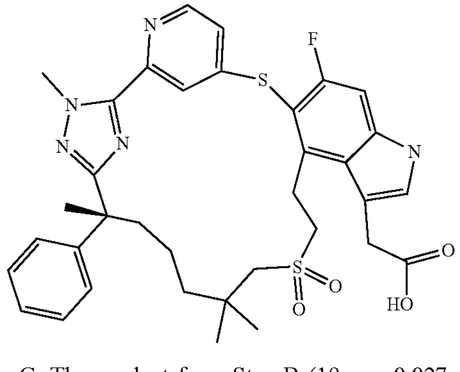

Step C: The product from Step B (19 mg, 0.027 mmol) was subjected to the reaction conditions described in Step D of Example 361 to afford the title compound (5.8 mg, 32%) as a white solid. LC-MS: MS (ESI): 676 m/z $[M+H]^+$, purity: >99% (254 nm), retention time: 1.72 minutes (LC-MS method 003). $^1H$ NMR (400 MHz, $CD_3OD$) δ 8.50 (d, J=5.6 Hz, 1H), 8.16-7.73 (m, 1H), 7.55-7.01 (m, 8H), 4.30 (s, 3H), 4.22-4.03 (m, 1H), 3.98-3.69 (m, 3H), 3.43-3.36 (m, 1H), 3.30-2.90 (m, 2H), 2.67-2.49 (m, 1H), 2.20-2.06 (m, 1H), 1.83-1.72 (m, 1H), 1.67 (s, 3H), 1.43-1.18 (m, 4H), 1.07 (s, 3H), 0.94 (s, 3H) ppm.

Example 363. 2-[(6R)-21,22-Difluoro-3,6,10,10-tetramethyl-12,12-dioxo-6-phenyl-24-oxa-12λ6-thia-3,4,19,28,30-pentazapentacyclo[23.3.1.12,5.015,23.016,20]triaconta-1(29),2(30),4,15,17,20,22,25,27-nonaen-17-yl]acetic acid

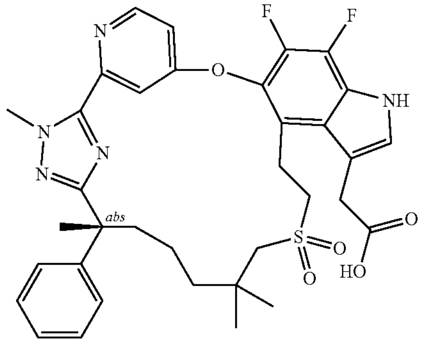 [SMILES: Cn1nc2nc1-c1cc(ccn1)Oc1c(F)c(F)c3[nH]cc(CC(=O)O)c3c1CCS(=O)(=O)CC(C)(C)CCC[C@]2(C)c1ccccc1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with (R)-7-((2-hydroxyethyl)sulfonyl)-N',2,6,6-tetramethyl-2-phenylheptanehydrazide (Intermediate 152, 1.90 g, 4.94 mmol), and methyl 5-((4-bromo-6-fluoro-1H-indol-5-yl)oxy)-2-fluorobenzimidothioate hydroiodide (Intermediate 14-1) with methyl 4-((4-bromo-6,7-difluoro-1H-indol-5-yl)oxy)pyridine-2-carbimidothioate (Intermediate 150, 2.16 g, 5.44 mmol) in Step A of Example 6, the reaction procedure sequence, Steps A to C of Example 6, then Step B of Example 361, Step D of Example 6, Step B and C of Example 362, in this order, was followed to afford the title compound (Compound 363, 18 mg) as a white solid. LC-MS: MS (ESI): 678 m/z $[M+H]^+$, purity: >99% (254 nm), retention time: 1.66 minutes (LC-MS method 030). $^1H$ NMR (400 MHz, $CD_3OD$) δ 8.64 (d, J=5.7 Hz, 1H), 7.91 (d, J=2.4 Hz, 1H), 7.32 (s, 1H), 7.26-7.21 (m, 2H), 7.20-7.10 (m, 4H), 4.37 (s, 3H), 4.11-4.08 (m, 1H), 3.96-3.90 (m, 1H), 3.55-3.48 (m, 1H), 3.37-3.34 (m, 1H), 3.23-3.17 (m, 1H), 3.10-2.99 (m, 1H), 2.79-2.67 (m, 2H), 2.120-2.15 (m, 1H), 1.87-1.78 (m, 1H), 1.67 (s, 3H), 1.57-1.50 (m, 1H), 1.27-1.17 (m, 3H), 1.04 (s, 3H), 0.97 (s, 3H) ppm.

Example 364. 2-[(6R)-22-Fluoro-3,6,10,10-tetramethyl-12,12-dioxo-6-phenyl-12λ6-thia-3,4,19,28,30-pentazapentacyclo[23.3.1.12,5.015,23.016,20]triaconta-1(29),2(30),4,15,17,20,22,25,27-nonaen-17-yl]acetic Acid

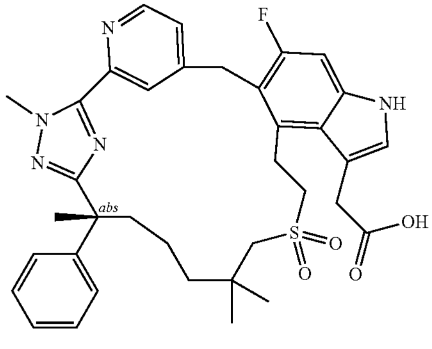 [SMILES: Cn1nc2nc1-c1cc(ccn1)Cc1c(F)cc3[nH]cc(CC(=O)O)c3c1CCS(=O)(=O)CC(C)(C)CCC[C@]2(C)c1ccccc1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with (R)-7-((2-hydroxyethyl)sulfonyl)-N',2,6,6-tetramethyl-2-phenylheptanehydrazide (Intermediate 152, 1.03 g, 2.67 mmol), and methyl 5-((4-bromo-6-fluoro-1H-indol-5-yl)oxy)-2-fluorobenzimidothioate hydroiodide (Intermediate 14-1) with methyl 4-((4-bromo-6-fluoro-1H-indol-5-yl)methyl)pyridine-2-carbimidothioate (Intermediate 150-3, 1.26 g, 2.67 mmol) in Step A of Example 6, the reaction procedure sequence, Steps A to C of Example 6, then Step B of Example 361, Step D of Example 6, Step C of Example 362, in this order, was followed to afford the title compound (Compound 364, 16 mg) as a white solid. LC-MS: MS (ESI): 658 m/z $[M+H]^+$, purity: 98% (214 nm), retention time: 1.64 minutes (LC-MS method 030). $^1H$ NMR (400 MHz, $CD_3OD$) δ 8.59-8.47 (m, 2H), 7.33 (d, J=5.1 Hz, 1H), 7.29-7.19 (m, 4H), 7.19-7.08 (m, 3H), 4.39-4.30 (m, 1H), 4.28 (s, 3H), 4.17-4.04 (m, 1H), 3.84 (s, 2H), 3.56-3.43 (m, 2H), 3.20-2.98 (m, 4H), 2.50-2.38 (m, 1H), 1.97-1.86 (m, 1H), 1.75 (s, 3H), 1.72-1.30 (m, 4H), 1.25 (s, 3H), 1.10 (s, 3H) ppm.

Example 365. Diastereomer 2 of 2-[(6R)-22-Fluoro-3,6,10,10-tetramethyl-12,12,24-trioxo-6-phenyl-12λ6,24λ4-dithia-3,4,19,28,30-pentazapentacyclo[23.3.1.12,5.015,23.016,20]triaconta-1(29),2(30),4,15,17,20,22,25,27-nonaen-17-yl]acetic Acid

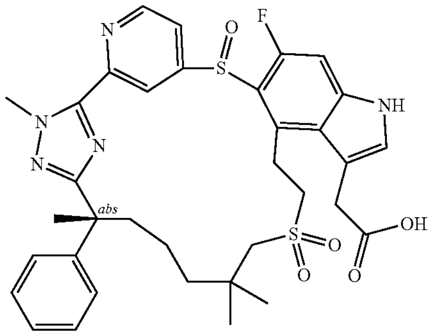 [SMILES: Cn1nc2nc1-c1cc(ccn1)S(=O)c1c(F)cc3[nH]cc(CC(=O)O)c3c1CCS(=O)(=O)CC(C)(C)CCC[C@]2(C)c1ccccc1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with ethyl 2-[(6R)-22-fluoro-3,6,10,10-tetramethyl-12,12-dioxo-6-phenyl-12λ6,24-dithia-3,4,19,28,30-pentazapentacyclo[23.3.1.12,5.015,23.016,20]triaconta-1(29),2(30),4,15,17,20,22,25,27-nonaen-17-yl]acetate (Step B product of Example 362, 120 mg, 0.17 mmol) in Step E of Example 204, the reaction procedure sequence, (Step E, F and H described for Example 204, was followed to give the title compound (Compound 365, 5.4 mg) as a white solid. LC-MS: MS (ESI): 692 m/z $[M+H]^+$, purity: 96% (214 nm), retention time: 1.60 minutes (LC-MS method 015). $^1H$ NMR (400 MHz, DMSO-$d_6$) δ 11.62 (s, 1H), 9.03-8.70 (m, 2H), 8.09-7.36 (m, 2H), 7.27-7.07 (m, 7H), 4.28 (s, 3H), 3.72-3.60 (m, 3H), 3.16-2.99 (m, 5H), 2.43-2.33 (m, 1H), 1.74-1.62 (m, 4H), 1.53-1.35 (m, 4H), 1.27 (s, 3H), 1.10 (s, 3H) ppm.

Example 366. 2-[(6R)-22-Fluoro-3,6,10,10-tetramethyl-12,12,24,24-tetraoxo-6-phenyl-12λ6,24λ6-dithia-3,4,19,28,30-pentazapentacyclo[23.3.1.12,5.015,23.016,20]triaconta-1(29),2(30),4,15,17,20,22,25,27-nonaen-17-yl]acetic acid

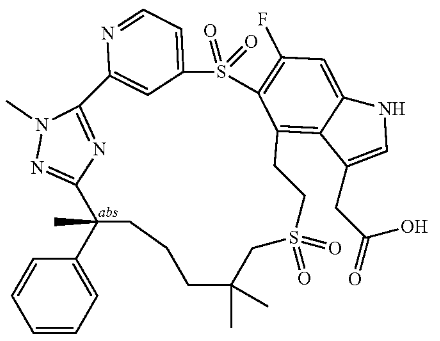 [SMILES: Cn1nc2nc1-c1cc(ccn1)S(=O)(=O)c1c(F)cc3[nH]cc(CC(=O)O)c3c1CCS(=O)(=O)CC(C)(C)CCC[C@]2(C)c1ccccc1]

Exchanging methyl (2S)-3-[3-[(6R)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step D product of Example 204) with ethyl 2-[(6R)-22-fluoro-3,6,10,10-tetramethyl-12,12-dioxo-6-phenyl-12λ6,24-dithia-3,4,19,28,30-pentazapentacyclo[23.3.1.12,5.015,23.016,20]triaconta-1(29),2(30),4,15,17,20,22,25,27-nonaen-17-yl]acetate (Step B product of Example 362, 120 mg, 0.17 mmol) in Step E of Example 204, the reaction procedure sequence, Step E described for Example 204, followed by Step C and E for Example 180, was followed to give the title compound (Compound 366, 1.5 mg) as a white solid. LC-MS: MS (ESI): 708 m/z $[M+H]^+$, purity: 95% (214 nm), retention time: 1.77 minutes (LC-MS method 015). $^1H$ NMR (400 MHz, $CD_3OD$). δ 8.95 (d, J=4.8 Hz, 1H), 8.82 (s, 1H), 8.02-8.00 (m, 1H), 7.30 (s, 1H), 7.26-7.18 (m, 5H), 7.15-7.12 (m, 1H), 4.27 (s, 3H), 3.94-3.88 (m, 2H), 3.78-3.71 (m, 1H), 3.25-3.19 (m, 5H), 1.78-1.71 (m, 4H), 1.66-1.35 (m, 4H), 1.32-1.15 (m, 7H) ppm.

Example 367. Diastereomers 1 and 2 of (2R)-3-[3-[(6R)-14-(dimethylamino)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-N,N,2-trimethyl-propanamide

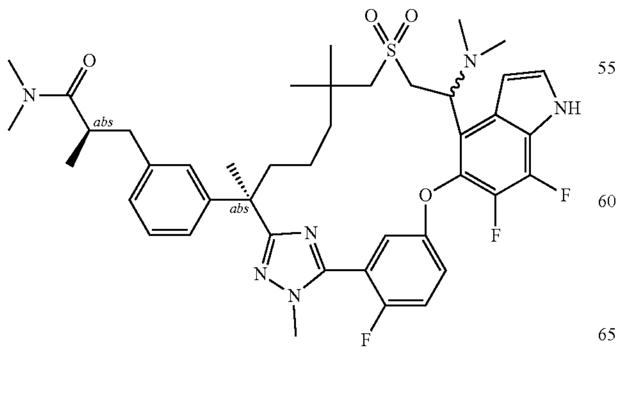

(2R)-2-Methyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanoic acid

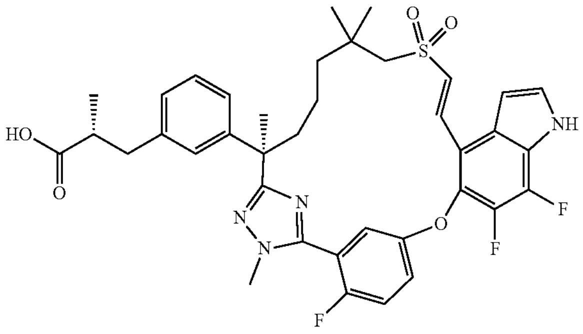 [SMILES: C[C@H](Cc1cccc([C@@]2(C)CCCC(C)(C)CS(=O)(=O)/C=C/c3c(c(F)c(F)c4[nH]ccc34)Oc3ccc(F)c(c3)-c3nc2nn3C)c1)C(=O)O]

Step A. Methyl (2R)-2-methyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanoate (Step C product of Example 200, 3.0 g, 4.08 mmol) was subjected to the hydrolysis conditions described for Step D of Example 361 to afford the title compound (2.60 g, 88%) as a white solid. LC-MS: MS (ESI): 721 m/z $[M+H]^+$, purity: >99% (214 nm), retention time: 1.61 minutes (LC-MS method 026).

(2R)—N,N,2-Trimethyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanamide

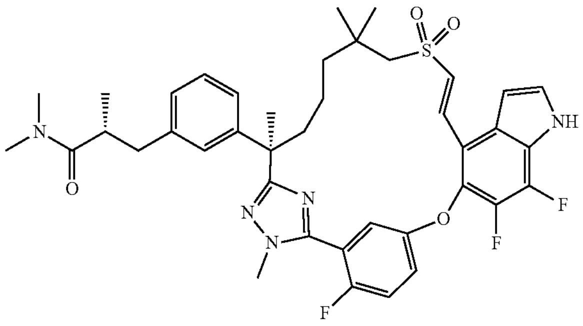 [SMILES: C[C@H](Cc1cccc([C@@]2(C)CCCC(C)(C)CS(=O)(=O)/C=C/c3c(c(F)c(F)c4[nH]ccc34)Oc3ccc(F)c(c3)-c3nc2nn3C)c1)C(=O)N(C)C]

Step B. To a stirred solution of the product from Step A (300 mg, 0.416 mmol) in dimethylformamide (10 mL) was added triethylamine (0.12 ml, 0.832 mmol), dimethylamine hydrochloride (51 mg, 0.624 mmol), and O-(7-azabenzotriazol-1-yl)-N,N,N',N'-tetramethyluronium hexafluorophosphate (190 mg, 0.499 mmol). The reaction mixture was stirred at room temperature for 1 hour, quenched with water (30 mL) and diluted with ethyl acetate (50 mL). The separated organic layer was washed with a solution of lithium chloride, brine, dried over magnesium sulfate, filtered, and concentrated. The residue was purified by automated flash column chromatography eluting with 0-5% methanol in dichloromethane to afford the title compound (280 mg, 90%) as a solid. LC-MS: MS (ESI): 748 m/z $[M+H]^+$, purity: >99% (214 nm), retention time: 1.92 minutes (LC-MS method 47).

Compounds 367A and 367B. Diastereomers 1 and 2 of (2R)-3-[3-[(6R)-14-(dimethylamino)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-N,N,2-trimethyl-propanamide

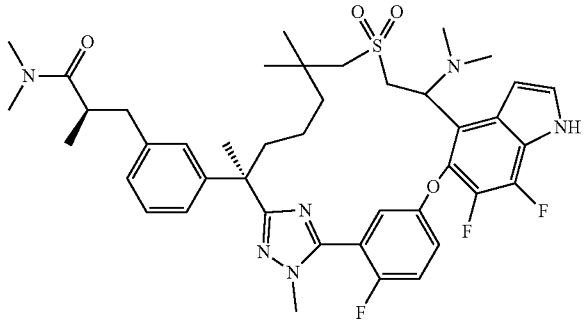 [SMILES: C[C@H](Cc1cccc([C@@]2(C)CCCC(C)(C)CS(=O)(=O)CC(N(C)C)c3c(c(F)c(F)c4[nH]ccc34)Oc3ccc(F)c(c3)-c3nc2nn3C)c1)C(=O)N(C)C]

Step C: To a stirred solution of the product from Step B (100 mg, 0.13 mmol) in tetrahydrofuran (2 mL) was added a solution of dimethylamine (0.067 mL, 0.134 mmol) (2M in tetrahydrofuran). The reaction mixture was stirred at 50° C. for 5 days. The reaction mixture was purified by reverse phase prep-HPLC. The first eluent was designated as Compound 367A (Diastereomer 1, 7.0 mg, 0.00883 mmol, 6.60%) and the second eluent was designated as Compound 367B (Diastereomer 2, 10 mg, 0.0126 mmol, 9.4%) as white solids.

Compound 367A: LC-MS: MS (ESI): 793 m/z $[M+H]^+$, purity: >99% (214 nm), retention time: 1.85 minutes (LC-MS method 024). $^1$H NMR (400 MHz, $CD_3OD$) δ 7.54-7.49 (m, 1H), 7.41 (d, J=3.2 Hz, 1H), 7.36 (t, J=9.2 Hz, 1H), 7.16-7.04 (m, 4H), 6.95 (d, J=7.6 Hz, 1H), 6.75 (t, J=3.2 Hz, 1H), 4.69-4.66 (m, 1H), 3.88-3.81 (m, 1H), 3.77-3.72 (m, 1H), 3.66 (s, 3H), 3.10-3.04 (m, 1H), 2.91-2.86 (m, 1H), 2.82-2.79 (m, 1H), 2.83-2.72 (m, 4H), 2.69 (s, 3H), 2.61-2.57 (m, 1H), 2.29 (s, 6H), 2.25-2.19 (m, 1H), 1.90-1.83 (m, 1H), 1.61 (s, 3H), 1.56-1.46 (m, 1H), 1.38-1.25 (m, 2H), 1.21-1.12 (m, 4H), 1.08 (d, J=6.8 Hz, 3H), 0.93 (s, 3H) ppm.

Compound 367B: LC-MS: MS (ESI): 793 m/z $[M+H]^+$, purity: >99% (214 nm), retention time: 1.87 minutes (LC-MS method 024). $^1$H NMR (400 MHz, $CD_3OD$) δ 7.52-7.48 (m, 1H), 7.39-7.34 (m, 2H), 7.32-7.26 (m, 1H), 7.10 (t, J=7.6 Hz, 1H), 7.01-6.90 (m, 3H), 6.77 (t, J=3.2 Hz, 1H), 4.69-4.64 (m, 1H), 4.02-3.98 (m, 1H), 3.77 (d, J=2.0 Hz, 3H), 3.68 (dd, J=14.0, 3.6 Hz, 1H), 3.06-2.97 (m, 1H), 2.91-2.76 (m, 3H), 2.74 (s, 3H), 2.65 (s, 3H), 2.54 (dd, J=13.2, 6.0 Hz, 1H), 2.30 (s, 6H), 2.13-2.06 (m, 1H), 1.88-1.80 (m, 1H), 1.60 (s, 3H), 1.53-1.42 (m, 1H), 1.32-1.20 (m, 3H), 1.05 (d, J=6.4 Hz, 3H), 0.99 (s, 3H), 0.94 (s, 3H) ppm.

Example 368. Diastereomer 1 and 2 of (2S)-3-[3-[(6R)-22,28-difluoro-3,6,10,10-tetramethyl-14-(methylamino)-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-N,2-dimethyl-propanamide

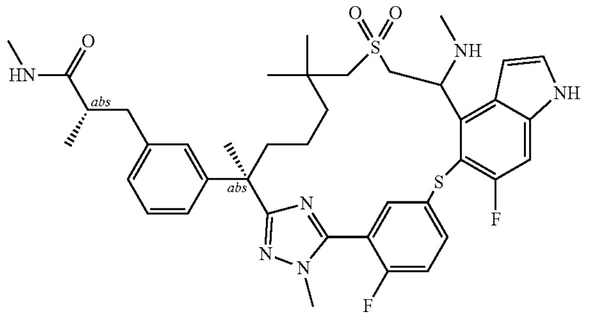 [SMILES: CNC(=O)[C@@H](C)Cc1cccc([C@@]2(C)CCCC(C)(C)CS(=O)(=O)CC(NC)c3c(c(F)cc4[nH]ccc34)Sc3ccc(F)c(c3)-c3nc2nn3C)c1]

Exchanging methyl (2R)-2-methyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanoate (Step C product of Example 200) with Methyl (2S)-3-[3-[(6R,13E)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,13,15,17,20,22,25,27-decaen-6-yl]phenyl]-2-methyl-propanoate (Step C product of Example 204, 1.00 g, 1.36 mmol) in Step A, dimethylamine hydrochloride with methylamine hydrochloride in Step B, and 2 M dimethylamine solution in tetrahydrofuran with methyl amine aqueous solution in water in Step C of Example 367, the reaction procedure sequence (Steps A to C) described for Example 367) was followed to provide the title compounds. The first eluent was designated as Compound 368A (Diastereomer 1, 10 mg, white solid) and the second eluent was designated as Compound 368B (Diastereomer 2, 15 mg, white solid).

Compound 368A: LC-MS: MS (ESI): 763 m/z $[M+H]^+$, purity: >99% (214 nm), retention time: 1.78 minutes (LC-MS method 026). $^1$H NMR (400 MHz, $CD_3OD$) δ 8.03-7.96 (m, 2H), 7.30-7.26 (m, 2H), 7.14-7.11 (m, 2H), 7.05-7.03 (m, 1H), 6.96-6.91 (m, 2H), 6.80-6.74 (m, 1H), 6.02 (d, J=8.0 Hz, 1H), 4.01-3.97 (m, 1H), 3.72-3.58 (m, 3H), 3.52-3.46 (m, 1H), 3.33-3.31 (m, 1H), 3.09-2.98 (m, 2H), 2.79 (dd, J=13.2, 8.8 Hz, 1H), 2.62-2.48 (m, 4H), 2.44-2.33 (m, 2H), 2.23 (s, 3H), 2.04-1.93 (m, 2H), 1.64 (s, 3H), 1.48-1.25 (m, 4H), 1.25-1.08 (m, 2H), 1.05 (d, J=6.8 Hz, 3H), 0.98 (s, 3H) ppm.

Compound 368B: LC-MS: MS (ESI): 763 m/z $[M+H]^+$, purity: >99% (214 nm), retention time: 1.80 minutes (LC-MS method 026). $^1$H NMR (400 MHz, $CD_3OD$) δ 7.87 (s, 1H), 7.38-7.25 (m, 2H), 7.22-6.71 (m, 7H), 5.78 (s, 1H), 4.05-3.68 (m, 4H), 3.62-3.57 (m, 1H), 3.33-3.31 (m, 1H), 3.10-2.70 (m, 3H), 2.60-2.47 (m, 4H), 2.44-2.40 (m, 1H), 2.29-2.08 (m, 4H), 1.94-1.86 (m, 1H), 1.64 (s, 3H), 1.49-1.20 (m, 3H), 1.13-0.97 (m, 9H) ppm.

Example 369. Diastereomers 1 and 2 of (2R)-3-[3-[(6R)-14-acetamido-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

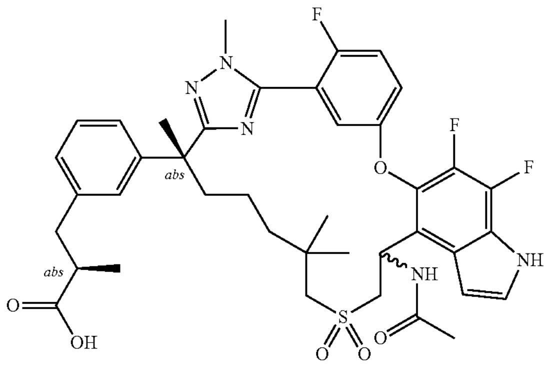 [SMILES: CC(=O)NC1CS(=O)(=O)CC(C)(C)CCC[C@](C)(c2cccc(C[C@@H](C)C(=O)O)c2)c2nc(n(C)n2)-c2cc(ccc2F)Oc2c(F)c(F)c3[nH]ccc3c21]

Diastereomers 1 and 2 of (2R)-3-[3-[(6R)-14-amino-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

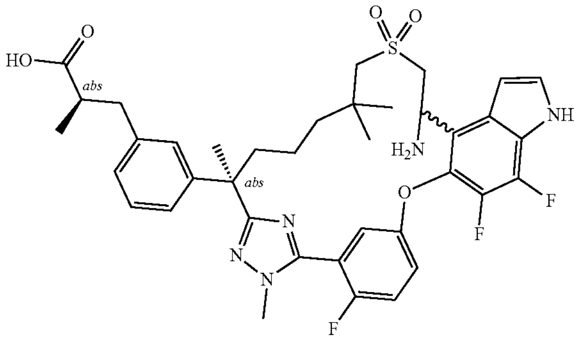 [SMILES: C[C@H](Cc1cccc([C@@]2(C)CCCC(C)(C)CS(=O)(=O)CC(N)c3c(c(F)c(F)c4[nH]ccc34)Oc3ccc(F)c(c3)-c3nc2nn3C)c1)C(=O)O]

Step A: To a stirred solution of (2R)-2-methyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanoic acid (Step A product of Example 367, 100 mg, 0.139 mmol) in methanol (2 mL) was added boric acid (8.6 mg, 0.139 mmol), ammonia (25-28% in water) (2.5 mL) and ammonia (7M in methanol) (2.5 mL). The reaction mixture was stirred at 50° C. for 12 days and concentrated. The residue was purified by prep-HPLC to give the first eluent as diastereomer 1 of (2R)-3-[3-[(6R)-14-amino-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid (Diastereomer 1, 20 mg, 0.0271 mmol, 20%) as a solid and the second eluent as diastereomer 2 of (2R)-3-[3-[(6R)-14-amino-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid (Diastereomer 2, 20 mg, 20%) as a solid.

Diastereomer 1: LC-MS: MS (ESI): 738 m/z $[M+H]^+$, purity: >99% (214 nm), retention time: 1.50 minutes (LC-MS method 003).

Diastereomer 2: LC-MS: MS (ESI): 738 m/z $[M+H]^+$, purity: >99% (214 nm), retention time: 1.54 minutes (LC-MS method 003).

Compound 369A. Diastereomers 1 of (2R)-3-[3-[(6R)-14-acetamido-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

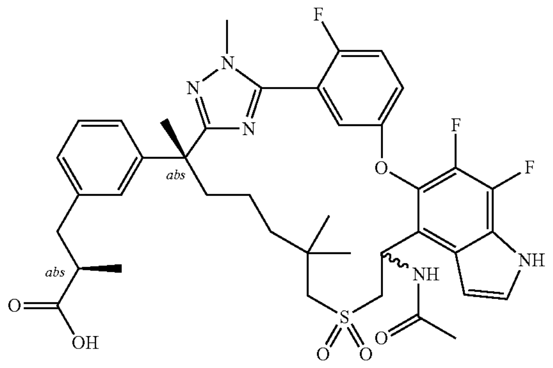 [SMILES: CC(=O)NC1CS(=O)(=O)CC(C)(C)CCC[C@](C)(c2cccc(C[C@@H](C)C(=O)O)c2)c2nc(n(C)n2)-c2cc(ccc2F)Oc2c(F)c(F)c3[nH]ccc3c21]

Step B: To a stirred solution of Diastereomer 1 (a product of Step A) (20 mg, 0.0271 mmol) in dichloromethane (2 mL) was added acetyl chloride (0.019 mL, 0.271 mmol). The reaction mixture was stirred at room temperature for 2 hours and concentrated. The residue was purified by prep-HPLC to give the title compound (15 mg, 71%) as a solid. LC-MS: MS (ESI): 780 m/z $[M+H]^+$, purity: >99% (214 nm), retention time: 1.49 minutes (LC-MS method 015). $^1H$ NMR (400 MHz, $CD_3OD$) δ 7.61-7.56 (m, 1H), 7.45-7.36 (m, 2H), 7.21-7.19 (m, 1H), 7.13 (t, J=7.6 Hz, 1H), 7.05 (s, 1H), 7.01-6.97 (m, 2H), 6.84 (t, J=3.2 Hz, 1H), 6.14 (t, J=6.8 Hz, 1H), 3.79 (s, 3H), 3.59 (d, J=6.8 Hz, 2H), 2.96-2.91 (m, 1H), 2.74 (d, J=13.2 Hz, 1H), 2.64-2.53 (m, 3H), 2.13-2.06 (m, 1H), 1.96 (s, 3H), 1.91-1.81 (m, 1H), 1.62 (s, 3H), 1.34-1.15 (m, 3H), 1.10-0.99 (m, 6H), 0.96 (s, 3H), 0.81-0.73 (m, 1H) ppm.

Compound 369B. Diastereomers 2 of (2R)-3-[3-[(6R)-14-acetamido-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid.

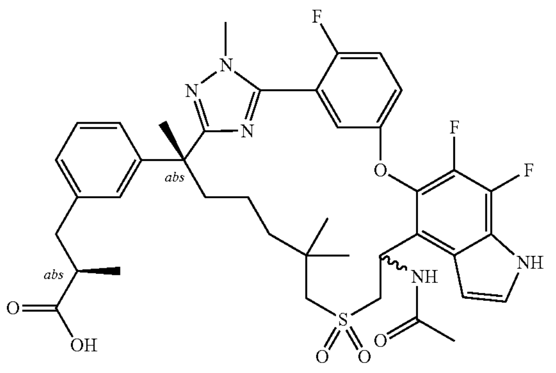 [SMILES: CC(=O)NC1CS(=O)(=O)CC(C)(C)CCC[C@](C)(c2cccc(C[C@@H](C)C(=O)O)c2)c2nc(n(C)n2)-c2cc(ccc2F)Oc2c(F)c(F)c3[nH]ccc3c21]

Step C: Diastereomer 2 (a product of Step A) (20 mg, 0.0271 mmol) was subjected to the same reaction conditions as described in Step B, above, to afford the title compound (14 mg, 66%) as a solid. LC-MS: MS (ESI): 780 m/z $[M+H]^+$, purity: >99% (214 nm), retention time: 1.50 minutes (LC-MS method 015). $^1H$ NMR (400 MHz, $CD_3OD$) δ 7.58-7.53 (m, 1H), 7.43-7.35 (m, 2H), 7.13-7.05 (m, 2H), 6.99-6.90 (m, 3H), 6.86 (t, J=3.2 Hz, 1H), 6.10 (t, J=6.8 Hz, 1H), 3.81 (d, J=2.0 Hz, 3H), 3.69 (dd, J=13.6, 6.4 Hz, 1H), 3.55 (dd, J=13.6, 6.4 Hz, 1H), 3.24 (d, J=13.6 Hz, 1H), 2.90-2.82 (m, 2H), 2.57-2.47 (m, 2H), 2.20-2.12 (m, 1H), 1.93 (s, 3H), 1.78-1.65 (m, 2H), 1.63 (s, 3H), 1.44-1.27 (m, 2H), 1.20-1.11 (m, 1H), 1.06-0.96 (m, 9H) ppm.

Example 370. (2S)-3-[3-[(6R)-14-Amino-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanamide

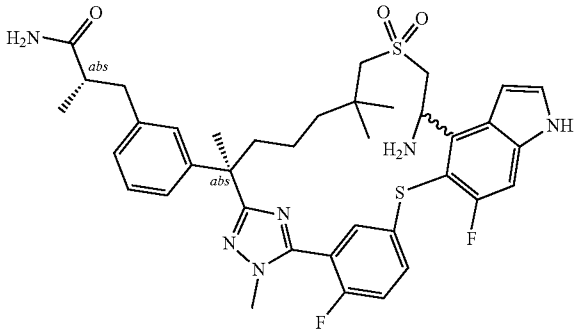 [SMILES: C[C@@H](Cc1cccc([C@@]2(C)CCCC(C)(C)CS(=O)(=O)CC(N)c3c(c(F)cc4[nH]ccc34)Sc3ccc(F)c(c3)-c3nc2nn3C)c1)C(N)=O]

Exchanging methyl (2R)-2-methyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanoate (Step C product of Example 200) with methyl (2S)-3-[3-[(6R,13E)-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,13,15,17,20,22,25,27-decaen-6-yl]phenyl]-2-methyl-propanoate (Step C product of Example 204, 1.00 g, 1.36 mmol) in Step A, and dimethylamine hydrochloride with ammonium chloride in Step B of Example 367, the reaction procedure sequence, Steps A, B of Example 367, followed by Step A of example 369, was followed to provide the title compounds. The first eluent was designated as Compound 367A (Diastereomer 1, 1.0 mg, white solid) and the second eluent was designated as Compound 367B (Diastereomer 2, 2.0 mg, white solid).

Compound 370A: LC-MS: MS (ESI): 735 m/z $[M+H]^+$, purity: >99% (214 nm), retention time: 1.67 minutes (LC-MS method 015).

Compound 370B: LC-MS: MS (ESI): 735 m/z $[M+H]^+$, purity: >99% (214 nm), retention time: 1.70 minutes (LC-MS method 015).

Example 371. Diastereomer 1 of 2-(methoxymethyl)-3-[3-[(6R)-21,22,28-trifluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

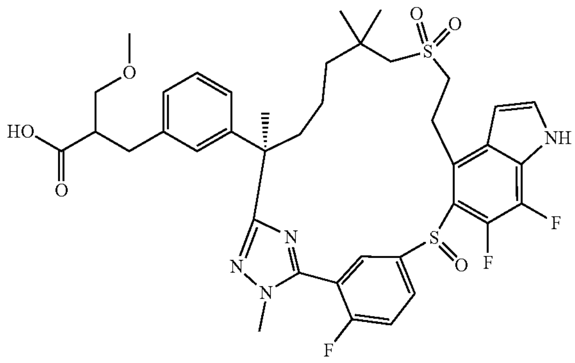 [SMILES: COCC(Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O]

Diastereomer 1 of Methyl 2-(3-((R)-2-(5-(5-((4-bromo-6,7-difluoro-1H-indol-5-yl)thio)-2-fluorophenyl)-1-methyl-1H-1,2,4-triazol-3-yl)-7-((2-hydroxyethyl)sulfonyl)-6,6-dimethylheptan-2-yl)benzyl)-3-methoxypropanoate

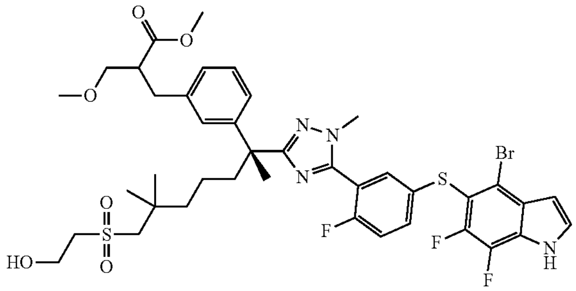 [SMILES: COCC(Cc1cccc([C@@](C)(CCCC(C)(C)CS(=O)(=O)CCO)c2nc(-c3cc(Sc4c(F)c(F)c5[nH]ccc5c4Br)ccc3F)n(C)n2)c1)C(=O)OC]

Step A: To a stirred solution of methyl 5-((4-bromo-6,7-difluoro-1H-indol-5-yl)thio)-2-fluorobenzimidothioate hydroiodide (Intermediate 14-16, 1.91 g, 3.42 mmol) and Diastereomer 1 of methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate (Intermediate 165A, 1.60 g, 3.11 mmol) in pyridine (50 mL) were added 4A molecular sieves (1.6 g). The reaction mixture was stirred at 50° C. for 1 hour, then at 80° C. for 16 hours, and concentrated. The residue was diluted with ethyl acetate (150 mL), washed with 1N hydrochloric acid, brine, dried over sodium sulfate, filtered, and concentrated. The residue was purified by flash chromatography (80 g silica gel column, eluting with 0-75% ethyl acetate in petroleum ether) to give the title compound product (2.00 g, 73%) as a yellow solid. LC-MS: MS (ESI): 879, 881 m/z $[M+H]^+$, purity: >99% (214 nm), retention time: 1.94 minutes (LC-MS method 026).

Diastereomer 1 of methyl 2-(3-((R)-2-(5-(5-((4-bromo-6,7-difluoro-1-(methylsulfonyl)-1H-indol-5-yl)thio)-2-fluorophenyl)-1-methyl-1H-1,2,4-triazol-3-yl)-6,6-dimethyl-7-(vinylsulfonyl)heptan-2-yl) benzyl)-3-methoxypropanoate

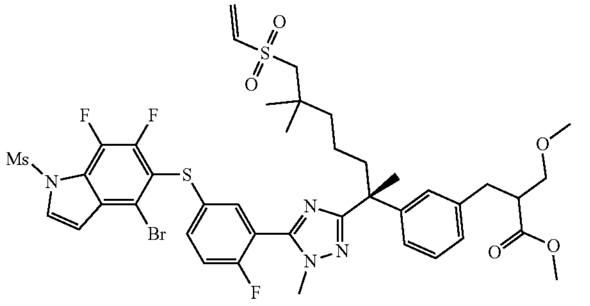 [SMILES: C=CS(=O)(=O)CC(C)(C)CCC[C@](C)(c1cccc(CC(COC)C(=O)OC)c1)c1nc(-c2cc(Sc3c(F)c(F)c4c(ccn4S(C)(=O)=O)c3Br)ccc2F)n(C)n1]

Step B: To a stirred solution of the product from Step A (2.00 g, 2.27 mmol) and triethylamine (0.95 mL, 6.82 mmol) in dichloromethane (20 mL) was added methanesulfonyl chloride (0.35 mL, 4.55 mmol). The reaction mixture was stirred at room temperature for 2 hours, diluted with water (50 mL), and extracted with dichloromethane (2×50 mL). The combined organic extracts were washed with saturated aqueous sodium bicarbonate, brine, dried over sodium sulfate, filtered, and concentrated. The residue was purified by flash chromatography 80 g silica gel column, eluting with 0-50% ethyl acetate in petroleum ether from) to give the title compound (1.90 g, 89%) as a solid. LC-MS: MS (ESI): 939, 941 m/z $[M+H]^+$, purity: 97% (214 nm), retention time: 1.92 minutes (LC-MS method 040).

Diastereomer 1 of methyl 3-methoxy-2-(3-((R,$1^4$Z, 5E)-$2^6$,$4^6$,$4^7$-trifluoro-$1^1$,9,9,13-tetramethyl-$4^1$-(methylsulfonyl)-7,7-dioxido-$1^1$H,$4^1$H-3,7-dithia-4 (5,4)-indola-1(5,3)-triazola-2(1,3)-benzenacyclotridecaphan-5-en-13-yl)benzyl) propanoate

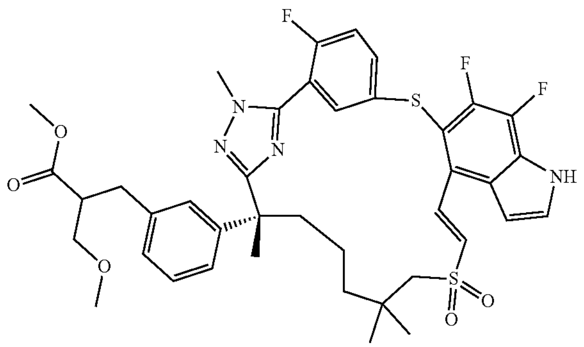 [SMILES: COCC(Cc1cccc([C@@]2(C)CCCC(C)(C)CS(=O)(=O)/C=C/c3c(c(F)c(F)c4[nH]ccc34)Sc3ccc(F)c(c3)-c3nc2nn3C)c1)C(=O)OC]

Step C: To a stirred mixture of chloro[(tri-tert-butylphosphine)(2-aminobiphenyl-2-yl)palladium(II) (0.10 g, 0.202 mmol), N-cyclohexyl-N-methyl-cyclohexanamine (0.79 g, 4.04 mmol) and tri-tert-butylphosphine tetrafluoroborate (0.12 g, 0.404 mmol) in toluene (100 mL) was added dropwise, over 1 hour at 120° C., and under an argon atmosphere a solution of the product from Step B (1.90 g, 2.02 mmol) in toluene (20 mL). After addition was complete, the reaction mixture was stirred at 120° C. for 2 hours and then concentrated. The residue was purified by flash chromatography (80 g silica gel column, eluting with 0-75% ethyl acetate in petroleum ether) to give the title compound (1.18 g, 68%) as a solid. LC-MS: MS (ESI): 859 m/z $[M+H]^+$, purity: 97% (214 nm), retention time: 1.99 minutes (LC-MS method 040).

Compound 371. Diastereomer 1 of 2-(methoxymethyl)-3-[3-[(6R)-21,22,28-trifluoro-3,6,10,10-tetramethyl-12,12,24-trioxo-12λ6,24λ4-dithia-3,4,19, 30-tetrazapentacyclo[23.3.1.12,5.015,23.016,20] triaconta-1(29),2(30),4,15,17,20,22,25,27-nonaen-6-yl]phenyl]propanoic Acid

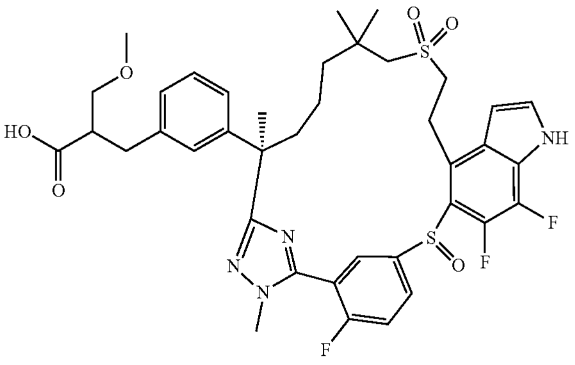 [SMILES: COCC(Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O]

Exchanging methyl (2R)-3-[3-[(6R,13E)-21,22-difluoro-3,6,10,10-tetramethyl-12,12-dioxo-12λ6,24-dithia-3,4,19, 28,30-pentazapentacyclo[23.3.1.12,5.015,23.016,20]triaconta-1(29),2(30),4,13,15,17,20,22,25,27-decaen-6-yl] phenyl]-2-methyl-propanoate (Step A product of Example 301) with the Step C product of this Example (1.13 g, 1.32 mmol) in Step B of Example 301, the reaction procedure sequence, Step B of Example 301, followed by Step F, G and H of Example 204, was followed to give the title compound (77 mg) as a white solid. LC-MS: MS (ESI): 785 m/z $[M+H]^+$, purity: >99% (214 nm), retention time: 1.62 minutes (LC-MS method 040). $^1$H NMR (400 MHz, $CD_3OD$) δ 8.11-7.98 (m, 2H), 7.61 (t, J=9.2 Hz, 1H), 7.44 (d, J=3.6 Hz, 1H), 7.14 (t, J=7.6 Hz, 1H), 7.09 (s, 1H), 7.04-6.98 (m, 2H), 6.77 (s, 1H), 3.97-3.90 (m, 1H), 3.85 (d, J=2.4 Hz, 3H), 3.70-3.63 (m, 1H), 3.53-3.38 (m, 3H), 3.30-3.24 (m, 1H), 3.25 (s, 3H), 3.09-2.99 (m, 2H), 2.86-2.72 (m, 3H), 2.29-2.23 (m, 1H), 1.94-1.87 (m, 1H), 1.70 (s, 3H), 1.49-1.31 (m, 3H), 1.20 (s, 3H), 1.11 (s, 3H), 1.06-0.99 (m, 1H) ppm.

Example 372. Diastereomer 2 of 2-(methoxymethyl)-3-[3-[(6R)-21,22,28-trifluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]propanoic Acid

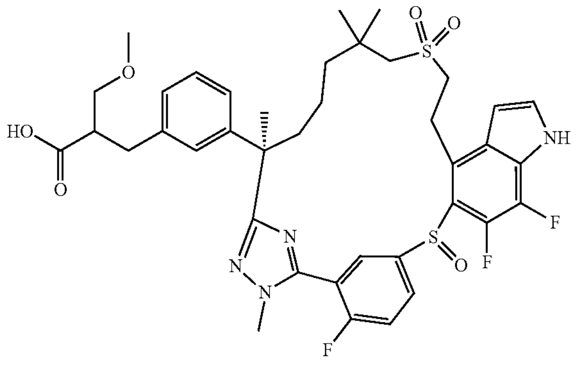 [SMILES: COCC(Cc1cccc([C@@]2(C)CCCC(C)(C)CS(=O)(=O)CCc3c(c(F)c(F)c4[nH]ccc34)S(=O)c3ccc(F)c(c3)-c3nc2nn3C)c1)C(=O)O]

Exchanging Diastereomer 1 of methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate (Intermediate 165A) with Diastereomer 2 of methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate (Intermediate 165B, 1.45 g, 2.82 mmol) in Step A of Example 371, the reaction procedure sequence, Steps A and B of Example 371, followed by Step B of Example 301, and Steps F, G and H of Example 204, was followed to afford the title compound (Compound 372, 64 mg) as a white solid. LC-MS: MS (ESI): 785 m/z $[M+H]^+$, purity: >99% (214 nm), retention time: 1.50 minutes (LC-MS method 040). $^1H$ NMR (500 MHz, $CD_3OD$) δ 8.35-7.76 (m, 2H), 7.64-7.56 (m, 1H), 7.43 (d, J=3.5 Hz, 1H), 7.16-7.11 (m, 1H), 7.07-7.01 (m, 2H), 7.00-6.96 (m, 1H), 6.76 (s, 1H), 4.04-3.87 (m, 1H), 3.85 (d, J=2.0 Hz, 3H), 3.69-3.62 (m, 1H), 3.53-3.37 (m, 3H), 3.26-3.20 (m, 4H), 3.08-2.98 (m, 2H), 2.86-2.72 (m, 3H), 2.32-2.21 (m, 1H), 1.95-1.86 (m, 1H), 1.69 (s, 3H), 1.50-1.31 (m, 3H), 1.19 (s, 3H), 1.10 (s, 3H), 1.05-0.97 (m, 1H) ppm.

Example 373. 3-[2-Methoxy-3-(21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl)phenyl]propanoic Acid

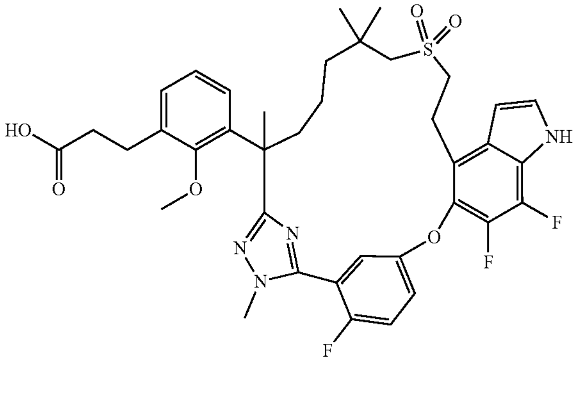 [SMILES: COc1c(CCC(=O)O)cccc1C1(C)CCCC(C)(C)CS(=O)(=O)CCc2c(c(F)c(F)c3[nH]ccc23)Oc2ccc(F)c(c2)-c2nc1nn2C]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (intermediate 69) with ethyl 3-(3-(7-((2-hydroxyethyl)sulfonyl)-2,6,6-trimethyl-1-(2-methylhydrazineyl)-1-oxoheptan-2-yl)-2-methoxyphenyl)propanoate (intermediate 129-1, 600 mg, 1.17 mmol) and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1H-indol-5-yl)oxy)-2-fluorobenzimidothioate hydroiodide (Intermediate 14-2, 630 mg, 1.52 mmol) in Step A of Example 6, the reaction procedure sequence (Steps A-D, and Step F) described for Example 6 was followed to prepare the title compound (Compound 373, 15.7 mg) as a white solid. Note that in Step A, the reaction was first heated at 50° C. for 16 hours, then at 80° C. for 2 days to improve yield. LC-MS: MS (ESI): 739 m/z $[M+H]^+$, retention time: 1.83 minutes; purity: >99% (254 nm) (LC-MS method 004). $^1H$ NMR (400 MHz, $CD_3OD$) δ 7.36 (d, J=3.2 Hz, 1H), 7.33-7.28 (m, 3H), 7.20 (d, J=7.6 Hz, 1H), 7.12 (d, J=7.6 Hz, 1H), 7.01 (t, J=7.2 Hz, 1H), 6.67 (t, J=2.8 Hz, 1H), 3.80 (s, 3H), 3.34-3.30 (m, 2H), 3.23 (s, 3H), 3.20-3.12 (m, 1H), 2.92-2.84 (m, 4H), 2.57-2.55 (m, 2H), 2.20-2.14 (m, 1H), 1.82-1.74 (m, 1H), 1.69 (s, 3H), 1.49-1.44 (m, 1H), 1.32-1.26 (m, 3H), 1.17-1.12 (m, 7H) ppm.

Example 374. Diastereomer 1 of 2-[[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]methyl]-3-methoxy-propanoic Acid

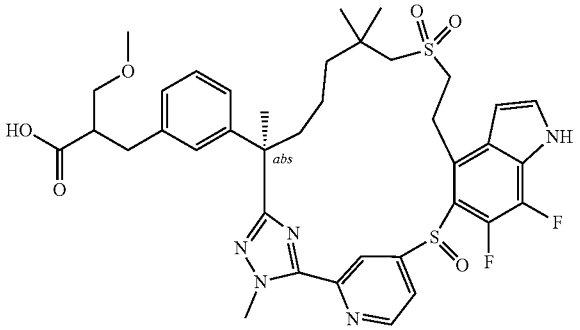 [SMILES: COCC(Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O]

Exchanging methyl 5-((4-bromo-6,7-difluoro-1H-indol-5-yl)thio)-2-fluorobenzimidothioate hydroiodide (Intermediate 14-16) with methyl 4-[(4-bromo-6,7-difluoro-1H-indol-5-yl)sulfanyl]pyridine-2-carboximidothioate (Intermediate 150-8, 0.89 g, 2.14 mmol)) in Step A of Example 371, the reaction procedure sequence, Steps A, B of Example 371, followed by Step B of Example 301, and Steps F, G and H of Example 204, was followed to afford the title compound (Compound 374, 100 mg) as a white solid. LC-MS: MS (ESI): 768 m/z $[M+H]^+$, purity: >99% (214 nm), retention time: 1.51 minutes (LC-MS method 026). $^1H$ NMR (400 MHz, $CD_3OD$) δ 9.03-8.07 (m, 2H), 7.44 (d, J=3.2 Hz, 1H), 7.08-6.59 (m, 6H), 4.30 (s, 3H), 3.63-3.61 (m, 1H), 3.48-3.41 (m, 3H), 3.23 (s, 3H), 3.12-3.06 (m, 2H), 2.87-2.71 (m, 4H), 1.79-1.70 (m, 4H), 1.56-1.41 (m, 4H), 1.34-1.11 (m, 8H) ppm.

Example 375. Diastereomer 2 of 2-[[3-[(6R)-21,22-difluoro-3,6,10,10-tetramethyl-12,12,24-trioxo-12λ6,24λ4-dithia-3,4,19,28,30-pentazapentacyclo[23.3.1.12,5.015,23.016,20]triaconta-1(29),2(30),4,15,17,20,22,25,27-nonaen-6-yl]phenyl]methyl]-3-methoxy-propanoic Acid

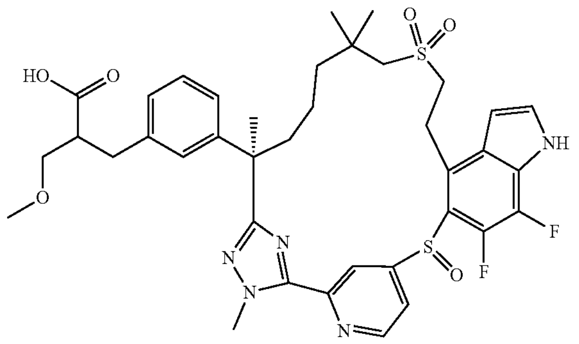 [SMILES: COCC(Cc1cccc([C@@]2(C)CCCC(C)(C)CS(=O)(=O)CCc3c(c(F)c(F)c4[nH]ccc34)S(=O)c3ccnc(c3)-c3nc2nn3C)c1)C(=O)O]

Exchanging Diastereomer 1 of methyl 2-(3-((R)-7-((2-hydroxyethyl)sulfonyl)-2,6,6-trimethyl-1-(2-methylhydrazineyl)-1-oxoheptan-2-yl)benzyl)-3-methoxypropanoate (Intermediate 165A) with Diastereomer 2 of methyl 2-(3-((R)-7-((2-hydroxyethyl)sulfonyl)-2,6,6-trimethyl-1-(2-methylhydrazineyl)-1-oxoheptan-2-yl)benzyl)-3-methoxy-propanoate (Intermediate 165B, 1.00 g, 1.94 mmol), and methyl 5-((4-bromo-6,7-difluoro-1H-indol-5-yl)thio)-2-fluorobenzimidothioate hydroiodide (Intermediate 14-16) with methyl 4-[(4-bromo-6,7-difluoro-1H-indol-5-yl)sulfanyl]pyridine-2-carboximidothioate (Intermediate 150-8, 0.89 g, 2.14 mmol) in Step A of Example 371, the reaction procedure sequence, Steps A, B of Example 371, followed by Step B of Example 301, and Steps F, G and H of Example 204, was followed to afford the title compound (Compound 375, 69 mg) as a white solid. LC-MS: MS (ESI): 768 m/z $[M+H]^+$, purity: >99% (214 nm), retention time: 1.97 minutes (LC-MS method 042). 1H NMR (500 MHz, $CD_3OD$) δ 9.07-8.00 (m, 2H), 7.47 (d, J=3.5 Hz, 1H), 7.37-6.45 (m, 6H), 4.33 (s, 3H), 3.80-3.34 (m, 5H), 3.29-2.71 (m, 9H), 2.48 (s, 1H), 1.87-0.99 (m, 14H) ppm.

Example 376. Methyl (2R)-3-[3-[(6R)-22,28-difluoro-26-hydroxy-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

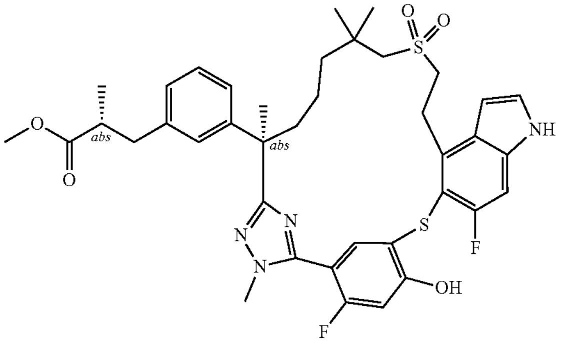 [SMILES: COC(=O)[C@H](C)Cc1cccc([C@@]2(C)CCCC(C)(C)CS(=O)(=O)CCc3c(c(F)cc4[nH]ccc34)Sc3cc(c(F)cc3O)-c3nc2nn3C)c1]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (R)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137, 3.05 g, 6.28 mmol), and methyl 5-((4-bromo-6-fluoro-1H-indol-5-yl)oxy)-2-fluorobenzimidothioate hydroiodide (Intermediate 14-1) with methyl 4-(benzyloxy)-5-((4-bromo-6-fluoro-1H-indol-5-yl)thio)-2-fluorobenzimidothioate hydroiodide (Intermediate 76-1, 3.7 g, 5.71 mmol) in Step A of Example 6, the reaction procedure sequence (Steps A to D described) for Example 6 was followed to afford the title compound (Compound 376, 0.94 g) as a white solid. LC-MS: MS (ESI): 751 m/z $[M+H]^+$, purity: >99% (214 nm), retention time: 2.30 minutes (LC-MS method 042). $^1H$ NMR (500 MHz, DMSO-d6) δ 11.44 (s, 1H), 11.40-11.20 (m, 1H), 7.43 (d, J=2.5 Hz, 1H), 7.27 (d, J=9.5 Hz, 1H), 7.07 (t, J=7.5 Hz, 1H), 7.00-6.90 (m, 3H), 6.83-6.76 (m, 2H), 6.57 (s, 1H), 3.63 (t, J=5.5 Hz, 3H), 3.62-3.53 (m, 2H), 3.49 (s, 3H), 3.28-3.16 (m, 2H), 2.84-2.69 (m, 3H), 2.64-2.55 (m, 3H), 2.03-1.90 (m, 1H), 1.55 (s, 3H), 1.42-1.21 (m, 2H), 1.18-1.07 (m, 2H), 1.03-0.96 (m, 6H), 0.89 (s, 3H) ppm.

Example 377. (2R)-3-[3-[(6R)-26-Amino-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

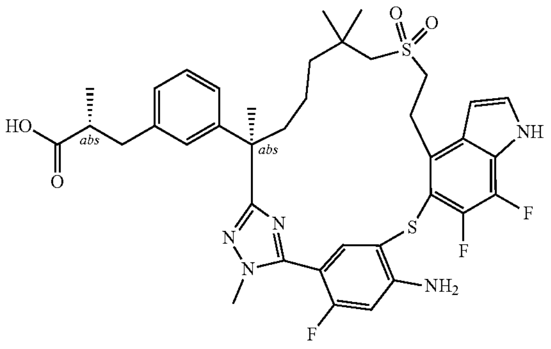 [SMILES: C[C@H](Cc1cccc([C@@]2(C)CCCC(C)(C)CS(=O)(=O)CCc3c(c(F)c(F)c4[nH]ccc34)Sc3cc(c(F)cc3N)-c3nc2nn3C)c1)C(=O)O]

Methyl (2R)-3-[3-[(6R)-22,28-difluoro-3,6,10,10-tetramethyl-12,12-dioxo-26-(trifluoromethylsulfonyloxy)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

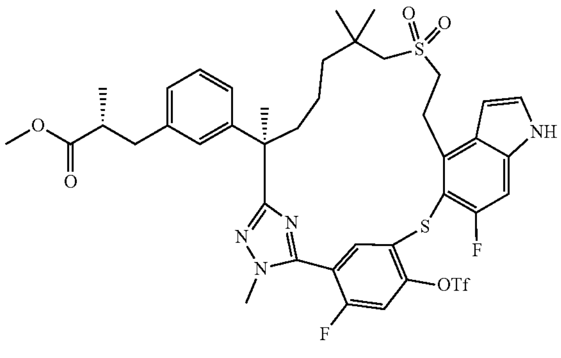 [SMILES: COC(=O)[C@H](C)Cc1cccc([C@@]2(C)CCCC(C)(C)CS(=O)(=O)CCc3c(c(F)cc4[nH]ccc34)Sc3cc(c(F)cc3OS(=O)(=O)C(F)(F)F)-c3nc2nn3C)c1]

Step A: To a stirred solution of methyl (2R)-3-[3-[(6R)-22,28-difluoro-26-hydroxy-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Example 376, 850 mg, 1.13 mmol) in dichloromethane (25 ml) were added pyridine (0.27 ml, 3.40 mmol) and trifluoromethanesulfonic anhydride (0.38 ml, 2.26 mmol). The reaction was stirred at room temperature for 16 hours and diluted with dichloromethane (40 ml). The mixture was washed with brine, dried over sodium sulfate, filtered, and concentrated. The residue was purified by automated flash chromatography (40 g silica gel column, eluting with 0-60% ethyl acetate in petroleum ether) to give the title compound (850 mg, 85%) as a white solid. LC-MS: MS (ESI): 883 m/z $[M+H]^+$, purity: 95% (254 nm), retention time: 2.30 minutes (LC-MS method 042).

Methyl (2R)-3-[3-[(6R)-26-[(2,4-dimethoxyphenyl)methylamino]-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

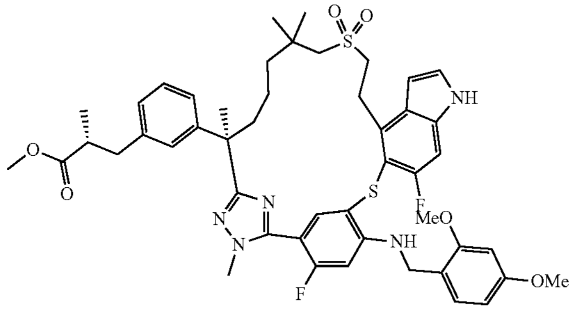 [SMILES: COC(=O)[C@H](C)Cc1cccc([C@@]2(C)CCCC(C)(C)CS(=O)(=O)CCc3c(c(F)cc4[nH]ccc34)Sc3cc(c(F)cc3NCc3ccc(OC)cc3OC)-c3nc2nn3C)c1]

Step B: To a stirred solution of the product from Step B (200 mg, 0.227 mmol) and (2,4-dimethoxyphenyl)methanamine (76 mg, 0.453 mmol) in 1,4-dioxane (5 ml) was added cesium carbonate (148 mg, 0.453 mmol) and [1,1'-Bis(diphenylphosphino)ferrocene]dichloropalladium(II) (50 mg, 0.0680 mmol). The reaction was stirred at 100° C. for 16 hours, cooled to room temperature, and diluted with ethyl acetate (15 ml). The mixture was washed with brine, dried over sodium sulfate, filtered, and concentrated. The residue was purified by automated flash chromatography (12 g silica gel column, eluting with 0-60% ethyl acetate in petroleum ether) to give the title compound (50 mg, 25%) as a white solid. LC-MS: MS (ESI): 900 m/z $[M+H]^+$, purity: >99% (254 nm), retention time: 2.05 minutes (LC-MS method 004). Methyl (2R)-3-[3-[(6R)-26-amino-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

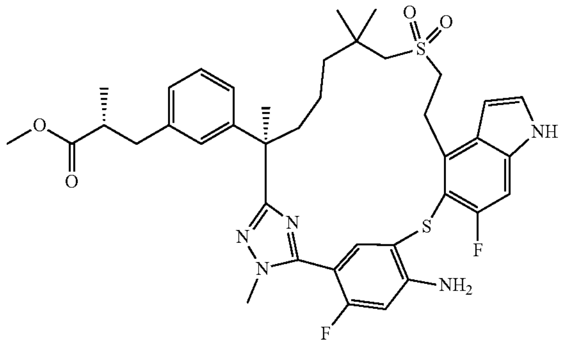 [SMILES: COC(=O)[C@H](C)Cc1cccc([C@@]2(C)CCCC(C)(C)CS(=O)(=O)CCc3c(c(F)cc4[nH]ccc34)Sc3cc(c(F)cc3N)-c3nc2nn3C)c1]

Step C: To a stirred solution of the product from Step B (30 mg, 0.028 mmol) in dichloromethane (2 ml) was added trifluoroacetic acid (2.0 ml). The reaction was stirred at room temperature for 2 hours, then diluted with dichloromethane (10 ml). The mixture was washed with brine, dried over sodium sulfate, filtered, and concentrated. The residue was purified by automated flash chromatography (12 g silica gel column, eluting with 0-60% ethyl acetate in petroleum ether) to the title compound (15 mg, 63%) as a white solid. LC-MS: MS (ESI): 750 m/z $[M+H]^+$, purity: 51% (214 nm), retention time: 2.51 minutes (LC-MS method 004).

Compound 377: (2R)-3-[3-[(6R)-26-Amino-22,28-di fluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

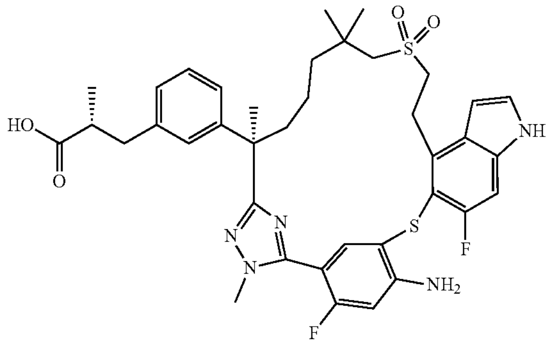 [SMILES: C[C@H](Cc1cccc([C@@]2(C)CCCC(C)(C)CS(=O)(=O)CCc3c(c(F)cc4[nH]ccc34)Sc3cc(c(F)cc3N)-c3nc2nn3C)c1)C(=O)O]

Step D: To a stirred solution of the product from Step C (15 mg, 0.0200 mmol) in tetrahydrofuran (1 ml) and water (1 ml) was added lithium hydroxide monohydrate (8 mg, 0.19 mmol). The reaction was stirred at room temperature overnight, then acidified with 1M hydrochloric acid (5 ml) and extracted with ethyl acetate (10 ml). The separated organic layer was washed with brine, dried over sodium sulfate, filtered, and concentrated. The residue was purified by pre-HPLC to give the title compound (2.4 mg, 16%) as a white solid. LC-MS: MS (ESI): 736 m/z $[M+H]^+$, purity: >99% (214 nm), retention time: 1.81 minutes (LC-MS method 004). $^1H$ NMR (400 MHz, $CD_3OD$) δ 8.28 (brs, 1H), 7.85 (d, J=7.6 Hz, 1H), 7.28 (d, J=3.2 Hz, 1H), 7.19-7.12 (m, 2H), 7.09 (s, 1H), 7.04-6.99 (m, 2H), 6.65-6.53 (m, 2H), 3.83-3.70 (m, 5H), 3.44-3.38 (m, 1H), 3.28-3.23 (m, 1H), 3.11-3.03 (m, 2H), 3.00-2.95 (m, 1H), 2.65-2.60 (m, 2H), 2.40-2.32 (m, 1H), 1.95-1.86 (m, 1H), 1.70 (s, 3H), 1.60-1.45 (m, 3H), 1.35-1.26 (m, 1H), 1.22 (s, 3H), 1.18 (s, 3H), 1.14-1.05 (m, 3H) ppm.

Example 378. (6R)-6-[3-[(2R)-2-Carboxypropyl]phenyl]-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaene-26-carboxylic Acid

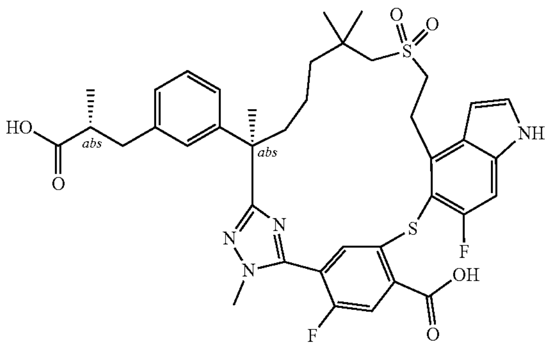 [SMILES: C[C@H](Cc1cccc([C@@]2(C)CCCC(C)(C)CS(=O)(=O)CCc3c(c(F)cc4[nH]ccc34)Sc3cc(c(F)cc3C(=O)O)-c3nc2nn3C)c1)C(=O)O]

Methyl (2R)-3-[3-[(6R)-22,28-difluoro-3,6,10,10-tetramethyl-19-methylsulfonyl-12,12-dioxo-26-(trifluoromethylsulfonyloxy)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

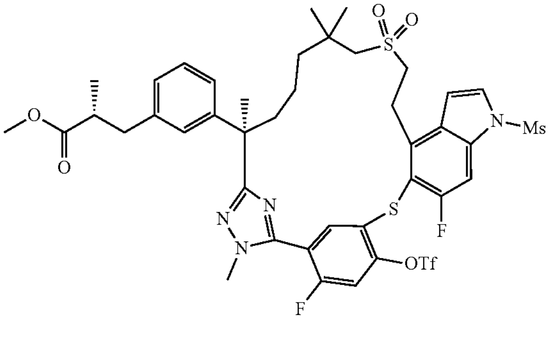 [SMILES: COC(=O)[C@H](C)Cc1cccc([C@@]2(C)CCCC(C)(C)CS(=O)(=O)CCc3c(c(F)cc4c3ccn4S(C)(=O)=O)Sc3cc(c(F)cc3OS(=O)(=O)C(F)(F)F)-c3nc2nn3C)c1]

Step A: To a stirred solution of methyl (2R)-3-[3-[(6R)-22,28-difluoro-3,6,10,10-tetramethyl-12,12-dioxo-26-(trifluoromethylsulfonyloxy)-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (Step A product of Example 377, 400 mg, 0.453 mmol) in dichloromethane (10 ml) was added triethylamine (0.38 ml, 2.72 mmol) and methanesulfonyl chloride (311 mg, 2.72 mmol). The reaction was stirred at room temperature for 2 hours, then diluted with dichloromethane (10 ml). The mixture was washed with brine, dried over sodium sulfate, filtered, and concentrated. The residue was purified by automated flash chromatography (12 g silica gel column, eluting with 0-60% ethyl acetate in petroleum ether) to give the title compound (350 mg, 80%) as a white solid. LC-MS: MS (ESI): 961 m/z $[M+H]^+$, purity: 95% (214 nm), retention time: 2.86 minutes (LC-MS method 004).

(6R)-22,28-Difluoro-6-[3-[(2R)-3-methoxy-2-methyl-3-oxo-propyl]phenyl]-3,6,10,10-tetramethyl-19-methylsulfonyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaene-26-carboxylic Acid

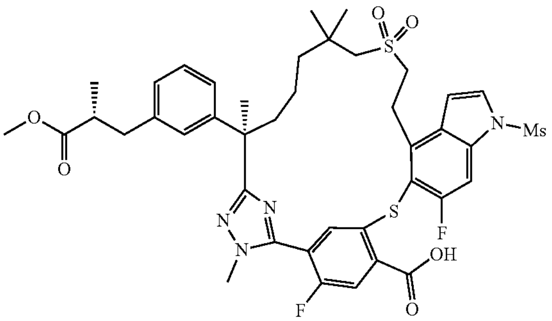 [SMILES: COC(=O)[C@H](C)Cc1cccc([C@@]2(C)CCCC(C)(C)CS(=O)(=O)CCc3c(c(F)cc4c3ccn4S(C)(=O)=O)Sc3cc(c(F)cc3C(=O)O)-c3nc2nn3C)c1]

Step B: To a stirred solution of the product from Step A (280 mg, 0.291 mmol) in dimethylformamide (8 ml) and water (1 ml) was added triethylamine (0.41 ml, 2.91 mmol) and $Pd(PPh_3)_4$ (67 mg, 0.0583 mmol). The reaction was stirred at 80° C. for 16 hours under an atmosphere of carbon monoxide, cooled to room temperature, and diluted with ethyl acetate (20 ml. The mixture was washed with water, dried over magnesium sulfate, filtered, and concentrated. The residue was purified by automated flash chromatography (12 g silica gel column, eluting with 0-80% ethyl acetate in petroleum) to give the title compound (130 mg, 57%) as a white solid. LC-MS: MS (ESI): 857 m/z $[M+H]^+$, purity: 87% (254 nm), retention time: 2.48 minutes (LC-MS method 004).

Compound 378: (6R)-6-[3-[(2R)-2-Carboxypropyl]phenyl]-22,28-difluoro-3,6,10,10-tetramethyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaene-26-carboxylic acid

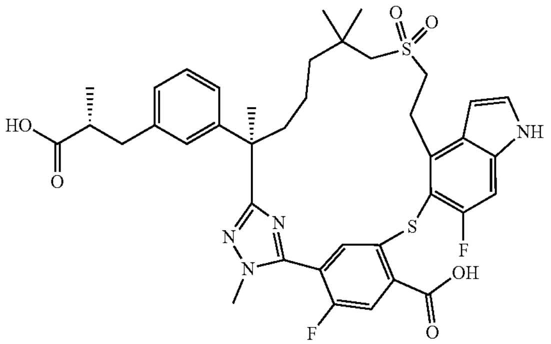 [SMILES: C[C@H](Cc1cccc([C@@]2(C)CCCC(C)(C)CS(=O)(=O)CCc3c(c(F)cc4[nH]ccc34)Sc3cc(c(F)cc3C(=O)O)-c3nc2nn3C)c1)C(=O)O]

Step C: To a stirred solution of the product from Step B (10 mg, 0.0117 mmol) in methanol (1 ml), tetrahydrofuran (1 ml) and water (1 ml) was added lithium hydroxide monohydrate (10 mg, 0.238 mmol). The reaction was stirred at room temperature for 16 hours, acidified with 1M hydrochloric acid (5 ml), and extracted with ethyl acetate (10 ml). The mixture was washed with brine, dried over sodium sulfate, filtered, and concentrated. The residue was purified by prep-HPLC to afford the title compound (5.0 mg, 56%) as a white solid. LC-MS: MS (ESI): 765 m/z $[M+H]^+$, purity: >99% (214 nm), retention time: 1.86 minutes (LC-MS method 004). 1H NMR (500 MHz, DMSO-$d_6$) δ 14.18 (brs, 1H), 12.13 (brs, 1H), 11.51 (s, 1H), 7.90 (d, J=10.5 Hz, 1H), 7.46 (s, 1H), 7.34 (d, J=9.5 Hz, 1H), 7.04 (t, J=7.5 Hz, 1H), 6.98-6.92 (m, 2H), 6.89 (d, J=6.3 Hz, 1H), 6.65-6.55 (m, 2H), 3.71-3.52 (m, 5H), 3.23-3.05 (m, 2H), 3.04-2.80 (m, 2H), 2.74 (d, J=14.5 Hz, 1H), 1.92-1.82 (m, 1H), 1.54 (s, 3H), 1.43-1.37 (m, 2H), 1.31-1.17 (m, 5H), 1.04 (s, 3H), 0.95 (d, J=6.5 Hz, 3H), 0.86 (s, 3H) ppm.

Example 379. Compound 379A and 379B, Diastereomer 1 and 2 of (2R)-3-[3-[(6R)-26-amino-22,28-difluoro-3,6,10,10-tetramethyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

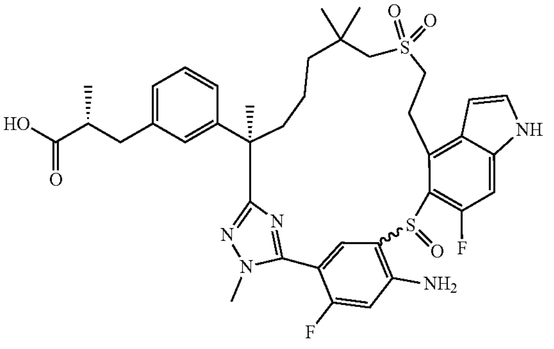 [SMILES: C[C@H](Cc1cccc([C@@]2(C)CCCC(C)(C)CS(=O)(=O)CCc3c(c(F)cc4[nH]ccc34)S(=O)c3cc(c(F)cc3N)-c3nc2nn3C)c1)C(=O)O]

and

Compound 379C. (2R)-3-[3-[(6R)-26-Amino-22,28-difluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic acid

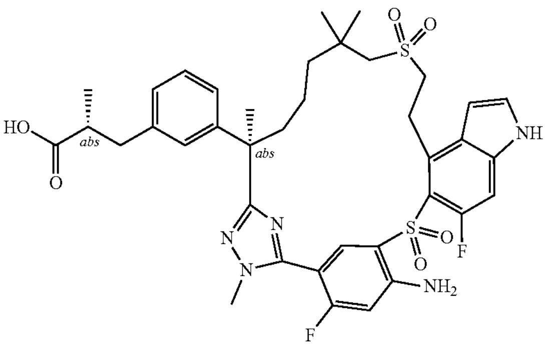

Methyl (2R)-3-[3-[(6R)-26-(benzyloxycarbonylamino)-22,28-difluoro-3,6,10,10-tetramethyl-19-methylsulfonyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

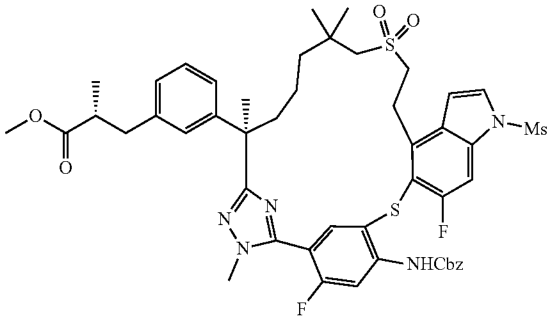 [SMILES: COC(=O)[C@H](C)Cc1cccc([C@@]2(C)CCCC(C)(C)CS(=O)(=O)CCc3c(c(F)cc4c3ccn4S(C)(=O)=O)Sc3cc(c(F)cc3NC(=O)OCc3ccccc3)-c3nc2nn3C)c1]

Step A: To a stirred solution of (6R)-22,28-difluoro-6-[3-[(2R)-3-methoxy-2-methyl-3-oxo-propyl]phenyl]-3,6,10,10-tetramethyl-19-methylsulfonyl-12,12-dioxo-12λ6,24-dithia-3,4,19,30-tetrazapentacyclo[23.3.1.12,5.015,23.016,20]triaconta-1(29),2(30),4,15,17,20,22,25,27-nonaene-26-carboxylic acid (Step B product of Example 378, 110 mg, 0.128 mmol) in toluene (7 ml) was added diphenylphosphoryl azide (53 mg, 0.193 mmol), triethylamine (0.054 mL, 0.385 mmol) and phenylmethanol (42 mg, 0.385 mmol). The reaction was stirred at 110° C. overnight, cooled to room temperature, and diluted with ethyl acetate (20 ml). The mixture was washed with water, dried over magnesium sulfate, filtered, and concentrated. The residue was purified by automated flash chromatography (12 g silica gel column, eluting with 0-80% ethyl acetate in petroleum) to give the title compound (83 mg, 67%) as a white solid. LC-MS: MS (ESI): 962 m/z $[M+H]^+$, purity: 68% (254 nm), retention time: 2.94 minutes (LC-MS method 004).

Methyl (2R)-3-[3-[(6R)-26-(benzyloxycarbonylamino)-22,28-difluoro-3,6,10,10-tetramethyl-19-methylsulfonyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate and methyl (2R)-3-[3-[(6R)-26-(benzyloxycarbonylamino)-22,28-difluoro-3,6,10,10-tetramethyl-19-methylsulfonyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

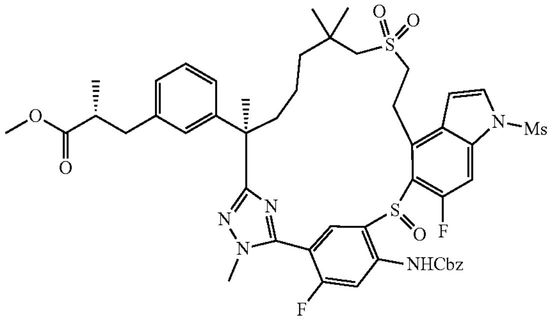

-continued

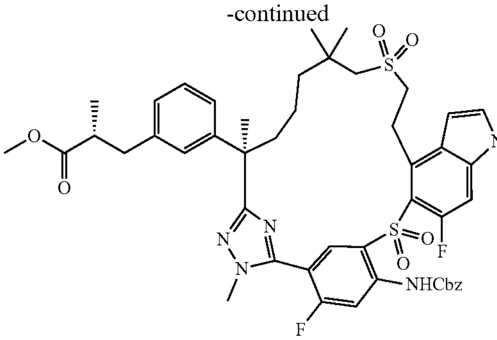

Step B: To a stirred solution of the product from Step A (83 mg, 0.0863 mmol) in methanol (5 ml) was added ammonium heptamolybdate tetrahydrate (21 mg, 0.0173 mmol) and hydrogen peroxide (0.60 ml, 19.6 mmol). The reaction was stirred at room temperature for 2 hours, diluted with water (15 ml), and extracted with ethyl acetate (3×15 ml). The combined organic layers were washed with brine, filtered, and concentrated. The residue was purified by automated flash chromatography (12 g silica gel column, eluting with 0%-100% ethyl acetate in petroleum ether). The peak eluting first was methyl (2R)-3-[3-[(6R)-26-(benzyloxycarbonylamino)-22,28-difluoro-3,6,10,10-tetramethyl-19-methylsulfonyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (26 mg, 30%) and the peak eluting second was methyl (2R)-3-[3-[(6R)-26-(benzyloxycarbonylamino)-22,28-difluoro-3,6,10,10-tetramethyl-19-methylsulfonyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate (50 mg, 59%).

First Peak: LC-MS: MS (ESI): 994 m/z $[M+H]^+$, purity: 85% (254 nm), retention time: 2.75 minutes (LC-MS method 017).

Second Peak: LC-MS: MS (ESI): 978 m/z $[M+H]^+$, purity: 76% (254 nm), retention time: 2.64 minutes (LC-MS method 017).

Methyl (2R)-3-[3-[(6R)-26-amino-22,28-difluoro-3,6,10,10-tetramethyl-19-methylsulfonyl-12,12,24-trioxo-12λ6,24λ4-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoate

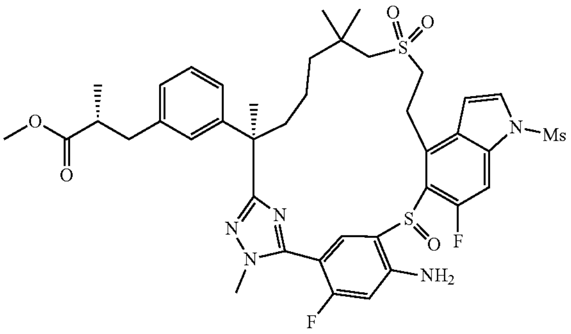 [SMILES: COC(=O)[C@H](C)Cc1cccc([C@@]2(C)CCCC(C)(C)CS(=O)(=O)CCc3c(c(F)cc4c3ccn4S(C)(=O)=O)S(=O)c3cc(c(F)cc3N)-c3nc2nn3C)c1]

Step C: A solution of the material from the second peak of the Step B product (50 mg, 0.0511 mmol) in hydrobromic acid (>33% in acetic acid, 5.0 ml) was stirred at room temperature for 2 hours. The mixture was diluted with water (20 ml) and extracted with ethyl acetate (3×15 ml). The combined organic layers were washed with brine, filtered, and concentrated. The residue was purified by automated flash chromatography (12 g silica gel column, eluting with 0%-100% ethyl acetate in petroleum ether) to give the title compound (35 mg, 81%) as light-yellow oil. LC-MS: MS (ESI): 844 m/z $[M+H]^+$, purity: 85% (254 nm), retention time: 2.39 minutes (LC-MS method 017).

Compound 379A (Diastereomers 1) and Compound 379B (Diastereomer 2) of (2R)-3-[3-[(6R)-26-amino-22,28-difluoro-3,6,10,10-tetramethyl-12,12,24-trioxo-12λ6,2414-dithia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanoic Acid

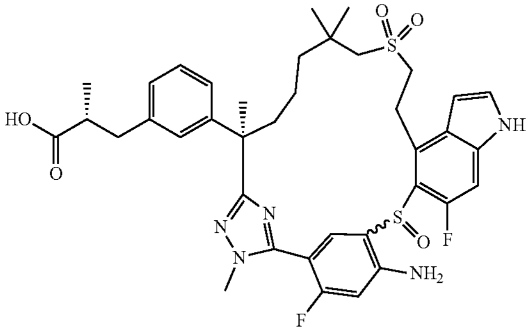 [SMILES: C[C@H](Cc1cccc([C@@]2(C)CCCC(C)(C)CS(=O)(=O)CCc3c(c(F)cc4[nH]ccc34)S(=O)c3cc(c(F)cc3N)-c3nc2nn3C)c1)C(=O)O]

Step D: To a stirred solution of the product from Step C (35 mg, 0.0415 mmol) in tetrahydrofuran (1 ml) and water (1 ml) was added lithium hydroxide monohydrate (206 mg, 4.91 mmol). The reaction was stirred at room temperature overnight, quenched with 1 M hydrochloric acid to pH ~5, and extracted with ethyl acetate (3×5 ml). The combined organic extracts were washed with brine, dried over sodium sulfate, filtered, and concentrated. The residue was purified by prep-HPLC. The first eluent (11 mg, 34%, white solid), Diastereomer 1, was designated as Compound 379A. The second eluent (3.5 mg, 10%, white solid), Diastereomer 2, was designated as Compound 379B.

Compound 379A: LC-MS: MS (ESI): 752 m/z $[M+H]^+$, purity: >99% (254 nm), retention time: 1.76 minutes (LC-MS method 004). $^1H$ NMR (500 MHz, DMSO-$d_6$) δ 12.11 (brs, 1H), 11.63 (s, 1H), 7.58 (brs, 1H), 7.52-7.47 (m, 1H), 7.32 (d, J=11.0 Hz, 1H), 7.15-7.09 (m, 2H), 6.99-6.86 (m, 2H), 6.70-6.60 (m, 2H), 6.42 (brs, 1H), 3.85-3.75 (m, 1H), 3.63 (s, 3H), 3.48-3.38 (m, 1H), 3.28-3.21 (m, 1H), 3.07-2.96 (m, 2H), 2.94-2.80 (m, 1H), 2.58-2.54 (m, 3H), 2.32-2.25 (m, 1H), 1.66-1.64 (m, 5H), 1.50-1.40 (s, 1H), 1.24-1.13 (m, 2H), 1.16 (s, 3H), 1.02 (s, 3H), 0.97 (d, J=6.5 Hz, 3H) ppm.

Compound 379B: LC-MS: MS (ESI): 752 m/z $[M+H]^+$, purity: 90% (214 nm), retention time: 2.17 minutes (LC-MS method 017). $^1H$ NMR (500 MHz, DMSO-$d_6$) δ 12.10 (s, 1H), 11.65 (s, 1H), 7.85-7.80 (m, 1H), 7.51 (s, 1H), 7.33 (d, J=11.5 Hz, 1H), 7.18-7.09 (m, 2H), 7.04-6.94 (m, 2H), 6.68 (d, J=12.5 Hz, 1H), 6.53 (s, 1H), 6.06 (brs, 1H), 3.80-3.70 (m, 4H), 3.60-3.51 (m, 1H), 3.27-3.19 (m, 1H), 3.10 (d, J=14.0 Hz, 1H), 3.00 (d, J=14 Hz, 1H), 2.90-2.80 (m, 1H), 2.58-2.54 (m, 3H), 2.25-2.20 (m, 1H), 1.82-1.76 (m, 1H), 1.66-1.64 (m, 4H), 1.39-1.33 (m, 1H), 1.24-1.21 (m, 2H), 1.18 (s, 3H), 1.08 (s, 3H), 0.98 (d, J=6.5 Hz, 3H) ppm.

Methyl (2R)-3-[3-[(6R)-26-amino-22,28-difluoro-3,6,10,10-tetramethyl-19-methylsulfonyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2-methylpropanoate

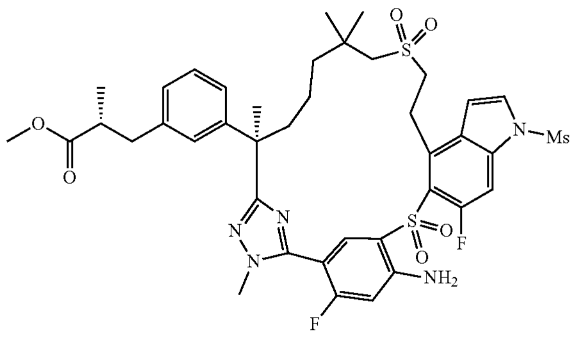 [SMILES: COC(=O)[C@H](C)Cc1cccc([C@@]2(C)CCCC(C)(C)CS(=O)(=O)CCc3c(c(F)cc4c3ccn4S(C)(=O)=O)S(=O)(=O)c3cc(c(F)cc3N)-c3nc2nn3C)c1]

Step E: A solution of the material from Peak 1 of the product from Step B (26 mg, 0.0262 mmol) in hydrobromic acid (>33% in acetic acid, 4.0 ml) was stirred at room temperature for 2 hours, diluted with water (15 ml), and extracted with ethyl acetate (3×15 ml). The combined organic layers were washed with brine (3×15 ml), filtered, and concentrated. The residue was purified by automated flash chromatography (12 g silica gel column, eluting with 0%-100% ethyl acetate in petroleum ether) to give the title compound (22 mg, 62%) as light-yellow oil. LC-MS: MS (ESI): 860 m/z $[M+H]^+$, purity: 63% (254 nm), retention time: 2.60 minutes (LC-MS method 017).

Compound 379C: (2R)-3-[3-[(6R)-26-amino-22,28-difluoro-3,6,10,10-tetramethyl-12,12,24,24-tetraoxo-12λ6,24λ6-dithia-3,4,19,30-tetrazapentacyclo[23.3.1.12,5.015,23.016,20]triaconta-1(29),2(30),4,15,17,20,22,25,27-nonaen-6-yl]phenyl]-2-methylpropanoic acid

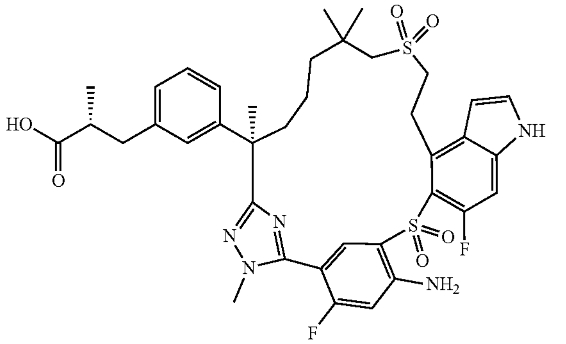 [SMILES: C[C@H](Cc1cccc([C@@]2(C)CCCC(C)(C)CS(=O)(=O)CCc3c(c(F)cc4[nH]ccc34)S(=O)(=O)c3cc(c(F)cc3N)-c3nc2nn3C)c1)C(=O)O]

Step F: To a stirred solution of the product from Step E (22 mg, 0.0161 mmol) in tetrahydrofuran (1 ml) and water (1 ml) was added lithium hydroxide monohydrate (80 mg, 1.91 mmol). The reaction was stirred at room temperature overnight, quenched with 1 M hydrochloric acid to pH ~5, and extracted with ethyl acetate (3×5 ml). The combined organic extracts were washed with brine, dried over anhydrous sodium sulfate, filtered, and concentrated. The residue was purified by prep-HPLC to give the title compound (10.3 mg, 83%) as a white solid. LC-MS: MS (ESI): 768 m/z $[M+H]^+$, purity: >99% (254 nm), retention time: 2.29 minutes (LC-MS method 048). $^1H$ NMR (500 MHz, DMSO-$d_6$) δ 12.11 (brs, 1H), 11.77 (s, 1H), 7.95 (d, J=7.8 Hz, 1H), 7.60-7.54 (m, 1H), 7.38 (d, J=12.5 Hz, 1H), 7.17-7.07 (m, 2H), 6.99-6.92 (m, 2H), 6.82-6.75 (m, 2H), 6.61 (s, 1H), 3.69 (d, J=2.5 Hz, 3H), 3.60-3.44 (m, 3H), 3.22-3.14 (m, 2H), 3.03 (d, J=13.5 Hz, 1H), 2.91-2.82 (m, 1H), 2.58-2.53 (m, 2H), 2.26-2.20 (m, 1H), 1.78-1.69 (m, 1H), 1.64 (s, 3H), 1.50-1.30 (m, 3H), 1.25-1.18 (m, 4H), 1.13 (s, 3H), 0.98 (d, J=6.5 Hz, 3H) ppm.

Example 380. (2R)-2-Methyl-3-[3-(9,9,21,22,28-pentafluoro-3-methyl-12,12-dioxo-24-oxa-12λ6-thia-3,4,7,19,30-pentazapentacyclo[23.3.1.12,5.015,23.016,20]triaconta-1(29),2(30),4,15,17,20,22,25,27-nonaen-6-yl)phenyl]propanoic Acid

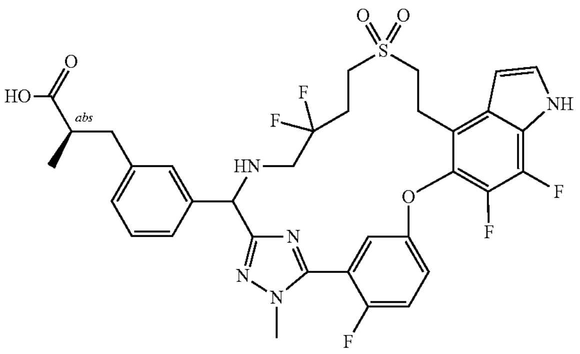 [SMILES: C[C@H](Cc1cccc(C2NCC(F)(F)CCS(=O)(=O)CCc3c(c(F)c(F)c4[nH]ccc34)Oc3ccc(F)c(c3)-c3nc2nn3C)c1)C(=O)O]

Methyl (2R)-3-(3-(acetoxy(5-(5-((4-bromo-6,7-difluoro-1H-indol-5-yl)oxy)-2-fluorophenyl)-1-methyl-1H-1,2,4-triazol-3-yl)methyl)phenyl)-2-methylpropanoate

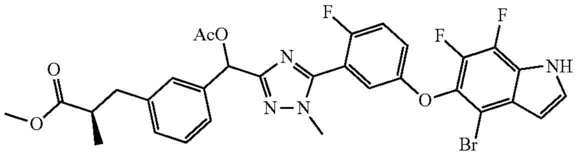 [SMILES: COC(=O)[C@H](C)Cc1cccc(C(OC(C)=O)c2nc(-c3cc(Oc4c(F)c(F)c5[nH]ccc5c4Br)ccc3F)n(C)n2)c1]

Step A: To a stirred solution of methyl 5-((4-bromo-6,7-difluoro-1H-indol-5-yl)oxy)-2-fluorobenzimidothioate hydroiodide (Intermediate 14-2, 1.85 g, 3.41 mmol) and methyl (2R)-3-(3-(1-acetoxy-2-(2-methylhydrazineyl)-2-oxoethyl)phenyl)-2-methylpropanoate (Intermediate 69-32, 1.00 g, 3.10 mmol) in pyridine (12 mL) were added 4A molecular sieves (2 g) at room temperature. The reaction was stirred at 50° C. overnight and concentrated. The residue was diluted with ethyl acetate (60 mL), washed water, brine, dried over sodium sulfate, filtered, and concentrated. The residue was purified by automated flash chromatography (40 g silica gel column, eluting with 0-100% ethyl acetate in petroleum ether) to give the title compound (1.30 g, 56%) as a solid. LC-MS: MS (ESI): 671 m/z $[M+H]^+$, purity: 93% (254 nm), retention time: 2.37 minutes (LC-MS method 026).

Methyl (2R)-3-(3-((5-(5-((4-bromo-6,7-difluoro-1H-indol-5-yl)oxy)-2-fluorophenyl)-1-methyl-1H-1,2,4-triazol-3-yl)(hydroxy)methyl)phenyl)-2-methylpropanoate

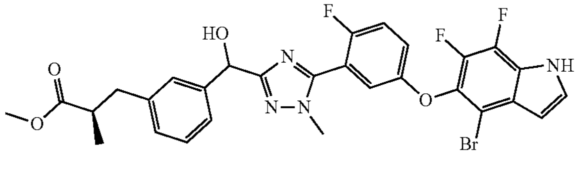 [SMILES: COC(=O)[C@H](C)Cc1cccc(C(O)c2nc(-c3cc(Oc4c(F)c(F)c5[nH]ccc5c4Br)ccc3F)n(C)n2)c1]

Step B: To a stirred solution of the product from Step A (1.30 g, 1.94 mmol) in methanol (20 mL) and dichloromethane (4 mL) was added under nitrogen acetyl chloride (0.14 mL, 1.94 mmol). The reaction was stirred at room temperature for 1 hour and concentrated in vacuo to provide the title compound (1.15 g, 94%) as yellow oil. LC-MS: MS (ESI): 629 m/z $[M+H]^+$, purity: 98% (254 nm), retention time: 2.20 minutes (LC-MS method 026).

Methyl (R)-3-(3-(5-(5-((4-bromo-6,7-difluoro-1H-indol-5-yl)oxy)-2-fluorophenyl)-1-methyl-1H-1,2,4-triazole-3-carbonyl)phenyl)-2-methylpropanoate

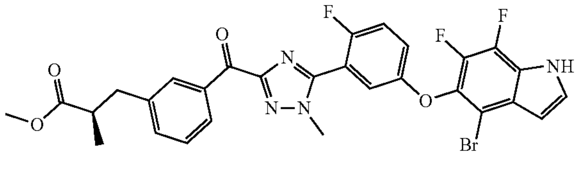 [SMILES: COC(=O)[C@H](C)Cc1cccc(C(=O)c2nc(-c3cc(Oc4c(F)c(F)c5[nH]ccc5c4Br)ccc3F)n(C)n2)c1]

Step C: To a stirred solution of the product from Step B (1.15 g, 1.83 mmol) in dichloromethane (30 mL) was added Dess-Martin periodinane (1550 mg, 3.65 mmol). The reaction was stirred at room temperature for 1 hour, then diluted with 30 mL of water, and extracted with dichloromethane (3×30 mL). The combined organic extracts were washed with brine, dried over sodium sulfate, filtered, and concentrated. The residue was purified by automated silica gel column chromatography (eluting with 0-70% of ethyl acetate in petroleum ether) to give the title compound (800 mg, 70%) as a brown solid. LC-MS: MS (ESI): 627 m/z $[M+H]^+$, purity: 90% (254 nm), retention time: 2.40 minutes (LC-MS method 026).

Isopropyl (2R)-3-(3-((5-(5-((4-bromo-6,7-difluoro-1H-indol-5-yl)oxy)-2-fluorophenyl)-1-methyl-1H-1,2,4-triazol-3-yl)((2,2-difluoro-4-((2-hydroxyethyl)sulfonyl)butyl)amino)methyl)phenyl)-2-methylpropanoate

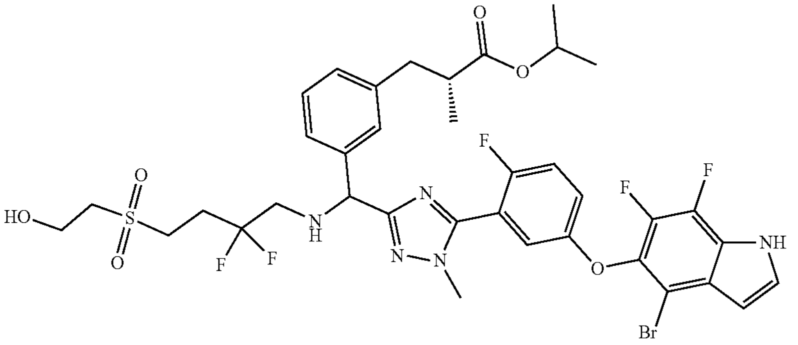 [SMILES: CC(C)OC(=O)[C@H](C)Cc1cccc(C(NCC(F)(F)CCS(=O)(=O)CCO)c2nc(-c3cc(Oc4c(F)c(F)c5[nH]ccc5c4Br)ccc3F)n(C)n2)c1]

Step D: A mixture of the product from Step C (1.85 g, 2.95 mmol), 2-((4-amino-3,3-difluorobutyl)sulfonyl)ethan-1-ol (Intermediate 148-1, 705 mg, 3.24 mmol) and titanium isopropoxide (2.6 mL, 8.85 mmol) in toluene (10 mL) was stirred at 120° C. for 16 hours and concentrated. The residue was dissolved in methanol (30 mL), treated with sodium cyanoborohydride (926 mg, 14.7 mmol), and stirred at room temperature for another hour. The mixture was quenched with saturated aqueous sodium bicarbonate (30 mL) and extracted with ethyl acetate (100 mL×3). The combined organic extracts were washed with brine, dried over sodium sulfate, filtered, and concentrated. The residue was purified by automated flash chromatography (40 g silica gel column, eluting with 0-80% ethyl acetate in petroleum ether) to give the title compound (1.65 g, 65%) as a solid. LC-MS: MS (ESI): 856 m/z $[M+H]^+$, purity: 80% (254 nm), retention time: 2.00 minutes (LC-MS method 026).

Compound 380. (2R)-2-Methyl-3-[3-(9,9,21,22,28-pentafluoro-3-methyl-12,12-dioxo-24-oxa-12λ6-thia-3,4,7,19,30-pentazapentacyclo[23.3.1.12,5.015,23.016,20]triaconta-1(29),2(30),4,15,17,20,22,25,27-nonaen-6-yl)phenyl] propanoic Acid

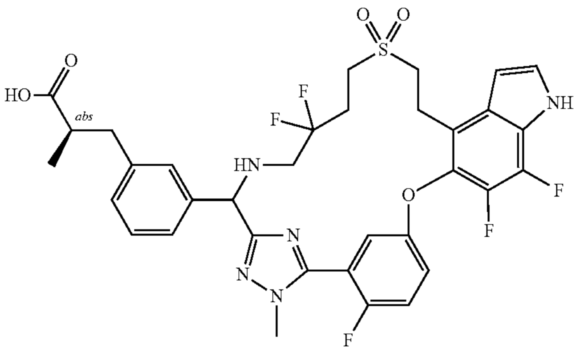 [SMILES: C[C@H](Cc1cccc(C2NCC(F)(F)CCS(=O)(=O)CCc3c(c(F)c(F)c4[nH]ccc34)Oc3ccc(F)c(c3)-c3nc2nn3C)c1)C(=O)O]

Exchanging methyl (2R)-3-(3-(2-(5-(5-((4-bromo-6-fluoro-1H-indol-5-yl)oxy)-2-fluorophenyl)-1-methyl-1H-1,2,4-triazol-3-yl)-7-((2-hydroxyethyl)sulfonyl)-6,6-dimethylheptan-2-yl)phenyl)-2-methylpropanoate (Step A product of Example 6) with the above Step D product (1.65 g, 1.93 mmol) in Step B of Example 6, the reaction procedure sequence, Step B, C of Example 6, followed by Step B of Example 301, then Step F of Example 6, was followed to afford the title compound (25 mg) as a white solid. LC-MS: MS (ESI): 718 m/z $[M+H]^+$, purity: >99% (214 nm), retention time: 1.87 minutes (LC-MS method 026). $^1H$ NMR (400 MHz, $CD_3OD$) δ 7.54-7.33 (m, 3H), 7.20 (s, 1H), 7.17-7.13 (m, 1H), 7.06-7.01 (m, 2H), 6.84-6.80 (m, 1H), 6.79-6.75 (m, 1H), 4.98 (s, 1H), 3.78 (d, J=2.4 Hz, 3H), 3.59-3.35 (m, 5H), 3.11-3.00 (m, 2H), 2.95-2.77 (m, 1H), 2.68-2.43 (m, 5H), 1.00 (d, J=6.8 Hz, 0.5H), 0.97 (d, J=6.8 Hz, 0.5H) ppm (1:1 mixture of two diastereomers).

Example 381. Diastereomer 1 and 2 of (2R)-2-methyl-3-[3-(21,22,28-trifluoro-3-methyl-13,13-dioxo-10,24-dioxa-13λ6-thia-3,4,7,19,30-pentaza-pentacyclo[23.3.1.12,5.015,23.016,20]triaconta-1(29),2(30),4,15,17,20,22,25,27-nonaen-6-yl)phenyl]propanoic Acid

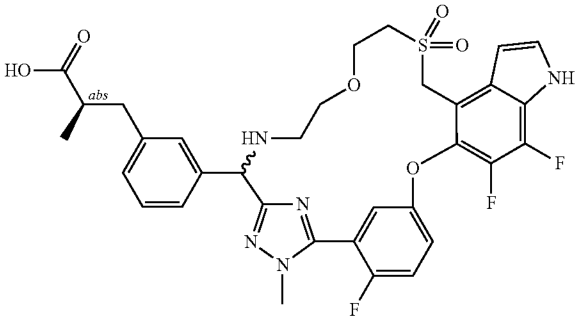 [SMILES: C[C@H](Cc1cccc(C2NCCOCCS(=O)(=O)Cc3c(c(F)c(F)c4[nH]ccc34)Oc3ccc(F)c(c3)-c3nc2nn3C)c1)C(=O)O]

Methyl (R)-3-(3-(5-(5-((6,7-difluoro-4-(hydroxymethyl)-1H-indol-5-yl)oxy)-2-fluorophenyl)-1-methyl-1H-1,2,4-triazole-3-carbonyl)phenyl)-2-methylpropanoate

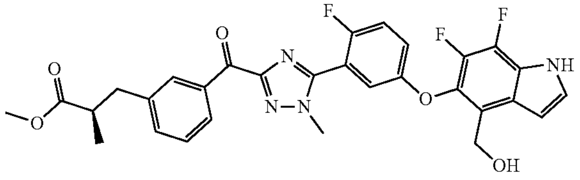 [SMILES: COC(=O)[C@H](C)Cc1cccc(C(=O)c2nc(-c3cc(Oc4c(F)c(F)c5[nH]ccc5c4CO)ccc3F)n(C)n2)c1]

Step A: A mixture of methyl (R)-3-(3-(5-(5-((4-bromo-6,7-difluoro-1H-indol-5-yl)oxy)-2-fluorophenyl)-1-methyl-1H-1,2,4-triazole-3-carbonyl)phenyl)-2-methylpropanoate (Step C product of Example 380, 2.20 g, 3.51 mmol), Xphos Pd G2 (275 mg, 0.351 mmol) and (tributylstannyl)methanol (3378 mg, 10.5 mmol) in 1,4-dioxane (50 mL) was stirred at 80° C. overnight under nitrogen atmosphere, then concentrated. The residue was purified by automated flash chromatography (40 g silica gel column, eluting with 0-83% ethyl acetate in petroleum ether) to give the title compound (1.60 g, 79%) as a white solid. LC-MS: MS (ESI): 579 m/z $[M+H]^+$, purity: 95% (214 nm), retention time: 2.07 minutes (LC-MS method 026).

Methyl (R)-3-(3-(5-(5-((4-((acetylthio)methyl)-6,7-difluoro-1H-indol-5-yl)oxy)-2-fluorophenyl)-1-methyl-1H-1,2,4-triazole-3-carbonyl)phenyl)-2-methylpropanoate

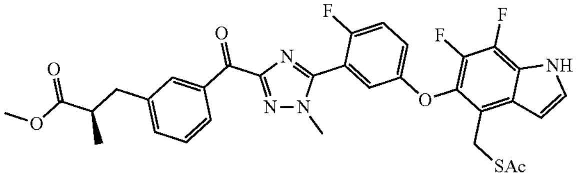

Step B. To a stirred solution of triphenylphosphine (1360 mg, 5.18 mmol) in tetrahydrofuran (60 mL) was added diisopropyl azodicarboxylate (1 mL, 5.18 mmol) dropwise at 0° C. under argon. The mixture was stirred at 0° C. for 15 min (formation of a white solid), then treated with a solution of the product from Step A (1 g, 1.72 mmol) and thioacetic acid (0.38 mL, 5.18 mmol) in tetrahydrofuran (20 mL). The reaction was stirred at 0° C. for 1 hour, warmed to room temperature for 1 hour, quenched with water (100 mL), and extracted with ethyl acetate (3×100 mL). The combined organic extracts were washed with brine, dried over sodium sulfate, filtered, and concentrated. The residue was purified by flash chromatography (40 g silica gel column, eluting with 0-20% ethyl acetate in petroleum ether) to give the title compound (920 mg, 91%) as a colorless oil. LC-MS: MS (ESI): 637 m/z $[M+H]^+$, purity: 95% (214 nm), retention time: 2.08 minutes (LC-MS method 017).

Ethyl (R)-3-(3-(5-(5-((4-(11,11-dimethyl-9-oxo-5,10-dioxa-2-thia-8-azadodecyl)-6,7-difluoro-1H-indol-5-yl)oxy)-2-fluorophenyl)-1-methyl-1H-1,2,4-triazole-3-carbonyl)phenyl)-2-methylpropanoate

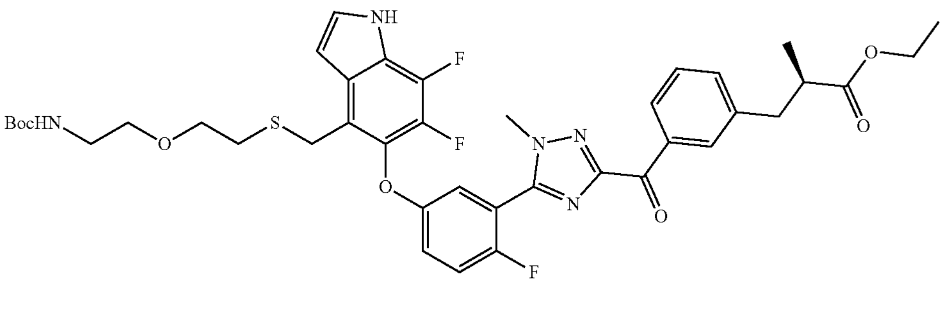 [SMILES: CCOC(=O)[C@H](C)Cc1cccc(C(=O)c2nc(-c3cc(Oc4c(F)c(F)c5[nH]ccc5c4CSCCOCCNC(=O)OC(C)(C)C)ccc3F)n(C)n2)c1]

Step C. To a stirred solution of the product from Step B (500 mg, 0.785 mmol) in ethanol (40 mL) was added tert-butyl N-[2-(2-bromoethoxy)ethyl]carbamate (274 mg, 1.02 mmol) and sodium ethoxide (53 mg, 0.785 mmol). The reaction was stirred at room temperature for 1 hour. The mixture was quenched with 0.5 M hydrochloric acid (10 mL) and extracted with ethyl acetate (3×80 mL). The combined organic phases were washed with brine, dried over sodium sulfate, filtered, and concentrated. The residue was purified by flash chromatography (eluting with 0-70% of Ethyl acetate in petroleum ether) to give the title compound (500 mg, 80%) as colorless oil. LC-MS: MS (ESI): 796 m/z $[M+H]^+$, purity: 75% (254 nm), retention time: 2.15 minutes (LC-MS method 017).

Ethyl (R)-3-(3-(5-(5-((4-(((2-(2-((tert-butoxycarbonyl)amino)ethoxy)ethyl)sulfonyl)methyl)-6,7-difluoro-1H-indol-5-yl)oxy)-2-fluorophenyl)-1-methyl-1H-1,2,4-triazole-3-carbonyl)phenyl)-2-methylpropanoate

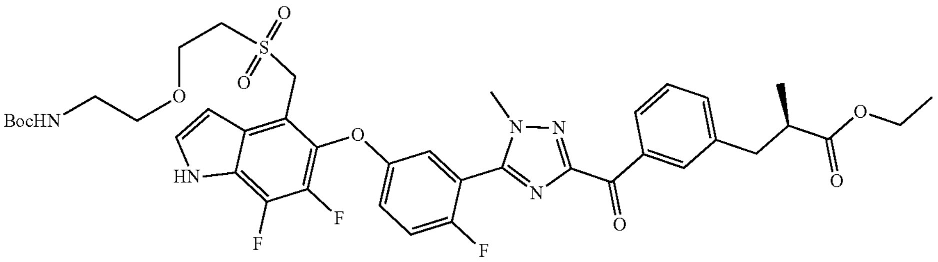 [SMILES: CCOC(=O)[C@H](C)Cc1cccc(C(=O)c2nc(-c3cc(Oc4c(F)c(F)c5[nH]ccc5c4CS(=O)(=O)CCOCCNC(=O)OC(C)(C)C)ccc3F)n(C)n2)c1]

Step D. To a stirred solution of the product from Step C (500 mg, 0.628 mmol) in dichloromethane (10 mL) was added 3-chloroperoxybenzoic acid (434 mg, 2.51 mmol). The reaction was stirred at room temperature for 6 hours, quenched with water (20 mL), and diluted with ethyl acetate (100 ml). The separated organic layer was washed with water, brine, dried over sodium sulfate, filtered, and concentrated. The residue was purified by automated flash chromatography (eluting with 0-50% of ethyl acetate in petroleum ether) to give the title compound (330 mg, 63%) as a solid. LC-MS: MS (ESI): 828 m/z $[M+H]^+$, purity: 75% (254 nm), retention time: 2.04 minutes (LC-MS method 41).

Ethyl (R)-3-(3-(5-(5-((4-(((2-(2-aminoethoxy)ethyl)sulfonyl)methyl)-6,7-difluoro-1H-indol-5-yl)oxy)-2-fluorophenyl)-1-methyl-1H-1,2,4-triazole-3-carbonyl)phenyl)-2-methylpropanoate

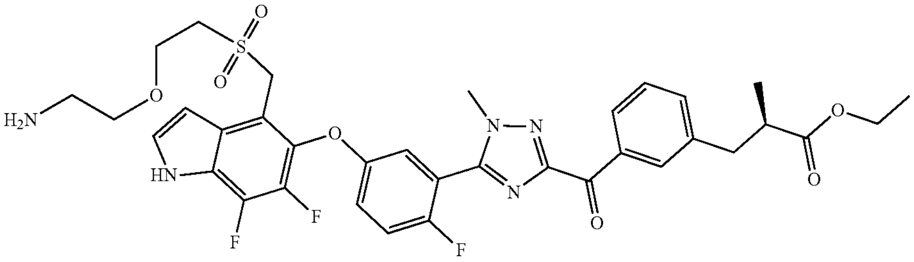 [SMILES: CCOC(=O)[C@H](C)Cc1cccc(C(=O)c2nc(-c3cc(Oc4c(F)c(F)c5[nH]ccc5c4CS(=O)(=O)CCOCCN)ccc3F)n(C)n2)c1]

Step E. To a stirred solution of the product from Step D (334 mg, 0.403 mmol) in dichloromethane (6 mL) was added trifluoroacetic acid (3 mL). The reaction was stirred at room temperature for 2 hours and concentrated. The residue was diluted with ethyl acetate (50 mL), washed with saturated aqueous sodium bicarbonate, brine, dried over sodium sulfate, filtered, and concentrated. The crude was purified by automated flash chromatography (eluting with 0-50% ethyl acetate in petroleum ether) to give the title compound (225 mg, 77%) as a solid. LC-MS: MS (ESI): 728 m/z $[M+H]^+$, purity: 62% (254 nm), retention time: 1.56 minutes (LC-MS method 41).

Ethyl (2R)-2-methyl-3-[3-(21,22,28-trifluoro-3-methyl-13,13-dioxo-10,24-dioxa-13 6-thia-3,4,7,19,30-pentazapentacyclo[23.3.1.12,5.015,23.016,20]triaconta-1(29),2(30),4,15,17,20,22,25,27-nonaen-6-yl)phenyl]propanoate

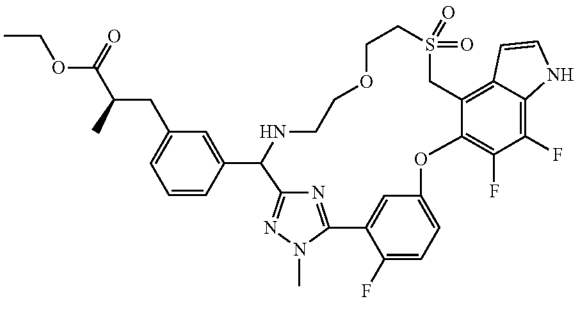 [SMILES: CCOC(=O)[C@H](C)Cc1cccc(C2NCCOCCS(=O)(=O)Cc3c(c(F)c(F)c4[nH]ccc34)Oc3ccc(F)c(c3)-c3nc2nn3C)c1]

Step F: A mixture of the product from Step E (175 mg, 0.152 mmol) and tetraethyl titanate (139 mg, 0.608 mmol) in toluene (20 mL) was stirred at 120° C. for 16 hours and concentrated. The residue was redissolved in ethanol (20 ml) and sodium cyanoborohydride (48 mg, 0.760 mmol) was added. The reaction was stirred at room temperature for another 1 hour, quenched with saturated aqueous sodium bicarbonate (20 mL), and extracted with ethyl acetate (3×20 mL). The combined organic extracts were washed with brine, dried over sodium sulfate, filtered, and concentrated. The residue was purified by automated flash chromatography (12 g silica gel column, eluting with 0-40% ethyl acetate in methanol) to give the title compound (38 mg, 35%) as a solid. LC-MS: MS (ESI): 712 m/z $[M+H]^+$, purity: 62% (254 nm), retention time: 1.68 minutes (LC-MS method 026).

Compound 381A and Compound 381B. Diastereomer 1 and 2 of (2R)-2-methyl-3-[3-(21,22,28-trifluoro-3-methyl-13,13-dioxo-10,24-dioxa-13 6-thia-3,4,7,19,30-pentazapentacyclo[23.3.1.12,5.015,23.016,20]triaconta-1(29),2(30),4,15,17,20,22,25,27-nonaen-6-yl)phenyl]propanoic Acid

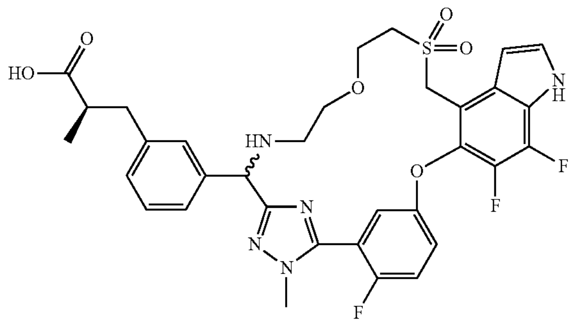 [SMILES: C[C@H](Cc1cccc(C2NCCOCCS(=O)(=O)Cc3c(c(F)c(F)c4[nH]ccc34)Oc3ccc(F)c(c3)-c3nc2nn3C)c1)C(=O)O]

Step G. A mixture of the product from Step F (27 mg, 0.0386 mmol) and lithium hydroxide monohydrate (16 mg, 0.386 mmol) in tetrahydrofuran (2 mL) and water (1 mL) was stirred at room temperature overnight, then acidified with 1.0 M hydrochloric acid to pH ~5, and extracted with ethyl acetate (2×30 mL). The combined organic phases were washed with brine, dried over sodium sulfate, filtered, and concentrated. The residue was purified by prep-HPLC. The first eluent, Diastereomer 1 (1.2 mg, 4.6%, white solid), was designated as Compound 381A. The second eluent, Diastereomer 2 (0.20 mg, 0.7%, white solid), was designated as Compound 381B.

Compound 381A: LC-MS: MS (ESI): 684 m/z $[M+H]^+$, purity: 90% (254 nm), retention time: 1.26 minutes (LC-MS method 26).

Compound 381B: LC-MS: MS (ESI): 684 m/z $[M+H]^+$, purity: >99% (254 nm), retention time: 1.31 minutes (LC-MS method 26).

Example 382. (2S)-2-Methyl-3-[3-[(6R)-21,22,28-trifluoro-3,6,10,10-tetramethyl-12,12-dioxo-24-oxa-12λ6-thia-3,4,18,19,30-pentazapentacyclo[23.3.1.12,5.015,23.016,20]triaconta-1(29),2(30),4,15,17,20,22,25,27-nonaen-6-yl]phenyl]propanoic Acid

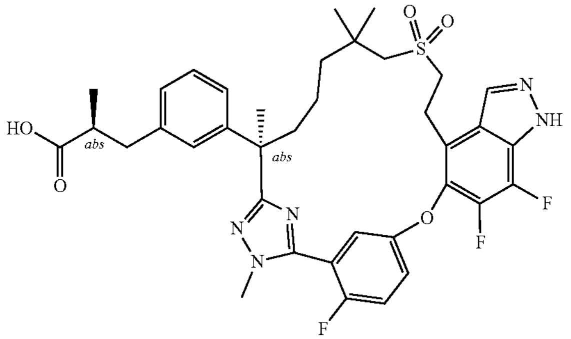 [SMILES: C[C@@H](Cc1cccc([C@@]2(C)CCCC(C)(C)CS(=O)(=O)CCc3c(c(F)c(F)c4[nH]ncc34)Oc3ccc(F)c(c3)-c3nc2nn3C)c1)C(=O)O]

Exchanging methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (S)-3-(3-((R)-7-((2-hydroxyethyl)sulfonyl)-2,6,6-trimethyl-1-(2-methylhydrazineyl)-1-oxoheptan-2-yl)phenyl)-2-methylpropanoate (Intermediate 137-1, 0.22 g, 0.46 mmol), and methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1-(tetrahydro-2H-pyran-2-yl)-1H-indazol-5-yl)oxy)-2-fluorobenzimidothioate (210 mg, 0.42 mmol) in Step A of Example 6, the reaction procedure sequence, Steps A to D, and step F, described for Example 6 was followed to afford the title compound (Compound 382, 9.9 mg) as a white solid. LC-MS: MS (ESI): 724 m/z $[M+H]^+$, purity: 90% (214 nm), retention time: 6.50 minutes (LC-MS method 26). $^1H$ NMR (400 MHz, $CD_3OD$) δ 8.32 (brs, 1H), 7.50-7.45 (m, 1H), 7.40 (t, J=7.2 Hz, 1H), 7.20-7.10 (m, 2H), 7.03-6.94 (m, 3H), 3.83 (d, J=1.6 Hz, 3H), 3.50-3.40 (m, 2H), 3.41-3.31 (m, 2H), 3.02 (d, J=11.2 Hz, 1H), 2.94-2.88 (m, 1H), 2.73 (d, J=11.2 Hz, 1H), 2.63-2.53 (m, 2H), 2.18-2.08 (m, 1H), 1.85-1.75 (m, 1H), 1.64 (s, 3H), 1.60-1.52 (m, 1H), 1.42-1.32 (m, 1H), 1.26-1.18 (m, 1H), 1.10-0.92 (m, 10H) ppm.

Example 383. (2S)-2-Methyl-3-[3-[(6R)-21,22,28-trifluoro-3,6,10,10-tetramethyl-12,12-dioxo-24-oxa-12λ6-thia-3,4,17,19,30-pentazapentacyclo[23.3.1.12,5.015,23.016,20]triaconta-1(29),2(30),4,15,17,20,22,25,27-nonaen-6-yl]phenyl]propanoic acid

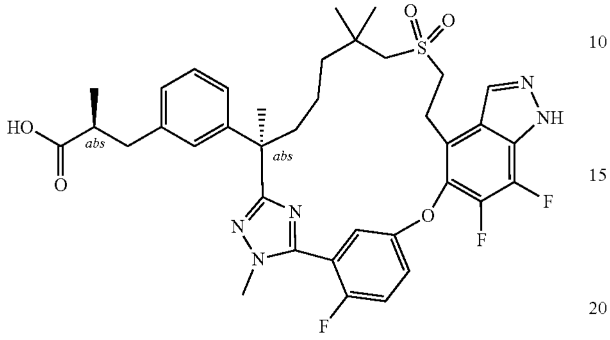

Exchanging methyl 5-((4-bromo-6-fluoro-1H-indol-5-yl)oxy)-2-fluorobenzimidothioate hydroiodide (Intermediate 14-1) with methyl 5-((4-bromo-6,7-difluoro-1-(tetrahydro-2H-pyran-2-yl)-1H-benzo[d]imidazol-5-yl)oxy)-2-fluorobenzimidothioate (Intermediate 150-11, 2.20 g, 4.40 mmol), and methyl (2R)-3-(3-(7-((2-hydroxyethyl)sulfonyl)-2,6,6-trimethyl-1-(2-methylhydrazineyl)-1-oxoheptan-2-yl)phenyl)-2-methylpropanoate (Intermediate 69) with methyl (2S)-3-[3-[(1R)-6-(2-hydroxyethylsulfonyl)-1,5,5-trimethyl-1-(methylaminocarbamoyl)hexyl]phenyl]-2-methyl-propanoate (Intermediate 137-1, 2131 mg, 4.40 mmol) in Step A of Example 6, the reaction procedure sequence, Step A, B, C, D of Example 6, followed by Step B of Example 99 (to deprotect THP group), then Step F of Example 6, was followed to give the title compound (Compound 383, 66 mg) as a white solid. LC-MS: MS (ESI): 724 m/z $[M+H]^+$, purity: 96% (214 nm), retention time: 2.21 minutes (LC-MS method 32). $^1H$ NMR (400 MHz, $CD_3OD$): δ 8.28 (s, 1H), 7.47-7.40 (m, 2H), 7.26 (dd, J=5.2, 2.4 Hz, 1H), 7.14 (t, J=7.6 Hz, 1H), 7.00-6.95 (m, 3H), 3.83 (d, J=2.0 Hz, 3H), 3.46-3.33 (m, 4H), 3.06 (d, J=14.0 Hz, 1H), 2.94-2.86 (m, 1H), 2.81 (d, J=13.6 Hz, 1H), 2.62-2.54 (m, 2H), 2.19-2.11 (m, 1H), 1.84-1.75 (m, 1H), 1.65 (s, 3H), 1.62-1.58 (m, 1H), 1.41-1.35 (m, 1H), 1.30-1.24 (m, 1H), 1.07 (s, 3H), 1.05-1.01 (m, 7H) ppm.

Example 384. (2R)—N-(4,5-Dimethylisoxazol-3-yl)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propenamide

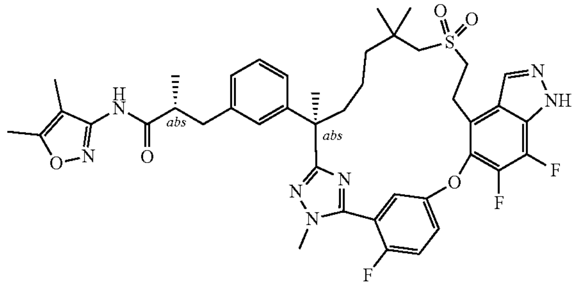 [SMILES: Cc1onc(NC(=O)[C@H](C)Cc2cccc([C@@]3(C)CCCC(C)(C)CS(=O)(=O)CCc4c(c(F)c(F)c5[nH]ncc45)Oc4ccc(F)c(c4)-c4nc3nn4C)c2)c1C]

To a stirred solution of (2R)-2-methyl-3-[3-[(6R)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]propanoic acid (Example 200, 100 mg, 0.138 mmol) and 4,5-dimethylisoxazol-3-amine (23 mg, 0.208 mmol) in pyridine (5 mL) was added phosphorus oxychloride (0.026 mL, 0.277 mmol). The reaction was stirred at room temperature for 4 hours, quenched with water (60 mL) and extracted with dichloromethane (3×60 mL). The combined organic extracts were washed with saturated aqueous sodium bicarbonate, brine, dried over sodium sulfate, filtered, and concentrated. The residue was purified by automated flash chromatography (12 g silica gel column, eluting with 0-60% ethyl acetate in petroleum ether) to give the title compound (Compound 384, 60 mg, 53%) as a white solid. LC-MS: MS (ESI): 817 m/z $[M+H]^+$; purity: >99% (214 nm); retention time: 2.01 minutes (LC-MS method 42). $^1H$ NMR (500 MHz, DMSO-$d_6$) δ 12.00 (s, 1H), 10.14 (s, 1H), 7.53 (t, J=7.2 Hz, 1H), 7.45-7.42 (m, 1H), 7.34-7.31 (m, 2H), 7.14-7.10 (m, 2H), 7.00 (d, J=7.6 Hz, 1H), 6.89 (d, J=8.0 Hz, 1H), 6.60-6.59 (m, 1H), 3.77 (s, 3H), 3.18-3.10 (m, 3H), 3.01-2.97 (m, 1H), 2.88-2.83 (m, 3H), 2.26 (s, 3H), 2.15-2.02 (m, 2H), 1.73 (s, 2H), 1.64-1.61 (m, 6H), 1.30-1.18 (m, 4H), 1.06-1.04 (m, 3H), 1.00-0.98 (m, 6H) ppm.

Example 385. Diastereomers 1 and 2 of (2R)-3-[3-[(6R)-14-amino-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,15,17,20,22,25,27-nonaen-6-yl]phenyl]-2-methyl-propanamide

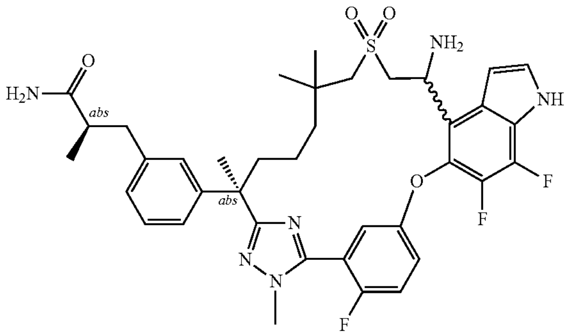 [SMILES: C[C@H](Cc1cccc([C@@]2(C)CCCC(C)(C)CS(=O)(=O)CC(N)c3c(c(F)c(F)c4[nH]ccc34)Oc3ccc(F)c(c3)-c3nc2nn3C)c1)C(N)=O]

Exchanging dimethylamine with ammonium chloride (2.0 eq, 52 mg, 0.97 mmol) and triethylamine (3.0 eq, 0.20 mL, 1.46 mmol) in Step B of Example 367, 2M dimethylamine in tetrahydrofuran with 25-28% ammonia in water in Step C of Example 367, the reaction procedure sequence (Steps B and C) described for Example 367 was followed to convert methyl (2R)-2-methyl-3-[3-[(6R,13E)-21,22,28-trifluoro-3,6,10,10-tetramethyl-12,12-dioxo-24-oxa-12λ6-thia-3,4,19,30-tetrazapentacyclo[23.3.1.12,5.015,23.016,20]triaconta-1(29),2(30),4,13,15,17,20,22,25,27-decaen-6-yl]phenyl]propanoate (Step C product of Example 200, 100 mg) to the title compounds. The first eluent was designated as Compound 368A (25 mg, white solid) and the second eluent was designated as Compound 385B (20 mg, white solid).

Compound 385A. LC-MS: MS (ESI): 737 m/z $[M+H]^+$, purity: >99% (214 nm), retention time: 1.46 minutes (LC-MS method 47). $^1H$ NMR (400 MHz, $CD_3OD$) δ 7.63-7.59 (m, 1H), 7.46-7.40 (m, 2H), 7.20-7.17 (m, 1H), 7.13-7.06

(m, 2H), 6.99-6.96 (m, 2H), 6.81 (s, 1H), 5.34 (s, 1H), 3.83-3.67 (m, 5H), 2.88-2.81 (m, 2H), 2.70-2.67 (m, 1H), 2.58-2.51 (m, 2H), 2.20-2.14 (m, 1H), 1.90-1.80 (m, 1H), 1.63 (s, 3H), 1.43-1.27 (m, 2H), 1.22-1.16 (m, 1H), 1.15-1.04 (m, 6H), 0.97 (s, 3H), 0.82 (m, 1H) ppm.

Compound 385B. LC-MS: MS (ESI): 737 m/z $[M+H]^+$, purity: >99% (214 nm), retention time: 1.48 minutes (LC-MS method 47). $^1H$ NMR (400 MHz, $CD_3OD$). $^1H$ NMR (400 MHz, $CD_3OD$) δ 7.56-7.50 (m, 1H), 7.43-7.35 (m, 2H), 7.13-7.05 (m, 2H), 7.00-6.95 (m, 2H), 6.91 (d, J=7.8 Hz, 1H), 6.81 (t, J=3.2 Hz, 1H), 5.08-5.02 (m, 1H), 3.80 (s, 3H), 3.64 (dd, J=13.6, 6.0 Hz, 1H), 3.54 (dd, J=13.6, 7.8 Hz, 1H), 3.08 (d, J=14.0 Hz, 1H), 2.88-2.80 (m, 2H), 2.55-2.46 (m, 2H), 2.13 (td, J=13.2, 3.6 Hz, 1H), 1.78 (td, J=12.4, 4.8 Hz, 1H), 1.70-1.57 (m, 4H), 1.42-1.34 (m, 1H), 1.18-1.10 (m, 1H), 1.09-0.94 (m, 10H) ppm.

Biological Assays

Example 386. Aggregation Analysis Using Differential Static Light Scattering (DSLS)

Purified recombinant NBD1 was produced using previously described methods (A. Schmidt, J. L. Mendoza, P. J. Thomas (2011) Biochemical and Biophysical Approaches to Probe CFTR Structure (365-376) M. D. Amaral, K. Kunzelmann (eds.), Cystic Fibrosis, Methods in Molecular Biology 741, Springer Science+Business Media). The effect of test compounds on thermal stability of NBD1 was evaluated by differential static light scattering (DSLS) using the Harbinger Stargazer-384 instrument (Epiphyte Three, Toronto, Canada). Test compounds were dissolved and diluted to desired concentrations in 100% DMSO. The compounds or DMSO controls (100 nL) were stamped into wells of a 385-well low volume optical plate (Corning Inc., Corning, NY) using the Echo 555 acoustic liquid handler (Labcyte Inc., San Jose, CA).

NBD1 protein was diluted to 0.2 mg/ml in S200 buffer (50 mM Tris-HCl, 150 mM NaCl, 5 mM $MgCl_2$, 2 mM ATP, 2 mM DTT, pH7.6) containing 1% glycerol. 10 uL of protein solution was aliquoted into the 384-well plate harboring the test compounds and 10 uL mineral oil was overlaid onto the protein solution, using the epMotion robotic liquid handler (Eppendorf North America, Hauppauge, NY). After placing into the Stargazer instrument, the plate was heated at 1° C. per minute to 70° C. Images were captured from 25° C. to 70° C. every 0.5° C. At the end of the experiment run, instrument software integrated image files and analyzed data automatically. A linear regression curve was generated for each well, representing the increase in light scattering over time. A temperature of aggregation ($T_{agg}$) was calculated based on the inflection point of the curve. To better compare data across experiments the average $T_{agg}$ for DMSO control wells was calculated and subtracted from values for wells containing compounds to obtain a "$\Delta T_{agg}$" value. These $\Delta T_{agg}$ values reflect stabilizing efficacy of the compounds. As set forth in Table 2 below, an $\Delta T_{agg}$ value less than or equal to 5° C. is marked "A"; a value above 5° C. and less than or equal to 10° C. is marked "B"; a value greater than 10° C. and less than or equal to 25° C. is marked "C".

Example 387. TECC24 AUC Fold Over DMSO @10 μM

The effects of a test agent on CFTR-mediated transepithelial chloride transport is measured using TECC24 recording analysis. Test agents are solubilized in DMSO. Solubilized test agents are mixed with incubation medium containing DMEM/F12, Ultroser G (2%; Crescent Chemical, catalog #67042), Hyclone Fetal Clone II (2%; GE Healthcare, catalog #SH30066.02), bovine brain extract (0.25%; Lonza, catalog #CC-4098), insulin (2.5 μg/mL), IL-13 (10 ng/mL), hydrocortisone (20 nM), transferrin (2.5 μg/mL), triiodothyronine (500 nM), ethanolamine (250 nM), epinephrine (1.5 μM), phosphoethanolamine (250 nM), and retinoic acid (10 nM). Primary human bronchial epithelial cells from a ΔF508 homozygous CF donor (CF-HBE cells; from University of North Carolina Cystic Fibrosis Tissue Procurement Center), grown on Transwell HTS 24-well cell culture inserts (Costar, catalog #3378), are exposed to test agents or controls dissolved in incubation medium. The CF-HBE cells are cultured at 36.5° C. for 48 hours before TECC24 recordings are performed in the presence or absence of test agent, a positive control or vehicle (DMSO).

Following incubation, the transwell cell culture inserts containing the test agent or control-treated CF-HBE cells are loaded onto a TECC24 apparatus (TECC v7 or MTECC v2; EP Design) to record the transepithelial voltage (VT) and resistance (TEER) using 4 AgCl electrodes per well configured in current-clamp mode. The apical and basolateral bath solutions both contain (in mM) 140 NaCl, 5 KCl, 2 $CaCl_2$, 1 $MgCl_2$, 10 Hepes, and 10 glucose (adjusted to pH 7.4 with NaOH). To inhibit basal Na+ absorption, the ENaC inhibitor benzamil (10 μM) is added to the bath. Then, the adenylate cyclase activator, forskolin (10 μM), is added to the bath to activate CFTR. The forskolin-stimulated Cl— transport is halted by addition of CFTR inhibitor-172 (20 μM) to the bath at the end of the experiment to confirm specificity. VT and TEER recordings are digitally acquired at routine intervals using TECC or MTECC software (EP Design). VT and TEER are transformed into equivalent transepithelial Cl— current (IEQ), and the Area Under the Curve (AUC) of the IEQ time course between forskolin and CFTR inhibitor-172 addition is generated using Excel (Microsoft). Efficacy is expressed as the ratio of the test agent AUC divided by vehicle AUC. EC50s based on AUC are generated using the non-linear regression log(agonist) vs. response function in Prism software (Graphpad) with HillSlope fixed=1.

If a test agent increases the AUC of the forskolin-stimulated IEQ relative to vehicle in CF-HBE cells, and this increase is inhibited by CFTR inhibitor-172, then the test agent is considered a CFTR corrector. TECC assay efficacy is expressed as the ratio of the test agent AUC divided by DMSO vehicle AUC. As set forth in Table 2 below, a TECC value less than 12 is marked "A"; a value between 12-20 is marked "B"; a value between 20 and 80 is marked "C". As set forth in Table 2 below, a DSLS value less than 12 is marked "A"; a value between 12-20 is marked "B"; a value between 20 and 80 is marked "C".

TABLE 2

| Compound No. | TECC (AUC, 10 μM) | DSLS 3D (100 μM ΔT) |
|---|---|---|
| 1A | C | C |
| 1B | A | A |
| 2A | B | B |
| 2B | A | A |
| 3 | B | C |
| 4A | C | C |
| 4B | A | A |
| 5A | B | C |
| 5B | B | B |
| 6A | B | C |

TABLE 2-continued

| Compound No. | TECC (AUC, 10 µM) | DSLS 3D (100 µM ΔT) |
|---|---|---|
| 6B | C | A |
| 7 | B | C |
| 8A | B | C |
| 8B | A | A |
| 9A | A | C |
| 9B | A | A |
| 10A | A | C |
| 10B | A | B |
| 11A | C | C |
| 11B | A | A |
| 12A | B | C |
| 12B | C | A |
| 13A | B | C |
| 13B | C | A |
| 14 | B | C |
| 15A | A | C |
| 15B | A | B |
| 16A | A | A |
| 16B | A | C |
| 17A | A | B |
| 17B | A | C |
| 18A | A | B |
| 18B | B | C |
| 19A | C | C |
| 19B | A | A |
| 20A | C | C |
| 20B | A | A |
| 21 | C | C |
| 22A | A | A |
| 22B | B | A |
| 22C | C | C |
| 23 | B | C |
| 24A | A | B |
| 24B | A | C |
| 25 | A | C |
| 26 | C | C |
| 27A | A | B |
| 27B | C | C |
| 28A | C | C |
| 28B | B | A |
| 29A | C | C |
| 29B | A | A |
| 30A | C | C |
| 30B | B | B |
| 30C | C | B |
| 30D | A | C |
| 31A | C | B |
| 31B | B | A |
| 31C | C | C |
| 31D | C | A |
| 32A | A | A |
| 32B | C | C |
| 33A | C | C |
| 33B | A | B |
| 34A | C | C |
| 34B | A | A |
| 35 | — | C |
| 36 | — | C |
| 37 | A | C |
| 38 | — | C |
| 39 | — | B |
| 40 | B | C |
| 41 | A | C |
| 42 | B | C |
| 43A | A | A |
| 43B | A | C |
| 44 | A | C |
| 45A | A | A |
| 45B | A | C |
| 46 | C | C |
| 47 | B | C |
| 48 | C | C |
| 49 | — | C |
| 50 | C | C |
| 51 | A | C |
| 52 | C | C |

TABLE 2-continued

| Compound No. | TECC (AUC, 10 µM) | DSLS 3D (100 µM ΔT) |
|---|---|---|
| 53 | A | A |
| 54A | C | C |
| 54B | A | B |
| 55A | A | C |
| 55B | A | B |
| 56 | A | C |
| 57 | C | B |
| 58 | B | C |
| 59 | C | C |
| 60 | A | A |
| 61 | B | C |
| 62 | C | C |
| 63A | C | B |
| 63B | C | C |
| 64 | B | C |
| 65A | A | B |
| 65B | A | C |
| 66 | B | C |
| 67A | B | C |
| 67B | B | C |
| 68 | B | C |
| 69 | A | C |
| 70 | A | C |
| 71 | A | C |
| 72A | A | C |
| 72B | A | A |
| 73A | A | C |
| 73B | B | A |
| 74 | A | C |
| 75 | A | C |
| 76 | A | C |
| 77 | A | C |
| 78 | A | B |
| 79A | C | C |
| 79B | A | B |
| 80 | A | B |
| 81 | A | A |
| 82 | A | C |
| 83 | A | B |
| 84A | B | B |
| 84B | A | A |
| 85 | A | A |
| 86A | A | A |
| 86B | A | B |
| 87A | A | B |
| 87B | A | C |
| 88 | — | A |
| 89A | — | C |
| 89B | — | A |
| 90A | — | C |
| 90B | — | A |
| 91A | A | C |
| 91B | A | A |
| 92 | A | A |
| 93 | A | A |
| 94 | A | A |
| 95A | A | A |
| 95B | A | C |
| 96A | A | C |
| 96B | A | A |
| 97A | A | C |
| 97B | A | A |
| 98A | B | C |
| 98B | C | C |
| 99 | A | A |
| 100A | A | C |
| 100B | A | A |
| 101A | A | A |
| 101B | A | B |
| 102A | A | A |
| 102B | B | B |
| 103 | A | C |
| 104 | C | C |
| 105 | A | B |
| 106 | A | C |
| 107 | A | C |

TABLE 2-continued

| Compound No. | TECC (AUC, 10 μM) | DSLS 3D (100 μM ΔT) |
|---|---|---|
| 108A | A | A |
| 108B | C | A |
| 109A | C | C |
| 109B | A | A |
| 110 | C | B |
| 111 | B | C |
| 112 | A | B |
| 113A | A | C |
| 113B | A | A |
| 114 | B | C |
| 115 | A | C |
| 116 | A | C |
| 117 | C | C |
| 118A | A | C |
| 118B | A | A |
| 119A | A | A |
| 119B | A | B |
| 120A | A | C |
| 120B | A | A |
| 121A | B | C |
| 121B | A | A |
| 122A | A | C |
| 122B | A | A |
| 123A | A | A |
| 123B | A | C |
| 124A | A | C |
| 124B | A | B |
| 125A | B | B |
| 125B | B | C |
| 126A | B | C |
| 126B | B | B |
| 127A | A | B |
| 127B | A | A |
| 128 | A | C |
| 129A | A | A |
| 129B | A | C |
| 130A | C | C |
| 130B | C | C |
| 131 | B | A |
| 132A | A | A |
| 132B | A | C |
| 133A | C | C |
| 133B | A | B |
| 134A | C | C |
| 134B | A | A |
| 135A | A | A |
| 135B | C | C |
| 136A | A | A |
| 136B | C | C |
| 137A | c | C |
| 137B | A | B |
| 138 | C | C |
| 139 | C | B |
| 140 | B | C |
| 141 | B | C |
| 142 | B | B |
| 143 | B | B |
| 144 | B | C |
| 145 | C | A |
| 146 | A | C |
| 147 | A | C |
| 148 | C | C |
| 149 | A | C |
| 150 | A | C |
| 151 | — | A |
| 152 | — | C |
| 153A | C | C |
| 153B | C | A |
| 153C | A | A |
| 154 | A | B |
| 155 | A | C |
| 156 | B | C |
| 157A | A | A |
| 157B | A | C |
| 158 | A | C |
| 159 | B | A |

TABLE 2-continued

| Compound No. | TECC (AUC, 10 μM) | DSLS 3D (100 μM ΔT) |
|---|---|---|
| 160 | A | C |
| 161 | — | A |
| 162 | — | A |
| 163 | A | A |
| 164 | A | A |
| 165 | C | B |
| 166A | B | C |
| 166B | A | A |
| 167 | A | C |
| 168 | B | C |
| 169A | A | C |
| 169B | A | A |
| 170 | A | A |
| 171A | A | A |
| 171B | A | C |
| 172 | A | B |
| 173 | C | B |
| 174 | A | C |
| 175 | A | C |
| 176 | B | C |
| 177 | C | B |
| 178 | C | C |
| 179A | A | B |
| 179B | A | A |
| 179C | C | C |
| 179D | A | A |
| 180A | B | C |
| 180B | A | A |
| 181A | A | B |
| 181B | A | A |
| 181C | A | A |
| 181D | A | C |
| 182 | A | — |
| 183A | A | A |
| 183B | A | C |
| 184 | A | B |
| 185 | B | C |
| 186 | B | B |
| 187 | A | B |
| 188 | B | B |
| 189 | B | B |
| 190 | B | C |
| 191 | B | C |
| 192 | C | C |
| 193 | C | B |
| 194 | B | A |
| 195A | C | C |
| 195B | C | C |
| 196A | A | C |
| 196B | A | A |
| 197 | C | C |
| 198 | C | C |
| 199 | C | C |
| 200 | C | C |
| 201 | B | C |
| 202 | C | C |
| 204 | C | C |
| 205 | A | B |
| 206A | C | C |
| 206B | A | B |
| 209A | A | B |
| 209B | C | C |
| 210A | C | — |
| 210B | A | — |
| 210C | B | — |
| 210D | C | — |
| 211A | B | C |
| 211B | A | C |
| 215A | A | C |
| 215B | C | C |
| 216A | B | B |
| 216B | C | C |
| 217A | A | B |
| 217B | C | C |
| 218A | A | B |
| 218B | C | C |

TABLE 2-continued

| Compound No. | TECC (AUC, 10 μM) | DSLS 3D (100 μM ΔT) |
|---|---|---|
| 219 | C | C |
| 220A | A | A |
| 220B | C | C |
| 221 | B | C |
| 222A | C | B |
| 222B | C | C |
| 223A | A | A |
| 223B | C | C |
| 224 | C | C |
| 225A | C | B |
| 225B | C | C |
| 226 | C | C |
| 227 | B | C |
| 228 | C | C |
| 229 | C | C |
| 230 | C | C |
| 231 | C | C |
| 233 | B | C |
| 234 | B | C |
| 235A | B | B |
| 235B | C | C |
| 236A | A | B |
| 236B | C | C |
| 237A | C | A |
| 237B | C | C |
| 238 | A | C |
| 239A | B | A |
| 239B | A | A |
| 240 | A | B |
| 241A | C | A |
| 241B | A | A |
| 242 | C | C |
| 243A | C | B |
| 243B | C | C |
| 244 | C | C |
| 245 | C | C |
| 246A | B | C |
| 246B | B | A |
| 247 | C | C |
| 248A | C | C |
| 248B | A | C |
| 249A | C | C |
| 249B | B | C |
| 250 | C | C |
| 251 | B | C |
| 252 | C | C |
| 253 | B | C |
| 254 | B | C |
| 255A | A | B |
| 255B | C | C |
| 256 | C | C |
| 257 | B | C |
| 258 | C | C |
| 259 | C | C |
| 260A | C | C |
| 260B | A | B |
| 261A | C | C |
| 261B | A | A |
| 262 | C | C |
| 263 | C | B |
| 264 | C | C |
| 265 | C | B |
| 266A | A | A |
| 266B | C | C |
| 267 | C | C |
| 268 | B | C |
| 269 | C | C |
| 270 | B | C |
| 271 | C | C |
| 272 | C | C |
| 273 | B | C |
| 274 | C | C |
| 275 | C | C |
| 276 | B | C |
| 277 | A | C |
| 278 | C | C |

TABLE 2-continued

| Compound No. | TECC (AUC, 10 μM) | DSLS 3D (100 μM ΔT) |
|---|---|---|
| 279 | C | C |
| 280 | C | C |
| 281 | C | C |
| 282 | C | C |
| 283 | C | C |
| 284 | C | C |
| 285 | C | C |
| 286 | C | C |
| 287 | C | C |
| 288 | C | C |
| 289 | C | C |
| 290 | C | C |
| 291 | C | C |
| 292 | C | C |
| 293 | B | C |
| 294 | A | C |
| 295 | B | B |
| 296 | A | A |
| 297 | A | B |
| 299A | | A |
| 299B | | B |
| 300A | | A |
| 300B | | A |
| 301 | | A |
| 302A | | B |
| 302B | | B |
| 303A | | B |
| 303B | | A |
| 304 | | B |
| 305 | | B |
| 306 | | A |
| 307 | | A |
| 308 | | B |
| 309 | | B |
| 310 | | A |
| 311 | | A |
| 312 | | A |
| 313 | | B |
| 314A | | A |
| 314B | | B |
| 315A | | A |
| 315B | | A |
| 315C | | A |
| 315D | | B |
| 315E | | A |
| 316A | | B |
| 316B | | A |
| 317A | | B |
| 317B | | A |
| 318A | | A |
| 318B | | A |
| 319 | | B |
| 320 | | B |
| 321 | | A |
| 322 | | B |
| 323 | | B |
| 324 | | B |
| 325 | | B |
| 326 | | A |
| 327 | | A |
| 328 | | B |
| 329 | | B |
| 330 | | A |
| 331 | | A |
| 332 | | A |
| 333 | | B |
| 334 | | B |
| 335 | | A |
| 336A | | A |
| 336B | | A |
| 337 | | A |
| 338 | | A |
| 339 | | A |
| 340 | | B |
| 341 | | B |
| 342 | | A |

TABLE 2-continued

| Compound No. | TECC (AUC, 10 μM) | DSLS 3D (100 μM ΔT) |
|---|---|---|
| 345 | | B |
| 346 | | B |
| 347 | | B |
| 348A | | A |
| 348B | | A |
| 349 | | B |
| 350 | | A |
| 351 | | B |
| 352 | | A |
| 353 | | A |
| 354 | | A |
| 355 | | A |
| 356 | | A |
| 357 | | B |
| 358 | | A |
| 359 | | B |
| 360A | | A |
| 360B | | B |
| 360C | | A |
| 360D | | A |
| 361 | | A |
| 362 | | A |
| 363 | | A |
| 364 | | A |
| 365 | | A |
| 366 | | A |
| 367A | | A |
| 367B | | A |
| 368A | | B |
| 368B | | A |
| 369A | | C |
| 369B | | B |
| 370A | | B |
| 370B | | A |
| 371 | | B |
| 372 | | B |
| 373 | | B |
| 374 | | B |
| 375 | | B |
| 376 | | A |
| 377 | | B |
| 378 | | A |
| 379A | | A |
| 379B | | A |
| 379C | | A |
| 380 | | A |
| 381A | | A |
| 381B | | A |
| 382 | | B |
| 383 | | B |
| 384 | | A |
| 385A | | B |
| 385B | | A |

EQUIVALENTS AND SCOPE

In the claims articles such as “a,” “an,” and “the” may mean one or more than one unless indicated to the contrary or otherwise evident from the context. Claims or descriptions that include “or” between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members, are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms “comprising” and “containing” are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

We claim:

1. A compound selected from the group consisting of:

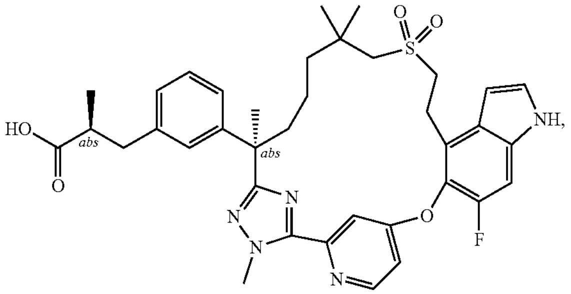 [SMILES: C[C@@H](Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O]

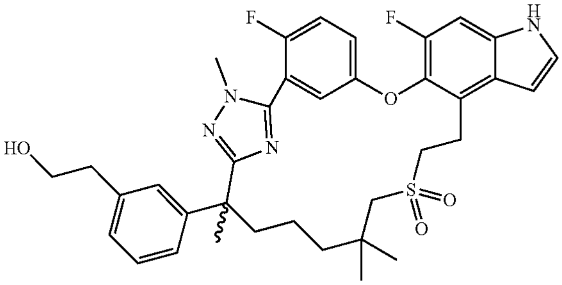

,

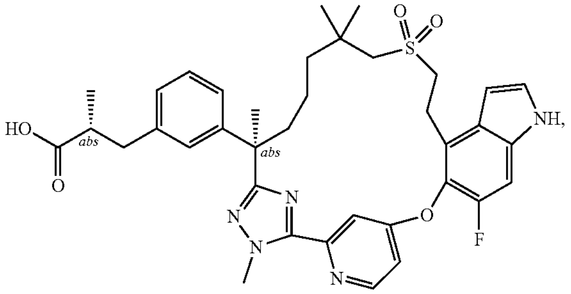 [SMILES: C[C@H](Cc1cccc([C@@]2(C)CCCC(C)(C)CS(=O)(=O)CCc3c(c(F)cc4[nH]ccc34)Oc3ccnc(c3)-c3nc2nn3C)c1)C(=O)O]

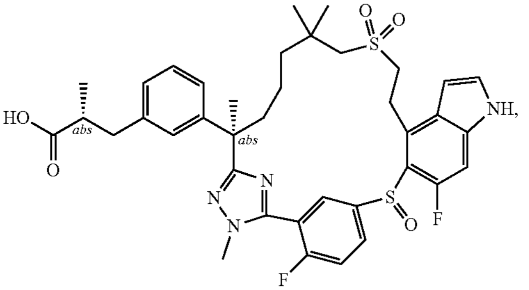

and

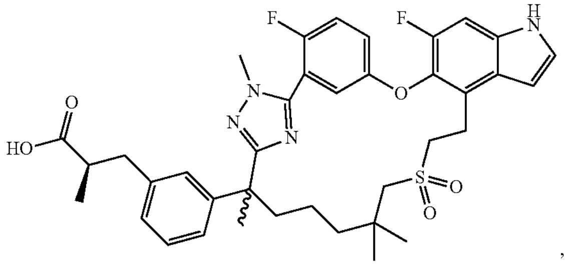

, or a pharmaceutically acceptable salt thereof.

2. The compound of claim 1, wherein the compound is:

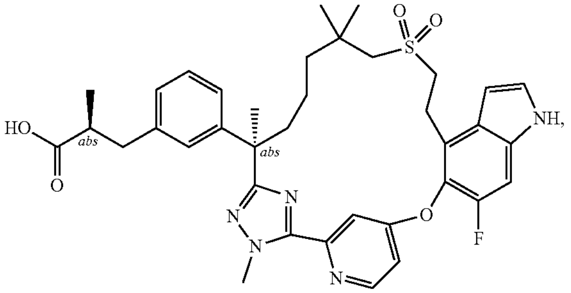

or a pharmaceutically acceptable salt thereof.

3. The compound of claim 1, wherein the compound is:

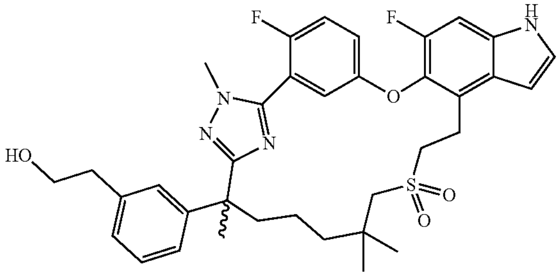

, or a pharmaceutically acceptable salt thereof.

4. The compound of claim 1, wherein the compound is:

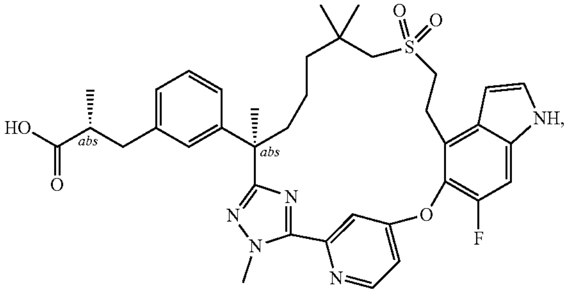

or a pharmaceutically acceptable salt thereof.

5. The compound of claim 1, wherein the compound is:

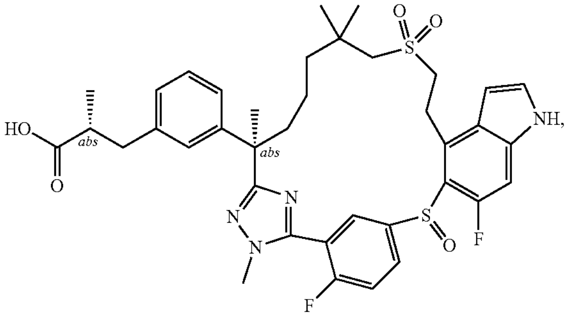 [SMILES: C[C@H](Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O]

or a pharmaceutically acceptable salt thereof.

6. The compound of claim 1, wherein the compound is

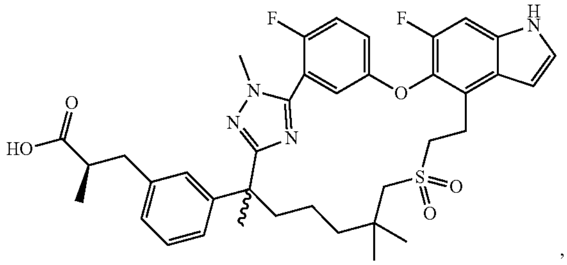 [SMILES: C[C@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

, or a pharmaceutically acceptable salt thereof.

7. A pharmaceutical composition comprising the compound of claim 2, or a pharmaceutically acceptable salt thereof and a pharmaceutically acceptable excipient.

8. A pharmaceutical composition comprising the compound of claim 3, or a pharmaceutically acceptable salt thereof and a pharmaceutically acceptable excipient.

9. A pharmaceutical composition comprising the compound of claim 4, or a pharmaceutically acceptable salt thereof and a pharmaceutically acceptable excipient.

10. A pharmaceutical composition comprising the compound of claim 5, or a pharmaceutically acceptable salt thereof and a pharmaceutically acceptable excipient.

11. A pharmaceutical composition comprising the compound of claim 6, or a pharmaceutically acceptable salt thereof and a pharmaceutically acceptable excipient.

12. A method of treating cystic fibrosis in a subject in need thereof, the method comprising administering to the subject a therapeutically effective amount of a compound selected from the group consisting of:

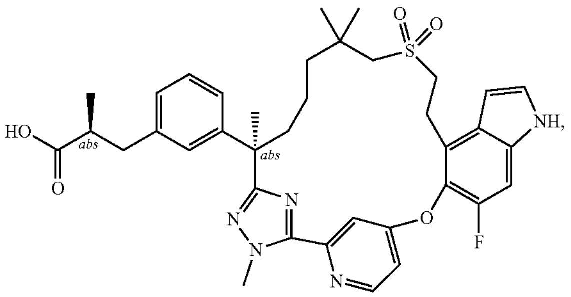

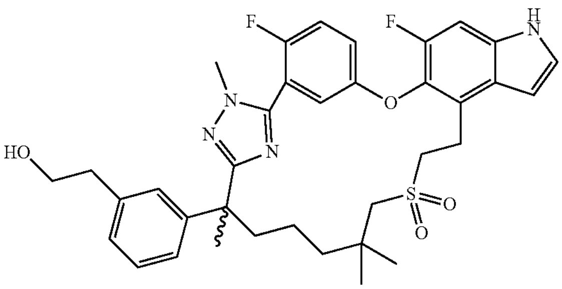

,

-continued

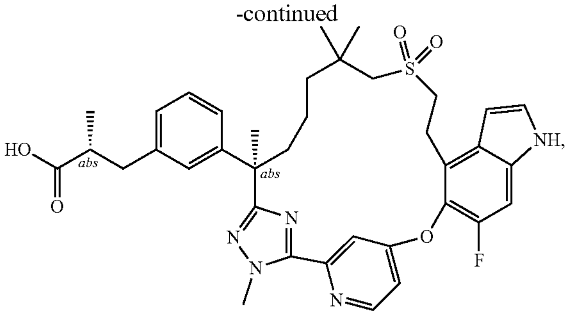

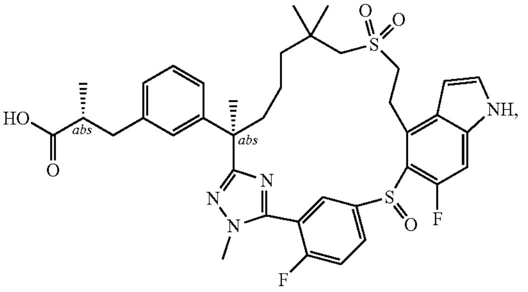

and

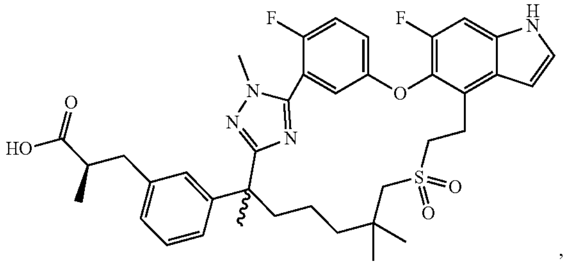

, or a pharmaceutically acceptable salt thereof.

13. The method of claim 12, wherein the compound is:

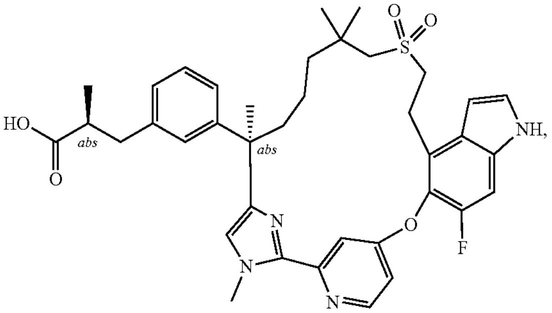 [SMILES: C[C@@H](Cc1cccc([C@@]2(C)CCCC(C)(C)CS(=O)(=O)CCc3c(c(F)cc4[nH]ccc34)Oc3ccnc(c3)-c3nc2cn3C)c1)C(=O)O]

or a pharmaceutically acceptable salt thereof.

14. The method of claim 12, wherein the compound is:

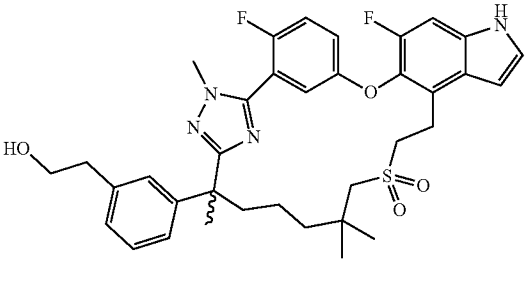

, or a pharmaceutically acceptable salt thereof.

15. The method of claim 12, wherein the compound is:

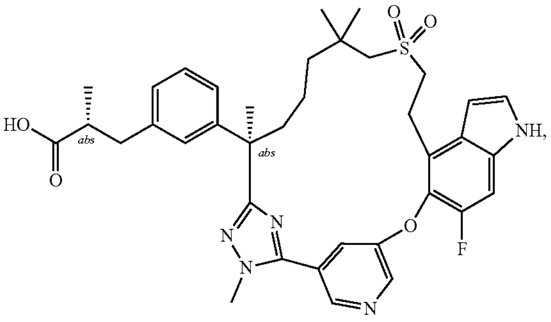 [SMILES: C[C@H](Cc1cccc([C@@]2(C)CCCC(C)(C)CS(=O)(=O)CCc3c(c(F)cc4[nH]ccc34)Oc3cncc(c3)-c3nc2nn3C)c1)C(=O)O]

or a pharmaceutically acceptable salt thereof.

16. The method of claim 12, wherein the compound is:

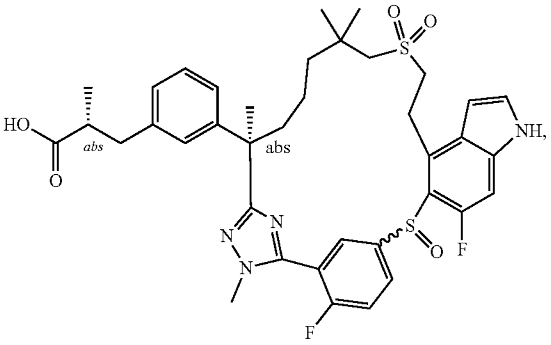 [SMILES: C[C@H](Cc1cccc([C@@]2(C)CCCC(C)(C)CS(=O)(=O)CCc3c(c(F)cc4[nH]ccc34)S(=O)c3ccc(F)c(c3)-c3nc2nn3C)c1)C(=O)O]

or a pharmaceutically acceptable salt thereof.

17. The method of claim 12, wherein the compound is:

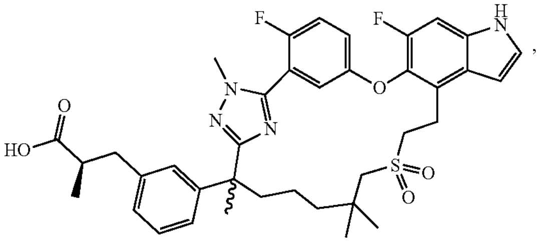 [SMILES: C[C@H](Cc1cccc(C2(C)CCCC(C)(C)CS(=O)(=O)CCc3c(c(F)cc4[nH]ccc34)Oc3ccc(F)c(c3)-c3nc2nn3C)c1)C(=O)O]

or a pharmaceutically acceptable salt thereof.

18. The method of claim 13, wherein the subject in need thereof has at least one copy of a CFTR mutation, wherein the CFTR mutation is a ΔF508-CFTR mutation.

19. The method of claim 14, wherein the subject in need thereof has at least one copy of a CFTR mutation, wherein the CFTR mutation is a ΔF508-CFTR mutation.

20. The method of claim 15, wherein the subject in need thereof has at least one copy of a CFTR mutation, wherein the CFTR mutation is a ΔF508-CFTR mutation.

21. The method of claim 16, wherein the subject in need thereof has at least one copy of a CFTR mutation, wherein the CFTR mutation is a ΔF508-CFTR mutation.

22. The method of claim 17, wherein the subject in need thereof has at least one copy of a CFTR mutation, wherein the CFTR mutation is a ΔF508-CFTR mutation.

* * * * *